(12) United States Patent
Curtin et al.

(10) Patent No.: US 9,302,989 B2
(45) Date of Patent: Apr. 5, 2016

(54) NAMPT AND ROCK INHIBITORS

(75) Inventors: Michael L. Curtin, Pleasant Prairie, WI (US); Bryan K. Sorensen, Antioch, IL (US); Howard R. Heyman, Deerfield, IL (US); Richard F. Clark, Gurnee, IL (US); Kevin R. Woller, Antioch, IL (US); Omar J. Shah, Issaquah, WA (US); Michael Michaelides, Libertyville, IL (US); Chris Tse, Libertyville, IL (US); Anil Vasudevan, Union Grove, WI (US); Helmut Mack, Ludwigshafen (DE); Todd M. Hansen, Grayslake, IL (US); Ramzi Sweis, Lake Bluff, IL (US); Marina A. Pliushchev, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/294,303

(22) Filed: Nov. 11, 2011

(65) Prior Publication Data

US 2012/0122842 A1    May 17, 2012

Related U.S. Application Data

(60) Provisional application No. 61/413,722, filed on Nov. 15, 2010, provisional application No. 61/474,015, filed on Apr. 11, 2011, provisional application No. 61/525,405, filed on Aug. 19, 2011.

(51) Int. Cl.

| | | |
|---|---|---|
| *A01N 43/38* | (2006.01) | |
| *A61K 31/40* | (2006.01) | |
| *C07D 209/44* | (2006.01) | |
| *C07D 401/12* | (2006.01) | |
| *C07D 401/14* | (2006.01) | |
| *C07D 403/10* | (2006.01) | |
| *C07D 407/12* | (2006.01) | |
| *C07D 407/14* | (2006.01) | |
| *C07D 413/12* | (2006.01) | |
| *C07D 417/12* | (2006.01) | |
| *C07D 471/04* | (2006.01) | |
| *C07D 491/048* | (2006.01) | |
| *C07D 495/04* | (2006.01) | |
| *C07D 403/12* | (2006.01) | |
| *C07D 403/14* | (2006.01) | |
| *C07D 405/12* | (2006.01) | |

(52) U.S. Cl.
CPC ............ *C07D 209/44* (2013.01); *C07D 401/12* (2013.01); *C07D 401/14* (2013.01); *C07D 403/10* (2013.01); *C07D 403/12* (2013.01); *C07D 403/14* (2013.01); *C07D 405/12* (2013.01); *C07D 407/12* (2013.01); *C07D 407/14* (2013.01); *C07D 413/12* (2013.01); *C07D 417/12* (2013.01); *C07D 471/04* (2013.01); *C07D 491/048* (2013.01); *C07D 495/04* (2013.01)

(58) Field of Classification Search
None
See application file for complete search history.

(56) References Cited

U.S. PATENT DOCUMENTS

| | | | |
|---|---|---|---|
| 3,535,323 | A | 10/1970 | Heidenbluth et al. |
| 4,419,360 | A | 12/1983 | Smolanoff |
| 5,514,654 | A | 5/1996 | Pecar et al. |
| 5,726,197 | A * | 3/1998 | Clark et al. ................... 514/387 |
| 6,677,333 | B1 | 1/2004 | Seko et al. |
| 7,511,013 | B2 | 3/2009 | Molino et al. |
| 7,514,068 | B2 | 4/2009 | Tung |
| 7,521,421 | B2 | 4/2009 | Naicker et al. |
| 7,528,131 | B2 | 5/2009 | Persichetti et al. |
| 7,531,685 | B2 | 5/2009 | Czarnik |
| 7,534,814 | B2 | 5/2009 | Ascher et al. |
| 7,538,189 | B2 | 5/2009 | Naicker et al. |
| 7,612,076 | B2 | 11/2009 | Nettekoven et al. |
| 8,778,936 | B2 | 7/2014 | Berdini et al. |
| 8,957,205 | B2 | 2/2015 | Kobayashi et al. |
| 2005/0084506 | A1 | 4/2005 | Tachdjian et al. |
| 2006/0045953 | A1 | 3/2006 | Tachdjian et al. |
| 2006/0223826 | A1 | 10/2006 | Abe et al. |
| 2007/0060566 | A1 | 3/2007 | Bailey et al. |
| 2009/0082471 | A1 | 3/2009 | Czarnik |
| 2009/0088416 | A1 | 4/2009 | Czarnik |
| 2009/0093422 | A1 | 4/2009 | Tung et al. |
| 2009/0105147 | A1 | 4/2009 | Masse |
| 2009/0105307 | A1 | 4/2009 | Galley et al. |
| 2009/0105338 | A1 | 4/2009 | Czarnik |
| 2009/0111840 | A1 | 4/2009 | Herold et al. |

(Continued)

FOREIGN PATENT DOCUMENTS

| | | | | |
|---|---|---|---|---|
| BE | 648616 | | 9/1964 | |
| CH | 433312 | * | 9/1967 | ............. C07D 27/48 |

(Continued)

OTHER PUBLICATIONS

Shoeb, et. al., Indian Journal of Chemistry (1967), 5(4), 142-4.*

(Continued)

*Primary Examiner* — Jeffrey H Murray
(74) *Attorney, Agent, or Firm* — Glen J. Gesicki

(57) ABSTRACT

Disclosed are 1,3-dihydro-2H-isoindole compounds which inhibit the activity of NAMPT, compositions containing the compounds and methods of using the compounds to treat diseases during which NAMPT is expressed, e.g., cancer, metabolic disorders, and inflammatory disorders. Disclosed are 1,3-dihydro-2H-isoindole compounds which inhibit the activity of ROCK, compositions containing the compounds and methods of using the compounds to treat diseases during which ROCK is expressed, e.g., cancer, cardiovascular disorders, and inflammatory disorders.

20 Claims, No Drawings

(56) References Cited

U.S. PATENT DOCUMENTS

| | | | |
|---|---|---|---|
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |
| 2010/0120769 A1 | 5/2010 | Nettekoven et al. | |

FOREIGN PATENT DOCUMENTS

| | | | |
|---|---|---|---|
| EP | 2067771 A1 | 6/2009 | |
| JP | 2003277340 A | 10/2003 | |
| WO | WO9507271 A1 | 3/1995 | |
| WO | WO9624587 A1 | 8/1996 | |
| WO | WO9634870 A1 | 11/1996 | |
| WO | WO9710223 A1 | 3/1997 | |
| WO | WO9748397 A1 | 12/1997 | |
| WO | WO9748696 A1 | 12/1997 | |
| WO | WO0234760 A2 | 5/2002 | |
| WO | WO02081443 A1 | 10/2002 | |
| WO | WO03041641 A2 | 5/2003 | |
| WO | WO03080054 A1 | 10/2003 | |
| WO | WO2004046107 A1 | 6/2004 | |
| WO | WO2004067509 A1 | 8/2004 | |
| WO | WO2004098609 A1 | 11/2004 | |
| WO | WO2004101533 A1 | 11/2004 | |
| WO | WO2005005392 A1 | 1/2005 | |
| WO | WO2005015158 | * | 2/2005 |
| WO | WO2005019240 A2 | 3/2005 | |
| WO | 2005037214 A2 | 4/2005 | |
| WO | WO2005051945 A1 | 6/2005 | |
| WO | WO2005095403 A2 | 10/2005 | |
| WO | WO2005099353 A2 | 10/2005 | |
| WO | 2006008754 A1 | 1/2006 | |
| WO | WO2006008754 A1 | 1/2006 | |
| WO | WO2006113919 A2 | 10/2006 | |
| WO | WO2007011290 A1 | 1/2007 | |
| WO | WO2007026920 A2 | 3/2007 | |
| WO | WO2007054453 A2 | 5/2007 | |
| WO | WO2007076055 A2 | 7/2007 | |
| WO | WO2007121124 A2 | 10/2007 | |
| WO | WO2007134958 A1 | 11/2007 | |
| WO | WO2007136703 A1 | 11/2007 | |
| WO | WO2007137955 A1 | 12/2007 | |
| WO | 2008027740 A2 | 3/2008 | |
| WO | WO2008025857 A2 | 3/2008 | |
| WO | WO2008086047 A1 | 7/2008 | |
| WO | WO2008104077 A1 | 9/2008 | |
| WO | WO2008116814 A1 | 10/2008 | |
| WO | WO2008130319 A2 | 10/2008 | |
| WO | WO2009017838 A2 | 2/2009 | |
| WO | WO2009052068 A1 | 4/2009 | |
| WO | WO2009056805 A1 | 5/2009 | |
| WO | WO2009071677 A1 | 6/2009 | |
| WO | WO2009086835 A1 | 7/2009 | |
| WO | WO2009109610 A1 | 9/2009 | |
| WO | WO2009118712 A2 | 10/2009 | |
| WO | WO2009156421 A1 | 12/2009 | |
| WO | WO2010023307 A1 | 3/2010 | |
| WO | WO2010033349 A1 | 3/2010 | |
| WO | WO2010045306 A2 | 4/2010 | |
| WO | WO2010057101 A2 | 5/2010 | |
| WO | WO2010066709 A1 | 6/2010 | |
| WO | WO2010089127 A1 | 8/2010 | |
| WO | WO2010122968 A1 | 10/2010 | |
| WO | WO2011006803 A1 | 1/2011 | |
| WO | 2011109441 A1 | 9/2011 | |
| WO | WO2012031196 A1 | 3/2012 | |
| WO | WO2012031197 A1 | 3/2012 | |
| WO | WO2012031199 A1 | 3/2012 | |

OTHER PUBLICATIONS

Adya R., et al., "Nuclear Factor-kB Induction by Visfatin in Human Vascular Endothelial Cells: Its Role in MMP-2/9 Production and Activation," Diabetes Care, 2008, vol. 31 (4), pp. 758-760.

Beylot, M. et al., "In Vivo Studies of Intrahepatic Metabolic Pathways," Diabetes Metabolism, 1997, vol. 23 (3), pp. 251-257.

Blagojevic, N. et al., "Role of heavy water in Boron Neutron Capture Therapy," Topics in Dosimetry & Treatment Planning for Neutron Capture Therapy, 1994, pp. 125-134.

Blake, M. I. et al., "Studies With Deuterated Drugs," Journal of Pharmaceutical Sciences, 1975, vol. 64 (3), pp. 367-391.

Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.

Bruzzone S., et al., "Catastrophic NAD+ Depletion in Activated T Lymphocytes through Nampt Inhibition Reduces Demyelination and Disability in EAE," PLoS One, 2009, vol. 4 (11), pp. e7897.

Busso N., et al., "Pharmacological Inhibition of Nicotinamide Phosphoribosyltransferase/visfatin Enzymatic Activity Identifies a New Inflammatory Pathway Linked to NAD," PLoS One, 2008, vol. 3 (5), pp. e2267.

Czajka, D. M. et al., "Effect of Deuterium Oxide on the Reproductive Potential of Mice," Annals of the New York Academy of Sciences, 1960, vol. 84, pp. 770-779.

Czajka, D. M. et al., "Physiological Effects of Deuterium on Dogs," American Journal of Physiology, 1961, vol. 201 (2), pp. 357-362.

Foster, A. B. et al., "Deuterium Isotope Effects in the Metabolism of Drugs and Xenobiotics: Implications for Drug Design," Advances in Drug Research, 1985, vol. 14, pp. 2-36.

Galli M., et al., "The Nicotinamide Phosphoribosyltransferase: A Molecular Link Between Metabolism, Inflammation, and Cancer," Cancer Research, 2010, vol. 70 (1), pp. 8-11.

Garten A., et al., "Nampt: Linking NAD Biology, Metabolism and Cancer," Trends in Endocrinology and Metabolism, 2009, vol. 20 (3), pp. 130-138.

Hansen C.M., et al., "Cyanoguanidine CHS 828 Induces Programmed Cell Death with Apoptotic Features in Human Breast Cancer Cells in Vitro," Anticancer Research, 2000, vol. 20 (6B), pp. 4211-4220.

Jesudason C.D., et al., "Synthesis and SAR of Novel Histamine H3 Receptor Antagonists," Bioorganic & Medicinal Chemistry Letters, 2006, vol. 16 (13), pp. 3415-3418.

Kato, S. et al., "Synthesis of Deuterated Mosapride Citrate," Journal of Labelled Compounds and Radiopharmaceuticals, 1995, vol. 36 (10), pp. 927-932.

Kim S.R., et al., "Visfatin Promotes Angiogenesis by Activation of Extracellular Signal-regulated Kinase 1/2," Biochemical and Biophysical Research Communications, 2007, vol. 357 (1), pp. 150-156.

Kushner, et al., "Pharmacological uses and perspectives of heavy water and deuterated compounds," Canadian Journal of Physiology and Pharmacology, 1999, vol. 77 (2), pp. 79-88.

Lemoucheux L., et al., "Debenzylation of Tertiary Amines Using Phosgene or Triphosgene: An Efficient and Rapid Procedure for the Preparation of Carbamoyl Chlorides and Unsymmetrical Ureas. Application in Carbon-11 Chemistry," Journal of Organic Chemistry, 2003, vol. 68 (19), pp. 7289-7297.

Lizondo, J. et al., "Linezolid: Oxazolidinone antibacterial," Drugs of the Future, 1996, vol. 21 (11), pp. 1116-1123.

Mallesham, B. et al., "Highly Efficient CuI-Catalyzed Coupling of Aryl Bromides With Oxazolidinones Using Buchwald's Protocol: A Short Route to Linezolid and Toloxatone," Organic Letters, 2003, vol. 5 (7), pp. 963-965.

Olesen U.H., et al., "A Preclinical Study on the Rescue of Normal Tissue by Nicotinic Acid in High-dose Treatment with APO866, a Specific Nicotinamide Phosphoribosyltransferase Inhibitor," Molecular Cancer Therapeutics, 2010, vol. 9 (6), pp. 1609-1617.

Peterson S.L., et al., "Parallel Synthesis of Ureas and Carbamates from Amines and CO2 Under Mild Conditions," Organic Letters, 2010, vol. 12 (6), pp. 1340-1343.

Shoeb A., et al., "Studies in Possible Oral Hypoglycaemic Agents: Part V—Synthesis of Carbamoylindoles, Carbamoylisoindolines, 3-Indolylethyl Urea (or Thiourea) & 2-Isoindolinylpropyl Urea (or Thiourea) Derivatives & their Biological Activity," Indian Journal of Chemistry, 1967, vol. 5, pp. 142-144.

STN Database Registry No. XP002665849 dated Oct. 23, 2008.

(56) References Cited

OTHER PUBLICATIONS

STN Database Registry No. XP002665850 dated Jul. 7, 2011.
Sutton, V.R. et al., "Bcl-2 Prevents Apoptosis Induced by Perforin and Granzyme B, but Not That Mediated by Whole Cytotoxic Lymphocytes," Journal of Immunology, 1997, vol. 158 (12), pp. 5783-5790.
Takahashi T., et al., "Novel Potent Neuropeptide Y Y5 Receptor Antagonists: Synthesis and Structure-activity Relationships of Phenylpiperazine Derivatives," Bioorganic & Medicinal Chemistry, 2006, vol. 14 (22), pp. 7501-7511.
Thomson, J.F., "Physiological Effects of D20 in Mammals," Annals of the New York Academy of Sciences, 1960, vol. 84, pp. 736-744.
Van Beijnum J.R., et al., "Target Validation for Genomics Using Peptide-specific Phage Antibodies: A Study of Five Gene Products Overexpressed in Colorectal Cancer," International Journal of Cancer, 2002, vol. 101 (2), pp. 118-127.
Wodka D., et al., "Activation of Carboxylic Acids by Burgess Reagent: an Efficient Route to Acyl ureas and Amides," Tetrahedron Letters, 2006, vol. 47, pp. 1825-1828.
Ziegler M., "New Functions of a Long-known Molecule. Emerging Roles of NAD in Cellular Signaling," European Journal of Biochemistry, 2000, vol. 267 (6), pp. 1550-1564.
Blagojevic N., et al., In "Dosimetry & Treatment Planning for Neutron Capture Therapy", Zamenhof R, et al., Edition, 1994, Advanced Medical Publishing, pp. 125-134.
International Search Report and Written Opinion for Application No. PCT/CN2011/082108, mailed on Aug. 23, 2012, 10 pages.
International Search Report and Written Opinion for Application No. PCT/US2011/060425, mailed on Mar. 1, 2012, 14 pages.
Lockman J.W., et al., "Analogues of 4-[(7-Bromo-2-Methyl-4-Oxo-3 H -Quinazolin-6-yl) Methylprop-2-Ynylamino]- N -(3-pyridylmethyl)benzamine (Cb-30865) as Potent Inhibitors of Nicotinamide Phosphoribosyltransferase (Nampt)," Journal of Medicinal Chemistry, 2010, vol. 53 (24), pp. 8734-8746.

* cited by examiner

NAMPT AND ROCK INHIBITORS

RELATED APPLICATION INFORMATION

This application claims the benefit of U.S. Provisional Patent Application Ser. No. 61/413,722, filed on Nov. 15, 2010, U.S. Provisional Patent Application Ser. No. 61/474,015, filed on Apr. 11, 2011, and U.S. Provisional Patent Application Ser. No. 61/525,405, filed on Aug. 19, 2011, the contents of each of which are herein incorporated by reference.

FIELD OF THE INVENTION

This invention pertains to compounds which inhibit the activity of NAMPT, compositions containing the compounds, and methods of treating diseases during which NAMPT is expressed. This invention also pertains to compounds which inhibit the activity of ROCK, compositions containing the compounds, and methods of treating diseases during which ROCK is expressed.

BACKGROUND OF THE INVENTION

NAD+ (nicotinamide adenine dinucleotide) is a coenzyme that plays a critical role in many physiologically essential processes (Ziegkel, M. *Eur. J. Biochem.* 267, 1550-1564, 2000). NAD is necessary for several signaling pathways including among others poly ADP-ribosylation in DNA repair, mono-ADP-ribosylation in both the immune system and G-protein-coupled signaling, and NAD is also required by sirtuins for their deacetylase activity (Gallen, A. et al *Trends in Endocrinology and Metabolism,* 20, 130-138, 2008).

NAMPT (also known as pre-B-cell-colony-enhancing factor (PBEF) and visfatin) is an enzyme that catalyzes the phosphoribosylation of nicotinamide and is the rate-limiting enzyme in one of two pathways that salvage NAD.

cancer (Van Beijnum, J. R. et al *Int. J. Cancer* 101, 118-127, 2002) and NAMPT is involved in angiogenesis (Kim, S. R. et al. *Biochem. Biophys. Res. Commun.* 357, 150-156, 2007). Small-molecule inhibitors of NAMPT have been shown to cause depletion of intracellular NAD+ levels and ultimately induce tumor cell death (Hansen, C M et al. *Anticancer Res.* 20, 42111-4220, 2000) as well as inhibit tumor growth in xenograft models (Olese, U. H. et al. *Mol Cancer Ther.* 9, 1609-1617, 2010).

NAMPT inhibitors also have potential as therapeutic agents in inflammatory and metabolic disorders (Galli, M. et al *Cancer Res.* 70, 8-11, 2010). For example, NAMPT is the predominant enzyme in T and B lymphocytes. Selective inhibition of NAMPT leads to NAD+ depletion in lymphocytes blocking the expansion that accompanies autoimmune disease progression whereas cell types expressing the other NAD+ generating pathways might be spared. A small molecule NAMPT inhibitor (FK866) has been shown to selectively block proliferation and induce apoptosis of activated T cells and was efficacious in animal models of arthritis (collagen-induced arthritis) (Busso, N. et al. *Plos One* 3, e2267, 2008). FK866 ameliorated the manifestations of experimental autoimmune encephalomyelitis (EAE), a model of T-cell mediated autoimmune disorders. (Bruzzone, S et al. *Plos One* 4, e7897, 2009). NaMPT activity increases NF-kB transcriptional activity in human vascular endothelial cell, resulting in MMP-2 and MMP-9 activation, suggesting a role for NAMPT inhibitors in the prevention of inflammatory mediated complications of obesity and type 2 diabetes (Adya, R. et. Al. *Diabetes Care,* 31, 758-760, 2008).

Rho kinases (ROCKs), the first Rho effectors to be described, are serine/threonine kinases that are important in fundamental processes of cell migration, cell proliferation and cell survival. Abnormal activation of the Rho/ROCK pathway has been observed in various disorders. Examples of disease states in which compounds with ROCK inhibition have potentially beneficial therapeutic effects due to their anti

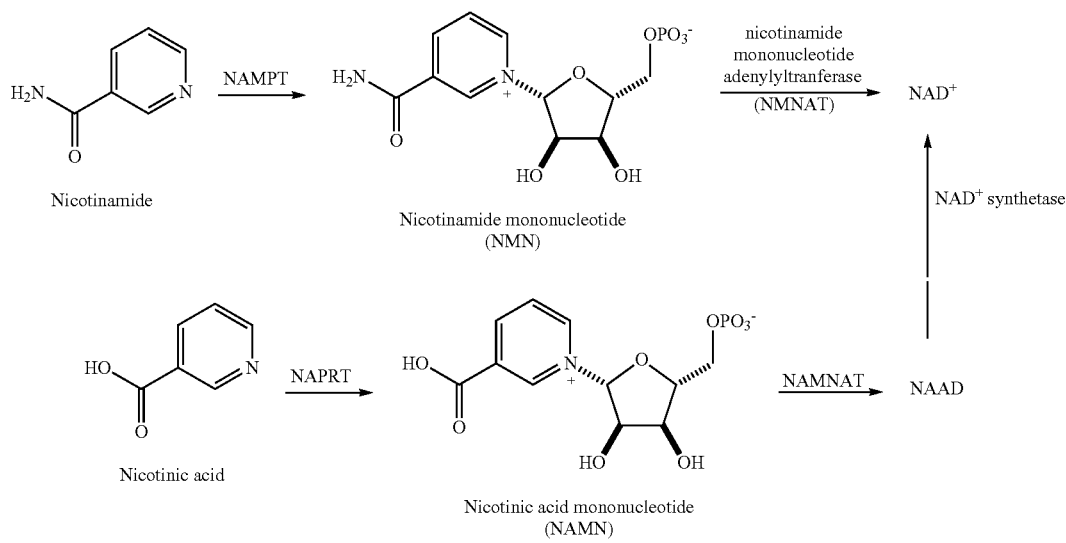

Increasing evidence suggests that NAMPT inhibitors have potential as anticancer agents. Cancer cells have a higher basal turnover of NAD and also display higher energy requirements compared with normal cells. Additionally, increased NAMPT expression has been reported in colorectal vasospasm activity includes cardiovascular diseases such as hypertension, chronic and congestive heart failure, cardiac hypertrophy, restenosis, chronic renal failure, cerebral vasospasm after subarachnoid bleeding, pulmonary hypertension and atherosclerosis. This muscle relaxing property is also beneficial for treating asthma, male erectile dysfunctions, female sexual dysfunction, and over-active bladder syndrome. Injury to the adult vertebrate brain and spinal cord activates ROCKs, thereby inhibiting neurite growth and sprouting Inhibition of ROCKs results in induction of new axonal growth, axonal rewiring across lesions within the CNS, accelerated regeneration and enhanced functional recovery after acute neuronal injury in mammals (spinal-cord injury, traumatic brain injury). Inhibition of the Rho/ROCK pathway has also proved to be efficacious in other animal models of neurodegeneration like stroke, inflammatory and demyelinating diseases, Alzheimer's disease as well as for the treatment of pain. Rho/ROCK pathway inhibitors therefore have potential for preventing neurodegeneration and stimulating neuroregeneration in various neurological disorders, including spinal-cord injury, Alzheimer's disease, stroke, multiple sclerosis, amyotrophic lateral sclerosis, as well as for the treatment of pain. ROCK inhibitors have been shown to possess anti-inflammatory properties. Thus, compounds of the invention can be used as treatment for neuroinflammatory diseases such as stroke, multiple sclerosis, Alzheimer's disease, Huntington's disease, Parkinson's disease, amyotrophic lateral sclerosis, and inflammatory pain, as well as other diseases such as rheumatoid arthritis, osteoarthritis, asthma, irritable bowel syndrome, Crohn's disease, psoriasis, ulcerative colitis, Lupus, and inflammatory bowel disease. Since ROCK inhibitors reduce cell proliferation and cell migration, they could be useful in treating cancer and tumor metastasis. Further more, there is evidence suggesting that ROCK inhibitors suppress cytoskeletal rearrangement upon virus invasion, thus they also have potential therapeutic value in anti-viral and anti-bacterial applications. ROCK inhibitors are also useful for the treatment of insulin resistance and diabetes. Further, ROCK inhibitors have been shown to ameliorate progression of cystic fibrosis (Abstract S02.3, 8th World Congress on Inflammation, Copenhagen, Denmark, Jun. 16-20, 2007).

In addition, Rho-associated coiled-coil forming protein kinases (ROCK)-1 and -2, have been shown to enhance myosin light chain (MLC) phosphorylation by inhibiting MLC phosphatase as well as phosphorylating MLC. This results in the regulation of actin-myosin contraction. Recent reports have demonstrated that inhibition of ROCK results in disruption of inflammatory cell chemotaxis as well as inhibition of smooth muscle contraction in models of pulmonary inflammation associated with asthma. Therefore, the inhibitors of the Rho/ROCK pathway may be useful for the treatment of asthma.

SUMMARY OF THE INVENTION

One embodiment of this invention, therefore, pertains to compounds and pharmaceutically acceptable salts thereof, which are useful as inhibitors of NAMPT or ROCK, the compounds having Formula (Ic)

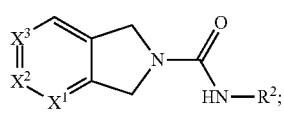

Formula (Ic)

wherein
$X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or
$X^1$ is CH; $X^2$ is N; and $X^3$ is $CR^1$; or
$X^1$ is $CR^1$; $X^2$ is N; and $X^3$ is CH; or
$X^1$ is N; $X^2$ is $CR^1$; and $X^3$ is CH; or
$X^1$ is N; $X^2$ is $CR^1$; and $X^3$ is N;

$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, C(O)H, $CF_3$, C(O)OH, or $C(O)NH_2$;

$R^2$ is alkyl, alkenyl, alkynyl, phenyl, heterocyclyl, cycloalkyl, or cycloalkenyl; wherein each $R^2$ alkyl, alkenyl, and alkynyl is optionally substituted with one, two, three or four independently selected $R^4$, $OR^4$, $SR^4$, $S(O)R^4$, $SO_2R^4$, $C(O)R^4$, $CO(O)R^4$, $OC(O)R^4$, $OC(O)OR^4$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, C(O)H, (O), CN, $N_3$, $NO_2$, $CF_3$, $CF_2CF_3$, $OCF_3$, $OCF_2CF_3$, F, Cl, Br or I; wherein each $R^2$ phenyl is optionally substituted at the para position with one independently selected $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $CHNOR^5$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, C(O)H, C(O)OH, OH, CN, $N_3$, $NO_2$, $CF_3$, $CF_2CF_3$, $OCF_3$, $OCF_2CF_3$, Br or I; wherein each $R^2$ phenyl is optionally additionally substituted with one F; wherein each $R^2$ heterocyclyl, cycloalkyl, and cycloalkenyl is optionally substituted with one, two, three or four independently selected $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N$ $(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, C(O)H, C(O)OH, OH, CN, $N_3$, $CF_3$, $CF_2CF_3$, $OCF_3$, $OCF_2CF_3$, F, Cl, Br or I;

$R^3$, at each occurrence, is independently selected alkyl, alkenyl, alkynyl, aryl, or heterocyclyl; wherein each $R^3$ alkyl, alkenyl, and alkynyl is optionally substituted with one, two, three or four independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, C(O)H, C(O)OH, OH, (O), CN, $N_3$, $NO_2$, $CF_3$, $CF_2CF_3$, $OCF_3$, $OCF_2CF_3$, F, Cl, Br or I;

$R^4$, at each occurrence, is independently selected alkyl, alkenyl, alkynyl, aryl, cycloalkyl, or heterocyclyl; wherein each $R^4$ alkyl, alkenyl, and alkynyl is optionally substituted with one, two, three or four independently selected $R^7$, $OR^7$, $SR^7$, $S(O)R^7$, $SO_2R^7$, $C(O)R^7$, $OC(O)R^7$, $OC(O)OR^7$, $NH_2$, $NHR^7$, $NHC(O)R^7$, $NR^7C(O)R^7$, $NHS(O)_2R^7$, $NR^7S(O)_2R^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, C(O)H, OH, (O), CN, N$_3$, NO$_2$, CF$_3$, CF$_2$CF$_3$, OCF$_3$, OCF$_2$CF$_3$, F, Cl, Br or I; wherein each R$^4$ aryl and heterocycyl is optionally substituted with one, two, three or four independently selected R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, C(O)H, C(O)OH, OH, CN, N$_3$, NO$_2$, CF$_3$, CF$_2$CF$_3$, OCF$_3$, OCF$_2$CF$_3$, F, Cl, Br or I;

R$^5$, at each occurrence, is independently selected alkyl, alkenyl, alkynyl, aryl, heterocyclyl, cycloalkyl, or cycloalkenyl; wherein each R$^5$ alkyl, alkenyl, and alkynyl is optionally substituted with one, two, three or four independently selected R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N(R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9$)$_2$, C(O)H, C(O)OH, OH, (O), CN, N$_3$, NO$_2$, CF$_3$, CF$_2$CF$_3$, OCF$_3$, OCF$_2$CF$_3$, F, Cl, Br or I;

R$^6$, at each occurrence, is independently selected alkyl, alkenyl, alkynyl, aryl, heterocyclyl, cycloalkyl, or cycloalkenyl; wherein each R$^6$ alkyl, alkenyl, and alkynyl is optionally substituted with one, two, three or four independently selected R$^{10}$, OR$^{10}$, SR$^{10}$, S(O)R$^{10}$, SO$_2$R$^{10}$, NHR$^{10}$, N(R$^{10}$)$_2$, C(O)R$^{10}$, C(O)NH$_2$, C(O)NHR$^{10}$, C(O)N(R$^{10}$)$_2$, NHC(O)R$^{10}$, NR$^{10}$C(O)R$^{10}$, NHSO$_2$R$^{10}$, NHC(O)OR$^{10}$, SO$_2$NH$_2$, SO$_2$NHR$^{10}$, SO$_2$N(R$^{10}$)$_2$, NHC(O)NH$_2$, NHC(O)NHR$^{10}$, OH, (O), C(O)OH, N$_3$, CN, NH$_2$, CF$_3$, CF$_2$CF$_3$, F, Cl, Br or I;

R$^7$, at each occurrence, is independently selected alkyl, alkenyl, alkynyl, aryl, heterocyclyl, cycloalkyl, or cycloalkenyl; wherein each R$^7$ alkyl, alkenyl, and alkynyl is optionally substituted with one, two, three or four independently selected R$^{11}$, OR$^{11}$, SR$^{11}$, S(O)R$^{11}$, SO$_2$R$^{11}$, NHR$^{11}$, N(R$^{11}$)$_2$, C(O)R$^{11}$, C(O)NH$_2$, C(O)NHR$^{11}$, C(O)N(R$^{11}$)$_2$, NHC(O)R$^{11}$, NR$^{11}$C(O)R$^{11}$, NHSO$_2$R$^{11}$, NHC(O)OR$^{11}$, SO$_2$NH$_2$, SO$_2$NHR$^{11}$, SO$_2$N(R$^{11}$)$_2$, NHC(O)NH$_2$, NHC(O)NHR$^{11}$, OH, (O), C(O)OH, N$_3$, CN, NH$_2$, CF$_3$, CF$_2$CF$_3$, F, Cl, Br or I;

R$^8$, at each occurrence, is independently selected alkyl, alkenyl, alkynyl, aryl, heterocyclyl, cycloalkyl, or cycloalkenyl; wherein each R$^8$ alkyl, alkenyl, and alkynyl is optionally substituted with one, two, three or four independently selected R$^{12}$, OR$^{12}$, SR$^{12}$, S(O)R$^{12}$, SO$_2$R$^{12}$, NHR$^{12}$, N(R$^{12}$)$_2$, C(O)R$^{12}$, C(O)NH$_2$, C(O)NHR$^{12}$, C(O)N(R$^{12}$)$_2$, NHC(O)R$^{12}$, NR$^{12}$C(O)R$^{12}$, NHSO$_2$R$^{12}$, NHC(O)OR$^{12}$, SO$_2$NH$_2$, SO$_2$NHR$^{12}$, SO$_2$N(R$^{12}$)$_2$, NHC(O)NH$_2$, NHC(O)NHR$^{12}$, OH, (O), C(O)OH, N$_3$, CN, NH$_2$, CF$_3$, CF$_2$CF$_3$, F, Cl, Br or I;

R$^9$, at each occurrence, is independently selected alkyl, alkenyl, alkynyl, aryl, heterocyclyl, cycloalkyl, or cycloalkenyl; wherein each R$^9$ alkyl, alkenyl, and alkynyl is optionally substituted with one, two, three or four independently selected alkoxy, OH, cycloalkyl, aryl, or heterocyclyl;

R$^{10}$, at each occurrence, is independently selected alkyl, alkenyl, alkynyl, aryl, heterocyclyl, cycloalkyl, or cycloalkenyl;

R$^{11}$, at each occurrence, is independently selected alkyl, alkenyl, alkynyl, aryl, heterocyclyl, cycloalkyl, or cycloalkenyl;

R$^{12}$, at each occurrence, is independently selected alkyl, alkenyl, alkynyl, aryl, heterocyclyl, cycloalkyl, or cycloalkenyl; wherein each R$^{12}$ alkyl, alkenyl, and alkynyl is optionally substituted with one or more alkoxy;

wherein the cyclic moieties represented by R$^3$, R$^5$, R$^6$, R$^7$, R$^8$, R$^9$, R$^{10}$, R$^{11}$, and R$^{12}$ are optionally substituted with one, two, three, four, five, or six independently selected R$^{13}$, OR$^{13}$, SR$^{13}$, S(O)R$^{13}$, SO$_2$R$^{13}$, C(O)R$^{13}$, CO(O)R$^{13}$, OC(O)R$^{13}$, OC(O)OR$^{13}$, NH$_2$, NHR$^{13}$, N(R$^{13}$)$_2$, NHC(O)R$^{13}$, NR$^{13}$C(O)R$^{13}$, NHS(O)$_2$R$^{13}$, NR$^{13}$S(O)$_2$R$^{13}$, NHC(O)OR$^{13}$, NR$^{13}$C(O)OR$^{13}$, NHC(O)NH$_2$, NHC(O)NHR$^{13}$, NHC(O)N(R$^{13}$)$_2$, NR$^{13}$C(O)NHR$^{13}$, NR$^{13}$C(O)N(R$^{13}$)$_2$, C(O)NH$_2$, C(O)NHR$^{13}$, C(O)N(R$^{13}$)$_2$, C(O)NHOH, C(O)NHOR$^{13}$, C(O)NHSO$_2$R$^{13}$, C(O)NR$^{13}$SO$_2$R$^{13}$, SO$_2$NH$_2$, SO$_2$NHR$^{13}$, SO$_2$N(R$^{13}$)$_2$, C(O)H, C(O)OH, OH, CN, N$_3$, NO$_2$, CF$_3$, CF$_2$CF$_3$, OCF$_3$, OCF$_2$CF$_3$, SCF$_3$, F, Cl, Br or I;

R$^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, or cycloalkenyl; wherein each R$^{13}$ alkyl, alkenyl, and alkynyl is optionally substituted with one, two, three or four independently selected R$^{14}$, OR$^{14}$, SR$^{14}$, S(O)R$^{14}$, SO$_2$R$^{14}$, C(O)R$^{14}$, OC(O)R$^{14}$, OC(O)OR$^{14}$, NH$_2$, NHR$^{14}$, N(R$^{14}$)$_2$, NHC(O)R$^{14}$, NR$^{14}$, C(O)R$^{14}$, NHS(O)$_2$R$^{14}$, NR$^{14}$S(O)$_2$R$^{14}$, NHC(O)OR$^{14}$, NR$^{14}$C(O)OR$^{14}$, NHC(O)NH$_2$, NHC(O)NHR$^{14}$, NHC(O)N(R$^{14}$)$_2$, NR$^{14}$C(O)NHR$^{14}$, NR$^{14}$C(O)N(R$^{14}$)$_2$, C(O)NH$_2$, C(O)NHR$^{14}$, C(O)N(R$^{14}$)$_2$, C(O)NHOH, C(O)NHOR$^{14}$, C(O)NHSO$_2$R$^{14}$, C(O)NR$^{14}$SO$_2$R$^{14}$, SO$_2$NH$_2$, SO$_2$NHR$^{14}$, SO$_2$N(R$^{14}$)$_2$, C(O)H, C(O)OH, OH, (O), CN, N$_3$, NO$_2$, CF$_3$, CF$_2$CF$_3$, OCF$_3$, OCF$_2$CF$_3$, F, Cl, Br or I; wherein each R$^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, and cycloalkenyl is optionally substituted with one, two, three or four independently selected R$^{15}$, OR$^{15}$, SR$^{15}$, S(O)R$^{15}$, SO$_2$R$^{15}$, C(O)R$^{15}$, CO(O)R$^{15}$, OC(O)R$^{15}$, OC(O)OR$^{15}$, NH$_2$, NHR$^{15}$, N(R$^{15}$)$_2$, NHC(O)R$^{15}$, NR$^{15}$C(O)R$^{15}$, NHS(O)$_2$R$^{15}$, NR$^{15}$S(O)$_2$R$^{15}$, NHC(O)OR$^{15}$, NR$^{15}$C(O)OR$^{15}$, NHC(O)NH$_2$, NHC(O)NHR$^{15}$, NHC(O)N(R$^{15}$)$_2$, NR$^{15}$C(O)NHR$^{15}$, NR$^{15}$C(O)N(R$^{15}$)$_2$, C(O)NH$_2$, C(O)NHR$^{15}$, C(O)N(R$^{15}$)$_2$, C(O)NHOH, C(O)NHOR$^{15}$, C(O)NHSO$_2$R$^{15}$, C(O)NR$^{15}$SO$_2$R$^{15}$, SO$_2$NH$_2$, SO$_2$NHR$^{15}$, SO$_2$N(R$^{15}$)$_2$, C(O)H, C(O)OH, OH, CN, N$_3$, NO$_2$, CF$_3$, CF$_2$CF$_3$, OCF$_3$, OCF$_2$CF$_3$, F, Cl, Br or I;

R$^{14}$, at each occurrence, is independently selected alkyl, alkenyl, alkynyl, aryl, heterocyclyl, cycloalkyl, or cycloalkenyl; wherein each R$^{14}$ alkyl, alkenyl, and alkynyl is optionally substituted with one, two, three or four independently selected heterocyclyl, alkoxy, NH$_2$, SO$_2$NH$_2$, C(O)H, C(O)OH, OH, (O), CN, N$_3$, NO$_2$, CF$_3$, CF$_2$CF$_3$, OCF$_3$, OCF$_2$CF$_3$, F, Cl, Br or I; wherein each R$^{14}$ aryl, heterocyclyl, cycloalkyl, and cycloalkenyl is optionally substituted with one, two, three or four independently selected R$^{16}$, OR$^{16}$, OH, F, Cl, Br, or I; wherein the R$^{16}$ alkyl is optionally substituted with one, two, three or four alkoxy;

$R^{15}$, at each occurrence, is independently selected alkyl; wherein the $R^{15}$ alkyl is optionally substituted with one, two, three or four alkoxy;

$R^{16}$, at each occurrence, is independently selected alkyl, wherein the $R^{16}$ alkyl is optionally substituted with one, two, three or four alkoxy;

with the proviso that when $X^1$, $X^2$, and $X^3$ are CH and $R^2$ is phenyl; $R^5$ is not methyl;

with the proviso that when $X^1$, $X^2$, and $X^3$ are CH, and $R^2$ is phenyl substituted with $OR^5$; $R^5$ is not methyl;

with the proviso that when $R^2$ is unsubstituted alkyl or optionally substituted alkyl; $R^2$ is $C_4$-$C_6$-alkyl;

with the proviso that when $R^{13}$ is piperidinyl, it is substituted piperidinyl; and with the proviso that when $R^{13}$ is pyrrolinyl, at least one of $X^1$, $X^2$, and $X^3$ is N.

Another embodiment pertains to compounds having Formula (Vc), and pharmaceutically acceptable salts thereof

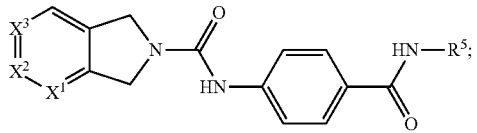

(Vc)

wherein $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N; or $X^1$ is CH; $X^2$ is N; and $X^3$ is $CR^1$; or $X^1$ is $CR^1$; $X^2$ is N; and $X^3$ is CH; or $X^1$ is N; $X^2$ is $CR^1$; and $X^3$ is CH; or $X^1$ is N; $X^2$ is $CR^1$; and $X^3$ is N;

$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, $C(O)H$, $CF_3$, $C(O)OH$, or $C(O)NH_2$;

$R^3$, at each occurrence, is independently selected alkyl, alkenyl, alkynyl, aryl, or heterocyclyl; wherein each $R^3$ alkyl, alkenyl, and alkynyl is optionally substituted with one, two, three or four independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I;

$R^5$, at each occurrence, is independently selected alkyl, alkenyl, alkynyl, aryl, heterocyclyl, cycloalkyl, or cycloalkenyl; wherein each $R^5$ alkyl, alkenyl, and alkynyl is optionally substituted with one, two, three or four independently selected $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I;

$R^6$, at each occurrence, is independently selected alkyl, alkenyl, alkynyl, aryl, heterocyclyl, cycloalkyl, or cycloalkenyl; wherein each $R^6$ alkyl, alkenyl, and alkynyl is optionally substituted with one, two, three or four independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, OH, (O), $C(O)OH$, $N_3$, CN, $NH_2$, $CF_3$, $CF_2CF_3$, F, Cl, Br or I;

$R^9$, at each occurrence, is independently selected alkyl, alkenyl, alkynyl, aryl, heterocyclyl, cycloalkyl, or cycloalkenyl; wherein each $R^9$ alkyl, alkenyl, and alkynyl is optionally substituted with one, two, three or four independently selected alkoxy, OH, cycloalkyl, aryl, or heterocyclyl;

$R^{10}$, at each occurrence, is independently selected alkyl, alkenyl, alkynyl, aryl, heterocyclyl, cycloalkyl, or cycloalkenyl;

wherein the cyclic moieties represented by $R^3$, $R^5$, $R^6$, $R^9$, and $R^{10}$ are optionally substituted with one, two, three, four, five, or six independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, $C(O)H$, $C(O)OH$, OH, CN, $N_3$, $NO_2$, $CF_3$, $CF_2CF_3$, $OCF_3$, $OCF_2CF_3$, $SCF_3$, F, Cl, Br or I;

$R^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, or cycloalkenyl; wherein each $R^{13}$ alkyl, alkenyl, and alkynyl is optionally substituted with one, two, three or four independently selected $R^{14}$, $OR^{14}$, $SR^{14}$, $S(O)R^{14}$, $SO_2R^{14}$, $C(O)R^{14}$, $OC(O)R^{14}$, $OC(O)OR^{14}$, $NH_2$, $NHR^{14}$, $N(R^{14})_2$, $NHC(O)R^{14}$, $NR^{14}C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, and cycloalkenyl is optionally substituted with one, two, three or four independently selected $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, C(O)NHR$^{15}$, C(O)N(R$^{15}$)$_2$, C(O)NHOH, C(O)NHOR$^{15}$, C(O)NHSO$_2$R$^{15}$, C(O)NR$^{15}$SO$_2$R$^{15}$, SO$_2$NH$_2$, SO$_2$NHR$^{15}$, SO$_2$N(R$^{15}$)$_2$, C(O)H, C(O)OH, OH, CN, N$_3$, NO$_2$, CF$_3$, CF$_2$CF$_3$, OCF$_3$, OCF$_2$CF$_3$, F, Cl, Br or I;

R$^{14}$, at each occurrence, is independently selected alkyl, alkenyl, alkynyl, aryl, heterocyclyl, cycloalkyl, or cycloalkenyl; wherein each R$^{14}$ alkyl, alkenyl, and alkynyl is optionally substituted with one, two, three or four independently selected heterocyclyl, alkoxy, NH$_2$, SO$_2$NH$_2$, C(O)H, C(O)OH, OH, (O), CN, N$_3$, NO$_2$, CF$_3$, CF$_2$CF$_3$, OCF$_3$, OCF$_2$CF$_3$, F, Cl, Br or I; wherein each R$^{14}$ aryl, heterocyclyl, cycloalkyl, and cycloalkenyl is optionally substituted with one, two, three or four independently selected R$^{16}$, OR$^{16}$, OH, F, Cl, Br, or I;

R$^{15}$, at each occurrence, is independently selected alkyl, wherein the R$^{15}$ alkyl is optionally substituted with one, two, three or four alkoxy; and R$^{16}$, at each occurrence, is independently selected alkyl, wherein the R$^{16}$ alkyl is optionally substituted with one, two, three or four alkoxy;

with the proviso that when R$^{13}$ is piperidinyl, it is substituted piperidinyl; and with the proviso that when R$^{13}$ is pyrrolinyl, at least one of X$^1$, X$^2$, and X$^3$ is N.

Another embodiment pertains to compounds having Formula (Ic) or Formula (Vc), and pharmaceutically acceptable salts thereof; wherein X$^1$, X$^2$, and X$^3$ are CH, or X$^1$ and X$^3$ are CH; and X$^2$ is CR$^1$; or X$^2$ and X$^3$ are CH; and X$^1$ is CR$^1$; or X$^1$ is CH; and X$^2$ and X$^3$ are CR$^1$.

Another embodiment pertains to compounds having Formula (Ic) or Formula (Vc), and pharmaceutically acceptable salts thereof; wherein X$^1$ and X$^3$ are CH; and X$^2$ is N; or X$^2$ is CH; and X$^1$ and X$^3$ are N; X$^2$ and X$^3$ are CH; and X$^1$ is N; or X$^1$ is CH; X$^2$ is N; and X$^3$ is CR$^1$; or X$^1$ is CR$^1$; X$^2$ is N; and X$^3$ is CH; or X$^1$ is N; X$^2$ is CR$^1$; and X$^3$ is CH; or X$^1$ is N; X$^2$ is CR$^1$; and X$^3$ is N.

Another embodiment pertains to compounds having Formula (Ic), and pharmaceutically acceptable salts thereof, wherein R$^2$ is phenyl which is substituted at the para position with R$^5$; and R$^5$ is phthalazin-1(2H)-onyl, isoquinolinyl, isoquinolin-1(2H)-onyl, 5,6,7,8-tetrahydrophthalazin-1(2H)-onyl, 5-fluorophthalazin-1(2H)-onyl, (Z)-3H-benzo[d][1,2]diazepin-4(5H)-onyl, 5-(trifluoromethyl)phthalazin-1(2H)-onyl, pyrrolo[1,2-d][1,2,4]triazin-1(2H)-one, or isoindolin-1-onyl.

Still another embodiment pertains to compounds of Formula (Ic), which are

N-{4-[(3-phenylpropyl)carbamoyl]phenyl}-1,3-dihydro-2H-isoindole-2-carboxamide;
N-(4-{[4-(aminomethyl)benzyl]carbamoyl}phenyl)-5-fluoro-1,3-dihydro-2H-isoindole-2-carboxamide;
5-cyano-N-{4-[(3-phenylpropyl)carbamoyl]phenyl}-1,3-dihydro-2H-isoindole-2-carboxamide;
N-{4-[(cyclopentylmethyl)carbamoyl]phenyl}-5-fluoro-1,3-dihydro-2H-isoindole-2-carboxamide;
5-cyano-N-[4-(propylcarbamoyl)phenyl]-1,3-dihydro-2H-isoindole-2-carboxamide;
N-(4-{[4-(furo[3,2-c]pyridin-4-yl)piperazin-1-yl]carbonyl}phenyl)-1,3-dihydro-2H-isoindole-2-carboxamide;
5-cyano-N-(4-{[4-(pyridin-2-yl)piperazin-1-yl]carbonyl}phenyl)-1,3-dihydro-2H-isoindole-2-carboxamide;
5-fluoro-N-{4-[(pyridin-2-ylmethyl)carbamoyl]phenyl}-1,3-dihydro-2H-isoindole-2-carboxamide;
N-[4-(benzylcarbamoyl)phenyl]-5-fluoro-1,3-dihydro-2H-isoindole-2-carboxamide;
N-{4-[(3,4-dimethoxybenzyl)carbamoyl]phenyl}-1,3-dihydro-2H-isoindole-2-carboxamide;
5-methyl-N-(4-{[4-(pyridin-2-yl)piperazin-1-yl]carbonyl}phenyl)-1,3-dihydro-2H-isoindole-2-carboxamide;
N-(4-{[4-(thieno[3,2-c]pyridin-4-yl)piperazin-1-yl]carbonyl}phenyl)-1,3-dihydro-2H-isoindole-2-carboxamide;
N-{4-[(2,3-dimethoxybenzyl)carbamoyl]phenyl}-1,3-dihydro-2H-isoindole-2-carboxamide;
5-fluoro-N-{4-[(3-phenylpropyl)carbamoyl]phenyl}-1,3-dihydro-2H-isoindole-2-carboxamide;
5-fluoro-N-(4-{[4-(pyridazin-3-yl)piperazin-1-yl]carbonyl}phenyl)-1,3-dihydro-2H-isoindole-2-carboxamide;
N-{4-[(2,3-dihydro-1,4-benzodioxin-5-ylmethyl)carbamoyl]phenyl}-1,3-dihydro-2H-isoindole-2-carboxamide;
5-fluoro-N-(4-{[1-(3-methylbutyl)-1H-pyrazol-4-yl]carbamoyl}phenyl)-1,3-dihydro-2H-isoindole-2-carboxamide;
N-{4-[(2-fluorobenzyl)carbamoyl]phenyl}-1,3-dihydro-2H-isoindole-2-carboxamide;
5-fluoro-N-(4-{[4-(pyrimidin-2-yl)piperazin-1-yl]carbonyl}phenyl)-1,3-dihydro-2H-isoindole-2-carboxamide;
5-fluoro-N-{4-[(3-methylbutyl)carbamoyl]phenyl}-1,3-dihydro-2H-isoindole-2-carboxamide;
N-{4-[(2-methoxybenzyl)carbamoyl]phenyl}-1,3-dihydro-2H-isoindole-2-carboxamide;
5-fluoro-N-(4-{[4-(pyridin-2-yl)piperazin-1-yl]carbonyl}phenyl)-1,3-dihydro-2H-isoindole-2-carboxamide;
N-{4-[(3-fluorobenzyl)carbamoyl]phenyl}-1,3-dihydro-2H-isoindole-2-carboxamide;
5-fluoro-N-(4-{[3-(2-oxopyrrolidin-1-yl)propyl]carbamoyl}phenyl)-1,3-dihydro-2H-isoindole-2-carboxamide;
5-cyano-N-{4-[(3-methylbutyl)carbamoyl]phenyl}-1,3-dihydro-2H-isoindole-2-carboxamide;
N-{4-[(cyclopentylmethyl)carbamoyl]phenyl}-5-methyl-1,3-dihydro-2H-isoindole-2-carboxamide;
N-(4-{[4-(4-cyanophenyl)piperazin-1-yl]carbonyl}phenyl)-1,3-dihydro-2H-isoindole-2-carboxamide;
N-{4-[(4-fluorobenzyl)carbamoyl]phenyl}-1,3-dihydro-2H-isoindole-2-carboxamide;
N-{4-[(3,5-dimethoxybenzyl)carbamoyl]phenyl}-1,3-dihydro-2H-isoindole-2-carboxamide;
5-fluoro-N-{4-[(tetrahydro furan-3-ylmethyl)carbamoyl]phenyl}-1,3-dihydro-2H-isoindole-2-carboxamide;
N-{4-[(2,2-dimethylpropyl)carbamoyl]phenyl}-1,3-dihydro-2H-isoindole-2-carboxamide;
5-fluoro-N-(4-{[2-(2-oxopyrrolidin-1-yl)ethyl]carbamoyl}phenyl)-1,3-dihydro-2H-isoindole-2-carboxamide;
N-(4-{[4-(trifluoromethoxy)benzyl]carbamoyl}phenyl)-1,3-dihydro-2H-isoindole-2-carboxamide;
N-(4-{[3-fluoro-5-(trifluoromethyl)benzyl]carbamoyl}phenyl)-1,3-dihydro-2H-isoindole-2-carboxamide;
5-fluoro-N-(4-{[4-(pyrazin-2-yl)piperazin-1-yl]carbonyl}phenyl)-1,3-dihydro-2H-isoindole-2-carboxamide;
N-{4-[(3-methylbutyl)carbamoyl]phenyl}-1,3-dihydro-2H-isoindole-2-carboxamide;
5-methoxy-N-{4-[(3-phenylpropyl)carbamoyl]phenyl}-1,3-dihydro-2H-isoindole-2-carboxamide;

N-{4-[(4-chlorobenzyl)carbamoyl]phenyl}-1,3-dihydro-2H-isoindole-2-carboxamide;
N-{4-[(cyclopentylmethyl)carbamoyl]phenyl}-1,3-dihydro-2H-isoindole-2-carboxamide;
N-{4-[(3,4,5-trimethoxybenzyl)carbamoyl]phenyl}-1,3-dihydro-2H-isoindole-2-carboxamide;
N-(4-{[4-(pyrimidin-2-yl)piperazin-1-yl]carbonyl}phenyl)-1,3-dihydro-2H-isoindole-2-carboxamide;
5-nitro-N-[4-(propylcarbamoyl)phenyl]-1,3-dihydro-2H-isoindole-2-carboxamide;
5-methyl-N-{4-[(3-methylbutyl)carbamoyl]phenyl}-1,3-dihydro-2H-isoindole-2-carboxamide;
N-(4-{[4-(4-fluorophenyl)piperazin-1-yl]carbonyl}phenyl)-1,3-dihydro-2H-isoindole-2-carboxamide;
N-{4-[(4-methoxybenzyl)carbamoyl]phenyl}-1,3-dihydro-2H-isoindole-2-carboxamide;
N-{4-[(2-thienylmethyl)carbamoyl]phenyl}-1,3-dihydro-2H-isoindole-2-carboxamide;
N-(4-{[4-(pyrimidin-2-yl)piperazin-1-yl]carbonyl}phenyl)-5-(trifluoromethyl)-1,3-dihydro-2H-isoindole-2-carboxamide;
N-{4-[(1-ethyl-1H-pyrazol-4-yl)carbamoyl]phenyl}-5-fluoro-1,3-dihydro-2H-isoindole-2-carboxamide;
N-{4-[(1-benzyl-1H-pyrazol-4-yl)carbamoyl]phenyl}-5-fluoro-1,3-dihydro-2H-isoindole-2-carboxamide;
N-(4-{[4-(pyridin-2-yl)piperazin-1-yl]carbonyl}phenyl)-1,3-dihydro-2H-isoindole-2-carboxamide;
N-(4-{[4-(pyrazin-2-yl)piperazin-1-yl]carbonyl}phenyl)-1,3-dihydro-2H-isoindole-2-carboxamide;
N-(4-{[4-(2-methoxyphenyl)piperazin-1-yl]carbonyl}phenyl)-1,3-dihydro-2H-isoindole-2-carboxamide;
N-{4-[(3,3-dimethylbutyl)carbamoyl]phenyl}-1,3-dihydro-2H-isoindole-2-carboxamide;
N-(4-{[(2R)-tetrahydrofuran-2-ylmethyl]carbamoyl}phenyl)-1,3-dihydro-2H-isoindole-2-carboxamide;
N-(4-{[4-(3-methoxyphenyl)piperazin-1-yl]carbonyl}phenyl)-1,3-dihydro-2H-isoindole-2-carboxamide;
N-(4-{[4-(4-acetylphenyl)piperazin-1-yl]carbonyl}phenyl)-1,3-dihydro-2H-isoindole-2-carboxamide;
N-(4-{[2-(2,3-dimethoxyphenyl)ethyl]carbamoyl}phenyl)-1,3-dihydro-2H-isoindole-2-carboxamide;
N-{4-[(3-thienylmethyl)carbamoyl]phenyl}-1,3-dihydro-2H-isoindole-2-carboxamide;
5-methoxy-N-{4-[(3-methylbutyl)carbamoyl]phenyl}-1,3-dihydro-2H-isoindole-2-carboxamide;
N-{4-[(pyridin-2-ylmethyl)carbamoyl]phenyl}-1,3-dihydro-2H-isoindole-2-carboxamide;
5-fluoro-N-(4-{[2-(2-thienyl)ethyl]carbamoyl}phenyl)-1,3-dihydro-2H-isoindole-2-carboxamide;
N-(4-{[(2S)-tetrahydrofuran-2-ylmethyl]carbamoyl}phenyl)-1,3-dihydro-2H-isoindole-2-carboxamide;
N-(4-{[1-(3-methylbutyl)-1H-pyrazol-4-yl]carbamoyl}phenyl)-1,3-dihydro-2H-isoindole-2-carboxamide;
4-chloro-N-(4-{[4-(pyridin-2-yl)piperazin-1-yl]carbonyl}phenyl)-1,3-dihydro-2H-isoindole-2-carboxamide;
N-{4-[(4-phenylpiperazin-1-yl)carbonyl]phenyl}-1,3-dihydro-2H-isoindole-2-carboxamide;
N-{4-[(6-aminohexyl)carbamoyl]phenyl}-1,3-dihydro-2H-isoindole-2-carboxamide;
4-chloro-N-{4-[(3-methylbutyl)carbamoyl]phenyl}-1,3-dihydro-2H-isoindole-2-carboxamide;
N-(4-{[2-(2-thienyl)ethyl]carbamoyl}phenyl)-1,3-dihydro-2H-isoindole-2-carboxamide;
5-methoxy-N-(4-{[4-(pyridin-2-yl)piperazin-1-yl]carbonyl}phenyl)-1,3-dihydro-2H-isoindole-2-carboxamide;
N-{4-[(1,3-benzodioxol-5-ylmethyl)carbamoyl]phenyl}-1,3-dihydro-2H-isoindole-2-carboxamide;
N-{4-[(3-methoxybenzyl)carbamoyl]phenyl}-1,3-dihydro-2H-isoindole-2-carboxamide;
N-(4-{[4-(pyridin-3-yl)piperazin-1-yl]carbonyl}phenyl)-1,3-dihydro-2H-isoindole-2-carboxamide;
N-[4-(benzylcarbamoyl)phenyl]-1,3-dihydro-2H-isoindole-2-carboxamide;
N-(4-{[4-(pyridazin-3-yl)piperazin-1-yl]carbonyl}phenyl)-1,3-dihydro-2H-isoindole-2-carboxamide;
N-{4-[(pyrimidin-4-ylmethyl)carbamoyl]phenyl}-1,3-dihydro-2H-isoindole-2-carboxamide;
N-(4-{[4-(3-fluorophenyl)piperazin-1-yl]carbonyl}phenyl)-1,3-dihydro-2H-isoindole-2-carboxamide;
N-{4-[(2-methylbutyl)carbamoyl]phenyl}-1,3-dihydro-2H-isoindole-2-carboxamide;
N-(4-{[4-(pyridin-2-yl)piperazin-1-yl]carbonyl}phenyl)-5-(trifluoromethyl)-1,3-dihydro-2H-isoindole-2-carboxamide;
N-{4-[(3-butoxypropyl)carbamoyl]phenyl}-1,3-dihydro-2H-isoindole-2-carboxamide;
N-(4-{[(1S)-2-hydroxy-1-phenylethyl]carbamoyl}phenyl)-1,3-dihydro-2H-isoindole-2-carboxamide;
N-(4-{[2-(3,4-dihydroxyphenyl)ethyl]carbamoyl}phenyl)-1,3-dihydro-2H-isoindole-2-carboxamide;
N-{4-[(3-propoxypropyl)carbamoyl]phenyl}-1,3-dihydro-2H-isoindole-2-carboxamide;
N-{4-[(3-furylmethyl)carbamoyl]phenyl}-1,3-dihydro-2H-isoindole-2-carboxamide;
N-(4-{[4-(2-cyanophenyl)piperazin-1-yl]carbonyl}phenyl)-1,3-dihydro-2H-isoindole-2-carboxamide;
N-{4-[(3-hydroxy-2-methylphenyl)carbamoyl]phenyl}-1,3-dihydro-2H-isoindole-2-carboxamide;
N-{4-[(3-methylbutyl)carbamoyl]phenyl}-5-(trifluoromethyl)-1,3-dihydro-2H-isoindole-2-carboxamide;
N-{4-[(3-methyl-1H-indazol-5-yl)carbamoyl]phenyl}-1,3-dihydro-2H-isoindole-2-carboxamide;
N-{4-[(3-ethoxypropyl)carbamoyl]phenyl}-1,3-dihydro-2H-isoindole-2-carboxamide;
N-(4-{[4-(pyrazin-2-yl)piperazin-1-yl]carbonyl}phenyl)-5-(trifluoromethyl)-1,3-dihydro-2H-isoindole-2-carboxamide;
N-(4-{[2-(2,5-dimethoxyphenyl)ethyl]carbamoyl}phenyl)-1,3-dihydro-2H-isoindole-2-carboxamide;
N-{4-[(tetrahydrofuran-3-ylmethyl)carbamoyl]phenyl}-1,3-dihydro-2H-isoindole-2-carboxamide;
N-{4-[(1-benzyl-1H-pyrazol-4-yl)carbamoyl]phenyl}-1,3-dihydro-2H-isoindole-2-carboxamide;
methyl 5-({4-[(1,3-dihydro-2H-isoindol-2-ylcarbonyl)amino]benzoyl}amino)-1H-indazole-3-carboxylate;
N-(4-{[2-(2-oxopyrrolidin-1-yl)ethyl]carbamoyl}phenyl)-1,3-dihydro-2H-isoindole-2-carboxamide;
N-{4-[(pyridin-4-ylmethyl)carbamoyl]phenyl}-1,3-dihydro-2H-isoindole-2-carboxamide;
N-(4-{[4-(5-chloropyridin-2-yl)piperazin-1-yl]carbonyl}phenyl)-1,3-dihydro-2H-isoindole-2-carboxamide;
N-(4-{[2-(1H-indol-3-yl)ethyl]carbamoyl}phenyl)-1,3-dihydro-2H-isoindole-2-carboxamide;
N-(4-{[4-(trifluoromethyl)benzyl]carbamoyl}phenyl)-1,3-dihydro-2H-isoindole-2-carboxamide;

N-{4-[(3,5-dimethoxyphenyl)carbamoyl]phenyl}-1,3-dihydro-2H-isoindole-2-carboxamide;
N-{4-[(pyridin-3-ylmethyl)carbamoyl]phenyl}-1,3-dihydro-2H-isoindole-2-carboxamide;
N-[4-(2,3-dihydro-1,4-benzodioxin-6-ylcarbamoyl)phenyl]-1,3-dihydro-2H-isoindole-2-carboxamide;
N-(4-{[4-(2-fluorobenzoyl)piperazin-1-yl]carbonyl}phenyl)-1,3-dihydro-2H-isoindole-2-carboxamide;
N-(4-{[2-(5-methoxy-1H-indol-3-yl)ethyl]carbamoyl}phenyl)-1,3-dihydro-2H-isoindole-2-carboxamide;
N-{4-[(3-aminobenzyl)carbamoyl]phenyl}-1,3-dihydro-2H-isoindole-2-carboxamide;
N-(4-{[2-(2-chlorophenyl)ethyl]carbamoyl}phenyl)-1,3-dihydro-2H-isoindole-2-carboxamide;
N-(4-{[(2R)-1-hydroxy-4-methylpentan-2-yl]carbamoyl}phenyl)-1,3-dihydro-2H-isoindole-2-carboxamide;
N-{4-[(2-propoxyethyl)carbamoyl]phenyl}-1,3-dihydro-2H-isoindole-2-carboxamide;
N-{4-[(3-isobutoxypropyl)carbamoyl]phenyl}-1,3-dihydro-2H-isoindole-2-carboxamide;
N-(4-{[4-(pyridin-4-yl)piperazin-1-yl]carbonyl}phenyl)-1,3-dihydro-2H-isoindole-2-carboxamide;
N-[4-({4-[5-(trifluoromethyl)pyridin-2-yl]piperazin-1-yl}carbonyl)phenyl]-1,3-dihydro-2H-isoindole-2-carboxamide;
N-{4-[(3,4,5-trimethoxyphenyl)carbamoyl]phenyl}-1,3-dihydro-2H-isoindole-2-carboxamide;
N-{4-[(4-methylpiperidin-1-yl)carbonyl]phenyl}-1,3-dihydro-2H-isoindole-2-carboxamide;
N-[4-({2-[4-(dimethylamino)phenyl]ethyl}carbamoyl)phenyl]-1,3-dihydro-2H-isoindole-2-carboxamide;
N-(4-{[3-(trifluoromethoxy)benzyl]carbamoyl}phenyl)-1,3-dihydro-2H-isoindole-2-carboxamide;
N-(4-{[(1R)-3-hydroxy-1-phenylpropyl]carbamoyl}phenyl)-1,3-dihydro-2H-isoindole-2-carboxamide;
N-{4-[(3-cyanophenyl)carbamoyl]phenyl}-1,3-dihydro-2H-isoindole-2-carboxamide;
N-{4-[(3-fluoro-4-methoxyphenyl)carbamoyl]phenyl}-1,3-dihydro-2H-isoindole-2-carboxamide;
N-{4-[(2,3-dimethoxyphenyl)carbamoyl]phenyl}-1,3-dihydro-2H-isoindole-2-carboxamide;
N-(4-{[2-(2-fluorophenyl)ethyl]carbamoyl}phenyl)-1,3-dihydro-2H-isoindole-2-carboxamide;
N-[4-(isobutylcarbamoyl)phenyl]-1,3-dihydro-2H-isoindole-2-carboxamide;
N-(4-{[2-(1,3-benzodioxol-5-yl)ethyl]carbamoyl}phenyl)-1,3-dihydro-2H-isoindole-2-carboxamide;
N-(4-{[2-(2-methoxyphenyl)ethyl]carbamoyl}phenyl)-1,3-dihydro-2H-isoindole-2-carboxamide;
N-[4-(butylcarbamoyl)phenyl]-1,3-dihydro-2H-isoindole-2-carboxamide;
N-{4-[(2-isopropoxyethyl)carbamoyl]phenyl}-1,3-dihydro-2H-isoindole-2-carboxamide;
N-{4-[(3-isopropoxypropyl)carbamoyl]phenyl}-1,3-dihydro-2H-isoindole-2-carboxamide;
4-chloro-N-{4-[(3-phenylpropyl)carbamoyl]phenyl}-1,3-dihydro-2H-isoindole-2-carboxamide;
N-(4-{[2-(4-methoxyphenyl)ethyl]carbamoyl}phenyl)-1,3-dihydro-2H-isoindole-2-carboxamide;
N-{4-[(3-methoxypropyl)carbamoyl]phenyl}-1,3-dihydro-2H-isoindole-2-carboxamide;
N-(4-{[2-(4-fluorophenyl)ethyl]carbamoyl}phenyl)-1,3-dihydro-2H-isoindole-2-carboxamide;
N-(4-{[3-(2-oxopyrrolidin-1-yl)propyl]carbamoyl}phenyl)-1,3-dihydro-2H-isoindole-2-carboxamide;
N-{4-[(2,4-dimethoxyphenyl)carbamoyl]phenyl}-1,3-dihydro-2H-isoindole-2-carboxamide;
$N^2$-[4-(propylcarbamoyl)phenyl]-1,3-dihydro-2H-isoindole-2,5-dicarboxamide;
N-{4-[(2-phenoxyethyl)carbamoyl]phenyl}-1,3-dihydro-2H-isoindole-2-carboxamide;
N-(4-{[2-(4-hydroxyphenyl)ethyl]carbamoyl}phenyl)-1,3-dihydro-2H-isoindole-2-carboxamide;
N-(4-{[2-(3-fluorophenyl)ethyl]carbamoyl}phenyl)-1,3-dihydro-2H-isoindole-2-carboxamide;
N-[4-({1-[(3S)-tetrahydrofuran-3-yl]-1H-pyrazol-4-yl}carbamoyl)phenyl]-1,3-dihydro-2H-isoindole-2-carboxamide;
5-methyl-N-{4-[(3-phenylpropyl)carbamoyl]phenyl}-1,3-dihydro-2H-isoindole-2-carboxamide;
N-[4-(1,4-dioxa-8-azaspiro[4.5]dec-8-ylcarbonyl)phenyl]-1,3-dihydro-2H-isoindole-2-carboxamide;
N-{4-[(2-phenylethyl)carbamoyl]phenyl}-1,3-dihydro-2H-isoindole-2-carboxamide;
N-(4-{[2-(2,4-dimethoxyphenyl)ethyl]carbamoyl}phenyl)-1,3-dihydro-2H-isoindole-2-carboxamide;
N-(4-{[3-(methylthio)propyl]carbamoyl}phenyl)-1,3-dihydro-2H-isoindole-2-carboxamide;
N-{4-[(2-ethoxyethyl)carbamoyl]phenyl}-1,3-dihydro-2H-isoindole-2-carboxamide;
N-{4-[(2-fluorophenyl)carbamoyl]phenyl}-1,3-dihydro-2H-isoindole-2-carboxamide;
N-(4-{[2-(pyridin-3-yl)ethyl]carbamoyl}phenyl)-1,3-dihydro-2H-isoindole-2-carboxamide;
N-[4-({4-[(trifluoromethyl)thio]benzyl}carbamoyl)phenyl]-1,3-dihydro-2H-isoindole-2-carboxamide;
N-{4-[(3,4-dimethoxyphenyl)carbamoyl]phenyl}-1,3-dihydro-2H-isoindole-2-carboxamide;
N-(4-{[3-(2-fluorophenyl)pyrrolidin-1-yl]carbonyl}phenyl)-1,3-dihydro-2H-isoindole-2-carboxamide;
N-(4-{[3-(1H-imidazol-1-yl)propyl]carbamoyl}phenyl)-1,3-dihydro-2H-isoindole-2-carboxamide;
N-(4-{[2-(3-chlorophenyl)ethyl]carbamoyl}phenyl)-1,3-dihydro-2H-isoindole-2-carboxamide;
N-{4-[(4-hydroxybutyl)carbamoyl]phenyl}-1,3-dihydro-2H-isoindole-2-carboxamide;
N-{4-[(3-phenylpropyl)carbamoyl]phenyl}-5-(trifluoromethyl)-1,3-dihydro-2H-isoindole-2-carboxamide;
N-(4-{[4-(hydroxymethyl)phenyl]carbamoyl}phenyl)-1,3-dihydro-2H-isoindole-2-carboxamide;
N-[4-(1,3-benzodioxol-5-ylcarbamoyl)phenyl]-1,3-dihydro-2H-isoindole-2-carboxamide;
N-{4-[(1-isopropyl-1H-pyrazol-4-yl)carbamoyl]phenyl}-1,3-dihydro-2H-isoindole-2-carboxamide;
N-{4-[(4-hydroxyphenyl)carbamoyl]phenyl}-1,3-dihydro-2H-isoindole-2-carboxamide;
N-{4-[(1-ethyl-1H-pyrazol-4-yl)carbamoyl]phenyl}-1,3-dihydro-2H-isoindole-2-carboxamide;
N-{4-[(2,5-dimethoxyphenyl)carbamoyl]phenyl}-1,3-dihydro-2H-isoindole-2-carboxamide;
N-{4-[methyl(3-phenylpropyl)carbamoyl]phenyl}-1,3-dihydro-2H-isoindole-2-carboxamide;
N-{4-[(2-hydroxy-2-methylpropyl)carbamoyl]phenyl}-1,3-dihydro-2H-isoindole-2-carboxamide;
N-(4-{[4-(trifluoromethyl)piperidin-1-yl]carbonyl}phenyl)-1,3-dihydro-2H-isoindole-2-carboxamide;
N-[4-(thiomorpholin-4-ylcarbonyl)phenyl]-1,3-dihydro-2H-isoindole-2-carboxamide;

N-[4-(5,6-dihydroimidazo[1,5-a]pyrazin-7(8H)-ylcarbonyl)phenyl]-1,3-dihydro-2H-isoindole-2-carboxamide;
N-(4-{[4-(2-furoyl)piperazin-1-yl]carbonyl}phenyl)-1,3-dihydro-2H-isoindole-2-carboxamide;
N-{4-[(1-benzylpiperidin-4-yl)carbamoyl]phenyl}-1,3-dihydro-2H-isoindole-2-carboxamide;
N-{4-[(4-methoxyphenyl)carbamoyl]phenyl}-1,3-dihydro-2H-isoindole-2-carboxamide;
N-{4-[(3-methoxyphenyl)carbamoyl]phenyl}-1,3-dihydro-2H-isoindole-2-carboxamide;
N-{4-[(5-acetamido-2-methoxyphenyl)carbamoyl]phenyl}-1,3-dihydro-2H-isoindole-2-carboxamide;
N-(4-{[2-(3,5-dimethoxyphenyl)ethyl]carbamoyl}phenyl)-1,3-dihydro-2H-isoindole-2-carboxamide;
N-[4-({2-[3-(trifluoromethyl)phenyl]ethyl}carbamoyl)phenyl]-1,3-dihydro-2H-isoindole-2-carboxamide;
N-{4-[(2-methylbutan-2-yl)carbamoyl]phenyl}-1,3-dihydro-2H-isoindole-2-carboxamide;
N-(4-{[2-(1H-imidazol-4-yl)ethyl]carbamoyl}phenyl)-1,3-dihydro-2H-isoindole-2-carboxamide;
N-(4-{[(2S)-2-hydroxypropyl]carbamoyl}phenyl)-1,3-dihydro-2H-isoindole-2-carboxamide;
N-(4-{[(1R)-1-(3-cyanophenyl)ethyl]carbamoyl}phenyl)-1,3-dihydro-2H-isoindole-2-carboxamide;
N-(4-{[(2S)-1-hydroxy-3-methylbutan-2-yl]carbamoyl}phenyl)-1,3-dihydro-2H-isoindole-2-carboxamide;
N-{4-[benzyl(2-hydroxyethyl)carbamoyl]phenyl}-1,3-dihydro-2H-isoindole-2-carboxamide;
N-{4-[(4-cyanophenyl)carbamoyl]phenyl}-1,3-dihydro-2H-isoindole-2-carboxamide;
N-(4-{[2-(4-chlorophenyl)ethyl]carbamoyl}phenyl)-1,3-dihydro-2H-isoindole-2-carboxamide;
N-(4-{[2-(4-methylpiperazin-1-yl)ethyl]carbamoyl}phenyl)-1,3-dihydro-2H-isoindole-2-carboxamide;
N-(4-{[2-(pyridin-2-yl)ethyl]carbamoyl}phenyl)-1,3-dihydro-2H-isoindole-2-carboxamide;
N-{4-[(cyanomethyl)carbamoyl]phenyl}-1,3-dihydro-2H-isoindole-2-carboxamide;
N-[4-(cyclohexylcarbamoyl)phenyl]-1,3-dihydro-2H-isoindole-2-carboxamide;
N-{4-[(3-hydroxyphenyl)carbamoyl]phenyl}-1,3-dihydro-2H-isoindole-2-carboxamide;
N-{4-[butyl(methyl)carbamoyl]phenyl}-1,3-dihydro-2H-isoindole-2-carboxamide;
N-(4-{[4-(dimethylamino)phenyl]carbamoyl}phenyl)-1,3-dihydro-2H-isoindole-2-carboxamide;
N-[4-(3,4-dihydroisoquinolin-2(1H)-ylcarbonyl)phenyl]-1,3-dihydro-2H-isoindole-2-carboxamide;
N-[4-(1,3-dihydro-2H-isoindol-2-ylcarbonyl)phenyl]-1,3-dihydro-2H-isoindole-2-carboxamide;
N-[4-(2,3-dihydro-1H-indol-1-ylcarbonyl)phenyl]-1,3-dihydro-2H-isoindole-2-carboxamide;
N-[4-(phenylcarbamoyl)phenyl]-1,3-dihydro-2H-isoindole-2-carboxamide;
N-{4-[(4-fluorophenyl)carbamoyl]phenyl}-1,3-dihydro-2H-isoindole-2-carboxamide;
N-(4-{[2-(diethylamino)ethyl]carbamoyl}phenyl)-1,3-dihydro-2H-isoindole-2-carboxamide;
N-{4-[(2-hydroxy-2-phenylethyl)(methyl)carbamoyl]phenyl}-1,3-dihydro-2H-isoindole-2-carboxamide;
N-{4-[(2-aminophenyl)carbamoyl]phenyl}-1,3-dihydro-2H-isoindole-2-carboxamide;
N-(4-{[(2R)-2-hydroxypropyl]carbamoyl}phenyl)-1,3-dihydro-2H-isoindole-2-carboxamide;
N-(4-{[(2S)-1-amino-4-methyl-1-oxopentan-2-yl]carbamoyl}phenyl)-1,3-dihydro-2H-isoindole-2-carboxamide;
tert-butyl(1-{4-[(1,3-dihydro-2H-isoindol-2-ylcarbonyl)amino]benzoyl}piperidin-4-yl)carbamate;
N-(4-{[3-(morpholin-4-yl)propyl]carbamoyl}phenyl)-1,3-dihydro-2H-isoindole-2-carboxamide;
N-[4-({4-[3-chloro-5-(trifluoromethyl)pyridin-2-yl]piperazin-1-yl}carbonyl)phenyl]-1,3-dihydro-2H-isoindole-2-carboxamide;
N-(4-{[4-(cyclohexylmethyl)piperazin-1-yl]carbonyl}phenyl)-1,3-dihydro-2H-isoindole-2-carboxamide;
N-(4-{[1-(3-chlorobenzyl)-1H-pyrazol-4-yl]carbamoyl}phenyl)-1,3-dihydro-2H-isoindole-2-carboxamide;
N-(4-{[3-(diethylcarbamoyl)piperidin-1-yl]carbonyl}phenyl)-1,3-dihydro-2H-isoindole-2-carboxamide;
N-(4-{[3-(piperidin-1-yl)propyl]carbamoyl}phenyl)-1,3-dihydro-2H-isoindole-2-carboxamide;
N-(4-{[4-(2-hydroxyethyl)piperazin-1-yl]carbonyl}phenyl)-1,3-dihydro-2H-isoindole-2-carboxamide;
N-{4-[(2-hydroxy-6-methylphenyl)carbamoyl]phenyl}-1,3-dihydro-2H-isoindole-2-carboxamide;
N-(4-{[4-(dimethylamino)butyl]carbamoyl}phenyl)-1,3-dihydro-2H-isoindole-2-carboxamide;
N-{4-[(3-hydroxypropyl)carbamoyl]phenyl}-1,3-dihydro-2H-isoindole-2-carboxamide;
N-{4-[(4-cyclohexylpiperazin-1-yl)carbonyl]phenyl}-1,3-dihydro-2H-isoindole-2-carboxamide;
N-[4-(5,6-dihydro[1,2,4]triazolo[4,3-a]pyrazin-7(8H)-ylcarbonyl)phenyl]-1,3-dihydro-2H-isoindole-2-carboxamide;
N-{4-[methyl(3-methylbutyl)carbamoyl]phenyl}-1,3-dihydro-2H-isoindole-2-carboxamide;
N-[4-(propylcarbamoyl)phenyl]-1,3-dihydro-2H-isoindole-2-carboxamide;
N-(4-{[(2S)-1-hydroxybutan-2-yl]carbamoyl}phenyl)-1,3-dihydro-2H-isoindole-2-carboxamide;
N-{4-[(5-fluoropyridin-2-yl)carbamoyl]phenyl}-1,3-dihydro-2H-isoindole-2-carboxamide;
N-{4-[(cyclopropylmethyl)(propyl)carbamoyl]phenyl}-1,3-dihydro-2H-isoindole-2-carboxamide;
N-(4-{[(2S)-1-methoxypropan-2-yl]carbamoyl}phenyl)-1,3-dihydro-2H-isoindole-2-carboxamide;
N-[4-(1,3,4,9-tetrahydro-2H-beta-carbolin-2-ylcarbonyl)phenyl]-1,3-dihydro-2H-isoindole-2-carboxamide;
N-[4-(tert-butylcarbamoyl)phenyl]-1,3-dihydro-2H-isoindole-2-carboxamide;
N-[4-({4-[4-(trifluoromethyl)phenyl]piperazin-1-yl}carbonyl)phenyl]-1,3-dihydro-2H-isoindole-2-carboxamide;
N-{4-[(3-methylbutan-2-yl)carbamoyl]phenyl}-1,3-dihydro-2H-isoindole-2-carboxamide;
N-{4-[(3,3-difluoropyrrolidin-1-yl)carbonyl]phenyl}-1,3-dihydro-2H-isoindole-2-carboxamide;
N-{4-[(2-methylpiperidin-1-yl)carbonyl]phenyl}-1,3-dihydro-2H-isoindole-2-carboxamide;
N-(4-{[(3S)-1-benzylpyrrolidin-3-yl]carbamoyl}phenyl)-1,3-dihydro-2H-isoindole-2-carboxamide;
N-{4-[(4-hydroxypiperidin-1-yl)carbonyl]phenyl}-1,3-dihydro-2H-isoindole-2-carboxamide;
N-{4-[bis(2-methoxyethyl)carbamoyl]phenyl}-1,3-dihydro-2H-isoindole-2-carboxamide;

N-{4-[(3-fluorophenyl)carbamoyl]phenyl}-1,3-dihydro-2H-isoindole-2-carboxamide;
N-[4-(cyclopentylcarbamoyl)phenyl]-1,3-dihydro-2H-isoindole-2-carboxamide;
N-{4-[(4-carbamoylpiperidin-1-yl)carbonyl]phenyl}-1,3-dihydro-2H-isoindole-2-carboxamide;
N-[4-(cyclopropylcarbamoyl)phenyl]-1,3-dihydro-2H-isoindole-2-carboxamide;
N-[4-(methylcarbamoyl)phenyl]-1,3-dihydro-2H-isoindole-2-carboxamide;
N-(4-{[3-(dimethylamino)propyl]carbamoyl}phenyl)-1,3-dihydro-2H-isoindole-2-carboxamide;
N-{4-[methyl(tetrahydrofuran-2-ylmethyl)carbamoyl]phenyl}-1,3-dihydro-2H-isoindole-2-carboxamide;
N-[4-(pentan-2-ylcarbamoyl)phenyl]-1,3-dihydro-2H-isoindole-2-carboxamide;
N-[4-(pentan-3-ylcarbamoyl)phenyl]-1,3-dihydro-2H-isoindole-2-carboxamide;
N-[4-(cyclobutylcarbamoyl)phenyl]-1,3-dihydro-2H-isoindole-2-carboxamide;
N-{4-[(1,3-dioxolan-2-ylmethyl)(methyl)carbamoyl]phenyl}-1,3-dihydro-2H-isoindole-2-carboxamide;
N-(4-{[1-(4-fluorophenyl)-1H-pyrazol-4-yl]carbamoyl}phenyl)-1,3-dihydro-2H-isoindole-2-carboxamide;
N-{4-[(1-hydroxy-2-methylpropan-2-yl)carbamoyl]phenyl}-1,3-dihydro-2H-isoindole-2-carboxamide;
N-{4-[(1-phenyl-1H-pyrazol-4-yl)carbamoyl]phenyl}-1,3-dihydro-2H-isoindole-2-carboxamide;
N-[4-({2-[4-(trifluoromethyl)phenyl]ethyl}carbamoyl)phenyl]-1,3-dihydro-2H-isoindole-2-carboxamide;
N-{4-[(2-methoxyethyl)(propyl)carbamoyl]phenyl}-1,3-dihydro-2H-isoindole-2-carboxamide;
N-[4-(sec-butylcarbamoyl)phenyl]-1,3-dihydro-2H-isoindole-2-carboxamide;
N-(4-{[3-(trifluoromethyl)piperidin-1-yl]carbonyl}phenyl)-1,3-dihydro-2H-isoindole-2-carboxamide;
N-{4-[bis(2-ethoxyethyl)carbamoyl]phenyl}-1,3-dihydro-2H-isoindole-2-carboxamide;
N-{4-[butyl(ethyl)carbamoyl]phenyl}-1,3-dihydro-2H-isoindole-2-carboxamide;
N-{4-[(1-methoxypropan-2-yl)carbamoyl]phenyl}-1,3-dihydro-2H-isoindole-2-carboxamide;
N-{4-[(2-methoxyethyl)(methyl)carbamoyl]phenyl}-1,3-dihydro-2H-isoindole-2-carboxamide;
N-{4-[(3R)-tetrahydrofuran-3-ylcarbamoyl]phenyl}-1,3-dihydro-2H-isoindole-2-carboxamide;
N-[4-(morpholin-4-ylcarbonyl)phenyl]-1,3-dihydro-2H-isoindole-2-carboxamide;
N-{4-[isobutyl(methyl)carbamoyl]phenyl}-1,3-dihydro-2H-isoindole-2-carboxamide;
N-[4-({4-[2-(2-hydroxyethoxy)ethyl]piperazin-1-yl}carbonyl)phenyl]-1,3-dihydro-2H-isoindole-2-carboxamide;
N-{4-[(3-methylpiperidin-1-yl)carbonyl]phenyl}-1,3-dihydro-2H-isoindole-2-carboxamide;
N-(4-carbamoylphenyl)-1,3-dihydro-2H-isoindole-2-carboxamide;
N-(4-{[(2S)-2-(trifluoromethyl)pyrrolidin-1-yl]carbonyl}phenyl)-1,3-dihydro-2H-isoindole-2-carboxamide;
N-(4-{[(2S)-1-hydroxy-4-methylpentan-2-yl]carbamoyl}phenyl)-1,3-dihydro-2H-isoindole-2-carboxamide;
N-(4-{[(1R)-2-hydroxy-1-phenylethyl]carbamoyl}phenyl)-1,3-dihydro-2H-isoindole-2-carboxamide;
N-{4-[(2-methylpyrrolidin-1-yl)carbonyl]phenyl}-1,3-dihydro-2H-isoindole-2-carboxamide;
N-{4-[ethyl(2-methoxyethyl)carbamoyl]phenyl}-1,3-dihydro-2H-isoindole-2-carboxamide;
N-(4-{[(2R)-1-hydroxy-3-methylbutan-2-yl]carbamoyl}phenyl)-1,3-dihydro-2H-isoindole-2-carboxamide;
N-{4-[(2,6-dimethylmorpholin-4-yl)carbonyl]phenyl}-1,3-dihydro-2H-isoindole-2-carboxamide;
N-(4-{[(2R)-1-hydroxybutan-2-yl]carbamoyl}phenyl)-1,3-dihydro-2H-isoindole-2-carboxamide;
N-{4-[(2,5-dimethylpyrrolidin-1-yl)carbonyl]phenyl}-1,3-dihydro-2H-isoindole-2-carboxamide;
N-[4-(prop-2-yn-1-ylcarbamoyl)phenyl]-1,3-dihydro-2H-isoindole-2-carboxamide;
N-{4-[isopropyl(2-methoxyethyl)carbamoyl]phenyl}-1,3-dihydro-2H-isoindole-2-carboxamide;
N-{4-[isopropyl(propyl)carbamoyl]phenyl}-1,3-dihydro-2H-isoindole-2-carboxamide;
N-{4-[(2-cyanoethyl)(cyclopropyl)carbamoyl]phenyl}-1,3-dihydro-2H-isoindole-2-carboxamide;
N-{4-[ethyl(isopropyl)carbamoyl]phenyl}-1,3-dihydro-2H-isoindole-2-carboxamide;
N-{4-[(3-fluoropyrrolidin-1-yl)carbonyl]phenyl}-1,3-dihydro-2H-isoindole-2-carboxamide;
N-{4-[(1,3-dihydro-2H-isoindol-2-ylcarbonyl)amino]benzoyl}-N-isopropyl-beta-alanine;
N-{4-[methyl(propyl)carbamoyl]phenyl}-1,3-dihydro-2H-isoindole-2-carboxamide;
5,6-dimethoxy-N-{4-[(3-phenylpropyl)carbamoyl]phenyl}-1,3-dihydro-2H-isoindole-2-carboxamide;
N-(4-{[3-(4-chlorophenoxy)propyl]carbamoyl}phenyl)-1,3-dihydro-2H-isoindole-2-carboxamide;
N-(4-{[4-(trifluoromethoxy)phenyl]carbamoyl}phenyl)-1,3-dihydro-2H-isoindole-2-carboxamide;
N-{4-[(4-phenyl-1,3-thiazol-2-yl)carbamoyl]phenyl}-1,3-dihydro-2H-isoindole-2-carboxamide;
methyl 2-{[4-(propylcarbamoyl)phenyl]carbamoyl}isoindoline-5-carboxylate;
2-{[4-(propylcarbamoyl)phenyl]carbamoyl}isoindoline-5-carboxylic acid;
5-amino-N-[4-(propylcarbamoyl)phenyl]-1,3-dihydro-2H-isoindole-2-carboxamide;
5-(hydroxymethyl)-N-[4-(propylcarbamoyl)phenyl]-1,3-dihydro-2H-isoindole-2-carboxamide;
5-(aminomethyl)-N-[4-(propylcarbamoyl)phenyl]-1,3-dihydro-2H-isoindole-2-carboxamide;
5-[(2-hydroxy-2-methylpropanoyl)amino]-N-[4-(propylcarbamoyl)phenyl]-1,3-dihydro-2H-isoindole-2-carboxamide;
5-acetamido-N-[4-(propylcarbamoyl)phenyl]-1,3-dihydro-2H-isoindole-2-carboxamide;
5-[(N,N-dimethylglycyl)amino]-N-[4-(propylcarbamoyl)phenyl]-1,3-dihydro-2H-isoindole-2-carboxamide;
N-[4-(propylcarbamoyl)phenyl]-5-(1H-pyrazol-3-yl)-1,3-dihydro-2H-isoindole-2-carboxamide;
N-[4-(propylcarbamoyl)phenyl]-5-(1H-pyrazol-4-yl)-1,3-dihydro-2H-isoindole-2-carboxamide;
5-[(methoxyacetyl)amino]-N-[4-(propylcarbamoyl)phenyl]-1,3-dihydro-2H-isoindole-2-carboxamide;
5-[(methylsulfonyl)amino]-N-[4-(propylcarbamoyl)phenyl]-1,3-dihydro-2H-isoindole-2-carboxamide;
5-bromo-N-[4-(propylcarbamoyl)phenyl]-1,3-dihydro-2H-isoindole-2-carboxamide;
N-{4-[(3,5-dimethoxybenzyl)carbamoyl]phenyl}-1,3-dihydro-2H-pyrrolo[3,4-c]pyridine-2-carboxamide;

N-{4-[(4-chlorobenzyl)carbamoyl]phenyl}-1,3-dihydro-2H-pyrrolo[3,4-c]pyridine-2-carboxamide;
N-(4-{[4-(pyridin-2-yl)piperazin-1-yl]carbonyl}phenyl)-1,3-dihydro-2H-pyrrolo[3,4-c]pyridine-2-carboxamide;
N-{4-[(3-phenylpropyl)carbamoyl]phenyl}-1,3-dihydro-2H-pyrrolo[3,4-c]pyridine-2-carboxamide;
N-{4-[(tetrahydrofuran-3-ylmethyl)carbamoyl]phenyl}-1,3-dihydro-2H-pyrrolo[3,4-c]pyridine-2-carboxamide;
N-{4-[(3-methylbutyl)carbamoyl]phenyl}-1,3-dihydro-2H-pyrrolo[3,4-c]pyridine-2-carboxamide;
N-{4-[(4,4,4-trifluorobutanoyl)amino]phenyl}-1,3-dihydro-2H-isoindole-2-carboxamide;
N-{4-[(3-ethoxypropanoyl)amino]phenyl}-1,3-dihydro-2H-isoindole-2-carboxamide;
N-{4-[(4-phenylbutanoyl)amino]phenyl}-1,3-dihydro-2H-isoindole-2-carboxamide;
N-{4-[(4-methylpentanoyl)amino]phenyl}-1,3-dihydro-2H-isoindole-2-carboxamide;
N-(4-{[(benzyloxy)acetyl]amino}phenyl)-1,3-dihydro-2H-isoindole-2-carboxamide;
N-{4-[(3-phenylpropanoyl)amino]phenyl}-1,3-dihydro-2H-isoindole-2-carboxamide;
N-{4-[(3-phenoxypropanoyl)amino]phenyl}-1,3-dihydro-2H-isoindole-2-carboxamide;
N-(4-{[N-(2-furoyl)glycyl]amino}phenyl)-1,3-dihydro-2H-isoindole-2-carboxamide;
N-(4-{[4-(2-thienyl)butanoyl]amino}phenyl)-1,3-dihydro-2H-isoindole-2-carboxamide;
N-{4-[(4-oxo-4-phenylbutanoyl)amino]phenyl}-1,3-dihydro-2H-isoindole-2-carboxamide;
N-{4-[(N-benzoylglycyl)amino]phenyl}-1,3-dihydro-2H-isoindole-2-carboxamide;
N-{4-[(4-phenoxybutanoyl)amino]phenyl}-1,3-dihydro-2H-isoindole-2-carboxamide;
N-[4-(propionylamino)phenyl]-1,3-dihydro-2H-isoindole-2-carboxamide;
N-[4-(pentanoylamino)phenyl]-1,3-dihydro-2H-isoindole-2-carboxamide;
N-[4-(hexanoylamino)phenyl]-1,3-dihydro-2H-isoindole-2-carboxamide;
N-[4-(heptanoylamino)phenyl]-1,3-dihydro-2H-isoindole-2-carboxamide;
N-[4-(pent-4-enoylamino)phenyl]-1,3-dihydro-2H-isoindole-2-carboxamide;
N-{4-[(ethoxyacetyl)amino]phenyl}-1,3-dihydro-2H-isoindole-2-carboxamide;
N-(4-{[(2-methoxyethoxy)acetyl]amino}phenyl)-1,3-dihydro-2H-isoindole-2-carboxamide;
N-{4-[(cyclopropylacetyl)amino]phenyl}-1,3-dihydro-2H-isoindole-2-carboxamide;
N-{4-[(cyclopentylacetyl)amino]phenyl}-1,3-dihydro-2H-isoindole-2-carboxamide;
N-(4-{[3-(4-methylpiperazin-1-yl)propanoyl]amino}phenyl)-1,3-dihydro-2H-isoindole-2-carboxamide;
methyl 2-({4-[(cyclopentylacetyl)amino]phenyl}carbamoyl)isoindoline-5-carboxylate;
2-({4-[(cyclopentylacetyl)amino]phenyl}carbamoyl)isoindoline-5-carboxylic acid;
N-{4-[(cyclopentylacetyl)amino]phenyl}-5-(hydroxymethyl)-1,3-dihydro-2H-isoindole-2-carboxamide;
N-{4-[(2-cyclopentylethyl)amino]phenyl}-5-(hydroxymethyl)-1,3-dihydro-2H-isoindole-2-carboxamide;
tert-butyl 4-{4-[(1,3-dihydro-2H-isoindol-2-ylcarbonyl)amino]phenyl}-3,6-dihydropyridine-1(2H)-carboxylate;
N-[4-(1,2,3,6-tetrahydropyridin-4-yl)phenyl]-1,3-dihydro-2H-isoindole-2-carboxamide;
N-{4-[1-(3-methylbutyl)-1H-pyrazol-4-yl]phenyl}-1,3-dihydro-2H-isoindole-2-carboxamide;
N-[4-(1-methyl-1H-pyrazol-4-yl)phenyl]-1,3-dihydro-2H-isoindole-2-carboxamide;
N-{4-[(1E)-5-phenylpent-1-en-1-yl]phenyl}-1,3-dihydro-2H-isoindole-2-carboxamide;
N-[4-(1-propyl-1H-pyrazol-4-yl)phenyl]-1,3-dihydro-2H-isoindole-2-carboxamide;
N-[4-(1-benzyl-1H-pyrazol-4-yl)phenyl]-1,3-dihydro-2H-isoindole-2-carboxamide;
N-{4-[1-(2-hydroxyethyl)-1H-pyrazol-4-yl]phenyl}-1,3-dihydro-2H-isoindole-2-carboxamide;
N-[6-(1-propyl-1H-pyrazol-4-yl)pyridin-3-yl]-1,3-dihydro-2H-isoindole-2-carboxamide;
N-{6-[1-(3-methylbutyl)-1H-pyrazol-4-yl]pyridin-3-yl}-1,3-dihydro-2H-isoindole-2-carboxamide;
N-[4-(5-phenylpentyl)phenyl]-1,3-dihydro-2H-isoindole-2-carboxamide;
N-[2-fluoro-4-(1-propyl-1H-pyrazol-4-yl)phenyl]-1,3-dihydro-2H-isoindole-2-carboxamide;
N-{2-fluoro-4-[1-(3-methylbutyl)-1H-pyrazol-4-yl]phenyl}-1,3-dihydro-2H-isoindole-2-carboxamide;
N-[4-(1-butyryl-1,2,3,6-tetrahydropyridin-4-yl)phenyl]-1,3-dihydro-2H-isoindole-2-carboxamide;
N-[4-(1-isobutyryl-1,2,3,6-tetrahydropyridin-4-yl)phenyl]-1,3-dihydro-2H-isoindole-2-carboxamide;
N-[4-(1-benzoyl-1,2,3,6-tetrahydropyridin-4-yl)phenyl]-1,3-dihydro-2H-isoindole-2-carboxamide;
N-{4-[1-(isopropylsulfonyl)-1,2,3,6-tetrahydropyridin-4-yl]phenyl}-1,3-dihydro-2H-isoindole-2-carboxamide;
N-(1'-isobutyl-1',2',3',6'-tetrahydro-2,4'-bipyridin-5-yl)-1,3-dihydro-2H-isoindole-2-carboxamide;
N-(1'-benzoyl-1',2',3',6'-tetrahydro-2,4'-bipyridin-5-yl)-1,3-dihydro-2H-isoindole-2-carboxamide;
N-[4-(4-benzoylpiperazin-1-yl)phenyl]-1,3-dihydro-2H-isoindole-2-carboxamide;
N-{4-[4-(isopropylsulfonyl)piperazin-1-yl]phenyl}-1,3-dihydro-2H-isoindole-2-carboxamide;
N-{4-[4-(phenylsulfonyl)piperazin-1-yl]phenyl}-1,3-dihydro-2H-isoindole-2-carboxamide;
N-{4-[3-(benzoylamino)pyrrolidin-1-yl]phenyl}-1,3-dihydro-2H-isoindole-2-carboxamide;
N-{4-[3-(butyrylamino)pyrrolidin-1-yl]phenyl}-1,3-dihydro-2H-isoindole-2-carboxamide;
tert-butyl 4-{4-[(1,3-dihydro-2H-isoindol-2-ylcarbonyl)amino]phenyl}piperazine-1-carboxylate;
N-[4-(4-propionylpiperazin-1-yl)phenyl]-1,3-dihydro-2H-isoindole-2-carboxamide;
N-{4-[4-(cyclopropylcarbonyl)piperazin-1-yl]phenyl}-1,3-dihydro-2H-isoindole-2-carboxamide;
N-(2-butyryl-2,3-dihydro-1H-isoindol-5-yl)-1,3-dihydro-2H-isoindole-2-carboxamide;
N-(2-isobutyryl-2,3-dihydro-1H-isoindol-5-yl)-1,3-dihydro-2H-isoindole-2-carboxamide;
N-(2-benzoyl-2,3-dihydro-1H-isoindol-5-yl)-1,3-dihydro-2H-isoindole-2-carboxamide;
N-[2-(3-methylbutyl)-2,3-dihydro-1H-isoindol-5-yl]-1,3-dihydro-2H-isoindole-2-carboxamide;
N-[4-(hexyloxy)phenyl]-1,3-dihydro-2H-isoindole-2-carboxamide;
N-[4-(1-benzoylpiperidin-4-yl)butyl]-1,3-dihydro-2H-isoindole-2-carboxamide;
N-{4-[1-(pyridin-3-ylcarbonyl)piperidin-4-yl]butyl}-1,3-dihydro-2H-isoindole-2-carboxamide;
N-[6-(4-chlorophenoxy)hexyl]-1,3-dihydro-2H-isoindole-2-carboxamide;

N-[4-(piperidin-4-yl)butyl]-1,3-dihydro-2H-isoindole-2-carboxamide;
N,N'-hexane-1,6-diylbis(1,3-dihydro-2H-isoindole-2-carboxamide);
N-(4-phenylbutyl)-1,3-dihydro-2H-isoindole-2-carboxamide;
ethyl 6-[(1,3-dihydro-2H-isoindol-2-ylcarbonyl)amino]hexanoate;
N-hexyl-1,3-dihydro-2H-isoindole-2-carboxamide;
N-octyl-1,3-dihydro-2H-isoindole-2-carboxamide;
N-{6-[(1-methyl-1H-pyrazol-4-yl)amino]-6-oxohexyl}-1,3-dihydro-2H-isoindole-2-carboxamide;
N-[6-(methylamino)-6-oxohexyl]-1,3-dihydro-2H-isoindole-2-carboxamide;
N-{6-oxo-6-[(3-phenylpropyl)amino]hexyl}-1,3-dihydro-2H-isoindole-2-carboxamide;
N-{6-[(3-methylbutyl)amino]-6-oxohexyl}-1,3-dihydro-2H-isoindole-2-carboxamide;
N-(5-{[4-(pyridin-2-yl)piperazin-1-yl]carbonyl}pyridin-2-yl)-1,3-dihydro-2H-isoindole-2-carboxamide;
N-{5-[(3-phenylpropyl)carbamoyl]pyridin-2-yl}-1,3-dihydro-2H-isoindole-2-carboxamide;
N-{5-[(3-methylbutyl)carbamoyl]pyridin-2-yl}-1,3-dihydro-2H-isoindole-2-carboxamide;
N-{5-[(3-phenylpropyl)carbamoyl]-1,3-thiazol-2-yl}-1,3-dihydro-2H-isoindole-2-carboxamide;
N-{5-[(3-methylbutyl)carbamoyl]-1,3-thiazol-2-yl}-1,3-dihydro-2H-isoindole-2-carboxamide;
5-fluoro-N-[4-(propylcarbamoyl)phenyl]-1,3-dihydro-2H-isoindole-2-carboxamide;
N-[4-(4-oxo-3,4-dihydrophthalazin-1-yl)phenyl]-1,3-dihydro-2H-isoindole-2-carboxamide;
N-[4-(isoquinolin-4-yl)phenyl]-1,3-dihydro-2H-isoindole-2-carboxamide;
N-[4-(1-oxo-1,2-dihydroisoquinolin-4-yl)phenyl]-1,3-dihydro-2H-isoindole-2-carboxamide;
N-[4-(4-oxo-3,4,5,6,7,8-hexahydrophthalazin-1-yl)phenyl]-1,3-dihydro-2H-isoindole-2-carboxamide;
N-[4-(8-fluoro-4-oxo-3,4-dihydrophthalazin-1-yl)phenyl]-1,3-dihydro-2H-isoindole-2-carboxamide;
5-fluoro-N-[4-(4-oxo-3,4-dihydrophthalazin-1-yl)phenyl]-1,3-dihydro-2H-isoindole-2-carboxamide;
N-[4-(4-oxo-3,4-dihydrophthalazin-1-yl)phenyl]-5-(pyrrolidin-1-ylmethyl)-1,3-dihydro-2H-isoindole-2-carboxamide;
5-(morpholin-4-ylmethyl)-N-[4-(1-oxo-1,2-dihydroisoquinolin-4-yl)phenyl]-1,3-dihydro-2H-isoindole-2-carboxamide;
5-methoxy-N-[4-(1-oxo-1,2-dihydroisoquinolin-4-yl)phenyl]-1,3-dihydro-2H-isoindole-2-carboxamide;
5-[(4-methylpiperazin-1-yl)methyl]-N-[4-(4-oxo-3,4-dihydrophthalazin-1-yl)phenyl]-1,3-dihydro-2H-isoindole-2-carboxamide;
5-cyano-N-[4-(1-oxo-1,2-dihydroisoquinolin-4-yl)phenyl]-1,3-dihydro-2H-isoindole-2-carboxamide;
5-chloro-N-[4-(1-oxo-1,2-dihydroisoquinolin-4-yl)phenyl]-1,3-dihydro-2H-isoindole-2-carboxamide;
N-[4-(4-oxo-4,5-dihydro-3H-2,3-benzodiazepin-1-yl)phenyl]-1,3-dihydro-2H-isoindole-2-carboxamide;
N-[4-(1-oxo-1,2-dihydroisoquinolin-4-yl)phenyl]-5-(pyrrolidin-1-ylmethyl)-1,3-dihydro-2H-isoindole-2-carboxamide;
N-{4-[4-oxo-8-(trifluoromethyl)-3,4-dihydrophthalazin-1-yl]phenyl}-1,3-dihydro-2H-isoindole-2-carboxamide;
5-[(dimethylamino)methyl]-N-[4-(1-oxo-1,2-dihydroisoquinolin-4-yl)phenyl]-1,3-dihydro-2H-isoindole-2-carboxamide;
5-[(diethylamino)methyl]-N-[4-(1-oxo-1,2-dihydroisoquinolin-4-yl)phenyl]-1,3-dihydro-2H-isoindole-2-carboxamide;
5-[(4-methylpiperazin-1-yl)methyl]-N-[4-(1-oxo-1,2-dihydroisoquinolin-4-yl)phenyl]-1,3-dihydro-2H-isoindole-2-carboxamide;
5-[(dimethylamino)methyl]-N-[4-(4-oxo-3,4-dihydrophthalazin-1-yl)phenyl]-1,3-dihydro-2H-isoindole-2-carboxamide;
5-[(diethylamino)methyl]-N-[4-(4-oxo-3,4-dihydrophthalazin-1-yl)phenyl]-1,3-dihydro-2H-isoindole-2-carboxamide;
N-{4-[4-oxo-8-(trifluoromethyl)-3,4-dihydrophthalazin-1-yl]phenyl}-5-(pyrrolidin-1-ylmethyl)-1,3-dihydro-2H-isoindole-2-carboxamide;
5-[(1-methylpiperidin-4-yl)oxy]-N-[4-(4-oxo-3,4-dihydrophthalazin-1-yl)phenyl]-1,3-dihydro-2H-isoindole-2-carboxamide;
5-{[(3R)-3-fluoropyrrolidin-1-yl]methyl}-N-[4-(4-oxo-3,4-dihydrophthalazin-1-yl)phenyl]-1,3-dihydro-2H-isoindole-2-carboxamide;
5-{[(3S)-3-fluoropyrrolidin-1-yl]methyl}-N-[4-(4-oxo-3,4-dihydrophthalazin-1-yl)phenyl]-1,3-dihydro-2H-isoindole-2-carboxamide;
5-(azetidin-1-ylmethyl)-N-[4-(4-oxo-3,4-dihydrophthalazin-1-yl)phenyl]-1,3-dihydro-2H-isoindole-2-carboxamide;
N-[4-(1-oxo-1,2-dihydropyrrolo[1,2-d][1,2,4]triazin-4-yl)phenyl]-1,3-dihydro-2H-isoindole-2-carboxamide;
N-[4-(1-oxo-1,2-dihydropyrrolo[1,2-d][1,2,4]triazin-4-yl)phenyl]-5-(pyrrolidin-1-ylmethyl)-1,3-dihydro-2H-isoindole-2-carboxamide;
tert-butyl 4-{4-[(1,3-dihydro-2H-isoindol-2-ylcarbonyl)amino]phenyl}piperidine-1-carboxylate;
N-[4-(5-propyl-1,2,4-oxadiazol-3-yl)phenyl]-1,3-dihydro-2H-isoindole-2-carboxamide;
N-[4-(piperidin-4-yl)phenyl]-1,3-dihydro-2H-isoindole-2-carboxamide;
N-{5-[(tetrahydrofuran-3-ylmethyl)carbamoyl]pyridin-2-yl}-1,3-dihydro-2H-isoindole-2-carboxamide;
N-[4-(1-butyrylpiperidin-4-yl)phenyl]-1,3-dihydro-2H-isoindole-2-carboxamide;
N-[4-(1-isobutyrylpiperidin-4-yl)phenyl]-1,3-dihydro-2H-isoindole-2-carboxamide;
N-[4-(1-benzoylpiperidin-4-yl)phenyl]-1,3-dihydro-2H-isoindole-2-carboxamide;
N-{4-[5-(3-methylbutyl)-1,2,4-oxadiazol-3-yl]phenyl}-1,3-dihydro-2H-isoindole-2-carboxamide;
N-[4-(5-benzyl-1,2,4-oxadiazol-3-yl)phenyl]-1,3-dihydro-2H-isoindole-2-carboxamide;
N-(4-{[(3R)-tetrahydrofuran-3-ylmethyl]carbamoyl}phenyl)-1,3-dihydro-2H-isoindole-2-carboxamide;
N-(4-{[(3S)-tetrahydrofuran-3-ylmethyl]carbamoyl}phenyl)-1,3-dihydro-2H-isoindole-2-carboxamide;
N-{4-[(2-methoxyethyl)carbamoyl]phenyl}-1,3-dihydro-2H-isoindole-2-carboxamide;
N-{4-[(5-chloropyridin-2-yl)carbamoyl]phenyl}-1,3-dihydro-2H-isoindole-2-carboxamide;
N-{4-[(3-hydroxy-4-methoxyphenyl)carbamoyl]phenyl}-1,3-dihydro-2H-isoindole-2-carboxamide;
N-{4-[(2,4-dimethoxybenzyl)carbamoyl]phenyl}-1,3-dihydro-2H-isoindole-2-carboxamide;
N-(4-{[4-(2-oxopyrrolidin-1-yl)benzyl]carbamoyl}phenyl)-1,3-dihydro-2H-isoindole-2-carboxamide;

N-(4-{[(1S,2S)-2-hydroxy-2,3-dihydro-1H-inden-1-yl]
carbamoyl}phenyl)-1,3-dihydro-2H-isoindole-2-carboxamide;
N-(4-{[(1-hydroxycyclopropyl)methyl]carbamoyl}phenyl)-1,3-dihydro-2H-isoindole-2-carboxamide;
N-{4-[(tetrahydro-2H-pyran-2-ylmethyl)carbamoyl]phenyl}-1,3-dihydro-2H-isoindole-2-carboxamide;
N-{4-[(tetrahydro-2H-pyran-3-ylmethyl)carbamoyl]phenyl}-1,3-dihydro-2H-isoindole-2-carboxamide;
N-{4-[(tetrahydro-2H-pyran-4-ylmethyl)carbamoyl]phenyl}-1,3-dihydro-2H-isoindole-2-carboxamide;
tert-butyl 4-{6-[(1,3-dihydro-2H-isoindol-2-ylcarbonyl)amino]-1H-benzimidazol-2-yl}piperazine-1-carboxylate;
N-[2-(piperazin-1-yl)-1H-benzimidazol-6-yl]-1,3-dihydro-2H-isoindole-2-carboxamide;
N-[4-(propylcarbamoyl)phenyl]-5-vinyl-1,3-dihydro-2H-isoindole-2-carboxamide;
N-{4-[(4-benzoylpiperazin-1-yl)carbonyl]phenyl}-1,3-dihydro-2H-isoindole-2-carboxamide;
N-(4-{[(2S)-tetrahydrofuran-2-ylmethyl]carbamoyl}phenyl)-1,3-dihydro-2H-pyrrolo[3,4-c]pyridine-2-carboxamide;
N-(4-{[(2R)-tetrahydrofuran-2-ylmethyl]carbamoyl}phenyl)-1,3-dihydro-2H-pyrrolo[3,4-c]pyridine-2-carboxamide;
N-{4-[5-(tetrahydrofuran-3-yl)-1,2,4-oxadiazol-3-yl]phenyl}-1,3-dihydro-2H-isoindole-2-carboxamide;
N-[4-(1-isobutyl-1,2,3,6-tetrahydropyridin-4-yl)phenyl]-1,3-dihydro-2H-isoindole-2-carboxamide;
N-(4-{[(3-methylbutyl)amino]carbonyl}phenyl)-5,7-dihydro-6H-pyrrolo[3,4-d]pyrimidine-6-carboxamide;
N-(4-{[(3-phenylpropyl)amino]carbonyl}phenyl)-5,7-dihydro-6H-pyrrolo[3,4-d]pyrimidine-6-carboxamide;
N-{4-[1-(4-methylbenzoyl)-1,2,3,6-tetrahydropyridin-4-yl]phenyl}-1,3-dihydro-2H-isoindole-2-carboxamide;
N-[4-(1-benzyl-1,2,3,6-tetrahydropyridin-4-yl)phenyl]-1,3-dihydro-2H-isoindole-2-carboxamide;
N-(4-{[4-(tetrahydrofuran-3-ylmethyl)piperazin-1-yl]carbonyl}phenyl)-1,3-dihydro-2H-isoindole-2-carboxamide;
5-fluoro-N-[4-({[(2S)-tetrahydrofuran-2-ylmethyl]amino}carbonyl)phenyl]-1,3-dihydro-2H-isoindole-2-carboxamide;
5-fluoro-N-[4-({[(2R)-tetrahydrofuran-2-ylmethyl]amino}carbonyl)phenyl]-1,3-dihydro-2H-isoindole-2-carboxamide;
N-[4-({[(1S)-2-hydroxy-1-phenylethyl]amino}carbonyl)phenyl]-1,3-dihydro-2H-pyrrolo[3,4-c]pyridine-2-carboxamide;
N-(4-{[4-(2-methoxyethyl)piperazin-1-yl]carbonyl}phenyl)-1,3-dihydro-2H-isoindole-2-carboxamide;
N-(4-{[(2S)-2-(2-hydroxyethyl)piperidin-1-yl]carbonyl}phenyl)-1,3-dihydro-2H-isoindole-2-carboxamide;
N-{4-[(propylamino)carbonyl]phenyl}-5-pyridin-3-yl-1,3-dihydro-2H-isoindole-2-carboxamide;
N-{4-[(propylamino)carbonyl]phenyl}-5-pyridin-4-yl-1,3-dihydro-2H-isoindole-2-carboxamide;
$N^5$-(2-methoxyethyl)-$N^2$-{4-[(propylamino)carbonyl]phenyl}-1,3-dihydro-2H-isoindole-2,5-dicarboxamide;
N-(4-cyanophenyl)-1,3-dihydro-2H-isoindole-2-carboxamide;
N-[4-(trifluoromethyl)phenyl]-1,3-dihydro-2H-isoindole-2-carboxamide;
N-[4-({[(1S)-2-hydroxy-1-pyridin-2-ylethyl]amino}carbonyl)phenyl]-1,3-dihydro-2H-pyrrolo[3,4-c]pyridine-2-carboxamide;
N-(4-{[(3-methylbutyl)amino]carbonyl}phenyl)-5,7-dihydro-6H-pyrrolo[3,4-b]pyridine-6-carboxamide;
N-(4-{[(tetrahydrofuran-3-ylmethyl)amino]carbonyl}phenyl)-5,7-dihydro-6H-pyrrolo[3,4-b]pyridine-6-carboxamide;
N-{4-[(4-pyridin-2-ylpiperazin-1-yl)carbonyl]phenyl}-5,7-dihydro-6H-pyrrolo[3,4-b]pyridine-6-carboxamide;
N-[4-({[(1S)-2-hydroxy-1-pyridin-2-ylethyl]amino}carbonyl)phenyl]-1,3-dihydro-2H-isoindole-2-carboxamide;
5-(1,2-dihydroxyethyl)-N-{4-[(propylamino)carbonyl]phenyl}-1,3-dihydro-2H-isoindole-2-carboxamide;
N-[4-(1-benzoylpiperidin-4-yl)butyl]-5-cyano-1,3-dihydro-2H-isoindole-2-carboxamide;
N-(1'-butyryl-1',2',3',6'-tetrahydro-3,4'-bipyridin-6-yl)-1,3-dihydro-2H-isoindole-2-carboxamide;
N-(1'-isobutyryl-1',2',3',6'-tetrahydro-3,4'-bipyridin-6-yl)-1,3-dihydro-2H-isoindole-2-carboxamide;
N-[1'-(tetrahydrofuran-3-ylcarbonyl)-1',2',3',6'-tetrahydro-3,4'-bipyridin-6-yl]-1,3-dihydro-2H-isoindole-2-carboxamide; and
N-[2-(4-acetylpiperazin-1-yl)-1H-benzimidazol-5-yl]-1,3-dihydro-2H-isoindole-2-carboxamide;
N-{4-[1-(5-oxo-L-prolyl)-1,2,3,6-tetrahydropyridin-4-yl]phenyl}-1,3-dihydro-2H-isoindole-2-carboxamide;
N-{4-[1-(5-oxo-D-prolyl)-1,2,3,6-tetrahydropyridin-4-yl]phenyl}-1,3-dihydro-2H-isoindole-2-carboxamide;
N-[4-(1-propionyl-1,2,3,6-tetrahydropyridin-4-yl)phenyl]-1,3-dihydro-2H-isoindole-2-carboxamide;
N-{4-[1-(2-methylbutanoyl)-1,2,3,6-tetrahydropyridin-4-yl]phenyl}-1,3-dihydro-2H-isoindole-2-carboxamide;
N-{4-[1-(2-ethylbutanoyl)-1,2,3,6-tetrahydropyridin-4-yl]phenyl}-1,3-dihydro-2H-isoindole-2-carboxamide;
N-{4-[1-(methoxyacetyl)-1,2,3,6-tetrahydropyridin-4-yl]phenyl}-1,3-dihydro-2H-isoindole-2-carboxamide;
N-{4-[1-(ethoxyacetyl)-1,2,3,6-tetrahydropyridin-4-yl]phenyl}-1,3-dihydro-2H-isoindole-2-carboxamide;
N-(4-{1-[(2-methoxyethoxy)acetyl]-1,2,3,6-tetrahydropyridin-4-yl}phenyl)-1,3-dihydro-2H-isoindole-2-carboxamide;
N-{4-[1-(tetrahydrofuran-2-ylcarbonyl)-1,2,3,6-tetrahydropyridin-4-yl]phenyl}-1,3-dihydro-2H-isoindole-2-carboxamide;
N-{4-[1-(tetrahydrofuran-3-ylcarbonyl)-1,2,3,6-tetrahydropyridin-4-yl]phenyl}-1,3-dihydro-2H-isoindole-2-carboxamide;
N-{4-[1-(cyclopropylacetyl)-1,2,3,6-tetrahydropyridin-4-yl]phenyl}-1,3-dihydro-2H-isoindole-2-carboxamide;
N-{4-[1-(cyclopentylcarbonyl)-1,2,3,6-tetrahydropyridin-4-yl]phenyl}-1,3-dihydro-2H-isoindole-2-carboxamide;
N-{4-[1-(2-methylbenzoyl)-1,2,3,6-tetrahydropyridin-4-yl]phenyl}-1,3-dihydro-2H-isoindole-2-carboxamide;
N-{4-[1-(3-methylbenzoyl)-1,2,3,6-tetrahydropyridin-4-yl]phenyl}-1,3-dihydro-2H-isoindole-2-carboxamide;
N-{4-[1-(2-methoxybenzoyl)-1,2,3,6-tetrahydropyridin-4-yl]phenyl}-1,3-dihydro-2H-isoindole-2-carboxamide;
N-{4-[1-(3-methoxybenzoyl)-1,2,3,6-tetrahydropyridin-4-yl]phenyl}-1,3-dihydro-2H-isoindole-2-carboxamide;
N-{4-[1-(4-methoxybenzoyl)-1,2,3,6-tetrahydropyridin-4-yl]phenyl}-1,3-dihydro-2H-isoindole-2-carboxamide;
N-{4-[1-(2-fluorobenzoyl)-1,2,3,6-tetrahydropyridin-4-yl]phenyl}-1,3-dihydro-2H-isoindole-2-carboxamide;
N-{4-[1-(3-fluorobenzoyl)-1,2,3,6-tetrahydropyridin-4-yl]phenyl}-1,3-dihydro-2H-isoindole-2-carboxamide;

N-{4-[1-(4-fluorobenzoyl)-1,2,3,6-tetrahydropyridin-4-yl]phenyl}-1,3-dihydro-2H-isoindole-2-carboxamide;
N-{4-[1-(4-chlorobenzoyl)-1,2,3,6-tetrahydropyridin-4-yl]phenyl}-1,3-dihydro-2H-isoindole-2-carboxamide;
N-(4-{1-[3-(dimethylamino)benzoyl]-1,2,3,6-tetrahydropyridin-4-yl}phenyl)-1,3-dihydro-2H-isoindole-2-carboxamide;
N-(4-{1-[4-(dimethylamino)benzoyl]-1,2,3,6-tetrahydropyridin-4-yl}phenyl)-1,3-dihydro-2H-isoindole-2-carboxamide;
N-{4-[1(3-furoyl)-1,2,3,6-tetrahydropyridin-4-yl]phenyl}-1,3-dihydro-2H-isoindole-2-carboxamide;
N-{4-[1-(3-thienylcarbonyl)-1,2,3,6-tetrahydropyridin-4-yl]phenyl}-1,3-dihydro-2H-isoindole-2-carboxamide;
N-{4-[1-(1H-pyrrol-2-ylcarbonyl)-1,2,3,6-tetrahydropyridin-4-yl]phenyl}-1,3-dihydro-2H-isoindole-2-carboxamide;
N-(4-{1-[(2,5-dimethyl-1H-pyrrol-3-yl)carbonyl]-1,2,3,6-tetrahydropyridin-4-yl}phenyl)-1,3-dihydro-2H-isoindole-2-carboxamide;
N-{4-[1-(1,3-thiazol-4-ylcarbonyl)-1,2,3,6-tetrahydropyridin-4-yl]phenyl}-1,3-dihydro-2H-isoindole-2-carboxamide;
N-{4-[1-(1H-pyrazol-4-ylcarbonyl)-1,2,3,6-tetrahydropyridin-4-yl]phenyl}-1,3-dihydro-2H-isoindole-2-carboxamide;
N-(4-{1-[(3,5-dimethyl-1,2-oxazol-4-yl)carbonyl]-1,2,3,6-tetrahydropyridin-4-yl}phenyl)-1,3-dihydro-2H-isoindole-2-carboxamide;
N-{4-[1-(pyridin-2-ylcarbonyl)-1,2,3,6-tetrahydropyridin-4-yl]phenyl}-1,3-dihydro-2H-isoindole-2-carboxamide;
N-{4-[1-(pyridin-3-ylcarbonyl)-1,2,3,6-tetrahydropyridin-4-yl]phenyl}-1,3-dihydro-2H-isoindole-2-carboxamide;
N-[4-(1-isonicotinoyl-1,2,3,6-tetrahydropyridin-4-yl)phenyl]-1,3-dihydro-2H-isoindole-2-carboxamide;
N-{4-[1-(pyridazin-3-ylcarbonyl)-1,2,3,6-tetrahydropyridin-4-yl]phenyl}-1,3-dihydro-2H-isoindole-2-carboxamide;
N-{4-[1-(pyrazin-2-ylcarbonyl)-1,2,3,6-tetrahydropyridin-4-yl]phenyl}-1,3-dihydro-2H-isoindole-2-carboxamide;
N-{4-[1-(pyrimidin-4-ylcarbonyl)-1,2,3,6-tetrahydropyridin-4-yl]phenyl}-1,3-dihydro-2H-isoindole-2-carboxamide;
N-(4-{1-[3-(piperidin-1-yl)propanoyl]-1,2,3,6-tetrahydropyridin-4-yl}phenyl)-1,3-dihydro-2H-isoindole-2-carboxamide;
N-{4-[1-(morpholin-4-ylacetyl)-1,2,3,6-tetrahydropyridin-4-yl]phenyl}-1,3-dihydro-2H-isoindole-2-carboxamide;
N-(4-{1-[(4-methylpiperazin-1-yl)acetyl]-1,2,3,6-tetrahydropyridin-4-yl}phenyl)-1,3-dihydro-2H-isoindole-2-carboxamide;
N-(1'-benzoyl-1',2',3',6'-tetrahydro-3,4'-bipyridin-6-yl)-1,3-dihydro-2H-isoindole-2-carboxamide;
N-(4-{[6-(benzoylamino)hexyl]carbamoyl}phenyl)-1,3-dihydro-2H-isoindole-2-carboxamide;
N-[4-({4-[(benzoylamino)methyl]benzyl}carbamoyl)phenyl]-5-fluoro-1,3-dihydro-2H-isoindole-2-carboxamide;
N-{4-[4-(5-oxo-L-prolyl)piperazin-1-yl]phenyl}-1,3-dihydro-2H-isoindole-2-carboxamide;
N-{4-[4-(5-oxo-D-prolyl)piperazin-1-yl]phenyl}-1,3-dihydro-2H-isoindole-2-carboxamide;
N-(4-{4-[(1-acetylpiperidin-4-yl)carbonyl]piperazin-1-yl}phenyl)-1,3-dihydro-2H-isoindole-2-carboxamide;
N-{4-[4-(2-acetamidobenzoyl)piperazin-1-yl]phenyl}-1,3-dihydro-2H-isoindole-2-carboxamide;
N-(4-{4-[4-(methylsulfonyl)benzoyl]piperazin-1-yl}phenyl)-1,3-dihydro-2H-isoindole-2-carboxamide;
N-[4-(4-butyrylpiperazin-1-yl)phenyl]-1,3-dihydro-2H-isoindole-2-carboxamide;
N-[4-(4-isobutyrylpiperazin-1-yl)phenyl]-1,3-dihydro-2H-isoindole-2-carboxamide;
N-{4-[4-(2-methylbutanoyl)piperazin-1-yl]phenyl}-1,3-dihydro-2H-isoindole-2-carboxamide;
N-{4-[4-(3,3,3-trifluoropropanoyl)piperazin-1-yl]phenyl}-1,3-dihydro-2H-isoindole-2-carboxamide;
N-{4-[4-(methoxyacetyl)piperazin-1-yl]phenyl}-1,3-dihydro-2H-isoindole-2-carboxamide;
N-{4-[4-(tetrahydrofuran-2-ylcarbonyl)piperazin-1-yl]phenyl}-1,3-dihydro-2H-isoindole-2-carboxamide;
N-{4-[4-(tetrahydrofuran-3-ylcarbonyl)piperazin-1-yl]phenyl}-1,3-dihydro-2H-isoindole-2-carboxamide;
N-{4-[4-(cyclopentylacetyl)piperazin-1-yl]phenyl}-1,3-dihydro-2H-isoindole-2-carboxamide;
N-{4-[4-(cyclohexylcarbonyl)piperazin-1-yl]phenyl}-1,3-dihydro-2H-isoindole-2-carboxamide;
N-{4-[4-(2-methoxybenzoyl)piperazin-1-yl]phenyl}-1,3-dihydro-2H-isoindole-2-carboxamide;
N-{4-[4-(3-methoxybenzoyl)piperazin-1-yl]phenyl}-1,3-dihydro-2H-isoindole-2-carboxamide;
N-{4-[4-(4-methoxybenzoyl)piperazin-1-yl]phenyl}-1,3-dihydro-2H-isoindole-2-carboxamide;
N-{4-[4-(3-fluorobenzoyl)piperazin-1-yl]phenyl}-1,3-dihydro-2H-isoindole-2-carboxamide;
N-{4-[4-(2-chlorobenzoyl)piperazin-1-yl]phenyl}-1,3-dihydro-2H-isoindole-2-carboxamide;
N-{4-[4-(4-chlorobenzoyl)piperazin-1-yl]phenyl}-1,3-dihydro-2H-isoindole-2-carboxamide;
N-{4-[4-(3-cyanobenzoyl)piperazin-1-yl]phenyl}-1,3-dihydro-2H-isoindole-2-carboxamide;
N-{4-[4-(4-cyanobenzoyl)piperazin-1-yl]phenyl}-1,3-dihydro-2H-isoindole-2-carboxamide;
N-(4-{4-[3-(dimethylamino)benzoyl]piperazin-1-yl}phenyl)-1,3-dihydro-2H-isoindole-2-carboxamide;
N-(4-{4-[4-(dimethylamino)benzoyl]piperazin-1-yl}phenyl)-1,3-dihydro-2H-isoindole-2-carboxamide;
N-{4-[4-(3,4-dimethoxybenzoyl)piperazin-1-yl]phenyl}-1,3-dihydro-2H-isoindole-2-carboxamide;
N-{4-[4-(3,5-dimethoxybenzoyl)piperazin-1-yl]phenyl}-1,3-dihydro-2H-isoindole-2-carboxamide;
N-(4-{4-[(3,4-dimethoxyphenyl)acetyl]piperazin-1-yl}phenyl)-1,3-dihydro-2H-isoindole-2-carboxamide;
N-{4-[4-(2-furoyl)piperazin-1-yl]phenyl}-1,3-dihydro-2H-isoindole-2-carboxamide;
N-{4-[4-(3-furoyl)piperazin-1-yl]phenyl}-1,3-dihydro-2H-isoindole-2-carboxamide;
N-{4-[4-(1H-pyrrol-2-ylcarbonyl)piperazin-1-yl]phenyl}-1,3-dihydro-2H-isoindole-2-carboxamide;
N-{4-[4-(1H-pyrazol-5-ylcarbonyl)piperazin-1-yl]phenyl}-1,3-dihydro-2H-isoindole-2-carboxamide;
N-{4-[4-(pyridin-2-ylcarbonyl)piperazin-1-yl]phenyl}-1,3-dihydro-2H-isoindole-2-carboxamide;
N-{4-[4-(pyridin-3-ylcarbonyl)piperazin-1-yl]phenyl}-1,3-dihydro-2H-isoindole-2-carboxamide;
N-[4-(4-isonicotinoylpiperazin-1-yl)phenyl]-1,3-dihydro-2H-isoindole-2-carboxamide;
N-{4-[4-(pyridazin-3-ylcarbonyl)piperazin-1-yl]phenyl}-1,3-dihydro-2H-isoindole-2-carboxamide;
N-{4-[4-(pyrazin-2-ylcarbonyl)piperazin-1-yl]phenyl}-1,3-dihydro-2H-isoindole-2-carboxamide;
N-{4-[4-(pyrimidin-4-ylcarbonyl)piperazin-1-yl]phenyl}-1,3-dihydro-2H-isoindole-2-carboxamide;
N-{4-[4-(N,N-dimethyl-beta-alanyl)piperazin-1-yl]phenyl}-1,3-dihydro-2H-isoindole-2-carboxamide;

N-[4-(4-acetylpiperazin-1-yl)phenyl]-1,3-dihydro-2H-isoindole-2-carboxamide;
N-{4-[4-(2-fluorobenzoyl)piperazin-1-yl]phenyl}-1,3-dihydro-2H-isoindole-2-carboxamide;
N-{4-[4-(4-fluorobenzoyl)piperazin-1-yl]phenyl}-1,3-dihydro-2H-isoindole-2-carboxamide;
N-{4-[4-(phenylacetyl)piperazin-1-yl]phenyl}-1,3-dihydro-2H-isoindole-2-carboxamide;
N-{4-[4-(1,3-thiazol-4-ylcarbonyl)piperazin-1-yl]phenyl}-1,3-dihydro-2H-isoindole-2-carboxamide;
N-{4-[4-(morpholin-4-ylacetyl)piperazin-1-yl]phenyl}-1,3-dihydro-2H-isoindole-2-carboxamide;
5-cyano-N-(4-phenylbutyl)-1,3-dihydro-2H-isoindole-2-carboxamide;
N-[4-(1-butyryl-1,2,3,6-tetrahydropyridin-4-yl)phenyl]-1,3-dihydro-2H-pyrrolo[3,4-c]pyridine-2-carboxamide;
N-[4-(1-isobutyryl-1,2,3,6-tetrahydropyridin-4-yl)phenyl]-1,3-dihydro-2H-pyrrolo[3,4-c]pyridine-2-carboxamide;
N-[4-(1-benzoyl-1,2,3,6-tetrahydropyridin-4-yl)phenyl]-1,3-dihydro-2H-pyrrolo[3,4-c]pyridine-2-carboxamide;
N-{4-[1-(tetrahydrofuran-3-ylcarbonyl)-1,2,3,6-tetrahydropyridin-4-yl]phenyl}-1,3-dihydro-2H-pyrrolo[3,4-c]pyridine-2-carboxamide;
N-[4-(1-oxo-2,3-dihydro-1H-isoindol-4-yl)phenyl]-1,3-dihydro-2H-isoindole-2-carboxamide;
N-[4-(4-oxo-3,4-dihydrophthalazin-1-yl)phenyl]-1,3-dihydro-2H-pyrrolo[3,4-c]pyridine-2-carboxamide;
N-[4-(4-oxo-3,4-dihydrophthalazin-1-yl)phenyl]-5,7-dihydro-6H-pyrrolo[3,4-b]pyridine-6-carboxamide;
N-[4-(1-oxo-1,2-dihydroisoquinolin-4-yl)cyclohex-3-en-1-yl]-1,3-dihydro-2H-isoindole-2-carboxamide;
N-[4-(4-oxo-3,4-dihydrophthalazin-1-yl)cyclohex-3-en-1-yl]-1,3-dihydro-2H-isoindole-2-carboxamide;
N-[4-(4-oxo-3,4-dihydrophthalazin-1-yl)cyclohex-3-en-1-yl]-5-(pyrrolidin-1-ylmethyl)-1,3-dihydro-2H-isoindole-2-carboxamide;
N-{4-[(tetrahydro-2H-pyran-2-ylmethyl)carbamoyl]phenyl}-1,3-dihydro-2H-pyrrolo[3,4-c]pyridine-2-carboxamide;
N-{4-[(tetrahydro-2H-pyran-3-ylmethyl)carbamoyl]phenyl}-1,3-dihydro-2H-pyrrolo[3,4-c]pyridine-2-carboxamide;
N-{4-[(tetrahydro-2H-pyran-4-ylmethyl)carbamoyl]phenyl}-1,3-dihydro-2H-pyrrolo[3,4-c]pyridine-2-carboxamide;
N-(4-{[(2S)-1-hydroxy-4-methylpentan-2-yl]carbamoyl}phenyl)-1,3-dihydro-2H-pyrrolo[3,4-c]pyridine-2-carboxamide;
N-[1-(3-methylbutyl)-1H-pyrazol-4-yl]-1,3-dihydro-2H-isoindole-2-carboxamide;
N-[1-(2-phenylethyl)-1H-pyrazol-4-yl]-1,3-dihydro-2H-isoindole-2-carboxamide;
$N^5$-[2-(dimethylamino)ethyl]-$N^2$-[4-(propylcarbamoyl)phenyl]-1,3-dihydro-2H-isoindole-2,5-dicarboxamide;
5-(morpholin-4-ylcarbonyl)-N-[4-(propylcarbamoyl)phenyl]-1,3-dihydro-2H-isoindole-2-carboxamide;
N-(4-{benzyl[3-(morpholin-4-yl)propyl]carbamoyl}phenyl)-1,3-dihydro-2H-isoindole-2-carboxamide;
N-[4-(isobutoxycarbamoyl)phenyl]-1,3-dihydro-2H-isoindole-2-carboxamide;
5-bromo-N-{4-[(cyclopentylacetyl)amino]phenyl}-1,3-dihydro-2H-isoindole-2-carboxamide;
5-cyano-N-{4-[(cyclopentylacetyl)amino]phenyl}-1,3-dihydro-2H-isoindole-2-carboxamide;
methyl 4-{[(5-cyano-1,3-dihydro-2H-isoindol-2-yl)carbonyl]amino}benzoate;
N-(4-{(E)-[(benzyloxy)imino]methyl}phenyl)-1,3-dihydro-2H-isoindole-2-carboxamide;
5-fluoro-N-{4-[(tetrahydro-2H-pyran-2-ylmethyl)carbamoyl]phenyl}-1,3-dihydro-2H-isoindole-2-carboxamide;
5-fluoro-N-{4-[(tetrahydro-2H-pyran-3-ylmethyl)carbamoyl]phenyl}-1,3-dihydro-2H-isoindole-2-carboxamide;
5-fluoro-N-{4-[(tetrahydro-2H-pyran-4-ylmethyl)carbamoyl]phenyl}-1,3-dihydro-2H-isoindole-2-carboxamide;
5-fluoro-N-(4-{[(1S)-2-hydroxy-1-phenylethyl]carbamoyl}phenyl)-1,3-dihydro-2H-isoindole-2-carboxamide;
5-fluoro-N-(4-{[(1S)-2-hydroxy-1-(pyridin-2-yl)ethyl]carbamoyl}phenyl)-1,3-dihydro-2H-isoindole-2-carboxamide;
5-fluoro-N-(4-{[(2S)-1-hydroxy-4-methylpentan-2-yl]carbamoyl}phenyl)-1,3-dihydro-2H-isoindole-2-carboxamide;
N-[4-(3-aminopyrrolidin-1-yl)phenyl]-1,3-dihydro-2H-isoindole-2-carboxamide;
N-{6-[(3-methylbutyl)carbamoyl]pyridin-3-yl}-1,3-dihydro-2H-isoindole-2-carboxamide;
N-{6-[(3-phenylpropyl)carbamoyl]pyridin-3-yl}-1,3-dihydro-2H-isoindole-2-carboxamide;
N-{6-[(tetrahydrofuran-3-ylmethyl)carbamoyl]pyridin-3-yl}-1,3-dihydro-2H-isoindole-2-carboxamide;
$N^2$-{4-[(cyclopentylacetyl)amino]phenyl}-1,3-dihydro-2H-isoindole-2,5-dicarboxamide;
N-[4-({benzyl[3-(morpholin-4-yl)propyl]amino}methyl)phenyl]-1,3-dihydro-2H-isoindole-2-carboxamide;
N-{4-[(cyclopentylacetyl)amino]phenyl}-5-(1H-pyrazol-3-yl)-1,3-dihydro-2H-isoindole-2-carboxamide;
N-{4-[(cyclopentylacetyl)amino]phenyl}-5-(pyridin-3-yl)-1,3-dihydro-2H-isoindole-2-carboxamide;
N-{4-[(cyclopentylacetyl)amino]phenyl}-5-(1-methyl-1H-pyrazol-4-yl)-1,3-dihydro-2H-isoindole-2-carboxamide;
$N^2$-{4-[(cyclopentylacetyl)amino]phenyl}-$N^5$-(2-methoxyethyl)-1,3-dihydro-2H-isoindole-2,5-dicarboxamide;
$N^2$-{4-[(cyclopentylacetyl)amino]phenyl}-$N^5$-(2-hydroxyethyl)-1,3-dihydro-2H-isoindole-2,5-dicarboxamide;
5-(aminomethyl)-N-{4-[(cyclopentylacetyl)amino]phenyl}-1,3-dihydro-2H-isoindole-2-carboxamide;
N-(4-{[(2S)-1-hydroxy-4-(methylthio)butan-2-yl]carbamoyl}phenyl)-1,3-dihydro-2H-isoindole-2-carboxamide;
N-(4-{[(2S,3S)-1-hydroxy-3-methylpentan-2-yl]carbamoyl}phenyl)-1,3-dihydro-2H-isoindole-2-carboxamide;
N-(4-{[(2S)-1-hydroxypropan-2-yl]carbamoyl}phenyl)-1,3-dihydro-2H-isoindole-2-carboxamide;
N-(4-{[(2S,3R)-1,3-dihydroxybutan-2-yl]carbamoyl}phenyl)-1,3-dihydro-2H-isoindole-2-carboxamide;
N-(4-{[(2S)-1-hydroxyhexan-2-yl]carbamoyl}phenyl)-1,3-dihydro-2H-isoindole-2-carboxamide;
N-(4-{[(2S)-1-hydroxypentan-2-yl]carbamoyl}phenyl)-1,3-dihydro-2H-isoindole-2-carboxamide;
N-(4-{[(1S,2S)-2-hydroxycyclopentyl]carbamoyl}phenyl)-1,3-dihydro-2H-isoindole-2-carboxamide;
N-(4-{[(1S,2R)-2-hydroxycyclopentyl]carbamoyl}phenyl)-1,3-dihydro-2H-isoindole-2-carboxamide;
N-(4-{[(2S)-1-cyclohexyl-3-hydroxypropan-2-yl]carbamoyl}phenyl)-1,3-dihydro-2H-isoindole-2-carboxamide;
N-[4-({(2R)-1-hydroxy-3-[(4-methylbenzyl)thio]propan-2-yl}carbamoyl)phenyl]-1,3-dihydro-2H-isoindole-2-carboxamide;

N-(4-{[(1S)-1-(4-tert-butylphenyl)-2-hydroxyethyl]carbamoyl}phenyl)-1,3-dihydro-2H-isoindole-2-carboxamide;
N-{4-[(cyclopentylacetyl)amino]phenyl}-5-methoxy-1,3-dihydro-2H-isoindole-2-carboxamide;
5-methoxy-N-[4-(propylcarbamoyl)phenyl]-1,3-dihydro-2H-isoindole-2-carboxamide;
5-methyl-N-[4-(propylcarbamoyl)phenyl]-1,3-dihydro-2H-isoindole-2-carboxamide;
N-[4-(propylcarbamoyl)phenyl]-1,3-dihydro-2H-pyrrolo[3,4-c]pyridine-2-carboxamide;
N-(4-{[(2S)-tetrahydrofuran-2-ylmethyl]carbamoyl}phenyl)-5,7-dihydro-6H-pyrrolo[3,4-b]pyridine-6-carboxamide;
N-(4-{[(2R)-tetrahydrofuran-2-ylmethyl]carbamoyl}phenyl)-5,7-dihydro-6H-pyrrolo[3,4-b]pyridine-6-carboxamide;
N-(4-{[(2S)-1-hydroxy-4-methylpentan-2-yl]carbamoyl}phenyl)-5,7-dihydro-6H-pyrrolo[3,4-b]pyridine-6-carboxamide;
N-(4-{[(1S)-2-hydroxy-1-phenylethyl]carbamoyl}phenyl)-5,7-dihydro-6H-pyrrolo[3,4-b]pyridine-6-carboxamide;
N-{4-[(tetrahydro-2H-pyran-4-ylmethyl)carbamoyl]phenyl}-5,7-dihydro-6H-pyrrolo[3,4-b]pyridine-6-carboxamide;
N-[6-(benzoylamino)hexyl]-1,3-dihydro-2H-isoindole-2-carboxamide;
N-{6-[(pyridin-3-ylcarbonyl)amino]hexyl}-1,3-dihydro-2H-isoindole-2-carboxamide;
N-{4-[(cyclopentylacetyl)amino]phenyl}-5-(pyridin-4-yl)-1,3-dihydro-2H-isoindole-2-carboxamide;
5-(hydroxymethyl)-N-{4-[(3-methylbutyl)carbamoyl]phenyl}-1,3-dihydro-2H-isoindole-2-carboxamide;
N-(6-{[(3S)-tetrahydrofuran-3-ylmethyl]carbamoyl}pyridazin-3-yl)-1,3-dihydro-2H-isoindole-2-carboxamide;
N-{6-[(cyclopentylmethyl)carbamoyl]pyridazin-3-yl}-1,3-dihydro-2H-isoindole-2-carboxamide;
N-(4-{[(1S)-2-hydroxy-1-(pyridin-2-yl)ethyl]carbamoyl}phenyl)-5,7-dihydro-6H-pyrrolo[3,4-b]pyridine-6-carboxamide;
N-[1'-(tetrahydrofuran-3-ylcarbonyl)-1',2',3',6'-tetrahydro-2,4'-bipyridin-5-yl]-1,3-dihydro-2H-isoindole-2-carboxamide;
N-{1'-[(2-methoxyethoxy)acetyl]-1',2',3',6'-tetrahydro-2,4'-bipyridin-5-yl}-1,3-dihydro-2H-isoindole-2-carboxamide;
5-(hydroxymethyl)-N-(4-phenylbutyl)-1,3-dihydro-2H-isoindole-2-carboxamide;
5-(hydroxymethyl)-N-[1-(3-methylbutyl)-1H-pyrazol-4-yl]-1,3-dihydro-2H-isoindole-2-carboxamide;
N-{5-[(3-methylbutyl)carbamoyl]pyrazin-2-yl}-1,3-dihydro-2H-isoindole-2-carboxamide;
N-(6-acetamidohexyl)-1,3-dihydro-2H-isoindole-2-carboxamide;
N-(4-{1-[(2-methoxyethoxy)acetyl]-1,2,3,6-tetrahydropyridin-4-yl}phenyl)-1,3-dihydro-2H-pyrrolo[3,4-c]pyridine-2-carboxamide;
N-(4-{(1E)-3-[benzyl(methyl)amino]prop-1-en-1-yl}phenyl)-1,3-dihydro-2H-isoindole-2-carboxamide;
N-[4-(4-phenoxypiperidin-1-yl)phenyl]-1,3-dihydro-2H-isoindole-2-carboxamide;
N-[4-(3-phenoxyazetidin-1-yl)phenyl]-1,3-dihydro-2H-isoindole-2-carboxamide;
N-(4-{[benzyl(methyl)amino]methyl}phenyl)-1,3-dihydro-2H-isoindole-2-carboxamide;
5-fluoro-N-(4-{[(3R)-tetrahydrofuran-3-ylmethyl]carbamoyl}phenyl)-1,3-dihydro-2H-isoindole-2-carboxamide;
5-fluoro-N-(4-{[(3S)-tetrahydrofuran-3-ylmethyl]carbamoyl}phenyl)-1,3-dihydro-2H-isoindole-2-carboxamide;
N-{4-[(4-hydroxypiperidin-1-yl)carbonyl]phenyl}-1,3-dihydro-2H-pyrrolo[3,4-c]pyridine-2-carboxamide;
N-{4-[(2-hydroxy-2-methylpropyl)carbamoyl]phenyl}-1,3-dihydro-2H-pyrrolo[3,4-c]pyridine-2-carboxamide;
N-{4-[(4-hydroxybutyl)carbamoyl]phenyl}-1,3-dihydro-2H-pyrrolo[3,4-c]pyridine-2-carboxamide;
N-(4-{[(2S)-1-hydroxy-3-methylbutan-2-yl]carbamoyl}phenyl)-1,3-dihydro-2H-pyrrolo[3,4-c]pyridine-2-carboxamide;
N-{4-[(1-hydroxy-2-methylpropan-2-yl)carbamoyl]phenyl}-1,3-dihydro-2H-pyrrolo[3,4-c]pyridine-2-carboxamide;
N-(4-{[(2R)-2-hydroxypropyl]carbamoyl}phenyl)-1,3-dihydro-2H-pyrrolo[3,4-c]pyridine-2-carboxamide;
N-(4-{[(2S)-2-hydroxypropyl]carbamoyl}phenyl)-1,3-dihydro-2H-pyrrolo[3,4-c]pyridine-2-carboxamide;
N-(4-{[3-(piperidin-1-yl)propyl]carbamoyl}phenyl)-1,3-dihydro-2H-pyrrolo[3,4-c]pyridine-2-carboxamide;
N-[4-(5,6-dihydroimidazo[1,5-a]pyrazin-7(8H)-ylcarbonyl)phenyl]-1,3-dihydro-2H-pyrrolo[3,4-c]pyridine-2-carboxamide;
N-[4-(1-benzyl-1H-1,2,3-triazol-4-yl)phenyl]-1,3-dihydro-2H-isoindole-2-carboxamide;
N-{4-[1-(3-methylbutyl)-1H-1,2,3-triazol-4-yl]phenyl}-1,3-dihydro-2H-isoindole-2-carboxamide;
N-{4-[1-(tetrahydrofuran-3-ylmethyl)-1H-1,2,3-triazol-4-yl]phenyl}-1,3-dihydro-2H-isoindole-2-carboxamide;
N-(4-{1-[2-(2-oxopyrrolidin-1-yl)ethyl]-1H-1,2,3-triazol-4-yl}phenyl)-1,3-dihydro-2H-isoindole-2-carboxamide;
N-{4-[1-(1-benzylpiperidin-4-yl)-1H-1,2,3-triazol-4-yl]phenyl}-1,3-dihydro-2H-isoindole-2-carboxamide;
N-{4-[1-(3-phenylpropyl)-1H-1,2,3-triazol-4-yl]phenyl}-1,3-dihydro-2H-isoindole-2-carboxamide;
N-(4-{1-[4-(morpholin-4-yl)benzyl]-1H-1,2,3-triazol-4-yl}phenyl)-1,3-dihydro-2H-isoindole-2-carboxamide;
N-[4-(1-isobutyl-1H-1,2,3-triazol-4-yl)phenyl]-1,3-dihydro-2H-isoindole-2-carboxamide;
N-{4-[1-(cyclopentylmethyl)-1H-1,2,3-triazol-4-yl]phenyl}-1,3-dihydro-2H-isoindole-2-carboxamide;
N-{4-[1-(3-methoxypropyl)-1H-1,2,3-triazol-4-yl]phenyl}-1,3-dihydro-2H-isoindole-2-carboxamide;
N-[4-(1-isobutyrylpiperidin-4-yl)phenyl]-1,3-dihydro-2H-pyrrolo[3,4-c]pyridine-2-carboxamide;
N-(4-{1-[(2-methoxyethoxy)acetyl]piperidin-4-yl}phenyl)-1,3-dihydro-2H-isoindole-2-carboxamide;
N-{5-[1-(tetrahydrofuran-3-ylcarbonyl)piperidin-4-yl]pyridin-2-yl}-1,3-dihydro-2H-isoindole-2-carboxamide;
5-(hydroxymethyl)-N-{4-[(tetrahydrofuran-3-ylacetyl)amino]phenyl}-1,3-dihydro-2H-isoindole-2-carboxamide;
5-(hydroxymethyl)-N-(4-{[(2-methoxyethoxy)acetyl]amino}phenyl)-1,3-dihydro-2H-isoindole-2-carboxamide;
N-(1'-isobutyryl-1',2',3',6'-tetrahydro-2,4'-bipyridin-5-yl)-1,3-dihydro-2H-pyrrolo[3,4-c]pyridine-2-carboxamide;
N-(1'-benzoyl-1',2',3',6'-tetrahydro-2,4'-bipyridin-5-yl)-1,3-dihydro-2H-pyrrolo[3,4-c]pyridine-2-carboxamide;
N-[1'-(tetrahydrofuran-3-ylcarbonyl)-1',2',3',6'-tetrahydro-2,4'-bipyridin-5-yl]-1,3-dihydro-2H-pyrrolo[3,4-c]pyridine-2-carboxamide;

N-{1'-[(2-methoxyethoxy)acetyl]-1',2',3',6'-tetrahydro-2,4'-bipyridin-5-yl}-1,3-dihydro-2H-pyrrolo[3,4-c]pyridine-2-carboxamide;
N-(6-{[4-(methylsulfonyl)benzoyl]amino}hexyl)-1,3-dihydro-2H-isoindole-2-carboxamide;
N-{6-[(ethoxyacetyl)amino]hexyl}-1,3-dihydro-2H-isoindole-2-carboxamide;
N-{6-[(cyclopentylcarbonyl)amino]hexyl}-1,3-dihydro-2H-isoindole-2-carboxamide;
N-{6-[(2-hydroxybenzoyl)amino]hexyl}-1,3-dihydro-2H-isoindole-2-carboxamide;
N-{6-[(3-hydroxybenzoyl)amino]hexyl}-1,3-dihydro-2H-isoindole-2-carboxamide;
N-{6-[(4-hydroxybenzoyl)amino]hexyl}-1,3-dihydro-2H-isoindole-2-carboxamide;
N-{6-[(2-methoxybenzoyl)amino]hexyl}-1,3-dihydro-2H-isoindole-2-carboxamide;
N-{6-[(3-methoxybenzoyl)amino]hexyl}-1,3-dihydro-2H-isoindole-2-carboxamide;
N-{6-[(4-methoxybenzoyl)amino]hexyl}-1,3-dihydro-2H-isoindole-2-carboxamide;
N-{6-[(2-fluorobenzoyl)amino]hexyl}-1,3-dihydro-2H-isoindole-2-carboxamide;
N-{6-[(3-fluorobenzoyl)amino]hexyl}-1,3-dihydro-2H-isoindole-2-carboxamide;
N-{6-[(4-fluorobenzoyl)amino]hexyl}-1,3-dihydro-2H-isoindole-2-carboxamide;
N-{6-[(2-chlorobenzoyl)amino]hexyl}-1,3-dihydro-2H-isoindole-2-carboxamide;
N-{6-[(3-chlorobenzoyl)amino]hexyl}-1,3-dihydro-2H-isoindole-2-carboxamide;
N-{6-[(4-chlorobenzoyl)amino]hexyl}-1,3-dihydro-2H-isoindole-2-carboxamide;
N-{6-[(3-cyanobenzoyl)amino]hexyl}-1,3-dihydro-2H-isoindole-2-carboxamide;
N-{6-[(4-cyanobenzoyl)amino]hexyl}-1,3-dihydro-2H-isoindole-2-carboxamide;
N-(6-{[3-(dimethylamino)benzoyl]amino}hexyl)-1,3-dihydro-2H-isoindole-2-carboxamide;
N-(6-{[4-(dimethylamino)benzoyl]amino}hexyl)-1,3-dihydro-2H-isoindole-2-carboxamide;
N-(6-{[3-(trifluoromethyl)benzoyl]amino}hexyl)-1,3-dihydro-2H-isoindole-2-carboxamide;
N-(6-{[4-(trifluoromethyl)benzoyl]amino}hexyl)-1,3-dihydro-2H-isoindole-2-carboxamide;
N-(6-{[3-(trifluoromethoxy)benzoyl]amino}hexyl)-1,3-dihydro-2H-isoindole-2-carboxamide;
N-{6-[(2,3-dimethoxybenzoyl)amino]hexyl}-1,3-dihydro-2H-isoindole-2-carboxamide;
N-{6-[(2,4-dimethoxybenzoyl)amino]hexyl}-1,3-dihydro-2H-isoindole-2-carboxamide;
N-{6-[(2,5-dimethoxybenzoyl)amino]hexyl}-1,3-dihydro-2H-isoindole-2-carboxamide;
N-{6-[(phenylacetyl)amino]hexyl}-1,3-dihydro-2H-isoindole-2-carboxamide;
N-(6-{[(3-fluorophenyl)acetyl]amino}hexyl)-1,3-dihydro-2H-isoindole-2-carboxamide;
5-(hydroxymethyl)-N-{4-[(tetrahydrofuran-2-ylacetyl)amino]phenyl}-1,3-dihydro-2H-isoindole-2-carboxamide;
N-{4-[(ethoxyacetyl)amino]phenyl}-5-(hydroxymethyl)-1,3-dihydro-2H-isoindole-2-carboxamide;
5-(hydroxymethyl)-N-{4-[(tetrahydro-2H-pyran-4-ylacetyl)amino]phenyl}-1,3-dihydro-2H-isoindole-2-carboxamide;
5-(hydroxymethyl)-N-{4-[(morpholin-4-ylacetyl)amino]phenyl}-1,3-dihydro-2H-isoindole-2-carboxamide;
N-[4-(morpholin-4-ylcarbonyl)phenyl]-1,3-dihydro-2H-pyrrolo[3,4-c]pyridine-2-carboxamide;
N-(4-{[3-(2-oxopyrrolidin-1-yl)propyl]carbamoyl}phenyl)-1,3-dihydro-2H-pyrrolo[3,4-c]pyridine-2-carboxamide;
N-[6-(benzoylamino)hexyl]-1,3-dihydro-2H-pyrrolo[3,4-c]pyridine-2-carboxamide;
4-fluoro-N-{6-[(pyridin-3-ylcarbonyl)amino]hexyl}-1,3-dihydro-2H-isoindole-2-carboxamide;
5-fluoro-N-{6-[(pyridin-3-ylcarbonyl)amino]hexyl}-1,3-dihydro-2H-isoindole-2-carboxamide;
5-methoxy-N-{6-[(pyridin-3-ylcarbonyl)amino]hexyl}-1,3-dihydro-2H-isoindole-2-carboxamide;
N-{6-[(pyridin-3-ylcarbonyl)amino]hexyl}-5-(trifluoromethyl)-1,3-dihydro-2H-isoindole-2-carboxamide;
4-cyano-N-{6-[(pyridin-3-ylcarbonyl)amino]hexyl}-1,3-dihydro-2H-isoindole-2-carboxamide;
5-methyl-N-{6-[(pyridin-3-ylcarbonyl)amino]hexyl}-1,3-dihydro-2H-isoindole-2-carboxamide;
4-chloro-N-{6-[(pyridin-3-ylcarbonyl)amino]hexyl}-1,3-dihydro-2H-isoindole-2-carboxamide;
5-cyano-N-{6-[(pyridin-3-ylcarbonyl)amino]hexyl}-1,3-dihydro-2H-isoindole-2-carboxamide;
5-chloro-N-{6-[(pyridin-3-ylcarbonyl)amino]hexyl}-1,3-dihydro-2H-isoindole-2-carboxamide;
N-{6-[(pyridin-2-ylcarbonyl)amino]hexyl}-1,3-dihydro-2H-isoindole-2-carboxamide;
N-{4-[1-(pyridin-2-ylcarbonyl)piperidin-4-yl]butyl}-1,3-dihydro-2H-isoindole-2-carboxamide;
N-[1'-(tetrahydrofuran-2-ylcarbonyl)-1',2',3',6'-tetrahydro-2,4'-bipyridin-5-yl]-1,3-dihydro-2H-pyrrolo[3,4-c]pyridine-2-carboxamide;
N-[1'-(tetrahydro-2H-pyran-4-ylcarbonyl)-1',2',3',6'-tetrahydro-2,4'-bipyridin-5-yl]-1,3-dihydro-2H-pyrrolo[3,4-c]pyridine-2-carboxamide;
N-[1'-(1,4-dioxan-2-ylcarbonyl)-1',2',3',6'-tetrahydro-2,4'-bipyridin-5-yl]-1,3-dihydro-2H-pyrrolo[3,4-c]pyridine-2-carboxamide;
N-{1'-[(1,1-dioxidotetrahydrothiophen-3-yl)carbonyl]-1',2',3',6'-tetrahydro-2,4'-bipyridin-5-yl}-1,3-dihydro-2H-pyrrolo[3,4-c]pyridine-2-carboxamide;
N-[1'-(2-hydroxy-2-methylpropanoyl)-1',2',3',6'-tetrahydro-2,4'-bipyridin-5-yl]-1,3-dihydro-2H-pyrrolo[3,4-c]pyridine-2-carboxamide;
N-{4-[1-(tetrahydrofuran-2-ylcarbonyl)-1,2,3,6-tetrahydropyridin-4-yl]phenyl}-1,3-dihydro-2H-pyrrolo[3,4-c]pyridine-2-carboxamide;
N-{4-[1-(tetrahydro-2H-pyran-4-ylcarbonyl)-1,2,3,6-tetrahydropyridin-4-yl]phenyl}-1,3-dihydro-2H-pyrrolo[3,4-c]pyridine-2-carboxamide;
N-{4-[1-(1,4-dioxan-2-ylcarbonyl)-1,2,3,6-tetrahydropyridin-4-yl]phenyl}-1,3-dihydro-2H-pyrrolo[3,4-c]pyridine-2-carboxamide;
N-(4-{1-[(1-methylpyrrolidin-3-yl)carbonyl]-1,2,3,6-tetrahydropyridin-4-yl}phenyl)-1,3-dihydro-2H-pyrrolo[3,4-c]pyridine-2-carboxamide;
N-(4-{1-[(1,1-dioxidotetrahydrothiophen-3-yl)carbonyl]-1,2,3,6-tetrahydropyridin-4-yl}phenyl)-1,3-dihydro-2H-pyrrolo[3,4-c]pyridine-2-carboxamide;
N-{4-[1-(2-hydroxy-2-methylpropanoyl)-1,2,3,6-tetrahydropyridin-4-yl]phenyl}-1,3-dihydro-2H-pyrrolo[3,4-c]pyridine-2-carboxamide;
N-[1'-(tetrahydrofuran-2-ylcarbonyl)-1',2',3',6'-tetrahydro-2,4'-bipyridin-5-yl]-1,3-dihydro-2H-isoindole-2-carboxamide;
N-[1'-(tetrahydro-2H-pyran-4-ylcarbonyl)-1',2',3',6'-tetrahydro-2,4'-bipyridin-5-yl]-1,3-dihydro-2H-isoindole-2-carboxamide;

N-[1'-(1,4-dioxan-2-ylcarbonyl)-1',2',3',6'-tetrahydro-2,4'-bipyridin-5-yl]-1,3-dihydro-2H-isoindole-2-carboxamide;

N-{1'-[(1-methylpyrrolidin-3-yl)carbonyl]-1',2',3',6'-tetrahydro-2,4'-bipyridin-5-yl}-1,3-dihydro-2H-isoindole-2-carboxamide;

N-{1'-[(1,1-dioxidotetrahydrothiophen-3-yl)carbonyl]-1',2',3',6'-tetrahydro-2,4'-bipyridin-5-yl}-1,3-dihydro-2H-isoindole-2-carboxamide;

N-(4-{[(1-methylpyrrolidin-3-yl)methyl]carbamoyl}phenyl)-1,3-dihydro-2H-isoindole-2-carboxamide;

N-{4-[(pyrrolidin-3-ylmethyl)carbamoyl]phenyl}-1,3-dihydro-2H-isoindole-2-carboxamide;

N-(4-{[(3S)-tetrahydrofuran-3-ylmethyl]carbamoyl}phenyl)-1,3-dihydro-2H-pyrrolo[3,4-c]pyridine-2-carboxamide;

N-(4-{[(1-methylpiperidin-4-yl)methyl]carbamoyl}phenyl)-1,3-dihydro-2H-isoindole-2-carboxamide;

N-(7-oxo-7-{[(3R)-tetrahydrofuran-3-ylmethyl]amino}heptyl)-1,3-dihydro-2H-isoindole-2-carboxamide;

N-{7-oxo-7-[(tetrahydro-2H-pyran-4-ylmethyl)amino]heptyl}-1,3-dihydro-2H-isoindole-2-carboxamide;

N-[4-(1-benzoylpiperidin-4-yl)butyl]-1,3-dihydro-2H-pyrrolo[3,4-c]pyridine-2-carboxamide;

N-{4-[(2-isopropoxyethyl)carbamoyl]phenyl}-1,3-dihydro-2H-pyrrolo[3,4-c]pyridine-2-carboxamide;

N-{4-[methyl(3-methylbutyl)carbamoyl]phenyl}-1,3-dihydro-2H-pyrrolo[3,4-c]pyridine-2-carboxamide;

N-[4-(azetidin-1-ylcarbonyl)phenyl]-1,3-dihydro-2H-pyrrolo[3,4-c]pyridine-2-carboxamide;

N-[4-(2,6-diazaspiro[3.5]non-2-ylcarbonyl)phenyl]-1,3-dihydro-2H-pyrrolo[3,4-c]pyridine-2-carboxamide;

N-[4-(1,7-diazaspiro[4.4]non-1-ylcarbonyl)phenyl]-1,3-dihydro-2H-pyrrolo[3,4-c]pyridine-2-carboxamide;

N-(4-{[4-(morpholin-4-yl)benzyl]carbamoyl}phenyl)-1,3-dihydro-2H-pyrrolo[3,4-c]pyridine-2-carboxamide;

N-{4-[(cyclopropylmethyl)carbamoyl]phenyl}-1,3-dihydro-2H-pyrrolo[3,4-c]pyridine-2-carboxamide;

N-{4-[methyl(propyl)carbamoyl]phenyl}-1,3-dihydro-2H-pyrrolo[3,4-c]pyridine-2-carboxamide;

N-[4-(isobutylcarbamoyl)phenyl]-1,3-dihydro-2H-pyrrolo[3,4-c]pyridine-2-carboxamide;

N-[4-(butylcarbamoyl)phenyl]-1,3-dihydro-2H-pyrrolo[3,4-c]pyridine-2-carboxamide;

N-{4-[(2-methoxyethyl)carbamoyl]phenyl}-1,3-dihydro-2H-pyrrolo[3,4-c]pyridine-2-carboxamide;

N-[4-(cyclopentylcarbamoyl)phenyl]-1,3-dihydro-2H-pyrrolo[3,4-c]pyridine-2-carboxamide;

N-{4-[(3R)-tetrahydrofuran-3-ylcarbamoyl]phenyl}-1,3-dihydro-2H-pyrrolo[3,4-c]pyridine-2-carboxamide;

N-{4-[(2-methoxyethyl)(methyl)carbamoyl]phenyl}-1,3-dihydro-2H-pyrrolo[3,4-c]pyridine-2-carboxamide;

N-{4-[(1-methoxypropan-2-yl)carbamoyl]phenyl}-1,3-dihydro-2H-pyrrolo[3,4-c]pyridine-2-carboxamide;

N-{4-[(cyclopentylmethyl)carbamoyl]phenyl}-1,3-dihydro-2H-pyrrolo[3,4-c]pyridine-2-carboxamide;

N-{4-[(2-thienylmethyl)carbamoyl]phenyl}-1,3-dihydro-2H-pyrrolo[3,4-c]pyridine-2-carboxamide;

N-{4-[methyl(tetrahydrofuran-2-ylmethyl)carbamoyl]phenyl}-1,3-dihydro-2H-pyrrolo[3,4-c]pyridine-2-carboxamide;

N-{4-[(3-isopropoxypropyl)carbamoyl]phenyl}-1,3-dihydro-2H-pyrrolo[3,4-c]pyridine-2-carboxamide;

N-{4-[benzyl(methyl)carbamoyl]phenyl}-1,3-dihydro-2H-pyrrolo[3,4-c]pyridine-2-carboxamide;

N-{4-[(3-aminobenzyl)carbamoyl]phenyl}-1,3-dihydro-2H-pyrrolo[3,4-c]pyridine-2-carboxamide;

N-{4-[(6-methoxypyridin-3-yl)carbamoyl]phenyl}-1,3-dihydro-2H-pyrrolo[3,4-c]pyridine-2-carboxamide;

N-{4-[(3-isobutoxypropyl)carbamoyl]phenyl}-1,3-dihydro-2H-pyrrolo[3,4-c]pyridine-2-carboxamide;

N-{4-[bis(2-methoxyethyl)carbamoyl]phenyl}-1,3-dihydro-2H-pyrrolo[3,4-c]pyridine-2-carboxamide;

N-{4-[(4-methoxybenzyl)carbamoyl]phenyl}-1,3-dihydro-2H-pyrrolo[3,4-c]pyridine-2-carboxamide;

N-{4-[(3-methoxybenzyl)carbamoyl]phenyl}-1,3-dihydro-2H-pyrrolo[3,4-c]pyridine-2-carboxamide;

N-(4-{[4-(trifluoromethyl)piperidin-1-yl]carbonyl}phenyl)-1,3-dihydro-2H-pyrrolo[3,4-c]pyridine-2-carboxamide;

N-(4-{[4-(pyrazin-2-yl)piperazin-1-yl]carbonyl}phenyl)-1,3-dihydro-2H-pyrrolo[3,4-c]pyridine-2-carboxamide;

N-{4-[(4-cyclohexylpiperazin-1-yl)carbonyl]phenyl}-1,3-dihydro-2H-pyrrolo[3,4-c]pyridine-2-carboxamide;

N-(4-{[2-(3,4-dimethoxyphenyl)ethyl]carbamoyl}phenyl)-1,3-dihydro-2H-pyrrolo[3,4-c]pyridine-2-carboxamide;

N-{4-[5-(morpholin-4-ylmethyl)-1,2,4-oxadiazol-3-yl]phenyl}-1,3-dihydro-2H-isoindole-2-carboxamide;

N-(4-{5-[(4-methylpiperazin-1-yl)methyl]-1,2,4-oxadiazol-3-yl}phenyl)-1,3-dihydro-2H-isoindole-2-carboxamide;

N-[4-(5-{[(3-methylbutyl)amino]methyl}-1,2,4-oxadiazol-3-yl)phenyl]-1,3-dihydro-2H-isoindole-2-carboxamide;

N-(4-{5-[(4-hydroxypiperidin-1-yl)methyl]-1,2,4-oxadiazol-3-yl}phenyl)-1,3-dihydro-2H-isoindole-2-carboxamide;

N-{4-[1-(2-chlorobenzoyl)piperidin-4-yl]butyl}-1,3-dihydro-2H-pyrrolo[3,4-c]pyridine-2-carboxamide;

N-[1'-(2-hydroxy-2-methylpropanoyl)-1',2',3',6'-tetrahydro-2,4'-bipyridin-5-yl]-1,3-dihydro-2H-isoindole-2-carboxamide;

N-{4-[1-(tetrahydro-2H-pyran-4-ylcarbonyl)-1,2,3,6-tetrahydropyridin-4-yl]phenyl}-1,3-dihydro-2H-isoindole-2-carboxamide;

N-{4-[1-(1,4-dioxan-2-ylcarbonyl)-1,2,3,6-tetrahydropyridin-4-yl]phenyl}-1,3-dihydro-2H-isoindole-2-carboxamide;

N-(4-{1-[(1-methylpyrrolidin-3-yl)carbonyl]-1,2,3,6-tetrahydropyridin-4-yl}phenyl)-1,3-dihydro-2H-isoindole-2-carboxamide;

N-(4-{1-[(1,1-dioxidotetrahydrothiophen-3-yl)carbonyl]-1,2,3,6-tetrahydropyridin-4-yl}phenyl)-1,3-dihydro-2H-isoindole-2-carboxamide;

N-{4-[1-(2-hydroxy-2-methylpropanoyl)-1,2,3,6-tetrahydropyridin-4-yl]phenyl}-1,3-dihydro-2H-isoindole-2-carboxamide;

N-[1'-(tetrahydrofuran-2-ylcarbonyl)-1',2',3',6'-tetrahydro-3,4'-bipyridin-6-yl]-1,3-dihydro-2H-isoindole-2-carboxamide;

N-[1'-(tetrahydro-2H-pyran-4-ylcarbonyl)-1',2',3',6'-tetrahydro-3,4'-bipyridin-6-yl]-1,3-dihydro-2H-isoindole-2-carboxamide;

N-[1'-(1,4-dioxan-2-ylcarbonyl)-1',2',3',6'-tetrahydro-3,4'-bipyridin-6-yl]-1,3-dihydro-2H-isoindole-2-carboxamide;

N-{1'-[(1-methylpyrrolidin-3-yl)carbonyl]-1',2',3',6'-tetrahydro-3,4'-bipyridin-6-yl}-1,3-dihydro-2H-isoindole-2-carboxamide;

N-{1'-[(1,1-dioxidotetrahydrothiophen-3-yl)carbonyl]-1',2',3',6'-tetrahydro-3,4'-bipyridin-6-yl}-1,3-dihydro-2H-isoindole-2-carboxamide;

N-[1'-(2-hydroxy-2-methylpropanoyl)-1',2',3',6'-tetrahydro-3,4'-bipyridin-6-yl]-1,3-dihydro-2H-isoindole-2-carboxamide;

N-(4-{[3-(dimethylamino)propyl]carbamoyl}phenyl)-1,3-dihydro-2H-pyrrolo[3,4-c]pyridine-2-carboxamide;
N-(4-{[3-(morpholin-4-yl)propyl]carbamoyl}phenyl)-1,3-dihydro-2H-pyrrolo[3,4-c]pyridine-2-carboxamide;
N-(4-{[4-(2-aminoethyl)-1H-imidazol-1-yl]carbonyl}phenyl)-1,3-dihydro-2H-pyrrolo[3,4-c]pyridine-2-carboxamide;
N-[4-({4-[2-(2-hydroxyethoxy)ethyl]piperazin-1-yl}carbonyl)phenyl]-1,3-dihydro-2H-pyrrolo[3,4-c]pyridine-2-carboxamide;
N-{4-[(3-hydroxypropyl)carbamoyl]phenyl}-1,3-dihydro-2H-pyrrolo[3,4-c]pyridine-2-carboxamide;
N-(4-{[4-(dimethylamino)butyl]carbamoyl}phenyl)-1,3-dihydro-2H-pyrrolo[3,4-c]pyridine-2-carboxamide;
N-{4-[(pyridin-4-ylmethyl)carbamoyl]phenyl}-1,3-dihydro-2H-pyrrolo[3,4-c]pyridine-2-carboxamide;
N-{4-[(pyridin-3-ylmethyl)carbamoyl]phenyl}-1,3-dihydro-2H-pyrrolo[3,4-c]pyridine-2-carboxamide;
N-{4-[(pyrimidin-4-ylmethyl)carbamoyl]phenyl}-1,3-dihydro-2H-pyrrolo[3,4-c]pyridine-2-carboxamide;
N-(4-{[2-(pyridin-3-yl)ethyl]carbamoyl}phenyl)-1,3-dihydro-2H-pyrrolo[3,4-c]pyridine-2-carboxamide;
N-(4-{[2-(4-methylpiperazin-1-yl)ethyl]carbamoyl}phenyl)-1,3-dihydro-2H-pyrrolo[3,4-c]pyridine-2-carboxamide;
N-(4-{[(1,1-dioxidotetrahydrothiophen-3-yl)methyl]carbamoyl}phenyl)-1,3-dihydro-2H-isoindole-2-carboxamide;
N-(4-{[(2,2-dimethyl-1,3-dioxolan-4-yl)methyl]carbamoyl}phenyl)-1,3-dihydro-2H-isoindole-2-carboxamide;
N-(4-{[(1S)-2-methoxy-1-phenylethyl]carbamoyl}phenyl)-1,3-dihydro-2H-isoindole-2-carboxamide;
N-[4-({[(4S)-2,2-dimethyl-1,3-dioxolan-4-yl]methyl}carbamoyl)phenyl]-1,3-dihydro-2H-isoindole-2-carboxamide;
N-[4-({[(4R)-2,2-dimethyl-1,3-dioxolan-4-yl]methyl}carbamoyl)phenyl]-1,3-dihydro-2H-isoindole-2-carboxamide;
N-[4-({[3-(hydroxymethyl)oxetan-3-yl]methyl}carbamoyl)phenyl]-1,3-dihydro-2H-isoindole-2-carboxamide;
N-[4-(2-{benzyl[3-(morpholin-4-yl)propyl]amino}-2-oxoethyl)phenyl]-1,3-dihydro-2H-isoindole-2-carboxamide;
N-[4-(3-{benzyl[3-(morpholin-4-yl)propyl]amino}-3-oxopropyl)phenyl]-1,3-dihydro-2H-isoindole-2-carboxamide;
N-{4-[(cyclopentylacetyl)amino]phenyl}-5-fluoro-1,3-dihydro-2H-isoindole-2-carboxamide;
N-{4-[(2R)-butan-2-ylcarbamoyl]phenyl}-1,3-dihydro-2H-isoindole-2-carboxamide;
N-{4-[(cyclopentylacetyl)amino]phenyl}-5-(trifluoromethyl)-1,3-dihydro-2H-isoindole-2-carboxamide;
4-cyano-N-{4-[(cyclopentylacetyl)amino]phenyl}-1,3-dihydro-2H-isoindole-2-carboxamide;
N-{4-[(cyclopentylacetyl)amino]phenyl}-5-methyl-1,3-dihydro-2H-isoindole-2-carboxamide;
4-chloro-N-{4-[(cyclopentylacetyl)amino]phenyl}-1,3-dihydro-2H-isoindole-2-carboxamide;
N-{6-[(tetrahydro-2H-pyran-4-ylmethyl)carbamoyl]pyridazin-3-yl}-1,3-dihydro-2H-isoindole-2-carboxamide;
5-chloro-N-{4-[(cyclopentylacetyl)amino]phenyl}-1,3-dihydro-2H-isoindole-2-carboxamide;
N-[4-(6-bromo-2-oxoquinolin-1(2H)-yl)butyl]-1,3-dihydro-2H-isoindole-2-carboxamide;
N-{4-[6-(3-acetylphenyl)-2-oxoquinolin-1(2H)-yl]butyl}-1,3-dihydro-2H-isoindole-2-carboxamide;
N-{4-[1-(morpholin-4-ylacetyl)-1,2,3,6-tetrahydropyridin-4-yl]phenyl}-1,3-dihydro-2H-pyrrolo[3,4-c]pyridine-2-carboxamide;
N-[1'-(morpholin-4-ylacetyl)-1',2',3',6'-tetrahydro-2,4'-bipyridin-5-yl]-1,3-dihydro-2H-isoindole-2-carboxamide;
N-[1'-(morpholin-4-ylacetyl)-1',2',3',6'-tetrahydro-3,4'-bipyridin-6-yl]-1,3-dihydro-2H-isoindole-2-carboxamide;
N-(4-{[(3-methyloxetan-3-yl)methyl]carbamoyl}phenyl)-1,3-dihydro-2H-isoindole-2-carboxamide;
N-(4-{[(3-methyloxetan-3-yl)methyl]carbamoyl}phenyl)-1,3-dihydro-2H-pyrrolo[3,4-c]pyridine-2-carboxamide;
N-(2-{(4-fluorobenzyl)[4-(pyridin-3-yl)benzyl]amino}-1,3-thiazol-5-yl)-1,3-dihydro-2H-pyrrolo[3,4-c]pyridine-2-carboxamide;
N-[4-(2-benzyl-1,3-thiazol-4-yl)phenyl]-1,3-dihydro-2H-isoindole-2-carboxamide;
N-(7-{benzyl[3-(morpholin-4-yl)propyl]amino}-7-oxoheptyl)-1,3-dihydro-2H-isoindole-2-carboxamide;
N-{4-[(3-methylbutyl)sulfamoyl]phenyl}-1,3-dihydro-2H-isoindole-2-carboxamide;
5-cyano-N-{4-[(cyclopentylmethyl)carbamoyl]phenyl}-1,3-dihydro-2H-isoindole-2-carboxamide;
5-cyano-N-{4-[(1,3-thiazol-5-ylmethyl)carbamoyl]phenyl}-1,3-dihydro-2H-isoindole-2-carboxamide;
5-cyano-N-(4-{[(1R)-3-hydroxy-1-phenylpropyl]carbamoyl}phenyl)-1,3-dihydro-2H-isoindole-2-carboxamide;
5-cyano-N-(4-{[2-hydroxy-1-(4-methylphenyl)ethyl]carbamoyl}phenyl)-1,3-dihydro-2H-isoindole-2-carboxamide;
5-cyano-N-{4-[(1,3-dihydroxypropan-2-yl)carbamoyl]phenyl}-1,3-dihydro-2H-isoindole-2-carboxamide;
5-cyano-N-(4-{[(2R)-2-hydroxypropyl]carbamoyl}phenyl)-1,3-dihydro-2H-isoindole-2-carboxamide;
5-cyano-N-{4-[(2-hydroxy-2-methylpropyl)carbamoyl]phenyl}-1,3-dihydro-2H-isoindole-2-carboxamide;
5-cyano-N-(4-{[(2R)-1-hydroxy-3-methylbutan-2-yl]carbamoyl}phenyl)-1,3-dihydro-2H-isoindole-2-carboxamide;
5-cyano-N-(4-{[(2S)-tetrahydrofuran-2-ylmethyl]carbamoyl}phenyl)-1,3-dihydro-2H-isoindole-2-carboxamide;
5-cyano-N-(4-{[2-(4-methylpiperazin-1-yl)ethyl]carbamoyl}phenyl)-1,3-dihydro-2H-isoindole-2-carboxamide;
5-cyano-N-(4-{[(1S)-2-hydroxy-1-phenylethyl]carbamoyl}phenyl)-1,3-dihydro-2H-isoindole-2-carboxamide;
5-cyano-N-{4-[(4-hydroxybutyl)carbamoyl]phenyl}-1,3-dihydro-2H-isoindole-2-carboxamide;
5-cyano-N-(4-{[(2S)-2-hydroxypropyl]carbamoyl}phenyl)-1,3-dihydro-2H-isoindole-2-carboxamide;
5-cyano-N-{4-[(3-furylmethyl)carbamoyl]phenyl}-1,3-dihydro-2H-isoindole-2-carboxamide;
5-cyano-N-{4-[(tetrahydrofuran-2-ylmethyl)carbamoyl]phenyl}-1,3-dihydro-2H-isoindole-2-carboxamide;
5-cyano-N-(4-{[4-(2-furoyl)piperazin-1-yl]carbonyl}phenyl)-1,3-dihydro-2H-isoindole-2-carboxamide;
5-cyano-N-(4-{[4-(tetrahydrofuran-2-ylcarbonyl)piperazin-1-yl]carbonyl}phenyl)-1,3-dihydro-2H-isoindole-2-carboxamide;
5-cyano-N-(4-{[3-(piperidin-1-yl)propyl]carbamoyl}phenyl)-1,3-dihydro-2H-isoindole-2-carboxamide;

5-cyano-N-(4-{[(2R)-tetrahydrofuran-2-ylmethyl]carbamoyl}phenyl)-1,3-dihydro-2H-isoindole-2-carboxamide;
5-cyano-N-(4-{[4-(ethylsulfonyl)piperazin-1-yl]carbonyl}phenyl)-1,3-dihydro-2H-isoindole-2-carboxamide;
5-cyano-N-{4-[(tetrahydrofuran-3-ylmethyl)carbamoyl]phenyl}-1,3-dihydro-2H-isoindole-2-carboxamide;
5-cyano-N-(4-{[(1R)-2-hydroxy-1-phenylethyl]carbamoyl}phenyl)-1,3-dihydro-2H-isoindole-2-carboxamide;
5-cyano-N-(4-{[(2S)-1-hydroxybutan-2-yl]carbamoyl}phenyl)-1,3-dihydro-2H-isoindole-2-carboxamide;
5-cyano-N-{4-[(2,3-dihydroxypropyl)carbamoyl]phenyl}-1,3-dihydro-2H-isoindole-2-carboxamide;
5-cyano-N-(4-{[(tetrahydro-2H-pyran-4-ylmethyl)carbamoyl]phenyl}-1,3-dihydro-2H-isoindole-2-carboxamide;
5-cyano-N-(4-{[2-hydroxy-1-(pyridin-2-yl)ethyl]carbamoyl}phenyl)-1,3-dihydro-2H-isoindole-2-carboxamide;
5-cyano-N-{4-[(1-hydroxy-4-methylpentan-2-yl)carbamoyl]phenyl}-1,3-dihydro-2H-isoindole-2-carboxamide;
5-cyano-N-(4-{[(1-methylpyrrolidin-3-yl)methyl]carbamoyl}phenyl)-1,3-dihydro-2H-isoindole-2-carboxamide;
5-cyano-N-(4-{[(1-methylpiperidin-4-yl)methyl]carbamoyl}phenyl)-1,3-dihydro-2H-isoindole-2-carboxamide;
5-cyano-N-{4-[(tetrahydro-2H-pyran-3-ylmethyl)carbamoyl]phenyl}-1,3-dihydro-2H-isoindole-2-carboxamide;
N-(5-{[(3S)-tetrahydrofuran-3-ylmethyl]carbamoyl}pyridin-2-yl)-1,3-dihydro-2H-isoindole-2-carboxamide;
N-[4-(2,6-diazaspiro[3.3]hept-2-ylcarbonyl)phenyl]-1,3-dihydro-2H-isoindole-2-carboxamide;
N-[4-(2,6-diazaspiro[3.4]oct-6-ylcarbonyl)phenyl]-1,3-dihydro-2H-isoindole-2-carboxamide;
N-[4-(2,7-diazaspiro[3.5]non-7-ylcarbonyl)phenyl]-1,3-dihydro-2H-isoindole-2-carboxamide;
N-[4-(2,6-diazaspiro[3.5]non-2-ylcarbonyl)phenyl]-1,3-dihydro-2H-isoindole-2-carboxamide;
N-[4-(1,7-diazaspiro[4.4]non-1-ylcarbonyl)phenyl]-1,3-dihydro-2H-isoindole-2-carboxamide;
N-[4-(1,7-diazaspiro[4.4]non-7-ylcarbonyl)phenyl]-1,3-dihydro-2H-isoindole-2-carboxamide;
N-[4-(2,7-diazaspiro[4.4]non-2-ylcarbonyl)phenyl]-1,3-dihydro-2H-isoindole-2-carboxamide;
N-[4-(2,8-diazaspiro[4.5]dec-2-ylcarbonyl)phenyl]-1,3-dihydro-2H-isoindole-2-carboxamide;
N-[4-(2,7-diazaspiro[4.5]dec-2-ylcarbonyl)phenyl]-1,3-dihydro-2H-isoindole-2-carboxamide;
N-[4-(2,6-diazaspiro[4.5]dec-2-ylcarbonyl)phenyl]-1,3-dihydro-2H-isoindole-2-carboxamide;
N-[4-(2,7-diazaspiro[4.5]dec-7-ylcarbonyl)phenyl]-1,3-dihydro-2H-isoindole-2-carboxamide;
N-[4-(3,9-diazaspiro[5.5]undec-3-ylcarbonyl)phenyl]-1,3-dihydro-2H-isoindole-2-carboxamide;
N-[4-(2,9-diazaspiro[5.5]undec-2-ylcarbonyl)phenyl]-1,3-dihydro-2H-isoindole-2-carboxamide;
N-[4-(2,8-diazaspiro[5.5]undec-2-ylcarbonyl)phenyl]-1,3-dihydro-2H-isoindole-2-carboxamide;
N-[4-(1,8-diazaspiro[5.5]undec-8-ylcarbonyl)phenyl]-1,3-dihydro-2H-isoindole-2-carboxamide;
N-[4-(1,8-diazaspiro[4.6]undec-8-ylcarbonyl)phenyl]-1,3-dihydro-2H-isoindole-2-carboxamide;
N-{4-[(1-oxa-8-azaspiro[4.5]dec-2-ylmethyl)carbamoyl]phenyl}-1,3-dihydro-2H-isoindole-2-carboxamide;
N-[4-(1-oxa-8-azaspiro[4.5]dec-3-ylcarbamoyl)phenyl]-1,3-dihydro-2H-isoindole-2-carboxamide;
N-{4-[(2-oxa-9-azaspiro[5.5]undec-3-ylmethyl)carbamoyl]phenyl}-1,3-dihydro-2H-isoindole-2-carboxamide;
N-[4-(1-oxa-4,8-diazaspiro[5.5]undec-4-ylcarbonyl)phenyl]-1,3-dihydro-2H-isoindole-2-carboxamide;
N-[4-(1,8-diazaspiro[4.5]dec-1-ylcarbonyl)phenyl]-1,3-dihydro-2H-isoindole-2-carboxamide;
N-[4-(1,8-diazaspiro[4.5]dec-8-ylcarbonyl)phenyl]-1,3-dihydro-2H-isoindole-2-carboxamide;
N-[4-(2,6-diazaspiro[3.4]oct-2-ylcarbonyl)phenyl]-1,3-dihydro-2H-isoindole-2-carboxamide;
N-[4-(1,7-diazaspiro[3.5]non-7-ylcarbonyl)phenyl]-1,3-dihydro-2H-isoindole-2-carboxamide;
N-[4-(1,6-diazaspiro[3.5]non-1-ylcarbonyl)phenyl]-1,3-dihydro-2H-isoindole-2-carboxamide;
N-[4-(2,5-diazaspiro[3.5]non-2-ylcarbonyl)phenyl]-1,3-dihydro-2H-isoindole-2-carboxamide;
N-[4-(5-oxa-2-azaspiro[3.4]oct-2-ylcarbonyl)phenyl]-1,3-dihydro-2H-isoindole-2-carboxamide;
N-[4-(6-oxa-2-azaspiro[3.5]non-2-ylcarbonyl)phenyl]-1,3-dihydro-2H-isoindole-2-carboxamide;
N-[4-(hexahydro-5H-furo[2,3-c]pyrrol-5-ylcarbonyl)phenyl]-1,3-dihydro-2H-isoindole-2-carboxamide;
N-[4-(tetrahydro-1H-furo[3,4-c]pyrrol-5(3H)-ylcarbonyl)phenyl]-1,3-dihydro-2H-isoindole-2-carboxamide;
N-[4-(hexahydrofuro[3,4-c]pyridin-5(3H)-ylcarbonyl)phenyl]-1,3-dihydro-2H-isoindole-2-carboxamide;
N-[4-(4-{benzyl[3-(morpholin-4-yl)propyl]amino}-4-oxobutyl)phenyl]-1,3-dihydro-2H-isoindole-2-carboxamide;
N-(4-phenylbutyl)-1,3-dihydro-2H-pyrrolo[3,4-c]pyridine-2-carboxamide;
N-[4-(2-{benzyl[3-(morpholin-4-yl)propyl]amino}ethyl)phenyl]-1,3-dihydro-2H-isoindole-2-carboxamide;
5-acetyl-N-{4-[(cyclopentylacetyl)amino]phenyl}-1,3-dihydro-2H-isoindole-2-carboxamide;
N-(4-{[(1,1-dioxidotetrahydrothiophen-3-yl)methyl]carbamoyl}phenyl)-1,3-dihydro-2H-pyrrolo[3,4-c]pyridine-2-carboxamide;
5-cyano-N-{4-[(3-methylbutyl)sulfamoyl]phenyl}-1,3-dihydro-2H-isoindole-2-carboxamide;
N-{4-[(3-methylbutyl)sulfamoyl]phenyl}-1,3-dihydro-2H-pyrrolo[3,4-c]pyridine-2-carboxamide;
N-{4-[(cyclopentylacetyl)amino]phenyl}-5-(1-hydroxyethyl)-1,3-dihydro-2H-isoindole-2-carboxamide;
N-[4-(butyrylamino)phenyl]-5-cyano-1,3-dihydro-2H-isoindole-2-carboxamide;
N-{4-[(pyrrolidin-3-ylmethyl)carbamoyl]phenyl}-1,3-dihydro-2H-pyrrolo[3,4-c]pyridine-2-carboxamide;
N-(4-{[(3S)-pyrrolidin-3-ylmethyl]carbamoyl}phenyl)-1,3-dihydro-2H-pyrrolo[3,4-c]pyridine-2-carboxamide;
N-(4-{[(1-methylpyrrolidin-3-yl)methyl]carbamoyl}phenyl)-1,3-dihydro-2H-pyrrolo[3,4-c]pyridine-2-carboxamide;
N-(4-{[(3-methoxybenzyl)sulfonyl]amino}phenyl)-1,3-dihydro-2H-isoindole-2-carboxamide;
N-(4-{[(1-methylpiperidin-4-yl)methyl]carbamoyl}phenyl)-1,3-dihydro-2H-pyrrolo[3,4-c]pyridine-2-carboxamide;
N-[4-(2,6-diazaspiro[3.4]oct-6-ylcarbonyl)phenyl]-5-fluoro-1,3-dihydro-2H-isoindole-2-carboxamide;
N-[4-(2,7-diazaspiro[3.5]non-7-ylcarbonyl)phenyl]-5-fluoro-1,3-dihydro-2H-isoindole-2-carboxamide;

N-[4-(1,7-diazaspiro[4.4]non-1-ylcarbonyl)phenyl]-5-fluoro-1,3-dihydro-2H-isoindole-2-carboxamide;
N-[4-(2,8-diazaspiro[4.5]dec-2-ylcarbonyl)phenyl]-5-fluoro-1,3-dihydro-2H-isoindole-2-carboxamide;
N-[4-(2,6-diazaspiro[4.5]dec-2-ylcarbonyl)phenyl]-5-fluoro-1,3-dihydro-2H-isoindole-2-carboxamide;
N-[4-(2,7-diazaspiro[4.5]dec-7-ylcarbonyl)phenyl]-5-fluoro-1,3-dihydro-2H-isoindole-2-carboxamide;
N-[4-(2,8-diazaspiro[5.5]undec-2-ylcarbonyl)phenyl]-5-fluoro-1,3-dihydro-2H-isoindole-2-carboxamide;
N-[4-(1,8-diazaspiro[5.5]undec-8-ylcarbonyl)phenyl]-5-fluoro-1,3-dihydro-2H-isoindole-2-carboxamide;
N-[4-(1,8-diazaspiro[4.6]undec-8-ylcarbonyl)phenyl]-5-fluoro-1,3-dihydro-2H-isoindole-2-carboxamide;
5-fluoro-N-{4-[(1-oxa-8-azaspiro[4.5]dec-2-ylmethyl)carbamoyl]phenyl}-1,3-dihydro-2H-isoindole-2-carboxamide;
5-fluoro-N-[4-(1-oxa-8-azaspiro[4.5]dec-3-ylcarbamoyl)phenyl]-1,3-dihydro-2H-isoindole-2-carboxamide;
5-fluoro-N-[4-(1-oxa-4,8-diazaspiro[5.5]undec-4-ylcarbonyl)phenyl]-1,3-dihydro-2H-isoindole-2-carboxamide;
N-[4-(1,8-diazaspiro[4.5]dec-1-ylcarbonyl)phenyl]-5-fluoro-1,3-dihydro-2H-isoindole-2-carboxamide;
N-[4-(1,8-diazaspiro[4.5]dec-8-ylcarbonyl)phenyl]-5-fluoro-1,3-dihydro-2H-isoindole-2-carboxamide;
N-[4-(2,6-diazaspiro[3.4]oct-2-ylcarbonyl)phenyl]-5-fluoro-1,3-dihydro-2H-isoindole-2-carboxamide;
N-[4-(1,7-diazaspiro[3.5]non-7-ylcarbonyl)phenyl]-5-fluoro-1,3-dihydro-2H-isoindole-2-carboxamide;
N-[4-(1,6-diazaspiro[3.5]non-1-ylcarbonyl)phenyl]-5-fluoro-1,3-dihydro-2H-isoindole-2-carboxamide;
N-[4-(2,5-diazaspiro[3.5]non-2-ylcarbonyl)phenyl]-5-fluoro-1,3-dihydro-2H-isoindole-2-carboxamide;
5-fluoro-N-[4-(5-oxa-2-azaspiro[3.4]oct-2-ylcarbonyl)phenyl]-1,3-dihydro-2H-isoindole-2-carboxamide;
5-fluoro-N-[4-(6-oxa-2-azaspiro[3.5]non-2-ylcarbonyl)phenyl]-1,3-dihydro-2H-isoindole-2-carboxamide;
5-fluoro-N-[4-(2-oxa-7-azaspiro[3.5]non-7-ylcarbonyl)phenyl]-1,3-dihydro-2H-isoindole-2-carboxamide;
5-fluoro-N-[4-(hexahydro-5H-furo[2,3-c]pyrrol-5-ylcarbonyl)phenyl]-1,3-dihydro-2H-isoindole-2-carboxamide;
5-fluoro-N-[4-(tetrahydro-1H-furo[3,4-c]pyrrol-5(3H)-ylcarbonyl)phenyl]-1,3-dihydro-2H-isoindole-2-carboxamide;
5-fluoro-N-[4-(hexahydrofuro[3,4-c]pyridin-5(3H)-ylcarbonyl)phenyl]-1,3-dihydro-2H-isoindole-2-carboxamide;
N-{4-[6-(3-acetylphenyl)-4-(3-hydroxypropyl)-2-oxoquinolin-1(2H)-yl]butyl}-1,3-dihydro-2H-isoindole-2-carboxamide;
N-{4-[1-(tetrahydrofuran-3-ylcarbonyl)piperidin-4-yl]phenyl}-1,3-dihydro-2H-pyrrolo[3,4-c]pyridine-2-carboxamide;
N-(4-{1-[(2-methoxyethoxy)acetyl]piperidin-4-yl}phenyl)-1,3-dihydro-2H-pyrrolo[3,4-c]pyridine-2-carboxamide;
N-{4-[1-(tetrahydrofuran-2-ylcarbonyl)piperidin-4-yl]phenyl}-1,3-dihydro-2H-pyrrolo[3,4-c]pyridine-2-carboxamide;
N-[4-1-(tetrahydro-2H-pyran-4-ylcarbonyl)piperidin-4-yl]phenyl}-1,3-dihydro-2H-pyrrolo[3,4-c]pyridine-2-carboxamide;
N-{4-[1-(1,4-dioxan-2-ylcarbonyl)piperidin-4-yl]phenyl}-1,3-dihydro-2H-pyrrolo[3,4-c]pyridine-2-carboxamide;
N-(4-{1-[(1-methylpyrrolidin-3-yl)carbonyl]piperidin-4-yl}phenyl)-1,3-dihydro-2H-pyrrolo[3,4-c]pyridine-2-carboxamide;
N-(4-{1-[(1,1-dioxidotetrahydrothiophen-3-yl)carbonyl]piperidin-4-yl}phenyl)-1,3-dihydro-2H-pyrrolo[3,4-c]pyridine-2-carboxamide;
N-{4-[1-(2-hydroxy-2-methylpropanoyl)piperidin-4-yl]phenyl}-1,3-dihydro-2H-pyrrolo[3,4-c]pyridine-2-carboxamide;
N-{4-[1-(morpholin-4-ylacetyl)piperidin-4-yl]phenyl}-1,3-dihydro-2H-pyrrolo[3,4-c]pyridine-2-carboxamide;
5-(acetamidomethyl)-N-{4-[(cyclopentylacetyl)amino]phenyl}-1,3-dihydro-2H-isoindole-2-carboxamide;
N-{5-[2-(2-chlorobenzyl)-1,3-thiazol-4-yl]-2-thienyl}-1,3-dihydro-2H-isoindole-2-carboxamide;
N-[4-(4-fluorophenyl)butyl]-5-(hydroxymethyl)-1,3-dihydro-2H-isoindole-2-carboxamide;
N-[4-({[(3R)-1-isobutyrylpyrrolidin-3-yl]methyl}carbamoyl)phenyl]-1,3-dihydro-2H-pyrrolo[3,4-c]pyridine-2-carboxamide;
N-[4-({[(3R)-1-benzoylpyrrolidin-3-yl]methyl}carbamoyl)phenyl]-1,3-dihydro-2H-pyrrolo[3,4-c]pyridine-2-carboxamide;
N-[4-({[1-(tetrahydrofuran-3-ylcarbonyl)pyrrolidin-3-yl]methyl}carbamoyl)phenyl]-1,3-dihydro-2H-pyrrolo[3,4-c]pyridine-2-carboxamide;
N-[4-({[1-(methylsulfonyl)pyrrolidin-3-yl]methyl}carbamoyl)phenyl]-1,3-dihydro-2H-pyrrolo[3,4-c]pyridine-2-carboxamide;
N-[4-(1-isobutyl-1,2,3,6-tetrahydropyridin-4-yl)phenyl]-1,3-dihydro-2H-pyrrolo[3,4-c]pyridine-2-carboxamide;
N-{4-[1-(tetrahydrofuran-3-ylmethyl)-1,2,3,6-tetrahydropyridin-4-yl]phenyl}-1,3-dihydro-2H-pyrrolo[3,4-c]pyridine-2-carboxamide;
N-{4-[1-(tetrahydro-2H-pyran-4-ylmethyl)-1,2,3,6-tetrahydropyridin-4-yl]phenyl}-1,3-dihydro-2H-pyrrolo[3,4-c]pyridine-2-carboxamide;
N-[4-(1-isobutylpiperidin-4-yl)phenyl]-1,3-dihydro-2H-pyrrolo[3,4-c]pyridine-2-carboxamide;
N-{4-[1-(tetrahydrofuran-3-ylmethyl)piperidin-4-yl]phenyl}-1,3-dihydro-2H-pyrrolo[3,4-c]pyridine-2-carboxamide;
N-{4-[1-(tetrahydro-2H-pyran-4-ylmethyl)piperidin-4-yl]phenyl}-1,3-dihydro-2H-pyrrolo[3,4-c]pyridine-2-carboxamide;
N-{4-[(cyclopentylacetyl)amino]phenyl}-5-(2-hydroxypropan-2-yl)-1,3-dihydro-2H-isoindole-2-carboxamide;
tert-butyl {4-[(1,3-dihydro-2H-isoindol-2-ylcarbonyl)amino]benzyl}carbamate;
N-{4-[(cyclopentylacetyl)amino]phenyl}-1,3-dihydro-2H-pyrrolo[3,4-c]pyridine-2-carboxamide;
N-{4-[(cyclopentylacetyl)amino]phenyl}-5-(methoxymethyl)-1,3-dihydro-2H-isoindole-2-carboxamide;
N-[4-(5-{[(tetrahydrofuran-2-ylmethyl)amino]methyl}-1,2,4-oxadiazol-3-yl)phenyl]-1,3-dihydro-2H-isoindole-2-carboxamide;
N-(4-{5-[(4-methoxypiperidin-1-yl)methyl]-1,2,4-oxadiazol-3-yl}phenyl)-1,3-dihydro-2H-isoindole-2-carboxamide;
N-[4-(5-{[4-(2-methoxyethyl)piperazin-1-yl]methyl}-1,2,4-oxadiazol-3-yl)phenyl]-1,3-dihydro-2H-isoindole-2-carboxamide;
N-[4-({[1-(morpholin-4-yl)cyclopentyl]methyl}carbamoyl)phenyl]-1,3-dihydro-2H-pyrrolo[3,4-c]pyridine-2-carboxamide;
N-{4-[(1-pentanoylpiperidin-4-yl)oxy]phenyl}-1,3-dihydro-2H-pyrrolo[3,4-c]pyridine-2-carboxamide;
N-{4-[(1-acetylpiperidin-4-yl)oxy]phenyl}-1,3-dihydro-2H-pyrrolo[3,4-c]pyridine-2-carboxamide;

N-{4-[(1-butyrylpiperidin-4-yl)oxy]phenyl}-1,3-dihydro-2H-pyrrolo[3,4-c]pyridine-2-carboxamide;
N-(4-{[1-(2-methylbutanoyl)piperidin-4-yl]oxy}phenyl)-1,3-dihydro-2H-pyrrolo[3,4-c]pyridine-2-carboxamide;
N-(4-{[1-(3,3,3-trifluoropropanoyl)piperidin-4-yl]oxy}phenyl)-1,3-dihydro-2H-pyrrolo[3,4-c]pyridine-2-carboxamide;
N-(4-{[1-(methoxyacetyl)piperidin-4-yl]oxy}phenyl)-1,3-dihydro-2H-pyrrolo[3,4-c]pyridine-2-carboxamide;
N-(4-{[1-(tetrahydrofuran-2-ylcarbonyl)piperidin-4-yl]oxy}phenyl)-1,3-dihydro-2H-pyrrolo[3,4-c]pyridine-2-carboxamide;
N-(4-{[1-(cyclopropylcarbonyl)piperidin-4-yl]oxy}phenyl)-1,3-dihydro-2H-pyrrolo[3,4-c]pyridine-2-carboxamide;
N-(4-{[1-(cyclopropylacetyl)piperidin-4-yl]oxy}phenyl)-1,3-dihydro-2H-pyrrolo[3,4-c]pyridine-2-carboxamide;
N-(4-{[1-(cyclobutylcarbonyl)piperidin-4-yl]oxy}phenyl)-1,3-dihydro-2H-pyrrolo[3,4-c]pyridine-2-carboxamide;
N-(4-{[1-(cyclopentylcarbonyl)piperidin-4-yl]oxy}phenyl)-1,3-dihydro-2H-pyrrolo[3,4-c]pyridine-2-carboxamide;
N-(4-{[1-(cyclopentylacetyl)piperidin-4-yl]oxy}phenyl)-1,3-dihydro-2H-pyrrolo[3,4-c]pyridine-2-carboxamide;
N-(4-{[1-(cyclohexylcarbonyl)piperidin-4-yl]oxy}phenyl)-1,3-dihydro-2H-pyrrolo[3,4-c]pyridine-2-carboxamide;
N-{6-[(1-acetylpiperidin-4-yl)oxy]pyridin-3-yl}-1,3-dihydro-2H-isoindole-2-carboxamide;
N-{6-[(1-isobutyrylpiperidin-4-yl)oxy]pyridin-3-yl}-1,3-dihydro-2H-isoindole-2-carboxamide;
N-(6-{[1-(3-methylbutanoyl)piperidin-4-yl]oxy}pyridin-3-yl)-1,3-dihydro-2H-isoindole-2-carboxamide;
N-(6-{[1-(4,4,4-trifluorobutanoyl)piperidin-4-yl]oxy}pyridin-3-yl)-1,3-dihydro-2H-isoindole-2-carboxamide;
N-(6-{[1-(methoxyacetyl)piperidin-4-yl]oxy}pyridin-3-yl)-1,3-dihydro-2H-isoindole-2-carboxamide;
N-(6-{[1-(tetrahydrofuran-2-ylcarbonyl)piperidin-4-yl]oxy}pyridin-3-yl)-1,3-dihydro-2H-isoindole-2-carboxamide;
N-(6-{[1-(tetrahydrofuran-3-ylcarbonyl)piperidin-4-yl]oxy}pyridin-3-yl)-1,3-dihydro-2H-isoindole-2-carboxamide;
N-(6-{[1-(cyclopropylcarbonyl)piperidin-4-yl]oxy}pyridin-3-yl)-1,3-dihydro-2H-isoindole-2-carboxamide;
N-(6-{[1-(cyclopropylacetyl)piperidin-4-yl]oxy}pyridin-3-yl)-1,3-dihydro-2H-isoindole-2-carboxamide;
N-(6-{[1-(cyclobutylcarbonyl)piperidin-4-yl]oxy}pyridin-3-yl)-1,3-dihydro-2H-isoindole-2-carboxamide;
N-(6-{[1-(cyclopentylcarbonyl)piperidin-4-yl]oxy}pyridin-3-yl)-1,3-dihydro-2H-isoindole-2-carboxamide;
N-(6-{[1-(cyclopentylacetyl)piperidin-4-yl]oxy}pyridin-3-yl)-1,3-dihydro-2H-isoindole-2-carboxamide;
N-(6-{[1-(cyclohexylcarbonyl)piperidin-4-yl]oxy}pyridin-3-yl)-1,3-dihydro-2H-isoindole-2-carboxamide;
tert-butyl (2-{4-[(1,3-dihydro-2H-isoindol-2-ylcarbonyl)amino]phenyl}ethyl)carbamate;
N-(4-{1-[(2R)-tetrahydrofuran-2-ylcarbonyl]-1,2,3,6-tetrahydropyridin-4-yl}phenyl)-1,3-dihydro-2H-pyrrolo[3,4-c]pyridine-2-carboxamide;
N-(4-{1-[(2S)-tetrahydrofuran-2-ylcarbonyl]-1,2,3,6-tetrahydropyridin-4-yl}phenyl)-1,3-dihydro-2H-pyrrolo[3,4-c]pyridine-2-carboxamide;
N-(4-{[(1S)-1-(4-fluorophenyl)-2-hydroxyethyl]carbamoyl}phenyl)-1,3-dihydro-2H-pyrrolo[3,4-c]pyridine-2-carboxamide;
N-(4-{[(1S)-2-hydroxy-1-(4-methoxyphenyl)ethyl]carbamoyl}phenyl)-1,3-dihydro-2H-pyrrolo[3,4-c]pyridine-2-carboxamide;
N-[4-({[3-(hydroxymethyl)oxetan-3-yl]methyl}carbamoyl)phenyl]-1,3-dihydro-2H-pyrrolo[3,4-c]pyridine-2-carboxamide;
N-(4-{[(1S)-1-(1,3-benzodioxol-5-yl)-2-hydroxyethyl]carbamoyl}phenyl)-1,3-dihydro-2H-pyrrolo[3,4-c]pyridine-2-carboxamide;
N-{4-[(tetrahydrofuran-3-ylmethyl)sulfamoyl]phenyl}-1,3-dihydro-2H-isoindole-2-carboxamide;
N-{4-[(tetrahydrofuran-3-ylmethyl)sulfamoyl]phenyl}-1,3-dihydro-2H-pyrrolo[3,4-c]pyridine-2-carboxamide;
5-cyano-N-{4-[(tetrahydrofuran-3-ylmethyl)sulfamoyl]phenyl}-1,3-dihydro-2H-isoindole-2-carboxamide;
N-(4-{[(1S)-1-(4-fluorophenyl)-2-hydroxyethyl]carbamoyl}phenyl)-1,3-dihydro-2H-isoindole-2-carboxamide;
N-(4-{[(1S)-2-hydroxy-1-(4-methoxyphenyl)ethyl]carbamoyl}phenyl)-1,3-dihydro-2H-isoindole-2-carboxamide;
N-(4-{[(1S)-1-(1,3-benzodioxol-5-yl)-2-hydroxyethyl]carbamoyl}phenyl)-1,3-dihydro-2H-isoindole-2-carboxamide;
N-{4-[1-(tetrahydrofuran-3-ylcarbonyl)piperidin-4-yl]phenyl}-1,3-dihydro-2H-isoindole-2-carboxamide;
N-{4-[1-(tetrahydrofuran-2-ylcarbonyl)piperidin-4-yl]phenyl}-1,3-dihydro-2H-isoindole-2-carboxamide;
N-{4-[1-(tetrahydro-2H-pyran-4-ylcarbonyl)piperidin-4-yl]phenyl}-1,3-dihydro-2H-isoindole-2-carboxamide;
N-{4-[1-(1,4-dioxan-2-ylcarbonyl)piperidin-4-yl]phenyl}-1,3-dihydro-2H-isoindole-2-carboxamide;
N-(4-{1-[(1-methylpyrrolidin-3-yl)carbonyl]piperidin-4-yl}-phenyl)-1,3-dihydro-2H-isoindole-2-carboxamide;
N-(4-{1-[(1,1-dioxidotetrahydrothiophen-3-yl)carbonyl]piperidin-4-yl}phenyl)-1,3-dihydro-2H-isoindole-2-carboxamide;
N-{4-[1-(2-hydroxy-2-methylpropanoyl)piperidin-4-yl]phenyl}-1,3-dihydro-2H-isoindole-2-carboxamide;
N-{4-[1-(morpholin-4-ylacetyl)piperidin-4-yl]phenyl}-1,3-dihydro-2H-isoindole-2-carboxamide;
N-(4-{[1-(3,3,3-trifluoropropanoyl)azetidin-3-yl]oxy}phenyl)-1,3-dihydro-2H-pyrrolo[3,4-c]pyridine-2-carboxamide;
N-(4-{[1-(4,4,4-trifluorobutanoyl)azetidin-3-yl]oxy}phenyl)-1,3-dihydro-2H-pyrrolo[3,4-c]pyridine-2-carboxamide;
N-(4-{[1-(tetrahydrofuran-2-ylcarbonyl)azetidin-3-yl]oxy}phenyl)-1,3-dihydro-2H-pyrrolo[3,4-c]pyridine-2-carboxamide;
N-(4-{[1-(tetrahydrofuran-3-ylacetyl)azetidin-3-yl]oxy}phenyl)-1,3-dihydro-2H-pyrrolo[3,4-c]pyridine-2-carboxamide;
N-(4-{[1-(cyclobutylcarbonyl)azetidin-3-yl]oxy}phenyl)-1,3-dihydro-2H-pyrrolo[3,4-c]pyridine-2-carboxamide;
N-(4-{[1-(cyclopentylcarbonyl)azetidin-3-yl]oxy}phenyl)-1,3-dihydro-2H-pyrrolo[3,4-c]pyridine-2-carboxamide;
N-(4-{[1-(3-phenylpropanoyl)pyrrolidin-3-yl]oxy}phenyl)-1,3-dihydro-2H-pyrrolo[3,4-c]pyridine-2-carboxamide;
N-(4-{[1-(phenylacetyl)pyrrolidin-3-yl]oxy}phenyl)-1,3-dihydro-2H-pyrrolo[3,4-c]pyridine-2-carboxamide;
N-[4-({1-[(4-methoxyphenyl)acetyl]pyrrolidin-3-yl}oxy)phenyl]-1,3-dihydro-2H-pyrrolo[3,4-c]pyridine-2-carboxamide;
N-(4-{[1-(methoxyacetyl)pyrrolidin-3-yl]oxy}phenyl)-1,3-dihydro-2H-pyrrolo[3,4-c]pyridine-2-carboxamide;

N-(4-{[1-(cyclopropylcarbonyl)pyrrolidin-3-yl]oxy}phenyl)-1,3-dihydro-2H-pyrrolo[3,4-c]pyridine-2-carboxamide;

N-(4-{[1-(cyclohexylcarbonyl)pyrrolidin-3-yl]oxy}phenyl)-1,3-dihydro-2H-pyrrolo[3,4-c]pyridine-2-carboxamide;

N-(4-{[1-(cyclopentylacetyl)pyrrolidin-3-yl]oxy}phenyl)-1,3-dihydro-2H-pyrrolo[3,4-c]pyridine-2-carboxamide;

N-(4-{[1-(cyclopentylcarbonyl)pyrrolidin-3-yl]oxy}phenyl)-1,3-dihydro-2H-pyrrolo[3,4-c]pyridine-2-carboxamide;

N-{4-[(1-benzoylpyrrolidin-3-yl)oxy]phenyl}-1,3-dihydro-2H-pyrrolo[3,4-c]pyridine-2-carboxamide;

N-(4-{[1-(3-ethoxypropanoyl)pyrrolidin-3-yl]oxy}phenyl)-1,3-dihydro-2H-pyrrolo[3,4-c]pyridine-2-carboxamide;

N-[4-({1-[(2-methylcyclopropyl)carbonyl]pyrrolidin-3-yl}oxy)phenyl]-1,3-dihydro-2H-pyrrolo[3,4-c]pyridine-2-carboxamide;

N-[4-({1-[(1-methylcyclopropyl)carbonyl]pyrrolidin-3-yl}oxy)phenyl]-1,3-dihydro-2H-pyrrolo[3,4-c]pyridine-2-carboxamide;

N-(4-{[1-(cyclobutylcarbonyl)pyrrolidin-3-yl]oxy}phenyl)-1,3-dihydro-2H-pyrrolo[3,4-c]pyridine-2-carboxamide;

N-(4-{[1-(3-methylbutanoyl)pyrrolidin-3-yl]oxy}phenyl)-1,3-dihydro-2H-pyrrolo[3,4-c]pyridine-2-carboxamide;

N-(4-{[1-(2-methylpropanoyl)pyrrolidin-3-yl]oxy}phenyl)-1,3-dihydro-2H-pyrrolo[3,4-c]pyridine-2-carboxamide;

N-{4-[(1-acetylpyrrolidin-3-yl)oxy]phenyl}-1,3-dihydro-2H-pyrrolo[3,4-c]pyridine-2-carboxamide;

N-(4-{[1-(4,4,4-trifluorobutanoyl)pyrrolidin-3-yl]oxy}phenyl)-1,3-dihydro-2H-pyrrolo[3,4-c]pyridine-2-carboxamide;

N-(4-{[1-(tetrahydrofuran-3-ylcarbonyl)pyrrolidin-3-yl]oxy}phenyl)-1,3-dihydro-2H-pyrrolo[3,4-c]pyridine-2-carboxamide;

N-(4-{[1-(tetrahydrofuran-2-ylcarbonyl)pyrrolidin-3-yl]oxy}phenyl)-1,3-dihydro-2H-pyrrolo[3,4-c]pyridine-2-carboxamide;

N-(4-{[1-(ethoxyacetyl)pyrrolidin-3-yl]oxy}phenyl)-1,3-dihydro-2H-pyrrolo[3,4-c]pyridine-2-carboxamide;

N-(4-{[1-(tetrahydrofuran-3-ylcarbonyl)piperidin-4-yl]oxy}phenyl)-1,3-dihydro-2H-isoindole-2-carboxamide;

N-(4-{1-[(1-methylpiperidin-4-yl)carbonyl]-1,2,3,6-tetrahydropyridin-4-yl}phenyl)-1,3-dihydro-2H-pyrrolo[3,4-c]pyridine-2-carboxamide;

N-(4-{1-[(1,1-dioxidotetrahydro-2H-thiopyran-4-yl)carbonyl]-1,2,3,6-tetrahydropyridin-4-yl}phenyl)-1,3-dihydro-2H-pyrrolo[3,4-c]pyridine-2-carboxamide;

N-(4-{1-[(3R)-tetrahydrofuran-3-ylcarbonyl]-1,2,3,6-tetrahydropyridin-4-yl}phenyl)-1,3-dihydro-2H-pyrrolo[3,4-c]pyridine-2-carboxamide;

N-(4-{1-[(3S)-tetrahydrofuran-3-ylcarbonyl]-1,2,3,6-tetrahydropyridin-4-yl}phenyl)-1,3-dihydro-2H-pyrrolo[3,4-c]pyridine-2-carboxamide;

N-(4-{4-[(2-methylpropanoyl)amino]cyclohex-1-en-1-yl}phenyl)-1,3-dihydro-2H-pyrrolo[3,4-c]pyridine-2-carboxamide;

5-cyano-N-{4-[1-(2-methylpropanoyl)-1,2,3,6-tetrahydropyridin-4-yl]phenyl}-1,3-dihydro-2H-isoindole-2-carboxamide;

tert-butyl [(1-{4-[(1,3-dihydro-2H-isoindol-2-ylcarbonyl)amino]phenyl}azetidin-3-yl)methyl]carbamate;

N-(4-{4-[(tetrahydrofuran-3-ylcarbonyl)amino]cyclohex-1-en-1-yl}phenyl)-1,3-dihydro-2H-pyrrolo[3,4-c]pyridine-2-carboxamide;

N-(4-{4-[(tetrahydro-2H-pyran-4-ylcarbonyl)amino]cyclohex-1-en-1-yl}phenyl)-1,3-dihydro-2H-pyrrolo[3,4-c]pyridine-2-carboxamide;

N-(4-{4-[(morpholin-4-ylacetyl)amino]cyclohex-1-en-1-yl}phenyl)-1,3-dihydro-2H-pyrrolo[3,4-c]pyridine-2-carboxamide;

N-[4-(4-{[(2-methoxyethoxy)acetyl]amino}cyclohex-1-en-1-yl)phenyl]-1,3-dihydro-2H-pyrrolo[3,4-c]pyridine-2-carboxamide;

N-(4-{[1-(cyclohexylacetyl)piperidin-4-yl]oxy}phenyl)-1,3-dihydro-2H-pyrrolo[3,4-c]pyridine-2-carboxamide;

N-(4-{[1-(tetrahydro-2H-pyran-4-ylacetyl)piperidin-4-yl]oxy}phenyl)-1,3-dihydro-2H-pyrrolo[3,4-c]pyridine-2-carboxamide;

N-(4-{[1-(2-methylbutanoyl)piperidin-4-yl]oxy}phenyl)-1,3-dihydro-2H-isoindole-2-carboxamide;

N-(4-{[1-(3-methylbutanoyl)piperidin-4-yl]oxy}phenyl)-1,3-dihydro-2H-isoindole-2-carboxamide;

N-(4-{[1-(2,3-dimethylbutanoyl)piperidin-4-yl]oxy}phenyl)-1,3-dihydro-2H-isoindole-2-carboxamide;

N-(4-{[1-(tetrahydrofuran-2-ylcarbonyl)piperidin-4-yl]oxy}phenyl)-1,3-dihydro-2H-isoindole-2-carboxamide;

N-(4-{[1-(cyclohexylcarbonyl)piperidin-4-yl]oxy}phenyl)-1,3-dihydro-2H-isoindole-2-carboxamide;

N-(4-{[1-(cyclohexylacetyl)piperidin-4-yl]oxy}phenyl)-1,3-dihydro-2H-isoindole-2-carboxamide;

N-(4-{[1-(tetrahydro-2H-pyran-4-ylacetyl)piperidin-4-yl]oxy}phenyl)-1,3-dihydro-2H-isoindole-2-carboxamide;

N-(4-{[1-(morpholin-4-ylacetyl)piperidin-4-yl]oxy}phenyl)-1,3-dihydro-2H-isoindole-2-carboxamide;

N-(4-{[1-(tetrahydrofuran-3-ylacetyl)piperidin-4-yl]oxy}phenyl)-1,3-dihydro-2H-isoindole-2-carboxamide;

N-(4-{[1-(tetrahydrofuran-2-ylacetyl)azetidin-3-yl]oxy}phenyl)-1,3-dihydro-2H-pyrrolo[3,4-c]pyridine-2-carboxamide;

N-(4-{[1-(tetrahydro-2H-pyran-4-ylacetyl)azetidin-3-yl]oxy}phenyl)-1,3-dihydro-2H-pyrrolo[3,4-c]pyridine-2-carboxamide;

N-(4-{[1-(morpholin-4-ylacetyl)azetidin-3-yl]oxy}phenyl)-1,3-dihydro-2H-pyrrolo[3,4-c]pyridine-2-carboxamide;

N-(4-{[1-(cyclohexylacetyl)azetidin-3-yl]oxy}phenyl)-1,3-dihydro-2H-pyrrolo[3,4-c]pyridine-2-carboxamide;

N-(4-{[1-(2-methylbutanoyl)azetidin-3-yl]oxy}phenyl)-1,3-dihydro-2H-pyrrolo[3,4-c]pyridine-2-carboxamide;

N-(4-{[1-(2,2-dimethylpropanoyl)azetidin-3-yl]oxy}phenyl)-1,3-dihydro-2H-pyrrolo[3,4-c]pyridine-2-carboxamide;

N-(4-{[1-(3,3-dimethylbutanoyl)azetidin-3-yl]oxy}phenyl)-1,3-dihydro-2H-pyrrolo[3,4-c]pyridine-2-carboxamide;

N-(4-{[1-(tricyclo[3.3.1.1~3,7~]dec-1-ylacetyl)azetidin-3-yl]oxy}phenyl)-1,3-dihydro-2H-pyrrolo[3,4-c]pyridine-2-carboxamide;

N-[4-({1-[(4-methoxycyclohexyl)carbonyl]azetidin-3-yl}oxy)phenyl]-1,3-dihydro-2H-pyrrolo[3,4-c]pyridine-2-carboxamide;

N-[4-({[4-(acetylamino)phenyl]sulfonyl}amino)phenyl]-1,3-dihydro-2H-pyrrolo[3,4-c]pyridine-2-carboxamide;

N-{4-[(propylsulfonyl)amino]phenyl}-1,3-dihydro-2H-pyrrolo[3,4-c]pyridine-2-carboxamide;

N-(4-{[(4-propylphenyl)sulfonyl]amino}phenyl)-1,3-dihydro-2H-pyrrolo[3,4-c]pyridine-2-carboxamide;

N-{4-[(butylsulfonyl)amino]phenyl}-1,3-dihydro-2H-pyrrolo[3,4-c]pyridine-2-carboxamide;

N-{4-[({[(1S,4R)-7,7-dimethyl-2-oxobicyclo[2.2.1]hept-1-yl]methyl}sulfonyl)amino]phenyl}-1,3-dihydro-2H-pyrrolo[3,4-c]pyridine-2-carboxamide;

N-{4-[(ethylsulfonyl)amino]phenyl}-1,3-dihydro-2H-pyrrolo[3,4-c]pyridine-2-carboxamide;

N-{4-[(benzylsulfonyl)amino]phenyl}-1,3-dihydro-2H-pyrrolo[3,4-c]pyridine-2-carboxamide;

N-(4-{[(4-fluorophenyl)sulfonyl]amino}phenyl)-1,3-dihydro-2H-pyrrolo[3,4-c]pyridine-2-carboxamide;
N-{4-[(thiophen-2-ylsulfonyl)amino]phenyl}-1,3-dihydro-2H-pyrrolo[3,4-c]pyridine-2-carboxamide;
N-[4-(1,7-diazaspiro[4.4]non-7-ylcarbonyl)phenyl]-1,3-dihydro-2H-pyrrolo[3,4-c]pyridine-2-carboxamide;
N-[4-(2,7-diazaspiro[4.5]dec-2-ylcarbonyl)phenyl]-1,3-dihydro-2H-pyrrolo[3,4-c]pyridine-2-carboxamide;
N-[4-(2,6-diazaspiro[4.5]dec-2-ylcarbonyl)phenyl]-1,3-dihydro-2H-pyrrolo[3,4-c]pyridine-2-carboxamide;
N-[4-(2,7-diazaspiro[4.5]dec-7-ylcarbonyl)phenyl]-1,3-dihydro-2H-pyrrolo[3,4-c]pyridine-2-carboxamide;
N-[4-(2,9-diazaspiro[5.5]undec-2-ylcarbonyl)phenyl]-1,3-dihydro-2H-pyrrolo[3,4-c]pyridine-2-carboxamide;
N-[4-(2,8-diazaspiro[5.5]undec-2-ylcarbonyl)phenyl]-1,3-dihydro-2H-pyrrolo[3,4-c]pyridine-2-carboxamide;
N-[4-(1,8-diazaspiro[5.5]undec-8-ylcarbonyl)phenyl]-1,3-dihydro-2H-pyrrolo[3,4-c]pyridine-2-carboxamide;
N-[4-(1,8-diazaspiro[4.6]undec-8-ylcarbonyl)phenyl]-1,3-dihydro-2H-pyrrolo[3,4-c]pyridine-2-carboxamide;
N-{4-[(1-oxa-8-azaspiro[4.5]dec-2-ylmethyl)carbamoyl]phenyl}-1,3-dihydro-2H-pyrrolo[3,4-c]pyridine-2-carboxamide;
N-[4-(1-oxa-8-azaspiro[4.5]dec-3-ylcarbamoyl)phenyl]-1,3-dihydro-2H-pyrrolo[3,4-c]pyridine-2-carboxamide;
N-{4-[(2-oxa-9-azaspiro[5.5]undec-3-ylmethyl)carbamoyl]phenyl}-1,3-dihydro-2H-pyrrolo[3,4-c]pyridine-2-carboxamide;
N-[4-(1-oxa-4,8-diazaspiro[5.5]undec-4-ylcarbonyl)phenyl]-1,3-dihydro-2H-pyrrolo[3,4-c]pyridine-2-carboxamide;
N-[4-(1,8-diazaspiro[4.5]dec-1-ylcarbonyl)phenyl]-1,3-dihydro-2H-pyrrolo[3,4-c]pyridine-2-carboxamide;
N-[4-(1,8-diazaspiro[4.5]dec-8-ylcarbonyl)phenyl]-1,3-dihydro-2H-pyrrolo[3,4-c]pyridine-2-carboxamide;
N-[4-(1,7-diazaspiro[3.5]non-7-ylcarbonyl)phenyl]-1,3-dihydro-2H-pyrrolo[3,4-c]pyridine-2-carboxamide;
N-[4-(1,6-diazaspiro[3.5]non-1-ylcarbonyl)phenyl]-1,3-dihydro-2H-pyrrolo[3,4-c]pyridine-2-carboxamide;
N-[4-(2,5-diazaspiro[3.5]non-2-ylcarbonyl)phenyl]-1,3-dihydro-2H-pyrrolo[3,4-c]pyridine-2-carboxamide;
N-[4-(5-oxa-2-azaspiro[3.4]oct-2-ylcarbonyl)phenyl]-1,3-dihydro-2H-pyrrolo[3,4-c]pyridine-2-carboxamide;
N-[4-(6-oxa-2-azaspiro[3.5]non-2-ylcarbonyl)phenyl]-1,3-dihydro-2H-pyrrolo[3,4-c]pyridine-2-carboxamide;
N-[4-(hexahydro-5H-furo[2,3-c]pyrrol-5-ylcarbonyl)phenyl]-1,3-dihydro-2H-pyrrolo[3,4-c]pyridine-2-carboxamide;
N-[4-(tetrahydro-1H-furo[3,4-c]pyrrol-5(3H)-ylcarbonyl)phenyl]-1,3-dihydro-2H-pyrrolo[3,4-c]pyridine-2-carboxamide;
N-[4-(hexahydrofuro[3,4-c]pyridin-5(3H)-ylcarbonyl)phenyl]-1,3-dihydro-2H-pyrrolo[3,4-c]pyridine-2-carboxamide;
N-{4-[1-(tetrahydrofuran-3-ylacetyl)-1,2,3,6-tetrahydropyridin-4-yl]phenyl}-1,3-dihydro-2H-pyrrolo[3,4-c]pyridine-2-carboxamide;
N-{4-[1-(tetrahydro-2H-pyran-4-ylacetyl)-1,2,3,6-tetrahydropyridin-4-yl]phenyl}-1,3-dihydro-2H-pyrrolo[3,4-c]pyridine-2-carboxamide;
N-{4-[1-(N,N-dimethylglycyl)-1,2,3,6-tetrahydropyridin-4-yl]phenyl}-1,3-dihydro-2H-pyrrolo[3,4-c]pyridine-2-carboxamide;
N-(4-{1-[(4-methylpiperazin-1-yl)acetyl]-1,2,3,6-tetrahydropyridin-4-yl}phenyl)-1,3-dihydro-2H-pyrrolo[3,4-c]pyridine-2-carboxamide;
N-(4-{4-[(tetrahydrofuran-2-ylacetyl)amino]cyclohex-1-en-1-yl}phenyl)-1,3-dihydro-2H-pyrrolo[3,4-c]pyridine-2-carboxamide;
N-(4-{4-[(tetrahydrofuran-3-ylacetyl)amino]cyclohex-1-en-1-yl}phenyl)-1,3-dihydro-2H-pyrrolo[3,4-c]pyridine-2-carboxamide;
N-(4-{4-[(cyclohexylcarbonyl)amino]cyclohex-1-en-1-yl}phenyl)-1,3-dihydro-2H-pyrrolo[3,4-c]pyridine-2-carboxamide;
N-[4-(4-{[(1,1-dioxidotetrahydrothiophen-3-yl)carbonyl]amino}cyclohex-1-en-1-yl)phenyl]-1,3-dihydro-2H-pyrrolo[3,4-c]pyridine-2-carboxamide;
N-[4-(4-{[(4,4-difluorocyclohexyl)carbonyl]amino}cyclohex-1-en-1-yl)phenyl]-1,3-dihydro-2H-pyrrolo[3,4-c]pyridine-2-carboxamide;
N-(4-{4-[(2-hydroxy-2-methylpropanoyl)amino]cyclohex-1-en-1-yl}phenyl)-1,3-dihydro-2H-pyrrolo[3,4-c]pyridine-2-carboxamide;
N-(4-{4-[(tetrahydrofuran-2-ylcarbonyl)amino]cyclohex-1-en-1-yl}phenyl)-1,3-dihydro-2H-pyrrolo[3,4-c]pyridine-2-carboxamide;
N-[4-(piperidin-1-ylsulfonyl)phenyl]-1,3-dihydro-2H-pyrrolo[3,4-c]pyridine-2-carboxamide;
5-fluoro-N-(4-{[1-(1,3-thiazol-2-yl)propan-2-yl]carbamoyl}phenyl)-1,3-dihydro-2H-isoindole-2-carboxamide;
N-{4-[(4,4-difluorocyclohexyl)carbamoyl]phenyl}-5-fluoro-1,3-dihydro-2H-isoindole-2-carboxamide;
N-(4-{[1-(3,5-dimethyl-1H-pyrazol-1-yl)propan-2-yl]carbamoyl}phenyl)-5-fluoro-1,3-dihydro-2H-isoindole-2-carboxamide;
5-fluoro-N-(4-{[2-methyl-2-(morpholin-4-yl)butyl]carbamoyl}phenyl)-1,3-dihydro-2H-isoindole-2-carboxamide;
5-fluoro-N-(4-{[2-(2-methyl-1,3-thiazol-4-yl)ethyl]carbamoyl}phenyl)-1,3-dihydro-2H-isoindole-2-carboxamide;
5-fluoro-N-(4-{[2-methyl-1-(morpholin-4-yl)propan-2-yl]carbamoyl}phenyl)-1,3-dihydro-2H-isoindole-2-carboxamide;
5-fluoro-N-{4-[(4-methoxybenzyl)carbamoyl]phenyl}-1,3-dihydro-2H-isoindole-2-carboxamide;
5-fluoro-N-(4-{[3-(morpholin-4-yl)propyl]carbamoyl}phenyl)-1,3-dihydro-2H-isoindole-2-carboxamide;
Nalpha-(4-{[(5-fluoro-1,3-dihydro-2H-isoindol-2-yl)carbonyl]amino}benzoyl)-D-phenylalaninamide;
N-(4-{[2-(acetylamino)phenyl]carbamoyl}phenyl)-5-fluoro-1,3-dihydro-2H-isoindole-2-carboxamide;
5-fluoro-N-[4-({4-[2-(2-hydroxyethoxy)ethyl]piperazin-1-yl}carbonyl)phenyl]-1,3-dihydro-2H-isoindole-2-carboxamide;
5-fluoro-N-(4-{[2-(furan-2-yl)-2-(pyrrolidin-1-yl)ethyl]carbamoyl}phenyl)-1,3-dihydro-2H-isoindole-2-carboxamide;
N-{4-[bis(2-methoxyethyl)carbamoyl]phenyl}-5-fluoro-1,3-dihydro-2H-isoindole-2-carboxamide;
N-{4-[(1-amino-1-oxohexan-2-yl)carbamoyl]phenyl}-5-fluoro-1,3-dihydro-2H-isoindole-2-carboxamide;
N-(4-{[2-(3,4-dimethoxyphenyl)ethyl]carbamoyl}phenyl)-5-fluoro-1,3-dihydro-2H-isoindole-2-carboxamide;
N-(4-{[(2S)-3,3-dimethyl-1-(methylamino)-1-oxobutan-2-yl]carbamoyl}phenyl)-5-fluoro-1,3-dihydro-2H-isoindole-2-carboxamide;
Nalpha-(4-{[(5-fluoro-1,3-dihydro-2H-isoindol-2-yl)carbonyl]amino}benzoyl)-L-phenylalaninamide;

N-(4-{[(2R)-1-amino-4-methyl-1-oxopentan-2-yl]carbamoyl}phenyl)-5-fluoro-1,3-dihydro-2H-isoindole-2-carboxamide;

N-{4-[(4-cyclohexylpiperazin-1-yl)carbonyl]phenyl}-5-fluoro-1,3-dihydro-2H-isoindole-2-carboxamide;

5-fluoro-N-(4-{[3-(methylcarbamoyl)phenyl]carbamoyl}phenyl)-1,3-dihydro-2H-isoindole-2-carboxamide;

N-{4-[(2-amino-2-oxo-1-phenylethyl)carbamoyl]phenyl}-5-fluoro-1,3-dihydro-2H-isoindole-2-carboxamide;

N-{4-[(3-tert-butoxypropyl)carbamoyl]phenyl}-5-fluoro-1,3-dihydro-2H-isoindole-2-carboxamide;

N-(4-{[2-(2,6-dimethylmorpholin-4-yl)ethyl]carbamoyl}phenyl)-5-fluoro-1,3-dihydro-2H-isoindole-2-carboxamide;

N-(4-{[(1R)-2-amino-2-oxo-1-phenylethyl]carbamoyl}phenyl)-5-fluoro-1,3-dihydro-2H-isoindole-2-carboxamide;

5-fluoro-N-{4-[(3-methoxybenzyl)carbamoyl]phenyl}-1,3-dihydro-2H-isoindole-2-carboxamide;

N-(4-{[2-(3,5-dimethyl-1H-pyrazol-1-yl)ethyl]carbamoyl}phenyl)-5-fluoro-1,3-dihydro-2H-isoindole-2-carboxamide;

5-fluoro-N-(4-{[2-methyl-2-(morpholin-4-yl)propyl]carbamoyl}phenyl)-1,3-dihydro-2H-isoindole-2-carboxamide;

5-fluoro-N-(4-{[(3S)-1-methyl-2-oxoazepan-3-yl]carbamoyl}phenyl)-1,3-dihydro-2H-isoindole-2-carboxamide;

5-fluoro-N-(4-{[2-(4-methylpiperazin-1-yl)ethyl]carbamoyl}phenyl)-1,3-dihydro-2H-isoindole-2-carboxamide;

5-fluoro-N-(4-{[4-(morpholin-4-yl)benzyl]carbamoyl}phenyl)-1,3-dihydro-2H-isoindole-2-carboxamide;

5-fluoro-N-(4-{[3-(piperidin-1-yl)propyl]carbamoyl}phenyl)-1,3-dihydro-2H-isoindole-2-carboxamide;

N-(4-{[3-(5-methyl-1H-pyrazol-1-yl)propyl]carbamoyl}phenyl)-5,7-dihydro-6H-pyrrolo[3,4-b]pyridine-6-carboxamide;

N-(4-{[2-(4-chloro-1H-pyrazol-1-yl)ethyl]carbamoyl}phenyl)-5,7-dihydro-6H-pyrrolo[3,4-b]pyridine-6-carboxamide;

N-(4-{[1-(3,5-dimethyl-1H-pyrazol-1-yl)propan-2-yl]carbamoyl}phenyl)-5,7-dihydro-6H-pyrrolo[3,4-b]pyridine-6-carboxamide;

N-(4-{[2-methyl-2-(morpholin-4-yl)butyl]carbamoyl}phenyl)-5,7-dihydro-6H-pyrrolo[3,4-b]pyridine-6-carboxamide;

N-{4-[(4-methoxybenzyl)carbamoyl]phenyl}-5,7-dihydro-6H-pyrrolo[3,4-b]pyridine-6-carboxamide;

N-(4-{[3-(morpholin-4-yl)propyl]carbamoyl}phenyl)-5,7-dihydro-6H-pyrrolo[3,4-b]pyridine-6-carboxamide;

N-[4-({4-[2-(2-hydroxyethoxy)ethyl]piperazin-1-yl}carbonyl)phenyl]-5,7-dihydro-6H-pyrrolo[3,4-b]pyridine-6-carboxamide;

N-{4-[(2-carbamoylbenzyl)carbamoyl]phenyl}-5,7-dihydro-6H-pyrrolo[3,4-b]pyridine-6-carboxamide;

N-{4-[bis(2-methoxyethyl)carbamoyl]phenyl}-5,7-dihydro-6H-pyrrolo[3,4-b]pyridine-6-carboxamide;

N-{4-[(1-amino-1-oxohexan-2-yl)carbamoyl]phenyl}-5,7-dihydro-6H-pyrrolo[3,4-b]pyridine-6-carboxamide;

N-(4-{[2-(3,4-dimethoxyphenyl)ethyl]carbamoyl}phenyl)-5,7-dihydro-6H-pyrrolo[3,4-b]pyridine-6-carboxamide;

N-(4-{[4-(pyrazin-2-yl)piperazin-1-yl]carbonyl}phenyl)-5,7-dihydro-6H-pyrrolo[3,4-b]pyridine-6-carboxamide;

Nalpha-{4-[(5,7-dihydro-6H-pyrrolo[3,4-b]pyridin-6-ylcarbonyl)amino]benzoyl}-L-phenylalaninamide;

N-(4-{[(2R)-1-amino-4-methyl-1-oxopentan-2-yl]carbamoyl}phenyl)-5,7-dihydro-6H-pyrrolo[3,4-b]pyridine-6-carboxamide;

N-{4-[(4-cyclohexylpiperazin-1-yl)carbonyl]phenyl}-5,7-dihydro-6H-pyrrolo[3,4-b]pyridine-6-carboxamide;

N-{4-[(3-tert-butoxypropyl)carbamoyl]phenyl}-5,7-dihydro-6H-pyrrolo[3,4-b]pyridine-6-carboxamide;

N-(4-{[2-(2,6-dimethylmorpholin-4-yl)ethyl]carbamoyl}phenyl)-5,7-dihydro-6H-pyrrolo[3,4-b]pyridine-6-carboxamide;

N-{4-[(3-methoxybenzyl)carbamoyl]phenyl}-5,7-dihydro-6H-pyrrolo[3,4-b]pyridine-6-carboxamide;

N-(4-{[2-methyl-2-(morpholin-4-yl)propyl]carbamoyl}phenyl)-5,7-dihydro-6H-pyrrolo[3,4-b]pyridine-6-carboxamide;

N-(4-{[(3S)-1-methyl-2-oxoazepan-3-yl]carbamoyl}phenyl)-5,7-dihydro-6H-pyrrolo[3,4-b]pyridine-6-carboxamide;

N-(4-{[2-(4-methylpiperazin-1-yl)ethyl]carbamoyl}phenyl)-5,7-dihydro-6H-pyrrolo[3,4-b]pyridine-6-carboxamide;

N-(4-{[4-(morpholin-4-yl)benzyl]carbamoyl}phenyl)-5,7-dihydro-6H-pyrrolo[3,4-b]pyridine-6-carboxamide;

N-(4-{[3-(piperidin-1-yl)propyl]carbamoyl}phenyl)-5,7-dihydro-6H-pyrrolo[3,4-b]pyridine-6-carboxamide;

N-[4-(4,5,6,7-tetrahydro-1H-indazol-5-ylcarbamoyl)phenyl]-5,7-dihydro-6H-pyrrolo[3,4-b]pyridine-6-carboxamide;

5-fluoro-N-{4-[(3-methoxy-2,2-dimethylpropyl)carbamoyl]phenyl}-1,3-dihydro-2H-isoindole-2-carboxamide;

N-{4-[(3,3-dimethylbutyl)carbamoyl]phenyl}-5-fluoro-1,3-dihydro-2H-isoindole-2-carboxamide;

5-fluoro-N-(4-{[1-(furan-2-yl)propan-2-yl]carbamoyl}phenyl)-1,3-dihydro-2H-isoindole-2-carboxamide;

5-fluoro-N-(4-{[(3-methyl-1,2-oxazol-5-yl)methyl]carbamoyl}phenyl)-1,3-dihydro-2H-isoindole-2-carboxamide;

N-(4-{[(2R)-1-cyanobutan-2-yl]carbamoyl}phenyl)-5-fluoro-1,3-dihydro-2H-isoindole-2-carboxamide;

N-{4-[(2R)-butan-2-ylcarbamoyl]phenyl}-5-fluoro-1,3-dihydro-2H-isoindole-2-carboxamide;

5-fluoro-N-(4-{[2-(1H-pyrazol-1-yl)ethyl]carbamoyl}phenyl)-1,3-dihydro-2H-isoindole-2-carboxamide;

5-fluoro-N-{4-[methyl(3-methylbutyl)carbamoyl]phenyl}-1,3-dihydro-2H-isoindole-2-carboxamide;

N-(4-{[1-(ethylamino)-1-oxopropan-2-yl]carbamoyl}phenyl)-5-fluoro-1,3-dihydro-2H-isoindole-2-carboxamide;

5-fluoro-N-(4-{[(1-methyl-1H-pyrazol-3-yl)methyl]carbamoyl}phenyl)-1,3-dihydro-2H-isoindole-2-carboxamide;

5-fluoro-N-{4-[(2-methoxybutyl)carbamoyl]phenyl}-1,3-dihydro-2H-isoindole-2-carboxamide;

N-(4-{[4-(dimethylamino)butyl]carbamoyl}phenyl)-5-fluoro-1,3-dihydro-2H-isoindole-2-carboxamide;

5-fluoro-N-{4-[(3S)-tetrahydrofuran-3-ylcarbamoyl]phenyl}-1,3-dihydro-2H-isoindole-2-carboxamide;

5-fluoro-N-{4-[(1-methoxybutan-2-yl)carbamoyl]phenyl}-1,3-dihydro-2H-isoindole-2-carboxamide;

N-{4-[(2-ethoxypropyl)carbamoyl]phenyl}-5-fluoro-1,3-dihydro-2H-isoindole-2-carboxamide;

N-{4-[benzyl(methyl)carbamoyl]phenyl}-5-fluoro-1,3-dihydro-2H-isoindole-2-carboxamide;

N-{4-[(2S)-butan-2-ylcarbamoyl]phenyl}-5-fluoro-1,3-dihydro-2H-isoindole-2-carboxamide;
5-fluoro-N-(4-{[2-(5-methyl-1H-pyrazol-1-yl)ethyl]carbamoyl}phenyl)-1,3-dihydro-2H-isoindole-2-carboxamide;
5-fluoro-N-(4-{[2-(3-methyl-1H-pyrazol-1-yl)ethyl]carbamoyl}phenyl)-1,3-dihydro-2H-isoindole-2-carboxamide;
5-fluoro-N-{4-[(2-methylpropyl)carbamoyl]phenyl}-1,3-dihydro-2H-isoindole-2-carboxamide;
5-fluoro-N-{4-[(pyridin-3-ylmethyl)carbamoyl]phenyl}-1,3-dihydro-2H-isoindole-2-carboxamide;
5-fluoro-N-{4-[(tetrahydrofuran-2-ylmethyl)carbamoyl]phenyl}-1,3-dihydro-2H-isoindole-2-carboxamide;
N-(4-{[(1R)-1-cyclopropylethyl]carbamoyl}phenyl)-5-fluoro-1,3-dihydro-2H-isoindole-2-carboxamide;
5-fluoro-N-(4-{[1-(1-methylcyclopropyl)ethyl]carbamoyl}phenyl)-1,3-dihydro-2H-isoindole-2-carboxamide;
5-fluoro-N-{4-[(thiophen-2-ylmethyl)carbamoyl]phenyl}-1,3-dihydro-2H-isoindole-2-carboxamide;
N-(4-{[(1S)-1-cyclopropylethyl]carbamoyl}phenyl)-5-fluoro-1,3-dihydro-2H-isoindole-2-carboxamide;
5-fluoro-N-{4-[(4-methoxybutyl)carbamoyl]phenyl}-1,3-dihydro-2H-isoindole-2-carboxamide;
5-fluoro-N-(4-{[(5-methyl-1,3-oxazol-2-yl)methyl]carbamoyl}phenyl)-1,3-dihydro-2H-isoindole-2-carboxamide;
5-fluoro-N-(4-{[2-(tetrahydro-2H-pyran-3-yl)ethyl]carbamoyl}phenyl)-1,3-dihydro-2H-isoindole-2-carboxamide;
5-fluoro-N-(4-{[(2S)-1-methoxypropan-2-yl]carbamoyl}phenyl)-1,3-dihydro-2H-isoindole-2-carboxamide;
N-{4-[(3,3-dimethyl-2-oxobutyl)carbamoyl]phenyl}-5-fluoro-1,3-dihydro-2H-isoindole-2-carboxamide;
5-fluoro-N-(4-{[(1-methyl-1H-pyrrol-2-yl)methyl]carbamoyl}phenyl)-1,3-dihydro-2H-isoindole-2-carboxamide;
5-fluoro-N-(4-{[2-(propan-2-yloxy)ethyl]carbamoyl}phenyl)-1,3-dihydro-2H-isoindole-2-carboxamide;
N-(4-{[3-(dimethylamino)propyl]carbamoyl}phenyl)-5-fluoro-1,3-dihydro-2H-isoindole-2-carboxamide;
N-(4-{[(2S)-1-amino-1-oxobutan-2-yl]carbamoyl}phenyl)-5-fluoro-1,3-dihydro-2H-isoindole-2-carboxamide;
5-fluoro-N-[4-(tetrahydro-2H-pyran-3-ylcarbamoyl)phenyl]-1,3-dihydro-2H-isoindole-2-carboxamide;
5-fluoro-N-(4-{[2-(1H-pyrrol-1-yl)ethyl]carbamoyl}phenyl)-1,3-dihydro-2H-isoindole-2-carboxamide;
5-fluoro-N-{4-[(1-methoxypropan-2-yl)carbamoyl]phenyl}-1,3-dihydro-2H-isoindole-2-carboxamide;
5-fluoro-N-{4-[(2-methoxyethyl)carbamoyl]phenyl}-1,3-dihydro-2H-isoindole-2-carboxamide;
N-[4-(cyclopentylcarbamoyl)phenyl]-5-fluoro-1,3-dihydro-2H-isoindole-2-carboxamide;
5-fluoro-N-(4-{[(2S)-3-methylbutan-2-yl]carbamoyl}phenyl)-1,3-dihydro-2H-isoindole-2-carboxamide;
5-fluoro-N-(4-{[(2R)-3-methylbutan-2-yl]carbamoyl}phenyl)-1,3-dihydro-2H-isoindole-2-carboxamide;
5-fluoro-N-(4-{[(2S)-2-methylbutyl]carbamoyl}phenyl)-1,3-dihydro-2H-isoindole-2-carboxamide;
5-fluoro-N-{4-[(2-hydroxy-2-methylpropyl)carbamoyl]phenyl}-1,3-dihydro-2H-isoindole-2-carboxamide;
5-fluoro-N-(4-{[2-(tetrahydro-2H-pyran-4-yl)ethyl]carbamoyl}phenyl)-1,3-dihydro-2H-isoindole-2-carboxamide;
N-[4-(butylcarbamoyl)phenyl]-5-fluoro-1,3-dihydro-2H-isoindole-2-carboxamide;
5-fluoro-N-{4-[methyl(tetrahydrofuran-2-ylmethyl)carbamoyl]phenyl}-1,3-dihydro-2H-isoindole-2-carboxamide;
5-fluoro-N-{4-[(2-methoxyethyl)(methyl)carbamoyl]phenyl}-1,3-dihydro-2H-isoindole-2-carboxamide;
N-{4-[(1-cyanoethyl)carbamoyl]phenyl}-5-fluoro-1,3-dihydro-2H-isoindole-2-carboxamide;
5-fluoro-N-(4-{[(5-methyl-1,2-oxazol-3-yl)methyl]carbamoyl}phenyl)-1,3-dihydro-2H-isoindole-2-carboxamide;
5-fluoro-N-{4-[(3R)-tetrahydrofuran-3-ylcarbamoyl]phenyl}-1,3-dihydro-2H-isoindole-2-carboxamide;
N-{4-[(3-methoxy-2,2-dimethylpropyl)carbamoyl]phenyl}-5,7-dihydro-6H-pyrrolo[3,4-b]pyridine-6-carboxamide;
N-{4-[(3,3-dimethylbutyl)carbamoyl]phenyl}-5,7-dihydro-6H-pyrrolo[3,4-b]pyridine-6-carboxamide;
N-(4-{[1-(furan-2-yl)propan-2-yl]carbamoyl}phenyl)-5,7-dihydro-6H-pyrrolo[3,4-b]pyridine-6-carboxamide;
N-(4-{[(3-methyl-1,2-oxazol-5-yl)methyl]carbamoyl}phenyl)-5,7-dihydro-6H-pyrrolo[3,4-b]pyridine-6-carboxamide;
N-(4-{[(2R)-1-cyanobutan-2-yl]carbamoyl}phenyl)-5,7-dihydro-6H-pyrrolo[3,4-b]pyridine-6-carboxamide;
N-{4-[methyl(3-methylbutyl)carbamoyl]phenyl}-5,7-dihydro-6H-pyrrolo[3,4-b]pyridine-6-carboxamide;
N-(4-{[(1-methyl-1H-pyrazol-3-yl)methyl]carbamoyl}phenyl)-5,7-dihydro-6H-pyrrolo[3,4-b]pyridine-6-carboxamide;
N-{4-[(2-methoxybutyl)carbamoyl]phenyl}-5,7-dihydro-6H-pyrrolo[3,4-b]pyridine-6-carboxamide;
N-(4-{[4-(dimethylamino)butyl]carbamoyl}phenyl)-5,7-dihydro-6H-pyrrolo[3,4-b]pyridine-6-carboxamide;
N-(4-{[1-(1,3-thiazol-2-yl)ethyl]carbamoyl}phenyl)-5,7-dihydro-6H-pyrrolo[3,4-b]pyridine-6-carboxamide;
N-(4-{[1-(1-methyl-1H-pyrazol-4-yl)ethyl]carbamoyl}phenyl)-5,7-dihydro-6H-pyrrolo[3,4-b]pyridine-6-carboxamide;
N-{4-[(3S)-tetrahydrofuran-3-ylcarbamoyl]phenyl}-5,7-dihydro-6H-pyrrolo[3,4-b]pyridine-6-carboxamide;
N-{4-[(1-methoxybutan-2-yl)carbamoyl]phenyl}-5,7-dihydro-6H-pyrrolo[3,4-b]pyridine-6-carboxamide;
N-{4-[(4-aminobenzyl)carbamoyl]phenyl}-5,7-dihydro-6H-pyrrolo[3,4-b]pyridine-6-carboxamide;
N-{4-[(2-ethoxypropyl)carbamoyl]phenyl}-5,7-dihydro-6H-pyrrolo[3,4-b]pyridine-6-carboxamide;
N-{4-[(6-methoxypyridin-3-yl)carbamoyl]phenyl}-5,7-dihydro-6H-pyrrolo[3,4-b]pyridine-6-carboxamide;
N-{4-[(2S)-butan-2-ylcarbamoyl]phenyl}-5,7-dihydro-6H-pyrrolo[3,4-b]pyridine-6-carboxamide;
N-{4-[(1-cyanocyclopropyl)carbamoyl]phenyl}-5,7-dihydro-6H-pyrrolo[3,4-b]pyridine-6-carboxamide;
N-(4-{[2-(5-methyl-1H-pyrazol-1-yl)ethyl]carbamoyl}phenyl)-5,7-dihydro-6H-pyrrolo[3,4-b]pyridine-6-carboxamide;
N-(4-{[(4-methyl-1,3-thiazol-2-yl)methyl]carbamoyl}phenyl)-5,7-dihydro-6H-pyrrolo[3,4-b]pyridine-6-carboxamide;
N-{4-[(3-hydroxypropyl)carbamoyl]phenyl}-5,7-dihydro-6H-pyrrolo[3,4-b]pyridine-6-carboxamide;
N-{4-[(2-methylpropyl)carbamoyl]phenyl}-5,7-dihydro-6H-pyrrolo[3,4-b]pyridine-6-carboxamide;
N-{4-[(tetrahydrofuran-2-ylmethyl)carbamoyl]phenyl}-5,7-dihydro-6H-pyrrolo[3,4-b]pyridine-6-carboxamide;

N-(4-{[(1R)-1-cyclopropylethyl]carbamoyl}phenyl)-5,7-dihydro-6H-pyrrolo[3,4-b]pyridine-6-carboxamide;
N-(4-{[1-(1-methylcyclopropyl)ethyl]carbamoyl}phenyl)-5,7-dihydro-6H-pyrrolo[3,4-b]pyridine-6-carboxamide;
N-{4-[(thiophen-2-ylmethyl)carbamoyl]phenyl}-5,7-dihydro-6H-pyrrolo[3,4-b]pyridine-6-carboxamide;
N-(4-{[(1S)-1-cyclopropylethyl]carbamoyl}phenyl)-5,7-dihydro-6H-pyrrolo[3,4-b]pyridine-6-carboxamide;
N-{4-[(4-methoxybutyl)carbamoyl]phenyl}-5,7-dihydro-6H-pyrrolo[3,4-b]pyridine-6-carboxamide;
N-(4-{[2-(tetrahydro-2H-pyran-3-yl)ethyl]carbamoyl}phenyl)-5,7-dihydro-6H-pyrrolo[3,4-b]pyridine-6-carboxamide;
N-(4-{[(2S)-1-methoxypropan-2-yl]carbamoyl}phenyl)-5,7-dihydro-6H-pyrrolo[3,4-b]pyridine-6-carboxamide;
N-{4-[(3,3-dimethyl-2-oxobutyl)carbamoyl]phenyl}-5,7-dihydro-6H-pyrrolo[3,4-b]pyridine-6-carboxamide;
N-(4-{[(1-methyl-1H-pyrrol-2-yl)methyl]carbamoyl}phenyl)-5,7-dihydro-6H-pyrrolo[3,4-b]pyridine-6-carboxamide;
N-(4-{[2-(propan-2-yloxy)ethyl]carbamoyl}phenyl)-5,7-dihydro-6H-pyrrolo[3,4-b]pyridine-6-carboxamide;
N-(4-{[3-(dimethylamino)propyl]carbamoyl}phenyl)-5,7-dihydro-6H-pyrrolo[3,4-b]pyridine-6-carboxamide;
N-[4-(tetrahydro-2H-pyran-3-ylcarbamoyl)phenyl]-5,7-dihydro-6H-pyrrolo[3,4-b]pyridine-6-carboxamide;
N-(4-{[2-(1H-pyrrol-1-yl)ethyl]carbamoyl}phenyl)-5,7-dihydro-6H-pyrrolo[3,4-b]pyridine-6-carboxamide;
N-{4-[(1-methoxypropan-2-yl)carbamoyl]phenyl}-5,7-dihydro-6H-pyrrolo[3,4-b]pyridine-6-carboxamide;
N-{4-[(3-aminobenzyl)carbamoyl]phenyl}-5,7-dihydro-6H-pyrrolo[3,4-b]pyridine-6-carboxamide;
N-(4-{[(2R)-3-methylbutan-2-yl]carbamoyl}phenyl)-5,7-dihydro-6H-pyrrolo[3,4-b]pyridine-6-carboxamide;
N-{4-[(tetrahydro-2H-pyran-3-ylmethyl)carbamoyl]phenyl}-5,7-dihydro-6H-pyrrolo[3,4-b]pyridine-6-carboxamide;
N-{4-[(2-hydroxy-2-methylpropyl)carbamoyl]phenyl}-5,7-dihydro-6H-pyrrolo[3,4-b]pyridine-6-carboxamide;
N-[4-(butylcarbamoyl)phenyl]-5,7-dihydro-6H-pyrrolo[3,4-b]pyridine-6-carboxamide;
N-{4-[methyl(tetrahydrofuran-2-ylmethyl)carbamoyl]phenyl}-5,7-dihydro-6H-pyrrolo[3,4-b]pyridine-6-carboxamide;
N-{4-[(2-methoxyethyl)(methyl)carbamoyl]phenyl}-5,7-dihydro-6H-pyrrolo[3,4-b]pyridine-6-carboxamide;
N-{4-[(1-cyanoethyl)carbamoyl]phenyl}-5,7-dihydro-6H-pyrrolo[3,4-b]pyridine-6-carboxamide;
N-{4-[(3R)-tetrahydrofuran-3-ylcarbamoyl]phenyl}-5,7-dihydro-6H-pyrrolo[3,4-b]pyridine-6-carboxamide;
N-{4-[(cyclopentylmethyl)carbamoyl]phenyl}-5,7-dihydro-6H-pyrrolo[3,4-b]pyridine-6-carboxamide;
N-{4-[(2-methoxy-2-methylpropyl)carbamoyl]phenyl}-5,7-dihydro-6H-pyrrolo[3,4-b]pyridine-6-carboxamide;
N-{4-[(cyclopropylmethyl)carbamoyl]phenyl}-5,7-dihydro-6H-pyrrolo[3,4-b]pyridine-6-carboxamide;
N-{4-[methyl(propyl)carbamoyl]phenyl}-5,7-dihydro-6H-pyrrolo[3,4-b]pyridine-6-carboxamide;
N-{4-[(pyridin-4-ylmethyl)carbamoyl]phenyl}-5,7-dihydro-6H-pyrrolo[3,4-b]pyridine-6-carboxamide;
methyl 1-{4-[(1,3-dihydro-2H-pyrrolo[3,4-c]pyridin-2-ylcarbonyl)amino]phenyl}azetidine-3-carboxylate;
N-(4-{3-[(3-methylbutyl)carbamoyl]azetidin-1-yl}phenyl)-1,3-dihydro-2H-pyrrolo[3,4-c]pyridine-2-carboxamide;
N-(4-{3-[(tetrahydrofuran-2-ylmethyl)carbamoyl]azetidin-1-yl}phenyl)-1,3-dihydro-2H-pyrrolo[3,4-c]pyridine-2-carboxamide;
N-(4-{3-[(tetrahydro-2H-pyran-4-ylmethyl)carbamoyl]azetidin-1-yl}phenyl)-1,3-dihydro-2H-pyrrolo[3,4-c]pyridine-2-carboxamide;
N-{4-[3-(benzylcarbamoyl)azetidin-1-yl]phenyl}-1,3-dihydro-2H-pyrrolo[3,4-c]pyridine-2-carboxamide;
N-{4-[3-(cyclopentylcarbamoyl)azetidin-1-yl]phenyl}-1,3-dihydro-2H-pyrrolo[3,4-c]pyridine-2-carboxamide;
N-(4-{3-[(cyclopentylmethyl)carbamoyl]azetidin-1-yl}phenyl)-1,3-dihydro-2H-pyrrolo[3,4-c]pyridine-2-carboxamide;
N-(4-{3-[(2-methoxyethyl)carbamoyl]azetidin-1-yl}phenyl)-1,3-dihydro-2H-pyrrolo[3,4-c]pyridine-2-carboxamide;
N-{4-[1-(3-methylbutanoyl)-1,2,3,6-tetrahydropyridin-4-yl]phenyl}-1,3-dihydro-2H-pyrrolo[3,4-c]pyridine-2-carboxamide;
N-{4-[1-(cyclopentylacetyl)-1,2,3,6-tetrahydropyridin-4-yl]phenyl}-1,3-dihydro-2H-pyrrolo[3,4-c]pyridine-2-carboxamide;
N-{4-[1-(tetrahydro furan-2-ylacetyl)-1,2,3,6-tetrahydropyridin-4-yl]phenyl}-1,3-dihydro-2H-pyrrolo[3,4-c]pyridine-2-carboxamide;
N-{4-[1-(tetrahydro-2H-pyran-2-ylacetyl)-1,2,3,6-tetrahydropyridin-4-yl]phenyl}-1,3-dihydro-2H-pyrrolo[3,4-c]pyridine-2-carboxamide;
N-{4-[1-(pyrrolidin-1-ylacetyl)-1,2,3,6-tetrahydropyridin-4-yl]phenyl}-1,3-dihydro-2H-pyrrolo[3,4-c]pyridine-2-carboxamide;
N-{4-[1-(pyrazin-2-ylcarbonyl)-1,2,3,6-tetrahydropyridin-4-yl]phenyl}-1,3-dihydro-2H-pyrrolo[3,4-c]pyridine-2-carboxamide;
N-{4-[(3-methoxy-2,2-dimethylpropyl)carbamoyl]phenyl}-1,3-dihydro-2H-isoindole-2-carboxamide;
N-{4-[(4,4-difluorocyclohexyl)carbamoyl]phenyl}-1,3-dihydro-2H-isoindole-2-carboxamide;
N-(4-{[(2R)-1-cyanobutan-2-yl]carbamoyl}phenyl)-1,3-dihydro-2H-isoindole-2-carboxamide;
N-{4-[(2-methoxybutyl)carbamoyl]phenyl}-1,3-dihydro-2H-isoindole-2-carboxamide;
N-(4-{[1-(ethylamino)-1-oxopropan-2-yl]carbamoyl}phenyl)-1,3-dihydro-2H-isoindole-2-carboxamide;
N-(4-{[2-methyl-2-(morpholin-4-yl)butyl]carbamoyl}phenyl)-1,3-dihydro-2H-isoindole-2-carboxamide;
N-(4-{[(1R)-1-cyclopropylethyl]carbamoyl}phenyl)-1,3-dihydro-2H-isoindole-2-carboxamide;
N-(4-{[(1S)-1-cyclopropylethyl]carbamoyl}phenyl)-1,3-dihydro-2H-isoindole-2-carboxamide;
N-(6-{[(2S)-tetrahydrofuran-2-ylmethyl]carbamoyl}pyridazin-3-yl)-1,3-dihydro-2H-isoindole-2-carboxamide;
N-{4-[(3S)-tetrahydrofuran-3-ylcarbamoyl]phenyl}-1,3-dihydro-2H-isoindole-2-carboxamide;
N-(4-{[2-(tetrahydro-2H-pyran-3-yl)ethyl]carbamoyl}phenyl)-1,3-dihydro-2H-isoindole-2-carboxamide;
N-(4-{[(5-methyl-1,3-oxazol-2-yl)methyl]carbamoyl}phenyl)-1,3-dihydro-2H-isoindole-2-carboxamide;
N-[4-({2-[(dimethylamino)methyl]benzyl}carbamoyl)phenyl]-1,3-dihydro-2H-isoindole-2-carboxamide;
N-(4-{[(1R)-2-amino-2-oxo-1-phenylethyl]carbamoyl}phenyl)-1,3-dihydro-2H-isoindole-2-carboxamide;
N-[4-(1,3-oxazol-2-ylcarbamoyl)phenyl]-1,3-dihydro-2H-isoindole-2-carboxamide;

N-[4-(tetrahydro-2H-pyran-3-ylcarbamoyl)phenyl]-1,3-dihydro-2H-isoindole-2-carboxamide;
N-(4-{[2-(2,6-dimethylmorpholin-4-yl)ethyl]carbamoyl}phenyl)-1,3-dihydro-2H-isoindole-2-carboxamide;
N-(4-{[1-(1-methylcyclopropyl)ethyl]carbamoyl}phenyl)-1,3-dihydro-2H-isoindole-2-carboxamide;
N-(4-{[2-(furan-2-yl)-2-(pyrrolidin-1-yl)ethyl]carbamoyl}phenyl)-1,3-dihydro-2H-isoindole-2-carboxamide;
N-(4-{1-[(2S)-tetrahydrofuran-2-ylcarbonyl]piperidin-4-yl}phenyl)-1,3-dihydro-2H-pyrrolo[3,4-c]pyridine-2-carboxamide;
N-(4-{1-[(3S)-tetrahydrofuran-3-ylcarbonyl]piperidin-4-yl}phenyl)-1,3-dihydro-2H-pyrrolo[3,4-c]pyridine-2-carboxamide;
5-cyano-N-{4-[1-(tetrahydrofuran-3-ylcarbonyl)-1,2,3,6-tetrahydropyridin-4-yl]phenyl}-1,3-dihydro-2H-isoindole-2-carboxamide;
5-cyano-N-{4-[1-(tetrahydro-2H-pyran-4-ylcarbonyl)-1,2,3,6-tetrahydropyridin-4-yl]phenyl}-1,3-dihydro-2H-isoindole-2-carboxamide;
5-cyano-N-{4-[1-(2-hydroxy-2-methylpropanoyl)-1,2,3,6-tetrahydropyridin-4-yl]phenyl}-1,3-dihydro-2H-isoindole-2-carboxamide;
5-cyano-N-{4-[1-(morpholin-4-ylacetyl)-1,2,3,6-tetrahydropyridin-4-yl]phenyl}-1,3-dihydro-2H-isoindole-2-carboxamide;
N-{4-[(4-fluorobenzyl)(3-methylbutanoyl)amino]butyl}-1,3-dihydro-2H-isoindole-2-carboxamide;
N-[4-(9-chloro-5-oxo-2,3,3a,4,4a,5-hexahydro-6H-furo[2',3',2,3]cyclobuta[1,2-c]quinolin-6-yl)butyl]-1,3-dihydro-2H-pyrrolo[3,4-c]pyridine-2-carboxamide;
N-{4-[7-chloro-1-(2-hydroxyethyl)-3-oxo-1,3-dihydrocyclobuta[c]quinolin-4(2H)-yl]butyl}-1,3-dihydro-2H-pyrrolo[3,4-c]pyridine-2-carboxamide;
N-(4-{[1-(tetrahydro-2H-pyran-2-ylcarbonyl)azetidin-3-yl]oxy}phenyl)-1,3-dihydro-2H-pyrrolo[3,4-c]pyridine-2-carboxamide;
N-(4-{[1-(tetrahydro-2H-pyran-2-ylcarbonyl)pyrrolidin-3-yl]oxy}phenyl)-1,3-dihydro-2H-pyrrolo[3,4-c]pyridine-2-carboxamide;
N-(6-{[(2R)-tetrahydrofuran-2-ylmethyl]carbamoyl}pyridazin-3-yl)-1,3-dihydro-2H-isoindole-2-carboxamide;
N-(4-{4-[(cyclopropylacetyl)amino]cyclohex-1-en-1-yl}phenyl)-1,3-dihydro-2H-pyrrolo[3,4-c]pyridine-2-carboxamide;
N-{4-[(1-acetylpiperidin-3-yl)oxy]phenyl}-1,3-dihydro-2H-pyrrolo[3,4-c]pyridine-2-carboxamide;
N-{4-[(1-butanoylpiperidin-3-yl)oxy]phenyl}-1,3-dihydro-2H-pyrrolo[3,4-c]pyridine-2-carboxamide;
N-(4-{[1-(3-methylbutanoyl)piperidin-3-yl]oxy}phenyl)-1,3-dihydro-2H-pyrrolo[3,4-c]pyridine-2-carboxamide;
N-(4-{[1-(methoxyacetyl)piperidin-3-yl]oxy}phenyl)-1,3-dihydro-2H-pyrrolo[3,4-c]pyridine-2-carboxamide;
N-(4-{[1-(2-methylbutanoyl)piperidin-3-yl]oxy}phenyl)-1,3-dihydro-2H-pyrrolo[3,4-c]pyridine-2-carboxamide;
N-(4-{[1-(3,3,3-trifluoropropanoyl)piperidin-3-yl]oxy}phenyl)-1,3-dihydro-2H-pyrrolo[3,4-c]pyridine-2-carboxamide;
N-(4-{[1-(cyclopropylacetyl)piperidin-3-yl]oxy}phenyl)-1,3-dihydro-2H-pyrrolo[3,4-c]pyridine-2-carboxamide;
N-(4-{[1-(cyclobutylcarbonyl)piperidin-3-yl]oxy}phenyl)-1,3-dihydro-2H-pyrrolo[3,4-c]pyridine-2-carboxamide;
N-(4-{[1-(cyclobutylacetyl)piperidin-3-yl]oxy}phenyl)-1,3-dihydro-2H-pyrrolo[3,4-c]pyridine-2-carboxamide;
N-(4-{[1-(cyclopentylcarbonyl)piperidin-3-yl]oxy}phenyl)-1,3-dihydro-2H-pyrrolo[3,4-c]pyridine-2-carboxamide;
N-(4-{[1-(cyclopentylacetyl)piperidin-3-yl]oxy}phenyl)-1,3-dihydro-2H-pyrrolo[3,4-c]pyridine-2-carboxamide;
N-[4-({1-[(2S)-tetrahydrofuran-2-ylcarbonyl]piperidin-3-yl}oxy)phenyl]-1,3-dihydro-2H-pyrrolo[3,4-c]pyridine-2-carboxamide;
N-[4-({1-[(2R)-tetrahydrofuran-2-ylcarbonyl]piperidin-3-yl}oxy)phenyl]-1,3-dihydro-2H-pyrrolo[3,4-c]pyridine-2-carboxamide;
N-(4-{[1-(tetrahydro-2H-pyran-4-ylcarbonyl)piperidin-3-yl]oxy}phenyl)-1,3-dihydro-2H-pyrrolo[3,4-c]pyridine-2-carboxamide;
N-(4-{[1-(tetrahydro-2H-pyran-2-ylcarbonyl)piperidin-3-yl]oxy}phenyl)-1,3-dihydro-2H-pyrrolo[3,4-c]pyridine-2-carboxamide;
N-(4-{[1-(tetrahydro-2H-pyran-4-ylacetyl)piperidin-3-yl]oxy}phenyl)-1,3-dihydro-2H-pyrrolo[3,4-c]pyridine-2-carboxamide;
N-(4-{[1-(tetrahydrofuran-2-ylacetyl)piperidin-3-yl]oxy}phenyl)-1,3-dihydro-2H-pyrrolo[3,4-c]pyridine-2-carboxamide;
N-(4-{[1-(tetrahydrofuran-3-ylacetyl)piperidin-3-yl]oxy}phenyl)-1,3-dihydro-2H-pyrrolo[3,4-c]pyridine-2-carboxamide;
N-(4-{[3-(3,5-dimethyl-1H-pyrazol-1-yl)propyl]carbamoyl}phenyl)-1,3-dihydro-2H-isoindole-2-carboxamide;
N-(4-{[(3S)-1-methyl-2-oxoazepan-3-yl]carbamoyl}phenyl)-1,3-dihydro-2H-isoindole-2-carboxamide;
N-(4-{[2-(1H-pyrazol-1-yl)ethyl]carbamoyl}phenyl)-1,3-dihydro-2H-isoindole-2-carboxamide;
N-(4-{[1-(1,3-thiazol-2-yl)ethyl]carbamoyl}phenyl)-1,3-dihydro-2H-isoindole-2-carboxamide;
N-(4-{[1-(furan-2-yl)propan-2-yl]carbamoyl}phenyl)-1,3-dihydro-2H-isoindole-2-carboxamide;
N-(4-{[1-(1-methyl-1H-pyrazol-4-yl)ethyl]carbamoyl}phenyl)-1,3-dihydro-2H-isoindole-2-carboxamide;
N-(4-{[(2R)-1-amino-4-methyl-1-oxopentan-2-yl]carbamoyl}phenyl)-1,3-dihydro-2H-isoindole-2-carboxamide;
N-(4-{[1-(3,5-dimethyl-1H-pyrazol-1-yl)propan-2-yl]carbamoyl}phenyl)-1,3-dihydro-2H-isoindole-2-carboxamide;
N-{4-[(2,2-difluoroethyl)carbamoyl]phenyl}-1,3-dihydro-2H-isoindole-2-carboxamide;
N-(4-{[2-(tetrahydro-2H-pyran-4-yl)ethyl]carbamoyl}phenyl)-1,3-dihydro-2H-isoindole-2-carboxamide;
N-{4-[(tetrahydrofuran-2-ylmethyl)carbamoyl]phenyl}-1,3-dihydro-2H-isoindole-2-carboxamide;
N-{4-[(2-methoxy-2-methylpropyl)carbamoyl]phenyl}-1,3-dihydro-2H-isoindole-2-carboxamide;
N-(4-{[(5-methyl-1,2-oxazol-3-yl)methyl]carbamoyl}phenyl)-1,3-dihydro-2H-isoindole-2-carboxamide;
N-(4-{[(1-methyl-1H-pyrazol-4-yl)methyl]carbamoyl}phenyl)-1,3-dihydro-2H-isoindole-2-carboxamide;
N-(4-{[2-(3,5-dimethyl-1H-pyrazol-1-yl)ethyl]carbamoyl}phenyl)-1,3-dihydro-2H-isoindole-2-carboxamide;
Nalpha-{4-[(1,3-dihydro-2H-isoindol-2-ylcarbonyl)amino]benzoyl}-L-phenylalaninamide;

N-(4-{[2-(2-methyl-1,3-thiazol-4-yl)ethyl]carbamoyl}phenyl)-1,3-dihydro-2H-isoindole-2-carboxamide;
N-(4-{[(2S)-3,3-dimethyl-1-(methylamino)-1-oxobutan-2-yl]carbamoyl}phenyl)-1,3-dihydro-2H-isoindole-2-carboxamide;
N-[4-(thiophen-3-ylcarbamoyl)phenyl]-1,3-dihydro-2H-isoindole-2-carboxamide;
N-(4-{[2-(5-methyl-1H-pyrazol-1-yl)ethyl]carbamoyl}phenyl)-1,3-dihydro-2H-isoindole-2-carboxamide;
N-(4-{[2-(3-methyl-1H-pyrazol-1-yl)ethyl]carbamoyl}phenyl)-1,3-dihydro-2H-isoindole-2-carboxamide;
N-{4-[(2S)-butan-2-ylcarbamoyl]phenyl}-1,3-dihydro-2H-isoindole-2-carboxamide;
N-{4-[(3,3-dimethyl-2-oxobutyl)carbamoyl]phenyl}-1,3-dihydro-2H-isoindole-2-carboxamide;
N-(4-{[(1-methyl-1H-pyrazol-3-yl)methyl]carbamoyl}phenyl)-1,3-dihydro-2H-isoindole-2-carboxamide;
N-(4-{[2-(acetylamino)phenyl]carbamoyl}phenyl)-1,3-dihydro-2H-isoindole-2-carboxamide;
N-{4-[(1-methoxybutan-2-yl)carbamoyl]phenyl}-1,3-dihydro-2H-isoindole-2-carboxamide;
N-[4-(tetrahydro-2H-pyran-4-ylcarbamoyl)phenyl]-1,3-dihydro-2H-isoindole-2-carboxamide;
N-[4-(pyrimidin-4-ylcarbamoyl)phenyl]-1,3-dihydro-2H-isoindole-2-carboxamide;
N-(4-{[2-(1H-pyrrol-1-yl)ethyl]carbamoyl}phenyl)-1,3-dihydro-2H-isoindole-2-carboxamide;
N-(4-{[(2S)-2-methylbutyl]carbamoyl}phenyl)-1,3-dihydro-2H-isoindole-2-carboxamide;
N-{4-[(1-amino-1-oxohexan-2-yl)carbamoyl]phenyl}-1,3-dihydro-2H-isoindole-2-carboxamide;
N-{4-[(2-amino-2-oxo-1-phenylethyl)carbamoyl]phenyl}-1,3-dihydro-2H-isoindole-2-carboxamide;
N-{4-[(3-tert-butoxypropyl)carbamoyl]phenyl}-1,3-dihydro-2H-isoindole-2-carboxamide;
N-(4-{[3-(methylcarbamoyl)phenyl]carbamoyl}phenyl)-1,3-dihydro-2H-isoindole-2-carboxamide;
N-(4-{[(2R)-3-methylbutan-2-yl]carbamoyl}phenyl)-1,3-dihydro-2H-isoindole-2-carboxamide;
N-(4-{[(2S)-3-methylbutan-2-yl]carbamoyl}phenyl)-1,3-dihydro-2H-isoindole-2-carboxamide;
N-(4-{[2-methyl-1-(morpholin-4-yl)propan-2-yl]carbamoyl}phenyl)-1,3-dihydro-2H-isoindole-2-carboxamide;
N-(4-{[1-(5-oxo-L-prolyl)piperidin-4-yl]oxy}phenyl)-1,3-dihydro-2H-pyrrolo[3,4-c]pyridine-2-carboxamide;
N-(4-{[2-methyl-2-(morpholin-4-yl)propyl]carbamoyl}phenyl)-1,3-dihydro-2H-isoindole-2-carboxamide;
N-{4-[(2-ethoxypropyl)carbamoyl]phenyl}-1,3-dihydro-2H-isoindole-2-carboxamide;
N-{4-[1-(tetrahydrofuran-2-ylacetyl)piperidin-4-yl]butyl}-1,3-dihydro-2H-pyrrolo[3,4-c]pyridine-2-carboxamide;
N-(4-{1-[(1,1-dioxidotetrahydrothiophen-3-yl)carbonyl]piperidin-4-yl}butyl)-1,3-dihydro-2H-pyrrolo[3,4-c]pyridine-2-carboxamide;
N-{4-[1-(tetrahydro furan-3-ylacetyl)piperidin-4-yl]butyl}-1,3-dihydro-2H-pyrrolo[3,4-c]pyridine-2-carboxamide;
N-{4-[1-(cyclohexylcarbonyl)piperidin-4-yl]butyl}-1,3-dihydro-2H-pyrrolo[3,4-c]pyridine-2-carboxamide;
N-(4-{1-[(4,4-difluorocyclohexyl)carbonyl]piperidin-4-yl}butyl)-1,3-dihydro-2H-pyrrolo[3,4-c]pyridine-2-carboxamide;
N-{4-[1-(2-hydroxy-2-methylpropanoyl)piperidin-4-yl]butyl}-1,3-dihydro-2H-pyrrolo[3,4-c]pyridine-2-carboxamide;
N-(4-{1-[(2R)-tetrahydrofuran-2-ylcarbonyl]piperidin-4-yl}butyl)-1,3-dihydro-2H-pyrrolo[3,4-c]pyridine-2-carboxamide;
N-(4-{1-[(2S)-tetrahydrofuran-2-ylcarbonyl]piperidin-4-yl}butyl)-1,3-dihydro-2H-pyrrolo[3,4-c]pyridine-2-carboxamide;
N-(4-{1-[(2-methoxyethoxy)acetyl]piperidin-4-yl}butyl)-1,3-dihydro-2H-pyrrolo[3,4-c]pyridine-2-carboxamide;
N-{4-[1-(tetrahydrofuran-3-ylcarbonyl)piperidin-4-yl]butyl}-1,3-dihydro-2H-pyrrolo[3,4-c]pyridine-2-carboxamide;
N-(4-{1-[(propan-2-yloxy)acetyl]piperidin-4-yl}butyl)-1,3-dihydro-2H-pyrrolo[3,4-c]pyridine-2-carboxamide;
N-{4-[1-(cyclopropylacetyl)piperidin-4-yl]butyl}-1,3-dihydro-2H-pyrrolo[3,4-c]pyridine-2-carboxamide;
N-{4-[1-(4,4,4-trifluorobutanoyl)piperidin-4-yl]butyl}-1,3-dihydro-2H-pyrrolo[3,4-c]pyridine-2-carboxamide;
N-{4-[(3-ethoxypropanoyl)amino]phenyl}-1,3-dihydro-2H-pyrrolo[3,4-c]pyridine-2-carboxamide;
N-(4-{[(1-acetylpiperidin-4-yl)carbonyl]amino}phenyl)-1,3-dihydro-2H-pyrrolo[3,4-c]pyridine-2-carboxamide;
N-{4-[(ethoxyacetyl)amino]phenyl}-1,3-dihydro-2H-pyrrolo[3,4-c]pyridine-2-carboxamide;
N-{4-[(tetrahydrofuran-2-ylcarbonyl)amino]phenyl}-1,3-dihydro-2H-pyrrolo[3,4-c]pyridine-2-carboxamide;
N-{4-[(tetrahydrofuran-3-ylcarbonyl)amino]phenyl}-1,3-dihydro-2H-pyrrolo[3,4-c]pyridine-2-carboxamide;
N-{4-[(cyclopentylcarbonyl)amino]phenyl}-1,3-dihydro-2H-pyrrolo[3,4-c]pyridine-2-carboxamide;
N-{7-oxo-7-[(3-phenylpropyl)amino]heptyl}-1,3-dihydro-2H-isoindole-2-carboxamide;
N-{4-[(bicyclo[2.2.1]hept-2-ylacetyl)amino]phenyl}-1,3-dihydro-2H-pyrrolo[3,4-c]pyridine-2-carboxamide;
N-{4-[(1,3-thiazol-5-ylcarbonyl)amino]phenyl}-1,3-dihydro-2H-pyrrolo[3,4-c]pyridine-2-carboxamide;
N-(4-{[(4-oxo-4,5,6,7-tetrahydro-1-benzo furan-3-yl)carbonyl]amino}phenyl)-1,3-dihydro-2H-pyrrolo[3,4-c]pyridine-2-carboxamide;
N-(4-{2-[(3-methylbutanoyl)amino]ethyl}phenyl)-1,3-dihydro-2H-isoindole-2-carboxamide;
N-(4-{2-[(4-methylpentanoyl)amino]ethyl}phenyl)-1,3-dihydro-2H-isoindole-2-carboxamide;
N-(4-{2-[(ethoxyacetyl)amino]ethyl}phenyl)-1,3-dihydro-2H-isoindole-2-carboxamide;
N-[4-(2-{[(2-methoxyethoxy)acetyl]amino}ethyl)phenyl]-1,3-dihydro-2H-isoindole-2-carboxamide;
N-(4-{2-[(tetrahydro furan-2-ylcarbonyl)amino]ethyl}phenyl)-1,3-dihydro-2H-isoindole-2-carboxamide;
N-(4-{2-[(cyclopentylcarbonyl)amino]ethyl}phenyl)-1,3-dihydro-2H-isoindole-2-carboxamide;
N-(4-{2-[(cyclopentylacetyl)amino]ethyl}phenyl)-1,3-dihydro-2H-isoindole-2-carboxamide;
N-{4-[2-(benzoylamino)ethyl]phenyl}-1,3-dihydro-2H-isoindole-2-carboxamide;
N-(4-{2-[(tetrahydro-2H-pyran-4-ylcarbonyl)amino]ethyl}phenyl)-1,3-dihydro-2H-isoindole-2-carboxamide;
N-(4-{2-[(tetrahydro-2H-pyran-4-ylacetyl)amino]ethyl}phenyl)-1,3-dihydro-2H-isoindole-2-carboxamide;
N-(4-{2-[(tetrahydro furan-3-ylacetyl)amino]ethyl}phenyl)-1,3-dihydro-2H-isoindole-2-carboxamide;
N-(4-{1-[(2R)-tetrahydro furan-2-ylcarbonyl]piperidin-4-yl}phenyl)-1,3-dihydro-2H-pyrrolo[3,4-c]pyridine-2-carboxamide;

N-(4-{1-[(3R)-tetrahydro furan-3-ylcarbonyl]piperidin-4-yl}phenyl)-1,3-dihydro-2H-pyrrolo[3,4-c]pyridine-2-carboxamide;

N-(4-{[1-(5-oxo-L-prolyl)azetidin-3-yl]oxy}phenyl)-1,3-dihydro-2H-pyrrolo[3,4-c]pyridine-2-carboxamide;

N-{4-[(1-propanoylazetidin-3-yl)oxy]phenyl}-1,3-dihydro-2H-pyrrolo[3,4-c]pyridine-2-carboxamide;

N-(4-{[1-(2,2-dimethylbutanoyl)azetidin-3-yl]oxy}phenyl)-1,3-dihydro-2H-pyrrolo[3,4-c]pyridine-2-carboxamide;

N-(4-{[1-(2-ethylbutanoyl)azetidin-3-yl]oxy}phenyl)-1,3-dihydro-2H-pyrrolo[3,4-c]pyridine-2-carboxamide;

N-(4-{[1-(pent-4-ynoyl)azetidin-3-yl]oxy}phenyl)-1,3-dihydro-2H-pyrrolo[3,4-c]pyridine-2-carboxamide;

N-(4-{[1-(furan-2-ylcarbonyl)azetidin-3-yl]oxy}phenyl)-1,3-dihydro-2H-pyrrolo[3,4-c]pyridine-2-carboxamide;

N-(4-{[1-(furan-3-ylcarbonyl)azetidin-3-yl]oxy}phenyl)-1,3-dihydro-2H-pyrrolo[3,4-c]pyridine-2-carboxamide;

N-(4-{[1-(thiophen-3-ylcarbonyl)azetidin-3-yl]oxy}phenyl)-1,3-dihydro-2H-pyrrolo[3,4-c]pyridine-2-carboxamide;

N-(4-{[1-(1H-pyrrol-2-ylcarbonyl)azetidin-3-yl]oxy}phenyl)-1,3-dihydro-2H-pyrrolo[3,4-c]pyridine-2-carboxamide;

N-(4-{[1-(pyrimidin-4-ylcarbonyl)azetidin-3-yl]oxy}phenyl)-1,3-dihydro-2H-pyrrolo[3,4-c]pyridine-2-carboxamide;

N-[4-({1-[(5-methylpyrazin-2-yl)carbonyl]azetidin-3-yl}oxy)phenyl]-1,3-dihydro-2H-pyrrolo[3,4-c]pyridine-2-carboxamide;

N-(4-{[1-(N,N-dimethylglycyl)azetidin-3-yl]oxy}phenyl)-1,3-dihydro-2H-pyrrolo[3,4-c]pyridine-2-carboxamide;

N-(4-{[1-(N,N-dimethyl-beta-alanyl)azetidin-3-yl]oxy}phenyl)-1,3-dihydro-2H-pyrrolo[3,4-c]pyridine-2-carboxamide;

N-(4-{[1-(pyrrolidin-1-ylacetyl)azetidin-3-yl]oxy}phenyl)-1,3-dihydro-2H-pyrrolo[3,4-c]pyridine-2-carboxamide;

N-[4-({1-[3-(pyrrolidin-1-yl)propanoyl]azetidin-3-yl}oxy)phenyl]-1,3-dihydro-2H-pyrrolo[3,4-c]pyridine-2-carboxamide;

N-[4-({1-[3-(piperidin-1-yl)propanoyl]azetidin-3-yl}oxy)phenyl]-1,3-dihydro-2H-pyrrolo[3,4-c]pyridine-2-carboxamide;

N-[4-({1-[(4-methylpiperazin-1-yl)acetyl]azetidin-3-yl}oxy)phenyl]-1,3-dihydro-2H-pyrrolo[3,4-c]pyridine-2-carboxamide;

N-[4-({1-[3-(4-methylpiperazin-1-yl)propanoyl]azetidin-3-yl}oxy)phenyl]-1,3-dihydro-2H-pyrrolo[3,4-c]pyridine-2-carboxamide;

N-(4-{[1-(2-cyclopropylethyl)piperidin-4-yl]oxy}phenyl)-1,3-dihydro-2H-pyrrolo[3,4-c]pyridine-2-carboxamide;

N-(4-{[1-(2-cyclopentylethyl)piperidin-4-yl]oxy}phenyl)-1,3-dihydro-2H-pyrrolo[3,4-c]pyridine-2-carboxamide;

N-(4-{[1-(2-methylbutyl)piperidin-4-yl]oxy}phenyl)-1,3-dihydro-2H-pyrrolo[3,4-c]pyridine-2-carboxamide;

N-(4-{[1-(tetrahydrofuran-3-ylmethyl)piperidin-4-yl]oxy}phenyl)-1,3-dihydro-2H-pyrrolo[3,4-c]pyridine-2-carboxamide;

N-(4-{[1-(3,3-dimethylbutyl)piperidin-4-yl]oxy}phenyl)-1,3-dihydro-2H-pyrrolo[3,4-c]pyridine-2-carboxamide;

N-(4-{[1-(cyclohexylmethyl)piperidin-4-yl]oxy}phenyl)-1,3-dihydro-2H-pyrrolo[3,4-c]pyridine-2-carboxamide;

N-(4-{[1-(3-methylbutyl)piperidin-4-yl]oxy}phenyl)-1,3-dihydro-2H-pyrrolo[3,4-c]pyridine-2-carboxamide;

N-(4-{[1-(cyclopentylmethyl)piperidin-4-yl]oxy}phenyl)-1,3-dihydro-2H-pyrrolo[3,4-c]pyridine-2-carboxamide;

N-(4-{[1-(tetrahydrofuran-2-ylmethyl)piperidin-4-yl]oxy}phenyl)-1,3-dihydro-2H-pyrrolo[3,4-c]pyridine-2-carboxamide;

N-(4-{[1-(2-methylpropyl)piperidin-4-yl]oxy}phenyl)-1,3-dihydro-2H-pyrrolo[3,4-c]pyridine-2-carboxamide;

N-(4-{[1-(butylsulfonyl)piperidin-4-yl]oxy}phenyl)-1,3-dihydro-2H-pyrrolo[3,4-c]pyridine-2-carboxamide;

N-(4-{[1-(cyclopropylsulfonyl)piperidin-4-yl]oxy}phenyl)-1,3-dihydro-2H-pyrrolo[3,4-c]pyridine-2-carboxamide;

N-(4-{[1-(phenylsulfonyl)piperidin-4-yl]oxy}phenyl)-1,3-dihydro-2H-pyrrolo[3,4-c]pyridine-2-carboxamide;

N-[4-({1-[(4-fluorophenyl)sulfonyl]piperidin-4-yl}oxy)phenyl]-1,3-dihydro-2H-pyrrolo[3,4-c]pyridine-2-carboxamide;

N-(4-{[1-(ethylsulfonyl)piperidin-4-yl]oxy}phenyl)-1,3-dihydro-2H-pyrrolo[3,4-c]pyridine-2-carboxamide;

N-(4-{[1-(propan-2-ylsulfonyl)piperidin-4-yl]oxy}phenyl)-1,3-dihydro-2H-pyrrolo[3,4-c]pyridine-2-carboxamide;

N-(4-{[1-(benzylsulfonyl)piperidin-4-yl]oxy}phenyl)-1,3-dihydro-2H-pyrrolo[3,4-c]pyridine-2-carboxamide;

N-(4-{[1-(propylsulfonyl)piperidin-4-yl]oxy}phenyl)-1,3-dihydro-2H-pyrrolo[3,4-c]pyridine-2-carboxamide;

N-(4-{[1-(thiophen-2-ylsulfonyl)piperidin-4-yl]oxy}phenyl)-1,3-dihydro-2H-pyrrolo[3,4-c]pyridine-2-carboxamide;

N-[4-({1-[(2S)-2-methylbutanoyl]piperidin-4-yl}oxy)phenyl]-1,3-dihydro-2H-pyrrolo[3,4-c]pyridine-2-carboxamide;

N-[4-({1-[(2S)-tetrahydrofuran-2-ylcarbonyl]piperidin-4-yl}oxy)phenyl]-1,3-dihydro-2H-pyrrolo[3,4-c]pyridine-2-carboxamide;

N-[4-({1-[(2R)-tetrahydrofuran-2-ylcarbonyl]piperidin-4-yl}oxy)phenyl]-1,3-dihydro-2H-pyrrolo[3,4-c]pyridine-2-carboxamide;

N-[4-({1-[(4,4-difluorocyclohexyl)carbonyl]azetidin-3-yl}oxy)phenyl]-1,3-dihydro-2H-pyrrolo[3,4-c]pyridine-2-carboxamide;

N-(4-{[1-(5-oxo-D-prolyl)piperidin-4-yl]oxy}phenyl)-1,3-dihydro-2H-pyrrolo[3,4-c]pyridine-2-carboxamide;

N-(4-{[1-(2,2-dimethylpropanoyl)piperidin-4-yl]oxy}phenyl)-1,3-dihydro-2H-pyrrolo[3,4-c]pyridine-2-carboxamide;

N-(4-{[1-(2-methylpentanoyl)piperidin-4-yl]oxy}phenyl)-1,3-dihydro-2H-pyrrolo[3,4-c]pyridine-2-carboxamide;

N-(4-{[1-(2-ethylbutanoyl)piperidin-4-yl]oxy}phenyl)-1,3-dihydro-2H-pyrrolo[3,4-c]pyridine-2-carboxamide;

N-(4-{[1-(1H-pyrrol-2-ylcarbonyl)piperidin-4-yl]oxy}phenyl)-1,3-dihydro-2H-pyrrolo[3,4-c]pyridine-2-carboxamide;

N-(4-{[1-(1,2-oxazol-5-ylcarbonyl)piperidin-4-yl]oxy}phenyl)-1,3-dihydro-2H-pyrrolo[3,4-c]pyridine-2-carboxamide;

N-(4-{[1-(pyridin-3-ylcarbonyl)piperidin-4-yl]oxy}phenyl)-1,3-dihydro-2H-pyrrolo[3,4-c]pyridine-2-carboxamide;

N-(4-{[1-(pyridazin-3-ylcarbonyl)piperidin-4-yl]oxy}phenyl)-1,3-dihydro-2H-pyrrolo[3,4-c]pyridine-2-carboxamide;

N-(4-{[1-(pyrazin-2-ylcarbonyl)piperidin-4-yl]oxy}phenyl)-1,3-dihydro-2H-pyrrolo[3,4-c]pyridine-2-carboxamide;

N-(4-{[1-(pyrimidin-4-ylcarbonyl)piperidin-4-yl]oxy}phenyl)-1,3-dihydro-2H-pyrrolo[3,4-c]pyridine-2-carboxamide;

N-[4-({1-[(5-methylpyrazin-2-yl)carbonyl]piperidin-4-yl}oxy)phenyl]-1,3-dihydro-2H-pyrrolo[3,4-c]pyridine-2-carboxamide;

N-[4-({1-[3-(piperidin-1-yl)propanoyl]piperidin-4-yl}oxy)phenyl]-1,3-dihydro-2H-pyrrolo[3,4-c]pyridine-2-carboxamide;

N-(4-{[1-(morpholin-4-ylacetyl)piperidin-4-yl]oxy}phenyl)-1,3-dihydro-2H-pyrrolo[3,4-c]pyridine-2-carboxamide;

N-[4-({1-[3-(4-methylpiperazin-1-yl)propanoyl]piperidin-4-yl}oxy)phenyl]-1,3-dihydro-2H-pyrrolo[3,4-c]pyridine-2-carboxamide;

benzyl trans-3-[(1,3-dihydro-2H-pyrrolo[3,4-c]pyridin-2-ylcarbonyl)amino]cyclobutanecarboxylate;

N-[4-(4-{[(4-methylpiperazin-1-yl)acetyl]amino}cyclohex-1-en-1-yl)phenyl]-1,3-dihydro-2H-pyrrolo[3,4-c]pyridine-2-carboxamide;

N-(4-{4-[(tetrahydro-2H-pyran-4-ylacetyl)amino]cyclohex-1-en-1-yl}phenyl)-1,3-dihydro-2H-pyrrolo[3,4-c]pyridine-2-carboxamide;

N-{4-[4-(benzoylamino)cyclohex-1-en-1-yl]phenyl}-1,3-dihydro-2H-pyrrolo[3,4-c]pyridine-2-carboxamide;

N-[4-(4-{[(2S)-tetrahydrofuran-2-ylcarbonyl]amino}cyclohex-1-en-1-yl)phenyl]-1,3-dihydro-2H-pyrrolo[3,4-c]pyridine-2-carboxamide;

N-[4-(4-{[(2R)-tetrahydrofuran-2-ylcarbonyl]amino}cyclohex-1-en-1-yl)phenyl]-1,3-dihydro-2H-pyrrolo[3,4-c]pyridine-2-carboxamide;

N-[4-(4-{[(1-methylpiperidin-4-yl)carbonyl]amino}cyclohex-1-en-1-yl)phenyl]-1,3-dihydro-2H-pyrrolo[3,4-c]pyridine-2-carboxamide;

N-[4-(4-{[(1,1-dioxidotetrahydro-2H-thiopyran-4-yl)carbonyl]amino}cyclohex-1-en-1-yl)phenyl]-1,3-dihydro-2H-pyrrolo[3,4-c]pyridine-2-carboxamide;

N-[4-(4-{[(3R)-tetrahydrofuran-3-ylcarbonyl]amino}cyclohex-1-en-1-yl)phenyl]-1,3-dihydro-2H-pyrrolo[3,4-c]pyridine-2-carboxamide;

N-[4-(4-{[(3S)-tetrahydrofuran-3-ylcarbonyl]amino}cyclohex-1-en-1-yl)phenyl]-1,3-dihydro-2H-pyrrolo[3,4-c]pyridine-2-carboxamide;

N-[4-(4-{[(2S)-2-methylbutanoyl]amino}cyclohex-1-en-1-yl)phenyl]-1,3-dihydro-2H-pyrrolo[3,4-c]pyridine-2-carboxamide;

N-(4-{3-[(3-methylbutanoyl)amino]oxetan-3-yl}phenyl)-1,3-dihydro-2H-pyrrolo[3,4-c]pyridine-2-carboxamide;

tert-butyl 4-({4-[(1,3-dihydro-2H-pyrrolo[3,4-c]pyridin-2-ylcarbonyl)amino]phenyl}sulfonyl)piperidine-1-carboxylate;

N-{4-[4-(propylcarbamoyl)piperidin-1-yl]phenyl}-1,3-dihydro-2H-pyrrolo[3,4-c]pyridine-2-carboxamide;

N-(4-{4-[(2-methoxyethyl)carbamoyl]piperidin-1-yl}phenyl)-1,3-dihydro-2H-pyrrolo[3,4-c]pyridine-2-carboxamide;

N-(4-{4-[(cyclopentylmethyl)carbamoyl]piperidin-1-yl}phenyl)-1,3-dihydro-2H-pyrrolo[3,4-c]pyridine-2-carboxamide;

N-(4-{4-[(1,4-dioxan-2-ylmethyl)carbamoyl]piperidin-1-yl}phenyl)-1,3-dihydro-2H-pyrrolo[3,4-c]pyridine-2-carboxamide;

N-{4-[4-(cyclopentylcarbamoyl)piperidin-1-yl]phenyl}-1,3-dihydro-2H-pyrrolo[3,4-c]pyridine-2-carboxamide;

N-{4-[4-(tetrahydro-2H-pyran-4-ylcarbamoyl)piperidin-1-yl]phenyl}-1,3-dihydro-2H-pyrrolo[3,4-c]pyridine-2-carboxamide;

N-{4-[4-(morpholin-4-ylcarbonyl)piperidin-1-yl]phenyl}-1,3-dihydro-2H-pyrrolo[3,4-c]pyridine-2-carboxamide;

N-(4-{4-[(tetrahydro-2H-pyran-4-ylmethyl)carbamoyl]piperidin-1-yl}phenyl)-1,3-dihydro-2H-pyrrolo[3,4-c]pyridine-2-carboxamide;

N-{4-[4-(cyclopropylcarbamoyl)piperidin-1-yl]phenyl}-1,3-dihydro-2H-pyrrolo[3,4-c]pyridine-2-carboxamide;

N-(4-{4-[(tetrahydrofuran-3-ylmethyl)carbamoyl]piperidin-1-yl}phenyl)-1,3-dihydro-2H-pyrrolo[3,4-c]pyridine-2-carboxamide;

N-(4-{4-[(2-hydroxy-2-methylpropyl)carbamoyl]piperidin-1-yl}phenyl)-1,3-dihydro-2H-pyrrolo[3,4-c]pyridine-2-carboxamide;

N-{4-[4-(butan-2-ylcarbamoyl)piperidin-1-yl]phenyl}-1,3-dihydro-2H-pyrrolo[3,4-c]pyridine-2-carboxamide;

N-(4-{1-[(3R)-tetrahydrofuran-3-ylcarbonyl]-1,2,3,6-tetrahydropyridin-4-yl}phenyl)-1,3-dihydro-2H-isoindole-2-carboxamide;

N-(4-{1-[(3S)-tetrahydrofuran-3-ylcarbonyl]-1,2,3,6-tetrahydropyridin-4-yl}phenyl)-1,3-dihydro-2H-isoindole-2-carboxamide;

N-(4-{1-[(1,1-dioxidotetrahydro-2H-thiopyran-4-yl)carbonyl]-1,2,3,6-tetrahydropyridin-4-yl}phenyl)-1,3-dihydro-2H-isoindole-2-carboxamide;

N-(4-{1-[(2R)-tetrahydrofuran-2-ylcarbonyl]piperidin-4-yl}phenyl)-1,3-dihydro-2H-isoindole-2-carboxamide;

N-(4-{1-[(2S)-tetrahydrofuran-2-ylcarbonyl]piperidin-4-yl}phenyl)-1,3-dihydro-2H-isoindole-2-carboxamide;

N-(4-{1-[(3R)-tetrahydrofuran-3-ylcarbonyl]piperidin-4-yl}phenyl)-1,3-dihydro-2H-isoindole-2-carboxamide;

N-(4-{(4R)-4-[(2-methylpropanoyl)amino]cyclohex-1-en-1-yl}phenyl)-1,3-dihydro-2H-pyrrolo[3,4-c]pyridine-2-carboxamide;

N-(4-{(4S)-4-[(2-methylpropanoyl)amino]cyclohex-1-en-1-yl}phenyl)-1,3-dihydro-2H-pyrrolo[3,4-c]pyridine-2-carboxamide;

N-[4-(1-benzoylazetidin-3-yl)butyl]-1,3-dihydro-2H-isoindole-2-carboxamide;

N-[4-(1-benzoylazetidin-3-yl)butyl]-1,3-dihydro-2H-pyrrolo[3,4-c]pyridine-2-carboxamide;

N-[trans-3-(benzylcarbamoyl)cyclobutyl]-1,3-dihydro-2H-pyrrolo[3,4-c]pyridine-2-carboxamide;

N-{trans-3-[(2-phenylethyl)carbamoyl]cyclobutyl}-1,3-dihydro-2H-pyrrolo[3,4-c]pyridine-2-carboxamide;

N-{trans-3-[(3-phenylpropyl)carbamoyl]cyclobutyl}-1,3-dihydro-2H-pyrrolo[3,4-c]pyridine-2-carboxamide;

N-(4-{1-[(2-methyl-1,3-oxazol-4-yl)carbonyl]-1,2,3,6-tetrahydropyridin-4-yl}phenyl)-1,3-dihydro-2H-pyrrolo[3,4-c]pyridine-2-carboxamide;

N-{4-[1-(furan-3-ylcarbonyl)-1,2,3,6-tetrahydropyridin-4-yl]phenyl}-1,3-dihydro-2H-pyrrolo[3,4-c]pyridine-2-carboxamide;

N-(4-{1-[(2E)-3-(furan-2-yl)prop-2-enoyl]-1,2,3,6-tetrahydropyridin-4-yl}phenyl)-1,3-dihydro-2H-pyrrolo[3,4-c]pyridine-2-carboxamide;

N-{4-[1-(1,3-oxazol-5-ylcarbonyl)-1,2,3,6-tetrahydropyridin-4-yl]phenyl}-1,3-dihydro-2H-pyrrolo[3,4-c]pyridine-2-carboxamide;

N-{4-[1-(3,3,3-trifluoropropanoyl)-1,2,3,6-tetrahydropyridin-4-yl]phenyl}-1,3-dihydro-2H-pyrrolo[3,4-c]pyridine-2-carboxamide;

N-(4-{1-[(1,5-dimethyl-1H-pyrazol-3-yl)carbonyl]-1,2,3,6-tetrahydropyridin-4-yl}phenyl)-1,3-dihydro-2H-pyrrolo[3,4-c]pyridine-2-carboxamide;

N-(4-{1-[(4-methoxycyclohexyl)carbonyl]-1,2,3,6-tetrahydropyridin-4-yl}phenyl)-1,3-dihydro-2H-pyrrolo[3,4-c]pyridine-2-carboxamide;

N-{4-[1-(2,3-dimethylbutanoyl)-1,2,3,6-tetrahydropyridin-4-yl]phenyl}-1,3-dihydro-2H-pyrrolo[3,4-c]pyridine-2-carboxamide;

N-(4-{1-[(2,2-difluorocyclopropyl)carbonyl]-1,2,3,6-tetrahydropyridin-4-yl}phenyl)-1,3-dihydro-2H-pyrrolo[3,4-c]pyridine-2-carboxamide;

N-{4-[1-(1H-pyrazol-5-ylcarbonyl)-1,2,3,6-tetrahydropyridin-4-yl]phenyl}-1,3-dihydro-2H-pyrrolo[3,4-c]pyridine-2-carboxamide;

N-{4-[1-(tert-butoxyacetyl)-1,2,3,6-tetrahydropyridin-4-yl]phenyl}-1,3-dihydro-2H-pyrrolo[3,4-c]pyridine-2-carboxamide;

N-(4-{1-[3-(1H-1,2,4-triazol-1-yl)propanoyl]-1,2,3,6-tetrahydropyridin-4-yl}phenyl)-1,3-dihydro-2H-pyrrolo[3,4-c]pyridine-2-carboxamide;

N-{4-[1-(3-ethoxypropanoyl)-1,2,3,6-tetrahydropyridin-4-yl]phenyl}-1,3-dihydro-2H-pyrrolo[3,4-c]pyridine-2-carboxamide;

N-{4-[1-(3-hydroxy-3-methylbutanoyl)-1,2,3,6-tetrahydropyridin-4-yl]phenyl}-1,3-dihydro-2H-pyrrolo[3,4-c]pyridine-2-carboxamide;

N-(4-{1-[3-(1H-pyrrol-1-yl)propanoyl]-1,2,3,6-tetrahydropyridin-4-yl}phenyl)-1,3-dihydro-2H-pyrrolo[3,4-c]pyridine-2-carboxamide;

N-(4-{1-[(1-methylcyclopropyl)carbonyl]-1,2,3,6-tetrahydropyridin-4-yl}phenyl)-1,3-dihydro-2H-pyrrolo[3,4-c]pyridine-2-carboxamide;

N-(4-{1-[(2-methylpropoxy)acetyl]-1,2,3,6-tetrahydropyridin-4-yl}phenyl)-1,3-dihydro-2H-pyrrolo[3,4-c]pyridine-2-carboxamide;

N-{4-[1-(1-methylprolyl)-1,2,3,6-tetrahydropyridin-4-yl]phenyl}-1,3-dihydro-2H-pyrrolo[3,4-c]pyridine-2-carboxamide;

N-{4-[1-(2-hydroxy-2-methylbutanoyl)-1,2,3,6-tetrahydropyridin-4-yl]phenyl}-1,3-dihydro-2H-pyrrolo[3,4-c]pyridine-2-carboxamide;

N-(4-{1-[(1-hydroxycyclopropyl)carbonyl]-1,2,3,6-tetrahydropyridin-4-yl}phenyl)-1,3-dihydro-2H-pyrrolo[3,4-c]pyridine-2-carboxamide;

N-{4-[1-(cyclopropylacetyl)-1,2,3,6-tetrahydropyridin-4-yl]phenyl}-1,3-dihydro-2H-pyrrolo[3,4-c]pyridine-2-carboxamide;

N-{4-[1-(cyclopentylcarbonyl)-1,2,3,6-tetrahydropyridin-4-yl]phenyl}-1,3-dihydro-2H-pyrrolo[3,4-c]pyridine-2-carboxamide;

N-[4-(1-{[1-(methoxymethyl)cyclopropyl]carbonyl}-1,2,3,6-tetrahydropyridin-4-yl)phenyl]-1,3-dihydro-2H-pyrrolo[3,4-c]pyridine-2-carboxamide;

N-(4-{1-[(methylsulfonyl)acetyl]-1,2,3,6-tetrahydropyridin-4-yl}phenyl)-1,3-dihydro-2H-pyrrolo[3,4-c]pyridine-2-carboxamide;

N-(4-{1-[(1-methyl-1H-pyrazol-4-yl)carbonyl]-1,2,3,6-tetrahydropyridin-4-yl}phenyl)-1,3-dihydro-2H-pyrrolo[3,4-c]pyridine-2-carboxamide;

N-[4-(1-acetyl-1,2,3,6-tetrahydropyridin-4-yl)phenyl]-1,3-dihydro-2H-pyrrolo[3,4-c]pyridine-2-carboxamide;

N-{4-[1-(cyclopropylcarbonyl)-1,2,3,6-tetrahydropyridin-4-yl]phenyl}-1,3-dihydro-2H-pyrrolo[3,4-c]pyridine-2-carboxamide;

N-{4-[1-(2-ethylbutanoyl)-1,2,3,6-tetrahydropyridin-4-yl]phenyl}-1,3-dihydro-2H-pyrrolo[3,4-c]pyridine-2-carboxamide;

N-{4-[1-(5-oxo-L-prolyl)-1,2,3,6-tetrahydropyridin-4-yl]phenyl}-1,3-dihydro-2H-pyrrolo[3,4-c]pyridine-2-carboxamide;

N-(4-{1-[(2E)-4-methylpent-2-enoyl]-1,2,3,6-tetrahydropyridin-4-yl]phenyl)-1,3-dihydro-2H-pyrrolo[3,4-c]pyridine-2-carboxamide;

N-{4-[1-(2-methoxy-2-methylpropanoyl)-1,2,3,6-tetrahydropyridin-4-yl]phenyl}-1,3-dihydro-2H-pyrrolo[3,4-c]pyridine-2-carboxamide;

N-{4-[1-(cyclopent-1-en-1-ylcarbonyl)-1,2,3,6-tetrahydropyridin-4-yl]phenyl}-1,3-dihydro-2H-pyrrolo[3,4-c]pyridine-2-carboxamide;

N-{4-[1-(thiophen-3-ylacetyl)-1,2,3,6-tetrahydropyridin-4-yl]phenyl}-1,3-dihydro-2H-pyrrolo[3,4-c]pyridine-2-carboxamide;

N-{4-[1-(cyclohexylcarbonyl)-1,2,3,6-tetrahydropyridin-4-yl]phenyl}-1,3-dihydro-2H-pyrrolo[3,4-c]pyridine-2-carboxamide;

N-[4-(1-propanoyl-1,2,3,6-tetrahydropyridin-4-yl)phenyl]-1,3-dihydro-2H-pyrrolo[3,4-c]pyridine-2-carboxamide;

N-{4-[1-(2,2-dimethylbutanoyl)-1,2,3,6-tetrahydropyridin-4-yl]phenyl}-1,3-dihydro-2H-pyrrolo[3,4-c]pyridine-2-carboxamide;

N-(4-{1-[(1-methyl-1H-pyrrol-2-yl)carbonyl]-1,2,3,6-tetrahydropyridin-4-yl}phenyl)-1,3-dihydro-2H-pyrrolo[3,4-c]pyridine-2-carboxamide;

N-{4-[1-(methoxyacetyl)-1,2,3,6-tetrahydropyridin-4-yl]phenyl}-1,3-dihydro-2H-pyrrolo[3,4-c]pyridine-2-carboxamide;

N-{4-[1-(2,2-dimethylpropanoyl)-1,2,3,6-tetrahydropyridin-4-yl]phenyl}-1,3-dihydro-2H-pyrrolo[3,4-c]pyridine-2-carboxamide;

N-{4-[1-(4-methylhexanoyl)-1,2,3,6-tetrahydropyridin-4-yl]phenyl}-1,3-dihydro-2H-pyrrolo[3,4-c]pyridine-2-carboxamide;

N-(4-{1-[(2,2-dimethylcyclopropyl)carbonyl]-1,2,3,6-tetrahydropyridin-4-yl}phenyl)-1,3-dihydro-2H-pyrrolo[3,4-c]pyridine-2-carboxamide;

N-(4-{1-[(1,3-dimethyl-1H-pyrazol-5-yl)carbonyl]-1,2,3,6-tetrahydropyridin-4-yl}phenyl)-1,3-dihydro-2H-pyrrolo[3,4-c]pyridine-2-carboxamide;

N-{4-[1-(cyclobutylacetyl)-1,2,3,6-tetrahydropyridin-4-yl]phenyl}-1,3-dihydro-2H-pyrrolo[3,4-c]pyridine-2-carboxamide;

N-{4-[1-(piperidin-1-ylacetyl)-1,2,3,6-tetrahydropyridin-4-yl]phenyl}-1,3-dihydro-2H-pyrrolo[3,4-c]pyridine-2-carboxamide;

N-(4-{1-[2-(pyrrolidin-1-yl)propanoyl]-1,2,3,6-tetrahydropyridin-4-yl}phenyl)-1,3-dihydro-2H-pyrrolo[3,4-c]pyridine-2-carboxamide;

N-(4-{1-[(1,3-dimethyl-1H-pyrazol-4-yl)carbonyl]-1,2,3,6-tetrahydropyridin-4-yl}phenyl)-1,3-dihydro-2H-pyrrolo[3,4-c]pyridine-2-carboxamide;

N-[4-(cis-4-{[(2-methoxyethoxy)acetyl]amino}cyclohexyl)phenyl]-1,3-dihydro-2H-pyrrolo[3,4-c]pyridine-2-carboxamide;

N-[4-(trans-4-{[(2-methoxyethoxy)acetyl]amino}cyclohexyl)phenyl]-1,3-dihydro-2H-pyrrolo[3,4-c]pyridine-2-carboxamide;

N-[4-(cis-4-{[(2S)-tetrahydrofuran-2-ylcarbonyl]amino}cyclohexyl)phenyl]-1,3-dihydro-2H-pyrrolo[3,4-c]pyridine-2-carboxamide;

N-[4-(trans-4-{[(2S)-tetrahydrofuran-2-ylcarbonyl]amino}cyclohexyl)phenyl]-1,3-dihydro-2H-pyrrolo[3,4-c]pyridine-2-carboxamide;

N-[4-(cis-4-{[(2R)-tetrahydrofuran-2-ylcarbonyl]amino}cyclohexyl)phenyl]-1,3-dihydro-2H-pyrrolo[3,4-c]pyridine-2-carboxamide;

N-[4-(trans-4-{[(2R)-tetrahydrofuran-2-ylcarbonyl]amino}cyclohexyl)phenyl]-1,3-dihydro-2H-pyrrolo[3,4-c]pyridine-2-carboxamide;

N-(6-{[(2S)-tetrahydrofuran-2-ylmethyl]
   carbamoyl}pyridazin-3-yl)-1,3-dihydro-2H-pyrrolo[3,4-c]pyridine-2-carboxamide;
N-(4-{[(3R)-1-(3-methylbutanoyl)pyrrolidin-3-yl]
   oxy}phenyl)-1,3-dihydro-2H-pyrrolo[3,4-c]pyridine-2-carboxamide;
N-(4-{[(3R)-1-(cyclobutylcarbonyl)pyrrolidin-3-yl]
   oxy}phenyl)-1,3-dihydro-2H-pyrrolo[3,4-c]pyridine-2-carboxamide;
N-[4-({(3R)-1-[(2R)-tetrahydrofuran-2-ylcarbonyl]pyrrolidin-3-yl}oxy)phenyl]-1,3-dihydro-2H-pyrrolo[3,4-c]pyridine-2-carboxamide;
N-[4-({(3R)-1-[(2S)-tetrahydrofuran-2-ylcarbonyl]pyrrolidin-3-yl}oxy)phenyl]-1,3-dihydro-2H-pyrrolo[3,4-c]pyridine-2-carboxamide;
N-(4-{[(3R)-1-(cyclopropylacetyl)pyrrolidin-3-yl]
   oxy}phenyl)-1,3-dihydro-2H-pyrrolo[3,4-c]pyridine-2-carboxamide;
N-(4-{[(3S)-1-(3-methylbutanoyl)pyrrolidin-3-yl]
   oxy}phenyl)-1,3-dihydro-2H-pyrrolo[3,4-c]pyridine-2-carboxamide;
N-(4-{[(3S)-1-(cyclobutylcarbonyl)pyrrolidin-3-yl]
   oxy}phenyl)-1,3-dihydro-2H-pyrrolo[3,4-c]pyridine-2-carboxamide;
N-[4-({(3S)-1-[(2R)-tetrahydrofuran-2-ylcarbonyl]pyrrolidin-3-yl}oxy)phenyl]-1,3-dihydro-2H-pyrrolo[3,4-c]pyridine-2-carboxamide;
N-[4-({(3S)-1-[(2S)-tetrahydrofuran-2-ylcarbonyl]pyrrolidin-3-yl}oxy)phenyl]-1,3-dihydro-2H-pyrrolo[3,4-c]pyridine-2-carboxamide;
N-(4-{[(3S)-1-(cyclopropylacetyl)pyrrolidin-3-yl]
   oxy}phenyl)-1,3-dihydro-2H-pyrrolo[3,4-c]pyridine-2-carboxamide;
N-(6-{[(2R)-tetrahydrofuran-2-ylmethyl]
   carbamoyl}pyridazin-3-yl)-1,3-dihydro-2H-pyrrolo[3,4-c]pyridine-2-carboxamide;
N-{6-[(tetrahydro-2H-pyran-4-ylmethyl)carbamoyl]pyridazin-3-yl}-1,3-dihydro-2H-pyrrolo[3,4-c]pyridine-2-carboxamide;
N-{6-[(cyclopentylmethyl)carbamoyl]pyridazin-3-yl}-1,3-dihydro-2H-pyrrolo[3,4-c]pyridine-2-carboxamide;
N-{6-[(tetrahydrofuran-3-ylmethyl)carbamoyl]pyridazin-3-yl}-1,3-dihydro-2H-pyrrolo[3,4-c]pyridine-2-carboxamide;
N-{6-[(bicyclo[2.2.1]hept-2-ylmethyl)carbamoyl]pyridazin-3-yl}-1,3-dihydro-2H-pyrrolo[3,4-c]pyridine-2-carboxamide;
N-(4-{trans-4-[(2-methylpropanoyl)amino]
   cyclohexyl}phenyl)-1,3-dihydro-2H-pyrrolo[3,4-c]pyridine-2-carboxamide;
N-(4-{cis-4-[(2-methylpropanoyl)amino]
   cyclohexyl}phenyl)-1,3-dihydro-2H-pyrrolo[3,4-c]pyridine-2-carboxamide;
N-(4-{cis-4-[(cyclohexylcarbonyl)amino]
   cyclohexyl}phenyl)-1,3-dihydro-2H-pyrrolo[3,4-c]pyridine-2-carboxamide;
N-(4-{trans-4-[(cyclohexylcarbonyl)amino]
   cyclohexyl}phenyl)-1,3-dihydro-2H-pyrrolo[3,4-c]pyridine-2-carboxamide;
N-(4-{trans-4-[(cyclopropylacetyl)amino]
   cyclohexyl}phenyl)-1,3-dihydro-2H-pyrrolo[3,4-c]pyridine-2-carboxamide;
N-(4-{cis-4-[(cyclopropylacetyl)amino]
   cyclohexyl}phenyl)-1,3-dihydro-2H-pyrrolo[3,4-c]pyridine-2-carboxamide;
N-(4-{4-[(2-methylpropanoyl)amino]cyclohex-1-en-1-yl}phenyl)-1,3-dihydro-2H-isoindole-2-carboxamide;
N-[4-(4-{[(2R)-tetrahydrofuran-2-ylcarbonyl]
   amino}cyclohex-1-en-1-yl)phenyl]-1,3-dihydro-2H-isoindole-2-carboxamide;
N-[4-(4-{[(2S)-tetrahydrofuran-2-ylcarbonyl]
   amino}cyclohex-1-en-1-yl)phenyl]-1,3-dihydro-2H-isoindole-2-carboxamide;
N-(4-{4-[(cyclopentylacetyl)amino]cyclohex-1-en-1-yl}phenyl)-1,3-dihydro-2H-isoindole-2-carboxamide;
N-(4-{4-[(cyclopropylacetyl)amino]cyclohex-1-en-1-yl}phenyl)-1,3-dihydro-2H-isoindole-2-carboxamide;
N-(4-{4-[(2-hydroxy-2-methylpropanoyl)amino]cyclohex-1-en-1-yl}phenyl)-1,3-dihydro-2H-isoindole-2-carboxamide;
N-(4-{4-[(tetrahydro-2H-pyran-4-ylcarbonyl)amino]cyclohex-1-en-1-yl}phenyl)-1,3-dihydro-2H-isoindole-2-carboxamide;
N-(4-{4-[(cyclohexylcarbonyl)amino]cyclohex-1-en-1-yl}phenyl)-1,3-dihydro-2H-isoindole-2-carboxamide;
and pharmaceutically acceptable salts thereof.

Still another embodiment pertains to compounds of Formula (Ic), which are
N-(4-{[(3S)-tetrahydrofuran-3-ylmethyl]
   carbamoyl}phenyl)-1,3-dihydro-2H-isoindole-2-carboxamide;
N-[4-(1-isobutyryl-1,2,3,6-tetrahydropyridin-4-yl)phenyl]-1,3-dihydro-2H-pyrrolo[3,4-c]pyridine-2-carboxamide;
5-fluoro-N-(4-{[(3S)-tetrahydrofuran-3-ylmethyl]
   carbamoyl}phenyl)-1,3-dihydro-2H-isoindole-2-carboxamide;
N-[4-(1-isobutyrylpiperidin-4-yl)phenyl]-1,3-dihydro-2H-pyrrolo[3,4-c]pyridine-2-carboxamide;
N-[4-(1-benzoylpiperidin-4-yl)butyl]-1,3-dihydro-2H-pyrrolo[3,4-c]pyridine-2-carboxamide;
N-{4-[1-(2-hydroxy-2-methylpropanoyl)piperidin-4-yl]
   phenyl}-1,3-dihydro-2H-pyrrolo[3,4-c]pyridine-2-carboxamide;
N-(4-{1-[(2S)-tetrahydrofuran-2-ylcarbonyl]-1,2,3,6-tetrahydropyridin-4-yl}phenyl)-1,3-dihydro-2H-pyrrolo[3,4-c]pyridine-2-carboxamide;
N-(4-{1-[(1,1-dioxidotetrahydro-2H-thiopyran-4-yl)carbonyl]-1,2,3,6-tetrahydropyridin-4-yl}phenyl)-1,3-dihydro-2H-pyrrolo[3,4-c]pyridine-2-carboxamide;
N-(4-{1-[(3S)-tetrahydrofuran-3-ylcarbonyl]-1,2,3,6-tetrahydropyridin-4-yl}phenyl)-1,3-dihydro-2H-pyrrolo[3,4-c]pyridine-2-carboxamide;
N-(4-{1-[(3S)-tetrahydrofuran-3-ylcarbonyl]piperidin-4-yl}phenyl)-1,3-dihydro-2H-pyrrolo[3,4-c]pyridine-2-carboxamide; and pharmaceutically acceptable salts thereof.

Still another embodiment pertains to compounds of Formula (Ic), which are
N-(4-{[(3S)-tetrahydrofuran-3-ylmethyl]
   carbamoyl}phenyl)-1,3-dihydro-2H-isoindole-2-carboxamide;
N-[4-(1-isobutyryl-1,2,3,6-tetrahydropyridin-4-yl)phenyl]-1,3-dihydro-2H-pyrrolo[3,4-c]pyridine-2-carboxamide;
N-[4-(1-isobutyrylpiperidin-4-yl)phenyl]-1,3-dihydro-2H-pyrrolo[3,4-c]pyridine-2-carboxamide;
N-[4-(1-benzoylpiperidin-4-yl)butyl]-1,3-dihydro-2H-pyrrolo[3,4-c]pyridine-2-carboxamide;
N-{4-[1-(2-hydroxy-2-methylpropanoyl)piperidin-4-yl]
   phenyl}-1,3-dihydro-2H-pyrrolo[3,4-c]pyridine-2-carboxamide; and pharmaceutically acceptable salts thereof.

Another embodiment pertains to a composition for treating hypertension, chronic and congestive heart failure, cardiac hypertrophy, restenosis, chronic renal failure, cerebral vasospasm after subarachnoid bleeding, pulmonary hypertension, atherosclerosis, asthma, male erectile dysfunctions, female sexual dysfunction, over-active bladder syndrome, spinal-cord injury, traumatic brain injury, stroke, inflammatory and demyelinating diseases, Alzheimer's disease, pain, multiple sclerosis, amyotrophic lateral sclerosis, Huntington's disease, Parkinson's disease, inflammatory pain, rheumatoid arthritis, osteoarthritis, irritable bowel syndrome, Crohn's disease, psoriasis, ulcerative colitis, lupus, inflammatory bowel disease, cancer, tumor metastasis, viral infections, bacterial infections, insulin resistance, diabetes, ocular hypertension, preterm labor, atherosclerosis, spinal muscular atrophy, encephalomyelitis, osteoporosis, HIV-1, encephalitis, ischemic CNS disorders, vascular or AD type dementia, glaucoma, retinopathy, benign prostatic hypertrophy, psychiatric disorders, in particular depression, schizophrenia, obsessive compulsive disorder and bipolar disorder, epilepsy and seizure disorders, for decreasing ischemia-reperfusion injury, myocardial infarct size and myocardial fibrosis, for the prevention of graft failure, and cystic fibrosis, said composition comprising an excipient and a therapeutically effective amount of a compound of Formula (Ic), or pharmaceutically acceptable salts thereof.

Another embodiment pertains to a composition for treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia, said composition comprising an excipient and a therapeutically effective amount of a compound of Formula (Ic), or pharmaceutically acceptable salts thereof.

Another embodiment pertains to a method of treating hypertension, chronic and congestive heart failure, cardiac hypertrophy, restenosis, chronic renal failure, cerebral vasospasm after subarachnoid bleeding, pulmonary hypertension, atherosclerosis, asthma, male erectile dysfunctions, female sexual dysfunction, over-active bladder syndrome, spinal-cord injury, traumatic brain injury, stroke, inflammatory and demyelinating diseases, Alzheimer's disease, pain, multiple sclerosis, amyotrophic lateral sclerosis, Huntington's disease, Parkinson's disease, inflammatory pain, rheumatoid arthritis, osteoarthritis, irritable bowel syndrome, Crohn's disease, psoriasis, ulcerative colitis, lupus, inflammatory bowel disease, cancer, tumor metastasis, viral infections, bacterial infections, insulin resistance, diabetes, ocular hypertension, preterm labor, atherosclerosis, spinal muscular atrophy, encephalomyelitis, osteoporosis, HIV-1, encephalitis, ischemic CNS disorders, vascular or AD type dementia, glaucoma, retinopathy, benign prostatic hypertrophy, psychiatric disorders, in particular depression, schizophrenia, obsessive compulsive disorder and bipolar disorder, epilepsy and seizure disorders, for decreasing ischemia-reperfusion injury, myocardial infarct size and myocardial fibrosis, for the prevention of graft failure, and cystic fibrosis, in a patient, said method comprising administering to the patient a therapeutically effective amount of a compound of Formula (Ic), or pharmaceutically acceptable salts thereof.

Another embodiment pertains to a method of treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia in a patient, said method comprising administering to the patient a therapeutically effective amount of a compound of Formula (Ic), or pharmaceutically acceptable salts thereof.

Another embodiment pertains to a method of treating hypertension, chronic and congestive heart failure, cardiac hypertrophy, restenosis, chronic renal failure, cerebral vasospasm after subarachnoid bleeding, pulmonary hypertension, atherosclerosis, asthma, male erectile dysfunctions, female sexual dysfunction, over-active bladder syndrome, spinal-cord injury, traumatic brain injury, stroke, inflammatory and demyelinating diseases, Alzheimer's disease, pain, multiple sclerosis, amyotrophic lateral sclerosis, Huntington's disease, Parkinson's disease, inflammatory pain, rheumatoid arthritis, osteoarthritis, irritable bowel syndrome, Crohn's disease, psoriasis, ulcerative colitis, lupus, inflammatory bowel disease, cancer, tumor metastasis, viral infections, bacterial infections, insulin resistance, diabetes, ocular hypertension, preterm labor, atherosclerosis, spinal muscular atrophy, encephalomyelitis, osteoporosis, HIV-1, encephalitis, ischemic CNS disorders, vascular or AD type dementia, glaucoma, retinopathy, benign prostatic hypertrophy, psychiatric disorders, in particular depression, schizophrenia, obsessive compulsive disorder and bipolar disorder, epilepsy and seizure disorders, for decreasing ischemia-reperfusion injury, myocardial infarct size and myocardial fibrosis, for the prevention of graft failure, and cystic fibrosis in a patient, said method comprising administering to the patient therapeutically effective amount of the compound of Formula (Ic), or pharmaceutically acceptable salts thereof; and a therapeutically effective amount of one additional therapeutic agent or more than one additional therapeutic agent.

Another embodiment pertains to a method of treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia or spleen cancer in a patient, said method comprising administering to the patient therapeutically effective amount of the compound of Formula (Ic), or pharmaceutically acceptable salts thereof; and a therapeutically effective amount of one additional therapeutic agent or more than one additional therapeutic agent.

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

ABBREVIATIONS AND DEFINITIONS

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated hydrocarbyl substituent typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight- or branched-chain hydrocarbyl substituent containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight- or branched-chain hydrocarbyl substituent containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 8 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls. In a bridged cycloalkyl, the rings share at least two common non-adjacent atoms. Examples of bridged cycloalkyls include bicyclo[2.2.1]heptanyl and adamantanyl.

The term "aryl" (alone or in combination with another term(s)) means an aromatic carbocyclyl containing from 6 to 14 carbon ring atoms. An aryl may be monocyclic or polycyclic (i.e., may contain more than one ring). In the case of polycyclic aromatic rings, only one ring in the polycyclic system is required to be unsaturated while the remaining ring(s) may be saturated, partially saturated or unsaturated. Examples of aryls include phenyl, naphthalenyl, indenyl, 2,3-dihydroindenyl, indanyl, and tetrahydronapthyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_8$-cycloalkyl means a saturated hydrocarbyl ring containing from 3 to 8 carbon ring atoms.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —$NH_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—$NH_2$.

The term "oxo" (alone or in combination with another term(s)) means (=O).

The term "oxy" (alone or in combination with another term(s)) means an ether substituent, and may be depicted as —O—.

The term "alkylhydroxy" (alone or in combination with another term(s)) means -alkyl-OH.

The term "alkylamino" (alone or in combination with another term(s)) means -alkyl-$NH_2$.

The term "alkyloxy" (alone or in combination with another term(s)) means an alkylether substituent, i.e., —O-alkyl. Examples of such a substituent include methoxy (—O—$CH_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-$NH_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-5-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—$NH_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 20 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include 1,2,3,6-tetrahydropyridine, thiomorpholinyl, tetrahydropyranyl, furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, pyrrolidin-2-onyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl(furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, pyrrolidin-2-only, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, diazepinyl, thiomorpholinyl, tetrahydrothiophenyl 1,1-dioxidyl, tetrahydro-2H-thiopyranyl, 1,1-dioxidyl, oxetanyl, azetidinyl, thiazolyl, azepanyl, azepan-2-onyl, and dioxolayl (including 1,3-dioxolanyl).

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, two or more rings may be fused together, such that two rings share one common bond. Examples of fused ring heterocyclyls containing two, three or four rings include hexahydro-furo[3,4-c]pyrrole, hexahydro-furo[3,4-b]pyrrole, octahydro-pyrrolo[3,4-b]pyridine, octahydro-pyrrolo[3,4-c]pyridine, (3aR,6aR)-5-methyl-octahydro-pyrrolo[3,4-b]pyrrole, (3aR,6aR)-octahydro-pyrrolo[3,4-b]pyrrole, 6-methyl-2,6-diaza-bicyclo[3.2.0]heptane, (3aS,6aR)-2-methyl-octahydro-pyrrolo[3,4-c]pyrrole, decahydro-[1,5]naphthyridine, 2,3-dihydrobenzofuranyl, 2,3,4,9-tetrahydro-1H-pyrido[3,4-b]indolyl, thieno[3,2-c]pyridinyl, furo[3,2-c]pyridinyl, isoindolin-1-onyl, phthalazin-1(2H)-onyl, isoquinolinyl, isoquinolin-1(2H)-onyl, 5,6,7,8-tetrahydro-phthalazin-1(2H)-onyl, fluorophthalazin-1(2H)-onyl, (Z)-3H-benzo[d][1,2]diazepin-4(5H)-onyl, (trifluoromethyl)phthalazin-1(2H)-onyl, pyrrolo[1,2-d][1,2,4]triazin-1(2H)-onyl, 1,2,3,4-tetrahydroisoquinolinyl, 2,3-dihydrobenzo[b][1,4]dioxinyl, 5,6,7,8-tetrahydrophthalazin-1(2H)-onyl, 5,6,7,8-tetrahydro-[1,2,4]triazolo[4,3-a]pyrazinyl, 5,6,7,8-tetrahydroimidazo[1,5-a]pyrazinyl, thieno[3,2-c]pyridinyl, furo[3,2-c]pyridinyl, indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), pteridinyl, 4,5,6,7-tetrahydro-indolyl, 5,6,7,8-tetrahydroimidazo[1,5-a]pyrazinyl, 6,7-dihydropyrrolo[3,4-d]pyrimidinyl, 6,7-dihydropyrrolo[3,4-b]pyridinyl, 2,3-dihydropyrrolo[3,4-c]pyridinyl, 6,7-dihydrobenzofuran-4(5H)-onyl, indolinyl, benzo[d][1,3]dioxolyl, isoquinolinyl, indolyl, quinolin-2(1H)-onyl, benzo[d]imidazolyl, 1,2,3,4-tetrahydrocyclobuta[c]quinolinyl, 1,2-dihydrocyclobuta[c]quinolin-3(4H)-onyl, and 3,3a,4,4a-tetrahydro-2H-furo[2',3':2,3]cyclobuta[1,2-c]quinolin-5(6H)-onyl. Other examples of fused-ring heterocyclyls include benzo-fused heterocyclyls, such as benzimidazolyl, benzo[d][1,3]dioxolyl, indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), benzisoxazinyl (including 1,2-benzisoxazinyl or 1,4-benzisoxazinyl), isoindolin-1-onyl, 2,3-dihydrobenzo[b][1,4]dioxinyl, 1,2,3,4-tetrahydroisoquinolinyl, quinolin-2(1H)-onyl, benzo[d]imidazolyl, 2,3,4,9-tetrahydro-pyrido[3,4-b]indolyl, 1,2,3,4-tetrahydrocyclobuta[c]quinolinyl, 1,2-dihydrocyclobuta[c]quinolin-3(4H)-onyl, and 3,3a,4,4a-tetrahydro-2H-furo[2',3':2,3]cyclobuta[1,2-c]quinolin-5(6H)-onyl. Examples of spirocyclic heterocyclyls include 1,4-dioxa-8-azaspiro[4.5]decanyl, 2-oxa-6-aza-spiro[3.3]heptanyl, bicyclo[2.2.1]heptan-2-only, 6-oxa-1-aza-spiro[3.3]heptanyl, 2-oxa-7-aza-spiro[3.5]nonanyl, 2-oxa-6-aza-spiro[3.5]nonanyl, 2-oxa-5-aza-spiro[3.5]nonanyl, 2-oxa-6-aza-spiro[3.4]octanyl, 2-oxa-5-aza-spiro[3.4]octanyl, 2,7-diazaspiro[3.5]nonane, 1,4-dioxa-8-azaspiro[4.5]decanyl, 2-oxa-9-azaspiro[5.5]undecanyl, 2,9-diazaspiro[5.5]undecanyl, 2,8-diazaspiro[5.5]undecanyl, 1-oxa-8-azaspiro[5.5]undecanyl, 1,8-diazaspiro[5.5]undecanyl, 3,9-diazaspiro[5.5]undecanyl, 1-oxa-4,8-diazaspiro[5.5]undecanyl, 1,8-diazaspiro[4.6]undecanyl, 1-oxa-8-azaspiro[4.5]decanyl, 2,7-diazaspiro[4.5]decanyl, 1,8-diazaspiro[4.5]decanyl, 2,8-diazaspiro[4.5]decanyl, 2,6-diazaspiro[4.5]decanyl, 1,4-dioxaspiro[4.5]decanyl, 1,7-diazaspiro[4.4]nonanyl, 2,7-diazaspiro[4.4]nonanyl, 2,5-diazaspiro[3.5]nonanyl, 2,6-diazaspiro[3.5]nonanyl, 1,7-diazaspiro[3.5]nonanyl, 6-oxa-2-azaspiro[3.5]nonanyl, 1,6-diazaspiro[3.5]nonanyl, 2,6-diazaspiro[3.4]octanyl, 6-oxa-2-azaspiro[3.4]octanyl, 5-oxa-2-azaspiro[3.4]octanyl, and 2,6-diazaspiro[3.3]heptanyl.

The term "heterocycloalkyl" (alone or in combination with another term(s)) means a saturated heterocyclyl. Examples of heterocycloalkyls include piperidine, tetrahydropyranyl, piperazinyl, morpholinyl, azepan-2-oneyl, pyrrolidinyl, 1,3-dioxolanyl, tetrahydrofuranyl, pyrrolidin-2-onyl, oxetanyl, azetidinyl, 2-oxa-9-azaspiro[5.5]undecanyl, 2,9-diazaspiro[5.5]undecanyl, 2,8-diazaspiro[5.5]undecanyl, 1-oxa-8-azaspiro[5.5]undecanyl, 1,8-diazaspiro[5.5]undecanyl, 3,9-diazaspiro[5.5]undecanyl, 1-oxa-4,8-diazaspiro[5.5]undecanyl, 1,8-diazaspiro[4.6]undecanyl, 1-oxa-8-azaspiro[4.5]decanyl, 2,7-diazaspiro[4.5]decanyl, 1,8-diazaspiro[4.5]decanyl, 2,8-diazaspiro[4.5]decanyl, 2,6-diazaspiro[4.5]decanyl, 1,4-dioxaspiro[4.5]decanyl, 1,7-diazaspiro[4.4]nonanyl, 2,7-diazaspiro[4.4]nonanyl, 2,5-diazaspiro[3.5]nonanyl, 2,6-diazaspiro[3.5]nonanyl, 1,7-diazaspiro[3.5]nonanyl, 6-oxa-2-azaspiro[3.5]nonanyl, 1,6-diazaspiro[3.5]nonanyl, 2,6-diazaspiro[3.4]octanyl, 6-oxa-2-azaspiro[3.4]octanyl, 5-oxa-2-azaspiro[3.4]octanyl, bicyclo[2.2.1]heptan-2-onyl, 1,4- dioxa-8-azaspiro[4.5]decanyl, 2,7-diazaspiro[3.5]nonanyl and 2,6-diazaspiro[3.3]heptanyl.

The term "heteroaryl" (alone or in combination with another term(s)) means an aromatic heterocyclyl containing from 5 to 14 ring atoms. A heteroaryl may be monocyclic or polycyclic (i.e., may contain more than one ring). In the case of a polycyclic heteroaryl, only one heterocyclyl ring in the polycyclic system is required to be unsaturated while the remaining ring(s) may be saturated, partially saturated or unsaturated. Examples of heteroaryl substituents include: 6-membered ring substituents such as pyridyl, pyrazyl, pyrrolyl, isoxazolyl, 1,2,3-triazolyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, and 1,3,4-, oxadiazolyl and isothiazolyl; 6/5-membered fused ring substituents such as indolyl, benzothiofuranyl, benzisoxazolyl, benzoxazolyl, purinyl, 4,5,6,7-tetrahydro-indolyl, furo[3,2-c]pyridinyl, pyrrolo[1,2-d][1,2,4]triazin-1(2H)-onyl, thieno[3,2-c]pyridinyl, 5,6,7,8-tetrahydroimidazo[1,5-a]pyrazinyl, benzo[d]imidazolyl, 6,7-dihydro-pyrrolo[3,4-d]pyrimidinyl, 6,7-dihydro-pyrrolo[3,4-b]pyridinyl, 2,3-dihydro-pyrrolo[3,4-c]pyridinyl, 5,6,7,8-tetrahydroimidazo[1,5-a]pyrazinyl, 6,7-dihydrobenzofuran-4(5H)-onyl, 6,7-dihydrobenzofuran-4(5H)-onyl, and indolyl; 6/6-membered fused rings such as benzopyranyl, quinolinyl, isoquinolinyl, cinnolinyl, quinazolinyl, benzoxazinyl, 5,6,7,8-tetrahydrophthalazin-1(2H)-onyl, phthalazin-1(2H)-onyl, isoquinolin-1(2H)-onyl, and quinolin-2(1H)-onyl; 6/5/6 membered rings such as 2,3,4,9-tetrahydro-1H-pyrido[3,4-b]indolyl, and 1,2-dihydrocyclobuta[c]quinolin-3(4H)-onyl; and 6/6/4/5 membered rings such as 2,3,4,9-tetrahydro-pyrido[3,4-b]indolyl.

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/ or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2$H, $^3$H, $^{13}$C, $^{14}$C, $^{15}$N, $^{18}$O, $^{32}$P, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. In addition to the above, relevant procedures and intermediates are disclosed, for instance, in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of Bcl-2 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.*, 36(10):927-932 (1995); Kushner et al., *Can. J. Physiol. Pharmacol.*, 77, 79-88 (1999)).

In addition, non-radio active isotope containing drugs, such as deuterated drugs called "heavy drugs," can be used for the treatment of diseases and conditions related to Bcl-2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., *Am. J. Physiol.* 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

Compounds

Suitable groups for $X^1$, $X^2$, $X^3$, and $R^2$ in compounds of Formula (I) are independently selected. The described embodiments of the present invention may be combined. Such combination is contemplated and within the scope of the present invention. For example, it is contemplated that embodiments for any of $X^1$, $X^2$, $X^3$, and $R^2$ can be combined with embodiments defined for any other of $X^1$, $X^2$, $X^3$, and $R^2$.

Embodiments of Formula (I)

One embodiment of this invention, therefore, pertains to compounds or pharmaceutically acceptable salts, which are useful as inhibitors of NAMPT, the compounds having Formula (I)

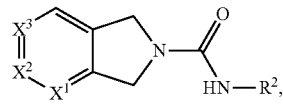

Formula (I)

wherein
$X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N;
$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, C(O)H, $CF_3$, C(O)OH, or $C(O)NH_2$;
$R^2$ is alkyl, alkenyl, alkynyl, phenyl, heterocyclyl, cycloalkyl, or cycloalkenyl; wherein each alkyl, alkenyl, and alkynyl is optionally substituted with one or more independently selected $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, C(O)H, C(O)OH, OH, (O), CN, $N_3$, $NO_2$, $CF_3$, $CF_2CF_3$, $OCF_3$, $OCF_2CF_3$, F, Cl, Br or I; wherein each phenyl is optionally substituted at the para position with one independently selected $R^5$, $OCH_2CH_2CH_2CH_2CH_2CH_3$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, C(O)H, C(O)OH, OH, CN, $N_3$, $NO_2$, $CF_3$, $CF_2CF_3$, $OCF_3$, $OCF_2CF_3$, Br or I; wherein each phenyl is optionally substituted with one F; wherein each heterocyclyl, cycloalkyl, and cycloalkenyl is optionally substituted with one or more independently selected $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, C(O)H, C(O)OH, OH, CN, $N_3$, $CF_3$, $CF_2CF_3$, $OCF_3$, $OCF_2CF_3$, F, Cl, Br or I; wherein $R^2$ is not 4-methylphenyl;
$R^3$ is alkyl, alkenyl, alkynyl, aryl, or heterocyclyl; wherein each alkyl, alkenyl, and alkynyl is optionally substituted with one or more independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, C(O)H, C(O)OH, OH, (O), CN, $N_3$, $NO_2$, $CF_3$, $CF_2CF_3$, $OCF_3$, $OCF_2CF_3$, F, Cl, Br or I;

$R^4$ is alkyl, alkenyl, alkynyl, aryl or heterocyclyl; wherein each alkyl, alkenyl, and alkynyl is optionally substituted with one or more independently selected $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, C(O)NHOH, $C(O)NHOR^7$, $C(O)NHSO_2R^7$, $C(O)NR^7SO_2R^7$, $SO_2NH_2$, $SO_2NHR^7$, $SO_2N(R^7)_2$, C(O)H, C(O)OH, OH, (O), CN, $N_3$, $NO_2$, $CF_3$, $CF_2CF_3$, $OCF_3$, $OCF_2CF_3$, F, Cl, Br or I; wherein each aryl and heterocycyl is optionally substituted with one or more independently selected $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, C(O)NHOH, $C(O)NHOR^8$, $C(O)NHSO_2R^8$, $C(O)NR^8SO_2R^8$, $SO_2NH_2$, $SO_2NHR^8$, $SO_2N(R^8)_2$, C(O)H, C(O)OH, OH, CN, $N_3$, $NO_2$, $CF_3$, $CF_2CF_3$, $OCF_3$, $OCF_2CF_3$, F, Cl, Br or I;

$R^5$ is alkyl, alkenyl, alkynyl, aryl, heterocyclyl, cycloalkyl, or cycloalkenyl; wherein each alkyl, alkenyl, and alkynyl is optionally substituted with one or more independently selected $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, C(O)NHOH, $C(O)NHOR^9$, $C(O)NHSO_2R^9$, $C(O)NR^9SO_2R^9$, $SO_2NH_2$, $SO_2NHR^9$, $SO_2N(R^9)_2$, C(O)H, C(O)OH, OH, (O), CN, $N_3$, $NO_2$, $CF_3$, $CF_2CF_3$, $OCF_3$, $OCF_2CF_3$, F, Cl, Br or I;

$R^6$ is alkyl, alkenyl, alkynyl, aryl, heterocyclyl, cycloalkyl, or cycloalkenyl; wherein each alkyl, alkenyl, and alkynyl is optionally substituted with one or more independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, OH, (O), C(O)OH, $N_3$, CN, $NH_2$, $CF_3$, $CF_2CF_3$, F, Cl, Br or I;

$R^7$ is alkyl, alkenyl, alkynyl, aryl, heterocyclyl, cycloalkyl, or cycloalkenyl; wherein each alkyl, alkenyl, and alkynyl is optionally substituted with one or more independently selected $R^{11}$, $OR^{11}$, $SR^{11}$, $S(O)R^{11}$, $SO_2R^{11}$, $NHR^{11}$, $N(R^{11})_2$, $C(O)R^{11}$, $C(O)NH_2$, $C(O)NHR^{11}$, $SO_2N(R^{11})_2$, $NHC(O)NH_2$, $NHC(O)NHR^{11}$, OH, (O), C(O)OH, $N_3$, CN, $NH_2$, $CF_3$, $CF_2CF_3$, F, Cl, Br or I;

$R^8$ is alkyl, alkenyl, alkynyl, aryl, heterocyclyl, cycloalkyl, or cycloalkenyl; wherein each alkyl, alkenyl, and alkynyl is optionally substituted with one or more independently selected $R^{12}$, $OR^{12}$, $SR^{12}$, $S(O)R^{12}$, $SO_2R^{12}$, $NHR^{12}$, $N(R^{12})_2$, $C(O)R^{12}$, $C(O)NH_2$, $C(O)NHR^{12}$, $C(O)N(R^{12})_2$, $NHC(O)R^{12}$, $NR^{12}C(O)R^{12}$, $NHSO_2R^{12}$, $NHC(O)OR^{12}$, $SO_2NH_2$, $SO_2NHR^{12}$, $SO_2N(R^{12})_2$, $NHC(O)NH_2$, $NHC(O)NHR^{12}$, OH, (O), C(O)OH, $N_3$, CN, $NH_2$, $CF_3$, $CF_2CF_3$, F, Cl, Br or I;

$R^9$ is alkyl, alkenyl, alkynyl, aryl, heterocyclyl, cycloalkyl, or cycloalkenyl; wherein each alkyl, alkenyl, and alkynyl is optionally substituted with one or more independently selected $OCH_3$, or aryl;

$R^{10}$ is alkyl, alkenyl, alkynyl, aryl, heterocyclyl, cycloalkyl, or cycloalkenyl;

$R^{11}$ is alkyl, alkenyl, alkynyl, aryl, heterocyclyl, cycloalkyl, or cycloalkenyl;

$R^{12}$ is alkyl, alkenyl, alkynyl, aryl, heterocyclyl, cycloalkyl, or cycloalkenyl;

wherein the cyclic moieties represented by $R^3$, $R^5$, $R^6$, $R^7$, $R^8$, $R^9$, $R^{10}$, $R^{11}$, and $R^{12}$ are optionally substituted with one or more independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, C(O)NHOH, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, C(O)H, C(O)OH, OH, CN, $N_3$, $NO_2$, $CF_3$, $CF_2CF_3$, $OCF_3$, $OCF_2CF_3$, $SCF_3$, F, Cl, Br or I;

$R^{13}$ is alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, cycloalkyl, or cycloalkenyl; wherein each alkyl, alkenyl, and alkynyl is optionally substituted with one or more independently selected $R^{14}$, $OR^{14}$, $SR^{14}$, $S(O)R^{14}$, $SO_2R^{14}$, $C(O)R^{14}$, $CO(O)R^{14}$, $OC(O)R^{14}$, $OC(O)OR^{14}$, $NH_2$, $NHR^{14}$, $N(R^{14})_2$, $NHC(O)R^{14}$, $NR^{14}$, $C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, C(O)NHOH, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, C(O)H, C(O)OH, OH, (O), CN, $N_3$, $NO_2$, $CF_3$, $CF_2CF_3$, $OCF_3$, $OCF_2CF_3$, F, Cl, Br or I; wherein each aryl, tetrahydrofuranyl, pyridazinyl, pyrazinyl, pyrimidinyl, pridinyl, thieno[3,2-c]pyridinyl, furo[3,2-c]pyridinyl, pyrrolidin-2-onyl, cycloalkyl, and cycloalkenyl is optionally substituted with one or more independently selected $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, C(O)NHOH, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, C(O)H, C(O)OH, OH, CN, $N_3$, $NO_2$, $CF_3$, $CF_2CF_3$, $OCF_3$, $OCF_2CF_3$, F, Cl, Br or I;

$R^{14}$ is alkyl, alkenyl, alkynyl, aryl, heterocyclyl, cycloalkyl, or cycloalkenyl; wherein each alkyl, alkenyl, and alkynyl is optionally substituted with one or more independently selected $NH_2$, $SO_2NH_2$, C(O)H, C(O)OH, OH, (O), CN, $N_3$, $NO_2$, $CF_3$, $CF_2CF_3$, $OCF_3$, $OCF_2CF_3$, F, Cl, Br or I; and $R^{15}$ is alkyl.

In one embodiment of Formula (I), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N. In another embodiment of Formula (I), $X^1$, $X^2$, and $X^3$ are CH. In another embodiment of Formula (I), $X^1$ and $X^3$ are CH; and $X^2$ is N. In another embodiment of Formula (I), $X^1$ and $X^3$ are CH; and $X^2$ is $CR^1$. In another embodiment of Formula (I), $X^2$ and $X^3$ are CH; and $X^1$ is $CR^1$. In another embodiment of Formula (I), $X^1$ is CH; and $X^2$ and $X^3$ are $CR^1$. In another embodiment of Formula (I), $X^2$ is CH; and $X^1$ and $X^3$ are N. In another embodiment of Formula (I), $X^2$ and $X^3$ are CH; and $X^1$ is N.

In another embodiment of Formula (I), $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (I), $R^1$ is $R^3$, $OR^3$, $C(O)OR^3$, C(O)

$NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $R^1$ is $C(O)NH_2$. In another embodiment of Formula (I), $R^1$ is F. In another embodiment of Formula (I), $R^1$ is Cl. In another embodiment of Formula (I), $R^1$ is Br. In another embodiment of Formula (I), $R^1$ is CN. In another embodiment of Formula (I), $R^1$ is $NH_2$. In another embodiment of Formula (I), $R^1$ is $NO_2$. In another embodiment of Formula (I), $R^1$ is $CF_3$. In another embodiment of Formula (I), $R^1$ is $C(O)OH$.

In another embodiment of Formula (I), $X^1$ and $X^3$ are CH; and $X^2$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (I), $X^1$ and $X^3$ are CH; and $X^2$ is $CR^1$; $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $X^1$ and $X^3$ are CH; and $X^2$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $X^1$ and $X^3$ are CH; and $X^2$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $X^1$ and $X^3$ are CH; and $X^2$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $X^1$ and $X^3$ are CH; and $X^2$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $X^1$ and $X^3$ are CH; and $X^2$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $X^1$ and $X^3$ are CH; and $X^2$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $X^1$ and $X^3$ are CH; and $X^2$ is $CR^1$; and $R^1$ is $C(O)NH_2$. In another embodiment of Formula (I), $X^1$ and $X^3$ are CH; and $X^2$ is $CR^1$; and $R^1$ is F. In another embodiment of Formula (I), $X^1$ and $X^3$ are CH; and $X^2$ is $CR^1$; and $R^1$ is Cl. In another embodiment of Formula (I), $X^1$ and $X^3$ are CH; and $X^2$ is $CR^1$; and $R^1$ is Br. In another embodiment of Formula (I), $X^1$ and $X^3$ are CH; and $X^2$ is $CR^1$; and $R^1$ is CN. In another embodiment of Formula (I), $X^1$ and $X^3$ are CH; and $X^2$ is $CR^1$; and $R^1$ is $NH_2$. In another embodiment of Formula (I), $X^1$ and $X^3$ are CH; and $X^2$ is $CR^1$; and $R^1$ is $NO_2$. In another embodiment of Formula (I), $X^1$ and $X^3$ are CH; and $X^2$ is $CR^1$; and $R^1$ is $CF_3$. In another embodiment of Formula (I), $X^1$ and $X^3$ are CH; and $X^2$ is $CR^1$; and $R^1$ is $C(O)OH$.

In another embodiment of Formula (I), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (I), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $X^2$ and $X^3$ are CH; and $X^1$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $X^2$ and $X^3$ are CH; and $X^1$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $X^2$ and $X^3$ are CH; and $X^1$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $X^2$ and $X^3$ are CH; and $X^1$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $X^2$ and $X^3$ are CH; and $X^1$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $X^2$ and $X^3$ are CH; and $X^1$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $X^2$ and $X^3$ are CH; and $X^1$ is $CR^1$; and $R^1$ is $C(O)NH_2$. In another embodiment of Formula (I), $X^2$ and $X^3$ are CH; and $X^1$ is $CR^1$; and $R^1$ is F. In another embodiment of Formula (I), $X^2$ and $X^3$ are CH; and $X^1$ is $CR^1$; and $R^1$ is Cl. In another embodiment of Formula (I), $X^2$ and $X^3$ are CH; and $X^1$ is $CR^1$; and $R^1$ is Br. In another embodiment of Formula (I), $X^2$ and $X^3$ are CH; and $X^1$ is $CR^1$; and $R^1$ is CN. In another embodiment of Formula (I), $X^2$ and $X^3$ are CH; and $X^1$ is $CR^1$; and $R^1$ is $NH_2$. In another embodiment of Formula (I), $X^2$ and $X^3$ are CH; and $X^1$ is $CR^1$; and $R^1$ is $NO_2$. In another embodiment of Formula (I), $X^2$ and $X^3$ are CH; and $X^1$ is $CR^1$; and $R^1$ is $CF_3$. In another embodiment of Formula (I), $X^2$ and $X^3$ are CH; and $X^1$ is $CR^1$; and $R^1$ is C(O)OH.

In another embodiment of Formula (I), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (I), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $X^1$ is CH; and $X^2$ and $X^3$ are $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $X^1$ is CH; and $X^2$ and $X^3$ are $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $X^1$ is CH; and $X^2$ and $X^3$ are $CR^1$; $R^1$ is C(O)$OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $X^1$ is CH; and $X^2$ and $X^3$ are $CR^1$; $R^1$ is C(O)$NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $X^1$ is CH; and $X^2$ and $X^3$ are $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $X^1$ is CH; and $X^2$ and $X^3$ are $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (I), $X^1$ is CH; and $X^2$ and $X^3$ are $CR^1$; and $R^1$ is $C(O)NH_2$. In another embodiment of Formula (I), $X^1$ is CH; and $X^2$ and $X^3$ are $CR^1$; and $R^1$ is F. In another embodiment of Formula (I), $X^1$ is CH; and $X^2$ and $X^3$ are $CR^1$; and $R^1$ is Cl. In another embodiment of Formula (I), $X^1$ is CH; and $X^2$ and $X^3$ are $CR^1$; and $R^1$ is Br. In another embodiment of Formula (I), $X^1$ is CH; and $X^2$ and $X^3$ are $CR^1$; and $R^1$ is CN. In another embodiment of Formula (I), $X^1$ is CH; and $X^2$ and $X^3$ are $CR^1$; and $R^1$ is $NH_2$. In another embodiment of Formula (I), $X^1$ is CH; and $X^2$ and $X^3$ are $CR^1$; and $R^1$ is $NO_2$. In another embodiment of Formula (I), $X^1$ is CH; and $X^2$ and $X^3$ are $CR^1$; and $R^1$ is $CF_3$. In another embodiment of Formula (I), $X^1$ is CH; and $X^2$ and $X^3$ are $CR^1$; and $R^1$ is C(O)OH.

In one embodiment of Formula (I),
$X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N;
$R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH;

$R^2$ is alkyl, phenyl, heterocyclyl; wherein each alkyl is optionally substituted with one or more independently selected $R^4$, $OR^4$, $C(O)R^4$, $CO(O)R^4$, $NHC(O)R^4$, $C(O)NHR^4$, F, Cl, Br or I; each phenyl is optionally substituted at the para position with one independently selected $R^5$, $OCH_2CH_2CH_2CH_2CH_2CH_3$, $C(O)R^5$, $NHR^5$, $NHC(O)R^5$, $C(O)NH_2$, $C(O)NHR^5$, $C(O)N(R^5)_2$, or $CF_3$; wherein each phenyl is optionally substituted with one F; wherein each heterocyclyl is optionally substituted with one or more independently selected $R^5$, $C(O)R^5$, $NHC(O)R^5$, $C(O)NHR^5$, F, Cl, Br or I; wherein $R^2$ is not 4-methylphenyl;

$R^3$ is alkyl, alkenyl, or heterocyclyl; wherein each alkyl is optionally substituted with one or more independently selected $R^6$, $OR^6$, $NH_2$, $N(R^6)_2$, OH, F, Cl, Br or I;

$R^4$ is alkyl, aryl or heterocyclyl; wherein each alkyl is optionally substituted with one or more independently selected $R^7$, F, Cl, Br or I; wherein each aryl and heterocycyl is optionally substituted with one or more independently selected $R^8$, $C(O)R^8$, F, Cl, Br or I;

$R^5$ is alkyl, alkenyl, alkynyl, aryl, heterocyclyl, or cycloalkyl; wherein each alkyl, alkenyl, and alkynyl is optionally substituted with one or more independently selected $R^9$, $OR^9$, $SR^9$, $C(O)R^9$, $NH_2$, $N(R^9)_2$, $NHC(O)R^9$, $C(O)NH_2$, C(O)OH, OH, CN, $CF_3$, F, Cl, Br or I;

$R^6$ is alkyl or heterocyclyl;

$R^7$ is aryl;

$R^8$ is alkyl, aryl, or heterocyclyl;

$R^9$ is alkyl, aryl, heterocyclyl, or cycloalkyl; wherein each alkyl is optionally substituted with one or more independently selected $OCH_3$, or aryl;

wherein the cyclic moieties represented by $R^3$, $R^5$, $R^6$, $R^7$, $R^8$, and $R^9$ are optionally substituted with one or more independently selected $R^{13}$, $OR^{13}SO_2R^{13}$, $C(O)R^{13}$, $CO(O)R^{13}$, $NH_2$, $N(R^{13})_2$, $NHC(O)R^{13}$, $NHC(O)OR^{13}$, $C(O)NH_2$, $C(O)N(R^{13})_2$, OH, CN, $CF_3$, $OCF_3$, $SCF_3$, F, Cl, Br or I;

$R^{13}$ is alkyl, aryl, tetrahydrofuranyl, pyridazinyl, pyrazinyl, pyrimidinyl, pyridinyl, thieno[3,2-c]pyridinyl, furo[3,2-c]pyridinyl, or pyrrolidin-2-onyl, wherein each alkyl is optionally substituted with one or more independently selected $R^{14}$, $OR^{14}$, $NH_2$, OH, F, Cl, Br or I; wherein each aryl, tetrahydrofuranyl, pyridazinyl, pyrazinyl, pyrimidinyl, pridinyl, thieno[3,2-c]pyridinyl, furo[3,2-c]pyridinyl, pyrrolidin-2-onyl, cycloalkyl, and cycloalkenyl is optionally substituted with one or more independently selected $R^{15}$, $OR^{15}$, $C(O)R^{15}$, CN, $CF_3$, F, Cl, Br or I;

$R^{14}$ is alkyl, aryl, or cycloalkyl; wherein each alkyl is optionally substituted with one or more independently selected OH, F, Cl, Br or I; and $R^{15}$ is alkyl.

Still another embodiment pertains to compounds having Formula (I), which include Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, and pharmaceutically acceptable salts thereof.

Embodiments of Formula (II)

In another aspect, the present invention provides compounds of Formula (II)

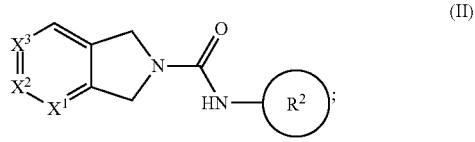

(II)

or pharmaceutically acceptable salts thereof; wherein $X^1$, $X^2$, $X^3$, are as described herein for Formula (I); and $R^2$ is phenyl, heterocyclyl, cycloalkyl, or cycloalkenyl; wherein the phenyl, heterocyclyl, cycloalkyl, and cycloalkenyl are optionally substituted as described herein for Formula (I).

In one embodiment of Formula (II), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N. In another embodiment of Formula (II), $X^1$, $X^2$, and $X^3$ are CH. In another embodiment of Formula (II), $X^1$ and $X^3$ are CH; and $X^2$ is N. In another embodiment of Formula (II), $X^1$ and $X^3$ are CH; and $X^2$ is $CR^1$. In another embodiment of Formula (II), $X^2$ and $X^3$ are CH; and $X^1$ is $CR^1$. In another embodiment of Formula (II), $X^1$ is CH; and $X^2$ and $X^3$ are $CR^1$. In another embodiment of Formula (II), $X^2$ is CH; and $X^1$ and $X^3$ are N. In another embodiment of Formula (II), $X^2$ and $X^3$ are CH; and $X^1$ is N.

In another embodiment of Formula (II), $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (II), $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $R^1$ is $C(O)NH_2$. In another embodiment of Formula (II), $R^1$ is F. In another embodiment of Formula (II), $R^1$ is Cl. In another embodiment of Formula (II), $R^1$ is Br. In another embodiment of Formula (II), $R^1$ is CN. In another embodiment of Formula (II), $R^1$ is $NH_2$. In another embodiment of Formula (II), $R^1$ is $NO_2$. In another embodiment of Formula (II), $R^1$ is $CF_3$. In another embodiment of Formula (II), $R^1$ is $C(O)OH$.

In another embodiment of Formula (II), $X^1$ and $X^3$ are CH; and $X^2$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (II), $X^1$ and $X^3$ are CH; and $X^2$ is $CR^1$; $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $X^1$ and $X^3$ are CH; and $X^2$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $X^1$ and $X^3$ are CH; and $X^2$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $X^1$ and $X^3$ are CH; and $X^2$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $X^1$ and $X^3$ are CH; and $X^2$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $X^1$ and $X^3$ are CH; and $X^2$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $X^1$ and $X^3$ are CH; and $X^2$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $X^1$ and $X^3$ are CH; and $X^2$ is $CR^1$; and $R^1$ is $C(O)NH_2$. In another embodiment of Formula (II), $X^1$ and $X^3$ are CH; and $X^2$ is $CR^1$; and $R^1$ is F. In another embodiment of Formula (II), $X^1$ and $X^3$ are CH; and $X^2$ is $CR^1$; and $R^1$ is Cl. In another embodiment of Formula (II), $X^1$ and $X^3$ are CH; and $X^2$ is $CR^1$; and $R^1$ is Br. In another embodiment of Formula (II), $X^1$ and $X^3$ are CH; and $X^2$ is $CR^1$; and $R^1$ is CN. In another embodiment of Formula (II), $X^1$ and $X^3$ are CH; and $X^2$ is $CR^1$; and $R^1$ is $NH_2$. In another embodiment of Formula (II), $X^1$ and $X^3$ are CH; and $X^2$ is $CR^1$; and $R^1$ is $NO_2$. In another embodiment of Formula (II), $X^1$ and $X^3$ are CH; and $X^2$ is $CR^1$; and $R^1$ is $CF_3$. In another embodiment of Formula (II), $X^1$ and $X^3$ are CH; and $X^2$ is $CR^1$; and $R^1$ is C(O)OH.

In another embodiment of Formula (II), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (II), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $X^2$ and $X^3$ are CH; and $X^1$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $X^2$ and $X^3$ are CH; and $X^1$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $X^2$ and $X^3$ are CH; and $X^1$ is $CR^1$; $R^1$ is C(O)$OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $X^2$ and $X^3$ are CH; and $X^1$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $X^2$ and $X^3$ are CH; and $X^1$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $X^2$ and $X^3$ are CH; and $X^1$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $X^2$ and $X^3$ are CH; and $X^1$ is $CR^1$; and $R^1$ is $C(O)NH_2$. In another embodiment of Formula (II), $X^2$ and $X^3$ are CH; and $X^1$ is $CR^1$; and $R^1$ is F. In another embodiment of Formula (II), $X^2$ and $X^3$ are CH; and $X^1$ is $CR^1$; and $R^1$ is Cl. In another embodiment of Formula (II), $X^2$ and $X^3$ are CH; and $X^1$ is $CR^1$; and $R^1$ is Br. In another embodiment of Formula (II), $X^2$ and $X^3$ are CH; and $X^1$ is $CR^1$; and $R^1$ is CN. In another embodiment of Formula (II), $X^2$ and $X^3$ are CH; and $X^1$ is $CR^1$; and $R^1$ is $NH_2$. In another embodiment of Formula (II), $X^2$ and $X^3$ are CH; and $X^1$ is $CR^1$; and $R^1$ is $NO_2$. In another embodiment of Formula (II), $X^2$ and $X^3$ are CH; and $X^1$ is $CR^1$; and $R^1$ is $CF_3$. In another embodiment of Formula (II), $X^2$ and $X^3$ are CH; and $X^1$ is $CR^1$; and $R^1$ is C(O)OH.

In another embodiment of Formula (II), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (II), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $X^1$ is CH; and $X^2$ and $X^3$ are $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $X^1$ is CH; and $X^2$ and $X^3$ are $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $X^1$ is CH; and $X^2$ and $X^3$ are $CR^1$; $R^1$ is C(O)$OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $X^1$ is CH; and $X^2$ and $X^3$ are $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $X^1$ is CH; and $X^2$ and $X^3$ are $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $X^1$ is CH; and $X^2$ and $X^3$ are $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (II), $X^1$ is CH; and $X^2$ and $X^3$ are $CR^1$; and $R^1$ is $C(O)NH_2$. In another embodiment of Formula (II), $X^1$ is CH; and $X^2$ and $X^3$ are $CR^1$; and $R^1$ is F. In another embodiment of Formula (II), $X^1$ is CH; and $X^2$ and $X^3$ are $CR^1$; and $R^1$ is Cl. In another embodiment of Formula (II), $X^1$ is CH; and $X^2$ and $X^3$ are $CR^1$; and $R^1$ is Br. In another embodiment of Formula (II), $X^1$ is CH; and $X^2$ and $X^3$ are $CR^1$; and $R^1$ is CN. In another embodiment of Formula (II), $X^1$ is CH; and $X^2$ and $X^3$ are $CR^1$; and $R^1$ is $NH_2$. In another embodiment of Formula (II), $X^1$ is CH; and $X^2$ and $X^3$ are $CR^1$; and $R^1$ is $NO_2$. In another embodiment of Formula (II), $X^1$ is CH; and $X^2$ and $X^3$ are $CR^1$; and $R^1$ is $CF_3$. In another embodiment of Formula (II), $X^1$ is CH; and $X^2$ and $X^3$ are $CR^1$; and $R^1$ is C(O)OH.

In one embodiment of Formula (II),
$X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N;
$R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH;

R² is phenyl, or heterocyclyl; wherein each phenyl is optionally substituted at the para position with one independently selected R⁵, OCH₂CH₂CH₂CH₂CH₃, C(O)R⁵, NHR⁵, NHC(O)R⁵, C(O)NH₂, C(O)NHR⁵, C(O)N(R⁵)₂, or CF₃; wherein each phenyl is optionally substituted with one F; wherein each heterocyclyl is optionally substituted with one or more independently selected R⁵, C(O)R⁵, NHC(O)R⁵, C(O)NHR⁵, F, Cl, Br or I; wherein R² is not 4-methylphenyl;

R³ is alkyl, alkenyl, or heterocyclyl; wherein each alkyl is optionally substituted with one or more independently selected R⁶, OR⁶, NH₂, N(R⁶)₂, OH, F, Cl, Br or I;

R⁵ is alkyl, alkenyl, alkynyl, aryl, heterocyclyl, or cycloalkyl; wherein each alkyl, alkenyl, and alkynyl is optionally substituted with one or more independently selected R⁹, OR⁹, SR⁹, C(O)R⁹, NH₂, N(R⁹)₂, NHC(O)R⁹, C(O)NH₂, C(O)OH, OH, CN, CF₃, F, Cl, Br or I;

R⁶ is alkyl or heterocyclyl;

R⁹ is alkyl, aryl, heterocyclyl, or cycloalkyl; wherein each alkyl is optionally substituted with one or more independently selected OCH₃, or aryl;

wherein the cyclic moieties represented by R³, R⁵, R⁶, and R⁹ are optionally substituted with one or more independently selected R¹³, OR¹³SO₂R¹³, C(O)R¹³, CO(O)R¹³, NH₂, N(R¹³)₂, NHC(O)R¹³, NHC(O)OR¹³, C(O)NH₂, C(O)N(R¹³)₂, OH, CN, CF₃, OCF₃, SCF₃, F, Cl, Br or I;

R¹³ is alkyl, aryl, tetrahydrofuranyl, pyridazinyl, pyrazinyl, pyrimidinyl, pyridinyl, thieno[3,2-c]pyridinyl, furo[3,2-c]pyridinyl, or pyrrolidin-2-onyl, wherein each alkyl is optionally substituted with one or more independently selected R¹⁴, OR¹⁴, NH₂, OH, F, Cl, Br or I; wherein each aryl, tetrahydrofuranyl, pyridazinyl, pyrazinyl, pyrimidinyl, pridinyl, thieno[3,2-c]pyridinyl, furo[3,2-c]pyridinyl, pyrrolidin-2-onyl, cycloalkyl, and cycloalkenyl is optionally substituted with one or more independently selected R¹⁵, OR¹⁵, C(O)R¹⁵, CN, CF₃, F, Cl, Br or I;

R¹⁴ is alkyl, aryl, or cycloalkyl; wherein each alkyl is optionally substituted with one or more independently selected OH, F, Cl, Br or I; and R¹⁵ is alkyl.

Still another embodiment pertains to compounds having Formula (II), which include Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 452, 453, 454, 455, and pharmaceutically acceptable salts thereof.

Embodiments of Formula (III)

In another aspect, the present invention provides compounds of Formula (III)

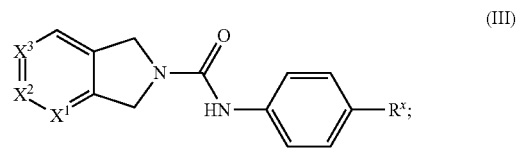

or pharmaceutically acceptable salts thereof; wherein X¹, X², X³, are as described herein for Formula (I); and Rˣ is as described herein for Formula (I) when R² is phenyl.

In one embodiment of Formula (III), X¹, X², and X³ are CH; or X¹ and X³ are CH; and X² is N; or X¹ and X³ are CH; and X² is CR¹; or X² and X³ are CH; and X¹ is CR¹; or X¹ is CH; and X² and X³ are CR¹; or X² is CH; and X¹ and X³ are N; or X² and X³ are CH; and X¹ is N. In another embodiment of Formula (III), X¹, X², and X³ are CH. In another embodiment of Formula (III), X¹ and X³ are CH; and X² is N. In another embodiment of Formula (III), X¹ and X³ are CH; and X² is CR¹. In another embodiment of Formula (III), X² and X³ are CH; and X¹ is CR¹. In another embodiment of Formula (III), X¹ is CH; and X² and X³ are CR¹. In another embodiment of Formula (III), X² is CH; and X¹ and X³ are N. In another embodiment of Formula (III), X² and X³ are CH; and X¹ is N.

In another embodiment of Formula (III), R¹ is R³, OR³, C(O)OR³, C(O)NH₂, C(O)NHR³, NHC(O)R³, NHSO₂R³, F, Cl, Br, I, CN, NH₂, NO₂, CF₃, or C(O)OH. In another embodiment of Formula (III), R¹ is R³, OR³, C(O)OR³, C(O)NH₂, C(O)NHR³, NHC(O)R³, NHSO₂R³, F, Cl, Br, I, CN, NH₂, NO₂, CF₃, or C(O)OH; wherein R³ is alkyl, alkenyl, or heterocyclyl; wherein each alkyl is optionally substituted with one or more independently selected R⁶, OR⁶, NH₂, N(R⁶)₂, or OH; wherein R⁶ is alkyl or heterocyclyl. In another embodiment of Formula (III), R¹ is R³; wherein R³ is alkyl, alkenyl, or heterocyclyl; wherein each alkyl is optionally substituted with one or more independently selected R⁶, OR⁶, NH₂, N(R⁶)₂, or OH; wherein R⁶ is alkyl or heterocyclyl. In another embodiment of Formula (III), R¹ is OR³; wherein R³ is alkyl, alkenyl, or heterocyclyl; wherein each alkyl is optionally substituted with one or more independently selected R⁶, OR⁶, NH₂, N(R⁶)₂, or OH; wherein R⁶ is alkyl or heterocyclyl. In another embodiment of Formula (III), R¹ is C(O)OR³; wherein R³ is alkyl, alkenyl, or heterocyclyl; wherein each alkyl is optionally substituted with one or more independently selected R⁶, OR⁶, NH₂, N(R⁶)₂, or OH; wherein R⁶ is alkyl or heterocyclyl. In another embodiment of Formula (III), R¹ is C(O)NHR³; wherein R³ is alkyl, alkenyl, or heterocyclyl; wherein each alkyl is optionally substituted with one or more independently selected R⁶, OR⁶, NH₂, N(R⁶)₂, or OH; wherein R⁶ is alkyl or heterocyclyl. In another embodiment of Formula (III), R¹ is NHC(O)R³; wherein R³ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $R^1$ is $C(O)NH_2$. In another embodiment of Formula (III), $R^1$ is F. In another embodiment of Formula (III), $R^1$ is Cl. In another embodiment of Formula (III), $R^1$ is Br. In another embodiment of Formula (III), $R^1$ is CN. In another embodiment of Formula (III), $R^1$ is $NH_2$. In another embodiment of Formula (III), $R^1$ is $NO_2$. In another embodiment of Formula (III), $R^1$ is $CF_3$. In another embodiment of Formula (III), $R^1$ is C(O)OH.

In another embodiment of Formula (III), $X^1$ and $X^3$ are CH; and $X^2$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (III), $X^1$ and $X^3$ are CH; and $X^2$ is $CR^1$; $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $X^1$ and $X^3$ are CH; and $X^2$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $X^1$ and $X^3$ are CH; and $X^2$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $X^1$ and $X^3$ are CH; and $X^2$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $X^1$ and $X^3$ are CH; and $X^2$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $X^1$ and $X^3$ are CH; and $X^2$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $X^1$ and $X^3$ are CH; and $X^2$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $X^1$ and $X^3$ are CH; and $X^2$ is $CR^1$; and $R^1$ is $C(O)NH_2$. In another embodiment of Formula (III), $X^1$ and $X^3$ are CH; and $X^2$ is $CR^1$; and $R^1$ is F. In another embodiment of Formula (III), $X^1$ and $X^3$ are CH; and $X^2$ is $CR^1$; and $R^1$ is Cl. In another embodiment of Formula (III), $X^1$ and $X^3$ are CH; and $X^2$ is $CR^1$; and $R^1$ is Br. In another embodiment of Formula (III), $X^1$ and $X^3$ are CH; and $X^2$ is $CR^1$; and $R^1$ is CN. In another embodiment of Formula (III), $X^1$ and $X^3$ are CH; and $X^2$ is $CR^1$; and $R^1$ is $NH_2$. In another embodiment of Formula (III), $X^1$ and $X^3$ are CH; and $X^2$ is $CR^1$; and $R^1$ is $NO_2$. In another embodiment of Formula (III), $X^1$ and $X^3$ are CH; and $X^2$ is $CR^1$; and $R^1$ is $CF_3$. In another embodiment of Formula (III), $X^1$ and $X^3$ are CH; and $X^2$ is $CR^1$; and $R^1$ is C(O)OH.

In another embodiment of Formula (III), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (III), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $X^2$ and $X^3$ are CH; and $X^1$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $X^2$ and $X^3$ are CH; and $X^1$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $X^2$ and $X^3$ are CH; and $X^1$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $X^2$ and $X^3$ are CH; and $X^1$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $X^2$ and $X^3$ are CH; and $X^1$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $X^2$ and $X^3$ are CH; and $X^1$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $X^2$ and $X^3$ are CH; and $X^1$ is $CR^1$; and $R^1$ is $C(O)NH_2$. In another embodiment of Formula (III), $X^2$ and $X^3$ are CH; and $X^1$ is $CR^1$; and $R^1$ is F. In another embodiment of Formula (III), $X^2$ and $X^3$ are CH; and $X^1$ is $CR^1$; and $R^1$ is Cl. In another embodiment of Formula (III), $X^2$ and $X^3$ are CH; and $X^1$ is $CR^1$; and $R^1$ is Br. In another embodiment of Formula (III), $X^2$ and $X^3$ are CH; and $X^1$ is $CR^1$; and $R^1$ is CN. In another embodiment of Formula (III), $X^2$ and $X^3$ are CH; and $X^1$ is $CR^1$; and $R^1$ is $NH_2$. In another embodiment of Formula (III), $X^2$ and $X^3$ are CH; and $X^1$ is $CR^1$; and $R^1$ is $NO_2$. In another embodiment of Formula (III), $X^2$ and $X^3$ are CH; and $X^1$ is $CR^1$; and $R^1$ is $CF_3$. In another embodiment of Formula (III), $X^2$ and $X^3$ are CH; and $X^1$ is $CR^1$; and $R^1$ is C(O)OH.

In another embodiment of Formula (III), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (III), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $X^1$ is CH; and $X^2$ and $X^3$ are $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $X^1$ is CH; and $X^2$ and $X^3$ are $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $X^1$ is CH; and $X^2$ and $X^3$ are $CR^1$; $R^1$ is C(O)$OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $X^1$ is CH; and $X^2$ and $X^3$ are $CR^1$; $R^1$ is C(O)NHR$^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $X^1$ is CH; and $X^2$ and $X^3$ are $CR^1$; $R^1$ is NHC(O)$R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $X^1$ is CH; and $X^2$ and $X^3$ are $CR^1$; $R^1$ is NHSO$_2$R$^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (III), $X^1$ is CH; and $X^2$ and $X^3$ are $CR^1$; and $R^1$ is C(O)NH$_2$. In another embodiment of Formula (III), $X^1$ is CH; and $X^2$ and $X^3$ are $CR^1$; and $R^1$ is F. In another embodiment of Formula (III), $X^1$ is CH; and $X^2$ and $X^3$ are $CR^1$; and $R^1$ is Cl. In another embodiment of Formula (III), $X^1$ is CH; and $X^2$ and $X^3$ are $CR^1$; and $R^1$ is Br. In another embodiment of Formula (III), $X^1$ is CH; and $X^2$ and $X^3$ are $CR^1$; and $R^1$ is CN. In another embodiment of Formula (III), $X^1$ is CH; and $X^2$ and $X^3$ are $CR^1$; and $R^1$ is NH$_2$. In another embodiment of Formula (III), $X^1$ is CH; and $X^2$ and $X^3$ are $CR^1$; and $R^1$ is NO$_2$. In another embodiment of Formula (III), $X^1$ is CH; and $X^2$ and $X^3$ are $CR^1$; and $R^1$ is CF$_3$. In another embodiment of Formula (III), $X^1$ is CH; and $X^2$ and $X^3$ are $CR^1$; and $R^1$ is C(O)OH.

In another embodiment of Formula (III), $R^x$ is phthalazin-1(2H)-onyl, isoquinolinyl, isoquinolin-1(2H)-onyl, 5,6,7,8-tetrahydrophthalazin-1(2H)-onyl, 5-fluorophthalazin-1(2H)-onyl, (Z)-3H-benzo[d][1,2]diazepin-4(5H)-onyl, 5-(trifluoromethyl)phthalazin-1(2H)-onyl, or pyrrolo[1,2-d][1,2,4]triazin-1(2H)-one.

In one embodiment of Formula (III), $X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N;
$R^1$ is $R^3$, $OR^3$, C(O)$OR^3$, C(O)NH$_2$, C(O)NHR$^3$, NHC(O)$R^3$, NHSO$_2$R$^3$, F, Cl, Br, I, CN, NH$_2$, NO$_2$, CF$_3$, or C(O)OH;
$R^x$ is $R^5$, OCH$_2$CH$_2$CH$_2$CH$_2$CH$_2$CH$_3$, C(O)$R^5$, NHR$^5$, NHC(O)$R^5$, C(O)NH$_2$, C(O)NHR$^5$, C(O)N(R$^5$)$_2$, CF$_3$ or F;
$R^3$ is alkyl, alkenyl, or heterocyclyl; wherein each alkyl is optionally substituted with one or more independently selected $R^6$, $OR^6$, NH$_2$, N(R$^6$)$_2$, OH, F, Cl, Br or I;
$R^5$ is alkyl, alkenyl, alkynyl, aryl, heterocyclyl, or cycloalkyl; wherein each alkyl, alkenyl, and alkynyl is optionally substituted with one or more independently selected $R^9$, $OR^9$, $SR^9$, C(O)$R^9$, NH$_2$, N(R$^9$)$_2$, NHC(O)$R^9$, C(O)NH$_2$, C(O)OH, OH, CN, CF$_3$, F, Cl, Br or I;

$R^6$ is alkyl or heterocyclyl;

$R^9$ is alkyl, aryl, heterocyclyl, or cycloalkyl; wherein each alkyl is optionally substituted with one or more independently selected OCH$_3$, or aryl;

wherein the cyclic moieties represented by $R^3$, $R^5$, $R^6$, and $R^9$ are optionally substituted with one or more independently selected $R^{13}$, $OR^{13}$SO$_2$R$^{13}$, C(O)$R^{13}$, CO(O)$R^{13}$, NH$_2$, N(R$^{13}$)$_2$, NHC(O)$R^{13}$, NHC(O)O$R^{13}$, C(O)NH$_2$, C(O)N(R$^{13}$)$_2$, OH, CN, CF$_3$, OCF$_3$, SCF$_3$, F, Cl, Br or I;

$R^{13}$ is alkyl, aryl, tetrahydrofuranyl, pyridazinyl, pyrazinyl, pyrimidinyl, pyridinyl, thieno[3,2-c]pyridinyl, furo[3,2-c]pyridinyl, or pyrrolidin-2-onyl, wherein each alkyl is optionally substituted with one or more independently selected $R^{14}$, $OR^{14}$, NH$_2$, OH, F, Cl, Br or I; wherein each aryl, tetrahydrofuranyl, pyridazinyl, pyrazinyl, pyrimidinyl, pridinyl, thieno[3,2-c]pyridinyl, furo[3,2-c]pyridinyl, pyrrolidin-2-onyl, cycloalkyl, and cycloalkenyl is optionally substituted with one or more independently selected $R^{15}$, $OR^{15}$, C(O)$R^{15}$, CN, CF$_3$, F, Cl, Br or I;

$R^{14}$ is alkyl, aryl, or cycloalkyl; wherein each alkyl is optionally substituted with one or more independently selected OH, F, Cl, Br or I; and $R^{15}$ is alkyl.

Still another embodiment pertains to compounds having Formula (III), which include Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 330, 331, 332, 333, 336, 337, 338, 339, 340, 341, 342, 343, 348, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 405, 406, 407, 408, 409, 410, 411, 412, 413, 414, 415, 416, 417, 418, 419, 420, 421, 424, 425, 426, 427, 428, 429, 430, 431, 432, 433, 434, 435, 436, 437, 438, 439, 440, 441, 442, 443, 444, 445, 446, 447, 448, 449, 450, 375, 376, 377, 378, 379, 380, 381, 382, 383, 384, 385, 386, 387, 388, 389, 390, 391, 392, 393, 394, 395, 396, 397, 398, 399, 400, 547, 548, 549, 550, 551, 552, and pharmaceutically acceptable salts thereof.

Embodiments of Formula (IV)

In another aspect, the present invention provides compounds of Formula (IV)

$$\text{(IV)}$$

or pharmaceutically acceptable salts thereof; wherein $X^1$, $X^2$, $X^3$, and $R^5$ are as described herein for Formula (I).

In one embodiment of Formula (IV), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N. In another embodiment of Formula (IV), $X^1$, $X^2$, and $X^3$ are CH. In another embodiment of Formula (IV), $X^1$ and $X^3$ are CH; and $X^2$ is N. In another embodiment of Formula (IV), $X^1$ and $X^3$ are CH; and $X^2$ is $CR^1$. In another embodiment of Formula (IV), $X^2$ and $X^3$ are CH; and $X^1$ is $CR^1$. In another embodiment of Formula (IV), $X^1$ is CH; and $X^2$ and $X^3$ are $CR^1$. In another embodiment of Formula (IV), $X^2$ is CH; and $X^1$ and $X^3$ are N. In another embodiment of Formula (IV), $X^2$ and $X^3$ are CH; and $X^1$ is N.

In another embodiment of Formula (IV), $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (IV), $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $R^1$ is $C(O)NH_2$. In another embodiment of Formula (IV), $R^1$ is F. In another embodiment of Formula (IV), $R^1$ is Cl. In another embodiment of Formula (IV), $R^1$ is Br. In another embodiment of Formula (IV), $R^1$ is CN. In another embodiment of Formula (IV), $R^1$ is $NH_2$. In another embodiment of Formula (IV), $R^1$ is $NO_2$. In another embodiment of Formula (IV), $R^1$ is $CF_3$. In another embodiment of Formula (IV), $R^1$ is C(O)OH.

In another embodiment of Formula (IV), $X^1$ and $X^3$ are CH; and $X^2$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (IV), $X^1$ and $X^3$ are CH; and $X^2$ is $CR^1$; $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $X^1$ and $X^3$ are CH; and $X^2$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $X^1$ and $X^3$ are CH; and $X^2$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $X^1$ and $X^3$ are CH; and $X^2$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $X^1$ and $X^3$ are CH; and $X^2$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $X^1$ and $X^3$ are CH; and $X^2$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $X^1$ and $X^3$ are CH; and $X^2$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $X^1$ and $X^3$ are CH; and $X^2$ is $CR^1$; and $R^1$ is $C(O)NH_2$. In another embodiment of Formula (IV), $X^1$ and $X^3$ are CH; and $X^2$ is $CR^1$; and $R^1$ is F. In another embodiment of Formula (IV), $X^1$ and $X^3$ are CH; and $X^2$ is $CR^1$; and $R^1$ is Cl. In another embodiment of Formula (IV), $X^1$ and $X^3$ are CH; and $X^2$ is $CR^1$; and $R^1$ is Br. In another embodiment of Formula (IV), $X^1$ and $X^3$ are CH; and $X^2$ is $CR^1$; and $R^1$ is CN. In another embodiment of Formula (IV), $X^1$ and $X^3$ are CH; and $X^2$ is $CR^1$; and $R^1$ is $NH_2$. In another embodiment of Formula (IV), $X^1$ and $X^3$ are CH; and $X^2$ is $CR^1$; and $R^1$ is $NO_2$. In another embodiment of Formula (IV), $X^1$ and $X^3$ are CH; and $X^2$ is $CR^1$; and $R^1$ is $CF_3$. In another embodiment of Formula (IV), $X^1$ and $X^3$ are CH; and $X^2$ is $CR^1$; and $R^1$ is C(O)OH.

In another embodiment of Formula (IV), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (IV), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $X^2$ and $X^3$ are CH; and $X^1$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $X^2$ and $X^3$ are CH; and $X^1$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $X^2$ and $X^3$ are CH; and $X^1$ is $CR^1$; $R^1$ is C(O)$OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $X^2$ and $X^3$ are CH; and $X^1$ is $CR^1$; $R^1$ is C(O)$NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $X^2$ and $X^3$ are CH; and $X^1$ is $CR^1$; $R^1$ is NHC(O)$R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $X^2$ and $X^3$ are CH; and $X^1$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $X^2$ and $X^3$ are CH; and $X^1$ is $CR^1$; and $R^1$ is C(O)$NH_2$. In another embodiment of Formula (IV), $X^2$ and $X^3$ are CH; and $X^1$ is $CR^1$; and $R^1$ is F. In another embodiment of Formula (IV), $X^2$ and $X^3$ are CH; and $X^1$ is $CR^1$; and $R^1$ is Cl. In another embodiment of Formula (IV), $X^2$ and $X^3$ are CH; and $X^1$ is $CR^1$; and $R^1$ is Br. In another embodiment of Formula (IV), $X^2$ and $X^3$ are CH; and $X^1$ is $CR^1$; and $R^1$ is CN. In another embodiment of Formula (IV), $X^2$ and $X^3$ are CH; and $X^1$ is $CR^1$; and $R^1$ is $NH_2$. In another embodiment of Formula (IV), $X^2$ and $X^3$ are CH; and $X^1$ is $CR^1$; and $R^1$ is $NO_2$. In another embodiment of Formula (IV), $X^2$ and $X^3$ are CH; and $X^1$ is $CR^1$; and $R^1$ is $CF_3$. In another embodiment of Formula (IV), $X^2$ and $X^3$ are CH; and $X^1$ is $CR^1$; and $R^1$ is C(O)OH.

In another embodiment of Formula (IV), $X^1$ is CH; and $X^2$ and $X^3$ are $CR^1$; and $R^1$ is $R^3$, $OR^3$, C(O)$OR^3$, C(O)$NH_2$, C(O)$NHR^3$, NHC(O)$R^3$, $NHSO_2R^3$, F, Cl, Br, I, CN, $NH_2$, $NO_2$, $CF_3$, or C(O)OH. In another embodiment of Formula (IV), $X^1$ is CH; and $X^2$ and $X^3$ are $CR^1$; and $R^1$ is $R^3$, $OR^3$, C(O)$OR^3$, C(O)$NH_2$, C(O)$NHR^3$, NHC(O)$R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $X^1$ is CH; and $X^2$ and $X^3$ are $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $X^1$ is CH; and $X^2$ and $X^3$ are $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $X^1$ is CH; and $X^2$ and $X^3$ are $CR^1$; $R^1$ is C(O)$OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $X^1$ is CH; and $X^2$ and $X^3$ are $CR^1$; $R^1$ is C(O)$NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $X^1$ is CH; and $X^2$ and $X^3$ are $CR^1$; $R^1$ is NHC(O)$R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $X^1$ is CH; and $X^2$ and $X^3$ are $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IV), $X^1$ is CH; and $X^2$ and $X^3$ are $CR^1$; and $R^1$ is C(O)$NH_2$. In another embodiment of Formula (IV), $X^1$ is CH; and $X^2$ and $X^3$ are $CR^1$; and $R^1$ is F. In another embodiment of Formula (IV), $X^1$ is CH; and $X^2$ and $X^3$ are $CR^1$; and $R^1$ is Cl. In another embodiment of Formula (IV), $X^1$ is CH; and $X^2$ and $X^3$ are $CR^1$; and $R^1$ is Br. In another embodiment of Formula (IV), $X^1$ is CH; and $X^2$ and $X^3$ are $CR^1$; and $R^1$ is CN. In another embodiment of Formula (IV), $X^1$ is CH; and $X^2$ and $X^3$ are $CR^1$; and $R^1$ is $NH_2$. In another embodiment of Formula (IV), $X^1$ is CH; and $X^2$ and $X^3$ are $CR^1$; and $R^1$ is $NO_2$. In another embodiment of Formula (IV), $X^1$ is CH; and $X^2$ and $X^3$ are $CR^1$; and $R^1$ is $CF_3$. In another embodiment of Formula (IV), $X^1$ is CH; and $X^2$ and $X^3$ are $CR^1$; and $R^1$ is C(O)OH.

In one embodiment of Formula (IV),
$X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N;
$R^1$ is $R^3$, $OR^3$, C(O)$OR^3$, C(O)$NH_2$, C(O)$NHR^3$, NHC(O)$R^3$, $NHSO_2R^3$, F, Cl, Br, I, CN, $NH_2$, $NO_2$, $CF_3$, or C(O)OH;
$R^3$ is alkyl, alkenyl, or heterocyclyl; wherein each alkyl is optionally substituted with one or more independently selected $R^6$, $OR^6$, $NH_2$, $N(R^6)_2$, OH, F, Cl, Br or I;
$R^5$ is alkyl, alkenyl, alkynyl, aryl, heterocyclyl, or cycloalkyl; wherein each alkyl, alkenyl, and alkynyl is optionally substituted with one or more independently selected $R^9$, $OR^9$, $SR^9$, C(O)$R^9$, $NH_2$, $N(R^9)_2$, NHC(O)$R^9$, C(O)$NH_2$, C(O)OH, OH, CN, $CF_3$, F, Cl, Br or I;
$R^6$ is alkyl or heterocyclyl;
$R^9$ is alkyl, aryl, heterocyclyl, or cycloalkyl; wherein each alkyl is optionally substituted with one or more independently selected $OCH_3$, or aryl;
wherein the cyclic moieties represented by $R^3$, $R^5$, $R^6$, and $R^9$ are optionally substituted with one or more independently selected $R^{13}$, $OR^{13}SO_2R^{13}$, C(O)$R^{13}$, CO(O)$R^{13}$, $NH_2$, $N(R^{13})_2$, NHC(O)$R^{13}$, NHC(O)$OR^{13}$, C(O)$NH_2$, C(O)N$(R^{13})_2$, OH, CN, $CF_3$, $OCF_3$, $SCF_3$, F, Cl, Br or I;
$R^{13}$ is alkyl, aryl, tetrahydrofuranyl, pyridazinyl, pyrazinyl, pyrimidinyl, pyridinyl, thieno[3,2-c]pyridinyl, furo[3,2-c]pyridinyl, or pyrrolidin-2-onyl, wherein each alkyl is optionally substituted with one or more independently selected $R^{14}$, $OR^{14}$, $NH_2$, OH, F, Cl, Br or I; wherein each aryl, tetrahydrofuranyl, pyridazinyl, pyrazinyl, pyrimidinyl, pridinyl, thieno[3,2-c]pyridinyl, furo[3,2-c]pyridinyl, pyrrolidin-2-onyl, cycloalkyl, and cycloalkenyl is optionally substituted with one or more independently selected $R^{15}$, $OR^{15}$, C(O)$R^{15}$, CN, $CF_3$, F, Cl, Br or I;
$R^{14}$ is alkyl, aryl, or cycloalkyl; wherein each alkyl is optionally substituted with one or more independently selected OH, F, Cl, Br or I; and
$R^{15}$ is alkyl.

Still another embodiment pertains to compounds having Formula (IV), which include Examples 291, 292, 293, 294, 295, 296, 297, 298, 299, 300, 301, 302, 303, 304, 305, 306, 307, 308, 309, 310, 311, 312, 313, 314, 315, and pharmaceutically acceptable salts thereof.

Embodiments of Formula (V)

In another aspect, the present invention provides compounds of Formula (V)

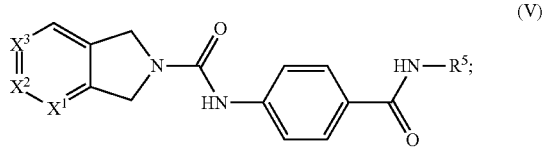

(V)

or pharmaceutically acceptable salts thereof; wherein $X^1$, $X^2$, $X^3$, and $R^5$ are as described herein for Formula (I).

In one embodiment of Formula (V), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N. In another embodiment of Formula (V), $X^1$, $X^2$, and $X^3$ are CH. In another embodiment of Formula (V), $X^1$ and $X^3$ are CH; and $X^2$ is N. In another embodiment of Formula (V), $X^1$ and $X^3$ are CH; and $X^2$ is $CR^1$. In another embodiment of Formula (V), $X^2$ and $X^3$ are CH; and $X^1$ is $CR^1$. In another embodiment of Formula (V), $X^1$ is CH; and $X^2$ and $X^3$ are $CR^1$. In another embodiment of Formula (V), $X^2$ is CH; and $X^1$ and $X^3$ are N. In another embodiment of Formula (V), $X^2$ and $X^3$ are CH; and $X^1$ is N.

In another embodiment of Formula (V), $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (V), $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (V), $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (V), $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (V), $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (V), $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (V), $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (V), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (V), $R^1$ is $C(O)NH_2$. In another embodiment of Formula (V), $R^1$ is F. In another embodiment of Formula (V), $R^1$ is Cl. In another embodiment of Formula (V), $R^1$ is Br. In another embodiment of Formula (V), $R^1$ is CN. In another embodiment of Formula (V), $R^1$ is $NH_2$. In another embodiment of Formula (V), $R^1$ is $NO_2$. In another embodiment of Formula (V), $R^1$ is $CF_3$. In another embodiment of Formula (V), $R^1$ is $C(O)OH$.

In another embodiment of Formula (V), $X^1$ and $X^3$ are CH; and $X^2$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (V), $X^1$ and $X^3$ are CH; and $X^2$ is $CR^1$; $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (V), $X^1$ and $X^3$ are CH; and $X^2$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (V), $X^1$ and $X^3$ are CH; and $X^2$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (V), $X^1$ and $X^3$ are CH; and $X^2$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (V), $X^1$ and $X^3$ are CH; and $X^2$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (V), $X^1$ and $X^3$ are CH; and $X^2$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (V), $X^1$ and $X^3$ are CH; and $X^2$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (V), $X^1$ and $X^3$ are CH; and $X^2$ is $CR^1$; and $R^1$ is $C(O)NH_2$. In another embodiment of Formula (V), $X^1$ and $X^3$ are CH; and $X^2$ is $CR^1$; and $R^1$ is F. In another embodiment of Formula (V), $X^1$ and $X^3$ are CH; and $X^2$ is $CR^1$; and $R^1$ is Cl. In another embodiment of Formula (V), $X^1$ and $X^3$ are CH; and $X^2$ is $CR^1$; and $R^1$ is Br. In another embodiment of Formula (V), $X^1$ and $X^3$ are CH; and $X^2$ is $CR^1$; and $R^1$ is CN. In another embodiment of Formula (V), $X^1$ and $X^3$ are CH; and $X^2$ is $CR^1$; and $R^1$ is $NH_2$. In another embodiment of Formula (V), $X^1$ and $X^3$ are CH; and $X^2$ is $CR^1$; and $R^1$ is $NO_2$. In another embodiment of Formula (V), $X^1$ and $X^3$ are CH; and $X^2$ is $CR^1$; and $R^1$ is $CF_3$. In another embodiment of Formula (V), $X^1$ and $X^3$ are CH; and $X^2$ is $CR^1$; and $R^1$ is $C(O)OH$.

In another embodiment of Formula (V), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (V), $X^2$ and $X^3$ are CH; and $X^1$ is $CR^1$; and $R^1$ is $R^3$, $OR^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl. In another embodiment of Formula (V), X$^2$ and X$^3$ are CH; and X$^1$ is CR$^1$; R$^1$ is R$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl. In another embodiment of Formula (V), X$^2$ and X$^3$ are CH; and X$^1$ is CR$^1$; R$^1$ is OR$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl. In another embodiment of Formula (V), X$^2$ and X$^3$ are CH; and X$^1$ is CR$^1$; R$^1$ is C(O)OR$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl. In another embodiment of Formula (V), X$^2$ and X$^3$ are CH; and X$^1$ is CR$^1$; R$^1$ is C(O)NHR$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl. In another embodiment of Formula (V), X$^2$ and X$^3$ are CH; and X$^1$ is CR$^1$; R$^1$ is NHC(O)R$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl. In another embodiment of Formula (V), X$^2$ and X$^3$ are CH; and X$^1$ is CR$^1$; R$^1$ is NHSO$_2$R$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl. In another embodiment of Formula (V), X$^2$ and X$^3$ are CH; and X$^1$ is CR$^1$; and R$^1$ is C(O)NH$_2$. In another embodiment of Formula (V), X$^2$ and X$^3$ are CH; and X$^1$ is CR$^1$; and R$^1$ is F. In another embodiment of Formula (V), X$^2$ and X$^3$ are CH; and X$^1$ is CR$^1$; and R$^1$ is Cl. In another embodiment of Formula (V), X$^2$ and X$^3$ are CH; and X$^1$ is CR$^1$; and R$^1$ is Br. In another embodiment of Formula (V), X$^2$ and X$^3$ are CH; and X$^1$ is CR$^1$; and R$^1$ is CN. In another embodiment of Formula (V), X$^2$ and X$^3$ are CH; and X$^1$ is CR$^1$; and R$^1$ is NH$_2$. In another embodiment of Formula (V), X$^2$ and X$^3$ are CH; and X$^1$ is CR$^1$; and R$^1$ is NO$_2$. In another embodiment of Formula (V), X$^2$ and X$^3$ are CH; and X$^1$ is CR$^1$; and R$^1$ is CF$_3$. In another embodiment of Formula (V), X$^2$ and X$^3$ are CH; and X$^1$ is CR$^1$; and R$^1$ is C(O)OH.

In another embodiment of Formula (V), X$^1$ is CH; and X$^2$ and X$^3$ are CR$^1$; and R$^1$ is R$^3$, OR$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH. In another embodiment of Formula (V), X$^1$ is CH; and X$^2$ and X$^3$ are CR$^1$; and R$^1$ is R$^3$, OR$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl. In another embodiment of Formula (V), X$^1$ is CH; and X$^2$ and X$^3$ are CR$^1$; R$^1$ is R$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl. In another embodiment of Formula (V), X$^1$ is CH; and X$^2$ and X$^3$ are CR$^1$; R$^1$ is OR$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl. In another embodiment of Formula (V), X$^1$ is CH; and X$^2$ and X$^3$ are CR$^1$; R$^1$ is C(O)OR$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl. In another embodiment of Formula (V), X$^1$ is CH; and X$^2$ and X$^3$ are CR$^1$; R$^1$ is C(O)NHR$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl. In another embodiment of Formula (V), X$^1$ is CH; and X$^2$ and X$^3$ are CR$^1$; R$^1$ is NHC(O)R$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl. In another embodiment of Formula (V), X$^1$ is CH; and X$^2$ and X$^3$ are CR$^1$; R$^1$ is NHSO$_2$R$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl. In another embodiment of Formula (V), X$^1$ is CH; and X$^2$ and X$^3$ are CR$^1$; and R$^1$ is C(O)NH$_2$. In another embodiment of Formula (V), X$^1$ is CH; and X$^2$ and X$^3$ are CR$^1$; and R$^1$ is F. In another embodiment of Formula (V), X$^1$ is CH; and X$^2$ and X$^3$ are CR$^1$; and R$^1$ is Cl. In another embodiment of Formula (V), X$^1$ is CH; and X$^2$ and X$^3$ are CR$^1$; and R$^1$ is Br. In another embodiment of Formula (V), X$^1$ is CH; and X$^2$ and X$^3$ are CR$^1$; and R$^1$ is CN. In another embodiment of Formula (V), X$^1$ is CH; and X$^2$ and X$^3$ are CR$^1$; and R$^1$ is NH$_2$. In another embodiment of Formula (V), X$^1$ is CH; and X$^2$ and X$^3$ are CR$^1$; and R$^1$ is NO$_2$. In another embodiment of Formula (V), X$^1$ is CH; and X$^2$ and X$^3$ are CR$^1$; and R$^1$ is CF$_3$. In another embodiment of Formula (V), X$^1$ is CH; and X$^2$ and X$^3$ are CR$^1$; and R$^1$ is C(O)OH.

In one embodiment of Formula (V),
X$^1$, X$^2$, and X$^3$ are CH; or
X$^1$ and X$^3$ are CH; and X$^2$ is N; or
X$^1$ and X$^3$ are CH; and X$^2$ is CR$^1$; or
X$^2$ and X$^3$ are CH; and X$^1$ is CR$^1$; or
X$^1$ is CH; and X$^2$ and X$^3$ are CR$^1$; or
X$^2$ is CH; and X$^1$ and X$^3$ are N; or
X$^2$ and X$^3$ are CH; and X$^1$ is N;
R$^1$ is R$^3$, OR$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH;
R$^3$ is alkyl, alkenyl, or heterocyclyl; wherein each alkyl is optionally substituted with one or more independently selected R$^6$, OR$^6$, NH$_2$, N(R$^6$)$_2$, OH, F, Cl, Br or I;
R$^5$ is alkyl, alkenyl, alkynyl, aryl, heterocyclyl, or cycloalkyl; wherein each alkyl, alkenyl, and alkynyl is optionally substituted with one or more independently selected R$^9$, OR$^9$, SR$^9$, C(O)R$^9$, NH$_2$, N(R$^9$)$_2$, NHC(O)R$^9$, C(O)NH$_2$, C(O)OH, OH, CN, CF$_3$, F, Cl, Br or I;
R$^6$ is alkyl or heterocyclyl;
R$^9$ is alkyl, aryl, heterocyclyl, or cycloalkyl; wherein each alkyl is optionally substituted with one or more independently selected OCH$_3$, or aryl;
wherein the cyclic moieties represented by R$^3$, R$^5$, R$^6$, and R$^9$ are optionally substituted with one or more independently selected R$^{13}$, OR$^{13}$SO$_2$R$^{13}$, C(O)R$^{13}$, CO(O)R$^{13}$, NH$_2$, N(R$^{13}$)$_2$, NHC(O)R$^{13}$, NHC(O)OR$^{13}$, C(O)NH$_2$, C(O)N(R$^{13}$)$_2$, OH, CN, CF$_3$, OCF$_3$, SCF$_3$, F, Cl, Br or I;
R$^{13}$ is alkyl, aryl, tetrahydrofuranyl, pyridazinyl, pyrazinyl, pyrimidinyl, pyridinyl, thieno[3,2-c]pyridinyl, furo[3,2-c]pyridinyl, or pyrrolidin-2-onyl, wherein each alkyl is optionally substituted with one or more independently selected R$^{14}$, OR$^{14}$, NH$_2$, OH, F, Cl, Br or I; wherein each aryl, tetrahydrofuranyl, pyridazinyl, pyrazinyl, pyrimidinyl, pridinyl, thieno[3,2-c]pyridinyl, furo[3,2-c]pyridinyl, pyrrolidin-2-onyl, cycloalkyl, and cycloalkenyl is optionally substituted with one or more independently selected $R^{15}$, $OR^{15}$, $C(O)R^{15}$, CN, $CF_3$, F, Cl, Br or I;

$R^{14}$ is alkyl, aryl, or cycloalkyl; wherein each alkyl is optionally substituted with one or more independently selected OH, F, Cl, Br or I; and $R^{15}$ is alkyl.

Still another embodiment pertains to compounds having Formula (V), which include Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 159, 160, 161, 162, 163, 164, 165, 166, 167, 168, 169, 170, 171, 172, 173, 174, 176, 177, 178, 179, 180, 181, 182, 184, 185, 186, 187, 188, 189, 190, 192, 193, 194, 195, 196, 197, 198, 199, 200, 201, 202, 203, 204, 205, 206, 207, 209, 210, 211, 213, 214, 215, 216, 217, 218, 219, 220, 221, 223, 224, 225, 226, 227, 228, 230, 231, 232, 234, 235, 236, 237, 239, 240, 243, 245, 246, 248, 249, 250, 251, 252, 253, 254, 256, 257, 258, 259, 260, 265, 268, 269, 270, 271, 272, 273, 274, 275, 276, 277, 278, 279, 280, 281, 282, 283, 284, 285, 286, 287, 288, 289, 290, 373, 410, 411, 412, 413, 414, 415, 416, 417, 418, 419, 420, 421, 424, 425, 426, 427, 430, 431, 434, 435, 436, 437, 438, 439, 440, 441, 442, 445, 449, 450, and pharmaceutically acceptable salts thereof.

Embodiments of Formula (Ia)

One embodiment of this invention, therefore, pertains to compounds or pharmaceutically acceptable salts, which are useful as inhibitors of NAMPT, the compounds having Formula (Ia)

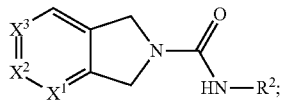

Formula (Ia)

wherein
$X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or
$X^1$ is CH; $X^2$ is N; and $X^3$ is $CR^1$; or
$X^1$ is $CR^1$; $X^2$ is N; and $X^3$ is CH; or
$X^1$ is N; $X^2$ is $CR^1$; and $X^3$ is CH; or
$X^1$ is N; $X^2$ is $CR^1$; and $X^3$ is N;

$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, C(O)H, $CF_3$, C(O)OH, or $C(O)NH_2$;

$R^2$ is alkyl, alkenyl, alkynyl, phenyl, heterocyclyl, cycloalkyl, or cycloalkenyl; wherein each $R^2$ alkyl, alkenyl, and alkynyl is optionally substituted with one or more independently selected $R^4$, $OR^4$, $SR^4$, $S(O)R^4$, $SO_2R^4$, $C(O)R^4$, $CO(O)R^4$, $OC(O)R^4$, $OC(O)OR^4$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, (O), CN, $N_3$, $NO_2$, $CF_3$, $CF_2CF_3$, $OCF_3$, $OCF_2CF_3$, F, Cl, Br or I; wherein each $R^2$ phenyl is optionally substituted at the para position with one independently selected $R^5$, $OCH_2CH_2CH_2CH_2CH_2CH_3$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $CHNOR^5$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, OH, CN, $N_3$, $NO_2$, $CF_3$, $CF_2CF_3$, $OCF_3$, $OCF_2CF_3$, Br or I; wherein each $R^2$ phenyl is optionally additionally substituted with one F; wherein each $R^2$ heterocyclyl, cycloalkyl, and cycloalkenyl is optionally substituted with one or more independently selected $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, OH, CN, $N_3$, $CF_3$, $CF_2CF_3$, $OCF_3$, $OCF_2CF_3$, F, Cl, Br or I; wherein $R^2$ is not 4-methylphenyl;

$R^3$ is alkyl, alkenyl, alkynyl, aryl, or heterocyclyl; wherein each $R^3$ alkyl, alkenyl, and alkynyl is optionally substituted with one or more independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I;

$R^4$ is alkyl, alkenyl, alkynyl, aryl, cycloalkyl, or heterocyclyl; wherein each $R^4$ alkyl, alkenyl, and alkynyl is optionally substituted with one or more independently selected $R^7$, $OR^7$, $SR^7$, $S(O)R^7$, $SO_2R^7$, $C(O)R^7$, $OC(O)R^7$, $OC(O)OR^7$, $NH_2$, $NHR^7$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, OH, (O), CN, $N_3$, $NO_2$, $CF_3$, $CF_2CF_3$, $OCF_3$, $OCF_2CF_3$, F, Cl, Br or I; wherein each $R^4$ aryl and heterocycyl is optionally substituted with one or more independently selected $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, OH, CN, $N_3$, $NO_2$, $CF_3$, $CF_2CF_3$, $OCF_3$, $OCF_2CF_3$, F, Cl, Br or I;

$R^5$ is alkyl, alkenyl, alkynyl, aryl, heterocyclyl, cycloalkyl, or cycloalkenyl; wherein each $R^5$ alkyl, alkenyl, and alkynyl is optionally substituted with one or more independently selected $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I;

$R^6$ is alkyl, alkenyl, alkynyl, aryl, heterocyclyl, cycloalkyl, or cycloalkenyl; wherein each $R^6$ alkyl, alkenyl, and alkynyl is optionally substituted with one or more independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, $OH$, $(O)$, $C(O)OH$, $N_3$, $CN$, $NH_2$, $CF_3$, $CF_2CF_3$, F, Cl, Br or I;

$R^7$ is alkyl, alkenyl, alkynyl, aryl, heterocyclyl, cycloalkyl, or cycloalkenyl; wherein each $R^7$ alkyl, alkenyl, and alkynyl is optionally substituted with one or more independently selected $R^{11}$, $OR^{11}$, $SR^{11}$, $S(O)R^{11}$, $SO_2R^{11}$, $NHR^{11}$, $N(R^{11})_2$, $C(O)R^{11}$, $C(O)NH_2$, $C(O)NHR^{11}$, $C(O)N(R^{11})_2$, $NHC(O)R^{11}$, $NR^{11}C(O)R^{11}$, $NHSO_2R^{11}$, $NHC(O)OR^{11}$, $SO_2NH_2$, $SO_2NHR^{11}$, $SO_2N(R^{11})_2$, $NHC(O)NH_2$, $NHC(O)NHR^{11}$, $OH$, $(O)$, $C(O)OH$, $N_3$, $CN$, $NH_2$, $CF_3$, $CF_2CF_3$, F, Cl, Br or I;

$R^8$ is alkyl, alkenyl, alkynyl, aryl, heterocyclyl, cycloalkyl, or cycloalkenyl; wherein each $R^8$ alkyl, alkenyl, and alkynyl is optionally substituted with one or more independently selected $R^{12}$, $OR^{12}$, $SR^{12}$, $S(O)R^{12}$, $SO_2R^{12}$, $NHR^{12}$, $N(R^{12})_2$, $C(O)R^{12}$, $C(O)NH_2$, $C(O)NHR^{12}$, $C(O)N(R^{12})_2$, $NHC(O)R^{12}$, $NR^{12}C(O)R^{12}$, $NHSO_2R^{12}$, $NHC(O)OR^{12}$, $SO_2NH_2$, $SO_2NHR^{12}$, $SO_2N(R^{12})_2$, $NHC(O)NH_2$, $NHC(O)NHR^{12}$, $OH$, $(O)$, $C(O)OH$, $N_3$, $CN$, $NH_2$, $CF_3$, $CF_2CF_3$, F, Cl, Br or I;

$R^9$ is alkyl, alkenyl, alkynyl, aryl, heterocyclyl, cycloalkyl, or cycloalkenyl; wherein each $R^9$ alkyl, alkenyl, and alkynyl is optionally substituted with one or more independently selected $OCH_3$, $OH$, aryl, or heterocyclyl;

$R^{10}$ is alkyl, alkenyl, alkynyl, aryl, heterocyclyl, cycloalkyl, or cycloalkenyl;

$R^{11}$ is alkyl, alkenyl, alkynyl, aryl, heterocyclyl, cycloalkyl, or cycloalkenyl;

$R^{12}$ is alkyl, alkenyl, alkynyl, aryl, heterocyclyl, cycloalkyl, or cycloalkenyl;

wherein the cyclic moieties represented by $R^3$, $R^5$, $R^6$, $R^7$, $R^8$, $R^9$, $R^{10}$, $R^{11}$, and $R^{12}$ are optionally substituted with one or more independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, $C(O)H$, $C(O)OH$, $OH$, $CN$, $N_3$, $NO_2$, $CF_3$, $CF_2CF_3$, $OCF_3$, $OCF_2CF_3$, $SCF_3$, F, Cl, Br or I;

$R^{13}$ is alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, dioxanyl, tetrahydropyranyl, piperidinyl, pyrimidinyl, oxazolyl, pyrazolyl, thiazolyl, pyrrolyl, thienyl, furanyl, cycloalkyl, or cycloalkenyl; wherein each $R^{13}$ alkyl, alkenyl, and alkynyl is optionally substituted with one or more independently selected $R^{14}$, $OR^{14}$, $SR^{14}$, $S(O)R^{14}$, $SO_2R^{14}$, $C(O)R^{14}$, $OC(O)R^{14}$, $OC(O)OR^{14}$, $NH_2$, $NHR^{14}$, $N(R^{14})_2$, $NHC(O)R^{14}$, $NR^{14}C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, dioxanyl, tetrahydropyranyl, piperidinyl, pyrimidinyl, oxazolyl, pyrazolyl, thiazolyl, pyrrolyl, thienyl, furanyl, cycloalkyl, and cycloalkenyl is optionally substituted with one or more independently selected $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $C(O)H$, $C(O)OH$, $OH$, $CN$, $N_3$, $NO_2$, $CF_3$, $CF_2CF_3$, $OCF_3$, $OCF_2CF_3$, F, Cl, Br or I;

$R^{14}$ is alkyl, alkenyl, alkynyl, aryl, heterocyclyl, cycloalkyl, or cycloalkenyl; wherein each $R^{14}$ alkyl, alkenyl, and alkynyl is optionally substituted with one or more independently selected $OCH_3$, $NH_2$, $SO_2NH_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{14}$ aryl, heterocyclyl, cycloalkyl, or cycloalkenyl is optionally substituted with one or more independently selected alkyl, or $OCH_3$; and $R^{15}$ is alkyl;

with the proviso that when $R^2$ is unsubstituted alkyl or optionally substituted alkyl; $R^2$ is $C_4$-$C_6$-alkyl.

In one embodiment of Formula (Ia), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N; or $X^1$ is CH; $X^2$ is N; and $X^3$ is $CR^1$; or $X^1$ is $CR^1$; $X^2$ is N; and $X^3$ is CH; or $X^1$ is N; $X^2$ is $CR^1$; and $X^3$ is CH; or $X^1$ is N; $X^2$ is $CR^1$; and $X^3$ is N. In another embodiment of Formula (Ia), $X^1$, $X^2$, and $X^3$ are CH. In another embodiment of Formula (Ia), $X^1$ and $X^3$ are CH; and $X^2$ is N. In another embodiment of Formula (Ia), $X^1$ and $X^3$ are CH; and $X^2$ is $CR^1$. In another embodiment of Formula (Ia), $X^2$ and $X^3$ are CH; and $X^1$ is $CR^1$. In another embodiment of Formula (Ia), $X^1$ is CH; and $X^2$ and $X^3$ are $CR^1$. In another embodiment of Formula (Ia), $X^2$ is CH; and $X^1$ and $X^3$ are N. In another embodiment of Formula (Ia), $X^2$ and $X^3$ are CH; and $X^1$ is N. In another embodiment of Formula (Ia), $X^1$ is CH; $X^2$ is N; and $X^3$ is $CR^1$. In another embodiment of Formula (Ia), $X^1$ is $CR^1$; $X^2$ is N; and $X^3$ is CH. In another embodiment of Formula (Ia), $X^1$ is N; $X^2$ is $CR^1$; and $X^3$ is CH. In another embodiment of Formula (Ia), $X^1$ is N; $X^2$ is $CR^1$; and $X^3$ is N.

In another embodiment of Formula (Ia), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (Ia), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $N(R^6)_2$, or $OH$; wherein $R^6$ is alkyl or heterocyclyl. In another embodiment of Formula (Ia), $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $R^1$ is $C(O)NH_2$. In another embodiment of Formula (Ia), $R^1$ is F. In another embodiment of Formula (Ia), $R^1$ is Cl. In another embodiment of Formula (Ia), $R^1$ is Br. In another embodiment of Formula (Ia), $R^1$ is CN. In another embodiment of Formula (Ia), $R^1$ is $NH_2$. In another embodiment of Formula (Ia), $R^1$ is $NO_2$. In another embodiment of Formula (Ia), $R^1$ is $CF_3$. In another embodiment of Formula (Ia), $R^1$ is C(O)OH. In another embodiment of Formula (Ia), $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl.

In another embodiment of Formula (Ia), $X^1$ and $X^3$ are CH; and $X^2$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (Ia), $X^1$ and $X^3$ are CH; and $X^2$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $X^1$ and $X^3$ are CH; and $X^2$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $X^1$ and $X^3$ are CH; and $X^2$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $X^1$ and $X^3$ are CH; and $X^2$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $X^1$ and $X^3$ are CH; and $X^2$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $X^1$ and $X^3$ are CH; and $X^2$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $X^1$ and $X^3$ are CH; and $X^2$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $X^1$ and $X^3$ are CH; and $X^2$ is $CR^1$; and $R^1$ is $C(O)NH_2$. In another embodiment of Formula (Ia), $X^1$ and $X^3$ are CH; and $X^2$ is $CR^1$; and $R^1$ is F. In another embodiment of Formula (Ia), $X^1$ and $X^3$ are CH; and $X^2$ is $CR^1$; and $R^1$ is Cl. In another embodiment of Formula (Ia), $X^1$ and $X^3$ are CH; and $X^2$ is $CR^1$; and $R^1$ is Br. In another embodiment of Formula (Ia), $X^1$ and $X^3$ are CH; and $X^2$ is $CR^1$; and $R^1$ is CN. In another embodiment of Formula (Ia), $X^1$ and $X^3$ are CH; and $X^2$ is $CR^1$; and $R^1$ is $NH_2$. In another embodiment of Formula (Ia), $X^1$ and $X^3$ are CH; and $X^2$ is $CR^1$; and $R^1$ is $NO_2$. In another embodiment of Formula (Ia), $X^1$ and $X^3$ are CH; and $X^2$ is $CR^1$; and $R^1$ is $CF_3$. In another embodiment of Formula (Ia), $X^1$ and $X^3$ are CH; and $X^2$ is $CR^1$; and $R^1$ is C(O)OH. In another embodiment of Formula (Ia), $X^1$ and $X^3$ are CH; and $X^2$ is $CR^1$; $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; and $R^6$ is alkyl or heterocyclyl.

In another embodiment of Formula (Ia), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (Ia), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $X^2$ and $X^3$ are CH; and $X^1$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $X^2$ and $X^3$ are CH; and $X^1$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $X^2$ and $X^3$ are CH; and $X^1$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $X^2$ and $X^3$ are CH; and $X^1$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $X^2$ and $X^3$ are CH; and $X^1$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $X^2$ and $X^3$ are CH; and $X^1$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $X^2$ and $X^3$ are CH; and $X^1$ is $CR^1$; and $R^1$ is $C(O)NH_2$. In another embodiment of Formula (Ia), $X^2$ and $X^3$ are CH; and $X^1$ is $CR^1$; and $R^1$ is F. In another embodiment of Formula (Ia), $X^2$ and $X^3$ are CH; and $X^1$ is $CR^1$; and $R^1$ is Cl. In another embodiment of Formula (Ia), $X^2$ and $X^3$ are CH; and $X^1$ is $CR^1$; and $R^1$ is Br. In another embodiment of Formula (Ia), $X^2$ and $X^3$ are CH; and $X^1$ is $CR^1$; and $R^1$ is CN. In another embodiment of Formula (Ia), $X^2$ and $X^3$ are CH; and $X^1$ is $CR^1$; and $R^1$ is $NH_2$. In another embodiment of Formula (Ia), $X^2$ and $X^3$ are CH; and $X^1$ is $CR^1$; and $R^1$ is $NO_2$. In another embodiment of Formula (Ia), $X^2$ and $X^3$ are CH; and $X^1$ is $CR^1$; and $R^1$ is $CF_3$. In another embodiment of Formula (Ia), $X^2$ and $X^3$ are CH; and $X^1$ is $CR^1$; and $R^1$ is C(O)OH. In another embodiment of Formula (Ia), $X^2$ and $X^3$ are CH; and $X^1$ is $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; and $R^6$ is alkyl or heterocyclyl.

In another embodiment of Formula (Ia), $X^1$ is CH; and $X^2$ and $X^3$ are $CR^1$; and $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (Ia), $X^1$ is CH; and $X^2$ and $X^3$ are $CR^1$; and $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $X^1$ is CH; and $X^2$ and $X^3$ are $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $X^1$ is CH; and $X^2$ and $X^3$ are $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $X^1$ is CH; and $X^2$ and $X^3$ are $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $X^1$ is CH; and $X^2$ and $X^3$ are $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $X^1$ is CH; and $X^2$ and $X^3$ are $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $X^1$ is CH; and $X^2$ and $X^3$ are $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Ia), $X^1$ is CH; and $X^2$ and $X^3$ are $CR^1$; and $R^1$ is $C(O)NH_2$. In another embodiment of Formula (Ia), $X^1$ is CH; and $X^2$ and $X^3$ are $CR^1$; and $R^1$ is F. In another embodiment of Formula (Ia), $X^1$ is CH; and $X^2$ and $X^3$ are $CR^1$; and $R^1$ is Cl. In another embodiment of Formula (Ia), $X^1$ is CH; and $X^2$ and $X^3$ are $CR^1$; and $R^1$ is Br. In another embodiment of Formula (Ia), $X^1$ is CH; and $X^2$ and $X^3$ are $CR^1$; and $R^1$ is CN. In another embodiment of Formula (Ia), $X^1$ is CH; and $X^2$ and $X^3$ are $CR^1$; and $R^1$ is $NH_2$. In another embodiment of Formula (Ia), $X^1$ is CH; and $X^2$ and $X^3$ are $CR^1$; and $R^1$ is $NO_2$. In another embodiment of Formula (Ia), $X^1$ is CH; and $X^2$ and $X^3$ are $CR^1$; and $R^1$ is $CF_3$. In another embodiment of Formula (Ia), $X^1$ is CH; and $X^2$ and $X^3$ are $CR^1$; and $R^1$ is C(O)OH. In another embodiment of Formula (Ia), $X^1$ is CH; and $X^2$ and $X^3$ are $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; and $R^6$ is alkyl or heterocyclyl.

In one embodiment of Formula (Ia), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N;

$R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH;

$R^2$ is alkyl, phenyl, heterocyclyl, wherein each $R^2$ alkyl is optionally substituted with one or more independently selected $R^4$, $OR^4$, $C(O)R^4$, $CO(O)R^4$, $NHC(O)R^4$, $C(O)NHR^4$, or F, Cl, Br or I; wherein each $R^2$ phenyl is optionally substituted at the para position with one independently selected $R^5$, $OCH_2CH_2CH_2CH_2CH_2CH_3$, $C(O)R^5$, $CO(O)R^5$, $NHR^5$, $NHC(O)R^5$, $C(O)NH_2$, $C(O)NHR^5$, $C(O)N(R^5)_2$, $CHNOR^5$, $C(O)NHOR^5$, $CF_3$, Br or I; wherein each $R^2$ phenyl is optionally additionally substituted with one F; wherein each $R^2$ heterocyclyl is optionally substituted with one or more independently selected $R^5$, $C(O)R^5$, $NHC(O)R^5$, $C(O)NHR^5$, F, Cl, Br or I; wherein $R^2$ is not 4-methylphenyl;

$R^3$ is alkyl, alkenyl, or heterocyclyl; wherein each $R^3$ alkyl is optionally substituted with one or more independently selected $R^6$, $OR^6$, $NH_2$, $N(R^6)_2$, OH, F, Cl, Br or I;

$R^4$ is alkyl, aryl, cycloalkyl, or heterocyclyl; wherein each $R^4$ alkyl is optionally substituted with one or more independently selected $R^7$, F, Cl, Br or I; wherein each $R^4$ aryl and heterocycyl is optionally substituted with one or more independently selected $R^8$, $C(O)R^8$, F, Cl, Br or I;

$R^5$ is alkyl, alkenyl, alkynyl, aryl, heterocyclyl, or cycloalkyl; wherein each $R^5$ alkyl, alkenyl, and alkynyl is optionally substituted with one or more independently selected $R^9$, $OR^9$, $SR^9$, $C(O)R^9$, $NH_2$, $N(R^9)_2$, $NHC(O)R^9$, $C(O)NH_2$, C(O)OH, OH, CN, $CF_3$, F, Cl, Br or I;

$R^6$ is alkyl, or heterocyclyl;

$R^7$ is aryl;

$R^8$ is alkyl, aryl, or heterocyclyl;

$R^9$ is alkyl, aryl, heterocyclyl, or cycloalkyl; wherein each $R^9$ alkyl is optionally substituted with one or more independently selected $OCH_3$, OH, aryl, or heterocyclyl;

wherein the cyclic moieties represented by $R^3$, $R^5$, $R^6$, $R^7$, $R^8$, and $R^9$, are optionally substituted with one or more independently selected $R^{13}$, $OR^{13}$, $SO_2R^{13}$, $C(O)R^{13}$, $CO(O)R^{13}$, $NH_2$, $N(R^{13})_2$, $NHC(O)R^{13}$, $NHC(O)OR^{13}$, $C(O)NH_2$, $C(O)N(R^{13})_2$, OH, CN, $CF_3$, $OCF_3$, $SCF_3$, F, Cl, Br or I;

$R^{13}$ is alkyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, dioxanyl, tetrahydropyranyl, piperidinyl, pyrimidinyl, oxazolyl, pyrazolyl, thiazolyl, pyrrolyl, thienyl, furanyl, or cycloalkyl; wherein each $R^{13}$ alkyl is optionally substituted with one or more independently selected $R^{14}$, $OR^{14}$, $NH_2$, $N(R^{14})_2$, $NHC(O)R^{14}$, OH, $CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, dioxanyl, tetrahydropyranyl, piperidinyl, pyrimidinyl, oxazolyl, pyrazolyl, thiazolyl, pyrrolyl, thienyl, furanyl, and cycloalkyl is optionally substituted with one or more independently selected $R^{15}$, $OR^{15}$, $SO_2R^{15}$, $C(O)R^{15}$, $N(R^{15})_2$, $NHC(O)R^{15}$, CN, $CF_3$, F, Cl Br or I;

$R^{14}$ is alkyl, aryl, heterocyclyl, or cycloalkyl; wherein each $R^{14}$ alkyl is optionally substituted with one or more independently selected $OCH_3$, OH, F, Cl, Br or I; wherein each $R^{14}$ aryl, heterocyclyl, cycloalkyl, or cycloalkenyl is optionally substituted with one or more independently selected alkyl, or $OCH_3$; and $R^{15}$ is alkyl;

with the proviso that when $R^2$ is unsubstituted alkyl or optionally substituted alkyl; $R^2$ is $C_4$-$C_6$-alkyl.

In another embodiment of Formula (Ia), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N;

$R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, CN, $NH_2$, $NO_2$, $CF_3$, or C(O)OH;

$R^2$ is alkyl, phenyl, heterocyclyl, wherein each $R^2$ alkyl is optionally substituted with one or more independently selected $R^4$, $OR^4$, $C(O)R^4$, $CO(O)R^4$, $NHC(O)R^4$, $C(O)NHR^4$, or F, Cl, Br or I; wherein each $R^2$ phenyl is optionally substituted at the para position with one independently selected $R^5$, $OCH_2CH_2CH_2CH_2CH_2CH_3$, $C(O)R^5$, $CO(O)R^5$, $NHR^5$, $NHC(O)R^5$, $C(O)NH_2$, $C(O)NHR^5$, $C(O)N(R^5)_2$, $CHNOR^5$, $C(O)NHOR^5$, or $CF_3$; wherein each $R^2$ phenyl is optionally additionally substituted with one F; wherein each $R^2$ heterocyclyl is optionally substituted with one or more independently selected $R^5$, $C(O)R^5$, $NHC(O)R^5$, or $C(O)NHR^5$; wherein $R^2$ is not 4-methylphenyl;

$R^3$ is alkyl, alkenyl, or heterocyclyl; wherein each $R^3$ alkyl is optionally substituted with one or more independently selected $R^6$, $OR^6$, $NH_2$, $N(R^6)_2$, or OH;

$R^4$ is alkyl, aryl, cycloalkyl, or heterocyclyl; wherein each $R^4$ alkyl is optionally substituted with one or more $R^7$; wherein each $R^4$ aryl and heterocycyl is optionally substituted with one or more independently selected $R^8$, $C(O)R^8$, or Cl;

$R^5$ is alkyl, alkenyl, alkynyl, aryl, heterocyclyl, or cycloalkyl; wherein each $R^5$ alkyl, alkenyl, and alkynyl is optionally substituted with one or more independently selected $R^9$, $OR^9$, $SR^9$, $C(O)R^9$, $NH_2$, $N(R^9)_2$, $NHC(O)R^9$, $C(O)NH_2$, C(O)OH, OH, CN, or $CF_3$;

$R^6$ is alkyl, or heterocyclyl;

$R^7$ is aryl;

$R^8$ is alkyl, aryl, or heterocyclyl;

$R^9$ is alkyl, aryl, heterocyclyl, or cycloalkyl; wherein each $R^9$ alkyl is optionally substituted with one or more independently selected $OCH_3$, OH, aryl, or heterocyclyl;

wherein the cyclic moieties represented by $R^3$, $R^5$, $R^6$, $R^7$, $R^8$, and $R^9$, are optionally substituted with one or more independently selected $R^{13}$, $OR^{13}$, $SO_2R^{13}$, $C(O)R^{13}$, $CO(O)R^{13}$, $NH_2$, $N(R^{13})_2$, $NHC(O)R^{13}$, $NHC(O)OR^{13}$, $C(O)NH_2$, $C(O)N(R^{13})_2$, OH, CN, $CF_3$, $OCF_3$, $SCF_3$, F, or Cl;

$R^{13}$ is alkyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, dioxanyl, tetrahydropyranyl, piperidinyl, pyrimidinyl, oxazolyl, pyrazolyl, thiazolyl, pyrrolyl, thienyl, furanyl, or cycloalkyl; wherein each $R^{13}$ alkyl is optionally substituted with one or more independently selected $R^{14}$, $OR^{14}$, $NH_2$, $N(R^{14})_2$, $NHC(O)R^{14}$, OH, or $CF_3$; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, dioxanyl, tetrahydropyranyl, piperidinyl, pyrimidinyl, oxazolyl, pyrazolyl, thiazolyl, pyrrolyl, thienyl, furanyl, and cycloalkyl is optionally substituted with one or more independently selected $R^{15}$, $OR^{15}$, $SO_2R^{15}$, $C(O)R^{15}$, $N(R^{15})_2$, $NHC(O)R^{15}$, CN, $CF_3$, F, or Cl;

$R^{14}$ is alkyl, aryl, heterocyclyl, or cycloalkyl; wherein each $R^{14}$ alkyl is optionally substituted with one or more independently selected $OCH_3$, or OH; wherein each $R^{14}$ aryl, heterocyclyl, cycloalkyl, or cycloalkenyl is optionally substituted with one or more independently selected alkyl, or $OCH_3$; and $R^{15}$ is alkyl;

with the proviso that when $R^2$ is unsubstituted alkyl or optionally substituted alkyl; $R^2$ is $C_4$-$C_6$-alkyl.

Still another embodiment pertains to compounds having Formula (Ia), which include Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 358, 359, 360, 361, 362, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, and pharmaceutically acceptable salts thereof.

Embodiments of Formula (IIa)

In another aspect, the present invention provides compounds of Formula (IIa)

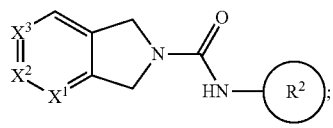

(IIa)

or pharmaceutically acceptable salts thereof; wherein $X^1$, $X^2$, $X^3$, are as described herein for Formula (Ia); and $R^2$ is phenyl, heterocyclyl, cycloalkyl, or cycloalkenyl; wherein the $R^2$ phenyl, heterocyclyl, cycloalkyl, and cycloalkenyl are optionally substituted as described herein for substituents on $R^2$ in Formula (Ia).

In one embodiment of formula (IIa), $X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or
$X^1$ is CH; $X^2$ is N; and $X^3$ is $CR^1$; or
$X^1$ is $CR^1$; $X^2$ is N; and $X^3$ is CH; or
$X^1$ is N; $X^2$ is $CR^1$; and $X^3$ is CH; or
$X^1$ is N; $X^2$ is $CR^1$; and $X^3$ is N;

$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, C(O)H, $CF_3$, C(O)OH, or $C(O)NH_2$;

$R^2$ is phenyl, heterocyclyl, cycloalkyl, or cycloalkenyl; wherein each $R^2$ phenyl is optionally substituted at the para position with one independently selected $R^5$, $OCH_2CH_2CH_2CH_2CH_2CH_3$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $CHNOR^5$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, C(O)H, C(O)OH, OH, CN, $N_3$, $NO_2$, $CF_3$, $CF_2CF_3$, $OCF_3$, $OCF_2CF_3$, Br or I; wherein each $R^2$ phenyl is optionally additionally substituted with one F; wherein each $R^2$ heterocyclyl, cycloalkyl, and cycloalkenyl is optionally substituted with one or more independently selected $R^5$, $OR^5$, $SR^5$, $S(O)R^5$, $SO_2R^5$, $C(O)R^5$, $CO(O)R^5$, $OC(O)R^5$, $OC(O)$ $OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, C(O)H, C(O)OH, OH, CN, $N_3$, $CF_3$, $CF_2CF_3$, $OCF_3$, $OCF_2CF_3$, F, Cl, Br or I; wherein $R^2$ is not 4-methylphenyl;

$R^3$ is alkyl, alkenyl, alkynyl, aryl, or heterocyclyl; wherein each $R^3$ alkyl, alkenyl, and alkynyl is optionally substituted with one or more independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, C(O)H, C(O)OH, OH, (O), CN, $N_3$, $NO_2$, $CF_3$, $CF_2CF_3$, $OCF_3$, $OCF_2CF_3$, F, Cl, Br or I;

$R^5$ is alkyl, alkenyl, alkynyl, aryl, heterocyclyl, cycloalkyl, or cycloalkenyl; wherein each $R^5$ alkyl, alkenyl, and alkynyl is optionally substituted with one or more independently selected $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, C(O)H, C(O)OH, OH, (O), CN, $N_3$, $NO_2$, $CF_3$, $CF_2CF_3$, $OCF_3$, $OCF_2CF_3$, F, Cl, Br or I;

$R^6$ is alkyl, alkenyl, alkynyl, aryl, heterocyclyl, cycloalkyl, or cycloalkenyl; wherein each $R^6$ alkyl, alkenyl, and alkynyl is optionally substituted with one or more independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, OH, (O), C(O)OH, $N_3$, CN, $NH_2$, $CF_3$, $CF_2CF_3$, F, Cl, Br or I;

$R^9$ is alkyl, alkenyl, alkynyl, aryl, heterocyclyl, cycloalkyl, or cycloalkenyl; wherein each $R^9$ alkyl, alkenyl, and alkynyl is optionally substituted with one or more independently selected $OCH_3$, OH, aryl, or heterocyclyl;

$R^{10}$ is alkyl, alkenyl, alkynyl, aryl, heterocyclyl, cycloalkyl, or cycloalkenyl;

wherein the cyclic moieties represented by $R^3$, $R^5$, $R^6$, $R^9$, and $R^{10}$, are optionally substituted with one or more independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, C(O)H, C(O)OH, OH, CN, $N_3$, $NO_2$, $CF_3$, $CF_2CF_3$, $OCF_3$, $OCF_2CF_3$, $SCF_3$, F, Cl, Br or I;

$R^{13}$ is alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, dioxanyl, tetrahydropyranyl, piperidinyl, pyrimidinyl, oxazolyl, pyrazolyl, thiazolyl, pyrrolyl, thienyl, furanyl, cycloalkyl, or cycloalkenyl; wherein each $R^{13}$ alkyl, alkenyl, and alkynyl is optionally substituted with one or more independently selected $R^{14}$, $OR^{14}$, $SR^{14}$, $S(O)R^{14}$, $SO_2R^{14}$, $C(O)R^{14}$, $OC(O)R^{14}$, $OC(O)OR^{14}$, $NH_2$, $NHR^{14}$, $N(R^{14})_2$, $NHC(O)R^{14}$, $NR^{14}C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, dioxanyl, tetrahydropyranyl, piperidinyl, pyrimidinyl, oxazolyl, pyrazolyl, thiazolyl, pyrrolyl, thienyl, furanyl, cycloalkyl, and cycloalkenyl is optionally substituted with one or more independently selected $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $C(O)H$, $C(O)OH$, $OH$, $CN$, $N_3$, $NO_2$, $CF_3$, $CF_2CF_3$, $OCF_3$, $OCF_2CF_3$, F, Cl, Br or I;

$R^{14}$ is alkyl, alkenyl, alkynyl, aryl, heterocyclyl, cycloalkyl, or cycloalkenyl; wherein each $R^{14}$ alkyl, alkenyl, and alkynyl is optionally substituted with one or more independently selected $OCH_3$, $NH_2$, $SO_2NH_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{14}$ aryl, heterocyclyl, cycloalkyl, or cycloalkenyl is optionally substituted with one or more independently selected alkyl, or $OCH_3$; and $R^{15}$ is alkyl.

In one embodiment of Formula (IIa), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N; or $X^1$ is CH; $X^2$ is N; and $X^3$ is $CR^1$; or $X^1$ is $CR^1$; $X^2$ is N; and $X^3$ is CH; or $X^1$ is N; $X^2$ is $CR^1$; and $X^3$ is CH; or $X^1$ is N; $X^2$ is $CR^1$; and $X^3$ is N. In another embodiment of Formula (IIa), $X^1$, $X^2$, and $X^3$ are CH. In another embodiment of Formula (IIa), $X^1$ and $X^3$ are CH; and $X^2$ is N. In another embodiment of Formula (IIa), $X^1$ and $X^3$ are CH; and $X^2$ is $CR^1$. In another embodiment of Formula (IIa), $X^2$ and $X^3$ are CH; and $X^1$ is $CR^1$. In another embodiment of Formula (IIa), $X^1$ is CH; and $X^2$ and $X^3$ are $CR^1$. In another embodiment of Formula (IIa), $X^2$ is CH; and $X^1$ and $X^3$ are N. In another embodiment of Formula (IIa), $X^2$ and $X^3$ are CH; and $X^1$ is N. In another embodiment of Formula (IIa), $X^1$ is CH; $X^2$ is N; and $X^3$ is $CR^1$. In another embodiment of Formula (IIa), $X^1$ is $CR^1$; $X^2$ is N; and $X^3$ is CH. In another embodiment of Formula (IIa), $X^1$ is N; $X^2$ is $CR^1$; and $X^3$ is CH. In another embodiment of Formula (IIa), $X^1$ is N; $X^2$ is $CR^1$; and $X^3$ is N.

In another embodiment of Formula (IIa), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (IIa), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $R^1$ is $C(O)NH_2$. In another embodiment of Formula (IIa), $R^1$ is F. In another embodiment of Formula (IIa), $R^1$ is Cl. In another embodiment of Formula (IIa), $R^1$ is Br. In another embodiment of Formula (IIa), $R^1$ is CN. In another embodiment of Formula (IIa), $R^1$ is $NH_2$. In another embodiment of Formula (IIa), $R^1$ is $NO_2$. In another embodiment of Formula (IIa), $R^1$ is $CF_3$. In another embodiment of Formula (IIa), $R^1$ is $C(O)OH$. In another embodiment of Formula (IIa), $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl.

In another embodiment of Formula (IIa), $X^1$ and $X^3$ are CH; and $X^2$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (IIa), $X^1$ and $X^3$ are CH; and $X^2$ is $CR^1$; $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $X^1$ and $X^3$ are CH; and $X^2$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $X^1$ and $X^3$ are CH; and $X^2$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $X^1$ and $X^3$ are CH; and $X^2$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $X^1$ and $X^3$ are CH; and $X^2$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $X^1$ and $X^3$ are CH; and $X^2$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $X^1$ and $X^3$ are CH; and $X^2$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $X^1$ and $X^3$ are CH; and $X^2$ is $CR^1$; and $R^1$ is $C(O)NH_2$. In another embodiment of Formula (IIa), $X^1$ and $X^3$ are CH; and $X^2$ is $CR^1$; and $R^1$ is F. In another embodiment of Formula (IIa), $X^1$ and $X^3$ are CH; and $X^2$ is $CR^1$; and $R^1$ is Cl. In another embodiment of Formula (IIa), $X^1$ and $X^3$ are CH; and $X^2$ is $CR^1$; and $R^1$ is Br. In another embodiment of Formula (IIa), $X^1$ and $X^3$ are CH; and $X^2$ is $CR^1$; and $R^1$ is CN. In another embodiment of Formula (IIa), $X^1$ and $X^3$ are CH; and $X^2$ is $CR^1$; and $R^1$ is $NH_2$. In another embodiment of Formula (IIa), $X^1$ and $X^3$ are CH; and $X^2$ is $CR^1$; and $R^1$ is $NO_2$. In another embodiment of Formula (IIa), $X^1$ and $X^3$ are CH; and $X^2$ is $CR^1$; and $R^1$ is $CF_3$. In another embodiment of Formula (IIa), $X^1$ and $X^3$ are CH; and $X^2$ is $CR^1$; and $R^1$ is C(O)OH. In another embodiment of Formula (IIa), $X^1$ and $X^3$ are CH; and $X^2$ is $CR^1$; $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; and $R^6$ is alkyl or heterocyclyl.

In another embodiment of Formula (IIa), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (IIa), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $X^2$ and $X^3$ are CH; and $X^1$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $X^2$ and $X^3$ are CH; and $X^1$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $X^2$ and $X^3$ are CH; and $X^1$ is $CR^1$; $R^1$ is C(O)$OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $X^2$ and $X^3$ are CH; and $X^1$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $X^2$ and $X^3$ are CH; and $X^1$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $X^2$ and $X^3$ are CH; and $X^1$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $X^2$ and $X^3$ are CH; and $X^1$ is $CR^1$; and $R^1$ is $C(O)NH_2$. In another embodiment of Formula (IIa), $X^2$ and $X^3$ are CH; and $X^1$ is $CR^1$; and $R^1$ is F. In another embodiment of Formula (IIa), $X^2$ and $X^3$ are CH; and $X^1$ is $CR^1$; and $R^1$ is Cl. In another embodiment of Formula (IIa), $X^2$ and $X^3$ are CH; and $X^1$ is $CR^1$; and $R^1$ is Br. In another embodiment of Formula (IIa), $X^2$ and $X^3$ are CH; and $X^1$ is $CR^1$; and $R^1$ is CN. In another embodiment of Formula (IIa), $X^2$ and $X^3$ are CH; and $X^1$ is $CR^1$; and $R^1$ is $NH_2$. In another embodiment of Formula (IIa), $X^2$ and $X^3$ are CH; and $X^1$ is $CR^1$; and $R^1$ is $NO_2$. In another embodiment of Formula (IIa), $X^2$ and $X^3$ are CH; and $X^1$ is $CR^1$; and $R^1$ is $CF_3$. In another embodiment of Formula (IIa), $X^2$ and $X^3$ are CH; and $X^1$ is $CR^1$; and $R^1$ is C(O)OH. In another embodiment of Formula (IIa), $X^2$ and $X^3$ are CH; and $X^1$ is $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; and $R^6$ is alkyl or heterocyclyl.

In another embodiment of Formula (IIa), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (IIa), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $X^1$ is CH; and $X^2$ and $X^3$ are $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $X^1$ is CH; and $X^2$ and $X^3$ are $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $X^1$ is CH; and $X^2$ and $X^3$ are $CR^1$; $R^1$ is C(O)$OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $X^1$ is CH; and $X^2$ and $X^3$ are $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $X^1$ is CH; and $X^2$ and $X^3$ are $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $X^1$ is CH; and $X^2$ and $X^3$ are $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIa), $X^1$ is CH; and $X^2$ and $X^3$ are $CR^1$; and $R^1$ is $C(O)NH_2$. In another embodiment of Formula (IIa), $X^1$ is CH; and $X^2$ and $X^3$ are $CR^1$; and $R^1$ is F. In another embodiment of Formula (IIa), $X^1$ is CH; and $X^2$ and $X^3$ are $CR^1$; and $R^1$ is Cl. In another embodiment of Formula (IIa), $X^1$ is CH; and $X^2$ and $X^3$ are $CR^1$; and $R^1$ is Br. In another embodiment of Formula (IIa), $X^1$ is CH; and $X^2$ and $X^3$ are $CR^1$; and $R^1$ is CN. In another embodiment of Formula (IIa), $X^1$ is CH; and $X^2$ and $X^3$ are $CR^1$; and $R^1$ is $NH_2$. In another embodiment of Formula (IIa), $X^1$ is CH; and $X^2$ and $X^3$ are $CR^1$; and $R^1$ is $NO_2$. In another embodiment of Formula (IIa), $X^1$ is CH; and $X^2$ and $X^3$ are $CR^1$; and $R^1$ is $CF_3$. In another embodiment of Formula (IIa), $X^1$ is CH; and $X^2$ and $X^3$ are $CR^1$; and $R^1$ is C(O)OH. In another embodiment of Formula (IIa), $X^1$ is CH; and $X^2$ and $X^3$ are $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; and $R^6$ is alkyl or heterocyclyl.

Still another embodiment pertains to compounds having Formula (IIa), which include Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 607, 608, 613, 614, 615, 617, 618, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 682, 683, 684, 685, 686, 687, 700, 701, 702, 703, 704, 705, 706, 707, 708, 709, 710, 711, 712, 713, 714, 715, 716, 717, and pharmaceutically acceptable salts thereof.

Embodiments of Formula (IIIa)

In another aspect, the present invention provides compounds of Formula (IIIa)

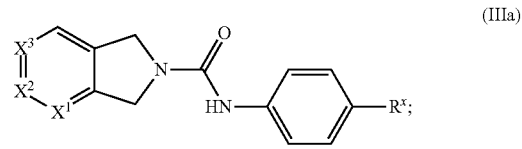

(IIIa)

or pharmaceutically acceptable salts thereof; wherein $X^1$, $X^2$, $X^3$, are as described herein for Formula (Ia); and $R^x$ is as described herein for substituents at the para position in Formula (Ia) when $R^2$ is phenyl.

In one embodiment of formula (IIIa),
$X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or
$X^1$ is CH; $X^2$ is N; and $X^3$ is $CR^1$; or
$X^1$ is $CR^1$; $X^2$ is N; and $X^3$ is CH; or
$X^1$ is N; $X^2$ is $CR^1$; and $X^3$ is CH; or
$X^1$ is N; $X^2$ is $CR^1$; and $X^3$ is N;

$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, $C(O)H$, $CF_3$, $C(O)OH$, or $C(O)NH_2$;

$R^x$ is $R^5$, $OCH_2CH_2CH_2CH_2CH_3$, $SR^5$, $S(O)R^5$, $SO_2R^5$, $C(O)R^5$, $CO(O)R^5$, $OC(O)R^5$, $OC(O)R^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $CHNOR^5$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, OH, CN, $N_3$, $NO_2$, $CF_3$, $CF_2CF_3$, $OCF_3$, $OCF_2CF_3$, Br or I; wherein $R^x$ is not 4-methyl;

$R^3$ is alkyl, alkenyl, alkynyl, aryl, or heterocyclyl; wherein each $R^3$ alkyl, alkenyl, and alkynyl is optionally substituted with one or more independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I;

$R^5$ is alkyl, alkenyl, alkynyl, aryl, heterocyclyl, cycloalkyl, or cycloalkenyl; wherein each $R^5$ alkyl, alkenyl, and alkynyl is optionally substituted with one or more independently selected $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I;

$R^6$ is alkyl, alkenyl, alkynyl, aryl, heterocyclyl, cycloalkyl, or cycloalkenyl; wherein each $R^6$ alkyl, alkenyl, and alkynyl is optionally substituted with one or more independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, OH, (O), C(O)OH, $N_3$, CN, $NH_2$, $CF_3$, $CF_2CF_3$, F, Cl, Br or I;

$R^9$ is alkyl, alkenyl, alkynyl, aryl, heterocyclyl, cycloalkyl, or cycloalkenyl; wherein each $R^9$ alkyl, alkenyl, and alkynyl is optionally substituted with one or more independently selected $OCH_3$, OH, aryl, or heterocyclyl;

$R^{10}$ is alkyl, alkenyl, alkynyl, aryl, heterocyclyl, cycloalkyl, or cycloalkenyl;

wherein the cyclic moieties represented by $R^3$, $R^5$, $R^6$, $R^9$, and $R^{10}$, are optionally substituted with one or more independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, C(O)NHOH, C(O)NHOR$^{13}$, $C(O)NHSO_2R^{13}$, $C(O)NR^{13}SO_2R^{13}$, $SO_2NH_2$, $SO_2NHR^{13}$, $SO_2N(R^{13})_2$, C(O)H, C(O)OH, OH, CN, $N_3$, $NO_2$, $CF_3$, $CF_2CF_3$, $OCF_3$, $OCF_2CF_3$, $SCF_3$, F, Cl, Br or I;

$R^{13}$ is alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, dioxanyl, tetrahydropyranyl, piperidinyl, pyrimidinyl, oxazolyl, pyrazolyl, thiazolyl, pyrrolyl, thienyl, furanyl, cycloalkyl, or cycloalkenyl; wherein each $R^{13}$ alkyl, alkenyl, and alkynyl is optionally substituted with one or more independently selected $R^{14}$, $OR^{14}$, $SR^{14}$, $S(O)R^{14}$, $SO_2R^{14}$, $C(O)R^{14}$, $OC(O)R^{14}$, $OC(O)OR^{14}$, $NH_2$, $NHR^{14}$, $N(R^{14})_2$, $NHC(O)R^{14}$, $NR^{14}$, $C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, C(O)NHOH, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, C(O)H, C(O)OH, OH, (O), CN, $N_3$, $NO_2$, $CF_3$, $CF_2CF_3$, $OCF_3$, $OCF_2CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, dioxanyl, tetrahydropyranyl, piperidinyl, pyrimidinyl, oxazolyl, pyrazolyl, thiazolyl, pyrrolyl, thienyl, furanyl, cycloalkyl, and cycloalkenyl is optionally substituted with one or more independently selected $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, C(O)NHOH, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, C(O)H, C(O)OH, OH, CN, $N_3$, $NO_2$, $CF_3$, $CF_2CF_3$, $OCF_3$, $OCF_2CF_3$, F, Cl, Br or I;

$R^{14}$ is alkyl, alkenyl, alkynyl, aryl, heterocyclyl, cycloalkyl, or cycloalkenyl; wherein each $R^{14}$ alkyl, alkenyl, and alkynyl is optionally substituted with one or more independently selected $OCH_3$, $NH_2$, $SO_2NH_2$, C(O)H, C(O)OH, OH, (O), CN, $N_3$, $NO_2$, $CF_3$, $CF_2CF_3$, $OCF_3$, $OCF_2CF_3$, F, Cl, Br or I; wherein each $R^{14}$ aryl, heterocyclyl, cycloalkyl, or cycloalkenyl is optionally substituted with one or more independently selected alkyl, or $OCH_3$; and $R^{15}$ is alkyl.

In one embodiment of Formula (IIIa), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N; or $X^1$ is CH; $X^2$ is N; and $X^3$ is $CR^1$; or $X^1$ is $CR^1$; $X^2$ is N; and $X^3$ is CH; or $X^1$ is N; $X^2$ is $CR^1$; and $X^3$ is CH; or $X^1$ is N; $X^2$ is $CR^1$; and $X^3$ is N. In another embodiment of Formula (IIIa), $X^1$, $X^2$, and $X^3$ are CH. In another embodiment of Formula (IIIa), $X^1$ and $X^3$ are CH; and $X^2$ is N. In another embodiment of Formula (IIIa), $X^1$ and $X^3$ are CH; and $X^2$ is $CR^1$. In another embodiment of Formula (IIIa), $X^2$ and $X^3$ are CH; and $X^1$ is $CR^1$. In another embodiment of Formula (IIIa), $X^1$ is CH; and $X^2$ and $X^3$ are $CR^1$. In another embodiment of Formula (IIIa), $X^2$ is CH; and $X^1$ and $X^3$ are N. In another embodiment of Formula (IIIa), $X^2$ and $X^3$ are CH; and $X^1$ is N. In another embodiment of Formula (IIIa), $X^1$ is CH; $X^2$ is N; and $X^3$ is $CR^1$. In another embodiment of Formula (IIIa), $X^1$ is $CR^1$; $X^2$ is N; and $X^3$ is CH. In another embodiment of Formula (IIIa), $X^1$ is N; $X^2$ is $CR^1$; and $X^3$ is CH. In another embodiment of Formula (IIIa), $X^1$ is N; $X^2$ is $CR^1$; and $X^3$ is N.

In another embodiment of Formula (IIIa), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (IIIa), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $R^1$ is $C(O)NH_2$. In another embodiment of Formula (IIIa), $R^1$ is F. In another embodiment of Formula (IIIa), $R^1$ is Cl. In another embodiment of Formula (IIIa), $R^1$ is Br. In another embodiment of Formula (IIIa), $R^1$ is CN. In another embodiment of Formula (IIIa), $R^1$ is $NH_2$. In another embodiment of Formula (IIIa), $R^1$ is $NO_2$. In another embodiment of Formula (IIIa), $R^1$ is $CF_3$. In another embodiment of Formula (IIIa), $R^1$ is C(O)OH. In another embodiment of Formula (IIIa), $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl.

In another embodiment of Formula (IIIa), $X^1$ and $X^3$ are CH; and $X^2$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (IIIa), $X^1$ and $X^3$ are CH; and $X^2$ is $CR^1$; $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $X^1$ and $X^3$ are CH; and $X^2$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $X^1$ and $X^3$ are CH; and $X^2$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $X^1$ and $X^3$ are CH; and $X^2$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $X^1$ and $X^3$ are CH; and $X^2$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $X^1$ and $X^3$ are CH; and $X^2$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $X^1$ and $X^3$ are CH; and $X^2$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $X^1$ and $X^3$ are CH; and $X^2$ is $CR^1$; and $R^1$ is $C(O)NH_2$. In another embodiment of Formula (IIIa), $X^1$ and $X^3$ are CH; and $X^2$ is $CR^1$; and $R^1$ is F. In another embodiment of Formula (IIIa), $X^1$ and $X^3$ are CH; and $X^2$ is $CR^1$; and $R^1$ is Cl. In another embodiment of Formula (IIIa), $X^1$ and $X^3$ are CH; and $X^2$ is $CR^1$; and $R^1$ is Br. In another embodiment of Formula (IIIa), $X^1$ and $X^3$ are CH; and $X^2$ is $CR^1$; and $R^1$ is CN. In another embodiment of Formula (IIIa), $X^1$ and $X^3$ are CH; and $X^2$ is $CR^1$; and $R^1$ is $NH_2$. In another embodiment of Formula (IIIa), $X^1$ and $X^3$ are CH; and $X^2$ is $CR^1$; and $R^1$ is $NO_2$. In another embodiment of Formula (IIIa), $X^1$ and $X^3$ are CH; and $X^2$ is $CR^1$; and $R^1$ is $CF_3$. In another embodiment of Formula (IIIa), $X^1$ and $X^3$ are CH; and $X^2$ is $CR^1$; and $R^1$ is C(O)OH. In another embodiment of Formula (IIIa), $X^1$ and $X^3$ are CH; and $X^2$ is $CR^1$; $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; and $R^6$ is alkyl or heterocyclyl.

In another embodiment of Formula (IIIa), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (IIIa), $X^2$ and $X^3$ are CH; and $X^1$ is $CR^1$; $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $X^2$ and $X^3$ are CH; and $X^1$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $X^2$ and $X^3$ are CH; and $X^1$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $X^2$ and $X^3$ are CH; and $X^1$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $X^2$ and $X^3$ are CH; and $X^1$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $X^2$ and $X^3$ are CH; and $X^1$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $X^2$ and $X^3$ are CH; and $X^1$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $X^2$ and $X^3$ are CH; and $X^1$ is $CR^1$; and $R^1$ is $C(O)NH_2$. In another embodiment of Formula (IIIa), $X^2$ and $X^3$ are CH; and $X^1$ is $CR^1$; and $R^1$ is F. In another embodiment of Formula (IIIa), $X^2$ and $X^3$ are CH; and $X^1$ is $CR^1$; and $R^1$ is Cl. In another embodiment of Formula (IIIa), $X^2$ and $X^3$ are CH; and $X^1$ is $CR^1$; and $R^1$ is Br. In another embodiment of Formula (IIIa), $X^2$ and $X^3$ are CH; and $X^1$ is $CR^1$; and $R^1$ is CN. In another embodiment of Formula (IIIa), $X^2$ and $X^3$ are CH; and $X^1$ is $CR^1$; and $R^1$ is $NH_2$. In another embodiment of Formula (IIIa), $X^2$ and $X^3$ are CH; and $X^1$ is $CR^1$; and $R^1$ is $NO_2$. In another embodiment of Formula (IIIa), $X^2$ and $X^3$ are CH; and $X^1$ is $CR^1$; and $R^1$ is $CF_3$. In another embodiment of Formula (IIIa), $X^2$ and $X^3$ are CH; and $X^1$ is $CR^1$; and $R^1$ is C(O)OH. In another embodiment of Formula (IIIa), $X^2$ and $X^3$ are CH; and $X^1$ is $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; and $R^6$ is alkyl or heterocyclyl.

In another embodiment of Formula (IIIa), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (IIIa), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $X^1$ is CH; and $X^2$ and $X^3$ are $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $X^1$ is CH; and $X^2$ and $X^3$ are $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $X^1$ is CH; and $X^2$ and $X^3$ are $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $X^1$ is CH; and $X^2$ and $X^3$ are $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $X^1$ is CH; and $X^2$ and $X^3$ are $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $X^1$ is CH; and $X^2$ and $X^3$ are $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IIIa), $X^1$ is CH; and $X^2$ and $X^3$ are $CR^1$; and $R^1$ is $C(O)NH_2$. In another embodiment of Formula (IIIa), $X^1$ is CH; and $X^2$ and $X^3$ are $CR^1$; and $R^1$ is F. In another embodiment of Formula (IIIa), $X^1$ is CH; and $X^2$ and $X^3$ are $CR^1$; and $R^1$ is Cl. In another embodiment of Formula (IIIa), $X^1$ is CH; and $X^2$ and $X^3$ are $CR^1$; and $R^1$ is Br. In another embodiment of Formula (IIIa), $X^1$ is CH; and $X^2$ and $X^3$ are $CR^1$; and $R^1$ is CN. In another embodiment of Formula (IIIa), $X^1$ is CH; and $X^2$ and $X^3$ are $CR^1$; and $R^1$ is $NH_2$. In another embodiment of Formula (IIIa), $X^1$ is CH; and $X^2$ and $X^3$ are $CR^1$; and $R^1$ is $NO_2$. In another embodiment of Formula (IIIa), $X^1$ is CH; and $X^2$ and $X^3$ are $CR^1$; and $R^1$ is $CF_3$. In another embodiment of Formula (IIIa), $X^1$ is CH; and $X^2$ and $X^3$ are $CR^1$; and $R^1$ is C(O)OH. In another embodiment of Formula (IIIa), $X^1$ is CH; and $X^2$ and $X^3$ are $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; and $R^6$ is alkyl or heterocyclyl.

In one embodiment of formula (IIIa), $R^x$ is $R^5$, $OCH_2CH_2CH_2CH_2CH_2CH_3$, $C(O)R^5$, $CO(O)R^5$, $NHR^5$, $NHC(O)R^5$, $C(O)NH_2$, $C(O)NHR^5$, $C(O)N(R^5)_2$, $CHNOR^5$, $C(O)NHOR^5$, or $CF_3$; wherein $R^x$ is not 4-methyl. In another embodiment of formula (IIIa), $R^x$ is $R^5$, $NHC(O)R^5$, $C(O)NH_2$, $C(O)NHR^5$, $C(O)N(R^5)_2$, $CHNOR^5$, or $C(O)NHOR^5$; wherein $R^x$ is not 4-methyl. In another embodiment of formula (IIIa), $R^x$ is $R^5$, and $R^5$ is heterocyclyl, which is optionally substituted as described in embodiments herein.

In another embodiment of Formula (III), $R^x$ is phthalazin-1(2H)-onyl, isoquinolinyl, isoquinolin-1(2H)-onyl, 5,6,7,8-tetrahydrophthalazin-1(2H)-onyl, 5-fluorophthalazin-1(2H)-onyl, (Z)-3H-benzo[d][1,2]diazepin-4(5H)-onyl, 5-(trifluoromethyl)phthalazin-1(2H)-onyl, pyrrolo[1,2-d][1,2,4]triazin-1(2H)-one, isoindolin-1-onyl, or 1,2,3,6-tetrahydropyridinyl. In another embodiment of Formula (III), $R^x$ is phthalazin-1(2H)-onyl, isoquinolinyl, isoquinolin-1(2H)-onyl, 5,6,7,8-tetrahydrophthalazin-1(2H)-onyl, 5-fluorophthalazin-1(2H)-onyl, (Z)-3H-benzo[d][1,2]diazepin-4(5H)-onyl, 5-(trifluoromethyl)phthalazin-1(2H)-onyl, isoindolin-1-onyl, or pyrrolo[1,2-d][1,2,4]triazin-1(2H)-one; which are optionally substituted as defined herein. In another embodiment of Formula (III), $R^x$ is ,2,3,6-tetrahydropyridinyl; which is optionally substituted as defined herein.

Still another embodiment pertains to compounds having Formula (IIIa), which include Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 327, 330, 331, 332, 333, 336, 337, 338, 339, 340, 341, 342, 343, 348, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 405, 406, 407, 408, 409, 410, 411, 412, 413, 414, 415, 416, 417, 418, 419, 420, 421, 424, 425, 426, 427, 428, 429, 430, 431, 432, 433, 434, 435, 436, 437, 438, 439, 440, 441, 442, 443, 444, 445, 446, 447, 448, 449, 450, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 543, 544, 545, 546, 547, 548, 549, 553, 554, 555, 556, 559, 560, 561, 562, 563, 564, 565, 566, 567, 568, 569, 570, 571, 572, 573, 577, 578, 579, 580, 581, 582, 583, 584, 585, 586, 587, 588, 589, 590, 591, 592, 593, 594, 595, 596, 597, 598, 599, 600, 601, 602, 603, 604, 607, 608, 613, 620, 621, 622, 623, 624, 625, 626, 627, 628, 629, 630, 631, 632, 633, 634, 635, 636, 637, 638, 639, 640, 641, 642, 643, 644, 645, 646, 647, 649, 650, 682, 683, 684, 685, 686, 687, 705, 706, 707, 708, 709, 710, 716, 717, and pharmaceutically acceptable salts thereof.

Still another embodiment pertains to compounds having Formula (IIIa), which include Examples 374, 375, 376, 377, 378, 379, 380, 381, 382, 383, 384, 385, 386, 387, 388, 389, 390, 391, 392, 393, 394, 395, 396, 397, 398, 399, 400, 547, 548, 549, 550, 551, 552, and pharmaceutically acceptable salts thereof.

Embodiments of Formula (IVa)

In another aspect, the present invention provides compounds of Formula (IVa)

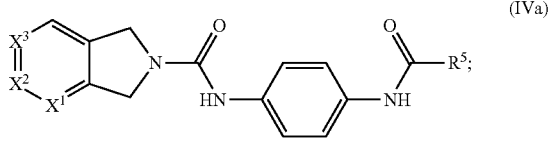

(IVa)

or pharmaceutically acceptable salts thereof; wherein $X^1$, $X^2$, $X^3$, and $R^5$ are as described herein for Formula (Ia).

In one embodiment of formula (IVa), $X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or
$X^1$ is CH; $X^2$ is N; and $X^3$ is $CR^1$; or
$X^1$ is $CR^1$; $X^2$ is N; and $X^3$ is CH; or
$X^1$ is N; $X^2$ is $CR^1$; and $X^3$ is CH; or
$X^1$ is N; $X^2$ is $CR^1$; and $X^3$ is N;

$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, C(O)H, $CF_3$, C(O)OH, or $C(O)NH_2$;

$R^3$ is alkyl, alkenyl, alkynyl, aryl, or heterocyclyl; wherein each $R^3$ alkyl, alkenyl, and alkynyl is optionally substituted with one or more independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, C(O)H, C(O)OH, OH, (O), CN, $N_3$, $NO_2$, $CF_3$, $CF_2CF_3$, $OCF_3$, $OCF_2CF_3$, F, Cl, Br or I;

$R^5$ is alkyl, alkenyl, alkynyl, aryl, heterocyclyl, cycloalkyl, or cycloalkenyl; wherein each $R^5$ alkyl, alkenyl, and alkynyl is optionally substituted with one or more independently selected $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, C(O)NHOH, $C(O)NHOR^9$, $C(O)NHSO_2R^9$, $C(O)NR^9SO_2R^9$, $SO_2NH_2$, $SO_2NHR^9$, $SO_2N(R^9)_2$, C(O)H, C(O)OH, OH, (O), CN, $N_3$, $NO_2$, $CF_3$, $CF_2CF_3$, $OCF_3$, $OCF_2CF_3$, F, Cl, Br or I;

$R^6$ is alkyl, alkenyl, alkynyl, aryl, heterocyclyl, cycloalkyl, or cycloalkenyl; wherein each $R^6$ alkyl, alkenyl, and alkynyl is optionally substituted with one or more independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, OH, (O), C(O)OH, $N_3$, CN, $NH_2$, $CF_3$, $CF_2CF_3$, F, Cl, Br or I;

$R^9$ is alkyl, alkenyl, alkynyl, aryl, heterocyclyl, cycloalkyl, or cycloalkenyl; wherein each $R^9$ alkyl, alkenyl, and alkynyl is optionally substituted with one or more independently selected $OCH_3$, OH, aryl, or heterocyclyl;

$R^{10}$ is alkyl, alkenyl, alkynyl, aryl, heterocyclyl, cycloalkyl, or cycloalkenyl;

wherein the cyclic moieties represented by $R^3$, $R^5$, $R^6$, $R^9$, and $R^{10}$, are optionally substituted with one or more independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, C(O)NHOH, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, C(O)H, C(O)OH, OH, CN, $N_3$, $NO_2$, $CF_3$, $CF_2CF_3$, $OCF_3$, $OCF_2CF_3$, $SCF_3$, F, Cl, Br or I;

$R^{13}$ is alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, dioxanyl, tetrahydropyranyl, piperidinyl, pyrimidinyl, oxazolyl, pyrazolyl, thiazolyl, pyrrolyl, thienyl, furanyl, cycloalkyl, or cycloalkenyl; wherein each $R^{13}$ alkyl, alkenyl, and alkynyl is optionally substituted with one or more independently selected $R^{14}$, $OR^{14}$, $SR^{14}$, $S(O)R^{14}$, $SO_2R^{14}$, $C(O)R^{14}$, $OC(O)R^{14}$, $OC(O)OR^{14}$, $NH_2$, $NHR^{14}$, $N(R^{14})_2$, $NHC(O)R^{14}$, $NR^{14}$, $C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, C(O)NHOH, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, C(O)H, C(O)OH, OH, (O), CN, $N_3$, $NO_2$, $CF_3$, $CF_2CF_3$, $OCF_3$, $OCF_2CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, dioxanyl, tetrahydropyranyl, piperidinyl, pyrimidinyl, oxazolyl, pyrazolyl, thiazolyl, pyrrolyl, thienyl, furanyl, cycloalkyl, and cycloalkenyl is optionally substituted with one or more independently selected $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, C(O)NHOH, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, C(O)H, C(O)OH, OH, CN, $N_3$, $NO_2$, $CF_3$, $CF_2CF_3$, $OCF_3$, $OCF_2CF_3$, F, Cl, Br or I;

$R^{14}$ is alkyl, alkenyl, alkynyl, aryl, heterocyclyl, cycloalkyl, or cycloalkenyl; wherein each $R^{14}$ alkyl, alkenyl, and alkynyl is optionally substituted with one or more independently selected $OCH_3$, $NH_2$, $SO_2NH_2$, C(O)H, C(O)OH, OH, (O), CN, $N_3$, $NO_2$, $CF_3$, $CF_2CF_3$, $OCF_3$, $OCF_2CF_3$, F, Cl, Br or I; wherein each $R^{14}$ aryl, heterocyclyl, cycloalkyl, or cycloalkenyl is optionally substituted with one or more independently selected alkyl, or $OCH_3$; and $R^{15}$ is alkyl;

with the proviso that when $R^2$ is unsubstituted alkyl or optionally substituted alkyl; $R^2$ is $C_4$-$C_6$-alkyl.

In one embodiment of Formula (IVa), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N; or $X^1$ is CH; $X^2$ is N; and $X^3$ is $CR^1$; or $X^1$ is $CR^1$; $X^2$ is N; and $X^3$ is CH; or $X^1$ is N; $X^2$ is $CR^1$; and $X^3$ is CH; or $X^1$ is N; $X^2$ is $CR^1$; and $X^3$ is N. In another embodiment of Formula (IVa), $X^1$, $X^2$, and $X^3$ are CH. In another embodiment of Formula (IVa), $X^1$ and $X^3$ are CH; and $X^2$ is N. In another embodiment of Formula (IVa), $X^1$ and $X^3$ are CH; and $X^2$ is $CR^1$. In another embodiment of Formula (IVa), $X^2$ and $X^3$ are CH; and $X^1$ is $CR^1$. In another embodiment of Formula (IVa), $X^1$ is CH; and $X^2$ and $X^3$ are $CR^1$. In another embodiment of Formula (IVa), $X^2$ is CH; and $X^1$ and $X^3$ are N. In another embodiment of Formula (IVa), $X^2$ and $X^3$ are CH; and $X^1$ is N. In another embodiment of Formula (IVa), $X^1$ is CH; $X^2$ is N; and $X^3$ is $CR^1$. In another embodiment of Formula (IVa), $X^1$ is $CR^1$; $X^2$ is N; and $X^3$ is CH. In another embodiment of Formula (IVa), $X^1$ is N; $X^2$ is $CR^1$; and $X^3$ is CH. In another embodiment of Formula (IVa), $X^1$ is N; $X^2$ is $CR^1$; and $X^3$ is N.

In another embodiment of Formula (IVa), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (IVa), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $R^1$ is $C(O)NH_2$. In another embodiment of Formula (IVa), $R^1$ is F. In another embodiment of Formula (IVa), $R^1$ is Cl. In another embodiment of Formula (IVa), $R^1$ is Br. In another embodiment of Formula (IVa), $R^1$ is CN. In another embodiment of Formula (IVa), $R^1$ is $NH_2$. In another embodiment of Formula (IVa), $R^1$ is $NO_2$. In another embodiment of Formula (IVa), $R^1$ is $CF_3$. In another embodiment of Formula (IVa), $R^1$ is C(O)OH. In another embodiment of Formula (IVa), $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl.

In another embodiment of Formula (IVa), $X^1$ and $X^3$ are CH; and $X^2$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (IVa), $X^1$ and $X^3$ are CH; and $X^2$ is $CR^1$; $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $X^1$ and $X^3$ are CH; and $X^2$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $X^1$ and $X^3$ are CH; and $X^2$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $X^1$ and $X^3$ are CH; and $X^2$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $X^1$ and $X^3$ are CH; and $X^2$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $X^1$ and $X^3$ are CH; and $X^2$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $X^1$ and $X^3$ are CH; and $X^2$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $X^1$ and $X^3$ are CH; and $X^2$ is $CR^1$; and $R^1$ is $C(O)NH_2$. In another embodiment of Formula (IVa), $X^1$ and $X^3$ are CH; and $X^2$ is $CR^1$; and $R^1$ is F. In another embodiment of Formula (IVa), $X^1$ and $X^3$ are CH; and $X^2$ is $CR^1$; and $R^1$ is Cl. In another embodiment of Formula (IVa), $X^1$ and $X^3$ are CH; and $X^2$ is $CR^1$; and $R^1$ is Br. In another embodiment of Formula (IVa), $X^1$ and $X^3$ are CH; and $X^2$ is $CR^1$; and $R^1$ is CN. In another embodiment of Formula (IVa), $X^1$ and $X^3$ are CH; and $X^2$ is $CR^1$; and $R^1$ is $NH_2$. In another embodiment of Formula (IVa), $X^1$ and $X^3$ are CH; and $X^2$ is $CR^1$; and $R^1$ is $NO_2$. In another embodiment of Formula (IVa), $X^1$ and $X^3$ are CH; and $X^2$ is $CR^1$; and $R^1$ is $CF_3$. In another embodiment of Formula (IVa), $X^1$ and $X^3$ are CH; and $X^2$ is $CR^1$; and $R^1$ is C(O)OH. In another embodiment of Formula (IVa), $X^1$ and $X^3$ are CH; and $X^2$ is $CR^1$; $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; and $R^6$ is alkyl or heterocyclyl.

In another embodiment of Formula (IVa), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (IVa), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $X^2$ and $X^3$ are CH; and $X^1$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $X^2$ and $X^3$ are CH; and $X^1$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $X^2$ and $X^3$ are CH; and $X^1$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $X^2$ and $X^3$ are CH; and $X^1$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $X^2$ and $X^3$ are CH; and $X^1$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $X^2$ and $X^3$ are CH; and $X^1$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $X^2$ and $X^3$ are CH; and $X^1$ is $CR^1$; and $R^1$ is $C(O)NH_2$. In another embodiment of Formula (IVa), $X^2$ and $X^3$ are CH; and $X^1$ is $CR^1$; and $R^1$ is F. In another embodiment of Formula (IVa), $X^2$ and $X^3$ are CH; and $X^1$ is $CR^1$; and $R^1$ is Cl. In another embodiment of Formula (IVa), $X^2$ and $X^3$ are CH; and $X^1$ is $CR^1$; and $R^1$ is Br. In another embodiment of Formula (IVa), $X^2$ and $X^3$ are CH; and $X^1$ is $CR^1$; and $R^1$ is CN. In another embodiment of Formula (IVa), $X^2$ and $X^3$ are CH; and $X^1$ is $CR^1$; and $R^1$ is $NH_2$. In another embodiment of Formula (IVa), $X^2$ and $X^3$ are CH; and $X^1$ is $CR^1$; and $R^1$ is $NO_2$. In another embodiment of Formula (IVa), $X^2$ and $X^3$ are CH; and $X^1$ is $CR^1$; and $R^1$ is $CF_3$. In another embodiment of Formula (IVa), $X^2$ and $X^3$ are CH; and $X^1$ is $CR^1$; and $R^1$ is $C(O)OH$. In another embodiment of Formula (IVa), $X^2$ and $X^3$ are CH; and $X^1$ is $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; and $R^6$ is alkyl or heterocyclyl.

In another embodiment of Formula (IVa), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (IVa), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $X^1$ is CH; and $X^2$ and $X^3$ are $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $X^1$ is CH; and $X^2$ and $X^3$ are $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $X^1$ is CH; and $X^2$ and $X^3$ are $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $X^1$ is CH; and $X^2$ and $X^3$ are $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $X^1$ is CH; and $X^2$ and $X^3$ are $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $X^1$ is CH; and $X^2$ and $X^3$ are $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (IVa), $X^1$ is CH; and $X^2$ and $X^3$ are $CR^1$; and $R^1$ is $C(O)NH_2$. In another embodiment of Formula (IVa), $X^1$ is CH; and $X^2$ and $X^3$ are $CR^1$; and $R^1$ is F. In another embodiment of Formula (IVa), $X^1$ is CH; and $X^2$ and $X^3$ are $CR^1$; and $R^1$ is Cl. In another embodiment of Formula (IVa), $X^1$ is CH; and $X^2$ and $X^3$ are $CR^1$; and $R^1$ is Br. In another embodiment of Formula (IVa), $X^1$ is CH; and $X^2$ and $X^3$ are $CR^1$; and $R^1$ is CN. In another embodiment of Formula (IVa), $X^1$ is CH; and $X^2$ and $X^3$ are $CR^1$; and $R^1$ is $NH_2$. In another embodiment of Formula (IVa), $X^1$ is CH; and $X^2$ and $X^3$ are $CR^1$; and $R^1$ is $NO_2$. In another embodiment of Formula (IVa), $X^1$ is CH; and $X^2$ and $X^3$ are $CR^1$; and $R^1$ is $CF_3$. In another embodiment of Formula (IVa), $X^1$ is CH; and $X^2$ and $X^3$ are $CR^1$; and $R^1$ is $C(O)OH$. In another embodiment of Formula (IVa), $X^1$ is CH; and $X^2$ and $X^3$ are $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; and $R^6$ is alkyl or heterocyclyl.

Still another embodiment pertains to compounds having Formula (IVa), which include Examples 291, 292, 293, 294, 295, 296, 297, 298, 299, 300, 301, 302, 303, 304, 305, 306, 307, 308, 309, 310, 311, 312, 313, 314, 315, 563, 564, 577, 579, 580, 581, 582, 583, 584, 596, 607, 649, 650, 682, 683, 684, 685, and pharmaceutically acceptable salts thereof.

Embodiments of Formula (Va)

In another aspect, the present invention provides compounds of Formula (Va)

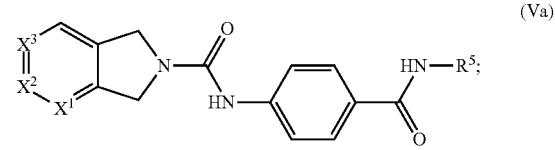

or pharmaceutically acceptable salts thereof; wherein $X^1$, $X^2$, $X^3$, and $R^5$ are as described herein for Formula (Ia).

In one embodiment of formula (Va),
$X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or
$X^1$ is CH; $X^2$ is N; and $X^3$ is $CR^1$; or
$X^1$ is $CR^1$; $X^2$ is N; and $X^3$ is CH; or
$X^1$ is N; $X^2$ is $CR^1$; and $X^3$ is CH; or
$X^1$ is N; $X^2$ is $CR^1$; and $X^3$ is N;
$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)$ OR³, SO₂NH₂, SO₂NHR³, SO₂N(R³)₂, NHSO₂R³, NR³SO₂R³, NHSO₂NHR³, NHSO₂N(R³)₂, NR³SO₂NHR³, NR³SO₂N(R³)₂, C(O)NHSO₂R³, NHSO₂NHR³, F, Cl, Br, I, CN, NH₂, NO₂, N₃, OH, C(O)H, CF₃, C(O)OH, or C(O)NH₂;

R³ is alkyl, alkenyl, aryl, or heterocyclyl; wherein each R³ alkyl, alkenyl, and alkynyl is optionally substituted with one or more independently selected R⁶, OR⁶, SR⁶, S(O)R⁶, SO₂R⁶, C(O)R⁶, CO(O)R⁶, OC(O)R⁶, OC(O)OR⁶, NH₂, NHR⁶, N(R⁶)₂, NHC(O)R⁶, NR⁶C(O)R⁶, NHS(O)₂R⁶, NR⁶S(O)₂R⁶, NHC(O)OR⁶, NR⁶C(O)OR⁶, NHC(O)NH₂, NHC(O)NHR⁶, NHC(O)N(R⁶)₂, NR⁶C(O)NHR⁶, NR⁶C(O)N(R⁶)₂, C(O)NH₂, C(O)NHR⁶, C(O)N(R⁶)₂, C(O)NHOH, C(O)NHOR⁶, C(O)NHSO₂R⁶, C(O)NR⁶SO₂R⁶, SO₂NH₂, SO₂NHR⁶, SO₂N(R⁶)₂, C(O)H, C(O)OH, OH, (O), CN, N₃, NO₂, CF₃, CF₂CF₃, OCF₃, OCF₂CF₃, F, Cl, Br or I;

R⁵ is alkyl, alkenyl, alkynyl, aryl, heterocyclyl, cycloalkyl, or cycloalkenyl; wherein each R⁵ alkyl, alkenyl, and alkynyl is optionally substituted with one or more independently selected R⁹, OR⁹, SR⁹, S(O)R⁹, SO₂R⁹, C(O)R⁹, CO(O)R⁹, OC(O)R⁹, OC(O)OR⁹, NH₂, NHR⁹, N(R⁹)₂, NHC(O)R⁹, NR⁹C(O)R⁹, NHS(O)₂R⁹, NR⁹S(O)₂R⁹, NHC(O)OR⁹, NR⁹C(O)OR⁹, NHC(O)NH₂, NHC(O)NHR⁹, NHC(O)N(R⁹)₂, NR⁹C(O)NHR⁹, NR⁹C(O)N(R⁹)₂, C(O)NH₂, C(O)NHR⁹, C(O)N(R⁹)₂, C(O)NHOH, C(O)NHOR⁹, C(O)NHSO₂R⁹, C(O)NR⁹SO₂R⁹, SO₂NH₂, SO₂NHR⁹, SO₂N(R⁹)₂, C(O)H, C(O)OH, OH, (O), CN, N₃, NO₂, CF₃, CF₂CF₃, OCF₃, OCF₂CF₃, F, Cl, Br or I;

R⁶ is alkyl, alkenyl, alkynyl, aryl, heterocyclyl, cycloalkyl, or cycloalkenyl; wherein each R⁶ alkyl, alkenyl, and alkynyl is optionally substituted with one or more independently selected R¹⁰, OR¹⁰, SR¹⁰, S(O)R¹⁰, SO₂R¹⁰, NHR¹⁰, N(R¹⁰)₂, C(O)R¹⁰, C(O)NH₂, C(O)NHR¹⁰, C(O)N(R¹⁰)₂, NHC(O)R¹⁰, NR¹⁰C(O)R¹⁰, NHSO₂R¹⁰, NHC(O)OR¹⁰, SO₂NH₂, SO₂NHR¹⁰, SO₂N(R¹⁰)₂, NHC(O)NH₂, NHC(O)NHR¹⁰, OH, (O), C(O)OH, N₃, CN, NH₂, CF₃, CF₂CF₃, F, Cl, Br or I;

R⁹ is alkyl, alkenyl, alkynyl, aryl, heterocyclyl, cycloalkyl, or cycloalkenyl; wherein each R⁹ alkyl, alkenyl, and alkynyl is optionally substituted with one or more independently selected OCH₃, OH, aryl, or heterocyclyl;

R¹⁰ is alkyl, alkenyl, alkynyl, aryl, heterocyclyl, cycloalkyl, or cycloalkenyl;

wherein the cyclic moieties represented by R³, R⁵, R⁶, R⁹, and R¹⁰, are optionally substituted with one or more independently selected R¹³, OR¹³, SR¹³, S(O)R¹³, SO₂R¹³, C(O)R¹³, CO(O)R¹³, OC(O)R¹³, OC(O)OR¹³, NH₂, NHR¹³, N(R¹³)₂, NHC(O)R¹³, NR¹³C(O)R¹³, NHS(O)₂R¹³, NR¹³S(O)₂R¹³, NHC(O)OR¹³, NR¹³C(O)OR¹³, NHC(O)NH₂, NHC(O)NHR¹³, NHC(O)N(R¹³)₂, NR¹³C(O)NHR¹³, NR¹³C(O)N(R¹³)₂, C(O)NH₂, C(O)NHR¹³, C(O)N(R¹³)₂, C(O)NHOH, C(O)NHOR¹³, C(O)NHSO₂R¹³, C(O)NR¹³SO₂R¹³, SO₂NH₂, SO₂NHR¹³, SO₂N(R¹³)₂, C(O)H, C(O)OH, OH, CN, N₃, NO₂, CF₃, CF₂CF₃, OCF₃, OCF₂CF₃, SCF₃, F, Cl, Br or I;

R¹³ is alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, dioxanyl, tetrahydropyranyl, piperidinyl, pyrimidinyl, oxazolyl, pyrazolyl, thiazolyl, pyrrolyl, thienyl, furanyl, cycloalkyl, or cycloalkenyl; wherein each R¹³ alkyl, alkenyl, and alkynyl is optionally substituted with one or more independently selected R¹⁴, OR¹⁴, SR¹⁴, S(O)R¹⁴, SO₂R¹⁴, C(O)R¹⁴, OC(O)R¹⁴, OC(O)OR¹⁴, NH₂, NHR¹⁴, N(R¹⁴)₂, NHC(O)R¹⁴, NR¹⁴, C(O)R¹⁴, NHS(O)₂R¹⁴, NR¹⁴S(O)₂R¹⁴, NHC(O)OR¹⁴, NR¹⁴C(O)OR¹⁴, NHC(O)NH₂, NHC(O)NHR¹⁴, NHC(O)N(R¹⁴)₂, NR¹⁴C(O)NHR¹⁴, NR¹⁴C(O)N(R¹⁴)₂, C(O)NH₂, C(O)NHR¹⁴, C(O)N(R¹⁴)₂, C(O)NHOH, C(O)NHOR¹⁴, C(O)NHSO₂R¹⁴, C(O)NR¹⁴SO₂R¹⁴, SO₂NH₂, SO₂NHR¹⁴, SO₂N(R¹⁴)₂, C(O)H, C(O)OH, OH, (O), CN, N₃, NO₂, CF₃, CF₂CF₃, OCF₃, OCF₂CF₃, F, Cl, Br or I; wherein each R¹³ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, dioxanyl, tetrahydropyranyl, piperidinyl, pyrimidinyl, oxazolyl, pyrazolyl, thiazolyl, pyrrolyl, thienyl, furanyl, cycloalkyl, and cycloalkenyl is optionally substituted with one or more independently selected R¹⁵, OR¹⁵, SR¹⁵, S(O)R¹⁵, SO₂R¹⁵, C(O)R¹⁵, CO(O)R¹⁵, OC(O)R¹⁵, OC(O)OR¹⁵, NH₂, NHR¹⁵, N(R¹⁵)₂, NHC(O)R¹⁵, NR¹⁵C(O)R¹⁵, NHS(O)₂R¹⁵, NR¹⁵S(O)₂R¹⁵, NHC(O)OR¹⁵, NR¹⁵C(O)OR¹⁵, NHC(O)NH₂, NHC(O)NHR¹⁵, NHC(O)N(R¹⁵)₂, NR¹⁵C(O)NHR¹⁵, NR¹⁵C(O)N(R¹⁵)₂, C(O)NH₂, C(O)NHR¹⁵, C(O)N(R¹⁵)₂, C(O)NHOH, C(O)NHOR¹⁵, C(O)NHSO₂R¹⁵, C(O)NR¹⁵SO₂R¹⁵, SO₂NH₂, SO₂NHR¹⁵, SO₂N(R¹⁵)₂, C(O)H, C(O)OH, OH, CN, N₃, NO₂, CF₃, CF₂CF₃, OCF₃, OCF₂CF₃, F, Cl, Br or I;

R¹⁴ is alkyl, alkenyl, alkynyl, aryl, heterocyclyl, cycloalkyl, or cycloalkenyl; wherein each R¹⁴ alkyl, alkenyl, and alkynyl is optionally substituted with one or more independently selected OCH₃, NH₂, SO₂NH₂, C(O)H, C(O)OH, OH, (O), CN, N₃, NO₂, CF₃, CF₂CF₃, OCF₃, OCF₂CF₃, F, Cl, Br or I; wherein each R¹⁴ aryl, heterocyclyl, cycloalkyl, or cycloalkenyl is optionally substituted with one or more independently selected alkyl, or OCH₃; and R¹⁵ is alkyl.

In one embodiment of Formula (Va), X¹, X², and X³ are CH; or X¹ and X³ are CH; and X² is N; or X¹ and X³ are CH; and X² is CR¹; or X² and X³ are CH; and X¹ is CR¹; or X¹ is CH; and X² and X³ are CR¹; or X² is CH; and X¹ and X³ are N; or X² and X³ are CH; and X¹ is N; or X¹ is CH; X² is N; and X³ is CR¹; or X¹ is CR¹; X² is N; and X³ is CH; or X¹ is N; X² is CR¹; and X³ is CH; or X¹ is N; X² is CR¹; and X³ is N. In another embodiment of Formula (Va), X¹, X², and X³ are CH. In another embodiment of Formula (Va), X¹ and X³ are CH; and X² is N. In another embodiment of Formula (Va), X¹ and X³ are CH; and X² is CR¹. In another embodiment of Formula (Va), X² and X³ are CH; and X¹ is CR¹. In another embodiment of Formula (Va), X¹ is CH; and X² and X³ are CR¹. In another embodiment of Formula (Va), X² is CH; and X¹ and X³ are N. In another embodiment of Formula (Va), X² and X³ are CH; and X¹ is N. In another embodiment of Formula (Va), X¹ is CH; X² is N; and X³ is CR¹. In another embodiment of Formula (Va), X¹ is CR¹; X² is N; and X³ is CH. In another embodiment of Formula (Va), X¹ is N; X² is CR¹; and X³ is CH. In another embodiment of Formula (Va), X¹ is N; X² is CR¹; and X³ is N.

In another embodiment of Formula (Va), R¹ is R³, OR³, C(O)R³, C(O)OR³, C(O)NH₂, C(O)NHR³, NHC(O)R³, NHSO₂R³, F, Cl, Br, I, CN, NH₂, NO₂, CF₃, or C(O)OH. In another embodiment of Formula (Va), R¹ is R³, OR³, C(O)R³, C(O)OR³, C(O)NH₂, C(O)NHR³, NHC(O)R³, NHSO₂R³, F, Cl, Br, I, CN, NH₂, NO₂, CF₃, or C(O)OH; wherein R³ is alkyl, alkenyl, or heterocyclyl; wherein each alkyl is optionally substituted with one or more independently selected R⁶, OR⁶, NH₂, N(R⁶)₂, or OH; wherein R⁶ is alkyl or heterocyclyl. In another embodiment of Formula (Va), R¹ is R³; wherein R³ is alkyl, alkenyl, or heterocyclyl; wherein each alkyl is optionally substituted with one or more independently selected R⁶, OR⁶, NH₂, N(R⁶)₂, or OH; wherein R⁶ is alkyl or heterocyclyl. In another embodiment of Formula (Va), R¹ is OR³; wherein R³ is alkyl, alkenyl, or heterocyclyl; wherein each alkyl is optionally substituted with one or more independently selected R⁶, OR⁶, NH₂, N(R⁶)₂, or OH; wherein R⁶ is alkyl or heterocyclyl. In another embodiment of Formula (Va), $R^1$ is C(O)OR$^3$; wherein $R^3$ is alkyl, alkenyl, or heterocyclyl; wherein each alkyl is optionally substituted with one or more independently selected $R^6$, OR$^6$, NH$_2$, N(R$^6$)$_2$, or OH; wherein R$^6$ is alkyl or heterocyclyl. In another embodiment of Formula (Va), $R^1$ is C(O)NHR$^3$; wherein R$^3$ is alkyl, alkenyl, or heterocyclyl; wherein each alkyl is optionally substituted with one or more independently selected $R^6$, OR$^6$, NH$_2$, N(R$^6$)$_2$, or OH; wherein R$^6$ is alkyl or heterocyclyl. In another embodiment of Formula (Va), $R^1$ is NHC(O)R$^3$; wherein R$^3$ is alkyl, alkenyl, or heterocyclyl; wherein each alkyl is optionally substituted with one or more independently selected $R^6$, OR$^6$, NH$_2$, N(R$^6$)$_2$, or OH; wherein R$^6$ is alkyl or heterocyclyl. In another embodiment of Formula (Va), $R^1$ is NHSO$_2$R$^3$; wherein R$^3$ is alkyl, alkenyl, or heterocyclyl; wherein each alkyl is optionally substituted with one or more independently selected $R^6$, OR$^6$, NH$_2$, N(R$^6$)$_2$, or OH; wherein R$^6$ is alkyl or heterocyclyl. In another embodiment of Formula (Va), $R^1$ is C(O)NH$_2$. In another embodiment of Formula (Va), $R^1$ is F. In another embodiment of Formula (Va), $R^1$ is Cl. In another embodiment of Formula (Va), $R^1$ is Br. In another embodiment of Formula (Va), $R^1$ is CN. In another embodiment of Formula (Va), $R^1$ is NH$_2$. In another embodiment of Formula (Va), $R^1$ is NO$_2$. In another embodiment of Formula (Va), $R^1$ is CF$_3$. In another embodiment of Formula (Va), $R^1$ is C(O)OH. In another embodiment of Formula (Va), $R^1$ is C(O)R$^3$; wherein R$^3$ is alkyl, alkenyl, or heterocyclyl; wherein each alkyl is optionally substituted with one or more independently selected $R^6$, OR$^6$, NH$_2$, N(R$^6$)$_2$, or OH; wherein R$^6$ is alkyl or heterocyclyl.

In another embodiment of Formula (Va), $X^1$ and $X^3$ are CH; and $X^2$ is CR$^1$; and $R^1$ is R$^3$, OR$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH. In another embodiment of Formula (Va), $X^1$ and $X^3$ are CH; and $X^2$ is CR$^1$; $R^1$ is R$^3$, OR$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH; wherein R$^3$ is alkyl, alkenyl, or heterocyclyl; wherein each alkyl is optionally substituted with one or more independently selected $R^6$, OR$^6$, NH$_2$, N(R$^6$)$_2$, or OH; wherein R$^6$ is alkyl or heterocyclyl. In another embodiment of Formula (Va), $X^1$ and $X^3$ are CH; and $X^2$ is CR$^1$; $R^1$ is R$^3$; wherein R$^3$ is alkyl, alkenyl, or heterocyclyl; wherein each alkyl is optionally substituted with one or more independently selected $R^6$, OR$^6$, NH$_2$, N(R$^6$)$_2$, or OH; wherein R$^6$ is alkyl or heterocyclyl. In another embodiment of Formula (Va), $X^1$ and $X^3$ are CH; and $X^2$ is CR$^1$; $R^1$ is OR$^3$; wherein R$^3$ is alkyl, alkenyl, or heterocyclyl; wherein each alkyl is optionally substituted with one or more independently selected $R^6$, OR$^6$, NH$_2$, N(R$^6$)$_2$, or OH; wherein R$^6$ is alkyl or heterocyclyl. In another embodiment of Formula (Va), $X^1$ and $X^3$ are CH; and $X^2$ is CR$^1$; $R^1$ is C(O)OR$^3$; wherein R$^3$ is alkyl, alkenyl, or heterocyclyl; wherein each alkyl is optionally substituted with one or more independently selected $R^6$, OR$^6$, NH$_2$, N(R$^6$)$_2$, or OH; wherein R$^6$ is alkyl or heterocyclyl. In another embodiment of Formula (Va), $X^1$ and $X^3$ are CH; and $X^2$ is CR$^1$; $R^1$ is C(O)NHR$^3$; wherein R$^3$ is alkyl, alkenyl, or heterocyclyl; wherein each alkyl is optionally substituted with one or more independently selected $R^6$, OR$^6$, NH$_2$, N(R$^6$)$_2$, or OH; wherein R$^6$ is alkyl or heterocyclyl. In another embodiment of Formula (Va), $X^1$ and $X^3$ are CH; and $X^2$ is CR$^1$; $R^1$ is NHC(O)R$^3$; wherein R$^3$ is alkyl, alkenyl, or heterocyclyl; wherein each alkyl is optionally substituted with one or more independently selected $R^6$, OR$^6$, NH$_2$, N(R$^6$)$_2$, or OH; wherein R$^6$ is alkyl or heterocyclyl. In another embodiment of Formula (Va), $X^1$ and $X^3$ are CH; and $X^2$ is CR$^1$; $R^1$ is NHSO$_2$R$^3$; wherein R$^3$ is alkyl, alkenyl, or heterocyclyl; wherein each alkyl is optionally substituted with one or more independently selected $R^6$, OR$^6$, NH$_2$, N(R$^6$)$_2$, or OH; wherein R$^6$ is alkyl or heterocyclyl. In another embodiment of Formula (Va), $X^1$ and $X^3$ are CH; and $X^2$ is CR$^1$; and $R^1$ is C(O)NH$_2$. In another embodiment of Formula (Va), $X^1$ and $X^3$ are CH; and $X^2$ is CR$^1$; and $R^1$ is F. In another embodiment of Formula (Va), $X^1$ and $X^3$ are CH; and $X^2$ is CR$^1$; and $R^1$ is Cl. In another embodiment of Formula (Va), $X^1$ and $X^3$ are CH; and $X^2$ is CR$^1$; and $R^1$ is Br. In another embodiment of Formula (Va), $X^1$ and $X^3$ are CH; and $X^2$ is CR$^1$; and $R^1$ is CN. In another embodiment of Formula (Va), $X^1$ and $X^3$ are CH; and $X^2$ is CR$^1$; and $R^1$ is NH$_2$. In another embodiment of Formula (Va), $X^1$ and $X^3$ are CH; and $X^2$ is CR$^1$; and $R^1$ is NO$_2$. In another embodiment of Formula (Va), $X^1$ and $X^3$ are CH; and $X^2$ is CR$^1$; and $R^1$ is CF$_3$. In another embodiment of Formula (Va), $X^1$ and $X^3$ are CH; and $X^2$ is CR$^1$; and $R^1$ is C(O)OH. In another embodiment of Formula (Va), $X^1$ and $X^3$ are CH; and $X^2$ is CR$^1$; $R^1$ is C(O)R$^3$; wherein R$^3$ is alkyl, alkenyl, or heterocyclyl; wherein each alkyl is optionally substituted with one or more independently selected $R^6$, OR$^6$, NH$_2$, N(R$^6$)$_2$, or OH; and R$^6$ is alkyl or heterocyclyl.

In another embodiment of Formula (Va), $X^2$ and $X^3$ are CH; and $X^1$ is CR$^1$; and $R^1$ is R$^3$, OR$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH. In another embodiment of Formula (Va), $X^2$ and $X^3$ are CH; and $X^1$ is CR$^1$; and $R^1$ is R$^3$, OR$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH; wherein R$^3$ is alkyl, alkenyl, or heterocyclyl; wherein each alkyl is optionally substituted with one or more independently selected $R^6$, OR$^6$, NH$_2$, N(R$^6$)$_2$, or OH; wherein R$^6$ is alkyl or heterocyclyl. In another embodiment of Formula (Va), $X^2$ and $X^3$ are CH; and $X^1$ is CR$^1$; $R^1$ is R$^3$; wherein R$^3$ is alkyl, alkenyl, or heterocyclyl; wherein each alkyl is optionally substituted with one or more independently selected $R^6$, OR$^6$, NH$_2$, N(R$^6$)$_2$, or OH; wherein R$^6$ is alkyl or heterocyclyl. In another embodiment of Formula (Va), $X^2$ and $X^3$ are CH; and $X^1$ is CR$^1$; $R^1$ is OR$^3$; wherein R$^3$ is alkyl, alkenyl, or heterocyclyl; wherein each alkyl is optionally substituted with one or more independently selected $R^6$, OR$^6$, NH$_2$, N(R$^6$)$_2$, or OH; wherein R$^6$ is alkyl or heterocyclyl. In another embodiment of Formula (Va), $X^2$ and $X^3$ are CH; and $X^1$ is CR$^1$; $R^1$ is C(O)OR$^3$; wherein R$^3$ is alkyl, alkenyl, or heterocyclyl; wherein each alkyl is optionally substituted with one or more independently selected $R^6$, OR$^6$, NH$_2$, N(R$^6$)$_2$, or OH; wherein R$^6$ is alkyl or heterocyclyl. In another embodiment of Formula (Va), $X^2$ and $X^3$ are CH; and $X^1$ is CR$^1$; $R^1$ is C(O)NHR$^3$; wherein R$^3$ is alkyl, alkenyl, or heterocyclyl; wherein each alkyl is optionally substituted with one or more independently selected $R^6$, OR$^6$, NH$_2$, N(R$^6$)$_2$, or OH; wherein R$^6$ is alkyl or heterocyclyl. In another embodiment of Formula (Va), $X^2$ and $X^3$ are CH; and $X^1$ is CR$^1$; $R^1$ is NHC(O)R$^3$; wherein R$^3$ is alkyl, alkenyl, or heterocyclyl; wherein each alkyl is optionally substituted with one or more independently selected $R^6$, OR$^6$, NH$_2$, N(R$^6$)$_2$, or OH; wherein R$^6$ is alkyl or heterocyclyl. In another embodiment of Formula (Va), $X^2$ and $X^3$ are CH; and $X^1$ is CR$^1$; $R^1$ is NHSO$_2$R$^3$; wherein R$^3$ is alkyl, alkenyl, or heterocyclyl; wherein each alkyl is optionally substituted with one or more independently selected $R^6$, OR$^6$, NH$_2$, N(R$^6$)$_2$, or OH; wherein R$^6$ is alkyl or heterocyclyl. In another embodiment of Formula (Va), $X^2$ and $X^3$ are CH; and $X^1$ is CR$^1$; and $R^1$ is C(O)NH$_2$. In another embodiment of Formula (Va), $X^2$ and $X^3$ are CH; and $X^1$ is CR$^1$; and $R^1$ is F. In another embodiment of Formula (Va), $X^2$ and $X^3$ are CH; and $X^1$ is CR$^1$; and $R^1$ is Cl. In another embodiment of Formula (Va), $X^2$ and $X^3$ are CH; and $X^1$ is CR$^1$; and $R^1$ is Br. In another embodiment of Formula (Va), $X^2$ and $X^3$ are CH; and $X^1$ is CR$^1$; and $R^1$ is CN. In another embodiment of Formula (Va), $X^2$ and $X^3$ are CH; and $X^1$ is $CR^1$; and $R^1$ is $NH_2$. In another embodiment of Formula (Va), $X^2$ and $X^3$ are CH; and $X^1$ is $CR^1$; and $R^1$ is $NO_2$. In another embodiment of Formula (Va), $X^2$ and $X^3$ are CH; and $X^1$ is $CR^1$; and $R^1$ is $CF_3$. In another embodiment of Formula (Va), $X^2$ and $X^3$ are CH; and $X^1$ is $CR^1$; and $R^1$ is C(O)OH. In another embodiment of Formula (Va), $X^2$ and $X^3$ are CH; and $X^1$ is $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; and $R^6$ is alkyl or heterocyclyl.

In another embodiment of Formula (Va), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (Va), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Va), $X^1$ is CH; and $X^2$ and $X^3$ are $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Va), $X^1$ is CH; and $X^2$ and $X^3$ are $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Va), $X^1$ is CH; and $X^2$ and $X^3$ are $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Va), $X^1$ is CH; and $X^2$ and $X^3$ are $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Va), $X^1$ is CH; and $X^2$ and $X^3$ are $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Va), $X^1$ is CH; and $X^2$ and $X^3$ are $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; wherein $R^6$ is alkyl or heterocyclyl. In another embodiment of Formula (Va), $X^1$ is CH; and $X^2$ and $X^3$ are $CR^1$; and $R^1$ is $C(O)NH_2$. In another embodiment of Formula (Va), $X^1$ is CH; and $X^2$ and $X^3$ are $CR^1$; and $R^1$ is F. In another embodiment of Formula (Va), $X^1$ is CH; and $X^2$ and $X^3$ are $CR^1$; and $R^1$ is Cl. In another embodiment of Formula (Va), $X^1$ is CH; and $X^2$ and $X^3$ are $CR^1$; and $R^1$ is Br. In another embodiment of Formula (Va), $X^1$ is CH; and $X^2$ and $X^3$ are $CR^1$; and $R^1$ is CN. In another embodiment of Formula (Va), $X^1$ is CH; and $X^2$ and $X^3$ are $CR^1$; and $R^1$ is $NH_2$. In another embodiment of Formula (Va), $X^1$ is CH; and $X^2$ and $X^3$ are $CR^1$; and $R^1$ is $NO_2$. In another embodiment of Formula (Va), $X^1$ is CH; and $X^2$ and $X^3$ are $CR^1$; and $R^1$ is $CF_3$. In another embodiment of Formula (Va), $X^1$ is CH; and $X^2$ and $X^3$ are $CR^1$; and $R^1$ is C(O)OH. In another embodiment of Formula (Va), $X^1$ is CH; and $X^2$ and $X^3$ are $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, or OH; and $R^6$ is alkyl or heterocyclyl.

Still another embodiment pertains to compounds having Formula (Va), which include Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 373, 410, 411, 412, 413, 414, 415, 416, 417, 418, 419, 420, 421, 424, 425, 426, 427, 430, 431, 434, 435, 436, 437, 438, 439, 440, 441, 442, 445, 446, 447, 448, 449, 450, 496, 497, 553, 554, 555, 556, 559, 560, 561, 562, 565, 567, 568, 569, 570, 571, 572, 585, 586, 587, 588, 589, 590, 591, 592, 593, 594, 595, 597, 598, 599, 600, 601, 602, 603, 604, 608, 613, 625, 626, 627, 628, 629, 630, 631, 632, 633, 634, 635, 686, 687, 716, 717, and pharmaceutically acceptable salts thereof.

Embodiments of Formula (VIa)

In another aspect, the present invention provides compounds of Formula (VIa)

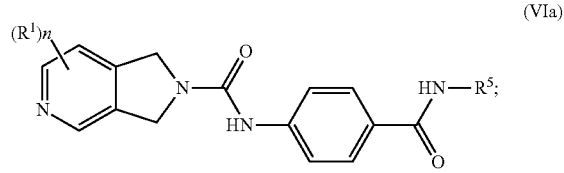

(VIa)

or pharmaceutically acceptable salts thereof; wherein $R^1$ and $R^5$ are as described herein for Formula (Ia); and n is 0 or 1.

In one embodiment of formula (VIa), n is 0 or 1;

$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, C(O)H, $CF_3$, C(O)OH, or $C(O)NH_2$;

$R^3$ is alkyl, alkenyl, alkynyl, aryl, or heterocyclyl; wherein each $R^3$ alkyl, alkenyl, and alkynyl is optionally substituted with one or more independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N$ (R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, SO$_2$NH$_2$, SO$_2$NHR$^6$, SO$_2$N(R$^6$)$_2$, C(O)H, C(O)OH, OH, (O), CN, N$_3$, NO$_2$, CF$_3$, CF$_2$CF$_3$, OCF$_3$, OCF$_2$CF$_3$, F, Cl, Br or I;

R$^5$ is alkyl, alkenyl, alkynyl, aryl, heterocyclyl, cycloalkyl, or cycloalkenyl; wherein each R$^5$ alkyl, alkenyl, and alkynyl is optionally substituted with one or more independently selected R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N(R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9$)$_2$, C(O)H, C(O)OH, OH, (O), CN, N$_3$, NO$_2$, CF$_3$, CF$_2$CF$_3$, OCF$_3$, OCF$_2$CF$_3$, F, Cl, Br or I;

R$^6$ is alkyl, alkenyl, alkynyl, aryl, heterocyclyl, cycloalkyl, or cycloalkenyl; wherein each R$^6$ alkyl, alkenyl, and alkynyl is optionally substituted with one or more independently selected R$^{10}$, OR$^{10}$, SR$^{10}$, S(O)R$^{10}$, SO$_2$R$^{10}$, NHR$^{10}$, N(R$^{10}$)$_2$, C(O)R$^{10}$, C(O)NH$_2$, C(O)NHR$^{10}$, C(O)N(R$^{10}$)$_2$, NHC(O)R$^{10}$, NR$^{10}$C(O)R$^{10}$, NHSO$_2$R$^{10}$, NHC(O)OR$^{10}$, SO$_2$NH$_2$, SO$_2$NHR$^{10}$, SO$_2$N(R$^{10}$)$_2$, NHC(O)NH$_2$, NHC(O)NHR$^{10}$, OH, (O), C(O)OH, N$_3$, CN, NH$_2$, CF$_3$, CF$_2$CF$_3$, F, Cl, Br or I;

R$^9$ is alkyl, alkenyl, alkynyl, aryl, heterocyclyl, cycloalkyl, or cycloalkenyl; wherein each R$^9$ alkyl, alkenyl, and alkynyl is optionally substituted with one or more independently selected OCH$_3$, OH, aryl, or heterocyclyl;

R$^{10}$ is alkyl, alkenyl, alkynyl, aryl, heterocyclyl, cycloalkyl, or cycloalkenyl;

wherein the cyclic moieties represented by R$^3$, R$^5$, R$^6$, R$^9$, and R$^{10}$, are optionally substituted with one or more independently selected R$^{13}$, OR$^{13}$, SR$^{13}$, S(O)R$^{13}$, SO$_2$R$^{13}$, C(O)R$^{13}$, CO(O)R$^{13}$, OC(O)R$^{13}$, OC(O)OR$^{13}$, NH$_2$, NHR$^{13}$, N(R$^{13}$)$_2$, NHC(O)R$^{13}$, NR$^{13}$C(O)R$^{13}$, NHS(O)$_2$R$^{13}$, NR$^{13}$S(O)$_2$R$^{13}$, NHC(O)OR$^{13}$, NR$^{13}$C(O)OR$^{13}$, NHC(O)NH$_2$, NHC(O)NHR$^{13}$, NHC(O)N(R$^{13}$)$_2$, NR$^{13}$C(O)NHR$^{13}$, NR$^{13}$C(O)N(R$^{13}$)$_2$, C(O)NH$_2$, C(O)NHR$^{13}$, C(O)N(R$^{13}$)$_2$, C(O)NHOH, C(O)NHOR$^{13}$, C(O)NHSO$_2$R$^{13}$, C(O)NR$^{13}$SO$_2$R$^{13}$, SO$_2$NH$_2$, SO$_2$NHR$^{13}$, SO$_2$N(R$^{13}$)$_2$, C(O)H, C(O)OH, OH, CN, N$_3$, NO$_2$, CF$_3$, CF$_2$CF$_3$, OCF$_3$, OCF$_2$CF$_3$, SCF$_3$, F, Cl, Br or I;

R$^{13}$ is alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, dioxanyl, tetrahydropyranyl, piperidinyl, pyrimidinyl, oxazolyl, pyrazolyl, thiazolyl, pyrrolyl, thienyl, furanyl, cycloalkyl, or cycloalkenyl; wherein each R$^{13}$ alkyl, alkenyl, and alkynyl is optionally substituted with one or more independently selected R$^{14}$, OR$^{14}$, SR$^{14}$, S(O)R$^{14}$, SO$_2$R$^{14}$, C(O)R$^{14}$, OC(O)R$^{14}$, OC(O)OR$^{14}$, NH$_2$, NHR$^{14}$, N(R$^{14}$)$_2$, NHC(O)R$^{14}$, NR$^{14}$, C(O)R$^{14}$, NHS(O)$_2$R$^{14}$, NR$^{14}$S(O)$_2$R$^{14}$, NHC(O)OR$^{14}$, NR$^{14}$C(O)OR$^{14}$, NHC(O)NH$_2$, NHC(O)NHR$^{14}$, NHC(O)N(R$^{14}$)$_2$, NR$^{14}$C(O)NHR$^{14}$, NR$^{14}$C(O)N(R$^{14}$)$_2$, C(O)NH$_2$, C(O)NHR$^{14}$, C(O)N(R$^{14}$)$_2$, C(O)NHOH, C(O)NHOR$^{14}$, C(O)NHSO$_2$R$^{14}$, C(O)NR$^{14}$SO$_2$R$^{14}$, SO$_2$NH$_2$, SO$_2$NHR$^{14}$, SO$_2$N(R$^{14}$)$_2$, C(O)H, C(O)OH, OH, (O), CN, N$_3$, NO$_2$, CF$_3$, CF$_2$CF$_3$, OCF$_3$, OCF$_2$CF$_3$, F, Cl, Br or I; wherein each R$^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, dioxanyl, tetrahydropyranyl, piperidinyl, pyrimidinyl, oxazolyl, pyrazolyl, thiazolyl, pyrrolyl, thienyl, furanyl, cycloalkyl, and cycloalkenyl is optionally substituted with one or more independently selected R$^{15}$, OR$^{15}$, SR$^{15}$, S(O)R$^{15}$, SO$_2$R$^{15}$, C(O)R$^{15}$, CO(O)R$^{15}$, OC(O)R$^{15}$, OC(O)OR$^{15}$, NH$_2$, NHR$^{15}$, N(R$^{15}$)$_2$, NHC(O)R$^{15}$, NR$^{15}$C(O)R$^{15}$, NHS(O)$_2$R$^{15}$, NR$^{15}$S(O)$_2$R$^{15}$, NHC(O)OR$^{15}$, NR$^{15}$C(O)OR$^{15}$, NHC(O)NH$_2$, NHC(O)NHR$^{15}$, NHC(O)N(R$^{15}$)$_2$, NR$^{15}$C(O)NHR$^{15}$, NR$^{15}$C(O)N(R$^{15}$)$_2$, C(O)NH$_2$, C(O)NHR$^{15}$, C(O)N(R$^{15}$)$_2$, C(O)NHOH, C(O)NHOR$^{15}$, C(O)NHSO$_2$R$^{15}$, C(O)NR$^{15}$SO$_2$R$^{15}$, SO$_2$NH$_2$, SO$_2$NHR$^{15}$, SO$_2$N(R$^{15}$)$_2$, C(O)H, C(O)OH, OH, CN, N$_3$, NO$_2$, CF$_3$, CF$_2$CF$_3$, OCF$_3$, OCF$_2$CF$_3$, F, Cl, Br or I;

R$^{14}$ is alkyl, alkenyl, alkynyl, aryl, heterocyclyl, cycloalkyl, or cycloalkenyl; wherein each R$^{14}$ alkyl, alkenyl, and alkynyl is optionally substituted with one or more independently selected OCH$_3$, NH$_2$, SO$_2$NH$_2$, C(O)H, C(O)OH, OH, (O), CN, N$_3$, NO$_2$, CF$_3$, CF$_2$CF$_3$, OCF$_3$, OCF$_2$CF$_3$, F, Cl, Br or I; wherein each R$^{14}$ aryl, heterocyclyl, cycloalkyl, or cycloalkenyl is optionally substituted with one or more independently selected alkyl, or OCH$_3$; and R$^{15}$ is alkyl.

In another embodiment of Formula (VIa), n is 0. In another embodiment of Formula (VIa), n is 1. In another embodiment of Formula (VIa), R$^1$ is R$^3$, OR$^3$, C(O)R$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH. In another embodiment of Formula (VIa), R$^1$ is R$^3$, OR$^3$, C(O)R$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl. In another embodiment of Formula (VIa), R$^1$ is R$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl. In another embodiment of Formula (VIa), R$^1$ is OR$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl. In another embodiment of Formula (VIa), R$^1$ is C(O)OR$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl. In another embodiment of Formula (VIa), R$^1$ is C(O)NHR$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl. In another embodiment of Formula (VIa), R$^1$ is NHC(O)R$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl. In another embodiment of Formula (VIa), R$^1$ is NHSO$_2$R$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl. In another embodiment of Formula (VIa), R$^1$ is C(O)NH$_2$. In another embodiment of Formula (VIa), R$^1$ is F. In another embodiment of Formula (VIa), R$^1$ is Cl. In another embodiment of Formula (VIa), R$^1$ is Br. In another embodiment of Formula (VIa), R$^1$ is CN. In another embodiment of Formula (VIa), R$^1$ is NH$_2$. In another embodiment of Formula (VIa), R$^1$ is NO$_2$. In another embodiment of Formula (VIa), R$^1$ is CF$_3$. In another embodiment of Formula (VIa), R$^1$ is C(O)OH. In another embodiment of Formula (VIa), R$^1$ is C(O)R$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, or OH; wherein R$^6$ is alkyl or heterocyclyl.

Still another embodiment pertains to compounds having Formula (VIa), which include Examples 285, 286, 287, 288, 289, 290, 426, 427, 437, 445, 553, 554, 555, 556, 599, 627, 628, 629, 630, 631, 632, 633, 634, 635, 686, 687, and pharmaceutically acceptable salts thereof.

Embodiments of Formula (Ib)

One embodiment of this invention, therefore, pertains to compounds or pharmaceutically acceptable salts, which are useful as inhibitors of NAMPT, the compounds having Formula (Ib)

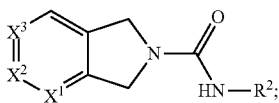

Formula (Ib)

wherein
$X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or
$X^1$ is CH; $X^2$ is N; and $X^3$ is $CR^1$; or
$X^1$ is $CR^1$; $X^2$ is N; and $X^3$ is CH; or
$X^1$ is N; $X^2$ is $CR^1$; and $X^3$ is CH; or
$X^1$ is N; $X^2$ is $CR^1$; and $X^3$ is N;

$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, C(O)H, $CF_3$, C(O)OH, or C(O)$NH_2$;

$R^2$ is alkyl, alkenyl, alkynyl, phenyl, heterocyclyl, cycloalkyl, or cycloalkenyl; wherein each $R^2$ alkyl, alkenyl, and alkynyl is optionally substituted with one, two, three or four independently selected $R^4$, $OR^4$, $SR^4$, $S(O)R^4$, $SO_2R^4$, $C(O)R^4$, $CO(O)R^4$, $OC(O)R^4$, $OC(O)OR^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, C(O)H, (O), CN, $N_3$, $NO_2$, $CF_3$, $CF_2CF_3$, $OCF_3$, $OCF_2CF_3$, F, Cl, Br or I; wherein each $R^2$ phenyl is optionally substituted at the para position with one independently selected $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $CHNOR^5$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, C(O)H, C(O)OH, OH, CN, $N_3$, $NO_2$, $CF_3$, $CF_2CF_3$, $OCF_3$, $OCF_2CF_3$, Br or I; wherein each $R^2$ phenyl is optionally additionally substituted with one F; wherein each $R^2$ heterocyclyl, cycloalkyl, and cycloalkenyl is optionally substituted with one, two, three or four independently selected $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, C(O)H, C(O)OH, OH, CN, $N_3$, $CF_3$, $CF_2CF_3$, $OCF_3$, $OCF_2CF_3$, F, Cl, Br or I;

$R^3$, at each occurrence, is independently selected alkyl, alkenyl, alkynyl, aryl, or heterocyclyl; wherein each $R^3$ alkyl, alkenyl, and alkynyl is optionally substituted with one, two, three or four independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, C(O)H, C(O)OH, OH, (O), CN, $N_3$, $NO_2$, $CF_3$, $CF_2CF_3$, $OCF_3$, $OCF_2CF_3$, F, Cl, Br or I;

$R^4$, at each occurrence, is independently selected alkyl, alkenyl, alkynyl, aryl, cycloalkyl, or heterocyclyl; wherein each $R^4$ alkyl, alkenyl, and alkynyl is optionally substituted with one, two, three or four independently selected $R^7$, $OR^7$, $SR^7$, $S(O)R^7$, $SO_2R^7$, $C(O)R^7$, $OC(O)R^7$, $OC(O)OR^7$, $NH_2$, $NHR^7$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, C(O)H, OH, (O), CN, $N_3$, $NO_2$, $CF_3$, $CF_2CF_3$, $OCF_3$, $OCF_2CF_3$, F, Cl, Br or I; wherein each $R^4$ aryl and heterocycyl is optionally substituted with one, two, three or four independently selected $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, C(O)H, C(O)OH, OH, CN, $N_3$, $NO_2$, $CF_3$, $CF_2CF_3$, $OCF_3$, $OCF_2CF_3$, F, Cl, Br or I;

$R^5$, at each occurrence, is independently selected alkyl, alkenyl, alkynyl, aryl, heterocyclyl, cycloalkyl, or cycloalkenyl; wherein each $R^5$ alkyl, alkenyl, and alkynyl is optionally substituted with one, two, three or four independently selected $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, C(O)H, C(O)OH, OH, (O), CN, $N_3$, $NO_2$, $CF_3$, $CF_2CF_3$, $OCF_3$, $OCF_2CF_3$, F, Cl, Br or I;

$R^6$, at each occurrence, is independently selected alkyl, alkenyl, alkynyl, aryl, heterocyclyl, cycloalkyl, or cycloalkenyl; wherein each $R^6$ alkyl, alkenyl, and alkynyl is optionally substituted with one, two, three or four independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, OH, (O), C(O)OH, $N_3$, CN, $NH_2$, $CF_3$, $CF_2CF_3$, F, Cl, Br or I;

$R^7$, at each occurrence, is independently selected alkyl, alkenyl, alkynyl, aryl, heterocyclyl, cycloalkyl, or cycloalkenyl; wherein each $R^7$ alkyl, alkenyl, and alkynyl is optionally substituted with one, two, three or four independently selected $R^{11}$, $OR^{11}$, $SR^{11}$, $S(O)R^{11}$, $SO_2R^{11}$, $NHR^{11}$, $N(R^{11})_2$, $C(O)R^{11}$, $C(O)NH_2$, $C(O)NHR^{11}$, $C(O)N(R^{11})_2$, $NHC(O)R^{11}$, $NR^{11}C(O)R^{11}$, $NHSO_2R^{11}$, $NHC(O)OR^{11}$, $SO_2NH_2$, $SO_2NHR^{11}$, $SO_2N(R^{11})_2$, $NHC(O)NH_2$, $NHC(O)NHR^{11}$, OH, (O), C(O)OH, $N_3$, CN, $NH_2$, $CF_3$, $CF_2CF_3$, F, Cl, Br or I;

$R^8$, at each occurrence, is independently selected alkyl, alkenyl, alkynyl, aryl, heterocyclyl, cycloalkyl, or cycloalkenyl; wherein each $R^8$ alkyl, alkenyl, and alkynyl is optionally substituted with one, two, three or four independently selected $R^{12}$, $OR^{12}$, $SR^{12}$, $S(O)R^{12}$, $SO_2R^{12}$, $NHR^{12}$, $N(R^{12})_2$, $C(O)R^{12}$, $C(O)NH_2$, $C(O)NHR^{12}$, $C(O)N(R^{12})_2$, $NHC(O)R^{12}$, $NR^{12}C(O)R^{12}$, $NHSO_2R^{12}$, $NHC(O)OR^{12}$, $SO_2NH_2$, $SO_2NHR^{12}$, $SO_2N(R^{12})_2$, $NHC(O)NH_2$, $NHC(O)NHR^{12}$, OH, (O), C(O)OH, $N_3$, CN, $NH_2$, $CF_3$, $CF_2CF_3$, F, Cl, Br or I;

$R^9$, at each occurrence, is independently selected alkyl, alkenyl, alkynyl, aryl, heterocyclyl, cycloalkyl, or cycloalkenyl; wherein each $R^9$ alkyl, alkenyl, and alkynyl is optionally substituted with one, two, three or four independently selected alkoxy, OH, cycloalkyl, aryl, or heterocyclyl;

$R^{10}$, at each occurrence, is independently selected alkyl, alkenyl, alkynyl, aryl, heterocyclyl, cycloalkyl, or cycloalkenyl;

$R^{11}$, at each occurrence, is independently selected alkyl, alkenyl, alkynyl, aryl, heterocyclyl, cycloalkyl, or cycloalkenyl;

$R^{12}$, at each occurrence, is independently selected alkyl, alkenyl, alkynyl, aryl, heterocyclyl, cycloalkyl, or cycloalkenyl; wherein each $R^{12}$ alkyl, alkenyl, and alkynyl is optionally substituted with one or more alkoxy;

wherein the cyclic moieties represented by $R^3$, $R^5$, $R^6$, $R^7$, $R^8$, $R^9$, $R^{10}$, $R^{11}$, and $R^{12}$ are optionally substituted with one, two, three, four, five, or six independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, C(O)NHOH, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, C(O)H, C(O)OH, OH, CN, $N_3$, $NO_2$, $CF_3$, $CF_2CF_3$, $OCF_3$, $OCF_2CF_3$, $SCF_3$, F, Cl, Br or I;

$R^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, cycloalkyl, or cycloalkenyl; wherein each $R^{13}$ alkyl, alkenyl, and alkynyl is optionally substituted with one, two, three or four independently selected $R^{14}$, $OR^{14}$, $SR^{14}$, $S(O)R^{14}$, $SO_2R^{14}$, $C(O)R^{14}$, $OC(O)R^{14}$, $OC(O)OR^{14}$, $NH_2$, $NHR^{14}$, $N(R^{14})_2$, $NHC(O)R^{14}$, $NR^{14}$, $C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, C(O)NHOH, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, C(O)H, C(O)OH, OH, (O), CN, $N_3$, $NO_2$, $CF_3$, $CF_2CF_3$, $OCF_3$, $OCF_2CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, cycloalkyl, and cycloalkenyl is optionally substituted with one, two, three or four independently selected $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, C(O)NHOH, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, C(O)H, C(O)OH, OH, CN, $N_3$, $NO_2$, $CF_3$, $CF_2CF_3$, $OCF_3$, $OCF_2CF_3$, F, Cl, Br or I;

$R^{14}$, at each occurrence, is independently selected alkyl, alkenyl, alkynyl, aryl, heterocyclyl, cycloalkyl, or cycloalkenyl; wherein each $R^{14}$ alkyl, alkenyl, and alkynyl is optionally substituted with one, two, three or four independently selected heterocyclyl, alkoxy, $NH_2$, $SO_2NH_2$, C(O)H, C(O)OH, OH, (O), CN, $N_3$, $NO_2$, $CF_3$, $CF_2CF_3$, $OCF_3$, $OCF_2CF_3$, F, Cl, Br or I; wherein each $R^{14}$ aryl, heterocyclyl, cycloalkyl, and cycloalkenyl is optionally substituted with one, two, three or four independently selected $R^{16}$, $OR^{16}$, OH, F, Cl, Br, or I;

$R^{15}$, at each occurrence, is independently selected alkyl; and $R^{16}$, at each occurrence, is independently selected alkyl, wherein the $R^{16}$ alkyl is optionally substituted with one, two, three or four independently selected alkoxy;

with the proviso that when $X^1$, $X^2$, and $X^3$ are CH and $R^2$ is phenyl; $R^5$ is not methyl;

with the proviso that when $X^1$, $X^2$, and $X^3$ are CH, and $R^2$ is phenyl substituted with $OR^5$; $R^5$ is not methyl;

with the proviso that when $R^2$ is unsubstituted alkyl or optionally substituted alkyl; $R^2$ is $C_4$-$C_6$-alkyl;

with the proviso that when $R^{13}$ is piperidinyl, it is substituted piperidinyl; and with the proviso that when $R^{13}$ is pyrrolinyl, at least one of $X^1$, $X^2$, and $X^3$ is N.

In one embodiment of Formula (Ib), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N; or $X^1$ is CH; $X^2$ is N; and $X^3$ is $CR^1$; or $X^1$ is $CR^1$; $X^2$ is N; and $X^3$ is CH; or $X^1$ is N; $X^2$ is $CR^1$; and $X^3$ is CH; or $X^1$ is N; $X^2$ is $CR^1$; and $X^3$ is N. In another embodiment of Formula (Ib), $X^1$, $X^2$, and $X^3$ are CH. In another embodiment of Formula (Ib), $X^1$ and $X^3$ are CH; and $X^2$ is N. In another embodiment of Formula (Ib), $X^1$ and $X^3$ are CH; and $X^2$ is $CR^1$. In another embodiment of Formula (Ib), $X^2$ and $X^3$ are CH; and $X^1$ is $CR^1$. In another embodiment of Formula (Ib), $X^1$ is CH; and $X^2$ and $X^3$ are $CR^1$. In another embodiment of Formula (Ib), $X^2$ is CH; and $X^1$ and $X^3$ are N. In another embodiment of Formula (Ib), $X^2$ and $X^3$ are CH; and $X^1$ is N. In another embodiment of Formula (Ib), $X^1$ is CH; $X^2$ is N; and $X^3$ is $CR^1$. In another embodiment of Formula (Ib), $X^1$ is $CR^1$; $X^2$ is N; and $X^3$ is CH. In another embodiment of Formula (Ib), $X^1$ is N; $X^2$ is $CR^1$; and $X^3$ is CH. In another embodiment of Formula (Ib), $X^1$ is N; $X^2$ is $CR^1$; and $X^3$ is N.

In another embodiment of Formula (Ib), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (Ib), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (Ib), $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (Ib), $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (Ib), $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (Ib), $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $R^1$ is $C(O)NH_2$. In another embodiment of Formula (Ib), $R^1$ is F. In another embodiment of Formula (Ib), $R^1$ is Cl. In another embodiment of Formula (Ib), $R^1$ is Br. In another embodiment of Formula (Ib), $R^1$ is CN. In another embodiment of Formula (Ib), $R^1$ is $NH_2$. In another embodiment of Formula (Ib), $R^1$ is $NO_2$. In another embodiment of Formula (Ib), $R^1$ is $CF_3$. In another embodiment of Formula (Ib), $R^1$ is C(O)OH. In another embodiment of Formula (Ib), $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl.

In another embodiment of Formula (Ib), $X^1$ and $X^3$ are CH; and $X^2$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (Ib), $X^1$ and $X^3$ are CH; and $X^2$ is $CR^1$; $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $X^1$ and $X^3$ are CH; and $X^2$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $X^1$ and $X^3$ are CH; and $X^2$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $X^1$ and $X^3$ are CH; and $X^2$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $X^1$ and $X^3$ are CH; and $X^2$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $X^1$ and $X^3$ are CH; and $X^2$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $X^1$ and $X^3$ are CH; and $X^2$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $X^1$ and $X^3$ are CH; and $X^2$ is $CR^1$; and $R^1$ is $C(O)NH_2$. In another embodiment of Formula (Ib), $X^1$ and $X^3$ are CH; and $X^2$ is $CR^1$; and $R^1$ is F. In another embodiment of Formula (Ib), $X^1$ and $X^3$ are CH; and $X^2$ is $CR^1$; and $R^1$ is Cl. In another embodiment of Formula (Ib), $X^1$ and $X^3$ are CH; and $X^2$ is $CR^1$; and $R^1$ is Br. In another embodiment of Formula (Ib), $X^1$ and $X^3$ are CH; and $X^2$ is $CR^1$; and $R^1$ is CN. In another embodiment of Formula (Ib), $X^1$ and $X^3$ are CH; and $X^2$ is $CR^1$; and $R^1$ is $NH_2$. In another embodiment of Formula (Ib), $X^1$ and $X^3$ are CH; and $X^2$ is $CR^1$; and $R^1$ is $NO_2$. In another embodiment of Formula (Ib), $X^1$ and $X^3$ are CH; and $X^2$ is $CR^1$; and $R^1$ is $CF_3$. In another embodiment of Formula (Ib), $X^1$ and $X^3$ are CH; and $X^2$ is $CR^1$; and $R^1$ is C(O)OH. In another embodiment of Formula (Ib), $X^1$ and $X^3$ are CH; and $X^2$ is $CR^1$; $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In another embodiment of Formula (Ib), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (Ib), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $X^2$ and $X^3$ are CH; and $X^1$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $X^2$ and $X^3$ are CH; and $X^1$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $X^2$ and $X^3$ are CH; and $X^1$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $X^2$ and $X^3$ are CH; and $X^1$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $X^2$ and $X^3$ are CH; and $X^1$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $X^2$ and $X^3$ are CH; and $X^1$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $X^2$ and $X^3$ are CH; and $X^1$ is $CR^1$; and $R^1$ is $C(O)NH_2$. In another embodiment of Formula (Ib), $X^2$ and $X^3$ are CH; and $X^1$ is $CR^1$; and $R^1$ is F. In another embodiment of Formula (Ib), $X^2$ and $X^3$ are CH; and $X^1$ is $CR^1$; and $R^1$ is Cl. In another embodiment of Formula (Ib), $X^2$ and $X^3$ are CH; and $X^1$ is $CR^1$; and $R^1$ is Br. In another embodiment of Formula (Ib), $X^2$ and $X^3$ are CH; and $X^1$ is $CR^1$; and $R^1$ is CN. In another embodiment of Formula (Ib), $X^2$ and $X^3$ are CH; and $X^1$ is $CR^1$; and $R^1$ is $NH_2$. In another embodiment of Formula (Ib), $X^2$ and $X^3$ are CH; and $X^1$ is $CR^1$; and $R^1$ is $NO_2$. In another embodiment of Formula (Ib), $X^2$ and $X^3$ are CH; and $X^1$ is $CR^1$; and $R^1$ is $CF_3$. In another embodiment of Formula (Ib), $X^2$ and $X^3$ are CH; and $X^1$ is $CR^1$; and $R^1$ is C(O)OH. In another embodiment of Formula (Ib), $X^2$ and $X^3$ are CH; and $X^1$ is $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In another embodiment of Formula (Ib), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (Ib), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $X^1$ is CH; and $X^2$ and $X^3$ are $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $X^1$ is CH; and $X^2$ and $X^3$ are $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $X^1$ is CH; and $X^2$ and $X^3$ are $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $X^1$ is CH; and $X^2$ and $X^3$ are $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $X^1$ is CH; and $X^2$ and $X^3$ are $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $X^1$ is CH; and $X^2$ and $X^3$ are $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ib), $X^1$ is CH; and $X^2$ and $X^3$ are $CR^1$; and $R^1$ is $C(O)NH_2$. In another embodiment of Formula (Ib), $X^1$ is CH; and $X^2$ and $X^3$ are $CR^1$; and $R^1$ is F. In another embodiment of Formula (Ib), $X^1$ is CH; and $X^2$ and $X^3$ are $CR^1$; and $R^1$ is Cl. In another embodiment of Formula (Ib), $X^1$ is CH; and $X^2$ and $X^3$ are $CR^1$; and $R^1$ is Br. In another embodiment of Formula (Ib), $X^1$ is CH; and $X^2$ and $X^3$ are $CR^1$; and $R^1$ is CN. In another embodiment of Formula (Ib), $X^1$ is CH; and $X^2$ and $X^3$ are $CR^1$; and $R^1$ is $NH_2$. In another embodiment of Formula (Ib), $X^1$ is CH; and $X^2$ and $X^3$ are $CR^1$; and $R^1$ is $NO_2$. In another embodiment of Formula (Ib), $X^1$ is CH; and $X^2$ and $X^3$ are $CR^1$; and $R^1$ is $CF_3$. In another embodiment of Formula (Ib), $X^1$ is CH; and $X^2$ and $X^3$ are $CR^1$; and $R^1$ is C(O)OH. In another embodiment of Formula (Ib), $X^1$ is CH; and $X^2$ and $X^3$ are $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In one embodiment of Formula (Ib), $R^2$ is phenyl which is substituted at the para position with $R^5$; and $R^5$ is phthalazin-1(2H)-onyl, isoquinolinyl, isoquinolin-1(2H)-onyl, 5,6,7,8-tetrahydrophthalazin-1(2H)-onyl, 5-fluorophthalazin-1(2H)-onyl, (Z)-3H-benzo[d][1,2]diazepin-4(5H)-onyl, 5-(trifluoromethyl)phthalazin-1(2H)-onyl, pyrrolo[1,2-d][1,2,4]triazin-1(2H)-one, or isoindolin-1-onyl.

In one embodiment of Formula (Ib), $X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or
$R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH;

$R^2$ is alkyl, phenyl, heterocyclyl; wherein each $R^2$ alkyl is optionally substituted with one, two, three or four independently selected $R^4$, $OR^4$, $C(O)R^4$, $CO(O)R^4NHC(O)R^4$, $NR^4C(O)R^4$, $C(O)NHR^4$, or $C(O)N(R^4)_2$; wherein each $R^2$ phenyl is optionally substituted at the para position with one independently selected $R^5$, $OR^5$, $SO_2R^5$, $C(O)R^5$, $CO(O)R^5$, $NHR^5$, $NHC(O)R^5$, $NHS(O)_2R^5$, $C(O)NH_2$, $C(O)NHR^5$, $C(O)N(R^5)_2$, $CHNOR^5$, $C(O)NHOR^5$, $SO_2NHR^5$, $CF_3$, Br or I; wherein each $R^2$ phenyl is optionally additionally substituted with one F; wherein each $R^2$ heterocyclyl is optionally substituted with one, two, three or four independently selected $R^5$, $OR^5$, $C(O)R^5$, $N(R^5)_2$, $NHC(O)R^5$, $C(O)NHR^5$, F, Cl, Br or I;

$R^3$, at each occurrence, is independently selected alkyl, alkenyl, or heterocyclyl; wherein each $R^3$ alkyl is optionally substituted with one, two, three or four independently selected $R^6$, $OR^6$, $NH_2$, $N(R^6)_2$, $NHC(O)R^6$, OH, F, Cl, Br or I;

$R^4$, at each occurrence, is independently selected alkyl, aryl, cycloalkyl, or heterocyclyl; wherein each $R^4$ alkyl is optionally substituted with one, two, three or four independently selected $R^7$, F, Cl, Br or I; wherein each $R^4$ aryl cycloalkyl, and heterocycyl is optionally substituted with one, two, three or four independently selected $R^8$, $C(O)R^8$, $CO(O)R^8$, F, Cl, Br or I;

$R^5$, at each occurrence, is independently selected alkyl, alkenyl, alkynyl, aryl, heterocyclyl, cycloalkyl, or cycloalkenyl; wherein each $R^5$ alkyl, alkenyl, and alkynyl is optionally substituted with one, two, three or four independently selected $R^9$, $OR^9$, $SR^9$, $C(O)R^9$, $NH_2$, $N(R^9)_2$, $NHC(O)R^9$, $NR^9C(O)OR^9$, $C(O)NH_2$, $C(O)NHR^9$, $C(O)N(R^9)_2$, C(O)OH, OH, CN, $CF_3$, F, Cl, Br or I;

$R^6$, at each occurrence, is independently selected alkyl or heterocyclyl; wherein each $R^6$ alkyl is optionally substituted with one, two, three or four independently selected F, Cl, Br or I;

$R^7$, at each occurrence, is independently selected aryl, or heterocyclyl;

$R^8$, at each occurrence, is independently selected alkyl, aryl, heterocyclyl, or cycloalkyl; wherein each $R^8$ alkyl is optionally substituted with one, two, three or four independently selected $R^{12}$, $OR^{12}OH$, $CF_3$, F, Cl, Br or I;

$R^9$, at each occurrence, is independently selected alkyl, aryl, heterocyclyl, or cycloalkyl; wherein each $R^9$ alkyl is optionally substituted with one, two, three or four independently selected alkoxy, OH, cycloalkyl, aryl, or heterocyclyl;

$R^{12}$, at each occurrence, is independently selected alkyl, heterocyclyl, or cycloalkyl; wherein each $R^{12}$ alkyl is optionally substituted with one or more alkoxy;

wherein the cyclic moieties represented by $R^3$, $R^5$, $R^6$, $R^7$, $R^8$, $R^9$, $R^{10}$, $R^{11}$, and $R^{12}$ are optionally substituted with one, two, three, four, five, or six independently selected $R^{13}$, $OR^{13}$, $SO_2R^{13}$, $C(O)R^{13}$, $CO(O)R^{13}$, $NH_2$, $N(R^{13})_2$, $NHC(O)R^{13}$, $NHC(O)OR^{13}$, $C(O)NH_2$, $C(O)NHR^{13}$, $C(O)N(R^{13})_2$, OH, CN, $CF_3$, $OCF_3$, $SCF_3$, F, Cl, Br or I;

$R^{13}$, at each occurrence, is independently selected alkyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, or cycloalkyl; wherein each $R^{13}$ alkyl and alkynyl is optionally substituted with one, two, three or four independently selected $R^{14}$, $OR^{14}$, $NH_2$, $NHR^{14}$, $N(R^{14})^2$, $NHC(O)R^{14}$, $NHC(O)OR^{14}$, OH, $CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, and cycloalkyl is optionally substituted with one, two, three or four independently selected $R^{15}$, $OR^{15}$, $SO_2R^{15}$, $C(O)R^{15}$, $N(R^{15})_2$, $NHC(O)R^{15}$, CN, $CF_3$, F, Cl, Br or I;

$R^{14}$, at each occurrence, is independently selected alkyl, aryl, heterocyclyl, or cycloalkyl; wherein each $R^{14}$ alkyl is optionally substituted with one, two, three or four independently selected heterocyclyl, alkoxy, OH, F, Cl, Br or I; wherein each $R^{14}$ aryl, heterocyclyl, and cycloalkyl is optionally substituted with one, two, three or four independently selected $R^{16}$, $OR^{16}$, OH, F, Cl, Br, or I;

$R^{15}$, at each occurrence, is independently selected alkyl; and $R^{16}$, at each occurrence, is independently selected alkyl, wherein the $R^{16}$ alkyl is optionally substituted with one, two, three or four independently selected alkoxy;

with the proviso that when $X^1$, $X^2$, and $X^3$ are CH and $R^2$ is phenyl; $R^5$ is not methyl;

with the proviso that when $X^1$, $X^2$, and $X^3$ are CH, and $R^2$ is phenyl substituted with $OR^5$; $R^5$ is not methyl;

with the proviso that when $R^2$ is unsubstituted alkyl or optionally substituted alkyl; $R^2$ is $C_4$-$C_6$-alkyl;

with the proviso that when $R^{13}$ is piperidinyl, it is substituted piperidinyl; and with the proviso that when $R^{13}$ is pyrrolinyl, at least one of $X^1$, $X^2$, and $X^3$ is N.

In another embodiment of Formula (Ib),
$X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$;

$R^2$ is alkyl, phenyl, heterocyclyl; wherein each $R^2$ alkyl is optionally substituted with one, two, three or four independently selected $R^4$, $OR^4$, $C(O)R^4$, $CO(O)R^4NHC(O)R^4$, $NR^4C(O)R^4$, $C(O)NHR^4$, or $C(O)N(R^4)_2$; wherein each $R^2$ phenyl is optionally substituted at the para position with one independently selected $R^5$, $OR^5$, $SO_2R^5$, $C(O)R^5$, $CO(O)R^5$, $NHR^5$, $NHC(O)R^5$, $NHS(O)_2R^5$, $C(O)NH_2$, $C(O)NHR^5$, $C(O)N(R^5)_2$, $CHNOR^5$, $C(O)NHOR^5$, $SO_2NHR^5$, or $CF_3$; wherein each $R^2$ phenyl is optionally additionally substituted with one F; wherein each $R^2$ heterocyclyl is optionally substituted with one, two, three or four independently selected $R^5$, $OR^5$, $C(O)R^5$, $N(R^5)_2$, $NHC(O)R^5$, or $C(O)NHR^5$;

$R^3$, at each occurrence, is independently selected alkyl, alkenyl, or heterocyclyl; wherein each $R^3$ alkyl is optionally substituted with one, two, three or four independently selected $R^6$, $OR^6$, $NH_2$, $N(R^6)_2$, $NHC(O)R^6$, or OH;

$R^4$, at each occurrence, is independently selected alkyl, aryl, cycloalkyl, or heterocyclyl; wherein each $R^4$ alkyl is optionally substituted with one, two, three or four independently selected $R^7$; wherein each $R^4$ aryl cycloalkyl, and heterocycyl is optionally substituted with one, two, three or four independently selected $R^8$, $C(O)R^8$, $CO(O)R^8$, F, Cl, or Br;

$R^5$, at each occurrence, is independently selected alkyl, alkenyl, alkynyl, aryl, heterocyclyl, cycloalkyl, or cycloalkenyl; wherein each $R^5$ alkyl, alkenyl, and alkynyl is optionally substituted with one, two, three or four independently selected $R^9$, $OR^9$, $SR^9$, $C(O)R^9$, $NH_2$, $N(R^9)_2$, $NHC(O)R^9$, $NR^9C(O)OR^9$, $C(O)NH_2$, $C(O)NHR^9$, $C(O)N(R^9)_2$, $C(O)OH$, OH, CN, $CF_3$, or F;

$R^6$, at each occurrence, is independently selected alkyl or heterocyclyl;

$R^7$, at each occurrence, is independently selected aryl, or heterocyclyl;

$R^8$, at each occurrence, is independently selected alkyl, aryl, heterocyclyl, or cycloalkyl; wherein each $R^8$ alkyl is optionally substituted with one, two, three or four independently selected $R^{12}$, $OR^{12}OH$, or $CF_3$;

$R^9$, at each occurrence, is independently selected alkyl, aryl, heterocyclyl, or cycloalkyl; wherein each $R^9$ alkyl is optionally substituted with one, two, three or four independently selected alkoxy, OH, cycloalkyl, aryl, or heterocyclyl;

$R^{12}$, at each occurrence, is independently selected alkyl, heterocyclyl, or cycloalkyl; wherein each $R^{12}$ alkyl is optionally substituted with one or more alkoxy;

wherein the cyclic moieties represented by $R^3$, $R^5$, $R^6$, $R^7$, $R^8$, $R^9$, $R^{10}$, $R^{11}$, and $R^{12}$ are optionally substituted with one, two, three, four, five, or six independently selected $R^{13}$, $OR^{13}$, $SO_2R^{13}$, $C(O)R^{13}$, $CO(O)R^{13}$, $NH_2$, $N(R^{13})_2$, $NHC(O)R^{13}$, $NHC(O)OR^{13}$, $C(O)NH_2$, $C(O)NHR^{13}$, $C(O)N(R^{13})_2$, OH, CN, $CF_3$, $OCF_3$, $SCF_3$, F, or Cl;

$R^{13}$, at each occurrence, is independently selected alkyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, or cycloalkyl; wherein each $R^{13}$ alkyl and alkynyl is optionally substituted with one, two, three or four independently selected $R^{14}$, $OR^{14}$, $NH_2$, $NHR^{14}$, $N(R^{14})_2$, $NHC(O)R^{14}$, $NHC(O)OR^{14}$, OH, or $CF_3$; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, and cycloalkyl is optionally substituted with one, two, three or four independently selected $R^{15}$, $OR^{15}$, $SO_2R^{15}$, $C(O)R^{15}$, $N(R^{15})_2$, $NHC(O)R^{15}$, CN, $CF_3$, F, or Cl;

$R^{14}$, at each occurrence, is independently selected alkyl, aryl, heterocyclyl, or cycloalkyl; wherein each $R^{14}$ alkyl is optionally substituted with one, two, three or four independently selected heterocyclyl, alkoxy, or OH; wherein each $R^{14}$ aryl, heterocyclyl, and cycloalkyl is optionally substituted with one, two, three or four independently selected $R^{16}$, $OR^{16}$, OH, or Cl;

$R^{15}$, at each occurrence, is independently selected alkyl; and $R^{16}$, at each occurrence, is independently selected alkyl, wherein the $R^{16}$ alkyl is optionally substituted with one, two, three or four independently selected alkoxy;

with the proviso that when $X^1$, $X^2$, and $X^3$ are CH and $R^2$ is phenyl; $R^5$ is not methyl;

with the proviso that when $X^1$, $X^2$, and $X^3$ are CH, and $R^2$ is phenyl substituted with $OR^5$; $R^5$ is not methyl;

with the proviso that when $R^2$ is unsubstituted alkyl or optionally substituted alkyl; $R^2$ is $C_4$-$C_6$-alkyl;

with the proviso that when $R^{13}$ is piperidinyl, it is substituted piperidinyl; and with the proviso that when $R^{13}$ is pyrrolinyl, at least one of $X^1$, $X^2$, and $X^3$ is N.

Still another embodiment pertains to compounds having Formula (Ib), which include Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 358, 359, 360, 361, 362, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 796, 797, 798, 799, 800, 801, 802, 803, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1269, 1270, 1271, 1272, 1273, 1274, 1275, 1276, 1277, 1278, 1279, 1280, 1281, 1282, 1283, 1284, 1285, 1286, 1287, 1288, 1289, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, or pharmaceutically acceptable salts thereof.

Embodiments of Formula (IIb)

In another aspect, the present invention provides compounds of Formula (IIb)

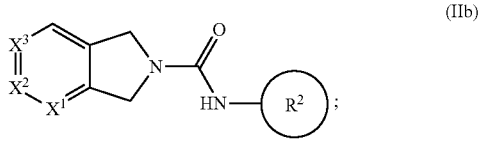

(IIb)

or pharmaceutically acceptable salts thereof; wherein $X^1$, $X^2$, $X^3$, are as described herein for Formula (Ib); and $R^2$ is phenyl, heterocyclyl, cycloalkyl, or cycloalkenyl; wherein the $R^2$ phenyl, heterocyclyl, cycloalkyl, and cycloalkenyl are optionally substituted as described herein for substituents on $R^2$ in Formula (Ib).

In one embodiment of formula (IIb),
$X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or
$X^1$ is CH; $X^2$ is N; and $X^3$ is $CR^1$; or
$X^1$ is $CR^1$; $X^2$ is N; and $X^3$ is CH; or
$X^1$ is N; $X^2$ is $CR^1$; and $X^3$ is CH; or
$X^1$ is N; $X^2$ is $CR^1$; and $X^3$ is N;
$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, $C(O)H$, $CF_3$, $C(O)OH$, or $C(O)NH_2$;
$R^2$ is phenyl, heterocyclyl, cycloalkyl, or cycloalkenyl; wherein each $R^2$ phenyl is optionally substituted at the para position with one independently selected $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $CHNOR^5$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, OH, CN, $N_3$, $NO_2$, $CF_3$, $CF_2CF_3$, $OCF_3$, $OCF_2CF_3$, Br or I; wherein each $R^2$ phenyl is optionally additionally substituted with one F; wherein each $R^2$ heterocyclyl, cycloalkyl, and cycloalkenyl is optionally substituted with one, two, three or four independently selected $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, OH, CN, $N_3$, $CF_3$, $CF_2CF_3$, $OCF_3$, $OCF_2CF_3$, F, Cl, Br or I;
$R^3$, at each occurrence, is independently selected alkyl, alkenyl, alkynyl, aryl, or heterocyclyl; wherein each $R^3$ alkyl, alkenyl, and alkynyl is optionally substituted with one, two, three or four independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I;
$R^5$, at each occurrence, is independently selected alkyl, alkenyl, alkynyl, aryl, heterocyclyl, cycloalkyl, or cycloalkenyl; wherein each $R^5$ alkyl, alkenyl, and alkynyl is optionally substituted with one, two, three or four independently selected $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I;
$R^6$, at each occurrence, is independently selected alkyl, alkenyl, alkynyl, aryl, heterocyclyl, cycloalkyl, or cycloalkenyl; wherein each $R^6$ alkyl, alkenyl, and alkynyl is optionally substituted with one, two, three or four independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, OH, (O), $C(O)OH$, $N_3$, CN, $NH_2$, $CF_3$, $CF_2CF_3$, F, Cl, Br or I;
$R^9$, at each occurrence, is independently selected alkyl, alkenyl, alkynyl, aryl, heterocyclyl, cycloalkyl, or cycloalkenyl; wherein each $R^9$ alkyl, alkenyl, and alkynyl is optionally substituted with one, two, three or four independently selected alkoxy, OH, cycloalkyl, aryl, or heterocyclyl;
$R^{10}$, at each occurrence, is independently selected alkyl, alkenyl, alkynyl, aryl, heterocyclyl, cycloalkyl, or cycloalkenyl;
wherein the cyclic moieties represented by $R^3$, $R^5$, $R^6$, $R^9$, and $R^{10}$ are optionally substituted with one, two, three, four, five, or six independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, $C(O)H$, $C(O)OH$, $OH$, $CN$, $N_3$, $NO_2$, $CF_3$, $CF_2CF_3$, $OCF_3$, $OCF_2CF_3$, $SCF_3$, F, Cl, Br or I;

$R^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, cycloalkyl, or cycloalkenyl; wherein each $R^{13}$ alkyl, alkenyl, and alkynyl is optionally substituted with one, two, three or four independently selected $R^{14}$, $OR^{14}$, $SR^{14}$, $S(O)R^{14}$, $SO_2R^{14}$, $C(O)R^{14}$, $OC(O)R^{14}$, $OC(O)OR^{14}$, $NH_2$, $NHR^{14}$, $N(R^{14})_2$, $NHC(O)R^{14}$, $NR^{14}$, $C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{13}$ aryl, tetrahydropyranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, cycloalkyl, and cycloalkenyl is optionally substituted with one, two, three or four independently selected $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $C(O)H$, $C(O)OH$, $OH$, $CN$, $N_3$, $NO_2$, $CF_3$, $CF_2CF_3$, $OCF_3$, $OCF_2CF_3$, F, Cl, Br or I;

$R^{14}$, at each occurrence, is independently selected alkyl, alkenyl, alkynyl, aryl, heterocyclyl, cycloalkyl, or cycloalkenyl; wherein each $R^{14}$ alkyl, alkenyl, and alkynyl is optionally substituted with one, two, three or four independently selected heterocyclyl, alkoxy, $NH_2$, $SO_2NH_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{14}$ aryl, heterocyclyl, cycloalkyl, and cycloalkenyl is optionally substituted with one, two, three or four independently selected $R^{16}$, $OR^{16}$, OH, F, Cl, Br, or I;

$R^{15}$, at each occurrence, is independently selected alkyl; and $R^{16}$, at each occurrence, is independently selected alkyl, wherein the $R^{16}$ alkyl is optionally substituted with one, two, three or four independently selected alkoxy;

with the proviso that when $X^1$, $X^2$, and $X^3$ are CH and $R^2$ is phenyl; $R^5$ is not methyl; with the proviso that when $X^1$, $X^2$, and $X^3$ are CH, and $R^2$ is phenyl substituted with $OR^5$; $R^5$ is not methyl;

with the proviso that when $R^{13}$ is piperidinyl, it is substituted piperidinyl; and with the proviso that when $R^{13}$ is pyrrolinyl, at least one of $X^1$, $X^2$, and $X^3$ is N.

In one embodiment of Formula (IIb), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N; or $X^1$ is CH; $X^2$ is N; and $X^3$ is $CR^1$; or $X^1$ is $CR^1$; $X^2$ is N; and $X^3$ is CH; or $X^1$ is N; $X^2$ is $CR^1$; and $X^3$ is CH; or $X^1$ is N; $X^2$ is $CR^1$; and $X^3$ is N. In another embodiment of Formula (IIb), $X^1$, $X^2$, and $X^3$ are CH. In another embodiment of Formula (IIb), $X^1$ and $X^3$ are CH; and $X^2$ is N. In another embodiment of Formula (IIb), $X^1$ and $X^3$ are CH; and $X^2$ is $CR^1$. In another embodiment of Formula (IIb), $X^2$ and $X^3$ are CH; and $X^1$ is $CR^1$. In another embodiment of Formula (IIb), $X^1$ is CH; and $X^2$ and $X^3$ are $CR^1$. In another embodiment of Formula (IIb), $X^2$ is CH; and $X^1$ and $X^3$ are N. In another embodiment of Formula (IIb), $X^2$ and $X^3$ are CH; and $X^1$ is N. In another embodiment of Formula (IIb), $X^1$ is CH; $X^2$ is N; and $X^3$ is $CR^1$. In another embodiment of Formula (IIb), $X^1$ is $CR^1$; $X^2$ is N; and $X^3$ is CH. In another embodiment of Formula (IIb), $X^1$ is N; $X^2$ is $CR^1$; and $X^3$ is CH. In another embodiment of Formula (IIb), $X^1$ is N; $X^2$ is $CR^1$; and $X^3$ is N.

In another embodiment of Formula (IIb), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (IIb), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or $OH$; wherein $R^6$ is alkyl or heterocyclyl. In another embodiment of Formula (IIb), $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or $OH$; wherein $R^6$ is alkyl or heterocyclyl. In another embodiment of Formula (IIb), $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or $OH$; wherein $R^6$ is alkyl or heterocyclyl. In another embodiment of Formula (IIb), $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or $OH$; wherein $R^6$ is alkyl or heterocyclyl. In another embodiment of Formula (IIb), $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or $OH$; wherein $R^6$ is alkyl or heterocyclyl. In another embodiment of Formula (IIb), $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or $OH$; wherein $R^6$ is alkyl or heterocyclyl. In another embodiment of Formula (IIb), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or $OH$; wherein $R^6$ is alkyl or heterocyclyl. In another embodiment of Formula (IIb), $R^1$ is $C(O)NH_2$. In another embodiment of Formula (IIb), $R^1$ is F. In another embodiment of Formula (IIb), $R^1$ is Cl. In another embodiment of Formula (IIb), $R^1$ is Br. In another embodiment of Formula (IIb), $R^1$ is CN. In another embodiment of Formula (IIb), $R^1$ is $NH_2$. In another embodiment of Formula (IIb), $R^1$ is $NO_2$. In another embodiment of Formula (IIb), $R^1$ is $CF_3$. In another embodiment of Formula (IIb), $R^1$ is $C(O)OH$. In another embodiment of Formula (IIb), $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl.

In another embodiment of Formula (IIb), $X^1$ and $X^3$ are CH; and $X^2$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (IIb), $X^1$ and $X^3$ are CH; and $X^2$ is $CR^1$; $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIb), $X^1$ and $X^3$ are CH; and $X^2$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIb), $X^1$ and $X^3$ are CH; and $X^2$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIb), $X^1$ and $X^3$ are CH; and $X^2$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIb), $X^1$ and $X^3$ are CH; and $X^2$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIb), $X^1$ and $X^3$ are CH; and $X^2$ is $CR^1$; $R^1$ is NHC(O)$R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIb), $X^1$ and $X^3$ are CH; and $X^2$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIb), $X^1$ and $X^3$ are CH; and $X^2$ is $CR^1$; $R^1$ is $C(O)NH_2$. In another embodiment of Formula (IIb), $X^1$ and $X^3$ are CH; and $X^2$ is $CR^1$; and $R^1$ is F. In another embodiment of Formula (IIb), $X^1$ and $X^3$ are CH; and $X^2$ is $CR^1$; and $R^1$ is Cl. In another embodiment of Formula (IIb), $X^1$ and $X^3$ are CH; and $X^2$ is $CR^1$; and $R^1$ is Br. In another embodiment of Formula (IIb), $X^1$ and $X^3$ are CH; and $X^2$ is $CR^1$; and $R^1$ is CN. In another embodiment of Formula (IIb), $X^1$ and $X^3$ are CH; and $X^2$ is $CR^1$; and $R^1$ is $NH_2$. In another embodiment of Formula (IIb), $X^1$ and $X^3$ are CH; and $X^2$ is $CR^1$; and $R^1$ is $NO_2$. In another embodiment of Formula (IIb), $X^1$ and $X^3$ are CH; and $X^2$ is $CR^1$; and $R^1$ is $CF_3$. In another embodiment of Formula (IIb), $X^1$ and $X^3$ are CH; and $X^2$ is $CR^1$; and $R^1$ is C(O)OH. In another embodiment of Formula (IIb), $X^1$ and $X^3$ are CH; and $X^2$ is $CR^1$; $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In another embodiment of Formula (IIb), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (IIb), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIb), $X^2$ and $X^3$ are CH; and $X^1$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIb), $X^2$ and $X^3$ are CH; and $X^1$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIb), $X^2$ and $X^3$ are CH; and $X^1$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIb), $X^2$ and $X^3$ are CH; and $X^1$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIb), $X^2$ and $X^3$ are CH; and $X^1$ is $CR^1$; $R^1$ is NHC(O)$R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIb), $X^2$ and $X^3$ are CH; and $X^1$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIb), $X^2$ and $X^3$ are CH; and $X^1$ is $CR^1$; and $R^1$ is $C(O)NH_2$. In another embodiment of Formula (IIb), $X^2$ and $X^3$ are CH; and $X^1$ is $CR^1$; and $R^1$ is F. In another embodiment of Formula (IIb), $X^2$ and $X^3$ are CH; and $X^1$ is $CR^1$; and $R^1$ is Cl. In another embodiment of Formula (IIb), $X^2$ and $X^3$ are CH; and $X^1$ is $CR^1$; and $R^1$ is Br. In another embodiment of Formula (IIb), $X^2$ and $X^3$ are CH; and $X^1$ is $CR^1$; and $R^1$ is CN. In another embodiment of Formula (IIb), $X^2$ and $X^3$ are CH; and $X^1$ is $CR^1$; and $R^1$ is $NH_2$. In another embodiment of Formula (IIb), $X^2$ and $X^3$ are CH; and $X^1$ is $CR^1$; and $R^1$ is $NO_2$. In another embodiment of Formula (IIb), $X^2$ and $X^3$ are CH; and $X^1$ is $CR^1$; and $R^1$ is $CF_3$. In another embodiment of Formula (IIb), $X^2$ and $X^3$ are CH; and $X^1$ is $CR^1$; and $R^1$ is C(O)OH. In another embodiment of Formula (IIb), $X^2$ and $X^3$ are CH; and $X^1$ is $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In another embodiment of Formula (IIb), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (IIb), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIb), $X^1$ is CH; and $X^2$ and $X^3$ are $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIb), $X^1$ is CH; and $X^2$ and $X^3$ are $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIb), $X^1$ is CH; and $X^2$ and $X^3$ are $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIb), $X^1$ is CH; and $X^2$ and $X^3$ are $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIb), $X^1$ is CH; and $X^2$ and $X^3$ are $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIb), $X^1$ is CH; and $X^2$ and $X^3$ are $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIb), $X^1$ is CH; and $X^2$ and $X^3$ are $CR^1$; and $R^1$ is $C(O)NH_2$. In another embodiment of Formula (IIb), $X^1$ is CH; and $X^2$ and $X^3$ are $CR^1$; and $R^1$ is F. In another embodiment of Formula (IIb), $X^1$ is CH; and $X^2$ and $X^3$ are $CR^1$; and $R^1$ is Cl. In another embodiment of Formula (IIb), $X^1$ is CH; and $X^2$ and $X^3$ are $CR^1$; and $R^1$ is Br. In another embodiment of Formula (IIb), $X^1$ is CH; and $X^2$ and $X^3$ are $CR^1$; and $R^1$ is CN. In another embodiment of Formula (IIb), $X^1$ is CH; and $X^2$ and $X^3$ are $CR^1$; and $R^1$ is $NH_2$. In another embodiment of Formula (IIb), $X^1$ is CH; and $X^2$ and $X^3$ are $CR^1$; and $R^1$ is $NO_2$. In another embodiment of Formula (IIb), $X^1$ is CH; and $X^2$ and $X^3$ are $CR^1$; and $R^1$ is $CF_3$. In another embodiment of Formula (IIb), $X^1$ is CH; and $X^2$ and $X^3$ are $CR^1$; and $R^1$ is C(O)OH. In another embodiment of Formula (IIb), $X^1$ is CH; and $X^2$ and $X^3$ are $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

Still another embodiment pertains to compounds having Formula (IIb), which include Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 607, 608, 613, 614, 615, 617, 618, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 682, 683, 684, 685, 686, 687, 700, 701, 702, 703, 704, 705, 706, 707, 708, 709, 710, 711, 712, 713, 714, 715, 716, 717, 718, 719, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 796, 799, 800, 801, 802, 803, 805, 806, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 910, 911, 912, 913, 914, 915, 916, 917, 918, 919, 920, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1269, 1270, 1271, 1272, 1273, 1274, 1275, 1276, 1277, 1278, 1279, 1280, 1281, 1282, 1283, 1284, 1288, 1289, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1363, 1364, 1365, 1366, 1367, 1368, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, or pharmaceutically acceptable salts thereof.

Embodiments of Formula (IIIb)

In another aspect, the present invention provides compounds of Formula (IIIb)

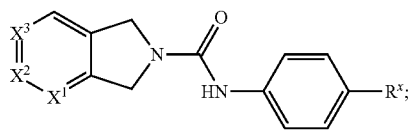
(IIIb)

or pharmaceutically acceptable salts thereof; wherein $X^1$, $X^2$, $X^3$, are as described herein for Formula (Ib); and $R^x$ is as described herein for substituents at the para position in Formula (Ib) when $R^2$ is phenyl.

In one embodiment of formula (IIIb), $X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or
$X^1$ is CH; $X^2$ is N; and $X^3$ is $CR^1$; or
$X^1$ is $CR^1$; $X^2$ is N; and $X^3$ is CH; or
$X^1$ is N; $X^2$ is $CR^1$; and $X^3$ is CH; or
$X^1$ is N; $X^2$ is $CR^1$; and $X^3$ is N;
$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, C(O)H, $CF_3$, C(O)OH, or $C(O)NH_2$;

$R^x$ is $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $CHNOR^5$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, C(O)H, C(O)OH, OH, CN, $N_3$, $NO_2$, $CF_3$, $CF_2CF_3$, $OCF_3$, $OCF_2CF_3$, Br or I;

$R^3$, at each occurrence, is independently selected alkyl, alkenyl, alkynyl, aryl, or heterocyclyl; wherein each $R^3$ alkyl, alkenyl, and alkynyl is optionally substituted with one, two, three or four independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, C(O)H, C(O)OH, OH, (O), CN, $N_3$, $NO_2$, $CF_3$, $CF_2CF_3$, $OCF_3$, $OCF_2CF_3$, F, Cl, Br or I;

$R^5$, at each occurrence, is independently selected alkyl, alkenyl, alkynyl, aryl, heterocyclyl, cycloalkyl, or cycloalkenyl; wherein each $R^5$ alkyl, alkenyl, and alkynyl is optionally substituted with one, two, three or four independently selected $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, C(O)H, C(O)OH, OH, (O), CN, $N_3$, $NO_2$, $CF_3$, $CF_2CF_3$, $OCF_3$, $OCF_2CF_3$, F, Cl, Br or I;

$R^6$, at each occurrence, is independently selected alkyl, alkenyl, alkynyl, aryl, heterocyclyl, cycloalkyl, or cycloalkenyl; wherein each $R^6$ alkyl, alkenyl, and alkynyl is optionally substituted with one, two, three or four independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, OH, (O), C(O)OH, $N_3$, CN, $NH_2$, $CF_3$, $CF_2CF_3$, F, Cl, Br or I;

$R^9$, at each occurrence, is independently selected alkyl, alkenyl, alkynyl, aryl, heterocyclyl, cycloalkyl, or cycloalkenyl; wherein each $R^9$ alkyl, alkenyl, and alkynyl is optionally substituted with one, two, three or four independently selected alkoxy, OH, cycloalkyl, aryl, or heterocyclyl;

$R^{10}$, at each occurrence, is independently selected alkyl, alkenyl, alkynyl, aryl, heterocyclyl, cycloalkyl, or cycloalkenyl;

wherein the cyclic moieties represented by $R^3$, $R^5$, $R^6$, $R^9$, and $R^{10}$ are optionally substituted with one, two, three, four, five, or six independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, C(O)H, C(O)OH, OH, CN, $N_3$, $NO_2$, $CF_3$, $CF_2CF_3$, $OCF_3$, $OCF_2CF_3$, $SCF_3$, F, Cl, Br or I;

$R^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, cycloalkyl, or cycloalkenyl; wherein each $R^{13}$ alkyl, alkenyl, and alkynyl is optionally substituted with one, two, three or four independently selected $R^{14}$, $OR^{14}$, $SR^{14}$, $S(O)R^{14}$, $SO_2R^{14}$, $C(O)R^{14}$, $OC(O)R^{14}$, $OC(O)OR^{14}$, $NH_2$, $NHR^{14}$, $N(R^{14})_2$, $NHC(O)R^{14}$, $NR^{14}$, $C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, cycloalkyl, and cycloalkenyl is optionally substituted with one, two, three or four independently selected $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $C(O)H$, $C(O)OH$, $OH$, $CN$, $N_3$, $NO_2$, $CF_3$, $CF_2CF_3$, $OCF_3$, $OCF_2CF_3$, F, Cl, Br or I;

$R^{14}$, at each occurrence, is independently selected alkyl, alkenyl, alkynyl, aryl, heterocyclyl, cycloalkyl, or cycloalkenyl; wherein each $R^{14}$ alkyl, alkenyl, and alkynyl is optionally substituted with one, two, three or four independently selected heterocyclyl, alkoxy, $NH_2$, $SO_2NH_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{14}$ aryl, heterocyclyl, cycloalkyl, and cycloalkenyl is optionally substituted with one, two, three or four independently selected $R^{16}$, $OR^{16}$, OH, F, Cl, Br, or I;

$R^{15}$, at each occurrence, is independently selected alkyl; and $R^{16}$, at each occurrence, is independently selected alkyl, wherein the $R^{16}$ alkyl is optionally substituted with one, two, three or four independently selected alkoxy;

with the proviso that when $X^1$, $X^2$, and $X^3$ are CH; $R^x$ is not methyl;

with the proviso that when $X^1$, $X^2$, and $X^3$ are CH; $R^x$ is not methoxy;

with the proviso that when $R^{13}$ is piperidinyl, it is substituted piperidinyl; and with the proviso that when $R^{13}$ is pyrrolinyl, at least one of $X^1$, $X^2$, and $X^3$ is N.

In one embodiment of Formula (IIIb), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N; or $X^1$ is CH; $X^2$ is N; and $X^3$ is $CR^1$; or $X^1$ is $CR^1$; $X^2$ is N; and $X^3$ is CH; or $X^1$ is N; $X^2$ is $CR^1$; and $X^3$ is CH; or $X^1$ is N; $X^2$ is $CR^1$; and $X^3$ is N. In another embodiment of Formula (IIIb), $X^1$, $X^2$, and $X^3$ are CH. In another embodiment of Formula (IIIb), $X^1$ and $X^3$ are CH; and $X^2$ is N. In another embodiment of Formula (IIIb), $X^1$ and $X^3$ are CH; and $X^2$ is $CR^1$. In another embodiment of Formula (IIIb), $X^2$ and $X^3$ are CH; and $X^1$ is $CR^1$. In another embodiment of Formula (IIIb), $X^1$ is CH; and $X^2$ and $X^3$ are $CR^1$. In another embodiment of Formula (IIIb), $X^2$ is CH; and $X^1$ and $X^3$ are N. In another embodiment of Formula (IIIb), $X^2$ and $X^3$ are CH; and $X^1$ is N. In another embodiment of Formula (IIIb), $X^1$ is CH; $X^2$ is N; and $X^3$ is $CR^1$. In another embodiment of Formula (IIIb), $X^1$ is $CR^1$; $X^2$ is N; and $X^3$ is CH. In another embodiment of Formula (IIIb), $X^1$ is N; $X^2$ is $CR^1$; and $X^3$ is CH. In another embodiment of Formula (IIIb), $X^1$ is N; $X^2$ is $CR^1$; and $X^3$ is N.

In another embodiment of Formula (IIIb), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (IIIb), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (IIIb), $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (IIIb), $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (IIIb), $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (IIIb), $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIb), $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIb), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIb), $R^1$ is $C(O)NH_2$. In another embodiment of Formula (IIIb), $R^1$ is F. In another embodiment of Formula (IIIb), $R^1$ is Cl. In another embodiment of Formula (IIIb), $R^1$ is Br. In another embodiment of Formula (IIIb), $R^1$ is CN. In another embodiment of Formula (IIIb), $R^1$ is $NH_2$. In another embodiment of Formula (IIIb), $R^1$ is $NO_2$. In another embodiment of Formula (IIIb), $R^1$ is $CF_3$. In another embodiment of Formula (IIIb), $R^1$ is $C(O)OH$. In another embodiment of Formula (IIIb), $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl.

In another embodiment of Formula (IIIb), $X^1$ and $X^3$ are CH; and $X^2$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (IIIb), $X^1$ and $X^3$ are CH; and $X^2$ is $CR^1$; $R^1$ is $R^3$, $OR^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IIIb), X$^1$ and X$^3$ are CH; and X$^2$ is CR$^1$; R$^1$ is R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IIIb), X$^1$ and X$^3$ are CH; and X$^2$ is CR$^1$; R$^1$ is OR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IIIb), X$^1$ and X$^3$ are CH; and X$^2$ is CR$^1$; R$^1$ is C(O)OR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IIIb), X$^1$ and X$^3$ are CH; and X$^2$ is CR$^1$; R$^1$ is C(O)NHR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IIIb), X$^1$ and X$^3$ are CH; and X$^2$ is CR$^1$; R$^1$ is NHC(O)R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IIIb), X$^1$ and X$^3$ are CH; and X$^2$ is CR$^1$; R$^1$ is NHSO$_2$R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IIIb), X$^1$ and X$^3$ are CH; and X$^2$ is CR$^1$; and R$^1$ is C(O)NH$_2$. In another embodiment of Formula (IIIb), X$^1$ and X$^3$ are CH; and X$^2$ is CR$^1$; and R$^1$ is F. In another embodiment of Formula (IIIb), X$^1$ and X$^3$ are CH; and X$^2$ is CR$^1$; and R$^1$ is Cl. In another embodiment of Formula (IIIb), X$^1$ and X$^3$ are CH; and X$^2$ is CR$^1$; and R$^1$ is Br. In another embodiment of Formula (IIIb), X$^1$ and X$^3$ are CH; and X$^2$ is CR$^1$; and R$^1$ is CN. In another embodiment of Formula (IIIb), X$^1$ and X$^3$ are CH; and X$^2$ is CR$^1$; and R$^1$ is NH$_2$. In another embodiment of Formula (IIIb), X$^1$ and X$^3$ are CH; and X$^2$ is CR$^1$; and R$^1$ is NO$_2$. In another embodiment of Formula (IIIb), X$^1$ and X$^3$ are CH; and X$^2$ is CR$^1$; and R$^1$ is CF$_3$. In another embodiment of Formula (IIIb), X$^1$ and X$^3$ are CH; and X$^2$ is CR$^1$; and R$^1$ is C(O)OH. In another embodiment of Formula (IIIb), X$^1$ and X$^3$ are CH; and X$^2$ is CR$^1$; R$^1$ is C(O)R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; and R$^6$ is alkyl or heterocyclyl.

In another embodiment of Formula (IIIb), X$^2$ and X$^3$ are CH; and X$^1$ is CR$^1$; and R$^1$ is R$^3$, OR$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH. In another embodiment of Formula (IIIb), X$^2$ and X$^3$ are CH; and X$^1$ is CR$^1$; and R$^1$ is R$^3$, OR$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IIIb), X$^2$ and X$^3$ are CH; and X$^1$ is CR$^1$; R$^1$ is R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IIIb), X$^2$ and X$^3$ are CH; and X$^1$ is CR$^1$; R$^1$ is OR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IIIb), X$^2$ and X$^3$ are CH; and X$^1$ is CR$^1$; R$^1$ is C(O)OR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IIIb), X$^2$ and X$^3$ are CH; and X$^1$ is CR$^1$; R$^1$ is C(O)NHR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IIIb), X$^2$ and X$^3$ are CH; and X$^1$ is CR$^1$; R$^1$ is NHC(O)R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IIIb), X$^2$ and X$^3$ are CH; and X$^1$ is CR$^1$; R$^1$ is NHSO$_2$R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IIIb), X$^2$ and X$^3$ are CH; and X$^1$ is CR$^1$; and R$^1$ is C(O)NH$_2$. In another embodiment of Formula (IIIb), X$^2$ and X$^3$ are CH; and X$^1$ is CR$^1$; and R$^1$ is F. In another embodiment of Formula (IIIb), X$^2$ and X$^3$ are CH; and X$^1$ is CR$^1$; and R$^1$ is Cl. In another embodiment of Formula (IIIb), X$^2$ and X$^3$ are CH; and X$^1$ is CR$^1$; and R$^1$ is Br. In another embodiment of Formula (IIIb), X$^2$ and X$^3$ are CH; and X$^1$ is CR$^1$; and R$^1$ is CN. In another embodiment of Formula (IIIb), X$^2$ and X$^3$ are CH; and X$^1$ is CR$^1$; and R$^1$ is NH$_2$. In another embodiment of Formula (IIIb), X$^2$ and X$^3$ are CH; and X$^1$ is CR$^1$; and R$^1$ is NO$_2$. In another embodiment of Formula (IIIb), X$^2$ and X$^3$ are CH; and X$^1$ is CR$^1$; and R$^1$ is CF$_3$. In another embodiment of Formula (IIIb), X$^2$ and X$^3$ are CH; and X$^1$ is CR$^1$; and R$^1$ is C(O)OH. In another embodiment of Formula (IIIb), X$^2$ and X$^3$ are CH; and X$^1$ is CR$^1$; and R$^1$ is C(O)R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; and R$^6$ is alkyl or heterocyclyl.

In another embodiment of Formula (IIIb), X$^1$ is CH; and X$^2$ and X$^3$ are CR$^1$; and R$^1$ is R$^3$, OR$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH. In another embodiment of Formula (IIIb), X$^1$ is CH; and X$^2$ and X$^3$ are CR$^1$; and R$^1$ is R$^3$, OR$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IIIb), X$^1$ is CH; and X$^2$ and X$^3$ are CR$^1$; R$^1$ is R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IIIb), X$^1$ is CH; and X$^2$ and X$^3$ are CR$^1$; R$^1$ is OR$^3$; wherein R$^3$ is alkyl, alkenyl, or heterocyclyl; wherein each alkyl is optionally substituted with one or more independently selected R$^6$, OR$^6$, $NH_2$, $NHC(O)R^6$, $N(R^6)_2$, or OH; wherein $R^6$ is alkyl or heterocyclyl. In another embodiment of Formula (IIIb), $X^1$ is CH; and $X^2$ and $X^3$ are $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIb), $X^1$ is CH; and $X^2$ and $X^3$ are $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIb), $X^1$ is CH; and $X^2$ and $X^3$ are $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIb), $X^1$ is CH; and $X^2$ and $X^3$ are $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIb), $X^1$ is CH; and $X^2$ and $X^3$ are $CR^1$; and $R^1$ is $C(O)NH_2$. In another embodiment of Formula (IIIb), $X^1$ is CH; and $X^2$ and $X^3$ are $CR^1$; and $R^1$ is F. In another embodiment of Formula (IIIb), $X^1$ is CH; and $X^2$ and $X^3$ are $CR^1$; and $R^1$ is Cl. In another embodiment of Formula (IIIb), $X^1$ is CH; and $X^2$ and $X^3$ are $CR^1$; and $R^1$ is Br. In another embodiment of Formula (IIIb), $X^1$ is CH; and $X^2$ and $X^3$ are $CR^1$; and $R^1$ is CN. In another embodiment of Formula (IIIb), $X^1$ is CH; and $X^2$ and $X^3$ are $CR^1$; and $R^1$ is $NH_2$. In another embodiment of Formula (IIIb), $X^1$ is CH; and $X^2$ and $X^3$ are $CR^1$; and $R^1$ is $NO_2$. In another embodiment of Formula (IIIb), $X^1$ is CH; and $X^2$ and $X^3$ are $CR^1$; and $R^1$ is $CF_3$. In another embodiment of Formula (IIIb), $X^1$ is CH; and $X^2$ and $X^3$ are $CR^1$; and $R^1$ is $C(O)OH$. In another embodiment of Formula (IIIb), $X^1$ is CH; and $X^2$ and $X^3$ are $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In one embodiment of formula (IIIb), $R^x$ is $R^5$, $OR^5$, $SO_2R^5$, $C(O)R^5$, $CO(O)R^5$, $NHR^5$, $NHC(O)R^5$, $NHS(O)_2R^5$, $C(O)NH_2$, $C(O)NHR^5$, $C(O)N(R^5)_2$, $CHNOR^5$, $C(O)NHOR^5$, $SO_2NHR^5$ or $CF_3$. In another embodiment of formula (IIIb), $R^x$ is $R^5$, and $R^5$ is heterocyclyl, which is optionally substituted as described in embodiments herein.

In another embodiment of Formula (IIIb), $R^x$ is phthalazin-1(2H)-onyl, isoquinolinyl, isoquinolin-1(2H)-onyl, 5,6,7,8-tetrahydrophthalazin-1(2H)-onyl, 5-fluorophthalazin-1(2H)-onyl, (Z)-3H-benzo[d][1,2]diazepin-4(5H)-onyl, 5-(trifluoromethyl)phthalazin-1(2H)-onyl, pyrrolo[1,2-d][1,2,4]triazin-1(2H)-one, isoindolin-1-onyl, or 1,2,3,6-tetrahydropyridinyl. In another embodiment of Formula (IIIb), $R^x$ is phthalazin-1(2H)-onyl, isoquinolinyl, isoquinolin-1(2H)-onyl, 5,6,7,8-tetrahydrophthalazin-1(2H)-onyl, 5-fluorophthalazin-1(2H)-onyl, (Z)-3H-benzo[d][1,2]diazepin-4(5H)-onyl, 5-(trifluoromethyl)phthalazin-1(2H)-onyl, isoindolin-1-onyl, or pyrrolo[1,2-d][1,2,4]triazin-1(2H)-one; which are optionally substituted as defined herein. In another embodiment of Formula (IIIb), $R^x$ is ,2,3,6-tetrahydropyridinyl; which is optionally substituted as defined herein.

Still another embodiment pertains to compounds having Formula (IIIb), which include Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 327, 330, 331, 332, 333, 336, 337, 338, 339, 340, 341, 342, 343, 348, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 405, 406, 407, 408, 409, 410, 411, 412, 413, 414, 415, 416, 417, 418, 419, 420, 421, 424, 425, 426, 427, 428, 429, 430, 431, 432, 433, 434, 435, 436, 437, 438, 439, 440, 441, 442, 443, 444, 445, 446, 447, 448, 449, 450, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 543, 544, 545, 546, 547, 548, 549, 553, 554, 555, 556, 559, 560, 561, 562, 563, 564, 565, 566, 567, 568, 569, 570, 571, 572, 573, 577, 578, 579, 580, 581, 582, 583, 584, 585, 586, 587, 588, 589, 590, 591, 592, 593, 594, 595, 596, 597, 598, 599, 600, 601, 602, 603, 604, 607, 608, 613, 620, 621, 622, 623, 624, 625, 626, 627, 628, 629, 630, 631, 632, 633, 634, 635, 636, 637, 638, 639, 640, 641, 642, 643, 644, 645, 646, 647, 649, 650, 682, 683, 684, 685, 686, 687, 705, 706, 707, 708, 709, 710, 716, 717, 718, 719, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 759, 760, 761, 762, 763, 770, 771, 772, 773, 774, 775, 776, 777, 778, 779, 780, 781, 782, 783, 784, 785, 786, 787, 788, 789, 790, 791, 792, 793, 794, 796, 799, 802, 803, 806, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 910, 911, 912, 913, 914, 915, 916, 917, 918, 919, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1269, 1270, 1271, 1272, 1273, 1274, 1275, 1276, 1277, 1278, 1279, 1280, 1281, 1282, 1283, 1284, 1288, 1289, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1363, 1364, 1365, 1366, 1367, 1368, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, or pharmaceutically acceptable salts thereof.

Still another embodiment pertains to compounds having Formula (IIIb), which include 374, 375, 376, 377, 378, 379, 380, 381, 382, 383, 384, 385, 386, 387, 388, 389, 390, 391, 392, 393, 394, 395, 396, 397, 398, 399, 400, 547, 548, 549, 550, 551, 552, and pharmaceutically acceptable salts thereof.

Embodiments of Formula (IVb)

In another aspect, the present invention provides compounds of Formula (IVb)

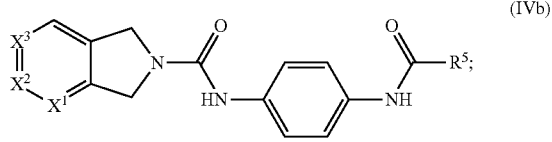

(IVb)

or pharmaceutically acceptable salts thereof; wherein $X^1$, $X^2$, $X^3$, and $R^5$ are as described herein for Formula (Ib).

In one embodiment of formula (IVb),
$X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or
$X^1$ is CH; $X^2$ is N; and $X^3$ is $CR^1$; or
$X^1$ is $CR^1$; $X^2$ is N; and $X^3$ is CH; or
$X^1$ is N; $X^2$ is $CR^1$; and $X^3$ is CH; or
$X^1$ is N; $X^2$ is $CR^1$; and $X^3$ is N;

$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, C(O)H, $CF_3$, C(O)OH, or $C(O)NH_2$;

$R^3$, at each occurrence, is independently selected alkyl, alkenyl, alkynyl, aryl, or heterocyclyl; wherein each $R^3$ alkyl, alkenyl, and alkynyl is optionally substituted with one, two, three or four independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, C(O)H, C(O)OH, OH, (O), CN, $N_3$, $NO_2$, $CF_3$, $CF_2CF_3$, $OCF_3$, $OCF_2CF_3$, F, Cl, Br or I;

$R^5$, at each occurrence, is independently selected alkyl, alkenyl, alkynyl, aryl, heterocyclyl, cycloalkyl, or cycloalkenyl; wherein each $R^5$ alkyl, alkenyl, and alkynyl is optionally substituted with one, two, three or four independently selected $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, C(O)H, C(O)OH, OH, (O), CN, $N_3$, $NO_2$, $CF_3$, $CF_2CF_3$, $OCF_3$, $OCF_2CF_3$, F, Cl, Br or I;

$R^6$, at each occurrence, is independently selected alkyl, alkenyl, alkynyl, aryl, heterocyclyl, cycloalkyl, or cycloalkenyl; wherein each $R^6$ alkyl, alkenyl, and alkynyl is optionally substituted with one, two, three or four independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, OH, (O), C(O)OH, $N_3$, CN, $NH_2$, $CF_3$, $CF_2CF_3$, F, Cl, Br or I;

$R^9$, at each occurrence, is independently selected alkyl, alkenyl, alkynyl, aryl, heterocyclyl, cycloalkyl, or cycloalkenyl; wherein each $R^9$ alkyl, alkenyl, and alkynyl is optionally substituted with one, two, three or four independently selected alkoxy, OH, cycloalkyl, aryl, or heterocyclyl;

$R^{10}$, at each occurrence, is independently selected alkyl, alkenyl, alkynyl, aryl, heterocyclyl, cycloalkyl, or cycloalkenyl;

wherein the cyclic moieties represented by $R^3$, $R^5$, $R^6$, $R^9$, and $R^{10}$ are optionally substituted with one, two, three, four, five, or six independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, C(O)H, C(O)OH, OH, CN, $N_3$, $NO_2$, $CF_3$, $CF_2CF_3$, $OCF_3$, $OCF_2CF_3$, $SCF_3$, F, Cl, Br or I;

$R^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, cycloalkyl, or cycloalkenyl; wherein each $R^{13}$ alkyl, alkenyl, and alkynyl is optionally substituted with one, two, three or four independently selected $R^{14}$, $OR^{14}$, $SR^{14}$, $S(O)R^{14}$, $SO_2R^{14}$, $C(O)R^{14}$, $OC(O)R^{14}$, $OC(O)OR^{14}$, $NH_2$, $NHR^{14}$, $N(R^{14})_2$, $NHC(O)R^{14}$, $NR^{14}$, $C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, cycloalkyl, and cycloalkenyl is optionally substituted with one, two, three or four independently selected $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $C(O)H$, $C(O)OH$, $OH$, $CN$, $N_3$, $NO_2$, $CF_3$, $CF_2CF_3$, $OCF_3$, $OCF_2CF_3$, F, Cl, Br or I;

$R^{14}$, at each occurrence, is independently selected alkyl, alkenyl, alkynyl, aryl, heterocyclyl, cycloalkyl, or cycloalkenyl; wherein each $R^{14}$ alkyl, alkenyl, and alkynyl is optionally substituted with one, two, three or four independently selected heterocyclyl, alkoxy, $NH_2$, $SO_2NH_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{14}$ aryl, heterocyclyl, cycloalkyl, and cycloalkenyl is optionally substituted with one, two, three or four independently selected $R^{16}$, $OR^{16}$, $OH$, F, Cl, Br, or I;

$R^{15}$, at each occurrence, is independently selected alkyl; and $R^{16}$, at each occurrence, is independently selected alkyl, wherein the $R^{16}$ alkyl is optionally substituted with one, two, three or four independently selected alkoxy;

with the proviso that when $R^{13}$ is piperidinyl, it is substituted piperidinyl; and with the proviso that when $R^{13}$ is pyrrolinyl, at least one of $X^1$, $X^2$, and $X^3$ is N.

In one embodiment of Formula (IVb), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N; or $X^1$ is CH; $X^2$ is N; and $X^3$ is $CR^1$; or $X^1$ is $CR^1$; $X^2$ is N; and $X^3$ is CH; or $X^1$ is N; $X^2$ is $CR^1$; and $X^3$ is CH; or $X^1$ is N; $X^2$ is $CR^1$; and $X^3$ is N. In another embodiment of Formula (IVb), $X^1$, $X^2$, and $X^3$ are CH. In another embodiment of Formula (IVb), $X^1$ and $X^3$ are CH; and $X^2$ is N. In another embodiment of Formula (IVb), $X^1$ and $X^3$ are CH; and $X^2$ is $CR^1$. In another embodiment of Formula (IVb), $X^2$ and $X^3$ are CH; and $X^1$ is $CR^1$. In another embodiment of Formula (IVb), $X^1$ is CH; and $X^2$ and $X^3$ are $CR^1$. In another embodiment of Formula (IVb), $X^2$ is CH; and $X^1$ and $X^3$ are N. In another embodiment of Formula (IVb), $X^2$ and $X^3$ are CH; and $X^1$ is N. In another embodiment of Formula (IVb), $X^1$ is CH; $X^2$ is N; and $X^3$ is $CR^1$. In another embodiment of Formula (IVb), $X^1$ is $CR^1$; $X^2$ is N; and $X^3$ is CH. In another embodiment of Formula (IVb), $X^1$ is N; $X^2$ is $CR^1$; and $X^3$ is CH. In another embodiment of Formula (IVb), $X^1$ is N; $X^2$ is $CR^1$; and $X^3$ is N.

In another embodiment of Formula (IVb), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (IVb), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or $OH$; wherein $R^6$ is alkyl or heterocyclyl. In another embodiment of Formula (IVb), $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or $OH$; wherein $R^6$ is alkyl or heterocyclyl. In another embodiment of Formula (IVb), $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or $OH$; wherein $R^6$ is alkyl or heterocyclyl. In another embodiment of Formula (IVb), $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or $OH$; wherein $R^6$ is alkyl or heterocyclyl. In another embodiment of Formula (IVb), $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or $OH$; wherein $R^6$ is alkyl or heterocyclyl. In another embodiment of Formula (IVb), $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or $OH$; wherein $R^6$ is alkyl or heterocyclyl. In another embodiment of Formula (IVb), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or $OH$; wherein $R^6$ is alkyl or heterocyclyl. In another embodiment of Formula (IVb), $R^1$ is $C(O)NH_2$. In another embodiment of Formula (IVb), $R^1$ is F. In another embodiment of Formula (IVb), $R^1$ is Cl. In another embodiment of Formula (IVb), $R^1$ is Br. In another embodiment of Formula (IVb), $R^1$ is CN. In another embodiment of Formula (IVb), $R^1$ is $NH_2$. In another embodiment of Formula (IVb), $R^1$ is $NO_2$. In another embodiment of Formula (IVb), $R^1$ is $CF_3$. In another embodiment of Formula (IVb), $R^1$ is $C(O)OH$. In another embodiment of Formula (IVb), $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or $OH$; wherein $R^6$ is alkyl or heterocyclyl.

In another embodiment of Formula (IVb), $X^1$ and $X^3$ are CH; and $X^2$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (IVb), $X^1$ and $X^3$ are CH; and $X^2$ is $CR^1$; $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, OR$^6$, NH$_2$, NHC(O)R$^6$, N(R$^6$)$_2$, or OH; wherein R$^6$ is alkyl or heterocyclyl. In another embodiment of Formula (IVb), X$^1$ and X$^3$ are CH; and X$^2$ is CR$^1$; R$^1$ is R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVb), X$^1$ and X$^3$ are CH; and X$^2$ is CR$^1$; R$^1$ is OR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVb), X$^1$ and X$^3$ are CH; and X$^2$ is CR$^1$; R$^1$ is C(O)OR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVb), X$^1$ and X$^3$ are CH; and X$^2$ is CR$^1$; R$^1$ is C(O)NHR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVb), X$^1$ and X$^3$ are CH; and X$^2$ is CR$^1$; R$^1$ is NHC(O)R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVb), X$^1$ and X$^3$ are CH; and X$^2$ is CR$^1$; R$^1$ is NHSO$_2$R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVb), X$^1$ and X$^3$ are CH; and X$^2$ is CR$^1$; and R$^1$ is C(O)NH$_2$. In another embodiment of Formula (IVb), X$^1$ and X$^3$ are CH; and X$^2$ is CR$^1$; and R$^1$ is F. In another embodiment of Formula (IVb), X$^1$ and X$^3$ are CH; and X$^2$ is CR$^1$; and R$^1$ is Cl. In another embodiment of Formula (IVb), X$^1$ and X$^3$ are CH; and X$^2$ is CR$^1$; and R$^1$ is Br. In another embodiment of Formula (IVb), X$^1$ and X$^3$ are CH; and X$^2$ is CR$^1$; and R$^1$ is CN. In another embodiment of Formula (IVb), X$^1$ and X$^3$ are CH; and X$^2$ is CR$^1$; and R$^1$ is NH$_2$. In another embodiment of Formula (IVb), X$^1$ and X$^3$ are CH; and X$^2$ is CR$^1$; and R$^1$ is NO$_2$. In another embodiment of Formula (IVb), X$^1$ and X$^3$ are CH; and X$^2$ is CR$^1$; and R$^1$ is CF$_3$. In another embodiment of Formula (IVb), X$^1$ and X$^3$ are CH; and X$^2$ is CR$^1$; and R$^1$ is C(O)OH. In another embodiment of Formula (IVb), X$^1$ and X$^3$ are CH; and X$^2$ is CR$^1$; R$^1$ is C(O)R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; and R$^6$ is alkyl or heterocyclyl.

In another embodiment of Formula (IVb), X$^2$ and X$^3$ are CH; and X$^1$ is CR$^1$; and R$^1$ is R$^3$, OR$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH. In another embodiment of Formula (IVb), X$^2$ and X$^3$ are CH; and X$^1$ is CR$^1$; and R$^1$ is R$^3$, OR$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVb), X$^2$ and X$^3$ are CH; and X$^1$ is CR$^1$; R$^1$ is OR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVb), X$^2$ and X$^3$ are CH; and X$^1$ is CR$^1$; R$^1$ is C(O)OR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVb), X$^2$ and X$^3$ are CH; and X$^1$ is CR$^1$; R$^1$ is C(O)NHR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVb), X$^2$ and X$^3$ are CH; and X$^1$ is CR$^1$; R$^1$ is NHC(O)R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVb), X$^2$ and X$^3$ are CH; and X$^1$ is CR$^1$; R$^1$ is NHSO$_2$R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVb), X$^2$ and X$^3$ are CH; and X$^1$ is CR$^1$; and R$^1$ is C(O)NH$_2$. In another embodiment of Formula (IVb), X$^2$ and X$^3$ are CH; and X$^1$ is CR$^1$; and R$^1$ is F. In another embodiment of Formula (IVb), X$^2$ and X$^3$ are CH; and X$^1$ is CR$^1$; and R$^1$ is Cl. In another embodiment of Formula (IVb), X$^2$ and X$^3$ are CH; and X$^1$ is CR$^1$; and R$^1$ is Br. In another embodiment of Formula (IVb), X$^2$ and X$^3$ are CH; and X$^1$ is CR$^1$; and R$^1$ is CN. In another embodiment of Formula (IVb), X$^2$ and X$^3$ are CH; and X$^1$ is CR$^1$; and R$^1$ is NH$_2$. In another embodiment of Formula (IVb), X$^2$ and X$^3$ are CH; and X$^1$ is CR$^1$; and R$^1$ is NO$_2$. In another embodiment of Formula (IVb), X$^2$ and X$^3$ are CH; and X$^1$ is CR$^1$; and R$^1$ is CF$_3$. In another embodiment of Formula (IVb), X$^2$ and X$^3$ are CH; and X$^1$ is CR$^1$; and R$^1$ is C(O)OH. In another embodiment of Formula (IVb), X$^2$ and X$^3$ are CH; and X$^1$ is CR$^1$; and R$^1$ is C(O)R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; and R$^6$ is alkyl or heterocyclyl.

In another embodiment of Formula (IVb), X$^1$ is CH; and X$^2$ and X$^3$ are CR$^1$; and R$^1$ is R$^3$, OR$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH. In another embodiment of Formula (IVb), X$^1$ is CH; and X$^2$ and X$^3$ are CR$^1$; and R$^1$ is R$^3$, OR$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVb), X$^1$ is CH; and X$^2$ and X$^3$ are CR$^1$; R$^1$ is R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVb), X$^1$ is CH; and X$^2$ and X$^3$ are CR$^1$; R$^1$ is OR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVb), X$^1$ is CH; and X$^2$ and X$^3$ are CR$^1$; R$^1$ is C(O)OR$^3$; wherein R$^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or $OH$; wherein $R^6$ is alkyl or heterocyclyl. In another embodiment of Formula (IVb), $X^1$ is CH; and $X^2$ and $X^3$ are $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or $OH$; wherein $R^6$ is alkyl or heterocyclyl. In another embodiment of Formula (IVb), $X^1$ is CH; and $X^2$ and $X^3$ are $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or $OH$; wherein $R^6$ is alkyl or heterocyclyl. In another embodiment of Formula (IVb), $X^1$ is CH; and $X^2$ and $X^3$ are $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or $OH$; wherein $R^6$ is alkyl or heterocyclyl. In another embodiment of Formula (IVb), $X^1$ is CH; and $X^2$ and $X^3$ are $CR^1$; and $R^1$ is $C(O)NH_2$. In another embodiment of Formula (IVb), $X^1$ is CH; and $X^2$ and $X^3$ are $CR^1$; and $R^1$ is F. In another embodiment of Formula (IVb), $X^1$ is CH; and $X^2$ and $X^3$ are $CR^1$; and $R^1$ is Cl. In another embodiment of Formula (IVb), $X^1$ is CH; and $X^2$ and $X^3$ are $CR^1$; and $R^1$ is Br. In another embodiment of Formula (IVb), $X^1$ is CH; and $X^2$ and $X^3$ are $CR^1$; and $R^1$ is CN. In another embodiment of Formula (IVb), $X^1$ is CH; and $X^2$ and $X^3$ are $CR^1$; and $R^1$ is $NH_2$. In another embodiment of Formula (IVb), $X^1$ is CH; and $X^2$ and $X^3$ are $CR^1$; and $R^1$ is $NO_2$. In another embodiment of Formula (IVb), $X^1$ is CH; and $X^2$ and $X^3$ are $CR^1$; and $R^1$ is $CF_3$. In another embodiment of Formula (IVb), $X^1$ is CH; and $X^2$ and $X^3$ are $CR^1$; and $R^1$ is $C(O)OH$. In another embodiment of Formula (IVb), $X^1$ is CH; and $X^2$ and $X^3$ are $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or $OH$; and $R^6$ is alkyl or heterocyclyl.

Still another embodiment pertains to compounds having Formula (IVb), which include Examples 291, 292, 293, 294, 295, 296, 297, 298, 299, 300, 301, 302, 303, 304, 305, 306, 307, 308, 309, 310, 311, 312, 313, 314, 315, 563, 564, 577, 579, 580, 581, 582, 583, 584, 596, 607, 649, 650, 682, 683, 684, 685, 789, 791, 792, 793, 794, 796, 874, 878, 879, 919, 932, 934, 935, 1363, 1364, 1365, 1366, 1367, 1368, 1370, 1371, 1372, or pharmaceutically acceptable salts thereof.

Embodiments of Formula (Vb)

In another aspect, the present invention provides compounds of Formula (Vb)

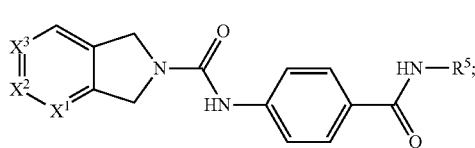

(Vb)

or pharmaceutically acceptable salts thereof; wherein $X^1$, $X^2$, $X^3$, and $R^5$ are as described herein for Formula (Ib).

In one embodiment of formula (Vb),
$X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or
$X^1$ is CH; $X^2$ is N; and $X^3$ is $CR^1$; or
$X^1$ is $CR^1$; $X^2$ is N; and $X^3$ is CH; or
$X^1$ is N; $X^2$ is $CR^1$; and $X^3$ is CH; or
$X^1$ is N; $X^2$ is $CR^1$; and $X^3$ is N;

$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, $C(O)H$, $CF_3$, $C(O)OH$, or $C(O)NH_2$;

$R^3$, at each occurrence, is independently selected alkyl, alkenyl, alkynyl, aryl, or heterocyclyl; wherein each $R^3$ alkyl, alkenyl, and alkynyl is optionally substituted with one, two, three or four independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I;

$R^5$, at each occurrence, is independently selected alkyl, alkenyl, alkynyl, aryl, heterocyclyl, cycloalkyl, or cycloalkenyl; wherein each $R^5$ alkyl, alkenyl, and alkynyl is optionally substituted with one, two, three or four independently selected $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I;

$R^6$, at each occurrence, is independently selected alkyl, alkenyl, alkynyl, aryl, heterocyclyl, cycloalkyl, or cycloalkenyl; wherein each $R^6$ alkyl, alkenyl, and alkynyl is optionally substituted with one, two, three or four independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, OH, (O), $C(O)OH$, $N_3$, CN, $NH_2$, $CF_3$, $CF_2CF_3$, F, Cl, Br or I;

$R^9$, at each occurrence, is independently selected alkyl, alkenyl, alkynyl, aryl, heterocyclyl, cycloalkyl, or cycloalkenyl; wherein each $R^9$ alkyl, alkenyl, and alkynyl is optionally substituted with one, two, three or four independently selected alkoxy, OH, cycloalkyl, aryl, or heterocyclyl;

$R^{10}$, at each occurrence, is independently selected alkyl, alkenyl, alkynyl, aryl, heterocyclyl, cycloalkyl, or cycloalkenyl;

wherein the cyclic moieties represented by $R^3$, $R^5$, $R^6$, $R^9$, and $R^{10}$ are optionally substituted with one, two, three, four, five, or six independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)$ NHSO$_2$R$^{13}$, C(O)NR$^{13}$SO$_2$R$^{13}$, SO$_2$NH$_2$, SO$_2$NHR$^{13}$, SO$_2$N(R$^{13}$)$_2$, C(O)H, C(O)OH, OH, CN, N$_3$, NO$_2$, CF$_3$, CF$_2$CF$_3$, OCF$_3$, OCF$_2$CF$_3$, SCF$_3$, F, Cl, Br or I;

R$^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, cycloalkyl, or cycloalkenyl; wherein each R$^{13}$ alkyl, alkenyl, and alkynyl is optionally substituted with one, two, three or four independently selected R$^{14}$, OR$^{14}$, SR$^{14}$, S(O)R$^{14}$, SO$_2$R$^{14}$, C(O)R$^{14}$, OC(O)R$^{14}$, OC(O)OR$^{14}$, NH$_2$, NHR$^{14}$, N(R$^{14}$)$_2$, NHC(O)R$^{14}$, NR$^{14}$, C(O)R$^{14}$, NHS(O)$_2$R$^{14}$, NR$^{14}$S(O)$_2$R$^{14}$, NHC(O)OR$^{14}$, NR$^{14}$C(O)OR$^{14}$, NHC(O)NH$_2$, NHC(O)NHR$^{14}$, NHC(O)N(R$^{14}$)$_2$, NR$^{14}$C(O)NHR$^{14}$, NR$^{14}$C(O)N(R$^{14}$)$_2$, C(O)NH$_2$, C(O)NHR$^{14}$, C(O)N(R$^{14}$)$_2$, C(O)NHOH, C(O)NHOR$^{14}$, C(O)NHSO$_2$R$^{14}$, C(O)NR$^{14}$SO$_2$R$^{14}$, SO$_2$NH$_2$, SO$_2$NHR$^{14}$, SO$_2$N(R$^{14}$)$_2$, C(O)H, C(O)OH, OH, (O), CN, N$_3$, NO$_2$, CF$_3$, CF$_2$CF$_3$, OCF$_3$, OCF$_2$CF$_3$, F, Cl, Br or I; wherein each R$^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, cycloalkyl, and cycloalkenyl is optionally substituted with one, two, three or four independently selected R$^{15}$, OR$^{15}$, SR$^{15}$, S(O)R$^{15}$, SO$_2$R$^{15}$, C(O)R$^{15}$, CO(O)R$^{15}$, OC(O)R$^{15}$, OC(O)OR$^{15}$, NH$_2$, NHR$^{15}$, N(R$^{15}$)$_2$, NHC(O)R$^{15}$, NR$^{15}$C(O)R$^{15}$, NHS(O)$_2$R$^{15}$, NR$^{15}$S(O)$_2$R$^{15}$, NHC(O)OR$^{15}$, NR$^{15}$C(O)OR$^{15}$, NHC(O)NH$_2$, NHC(O)NHR$^{15}$, NHC(O)N(R$^{15}$)$_2$, NR$^{15}$C(O)NHR$^{15}$, NR$^{15}$C(O)N(R$^{15}$)$_2$, C(O)NH$_2$, C(O)NHR$^{15}$, C(O)N(R$^{15}$)$_2$, C(O)NHOH, C(O)NHOR$^{15}$, C(O)NHSO$_2$R$^{15}$, C(O)NR$^{15}$SO$_2$R$^{15}$, SO$_2$NH$_2$, SO$_2$NHR$^{15}$, SO$_2$N(R$^{15}$)$_2$, C(O)H, C(O)OH, OH, CN, N$_3$, NO$_2$, CF$_3$, CF$_2$CF$_3$, OCF$_3$, OCF$_2$CF$_3$, F, Cl, Br or I;

R$^{14}$, at each occurrence, is independently selected alkyl, alkenyl, alkynyl, aryl, heterocyclyl, cycloalkyl, or cycloalkenyl; wherein each R$^{14}$ alkyl, alkenyl, and alkynyl is optionally substituted with one, two, three or four independently selected heterocyclyl, alkoxy, NH$_2$, SO$_2$NH$_2$, C(O)H, C(O)OH, OH, (O), CN, N$_3$, NO$_2$, CF$_3$, CF$_2$CF$_3$, OCF$_3$, OCF$_2$CF$_3$, F, Cl, Br or I; wherein each R$^{14}$ aryl, heterocyclyl, cycloalkyl, and cycloalkenyl is optionally substituted with one, two, three or four independently selected R$^{16}$, OR$^{16}$, OH, F, Cl, Br, or I;

R$^{15}$, at each occurrence, is independently selected alkyl; and

R$^{16}$, at each occurrence, is independently selected alkyl, wherein the R$^{16}$ alkyl is optionally substituted with one, two, three or four independently selected alkoxy;

with the proviso that when R$^{13}$ is piperidinyl, it is substituted piperidinyl; and with the proviso that when R$^{13}$ is pyrrolinyl, at least one of X$^1$, X$^2$, and X$^3$ is N.

In one embodiment of Formula (Vb), X$^1$, X$^2$, and X$^3$ are CH; or X$^1$ and X$^3$ are CH; and X$^2$ is N; or X$^1$ and X$^3$ are CH; and X$^2$ is CR$^1$; or X$^2$ and X$^3$ are CH; and X$^1$ is CR$^1$; or X$^1$ is CH; and X$^2$ and X$^3$ are CR$^1$; or X$^2$ is CH; and X$^1$ and X$^3$ are N; or X$^2$ and X$^3$ are CH; and X$^1$ is N; or X$^1$ is CH; X$^2$ is N; and X$^3$ is CR$^1$; or X$^1$ is CR$^1$; X$^2$ is N; and X$^3$ is CH; or X$^1$ is N; X$^2$ is CR$^1$; and X$^3$ is CH; or X$^1$ is N; X$^2$ is CR$^1$; and X$^3$ is N. In another embodiment of Formula (Vb), X$^1$, X$^2$, and X$^3$ are CH. In another embodiment of Formula (Vb), X$^1$ and X$^3$ are CH; and X$^2$ is N. In another embodiment of Formula (Vb), X$^1$ and X$^3$ are CH; and X$^2$ is CR$^1$. In another embodiment of Formula (Vb), X$^2$ and X$^3$ are CH; and X$^1$ is CR$^1$. In another embodiment of Formula (Vb), X$^1$ is CH; and X$^2$ and X$^3$ are CR$^1$. In another embodiment of Formula (Vb), X$^2$ is CH; and X$^1$ and X$^3$ are N. In another embodiment of Formula (Vb), X$^2$ and X$^3$ are CH; and X$^1$ is N. In another embodiment of Formula (Vb), X$^1$ is CH; X$^2$ is N; and X$^3$ is CR$^1$. In another embodiment of Formula (Vb), X$^1$ is CR$^1$; X$^2$ is N; and X$^3$ is CH. In another embodiment of Formula (Vb), X$^1$ is N; X$^2$ is CR$^1$; and X$^3$ is CH. In another embodiment of Formula (Vb), X$^1$ is N; X$^2$ is CR$^1$; and X$^3$ is N.

In another embodiment of Formula (Vb), R$^1$ is R$^3$, OR$^3$, C(O)R$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH. In another embodiment of Formula (Vb), R$^1$ is R$^3$, OR$^3$, C(O)R$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH; wherein R$^3$ is alkyl, alkenyl, or heterocyclyl; wherein each alkyl is optionally substituted with one or more independently selected R$^6$, OR$^6$, NH$_2$, N(R$^6$)$_2$, NHC(O)R$^6$, or OH; wherein R$^6$ is alkyl or heterocyclyl. In another embodiment of Formula (Vb), R$^1$ is R$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, NHC(O)R$^6$, or OH; wherein R$^6$ is alkyl or heterocyclyl. In another embodiment of Formula (Vb), R$^1$ is OR$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, NHC(O)R$^6$, or OH; wherein R$^6$ is alkyl or heterocyclyl. In another embodiment of Formula (Vb), R$^1$ is C(O)OR$^3$; wherein R$^3$ is alkyl, alkenyl, or heterocyclyl; wherein each alkyl is optionally substituted with one or more independently selected R$^6$, OR$^6$, NH$_2$, N(R$^6$)$_2$, NHC(O)R$^6$, or OH; wherein R$^6$ is alkyl or heterocyclyl. In another embodiment of Formula (Vb), R$^1$ is C(O)NHR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (Vb), R$^1$ is NHC(O)R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (Vb), R$^1$ is NHSO$_2$R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (Vb), R$^1$ is C(O)NH$_2$. In another embodiment of Formula (Vb), R$^1$ is F. In another embodiment of Formula (Vb), R$^1$ is Cl. In another embodiment of Formula (Vb), R$^1$ is Br. In another embodiment of Formula (Vb), R$^1$ is CN. In another embodiment of Formula (Vb), R$^1$ is NH$_2$. In another embodiment of Formula (Vb), R$^1$ is NO$_2$. In another embodiment of Formula (Vb), R$^1$ is CF$_3$. In another embodiment of Formula (Vb), R$^1$ is C(O)OH. In another embodiment of Formula (Vb), R$^1$ is C(O)R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl.

In another embodiment of Formula (Vb), X$^1$ and X$^3$ are CH; and X$^2$ is CR$^1$; and R$^1$ is R$^3$, OR$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH. In another embodiment of Formula (Vb), X$^1$ and X$^3$ are CH; and X$^2$ is CR$^1$; R$^1$ is R$^3$, OR$^3$, C(O)OR$^3$, C(O)NH$_2$, C(O)NHR$^3$, NHC(O)R$^3$, NHSO$_2$R$^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vb), $X^1$ and $X^3$ are CH; and $X^2$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vb), $X^1$ and $X^3$ are CH; and $X^2$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vb), $X^1$ and $X^3$ are CH; and $X^2$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vb), $X^1$ and $X^3$ are CH; and $X^2$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vb), $X^1$ and $X^3$ are CH; and $X^2$ is $CR^1$; $R^1$ is NHC(O)$R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vb), $X^1$ and $X^3$ are CH; and $X^2$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vb), $X^1$ and $X^3$ are CH; and $X^2$ is $CR^1$; and $R^1$ is $C(O)NH_2$. In another embodiment of Formula (Vb), $X^1$ and $X^3$ are CH; and $X^2$ is $CR^1$; and $R^1$ is F. In another embodiment of Formula (Vb), $X^1$ and $X^3$ are CH; and $X^2$ is $CR^1$; and $R^1$ is Cl. In another embodiment of Formula (Vb), $X^1$ and $X^3$ are CH; and $X^2$ is $CR^1$; and $R^1$ is Br. In another embodiment of Formula (Vb), $X^1$ and $X^3$ are CH; and $X^2$ is $CR^1$; and $R^1$ is CN. In another embodiment of Formula (Vb), $X^1$ and $X^3$ are CH; and $X^2$ is $CR^1$; and $R^1$ is $NH_2$. In another embodiment of Formula (Vb), $X^1$ and $X^3$ are CH; and $X^2$ is $CR^1$; and $R^1$ is $NO_2$. In another embodiment of Formula (Vb), $X^1$ and $X^3$ are CH; and $X^2$ is $CR^1$; and $R^1$ is $CF_3$. In another embodiment of Formula (Vb), $X^1$ and $X^3$ are CH; and $X^2$ is $CR^1$; and $R^1$ is C(O)OH. In another embodiment of Formula (Vb), $X^1$ and $X^3$ are CH; and $X^2$ is $CR^1$; $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In another embodiment of Formula (Vb), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (Vb), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vb), $X^1$ is CH; and $X^2$ and $X^3$ are $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vb), $X^1$ is CH; and $X^2$ and $X^3$ are $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vb), $X^1$ is CH; and $X^2$ and $X^3$ are $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vb), $X^1$ is CH; and $X^2$ and $X^3$ are $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vb), $X^1$ is CH; and $X^2$ and $X^3$ are $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vb), $X^1$ is CH; and $X^2$ and $X^3$ are $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vb), $X^1$ is CH; and $X^2$ and $X^3$ are $CR^1$; and $R^1$ is $C(O)NH_2$. In another embodiment of Formula (Vb), $X^1$ is CH; and $X^2$ and $X^3$ are $CR^1$; and $R^1$ is F. In another embodiment of Formula (Vb), $X^1$ is CH; and $X^2$ and $X^3$ are $CR^1$; and $R^1$ is Cl. In another embodiment of Formula (Vb), $X^1$ is CH; and $X^2$ and $X^3$ are $CR^1$; and $R^1$ is Br. In another embodiment of Formula (Vb), $X^1$ is CH; and $X^2$ and $X^3$ are $CR^1$; and $R^1$ is CN. In another embodiment of Formula (Vb), $X^1$ is CH; and $X^2$ and $X^3$ are $CR^1$; and $R^1$ is $NH_2$. In another embodiment of Formula (Vb), $X^1$ is CH; and $X^2$ and $X^3$ are $CR^1$; and $R^1$ is $NO_2$. In another embodiment of Formula (Vb), $X^1$ is CH; and $X^2$ and $X^3$ are $CR^1$; and $R^1$ is $CF_3$. In another embodiment of Formula (Vb), $X^1$ is CH; and $X^2$ and $X^3$ are $CR^1$; and $R^1$ is C(O)OH. In another embodiment of Formula (Vb), $X^1$ is CH; and $X^2$ and $X^3$ are $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

Still another embodiment pertains to compounds having Formula (Vb), which include Examples 1, 2, 3, 4, 5, 8, 9, 10, 13, 14, 16, 17, 18, 20, 21, 23, 24, 25, 26, 28, 29, 30, 31, 32, 33, 34, 36, 37, 38, 39, 40, 42, 43, 45, 46, 48, 49, 53, 54, 57, 58, 59, 60, 61, 62, 63, 66, 67, 68, 70, 71, 73, 75, 77, 79, 80, 81, 82, 83, 85, 86, 87, 88, 90, 91, 92, 93, 94, 95, 97, 98, 99, 100, 101, 103, 104, 105, 106, 107, 108, 111, 112, 113, 114, 115, 116, 117, 118, 119, 120, 121, 122, 123, 124, 125, 126, 127, 128, 129, 130, 131, 132, 133, 134, 135, 136, 137, 139, 140, 141, 142, 143, 144, 145, 146, 148, 149, 150, 151, 152, 153, 154, 155, 156, 157, 159, 164, 165, 166, 167, 168, 169, 170, 171, 172, 173, 174, 176, 177, 178, 179, 180, 181, 182, 184, 188, 189, 190, 192, 193, 194, 196, 199, 201, 203, 204, 205, 209, 210, 211, 213, 215, 217, 220, 223, 224, 226, 227, 228, 230, 231, 232, 234, 235, 236, 237, 239, 243, 245, 252, 253, 256, 258, 260, 268, 269, 270, 271, 272, 273, 274, 275, 276, 277, 278, 279, 280, 281, 282, 283, 284, 285, 286, 288, 289, 290, 373, 410, 411, 412, 413, 414, 415, 416, 417, 418, 419, 420, 421, 424, 426, 427, 430, 431, 435, 436, 437, 440, 441, 442, 445, 446, 447, 449, 450, 496, 497, 553, 554, 555, 556, 559, 560, 562, 567, 568, 569, 570, 571, 572, 585, 586, 587, 588, 589, 590, 591, 592, 593, 594, 595, 597, 598, 599, 600, 601, 602, 603, 604, 608, 613, 625, 626, 628, 629, 630, 631, 632, 633, 634, 687, 716, 717, 718, 719, 723, 728, 729, 731, 732, 733, 734, 735, 737, 738, 739, 741, 743, 744, 745, 747, 748, 752, 770, 771, 774, 775, 776, 777, 778, 779, 780, 781, 782, 783, 784, 785, 786, 790, 802, 803, 809, 810, 811, 812, 813, 814, 815, 816, 817, 818, 819, 820, 821, 822, 823, 826, 827, 829, 830, 831, 832, 833, 834, 835, 836, 837, 838, 856, 857, 858, 875, 880, 881, 882, 884, 894, 895, 922, 923, 924, 925, 939, 969, 970, 971, 972, 976, 977, 978, 1063, 1064, 1065, 1089, 1090, 1091, 1092, 1093, 1094, 1095, 1096, 1097, 1098, 1100, 1102, 1103, 1104, 1105, 1106, 1108, 1109, 1110, 1111, 1112, 1113, 1114, 1115, 1116, 1117, 1118, 1119, 1120, 1121, 1122, 1123, 1124, 1125, 1127, 1129, 1130, 1132, 1133, 1135, 1136, 1137, 1138, 1139, 1140, 1141, 1142, 1143, 1144, 1145, 1146, 1147, 1148, 1149, 1150, 1152, 1153, 1154, 1155, 1156, 1157, 1158, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1192, 1193, 1194, 1195, 1196, 1197, 1198, 1199, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1239, 1240, 1241, 1242, 1243, 1245, 1260, 1261, 1262, 1263, 1264, 1266, 1267, 1268, 1269, 1270, 1271, 1272, 1273, 1274, 1275, 1276, 1277, 1278, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1348, 1349, or pharmaceutically acceptable salts thereof.

Embodiments of Formula (VIb)

In another aspect, the present invention provides compounds of Formula (VIb)

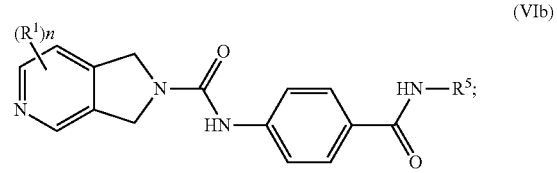

(VIb)

or pharmaceutically acceptable salts thereof; wherein $R^1$ and $R^5$ are as described herein for Formula (Ia); and n is 0 or 1.

In one embodiment of formula (VIb),
n is 0 or 1;
$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, C(O)H, $CF_3$, C(O)OH, or $C(O)NH_2$;

$R^3$, at each occurrence, is independently selected alkyl, alkenyl, alkynyl, aryl, or heterocyclyl; wherein each $R^3$ alkyl, alkenyl, and alkynyl is optionally substituted with one, two, three or four independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, C(O)H, C(O)OH, OH, (O), CN, $N_3$, $NO_2$, $CF_3$, $CF_2CF_3$, $OCF_3$, $OCF_2CF_3$, F, Cl, Br or I;

$R^5$, at each occurrence, is independently selected alkyl, alkenyl, alkynyl, aryl, heterocyclyl, cycloalkyl, or cycloalkenyl; wherein each $R^5$ alkyl, alkenyl, and alkynyl is optionally substituted with one, two, three or four independently selected $R^9$, $OR^9$, $SR^9$, $S(O)R^9$, $SO_2R^9$, $C(O)R^9$, $CO(O)R^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N (R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9$)$_2$, C(O)H, C(O)OH, OH, (O), CN, N$_3$, NO$_2$, CF$_3$, CF$_2$CF$_3$, OCF$_3$, OCF$_2$CF$_3$, F, Cl, Br or I;

R$^6$, at each occurrence, is independently selected alkyl, alkenyl, alkynyl, aryl, heterocyclyl, cycloalkyl, or cycloalkenyl; wherein each R$^6$ alkyl, alkenyl, and alkynyl is optionally substituted with one, two, three or four independently selected R$^{10}$, OR$^{10}$, SR$^{10}$, S(O)R$^{10}$, SO$_2$R$^{10}$, NHR$^{10}$, N(R$^{10}$)$_2$, C(O)R$^{10}$, C(O)NH$_2$, C(O)NHR$^{10}$, C(O)N(R$^1$)$_2$, NHC(O)R$^{10}$, NR$^{10}$C(O)R$^{10}$, NHSO$_2$R$^{10}$, NHC(O)OR$^{10}$, SO$_2$NH$_2$, SO$_2$NHR$^{10}$, SO$_2$N(R$^{10}$)$_2$, NHC(O)NH$_2$, NHC(O)NHR$^{10}$, OH, (O), C(O)OH, N$_3$, CN, NH$_2$, CF$_3$, CF$_2$CF$_3$, F, Cl, Br or I;

R$^9$, at each occurrence, is independently selected alkyl, alkenyl, alkynyl, aryl, heterocyclyl, cycloalkyl, or cycloalkenyl; wherein each R$^9$ alkyl, alkenyl, and alkynyl is optionally substituted with one, two, three or four independently selected alkoxy, OH, cycloalkyl, aryl, or heterocyclyl;

R$^{10}$, at each occurrence, is independently selected alkyl, alkenyl, alkynyl, aryl, heterocyclyl, cycloalkyl, or cycloalkenyl;

wherein the cyclic moieties represented by R$^3$, R$^5$, R$^6$, R$^9$, and R$^{10}$ are optionally substituted with one, two, three, four, five, or six independently selected R$^{13}$, OR$^{13}$, SR$^{13}$, S(O)R$^{13}$, SO$_2$R$^{13}$, C(O)R$^{13}$, CO(O)R$^{13}$, OC(O)R$^{13}$, OC(O)OR$^{13}$, NH$_2$, NHR$^{13}$, N(R$^{13}$)$_2$, NHC(O)R$^{13}$, NR$^{13}$C(O)R$^{13}$, NHS(O)$_2$R$^{13}$, NR$^{13}$S(O)$_2$R$^{13}$, NHC(O)OR$^{13}$, NR$^{13}$C(O)OR$^{13}$, NHC(O)NH$_2$, NHC(O)NHR$^{13}$, NHC(O)N(R$^{13}$)$_2$, NR$^{13}$C(O)NHR$^{13}$, NR$^{13}$C(O)N(R$^{13}$)$_2$, C(O)NH$_2$, C(O)NHR$^{13}$, C(O)N(R$^{13}$)$_2$, C(O)NHOH, C(O)NHOR$^{13}$, C(O)NHSO$_2$R$^{13}$, C(O)NR$^{13}$SO$_2$R$^{13}$, SO$_2$NH$_2$, SO$_2$NHR$^{13}$, SO$_2$N (R$^{13}$)$_2$, C(O)H, C(O)OH, OH, CN, N$_3$, NO$_2$, CF$_3$, CF$_2$CF$_3$, OCF$_3$, OCF$_2$CF$_3$, SCF$_3$, F, Cl, Br or I;

R$^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, cycloalkyl, or cycloalkenyl; wherein each R$^{13}$ alkyl, alkenyl, and alkynyl is optionally substituted with one, two, three or four independently selected R$^{14}$, OR$^{14}$, SR$^{14}$, S(O)R$^{14}$, SO$_2$R$^{14}$, C(O)R$^{14}$, OC(O)R$^{14}$, OC(O)OR$^{14}$, NH$_2$, NHR$^{14}$, N(R$^{14}$)$_2$, NHC(O)R$^{14}$, NR$^{14}$, C(O)R$^{14}$, NHS(O)$_2$R$^{14}$, NR$^{14}$S(O)$_2$R$^{14}$, NHC(O)OR$^{14}$, NR$^{14}$C(O)OR$^{14}$, NHC(O)NH$_2$, NHC(O)NHR$^{14}$, NHC(O)N(R$^{14}$)$_2$, NR$^{14}$C(O)NHR$^{14}$, NR$^{14}$C(O)N(R$^{14}$)$_2$, C(O)NH$_2$, C(O)NHR$^{14}$, C(O)N(R$^{14}$)$_2$, C(O)NHOH, C(O)NHOR$^{14}$, C(O)NHSO$_2$R$^{14}$, C(O)NR$^{14}$SO$_2$R$^{14}$, SO$_2$NH$_2$, SO$_2$NHR$^{14}$, SO$_2$N (R$^{14}$)$_2$, C(O)H, C(O)OH, OH, (O), CN, N$_3$, NO$_2$, CF$_3$, CF$_2$CF$_3$, OCF$_3$, OCF$_2$CF$_3$, F, Cl, Br or I; wherein each R$^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, cycloalkyl, and cycloalkenyl is optionally substituted with one, two, three or four independently selected R$^{15}$, OR$^{15}$, SR$^{15}$, S(O)R$^{15}$, SO$_2$R$^{15}$, C(O)R$^{15}$, CO(O)R$^{15}$, OC(O)R$^{15}$, OC(O)OR$^{15}$, NH$_2$, NHR$^{15}$, N(R$^{15}$)$_2$, NHC(O)R$^{15}$, NR$^{15}$C (O)R$^{15}$, NHS(O)$_2$R$^{15}$, NR$^{15}$S(O)$_2$R$^{15}$, NHC(O)OR$^{15}$, NR$^{15}$C(O)OR$^{15}$, NHC(O)NH$_2$, NHC(O)NHR$^{15}$, NHC(O)N (R$^{15}$)$_2$, NR$^{15}$C(O)NHR$^{15}$, NR$^{15}$C(O)N(R$^{15}$)$_2$, C(O)NH$_2$, C(O)NHR$^{15}$, C(O)N(R$^{15}$)$_2$, C(O)NHOH, C(O)NHOR$^{15}$, C(O)NHSO$_2$R$^{15}$, C(O)NR$^{15}$SO$_2$R$^{15}$, SO$_2$NH$_2$, SO$_2$NHR$^{15}$, SO$_2$N(R$^{15}$)$_2$, C(O)H, C(O)OH, OH, CN, N$_3$, NO$_2$, CF$_3$, CF$_2$CF$_3$, OCF$_3$, OCF$_2$CF$_3$, F, Cl, Br or I;

R$^{14}$, at each occurrence, is independently selected alkyl, alkenyl, alkynyl, aryl, heterocyclyl, cycloalkyl, or cycloalkenyl; wherein each R$^{14}$ alkyl, alkenyl, and alkynyl is optionally substituted with one, two, three or four independently selected heterocyclyl, alkoxy, NH$_2$, SO$_2$NH$_2$, C(O)H, C(O) OH, OH, (O), CN, N$_3$, NO$_2$, CF$_3$, CF$_2$CF$_3$, OCF$_3$, OCF$_2$CF$_3$, F, Cl, Br or I; wherein each R$^{14}$ aryl, heterocyclyl, cycloalkyl, and cycloalkenyl is optionally substituted with one, two, three or four independently selected R$^{16}$, OR$^{16}$, OH, F, Cl, Br, or I;

R$^{15}$, at each occurrence, is independently selected alkyl; and

R$^{16}$, at each occurrence, is independently selected alkyl, wherein the R$^{16}$ alkyl is optionally substituted with one, two, three or four independently selected alkoxy;

with the proviso that when R$^{13}$ is piperidinyl, it is substituted piperidinyl.

In another embodiment of Formula (VIb), n is 0. In another embodiment of Formula (VIb), n is 1. In another embodiment of Formula (VIb), R$^1$ is R$^3$, OR$^3$, C(O)R$^3$, C(O)OR$^3$, C(O) NH$_2$, C(O)NHR$^3$, NHC(O)R$^3$, NHSO$_2$R$^3$, F, Cl, Br, I, CN, NH$_2$, NO$_2$, CF$_3$, or C(O)OH. In another embodiment of Formula (VIb), R$^1$ is R$^3$, OR$^3$, C(O)R$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH; wherein R$^3$ is alkyl, alkenyl, or heterocyclyl; wherein each alkyl is optionally substituted with one or more independently selected R$^6$, OR$^6$, NH$_2$, NHC(O) R$^6$, N(R$^6$)$_2$, or OH; wherein R$^6$ is alkyl or heterocyclyl. In another embodiment of Formula (VIb), R$^1$ is R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (VIb), R$^1$ is OR$^3$; wherein R$^3$ is alkyl, alkenyl, or heterocyclyl; wherein each alkyl is optionally substituted with one or more independently selected R$^6$, OR$^6$, NH$_2$, NHC(O) R$^6$, N(R$^6$)$_2$, or OH; wherein R$^6$ is alkyl or heterocyclyl. In another embodiment of Formula (VIb), R$^1$ is C(O)OR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (VIb), R$^1$ is C(O)NHR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (VIb), R$^1$ is NHC(O) R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (VIb), R$^1$ is NHSO$_2$R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (VIb), R$^1$ is C(O)NH$_2$. In another embodiment of Formula (VIb), R$^1$ is F. In another embodiment of Formula (VIb), R$^1$ is Cl. In another embodiment of Formula (VIb), R$^1$ is Br. In another embodiment of Formula (VIb), R$^1$ is CN. In another embodiment of Formula (VIb), R$^1$ is NH$_2$. In another embodiment of Formula (VIb), $R^1$ is $NO_2$. In another embodiment of Formula (VIb), $R^1$ is $CF_3$. In another embodiment of Formula (VIb), $R^1$ is C(O)OH. In another embodiment of Formula (VIb), $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl.

Still another embodiment pertains to compounds having Formula (VIb), which include Examples 285, 286, 288, 289, 290, 426, 427, 437, 445, 553, 554, 555, 556, 599, 627, 628, 629, 630, 631, 632, 633, 634, 635, 686, 687, 718, 723, 725, 726, 727, 728, 729, 731, 732, 733, 734, 735, 737, 738, 739, 741, 743, 744, 745, 747, 748, 749, 750, 751, 752, 770, 771, 773, 774, 775, 776, 777, 778, 779, 780, 803, 875, 880, 881, 882, 884, 922, 923, 924, 925, 939, 969, 970, 971, 972, 1055, 1056, 1057, 1058, 1059, 1060, 1061, 1062, 1063, 1064, 1065, 1066, 1067, 1068, 1069, 1070, 1071, 1072, 1073, 1074, 1075, 1076, or pharmaceutically acceptable salts thereof.

Embodiments of Formula (VIIb)

In another aspect, the present invention provides compounds of Formula (VIIb)

(VIIb)

or pharmaceutically acceptable salts thereof; wherein $X^1$, $X^2$, $X^3$, and $R^{13}$ are as described herein for Formula (Ib), and ⌇ indicates a single or a double bond.

In one embodiment of formula (VIIb),
$X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or
$X^1$ is CH; $X^2$ is N; and $X^3$ is $CR^1$; or
$X^1$ is $CR^1$; $X^2$ is N; and $X^3$ is CH; or
$X^1$ is N; $X^2$ is $CR^1$; and $X^3$ is CH; or
$X^1$ is N; $X^2$ is $CR^1$; and $X^3$ is N;
$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, C(O)H, $CF_3$, C(O)OH, or $C(O)NH_2$;
$R^3$, at each occurrence, is independently selected alkyl, alkenyl, alkynyl, aryl, or heterocyclyl; wherein each $R^3$ alkyl, alkenyl, and alkynyl is optionally substituted with one, two, three or four independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, C(O)H, C(O)OH, OH, (O), CN, $N_3$, $NO_2$, $CF_3$, $CF_2CF_3$, $OCF_3$, $OCF_2CF_3$, F, Cl, Br or I;

$R^6$, at each occurrence, is independently selected alkyl, alkenyl, alkynyl, aryl, heterocyclyl, cycloalkyl, or cycloalkenyl; wherein each $R^6$ alkyl, alkenyl, and alkynyl is optionally substituted with one, two, three or four independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, OH, (O), C(O)OH, $N_3$, CN, $NH_2$, $CF_3$, $CF_2CF_3$, F, Cl, Br or I;

$R^{10}$, at each occurrence, is independently selected alkyl, alkenyl, alkynyl, aryl, heterocyclyl, cycloalkyl, or cycloalkenyl;

wherein the cyclic moieties represented by $R^3$, $R^6$, and $R^{10}$ are optionally substituted with one, two, three, four, five, or six independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, C(O)H, C(O)OH, OH, CN, $N_3$, $NO_2$, $CF_3$, $CF_2CF_3$, $OCF_3$, $OCF_2CF_3$, $SCF_3$, F, Cl, Br or I;

$R^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, cycloalkyl, or cycloalkenyl; wherein each $R^{13}$ alkyl, alkenyl, and alkynyl is optionally substituted with one, two, three or four independently selected $R^{14}$, $OR^{14}$, $SR^{14}$, $S(O)R^{14}$, $SO_2R^{14}$, $C(O)R^{14}$, $OC(O)R^{14}$, $OC(O)OR^{14}$, $NH_2$, $NHR^{14}$, $N(R^{14})_2$, $NHC(O)R^{14}$, $NR^{14}$, $C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, C(O)H, C(O)OH, OH, (O), CN, $N_3$, $NO_2$, $CF_3$, $CF_2CF_3$, $OCF_3$, $OCF_2CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, cycloalkyl, and cycloalkenyl is optionally substituted with one, two, three or four independently selected $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, C(O)H, C(O)OH, OH, CN, $N_3$, $NO_2$, $CF_3$, $CF_2CF_3$, $OCF_3$, $OCF_2CF_3$, F, Cl, Br or I;

$R^{14}$, at each occurrence, is independently selected alkyl, alkenyl, alkynyl, aryl, heterocyclyl, cycloalkyl, or cycloalkenyl; wherein each $R^{14}$ alkyl, alkenyl, and alkynyl is optionally substituted with one, two, three or four independently selected heterocyclyl, alkoxy, $NH_2$, $SO_2NH_2$, C(O)H, C(O) OH, OH, (O), CN, $N_3$, $NO_2$, $CF_3$, $CF_2CF_3$, $OCF_3$, $OCF_2CF_3$, F, Cl, Br or I; wherein each $R^{14}$ aryl, heterocyclyl, cycloalkyl, and cycloalkenyl is optionally substituted with one, two, three or four independently selected $R^{16}$, $OR^{16}$, OH, F, Cl, Br, or I;

$R^{15}$, at each occurrence, is independently selected alkyl; and $R^{16}$, at each occurrence, is independently selected alkyl, wherein the $R^{16}$ alkyl is optionally substituted with one, two, three or four independently selected alkoxy;

with the proviso that when $R^{13}$ is piperidinyl, it is substituted piperidinyl; and with the proviso that when $R^{13}$ is pyrrolinyl, at least one of $X^1$, $X^2$, and $X^3$ is N.

In one embodiment of Formula (VIIb), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N; or $X^1$ is CH; $X^2$ is N; and $X^3$ is $CR^1$; or $X^1$ is $CR^1$; $X^2$ is N; and $X^3$ is CH; or $X^1$ is N; $X^2$ is $CR^1$; and $X^3$ is CH; or $X^1$ is N; $X^2$ is $CR^1$; and $X^3$ is N. In another embodiment of Formula (VIIb), $X^1$, $X^2$, and $X^3$ are CH. In another embodiment of Formula (VIIb), $X^1$ and $X^3$ are CH; and $X^2$ is N. In another embodiment of Formula (VIIb), $X^1$ and $X^3$ are CH; and $X^2$ is $CR^1$. In another embodiment of Formula (VIIb), $X^2$ and $X^3$ are CH; and $X^1$ is $CR^1$. In another embodiment of Formula (VIIb), $X^1$ is CH; and $X^2$ and $X^3$ are $CR^1$. In another embodiment of Formula (VIIb), $X^2$ is CH; and $X^1$ and $X^3$ are N. In another embodiment of Formula (VIIb), $X^2$ and $X^3$ are CH; and $X^1$ is N. In another embodiment of Formula (VIIb), $X^1$ is CH; $X^2$ is N; and $X^3$ is $CR^1$. In another embodiment of Formula (VIIb), $X^1$ is $CR^1$; $X^2$ is N; and $X^3$ is CH.

In another embodiment of Formula (VIIb), $X^1$ is N; $X^2$ is $CR^1$; and $X^3$ is CH. In another embodiment of Formula (VIIb), $X^1$ is N; $X^2$ is $CR^1$; and $X^3$ is N.

In another embodiment of Formula (VIIb), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (VIIb), $R^1$ is $R^3$, $OR^3$, C(O)$R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, NHC(O)$R^6$, or OH; wherein $R^6$ is alkyl or heterocyclyl. In another embodiment of Formula (VIIb), $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, NHC(O)$R^6$, or OH; wherein $R^6$ is alkyl or heterocyclyl. In another embodiment of Formula (VIIb), $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, NHC(O)$R^6$, or OH; wherein $R^6$ is alkyl or heterocyclyl. In another embodiment of Formula (VIIb), $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, NHC(O)$R^6$, or OH; wherein $R^6$ is alkyl or heterocyclyl. In another embodiment of Formula (VIIb), $R^1$ is C(O) $NHR^3$; wherein $R^3$ is alkyl, alkenyl, or heterocyclyl; wherein each alkyl is optionally substituted with one or more independently selected $R^6$, $OR^6$, $NH_2$, NHC(O)$R^6$, $N(R^6)_2$, or OH; wherein $R^6$ is alkyl or heterocyclyl. In another embodiment of Formula (VIIb), $R^1$ is NHC(O)$R^3$; wherein $R^3$ is alkyl, alkenyl, or heterocyclyl; wherein each alkyl is optionally substituted with one or more independently selected $R^6$, $OR^6$, $NH_2$, NHC(O)$R^6$, $N(R^6)_2$, or OH; wherein $R^6$ is alkyl or heterocyclyl. In another embodiment of Formula (VIIb), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, NHC(O)$R^6$, $N(R^6)_2$, or OH; wherein $R^6$ is alkyl or heterocyclyl. In another embodiment of Formula (VIIb), $R^1$ is $C(O)NH_2$. In another embodiment of Formula (VIIb), $R^1$ is F. In another embodiment of Formula (VIIb), $R^1$ is Cl. In another embodiment of Formula (VIIb), $R^1$ is Br. In another embodiment of Formula (VIIb), $R^1$ is CN. In another embodiment of Formula (VIIb), $R^1$ is $NH_2$. In another embodiment of Formula (VIIb), $R^1$ is $NO_2$. In another embodiment of Formula (VIIb), $R^1$ is $CF_3$. In another embodiment of Formula (VIIb), $R^1$ is C(O)OH. In another embodiment of Formula (VIIb), $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, NHC(O)$R^6$, $N(R^6)_2$, or OH; wherein $R^6$ is alkyl or heterocyclyl.

In another embodiment of Formula (VIIb), $X^1$ and $X^3$ are CH; and $X^2$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (VIIb), $X^1$ and $X^3$ are CH; and $X^2$ is $CR^1$; $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, NHC(O)$R^6$, $N(R^6)_2$, or OH; wherein $R^6$ is alkyl or heterocyclyl. In another embodiment of Formula (VIIb), $X^1$ and $X^3$ are CH; and $X^2$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, NHC(O)$R^6$, $N(R^6)_2$, or OH; wherein $R^6$ is alkyl or heterocyclyl. In another embodiment of Formula (VIIb), $X^1$ and $X^3$ are CH; and $X^2$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, NHC(O)$R^6$, $N(R^6)_2$, or OH; wherein $R^6$ is alkyl or heterocyclyl. In another embodiment of Formula (VIIb), $X^1$ and $X^3$ are CH; and $X^2$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, NHC(O)$R^6$, $N(R^6)_2$, or OH; wherein $R^6$ is alkyl or heterocyclyl. In another embodiment of Formula (VIIb), $X^1$ and $X^3$ are CH; and $X^2$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, NHC(O)$R^6$, $N(R^6)_2$, or OH; wherein $R^6$ is alkyl or heterocyclyl. In another embodiment of Formula (VIIb), $X^1$ and $X^3$ are CH; and $X^2$ is $CR^1$; $R^1$ is NHC (O)$R^3$; wherein $R^3$ is alkyl, alkenyl, or heterocyclyl; wherein each alkyl is optionally substituted with one or more independently selected $R^6$, $OR^6$, $NH_2$, NHC(O)$R^6$, $N(R^6)_2$, or OH; wherein $R^6$ is alkyl or heterocyclyl. In another embodiment of Formula (VIIb), $X^1$ and $X^3$ are CH; and $X^2$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, NHC(O)$R^6$, $N(R^6)_2$, or OH; wherein $R^6$ is alkyl or heterocyclyl. In another embodiment of Formula (VIIb), $X^1$ and $X^3$ are CH; and $X^2$ is $CR^1$; and $R^1$ is $C(O)NH_2$. In another embodiment of Formula (VIIb), $X^1$ and $X^3$ are CH; and $X^2$ is $CR^1$; and $R^1$ is F. In another embodiment of Formula (VIIb), $X^1$ and $X^3$ are CH; and $X^2$ is $CR^1$; and $R^1$ is Cl. In another embodiment of Formula (VIIb), $X^1$ and $X^3$ are CH; and $X^2$ is $CR^1$; and $R^1$ is Br. In another embodiment of Formula (VIIb), $X^1$ and $X^3$ are CH;

and $X^2$ is $CR^1$; and $R^1$ is CN. In another embodiment of Formula (VIIb), $X^1$ and $X^3$ are CH; and $X^2$ is $CR^1$; and $R^1$ is $NH_2$. In another embodiment of Formula (VIIb), $X^1$ and $X^3$ are CH; and $X^2$ is $CR^1$; and $R^1$ is $NO_2$. In another embodiment of Formula (VIIb), $X^1$ and $X^3$ are CH; and $X^2$ is $CR^1$; and $R^1$ is $CF_3$. In another embodiment of Formula (VIIb), $X^1$ and $X^3$ are CH; and $X^2$ is $CR^1$; and $R^1$ is C(O)OH. In another embodiment of Formula (VIIb), $X^1$ and $X^3$ are CH; and $X^2$ is $CR^1$; $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In another embodiment of Formula (VIIb), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (VIIb), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIb), $X^2$ and $X^3$ are CH; and $X^1$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIb), $X^2$ and $X^3$ are CH; and $X^1$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIb), $X^2$ and $X^3$ are CH; and $X^1$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIb), $X^2$ and $X^3$ are CH; and $X^1$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIb), $X^2$ and $X^3$ are CH; and $X^1$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIb), $X^2$ and $X^3$ are CH; and $X^1$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIb), $X^2$ and $X^3$ are CH; and $X^1$ is $CR^1$; and $R^1$ is $C(O)NH_2$. In another embodiment of Formula (VIIb), $X^2$ and $X^3$ are CH; and $X^1$ is $CR^1$; and $R^1$ is F. In another embodiment of Formula (VIIb), $X^2$ and $X^3$ are CH; and $X^1$ is $CR^1$; and $R^1$ is Cl. In another embodiment of Formula (VIIb), $X^2$ and $X^3$ are CH; and $X^1$ is $CR^1$; and $R^1$ is Br. In another embodiment of Formula (VIIb), $X^2$ and $X^3$ are CH; and $X^1$ is $CR^1$; and $R^1$ is CN. In another embodiment of Formula (VIIb), $X^2$ and $X^3$ are CH; and $X^1$ is $CR^1$; and $R^1$ is $NH_2$. In another embodiment of Formula (VIIb), $X^2$ and $X^3$ are CH; and $X^1$ is $CR^1$; and $R^1$ is $NO_2$. In another embodiment of Formula (VIIb), $X^2$ and $X^3$ are CH; and $X^1$ is $CR^1$; and $R^1$ is $CF_3$. In another embodiment of Formula (VIIb), $X^2$ and $X^3$ are CH; and $X^1$ is $CR^1$; and $R^1$ is C(O)OH. In another embodiment of Formula (VIIb), $X^1$ is CH; and $X^2$ and $X^3$ are $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In another embodiment of Formula (VIIb), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (VIIb), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIb), $X^1$ is CH; and $X^2$ and $X^3$ are $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIb), $X^1$ is CH; and $X^2$ and $X^3$ are $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIb), $X^1$ is CH; and $X^2$ and $X^3$ are $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIb), $X^1$ is CH; and $X^2$ and $X^3$ are $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIb), $X^1$ is CH; and $X^2$ and $X^3$ are $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIb), $X^1$ is CH; and $X^2$ and $X^3$ are $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIb), $X^1$ is CH; and $X^2$ and $X^3$ are $CR^1$; and $R^1$ is $C(O)NH_2$. In another embodiment of Formula (VIIb), $X^1$ is CH; and $X^2$ and $X^3$ are $CR^1$; and $R^1$ is F. In another embodiment of Formula (VIIb), $X^1$ is CH; and $X^2$ and $X^3$ are $CR^1$; and $R^1$ is Cl. In another embodiment of Formula (VIIb), $X^1$ is CH; and $X^2$ and $X^3$ are $CR^1$; and $R^1$ is Br. In another embodiment of Formula (VIIb), $X^1$ is CH; and $X^2$ and $X^3$ are $CR^1$; and $R^1$ is CN. In another embodiment of Formula (VIIb), $X^1$ is CH; and $X^2$ and $X^3$ are $CR^1$; and $R^1$ is $NH_2$. In another embodiment of Formula (VIIb), $X^1$ is CH; and $X^2$ and $X^3$ are $CR^1$; and $R^1$ is $NO_2$. In another embodiment of Formula (VIIb), $X^1$ is CH; and $X^2$ and $X^3$ are $CR^1$; and $R^1$ is $CF_3$. In another embodiment of Formula (VIIb), $X^1$ is CH; and $X^2$ and $X^3$ are $CR^1$; and $R^1$ is C(O)OH. In another embodiment of Formula (VIIb), $X^1$ is CH; and $X^2$ and $X^3$ are $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

Still another embodiment pertains to compounds having Formula (VIIb), which include Examples 317, 330, 331, 332, 401, 405, 406, 407, 432, 456, 457, 458, 459, 460, 462, 463, 464, 465, 466, 467, 468, 469, 470, 471, 472, 473, 474, 475, 476, 477, 478, 480, 481, 482, 483, 484, 485, 486, 487, 488, 489, 490, 491, 492, 493, 494, 543, 544, 545, 546, 620, 646, 647, 705, 706, 707, 708, 709, 710, 759, 760, 761, 762, 763, 799, 910, 911, 912, 913, 914, 915, 916, 917, 918, 967, 968, 979, 980, 981, 982, 983, 984, 985, 986, 1014, 1015, 1016, 1017, 1019, 1077, 1078, 1079, 1080, 1254, 1255, 1256, 1257, 1258, 1259, 1279, 1280, 1281, 1282, 1283, 1284, 1384, 1385, or pharmaceutically acceptable salts thereof.

Embodiments of Formula (Ic)

One embodiment of this invention, therefore, pertains to compounds or pharmaceutically acceptable salts, which are useful as inhibitors of NAMPT, the compounds having Formula (Ic)

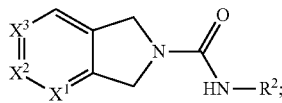

Formula (Ic)

wherein
$X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or
$X^1$ is CH; $X^2$ is N; and $X^3$ is $CR^1$; or
$X^1$ is $CR^1$; $X^2$ is N; and $X^3$ is CH; or
$X^1$ is N; $X^2$ is $CR^1$; and $X^3$ is CH; or
$X^1$ is N; $X^2$ is $CR^1$; and $X^3$ is N;
$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, $C(O)H$, $CF_3$, $C(O)OH$, or $C(O)NH_2$;
$R^2$ is alkyl, alkenyl, alkynyl, phenyl, heterocyclyl, cycloalkyl, or cycloalkenyl; wherein each $R^2$ alkyl, alkenyl, and alkynyl is optionally substituted with one, two, three or four independently selected $R^4$, $OR^4$, $SR^4$, $S(O)R^4$, $SO_2R^4$, $C(O)R^4$, $CO(O)R^4$, $OC(O)R^4$, $OC(O)OR^4$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, (O), CN, $N_3$, $NO_2$, $CF_3$, $CF_2CF_3$, $OCF_3$, $OCF_2CF_3$, F, Cl, Br or I; wherein each $R^2$ phenyl is optionally substituted at the para position with one independently selected $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, CHNOR$^5$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, OH, CN, $N_3$, $NO_2$, $CF_3$, $CF_2CF_3$, $OCF_3$, $OCF_2CF_3$, Br or I; wherein each $R^2$ phenyl is optionally additionally substituted with one F; wherein each $R^2$ heterocyclyl, cycloalkyl, and cycloalkenyl is optionally substituted with one, two, three or four independently selected $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, OH, CN, $N_3$, $CF_3$, $CF_2CF_3$, $OCF_3$, $OCF_2CF_3$, F, Cl, Br or I;
$R^3$, at each occurrence, is independently selected alkyl, alkenyl, alkynyl, aryl, or heterocyclyl; wherein each $R^3$ alkyl, alkenyl, and alkynyl is optionally substituted with one, two, three or four independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I;
$R^4$, at each occurrence, is independently selected alkyl, alkenyl, alkynyl, aryl, cycloalkyl, or heterocyclyl; wherein each $R^4$ alkyl, alkenyl, and alkynyl is optionally substituted with one, two, three or four independently selected $R^7$, $OR^7$, $SR^7$, $S(O)R^7$, $SO_2R^7$, $C(O)R^7$, $OC(O)R^7$, $OC(O)OR^7$, $NH_2$, $NHR^7$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, OH, (O), CN, $N_3$, $NO_2$, $CF_3$, $CF_2CF_3$, $OCF_3$, $OCF_2CF_3$, F, Cl, Br or I; wherein each $R^4$ aryl and heterocyclyl is optionally substituted with one, two, three or four independently selected $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, OH, CN, $N_3$, $NO_2$, $CF_3$, $CF_2CF_3$, $OCF_3$, $OCF_2CF_3$, F, Cl, Br or I;
$R^5$, at each occurrence, is independently selected alkyl, alkenyl, alkynyl, aryl, heterocyclyl, cycloalkyl, or cycloalkenyl; wherein each $R^5$ alkyl, alkenyl, and alkynyl is optionally substituted with one, two, three or four independently selected $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I;
$R^6$, at each occurrence, is independently selected alkyl, alkenyl, alkynyl, aryl, heterocyclyl, cycloalkyl, or cycloalkenyl; wherein each $R^6$ alkyl, alkenyl, and alkynyl is optionally substituted with one, two, three or four independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, OH, (O), C(O)OH, $N_3$, CN, $NH_2$, $CF_3$, $CF_2CF_3$, F, Cl, Br or I;

$R^7$, at each occurrence, is independently selected alkyl, alkenyl, alkynyl, aryl, heterocyclyl, cycloalkyl, or cycloalkenyl; wherein each $R^7$ alkyl, alkenyl, and alkynyl is optionally substituted with one, two, three or four independently selected $R^{11}$, $OR^{11}$, $SR^{11}$, $S(O)R^{11}$, $SO_2R^{11}$, $NHR^{11}$, $N(R^{11})_2$, $C(O)R^{11}$, $C(O)NH_2$, $C(O)NHR^{11}$, $C(O)N(R^{11})_2$, $NHC(O)R^{11}$, $NR^{11}C(O)R^{11}$, $NHSO_2R^{11}$, $NHC(O)OR^{11}$, $SO_2NH_2$, $SO_2NHR^{11}$, $SO_2N(R^{11})_2$, $NHC(O)NH_2$, $NHC(O)NHR^{11}$, OH, (O), C(O)OH, $N_3$, CN, $NH_2$, $CF_3$, $CF_2CF_3$, F, Cl, Br or I;

$R^8$, at each occurrence, is independently selected alkyl, alkenyl, alkynyl, aryl, heterocyclyl, cycloalkyl, or cycloalkenyl; wherein each $R^8$ alkyl, alkenyl, and alkynyl is optionally substituted with one, two, three or four independently selected $R^{12}$, $OR^{12}$, $SR^{12}$, $S(O)R^{12}$, $SO_2R^{12}$, $NHR^{12}$, $N(R^{12})_2$, $C(O)R^{12}$, $C(O)NH_2$, $C(O)NHR^{12}$, $C(O)N(R^{12})_2$, $NHC(O)R^{12}$, $NR^{12}C(O)R^{12}$, $NHSO_2R^{12}$, $NHC(O)OR^{12}$, $SO_2NH_2$, $SO_2NHR^{12}$, $SO_2N(R^{12})_2$, $NHC(O)NH_2$, $NHC(O)NHR^{12}$, OH, (O), C(O)OH, $N_3$, CN, $NH_2$, $CF_3$, $CF_2CF_3$, F, Cl, Br or I;

$R^9$, at each occurrence, is independently selected alkyl, alkenyl, alkynyl, aryl, heterocyclyl, cycloalkyl, or cycloalkenyl; wherein each $R^9$ alkyl, alkenyl, and alkynyl is optionally substituted with one, two, three or four independently selected alkoxy, OH, cycloalkyl, aryl, or heterocyclyl;

$R^{10}$, at each occurrence, is independently selected alkyl, alkenyl, alkynyl, aryl, heterocyclyl, cycloalkyl, or cycloalkenyl;

$R^{11}$, at each occurrence, is independently selected alkyl, alkenyl, alkynyl, aryl, heterocyclyl, cycloalkyl, or cycloalkenyl;

$R^{12}$, at each occurrence, is independently selected alkyl, alkenyl, alkynyl, aryl, heterocyclyl, cycloalkyl, or cycloalkenyl; wherein each $R^{12}$ alkyl, alkenyl, and alkynyl is optionally substituted with one or more alkoxy;

wherein the cyclic moieties represented by $R^3$, $R^5$, $R^6$, $R^7$, $R^8$, $R^9$, $R^{10}$, $R^{11}$, and $R^{12}$ are optionally substituted with one, two, three, four, five, or six independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, C(O)NHOH, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, C(O)H, C(O)OH, OH, CN, $N_3$, $NO_2$, $CF_3$, $CF_2CF_3$, $OCF_3$, $OCF_2CF_3$, $SCF_3$, F, Cl, Br or I;

$R^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, or cycloalkenyl; wherein each $R^{13}$ alkyl, alkenyl, and alkynyl is optionally substituted with one, two, three or four independently selected $R^{14}$, $OR^{14}$, $SR^{14}$, $S(O)R^{14}$, $SO_2R^{14}$, $C(O)R^{14}$, $OC(O)R^{14}$, $OC(O)OR^{14}$, $NH_2$, $NHR^{14}$, $N(R^{14})_2$, $NHC(O)R^{14}$, $NR^{14}C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, C(O)NHOH, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, C(O)H, C(O)OH, OH, (O), CN, $N_3$, $NO_2$, $CF_3$, $CF_2CF_3$, $OCF_3$, $OCF_2CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, and cycloalkenyl is optionally substituted with one, two, three or four independently selected $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, C(O)NHOH, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, C(O)H, C(O)OH, OH, CN, $N_3$, $NO_2$, $CF_3$, $CF_2CF_3$, $OCF_3$, $OCF_2CF_3$, F, Cl, Br or I;

$R^{14}$, at each occurrence, is independently selected alkyl, alkenyl, alkynyl, aryl, heterocyclyl, cycloalkyl, or cycloalkenyl; wherein each $R^{14}$ alkyl, alkenyl, and alkynyl is optionally substituted with one, two, three or four independently selected heterocyclyl, alkoxy, $NH_2$, $SO_2NH_2$, C(O)H, C(O)OH, OH, (O), CN, $N_3$, $NO_2$, $CF_3$, $CF_2CF_3$, $OCF_3$, $OCF_2CF_3$, F, Cl, Br or I; wherein each $R^{14}$ aryl, heterocyclyl, cycloalkyl, and cycloalkenyl is optionally substituted with one, two, three or four independently selected $R^{16}$, $OR^{16}$, OH, F, Cl, Br, or I; wherein the $R^{16}$ alkyl is optionally substituted with one, two, three or four alkoxy;

$R^{15}$, at each occurrence, is independently selected alkyl; wherein the $R^{15}$ alkyl is optionally substituted with one, two, three or four alkoxy;

$R^{16}$, at each occurrence, is independently selected alkyl, wherein the $R^{16}$ alkyl is optionally substituted with one, two, three or four alkoxy;

with the proviso that when $X^1$, $X^2$, and $X^3$ are CH and $R^2$ is phenyl; $R^5$ is not methyl;

with the proviso that when $X^1$, $X^2$, and $X^3$ are CH, and $R^2$ is phenyl substituted with $OR^5$; $R^5$ is not methyl;

with the proviso that when $R^2$ is unsubstituted alkyl or optionally substituted alkyl; $R^2$ is $C_4$-$C_6$-alkyl;

with the proviso that when $R^{13}$ is piperidinyl, it is substituted piperidinyl; and with the proviso that when $R^{13}$ is pyrrolinyl, at least one of $X^1$, $X^2$, and $X^3$ is N.

In one embodiment of Formula (Ic), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N; or $X^1$ is CH; $X^2$ is N; and $X^3$ is $CR^1$; or $X^1$ is $CR^1$; $X^2$ is N; and $X^3$ is CH; or $X^1$ is N; $X^2$ is $CR^1$; and $X^3$ is CH; or $X^1$ is N; $X^2$ is $CR^1$; and $X^3$ is N. In another embodiment of Formula (Ic), $X^1$, $X^2$, and $X^3$ are CH. In another embodiment of Formula (Ic), $X^1$ and $X^3$ are CH; and $X^2$ is N. In another embodiment of Formula (Ic), $X^1$ and $X^3$ are CH; and $X^2$ is $CR^1$. In another embodiment of Formula (Ic), $X^2$ and $X^3$ are CH; and $X^1$ is $CR^1$. In another embodiment of Formula (Ic), $X^1$ is CH; and $X^2$ and $X^3$ are $CR^1$. In another embodiment of Formula (Ic), $X^2$ is CH; and $X^1$ and $X^3$ are N. In another embodiment of Formula (Ic), $X^2$ and $X^3$ are CH; and $X^1$ is N. In another embodiment of Formula (Ic), $X^1$ is CH; $X^2$ is N; and $X^3$ is $CR^1$. In another embodiment of Formula (Ic), $X^1$ is $CR^1$; $X^2$ is N; and $X^3$ is CH. In another embodiment of Formula (Ic), $X^1$ is N; $X^2$ is $CR^1$; and $X^3$ is CH. In another embodiment of Formula (Ic), $X^1$ is N; $X^2$ is $CR^1$; and $X^3$ is N.

In another embodiment of Formula (Ic), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (Ic), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (Ic), $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (Ic), $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (Ic), $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (Ic), $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $R^1$ is $C(O)NH_2$. In another embodiment of Formula (Ic), $R^1$ is F. In another embodiment of Formula (Ic), $R^1$ is Cl. In another embodiment of Formula (Ic), $R^1$ is Br. In another embodiment of Formula (Ic), $R^1$ is CN. In another embodiment of Formula (Ic), $R^1$ is $NH_2$. In another embodiment of Formula (Ic), $R^1$ is $NO_2$. In another embodiment of Formula (Ic), $R^1$ is $CF_3$. In another embodiment of Formula (Ic), $R^1$ is $C(O)OH$. In another embodiment of Formula (Ic), $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl.

In another embodiment of Formula (Ic), $X^1$ and $X^3$ are CH; and $X^2$ is $CR^1$; $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (Ic), $X^1$ and $X^3$ are CH; and $X^2$ is $CR^1$; $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $X^1$ and $X^3$ are CH; and $X^2$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $X^1$ and $X^3$ are CH; and $X^2$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $X^1$ and $X^3$ are CH; and $X^2$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $X^1$ and $X^3$ are CH; and $X^2$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $X^1$ and $X^3$ are CH; and $X^2$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $X^1$ and $X^3$ are CH; and $X^2$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $X^1$ and $X^3$ are CH; and $X^2$ is $CR^1$; and $R^1$ is $C(O)NH_2$. In another embodiment of Formula (Ic), $X^1$ and $X^3$ are CH; and $X^2$ is $CR^1$; and $R^1$ is F. In another embodiment of Formula (Ic), $X^1$ and $X^3$ are CH; and $X^2$ is $CR^1$; and $R^1$ is Cl. In another embodiment of Formula (Ic), $X^1$ and $X^3$ are CH; and $X^2$ is $CR^1$; and $R^1$ is Br. In another embodiment of Formula (Ic), $X^1$ and $X^3$ are CH; and $X^2$ is $CR^1$; and $R^1$ is CN. In another embodiment of Formula (Ic), $X^1$ and $X^3$ are CH; and $X^2$ is $CR^1$; and $R^1$ is $NH_2$. In another embodiment of Formula (Ic), $X^1$ and $X^3$ are CH; and $X^2$ is $CR^1$; and $R^1$ is $NO_2$. In another embodiment of Formula (Ic), $X^1$ and $X^3$ are CH; and $X^2$ is $CR^1$; and $R^1$ is $CF_3$. In another embodiment of Formula (Ic), $X^1$ and $X^3$ are CH; and $X^2$ is $CR^1$; and $R^1$ is $C(O)OH$. In another embodiment of Formula (Ic), $X^1$ and $X^3$ are CH; and $X^2$ is $CR^1$; $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In another embodiment of Formula (Ic), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (Ic), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $X^2$ and $X^3$ are CH; and $X^1$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $X^2$ and $X^3$ are CH; and $X^1$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $X^2$ and $X^3$ are CH; and $X^1$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $X^2$ and $X^3$ are CH; and $X^1$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $X^2$ and $X^3$ are CH; and $X^1$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $X^2$ and $X^3$ are CH; and $X^1$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $X^2$ and $X^3$ are CH; and $X^1$ is $CR^1$; and $R^1$ is $C(O)NH_2$. In another embodiment of Formula (Ic), $X^2$ and $X^3$ are CH; and $X^1$ is $CR^1$; and $R^1$ is F. In another embodiment of Formula (Ic), $X^2$ and $X^3$ are CH; and $X^1$ is $CR^1$; and $R^1$ is Cl. In another embodiment of Formula (Ic), $X^2$ and $X^3$ are CH; and $X^1$ is $CR^1$; and $R^1$ is Br. In another embodiment of Formula (Ic), $X^2$ and $X^3$ are CH; and $X^1$ is $CR^1$; and $R^1$ is CN. In another embodiment of Formula (Ic), $X^2$ and $X^3$ are CH; and $X^1$ is $CR^1$; and $R^1$ is $NH_2$. In another embodiment of Formula (Ic), $X^2$ and $X^3$ are CH; and $X^1$ is $CR^1$; and $R^1$ is $NO_2$. In another embodiment of Formula (Ic), $X^2$ and $X^3$ are CH; and $X^1$ is $CR^1$; and $R^1$ is $CF_3$. In another embodiment of Formula (Ic), $X^2$ and $X^3$ are CH; and $X^1$ is $CR^1$; and $R^1$ is $C(O)OH$. In another embodiment of Formula (Ic), $X^2$ and $X^3$ are CH; and $X^1$ is $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In another embodiment of Formula (Ic), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (Ic), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $X^1$ is CH; and $X^2$ and $X^3$ are $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $X^1$ is CH; and $X^2$ and $X^3$ are $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $X^1$ is CH; and $X^2$ and $X^3$ are $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $X^1$ is CH; and $X^2$ and $X^3$ are $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $X^1$ is CH; and $X^2$ and $X^3$ are $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $X^1$ is CH; and $X^2$ and $X^3$ are $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Ic), $X^1$ is CH; and $X^2$ and $X^3$ are $CR^1$; and $R^1$ is $C(O)NH_2$. In another embodiment of Formula (Ic), $X^1$ is CH; and $X^2$ and $X^3$ are $CR^1$; and $R^1$ is F. In another embodiment of Formula (Ic), $X^1$ is CH; and $X^2$ and $X^3$ are $CR^1$; and $R^1$ is Cl. In another embodiment of Formula (Ic), $X^1$ is CH; and $X^2$ and $X^3$ are $CR^1$; and $R^1$ is Br. In another embodiment of Formula (Ic), $X^1$ is CH; and $X^2$ and $X^3$ are $CR^1$; and $R^1$ is CN. In another embodiment of Formula (Ic), $X^1$ is CH; and $X^2$ and $X^3$ are $CR^1$; and $R^1$ is $NH_2$. In another embodiment of Formula (Ic), $X^1$ is CH; and $X^2$ and $X^3$ are $CR^1$; and $R^1$ is $NO_2$. In another embodiment of Formula (Ic), $X^1$ is CH; and $X^2$ and $X^3$ are $CR^1$; and $R^1$ is $CF_3$. In another embodiment of Formula (Ic), $X^1$ is CH; and $X^2$ and $X^3$ are $CR^1$; and $R^1$ is $C(O)OH$. In another embodiment of Formula (Ic), $X^1$ is CH; and $X^2$ and $X^3$ are $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In one embodiment of Formula (Ic), $R^2$ is phenyl which is substituted at the para position with $R^5$; and $R^5$ is phthalazin-1(2H)-onyl, isoquinolinyl, isoquinolin-1(2H)-onyl, 5,6,7,8-tetrahydrophthalazin-1(2H)-onyl, 5-fluorophthalazin-1(2H)-onyl, (Z)-3H-benzo[d][1,2]diazepin-4(5H)-onyl, 5-(trifluoromethyl)phthalazin-1(2H)-onyl, pyrrolo[1,2-d][1,2,4]triazin-1(2H)-one, or isoindolin-1-onyl.

In one embodiment of Formula (Ic), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N; or $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$;

$R^2$ is alkyl, phenyl, cycloalkyl, or heterocyclyl; wherein each $R^2$ alkyl is optionally substituted with one, two, three or four independently selected $R^4$, $OR^4$, $C(O)R^4$, $CO(O)R^4NHC(O)R^4$, $NR^4C(O)R^4$, $C(O)NHR^4$, or $C(O)N(R^4)_2$; wherein each $R^2$ phenyl is optionally substituted at the para position with one independently selected $R^5$, $OR^5$, $SO_2R^5$, $C(O)R^5$, $CO(O)R^5$, $NHR^5$, $NHC(O)R^5$, $NHS(O)_2R^5$, $C(O)NH_2$, $C(O)NHR^5$, $C(O)N(R^5)_2$, $CHNOR^5$, $C(O)NHOR^5$, $SO_2NHR^5$, $CF_3$, Br or I; wherein each $R^2$ phenyl is optionally additionally substituted with one F; wherein each $R^2$ heterocyclyl and cycloalkyl are optionally substituted with one, two, three or four independently selected $R^5$, $OR^5$, $C(O)R^5$, $C(O)OR^5$, $N(R^5)_2$, $NHC(O)R^5$, $C(O)NHR^5$, F, Cl, Br or I;

$R^3$, at each occurrence, is independently selected alkyl, alkenyl, or heterocyclyl; wherein each $R^3$ alkyl is optionally substituted with one, two, three or four independently selected $R^6$, $OR^6$, $NH_2$, $N(R^6)_2$, $NHC(O)R^6$, OH, F, Cl, Br or I;

$R^4$, at each occurrence, is independently selected alkyl, aryl, cycloalkyl, or heterocyclyl; wherein each $R^4$ alkyl is optionally substituted with one, two, three or four independently selected $R^7$, F, Cl, Br or I; wherein each $R^4$ aryl cycloalkyl, and heterocycyl is optionally substituted with one, two, three or four independently selected $R^8$, $C(O)R^8$, $CO(O)R^8$, F, Cl, Br or I;

$R^5$, at each occurrence, is independently selected alkyl, alkenyl, alkynyl, aryl, heterocyclyl, cycloalkyl, or cycloalkenyl; wherein each $R^5$ alkyl, alkenyl, and alkynyl is optionally substituted with one, two, three or four independently selected $R^9$, $OR^9$, $SR^9$, $C(O)R^9$, $NH_2$, $N(R^9)_2$, $NHC(O)R^9$, $NR^9C(O)OR^9$, $C(O)NH_2$, $C(O)NHR^9$, $C(O)N(R^9)_2$, $C(O)OH$, OH, CN, $CF_3$, F, Cl, Br or I;

$R^6$, at each occurrence, is independently selected alkyl or heterocyclyl; wherein each $R^6$ alkyl is optionally substituted with one, two, three or four independently selected F, Cl, Br or I;

$R^7$, at each occurrence, is independently selected aryl, or heterocyclyl;

$R^8$, at each occurrence, is independently selected alkyl, aryl, heterocyclyl, or cycloalkyl; wherein each $R^8$ alkyl is optionally substituted with one, two, three or four independently selected $R^{12}$, $OR^{12}OH$, $CF_3$, F, Cl, Br or I;

$R^9$, at each occurrence, is independently selected alkyl, aryl, heterocyclyl, or cycloalkyl; wherein each $R^9$ alkyl is optionally substituted with one, two, three or four independently selected alkoxy, OH, cycloalkyl, aryl, or heterocyclyl;

$R^{12}$, at each occurrence, is independently selected alkyl, heterocyclyl, or cycloalkyl; wherein each $R^{12}$ alkyl is optionally substituted with one or more alkoxy;

wherein the $R^3$, $R^5$, $R^6$, $R^7$, $R^8$, $R^9$, $R^{10}$, $R^{11}$, and $R^{12}$ are optionally substituted with one, two, three, four, five, or six independently selected $R^{13}$, $OR^{13}$, $SO_2R^{13}$, $C(O)R^{13}$, $CO(O)R^{13}$, $NH_2$, $N(R^{13})_2$, $NHC(O)R^{13}$, $NHC(O)OR^{13}$, $C(O)NH_2$, $C(O)NHR^{13}$, $C(O)N(R^{13})_2$, OH, CN, $CF_3$, $OCF_3$, $SCF_3$, F, Cl, Br or I;

$R^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, or cycloalkenyl; wherein each $R^{13}$ alkyl, alkenyl, and alkynyl is optionally substituted with one, two, three or four independently selected $R^{14}$, $OR^{14}$, $SO_2R^{14}$, $NH_2$, $NHR^{14}$, $N(R^{14})_2$, $NHC(O)R^{14}$, $NHC(O)OR^{14}$, OH, $CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, or cycloalkenyl is optionally substituted with one, two, three or four independently selected $R^{15}$, $OR^{15}$, $SO_2R^{15}$, $C(O)R^{15}$, $N(R^{15})_2$, $NHC(O)R^{15}$, OH, CN, $CF_3$, F, Cl, Br or I;

$R^{14}$, at each occurrence, is independently selected alkyl, aryl, heterocyclyl, or cycloalkyl; wherein each $R^{14}$ alkyl is optionally substituted with one, two, three or four independently selected heterocyclyl, alkoxy, OH, F, Cl, Br or I; wherein each $R^{14}$ aryl, heterocyclyl, and cycloalkyl is optionally substituted with one, two, three or four independently selected $R^{16}$, $OR^{16}$, OH, F, Cl, Br, or I;

$R^{15}$, at each occurrence, is independently selected alkyl; wherein the $R^{15}$ alkyl is optionally substituted with one, two, three or four alkoxy; and $R^{16}$, at each occurrence, is independently selected alkyl, wherein the $R^{16}$ alkyl is optionally substituted with one, two, three or four alkoxy;

with the proviso that when $X^1$, $X^2$, and $X^3$ are CH and $R^2$ is phenyl; $R^5$ is not methyl;

with the proviso that when $X^1$, $X^2$, and $X^3$ are CH, and $R^2$ is phenyl substituted with $OR^5$; $R^5$ is not methyl;

with the proviso that when $R^2$ is unsubstituted alkyl or optionally substituted alkyl; $R^2$ is $C_4$-$C_6$-alkyl;

with the proviso that when $R^{13}$ is piperidinyl, it is substituted piperidinyl; and with the proviso that when $R^{13}$ is pyrrolinyl, at least one of $X^1$, $X^2$, and $X^3$ is N.

In another embodiment of Formula (Ic), $X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$;

$R^2$ is alkyl, phenyl, cycloalkyl, or heterocyclyl; wherein each $R^2$ alkyl is optionally substituted with one, two, three or four independently selected $R^4$, $OR^4$, $C(O)R^4$, $CO(O)R^4NHC(O)R^4$, $NR^4C(O)R^4$, $C(O)NHR^4$, or $C(O)N(R^4)_2$; wherein each $R^2$ phenyl is optionally substituted at the para position with one independently selected $R^5$, $OR^5$, $SO_2R^5$, $C(O)R^5$, $CO(O)R^5$, $NHR^5$, $NHC(O)R^5$, $NHS(O)_2R^5$, $C(O)NH_2$, $C(O)NHR^5$, $C(O)N(R^5)_2$, $CHNOR^5$, $C(O)NHOR^5$, $SO_2NHR^5$, or $CF_3$; wherein each $R^2$ phenyl is optionally additionally substituted with one F; wherein each $R^2$ heterocyclyl and cycloalkyl are optionally substituted with one, two, three or four independently selected $R^5$, $OR^5$, $C(O)R^5$, $C(O)OR^5$, $N(R^5)_2$, $NHC(O)R^5$, or $C(O)NHR^5$;

$R^3$, at each occurrence, is independently selected alkyl, alkenyl, or heterocyclyl; wherein each $R^3$ alkyl is optionally substituted with one, two, three or four independently selected $R^6$, $OR^6$, $NH_2$, $N(R^6)_2$, $NHC(O)R^6$, or OH;

$R^4$, at each occurrence, is independently selected alkyl, aryl, cycloalkyl, or heterocyclyl; wherein each $R^4$ alkyl is optionally substituted with one, two, three or four independently selected $R^7$; wherein each $R^4$ aryl cycloalkyl, and heterocycyl is optionally substituted with one, two, three or four independently selected $R^8$, $C(O)R^8$, $CO(O)R^8$, F, Cl, or Br;

$R^5$, at each occurrence, is independently selected alkyl, alkenyl, alkynyl, aryl, heterocyclyl, cycloalkyl, or cycloalkenyl; wherein each $R^5$ alkyl, alkenyl, and alkynyl is optionally substituted with one, two, three or four independently selected $R^9$, $OR^9$, $SR^9$, $C(O)R^9$, $NH_2$, $N(R^9)_2$, $NHC(O)R^9$, $NR^9C(O)OR^9$, $C(O)NH_2$, $C(O)NHR^9$, $C(O)N(R^9)_2$, $C(O)OH$, OH, CN, $CF_3$, or F;

$R^6$, at each occurrence, is independently selected alkyl or heterocyclyl;

$R^7$, at each occurrence, is independently selected aryl, or heterocyclyl;

$R^8$, at each occurrence, is independently selected alkyl, aryl, heterocyclyl, or cycloalkyl; wherein each $R^8$ alkyl is optionally substituted with one, two, three or four independently selected $R^{12}$, $OR^{12}OH$, or $CF_3$;

$R^9$, at each occurrence, is independently selected alkyl, aryl, heterocyclyl, or cycloalkyl; wherein each $R^9$ alkyl is optionally substituted with one, two, three or four independently selected alkoxy, OH, cycloalkyl, aryl, or heterocyclyl;

R¹², at each occurrence, is independently selected alkyl, heterocyclyl, or cycloalkyl; wherein each R¹² alkyl is optionally substituted with one or more alkoxy;

wherein the cyclic moieties represented by $R^3$, $R^5$, $R^6$, $R^7$, $R^8$, $R^9$, $R^{10}$, $R^{11}$, and $R^{12}$ are optionally substituted with one, two, three, four, five, or six independently selected $R^{13}$, $OR^{13}$, $SO_2R^{13}$, $C(O)R^{13}$, $CO(O)R^{13}$, $NH_2$, $N(R^{13})_2$, $NHC(O)R^{13}$, $NHC(O)OR^{13}$, $C(O)NH_2$, $C(O)NHR^{13}$, $C(O)N(R^{13})_2$, OH, CN, $CF_3$, $OCF_3$, $SCF_3$, F, or Cl;

$R^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, or cycloalkenyl; wherein each $R^{13}$ alkyl and alkynyl is optionally substituted with one, two, three or four independently selected $R^{14}$, $OR^{14}$, $SO_2R^{14}$, $NH_2$, $NHR^{14}$, $N(R^{14})_2$, $NHC(O)R^{14}$, $NHC(O)OR^{14}$, OH, or $CF_3$; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, and cycloalkenyl is optionally substituted with one, two, three or four independently selected $R^{15}$, $OR^{15}$, $SO_2R^{15}$, $C(O)R^{15}$, $N(R^{15})_2$, $NHC(O)R^{15}$, CN, OH, $CF_3$, F, or Cl;

$R^{14}$, at each occurrence, is independently selected alkyl, aryl, heterocyclyl, or cycloalkyl; wherein each $R^{14}$ alkyl is optionally substituted with one, two, three or four independently selected heterocyclyl, alkoxy, or OH; wherein each $R^{14}$ aryl, heterocyclyl, and cycloalkyl is optionally substituted with one, two, three or four independently selected $R^{16}$, $OR^{16}$, OH, or Cl;

$R^{15}$, at each occurrence, is independently selected alkyl; wherein the $R^{15}$ alkyl is optionally substituted with one, two, three or four alkoxy; and $R^{16}$, at each occurrence, is independently selected alkyl, wherein the $R^{16}$ alkyl is optionally substituted with one, two, three or four independently selected alkoxy;

with the proviso that when $X^1$, $X^2$, and $X^3$ are CH and $R^2$ is phenyl; $R^5$ is not methyl;

with the proviso that when $X^1$, $X^2$, and $X^3$ are CH, and $R^2$ is phenyl substituted with $OR^5$; $R^5$ is not methyl;

with the proviso that when $R^2$ is unsubstituted alkyl or optionally substituted alkyl; $R^2$ is $C_4$-$C_6$-alkyl;

with the proviso that when $R^{13}$ is piperidinyl, it is substituted piperidinyl; and with the proviso that when $R^{13}$ is pyrrolinyl, at least one of $X^1$, $X^2$, and $X^3$ is N.

Still another embodiment pertains to compounds having Formula (Ic), which include N-{4-[(3-phenylpropyl)carbamoyl]phenyl}-1,3-dihydro-2H-isoindole-2-carboxamide;
N-(4-{[4-(aminomethyl)benzyl]carbamoyl}phenyl)-5-fluoro-1,3-dihydro-2H-isoindole-2-carboxamide;
5-cyano-N-{4-[(3-phenylpropyl)carbamoyl]phenyl}-1,3-dihydro-2H-isoindole-2-carboxamide;
N-{4-[(cyclopentylmethyl)carbamoyl]phenyl}-5-fluoro-1,3-dihydro-2H-isoindole-2-carboxamide;
5-cyano-N-[4-(propylcarbamoyl)phenyl]-1,3-dihydro-2H-isoindole-2-carboxamide;
N-(4-{[4-(furo[3,2-c]pyridin-4-yl)piperazin-1-yl]carbonyl}phenyl)-1,3-dihydro-2H-isoindole-2-carboxamide;
5-cyano-N-(4-{[4-(pyridin-2-yl)piperazin-1-yl]carbonyl}phenyl)-1,3-dihydro-2H-isoindole-2-carboxamide;
5-fluoro-N-{4-[(pyridin-2-ylmethyl)carbamoyl]phenyl}-1,3-dihydro-2H-isoindole-2-carboxamide;
N-[4-(benzylcarbamoyl)phenyl]-5-fluoro-1,3-dihydro-2H-isoindole-2-carboxamide;
N-{4-[(3,4-dimethoxybenzyl)carbamoyl]phenyl}-1,3-dihydro-2H-isoindole-2-carboxamide;
5-methyl-N-(4-{[4-(pyridin-2-yl)piperazin-1-yl]carbonyl}phenyl)-1,3-dihydro-2H-isoindole-2-carboxamide;
N-(4-{[4-(thieno[3,2-c]pyridin-4-yl)piperazin-1-yl]carbonyl}phenyl)-1,3-dihydro-2H-isoindole-2-carboxamide;
N-{4-[(2,3-dimethoxybenzyl)carbamoyl]phenyl}-1,3-dihydro-2H-isoindole-2-carboxamide;
5-fluoro-N-{4-[(3-phenylpropyl)carbamoyl]phenyl}-1,3-dihydro-2H-isoindole-2-carboxamide;
5-fluoro-N-(4-{[4-(pyridazin-3-yl)piperazin-1-yl]carbonyl}phenyl)-1,3-dihydro-2H-isoindole-2-carboxamide;
N-{4-[(2,3-dihydro-1,4-benzo dioxin-5-ylmethyl)carbamoyl]phenyl}-1,3-dihydro-2H-isoindole-2-carboxamide;
5-fluoro-N-(4-{[1-(3-methylbutyl)-1H-pyrazol-4-yl]carbamoyl}phenyl)-1,3-dihydro-2H-isoindole-2-carboxamide;
N-{4-[(2-fluorobenzyl)carbamoyl]phenyl}-1,3-dihydro-2H-isoindole-2-carboxamide;
5-fluoro-N-(4-{[4-(pyrimidin-2-yl)piperazin-1-yl]carbonyl}phenyl)-1,3-dihydro-2H-isoindole-2-carboxamide;
5-fluoro-N-{4-[(3-methylbutyl)carbamoyl]phenyl}-1,3-dihydro-2H-isoindole-2-carboxamide;
N-{4-[(2-methoxybenzyl)carbamoyl]phenyl}-1,3-dihydro-2H-isoindole-2-carboxamide;
5-fluoro-N-(4-{[4-(pyridin-2-yl)piperazin-1-yl]carbonyl}phenyl)-1,3-dihydro-2H-isoindole-2-carboxamide;
N-{4-[(3-fluorobenzyl)carbamoyl]phenyl}-1,3-dihydro-2H-isoindole-2-carboxamide;
5-fluoro-N-(4-{[3-(2-oxopyrrolidin-1-yl)propyl]carbamoyl}phenyl)-1,3-dihydro-2H-isoindole-2-carboxamide;
5-cyano-N-{4-[(3-methylbutyl)carbamoyl]phenyl}-1,3-dihydro-2H-isoindole-2-carboxamide;
N-{4-[(cyclopentylmethyl)carbamoyl]phenyl}-5-methyl-1,3-dihydro-2H-isoindole-2-carboxamide;
N-(4-{[4-(4-cyanophenyl)piperazin-1-yl]carbonyl}phenyl)-1,3-dihydro-2H-isoindole-2-carboxamide;
N-{4-[(4-fluorobenzyl)carbamoyl]phenyl}-1,3-dihydro-2H-isoindole-2-carboxamide;
N-{4-[(3,5-dimethoxybenzyl)carbamoyl]phenyl}-1,3-dihydro-2H-isoindole-2-carboxamide;
5-fluoro-N-{4-[(tetrahydro furan-3-ylmethyl)carbamoyl]phenyl}-1,3-dihydro-2H-isoindole-2-carboxamide;
N-{4-[(2,2-dimethylpropyl)carbamoyl]phenyl}-1,3-dihydro-2H-isoindole-2-carboxamide;
5-fluoro-N-(4-{[2-(2-oxopyrrolidin-1-yl)ethyl]carbamoyl}phenyl)-1,3-dihydro-2H-isoindole-2-carboxamide;
N-(4-{[4-(trifluoromethoxy)benzyl]carbamoyl}phenyl)-1,3-dihydro-2H-isoindole-2-carboxamide;

N-(4-{[3-fluoro-5-(trifluoromethyl)benzyl]
carbamoyl}phenyl)-1,3-dihydro-2H-isoindole-2-carboxamide;
5-fluoro-N-(4-{[4-(pyrazin-2-yl)piperazin-1-yl]
carbonyl}phenyl)-1,3-dihydro-2H-isoindole-2-carboxamide;
N-{4-[(3-methylbutyl)carbamoyl]phenyl}-1,3-dihydro-2H-isoindole-2-carboxamide;
5-methoxy-N-{4-[(3-phenylpropyl)carbamoyl]phenyl}-1,3-dihydro-2H-isoindole-2-carboxamide;
N-{4-[(4-chlorobenzyl)carbamoyl]phenyl}-1,3-dihydro-2H-isoindole-2-carboxamide;
N-{4-[(cyclopentylmethyl)carbamoyl]phenyl}-1,3-dihydro-2H-isoindole-2-carboxamide;
N-{4-[(3,4,5-trimethoxybenzyl)carbamoyl]phenyl}-1,3-dihydro-2H-isoindole-2-carboxamide;
N-(4-{[4-(pyrimidin-2-yl)piperazin-1-yl]carbonyl}phenyl)-1,3-dihydro-2H-isoindole-2-carboxamide;
5-nitro-N-[4-(propylcarbamoyl)phenyl]-1,3-dihydro-2H-isoindole-2-carboxamide;
5-methyl-N-{4-[(3-methylbutyl)carbamoyl]phenyl}-1,3-dihydro-2H-isoindole-2-carboxamide;
N-(4-{[4-(4-fluorophenyl)piperazin-1-yl]carbonyl}phenyl)-1,3-dihydro-2H-isoindole-2-carboxamide;
N-{4-[(4-methoxybenzyl)carbamoyl]phenyl}-1,3-dihydro-2H-isoindole-2-carboxamide;
N-{4-[(2-thienylmethyl)carbamoyl]phenyl}-1,3-dihydro-2H-isoindole-2-carboxamide;
N-(4-{[4-(pyrimidin-2-yl)piperazin-1-yl]carbonyl}phenyl)-5-(trifluoromethyl)-1,3-dihydro-2H-isoindole-2-carboxamide;
N-{4-[(1-ethyl-1H-pyrazol-4-yl)carbamoyl]phenyl}-5-fluoro-1,3-dihydro-2H-isoindole-2-carboxamide;
N-{4-[(1-benzyl-1H-pyrazol-4-yl)carbamoyl]phenyl}-5-fluoro-1,3-dihydro-2H-isoindole-2-carboxamide;
N-(4-{[4-(pyridin-2-yl)piperazin-1-yl]carbonyl}phenyl)-1,3-dihydro-2H-isoindole-2-carboxamide;
N-(4-{[4-(pyrazin-2-yl)piperazin-1-yl]carbonyl}phenyl)-1,3-dihydro-2H-isoindole-2-carboxamide;
N-(4-{[4-(2-methoxyphenyl)piperazin-1-yl]
carbonyl}phenyl)-1,3-dihydro-2H-isoindole-2-carboxamide;
N-{4-[(3,3-dimethylbutyl)carbamoyl]phenyl}-1,3-dihydro-2H-isoindole-2-carboxamide;
N-(4-{[(2R)-tetrahydrofuran-2-ylmethyl]
carbamoyl}phenyl)-1,3-dihydro-2H-isoindole-2-carboxamide;
N-(4-{[4-(3-methoxyphenyl)piperazin-1-yl]
carbonyl}phenyl)-1,3-dihydro-2H-isoindole-2-carboxamide;
N-(4-{[4-(4-acetylphenyl)piperazin-1-yl]carbonyl}phenyl)-1,3-dihydro-2H-isoindole-2-carboxamide;
N-(4-{[2-(2,3-dimethoxyphenyl)ethyl]carbamoyl}phenyl)-1,3-dihydro-2H-isoindole-2-carboxamide;
N-{4-[(3-thienylmethyl)carbamoyl]phenyl}-1,3-dihydro-2H-isoindole-2-carboxamide;
5-methoxy-N-{4-[(3-methylbutyl)carbamoyl]phenyl}-1,3-dihydro-2H-isoindole-2-carboxamide;
N-{4-[(pyridin-2-ylmethyl)carbamoyl]phenyl}-1,3-dihydro-2H-isoindole-2-carboxamide;
5-fluoro-N-(4-{[2-(2-thienyl)ethyl]carbamoyl}phenyl)-1,3-dihydro-2H-isoindole-2-carboxamide;
N-(4-{[(2S)-tetrahydrofuran-2-ylmethyl]
carbamoyl}phenyl)-1,3-dihydro-2H-isoindole-2-carboxamide;
N-(4-{[1-(3-methylbutyl)-1H-pyrazol-4-yl]
carbamoyl}phenyl)-1,3-dihydro-2H-isoindole-2-carboxamide;
4-chloro-N-(4-{[4-(pyridin-2-yl)piperazin-1-yl]
carbonyl}phenyl)-1,3-dihydro-2H-isoindole-2-carboxamide;
N-{4-[(4-phenylpiperazin-1-yl)carbonyl]phenyl}-1,3-dihydro-2H-isoindole-2-carboxamide;
N-{4-[(6-aminohexyl)carbamoyl]phenyl}-1,3-dihydro-2H-isoindole-2-carboxamide;
4-chloro-N-{4-[(3-methylbutyl)carbamoyl]phenyl}-1,3-dihydro-2H-isoindole-2-carboxamide;
N-(4-{[2-(2-thienyl)ethyl]carbamoyl}phenyl)-1,3-dihydro-2H-isoindole-2-carboxamide;
5-methoxy-N-(4-{[4-(pyridin-2-yl)piperazin-1-yl]
carbonyl}phenyl)-1,3-dihydro-2H-isoindole-2-carboxamide;
N-{4-[(1,3-benzodioxol-5-ylmethyl)carbamoyl]phenyl}-1,3-dihydro-2H-isoindole-2-carboxamide;
N-{4-[(3-methoxybenzyl)carbamoyl]phenyl}-1,3-dihydro-2H-isoindole-2-carboxamide;
N-(4-{[4-(pyridin-3-yl)piperazin-1-yl]carbonyl}phenyl)-1,3-dihydro-2H-isoindole-2-carboxamide;
N-[4-(benzylcarbamoyl)phenyl]-1,3-dihydro-2H-isoindole-2-carboxamide;
N-(4-{[4-(pyridazin-3-yl)piperazin-1-yl]carbonyl}phenyl)-1,3-dihydro-2H-isoindole-2-carboxamide;
N-{4-[(pyrimidin-4-ylmethyl)carbamoyl]phenyl}-1,3-dihydro-2H-isoindole-2-carboxamide;
N-(4-{[4-(3-fluorophenyl)piperazin-1-yl]carbonyl}phenyl)-1,3-dihydro-2H-isoindole-2-carboxamide;
N-{4-[(2-methylbutyl)carbamoyl]phenyl}-1,3-dihydro-2H-isoindole-2-carboxamide;
N-(4-{[4-(pyridin-2-yl)piperazin-1-yl]carbonyl}phenyl)-5-(trifluoromethyl)-1,3-dihydro-2H-isoindole-2-carboxamide;
N-{4-[(3-butoxypropyl)carbamoyl]phenyl}-1,3-dihydro-2H-isoindole-2-carboxamide;
N-(4-{[(1S)-2-hydroxy-1-phenylethyl]carbamoyl}phenyl)-1,3-dihydro-2H-isoindole-2-carboxamide;
N-(4-{[2-(3,4-dihydroxyphenyl)ethyl]carbamoyl}phenyl)-1,3-dihydro-2H-isoindole-2-carboxamide;
N-{4-[(3-propoxypropyl)carbamoyl]phenyl}-1,3-dihydro-2H-isoindole-2-carboxamide;
N-{4-[(3-furylmethyl)carbamoyl]phenyl}-1,3-dihydro-2H-isoindole-2-carboxamide;
N-(4-{[4-(2-cyanophenyl)piperazin-1-yl]carbonyl}phenyl)-1,3-dihydro-2H-isoindole-2-carboxamide;
N-{4-[(3-hydroxy-2-methylphenyl)carbamoyl]phenyl}-1,3-dihydro-2H-isoindole-2-carboxamide;
N-{4-[(3-methylbutyl)carbamoyl]phenyl}-5-(trifluoromethyl)-1,3-dihydro-2H-isoindole-2-carboxamide;
N-{4-[(3-methyl-1H-indazol-5-yl)carbamoyl]phenyl}-1,3-dihydro-2H-isoindole-2-carboxamide;
N-{4-[(3-ethoxypropyl)carbamoyl]phenyl}-1,3-dihydro-2H-isoindole-2-carboxamide;
N-(4-{[4-(pyrazin-2-yl)piperazin-1-yl]carbonyl}phenyl)-5-(trifluoromethyl)-1,3-dihydro-2H-isoindole-2-carboxamide;
N-(4-{[2-(2,5-dimethoxyphenyl)ethyl]carbamoyl}phenyl)-1,3-dihydro-2H-isoindole-2-carboxamide;
N-{4-[(tetrahydrofuran-3-ylmethyl)carbamoyl]phenyl}-1,3-dihydro-2H-isoindole-2-carboxamide;
N-{4-[(1-benzyl-1H-pyrazol-4-yl)carbamoyl]phenyl}-1,3-dihydro-2H-isoindole-2-carboxamide;
methyl 5-({4-[(1,3-dihydro-2H-isoindol-2-ylcarbonyl)amino]benzoyl}amino)-1H-indazole-3-carboxylate;

N-(4-{[2-(2-oxopyrrolidin-1-yl)ethyl]carbamoyl}phenyl)-1,3-dihydro-2H-isoindole-2-carboxamide;
N-{4-[(pyridin-4-ylmethyl)carbamoyl]phenyl}-1,3-dihydro-2H-isoindole-2-carboxamide;
N-(4-{[4-(5-chloropyridin-2-yl)piperazin-1-yl]carbonyl}phenyl)-1,3-dihydro-2H-isoindole-2-carboxamide;
N-(4-{[2-(1H-indol-3-yl)ethyl]carbamoyl}phenyl)-1,3-dihydro-2H-isoindole-2-carboxamide;
N-(4-{[4-(trifluoromethyl)benzyl]carbamoyl}phenyl)-1,3-dihydro-2H-isoindole-2-carboxamide;
N-{4-[(3,5-dimethoxyphenyl)carbamoyl]phenyl}-1,3-dihydro-2H-isoindole-2-carboxamide;
N-{4-[(pyridin-3-ylmethyl)carbamoyl]phenyl}-1,3-dihydro-2H-isoindole-2-carboxamide;
N-[4-(2,3-dihydro-1,4-benzodioxin-6-ylcarbamoyl)phenyl]-1,3-dihydro-2H-isoindole-2-carboxamide;
N-(4-{[4-(2-fluorobenzoyl)piperazin-1-yl]carbonyl}phenyl)-1,3-dihydro-2H-isoindole-2-carboxamide;
N-(4-{[2-(5-methoxy-1H-indol-3-yl)ethyl]carbamoyl}phenyl)-1,3-dihydro-2H-isoindole-2-carboxamide;
N-{4-[(3-aminobenzyl)carbamoyl]phenyl}-1,3-dihydro-2H-isoindole-2-carboxamide;
N-(4-{[2-(2-chlorophenyl)ethyl]carbamoyl}phenyl)-1,3-dihydro-2H-isoindole-2-carboxamide;
N-(4-{[(2R)-1-hydroxy-4-methylpentan-2-yl]carbamoyl}phenyl)-1,3-dihydro-2H-isoindole-2-carboxamide;
N-{4-[(2-propoxyethyl)carbamoyl]phenyl}-1,3-dihydro-2H-isoindole-2-carboxamide;
N-{4-[(3-isobutoxypropyl)carbamoyl]phenyl}-1,3-dihydro-2H-isoindole-2-carboxamide;
N-(4-{[4-(pyridin-4-yl)piperazin-1-yl]carbonyl}phenyl)-1,3-dihydro-2H-isoindole-2-carboxamide;
N-[4-({4-[5-(trifluoromethyl)pyridin-2-yl]piperazin-1-yl}carbonyl)phenyl]-1,3-dihydro-2H-isoindole-2-carboxamide;
N-{4-[(3,4,5-trimethoxyphenyl)carbamoyl]phenyl}-1,3-dihydro-2H-isoindole-2-carboxamide;
N-{4-[(4-methylpiperidin-1-yl)carbonyl]phenyl}-1,3-dihydro-2H-isoindole-2-carboxamide;
N-[4-({2-[4-(dimethylamino)phenyl]ethyl}carbamoyl)phenyl]-1,3-dihydro-2H-isoindole-2-carboxamide;
N-(4-{[3-(trifluoromethoxy)benzyl]carbamoyl}phenyl)-1,3-dihydro-2H-isoindole-2-carboxamide;
N-(4-{[(1R)-3-hydroxy-1-phenylpropyl]carbamoyl}phenyl)-1,3-dihydro-2H-isoindole-2-carboxamide;
N-{4-[(3-cyanophenyl)carbamoyl]phenyl}-1,3-dihydro-2H-isoindole-2-carboxamide;
N-{4-[(3-fluoro-4-methoxyphenyl)carbamoyl]phenyl}-1,3-dihydro-2H-isoindole-2-carboxamide;
N-{4-[(2,3-dimethoxyphenyl)carbamoyl]phenyl}-1,3-dihydro-2H-isoindole-2-carboxamide;
N-(4-{[2-(2-fluorophenyl)ethyl]carbamoyl}phenyl)-1,3-dihydro-2H-isoindole-2-carboxamide;
N-[4-(isobutylcarbamoyl)phenyl]-1,3-dihydro-2H-isoindole-2-carboxamide;
N-(4-{[2-(1,3-benzodioxol-5-yl)ethyl]carbamoyl}phenyl)-1,3-dihydro-2H-isoindole-2-carboxamide;
N-(4-{[2-(2-methoxyphenyl)ethyl]carbamoyl}phenyl)-1,3-dihydro-2H-isoindole-2-carboxamide;
N-[4-(butylcarbamoyl)phenyl]-1,3-dihydro-2H-isoindole-2-carboxamide;
N-{4-[(2-isopropoxyethyl)carbamoyl]phenyl}-1,3-dihydro-2H-isoindole-2-carboxamide;
N-{4-[(3-isopropoxypropyl)carbamoyl]phenyl}-1,3-dihydro-2H-isoindole-2-carboxamide;
4-chloro-N-{4-[(3-phenylpropyl)carbamoyl]phenyl}-1,3-dihydro-2H-isoindole-2-carboxamide;
N-(4-{[2-(4-methoxyphenyl)ethyl]carbamoyl}phenyl)-1,3-dihydro-2H-isoindole-2-carboxamide;
N-{4-[(3-methoxypropyl)carbamoyl]phenyl}-1,3-dihydro-2H-isoindole-2-carboxamide;
N-(4-{[2-(4-fluorophenyl)ethyl]carbamoyl}phenyl)-1,3-dihydro-2H-isoindole-2-carboxamide;
N-(4-{[3-(2-oxopyrrolidin-1-yl)propyl]carbamoyl}phenyl)-1,3-dihydro-2H-isoindole-2-carboxamide;
N-{4-[(2,4-dimethoxyphenyl)carbamoyl]phenyl}-1,3-dihydro-2H-isoindole-2-carboxamide;
$N^2$-[4-(propylcarbamoyl)phenyl]-1,3-dihydro-2H-isoindole-2,5-dicarboxamide;
N-{4-[(2-phenoxyethyl)carbamoyl]phenyl}-1,3-dihydro-2H-isoindole-2-carboxamide;
N-(4-{[2-(4-hydroxyphenyl)ethyl]carbamoyl}phenyl)-1,3-dihydro-2H-isoindole-2-carboxamide;
N-(4-{[2-(3-fluorophenyl)ethyl]carbamoyl}phenyl)-1,3-dihydro-2H-isoindole-2-carboxamide;
N-[4-({1-[(3S)-tetrahydrofuran-3-yl]-1H-pyrazol-4-yl}carbamoyl)phenyl]-1,3-dihydro-2H-isoindole-2-carboxamide;
5-methyl-N-{4-[(3-phenylpropyl)carbamoyl]phenyl}-1,3-dihydro-2H-isoindole-2-carboxamide;
N-[4-(1,4-dioxa-8-azaspiro[4.5]dec-8-ylcarbonyl)phenyl]-1,3-dihydro-2H-isoindole-2-carboxamide;
N-{4-[(2-phenylethyl)carbamoyl]phenyl}-1,3-dihydro-2H-isoindole-2-carboxamide;
N-(4-{[2-(2,4-dimethoxyphenyl)ethyl]carbamoyl}phenyl)-1,3-dihydro-2H-isoindole-2-carboxamide;
N-(4-{[3-(methylthio)propyl]carbamoyl}phenyl)-1,3-dihydro-2H-isoindole-2-carboxamide;
N-{4-[(2-ethoxyethyl)carbamoyl]phenyl}-1,3-dihydro-2H-isoindole-2-carboxamide;
N-{4-[(2-fluorophenyl)carbamoyl]phenyl}-1,3-dihydro-2H-isoindole-2-carboxamide;
N-(4-{[2-(pyridin-3-yl)ethyl]carbamoyl}phenyl)-1,3-dihydro-2H-isoindole-2-carboxamide;
N-[4-({4-[(trifluoromethyl)thio]benzyl}carbamoyl)phenyl]-1,3-dihydro-2H-isoindole-2-carboxamide;
N-{4-[(3,4-dimethoxyphenyl)carbamoyl]phenyl}-1,3-dihydro-2H-isoindole-2-carboxamide;
N-(4-{[3-(2-fluorophenyl)pyrrolidin-1-yl]carbonyl}phenyl)-1,3-dihydro-2H-isoindole-2-carboxamide;
N-(4-{[3-(1H-imidazol-1-yl)propyl]carbamoyl}phenyl)-1,3-dihydro-2H-isoindole-2-carboxamide;
N-(4-{[2-(3-chlorophenyl)ethyl]carbamoyl}phenyl)-1,3-dihydro-2H-isoindole-2-carboxamide;
N-{4-[(4-hydroxybutyl)carbamoyl]phenyl}-1,3-dihydro-2H-isoindole-2-carboxamide;
N-{4-[(3-phenylpropyl)carbamoyl]phenyl}-5-(trifluoromethyl)-1,3-dihydro-2H-isoindole-2-carboxamide;
N-(4-{[4-(hydroxymethyl)phenyl]carbamoyl}phenyl)-1,3-dihydro-2H-isoindole-2-carboxamide;
N-[4-(1,3-benzodioxol-5-ylcarbamoyl)phenyl]-1,3-dihydro-2H-isoindole-2-carboxamide;
N-{4-[(1-isopropyl-1H-pyrazol-4-yl)carbamoyl]phenyl}-1,3-dihydro-2H-isoindole-2-carboxamide;
N-{4-[(4-hydroxyphenyl)carbamoyl]phenyl}-1,3-dihydro-2H-isoindole-2-carboxamide;

N-{4-[(1-ethyl-1H-pyrazol-4-yl)carbamoyl]phenyl}-1,3-dihydro-2H-isoindole-2-carboxamide;
N-{4-[(2,5-dimethoxyphenyl)carbamoyl]phenyl}-1,3-dihydro-2H-isoindole-2-carboxamide;
N-{4-[methyl(3-phenylpropyl)carbamoyl]phenyl}-1,3-dihydro-2H-isoindole-2-carboxamide;
N-{4-[(2-hydroxy-2-methylpropyl)carbamoyl]phenyl}-1,3-dihydro-2H-isoindole-2-carboxamide;
N-(4-{[4-(trifluoromethyl)piperidin-1-yl]carbonyl}phenyl)-1,3-dihydro-2H-isoindole-2-carboxamide;
N-[4-(thiomorpholin-4-ylcarbonyl)phenyl]-1,3-dihydro-2H-isoindole-2-carboxamide;
N-[4-(5,6-dihydroimidazo[1,5-a]pyrazin-7(8H)-ylcarbonyl)phenyl]-1,3-dihydro-2H-isoindole-2-carboxamide;
N-(4-{[4-(2-furoyl)piperazin-1-yl]carbonyl}phenyl)-1,3-dihydro-2H-isoindole-2-carboxamide;
N-{4-[(1-benzylpiperidin-4-yl)carbamoyl]phenyl}-1,3-dihydro-2H-isoindole-2-carboxamide;
N-{4-[(4-methoxyphenyl)carbamoyl]phenyl}-1,3-dihydro-2H-isoindole-2-carboxamide;
N-{4-[(3-methoxyphenyl)carbamoyl]phenyl}-1,3-dihydro-2H-isoindole-2-carboxamide;
N-{4-[(5-acetamido-2-methoxyphenyl)carbamoyl]phenyl}-1,3-dihydro-2H-isoindole-2-carboxamide;
N-(4-{[2-(3,5-dimethoxyphenyl)ethyl]carbamoyl}phenyl)-1,3-dihydro-2H-isoindole-2-carboxamide;
N-[4-({2-[3-(trifluoromethyl)phenyl]ethyl}carbamoyl)phenyl]-1,3-dihydro-2H-isoindole-2-carboxamide;
N-{4-[(2-methylbutan-2-yl)carbamoyl]phenyl}-1,3-dihydro-2H-isoindole-2-carboxamide;
N-(4-{[2-(1H-imidazol-4-yl)ethyl]carbamoyl}phenyl)-1,3-dihydro-2H-isoindole-2-carboxamide;
N-(4-{[(2S)-2-hydroxypropyl]carbamoyl}phenyl)-1,3-dihydro-2H-isoindole-2-carboxamide;
N-(4-{[(1R)-1-(3-cyanophenyl)ethyl]carbamoyl}phenyl)-1,3-dihydro-2H-isoindole-2-carboxamide;
N-(4-{[(2S)-1-hydroxy-3-methylbutan-2-yl]carbamoyl}phenyl)-1,3-dihydro-2H-isoindole-2-carboxamide;
N-{4-[benzyl(2-hydroxyethyl)carbamoyl]phenyl}-1,3-dihydro-2H-isoindole-2-carboxamide;
N-{4-[(4-cyanophenyl)carbamoyl]phenyl}-1,3-dihydro-2H-isoindole-2-carboxamide;
N-(4-{[2-(4-chlorophenyl)ethyl]carbamoyl}phenyl)-1,3-dihydro-2H-isoindole-2-carboxamide;
N-(4-{[2-(4-methylpiperazin-1-yl)ethyl]carbamoyl}phenyl)-1,3-dihydro-2H-isoindole-2-carboxamide;
N-(4-{[2-(pyridin-2-yl)ethyl]carbamoyl}phenyl)-1,3-dihydro-2H-isoindole-2-carboxamide;
N-{4-[(cyanomethyl)carbamoyl]phenyl}-1,3-dihydro-2H-isoindole-2-carboxamide;
N-[4-(cyclohexylcarbamoyl)phenyl]-1,3-dihydro-2H-isoindole-2-carboxamide;
N-{4-[(3-hydroxyphenyl)carbamoyl]phenyl}-1,3-dihydro-2H-isoindole-2-carboxamide;
N-{4-[butyl(methyl)carbamoyl]phenyl}-1,3-dihydro-2H-isoindole-2-carboxamide;
N-(4-{[4-(dimethylamino)phenyl]carbamoyl}phenyl)-1,3-dihydro-2H-isoindole-2-carboxamide;
N-[4-(3,4-dihydroisoquinolin-2(1H)-ylcarbonyl)phenyl]-1,3-dihydro-2H-isoindole-2-carboxamide;
N-[4-(1,3-dihydro-2H-isoindol-2-ylcarbonyl)phenyl]-1,3-dihydro-2H-isoindole-2-carboxamide;
N-[4-(2,3-dihydro-1H-indol-1-ylcarbonyl)phenyl]-1,3-dihydro-2H-isoindole-2-carboxamide;
N-[4-(phenylcarbamoyl)phenyl]-1,3-dihydro-2H-isoindole-2-carboxamide;
N-{4-[(4-fluorophenyl)carbamoyl]phenyl}-1,3-dihydro-2H-isoindole-2-carboxamide;
N-(4-{[2-(diethylamino)ethyl]carbamoyl}phenyl)-1,3-dihydro-2H-isoindole-2-carboxamide;
N-{4-[(2-hydroxy-2-phenylethyl)(methyl)carbamoyl]phenyl}-1,3-dihydro-2H-isoindole-2-carboxamide;
N-{4-[(2-aminophenyl)carbamoyl]phenyl}-1,3-dihydro-2H-isoindole-2-carboxamide;
N-(4-{[(2R)-2-hydroxypropyl]carbamoyl}phenyl)-1,3-dihydro-2H-isoindole-2-carboxamide;
N-(4-{[(2S)-1-amino-4-methyl-1-oxopentan-2-yl]carbamoyl}phenyl)-1,3-dihydro-2H-isoindole-2-carboxamide;
tert-butyl (1-{4-[(1,3-dihydro-2H-isoindol-2-ylcarbonyl)amino]benzoyl}piperidin-4-yl)carbamate;
N-(4-{[3-(morpholin-4-yl)propyl]carbamoyl}phenyl)-1,3-dihydro-2H-isoindole-2-carboxamide;
N-[4-({4-[3-chloro-5-(trifluoromethyl)pyridin-2-yl]piperazin-1-yl}carbonyl)phenyl]-1,3-dihydro-2H-isoindole-2-carboxamide;
N-(4-{[4-(cyclohexylmethyl)piperazin-1-yl]carbonyl}phenyl)-1,3-dihydro-2H-isoindole-2-carboxamide;
N-(4-{[1-(3-chlorobenzyl)-1H-pyrazol-4-yl]carbamoyl}phenyl)-1,3-dihydro-2H-isoindole-2-carboxamide;
N-(4-{[3-(diethylcarbamoyl)piperidin-1-yl]carbonyl}phenyl)-1,3-dihydro-2H-isoindole-2-carboxamide;
N-(4-{[3-(piperidin-1-yl)propyl]carbamoyl}phenyl)-1,3-dihydro-2H-isoindole-2-carboxamide;
N-(4-{[4-(2-hydroxyethyl)piperazin-1-yl]carbonyl}phenyl)-1,3-dihydro-2H-isoindole-2-carboxamide;
N-{4-[(2-hydroxy-6-methylphenyl)carbamoyl]phenyl}-1,3-dihydro-2H-isoindole-2-carboxamide;
N-(4-{[4-(dimethylamino)butyl]carbamoyl}phenyl)-1,3-dihydro-2H-isoindole-2-carboxamide;
N-{4-[(3-hydroxypropyl)carbamoyl]phenyl}-1,3-dihydro-2H-isoindole-2-carboxamide;
N-{4-[(4-cyclohexylpiperazin-1-yl)carbonyl]phenyl}-1,3-dihydro-2H-isoindole-2-carboxamide;
N-[4-(5,6-dihydro[1,2,4]triazolo[4,3-a]pyrazin-7(8H)-ylcarbonyl)phenyl]-1,3-dihydro-2H-isoindole-2-carboxamide;
N-{4-[methyl(3-methylbutyl)carbamoyl]phenyl}-1,3-dihydro-2H-isoindole-2-carboxamide;
N-[4-(propylcarbamoyl)phenyl]-1,3-dihydro-2H-isoindole-2-carboxamide;
N-(4-{[(2S)-1-hydroxybutan-2-yl]carbamoyl}phenyl)-1,3-dihydro-2H-isoindole-2-carboxamide;
N-{4-[(5-fluoropyridin-2-yl)carbamoyl]phenyl}-1,3-dihydro-2H-isoindole-2-carboxamide;
N-{4-[(cyclopropylmethyl)(propyl)carbamoyl]phenyl}-1,3-dihydro-2H-isoindole-2-carboxamide;
N-(4-{[(2S)-1-methoxypropan-2-yl]carbamoyl}phenyl)-1,3-dihydro-2H-isoindole-2-carboxamide;
N-[4-(1,3,4,9-tetrahydro-2H-beta-carbolin-2-ylcarbonyl)phenyl]-1,3-dihydro-2H-isoindole-2-carboxamide;
N-[4-(tert-butylcarbamoyl)phenyl]-1,3-dihydro-2H-isoindole-2-carboxamide;
N-[4-({4-[4-(trifluoromethyl)phenyl]piperazin-1-yl}carbonyl)phenyl]-1,3-dihydro-2H-isoindole-2-carboxamide;

N-{4-[(3-methylbutan-2-yl)carbamoyl]phenyl}-1,3-dihydro-2H-isoindole-2-carboxamide;
N-{4-[(3,3-difluoropyrrolidin-1-yl)carbonyl]phenyl}-1,3-dihydro-2H-isoindole-2-carboxamide;
N-{4-[(2-methylpiperidin-1-yl)carbonyl]phenyl}-1,3-dihydro-2H-isoindole-2-carboxamide;
N-(4-{[(3S)-1-benzylpyrrolidin-3-yl]carbamoyl}phenyl)-1,3-dihydro-2H-isoindole-2-carboxamide;
N-{4-[(4-hydroxypiperidin-1-yl)carbonyl]phenyl}-1,3-dihydro-2H-isoindole-2-carboxamide;
N-{4-[bis(2-methoxyethyl)carbamoyl]phenyl}-1,3-dihydro-2H-isoindole-2-carboxamide;
N-{4-[(3-fluorophenyl)carbamoyl]phenyl}-1,3-dihydro-2H-isoindole-2-carboxamide;
N-[4-(cyclopentylcarbamoyl)phenyl]-1,3-dihydro-2H-isoindole-2-carboxamide;
N-{4-[(4-carbamoylpiperidin-1-yl)carbonyl]phenyl}-1,3-dihydro-2H-isoindole-2-carboxamide;
N-[4-(cyclopropylcarbamoyl)phenyl]-1,3-dihydro-2H-isoindole-2-carboxamide;
N-[4-(methylcarbamoyl)phenyl]-1,3-dihydro-2H-isoindole-2-carboxamide;
N-(4-{[3-(dimethylamino)propyl]carbamoyl}phenyl)-1,3-dihydro-2H-isoindole-2-carboxamide;
N-{4-[methyl(tetrahydrofuran-2-ylmethyl)carbamoyl]phenyl}-1,3-dihydro-2H-isoindole-2-carboxamide;
N-[4-(pentan-2-ylcarbamoyl)phenyl]-1,3-dihydro-2H-isoindole-2-carboxamide;
N-[4-(pentan-3-ylcarbamoyl)phenyl]-1,3-dihydro-2H-isoindole-2-carboxamide;
N-[4-(cyclobutylcarbamoyl)phenyl]-1,3-dihydro-2H-isoindole-2-carboxamide;
N-{4-[(1,3-dioxolan-2-ylmethyl)(methyl)carbamoyl]phenyl}-1,3-dihydro-2H-isoindole-2-carboxamide;
N-(4-{[1-(4-fluorophenyl)-1H-pyrazol-4-yl]carbamoyl}phenyl)-1,3-dihydro-2H-isoindole-2-carboxamide;
N-{4-[(1-hydroxy-2-methylpropan-2-yl)carbamoyl]phenyl}-1,3-dihydro-2H-isoindole-2-carboxamide;
N-{4-[(1-phenyl-1H-pyrazol-4-yl)carbamoyl]phenyl}-1,3-dihydro-2H-isoindole-2-carboxamide;
N-[4-({2-[4-(trifluoromethyl)phenyl]ethyl}carbamoyl)phenyl]-1,3-dihydro-2H-isoindole-2-carboxamide;
N-{4-[(2-methoxyethyl)(propyl)carbamoyl]phenyl}-1,3-dihydro-2H-isoindole-2-carboxamide;
N-[4-(sec-butylcarbamoyl)phenyl]-1,3-dihydro-2H-isoindole-2-carboxamide;
N-(4-{[3-(trifluoromethyl)piperidin-1-yl]carbonyl}phenyl)-1,3-dihydro-2H-isoindole-2-carboxamide;
N-{4-[bis(2-ethoxyethyl)carbamoyl]phenyl}-1,3-dihydro-2H-isoindole-2-carboxamide;
N-{4-[butyl(ethyl)carbamoyl]phenyl}-1,3-dihydro-2H-isoindole-2-carboxamide;
N-{4-[(1-methoxypropan-2-yl)carbamoyl]phenyl}-1,3-dihydro-2H-isoindole-2-carboxamide;
N-{4-[(2-methoxyethyl)(methyl)carbamoyl]phenyl}-1,3-dihydro-2H-isoindole-2-carboxamide;
N-{4-[(3R)-tetrahydrofuran-3-ylcarbamoyl]phenyl}-1,3-dihydro-2H-isoindole-2-carboxamide;
N-{4-(morpholin-4-ylcarbonyl)phenyl]-1,3-dihydro-2H-isoindole-2-carboxamide;
N-{4-[isobutyl(methyl)carbamoyl]phenyl}-1,3-dihydro-2H-isoindole-2-carboxamide;
N-[4-({4-[2-(2-hydroxyethoxy)ethyl]piperazin-1-yl}carbonyl)phenyl]-1,3-dihydro-2H-isoindole-2-carboxamide;
N-{4-[(3-methylpiperidin-1-yl)carbonyl]phenyl}-1,3-dihydro-2H-isoindole-2-carboxamide;
N-(4-carbamoylphenyl)-1,3-dihydro-2H-isoindole-2-carboxamide;
N-(4-{[(2S)-2-(trifluoromethyl)pyrrolidin-1-yl]carbonyl}phenyl)-1,3-dihydro-2H-isoindole-2-carboxamide;
N-(4-{[(2S)-1-hydroxy-4-methylpentan-2-yl]carbamoyl}phenyl)-1,3-dihydro-2H-isoindole-2-carboxamide;
N-(4-{[(1R)-2-hydroxy-1-phenylethyl]carbamoyl}phenyl)-1,3-dihydro-2H-isoindole-2-carboxamide;
N-{4-[(2-methylpyrrolidin-1-yl)carbonyl]phenyl}-1,3-dihydro-2H-isoindole-2-carboxamide;
N-{4-[ethyl(2-methoxyethyl)carbamoyl]phenyl}-1,3-dihydro-2H-isoindole-2-carboxamide;
N-(4-{[(2R)-1-hydroxy-3-methylbutan-2-yl]carbamoyl}phenyl)-1,3-dihydro-2H-isoindole-2-carboxamide;
N-{4-[(2,6-dimethylmorpholin-4-yl)carbonyl]phenyl}-1,3-dihydro-2H-isoindole-2-carboxamide;
N-(4-{[(2R)-1-hydroxybutan-2-yl]carbamoyl}phenyl)-1,3-dihydro-2H-isoindole-2-carboxamide;
N-{4-[(2,5-dimethylpyrrolidin-1-yl)carbonyl]phenyl}-1,3-dihydro-2H-isoindole-2-carboxamide;
N-[4-(prop-2-yn-1-ylcarbamoyl)phenyl]-1,3-dihydro-2H-isoindole-2-carboxamide;
N-{4-[isopropyl(2-methoxyethyl)carbamoyl]phenyl}-1,3-dihydro-2H-isoindole-2-carboxamide;
N-{4-[isopropyl(propyl)carbamoyl]phenyl}-1,3-dihydro-2H-isoindole-2-carboxamide;
N-{4-[(2-cyanoethyl)(cyclopropyl)carbamoyl]phenyl}-1,3-dihydro-2H-isoindole-2-carboxamide;
N-{4-[ethyl(isopropyl)carbamoyl]phenyl}-1,3-dihydro-2H-isoindole-2-carboxamide;
N-{4-[(3-fluoropyrrolidin-1-yl)carbonyl]phenyl}-1,3-dihydro-2H-isoindole-2-carboxamide;
N-{4-[(1,3-dihydro-2H-isoindol-2-ylcarbonyl)amino]benzoyl}-N-isopropyl-beta-alanine;
N-{4-[methyl(propyl)carbamoyl]phenyl}-1,3-dihydro-2H-isoindole-2-carboxamide;
5,6-dimethoxy-N-{4-[(3-phenylpropyl)carbamoyl]phenyl}-1,3-dihydro-2H-isoindole-2-carboxamide;
N-(4-{[3-(4-chlorophenoxy)propyl]carbamoyl}phenyl)-1,3-dihydro-2H-isoindole-2-carboxamide;
N-(4-{[4-(trifluoromethoxy)phenyl]carbamoyl}phenyl)-1,3-dihydro-2H-isoindole-2-carboxamide;
N-{4-[(4-phenyl-1,3-thiazol-2-yl)carbamoyl]phenyl}-1,3-dihydro-2H-isoindole-2-carboxamide;
methyl 2-{[4-(propylcarbamoyl)phenyl]carbamoyl}isoindoline-5-carboxylate;
2-{[4-(propylcarbamoyl)phenyl]carbamoyl}isoindoline-5-carboxylic acid;
5-amino-N-[4-(propylcarbamoyl)phenyl]-1,3-dihydro-2H-isoindole-2-carboxamide;
5-(hydroxymethyl)-N-[4-(propylcarbamoyl)phenyl]-1,3-dihydro-2H-isoindole-2-carboxamide;
5-(aminomethyl)-N-[4-(propylcarbamoyl)phenyl]-1,3-dihydro-2H-isoindole-2-carboxamide;
5-[(2-hydroxy-2-methylpropanoyl)amino]-N-[4-(propylcarbamoyl)phenyl]-1,3-dihydro-2H-isoindole-2-carboxamide;
5-acetamido-N-[4-(propylcarbamoyl)phenyl]-1,3-dihydro-2H-isoindole-2-carboxamide;
5-[(N,N-dimethylglycyl)amino]-N-[4-(propylcarbamoyl)phenyl]-1,3-dihydro-2H-isoindole-2-carboxamide;

N-[4-(propylcarbamoyl)phenyl]-5-(1H-pyrazol-3-yl)-1,3-dihydro-2H-isoindole-2-carboxamide;
N-[4-(propylcarbamoyl)phenyl]-5-(1H-pyrazol-4-yl)-1,3-dihydro-2H-isoindole-2-carboxamide;
5-[(methoxyacetyl)amino]-N-[4-(propylcarbamoyl)phenyl]-1,3-dihydro-2H-isoindole-2-carboxamide;
5-[(methylsulfonyl)amino]-N-[4-(propylcarbamoyl)phenyl]-1,3-dihydro-2H-isoindole-2-carboxamide;
5-bromo-N-[4-(propylcarbamoyl)phenyl]-1,3-dihydro-2H-isoindole-2-carboxamide;
N-{4-[(3,5-dimethoxybenzyl)carbamoyl]phenyl}-1,3-dihydro-2H-pyrrolo[3,4-c]pyridine-2-carboxamide;
N-{4-[(4-chlorobenzyl)carbamoyl]phenyl}-1,3-dihydro-2H-pyrrolo[3,4-c]pyridine-2-carboxamide;
N-(4-{[4-(pyridin-2-yl)piperazin-1-yl]carbonyl}phenyl)-1,3-dihydro-2H-pyrrolo[3,4-c]pyridine-2-carboxamide;
N-{4-[(3-phenylpropyl)carbamoyl]phenyl}-1,3-dihydro-2H-pyrrolo[3,4-c]pyridine-2-carboxamide;
N-{4-[(tetrahydrofuran-3-ylmethyl)carbamoyl]phenyl}-1,3-dihydro-2H-pyrrolo[3,4-c]pyridine-2-carboxamide;
N-{4-[(3-methylbutyl)carbamoyl]phenyl}-1,3-dihydro-2H-pyrrolo[3,4-c]pyridine-2-carboxamide;
N-{4-[(4,4,4-trifluorobutanoyl)amino]phenyl}-1,3-dihydro-2H-isoindole-2-carboxamide;
N-{4-[(3-ethoxypropanoyl)amino]phenyl}-1,3-dihydro-2H-isoindole-2-carboxamide;
N-{4-[(4-phenylbutanoyl)amino]phenyl}-1,3-dihydro-2H-isoindole-2-carboxamide;
N-{4-[(4-methylpentanoyl)amino]phenyl}-1,3-dihydro-2H-isoindole-2-carboxamide;
N-(4-{[(benzyloxy)acetyl]amino}phenyl)-1,3-dihydro-2H-isoindole-2-carboxamide;
N-{4-[(3-phenylpropanoyl)amino]phenyl}-1,3-dihydro-2H-isoindole-2-carboxamide;
N-{4-[(3-phenoxypropanoyl)amino]phenyl}-1,3-dihydro-2H-isoindole-2-carboxamide;
N-(4-{[N-(2-furoyl)glycyl]amino}phenyl)-1,3-dihydro-2H-isoindole-2-carboxamide;
N-(4-{[4-(2-thienyl)butanoyl]amino}phenyl)-1,3-dihydro-2H-isoindole-2-carboxamide;
N-{4-[(4-oxo-4-phenylbutanoyl)amino]phenyl}-1,3-dihydro-2H-isoindole-2-carboxamide;
N-{4-[(N-benzoylglycyl)amino]phenyl}-1,3-dihydro-2H-isoindole-2-carboxamide;
N-{4-[(4-phenoxybutanoyl)amino]phenyl}-1,3-dihydro-2H-isoindole-2-carboxamide;
N-[4-(propionylamino)phenyl]-1,3-dihydro-2H-isoindole-2-carboxamide;
N-[4-(pentanoylamino)phenyl]-1,3-dihydro-2H-isoindole-2-carboxamide;
N-[4-(hexanoylamino)phenyl]-1,3-dihydro-2H-isoindole-2-carboxamide;
N-[4-(heptanoylamino)phenyl]-1,3-dihydro-2H-isoindole-2-carboxamide;
N-[4-(pent-4-enoylamino)phenyl]-1,3-dihydro-2H-isoindole-2-carboxamide;
N-{4-[(ethoxyacetyl)amino]phenyl}-1,3-dihydro-2H-isoindole-2-carboxamide;
N-(4-{[(2-methoxyethoxy)acetyl]amino}phenyl)-1,3-dihydro-2H-isoindole-2-carboxamide;
N-{4-[(cyclopropylacetyl)amino]phenyl}-1,3-dihydro-2H-isoindole-2-carboxamide;
N-{4-[(cyclopentylacetyl)amino]phenyl}-1,3-dihydro-2H-isoindole-2-carboxamide;
N-(4-{[3-(4-methylpiperazin-1-yl)propanoyl]amino}phenyl)-1,3-dihydro-2H-isoindole-2-carboxamide;
methyl 2-({4-[(cyclopentylacetyl)amino]phenyl}carbamoyl)isoindoline-5-carboxylate;
2-({4-[(cyclopentylacetyl)amino]phenyl}carbamoyl)isoindoline-5-carboxylic acid;
N-{4-[(cyclopentylacetyl)amino]phenyl}-5-(hydroxymethyl)-1,3-dihydro-2H-isoindole-2-carboxamide;
N-{4-[(2-cyclopentylethyl)amino]phenyl}-5-(hydroxymethyl)-1,3-dihydro-2H-isoindole-2-carboxamide;
tert-butyl 4-{4-[(1,3-dihydro-2H-isoindol-2-ylcarbonyl)amino]phenyl}-3,6-dihydropyridine-1(2H)-carboxylate;
N-[4-(1,2,3,6-tetrahydropyridin-4-yl)phenyl]-1,3-dihydro-2H-isoindole-2-carboxamide;
N-{4-[1-(3-methylbutyl)-1H-pyrazol-4-yl]phenyl}-1,3-dihydro-2H-isoindole-2-carboxamide;
N-[4-(1-methyl-1H-pyrazol-4-yl)phenyl]-1,3-dihydro-2H-isoindole-2-carboxamide;
N-{4-[(1E)-5-phenylpent-1-en-1-yl]phenyl}-1,3-dihydro-2H-isoindole-2-carboxamide;
N-[4-(1-propyl-1H-pyrazol-4-yl)phenyl]-1,3-dihydro-2H-isoindole-2-carboxamide;
N-[4-(1-benzyl-1H-pyrazol-4-yl)phenyl]-1,3-dihydro-2H-isoindole-2-carboxamide;
N-{4-[1-(2-hydroxyethyl)-1H-pyrazol-4-yl]phenyl}-1,3-dihydro-2H-isoindole-2-carboxamide;
N-[6-(1-propyl-1H-pyrazol-4-yl)pyridin-3-yl]-1,3-dihydro-2H-isoindole-2-carboxamide;
N-{6-[1-(3-methylbutyl)-1H-pyrazol-4-yl]pyridin-3-yl}-1,3-dihydro-2H-isoindole-2-carboxamide;
N-[4-(5-phenylpentyl)phenyl]-1,3-dihydro-2H-isoindole-2-carboxamide;
N-[2-fluoro-4-(1-propyl-1H-pyrazol-4-yl)phenyl]-1,3-dihydro-2H-isoindole-2-carboxamide;
N-{2-fluoro-4-[1-(3-methylbutyl)-1H-pyrazol-4-yl]phenyl}-1,3-dihydro-2H-isoindole-2-carboxamide;
N-[4-(1-butyryl-1,2,3,6-tetrahydropyridin-4-yl)phenyl]-1,3-dihydro-2H-isoindole-2-carboxamide;
N-[4-(1-isobutyryl-1,2,3,6-tetrahydropyridin-4-yl)phenyl]-1,3-dihydro-2H-isoindole-2-carboxamide;
N-[4-(1-benzoyl-1,2,3,6-tetrahydropyridin-4-yl)phenyl]-1,3-dihydro-2H-isoindole-2-carboxamide;
N-{4-[1-(isopropylsulfonyl)-1,2,3,6-tetrahydropyridin-4-yl]phenyl}-1,3-dihydro-2H-isoindole-2-carboxamide;
N-(1'-isobutyryl-1',2',3',6'-tetrahydro-2,4'-bipyridin-5-yl)-1,3-dihydro-2H-isoindole-2-carboxamide;
N-(1'-benzoyl-1',2',3',6'-tetrahydro-2,4'-bipyridin-5-yl)-1,3-dihydro-2H-isoindole-2-carboxamide;
N-[4-(4-benzoylpiperazin-1-yl)phenyl]-1,3-dihydro-2H-isoindole-2-carboxamide;
N-{4-[4-(isopropylsulfonyl)piperazin-1-yl]phenyl}-1,3-dihydro-2H-isoindole-2-carboxamide;
N-{4-[4-(phenylsulfonyl)piperazin-1-yl]phenyl}-1,3-dihydro-2H-isoindole-2-carboxamide;
N-{4-[3-(benzoylamino)pyrrolidin-1-yl]phenyl}-1,3-dihydro-2H-isoindole-2-carboxamide;
N-{4-[3-(butyrylamino)pyrrolidin-1-yl]phenyl}-1,3-dihydro-2H-isoindole-2-carboxamide;
tert-butyl 4-{4-[(1,3-dihydro-2H-isoindol-2-ylcarbonyl)amino]phenyl}piperazine-1-carboxylate;
N-[4-(4-propionylpiperazin-1-yl)phenyl]-1,3-dihydro-2H-isoindole-2-carboxamide;
N-{4-[4-(cyclopropylcarbonyl)piperazin-1-yl]phenyl}-1,3-dihydro-2H-isoindole-2-carboxamide;
N-(2-butyryl-2,3-dihydro-1H-isoindol-5-yl)-1,3-dihydro-2H-isoindole-2-carboxamide;
N-(2-isobutyryl-2,3-dihydro-1H-isoindol-5-yl)-1,3-dihydro-2H-isoindole-2-carboxamide;

N-(2-benzoyl-2,3-dihydro-1H-isoindol-5-yl)-1,3-dihydro-2H-isoindole-2-carboxamide;
N-[2-(3-methylbutyl)-2,3-dihydro-1H-isoindol-5-yl]-1,3-dihydro-2H-isoindole-2-carboxamide;
N-[4-(hexyloxy)phenyl]-1,3-dihydro-2H-isoindole-2-carboxamide;
N-[4-(1-benzoylpiperidin-4-yl)butyl]-1,3-dihydro-2H-isoindole-2-carboxamide;
N-{4-[1-(pyridin-3-ylcarbonyl)piperidin-4-yl]butyl}-1,3-dihydro-2H-isoindole-2-carboxamide;
N-[6-(4-chlorophenoxy)hexyl]-1,3-dihydro-2H-isoindole-2-carboxamide;
N-[4-(piperidin-4-yl)butyl]-1,3-dihydro-2H-isoindole-2-carboxamide;
N,N'-hexane-1,6-diylbis(1,3-dihydro-2H-isoindole-2-carboxamide);
N-(4-phenylbutyl)-1,3-dihydro-2H-isoindole-2-carboxamide;
ethyl 6-[(1,3-dihydro-2H-isoindol-2-ylcarbonyl)amino]hexanoate;
N-hexyl-1,3-dihydro-2H-isoindole-2-carboxamide;
N-octyl-1,3-dihydro-2H-isoindole-2-carboxamide;
N-{6-[(1-methyl-1H-pyrazol-4-yl)amino]-6-oxohexyl}-1,3-dihydro-2H-isoindole-2-carboxamide;
N-[6-(methylamino)-6-oxohexyl]-1,3-dihydro-2H-isoindole-2-carboxamide;
N-{6-oxo-6-[(3-phenylpropyl)amino]hexyl}-1,3-dihydro-2H-isoindole-2-carboxamide;
N-{6-[(3-methylbutyl)amino]-6-oxohexyl}-1,3-dihydro-2H-isoindole-2-carboxamide;
N-(5-{[4-(pyridin-2-yl)piperazin-1-yl]carbonyl}pyridin-2-yl)-1,3-dihydro-2H-isoindole-2-carboxamide;
N-{5-[(3-phenylpropyl)carbamoyl]pyridin-2-yl}-1,3-dihydro-2H-isoindole-2-carboxamide;
N-{5-[(3-methylbutyl)carbamoyl]pyridin-2-yl}-1,3-dihydro-2H-isoindole-2-carboxamide;
N-{5-[(3-phenylpropyl)carbamoyl]-1,3-thiazol-2-yl}-1,3-dihydro-2H-isoindole-2-carboxamide;
N-{5-[(3-methylbutyl)carbamoyl]-1,3-thiazol-2-yl}-1,3-dihydro-2H-isoindole-2-carboxamide;
5-fluoro-N-[4-(propylcarbamoyl)phenyl]-1,3-dihydro-2H-isoindole-2-carboxamide;
N-[4-(4-oxo-3,4-dihydrophthalazin-1-yl)phenyl]-1,3-dihydro-2H-isoindole-2-carboxamide;
N-[4-(isoquinolin-4-yl)phenyl]-1,3-dihydro-2H-isoindole-2-carboxamide;
N-[4-(1-oxo-1,2-dihydroisoquinolin-4-yl)phenyl]-1,3-dihydro-2H-isoindole-2-carboxamide;
N-[4-(4-oxo-3,4,5,6,7,8-hexahydrophthalazin-1-yl)phenyl]-1,3-dihydro-2H-isoindole-2-carboxamide;
N-[4-(8-fluoro-4-oxo-3,4-dihydrophthalazin-1-yl)phenyl]-1,3-dihydro-2H-isoindole-2-carboxamide;
5-fluoro-N-[4-(4-oxo-3,4-dihydrophthalazin-1-yl)phenyl]-1,3-dihydro-2H-isoindole-2-carboxamide;
N-[4-(4-oxo-3,4-dihydrophthalazin-1-yl)phenyl]-5-(pyrrolidin-1-ylmethyl)-1,3-dihydro-2H-isoindole-2-carboxamide;
5-(morpholin-4-ylmethyl)-N-[4-(1-oxo-1,2-dihydroisoquinolin-4-yl)phenyl]-1,3-dihydro-2H-isoindole-2-carboxamide;
5-methoxy-N-[4-(1-oxo-1,2-dihydroisoquinolin-4-yl)phenyl]-1,3-dihydro-2H-isoindole-2-carboxamide;
5-[(4-methylpiperazin-1-yl)methyl]-N-[4-(4-oxo-3,4-dihydrophthalazin-1-yl)phenyl]-1,3-dihydro-2H-isoindole-2-carboxamide;
5-cyano-N-[4-(1-oxo-1,2-dihydroisoquinolin-4-yl)phenyl]-1,3-dihydro-2H-isoindole-2-carboxamide;
5-chloro-N-[4-(1-oxo-1,2-dihydroisoquinolin-4-yl)phenyl]-1,3-dihydro-2H-isoindole-2-carboxamide;
N-[4-(4-oxo-4,5-dihydro-3H-2,3-benzodiazepin-1-yl)phenyl]-1,3-dihydro-2H-isoindole-2-carboxamide;
N-[4-(1-oxo-1,2-dihydroisoquinolin-4-yl)phenyl]-5-(pyrrolidin-1-ylmethyl)-1,3-dihydro-2H-isoindole-2-carboxamide;
N-{4-[4-oxo-8-(trifluoromethyl)-3,4-dihydrophthalazin-1-yl]phenyl}-1,3-dihydro-2H-isoindole-2-carboxamide;
5-[(dimethylamino)methyl]-N-[4-(1-oxo-1,2-dihydroisoquinolin-4-yl)phenyl]-1,3-dihydro-2H-isoindole-2-carboxamide;
5-[(diethylamino)methyl]-N-[4-(1-oxo-1,2-dihydroisoquinolin-4-yl)phenyl]-1,3-dihydro-2H-isoindole-2-carboxamide;
5-[(4-methylpiperazin-1-yl)methyl]-N-[4-(1-oxo-1,2-dihydroisoquinolin-4-yl)phenyl]-1,3-dihydro-2H-isoindole-2-carboxamide;
5-[(dimethylamino)methyl]-N-[4-(4-oxo-3,4-dihydrophthalazin-1-yl)phenyl]-1,3-dihydro-2H-isoindole-2-carboxamide;
5-[(diethylamino)methyl]-N-[4-(4-oxo-3,4-dihydrophthalazin-1-yl)phenyl]-1,3-dihydro-2H-isoindole-2-carboxamide;
N-{4-[4-oxo-8-(trifluoromethyl)-3,4-dihydrophthalazin-1-yl]phenyl}-5-(pyrrolidin-1-ylmethyl)-1,3-dihydro-2H-isoindole-2-carboxamide;
5-[(1-methylpiperidin-4-yl)oxy]-N-[4-(4-oxo-3,4-dihydrophthalazin-1-yl)phenyl]-1,3-dihydro-2H-isoindole-2-carboxamide;
5-{[(3R)-3-fluoropyrrolidin-1-yl]methyl}-N-[4-(4-oxo-3,4-dihydrophthalazin-1-yl)phenyl]-1,3-dihydro-2H-isoindole-2-carboxamide;
5-{[(3S)-3-fluoropyrrolidin-1-yl]methyl}-N-[4-(4-oxo-3,4-dihydrophthalazin-1-yl)phenyl]-1,3-dihydro-2H-isoindole-2-carboxamide;
5-(azetidin-1-ylmethyl)-N-[4-(4-oxo-3,4-dihydrophthalazin-1-yl)phenyl]-1,3-dihydro-2H-isoindole-2-carboxamide;
N-[4-(1-oxo-1,2-dihydropyrrolo[1,2-d][1,2,4]triazin-4-yl)phenyl]-1,3-dihydro-2H-isoindole-2-carboxamide;
N-[4-(1-oxo-1,2-dihydropyrrolo[1,2-d][1,2,4]triazin-4-yl)phenyl]-5-(pyrrolidin-1-ylmethyl)-1,3-dihydro-2H-isoindole-2-carboxamide;
tert-butyl 4-{4-[(1,3-dihydro-2H-isoindol-2-ylcarbonyl)amino]phenyl}piperidine-1-carboxylate;
N-[4-(5-propyl-1,2,4-oxadiazol-3-yl)phenyl]-1,3-dihydro-2H-isoindole-2-carboxamide;
N-[4-(piperidin-4-yl)phenyl]-1,3-dihydro-2H-isoindole-2-carboxamide;
N-{5-[(tetrahydrofuran-3-ylmethyl)carbamoyl]pyridin-2-yl}-1,3-dihydro-2H-isoindole-2-carboxamide;
N-[4-(1-butyrylpiperidin-4-yl)phenyl]-1,3-dihydro-2H-isoindole-2-carboxamide;
N-[4-(1-isobutyrylpiperidin-4-yl)phenyl]-1,3-dihydro-2H-isoindole-2-carboxamide;
N-[4-(1-benzoylpiperidin-4-yl)phenyl]-1,3-dihydro-2H-isoindole-2-carboxamide;
N-{4-[5-(3-methylbutyl)-1,2,4-oxadiazol-3-yl]phenyl}-1,3-dihydro-2H-isoindole-2-carboxamide;
N-[4-(5-benzyl-1,2,4-oxadiazol-3-yl)phenyl]-1,3-dihydro-2H-isoindole-2-carboxamide;
N-(4-{[(3R)-tetrahydrofuran-3-ylmethyl]carbamoyl}phenyl)-1,3-dihydro-2H-isoindole-2-carboxamide;

N-(4-{[(3S)-tetrahydrofuran-3-ylmethyl]carbamoyl}phenyl)-1,3-dihydro-2H-isoindole-2-carboxamide;
N-{4-[(2-methoxyethyl)carbamoyl]phenyl}-1,3-dihydro-2H-isoindole-2-carboxamide;
N-{4-[(5-chloropyridin-2-yl)carbamoyl]phenyl}-1,3-dihydro-2H-isoindole-2-carboxamide;
N-{4-[(3-hydroxy-4-methoxyphenyl)carbamoyl]phenyl}-1,3-dihydro-2H-isoindole-2-carboxamide;
N-{4-[(2,4-dimethoxybenzyl)carbamoyl]phenyl}-1,3-dihydro-2H-isoindole-2-carboxamide;
N-(4-{[4-(2-oxopyrrolidin-1-yl)benzyl]carbamoyl}phenyl)-1,3-dihydro-2H-isoindole-2-carboxamide;
N-(4-{[(1S,2S)-2-hydroxy-2,3-dihydro-1H-inden-1-yl]carbamoyl}phenyl)-1,3-dihydro-2H-isoindole-2-carboxamide;
N-(4-{[(1-hydroxycyclopropyl)methyl]carbamoyl}phenyl)-1,3-dihydro-2H-isoindole-2-carboxamide;
N-{4-[(tetrahydro-2H-pyran-2-ylmethyl)carbamoyl]phenyl}-1,3-dihydro-2H-isoindole-2-carboxamide;
N-{4-[(tetrahydro-2H-pyran-3-ylmethyl)carbamoyl]phenyl}-1,3-dihydro-2H-isoindole-2-carboxamide;
N-{4-[(tetrahydro-2H-pyran-4-ylmethyl)carbamoyl]phenyl}-1,3-dihydro-2H-isoindole-2-carboxamide;
tert-butyl 4-{6-[(1,3-dihydro-2H-isoindol-2-ylcarbonyl)amino]-1H-benzimidazol-2-yl}piperazine-1-carboxylate;
N-[2-(piperazin-1-yl)-1H-benzimidazol-6-yl]-1,3-dihydro-2H-isoindole-2-carboxamide;
N-[4-(propylcarbamoyl)phenyl]-5-vinyl-1,3-dihydro-2H-isoindole-2-carboxamide;
N-{4-[(4-benzoylpiperazin-1-yl)carbonyl]phenyl}-1,3-dihydro-2H-isoindole-2-carboxamide;
N-(4-{[(2S)-tetrahydrofuran-2-ylmethyl]carbamoyl}phenyl)-1,3-dihydro-2H-pyrrolo[3,4-c]pyridine-2-carboxamide;
N-(4-{[(2R)-tetrahydrofuran-2-ylmethyl]carbamoyl}phenyl)-1,3-dihydro-2H-pyrrolo[3,4-c]pyridine-2-carboxamide;
N-{4-[5-(tetrahydrofuran-3-yl)-1,2,4-oxadiazol-3-yl]phenyl}-1,3-dihydro-2H-isoindole-2-carboxamide;
N-[4-(1-isobutyl-1,2,3,6-tetrahydropyridin-4-yl)phenyl]-1,3-dihydro-2H-isoindole-2-carboxamide;
N-(4-{[(3-methylbutyl)amino]carbonyl}phenyl)-5,7-dihydro-6H-pyrrolo[3,4-d]pyrimidine-6-carboxamide;
N-(4-{[(3-phenylpropyl)amino]carbonyl}phenyl)-5,7-dihydro-6H-pyrrolo[3,4-d]pyrimidine-6-carboxamide;
N-{4-[1-(4-methylbenzoyl)-1,2,3,6-tetrahydropyridin-4-yl]phenyl}-1,3-dihydro-2H-isoindole-2-carboxamide;
N-[4-(1-benzyl-1,2,3,6-tetrahydropyridin-4-yl)phenyl]-1,3-dihydro-2H-isoindole-2-carboxamide;
N-(4-{[4-(tetrahydrofuran-3-ylmethyl)piperazin-1-yl]carbonyl}phenyl)-1,3-dihydro-2H-isoindole-2-carboxamide;
5-fluoro-N-[4-({[(2S)-tetrahydrofuran-2-ylmethyl]amino}carbonyl)phenyl]-1,3-dihydro-2H-isoindole-2-carboxamide;
5-fluoro-N-[4-({[(2R)-tetrahydrofuran-2-ylmethyl]amino}carbonyl)phenyl]-1,3-dihydro-2H-isoindole-2-carboxamide;
N-[4-({[(1S)-2-hydroxy-1-phenylethyl]amino}carbonyl)phenyl]-1,3-dihydro-2H-pyrrolo[3,4-c]pyridine-2-carboxamide;
N-(4-{[4-(2-methoxyethyl)piperazin-1-yl]carbonyl}phenyl)-1,3-dihydro-2H-isoindole-2-carboxamide;
N-(4-{[(2S)-2-(2-hydroxyethyl)piperidin-1-yl]carbonyl}phenyl)-1,3-dihydro-2H-isoindole-2-carboxamide;
N-{4-[(propylamino)carbonyl]phenyl}-5-pyridin-3-yl-1,3-dihydro-2H-isoindole-2-carboxamide;
N-{4-[(propylamino)carbonyl]phenyl}-5-pyridin-4-yl-1,3-dihydro-2H-isoindole-2-carboxamide;
$N^5$-(2-methoxyethyl)-$N^2$-{4-[(propylamino)carbonyl]phenyl}-1,3-dihydro-2H-isoindole-2,5-dicarboxamide;
N-(4-cyanophenyl)-1,3-dihydro-2H-isoindole-2-carboxamide;
N-[4-(trifluoromethyl)phenyl]-1,3-dihydro-2H-isoindole-2-carboxamide;
N-[4-({[(1S)-2-hydroxy-1-pyridin-2-ylethyl]amino}carbonyl)phenyl]-1,3-dihydro-2H-pyrrolo[3,4-c]pyridine-2-carboxamide;
N-(4-{[(3-methylbutyl)amino]carbonyl}phenyl)-5,7-dihydro-6H-pyrrolo[3,4-b]pyridine-6-carboxamide;
N-(4-{[(tetrahydrofuran-3-ylmethyl)amino]carbonyl}phenyl)-5,7-dihydro-6H-pyrrolo[3,4-b]pyridine-6-carboxamide;
N-{4-[(4-pyridin-2-ylpiperazin-1-yl)carbonyl]phenyl}-5,7-dihydro-6H-pyrrolo[3,4-b]pyridine-6-carboxamide;
N-[4-({[(1S)-2-hydroxy-1-pyridin-2-ylethyl]amino}carbonyl)phenyl]-1,3-dihydro-2H-isoindole-2-carboxamide;
5-(1,2-dihydroxyethyl)-N-{4-[(propylamino)carbonyl]phenyl}-1,3-dihydro-2H-isoindole-2-carboxamide;
N-[4-(1-benzoylpiperidin-4-yl)butyl]-5-cyano-1,3-dihydro-2H-isoindole-2-carboxamide;
N-(1'-butyryl-1',2',3',6'-tetrahydro-3,4'-bipyridin-6-yl)-1,3-dihydro-2H-isoindole-2-carboxamide;
N-(1'-isobutyryl-1',2',3',6'-tetrahydro-3,4'-bipyridin-6-yl)-1,3-dihydro-2H-isoindole-2-carboxamide;
N-[1'-(tetrahydrofuran-3-ylcarbonyl)-1',2',3',6'-tetrahydro-3,4'-bipyridin-6-yl]-1,3-dihydro-2H-isoindole-2-carboxamide; and
N-[2-(4-acetylpiperazin-1-yl)-1H-benzimidazol-5-yl]-1,3-dihydro-2H-isoindole-2-carboxamide;
N-{4-[1-(5-oxo-L-prolyl)-1,2,3,6-tetrahydropyridin-4-yl]phenyl}-1,3-dihydro-2H-isoindole-2-carboxamide;
N-{4-[1-(5-oxo-D-prolyl)-1,2,3,6-tetrahydropyridin-4-yl]phenyl}-1,3-dihydro-2H-isoindole-2-carboxamide;
N-[4-(1-propionyl-1,2,3,6-tetrahydropyridin-4-yl)phenyl]-1,3-dihydro-2H-isoindole-2-carboxamide;
N-{4-[1-(2-methylbutanoyl)-1,2,3,6-tetrahydropyridin-4-yl]phenyl}-1,3-dihydro-2H-isoindole-2-carboxamide;
N-{4-[1-(2-ethylbutanoyl)-1,2,3,6-tetrahydropyridin-4-yl]phenyl}-1,3-dihydro-2H-isoindole-2-carboxamide;
N-{4-[1-(methoxyacetyl)-1,2,3,6-tetrahydropyridin-4-yl]phenyl}-1,3-dihydro-2H-isoindole-2-carboxamide;
N-{4-[1-(ethoxyacetyl)-1,2,3,6-tetrahydropyridin-4-yl]phenyl}-1,3-dihydro-2H-isoindole-2-carboxamide;
N-(4-{1-[(2-methoxyethoxy)acetyl]-1,2,3,6-tetrahydropyridin-4-yl}phenyl)-1,3-dihydro-2H-isoindole-2-carboxamide;
N-{4-[1-(tetrahydrofuran-2-ylcarbonyl)-1,2,3,6-tetrahydropyridin-4-yl]phenyl}-1,3-dihydro-2H-isoindole-2-carboxamide;
N-{4-[1-(tetrahydrofuran-3-ylcarbonyl)-1,2,3,6-tetrahydropyridin-4-yl]phenyl}-1,3-dihydro-2H-isoindole-2-carboxamide;
N-{4-[1-(cyclopropylacetyl)-1,2,3,6-tetrahydropyridin-4-yl]phenyl}-1,3-dihydro-2H-isoindole-2-carboxamide;
N-{4-[1-(cyclopentylcarbonyl)-1,2,3,6-tetrahydropyridin-4-yl]phenyl}-1,3-dihydro-2H-isoindole-2-carboxamide;

N-{4-[1-(2-methylbenzoyl)-1,2,3,6-tetrahydropyridin-4-yl]
phenyl}-1,3-dihydro-2H-isoindole-2-carboxamide;
N-{4-[1-(3-methylbenzoyl)-1,2,3,6-tetrahydropyridin-4-yl]
phenyl}-1,3-dihydro-2H-isoindole-2-carboxamide;
N-{4-[1-(2-methoxybenzoyl)-1,2,3,6-tetrahydropyridin-4-yl]phenyl}-1,3-dihydro-2H-isoindole-2-carboxamide;
N-{4-[1-(3-methoxybenzoyl)-1,2,3,6-tetrahydropyridin-4-yl]phenyl}-1,3-dihydro-2H-isoindole-2-carboxamide;
N-{4-[1-(4-methoxybenzoyl)-1,2,3,6-tetrahydropyridin-4-yl]phenyl}-1,3-dihydro-2H-isoindole-2-carboxamide;
N-{4-[1-(2-fluorobenzoyl)-1,2,3,6-tetrahydropyridin-4-yl]
phenyl}-1,3-dihydro-2H-isoindole-2-carboxamide;
N-{4-[1-(3-fluorobenzoyl)-1,2,3,6-tetrahydropyridin-4-yl]
phenyl}-1,3-dihydro-2H-isoindole-2-carboxamide;
N-{4-[1-(4-fluorobenzoyl)-1,2,3,6-tetrahydropyridin-4-yl]
phenyl}-1,3-dihydro-2H-isoindole-2-carboxamide;
N-{4-[1-(4-chlorobenzoyl)-1,2,3,6-tetrahydropyridin-4-yl]
phenyl}-1,3-dihydro-2H-isoindole-2-carboxamide;
N-(4-{1-[3-(dimethylamino)benzoyl]-1,2,3,6-tetrahydropyridin-4-yl}phenyl)-1,3-dihydro-2H-isoindole-2-carboxamide;
N-(4-{1-[4-(dimethylamino)benzoyl]-1,2,3,6-tetrahydropyridin-4-yl}phenyl)-1,3-dihydro-2H-isoindole-2-carboxamide;
N-{4-[1(3-furoyl)-1,2,3,6-tetrahydropyridin-4-yl]phenyl}-1,3-dihydro-2H-isoindole-2-carboxamide;
N-{4-[1-(3-thienylcarbonyl)-1,2,3,6-tetrahydropyridin-4-yl]phenyl}-1,3-dihydro-2H-isoindole-2-carboxamide;
N-{4-[1-(1H-pyrrol-2-ylcarbonyl)-1,2,3,6-tetrahydropyridin-4-yl]phenyl}-1,3-dihydro-2H-isoindole-2-carboxamide;
N-(4-{1-[(2,5-dimethyl-1H-pyrrol-3-yl)carbonyl]-1,2,3,6-tetrahydropyridin-4-yl}phenyl)-1,3-dihydro-2H-isoindole-2-carboxamide;
N-{4-[1-(1,3-thiazol-4-ylcarbonyl)-1,2,3,6-tetrahydropyridin-4-yl]phenyl}-1,3-dihydro-2H-isoindole-2-carboxamide;
N-{4-[1-(1H-pyrazol-4-ylcarbonyl)-1,2,3,6-tetrahydropyridin-4-yl]phenyl}-1,3-dihydro-2H-isoindole-2-carboxamide;
N-(4-{1-[(3,5-dimethyl-1,2-oxazol-4-yl)carbonyl]-1,2,3,6-tetrahydropyridin-4-yl}phenyl)-1,3-dihydro-2H-isoindole-2-carboxamide;
N-{4-[1-(pyridin-2-ylcarbonyl)-1,2,3,6-tetrahydropyridin-4-yl]phenyl}-1,3-dihydro-2H-isoindole-2-carboxamide;
N-{4-[1-(pyridin-3-ylcarbonyl)-1,2,3,6-tetrahydropyridin-4-yl]phenyl}-1,3-dihydro-2H-isoindole-2-carboxamide;
N-[4-(1-isonicotinoyl-1,2,3,6-tetrahydropyridin-4-yl)phenyl]-1,3-dihydro-2H-isoindole-2-carboxamide;
N-{4-[1-(pyridazin-3-ylcarbonyl)-1,2,3,6-tetrahydropyridin-4-yl]phenyl}-1,3-dihydro-2H-isoindole-2-carboxamide;
N-{4-[1-(pyrazin-2-ylcarbonyl)-1,2,3,6-tetrahydropyridin-4-yl]phenyl}-1,3-dihydro-2H-isoindole-2-carboxamide;
N-{4-[1-(pyrimidin-4-ylcarbonyl)-1,2,3,6-tetrahydropyridin-4-yl]phenyl}-1,3-dihydro-2H-isoindole-2-carboxamide;
N-(4-{1-[3-(piperidin-1-yl)propanoyl]-1,2,3,6-tetrahydropyridin-4-yl}phenyl)-1,3-dihydro-2H-isoindole-2-carboxamide;
N-{4-[1-(morpholin-4-ylacetyl)-1,2,3,6-tetrahydropyridin-4-yl]phenyl}-1,3-dihydro-2H-isoindole-2-carboxamide;
N-(4-{1-[(4-methylpiperazin-1-yl)acetyl]-1,2,3,6-tetrahydropyridin-4-yl}phenyl)-1,3-dihydro-2H-isoindole-2-carboxamide;
N-(1'-benzoyl-1',2',3',6'-tetrahydro-3,4'-bipyridin-6-yl)-1,3-dihydro-2H-isoindole-2-carboxamide;
N-(4-{[6-(benzoylamino)hexyl]carbamoyl}phenyl)-1,3-dihydro-2H-isoindole-2-carboxamide;
N-[4-({4-[(benzoylamino)methyl]benzyl}carbamoyl)phenyl]-5-fluoro-1,3-dihydro-2H-isoindole-2-carboxamide;
N-{4-[4-(5-oxo-L-prolyl)piperazin-1-yl]phenyl}-1,3-dihydro-2H-isoindole-2-carboxamide;
N-{4-[4-(5-oxo-D-prolyl)piperazin-1-yl]phenyl}-1,3-dihydro-2H-isoindole-2-carboxamide;
N-(4-{4-[(1-acetylpiperidin-4-yl)carbonyl]piperazin-1-yl}phenyl)-1,3-dihydro-2H-isoindole-2-carboxamide;
N-{4-[4-(2-acetamidobenzoyl)piperazin-1-yl]phenyl}-1,3-dihydro-2H-isoindole-2-carboxamide;
N-{4-{4-[4-(methylsulfonyl)benzoyl]piperazin-1-yl}-phenyl)-1,3-dihydro-2H-isoindole-2-carboxamide;
N-[4-(4-butyrylpiperazin-1-yl)phenyl]-1,3-dihydro-2H-isoindole-2-carboxamide;
N-[4-(4-isobutyrylpiperazin-1-yl)phenyl]-1,3-dihydro-2H-isoindole-2-carboxamide;
N-{4-[4-(2-methylbutanoyl)piperazin-1-yl]phenyl}-1,3-dihydro-2H-isoindole-2-carboxamide;
N-{4-[4-(3,3,3-trifluoropropanoyl)piperazin-1-yl]phenyl}-1,3-dihydro-2H-isoindole-2-carboxamide;
N-{4-[4-(methoxyacetyl)piperazin-1-yl]phenyl}-1,3-dihydro-2H-isoindole-2-carboxamide;
N-{4-[4-(tetrahydrofuran-2-ylcarbonyl)piperazin-1-yl]phenyl}-1,3-dihydro-2H-isoindole-2-carboxamide;
N-{4-[4-(tetrahydrofuran-3-ylcarbonyl)piperazin-1-yl]phenyl}-1,3-dihydro-2H-isoindole-2-carboxamide;
N-{4-[4-(cyclopentylacetyl)piperazin-1-yl]phenyl}-1,3-dihydro-2H-isoindole-2-carboxamide;
N-{4-[4-(cyclohexylcarbonyl)piperazin-1-yl]phenyl}-1,3-dihydro-2H-isoindole-2-carboxamide;
N-{4-[4-(2-methoxybenzoyl)piperazin-1-yl]phenyl}-1,3-dihydro-2H-isoindole-2-carboxamide;
N-{4-[4-(3-methoxybenzoyl)piperazin-1-yl]phenyl}-1,3-dihydro-2H-isoindole-2-carboxamide;
N-{4-[4-(4-methoxybenzoyl)piperazin-1-yl]phenyl}-1,3-dihydro-2H-isoindole-2-carboxamide;
N-{4-[4-(3-fluorobenzoyl)piperazin-1-yl]phenyl}-1,3-dihydro-2H-isoindole-2-carboxamide;
N-{4-[4-(2-chlorobenzoyl)piperazin-1-yl]phenyl}-1,3-dihydro-2H-isoindole-2-carboxamide;
N-{4-[4-(4-chlorobenzoyl)piperazin-1-yl]phenyl}-1,3-dihydro-2H-isoindole-2-carboxamide;
N-{4-[4-(3-cyanobenzoyl)piperazin-1-yl]phenyl}-1,3-dihydro-2H-isoindole-2-carboxamide;
N-{4-[4-(4-cyanobenzoyl)piperazin-1-yl]phenyl}-1,3-dihydro-2H-isoindole-2-carboxamide;
N-(4-{4-[3-(dimethylamino)benzoyl]piperazin-1-yl}phenyl)-1,3-dihydro-2H-isoindole-2-carboxamide;
N-(4-{4-[4-(dimethylamino)benzoyl]piperazin-1-yl}phenyl)-1,3-dihydro-2H-isoindole-2-carboxamide;
N-{4-[4-(3,4-dimethoxybenzoyl)piperazin-1-yl]phenyl}-1,3-dihydro-2H-isoindole-2-carboxamide;
N-{4-[4-(3,5-dimethoxybenzoyl)piperazin-1-yl]phenyl}-1,3-dihydro-2H-isoindole-2-carboxamide;
N-(4-{4-[(3,4-dimethoxyphenyl)acetyl]piperazin-1-yl}phenyl)-1,3-dihydro-2H-isoindole-2-carboxamide;
N-{4-[4-(2-furoyl)piperazin-1-yl]phenyl}-1,3-dihydro-2H-isoindole-2-carboxamide;
N-{4-[4-(3-furoyl)piperazin-1-yl]phenyl}-1,3-dihydro-2H-isoindole-2-carboxamide;
N-{4-[4-(1H-pyrrol-2-ylcarbonyl)piperazin-1-yl]phenyl}-1,3-dihydro-2H-isoindole-2-carboxamide;
N-{4-[4-(1H-pyrazol-5-ylcarbonyl)piperazin-1-yl]phenyl}-1,3-dihydro-2H-isoindole-2-carboxamide;

N-{4-[4-(pyridin-2-ylcarbonyl)piperazin-1-yl]phenyl}-1,3-dihydro-2H-isoindole-2-carboxamide;
N-{4-[4-(pyridin-3-ylcarbonyl)piperazin-1-yl]phenyl}-1,3-dihydro-2H-isoindole-2-carboxamide;
N-[4-(4-isonicotinoylpiperazin-1-yl)phenyl]-1,3-dihydro-2H-isoindole-2-carboxamide;
N-{4-[4-(pyridazin-3-ylcarbonyl)piperazin-1-yl]phenyl}-1,3-dihydro-2H-isoindole-2-carboxamide;
N-{4-[4-(pyrazin-2-ylcarbonyl)piperazin-1-yl]phenyl}-1,3-dihydro-2H-isoindole-2-carboxamide;
N-{4-[4-(pyrimidin-4-ylcarbonyl)piperazin-1-yl]phenyl}-1,3-dihydro-2H-isoindole-2-carboxamide;
N-{4-[4-(N,N-dimethyl-beta-alanyl)piperazin-1-yl]phenyl}-1,3-dihydro-2H-isoindole-2-carboxamide;
N-[4-(4-acetylpiperazin-1-yl)phenyl]-1,3-dihydro-2H-isoindole-2-carboxamide;
N-{4-[4-(2-fluorobenzoyl)piperazin-1-yl]phenyl}-1,3-dihydro-2H-isoindole-2-carboxamide;
N-{4-[4-(4-fluorobenzoyl)piperazin-1-yl]phenyl}-1,3-dihydro-2H-isoindole-2-carboxamide;
N-{4-[4-(phenylacetyl)piperazin-1-yl]phenyl}-1,3-dihydro-2H-isoindole-2-carboxamide;
N-{4-[4-(1,3-thiazol-4-ylcarbonyl)piperazin-1-yl]phenyl}-1,3-dihydro-2H-isoindole-2-carboxamide;
N-{4-[4-(morpholin-4-ylacetyl)piperazin-1-yl]phenyl}-1,3-dihydro-2H-isoindole-2-carboxamide;
5-cyano-N-(4-phenylbutyl)-1,3-dihydro-2H-isoindole-2-carboxamide;
N-[4-(1-butyryl-1,2,3,6-tetrahydropyridin-4-yl)phenyl]-1,3-dihydro-2H-pyrrolo[3,4-c]pyridine-2-carboxamide;
N-[4-(1-isobutyryl-1,2,3,6-tetrahydropyridin-4-yl)phenyl]-1,3-dihydro-2H-pyrrolo[3,4-c]pyridine-2-carboxamide;
N-[4-(1-benzoyl-1,2,3,6-tetrahydropyridin-4-yl)phenyl]-1,3-dihydro-2H-pyrrolo[3,4-c]pyridine-2-carboxamide;
N-{4-[1-(tetrahydrofuran-3-ylcarbonyl)-1,2,3,6-tetrahydropyridin-4-yl]phenyl}-1,3-dihydro-2H-pyrrolo[3,4-c]pyridine-2-carboxamide;
N-[4-(1-oxo-2,3-dihydro-1H-isoindol-4-yl)phenyl]-1,3-dihydro-2H-isoindole-2-carboxamide;
N-[4-(4-oxo-3,4-dihydrophthalazin-1-yl)phenyl]-1,3-dihydro-2H-pyrrolo[3,4-c]pyridine-2-carboxamide;
N-[4-(4-oxo-3,4-dihydrophthalazin-1-yl)phenyl]-5,7-dihydro-6H-pyrrolo[3,4-b]pyridine-6-carboxamide;
N-[4-(1-oxo-1,2-dihydroisoquinolin-4-yl)cyclohex-3-en-1-yl]-1,3-dihydro-2H-isoindole-2-carboxamide;
N-[4-(4-oxo-3,4-dihydrophthalazin-1-yl)cyclohex-3-en-1-yl]-1,3-dihydro-2H-isoindole-2-carboxamide;
N-[4-(4-oxo-3,4-dihydrophthalazin-1-yl)cyclohex-3-en-1-yl]-5-(pyrrolidin-1-ylmethyl)-1,3-dihydro-2H-isoindole-2-carboxamide;
N-{4-[(tetrahydro-2H-pyran-2-ylmethyl)carbamoyl]phenyl}-1,3-dihydro-2H-pyrrolo[3,4-c]pyridine-2-carboxamide;
N-{4-[(tetrahydro-2H-pyran-3-ylmethyl)carbamoyl]phenyl}-1,3-dihydro-2H-pyrrolo[3,4-c]pyridine-2-carboxamide;
N-{4-[(tetrahydro-2H-pyran-4-ylmethyl)carbamoyl]phenyl}-1,3-dihydro-2H-pyrrolo[3,4-c]pyridine-2-carboxamide;
N-(4-{[(2S)-1-hydroxy-4-methylpentan-2-yl]carbamoyl}phenyl)-1,3-dihydro-2H-pyrrolo[3,4-c]pyridine-2-carboxamide;
N-[1-(3-methylbutyl)-1H-pyrazol-4-yl]-1,3-dihydro-2H-isoindole-2-carboxamide;
N-[1-(2-phenylethyl)-1H-pyrazol-4-yl]-1,3-dihydro-2H-isoindole-2-carboxamide;
$N^5$-[2-(dimethylamino)ethyl]-$N^2$-[4-(propylcarbamoyl)phenyl]-1,3-dihydro-2H-isoindole-2,5-dicarboxamide;
5-(morpholin-4-ylcarbonyl)-N-[4-(propylcarbamoyl)phenyl]-1,3-dihydro-2H-isoindole-2-carboxamide;
N-(4-{benzyl[3-(morpholin-4-yl)propyl]carbamoyl}phenyl)-1,3-dihydro-2H-isoindole-2-carboxamide;
N-[4-(isobutoxycarbamoyl)phenyl]-1,3-dihydro-2H-isoindole-2-carboxamide;
5-bromo-N-{4-[(cyclopentylacetyl)amino]phenyl}-1,3-dihydro-2H-isoindole-2-carboxamide;
5-cyano-N-{4-[(cyclopentylacetyl)amino]phenyl}-1,3-dihydro-2H-isoindole-2-carboxamide;
methyl 4-{[(5-cyano-1,3-dihydro-2H-isoindol-2-yl)carbonyl]amino}benzoate;
N-(4-{(E)-[(benzyloxy)imino]methyl}phenyl)-1,3-dihydro-2H-isoindole-2-carboxamide;
5-fluoro-N-{4-[(tetrahydro-2H-pyran-2-ylmethyl)carbamoyl]phenyl}-1,3-dihydro-2H-isoindole-2-carboxamide;
5-fluoro-N-{4-[(tetrahydro-2H-pyran-3-ylmethyl)carbamoyl]phenyl}-1,3-dihydro-2H-isoindole-2-carboxamide;
5-fluoro-N-{4-[(tetrahydro-2H-pyran-4-ylmethyl)carbamoyl]phenyl}-1,3-dihydro-2H-isoindole-2-carboxamide;
5-fluoro-N-(4-{[(1S)-2-hydroxy-1-phenylethyl]carbamoyl}phenyl)-1,3-dihydro-2H-isoindole-2-carboxamide;
5-fluoro-N-(4-{[(1S)-2-hydroxy-1-(pyridin-2-yl)ethyl]carbamoyl}phenyl)-1,3-dihydro-2H-isoindole-2-carboxamide;
5-fluoro-N-(4-{[(2S)-1-hydroxy-4-methylpentan-2-yl]carbamoyl}phenyl)-1,3-dihydro-2H-isoindole-2-carboxamide;
N-[4-(3-aminopyrrolidin-1-yl)phenyl]-1,3-dihydro-2H-isoindole-2-carboxamide;
N-{6-[(3-methylbutyl)carbamoyl]pyridin-3-yl}-1,3-dihydro-2H-isoindole-2-carboxamide;
N-{6-[(3-phenylpropyl)carbamoyl]pyridin-3-yl}-1,3-dihydro-2H-isoindole-2-carboxamide;
N-{6-[(tetrahydrofuran-3-ylmethyl)carbamoyl]pyridin-3-yl}-1,3-dihydro-2H-isoindole-2-carboxamide;
$N^2$-{4-[(cyclopentylacetyl)amino]phenyl}-1,3-dihydro-2H-isoindole-2,5-dicarboxamide;
N-[4-({benzyl[3-(morpholin-4-yl)propyl]amino}methyl)phenyl]-1,3-dihydro-2H-isoindole-2-carboxamide;
N-{4-[(cyclopentylacetyl)amino]phenyl}-5-(1H-pyrazol-3-yl)-1,3-dihydro-2H-isoindole-2-carboxamide;
N-{4-[(cyclopentylacetyl)amino]phenyl}-5-(pyridin-3-yl)-1,3-dihydro-2H-isoindole-2-carboxamide;
N-{4-[(cyclopentylacetyl)amino]phenyl}-5-(1-methyl-1H-pyrazol-4-yl)-1,3-dihydro-2H-isoindole-2-carboxamide;
$N^2$-{4-[(cyclopentylacetyl)amino]phenyl}-$N^5$-(2-methoxyethyl)-1,3-dihydro-2H-isoindole-2,5-dicarboxamide;
$N^2$-{4-[(cyclopentylacetyl)amino]phenyl}-$N^5$-(2-hydroxyethyl)-1,3-dihydro-2H-isoindole-2,5-dicarboxamide;
5-(aminomethyl)-N-{4-[(cyclopentylacetyl)amino]phenyl}-1,3-dihydro-2H-isoindole-2-carboxamide;
N-(4-{[(2S)-1-hydroxy-4-(methylthio)butan-2-yl]carbamoyl}phenyl)-1,3-dihydro-2H-isoindole-2-carboxamide;
N-(4-{[(2S,3S)-1-hydroxy-3-methylpentan-2-yl]carbamoyl}phenyl)-1,3-dihydro-2H-isoindole-2-carboxamide;
N-(4-{[(2S)-1-hydroxypropan-2-yl]carbamoyl}phenyl)-1,3-dihydro-2H-isoindole-2-carboxamide;
N-(4-{[(2S,3R)-1,3-dihydroxybutan-2-yl]carbamoyl}phenyl)-1,3-dihydro-2H-isoindole-2-carboxamide;

N-(4-{[(2S)-1-hydroxyhexan-2-yl]carbamoyl}phenyl)-1,3-dihydro-2H-isoindole-2-carboxamide;
N-(4-{[(2S)-1-hydroxypentan-2-yl]carbamoyl}phenyl)-1,3-dihydro-2H-isoindole-2-carboxamide;
N-(4-{[(1S,2S)-2-hydroxycyclopentyl]carbamoyl}phenyl)-1,3-dihydro-2H-isoindole-2-carboxamide;
N-(4-{[(1S,2R)-2-hydroxycyclopentyl]carbamoyl}phenyl)-1,3-dihydro-2H-isoindole-2-carboxamide;
N-(4-{[(2S)-1-cyclohexyl-3-hydroxypropan-2-yl]carbamoyl}phenyl)-1,3-dihydro-2H-isoindole-2-carboxamide;
N-[4-({(2R)-1-hydroxy-3-[(4-methylbenzyl)thio]propan-2-yl}carbamoyl)phenyl]-1,3-dihydro-2H-isoindole-2-carboxamide;
N-(4-{[(1S)-1-(4-tert-butylphenyl)-2-hydroxyethyl]carbamoyl}phenyl)-1,3-dihydro-2H-isoindole-2-carboxamide;
N-{4-[(cyclopentylacetyl)amino]phenyl}-5-methoxy-1,3-dihydro-2H-isoindole-2-carboxamide;
5-methoxy-N-[4-(propylcarbamoyl)phenyl]-1,3-dihydro-2H-isoindole-2-carboxamide;
5-methyl-N-[4-(propylcarbamoyl)phenyl]-1,3-dihydro-2H-isoindole-2-carboxamide;
N-[4-(propylcarbamoyl)phenyl]-1,3-dihydro-2H-pyrrolo[3,4-c]pyridine-2-carboxamide;
N-(4-{[(2S)-tetrahydrofuran-2-ylmethyl]carbamoyl}phenyl)-5,7-dihydro-6H-pyrrolo[3,4-b]pyridine-6-carboxamide;
N-(4-{[(2R)-tetrahydrofuran-2-ylmethyl]carbamoyl}phenyl)-5,7-dihydro-6H-pyrrolo[3,4-b]pyridine-6-carboxamide;
N-(4-{[(2S)-1-hydroxy-4-methylpentan-2-yl]carbamoyl}phenyl)-5,7-dihydro-6H-pyrrolo[3,4-b]pyridine-6-carboxamide;
N-(4-{[(1S)-2-hydroxy-1-phenylethyl]carbamoyl}phenyl)-5,7-dihydro-6H-pyrrolo[3,4-b]pyridine-6-carboxamide;
N-{4-[(tetrahydro-2H-pyran-4-ylmethyl)carbamoyl]phenyl}-5,7-dihydro-6H-pyrrolo[3,4-b]pyridine-6-carboxamide;
N-[6-(benzoylamino)hexyl]-1,3-dihydro-2H-isoindole-2-carboxamide;
N-{6-[(pyridin-3-ylcarbonyl)amino]hexyl}-1,3-dihydro-2H-isoindole-2-carboxamide;
N-{4-[(cyclopentylacetyl)amino]phenyl}-5-(pyridin-4-yl)-1,3-dihydro-2H-isoindole-2-carboxamide;
5-(hydroxymethyl)-N-{4-[(3-methylbutyl)carbamoyl]phenyl}-1,3-dihydro-2H-isoindole-2-carboxamide;
N-(6-{[(3S)-tetrahydrofuran-3-ylmethyl]carbamoyl}pyridazin-3-yl)-1,3-dihydro-2H-isoindole-2-carboxamide;
N-{6-[(cyclopentylmethyl)carbamoyl]pyridazin-3-yl}-1,3-dihydro-2H-isoindole-2-carboxamide;
N-(4-{[(1S)-2-hydroxy-1-(pyridin-2-yl)ethyl]carbamoyl}phenyl)-5,7-dihydro-6H-pyrrolo[3,4-b]pyridine-6-carboxamide;
N-[1'-(tetrahydrofuran-3-ylcarbonyl)-1',2',3',6'-tetrahydro-2,4'-bipyridin-5-yl]-1,3-dihydro-2H-isoindole-2-carboxamide;
N-{1'-[(2-methoxyethoxy)acetyl]-1',2',3',6'-tetrahydro-2,4'-bipyridin-5-yl}-1,3-dihydro-2H-isoindole-2-carboxamide;
5-(hydroxymethyl)-N-(4-phenylbutyl)-1,3-dihydro-2H-isoindole-2-carboxamide;
5-(hydroxymethyl)-N-[1-(3-methylbutyl)-1H-pyrazol-4-yl]-1,3-dihydro-2H-isoindole-2-carboxamide;
N-{5-[(3-methylbutyl)carbamoyl]pyrazin-2-yl}-1,3-dihydro-2H-isoindole-2-carboxamide;
N-(6-acetamidohexyl)-1,3-dihydro-2H-isoindole-2-carboxamide;
N-(4-{1-[(2-methoxyethoxy)acetyl]-1,2,3,6-tetrahydropyridin-4-yl}phenyl)-1,3-dihydro-2H-pyrrolo[3,4-c]pyridine-2-carboxamide;
N-(4-{(1E)-3-[benzyl(methyl)amino]prop-1-en-1-yl}phenyl)-1,3-dihydro-2H-isoindole-2-carboxamide;
N-[4-(4-phenoxypiperidin-1-yl)phenyl]-1,3-dihydro-2H-isoindole-2-carboxamide;
N-[4-(3-phenoxyazetidin-1-yl)phenyl]-1,3-dihydro-2H-isoindole-2-carboxamide;
N-(4-{[benzyl(methyl)amino]methyl}phenyl)-1,3-dihydro-2H-isoindole-2-carboxamide;
5-fluoro-N-(4-{[(3R)-tetrahydrofuran-3-ylmethyl]carbamoyl}phenyl)-1,3-dihydro-2H-isoindole-2-carboxamide;
5-fluoro-N-(4-{[(3S)-tetrahydrofuran-3-ylmethyl]carbamoyl}phenyl)-1,3-dihydro-2H-isoindole-2-carboxamide;
N-{4-[(4-hydroxypiperidin-1-yl)carbonyl]phenyl}-1,3-dihydro-2H-pyrrolo[3,4-c]pyridine-2-carboxamide;
N-{4-[(2-hydroxy-2-methylpropyl)carbamoyl]phenyl}-1,3-dihydro-2H-pyrrolo[3,4-c]pyridine-2-carboxamide;
N-{4-[(4-hydroxybutyl)carbamoyl]phenyl}-1,3-dihydro-2H-pyrrolo[3,4-c]pyridine-2-carboxamide;
N-(4-{[(2S)-1-hydroxy-3-methylbutan-2-yl]carbamoyl}phenyl)-1,3-dihydro-2H-pyrrolo[3,4-c]pyridine-2-carboxamide;
N-{4-[(1-hydroxy-2-methylpropan-2-yl)carbamoyl]phenyl}-1,3-dihydro-2H-pyrrolo[3,4-c]pyridine-2-carboxamide;
N-(4-{[(2R)-2-hydroxypropyl]carbamoyl}phenyl)-1,3-dihydro-2H-pyrrolo[3,4-c]pyridine-2-carboxamide;
N-(4-{[(2S)-2-hydroxypropyl]carbamoyl}phenyl)-1,3-dihydro-2H-pyrrolo[3,4-c]pyridine-2-carboxamide;
N-(4-{[3-(piperidin-1-yl)propyl]carbamoyl}phenyl)-1,3-dihydro-2H-pyrrolo[3,4-c]pyridine-2-carboxamide;
N-[4-(5,6-dihydroimidazo[1,5-a]pyrazin-7(8H)-ylcarbonyl)phenyl]-1,3-dihydro-2H-pyrrolo[3,4-c]pyridine-2-carboxamide;
N-[4-(1-benzyl-1H-1,2,3-triazol-4-yl)phenyl]-1,3-dihydro-2H-isoindole-2-carboxamide;
N-{4-[1-(3-methylbutyl)-1H-1,2,3-triazol-4-yl]phenyl}-1,3-dihydro-2H-isoindole-2-carboxamide;
N-{4-[1-(tetrahydrofuran-3-ylmethyl)-1H-1,2,3-triazol-4-yl]phenyl}-1,3-dihydro-2H-isoindole-2-carboxamide;
N-(4-{1-[2-(2-oxopyrrolidin-1-yl)ethyl]-1H-1,2,3-triazol-4-yl}phenyl)-1,3-dihydro-2H-isoindole-2-carboxamide;
N-{4-[1-(1-benzylpiperidin-4-yl)-1H-1,2,3-triazol-4-yl]phenyl}-1,3-dihydro-2H-isoindole-2-carboxamide;
N-{4-[1(3-phenylpropyl)-1H-1,2,3-triazol-4-yl]phenyl}-1,3-dihydro-2H-isoindole-2-carboxamide;
N-(4-{1-[4-(morpholin-4-yl)benzyl]-1H-1,2,3-triazol-4-yl}phenyl)-1,3-dihydro-2H-isoindole-2-carboxamide;
N-[4-(1-isobutyl-1H-1,2,3-triazol-4-yl)phenyl]-1,3-dihydro-2H-isoindole-2-carboxamide;
N-{4-[1-(cyclopentylmethyl)-1H-1,2,3-triazol-4-yl]phenyl}-1,3-dihydro-2H-isoindole-2-carboxamide;
N-{4-[1-(3-methoxypropyl)-1H-1,2,3-triazol-4-yl]phenyl}-1,3-dihydro-2H-isoindole-2-carboxamide;
N-[4-(1-isobutyrylpiperidin-4-yl)phenyl]-1,3-dihydro-2H-pyrrolo[3,4-c]pyridine-2-carboxamide;
N-(4-{1-[(2-methoxyethoxy)acetyl]piperidin-4-yl}phenyl)-1,3-dihydro-2H-isoindole-2-carboxamide;
N-{5-[1-(tetrahydrofuran-3-ylcarbonyl)piperidin-4-yl]pyridin-2-yl}-1,3-dihydro-2H-isoindole-2-carboxamide;

5-(hydroxymethyl)-N-{4-[(tetrahydrofuran-3-ylacetyl) amino]phenyl}-1,3-dihydro-2H-isoindole-2-carboxamide;

5-(hydroxymethyl)-N-(4-{[(2-methoxyethoxy)acetyl]amino}phenyl)-1,3-dihydro-2H-isoindole-2-carboxamide;

N-(1'-isobutyryl-1',2',3',6'-tetrahydro-2,4'-bipyridin-5-yl)-1,3-dihydro-2H-pyrrolo[3,4-c]pyridine-2-carboxamide;

N-(1'-benzoyl-1',2',3',6'-tetrahydro-2,4'-bipyridin-5-yl)-1,3-dihydro-2H-pyrrolo[3,4-c]pyridine-2-carboxamide;

N-[1'-(tetrahydro furan-3-ylcarbonyl)-1',2',3',6'-tetrahydro-2,4'-bipyridin-5-yl]-1,3-dihydro-2H-pyrrolo[3,4-c]pyridine-2-carboxamide;

N-{1'-[(2-methoxyethoxy)acetyl]-1',2',3',6'-tetrahydro-2,4'-bipyridin-5-yl}-1,3-dihydro-2H-pyrrolo[3,4-c]pyridine-2-carboxamide;

N-(6-{[4-(methylsulfonyl)benzoyl]amino}hexyl)-1,3-dihydro-2H-isoindole-2-carboxamide;

N-{6-[(ethoxyacetyl)amino]hexyl}-1,3-dihydro-2H-isoindole-2-carboxamide;

N-{6-[(cyclopentylcarbonyl)amino]hexyl}-1,3-dihydro-2H-isoindole-2-carboxamide;

N-{6-[(2-hydroxybenzoyl)amino]hexyl}-1,3-dihydro-2H-isoindole-2-carboxamide;

N-{6-[(3-hydroxybenzoyl)amino]hexyl}-1,3-dihydro-2H-isoindole-2-carboxamide;

N-{6-[(4-hydroxybenzoyl)amino]hexyl}-1,3-dihydro-2H-isoindole-2-carboxamide;

N-{6-[(2-methoxybenzoyl)amino]hexyl}-1,3-dihydro-2H-isoindole-2-carboxamide;

N-{6-[(3-methoxybenzoyl)amino]hexyl}-1,3-dihydro-2H-isoindole-2-carboxamide;

N-{6-[(4-methoxybenzoyl)amino]hexyl}-1,3-dihydro-2H-isoindole-2-carboxamide;

N-{6-[(2-fluorobenzoyl)amino]hexyl}-1,3-dihydro-2H-isoindole-2-carboxamide;

N-{6-[(3-fluorobenzoyl)amino]hexyl}-1,3-dihydro-2H-isoindole-2-carboxamide;

N-{6-[(4-fluorobenzoyl)amino]hexyl}-1,3-dihydro-2H-isoindole-2-carboxamide;

N-{6-[(2-chlorobenzoyl)amino]hexyl}-1,3-dihydro-2H-isoindole-2-carboxamide;

N-{6-[(3-chlorobenzoyl)amino]hexyl}-1,3-dihydro-2H-isoindole-2-carboxamide;

N-{6-[(4-chlorobenzoyl)amino]hexyl}-1,3-dihydro-2H-isoindole-2-carboxamide;

N-{6-[(3-cyanobenzoyl)amino]hexyl}-1,3-dihydro-2H-isoindole-2-carboxamide;

N-{6-[(4-cyanobenzoyl)amino]hexyl}-1,3-dihydro-2H-isoindole-2-carboxamide;

N-(6-{[3-(dimethylamino)benzoyl]amino}hexyl)-1,3-dihydro-2H-isoindole-2-carboxamide;

N-(6-{[4-(dimethylamino)benzoyl]amino}hexyl)-1,3-dihydro-2H-isoindole-2-carboxamide;

N-(6-{[3-(trifluoromethyl)benzoyl]amino}hexyl)-1,3-dihydro-2H-isoindole-2-carboxamide;

N-(6-{[4-(trifluoromethyl)benzoyl]amino}hexyl)-1,3-dihydro-2H-isoindole-2-carboxamide;

N-(6-{[3-(trifluoromethoxy)benzoyl]amino}hexyl)-1,3-dihydro-2H-isoindole-2-carboxamide;

N-{6-[(2,3-dimethoxybenzoyl)amino]hexyl}-1,3-dihydro-2H-isoindole-2-carboxamide;

N-{6-[(2,4-dimethoxybenzoyl)amino]hexyl}-1,3-dihydro-2H-isoindole-2-carboxamide;

N-{6-[(2,5-dimethoxybenzoyl)amino]hexyl}-1,3-dihydro-2H-isoindole-2-carboxamide;

N-{6-[(phenylacetyl)amino]hexyl}-1,3-dihydro-2H-isoindole-2-carboxamide;

N-(6-{[(3-fluorophenyl)acetyl]amino}hexyl)-1,3-dihydro-2H-isoindole-2-carboxamide;

5-(hydroxymethyl)-N-{4-[(tetrahydrofuran-2-ylacetyl) amino]phenyl}-1,3-dihydro-2H-isoindole-2-carboxamide;

N-{4-[(ethoxyacetyl)amino]phenyl}-5-(hydroxymethyl)-1,3-dihydro-2H-isoindole-2-carboxamide;

5-(hydroxymethyl)-N-{4-[(tetrahydro-2H-pyran-4-ylacetyl) amino]phenyl}-1,3-dihydro-2H-isoindole-2-carboxamide;

5-(hydroxymethyl)-N-{4-[(morpholin-4-ylacetyl)amino] phenyl}-1,3-dihydro-2H-isoindole-2-carboxamide;

N-[4-(morpholin-4-ylcarbonyl)phenyl]-1,3-dihydro-2H-pyrrolo[3,4-c]pyridine-2-carboxamide;

N-(4-{[3-(2-oxopyrrolidin-1-yl)propyl]carbamoyl}phenyl)-1,3-dihydro-2H-pyrrolo[3,4-c]pyridine-2-carboxamide;

N-[6-(benzoylamino)hexyl]-1,3-dihydro-2H-pyrrolo[3,4-c]pyridine-2-carboxamide;

4-fluoro-N-{6-[(pyridin-3-ylcarbonyl)amino]hexyl}-1,3-dihydro-2H-isoindole-2-carboxamide;

5-fluoro-N-{6-[(pyridin-3-ylcarbonyl)amino]hexyl}-1,3-dihydro-2H-isoindole-2-carboxamide;

5-methoxy-N-{6-[(pyridin-3-ylcarbonyl)amino]hexyl}-1,3-dihydro-2H-isoindole-2-carboxamide;

N-{6-[(pyridin-3-ylcarbonyl)amino]hexyl}-5-(trifluoromethyl)-1,3-dihydro-2H-isoindole-2-carboxamide;

4-cyano-N-{6-[(pyridin-3-ylcarbonyl)amino]hexyl}-1,3-dihydro-2H-isoindole-2-carboxamide;

5-methyl-N-{6-[(pyridin-3-ylcarbonyl)amino]hexyl}-1,3-dihydro-2H-isoindole-2-carboxamide;

4-chloro-N-{6-[(pyridin-3-ylcarbonyl)amino]hexyl}-1,3-dihydro-2H-isoindole-2-carboxamide;

5-cyano-N-{6-[(pyridin-3-ylcarbonyl)amino]hexyl}-1,3-dihydro-2H-isoindole-2-carboxamide;

5-chloro-N-{6-[(pyridin-3-ylcarbonyl)amino]hexyl}-1,3-dihydro-2H-isoindole-2-carboxamide;

N-{6-[(pyridin-2-ylcarbonyl)amino]hexyl}-1,3-dihydro-2H-isoindole-2-carboxamide;

N-{4-[1-(pyridin-2-ylcarbonyl)piperidin-4-yl]butyl}-1,3-dihydro-2H-isoindole-2-carboxamide;

N-[1'-(tetrahydrofuran-2-ylcarbonyl)-1',2',3',6'-tetrahydro-2,4'-bipyridin-5-yl]-1,3-dihydro-2H-pyrrolo[3,4-c]pyridine-2-carboxamide;

N-[1'-(tetrahydro-2H-pyran-4-ylcarbonyl)-1',2',3',6'-tetrahydro-2,4'-bipyridin-5-yl]-1,3-dihydro-2H-pyrrolo[3,4-c]pyridine-2-carboxamide;

N-[1'-(1,4-dioxan-2-ylcarbonyl)-1',2',3',6'-tetrahydro-2,4'-bipyridin-5-yl]-1,3-dihydro-2H-pyrrolo[3,4-c]pyridine-2-carboxamide;

N-{1'-[(1,1-dioxidotetrahydrothiophen-3-yl)carbonyl]-1',2',3',6'-tetrahydro-2,4'-bipyridin-5-yl}-1,3-dihydro-2H-pyrrolo[3,4-c]pyridine-2-carboxamide;

N-[1'-(2-hydroxy-2-methylpropanoyl)-1',2',3',6'-tetrahydro-2,4'-bipyridin-5-yl]-1,3-dihydro-2H-pyrrolo[3,4-c]pyridine-2-carboxamide;

N-{4-[1-(tetrahydrofuran-2-ylcarbonyl)-1,2,3,6-tetrahydropyridin-4-yl]phenyl}-1,3-dihydro-2H-pyrrolo[3,4-c]pyridine-2-carboxamide;

N-{4-[1-(tetrahydro-2H-pyran-4-ylcarbonyl)-1,2,3,6-tetrahydropyridin-4-yl]phenyl}-1,3-dihydro-2H-pyrrolo[3,4-c]pyridine-2-carboxamide;

N-{4-[1-(1,4-dioxan-2-ylcarbonyl)-1,2,3,6-tetrahydropyridin-4-yl]phenyl}-1,3-dihydro-2H-pyrrolo[3,4-c]pyridine-2-carboxamide;

N-(4-{1-[(1-methylpyrrolidin-3-yl)carbonyl]-1,2,3,6-tetrahydropyridin-4-yl}phenyl)-1,3-dihydro-2H-pyrrolo[3,4-c]pyridine-2-carboxamide;

N-(4-{1-[(1,1-dioxidotetrahydrothiophen-3-yl)carbonyl]-1,2,3,6-tetrahydropyridin-4-yl}phenyl)-1,3-dihydro-2H-pyrrolo[3,4-c]pyridine-2-carboxamide;

N-{4-[1-(2-hydroxy-2-methylpropanoyl)-1,2,3,6-tetrahydropyridin-4-yl]phenyl}-1,3-dihydro-2H-pyrrolo[3,4-c]pyridine-2-carboxamide;

N-[1'-(tetrahydro furan-2-ylcarbonyl)-1',2',3',6'-tetrahydro-2,4'-bipyridin-5-yl]-1,3-dihydro-2H-isoindole-2-carboxamide;

N-[1'-(tetrahydro-2H-pyran-4-ylcarbonyl)-1',2',3',6'-tetrahydro-2,4'-bipyridin-5-yl]-1,3-dihydro-2H-isoindole-2-carboxamide;

N-[1'-(1,4-dioxan-2-ylcarbonyl)-1',2',3',6'-tetrahydro-2,4'-bipyridin-5-yl]-1,3-dihydro-2H-isoindole-2-carboxamide;

N-{1'-[(1-methylpyrrolidin-3-yl)carbonyl]-1',2',3',6'-tetrahydro-2,4'-bipyridin-5-yl}-1,3-dihydro-2H-isoindole-2-carboxamide;

N-{1'-[(1,1-dioxidotetrahydrothiophen-3-yl)carbonyl]-1',2',3',6'-tetrahydro-2,4'-bipyridin-5-yl}-1,3-dihydro-2H-isoindole-2-carboxamide;

N-(4-{[(1-methylpyrrolidin-3-yl)methyl]carbamoyl}phenyl)-1,3-dihydro-2H-isoindole-2-carboxamide;

N-{4-[(pyrrolidin-3-ylmethyl)carbamoyl]phenyl}-1,3-dihydro-2H-isoindole-2-carboxamide;

N-(4-{[(3S)-tetrahydrofuran-3-ylmethyl]carbamoyl}phenyl)-1,3-dihydro-2H-pyrrolo[3,4-c]pyridine-2-carboxamide;

N-(4-{[(1-methylpiperidin-4-yl)methyl]carbamoyl}phenyl)-1,3-dihydro-2H-isoindole-2-carboxamide;

N-(7-oxo-7-{[(3R)-tetrahydro furan-3-ylmethyl]amino}heptyl)-1,3-dihydro-2H-isoindole-2-carboxamide;

N-{7-oxo-7-[(tetrahydro-2H-pyran-4-ylmethyl)amino]heptyl}-1,3-dihydro-2H-isoindole-2-carboxamide;

N-[4-(1-benzoylpiperidin-4-yl)butyl]-1,3-dihydro-2H-pyrrolo[3,4-c]pyridine-2-carboxamide;

N-{4-[(2-isopropoxyethyl)carbamoyl]phenyl}-1,3-dihydro-2H-pyrrolo[3,4-c]pyridine-2-carboxamide;

N-{4-[methyl(3-methylbutyl)carbamoyl]phenyl}-1,3-dihydro-2H-pyrrolo[3,4-c]pyridine-2-carboxamide;

N-[4-(azetidin-1-ylcarbonyl)phenyl]-1,3-dihydro-2H-pyrrolo[3,4-c]pyridine-2-carboxamide;

N-[4-(2,6-diazaspiro[3.5]non-2-ylcarbonyl)phenyl]-1,3-dihydro-2H-pyrrolo[3,4-c]pyridine-2-carboxamide;

N-[4-(1,7-diazaspiro[4.4]non-1-ylcarbonyl)phenyl]-1,3-dihydro-2H-pyrrolo[3,4-c]pyridine-2-carboxamide;

N-(4-{[4-(morpholin-4-yl)benzyl]carbamoyl}phenyl)-1,3-dihydro-2H-pyrrolo[3,4-c]pyridine-2-carboxamide;

N-{4-[(cyclopropylmethyl)carbamoyl]phenyl}-1,3-dihydro-2H-pyrrolo[3,4-c]pyridine-2-carboxamide;

N-{4-[methyl(propyl)carbamoyl]phenyl}-1,3-dihydro-2H-pyrrolo[3,4-c]pyridine-2-carboxamide;

N-[4-(isobutylcarbamoyl)phenyl]-1,3-dihydro-2H-pyrrolo[3,4-c]pyridine-2-carboxamide;

N-[4-(butylcarbamoyl)phenyl]-1,3-dihydro-2H-pyrrolo[3,4-c]pyridine-2-carboxamide;

N-{4-[(2-methoxyethyl)carbamoyl]phenyl}-1,3-dihydro-2H-pyrrolo[3,4-c]pyridine-2-carboxamide;

N-{4-(cyclopentylcarbamoyl)phenyl]-1,3-dihydro-2H-pyrrolo[3,4-c]pyridine-2-carboxamide;

N-{4-[(3R)-tetrahydrofuran-3-ylcarbamoyl]phenyl}-1,3-dihydro-2H-pyrrolo[3,4-c]pyridine-2-carboxamide;

N-{4-[(2-methoxyethyl)(methyl)carbamoyl]phenyl}-1,3-dihydro-2H-pyrrolo[3,4-c]pyridine-2-carboxamide;

N-{4-[(1-methoxypropan-2-yl)carbamoyl]phenyl}-1,3-dihydro-2H-pyrrolo[3,4-c]pyridine-2-carboxamide;

N-{4-[(cyclopentylmethyl)carbamoyl]phenyl}-1,3-dihydro-2H-pyrrolo[3,4-c]pyridine-2-carboxamide;

N-{4-[(2-thienylmethyl)carbamoyl]phenyl}-1,3-dihydro-2H-pyrrolo[3,4-c]pyridine-2-carboxamide;

N-{4-[methyl(tetrahydrofuran-2-ylmethyl)carbamoyl]phenyl}-1,3-dihydro-2H-pyrrolo[3,4-c]pyridine-2-carboxamide;

N-{4-[(3-isopropoxypropyl)carbamoyl]phenyl}-1,3-dihydro-2H-pyrrolo[3,4-c]pyridine-2-carboxamide;

N-{4-[benzyl(methyl)carbamoyl]phenyl}-1,3-dihydro-2H-pyrrolo[3,4-c]pyridine-2-carboxamide;

N-{4-[(3-aminobenzyl)carbamoyl]phenyl}-1,3-dihydro-2H-pyrrolo[3,4-c]pyridine-2-carboxamide;

N-{4-[(6-methoxypyridin-3-yl)carbamoyl]phenyl}-1,3-dihydro-2H-pyrrolo[3,4-c]pyridine-2-carboxamide;

N-{4-[(3-isobutoxypropyl)carbamoyl]phenyl}-1,3-dihydro-2H-pyrrolo[3,4-c]pyridine-2-carboxamide;

N-{4-[bis(2-methoxyethyl)carbamoyl]phenyl}-1,3-dihydro-2H-pyrrolo[3,4-c]pyridine-2-carboxamide;

N-{4-[(4-methoxybenzyl)carbamoyl]phenyl}-1,3-dihydro-2H-pyrrolo[3,4-c]pyridine-2-carboxamide;

N-{4-[(3-methoxybenzyl)carbamoyl]phenyl}-1,3-dihydro-2H-pyrrolo[3,4-c]pyridine-2-carboxamide;

N-(4-{[4-(trifluoromethyl)piperidin-1-yl]carbonyl}phenyl)-1,3-dihydro-2H-pyrrolo[3,4-c]pyridine-2-carboxamide;

N-(4-{[4-(pyrazin-2-yl)piperazin-1-yl]carbonyl}phenyl)-1,3-dihydro-2H-pyrrolo[3,4-c]pyridine-2-carboxamide;

N-{4-[(4-cyclohexylpiperazin-1-yl)carbonyl]phenyl}-1,3-dihydro-2H-pyrrolo[3,4-c]pyridine-2-carboxamide;

N-(4-{[2-(3,4-dimethoxyphenyl)ethyl]carbamoyl}phenyl)-1,3-dihydro-2H-pyrrolo[3,4-c]pyridine-2-carboxamide;

N-{4-[5-(morpholin-4-ylmethyl)-1,2,4-oxadiazol-3-yl]phenyl}-1,3-dihydro-2H-isoindole-2-carboxamide;

N-(4-{5-[(4-methylpiperazin-1-yl)methyl]-1,2,4-oxadiazol-3-yl}phenyl)-1,3-dihydro-2H-isoindole-2-carboxamide;

N-[4-(5-{[(3-methylbutyl)amino]methyl}-1,2,4-oxadiazol-3-yl)phenyl]-1,3-dihydro-2H-isoindole-2-carboxamide;

N-(4-{5-[(4-hydroxypiperidin-1-yl)methyl]-1,2,4-oxadiazol-3-yl}phenyl)-1,3-dihydro-2H-isoindole-2-carboxamide;

N-{4-[1-(2-chlorobenzoyl)piperidin-4-yl]butyl}-1,3-dihydro-2H-pyrrolo[3,4-c]pyridine-2-carboxamide;

N-[1'-(2-hydroxy-2-methylpropanoyl)-1',2',3',6'-tetrahydro-2,4'-bipyridin-5-yl]-1,3-dihydro-2H-isoindole-2-carboxamide;

N-{4-[1-(tetrahydro-2H-pyran-4-ylcarbonyl)-1,2,3,6-tetrahydropyridin-4-yl]phenyl}-1,3-dihydro-2H-isoindole-2-carboxamide;

N-{4-[1-(1,4-dioxan-2-ylcarbonyl)-1,2,3,6-tetrahydropyridin-4-yl]phenyl}-1,3-dihydro-2H-isoindole-2-carboxamide;

N-(4-{1-[(1-methylpyrrolidin-3-yl)carbonyl]-1,2,3,6-tetrahydropyridin-4-yl}phenyl)-1,3-dihydro-2H-isoindole-2-carboxamide;

N-(4-{1-[(1,1-dioxidotetrahydrothiophen-3-yl)carbonyl]-1,2,3,6-tetrahydropyridin-4-yl}phenyl)-1,3-dihydro-2H-isoindole-2-carboxamide;

N-{4-[1-(2-hydroxy-2-methylpropanoyl)-1,2,3,6-tetrahydropyridin-4-yl]phenyl}-1,3-dihydro-2H-isoindole-2-carboxamide;

N-[1'-(tetrahydro furan-2-ylcarbonyl)-1',2',3',6'-tetrahydro-3,4'-bipyridin-6-yl]-1,3-dihydro-2H-isoindole-2-carboxamide;

N-[1'-(tetrahydro-2H-pyran-4-ylcarbonyl)-1',2',3',6'-tetrahydro-3,4'-bipyridin-6-yl]-1,3-dihydro-2H-isoindole-2-carboxamide;

N-[1'-(1,4-dioxan-2-ylcarbonyl)-1',2',3',6'-tetrahydro-3,4'-bipyridin-6-yl]-1,3-dihydro-2H-isoindole-2-carboxamide;

N-{1'-[(1-methylpyrrolidin-3-yl)carbonyl]-1',2',3',6'-tetrahydro-3,4'-bipyridin-6-yl}-1,3-dihydro-2H-isoindole-2-carboxamide;

N-{1'-[(1,1-dioxidotetrahydrothiophen-3-yl)carbonyl]-1',2',3',6'-tetrahydro-3,4'-bipyridin-6-yl}-1,3-dihydro-2H-isoindole-2-carboxamide;

N-[1'-(2-hydroxy-2-methylpropanoyl)-1',2',3',6'-tetrahydro-3,4'-bipyridin-6-yl]-1,3-dihydro-2H-isoindole-2-carboxamide;

N-(4-{[3-(dimethylamino)propyl]carbamoyl}phenyl)-1,3-dihydro-2H-pyrrolo[3,4-c]pyridine-2-carboxamide;

N-(4-{[3-(morpholin-4-yl)propyl]carbamoyl}phenyl)-1,3-dihydro-2H-pyrrolo[3,4-c]pyridine-2-carboxamide;

N-(4-{[4-(2-aminoethyl)-1H-imidazol-1-yl]carbonyl}phenyl)-1,3-dihydro-2H-pyrrolo[3,4-c]pyridine-2-carboxamide;

N-[4-({4-[2-(2-hydroxyethoxy)ethyl]piperazin-1-yl}carbonyl)phenyl]-1,3-dihydro-2H-pyrrolo[3,4-c]pyridine-2-carboxamide;

N-{4-[(3-hydroxypropyl)carbamoyl]phenyl}-1,3-dihydro-2H-pyrrolo[3,4-c]pyridine-2-carboxamide;

N-(4-{[4-(dimethylamino)butyl]carbamoyl}phenyl)-1,3-dihydro-2H-pyrrolo[3,4-c]pyridine-2-carboxamide;

N-{4-[(pyridin-4-ylmethyl)carbamoyl]phenyl}-1,3-dihydro-2H-pyrrolo[3,4-c]pyridine-2-carboxamide;

N-{4-[(pyridin-3-ylmethyl)carbamoyl]phenyl}-1,3-dihydro-2H-pyrrolo[3,4-c]pyridine-2-carboxamide;

N-{4-[(pyrimidin-4-ylmethyl)carbamoyl]phenyl}-1,3-dihydro-2H-pyrrolo[3,4-c]pyridine-2-carboxamide;

N-(4-{[2-(pyridin-3-yl)ethyl]carbamoyl}phenyl)-1,3-dihydro-2H-pyrrolo[3,4-c]pyridine-2-carboxamide;

N-(4-{[2-(4-methylpiperazin-1-yl)ethyl]carbamoyl}phenyl)-1,3-dihydro-2H-pyrrolo[3,4-c]pyridine-2-carboxamide;

N-(4-{[(1,1-dioxidotetrahydrothiophen-3-yl)methyl]carbamoyl}phenyl)-1,3-dihydro-2H-isoindole-2-carboxamide;

N-(4-{[(2,2-dimethyl-1,3-dioxolan-4-yl)methyl]carbamoyl}phenyl)-1,3-dihydro-2H-isoindole-2-carboxamide;

N-(4-{[(1S)-2-methoxy-1-phenylethyl]carbamoyl}phenyl)-1,3-dihydro-2H-isoindole-2-carboxamide;

N-[4-({[(4S)-2,2-dimethyl-1,3-dioxolan-4-yl]methyl}carbamoyl)phenyl]-1,3-dihydro-2H-isoindole-2-carboxamide;

N-[4-({[(4R)-2,2-dimethyl-1,3-dioxolan-4-yl]methyl}carbamoyl)phenyl]-1,3-dihydro-2H-isoindole-2-carboxamide;

N-[4-({[3-(hydroxymethyl)oxetan-3-yl]methyl}carbamoyl)phenyl]-1,3-dihydro-2H-isoindole-2-carboxamide;

N-[4-(2-{benzyl[3-(morpholin-4-yl)propyl]amino}-2-oxoethyl)phenyl]-1,3-dihydro-2H-isoindole-2-carboxamide;

N-[4-(3-{benzyl[3-(morpholin-4-yl)propyl]amino}-3-oxopropyl)phenyl]-1,3-dihydro-2H-isoindole-2-carboxamide;

N-{4-[(cyclopentylacetyl)amino]phenyl}-5-fluoro-1,3-dihydro-2H-isoindole-2-carboxamide;

N-{4-[(2R)-butan-2-ylcarbamoyl]phenyl}-1,3-dihydro-2H-isoindole-2-carboxamide;

N-{4-[(cyclopentylacetyl)amino]phenyl}-5-(trifluoromethyl)-1,3-dihydro-2H-isoindole-2-carboxamide;

4-cyano-N-{4-[(cyclopentylacetyl)amino]phenyl}-1,3-dihydro-2H-isoindole-2-carboxamide;

N-{4-[(cyclopentylacetyl)amino]phenyl}-5-methyl-1,3-dihydro-2H-isoindole-2-carboxamide;

4-chloro-N-{4-[(cyclopentylacetyl)amino]phenyl}-1,3-dihydro-2H-isoindole-2-carboxamide;

N-{6-[(tetrahydro-2H-pyran-4-ylmethyl)carbamoyl]pyridazin-3-yl}-1,3-dihydro-2H-isoindole-2-carboxamide;

5-chloro-N-{4-[(cyclopentylacetyl)amino]phenyl}-1,3-dihydro-2H-isoindole-2-carboxamide;

N-[4-(6-bromo-2-oxoquinolin-1(2H)-yl)butyl]-1,3-dihydro-2H-isoindole-2-carboxamide;

N-{4-[6-(3-acetylphenyl)-2-oxoquinolin-1(2H)-yl]butyl}-1,3-dihydro-2H-isoindole-2-carboxamide;

N-{4-[1-(morpholin-4-ylacetyl)-1,2,3,6-tetrahydropyridin-4-yl]phenyl}-1,3-dihydro-2H-pyrrolo[3,4-c]pyridine-2-carboxamide;

N-[1'-(morpholin-4-ylacetyl)-1',2',3',6'-tetrahydro-2,4'-bipyridin-5-yl]-1,3-dihydro-2H-isoindole-2-carboxamide;

N-[1'-(morpholin-4-ylacetyl)-1',2',3',6'-tetrahydro-3,4'-bipyridin-6-yl]-1,3-dihydro-2H-isoindole-2-carboxamide;

N-(4-{[(3-methyloxetan-3-yl)methyl]carbamoyl}phenyl)-1,3-dihydro-2H-isoindole-2-carboxamide;

N-(4-{[(3-methyloxetan-3-yl)methyl]carbamoyl}phenyl)-1,3-dihydro-2H-pyrrolo[3,4-c]pyridine-2-carboxamide;

N-(2-{(4-fluorobenzyl)[4-(pyridin-3-yl)benzyl]amino}-1,3-thiazol-5-yl)-1,3-dihydro-2H-pyrrolo[3,4-c]pyridine-2-carboxamide;

N-[4-(2-benzyl-1,3-thiazol-4-yl)phenyl]-1,3-dihydro-2H-isoindole-2-carboxamide;

N-(7-{benzyl[3-(morpholin-4-yl)propyl]amino}-7-oxoheptyl)-1,3-dihydro-2H-isoindole-2-carboxamide;

N-{4-[(3-methylbutyl)sulfamoyl]phenyl}-1,3-dihydro-2H-isoindole-2-carboxamide;

5-cyano-N-{4-[(cyclopentylmethyl)carbamoyl]phenyl}-1,3-dihydro-2H-isoindole-2-carboxamide;

5-cyano-N-{4-[(1,3-thiazol-5-ylmethyl)carbamoyl]phenyl}-1,3-dihydro-2H-isoindole-2-carboxamide;

5-cyano-N-(4-{[(1R)-3-hydroxy-1-phenylpropyl]carbamoyl}phenyl)-1,3-dihydro-2H-isoindole-2-carboxamide;

5-cyano-N-(4-{[2-hydroxy-1-(4-methylphenyl)ethyl]carbamoyl}phenyl)-1,3-dihydro-2H-isoindole-2-carboxamide;

5-cyano-N-{4-[(1,3-dihydroxypropan-2-yl)carbamoyl]phenyl}-1,3-dihydro-2H-isoindole-2-carboxamide;

5-cyano-N-(4-{[(2R)-2-hydroxypropyl]carbamoyl}phenyl)-1,3-dihydro-2H-isoindole-2-carboxamide;

5-cyano-N-{4-[(2-hydroxy-2-methylpropyl)carbamoyl]phenyl}-1,3-dihydro-2H-isoindole-2-carboxamide;

5-cyano-N-(4-{[(2R)-1-hydroxy-3-methylbutan-2-yl]carbamoyl}phenyl)-1,3-dihydro-2H-isoindole-2-carboxamide;

5-cyano-N-(4-{[(2S)-tetrahydrofuran-2-ylmethyl]carbamoyl}phenyl)-1,3-dihydro-2H-isoindole-2-carboxamide;

5-cyano-N-(4-{[2-(4-methylpiperazin-1-yl)ethyl]carbamoyl}phenyl)-1,3-dihydro-2H-isoindole-2-carboxamide;

5-cyano-N-(4-{[(1S)-2-hydroxy-1-phenylethyl]carbamoyl}phenyl)-1,3-dihydro-2H-isoindole-2-carboxamide;

5-cyano-N-{4-[(4-hydroxybutyl)carbamoyl]phenyl}-1,3-dihydro-2H-isoindole-2-carboxamide;

5-cyano-N-(4-{[(2S)-2-hydroxypropyl]carbamoyl}phenyl)-1,3-dihydro-2H-isoindole-2-carboxamide;

5-cyano-N-{4-[(3-furylmethyl)carbamoyl]phenyl}-1,3-dihydro-2H-isoindole-2-carboxamide;
5-cyano-N-{4-[(tetrahydrofuran-2-ylmethyl)carbamoyl]phenyl}-1,3-dihydro-2H-isoindole-2-carboxamide;
5-cyano-N-(4-{[4-(2-furoyl)piperazin-1-yl]carbonyl}phenyl)-1,3-dihydro-2H-isoindole-2-carboxamide;
5-cyano-N-(4-{[4-(tetrahydrofuran-2-ylcarbonyl)piperazin-1-yl]carbonyl}phenyl)-1,3-dihydro-2H-isoindole-2-carboxamide;
5-cyano-N-(4-{[3-(piperidin-1-yl)propyl]carbamoyl}phenyl)-1,3-dihydro-2H-isoindole-2-carboxamide;
5-cyano-N-(4-{[(2R)-tetrahydrofuran-2-ylmethyl]carbamoyl}phenyl)-1,3-dihydro-2H-isoindole-2-carboxamide;
5-cyano-N-(4-{[4-(ethylsulfonyl)piperazin-1-yl]carbonyl}phenyl)-1,3-dihydro-2H-isoindole-2-carboxamide;
5-cyano-N-{4-[(tetrahydrofuran-3-ylmethyl)carbamoyl]phenyl}-1,3-dihydro-2H-isoindole-2-carboxamide;
5-cyano-N-(4-{[(1R)-2-hydroxy-1-phenylethyl]carbamoyl}phenyl)-1,3-dihydro-2H-isoindole-2-carboxamide;
5-cyano-N-(4-{[(2S)-1-hydroxybutan-2-yl]carbamoyl}phenyl)-1,3-dihydro-2H-isoindole-2-carboxamide;
5-cyano-N-{4-[(2,3-dihydroxypropyl)carbamoyl]phenyl}-1,3-dihydro-2H-isoindole-2-carboxamide;
5-cyano-N-{4-[(tetrahydro-2H-pyran-4-ylmethyl)carbamoyl]phenyl}-1,3-dihydro-2H-isoindole-2-carboxamide;
5-cyano-N-(4-{[2-hydroxy-1-(pyridin-2-yl)ethyl]carbamoyl}phenyl)-1,3-dihydro-2H-isoindole-2-carboxamide;
5-cyano-N-{4-[(1-hydroxy-4-methylpentan-2-yl)carbamoyl]phenyl}-1,3-dihydro-2H-isoindole-2-carboxamide;
5-cyano-N-(4-{[(1-methylpyrrolidin-3-yl)methyl]carbamoyl}phenyl)-1,3-dihydro-2H-isoindole-2-carboxamide;
5-cyano-N-(4-{[(1-methylpiperidin-4-yl)methyl]carbamoyl}phenyl)-1,3-dihydro-2H-isoindole-2-carboxamide;
5-cyano-N-{4-[(tetrahydro-2H-pyran-3-ylmethyl)carbamoyl]phenyl}-1,3-dihydro-2H-isoindole-2-carboxamide;
N-(5-{[(3S)-tetrahydrofuran-3-ylmethyl]carbamoyl}pyridin-2-yl)-1,3-dihydro-2H-isoindole-2-carboxamide;
N-[4-(2,6-diazaspiro[3.3]hept-2-ylcarbonyl)phenyl]-1,3-dihydro-2H-isoindole-2-carboxamide;
N-[4-(2,6-diazaspiro[3.4]oct-6-ylcarbonyl)phenyl]-1,3-dihydro-2H-isoindole-2-carboxamide;
N-[4-(2,7-diazaspiro[3.5]non-7-ylcarbonyl)phenyl]-1,3-dihydro-2H-isoindole-2-carboxamide;
N-[4-(2,6-diazaspiro[3.5]non-2-ylcarbonyl)phenyl]-1,3-dihydro-2H-isoindole-2-carboxamide;
N-[4-(1,7-diazaspiro[4.4]non-1-ylcarbonyl)phenyl]-1,3-dihydro-2H-isoindole-2-carboxamide;
N-[4-(1,7-diazaspiro[4.4]non-7-ylcarbonyl)phenyl]-1,3-dihydro-2H-isoindole-2-carboxamide;
N-[4-(2,7-diazaspiro[4.4]non-2-ylcarbonyl)phenyl]-1,3-dihydro-2H-isoindole-2-carboxamide;
N-[4-(2,8-diazaspiro[4.5]dec-2-ylcarbonyl)phenyl]-1,3-dihydro-2H-isoindole-2-carboxamide;
N-[4-(2,7-diazaspiro[4.5]dec-2-ylcarbonyl)phenyl]-1,3-dihydro-2H-isoindole-2-carboxamide;
N-[4-(2,6-diazaspiro[4.5]dec-2-ylcarbonyl)phenyl]-1,3-dihydro-2H-isoindole-2-carboxamide;
N-[4-(2,7-diazaspiro[4.5]dec-7-ylcarbonyl)phenyl]-1,3-dihydro-2H-isoindole-2-carboxamide;
N-[4-(3,9-diazaspiro[5.5]undec-3-ylcarbonyl)phenyl]-1,3-dihydro-2H-isoindole-2-carboxamide;
N-[4-(2,9-diazaspiro[5.5]undec-2-ylcarbonyl)phenyl]-1,3-dihydro-2H-isoindole-2-carboxamide;
N-[4-(2,8-diazaspiro[5.5]undec-2-ylcarbonyl)phenyl]-1,3-dihydro-2H-isoindole-2-carboxamide;
N-[4-(1,8-diazaspiro[5.5]undec-8-ylcarbonyl)phenyl]-1,3-dihydro-2H-isoindole-2-carboxamide;
N-[4-(1,8-diazaspiro[4.6]undec-8-ylcarbonyl)phenyl]-1,3-dihydro-2H-isoindole-2-carboxamide;
N-{4-[(1-oxa-8-azaspiro[4.5]dec-2-ylmethyl)carbamoyl]phenyl}-1,3-dihydro-2H-isoindole-2-carboxamide;
N-[4-(1-oxa-8-azaspiro[4.5]dec-3-ylcarbamoyl)phenyl]-1,3-dihydro-2H-isoindole-2-carboxamide;
N-{4-[(2-oxa-9-azaspiro[5.5]undec-3-ylmethyl)carbamoyl]phenyl}-1,3-dihydro-2H-isoindole-2-carboxamide;
N-[4-(1-oxa-4,8-diazaspiro[5.5]undec-4-ylcarbonyl)phenyl]-1,3-dihydro-2H-isoindole-2-carboxamide;
N-[4-(1,8-diazaspiro[4.5]dec-1-ylcarbonyl)phenyl]-1,3-dihydro-2H-isoindole-2-carboxamide;
N-[4-(1,8-diazaspiro[4.5]dec-8-ylcarbonyl)phenyl]-1,3-dihydro-2H-isoindole-2-carboxamide;
N-[4-(2,6-diazaspiro[3.4]oct-2-ylcarbonyl)phenyl]-1,3-dihydro-2H-isoindole-2-carboxamide;
N-[4-(1,7-diazaspiro[3.5]non-7-ylcarbonyl)phenyl]-1,3-dihydro-2H-isoindole-2-carboxamide;
N-[4-(1,6-diazaspiro[3.5]non-1-ylcarbonyl)phenyl]-1,3-dihydro-2H-isoindole-2-carboxamide;
N-[4-(2,5-diazaspiro[3.5]non-2-ylcarbonyl)phenyl]-1,3-dihydro-2H-isoindole-2-carboxamide;
N-[4-(5-oxa-2-azaspiro[3.4]oct-2-ylcarbonyl)phenyl]-1,3-dihydro-2H-isoindole-2-carboxamide;
N-[4-(6-oxa-2-azaspiro[3.5]non-2-ylcarbonyl)phenyl]-1,3-dihydro-2H-isoindole-2-carboxamide;
N-[4-(hexahydro-5H-furo[2,3-c]pyrrol-5-ylcarbonyl)phenyl]-1,3-dihydro-2H-isoindole-2-carboxamide;
N-[4-(tetrahydro-1H-furo[3,4-c]pyrrol-5(3H)-ylcarbonyl)phenyl]-1,3-dihydro-2H-isoindole-2-carboxamide;
N-[4-(hexahydrofuro[3,4-c]pyridin-5(3H)-ylcarbonyl)phenyl]-1,3-dihydro-2H-isoindole-2-carboxamide;
N-[4-(4-{benzyl[3-(morpholin-4-yl)propyl]amino}-4-oxobutyl)phenyl]-1,3-dihydro-2H-isoindole-2-carboxamide;
N-(4-phenylbutyl)-1,3-dihydro-2H-pyrrolo[3,4-c]pyridine-2-carboxamide;
N-[4-(2-{benzyl[3-(morpholin-4-yl)propyl]amino}ethyl)phenyl]-1,3-dihydro-2H-isoindole-2-carboxamide;
5-acetyl-N-{4-[(cyclopentylacetyl)amino]phenyl}-1,3-dihydro-2H-isoindole-2-carboxamide;
N-(4-{[(1,1-dioxidotetrahydrothiophen-3-yl)methyl]carbamoyl}phenyl)-1,3-dihydro-2H-pyrrolo[3,4-c]pyridine-2-carboxamide;
5-cyano-N-{4-[(3-methylbutyl)sulfamoyl]phenyl}-1,3-dihydro-2H-isoindole-2-carboxamide;
N-{4-[(3-methylbutyl)sulfamoyl]phenyl}-1,3-dihydro-2H-pyrrolo[3,4-c]pyridine-2-carboxamide;
N-{4-[(cyclopentylacetyl)amino]phenyl}-5-(1-hydroxyethyl)-1,3-dihydro-2H-isoindole-2-carboxamide;
N-[4-(butyrylamino)phenyl]-5-cyano-1,3-dihydro-2H-isoindole-2-carboxamide;
N-{4-[(pyrrolidin-3-ylmethyl)carbamoyl]phenyl}-1,3-dihydro-2H-pyrrolo[3,4-c]pyridine-2-carboxamide;
N-(4-{[(3S)-pyrrolidin-3-ylmethyl]carbamoyl}phenyl)-1,3-dihydro-2H-pyrrolo[3,4-c]pyridine-2-carboxamide;

N-(4-{[(1-methylpyrrolidin-3-yl)methyl]carbamoyl}phenyl)-1,3-dihydro-2H-pyrrolo[3,4-c]pyridine-2-carboxamide;

N-(4-{[(3-methoxybenzyl)sulfonyl]amino}phenyl)-1,3-dihydro-2H-isoindole-2-carboxamide;

N-(4-{[(1-methylpiperidin-4-yl)methyl]carbamoyl}phenyl)-1,3-dihydro-2H-pyrrolo[3,4-c]pyridine-2-carboxamide;

N-[4-(2,6-diazaspiro[3.4]oct-6-ylcarbonyl)phenyl]-5-fluoro-1,3-dihydro-2H-isoindole-2-carboxamide;

N-[4-(2,7-diazaspiro[3.5]non-7-ylcarbonyl)phenyl]-5-fluoro-1,3-dihydro-2H-isoindole-2-carboxamide;

N-[4-(1,7-diazaspiro[4.4]non-1-ylcarbonyl)phenyl]-5-fluoro-1,3-dihydro-2H-isoindole-2-carboxamide;

N-[4-(2,8-diazaspiro[4.5]dec-2-ylcarbonyl)phenyl]-5-fluoro-1,3-dihydro-2H-isoindole-2-carboxamide;

N-[4-(2,6-diazaspiro[4.5]dec-2-ylcarbonyl)phenyl]-5-fluoro-1,3-dihydro-2H-isoindole-2-carboxamide;

N-[4-(2,7-diazaspiro[4.5]dec-7-ylcarbonyl)phenyl]-5-fluoro-1,3-dihydro-2H-isoindole-2-carboxamide;

N-[4-(2,8-diazaspiro[5.5]undec-2-ylcarbonyl)phenyl]-5-fluoro-1,3-dihydro-2H-isoindole-2-carboxamide;

N-[4-(1,8-diazaspiro[5.5]undec-8-ylcarbonyl)phenyl]-5-fluoro-1,3-dihydro-2H-isoindole-2-carboxamide;

N-[4-(1,8-diazaspiro[4.6]undec-8-ylcarbonyl)phenyl]-5-fluoro-1,3-dihydro-2H-isoindole-2-carboxamide;

5-fluoro-N-{4-[(1-oxa-8-azaspiro[4.5]dec-2-ylmethyl)carbamoyl]phenyl}-1,3-dihydro-2H-isoindole-2-carboxamide;

5-fluoro-N-[4-(1-oxa-8-azaspiro[4.5]dec-3-ylcarbamoyl)phenyl]-1,3-dihydro-2H-isoindole-2-carboxamide;

5-fluoro-N-[4-(1-oxa-4,8-diazaspiro[5.5]undec-4-ylcarbonyl)phenyl]-1,3-dihydro-2H-isoindole-2-carboxamide;

N-[4-(1,8-diazaspiro[4.5]dec-1-ylcarbonyl)phenyl]-5-fluoro-1,3-dihydro-2H-isoindole-2-carboxamide;

N-[4-(1,8-diazaspiro[4.5]dec-8-ylcarbonyl)phenyl]-5-fluoro-1,3-dihydro-2H-isoindole-2-carboxamide;

N-[4-(2,6-diazaspiro[3.4]oct-2-ylcarbonyl)phenyl]-5-fluoro-1,3-dihydro-2H-isoindole-2-carboxamide;

N-[4-(1,7-diazaspiro[3.5]non-7-ylcarbonyl)phenyl]-5-fluoro-1,3-dihydro-2H-isoindole-2-carboxamide;

N-[4-(1,6-diazaspiro[3.5]non-1-ylcarbonyl)phenyl]-5-fluoro-1,3-dihydro-2H-isoindole-2-carboxamide;

N-[4-(2,5-diazaspiro[3.5]non-2-ylcarbonyl)phenyl]-5-fluoro-1,3-dihydro-2H-isoindole-2-carboxamide;

5-fluoro-N-[4-(5-oxa-2-azaspiro[3.4]oct-2-ylcarbonyl)phenyl]-1,3-dihydro-2H-isoindole-2-carboxamide;

5-fluoro-N-[4-(6-oxa-2-azaspiro[3.5]non-2-ylcarbonyl)phenyl]-1,3-dihydro-2H-isoindole-2-carboxamide;

5-fluoro-N-[4-(2-oxa-7-azaspiro[3.5]non-7-ylcarbonyl)phenyl]-1,3-dihydro-2H-isoindole-2-carboxamide;

5-fluoro-N-[4-(hexahydro-5H-furo[2,3-c]pyrrol-5-ylcarbonyl)phenyl]-1,3-dihydro-2H-isoindole-2-carboxamide;

5-fluoro-N-[4-(tetrahydro-1H-furo[3,4-c]pyrrol-5(3H)-ylcarbonyl)phenyl]-1,3-dihydro-2H-isoindole-2-carboxamide;

5-fluoro-N-[4-(hexahydrofuro[3,4-c]pyridin-5(3H)-ylcarbonyl)phenyl]-1,3-dihydro-2H-isoindole-2-carboxamide;

N-{4-[6-(3-acetylphenyl)-4-(3-hydroxypropyl)-2-oxoquinolin-1(2H)-yl]butyl}-1,3-dihydro-2H-isoindole-2-carboxamide;

N-{4-[1-(tetrahydrofuran-3-ylcarbonyl)piperidin-4-yl]phenyl}-1,3-dihydro-2H-pyrrolo[3,4-c]pyridine-2-carboxamide;

N-(4-{1-[(2-methoxyethoxy)acetyl]piperidin-4-yl}phenyl)-1,3-dihydro-2H-pyrrolo[3,4-c]pyridine-2-carboxamide;

N-{4-[1-(tetrahydrofuran-2-ylcarbonyl)piperidin-4-yl]phenyl}-1,3-dihydro-2H-pyrrolo[3,4-c]pyridine-2-carboxamide;

N-{4-[1-(tetrahydro-2H-pyran-4-ylcarbonyl)piperidin-4-yl]phenyl}-1,3-dihydro-2H-pyrrolo[3,4-c]pyridine-2-carboxamide;

N-{4-[1-(1,4-dioxan-2-ylcarbonyl)piperidin-4-yl]phenyl}-1,3-dihydro-2H-pyrrolo[3,4-c]pyridine-2-carboxamide;

N-(4-{1-[(1-methylpyrrolidin-3-yl)carbonyl]piperidin-4-yl}phenyl)-1,3-dihydro-2H-pyrrolo[3,4-c]pyridine-2-carboxamide;

N-(4-{1-[(1,1-dioxidotetrahydrothiophen-3-yl)carbonyl]piperidin-4-yl}phenyl)-1,3-dihydro-2H-pyrrolo[3,4-c]pyridine-2-carboxamide;

N-{4-[1-(2-hydroxy-2-methylpropanoyl)piperidin-4-yl]phenyl}-1,3-dihydro-2H-pyrrolo[3,4-c]pyridine-2-carboxamide;

N-{4-[1-(morpholin-4-ylacetyl)piperidin-4-yl]phenyl}-1,3-dihydro-2H-pyrrolo[3,4-c]pyridine-2-carboxamide;

5-(acetamidomethyl)-N-{4-[(cyclopentylacetyl)amino]phenyl}-1,3-dihydro-2H-isoindole-2-carboxamide;

N-{5-[2-(2-chlorobenzyl)-1,3-thiazol-4-yl]-2-thienyl}-1,3-dihydro-2H-isoindole-2-carboxamide;

N-[4-(4-fluorophenyl)butyl]-5-(hydroxymethyl)-1,3-dihydro-2H-isoindole-2-carboxamide;

N-[4-({[(3R)-1-isobutyrylpyrrolidin-3-yl]methyl}carbamoyl)phenyl]-1,3-dihydro-2H-pyrrolo[3,4-c]pyridine-2-carboxamide;

N-[4-({[(3R)-1-benzoylpyrrolidin-3-yl]methyl}carbamoyl)phenyl]-1,3-dihydro-2H-pyrrolo[3,4-c]pyridine-2-carboxamide;

N-[4-({[1-(tetrahydrofuran-3-ylcarbonyl)pyrrolidin-3-yl]methyl}carbamoyl)phenyl]-1,3-dihydro-2H-pyrrolo[3,4-c]pyridine-2-carboxamide;

N-[4-({[1-(methylsulfonyl)pyrrolidin-3-yl]methyl}carbamoyl)phenyl]-1,3-dihydro-2H-pyrrolo[3,4-c]pyridine-2-carboxamide;

N-[4-(1-isobutyl-1,2,3,6-tetrahydropyridin-4-yl)phenyl]-1,3-dihydro-2H-pyrrolo[3,4-c]pyridine-2-carboxamide;

N-{4-[1-(tetrahydrofuran-3-ylmethyl)-1,2,3,6-tetrahydropyridin-4-yl]phenyl}-1,3-dihydro-2H-pyrrolo[3,4-c]pyridine-2-carboxamide;

N-{4-[1-(tetrahydro-2H-pyran-4-ylmethyl)-1,2,3,6-tetrahydropyridin-4-yl]phenyl}-1,3-dihydro-2H-pyrrolo[3,4-c]pyridine-2-carboxamide;

N-[4-(1-isobutylpiperidin-4-yl)phenyl]-1,3-dihydro-2H-pyrrolo[3,4-c]pyridine-2-carboxamide;

N-{4-[1-(tetrahydrofuran-3-ylmethyl)piperidin-4-yl]phenyl}-1,3-dihydro-2H-pyrrolo[3,4-c]pyridine-2-carboxamide;

N-{4-[1-(tetrahydro-2H-pyran-4-ylmethyl)piperidin-4-yl]phenyl}-1,3-dihydro-2H-pyrrolo[3,4-c]pyridine-2-carboxamide;

N-{4-[(cyclopentylacetyl)amino]phenyl}-5-(2-hydroxypropan-2-yl)-1,3-dihydro-2H-isoindole-2-carboxamide;

tert-butyl {4-[(1,3-dihydro-2H-isoindol-2-ylcarbonyl)amino]benzyl}carbamate;

N-{4-[(cyclopentylacetyl)amino]phenyl}-1,3-dihydro-2H-pyrrolo[3,4-c]pyridine-2-carboxamide;

N-{4-[(cyclopentylacetyl)amino]phenyl}-5-(methoxymethyl)-1,3-dihydro-2H-isoindole-2-carboxamide;

N-[4-(5-{[(tetrahydrofuran-2-ylmethyl)amino]methyl}-1,2,4-oxadiazol-3-yl)phenyl]-1,3-dihydro-2H-isoindole-2-carboxamide;

N-(4-{5-[(4-methoxypiperidin-1-yl)methyl]-1,2,4-oxadiazol-3-yl}phenyl)-1,3-dihydro-2H-isoindole-2-carboxamide;

N-[4-(5-{[4-(2-methoxyethyl)piperazin-1-yl]methyl}-1,2,4-oxadiazol-3-yl)phenyl]-1,3-dihydro-2H-isoindole-2-carboxamide;

N-[4-({[1-(morpholin-4-yl)cyclopentyl]methyl}carbamoyl)phenyl]-1,3-dihydro-2H-pyrrolo[3,4-c]pyridine-2-carboxamide;

N-{4-[(1-pentanoylpiperidin-4-yl)oxy]phenyl}-1,3-dihydro-2H-pyrrolo[3,4-c]pyridine-2-carboxamide;

N-{4-[(1-acetylpiperidin-4-yl)oxy]phenyl}-1,3-dihydro-2H-pyrrolo[3,4-c]pyridine-2-carboxamide;

N-{4-[(1-butyrylpiperidin-4-yl)oxy]phenyl}-1,3-dihydro-2H-pyrrolo[3,4-c]pyridine-2-carboxamide;

N-(4-{[1-(2-methylbutanoyl)piperidin-4-yl]oxy}phenyl)-1,3-dihydro-2H-pyrrolo[3,4-c]pyridine-2-carboxamide;

N-(4-{[1-(3,3,3-trifluoropropanoyl)piperidin-4-yl]oxy}phenyl)-1,3-dihydro-2H-pyrrolo[3,4-c]pyridine-2-carboxamide;

N-(4-{[1-(methoxyacetyl)piperidin-4-yl]oxy}phenyl)-1,3-dihydro-2H-pyrrolo[3,4-c]pyridine-2-carboxamide;

N-(4-{[1-(tetrahydrofuran-2-ylcarbonyl)piperidin-4-yl]oxy}phenyl)-1,3-dihydro-2H-pyrrolo[3,4-c]pyridine-2-carboxamide;

N-(4-{[1-(cyclopropylcarbonyl)piperidin-4-yl]oxy}phenyl)-1,3-dihydro-2H-pyrrolo[3,4-c]pyridine-2-carboxamide;

N-(4-{[1-(cyclopropylacetyl)piperidin-4-yl]oxy}phenyl)-1,3-dihydro-2H-pyrrolo[3,4-c]pyridine-2-carboxamide;

N-(4-{[1-(cyclobutylcarbonyl)piperidin-4-yl]oxy}phenyl)-1,3-dihydro-2H-pyrrolo[3,4-c]pyridine-2-carboxamide;

N-(4-{[1-(cyclopentylcarbonyl)piperidin-4-yl]oxy}phenyl)-1,3-dihydro-2H-pyrrolo[3,4-c]pyridine-2-carboxamide;

N-(4-{[1-(cyclopentylacetyl)piperidin-4-yl]oxy}phenyl)-1,3-dihydro-2H-pyrrolo[3,4-c]pyridine-2-carboxamide;

N-(4-{[1-(cyclohexylcarbonyl)piperidin-4-yl]oxy}phenyl)-1,3-dihydro-2H-pyrrolo[3,4-c]pyridine-2-carboxamide;

N-{6-[(1-acetylpiperidin-4-yl)oxy]pyridin-3-yl}-1,3-dihydro-2H-isoindole-2-carboxamide;

N-{6-[(1-isobutyrylpiperidin-4-yl)oxy]pyridin-3-yl}-1,3-dihydro-2H-isoindole-2-carboxamide;

N-(6-{[1-(3-methylbutanoyl)piperidin-4-yl]oxy}pyridin-3-yl)-1,3-dihydro-2H-isoindole-2-carboxamide;

N-(6-{[1-(4,4,4-trifluorobutanoyl)piperidin-4-yl]oxy}pyridin-3-yl)-1,3-dihydro-2H-isoindole-2-carboxamide;

N-(6-{[1-(methoxyacetyl)piperidin-4-yl]oxy}pyridin-3-yl)-1,3-dihydro-2H-isoindole-2-carboxamide;

N-(6-{[1-(tetrahydrofuran-2-ylcarbonyl)piperidin-4-yl]oxy}pyridin-3-yl)-1,3-dihydro-2H-isoindole-2-carboxamide;

N-(6-{[1-(tetrahydrofuran-3-ylcarbonyl)piperidin-4-yl]oxy}pyridin-3-yl)-1,3-dihydro-2H-isoindole-2-carboxamide;

N-(6-{[1-(cyclopropylcarbonyl)piperidin-4-yl]oxy}pyridin-3-yl)-1,3-dihydro-2H-isoindole-2-carboxamide;

N-(6-{[1-(cyclopropylacetyl)piperidin-4-yl]oxy}pyridin-3-yl)-1,3-dihydro-2H-isoindole-2-carboxamide;

N-(6-{[1-(cyclobutylcarbonyl)piperidin-4-yl]oxy}pyridin-3-yl)-1,3-dihydro-2H-isoindole-2-carboxamide;

N-(6-{[1-(cyclopentylcarbonyl)piperidin-4-yl]oxy}pyridin-3-yl)-1,3-dihydro-2H-isoindole-2-carboxamide;

N-(6-{[1-(cyclopentylacetyl)piperidin-4-yl]oxy}pyridin-3-yl)-1,3-dihydro-2H-isoindole-2-carboxamide;

N-(6-{[1-(cyclohexylcarbonyl)piperidin-4-yl]oxy}pyridin-3-yl)-1,3-dihydro-2H-isoindole-2-carboxamide;

tert-butyl (2-{4-[(1,3-dihydro-2H-isoindol-2-ylcarbonyl)amino]phenyl}ethyl)carbamate;

N-(4-{1-[(2R)-tetrahydrofuran-2-ylcarbonyl]-1,2,3,6-tetrahydropyridin-4-yl}phenyl)-1,3-dihydro-2H-pyrrolo[3,4-c]pyridine-2-carboxamide;

N-(4-{1-[(2S)-tetrahydrofuran-2-ylcarbonyl]-1,2,3,6-tetrahydropyridin-4-yl}phenyl)-1,3-dihydro-2H-pyrrolo[3,4-c]pyridine-2-carboxamide;

N-(4-{[(1S)-1-(4-fluorophenyl)-2-hydroxyethyl]carbamoyl}phenyl)-1,3-dihydro-2H-pyrrolo[3,4-c]pyridine-2-carboxamide;

N-(4-{[(1S)-2-hydroxy-1-(4-methoxyphenyl)ethyl]carbamoyl}phenyl)-1,3-dihydro-2H-pyrrolo[3,4-c]pyridine-2-carboxamide;

N-[4-({[3-(hydroxymethyl)oxetan-3-yl]methyl}carbamoyl)phenyl]-1,3-dihydro-2H-pyrrolo[3,4-c]pyridine-2-carboxamide;

N-(4-{[(1S)-1-(1,3-benzodioxol-5-yl)-2-hydroxyethyl]carbamoyl}phenyl)-1,3-dihydro-2H-pyrrolo[3,4-c]pyridine-2-carboxamide;

N-{4-[(tetrahydrofuran-3-ylmethyl)sulfamoyl]phenyl}-1,3-dihydro-2H-isoindole-2-carboxamide;

N-{4-[(tetrahydrofuran-3-ylmethyl)sulfamoyl]phenyl}-1,3-dihydro-2H-pyrrolo[3,4-c]pyridine-2-carboxamide;

5-cyano-N-{4-[(tetrahydrofuran-3-ylmethyl)sulfamoyl]phenyl}-1,3-dihydro-2H-isoindole-2-carboxamide;

N-(4-{[(1S)-1-(4-fluorophenyl)-2-hydroxyethyl]carbamoyl}phenyl)-1,3-dihydro-2H-isoindole-2-carboxamide;

N-(4-{[(1S)-2-hydroxy-1-(4-methoxyphenyl)ethyl]carbamoyl}phenyl)-1,3-dihydro-2H-isoindole-2-carboxamide;

N-(4-{[(1S)-1-(1,3-benzodioxol-5-yl)-2-hydroxyethyl]carbamoyl}phenyl)-1,3-dihydro-2H-isoindole-2-carboxamide;

N-{4-[1-(tetrahydrofuran-3-ylcarbonyl)piperidin-4-yl]phenyl}-1,3-dihydro-2H-isoindole-2-carboxamide;

N-{4-[1-(tetrahydrofuran-2-ylcarbonyl)piperidin-4-yl]phenyl}-1,3-dihydro-2H-isoindole-2-carboxamide;

N-{4-[1-(tetrahydro-2H-pyran-4-ylcarbonyl)piperidin-4-yl]phenyl}-1,3-dihydro-2H-isoindole-2-carboxamide;

N-{4-[1-(1,4-dioxan-2-ylcarbonyl)piperidin-4-yl]phenyl}-1,3-dihydro-2H-isoindole-2-carboxamide;

N-(4-{1-[(1-methylpyrrolidin-3-yl)carbonyl]piperidin-4-yl}phenyl)-1,3-dihydro-2H-isoindole-2-carboxamide;

N-(4-{1-[(1,1-dioxidotetrahydrothiophen-3-yl)carbonyl]piperidin-4-yl}phenyl)-1,3-dihydro-2H-isoindole-2-carboxamide;

N-{4-[1-(2-hydroxy-2-methylpropanoyl)piperidin-4-yl]phenyl}-1,3-dihydro-2H-isoindole-2-carboxamide;

N-{4-[1-(morpholin-4-ylacetyl)piperidin-4-yl]phenyl}-1,3-dihydro-2H-isoindole-2-carboxamide;

N-(4-{[1-(3,3,3-trifluoropropanoyl)azetidin-3-yl]oxy}phenyl)-1,3-dihydro-2H-pyrrolo[3,4-c]pyridine-2-carboxamide;

N-(4-{[1-(4,4,4-trifluorobutanoyl)azetidin-3-yl]oxy}phenyl)-1,3-dihydro-2H-pyrrolo[3,4-c]pyridine-2-carboxamide;

N-(4-{[1-(tetrahydrofuran-2-ylcarbonyl)azetidin-3-yl]oxy}phenyl)-1,3-dihydro-2H-pyrrolo[3,4-c]pyridine-2-carboxamide;

N-(4-{[1-(tetrahydrofuran-3-ylacetyl)azetidin-3-yl]oxy}phenyl)-1,3-dihydro-2H-pyrrolo[3,4-c]pyridine-2-carboxamide;

N-(4-{[1-(cyclobutylcarbonyl)azetidin-3-yl]oxy}phenyl)-1,3-dihydro-2H-pyrrolo[3,4-c]pyridine-2-carboxamide;

N-(4-{[1-(cyclopentylcarbonyl)azetidin-3-yl]oxy}phenyl)-1,3-dihydro-2H-pyrrolo[3,4-c]pyridine-2-carboxamide;

N-(4-{[1-(3-phenylpropanoyl)pyrrolidin-3-yl]oxy}phenyl)-1,3-dihydro-2H-pyrrolo[3,4-c]pyridine-2-carboxamide;
N-(4-{[1-(phenylacetyl)pyrrolidin-3-yl]oxy}phenyl)-1,3-dihydro-2H-pyrrolo[3,4-c]pyridine-2-carboxamide;
N-[4-({1-[(4-methoxyphenyl)acetyl]pyrrolidin-3-yl}oxy)phenyl]-1,3-dihydro-2H-pyrrolo[3,4-c]pyridine-2-carboxamide;
N-(4-{[1-(methoxyacetyl)pyrrolidin-3-yl]oxy}phenyl)-1,3-dihydro-2H-pyrrolo[3,4-c]pyridine-2-carboxamide;
N-(4-{[1-(cyclopropylcarbonyl)pyrrolidin-3-yl]oxy}phenyl)-1,3-dihydro-2H-pyrrolo[3,4-c]pyridine-2-carboxamide;
N-(4-{[1-(cyclohexylcarbonyl)pyrrolidin-3-yl]oxy}phenyl)-1,3-dihydro-2H-pyrrolo[3,4-c]pyridine-2-carboxamide;
N-(4-{[1-(cyclopentylacetyl)pyrrolidin-3-yl]oxy}phenyl)-1,3-dihydro-2H-pyrrolo[3,4-c]pyridine-2-carboxamide;
N-(4-{[1-(cyclopentylcarbonyl)pyrrolidin-3-yl]oxy}phenyl)-1,3-dihydro-2H-pyrrolo[3,4-c]pyridine-2-carboxamide;
N-{4-[(1-benzoylpyrrolidin-3-yl)oxy]phenyl}-1,3-dihydro-2H-pyrrolo[3,4-c]pyridine-2-carboxamide;
N-(4-{[1-(3-ethoxypropanoyl)pyrrolidin-3-yl]oxy}phenyl)-1,3-dihydro-2H-pyrrolo[3,4-c]pyridine-2-carboxamide;
N-[4-({1-[(2-methylcyclopropyl)carbonyl]pyrrolidin-3-yl}oxy)phenyl]-1,3-dihydro-2H-pyrrolo[3,4-c]pyridine-2-carboxamide;
N-[4-({1-[(1-methylcyclopropyl)carbonyl]pyrrolidin-3-yl}oxy)phenyl]-1,3-dihydro-2H-pyrrolo[3,4-c]pyridine-2-carboxamide;
N-(4-{[1-(cyclobutylcarbonyl)pyrrolidin-3-yl]oxy}phenyl)-1,3-dihydro-2H-pyrrolo[3,4-c]pyridine-2-carboxamide;
N-(4-{[1-(3-methylbutanoyl)pyrrolidin-3-yl]oxy}phenyl)-1,3-dihydro-2H-pyrrolo[3,4-c]pyridine-2-carboxamide;
N-(4-{[1-(2-methylpropanoyl)pyrrolidin-3-yl]oxy}phenyl)-1,3-dihydro-2H-pyrrolo[3,4-c]pyridine-2-carboxamide;
N-{4-[(1-acetylpyrrolidin-3-yl)oxy]phenyl}-1,3-dihydro-2H-pyrrolo[3,4-c]pyridine-2-carboxamide;
N-(4-{[1-(4,4,4-trifluorobutanoyl)pyrrolidin-3-yl]oxy}phenyl)-1,3-dihydro-2H-pyrrolo[3,4-c]pyridine-2-carboxamide;
N-(4-{[1-(tetrahydrofuran-3-ylcarbonyl)pyrrolidin-3-yl]oxy}phenyl)-1,3-dihydro-2H-pyrrolo[3,4-c]pyridine-2-carboxamide;
N-(4-{[1-(tetrahydrofuran-2-ylcarbonyl)pyrrolidin-3-yl]oxy}phenyl)-1,3-dihydro-2H-pyrrolo[3,4-c]pyridine-2-carboxamide;
N-(4-{[1-(ethoxyacetyl)pyrrolidin-3-yl]oxy}phenyl)-1,3-dihydro-2H-pyrrolo[3,4-c]pyridine-2-carboxamide;
N-(4-{[1-(tetrahydrofuran-3-ylcarbonyl)piperidin-4-yl]oxy}phenyl)-1,3-dihydro-2H-isoindole-2-carboxamide;
N-(4-{1-[(1-methylpiperidin-4-yl)carbonyl]-1,2,3,6-tetrahydropyridin-4-yl}phenyl)-1,3-dihydro-2H-pyrrolo[3,4-c]pyridine-2-carboxamide;
N-(4-{1-[(1,1-dioxidotetrahydro-2H-thiopyran-4-yl)carbonyl]-1,2,3,6-tetrahydropyridin-4-yl}phenyl)-1,3-dihydro-2H-pyrrolo[3,4-c]pyridine-2-carboxamide;
N-(4-{1-[(3R)-tetrahydrofuran-3-ylcarbonyl]-1,2,3,6-tetrahydropyridin-4-yl}phenyl)-1,3-dihydro-2H-pyrrolo[3,4-c]pyridine-2-carboxamide;
N-(4-{1-[(3S)-tetrahydrofuran-3-ylcarbonyl]-1,2,3,6-tetrahydropyridin-4-yl}phenyl)-1,3-dihydro-2H-pyrrolo[3,4-c]pyridine-2-carboxamide;
N-(4-{4-[(2-methylpropanoyl)amino]cyclohex-1-en-1-yl}phenyl)-1,3-dihydro-2H-pyrrolo[3,4-c]pyridine-2-carboxamide;
5-cyano-N-{4-[1-(2-methylpropanoyl)-1,2,3,6-tetrahydropyridin-4-yl]phenyl}-1,3-dihydro-2H-isoindole-2-carboxamide;
tert-butyl [(1-{4-[(1,3-dihydro-2H-isoindol-2-ylcarbonyl)amino]phenyl}azetidin-3-yl)methyl]carbamate;
N-(4-{4-[(tetrahydrofuran-3-ylcarbonyl)amino]cyclohex-1-en-1-yl}phenyl)-1,3-dihydro-2H-pyrrolo[3,4-c]pyridine-2-carboxamide;
N-(4-{4-[(tetrahydro-2H-pyran-4-ylcarbonyl)amino]cyclohex-1-en-1-yl}phenyl)-1,3-dihydro-2H-pyrrolo[3,4-c]pyridine-2-carboxamide;
N-(4-{4-[(morpholin-4-ylacetyl)amino]cyclohex-1-en-1-yl}phenyl)-1,3-dihydro-2H-pyrrolo[3,4-c]pyridine-2-carboxamide;
N-[4-(4-{[(2-methoxyethoxy)acetyl]amino}cyclohex-1-en-1-yl)phenyl]-1,3-dihydro-2H-pyrrolo[3,4-c]pyridine-2-carboxamide;
N-(4-{[1-(cyclohexylacetyl)piperidin-4-yl]oxy}phenyl)-1,3-dihydro-2H-pyrrolo[3,4-c]pyridine-2-carboxamide;
N-(4-{[1-(tetrahydro-2H-pyran-4-ylacetyl)piperidin-4-yl]oxy}phenyl)-1,3-dihydro-2H-pyrrolo[3,4-c]pyridine-2-carboxamide;
N-(4-{[1-(2-methylbutanoyl)piperidin-4-yl]oxy}phenyl)-1,3-dihydro-2H-isoindole-2-carboxamide;
N-(4-{[1-(3-methylbutanoyl)piperidin-4-yl]oxy}phenyl)-1,3-dihydro-2H-isoindole-2-carboxamide;
N-(4-{[1-(2,3-dimethylbutanoyl)piperidin-4-yl]oxy}phenyl)-1,3-dihydro-2H-isoindole-2-carboxamide;
N-(4-{[1-(tetrahydrofuran-2-ylcarbonyl)piperidin-4-yl]oxy}phenyl)-1,3-dihydro-2H-isoindole-2-carboxamide;
N-(4-{[1-(cyclohexylcarbonyl)piperidin-4-yl]oxy}phenyl)-1,3-dihydro-2H-isoindole-2-carboxamide;
N-(4-{[1-(cyclohexylacetyl)piperidin-4-yl]oxy}phenyl)-1,3-dihydro-2H-isoindole-2-carboxamide;
N-(4-{[1-(tetrahydro-2H-pyran-4-ylacetyl)piperidin-4-yl]oxy}phenyl)-1,3-dihydro-2H-isoindole-2-carboxamide;
N-(4-{[1-(morpholin-4-ylacetyl)piperidin-4-yl]oxy}phenyl)-1,3-dihydro-2H-isoindole-2-carboxamide;
N-(4-{[1-(tetrahydrofuran-3-ylacetyl)piperidin-4-yl]oxy}phenyl)-1,3-dihydro-2H-isoindole-2-carboxamide;
N-(4-{[1-(tetrahydrofuran-2-ylacetyl)azetidin-3-yl]oxy}phenyl)-1,3-dihydro-2H-pyrrolo[3,4-c]pyridine-2-carboxamide;
N-(4-{[1-(tetrahydro-2H-pyran-4-ylacetyl)azetidin-3-yl]oxy}phenyl)-1,3-dihydro-2H-pyrrolo[3,4-c]pyridine-2-carboxamide;
N-(4-{[1-(morpholin-4-ylacetyl)azetidin-3-yl]oxy}phenyl)-1,3-dihydro-2H-pyrrolo[3,4-c]pyridine-2-carboxamide;
N-(4-{[1-(cyclohexylacetyl)azetidin-3-yl]oxy}phenyl)-1,3-dihydro-2H-pyrrolo[3,4-c]pyridine-2-carboxamide;
N-(4-{[1-(2-methylbutanoyl)azetidin-3-yl]oxy}phenyl)-1,3-dihydro-2H-pyrrolo[3,4-c]pyridine-2-carboxamide;
N-(4-{[1-(2,2-dimethylpropanoyl)azetidin-3-yl]oxy}phenyl)-1,3-dihydro-2H-pyrrolo[3,4-c]pyridine-2-carboxamide;
N-(4-{[1-(3,3-dimethylbutanoyl)azetidin-3-yl]oxy}phenyl)-1,3-dihydro-2H-pyrrolo[3,4-c]pyridine-2-carboxamide;
N-(4-{[1-(tricyclo[3.3.1.1~3,7~]dec-1-ylacetyl)azetidin-3-yl]oxy}phenyl)-1,3-dihydro-2H-pyrrolo[3,4-c]pyridine-2-carboxamide;
N-[4-({1-[(4-methoxycyclohexyl)carbonyl]azetidin-3-yl}oxy)phenyl]-1,3-dihydro-2H-pyrrolo[3,4-c]pyridine-2-carboxamide;
N-[4-({[4-(acetylamino)phenyl]sulfonyl}amino)phenyl]-1,3-dihydro-2H-pyrrolo[3,4-c]pyridine-2-carboxamide;
N-{4-[(propylsulfonyl)amino]phenyl}-1,3-dihydro-2H-pyrrolo[3,4-c]pyridine-2-carboxamide;

N-(4-{[(4-propylphenyl)sulfonyl]amino}phenyl)-1,3-dihydro-2H-pyrrolo[3,4-c]pyridine-2-carboxamide;
N-{4-[(butylsulfonyl)amino]phenyl}-1,3-dihydro-2H-pyrrolo[3,4-c]pyridine-2-carboxamide;
N-{4-[({[(1S,4R)-7,7-dimethyl-2-oxobicyclo[2.2.1]hept-1-yl]methyl}sulfonyl)amino]phenyl}-1,3-dihydro-2H-pyrrolo[3,4-c]pyridine-2-carboxamide;
N-{4-[(ethylsulfonyl)amino]phenyl}-1,3-dihydro-2H-pyrrolo[3,4-c]pyridine-2-carboxamide;
N-{4-[(benzylsulfonyl)amino]phenyl}-1,3-dihydro-2H-pyrrolo[3,4-c]pyridine-2-carboxamide;
N-(4-{[(4-fluorophenyl)sulfonyl]amino}phenyl)-1,3-dihydro-2H-pyrrolo[3,4-c]pyridine-2-carboxamide;
N-{4-[(thiophen-2-ylsulfonyl)amino]phenyl}-1,3-dihydro-2H-pyrrolo[3,4-c]pyridine-2-carboxamide;
N-[4-(1,7-diazaspiro[4.4]non-7-ylcarbonyl)phenyl]-1,3-dihydro-2H-pyrrolo[3,4-c]pyridine-2-carboxamide;
N-[4-(2,7-diazaspiro[4.5]dec-2-ylcarbonyl)phenyl]-1,3-dihydro-2H-pyrrolo[3,4-c]pyridine-2-carboxamide;
N-[4-(2,6-diazaspiro[4.5]dec-2-ylcarbonyl)phenyl]-1,3-dihydro-2H-pyrrolo[3,4-c]pyridine-2-carboxamide;
N-[4-(2,7-diazaspiro[4.5]dec-7-ylcarbonyl)phenyl]-1,3-dihydro-2H-pyrrolo[3,4-c]pyridine-2-carboxamide;
N-[4-(2,9-diazaspiro[5.5]undec-2-ylcarbonyl)phenyl]-1,3-dihydro-2H-pyrrolo[3,4-c]pyridine-2-carboxamide;
N-[4-(2,8-diazaspiro[5.5]undec-2-ylcarbonyl)phenyl]-1,3-dihydro-2H-pyrrolo[3,4-c]pyridine-2-carboxamide;
N-[4-(1,8-diazaspiro[5.5]undec-8-ylcarbonyl)phenyl]-1,3-dihydro-2H-pyrrolo[3,4-c]pyridine-2-carboxamide;
N-[4-(1,8-diazaspiro[4.6]undec-8-ylcarbonyl)phenyl]-1,3-dihydro-2H-pyrrolo[3,4-c]pyridine-2-carboxamide;
N-{4-[(1-oxa-8-azaspiro[4.5]dec-2-ylmethyl)carbamoyl]phenyl}-1,3-dihydro-2H-pyrrolo[3,4-c]pyridine-2-carboxamide;
N-[4-(1-oxa-8-azaspiro[4.5]dec-3-ylcarbamoyl)phenyl]-1,3-dihydro-2H-pyrrolo[3,4-c]pyridine-2-carboxamide;
N-{4-[(2-oxa-9-azaspiro[5.5]undec-3-ylmethyl)carbamoyl]phenyl}-1,3-dihydro-2H-pyrrolo[3,4-c]pyridine-2-carboxamide;
N-[4-(1-oxa-4,8-diazaspiro[5.5]undec-4-ylcarbonyl)phenyl]-1,3-dihydro-2H-pyrrolo[3,4-c]pyridine-2-carboxamide;
N-[4-(1,8-diazaspiro[4.5]dec-1-ylcarbonyl)phenyl]-1,3-dihydro-2H-pyrrolo[3,4-c]pyridine-2-carboxamide;
N-[4-(1,8-diazaspiro[4.5]dec-8-ylcarbonyl)phenyl]-1,3-dihydro-2H-pyrrolo[3,4-c]pyridine-2-carboxamide;
N-[4-(1,7-diazaspiro[3.5]non-7-ylcarbonyl)phenyl]-1,3-dihydro-2H-pyrrolo[3,4-c]pyridine-2-carboxamide;
N-[4-(1,6-diazaspiro[3.5]non-1-ylcarbonyl)phenyl]-1,3-dihydro-2H-pyrrolo[3,4-c]pyridine-2-carboxamide;
N-[4-(2,5-diazaspiro[3.5]non-2-ylcarbonyl)phenyl]-1,3-dihydro-2H-pyrrolo[3,4-c]pyridine-2-carboxamide;
N-[4-(5-oxa-2-azaspiro[3.4]oct-2-ylcarbonyl)phenyl]-1,3-dihydro-2H-pyrrolo[3,4-c]pyridine-2-carboxamide;
N-[4-(6-oxa-2-azaspiro[3.5]non-2-ylcarbonyl)phenyl]-1,3-dihydro-2H-pyrrolo[3,4-c]pyridine-2-carboxamide;
N-[4-(hexahydro-5H-furo[2,3-c]pyrrol-5-ylcarbonyl)phenyl]-1,3-dihydro-2H-pyrrolo[3,4-c]pyridine-2-carboxamide;
N-[4-(tetrahydro-1H-furo[3,4-c]pyrrol-5(3H)-ylcarbonyl)phenyl]-1,3-dihydro-2H-pyrrolo[3,4-c]pyridine-2-carboxamide;
N-[4-(hexahydrofuro[3,4-c]pyridin-5(3H)-ylcarbonyl)phenyl]-1,3-dihydro-2H-pyrrolo[3,4-c]pyridine-2-carboxamide;
N-{4-[1-(tetrahydrofuran-3-ylacetyl)-1,2,3,6-tetrahydropyridin-4-yl]phenyl}-1,3-dihydro-2H-pyrrolo[3,4-c]pyridine-2-carboxamide;
N-{4-[1-(tetrahydro-2H-pyran-4-ylacetyl)-1,2,3,6-tetrahydropyridin-4-yl]phenyl}-1,3-dihydro-2H-pyrrolo[3,4-c]pyridine-2-carboxamide;
N-{4-[1-(N,N-dimethylglycyl)-1,2,3,6-tetrahydropyridin-4-yl]phenyl}-1,3-dihydro-2H-pyrrolo[3,4-c]pyridine-2-carboxamide;
N-(4-{1-[(4-methylpiperazin-1-yl)acetyl]-1,2,3,6-tetrahydropyridin-4-yl}phenyl)-1,3-dihydro-2H-pyrrolo[3,4-c]pyridine-2-carboxamide;
N-(4-{4-[(tetrahydrofuran-2-ylacetyl)amino]cyclohex-1-en-1-yl}phenyl)-1,3-dihydro-2H-pyrrolo[3,4-c]pyridine-2-carboxamide;
N-(4-{4-[(tetrahydrofuran-3-ylacetyl)amino]cyclohex-1-en-1-yl}phenyl)-1,3-dihydro-2H-pyrrolo[3,4-c]pyridine-2-carboxamide;
N-(4-{4-[(cyclohexylcarbonyl)amino]cyclohex-1-en-1-yl}phenyl)-1,3-dihydro-2H-pyrrolo[3,4-c]pyridine-2-carboxamide;
N-[4-(4-{[(1,1-dioxidotetrahydrothiophen-3-yl)carbonyl]amino}cyclohex-1-en-1-yl)phenyl]-1,3-dihydro-2H-pyrrolo[3,4-c]pyridine-2-carboxamide;
N-[4-(4-{[(4,4-difluorocyclohexyl)carbonyl]amino}cyclohex-1-en-1-yl)phenyl]-1,3-dihydro-2H-pyrrolo[3,4-c]pyridine-2-carboxamide;
N-(4-{4-[(2-hydroxy-2-methylpropanoyl)amino]cyclohex-1-en-1-yl}phenyl)-1,3-dihydro-2H-pyrrolo[3,4-c]pyridine-2-carboxamide;
N-(4-{4-[(tetrahydrofuran-2-ylcarbonyl)amino]cyclohex-1-en-1-yl}phenyl)-1,3-dihydro-2H-pyrrolo[3,4-c]pyridine-2-carboxamide;
N-[4-(piperidin-1-ylsulfonyl)phenyl]-1,3-dihydro-2H-pyrrolo[3,4-c]pyridine-2-carboxamide;
5-fluoro-N-(4-{[1-(1,3-thiazol-2-yl)propan-2-yl]carbamoyl}phenyl)-1,3-dihydro-2H-isoindole-2-carboxamide;
N-{4-[(4,4-difluorocyclohexyl)carbamoyl]phenyl}-5-fluoro-1,3-dihydro-2H-isoindole-2-carboxamide;
N-(4-{[1-(3,5-dimethyl-1H-pyrazol-1-yl)propan-2-yl]carbamoyl}phenyl)-5-fluoro-1,3-dihydro-2H-isoindole-2-carboxamide;
5-fluoro-N-(4-{[2-methyl-2-(morpholin-4-yl)butyl]carbamoyl}phenyl)-1,3-dihydro-2H-isoindole-2-carboxamide;
5-fluoro-N-(4-{[2-(2-methyl-1,3-thiazol-4-yl)ethyl]carbamoyl}phenyl)-1,3-dihydro-2H-isoindole-2-carboxamide;
5-fluoro-N-(4-{[2-methyl-1-(morpholin-4-yl)propan-2-yl]carbamoyl}phenyl)-1,3-dihydro-2H-isoindole-2-carboxamide;
5-fluoro-N-{4-[(4-methoxybenzyl)carbamoyl]phenyl}-1,3-dihydro-2H-isoindole-2-carboxamide;
5-fluoro-N-(4-{[3-(morpholin-4-yl)propyl]carbamoyl}phenyl)-1,3-dihydro-2H-isoindole-2-carboxamide;
Nalpha-(4-{[(5-fluoro-1,3-dihydro-2H-isoindol-2-yl)carbonyl]amino}benzoyl)-D-phenylalaninamide;
N-(4-{[2-(acetylamino)phenyl]carbamoyl}phenyl)-5-fluoro-1,3-dihydro-2H-isoindole-2-carboxamide;
5-fluoro-N-[4-({4-[2-(2-hydroxyethoxy)ethyl]piperazin-1-yl}carbonyl)phenyl]-1,3-dihydro-2H-isoindole-2-carboxamide;
5-fluoro-N-(4-{[2-(furan-2-yl)-2-(pyrrolidin-1-yl)ethyl]carbamoyl}phenyl)-1,3-dihydro-2H-isoindole-2-carboxamide;

N-{4-[bis(2-methoxyethyl)carbamoyl]phenyl}-5-fluoro-1,3-dihydro-2H-isoindole-2-carboxamide;

N-{4-[(1-amino-1-oxohexan-2-yl)carbamoyl]phenyl}-5-fluoro-1,3-dihydro-2H-isoindole-2-carboxamide;

N-(4-{[2-(3,4-dimethoxyphenyl)ethyl]carbamoyl}phenyl)-5-fluoro-1,3-dihydro-2H-isoindole-2-carboxamide;

N-(4-{[(2S)-3,3-dimethyl-1-(methylamino)-1-oxobutan-2-yl]carbamoyl}phenyl)-5-fluoro-1,3-dihydro-2H-isoindole-2-carboxamide;

Nalpha-(4-{[(5-fluoro-1,3-dihydro-2H-isoindol-2-yl)carbonyl]amino}benzoyl)-L-phenylalaninamide;

N-(4-{[(2R)-1-amino-4-methyl-1-oxopentan-2-yl]carbamoyl}phenyl)-5-fluoro-1,3-dihydro-2H-isoindole-2-carboxamide;

N-{4-[(4-cyclohexylpiperazin-1-yl)carbonyl]phenyl}-5-fluoro-1,3-dihydro-2H-isoindole-2-carboxamide;

5-fluoro-N-(4-{[3-(methylcarbamoyl)phenyl]carbamoyl}phenyl)-1,3-dihydro-2H-isoindole-2-carboxamide;

N-{4-[(2-amino-2-oxo-1-phenylethyl)carbamoyl]phenyl}-5-fluoro-1,3-dihydro-2H-isoindole-2-carboxamide;

N-{4-[(3-tert-butoxypropyl)carbamoyl]phenyl}-5-fluoro-1,3-dihydro-2H-isoindole-2-carboxamide;

N-(4-{[2-(2,6-dimethylmorpholin-4-yl)ethyl]carbamoyl}phenyl)-5-fluoro-1,3-dihydro-2H-isoindole-2-carboxamide;

N-(4-{[(1R)-2-amino-2-oxo-1-phenylethyl]carbamoyl}phenyl)-5-fluoro-1,3-dihydro-2H-isoindole-2-carboxamide;

5-fluoro-N-{4-[(3-methoxybenzyl)carbamoyl]phenyl}-1,3-dihydro-2H-isoindole-2-carboxamide;

N-(4-{[2-(3,5-dimethyl-1H-pyrazol-1-yl)ethyl]carbamoyl}phenyl)-5-fluoro-1,3-dihydro-2H-isoindole-2-carboxamide;

5-fluoro-N-(4-{[2-methyl-2-(morpholin-4-yl)propyl]carbamoyl}phenyl)-1,3-dihydro-2H-isoindole-2-carboxamide;

5-fluoro-N-(4-{[(3S)-1-methyl-2-oxoazepan-3-yl]carbamoyl}phenyl)-1,3-dihydro-2H-isoindole-2-carboxamide;

5-fluoro-N-(4-{[2-(4-methylpiperazin-1-yl)ethyl]carbamoyl}phenyl)-1,3-dihydro-2H-isoindole-2-carboxamide;

5-fluoro-N-(4-{[4-(morpholin-4-yl)benzyl]carbamoyl}phenyl)-1,3-dihydro-2H-isoindole-2-carboxamide;

5-fluoro-N-(4-{[3-(piperidin-1-yl)propyl]carbamoyl}phenyl)-1,3-dihydro-2H-isoindole-2-carboxamide;

N-(4-{[3-(5-methyl-1H-pyrazol-1-yl)propyl]carbamoyl}phenyl)-5,7-dihydro-6H-pyrrolo[3,4-b]pyridine-6-carboxamide;

N-(4-{[2-(4-chloro-1H-pyrazol-1-yl)ethyl]carbamoyl}phenyl)-5,7-dihydro-6H-pyrrolo[3,4-b]pyridine-6-carboxamide;

N-(4-{[1-(3,5-dimethyl-1H-pyrazol-1-yl)propan-2-yl]carbamoyl}phenyl)-5,7-dihydro-6H-pyrrolo[3,4-b]pyridine-6-carboxamide;

N-(4-{[2-methyl-2-(morpholin-4-yl)butyl]carbamoyl}phenyl)-5,7-dihydro-6H-pyrrolo[3,4-b]pyridine-6-carboxamide;

N-{4-[(4-methoxybenzyl)carbamoyl]phenyl}-5,7-dihydro-6H-pyrrolo[3,4-b]pyridine-6-carboxamide;

N-(4-{[3-(morpholin-4-yl)propyl]carbamoyl}phenyl)-5,7-dihydro-6H-pyrrolo[3,4-b]pyridine-6-carboxamide;

N-[4-({4-[2-(2-hydroxyethoxy)ethyl]piperazin-1-yl}carbonyl)phenyl]-5,7-dihydro-6H-pyrrolo[3,4-b]pyridine-6-carboxamide;

N-{4-[(2-carbamoylbenzyl)carbamoyl]phenyl}-5,7-dihydro-6H-pyrrolo[3,4-b]pyridine-6-carboxamide;

N-{4-[bis(2-methoxyethyl)carbamoyl]phenyl}-5,7-dihydro-6H-pyrrolo[3,4-b]pyridine-6-carboxamide;

N-{4-[(1-amino-1-oxohexan-2-yl)carbamoyl]phenyl}-5,7-dihydro-6H-pyrrolo[3,4-b]pyridine-6-carboxamide;

N-(4-{[2-(3,4-dimethoxyphenyl)ethyl]carbamoyl}phenyl)-5,7-dihydro-6H-pyrrolo[3,4-b]pyridine-6-carboxamide;

N-(4-{[4-(pyrazin-2-yl)piperazin-1-yl]carbonyl}phenyl)-5,7-dihydro-6H-pyrrolo[3,4-b]pyridine-6-carboxamide;

Nalpha-{4-[(5,7-dihydro-6H-pyrrolo[3,4-b]pyridin-6-ylcarbonyl)amino]benzoyl}-L-phenylalaninamide;

N-(4-{[(2R)-1-amino-4-methyl-1-oxopentan-2-yl]carbamoyl}phenyl)-5,7-dihydro-6H-pyrrolo[3,4-b]pyridine-6-carboxamide;

N-{4-[(4-cyclohexylpiperazin-1-yl)carbonyl]phenyl}-5,7-dihydro-6H-pyrrolo[3,4-b]pyridine-6-carboxamide;

N-{4-[(3-tert-butoxypropyl)carbamoyl]phenyl}-5,7-dihydro-6H-pyrrolo[3,4-b]pyridine-6-carboxamide;

N-(4-{[2-(2,6-dimethylmorpholin-4-yl)ethyl]carbamoyl}phenyl)-5,7-dihydro-6H-pyrrolo[3,4-b]pyridine-6-carboxamide;

N-{4-[(3-methoxybenzyl)carbamoyl]phenyl}-5,7-dihydro-6H-pyrrolo[3,4-b]pyridine-6-carboxamide;

N-(4-{[2-methyl-2-(morpholin-4-yl)propyl]carbamoyl}phenyl)-5,7-dihydro-6H-pyrrolo[3,4-b]pyridine-6-carboxamide;

N-(4-{[(3S)-1-methyl-2-oxoazepan-3-yl]carbamoyl}phenyl)-5,7-dihydro-6H-pyrrolo[3,4-b]pyridine-6-carboxamide;

N-(4-{[2-(4-methylpiperazin-1-yl)ethyl]carbamoyl}phenyl)-5,7-dihydro-6H-pyrrolo[3,4-b]pyridine-6-carboxamide;

N-(4-{[4-(morpholin-4-yl)benzyl]carbamoyl}phenyl)-5,7-dihydro-6H-pyrrolo[3,4-b]pyridine-6-carboxamide;

N-(4-{[3-(piperidin-1-yl)propyl]carbamoyl}phenyl)-5,7-dihydro-6H-pyrrolo[3,4-b]pyridine-6-carboxamide;

N-[4-(4,5,6,7-tetrahydro-1H-indazol-5-ylcarbamoyl)phenyl]-5,7-dihydro-6H-pyrrolo[3,4-b]pyridine-6-carboxamide;

5-fluoro-N-{4-[(3-methoxy-2,2-dimethylpropyl)carbamoyl]phenyl}-1,3-dihydro-2H-isoindole-2-carboxamide;

N-{4-[(3,3-dimethylbutyl)carbamoyl]phenyl}-5-fluoro-1,3-dihydro-2H-isoindole-2-carboxamide;

5-fluoro-N-(4-{[1-(furan-2-yl)propan-2-yl]carbamoyl}phenyl)-1,3-dihydro-2H-isoindole-2-carboxamide;

5-fluoro-N-(4-{[(3-methyl-1,2-oxazol-5-yl)methyl]carbamoyl}phenyl)-1,3-dihydro-2H-isoindole-2-carboxamide;

N-(4-{[(2R)-1-cyanobutan-2-yl]carbamoyl}phenyl)-5-fluoro-1,3-dihydro-2H-isoindole-2-carboxamide;

N-{4-[(2R)-butan-2-ylcarbamoyl]phenyl}-5-fluoro-1,3-dihydro-2H-isoindole-2-carboxamide;

5-fluoro-N-(4-{[2-(1H-pyrazol-1-yl)ethyl]carbamoyl}phenyl)-1,3-dihydro-2H-isoindole-2-carboxamide;

5-fluoro-N-{4-[methyl(3-methylbutyl)carbamoyl]phenyl}-1,3-dihydro-2H-isoindole-2-carboxamide;

N-(4-{[1-(ethylamino)-1-oxopropan-2-yl]carbamoyl}phenyl)-5-fluoro-1,3-dihydro-2H-isoindole-2-carboxamide;

5-fluoro-N-(4-{[(1-methyl-1H-pyrazol-3-yl)methyl]carbamoyl}phenyl)-1,3-dihydro-2H-isoindole-2-carboxamide;
5-fluoro-N-{4-[(2-methoxybutyl)carbamoyl]phenyl}-1,3-dihydro-2H-isoindole-2-carboxamide;
N-(4-{[4-(dimethylamino)butyl]carbamoyl}phenyl)-5-fluoro-1,3-dihydro-2H-isoindole-2-carboxamide;
5-fluoro-N-{4-[(3S)-tetrahydrofuran-3-ylcarbamoyl]phenyl}-1,3-dihydro-2H-isoindole-2-carboxamide;
5-fluoro-N-{4-[(1-methoxybutan-2-yl)carbamoyl]phenyl}-1,3-dihydro-2H-isoindole-2-carboxamide;
N-{4-[(2-ethoxypropyl)carbamoyl]phenyl}-5-fluoro-1,3-dihydro-2H-isoindole-2-carboxamide;
N-{4-[benzyl(methyl)carbamoyl]phenyl}-5-fluoro-1,3-dihydro-2H-isoindole-2-carboxamide;
N-{4-[(2S)-butan-2-ylcarbamoyl]phenyl}-5-fluoro-1,3-dihydro-2H-isoindole-2-carboxamide;
5-fluoro-N-(4-{[2-(5-methyl-1H-pyrazol-1-yl)ethyl]carbamoyl}phenyl)-1,3-dihydro-2H-isoindole-2-carboxamide;
5-fluoro-N-(4-{[2-(3-methyl-1H-pyrazol-1-yl)ethyl]carbamoyl}phenyl)-1,3-dihydro-2H-isoindole-2-carboxamide;
5-fluoro-N-{4-[(2-methylpropyl)carbamoyl]phenyl}-1,3-dihydro-2H-isoindole-2-carboxamide;
5-fluoro-N-{4-[(pyridin-3-ylmethyl)carbamoyl]phenyl}-1,3-dihydro-2H-isoindole-2-carboxamide;
5-fluoro-N-{4-[(tetrahydrofuran-2-ylmethyl)carbamoyl]phenyl}-1,3-dihydro-2H-isoindole-2-carboxamide;
N-(4-{[(1R)-1-cyclopropylethyl]carbamoyl}phenyl)-5-fluoro-1,3-dihydro-2H-isoindole-2-carboxamide;
5-fluoro-N-(4-{[1-(1-methylcyclopropyl)ethyl]carbamoyl}phenyl)-1,3-dihydro-2H-isoindole-2-carboxamide;
5-fluoro-N-{4-[(thiophen-2-ylmethyl)carbamoyl]phenyl}-1,3-dihydro-2H-isoindole-2-carboxamide;
N-(4-{[(1S)-1-cyclopropylethyl]carbamoyl}phenyl)-5-fluoro-1,3-dihydro-2H-isoindole-2-carboxamide;
5-fluoro-N-{4-[(4-methoxybutyl)carbamoyl]phenyl}-1,3-dihydro-2H-isoindole-2-carboxamide;
5-fluoro-N-(4-{[(5-methyl-1,3-oxazol-2-yl)methyl]carbamoyl}phenyl)-1,3-dihydro-2H-isoindole-2-carboxamide;
5-fluoro-N-(4-{[2-(tetrahydro-2H-pyran-3-yl)ethyl]carbamoyl}phenyl)-1,3-dihydro-2H-isoindole-2-carboxamide;
5-fluoro-N-(4-{[(2S)-1-methoxypropan-2-yl]carbamoyl}phenyl)-1,3-dihydro-2H-isoindole-2-carboxamide;
N-{4-[(3,3-dimethyl-2-oxobutyl)carbamoyl]phenyl}-5-fluoro-1,3-dihydro-2H-isoindole-2-carboxamide;
5-fluoro-N-(4-{[(1-methyl-1H-pyrrol-2-yl)methyl]carbamoyl}phenyl)-1,3-dihydro-2H-isoindole-2-carboxamide;
5-fluoro-N-(4-{[2-(propan-2-yloxy)ethyl]carbamoyl}phenyl)-1,3-dihydro-2H-isoindole-2-carboxamide;
N-(4-{[3-(dimethylamino)propyl]carbamoyl}phenyl)-5-fluoro-1,3-dihydro-2H-isoindole-2-carboxamide;
N-(4-{[(2S)-1-amino-1-oxobutan-2-yl]carbamoyl}phenyl)-5-fluoro-1,3-dihydro-2H-isoindole-2-carboxamide;
5-fluoro-N-[4-(tetrahydro-2H-pyran-3-ylcarbamoyl)phenyl]-1,3-dihydro-2H-isoindole-2-carboxamide;
5-fluoro-N-(4-{[2-(1H-pyrrol-1-yl)ethyl]carbamoyl}phenyl)-1,3-dihydro-2H-isoindole-2-carboxamide;
5-fluoro-N-{4-[(1-methoxypropan-2-yl)carbamoyl]phenyl}-1,3-dihydro-2H-isoindole-2-carboxamide;
5-fluoro-N-{4-[(2-methoxyethyl)carbamoyl]phenyl}-1,3-dihydro-2H-isoindole-2-carboxamide;
N-[4-(cyclopentylcarbamoyl)phenyl]-5-fluoro-1,3-dihydro-2H-isoindole-2-carboxamide;
5-fluoro-N-(4-{[(2S)-3-methylbutan-2-yl]carbamoyl}phenyl)-1,3-dihydro-2H-isoindole-2-carboxamide;
5-fluoro-N-(4-{[(2R)-3-methylbutan-2-yl]carbamoyl}phenyl)-1,3-dihydro-2H-isoindole-2-carboxamide;
5-fluoro-N-(4-{[(2S)-2-methylbutyl]carbamoyl}phenyl)-1,3-dihydro-2H-isoindole-2-carboxamide;
5-fluoro-N-{4-[(2-hydroxy-2-methylpropyl)carbamoyl]phenyl}-1,3-dihydro-2H-isoindole-2-carboxamide;
5-fluoro-N-(4-{[2-(tetrahydro-2H-pyran-4-yl)ethyl]carbamoyl}phenyl)-1,3-dihydro-2H-isoindole-2-carboxamide;
N-[4-(butylcarbamoyl)phenyl]-5-fluoro-1,3-dihydro-2H-isoindole-2-carboxamide;
5-fluoro-N-{4-[methyl(tetrahydrofuran-2-ylmethyl)carbamoyl]phenyl}-1,3-dihydro-2H-isoindole-2-carboxamide;
5-fluoro-N-{4-[(2-methoxyethyl)(methyl)carbamoyl]phenyl}-1,3-dihydro-2H-isoindole-2-carboxamide;
N-{4-[(1-cyanoethyl)carbamoyl]phenyl}-5-fluoro-1,3-dihydro-2H-isoindole-2-carboxamide;
5-fluoro-N-(4-{[(5-methyl-1,2-oxazol-3-yl)methyl]carbamoyl}phenyl)-1,3-dihydro-2H-isoindole-2-carboxamide;
5-fluoro-N-{4-[(3R)-tetrahydrofuran-3-ylcarbamoyl]phenyl}-1,3-dihydro-2H-isoindole-2-carboxamide;
N-{4-[(3-methoxy-2,2-dimethylpropyl)carbamoyl]phenyl}-5,7-dihydro-6H-pyrrolo[3,4-b]pyridine-6-carboxamide;
N-{4-[(3,3-dimethylbutyl)carbamoyl]phenyl}-5,7-dihydro-6H-pyrrolo[3,4-b]pyridine-6-carboxamide;
N-(4-{[1-(furan-2-yl)propan-2-yl]carbamoyl}phenyl)-5,7-dihydro-6H-pyrrolo[3,4-b]pyridine-6-carboxamide;
N-(4-{[(3-methyl-1,2-oxazol-5-yl)methyl]carbamoyl}phenyl)-5,7-dihydro-6H-pyrrolo[3,4-b]pyridine-6-carboxamide;
N-(4-{[(2R)-1-cyanobutan-2-yl]carbamoyl}phenyl)-5,7-dihydro-6H-pyrrolo[3,4-b]pyridine-6-carboxamide;
N-{4-[methyl(3-methylbutyl)carbamoyl]phenyl}-5,7-dihydro-6H-pyrrolo[3,4-b]pyridine-6-carboxamide;
N-(4-{[(1-methyl-1H-pyrazol-3-yl)methyl]carbamoyl}phenyl)-5,7-dihydro-6H-pyrrolo[3,4-b]pyridine-6-carboxamide;
N-{4-[(2-methoxybutyl)carbamoyl]phenyl}-5,7-dihydro-6H-pyrrolo[3,4-b]pyridine-6-carboxamide;
N-(4-{[4-(dimethylamino)butyl]carbamoyl}phenyl)-5,7-dihydro-6H-pyrrolo[3,4-b]pyridine-6-carboxamide;
N-(4-{[1-(1,3-thiazol-2-yl)ethyl]carbamoyl}phenyl)-5,7-dihydro-6H-pyrrolo[3,4-b]pyridine-6-carboxamide;
N-(4-{[1-(1-methyl-1H-pyrazol-4-yl)ethyl]carbamoyl}phenyl)-5,7-dihydro-6H-pyrrolo[3,4-b]pyridine-6-carboxamide;
N-{4-[(3S)-tetrahydrofuran-3-ylcarbamoyl]phenyl}-5,7-dihydro-6H-pyrrolo[3,4-b]pyridine-6-carboxamide;
N-{4-[(1-methoxybutan-2-yl)carbamoyl]phenyl}-5,7-dihydro-6H-pyrrolo[3,4-b]pyridine-6-carboxamide;
N-{4-[(4-aminobenzyl)carbamoyl]phenyl}-5,7-dihydro-6H-pyrrolo[3,4-b]pyridine-6-carboxamide;
N-{4-[(2-ethoxypropyl)carbamoyl]phenyl}-5,7-dihydro-6H-pyrrolo[3,4-b]pyridine-6-carboxamide;
N-{4-[(6-methoxypyridin-3-yl)carbamoyl]phenyl}-5,7-dihydro-6H-pyrrolo[3,4-b]pyridine-6-carboxamide;

N-{4-[(2S)-butan-2-ylcarbamoyl]phenyl}-5,7-dihydro-6H-pyrrolo[3,4-b]pyridine-6-carboxamide;
N-{4-[(1-cyanocyclopropyl)carbamoyl]phenyl}-5,7-dihydro-6H-pyrrolo[3,4-b]pyridine-6-carboxamide;
N-(4-{[2-(5-methyl-1H-pyrazol-1-yl)ethyl]carbamoyl}phenyl)-5,7-dihydro-6H-pyrrolo[3,4-b]pyridine-6-carboxamide;
N-(4-{[(4-methyl-1,3-thiazol-2-yl)methyl]carbamoyl}phenyl)-5,7-dihydro-6H-pyrrolo[3,4-b]pyridine-6-carboxamide;
N-{4-[(3-hydroxypropyl)carbamoyl]phenyl}-5,7-dihydro-6H-pyrrolo[3,4-b]pyridine-6-carboxamide;
N-{4-[(2-methylpropyl)carbamoyl]phenyl}-5,7-dihydro-6H-pyrrolo[3,4-b]pyridine-6-carboxamide;
N-{4-[(tetrahydrofuran-2-ylmethyl)carbamoyl]phenyl}-5,7-dihydro-6H-pyrrolo[3,4-b]pyridine-6-carboxamide;
N-(4-{[(1R)-1-cyclopropylethyl]carbamoyl}phenyl)-5,7-dihydro-6H-pyrrolo[3,4-b]pyridine-6-carboxamide;
N-(4-{[1-(1-methylcyclopropyl)ethyl]carbamoyl}phenyl)-5,7-dihydro-6H-pyrrolo[3,4-b]pyridine-6-carboxamide;
N-{4-[(thiophen-2-ylmethyl)carbamoyl]phenyl}-5,7-dihydro-6H-pyrrolo[3,4-b]pyridine-6-carboxamide;
N-(4-{[(1S)-1-cyclopropylethyl]carbamoyl}phenyl)-5,7-dihydro-6H-pyrrolo[3,4-b]pyridine-6-carboxamide;
N-{4-[(4-methoxybutyl)carbamoyl]phenyl}-5,7-dihydro-6H-pyrrolo[3,4-b]pyridine-6-carboxamide;
N-(4-{[2-(tetrahydro-2H-pyran-3-yl)ethyl]carbamoyl}phenyl)-5,7-dihydro-6H-pyrrolo[3,4-b]pyridine-6-carboxamide;
N-(4-{[(2S)-1-methoxypropan-2-yl]carbamoyl}phenyl)-5,7-dihydro-6H-pyrrolo[3,4-b]pyridine-6-carboxamide;
N-{4-[(3,3-dimethyl-2-oxobutyl)carbamoyl]phenyl}-5,7-dihydro-6H-pyrrolo[3,4-b]pyridine-6-carboxamide;
N-(4-{[(1-methyl-1H-pyrrol-2-yl)methyl]carbamoyl}phenyl)-5,7-dihydro-6H-pyrrolo[3,4-b]pyridine-6-carboxamide;
N-(4-{[2-(propan-2-yloxy)ethyl]carbamoyl}phenyl)-5,7-dihydro-6H-pyrrolo[3,4-b]pyridine-6-carboxamide;
N-(4-{[3-(dimethylamino)propyl]carbamoyl}phenyl)-5,7-dihydro-6H-pyrrolo[3,4-b]pyridine-6-carboxamide;
N-[4-(tetrahydro-2H-pyran-3-ylcarbamoyl)phenyl]-5,7-dihydro-6H-pyrrolo[3,4-b]pyridine-6-carboxamide;
N-(4-{[2-(1H-pyrrol-1-yl)ethyl]carbamoyl}phenyl)-5,7-dihydro-6H-pyrrolo[3,4-b]pyridine-6-carboxamide;
N-{4-[(1-methoxypropan-2-yl)carbamoyl]phenyl}-5,7-dihydro-6H-pyrrolo[3,4-b]pyridine-6-carboxamide;
N-{4-[(3-aminobenzyl)carbamoyl]phenyl}-5,7-dihydro-6H-pyrrolo[3,4-b]pyridine-6-carboxamide;
N-(4-{[(2R)-3-methylbutan-2-yl]carbamoyl}phenyl)-5,7-dihydro-6H-pyrrolo[3,4-b]pyridine-6-carboxamide;
N-{4-[(tetrahydro-2H-pyran-3-ylmethyl)carbamoyl]phenyl}-5,7-dihydro-6H-pyrrolo[3,4-b]pyridine-6-carboxamide;
N-{4-[(2-hydroxy-2-methylpropyl)carbamoyl]phenyl}-5,7-dihydro-6H-pyrrolo[3,4-b]pyridine-6-carboxamide;
N-[4-(butylcarbamoyl)phenyl]-5,7-dihydro-6H-pyrrolo[3,4-b]pyridine-6-carboxamide;
N-{4-[methyl(tetrahydrofuran-2-ylmethyl)carbamoyl]phenyl}-5,7-dihydro-6H-pyrrolo[3,4-b]pyridine-6-carboxamide;
N-{4-[(2-methoxyethyl)(methyl)carbamoyl]phenyl}-5,7-dihydro-6H-pyrrolo[3,4-b]pyridine-6-carboxamide;
N-{4-[(1-cyanoethyl)carbamoyl]phenyl}-5,7-dihydro-6H-pyrrolo[3,4-b]pyridine-6-carboxamide;
N-{4-[(3R)-tetrahydrofuran-3-ylcarbamoyl]phenyl}-5,7-dihydro-6H-pyrrolo[3,4-b]pyridine-6-carboxamide;
N-{4-[(cyclopentylmethyl)carbamoyl]phenyl}-5,7-dihydro-6H-pyrrolo[3,4-b]pyridine-6-carboxamide;
N-{4-[(2-methoxy-2-methylpropyl)carbamoyl]phenyl}-5,7-dihydro-6H-pyrrolo[3,4-b]pyridine-6-carboxamide;
N-{4-[(cyclopropylmethyl)carbamoyl]phenyl}-5,7-dihydro-6H-pyrrolo[3,4-b]pyridine-6-carboxamide;
N-{4-[methyl(propyl)carbamoyl]phenyl}-5,7-dihydro-6H-pyrrolo[3,4-b]pyridine-6-carboxamide;
N-{4-[(pyridin-4-ylmethyl)carbamoyl]phenyl}-5,7-dihydro-6H-pyrrolo[3,4-b]pyridine-6-carboxamide;
methyl 1-{4-[(1,3-dihydro-2H-pyrrolo[3,4-c]pyridin-2-ylcarbonyl)amino]phenyl}azetidine-3-carboxylate;
N-(4-{3-[(3-methylbutyl)carbamoyl]azetidin-1-yl}phenyl)-1,3-dihydro-2H-pyrrolo[3,4-c]pyridine-2-carboxamide;
N-(4-{3-[(tetrahydrofuran-2-ylmethyl)carbamoyl]azetidin-1-yl}phenyl)-1,3-dihydro-2H-pyrrolo[3,4-c]pyridine-2-carboxamide;
N-(4-{3-[(tetrahydro-2H-pyran-4-ylmethyl)carbamoyl]azetidin-1-yl}phenyl)-1,3-dihydro-2H-pyrrolo[3,4-c]pyridine-2-carboxamide;
N-{4-[3-(benzylcarbamoyl)azetidin-1-yl]phenyl}-1,3-dihydro-2H-pyrrolo[3,4-c]pyridine-2-carboxamide;
N-{4-[3-(cyclopentylcarbamoyl)azetidin-1-yl]phenyl}-1,3-dihydro-2H-pyrrolo[3,4-c]pyridine-2-carboxamide;
N-(4-{3-[(cyclopentylmethyl)carbamoyl]azetidin-1-yl}phenyl)-1,3-dihydro-2H-pyrrolo[3,4-c]pyridine-2-carboxamide;
N-(4-{3-[(2-methoxyethyl)carbamoyl]azetidin-1-yl}phenyl)-1,3-dihydro-2H-pyrrolo[3,4-c]pyridine-2-carboxamide;
N-{4-[1-(3-methylbutanoyl)-1,2,3,6-tetrahydropyridin-4-yl]phenyl}-1,3-dihydro-2H-pyrrolo[3,4-c]pyridine-2-carboxamide;
N-{4-[1-(cyclopentylacetyl)-1,2,3,6-tetrahydropyridin-4-yl]phenyl}-1,3-dihydro-2H-pyrrolo[3,4-c]pyridine-2-carboxamide;
N-{4-[1-(tetrahydro furan-2-ylacetyl)-1,2,3,6-tetrahydropyridin-4-yl]phenyl}-1,3-dihydro-2H-pyrrolo[3,4-c]pyridine-2-carboxamide;
N-{4-[1-(tetrahydro-2H-pyran-2-ylacetyl)-1,2,3,6-tetrahydropyridin-4-yl]phenyl}-1,3-dihydro-2H-pyrrolo[3,4-c]pyridine-2-carboxamide;
N-{4-[1-(pyrrolidin-1-ylacetyl)-1,2,3,6-tetrahydropyridin-4-yl]phenyl}-1,3-dihydro-2H-pyrrolo[3,4-c]pyridine-2-carboxamide;
N-{4-[1-(pyrazin-2-ylcarbonyl)-1,2,3,6-tetrahydropyridin-4-yl]phenyl}-1,3-dihydro-2H-pyrrolo[3,4-c]pyridine-2-carboxamide;
N-{4-[(3-methoxy-2,2-dimethylpropyl)carbamoyl]phenyl}-1,3-dihydro-2H-isoindole-2-carboxamide;
N-{4-[(4,4-difluorocyclohexyl)carbamoyl]phenyl}-1,3-dihydro-2H-isoindole-2-carboxamide;
N-(4-{[(2R)-1-cyanobutan-2-yl]carbamoyl}phenyl)-1,3-dihydro-2H-isoindole-2-carboxamide;
N-{4-[(2-methoxybutyl)carbamoyl]phenyl}-1,3-dihydro-2H-isoindole-2-carboxamide;
N-(4-{[1-(ethylamino)-1-oxopropan-2-yl]carbamoyl}phenyl)-1,3-dihydro-2H-isoindole-2-carboxamide;
N-(4-{[2-methyl-2-(morpholin-4-yl)butyl]carbamoyl}phenyl)-1,3-dihydro-2H-isoindole-2-carboxamide;
N-(4-{[(1R)-1-cyclopropylethyl]carbamoyl}phenyl)-1,3-dihydro-2H-isoindole-2-carboxamide;
N-(4-{[(1S)-1-cyclopropylethyl]carbamoyl}phenyl)-1,3-dihydro-2H-isoindole-2-carboxamide;

N-(6-{[(2S)-tetrahydrofuran-2-ylmethyl]
carbamoyl}pyridazin-3-yl)-1,3-dihydro-2H-isoindole-2-
carboxamide;
N-{4-[(3S)-tetrahydrofuran-3-ylcarbamoyl]phenyl}-1,3-di-
hydro-2H-isoindole-2-carboxamide;
N-(4-{[2-(tetrahydro-2H-pyran-3-yl)ethyl]
carbamoyl}phenyl)-1,3-dihydro-2H-isoindole-2-carboxa-
mide;
N-(4-{[(5-methyl-1,3-oxazol-2-yl)methyl]
carbamoyl}phenyl)-1,3-dihydro-2H-isoindole-2-carboxa-
mide;
N-[4-({2-[(dimethylamino)methyl]benzyl}carbamoyl)phe-
nyl]-1,3-dihydro-2H-isoindole-2-carboxamide;
N-(4-{[(1R)-2-amino-2-oxo-1-phenylethyl]
carbamoyl}phenyl)-1,3-dihydro-2H-isoindole-2-carboxa-
mide;
N-[4-(1,3-oxazol-2-ylcarbamoyl)phenyl]-1,3-dihydro-2H-
isoindole-2-carboxamide;
N-[4-(tetrahydro-2H-pyran-3-ylcarbamoyl)phenyl]-1,3-di-
hydro-2H-isoindole-2-carboxamide;
N-(4-{[2-(2,6-dimethylmorpholin-4-yl)ethyl]
carbamoyl}phenyl)-1,3-dihydro-2H-isoindole-2-carboxa-
mide;
N-(4-{[1-(1-methylcyclopropyl)ethyl]carbamoyl}phenyl)-
1,3-dihydro-2H-isoindole-2-carboxamide;
N-(4-{[2-(furan-2-yl)-2-(pyrrolidin-1-yl)ethyl]
carbamoyl}phenyl)-1,3-dihydro-2H-isoindole-2-carboxa-
mide;
N-(4-{1-[(2S)-tetrahydrofuran-2-ylcarbonyl]piperidin-4-
yl}phenyl)-1,3-dihydro-2H-pyrrolo[3,4-c]pyridine-2-car-
boxamide;
N-(4-{1-[(3S)-tetrahydrofuran-3-ylcarbonyl]piperidin-4-
yl}phenyl)-1,3-dihydro-2H-pyrrolo[3,4-c]pyridine-2-car-
boxamide;
5-cyano-N-{4-[1-(tetrahydrofuran-3-ylcarbonyl)-1,2,3,6-
tetrahydropyridin-4-yl]phenyl}-1,3-dihydro-2H-isoin-
dole-2-carboxamide;
5-cyano-N-{4-[1-(tetrahydro-2H-pyran-4-ylcarbonyl)-1,2,
3,6-tetrahydropyridin-4-yl]phenyl}-1,3-dihydro-2H-
isoindole-2-carboxamide;
5-cyano-N-{4-[1-(2-hydroxy-2-methylpropanoyl)-1,2,3,6-
tetrahydropyridin-4-yl]phenyl}-1,3-dihydro-2H-isoin-
dole-2-carboxamide;
5-cyano-N-{4-[1-(morpholin-4-ylacetyl)-1,2,3,6-tetrahy-
dropyridin-4-yl]phenyl}-1,3-dihydro-2H-isoindole-2-car-
boxamide;
N-{4-[(4-fluorobenzyl)(3-methylbutanoyl)amino]butyl}-1,
3-dihydro-2H-isoindole-2-carboxamide;
N-[4-(9-chloro-5-oxo-2,3,3a,4,4a,5-hexahydro-6H-furo[2',
3':2,3]cyclobuta[1,2-c]quinolin-6-yl)butyl]-1,3-dihydro-
2H-pyrrolo[3,4-c]pyridine-2-carboxamide;
N-{4-[7-chloro-1-(2-hydroxyethyl)-3-oxo-1,3-dihydrocy-
clobuta[c]quinolin-4(2H)-yl]butyl}-1,3-dihydro-2H-pyr-
rolo[3,4-c]pyridine-2-carboxamide;
N-(4-{[1-(tetrahydro-2H-pyran-2-ylcarbonyl)azetidin-3-yl]
oxy}phenyl)-1,3-dihydro-2H-pyrrolo[3,4-c]pyridine-2-
carboxamide;
N-(4-{[1-(tetrahydro-2H-pyran-2-ylcarbonyl)pyrrolidin-3-
yl]oxy}phenyl)-1,3-dihydro-2H-pyrrolo[3,4-c]pyridine-
2-carboxamide;
N-(6-{[(2R)-tetrahydrofuran-2-ylmethyl]
carbamoyl}pyridazin-3-yl)-1,3-dihydro-2H-isoindole-2-
carboxamide;
N-(4-{4-[(cyclopropylacetyl)amino]cyclohex-1-en-1-
yl}phenyl)-1,3-dihydro-2H-pyrrolo[3,4-c]pyridine-2-car-
boxamide;
N-{4-[(1-acetylpiperidin-3-yl)oxy]phenyl}-1,3-dihydro-
2H-pyrrolo[3,4-c]pyridine-2-carboxamide;
N-{4-[(1-butanoylpiperidin-3-yl)oxy]phenyl}-1,3-dihydro-
2H-pyrrolo[3,4-c]pyridine-2-carboxamide;
N-(4-{[1-(3-methylbutanoyl)piperidin-3-yl]oxy}phenyl)-1,
3-dihydro-2H-pyrrolo[3,4-c]pyridine-2-carboxamide;
N-(4-{[1-(methoxyacetyl)piperidin-3-yl]oxy}phenyl)-1,3-
dihydro-2H-pyrrolo[3,4-c]pyridine-2-carboxamide;
N-(4-{[1-(2-methylbutanoyl)piperidin-3-yl]oxy}phenyl)-1,
3-dihydro-2H-pyrrolo[3,4-c]pyridine-2-carboxamide;
N-(4-{[1-(3,3,3-trifluoropropanoyl)piperidin-3-yl]
oxy}phenyl)-1,3-dihydro-2H-pyrrolo[3,4-c]pyridine-2-
carboxamide;
N-(4-{[1-(cyclopropylacetyl)piperidin-3-yl]oxy}phenyl)-1,
3-dihydro-2H-pyrrolo[3,4-c]pyridine-2-carboxamide;
N-(4-{[1-(cyclobutylcarbonyl)piperidin-3-yl]oxy}phenyl)-
1,3-dihydro-2H-pyrrolo[3,4-c]pyridine-2-carboxamide;
N-(4-{[1-(cyclobutylacetyl)piperidin-3-yl]oxy}phenyl)-1,3-
dihydro-2H-pyrrolo[3,4-c]pyridine-2-carboxamide;
N-(4-{[1-(cyclopentylcarbonyl)piperidin-3-yl]oxy}phenyl)-
1,3-dihydro-2H-pyrrolo[3,4-c]pyridine-2-carboxamide;
N-(4-{[1-(cyclopentylacetyl)piperidin-3-yl]oxy}phenyl)-1,
3-dihydro-2H-pyrrolo[3,4-c]pyridine-2-carboxamide;
N-[4-({1-[(2S)-tetrahydrofuran-2-ylcarbonyl]piperidin-3-
yl}oxy)phenyl]-1,3-dihydro-2H-pyrrolo[3,4-c]pyridine-
2-carboxamide;
N-[4-({1-[(2R)-tetrahydrofuran-2-ylcarbonyl]piperidin-3-
yl}oxy)phenyl]-1,3-dihydro-2H-pyrrolo[3,4-c]pyridine-
2-carboxamide;
N-(4-{[1-(tetrahydro-2H-pyran-4-ylcarbonyl)piperidin-3-
yl]oxy}phenyl)-1,3-dihydro-2H-pyrrolo[3,4-c]pyridine-
2-carboxamide;
N-(4-{[1-(tetrahydro-2H-pyran-2-ylcarbonyl)piperidin-3-
yl]oxy}phenyl)-1,3-dihydro-2H-pyrrolo[3,4-c]pyridine-
2-carboxamide;
N-(4-{[1-(tetrahydro-2H-pyran-4-ylacetyl)piperidin-3-yl]
oxy}phenyl)-1,3-dihydro-2H-pyrrolo[3,4-c]pyridine-2-
carboxamide;
N-(4-{[1-(tetrahydrofuran-2-ylacetyl)piperidin-3-yl]
oxy}phenyl)-1,3-dihydro-2H-pyrrolo[3,4-c]pyridine-2-
carboxamide;
N-(4-{[1-(tetrahydrofuran-3-ylacetyl)piperidin-3-yl]
oxy}phenyl)-1,3-dihydro-2H-pyrrolo[3,4-c]pyridine-2-
carboxamide;
N-(4-{[3-(3,5-dimethyl-1H-pyrazol-1-yl)propyl]
carbamoyl}phenyl)-1,3-dihydro-2H-isoindole-2-carboxa-
mide;
N-(4-{[(3S)-1-methyl-2-oxoazepan-3-yl]
carbamoyl}phenyl)-1,3-dihydro-2H-isoindole-2-carboxa-
mide;
N-(4-{[2-(1H-pyrazol-1-yl)ethyl]carbamoyl}phenyl)-1,3-
dihydro-2H-isoindole-2-carboxamide;
N-(4-{[1-(1,3-thiazol-2-yl)ethyl]carbamoyl}phenyl)-1,3-di-
hydro-2H-isoindole-2-carboxamide;
N-(4-{[1-(furan-2-yl)propan-2-yl]carbamoyl}phenyl)-1,3-
dihydro-2H-isoindole-2-carboxamide;
N-(4-{[1-(1-methyl-1H-pyrazol-4-yl)ethyl]
carbamoyl}phenyl)-1,3-dihydro-2H-isoindole-2-carboxa-
mide;
N-(4-{[(2R)-1-amino-4-methyl-1-oxopentan-2-yl]
carbamoyl}phenyl)-1,3-dihydro-2H-isoindole-2-carboxa-
mide;
N-(4-{[1-(3,5-dimethyl-1H-pyrazol-1-yl)propan-2-yl]
carbamoyl}phenyl)-1,3-dihydro-2H-isoindole-2-carboxa-
mide;
N-{4-[(2,2-difluoroethyl)carbamoyl]phenyl}-1,3-dihydro-
2H-isoindole-2-carboxamide;

N-(4-{[2-(tetrahydro-2H-pyran-4-yl)ethyl]
carbamoyl}phenyl)-1,3-dihydro-2H-isoindole-2-carboxamide;
N-{4-[(tetrahydrofuran-2-ylmethyl)carbamoyl]phenyl}-1,3-dihydro-2H-isoindole-2-carboxamide;
N-{4-[(2-methoxy-2-methylpropyl)carbamoyl]phenyl}-1,3-dihydro-2H-isoindole-2-carboxamide;
N-(4-{[(5-methyl-1,2-oxazol-3-yl)methyl]
carbamoyl}phenyl)-1,3-dihydro-2H-isoindole-2-carboxamide;
N-(4-{[(1-methyl-1H-pyrazol-4-yl)methyl]
carbamoyl}phenyl)-1,3-dihydro-2H-isoindole-2-carboxamide;
N-(4-{[2-(3,5-dimethyl-1H-pyrazol-1-yl)ethyl]
carbamoyl}phenyl)-1,3-dihydro-2H-isoindole-2-carboxamide;
Nalpha-{4-[(1,3-dihydro-2H-isoindol-2-ylcarbonyl)amino]
benzoyl}-L-phenylalaninamide;
N-(4-{[2-(2-methyl-1,3-thiazol-4-yl)ethyl]
carbamoyl}phenyl)-1,3-dihydro-2H-isoindole-2-carboxamide;
N-(4-{[(2S)-3,3-dimethyl-1-(methylamino)-1-oxobutan-2-yl]carbamoyl}phenyl)-1,3-dihydro-2H-isoindole-2-carboxamide;
N-[4-(thiophen-3-ylcarbamoyl)phenyl]-1,3-dihydro-2H-isoindole-2-carboxamide;
N-(4-{[2-(5-methyl-1H-pyrazol-1-yl)ethyl]
carbamoyl}phenyl)-1,3-dihydro-2H-isoindole-2-carboxamide;
N-(4-{[2-(3-methyl-1H-pyrazol-1-yl)ethyl]
carbamoyl}phenyl)-1,3-dihydro-2H-isoindole-2-carboxamide;
N-{4-[(2S)-butan-2-ylcarbamoyl]phenyl}-1,3-dihydro-2H-isoindole-2-carboxamide;
N-{4-[(3,3-dimethyl-2-oxobutyl)carbamoyl]phenyl}-1,3-dihydro-2H-isoindole-2-carboxamide;
N-(4-{[(1-methyl-1H-pyrazol-3-yl)methyl]
carbamoyl}phenyl)-1,3-dihydro-2H-isoindole-2-carboxamide;
N-(4-{[2-(acetylamino)phenyl]carbamoyl}phenyl)-1,3-dihydro-2H-isoindole-2-carboxamide;
N-{4-[(1-methoxybutan-2-yl)carbamoyl]phenyl}-1,3-dihydro-2H-isoindole-2-carboxamide;
N-[4-(tetrahydro-2H-pyran-4-ylcarbamoyl)phenyl]-1,3-dihydro-2H-isoindole-2-carboxamide;
N-[4-(pyrimidin-4-ylcarbamoyl)phenyl]-1,3-dihydro-2H-isoindole-2-carboxamide;
N-(4-{[2-(1H-pyrrol-1-yl)ethyl]carbamoyl}phenyl)-1,3-dihydro-2H-isoindole-2-carboxamide;
N-(4-{[(2S)-2-methylbutyl]carbamoyl}phenyl)-1,3-dihydro-2H-isoindole-2-carboxamide;
N-{4-[(1-amino-1-oxohexan-2-yl)carbamoyl]phenyl}-1,3-dihydro-2H-isoindole-2-carboxamide;
N-{4-[(2-amino-2-oxo-1-phenylethyl)carbamoyl]phenyl}-1,3-dihydro-2H-isoindole-2-carboxamide;
N-{4-[(3-tert-butoxypropyl)carbamoyl]phenyl}-1,3-dihydro-2H-isoindole-2-carboxamide;
N-(4-{[3-(methylcarbamoyl)phenyl]carbamoyl}phenyl)-1,3-dihydro-2H-isoindole-2-carboxamide;
N-(4-{[(2R)-3-methylbutan-2-yl]carbamoyl}phenyl)-1,3-dihydro-2H-isoindole-2-carboxamide;
N-(4-{[(2S)-3-methylbutan-2-yl]carbamoyl}phenyl)-1,3-dihydro-2H-isoindole-2-carboxamide;
N-(4-{[2-methyl-1-(morpholin-4-yl)propan-2-yl]
carbamoyl}phenyl)-1,3-dihydro-2H-isoindole-2-carboxamide;
N-(4-{[1-(5-oxo-L-prolyl)piperidin-4-yl]oxy}phenyl)-1,3-dihydro-2H-pyrrolo[3,4-c]pyridine-2-carboxamide;
N-(4-{[2-methyl-2-(morpholin-4-yl)propyl]
carbamoyl}phenyl)-1,3-dihydro-2H-isoindole-2-carboxamide;
N-{4-[(2-ethoxypropyl)carbamoyl]phenyl}-1,3-dihydro-2H-isoindole-2-carboxamide;
N-{4-[1-(tetrahydro furan-2-ylacetyl)piperidin-4-yl]butyl}-1,3-dihydro-2H-pyrrolo[3,4-c]pyridine-2-carboxamide;
N-(4-{1-[(1,1-dioxidotetrahydrothiophen-3-yl)carbonyl]piperidin-4-yl}butyl)-1,3-dihydro-2H-pyrrolo[3,4-c]pyridine-2-carboxamide;
N-{4-[1-(tetrahydro furan-3-ylacetyl)piperidin-4-yl]butyl}-1,3-dihydro-2H-pyrrolo[3,4-c]pyridine-2-carboxamide;
N-{4-[1-(cyclohexylcarbonyl)piperidin-4-yl]butyl}-1,3-dihydro-2H-pyrrolo[3,4-c]pyridine-2-carboxamide;
N-(4-{1-[(4,4-difluorocyclohexyl)carbonyl]piperidin-4-yl}butyl)-1,3-dihydro-2H-pyrrolo[3,4-c]pyridine-2-carboxamide;
N-{4-[1-(2-hydroxy-2-methylpropanoyl)piperidin-4-yl]butyl}-1,3-dihydro-2H-pyrrolo[3,4-c]pyridine-2-carboxamide;
N-(4-{1-[(2R)-tetrahydrofuran-2-ylcarbonyl]piperidin-4-yl}butyl)-1,3-dihydro-2H-pyrrolo[3,4-c]pyridine-2-carboxamide;
N-(4-{1-[(2S)-tetrahydrofuran-2-ylcarbonyl]piperidin-4-yl}butyl)-1,3-dihydro-2H-pyrrolo[3,4-c]pyridine-2-carboxamide;
N-(4-{1-[(2-methoxyethoxy)acetyl]piperidin-4-yl}butyl)-1,3-dihydro-2H-pyrrolo[3,4-c]pyridine-2-carboxamide;
N-{4-[1-(tetrahydrofuran-3-ylcarbonyl)piperidin-4-yl]butyl}-1,3-dihydro-2H-pyrrolo[3,4-c]pyridine-2-carboxamide;
N-(4-{1-[(propan-2-yloxy)acetyl]piperidin-4-yl}butyl)-1,3-dihydro-2H-pyrrolo[3,4-c]pyridine-2-carboxamide;
N-{4-[1-(cyclopropylacetyl)piperidin-4-yl]butyl}-1,3-dihydro-2H-pyrrolo[3,4-c]pyridine-2-carboxamide;
N-{4-[1-(4,4,4-trifluorobutanoyl)piperidin-4-yl]butyl}-1,3-dihydro-2H-pyrrolo[3,4-c]pyridine-2-carboxamide;
N-{4-[(3-ethoxypropanoyl)amino]phenyl}-1,3-dihydro-2H-pyrrolo[3,4-c]pyridine-2-carboxamide;
N-(4-{[(1-acetylpiperidin-4-yl)carbonyl]amino}phenyl)-1,3-dihydro-2H-pyrrolo[3,4-c]pyridine-2-carboxamide;
N-{4-[(ethoxyacetyl)amino]phenyl}-1,3-dihydro-2H-pyrrolo[3,4-c]pyridine-2-carboxamide;
N-{4-[(tetrahydrofuran-2-ylcarbonyl)amino]phenyl}-1,3-dihydro-2H-pyrrolo[3,4-c]pyridine-2-carboxamide;
N-{4-[(tetrahydrofuran-3-ylcarbonyl)amino]phenyl}-1,3-dihydro-2H-pyrrolo[3,4-c]pyridine-2-carboxamide;
N-{4-[(cyclopentylcarbonyl)amino]phenyl}-1,3-dihydro-2H-pyrrolo[3,4-c]pyridine-2-carboxamide;
N-{7-oxo-7-[(3-phenylpropyl)amino]heptyl}-1,3-dihydro-2H-isoindole-2-carboxamide;
N-{4-[(bicyclo[2.2.1]hept-2-ylacetyl)amino]phenyl}-1,3-dihydro-2H-pyrrolo[3,4-c]pyridine-2-carboxamide;
N-{4-[(1,3-thiazol-5-ylcarbonyl)amino]phenyl}-1,3-dihydro-2H-pyrrolo[3,4-c]pyridine-2-carboxamide;
N-(4-{[(4-oxo-4,5,6,7-tetrahydro-1-benzo furan-3-yl)carbonyl]amino}phenyl)-1,3-dihydro-2H-pyrrolo[3,4-c]pyridine-2-carboxamide;
N-(4-{2-[(3-methylbutanoyl)amino]ethyl}phenyl)-1,3-dihydro-2H-isoindole-2-carboxamide;
N-(4-{2-[(4-methylpentanoyl)amino]ethyl}phenyl)-1,3-dihydro-2H-isoindole-2-carboxamide;
N-(4-{2-[(ethoxyacetyl)amino]ethyl}phenyl)-1,3-dihydro-2H-isoindole-2-carboxamide;

N-[4-(2-{[(2-methoxyethoxy)acetyl]amino}ethyl)phenyl]-1,3-dihydro-2H-isoindole-2-carboxamide;
N-(4-{2-[(tetrahydro furan-2-ylcarbonyl)amino]ethyl}phenyl)-1,3-dihydro-2H-isoindole-2-carboxamide;
N-(4-{2-[(cyclopentylcarbonyl)amino]ethyl}phenyl)-1,3-dihydro-2H-isoindole-2-carboxamide;
N-(4-{2-[(cyclopentylacetyl)amino]ethyl}phenyl)-1,3-dihydro-2H-isoindole-2-carboxamide;
N-{4-[2-(benzoylamino)ethyl]phenyl}-1,3-dihydro-2H-isoindole-2-carboxamide;
N-(4-{2-[(tetrahydro-2H-pyran-4-ylcarbonyl)amino]ethyl}phenyl)-1,3-dihydro-2H-isoindole-2-carboxamide;
N-(4-{2-[(tetrahydro-2H-pyran-4-ylacetyl)amino]ethyl}phenyl)-1,3-dihydro-2H-isoindole-2-carboxamide;
N-(4-{2-[(tetrahydro furan-3-ylacetyl)amino]ethyl}phenyl)-1,3-dihydro-2H-isoindole-2-carboxamide;
N-(4-{1-[(2R)-tetrahydrofuran-2-ylcarbonyl]piperidin-4-yl}phenyl)-1,3-dihydro-2H-pyrrolo[3,4-c]pyridine-2-carboxamide;
N-(4-{1-[(3R)-tetrahydrofuran-3-ylcarbonyl]piperidin-4-yl}phenyl)-1,3-dihydro-2H-pyrrolo[3,4-c]pyridine-2-carboxamide;
N-(4-{[1-(5-oxo-L-prolyl)azetidin-3-yl]oxy}phenyl)-1,3-dihydro-2H-pyrrolo[3,4-c]pyridine-2-carboxamide;
N-{4-[(1-propanoylazetidin-3-yl)oxy]phenyl}-1,3-dihydro-2H-pyrrolo[3,4-c]pyridine-2-carboxamide;
N-(4-{[1-(2,2-dimethylbutanoyl)azetidin-3-yl]oxy}phenyl)-1,3-dihydro-2H-pyrrolo[3,4-c]pyridine-2-carboxamide;
N-(4-{[1-(2-ethylbutanoyl)azetidin-3-yl]oxy}phenyl)-1,3-dihydro-2H-pyrrolo[3,4-c]pyridine-2-carboxamide;
N-(4-{[1-(pent-4-ynoyl)azetidin-3-yl]oxy}phenyl)-1,3-dihydro-2H-pyrrolo[3,4-c]pyridine-2-carboxamide;
N-(4-{[1-(furan-2-ylcarbonyl)azetidin-3-yl]oxy}phenyl)-1,3-dihydro-2H-pyrrolo[3,4-c]pyridine-2-carboxamide;
N-(4-{[1-(furan-3-ylcarbonyl)azetidin-3-yl]oxy}phenyl)-1,3-dihydro-2H-pyrrolo[3,4-c]pyridine-2-carboxamide;
N-(4-{[1-(thiophen-3-ylcarbonyl)azetidin-3-yl]oxy}phenyl)-1,3-dihydro-2H-pyrrolo[3,4-c]pyridine-2-carboxamide;
N-(4-{[1-(1H-pyrrol-2-ylcarbonyl)azetidin-3-yl]oxy}phenyl)-1,3-dihydro-2H-pyrrolo[3,4-c]pyridine-2-carboxamide;
N-(4-{[1-(pyrimidin-4-ylcarbonyl)azetidin-3-yl]oxy}phenyl)-1,3-dihydro-2H-pyrrolo[3,4-c]pyridine-2-carboxamide;
N-[4-({1-[(5-methylpyrazin-2-yl)carbonyl]azetidin-3-yl}oxy)phenyl]-1,3-dihydro-2H-pyrrolo[3,4-c]pyridine-2-carboxamide;
N-(4-{[1-(N,N-dimethylglycyl)azetidin-3-yl]oxy}phenyl)-1,3-dihydro-2H-pyrrolo[3,4-c]pyridine-2-carboxamide;
N-(4-{[1-(N,N-dimethyl-beta-alanyl)azetidin-3-yl]oxy}phenyl)-1,3-dihydro-2H-pyrrolo[3,4-c]pyridine-2-carboxamide;
N-(4-{[1-(pyrrolidin-1-ylacetyl)azetidin-3-yl]oxy}phenyl)-1,3-dihydro-2H-pyrrolo[3,4-c]pyridine-2-carboxamide;
N-[4-({1-[3-(pyrrolidin-1-yl)propanoyl]azetidin-3-yl}oxy)phenyl]-1,3-dihydro-2H-pyrrolo[3,4-c]pyridine-2-carboxamide;
N-[4-({1-[3-(piperidin-1-yl)propanoyl]azetidin-3-yl}oxy)phenyl]-1,3-dihydro-2H-pyrrolo[3,4-c]pyridine-2-carboxamide;
N-[4-({1-[(4-methylpiperazin-1-yl)acetyl]azetidin-3-yl}oxy)phenyl]-1,3-dihydro-2H-pyrrolo[3,4-c]pyridine-2-carboxamide;
N-[4-({1-[3-(4-methylpiperazin-1-yl)propanoyl]azetidin-3-yl}oxy)phenyl]-1,3-dihydro-2H-pyrrolo[3,4-c]pyridine-2-carboxamide;
N-(4-{[1-(2-cyclopropylethyl)piperidin-4-yl]oxy}phenyl)-1,3-dihydro-2H-pyrrolo[3,4-c]pyridine-2-carboxamide;
N-(4-{[1-(2-cyclopentylethyl)piperidin-4-yl]oxy}phenyl)-1,3-dihydro-2H-pyrrolo[3,4-c]pyridine-2-carboxamide;
N-(4-{[1-(2-methylbutyl)piperidin-4-yl]oxy}phenyl)-1,3-dihydro-2H-pyrrolo[3,4-c]pyridine-2-carboxamide;
N-(4-{[1-(tetrahydrofuran-3-ylmethyl)piperidin-4-yl]oxy}phenyl)-1,3-dihydro-2H-pyrrolo[3,4-c]pyridine-2-carboxamide;
N-(4-{[1-(3,3-dimethylbutyl)piperidin-4-yl]oxy}phenyl)-1,3-dihydro-2H-pyrrolo[3,4-c]pyridine-2-carboxamide;
N-(4-{[1-(cyclohexylmethyl)piperidin-4-yl]oxy}phenyl)-1,3-dihydro-2H-pyrrolo[3,4-c]pyridine-2-carboxamide;
N-(4-{[1-(3-methylbutyl)piperidin-4-yl]oxy}phenyl)-1,3-dihydro-2H-pyrrolo[3,4-c]pyridine-2-carboxamide;
N-(4-{[1-(cyclopentylmethyl)piperidin-4-yl]oxy}phenyl)-1,3-dihydro-2H-pyrrolo[3,4-c]pyridine-2-carboxamide;
N-(4-{[1-(tetrahydrofuran-2-ylmethyl)piperidin-4-yl]oxy}phenyl)-1,3-dihydro-2H-pyrrolo[3,4-c]pyridine-2-carboxamide;
N-(4-{[1-(2-methylpropyl)piperidin-4-yl]oxy}phenyl)-1,3-dihydro-2H-pyrrolo[3,4-c]pyridine-2-carboxamide;
N-(4-{[1-(butylsulfonyl)piperidin-4-yl]oxy}phenyl)-1,3-dihydro-2H-pyrrolo[3,4-c]pyridine-2-carboxamide;
N-(4-{[1-(cyclopropylsulfonyl)piperidin-4-yl]oxy}phenyl)-1,3-dihydro-2H-pyrrolo[3,4-c]pyridine-2-carboxamide;
N-(4-{[1-(phenylsulfonyl)piperidin-4-yl]oxy}phenyl)-1,3-dihydro-2H-pyrrolo[3,4-c]pyridine-2-carboxamide;
N-[4-({1-[(4-fluorophenyl)sulfonyl]piperidin-4-yl}oxy)phenyl]-1,3-dihydro-2H-pyrrolo[3,4-c]pyridine-2-carboxamide;
N-(4-{[1-(ethylsulfonyl)piperidin-4-yl]oxy}phenyl)-1,3-dihydro-2H-pyrrolo[3,4-c]pyridine-2-carboxamide;
N-(4-{[1-(propan-2-ylsulfonyl)piperidin-4-yl]oxy}phenyl)-1,3-dihydro-2H-pyrrolo[3,4-c]pyridine-2-carboxamide;
N-(4-{[1-(benzylsulfonyl)piperidin-4-yl]oxy}phenyl)-1,3-dihydro-2H-pyrrolo[3,4-c]pyridine-2-carboxamide;
N-(4-{[1-(propylsulfonyl)piperidin-4-yl]oxy}phenyl)-1,3-dihydro-2H-pyrrolo[3,4-c]pyridine-2-carboxamide;
N-(4-{[1-(thiophen-2-ylsulfonyl)piperidin-4-yl]oxy}phenyl)-1,3-dihydro-2H-pyrrolo[3,4-c]pyridine-2-carboxamide;
N-[4-({1-[(2S)-2-methylbutanoyl]piperidin-4-yl}oxy)phenyl]-1,3-dihydro-2H-pyrrolo[3,4-c]pyridine-2-carboxamide;
N-[4-({1-[(2S)-tetrahydrofuran-2-ylcarbonyl]piperidin-4-yl}oxy)phenyl]-1,3-dihydro-2H-pyrrolo[3,4-c]pyridine-2-carboxamide;
N-[4-({1-[(2R)-tetrahydrofuran-2-ylcarbonyl]piperidin-4-yl}oxy)phenyl]-1,3-dihydro-2H-pyrrolo[3,4-c]pyridine-2-carboxamide;
N-[4-({1-[(4,4-difluorocyclohexyl)carbonyl]azetidin-3-yl}oxy)phenyl]-1,3-dihydro-2H-pyrrolo[3,4-c]pyridine-2-carboxamide;
N-(4-{[1-(5-oxo-D-prolyl)piperidin-4-yl]oxy}phenyl)-1,3-dihydro-2H-pyrrolo[3,4-c]pyridine-2-carboxamide;
N-(4-{[1-(2,2-dimethylpropanoyl)piperidin-4-yl]oxy}phenyl)-1,3-dihydro-2H-pyrrolo[3,4-c]pyridine-2-carboxamide;
N-(4-{[1-(2-methylpentanoyl)piperidin-4-yl]oxy}phenyl)-1,3-dihydro-2H-pyrrolo[3,4-c]pyridine-2-carboxamide;
N-(4-{[1-(2-ethylbutanoyl)piperidin-4-yl]oxy}phenyl)-1,3-dihydro-2H-pyrrolo[3,4-c]pyridine-2-carboxamide;
N-(4-{[1-(1H-pyrrol-2-ylcarbonyl)piperidin-4-yl]oxy}phenyl)-1,3-dihydro-2H-pyrrolo[3,4-c]pyridine-2-carboxamide;

N-(4-{[1-(1,2-oxazol-5-ylcarbonyl)piperidin-4-yl]oxy}phenyl)-1,3-dihydro-2H-pyrrolo[3,4-c]pyridine-2-carboxamide;
N-(4-{[1-(pyridin-3-ylcarbonyl)piperidin-4-yl]oxy}phenyl)-1,3-dihydro-2H-pyrrolo[3,4-c]pyridine-2-carboxamide;
N-(4-{[1-(pyridazin-3-ylcarbonyl)piperidin-4-yl]oxy}phenyl)-1,3-dihydro-2H-pyrrolo[3,4-c]pyridine-2-carboxamide;
N-(4-{[1-(pyrazin-2-ylcarbonyl)piperidin-4-yl]oxy}phenyl)-1,3-dihydro-2H-pyrrolo[3,4-c]pyridine-2-carboxamide;
N-(4-{[1-(pyrimidin-4-ylcarbonyl)piperidin-4-yl]oxy}phenyl)-1,3-dihydro-2H-pyrrolo[3,4-c]pyridine-2-carboxamide;
N-[4-({1-[(5-methylpyrazin-2-yl)carbonyl]piperidin-4-yl}oxy)phenyl]-1,3-dihydro-2H-pyrrolo[3,4-c]pyridine-2-carboxamide;
N-[4-({1-[3-(piperidin-1-yl)propanoyl]piperidin-4-yl}oxy)phenyl]-1,3-dihydro-2H-pyrrolo[3,4-c]pyridine-2-carboxamide;
N-(4-{[1-(morpholin-4-ylacetyl)piperidin-4-yl]oxy}phenyl)-1,3-dihydro-2H-pyrrolo[3,4-c]pyridine-2-carboxamide;
N-[4-({1-[3-(4-methylpiperazin-1-yl)propanoyl]piperidin-4-yl}oxy)phenyl]-1,3-dihydro-2H-pyrrolo[3,4-c]pyridine-2-carboxamide;
benzyl trans-3-[(1,3-dihydro-2H-pyrrolo[3,4-c]pyridin-2-ylcarbonyl)amino]cyclobutanecarboxylate;
N-[4-(4-{[(4-methylpiperazin-1-yl)acetyl]amino}cyclohex-1-en-1-yl)phenyl]-1,3-dihydro-2H-pyrrolo[3,4-c]pyridine-2-carboxamide;
N-(4-{4-[(tetrahydro-2H-pyran-4-ylacetyl)amino]cyclohex-1-en-1-yl}phenyl)-1,3-dihydro-2H-pyrrolo[3,4-c]pyridine-2-carboxamide;
N-{4-[4-(benzoylamino)cyclohex-1-en-1-yl]phenyl}-1,3-dihydro-2H-pyrrolo[3,4-c]pyridine-2-carboxamide;
N-[4-(4-{[(2S)-tetrahydrofuran-2-ylcarbonyl]amino}cyclohex-1-en-1-yl)phenyl]-1,3-dihydro-2H-pyrrolo[3,4-c]pyridine-2-carboxamide;
N-[4-(4-{[(2R)-tetrahydrofuran-2-ylcarbonyl]amino}cyclohex-1-en-1-yl)phenyl]-1,3-dihydro-2H-pyrrolo[3,4-c]pyridine-2-carboxamide;
N-[4-(4-{[(1-methylpiperidin-4-yl)carbonyl]amino}cyclohex-1-en-1-yl)phenyl]-1,3-dihydro-2H-pyrrolo[3,4-c]pyridine-2-carboxamide;
N-[4-(4-{[(1,1-dioxidotetrahydro-2H-thiopyran-4-yl)carbonyl]amino}cyclohex-1-en-1-yl)phenyl]-1,3-dihydro-2H-pyrrolo[3,4-c]pyridine-2-carboxamide;
N-[4-(4-{[(3R)-tetrahydrofuran-3-ylcarbonyl]amino}cyclohex-1-en-1-yl)phenyl]-1,3-dihydro-2H-pyrrolo[3,4-c]pyridine-2-carboxamide;
N-[4-(4-{[(3S)-tetrahydrofuran-3-ylcarbonyl]amino}cyclohex-1-en-1-yl)phenyl]-1,3-dihydro-2H-pyrrolo[3,4-c]pyridine-2-carboxamide;
N-[4-(4-{[(2S)-2-methylbutanoyl]amino}cyclohex-1-en-1-yl)phenyl]-1,3-dihydro-2H-pyrrolo[3,4-c]pyridine-2-carboxamide;
N-(4-{3-[(3-methylbutanoyl)amino]oxetan-3-yl}phenyl)-1,3-dihydro-2H-pyrrolo[3,4-c]pyridine-2-carboxamide;
tert-butyl 4-({4-[(1,3-dihydro-2H-pyrrolo[3,4-c]pyridin-2-ylcarbonyl)amino]phenyl}sulfonyl)piperidine-1-carboxylate;
N-{4-[4-(propylcarbamoyl)piperidin-1-yl]phenyl}-1,3-dihydro-2H-pyrrolo[3,4-c]pyridine-2-carboxamide;
N-(4-{4-[(2-methoxyethyl)carbamoyl]piperidin-1-yl}phenyl)-1,3-dihydro-2H-pyrrolo[3,4-c]pyridine-2-carboxamide;
N-(4-{4-[(cyclopentylmethyl)carbamoyl]piperidin-1-yl}phenyl)-1,3-dihydro-2H-pyrrolo[3,4-c]pyridine-2-carboxamide;
N-(4-{4-[(1,4-dioxan-2-ylmethyl)carbamoyl]piperidin-1-yl}phenyl)-1,3-dihydro-2H-pyrrolo[3,4-c]pyridine-2-carboxamide;
N-{4-[4-(cyclopentylcarbamoyl)piperidin-1-yl]phenyl}-1,3-dihydro-2H-pyrrolo[3,4-c]pyridine-2-carboxamide;
N-{4-[4-(tetrahydro-2H-pyran-4-ylcarbamoyl)piperidin-1-yl]phenyl}-1,3-dihydro-2H-pyrrolo[3,4-c]pyridine-2-carboxamide;
N-{4-[4-(morpholin-4-ylcarbonyl)piperidin-1-yl]phenyl}-1,3-dihydro-2H-pyrrolo[3,4-c]pyridine-2-carboxamide;
N-{4-[4-((tetrahydro-2H-pyran-4-ylmethyl)carbamoyl]piperidin-1-yl}phenyl}-1,3-dihydro-2H-pyrrolo[3,4-c]pyridine-2-carboxamide;
N-{4-[4-(cyclopropylcarbamoyl)piperidin-1-yl]phenyl}-1,3-dihydro-2H-pyrrolo[3,4-c]pyridine-2-carboxamide;
N-{4-[4-[(tetrahydrofuran-3-ylmethyl)carbamoyl]piperidin-1-yl}phenyl)-1,3-dihydro-2H-pyrrolo[3,4-c]pyridine-2-carboxamide;
N-(4-{4-[(2-hydroxy-2-methylpropyl)carbamoyl]piperidin-1-yl}phenyl)-1,3-dihydro-2H-pyrrolo[3,4-c]pyridine-2-carboxamide;
N-{4-[4-(butan-2-ylcarbamoyl)piperidin-1-yl]phenyl}-1,3-dihydro-2H-pyrrolo[3,4-c]pyridine-2-carboxamide;
N-(4-{1-[(3R)-tetrahydrofuran-3-ylcarbonyl]-1,2,3,6-tetrahydropyridin-4-yl}phenyl)-1,3-dihydro-2H-isoindole-2-carboxamide;
N-(4-{1-[(3S)-tetrahydrofuran-3-ylcarbonyl]-1,2,3,6-tetrahydropyridin-4-yl}phenyl)-1,3-dihydro-2H-isoindole-2-carboxamide;
N-(4-{1-[(1,1-dioxidotetrahydro-2H-thiopyran-4-yl)carbonyl]-1,2,3,6-tetrahydropyridin-4-yl}phenyl)-1,3-dihydro-2H-isoindole-2-carboxamide;
N-(4-{1-[(2R)-tetrahydrofuran-2-ylcarbonyl]piperidin-4-yl}phenyl)-1,3-dihydro-2H-isoindole-2-carboxamide;
N-(4-{1-[(2S)-tetrahydrofuran-2-ylcarbonyl]piperidin-4-yl}phenyl)-1,3-dihydro-2H-isoindole-2-carboxamide;
N-(4-{1-[(3R)-tetrahydrofuran-3-ylcarbonyl]piperidin-4-yl}phenyl)-1,3-dihydro-2H-isoindole-2-carboxamide;
N-(4-{(4R)-4-[(2-methylpropanoyl)amino]cyclohex-1-en-1-yl}phenyl)-1,3-dihydro-2H-pyrrolo[3,4-c]pyridine-2-carboxamide;
N-(4-{(4S)-4-[(2-methylpropanoyl)amino]cyclohex-1-en-1-yl}phenyl)-1,3-dihydro-2H-pyrrolo[3,4-c]pyridine-2-carboxamide;
N-[4-(1-benzoylazetidin-3-yl)butyl]-1,3-dihydro-2H-isoindole-2-carboxamide;
N-[4-(1-benzoylazetidin-3-yl)butyl]-1,3-dihydro-2H-pyrrolo[3,4-c]pyridine-2-carboxamide;
N-[trans-3-(benzylcarbamoyl)cyclobutyl]-1,3-dihydro-2H-pyrrolo[3,4-c]pyridine-2-carboxamide;
N-{trans-3-[(2-phenylethyl)carbamoyl]cyclobutyl}-1,3-dihydro-2H-pyrrolo[3,4-c]pyridine-2-carboxamide;
N-{trans-3-[(3-phenylpropyl)carbamoyl]cyclobutyl}-1,3-dihydro-2H-pyrrolo[3,4-c]pyridine-2-carboxamide;
N-(4-{1-[(2-methyl-1,3-oxazol-4-yl)carbonyl]-1,2,3,6-tetrahydropyridin-4-yl}phenyl)-1,3-dihydro-2H-pyrrolo[3,4-c]pyridine-2-carboxamide;
N-{4-[1-(furan-3-ylcarbonyl)-1,2,3,6-tetrahydropyridin-4-yl]phenyl}-1,3-dihydro-2H-pyrrolo[3,4-c]pyridine-2-carboxamide;

N-(4-{1-[(2E)-3-(furan-2-yl)prop-2-enoyl]-1,2,3,6-tetrahydropyridin-4-yl}phenyl)-1,3-dihydro-2H-pyrrolo[3,4-c]pyridine-2-carboxamide;
N-{4-[1-(1,3-oxazol-5-ylcarbonyl)-1,2,3,6-tetrahydropyridin-4-yl]phenyl}-1,3-dihydro-2H-pyrrolo[3,4-c]pyridine-2-carboxamide;
N-{4-[1-(3,3,3-trifluoropropanoyl)-1,2,3,6-tetrahydropyridin-4-yl]phenyl}-1,3-dihydro-2H-pyrrolo[3,4-c]pyridine-2-carboxamide;
N-(4-{1-[(1,5-dimethyl-1H-pyrazol-3-yl)carbonyl]-1,2,3,6-tetrahydropyridin-4-yl}phenyl)-1,3-dihydro-2H-pyrrolo[3,4-c]pyridine-2-carboxamide;
N-(4-{1-[(4-methoxycyclohexyl)carbonyl]-1,2,3,6-tetrahydropyridin-4-yl}phenyl)-1,3-dihydro-2H-pyrrolo[3,4-c]pyridine-2-carboxamide;
N-{4-[1-(2,3-dimethylbutanoyl)-1,2,3,6-tetrahydropyridin-4-yl]phenyl}-1,3-dihydro-2H-pyrrolo[3,4-c]pyridine-2-carboxamide;
N-(4-{1-[(2,2-difluorocyclopropyl)carbonyl]-1,2,3,6-tetrahydropyridin-4-yl}phenyl)-1,3-dihydro-2H-pyrrolo[3,4-c]pyridine-2-carboxamide;
N-{4-[1-(1H-pyrazol-5-ylcarbonyl)-1,2,3,6-tetrahydropyridin-4-yl]phenyl}-1,3-dihydro-2H-pyrrolo[3,4-c]pyridine-2-carboxamide;
N-{4-[1-(tert-butoxyacetyl)-1,2,3,6-tetrahydropyridin-4-yl]phenyl}-1,3-dihydro-2H-pyrrolo[3,4-c]pyridine-2-carboxamide;
N-(4-{1-[3-(1H-1,2,4-triazol-1-yl)propanoyl]-1,2,3,6-tetrahydropyridin-4-yl}phenyl)-1,3-dihydro-2H-pyrrolo[3,4-c]pyridine-2-carboxamide;
N-{4-[1-(3-ethoxypropanoyl)-1,2,3,6-tetrahydropyridin-4-yl]phenyl}-1,3-dihydro-2H-pyrrolo[3,4-c]pyridine-2-carboxamide;
N-{4-[1-(3-hydroxy-3-methylbutanoyl)-1,2,3,6-tetrahydropyridin-4-yl]phenyl}-1,3-dihydro-2H-pyrrolo[3,4-c]pyridine-2-carboxamide;
N-(4-{1-[3-(1H-pyrrol-1-yl)propanoyl]-1,2,3,6-tetrahydropyridin-4-yl}phenyl)-1,3-dihydro-2H-pyrrolo[3,4-c]pyridine-2-carboxamide;
N-(4-{1-[(1-methylcyclopropyl)carbonyl]-1,2,3,6-tetrahydropyridin-4-yl}phenyl)-1,3-dihydro-2H-pyrrolo[3,4-c]pyridine-2-carboxamide;
N-(4-{1-[(2-methylpropoxy)acetyl]-1,2,3,6-tetrahydropyridin-4-yl}phenyl)-1,3-dihydro-2H-pyrrolo[3,4-c]pyridine-2-carboxamide;
N-{4-[1-(1-methylprolyl)-1,2,3,6-tetrahydropyridin-4-yl]phenyl}-1,3-dihydro-2H-pyrrolo[3,4-c]pyridine-2-carboxamide;
N-{4-[1-(2-hydroxy-2-methylbutanoyl)-1,2,3,6-tetrahydropyridin-4-yl]phenyl}-1,3-dihydro-2H-pyrrolo[3,4-c]pyridine-2-carboxamide;
N-(4-{1-[(1-hydroxycyclopropyl)carbonyl]-1,2,3,6-tetrahydropyridin-4-yl}phenyl)-1,3-dihydro-2H-pyrrolo[3,4-c]pyridine-2-carboxamide;
N-{4-[1-(cyclopropylacetyl)-1,2,3,6-tetrahydropyridin-4-yl]phenyl}-1,3-dihydro-2H-pyrrolo[3,4-c]pyridine-2-carboxamide;
N-{4-[1-(cyclopentylcarbonyl)-1,2,3,6-tetrahydropyridin-4-yl]phenyl}-1,3-dihydro-2H-pyrrolo[3,4-c]pyridine-2-carboxamide;
N-[4-(1-{[1-(methoxymethyl)cyclopropyl]carbonyl}-1,2,3,6-tetrahydropyridin-4-yl)phenyl]-1,3-dihydro-2H-pyrrolo[3,4-c]pyridine-2-carboxamide;
N-(4-{1-[(methylsulfonyl)acetyl]-1,2,3,6-tetrahydropyridin-4-yl}phenyl)-1,3-dihydro-2H-pyrrolo[3,4-c]pyridine-2-carboxamide;
N-(4-{1-[(1-methyl-1H-pyrazol-4-yl)carbonyl]-1,2,3,6-tetrahydropyridin-4-yl}phenyl)-1,3-dihydro-2H-pyrrolo[3,4-c]pyridine-2-carboxamide;
N-[4-(1-acetyl-1,2,3,6-tetrahydropyridin-4-yl)phenyl]-1,3-dihydro-2H-pyrrolo[3,4-c]pyridine-2-carboxamide;
N-{4-[1-(cyclopropylcarbonyl)-1,2,3,6-tetrahydropyridin-4-yl]phenyl}-1,3-dihydro-2H-pyrrolo[3,4-c]pyridine-2-carboxamide;
N-{4-[1-(2-ethylbutanoyl)-1,2,3,6-tetrahydropyridin-4-yl]phenyl}-1,3-dihydro-2H-pyrrolo[3,4-c]pyridine-2-carboxamide;
N-{4-[1-(5-oxo-L-prolyl)-1,2,3,6-tetrahydropyridin-4-yl]phenyl}-1,3-dihydro-2H-pyrrolo[3,4-c]pyridine-2-carboxamide;
N-(4-{1-[(2E)-4-methylpent-2-enoyl]-1,2,3,6-tetrahydropyridin-4-yl}phenyl)-1,3-dihydro-2H-pyrrolo[3,4-c]pyridine-2-carboxamide;
N-{4-[1-(2-methoxy-2-methylpropanoyl)-1,2,3,6-tetrahydropyridin-4-yl]phenyl}-1,3-dihydro-2H-pyrrolo[3,4-c]pyridine-2-carboxamide;
N-{4-[1-(cyclopent-1-en-1-ylcarbonyl)-1,2,3,6-tetrahydropyridin-4-yl]phenyl}-1,3-dihydro-2H-pyrrolo[3,4-c]pyridine-2-carboxamide;
N-{4-[1-(thiophen-3-ylacetyl)-1,2,3,6-tetrahydropyridin-4-yl]phenyl}-1,3-dihydro-2H-pyrrolo[3,4-c]pyridine-2-carboxamide;
N-{4-[1-(cyclohexylcarbonyl)-1,2,3,6-tetrahydropyridin-4-yl]phenyl}-1,3-dihydro-2H-pyrrolo[3,4-c]pyridine-2-carboxamide;
N-[4-(1-propanoyl-1,2,3,6-tetrahydropyridin-4-yl)phenyl]-1,3-dihydro-2H-pyrrolo[3,4-c]pyridine-2-carboxamide;
N-{4-[1-(2,2-dimethylbutanoyl)-1,2,3,6-tetrahydropyridin-4-yl]phenyl}-1,3-dihydro-2H-pyrrolo[3,4-c]pyridine-2-carboxamide;
N-(4-{1-[(1-methyl-1H-pyrrol-2-yl)carbonyl]-1,2,3,6-tetrahydropyridin-4-yl}phenyl)-1,3-dihydro-2H-pyrrolo[3,4-c]pyridine-2-carboxamide;
N-{4-[1-(methoxyacetyl)-1,2,3,6-tetrahydropyridin-4-yl]phenyl}-1,3-dihydro-2H-pyrrolo[3,4-c]pyridine-2-carboxamide;
N-{4-[1-(2,2-dimethylpropanoyl)-1,2,3,6-tetrahydropyridin-4-yl]phenyl}-1,3-dihydro-2H-pyrrolo[3,4-c]pyridine-2-carboxamide;
N-{4-[1-(4-methylhexanoyl)-1,2,3,6-tetrahydropyridin-4-yl]phenyl}-1,3-dihydro-2H-pyrrolo[3,4-c]pyridine-2-carboxamide;
N-(4-{1-[(2,2-dimethylcyclopropyl)carbonyl]-1,2,3,6-tetrahydropyridin-4-yl}phenyl)-1,3-dihydro-2H-pyrrolo[3,4-c]pyridine-2-carboxamide;
N-(4-{1-[(1,3-dimethyl-1H-pyrazol-5-yl)carbonyl]-1,2,3,6-tetrahydropyridin-4-yl}phenyl)-1,3-dihydro-2H-pyrrolo[3,4-c]pyridine-2-carboxamide;
N-{4-[1-(cyclobutylacetyl)-1,2,3,6-tetrahydropyridin-4-yl]phenyl}-1,3-dihydro-2H-pyrrolo[3,4-c]pyridine-2-carboxamide;
N-{4-[1-(piperidin-1-ylacetyl)-1,2,3,6-tetrahydropyridin-4-yl]phenyl}-1,3-dihydro-2H-pyrrolo[3,4-c]pyridine-2-carboxamide;
N-(4-{1-[2-(pyrrolidin-1-yl)propanoyl]-1,2,3,6-tetrahydropyridin-4-yl}phenyl)-1,3-dihydro-2H-pyrrolo[3,4-c]pyridine-2-carboxamide;
N-(4-{1-[(1,3-dimethyl-1H-pyrazol-4-yl)carbonyl]-1,2,3,6-tetrahydropyridin-4-yl}phenyl)-1,3-dihydro-2H-pyrrolo[3,4-c]pyridine-2-carboxamide;
N-[4-(cis-4-{[(2-methoxyethoxy)acetyl]amino}cyclohexyl)phenyl]-1,3-dihydro-2H-pyrrolo[3,4-c]pyridine-2-carboxamide;

N-[4-(trans-4-{[(2-methoxyethoxy)acetyl]amino}cyclohexyl)phenyl]-1,3-dihydro-2H-pyrrolo[3,4-c]pyridine-2-carboxamide;
N-[4-(cis-4-{[(2S)-tetrahydrofuran-2-ylcarbonyl]amino}cyclohexyl)phenyl]-1,3-dihydro-2H-pyrrolo[3,4-c]pyridine-2-carboxamide;
N-[4-(trans-4-{[(2S)-tetrahydrofuran-2-ylcarbonyl]amino}cyclohexyl)phenyl]-1,3-dihydro-2H-pyrrolo[3,4-c]pyridine-2-carboxamide;
N-[4-(cis-4-{[(2R)-tetrahydrofuran-2-ylcarbonyl]amino}cyclohexyl)phenyl]-1,3-dihydro-2H-pyrrolo[3,4-c]pyridine-2-carboxamide;
N-[4-(trans-4-{[(2R)-tetrahydrofuran-2-ylcarbonyl]amino}cyclohexyl)phenyl]-1,3-dihydro-2H-pyrrolo[3,4-c]pyridine-2-carboxamide;
N-(6-{[(2S)-tetrahydrofuran-2-ylmethyl]carbamoyl}pyridazin-3-yl)-1,3-dihydro-2H-pyrrolo[3,4-c]pyridine-2-carboxamide;
N-(4-{[(3R)-1-(3-methylbutanoyl)pyrrolidin-3-yl]oxy}phenyl)-1,3-dihydro-2H-pyrrolo[3,4-c]pyridine-2-carboxamide;
N-(4-{[(3R)-1-(cyclobutylcarbonyl)pyrrolidin-3-yl]oxy}phenyl)-1,3-dihydro-2H-pyrrolo[3,4-c]pyridine-2-carboxamide;
N-[4-({(3R)-1-[(2R)-tetrahydrofuran-2-ylcarbonyl]pyrrolidin-3-yl}oxy)phenyl]-1,3-dihydro-2H-pyrrolo[3,4-c]pyridine-2-carboxamide;
N-[4-({(3R)-1-[(2S)-tetrahydrofuran-2-ylcarbonyl]pyrrolidin-3-yl}oxy)phenyl]-1,3-dihydro-2H-pyrrolo[3,4-c]pyridine-2-carboxamide;
N-(4-{[(3R)-1-(cyclopropylacetyl)pyrrolidin-3-yl]oxy}phenyl)-1,3-dihydro-2H-pyrrolo[3,4-c]pyridine-2-carboxamide;
N-(4-{[(3S)-1-(3-methylbutanoyl)pyrrolidin-3-yl]oxy}phenyl)-1,3-dihydro-2H-pyrrolo[3,4-c]pyridine-2-carboxamide;
N-(4-{[(3S)-1-(cyclobutylcarbonyl)pyrrolidin-3-yl]oxy}phenyl)-1,3-dihydro-2H-pyrrolo[3,4-c]pyridine-2-carboxamide;
N-[4-({(3S)-1-[(2R)-tetrahydrofuran-2-ylcarbonyl]pyrrolidin-3-yl}oxy)phenyl]-1,3-dihydro-2H-pyrrolo[3,4-c]pyridine-2-carboxamide;
N-[4-({(3S)-1-[(2S)-tetrahydrofuran-2-ylcarbonyl]pyrrolidin-3-yl}oxy)phenyl]-1,3-dihydro-2H-pyrrolo[3,4-c]pyridine-2-carboxamide;
N-(4-{[(3S)-1-(cyclopropylacetyl)pyrrolidin-3-yl]oxy}phenyl)-1,3-dihydro-2H-pyrrolo[3,4-c]pyridine-2-carboxamide;
N-(6-{[(2R)-tetrahydrofuran-2-ylmethyl]carbamoyl}pyridazin-3-yl)-1,3-dihydro-2H-pyrrolo[3,4-c]pyridine-2-carboxamide;
N-{6-[(tetrahydro-2H-pyran-4-ylmethyl)carbamoyl]pyridazin-3-yl}-1,3-dihydro-2H-pyrrolo[3,4-c]pyridine-2-carboxamide;
N-{6-[(cyclopentylmethyl)carbamoyl]pyridazin-3-yl}-1,3-dihydro-2H-pyrrolo[3,4-c]pyridine-2-carboxamide;
N-{6-[(tetrahydrofuran-3-ylmethyl)carbamoyl]pyridazin-3-yl}-1,3-dihydro-2H-pyrrolo[3,4-c]pyridine-2-carboxamide;
N-{6-[(bicyclo[2.2.1]hept-2-ylmethyl)carbamoyl]pyridazin-3-yl}-1,3-dihydro-2H-pyrrolo[3,4-c]pyridine-2-carboxamide;
N-(4-{trans-4-[(2-methylpropanoyl)amino]cyclohexyl}phenyl)-1,3-dihydro-2H-pyrrolo[3,4-c]pyridine-2-carboxamide;
N-(4-{cis-4-[(2-methylpropanoyl)amino]cyclohexyl}phenyl)-1,3-dihydro-2H-pyrrolo[3,4-c]pyridine-2-carboxamide;
N-(4-{cis-4-[(cyclohexylcarbonyl)amino]cyclohexyl}phenyl)-1,3-dihydro-2H-pyrrolo[3,4-c]pyridine-2-carboxamide;
N-(4-{trans-4-[(cyclohexylcarbonyl)amino]cyclohexyl}phenyl)-1,3-dihydro-2H-pyrrolo[3,4-c]pyridine-2-carboxamide;
N-(4-{trans-4-[(cyclopropylacetyl)amino]cyclohexyl}phenyl)-1,3-dihydro-2H-pyrrolo[3,4-c]pyridine-2-carboxamide;
N-(4-{cis-4-[(cyclopropylacetyl)amino]cyclohexyl}phenyl)-1,3-dihydro-2H-pyrrolo[3,4-c]pyridine-2-carboxamide;
N-(4-{4-[(2-methylpropanoyl)amino]cyclohex-1-en-1-yl}phenyl)-1,3-dihydro-2H-isoindole-2-carboxamide;
N-[4-(4-{[(2R)-tetrahydrofuran-2-ylcarbonyl]amino}cyclohex-1-en-1-yl)phenyl]-1,3-dihydro-2H-isoindole-2-carboxamide;
N-[4-(4-{[(2S)-tetrahydrofuran-2-ylcarbonyl]amino}cyclohex-1-en-1-yl)phenyl]-1,3-dihydro-2H-isoindole-2-carboxamide;
N-(4-{4-[(cyclopentylacetyl)amino]cyclohex-1-en-1-yl}phenyl)-1,3-dihydro-2H-isoindole-2-carboxamide;
N-(4-{4-[(cyclopropylacetyl)amino]cyclohex-1-en-1-yl}phenyl)-1,3-dihydro-2H-isoindole-2-carboxamide;
N-(4-{4-[(2-hydroxy-2-methylpropanoyl)amino]cyclohex-1-en-1-yl}phenyl)-1,3-dihydro-2H-isoindole-2-carboxamide;
N-(4-{4-[(tetrahydro-2H-pyran-4-ylcarbonyl)amino]cyclohex-1-en-1-yl}phenyl)-1,3-dihydro-2H-isoindole-2-carboxamide;
N-(4-{4-[(cyclohexylcarbonyl)amino]cyclohex-1-en-1-yl}phenyl)-1,3-dihydro-2H-isoindole-2-carboxamide;
and pharmaceutically acceptable salts thereof.

Still another embodiment pertains to compounds of Formula (Ic), which are

N-(4-{[(3S)-tetrahydrofuran-3-ylmethyl]carbamoyl}phenyl)-1,3-dihydro-2H-isoindole-2-carboxamide;
N-[4-(1-isobutyryl-1,2,3,6-tetrahydropyridin-4-yl)phenyl]-1,3-dihydro-2H-pyrrolo[3,4-c]pyridine-2-carboxamide;
5-fluoro-N-(4-{[(3S)-tetrahydrofuran-3-ylmethyl]carbamoyl}phenyl)-1,3-dihydro-2H-isoindole-2-carboxamide;
N-[4-(1-isobutyrylpiperidin-4-yl)phenyl]-1,3-dihydro-2H-pyrrolo[3,4-c]pyridine-2-carboxamide;
N-[4-(1-benzoylpiperidin-4-yl)butyl]-1,3-dihydro-2H-pyrrolo[3,4-c]pyridine-2-carboxamide;
N-{4-[1-(2-hydroxy-2-methylpropanoyl)piperidin-4-yl]phenyl}-1,3-dihydro-2H-pyrrolo[3,4-c]pyridine-2-carboxamide;
N-(4-{1-[(2S)-tetrahydrofuran-2-ylcarbonyl]-1,2,3,6-tetrahydropyridin-4-yl}phenyl)-1,3-dihydro-2H-pyrrolo[3,4-c]pyridine-2-carboxamide;
N-(4-{1-[(1,1-dioxidotetrahydro-2H-thiopyran-4-yl)carbonyl]-1,2,3,6-tetrahydropyridin-4-yl}phenyl)-1,3-dihydro-2H-pyrrolo[3,4-c]pyridine-2-carboxamide;
N-(4-{1-[(3S)-tetrahydrofuran-3-ylcarbonyl]-1,2,3,6-tetrahydropyridin-4-yl}phenyl)-1,3-dihydro-2H-pyrrolo[3,4-c]pyridine-2-carboxamide;
N-(4-{1-[(3S)-tetrahydrofuran-3-ylcarbonyl]piperidin-4-yl}phenyl)-1,3-dihydro-2H-pyrrolo[3,4-c]pyridine-2-carboxamide; and pharmaceutically acceptable salts thereof.

Still another embodiment pertains to compounds of Formula (Ic), which are

N-(4-{[(3S)-tetrahydrofuran-3-ylmethyl]carbamoyl}phenyl)-1,3-dihydro-2H-isoindole-2-carboxamide;

N-[4-(1-isobutyryl-1,2,3,6-tetrahydropyridin-4-yl)phenyl]-1,3-dihydro-2H-pyrrolo[3,4-c]pyridine-2-carboxamide;

N-[4-(1-isobutyrylpiperidin-4-yl)phenyl]-1,3-dihydro-2H-pyrrolo[3,4-c]pyridine-2-carboxamide;

N-[4-(1-benzoylpiperidin-4-yl)butyl]-1,3-dihydro-2H-pyrrolo[3,4-c]pyridine-2-carboxamide;

N-{4-[1-(2-hydroxy-2-methylpropanoyl)piperidin-4-yl]phenyl}-1,3-dihydro-2H-pyrrolo[3,4-c]pyridine-2-carboxamide; and pharmaceutically acceptable salts thereof.

Embodiments of Formula (IIc)

In another aspect, the present invention provides compounds of Formula (IIc)

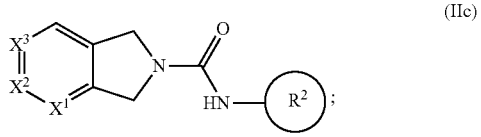

(IIc)

and pharmaceutically acceptable salts thereof; wherein $X^1$, $X^2$, $X^3$, are as described herein for Formula (Ic); and $R^2$ is phenyl, heterocyclyl, cycloalkyl, or cycloalkenyl; wherein the $R^2$ phenyl, heterocyclyl, cycloalkyl, and cycloalkenyl are optionally substituted as described herein for substituents on $R^2$ in Formula (Ic).

In one embodiment of formula (IIc), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N; or $X^1$ is CH; $X^2$ is N; and $X^3$ is $CR^1$; or $X^1$ is $CR^1$; $X^2$ is N; and $X^3$ is CH; or $X^1$ is N; $X^2$ is $CR^1$; and $X^3$ is CH; or $X^1$ is N; $X^2$ is $CR^1$; and $X^3$ is N;

$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, C(O)H, $CF_3$, C(O)OH, or $C(O)NH_2$;

$R^2$ is phenyl, heterocyclyl, cycloalkyl, or cycloalkenyl; wherein each $R^2$ phenyl is optionally substituted at the para position with one independently selected $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $CHNOR^5$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, OH, CN, $N_3$, $NO_2$, $CF_3$, $CF_2CF_3$, $OCF_3$, $OCF_2CF_3$, Br or I; wherein each $R^2$ phenyl is optionally additionally substituted with one F; wherein each $R^2$ heterocyclyl, cycloalkyl, and cycloalkenyl is optionally substituted with one, two, three or four independently selected $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, NHC(O)OR$^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, OH, CN, $N_3$, $CF_3$, $CF_2CF_3$, $OCF_3$, $OCF_2CF_3$, F, Cl, Br or I;

$R^3$, at each occurrence, is independently selected alkyl, alkenyl, alkynyl, aryl, or heterocyclyl; wherein each $R^3$ alkyl, alkenyl, and alkynyl is optionally substituted with one, two, three or four independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I;

$R^5$, at each occurrence, is independently selected alkyl, alkenyl, alkynyl, aryl, heterocyclyl, cycloalkyl, or cycloalkenyl; wherein each $R^5$ alkyl, alkenyl, and alkynyl is optionally substituted with one, two, three or four independently selected $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I;

$R^6$, at each occurrence, is independently selected alkyl, alkenyl, alkynyl, aryl, heterocyclyl, cycloalkyl, or cycloalkenyl; wherein each $R^6$ alkyl, alkenyl, and alkynyl is optionally substituted with one, two, three or four independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, OH, (O), C(O)OH, $N_3$, CN, $NH_2$, $CF_3$, $CF_2CF_3$, F, Cl, Br or I;

$R^9$, at each occurrence, is independently selected alkyl, alkenyl, alkynyl, aryl, heterocyclyl, cycloalkyl, or cycloalkenyl; wherein each $R^9$ alkyl, alkenyl, and alkynyl is optionally substituted with one, two, three or four independently selected alkoxy, OH, cycloalkyl, aryl, or heterocyclyl;

$R^{10}$, at each occurrence, is independently selected alkyl, alkenyl, alkynyl, aryl, heterocyclyl, cycloalkyl, or cycloalkenyl;

wherein the cyclic moieties represented by $R^3$, $R^5$, $R^6$, $R^9$, and $R^{10}$ are optionally substituted with one, two, three, four, five, or six independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, $C(O)H$, $C(O)OH$, OH, CN, $N_3$, $NO_2$, $CF_3$, $CF_2CF_3$, $OCF_3$, $OCF_2CF_3$, $SCF_3$, F, Cl, Br or I;

$R^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, or cycloalkenyl; wherein each $R^{13}$ alkyl, alkenyl, and alkynyl is optionally substituted with one, two, three or four independently selected $R^{14}$, $OR^{14}$, $SR^{14}$, $S(O)R^{14}$, $SO_2R^{14}$, $C(O)R^{14}$, $OC(O)R^{14}$, $OC(O)OR^{14}$, $NH_2$, $NHR^{14}$, $N(R^{14})_2$, $NHC(O)R^{14}$, $NR^{14}C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NH_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, and cycloalkenyl is optionally substituted with one, two, three or four independently selected $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $C(O)H$, $C(O)OH$, $OH$, $CN$, $N_3$, $NO_2$, $CF_3$, $CF_2CF_3$, $OCF_3$, $OCF_2CF_3$, F, Cl, Br or I;

$R^{14}$, at each occurrence, is independently selected alkyl, alkenyl, alkynyl, aryl, heterocyclyl, cycloalkyl, or cycloalkenyl; wherein each $R^{14}$ alkyl, alkenyl, and alkynyl is optionally substituted with one, two, three or four independently selected heterocyclyl, alkoxy, $NH_2$, $SO_2NH_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{14}$ aryl, heterocyclyl, cycloalkyl, and cycloalkenyl is optionally substituted with one, two, three or four independently selected $R^{16}$, $OR^{16}$, $OH$, F, Cl, Br, or I;

$R^{15}$, at each occurrence, is independently selected alkyl; wherein the $R^{15}$ alkyl is optionally substituted with one, two, three or four alkoxy; and $R^{16}$, at each occurrence, is independently selected alkyl, wherein the $R^{16}$ alkyl is optionally substituted with one, two, three or four alkoxy;

with the proviso that when $X^1$, $X^2$, and $X^3$ are CH and $R^2$ is phenyl; $R^5$ is not methyl;

with the proviso that when $X^1$, $X^2$, and $X^3$ are CH, and $R^2$ is phenyl substituted with $OR^5$; $R^5$ is not methyl;

with the proviso that when $R^{13}$ is piperidinyl, it is substituted piperidinyl; and with the proviso that when $R^{13}$ is pyrrolinyl, at least one of $X^1$, $X^2$, and $X^3$ is N.

In one embodiment of Formula (IIc), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N; or $X^1$ is CH; $X^2$ is N; and $X^3$ is $CR^1$; or $X^1$ is $CR^1$; $X^2$ is N; and $X^3$ is CH; or $X^1$ is N; $X^2$ is $CR^1$; and $X^3$ is CH; or $X^1$ is N; $X^2$ is $CR^1$; and $X^3$ is N. In another embodiment of Formula (IIc), $X^1$, $X^2$, and $X^3$ are CH. In another embodiment of Formula (IIc), $X^1$ and $X^3$ are CH; and $X^2$ is N. In another embodiment of Formula (IIc), $X^1$ and $X^3$ are CH; and $X^2$ is $CR^1$. In another embodiment of Formula (IIc), $X^2$ and $X^3$ are CH; and $X^1$ is $CR^1$. In another embodiment of Formula (IIc), $X^1$ is CH; and $X^2$ and $X^3$ are $CR^1$. In another embodiment of Formula (IIc), $X^2$ is CH; and $X^1$ and $X^3$ are N. In another embodiment of Formula (IIc), $X^2$ and $X^3$ are CH; and $X^1$ is N. In another embodiment of Formula (IIc), $X^1$ is CH; $X^2$ is N; and $X^3$ is $CR^1$. In another embodiment of Formula (IIc), $X^1$ is $CR^1$; $X^2$ is N; and $X^3$ is CH. In another embodiment of Formula (IIc), $X^1$ is N; $X^2$ is $CR^1$; and $X^3$ is CH. In another embodiment of Formula (IIc), $X^1$ is N; $X^2$ is $CR^1$; and $X^3$ is N.

In another embodiment of Formula (IIc), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (IIc), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (IIc), $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (IIc), $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (IIc), $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (IIc), $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $R^1$ is NHC(O)$R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $R^1$ is $C(O)NH_2$. In another embodiment of Formula (IIc), $R^1$ is F. In another embodiment of Formula (IIc), $R^1$ is Cl. In another embodiment of Formula (IIc), $R^1$ is Br. In another embodiment of Formula (IIc), $R^1$ is CN. In another embodiment of Formula (IIc), $R^1$ is $NH_2$. In another embodiment of Formula (IIc), $R^1$ is $NO_2$. In another embodiment of Formula (IIc), $R^1$ is $CF_3$. In another embodiment of Formula (IIc), $R^1$ is $C(O)OH$. In another embodiment of Formula (IIc), $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl.

In another embodiment of Formula (IIc), $X^1$ and $X^3$ are CH; and $X^2$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (IIc), $X^1$ and $X^3$ are CH; and $X^2$ is $CR^1$; $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $X^1$ and $X^3$ are CH; and $X^2$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $X^1$ and $X^3$ are CH; and $X^2$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $X^1$ and $X^3$ are CH; and $X^2$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $X^1$ and $X^3$ are CH; and $X^2$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $X^1$ and $X^3$ are CH; and $X^2$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $X^1$ and $X^3$ are CH; and $X^2$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $X^1$ and $X^3$ are CH; and $X^2$ is $CR^1$; and $R^1$ is $C(O)NH_2$. In another embodiment of Formula (IIc), $X^1$ and $X^3$ are CH; and $X^2$ is $CR^1$; and $R^1$ is F. In another embodiment of Formula (IIc), $X^1$ and $X^3$ are CH; and $X^2$ is $CR^1$; and $R^1$ is Cl. In another embodiment of Formula (IIc), $X^1$ and $X^3$ are CH; and $X^2$ is $CR^1$; and $R^1$ is Br. In another embodiment of Formula (IIc), $X^1$ and $X^3$ are CH; and $X^2$ is $CR^1$; and $R^1$ is CN. In another embodiment of Formula (IIc), $X^1$ and $X^3$ are CH; and $X^2$ is $CR^1$; and $R^1$ is $NH_2$. In another embodiment of Formula (IIc), $X^1$ and $X^3$ are CH; and $X^2$ is $CR^1$; and $R^1$ is $NO_2$. In another embodiment of Formula (IIc), $X^1$ and $X^3$ are CH; and $X^2$ is $CR^1$; and $R^1$ is $CF_3$. In another embodiment of Formula (IIc), $X^1$ and $X^3$ are CH; and $X^2$ is $CR^1$; and $R^1$ is C(O)OH. In another embodiment of Formula (IIc), $X^1$ and $X^3$ are CH; and $X^2$ is $CR^1$; $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In another embodiment of Formula (IIc), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (IIc), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $X^2$ and $X^3$ are CH; and $X^1$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $X^2$ and $X^3$ are CH; and $X^1$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $X^2$ and $X^3$ are CH; and $X^1$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $X^2$ and $X^3$ are CH; and $X^1$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $X^2$ and $X^3$ are CH; and $X^1$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $X^2$ and $X^3$ are CH; and $X^1$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $X^2$ and $X^3$ are CH; and $X^1$ is $CR^1$; and $R^1$ is $C(O)NH_2$. In another embodiment of Formula (IIc), $X^2$ and $X^3$ are CH; and $X^1$ is $CR^1$; and $R^1$ is F. In another embodiment of Formula (IIc), $X^2$ and $X^3$ are CH; and $X^1$ is $CR^1$; and $R^1$ is Cl. In another embodiment of Formula (IIc), $X^2$ and $X^3$ are CH; and $X^1$ is $CR^1$; and $R^1$ is Br. In another embodiment of Formula (IIc), $X^2$ and $X^3$ are CH; and $X^1$ is $CR^1$; and $R^1$ is CN. In another embodiment of Formula (IIc), $X^2$ and $X^3$ are CH; and $X^1$ is $CR^1$; and $R^1$ is $NH_2$. In another embodiment of Formula (IIc), $X^2$ and $X^3$ are CH; and $X^1$ is $CR^1$; and $R^1$ is $NO_2$. In another embodiment of Formula (IIc), $X^2$ and $X^3$ are CH; and $X^1$ is $CR^1$; and $R^1$ is $CF_3$. In another embodiment of Formula (IIc), $X^2$ and $X^3$ are CH; and $X^1$ is $CR^1$; and $R^1$ is C(O)OH. In another embodiment of Formula (IIc), $X^2$ and $X^3$ are CH; and $X^1$ is $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In another embodiment of Formula (IIc), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (IIc), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $X^1$ is CH; and $X^2$ and $X^3$ are $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $X^1$ is CH; and $X^2$ and $X^3$ are $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $X^1$ is CH; and $X^2$ and $X^3$ are $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $X^1$ is CH; and $X^2$ and $X^3$ are $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $X^1$ is CH; and $X^2$ and $X^3$ are $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $X^1$ is CH; and $X^2$ and $X^3$ are $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIc), $X^1$ is CH; and $X^2$ and $X^3$ are $CR^1$; and $R^1$ is $C(O)NH_2$. In another embodiment of Formula (IIc), $X^1$ is CH; and $X^2$ and $X^3$ are $CR^1$; and $R^1$ is F. In another embodiment of Formula (IIc), $X^1$ is CH; and $X^2$ and $X^3$ are $CR^1$; and $R^1$ is Cl. In another embodiment of Formula (IIc), $X^1$ is CH; and $X^2$ and $X^3$ are $CR^1$; and $R^1$ is Br. In another embodiment of Formula (IIc), $X^1$ is CH; and $X^2$ and $X^3$ are $CR^1$; and $R^1$ is CN. In another embodiment of Formula (IIc), $X^1$ is CH; and $X^2$ and $X^3$ are $CR^1$; and $R^1$ is $NH_2$. In another embodiment of Formula (IIc), $X^1$ is CH; and $X^2$ and $X^3$ are $CR^1$; and $R^1$ is $NO_2$. In another embodiment of Formula (IIc), $X^1$ is CH; and $X^2$ and $X^3$ are $CR^1$; and $R^1$ is $CF_3$. In another embodiment of Formula (IIc), $X^1$ is CH; and $X^2$ and $X^3$ are $CR^1$; and $R^1$ is C(O)OH. In another embodiment of Formula (IIc), $X^1$ is CH; and $X^2$ and $X^3$ are $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

Still another embodiment pertains to compounds having Formula (IIc), which include N-{4-[(3-phenylpropyl)carbamoyl]phenyl}-1,3-dihydro-2H-isoindole-2-carboxamide;
N-(4-{[4-(aminomethyl)benzyl]carbamoyl}phenyl)-5-fluoro-1,3-dihydro-2H-isoindole-2-carboxamide;
5-cyano-N-{4-[(3-phenylpropyl)carbamoyl]phenyl}-1,3-dihydro-2H-isoindole-2-carboxamide;
N-{4-[(cyclopentylmethyl)carbamoyl]phenyl}-5-fluoro-1,3-dihydro-2H-isoindole-2-carboxamide;
5-cyano-N-[4-(propylcarbamoyl)phenyl]-1,3-dihydro-2H-isoindole-2-carboxamide;
N-(4-{[4-(furo[3,2-c]pyridin-4-yl)piperazin-1-yl]carbonyl}phenyl)-1,3-dihydro-2H-isoindole-2-carboxamide;
5-cyano-N-(4-{[4-(pyridin-2-yl)piperazin-1-yl]carbonyl}phenyl)-1,3-dihydro-2H-isoindole-2-carboxamide;
5-fluoro-N-{4-[(pyridin-2-ylmethyl)carbamoyl]phenyl}-1,3-dihydro-2H-isoindole-2-carboxamide;
N-[4-(benzylcarbamoyl)phenyl]-5-fluoro-1,3-dihydro-2H-isoindole-2-carboxamide;
N-{4-[(3,4-dimethoxybenzyl)carbamoyl]phenyl}-1,3-dihydro-2H-isoindole-2-carboxamide;
5-methyl-N-(4-{[4-(pyridin-2-yl)piperazin-1-yl]carbonyl}phenyl)-1,3-dihydro-2H-isoindole-2-carboxamide;
N-(4-{[4-(thieno[3,2-c]pyridin-4-yl)piperazin-1-yl]carbonyl}phenyl)-1,3-dihydro-2H-isoindole-2-carboxamide;
N-{4-[(2,3-dimethoxybenzyl)carbamoyl]phenyl}-1,3-dihydro-2H-isoindole-2-carboxamide;
5-fluoro-N-{4-[(3-phenylpropyl)carbamoyl]phenyl}-1,3-dihydro-2H-isoindole-2-carboxamide;
5-fluoro-N-(4-{[4-(pyridazin-3-yl)piperazin-1-yl]carbonyl}phenyl)-1,3-dihydro-2H-isoindole-2-carboxamide;
N-{4-[(2,3-dihydro-1,4-benzodioxin-5-ylmethyl)carbamoyl]phenyl}-1,3-dihydro-2H-isoindole-2-carboxamide;
5-fluoro-N-(4-{[1-(3-methylbutyl)-1H-pyrazol-4-yl]carbamoyl}phenyl)-1,3-dihydro-2H-isoindole-2-carboxamide;
N-{4-[(2-fluorobenzyl)carbamoyl]phenyl}-1,3-dihydro-2H-isoindole-2-carboxamide;
5-fluoro-N-(4-{[4-(pyrimidin-2-yl)piperazin-1-yl]carbonyl}phenyl)-1,3-dihydro-2H-isoindole-2-carboxamide;
5-fluoro-N-{4-[(3-methylbutyl)carbamoyl]phenyl}-1,3-dihydro-2H-isoindole-2-carboxamide;
N-{4-[(2-methoxybenzyl)carbamoyl]phenyl}-1,3-dihydro-2H-isoindole-2-carboxamide;
5-fluoro-N-(4-{[4-(pyridin-2-yl)piperazin-1-yl]carbonyl}phenyl)-1,3-dihydro-2H-isoindole-2-carboxamide;
N-{4-[(3-fluorobenzyl)carbamoyl]phenyl}-1,3-dihydro-2H-isoindole-2-carboxamide;
5-fluoro-N-(4-{[3-(2-oxopyrrolidin-1-yl)propyl]carbamoyl}phenyl)-1,3-dihydro-2H-isoindole-2-carboxamide;
5-cyano-N-{4-[(3-methylbutyl)carbamoyl]phenyl}-1,3-dihydro-2H-isoindole-2-carboxamide;
N-{4-[(cyclopentylmethyl)carbamoyl]phenyl}-5-methyl-1,3-dihydro-2H-isoindole-2-carboxamide;
N-(4-{[4-(4-cyanophenyl)piperazin-1-yl]carbonyl}phenyl)-1,3-dihydro-2H-isoindole-2-carboxamide;
N-{4-[(4-fluorobenzyl)carbamoyl]phenyl}-1,3-dihydro-2H-isoindole-2-carboxamide;
N-{4-[(3,5-dimethoxybenzyl)carbamoyl]phenyl}-1,3-dihydro-2H-isoindole-2-carboxamide;
5-fluoro-N-{4-[(tetrahydro furan-3-ylmethyl)carbamoyl]phenyl}-1,3-dihydro-2H-isoindole-2-carboxamide;
N-{4-[(2,2-dimethylpropyl)carbamoyl]phenyl}-1,3-dihydro-2H-isoindole-2-carboxamide;
5-fluoro-N-(4-{[2-(2-oxopyrrolidin-1-yl)ethyl]carbamoyl}phenyl)-1,3-dihydro-2H-isoindole-2-carboxamide;
N-(4-{[4-(trifluoromethoxy)benzyl]carbamoyl}phenyl)-1,3-dihydro-2H-isoindole-2-carboxamide;
N-(4-{[3-fluoro-5-(trifluoromethyl)benzyl]carbamoyl}phenyl)-1,3-dihydro-2H-isoindole-2-carboxamide;
5-fluoro-N-(4-{[4-(pyrazin-2-yl)piperazin-1-yl]carbonyl}phenyl)-1,3-dihydro-2H-isoindole-2-carboxamide;
N-{4-[(3-methylbutyl)carbamoyl]phenyl}-1,3-dihydro-2H-isoindole-2-carboxamide;
5-methoxy-N-{4-[(3-phenylpropyl)carbamoyl]phenyl}-1,3-dihydro-2H-isoindole-2-carboxamide;
N-{4-[(4-chlorobenzyl)carbamoyl]phenyl}-1,3-dihydro-2H-isoindole-2-carboxamide;
N-{4-[(cyclopentylmethyl)carbamoyl]phenyl}-1,3-dihydro-2H-isoindole-2-carboxamide;
N-{4-[(3,4,5-trimethoxybenzyl)carbamoyl]phenyl}-1,3-dihydro-2H-isoindole-2-carboxamide;
N-(4-{[4-(pyrimidin-2-yl)piperazin-1-yl]carbonyl}phenyl)-1,3-dihydro-2H-isoindole-2-carboxamide;
5-nitro-N-[4-(propylcarbamoyl)phenyl]-1,3-dihydro-2H-isoindole-2-carboxamide;
5-methyl-N-{4-[(3-methylbutyl)carbamoyl]phenyl}-1,3-dihydro-2H-isoindole-2-carboxamide;

N-(4-{[4-(4-fluorophenyl)piperazin-1-yl]carbonyl}phenyl)-1,3-dihydro-2H-isoindole-2-carboxamide;
N-{4-[(4-methoxybenzyl)carbamoyl]phenyl}-1,3-dihydro-2H-isoindole-2-carboxamide;
N-{4-[(2-thienylmethyl)carbamoyl]phenyl}-1,3-dihydro-2H-isoindole-2-carboxamide;
N-(4-{[4-(pyrimidin-2-yl)piperazin-1-yl]carbonyl}phenyl)-5-(trifluoromethyl)-1,3-dihydro-2H-isoindole-2-carboxamide;
N-{4-[(1-ethyl-1H-pyrazol-4-yl)carbamoyl]phenyl}-5-fluoro-1,3-dihydro-2H-isoindole-2-carboxamide;
N-{4-[(1-benzyl-1H-pyrazol-4-yl)carbamoyl]phenyl}-5-fluoro-1,3-dihydro-2H-isoindole-2-carboxamide;
N-(4-{[4-(pyridin-2-yl)piperazin-1-yl]carbonyl}phenyl)-1,3-dihydro-2H-isoindole-2-carboxamide;
N-(4-{[4-(pyrazin-2-yl)piperazin-1-yl]carbonyl}phenyl)-1,3-dihydro-2H-isoindole-2-carboxamide;
N-(4-{[4-(2-methoxyphenyl)piperazin-1-yl]carbonyl}phenyl)-1,3-dihydro-2H-isoindole-2-carboxamide;
N-{4-[(3,3-dimethylbutyl)carbamoyl]phenyl}-1,3-dihydro-2H-isoindole-2-carboxamide;
N-(4-{[(2R)-tetrahydrofuran-2-ylmethyl]carbamoyl}phenyl)-1,3-dihydro-2H-isoindole-2-carboxamide;
N-(4-{[4-(3-methoxyphenyl)piperazin-1-yl]carbonyl}phenyl)-1,3-dihydro-2H-isoindole-2-carboxamide;
N-(4-{[4-(4-acetylphenyl)piperazin-1-yl]carbonyl}phenyl)-1,3-dihydro-2H-isoindole-2-carboxamide;
N-(4-{[2-(2,3-dimethoxyphenyl)ethyl]carbamoyl}phenyl)-1,3-dihydro-2H-isoindole-2-carboxamide;
N-{4-[(3-thienylmethyl)carbamoyl]phenyl}-1,3-dihydro-2H-isoindole-2-carboxamide;
5-methoxy-N-{4-[(3-methylbutyl)carbamoyl]phenyl}-1,3-dihydro-2H-isoindole-2-carboxamide;
N-{4-[(pyridin-2-ylmethyl)carbamoyl]phenyl}-1,3-dihydro-2H-isoindole-2-carboxamide;
5-fluoro-N-(4-{[2-(2-thienyl)ethyl]carbamoyl}phenyl)-1,3-dihydro-2H-isoindole-2-carboxamide;
N-(4-{[(2S)-tetrahydrofuran-2-ylmethyl]carbamoyl}phenyl)-1,3-dihydro-2H-isoindole-2-carboxamide;
N-(4-{[1-(3-methylbutyl)-1H-pyrazol-4-yl]carbamoyl}phenyl)-1,3-dihydro-2H-isoindole-2-carboxamide;
4-chloro-N-(4-{[4-(pyridin-2-yl)piperazin-1-yl]carbonyl}phenyl)-1,3-dihydro-2H-isoindole-2-carboxamide;
N-{4-[(4-phenylpiperazin-1-yl)carbonyl]phenyl}-1,3-dihydro-2H-isoindole-2-carboxamide;
N-{4-[(6-aminohexyl)carbamoyl]phenyl}-1,3-dihydro-2H-isoindole-2-carboxamide;
4-chloro-N-{4-[(3-methylbutyl)carbamoyl]phenyl}-1,3-dihydro-2H-isoindole-2-carboxamide;
N-(4-{[2-(2-thienyl)ethyl]carbamoyl}phenyl)-1,3-dihydro-2H-isoindole-2-carboxamide;
5-methoxy-N-(4-{[4-(pyridin-2-yl)piperazin-1-yl]carbonyl}phenyl)-1,3-dihydro-2H-isoindole-2-carboxamide;
N-{4-[(1,3-benzodioxol-5-ylmethyl)carbamoyl]phenyl}-1,3-dihydro-2H-isoindole-2-carboxamide;
N-{4-[(3-methoxybenzyl)carbamoyl]phenyl}-1,3-dihydro-2H-isoindole-2-carboxamide;
N-(4-{[4-(pyridin-3-yl)piperazin-1-yl]carbonyl}phenyl)-1,3-dihydro-2H-isoindole-2-carboxamide;
N-[4-(benzylcarbamoyl)phenyl]-1,3-dihydro-2H-isoindole-2-carboxamide;
N-(4-{[4-(pyridazin-3-yl)piperazin-1-yl]carbonyl}phenyl)-1,3-dihydro-2H-isoindole-2-carboxamide;
N-{4-[(pyrimidin-4-ylmethyl)carbamoyl]phenyl}-1,3-dihydro-2H-isoindole-2-carboxamide;
N-(4-{[4-(3-fluorophenyl)piperazin-1-yl]carbonyl}phenyl)-1,3-dihydro-2H-isoindole-2-carboxamide;
N-{4-[(2-methylbutyl)carbamoyl]phenyl}-1,3-dihydro-2H-isoindole-2-carboxamide;
N-(4-{[4-(pyridin-2-yl)piperazin-1-yl]carbonyl}phenyl)-5-(trifluoromethyl)-1,3-dihydro-2H-isoindole-2-carboxamide;
N-{4-[(3-butoxypropyl)carbamoyl]phenyl}-1,3-dihydro-2H-isoindole-2-carboxamide;
N-(4-{[(1S)-2-hydroxy-1-phenylethyl]carbamoyl}phenyl)-1,3-dihydro-2H-isoindole-2-carboxamide;
N-(4-{[2-(3,4-dihydroxyphenyl)ethyl]carbamoyl}phenyl)-1,3-dihydro-2H-isoindole-2-carboxamide;
N-{4-[(3-propoxypropyl)carbamoyl]phenyl}-1,3-dihydro-2H-isoindole-2-carboxamide;
N-{4-[(3-furylmethyl)carbamoyl]phenyl}-1,3-dihydro-2H-isoindole-2-carboxamide;
N-(4-{[4-(2-cyanophenyl)piperazin-1-yl]carbonyl}phenyl)-1,3-dihydro-2H-isoindole-2-carboxamide;
N-{4-[(3-hydroxy-2-methylphenyl)carbamoyl]phenyl}-1,3-dihydro-2H-isoindole-2-carboxamide;
N-{4-[(3-methylbutyl)carbamoyl]phenyl}-5-(trifluoromethyl)-1,3-dihydro-2H-isoindole-2-carboxamide;
N-{4-[(3-methyl-1H-indazol-5-yl)carbamoyl]phenyl}-1,3-dihydro-2H-isoindole-2-carboxamide;
N-{4-[(3-ethoxypropyl)carbamoyl]phenyl}-1,3-dihydro-2H-isoindole-2-carboxamide;
N-(4-{[4-(pyrazin-2-yl)piperazin-1-yl]carbonyl}phenyl)-5-(trifluoromethyl)-1,3-dihydro-2H-isoindole-2-carboxamide;
N-(4-{[2-(2,5-dimethoxyphenyl)ethyl]carbamoyl}phenyl)-1,3-dihydro-2H-isoindole-2-carboxamide;
N-{4-[(tetrahydrofuran-3-ylmethyl)carbamoyl]phenyl}-1,3-dihydro-2H-isoindole-2-carboxamide;
N-{4-[(1-benzyl-1H-pyrazol-4-yl)carbamoyl]phenyl}-1,3-dihydro-2H-isoindole-2-carboxamide;
methyl 5-({4-[(1,3-dihydro-2H-isoindol-2-ylcarbonyl)amino]benzoyl}amino)-1H-indazole-3-carboxylate;
N-{4-{[2-(2-oxopyrrolidin-1-yl)ethyl]carbamoyl}phenyl)-1,3-dihydro-2H-isoindole-2-carboxamide;
N-{4-[(pyridin-4-ylmethyl)carbamoyl]phenyl}-1,3-dihydro-2H-isoindole-2-carboxamide;
N-(4-{[4-(5-chloropyridin-2-yl)piperazin-1-yl]carbonyl}phenyl)-1,3-dihydro-2H-isoindole-2-carboxamide;
N-(4-{[2-(1H-indol-3-yl)ethyl]carbamoyl}phenyl)-1,3-dihydro-2H-isoindole-2-carboxamide;
N-(4-{[4-(trifluoromethyl)benzyl]carbamoyl}phenyl)-1,3-dihydro-2H-isoindole-2-carboxamide;
N-{4-[(3,5-dimethoxyphenyl)carbamoyl]phenyl}-1,3-dihydro-2H-isoindole-2-carboxamide;
N-{4-[(pyridin-3-ylmethyl)carbamoyl]phenyl}-1,3-dihydro-2H-isoindole-2-carboxamide;
N-[4-(2,3-dihydro-1,4-benzodioxin-6-ylcarbamoyl)phenyl]-1,3-dihydro-2H-isoindole-2-carboxamide;
N-(4-{[4-(2-fluorobenzoyl)piperazin-1-yl]carbonyl}phenyl)-1,3-dihydro-2H-isoindole-2-carboxamide;
N-(4-{[2-(5-methoxy-1H-indol-3-yl)ethyl]carbamoyl}phenyl)-1,3-dihydro-2H-isoindole-2-carboxamide;

N-{4-[(3-aminobenzyl)carbamoyl]phenyl}-1,3-dihydro-2H-isoindole-2-carboxamide;
N-(4-{[2-(2-chlorophenyl)ethyl]carbamoyl}phenyl)-1,3-dihydro-2H-isoindole-2-carboxamide;
N-(4-{[(2R)-1-hydroxy-4-methylpentan-2-yl]carbamoyl}phenyl)-1,3-dihydro-2H-isoindole-2-carboxamide;
N-{4-[(2-propoxyethyl)carbamoyl]phenyl}-1,3-dihydro-2H-isoindole-2-carboxamide;
N-{4-[(3-isobutoxypropyl)carbamoyl]phenyl}-1,3-dihydro-2H-isoindole-2-carboxamide;
N-(4-{[4-(pyridin-4-yl)piperazin-1-yl]carbonyl}phenyl)-1,3-dihydro-2H-isoindole-2-carboxamide;
N-[4-({4-[5-(trifluoromethyl)pyridin-2-yl]piperazin-1-yl}carbonyl)phenyl]-1,3-dihydro-2H-isoindole-2-carboxamide;
N-{4-[(3,4,5-trimethoxyphenyl)carbamoyl]phenyl}-1,3-dihydro-2H-isoindole-2-carboxamide;
N-{4-[(4-methylpiperidin-1-yl)carbonyl]phenyl}-1,3-dihydro-2H-isoindole-2-carboxamide;
N-(4-{[2-[4-(dimethylamino)phenyl]ethyl]carbamoyl}phenyl)-1,3-dihydro-2H-isoindole-2-carboxamide;
N-(4-{[3-(trifluoromethoxy)benzyl]carbamoyl}phenyl)-1,3-dihydro-2H-isoindole-2-carboxamide;
N-(4-{[(1R)-3-hydroxy-1-phenylpropyl]carbamoyl}phenyl)-1,3-dihydro-2H-isoindole-2-carboxamide;
N-{4-[(3-cyanophenyl)carbamoyl]phenyl}-1,3-dihydro-2H-isoindole-2-carboxamide;
N-{4-[(3-fluoro-4-methoxyphenyl)carbamoyl]phenyl}-1,3-dihydro-2H-isoindole-2-carboxamide;
N-{4-[(2,3-dimethoxyphenyl)carbamoyl]phenyl}-1,3-dihydro-2H-isoindole-2-carboxamide;
N-(4-{[2-(2-fluorophenyl)ethyl]carbamoyl}phenyl)-1,3-dihydro-2H-isoindole-2-carboxamide;
N-[4-(isobutylcarbamoyl)phenyl]-1,3-dihydro-2H-isoindole-2-carboxamide;
N-(4-{[2-(1,3-benzodioxol-5-yl)ethyl]carbamoyl}phenyl)-1,3-dihydro-2H-isoindole-2-carboxamide;
N-(4-{[2-(2-methoxyphenyl)ethyl]carbamoyl}phenyl)-1,3-dihydro-2H-isoindole-2-carboxamide;
N-[4-(butylcarbamoyl)phenyl]-1,3-dihydro-2H-isoindole-2-carboxamide;
N-{4-[(2-isopropoxyethyl)carbamoyl]phenyl}-1,3-dihydro-2H-isoindole-2-carboxamide;
N-{4-[(3-isopropoxypropyl)carbamoyl]phenyl}-1,3-dihydro-2H-isoindole-2-carboxamide;
4-chloro-N-{4-[(3-phenylpropyl)carbamoyl]phenyl}-1,3-dihydro-2H-isoindole-2-carboxamide;
N-(4-{[2-(4-methoxyphenyl)ethyl]carbamoyl}phenyl)-1,3-dihydro-2H-isoindole-2-carboxamide;
N-{4-[(3-methoxypropyl)carbamoyl]phenyl}-1,3-dihydro-2H-isoindole-2-carboxamide;
N-(4-{[2-(4-fluorophenyl)ethyl]carbamoyl}phenyl)-1,3-dihydro-2H-isoindole-2-carboxamide;
N-(4-{[3-(2-oxopyrrolidin-1-yl)propyl]carbamoyl}phenyl)-1,3-dihydro-2H-isoindole-2-carboxamide;
N-{4-[(2,4-dimethoxyphenyl)carbamoyl]phenyl}-1,3-dihydro-2H-isoindole-2-carboxamide;
$N^2$-[4-(propylcarbamoyl)phenyl]-1,3-dihydro-2H-isoindole-2,5-dicarboxamide;
N-{4-[(2-phenoxyethyl)carbamoyl]phenyl}-1,3-dihydro-2H-isoindole-2-carboxamide;
N-(4-{[2-(4-hydroxyphenyl)ethyl]carbamoyl}phenyl)-1,3-dihydro-2H-isoindole-2-carboxamide;
N-(4-{[2-(3-fluorophenyl)ethyl]carbamoyl}phenyl)-1,3-dihydro-2H-isoindole-2-carboxamide;
N-[4-({1-[(3S)-tetrahydrofuran-3-yl]-1H-pyrazol-4-yl}carbamoyl)phenyl]-1,3-dihydro-2H-isoindole-2-carboxamide;
5-methyl-N-{4-[(3-phenylpropyl)carbamoyl]phenyl}-1,3-dihydro-2H-isoindole-2-carboxamide;
N-[4-(1,4-dioxa-8-azaspiro[4.5]dec-8-ylcarbonyl)phenyl]-1,3-dihydro-2H-isoindole-2-carboxamide;
N-{4-[(2-phenylethyl)carbamoyl]phenyl}-1,3-dihydro-2H-isoindole-2-carboxamide;
N-(4-{[2-(2,4-dimethoxyphenyl)ethyl]carbamoyl}phenyl)-1,3-dihydro-2H-isoindole-2-carboxamide;
N-{4-[(3-(methylthio)propyl)carbamoyl]phenyl}-1,3-dihydro-2H-isoindole-2-carboxamide;
N-{4-[(2-ethoxyethyl)carbamoyl]phenyl}-1,3-dihydro-2H-isoindole-2-carboxamide;
N-{4-[(2-fluorophenyl)carbamoyl]phenyl}-1,3-dihydro-2H-isoindole-2-carboxamide;
N-(4-{[2-(pyridin-3-yl)ethyl]carbamoyl}phenyl)-1,3-dihydro-2H-isoindole-2-carboxamide;
N-[4-({4-[(trifluoromethyl)thio]benzyl}carbamoyl)phenyl]-1,3-dihydro-2H-isoindole-2-carboxamide;
N-{4-[(3,4-dimethoxyphenyl)carbamoyl]phenyl}-1,3-dihydro-2H-isoindole-2-carboxamide;
N-(4-{[3-(2-fluorophenyl)pyrrolidin-1-yl]carbonyl}phenyl)-1,3-dihydro-2H-isoindole-2-carboxamide;
N-(4-{[3-(1H-imidazol-1-yl)propyl]carbamoyl}phenyl)-1,3-dihydro-2H-isoindole-2-carboxamide;
N-(4-{[2-(3-chlorophenyl)ethyl]carbamoyl}phenyl)-1,3-dihydro-2H-isoindole-2-carboxamide;
N-{4-[(4-hydroxybutyl)carbamoyl]phenyl}-1,3-dihydro-2H-isoindole-2-carboxamide;
N-{4-[(3-phenylpropyl)carbamoyl]phenyl}-5-(trifluoromethyl)-1,3-dihydro-2H-isoindole-2-carboxamide;
N-(4-{[4-(hydroxymethyl)phenyl]carbamoyl}phenyl)-1,3-dihydro-2H-isoindole-2-carboxamide;
N-[4-(1,3-benzodioxol-5-ylcarbamoyl)phenyl]-1,3-dihydro-2H-isoindole-2-carboxamide;
N-{4-[(1-isopropyl-1H-pyrazol-4-yl)carbamoyl]phenyl}-1,3-dihydro-2H-isoindole-2-carboxamide;
N-{4-[(4-hydroxyphenyl)carbamoyl]phenyl}-1,3-dihydro-2H-isoindole-2-carboxamide;
N-{4-[(1-ethyl-1H-pyrazol-4-yl)carbamoyl]phenyl}-1,3-dihydro-2H-isoindole-2-carboxamide;
N-{4-[(2,5-dimethoxyphenyl)carbamoyl]phenyl}-1,3-dihydro-2H-isoindole-2-carboxamide;
N-{4-[methyl(3-phenylpropyl)carbamoyl]phenyl}-1,3-dihydro-2H-isoindole-2-carboxamide;
N-{4-[(2-hydroxy-2-methylpropyl)carbamoyl]phenyl}-1,3-dihydro-2H-isoindole-2-carboxamide;
N-(4-{[4-(trifluoromethyl)piperidin-1-yl]carbonyl}phenyl)-1,3-dihydro-2H-isoindole-2-carboxamide;
N-[4-(thiomorpholin-4-ylcarbonyl)phenyl]-1,3-dihydro-2H-isoindole-2-carboxamide;
N-[4-(5,6-dihydroimidazo[1,5-a]pyrazin-7(8H)-ylcarbonyl)phenyl]-1,3-dihydro-2H-isoindole-2-carboxamide;
N-(4-{[4-(2-furoyl)piperazin-1-yl]carbonyl}phenyl)-1,3-dihydro-2H-isoindole-2-carboxamide;
N-{4-[(1-benzylpiperidin-4-yl)carbamoyl]phenyl}-1,3-dihydro-2H-isoindole-2-carboxamide;
N-{4-[(4-methoxyphenyl)carbamoyl]phenyl}-1,3-dihydro-2H-isoindole-2-carboxamide;
N-{4-[(3-methoxyphenyl)carbamoyl]phenyl}-1,3-dihydro-2H-isoindole-2-carboxamide;
N-{4-[(5-acetamido-2-methoxyphenyl)carbamoyl]phenyl}-1,3-dihydro-2H-isoindole-2-carboxamide;

N-(4-{[2-(3,5-dimethoxyphenyl)ethyl]carbamoyl}phenyl)-1,3-dihydro-2H-isoindole-2-carboxamide;
N-[4-({2-[3-(trifluoromethyl)phenyl]ethyl}carbamoyl)phenyl]-1,3-dihydro-2H-isoindole-2-carboxamide;
N-{4-[(2-methylbutan-2-yl)carbamoyl]phenyl}-1,3-dihydro-2H-isoindole-2-carboxamide;
N-(4-{[2-(1H-imidazol-4-yl)ethyl]carbamoyl}phenyl)-1,3-dihydro-2H-isoindole-2-carboxamide;
N-(4-{[(2S)-2-hydroxypropyl]carbamoyl}phenyl)-1,3-dihydro-2H-isoindole-2-carboxamide;
N-(4-{[(1R)-1-(3-cyanophenyl)ethyl]carbamoyl}phenyl)-1,3-dihydro-2H-isoindole-2-carboxamide;
N-(4-{[(2S)-1-hydroxy-3-methylbutan-2-yl]carbamoyl}phenyl)-1,3-dihydro-2H-isoindole-2-carboxamide;
N-{4-[benzyl(2-hydroxyethyl)carbamoyl]phenyl}-1,3-dihydro-2H-isoindole-2-carboxamide;
N-{4-[(4-cyanophenyl)carbamoyl]phenyl}-1,3-dihydro-2H-isoindole-2-carboxamide;
N-(4-{[2-(4-chlorophenyl)ethyl]carbamoyl}phenyl)-1,3-dihydro-2H-isoindole-2-carboxamide;
N-(4-{[2-(4-methylpiperazin-1-yl)ethyl]carbamoyl}phenyl)-1,3-dihydro-2H-isoindole-2-carboxamide;
N-(4-{[2-(pyridin-2-yl)ethyl]carbamoyl}phenyl)-1,3-dihydro-2H-isoindole-2-carboxamide;
N-{4-[(cyanomethyl)carbamoyl]phenyl}-1,3-dihydro-2H-isoindole-2-carboxamide;
N-[4-(cyclohexylcarbamoyl)phenyl]-1,3-dihydro-2H-isoindole-2-carboxamide;
N-{4-[(3-hydroxyphenyl)carbamoyl]phenyl}-1,3-dihydro-2H-isoindole-2-carboxamide;
N-{4-[butyl(methyl)carbamoyl]phenyl}-1,3-dihydro-2H-isoindole-2-carboxamide;
N-(4-{[4-(dimethylamino)phenyl]carbamoyl}phenyl)-1,3-dihydro-2H-isoindole-2-carboxamide;
N-[4-(3,4-dihydroisoquinolin-2(1H)-ylcarbonyl)phenyl]-1,3-dihydro-2H-isoindole-2-carboxamide;
N-[4-(1,3-dihydro-2H-isoindol-2-ylcarbonyl)phenyl]-1,3-dihydro-2H-isoindole-2-carboxamide;
N-[4-(2,3-dihydro-1H-indol-1-ylcarbonyl)phenyl]-1,3-dihydro-2H-isoindole-2-carboxamide;
N-[4-(phenylcarbamoyl)phenyl]-1,3-dihydro-2H-isoindole-2-carboxamide;
N-{4-[(4-fluorophenyl)carbamoyl]phenyl}-1,3-dihydro-2H-isoindole-2-carboxamide;
N-(4-{[2-(diethylamino)ethyl]carbamoyl}phenyl)-1,3-dihydro-2H-isoindole-2-carboxamide;
N-{4-[(2-hydroxy-2-phenylethyl)(methyl)carbamoyl]phenyl}-1,3-dihydro-2H-isoindole-2-carboxamide;
N-{4-[(2-aminophenyl)carbamoyl]phenyl}-1,3-dihydro-2H-isoindole-2-carboxamide;
N-(4-{[(2R)-2-hydroxypropyl]carbamoyl}phenyl)-1,3-dihydro-2H-isoindole-2-carboxamide;
N-(4-{[(2S)-1-amino-4-methyl-1-oxopentan-2-yl]carbamoyl}phenyl)-1,3-dihydro-2H-isoindole-2-carboxamide;
tert-butyl (1-{4-[(1,3-dihydro-2H-isoindol-2-ylcarbonyl)amino]benzoyl}piperidin-4-yl)carbamate;
N-(4-{[3-(morpholin-4-yl)propyl]carbamoyl}phenyl)-1,3-dihydro-2H-isoindole-2-carboxamide;
N-[4-({4-[3-chloro-5-(trifluoromethyl)pyridin-2-yl]piperazin-1-yl}carbonyl)phenyl]-1,3-dihydro-2H-isoindole-2-carboxamide;
N-(4-{[4-(cyclohexylmethyl)piperazin-1-yl]carbonyl}phenyl)-1,3-dihydro-2H-isoindole-2-carboxamide;
N-(4-{[1-(3-chlorobenzyl)-1H-pyrazol-4-yl]carbamoyl}phenyl)-1,3-dihydro-2H-isoindole-2-carboxamide;
N-(4-{[3-(diethylcarbamoyl)piperidin-1-yl]carbonyl}phenyl)-1,3-dihydro-2H-isoindole-2-carboxamide;
N-(4-{[3-(piperidin-1-yl)propyl]carbamoyl}phenyl)-1,3-dihydro-2H-isoindole-2-carboxamide;
N-(4-{[4-(2-hydroxyethyl)piperazin-1-yl]carbonyl}phenyl)-1,3-dihydro-2H-isoindole-2-carboxamide;
N-{4-[(2-hydroxy-6-methylphenyl)carbamoyl]phenyl}-1,3-dihydro-2H-isoindole-2-carboxamide;
N-(4-{[4-(dimethylamino)butyl]carbamoyl}phenyl)-1,3-dihydro-2H-isoindole-2-carboxamide;
N-{4-[(3-hydroxypropyl)carbamoyl]phenyl}-1,3-dihydro-2H-isoindole-2-carboxamide;
N-{4-[(4-cyclohexylpiperazin-1-yl)carbonyl]phenyl}-1,3-dihydro-2H-isoindole-2-carboxamide;
N-[4-(5,6-dihydro[1,2,4]triazolo[4,3-a]pyrazin-7(8H)-ylcarbonyl)phenyl]-1,3-dihydro-2H-isoindole-2-carboxamide;
N-{4-[methyl(3-methylbutyl)carbamoyl]phenyl}-1,3-dihydro-2H-isoindole-2-carboxamide;
N-[4-(propylcarbamoyl)phenyl]-1,3-dihydro-2H-isoindole-2-carboxamide;
N-(4-{[(2S)-1-hydroxybutan-2-yl]carbamoyl}phenyl)-1,3-dihydro-2H-isoindole-2-carboxamide;
N-{4-[(5-fluoropyridin-2-yl)carbamoyl]phenyl}-1,3-dihydro-2H-isoindole-2-carboxamide;
N-{4-[(cyclopropylmethyl)(propyl)carbamoyl]phenyl}-1,3-dihydro-2H-isoindole-2-carboxamide;
N-(4-{[(2S)-1-methoxypropan-2-yl]carbamoyl}phenyl)-1,3-dihydro-2H-isoindole-2-carboxamide;
N-[4-(1,3,4,9-tetrahydro-2H-beta-carbolin-2-ylcarbonyl)phenyl]-1,3-dihydro-2H-isoindole-2-carboxamide;
N-[4-(tert-butylcarbamoyl)phenyl]-1,3-dihydro-2H-isoindole-2-carboxamide;
N-[4-({4-[4-(trifluoromethyl)phenyl]piperazin-1-yl}carbonyl)phenyl]-1,3-dihydro-2H-isoindole-2-carboxamide;
N-{4-[(3-methylbutan-2-yl)carbamoyl]phenyl}-1,3-dihydro-2H-isoindole-2-carboxamide;
N-{4-[(3,3-difluoropyrrolidin-1-yl)carbonyl]phenyl}-1,3-dihydro-2H-isoindole-2-carboxamide;
N-{4-[(2-methylpiperidin-1-yl)carbonyl]phenyl}-1,3-dihydro-2H-isoindole-2-carboxamide;
N-(4-{[(3S)-1-benzylpyrrolidin-3-yl]carbamoyl}phenyl)-1,3-dihydro-2H-isoindole-2-carboxamide;
N-{4-[(4-hydroxypiperidin-1-yl)carbonyl]phenyl}-1,3-dihydro-2H-isoindole-2-carboxamide;
N-{4-[bis(2-methoxyethyl)carbamoyl]phenyl}-1,3-dihydro-2H-isoindole-2-carboxamide;
N-{4-[(3-fluorophenyl)carbamoyl]phenyl}-1,3-dihydro-2H-isoindole-2-carboxamide;
N-[4-(cyclopentylcarbamoyl)phenyl]-1,3-dihydro-2H-isoindole-2-carboxamide;
N-{4-[(4-carbamoylpiperidin-1-yl)carbonyl]phenyl}-1,3-dihydro-2H-isoindole-2-carboxamide;
N-[4-(cyclopropylcarbamoyl)phenyl]-1,3-dihydro-2H-isoindole-2-carboxamide;
N-[4-(methylcarbamoyl)phenyl]-1,3-dihydro-2H-isoindole-2-carboxamide;
N-(4-{[3-(dimethylamino)propyl]carbamoyl}phenyl)-1,3-dihydro-2H-isoindole-2-carboxamide;
N-{4-[methyl(tetrahydrofuran-2-ylmethyl)carbamoyl]phenyl}-1,3-dihydro-2H-isoindole-2-carboxamide;

N-[4-(pentan-2-ylcarbamoyl)phenyl]-1,3-dihydro-2H-isoindole-2-carboxamide;
N-[4-(pentan-3-ylcarbamoyl)phenyl]-1,3-dihydro-2H-isoindole-2-carboxamide;
N-[4-(cyclobutylcarbamoyl)phenyl]-1,3-dihydro-2H-isoindole-2-carboxamide;
N-{4-[(1,3-dioxolan-2-ylmethyl)(methyl)carbamoyl]phenyl}-1,3-dihydro-2H-isoindole-2-carboxamide;
N-(4-{[1-(4-fluorophenyl)-1H-pyrazol-4-yl]carbamoyl}phenyl)-1,3-dihydro-2H-isoindole-2-carboxamide;
N-{4-[(1-hydroxy-2-methylpropan-2-yl)carbamoyl]phenyl}-1,3-dihydro-2H-isoindole-2-carboxamide;
N-{4-[(1-phenyl-1H-pyrazol-4-yl)carbamoyl]phenyl}-1,3-dihydro-2H-isoindole-2-carboxamide;
N-[4-({2-[4-(trifluoromethyl)phenyl]ethyl}carbamoyl)phenyl]-1,3-dihydro-2H-isoindole-2-carboxamide;
N-{4-[(2-methoxyethyl)(propyl)carbamoyl]phenyl}-1,3-dihydro-2H-isoindole-2-carboxamide;
N-[4-(sec-butylcarbamoyl)phenyl]-1,3-dihydro-2H-isoindole-2-carboxamide;
N-(4-{[3-(trifluoromethyl)piperidin-1-yl]carbonyl}phenyl)-1,3-dihydro-2H-isoindole-2-carboxamide;
N-{4-[bis(2-ethoxyethyl)carbamoyl]phenyl}-1,3-dihydro-2H-isoindole-2-carboxamide;
N-{4-[butyl(ethyl)carbamoyl]phenyl}-1,3-dihydro-2H-isoindole-2-carboxamide;
N-{4-[(1-methoxypropan-2-yl)carbamoyl]phenyl}-1,3-dihydro-2H-isoindole-2-carboxamide;
N-{4-[(2-methoxyethyl)(methyl)carbamoyl]phenyl}-1,3-dihydro-2H-isoindole-2-carboxamide;
N-{4-[(3R)-tetrahydrofuran-3-ylcarbamoyl]phenyl}-1,3-dihydro-2H-isoindole-2-carboxamide;
N-[4-(morpholin-4-ylcarbonyl)phenyl]-1,3-dihydro-2H-isoindole-2-carboxamide;
N-{4-[isobutyl(methyl)carbamoyl]phenyl}-1,3-dihydro-2H-isoindole-2-carboxamide;
N-[4-({4-[2-(2-hydroxyethoxy)ethyl]piperazin-1-yl}carbonyl)phenyl]-1,3-dihydro-2H-isoindole-2-carboxamide;
N-{4-[(3-methylpiperidin-1-yl)carbonyl]phenyl}-1,3-dihydro-2H-isoindole-2-carboxamide;
N-(4-carbamoylphenyl)-1,3-dihydro-2H-isoindole-2-carboxamide;
N-(4-{[(2S)-2-(trifluoromethyl)pyrrolidin-1-yl]carbonyl}phenyl)-1,3-dihydro-2H-isoindole-2-carboxamide;
N-(4-{[(2S)-1-hydroxy-4-methylpentan-2-yl]carbamoyl}phenyl)-1,3-dihydro-2H-isoindole-2-carboxamide;
N-(4-{[(1R)-2-hydroxy-1-phenylethyl]carbamoyl}phenyl)-1,3-dihydro-2H-isoindole-2-carboxamide;
N-{4-[(2-methylpyrrolidin-1-yl)carbonyl]phenyl}-1,3-dihydro-2H-isoindole-2-carboxamide;
N-{4-[ethyl(2-methoxyethyl)carbamoyl]phenyl}-1,3-dihydro-2H-isoindole-2-carboxamide;
N-(4-{[(2R)-1-hydroxy-3-methylbutan-2-yl]carbamoyl}phenyl)-1,3-dihydro-2H-isoindole-2-carboxamide;
N-{4-[(2,6-dimethylmorpholin-4-yl)carbonyl]phenyl}-1,3-dihydro-2H-isoindole-2-carboxamide;
N-(4-{[(2R)-1-hydroxybutan-2-yl]carbamoyl}phenyl)-1,3-dihydro-2H-isoindole-2-carboxamide;
N-{4-[(2,5-dimethylpyrrolidin-1-yl)carbonyl]phenyl}-1,3-dihydro-2H-isoindole-2-carboxamide;
N-[4-(prop-2-yn-1-ylcarbamoyl)phenyl]-1,3-dihydro-2H-isoindole-2-carboxamide;
N-{4-[isopropyl(2-methoxyethyl)carbamoyl]phenyl}-1,3-dihydro-2H-isoindole-2-carboxamide;
N-{4-[isopropyl(propyl)carbamoyl]phenyl}-1,3-dihydro-2H-isoindole-2-carboxamide;
N-{4-[(2-cyanoethyl)(cyclopropyl)carbamoyl]phenyl}-1,3-dihydro-2H-isoindole-2-carboxamide;
N-{4-[ethyl(isopropyl)carbamoyl]phenyl}-1,3-dihydro-2H-isoindole-2-carboxamide;
N-{4-[(3-fluoropyrrolidin-1-yl)carbonyl]phenyl}-1,3-dihydro-2H-isoindole-2-carboxamide;
N-{4-[(1,3-dihydro-2H-isoindol-2-ylcarbonyl)amino]benzoyl}-N-isopropyl-beta-alanine;
N-{4-[methyl(propyl)carbamoyl]phenyl}-1,3-dihydro-2H-isoindole-2-carboxamide;
5,6-dimethoxy-N-{4-[(3-phenylpropyl)carbamoyl]phenyl}-1,3-dihydro-2H-isoindole-2-carboxamide;
N-(4-{[3-(4-chlorophenoxy)propyl]carbamoyl}phenyl)-1,3-dihydro-2H-isoindole-2-carboxamide;
N-(4-{[4-(trifluoromethoxy)phenyl]carbamoyl}phenyl)-1,3-dihydro-2H-isoindole-2-carboxamide;
N-{4-[(4-phenyl-1,3-thiazol-2-yl)carbamoyl]phenyl}-1,3-dihydro-2H-isoindole-2-carboxamide;
methyl 2-{[4-(propylcarbamoyl)phenyl]carbamoyl}isoindoline-5-carboxylate;
2-{[4-(propylcarbamoyl)phenyl]carbamoyl}isoindoline-5-carboxylic acid;
5-amino-N-[4-(propylcarbamoyl)phenyl]-1,3-dihydro-2H-isoindole-2-carboxamide;
5-(hydroxymethyl)-N-[4-(propylcarbamoyl)phenyl]-1,3-dihydro-2H-isoindole-2-carboxamide;
5-(aminomethyl)-N-[4-(propylcarbamoyl)phenyl]-1,3-dihydro-2H-isoindole-2-carboxamide;
5-[(2-hydroxy-2-methylpropanoyl)amino]-N-[4-(propylcarbamoyl)phenyl]-1,3-dihydro-2H-isoindole-2-carboxamide;
5-acetamido-N-[4-(propylcarbamoyl)phenyl]-1,3-dihydro-2H-isoindole-2-carboxamide;
5-[(N,N-dimethylglycyl)amino]-N-[4-(propylcarbamoyl)phenyl]-1,3-dihydro-2H-isoindole-2-carboxamide;
N-[4-(propylcarbamoyl)phenyl]-5-(1H-pyrazol-3-yl)-1,3-dihydro-2H-isoindole-2-carboxamide;
N-[4-(propylcarbamoyl)phenyl]-5-(1H-pyrazol-4-yl)-1,3-dihydro-2H-isoindole-2-carboxamide;
5-[(methoxyacetyl)amino]-N-[4-(propylcarbamoyl)phenyl]-1,3-dihydro-2H-isoindole-2-carboxamide;
5-[(methylsulfonyl)amino]-N-[4-(propylcarbamoyl)phenyl]-1,3-dihydro-2H-isoindole-2-carboxamide;
5-bromo-N-[4-(propylcarbamoyl)phenyl]-1,3-dihydro-2H-isoindole-2-carboxamide;
N-{4-[(3,5-dimethoxybenzyl)carbamoyl]phenyl}-1,3-dihydro-2H-pyrrolo[3,4-c]pyridine-2-carboxamide;
N-{4-[(4-chlorobenzyl)carbamoyl]phenyl}-1,3-dihydro-2H-pyrrolo[3,4-c]pyridine-2-carboxamide;
N-(4-{[4-(pyridin-2-yl)piperazin-1-yl]carbonyl}phenyl)-1,3-dihydro-2H-pyrrolo[3,4-c]pyridine-2-carboxamide;
N-{4-[(3-phenylpropyl)carbamoyl]phenyl}-1,3-dihydro-2H-pyrrolo[3,4-c]pyridine-2-carboxamide;
N-{4-[(tetrahydrofuran-3-ylmethyl)carbamoyl]phenyl}-1,3-dihydro-2H-pyrrolo[3,4-c]pyridine-2-carboxamide;
N-{4-[(3-methylbutyl)carbamoyl]phenyl}-1,3-dihydro-2H-pyrrolo[3,4-c]pyridine-2-carboxamide;
N-{4-[(4,4,4-trifluorobutanoyl)amino]phenyl}-1,3-dihydro-2H-isoindole-2-carboxamide;
N-{4-[(3-ethoxypropanoyl)amino]phenyl}-1,3-dihydro-2H-isoindole-2-carboxamide;
N-{4-[(4-phenylbutanoyl)amino]phenyl}-1,3-dihydro-2H-isoindole-2-carboxamide;

N-{4-[(4-methylpentanoyl)amino]phenyl}-1,3-dihydro-2H-isoindole-2-carboxamide;
N-(4-{[(benzyloxy)acetyl]amino}phenyl)-1,3-dihydro-2H-isoindole-2-carboxamide;
N-{4-[(3-phenylpropanoyl)amino]phenyl}-1,3-dihydro-2H-isoindole-2-carboxamide;
N-{4-[(3-phenoxypropanoyl)amino]phenyl}-1,3-dihydro-2H-isoindole-2-carboxamide;
N-(4-{[N-(2-furoyl)glycyl]amino}phenyl)-1,3-dihydro-2H-isoindole-2-carboxamide;
N-(4-{[4-(2-thienyl)butanoyl]amino}phenyl)-1,3-dihydro-2H-isoindole-2-carboxamide;
N-{4-[(4-oxo-4-phenylbutanoyl)amino]phenyl}-1,3-dihydro-2H-isoindole-2-carboxamide;
N-{4-[(N-benzoylglycyl)amino]phenyl}-1,3-dihydro-2H-isoindole-2-carboxamide;
N-{4-[(4-phenoxybutanoyl)amino]phenyl}-1,3-dihydro-2H-isoindole-2-carboxamide;
N-[4-(propionylamino)phenyl]-1,3-dihydro-2H-isoindole-2-carboxamide;
N-[4-(pentanoylamino)phenyl]-1,3-dihydro-2H-isoindole-2-carboxamide;
N-[4-(hexanoylamino)phenyl]-1,3-dihydro-2H-isoindole-2-carboxamide;
N-[4-(heptanoylamino)phenyl]-1,3-dihydro-2H-isoindole-2-carboxamide;
N-[4-(pent-4-enoylamino)phenyl]-1,3-dihydro-2H-isoindole-2-carboxamide;
N-{4-[(ethoxyacetyl)amino]phenyl}-1,3-dihydro-2H-isoindole-2-carboxamide;
N-(4-{[(2-methoxyethoxy)acetyl]amino}phenyl)-1,3-dihydro-2H-isoindole-2-carboxamide;
N-{4-[(cyclopropylacetyl)amino]phenyl}-1,3-dihydro-2H-isoindole-2-carboxamide;
N-{4-[(cyclopentylacetyl)amino]phenyl}-1,3-dihydro-2H-isoindole-2-carboxamide;
N-(4-{[3-(4-methylpiperazin-1-yl)propanoyl]amino}phenyl)-1,3-dihydro-2H-isoindole-2-carboxamide;
methyl 2-({4-[(cyclopentylacetyl)amino]phenyl}carbamoyl)isoindoline-5-carboxylate;
2-({4-[(cyclopentylacetyl)amino]phenyl}carbamoyl)isoindoline-5-carboxylic acid;
N-{4-[(cyclopentylacetyl)amino]phenyl}-5-(hydroxymethyl)-1,3-dihydro-2H-isoindole-2-carboxamide;
N-{4-[(2-cyclopentylethyl)amino]phenyl}-5-(hydroxymethyl)-1,3-dihydro-2H-isoindole-2-carboxamide;
tert-butyl 4-{4-[(1,3-dihydro-2H-isoindol-2-ylcarbonyl)amino]phenyl}-3,6-dihydropyridine-1(2H)-carboxylate;
N-[4-(1,2,3,6-tetrahydropyridin-4-yl)phenyl]-1,3-dihydro-2H-isoindole-2-carboxamide;
N-{4-[1-(3-methylbutyl)-1H-pyrazol-4-yl]phenyl}-1,3-dihydro-2H-isoindole-2-carboxamide;
N-[4-(1-methyl-1H-pyrazol-4-yl)phenyl]-1,3-dihydro-2H-isoindole-2-carboxamide;
N-{4-[(1E)-5-phenylpent-1-en-1-yl]phenyl}-1,3-dihydro-2H-isoindole-2-carboxamide;
N-[4-(1-propyl-1H-pyrazol-4-yl)phenyl]-1,3-dihydro-2H-isoindole-2-carboxamide;
N-[4-(1-benzyl-1H-pyrazol-4-yl)phenyl]-1,3-dihydro-2H-isoindole-2-carboxamide;
N-{4-[1-(2-hydroxyethyl)-1H-pyrazol-4-yl]phenyl}-1,3-dihydro-2H-isoindole-2-carboxamide;
N-[6-(1-propyl-1H-pyrazol-4-yl)pyridin-3-yl]-1,3-dihydro-2H-isoindole-2-carboxamide;
N-{6-[1-(3-methylbutyl)-1H-pyrazol-4-yl]pyridin-3-yl}-1,3-dihydro-2H-isoindole-2-carboxamide;
N-[4-(5-phenylpentyl)phenyl]-1,3-dihydro-2H-isoindole-2-carboxamide;
N-[2-fluoro-4-(1-propyl-1H-pyrazol-4-yl)phenyl]-1,3-dihydro-2H-isoindole-2-carboxamide;
N-{2-fluoro-4-[1-(3-methylbutyl)-1H-pyrazol-4-yl]phenyl}-1,3-dihydro-2H-isoindole-2-carboxamide;
N-[4-(1-butyryl-1,2,3,6-tetrahydropyridin-4-yl)phenyl]-1,3-dihydro-2H-isoindole-2-carboxamide;
N-[4-(1-isobutyryl-1,2,3,6-tetrahydropyridin-4-yl)phenyl]-1,3-dihydro-2H-isoindole-2-carboxamide;
N-[4-(1-benzoyl-1,2,3,6-tetrahydropyridin-4-yl)phenyl]-1,3-dihydro-2H-isoindole-2-carboxamide;
N-{4-[1-(isopropylsulfonyl)-1,2,3,6-tetrahydropyridin-4-yl]phenyl}-1,3-dihydro-2H-isoindole-2-carboxamide;
N-(1'-isobutyryl-1',2',3',6'-tetrahydro-2,4'-bipyridin-5-yl)-1,3-dihydro-2H-isoindole-2-carboxamide;
N-(1'-benzoyl-1',2',3',6'-tetrahydro-2,4'-bipyridin-5-yl)-1,3-dihydro-2H-isoindole-2-carboxamide;
N-[4-(4-benzoylpiperazin-1-yl)phenyl]-1,3-dihydro-2H-isoindole-2-carboxamide;
N-{4-[4-(isopropylsulfonyl)piperazin-1-yl]phenyl}-1,3-dihydro-2H-isoindole-2-carboxamide;
N-{4-[4-(phenylsulfonyl)piperazin-1-yl]phenyl}-1,3-dihydro-2H-isoindole-2-carboxamide;
N-{4-[3-(benzoylamino)pyrrolidin-1-yl]phenyl}-1,3-dihydro-2H-isoindole-2-carboxamide;
N-{4-[3-(butyrylamino)pyrrolidin-1-yl]phenyl}-1,3-dihydro-2H-isoindole-2-carboxamide;
tert-butyl 4-{4-[(1,3-dihydro-2H-isoindol-2-ylcarbonyl)amino]phenyl}piperazine-1-carboxylate;
N-[4-(4-propionylpiperazin-1-yl)phenyl]-1,3-dihydro-2H-isoindole-2-carboxamide;
N-{4-[4-(cyclopropylcarbonyl)piperazin-1-yl]phenyl}-1,3-dihydro-2H-isoindole-2-carboxamide;
N-(2-butyryl-2,3-dihydro-1H-isoindol-5-yl)-1,3-dihydro-2H-isoindole-2-carboxamide;
N-(2-isobutyryl-2,3-dihydro-1H-isoindol-5-yl)-1,3-dihydro-2H-isoindole-2-carboxamide;
N-(2-benzoyl-2,3-dihydro-1H-isoindol-5-yl)-1,3-dihydro-2H-isoindole-2-carboxamide;
N-[2-(3-methylbutyl)-2,3-dihydro-1H-isoindol-5-yl]-1,3-dihydro-2H-isoindole-2-carboxamide;
N-[4-(hexyloxy)phenyl]-1,3-dihydro-2H-isoindole-2-carboxamide;
N-(5-{[4-(pyridin-2-yl)piperazin-1-yl]carbonyl}pyridin-2-yl)-1,3-dihydro-2H-isoindole-2-carboxamide;
N-{5-[(3-phenylpropyl)carbamoyl]pyridin-2-yl}-1,3-dihydro-2H-isoindole-2-carboxamide;
N-{5-[(3-methylbutyl)carbamoyl]pyridin-2-yl}-1,3-dihydro-2H-isoindole-2-carboxamide;
N-{5-[(3-phenylpropyl)carbamoyl]-1,3-thiazol-2-yl}-1,3-dihydro-2H-isoindole-2-carboxamide;
N-{5-[(3-methylbutyl)carbamoyl]-1,3-thiazol-2-yl}-1,3-dihydro-2H-isoindole-2-carboxamide;
5-fluoro-N-[4-(propylcarbamoyl)phenyl]-1,3-dihydro-2H-isoindole-2-carboxamide;
N-[4-(4-oxo-3,4-dihydrophthalazin-1-yl)phenyl]-1,3-dihydro-2H-isoindole-2-carboxamide;
N-[4-(isoquinolin-4-yl)phenyl]-1,3-dihydro-2H-isoindole-2-carboxamide;
N-[4-(1-oxo-1,2-dihydroisoquinolin-4-yl)phenyl]-1,3-dihydro-2H-isoindole-2-carboxamide;
N-[4-(4-oxo-3,4,5,6,7,8-hexahydrophthalazin-1-yl)phenyl]-1,3-dihydro-2H-isoindole-2-carboxamide;
N-[4-(8-fluoro-4-oxo-3,4-dihydrophthalazin-1-yl)phenyl]-1,3-dihydro-2H-isoindole-2-carboxamide;

5-fluoro-N-[4-(4-oxo-3,4-dihydrophthalazin-1-yl)phenyl]-1,3-dihydro-2H-isoindole-2-carboxamide;
N-[4-(4-oxo-3,4-dihydrophthalazin-1-yl)phenyl]-5-(pyrrolidin-1-ylmethyl)-1,3-dihydro-2H-isoindole-2-carboxamide;
5-(morpholin-4-ylmethyl)-N-[4-(1-oxo-1,2-dihydroisoquinolin-4-yl)phenyl]-1,3-dihydro-2H-isoindole-2-carboxamide;
5-methoxy-N-[4-(1-oxo-1,2-dihydroisoquinolin-4-yl)phenyl]-1,3-dihydro-2H-isoindole-2-carboxamide;
5-[(4-methylpiperazin-1-yl)methyl]-N-[4-(4-oxo-3,4-dihydrophthalazin-1-yl)phenyl]-1,3-dihydro-2H-isoindole-2-carboxamide;
5-cyano-N-[4-(1-oxo-1,2-dihydroisoquinolin-4-yl)phenyl]-1,3-dihydro-2H-isoindole-2-carboxamide;
5-chloro-N-[4-(1-oxo-1,2-dihydroisoquinolin-4-yl)phenyl]-1,3-dihydro-2H-isoindole-2-carboxamide;
N-[4-(4-oxo-4,5-dihydro-3H-2,3-benzodiazepin-1-yl)phenyl]-1,3-dihydro-2H-isoindole-2-carboxamide;
N-[4-(1-oxo-1,2-dihydroisoquinolin-4-yl)phenyl]-5-(pyrrolidin-1-ylmethyl)-1,3-dihydro-2H-isoindole-2-carboxamide;
N-{4-[4-oxo-8-(trifluoromethyl)-3,4-dihydrophthalazin-1-yl]phenyl}-1,3-dihydro-2H-isoindole-2-carboxamide;
5-[(dimethylamino)methyl]-N-[4-(1-oxo-1,2-dihydroisoquinolin-4-yl)phenyl]-1,3-dihydro-2H-isoindole-2-carboxamide;
5-[(diethylamino)methyl]-N-[4-(1-oxo-1,2-dihydroisoquinolin-4-yl)phenyl]-1,3-dihydro-2H-isoindole-2-carboxamide;
5-[(4-methylpiperazin-1-yl)methyl]-N-[4-(1-oxo-1,2-dihydroisoquinolin-4-yl)phenyl]-1,3-dihydro-2H-isoindole-2-carboxamide;
5-[(dimethylamino)methyl]-N-[4-(4-oxo-3,4-dihydrophthalazin-1-yl)phenyl]-1,3-dihydro-2H-isoindole-2-carboxamide;
5-[(diethylamino)methyl]-N-[4-(4-oxo-3,4-dihydrophthalazin-1-yl)phenyl]-1,3-dihydro-2H-isoindole-2-carboxamide;
N-{4-[4-oxo-8-(trifluoromethyl)-3,4-dihydrophthalazin-1-yl]phenyl}-5-(pyrrolidin-1-ylmethyl)-1,3-dihydro-2H-isoindole-2-carboxamide;
5-[(1-methylpiperidin-4-yl)oxy]-N-[4-(4-oxo-3,4-dihydrophthalazin-1-yl)phenyl]-1,3-dihydro-2H-isoindole-2-carboxamide;
5-{[(3R)-3-fluoropyrrolidin-1-yl]methyl}-N-[4-(4-oxo-3,4-dihydrophthalazin-1-yl)phenyl]-1,3-dihydro-2H-isoindole-2-carboxamide;
5-{[(3S)-3-fluoropyrrolidin-1-yl]methyl}-N-[4-(4-oxo-3,4-dihydrophthalazin-1-yl)phenyl]-1,3-dihydro-2H-isoindole-2-carboxamide;
5-(azetidin-1-ylmethyl)-N-[4-(4-oxo-3,4-dihydrophthalazin-1-yl)phenyl]-1,3-dihydro-2H-isoindole-2-carboxamide;
N-[4-(1-oxo-1,2-dihydropyrrolo[1,2-d][1,2,4]triazin-4-yl)phenyl]-1,3-dihydro-2H-isoindole-2-carboxamide;
N-[4-(1-oxo-1,2-dihydropyrrolo[1,2-d][1,2,4]triazin-4-yl)phenyl]-5-(pyrrolidin-1-ylmethyl)-1,3-dihydro-2H-isoindole-2-carboxamide;
tert-butyl 4-{4-[(1,3-dihydro-2H-isoindol-2-ylcarbonyl)amino]phenyl}piperidine-1-carboxylate;
N-[4-(5-propyl-1,2,4-oxadiazol-3-yl)phenyl]-1,3-dihydro-2H-isoindole-2-carboxamide;
N-[4-(piperidin-4-yl)phenyl]-1,3-dihydro-2H-isoindole-2-carboxamide;
N-{5-[(tetrahydro furan-3-ylmethyl)carbamoyl]pyridin-2-yl}-1,3-dihydro-2H-isoindole-2-carboxamide;
N-[4-(1-butyrylpiperidin-4-yl)phenyl]-1,3-dihydro-2H-isoindole-2-carboxamide;
N-[4-(1-isobutyrylpiperidin-4-yl)phenyl]-1,3-dihydro-2H-isoindole-2-carboxamide;
N-[4-(1-benzoylpiperidin-4-yl)phenyl]-1,3-dihydro-2H-isoindole-2-carboxamide;
N-{4-[5-(3-methylbutyl)-1,2,4-oxadiazol-3-yl]phenyl}-1,3-dihydro-2H-isoindole-2-carboxamide;
N-[4-(5-benzyl-1,2,4-oxadiazol-3-yl)phenyl]-1,3-dihydro-2H-isoindole-2-carboxamide;
N-(4-{[(3R)-tetrahydrofuran-3-ylmethyl]carbamoyl}phenyl)-1,3-dihydro-2H-isoindole-2-carboxamide;
N-(4-{[(3S)-tetrahydrofuran-3-ylmethyl]carbamoyl}phenyl)-1,3-dihydro-2H-isoindole-2-carboxamide;
N-{4-[(2-methoxyethyl)carbamoyl]phenyl}-1,3-dihydro-2H-isoindole-2-carboxamide;
N-{4-[(5-chloropyridin-2-yl)carbamoyl]phenyl}-1,3-dihydro-2H-isoindole-2-carboxamide;
N-{4-[(3-hydroxy-4-methoxyphenyl)carbamoyl]phenyl}-1,3-dihydro-2H-isoindole-2-carboxamide;
N-{4-[(2,4-dimethoxybenzyl)carbamoyl]phenyl}-1,3-dihydro-2H-isoindole-2-carboxamide;
N-(4-{[4-(2-oxopyrrolidin-1-yl)benzyl]carbamoyl}phenyl)-1,3-dihydro-2H-isoindole-2-carboxamide;
N-(4-{[(1S,2S)-2-hydroxy-2,3-dihydro-1H-inden-1-yl]carbamoyl}phenyl)-1,3-dihydro-2H-isoindole-2-carboxamide;
N-(4-{[(1-hydroxycyclopropyl)methyl]carbamoyl}phenyl)-1,3-dihydro-2H-isoindole-2-carboxamide;
N-{4-[(tetrahydro-2H-pyran-2-ylmethyl)carbamoyl]phenyl}-1,3-dihydro-2H-isoindole-2-carboxamide;
N-{4-[(tetrahydro-2H-pyran-3-ylmethyl)carbamoyl]phenyl}-1,3-dihydro-2H-isoindole-2-carboxamide;
N-{4-[(tetrahydro-2H-pyran-4-ylmethyl)carbamoyl]phenyl}-1,3-dihydro-2H-isoindole-2-carboxamide;
tert-butyl 4-{6-[(1,3-dihydro-2H-isoindol-2-ylcarbonyl)amino]-1H-benzimidazol-2-yl}piperazine-1-carboxylate;
N-[2-(piperazin-1-yl)-1H-benzimidazol-6-yl]-1,3-dihydro-2H-isoindole-2-carboxamide;
N-[4-(propylcarbamoyl)phenyl]-5-vinyl-1,3-dihydro-2H-isoindole-2-carboxamide;
N-{4-[(4-benzoylpiperazin-1-yl)carbonyl]phenyl}-1,3-dihydro-2H-isoindole-2-carboxamide;
N-(4-{[(2S)-tetrahydrofuran-2-ylmethyl]carbamoyl}phenyl)-1,3-dihydro-2H-pyrrolo[3,4-c]pyridine-2-carboxamide;
N-(4-{[(2R)-tetrahydrofuran-2-ylmethyl]carbamoyl}phenyl)-1,3-dihydro-2H-pyrrolo[3,4-c]pyridine-2-carboxamide;
N-{4-[5-(tetrahydrofuran-3-yl)-1,2,4-oxadiazol-3-yl]phenyl}-1,3-dihydro-2H-isoindole-2-carboxamide;
N-[4-(1-isobutyl-1,2,3,6-tetrahydropyridin-4-yl)phenyl]-1,3-dihydro-2H-isoindole-2-carboxamide;
N-(4-{[(3-methylbutyl)amino]carbonyl}phenyl)-5,7-dihydro-6H-pyrrolo[3,4-d]pyrimidine-6-carboxamide;
N-(4-{[(3-phenylpropyl)amino]carbonyl}phenyl)-5,7-dihydro-6H-pyrrolo[3,4-d]pyrimidine-6-carboxamide;
N-{4-[1-(4-methylbenzoyl)-1,2,3,6-tetrahydropyridin-4-yl]phenyl}-1,3-dihydro-2H-isoindole-2-carboxamide;
N-[4-(1-benzyl-1,2,3,6-tetrahydropyridin-4-yl)phenyl]-1,3-dihydro-2H-isoindole-2-carboxamide;
N-(4-{[4-(tetrahydro furan-3-ylmethyl)piperazin-1-yl]carbonyl}phenyl)-1,3-dihydro-2H-isoindole-2-carboxamide;

5-fluoro-N-[4-({[(2S)-tetrahydro furan-2-ylmethyl]amino}carbonyl)phenyl]-1,3-dihydro-2H-isoindole-2-carboxamide;

5-fluoro-N-[4-({[(2R)-tetrahydro furan-2-ylmethyl]amino}carbonyl)phenyl]-1,3-dihydro-2H-isoindole-2-carboxamide;

N-[4-({[(1S)-2-hydroxy-1-phenylethyl]amino}carbonyl)phenyl]-1,3-dihydro-2H-pyrrolo[3,4-c]pyridine-2-carboxamide;

N-(4-{[4-(2-methoxyethyl)piperazin-1-yl]carbonyl}phenyl)-1,3-dihydro-2H-isoindole-2-carboxamide;

N-(4-{[(2S)-2-(2-hydroxyethyl)piperidin-1-yl]carbonyl}phenyl)-1,3-dihydro-2H-isoindole-2-carboxamide;

N-{4-[(propylamino)carbonyl]phenyl}-5-pyridin-3-yl-1,3-dihydro-2H-isoindole-2-carboxamide;

N-{4-[(propylamino)carbonyl]phenyl}-5-pyridin-4-yl-1,3-dihydro-2H-isoindole-2-carboxamide;

$N^5$-(2-methoxyethyl)-$N^2$-{4-[(propylamino)carbonyl]phenyl}-1,3-dihydro-2H-isoindole-2,5-dicarboxamide;

N-(4-cyanophenyl)-1,3-dihydro-2H-isoindole-2-carboxamide;

N-[4-(trifluoromethyl)phenyl]-1,3-dihydro-2H-isoindole-2-carboxamide;

N-[4-({[(1S)-2-hydroxy-1-pyridin-2-ylethyl]amino}carbonyl)phenyl]-1,3-dihydro-2H-pyrrolo[3,4-c]pyridine-2-carboxamide;

N-(4-{[(3-methylbutyl)amino]carbonyl}phenyl)-5,7-dihydro-6H-pyrrolo[3,4-b]pyridine-6-carboxamide;

N-(4-{[(tetrahydrofuran-3-ylmethyl)amino]carbonyl}phenyl)-5,7-dihydro-6H-pyrrolo[3,4-b]pyridine-6-carboxamide;

N-{4-[(4-pyridin-2-ylpiperazin-1-yl)carbonyl]phenyl}-5,7-dihydro-6H-pyrrolo[3,4-b]pyridine-6-carboxamide;

N-[4-({[(1S)-2-hydroxy-1-pyridin-2-ylethyl]amino}carbonyl)phenyl]-1,3-dihydro-2H-isoindole-2-carboxamide;

5-(1,2-dihydroxyethyl)-N-{4-[(propylamino)carbonyl]phenyl}-1,3-dihydro-2H-isoindole-2-carboxamide;

N-(1'-butyryl-1',2',3',6'-tetrahydro-3,4'-bipyridin-6-yl)-1,3-dihydro-2H-isoindole-2-carboxamide;

N-(1'-isobutyryl-1',2',3',6'-tetrahydro-3,4'-bipyridin-6-yl)-1,3-dihydro-2H-isoindole-2-carboxamide;

N-[1'-(tetrahydrofuran-3-ylcarbonyl)-1',2',3',6'-tetrahydro-3,4'-bipyridin-6-yl]-1,3-dihydro-2H-isoindole-2-carboxamide; and N-[2-(4-acetylpiperazin-1-yl)-1H-benzimidazol-5-yl]-1,3-dihydro-2H-isoindole-2-carboxamide;

N-{4-[1-(5-oxo-L-prolyl)-1,2,3,6-tetrahydropyridin-4-yl]phenyl}-1,3-dihydro-2H-isoindole-2-carboxamide;

N-{4-[1-(5-oxo-D-prolyl)-1,2,3,6-tetrahydropyridin-4-yl]phenyl}-1,3-dihydro-2H-isoindole-2-carboxamide;

N-[4-(1-propionyl-1,2,3,6-tetrahydropyridin-4-yl)phenyl]-1,3-dihydro-2H-isoindole-2-carboxamide;

N-{4-[1-(2-methylbutanoyl)-1,2,3,6-tetrahydropyridin-4-yl]phenyl}-1,3-dihydro-2H-isoindole-2-carboxamide;

N-{4-[1-(2-ethylbutanoyl)-1,2,3,6-tetrahydropyridin-4-yl]phenyl}-1,3-dihydro-2H-isoindole-2-carboxamide;

N-{4-[1-(methoxyacetyl)-1,2,3,6-tetrahydropyridin-4-yl]phenyl}-1,3-dihydro-2H-isoindole-2-carboxamide;

N-{4-[1-(ethoxyacetyl)-1,2,3,6-tetrahydropyridin-4-yl]phenyl}-1,3-dihydro-2H-isoindole-2-carboxamide;

N-(4-{1-[(2-methoxyethoxy)acetyl]-1,2,3,6-tetrahydropyridin-4-yl}phenyl)-1,3-dihydro-2H-isoindole-2-carboxamide;

N-{4-[1-(tetrahydrofuran-2-ylcarbonyl)-1,2,3,6-tetrahydropyridin-4-yl]phenyl}-1,3-dihydro-2H-isoindole-2-carboxamide;

N-{4-[1-(tetrahydrofuran-3-ylcarbonyl)-1,2,3,6-tetrahydropyridin-4-yl]phenyl}-1,3-dihydro-2H-isoindole-2-carboxamide;

N-{4-[1-(cyclopropylacetyl)-1,2,3,6-tetrahydropyridin-4-yl]phenyl}-1,3-dihydro-2H-isoindole-2-carboxamide;

N-{4-[1-(cyclopentylcarbonyl)-1,2,3,6-tetrahydropyridin-4-yl]phenyl}-1,3-dihydro-2H-isoindole-2-carboxamide;

N-{4-[1-(2-methylbenzoyl)-1,2,3,6-tetrahydropyridin-4-yl]phenyl}-1,3-dihydro-2H-isoindole-2-carboxamide;

N-{4-[1-(3-methylbenzoyl)-1,2,3,6-tetrahydropyridin-4-yl]phenyl}-1,3-dihydro-2H-isoindole-2-carboxamide;

N-{4-[1-(2-methoxybenzoyl)-1,2,3,6-tetrahydropyridin-4-yl]phenyl}-1,3-dihydro-2H-isoindole-2-carboxamide;

N-{4-[1-(3-methoxybenzoyl)-1,2,3,6-tetrahydropyridin-4-yl]phenyl}-1,3-dihydro-2H-isoindole-2-carboxamide;

N-{4-[1-(4-methoxybenzoyl)-1,2,3,6-tetrahydropyridin-4-yl]phenyl}-1,3-dihydro-2H-isoindole-2-carboxamide;

N-{4-[1-(2-fluorobenzoyl)-1,2,3,6-tetrahydropyridin-4-yl]phenyl}-1,3-dihydro-2H-isoindole-2-carboxamide;

N-{4-[1-(3-fluorobenzoyl)-1,2,3,6-tetrahydropyridin-4-yl]phenyl}-1,3-dihydro-2H-isoindole-2-carboxamide;

N-{4-[1-(4-fluorobenzoyl)-1,2,3,6-tetrahydropyridin-4-yl]phenyl}-1,3-dihydro-2H-isoindole-2-carboxamide;

N-{4-[1-(4-chlorobenzoyl)-1,2,3,6-tetrahydropyridin-4-yl]phenyl}-1,3-dihydro-2H-isoindole-2-carboxamide;

N-(4-{1-[3-(dimethylamino)benzoyl]-1,2,3,6-tetrahydropyridin-4-yl}phenyl)-1,3-dihydro-2H-isoindole-2-carboxamide;

N-(4-{1-[4-(dimethylamino)benzoyl]-1,2,3,6-tetrahydropyridin-4-yl}phenyl)-1,3-dihydro-2H-isoindole-2-carboxamide;

N-{4-[1-(3-furoyl)-1,2,3,6-tetrahydropyridin-4-yl]phenyl}-1,3-dihydro-2H-isoindole-2-carboxamide;

N-{4-[1-(3-thienylcarbonyl)-1,2,3,6-tetrahydropyridin-4-yl]phenyl}-1,3-dihydro-2H-isoindole-2-carboxamide;

N-{4-[1-(1H-pyrrol-2-ylcarbonyl)-1,2,3,6-tetrahydropyridin-4-yl]phenyl}-1,3-dihydro-2H-isoindole-2-carboxamide;

N-(4-{1-[(2,5-dimethyl-1H-pyrrol-3-yl)carbonyl]-1,2,3,6-tetrahydropyridin-4-yl}phenyl)-1,3-dihydro-2H-isoindole-2-carboxamide;

N-{4-[1-(1,3-thiazol-4-ylcarbonyl)-1,2,3,6-tetrahydropyridin-4-yl]phenyl}-1,3-dihydro-2H-isoindole-2-carboxamide;

N-{4-[1-(1H-pyrazol-4-ylcarbonyl)-1,2,3,6-tetrahydropyridin-4-yl]phenyl}-1,3-dihydro-2H-isoindole-2-carboxamide;

N-(4-{1-[(3,5-dimethyl-1,2-oxazol-4-yl)carbonyl]-1,2,3,6-tetrahydropyridin-4-yl}phenyl)-1,3-dihydro-2H-isoindole-2-carboxamide;

N-{4-[1-(pyridin-2-ylcarbonyl)-1,2,3,6-tetrahydropyridin-4-yl]phenyl}-1,3-dihydro-2H-isoindole-2-carboxamide;

N-{4-[1-(pyridin-3-ylcarbonyl)-1,2,3,6-tetrahydropyridin-4-yl]phenyl}-1,3-dihydro-2H-isoindole-2-carboxamide;

N-[4-(1-isonicotinoyl-1,2,3,6-tetrahydropyridin-4-yl)phenyl]-1,3-dihydro-2H-isoindole-2-carboxamide;

N-{4-[1-(pyridazin-3-ylcarbonyl)-1,2,3,6-tetrahydropyridin-4-yl]phenyl}-1,3-dihydro-2H-isoindole-2-carboxamide;

N-{4-[1-(pyrazin-2-ylcarbonyl)-1,2,3,6-tetrahydropyridin-4-yl]phenyl}-1,3-dihydro-2H-isoindole-2-carboxamide;

N-{4-[1-(pyrimidin-4-ylcarbonyl)-1,2,3,6-tetrahydropyridin-4-yl]phenyl}-1,3-dihydro-2H-isoindole-2-carboxamide;

N-(4-{1-[3-(piperidin-1-yl)propanoyl]-1,2,3,6-tetrahydropyridin-4-yl}phenyl)-1,3-dihydro-2H-isoindole-2-carboxamide;
N-{4-[1-(morpholin-4-ylacetyl)-1,2,3,6-tetrahydropyridin-4-yl]phenyl}-1,3-dihydro-2H-isoindole-2-carboxamide;
N-(4-{1-[(4-methylpiperazin-1-yl)acetyl]-1,2,3,6-tetrahydropyridin-4-yl}phenyl)-1,3-dihydro-2H-isoindole-2-carboxamide;
N-(1'-benzoyl-1',2',3',6'-tetrahydro-3,4'-bipyridin-6-yl)-1,3-dihydro-2H-isoindole-2-carboxamide;
N-(4-{[6-(benzoylamino)hexyl]carbamoyl}phenyl)-1,3-dihydro-2H-isoindole-2-carboxamide;
N-(4-({4-[(benzoylamino)methyl]benzyl}carbamoyl)phenyl)-5-fluoro-1,3-dihydro-2H-isoindole-2-carboxamide;
N-{4-[4-(5-oxo-L-prolyl)piperazin-1-yl]phenyl}-1,3-dihydro-2H-isoindole-2-carboxamide;
N-{4-[4-(5-oxo-D-prolyl)piperazin-1-yl]phenyl}-1,3-dihydro-2H-isoindole-2-carboxamide;
N-(4-{4-[(1-acetylpiperidin-4-yl)carbonyl]piperazin-1-yl}phenyl)-1,3-dihydro-2H-isoindole-2-carboxamide;
N-{4-[4-(2-acetamidobenzoyl)piperazin-1-yl]phenyl}-1,3-dihydro-2H-isoindole-2-carboxamide;
N-(4-{4-[(methylsulfonyl)benzoyl]piperazin-1-yl}-phenyl)-1,3-dihydro-2H-isoindole-2-carboxamide;
N-[4-(4-butyrylpiperazin-1-yl)phenyl]-1,3-dihydro-2H-isoindole-2-carboxamide;
N-[4-(4-isobutyrylpiperazin-1-yl)phenyl]-1,3-dihydro-2H-isoindole-2-carboxamide;
N-{4-[4-(2-methylbutanoyl)piperazin-1-yl]phenyl}-1,3-dihydro-2H-isoindole-2-carboxamide;
N-{4-[4-(3,3,3-trifluoropropanoyl)piperazin-1-yl]phenyl}-1,3-dihydro-2H-isoindole-2-carboxamide;
N-{4-[4-(methoxyacetyl)piperazin-1-yl]phenyl}-1,3-dihydro-2H-isoindole-2-carboxamide;
N-{4-[4-(tetrahydrofuran-2-ylcarbonyl)piperazin-1-yl]phenyl}-1,3-dihydro-2H-isoindole-2-carboxamide;
N-{4-[4-(tetrahydrofuran-3-ylcarbonyl)piperazin-1-yl]phenyl}-1,3-dihydro-2H-isoindole-2-carboxamide;
N-{4-[4-(cyclopentylacetyl)piperazin-1-yl]phenyl}-1,3-dihydro-2H-isoindole-2-carboxamide;
N-{4-[4-(cyclohexylcarbonyl)piperazin-1-yl]phenyl}-1,3-dihydro-2H-isoindole-2-carboxamide;
N-{4-[4-(2-methoxybenzoyl)piperazin-1-yl]phenyl}-1,3-dihydro-2H-isoindole-2-carboxamide;
N-{4-[4-(3-methoxybenzoyl)piperazin-1-yl]phenyl}-1,3-dihydro-2H-isoindole-2-carboxamide;
N-{4-[4-(4-methoxybenzoyl)piperazin-1-yl]phenyl}-1,3-dihydro-2H-isoindole-2-carboxamide;
N-{4-[4-(3-fluorobenzoyl)piperazin-1-yl]phenyl}-1,3-dihydro-2H-isoindole-2-carboxamide;
N-{4-[4-(2-chlorobenzoyl)piperazin-1-yl]phenyl}-1,3-dihydro-2H-isoindole-2-carboxamide;
N-{4-[4-(4-chlorobenzoyl)piperazin-1-yl]phenyl}-1,3-dihydro-2H-isoindole-2-carboxamide;
N-{4-[4-(3-cyanobenzoyl)piperazin-1-yl]phenyl}-1,3-dihydro-2H-isoindole-2-carboxamide;
N-{4-[4-(4-cyanobenzoyl)piperazin-1-yl]phenyl}-1,3-dihydro-2H-isoindole-2-carboxamide;
N-(4-{4-[3-(dimethylamino)benzoyl]piperazin-1-yl}phenyl)-1,3-dihydro-2H-isoindole-2-carboxamide;
N-(4-{4-[4-(dimethylamino)benzoyl]piperazin-1-yl}phenyl)-1,3-dihydro-2H-isoindole-2-carboxamide;
N-{4-[4-(3,4-dimethoxybenzoyl)piperazin-1-yl]phenyl}-1,3-dihydro-2H-isoindole-2-carboxamide;
N-{4-[4-(3,5-dimethoxybenzoyl)piperazin-1-yl]phenyl}-1,3-dihydro-2H-isoindole-2-carboxamide;
N-(4-{4-[(3,4-dimethoxyphenyl)acetyl]piperazin-1-yl}phenyl)-1,3-dihydro-2H-isoindole-2-carboxamide;
N-{4-[4-(2-furoyl)piperazin-1-yl]phenyl}-1,3-dihydro-2H-isoindole-2-carboxamide;
N-{4-[4-(3-furoyl)piperazin-1-yl]phenyl}-1,3-dihydro-2H-isoindole-2-carboxamide;
N-{4-[4-(1H-pyrrol-2-ylcarbonyl)piperazin-1-yl]phenyl}-1,3-dihydro-2H-isoindole-2-carboxamide;
N-{4-[4-(1H-pyrazol-5-ylcarbonyl)piperazin-1-yl]phenyl}-1,3-dihydro-2H-isoindole-2-carboxamide;
N-{4-[4-(pyridin-2-ylcarbonyl)piperazin-1-yl]phenyl}-1,3-dihydro-2H-isoindole-2-carboxamide;
N-{4-[4-(pyridin-3-ylcarbonyl)piperazin-1-yl]phenyl}-1,3-dihydro-2H-isoindole-2-carboxamide;
N-[4-(4-isonicotinoylpiperazin-1-yl)phenyl]-1,3-dihydro-2H-isoindole-2-carboxamide;
N-{4-[4-(pyridazin-3-ylcarbonyl)piperazin-1-yl]phenyl}-1,3-dihydro-2H-isoindole-2-carboxamide;
N-{4-[4-(pyrazin-2-ylcarbonyl)piperazin-1-yl]phenyl}-1,3-dihydro-2H-isoindole-2-carboxamide;
N-{4-[4-(pyrimidin-4-ylcarbonyl)piperazin-1-yl]phenyl}-1,3-dihydro-2H-isoindole-2-carboxamide;
N-{4-[4-(N,N-dimethyl-beta-alanyl)piperazin-1-yl]phenyl}-1,3-dihydro-2H-isoindole-2-carboxamide;
N-[4-(4-acetylpiperazin-1-yl)phenyl]-1,3-dihydro-2H-isoindole-2-carboxamide;
N-{4-[4-(2-fluorobenzoyl)piperazin-1-yl]phenyl}-1,3-dihydro-2H-isoindole-2-carboxamide;
N-{4-[4-(4-fluorobenzoyl)piperazin-1-yl]phenyl}-1,3-dihydro-2H-isoindole-2-carboxamide;
N-{4-[4-(phenylacetyl)piperazin-1-yl]phenyl}-1,3-dihydro-2H-isoindole-2-carboxamide;
N-{4-[4-(1,3-thiazol-4-ylcarbonyl)piperazin-1-yl]phenyl}-1,3-dihydro-2H-isoindole-2-carboxamide;
N-{4-[4-(morpholin-4-ylacetyl)piperazin-1-yl]phenyl}-1,3-dihydro-2H-isoindole-2-carboxamide;
N-[4-(1-butyryl-1,2,3,6-tetrahydropyridin-4-yl)phenyl]-1,3-dihydro-2H-pyrrolo[3,4-c]pyridine-2-carboxamide;
N-[4-(1-isobutyryl-1,2,3,6-tetrahydropyridin-4-yl)phenyl]-1,3-dihydro-2H-pyrrolo[3,4-c]pyridine-2-carboxamide;
N-[4-(1-benzoyl-1,2,3,6-tetrahydropyridin-4-yl)phenyl]-1,3-dihydro-2H-pyrrolo[3,4-c]pyridine-2-carboxamide;
N-{4-[1-(tetrahydrofuran-3-ylcarbonyl)-1,2,3,6-tetrahydropyridin-4-yl]phenyl}-1,3-dihydro-2H-pyrrolo[3,4-c]pyridine-2-carboxamide;
N-[4-(1-oxo-2,3-dihydro-1H-isoindol-4-yl)phenyl]-1,3-dihydro-2H-isoindole-2-carboxamide;
N-[4-(4-oxo-3,4-dihydrophthalazin-1-yl)phenyl]-1,3-dihydro-2H-pyrrolo[3,4-c]pyridine-2-carboxamide;
N-[4-(4-oxo-3,4-dihydrophthalazin-1-yl)phenyl]-5,7-dihydro-6H-pyrrolo[3,4-b]pyridine-6-carboxamide;
N-[4-(1-oxo-1,2-dihydroisoquinolin-4-yl)cyclohex-3-en-1-yl]-1,3-dihydro-2H-isoindole-2-carboxamide;
N-[4-(4-oxo-3,4-dihydrophthalazin-1-yl)cyclohex-3-en-1-yl]-1,3-dihydro-2H-isoindole-2-carboxamide;
N-[4-(4-oxo-3,4-dihydrophthalazin-1-yl)cyclohex-3-en-1-yl]-5-(pyrrolidin-1-ylmethyl)-1,3-dihydro-2H-isoindole-2-carboxamide;
N-{4-[(tetrahydro-2H-pyran-2-ylmethyl)carbamoyl]phenyl}-1,3-dihydro-2H-pyrrolo[3,4-c]pyridine-2-carboxamide;
N-{4-[(tetrahydro-2H-pyran-3-ylmethyl)carbamoyl]phenyl}-1,3-dihydro-2H-pyrrolo[3,4-c]pyridine-2-carboxamide;
N-{4-[(tetrahydro-2H-pyran-4-ylmethyl)carbamoyl]phenyl}-1,3-dihydro-2H-pyrrolo[3,4-c]pyridine-2-carboxamide;

N-(4-{[(2S)-1-hydroxy-4-methylpentan-2-yl]carbamoyl}phenyl)-1,3-dihydro-2H-pyrrolo[3,4-c]pyridine-2-carboxamide;

N-[1-(3-methylbutyl)-1H-pyrazol-4-yl]-1,3-dihydro-2H-isoindole-2-carboxamide;

N-[1-(2-phenylethyl)-1H-pyrazol-4-yl]-1,3-dihydro-2H-isoindole-2-carboxamide;

$N^5$-[2-(dimethylamino)ethyl]-$N^2$-[4-(propylcarbamoyl)phenyl]-1,3-dihydro-2H-isoindole-2,5-dicarboxamide;

5-(morpholin-4-ylcarbonyl)-N-[4-(propylcarbamoyl)phenyl]-1,3-dihydro-2H-isoindole-2-carboxamide;

N-(4-{benzyl[3-(morpholin-4-yl)propyl]carbamoyl}phenyl)-1,3-dihydro-2H-isoindole-2-carboxamide;

N-[4-(isobutoxycarbamoyl)phenyl]-1,3-dihydro-2H-isoindole-2-carboxamide;

5-bromo-N-{4-[(cyclopentylacetyl)amino]phenyl}-1,3-dihydro-2H-isoindole-2-carboxamide;

5-cyano-N-{4-[(cyclopentylacetyl)amino]phenyl}-1,3-dihydro-2H-isoindole-2-carboxamide;

methyl 4-{[(5-cyano-1,3-dihydro-2H-isoindol-2-yl)carbonyl]amino}benzoate;

N-(4-{(E)-[(benzyloxy)imino]methyl}phenyl)-1,3-dihydro-2H-isoindole-2-carboxamide;

5-fluoro-N-{4-[(tetrahydro-2H-pyran-2-ylmethyl)carbamoyl]phenyl}-1,3-dihydro-2H-isoindole-2-carboxamide;

5-fluoro-N-{4-[(tetrahydro-2H-pyran-3-ylmethyl)carbamoyl]phenyl}-1,3-dihydro-2H-isoindole-2-carboxamide;

5-fluoro-N-{4-[(tetrahydro-2H-pyran-4-ylmethyl)carbamoyl]phenyl}-1,3-dihydro-2H-isoindole-2-carboxamide;

5-fluoro-N-(4-{[(1S)-2-hydroxy-1-phenylethyl]carbamoyl}phenyl)-1,3-dihydro-2H-isoindole-2-carboxamide;

5-fluoro-N-(4-{[(1S)-2-hydroxy-1-(pyridin-2-yl)ethyl]carbamoyl}phenyl)-1,3-dihydro-2H-isoindole-2-carboxamide;

5-fluoro-N-(4-{[(2S)-1-hydroxy-4-methylpentan-2-yl]carbamoyl}phenyl)-1,3-dihydro-2H-isoindole-2-carboxamide;

N-[4-(3-aminopyrrolidin-1-yl)phenyl]-1,3-dihydro-2H-isoindole-2-carboxamide;

N-{6-[(3-methylbutyl)carbamoyl]pyridin-3-yl}-1,3-dihydro-2H-isoindole-2-carboxamide;

N-{6-[(3-phenylpropyl)carbamoyl]pyridin-3-yl}-1,3-dihydro-2H-isoindole-2-carboxamide;

N-{6-[(tetrahydro furan-3-ylmethyl)carbamoyl]pyridin-3-yl}-1,3-dihydro-2H-isoindole-2-carboxamide;

$N^2$-{4-[(cyclopentylacetyl)amino]phenyl}-1,3-dihydro-2H-isoindole-2,5-dicarboxamide;

N-[4-({benzyl[3-(morpholin-4-yl)propyl]amino}methyl)phenyl]-1,3-dihydro-2H-isoindole-2-carboxamide;

N-{4-[(cyclopentylacetyl)amino]phenyl}-5-(1H-pyrazol-3-yl)-1,3-dihydro-2H-isoindole-2-carboxamide;

N-{4-[(cyclopentylacetyl)amino]phenyl}-5-(pyridin-3-yl)-1,3-dihydro-2H-isoindole-2-carboxamide;

N-{4-[(cyclopentylacetyl)amino]phenyl}-5-(1-methyl-1H-pyrazol-4-yl)-1,3-dihydro-2H-isoindole-2-carboxamide;

$N^2$-{4-[(cyclopentylacetyl)amino]phenyl}-$N^5$-(2-methoxyethyl)-1,3-dihydro-2H-isoindole-2,5-dicarboxamide;

$N^2$-{4-[(cyclopentylacetyl)amino]phenyl}-$N^5$-(2-hydroxyethyl)-1,3-dihydro-2H-isoindole-2,5-dicarboxamide;

5-(aminomethyl)-N-{4-[(cyclopentylacetyl)amino]phenyl}-1,3-dihydro-2H-isoindole-2-carboxamide;

N-(4-{[(2S)-1-hydroxy-4-(methylthio)butan-2-yl]carbamoyl}phenyl)-1,3-dihydro-2H-isoindole-2-carboxamide;

N-(4-{[(2S,3S)-1-hydroxy-3-methylpentan-2-yl]carbamoyl}phenyl)-1,3-dihydro-2H-isoindole-2-carboxamide;

N-(4-{[(2S)-1-hydroxypropan-2-yl]carbamoyl}phenyl)-1,3-dihydro-2H-isoindole-2-carboxamide;

N-(4-{[(2S,3R)-1,3-dihydroxybutan-2-yl]carbamoyl}phenyl)-1,3-dihydro-2H-isoindole-2-carboxamide;

N-(4-{[(2S)-1-hydroxyhexan-2-yl]carbamoyl}phenyl)-1,3-dihydro-2H-isoindole-2-carboxamide;

N-(4-{[(2S)-1-hydroxypentan-2-yl]carbamoyl}phenyl)-1,3-dihydro-2H-isoindole-2-carboxamide;

N-(4-{[(1S,2S)-2-hydroxycyclopentyl]carbamoyl}phenyl)-1,3-dihydro-2H-isoindole-2-carboxamide;

N-(4-{[(1S,2R)-2-hydroxycyclopentyl]carbamoyl}phenyl)-1,3-dihydro-2H-isoindole-2-carboxamide;

N-(4-{[(2S)-1-cyclohexyl-3-hydroxypropan-2-yl]carbamoyl}phenyl)-1,3-dihydro-2H-isoindole-2-carboxamide;

N-[4-({(2R)-1-hydroxy-3-[(4-methylbenzyl)thio]propan-2-yl}carbamoyl)phenyl]-1,3-dihydro-2H-isoindole-2-carboxamide;

N-(4-{[(1S)-1-(4-tert-butylphenyl)-2-hydroxyethyl]carbamoyl}phenyl)-1,3-dihydro-2H-isoindole-2-carboxamide;

N-{4-[(cyclopentylacetyl)amino]phenyl}-5-methoxy-1,3-dihydro-2H-isoindole-2-carboxamide;

5-methoxy-N-[4-(propylcarbamoyl)phenyl]-1,3-dihydro-2H-isoindole-2-carboxamide;

5-methyl-N-[4-(propylcarbamoyl)phenyl]-1,3-dihydro-2H-isoindole-2-carboxamide;

N-[4-(propylcarbamoyl)phenyl]-1,3-dihydro-2H-pyrrolo[3,4-c]pyridine-2-carboxamide;

N-(4-{[(2S)-tetrahydrofuran-2-ylmethyl]carbamoyl}phenyl)-5,7-dihydro-6H-pyrrolo[3,4-b]pyridine-6-carboxamide;

N-(4-{[(2R)-tetrahydrofuran-2-ylmethyl]carbamoyl}phenyl)-5,7-dihydro-6H-pyrrolo[3,4-b]pyridine-6-carboxamide;

N-(4-{[(2S)-1-hydroxy-4-methylpentan-2-yl]carbamoyl}phenyl)-5,7-dihydro-6H-pyrrolo[3,4-b]pyridine-6-carboxamide;

N-(4-{[(1S)-2-hydroxy-1-phenylethyl]carbamoyl}phenyl)-5,7-dihydro-6H-pyrrolo[3,4-b]pyridine-6-carboxamide;

N-{4-[(tetrahydro-2H-pyran-4-ylmethyl)carbamoyl]phenyl}-5,7-dihydro-6H-pyrrolo[3,4-b]pyridine-6-carboxamide;

N-{4-[(cyclopentylacetyl)amino]phenyl}-5-(pyridin-4-yl)-1,3-dihydro-2H-isoindole-2-carboxamide;

5-(hydroxymethyl)-N-{4-[(3-methylbutyl)carbamoyl]phenyl}-1,3-dihydro-2H-isoindole-2-carboxamide;

N-(6-{[(3S)-tetrahydrofuran-3-ylmethyl]carbamoyl}pyridazin-3-yl)-1,3-dihydro-2H-isoindole-2-carboxamide;

N-{6-[(cyclopentylmethyl)carbamoyl]pyridazin-3-yl}-1,3-dihydro-2H-isoindole-2-carboxamide;

N-(4-{[(1S)-2-hydroxy-1-(pyridin-2-yl)ethyl]carbamoyl}phenyl)-5,7-dihydro-6H-pyrrolo[3,4-b]pyridine-6-carboxamide;

N-[1'-(tetrahydrofuran-3-ylcarbonyl)-1',2',3',6'-tetrahydro-2,4'-bipyridin-5-yl]-1,3-dihydro-2H-isoindole-2-carboxamide;

N-{1'-[(2-methoxyethoxy)acetyl]-1',2',3',6'-tetrahydro-2,4'-bipyridin-5-yl}-1,3-dihydro-2H-isoindole-2-carboxamide;

5-(hydroxymethyl)-N-[1-(3-methylbutyl)-1H-pyrazol-4-yl]-1,3-dihydro-2H-isoindole-2-carboxamide;

N-{5-[(3-methylbutyl)carbamoyl]pyrazin-2-yl}-1,3-dihydro-2H-isoindole-2-carboxamide;
N-(4-{1-[(2-methoxyethoxy)acetyl]-1,2,3,6-tetrahydropyridin-4-yl}phenyl)-1,3-dihydro-2H-pyrrolo[3,4-c]pyridine-2-carboxamide;
N-(4-{(1E)-3-[benzyl(methyl)amino]prop-1-en-1-yl}phenyl)-1,3-dihydro-2H-isoindole-2-carboxamide;
N-[4-(4-phenoxypiperidin-1-yl)phenyl]-1,3-dihydro-2H-isoindole-2-carboxamide;
N-[4-(3-phenoxyazetidin-1-yl)phenyl]-1,3-dihydro-2H-isoindole-2-carboxamide;
N-(4-{[benzyl(methyl)amino]methyl}phenyl)-1,3-dihydro-2H-isoindole-2-carboxamide;
5-fluoro-N-(4-{[(3R)-tetrahydrofuran-3-ylmethyl]carbamoyl}phenyl)-1,3-dihydro-2H-isoindole-2-carboxamide;
5-fluoro-N-(4-{[(3S)-tetrahydrofuran-3-ylmethyl]carbamoyl}phenyl)-1,3-dihydro-2H-isoindole-2-carboxamide;
N-{4-[(4-hydroxypiperidin-1-yl)carbonyl]phenyl}-1,3-dihydro-2H-pyrrolo[3,4-c]pyridine-2-carboxamide;
N-{4-[(2-hydroxy-2-methylpropyl)carbamoyl]phenyl}-1,3-dihydro-2H-pyrrolo[3,4-c]pyridine-2-carboxamide;
N-{4-[(4-hydroxybutyl)carbamoyl]phenyl}-1,3-dihydro-2H-pyrrolo[3,4-c]pyridine-2-carboxamide;
N-(4-{[(2S)-1-hydroxy-3-methylbutan-2-yl]carbamoyl}phenyl)-1,3-dihydro-2H-pyrrolo[3,4-c]pyridine-2-carboxamide;
N-{4-[(1-hydroxy-2-methylpropan-2-yl)carbamoyl]phenyl}-1,3-dihydro-2H-pyrrolo[3,4-c]pyridine-2-carboxamide;
N-(4-{[(2R)-2-hydroxypropyl]carbamoyl}phenyl)-1,3-dihydro-2H-pyrrolo[3,4-c]pyridine-2-carboxamide;
N-(4-{[(2S)-2-hydroxypropyl]carbamoyl}phenyl)-1,3-dihydro-2H-pyrrolo[3,4-c]pyridine-2-carboxamide;
N-(4-{[3-(piperidin-1-yl)propyl]carbamoyl}phenyl)-1,3-dihydro-2H-pyrrolo[3,4-c]pyridine-2-carboxamide;
N-[4-(5,6-dihydroimidazo[1,5-a]pyrazin-7(8H)-ylcarbonyl)phenyl]-1,3-dihydro-2H-pyrrolo[3,4-c]pyridine-2-carboxamide;
N-[4-(1-benzyl-1H-1,2,3-triazol-4-yl)phenyl]-1,3-dihydro-2H-isoindole-2-carboxamide;
N-{4-[1-(3-methylbutyl)-1H-1,2,3-triazol-4-yl]phenyl}-1,3-dihydro-2H-isoindole-2-carboxamide;
N-{4-[1-(tetrahydrofuran-3-ylmethyl)-1H-1,2,3-triazol-4-yl]phenyl}-1,3-dihydro-2H-isoindole-2-carboxamide;
N-(4-{1-[2-(2-oxopyrrolidin-1-yl)ethyl]-1H-1,2,3-triazol-4-yl}phenyl)-1,3-dihydro-2H-isoindole-2-carboxamide;
N-{4-[1-(1-benzylpiperidin-4-yl)-1H-1,2,3-triazol-4-yl]phenyl}-1,3-dihydro-2H-isoindole-2-carboxamide;
N-{4-[1(3-phenylpropyl)-1H-1,2,3-triazol-4-yl]phenyl}-1,3-dihydro-2H-isoindole-2-carboxamide;
N-(4-{1-[4-(morpholin-4-yl)benzyl]-1H-1,2,3-triazol-4-yl}phenyl)-1,3-dihydro-2H-isoindole-2-carboxamide;
N-[4-(1-isobutyl-1H-1,2,3-triazol-4-yl)phenyl]-1,3-dihydro-2H-isoindole-2-carboxamide;
N-{4-[1-(cyclopentylmethyl)-1H-1,2,3-triazol-4-yl]phenyl}-1,3-dihydro-2H-isoindole-2-carboxamide;
N-{4-[1-(3-methoxypropyl)-1H-1,2,3-triazol-4-yl]phenyl}-1,3-dihydro-2H-isoindole-2-carboxamide;
N-[4-(1-isobutyrylpiperidin-4-yl)phenyl]-1,3-dihydro-2H-pyrrolo[3,4-c]pyridine-2-carboxamide;
N-(4-{1-[(2-methoxyethoxy)acetyl]piperidin-4-yl}phenyl)-1,3-dihydro-2H-isoindole-2-carboxamide;
N-{5-[1-(tetrahydrofuran-3-ylcarbonyl)piperidin-4-yl]pyridin-2-yl}-1,3-dihydro-2H-isoindole-2-carboxamide;
5-(hydroxymethyl)-N-{4-[(tetrahydrofuran-3-ylacetyl)amino]phenyl}-1,3-dihydro-2H-isoindole-2-carboxamide;
5-(hydroxymethyl)-N-(4-{[(2-methoxyethoxy)acetyl]amino}phenyl)-1,3-dihydro-2H-isoindole-2-carboxamide;
N-(1'-isobutyryl-1',2',3',6'-tetrahydro-2,4'-bipyridin-5-yl)-1,3-dihydro-2H-pyrrolo[3,4-c]pyridine-2-carboxamide;
N-(1'-benzoyl-1',2',3',6'-tetrahydro-2,4'-bipyridin-5-yl)-1,3-dihydro-2H-pyrrolo[3,4-c]pyridine-2-carboxamide;
N-[1'-(tetrahydrofuran-3-ylcarbonyl)-1',2',3',6'-tetrahydro-2,4'-bipyridin-5-yl]-1,3-dihydro-2H-pyrrolo[3,4-c]pyridine-2-carboxamide;
N-{1'-[(2-methoxyethoxy)acetyl]-1',2',3',6'-tetrahydro-2,4'-bipyridin-5-yl}-1,3-dihydro-2H-pyrrolo[3,4-c]pyridine-2-carboxamide;
5-(hydroxymethyl)-N-{4-[(tetrahydrofuran-2-ylacetyl)amino]phenyl}-1,3-dihydro-2H-isoindole-2-carboxamide;
N-{4-[(ethoxyacetyl)amino]phenyl}-5-(hydroxymethyl)-1,3-dihydro-2H-isoindole-2-carboxamide;
5-(hydroxymethyl)-N-{4-[(tetrahydro-2H-pyran-4-ylacetyl)amino]phenyl}-1,3-dihydro-2H-isoindole-2-carboxamide;
5-(hydroxymethyl)-N-{4-[(morpholin-4-ylacetyl)amino]phenyl}-1,3-dihydro-2H-isoindole-2-carboxamide;
N-[4-(morpholin-4-ylcarbonyl)phenyl]-1,3-dihydro-2H-pyrrolo[3,4-c]pyridine-2-carboxamide;
N-(4-{[3-(2-oxopyrrolidin-1-yl)propyl]carbamoyl}phenyl)-1,3-dihydro-2H-pyrrolo[3,4-c]pyridine-2-carboxamide;
N-[1'-(tetrahydrofuran-2-ylcarbonyl)-1',2',3',6'-tetrahydro-2,4'-bipyridin-5-yl]-1,3-dihydro-2H-pyrrolo[3,4-c]pyridine-2-carboxamide;
N-[1'-(tetrahydro-2H-pyran-4-ylcarbonyl)-1',2',3',6'-tetrahydro-2,4'-bipyridin-5-yl]-1,3-dihydro-2H-pyrrolo[3,4-c]pyridine-2-carboxamide;
N-[1'-(1,4-dioxan-2-ylcarbonyl)-1',2',3',6'-tetrahydro-2,4'-bipyridin-5-yl]-1,3-dihydro-2H-pyrrolo[3,4-c]pyridine-2-carboxamide;
N-{1'-[(1,1-dioxidotetrahydrothiophen-3-yl)carbonyl]-1',2',3',6'-tetrahydro-2,4'-bipyridin-5-yl}-1,3-dihydro-2H-pyrrolo[3,4-c]pyridine-2-carboxamide;
N-[1'-(2-hydroxy-2-methylpropanoyl)-1',2',3',6'-tetrahydro-2,4'-bipyridin-5-yl]-1,3-dihydro-2H-pyrrolo[3,4-c]pyridine-2-carboxamide;
N-{4-[1-(tetrahydrofuran-2-ylcarbonyl)-1,2,3,6-tetrahydropyridin-4-yl]phenyl}-1,3-dihydro-2H-pyrrolo[3,4-c]pyridine-2-carboxamide;
N-{4-[1-(tetrahydro-2H-pyran-4-ylcarbonyl)-1,2,3,6-tetrahydropyridin-4-yl]phenyl}-1,3-dihydro-2H-pyrrolo[3,4-c]pyridine-2-carboxamide;
N-{4-[1-(1,4-dioxan-2-ylcarbonyl)-1,2,3,6-tetrahydropyridin-4-yl]phenyl}-1,3-dihydro-2H-pyrrolo[3,4-c]pyridine-2-carboxamide;
N-(4-{1-[(1-methylpyrrolidin-3-yl)carbonyl]-1,2,3,6-tetrahydropyridin-4-yl}phenyl)-1,3-dihydro-2H-pyrrolo[3,4-c]pyridine-2-carboxamide;
N-(4-{1-[(1,1-dioxidotetrahydrothiophen-3-yl)carbonyl]-1,2,3,6-tetrahydropyridin-4-yl}phenyl)-1,3-dihydro-2H-pyrrolo[3,4-c]pyridine-2-carboxamide;
N-{4-[1-(2-hydroxy-2-methylpropanoyl)-1,2,3,6-tetrahydropyridin-4-yl]phenyl}-1,3-dihydro-2H-pyrrolo[3,4-c]pyridine-2-carboxamide;
N-[1'-(tetrahydrofuran-2-ylcarbonyl)-1',2',3',6'-tetrahydro-2,4'-bipyridin-5-yl]-1,3-dihydro-2H-isoindole-2-carboxamide;

N-[1'-(tetrahydro-2H-pyran-4-ylcarbonyl)-1',2',3',6'-tetrahydro-2,4'-bipyridin-5-yl]-1,3-dihydro-2H-isoindole-2-carboxamide;

N-[1'-(1,4-dioxan-2-ylcarbonyl)-1',2',3',6'-tetrahydro-2,4'-bipyridin-5-yl]-1,3-dihydro-2H-isoindole-2-carboxamide;

N-{1'-[(1-methylpyrrolidin-3-yl)carbonyl]-1',2',3',6'-tetrahydro-2,4'-bipyridin-5-yl}-1,3-dihydro-2H-isoindole-2-carboxamide;

N-{1'-[(1,1-dioxidotetrahydrothiophen-3-yl)carbonyl]-1',2',3',6'-tetrahydro-2,4'-bipyridin-5-yl}-1,3-dihydro-2H-isoindole-2-carboxamide;

N-(4-{[(1-methylpyrrolidin-3-yl)methyl]carbamoyl}phenyl)-1,3-dihydro-2H-isoindole-2-carboxamide;

N-{4-[(pyrrolidin-3-ylmethyl)carbamoyl]phenyl}-1,3-dihydro-2H-isoindole-2-carboxamide;

N-(4-{[(3S)-tetrahydrofuran-3-ylmethyl]carbamoyl}phenyl)-1,3-dihydro-2H-pyrrolo[3,4-c]pyridine-2-carboxamide;

N-(4-{[(1-methylpiperidin-4-yl)methyl]carbamoyl}phenyl)-1,3-dihydro-2H-isoindole-2-carboxamide;

N-{4-[(2-isopropoxyethyl)carbamoyl]phenyl}-1,3-dihydro-2H-pyrrolo[3,4-c]pyridine-2-carboxamide;

N-{4-[methyl(3-methylbutyl)carbamoyl]phenyl}-1,3-dihydro-2H-pyrrolo[3,4-c]pyridine-2-carboxamide;

N-[4-(azetidin-1-ylcarbonyl)phenyl]-1,3-dihydro-2H-pyrrolo[3,4-c]pyridine-2-carboxamide;

N-[4-(2,6-diazaspiro[3.5]non-2-ylcarbonyl)phenyl]-1,3-dihydro-2H-pyrrolo[3,4-c]pyridine-2-carboxamide;

N-[4-(1,7-diazaspiro[4.4]non-1-ylcarbonyl)phenyl]-1,3-dihydro-2H-pyrrolo[3,4-c]pyridine-2-carboxamide;

N-(4-{[4-(morpholin-4-yl)benzyl]carbamoyl}phenyl)-1,3-dihydro-2H-pyrrolo[3,4-c]pyridine-2-carboxamide;

N-{4-[(cyclopropylmethyl)carbamoyl]phenyl}-1,3-dihydro-2H-pyrrolo[3,4-c]pyridine-2-carboxamide;

N-{4-[methyl(propyl)carbamoyl]phenyl}-1,3-dihydro-2H-pyrrolo[3,4-c]pyridine-2-carboxamide;

N-[4-(isobutylcarbamoyl)phenyl]-1,3-dihydro-2H-pyrrolo[3,4-c]pyridine-2-carboxamide;

N-[4-(butylcarbamoyl)phenyl]-1,3-dihydro-2H-pyrrolo[3,4-c]pyridine-2-carboxamide;

N-{4-[(2-methoxyethyl)carbamoyl]phenyl}-1,3-dihydro-2H-pyrrolo[3,4-c]pyridine-2-carboxamide;

N-[4-(cyclopentylcarbamoyl)phenyl]-1,3-dihydro-2H-pyrrolo[3,4-c]pyridine-2-carboxamide;

N-{4-[(3R)-tetrahydrofuran-3-ylcarbamoyl]phenyl}-1,3-dihydro-2H-pyrrolo[3,4-c]pyridine-2-carboxamide;

N-{4-[(2-methoxyethyl)(methyl)carbamoyl]phenyl}-1,3-dihydro-2H-pyrrolo[3,4-c]pyridine-2-carboxamide;

N-{4-[(1-methoxypropan-2-yl)carbamoyl]phenyl}-1,3-dihydro-2H-pyrrolo[3,4-c]pyridine-2-carboxamide;

N-{4-[(cyclopentylmethyl)carbamoyl]phenyl}-1,3-dihydro-2H-pyrrolo[3,4-c]pyridine-2-carboxamide;

N-{4-[(2-thienylmethyl)carbamoyl]phenyl}-1,3-dihydro-2H-pyrrolo[3,4-c]pyridine-2-carboxamide;

N-{4-[methyl(tetrahydrofuran-2-ylmethyl)carbamoyl]phenyl}-1,3-dihydro-2H-pyrrolo[3,4-c]pyridine-2-carboxamide;

N-{4-[(3-isopropoxypropyl)carbamoyl]phenyl}-1,3-dihydro-2H-pyrrolo[3,4-c]pyridine-2-carboxamide;

N-{4-[benzyl(methyl)carbamoyl]phenyl}-1,3-dihydro-2H-pyrrolo[3,4-c]pyridine-2-carboxamide;

N-{4-[(3-aminobenzyl)carbamoyl]phenyl}-1,3-dihydro-2H-pyrrolo[3,4-c]pyridine-2-carboxamide;

N-{4-[(6-methoxypyridin-3-yl)carbamoyl]phenyl}-1,3-dihydro-2H-pyrrolo[3,4-c]pyridine-2-carboxamide;

N-{4-[(3-isobutoxypropyl)carbamoyl]phenyl}-1,3-dihydro-2H-pyrrolo[3,4-c]pyridine-2-carboxamide;

N-{4-[bis(2-methoxyethyl)carbamoyl]phenyl}-1,3-dihydro-2H-pyrrolo[3,4-c]pyridine-2-carboxamide;

N-{4-[(4-methoxybenzyl)carbamoyl]phenyl}-1,3-dihydro-2H-pyrrolo[3,4-c]pyridine-2-carboxamide;

N-{4-[(3-methoxybenzyl)carbamoyl]phenyl}-1,3-dihydro-2H-pyrrolo[3,4-c]pyridine-2-carboxamide;

N-(4-{[4-(trifluoromethyl)piperidin-1-yl]carbonyl}phenyl)-1,3-dihydro-2H-pyrrolo[3,4-c]pyridine-2-carboxamide;

N-(4-{[4-(pyrazin-2-yl)piperazin-1-yl]carbonyl}phenyl)-1,3-dihydro-2H-pyrrolo[3,4-c]pyridine-2-carboxamide;

N-{4-[(4-cyclohexylpiperazin-1-yl)carbonyl]phenyl}-1,3-dihydro-2H-pyrrolo[3,4-c]pyridine-2-carboxamide;

N-(4-{[2-(3,4-dimethoxyphenyl)ethyl]carbamoyl}phenyl)-1,3-dihydro-2H-pyrrolo[3,4-c]pyridine-2-carboxamide;

N-{4-[5-(morpholin-4-ylmethyl)-1,2,4-oxadiazol-3-yl]phenyl}-1,3-dihydro-2H-isoindole-2-carboxamide;

N-(4-{5-[(4-methylpiperazin-1-yl)methyl]-1,2,4-oxadiazol-3-yl}phenyl)-1,3-dihydro-2H-isoindole-2-carboxamide;

N-[4-(5-{[(3-methylbutyl)amino]methyl}-1,2,4-oxadiazol-3-yl)phenyl]-1,3-dihydro-2H-isoindole-2-carboxamide;

N-(4-{5-[(4-hydroxypiperidin-1-yl)methyl]-1,2,4-oxadiazol-3-yl}phenyl)-1,3-dihydro-2H-isoindole-2-carboxamide;

N-[1'-(2-hydroxy-2-methylpropanoyl)-1',2',3',6'-tetrahydro-2,4'-bipyridin-5-yl]-1,3-dihydro-2H-isoindole-2-carboxamide;

N-{4-[1-(tetrahydro-2H-pyran-4-ylcarbonyl)-1,2,3,6-tetrahydropyridin-4-yl]phenyl}-1,3-dihydro-2H-isoindole-2-carboxamide;

N-{4-[1-(1,4-dioxan-2-ylcarbonyl)-1,2,3,6-tetrahydropyridin-4-yl]phenyl}-1,3-dihydro-2H-isoindole-2-carboxamide;

N-(4-{1-[(1-methylpyrrolidin-3-yl)carbonyl]-1,2,3,6-tetrahydropyridin-4-yl}phenyl)-1,3-dihydro-2H-isoindole-2-carboxamide;

N-(4-{1-[(1,1-dioxidotetrahydrothiophen-3-yl)carbonyl]-1,2,3,6-tetrahydropyridin-4-yl}phenyl)-1,3-dihydro-2H-isoindole-2-carboxamide;

N-{4-[1-(2-hydroxy-2-methylpropanoyl)-1,2,3,6-tetrahydropyridin-4-yl]phenyl}-1,3-dihydro-2H-isoindole-2-carboxamide;

N-[1'-(tetrahydrofuran-2-ylcarbonyl)-1',2',3',6'-tetrahydro-3,4'-bipyridin-6-yl]-1,3-dihydro-2H-isoindole-2-carboxamide;

N-[1'-(tetrahydro-2H-pyran-4-ylcarbonyl)-1',2',3',6'-tetrahydro-3,4'-bipyridin-6-yl]-1,3-dihydro-2H-isoindole-2-carboxamide;

N-[1'-(1,4-dioxan-2-ylcarbonyl)-1',2',3',6'-tetrahydro-3,4'-bipyridin-6-yl]-1,3-dihydro-2H-isoindole-2-carboxamide;

N-{1'-[(1-methylpyrrolidin-3-yl)carbonyl]-1',2',3',6'-tetrahydro-3,4'-bipyridin-6-yl}-1,3-dihydro-2H-isoindole-2-carboxamide;

N-{1'-[(1,1-dioxidotetrahydrothiophen-3-yl)carbonyl]-1',2',3',6'-tetrahydro-3,4'-bipyridin-6-yl}-1,3-dihydro-2H-isoindole-2-carboxamide;

N-[1'-(2-hydroxy-2-methylpropanoyl)-1',2',3',6'-tetrahydro-3,4'-bipyridin-6-yl]-1,3-dihydro-2H-isoindole-2-carboxamide;

N-(4-{[3-(dimethylamino)propyl]carbamoyl}phenyl)-1,3-dihydro-2H-pyrrolo[3,4-c]pyridine-2-carboxamide;

N-(4-{[3-(morpholin-4-yl)propyl]carbamoyl}phenyl)-1,3-dihydro-2H-pyrrolo[3,4-c]pyridine-2-carboxamide;

N-(4-{[4-(2-aminoethyl)-1H-imidazol-1-yl]carbonyl}phenyl)-1,3-dihydro-2H-pyrrolo[3,4-c]pyridine-2-carboxamide;
N-[4-({4-[2-(2-hydroxyethoxy)ethyl]piperazin-1-yl}carbonyl)phenyl]-1,3-dihydro-2H-pyrrolo[3,4-c]pyridine-2-carboxamide;
N-{4-[(3-hydroxypropyl)carbamoyl]phenyl}-1,3-dihydro-2H-pyrrolo[3,4-c]pyridine-2-carboxamide;
N-(4-{[4-(dimethylamino)butyl]carbamoyl}phenyl)-1,3-dihydro-2H-pyrrolo[3,4-c]pyridine-2-carboxamide;
N-{4-[(pyridin-4-ylmethyl)carbamoyl]phenyl}-1,3-dihydro-2H-pyrrolo[3,4-c]pyridine-2-carboxamide;
N-{4-[(pyridin-3-ylmethyl)carbamoyl]phenyl}-1,3-dihydro-2H-pyrrolo[3,4-c]pyridine-2-carboxamide;
N-{4-[(pyrimidin-4-ylmethyl)carbamoyl]phenyl}-1,3-dihydro-2H-pyrrolo[3,4-c]pyridine-2-carboxamide;
N-(4-{[2-(pyridin-3-yl)ethyl]carbamoyl}phenyl)-1,3-dihydro-2H-pyrrolo[3,4-c]pyridine-2-carboxamide;
N-(4-{[2-(4-methylpiperazin-1-yl)ethyl]carbamoyl}phenyl)-1,3-dihydro-2H-pyrrolo[3,4-c]pyridine-2-carboxamide;
N-(4-{[(1,1-dioxidotetrahydrothiophen-3-yl)methyl]carbamoyl}phenyl)-1,3-dihydro-2H-isoindole-2-carboxamide;
N-(4-{[(2,2-dimethyl-1,3-dioxolan-4-yl)methyl]carbamoyl}phenyl)-1,3-dihydro-2H-isoindole-2-carboxamide;
N-(4-{[(1S)-2-methoxy-1-phenylethyl]carbamoyl}phenyl)-1,3-dihydro-2H-isoindole-2-carboxamide;
N-[4-({[(4S)-2,2-dimethyl-1,3-dioxolan-4-yl]methyl}carbamoyl)phenyl]-1,3-dihydro-2H-isoindole-2-carboxamide;
N-[4-({[(4R)-2,2-dimethyl-1,3-dioxolan-4-yl]methyl}carbamoyl)phenyl]-1,3-dihydro-2H-isoindole-2-carboxamide;
N-[4-({[3-(hydroxymethyl)oxetan-3-yl]methyl}carbamoyl)phenyl]-1,3-dihydro-2H-isoindole-2-carboxamide;
N-[4-(2-{benzyl[3-(morpholin-4-yl)propyl]amino}-2-oxoethyl)phenyl]-1,3-dihydro-2H-isoindole-2-carboxamide;
N-[4-(3-{benzyl[3-(morpholin-4-yl)propyl]amino}-3-oxopropyl)phenyl]-1,3-dihydro-2H-isoindole-2-carboxamide;
N-{4-[(cyclopentylacetyl)amino]phenyl}-5-fluoro-1,3-dihydro-2H-isoindole-2-carboxamide;
N-{4-[(2R)-butan-2-ylcarbamoyl]phenyl}-1,3-dihydro-2H-isoindole-2-carboxamide;
N-{4-[(cyclopentylacetyl)amino]phenyl}-5-(trifluoromethyl)-1,3-dihydro-2H-isoindole-2-carboxamide;
4-cyano-N-{4-[(cyclopentylacetyl)amino]phenyl}-1,3-dihydro-2H-isoindole-2-carboxamide;
N-{4-[(cyclopentylacetyl)amino]phenyl}-5-methyl-1,3-dihydro-2H-isoindole-2-carboxamide;
4-chloro-N-{4-[(cyclopentylacetyl)amino]phenyl}-1,3-dihydro-2H-isoindole-2-carboxamide;
N-{6-[(tetrahydro-2H-pyran-4-ylmethyl)carbamoyl]pyridazin-3-yl}-1,3-dihydro-2H-isoindole-2-carboxamide;
5-chloro-N-{4-[(cyclopentylacetyl)amino]phenyl}-1,3-dihydro-2H-isoindole-2-carboxamide;
N-{4-[1-(morpholin-4-ylacetyl)-1,2,3,6-tetrahydropyridin-4-yl]phenyl}-1,3-dihydro-2H-pyrrolo[3,4-c]pyridine-2-carboxamide;
N-[1'-(morpholin-4-ylacetyl)-1',2',3',6'-tetrahydro-2,4'-bipyridin-5-yl]-1,3-dihydro-2H-isoindole-2-carboxamide;
N-[1'-(morpholin-4-ylacetyl)-1',2',3',6'-tetrahydro-3,4'-bipyridin-6-yl]-1,3-dihydro-2H-isoindole-2-carboxamide;
N-(4-{[(3-methyloxetan-3-yl)methyl]carbamoyl}phenyl)-1,3-dihydro-2H-isoindole-2-carboxamide;
N-(4-{[(3-methyloxetan-3-yl)methyl]carbamoyl}phenyl)-1,3-dihydro-2H-pyrrolo[3,4-c]pyridine-2-carboxamide;
N-(2-{(4-fluorobenzyl)[4-(pyridin-3-yl)benzyl]amino}-1,3-thiazol-5-yl)-1,3-dihydro-2H-pyrrolo[3,4-c]pyridine-2-carboxamide;
N-[4-(2-benzyl-1,3-thiazol-4-yl)phenyl]-1,3-dihydro-2H-isoindole-2-carboxamide;
N-{4-[(3-methylbutyl)sulfamoyl]phenyl}-1,3-dihydro-2H-isoindole-2-carboxamide;
5-cyano-N-{4-[(cyclopentylmethyl)carbamoyl]phenyl}-1,3-dihydro-2H-isoindole-2-carboxamide;
5-cyano-N-{4-[(1,3-thiazol-5-ylmethyl)carbamoyl]phenyl}-1,3-dihydro-2H-isoindole-2-carboxamide;
5-cyano-N-(4-{[(1R)-3-hydroxy-1-phenylpropyl]carbamoyl}phenyl)-1,3-dihydro-2H-isoindole-2-carboxamide;
5-cyano-N-(4-{[2-hydroxy-1-(4-methylphenyl)ethyl]carbamoyl}phenyl)-1,3-dihydro-2H-isoindole-2-carboxamide;
5-cyano-N-{4-[(1,3-dihydroxypropan-2-yl)carbamoyl]phenyl}-1,3-dihydro-2H-isoindole-2-carboxamide;
5-cyano-N-(4-{[(2R)-2-hydroxypropyl]carbamoyl}phenyl)-1,3-dihydro-2H-isoindole-2-carboxamide;
5-cyano-N-{4-[(2-hydroxy-2-methylpropyl)carbamoyl]phenyl}-1,3-dihydro-2H-isoindole-2-carboxamide;
5-cyano-N-(4-{[(2R)-1-hydroxy-3-methylbutan-2-yl]carbamoyl}phenyl)-1,3-dihydro-2H-isoindole-2-carboxamide;
5-cyano-N-(4-{[(2S)-tetrahydrofuran-2-ylmethyl]carbamoyl}phenyl)-1,3-dihydro-2H-isoindole-2-carboxamide;
5-cyano-N-(4-{[2-(4-methylpiperazin-1-yl)ethyl]carbamoyl}phenyl)-1,3-dihydro-2H-isoindole-2-carboxamide;
5-cyano-N-(4-{[(1S)-2-hydroxy-1-phenylethyl]carbamoyl}phenyl)-1,3-dihydro-2H-isoindole-2-carboxamide;
5-cyano-N-{4-[(4-hydroxybutyl)carbamoyl]phenyl}-1,3-dihydro-2H-isoindole-2-carboxamide;
5-cyano-N-(4-{[(2S)-2-hydroxypropyl]carbamoyl}phenyl)-1,3-dihydro-2H-isoindole-2-carboxamide;
5-cyano-N-{4-[(3-furylmethyl)carbamoyl]phenyl}-1,3-dihydro-2H-isoindole-2-carboxamide;
5-cyano-N-{4-[(tetrahydrofuran-2-ylmethyl)carbamoyl]phenyl}-1,3-dihydro-2H-isoindole-2-carboxamide;
5-cyano-N-(4-{[4-(2-furoyl)piperazin-1-yl]carbonyl}phenyl)-1,3-dihydro-2H-isoindole-2-carboxamide;
5-cyano-N-(4-{[4-(tetrahydrofuran-2-ylcarbonyl)piperazin-1-yl]carbonyl}phenyl)-1,3-dihydro-2H-isoindole-2-carboxamide;
5-cyano-N-(4-{[3-(piperidin-1-yl)propyl]carbamoyl}phenyl)-1,3-dihydro-2H-isoindole-2-carboxamide;
5-cyano-N-(4-{[(2R)-tetrahydrofuran-2-ylmethyl]carbamoyl}phenyl)-1,3-dihydro-2H-isoindole-2-carboxamide;
5-cyano-N-(4-{[4-(ethylsulfonyl)piperazin-1-yl]carbonyl}phenyl)-1,3-dihydro-2H-isoindole-2-carboxamide;
5-cyano-N-{4-[(tetrahydrofuran-3-ylmethyl)carbamoyl]phenyl}-1,3-dihydro-2H-isoindole-2-carboxamide;
5-cyano-N-(4-{[(1R)-2-hydroxy-1-phenylethyl]carbamoyl}phenyl)-1,3-dihydro-2H-isoindole-2-carboxamide;

5-cyano-N-(4-{[(2S)-1-hydroxybutan-2-yl]
carbamoyl}phenyl)-1,3-dihydro-2H-isoindole-2-carboxamide;
5-cyano-N-{4-[(2,3-dihydroxypropyl)carbamoyl]phenyl}-1,3-dihydro-2H-isoindole-2-carboxamide;
5-cyano-N-{4-[(tetrahydro-2H-pyran-4-ylmethyl)carbamoyl]phenyl}-1,3-dihydro-2H-isoindole-2-carboxamide;
5-cyano-N-(4-{[2-hydroxy-1-(pyridin-2-yl)ethyl]
carbamoyl}phenyl)-1,3-dihydro-2H-isoindole-2-carboxamide;
5-cyano-N-{4-[(1-hydroxy-4-methylpentan-2-yl)carbamoyl]phenyl}-1,3-dihydro-2H-isoindole-2-carboxamide;
5-cyano-N-(4-{[(1-methylpyrrolidin-3-yl)methyl]
carbamoyl}phenyl)-1,3-dihydro-2H-isoindole-2-carboxamide;
5-cyano-N-(4-{[(1-methylpiperidin-4-yl)methyl]
carbamoyl}phenyl)-1,3-dihydro-2H-isoindole-2-carboxamide;
5-cyano-N-{4-[(tetrahydro-2H-pyran-3-ylmethyl)carbamoyl]phenyl}-1,3-dihydro-2H-isoindole-2-carboxamide;
N-(5-{[(3S)-tetrahydrofuran-3-ylmethyl]
carbamoyl}pyridin-2-yl)-1,3-dihydro-2H-isoindole-2-carboxamide;
N-[4-(2,6-diazaspiro[3.3]hept-2-ylcarbonyl)phenyl]-1,3-dihydro-2H-isoindole-2-carboxamide;
N-[4-(2,6-diazaspiro[3.4]oct-6-ylcarbonyl)phenyl]-1,3-dihydro-2H-isoindole-2-carboxamide;
N-[4-(2,7-diazaspiro[3.5]non-7-ylcarbonyl)phenyl]-1,3-dihydro-2H-isoindole-2-carboxamide;
N-[4-(2,6-diazaspiro[3.5]non-2-ylcarbonyl)phenyl]-1,3-dihydro-2H-isoindole-2-carboxamide;
N-[4-(1,7-diazaspiro[4.4]non-1-ylcarbonyl)phenyl]-1,3-dihydro-2H-isoindole-2-carboxamide;
N-[4-(1,7-diazaspiro[4.4]non-7-ylcarbonyl)phenyl]-1,3-dihydro-2H-isoindole-2-carboxamide;
N-[4-(2,7-diazaspiro[4.4]non-2-ylcarbonyl)phenyl]-1,3-dihydro-2H-isoindole-2-carboxamide;
N-[4-(2,8-diazaspiro[4.5]dec-2-ylcarbonyl)phenyl]-1,3-dihydro-2H-isoindole-2-carboxamide;
N-[4-(2,7-diazaspiro[4.5]dec-2-ylcarbonyl)phenyl]-1,3-dihydro-2H-isoindole-2-carboxamide;
N-[4-(2,6-diazaspiro[4.5]dec-2-ylcarbonyl)phenyl]-1,3-dihydro-2H-isoindole-2-carboxamide;
N-[4-(2,7-diazaspiro[4.5]dec-7-ylcarbonyl)phenyl]-1,3-dihydro-2H-isoindole-2-carboxamide;
N-[4-(3,9-diazaspiro[5.5]undec-3-ylcarbonyl)phenyl]-1,3-dihydro-2H-isoindole-2-carboxamide;
N-[4-(2,9-diazaspiro[5.5]undec-2-ylcarbonyl)phenyl]-1,3-dihydro-2H-isoindole-2-carboxamide;
N-[4-(2,8-diazaspiro[5.5]undec-2-ylcarbonyl)phenyl]-1,3-dihydro-2H-isoindole-2-carboxamide;
N-[4-(1,8-diazaspiro[5.5]undec-8-ylcarbonyl)phenyl]-1,3-dihydro-2H-isoindole-2-carboxamide;
N-[4-(1,8-diazaspiro[4.6]undec-8-ylcarbonyl)phenyl]-1,3-dihydro-2H-isoindole-2-carboxamide;
N-{4-[(1-oxa-8-azaspiro[4.5]dec-2-ylmethyl)carbamoyl]phenyl}-1,3-dihydro-2H-isoindole-2-carboxamide;
N-[4-(1-oxa-8-azaspiro[4.5]dec-3-ylcarbamoyl)phenyl]-1,3-dihydro-2H-isoindole-2-carboxamide;
N-{4-[(2-oxa-9-azaspiro[5.5]undec-3-ylmethyl)carbamoyl]phenyl}-1,3-dihydro-2H-isoindole-2-carboxamide;
N-[4-(1-oxa-4,8-diazaspiro[5.5]undec-4-ylcarbonyl)phenyl]-1,3-dihydro-2H-isoindole-2-carboxamide;
N-[4-(1,8-diazaspiro[4.5]dec-1-ylcarbonyl)phenyl]-1,3-dihydro-2H-isoindole-2-carboxamide;
N-[4-(1,8-diazaspiro[4.5]dec-8-ylcarbonyl)phenyl]-1,3-dihydro-2H-isoindole-2-carboxamide;
N-[4-(2,6-diazaspiro[3.4]oct-2-ylcarbonyl)phenyl]-1,3-dihydro-2H-isoindole-2-carboxamide;
N-[4-(1,7-diazaspiro[3.5]non-7-ylcarbonyl)phenyl]-1,3-dihydro-2H-isoindole-2-carboxamide;
N-[4-(1,6-diazaspiro[3.5]non-1-ylcarbonyl)phenyl]-1,3-dihydro-2H-isoindole-2-carboxamide;
N-[4-(2,5-diazaspiro[3.5]non-2-ylcarbonyl)phenyl]-1,3-dihydro-2H-isoindole-2-carboxamide;
N-[4-(5-oxa-2-azaspiro[3.4]oct-2-ylcarbonyl)phenyl]-1,3-dihydro-2H-isoindole-2-carboxamide;
N-[4-(6-oxa-2-azaspiro[3.5]non-2-ylcarbonyl)phenyl]-1,3-dihydro-2H-isoindole-2-carboxamide;
N-[4-(hexahydro-5H-furo[2,3-c]pyrrol-5-ylcarbonyl)phenyl]-1,3-dihydro-2H-isoindole-2-carboxamide;
N-[4-(tetrahydro-1H-furo[3,4-c]pyrrol-5(3H)-ylcarbonyl)phenyl]-1,3-dihydro-2H-isoindole-2-carboxamide;
N-[4-(hexahydrofuro[3,4-c]pyridin-5(3H)-ylcarbonyl)phenyl]-1,3-dihydro-2H-isoindole-2-carboxamide;
N-[4-(4-{benzyl[3-(morpholin-4-yl)propyl]amino}-4-oxobutyl)phenyl]-1,3-dihydro-2H-isoindole-2-carboxamide;
N-[4-(2-{benzyl[3-(morpholin-4-yl)propyl]amino}ethyl)
phenyl]-1,3-dihydro-2H-isoindole-2-carboxamide;
5-acetyl-N-{4-[(cyclopentylacetyl)amino]phenyl}-1,3-dihydro-2H-isoindole-2-carboxamide;
N-(4-{[(1,1-dioxidotetrahydrothiophen-3-yl)methyl]
carbamoyl}phenyl)-1,3-dihydro-2H-pyrrolo[3,4-c]pyridine-2-carboxamide;
5-cyano-N-{4-[(3-methylbutyl)sulfamoyl]phenyl}-1,3-dihydro-2H-isoindole-2-carboxamide;
N-{4-[(3-methylbutyl)sulfamoyl]phenyl}-1,3-dihydro-2H-pyrrolo[3,4-c]pyridine-2-carboxamide;
N-{4-[(cyclopentylacetyl)amino]phenyl}-5-(1-hydroxyethyl)-1,3-dihydro-2H-isoindole-2-carboxamide;
N-[4-(butyrylamino)phenyl]-5-cyano-1,3-dihydro-2H-isoindole-2-carboxamide;
N-{4-[(pyrrolidin-3-ylmethyl)carbamoyl]phenyl}-1,3-dihydro-2H-pyrrolo[3,4-c]pyridine-2-carboxamide;
N-(4-{[(3S)-pyrrolidin-3-ylmethyl]carbamoyl}phenyl)-1,3-dihydro-2H-pyrrolo[3,4-c]pyridine-2-carboxamide;
N-(4-{[(1-methylpyrrolidin-3-yl)methyl]
carbamoyl}phenyl)-1,3-dihydro-2H-pyrrolo[3,4-c]pyridine-2-carboxamide;
N-(4-{[(3-methoxybenzyl)sulfonyl]amino}phenyl)-1,3-dihydro-2H-isoindole-2-carboxamide;
N-(4-{[(1-methylpiperidin-4-yl)methyl]
carbamoyl}phenyl)-1,3-dihydro-2H-pyrrolo[3,4-c]pyridine-2-carboxamide;
N-[4-(2,6-diazaspiro[3.4]oct-6-ylcarbonyl)phenyl]-5-fluoro-1,3-dihydro-2H-isoindole-2-carboxamide;
N-[4-(2,7-diazaspiro[3.5]non-7-ylcarbonyl)phenyl]-5-fluoro-1,3-dihydro-2H-isoindole-2-carboxamide;
N-[4-(1,7-diazaspiro[4.4]non-1-ylcarbonyl)phenyl]-5-fluoro-1,3-dihydro-2H-isoindole-2-carboxamide;
N-[4-(2,8-diazaspiro[4.5]dec-2-ylcarbonyl)phenyl]-5-fluoro-1,3-dihydro-2H-isoindole-2-carboxamide;
N-[4-(2,6-diazaspiro[4.5]dec-2-ylcarbonyl)phenyl]-5-fluoro-1,3-dihydro-2H-isoindole-2-carboxamide;
N-[4-(2,7-diazaspiro[4.5]dec-7-ylcarbonyl)phenyl]-5-fluoro-1,3-dihydro-2H-isoindole-2-carboxamide;
N-[4-(2,8-diazaspiro[5.5]undec-2-ylcarbonyl)phenyl]-5-fluoro-1,3-dihydro-2H-isoindole-2-carboxamide;
N-[4-(1,8-diazaspiro[5.5]undec-8-ylcarbonyl)phenyl]-5-fluoro-1,3-dihydro-2H-isoindole-2-carboxamide;
N-[4-(1,8-diazaspiro[4.6]undec-8-ylcarbonyl)phenyl]-5-fluoro-1,3-dihydro-2H-isoindole-2-carboxamide;

5-fluoro-N-{4-[(1-oxa-8-azaspiro[4.5]dec-2-ylmethyl)carbamoyl]phenyl}-1,3-dihydro-2H-isoindole-2-carboxamide;
5-fluoro-N-[4-(1-oxa-8-azaspiro[4.5]dec-3-ylcarbamoyl)phenyl]-1,3-dihydro-2H-isoindole-2-carboxamide;
5-fluoro-N-[4-(1-oxa-4,8-diazaspiro[5.5]undec-4-ylcarbonyl)phenyl]-1,3-dihydro-2H-isoindole-2-carboxamide;
N-[4-(1,8-diazaspiro[4.5]dec-1-ylcarbonyl)phenyl]-5-fluoro-1,3-dihydro-2H-isoindole-2-carboxamide;
N-[4-(1,8-diazaspiro[4.5]dec-8-ylcarbonyl)phenyl]-5-fluoro-1,3-dihydro-2H-isoindole-2-carboxamide;
N-[4-(2,6-diazaspiro[3.4]oct-2-ylcarbonyl)phenyl]-5-fluoro-1,3-dihydro-2H-isoindole-2-carboxamide;
N-[4-(1,7-diazaspiro[3.5]non-7-ylcarbonyl)phenyl]-5-fluoro-1,3-dihydro-2H-isoindole-2-carboxamide;
N-[4-(1,6-diazaspiro[3.5]non-1-ylcarbonyl)phenyl]-5-fluoro-1,3-dihydro-2H-isoindole-2-carboxamide;
N-[4-(2,5-diazaspiro[3.5]non-2-ylcarbonyl)phenyl]-5-fluoro-1,3-dihydro-2H-isoindole-2-carboxamide;
5-fluoro-N-[4-(5-oxa-2-azaspiro[3.4]oct-2-ylcarbonyl)phenyl]-1,3-dihydro-2H-isoindole-2-carboxamide;
5-fluoro-N-[4-(6-oxa-2-azaspiro[3.5]non-2-ylcarbonyl)phenyl]-1,3-dihydro-2H-isoindole-2-carboxamide;
5-fluoro-N-[4-(2-oxa-7-azaspiro[3.5]non-7-ylcarbonyl)phenyl]-1,3-dihydro-2H-isoindole-2-carboxamide;
5-fluoro-N-[4-(hexahydro-5H-furo[2,3-c]pyrrol-5-ylcarbonyl)phenyl]-1,3-dihydro-2H-isoindole-2-carboxamide;
5-fluoro-N-[4-(tetrahydro-1H-furo[3,4-c]pyrrol-5(3H)-ylcarbonyl)phenyl]-1,3-dihydro-2H-isoindole-2-carboxamide;
5-fluoro-N-[4-(hexahydrofuro[3,4-c]pyridin-5(3H)-ylcarbonyl)phenyl]-1,3-dihydro-2H-isoindole-2-carboxamide;
N-{4-[1-(tetrahydrofuran-3-ylcarbonyl)piperidin-4-yl]phenyl}-1,3-dihydro-2H-pyrrolo[3,4-c]pyridine-2-carboxamide;
N-(4-{1-[(2-methoxyethoxy)acetyl]piperidin-4-yl}phenyl)-1,3-dihydro-2H-pyrrolo[3,4-c]pyridine-2-carboxamide;
N-{4-[1-(tetrahydrofuran-2-ylcarbonyl)piperidin-4-yl]phenyl}-1,3-dihydro-2H-pyrrolo[3,4-c]pyridine-2-carboxamide;
N-{4-[1-(tetrahydro-2H-pyran-4-ylcarbonyl)piperidin-4-yl]phenyl}-1,3-dihydro-2H-pyrrolo[3,4-c]pyridine-2-carboxamide;
N-{4-[1-(1,4-dioxan-2-ylcarbonyl)piperidin-4-yl]phenyl}-1,3-dihydro-2H-pyrrolo[3,4-c]pyridine-2-carboxamide;
N-(4-{1-[(1-methylpyrrolidin-3-yl)carbonyl]piperidin-4-yl}phenyl)-1,3-dihydro-2H-pyrrolo[3,4-c]pyridine-2-carboxamide;
N-(4-{1-[(1,1-dioxidotetrahydrothiophen-3-yl)carbonyl]piperidin-4-yl}phenyl)-1,3-dihydro-2H-pyrrolo[3,4-c]pyridine-2-carboxamide;
N-{4-[1-(2-hydroxy-2-methylpropanoyl)piperidin-4-yl]phenyl}-1,3-dihydro-2H-pyrrolo[3,4-c]pyridine-2-carboxamide;
N-{4-[1-(morpholin-4-ylacetyl)piperidin-4-yl]phenyl}-1,3-dihydro-2H-pyrrolo[3,4-c]pyridine-2-carboxamide;
5-(acetamidomethyl)-N-{4-[(cyclopentylacetyl)amino]phenyl}-1,3-dihydro-2H-isoindole-2-carboxamide;
N-{5-[2-(2-chlorobenzyl)-1,3-thiazol-4-yl]-2-thienyl}-1,3-dihydro-2H-isoindole-2-carboxamide;
N-[4-({[(3R)-1-isobutyrylpyrrolidin-3-yl]methyl}carbamoyl)phenyl]-1,3-dihydro-2H-pyrrolo[3,4-c]pyridine-2-carboxamide;
N-[4-({[(3R)-1-benzoylpyrrolidin-3-yl]methyl}carbamoyl)phenyl]-1,3-dihydro-2H-pyrrolo[3,4-c]pyridine-2-carboxamide;
N-[4-({[1-(tetrahydrofuran-3-ylcarbonyl)pyrrolidin-3-yl]methyl}carbamoyl)phenyl]-1,3-dihydro-2H-pyrrolo[3,4-c]pyridine-2-carboxamide;
N-[4-({[1-(methylsulfonyl)pyrrolidin-3-yl]methyl}carbamoyl)phenyl]-1,3-dihydro-2H-pyrrolo[3,4-c]pyridine-2-carboxamide;
N-[4-(1-isobutyl-1,2,3,6-tetrahydropyridin-4-yl)phenyl]-1,3-dihydro-2H-pyrrolo[3,4-c]pyridine-2-carboxamide;
N-{4-[1-(tetrahydrofuran-3-ylmethyl)-1,2,3,6-tetrahydropyridin-4-yl]phenyl}-1,3-dihydro-2H-pyrrolo[3,4-c]pyridine-2-carboxamide;
N-{4-[1-(tetrahydro-2H-pyran-4-ylmethyl)-1,2,3,6-tetrahydropyridin-4-yl]phenyl}-1,3-dihydro-2H-pyrrolo[3,4-c]pyridine-2-carboxamide;
N-[4-(1-isobutylpiperidin-4-yl)phenyl]-1,3-dihydro-2H-pyrrolo[3,4-c]pyridine-2-carboxamide;
N-{4-[1-(tetrahydrofuran-3-ylmethyl)piperidin-4-yl]phenyl}-1,3-dihydro-2H-pyrrolo[3,4-c]pyridine-2-carboxamide;
N-{4-[1-(tetrahydro-2H-pyran-4-ylmethyl)piperidin-4-yl]phenyl}-1,3-dihydro-2H-pyrrolo[3,4-c]pyridine-2-carboxamide;
N-{4-[(cyclopentylacetyl)amino]phenyl}-5-(2-hydroxypropan-2-yl)-1,3-dihydro-2H-isoindole-2-carboxamide;
tert-butyl {4-[(1,3-dihydro-2H-isoindol-2-ylcarbonyl)amino]benzyl}carbamate;
N-{4-[(cyclopentylacetyl)amino]phenyl}-1,3-dihydro-2H-pyrrolo[3,4-c]pyridine-2-carboxamide;
N-{4-[(cyclopentylacetyl)amino]phenyl}-5-(methoxymethyl)-1,3-dihydro-2H-isoindole-2-carboxamide;
N-[4-(5-{[(tetrahydrofuran-2-ylmethyl)amino]methyl}-1,2,4-oxadiazol-3-yl)phenyl]-1,3-dihydro-2H-isoindole-2-carboxamide;
N-(4-{5-[(4-methoxypiperidin-1-yl)methyl]-1,2,4-oxadiazol-3-yl}phenyl)-1,3-dihydro-2H-isoindole-2-carboxamide;
N-[4-(5-{[4-(2-methoxyethyl)piperazin-1-yl]methyl}-1,2,4-oxadiazol-3-yl)phenyl]-1,3-dihydro-2H-isoindole-2-carboxamide;
N-[4-({[1-(morpholin-4-yl)cyclopentyl]methyl}carbamoyl)phenyl]-1,3-dihydro-2H-pyrrolo[3,4-c]pyridine-2-carboxamide;
N-{4-[(1-pentanoylpiperidin-4-yl)oxy]phenyl}-1,3-dihydro-2H-pyrrolo[3,4-c]pyridine-2-carboxamide;
N-{4-[(1-acetylpiperidin-4-yl)oxy]phenyl}-1,3-dihydro-2H-pyrrolo[3,4-c]pyridine-2-carboxamide;
N-{4-[(1-butyrylpiperidin-4-yl)oxy]phenyl}-1,3-dihydro-2H-pyrrolo[3,4-c]pyridine-2-carboxamide;
N-(4-{[1-(2-methylbutanoyl)piperidin-4-yl]oxy}phenyl)-1,3-dihydro-2H-pyrrolo[3,4-c]pyridine-2-carboxamide;
N-(4-{[1-(3,3,3-trifluoropropanoyl)piperidin-4-yl]oxy}phenyl)-1,3-dihydro-2H-pyrrolo[3,4-c]pyridine-2-carboxamide;
N-(4-{[1-(methoxyacetyl)piperidin-4-yl]oxy}phenyl)-1,3-dihydro-2H-pyrrolo[3,4-c]pyridine-2-carboxamide;
N-(4-{[1-(tetrahydrofuran-2-ylcarbonyl)piperidin-4-yl]oxy}phenyl)-1,3-dihydro-2H-pyrrolo[3,4-c]pyridine-2-carboxamide;
N-(4-{[1-(cyclopropylcarbonyl)piperidin-4-yl]oxy}phenyl)-1,3-dihydro-2H-pyrrolo[3,4-c]pyridine-2-carboxamide;
N-(4-{[1-(cyclopropylacetyl)piperidin-4-yl]oxy}phenyl)-1,3-dihydro-2H-pyrrolo[3,4-c]pyridine-2-carboxamide;
N-(4-{[1-(cyclobutylcarbonyl)piperidin-4-yl]oxy}phenyl)-1,3-dihydro-2H-pyrrolo[3,4-c]pyridine-2-carboxamide;
N-(4-{[1-(cyclopentylcarbonyl)piperidin-4-yl]oxy}phenyl)-1,3-dihydro-2H-pyrrolo[3,4-c]pyridine-2-carboxamide;

N-(4-{[1-(cyclopentylacetyl)piperidin-4-yl]oxy}phenyl)-1,3-dihydro-2H-pyrrolo[3,4-c]pyridine-2-carboxamide;
N-(4-{[1-(cyclohexylcarbonyl)piperidin-4-yl]oxy}phenyl)-1,3-dihydro-2H-pyrrolo[3,4-c]pyridine-2-carboxamide;
N-{6-[(1-acetylpiperidin-4-yl)oxy]pyridin-3-yl}-1,3-dihydro-2H-isoindole-2-carboxamide;
N-{6-[(1-isobutyrylpiperidin-4-yl)oxy]pyridin-3-yl}-1,3-dihydro-2H-isoindole-2-carboxamide;
N-(6-{[1-(3-methylbutanoyl)piperidin-4-yl]oxy}pyridin-3-yl)-1,3-dihydro-2H-isoindole-2-carboxamide;
N-(6-{[1-(4,4,4-trifluorobutanoyl)piperidin-4-yl]oxy}pyridin-3-yl)-1,3-dihydro-2H-isoindole-2-carboxamide;
N-(6-{[1-(methoxyacetyl)piperidin-4-yl]oxy}pyridin-3-yl)-1,3-dihydro-2H-isoindole-2-carboxamide;
N-(6-{[1-(tetrahydro furan-2-ylcarbonyl)piperidin-4-yl]oxy}pyridin-3-yl)-1,3-dihydro-2H-isoindole-2-carboxamide;
N-(6-{[1-(tetrahydrofuran-3-ylcarbonyl)piperidin-4-yl]oxy}pyridin-3-yl)-1,3-dihydro-2H-isoindole-2-carboxamide;
N-(6-{[1-(cyclopropylcarbonyl)piperidin-4-yl]oxy}pyridin-3-yl)-1,3-dihydro-2H-isoindole-2-carboxamide;
N-(6-{[1-(cyclopropylacetyl)piperidin-4-yl]oxy}pyridin-3-yl)-1,3-dihydro-2H-isoindole-2-carboxamide;
N-(6-{[1-(cyclobutylcarbonyl)piperidin-4-yl]oxy}pyridin-3-yl)-1,3-dihydro-2H-isoindole-2-carboxamide;
N-(6-{[1-(cyclopentylcarbonyl)piperidin-4-yl]oxy}pyridin-3-yl)-1,3-dihydro-2H-isoindole-2-carboxamide;
N-(6-{[1-(cyclopentylacetyl)piperidin-4-yl]oxy}pyridin-3-yl)-1,3-dihydro-2H-isoindole-2-carboxamide;
N-(6-{[1-(cyclohexylcarbonyl)piperidin-4-yl]oxy}pyridin-3-yl)-1,3-dihydro-2H-isoindole-2-carboxamide;
tert-butyl (2-{4-[(1,3-dihydro-2H-isoindol-2-ylcarbonyl)amino]phenyl}ethyl)carbamate;
N-(4-{1-[(2R)-tetrahydrofuran-2-ylcarbonyl]-1,2,3,6-tetrahydropyridin-4-yl}phenyl)-1,3-dihydro-2H-pyrrolo[3,4-c]pyridine-2-carboxamide;
N-(4-{1-[(2S)-tetrahydrofuran-2-ylcarbonyl]-1,2,3,6-tetrahydropyridin-4-yl}phenyl)-1,3-dihydro-2H-pyrrolo[3,4-c]pyridine-2-carboxamide;
N-(4-{[(1S)-1-(4-fluorophenyl)-2-hydroxyethyl]carbamoyl}phenyl)-1,3-dihydro-2H-pyrrolo[3,4-c]pyridine-2-carboxamide;
N-(4-{[(1S)-2-hydroxy-1-(4-methoxyphenyl)ethyl]carbamoyl}phenyl)-1,3-dihydro-2H-pyrrolo[3,4-c]pyridine-2-carboxamide;
N-[4-({[3-(hydroxymethyl)oxetan-3-yl]methyl}carbamoyl)phenyl]-1,3-dihydro-2H-pyrrolo[3,4-c]pyridine-2-carboxamide;
N-(4-{[(1S)-1-(1,3-benzodioxol-5-yl)-2-hydroxyethyl]carbamoyl}phenyl)-1,3-dihydro-2H-pyrrolo[3,4-c]pyridine-2-carboxamide;
N-{4-[(tetrahydrofuran-3-ylmethyl)sulfamoyl]phenyl}-1,3-dihydro-2H-isoindole-2-carboxamide;
N-{4-[(tetrahydrofuran-3-ylmethyl)sulfamoyl]phenyl}-1,3-dihydro-2H-pyrrolo[3,4-c]pyridine-2-carboxamide;
5-cyano-N-{4-[(tetrahydrofuran-3-ylmethyl)sulfamoyl]phenyl}-1,3-dihydro-2H-isoindole-2-carboxamide;
N-(4-{[(1S)-1-(4-fluorophenyl)-2-hydroxyethyl]carbamoyl}phenyl)-1,3-dihydro-2H-isoindole-2-carboxamide;
N-(4-{[(1S)-2-hydroxy-1-(4-methoxyphenyl)ethyl]carbamoyl}phenyl)-1,3-dihydro-2H-isoindole-2-carboxamide;
N-(4-{[(1S)-1-(1,3-benzodioxol-5-yl)-2-hydroxyethyl]carbamoyl}phenyl)-1,3-dihydro-2H-isoindole-2-carboxamide;
N-{4-[1-(tetrahydrofuran-3-ylcarbonyl)piperidin-4-yl]phenyl}-1,3-dihydro-2H-isoindole-2-carboxamide;
N-{4-[1-(tetrahydrofuran-2-ylcarbonyl)piperidin-4-yl]phenyl}-1,3-dihydro-2H-isoindole-2-carboxamide;
N-{4-[1-(tetrahydro-2H-pyran-4-ylcarbonyl)piperidin-4-yl]phenyl}-1,3-dihydro-2H-isoindole-2-carboxamide;
N-{4-[1-(1,4-dioxan-2-ylcarbonyl)piperidin-4-yl]phenyl}-1,3-dihydro-2H-isoindole-2-carboxamide;
N-(4-{1-[(1-methylpyrrolidin-3-yl)carbonyl]piperidin-4-yl}phenyl)-1,3-dihydro-2H-isoindole-2-carboxamide;
N-(4-{1-[(1,1-dioxidotetrahydrothiophen-3-yl)carbonyl]piperidin-4-yl}phenyl)-1,3-dihydro-2H-isoindole-2-carboxamide;
N-{4-[1-(2-hydroxy-2-methylpropanoyl)piperidin-4-yl]phenyl}-1,3-dihydro-2H-isoindole-2-carboxamide;
N-{4-[1-(morpholin-4-ylacetyl)piperidin-4-yl]phenyl}-1,3-dihydro-2H-isoindole-2-carboxamide;
N-(4-{[1-(3,3,3-trifluoropropanoyl)azetidin-3-yl]oxy}phenyl)-1,3-dihydro-2H-pyrrolo[3,4-c]pyridine-2-carboxamide;
N-(4-{[1-(4,4,4-trifluorobutanoyl)azetidin-3-yl]oxy}phenyl)-1,3-dihydro-2H-pyrrolo[3,4-c]pyridine-2-carboxamide;
N-(4-{[1-(tetrahydrofuran-2-ylcarbonyl)azetidin-3-yl]oxy}phenyl)-1,3-dihydro-2H-pyrrolo[3,4-c]pyridine-2-carboxamide;
N-(4-{[1-(tetrahydrofuran-3-ylacetyl)azetidin-3-yl]oxy}phenyl)-1,3-dihydro-2H-pyrrolo[3,4-c]pyridine-2-carboxamide;
N-(4-{[1-(cyclobutylcarbonyl)azetidin-3-yl]oxy}phenyl)-1,3-dihydro-2H-pyrrolo[3,4-c]pyridine-2-carboxamide;
N-(4-{[1-(cyclopentylcarbonyl)azetidin-3-yl]oxy}phenyl)-1,3-dihydro-2H-pyrrolo[3,4-c]pyridine-2-carboxamide;
N-(4-{[1-(3-phenylpropanoyl)pyrrolidin-3-yl]oxy}phenyl)-1,3-dihydro-2H-pyrrolo[3,4-c]pyridine-2-carboxamide;
N-(4-{[1-(phenylacetyl)pyrrolidin-3-yl]oxy}phenyl)-1,3-dihydro-2H-pyrrolo[3,4-c]pyridine-2-carboxamide;
N-[4-({1-[(4-methoxyphenyl)acetyl]pyrrolidin-3-yl}oxy)phenyl]-1,3-dihydro-2H-pyrrolo[3,4-c]pyridine-2-carboxamide;
N-(4-{[1-(methoxyacetyl)pyrrolidin-3-yl]oxy}phenyl)-1,3-dihydro-2H-pyrrolo[3,4-c]pyridine-2-carboxamide;
N-(4-{[1-(cyclopropylcarbonyl)pyrrolidin-3-yl]oxy}phenyl)-1,3-dihydro-2H-pyrrolo[3,4-c]pyridine-2-carboxamide;
N-(4-{[1-(cyclohexylcarbonyl)pyrrolidin-3-yl]oxy}phenyl)-1,3-dihydro-2H-pyrrolo[3,4-c]pyridine-2-carboxamide;
N-(4-{[1-(cyclopentylacetyl)pyrrolidin-3-yl]oxy}phenyl)-1,3-dihydro-2H-pyrrolo[3,4-c]pyridine-2-carboxamide;
N-(4-{[1-(cyclopentylcarbonyl)pyrrolidin-3-yl]oxy}phenyl)-1,3-dihydro-2H-pyrrolo[3,4-c]pyridine-2-carboxamide;
N-{4-[(1-benzoylpyrrolidin-3-yl)oxy]phenyl}-1,3-dihydro-2H-pyrrolo[3,4-c]pyridine-2-carboxamide;
N-(4-{[1-(3-ethoxypropanoyl)pyrrolidin-3-yl]oxy}phenyl)-1,3-dihydro-2H-pyrrolo[3,4-c]pyridine-2-carboxamide;
N-[4-({1-[(2-methylcyclopropyl)carbonyl]pyrrolidin-3-yl}oxy)phenyl]-1,3-dihydro-2H-pyrrolo[3,4-c]pyridine-2-carboxamide;
N-[4-({1-[(1-methylcyclopropyl)carbonyl]pyrrolidin-3-yl}oxy)phenyl]-1,3-dihydro-2H-pyrrolo[3,4-c]pyridine-2-carboxamide;
N-(4-{[1-(cyclobutylcarbonyl)pyrrolidin-3-yl]oxy}phenyl)-1,3-dihydro-2H-pyrrolo[3,4-c]pyridine-2-carboxamide;

N-(4-{[1-(3-methylbutanoyl)pyrrolidin-3-yl]oxy}phenyl)-1,3-dihydro-2H-pyrrolo[3,4-c]pyridine-2-carboxamide;
N-(4-{[1-(2-methylpropanoyl)pyrrolidin-3-yl]oxy}phenyl)-1,3-dihydro-2H-pyrrolo[3,4-c]pyridine-2-carboxamide;
N-{4-[(1-acetylpyrrolidin-3-yl)oxy]phenyl}-1,3-dihydro-2H-pyrrolo[3,4-c]pyridine-2-carboxamide;
N-(4-{[1-(4,4,4-trifluorobutanoyl)pyrrolidin-3-yl]oxy}phenyl)-1,3-dihydro-2H-pyrrolo[3,4-c]pyridine-2-carboxamide;
N-(4-{[1-(tetrahydrofuran-3-ylcarbonyl)pyrrolidin-3-yl]oxy}phenyl)-1,3-dihydro-2H-pyrrolo[3,4-c]pyridine-2-carboxamide;
N-(4-{[1-(tetrahydrofuran-2-ylcarbonyl)pyrrolidin-3-yl]oxy}phenyl)-1,3-dihydro-2H-pyrrolo[3,4-c]pyridine-2-carboxamide;
N-(4-{[1-(ethoxyacetyl)pyrrolidin-3-yl]oxy}phenyl)-1,3-dihydro-2H-pyrrolo[3,4-c]pyridine-2-carboxamide;
N-(4-{[1-(tetrahydrofuran-3-ylcarbonyl)piperidin-4-yl]oxy}phenyl)-1,3-dihydro-2H-isoindole-2-carboxamide;
N-(4-{1-[(1-methylpiperidin-4-yl)carbonyl]-1,2,3,6-tetrahydropyridin-4-yl}phenyl)-1,3-dihydro-2H-pyrrolo[3,4-c]pyridine-2-carboxamide;
N-(4-{1-[(1,1-dioxidotetrahydro-2H-thiopyran-4-yl)carbonyl]-1,2,3,6-tetrahydropyridin-4-yl}phenyl)-1,3-dihydro-2H-pyrrolo[3,4-c]pyridine-2-carboxamide;
N-(4-{1-[(3R)-tetrahydrofuran-3-ylcarbonyl]-1,2,3,6-tetrahydropyridin-4-yl}phenyl)-1,3-dihydro-2H-pyrrolo[3,4-c]pyridine-2-carboxamide;
N-(4-{1-[(3S)-tetrahydrofuran-3-ylcarbonyl]-1,2,3,6-tetrahydropyridin-4-yl}phenyl)-1,3-dihydro-2H-pyrrolo[3,4-c]pyridine-2-carboxamide;
N-(4-{4-[(2-methylpropanoyl)amino]cyclohex-1-en-1-yl}phenyl)-1,3-dihydro-2H-pyrrolo[3,4-c]pyridine-2-carboxamide;
5-cyano-N-{4-[1-(2-methylpropanoyl)-1,2,3,6-tetrahydropyridin-4-yl]phenyl}-1,3-dihydro-2H-isoindole-2-carboxamide;
tert-butyl [(1-{4-[(1,3-dihydro-2H-isoindol-2-ylcarbonyl)amino]phenyl}azetidin-3-yl)methyl]carbamate;
N-(4-{4-[(tetrahydrofuran-3-ylcarbonyl)amino]cyclohex-1-en-1-yl}phenyl)-1,3-dihydro-2H-pyrrolo[3,4-c]pyridine-2-carboxamide;
N-(4-{4-[(tetrahydro-2H-pyran-4-ylcarbonyl)amino]cyclohex-1-en-1-yl}phenyl)-1,3-dihydro-2H-pyrrolo[3,4-c]pyridine-2-carboxamide;
N-(4-{4-[(morpholin-4-ylacetyl)amino]cyclohex-1-en-1-yl}phenyl)-1,3-dihydro-2H-pyrrolo[3,4-c]pyridine-2-carboxamide;
N-[4-(4-{[(2-methoxyethoxy)acetyl]amino}cyclohex-1-en-1-yl)phenyl]-1,3-dihydro-2H-pyrrolo[3,4-c]pyridine-2-carboxamide;
N-(4-{[1-(cyclohexylacetyl)piperidin-4-yl]oxy}phenyl)-1,3-dihydro-2H-pyrrolo[3,4-c]pyridine-2-carboxamide;
N-(4-{[1-(tetrahydro-2H-pyran-4-ylacetyl)piperidin-4-yl]oxy}phenyl)-1,3-dihydro-2H-pyrrolo[3,4-c]pyridine-2-carboxamide;
N-(4-{[1-(2-methylbutanoyl)piperidin-4-yl]oxy}phenyl)-1,3-dihydro-2H-isoindole-2-carboxamide;
N-(4-{[1-(3-methylbutanoyl)piperidin-4-yl]oxy}phenyl)-1,3-dihydro-2H-isoindole-2-carboxamide;
N-(4-{[1-(2,3-dimethylbutanoyl)piperidin-4-yl]oxy}phenyl)-1,3-dihydro-2H-isoindole-2-carboxamide;
N-(4-{[1-(tetrahydrofuran-2-ylcarbonyl)piperidin-4-yl]oxy}phenyl)-1,3-dihydro-2H-isoindole-2-carboxamide;
N-(4-{[1-(cyclohexylcarbonyl)piperidin-4-yl]oxy}phenyl)-1,3-dihydro-2H-isoindole-2-carboxamide;
N-(4-{[1-(cyclohexylacetyl)piperidin-4-yl]oxy}phenyl)-1,3-dihydro-2H-isoindole-2-carboxamide;
N-(4-{[1-(tetrahydro-2H-pyran-4-ylacetyl)piperidin-4-yl]oxy}phenyl)-1,3-dihydro-2H-isoindole-2-carboxamide;
N-(4-{[1-(morpholin-4-ylacetyl)piperidin-4-yl]oxy}phenyl)-1,3-dihydro-2H-isoindole-2-carboxamide;
N-(4-{[1-(tetrahydrofuran-3-ylacetyl)piperidin-4-yl]oxy}phenyl)-1,3-dihydro-2H-isoindole-2-carboxamide;
N-(4-{[1-(tetrahydrofuran-2-ylacetyl)azetidin-3-yl]oxy}phenyl)-1,3-dihydro-2H-pyrrolo[3,4-c]pyridine-2-carboxamide;
N-(4-{[1-(tetrahydro-2H-pyran-4-ylacetyl)azetidin-3-yl]oxy}phenyl)-1,3-dihydro-2H-pyrrolo[3,4-c]pyridine-2-carboxamide;
N-(4-{[1-(morpholin-4-ylacetyl)azetidin-3-yl]oxy}phenyl)-1,3-dihydro-2H-pyrrolo[3,4-c]pyridine-2-carboxamide;
N-(4-{[1-(cyclohexylacetyl)azetidin-3-yl]oxy}phenyl)-1,3-dihydro-2H-pyrrolo[3,4-c]pyridine-2-carboxamide;
N-(4-{[1-(2-methylbutanoyl)azetidin-3-yl]oxy}phenyl)-1,3-dihydro-2H-pyrrolo[3,4-c]pyridine-2-carboxamide;
N-(4-{[1-(2,2-dimethylpropanoyl)azetidin-3-yl]oxy}phenyl)-1,3-dihydro-2H-pyrrolo[3,4-c]pyridine-2-carboxamide;
N-(4-{[1-(3,3-dimethylbutanoyl)azetidin-3-yl]oxy}phenyl)-1,3-dihydro-2H-pyrrolo[3,4-c]pyridine-2-carboxamide;
N-(4-{[1-(tricyclo[3.3.1.1~3,7~]dec-1-ylacetyl)azetidin-3-yl]oxy}phenyl)-1,3-dihydro-2H-pyrrolo[3,4-c]pyridine-2-carboxamide;
N-[4-({1-[(4-methoxycyclohexyl)carbonyl]azetidin-3-yl}oxy)phenyl]-1,3-dihydro-2H-pyrrolo[3,4-c]pyridine-2-carboxamide;
N-[4-({[4-(acetylamino)phenyl]sulfonyl}amino)phenyl]-1,3-dihydro-2H-pyrrolo[3,4-c]pyridine-2-carboxamide;
N-{4-[(propylsulfonyl)amino]phenyl}-1,3-dihydro-2H-pyrrolo[3,4-c]pyridine-2-carboxamide;
N-(4-{[(4-propylphenyl)sulfonyl]amino}phenyl)-1,3-dihydro-2H-pyrrolo[3,4-c]pyridine-2-carboxamide;
N-{4-[(butylsulfonyl)amino]phenyl}-1,3-dihydro-2H-pyrrolo[3,4-c]pyridine-2-carboxamide;
N-{4-[({[(1S,4R)-7,7-dimethyl-2-oxobicyclo[2.2.1]hept-1-yl]methyl}sulfonyl)amino]phenyl}-1,3-dihydro-2H-pyrrolo[3,4-c]pyridine-2-carboxamide;
N-{4-[(ethylsulfonyl)amino]phenyl}-1,3-dihydro-2H-pyrrolo[3,4-c]pyridine-2-carboxamide;
N-{4-[(benzylsulfonyl)amino]phenyl}-1,3-dihydro-2H-pyrrolo[3,4-c]pyridine-2-carboxamide;
N-(4-{[(4-fluorophenyl)sulfonyl]amino}phenyl)-1,3-dihydro-2H-pyrrolo[3,4-c]pyridine-2-carboxamide;
N-{4-[(thiophen-2-ylsulfonyl)amino]phenyl}-1,3-dihydro-2H-pyrrolo[3,4-c]pyridine-2-carboxamide;
N-[4-(1,7-diazaspiro[4.4]non-7-ylcarbonyl)phenyl]-1,3-dihydro-2H-pyrrolo[3,4-c]pyridine-2-carboxamide;
N-[4-(2,7-diazaspiro[4.5]dec-2-ylcarbonyl)phenyl]-1,3-dihydro-2H-pyrrolo[3,4-c]pyridine-2-carboxamide;
N-[4-(2,6-diazaspiro[4.5]dec-2-ylcarbonyl)phenyl]-1,3-dihydro-2H-pyrrolo[3,4-c]pyridine-2-carboxamide;
N-[4-(2,7-diazaspiro[4.5]dec-7-ylcarbonyl)phenyl]-1,3-dihydro-2H-pyrrolo[3,4-c]pyridine-2-carboxamide;
N-[4-(2,9-diazaspiro[5.5]undec-2-ylcarbonyl)phenyl]-1,3-dihydro-2H-pyrrolo[3,4-c]pyridine-2-carboxamide;
N-[4-(2,8-diazaspiro[5.5]undec-2-ylcarbonyl)phenyl]-1,3-dihydro-2H-pyrrolo[3,4-c]pyridine-2-carboxamide;
N-[4-(1,8-diazaspiro[5.5]undec-8-ylcarbonyl)phenyl]-1,3-dihydro-2H-pyrrolo[3,4-c]pyridine-2-carboxamide;
N-[4-(1,8-diazaspiro[4.6]undec-8-ylcarbonyl)phenyl]-1,3-dihydro-2H-pyrrolo[3,4-c]pyridine-2-carboxamide;

N-{4-[(1-oxa-8-azaspiro[4.5]dec-2-ylmethyl)carbamoyl]phenyl}-1,3-dihydro-2H-pyrrolo[3,4-c]pyridine-2-carboxamide;
N-[4-(1-oxa-8-azaspiro[4.5]dec-3-ylcarbamoyl)phenyl]-1,3-dihydro-2H-pyrrolo[3,4-c]pyridine-2-carboxamide;
N-{4-[(2-oxa-9-azaspiro[5.5]undec-3-ylmethyl)carbamoyl]phenyl}-1,3-dihydro-2H-pyrrolo[3,4-c]pyridine-2-carboxamide;
N-[4-(1-oxa-4,8-diazaspiro[5.5]undec-4-ylcarbonyl)phenyl]-1,3-dihydro-2H-pyrrolo[3,4-c]pyridine-2-carboxamide;
N-[4-(1,8-diazaspiro[4.5]dec-1-ylcarbonyl)phenyl]-1,3-dihydro-2H-pyrrolo[3,4-c]pyridine-2-carboxamide;
N-[4-(1,8-diazaspiro[4.5]dec-8-ylcarbonyl)phenyl]-1,3-dihydro-2H-pyrrolo[3,4-c]pyridine-2-carboxamide;
N-[4-(1,7-diazaspiro[3.5]non-7-ylcarbonyl)phenyl]-1,3-dihydro-2H-pyrrolo[3,4-c]pyridine-2-carboxamide;
N-[4-(1,6-diazaspiro[3.5]non-1-ylcarbonyl)phenyl]-1,3-dihydro-2H-pyrrolo[3,4-c]pyridine-2-carboxamide;
N-[4-(2,5-diazaspiro[3.5]non-2-ylcarbonyl)phenyl]-1,3-dihydro-2H-pyrrolo[3,4-c]pyridine-2-carboxamide;
N-[4-(5-oxa-2-azaspiro[3.4]oct-2-ylcarbonyl)phenyl]-1,3-dihydro-2H-pyrrolo[3,4-c]pyridine-2-carboxamide;
N-[4-(6-oxa-2-azaspiro[3.5]non-2-ylcarbonyl)phenyl]-1,3-dihydro-2H-pyrrolo[3,4-c]pyridine-2-carboxamide;
N-[4-(hexahydro-5H-furo[2,3-c]pyrrol-5-ylcarbonyl)phenyl]-1,3-dihydro-2H-pyrrolo[3,4-c]pyridine-2-carboxamide;
N-[4-(tetrahydro-1H-furo[3,4-c]pyrrol-5(3H)-ylcarbonyl)phenyl]-1,3-dihydro-2H-pyrrolo[3,4-c]pyridine-2-carboxamide;
N-[4-(hexahydrofuro[3,4-c]pyridin-5(3H)-ylcarbonyl)phenyl]-1,3-dihydro-2H-pyrrolo[3,4-c]pyridine-2-carboxamide;
N-{4-[1-(tetrahydrofuran-3-ylacetyl)-1,2,3,6-tetrahydropyridin-4-yl]phenyl}-1,3-dihydro-2H-pyrrolo[3,4-c]pyridine-2-carboxamide;
N-{4-[1-(tetrahydro-2H-pyran-4-ylacetyl)-1,2,3,6-tetrahydropyridin-4-yl]phenyl}-1,3-dihydro-2H-pyrrolo[3,4-c]pyridine-2-carboxamide;
N-{4-[1-(N,N-dimethylglycyl)-1,2,3,6-tetrahydropyridin-4-yl]phenyl}-1,3-dihydro-2H-pyrrolo[3,4-c]pyridine-2-carboxamide;
N-(4-{1-[(4-methylpiperazin-1-yl)acetyl]-1,2,3,6-tetrahydropyridin-4-yl}phenyl)-1,3-dihydro-2H-pyrrolo[3,4-c]pyridine-2-carboxamide;
N-(4-{4-[(tetrahydrofuran-2-ylacetyl)amino]cyclohex-1-en-1-yl}phenyl)-1,3-dihydro-2H-pyrrolo[3,4-c]pyridine-2-carboxamide;
N-(4-{4-[(tetrahydrofuran-3-ylacetyl)amino]cyclohex-1-en-1-yl}phenyl)-1,3-dihydro-2H-pyrrolo[3,4-c]pyridine-2-carboxamide;
N-(4-{4-[(cyclohexylcarbonyl)amino]cyclohex-1-en-1-yl}phenyl)-1,3-dihydro-2H-pyrrolo[3,4-c]pyridine-2-carboxamide;
N-[4-(4-{[(1,1-dioxidotetrahydrothiophen-3-yl)carbonyl]amino}cyclohex-1-en-1-yl)phenyl]-1,3-dihydro-2H-pyrrolo[3,4-c]pyridine-2-carboxamide;
N-[4-(4-{[(4,4-difluorocyclohexyl)carbonyl]amino}cyclohex-1-en-1-yl)phenyl]-1,3-dihydro-2H-pyrrolo[3,4-c]pyridine-2-carboxamide;
N-(4-{4-[(2-hydroxy-2-methylpropanoyl)amino]cyclohex-1-en-1-yl}phenyl)-1,3-dihydro-2H-pyrrolo[3,4-c]pyridine-2-carboxamide;
N-(4-{4-[(tetrahydrofuran-2-ylcarbonyl)amino]cyclohex-1-en-1-yl}phenyl)-1,3-dihydro-2H-pyrrolo[3,4-c]pyridine-2-carboxamide;
N-[4-(piperidin-1-ylsulfonyl)phenyl]-1,3-dihydro-2H-pyrrolo[3,4-c]pyridine-2-carboxamide;
5-fluoro-N-(4-{[1-(1,3-thiazol-2-yl)propan-2-yl]carbamoyl}phenyl)-1,3-dihydro-2H-isoindole-2-carboxamide;
N-{4-[(4,4-difluorocyclohexyl)carbamoyl]phenyl}-5-fluoro-1,3-dihydro-2H-isoindole-2-carboxamide;
N-(4-{[1-(3,5-dimethyl-1H-pyrazol-1-yl)propan-2-yl]carbamoyl}phenyl)-5-fluoro-1,3-dihydro-2H-isoindole-2-carboxamide;
5-fluoro-N-(4-{[2-methyl-2-(morpholin-4-yl)butyl]carbamoyl}phenyl)-1,3-dihydro-2H-isoindole-2-carboxamide;
5-fluoro-N-(4-{[2-(2-methyl-1,3-thiazol-4-yl)ethyl]carbamoyl}phenyl)-1,3-dihydro-2H-isoindole-2-carboxamide;
5-fluoro-N-(4-{[2-methyl-1-(morpholin-4-yl)propan-2-yl]carbamoyl}phenyl)-1,3-dihydro-2H-isoindole-2-carboxamide;
5-fluoro-N-{4-[(4-methoxybenzyl)carbamoyl]phenyl}-1,3-dihydro-2H-isoindole-2-carboxamide;
5-fluoro-N-(4-{[3-(morpholin-4-yl)propyl]carbamoyl}phenyl)-1,3-dihydro-2H-isoindole-2-carboxamide;
Nalpha-(4-{[(5-fluoro-1,3-dihydro-2H-isoindol-2-yl)carbonyl]amino}benzoyl)-D-phenylalaninamide;
N-(4-{[2-(acetylamino)phenyl]carbamoyl}phenyl)-5-fluoro-1,3-dihydro-2H-isoindole-2-carboxamide;
5-fluoro-N-[4-({4-[2-(2-hydroxyethoxy)ethyl]piperazin-1-yl}carbonyl)phenyl]-1,3-dihydro-2H-isoindole-2-carboxamide;
5-fluoro-N-(4-{[2-(furan-2-yl)-2-(pyrrolidin-1-yl)ethyl]carbamoyl}phenyl)-1,3-dihydro-2H-isoindole-2-carboxamide;
N-{4-[bis(2-methoxyethyl)carbamoyl]phenyl}-5-fluoro-1,3-dihydro-2H-isoindole-2-carboxamide;
N-{4-[(1-amino-1-oxohexan-2-yl)carbamoyl]phenyl}-5-fluoro-1,3-dihydro-2H-isoindole-2-carboxamide;
N-(4-{[2-(3,4-dimethoxyphenyl)ethyl]carbamoyl}phenyl)-5-fluoro-1,3-dihydro-2H-isoindole-2-carboxamide;
N-(4-{[(2S)-3,3-dimethyl-1-(methylamino)-1-oxobutan-2-yl]carbamoyl}phenyl)-5-fluoro-1,3-dihydro-2H-isoindole-2-carboxamide;
Nalpha-(4-{[(5-fluoro-1,3-dihydro-2H-isoindol-2-yl)carbonyl]amino}benzoyl)-L-phenylalaninamide;
N-(4-{[(2R)-1-amino-4-methyl-1-oxopentan-2-yl]carbamoyl}phenyl)-5-fluoro-1,3-dihydro-2H-isoindole-2-carboxamide;
N-{4-[(4-cyclohexylpiperazin-1-yl)carbonyl]phenyl}-5-fluoro-1,3-dihydro-2H-isoindole-2-carboxamide;
5-fluoro-N-(4-{[3-(methylcarbamoyl)phenyl]carbamoyl}phenyl)-1,3-dihydro-2H-isoindole-2-carboxamide;
N-{4-[(2-amino-2-oxo-1-phenylethyl)carbamoyl]phenyl}-5-fluoro-1,3-dihydro-2H-isoindole-2-carboxamide;
N-{4-[(3-tert-butoxypropyl)carbamoyl]phenyl}-5-fluoro-1,3-dihydro-2H-isoindole-2-carboxamide;
N-(4-{[2-(2,6-dimethylmorpholin-4-yl)ethyl]carbamoyl}phenyl)-5-fluoro-1,3-dihydro-2H-isoindole-2-carboxamide;
N-(4-{[(1R)-2-amino-2-oxo-1-phenylethyl]carbamoyl}phenyl)-5-fluoro-1,3-dihydro-2H-isoindole-2-carboxamide;
5-fluoro-N-{4-[(3-methoxybenzyl)carbamoyl]phenyl}-1,3-dihydro-2H-isoindole-2-carboxamide;

N-(4-{[2-(3,5-dimethyl-1H-pyrazol-1-yl)ethyl]
  carbamoyl}phenyl)-5-fluoro-1,3-dihydro-2H-isoindole-
  2-carboxamide;
5-fluoro-N-(4-{[2-methyl-2-(morpholin-4-yl)propyl]
  carbamoyl}phenyl)-1,3-dihydro-2H-isoindole-2-carboxa-
  mide;
5-fluoro-N-(4-{[(3S)-1-methyl-2-oxoazepan-3-yl]
  carbamoyl}phenyl)-1,3-dihydro-2H-isoindole-2-carboxa-
  mide;
5-fluoro-N-(4-{[2-(4-methylpiperazin-1-yl)ethyl]
  carbamoyl}phenyl)-1,3-dihydro-2H-isoindole-2-carboxa-
  mide;
5-fluoro-N-(4-{[4-(morpholin-4-yl)benzyl]
  carbamoyl}phenyl)-1,3-dihydro-2H-isoindole-2-carboxa-
  mide;
5-fluoro-N-(4-{[3-(piperidin-1-yl)propyl]
  carbamoyl}phenyl)-1,3-dihydro-2H-isoindole-2-carboxa-
  mide;
N-(4-{[3-(5-methyl-1H-pyrazol-1-yl)propyl]
  carbamoyl}phenyl)-5,7-dihydro-6H-pyrrolo[3,4-b]pyri-
  dine-6-carboxamide;
N-(4-{[2-(4-chloro-1H-pyrazol-1-yl)ethyl]
  carbamoyl}phenyl)-5,7-dihydro-6H-pyrrolo[3,4-b]pyri-
  dine-6-carboxamide;
N-(4-{[1-(3,5-dimethyl-1H-pyrazol-1-yl)propan-2-yl]
  carbamoyl}phenyl)-5,7-dihydro-6H-pyrrolo[3,4-b]pyri-
  dine-6-carboxamide;
N-(4-{[2-methyl-2-(morpholin-4-yl)butyl]
  carbamoyl}phenyl)-5,7-dihydro-6H-pyrrolo[3,4-b]pyri-
  dine-6-carboxamide;
N-{4-[(4-methoxybenzyl)carbamoyl]phenyl}-5,7-dihydro-
  6H-pyrrolo[3,4-b]pyridine-6-carboxamide;
N-(4-{[3-(morpholin-4-yl)propyl]carbamoyl}phenyl)-5,7-
  dihydro-6H-pyrrolo[3,4-b]pyridine-6-carboxamide;
N-[4-({4-[2-(2-hydroxyethoxy)ethyl]piperazin-1-
  yl}carbonyl)phenyl]-5,7-dihydro-6H-pyrrolo[3,4-b]pyri-
  dine-6-carboxamide;
N-{4-[(2-carbamoylbenzyl)carbamoyl]phenyl}-5,7-dihy-
  dro-6H-pyrrolo[3,4-b]pyridine-6-carboxamide;
N-{4-[bis(2-methoxyethyl)carbamoyl]phenyl}-5,7-dihydro-
  6H-pyrrolo[3,4-b]pyridine-6-carboxamide;
N-{4-[(1-amino-1-oxohexan-2-yl)carbamoyl]phenyl}-5,7-
  dihydro-6H-pyrrolo[3,4-b]pyridine-6-carboxamide;
N-(4-{[2-(3,4-dimethoxyphenyl)ethyl]carbamoyl}phenyl)-
  5,7-dihydro-6H-pyrrolo[3,4-b]pyridine-6-carboxamide;
N-(4-{[4-(pyrazin-2-yl)piperazin-1-yl]carbonyl}phenyl)-5,
  7-dihydro-6H-pyrrolo[3,4-b]pyridine-6-carboxamide;
Nalpha-{4-[(5,7-dihydro-6H-pyrrolo[3,4-b]pyridin-6-ylcar-
  bonyl)amino]benzoyl}-L-phenylalaninamide;
N-(4-{[(2R)-1-amino-4-methyl-1-oxopentan-2-yl]
  carbamoyl}phenyl)-5,7-dihydro-6H-pyrrolo[3,4-b]pyri-
  dine-6-carboxamide;
N-{4-[(4-cyclohexylpiperazin-1-yl)carbonyl]phenyl}-5,7-
  dihydro-6H-pyrrolo[3,4-b]pyridine-6-carboxamide;
N-{4-[(3-tert-butoxypropyl)carbamoyl]phenyl}-5,7-dihy-
  dro-6H-pyrrolo[3,4-b]pyridine-6-carboxamide;
N-(4-{[2-(2,6-dimethylmorpholin-4-yl)ethyl]
  carbamoyl}phenyl)-5,7-dihydro-6H-pyrrolo[3,4-b]pyri-
  dine-6-carboxamide;
N-{4-[(3-methoxybenzyl)carbamoyl]phenyl}-5,7-dihydro-
  6H-pyrrolo[3,4-b]pyridine-6-carboxamide;
N-(4-{[2-methyl-2-(morpholin-4-yl)propyl]
  carbamoyl}phenyl)-5,7-dihydro-6H-pyrrolo[3,4-b]pyri-
  dine-6-carboxamide;
N-(4-{[(3S)-1-methyl-2-oxoazepan-3-yl]
  carbamoyl}phenyl)-5,7-dihydro-6H-pyrrolo[3,4-b]pyri-
  dine-6-carboxamide;
N-(4-{[2-(4-methylpiperazin-1-yl)ethyl]
  carbamoyl}phenyl)-5,7-dihydro-6H-pyrrolo[3,4-b]pyri-
  dine-6-carboxamide;
N-(4-{[4-(morpholin-4-yl)benzyl]carbamoyl}phenyl)-5,7-
  dihydro-6H-pyrrolo[3,4-b]pyridine-6-carboxamide;
N-(4-{[3-(piperidin-1-yl)propyl]carbamoyl}phenyl)-5,7-di-
  hydro-6H-pyrrolo[3,4-b]pyridine-6-carboxamide;
N-[4-(4,5,6,7-tetrahydro-1H-indazol-5-ylcarbamoyl)phe-
  nyl]-5,7-dihydro-6H-pyrrolo[3,4-b]pyridine-6-carboxam-
  ide;
5-fluoro-N-{4-[(3-methoxy-2,2-dimethylpropyl)carbamoyl]
  phenyl}-1,3-dihydro-2H-isoindole-2-carboxamide;
N-{4-[(3,3-dimethylbutyl)carbamoyl]phenyl}-5-fluoro-1,3-
  dihydro-2H-isoindole-2-carboxamide;
5-fluoro-N-(4-{[1-(furan-2-yl)propan-2-yl]
  carbamoyl}phenyl)-1,3-dihydro-2H-isoindole-2-carboxa-
  mide;
5-fluoro-N-(4-{[(3-methyl-1,2-oxazol-5-yl)methyl]
  carbamoyl}phenyl)-1,3-dihydro-2H-isoindole-2-carboxa-
  mide;
N-(4-{[(2R)-1-cyanobutan-2-yl]carbamoyl}phenyl)-5-
  fluoro-1,3-dihydro-2H-isoindole-2-carboxamide;
N-{4-[(2R)-butan-2-ylcarbamoyl]phenyl}-5-fluoro-1,3-di-
  hydro-2H-isoindole-2-carboxamide;
5-fluoro-N-(4-{[2-(1H-pyrazol-1-yl)ethyl]
  carbamoyl}phenyl)-1,3-dihydro-2H-isoindole-2-carboxa-
  mide;
5-fluoro-N-{4-[methyl(3-methylbutyl)carbamoyl]phenyl}-
  1,3-dihydro-2H-isoindole-2-carboxamide;
N-(4-{[1-(ethylamino)-1-oxopropan-2-yl]
  carbamoyl}phenyl)-5-fluoro-1,3-dihydro-2H-isoindole-
  2-carboxamide;
5-fluoro-N-(4-{[(1-methyl-1H-pyrazol-3-yl)methyl]
  carbamoyl}phenyl)-1,3-dihydro-2H-isoindole-2-carboxa-
  mide;
5-fluoro-N-{4-[(2-methoxybutyl)carbamoyl]phenyl}-1,3-
  dihydro-2H-isoindole-2-carboxamide;
N-(4-{[4-(dimethylamino)butyl]carbamoyl}phenyl)-5-
  fluoro-1,3-dihydro-2H-isoindole-2-carboxamide;
5-fluoro-N-{4-[(3S)-tetrahydrofuran-3-ylcarbamoyl]phe-
  nyl}-1,3-dihydro-2H-isoindole-2-carboxamide;
5-fluoro-N-{4-[(1-methoxybutan-2-yl)carbamoyl]phenyl}-
  1,3-dihydro-2H-isoindole-2-carboxamide;
N-{4-[(2-ethoxypropyl)carbamoyl]phenyl}-5-fluoro-1,3-di-
  hydro-2H-isoindole-2-carboxamide;
N-{4-[benzyl(methyl)carbamoyl]phenyl}-5-fluoro-1,3-di-
  hydro-2H-isoindole-2-carboxamide;
N-{4-[(2S)-butan-2-ylcarbamoyl]phenyl}-5-fluoro-1,3-di-
  hydro-2H-isoindole-2-carboxamide;
5-fluoro-N-(4-{[2-(5-methyl-1H-pyrazol-1-yl)ethyl]
  carbamoyl}phenyl)-1,3-dihydro-2H-isoindole-2-carboxa-
  mide;
5-fluoro-N-(4-{[2-(3-methyl-1H-pyrazol-1-yl)ethyl]
  carbamoyl}phenyl)-1,3-dihydro-2H-isoindole-2-carboxa-
  mide;
5-fluoro-N-{4-[(2-methylpropyl)carbamoyl]phenyl}-1,3-di-
  hydro-2H-isoindole-2-carboxamide;
5-fluoro-N-{4-[(pyridin-3-ylmethyl)carbamoyl]phenyl}-1,
  3-dihydro-2H-isoindole-2-carboxamide;
5-fluoro-N-{4-[(tetrahydrofuran-2-ylmethyl)carbamoyl]
  phenyl}-1,3-dihydro-2H-isoindole-2-carboxamide;
N-(4-{[(1R)-1-cyclopropylethyl]carbamoyl}phenyl)-5-
  fluoro-1,3-dihydro-2H-isoindole-2-carboxamide;
5-fluoro-N-(4-{[1-(1-methylcyclopropyl)ethyl]
  carbamoyl}phenyl)-1,3-dihydro-2H-isoindole-2-carboxa-
  mide;

5-fluoro-N-{4-[(thiophen-2-ylmethyl)carbamoyl]phenyl}-1,3-dihydro-2H-isoindole-2-carboxamide;
N-(4-{[(1S)-1-cyclopropylethyl]carbamoyl}phenyl)-5-fluoro-1,3-dihydro-2H-isoindole-2-carboxamide;
5-fluoro-N-{4-[(4-methoxybutyl)carbamoyl]phenyl}-1,3-dihydro-2H-isoindole-2-carboxamide;
5-fluoro-N-(4-{[(5-methyl-1,3-oxazol-2-yl)methyl]carbamoyl}phenyl)-1,3-dihydro-2H-isoindole-2-carboxamide;
5-fluoro-N-(4-{[2-(tetrahydro-2H-pyran-3-yl)ethyl]carbamoyl}phenyl)-1,3-dihydro-2H-isoindole-2-carboxamide;
5-fluoro-N-(4-{[(2S)-1-methoxypropan-2-yl]carbamoyl}phenyl)-1,3-dihydro-2H-isoindole-2-carboxamide;
N-{4-[(3,3-dimethyl-2-oxobutyl)carbamoyl]phenyl}-5-fluoro-1,3-dihydro-2H-isoindole-2-carboxamide;
5-fluoro-N-(4-{[(1-methyl-1H-pyrrol-2-yl)methyl]carbamoyl}phenyl)-1,3-dihydro-2H-isoindole-2-carboxamide;
5-fluoro-N-(4-{[2-(propan-2-yloxy)ethyl]carbamoyl}phenyl)-1,3-dihydro-2H-isoindole-2-carboxamide;
N-(4-{[3-(dimethylamino)propyl]carbamoyl}phenyl)-5-fluoro-1,3-dihydro-2H-isoindole-2-carboxamide;
N-(4-{[(2S)-1-amino-1-oxobutan-2-yl]carbamoyl}phenyl)-5-fluoro-1,3-dihydro-2H-isoindole-2-carboxamide;
5-fluoro-N-[4-(tetrahydro-2H-pyran-3-ylcarbamoyl)phenyl]-1,3-dihydro-2H-isoindole-2-carboxamide;
5-fluoro-N-(4-{[2-(1H-pyrrol-1-yl)ethyl]carbamoyl}phenyl)-1,3-dihydro-2H-isoindole-2-carboxamide;
5-fluoro-N-{4-[(1-methoxypropan-2-yl)carbamoyl]phenyl}-1,3-dihydro-2H-isoindole-2-carboxamide;
5-fluoro-N-{4-[(2-methoxyethyl)carbamoyl]phenyl}-1,3-dihydro-2H-isoindole-2-carboxamide;
N-[4-(cyclopentylcarbamoyl)phenyl]-5-fluoro-1,3-dihydro-2H-isoindole-2-carboxamide;
5-fluoro-N-(4-{[(2S)-3-methylbutan-2-yl]carbamoyl}phenyl)-1,3-dihydro-2H-isoindole-2-carboxamide;
5-fluoro-N-(4-{[(2R)-3-methylbutan-2-yl]carbamoyl}phenyl)-1,3-dihydro-2H-isoindole-2-carboxamide;
5-fluoro-N-(4-{[(2S)-2-methylbutyl]carbamoyl}phenyl)-1,3-dihydro-2H-isoindole-2-carboxamide;
5-fluoro-N-{4-[(2-hydroxy-2-methylpropyl)carbamoyl]phenyl}-1,3-dihydro-2H-isoindole-2-carboxamide;
5-fluoro-N-(4-{[2-(tetrahydro-2H-pyran-4-yl)ethyl]carbamoyl}phenyl)-1,3-dihydro-2H-isoindole-2-carboxamide;
N-[4-(butylcarbamoyl)phenyl]-5-fluoro-1,3-dihydro-2H-isoindole-2-carboxamide;
5-fluoro-N-{4-[methyl(tetrahydrofuran-2-ylmethyl)carbamoyl]phenyl}-1,3-dihydro-2H-isoindole-2-carboxamide;
5-fluoro-N-{4-[(2-methoxyethyl)(methyl)carbamoyl]phenyl}-1,3-dihydro-2H-isoindole-2-carboxamide;
N-{4-[(1-cyanoethyl)carbamoyl]phenyl}-5-fluoro-1,3-dihydro-2H-isoindole-2-carboxamide;
5-fluoro-N-(4-{[(5-methyl-1,2-oxazol-3-yl)methyl]carbamoyl}phenyl)-1,3-dihydro-2H-isoindole-2-carboxamide;
5-fluoro-N-{4-[(3R)-tetrahydrofuran-3-ylcarbamoyl]phenyl}-1,3-dihydro-2H-isoindole-2-carboxamide;
N-{4-[(3-methoxy-2,2-dimethylpropyl)carbamoyl]phenyl}-5,7-dihydro-6H-pyrrolo[3,4-b]pyridine-6-carboxamide;
N-{4-[(3,3-dimethylbutyl)carbamoyl]phenyl}-5,7-dihydro-6H-pyrrolo[3,4-b]pyridine-6-carboxamide;
N-(4-{[1-(furan-2-yl)propan-2-yl]carbamoyl}phenyl)-5,7-dihydro-6H-pyrrolo[3,4-b]pyridine-6-carboxamide;
N-(4-{[(3-methyl-1,2-oxazol-5-yl)methyl]carbamoyl}phenyl)-5,7-dihydro-6H-pyrrolo[3,4-b]pyridine-6-carboxamide;
N-(4-{[(2R)-1-cyanobutan-2-yl]carbamoyl}phenyl)-5,7-dihydro-6H-pyrrolo[3,4-b]pyridine-6-carboxamide;
N-{4-[methyl(3-methylbutyl)carbamoyl]phenyl}-5,7-dihydro-6H-pyrrolo[3,4-b]pyridine-6-carboxamide;
N-(4-{[(1-methyl-1H-pyrazol-3-yl)methyl]carbamoyl}phenyl)-5,7-dihydro-6H-pyrrolo[3,4-b]pyridine-6-carboxamide;
N-{4-[(2-methoxybutyl)carbamoyl]phenyl}-5,7-dihydro-6H-pyrrolo[3,4-b]pyridine-6-carboxamide;
N-(4-{[4-(dimethylamino)butyl]carbamoyl}phenyl)-5,7-dihydro-6H-pyrrolo[3,4-b]pyridine-6-carboxamide;
N-(4-{[1-(1,3-thiazol-2-yl)ethyl]carbamoyl}phenyl)-5,7-dihydro-6H-pyrrolo[3,4-b]pyridine-6-carboxamide;
N-(4-{[1-(1-methyl-1H-pyrazol-4-yl)ethyl]carbamoyl}phenyl)-5,7-dihydro-6H-pyrrolo[3,4-b]pyridine-6-carboxamide;
N-{4-[(3S)-tetrahydrofuran-3-ylcarbamoyl]phenyl}-5,7-dihydro-6H-pyrrolo[3,4-b]pyridine-6-carboxamide;
N-{4-[(1-methoxybutan-2-yl)carbamoyl]phenyl}-5,7-dihydro-6H-pyrrolo[3,4-b]pyridine-6-carboxamide;
N-{4-[(4-aminobenzyl)carbamoyl]phenyl}-5,7-dihydro-6H-pyrrolo[3,4-b]pyridine-6-carboxamide;
N-{4-[(2-ethoxypropyl)carbamoyl]phenyl}-5,7-dihydro-6H-pyrrolo[3,4-b]pyridine-6-carboxamide;
N-{4-[(6-methoxypyridin-3-yl)carbamoyl]phenyl}-5,7-dihydro-6H-pyrrolo[3,4-b]pyridine-6-carboxamide;
N-{4-[(2S)-butan-2-ylcarbamoyl]phenyl}-5,7-dihydro-6H-pyrrolo[3,4-b]pyridine-6-carboxamide;
N-{4-[(1-cyanocyclopropyl)carbamoyl]phenyl}-5,7-dihydro-6H-pyrrolo[3,4-b]pyridine-6-carboxamide;
N-(4-{[2-(5-methyl-1H-pyrazol-1-yl)ethyl]carbamoyl}phenyl)-5,7-dihydro-6H-pyrrolo[3,4-b]pyridine-6-carboxamide;
N-(4-{[(4-methyl-1,3-thiazol-2-yl)methyl]carbamoyl}phenyl)-5,7-dihydro-6H-pyrrolo[3,4-b]pyridine-6-carboxamide;
N-{4-[(3-hydroxypropyl)carbamoyl]phenyl}-5,7-dihydro-6H-pyrrolo[3,4-b]pyridine-6-carboxamide;
N-{4-[(2-methylpropyl)carbamoyl]phenyl}-5,7-dihydro-6H-pyrrolo[3,4-b]pyridine-6-carboxamide;
N-{4-[(tetrahydrofuran-2-ylmethyl)carbamoyl]phenyl}-5,7-dihydro-6H-pyrrolo[3,4-b]pyridine-6-carboxamide;
N-(4-{[(1R)-1-cyclopropylethyl]carbamoyl}phenyl)-5,7-dihydro-6H-pyrrolo[3,4-b]pyridine-6-carboxamide;
N-(4-{[1-(1-methylcyclopropyl)ethyl]carbamoyl}phenyl)-5,7-dihydro-6H-pyrrolo[3,4-b]pyridine-6-carboxamide;
N-{4-[(thiophen-2-ylmethyl)carbamoyl]phenyl}-5,7-dihydro-6H-pyrrolo[3,4-b]pyridine-6-carboxamide;
N-(4-{[(1S)-1-cyclopropylethyl]carbamoyl}phenyl)-5,7-dihydro-6H-pyrrolo[3,4-b]pyridine-6-carboxamide;
N-{4-[(4-methoxybutyl)carbamoyl]phenyl}-5,7-dihydro-6H-pyrrolo[3,4-b]pyridine-6-carboxamide;
N-(4-{[2-(tetrahydro-2H-pyran-3-yl)ethyl]carbamoyl}phenyl)-5,7-dihydro-6H-pyrrolo[3,4-b]pyridine-6-carboxamide;
N-(4-{[(2S)-1-methoxypropan-2-yl]carbamoyl}phenyl)-5,7-dihydro-6H-pyrrolo[3,4-b]pyridine-6-carboxamide;
N-{4-[(3,3-dimethyl-2-oxobutyl)carbamoyl]phenyl}-5,7-dihydro-6H-pyrrolo[3,4-b]pyridine-6-carboxamide;

N-(4-{[(1-methyl-1H-pyrrol-2-yl)methyl]carbamoyl}phenyl)-5,7-dihydro-6H-pyrrolo[3,4-b]pyridine-6-carboxamide;
N-(4-{[2-(propan-2-yloxy)ethyl]carbamoyl}phenyl)-5,7-dihydro-6H-pyrrolo[3,4-b]pyridine-6-carboxamide;
N-(4-{[3-(dimethylamino)propyl]carbamoyl}phenyl)-5,7-dihydro-6H-pyrrolo[3,4-b]pyridine-6-carboxamide;
N-[4-(tetrahydro-2H-pyran-3-ylcarbamoyl)phenyl]-5,7-dihydro-6H-pyrrolo[3,4-b]pyridine-6-carboxamide;
N-(4-{[2-(1H-pyrrol-1-yl)ethyl]carbamoyl}phenyl)-5,7-dihydro-6H-pyrrolo[3,4-b]pyridine-6-carboxamide;
N-{4-[(1-methoxypropan-2-yl)carbamoyl]phenyl}-5,7-dihydro-6H-pyrrolo[3,4-b]pyridine-6-carboxamide;
N-{4-[(3-aminobenzyl)carbamoyl]phenyl}-5,7-dihydro-6H-pyrrolo[3,4-b]pyridine-6-carboxamide;
N-(4-{[(2R)-3-methylbutan-2-yl]carbamoyl}phenyl)-5,7-dihydro-6H-pyrrolo[3,4-b]pyridine-6-carboxamide;
N-{4-[(tetrahydro-2H-pyran-3-ylmethyl)carbamoyl]phenyl}-5,7-dihydro-6H-pyrrolo[3,4-b]pyridine-6-carboxamide;
N-{4-[(2-hydroxy-2-methylpropyl)carbamoyl]phenyl}-5,7-dihydro-6H-pyrrolo[3,4-b]pyridine-6-carboxamide;
N-[4-(butylcarbamoyl)phenyl]-5,7-dihydro-6H-pyrrolo[3,4-b]pyridine-6-carboxamide;
N-{4-[methyl(tetrahydrofuran-2-ylmethyl)carbamoyl]phenyl}-5,7-dihydro-6H-pyrrolo[3,4-b]pyridine-6-carboxamide;
N-{4-[(2-methoxyethyl)(methyl)carbamoyl]phenyl}-5,7-dihydro-6H-pyrrolo[3,4-b]pyridine-6-carboxamide;
N-{4-[(1-cyanoethyl)carbamoyl]phenyl}-5,7-dihydro-6H-pyrrolo[3,4-b]pyridine-6-carboxamide;
N-{4-[(3R)-tetrahydrofuran-3-ylcarbamoyl]phenyl}-5,7-dihydro-6H-pyrrolo[3,4-b]pyridine-6-carboxamide;
N-{4-[(cyclopentylmethyl)carbamoyl]phenyl}-5,7-dihydro-6H-pyrrolo[3,4-b]pyridine-6-carboxamide;
N-{4-[(2-methoxy-2-methylpropyl)carbamoyl]phenyl}-5,7-dihydro-6H-pyrrolo[3,4-b]pyridine-6-carboxamide;
N-{4-[(cyclopropylmethyl)carbamoyl]phenyl}-5,7-dihydro-6H-pyrrolo[3,4-b]pyridine-6-carboxamide;
N-{4-[methyl(propyl)carbamoyl]phenyl}-5,7-dihydro-6H-pyrrolo[3,4-b]pyridine-6-carboxamide;
N-{4-[(pyridin-4-ylmethyl)carbamoyl]phenyl}-5,7-dihydro-6H-pyrrolo[3,4-b]pyridine-6-carboxamide;
methyl 1-{4-[(1,3-dihydro-2H-pyrrolo[3,4-c]pyridin-2-ylcarbonyl)amino]phenyl}azetidine-3-carboxylate;
N-(4-{3-[(3-methylbutyl)carbamoyl]azetidin-1-yl}phenyl)-1,3-dihydro-2H-pyrrolo[3,4-c]pyridine-2-carboxamide;
N-(4-{3-[(tetrahydro furan-2-ylmethyl)carbamoyl]azetidin-1-yl}phenyl)-1,3-dihydro-2H-pyrrolo[3,4-c]pyridine-2-carboxamide;
N-(4-{3-[(tetrahydro-2H-pyran-4-ylmethyl)carbamoyl]azetidin-1-yl}phenyl)-1,3-dihydro-2H-pyrrolo[3,4-c]pyridine-2-carboxamide;
N-{4-[3-(benzylcarbamoyl)azetidin-1-yl]phenyl}-1,3-dihydro-2H-pyrrolo[3,4-c]pyridine-2-carboxamide;
N-{4-[3-(cyclopentylcarbamoyl)azetidin-1-yl]phenyl}-1,3-dihydro-2H-pyrrolo[3,4-c]pyridine-2-carboxamide;
N-(4-{3-[(cyclopentylmethyl)carbamoyl]azetidin-1-yl}phenyl)-1,3-dihydro-2H-pyrrolo[3,4-c]pyridine-2-carboxamide;
N-(4-{3-[(2-methoxyethyl)carbamoyl]azetidin-1-yl}phenyl)-1,3-dihydro-2H-pyrrolo[3,4-c]pyridine-2-carboxamide;
N-{4-[1-(3-methylbutanoyl)-1,2,3,6-tetrahydropyridin-4-yl]phenyl}-1,3-dihydro-2H-pyrrolo[3,4-c]pyridine-2-carboxamide;
N-{4-[1-(cyclopentylacetyl)-1,2,3,6-tetrahydropyridin-4-yl]phenyl}-1,3-dihydro-2H-pyrrolo[3,4-c]pyridine-2-carboxamide;
N-{4-[1-(tetrahydro furan-2-ylacetyl)-1,2,3,6-tetrahydropyridin-4-yl]phenyl}-1,3-dihydro-2H-pyrrolo[3,4-c]pyridine-2-carboxamide;
N-{4-[1-(tetrahydro-2H-pyran-2-ylacetyl)-1,2,3,6-tetrahydropyridin-4-yl]phenyl}-1,3-dihydro-2H-pyrrolo[3,4-c]pyridine-2-carboxamide;
N-{4-[1-(pyrrolidin-1-ylacetyl)-1,2,3,6-tetrahydropyridin-4-yl]phenyl}-1,3-dihydro-2H-pyrrolo[3,4-c]pyridine-2-carboxamide;
N-{4-[1-(pyrazin-2-ylcarbonyl)-1,2,3,6-tetrahydropyridin-4-yl]phenyl}-1,3-dihydro-2H-pyrrolo[3,4-c]pyridine-2-carboxamide;
N-{4-[(3-methoxy-2,2-dimethylpropyl)carbamoyl]phenyl}-1,3-dihydro-2H-isoindole-2-carboxamide;
N-{4-[(4,4-difluorocyclohexyl)carbamoyl]phenyl}-1,3-dihydro-2H-isoindole-2-carboxamide;
N-(4-{[(2R)-1-cyanobutan-2-yl]carbamoyl}phenyl)-1,3-dihydro-2H-isoindole-2-carboxamide;
N-{4-[(2-methoxybutyl)carbamoyl]phenyl}-1,3-dihydro-2H-isoindole-2-carboxamide;
N-(4-{[1-(ethylamino)-1-oxopropan-2-yl]carbamoyl}phenyl)-1,3-dihydro-2H-isoindole-2-carboxamide;
N-(4-{[2-methyl-2-(morpholin-4-yl)butyl]carbamoyl}phenyl)-1,3-dihydro-2H-isoindole-2-carboxamide;
N-(4-{[(1R)-1-cyclopropylethyl]carbamoyl}phenyl)-1,3-dihydro-2H-isoindole-2-carboxamide;
N-(4-{[(1S)-1-cyclopropylethyl]carbamoyl}phenyl)-1,3-dihydro-2H-isoindole-2-carboxamide;
N-(6-{[(2S)-tetrahydrofuran-2-ylmethyl]carbamoyl}pyridazin-3-yl)-1,3-dihydro-2H-isoindole-2-carboxamide;
N-{4-[(3S)-tetrahydrofuran-3-ylcarbamoyl]phenyl}-1,3-dihydro-2H-isoindole-2-carboxamide;
N-(4-{[2-(tetrahydro-2H-pyran-3-yl)ethyl]carbamoyl}phenyl)-1,3-dihydro-2H-isoindole-2-carboxamide;
N-(4-{[(5-methyl-1,3-oxazol-2-yl)methyl]carbamoyl}phenyl)-1,3-dihydro-2H-isoindole-2-carboxamide;
N-[4-({2-[(dimethylamino)methyl]benzyl}carbamoyl)phenyl]-1,3-dihydro-2H-isoindole-2-carboxamide;
N-(4-{[(1R)-2-amino-2-oxo-1-phenylethyl]carbamoyl}phenyl)-1,3-dihydro-2H-isoindole-2-carboxamide;
N-[4-(1,3-oxazol-2-ylcarbamoyl)phenyl]-1,3-dihydro-2H-isoindole-2-carboxamide;
N-[4-(tetrahydro-2H-pyran-3-ylcarbamoyl)phenyl]-1,3-dihydro-2H-isoindole-2-carboxamide;
N-(4-{[2-(2,6-dimethylmorpholin-4-yl)ethyl]carbamoyl}phenyl)-1,3-dihydro-2H-isoindole-2-carboxamide;
N-(4-{[1-(1-methylcyclopropyl)ethyl]carbamoyl}phenyl)-1,3-dihydro-2H-isoindole-2-carboxamide;
N-(4-{[2-(furan-2-yl)-2-(pyrrolidin-1-yl)ethyl]carbamoyl}phenyl)-1,3-dihydro-2H-isoindole-2-carboxamide;
N-(4-{1-[(2S)-tetrahydrofuran-2-ylcarbonyl]piperidin-4-yl}phenyl)-1,3-dihydro-2H-pyrrolo[3,4-c]pyridine-2-carboxamide;
N-(4-{1-[(3S)-tetrahydrofuran-3-ylcarbonyl]piperidin-4-yl}phenyl)-1,3-dihydro-2H-pyrrolo[3,4-c]pyridine-2-carboxamide;

5-cyano-N-{4-[1-(tetrahydrofuran-3-ylcarbonyl)-1,2,3,6-tetrahydropyridin-4-yl]phenyl}-1,3-dihydro-2H-isoindole-2-carboxamide;

5-cyano-N-{4-[1-(tetrahydro-2H-pyran-4-ylcarbonyl)-1,2,3,6-tetrahydropyridin-4-yl]phenyl}-1,3-dihydro-2H-isoindole-2-carboxamide;

5-cyano-N-{4-[1-(2-hydroxy-2-methylpropanoyl)-1,2,3,6-tetrahydropyridin-4-yl]phenyl}-1,3-dihydro-2H-isoindole-2-carboxamide;

5-cyano-N-{4-[1-(morpholin-4-ylacetyl)-1,2,3,6-tetrahydropyridin-4-yl]phenyl}-1,3-dihydro-2H-isoindole-2-carboxamide;

N-(4-{[1-(tetrahydro-2H-pyran-2-ylcarbonyl)azetidin-3-yl]oxy}phenyl)-1,3-dihydro-2H-pyrrolo[3,4-c]pyridine-2-carboxamide;

N-(4-{[1-(tetrahydro-2H-pyran-2-ylcarbonyl)pyrrolidin-3-yl]oxy}phenyl)-1,3-dihydro-2H-pyrrolo[3,4-c]pyridine-2-carboxamide;

N-(6-{[(2R)-tetrahydrofuran-2-ylmethyl]carbamoyl}pyridazin-3-yl)-1,3-dihydro-2H-isoindole-2-carboxamide;

N-(4-{4-[(cyclopropylacetyl)amino]cyclohex-1-en-1-yl}phenyl)-1,3-dihydro-2H-pyrrolo[3,4-c]pyridine-2-carboxamide;

N-{4-[(1-acetylpiperidin-3-yl)oxy]phenyl}-1,3-dihydro-2H-pyrrolo[3,4-c]pyridine-2-carboxamide;

N-{4-[(1-butanoylpiperidin-3-yl)oxy]phenyl}-1,3-dihydro-2H-pyrrolo[3,4-c]pyridine-2-carboxamide;

N-(4-{[1-(3-methylbutanoyl)piperidin-3-yl]oxy}phenyl)-1,3-dihydro-2H-pyrrolo[3,4-c]pyridine-2-carboxamide;

N-(4-{[1-(methoxyacetyl)piperidin-3-yl]oxy}phenyl)-1,3-dihydro-2H-pyrrolo[3,4-c]pyridine-2-carboxamide;

N-(4-{[1-(2-methylbutanoyl)piperidin-3-yl]oxy}phenyl)-1,3-dihydro-2H-pyrrolo[3,4-c]pyridine-2-carboxamide;

N-(4-{[1-(3,3,3-trifluoropropanoyl)piperidin-3-yl]oxy}phenyl)-1,3-dihydro-2H-pyrrolo[3,4-c]pyridine-2-carboxamide;

N-(4-{[1-(cyclopropylacetyl)piperidin-3-yl]oxy}phenyl)-1,3-dihydro-2H-pyrrolo[3,4-c]pyridine-2-carboxamide;

N-(4-{[1-(cyclobutylcarbonyl)piperidin-3-yl]oxy}phenyl)-1,3-dihydro-2H-pyrrolo[3,4-c]pyridine-2-carboxamide;

N-(4-{[1-(cyclobutylacetyl)piperidin-3-yl]oxy}phenyl)-1,3-dihydro-2H-pyrrolo[3,4-c]pyridine-2-carboxamide;

N-(4-{[1-(cyclopentylcarbonyl)piperidin-3-yl]oxy}phenyl)-1,3-dihydro-2H-pyrrolo[3,4-c]pyridine-2-carboxamide;

N-(4-{[1-(cyclopentylacetyl)piperidin-3-yl]oxy}phenyl)-1,3-dihydro-2H-pyrrolo[3,4-c]pyridine-2-carboxamide;

N-[4-({1-[(2S)-tetrahydrofuran-2-ylcarbonyl]piperidin-3-yl}oxy)phenyl]-1,3-dihydro-2H-pyrrolo[3,4-c]pyridine-2-carboxamide;

N-[4-({1-[(2R)-tetrahydrofuran-2-ylcarbonyl]piperidin-3-yl}oxy)phenyl]-1,3-dihydro-2H-pyrrolo[3,4-c]pyridine-2-carboxamide;

N-(4-{[1-(tetrahydro-2H-pyran-4-ylcarbonyl)piperidin-3-yl]oxy}phenyl)-1,3-dihydro-2H-pyrrolo[3,4-c]pyridine-2-carboxamide;

N-(4-{[1-(tetrahydro-2H-pyran-2-ylcarbonyl)piperidin-3-yl]oxy}phenyl)-1,3-dihydro-2H-pyrrolo[3,4-c]pyridine-2-carboxamide;

N-(4-{[1-(tetrahydro-2H-pyran-4-ylacetyl)piperidin-3-yl]oxy}phenyl)-1,3-dihydro-2H-pyrrolo[3,4-c]pyridine-2-carboxamide;

N-(4-{[1-(tetrahydrofuran-2-ylacetyl)piperidin-3-yl]oxy}phenyl)-1,3-dihydro-2H-pyrrolo[3,4-c]pyridine-2-carboxamide;

N-(4-{[1-(tetrahydrofuran-3-ylacetyl)piperidin-3-yl]oxy}phenyl)-1,3-dihydro-2H-pyrrolo[3,4-c]pyridine-2-carboxamide;

N-(4-{[3-(3,5-dimethyl-1H-pyrazol-1-yl)propyl]carbamoyl}phenyl)-1,3-dihydro-2H-isoindole-2-carboxamide;

N-(4-{[(3S)-1-methyl-2-oxoazepan-3-yl]carbamoyl}phenyl)-1,3-dihydro-2H-isoindole-2-carboxamide;

N-(4-{[2-(1H-pyrazol-1-yl)ethyl]carbamoyl}phenyl)-1,3-dihydro-2H-isoindole-2-carboxamide;

N-(4-{[1-(1,3-thiazol-2-yl)ethyl]carbamoyl}phenyl)-1,3-dihydro-2H-isoindole-2-carboxamide;

N-(4-{[1-(furan-2-yl)propan-2-yl]carbamoyl}phenyl)-1,3-dihydro-2H-isoindole-2-carboxamide;

N-(4-{[1-(1-methyl-1H-pyrazol-4-yl)ethyl]carbamoyl}phenyl)-1,3-dihydro-2H-isoindole-2-carboxamide;

N-(4-{[(2R)-1-amino-4-methyl-1-oxopentan-2-yl]carbamoyl}phenyl)-1,3-dihydro-2H-isoindole-2-carboxamide;

N-(4-{[1-(3,5-dimethyl-1H-pyrazol-1-yl)propan-2-yl]carbamoyl}phenyl)-1,3-dihydro-2H-isoindole-2-carboxamide;

N-{4-[(2,2-difluoroethyl)carbamoyl]phenyl}-1,3-dihydro-2H-isoindole-2-carboxamide;

N-(4-{[2-(tetrahydro-2H-pyran-4-yl)ethyl]carbamoyl}phenyl)-1,3-dihydro-2H-isoindole-2-carboxamide;

N-{4-[(tetrahydrofuran-2-ylmethyl)carbamoyl]phenyl}-1,3-dihydro-2H-isoindole-2-carboxamide;

N-{4-[(2-methoxy-2-methylpropyl)carbamoyl]phenyl}-1,3-dihydro-2H-isoindole-2-carboxamide;

N-(4-{[(5-methyl-1,2-oxazol-3-yl)methyl]carbamoyl}phenyl)-1,3-dihydro-2H-isoindole-2-carboxamide;

N-(4-{[(1-methyl-1H-pyrazol-4-yl)methyl]carbamoyl}phenyl)-1,3-dihydro-2H-isoindole-2-carboxamide;

N-(4-{[2-(3,5-dimethyl-1H-pyrazol-1-yl)ethyl]carbamoyl}phenyl)-1,3-dihydro-2H-isoindole-2-carboxamide;

Nalpha-{4-[(1,3-dihydro-2H-isoindol-2-ylcarbonyl)amino]benzoyl}-L-phenylalaninamide;

N-(4-{[2-(2-methyl-1,3-thiazol-4-yl)ethyl]carbamoyl}phenyl)-1,3-dihydro-2H-isoindole-2-carboxamide;

N-(4-{[(2S)-3,3-dimethyl-1-(methylamino)-1-oxobutan-2-yl]carbamoyl}phenyl)-1,3-dihydro-2H-isoindole-2-carboxamide;

N-[4-(thiophen-3-ylcarbamoyl)phenyl]-1,3-dihydro-2H-isoindole-2-carboxamide;

N-(4-{[2-(5-methyl-1H-pyrazol-1-yl)ethyl]carbamoyl}phenyl)-1,3-dihydro-2H-isoindole-2-carboxamide;

N-(4-{[2-(3-methyl-1H-pyrazol-1-yl)ethyl]carbamoyl}phenyl)-1,3-dihydro-2H-isoindole-2-carboxamide;

N-{4-[(2S)-butan-2-ylcarbamoyl]phenyl}-1,3-dihydro-2H-isoindole-2-carboxamide;

N-{4-[(3,3-dimethyl-2-oxobutyl)carbamoyl]phenyl}-1,3-dihydro-2H-isoindole-2-carboxamide;

N-(4-{[(1-methyl-1H-pyrazol-3-yl)methyl]carbamoyl}phenyl)-1,3-dihydro-2H-isoindole-2-carboxamide;

N-(4-{[2-(acetylamino)phenyl]carbamoyl}phenyl)-1,3-dihydro-2H-isoindole-2-carboxamide;

N-{4-[(1-methoxybutan-2-yl)carbamoyl]phenyl}-1,3-dihydro-2H-isoindole-2-carboxamide;
N-[4-(tetrahydro-2H-pyran-4-ylcarbamoyl)phenyl]-1,3-dihydro-2H-isoindole-2-carboxamide;
N-(4-(pyrimidin-4-ylcarbamoyl)phenyl]-1,3-dihydro-2H-isoindole-2-carboxamide;
N-(4-{[2-(1H-pyrrol-1-yl)ethyl]carbamoyl}phenyl)-1,3-dihydro-2H-isoindole-2-carboxamide;
N-(4-{[(2S)-2-methylbutyl]carbamoyl}phenyl)-1,3-dihydro-2H-isoindole-2-carboxamide;
N-{4-[(1-amino-1-oxohexan-2-yl)carbamoyl]phenyl}-1,3-dihydro-2H-isoindole-2-carboxamide;
N-{4-[(2-amino-2-oxo-1-phenylethyl)carbamoyl]phenyl}-1,3-dihydro-2H-isoindole-2-carboxamide;
N-{4-[(3-tert-butoxypropyl)carbamoyl]phenyl}-1,3-dihydro-2H-isoindole-2-carboxamide;
N-(4-{[3-(methylcarbamoyl)phenyl]carbamoyl}phenyl)-1,3-dihydro-2H-isoindole-2-carboxamide;
N-(4-{[(2R)-3-methylbutan-2-yl]carbamoyl}phenyl)-1,3-dihydro-2H-isoindole-2-carboxamide;
N-(4-{[(2S)-3-methylbutan-2-yl]carbamoyl}phenyl)-1,3-dihydro-2H-isoindole-2-carboxamide;
N-(4-{[2-methyl-1-(morpholin-4-yl)propan-2-yl]carbamoyl}phenyl)-1,3-dihydro-2H-isoindole-2-carboxamide;
N-(4-{[1-(5-oxo-L-prolyl)piperidin-4-yl]oxy}phenyl)-1,3-dihydro-2H-pyrrolo[3,4-c]pyridine-2-carboxamide;
N-(4-{[2-methyl-2-(morpholin-4-yl)propyl]carbamoyl}phenyl)-1,3-dihydro-2H-isoindole-2-carboxamide;
N-{4-[(2-ethoxypropyl)carbamoyl]phenyl}-1,3-dihydro-2H-isoindole-2-carboxamide;
N-{4-[(3-ethoxypropanoyl)amino]phenyl}-1,3-dihydro-2H-pyrrolo[3,4-c]pyridine-2-carboxamide;
N-(4-{[(1-acetylpiperidin-4-yl)carbonyl]amino}phenyl)-1,3-dihydro-2H-pyrrolo[3,4-c]pyridine-2-carboxamide;
N-{4-[(ethoxyacetyl)amino]phenyl}-1,3-dihydro-2H-pyrrolo[3,4-c]pyridine-2-carboxamide;
N-{4-[(tetrahydrofuran-2-ylcarbonyl)amino]phenyl}-1,3-dihydro-2H-pyrrolo[3,4-c]pyridine-2-carboxamide;
N-{4-[(tetrahydrofuran-3-ylcarbonyl)amino]phenyl}-1,3-dihydro-2H-pyrrolo[3,4-c]pyridine-2-carboxamide;
N-{4-[(cyclopentylcarbonyl)amino]phenyl}-1,3-dihydro-2H-pyrrolo[3,4-c]pyridine-2-carboxamide;
N-{4-[(bicyclo[2.2.1]hept-2-ylacetyl)amino]phenyl}-1,3-dihydro-2H-pyrrolo[3,4-c]pyridine-2-carboxamide;
N-{4-[(1,3-thiazol-5-ylcarbonyl)amino]phenyl}-1,3-dihydro-2H-pyrrolo[3,4-c]pyridine-2-carboxamide;
N-(4-{[(4-oxo-4,5,6,7-tetrahydro-1-benzo furan-3-yl)carbonyl]amino}phenyl)-1,3-dihydro-2H-pyrrolo[3,4-c]pyridine-2-carboxamide;
N-(4-{2-[(3-methylbutanoyl)amino]ethyl}phenyl)-1,3-dihydro-2H-isoindole-2-carboxamide;
N-(4-{2-[(4-methylpentanoyl)amino]ethyl}phenyl)-1,3-dihydro-2H-isoindole-2-carboxamide;
N-(4-{2-[(ethoxyacetyl)amino]ethyl}phenyl)-1,3-dihydro-2H-isoindole-2-carboxamide;
N-(4-(2-{[(2-methoxyethoxy)acetyl]amino}ethyl)phenyl]-1,3-dihydro-2H-isoindole-2-carboxamide;
N-(4-{2-[(tetrahydro furan-2-ylcarbonyl)amino]ethyl}phenyl)-1,3-dihydro-2H-isoindole-2-carboxamide;
N-(4-{2-[(cyclopentylcarbonyl)amino]ethyl}phenyl)-1,3-dihydro-2H-isoindole-2-carboxamide;
N-(4-{2-[(cyclopentylacetyl)amino]ethyl}phenyl)-1,3-dihydro-2H-isoindole-2-carboxamide;
N-{4-[2-(benzoylamino)ethyl]phenyl}-1,3-dihydro-2H-isoindole-2-carboxamide;
N-(4-{2-[(tetrahydro-2H-pyran-4-ylcarbonyl)amino]ethyl}phenyl)-1,3-dihydro-2H-isoindole-2-carboxamide;
N-(4-{2-[(tetrahydro-2H-pyran-4-ylacetyl)amino]ethyl}phenyl)-1,3-dihydro-2H-isoindole-2-carboxamide;
N-(4-{2-[(tetrahydrofuran-3-ylacetyl)amino]ethyl}phenyl)-1,3-dihydro-2H-isoindole-2-carboxamide;
N-(4-{1-[(2R)-tetrahydrofuran-2-ylcarbonyl]piperidin-4-yl}phenyl)-1,3-dihydro-2H-pyrrolo[3,4-c]pyridine-2-carboxamide;
N-(4-{1-[(3R)-tetrahydrofuran-3-ylcarbonyl]piperidin-4-yl}phenyl)-1,3-dihydro-2H-pyrrolo[3,4-c]pyridine-2-carboxamide;
N-(4-{[1-(5-oxo-L-prolyl)azetidin-3-yl]oxy}phenyl)-1,3-dihydro-2H-pyrrolo[3,4-c]pyridine-2-carboxamide;
N-{4-[(1-propanoylazetidin-3-yl)oxy]phenyl}-1,3-dihydro-2H-pyrrolo[3,4-c]pyridine-2-carboxamide;
N-(4-{[1-(2,2-dimethylbutanoyl)azetidin-3-yl]oxy}phenyl)-1,3-dihydro-2H-pyrrolo[3,4-c]pyridine-2-carboxamide;
N-(4-{[1-(2-ethylbutanoyl)azetidin-3-yl]oxy}phenyl)-1,3-dihydro-2H-pyrrolo[3,4-c]pyridine-2-carboxamide;
N-(4-{[1-(pent-4-ynoyl)azetidin-3-yl]oxy}phenyl)-1,3-dihydro-2H-pyrrolo[3,4-c]pyridine-2-carboxamide;
N-(4-{[1-(furan-2-ylcarbonyl)azetidin-3-yl]oxy}phenyl)-1,3-dihydro-2H-pyrrolo[3,4-c]pyridine-2-carboxamide;
N-(4-{[1-(furan-3-ylcarbonyl)azetidin-3-yl]oxy}phenyl)-1,3-dihydro-2H-pyrrolo[3,4-c]pyridine-2-carboxamide;
N-(4-{[1-(thiophen-3-ylcarbonyl)azetidin-3-yl]oxy}phenyl)-1,3-dihydro-2H-pyrrolo[3,4-c]pyridine-2-carboxamide;
N-(4-{[1-(1H-pyrrol-2-ylcarbonyl)azetidin-3-yl]oxy}phenyl)-1,3-dihydro-2H-pyrrolo[3,4-c]pyridine-2-carboxamide;
N-(4-{[1-(pyrimidin-4-ylcarbonyl)azetidin-3-yl]oxy}phenyl)-1,3-dihydro-2H-pyrrolo[3,4-c]pyridine-2-carboxamide;
N-[4-({1-[(5-methylpyrazin-2-yl)carbonyl]azetidin-3-yl}oxy)phenyl]-1,3-dihydro-2H-pyrrolo[3,4-c]pyridine-2-carboxamide;
N-(4-{[1-(N,N-dimethylglycyl)azetidin-3-yl]oxy}phenyl)-1,3-dihydro-2H-pyrrolo[3,4-c]pyridine-2-carboxamide;
N-(4-{[1-(N,N-dimethyl-beta-alanyl)azetidin-3-yl]oxy}phenyl)-1,3-dihydro-2H-pyrrolo[3,4-c]pyridine-2-carboxamide;
N-(4-{[1-(pyrrolidin-1-ylacetyl)azetidin-3-yl]oxy}phenyl)-1,3-dihydro-2H-pyrrolo[3,4-c]pyridine-2-carboxamide;
N-[4-({1-[3-(pyrrolidin-1-yl)propanoyl]azetidin-3-yl}oxy)phenyl]-1,3-dihydro-2H-pyrrolo[3,4-c]pyridine-2-carboxamide;
N-[4-({1-[3-(piperidin-1-yl)propanoyl]azetidin-3-yl}oxy)phenyl]-1,3-dihydro-2H-pyrrolo[3,4-c]pyridine-2-carboxamide;
N-[4-({1-[(4-methylpiperazin-1-yl)acetyl]azetidin-3-yl}oxy)phenyl]-1,3-dihydro-2H-pyrrolo[3,4-c]pyridine-2-carboxamide;
N-[4-({1-[3-(4-methylpiperazin-1-yl)propanoyl]azetidin-3-yl}oxy)phenyl]-1,3-dihydro-2H-pyrrolo[3,4-c]pyridine-2-carboxamide;
N-(4-{[1-(2-cyclopropylethyl)piperidin-4-yl]oxy}phenyl)-1,3-dihydro-2H-pyrrolo[3,4-c]pyridine-2-carboxamide;
N-(4-{[1-(2-cyclopentylethyl)piperidin-4-yl]oxy}phenyl)-1,3-dihydro-2H-pyrrolo[3,4-c]pyridine-2-carboxamide;
N-(4-{[1-(2-methylbutyl)piperidin-4-yl]oxy}phenyl)-1,3-dihydro-2H-pyrrolo[3,4-c]pyridine-2-carboxamide;
N-(4-{[1-(tetrahydrofuran-3-ylmethyl)piperidin-4-yl]oxy}phenyl)-1,3-dihydro-2H-pyrrolo[3,4-c]pyridine-2-carboxamide;

N-(4-{[1-(3,3-dimethylbutyl)piperidin-4-yl]oxy}phenyl)-1,3-dihydro-2H-pyrrolo[3,4-c]pyridine-2-carboxamide;
N-(4-{[1-(cyclohexylmethyl)piperidin-4-yl]oxy}phenyl)-1,3-dihydro-2H-pyrrolo[3,4-c]pyridine-2-carboxamide;
N-(4-{[1-(3-methylbutyl)piperidin-4-yl]oxy}phenyl)-1,3-dihydro-2H-pyrrolo[3,4-c]pyridine-2-carboxamide;
N-(4-{[1-(cyclopentylmethyl)piperidin-4-yl]oxy}phenyl)-1,3-dihydro-2H-pyrrolo[3,4-c]pyridine-2-carboxamide;
N-(4-{[1-(tetrahydrofuran-2-ylmethyl)piperidin-4-yl]oxy}phenyl)-1,3-dihydro-2H-pyrrolo[3,4-c]pyridine-2-carboxamide;
N-(4-{[1-(2-methylpropyl)piperidin-4-yl]oxy}phenyl)-1,3-dihydro-2H-pyrrolo[3,4-c]pyridine-2-carboxamide;
N-(4-{[1-(butylsulfonyl)piperidin-4-yl]oxy}phenyl)-1,3-dihydro-2H-pyrrolo[3,4-c]pyridine-2-carboxamide;
N-(4-{[1-(cyclopropylsulfonyl)piperidin-4-yl]oxy}phenyl)-1,3-dihydro-2H-pyrrolo[3,4-c]pyridine-2-carboxamide;
N-(4-{[1-(phenylsulfonyl)piperidin-4-yl]oxy}phenyl)-1,3-dihydro-2H-pyrrolo[3,4-c]pyridine-2-carboxamide;
N-[4-({1-[(4-fluorophenyl)sulfonyl]piperidin-4-yl}oxy)phenyl]-1,3-dihydro-2H-pyrrolo[3,4-c]pyridine-2-carboxamide;
N-(4-{[1-(ethylsulfonyl)piperidin-4-yl]oxy}phenyl)-1,3-dihydro-2H-pyrrolo[3,4-c]pyridine-2-carboxamide;
N-(4-{[1-(propan-2-ylsulfonyl)piperidin-4-yl]oxy}phenyl)-1,3-dihydro-2H-pyrrolo[3,4-c]pyridine-2-carboxamide;
N-(4-{[1-(benzylsulfonyl)piperidin-4-yl]oxy}phenyl)-1,3-dihydro-2H-pyrrolo[3,4-c]pyridine-2-carboxamide;
N-(4-{[1-(propylsulfonyl)piperidin-4-yl]oxy}phenyl)-1,3-dihydro-2H-pyrrolo[3,4-c]pyridine-2-carboxamide;
N-(4-{[1-(thiophen-2-ylsulfonyl)piperidin-4-yl]oxy}phenyl)-1,3-dihydro-2H-pyrrolo[3,4-c]pyridine-2-carboxamide;
N-[4-({1-[(2S)-2-methylbutanoyl]piperidin-4-yl}oxy)phenyl]-1,3-dihydro-2H-pyrrolo[3,4-c]pyridine-2-carboxamide;
N-[4-({1-[(2S)-tetrahydrofuran-2-ylcarbonyl]piperidin-4-yl}oxy)phenyl]-1,3-dihydro-2H-pyrrolo[3,4-c]pyridine-2-carboxamide;
N-[4-({1-[(2R)-tetrahydrofuran-2-ylcarbonyl]piperidin-4-yl}oxy)phenyl]-1,3-dihydro-2H-pyrrolo[3,4-c]pyridine-2-carboxamide;
N-[4-({1-[(4,4-difluorocyclohexyl)carbonyl]azetidin-3-yl}oxy)phenyl]-1,3-dihydro-2H-pyrrolo[3,4-c]pyridine-2-carboxamide;
N-(4-{[1-(5-oxo-D-prolyl)piperidin-4-yl]oxy}phenyl)-1,3-dihydro-2H-pyrrolo[3,4-c]pyridine-2-carboxamide;
N-(4-{[1-(2,2-dimethylpropanoyl)piperidin-4-yl]oxy}phenyl)-1,3-dihydro-2H-pyrrolo[3,4-c]pyridine-2-carboxamide;
N-(4-{[1-(2-methylpentanoyl)piperidin-4-yl]oxy}phenyl)-1,3-dihydro-2H-pyrrolo[3,4-c]pyridine-2-carboxamide;
N-(4-{[1-(2-ethylbutanoyl)piperidin-4-yl]oxy}phenyl)-1,3-dihydro-2H-pyrrolo[3,4-c]pyridine-2-carboxamide;
N-(4-{[1-(1H-pyrrol-2-ylcarbonyl)piperidin-4-yl]oxy}phenyl)-1,3-dihydro-2H-pyrrolo[3,4-c]pyridine-2-carboxamide;
N-(4-{[1-(1,2-oxazol-5-ylcarbonyl)piperidin-4-yl]oxy}phenyl)-1,3-dihydro-2H-pyrrolo[3,4-c]pyridine-2-carboxamide;
N-(4-{[1-(pyridin-3-ylcarbonyl)piperidin-4-yl]oxy}phenyl)-1,3-dihydro-2H-pyrrolo[3,4-c]pyridine-2-carboxamide;
N-(4-{[1-(pyridazin-3-ylcarbonyl)piperidin-4-yl]oxy}phenyl)-1,3-dihydro-2H-pyrrolo[3,4-c]pyridine-2-carboxamide;
N-(4-{[1-(pyrazin-2-ylcarbonyl)piperidin-4-yl]oxy}phenyl)-1,3-dihydro-2H-pyrrolo[3,4-c]pyridine-2-carboxamide;
N-(4-{[1-(pyrimidin-4-ylcarbonyl)piperidin-4-yl]oxy}phenyl)-1,3-dihydro-2H-pyrrolo[3,4-c]pyridine-2-carboxamide;
N-[4-({1-[(5-methylpyrazin-2-yl)carbonyl]piperidin-4-yl}oxy)phenyl]-1,3-dihydro-2H-pyrrolo[3,4-c]pyridine-2-carboxamide;
N-[4-({1-[3-(piperidin-1-yl)propanoyl]piperidin-4-yl}oxy)phenyl]-1,3-dihydro-2H-pyrrolo[3,4-c]pyridine-2-carboxamide;
N-(4-{[1-(morpholin-4-ylacetyl)piperidin-4-yl]oxy}phenyl)-1,3-dihydro-2H-pyrrolo[3,4-c]pyridine-2-carboxamide;
N-[4-({1-[3-(4-methylpiperazin-1-yl)propanoyl]piperidin-4-yl}oxy)phenyl]-1,3-dihydro-2H-pyrrolo[3,4-c]pyridine-2-carboxamide;
benzyl trans-3-[(1,3-dihydro-2H-pyrrolo[3,4-c]pyridin-2-ylcarbonyl)amino]cyclobutanecarboxylate;
N-[4-(4-{[(4-methylpiperazin-1-yl)acetyl]amino}cyclohex-1-en-1-yl)phenyl]-1,3-dihydro-2H-pyrrolo[3,4-c]pyridine-2-carboxamide;
N-(4-{4-[(tetrahydro-2H-pyran-4-ylacetyl)amino]cyclohex-1-en-1-yl}phenyl)-1,3-dihydro-2H-pyrrolo[3,4-c]pyridine-2-carboxamide;
N-{4-[4-(benzoylamino)cyclohex-1-en-1-yl]phenyl}-1,3-dihydro-2H-pyrrolo[3,4-c]pyridine-2-carboxamide;
N-[4-(4-{[(2S)-tetrahydrofuran-2-ylcarbonyl]amino}cyclohex-1-en-1-yl)phenyl]-1,3-dihydro-2H-pyrrolo[3,4-c]pyridine-2-carboxamide;
N-[4-(4-{[(2R)-tetrahydrofuran-2-ylcarbonyl]amino}cyclohex-1-en-1-yl)phenyl]-1,3-dihydro-2H-pyrrolo[3,4-c]pyridine-2-carboxamide;
N-[4-(4-{[(1-methylpiperidin-4-yl)carbonyl]amino}cyclohex-1-en-1-yl)phenyl]-1,3-dihydro-2H-pyrrolo[3,4-c]pyridine-2-carboxamide;
N-[4-(4-{[(1,1-dioxidotetrahydro-2H-thiopyran-4-yl)carbonyl]amino}cyclohex-1-en-1-yl)phenyl]-1,3-dihydro-2H-pyrrolo[3,4-c]pyridine-2-carboxamide;
N-[4-(4-{[(3R)-tetrahydrofuran-3-ylcarbonyl]amino}cyclohex-1-en-1-yl)phenyl]-1,3-dihydro-2H-pyrrolo[3,4-c]pyridine-2-carboxamide;
N-[4-(4-{[(3S)-tetrahydrofuran-3-ylcarbonyl]amino}cyclohex-1-en-1-yl)phenyl]-1,3-dihydro-2H-pyrrolo[3,4-c]pyridine-2-carboxamide;
N-[4-(4-{[(2S)-2-methylbutanoyl]amino}cyclohex-1-en-1-yl)phenyl]-1,3-dihydro-2H-pyrrolo[3,4-c]pyridine-2-carboxamide;
N-(4-{3-[(3-methylbutanoyl)amino]oxetan-3-yl}phenyl)-1,3-dihydro-2H-pyrrolo[3,4-c]pyridine-2-carboxamide;
tert-butyl 4-({4-[(1,3-dihydro-2H-pyrrolo[3,4-c]pyridin-2-ylcarbonyl)amino]phenyl}sulfonyl)piperidine-1-carboxylate;
N-{4-[4-(propylcarbamoyl)piperidin-1-yl]phenyl}-1,3-dihydro-2H-pyrrolo[3,4-c]pyridine-2-carboxamide;
N-(4-{4-[(2-methoxyethyl)carbamoyl]piperidin-1-yl}phenyl)-1,3-dihydro-2H-pyrrolo[3,4-c]pyridine-2-carboxamide;
N-(4-{4-[(cyclopentylmethyl)carbamoyl]piperidin-1-yl}phenyl)-1,3-dihydro-2H-pyrrolo[3,4-c]pyridine-2-carboxamide;
N-(4-{4-[(1,4-dioxan-2-ylmethyl)carbamoyl]piperidin-1-yl}phenyl)-1,3-dihydro-2H-pyrrolo[3,4-c]pyridine-2-carboxamide;
N-{4-[4-(cyclopentylcarbamoyl)piperidin-1-yl]phenyl}-1,3-dihydro-2H-pyrrolo[3,4-c]pyridine-2-carboxamide;

N-{4-[4-(tetrahydro-2H-pyran-4-ylcarbamoyl)piperidin-1-yl]phenyl}-1,3-dihydro-2H-pyrrolo[3,4-c]pyridine-2-carboxamide;
N-{4-[4-(morpholin-4-ylcarbonyl)piperidin-1-yl]phenyl}-1,3-dihydro-2H-pyrrolo[3,4-c]pyridine-2-carboxamide;
N-(4-{4-[(tetrahydro-2H-pyran-4-ylmethyl)carbamoyl]piperidin-1-yl}phenyl)-1,3-dihydro-2H-pyrrolo[3,4-c]pyridine-2-carboxamide;
N-{4-[4-(cyclopropylcarbamoyl)piperidin-1-yl]phenyl}-1,3-dihydro-2H-pyrrolo[3,4-c]pyridine-2-carboxamide;
N-(4-{4-[(tetrahydrofuran-3-ylmethyl)carbamoyl]piperidin-1-yl}phenyl)-1,3-dihydro-2H-pyrrolo[3,4-c]pyridine-2-carboxamide;
N-(4-{4-[(2-hydroxy-2-methylpropyl)carbamoyl]piperidin-1-yl}phenyl)-1,3-dihydro-2H-pyrrolo[3,4-c]pyridine-2-carboxamide;
N-{4-[4-(butan-2-ylcarbamoyl)piperidin-1-yl]phenyl}-1,3-dihydro-2H-pyrrolo[3,4-c]pyridine-2-carboxamide;
N-(4-{1-[(3R)-tetrahydrofuran-3-ylcarbonyl]-1,2,3,6-tetrahydropyridin-4-yl}phenyl)-1,3-dihydro-2H-isoindole-2-carboxamide;
N-(4-{1-[(3S)-tetrahydrofuran-3-ylcarbonyl]-1,2,3,6-tetrahydropyridin-4-yl}phenyl)-1,3-dihydro-2H-isoindole-2-carboxamide;
N-(4-{1-[(1,1-dioxidotetrahydro-2H-thiopyran-4-yl)carbonyl]-1,2,3,6-tetrahydropyridin-4-yl}phenyl)-1,3-dihydro-2H-isoindole-2-carboxamide;
N-(4-{1-[(2R)-tetrahydrofuran-2-ylcarbonyl]piperidin-4-yl}phenyl)-1,3-dihydro-2H-isoindole-2-carboxamide;
N-(4-{1-[(2S)-tetrahydrofuran-2-ylcarbonyl]piperidin-4-yl}phenyl)-1,3-dihydro-2H-isoindole-2-carboxamide;
N-(4-{1-[(3R)-tetrahydrofuran-3-ylcarbonyl]piperidin-4-yl}phenyl)-1,3-dihydro-2H-isoindole-2-carboxamide;
N-(4-{(4R)-4-[(2-methylpropanoyl)amino]cyclohex-1-en-1-yl}phenyl)-1,3-dihydro-2H-pyrrolo[3,4-c]pyridine-2-carboxamide;
N-(4-{(4S)-4-[(2-methylpropanoyl)amino]cyclohex-1-en-1-yl}phenyl)-1,3-dihydro-2H-pyrrolo[3,4-c]pyridine-2-carboxamide;
N-[trans-3-(benzylcarbamoyl)cyclobutyl]-1,3-dihydro-2H-pyrrolo[3,4-c]pyridine-2-carboxamide;
N-{trans-3-[(2-phenylethyl)carbamoyl]cyclobutyl}-1,3-dihydro-2H-pyrrolo[3,4-c]pyridine-2-carboxamide;
N-{trans-3-[(3-phenylpropyl)carbamoyl]cyclobutyl}-1,3-dihydro-2H-pyrrolo[3,4-c]pyridine-2-carboxamide;
N-(4-{1-[(2-methyl-1,3-oxazol-4-yl)carbonyl]-1,2,3,6-tetrahydropyridin-4-yl}phenyl)-1,3-dihydro-2H-pyrrolo[3,4-c]pyridine-2-carboxamide;
N-{4-[1-(furan-3-ylcarbonyl)-1,2,3,6-tetrahydropyridin-4-yl]phenyl}-1,3-dihydro-2H-pyrrolo[3,4-c]pyridine-2-carboxamide;
N-(4-{1-[(2E)-3-(furan-2-yl)prop-2-enoyl]-1,2,3,6-tetrahydropyridin-4-yl}phenyl)-1,3-dihydro-2H-pyrrolo[3,4-c]pyridine-2-carboxamide;
N-{4-[1-(1,3-oxazol-5-ylcarbonyl)-1,2,3,6-tetrahydropyridin-4-yl]phenyl}-1,3-dihydro-2H-pyrrolo[3,4-c]pyridine-2-carboxamide;
N-{4-[1-(3,3,3-trifluoropropanoyl)-1,2,3,6-tetrahydropyridin-4-yl]phenyl}-1,3-dihydro-2H-pyrrolo[3,4-c]pyridine-2-carboxamide;
N-(4-{1-[(1,5-dimethyl-1H-pyrazol-3-yl)carbonyl]-1,2,3,6-tetrahydropyridin-4-yl}phenyl)-1,3-dihydro-2H-pyrrolo[3,4-c]pyridine-2-carboxamide;
N-(4-{1-[(4-methoxycyclohexyl)carbonyl]-1,2,3,6-tetrahydropyridin-4-yl}phenyl)-1,3-dihydro-2H-pyrrolo[3,4-c]pyridine-2-carboxamide;
N-{4-[1-(2,3-dimethylbutanoyl)-1,2,3,6-tetrahydropyridin-4-yl]phenyl}-1,3-dihydro-2H-pyrrolo[3,4-c]pyridine-2-carboxamide;
N-(4-{1-[(2,2-difluorocyclopropyl)carbonyl]-1,2,3,6-tetrahydropyridin-4-yl}phenyl)-1,3-dihydro-2H-pyrrolo[3,4-c]pyridine-2-carboxamide;
N-{4-[1-(1H-pyrazol-5-ylcarbonyl)-1,2,3,6-tetrahydropyridin-4-yl]phenyl}-1,3-dihydro-2H-pyrrolo[3,4-c]pyridine-2-carboxamide;
N-{4-[1-(tert-butoxyacetyl)-1,2,3,6-tetrahydropyridin-4-yl]phenyl}-1,3-dihydro-2H-pyrrolo[3,4-c]pyridine-2-carboxamide;
N-(4-{1-[3-(1H-1,2,4-triazol-1-yl)propanoyl]-1,2,3,6-tetrahydropyridin-4-yl}phenyl)-1,3-dihydro-2H-pyrrolo[3,4-c]pyridine-2-carboxamide;
N-{4-[1-(3-ethoxypropanoyl)-1,2,3,6-tetrahydropyridin-4-yl]phenyl}-1,3-dihydro-2H-pyrrolo[3,4-c]pyridine-2-carboxamide;
N-{4-[1-(3-hydroxy-3-methylbutanoyl)-1,2,3,6-tetrahydropyridin-4-yl]phenyl}-1,3-dihydro-2H-pyrrolo[3,4-c]pyridine-2-carboxamide;
N-(4-{1-[3-(1H-pyrrol-1-yl)propanoyl]-1,2,3,6-tetrahydropyridin-4-yl}phenyl)-1,3-dihydro-2H-pyrrolo[3,4-c]pyridine-2-carboxamide;
N-(4-{1-[(1-methylcyclopropyl)carbonyl]-1,2,3,6-tetrahydropyridin-4-yl}phenyl)-1,3-dihydro-2H-pyrrolo[3,4-c]pyridine-2-carboxamide;
N-(4-{1-[(2-methylpropoxy)acetyl]-1,2,3,6-tetrahydropyridin-4-yl}phenyl)-1,3-dihydro-2H-pyrrolo[3,4-c]pyridine-2-carboxamide;
N-{4-[1-(1-methylprolyl)-1,2,3,6-tetrahydropyridin-4-yl]phenyl}-1,3-dihydro-2H-pyrrolo[3,4-c]pyridine-2-carboxamide;
N-{4-[1-(2-hydroxy-2-methylbutanoyl)-1,2,3,6-tetrahydropyridin-4-yl]phenyl}-1,3-dihydro-2H-pyrrolo[3,4-c]pyridine-2-carboxamide;
N-(4-{1-[(1-hydroxycyclopropyl)carbonyl]-1,2,3,6-tetrahydropyridin-4-yl}phenyl)-1,3-dihydro-2H-pyrrolo[3,4-c]pyridine-2-carboxamide;
N-{4-[1-(cyclopropylacetyl)-1,2,3,6-tetrahydropyridin-4-yl]phenyl}-1,3-dihydro-2H-pyrrolo[3,4-c]pyridine-2-carboxamide;
N-{4-[1-(cyclopentylcarbonyl)-1,2,3,6-tetrahydropyridin-4-yl]phenyl}-1,3-dihydro-2H-pyrrolo[3,4-c]pyridine-2-carboxamide;
N-[4-(1-{[1-(methoxymethyl)cyclopropyl]carbonyl}-1,2,3,6-tetrahydropyridin-4-yl)phenyl]-1,3-dihydro-2H-pyrrolo[3,4-c]pyridine-2-carboxamide;
N-(4-{1-[(methylsulfonyl)acetyl]-1,2,3,6-tetrahydropyridin-4-yl}phenyl)-1,3-dihydro-2H-pyrrolo[3,4-c]pyridine-2-carboxamide;
N-(4-{1-[(1-methyl-1H-pyrazol-4-yl)carbonyl]-1,2,3,6-tetrahydropyridin-4-yl}phenyl)-1,3-dihydro-2H-pyrrolo[3,4-c]pyridine-2-carboxamide;
N-[4-(1-acetyl-1,2,3,6-tetrahydropyridin-4-yl)phenyl]-1,3-dihydro-2H-pyrrolo[3,4-c]pyridine-2-carboxamide;
N-{4-[1-(cyclopropylcarbonyl)-1,2,3,6-tetrahydropyridin-4-yl]phenyl}-1,3-dihydro-2H-pyrrolo[3,4-c]pyridine-2-carboxamide;
N-{4-[1-(2-ethylbutanoyl)-1,2,3,6-tetrahydropyridin-4-yl]phenyl}-1,3-dihydro-2H-pyrrolo[3,4-c]pyridine-2-carboxamide;
N-{4-[1-(5-oxo-L-prolyl)-1,2,3,6-tetrahydropyridin-4-yl]phenyl}-1,3-dihydro-2H-pyrrolo[3,4-c]pyridine-2-carboxamide;

N-(4-{1-[(2E)-4-methylpent-2-enoyl]-1,2,3,6-tetrahydropyridin-4-yl}phenyl)-1,3-dihydro-2H-pyrrolo[3,4-c]pyridine-2-carboxamide;

N-{4-[1-(2-methoxy-2-methylpropanoyl)-1,2,3,6-tetrahydropyridin-4-yl]phenyl}-1,3-dihydro-2H-pyrrolo[3,4-c]pyridine-2-carboxamide;

N-{4-[1-(cyclopent-1-en-1-ylcarbonyl)-1,2,3,6-tetrahydropyridin-4-yl]phenyl}-1,3-dihydro-2H-pyrrolo[3,4-c]pyridine-2-carboxamide;

N-{4-[1-(thiophen-3-ylacetyl)-1,2,3,6-tetrahydropyridin-4-yl]phenyl}-1,3-dihydro-2H-pyrrolo[3,4-c]pyridine-2-carboxamide;

N-{4-[1-(cyclohexylcarbonyl)-1,2,3,6-tetrahydropyridin-4-yl]phenyl}-1,3-dihydro-2H-pyrrolo[3,4-c]pyridine-2-carboxamide;

N-[4-(1-propanoyl-1,2,3,6-tetrahydropyridin-4-yl)phenyl]-1,3-dihydro-2H-pyrrolo[3,4-c]pyridine-2-carboxamide;

N-{4-[1-(2,2-dimethylbutanoyl)-1,2,3,6-tetrahydropyridin-4-yl]phenyl}-1,3-dihydro-2H-pyrrolo[3,4-c]pyridine-2-carboxamide;

N-(4-{1-[(1-methyl-1H-pyrrol-2-yl)carbonyl]-1,2,3,6-tetrahydropyridin-4-yl}phenyl)-1,3-dihydro-2H-pyrrolo[3,4-c]pyridine-2-carboxamide;

N-{4-[1-(methoxyacetyl)-1,2,3,6-tetrahydropyridin-4-yl]phenyl}-1,3-dihydro-2H-pyrrolo[3,4-c]pyridine-2-carboxamide;

N-{4-[1-(2,2-dimethylpropanoyl)-1,2,3,6-tetrahydropyridin-4-yl]phenyl}-1,3-dihydro-2H-pyrrolo[3,4-c]pyridine-2-carboxamide;

N-{4-[1-(4-methylhexanoyl)-1,2,3,6-tetrahydropyridin-4-yl]phenyl}-1,3-dihydro-2H-pyrrolo[3,4-c]pyridine-2-carboxamide;

N-(4-{1-[(2,2-dimethylcyclopropyl)carbonyl]-1,2,3,6-tetrahydropyridin-4-yl}phenyl)-1,3-dihydro-2H-pyrrolo[3,4-c]pyridine-2-carboxamide;

N-(4-{1-[(1,3-dimethyl-1H-pyrazol-5-yl)carbonyl]-1,2,3,6-tetrahydropyridin-4-yl}phenyl)-1,3-dihydro-2H-pyrrolo[3,4-c]pyridine-2-carboxamide;

N-{4-[1-(cyclobutylacetyl)-1,2,3,6-tetrahydropyridin-4-yl]phenyl}-1,3-dihydro-2H-pyrrolo[3,4-c]pyridine-2-carboxamide;

N-{4-[1-(piperidin-1-ylacetyl)-1,2,3,6-tetrahydropyridin-4-yl]phenyl}-1,3-dihydro-2H-pyrrolo[3,4-c]pyridine-2-carboxamide;

N-(4-{1-[2-(pyrrolidin-1-yl)propanoyl]-1,2,3,6-tetrahydropyridin-4-yl}phenyl)-1,3-dihydro-2H-pyrrolo[3,4-c]pyridine-2-carboxamide;

N-(4-{1-[(1,3-dimethyl-1H-pyrazol-4-yl)carbonyl]-1,2,3,6-tetrahydropyridin-4-yl}phenyl)-1,3-dihydro-2H-pyrrolo[3,4-c]pyridine-2-carboxamide;

N-[4-(cis-4-{[(2-methoxyethoxy)acetyl]amino}cyclohexyl)phenyl]-1,3-dihydro-2H-pyrrolo[3,4-c]pyridine-2-carboxamide;

N-[4-(trans-4-{[(2-methoxyethoxy)acetyl]amino}cyclohexyl)phenyl]-1,3-dihydro-2H-pyrrolo[3,4-c]pyridine-2-carboxamide;

N-[4-(cis-4-{[(2S)-tetrahydrofuran-2-ylcarbonyl]amino}cyclohexyl)phenyl]-1,3-dihydro-2H-pyrrolo[3,4-c]pyridine-2-carboxamide;

N-[4-(trans-4-{[(2S)-tetrahydrofuran-2-ylcarbonyl]amino}cyclohexyl)phenyl]-1,3-dihydro-2H-pyrrolo[3,4-c]pyridine-2-carboxamide;

N-[4-(cis-4-{[(2R)-tetrahydrofuran-2-ylcarbonyl]amino}cyclohexyl)phenyl]-1,3-dihydro-2H-pyrrolo[3,4-c]pyridine-2-carboxamide;

N-[4-(trans-4-{[(2R)-tetrahydrofuran-2-ylcarbonyl]amino}cyclohexyl)phenyl]-1,3-dihydro-2H-pyrrolo[3,4-c]pyridine-2-carboxamide;

N-(6-{[(2S)-tetrahydrofuran-2-ylmethyl]carbamoyl}pyridazin-3-yl)-1,3-dihydro-2H-pyrrolo[3,4-c]pyridine-2-carboxamide;

N-(4-{[(3R)-1-(3-methylbutanoyl)pyrrolidin-3-yl]oxy}phenyl)-1,3-dihydro-2H-pyrrolo[3,4-c]pyridine-2-carboxamide;

N-(4-{[(3R)-1-(cyclobutylcarbonyl)pyrrolidin-3-yl]oxy}phenyl)-1,3-dihydro-2H-pyrrolo[3,4-c]pyridine-2-carboxamide;

N-[4-({(3R)-1-[(2R)-tetrahydrofuran-2-ylcarbonyl]pyrrolidin-3-yl}oxy)phenyl]-1,3-dihydro-2H-pyrrolo[3,4-c]pyridine-2-carboxamide;

N-[4-({(3R)-1-[(2S)-tetrahydrofuran-2-ylcarbonyl]pyrrolidin-3-yl}oxy)phenyl]-1,3-dihydro-2H-pyrrolo[3,4-c]pyridine-2-carboxamide;

N-(4-{[(3R)-1-(cyclopropylacetyl)pyrrolidin-3-yl]oxy}phenyl)-1,3-dihydro-2H-pyrrolo[3,4-c]pyridine-2-carboxamide;

N-(4-{[(3S)-1-(3-methylbutanoyl)pyrrolidin-3-yl]oxy}phenyl)-1,3-dihydro-2H-pyrrolo[3,4-c]pyridine-2-carboxamide;

N-(4-{[(3S)-1-(cyclobutylcarbonyl)pyrrolidin-3-yl]oxy}phenyl)-1,3-dihydro-2H-pyrrolo[3,4-c]pyridine-2-carboxamide;

N-[4-({(3S)-1-[(2R)-tetrahydrofuran-2-ylcarbonyl]pyrrolidin-3-yl}oxy)phenyl]-1,3-dihydro-2H-pyrrolo[3,4-c]pyridine-2-carboxamide;

N-[4-({(3S)-1-[(2S)-tetrahydrofuran-2-ylcarbonyl]pyrrolidin-3-yl}oxy)phenyl]-1,3-dihydro-2H-pyrrolo[3,4-c]pyridine-2-carboxamide;

N-(4-{[(3S)-1-(cyclopropylacetyl)pyrrolidin-3-yl]oxy}phenyl)-1,3-dihydro-2H-pyrrolo[3,4-c]pyridine-2-carboxamide;

N-(6-{[(2R)-tetrahydrofuran-2-ylmethyl]carbamoyl}pyridazin-3-yl)-1,3-dihydro-2H-pyrrolo[3,4-c]pyridine-2-carboxamide;

N-{6-[(tetrahydro-2H-pyran-4-ylmethyl)carbamoyl]pyridazin-3-yl}-1,3-dihydro-2H-pyrrolo[3,4-c]pyridine-2-carboxamide;

N-{6-[(cyclopentylmethyl)carbamoyl]pyridazin-3-yl}-1,3-dihydro-2H-pyrrolo[3,4-c]pyridine-2-carboxamide;

N-{6-[(tetrahydrofuran-3-ylmethyl)carbamoyl]pyridazin-3-yl}-1,3-dihydro-2H-pyrrolo[3,4-c]pyridine-2-carboxamide;

N-{6-[(bicyclo[2.2.1]hept-2-ylmethyl)carbamoyl]pyridazin-3-yl}-1,3-dihydro-2H-pyrrolo[3,4-c]pyridine-2-carboxamide;

N-(4-{trans-4-[(2-methylpropanoyl)amino]cyclohexyl}phenyl)-1,3-dihydro-2H-pyrrolo[3,4-c]pyridine-2-carboxamide;

N-(4-{cis-4-[(2-methylpropanoyl)amino]cyclohexyl}phenyl)-1,3-dihydro-2H-pyrrolo[3,4-c]pyridine-2-carboxamide;

N-(4-{cis-4-[(cyclohexylcarbonyl)amino]cyclohexyl}phenyl)-1,3-dihydro-2H-pyrrolo[3,4-c]pyridine-2-carboxamide;

N-(4-{trans-4-[(cyclohexylcarbonyl)amino]cyclohexyl}phenyl)-1,3-dihydro-2H-pyrrolo[3,4-c]pyridine-2-carboxamide;

N-(4-{trans-4-[(cyclopropylacetyl)amino]cyclohexyl}phenyl)-1,3-dihydro-2H-pyrrolo[3,4-c]pyridine-2-carboxamide;

N-(4-{cis-4-[(cyclopropylacetyl)amino]
cyclohexyl}phenyl)-1,3-dihydro-2H-pyrrolo[3,4-c]pyridine-2-carboxamide;

N-(4-{4-[(2-methylpropanoyl)amino]cyclohex-1-en-1-yl}phenyl)-1,3-dihydro-2H-isoindole-2-carboxamide;

N-[4-(4-{[(2R)-tetrahydrofuran-2-ylcarbonyl]amino}cyclohex-1-en-1-yl)phenyl]-1,3-dihydro-2H-isoindole-2-carboxamide;

N-[4-(4-{[(2S)-tetrahydrofuran-2-ylcarbonyl]amino}cyclohex-1-en-1-yl)phenyl]-1,3-dihydro-2H-isoindole-2-carboxamide;

N-(4-{4-[(cyclopentylacetyl)amino]cyclohex-1-en-1-yl}phenyl)-1,3-dihydro-2H-isoindole-2-carboxamide;

N-(4-{4-[(cyclopropylacetyl)amino]cyclohex-1-en-1-yl}phenyl)-1,3-dihydro-2H-isoindole-2-carboxamide;

N-(4-{4-[(2-hydroxy-2-methylpropanoyl)amino]cyclohex-1-en-1-yl}phenyl)-1,3-dihydro-2H-isoindole-2-carboxamide;

N-(4-{4-[(tetrahydro-2H-pyran-4-ylcarbonyl)amino]cyclohex-1-en-1-yl}phenyl)-1,3-dihydro-2H-isoindole-2-carboxamide;

N-(4-{4-[(cyclohexylcarbonyl)amino]cyclohex-1-en-1-yl}phenyl)-1,3-dihydro-2H-isoindole-2-carboxamide;

and pharmaceutically acceptable salts thereof.

Embodiments of Formula (IIIc)

In another aspect, the present invention provides compounds of Formula (IIIc)

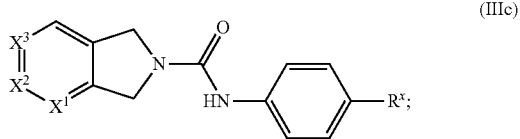

(IIIc)

and pharmaceutically acceptable salts thereof; wherein $X^1$, $X^2$, $X^3$, are as described herein for Formula (Ic); and $R^x$ is as described herein for substituents at the para position in Formula (Ic) when $R^2$ is phenyl.

In one embodiment of formula (IIIc),
$X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or
$X^1$ is CH; $X^2$ is N; and $X^3$ is $CR^1$; or
$X^1$ is $CR^1$; $X^2$ is N; and $X^3$ is CH; or
$X^1$ is N; $X^2$ is $CR^1$; and $X^3$ is CH; or
$X^1$ is N; $X^2$ is $CR^1$; and $X^3$ is N;

$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, C(O)H, $CF_3$, C(O)OH, or $C(O)NH_2$;

$R^x$ is $R^5$, $OR^5$, $SR^5$, $S(O)R^5$, $SO_2R^5$, $C(O)R^5$, $C(O)OR^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $CHNOR^5$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, C(O)H, C(O)OH, OH, CN, $N_3$, $NO_2$, $CF_3$, $CF_2CF_3$, $OCF_3$, $OCF_2CF_3$, Br or I;

$R^3$, at each occurrence, is independently selected alkyl, alkenyl, alkynyl, aryl, or heterocyclyl; wherein each $R^3$ alkyl, alkenyl, and alkynyl is optionally substituted with one, two, three or four independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, C(O)H, C(O)OH, OH, (O), CN, $N_3$, $NO_2$, $CF_3$, $CF_2CF_3$, $OCF_3$, $OCF_2CF_3$, F, Cl, Br or I;

$R^5$, at each occurrence, is independently selected alkyl, alkenyl, alkynyl, aryl, heterocyclyl, cycloalkyl, or cycloalkenyl; wherein each $R^5$ alkyl, alkenyl, and alkynyl is optionally substituted with one, two, three or four independently selected $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, C(O)NHR^9, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, C(O)H, C(O)OH, OH, (O), CN, $N_3$, $NO_2$, $CF_3$, $CF_2CF_3$, $OCF_3$, $OCF_2CF_3$, F, Cl, Br or I;

$R^6$, at each occurrence, is independently selected alkyl, alkenyl, alkynyl, aryl, heterocyclyl, cycloalkyl, or cycloalkenyl; wherein each $R^6$ alkyl, alkenyl, and alkynyl is optionally substituted with one, two, three or four independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, OH, (O), C(O)OH, $N_3$, CN, $NH_2$, $CF_3$, $CF_2CF_3$, F, Cl, Br or I;

$R^9$, at each occurrence, is independently selected alkyl, alkenyl, alkynyl, aryl, heterocyclyl, cycloalkyl, or cycloalkenyl; wherein each $R^9$ alkyl, alkenyl, and alkynyl is optionally substituted with one, two, three or four independently selected alkoxy, OH, cycloalkyl, aryl, or heterocyclyl;

$R^{10}$, at each occurrence, is independently selected alkyl, alkenyl, alkynyl, aryl, heterocyclyl, cycloalkyl, or cycloalkenyl;

wherein the cyclic moieties represented by $R^3$, $R^5$, $R^6$, $R^9$, and $R^{10}$ are optionally substituted with one, two, three, four, five, or six independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, C(O)H, C(O)OH, OH, CN, $N_3$, $NO_2$, $CF_3$, $CF_2CF_3$, $OCF_3$, $OCF_2CF_3$, $SCF_3$, F, Cl, Br or I;

$R^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, or cycloalkenyl; wherein each $R^{13}$ alkyl, alkenyl, and alkynyl is optionally substituted with one, two, three or four independently selected $R^{14}$, $OR^{14}$, $SR^{14}$, $S(O)R^{14}$, $SO_2R^{14}$, $C(O)R^{14}$, $OC(O)R^{14}$, $OC(O)OR^{14}$, $NH_2$, $NHR^{14}$, $N(R^{14})_2$, $NHC(O)R^{14}$, $NR^{14}$, $C(O)R^{14}$, $NHS(O)_2R^{14}$, $NR^{14}S(O)_2R^{14}$, $NHC(O)R^{14}$, $NR^{14}C(O)OR^{14}$, $NHC(O)NH_2$, $NHC(O)NHR^{14}$, $NHC(O)N(R^{14})_2$, $NR^{14}C(O)NH_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, and cycloalkenyl is optionally substituted with one, two, three or four independently selected $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $C(O)H$, $C(O)OH$, $OH$, $CN$, $N_3$, $NO_2$, $CF_3$, $CF_2CF_3$, $OCF_3$, $OCF_2CF_3$, F, Cl, Br or I;

$R^{14}$, at each occurrence, is independently selected alkyl, alkenyl, alkynyl, aryl, heterocyclyl, cycloalkyl, or cycloalkenyl; wherein each $R^{14}$ alkyl, alkenyl, and alkynyl is optionally substituted with one, two, three or four independently selected heterocyclyl, alkoxy, $NH_2$, $SO_2NH_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{14}$ aryl, heterocyclyl, cycloalkyl, and cycloalkenyl is optionally substituted with one, two, three or four independently selected $R^{16}$, $OR^{16}$, $OH$, F, Cl, Br, or I;

$R^{15}$, at each occurrence, is independently selected alkyl, wherein the $R^{15}$ alkyl is optionally substituted with one, two, three or four alkoxy; and $R^{16}$, at each occurrence, is independently selected alkyl, wherein the $R^{16}$ alkyl is optionally substituted with one, two, three or four alkoxy;

with the proviso that when $X^1$, $X^2$, and $X^3$ are CH; $R^x$ is not methyl;

with the proviso that when $X^1$, $X^2$, and $X^3$ are CH; $R^x$ is not methoxy;

with the proviso that when $R^{13}$ is piperidinyl, it is substituted piperidinyl; and with the proviso that when $R^{13}$ is pyrrolinyl, at least one of $X^1$, $X^2$, and $X^3$ is N.

In one embodiment of Formula (IIIc), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N; or $X^1$ is CH; $X^2$ is N; and $X^3$ is $CR^1$; or $X^1$ is $CR^1$; $X^2$ is N; and $X^3$ is CH; or $X^1$ is N; $X^2$ is $CR^1$; and $X^3$ is CH; or $X^1$ is N; $X^2$ is $CR^1$; and $X^3$ is N. In another embodiment of Formula (IIIc), $X^1$, $X^2$, and $X^3$ are CH. In another embodiment of Formula (IIIc), $X^1$ and $X^3$ are CH; and $X^2$ is N. In another embodiment of Formula (IIIc), $X^1$ and $X^3$ are CH; and $X^2$ is $CR^1$. In another embodiment of Formula (IIIc), $X^2$ and $X^3$ are CH; and $X^1$ is $CR^1$. In another embodiment of Formula (IIIc), $X^1$ is CH; and $X^2$ and $X^3$ is $CR^1$. In another embodiment of Formula (IIIc), $X^2$ is CH; and $X^1$ and $X^3$ are N. In another embodiment of Formula (IIIc), $X^2$ and $X^3$ are CH; and $X^1$ is N. In another embodiment of Formula (IIIc), $X^1$ is CH; $X^2$ is N; and $X^3$ is $CR^1$. In another embodiment of Formula (IIIc), $X^1$ is $CR^1$; $X^2$ is N; and $X^3$ is CH. In another embodiment of Formula (IIIc), $X^1$ is N; $X^2$ is $CR^1$; and $X^3$ is CH. In another embodiment of Formula (IIIc), $X^1$ is N; $X^2$ is $CR^1$; and $X^3$ is N.

In another embodiment of Formula (IIIc), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (IIIc), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or $OH$; wherein $R^6$ is alkyl or heterocyclyl. In another embodiment of Formula (IIIc), $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or $OH$; wherein $R^6$ is alkyl or heterocyclyl. In another embodiment of Formula (IIIc), $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or $OH$; wherein $R^6$ is alkyl or heterocyclyl. In another embodiment of Formula (IIIc), $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or $OH$; wherein $R^6$ is alkyl or heterocyclyl. In another embodiment of Formula (IIIc), $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or $OH$; wherein $R^6$ is alkyl or heterocyclyl. In another embodiment of Formula (IIIc), $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or $OH$; wherein $R^6$ is alkyl or heterocyclyl. In another embodiment of Formula (IIIc), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or $OH$; wherein $R^6$ is alkyl or heterocyclyl. In another embodiment of Formula (IIIc), $R^1$ is $C(O)NH_2$. In another embodiment of Formula (IIIc), $R^1$ is F. In another embodiment of Formula (IIIc), $R^1$ is Cl. In another embodiment of Formula (IIIc), $R^1$ is Br. In another embodiment of Formula (IIIc), $R^1$ is CN. In another embodiment of Formula (IIIc), $R^1$ is $NH_2$. In another embodiment of Formula (IIIc), $R^1$ is $NO_2$. In another embodiment of Formula (IIIc), $R^1$ is $CF_3$. In another embodiment of Formula (IIIc), $R^1$ is $C(O)OH$. In another embodiment of Formula (IIIc), $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or $OH$; wherein $R^6$ is alkyl or heterocyclyl.

In another embodiment of Formula (IIIc), $X^1$ and $X^3$ are CH; and $X^2$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (IIIc), $X^1$ and $X^3$ are CH; and $X^2$ is $CR^1$; $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or $OH$; wherein $R^6$ is alkyl or heterocyclyl. In another embodiment of Formula (IIIc), $X^1$ and $X^3$ are CH; and $X^2$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIc), $X^1$ and $X^3$ are CH; and $X^2$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIc), $X^1$ and $X^3$ are CH; and $X^2$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIc), $X^1$ and $X^3$ are CH; and $X^2$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIc), $X^1$ and $X^3$ are CH; and $X^2$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIc), $X^1$ and $X^3$ are CH; and $X^2$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIc), $X^1$ and $X^3$ are CH; and $X^2$ is $CR^1$; and $R^1$ is $C(O)NH_2$. In another embodiment of Formula (IIIc), $X^1$ and $X^3$ are CH; and $X^2$ is $CR^1$; and $R^1$ is F. In another embodiment of Formula (IIIc), $X^1$ and $X^3$ are CH; and $X^2$ is $CR^1$; and $R^1$ is Cl. In another embodiment of Formula (IIIc), $X^1$ and $X^3$ are CH; and $X^2$ is $CR^1$; and $R^1$ is Br. In another embodiment of Formula (IIIc), $X^1$ and $X^3$ are CH; and $X^2$ is $CR^1$; and $R^1$ is CN. In another embodiment of Formula (IIIc), $X^1$ and $X^3$ are CH; and $X^2$ is $CR^1$; and $R^1$ is $NH_2$. In another embodiment of Formula (IIIc), $X^1$ and $X^3$ are CH; and $X^2$ is $CR^1$; and $R^1$ is $NO_2$. In another embodiment of Formula (IIIc), $X^1$ and $X^3$ are CH; and $X^2$ is $CR^1$; and $R^1$ is $CF_3$. In another embodiment of Formula (IIIc), $X^1$ and $X^3$ are CH; and $X^2$ is $CR^1$; and $R^1$ is C(O)OH. In another embodiment of Formula (IIIc), $X^1$ and $X^3$ are CH; and $X^2$ is $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In another embodiment of Formula (IIIc), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (IIIc), $X^2$ and $X^3$ are CH; and $X^1$ is $CR^1$; and $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIc), $X^2$ and $X^3$ are CH; and $X^1$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIc), $X^2$ and $X^3$ are CH; and $X^1$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIc), $X^2$ and $X^3$ are CH; and $X^1$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIc), $X^2$ and $X^3$ are CH; and $X^1$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIc), $X^2$ and $X^3$ are CH; and $X^1$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIc), $X^2$ and $X^3$ are CH; and $X^1$ is $CR^1$; and $R^1$ is $C(O)NH_2$. In another embodiment of Formula (IIIc), $X^2$ and $X^3$ are CH; and $X^1$ is $CR^1$; and $R^1$ is F. In another embodiment of Formula (IIIc), $X^2$ and $X^3$ are CH; and $X^1$ is $CR^1$; and $R^1$ is Cl. In another embodiment of Formula (IIIc), $X^2$ and $X^3$ are CH; and $X^1$ is $CR^1$; and $R^1$ is Br. In another embodiment of Formula (IIIc), $X^2$ and $X^3$ are CH; and $X^1$ is $CR^1$; and $R^1$ is CN. In another embodiment of Formula (IIIc), $X^2$ and $X^3$ are CH; and $X^1$ is $CR^1$; and $R^1$ is $NH_2$. In another embodiment of Formula (IIIc), $X^2$ and $X^3$ are CH; and $X^1$ is $CR^1$; and $R^1$ is $NO_2$. In another embodiment of Formula (IIIc), $X^2$ and $X^3$ are CH; and $X^1$ is $CR^1$; and $R^1$ is $CF_3$. In another embodiment of Formula (IIIc), $X^2$ and $X^3$ are CH; and $X^1$ is $CR^1$; and $R^1$ is C(O)OH. In another embodiment of Formula (IIIc), $X^2$ and $X^3$ are CH; and $X^1$ is $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In another embodiment of Formula (IIIc), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (IIIc), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIc), $X^1$ is CH; and $X^2$ and $X^3$ are $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIc), $X^1$ is CH; and $X^2$ and $X^3$ are $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIc), $X^1$ is CH; and $X^2$ and $X^3$ are $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIc), $X^1$ is CH; and $X^2$ and $X^3$ are $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIc), $X^1$ is CH; and $X^2$ and $X^3$ are $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIc), $X^1$ is CH; and $X^2$ and $X^3$ are $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IIIc), $X^1$ is CH; and $X^2$ and $X^3$ are $CR^1$; and $R^1$ is $C(O)NH_2$. In another embodiment of Formula (IIIc), $X^1$ is CH; and $X^2$ and $X^3$ are $CR^1$; and $R^1$ is F. In another embodiment of Formula (IIIc), $X^1$ is CH; and $X^2$ and $X^3$ are $CR^1$; and $R^1$ is Cl. In another embodiment of Formula (IIIc), $X^1$ is CH; and $X^2$ and $X^3$ are $CR^1$; and $R^1$ is Br. In another embodiment of Formula (IIIc), $X^1$ is CH; and $X^2$ and $X^3$ are $CR^1$; and $R^1$ is CN. In another embodiment of Formula (IIIc), $X^1$ is CH; and $X^2$ and $X^3$ are $CR^1$; and $R^1$ is $NH_2$. In another embodiment of Formula (IIIc), $X^1$ is CH; and $X^2$ and $X^3$ are $CR^1$; and $R^1$ is $NO_2$. In another embodiment of Formula (IIIc), $X^1$ is CH; and $X^2$ and $X^3$ are $CR^1$; and $R^1$ is $CF_3$. In another embodiment of Formula (IIIc), $X^1$ is CH; and $X^2$ and $X^3$ are $CR^1$; and $R^1$ is C(O)OH. In another embodiment of Formula (IIIc), $X^1$ is CH; and $X^2$ and $X^3$ are $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In one embodiment of formula (IIIc), $R^x$ is $R^5$, $OR^5$, $SO_2R^5$, $C(O)R^5$, $CO(O)R^5$, $NHR^5$, $NHC(O)R^5$, $NHS(O)_2R^5$, $C(O)NH_2$, $C(O)NHR^5$, $C(O)N(R^5)_2$, $CHNOR^5$, $C(O)NHOR^5$, $SO_2NHR^5$ or $CF_3$. In another embodiment of formula (IIIc), $R^x$ is $R^5$, and $R^5$ is heterocyclyl, which is optionally substituted as described in embodiments herein.

In another embodiment of Formula (IIIc), $R^x$ is phthalazin-1(2H)-onyl, isoquinolinyl, isoquinolin-1(2H)-onyl, 5,6,7,8-tetrahydrophthalazin-1(2H)-onyl, 5-fluorophthalazin-1(2H)-onyl, (Z)-3H-benzo[d][1,2]diazepin-4(5H)-onyl, 5-(trifluoromethyl)phthalazin-1(2H)-onyl, pyrrolo[1,2-d][1,2,4]triazin-1(2H)-one, isoindolin-1-onyl, or 1,2,3,6-tetrahydropyridinyl. In another embodiment of Formula (IIIc), $R^x$ is phthalazin-1(2H)-onyl, isoquinolinyl, isoquinolin-1(2H)-onyl, 5,6,7,8-tetrahydrophthalazin-1(2H)-onyl, 5-fluorophthalazin-1(2H)-onyl, (Z)-3H-benzo[d][1,2]diazepin-4(5H)-onyl, 5-(trifluoromethyl)phthalazin-1(2H)-onyl, isoindolin-1-onyl, or pyrrolo[1,2-d][1,2,4]triazin-1(2H)-one; which are optionally substituted as defined herein. In another embodiment of Formula (IIIc), $R^x$ is ,2,3,6-tetrahydropyridinyl; which is optionally substituted as defined herein.

Still another embodiment pertains to compounds having Formula (IIIc), which include N-{4-[(3-phenylpropyl)carbamoyl]phenyl}-1,3-dihydro-2H-isoindole-2-carboxamide;
N-(4-{[4-(aminomethyl)benzyl]carbamoyl}phenyl)-5-fluoro-1,3-dihydro-2H-isoindole-2-carboxamide;
5-cyano-N-{4-[(3-phenylpropyl)carbamoyl]phenyl}-1,3-dihydro-2H-isoindole-2-carboxamide;
N-{4-[(cyclopentylmethyl)carbamoyl]phenyl}-5-fluoro-1,3-dihydro-2H-isoindole-2-carboxamide;
5-cyano-N-[4-(propylcarbamoyl)phenyl]-1,3-dihydro-2H-isoindole-2-carboxamide;
N-(4-{[4-(furo[3,2-c]pyridin-4-yl)piperazin-1-yl]carbonyl}phenyl)-1,3-dihydro-2H-isoindole-2-carboxamide;
5-cyano-N-(4-{[4-(pyridin-2-yl)piperazin-1-yl]carbonyl}phenyl)-1,3-dihydro-2H-isoindole-2-carboxamide;
5-fluoro-N-{4-[(pyridin-2-ylmethyl)carbamoyl]phenyl}-1,3-dihydro-2H-isoindole-2-carboxamide;
N-[4-(benzylcarbamoyl)phenyl]-5-fluoro-1,3-dihydro-2H-isoindole-2-carboxamide;
N-{4-[(3,4-dimethoxybenzyl)carbamoyl]phenyl}-1,3-dihydro-2H-isoindole-2-carboxamide;
5-methyl-N-(4-{[4-(pyridin-2-yl)piperazin-1-yl]carbonyl}phenyl)-1,3-dihydro-2H-isoindole-2-carboxamide;
N-(4-{[4-(thieno[3,2-c]pyridin-4-yl)piperazin-1-yl]carbonyl}phenyl)-1,3-dihydro-2H-isoindole-2-carboxamide;
N-{4-[(2,3-dimethoxybenzyl)carbamoyl]phenyl}-1,3-dihydro-2H-isoindole-2-carboxamide;
5-fluoro-N-{4-[(3-phenylpropyl)carbamoyl]phenyl}-1,3-dihydro-2H-isoindole-2-carboxamide;
5-fluoro-N-(4-{[4-(pyridazin-3-yl)piperazin-1-yl]carbonyl}phenyl)-1,3-dihydro-2H-isoindole-2-carboxamide;
N-{4-[(2,3-dihydro-1,4-benzodioxin-5-ylmethyl)carbamoyl]phenyl}-1,3-dihydro-2H-isoindole-2-carboxamide;
5-fluoro-N-(4-{[1-(3-methylbutyl)-1H-pyrazol-4-yl]carbamoyl}phenyl)-1,3-dihydro-2H-isoindole-2-carboxamide;
N-{4-[(2-fluorobenzyl)carbamoyl]phenyl}-1,3-dihydro-2H-isoindole-2-carboxamide;
5-fluoro-N-(4-{[4-(pyrimidin-2-yl)piperazin-1-yl]carbonyl}phenyl)-1,3-dihydro-2H-isoindole-2-carboxamide;
5-fluoro-N-{4-[(3-methylbutyl)carbamoyl]phenyl}-1,3-dihydro-2H-isoindole-2-carboxamide;
N-{4-[(2-methoxybenzyl)carbamoyl]phenyl}-1,3-dihydro-2H-isoindole-2-carboxamide;
5-fluoro-N-(4-{[4-(pyridin-2-yl)piperazin-1-yl]carbonyl}phenyl)-1,3-dihydro-2H-isoindole-2-carboxamide;
N-{4-[(3-fluorobenzyl)carbamoyl]phenyl}-1,3-dihydro-2H-isoindole-2-carboxamide;
5-fluoro-N-(4-{[3-(2-oxopyrrolidin-1-yl)propyl]carbamoyl}phenyl)-1,3-dihydro-2H-isoindole-2-carboxamide;
5-cyano-N-{4-[(3-methylbutyl)carbamoyl]phenyl}-1,3-dihydro-2H-isoindole-2-carboxamide;
N-{4-[(cyclopentylmethyl)carbamoyl]phenyl}-5-methyl-1,3-dihydro-2H-isoindole-2-carboxamide;
N-(4-{[4-(4-cyanophenyl)piperazin-1-yl]carbonyl}phenyl)-1,3-dihydro-2H-isoindole-2-carboxamide;
N-{4-[(4-fluorobenzyl)carbamoyl]phenyl}-1,3-dihydro-2H-isoindole-2-carboxamide;
N-{4-[(3,5-dimethoxybenzyl)carbamoyl]phenyl}-1,3-dihydro-2H-isoindole-2-carboxamide;
5-fluoro-N-{4-[(tetrahydrofuran-3-ylmethyl)carbamoyl]phenyl}-1,3-dihydro-2H-isoindole-2-carboxamide;
N-{4-[(2,2-dimethylpropyl)carbamoyl]phenyl}-1,3-dihydro-2H-isoindole-2-carboxamide;
5-fluoro-N-(4-{[2-(2-oxopyrrolidin-1-yl)ethyl]carbamoyl}phenyl)-1,3-dihydro-2H-isoindole-2-carboxamide;
N-(4-{[4-(trifluoromethoxy)benzyl]carbamoyl}phenyl)-1,3-dihydro-2H-isoindole-2-carboxamide;

N-(4-{[3-fluoro-5-(trifluoromethyl)benzyl]
carbamoyl}phenyl)-1,3-dihydro-2H-isoindole-2-carboxamide;
5-fluoro-N-(4-{[4-(pyrazin-2-yl)piperazin-1-yl]
carbonyl}phenyl)-1,3-dihydro-2H-isoindole-2-carboxamide;
N-{4-[(3-methylbutyl)carbamoyl]phenyl}-1,3-dihydro-2H-isoindole-2-carboxamide;
5-methoxy-N-{4-[(3-phenylpropyl)carbamoyl]phenyl}-1,3-dihydro-2H-isoindole-2-carboxamide;
N-{4-[(4-chlorobenzyl)carbamoyl]phenyl}-1,3-dihydro-2H-isoindole-2-carboxamide;
N-{4-[(cyclopentylmethyl)carbamoyl]phenyl}-1,3-dihydro-2H-isoindole-2-carboxamide;
N-{4-[(3,4,5-trimethoxybenzyl)carbamoyl]phenyl}-1,3-dihydro-2H-isoindole-2-carboxamide;
N-(4-{[4-(pyrimidin-2-yl)piperazin-1-yl]carbonyl}phenyl)-1,3-dihydro-2H-isoindole-2-carboxamide;
5-nitro-N-[4-(propylcarbamoyl)phenyl]-1,3-dihydro-2H-isoindole-2-carboxamide;
5-methyl-N-{4-[(3-methylbutyl)carbamoyl]phenyl}-1,3-dihydro-2H-isoindole-2-carboxamide;
N-(4-{[4-(4-fluorophenyl)piperazin-1-yl]carbonyl}phenyl)-1,3-dihydro-2H-isoindole-2-carboxamide;
N-{4-[(4-methoxybenzyl)carbamoyl]phenyl}-1,3-dihydro-2H-isoindole-2-carboxamide;
N-{4-[(2-thienylmethyl)carbamoyl]phenyl}-1,3-dihydro-2H-isoindole-2-carboxamide;
N-(4-{[4-(pyrimidin-2-yl)piperazin-1-yl]carbonyl}phenyl)-5-(trifluoromethyl)-1,3-dihydro-2H-isoindole-2-carboxamide;
N-{4-[(1-ethyl-1H-pyrazol-4-yl)carbamoyl]phenyl}-5-fluoro-1,3-dihydro-2H-isoindole-2-carboxamide;
N-{4-[(1-benzyl-1H-pyrazol-4-yl)carbamoyl]phenyl}-5-fluoro-1,3-dihydro-2H-isoindole-2-carboxamide;
N-(4-{[4-(pyridin-2-yl)piperazin-1-yl]carbonyl}phenyl)-1,3-dihydro-2H-isoindole-2-carboxamide;
N-(4-{[4-(pyrazin-2-yl)piperazin-1-yl]carbonyl}phenyl)-1,3-dihydro-2H-isoindole-2-carboxamide;
N-(4-{[4-(2-methoxyphenyl)piperazin-1-yl]
carbonyl}phenyl)-1,3-dihydro-2H-isoindole-2-carboxamide;
N-{4-[(3,3-dimethylbutyl)carbamoyl]phenyl}-1,3-dihydro-2H-isoindole-2-carboxamide;
N-(4-{[(2R)-tetrahydrofuran-2-ylmethyl]
carbamoyl}phenyl)-1,3-dihydro-2H-isoindole-2-carboxamide;
N-(4-{[4-(3-methoxyphenyl)piperazin-1-yl]
carbonyl}phenyl)-1,3-dihydro-2H-isoindole-2-carboxamide;
N-(4-{[4-(4-acetylphenyl)piperazin-1-yl]carbonyl}phenyl)-1,3-dihydro-2H-isoindole-2-carboxamide;
N-(4-{[2-(2,3-dimethoxyphenyl)ethyl]carbamoyl}phenyl)-1,3-dihydro-2H-isoindole-2-carboxamide;
N-{4-[(3-thienylmethyl)carbamoyl]phenyl}-1,3-dihydro-2H-isoindole-2-carboxamide;
5-methoxy-N-{4-[(3-methylbutyl)carbamoyl]phenyl}-1,3-dihydro-2H-isoindole-2-carboxamide;
N-{4-[(pyridin-2-ylmethyl)carbamoyl]phenyl}-1,3-dihydro-2H-isoindole-2-carboxamide;
5-fluoro-N-(4-{[2-(2-thienyl)ethyl]carbamoyl}phenyl)-1,3-dihydro-2H-isoindole-2-carboxamide;
N-(4-{[(2S)-tetrahydrofuran-2-ylmethyl]
carbamoyl}phenyl)-1,3-dihydro-2H-isoindole-2-carboxamide;

N-(4-{[1-(3-methylbutyl)-1H-pyrazol-4-yl]
carbamoyl}phenyl)-1,3-dihydro-2H-isoindole-2-carboxamide;
4-chloro-N-(4-{[4-(pyridin-2-yl)piperazin-1-yl]
carbonyl}phenyl)-1,3-dihydro-2H-isoindole-2-carboxamide;
N-{4-[(4-phenylpiperazin-1-yl)carbonyl]phenyl}-1,3-dihydro-2H-isoindole-2-carboxamide;
N-{4-[(6-aminohexyl)carbamoyl]phenyl}-1,3-dihydro-2H-isoindole-2-carboxamide;
4-chloro-N-{4-[(3-methylbutyl)carbamoyl]phenyl}-1,3-dihydro-2H-isoindole-2-carboxamide;
N-(4-{[2-(2-thienyl)ethyl]carbamoyl}phenyl)-1,3-dihydro-2H-isoindole-2-carboxamide;
5-methoxy-N-(4-{[4-(pyridin-2-yl)piperazin-1-yl]
carbonyl}phenyl)-1,3-dihydro-2H-isoindole-2-carboxamide;
N-{4-[(1,3-benzodioxol-5-ylmethyl)carbamoyl]phenyl}-1,3-dihydro-2H-isoindole-2-carboxamide;
N-{4-[(3-methoxybenzyl)carbamoyl]phenyl}-1,3-dihydro-2H-isoindole-2-carboxamide;
N-(4-{[4-(pyridin-3-yl)piperazin-1-yl]carbonyl}phenyl)-1,3-dihydro-2H-isoindole-2-carboxamide;
N-[4-(benzylcarbamoyl)phenyl]-1,3-dihydro-2H-isoindole-2-carboxamide;
N-(4-{[4-(pyridazin-3-yl)piperazin-1-yl]carbonyl}phenyl)-1,3-dihydro-2H-isoindole-2-carboxamide;
N-{4-[(pyrimidin-4-ylmethyl)carbamoyl]phenyl}-1,3-dihydro-2H-isoindole-2-carboxamide;
N-(4-{[4-(3-fluorophenyl)piperazin-1-yl]carbonyl}phenyl)-1,3-dihydro-2H-isoindole-2-carboxamide;
N-{4-[(2-methylbutyl)carbamoyl]phenyl}-1,3-dihydro-2H-isoindole-2-carboxamide;
N-(4-{[4-(pyridin-2-yl)piperazin-1-yl]carbonyl}phenyl)-5-(trifluoromethyl)-1,3-dihydro-2H-isoindole-2-carboxamide;
N-{4-[(3-butoxypropyl)carbamoyl]phenyl}-1,3-dihydro-2H-isoindole-2-carboxamide;
N-(4-{[(1S)-2-hydroxy-1-phenylethyl]carbamoyl}phenyl)-1,3-dihydro-2H-isoindole-2-carboxamide;
N-(4-{[2-(3,4-dihydroxyphenyl)ethyl]carbamoyl}phenyl)-1,3-dihydro-2H-isoindole-2-carboxamide;
N-{4-[(3-propoxypropyl)carbamoyl]phenyl}-1,3-dihydro-2H-isoindole-2-carboxamide;
N-{4-[(3-furylmethyl)carbamoyl]phenyl}-1,3-dihydro-2H-isoindole-2-carboxamide;
N-(4-{[4-(2-cyanophenyl)piperazin-1-yl]carbonyl}phenyl)-1,3-dihydro-2H-isoindole-2-carboxamide;
N-{4-[(3-hydroxy-2-methylphenyl)carbamoyl]phenyl}-1,3-dihydro-2H-isoindole-2-carboxamide;
N-{4-[(3-methylbutyl)carbamoyl]phenyl}-5-(trifluoromethyl)-1,3-dihydro-2H-isoindole-2-carboxamide;
N-{4-[(3-methyl-1H-indazol-5-yl)carbamoyl]phenyl}-1,3-dihydro-2H-isoindole-2-carboxamide;
N-{4-[(3-ethoxypropyl)carbamoyl]phenyl}-1,3-dihydro-2H-isoindole-2-carboxamide;
N-(4-{[4-(pyrazin-2-yl)piperazin-1-yl]carbonyl}phenyl)-5-(trifluoromethyl)-1,3-dihydro-2H-isoindole-2-carboxamide;
N-(4-{[2-(2,5-dimethoxyphenyl)ethyl]carbamoyl}phenyl)-1,3-dihydro-2H-isoindole-2-carboxamide;
N-{4-[(tetrahydrofuran-3-ylmethyl)carbamoyl]phenyl}-1,3-dihydro-2H-isoindole-2-carboxamide;
N-{4-[(1-benzyl-1H-pyrazol-4-yl)carbamoyl]phenyl}-1,3-dihydro-2H-isoindole-2-carboxamide;
methyl 5-({4-[(1,3-dihydro-2H-isoindol-2-ylcarbonyl)amino]benzoyl}amino)-1H-indazole-3-carboxylate;

N-(4-{[2-(2-oxopyrrolidin-1-yl)ethyl]carbamoyl}phenyl)-1,3-dihydro-2H-isoindole-2-carboxamide;
N-{4-[(pyridin-4-ylmethyl)carbamoyl]phenyl}-1,3-dihydro-2H-isoindole-2-carboxamide;
N-(4-{[4-(5-chloropyridin-2-yl)piperazin-1-yl]carbonyl}phenyl)-1,3-dihydro-2H-isoindole-2-carboxamide;
N-(4-{[2-(1H-indol-3-yl)ethyl]carbamoyl}phenyl)-1,3-dihydro-2H-isoindole-2-carboxamide;
N-(4-{[4-(trifluoromethyl)benzyl]carbamoyl}phenyl)-1,3-dihydro-2H-isoindole-2-carboxamide;
N-{4-[(3,5-dimethoxyphenyl)carbamoyl]phenyl}-1,3-dihydro-2H-isoindole-2-carboxamide;
N-{4-[(pyridin-3-ylmethyl)carbamoyl]phenyl}-1,3-dihydro-2H-isoindole-2-carboxamide;
N-[4-(2,3-dihydro-1,4-benzodioxin-6-ylcarbamoyl)phenyl]-1,3-dihydro-2H-isoindole-2-carboxamide;
N-(4-{[4-(2-fluorobenzoyl)piperazin-1-yl]carbonyl}phenyl)-1,3-dihydro-2H-isoindole-2-carboxamide;
N-(4-{[2-(5-methoxy-1H-indol-3-yl)ethyl]carbamoyl}phenyl)-1,3-dihydro-2H-isoindole-2-carboxamide;
N-{4-[(3-aminobenzyl)carbamoyl]phenyl}-1,3-dihydro-2H-isoindole-2-carboxamide;
N-(4-{[2-(2-chlorophenyl)ethyl]carbamoyl}phenyl)-1,3-dihydro-2H-isoindole-2-carboxamide;
N-(4-{[(2R)-1-hydroxy-4-methylpentan-2-yl]carbamoyl}phenyl)-1,3-dihydro-2H-isoindole-2-carboxamide;
N-{4-[(2-propoxyethyl)carbamoyl]phenyl}-1,3-dihydro-2H-isoindole-2-carboxamide;
N-{4-[(3-isobutoxypropyl)carbamoyl]phenyl}-1,3-dihydro-2H-isoindole-2-carboxamide;
N-(4-{[4-(pyridin-4-yl)piperazin-1-yl]carbonyl}phenyl)-1,3-dihydro-2H-isoindole-2-carboxamide;
N-[4-({4-[5-(trifluoromethyl)pyridin-2-yl]piperazin-1-yl}carbonyl)phenyl]-1,3-dihydro-2H-isoindole-2-carboxamide;
N-{4-[(3,4,5-trimethoxyphenyl)carbamoyl]phenyl}-1,3-dihydro-2H-isoindole-2-carboxamide;
N-{4-[(4-methylpiperidin-1-yl)carbonyl]phenyl}-1,3-dihydro-2H-isoindole-2-carboxamide;
N-[4-({2-[4-(dimethylamino)phenyl]ethyl}carbamoyl)phenyl]-1,3-dihydro-2H-isoindole-2-carboxamide;
N-(4-{[3-(trifluoromethoxy)benzyl]carbamoyl}phenyl)-1,3-dihydro-2H-isoindole-2-carboxamide;
N-(4-{[(1R)-3-hydroxy-1-phenylpropyl]carbamoyl}phenyl)-1,3-dihydro-2H-isoindole-2-carboxamide;
N-{4-[(3-cyanophenyl)carbamoyl]phenyl}-1,3-dihydro-2H-isoindole-2-carboxamide;
N-{4-[(3-fluoro-4-methoxyphenyl)carbamoyl]phenyl}-1,3-dihydro-2H-isoindole-2-carboxamide;
N-{4-[(2,3-dimethoxyphenyl)carbamoyl]phenyl}-1,3-dihydro-2H-isoindole-2-carboxamide;
N-(4-{[2-(2-fluorophenyl)ethyl]carbamoyl}phenyl)-1,3-dihydro-2H-isoindole-2-carboxamide;
N-[4-(isobutylcarbamoyl)phenyl]-1,3-dihydro-2H-isoindole-2-carboxamide;
N-(4-{[2-(1,3-benzodioxol-5-yl)ethyl]carbamoyl}phenyl)-1,3-dihydro-2H-isoindole-2-carboxamide;
N-(4-{[2-(2-methoxyphenyl)ethyl]carbamoyl}phenyl)-1,3-dihydro-2H-isoindole-2-carboxamide;
N-[4-(butylcarbamoyl)phenyl]-1,3-dihydro-2H-isoindole-2-carboxamide;
N-{4-[(2-isopropoxyethyl)carbamoyl]phenyl}-1,3-dihydro-2H-isoindole-2-carboxamide;
N-{4-[(3-isopropoxypropyl)carbamoyl]phenyl}-1,3-dihydro-2H-isoindole-2-carboxamide;
4-chloro-N-{4-[(3-phenylpropyl)carbamoyl]phenyl}-1,3-dihydro-2H-isoindole-2-carboxamide;
N-(4-{[2-(4-methoxyphenyl)ethyl]carbamoyl}phenyl)-1,3-dihydro-2H-isoindole-2-carboxamide;
N-{4-[(3-methoxypropyl)carbamoyl]phenyl}-1,3-dihydro-2H-isoindole-2-carboxamide;
N-(4-{[2-(4-fluorophenyl)ethyl]carbamoyl}phenyl)-1,3-dihydro-2H-isoindole-2-carboxamide;
N-(4-{[3-(2-oxopyrrolidin-1-yl)propyl]carbamoyl}phenyl)-1,3-dihydro-2H-isoindole-2-carboxamide;
N-{4-[(2,4-dimethoxyphenyl)carbamoyl]phenyl}-1,3-dihydro-2H-isoindole-2-carboxamide;
$N^2$-[4-(propylcarbamoyl)phenyl]-1,3-dihydro-2H-isoindole-2,5-dicarboxamide;
N-{4-[(2-phenoxyethyl)carbamoyl]phenyl}-1,3-dihydro-2H-isoindole-2-carboxamide;
N-(4-{[2-(4-hydroxyphenyl)ethyl]carbamoyl}phenyl)-1,3-dihydro-2H-isoindole-2-carboxamide;
N-(4-{[2-(3-fluorophenyl)ethyl]carbamoyl}phenyl)-1,3-dihydro-2H-isoindole-2-carboxamide;
N-[4-({1-[(3S)-tetrahydrofuran-3-yl]-1H-pyrazol-4-yl}carbamoyl)phenyl]-1,3-dihydro-2H-isoindole-2-carboxamide;
5-methyl-N-{4-[(3-phenylpropyl)carbamoyl]phenyl}-1,3-dihydro-2H-isoindole-2-carboxamide;
N-[4-(1,4-dioxa-8-azaspiro[4.5]dec-8-ylcarbonyl)phenyl]-1,3-dihydro-2H-isoindole-2-carboxamide;
N-{4-[(2-phenylethyl)carbamoyl]phenyl}-1,3-dihydro-2H-isoindole-2-carboxamide;
N-(4-{[2-(2,4-dimethoxyphenyl)ethyl]carbamoyl}phenyl)-1,3-dihydro-2H-isoindole-2-carboxamide;
N-(4-{[3-(methylthio)propyl]carbamoyl}phenyl)-1,3-dihydro-2H-isoindole-2-carboxamide;
N-{4-[(2-ethoxyethyl)carbamoyl]phenyl}-1,3-dihydro-2H-isoindole-2-carboxamide;
N-{4-[(2-fluorophenyl)carbamoyl]phenyl}-1,3-dihydro-2H-isoindole-2-carboxamide;
N-(4-{[2-(pyridin-3-yl)ethyl]carbamoyl}phenyl)-1,3-dihydro-2H-isoindole-2-carboxamide;
N-[4-({4-[(trifluoromethyl)thio]benzyl}carbamoyl)phenyl]-1,3-dihydro-2H-isoindole-2-carboxamide;
N-{4-[(3,4-dimethoxyphenyl)carbamoyl]phenyl}-1,3-dihydro-2H-isoindole-2-carboxamide;
N-(4-{[3-(2-fluorophenyl)pyrrolidin-1-yl]carbonyl}phenyl)-1,3-dihydro-2H-isoindole-2-carboxamide;
N-(4-{[3-(1H-imidazol-1-yl)propyl]carbamoyl}phenyl)-1,3-dihydro-2H-isoindole-2-carboxamide;
N-(4-{[2-(3-chlorophenyl)ethyl]carbamoyl}phenyl)-1,3-dihydro-2H-isoindole-2-carboxamide;
N-{4-[(4-hydroxybutyl)carbamoyl]phenyl}-1,3-dihydro-2H-isoindole-2-carboxamide;
N-{4-[(3-phenylpropyl)carbamoyl]phenyl}-5-(trifluoromethyl)-1,3-dihydro-2H-isoindole-2-carboxamide;
N-(4-{[4-(hydroxymethyl)phenyl]carbamoyl}phenyl)-1,3-dihydro-2H-isoindole-2-carboxamide;
N-[4-(1,3-benzodioxol-5-ylcarbamoyl)phenyl]-1,3-dihydro-2H-isoindole-2-carboxamide;
N-{4-[(1-isopropyl-1H-pyrazol-4-yl)carbamoyl]phenyl}-1,3-dihydro-2H-isoindole-2-carboxamide;
N-{4-[(4-hydroxyphenyl)carbamoyl]phenyl}-1,3-dihydro-2H-isoindole-2-carboxamide;

N-{4-[(1-ethyl-1H-pyrazol-4-yl)carbamoyl]phenyl}-1,3-dihydro-2H-isoindole-2-carboxamide;
N-{4-[(2,5-dimethoxyphenyl)carbamoyl]phenyl}-1,3-dihydro-2H-isoindole-2-carboxamide;
N-{4-[methyl(3-phenylpropyl)carbamoyl]phenyl}-1,3-dihydro-2H-isoindole-2-carboxamide;
N-{4-[(2-hydroxy-2-methylpropyl)carbamoyl]phenyl}-1,3-dihydro-2H-isoindole-2-carboxamide;
N-(4-{[4-(trifluoromethyl)piperidin-1-yl]carbonyl}phenyl)-1,3-dihydro-2H-isoindole-2-carboxamide;
N-[4-(thiomorpholin-4-ylcarbonyl)phenyl]-1,3-dihydro-2H-isoindole-2-carboxamide;
N-[4-(5,6-dihydroimidazo[1,5-a]pyrazin-7(8H)-ylcarbonyl)phenyl]-1,3-dihydro-2H-isoindole-2-carboxamide;
N-(4-{[4-(2-furoyl)piperazin-1-yl]carbonyl}phenyl)-1,3-dihydro-2H-isoindole-2-carboxamide;
N-{4-[(1-benzylpiperidin-4-yl)carbamoyl]phenyl}-1,3-dihydro-2H-isoindole-2-carboxamide;
N-{4-[(4-methoxyphenyl)carbamoyl]phenyl}-1,3-dihydro-2H-isoindole-2-carboxamide;
N-{4-[(3-methoxyphenyl)carbamoyl]phenyl}-1,3-dihydro-2H-isoindole-2-carboxamide;
N-{4-[(5-acetamido-2-methoxyphenyl)carbamoyl]phenyl}-1,3-dihydro-2H-isoindole-2-carboxamide;
N-(4-{[2-(3,5-dimethoxyphenyl)ethyl]carbamoyl}phenyl)-1,3-dihydro-2H-isoindole-2-carboxamide;
N-[4-({2-[3-(trifluoromethyl)phenyl]ethyl}carbamoyl)phenyl]-1,3-dihydro-2H-isoindole-2-carboxamide;
N-{4-[(2-methylbutan-2-yl)carbamoyl]phenyl}-1,3-dihydro-2H-isoindole-2-carboxamide;
N-(4-{[2-(1H-imidazol-4-yl)ethyl]carbamoyl}phenyl)-1,3-dihydro-2H-isoindole-2-carboxamide;
N-(4-{[(2S)-2-hydroxypropyl]carbamoyl}phenyl)-1,3-dihydro-2H-isoindole-2-carboxamide;
N-(4-{[(1R)-1-(3-cyanophenyl)ethyl]carbamoyl}phenyl)-1,3-dihydro-2H-isoindole-2-carboxamide;
N-(4-{[(2S)-1-hydroxy-3-methylbutan-2-yl]carbamoyl}phenyl)-1,3-dihydro-2H-isoindole-2-carboxamide;
N-{4-[benzyl(2-hydroxyethyl)carbamoyl]phenyl}-1,3-dihydro-2H-isoindole-2-carboxamide;
N-{4-[(4-cyanophenyl)carbamoyl]phenyl}-1,3-dihydro-2H-isoindole-2-carboxamide;
N-(4-{[2-(4-chlorophenyl)ethyl]carbamoyl}phenyl)-1,3-dihydro-2H-isoindole-2-carboxamide;
N-(4-{[2-(4-methylpiperazin-1-yl)ethyl]carbamoyl}phenyl)-1,3-dihydro-2H-isoindole-2-carboxamide;
N-(4-{[2-(pyridin-2-yl)ethyl]carbamoyl}phenyl)-1,3-dihydro-2H-isoindole-2-carboxamide;
N-{4-[(cyanomethyl)carbamoyl]phenyl}-1,3-dihydro-2H-isoindole-2-carboxamide;
N-[4-(cyclohexylcarbamoyl)phenyl]-1,3-dihydro-2H-isoindole-2-carboxamide;
N-{4-[(3-hydroxyphenyl)carbamoyl]phenyl}-1,3-dihydro-2H-isoindole-2-carboxamide;
N-{4-[butyl(methyl)carbamoyl]phenyl}-1,3-dihydro-2H-isoindole-2-carboxamide;
N-(4-{[4-(dimethylamino)phenyl]carbamoyl}phenyl)-1,3-dihydro-2H-isoindole-2-carboxamide;
N-[4-(3,4-dihydroisoquinolin-2(1H)-ylcarbonyl)phenyl]-1,3-dihydro-2H-isoindole-2-carboxamide;
N-[4-(1,3-dihydro-2H-isoindol-2-ylcarbonyl)phenyl]-1,3-dihydro-2H-isoindole-2-carboxamide;
N-[4-(2,3-dihydro-1H-indol-1-ylcarbonyl)phenyl]-1,3-dihydro-2H-isoindole-2-carboxamide;
N-[4-(phenylcarbamoyl)phenyl]-1,3-dihydro-2H-isoindole-2-carboxamide;
N-{4-[(4-fluorophenyl)carbamoyl]phenyl}-1,3-dihydro-2H-isoindole-2-carboxamide;
N-(4-{[2-(diethylamino)ethyl]carbamoyl}phenyl)-1,3-dihydro-2H-isoindole-2-carboxamide;
N-{4-[(2-hydroxy-2-phenylethyl)(methyl)carbamoyl]phenyl}-1,3-dihydro-2H-isoindole-2-carboxamide;
N-{4-[(2-aminophenyl)carbamoyl]phenyl}-1,3-dihydro-2H-isoindole-2-carboxamide;
N-(4-{[(2R)-2-hydroxypropyl]carbamoyl}phenyl)-1,3-dihydro-2H-isoindole-2-carboxamide;
N-(4-{[(2S)-1-amino-4-methyl-1-oxopentan-2-yl]carbamoyl}phenyl)-1,3-dihydro-2H-isoindole-2-carboxamide;
tert-butyl (1-{4-[(1,3-dihydro-2H-isoindol-2-ylcarbonyl)amino]benzoyl}piperidin-4-yl)carbamate;
N-(4-{[3-(morpholin-4-yl)propyl]carbamoyl}phenyl)-1,3-dihydro-2H-isoindole-2-carboxamide;
N-[4-({4-[3-chloro-5-(trifluoromethyl)pyridin-2-yl]piperazin-1-yl}carbonyl)phenyl]-1,3-dihydro-2H-isoindole-2-carboxamide;
N-(4-{[4-(cyclohexylmethyl)piperazin-1-yl]carbonyl}phenyl)-1,3-dihydro-2H-isoindole-2-carboxamide;
N-(4-{[1-(3-chlorobenzyl)-1H-pyrazol-4-yl]carbamoyl}phenyl)-1,3-dihydro-2H-isoindole-2-carboxamide;
N-(4-{[3-(diethylcarbamoyl)piperidin-1-yl]carbonyl}phenyl)-1,3-dihydro-2H-isoindole-2-carboxamide;
N-(4-{[3-(piperidin-1-yl)propyl]carbamoyl}phenyl)-1,3-dihydro-2H-isoindole-2-carboxamide;
N-(4-{[4-(2-hydroxyethyl)piperazin-1-yl]carbonyl}phenyl)-1,3-dihydro-2H-isoindole-2-carboxamide;
N-{4-[(2-hydroxy-6-methylphenyl)carbamoyl]phenyl}-1,3-dihydro-2H-isoindole-2-carboxamide;
N-(4-{[4-(dimethylamino)butyl]carbamoyl}phenyl)-1,3-dihydro-2H-isoindole-2-carboxamide;
N-{4-[(3-hydroxypropyl)carbamoyl]phenyl}-1,3-dihydro-2H-isoindole-2-carboxamide;
N-{4-[(4-cyclohexylpiperazin-1-yl)carbonyl]phenyl}-1,3-dihydro-2H-isoindole-2-carboxamide;
N-[4-(5,6-dihydro[1,2,4]triazolo[4,3-a]pyrazin-7(8H)-ylcarbonyl)phenyl]-1,3-dihydro-2H-isoindole-2-carboxamide;
N-{4-[methyl(3-methylbutyl)carbamoyl]phenyl}-1,3-dihydro-2H-isoindole-2-carboxamide;
N-[4-(propylcarbamoyl)phenyl]-1,3-dihydro-2H-isoindole-2-carboxamide;
N-(4-{[(2S)-1-hydroxybutan-2-yl]carbamoyl}phenyl)-1,3-dihydro-2H-isoindole-2-carboxamide;
N-{4-[(5-fluoropyridin-2-yl)carbamoyl]phenyl}-1,3-dihydro-2H-isoindole-2-carboxamide;
N-{4-[(cyclopropylmethyl)(propyl)carbamoyl]phenyl}-1,3-dihydro-2H-isoindole-2-carboxamide;
N-(4-{[(2S)-1-methoxypropan-2-yl]carbamoyl}phenyl)-1,3-dihydro-2H-isoindole-2-carboxamide;
N-[4-(1,3,4,9-tetrahydro-2H-beta-carbolin-2-ylcarbonyl)phenyl]-1,3-dihydro-2H-isoindole-2-carboxamide;
N-[4-(tert-butylcarbamoyl)phenyl]-1,3-dihydro-2H-isoindole-2-carboxamide;
N-[4-({4-[4-(trifluoromethyl)phenyl]piperazin-1-yl}carbonyl)phenyl]-1,3-dihydro-2H-isoindole-2-carboxamide;

N-{4-[(3-methylbutan-2-yl)carbamoyl]phenyl}-1,3-dihydro-2H-isoindole-2-carboxamide;
N-{4-[(3,3-difluoropyrrolidin-1-yl)carbonyl]phenyl}-1,3-dihydro-2H-isoindole-2-carboxamide;
N-{4-[(2-methylpiperidin-1-yl)carbonyl]phenyl}-1,3-dihydro-2H-isoindole-2-carboxamide;
N-(4-{[(3S)-1-benzylpyrrolidin-3-yl]carbamoyl}phenyl)-1,3-dihydro-2H-isoindole-2-carboxamide;
N-{4-[(4-hydroxypiperidin-1-yl)carbonyl]phenyl}-1,3-dihydro-2H-isoindole-2-carboxamide;
N-{4-[bis(2-methoxyethyl)carbamoyl]phenyl}-1,3-dihydro-2H-isoindole-2-carboxamide;
N-{4-[(3-fluorophenyl)carbamoyl]phenyl}-1,3-dihydro-2H-isoindole-2-carboxamide;
N-[4-(cyclopentylcarbamoyl)phenyl]-1,3-dihydro-2H-isoindole-2-carboxamide;
N-{4-[(4-carbamoylpiperidin-1-yl)carbonyl]phenyl}-1,3-dihydro-2H-isoindole-2-carboxamide;
N-[4-(cyclopropylcarbamoyl)phenyl]-1,3-dihydro-2H-isoindole-2-carboxamide;
N-[4-(methylcarbamoyl)phenyl]-1,3-dihydro-2H-isoindole-2-carboxamide;
N-(4-{[3-(dimethylamino)propyl]carbamoyl}phenyl)-1,3-dihydro-2H-isoindole-2-carboxamide;
N-{4-[methyl(tetrahydrofuran-2-ylmethyl)carbamoyl]phenyl}-1,3-dihydro-2H-isoindole-2-carboxamide;
N-[4-(pentan-2-ylcarbamoyl)phenyl]-1,3-dihydro-2H-isoindole-2-carboxamide;
N-[4-(pentan-3-ylcarbamoyl)phenyl]-1,3-dihydro-2H-isoindole-2-carboxamide;
N-[4-(cyclobutylcarbamoyl)phenyl]-1,3-dihydro-2H-isoindole-2-carboxamide;
N-{4-[(1,3-dioxolan-2-ylmethyl)(methyl)carbamoyl]phenyl}-1,3-dihydro-2H-isoindole-2-carboxamide;
N-(4-{[1-(4-fluorophenyl)-1H-pyrazol-4-yl]carbamoyl}phenyl)-1,3-dihydro-2H-isoindole-2-carboxamide;
N-{4-[(1-hydroxy-2-methylpropan-2-yl)carbamoyl]phenyl}-1,3-dihydro-2H-isoindole-2-carboxamide;
N-{4-[(1-phenyl-1H-pyrazol-4-yl)carbamoyl]phenyl}-1,3-dihydro-2H-isoindole-2-carboxamide;
N-[4-({2-[4-(trifluoromethyl)phenyl]ethyl}carbamoyl)phenyl]-1,3-dihydro-2H-isoindole-2-carboxamide;
N-{4-[(2-methoxyethyl)(propyl)carbamoyl]phenyl}-1,3-dihydro-2H-isoindole-2-carboxamide;
N-[4-(sec-butylcarbamoyl)phenyl]-1,3-dihydro-2H-isoindole-2-carboxamide;
N-(4-{[3-(trifluoromethyl)piperidin-1-yl]carbonyl}phenyl)-1,3-dihydro-2H-isoindole-2-carboxamide;
N-{4-[bis(2-ethoxyethyl)carbamoyl]phenyl}-1,3-dihydro-2H-isoindole-2-carboxamide;
N-{4-[butyl(ethyl)carbamoyl]phenyl}-1,3-dihydro-2H-isoindole-2-carboxamide;
N-{4-[(1-methoxypropan-2-yl)carbamoyl]phenyl}-1,3-dihydro-2H-isoindole-2-carboxamide;
N-{4-[(2-methoxyethyl)(methyl)carbamoyl]phenyl}-1,3-dihydro-2H-isoindole-2-carboxamide;
N-{4-[(3R)-tetrahydrofuran-3-ylcarbamoyl]phenyl}-1,3-dihydro-2H-isoindole-2-carboxamide;
N-[4-(morpholin-4-ylcarbonyl)phenyl]-1,3-dihydro-2H-isoindole-2-carboxamide;
N-{4-[isobutyl(methyl)carbamoyl]phenyl}-1,3-dihydro-2H-isoindole-2-carboxamide;
N-[4-({4-[2-(2-hydroxyethoxy)ethyl]piperazin-1-yl}carbonyl)phenyl]-1,3-dihydro-2H-isoindole-2-carboxamide;
N-{4-[(3-methylpiperidin-1-yl)carbonyl]phenyl}-1,3-dihydro-2H-isoindole-2-carboxamide;
N-(4-carbamoylphenyl)-1,3-dihydro-2H-isoindole-2-carboxamide;
N-(4-{[(2S)-2-(trifluoromethyl)pyrrolidin-1-yl]carbonyl}phenyl)-1,3-dihydro-2H-isoindole-2-carboxamide;
N-(4-{[(2S)-1-hydroxy-4-methylpentan-2-yl]carbamoyl}phenyl)-1,3-dihydro-2H-isoindole-2-carboxamide;
N-(4-{[(1R)-2-hydroxy-1-phenylethyl]carbamoyl}phenyl)-1,3-dihydro-2H-isoindole-2-carboxamide;
N-{4-[(2-methylpyrrolidin-1-yl)carbonyl]phenyl}-1,3-dihydro-2H-isoindole-2-carboxamide;
N-{4-[ethyl(2-methoxyethyl)carbamoyl]phenyl}-1,3-dihydro-2H-isoindole-2-carboxamide;
N-(4-{[(2R)-1-hydroxy-3-methylbutan-2-yl]carbamoyl}phenyl)-1,3-dihydro-2H-isoindole-2-carboxamide;
N-{4-[(2,6-dimethylmorpholin-4-yl)carbonyl]phenyl}-1,3-dihydro-2H-isoindole-2-carboxamide;
N-(4-{[(2R)-1-hydroxybutan-2-yl]carbamoyl}phenyl)-1,3-dihydro-2H-isoindole-2-carboxamide;
N-{4-[(2,5-dimethylpyrrolidin-1-yl)carbonyl]phenyl}-1,3-dihydro-2H-isoindole-2-carboxamide;
N-[4-(prop-2-yn-1-ylcarbamoyl)phenyl]-1,3-dihydro-2H-isoindole-2-carboxamide;
N-{4-[isopropyl(2-methoxyethyl)carbamoyl]phenyl}-1,3-dihydro-2H-isoindole-2-carboxamide;
N-{4-[isopropyl(propyl)carbamoyl]phenyl}-1,3-dihydro-2H-isoindole-2-carboxamide;
N-{4-[(2-cyanoethyl)(cyclopropyl)carbamoyl]phenyl}-1,3-dihydro-2H-isoindole-2-carboxamide;
N-{4-[ethyl(isopropyl)carbamoyl]phenyl}-1,3-dihydro-2H-isoindole-2-carboxamide;
N-{4-[(3-fluoropyrrolidin-1-yl)carbonyl]phenyl}-1,3-dihydro-2H-isoindole-2-carboxamide;
N-{4-[(1,3-dihydro-2H-isoindol-2-ylcarbonyl)amino]benzoyl}-N-isopropyl-b eta-alanine;
N-{4-[methyl(propyl)carbamoyl]phenyl}-1,3-dihydro-2H-isoindole-2-carboxamide;
5,6-dimethoxy-N-{4-[(3-phenylpropyl)carbamoyl]phenyl}-1,3-dihydro-2H-isoindole-2-carboxamide;
N-(4-{[3-(4-chlorophenoxy)propyl]carbamoyl}phenyl)-1,3-dihydro-2H-isoindole-2-carboxamide;
N-(4-{[4-(trifluoromethoxy)phenyl]carbamoyl}phenyl)-1,3-dihydro-2H-isoindole-2-carboxamide;
N-{4-[(4-phenyl-1,3-thiazol-2-yl)carbamoyl]phenyl}-1,3-dihydro-2H-isoindole-2-carboxamide;
methyl 2-{[4-(propylcarbamoyl)phenyl]carbamoyl}isoindoline-5-carboxylate;
2-{[4-(propylcarbamoyl)phenyl]carbamoyl}isoindoline-5-carboxylic acid;
5-amino-N-[4-(propylcarbamoyl)phenyl]-1,3-dihydro-2H-isoindole-2-carboxamide;
5-(hydroxymethyl)-N-[4-(propylcarbamoyl)phenyl]-1,3-dihydro-2H-isoindole-2-carboxamide;
5-(aminomethyl)-N-[4-(propylcarbamoyl)phenyl]-1,3-dihydro-2H-isoindole-2-carboxamide;
5-[(2-hydroxy-2-methylpropanoyl)amino]-N-[4-(propylcarbamoyl)phenyl]-1,3-dihydro-2H-isoindole-2-carboxamide;
5-acetamido-N-[4-(propylcarbamoyl)phenyl]-1,3-dihydro-2H-isoindole-2-carboxamide;
5-[(N,N-dimethylglycyl)amino]-N-[4-(propylcarbamoyl)phenyl]-1,3-dihydro-2H-isoindole-2-carboxamide;

N-[4-(propylcarbamoyl)phenyl]-5-(1H-pyrazol-3-yl)-1,3-dihydro-2H-isoindole-2-carboxamide;
N-[4-(propylcarbamoyl)phenyl]-5-(1H-pyrazol-4-yl)-1,3-dihydro-2H-isoindole-2-carboxamide;
5-[(methoxyacetyl)amino]-N-[4-(propylcarbamoyl)phenyl]-1,3-dihydro-2H-isoindole-2-carboxamide;
5-[(methylsulfonyl)amino]-N-[4-(propylcarbamoyl)phenyl]-1,3-dihydro-2H-isoindole-2-carboxamide;
5-bromo-N-[4-(propylcarbamoyl)phenyl]-1,3-dihydro-2H-isoindole-2-carboxamide;
N-{4-[(3,5-dimethoxybenzyl)carbamoyl]phenyl}-1,3-dihydro-2H-pyrrolo[3,4-c]pyridine-2-carboxamide;
N-{4-[(4-chlorobenzyl)carbamoyl]phenyl}-1,3-dihydro-2H-pyrrolo[3,4-c]pyridine-2-carboxamide;
N-(4-{[4-(pyridin-2-yl)piperazin-1-yl]carbonyl}phenyl)-1,3-dihydro-2H-pyrrolo[3,4-c]pyridine-2-carboxamide;
N-{4-[(3-phenylpropyl)carbamoyl]phenyl}-1,3-dihydro-2H-pyrrolo[3,4-c]pyridine-2-carboxamide;
N-{4-[(tetrahydrofuran-3-ylmethyl)carbamoyl]phenyl}-1,3-dihydro-2H-pyrrolo[3,4-c]pyridine-2-carboxamide;
N-{4-[(3-methylbutyl)carbamoyl]phenyl}-1,3-dihydro-2H-pyrrolo[3,4-c]pyridine-2-carboxamide;
N-{4-[(4,4,4-trifluorobutanoyl)amino]phenyl}-1,3-dihydro-2H-isoindole-2-carboxamide;
N-{4-[(3-ethoxypropanoyl)amino]phenyl}-1,3-dihydro-2H-isoindole-2-carboxamide;
N-{4-[(4-phenylbutanoyl)amino]phenyl}-1,3-dihydro-2H-isoindole-2-carboxamide;
N-{4-[(4-methylpentanoyl)amino]phenyl}-1,3-dihydro-2H-isoindole-2-carboxamide;
N-(4-{[(benzyloxy)acetyl]amino}phenyl)-1,3-dihydro-2H-isoindole-2-carboxamide;
N-{4-[(3-phenylpropanoyl)amino]phenyl}-1,3-dihydro-2H-isoindole-2-carboxamide;
N-{4-[(3-phenoxypropanoyl)amino]phenyl}-1,3-dihydro-2H-isoindole-2-carboxamide;
N-(4-{[N-(2-furoyl)glycyl]amino}phenyl)-1,3-dihydro-2H-isoindole-2-carboxamide;
N-(4-{[4-(2-thienyl)butanoyl]amino}phenyl)-1,3-dihydro-2H-isoindole-2-carboxamide;
N-{4-[(4-oxo-4-phenylbutanoyl)amino]phenyl}-1,3-dihydro-2H-isoindole-2-carboxamide;
N-{4-[(N-benzoylglycyl)amino]phenyl}-1,3-dihydro-2H-isoindole-2-carboxamide;
N-{4-[(4-phenoxybutanoyl)amino]phenyl}-1,3-dihydro-2H-isoindole-2-carboxamide;
N-[4-(propionylamino)phenyl]-1,3-dihydro-2H-isoindole-2-carboxamide;
N-[4-(pentanoylamino)phenyl]-1,3-dihydro-2H-isoindole-2-carboxamide;
N-[4-(hexanoylamino)phenyl]-1,3-dihydro-2H-isoindole-2-carboxamide;
N-[4-(heptanoylamino)phenyl]-1,3-dihydro-2H-isoindole-2-carboxamide;
N-[4-(pent-4-enoylamino)phenyl]-1,3-dihydro-2H-isoindole-2-carboxamide;
N-{4-[(ethoxyacetyl)amino]phenyl}-1,3-dihydro-2H-isoindole-2-carboxamide;
N-(4-{[(2-methoxyethoxy)acetyl]amino}phenyl)-1,3-dihydro-2H-isoindole-2-carboxamide;
N-{4-[(cyclopropylacetyl)amino]phenyl}-1,3-dihydro-2H-isoindole-2-carboxamide;
N-{4-[(cyclopentylacetyl)amino]phenyl}-1,3-dihydro-2H-isoindole-2-carboxamide;
N-(4-{[3-(4-methylpiperazin-1-yl)propanoyl]amino}phenyl)-1,3-dihydro-2H-isoindole-2-carboxamide;
methyl 2-({4-[(cyclopentylacetyl)amino]phenyl}carbamoyl)isoindoline-5-carboxylate;
2-({4-[(cyclopentylacetyl)amino]phenyl}carbamoyl)isoindoline-5-carboxylic acid;
N-{4-[(cyclopentylacetyl)amino]phenyl}-5-(hydroxymethyl)-1,3-dihydro-2H-isoindole-2-carboxamide;
N-{4-[(2-cyclopentylethyl)amino]phenyl}-5-(hydroxymethyl)-1,3-dihydro-2H-isoindole-2-carboxamide;
tert-butyl 4-{4-[(1,3-dihydro-2H-isoindol-2-ylcarbonyl)amino]phenyl}-3,6-dihydropyridine-1(2H)-carboxylate;
N-[4-(1,2,3,6-tetrahydropyridin-4-yl)phenyl]-1,3-dihydro-2H-isoindole-2-carboxamide;
N-{4-[1-(3-methylbutyl)-1H-pyrazol-4-yl]phenyl}-1,3-dihydro-2H-isoindole-2-carboxamide;
N-[4-(1-methyl-1H-pyrazol-4-yl)phenyl]-1,3-dihydro-2H-isoindole-2-carboxamide;
N-{4-[(1E)-5-phenylpent-1-en-1-yl]phenyl}-1,3-dihydro-2H-isoindole-2-carboxamide;
N-[4-(1-propyl-1H-pyrazol-4-yl)phenyl]-1,3-dihydro-2H-isoindole-2-carboxamide;
N-[4-(1-benzyl-1H-pyrazol-4-yl)phenyl]-1,3-dihydro-2H-isoindole-2-carboxamide;
N-{4-[1-(2-hydroxyethyl)-1H-pyrazol-4-yl]phenyl}-1,3-dihydro-2H-isoindole-2-carboxamide;
N-[4-(5-phenylpentyl)phenyl]-1,3-dihydro-2H-isoindole-2-carboxamide;
N-[4-(1-butyryl-1,2,3,6-tetrahydropyridin-4-yl)phenyl]-1,3-dihydro-2H-isoindole-2-carboxamide;
N-[4-(1-isobutyryl-1,2,3,6-tetrahydropyridin-4-yl)phenyl]-1,3-dihydro-2H-isoindole-2-carboxamide;
N-[4-(1-benzoyl-1,2,3,6-tetrahydropyridin-4-yl)phenyl]-1,3-dihydro-2H-isoindole-2-carboxamide;
N-{4-[1-(isopropylsulfonyl)-1,2,3,6-tetrahydropyridin-4-yl]phenyl}-1,3-dihydro-2H-isoindole-2-carboxamide;
N-[4-(4-benzoylpiperazin-1-yl)phenyl]-1,3-dihydro-2H-isoindole-2-carboxamide;
N-{4-[4-(isopropylsulfonyl)piperazin-1-yl]phenyl}-1,3-dihydro-2H-isoindole-2-carboxamide;
N-{4-[4-(phenylsulfonyl)piperazin-1-yl]phenyl}-1,3-dihydro-2H-isoindole-2-carboxamide;
N-{4-[3-(benzoylamino)pyrrolidin-1-yl]phenyl}-1,3-dihydro-2H-isoindole-2-carboxamide;
N-{4-[3-(butyrylamino)pyrrolidin-1-yl]phenyl}-1,3-dihydro-2H-isoindole-2-carboxamide;
tert-butyl 4-{4-[(1,3-dihydro-2H-isoindol-2-ylcarbonyl)amino]phenyl}piperazine-1-carboxylate;
N-[4-(4-propionylpiperazin-1-yl)phenyl]-1,3-dihydro-2H-isoindole-2-carboxamide;
N-{4-[4-(cyclopropylcarbonyl)piperazin-1-yl]phenyl}-1,3-dihydro-2H-isoindole-2-carboxamide;
N-[4-(hexyloxy)phenyl]-1,3-dihydro-2H-isoindole-2-carboxamide;
5-fluoro-N-[4-(propylcarbamoyl)phenyl]-1,3-dihydro-2H-isoindole-2-carboxamide;
N-[4-(4-oxo-3,4-dihydrophthalazin-1-yl)phenyl]-1,3-dihydro-2H-isoindole-2-carboxamide;
N-[4-(isoquinolin-4-yl)phenyl]-1,3-dihydro-2H-isoindole-2-carboxamide;
N-[4-(1-oxo-1,2-dihydroisoquinolin-4-yl)phenyl]-1,3-dihydro-2H-isoindole-2-carboxamide;
N-[4-(4-oxo-3,4,5,6,7,8-hexahydrophthalazin-1-yl)phenyl]-1,3-dihydro-2H-isoindole-2-carboxamide;
N-[4-(8-fluoro-4-oxo-3,4-dihydrophthalazin-1-yl)phenyl]-1,3-dihydro-2H-isoindole-2-carboxamide;
5-fluoro-N-[4-(4-oxo-3,4-dihydrophthalazin-1-yl)phenyl]-1,3-dihydro-2H-isoindole-2-carboxamide;

N-[4-(4-oxo-3,4-dihydrophthalazin-1-yl)phenyl]-5-(pyrrolidin-1-ylmethyl)-1,3-dihydro-2H-isoindole-2-carboxamide;
5-(morpholin-4-ylmethyl)-N-[4-(1-oxo-1,2-dihydroisoquinolin-4-yl)phenyl]-1,3-dihydro-2H-isoindole-2-carboxamide;
5-methoxy-N-[4-(1-oxo-1,2-dihydroisoquinolin-4-yl)phenyl]-1,3-dihydro-2H-isoindole-2-carboxamide;
5-[(4-methylpiperazin-1-yl)methyl]-N-[4-(4-oxo-3,4-dihydrophthalazin-1-yl)phenyl]-1,3-dihydro-2H-isoindole-2-carboxamide;
5-cyano-N-[4-(1-oxo-1,2-dihydroisoquinolin-4-yl)phenyl]-1,3-dihydro-2H-isoindole-2-carboxamide;
5-chloro-N-[4-(1-oxo-1,2-dihydroisoquinolin-4-yl)phenyl]-1,3-dihydro-2H-isoindole-2-carboxamide;
N-[4-(4-oxo-4,5-dihydro-3H-2,3-benzodiazepin-1-yl)phenyl]-1,3-dihydro-2H-isoindole-2-carboxamide;
N-[4-(1-oxo-1,2-dihydroisoquinolin-4-yl)phenyl]-5-(pyrrolidin-1-ylmethyl)-1,3-dihydro-2H-isoindole-2-carboxamide;
N-{4-[4-oxo-8-(trifluoromethyl)-3,4-dihydrophthalazin-1-yl]phenyl}-1,3-dihydro-2H-isoindole-2-carboxamide;
5-[(dimethylamino)methyl]-N-[4-(1-oxo-1,2-dihydroisoquinolin-4-yl)phenyl]-1,3-dihydro-2H-isoindole-2-carboxamide;
5-[(diethylamino)methyl]-N-[4-(1-oxo-1,2-dihydroisoquinolin-4-yl)phenyl]-1,3-dihydro-2H-isoindole-2-carboxamide;
5-[(4-methylpiperazin-1-yl)methyl]-N-[4-(1-oxo-1,2-dihydroisoquinolin-4-yl)phenyl]-1,3-dihydro-2H-isoindole-2-carboxamide;
5-[(dimethylamino)methyl]-N-[4-(4-oxo-3,4-dihydrophthalazin-1-yl)phenyl]-1,3-dihydro-2H-isoindole-2-carboxamide;
5-[(diethylamino)methyl]-N-[4-(4-oxo-3,4-dihydrophthalazin-1-yl)phenyl]-1,3-dihydro-2H-isoindole-2-carboxamide;
N-{4-[4-oxo-8-(trifluoromethyl)-3,4-dihydrophthalazin-1-yl]phenyl}-5-(pyrrolidin-1-ylmethyl)-1,3-dihydro-2H-isoindole-2-carboxamide;
5-[(1-methylpiperidin-4-yl)oxy]-N-[4-(4-oxo-3,4-dihydrophthalazin-1-yl)phenyl]-1,3-dihydro-2H-isoindole-2-carboxamide;
5-{[(3R)-3-fluoropyrrolidin-1-yl]methyl}-N-[4-(4-oxo-3,4-dihydrophthalazin-1-yl)phenyl]-1,3-dihydro-2H-isoindole-2-carboxamide;
5-{[(3S)-3-fluoropyrrolidin-1-yl]methyl}-N-[4-(4-oxo-3,4-dihydrophthalazin-1-yl)phenyl]-1,3-dihydro-2H-isoindole-2-carboxamide;
5-(azetidin-1-ylmethyl)-N-[4-(4-oxo-3,4-dihydrophthalazin-1-yl)phenyl]-1,3-dihydro-2H-isoindole-2-carboxamide;
N-[4-(1-oxo-1,2-dihydropyrrolo[1,2-d][1,2,4]triazin-4-yl)phenyl]-1,3-dihydro-2H-isoindole-2-carboxamide;
N-[4-(1-oxo-1,2-dihydropyrrolo[1,2-d][1,2,4]triazin-4-yl)phenyl]-5-(pyrrolidin-1-ylmethyl)-1,3-dihydro-2H-isoindole-2-carboxamide;
tert-butyl 4-{4-[(1,3-dihydro-2H-isoindol-2-ylcarbonyl)amino]phenyl}piperidine-1-carboxylate;
N-[4-(5-propyl-1,2,4-oxadiazol-3-yl)phenyl]-1,3-dihydro-2H-isoindole-2-carboxamide;
N-[4-(piperidin-4-yl)phenyl]-1,3-dihydro-2H-isoindole-2-carboxamide;
N-[4-(1-butyrylpiperidin-4-yl)phenyl]-1,3-dihydro-2H-isoindole-2-carboxamide;
N-[4-(1-isobutyrylpiperidin-4-yl)phenyl]-1,3-dihydro-2H-isoindole-2-carboxamide;
N-[4-(1-benzoylpiperidin-4-yl)phenyl]-1,3-dihydro-2H-isoindole-2-carboxamide;
N-{4-[5-(3-methylbutyl)-1,2,4-oxadiazol-3-yl]phenyl}-1,3-dihydro-2H-isoindole-2-carboxamide;
N-[4-(5-benzyl-1,2,4-oxadiazol-3-yl)phenyl]-1,3-dihydro-2H-isoindole-2-carboxamide;
N-(4-{[(3R)-tetrahydrofuran-3-ylmethyl]carbamoyl}phenyl)-1,3-dihydro-2H-isoindole-2-carboxamide;
N-(4-{[(3S)-tetrahydrofuran-3-ylmethyl]carbamoyl}phenyl)-1,3-dihydro-2H-isoindole-2-carboxamide;
N-{4-[(2-methoxyethyl)carbamoyl]phenyl}-1,3-dihydro-2H-isoindole-2-carboxamide;
N-{4-[(5-chloropyridin-2-yl)carbamoyl]phenyl}-1,3-dihydro-2H-isoindole-2-carboxamide;
N-{4-[(3-hydroxy-4-methoxyphenyl)carbamoyl]phenyl}-1,3-dihydro-2H-isoindole-2-carboxamide;
N-{4-[(2,4-dimethoxybenzyl)carbamoyl]phenyl}-1,3-dihydro-2H-isoindole-2-carboxamide;
N-(4-{[4-(2-oxopyrrolidin-1-yl)benzyl]carbamoyl}phenyl)-1,3-dihydro-2H-isoindole-2-carboxamide;
N-(4-{[(1S,2S)-2-hydroxy-2,3-dihydro-1H-inden-1-yl]carbamoyl}phenyl)-1,3-dihydro-2H-isoindole-2-carboxamide;
N-(4-{[(1-hydroxycyclopropyl)methyl]carbamoyl}phenyl)-1,3-dihydro-2H-isoindole-2-carboxamide;
N-{4-[(tetrahydro-2H-pyran-2-ylmethyl)carbamoyl]phenyl}-1,3-dihydro-2H-isoindole-2-carboxamide;
N-{4-[(tetrahydro-2H-pyran-3-ylmethyl)carbamoyl]phenyl}-1,3-dihydro-2H-isoindole-2-carboxamide;
N-{4-[(tetrahydro-2H-pyran-4-ylmethyl)carbamoyl]phenyl}-1,3-dihydro-2H-isoindole-2-carboxamide;
N-[4-(propylcarbamoyl)phenyl]-5-vinyl-1,3-dihydro-2H-isoindole-2-carboxamide;
N-{4-[(4-benzoylpiperazin-1-yl)carbonyl]phenyl}-1,3-dihydro-2H-isoindole-2-carboxamide;
N-(4-{[(2S)-tetrahydrofuran-2-ylmethyl]carbamoyl}phenyl)-1,3-dihydro-2H-pyrrolo[3,4-c]pyridine-2-carboxamide;
N-(4-{[(2R)-tetrahydrofuran-2-ylmethyl]carbamoyl}phenyl)-1,3-dihydro-2H-pyrrolo[3,4-c]pyridine-2-carboxamide;
N-{4-[5-(tetrahydrofuran-3-yl)-1,2,4-oxadiazol-3-yl]phenyl}-1,3-dihydro-2H-isoindole-2-carboxamide;
N-[4-(1-isobutyl-1,2,3,6-tetrahydropyridin-4-yl)phenyl]-1,3-dihydro-2H-isoindole-2-carboxamide;
N-(4-{[(3-methylbutyl)amino]carbonyl}phenyl)-5,7-dihydro-6H-pyrrolo[3,4-d]pyrimidine-6-carboxamide;
N-(4-{[(3-phenylpropyl)amino]carbonyl}phenyl)-5,7-dihydro-6H-pyrrolo[3,4-d]pyrimidine-6-carboxamide;
N-{4-[1-(4-methylbenzoyl)-1,2,3,6-tetrahydropyridin-4-yl]phenyl}-1,3-dihydro-2H-isoindole-2-carboxamide;
N-[4-(1-benzyl-1,2,3,6-tetrahydropyridin-4-yl)phenyl]-1,3-dihydro-2H-isoindole-2-carboxamide;
N-(4-{[4-(tetrahydrofuran-3-ylmethyl)piperazin-1-yl]carbonyl}phenyl)-1,3-dihydro-2H-isoindole-2-carboxamide;
5-fluoro-N-[4-({[(2S)-tetrahydrofuran-2-ylmethyl]amino}carbonyl)phenyl]-1,3-dihydro-2H-isoindole-2-carboxamide;
5-fluoro-N-[4-({[(2R)-tetrahydrofuran-2-ylmethyl]amino}carbonyl)phenyl]-1,3-dihydro-2H-isoindole-2-carboxamide;
N-[4-({[(1S)-2-hydroxy-1-phenylethyl]amino}carbonyl)phenyl]-1,3-dihydro-2H-pyrrolo[3,4-c]pyridine-2-carboxamide;

N-(4-{[4-(2-methoxyethyl)piperazin-1-yl]
carbonyl}phenyl)-1,3-dihydro-2H-isoindole-2-carboxamide;
N-(4-{[(2S)-2-(2-hydroxyethyl)piperidin-1-yl]
carbonyl}phenyl)-1,3-dihydro-2H-isoindole-2-carboxamide;
N-{4-[(propylamino)carbonyl]phenyl}-5-pyridin-3-yl-1,3-dihydro-2H-isoindole-2-carboxamide;
N-{4-[(propylamino)carbonyl]phenyl}-5-pyridin-4-yl-1,3-dihydro-2H-isoindole-2-carboxamide;
$N^5$-(2-methoxyethyl)-$N^2$-{4-[(propylamino)carbonyl]phenyl}-1,3-dihydro-2H-isoindole-2,5-dicarboxamide;
N-(4-cyanophenyl)-1,3-dihydro-2H-isoindole-2-carboxamide;
N-[4-(trifluoromethyl)phenyl]-1,3-dihydro-2H-isoindole-2-carboxamide;
N-[4-({[(1S)-2-hydroxy-1-pyridin-2-ylethyl]
amino}carbonyl)phenyl]-1,3-dihydro-2H-pyrrolo[3,4-c]pyridine-2-carboxamide;
N-(4-{[[(3-methylbutyl)amino]carbonyl}phenyl)-5,7-dihydro-6H-pyrrolo[3,4-b]pyridine-6-carboxamide;
N-(4-{[[(tetrahydrofuran-3-ylmethyl)amino]
carbonyl}phenyl)-5,7-dihydro-6H-pyrrolo[3,4-b]pyridine-6-carboxamide;
N-{4-[(4-pyridin-2-ylpiperazin-1-yl)carbonyl]phenyl}-5,7-dihydro-6H-pyrrolo[3,4-b]pyridine-6-carboxamide;
N-[4-({[(1S)-2-hydroxy-1-pyridin-2-ylethyl]
amino}carbonyl)phenyl]-1,3-dihydro-2H-isoindole-2-carboxamide;
5-(1,2-dihydroxyethyl)-N-{4-[(propylamino)carbonyl]phenyl}-1,3-dihydro-2H-isoindole-2-carboxamide;
N-{4-[1-(5-oxo-L-prolyl)-1,2,3,6-tetrahydropyridin-4-yl]
phenyl}-1,3-dihydro-2H-isoindole-2-carboxamide;
N-{4-[1-(5-oxo-D-prolyl)-1,2,3,6-tetrahydropyridin-4-yl]
phenyl}-1,3-dihydro-2H-isoindole-2-carboxamide;
N-[4-(1-propionyl-1,2,3,6-tetrahydropyridin-4-yl)phenyl]-1,3-dihydro-2H-isoindole-2-carboxamide;
N-{4-[1-(2-methylbutanoyl)-1,2,3,6-tetrahydropyridin-4-yl]
phenyl}-1,3-dihydro-2H-isoindole-2-carboxamide;
N-{4-[1-(2-ethylbutanoyl)-1,2,3,6-tetrahydropyridin-4-yl]
phenyl}-1,3-dihydro-2H-isoindole-2-carboxamide;
N-{4-[1-(methoxyacetyl)-1,2,3,6-tetrahydropyridin-4-yl]
phenyl}-1,3-dihydro-2H-isoindole-2-carboxamide;
N-{4-[1-(ethoxyacetyl)-1,2,3,6-tetrahydropyridin-4-yl]phenyl}-1,3-dihydro-2H-isoindole-2-carboxamide;
N-(4-{1-[(2-methoxyethoxy)acetyl]-1,2,3,6-tetrahydropyridin-4-yl}phenyl)-1,3-dihydro-2H-isoindole-2-carboxamide;
N-{4-[1-(tetrahydrofuran-2-ylcarbonyl)-1,2,3,6-tetrahydropyridin-4-yl]phenyl}-1,3-dihydro-2H-isoindole-2-carboxamide;
N-{4-[1-(tetrahydrofuran-3-ylcarbonyl)-1,2,3,6-tetrahydropyridin-4-yl]phenyl}-1,3-dihydro-2H-isoindole-2-carboxamide;
N-{4-[1-(cyclopropylacetyl)-1,2,3,6-tetrahydropyridin-4-yl]phenyl}-1,3-dihydro-2H-isoindole-2-carboxamide;
N-{4-[1-(cyclopentylcarbonyl)-1,2,3,6-tetrahydropyridin-4-yl]phenyl}-1,3-dihydro-2H-isoindole-2-carboxamide;
N-{4-[1-(2-methylbenzoyl)-1,2,3,6-tetrahydropyridin-4-yl]phenyl}-1,3-dihydro-2H-isoindole-2-carboxamide;
N-{4-[1-(3-methylbenzoyl)-1,2,3,6-tetrahydropyridin-4-yl]phenyl}-1,3-dihydro-2H-isoindole-2-carboxamide;
N-{4-[1-(2-methoxybenzoyl)-1,2,3,6-tetrahydropyridin-4-yl]phenyl}-1,3-dihydro-2H-isoindole-2-carboxamide;
N-{4-[1-(3-methoxybenzoyl)-1,2,3,6-tetrahydropyridin-4-yl]phenyl}-1,3-dihydro-2H-isoindole-2-carboxamide;
N-{4-[1-(4-methoxybenzoyl)-1,2,3,6-tetrahydropyridin-4-yl]phenyl}-1,3-dihydro-2H-isoindole-2-carboxamide;
N-{4-[1-(2-fluorobenzoyl)-1,2,3,6-tetrahydropyridin-4-yl]phenyl}-1,3-dihydro-2H-isoindole-2-carboxamide;
N-{4-[1-(3-fluorobenzoyl)-1,2,3,6-tetrahydropyridin-4-yl]phenyl}-1,3-dihydro-2H-isoindole-2-carboxamide;
N-{4-[1-(4-fluorobenzoyl)-1,2,3,6-tetrahydropyridin-4-yl]phenyl}-1,3-dihydro-2H-isoindole-2-carboxamide;
N-{4-[1-(4-chlorobenzoyl)-1,2,3,6-tetrahydropyridin-4-yl]phenyl}-1,3-dihydro-2H-isoindole-2-carboxamide;
N-(4-{1-[3-(dimethylamino)benzoyl]-1,2,3,6-tetrahydropyridin-4-yl}phenyl)-1,3-dihydro-2H-isoindole-2-carboxamide;
N-(4-{1-[4-(dimethylamino)benzoyl]-1,2,3,6-tetrahydropyridin-4-yl}phenyl)-1,3-dihydro-2H-isoindole-2-carboxamide;
N-{4-[1-(3-furoyl)-1,2,3,6-tetrahydropyridin-4-yl]phenyl}-1,3-dihydro-2H-isoindole-2-carboxamide;
N-{4-[1-(3-thienylcarbonyl)-1,2,3,6-tetrahydropyridin-4-yl]phenyl}-1,3-dihydro-2H-isoindole-2-carboxamide;
N-{4-[1-(1H-pyrrol-2-ylcarbonyl)-1,2,3,6-tetrahydropyridin-4-yl]phenyl}-1,3-dihydro-2H-isoindole-2-carboxamide;
N-(4-{1-[(2,5-dimethyl-1H-pyrrol-3-yl)carbonyl]-1,2,3,6-tetrahydropyridin-4-yl}phenyl)-1,3-dihydro-2H-isoindole-2-carboxamide;
N-{4-[1-(1,3-thiazol-4-ylcarbonyl)-1,2,3,6-tetrahydropyridin-4-yl]phenyl}-1,3-dihydro-2H-isoindole-2-carboxamide;
N-{4-[1-(1H-pyrazol-4-ylcarbonyl)-1,2,3,6-tetrahydropyridin-4-yl]phenyl}-1,3-dihydro-2H-isoindole-2-carboxamide;
N-(4-{1-[(3,5-dimethyl-1,2-oxazol-4-yl)carbonyl]-1,2,3,6-tetrahydropyridin-4-yl}phenyl)-1,3-dihydro-2H-isoindole-2-carboxamide;
N-{4-[1-(pyridin-2-ylcarbonyl)-1,2,3,6-tetrahydropyridin-4-yl]phenyl}-1,3-dihydro-2H-isoindole-2-carboxamide;
N-{4-[1-(pyridin-3-ylcarbonyl)-1,2,3,6-tetrahydropyridin-4-yl]phenyl}-1,3-dihydro-2H-isoindole-2-carboxamide;
N-[4-(1-isonicotinoyl-1,2,3,6-tetrahydropyridin-4-yl)phenyl]-1,3-dihydro-2H-isoindole-2-carboxamide;
N-{4-[1-(pyridazin-3-ylcarbonyl)-1,2,3,6-tetrahydropyridin-4-yl]phenyl}-1,3-dihydro-2H-isoindole-2-carboxamide;
N-{4-[1-(pyrazin-2-ylcarbonyl)-1,2,3,6-tetrahydropyridin-4-yl]phenyl}-1,3-dihydro-2H-isoindole-2-carboxamide;
N-{4-[1-(pyrimidin-4-ylcarbonyl)-1,2,3,6-tetrahydropyridin-4-yl]phenyl}-1,3-dihydro-2H-isoindole-2-carboxamide;
N-(4-{1-[3-(piperidin-1-yl)propanoyl]-1,2,3,6-tetrahydropyridin-4-yl}phenyl)-1,3-dihydro-2H-isoindole-2-carboxamide;
N-{4-[1-(morpholin-4-ylacetyl)-1,2,3,6-tetrahydropyridin-4-yl]phenyl}-1,3-dihydro-2H-isoindole-2-carboxamide;
N-(4-{1-[(4-methylpiperazin-1-yl)acetyl]-1,2,3,6-tetrahydropyridin-4-yl}phenyl)-1,3-dihydro-2H-isoindole-2-carboxamide;
N-(4-{[6-(benzoylamino)hexyl]carbamoyl}phenyl)-1,3-dihydro-2H-isoindole-2-carboxamide;
N-[4-({4-[(benzoylamino)methyl]benzyl}carbamoyl)phenyl]-5-fluoro-1,3-dihydro-2H-isoindole-2-carboxamide;
N-{4-[4-(5-oxo-L-prolyl)piperazin-1-yl]phenyl}-1,3-dihydro-2H-isoindole-2-carboxamide;
N-{4-[4-(5-oxo-D-prolyl)piperazin-1-yl]phenyl}-1,3-dihydro-2H-isoindole-2-carboxamide;
N-(4-{4-[(1-acetylpiperidin-4-yl)carbonyl]piperazin-1-yl}phenyl)-1,3-dihydro-2H-isoindole-2-carboxamide;

N-{4-[4-(2-acetamidobenzoyl)piperazin-1-yl]phenyl}-1,3-dihydro-2H-isoindole-2-carboxamide;
N-(4-{4-[(methylsulfonyl)benzoyl]piperazin-1-yl}phenyl)-1,3-dihydro-2H-isoindole-2-carboxamide;
N-[4-(4-butyrylpiperazin-1-yl)phenyl]-1,3-dihydro-2H-isoindole-2-carboxamide;
N-[4-(4-isobutyrylpiperazin-1-yl)phenyl]-1,3-dihydro-2H-isoindole-2-carboxamide;
N-{4-[4-(2-methylbutanoyl)piperazin-1-yl]phenyl}-1,3-dihydro-2H-isoindole-2-carboxamide;
N-{4-[4-(3,3,3-trifluoropropanoyl)piperazin-1-yl]phenyl}-1,3-dihydro-2H-isoindole-2-carboxamide;
N-{4-[4-(methoxyacetyl)piperazin-1-yl]phenyl}-1,3-dihydro-2H-isoindole-2-carboxamide;
N-{4-[4-(tetrahydrofuran-2-ylcarbonyl)piperazin-1-yl]phenyl}-1,3-dihydro-2H-isoindole-2-carboxamide;
N-{4-[4-(tetrahydrofuran-3-ylcarbonyl)piperazin-1-yl]phenyl}-1,3-dihydro-2H-isoindole-2-carboxamide;
N-{4-[4-(cyclopentylacetyl)piperazin-1-yl]phenyl}-1,3-dihydro-2H-isoindole-2-carboxamide;
N-{4-[4-(cyclohexylcarbonyl)piperazin-1-yl]phenyl}-1,3-dihydro-2H-isoindole-2-carboxamide;
N-{4-[4-(2-methoxybenzoyl)piperazin-1-yl]phenyl}-1,3-dihydro-2H-isoindole-2-carboxamide;
N-{4-[4-(3-methoxybenzoyl)piperazin-1-yl]phenyl}-1,3-dihydro-2H-isoindole-2-carboxamide;
N-{4-[4-(4-methoxybenzoyl)piperazin-1-yl]phenyl}-1,3-dihydro-2H-isoindole-2-carboxamide;
N-{4-[4-(3-fluorobenzoyl)piperazin-1-yl]phenyl}-1,3-dihydro-2H-isoindole-2-carboxamide;
N-{4-[4-(2-chlorobenzoyl)piperazin-1-yl]phenyl}-1,3-dihydro-2H-isoindole-2-carboxamide;
N-{4-[4-(4-chlorobenzoyl)piperazin-1-yl]phenyl}-1,3-dihydro-2H-isoindole-2-carboxamide;
N-{4-[4-(3-cyanobenzoyl)piperazin-1-yl]phenyl}-1,3-dihydro-2H-isoindole-2-carboxamide;
N-{4-[4-(4-cyanobenzoyl)piperazin-1-yl]phenyl}-1,3-dihydro-2H-isoindole-2-carboxamide;
N-(4-{4-[3-(dimethylamino)benzoyl]piperazin-1-yl}phenyl)-1,3-dihydro-2H-isoindole-2-carboxamide;
N-(4-{4-[4-(dimethylamino)benzoyl]piperazin-1-yl}phenyl)-1,3-dihydro-2H-isoindole-2-carboxamide;
N-{4-[4-(3,4-dimethoxybenzoyl)piperazin-1-yl]phenyl}-1,3-dihydro-2H-isoindole-2-carboxamide;
N-{4-[4-(3,5-dimethoxybenzoyl)piperazin-1-yl]phenyl}-1,3-dihydro-2H-isoindole-2-carboxamide;
N-(4-{4-[(3,4-dimethoxyphenyl)acetyl]piperazin-1-yl}phenyl)-1,3-dihydro-2H-isoindole-2-carboxamide;
N-{4-[4-(2-furoyl)piperazin-1-yl]phenyl}-1,3-dihydro-2H-isoindole-2-carboxamide;
N-{4-[4-(3-furoyl)piperazin-1-yl]phenyl}-1,3-dihydro-2H-isoindole-2-carboxamide;
N-{4-[4-(1H-pyrrol-2-ylcarbonyl)piperazin-1-yl]phenyl}-1,3-dihydro-2H-isoindole-2-carboxamide;
N-{4-[4-(1H-pyrazol-5-ylcarbonyl)piperazin-1-yl]phenyl}-1,3-dihydro-2H-isoindole-2-carboxamide;
N-{4-[4-(pyridin-2-ylcarbonyl)piperazin-1-yl]phenyl}-1,3-dihydro-2H-isoindole-2-carboxamide;
N-{4-[4-(pyridin-3-ylcarbonyl)piperazin-1-yl]phenyl}-1,3-dihydro-2H-isoindole-2-carboxamide;
N-[4-(4-isonicotinoylpiperazin-1-yl)phenyl]-1,3-dihydro-2H-isoindole-2-carboxamide;
N-{4-[4-(pyridazin-3-ylcarbonyl)piperazin-1-yl]phenyl}-1,3-dihydro-2H-isoindole-2-carboxamide;
N-{4-[4-(pyrazin-2-ylcarbonyl)piperazin-1-yl]phenyl}-1,3-dihydro-2H-isoindole-2-carboxamide;
N-{4-[4-(pyrimidin-4-ylcarbonyl)piperazin-1-yl]phenyl}-1,3-dihydro-2H-isoindole-2-carboxamide;
N-{4-[4-(N,N-dimethyl-beta-alanyl)piperazin-1-yl]phenyl}-1,3-dihydro-2H-isoindole-2-carboxamide;
N-[4-(4-acetylpiperazin-1-yl)phenyl]-1,3-dihydro-2H-isoindole-2-carboxamide;
N-{4-[4-(2-fluorobenzoyl)piperazin-1-yl]phenyl}-1,3-dihydro-2H-isoindole-2-carboxamide;
N-{4-[4-(4-fluorobenzoyl)piperazin-1-yl]phenyl}-1,3-dihydro-2H-isoindole-2-carboxamide;
N-{4-[4-(phenylacetyl)piperazin-1-yl]phenyl}-1,3-dihydro-2H-isoindole-2-carboxamide;
N-{4-[4-(1,3-thiazol-4-ylcarbonyl)piperazin-1-yl]phenyl}-1,3-dihydro-2H-isoindole-2-carboxamide;
N-{4-[4-(morpholin-4-ylacetyl)piperazin-1-yl]phenyl}-1,3-dihydro-2H-isoindole-2-carboxamide;
N-[4-(1-butyryl-1,2,3,6-tetrahydropyridin-4-yl)phenyl]-1,3-dihydro-2H-pyrrolo[3,4-c]pyridine-2-carboxamide;
N-[4-(1-isobutyryl-1,2,3,6-tetrahydropyridin-4-yl)phenyl]-1,3-dihydro-2H-pyrrolo[3,4-c]pyridine-2-carboxamide;
N-[4-(1-benzoyl-1,2,3,6-tetrahydropyridin-4-yl)phenyl]-1,3-dihydro-2H-pyrrolo[3,4-c]pyridine-2-carboxamide;
N-{4-[1-(tetrahydrofuran-3-ylcarbonyl)-1,2,3,6-tetrahydropyridin-4-yl]phenyl}-1,3-dihydro-2H-pyrrolo[3,4-c]pyridine-2-carboxamide;
N-[4-(1-oxo-2,3-dihydro-1H-isoindol-4-yl)phenyl]-1,3-dihydro-2H-isoindole-2-carboxamide;
N-[4-(4-oxo-3,4-dihydrophthalazin-1-yl)phenyl]-1,3-dihydro-2H-pyrrolo[3,4-c]pyridine-2-carboxamide;
N-[4-(4-oxo-3,4-dihydrophthalazin-1-yl)phenyl]-5,7-dihydro-6H-pyrrolo[3,4-b]pyridine-6-carboxamide;
N-{4-[(tetrahydro-2H-pyran-2-ylmethyl)carbamoyl]phenyl}-1,3-dihydro-2H-pyrrolo[3,4-c]pyridine-2-carboxamide;
N-{4-[(tetrahydro-2H-pyran-3-ylmethyl)carbamoyl]phenyl}-1,3-dihydro-2H-pyrrolo[3,4-c]pyridine-2-carboxamide;
N-{4-[(tetrahydro-2H-pyran-4-ylmethyl)carbamoyl]phenyl}-1,3-dihydro-2H-pyrrolo[3,4-c]pyridine-2-carboxamide;
N-(4-{[(2S)-1-hydroxy-4-methylpentan-2-yl]carbamoyl}phenyl)-1,3-dihydro-2H-pyrrolo[3,4-c]pyridine-2-carboxamide;
$N^5$-[2-(dimethylamino)ethyl]-$N^2$-[4-(propylcarbamoyl)phenyl]-1,3-dihydro-2H-isoindole-2,5-dicarboxamide;
5-(morpholin-4-ylcarbonyl)-N-[4-(propylcarbamoyl)phenyl]-1,3-dihydro-2H-isoindole-2-carboxamide;
N-(4-{benzyl[3-(morpholin-4-yl)propyl]carbamoyl}phenyl)-1,3-dihydro-2H-isoindole-2-carboxamide;
N-[4-(isobutoxycarbamoyl)phenyl]-1,3-dihydro-2H-isoindole-2-carboxamide;
5-bromo-N-{4-[(cyclopentylacetyl)amino]phenyl}-1,3-dihydro-2H-isoindole-2-carboxamide;
5-cyano-N-{4-[(cyclopentylacetyl)amino]phenyl}-1,3-dihydro-2H-isoindole-2-carboxamide;
methyl 4-{[(5-cyano-1,3-dihydro-2H-isoindol-2-yl)carbonyl]amino}benzoate;
N-(4-{(E)-[(benzyloxy)imino]methyl}phenyl)-1,3-dihydro-2H-isoindole-2-carboxamide;
5-fluoro-N-{4-[(tetrahydro-2H-pyran-2-ylmethyl)carbamoyl]phenyl}-1,3-dihydro-2H-isoindole-2-carboxamide;
5-fluoro-N-{4-[(tetrahydro-2H-pyran-3-ylmethyl)carbamoyl]phenyl}-1,3-dihydro-2H-isoindole-2-carboxamide;
5-fluoro-N-{4-[(tetrahydro-2H-pyran-4-ylmethyl)carbamoyl]phenyl}-1,3-dihydro-2H-isoindole-2-carboxamide;

5-fluoro-N-(4-{[(1S)-2-hydroxy-1-phenylethyl]
  carbamoyl}phenyl)-1,3-dihydro-2H-isoindole-2-carboxamide;
5-fluoro-N-(4-{[(1S)-2-hydroxy-1-(pyridin-2-yl)ethyl]
  carbamoyl}phenyl)-1,3-dihydro-2H-isoindole-2-carboxamide;
5-fluoro-N-(4-{[(2S)-1-hydroxy-4-methylpentan-2-yl]
  carbamoyl}phenyl)-1,3-dihydro-2H-isoindole-2-carboxamide;
N-[4-(3-aminopyrrolidin-1-yl)phenyl]-1,3-dihydro-2H-isoindole-2-carboxamide;
$N^2$-{4-[(cyclopentylacetyl)amino]phenyl}-1,3-dihydro-2H-isoindole-2,5-dicarboxamide;
N-[4-({benzyl[3-(morpholin-4-yl)propyl]amino}methyl)phenyl]-1,3-dihydro-2H-isoindole-2-carboxamide;
N-{4-[(cyclopentylacetyl)amino]phenyl}-5-(1H-pyrazol-3-yl)-1,3-dihydro-2H-isoindole-2-carboxamide;
N-{4-[(cyclopentylacetyl)amino]phenyl}-5-(pyridin-3-yl)-1,3-dihydro-2H-isoindole-2-carboxamide;
N-{4-[(cyclopentylacetyl)amino]phenyl}-5-(1-methyl-1H-pyrazol-4-yl)-1,3-dihydro-2H-isoindole-2-carboxamide;
$N^2$-{4-[(cyclopentylacetyl)amino]phenyl}-$N^5$-(2-methoxyethyl)-1,3-dihydro-2H-isoindole-2,5-dicarboxamide;
$N^2$-{4-[(cyclopentylacetyl)amino]phenyl}-$N^5$-(2-hydroxyethyl)-1,3-dihydro-2H-isoindole-2,5-dicarboxamide;
5-(aminomethyl)-N-{4-[(cyclopentylacetyl)amino]phenyl}-1,3-dihydro-2H-isoindole-2-carboxamide;
N-(4-{[(2S)-1-hydroxy-4-(methylthio)butan-2-yl]
  carbamoyl}phenyl)-1,3-dihydro-2H-isoindole-2-carboxamide;
N-(4-{[(2S,3S)-1-hydroxy-3-methylpentan-2-yl]
  carbamoyl}phenyl)-1,3-dihydro-2H-isoindole-2-carboxamide;
N-(4-{[(2S)-1-hydroxypropan-2-yl]carbamoyl}phenyl)-1,3-dihydro-2H-isoindole-2-carboxamide;
N-(4-{[(2S,3R)-1,3-dihydroxybutan-2-yl]
  carbamoyl}phenyl)-1,3-dihydro-2H-isoindole-2-carboxamide;
N-(4-{[(2S)-1-hydroxyhexan-2-yl]carbamoyl}phenyl)-1,3-dihydro-2H-isoindole-2-carboxamide;
N-(4-{[(2S)-1-hydroxypentan-2-yl]carbamoyl}phenyl)-1,3-dihydro-2H-isoindole-2-carboxamide;
N-(4-{[(1S,2S)-2-hydroxycyclopentyl]carbamoyl}phenyl)-1,3-dihydro-2H-isoindole-2-carboxamide;
N-(4-{[(1S,2R)-2-hydroxycyclopentyl]carbamoyl}phenyl)-1,3-dihydro-2H-isoindole-2-carboxamide;
N-(4-{[(2S)-1-cyclohexyl-3-hydroxypropan-2-yl]
  carbamoyl}phenyl)-1,3-dihydro-2H-isoindole-2-carboxamide;
N-[4-({(2R)-1-hydroxy-3-[(4-methylbenzyl)thio]propan-2-yl}carbamoyl)phenyl]-1,3-dihydro-2H-isoindole-2-carboxamide;
N-(4-{[(1S)-1-(4-tert-butylphenyl)-2-hydroxyethyl]
  carbamoyl}phenyl)-1,3-dihydro-2H-isoindole-2-carboxamide;
N-{4-[(cyclopentylacetyl)amino]phenyl}-5-methoxy-1,3-dihydro-2H-isoindole-2-carboxamide;
5-methoxy-N-[4-(propylcarbamoyl)phenyl]-1,3-dihydro-2H-isoindole-2-carboxamide;
5-methyl-N-[4-(propylcarbamoyl)phenyl]-1,3-dihydro-2H-isoindole-2-carboxamide;
N-[4-(propylcarbamoyl)phenyl]-1,3-dihydro-2H-pyrrolo[3,4-c]pyridine-2-carboxamide;
N-(4-{[(2S)-tetrahydrofuran-2-ylmethyl]
  carbamoyl}phenyl)-5,7-dihydro-6H-pyrrolo[3,4-b]pyridine-6-carboxamide;
N-(4-{[(2R)-tetrahydrofuran-2-ylmethyl]
  carbamoyl}phenyl)-5,7-dihydro-6H-pyrrolo[3,4-b]pyridine-6-carboxamide;
N-(4-{[(2S)-1-hydroxy-4-methylpentan-2-yl]
  carbamoyl}phenyl)-5,7-dihydro-6H-pyrrolo[3,4-b]pyridine-6-carboxamide;
N-(4-{[(1S)-2-hydroxy-1-phenylethyl]carbamoyl}phenyl)-5,7-dihydro-6H-pyrrolo[3,4-b]pyridine-6-carboxamide;
N-{4-[(tetrahydro-2H-pyran-4-ylmethyl)carbamoyl]phenyl}-5,7-dihydro-6H-pyrrolo[3,4-b]pyridine-6-carboxamide;
N-{4-[(cyclopentylacetyl)amino]phenyl}-5-(pyridin-4-yl)-1,3-dihydro-2H-isoindole-2-carboxamide;
5-(hydroxymethyl)-N-{4-[(3-methylbutyl)carbamoyl]phenyl}-1,3-dihydro-2H-isoindole-2-carboxamide;
N-(4-{[(1S)-2-hydroxy-1-(pyridin-2-yl)ethyl]
  carbamoyl}phenyl)-5,7-dihydro-6H-pyrrolo[3,4-b]pyridine-6-carboxamide;
N-(4-{1-[(2-methoxyethoxy)acetyl]-1,2,3,6-tetrahydropyridin-4-yl}phenyl)-1,3-dihydro-2H-pyrrolo[3,4-c]pyridine-2-carboxamide;
N-(4-{(1E)-3-[benzyl(methyl)amino]prop-1-en-1-yl}phenyl)-1,3-dihydro-2H-isoindole-2-carboxamide;
N-[4-(4-phenoxypiperidin-1-yl)phenyl]-1,3-dihydro-2H-isoindole-2-carboxamide;
N-[4-(3-phenoxyazetidin-1-yl)phenyl]-1,3-dihydro-2H-isoindole-2-carboxamide;
N-(4-{[benzyl(methyl)amino]methyl}phenyl)-1,3-dihydro-2H-isoindole-2-carboxamide;
5-fluoro-N-(4-{[(3R)-tetrahydrofuran-3-ylmethyl]
  carbamoyl}phenyl)-1,3-dihydro-2H-isoindole-2-carboxamide;
5-fluoro-N-(4-{[(3S)-tetrahydrofuran-3-ylmethyl]
  carbamoyl}phenyl)-1,3-dihydro-2H-isoindole-2-carboxamide;
N-{4-[(4-hydroxypiperidin-1-yl)carbonyl]phenyl}-1,3-dihydro-2H-pyrrolo[3,4-c]pyridine-2-carboxamide;
N-{4-[(2-hydroxy-2-methylpropyl)carbamoyl]phenyl}-1,3-dihydro-2H-pyrrolo[3,4-c]pyridine-2-carboxamide;
N-{4-[(4-hydroxybutyl)carbamoyl]phenyl}-1,3-dihydro-2H-pyrrolo[3,4-c]pyridine-2-carboxamide;
N-(4-{[(2S)-1-hydroxy-3-methylbutan-2-yl]
  carbamoyl}phenyl)-1,3-dihydro-2H-pyrrolo[3,4-c]pyridine-2-carboxamide;
N-{4-[(1-hydroxy-2-methylpropan-2-yl)carbamoyl]phenyl}-1,3-dihydro-2H-pyrrolo[3,4-c]pyridine-2-carboxamide;
N-(4-{[(2R)-2-hydroxypropyl]carbamoyl}phenyl)-1,3-dihydro-2H-pyrrolo[3,4-c]pyridine-2-carboxamide;
N-(4-{[(2S)-2-hydroxypropyl]carbamoyl}phenyl)-1,3-dihydro-2H-pyrrolo[3,4-c]pyridine-2-carboxamide;
N-(4-{[3-(piperidin-1-yl)propyl]carbamoyl}phenyl)-1,3-dihydro-2H-pyrrolo[3,4-c]pyridine-2-carboxamide;
N-[4-(5,6-dihydroimidazo[1,5-a]pyrazin-7(8H)-ylcarbonyl)phenyl]-1,3-dihydro-2H-pyrrolo[3,4-c]pyridine-2-carboxamide;
N-[4-(1-benzyl-1H-1,2,3-triazol-4-yl)phenyl]-1,3-dihydro-2H-isoindole-2-carboxamide;
N-{4-[1-(3-methylbutyl)-1H-1,2,3-triazol-4-yl]phenyl}-1,3-dihydro-2H-isoindole-2-carboxamide;
N-{4-[1-(tetrahydrofuran-3-ylmethyl)-1H-1,2,3-triazol-4-yl]phenyl}-1,3-dihydro-2H-isoindole-2-carboxamide;
N-(4-{1-[2-(2-oxopyrrolidin-1-yl)ethyl]-1H-1,2,3-triazol-4-yl}phenyl)-1,3-dihydro-2H-isoindole-2-carboxamide;
N-{4-[1-(1-benzylpiperidin-4-yl)-1H-1,2,3-triazol-4-yl]
  phenyl}-1,3-dihydro-2H-isoindole-2-carboxamide;

N-{4-[1-(3-phenylpropyl)-1H-1,2,3-triazol-4-yl]phenyl}-1,3-dihydro-2H-isoindole-2-carboxamide;
N-(4-{1-[4-(morpholin-4-yl)benzyl]-1H-1,2,3-triazol-4-yl}phenyl)-1,3-dihydro-2H-isoindole-2-carboxamide;
N-[4-(1-isobutyl-1H-1,2,3-triazol-4-yl)phenyl]-1,3-dihydro-2H-isoindole-2-carboxamide;
N-{4-[1-(cyclopentylmethyl)-1H-1,2,3-triazol-4-yl]phenyl}-1,3-dihydro-2H-isoindole-2-carboxamide;
N-{4-[1-(3-methoxypropyl)-1H-1,2,3-triazol-4-yl]phenyl}-1,3-dihydro-2H-isoindole-2-carboxamide;
N-[4-(1-isobutyrylpiperidin-4-yl)phenyl]-1,3-dihydro-2H-pyrrolo[3,4-c]pyridine-2-carboxamide;
N-(4-{1-[(2-methoxyethoxy)acetyl]piperidin-4-yl}phenyl)-1,3-dihydro-2H-isoindole-2-carboxamide;
5-(hydroxymethyl)-N-{4-[(tetrahydrofuran-3-ylacetyl)amino]phenyl}-1,3-dihydro-2H-isoindole-2-carboxamide;
5-(hydroxymethyl)-N-(4-{[(2-methoxyethoxy)acetyl]amino}phenyl)-1,3-dihydro-2H-isoindole-2-carboxamide;
5-(hydroxymethyl)-N-{4-[(tetrahydrofuran-2-ylacetyl)amino]phenyl}-1,3-dihydro-2H-isoindole-2-carboxamide;
N-{4-[(ethoxyacetyl)amino]phenyl}-5-(hydroxymethyl)-1,3-dihydro-2H-isoindole-2-carboxamide;
5-(hydroxymethyl)-N-{4-[(tetrahydro-2H-pyran-4-ylacetyl)amino]phenyl}-1,3-dihydro-2H-isoindole-2-carboxamide;
5-(hydroxymethyl)-N-{4-[(morpholin-4-ylacetyl)amino]phenyl}-1,3-dihydro-2H-isoindole-2-carboxamide;
N-[4-(morpholin-4-ylcarbonyl)phenyl]-1,3-dihydro-2H-pyrrolo[3,4-c]pyridine-2-carboxamide;
N-(4-{[3-(2-oxopyrrolidin-1-yl)propyl]carbamoyl}phenyl)-1,3-dihydro-2H-pyrrolo[3,4-c]pyridine-2-carboxamide;
N-{4-[1-(tetrahydrofuran-2-ylcarbonyl)-1,2,3,6-tetrahydropyridin-4-yl]phenyl}-1,3-dihydro-2H-pyrrolo[3,4-c]pyridine-2-carboxamide;
N-{4-[1-(tetrahydro-2H-pyran-4-ylcarbonyl)-1,2,3,6-tetrahydropyridin-4-yl]phenyl}-1,3-dihydro-2H-pyrrolo[3,4-c]pyridine-2-carboxamide;
N-{4-[1-(1,4-dioxan-2-ylcarbonyl)-1,2,3,6-tetrahydropyridin-4-yl]phenyl}-1,3-dihydro-2H-pyrrolo[3,4-c]pyridine-2-carboxamide;
N-(4-{1-[(1-methylpyrrolidin-3-yl)carbonyl]-1,2,3,6-tetrahydropyridin-4-yl}phenyl)-1,3-dihydro-2H-pyrrolo[3,4-c]pyridine-2-carboxamide;
N-(4-{1-[(1,1-dioxidotetrahydrothiophen-3-yl)carbonyl]-1,2,3,6-tetrahydropyridin-4-yl}phenyl)-1,3-dihydro-2H-pyrrolo[3,4-c]pyridine-2-carboxamide;
N-{4-[1-(2-hydroxy-2-methylpropanoyl)-1,2,3,6-tetrahydropyridin-4-yl]phenyl}-1,3-dihydro-2H-pyrrolo[3,4-c]pyridine-2-carboxamide;
N-(4-{[(1-methylpyrrolidin-3-yl)methyl]carbamoyl}phenyl)-1,3-dihydro-2H-isoindole-2-carboxamide;
N-{4-[(pyrrolidin-3-ylmethyl)carbamoyl]phenyl}-1,3-dihydro-2H-isoindole-2-carboxamide;
N-(4-{[(3S)-tetrahydrofuran-3-ylmethyl]carbamoyl}phenyl)-1,3-dihydro-2H-pyrrolo[3,4-c]pyridine-2-carboxamide;
N-(4-{[(1-methylpiperidin-4-yl)methyl]carbamoyl}phenyl)-1,3-dihydro-2H-isoindole-2-carboxamide;
N-{4-[(2-isopropoxyethyl)carbamoyl]phenyl}-1,3-dihydro-2H-pyrrolo[3,4-c]pyridine-2-carboxamide;
N-{4-[methyl(3-methylbutyl)carbamoyl]phenyl}-1,3-dihydro-2H-pyrrolo[3,4-c]pyridine-2-carboxamide;
N-[4-(azetidin-1-ylcarbonyl)phenyl]-1,3-dihydro-2H-pyrrolo[3,4-c]pyridine-2-carboxamide;
N-[4-(2,6-diazaspiro[3.5]non-2-ylcarbonyl)phenyl]-1,3-dihydro-2H-pyrrolo[3,4-c]pyridine-2-carboxamide;
N-[4-(1,7-diazaspiro[4.4]non-1-ylcarbonyl)phenyl]-1,3-dihydro-2H-pyrrolo[3,4-c]pyridine-2-carboxamide;
N-(4-{[4-(morpholin-4-yl)benzyl]carbamoyl}phenyl)-1,3-dihydro-2H-pyrrolo[3,4-c]pyridine-2-carboxamide;
N-{4-[(cyclopropylmethyl)carbamoyl]phenyl}-1,3-dihydro-2H-pyrrolo[3,4-c]pyridine-2-carboxamide;
N-{4-[methyl(propyl)carbamoyl]phenyl}-1,3-dihydro-2H-pyrrolo[3,4-c]pyridine-2-carboxamide;
N-[4-(isobutylcarbamoyl)phenyl]-1,3-dihydro-2H-pyrrolo[3,4-c]pyridine-2-carboxamide;
N-[4-(butylcarbamoyl)phenyl]-1,3-dihydro-2H-pyrrolo[3,4-c]pyridine-2-carboxamide;
N-{4-[(2-methoxyethyl)carbamoyl]phenyl}-1,3-dihydro-2H-pyrrolo[3,4-c]pyridine-2-carboxamide;
N-[4-(cyclopentylcarbamoyl)phenyl]-1,3-dihydro-2H-pyrrolo[3,4-c]pyridine-2-carboxamide;
N-{4-[(3R)-tetrahydrofuran-3-ylcarbamoyl]phenyl}-1,3-dihydro-2H-pyrrolo[3,4-c]pyridine-2-carboxamide;
N-{4-[(2-methoxyethyl)(methyl)carbamoyl]phenyl}-1,3-dihydro-2H-pyrrolo[3,4-c]pyridine-2-carboxamide;
N-{4-[(1-methoxypropan-2-yl)carbamoyl]phenyl}-1,3-dihydro-2H-pyrrolo[3,4-c]pyridine-2-carboxamide;
N-{4-[(cyclopentylmethyl)carbamoyl]phenyl}-1,3-dihydro-2H-pyrrolo[3,4-c]pyridine-2-carboxamide;
N-{4-[(2-thienylmethyl)carbamoyl]phenyl}-1,3-dihydro-2H-pyrrolo[3,4-c]pyridine-2-carboxamide;
N-{4-[methyl(tetrahydrofuran-2-ylmethyl)carbamoyl]phenyl}-1,3-dihydro-2H-pyrrolo[3,4-c]pyridine-2-carboxamide;
N-{4-[(3-isopropoxypropyl)carbamoyl]phenyl}-1,3-dihydro-2H-pyrrolo[3,4-c]pyridine-2-carboxamide;
N-{4-[benzyl(methyl)carbamoyl]phenyl}-1,3-dihydro-2H-pyrrolo[3,4-c]pyridine-2-carboxamide;
N-{4-[(3-aminobenzyl)carbamoyl]phenyl}-1,3-dihydro-2H-pyrrolo[3,4-c]pyridine-2-carboxamide;
N-{4-[(6-methoxypyridin-3-yl)carbamoyl]phenyl}-1,3-dihydro-2H-pyrrolo[3,4-c]pyridine-2-carboxamide;
N-{4-[(3-isobutoxypropyl)carbamoyl]phenyl}-1,3-dihydro-2H-pyrrolo[3,4-c]pyridine-2-carboxamide;
N-{4-[bis(2-methoxyethyl)carbamoyl]phenyl}-1,3-dihydro-2H-pyrrolo[3,4-c]pyridine-2-carboxamide;
N-{4-[(4-methoxybenzyl)carbamoyl]phenyl}-1,3-dihydro-2H-pyrrolo[3,4-c]pyridine-2-carboxamide;
N-{4-[(3-methoxybenzyl)carbamoyl]phenyl}-1,3-dihydro-2H-pyrrolo[3,4-c]pyridine-2-carboxamide;
N-(4-{[4-(trifluoromethyl)piperidin-1-yl]carbonyl}phenyl)-1,3-dihydro-2H-pyrrolo[3,4-c]pyridine-2-carboxamide;
N-(4-{[4-(pyrazin-2-yl)piperazin-1-yl]carbonyl}phenyl)-1,3-dihydro-2H-pyrrolo[3,4-c]pyridine-2-carboxamide;
N-{4-[(4-cyclohexylpiperazin-1-yl)carbonyl]phenyl}-1,3-dihydro-2H-pyrrolo[3,4-c]pyridine-2-carboxamide;
N-(4-{[2-(3,4-dimethoxyphenyl)ethyl]carbamoyl}phenyl)-1,3-dihydro-2H-pyrrolo[3,4-c]pyridine-2-carboxamide;
N-{4-[5-(morpholin-4-ylmethyl)-1,2,4-oxadiazol-3-yl]phenyl}-1,3-dihydro-2H-isoindole-2-carboxamide;
N-(4-{5-[(4-methylpiperazin-1-yl)methyl]-1,2,4-oxadiazol-3-yl}phenyl)-1,3-dihydro-2H-isoindole-2-carboxamide;
N-[4-(5-{[(3-methylbutyl)amino]methyl}-1,2,4-oxadiazol-3-yl)phenyl]-1,3-dihydro-2H-isoindole-2-carboxamide;
N-(4-{5-[(4-hydroxypiperidin-1-yl)methyl]-1,2,4-oxadiazol-3-yl}phenyl)-1,3-dihydro-2H-isoindole-2-carboxamide;

N-{4-[1-(tetrahydro-2H-pyran-4-ylcarbonyl)-1,2,3,6-tetrahydropyridin-4-yl]phenyl}-1,3-dihydro-2H-isoindole-2-carboxamide;
N-{4-[1-(1,4-dioxan-2-ylcarbonyl)-1,2,3,6-tetrahydropyridin-4-yl]phenyl}-1,3-dihydro-2H-isoindole-2-carboxamide;
N-(4-{1-[(1-methylpyrrolidin-3-yl)carbonyl]-1,2,3,6-tetrahydropyridin-4-yl}phenyl)-1,3-dihydro-2H-isoindole-2-carboxamide;
N-(4-{1-[(1,1-dioxidotetrahydrothiophen-3-yl)carbonyl]-1,2,3,6-tetrahydropyridin-4-yl}phenyl)-1,3-dihydro-2H-isoindole-2-carboxamide;
N-{4-[1-(2-hydroxy-2-methylpropanoyl)-1,2,3,6-tetrahydropyridin-4-yl]phenyl}-1,3-dihydro-2H-isoindole-2-carboxamide;
N-(4-{[3-(dimethylamino)propyl]carbamoyl}phenyl)-1,3-dihydro-2H-pyrrolo[3,4-c]pyridine-2-carboxamide;
N-(4-{[3-(morpholin-4-yl)propyl]carbamoyl}phenyl)-1,3-dihydro-2H-pyrrolo[3,4-c]pyridine-2-carboxamide;
N-(4-{[4-(2-aminoethyl)-1H-imidazol-1-yl]carbonyl}phenyl)-1,3-dihydro-2H-pyrrolo[3,4-c]pyridine-2-carboxamide;
N-[4-({4-[2-(2-hydroxyethoxy)ethyl]piperazin-1-yl}carbonyl)phenyl]-1,3-dihydro-2H-pyrrolo[3,4-c]pyridine-2-carboxamide;
N-{4-[(3-hydroxypropyl)carbamoyl]phenyl}-1,3-dihydro-2H-pyrrolo[3,4-c]pyridine-2-carboxamide;
N-(4-{[4-(dimethylamino)butyl]carbamoyl}phenyl)-1,3-dihydro-2H-pyrrolo[3,4-c]pyridine-2-carboxamide;
N-{4-[(pyridin-4-ylmethyl)carbamoyl]phenyl}-1,3-dihydro-2H-pyrrolo[3,4-c]pyridine-2-carboxamide;
N-{4-[(pyridin-3-ylmethyl)carbamoyl]phenyl}-1,3-dihydro-2H-pyrrolo[3,4-c]pyridine-2-carboxamide;
N-{4-[(pyrimidin-4-ylmethyl)carbamoyl]phenyl}-1,3-dihydro-2H-pyrrolo[3,4-c]pyridine-2-carboxamide;
N-(4-{[2-(pyridin-3-yl)ethyl]carbamoyl}phenyl)-1,3-dihydro-2H-pyrrolo[3,4-c]pyridine-2-carboxamide;
N-(4-{[2-(4-methylpiperazin-1-yl)ethyl]carbamoyl}phenyl)-1,3-dihydro-2H-pyrrolo[3,4-c]pyridine-2-carboxamide;
N-(4-{[(1,1-dioxidotetrahydrothiophen-3-yl)methyl]carbamoyl}phenyl)-1,3-dihydro-2H-isoindole-2-carboxamide;
N-(4-{[(2,2-dimethyl-1,3-dioxolan-4-yl)methyl]carbamoyl}phenyl)-1,3-dihydro-2H-isoindole-2-carboxamide;
N-(4-{[(1S)-2-methoxy-1-phenylethyl]carbamoyl}phenyl)-1,3-dihydro-2H-isoindole-2-carboxamide;
N-[4-({[(4S)-2,2-dimethyl-1,3-dioxolan-4-yl]methyl}carbamoyl)phenyl]-1,3-dihydro-2H-isoindole-2-carboxamide;
N-[4-({[(4R)-2,2-dimethyl-1,3-dioxolan-4-yl]methyl}carbamoyl)phenyl]-1,3-dihydro-2H-isoindole-2-carboxamide;
N-[4-({[3-(hydroxymethyl)oxetan-3-yl]methyl}carbamoyl)phenyl]-1,3-dihydro-2H-isoindole-2-carboxamide;
N-[4-(2-{benzyl[3-(morpholin-4-yl)propyl]amino}-2-oxoethyl)phenyl]-1,3-dihydro-2H-isoindole-2-carboxamide;
N-[4-(3-{benzyl[3-(morpholin-4-yl)propyl]amino}-3-oxopropyl)phenyl]-1,3-dihydro-2H-isoindole-2-carboxamide;
N-{4-[(cyclopentylacetyl)amino]phenyl}-5-fluoro-1,3-dihydro-2H-isoindole-2-carboxamide;
N-{4-[(2R)-butan-2-ylcarbamoyl]phenyl}-1,3-dihydro-2H-isoindole-2-carboxamide;
N-{4-[(cyclopentylacetyl)amino]phenyl}-5-(trifluoromethyl)-1,3-dihydro-2H-isoindole-2-carboxamide;
4-cyano-N-{4-[(cyclopentylacetyl)amino]phenyl}-1,3-dihydro-2H-isoindole-2-carboxamide;
N-{4-[(cyclopentylacetyl)amino]phenyl}-5-methyl-1,3-dihydro-2H-isoindole-2-carboxamide;
4-chloro-N-{4-[(cyclopentylacetyl)amino]phenyl}-1,3-dihydro-2H-isoindole-2-carboxamide;
5-chloro-N-{4-[(cyclopentylacetyl)amino]phenyl}-1,3-dihydro-2H-isoindole-2-carboxamide;
N-{4-[1-(morpholin-4-ylacetyl)-1,2,3,6-tetrahydropyridin-4-yl]phenyl}-1,3-dihydro-2H-pyrrolo[3,4-c]pyridine-2-carboxamide;
N-(4-{[(3-methyloxetan-3-yl)methyl]carbamoyl}phenyl)-1,3-dihydro-2H-isoindole-2-carboxamide;
N-(4-{[(3-methyloxetan-3-yl)methyl]carbamoyl}phenyl)-1,3-dihydro-2H-pyrrolo[3,4-c]pyridine-2-carboxamide;
N-[4-(2-benzyl-1,3-thiazol-4-yl)phenyl]-1,3-dihydro-2H-isoindole-2-carboxamide;
N-{4-[(3-methylbutyl)sulfamoyl]phenyl}-1,3-dihydro-2H-isoindole-2-carboxamide;
5-cyano-N-{4-[(cyclopentylmethyl)carbamoyl]phenyl}-1,3-dihydro-2H-isoindole-2-carboxamide;
5-cyano-N-{4-[(1,3-thiazol-5-ylmethyl)carbamoyl]phenyl}-1,3-dihydro-2H-isoindole-2-carboxamide;
5-cyano-N-(4-{[(1R)-3-hydroxy-1-phenylpropyl]carbamoyl}phenyl)-1,3-dihydro-2H-isoindole-2-carboxamide;
5-cyano-N-(4-{[2-hydroxy-1-(4-methylphenyl)ethyl]carbamoyl}phenyl)-1,3-dihydro-2H-isoindole-2-carboxamide;
5-cyano-N-{4-[(1,3-dihydroxypropan-2-yl)carbamoyl]phenyl}-1,3-dihydro-2H-isoindole-2-carboxamide;
5-cyano-N-(4-{[(2R)-2-hydroxypropyl]carbamoyl}phenyl)-1,3-dihydro-2H-isoindole-2-carboxamide;
5-cyano-N-{4-[(2-hydroxy-2-methylpropyl)carbamoyl]phenyl}-1,3-dihydro-2H-isoindole-2-carboxamide;
5-cyano-N-(4-{[(2R)-1-hydroxy-3-methylbutan-2-yl]carbamoyl}phenyl)-1,3-dihydro-2H-isoindole-2-carboxamide;
5-cyano-N-(4-{[(2S)-tetrahydrofuran-2-ylmethyl]carbamoyl}phenyl)-1,3-dihydro-2H-isoindole-2-carboxamide;
5-cyano-N-(4-{[2-(4-methylpiperazin-1-yl)ethyl]carbamoyl}phenyl)-1,3-dihydro-2H-isoindole-2-carboxamide;
5-cyano-N-(4-{[(1S)-2-hydroxy-1-phenylethyl]carbamoyl}phenyl)-1,3-dihydro-2H-isoindole-2-carboxamide;
5-cyano-N-{4-[(4-hydroxybutyl)carbamoyl]phenyl}-1,3-dihydro-2H-isoindole-2-carboxamide;
5-cyano-N-(4-{[(2S)-2-hydroxypropyl]carbamoyl}phenyl)-1,3-dihydro-2H-isoindole-2-carboxamide;
5-cyano-N-{4-[(3-furylmethyl)carbamoyl]phenyl}-1,3-dihydro-2H-isoindole-2-carboxamide;
5-cyano-N-{4-[(tetrahydrofuran-2-ylmethyl)carbamoyl]phenyl}-1,3-dihydro-2H-isoindole-2-carboxamide;
5-cyano-N-(4-{[4-(2-furoyl)piperazin-1-yl]carbonyl}phenyl)-1,3-dihydro-2H-isoindole-2-carboxamide;
5-cyano-N-(4-{[4-(tetrahydrofuran-2-ylcarbonyl)piperazin-1-yl]carbonyl}phenyl)-1,3-dihydro-2H-isoindole-2-carboxamide;
5-cyano-N-(4-{[3-(piperidin-1-yl)propyl]carbamoyl}phenyl)-1,3-dihydro-2H-isoindole-2-carboxamide;
5-cyano-N-(4-{[(2R)-tetrahydrofuran-2-ylmethyl]carbamoyl}phenyl)-1,3-dihydro-2H-isoindole-2-carboxamide;

5-cyano-N-(4-{[4-(ethylsulfonyl)piperazin-1-yl] carbonyl}phenyl)-1,3-dihydro-2H-isoindole-2-carboxamide;
5-cyano-N-{4-[(tetrahydrofuran-3-ylmethyl)carbamoyl] phenyl}-1,3-dihydro-2H-isoindole-2-carboxamide;
5-cyano-N-(4-{[(1R)-2-hydroxy-1-phenylethyl] carbamoyl}phenyl)-1,3-dihydro-2H-isoindole-2-carboxamide;
5-cyano-N-(4-{[(2S)-1-hydroxybutan-2-yl] carbamoyl}phenyl)-1,3-dihydro-2H-isoindole-2-carboxamide;
5-cyano-N-{4-[(2,3-dihydroxypropyl)carbamoyl]phenyl}-1,3-dihydro-2H-isoindole-2-carboxamide;
5-cyano-N-{4-[(tetrahydro-2H-pyran-4-ylmethyl)carbamoyl]phenyl}-1,3-dihydro-2H-isoindole-2-carboxamide;
5-cyano-N-(4-{[2-hydroxy-1-(pyridin-2-yl)ethyl] carbamoyl}phenyl)-1,3-dihydro-2H-isoindole-2-carboxamide;
5-cyano-N-{4-[(1-hydroxy-4-methylpentan-2-yl)carbamoyl]phenyl}-1,3-dihydro-2H-isoindole-2-carboxamide;
5-cyano-N-(4-{[(1-methylpyrrolidin-3-yl)methyl] carbamoyl}phenyl)-1,3-dihydro-2H-isoindole-2-carboxamide;
5-cyano-N-(4-{[(1-methylpiperidin-4-yl)methyl] carbamoyl}phenyl)-1,3-dihydro-2H-isoindole-2-carboxamide;
5-cyano-N-{4-[(tetrahydro-2H-pyran-3-ylmethyl)carbamoyl]phenyl}-1,3-dihydro-2H-isoindole-2-carboxamide;
N-[4-(2,6-diazaspiro[3.3]hept-2-ylcarbonyl)phenyl]-1,3-dihydro-2H-isoindole-2-carboxamide;
N-[4-(2,6-diazaspiro[3.4]oct-6-ylcarbonyl)phenyl]-1,3-dihydro-2H-isoindole-2-carboxamide;
N-[4-(2,7-diazaspiro[3.5]non-7-ylcarbonyl)phenyl]-1,3-dihydro-2H-isoindole-2-carboxamide;
N-[4-(2,6-diazaspiro[3.5]non-2-ylcarbonyl)phenyl]-1,3-dihydro-2H-isoindole-2-carboxamide;
N-[4-(1,7-diazaspiro[4.4]non-1-ylcarbonyl)phenyl]-1,3-dihydro-2H-isoindole-2-carboxamide;
N-[4-(1,7-diazaspiro[4.4]non-7-ylcarbonyl)phenyl]-1,3-dihydro-2H-isoindole-2-carboxamide;
N-[4-(2,7-diazaspiro[4.4]non-2-ylcarbonyl)phenyl]-1,3-dihydro-2H-isoindole-2-carboxamide;
N-[4-(2,8-diazaspiro[4.5]dec-2-ylcarbonyl)phenyl]-1,3-dihydro-2H-isoindole-2-carboxamide;
N-[4-(2,7-diazaspiro[4.5]dec-2-ylcarbonyl)phenyl]-1,3-dihydro-2H-isoindole-2-carboxamide;
N-[4-(2,6-diazaspiro[4.5]dec-2-ylcarbonyl)phenyl]-1,3-dihydro-2H-isoindole-2-carboxamide;
N-[4-(2,7-diazaspiro[4.5]dec-7-ylcarbonyl)phenyl]-1,3-dihydro-2H-isoindole-2-carboxamide;
N-[4-(3,9-diazaspiro[5.5]undec-3-ylcarbonyl)phenyl]-1,3-dihydro-2H-isoindole-2-carboxamide;
N-[4-(2,9-diazaspiro[5.5]undec-2-ylcarbonyl)phenyl]-1,3-dihydro-2H-isoindole-2-carboxamide;
N-[4-(2,8-diazaspiro[5.5]undec-2-ylcarbonyl)phenyl]-1,3-dihydro-2H-isoindole-2-carboxamide;
N-[4-(1,8-diazaspiro[5.5]undec-8-ylcarbonyl)phenyl]-1,3-dihydro-2H-isoindole-2-carboxamide;
N-[4-(1,8-diazaspiro[4.6]undec-8-ylcarbonyl)phenyl]-1,3-dihydro-2H-isoindole-2-carboxamide;
N-{4-[(1-oxa-8-azaspiro[4.5]dec-2-ylmethyl)carbamoyl]phenyl}-1,3-dihydro-2H-isoindole-2-carboxamide;
N-(1-oxa-8-azaspiro[4.5]dec-3-ylcarbamoyl)phenyl]-1,3-dihydro-2H-isoindole-2-carboxamide;
N-{4-[(2-oxa-9-azaspiro[5.5]undec-3-ylmethyl)carbamoyl]phenyl}-1,3-dihydro-2H-isoindole-2-carboxamide;
N-[4-(1-oxa-4,8-diazaspiro[5.5]undec-4-ylcarbonyl)phenyl]-1,3-dihydro-2H-isoindole-2-carboxamide;
N-[4-(1,8-diazaspiro[4.5]dec-1-ylcarbonyl)phenyl]-1,3-dihydro-2H-isoindole-2-carboxamide;
N-[4-(1,8-diazaspiro[4.5]dec-8-ylcarbonyl)phenyl]-1,3-dihydro-2H-isoindole-2-carboxamide;
N-[4-(2,6-diazaspiro[3.4]oct-2-ylcarbonyl)phenyl]-1,3-dihydro-2H-isoindole-2-carboxamide;
N-[4-(1,7-diazaspiro[3.5]non-7-ylcarbonyl)phenyl]-1,3-dihydro-2H-isoindole-2-carboxamide;
N-[4-(1,6-diazaspiro[3.5]non-1-ylcarbonyl)phenyl]-1,3-dihydro-2H-isoindole-2-carboxamide;
N-[4-(2,5-diazaspiro[3.5]non-2-ylcarbonyl)phenyl]-1,3-dihydro-2H-isoindole-2-carboxamide;
N-[4-(5-oxa-2-azaspiro[3.4]oct-2-ylcarbonyl)phenyl]-1,3-dihydro-2H-isoindole-2-carboxamide;
N-[4-(6-oxa-2-azaspiro[3.5]non-2-ylcarbonyl)phenyl]-1,3-dihydro-2H-isoindole-2-carboxamide;
N-[4-(hexahydro-5H-furo[2,3-c]pyrrol-5-ylcarbonyl)phenyl]-1,3-dihydro-2H-isoindole-2-carboxamide;
N-[4-(tetrahydro-1H-furo[3,4-c]pyrrol-5 (3H)-ylcarbonyl)phenyl]-1,3-dihydro-2H-isoindole-2-carboxamide;
N-[4-(hexahydro furo[3,4-c]pyridin-5 (3H)-ylcarbonyl)phenyl]-1,3-dihydro-2H-isoindole-2-carboxamide;
N-[4-(4-{benzyl[3-(morpholin-4-yl)propyl]amino}-4-oxobutyl)phenyl]-1,3-dihydro-2H-isoindole-2-carboxamide;
N-[4-(2-{benzyl[3-(morpholin-4-yl)propyl]amino}ethyl)phenyl]-1,3-dihydro-2H-isoindole-2-carboxamide;
5-acetyl-N-{4-[(cyclopentylacetyl)amino]phenyl}-1,3-dihydro-2H-isoindole-2-carboxamide;
N-(4-{[(1,1-dioxidotetrahydrothiophen-3-yl)methyl] carbamoyl}phenyl)-1,3-dihydro-2H-pyrrolo[3,4-c]pyridine-2-carboxamide;
5-cyano-N-{4-[(3-methylbutyl)sulfamoyl]phenyl}-1,3-dihydro-2H-isoindole-2-carboxamide;
N-{4-[(3-methylbutyl)sulfamoyl]phenyl}-1,3-dihydro-2H-pyrrolo[3,4-c]pyridine-2-carboxamide;
N-{4-[(cyclopentylacetyl)amino]phenyl}-5-(1-hydroxyethyl)-1,3-dihydro-2H-isoindole-2-carboxamide;
N-[4-(butyrylamino)phenyl]-5-cyano-1,3-dihydro-2H-isoindole-2-carboxamide;
N-{4-[(pyrrolidin-3-ylmethyl)carbamoyl]phenyl}-1,3-dihydro-2H-pyrrolo[3,4-c]pyridine-2-carboxamide;
N-(4-{[(3S)-pyrrolidin-3-ylmethyl]carbamoyl}phenyl)-1,3-dihydro-2H-pyrrolo[3,4-c]pyridine-2-carboxamide;
N-(4-{[(1-methylpyrrolidin-3-yl)methyl] carbamoyl}phenyl)-1,3-dihydro-2H-pyrrolo[3,4-c]pyridine-2-carboxamide;
N-(4-{[(3-methoxybenzyl)sulfonyl]amino}phenyl)-1,3-dihydro-2H-isoindole-2-carboxamide;
N-(4-{[(1-methylpiperidin-4-yl)methyl] carbamoyl}phenyl)-1,3-dihydro-2H-pyrrolo[3,4-c]pyridine-2-carboxamide;
N-[4-(2,6-diazaspiro[3.4]oct-6-ylcarbonyl)phenyl]-5-fluoro-1,3-dihydro-2H-isoindole-2-carboxamide;
N-[4-(2,7-diazaspiro[3.5]non-7-ylcarbonyl)phenyl]-5-fluoro-1,3-dihydro-2H-isoindole-2-carboxamide;
N-[4-(1,7-diazaspiro[4.4]non-1-ylcarbonyl)phenyl]-5-fluoro-1,3-dihydro-2H-isoindole-2-carboxamide;
N-[4-(2,8-diazaspiro[4.5]dec-2-ylcarbonyl)phenyl]-5-fluoro-1,3-dihydro-2H-isoindole-2-carboxamide;
N-[4-(2,6-diazaspiro[4.5]dec-2-ylcarbonyl)phenyl]-5-fluoro-1,3-dihydro-2H-isoindole-2-carboxamide;
N-[4-(2,7-diazaspiro[4.5]dec-7-ylcarbonyl)phenyl]-5-fluoro-1,3-dihydro-2H-isoindole-2-carboxamide;

N-[4-(2,8-diazaspiro[5.5]undec-2-ylcarbonyl)phenyl]-5-fluoro-1,3-dihydro-2H-isoindole-2-carboxamide;
N-[4-(1,8-diazaspiro[5.5]undec-8-ylcarbonyl)phenyl]-5-fluoro-1,3-dihydro-2H-isoindole-2-carboxamide;
N-[4-(1,8-diazaspiro[4.6]undec-8-ylcarbonyl)phenyl]-5-fluoro-1,3-dihydro-2H-isoindole-2-carboxamide;
5-fluoro-N-{4-[(1-oxa-8-azaspiro[4.5]dec-2-ylmethyl)carbamoyl]phenyl}-1,3-dihydro-2H-isoindole-2-carboxamide;
5-fluoro-N-[4-(1-oxa-8-azaspiro[4.5]dec-3-ylcarbamoyl)phenyl]-1,3-dihydro-2H-isoindole-2-carboxamide;
5-fluoro-N-[4-(1-oxa-4,8-diazaspiro[5.5]undec-4-ylcarbonyl)phenyl]-1,3-dihydro-2H-isoindole-2-carboxamide;
N-[4-(1,8-diazaspiro[4.5]dec-1-ylcarbonyl)phenyl]-5-fluoro-1,3-dihydro-2H-isoindole-2-carboxamide;
N-[4-(1,8-diazaspiro[4.5]dec-8-ylcarbonyl)phenyl]-5-fluoro-1,3-dihydro-2H-isoindole-2-carboxamide;
N-[4-(2,6-diazaspiro[3.4]oct-2-ylcarbonyl)phenyl]-5-fluoro-1,3-dihydro-2H-isoindole-2-carboxamide;
N-[4-(1,7-diazaspiro[3.5]non-7-ylcarbonyl)phenyl]-5-fluoro-1,3-dihydro-2H-isoindole-2-carboxamide;
N-[4-(1,6-diazaspiro[3.5]non-1-ylcarbonyl)phenyl]-5-fluoro-1,3-dihydro-2H-isoindole-2-carboxamide;
N-[4-(2,5-diazaspiro[3.5]non-2-ylcarbonyl)phenyl]-5-fluoro-1,3-dihydro-2H-isoindole-2-carboxamide;
5-fluoro-N-[4-(5-oxa-2-azaspiro[3.4]oct-2-ylcarbonyl)phenyl]-1,3-dihydro-2H-isoindole-2-carboxamide;
5-fluoro-N-[4-(6-oxa-2-azaspiro[3.5]non-2-ylcarbonyl)phenyl]-1,3-dihydro-2H-isoindole-2-carboxamide;
5-fluoro-N-[4-(2-oxa-7-azaspiro[3.5]non-7-ylcarbonyl)phenyl]-1,3-dihydro-2H-isoindole-2-carboxamide;
5-fluoro-N-[4-(hexahydro-5H-furo[2,3-c]pyrrol-5-ylcarbonyl)phenyl]-1,3-dihydro-2H-isoindole-2-carboxamide;
5-fluoro-N-[4-(tetrahydro-1H-furo[3,4-c]pyrrol-5(3H)-ylcarbonyl)phenyl]-1,3-dihydro-2H-isoindole-2-carboxamide;
5-fluoro-N-[4-(hexahydrofuro[3,4-c]pyridin-5(3H)-ylcarbonyl)phenyl]-1,3-dihydro-2H-isoindole-2-carboxamide;
N-{4-[1-(tetrahydrofuran-3-ylcarbonyl)piperidin-4-yl]phenyl}-1,3-dihydro-2H-pyrrolo[3,4-c]pyridine-2-carboxamide;
N-(4-{1-[(2-methoxyethoxy)acetyl]piperidin-4-yl}phenyl)-1,3-dihydro-2H-pyrrolo[3,4-c]pyridine-2-carboxamide;
N-{4-[1-(tetrahydrofuran-2-ylcarbonyl)piperidin-4-yl]phenyl}-1,3-dihydro-2H-pyrrolo[3,4-c]pyridine-2-carboxamide;
N-{4-[1-(tetrahydro-2H-pyran-4-ylcarbonyl)piperidin-4-yl]phenyl}-1,3-dihydro-2H-pyrrolo[3,4-c]pyridine-2-carboxamide;
N-{4-[1-(1,4-dioxan-2-ylcarbonyl)piperidin-4-yl]phenyl}-1,3-dihydro-2H-pyrrolo[3,4-c]pyridine-2-carboxamide;
N-(4-{1-[(1-methylpyrrolidin-3-yl)carbonyl]piperidin-4-yl}phenyl)-1,3-dihydro-2H-pyrrolo[3,4-c]pyridine-2-carboxamide;
N-(4-{1-[(1,1-dioxidotetrahydrothiophen-3-yl)carbonyl]piperidin-4-yl}phenyl)-1,3-dihydro-2H-pyrrolo[3,4-c]pyridine-2-carboxamide;
N-{4-[1-(2-hydroxy-2-methylpropanoyl)piperidin-4-yl]phenyl}-1,3-dihydro-2H-pyrrolo[3,4-c]pyridine-2-carboxamide;
N-{4-[1-(morpholin-4-ylacetyl)piperidin-4-yl]phenyl}-1,3-dihydro-2H-pyrrolo[3,4-c]pyridine-2-carboxamide;
5-(acetamidomethyl)-N-{4-[(cyclopentylacetyl)amino]phenyl}-1,3-dihydro-2H-isoindole-2-carboxamide;
N-[4-({[(3R)-1-isobutyrylpyrrolidin-3-yl]methyl}carbamoyl)phenyl]-1,3-dihydro-2H-pyrrolo[3,4-c]pyridine-2-carboxamide;
N-[4-({[(3R)-1-benzoylpyrrolidin-3-yl]methyl}carbamoyl)phenyl]-1,3-dihydro-2H-pyrrolo[3,4-c]pyridine-2-carboxamide;
N-[4-({[1-(tetrahydrofuran-3-ylcarbonyl)pyrrolidin-3-yl]methyl}carbamoyl)phenyl]-1,3-dihydro-2H-pyrrolo[3,4-c]pyridine-2-carboxamide;
N-[4-({[1-(methylsulfonyl)pyrrolidin-3-yl]methyl}carbamoyl)phenyl]-1,3-dihydro-2H-pyrrolo[3,4-c]pyridine-2-carboxamide;
N-[4-(1-isobutyl-1,2,3,6-tetrahydropyridin-4-yl)phenyl]-1,3-dihydro-2H-pyrrolo[3,4-c]pyridine-2-carboxamide;
N-{4-[1-(tetrahydrofuran-3-ylmethyl)-1,2,3,6-tetrahydropyridin-4-yl]phenyl}-1,3-dihydro-2H-pyrrolo[3,4-c]pyridine-2-carboxamide;
N-{4-[1-(tetrahydro-2H-pyran-4-ylmethyl)-1,2,3,6-tetrahydropyridin-4-yl]phenyl}-1,3-dihydro-2H-pyrrolo[3,4-c]pyridine-2-carboxamide;
N-[4-(1-isobutylpiperidin-4-yl)phenyl]-1,3-dihydro-2H-pyrrolo[3,4-c]pyridine-2-carboxamide;
N-{4-[1-(tetrahydrofuran-3-ylmethyl)piperidin-4-yl]phenyl}-1,3-dihydro-2H-pyrrolo[3,4-c]pyridine-2-carboxamide;
N-{4-[1-(tetrahydro-2H-pyran-4-ylmethyl)piperidin-4-yl]phenyl}-1,3-dihydro-2H-pyrrolo[3,4-c]pyridine-2-carboxamide;
N-{4-[(cyclopentylacetyl)amino]phenyl}-5-(2-hydroxypropan-2-yl)-1,3-dihydro-2H-isoindole-2-carboxamide;
tert-butyl {4-[(1,3-dihydro-2H-isoindol-2-ylcarbonyl)amino]benzyl}carbamate;
N-{4-[(cyclopentylacetyl)amino]phenyl}-1,3-dihydro-2H-pyrrolo[3,4-c]pyridine-2-carboxamide;
N-{4-[(cyclopentylacetyl)amino]phenyl}-5-(methoxymethyl)-1,3-dihydro-2H-isoindole-2-carboxamide;
N-[4-(5-{[(tetrahydrofuran-2-ylmethyl)amino]methyl}-1,2,4-oxadiazol-3-yl)phenyl]-1,3-dihydro-2H-isoindole-2-carboxamide;
N-(4-{5-[(4-methoxypiperidin-1-yl)methyl]-1,2,4-oxadiazol-3-yl}phenyl)-1,3-dihydro-2H-isoindole-2-carboxamide;
N-[4-(5-{[4-(2-methoxyethyl)piperazin-1-yl]methyl}-1,2,4-oxadiazol-3-yl)phenyl]-1,3-dihydro-2H-isoindole-2-carboxamide;
N-[4-({[1-(morpholin-4-yl)cyclopentyl]methyl}carbamoyl)phenyl]-1,3-dihydro-2H-pyrrolo[3,4-c]pyridine-2-carboxamide;
N-{4-[(1-pentanoylpiperidin-4-yl)oxy]phenyl}-1,3-dihydro-2H-pyrrolo[3,4-c]pyridine-2-carboxamide;
N-{4-[(1-acetylpiperidin-4-yl)oxy]phenyl}-1,3-dihydro-2H-pyrrolo[3,4-c]pyridine-2-carboxamide;
N-{4-[(1-butyrylpiperidin-4-yl)oxy]phenyl}-1,3-dihydro-2H-pyrrolo[3,4-c]pyridine-2-carboxamide;
N-(4-{[1-(2-methylbutanoyl)piperidin-4-yl]oxy}phenyl)-1,3-dihydro-2H-pyrrolo[3,4-c]pyridine-2-carboxamide;
N-(4-{[1-(3,3,3-trifluoropropanoyl)piperidin-4-yl]oxy}phenyl)-1,3-dihydro-2H-pyrrolo[3,4-c]pyridine-2-carboxamide;
N-(4-{[1-(methoxyacetyl)piperidin-4-yl]oxy}phenyl)-1,3-dihydro-2H-pyrrolo[3,4-c]pyridine-2-carboxamide;
N-(4-{[1-(tetrahydrofuran-2-ylcarbonyl)piperidin-4-yl]oxy}phenyl)-1,3-dihydro-2H-pyrrolo[3,4-c]pyridine-2-carboxamide;
N-(4-{[1-(cyclopropylcarbonyl)piperidin-4-yl]oxy}phenyl)-1,3-dihydro-2H-pyrrolo[3,4-c]pyridine-2-carboxamide;
N-(4-{[1-(cyclopropylacetyl)piperidin-4-yl]oxy}phenyl)-1,3-dihydro-2H-pyrrolo[3,4-c]pyridine-2-carboxamide;

N-(4-{[1-(cyclobutylcarbonyl)piperidin-4-yl]oxy}phenyl)-1,3-dihydro-2H-pyrrolo[3,4-c]pyridine-2-carboxamide;
N-(4-{[1-(cyclopentylcarbonyl)piperidin-4-yl]oxy}phenyl)-1,3-dihydro-2H-pyrrolo[3,4-c]pyridine-2-carboxamide;
N-(4-{[1-(cyclopentylacetyl)piperidin-4-yl]oxy}phenyl)-1,3-dihydro-2H-pyrrolo[3,4-c]pyridine-2-carboxamide;
N-(4-{[1-(cyclohexylcarbonyl)piperidin-4-yl]oxy}phenyl)-1,3-dihydro-2H-pyrrolo[3,4-c]pyridine-2-carboxamide;
tert-butyl (2-{4-[(1,3-dihydro-2H-isoindol-2-ylcarbonyl)amino]phenyl}ethyl)carbamate;
N-(4-{1-[(2R)-tetrahydrofuran-2-ylcarbonyl]-1,2,3,6-tetrahydropyridin-4-yl}phenyl)-1,3-dihydro-2H-pyrrolo[3,4-c]pyridine-2-carboxamide;
N-(4-{1-[(2S)-tetrahydrofuran-2-ylcarbonyl]-1,2,3,6-tetrahydropyridin-4-yl}phenyl)-1,3-dihydro-2H-pyrrolo[3,4-c]pyridine-2-carboxamide;
N-(4-{[(1S)-1-(4-fluorophenyl)-2-hydroxyethyl]carbamoyl}phenyl)-1,3-dihydro-2H-pyrrolo[3,4-c]pyridine-2-carboxamide;
N-(4-{[(1S)-2-hydroxy-1-(4-methoxyphenyl)ethyl]carbamoyl}phenyl)-1,3-dihydro-2H-pyrrolo[3,4-c]pyridine-2-carboxamide;
N-[4-({[3-(hydroxymethyl)oxetan-3-yl]methyl}carbamoyl)phenyl]-1,3-dihydro-2H-pyrrolo[3,4-c]pyridine-2-carboxamide;
N-(4-{[(1S)-1-(1,3-benzodioxol-5-yl)-2-hydroxyethyl]carbamoyl}phenyl)-1,3-dihydro-2H-pyrrolo[3,4-c]pyridine-2-carboxamide;
N-{4-[(tetrahydrofuran-3-ylmethyl)sulfamoyl]phenyl}-1,3-dihydro-2H-isoindole-2-carboxamide;
N-{4-[(tetrahydrofuran-3-ylmethyl)sulfamoyl]phenyl}-1,3-dihydro-2H-pyrrolo[3,4-c]pyridine-2-carboxamide;
5-cyano-N-{4-[(tetrahydrofuran-3-ylmethyl)sulfamoyl]phenyl}-1,3-dihydro-2H-isoindole-2-carboxamide;
N-(4-{[(1S)-1-(4-fluorophenyl)-2-hydroxyethyl]carbamoyl}phenyl)-1,3-dihydro-2H-isoindole-2-carboxamide;
N-(4-{[(1S)-2-hydroxy-1-(4-methoxyphenyl)ethyl]carbamoyl}phenyl)-1,3-dihydro-2H-isoindole-2-carboxamide;
N-(4-{[(1S)-1-(1,3-benzodioxol-5-yl)-2-hydroxyethyl]carbamoyl}phenyl)-1,3-dihydro-2H-isoindole-2-carboxamide;
N-{4-[1-(tetrahydrofuran-3-ylcarbonyl)piperidin-4-yl]phenyl}-1,3-dihydro-2H-isoindole-2-carboxamide;
N-{4-[1-(tetrahydrofuran-2-ylcarbonyl)piperidin-4-yl]phenyl}-1,3-dihydro-2H-isoindole-2-carboxamide;
N-{4-[1-(tetrahydro-2H-pyran-4-ylcarbonyl)piperidin-4-yl]phenyl}-1,3-dihydro-2H-isoindole-2-carboxamide;
N-{4-[1-(1,4-dioxan-2-ylcarbonyl)piperidin-4-yl]phenyl}-1,3-dihydro-2H-isoindole-2-carboxamide;
N-(4-{1-[(1-methylpyrrolidin-3-yl)carbonyl]piperidin-4-yl}phenyl)-1,3-dihydro-2H-isoindole-2-carboxamide;
N-(4-{1-[(1,1-dioxidotetrahydrothiophen-3-yl)carbonyl]piperidin-4-yl}phenyl)-1,3-dihydro-2H-isoindole-2-carboxamide;
N-{4-[1-(2-hydroxy-2-methylpropanoyl)piperidin-4-yl]phenyl}-1,3-dihydro-2H-isoindole-2-carboxamide;
N-{4-[1-(morpholin-4-ylacetyl)piperidin-4-yl]phenyl}-1,3-dihydro-2H-isoindole-2-carboxamide;
N-(4-{[1-(3,3,3-trifluoropropanoyl)azetidin-3-yl]oxy}phenyl)-1,3-dihydro-2H-pyrrolo[3,4-c]pyridine-2-carboxamide;
N-(4-{[1-(4,4,4-trifluorobutanoyl)azetidin-3-yl]oxy}phenyl)-1,3-dihydro-2H-pyrrolo[3,4-c]pyridine-2-carboxamide;
N-(4-{[1-(tetrahydrofuran-2-ylcarbonyl)azetidin-3-yl]oxy}phenyl)-1,3-dihydro-2H-pyrrolo[3,4-c]pyridine-2-carboxamide;
N-(4-{[1-(tetrahydrofuran-3-ylacetyl)azetidin-3-yl]oxy}phenyl)-1,3-dihydro-2H-pyrrolo[3,4-c]pyridine-2-carboxamide;
N-(4-{[1-(cyclobutylcarbonyl)azetidin-3-yl]oxy}phenyl)-1,3-dihydro-2H-pyrrolo[3,4-c]pyridine-2-carboxamide;
N-(4-{[1-(cyclopentylcarbonyl)azetidin-3-yl]oxy}phenyl)-1,3-dihydro-2H-pyrrolo[3,4-c]pyridine-2-carboxamide;
N-(4-{[1-(3-phenylpropanoyl)pyrrolidin-3-yl]oxy}phenyl)-1,3-dihydro-2H-pyrrolo[3,4-c]pyridine-2-carboxamide;
N-(4-{[1-(phenylacetyl)pyrrolidin-3-yl]oxy}phenyl)-1,3-dihydro-2H-pyrrolo[3,4-c]pyridine-2-carboxamide;
N-[4-({1-[(4-methoxyphenyl)acetyl]pyrrolidin-3-yl}oxy)phenyl]-1,3-dihydro-2H-pyrrolo[3,4-c]pyridine-2-carboxamide;
N-(4-{[1-(methoxyacetyl)pyrrolidin-3-yl]oxy}phenyl)-1,3-dihydro-2H-pyrrolo[3,4-c]pyridine-2-carboxamide;
N-(4-{[1-(cyclopropylcarbonyl)pyrrolidin-3-yl]oxy}phenyl)-1,3-dihydro-2H-pyrrolo[3,4-c]pyridine-2-carboxamide;
N-(4-{[1-(cyclohexylcarbonyl)pyrrolidin-3-yl]oxy}phenyl)-1,3-dihydro-2H-pyrrolo[3,4-c]pyridine-2-carboxamide;
N-(4-{[1-(cyclopentylacetyl)pyrrolidin-3-yl]oxy}phenyl)-1,3-dihydro-2H-pyrrolo[3,4-c]pyridine-2-carboxamide;
N-(4-{[1-(cyclopentylcarbonyl)pyrrolidin-3-yl]oxy}phenyl)-1,3-dihydro-2H-pyrrolo[3,4-c]pyridine-2-carboxamide;
N-{4-[(1-benzoylpyrrolidin-3-yl)oxy]phenyl}-1,3-dihydro-2H-pyrrolo[3,4-c]pyridine-2-carboxamide;
N-(4-{[1-(3-ethoxypropanoyl)pyrrolidin-3-yl]oxy}phenyl)-1,3-dihydro-2H-pyrrolo[3,4-c]pyridine-2-carboxamide;
N-[4-({1-[(2-methylcyclopropyl)carbonyl]pyrrolidin-3-yl}oxy)phenyl]-1,3-dihydro-2H-pyrrolo[3,4-c]pyridine-2-carboxamide;
N-[4-({1-[(1-methylcyclopropyl)carbonyl]pyrrolidin-3-yl}oxy)phenyl]-1,3-dihydro-2H-pyrrolo[3,4-c]pyridine-2-carboxamide;
N-(4-{[1-(cyclobutylcarbonyl)pyrrolidin-3-yl]oxy}phenyl)-1,3-dihydro-2H-pyrrolo[3,4-c]pyridine-2-carboxamide;
N-(4-{[1-(3-methylbutanoyl)pyrrolidin-3-yl]oxy}phenyl)-1,3-dihydro-2H-pyrrolo[3,4-c]pyridine-2-carboxamide;
N-(4-{[1-(2-methylpropanoyl)pyrrolidin-3-yl]oxy}phenyl)-1,3-dihydro-2H-pyrrolo[3,4-c]pyridine-2-carboxamide;
N-{4-[(1-acetylpyrrolidin-3-yl)oxy]phenyl}-1,3-dihydro-2H-pyrrolo[3,4-c]pyridine-2-carboxamide;
N-(4-{[1-(4,4,4-trifluorobutanoyl)pyrrolidin-3-yl]oxy}phenyl)-1,3-dihydro-2H-pyrrolo[3,4-c]pyridine-2-carboxamide;
N-(4-{[1-(tetrahydrofuran-3-ylcarbonyl)pyrrolidin-3-yl]oxy}phenyl)-1,3-dihydro-2H-pyrrolo[3,4-c]pyridine-2-carboxamide;
N-(4-{[1-(tetrahydrofuran-2-ylcarbonyl)pyrrolidin-3-yl]oxy}phenyl)-1,3-dihydro-2H-pyrrolo[3,4-c]pyridine-2-carboxamide;
N-(4-{[1-(ethoxyacetyl)pyrrolidin-3-yl]oxy}phenyl)-1,3-dihydro-2H-pyrrolo[3,4-c]pyridine-2-carboxamide;
N-(4-{[1-(tetrahydrofuran-3-ylcarbonyl)piperidin-4-yl]oxy}phenyl)-1,3-dihydro-2H-isoindole-2-carboxamide;
N-(4-{1-[(1-methylpiperidin-4-yl)carbonyl]-1,2,3,6-tetrahydropyridin-4-yl}phenyl)-1,3-dihydro-2H-pyrrolo[3,4-c]pyridine-2-carboxamide;
N-(4-{1-[(1,1-dioxidotetrahydro-2H-thiopyran-4-yl)carbonyl]-1,2,3,6-tetrahydropyridin-4-yl}phenyl)-1,3-dihydro-2H-pyrrolo[3,4-c]pyridine-2-carboxamide;

N-(4-{1-[(3R)-tetrahydrofuran-3-ylcarbonyl]-1,2,3,6-tetrahydropyridin-4-yl}phenyl)-1,3-dihydro-2H-pyrrolo[3,4-c]pyridine-2-carboxamide;
N-(4-{1-[(3S)-tetrahydrofuran-3-ylcarbonyl]-1,2,3,6-tetrahydropyridin-4-yl}phenyl)-1,3-dihydro-2H-pyrrolo[3,4-c]pyridine-2-carboxamide;
N-(4-{4-[(2-methylpropanoyl)amino]cyclohex-1-en-1-yl}phenyl)-1,3-dihydro-2H-pyrrolo[3,4-c]pyridine-2-carboxamide;
5-cyano-N-{4-[1-(2-methylpropanoyl)-1,2,3,6-tetrahydropyridin-4-yl]phenyl}-1,3-dihydro-2H-isoindole-2-carboxamide;
tert-butyl [(1-{4-[(1,3-dihydro-2H-isoindol-2-ylcarbonyl)amino]phenyl}azetidin-3-yl)methyl]carbamate;
N-(4-{4-[(tetrahydrofuran-3-ylcarbonyl)amino]cyclohex-1-en-1-yl}phenyl)-1,3-dihydro-2H-pyrrolo[3,4-c]pyridine-2-carboxamide;
N-(4-{4-[(tetrahydro-2H-pyran-4-ylcarbonyl)amino]cyclohex-1-en-1-yl}phenyl)-1,3-dihydro-2H-pyrrolo[3,4-c]pyridine-2-carboxamide;
N-(4-{4-[(morpholin-4-ylacetyl)amino]cyclohex-1-en-1-yl}phenyl)-1,3-dihydro-2H-pyrrolo[3,4-c]pyridine-2-carboxamide;
N-[4-(4-{[(2-methoxyethoxy)acetyl]amino}cyclohex-1-en-1-yl)phenyl]-1,3-dihydro-2H-pyrrolo[3,4-c]pyridine-2-carboxamide;
N-(4-{[1-(cyclohexylacetyl)piperidin-4-yl]oxy}phenyl)-1,3-dihydro-2H-pyrrolo[3,4-c]pyridine-2-carboxamide;
N-(4-{[1-(tetrahydro-2H-pyran-4-ylacetyl)piperidin-4-yl]oxy}phenyl)-1,3-dihydro-2H-pyrrolo[3,4-c]pyridine-2-carboxamide;
N-(4-{[1-(2-methylbutanoyl)piperidin-4-yl]oxy}phenyl)-1,3-dihydro-2H-isoindole-2-carboxamide;
N-(4-{[1-(3-methylbutanoyl)piperidin-4-yl]oxy}phenyl)-1,3-dihydro-2H-isoindole-2-carboxamide;
N-(4-{[1-(2,3-dimethylbutanoyl)piperidin-4-yl]oxy}phenyl)-1,3-dihydro-2H-isoindole-2-carboxamide;
N-(4-{[1-(tetrahydrofuran-2-ylcarbonyl)piperidin-4-yl]oxy}phenyl)-1,3-dihydro-2H-isoindole-2-carboxamide;
N-(4-{[1-(cyclohexylcarbonyl)piperidin-4-yl]oxy}phenyl)-1,3-dihydro-2H-isoindole-2-carboxamide;
N-(4-{[1-(cyclohexylacetyl)piperidin-4-yl]oxy}phenyl)-1,3-dihydro-2H-isoindole-2-carboxamide;
N-(4-{[1-(tetrahydro-2H-pyran-4-ylacetyl)piperidin-4-yl]oxy}phenyl)-1,3-dihydro-2H-isoindole-2-carboxamide;
N-(4-{[1-(morpholin-4-ylacetyl)piperidin-4-yl]oxy}phenyl)-1,3-dihydro-2H-isoindole-2-carboxamide;
N-(4-{[1-(tetrahydrofuran-3-ylacetyl)piperidin-4-yl]oxy}phenyl)-1,3-dihydro-2H-isoindole-2-carboxamide;
N-(4-{[1-(tetrahydrofuran-2-ylacetyl)azetidin-3-yl]oxy}phenyl)-1,3-dihydro-2H-pyrrolo[3,4-c]pyridine-2-carboxamide;
N-(4-{[1-(tetrahydro-2H-pyran-4-ylacetyl)azetidin-3-yl]oxy}phenyl)-1,3-dihydro-2H-pyrrolo[3,4-c]pyridine-2-carboxamide;
N-(4-{[1-(morpholin-4-ylacetyl)azetidin-3-yl]oxy}phenyl)-1,3-dihydro-2H-pyrrolo[3,4-c]pyridine-2-carboxamide;
N-(4-{[1-(cyclohexylacetyl)azetidin-3-yl]oxy}phenyl)-1,3-dihydro-2H-pyrrolo[3,4-c]pyridine-2-carboxamide;
N-(4-{[1-(2-methylbutanoyl)azetidin-3-yl]oxy}phenyl)-1,3-dihydro-2H-pyrrolo[3,4-c]pyridine-2-carboxamide;
N-(4-{[1-(2,2-dimethylpropanoyl)azetidin-3-yl]oxy}phenyl)-1,3-dihydro-2H-pyrrolo[3,4-c]pyridine-2-carboxamide;
N-(4-{[1-(3,3-dimethylbutanoyl)azetidin-3-yl]oxy}phenyl)-1,3-dihydro-2H-pyrrolo[3,4-c]pyridine-2-carboxamide;
N-(4-{[1-(tricyclo[3.3.1.1~3,7~]dec-1-ylacetyl)azetidin-3-yl]oxy}phenyl)-1,3-dihydro-2H-pyrrolo[3,4-c]pyridine-2-carboxamide;
N-[4-({1-[(4-methoxycyclohexyl)carbonyl]azetidin-3-yl}oxy)phenyl]-1,3-dihydro-2H-pyrrolo[3,4-c]pyridine-2-carboxamide;
N-[4-({[4-(acetylamino)phenyl]sulfonyl}amino)phenyl]-1,3-dihydro-2H-pyrrolo[3,4-c]pyridine-2-carboxamide;
N-{4-[(propylsulfonyl)amino]phenyl}-1,3-dihydro-2H-pyrrolo[3,4-c]pyridine-2-carboxamide;
N-(4-{[(4-propylphenyl)sulfonyl]amino}phenyl)-1,3-dihydro-2H-pyrrolo[3,4-c]pyridine-2-carboxamide;
N-{4-[(butylsulfonyl)amino]phenyl}-1,3-dihydro-2H-pyrrolo[3,4-c]pyridine-2-carboxamide;
N-{4-[({[(1S,4R)-7,7-dimethyl-2-oxobicyclo[2.2.1]hept-1-yl]methyl}sulfonyl)amino]phenyl}-1,3-dihydro-2H-pyrrolo[3,4-c]pyridine-2-carboxamide;
N-{4-[(ethylsulfonyl)amino]phenyl}-1,3-dihydro-2H-pyrrolo[3,4-c]pyridine-2-carboxamide;
N-{4-[(benzylsulfonyl)amino]phenyl}-1,3-dihydro-2H-pyrrolo[3,4-c]pyridine-2-carboxamide;
N-(4-{[(4-fluorophenyl)sulfonyl]amino}phenyl)-1,3-dihydro-2H-pyrrolo[3,4-c]pyridine-2-carboxamide;
N-{4-[(thiophen-2-ylsulfonyl)amino]phenyl}-1,3-dihydro-2H-pyrrolo[3,4-c]pyridine-2-carboxamide;
N-[4-(1,7-diazaspiro[4.4]non-7-ylcarbonyl)phenyl]-1,3-dihydro-2H-pyrrolo[3,4-c]pyridine-2-carboxamide;
N-[4-(2,7-diazaspiro[4.5]dec-2-ylcarbonyl)phenyl]-1,3-dihydro-2H-pyrrolo[3,4-c]pyridine-2-carboxamide;
N-[4-(2,6-diazaspiro[4.5]dec-2-ylcarbonyl)phenyl]-1,3-dihydro-2H-pyrrolo[3,4-c]pyridine-2-carboxamide;
N-[4-(2,7-diazaspiro[4.5]dec-7-ylcarbonyl)phenyl]-1,3-dihydro-2H-pyrrolo[3,4-c]pyridine-2-carboxamide;
N-[4-(2,9-diazaspiro[5.5]undec-2-ylcarbonyl)phenyl]-1,3-dihydro-2H-pyrrolo[3,4-c]pyridine-2-carboxamide;
N-[4-(2,8-diazaspiro[5.5]undec-2-ylcarbonyl)phenyl]-1,3-dihydro-2H-pyrrolo[3,4-c]pyridine-2-carboxamide;
N-[4-(1,8-diazaspiro[5.5]undec-8-ylcarbonyl)phenyl]-1,3-dihydro-2H-pyrrolo[3,4-c]pyridine-2-carboxamide;
N-[4-(1,8-diazaspiro[4.6]undec-8-ylcarbonyl)phenyl]-1,3-dihydro-2H-pyrrolo[3,4-c]pyridine-2-carboxamide;
N-{4-[(1-oxa-8-azaspiro[4.5]dec-2-ylmethyl)carbamoyl]phenyl}-1,3-dihydro-2H-pyrrolo[3,4-c]pyridine-2-carboxamide;
N-[4-(1-oxa-8-azaspiro[4.5]dec-3-ylcarbamoyl)phenyl]-1,3-dihydro-2H-pyrrolo[3,4-c]pyridine-2-carboxamide;
N-{4-[(2-oxa-9-azaspiro[5.5]undec-3-ylmethyl)carbamoyl]phenyl}-1,3-dihydro-2H-pyrrolo[3,4-c]pyridine-2-carboxamide;
N-[4-(1-oxa-4,8-diazaspiro[5.5]undec-4-ylcarbonyl)phenyl]-1,3-dihydro-2H-pyrrolo[3,4-c]pyridine-2-carboxamide;
N-[4-(1,8-diazaspiro[4.5]dec-1-ylcarbonyl)phenyl]-1,3-dihydro-2H-pyrrolo[3,4-c]pyridine-2-carboxamide;
N-[4-(1,8-diazaspiro[4.5]dec-8-ylcarbonyl)phenyl]-1,3-dihydro-2H-pyrrolo[3,4-c]pyridine-2-carboxamide;
N-[4-(1,7-diazaspiro[3.5]non-7-ylcarbonyl)phenyl]-1,3-dihydro-2H-pyrrolo[3,4-c]pyridine-2-carboxamide;
N-[4-(1,6-diazaspiro[3.5]non-1-ylcarbonyl)phenyl]-1,3-dihydro-2H-pyrrolo[3,4-c]pyridine-2-carboxamide;
N-[4-(2,5-diazaspiro[3.5]non-2-ylcarbonyl)phenyl]-1,3-dihydro-2H-pyrrolo[3,4-c]pyridine-2-carboxamide;
N-[4-(5-oxa-2-azaspiro[3.4]oct-2-ylcarbonyl)phenyl]-1,3-dihydro-2H-pyrrolo[3,4-c]pyridine-2-carboxamide;
N-[4-(6-oxa-2-azaspiro[3.5]non-2-ylcarbonyl)phenyl]-1,3-dihydro-2H-pyrrolo[3,4-c]pyridine-2-carboxamide;

N-[4-(hexahydro-5H-furo[2,3-c]pyrrol-5-ylcarbonyl)phenyl]-1,3-dihydro-2H-pyrrolo[3,4-c]pyridine-2-carboxamide;

N-[4-(tetrahydro-1H-furo[3,4-c]pyrrol-5(3H)-ylcarbonyl)phenyl]-1,3-dihydro-2H-pyrrolo[3,4-c]pyridine-2-carboxamide;

N-[4-(hexahydrofuro[3,4-c]pyridin-5(3H)-ylcarbonyl)phenyl]-1,3-dihydro-2H-pyrrolo[3,4-c]pyridine-2-carboxamide;

N-{4-[1-(tetrahydro furan-3-ylacetyl)-1,2,3,6-tetrahydropyridin-4-yl]phenyl}-1,3-dihydro-2H-pyrrolo[3,4-c]pyridine-2-carboxamide;

N-{4-[1-(tetrahydro-2H-pyran-4-ylacetyl)-1,2,3,6-tetrahydropyridin-4-yl]phenyl}-1,3-dihydro-2H-pyrrolo[3,4-c]pyridine-2-carboxamide;

N-{4-[1-(N,N-dimethylglycyl)-1,2,3,6-tetrahydropyridin-4-yl]phenyl}-1,3-dihydro-2H-pyrrolo[3,4-c]pyridine-2-carboxamide;

N-(4-{1-[(4-methylpiperazin-1-yl)acetyl]-1,2,3,6-tetrahydropyridin-4-yl}phenyl)-1,3-dihydro-2H-pyrrolo[3,4-c]pyridine-2-carboxamide;

N-(4-{4-[(tetrahydro furan-2-ylacetyl)amino]cyclohex-1-en-1-yl}phenyl)-1,3-dihydro-2H-pyrrolo[3,4-c]pyridine-2-carboxamide;

N-(4-{4-[(tetrahydro furan-3-ylacetyl)amino]cyclohex-1-en-1-yl}phenyl)-1,3-dihydro-2H-pyrrolo[3,4-c]pyridine-2-carboxamide;

N-(4-{4-[(cyclohexylcarbonyl)amino]cyclohex-1-en-1-yl}phenyl)-1,3-dihydro-2H-pyrrolo[3,4-c]pyridine-2-carboxamide;

N-[4-(4-{[(1,1-dioxidotetrahydrothiophen-3-yl)carbonyl]amino}cyclohex-1-en-1-yl)phenyl]-1,3-dihydro-2H-pyrrolo[3,4-c]pyridine-2-carboxamide;

N-[4-(4-{[(4,4-difluorocyclohexyl)carbonyl]amino}cyclohex-1-en-1-yl)phenyl]-1,3-dihydro-2H-pyrrolo[3,4-c]pyridine-2-carboxamide;

N-(4-{4-[(2-hydroxy-2-methylpropanoyl)amino]cyclohex-1-en-1-yl}phenyl)-1,3-dihydro-2H-pyrrolo[3,4-c]pyridine-2-carboxamide;

N-(4-{4-[(tetrahydrofuran-2-ylcarbonyl)amino]cyclohex-1-en-1-yl}phenyl)-1,3-dihydro-2H-pyrrolo[3,4-c]pyridine-2-carboxamide;

N-[4-(piperidin-1-ylsulfonyl)phenyl]-1,3-dihydro-2H-pyrrolo[3,4-c]pyridine-2-carboxamide;

5-fluoro-N-(4-{[1-(1,3-thiazol-2-yl)propan-2-yl]carbamoyl}phenyl)-1,3-dihydro-2H-isoindole-2-carboxamide;

N-{4-[(4,4-difluorocyclohexyl)carbamoyl]phenyl}-5-fluoro-1,3-dihydro-2H-isoindole-2-carboxamide;

N-(4-{[1-(3,5-dimethyl-1H-pyrazol-1-yl)propan-2-yl]carbamoyl}phenyl)-5-fluoro-1,3-dihydro-2H-isoindole-2-carboxamide;

5-fluoro-N-(4-{[2-methyl-2-(morpholin-4-yl)butyl]carbamoyl}phenyl)-1,3-dihydro-2H-isoindole-2-carboxamide;

5-fluoro-N-(4-{[2-(2-methyl-1,3-thiazol-4-yl)ethyl]carbamoyl}phenyl)-1,3-dihydro-2H-isoindole-2-carboxamide;

5-fluoro-N-(4-{[2-methyl-1-(morpholin-4-yl)propan-2-yl]carbamoyl}phenyl)-1,3-dihydro-2H-isoindole-2-carboxamide;

5-fluoro-N-{4-[(4-methoxybenzyl)carbamoyl]phenyl}-1,3-dihydro-2H-isoindole-2-carboxamide;

5-fluoro-N-(4-{[3-(morpholin-4-yl)propyl]carbamoyl}phenyl)-1,3-dihydro-2H-isoindole-2-carboxamide;

Nalpha-(4-{[(5-fluoro-1,3-dihydro-2H-isoindol-2-yl)carbonyl]amino}benzoyl)-D-phenylalaninamide;

N-(4-{[2-(acetylamino)phenyl]carbamoyl}phenyl)-5-fluoro-1,3-dihydro-2H-isoindole-2-carboxamide;

5-fluoro-N-[4-({4-[2-(2-hydroxyethoxy)ethyl]piperazin-1-yl}carbonyl)phenyl]-1,3-dihydro-2H-isoindole-2-carboxamide;

5-fluoro-N-(4-{[2-(furan-2-yl)-2-(pyrrolidin-1-yl)ethyl]carbamoyl}phenyl)-1,3-dihydro-2H-isoindole-2-carboxamide;

N-{4-[bis(2-methoxyethyl)carbamoyl]phenyl}-5-fluoro-1,3-dihydro-2H-isoindole-2-carboxamide;

N-{4-[(1-amino-1-oxohexan-2-yl)carbamoyl]phenyl}-5-fluoro-1,3-dihydro-2H-isoindole-2-carboxamide;

N-(4-{[2-(3,4-dimethoxyphenyl)ethyl]carbamoyl}phenyl)-5-fluoro-1,3-dihydro-2H-isoindole-2-carboxamide;

N-(4-{[(2S)-3,3-dimethyl-1-(methylamino)-1-oxobutan-2-yl]carbamoyl}phenyl)-5-fluoro-1,3-dihydro-2H-isoindole-2-carboxamide;

Nalpha-(4-{[(5-fluoro-1,3-dihydro-2H-isoindol-2-yl)carbonyl]amino}benzoyl)-L-phenylalaninamide;

N-(4-{[(2R)-1-amino-4-methyl-1-oxopentan-2-yl]carbamoyl}phenyl)-5-fluoro-1,3-dihydro-2H-isoindole-2-carboxamide;

N-{4-[(4-cyclohexylpiperazin-1-yl)carbonyl]phenyl}-5-fluoro-1,3-dihydro-2H-isoindole-2-carboxamide;

5-fluoro-N-(4-{[3-(methylcarbamoyl)phenyl]carbamoyl}phenyl)-1,3-dihydro-2H-isoindole-2-carboxamide;

N-{4-[(2-amino-2-oxo-1-phenylethyl)carbamoyl]phenyl}-5-fluoro-1,3-dihydro-2H-isoindole-2-carboxamide;

N-{4-[(3-tert-butoxypropyl)carbamoyl]phenyl}-5-fluoro-1,3-dihydro-2H-isoindole-2-carboxamide;

N-(4-{[2-(2,6-dimethylmorpholin-4-yl)ethyl]carbamoyl}phenyl)-5-fluoro-1,3-dihydro-2H-isoindole-2-carboxamide;

N-(4-{[(1R)-2-amino-2-oxo-1-phenylethyl]carbamoyl}phenyl)-5-fluoro-1,3-dihydro-2H-isoindole-2-carboxamide;

5-fluoro-N-{4-[(3-methoxybenzyl)carbamoyl]phenyl}-1,3-dihydro-2H-isoindole-2-carboxamide;

N-(4-{[2-(3,5-dimethyl-1H-pyrazol-1-yl)ethyl]carbamoyl}phenyl)-5-fluoro-1,3-dihydro-2H-isoindole-2-carboxamide;

5-fluoro-N-(4-{[2-methyl-2-(morpholin-4-yl)propyl]carbamoyl}phenyl)-1,3-dihydro-2H-isoindole-2-carboxamide;

5-fluoro-N-(4-{[(3S)-1-methyl-2-oxoazepan-3-yl]carbamoyl}phenyl)-1,3-dihydro-2H-isoindole-2-carboxamide;

5-fluoro-N-(4-{[2-(4-methylpiperazin-1-yl)ethyl]carbamoyl}phenyl)-1,3-dihydro-2H-isoindole-2-carboxamide;

5-fluoro-N-(4-{[4-(morpholin-4-yl)benzyl]carbamoyl}phenyl)-1,3-dihydro-2H-isoindole-2-carboxamide;

5-fluoro-N-(4-{[3-(piperidin-1-yl)propyl]carbamoyl}phenyl)-1,3-dihydro-2H-isoindole-2-carboxamide;

N-(4-{[3-(5-methyl-1H-pyrazol-1-yl)propyl]carbamoyl}phenyl)-5,7-dihydro-6H-pyrrolo[3,4-b]pyridine-6-carboxamide;

N-(4-{[2-(4-chloro-1H-pyrazol-1-yl)ethyl]carbamoyl}phenyl)-5,7-dihydro-6H-pyrrolo[3,4-b]pyridine-6-carboxamide;

N-(4-{[1-(3,5-dimethyl-1H-pyrazol-1-yl)propan-2-yl]
carbamoyl}phenyl)-5,7-dihydro-6H-pyrrolo[3,4-b]pyridine-6-carboxamide;

N-(4-{[2-methyl-2-(morpholin-4-yl)butyl]
carbamoyl}phenyl)-5,7-dihydro-6H-pyrrolo[3,4-b]pyridine-6-carboxamide;

N-{4-[(4-methoxybenzyl)carbamoyl]phenyl}-5,7-dihydro-6H-pyrrolo[3,4-b]pyridine-6-carboxamide;

N-(4-{[3-(morpholin-4-yl)propyl]carbamoyl}phenyl)-5,7-dihydro-6H-pyrrolo[3,4-b]pyridine-6-carboxamide;

N-[4-({4-[2-(2-hydroxyethoxy)ethyl]piperazin-1-yl}carbonyl)phenyl]-5,7-dihydro-6H-pyrrolo[3,4-b]pyridine-6-carboxamide;

N-{4-[(2-carbamoylbenzyl)carbamoyl]phenyl}-5,7-dihydro-6H-pyrrolo[3,4-b]pyridine-6-carboxamide;

N-{4-[bis(2-methoxyethyl)carbamoyl]phenyl}-5,7-dihydro-6H-pyrrolo[3,4-b]pyridine-6-carboxamide;

N-{4-[(1-amino-1-oxohexan-2-yl)carbamoyl]phenyl}-5,7-dihydro-6H-pyrrolo[3,4-b]pyridine-6-carboxamide;

N-(4-{[2-(3,4-dimethoxyphenyl)ethyl]carbamoyl}phenyl)-5,7-dihydro-6H-pyrrolo[3,4-b]pyridine-6-carboxamide;

N-(4-{[4-(pyrazin-2-yl)piperazin-1-yl]carbonyl}phenyl)-5,7-dihydro-6H-pyrrolo[3,4-b]pyridine-6-carboxamide;

Nalpha-{4-[(5,7-dihydro-6H-pyrrolo[3,4-b]pyridin-6-ylcarbonyl)amino]benzoyl}-L-phenylalaninamide;

N-(4-{[(2R)-1-amino-4-methyl-1-oxopentan-2-yl]
carbamoyl}phenyl)-5,7-dihydro-6H-pyrrolo[3,4-b]pyridine-6-carboxamide;

N-{4-[(4-cyclohexylpiperazin-1-yl)carbonyl]phenyl}-5,7-dihydro-6H-pyrrolo[3,4-b]pyridine-6-carboxamide;

N-{4-[(3-tert-butoxypropyl)carbamoyl]phenyl}-5,7-dihydro-6H-pyrrolo[3,4-b]pyridine-6-carboxamide;

N-(4-{[2-(2,6-dimethylmorpholin-4-yl)ethyl]
carbamoyl}phenyl)-5,7-dihydro-6H-pyrrolo[3,4-b]pyridine-6-carboxamide;

N-{4-[(3-methoxybenzyl)carbamoyl]phenyl}-5,7-dihydro-6H-pyrrolo[3,4-b]pyridine-6-carboxamide;

N-(4-{[2-methyl-2-(morpholin-4-yl)propyl]
carbamoyl}phenyl)-5,7-dihydro-6H-pyrrolo[3,4-b]pyridine-6-carboxamide;

N-(4-{[(3S)-1-methyl-2-oxoazepan-3-yl]
carbamoyl}phenyl)-5,7-dihydro-6H-pyrrolo[3,4-b]pyridine-6-carboxamide;

N-(4-{[2-(4-methylpiperazin-1-yl)ethyl]
carbamoyl}phenyl)-5,7-dihydro-6H-pyrrolo[3,4-b]pyridine-6-carboxamide;

N-(4-{[4-(morpholin-4-yl)benzyl]carbamoyl}phenyl)-5,7-dihydro-6H-pyrrolo[3,4-b]pyridine-6-carboxamide;

N-(4-{[3-(piperidin-1-yl)propyl]carbamoyl}phenyl)-5,7-dihydro-6H-pyrrolo[3,4-b]pyridine-6-carboxamide;

N-[4-(4,5,6,7-tetrahydro-1H-indazol-5-ylcarbamoyl)phenyl]-5,7-dihydro-6H-pyrrolo[3,4-b]pyridine-6-carboxamide;

5-fluoro-N-{4-[(3-methoxy-2,2-dimethylpropyl)carbamoyl]phenyl}-1,3-dihydro-2H-isoindole-2-carboxamide;

N-{4-[(3,3-dimethylbutyl)carbamoyl]phenyl}-5-fluoro-1,3-dihydro-2H-isoindole-2-carboxamide;

5-fluoro-N-(4-{[1-(furan-2-yl)propan-2-yl]
carbamoyl}phenyl)-1,3-dihydro-2H-isoindole-2-carboxamide;

5-fluoro-N-(4-{[(3-methyl-1,2-oxazol-5-yl)methyl]
carbamoyl}phenyl)-1,3-dihydro-2H-isoindole-2-carboxamide;

N-(4-{[(2R)-1-cyanobutan-2-yl]carbamoyl}phenyl)-5-fluoro-1,3-dihydro-2H-isoindole-2-carboxamide;

N-{4-[(2R)-butan-2-ylcarbamoyl]phenyl}-5-fluoro-1,3-dihydro-2H-isoindole-2-carboxamide;

5-fluoro-N-(4-{[2-(1H-pyrazol-1-yl)ethyl]
carbamoyl}phenyl)-1,3-dihydro-2H-isoindole-2-carboxamide;

5-fluoro-N-{4-[methyl(3-methylbutyl)carbamoyl]phenyl}-1,3-dihydro-2H-isoindole-2-carboxamide;

N-(4-{[1-(ethylamino)-1-oxopropan-2-yl]
carbamoyl}phenyl)-5-fluoro-1,3-dihydro-2H-isoindole-2-carboxamide;

5-fluoro-N-(4-{[(1-methyl-1H-pyrazol-3-yl)methyl]
carbamoyl}phenyl)-1,3-dihydro-2H-isoindole-2-carboxamide;

5-fluoro-N-{4-[(2-methoxybutyl)carbamoyl]phenyl}-1,3-dihydro-2H-isoindole-2-carboxamide;

N-(4-{[4-(dimethylamino)butyl]carbamoyl}phenyl)-5-fluoro-1,3-dihydro-2H-isoindole-2-carboxamide;

5-fluoro-N-{4-[(3S)-tetrahydrofuran-3-ylcarbamoyl]phenyl}-1,3-dihydro-2H-isoindole-2-carboxamide;

5-fluoro-N-{4-[(1-methoxybutan-2-yl)carbamoyl]phenyl}-1,3-dihydro-2H-isoindole-2-carboxamide;

N-{4-[(2-ethoxypropyl)carbamoyl]phenyl}-5-fluoro-1,3-dihydro-2H-isoindole-2-carboxamide;

N-{4-[benzyl(methyl)carbamoyl]phenyl}-5-fluoro-1,3-dihydro-2H-isoindole-2-carboxamide;

N-{4-[(2S)-butan-2-ylcarbamoyl]phenyl}-5-fluoro-1,3-dihydro-2H-isoindole-2-carboxamide;

5-fluoro-N-(4-{[2-(5-methyl-1H-pyrazol-1-yl)ethyl]
carbamoyl}phenyl)-1,3-dihydro-2H-isoindole-2-carboxamide;

5-fluoro-N-(4-{[2-(3-methyl-1H-pyrazol-1-yl)ethyl]
carbamoyl}phenyl)-1,3-dihydro-2H-isoindole-2-carboxamide;

5-fluoro-N-{4-[(2-methylpropyl)carbamoyl]phenyl}-1,3-dihydro-2H-isoindole-2-carboxamide;

5-fluoro-N-{4-[(pyridin-3-ylmethyl)carbamoyl]phenyl}-1,3-dihydro-2H-isoindole-2-carboxamide;

5-fluoro-N-{4-[(tetrahydrofuran-2-ylmethyl)carbamoyl]phenyl}-1,3-dihydro-2H-isoindole-2-carboxamide;

N-(4-{[(1R)-1-cyclopropylethyl]carbamoyl}phenyl)-5-fluoro-1,3-dihydro-2H-isoindole-2-carboxamide;

5-fluoro-N-(4-{[1-(1-methylcyclopropyl)ethyl]
carbamoyl}phenyl)-1,3-dihydro-2H-isoindole-2-carboxamide;

5-fluoro-N-{4-[(thiophen-2-ylmethyl)carbamoyl]phenyl}-1,3-dihydro-2H-isoindole-2-carboxamide;

N-(4-{[(1S)-1-cyclopropylethyl]carbamoyl}phenyl)-5-fluoro-1,3-dihydro-2H-isoindole-2-carboxamide;

5-fluoro-N-{4-[(4-methoxybutyl)carbamoyl]phenyl}-1,3-dihydro-2H-isoindole-2-carboxamide;

5-fluoro-N-(4-{[(5-methyl-1,3-oxazol-2-yl)methyl]
carbamoyl}phenyl)-1,3-dihydro-2H-isoindole-2-carboxamide;

5-fluoro-N-(4-{[2-(tetrahydro-2H-pyran-3-yl)ethyl]
carbamoyl}phenyl)-1,3-dihydro-2H-isoindole-2-carboxamide;

5-fluoro-N-(4-{[(2S)-1-methoxypropan-2-yl]
carbamoyl}phenyl)-1,3-dihydro-2H-isoindole-2-carboxamide;

N-{4-[(3,3-dimethyl-2-oxobutyl)carbamoyl]phenyl}-5-fluoro-1,3-dihydro-2H-isoindole-2-carboxamide;

5-fluoro-N-(4-{[(1-methyl-1H-pyrrol-2-yl)methyl]
carbamoyl}phenyl)-1,3-dihydro-2H-isoindole-2-carboxamide;

5-fluoro-N-(4-{[2-(propan-2-yloxy)ethyl]
carbamoyl}phenyl)-1,3-dihydro-2H-isoindole-2-carboxamide;

N-(4-{[3-(dimethylamino)propyl]carbamoyl}phenyl)-5-fluoro-1,3-dihydro-2H-isoindole-2-carboxamide;

N-(4-{[(2S)-1-amino-1-oxobutan-2-yl]carbamoyl}phenyl)-5-fluoro-1,3-dihydro-2H-isoindole-2-carboxamide;
5-fluoro-N-[4-(tetrahydro-2H-pyran-3-ylcarbamoyl)phenyl]-1,3-dihydro-2H-isoindole-2-carboxamide;
5-fluoro-N-(4-{[2-(1H-pyrrol-1-yl)ethyl]carbamoyl}phenyl)-1,3-dihydro-2H-isoindole-2-carboxamide;
5-fluoro-N-{4-[(1-methoxypropan-2-yl)carbamoyl]phenyl}-1,3-dihydro-2H-isoindole-2-carboxamide;
5-fluoro-N-{4-[(2-methoxyethyl)carbamoyl]phenyl}-1,3-dihydro-2H-isoindole-2-carboxamide;
N-[4-(cyclopentylcarbamoyl)phenyl]-5-fluoro-1,3-dihydro-2H-isoindole-2-carboxamide;
5-fluoro-N-(4-{[(2S)-3-methylbutan-2-yl]carbamoyl}phenyl)-1,3-dihydro-2H-isoindole-2-carboxamide;
5-fluoro-N-(4-{[(2R)-3-methylbutan-2-yl]carbamoyl}phenyl)-1,3-dihydro-2H-isoindole-2-carboxamide;
5-fluoro-N-(4-{[(2S)-2-methylbutyl]carbamoyl}phenyl)-1,3-dihydro-2H-isoindole-2-carboxamide;
5-fluoro-N-{4-[(2-hydroxy-2-methylpropyl)carbamoyl]phenyl}-1,3-dihydro-2H-isoindole-2-carboxamide;
5-fluoro-N-(4-{[2-(tetrahydro-2H-pyran-4-yl)ethyl]carbamoyl}phenyl)-1,3-dihydro-2H-isoindole-2-carboxamide;
N-[4-(butylcarbamoyl)phenyl]-5-fluoro-1,3-dihydro-2H-isoindole-2-carboxamide;
5-fluoro-N-{4-[methyl(tetrahydro furan-2-ylmethyl)carbamoyl]phenyl}-1,3-dihydro-2H-isoindole-2-carboxamide;
5-fluoro-N-{4-[(2-methoxyethyl)(methyl)carbamoyl]phenyl}-1,3-dihydro-2H-isoindole-2-carboxamide;
N-{4-[(1-cyanoethyl)carbamoyl]phenyl}-5-fluoro-1,3-dihydro-2H-isoindole-2-carboxamide;
5-fluoro-N-(4-{[(5-methyl-1,2-oxazol-3-yl)methyl]carbamoyl}phenyl)-1,3-dihydro-2H-isoindole-2-carboxamide;
5-fluoro-N-{4-[(3R)-tetrahydrofuran-3-ylcarbamoyl]phenyl}-1,3-dihydro-2H-isoindole-2-carboxamide;
N-{4-[(3-methoxy-2,2-dimethylpropyl)carbamoyl]phenyl}-5,7-dihydro-6H-pyrrolo[3,4-b]pyridine-6-carboxamide;
N-{4-[(3,3-dimethylbutyl)carbamoyl]phenyl}-5,7-dihydro-6H-pyrrolo[3,4-b]pyridine-6-carboxamide;
N-(4-{[1-(furan-2-yl)propan-2-yl]carbamoyl}phenyl)-5,7-dihydro-6H-pyrrolo[3,4-b]pyridine-6-carboxamide;
N-(4-{[(3-methyl-1,2-oxazol-5-yl)methyl]carbamoyl}phenyl)-5,7-dihydro-6H-pyrrolo[3,4-b]pyridine-6-carboxamide;
N-(4-{[(2R)-1-cyanobutan-2-yl]carbamoyl}phenyl)-5,7-dihydro-6H-pyrrolo[3,4-b]pyridine-6-carboxamide;
N-{4-[methyl(3-methylbutyl)carbamoyl]phenyl}-5,7-dihydro-6H-pyrrolo[3,4-b]pyridine-6-carboxamide;
N-(4-{[(1-methyl-1H-pyrazol-3-yl)methyl]carbamoyl}phenyl)-5,7-dihydro-6H-pyrrolo[3,4-b]pyridine-6-carboxamide;
N-{4-[(2-methoxybutyl)carbamoyl]phenyl}-5,7-dihydro-6H-pyrrolo[3,4-b]pyridine-6-carboxamide;
N-(4-{[4-(dimethylamino)butyl]carbamoyl}phenyl)-5,7-dihydro-6H-pyrrolo[3,4-b]pyridine-6-carboxamide;
N-(4-{[1-(1,3-thiazol-2-yl)ethyl]carbamoyl}phenyl)-5,7-dihydro-6H-pyrrolo[3,4-b]pyridine-6-carboxamide;
N-(4-{[1-(1-methyl-1H-pyrazol-4-yl)ethyl]carbamoyl}phenyl)-5,7-dihydro-6H-pyrrolo[3,4-b]pyridine-6-carboxamide;
N-{4-[(3S)-tetrahydrofuran-3-ylcarbamoyl]phenyl}-5,7-dihydro-6H-pyrrolo[3,4-b]pyridine-6-carboxamide;
N-{4-[(1-methoxybutan-2-yl)carbamoyl]phenyl}-5,7-dihydro-6H-pyrrolo[3,4-b]pyridine-6-carboxamide;
N-{4-[(4-aminobenzyl)carbamoyl]phenyl}-5,7-dihydro-6H-pyrrolo[3,4-b]pyridine-6-carboxamide;
N-{4-[(2-ethoxypropyl)carbamoyl]phenyl}-5,7-dihydro-6H-pyrrolo[3,4-b]pyridine-6-carboxamide;
N-{4-[(6-methoxypyridin-3-yl)carbamoyl]phenyl}-5,7-dihydro-6H-pyrrolo[3,4-b]pyridine-6-carboxamide;
N-{4-[(2S)-butan-2-ylcarbamoyl]phenyl}-5,7-dihydro-6H-pyrrolo[3,4-b]pyridine-6-carboxamide;
N-{4-[(1-cyanocyclopropyl)carbamoyl]phenyl}-5,7-dihydro-6H-pyrrolo[3,4-b]pyridine-6-carboxamide;
N-(4-{[2-(5-methyl-1H-pyrazol-1-yl)ethyl]carbamoyl}phenyl)-5,7-dihydro-6H-pyrrolo[3,4-b]pyridine-6-carboxamide;
N-(4-{[(4-methyl-1,3-thiazol-2-yl)methyl]carbamoyl}phenyl)-5,7-dihydro-6H-pyrrolo[3,4-b]pyridine-6-carboxamide;
N-{4-[(3-hydroxypropyl)carbamoyl]phenyl}-5,7-dihydro-6H-pyrrolo[3,4-b]pyridine-6-carboxamide;
N-{4-[(2-methylpropyl)carbamoyl]phenyl}-5,7-dihydro-6H-pyrrolo[3,4-b]pyridine-6-carboxamide;
N-{4-[(tetrahydro furan-2-ylmethyl)carbamoyl]phenyl}-5,7-dihydro-6H-pyrrolo[3,4-b]pyridine-6-carboxamide;
N-(4-{[(1R)-1-cyclopropylethyl]carbamoyl}phenyl)-5,7-dihydro-6H-pyrrolo[3,4-b]pyridine-6-carboxamide;
N-(4-{[1-(1-methylcyclopropyl)ethyl]carbamoyl}phenyl)-5,7-dihydro-6H-pyrrolo[3,4-b]pyridine-6-carboxamide;
N-{4-[(thiophen-2-ylmethyl)carbamoyl]phenyl}-5,7-dihydro-6H-pyrrolo[3,4-b]pyridine-6-carboxamide;
N-(4-{[(1S)-1-cyclopropylethyl]carbamoyl}phenyl)-5,7-dihydro-6H-pyrrolo[3,4-b]pyridine-6-carboxamide;
N-{4-[(4-methoxybutyl)carbamoyl]phenyl}-5,7-dihydro-6H-pyrrolo[3,4-b]pyridine-6-carboxamide;
N-(4-{[2-(tetrahydro-2H-pyran-3-yl)ethyl]carbamoyl}phenyl)-5,7-dihydro-6H-pyrrolo[3,4-b]pyridine-6-carboxamide;
N-(4-{[(2S)-1-methoxypropan-2-yl]carbamoyl}phenyl)-5,7-dihydro-6H-pyrrolo[3,4-b]pyridine-6-carboxamide;
N-{4-[(3,3-dimethyl-2-oxobutyl)carbamoyl]phenyl}-5,7-dihydro-6H-pyrrolo[3,4-b]pyridine-6-carboxamide;
N-(4-{[(1-methyl-1H-pyrrol-2-yl)methyl]carbamoyl}phenyl)-5,7-dihydro-6H-pyrrolo[3,4-b]pyridine-6-carboxamide;
N-(4-{[2-(propan-2-yloxy)ethyl]carbamoyl}phenyl)-5,7-dihydro-6H-pyrrolo[3,4-b]pyridine-6-carboxamide;
N-(4-{[3-(dimethylamino)propyl]carbamoyl}phenyl)-5,7-dihydro-6H-pyrrolo[3,4-b]pyridine-6-carboxamide;
N-[4-(tetrahydro-2H-pyran-3-ylcarbamoyl)phenyl]-5,7-dihydro-6H-pyrrolo[3,4-b]pyridine-6-carboxamide;
N-(4-{[2-(1H-pyrrol-1-yl)ethyl]carbamoyl}phenyl)-5,7-dihydro-6H-pyrrolo[3,4-b]pyridine-6-carboxamide;
N-{4-[(1-methoxypropan-2-yl)carbamoyl]phenyl}-5,7-dihydro-6H-pyrrolo[3,4-b]pyridine-6-carboxamide;
N-{4-[(3-aminobenzyl)carbamoyl]phenyl}-5,7-dihydro-6H-pyrrolo[3,4-b]pyridine-6-carboxamide;
N-(4-{[(2R)-3-methylbutan-2-yl]carbamoyl}phenyl)-5,7-dihydro-6H-pyrrolo[3,4-b]pyridine-6-carboxamide;
N-{4-[(tetrahydro-2H-pyran-3-ylmethyl)carbamoyl]phenyl}-5,7-dihydro-6H-pyrrolo[3,4-b]pyridine-6-carboxamide;
N-{4-[(2-hydroxy-2-methylpropyl)carbamoyl]phenyl}-5,7-dihydro-6H-pyrrolo[3,4-b]pyridine-6-carboxamide;
N-[4-(butylcarbamoyl)phenyl]-5,7-dihydro-6H-pyrrolo[3,4-b]pyridine-6-carboxamide;

N-{4-[methyl(tetrahydrofuran-2-ylmethyl)carbamoyl]phenyl}-5,7-dihydro-6H-pyrrolo[3,4-b]pyridine-6-carboxamide;

N-{4-[(2-methoxyethyl)(methyl)carbamoyl]phenyl}-5,7-dihydro-6H-pyrrolo[3,4-b]pyridine-6-carboxamide;

N-{4-[(1-cyanoethyl)carbamoyl]phenyl}-5,7-dihydro-6H-pyrrolo[3,4-b]pyridine-6-carboxamide;

N-{4-[(3R)-tetrahydrofuran-3-ylcarbamoyl]phenyl}-5,7-dihydro-6H-pyrrolo[3,4-b]pyridine-6-carboxamide;

N-{4-[(cyclopentylmethyl)carbamoyl]phenyl}-5,7-dihydro-6H-pyrrolo[3,4-b]pyridine-6-carboxamide;

N-{4-[(2-methoxy-2-methylpropyl)carbamoyl]phenyl}-5,7-dihydro-6H-pyrrolo[3,4-b]pyridine-6-carboxamide;

N-{4-[(cyclopropylmethyl)carbamoyl]phenyl}-5,7-dihydro-6H-pyrrolo[3,4-b]pyridine-6-carboxamide;

N-{4-[methyl(propyl)carbamoyl]phenyl}-5,7-dihydro-6H-pyrrolo[3,4-b]pyridine-6-carboxamide;

N-{4-[(pyridin-4-ylmethyl)carbamoyl]phenyl}-5,7-dihydro-6H-pyrrolo[3,4-b]pyridine-6-carboxamide;

methyl 1-{4-[(1,3-dihydro-2H-pyrrolo[3,4-c]pyridin-2-ylcarbonyl)amino]phenyl}azetidine-3-carboxylate;

N-(4-{3-[(3-methylbutyl)carbamoyl]azetidin-1-yl}phenyl)-1,3-dihydro-2H-pyrrolo[3,4-c]pyridine-2-carboxamide;

N-(4-{3-[(tetrahydrofuran-2-ylmethyl)carbamoyl]azetidin-1-yl}phenyl)-1,3-dihydro-2H-pyrrolo[3,4-c]pyridine-2-carboxamide;

N-(4-{3-[(tetrahydro-2H-pyran-4-ylmethyl)carbamoyl]azetidin-1-yl}phenyl)-1,3-dihydro-2H-pyrrolo[3,4-c]pyridine-2-carboxamide;

N-{4-[3-(benzylcarbamoyl)azetidin-1-yl]phenyl}-1,3-dihydro-2H-pyrrolo[3,4-c]pyridine-2-carboxamide;

N-{4-[3-(cyclopentylcarbamoyl)azetidin-1-yl]phenyl}-1,3-dihydro-2H-pyrrolo[3,4-c]pyridine-2-carboxamide;

N-(4-{3-[(cyclopentylmethyl)carbamoyl]azetidin-1-yl}phenyl)-1,3-dihydro-2H-pyrrolo[3,4-c]pyridine-2-carboxamide;

N-(4-{3-[(2-methoxyethyl)carbamoyl]azetidin-1-yl}phenyl)-1,3-dihydro-2H-pyrrolo[3,4-c]pyridine-2-carboxamide;

N-{4-[1-(3-methylbutanoyl)-1,2,3,6-tetrahydropyridin-4-yl]phenyl}-1,3-dihydro-2H-pyrrolo[3,4-c]pyridine-2-carboxamide;

N-{4-[1-(cyclopentylacetyl)-1,2,3,6-tetrahydropyridin-4-yl]phenyl}-1,3-dihydro-2H-pyrrolo[3,4-c]pyridine-2-carboxamide;

N-{4-[1-(tetrahydro furan-2-ylacetyl)-1,2,3,6-tetrahydropyridin-4-yl]phenyl}-1,3-dihydro-2H-pyrrolo[3,4-c]pyridine-2-carboxamide;

N-{4-[1-(tetrahydro-2H-pyran-2-ylacetyl)-1,2,3,6-tetrahydropyridin-4-yl]phenyl}-1,3-dihydro-2H-pyrrolo[3,4-c]pyridine-2-carboxamide;

N-{4-[1-(pyrrolidin-1-ylacetyl)-1,2,3,6-tetrahydropyridin-4-yl]phenyl}-1,3-dihydro-2H-pyrrolo[3,4-c]pyridine-2-carboxamide;

N-{4-[1-(pyrazin-2-ylcarbonyl)-1,2,3,6-tetrahydropyridin-4-yl]phenyl}-1,3-dihydro-2H-pyrrolo[3,4-c]pyridine-2-carboxamide;

N-{4-[(3-methoxy-2,2-dimethylpropyl)carbamoyl]phenyl}-1,3-dihydro-2H-isoindole-2-carboxamide;

N-{4-[(4,4-difluorocyclohexyl)carbamoyl]phenyl}-1,3-dihydro-2H-isoindole-2-carboxamide;

N-(4-{[(2R)-1-cyanobutan-2-yl]carbamoyl}phenyl)-1,3-dihydro-2H-isoindole-2-carboxamide;

N-{4-[(2-methoxybutyl)carbamoyl]phenyl}-1,3-dihydro-2H-isoindole-2-carboxamide;

N-(4-{[1-(ethylamino)-1-oxopropan-2-yl]carbamoyl}phenyl)-1,3-dihydro-2H-isoindole-2-carboxamide;

N-(4-{[2-methyl-2-(morpholin-4-yl)butyl]carbamoyl}phenyl)-1,3-dihydro-2H-isoindole-2-carboxamide;

N-(4-{[(1R)-1-cyclopropylethyl]carbamoyl}phenyl)-1,3-dihydro-2H-isoindole-2-carboxamide;

N-(4-{[(1S)-1-cyclopropylethyl]carbamoyl}phenyl)-1,3-dihydro-2H-isoindole-2-carboxamide;

N-{4-[(3S)-tetrahydrofuran-3-ylcarbamoyl]phenyl}-1,3-dihydro-2H-isoindole-2-carboxamide;

N-(4-{[2-(tetrahydro-2H-pyran-3-yl)ethyl]carbamoyl}phenyl)-1,3-dihydro-2H-isoindole-2-carboxamide;

N-(4-{[(5-methyl-1,3-oxazol-2-yl)methyl]carbamoyl}-phenyl)-1,3-dihydro-2H-isoindole-2-carboxamide;

N-[4-({2-[(dimethylamino)methyl]benzyl}carbamoyl)phenyl]-1,3-dihydro-2H-isoindole-2-carboxamide;

N-(4-{[(1R)-2-amino-2-oxo-1-phenylethyl]carbamoyl}phenyl)-1,3-dihydro-2H-isoindole-2-carboxamide;

N-[4-(1,3-oxazol-2-ylcarbamoyl)phenyl]-1,3-dihydro-2H-isoindole-2-carboxamide;

N-[4-(tetrahydro-2H-pyran-3-ylcarbamoyl)phenyl]-1,3-dihydro-2H-isoindole-2-carboxamide;

N-(4-{[2-(2,6-dimethylmorpholin-4-yl)ethyl]carbamoyl}phenyl)-1,3-dihydro-2H-isoindole-2-carboxamide;

N-(4-{[1-(1-methylcyclopropyl)ethyl]carbamoyl}phenyl)-1,3-dihydro-2H-isoindole-2-carboxamide;

N-(4-{[2-(furan-2-yl)-2-(pyrrolidin-1-yl)ethyl]carbamoyl}phenyl)-1,3-dihydro-2H-isoindole-2-carboxamide;

N-(4-{1-[(2S)-tetrahydrofuran-2-ylcarbonyl]piperidin-4-yl}phenyl)-1,3-dihydro-2H-pyrrolo[3,4-c]pyridine-2-carboxamide;

N-(4-{1-[(3S)-tetrahydrofuran-3-ylcarbonyl]piperidin-4-yl}phenyl)-1,3-dihydro-2H-pyrrolo[3,4-c]pyridine-2-carboxamide;

5-cyano-N-{4-[1-(tetrahydrofuran-3-ylcarbonyl)-1,2,3,6-tetrahydropyridin-4-yl]phenyl}-1,3-dihydro-2H-isoindole-2-carboxamide;

5-cyano-N-{4-[1-(tetrahydro-2H-pyran-4-ylcarbonyl)-1,2,3,6-tetrahydropyridin-4-yl]phenyl}-1,3-dihydro-2H-isoindole-2-carboxamide;

5-cyano-N-{4-[1-(2-hydroxy-2-methylpropanoyl)-1,2,3,6-tetrahydropyridin-4-yl]phenyl}-1,3-dihydro-2H-isoindole-2-carboxamide;

5-cyano-N-{4-[1-(morpholin-4-ylacetyl)-1,2,3,6-tetrahydropyridin-4-yl]phenyl}-1,3-dihydro-2H-isoindole-2-carboxamide;

N-(4-{[1-(tetrahydro-2H-pyran-2-ylcarbonyl)azetidin-3-yl]oxy}phenyl)-1,3-dihydro-2H-pyrrolo[3,4-c]pyridine-2-carboxamide;

N-(4-{[1-(tetrahydro-2H-pyran-2-ylcarbonyl)pyrrolidin-3-yl]oxy}phenyl)-1,3-dihydro-2H-pyrrolo[3,4-c]pyridine-2-carboxamide;

N-(6-{[(2R)-tetrahydrofuran-2-ylmethyl]carbamoyl}pyridazin-3-yl)-1,3-dihydro-2H-isoindole-2-carboxamide;

N-(4-{4-[(cyclopropylacetyl)amino]cyclohex-1-en-1-yl}phenyl)-1,3-dihydro-2H-pyrrolo[3,4-c]pyridine-2-carboxamide;

N-{4-[(1-acetylpiperidin-3-yl)oxy]phenyl}-1,3-dihydro-2H-pyrrolo[3,4-c]pyridine-2-carboxamide;

N-{4-[(1-butanoylpiperidin-3-yl)oxy]phenyl}-1,3-dihydro-2H-pyrrolo[3,4-c]pyridine-2-carboxamide;
N-(4-{[1-(3-methylbutanoyl)piperidin-3-yl]oxy}phenyl)-1,3-dihydro-2H-pyrrolo[3,4-c]pyridine-2-carboxamide;
N-(4-{[1-(methoxyacetyl)piperidin-3-yl]oxy}phenyl)-1,3-dihydro-2H-pyrrolo[3,4-c]pyridine-2-carboxamide;
N-(4-{[1-(2-methylbutanoyl)piperidin-3-yl]oxy}phenyl)-1,3-dihydro-2H-pyrrolo[3,4-c]pyridine-2-carboxamide;
N-(4-{[1-(3,3,3-trifluoropropanoyl)piperidin-3-yl]oxy}phenyl)-1,3-dihydro-2H-pyrrolo[3,4-c]pyridine-2-carboxamide;
N-(4-{[1-(cyclopropylacetyl)piperidin-3-yl]oxy}phenyl)-1,3-dihydro-2H-pyrrolo[3,4-c]pyridine-2-carboxamide;
N-(4-{[1-(cyclobutylcarbonyl)piperidin-3-yl]oxy}phenyl)-1,3-dihydro-2H-pyrrolo[3,4-c]pyridine-2-carboxamide;
N-(4-{[1-(cyclobutylacetyl)piperidin-3-yl]oxy}phenyl)-1,3-dihydro-2H-pyrrolo[3,4-c]pyridine-2-carboxamide;
N-(4-{[1-(cyclopentylcarbonyl)piperidin-3-yl]oxy}phenyl)-1,3-dihydro-2H-pyrrolo[3,4-c]pyridine-2-carboxamide;
N-(4-{[1-(cyclopentylacetyl)piperidin-3-yl]oxy}phenyl)-1,3-dihydro-2H-pyrrolo[3,4-c]pyridine-2-carboxamide;
N-[4-({1-[(2S)-tetrahydrofuran-2-ylcarbonyl]piperidin-3-yl}oxy)phenyl]-1,3-dihydro-2H-pyrrolo[3,4-c]pyridine-2-carboxamide;
N-[4-({1-[(2R)-tetrahydrofuran-2-ylcarbonyl]piperidin-3-yl}oxy)phenyl]-1,3-dihydro-2H-pyrrolo[3,4-c]pyridine-2-carboxamide;
N-(4-{[1-(tetrahydro-2H-pyran-4-ylcarbonyl)piperidin-3-yl]oxy}phenyl)-1,3-dihydro-2H-pyrrolo[3,4-c]pyridine-2-carboxamide;
N-(4-{[1-(tetrahydro-2H-pyran-2-ylcarbonyl)piperidin-3-yl]oxy}phenyl)-1,3-dihydro-2H-pyrrolo[3,4-c]pyridine-2-carboxamide;
N-(4-{[1-(tetrahydro-2H-pyran-4-ylacetyl)piperidin-3-yl]oxy}phenyl)-1,3-dihydro-2H-pyrrolo[3,4-c]pyridine-2-carboxamide;
N-[1-(tetrahydrofuran-2-ylacetyl)piperidin-3-yl]oxy}phenyl)-1,3-dihydro-2H-pyrrolo[3,4-c]pyridine-2-carboxamide;
N-{[1-(tetrahydrofuran-3-ylacetyl)piperidin-3-yl]oxy}phenyl)-1,3-dihydro-2H-pyrrolo[3,4-c]pyridine-2-carboxamide;
N-(4-{[3-(3,5-dimethyl-1H-pyrazol-1-yl)propyl]carbamoyl}phenyl)-1,3-dihydro-2H-isoindole-2-carboxamide;
N-(4-{[(3S)-1-methyl-2-oxoazepan-3-yl]carbamoyl}phenyl)-1,3-dihydro-2H-isoindole-2-carboxamide;
N-(4-{[2-(1H-pyrazol-1-yl)ethyl]carbamoyl}phenyl)-1,3-dihydro-2H-isoindole-2-carboxamide;
N-(4-{[1-(1,3-thiazol-2-yl)ethyl]carbamoyl}phenyl)-1,3-dihydro-2H-isoindole-2-carboxamide;
N-(4-{[1-(furan-2-yl)propan-2-yl]carbamoyl}phenyl)-1,3-dihydro-2H-isoindole-2-carboxamide;
N-(4-{[1-(1-methyl-1H-pyrazol-4-yl)ethyl]carbamoyl}phenyl)-1,3-dihydro-2H-isoindole-2-carboxamide;
N-(4-{[(2R)-1-amino-4-methyl-1-oxopentan-2-yl]carbamoyl}phenyl)-1,3-dihydro-2H-isoindole-2-carboxamide;
N-(4-{[1-(3,5-dimethyl-1H-pyrazol-1-yl)propan-2-yl]carbamoyl}phenyl)-1,3-dihydro-2H-isoindole-2-carboxamide;
N-{4-[(2,2-difluoroethyl)carbamoyl]phenyl}-1,3-dihydro-2H-isoindole-2-carboxamide;
N-(4-{[2-(tetrahydro-2H-pyran-4-yl)ethyl]carbamoyl}phenyl)-1,3-dihydro-2H-isoindole-2-carboxamide;
N-{4-[(tetrahydrofuran-2-ylmethyl)carbamoyl]phenyl}-1,3-dihydro-2H-isoindole-2-carboxamide;
N-{4-[(2-methoxy-2-methylpropyl)carbamoyl]phenyl}-1,3-dihydro-2H-isoindole-2-carboxamide;
N-(4-{[(5-methyl-1,2-oxazol-3-yl)methyl]carbamoyl}phenyl)-1,3-dihydro-2H-isoindole-2-carboxamide;
N-(4-{[(1-methyl-1H-pyrazol-4-yl)methyl]carbamoyl}phenyl)-1,3-dihydro-2H-isoindole-2-carboxamide;
N-(4-{[2-(3,5-dimethyl-1H-pyrazol-1-yl)ethyl]carbamoyl}phenyl)-1,3-dihydro-2H-isoindole-2-carboxamide;
Nalpha-{4-[(1,3-dihydro-2H-isoindol-2-ylcarbonyl)amino]benzoyl}-L-phenylalaninamide;
N-(4-{[2-(2-methyl-1,3-thiazol-4-yl)ethyl]carbamoyl}phenyl)-1,3-dihydro-2H-isoindole-2-carboxamide;
N-(4-{[(2S)-3,3-dimethyl-1-(methylamino)-1-oxobutan-2-yl]carbamoyl}phenyl)-1,3-dihydro-2H-isoindole-2-carboxamide;
N-[4-(thiophen-3-ylcarbamoyl)phenyl]-1,3-dihydro-2H-isoindole-2-carboxamide;
N-(4-{[2-(5-methyl-1H-pyrazol-1-yl)ethyl]carbamoyl}phenyl)-1,3-dihydro-2H-isoindole-2-carboxamide;
N-(4-{[2-(3-methyl-1H-pyrazol-1-yl)ethyl]carbamoyl}phenyl)-1,3-dihydro-2H-isoindole-2-carboxamide;
N-{4-[(2S)-butan-2-ylcarbamoyl]phenyl}-1,3-dihydro-2H-isoindole-2-carboxamide;
N-{4-[(3,3-dimethyl-2-oxobutyl)carbamoyl]phenyl}-1,3-dihydro-2H-isoindole-2-carboxamide;
N-(4-{[(1-methyl-1H-pyrazol-3-yl)methyl]carbamoyl}phenyl)-1,3-dihydro-2H-isoindole-2-carboxamide;
N-(4-{[2-(acetylamino)phenyl]carbamoyl}phenyl)-1,3-dihydro-2H-isoindole-2-carboxamide;
N-{4-[(1-methoxybutan-2-yl)carbamoyl]phenyl}-1,3-dihydro-2H-isoindole-2-carboxamide;
N-[4-(tetrahydro-2H-pyran-4-ylcarbamoyl)phenyl]-1,3-dihydro-2H-isoindole-2-carboxamide;
N-[4-(pyrimidin-4-ylcarbamoyl)phenyl]-1,3-dihydro-2H-isoindole-2-carboxamide;
N-(4-{[2-(1H-pyrrol-1-yl)ethyl]carbamoyl}phenyl)-1,3-dihydro-2H-isoindole-2-carboxamide;
N-(4-{[(2S)-2-methylbutyl]carbamoyl}phenyl)-1,3-dihydro-2H-isoindole-2-carboxamide;
N-{4-[(1-amino-1-oxohexan-2-yl)carbamoyl]phenyl}-1,3-dihydro-2H-isoindole-2-carboxamide;
N-{4-[(2-amino-2-oxo-1-phenylethyl)carbamoyl]phenyl}-1,3-dihydro-2H-isoindole-2-carboxamide;
N-{4-[(3-tert-butoxypropyl)carbamoyl]phenyl}-1,3-dihydro-2H-isoindole-2-carboxamide;
N-(4-{[3-(methylcarbamoyl)phenyl]carbamoyl}phenyl)-1,3-dihydro-2H-isoindole-2-carboxamide;
N-(4-{[(2R)-3-methylbutan-2-yl]carbamoyl}phenyl)-1,3-dihydro-2H-isoindole-2-carboxamide;
N-(4-{[(2S)-3-methylbutan-2-yl]carbamoyl}phenyl)-1,3-dihydro-2H-isoindole-2-carboxamide;
N-(4-{[2-methyl-1-(morpholin-4-yl)propan-2-yl]carbamoyl}phenyl)-1,3-dihydro-2H-isoindole-2-carboxamide;

N-(4-{[1-(5-oxo-L-prolyl)piperidin-4-yl]oxy}phenyl)-1,3-dihydro-2H-pyrrolo[3,4-c]pyridine-2-carboxamide;
N-(4-{[2-methyl-2-(morpholin-4-yl)propyl]carbamoyl}phenyl)-1,3-dihydro-2H-isoindole-2-carboxamide;
N-{4-[(2-ethoxypropyl)carbamoyl]phenyl}-1,3-dihydro-2H-isoindole-2-carboxamide;
N-{4-[(3-ethoxypropanoyl)amino]phenyl}-1,3-dihydro-2H-pyrrolo[3,4-c]pyridine-2-carboxamide;
N-(4-{[(1-acetylpiperidin-4-yl)carbonyl]amino}phenyl)-1,3-dihydro-2H-pyrrolo[3,4-c]pyridine-2-carboxamide;
N-{4-[(ethoxyacetyl)amino]phenyl}-1,3-dihydro-2H-pyrrolo[3,4-c]pyridine-2-carboxamide;
N-{4-[(tetrahydrofuran-2-ylcarbonyl)amino]phenyl}-1,3-dihydro-2H-pyrrolo[3,4-c]pyridine-2-carboxamide;
N-{4-[(tetrahydrofuran-3-ylcarbonyl)amino]phenyl}-1,3-dihydro-2H-pyrrolo[3,4-c]pyridine-2-carboxamide;
N-{4-[(cyclopentylcarbonyl)amino]phenyl}-1,3-dihydro-2H-pyrrolo[3,4-c]pyridine-2-carboxamide;
N-{4-[(bicyclo[2.2.1]hept-2-ylacetyl)amino]phenyl}-1,3-dihydro-2H-pyrrolo[3,4-c]pyridine-2-carboxamide;
N-{4-[(1,3-thiazol-5-ylcarbonyl)amino]phenyl}-1,3-dihydro-2H-pyrrolo[3,4-c]pyridine-2-carboxamide;
N-(4-{[(4-oxo-4,5,6,7-tetrahydro-1-benzo furan-3-yl)carbonyl]amino}phenyl)-1,3-dihydro-2H-pyrrolo[3,4-c]pyridine-2-carboxamide;
N-(4-{2-[(3-methylbutanoyl)amino]ethyl}phenyl)-1,3-dihydro-2H-isoindole-2-carboxamide;
N-(4-{2-[(4-methylpentanoyl)amino]ethyl}phenyl)-1,3-dihydro-2H-isoindole-2-carboxamide;
N-(4-{2-[(ethoxyacetyl)amino]ethyl}phenyl)-1,3-dihydro-2H-isoindole-2-carboxamide;
N-[4-(2-{[(2-methoxyethoxy)acetyl]amino}ethyl)phenyl]-1,3-dihydro-2H-isoindole-2-carboxamide;
N-(4-{2-[(tetrahydrofuran-2-ylcarbonyl)amino]ethyl}phenyl)-1,3-dihydro-2H-isoindole-2-carboxamide;
N-(4-{2-[(cyclopentylcarbonyl)amino]ethyl}phenyl)-1,3-dihydro-2H-isoindole-2-carboxamide;
N-(4-{2-[(cyclopentylacetyl)amino]ethyl}phenyl)-1,3-dihydro-2H-isoindole-2-carboxamide;
N-{4-[2-(benzoylamino)ethyl]phenyl}-1,3-dihydro-2H-isoindole-2-carboxamide;
N-(4-{2-[(tetrahydro-2H-pyran-4-ylcarbonyl)amino]ethyl}phenyl)-1,3-dihydro-2H-isoindole-2-carboxamide;
N-(4-{2-[(tetrahydro-2H-pyran-4-ylacetyl)amino]ethyl}phenyl)-1,3-dihydro-2H-isoindole-2-carboxamide;
N-(4-{2-[(tetrahydrofuran-3-ylacetyl)amino]ethyl}phenyl)-1,3-dihydro-2H-isoindole-2-carboxamide;
N-(4-{1-[(2R)-tetrahydrofuran-2-ylcarbonyl]piperidin-4-yl}phenyl)-1,3-dihydro-2H-pyrrolo[3,4-c]pyridine-2-carboxamide;
N-(4-{1-[(3R)-tetrahydrofuran-3-ylcarbonyl]piperidin-4-yl}phenyl)-1,3-dihydro-2H-pyrrolo[3,4-c]pyridine-2-carboxamide;
N-(4-{[1-(5-oxo-L-prolyl)azetidin-3-yl]oxy}phenyl)-1,3-dihydro-2H-pyrrolo[3,4-c]pyridine-2-carboxamide;
N-{4-[(1-propanoylazetidin-3-yl)oxy]phenyl}-1,3-dihydro-2H-pyrrolo[3,4-c]pyridine-2-carboxamide;
N-(4-{[1-(2,2-dimethylbutanoyl)azetidin-3-yl]oxy}phenyl)-1,3-dihydro-2H-pyrrolo[3,4-c]pyridine-2-carboxamide;
N-(4-{[1-(2-ethylbutanoyl)azetidin-3-yl]oxy}phenyl)-1,3-dihydro-2H-pyrrolo[3,4-c]pyridine-2-carboxamide;
N-(4-{[1-(pent-4-ynoyl)azetidin-3-yl]oxy}phenyl)-1,3-dihydro-2H-pyrrolo[3,4-c]pyridine-2-carboxamide;
N-(4-{[1-(furan-2-ylcarbonyl)azetidin-3-yl]oxy}phenyl)-1,3-dihydro-2H-pyrrolo[3,4-c]pyridine-2-carboxamide;
N-(4-{[1-(furan-3-ylcarbonyl)azetidin-3-yl]oxy}phenyl)-1,3-dihydro-2H-pyrrolo[3,4-c]pyridine-2-carboxamide;
N-(4-{[1-(thiophen-3-ylcarbonyl)azetidin-3-yl]oxy}phenyl)-1,3-dihydro-2H-pyrrolo[3,4-c]pyridine-2-carboxamide;
N-(4-{[1-(1H-pyrrol-2-ylcarbonyl)azetidin-3-yl]oxy}phenyl)-1,3-dihydro-2H-pyrrolo[3,4-c]pyridine-2-carboxamide;
N-(4-{[1-(pyrimidin-4-ylcarbonyl)azetidin-3-yl]oxy}phenyl)-1,3-dihydro-2H-pyrrolo[3,4-c]pyridine-2-carboxamide;
N-[4-({1-[(5-methylpyrazin-2-yl)carbonyl]azetidin-3-yl}oxy)phenyl]-1,3-dihydro-2H-pyrrolo[3,4-c]pyridine-2-carboxamide;
N-(4-{[1-(N,N-dimethylglycyl)azetidin-3-yl]oxy}phenyl)-1,3-dihydro-2H-pyrrolo[3,4-c]pyridine-2-carboxamide;
N-(4-{[1-(N,N-dimethyl-beta-alanyl)azetidin-3-yl]oxy}phenyl)-1,3-dihydro-2H-pyrrolo[3,4-c]pyridine-2-carboxamide;
N-(4-{[1-(pyrrolidin-1-ylacetyl)azetidin-3-yl]oxy}phenyl)-1,3-dihydro-2H-pyrrolo[3,4-c]pyridine-2-carboxamide;
N-[4-({1-[3-(pyrrolidin-1-yl)propanoyl]azetidin-3-yl}oxy)phenyl]-1,3-dihydro-2H-pyrrolo[3,4-c]pyridine-2-carboxamide;
N-[4-({1-[3-(piperidin-1-yl)propanoyl]azetidin-3-yl}oxy)phenyl]-1,3-dihydro-2H-pyrrolo[3,4-c]pyridine-2-carboxamide;
N-[4-({1-[(4-methylpiperazin-1-yl)acetyl]azetidin-3-yl}oxy)phenyl]-1,3-dihydro-2H-pyrrolo[3,4-c]pyridine-2-carboxamide;
N-[4-({1-[3-(4-methylpiperazin-1-yl)propanoyl]azetidin-3-yl}oxy)phenyl]-1,3-dihydro-2H-pyrrolo[3,4-c]pyridine-2-carboxamide;
N-(4-{[1-(2-cyclopropylethyl)piperidin-4-yl]oxy}phenyl)-1,3-dihydro-2H-pyrrolo[3,4-c]pyridine-2-carboxamide;
N-(4-{[1-(2-cyclopentylethyl)piperidin-4-yl]oxy}phenyl)-1,3-dihydro-2H-pyrrolo[3,4-c]pyridine-2-carboxamide;
N-(4-{[1-(2-methylbutyl)piperidin-4-yl]oxy}phenyl)-1,3-dihydro-2H-pyrrolo[3,4-c]pyridine-2-carboxamide;
N-(4-{[1-(tetrahydrofuran-3-ylmethyl)piperidin-4-yl]oxy}phenyl)-1,3-dihydro-2H-pyrrolo[3,4-c]pyridine-2-carboxamide;
N-(4-{[1-(3,3-dimethylbutyl)piperidin-4-yl]oxy}phenyl)-1,3-dihydro-2H-pyrrolo[3,4-c]pyridine-2-carboxamide;
N-(4-{[1-(cyclohexylmethyl)piperidin-4-yl]oxy}phenyl)-1,3-dihydro-2H-pyrrolo[3,4-c]pyridine-2-carboxamide;
N-(4-{[1-(3-methylbutyl)piperidin-4-yl]oxy}phenyl)-1,3-dihydro-2H-pyrrolo[3,4-c]pyridine-2-carboxamide;
N-(4-{[1-(cyclopentylmethyl)piperidin-4-yl]oxy}phenyl)-1,3-dihydro-2H-pyrrolo[3,4-c]pyridine-2-carboxamide;
N-(4-{[1-(tetrahydrofuran-2-ylmethyl)piperidin-4-yl]oxy}phenyl)-1,3-dihydro-2H-pyrrolo[3,4-c]pyridine-2-carboxamide;
N-(4-{[1-(2-methylpropyl)piperidin-4-yl]oxy}phenyl)-1,3-dihydro-2H-pyrrolo[3,4-c]pyridine-2-carboxamide;
N-(4-{[1-(butylsulfonyl)piperidin-4-yl]oxy}phenyl)-1,3-dihydro-2H-pyrrolo[3,4-c]pyridine-2-carboxamide;
N-(4-{[1-(cyclopropylsulfonyl)piperidin-4-yl]oxy}phenyl)-1,3-dihydro-2H-pyrrolo[3,4-c]pyridine-2-carboxamide;
N-(4-{[1-(phenylsulfonyl)piperidin-4-yl]oxy}phenyl)-1,3-dihydro-2H-pyrrolo[3,4-c]pyridine-2-carboxamide;
N-[4-({1-[(4-fluorophenyl)sulfonyl]piperidin-4-yl}oxy)phenyl]-1,3-dihydro-2H-pyrrolo[3,4-c]pyridine-2-carboxamide;
N-(4-{[1-(ethylsulfonyl)piperidin-4-yl]oxy}phenyl)-1,3-dihydro-2H-pyrrolo[3,4-c]pyridine-2-carboxamide;

N-(4-{[1-(propan-2-ylsulfonyl)piperidin-4-yl]oxy}phenyl)-1,3-dihydro-2H-pyrrolo[3,4-c]pyridine-2-carboxamide;
N-(4-{[1-(benzylsulfonyl)piperidin-4-yl]oxy}phenyl)-1,3-dihydro-2H-pyrrolo[3,4-c]pyridine-2-carboxamide;
N-(4-{[1-(propylsulfonyl)piperidin-4-yl]oxy}phenyl)-1,3-dihydro-2H-pyrrolo[3,4-c]pyridine-2-carboxamide;
N-(4-{[1-(thiophen-2-ylsulfonyl)piperidin-4-yl]oxy}phenyl)-1,3-dihydro-2H-pyrrolo[3,4-c]pyridine-2-carboxamide;
N-[4-({1-[(2S)-2-methylbutanoyl]piperidin-4-yl}oxy)phenyl]-1,3-dihydro-2H-pyrrolo[3,4-c]pyridine-2-carboxamide;
N-[4-({1-[(2S)-tetrahydrofuran-2-ylcarbonyl]piperidin-4-yl}oxy)phenyl]-1,3-dihydro-2H-pyrrolo[3,4-c]pyridine-2-carboxamide;
N-[4-({1-[(2R)-tetrahydrofuran-2-ylcarbonyl]piperidin-4-yl}oxy)phenyl]-1,3-dihydro-2H-pyrrolo[3,4-c]pyridine-2-carboxamide;
N-[4-({1-[(4,4-difluorocyclohexyl)carbonyl]azetidin-3-yl}oxy)phenyl]-1,3-dihydro-2H-pyrrolo[3,4-c]pyridine-2-carboxamide;
N-(4-{[1-(5-oxo-D-prolyl)piperidin-4-yl]oxy}phenyl)-1,3-dihydro-2H-pyrrolo[3,4-c]pyridine-2-carboxamide;
N-(4-{[1-(2,2-dimethylpropanoyl)piperidin-4-yl]oxy}phenyl)-1,3-dihydro-2H-pyrrolo[3,4-c]pyridine-2-carboxamide;
N-(4-{[1-(2-methylpentanoyl)piperidin-4-yl]oxy}phenyl)-1,3-dihydro-2H-pyrrolo[3,4-c]pyridine-2-carboxamide;
N-(4-{[1-(2-ethylbutanoyl)piperidin-4-yl]oxy}phenyl)-1,3-dihydro-2H-pyrrolo[3,4-c]pyridine-2-carboxamide;
N-(4-{[1-(1H-pyrrol-2-ylcarbonyl)piperidin-4-yl]oxy}phenyl)-1,3-dihydro-2H-pyrrolo[3,4-c]pyridine-2-carboxamide;
N-(4-{[1-(1,2-oxazol-5-ylcarbonyl)piperidin-4-yl]oxy}phenyl)-1,3-dihydro-2H-pyrrolo[3,4-c]pyridine-2-carboxamide;
N-(4-{[1-(pyridin-3-ylcarbonyl)piperidin-4-yl]oxy}phenyl)-1,3-dihydro-2H-pyrrolo[3,4-c]pyridine-2-carboxamide;
N-(4-{[1-(pyridazin-3-ylcarbonyl)piperidin-4-yl]oxy}phenyl)-1,3-dihydro-2H-pyrrolo[3,4-c]pyridine-2-carboxamide;
N-(4-{[1-(pyrazin-2-ylcarbonyl)piperidin-4-yl]oxy}phenyl)-1,3-dihydro-2H-pyrrolo[3,4-c]pyridine-2-carboxamide;
N-(4-{[1-(pyrimidin-4-ylcarbonyl)piperidin-4-yl]oxy}phenyl)-1,3-dihydro-2H-pyrrolo[3,4-c]pyridine-2-carboxamide;
N-[4-({1-[(5-methylpyrazin-2-yl)carbonyl]piperidin-4-yl}oxy)phenyl]-1,3-dihydro-2H-pyrrolo[3,4-c]pyridine-2-carboxamide;
N-[4-({1-[3-(piperidin-1-yl)propanoyl]piperidin-4-yl}oxy)phenyl]-1,3-dihydro-2H-pyrrolo[3,4-c]pyridine-2-carboxamide;
N-(4-{[1-(morpholin-4-ylacetyl)piperidin-4-yl]oxy}phenyl)-1,3-dihydro-2H-pyrrolo[3,4-c]pyridine-2-carboxamide;
N-[4-({1-[3-(4-methylpiperazin-1-yl)propanoyl]piperidin-4-yl}oxy)phenyl]-1,3-dihydro-2H-pyrrolo[3,4-c]pyridine-2-carboxamide;
N-[4-(4-{[(4-methylpiperazin-1-yl)acetyl]amino}cyclohex-1-en-1-yl)phenyl]-1,3-dihydro-2H-pyrrolo[3,4-c]pyridine-2-carboxamide;
N-(4-{4-[(tetrahydro-2H-pyran-4-ylacetyl)amino]cyclohex-1-en-1-yl}phenyl)-1,3-dihydro-2H-pyrrolo[3,4-c]pyridine-2-carboxamide;
N-{4-[4-(benzoylamino)cyclohex-1-en-1-yl]phenyl}-1,3-dihydro-2H-pyrrolo[3,4-c]pyridine-2-carboxamide;
N-[4-(4-{[(2S)-tetrahydrofuran-2-ylcarbonyl]amino}cyclohex-1-en-1-yl)phenyl]-1,3-dihydro-2H-pyrrolo[3,4-c]pyridine-2-carboxamide;
N-[4-(4-{[(2R)-tetrahydrofuran-2-ylcarbonyl]amino}cyclohex-1-en-1-yl)phenyl]-1,3-dihydro-2H-pyrrolo[3,4-c]pyridine-2-carboxamide;
N-[4-(4-{[(1-methylpiperidin-4-yl)carbonyl]amino}cyclohex-1-en-1-yl)phenyl]-1,3-dihydro-2H-pyrrolo[3,4-c]pyridine-2-carboxamide;
N-[4-(4-{[(1,1-dioxidotetrahydro-2H-thiopyran-4-yl)carbonyl]amino}cyclohex-1-en-1-yl)phenyl]-1,3-dihydro-2H-pyrrolo[3,4-c]pyridine-2-carboxamide;
N-[4-(4-{[(3R)-tetrahydrofuran-3-ylcarbonyl]amino}cyclohex-1-en-1-yl)phenyl]-1,3-dihydro-2H-pyrrolo[3,4-c]pyridine-2-carboxamide;
N-[4-(4-{[(3S)-tetrahydrofuran-3-ylcarbonyl]amino}cyclohex-1-en-1-yl)phenyl]-1,3-dihydro-2H-pyrrolo[3,4-c]pyridine-2-carboxamide;
N-[4-(4-{[(2S)-2-methylbutanoyl]amino}cyclohex-1-en-1-yl)phenyl]-1,3-dihydro-2H-pyrrolo[3,4-c]pyridine-2-carboxamide;
N-(4-{3-[(3-methylbutanoyl)amino]oxetan-3-yl}phenyl)-1,3-dihydro-2H-pyrrolo[3,4-c]pyridine-2-carboxamide;
tert-butyl 4-({4-[(1,3-dihydro-2H-pyrrolo[3,4-c]pyridin-2-ylcarbonyl)amino]phenyl}sulfonyl)piperidine-1-carboxylate;
N-{4-[4-(propylcarbamoyl)piperidin-1-yl]phenyl}-1,3-dihydro-2H-pyrrolo[3,4-c]pyridine-2-carboxamide;
N-(4-{4-[(2-methoxyethyl)carbamoyl]piperidin-1-yl}phenyl)-1,3-dihydro-2H-pyrrolo[3,4-c]pyridine-2-carboxamide;
N-(4-{4-[(cyclopentylmethyl)carbamoyl]piperidin-1-yl}phenyl)-1,3-dihydro-2H-pyrrolo[3,4-c]pyridine-2-carboxamide;
N-(4-{4-[(1,4-dioxan-2-ylmethyl)carbamoyl]piperidin-1-yl}phenyl)-1,3-dihydro-2H-pyrrolo[3,4-c]pyridine-2-carboxamide;
N-{4-[4-(cyclopentylcarbamoyl)piperidin-1-yl]phenyl}-1,3-dihydro-2H-pyrrolo[3,4-c]pyridine-2-carboxamide;
N-{4-[4-(tetrahydro-2H-pyran-4-ylcarbamoyl)piperidin-1-yl]phenyl}-1,3-dihydro-2H-pyrrolo[3,4-c]pyridine-2-carboxamide;
N-{4-[4-(morpholin-4-ylcarbonyl)piperidin-1-yl]phenyl}-1,3-dihydro-2H-pyrrolo[3,4-c]pyridine-2-carboxamide;
N-(4-{4-[(tetrahydro-2H-pyran-4-ylmethyl)carbamoyl]piperidin-1-yl}phenyl)-1,3-dihydro-2H-pyrrolo[3,4-c]pyridine-2-carboxamide;
N-{4-[4-(cyclopropylcarbamoyl)piperidin-1-yl]phenyl}-1,3-dihydro-2H-pyrrolo[3,4-c]pyridine-2-carboxamide;
N-(4-{4-[(tetrahydrofuran-3-ylmethyl)carbamoyl]piperidin-1-yl}phenyl)-1,3-dihydro-2H-pyrrolo[3,4-c]pyridine-2-carboxamide;
N-(4-{4-[(2-hydroxy-2-methylpropyl)carbamoyl]piperidin-1-yl}phenyl)-1,3-dihydro-2H-pyrrolo[3,4-c]pyridine-2-carboxamide;
N-{4-[4-(butan-2-ylcarbamoyl)piperidin-1-yl]phenyl}-1,3-dihydro-2H-pyrrolo[3,4-c]pyridine-2-carboxamide;
N-(4-{1-[(3R)-tetrahydrofuran-3-ylcarbonyl]-1,2,3,6-tetrahydropyridin-4-yl}phenyl)-1,3-dihydro-2H-isoindole-2-carboxamide;
N-(4-{1-[(3S)-tetrahydrofuran-3-ylcarbonyl]-1,2,3,6-tetrahydropyridin-4-yl}phenyl)-1,3-dihydro-2H-isoindole-2-carboxamide;

N-(4-{1-[(1,1-dioxidotetrahydro-2H-thiopyran-4-yl)carbonyl]-1,2,3,6-tetrahydropyridin-4-yl}phenyl)-1,3-dihydro-2H-isoindole-2-carboxamide;

N-(4-{1-[(2R)-tetrahydrofuran-2-ylcarbonyl]piperidin-4-yl}phenyl)-1,3-dihydro-2H-isoindole-2-carboxamide;

N-(4-{1-[(2S)-tetrahydrofuran-2-ylcarbonyl]piperidin-4-yl}phenyl)-1,3-dihydro-2H-isoindole-2-carboxamide;

N-(4-{1-[(3R)-tetrahydrofuran-3-ylcarbonyl]piperidin-4-yl}phenyl)-1,3-dihydro-2H-isoindole-2-carboxamide;

N-(4-{(4R)-4-[(2-methylpropanoyl)amino]cyclohex-1-en-1-yl}phenyl)-1,3-dihydro-2H-pyrrolo[3,4-c]pyridine-2-carboxamide;

N-(4-{(4S)-4-[(2-methylpropanoyl)amino]cyclohex-1-en-1-yl}phenyl)-1,3-dihydro-2H-pyrrolo[3,4-c]pyridine-2-carboxamide;

N-(4-{1-[(2-methyl-1,3-oxazol-4-yl)carbonyl]-1,2,3,6-tetrahydropyridin-4-yl}phenyl)-1,3-dihydro-2H-pyrrolo[3,4-c]pyridine-2-carboxamide;

N-{4-[1-(furan-3-ylcarbonyl)-1,2,3,6-tetrahydropyridin-4-yl]phenyl}-1,3-dihydro-2H-pyrrolo[3,4-c]pyridine-2-carboxamide;

N-(4-{1-[(2E)-3-(furan-2-yl)prop-2-enoyl]-1,2,3,6-tetrahydropyridin-4-yl}phenyl)-1,3-dihydro-2H-pyrrolo[3,4-c]pyridine-2-carboxamide;

N-{4-[1-(1,3-oxazol-5-ylcarbonyl)-1,2,3,6-tetrahydropyridin-4-yl]phenyl}-1,3-dihydro-2H-pyrrolo[3,4-c]pyridine-2-carboxamide;

N-{4-[1-(3,3,3-trifluoropropanoyl)-1,2,3,6-tetrahydropyridin-4-yl]phenyl}-1,3-dihydro-2H-pyrrolo[3,4-c]pyridine-2-carboxamide;

N-(4-{1-[(1,5-dimethyl-1H-pyrazol-3-yl)carbonyl]-1,2,3,6-tetrahydropyridin-4-yl}phenyl)-1,3-dihydro-2H-pyrrolo[3,4-c]pyridine-2-carboxamide;

N-(4-{1-[(4-methoxycyclohexyl)carbonyl]-1,2,3,6-tetrahydropyridin-4-yl}phenyl)-1,3-dihydro-2H-pyrrolo[3,4-c]pyridine-2-carboxamide;

N-{4-[1-(2,3-dimethylbutanoyl)-1,2,3,6-tetrahydropyridin-4-yl]phenyl}-1,3-dihydro-2H-pyrrolo[3,4-c]pyridine-2-carboxamide;

N-(4-{1-[(2,2-difluorocyclopropyl)carbonyl]-1,2,3,6-tetrahydropyridin-4-yl}phenyl)-1,3-dihydro-2H-pyrrolo[3,4-c]pyridine-2-carboxamide;

N-{4-[1-(1H-pyrazol-5-ylcarbonyl)-1,2,3,6-tetrahydropyridin-4-yl]phenyl}-1,3-dihydro-2H-pyrrolo[3,4-c]pyridine-2-carboxamide;

N-{4-[1-(tert-butoxyacetyl)-1,2,3,6-tetrahydropyridin-4-yl]phenyl}-1,3-dihydro-2H-pyrrolo[3,4-c]pyridine-2-carboxamide;

N-(4-{1-[3-(1H-1,2,4-triazol-1-yl)propanoyl]-1,2,3,6-tetrahydropyridin-4-yl}phenyl)-1,3-dihydro-2H-pyrrolo[3,4-c]pyridine-2-carboxamide;

N-{4-[1-(3-ethoxypropanoyl)-1,2,3,6-tetrahydropyridin-4-yl]phenyl}-1,3-dihydro-2H-pyrrolo[3,4-c]pyridine-2-carboxamide;

N-{4-[1-(3-hydroxy-3-methylbutanoyl)-1,2,3,6-tetrahydropyridin-4-yl]phenyl}-1,3-dihydro-2H-pyrrolo[3,4-c]pyridine-2-carboxamide;

N-{4-[1-[3-(1H-pyrrol-1-yl)propanoyl]-1,2,3,6-tetrahydropyridin-4-yl]phenyl}-1,3-dihydro-2H-pyrrolo[3,4-c]pyridine-2-carboxamide;

N-(4-{1-[(1-methylcyclopropyl)carbonyl]-1,2,3,6-tetrahydropyridin-4-yl}phenyl)-1,3-dihydro-2H-pyrrolo[3,4-c]pyridine-2-carboxamide;

N-(4-{1-[(2-methylpropoxy)acetyl]-1,2,3,6-tetrahydropyridin-4-yl}phenyl)-1,3-dihydro-2H-pyrrolo[3,4-c]pyridine-2-carboxamide;

N-{4-[1-(1-methylprolyl)-1,2,3,6-tetrahydropyridin-4-yl]phenyl}-1,3-dihydro-2H-pyrrolo[3,4-c]pyridine-2-carboxamide;

N-{4-[1-(2-hydroxy-2-methylbutanoyl)-1,2,3,6-tetrahydropyridin-4-yl]phenyl}-1,3-dihydro-2H-pyrrolo[3,4-c]pyridine-2-carboxamide;

N-(4-{1-[(1-hydroxycyclopropyl)carbonyl]-1,2,3,6-tetrahydropyridin-4-yl}phenyl)-1,3-dihydro-2H-pyrrolo[3,4-c]pyridine-2-carboxamide;

N-{4-[1-(cyclopropylacetyl)-1,2,3,6-tetrahydropyridin-4-yl]phenyl}-1,3-dihydro-2H-pyrrolo[3,4-c]pyridine-2-carboxamide;

N-{4-[1-(cyclopentylcarbonyl)-1,2,3,6-tetrahydropyridin-4-yl]phenyl}-1,3-dihydro-2H-pyrrolo[3,4-c]pyridine-2-carboxamide;

N-[4-(1-{[1-(methoxymethyl)cyclopropyl]carbonyl}-1,2,3,6-tetrahydropyridin-4-yl)phenyl]-1,3-dihydro-2H-pyrrolo[3,4-c]pyridine-2-carboxamide;

N-(4-{1-[(methylsulfonyl)acetyl]-1,2,3,6-tetrahydropyridin-4-yl}phenyl)-1,3-dihydro-2H-pyrrolo[3,4-c]pyridine-2-carboxamide;

N-(4-{1-[(1-methyl-1H-pyrazol-4-yl)carbonyl]-1,2,3,6-tetrahydropyridin-4-yl}phenyl)-1,3-dihydro-2H-pyrrolo[3,4-c]pyridine-2-carboxamide;

N-[4-(1-acetyl-1,2,3,6-tetrahydropyridin-4-yl)phenyl]-1,3-dihydro-2H-pyrrolo[3,4-c]pyridine-2-carboxamide;

N-{4-[1-(cyclopropylcarbonyl)-1,2,3,6-tetrahydropyridin-4-yl]phenyl}-1,3-dihydro-2H-pyrrolo[3,4-c]pyridine-2-carboxamide;

N-{4-[1-(2-ethylbutanoyl)-1,2,3,6-tetrahydropyridin-4-yl]phenyl}-1,3-dihydro-2H-pyrrolo[3,4-c]pyridine-2-carboxamide;

N-{4-[1-(5-oxo-L-prolyl)-1,2,3,6-tetrahydropyridin-4-yl]phenyl}-1,3-dihydro-2H-pyrrolo[3,4-c]pyridine-2-carboxamide;

N-(4-{1-[(2E)-4-methylpent-2-enoyl]-1,2,3,6-tetrahydropyridin-4-yl}phenyl)-1,3-dihydro-2H-pyrrolo[3,4-c]pyridine-2-carboxamide;

N-{4-[1-(2-methoxy-2-methylpropanoyl)-1,2,3,6-tetrahydropyridin-4-yl]phenyl}-1,3-dihydro-2H-pyrrolo[3,4-c]pyridine-2-carboxamide;

N-{4-[1-(cyclopent-1-en-1-ylcarbonyl)-1,2,3,6-tetrahydropyridin-4-yl]phenyl}-1,3-dihydro-2H-pyrrolo[3,4-c]pyridine-2-carboxamide;

N-{4-[1-(thiophen-3-ylacetyl)-1,2,3,6-tetrahydropyridin-4-yl]phenyl}-1,3-dihydro-2H-pyrrolo[3,4-c]pyridine-2-carboxamide;

N-{4-[1-(cyclohexylcarbonyl)-1,2,3,6-tetrahydropyridin-4-yl]phenyl}-1,3-dihydro-2H-pyrrolo[3,4-c]pyridine-2-carboxamide;

N-[4-(1-propanoyl-1,2,3,6-tetrahydropyridin-4-yl)phenyl]-1,3-dihydro-2H-pyrrolo[3,4-c]pyridine-2-carboxamide;

N-{4-[1-(2,2-dimethylbutanoyl)-1,2,3,6-tetrahydropyridin-4-yl]phenyl}-1,3-dihydro-2H-pyrrolo[3,4-c]pyridine-2-carboxamide;

N-(4-{1-[(1-methyl-1H-pyrrol-2-yl)carbonyl]-1,2,3,6-tetrahydropyridin-4-yl}phenyl)-1,3-dihydro-2H-pyrrolo[3,4-c]pyridine-2-carboxamide;

N-{4-[1-(methoxyacetyl)-1,2,3,6-tetrahydropyridin-4-yl]phenyl}-1,3-dihydro-2H-pyrrolo[3,4-c]pyridine-2-carboxamide;

N-{4-[1-(2,2-dimethylpropanoyl)-1,2,3,6-tetrahydropyridin-4-yl]phenyl}-1,3-dihydro-2H-pyrrolo[3,4-c]pyridine-2-carboxamide;

N-{4-[1-(4-methylhexanoyl)-1,2,3,6-tetrahydropyridin-4-yl]phenyl}-1,3-dihydro-2H-pyrrolo[3,4-c]pyridine-2-carboxamide;

N-(4-{1-[(2,2-dimethylcyclopropyl)carbonyl]-1,2,3,6-tetrahydropyridin-4-yl}phenyl)-1,3-dihydro-2H-pyrrolo[3,4-c]pyridine-2-carboxamide;
N-(4-{1-[(1,3-dimethyl-1H-pyrazol-5-yl)carbonyl]-1,2,3,6-tetrahydropyridin-4-yl}phenyl)-1,3-dihydro-2H-pyrrolo[3,4-c]pyridine-2-carboxamide;
N-{4-[1-(cyclobutylacetyl)-1,2,3,6-tetrahydropyridin-4-yl]phenyl}-1,3-dihydro-2H-pyrrolo[3,4-c]pyridine-2-carboxamide;
N-{4-[1-(piperidin-1-ylacetyl)-1,2,3,6-tetrahydropyridin-4-yl]phenyl}-1,3-dihydro-2H-pyrrolo[3,4-c]pyridine-2-carboxamide;
N-(4-{1-[2-(pyrrolidin-1-yl)propanoyl]-1,2,3,6-tetrahydropyridin-4-yl}phenyl)-1,3-dihydro-2H-pyrrolo[3,4-c]pyridine-2-carboxamide;
N-(4-{1-[(1,3-dimethyl-1H-pyrazol-4-yl)carbonyl]-1,2,3,6-tetrahydropyridin-4-yl}phenyl)-1,3-dihydro-2H-pyrrolo[3,4-c]pyridine-2-carboxamide;
N-[4-(cis-4-{[(2-methoxyethoxy)acetyl]amino}cyclohexyl)phenyl]-1,3-dihydro-2H-pyrrolo[3,4-c]pyridine-2-carboxamide;
N-[4-(trans-4-{[(2-methoxyethoxy)acetyl]amino}cyclohexyl)phenyl]-1,3-dihydro-2H-pyrrolo[3,4-c]pyridine-2-carboxamide;
N-[4-(cis-4-{[(2S)-tetrahydrofuran-2-ylcarbonyl]amino}cyclohexyl)phenyl]-1,3-dihydro-2H-pyrrolo[3,4-c]pyridine-2-carboxamide;
N-[4-(trans-4-{[(2S)-tetrahydrofuran-2-ylcarbonyl]amino}cyclohexyl)phenyl]-1,3-dihydro-2H-pyrrolo[3,4-c]pyridine-2-carboxamide;
N-[4-(cis-4-{[(2R)-tetrahydrofuran-2-ylcarbonyl]amino}cyclohexyl)phenyl]-1,3-dihydro-2H-pyrrolo[3,4-c]pyridine-2-carboxamide;
N-[4-(trans-4-{[(2R)-tetrahydrofuran-2-ylcarbonyl]amino}cyclohexyl)phenyl]-1,3-dihydro-2H-pyrrolo[3,4-c]pyridine-2-carboxamide;
N-(4-{[(3R)-1-(3-methylbutanoyl)pyrrolidin-3-yl]oxy}phenyl)-1,3-dihydro-2H-pyrrolo[3,4-c]pyridine-2-carboxamide;
N-(4-{[(3R)-1-(cyclobutylcarbonyl)pyrrolidin-3-yl]oxy}phenyl)-1,3-dihydro-2H-pyrrolo[3,4-c]pyridine-2-carboxamide;
N-[4-({(3R)-1-[(2R)-tetrahydrofuran-2-ylcarbonyl]pyrrolidin-3-yl}oxy)phenyl]-1,3-dihydro-2H-pyrrolo[3,4-c]pyridine-2-carboxamide;
N-[4-({(3R)-1-[(2S)-tetrahydrofuran-2-ylcarbonyl]pyrrolidin-3-yl}oxy)phenyl]-1,3-dihydro-2H-pyrrolo[3,4-c]pyridine-2-carboxamide;
N-(4-{[(3R)-1-(cyclopropylacetyl)pyrrolidin-3-yl]oxy}phenyl)-1,3-dihydro-2H-pyrrolo[3,4-c]pyridine-2-carboxamide;
N-(4-{[(3S)-1-(3-methylbutanoyl)pyrrolidin-3-yl]oxy}phenyl)-1,3-dihydro-2H-pyrrolo[3,4-c]pyridine-2-carboxamide;
N-(4-{[(3S)-1-(cyclobutylcarbonyl)pyrrolidin-3-yl]oxy}phenyl)-1,3-dihydro-2H-pyrrolo[3,4-c]pyridine-2-carboxamide;
N-[4-({(3S)-1-[(2R)-tetrahydrofuran-2-ylcarbonyl]pyrrolidin-3-yl}oxy)phenyl]-1,3-dihydro-2H-pyrrolo[3,4-c]pyridine-2-carboxamide;
N-[4-({(3S)-1-[(2S)-tetrahydrofuran-2-ylcarbonyl]pyrrolidin-3-yl}oxy)phenyl]-1,3-dihydro-2H-pyrrolo[3,4-c]pyridine-2-carboxamide;
N-(4-{[(3S)-1-(cyclopropylacetyl)pyrrolidin-3-yl]oxy}phenyl)-1,3-dihydro-2H-pyrrolo[3,4-c]pyridine-2-carboxamide;
N-(4-{trans-4-[(2-methylpropanoyl)amino]cyclohexyl}phenyl)-1,3-dihydro-2H-pyrrolo[3,4-c]pyridine-2-carboxamide;
N-(4-{cis-4-[(2-methylpropanoyl)amino]cyclohexyl}phenyl)-1,3-dihydro-2H-pyrrolo[3,4-c]pyridine-2-carboxamide;
N-(4-{cis-4-[(cyclohexylcarbonyl)amino]cyclohexyl}phenyl)-1,3-dihydro-2H-pyrrolo[3,4-c]pyridine-2-carboxamide;
N-(4-{trans-4-[(cyclohexylcarbonyl)amino]cyclohexyl}phenyl)-1,3-dihydro-2H-pyrrolo[3,4-c]pyridine-2-carboxamide;
N-(4-{trans-4-[(cyclopropylacetyl)amino]cyclohexyl}phenyl)-1,3-dihydro-2H-pyrrolo[3,4-c]pyridine-2-carboxamide;
N-(4-{cis-4-[(cyclopropylacetyl)amino]cyclohexyl}phenyl)-1,3-dihydro-2H-pyrrolo[3,4-c]pyridine-2-carboxamide;
N-(4-{4-[(2-methylpropanoyl)amino]cyclohex-1-en-1-yl}phenyl)-1,3-dihydro-2H-isoindole-2-carboxamide;
N-[4-(4-{[(2R)-tetrahydrofuran-2-ylcarbonyl]amino}cyclohex-1-en-1-yl)phenyl]-1,3-dihydro-2H-isoindole-2-carboxamide;
N-[4-(4-{[(2S)-tetrahydrofuran-2-ylcarbonyl]amino}cyclohex-1-en-1-yl)phenyl]-1,3-dihydro-2H-isoindole-2-carboxamide;
N-(4-{4-[(cyclopentylacetyl)amino]cyclohex-1-en-1-yl}phenyl)-1,3-dihydro-2H-isoindole-2-carboxamide;
N-(4-{4-[(cyclopropylacetyl)amino]cyclohex-1-en-1-yl}phenyl)-1,3-dihydro-2H-isoindole-2-carboxamide;
N-(4-{4-[(2-hydroxy-2-methylpropanoyl)amino]cyclohex-1-en-1-yl}phenyl)-1,3-dihydro-2H-isoindole-2-carboxamide;
N-(4-{4-[(tetrahydro-2H-pyran-4-ylcarbonyl)amino]cyclohex-1-en-1-yl}phenyl)-1,3-dihydro-2H-isoindole-2-carboxamide;
N-(4-{4-[(cyclohexylcarbonyl)amino]cyclohex-1-en-1-yl}phenyl)-1,3-dihydro-2H-isoindole-2-carboxamide;
and pharmaceutically acceptable salts thereof.

Still another embodiment pertains to compounds having Formula (IIIc), which include
N-[4-(4-oxo-3,4-dihydrophthalazin-1-yl)phenyl]-1,3-dihydro-2H-isoindole-2-carboxamide;
N-[4-(isoquinolin-4-yl)phenyl]-1,3-dihydro-2H-isoindole-2-carboxamide;
N-[4-(1-oxo-1,2-dihydroisoquinolin-4-yl)phenyl]-1,3-dihydro-2H-isoindole-2-carboxamide;
N-[4-(4-oxo-3,4,5,6,7,8-hexahydrophthalazin-1-yl)phenyl]-1,3-dihydro-2H-isoindole-2-carboxamide;
N-[4-(8-fluoro-4-oxo-3,4-dihydrophthalazin-1-yl)phenyl]-1,3-dihydro-2H-isoindole-2-carboxamide;
5-fluoro-N-[4-(4-oxo-3,4-dihydrophthalazin-1-yl)phenyl]-1,3-dihydro-2H-isoindole-2-carboxamide;
N-[4-(4-oxo-3,4-dihydrophthalazin-1-yl)phenyl]-5-(pyrrolidin-1-ylmethyl)-1,3-dihydro-2H-isoindole-2-carboxamide;
5-(morpholin-4-ylmethyl)-N-[4-(1-oxo-1,2-dihydroisoquinolin-4-yl)phenyl]-1,3-dihydro-2H-isoindole-2-carboxamide;
5-methoxy-N-[4-(1-oxo-1,2-dihydroisoquinolin-4-yl)phenyl]-1,3-dihydro-2H-isoindole-2-carboxamide;
5-[(4-methylpiperazin-1-yl)methyl]-N-[4-(4-oxo-3,4-dihydrophthalazin-1-yl)phenyl]-1,3-dihydro-2H-isoindole-2-carboxamide;
5-cyano-N-[4-(1-oxo-1,2-dihydroisoquinolin-4-yl)phenyl]-1,3-dihydro-2H-isoindole-2-carboxamide;

5-chloro-N-[4-(1-oxo-1,2-dihydroisoquinolin-4-yl)phenyl]-1,3-dihydro-2H-isoindole-2-carboxamide;

N-[4-(4-oxo-4,5-dihydro-3H-2,3-benzodiazepin-1-yl)phenyl]-1,3-dihydro-2H-isoindole-2-carboxamide;

N-[4-(1-oxo-1,2-dihydroisoquinolin-4-yl)phenyl]-5-(pyrrolidin-1-ylmethyl)-1,3-dihydro-2H-isoindole-2-carboxamide;

N-{4-[4-oxo-8-(trifluoromethyl)-3,4-dihydrophthalazin-1-yl]phenyl}-1,3-dihydro-2H-isoindole-2-carboxamide;

5-[(dimethylamino)methyl]-N-[4-(1-oxo-1,2-dihydroisoquinolin-4-yl)phenyl]-1,3-dihydro-2H-isoindole-2-carboxamide;

5-[(diethylamino)methyl]-N-[4-(1-oxo-1,2-dihydroisoquinolin-4-yl)phenyl]-1,3-dihydro-2H-isoindole-2-carboxamide;

5-[(4-methylpiperazin-1-yl)methyl]-N-[4-(1-oxo-1,2-dihydroisoquinolin-4-yl)phenyl]-1,3-dihydro-2H-isoindole-2-carboxamide;

5-[(dimethylamino)methyl]-N-[4-(4-oxo-3,4-dihydrophthalazin-1-yl)phenyl]-1,3-dihydro-2H-isoindole-2-carboxamide;

5-[(diethylamino)methyl]-N-[4-(4-oxo-3,4-dihydrophthalazin-1-yl)phenyl]-1,3-dihydro-2H-isoindole-2-carboxamide;

N-{4-[4-oxo-8-(trifluoromethyl)-3,4-dihydrophthalazin-1-yl]phenyl}-5-(pyrrolidin-1-ylmethyl)-1,3-dihydro-2H-isoindole-2-carboxamide;

5-[(1-methylpiperidin-4-yl)oxy]-N-[4-(4-oxo-3,4-dihydrophthalazin-1-yl)phenyl]-1,3-dihydro-2H-isoindole-2-carboxamide;

5-{[(3R)-3-fluoropyrrolidin-1-yl]methyl}-N-[4-(4-oxo-3,4-dihydrophthalazin-1-yl)phenyl]-1,3-dihydro-2H-isoindole-2-carboxamide;

5-{[(3S)-3-fluoropyrrolidin-1-yl]methyl}-N-[4-(4-oxo-3,4-dihydrophthalazin-1-yl)phenyl]-1,3-dihydro-2H-isoindole-2-carboxamide;

5-(azetidin-1-ylmethyl)-N-[4-(4-oxo-3,4-dihydrophthalazin-1-yl)phenyl]-1,3-dihydro-2H-isoindole-2-carboxamide;

N-[4-(1-oxo-1,2-dihydropyrrolo[1,2-d][1,2,4]triazin-4-yl)phenyl]-1,3-dihydro-2H-isoindole-2-carboxamide; and N-[4-(1-oxo-1,2-dihydropyrrolo[1,2-d][1,2,4]triazin-4-yl)phenyl]-5-(pyrrolidin-1-ylmethyl)-1,3-dihydro-2H-isoindole-2-carboxamide;

N-[4-(1-oxo-2,3-dihydro-1H-isoindol-4-yl)phenyl]-1,3-dihydro-2H-isoindole-2-carboxamide;

N-[4-(4-oxo-3,4-dihydrophthalazin-1-yl)phenyl]-1,3-dihydro-2H-pyrrolo[3,4-c]pyridine-2-carboxamide;

N-[4-(4-oxo-3,4-dihydrophthalazin-1-yl)phenyl]-5,7-dihydro-6H-pyrrolo[3,4-b]pyridine-6-carboxamide;

N-[4-(1-oxo-1,2-dihydroisoquinolin-4-yl)cyclohex-3-en-1-yl]-1,3-dihydro-2H-isoindole-2-carboxamide;

N-[4-(4-oxo-3,4-dihydrophthalazin-1-yl)cyclohex-3-en-1-yl]-1,3-dihydro-2H-isoindole-2-carboxamide;

N-[4-(4-oxo-3,4-dihydrophthalazin-1-yl)cyclohex-3-en-1-yl]-5-(pyrrolidin-1-ylmethyl)-1,3-dihydro-2H-isoindole-2-carboxamide; and pharmaceutically acceptable salts thereof.

Embodiments of Formula (IVc)

In another aspect, the present invention provides compounds of Formula (IVc)

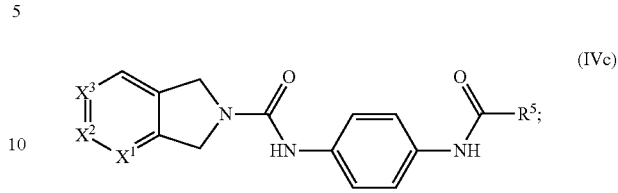

(IVc)

and pharmaceutically acceptable salts thereof; wherein $X^1$, $X^2$, $X^3$, and $R^5$ are as described herein for Formula (Ic).

In one embodiment of formula (IVc),
$X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or
$X^1$ is CH; $X^2$ is N; and $X^3$ is $CR^1$; or
$X^1$ is $CR^1$; $X^2$ is N; and $X^3$ is CH; or
$X^1$ is N; $X^2$ is $CR^1$; and $X^3$ is CH; or
$X^1$ is N; $X^2$ is $CR^1$; and $X^3$ is N;
$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, $C(O)H$, $CF_3$, $C(O)OH$, or $C(O)NH_2$;

$R^3$, at each occurrence, is independently selected alkyl, alkenyl, alkynyl, aryl, or heterocyclyl; wherein each $R^3$ alkyl, alkenyl, and alkynyl is optionally substituted with one, two, three or four independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I;

$R^5$, at each occurrence, is independently selected alkyl, alkenyl, alkynyl, aryl, heterocyclyl, cycloalkyl, or cycloalkenyl; wherein each $R^5$ alkyl, alkenyl, and alkynyl is optionally substituted with one, two, three or four independently selected $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I;

$R^6$, at each occurrence, is independently selected alkyl, alkenyl, alkynyl, aryl, heterocyclyl, cycloalkyl, or cycloalkenyl; wherein each $R^6$ alkyl, alkenyl, and alkynyl is optionally substituted with one, two, three or four independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, OH, (O), $C(O)OH$, $N_3$, CN, $NH_2$, $CF_3$, $CF_2CF_3$, F, Cl, Br or I;

$R^9$, at each occurrence, is independently selected alkyl, alkenyl, alkynyl, aryl, heterocyclyl, cycloalkyl, or cycloalkenyl; wherein each $R^9$ alkyl, alkenyl, and alkynyl is optionally substituted with one, two, three or four independently selected alkoxy, OH, cycloalkyl, aryl, or heterocyclyl;

$R^{10}$, at each occurrence, is independently selected alkyl, alkenyl, alkynyl, aryl, heterocyclyl, cycloalkyl, or cycloalkenyl;

wherein the cyclic moieties represented by $R^3$, $R^5$, $R^6$, $R^9$, and $R^{10}$ are optionally substituted with one, two, three, four, five, or six independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^3$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, $C(O)H$, $C(O)OH$, $OH$, $CN$, $N_3$, $NO_2$, $CF_3$, $CF_2CF_3$, $OCF_3$, $OCF_2CF_3$, $SCF_3$, F, Cl, Br or I;

$R^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, or cycloalkenyl; wherein each $R^{13}$ alkyl, alkenyl, and alkynyl is optionally substituted with one, two, three or four independently selected $R^{14}$, $OR^{14}$, $SR^{14}$, $S(O)R^{14}$, $SO_2R^{14}$, $C(O)R^{14}$, $OC(O)R^{14}$, $OC(O)OR^{14}$, $NH_2$, $NHR^{14}$, $N(R^{14})_2$, $NHC(O)R^{14}$, $NR^{14}C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, $C(O)H$, $C(O)OH$, $OH$, (O), $CN$, $N_3$, $NO_2$, $CF_3$, $CF_2CF_3$, $OCF_3$, $OCF_2CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, and cycloalkenyl is optionally substituted with one, two, three or four independently selected $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $C(O)H$, $C(O)OH$, $OH$, $CN$, $N_3$, $NO_2$, $CF_3$, $CF_2CF_3$, $OCF_3$, $OCF_2CF_3$, F, Cl, Br or I;

$R^{14}$, at each occurrence, is independently selected alkyl, alkenyl, alkynyl, aryl, heterocyclyl, cycloalkyl, or cycloalkenyl; wherein each $R^{14}$ alkyl, alkenyl, and alkynyl is optionally substituted with one, two, three or four independently selected heterocyclyl, alkoxy, $NH_2$, $SO_2NH_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I; wherein each $R^{14}$ aryl, heterocyclyl, cycloalkyl, and cycloalkenyl is optionally substituted with one, two, three or four independently selected $R^{16}$, $OR^{16}$, OH, F, Cl, Br, or I;

$R^{15}$, at each occurrence, is independently selected alkyl; wherein the $R^{15}$ alkyl is optionally substituted with one, two, three or four alkoxy; and $R^{16}$, at each occurrence, is independently selected alkyl, wherein the $R^{16}$ alkyl is optionally substituted with one, two, three or four alkoxy;

with the proviso that when $R^{13}$ is piperidinyl, it is substituted piperidinyl; and with the proviso that when $R^{13}$ is pyrrolinyl, at least one of $X^1$, $X^2$, and $X^3$ is N.

In one embodiment of Formula (IVc), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N; or $X^1$ is CH; $X^2$ is N; and $X^3$ is $CR^1$; or $X^1$ is $CR^1$; $X^2$ is N; and $X^3$ is CH; or $X^1$ is N; $X^2$ is $CR^1$; and $X^3$ is CH; or $X^1$ is N; $X^2$ is $CR^1$; and $X^3$ is N. In another embodiment of Formula (IVc), $X^1$, $X^2$, and $X^3$ are CH. In another embodiment of Formula (IVc), $X^1$ and $X^3$ are CH; and $X^2$ is N. In another embodiment of Formula (IVc), $X^1$ and $X^3$ are CH; and $X^2$ is $CR^1$. In another embodiment of Formula (IVc), $X^2$ and $X^3$ are CH; and $X^1$ is $CR^1$. In another embodiment of Formula (IVc), $X^1$ is CH; and $X^2$ and $X^3$ are $CR^1$. In another embodiment of Formula (IVc), $X^2$ is CH; and $X^1$ and $X^3$ are N. In another embodiment of Formula (IVc), $X^2$ and $X^3$ are CH; and $X^1$ is N. In another embodiment of Formula (IVc), $X^1$ is CH; $X^2$ is N; and $X^3$ is $CR^1$. In another embodiment of Formula (IVc), $X^1$ is $CR^1$; $X^2$ is N; and $X^3$ is CH. In another embodiment of Formula (IVc), $X^1$ is N; $X^2$ is $CR^1$; and $X^3$ is CH. In another embodiment of Formula (IVc), $X^1$ is N; $X^2$ is $CR^1$; and $X^3$ is N.

In another embodiment of Formula (IVc), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (IVc), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (IVc), $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (IVc), $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (IVc), $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (IVc), $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IVc), $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IVc), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IVc), $R^1$ is $C(O)NH_2$. In another embodiment of Formula (IVc), $R^1$ is F. In another embodiment of Formula (IVc), $R^1$ is Cl. In another embodiment of Formula (IVc), $R^1$ is Br. In another embodiment of Formula (IVc), $R^1$ is CN. In another embodiment of Formula (IVc), $R^1$ is $NH_2$. In another embodiment of Formula (IVc), $R^1$ is $NO_2$. In another embodiment of Formula (IVc), $R^1$ is $CF_3$. In another embodiment of Formula (IVc), $R^1$ is C(O)OH. In another embodiment of Formula (IVc), $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl.

In another embodiment of Formula (IVc), $X^1$ and $X^3$ are CH; and $X^2$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (IVc), $X^1$ and $X^3$ are CH; and $X^2$ is $CR^1$; $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IVc), $X^1$ and $X^3$ are CH; and $X^2$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IVc), $X^1$ and $X^3$ are CH; and $X^2$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IVc), $X^1$ and $X^3$ are CH; and $X^2$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IVc), $X^1$ and $X^3$ are CH; and $X^2$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IVc), $X^1$ and $X^3$ are CH; and $X^2$ is $CR^1$; $R^1$ is NHC(O)$R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IVc), $X^1$ and $X^3$ are CH; and $X^2$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IVc), $X^1$ and $X^3$ are CH; and $X^2$ is $CR^1$; and $R^1$ is $C(O)NH_2$. In another embodiment of Formula (IVc), $X^1$ and $X^3$ are CH; and $X^2$ is $CR^1$; and $R^1$ is F. In another embodiment of Formula (IVc), $X^1$ and $X^3$ are CH; and $X^2$ is $CR^1$; and $R^1$ is Cl. In another embodiment of Formula (IVc), $X^1$ and $X^3$ are CH; and $X^2$ is $CR^1$; and $R^1$ is Br. In another embodiment of Formula (IVc), $X^1$ and $X^3$ are CH; and $X^2$ is $CR^1$; and $R^1$ is CN. In another embodiment of Formula (IVc), $X^1$ and $X^3$ are CH; and $X^2$ is $CR^1$; and $R^1$ is $NH_2$. In another embodiment of Formula (IVc), $X^1$ and $X^3$ are CH; and $X^2$ is $CR^1$; and $R^1$ is $NO_2$. In another embodiment of Formula (IVc), $X^1$ and $X^3$ are CH; and $X^2$ is $CR^1$; and $R^1$ is $CF_3$. In another embodiment of Formula (IVc), $X^1$ and $X^3$ are CH; and $X^2$ is $CR^1$; and $R^1$ is C(O)OH. In another embodiment of Formula (IVc), $X^1$ and $X^3$ are CH; and $X^2$ is $CR^1$; $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In another embodiment of Formula (IVc), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (IVc), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IVc), $X^2$ and $X^3$ are CH; and $X^1$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IVc), $X^2$ and $X^3$ are CH; and $X^1$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IVc), $X^2$ and $X^3$ are CH; and $X^1$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IVc), $X^2$ and $X^3$ are CH; and $X^1$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IVc), $X^2$ and $X^3$ are CH; and $X^1$ is $CR^1$; $R^1$ is NHC(O)$R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IVc), $X^2$ and $X^3$ are CH; and $X^1$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (IVc), $X^2$ and $X^3$ are CH; and $X^1$ is $CR^1$; and $R^1$ is $C(O)NH_2$. In another embodiment of Formula (IVc), $X^2$ and $X^3$ are CH; and $X^1$ is $CR^1$; and $R^1$ is F. In another embodiment of Formula (IVc), $X^2$ and $X^3$ are CH; and $X^1$ is $CR^1$; and $R^1$ is Cl. In another embodiment of Formula (IVc), $X^2$ and $X^3$ are CH; and $X^1$ is $CR^1$; and $R^1$ is Br. In another embodiment of Formula (IVc), $X^2$ and $X^3$ are CH; and $X^1$ is $CR^1$; and $R^1$ is CN. In another embodiment of Formula (IVc), $X^2$ and $X^3$ are CH; and $X^1$ is $CR^1$; and $R^1$ is $NH_2$. In another embodiment of Formula (IVc), $X^2$ and $X^3$ are CH; and $X^1$ is $CR^1$; and $R^1$ is $NO_2$. In another embodiment of Formula (IVc), $X^2$ and $X^3$ are CH; and $X^1$ is $CR^1$; and $R^1$ is $CF_3$. In another embodiment of Formula (IVc), $X^2$ and $X^3$ are CH; and $X^1$ is $CR^1$; and $R^1$ is C(O)OH. In another embodiment of Formula (IVc), $X^2$ and $X^3$ are CH; and $X^1$ is $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In another embodiment of Formula (IVc), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, NO$_2$, CF$_3$, or C(O)OH. In another embodiment of Formula (IVc), X$^1$ is CH; and X$^2$ and X$^3$ are CR$^1$; and R$^1$ is R$^3$, OR$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVc), X$^1$ is CH; and X$^2$ and X$^3$ are CR$^1$; R$^1$ is R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVc), X$^1$ is CH; and X$^2$ and X$^3$ are CR$^1$; R$^1$ is OR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVc), X$^1$ is CH; and X$^2$ and X$^3$ are CR$^1$; R$^1$ is C(O)OR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVc), X$^1$ is CH; and X$^2$ and X$^3$ are CR$^1$; R$^1$ is C(O)NHR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVc), X$^1$ is CH; and X$^2$ and X$^3$ are CR$^1$; R$^1$ is NHC(O)R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVc), X$^1$ is CH; and X$^2$ and X$^3$ are CR$^1$; R$^1$ is NHSO$_2$R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (IVc), X$^1$ is CH; and X$^2$ and X$^3$ are CR$^1$; and R$^1$ is C(O)NH$_2$. In another embodiment of Formula (IVc), X$^1$ is CH; and X$^2$ and X$^3$ are CR$^1$; and R$^1$ is F. In another embodiment of Formula (IVc), X$^1$ is CH; and X$^2$ and X$^3$ are CR$^1$; and R$^1$ is Cl. In another embodiment of Formula (IVc), X$^1$ is CH; and X$^2$ and X$^3$ are CR$^1$; and R$^1$ is Br. In another embodiment of Formula (IVc), X$^1$ is CH; and X$^2$ and X$^3$ are CR$^1$; and R$^1$ is CN. In another embodiment of Formula (IVc), X$^1$ is CH; and X$^2$ and X$^3$ are CR$^1$; and R$^1$ is NH$_2$. In another embodiment of Formula (IVc), X$^1$ is CH; and X$^2$ and X$^3$ are CR$^1$; and R$^1$ is NO$_2$. In another embodiment of Formula (IVc), X$^1$ is CH; and X$^2$ and X$^3$ are CR$^1$; and R$^1$ is CF$_3$. In another embodiment of Formula (IVc), X$^1$ is CH; and X$^2$ and X$^3$ are CR$^1$; and R$^1$ is C(O)OH. In another embodiment of Formula (IVc), X$^1$ is CH; and X$^2$ and X$^3$ are CR$^1$; and R$^1$ is C(O)R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; and R$^6$ is alkyl or heterocyclyl.

Still another embodiment pertains to compounds having Formula (IVc), which include
N-{4-[(4,4,4-trifluorobutanoyl)amino]phenyl}-1,3-dihydro-2H-isoindole-2-carboxamide;
N-{4-[(3-ethoxypropanoyl)amino]phenyl}-1,3-dihydro-2H-isoindole-2-carboxamide;
N-{4-[(4-phenylbutanoyl)amino]phenyl}-1,3-dihydro-2H-isoindole-2-carboxamide;
N-{4-[(4-methylpentanoyl)amino]phenyl}-1,3-dihydro-2H-isoindole-2-carboxamide;
N-(4-{[(benzyloxy)acetyl]amino}phenyl)-1,3-dihydro-2H-isoindole-2-carboxamide;
N-{4-[(3-phenylpropanoyl)amino]phenyl}-1,3-dihydro-2H-isoindole-2-carboxamide;
N-{4-[(3-phenoxypropanoyl)amino]phenyl}-1,3-dihydro-2H-isoindole-2-carboxamide;
N-(4-{[N-(2-furoyl)glycyl]amino}phenyl)-1,3-dihydro-2H-isoindole-2-carboxamide;
N-(4-{[4-(2-thienyl)butanoyl]amino}phenyl)-1,3-dihydro-2H-isoindole-2-carboxamide;
N-{4-[(4-oxo-4-phenylbutanoyl)amino]phenyl}-1,3-dihydro-2H-isoindole-2-carboxamide;
N-{4-[(N-benzoylglycyl)amino]phenyl}-1,3-dihydro-2H-isoindole-2-carboxamide;
N-{4-[(4-phenoxybutanoyl)amino]phenyl}-1,3-dihydro-2H-isoindole-2-carboxamide;
N-[4-(propionylamino)phenyl]-1,3-dihydro-2H-isoindole-2-carboxamide;
N-[4-(pentanoylamino)phenyl]-1,3-dihydro-2H-isoindole-2-carboxamide;
N-[4-(hexanoylamino)phenyl]-1,3-dihydro-2H-isoindole-2-carboxamide;
N-[4-(heptanoylamino)phenyl]-1,3-dihydro-2H-isoindole-2-carboxamide;
N-[4-(pent-4-enoylamino)phenyl]-1,3-dihydro-2H-isoindole-2-carboxamide;
N-{4-[(ethoxyacetyl)amino]phenyl}-1,3-dihydro-2H-isoindole-2-carboxamide;
N-(4-{[(2-methoxyethoxy)acetyl]amino}phenyl)-1,3-dihydro-2H-isoindole-2-carboxamide;
N-{4-[(cyclopropylacetyl)amino]phenyl}-1,3-dihydro-2H-isoindole-2-carboxamide;
N-{4-[(cyclopentylacetyl)amino]phenyl}-1,3-dihydro-2H-isoindole-2-carboxamide;
N-(4-{[3-(4-methylpiperazin-1-yl)propanoyl]amino}phenyl)-1,3-dihydro-2H-isoindole-2-carboxamide;
methyl 2-({4-[(cyclopentylacetyl)amino]phenyl}carbamoyl)isoindoline-5-carboxylate;
2-({4-[(cyclopentylacetyl)amino]phenyl}carbamoyl)isoindoline-5-carboxylic acid;
N-{4-[(cyclopentylacetyl)amino]phenyl}-5-(hydroxymethyl)-1,3-dihydro-2H-isoindole-2-carboxamide;
5-bromo-N-{4-[(cyclopentylacetyl)amino]phenyl}-1,3-dihydro-2H-isoindole-2-carboxamide;
5-cyano-N-{4-[(cyclopentylacetyl)amino]phenyl}-1,3-dihydro-2H-isoindole-2-carboxamide;
N$^2$-{4-[(cyclopentylacetyl)amino]phenyl}-1,3-dihydro-2H-isoindole-2,5-dicarboxamide;
N-{4-[(cyclopentylacetyl)amino]phenyl}-5-(1H-pyrazol-3-yl)-1,3-dihydro-2H-isoindole-2-carboxamide;
N-{4-[(cyclopentylacetyl)amino]phenyl}-5-(pyridin-3-yl)-1,3-dihydro-2H-isoindole-2-carboxamide;
N-{4-[(cyclopentylacetyl)amino]phenyl}-5-(1-methyl-1H-pyrazol-4-yl)-1,3-dihydro-2H-isoindole-2-carboxamide;
N$^2$-{4-[(cyclopentylacetyl)amino]phenyl}-N$^5$-(2-methoxyethyl)-1,3-dihydro-2H-isoindole-2,5-dicarboxamide;
N$^2$-{4-[(cyclopentylacetyl)amino]phenyl}-N$^5$-(2-hydroxyethyl)-1,3-dihydro-2H-isoindole-2,5-dicarboxamide;
5-(aminomethyl)-N-{4-[(cyclopentylacetyl)amino]phenyl}-1,3-dihydro-2H-isoindole-2-carboxamide;
N-{4-[(cyclopentylacetyl)amino]phenyl}-5-methoxy-1,3-dihydro-2H-isoindole-2-carboxamide;
N-{4-[(cyclopentylacetyl)amino]phenyl}-5-(pyridin-4-yl)-1,3-dihydro-2H-isoindole-2-carboxamide;

5-(hydroxymethyl)-N-{4-[(tetrahydrofuran-3-ylacetyl) amino]phenyl}-1,3-dihydro-2H-isoindole-2-carboxamide;

5-(hydroxymethyl)-N-(4-{[(2-methoxyethoxy)acetyl] amino}phenyl)-1,3-dihydro-2H-isoindole-2-carboxamide;

5-(hydroxymethyl)-N-{4-[(tetrahydrofuran-2-ylacetyl) amino]phenyl}-1,3-dihydro-2H-isoindole-2-carboxamide;

N-{4-[(ethoxyacetyl)amino]phenyl}-5-(hydroxymethyl)-1, 3-dihydro-2H-isoindole-2-carboxamide;

5-(hydroxymethyl)-N-{4-[(tetrahydro-2H-pyran-4-ylacetyl) amino]phenyl}-1,3-dihydro-2H-isoindole-2-carboxamide;

5-(hydroxymethyl)-N-{4-[(morpholin-4-ylacetyl)amino] phenyl}-1,3-dihydro-2H-isoindole-2-carboxamide;

N-{4-[(cyclopentylacetyl)amino]phenyl}-5-fluoro-1,3-dihydro-2H-isoindole-2-carboxamide;

N-{4-[(cyclopentylacetyl)amino]phenyl}-5-(trifluoromethyl)-1,3-dihydro-2H-isoindole-2-carboxamide;

4-cyano-N-{4-[(cyclopentylacetyl)amino]phenyl}-1,3-dihydro-2H-isoindole-2-carboxamide;

N-{4-[(cyclopentylacetyl)amino]phenyl}-5-methyl-1,3-dihydro-2H-isoindole-2-carboxamide;

4-chloro-N-{4-[(cyclopentylacetyl)amino]phenyl}-1,3-dihydro-2H-isoindole-2-carboxamide;

5-chloro-N-{4-[(cyclopentylacetyl)amino]phenyl}-1,3-dihydro-2H-isoindole-2-carboxamide;

5-acetyl-N-{4-[(cyclopentylacetyl)amino]phenyl}-1,3-dihydro-2H-isoindole-2-carboxamide;

N-{4-[(cyclopentylacetyl)amino]phenyl}-5-(1-hydroxyethyl)-1,3-dihydro-2H-isoindole-2-carboxamide;

N-[4-(butyrylamino)phenyl]-5-cyano-1,3-dihydro-2H-isoindole-2-carboxamide;

–4-yl]phenyl}-1,3-dihydro-2H-pyrrolo[3,4-c]pyridine-2-carboxamide;

5-(acetamidomethyl)-N-{4-[(cyclopentylacetyl)amino]phenyl}-1,3-dihydro-2H-isoindole-2-carboxamide;

N-{4-[(cyclopentylacetyl)amino]phenyl}-5-(2-hydroxypropan-2-yl)-1,3-dihydro-2H-isoindole-2-carboxamide;

N-{4-[(cyclopentylacetyl)amino]phenyl}-1,3-dihydro-2H-pyrrolo[3,4-c]pyridine-2-carboxamide;

N-{4-[(cyclopentylacetyl)amino]phenyl}-5-(methoxymethyl)-1,3-dihydro-2H-isoindole-2-carboxamide;

N-{4-[(3-ethoxypropanoyl)amino]phenyl}-1,3-dihydro-2H-pyrrolo[3,4-c]pyridine-2-carboxamide;

N-(4-{[(1-acetylpiperidin-4-yl)carbonyl]amino}phenyl)-1, 3-dihydro-2H-pyrrolo[3,4-c]pyridine-2-carboxamide;

N-{4-[(ethoxyacetyl)amino]phenyl}-1,3-dihydro-2H-pyrrolo[3,4-c]pyridine-2-carboxamide;

N-{4-[(tetrahydrofuran-2-ylcarbonyl)amino]phenyl}-1,3-dihydro-2H-pyrrolo[3,4-c]pyridine-2-carboxamide;

N-{4-[(tetrahydrofuran-3-ylcarbonyl)amino]phenyl}-1,3-dihydro-2H-pyrrolo[3,4-c]pyridine-2-carboxamide;

N-{4-[(cyclopentylcarbonyl)amino]phenyl}-1,3-dihydro-2H-pyrrolo[3,4-c]pyridine-2-carboxamide;

N-{4-[(bicyclo[2.2.1]hept-2-ylacetyl)amino]phenyl}-1,3-dihydro-2H-pyrrolo[3,4-c]pyridine-2-carboxamide;

N-{4-[(1,3-thiazol-5-ylcarbonyl)amino]phenyl}-1,3-dihydro-2H-pyrrolo[3,4-c]pyridine-2-carboxamide;

N-(4-{[(4-oxo-4,5,6,7-tetrahydro-1-benzo furan-3-yl)carbonyl]amino}phenyl)-1,3-dihydro-2H-pyrrolo[3,4-c]pyridine-2-carboxamide; and pharmaceutically acceptable salts thereof.

Embodiments of Formula (Vc)

In another aspect, the present invention provides compounds of Formula (Vc)

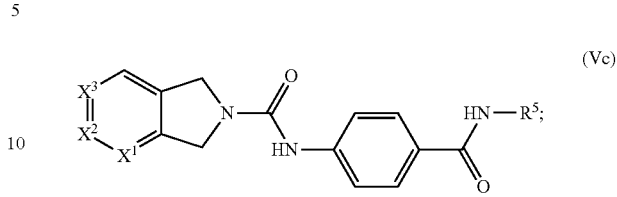

and pharmaceutically acceptable salts thereof; wherein $X^1$, $X^2$, $X^3$, and $R^5$ are as described herein for Formula (Ic).

In one embodiment of formula (Vc), $X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or
$X^1$ is CH; $X^2$ is N; and $X^3$ is $CR^1$; or
$X^1$ is $CR^1$; $X^2$ is N; and $X^3$ is CH; or
$X^1$ is N; $X^2$ is $CR^1$; and $X^3$ is CH; or
$X^1$ is N; $X^2$ is $CR^1$; and $X^3$ is N;

$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, C(O)H, $CF_3$, C(O)OH, or $C(O)NH_2$;

$R^3$, at each occurrence, is independently selected alkyl, alkenyl, alkynyl, aryl, or heterocyclyl; wherein each $R^3$ alkyl, alkenyl, and alkynyl is optionally substituted with one, two, three or four independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, C(O)H, C(O)OH, OH, (O), CN, $N_3$, $NO_2$, $CF_3$, $CF_2CF_3$, $OCF_3$, $OCF_2CF_3$, F, Cl, Br or I;

$R^5$, at each occurrence, is independently selected alkyl, alkenyl, alkynyl, aryl, heterocyclyl, cycloalkyl, or cycloalkenyl; wherein each $R^5$ alkyl, alkenyl, and alkynyl is optionally substituted with one, two, three or four independently selected $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, C(O)H, C(O)OH, OH, (O), CN, $N_3$, $NO_2$, $CF_3$, $CF_2CF_3$, $OCF_3$, $OCF_2CF_3$, F, Cl, Br or I;

$R^6$, at each occurrence, is independently selected alkyl, alkenyl, alkynyl, aryl, heterocyclyl, cycloalkyl, or cycloalkenyl; wherein each $R^6$ alkyl, alkenyl, and alkynyl is optionally substituted with one, two, three or four independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, OH, (O), C(O)OH, $N_3$, CN, $NH_2$, $CF_3$, $CF_2CF_3$, F, Cl, Br or I;

$R^9$, at each occurrence, is independently selected alkyl, alkenyl, alkynyl, aryl, heterocyclyl, cycloalkyl, or cycloalkenyl; wherein each $R^9$ alkyl, alkenyl, and alkynyl is optionally substituted with one, two, three or four independently selected alkoxy, OH, cycloalkyl, aryl, or heterocyclyl;

$R^{10}$, at each occurrence, is independently selected alkyl, alkenyl, alkynyl, aryl, heterocyclyl, cycloalkyl, or cycloalkenyl;

wherein the cyclic moieties represented by $R^3$, $R^5$, $R^6$, $R^9$, and $R^{10}$ are optionally substituted with one, two, three, four, five, or six independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, $C(O)H$, $C(O)OH$, $OH$, $CN$, $N_3$, $NO_2$, $CF_3$, $CF_2CF_3$, $OCF_3$, $OCF_2CF_3$, $SCF_3$, F, Cl, Br or I;

$R^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, or cycloalkenyl; wherein each $R^{13}$ alkyl, alkenyl, and alkynyl is optionally substituted with one, two, three or four independently selected $R^{14}$, $OR^{14}$, $SR^{14}$, $S(O)R^{14}$, $SO_2R^{14}$, $C(O)R^{14}$, $OC(O)R^{14}$, $OC(O)OR^{14}$, $NH_2$, $NHR^{14}$, $N(R^{14})_2$, $NHC(O)R^{14}$, $NR^{14}C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, $C(O)H$, $C(O)OH$, $OH$, (O), $CN$, $N_3$, $NO_2$, $CF_3$, $CF_2CF_3$, $OCF_3$, $OCF_2CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, and cycloalkenyl is optionally substituted with one, two, three or four independently selected $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $C(O)H$, $C(O)OH$, $OH$, $CN$, $N_3$, $NO_2$, $CF_3$, $CF_2CF_3$, $OCF_3$, $OCF_2CF_3$, F, Cl, Br or I;

$R^{14}$, at each occurrence, is independently selected alkyl, alkenyl, alkynyl, aryl, heterocyclyl, cycloalkyl, or cycloalkenyl; wherein each $R^{14}$ alkyl, alkenyl, and alkynyl is optionally substituted with one, two, three or four independently selected heterocyclyl, alkoxy, $NH_2$, $SO_2NH_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I; wherein each $R^{14}$ aryl, heterocyclyl, cycloalkyl, and cycloalkenyl is optionally substituted with one, two, three or four independently selected $R^{16}$, $OR^{16}$, OH, F, Cl, Br, or I;

$R^{15}$, at each occurrence, is independently selected alkyl, wherein the $R^{15}$ alkyl is optionally substituted with one, two, three or four alkoxy; and $R^{16}$, at each occurrence, is independently selected alkyl, wherein the $R^{16}$ alkyl is optionally substituted with one, two, three or four alkoxy;

with the proviso that when $R^{13}$ is piperidinyl, it is substituted piperidinyl; and with the proviso that when $R^{13}$ is pyrrolinyl, at least one of $X^1$, $X^2$, and $X^3$ is N.

In one embodiment of Formula (Vc), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N; or $X^1$ is CH; $X^2$ is N; and $X^3$ is $CR^1$; or $X^1$ is $CR^1$; $X^2$ is N; and $X^3$ is CH; or $X^1$ is N; $X^2$ is $CR^1$; and $X^3$ is CH; or $X^1$ is N; $X^2$ is $CR^1$; and $X^3$ is N. In another embodiment of Formula (Vc), $X^1$, $X^2$, and $X^3$ are CH. In another embodiment of Formula (Vc), $X^1$ and $X^3$ are CH; and $X^2$ is N. In another embodiment of Formula (Vc), $X^1$ and $X^3$ are CH; and $X^2$ is $CR^1$. In another embodiment of Formula (Vc), $X^2$ and $X^3$ are CH; and $X^1$ is $CR^1$. In another embodiment of Formula (Vc), $X^1$ is CH; and $X^2$ and $X^3$ are $CR^1$. In another embodiment of Formula (Vc), $X^2$ is CH; and $X^1$ and $X^3$ are N. In another embodiment of Formula (Vc), $X^2$ and $X^3$ are CH; and $X^1$ is N. In another embodiment of Formula (Vc), $X^1$ is CH; $X^2$ is N; and $X^3$ is $CR^1$. In another embodiment of Formula (Vc), $X^1$ is $CR^1$; $X^2$ is N; and $X^3$ is CH. In another embodiment of Formula (Vc), $X^1$ is N; $X^2$ is $CR^1$; and $X^3$ is CH. In another embodiment of Formula (Vc), $X^1$ is N; $X^2$ is $CR^1$; and $X^3$ is N.

In another embodiment of Formula (Vc), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (Vc), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (Vc), $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (Vc), $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (Vc), $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (Vc), $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vc), $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vc), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vc), $R^1$ is $C(O)NH_2$. In another embodiment of Formula (Vc), $R^1$ is F. In another embodiment of Formula (Vc), $R^1$ is Cl. In another embodiment of Formula (Vc), $R^1$ is Br. In another embodiment of Formula (Vc), $R^1$ is CN. In another embodiment of Formula (Vc), $R^1$ is $NH_2$. In another embodiment of Formula (Vc), $R^1$ is $NO_2$.

In another embodiment of Formula (Vc), $R^1$ is $CF_3$. In another embodiment of Formula (Vc), $R^1$ is C(O)OH. In another embodiment of Formula (Vc), $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl.

In another embodiment of Formula (Vc), $X^1$ and $X^3$ are CH; and $X^2$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (Vc), $X^1$ and $X^3$ are CH; and $X^2$ is $CR^1$; $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vc), $X^1$ and $X^3$ are CH; and $X^2$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vc), $X^1$ and $X^3$ are CH; and $X^2$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vc), $X^1$ and $X^3$ are CH; and $X^2$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vc), $X^1$ and $X^3$ are CH; and $X^2$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vc), $X^1$ and $X^3$ are CH; and $X^2$ is $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vc), $X^1$ and $X^3$ are CH; and $X^2$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vc), $X^1$ and $X^3$ are CH; and $X^2$ is $CR^1$; and $R^1$ is $C(O)NH_2$. In another embodiment of Formula (Vc), $X^1$ and $X^3$ are CH; and $X^2$ is $CR^1$; and $R^1$ is F. In another embodiment of Formula (Vc), $X^1$ and $X^3$ are CH; and $X^2$ is $CR^1$; and $R^1$ is Cl. In another embodiment of Formula (Vc), $X^1$ and $X^3$ are CH; and $X^2$ is $CR^1$; and $R^1$ is Br. In another embodiment of Formula (Vc), $X^1$ and $X^3$ are CH; and $X^2$ is $CR^1$; and $R^1$ is CN. In another embodiment of Formula (Vc), $X^1$ and $X^3$ are CH; and $X^2$ is $CR^1$; and $R^1$ is $NH_2$. In another embodiment of Formula (Vc), $X^1$ and $X^3$ are CH; and $X^2$ is $CR^1$; and $R^1$ is $NO_2$. In another embodiment of Formula (Vc), $X^1$ and $X^3$ are CH; and $X^2$ is $CR^1$; and $R^1$ is $CF_3$. In another embodiment of Formula (Vc), $X^1$ and $X^3$ are CH; and $X^2$ is $CR^1$; and $R^1$ is C(O)OH. In another embodiment of Formula (Vc), $X^1$ and $X^3$ are CH; and $X^2$ is $CR^1$; $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl.

In another embodiment of Formula (Vc), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (Vc), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vc), $X^2$ and $X^3$ are CH; and $X^1$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vc), $X^2$ and $X^3$ are CH; and $X^1$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vc), $X^2$ and $X^3$ are CH; and $X^1$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vc), $X^2$ and $X^3$ are CH; and $X^1$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vc), $X^2$ and $X^3$ are CH; and $X^1$ is $CR^1$; $R^1$ is NHC(O)$R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vc), $X^2$ and $X^3$ are CH; and $X^1$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (Vc), $X^2$ and $X^3$ are CH; and $X^1$ is $CR^1$; and $R^1$ is $C(O)NH_2$. In another embodiment of Formula (Vc), $X^2$ and $X^3$ are CH; and $X^1$ is $CR^1$; and $R^1$ is F. In another embodiment of Formula (Vc), $X^2$ and $X^3$ are CH; and $X^1$ is $CR^1$; and $R^1$ is Cl. In another embodiment of Formula (Vc), $X^2$ and $X^3$ are CH; and $X^1$ is $CR^1$; and $R^1$ is Br. In another embodiment of Formula (Vc), $X^2$ and $X^3$ are CH; and $X^1$ is $CR^1$; and $R^1$ is CN. In another embodiment of Formula (Vc), $X^2$ and $X^3$ are CH; and $X^1$ is $CR^1$; and $R^1$ is $NH_2$. In another embodiment of Formula (Vc), $X^2$ and $X^3$ are CH; and $X^1$ is $CR^1$; and $R^1$ is $NO_2$. In another embodiment of Formula (Vc), $X^2$ and $X^3$ are CH; and $X^1$ is $CR^1$; and $R^1$ is $CF_3$. In another embodiment of Formula (Vc), $X^2$ and $X^3$ are CH; and $X^1$ is $CR^1$; and $R^1$ is C(O)OH. In another embodiment of Formula (Vc), $X^2$ and $X^3$ are CH; and $X^1$ is $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In another embodiment of Formula (Vc), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, NO$_2$, CF$_3$, or C(O)OH. In another embodiment of Formula (Vc), X$^1$ is CH; and X$^2$ and X$^3$ are CR$^1$; and R$^1$ is R$^3$, OR$^3$, C(O)OR$^3$, C(O)NH$_2$, C(O)NHR$^3$, NHC(O)R$^3$, NHSO$_2$R$^3$, F, Cl, Br, I, CN, NH$_2$, NO$_2$, CF$_3$, or C(O)OH; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (Vc), X$^1$ is CH; and X$^2$ and X$^3$ are CR$^1$; R$^1$ is R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (Vc), X$^1$ is CH; and X$^2$ and X$^3$ are CR$^1$; R$^1$ is OR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (Vc), X$^1$ is CH; and X$^2$ and X$^3$ are CR$^1$; R$^1$ is C(O)OR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (Vc), X$^1$ is CH; and X$^2$ and X$^3$ are CR$^1$; R$^1$ is C(O)NHR$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (Vc), X$^1$ is CH; and X$^2$ and X$^3$ are CR$^1$; R$^1$ is NHC(O)R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (Vc), X$^1$ is CH; and X$^2$ and X$^3$ are CR$^1$; R$^1$ is NHSO$_2$R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; wherein R$^6$ is alkyl or heterocyclyl. In another embodiment of Formula (Vc), X$^1$ is CH; and X$^2$ and X$^3$ are CR$^1$; and R$^1$ is C(O)NH$_2$. In another embodiment of Formula (Vc), X$^1$ is CH; and X$^2$ and X$^3$ are CR$^1$; and R$^1$ is F. In another embodiment of Formula (Vc), X$^1$ is CH; and X$^2$ and X$^3$ are CR$^1$; and R$^1$ is Cl. In another embodiment of Formula (Vc), X$^1$ is CH; and X$^2$ and X$^3$ are CR$^1$; and R$^1$ is Br. In another embodiment of Formula (Vc), X$^1$ is CH; and X$^2$ and X$^3$ are CR$^1$; and R$^1$ is CN. In another embodiment of Formula (Vc), X$^1$ is CH; and X$^2$ and X$^3$ are CR$^1$; and R$^1$ is NH$_2$. In another embodiment of Formula (Vc), X$^1$ is CH; and X$^2$ and X$^3$ are CR$^1$; and R$^1$ is NO$_2$. In another embodiment of Formula (Vc), X$^1$ is CH; and X$^2$ and X$^3$ are CR$^1$; and R$^1$ is CF$_3$. In another embodiment of Formula (Vc), X$^1$ is CH; and X$^2$ and X$^3$ are CR$^1$; and R$^1$ is C(O)OH. In another embodiment of Formula (Vc), X$^1$ is CH; and X$^2$ and X$^3$ are CR$^1$; and R$^1$ is C(O)R$^3$; wherein R$^3$ is alkyl, alkenyl, or heterocyclyl; wherein each alkyl is optionally substituted with one or more independently selected R$^6$, OR$^6$, NH$_2$, NHC(O)R$^6$, N(R$^6$)$_2$, or OH; and R$^6$ is alkyl or heterocyclyl.

Still another embodiment pertains to compounds having Formula (Vc), which include N-{4-[(3-phenylpropyl)carbamoyl]phenyl}-1,3-dihydro-2H-isoindole-2-carboxamide;
N-(4-{[4-(aminomethyl)benzyl]carbamoyl}phenyl)-5-fluoro-1,3-dihydro-2H-isoindole-2-carboxamide;
5-cyano-N-{4-[(3-phenylpropyl)carbamoyl]phenyl}-1,3-dihydro-2H-isoindole-2-carboxamide;
N-{4-[(cyclopentylmethyl)carbamoyl]phenyl}-5-fluoro-1,3-dihydro-2H-isoindole-2-carboxamide;
5-cyano-N-[4-(propylcarbamoyl)phenyl]-1,3-dihydro-2H-isoindole-2-carboxamide;
5-fluoro-N-{4-[(pyridin-2-ylmethyl)carbamoyl]phenyl}-1,3-dihydro-2H-isoindole-2-carboxamide;
N-[4-(benzylcarbamoyl)phenyl]-5-fluoro-1,3-dihydro-2H-isoindole-2-carboxamide;
N-{4-[(3,4-dimethoxybenzyl)carbamoyl]phenyl}-1,3-dihydro-2H-isoindole-2-carboxamide;
N-{4-[(2,3-dimethoxybenzyl)carbamoyl]phenyl}-1,3-dihydro-2H-isoindole-2-carboxamide;
5-fluoro-N-{4-[(3-phenylpropyl)carbamoyl]phenyl}-1,3-dihydro-2H-isoindole-2-carboxamide;
N-{4-[(2,3-dihydro-1,4-benzo dioxin-5-ylmethyl)carbamoyl]phenyl}-1,3-dihydro-2H-isoindole-2-carboxamide;
5-fluoro-N-(4-{[1-(3-methylbutyl)-1H-pyrazol-4-yl]carbamoyl}phenyl)-1,3-dihydro-2H-isoindole-2-carboxamide;
N-{4-[(2-fluorobenzyl)carbamoyl]phenyl}-1,3-dihydro-2H-isoindole-2-carboxamide;
5-fluoro-N-{4-[(3-methylbutyl)carbamoyl]phenyl}-1,3-dihydro-2H-isoindole-2-carboxamide;
N-{4-[(2-methoxybenzyl)carbamoyl]phenyl}-1,3-dihydro-2H-isoindole-2-carboxamide;
N-{4-[(3-fluorobenzyl)carbamoyl]phenyl}-1,3-dihydro-2H-isoindole-2-carboxamide;
5-fluoro-N-(4-{[3-(2-oxopyrrolidin-1-yl)propyl]carbamoyl}-phenyl)-1,3-dihydro-2H-isoindole-2-carboxamide;
5-cyano-N-{4-[(3-methylbutyl)carbamoyl]phenyl}-1,3-dihydro-2H-isoindole-2-carboxamide;
N-{4-[(cyclopentylmethyl)carbamoyl]phenyl}-5-methyl-1,3-dihydro-2H-isoindole-2-carboxamide;
N-{4-[(4-fluorobenzyl)carbamoyl]phenyl}-1,3-dihydro-2H-isoindole-2-carboxamide;
N-{4-[(3,5-dimethoxybenzyl)carbamoyl]phenyl}-1,3-dihydro-2H-isoindole-2-carboxamide;
5-fluoro-N-{4-[(tetrahydrofuran-3-ylmethyl)carbamoyl]phenyl}-1,3-dihydro-2H-isoindole-2-carboxamide;
N-{4-[(2,2-dimethylpropyl)carbamoyl]phenyl}-1,3-dihydro-2H-isoindole-2-carboxamide;
5-fluoro-N-(4-{[2-(2-oxopyrrolidin-1-yl)ethyl]carbamoyl}phenyl)-1,3-dihydro-2H-isoindole-2-carboxamide;
N-(4-{[4-(trifluoromethoxy)benzyl]carbamoyl}phenyl)-1,3-dihydro-2H-isoindole-2-carboxamide;
N-(4-{[3-fluoro-5-(trifluoromethyl)benzyl]carbamoyl}phenyl)-1,3-dihydro-2H-isoindole-2-carboxamide;
N-{4-[(3-methylbutyl)carbamoyl]phenyl}-1,3-dihydro-2H-isoindole-2-carboxamide;
5-methoxy-N-{4-[(3-phenylpropyl)carbamoyl]phenyl}-1,3-dihydro-2H-isoindole-2-carboxamide;
N-{4-[(4-chlorobenzyl)carbamoyl]phenyl}-1,3-dihydro-2H-isoindole-2-carboxamide;
N-{4-[(cyclopentylmethyl)carbamoyl]phenyl}-1,3-dihydro-2H-isoindole-2-carboxamide;
N-{4-[(3,4,5-trimethoxybenzyl)carbamoyl]phenyl}-1,3-dihydro-2H-isoindole-2-carboxamide;
5-nitro-N-[4-(propylcarbamoyl)phenyl]-1,3-dihydro-2H-isoindole-2-carboxamide;
5-methyl-N-{4-[(3-methylbutyl)carbamoyl]phenyl}-1,3-dihydro-2H-isoindole-2-carboxamide;
N-{4-[(4-methoxybenzyl)carbamoyl]phenyl}-1,3-dihydro-2H-isoindole-2-carboxamide;
N-{4-[(2-thienylmethyl)carbamoyl]phenyl}-1,3-dihydro-2H-isoindole-2-carboxamide;
N-{4-[(1-ethyl-1H-pyrazol-4-yl)carbamoyl]phenyl}-5-fluoro-1,3-dihydro-2H-isoindole-2-carboxamide;

N-{4-[(1-benzyl-1H-pyrazol-4-yl)carbamoyl]phenyl}-5-fluoro-1,3-dihydro-2H-isoindole-2-carboxamide;
N-{4-[(3,3-dimethylbutyl)carbamoyl]phenyl}-1,3-dihydro-2H-isoindole-2-carboxamide;
N-(4-{[(2R)-tetrahydrofuran-2-ylmethyl]carbamoyl}phenyl)-1,3-dihydro-2H-isoindole-2-carboxamide;
N-(4-{[2-(2,3-dimethoxyphenyl)ethyl]carbamoyl}phenyl)-1,3-dihydro-2H-isoindole-2-carboxamide;
N-{4-[(3-thienylmethyl)carbamoyl]phenyl}-1,3-dihydro-2H-isoindole-2-carboxamide;
5-methoxy-N-{4-[(3-methylbutyl)carbamoyl]phenyl}-1,3-dihydro-2H-isoindole-2-carboxamide;
N-{4-[(pyridin-2-ylmethyl)carbamoyl]phenyl}-1,3-dihydro-2H-isoindole-2-carboxamide;
5-fluoro-N-(4-{[2-(2-thienyl)ethyl]carbamoyl}phenyl)-1,3-dihydro-2H-isoindole-2-carboxamide;
N-(4-{[(2S)-tetrahydrofuran-2-ylmethyl]carbamoyl}phenyl)-1,3-dihydro-2H-isoindole-2-carboxamide;
N-(4-{[1-(3-methylbutyl)-1H-pyrazol-4-yl]carbamoyl}phenyl)-1,3-dihydro-2H-isoindole-2-carboxamide;
N-{4-[(6-aminohexyl)carbamoyl]phenyl}-1,3-dihydro-2H-isoindole-2-carboxamide;
4-chloro-N-{4-[(3-methylbutyl)carbamoyl]phenyl}-1,3-dihydro-2H-isoindole-2-carboxamide;
N-(4-{[2-(2-thienyl)ethyl]carbamoyl}phenyl)-1,3-dihydro-2H-isoindole-2-carboxamide;
N-{4-[(1,3-benzodioxol-5-ylmethyl)carbamoyl]phenyl}-1,3-dihydro-2H-isoindole-2-carboxamide;
N-{4-[(3-methoxybenzyl)carbamoyl]phenyl}-1,3-dihydro-2H-isoindole-2-carboxamide;
N-[4-(benzylcarbamoyl)phenyl]-1,3-dihydro-2H-isoindole-2-carboxamide;
N-{4-[(pyrimidin-4-ylmethyl)carbamoyl]phenyl}-1,3-dihydro-2H-isoindole-2-carboxamide;
N-{4-[(2-methylbutyl)carbamoyl]phenyl}-1,3-dihydro-2H-isoindole-2-carboxamide;
N-{4-[(3-butoxypropyl)carbamoyl]phenyl}-1,3-dihydro-2H-isoindole-2-carboxamide;
N-(4-{[(1S)-2-hydroxy-1-phenylethyl]carbamoyl}phenyl)-1,3-dihydro-2H-isoindole-2-carboxamide;
N-(4-{[2-(3,4-dihydroxyphenyl)ethyl]carbamoyl}phenyl)-1,3-dihydro-2H-isoindole-2-carboxamide;
N-{4-[(3-propoxypropyl)carbamoyl]phenyl}-1,3-dihydro-2H-isoindole-2-carboxamide;
N-{4-[(3-furylmethyl)carbamoyl]phenyl}-1,3-dihydro-2H-isoindole-2-carboxamide;
N-{4-[(3-hydroxy-2-methylphenyl)carbamoyl]phenyl}-1,3-dihydro-2H-isoindole-2-carboxamide;
N-{4-[(3-methylbutyl)carbamoyl]phenyl}-5-(trifluoromethyl)-1,3-dihydro-2H-isoindole-2-carboxamide;
N-{4-[(3-methyl-1H-indazol-5-yl)carbamoyl]phenyl}-1,3-dihydro-2H-isoindole-2-carboxamide;
N-{4-[(3-ethoxypropyl)carbamoyl]phenyl}-1,3-dihydro-2H-isoindole-2-carboxamide;
N-(4-{[2-(2,5-dimethoxyphenyl)ethyl]carbamoyl}phenyl)-1,3-dihydro-2H-isoindole-2-carboxamide;
N-{4-[(tetrahydrofuran-3-ylmethyl)carbamoyl]phenyl}-1,3-dihydro-2H-isoindole-2-carboxamide;
N-{4-[(1-benzyl-1H-pyrazol-4-yl)carbamoyl]phenyl}-1,3-dihydro-2H-isoindole-2-carboxamide;
methyl 5-({4-[(1,3-dihydro-2H-isoindol-2-ylcarbonyl)amino]benzoyl}amino)-1H-indazole-3-carboxylate;
N-(4-{[2-(2-oxopyrrolidin-1-yl)ethyl]carbamoyl}phenyl)-1,3-dihydro-2H-isoindole-2-carboxamide;
N-{4-[(pyridin-4-ylmethyl)carbamoyl]phenyl}-1,3-dihydro-2H-isoindole-2-carboxamide;
N-(4-{[2-(1H-indol-3-yl)ethyl]carbamoyl}phenyl)-1,3-dihydro-2H-isoindole-2-carboxamide;
N-(4-{[4-(trifluoromethyl)benzyl]carbamoyl}phenyl)-1,3-dihydro-2H-isoindole-2-carboxamide;
N-{4-[(3,5-dimethoxyphenyl)carbamoyl]phenyl}-1,3-dihydro-2H-isoindole-2-carboxamide;
N-{4-[(pyridin-3-ylmethyl)carbamoyl]phenyl}-1,3-dihydro-2H-isoindole-2-carboxamide;
N-[4-(2,3-dihydro-1,4-benzodioxin-6-ylcarbamoyl)phenyl]-1,3-dihydro-2H-isoindole-2-carboxamide;
N-(4-{[2-(5-methoxy-1H-indol-3-yl)ethyl]carbamoyl}phenyl)-1,3-dihydro-2H-isoindole-2-carboxamide;
N-{4-[(3-aminobenzyl)carbamoyl]phenyl}-1,3-dihydro-2H-isoindole-2-carboxamide;
N-(4-{[2-(2-chlorophenyl)ethyl]carbamoyl}phenyl)-1,3-dihydro-2H-isoindole-2-carboxamide;
N-(4-{[(2R)-1-hydroxy-4-methylpentan-2-yl]carbamoyl}phenyl)-1,3-dihydro-2H-isoindole-2-carboxamide;
N-{4-[(2-propoxyethyl)carbamoyl]phenyl}-1,3-dihydro-2H-isoindole-2-carboxamide;
N-{4-[(3-isobutoxypropyl)carbamoyl]phenyl}-1,3-dihydro-2H-isoindole-2-carboxamide;
N-{4-[(3,4,5-trimethoxyphenyl)carbamoyl]phenyl}-1,3-dihydro-2H-isoindole-2-carboxamide;
N-{4-[(4-methylpiperidin-1-yl)carbonyl]phenyl}-1,3-dihydro-2H-isoindole-2-carboxamide;
N-[4-({2-[4-(dimethylamino)phenyl]ethyl}carbamoyl)phenyl]-1,3-dihydro-2H-isoindole-2-carboxamide;
N-(4-{[3-(trifluoromethoxy)benzyl]carbamoyl}phenyl)-1,3-dihydro-2H-isoindole-2-carboxamide;
N-(4-{[(1R)-3-hydroxy-1-phenylpropyl]carbamoyl}phenyl)-1,3-dihydro-2H-isoindole-2-carboxamide;
N-{4-[(3-cyanophenyl)carbamoyl]phenyl}-1,3-dihydro-2H-isoindole-2-carboxamide;
N-{4-[(3-fluoro-4-methoxyphenyl)carbamoyl]phenyl}-1,3-dihydro-2H-isoindole-2-carboxamide;
N-{4-[(2,3-dimethoxyphenyl)carbamoyl]phenyl}-1,3-dihydro-2H-isoindole-2-carboxamide;
N-(4-{[2-(2-fluorophenyl)ethyl]carbamoyl}phenyl)-1,3-dihydro-2H-isoindole-2-carboxamide;
N-[4-(isobutylcarbamoyl)phenyl]-1,3-dihydro-2H-isoindole-2-carboxamide;
N-(4-{[2-(1,3-benzodioxol-5-yl)ethyl]carbamoyl}phenyl)-1,3-dihydro-2H-isoindole-2-carboxamide;
N-(4-{[2-(2-methoxyphenyl)ethyl]carbamoyl}phenyl)-1,3-dihydro-2H-isoindole-2-carboxamide;
N-[4-(butylcarbamoyl)phenyl]-1,3-dihydro-2H-isoindole-2-carboxamide;
N-{4-[(2-isopropoxyethyl)carbamoyl]phenyl}-1,3-dihydro-2H-isoindole-2-carboxamide;
N-{4-[(3-isopropoxypropyl)carbamoyl]phenyl}-1,3-dihydro-2H-isoindole-2-carboxamide;
4-chloro-N-{4-[(3-phenylpropyl)carbamoyl]phenyl}-1,3-dihydro-2H-isoindole-2-carboxamide;
N-(4-{[2-(4-methoxyphenyl)ethyl]carbamoyl}phenyl)-1,3-dihydro-2H-isoindole-2-carboxamide;
N-{4-[(3-methoxypropyl)carbamoyl]phenyl}-1,3-dihydro-2H-isoindole-2-carboxamide;
N-(4-{[2-(4-fluorophenyl)ethyl]carbamoyl}phenyl)-1,3-dihydro-2H-isoindole-2-carboxamide;
N-(4-{[3-(2-oxopyrrolidin-1-yl)propyl]carbamoyl}phenyl)-1,3-dihydro-2H-isoindole-2-carboxamide;

N-{4-[(2,4-dimethoxyphenyl)carbamoyl]phenyl}-1,3-dihydro-2H-isoindole-2-carboxamide;
N²-[4-(propylcarbamoyl)phenyl]-1,3-dihydro-2H-isoindole-2,5-dicarboxamide;
N-{4-[(2-phenoxyethyl)carbamoyl]phenyl}-1,3-dihydro-2H-isoindole-2-carboxamide;
N-(4-{[2-(4-hydroxyphenyl)ethyl]carbamoyl}phenyl)-1,3-dihydro-2H-isoindole-2-carboxamide;
N-(4-{[2-(3-fluorophenyl)ethyl]carbamoyl}phenyl)-1,3-dihydro-2H-isoindole-2-carboxamide;
N-[4-({1-[(3S)-tetrahydro furan-3-yl]-1H-pyrazol-4-yl}carbamoyl)phenyl]-1,3-dihydro-2H-isoindole-2-carboxamide;
5-methyl-N-{4-[(3-phenylpropyl)carbamoyl]phenyl}-1,3-dihydro-2H-isoindole-2-carboxamide;
N-{4-[(2-phenylethyl)carbamoyl]phenyl}-1,3-dihydro-2H-isoindole-2-carboxamide;
N-(4-{[2-(2,4-dimethoxyphenyl)ethyl]carbamoyl}phenyl)-1,3-dihydro-2H-isoindole-2-carboxamide;
N-(4-{[3-(methylthio)propyl]carbamoyl}phenyl)-1,3-dihydro-2H-isoindole-2-carboxamide;
N-{4-[(2-ethoxyethyl)carbamoyl]phenyl}-1,3-dihydro-2H-isoindole-2-carboxamide;
N-{4-[(2-fluorophenyl)carbamoyl]phenyl}-1,3-dihydro-2H-isoindole-2-carboxamide;
N-(4-{[2-(pyridin-3-yl)ethyl]carbamoyl}phenyl)-1,3-dihydro-2H-isoindole-2-carboxamide;
N-[4-({4-[(trifluoromethyl)thio]benzyl}carbamoyl)phenyl]-1,3-dihydro-2H-isoindole-2-carboxamide;
N-{4-[(3,4-dimethoxyphenyl)carbamoyl]phenyl}-1,3-dihydro-2H-isoindole-2-carboxamide;
N-(4-{[3-(1H-imidazol-1-yl)propyl]carbamoyl}phenyl)-1,3-dihydro-2H-isoindole-2-carboxamide;
N-(4-{[2-(3-chlorophenyl)ethyl]carbamoyl}phenyl)-1,3-dihydro-2H-isoindole-2-carboxamide;
N-{4-[(4-hydroxybutyl)carbamoyl]phenyl}-1,3-dihydro-2H-isoindole-2-carboxamide;
N-{4-[(3-phenylpropyl)carbamoyl]phenyl}-5-(trifluoromethyl)-1,3-dihydro-2H-isoindole-2-carboxamide;
N-(4-{[4-(hydroxymethyl)phenyl]carbamoyl}phenyl)-1,3-dihydro-2H-isoindole-2-carboxamide;
N-[4-(1,3-benzodioxol-5-ylcarbamoyl)phenyl]-1,3-dihydro-2H-isoindole-2-carboxamide;
N-{4-[(1-isopropyl-1H-pyrazol-4-yl)carbamoyl]phenyl}-1,3-dihydro-2H-isoindole-2-carboxamide;
N-{4-[(4-hydroxyphenyl)carbamoyl]phenyl}-1,3-dihydro-2H-isoindole-2-carboxamide;
N-{4-[(1-ethyl-1H-pyrazol-4-yl)carbamoyl]phenyl}-1,3-dihydro-2H-isoindole-2-carboxamide;
N-{4-[(2,5-dimethoxyphenyl)carbamoyl]phenyl}-1,3-dihydro-2H-isoindole-2-carboxamide;
N-{4-[(2-hydroxy-2-methylpropyl)carbamoyl]phenyl}-1,3-dihydro-2H-isoindole-2-carboxamide;
N-{4-[(1-benzylpiperidin-4-yl)carbamoyl]phenyl}-1,3-dihydro-2H-isoindole-2-carboxamide;
N-{4-[(4-methoxyphenyl)carbamoyl]phenyl}-1,3-dihydro-2H-isoindole-2-carboxamide;
N-{4-[(3-methoxyphenyl)carbamoyl]phenyl}-1,3-dihydro-2H-isoindole-2-carboxamide;
N-{4-[(5-acetamido-2-methoxyphenyl)carbamoyl]phenyl}-1,3-dihydro-2H-isoindole-2-carboxamide;
N-(4-{[2-(3,5-dimethoxyphenyl)ethyl]carbamoyl}phenyl)-1,3-dihydro-2H-isoindole-2-carboxamide;
N-[4-({2-[3-(trifluoromethyl)phenyl]ethyl}carbamoyl)phenyl]-1,3-dihydro-2H-isoindole-2-carboxamide;
N-{4-[(2-methylbutan-2-yl)carbamoyl]phenyl}-1,3-dihydro-2H-isoindole-2-carboxamide;
N-(4-{[2-(1H-imidazol-4-yl)ethyl]carbamoyl}phenyl)-1,3-dihydro-2H-isoindole-2-carboxamide;
N-(4-{[(2S)-2-hydroxypropyl]carbamoyl}phenyl)-1,3-dihydro-2H-isoindole-2-carboxamide;
N-(4-{[(1R)-1-(3-cyanophenyl)ethyl]carbamoyl}phenyl)-1,3-dihydro-2H-isoindole-2-carboxamide;
N-(4-{[(2S)-1-hydroxy-3-methylbutan-2-yl]carbamoyl}phenyl)-1,3-dihydro-2H-isoindole-2-carboxamide;
N-{4-[(4-cyanophenyl)carbamoyl]phenyl}-1,3-dihydro-2H-isoindole-2-carboxamide;
N-(4-{[2-(4-chlorophenyl)ethyl]carbamoyl}phenyl)-1,3-dihydro-2H-isoindole-2-carboxamide;
N-(4-{[2-(4-methylpiperazin-1-yl)ethyl]carbamoyl}phenyl)-1,3-dihydro-2H-isoindole-2-carboxamide;
N-(4-{[2-(pyridin-2-yl)ethyl]carbamoyl}phenyl)-1,3-dihydro-2H-isoindole-2-carboxamide;
N-{4-[(cyanomethyl)carbamoyl]phenyl}-1,3-dihydro-2H-isoindole-2-carboxamide;
N-[4-(cyclohexylcarbamoyl)phenyl]-1,3-dihydro-2H-isoindole-2-carboxamide;
N-{4-[(3-hydroxyphenyl)carbamoyl]phenyl}-1,3-dihydro-2H-isoindole-2-carboxamide;
N-(4-{[4-(dimethylamino)phenyl]carbamoyl}phenyl)-1,3-dihydro-2H-isoindole-2-carboxamide;
N-[4-(phenylcarbamoyl)phenyl]-1,3-dihydro-2H-isoindole-2-carboxamide;
N-{4-[(4-fluorophenyl)carbamoyl]phenyl}-1,3-dihydro-2H-isoindole-2-carboxamide;
N-(4-{[2-(diethylamino)ethyl]carbamoyl}phenyl)-1,3-dihydro-2H-isoindole-2-carboxamide;
N-{4-[(2-aminophenyl)carbamoyl]phenyl}-1,3-dihydro-2H-isoindole-2-carboxamide;
N-(4-{[(2R)-2-hydroxypropyl]carbamoyl}phenyl)-1,3-dihydro-2H-isoindole-2-carboxamide;
N-(4-{[(2S)-1-amino-4-methyl-1-oxopentan-2-yl]carbamoyl}phenyl)-1,3-dihydro-2H-isoindole-2-carboxamide;
N-(4-{[3-(morpholin-4-yl)propyl]carbamoyl}phenyl)-1,3-dihydro-2H-isoindole-2-carboxamide;
N-(4-{[1-(3-chlorobenzyl)-1H-pyrazol-4-yl]carbamoyl}phenyl)-1,3-dihydro-2H-isoindole-2-carboxamide;
N-(4-{[3-(piperidin-1-yl)propyl]carbamoyl}phenyl)-1,3-dihydro-2H-isoindole-2-carboxamide;
N-{4-[(2-hydroxy-6-methylphenyl)carbamoyl]phenyl}-1,3-dihydro-2H-isoindole-2-carboxamide;
N-(4-{[4-(dimethylamino)butyl]carbamoyl}phenyl)-1,3-dihydro-2H-isoindole-2-carboxamide;
N-{4-[(3-hydroxypropyl)carbamoyl]phenyl}-1,3-dihydro-2H-isoindole-2-carboxamide;
N-[4-(propylcarbamoyl)phenyl]-1,3-dihydro-2H-isoindole-2-carboxamide;
N-(4-{[(2S)-1-hydroxybutan-2-yl]carbamoyl}phenyl)-1,3-dihydro-2H-isoindole-2-carboxamide;
N-{4-[(5-fluoropyridin-2-yl)carbamoyl]phenyl}-1,3-dihydro-2H-isoindole-2-carboxamide;
N-(4-{[(2S)-1-methoxypropan-2-yl]carbamoyl}phenyl)-1,3-dihydro-2H-isoindole-2-carboxamide;
N-[4-(tert-butylcarbamoyl)phenyl]-1,3-dihydro-2H-isoindole-2-carboxamide;
N-{4-[(3-methylbutan-2-yl)carbamoyl]phenyl}-1,3-dihydro-2H-isoindole-2-carboxamide;
N-(4-{[(3S)-1-benzylpyrrolidin-3-yl]carbamoyl}phenyl)-1,3-dihydro-2H-isoindole-2-carboxamide;

N-{4-[(3-fluorophenyl)carbamoyl]phenyl}-1,3-dihydro-2H-isoindole-2-carboxamide;
N-[4-(cyclopentylcarbamoyl)phenyl]-1,3-dihydro-2H-isoindole-2-carboxamide;
N-[4-(cyclopropylcarbamoyl)phenyl]-1,3-dihydro-2H-isoindole-2-carboxamide;
N-[4-(methylcarbamoyl)phenyl]-1,3-dihydro-2H-isoindole-2-carboxamide;
N-(4-{[3-(dimethylamino)propyl]carbamoyl}phenyl)-1,3-dihydro-2H-isoindole-2-carboxamide;
N-[4-(pentan-2-ylcarbamoyl)phenyl]-1,3-dihydro-2H-isoindole-2-carboxamide;
N-[4-(pentan-3-ylcarbamoyl)phenyl]-1,3-dihydro-2H-isoindole-2-carboxamide;
N-[4-(cyclobutylcarbamoyl)phenyl]-1,3-dihydro-2H-isoindole-2-carboxamide;
N-(4-{[1-(4-fluorophenyl)-1H-pyrazol-4-yl]carbamoyl}phenyl)-1,3-dihydro-2H-isoindole-2-carboxamide;
N-{4-[(1-hydroxy-2-methylpropan-2-yl)carbamoyl]phenyl}-1,3-dihydro-2H-isoindole-2-carboxamide;
N-{4-[(1-phenyl-1H-pyrazol-4-yl)carbamoyl]phenyl}-1,3-dihydro-2H-isoindole-2-carboxamide;
N-[4-({2-[4-(trifluoromethyl)phenyl]ethyl}carbamoyl)phenyl]-1,3-dihydro-2H-isoindole-2-carboxamide;
N-[4-(sec-butylcarbamoyl)phenyl]-1,3-dihydro-2H-isoindole-2-carboxamide;
N-{4-[(1-methoxypropan-2-yl)carbamoyl]phenyl}-1,3-dihydro-2H-isoindole-2-carboxamide;
N-{4-[(3R)-tetrahydrofuran-3-ylcarbamoyl]phenyl}-1,3-dihydro-2H-isoindole-2-carboxamide;
N-(4-{[(2S)-1-hydroxy-4-methylpentan-2-yl]carbamoyl}phenyl)-1,3-dihydro-2H-isoindole-2-carboxamide;
N-(4-{[(1R)-2-hydroxy-1-phenylethyl]carbamoyl}phenyl)-1,3-dihydro-2H-isoindole-2-carboxamide;
N-(4-{[(2R)-1-hydroxy-3-methylbutan-2-yl]carbamoyl}phenyl)-1,3-dihydro-2H-isoindole-2-carboxamide;
N-(4-{[(2R)-1-hydroxybutan-2-yl]carbamoyl}phenyl)-1,3-dihydro-2H-isoindole-2-carboxamide;
N-[4-(prop-2-yn-1-ylcarbamoyl)phenyl]-1,3-dihydro-2H-isoindole-2-carboxamide;
5,6-dimethoxy-N-{4-[(3-phenylpropyl)carbamoyl]phenyl}-1,3-dihydro-2H-isoindole-2-carboxamide;
N-(4-{[3-(4-chlorophenoxy)propyl]carbamoyl}phenyl)-1,3-dihydro-2H-isoindole-2-carboxamide;
N-(4-{[4-(trifluoromethoxy)phenyl]carbamoyl}phenyl)-1,3-dihydro-2H-isoindole-2-carboxamide;
N-{4-[(4-phenyl-1,3-thiazol-2-yl)carbamoyl]phenyl}-1,3-dihydro-2H-isoindole-2-carboxamide;
methyl 2-{[4-(propylcarbamoyl)phenyl]carbamoyl}isoindoline-5-carboxylate;
2-{[4-(propylcarbamoyl)phenyl]carbamoyl}isoindoline-5-carboxylic acid;
5-amino-N-[4-(propylcarbamoyl)phenyl]-1,3-dihydro-2H-isoindole-2-carboxamide;
5-(hydroxymethyl)-N-[4-(propylcarbamoyl)phenyl]-1,3-dihydro-2H-isoindole-2-carboxamide;
5-(aminomethyl)-N-[4-(propylcarbamoyl)phenyl]-1,3-dihydro-2H-isoindole-2-carboxamide;
5-[(2-hydroxy-2-methylpropanoyl)amino]-N-[4-(propylcarbamoyl)phenyl]-1,3-dihydro-2H-isoindole-2-carboxamide;
5-acetamido-N-[4-(propylcarbamoyl)phenyl]-1,3-dihydro-2H-isoindole-2-carboxamide;
5-[(N,N-dimethylglycyl)amino]-N-[4-(propylcarbamoyl)phenyl]-1,3-dihydro-2H-isoindole-2-carboxamide;
N-[4-(propylcarbamoyl)phenyl]-5-(1H-pyrazol-3-yl)-1,3-dihydro-2H-isoindole-2-carboxamide;
N-[4-(propylcarbamoyl)phenyl]-5-(1H-pyrazol-4-yl)-1,3-dihydro-2H-isoindole-2-carboxamide;
5-[(methoxyacetyl)amino]-N-[4-(propylcarbamoyl)phenyl]-1,3-dihydro-2H-isoindole-2-carboxamide;
5-[(methylsulfonyl)amino]-N-[4-(propylcarbamoyl)phenyl]-1,3-dihydro-2H-isoindole-2-carboxamide;
5-bromo-N-[4-(propylcarbamoyl)phenyl]-1,3-dihydro-2H-isoindole-2-carboxamide;
N-{4-[(3,5-dimethoxybenzyl)carbamoyl]phenyl}-1,3-dihydro-2H-pyrrolo[3,4-c]pyridine-2-carboxamide;
N-{4-[(4-chlorobenzyl)carbamoyl]phenyl}-1,3-dihydro-2H-pyrrolo[3,4-c]pyridine-2-carboxamide;
N-{4-[(3-phenylpropyl)carbamoyl]phenyl}-1,3-dihydro-2H-pyrrolo[3,4-c]pyridine-2-carboxamide;
N-{4-[(tetrahydrofuran-3-ylmethyl)carbamoyl]phenyl}-1,3-dihydro-2H-pyrrolo[3,4-c]pyridine-2-carboxamide;
N-{4-[(3-methylbutyl)carbamoyl]phenyl}-1,3-dihydro-2H-pyrrolo[3,4-c]pyridine-2-carboxamide;
5-fluoro-N-[4-(propylcarbamoyl)phenyl]-1,3-dihydro-2H-isoindole-2-carboxamide;
N-(4-{[(3R)-tetrahydrofuran-3-ylmethyl]carbamoyl}phenyl)-1,3-dihydro-2H-isoindole-2-carboxamide;
N-(4-{[(3S)-tetrahydrofuran-3-ylmethyl]carbamoyl}phenyl)-1,3-dihydro-2H-isoindole-2-carboxamide;
N-{4-[(2-methoxyethyl)carbamoyl]phenyl}-1,3-dihydro-2H-isoindole-2-carboxamide;
N-{4-[(5-chloropyridin-2-yl)carbamoyl]phenyl}-1,3-dihydro-2H-isoindole-2-carboxamide;
N-{4-[(3-hydroxy-4-methoxyphenyl)carbamoyl]phenyl}-1,3-dihydro-2H-isoindole-2-carboxamide;
N-{4-[(2,4-dimethoxybenzyl)carbamoyl]phenyl}-1,3-dihydro-2H-isoindole-2-carboxamide;
N-(4-{[4-(2-oxopyrrolidin-1-yl)benzyl]carbamoyl}phenyl)-1,3-dihydro-2H-isoindole-2-carboxamide;
N-(4-{[(1S,2S)-2-hydroxy-2,3-dihydro-1H-inden-1-yl]carbamoyl}phenyl)-1,3-dihydro-2H-isoindole-2-carboxamide;
N-(4-{[(1-hydroxycyclopropyl)methyl]carbamoyl}phenyl)-1,3-dihydro-2H-isoindole-2-carboxamide;
N-{4-[(tetrahydro-2H-pyran-2-ylmethyl)carbamoyl]phenyl}-1,3-dihydro-2H-isoindole-2-carboxamide;
N-{4-[(tetrahydro-2H-pyran-3-ylmethyl)carbamoyl]phenyl}-1,3-dihydro-2H-isoindole-2-carboxamide;
N-{4-[(tetrahydro-2H-pyran-4-ylmethyl)carbamoyl]phenyl}-1,3-dihydro-2H-isoindole-2-carboxamide;
N-[4-(propylcarbamoyl)phenyl]-5-vinyl-1,3-dihydro-2H-isoindole-2-carboxamide;
N-(4-{[(2S)-tetrahydrofuran-2-ylmethyl]carbamoyl}phenyl)-1,3-dihydro-2H-pyrrolo[3,4-c]pyridine-2-carboxamide;
N-(4-{[(2R)-tetrahydrofuran-2-ylmethyl]carbamoyl}phenyl)-1,3-dihydro-2H-pyrrolo[3,4-c]pyridine-2-carboxamide;
N-(4-{[(3-methylbutyl)amino]carbonyl}phenyl)-5,7-dihydro-6H-pyrrolo[3,4-d]pyrimidine-6-carboxamide;
N-(4-{[(3-phenylpropyl)amino]carbonyl}phenyl)-5,7-dihydro-6H-pyrrolo[3,4-d]pyrimidine-6-carboxamide;
5-fluoro-N-[4-({[(2S)-tetrahydrofuran-2-ylmethyl]amino}carbonyl)phenyl]-1,3-dihydro-2H-isoindole-2-carboxamide;

5-fluoro-N-[4-({[(2R)-tetrahydro furan-2-ylmethyl]amino}carbonyl)phenyl]-1,3-dihydro-2H-isoindole-2-carboxamide;
N-[4-({[(1S)-2-hydroxy-1-phenylethyl]amino}carbonyl)phenyl]-1,3-dihydro-2H-pyrrolo[3,4-c]pyridine-2-carboxamide;
N-{4-[(propylamino)carbonyl]phenyl}-5-pyridin-3-yl-1,3-dihydro-2H-isoindole-2-carboxamide;
N-{4-[(propylamino)carbonyl]phenyl}-5-pyridin-4-yl-1,3-dihydro-2H-isoindole-2-carboxamide;
$N^5$-(2-methoxyethyl)-$N^2$-{4-[(propylamino)carbonyl]phenyl}-1,3-dihydro-2H-isoindole-2,5-dicarboxamide;
N-[4-({[(1S)-2-hydroxy-1-pyridin-2-ylethyl]amino}carbonyl)phenyl]-1,3-dihydro-2H-pyrrolo[3,4-c]pyridine-2-carboxamide;
N-(4-{[(3-methylbutyl)amino]carbonyl}phenyl)-5,7-dihydro-6H-pyrrolo[3,4-b]pyridine-6-carboxamide;
N-(4-{[(tetrahydrofuran-3-ylmethyl)amino]carbonyl}phenyl)-5,7-dihydro-6H-pyrrolo[3,4-b]pyridine-6-carboxamide;
N-[4-({[(1S)-2-hydroxy-1-pyridin-2-ylethyl]amino}carbonyl)phenyl]-1,3-dihydro-2H-isoindole-2-carboxamide;
5-(1,2-dihydroxyethyl)-N-{4-[(propylamino)carbonyl]phenyl}-1,3-dihydro-2H-isoindole-2-carboxamide;
N-(4-{[6-(benzoylamino)hexyl]carbamoyl}phenyl)-1,3-dihydro-2H-isoindole-2-carboxamide;
N-[4-({4-[(benzoylamino)methyl]benzyl}carbamoyl)phenyl]-5-fluoro-1,3-dihydro-2H-isoindole-2-carboxamide;
N-{4-[(tetrahydro-2H-pyran-2-ylmethyl)carbamoyl]phenyl}-1,3-dihydro-2H-pyrrolo[3,4-c]pyridine-2-carboxamide;
N-{4-[(tetrahydro-2H-pyran-3-ylmethyl)carbamoyl]phenyl}-1,3-dihydro-2H-pyrrolo[3,4-c]pyridine-2-carboxamide;
N-{4-[(tetrahydro-2H-pyran-4-ylmethyl)carbamoyl]phenyl}-1,3-dihydro-2H-pyrrolo[3,4-c]pyridine-2-carboxamide;
N-(4-{[(2S)-1-hydroxy-4-methylpentan-2-yl]carbamoyl}phenyl)-1,3-dihydro-2H-pyrrolo[3,4-c]pyridine-2-carboxamide;
$N^5$-[2-(dimethylamino)ethyl]-$N^2$-[4-(propylcarbamoyl)phenyl]-1,3-dihydro-2H-isoindole-2,5-dicarboxamide;
5-(morpholin-4-ylcarbonyl)-N-[4-(propylcarbamoyl)phenyl]-1,3-dihydro-2H-isoindole-2-carboxamide;
N-[4-(isobutoxycarbamoyl)phenyl]-1,3-dihydro-2H-isoindole-2-carboxamide;
5-fluoro-N-{4-[(tetrahydro-2H-pyran-2-ylmethyl)carbamoyl]phenyl}-1,3-dihydro-2H-isoindole-2-carboxamide;
5-fluoro-N-{4-[(tetrahydro-2H-pyran-3-ylmethyl)carbamoyl]phenyl}-1,3-dihydro-2H-isoindole-2-carboxamide;
5-fluoro-N-{4-[(tetrahydro-2H-pyran-4-ylmethyl)carbamoyl]phenyl}-1,3-dihydro-2H-isoindole-2-carboxamide;
5-fluoro-N-(4-{[(1S)-2-hydroxy-1-phenylethyl]carbamoyl}phenyl)-1,3-dihydro-2H-isoindole-2-carboxamide;
5-fluoro-N-(4-{[(1S)-2-hydroxy-1-(pyridin-2-yl)ethyl]carbamoyl}phenyl)-1,3-dihydro-2H-isoindole-2-carboxamide;
5-fluoro-N-(4-{[(2S)-1-hydroxy-4-methylpentan-2-yl]carbamoyl}phenyl)-1,3-dihydro-2H-isoindole-2-carboxamide;
N-(4-{[(2S)-1-hydroxy-4-(methylthio)butan-2-yl]carbamoyl}phenyl)-1,3-dihydro-2H-isoindole-2-carboxamide;
N-(4-{[(2S,3S)-1-hydroxy-3-methylpentan-2-yl]carbamoyl}phenyl)-1,3-dihydro-2H-isoindole-2-carboxamide;
N-(4-{[(2S)-1-hydroxypropan-2-yl]carbamoyl}phenyl)-1,3-dihydro-2H-isoindole-2-carboxamide;
N-(4-{[(2S,3R)-1,3-dihydroxybutan-2-yl]carbamoyl}phenyl)-1,3-dihydro-2H-isoindole-2-carboxamide;
N-(4-{[(2S)-1-hydroxyhexan-2-yl]carbamoyl}phenyl)-1,3-dihydro-2H-isoindole-2-carboxamide;
N-(4-{[(2S)-1-hydroxypentan-2-yl]carbamoyl}phenyl)-1,3-dihydro-2H-isoindole-2-carboxamide;
N-(4-{[(1S,2S)-2-hydroxycyclopentyl]carbamoyl}phenyl)-1,3-dihydro-2H-isoindole-2-carboxamide;
N-(4-{[(1S,2R)-2-hydroxycyclopentyl]carbamoyl}phenyl)-1,3-dihydro-2H-isoindole-2-carboxamide;
N-(4-{[(2S)-1-cyclohexyl-3-hydroxypropan-2-yl]carbamoyl}phenyl)-1,3-dihydro-2H-isoindole-2-carboxamide;
N-[4-({(2R)-1-hydroxy-3-[(4-methylbenzyl)thio]propan-2-yl}carbamoyl)phenyl]-1,3-dihydro-2H-isoindole-2-carboxamide;
N-(4-{[(1S)-1-(4-tert-butylphenyl)-2-hydroxyethyl]carbamoyl}phenyl)-1,3-dihydro-2H-isoindole-2-carboxamide;
5-methoxy-N-[4-(propylcarbamoyl)phenyl]-1,3-dihydro-2H-isoindole-2-carboxamide;
5-methyl-N-[4-(propylcarbamoyl)phenyl]-1,3-dihydro-2H-isoindole-2-carboxamide;
N-[4-(propylcarbamoyl)phenyl]-1,3-dihydro-2H-pyrrolo[3,4-c]pyridine-2-carboxamide;
N-(4-{[(2S)-tetrahydrofuran-2-ylmethyl]carbamoyl}phenyl)-5,7-dihydro-6H-pyrrolo[3,4-b]pyridine-6-carboxamide;
N-(4-{[(2R)-tetrahydrofuran-2-ylmethyl]carbamoyl}phenyl)-5,7-dihydro-6H-pyrrolo[3,4-b]pyridine-6-carboxamide;
N-(4-{[(2S)-1-hydroxy-4-methylpentan-2-yl]carbamoyl}phenyl)-5,7-dihydro-6H-pyrrolo[3,4-b]pyridine-6-carboxamide;
N-(4-{[(1S)-2-hydroxy-1-phenylethyl]carbamoyl}phenyl)-5,7-dihydro-6H-pyrrolo[3,4-b]pyridine-6-carboxamide;
N-{4-[(tetrahydro-2H-pyran-4-ylmethyl)carbamoyl]phenyl}-5,7-dihydro-6H-pyrrolo[3,4-b]pyridine-6-carboxamide;
5-(hydroxymethyl)-N-{4-[(3-methylbutyl)carbamoyl]phenyl}-1,3-dihydro-2H-isoindole-2-carboxamide;
N-(4-{[(1S)-2-hydroxy-1-(pyridin-2-yl)ethyl]carbamoyl}phenyl)-5,7-dihydro-6H-pyrrolo[3,4-b]pyridine-6-carboxamide;
5-fluoro-N-(4-{[(3R)-tetrahydrofuran-3-ylmethyl]carbamoyl}phenyl)-1,3-dihydro-2H-isoindole-2-carboxamide;
5-fluoro-N-(4-{[(3S)-tetrahydrofuran-3-ylmethyl]carbamoyl}phenyl)-1,3-dihydro-2H-isoindole-2-carboxamide;
N-{4-[(2-hydroxy-2-methylpropyl)carbamoyl]phenyl}-1,3-dihydro-2H-pyrrolo[3,4-c]pyridine-2-carboxamide;
N-{4-[(4-hydroxybutyl)carbamoyl]phenyl}-1,3-dihydro-2H-pyrrolo[3,4-c]pyridine-2-carboxamide;
N-(4-{[(2S)-1-hydroxy-3-methylbutan-2-yl]carbamoyl}phenyl)-1,3-dihydro-2H-pyrrolo[3,4-c]pyridine-2-carboxamide;
N-{4-[(1-hydroxy-2-methylpropan-2-yl)carbamoyl]phenyl}-1,3-dihydro-2H-pyrrolo[3,4-c]pyridine-2-carboxamide;

N-(4-{[(2R)-2-hydroxypropyl]carbamoyl}phenyl)-1,3-dihydro-2H-pyrrolo[3,4-c]pyridine-2-carboxamide;
N-(4-{[(2S)-2-hydroxypropyl]carbamoyl}phenyl)-1,3-dihydro-2H-pyrrolo[3,4-c]pyridine-2-carboxamide;
N-(4-{[3-(piperidin-1-yl)propyl]carbamoyl}phenyl)-1,3-dihydro-2H-pyrrolo[3,4-c]pyridine-2-carboxamide;
N-(4-{[3-(2-oxopyrrolidin-1-yl)propyl]carbamoyl}phenyl)-1,3-dihydro-2H-pyrrolo[3,4-c]pyridine-2-carboxamide;
N-(4-{[(1-methylpyrrolidin-3-yl)methyl]carbamoyl}phenyl)-1,3-dihydro-2H-isoindole-2-carboxamide;
N-{4-[(pyrrolidin-3-ylmethyl)carbamoyl]phenyl}-1,3-dihydro-2H-isoindole-2-carboxamide;
N-(4-{[(3S)-tetrahydrofuran-3-ylmethyl]carbamoyl}phenyl)-1,3-dihydro-2H-pyrrolo[3,4-c]pyridine-2-carboxamide;
N-(4-{[(1-methylpiperidin-4-yl)methyl]carbamoyl}phenyl)-1,3-dihydro-2H-isoindole-2-carboxamide;
N-{4-[(2-isopropoxyethyl)carbamoyl]phenyl}-1,3-dihydro-2H-pyrrolo[3,4-c]pyridine-2-carboxamide;
N-(4-{[4-(morpholin-4-yl)benzyl]carbamoyl}phenyl)-1,3-dihydro-2H-pyrrolo[3,4-c]pyridine-2-carboxamide;
N-{4-[(cyclopropylmethyl)carbamoyl]phenyl}-1,3-dihydro-2H-pyrrolo[3,4-c]pyridine-2-carboxamide;
N-[4-(isobutylcarbamoyl)phenyl]-1,3-dihydro-2H-pyrrolo[3,4-c]pyridine-2-carboxamide;
N-[4-(butylcarbamoyl)phenyl]-1,3-dihydro-2H-pyrrolo[3,4-c]pyridine-2-carboxamide;
N-{4-[(2-methoxyethyl)carbamoyl]phenyl}-1,3-dihydro-2H-pyrrolo[3,4-c]pyridine-2-carboxamide;
N-[4-(cyclopentylcarbamoyl)phenyl]-1,3-dihydro-2H-pyrrolo[3,4-c]pyridine-2-carboxamide;
N-{4-[(3R)-tetrahydrofuran-3-ylcarbamoyl]phenyl}-1,3-dihydro-2H-pyrrolo[3,4-c]pyridine-2-carboxamide;
N-{4-[(1-methoxypropan-2-yl)carbamoyl]phenyl}-1,3-dihydro-2H-pyrrolo[3,4-c]pyridine-2-carboxamide;
N-{4-[(cyclopentylmethyl)carbamoyl]phenyl}-1,3-dihydro-2H-pyrrolo[3,4-c]pyridine-2-carboxamide;
N-{4-[(2-thienylmethyl)carbamoyl]phenyl}-1,3-dihydro-2H-pyrrolo[3,4-c]pyridine-2-carboxamide;
N-{4-[(3-isopropoxypropyl)carbamoyl]phenyl}-1,3-dihydro-2H-pyrrolo[3,4-c]pyridine-2-carboxamide;
N-{4-[(3-aminobenzyl)carbamoyl]phenyl}-1,3-dihydro-2H-pyrrolo[3,4-c]pyridine-2-carboxamide;
N-{4-[(6-methoxypyridin-3-yl)carbamoyl]phenyl}-1,3-dihydro-2H-pyrrolo[3,4-c]pyridine-2-carboxamide;
N-{4-[(3-isobutoxypropyl)carbamoyl]phenyl}-1,3-dihydro-2H-pyrrolo[3,4-c]pyridine-2-carboxamide;
N-{4-[(4-methoxybenzyl)carbamoyl]phenyl}-1,3-dihydro-2H-pyrrolo[3,4-c]pyridine-2-carboxamide;
N-{4-[(3-methoxybenzyl)carbamoyl]phenyl}-1,3-dihydro-2H-pyrrolo[3,4-c]pyridine-2-carboxamide;
N-(4-{[2-(3,4-dimethoxyphenyl)ethyl]carbamoyl}phenyl)-1,3-dihydro-2H-pyrrolo[3,4-c]pyridine-2-carboxamide;
N-(4-{[3-(dimethylamino)propyl]carbamoyl}phenyl)-1,3-dihydro-2H-pyrrolo[3,4-c]pyridine-2-carboxamide;
N-(4-{[3-(morpholin-4-yl)propyl]carbamoyl}phenyl)-1,3-dihydro-2H-pyrrolo[3,4-c]pyridine-2-carboxamide;
N-{4-[(3-hydroxypropyl)carbamoyl]phenyl}-1,3-dihydro-2H-pyrrolo[3,4-c]pyridine-2-carboxamide;
N-(4-{[4-(dimethylamino)butyl]carbamoyl}phenyl)-1,3-dihydro-2H-pyrrolo[3,4-c]pyridine-2-carboxamide;
N-{4-[(pyridin-4-ylmethyl)carbamoyl]phenyl}-1,3-dihydro-2H-pyrrolo[3,4-c]pyridine-2-carboxamide;
N-{4-[(pyridin-3-ylmethyl)carbamoyl]phenyl}-1,3-dihydro-2H-pyrrolo[3,4-c]pyridine-2-carboxamide;
N-{4-[(pyrimidin-4-ylmethyl)carbamoyl]phenyl}-1,3-dihydro-2H-pyrrolo[3,4-c]pyridine-2-carboxamide;
N-(4-{[2-(pyridin-3-yl)ethyl]carbamoyl}phenyl)-1,3-dihydro-2H-pyrrolo[3,4-c]pyridine-2-carboxamide;
N-(4-{[2-(4-methylpiperazin-1-yl)ethyl]carbamoyl}phenyl)-1,3-dihydro-2H-pyrrolo[3,4-c]pyridine-2-carboxamide;
N-(4-{[(1,1-dioxidotetrahydrothiophen-3-yl)methyl]carbamoyl}phenyl)-1,3-dihydro-2H-isoindole-2-carboxamide;
N-(4-{[(2,2-dimethyl-1,3-dioxolan-4-yl)methyl]carbamoyl}phenyl)-1,3-dihydro-2H-isoindole-2-carboxamide;
N-(4-{[(1S)-2-methoxy-1-phenylethyl]carbamoyl}phenyl)-1,3-dihydro-2H-isoindole-2-carboxamide;
N-[4-({[(4S)-2,2-dimethyl-1,3-dioxolan-4-yl]methyl}carbamoyl)phenyl]-1,3-dihydro-2H-isoindole-2-carboxamide;
N-[4-({[(4R)-2,2-dimethyl-1,3-dioxolan-4-yl]methyl}carbamoyl)phenyl]-1,3-dihydro-2H-isoindole-2-carboxamide;
N-[4-({[3-(hydroxymethyl)oxetan-3-yl]methyl}carbamoyl)phenyl]-1,3-dihydro-2H-isoindole-2-carboxamide;
N-{4-[(2R)-butan-2-ylcarbamoyl]phenyl}-1,3-dihydro-2H-isoindole-2-carboxamide;
N-(4-{[(3-methyloxetan-3-yl)methyl]carbamoyl}phenyl)-1,3-dihydro-2H-isoindole-2-carboxamide;
N-(4-{[(3-methyloxetan-3-yl)methyl]carbamoyl}phenyl)-1,3-dihydro-2H-pyrrolo[3,4-c]pyridine-2-carboxamide;
5-cyano-N-{4-[(cyclopentylmethyl)carbamoyl]phenyl}-1,3-dihydro-2H-isoindole-2-carboxamide;
5-cyano-N-{4-[(1,3-thiazol-5-ylmethyl)carbamoyl]phenyl}-1,3-dihydro-2H-isoindole-2-carboxamide;
5-cyano-N-(4-{[(1R)-3-hydroxy-1-phenylpropyl]carbamoyl}phenyl)-1,3-dihydro-2H-isoindole-2-carboxamide;
5-cyano-N-(4-{[2-hydroxy-1-(4-methylphenyl)ethyl]carbamoyl}phenyl)-1,3-dihydro-2H-isoindole-2-carboxamide;
5-cyano-N-{4-[(1,3-dihydroxypropan-2-yl)carbamoyl]phenyl}-1,3-dihydro-2H-isoindole-2-carboxamide;
5-cyano-N-(4-{[(2R)-2-hydroxypropyl]carbamoyl}phenyl)-1,3-dihydro-2H-isoindole-2-carboxamide;
5-cyano-N-{4-[(2-hydroxy-2-methylpropyl)carbamoyl]phenyl}-1,3-dihydro-2H-isoindole-2-carboxamide;
5-cyano-N-(4-{[(2R)-1-hydroxy-3-methylbutan-2-yl]carbamoyl}phenyl)-1,3-dihydro-2H-isoindole-2-carboxamide;
5-cyano-N-(4-{[(2S)-tetrahydrofuran-2-ylmethyl]carbamoyl}phenyl)-1,3-dihydro-2H-isoindole-2-carboxamide;
5-cyano-N-(4-{[2-(4-methylpiperazin-1-yl)ethyl]carbamoyl}phenyl)-1,3-dihydro-2H-isoindole-2-carboxamide;
5-cyano-N-(4-{[(1S)-2-hydroxy-1-phenylethyl]carbamoyl}phenyl)-1,3-dihydro-2H-isoindole-2-carboxamide;
5-cyano-N-{4-[(4-hydroxybutyl)carbamoyl]phenyl}-1,3-dihydro-2H-isoindole-2-carboxamide;
5-cyano-N-(4-{[(2S)-2-hydroxypropyl]carbamoyl}phenyl)-1,3-dihydro-2H-isoindole-2-carboxamide;
5-cyano-N-{4-[(3-furylmethyl)carbamoyl]phenyl}-1,3-dihydro-2H-isoindole-2-carboxamide;
5-cyano-N-{4-[(tetrahydrofuran-2-ylmethyl)carbamoyl]phenyl}-1,3-dihydro-2H-isoindole-2-carboxamide;

5-cyano-N-(4-{[3-(piperidin-1-yl)propyl]carbamoyl}phenyl)-1,3-dihydro-2H-isoindole-2-carboxamide;

5-cyano-N-(4-{[(2R)-tetrahydrofuran-2-ylmethyl]carbamoyl}phenyl)-1,3-dihydro-2H-isoindole-2-carboxamide;

5-cyano-N-{4-[(tetrahydrofuran-3-ylmethyl)carbamoyl]phenyl}-1,3-dihydro-2H-isoindole-2-carboxamide;

5-cyano-N-(4-{[(1R)-2-hydroxy-1-phenylethyl]carbamoyl}phenyl)-1,3-dihydro-2H-isoindole-2-carboxamide;

5-cyano-N-(4-{[(2S)-1-hydroxybutan-2-yl]carbamoyl}phenyl)-1,3-dihydro-2H-isoindole-2-carboxamide;

5-cyano-N-{4-[(2,3-dihydroxypropyl)carbamoyl]phenyl}-1,3-dihydro-2H-isoindole-2-carboxamide;

5-cyano-N-(4-{[(tetrahydro-2H-pyran-4-ylmethyl)carbamoyl]phenyl}-1,3-dihydro-2H-isoindole-2-carboxamide;

5-cyano-N-(4-{[2-hydroxy-1-(pyridin-2-yl)ethyl]carbamoyl}phenyl)-1,3-dihydro-2H-isoindole-2-carboxamide;

5-cyano-N-{4-[(1-hydroxy-4-methylpentan-2-yl)carbamoyl]phenyl}-1,3-dihydro-2H-isoindole-2-carboxamide;

5-cyano-N-(4-{[(1-methylpyrrolidin-3-yl)methyl]carbamoyl}phenyl)-1,3-dihydro-2H-isoindole-2-carboxamide;

5-cyano-N-(4-{[(1-methylpiperidin-4-yl)methyl]carbamoyl}phenyl)-1,3-dihydro-2H-isoindole-2-carboxamide;

5-cyano-N-{4-[(tetrahydro-2H-pyran-3-ylmethyl)carbamoyl]phenyl}-1,3-dihydro-2H-isoindole-2-carboxamide;

N-{4-[(1-oxa-8-azaspiro[4.5]dec-2-ylmethyl)carbamoyl]phenyl}-1,3-dihydro-2H-isoindole-2-carboxamide;

N-[4-(1-oxa-8-azaspiro[4.5]dec-3-ylcarbamoyl)phenyl]-1,3-dihydro-2H-isoindole-2-carboxamide;

N-{4-[(2-oxa-9-azaspiro[5.5]undec-3-ylmethyl)carbamoyl]phenyl}-1,3-dihydro-2H-isoindole-2-carboxamide;

N-(4-{[(1,1-dioxidotetrahydrothiophen-3-yl)methyl]carbamoyl}phenyl)-1,3-dihydro-2H-pyrrolo[3,4-c]pyridine-2-carboxamide;

N-{4-[(pyrrolidin-3-ylmethyl)carbamoyl]phenyl}-1,3-dihydro-2H-pyrrolo[3,4-c]pyridine-2-carboxamide;

N-(4-{[(3S)-pyrrolidin-3-ylmethyl]carbamoyl}phenyl)-1,3-dihydro-2H-pyrrolo[3,4-c]pyridine-2-carboxamide;

N-(4-{[(1-methylpyrrolidin-3-yl)methyl]carbamoyl}phenyl)-1,3-dihydro-2H-pyrrolo[3,4-c]pyridine-2-carboxamide;

N-(4-{[(1-methylpiperidin-4-yl)methyl]carbamoyl}phenyl)-1,3-dihydro-2H-pyrrolo[3,4-c]pyridine-2-carboxamide;

5-fluoro-N-{4-[(1-oxa-8-azaspiro[4.5]dec-2-ylmethyl)carbamoyl]phenyl}-1,3-dihydro-2H-isoindole-2-carboxamide;

5-fluoro-N-[4-(1-oxa-8-azaspiro[4.5]dec-3-ylcarbamoyl)phenyl]-1,3-dihydro-2H-isoindole-2-carboxamide;

N-[4-({[(3R)-1-isobutyrylpyrrolidin-3-yl]methyl}carbamoyl)phenyl]-1,3-dihydro-2H-pyrrolo[3,4-c]pyridine-2-carboxamide;

N-[4-({[(3R)-1-benzoylpyrrolidin-3-yl]methyl}carbamoyl)phenyl]-1,3-dihydro-2H-pyrrolo[3,4-c]pyridine-2-carboxamide;

N-[4-({[1-(tetrahydrofuran-3-ylcarbonyl)pyrrolidin-3-yl]methyl}carbamoyl)phenyl]-1,3-dihydro-2H-pyrrolo[3,4-c]pyridine-2-carboxamide;

N-[4-({[1-(methylsulfonyl)pyrrolidin-3-yl]methyl}carbamoyl)phenyl]-1,3-dihydro-2H-pyrrolo[3,4-c]pyridine-2-carboxamide;

N-[4-({[1-(morpholin-4-yl)cyclopentyl]methyl}carbamoyl)phenyl]-1,3-dihydro-2H-pyrrolo[3,4-c]pyridine-2-carboxamide;

N-(4-{[(1S)-1-(4-fluorophenyl)-2-hydroxyethyl]carbamoyl}phenyl)-1,3-dihydro-2H-pyrrolo[3,4-c]pyridine-2-carboxamide;

N-(4-{[(1S)-2-hydroxy-1-(4-methoxyphenyl)ethyl]carbamoyl}phenyl)-1,3-dihydro-2H-pyrrolo[3,4-c]pyridine-2-carboxamide;

N-[4-({[3-(hydroxymethyl)oxetan-3-yl]methyl}carbamoyl)phenyl]-1,3-dihydro-2H-pyrrolo[3,4-c]pyridine-2-carboxamide;

N-(4-{[(1S)-1-(1,3-benzodioxol-5-yl)-2-hydroxyethyl]carbamoyl}phenyl)-1,3-dihydro-2H-pyrrolo[3,4-c]pyridine-2-carboxamide;

N-(4-{[(1S)-1-(4-fluorophenyl)-2-hydroxyethyl]carbamoyl}phenyl)-1,3-dihydro-2H-isoindole-2-carboxamide;

N-(4-{[(1S)-2-hydroxy-1-(4-methoxyphenyl)ethyl]carbamoyl}phenyl)-1,3-dihydro-2H-isoindole-2-carboxamide;

N-(4-{[(1S)-1-(1,3-benzodioxol-5-yl)-2-hydroxyethyl]carbamoyl}phenyl)-1,3-dihydro-2H-isoindole-2-carboxamide;

N-{4-[(1-oxa-8-azaspiro[4.5]dec-2-ylmethyl)carbamoyl]phenyl}-1,3-dihydro-2H-pyrrolo[3,4-c]pyridine-2-carboxamide;

N-[4-(1-oxa-8-azaspiro[4.5]dec-3-ylcarbamoyl)phenyl]-1,3-dihydro-2H-pyrrolo[3,4-c]pyridine-2-carboxamide;

N-{4-[(2-oxa-9-azaspiro[5.5]undec-3-ylmethyl)carbamoyl]phenyl}-1,3-dihydro-2H-pyrrolo[3,4-c]pyridine-2-carboxamide;

5-fluoro-N-(4-{[1-(1,3-thiazol-2-yl)propan-2-yl]carbamoyl}phenyl)-1,3-dihydro-2H-isoindole-2-carboxamide;

N-{4-[(4,4-difluorocyclohexyl)carbamoyl]phenyl}-5-fluoro-1,3-dihydro-2H-isoindole-2-carboxamide;

N-(4-{[1-(3,5-dimethyl-1H-pyrazol-1-yl)propan-2-yl]carbamoyl}phenyl)-5-fluoro-1,3-dihydro-2H-isoindole-2-carboxamide;

5-fluoro-N-(4-{[2-methyl-2-(morpholin-4-yl)butyl]carbamoyl}phenyl)-1,3-dihydro-2H-isoindole-2-carboxamide;

5-fluoro-N-(4-{[2-(2-methyl-1,3-thiazol-4-yl)ethyl]carbamoyl}phenyl)-1,3-dihydro-2H-isoindole-2-carboxamide;

5-fluoro-N-(4-{[2-methyl-1-(morpholin-4-yl)propan-2-yl]carbamoyl}phenyl)-1,3-dihydro-2H-isoindole-2-carboxamide;

5-fluoro-N-{4-[(4-methoxybenzyl)carbamoyl]phenyl}-1,3-dihydro-2H-isoindole-2-carboxamide;

5-fluoro-N-(4-{[3-(morpholin-4-yl)propyl]carbamoyl}phenyl)-1,3-dihydro-2H-isoindole-2-carboxamide;

Nalpha-(4-{[(5-fluoro-1,3-dihydro-2H-isoindol-2-yl)carbonyl]amino}benzoyl)-D-phenylalaninamide;

N-(4-{[2-(acetylamino)phenyl]carbamoyl}phenyl)-5-fluoro-1,3-dihydro-2H-isoindole-2-carboxamide;

5-fluoro-N-(4-{[2-(furan-2-yl)-2-(pyrrolidin-1-yl)ethyl]carbamoyl}phenyl)-1,3-dihydro-2H-isoindole-2-carboxamide;

N-{4-[(1-amino-1-oxohexan-2-yl)carbamoyl]phenyl}-5-fluoro-1,3-dihydro-2H-isoindole-2-carboxamide;

N-(4-{[2-(3,4-dimethoxyphenyl)ethyl]carbamoyl}phenyl)-5-fluoro-1,3-dihydro-2H-isoindole-2-carboxamide;

N-(4-{[(2S)-3,3-dimethyl-1-(methylamino)-1-oxobutan-2-yl]carbamoyl}phenyl)-5-fluoro-1,3-dihydro-2H-isoindole-2-carboxamide;

Nalpha-(4-{[(5-fluoro-1,3-dihydro-2H-isoindol-2-yl)carbonyl]amino}benzoyl)-L-phenylalaninamide;

N-(4-{[(2R)-1-amino-4-methyl-1-oxopentan-2-yl]carbamoyl}phenyl)-5-fluoro-1,3-dihydro-2H-isoindole-2-carboxamide;

5-fluoro-N-(4-{[3-(methylcarbamoyl)phenyl]carbamoyl}phenyl)-1,3-dihydro-2H-isoindole-2-carboxamide;

N-{4-[(2-amino-2-oxo-1-phenylethyl)carbamoyl]phenyl}-5-fluoro-1,3-dihydro-2H-isoindole-2-carboxamide;

N-{4-[(3-tert-butoxypropyl)carbamoyl]phenyl}-5-fluoro-1,3-dihydro-2H-isoindole-2-carboxamide;

N-(4-{[2-(2,6-dimethylmorpholin-4-yl)ethyl]carbamoyl}phenyl)-5-fluoro-1,3-dihydro-2H-isoindole-2-carboxamide;

N-(4-{[(1R)-2-amino-2-oxo-1-phenylethyl]carbamoyl}phenyl)-5-fluoro-1,3-dihydro-2H-isoindole-2-carboxamide;

5-fluoro-N-{4-[(3-methoxybenzyl)carbamoyl]phenyl}-1,3-dihydro-2H-isoindole-2-carboxamide;

N-(4-{[2-(3,5-dimethyl-1H-pyrazol-1-yl)ethyl]carbamoyl}phenyl)-5-fluoro-1,3-dihydro-2H-isoindole-2-carboxamide;

5-fluoro-N-(4-{[2-methyl-2-(morpholin-4-yl)propyl]carbamoyl}phenyl)-1,3-dihydro-2H-isoindole-2-carboxamide;

5-fluoro-N-(4-{[(3S)-1-methyl-2-oxoazepan-3-yl]carbamoyl}phenyl)-1,3-dihydro-2H-isoindole-2-carboxamide;

5-fluoro-N-(4-{[2-(4-methylpiperazin-1-yl)ethyl]carbamoyl}phenyl)-1,3-dihydro-2H-isoindole-2-carboxamide;

5-fluoro-N-(4-{[4-(morpholin-4-yl)benzyl]carbamoyl}phenyl)-1,3-dihydro-2H-isoindole-2-carboxamide;

5-fluoro-N-(4-{[3-(piperidin-1-yl)propyl]carbamoyl}phenyl)-1,3-dihydro-2H-isoindole-2-carboxamide;

N-(4-{[3-(5-methyl-1H-pyrazol-1-yl)propyl]carbamoyl}phenyl)-5,7-dihydro-6H-pyrrolo[3,4-b]pyridine-6-carboxamide;

N-(4-{[2-(4-chloro-1H-pyrazol-1-yl)ethyl]carbamoyl}phenyl)-5,7-dihydro-6H-pyrrolo[3,4-b]pyridine-6-carboxamide;

N-(4-{[1-(3,5-dimethyl-1H-pyrazol-1-yl)propan-2-yl]carbamoyl}phenyl)-5,7-dihydro-6H-pyrrolo[3,4-b]pyridine-6-carboxamide;

N-(4-{[2-methyl-2-(morpholin-4-yl)butyl]carbamoyl}phenyl)-5,7-dihydro-6H-pyrrolo[3,4-b]pyridine-6-carboxamide;

N-{4-[(4-methoxybenzyl)carbamoyl]phenyl}-5,7-dihydro-6H-pyrrolo[3,4-b]pyridine-6-carboxamide;

N-(4-{[3-(morpholin-4-yl)propyl]carbamoyl}phenyl)-5,7-dihydro-6H-pyrrolo[3,4-b]pyridine-6-carboxamide;

N-{4-[(2-carbamoylbenzyl)carbamoyl]phenyl}-5,7-dihydro-6H-pyrrolo[3,4-b]pyridine-6-carboxamide;

N-{4-[(1-amino-1-oxohexan-2-yl)carbamoyl]phenyl}-5,7-dihydro-6H-pyrrolo[3,4-b]pyridine-6-carboxamide;

N-(4-{[2-(3,4-dimethoxyphenyl)ethyl]carbamoyl}phenyl)-5,7-dihydro-6H-pyrrolo[3,4-b]pyridine-6-carboxamide;

Nalpha-{4-[(5,7-dihydro-6H-pyrrolo[3,4-b]pyridin-6-ylcarbonyl)amino]benzoyl}-L-phenylalaninamide;

N-(4-{[(2R)-1-amino-4-methyl-1-oxopentan-2-yl]carbamoyl}phenyl)-5,7-dihydro-6H-pyrrolo[3,4-b]pyridine-6-carboxamide;

N-{4-[(3-tert-butoxypropyl)carbamoyl]phenyl}-5,7-dihydro-6H-pyrrolo[3,4-b]pyridine-6-carboxamide;

N-(4-{[2-(2,6-dimethylmorpholin-4-yl)ethyl]carbamoyl}phenyl)-5,7-dihydro-6H-pyrrolo[3,4-b]pyridine-6-carboxamide;

N-{4-[(3-methoxybenzyl)carbamoyl]phenyl}-5,7-dihydro-6H-pyrrolo[3,4-b]pyridine-6-carboxamide;

N-(4-{[2-methyl-2-(morpholin-4-yl)propyl]carbamoyl}phenyl)-5,7-dihydro-6H-pyrrolo[3,4-b]pyridine-6-carboxamide;

N-(4-{[(3S)-1-methyl-2-oxoazepan-3-yl]carbamoyl}phenyl)-5,7-dihydro-6H-pyrrolo[3,4-b]pyridine-6-carboxamide;

N-(4-{[2-(4-methylpiperazin-1-yl)ethyl]carbamoyl}phenyl)-5,7-dihydro-6H-pyrrolo[3,4-b]pyridine-6-carboxamide;

N-(4-{[4-(morpholin-4-yl)benzyl]carbamoyl}phenyl)-5,7-dihydro-6H-pyrrolo[3,4-b]pyridine-6-carboxamide;

N-(4-{[3-(piperidin-1-yl)propyl]carbamoyl}phenyl)-5,7-dihydro-6H-pyrrolo[3,4-b]pyridine-6-carboxamide;

N-[4-(4,5,6,7-tetrahydro-1H-indazol-5-ylcarbamoyl)phenyl]-5,7-dihydro-6H-pyrrolo[3,4-b]pyridine-6-carboxamide;

5-fluoro-N-{4-[(3-methoxy-2,2-dimethylpropyl)carbamoyl]phenyl}-1,3-dihydro-2H-isoindole-2-carboxamide;

N-{4-[(3,3-dimethylbutyl)carbamoyl]phenyl}-5-fluoro-1,3-dihydro-2H-isoindole-2-carboxamide;

5-fluoro-N-(4-{[1-(furan-2-yl)propan-2-yl]carbamoyl}phenyl)-1,3-dihydro-2H-isoindole-2-carboxamide;

5-fluoro-N-(4-{[(3-methyl-1,2-oxazol-5-yl)methyl]carbamoyl}phenyl)-1,3-dihydro-2H-isoindole-2-carboxamide;

N-(4-{[(2R)-1-cyanobutan-2-yl]carbamoyl}phenyl)-5-fluoro-1,3-dihydro-2H-isoindole-2-carboxamide;

N-{4-[(2R)-butan-2-ylcarbamoyl]phenyl}-5-fluoro-1,3-dihydro-2H-isoindole-2-carboxamide;

5-fluoro-N-(4-{[2-(1H-pyrazol-1-yl)ethyl]carbamoyl}phenyl)-1,3-dihydro-2H-isoindole-2-carboxamide;

N-(4-{[1-(ethylamino)-1-oxopropan-2-yl]carbamoyl}phenyl)-5-fluoro-1,3-dihydro-2H-isoindole-2-carboxamide;

5-fluoro-N-(4-{[(1-methyl-1H-pyrazol-3-yl)methyl]carbamoyl}phenyl)-1,3-dihydro-2H-isoindole-2-carboxamide;

5-fluoro-N-{4-[(2-methoxybutyl)carbamoyl]phenyl}-1,3-dihydro-2H-isoindole-2-carboxamide;

N-(4-{[4-(dimethylamino)butyl]carbamoyl}phenyl)-5-fluoro-1,3-dihydro-2H-isoindole-2-carboxamide;

5-fluoro-N-{4-[(3S)-tetrahydrofuran-3-ylcarbamoyl]phenyl}-1,3-dihydro-2H-isoindole-2-carboxamide;

5-fluoro-N-{4-[(1-methoxybutan-2-yl)carbamoyl]phenyl}-1,3-dihydro-2H-isoindole-2-carboxamide;

N-{4-[(2-ethoxypropyl)carbamoyl]phenyl}-5-fluoro-1,3-dihydro-2H-isoindole-2-carboxamide;

N-{4-[(2S)-butan-2-ylcarbamoyl]phenyl}-5-fluoro-1,3-dihydro-2H-isoindole-2-carboxamide;

5-fluoro-N-(4-{[2-(5-methyl-1H-pyrazol-1-yl)ethyl]carbamoyl}phenyl)-1,3-dihydro-2H-isoindole-2-carboxamide;

5-fluoro-N-(4-{[2-(3-methyl-1H-pyrazol-1-yl)ethyl]carbamoyl}phenyl)-1,3-dihydro-2H-isoindole-2-carboxamide;

5-fluoro-N-{4-[(2-methylpropyl)carbamoyl]phenyl}-1,3-dihydro-2H-isoindole-2-carboxamide;
5-fluoro-N-{4-[(pyridin-3-ylmethyl)carbamoyl]phenyl}-1,3-dihydro-2H-isoindole-2-carboxamide;
5-fluoro-N-{4-[(tetrahydrofuran-2-ylmethyl)carbamoyl]phenyl}-1,3-dihydro-2H-isoindole-2-carboxamide;
N-(4-{[(1R)-1-cyclopropylethyl]carbamoyl}phenyl)-5-fluoro-1,3-dihydro-2H-isoindole-2-carboxamide;
5-fluoro-N-(4-{[1-(1-methylcyclopropyl)ethyl]carbamoyl}phenyl)-1,3-dihydro-2H-isoindole-2-carboxamide;
5-fluoro-N-{4-[(thiophen-2-ylmethyl)carbamoyl]phenyl}-1,3-dihydro-2H-isoindole-2-carboxamide;
N-(4-{[(1S)-1-cyclopropylethyl]carbamoyl}phenyl)-5-fluoro-1,3-dihydro-2H-isoindole-2-carboxamide;
5-fluoro-N-{4-[(4-methoxybutyl)carbamoyl]phenyl}-1,3-dihydro-2H-isoindole-2-carboxamide;
5-fluoro-N-(4-{[(5-methyl-1,3-oxazol-2-yl)methyl]carbamoyl}phenyl)-1,3-dihydro-2H-isoindole-2-carboxamide;
5-fluoro-N-(4-{[2-(tetrahydro-2H-pyran-3-yl)ethyl]carbamoyl}phenyl)-1,3-dihydro-2H-isoindole-2-carboxamide;
5-fluoro-N-(4-{[(2S)-1-methoxypropan-2-yl]carbamoyl}phenyl)-1,3-dihydro-2H-isoindole-2-carboxamide;
N-{4-[(3,3-dimethyl-2-oxobutyl)carbamoyl]phenyl}-5-fluoro-1,3-dihydro-2H-isoindole-2-carboxamide;
5-fluoro-N-(4-{[(1-methyl-1H-pyrrol-2-yl)methyl]carbamoyl}phenyl)-1,3-dihydro-2H-isoindole-2-carboxamide;
5-fluoro-N-(4-{[2-(propan-2-yloxy)ethyl]carbamoyl}phenyl)-1,3-dihydro-2H-isoindole-2-carboxamide;
N-(4-{[3-(dimethylamino)propyl]carbamoyl}phenyl)-5-fluoro-1,3-dihydro-2H-isoindole-2-carboxamide;
N-(4-{[(2S)-1-amino-1-oxobutan-2-yl]carbamoyl}phenyl)-5-fluoro-1,3-dihydro-2H-isoindole-2-carboxamide;
5-fluoro-N-[4-(tetrahydro-2H-pyran-3-ylcarbamoyl)phenyl]-1,3-dihydro-2H-isoindole-2-carboxamide;
5-fluoro-N-(4-{[2-(1H-pyrrol-1-yl)ethyl]carbamoyl}phenyl)-1,3-dihydro-2H-isoindole-2-carboxamide;
5-fluoro-N-{4-[(1-methoxypropan-2-yl)carbamoyl]phenyl}-1,3-dihydro-2H-isoindole-2-carboxamide;
5-fluoro-N-{4-[(2-methoxyethyl)carbamoyl]phenyl}-1,3-dihydro-2H-isoindole-2-carboxamide;
N-[4-(cyclopentylcarbamoyl)phenyl]-5-fluoro-1,3-dihydro-2H-isoindole-2-carboxamide;
5-fluoro-N-(4-{[(2S)-3-methylbutan-2-yl]carbamoyl}phenyl)-1,3-dihydro-2H-isoindole-2-carboxamide;
5-fluoro-N-(4-{[(2R)-3-methylbutan-2-yl]carbamoyl}phenyl)-1,3-dihydro-2H-isoindole-2-carboxamide;
5-fluoro-N-(4-{[(2S)-2-methylbutyl]carbamoyl}phenyl)-1,3-dihydro-2H-isoindole-2-carboxamide;
5-fluoro-N-{4-[(2-hydroxy-2-methylpropyl)carbamoyl]phenyl}-1,3-dihydro-2H-isoindole-2-carboxamide;
5-fluoro-N-(4-{[2-(tetrahydro-2H-pyran-4-yl)ethyl]carbamoyl}phenyl)-1,3-dihydro-2H-isoindole-2-carboxamide;
N-[4-(butylcarbamoyl)phenyl]-5-fluoro-1,3-dihydro-2H-isoindole-2-carboxamide;
N-{4-[(1-cyanoethyl)carbamoyl]phenyl}-5-fluoro-1,3-dihydro-2H-isoindole-2-carboxamide;
5-fluoro-N-(4-{[(5-methyl-1,2-oxazol-3-yl)methyl]carbamoyl}phenyl)-1,3-dihydro-2H-isoindole-2-carboxamide;
5-fluoro-N-{4-[(3R)-tetrahydrofuran-3-ylcarbamoyl]phenyl}-1,3-dihydro-2H-isoindole-2-carboxamide;
N-{4-[(3-methoxy-2,2-dimethylpropyl)carbamoyl]phenyl}-5,7-dihydro-6H-pyrrolo[3,4-b]pyridine-6-carboxamide;
N-{4-[(3,3-dimethylbutyl)carbamoyl]phenyl}-5,7-dihydro-6H-pyrrolo[3,4-b]pyridine-6-carboxamide;
N-(4-{[1-(furan-2-yl)propan-2-yl]carbamoyl}phenyl)-5,7-dihydro-6H-pyrrolo[3,4-b]pyridine-6-carboxamide;
N-(4-{[(3-methyl-1,2-oxazol-5-yl)methyl]carbamoyl}phenyl)-5,7-dihydro-6H-pyrrolo[3,4-b]pyridine-6-carboxamide;
N-(4-{[(2R)-1-cyanobutan-2-yl]carbamoyl}phenyl)-5,7-dihydro-6H-pyrrolo[3,4-b]pyridine-6-carboxamide;
N-(4-{[(1-methyl-1H-pyrazol-3-yl)methyl]carbamoyl}phenyl)-5,7-dihydro-6H-pyrrolo[3,4-b]pyridine-6-carboxamide;
N-{4-[(2-methoxybutyl)carbamoyl]phenyl}-5,7-dihydro-6H-pyrrolo[3,4-b]pyridine-6-carboxamide;
N-(4-{[4-(dimethylamino)butyl]carbamoyl}phenyl)-5,7-dihydro-6H-pyrrolo[3,4-b]pyridine-6-carboxamide;
N-(4-{[1-(1,3-thiazol-2-yl)ethyl]carbamoyl}phenyl)-5,7-dihydro-6H-pyrrolo[3,4-b]pyridine-6-carboxamide;
N-(4-{[1-(1-methyl-1H-pyrazol-4-yl)ethyl]carbamoyl}phenyl)-5,7-dihydro-6H-pyrrolo[3,4-b]pyridine-6-carboxamide;
N-{4-[(3S)-tetrahydrofuran-3-ylcarbamoyl]phenyl}-5,7-dihydro-6H-pyrrolo[3,4-b]pyridine-6-carboxamide;
N-{4-[(1-methoxybutan-2-yl)carbamoyl]phenyl}-5,7-dihydro-6H-pyrrolo[3,4-b]pyridine-6-carboxamide;
N-{4-[(4-aminobenzyl)carbamoyl]phenyl}-5,7-dihydro-6H-pyrrolo[3,4-b]pyridine-6-carboxamide;
N-{4-[(2-ethoxypropyl)carbamoyl]phenyl}-5,7-dihydro-6H-pyrrolo[3,4-b]pyridine-6-carboxamide;
N-{4-[(6-methoxypyridin-3-yl)carbamoyl]phenyl}-5,7-dihydro-6H-pyrrolo[3,4-b]pyridine-6-carboxamide;
N-{4-[(2S)-butan-2-ylcarbamoyl]phenyl}-5,7-dihydro-6H-pyrrolo[3,4-b]pyridine-6-carboxamide;
N-{4-[(1-cyanocyclopropyl)carbamoyl]phenyl}-5,7-dihydro-6H-pyrrolo[3,4-b]pyridine-6-carboxamide;
N-(4-{[2-(5-methyl-1H-pyrazol-1-yl)ethyl]carbamoyl}phenyl)-5,7-dihydro-6H-pyrrolo[3,4-b]pyridine-6-carboxamide;
N-(4-{[(4-methyl-1,3-thiazol-2-yl)methyl]carbamoyl}phenyl)-5,7-dihydro-6H-pyrrolo[3,4-b]pyridine-6-carboxamide;
N-{4-[(3-hydroxypropyl)carbamoyl]phenyl}-5,7-dihydro-6H-pyrrolo[3,4-b]pyridine-6-carboxamide;
N-{4-[(2-methylpropyl)carbamoyl]phenyl}-5,7-dihydro-6H-pyrrolo[3,4-b]pyridine-6-carboxamide;
N-{4-[(tetrahydrofuran-2-ylmethyl)carbamoyl]phenyl}-5,7-dihydro-6H-pyrrolo[3,4-b]pyridine-6-carboxamide;
N-(4-{[(1R)-1-cyclopropylethyl]carbamoyl}phenyl)-5,7-dihydro-6H-pyrrolo[3,4-b]pyridine-6-carboxamide;
N-(4-{[1-(1-methylcyclopropyl)ethyl]carbamoyl}phenyl)-5,7-dihydro-6H-pyrrolo[3,4-b]pyridine-6-carboxamide;
N-{4-[(thiophen-2-ylmethyl)carbamoyl]phenyl}-5,7-dihydro-6H-pyrrolo[3,4-b]pyridine-6-carboxamide;
N-(4-{[(1S)-1-cyclopropylethyl]carbamoyl}phenyl)-5,7-dihydro-6H-pyrrolo[3,4-b]pyridine-6-carboxamide;
N-{4-[(4-methoxybutyl)carbamoyl]phenyl}-5,7-dihydro-6H-pyrrolo[3,4-b]pyridine-6-carboxamide;
N-(4-{[2-(tetrahydro-2H-pyran-3-yl)ethyl]carbamoyl}phenyl)-5,7-dihydro-6H-pyrrolo[3,4-b]pyridine-6-carboxamide;

N-(4-{[(2S)-1-methoxypropan-2-yl]carbamoyl}phenyl)-5,7-dihydro-6H-pyrrolo[3,4-b]pyridine-6-carboxamide;
N-{4-[(3,3-dimethyl-2-oxobutyl)carbamoyl]phenyl}-5,7-dihydro-6H-pyrrolo[3,4-b]pyridine-6-carboxamide;
N-(4-{[(1-methyl-1H-pyrrol-2-yl)methyl]carbamoyl}phenyl)-5,7-dihydro-6H-pyrrolo[3,4-b]pyridine-6-carboxamide;
N-(4-{[2-(propan-2-yloxy)ethyl]carbamoyl}phenyl)-5,7-dihydro-6H-pyrrolo[3,4-b]pyridine-6-carboxamide;
N-(4-{[3-(dimethylamino)propyl]carbamoyl}phenyl)-5,7-dihydro-6H-pyrrolo[3,4-b]pyridine-6-carboxamide;
N-[4-(tetrahydro-2H-pyran-3-ylcarbamoyl)phenyl]-5,7-dihydro-6H-pyrrolo[3,4-b]pyridine-6-carboxamide;
N-(4-{[2-(1H-pyrrol-1-yl)ethyl]carbamoyl}phenyl)-5,7-dihydro-6H-pyrrolo[3,4-b]pyridine-6-carboxamide;
N-{4-[(1-methoxypropan-2-yl)carbamoyl]phenyl}-5,7-dihydro-6H-pyrrolo[3,4-b]pyridine-6-carboxamide;
N-{4-[(3-aminobenzyl)carbamoyl]phenyl}-5,7-dihydro-6H-pyrrolo[3,4-b]pyridine-6-carboxamide;
N-(4-{[(2R)-3-methylbutan-2-yl]carbamoyl}phenyl)-5,7-dihydro-6H-pyrrolo[3,4-b]pyridine-6-carboxamide;
N-{4-[(tetrahydro-2H-pyran-3-ylmethyl)carbamoyl]phenyl}-5,7-dihydro-6H-pyrrolo[3,4-b]pyridine-6-carboxamide;
N-{4-[(2-hydroxy-2-methylpropyl)carbamoyl]phenyl}-5,7-dihydro-6H-pyrrolo[3,4-b]pyridine-6-carboxamide;
N-[4-(butylcarbamoyl)phenyl]-5,7-dihydro-6H-pyrrolo[3,4-b]pyridine-6-carboxamide;
N-{4-[(1-cyanoethyl)carbamoyl]phenyl}-5,7-dihydro-6H-pyrrolo[3,4-b]pyridine-6-carboxamide;
N-{4-[(3R)-tetrahydrofuran-3-ylcarbamoyl]phenyl}-5,7-dihydro-6H-pyrrolo[3,4-b]pyridine-6-carboxamide;
N-{4-[(cyclopentylmethyl)carbamoyl]phenyl}-5,7-dihydro-6H-pyrrolo[3,4-b]pyridine-6-carboxamide;
N-{4-[(2-methoxy-2-methylpropyl)carbamoyl]phenyl}-5,7-dihydro-6H-pyrrolo[3,4-b]pyridine-6-carboxamide;
N-{4-[(cyclopropylmethyl)carbamoyl]phenyl}-5,7-dihydro-6H-pyrrolo[3,4-b]pyridine-6-carboxamide;
N-{4-[(pyridin-4-ylmethyl)carbamoyl]phenyl}-5,7-dihydro-6H-pyrrolo[3,4-b]pyridine-6-carboxamide;
N-{4-[(3-methoxy-2,2-dimethylpropyl)carbamoyl]phenyl}-1,3-dihydro-2H-isoindole-2-carboxamide;
N-{4-[(4,4-difluorocyclohexyl)carbamoyl]phenyl}-1,3-dihydro-2H-isoindole-2-carboxamide;
N-(4-{[(2R)-1-cyanobutan-2-yl]carbamoyl}phenyl)-1,3-dihydro-2H-isoindole-2-carboxamide;
N-{4-[(2-methoxybutyl)carbamoyl]phenyl}-1,3-dihydro-2H-isoindole-2-carboxamide;
N-(4-{[1-(ethylamino)-1-oxopropan-2-yl]carbamoyl}phenyl)-1,3-dihydro-2H-isoindole-2-carboxamide;
N-(4-{[(1R)-1-cyclopropylethyl]carbamoyl}phenyl)-1,3-dihydro-2H-isoindole-2-carboxamide;
N-(4-{[(1S)-1-cyclopropylethyl]carbamoyl}phenyl)-1,3-dihydro-2H-isoindole-2-carboxamide;
N-{4-[(3S)-tetrahydro furan-3-ylcarbamoyl]phenyl}-1,3-dihydro-2H-isoindole-2-carboxamide;
N-(4-{[2-(tetrahydro-2H-pyran-3-yl)ethyl]carbamoyl}phenyl)-1,3-dihydro-2H-isoindole-2-carboxamide;
N-(4-{[(5-methyl-1,3-oxazol-2-yl)methyl]carbamoyl}phenyl)-1,3-dihydro-2H-isoindole-2-carboxamide;
N-[4-({2-[(dimethylamino)methyl]benzyl}carbamoyl)phenyl]-1,3-dihydro-2H-isoindole-2-carboxamide;
N-(4-{[(1R)-2-amino-2-oxo-1-phenylethyl]carbamoyl}phenyl)-1,3-dihydro-2H-isoindole-2-carboxamide;
N-[4-(1,3-oxazol-2-ylcarbamoyl)phenyl]-1,3-dihydro-2H-isoindole-2-carboxamide;
N-[4-(tetrahydro-2H-pyran-3-ylcarbamoyl)phenyl]-1,3-dihydro-2H-isoindole-2-carboxamide;
N-(4-{[2-(2,6-dimethylmorpholin-4-yl)ethyl]carbamoyl}phenyl)-1,3-dihydro-2H-isoindole-2-carboxamide;
N-(4-{[1-(1-methylcyclopropyl)ethyl]carbamoyl}phenyl)-1,3-dihydro-2H-isoindole-2-carboxamide;
N-(4-{[2-(furan-2-yl)-2-(pyrrolidin-1-yl)ethyl]carbamoyl}phenyl)-1,3-dihydro-2H-isoindole-2-carboxamide;
N-(4-{[3-(3,5-dimethyl-1H-pyrazol-1-yl)propyl]carbamoyl}phenyl)-1,3-dihydro-2H-isoindole-2-carboxamide;
N-(4-{[(3S)-1-methyl-2-oxoazepan-3-yl]carbamoyl}phenyl)-1,3-dihydro-2H-isoindole-2-carboxamide;
N-(4-{[2-(1H-pyrazol-1-yl)ethyl]carbamoyl}phenyl)-1,3-dihydro-2H-isoindole-2-carboxamide;
N-(4-{[1-(1,3-thiazol-2-yl)ethyl]carbamoyl}phenyl)-1,3-dihydro-2H-isoindole-2-carboxamide;
N-(4-{[1-(furan-2-yl)propan-2-yl]carbamoyl}phenyl)-1,3-dihydro-2H-isoindole-2-carboxamide;
N-(4-{[1-(1-methyl-1H-pyrazol-4-yl)ethyl]carbamoyl}phenyl)-1,3-dihydro-2H-isoindole-2-carboxamide;
N-(4-{[(2R)-1-amino-4-methyl-1-oxopentan-2-yl]carbamoyl}phenyl)-1,3-dihydro-2H-isoindole-2-carboxamide;
N-(4-{[1-(3,5-dimethyl-1H-pyrazol-1-yl)propan-2-yl]carbamoyl}phenyl)-1,3-dihydro-2H-isoindole-2-carboxamide;
N-{4-[(2,2-difluoroethyl)carbamoyl]phenyl}-1,3-dihydro-2H-isoindole-2-carboxamide;
N-(4-{[2-(tetrahydro-2H-pyran-4-yl)ethyl]carbamoyl}phenyl)-1,3-dihydro-2H-isoindole-2-carboxamide;
N-{4-[(tetrahydrofuran-2-ylmethyl)carbamoyl]phenyl}-1,3-dihydro-2H-isoindole-2-carboxamide;
N-{4-[(2-methoxy-2-methylpropyl)carbamoyl]phenyl}-1,3-dihydro-2H-isoindole-2-carboxamide;
N-(4-{[(5-methyl-1,2-oxazol-3-yl)methyl]carbamoyl}phenyl)-1,3-dihydro-2H-isoindole-2-carboxamide;
N-(4-{[(1-methyl-1H-pyrazol-4-yl)methyl]carbamoyl}phenyl)-1,3-dihydro-2H-isoindole-2-carboxamide;
N-(4-{[2-(3,5-dimethyl-1H-pyrazol-1-yl)ethyl]carbamoyl}phenyl)-1,3-dihydro-2H-isoindole-2-carboxamide;
Nalpha-{4-[(1,3-dihydro-2H-isoindol-2-ylcarbonyl)amino]benzoyl}-L-phenylalaninamide;
N-(4-{[2-(2-methyl-1,3-thiazol-4-yl)ethyl]carbamoyl}phenyl)-1,3-dihydro-2H-isoindole-2-carboxamide;
N-(4-{[(2S)-3,3-dimethyl-1-(methylamino)-1-oxobutan-2-yl]carbamoyl}phenyl)-1,3-dihydro-2H-isoindole-2-carboxamide;
N-[4-(thiophen-3-ylcarbamoyl)phenyl]-1,3-dihydro-2H-isoindole-2-carboxamide;
N-(4-{[2-(5-methyl-1H-pyrazol-1-yl)ethyl]carbamoyl}phenyl)-1,3-dihydro-2H-isoindole-2-carboxamide;

N-(4-{[2-(3-methyl-1H-pyrazol-1-yl)ethyl]
  carbamoyl}phenyl)-1,3-dihydro-2H-isoindole-2-carboxa-
  mide;
N-{4-[(2S)-butan-2-ylcarbamoyl]phenyl}-1,3-dihydro-2H-
  isoindole-2-carboxamide;
N-{4-[(3,3-dimethyl-2-oxobutyl)carbamoyl]phenyl}-1,3-di-
  hydro-2H-isoindole-2-carboxamide;
N-(4-{[(1-methyl-1H-pyrazol-3-yl)methyl]
  carbamoyl}phenyl)-1,3-dihydro-2H-isoindole-2-carboxa-
  mide;
N-(4-{[2-(acetylamino)phenyl]carbamoyl}phenyl)-1,3-di-
  hydro-2H-isoindole-2-carboxamide;
N-{4-[(1-methoxybutan-2-yl)carbamoyl]phenyl}-1,3-dihy-
  dro-2H-isoindole-2-carboxamide;
N-[4-(tetrahydro-2H-pyran-4-ylcarbamoyl)phenyl]-1,3-di-
  hydro-2H-isoindole-2-carboxamide;
N-[4-(pyrimidin-4-ylcarbamoyl)phenyl]-1,3-dihydro-2H-
  isoindole-2-carboxamide;
N-(4-{[2-(1H-pyrrol-1-yl)ethyl]carbamoyl}phenyl)-1,3-di-
  hydro-2H-isoindole-2-carboxamide;
N-(4-{[(2S)-2-methylbutyl]carbamoyl}phenyl)-1,3-dihy-
  dro-2H-isoindole-2-carboxamide;
N-{4-[(1-amino-1-oxohexan-2-yl)carbamoyl]phenyl}-1,3-
  dihydro-2H-isoindole-2-carboxamide;
N-{4-[(2-amino-2-oxo-1-phenylethyl)carbamoyl]phenyl}-
  1,3-dihydro-2H-isoindole-2-carboxamide;
N-{4-[(3-tert-butoxypropyl)carbamoyl]phenyl}-1,3-dihy-
  dro-2H-isoindole-2-carboxamide;
N-(4-{[3-(methylcarbamoyl)phenyl]carbamoyl}phenyl)-1,
  3-dihydro-2H-isoindole-2-carboxamide;
N-(4-{[(2R)-3-methylbutan-2-yl]carbamoyl}phenyl)-1,3-
  dihydro-2H-isoindole-2-carboxamide;
N-(4-{[(2S)-3-methylbutan-2-yl]carbamoyl}phenyl)-1,3-di-
  hydro-2H-isoindole-2-carboxamide;
N-(4-{[2-methyl-1-(morpholin-4-yl)propan-2-yl]
  carbamoyl}phenyl)-1,3-dihydro-2H-isoindole-2-carboxa-
  mide;
N-(4-{[2-methyl-2-(morpholin-4-yl)propyl]
  carbamoyl}phenyl)-1,3-dihydro-2H-isoindole-2-carboxa-
  mide;
N-{4-[(2-ethoxypropyl)carbamoyl]phenyl}-1,3-dihydro-
  2H-isoindole-2-carboxamide;
and pharmaceutically acceptable salts thereof.

Embodiments of Formula (VIc)

In another aspect, the present invention provides compounds of Formula (VIc)

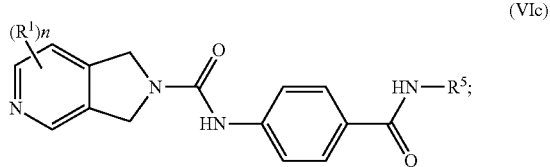

(VIc)

and pharmaceutically acceptable salts thereof; wherein $R^1$ and $R^5$ are as described herein for Formula (Ic); and n is 0 or 1.

In one embodiment of formula (VIc),
n is 0 or 1;
$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, C(O)H, $CF_3$, C(O)OH, or $C(O)NH_2$;

$R^3$, at each occurrence, is independently selected alkyl, alkenyl, alkynyl, aryl, or heterocyclyl; wherein each $R^3$ alkyl, alkenyl, and alkynyl is optionally substituted with one, two, three or four independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I;

$R^5$, at each occurrence, is independently selected alkyl, alkenyl, alkynyl, aryl, heterocyclyl, cycloalkyl, or cycloalkenyl; wherein each $R^5$ alkyl, alkenyl, and alkynyl is optionally substituted with one, two, three or four independently selected $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I;

$R^6$, at each occurrence, is independently selected alkyl, alkenyl, alkynyl, aryl, heterocyclyl, cycloalkyl, or cycloalkenyl; wherein each $R^6$ alkyl, alkenyl, and alkynyl is optionally substituted with one, two, three or four independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, OH, (O), C(O)OH, $N_3$, CN, $NH_2$, $CF_3$, $CF_2CF_3$, F, Cl, Br or I;

$R^9$, at each occurrence, is independently selected alkyl, alkenyl, alkynyl, aryl, heterocyclyl, cycloalkyl, or cycloalkenyl; wherein each $R^9$ alkyl, alkenyl, and alkynyl is optionally substituted alkoxy, OH, cycloalkyl, aryl, or heterocyclyl;

$R^{10}$, at each occurrence, is independently selected alkyl, alkenyl, alkynyl, aryl, heterocyclyl, cycloalkyl, or cycloalkenyl;

wherein the cyclic moieties represented by $R^3$, $R^5$, $R^6$, $R^9$, and $R^{10}$ are optionally substituted with one, two, three, four, five, or six independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, $C(O)H$, $C(O)OH$, OH, CN, $N_3$, $NO_2$, $CF_3$, $CF_2CF_3$, $OCF_3$, $OCF_2CF_3$, $SCF_3$, F, Cl, Br or I;

$R^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, or cycloalkenyl; wherein each $R^{13}$ alkyl, alkenyl, and alkynyl is optionally substituted with one, two, three or four independently selected $R^{14}$, $OR^{14}$, $SR^{14}$, $S(O)R^{14}$, $SO_2R^{14}$, $C(O)R^{14}$, $OC(O)R^{14}$, $OC(O)OR^{14}$, $NH_2$, $NHR^{14}$, $N(R^{14})_2$, $NHC(O)R^{14}$, $NR^{14}C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NH_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, and cycloalkenyl is optionally substituted with one, two, three or four independently selected $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $C(O)H$, $C(O)OH$, $OH$, $CN$, $N_3$, $NO_2$, $CF_3$, $CF_2CF_3$, $OCF_3$, $OCF_2CF_3$, F, Cl, Br or I;

$R^{14}$, at each occurrence, is independently selected alkyl, alkenyl, alkynyl, aryl, heterocyclyl, cycloalkyl, or cycloalkenyl; wherein each $R^{14}$ alkyl, alkenyl, and alkynyl is optionally substituted with one, two, three or four independently selected heterocyclyl, alkoxy, $NH_2$, $SO_2NH_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{14}$ aryl, heterocyclyl, cycloalkyl, and cycloalkenyl is optionally substituted with one, two, three or four independently selected $R^{16}$, $OR^{16}$, OH, F, Cl, Br, or I;

$R^{15}$, at each occurrence, is independently selected alkyl, wherein the $R^{15}$ alkyl is optionally substituted with one, two, three or four alkoxy; and $R^{16}$, at each occurrence, is independently selected alkyl, wherein the $R^{16}$ alkyl is optionally substituted with one, two, three or four independently selected alkoxy;

with the proviso that when $R^{13}$ is piperidinyl, it is substituted piperidinyl.

In another embodiment of Formula (VIc), n is 0. In another embodiment of Formula (VIc), n is 1. In another embodiment of Formula (VIc), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (VIc), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIc), $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIc), $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIc), $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIc), $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIc), $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIc), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIc), $R^1$ is $C(O)NH_2$. In another embodiment of Formula (VIc), $R^1$ is F. In another embodiment of Formula (VIc), $R^1$ is Cl. In another embodiment of Formula (VIc), $R^1$ is Br. In another embodiment of Formula (VIc), $R^1$ is CN. In another embodiment of Formula (VIc), $R^1$ is $NH_2$. In another embodiment of Formula (VIc), $R^1$ is $NO_2$. In another embodiment of Formula (VIc), $R^1$ is $CF_3$. In another embodiment of Formula (VIc), $R^1$ is $C(O)OH$. In another embodiment of Formula (VIc), $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl.

Still another embodiment pertains to compounds having Formula (VIc), which include N-{4-[(3,5-dimethoxybenzyl)carbamoyl]phenyl}-1,3-dihydro-2H-pyrrolo[3,4-c]pyridine-2-carboxamide;

N-{4-[(4-chlorobenzyl)carbamoyl]phenyl}-1,3-dihydro-2H-pyrrolo[3,4-c]pyridine-2-carboxamide;

N-{4-[(3-phenylpropyl)carbamoyl]phenyl}-1,3-dihydro-2H-pyrrolo[3,4-c]pyridine-2-carboxamide;

N-{4-[(tetrahydrofuran-3-ylmethyl)carbamoyl]phenyl}-1,3-dihydro-2H-pyrrolo[3,4-c]pyridine-2-carboxamide;

N-{4-[(3-methylbutyl)carbamoyl]phenyl}-1,3-dihydro-2H-pyrrolo[3,4-c]pyridine-2-carboxamide;

N-(4-{[(2S)-tetrahydrofuran-2-ylmethyl]carbamoyl}phenyl)-1,3-dihydro-2H-pyrrolo[3,4-c]pyridine-2-carboxamide;

N-(4-{[(2R)-tetrahydrofuran-2-ylmethyl]carbamoyl}phenyl)-1,3-dihydro-2H-pyrrolo[3,4-c]pyridine-2-carboxamide;

N-[4-({[(1S)-2-hydroxy-1-phenylethyl]amino}carbonyl)phenyl]-1,3-dihydro-2H-pyrrolo[3,4-c]pyridine-2-carboxamide;

N-[4-({[(1S)-2-hydroxy-1-pyridin-2-ylethyl]amino}carbonyl)phenyl]-1,3-dihydro-2H-pyrrolo[3,4-c]pyridine-2-carboxamide;

N-{4-[(tetrahydro-2H-pyran-2-ylmethyl)carbamoyl]phenyl}-1,3-dihydro-2H-pyrrolo[3,4-c]pyridine-2-carboxamide;

N-{4-[(tetrahydro-2H-pyran-3-ylmethyl)carbamoyl]phenyl}-1,3-dihydro-2H-pyrrolo[3,4-c]pyridine-2-carboxamide;

N-{4-[(tetrahydro-2H-pyran-4-ylmethyl)carbamoyl]phenyl}-1,3-dihydro-2H-pyrrolo[3,4-c]pyridine-2-carboxamide;

N-(4-{[(2S)-1-hydroxy-4-methylpentan-2-yl]carbamoyl}phenyl)-1,3-dihydro-2H-pyrrolo[3,4-c]pyridine-2-carboxamide;

N-[4-(propylcarbamoyl)phenyl]-1,3-dihydro-2H-pyrrolo[3,4-c]pyridine-2-carboxamide;

N-{4-[(4-hydroxypiperidin-1-yl)carbonyl]phenyl}-1,3-dihydro-2H-pyrrolo[3,4-c]pyridine-2-carboxamide;
N-{4-[(2-hydroxy-2-methylpropyl)carbamoyl]phenyl}-1,3-dihydro-2H-pyrrolo[3,4-c]pyridine-2-carboxamide;
N-{4-[(4-hydroxybutyl)carbamoyl]phenyl}-1,3-dihydro-2H-pyrrolo[3,4-c]pyridine-2-carboxamide;
N-(4-{[(2S)-1-hydroxy-3-methylbutan-2-yl]carbamoyl}phenyl)-1,3-dihydro-2H-pyrrolo[3,4-c]pyridine-2-carboxamide;
N-{4-[(1-hydroxy-2-methylpropan-2-yl)carbamoyl]phenyl}-1,3-dihydro-2H-pyrrolo[3,4-c]pyridine-2-carboxamide;
N-(4-{[(2R)-2-hydroxypropyl]carbamoyl}phenyl)-1,3-dihydro-2H-pyrrolo[3,4-c]pyridine-2-carboxamide;
N-(4-{[(2S)-2-hydroxypropyl]carbamoyl}phenyl)-1,3-dihydro-2H-pyrrolo[3,4-c]pyridine-2-carboxamide;
N-(4-{[3-(piperidin-1-yl)propyl]carbamoyl}phenyl)-1,3-dihydro-2H-pyrrolo[3,4-c]pyridine-2-carboxamide;
N-[4-(5,6-dihydroimidazo[1,5-a]pyrazin-7(8H)-ylcarbonyl)phenyl]-1,3-dihydro-2H-pyrrolo[3,4-c]pyridine-2-carboxamide;
N-[4-(morpholin-4-ylcarbonyl)phenyl]-1,3-dihydro-2H-pyrrolo[3,4-c]pyridine-2-carboxamide;
N-(4-{[3-(2-oxopyrrolidin-1-yl)propyl]carbamoyl}phenyl)-1,3-dihydro-2H-pyrrolo[3,4-c]pyridine-2-carboxamide;
N-(4-{[(3S)-tetrahydrofuran-3-ylmethyl]carbamoyl}phenyl)-1,3-dihydro-2H-pyrrolo[3,4-c]pyridine-2-carboxamide;
N-{4-[(2-isopropoxyethyl)carbamoyl]phenyl}-1,3-dihydro-2H-pyrrolo[3,4-c]pyridine-2-carboxamide;
N-[4-(azetidin-1-ylcarbonyl)phenyl]-1,3-dihydro-2H-pyrrolo[3,4-c]pyridine-2-carboxamide;
N-[4-(2,6-diazaspiro[3.5]non-2-ylcarbonyl)phenyl]-1,3-dihydro-2H-pyrrolo[3,4-c]pyridine-2-carboxamide;
N-[4-(1,7-diazaspiro[4.4]non-1-ylcarbonyl)phenyl]-1,3-dihydro-2H-pyrrolo[3,4-c]pyridine-2-carboxamide;
N-(4-{[4-(morpholin-4-yl)benzyl]carbamoyl}phenyl)-1,3-dihydro-2H-pyrrolo[3,4-c]pyridine-2-carboxamide;
N-{4-[(cyclopropylmethyl)carbamoyl]phenyl}-1,3-dihydro-2H-pyrrolo[3,4-c]pyridine-2-carboxamide;
N-[4-(isobutylcarbamoyl)phenyl]-1,3-dihydro-2H-pyrrolo[3,4-c]pyridine-2-carboxamide;
N-[4-(butylcarbamoyl)phenyl]-1,3-dihydro-2H-pyrrolo[3,4-c]pyridine-2-carboxamide;
N-{4-[(2-methoxyethyl)carbamoyl]phenyl}-1,3-dihydro-2H-pyrrolo[3,4-c]pyridine-2-carboxamide;
N-[4-(cyclopentylcarbamoyl)phenyl]-1,3-dihydro-2H-pyrrolo[3,4-c]pyridine-2-carboxamide;
N-{4-[(3R)-tetrahydrofuran-3-ylcarbamoyl]phenyl}-1,3-dihydro-2H-pyrrolo[3,4-c]pyridine-2-carboxamide;
N-{4-[(1-methoxypropan-2-yl)carbamoyl]phenyl}-1,3-dihydro-2H-pyrrolo[3,4-c]pyridine-2-carboxamide;
N-{4-[(cyclopentylmethyl)carbamoyl]phenyl}-1,3-dihydro-2H-pyrrolo[3,4-c]pyridine-2-carboxamide;
N-{4-[(2-thienylmethyl)carbamoyl]phenyl}-1,3-dihydro-2H-pyrrolo[3,4-c]pyridine-2-carboxamide;
N-{4-[(3-isopropoxypropyl)carbamoyl]phenyl}-1,3-dihydro-2H-pyrrolo[3,4-c]pyridine-2-carboxamide;
N-{4-[(3-aminobenzyl)carbamoyl]phenyl}-1,3-dihydro-2H-pyrrolo[3,4-c]pyridine-2-carboxamide;
N-{4-[(6-methoxypyridin-3-yl)carbamoyl]phenyl}-1,3-dihydro-2H-pyrrolo[3,4-c]pyridine-2-carboxamide;
N-{4-[(3-isobutoxypropyl)carbamoyl]phenyl}-1,3-dihydro-2H-pyrrolo[3,4-c]pyridine-2-carboxamide;
N-{4-[(4-methoxybenzyl)carbamoyl]phenyl}-1,3-dihydro-2H-pyrrolo[3,4-c]pyridine-2-carboxamide;
N-{4-[(3-methoxybenzyl)carbamoyl]phenyl}-1,3-dihydro-2H-pyrrolo[3,4-c]pyridine-2-carboxamide;
N-(4-{[4-(trifluoromethyl)piperidin-1-yl]carbonyl}phenyl)-1,3-dihydro-2H-pyrrolo[3,4-c]pyridine-2-carboxamide;
N-(4-{[4-(pyrazin-2-yl)piperazin-1-yl]carbonyl}phenyl)-1,3-dihydro-2H-pyrrolo[3,4-c]pyridine-2-carboxamide;
N-{4-[(4-cyclohexylpiperazin-1-yl)carbonyl]phenyl}-1,3-dihydro-2H-pyrrolo[3,4-c]pyridine-2-carboxamide;
N-(4-{[2-(3,4-dimethoxyphenyl)ethyl]carbamoyl}phenyl)-1,3-dihydro-2H-pyrrolo[3,4-c]pyridine-2-carboxamide;
N-(4-{[3-(dimethylamino)propyl]carbamoyl}phenyl)-1,3-dihydro-2H-pyrrolo[3,4-c]pyridine-2-carboxamide;
N-(4-{[3-(morpholin-4-yl)propyl]carbamoyl}phenyl)-1,3-dihydro-2H-pyrrolo[3,4-c]pyridine-2-carboxamide;
N-[4-({4-[2-(2-hydroxyethoxy)ethyl]piperazin-1-yl}carbonyl)phenyl]-1,3-dihydro-2H-pyrrolo[3,4-c]pyridine-2-carboxamide;
N-{4-[(3-hydroxypropyl)carbamoyl]phenyl}-1,3-dihydro-2H-pyrrolo[3,4-c]pyridine-2-carboxamide;
N-(4-{[4-(dimethylamino)butyl]carbamoyl}phenyl)-1,3-dihydro-2H-pyrrolo[3,4-c]pyridine-2-carboxamide;
N-{4-[(pyridin-4-ylmethyl)carbamoyl]phenyl}-1,3-dihydro-2H-pyrrolo[3,4-c]pyridine-2-carboxamide;
N-{4-[(pyridin-3-ylmethyl)carbamoyl]phenyl}-1,3-dihydro-2H-pyrrolo[3,4-c]pyridine-2-carboxamide;
N-{4-[(pyrimidin-4-ylmethyl)carbamoyl]phenyl}-1,3-dihydro-2H-pyrrolo[3,4-c]pyridine-2-carboxamide;
N-(4-{[2-(pyridin-3-yl)ethyl]carbamoyl}phenyl)-1,3-dihydro-2H-pyrrolo[3,4-c]pyridine-2-carboxamide;
N-(4-{[2-(4-methylpiperazin-1-yl)ethyl]carbamoyl}phenyl)-1,3-dihydro-2H-pyrrolo[3,4-c]pyridine-2-carboxamide;
N-(4-{[(3-methyloxetan-3-yl)methyl]carbamoyl}phenyl)-1,3-dihydro-2H-pyrrolo[3,4-c]pyridine-2-carboxamide;
N-(4-{[(1,1-dioxidotetrahydrothiophen-3-yl)methyl]carbamoyl}phenyl)-1,3-dihydro-2H-pyrrolo[3,4-c]pyridine-2-carboxamide;
N-{4-[(pyrrolidin-3-ylmethyl)carbamoyl]phenyl}-1,3-dihydro-2H-pyrrolo[3,4-c]pyridine-2-carboxamide;
N-(4-{[(3S)-pyrrolidin-3-ylmethyl]carbamoyl}phenyl)-1,3-dihydro-2H-pyrrolo[3,4-c]pyridine-2-carboxamide;
N-(4-{[(1-methylpyrrolidin-3-yl)methyl]carbamoyl}phenyl)-1,3-dihydro-2H-pyrrolo[3,4-c]pyridine-2-carboxamide;
N-(4-{[(1-methylpiperidin-4-yl)methyl]carbamoyl}phenyl)-1,3-dihydro-2H-pyrrolo[3,4-c]pyridine-2-carboxamide;
N-[4-({[(3R)-1-isobutyrylpyrrolidin-3-yl]methyl}carbamoyl)phenyl]-1,3-dihydro-2H-pyrrolo[3,4-c]pyridine-2-carboxamide;
N-[4-({[(3R)-1-benzoylpyrrolidin-3-yl]methyl}carbamoyl)phenyl]-1,3-dihydro-2H-pyrrolo[3,4-c]pyridine-2-carboxamide;
N-[4-({[1-(tetrahydrofuran-3-ylcarbonyl)pyrrolidin-3-yl]methyl}carbamoyl)phenyl]-1,3-dihydro-2H-pyrrolo[3,4-c]pyridine-2-carboxamide;
N-[4-({[1-(methylsulfonyl)pyrrolidin-3-yl]methyl}carbamoyl)phenyl]-1,3-dihydro-2H-pyrrolo[3,4-c]pyridine-2-carboxamide;
N-[4-({[1-(morpholin-4-yl)cyclopentyl]methyl}carbamoyl)phenyl]-1,3-dihydro-2H-pyrrolo[3,4-c]pyridine-2-carboxamide;
N-(4-{[(1S)-1-(4-fluorophenyl)-2-hydroxyethyl]carbamoyl}phenyl)-1,3-dihydro-2H-pyrrolo[3,4-c]pyridine-2-carboxamide;

N-(4-{[(1S)-2-hydroxy-1-(4-methoxyphenyl)ethyl]
carbamoyl}phenyl)-1,3-dihydro-2H-pyrrolo[3,4-c]pyri-
dine-2-carboxamide;

N-[4-({[3-(hydroxymethyl)oxetan-3-yl]methyl}carbamoyl)
phenyl]-1,3-dihydro-2H-pyrrolo[3,4-c]pyridine-2-car-
boxamide;

N-(4-{[(1S)-1-(1,3-benzodioxol-5-yl)-2-hydroxyethyl]
carbamoyl}phenyl)-1,3-dihydro-2H-pyrrolo[3,4-c]pyri-
dine-2-carboxamide;

N-[4-(1,7-diazaspiro[4.4]non-7-ylcarbonyl)phenyl]-1,3-di-
hydro-2H-pyrrolo[3,4-c]pyridine-2-carboxamide;

N-[4-(2,7-diazaspiro[4.5]dec-2-ylcarbonyl)phenyl]-1,3-di-
hydro-2H-pyrrolo[3,4-c]pyridine-2-carboxamide;

N-[4-(2,6-diazaspiro[4.5]dec-2-ylcarbonyl)phenyl]-1,3-di-
hydro-2H-pyrrolo[3,4-c]pyridine-2-carboxamide;

N-[4-(2,7-diazaspiro[4.5]dec-7-ylcarbonyl)phenyl]-1,3-di-
hydro-2H-pyrrolo[3,4-c]pyridine-2-carboxamide;

N-[4-(2,9-diazaspiro[5.5]undec-2-ylcarbonyl)phenyl]-1,3-
dihydro-2H-pyrrolo[3,4-c]pyridine-2-carboxamide;

N-[4-(2,8-diazaspiro[5.5]undec-2-ylcarbonyl)phenyl]-1,3-
dihydro-2H-pyrrolo[3,4-c]pyridine-2-carboxamide;

N-[4-(1,8-diazaspiro[5.5]undec-8-ylcarbonyl)phenyl]-1,3-
dihydro-2H-pyrrolo[3,4-c]pyridine-2-carboxamide;

N-[4-(1,8-diazaspiro[4.6]undec-8-ylcarbonyl)phenyl]-1,3-
dihydro-2H-pyrrolo[3,4-c]pyridine-2-carboxamide;

N-{4-[(1-oxa-8-azaspiro[4.5]dec-2-ylmethyl)carbamoyl]
phenyl}-1,3-dihydro-2H-pyrrolo[3,4-c]pyridine-2-car-
boxamide;

N-[4-(1-oxa-8-azaspiro[4.5]dec-3-ylcarbamoyl)phenyl]-1,
3-dihydro-2H-pyrrolo[3,4-c]pyridine-2-carboxamide;

N-{4-[(2-oxa-9-azaspiro[5.5]undec-3-ylmethyl)carbamoyl]
phenyl}-1,3-dihydro-2H-pyrrolo[3,4-c]pyridine-2-car-
boxamide;

N-[4-(1-oxa-4,8-diazaspiro[5.5]undec-4-ylcarbonyl)phe-
nyl]-1,3-dihydro-2H-pyrrolo[3,4-c]pyridine-2-carboxam-
ide;

N-[4-(1,8-diazaspiro[4.5]dec-1-ylcarbonyl)phenyl]-1,3-di-
hydro-2H-pyrrolo[3,4-c]pyridine-2-carboxamide;

N-[4-(1,8-diazaspiro[4.5]dec-8-ylcarbonyl)phenyl]-1,3-di-
hydro-2H-pyrrolo[3,4-c]pyridine-2-carboxamide;

N-[4-(1,7-diazaspiro[3.5]non-7-ylcarbonyl)phenyl]-1,3-di-
hydro-2H-pyrrolo[3,4-c]pyridine-2-carboxamide;

N-[4-(1,6-diazaspiro[3.5]non-1-ylcarbonyl)phenyl]-1,3-di-
hydro-2H-pyrrolo[3,4-c]pyridine-2-carboxamide;

N-[4-(2,5-diazaspiro[3.5]non-2-ylcarbonyl)phenyl]-1,3-di-
hydro-2H-pyrrolo[3,4-c]pyridine-2-carboxamide;

N-[4-(5-oxa-2-azaspiro[3.4]oct-2-ylcarbonyl)phenyl]-1,3-
dihydro-2H-pyrrolo[3,4-c]pyridine-2-carboxamide;

N-[4-(6-oxa-2-azaspiro[3.5]non-2-ylcarbonyl)phenyl]-1,3-
dihydro-2H-pyrrolo[3,4-c]pyridine-2-carboxamide;

N-[4-(hexahydro-5H-furo[2,3-c]pyrrol-5-ylcarbonyl)phe-
nyl]-1,3-dihydro-2H-pyrrolo[3,4-c]pyridine-2-carboxam-
ide;

N-[4-(tetrahydro-1H-furo[3,4-c]pyrrol-5(3H)-ylcarbonyl)
phenyl]-1,3-dihydro-2H-pyrrolo[3,4-c]pyridine-2-car-
boxamide;

N-[4-(hexahydrofuro[3,4-c]pyridin-5(3H)-ylcarbonyl)phe-
nyl]-1,3-dihydro-2H-pyrrolo[3,4-c]pyridine-2-carboxam-
ide; and pharmaceutically acceptable salts thereof.

Embodiments of Formula (VIIc)

In another aspect, the present invention provides compounds of Formula (VIIc)

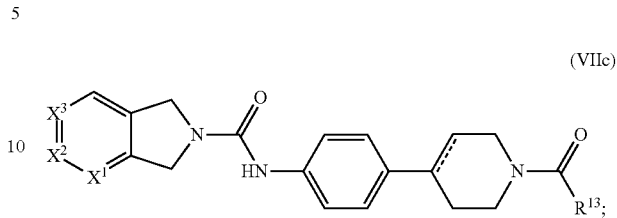

(VIIc)

and pharmaceutically acceptable salts thereof; wherein $X^1$, $X^2$, $X^3$, and $R^{13}$ are as described herein for Formula (Ic), and ⋰ indicates a single or a double bond.

In one embodiment of formula (VIIc),
$X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or
$X^1$ is CH; $X^2$ is N; and $X^3$ is $CR^1$; or
$X^1$ is $CR^1$; $X^2$ is N; and $X^3$ is CH; or
$X^1$ is N; $X^2$ is $CR^1$; and $X^3$ is CH; or
$X^1$ is N; $X^2$ is $CR^1$; and $X^3$ is N;

⋰ indicates a single or double bond;
$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, $C(O)H$, $CF_3$, $C(O)OH$, or $C(O)NH_2$;

$R^3$, at each occurrence, is independently selected alkyl, alkenyl, alkynyl, aryl, or heterocyclyl; wherein each $R^3$ alkyl, alkenyl, and alkynyl is optionally substituted with one, two, three or four independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I;

$R^6$, at each occurrence, is independently selected alkyl, alkenyl, alkynyl, aryl, heterocyclyl, cycloalkyl, or cycloalkenyl; wherein each $R^6$ alkyl, alkenyl, and alkynyl is optionally substituted with one, two, three or four independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, OH, (O), $C(O)OH$, $N_3$, CN, $NH_2$, $CF_3$, $CF_2CF_3$, F, Cl, Br or I;

$R^{10}$, at each occurrence, is independently selected alkyl, alkenyl, alkynyl, aryl, heterocyclyl, cycloalkyl, or cycloalkenyl;

wherein the cyclic moieties represented by $R^3$, $R^6$, and $R^{10}$ are optionally substituted with one, two, three, four, five, or six independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, $C(O)H$, $C(O)OH$, $OH$, $CN$, $N_3$, $NO_2$, $CF_3$, $CF_2CF_3$, $OCF_3$, $OCF_2CF_3$, $SCF_3$, F, Cl, Br or I;

$R^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, or cycloalkenyl; wherein each $R^{13}$ alkyl, alkenyl, and alkynyl is optionally substituted with one, two, three or four independently selected $R^{14}$, $OR^{14}$, $SR^{14}$, $S(O)R^{14}$, $SO_2R^{14}$, $C(O)R^{14}$, $OC(O)R^{14}$, $OC(O)OR^{14}$, $NH_2$, $NHR^{14}$, $N(R^{14})_2$, $NHC(O)R^{14}$, $NR^{14}C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, and cycloalkenyl is optionally substituted with one, two, three or four independently selected $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $C(O)H$, $C(O)OH$, $OH$, $CN$, $N_3$, $NO_2$, $CF_3$, $CF_2CF_3$, $OCF_3$, $OCF_2CF_3$, F, Cl, Br or I;

$R^{14}$, at each occurrence, is independently selected alkyl, alkenyl, alkynyl, aryl, heterocyclyl, cycloalkyl, or cycloalkenyl; wherein each $R^{14}$ alkyl, alkenyl, and alkynyl is optionally substituted with one, two, three or four independently selected heterocyclyl, alkoxy, $NH_2$, $SO_2NH_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{14}$ aryl, heterocyclyl, cycloalkyl, and cycloalkenyl is optionally substituted with one, two, three or four independently selected $R^{16}$, $OR^{16}$, OH, F, Cl, Br or I;

$R^{15}$, at each occurrence, is independently selected alkyl, wherein the $R^{15}$ alkyl is optionally substituted with one, two, three or four alkoxy; and $R^{16}$, at each occurrence, is independently selected alkyl, wherein the $R^{16}$ alkyl is optionally substituted with one, two, three or four alkoxy;

with the proviso that when $R^{13}$ is piperidinyl, it is substituted piperidinyl; and with the proviso that when $R^{13}$ is pyrrolinyl, at least one of $X^1$, $X^2$, and $X^3$ is N.

In one embodiment of Formula (VIIc), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^2$ and $X^3$ are CH; and $X^1$ is $CR^1$; or $X^2$ is CH; and $X^1$ and $X^3$ are $CR^1$; or $X^2$ is CH; and $X^1$ and $X^3$ are N; or $X^2$ and $X^3$ are CH; and $X^1$ is N; or $X^1$ is CH; $X^2$ is N; and $X^3$ is $CR^1$; or $X^1$ is $CR^1$; $X^2$ is N; and $X^3$ is CH; or $X^1$ is N; $X^2$ is $CR^1$; and $X^3$ is CH; or $X^1$ is N; $X^2$ is $CR^1$; and $X^3$ is N. In another embodiment of Formula (VIIc), $X^1$, $X^2$, and $X^3$ are CH. In another embodiment of Formula (VIIc), $X^1$ and $X^3$ are CH; and $X^2$ is N. In another embodiment of Formula (VIIc), $X^1$ and $X^3$ are CH; and $X^2$ is $CR^1$. In another embodiment of Formula (VIIc), $X^2$ and $X^3$ are CH; and $X^1$ is $CR^1$. In another embodiment of Formula (VIIc), $X^1$ is CH; and $X^2$ and $X^3$ are $CR^1$. In another embodiment of Formula (VIIc), $X^2$ is CH; and $X^1$ and $X^3$ are N. In another embodiment of Formula (VIIc), $X^2$ and $X^3$ are CH; and $X^1$ is N. In another embodiment of Formula (VIIc), $X^1$ is CH; $X^2$ is N; and $X^3$ is $CR^1$. In another embodiment of Formula (VIIc), $X^1$ is $CR^1$; $X^2$ is N; and $X^3$ is CH. In another embodiment of Formula (VIIc), $X^1$ is N; $X^2$ is $CR^1$; and $X^3$ is CH. In another embodiment of Formula (VIIc), $X^1$ is N; $X^2$ is $CR^1$; and $X^3$ is N.

In one embodiment of Formula (VIIc),  is a single bond. In another embodiment of Formula (VIIc),  is a double bond.

In another embodiment of Formula (VIIc), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (VIIc), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (VIIc), $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (VIIc), $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (VIIc), $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (VIIc), $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $R^1$ is $C(O)NH_2$. In another embodiment of Formula (VIIc), $R^1$ is F. In another embodiment of Formula (VIIc), $R^1$ is Cl. In another embodiment of Formula (VIIc), $R^1$ is Br. In another embodiment of Formula (VIIc), $R^1$ is CN. In another embodiment of Formula (VIIc), $R^1$ is $NH_2$. In another embodiment of Formula (VIIc), $R^1$ is $NO_2$. In another embodiment of Formula (VIIc), $R^1$ is $CF_3$. In another embodiment of Formula (VIIc), $R^1$ is $C(O)OH$. In another embodiment of Formula (VIIc), $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl.

In another embodiment of Formula (VIIc), $X^1$ and $X^3$ are CH; and $X^2$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (VIIc), $X^1$ and $X^3$ are CH; and $X^2$ is $CR^1$; $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $X^1$ and $X^3$ are CH; and $X^2$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $X^1$ and $X^3$ are CH; and $X^2$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $X^1$ and $X^3$ are CH; and $X^2$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $X^1$ and $X^3$ are CH; and $X^2$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $X^1$ and $X^3$ are CH; and $X^2$ is $CR^1$; $R^1$ is NHC$(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $X^1$ and $X^3$ are CH; and $X^2$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $X^1$ and $X^3$ are CH; and $X^2$ is $CR^1$; $R^1$ is $C(O)NH_2$. In another embodiment of Formula (VIIc), $X^1$ and $X^3$ are CH; and $X^2$ is $CR^1$; and $R^1$ is F. In another embodiment of Formula (VIIc), $X^1$ and $X^3$ are CH; and $X^2$ is $CR^1$; and $R^1$ is Cl. In another embodiment of Formula (VIIc), $X^1$ and $X^3$ are CH; and $X^2$ is $CR^1$; and $R^1$ is Br. In another embodiment of Formula (VIIc), $X^1$ and $X^3$ are CH; and $X^2$ is $CR^1$; and $R^1$ is CN. In another embodiment of Formula (VIIc), $X^1$ and $X^3$ are CH; and $X^2$ is $CR^1$; and $R^1$ is $NH_2$. In another embodiment of Formula (VIIc), $X^1$ and $X^3$ are CH; and $X^2$ is $CR^1$; and $R^1$ is $NO_2$. In another embodiment of Formula (VIIc), $X^1$ and $X^3$ are CH; and $X^2$ is $CR^1$; and $R^1$ is $CF_3$. In another embodiment of Formula (VIIc), $X^1$ and $X^3$ are CH; and $X^2$ is $CR^1$; and $R^1$ is $C(O)OH$. In another embodiment of Formula (VIIc), $X^1$ and $X^3$ are CH; and $X^2$ is $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In another embodiment of Formula (VIIc), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (VIIc), $X^2$ and $X^3$ are CH; and $X^1$ is $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $X^2$ and $X^3$ are CH; and $X^1$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $X^2$ and $X^3$ are CH; and $X^1$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $X^2$ and $X^3$ are CH; and $X^1$ is $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $X^2$ and $X^3$ are CH; and $X^1$ is $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $X^2$ and $X^3$ are CH; and $X^1$ is $CR^1$; $R^1$ is NHC$(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $X^2$ and $X^3$ are CH; and $X^1$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $X^2$ and $X^3$ are CH; and $X^1$ is $CR^1$; and $R^1$ is $C(O)NH_2$. In another embodiment of Formula (VIIc), $X^2$ and $X^3$ are CH; and $X^1$ is $CR^1$; and $R^1$ is F. In another embodiment of Formula (VIIc), $X^2$ and $X^3$ are CH; and $X^1$ is $CR^1$; and $R^1$ is Cl. In another embodiment of Formula (VIIc), $X^2$ and $X^3$ are CH; and $X^1$ is $CR^1$; and $R^1$ is Br. In another embodiment of Formula (VIIc), $X^2$ and $X^3$ are CH; and $X^1$ is $CR^1$; and $R^1$ is CN. In another embodiment of Formula (VIIc), $X^2$ and $X^3$ are CH; and $X^1$ is $CR^1$; and $R^1$ is $NH_2$. In another embodiment of Formula (VIIc), $X^2$ and $X^3$ are CH; and $X^1$ is $CR^1$; and $R^1$ is $NO_2$. In another embodiment of Formula (VIIc), $X^2$ and $X^3$ are CH; and $X^1$ is $CR^1$; and $R^1$ is $CF_3$. In another embodiment of Formula (VIIc), $X^2$ and $X^3$ are CH; and $X^1$ is $CR^1$; and $R^1$ is $C(O)OH$. In another embodiment of Formula (VIIc), $X^2$ and $X^3$ are CH; and $X^1$ is $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In another embodiment of Formula (VIIc), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$. In another embodiment of Formula (VIIc), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or $C(O)OH$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $X^1$ is CH; and $X^2$ and $X^3$ are $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $X^1$ is CH; and $X^2$ and $X^3$ are $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $X^1$ is CH; and $X^2$ and $X^3$ are $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $X^1$ is CH; and $X^2$ and $X^3$ are $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $X^1$ is CH; and $X^2$ and $X^3$ are $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $X^1$ is CH; and $X^2$ and $X^3$ are $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIc), $X^1$ is CH; and $X^2$ and $X^3$ are $CR^1$; and $R^1$ is $C(O)NH_2$. In another embodiment of Formula (VIIc), $X^1$ is CH; and $X^2$ and $X^3$ are $CR^1$; and $R^1$ is F. In another embodiment of Formula (VIIc), $X^1$ is CH; and $X^2$ and $X^3$ are $CR^1$; and $R^1$ is Cl. In another embodiment of Formula (VIIc), $X^1$ is CH; and $X^2$ and $X^3$ are $CR^1$; and $R^1$ is Br. In another embodiment of Formula (VIIc), $X^1$ is CH; and $X^2$ and $X^3$ are $CR^1$; and $R^1$ is CN. In another embodiment of Formula (VIIc), $X^1$ is CH; and $X^2$ and $X^3$ are $CR^1$; and $R^1$ is $NH_2$. In another embodiment of Formula (VIIc), $X^1$ is CH; and $X^2$ and $X^3$ are $CR^1$; and $R^1$ is $NO_2$. In another embodiment of Formula (VIIc), $X^1$ is CH; and $X^2$ and $X^3$ are $CR^1$; and $R^1$ is $CF_3$. In another embodiment of Formula (VIIc), $X^1$ is CH; and $X^2$ and $X^3$ are $CR^1$; and $R^1$ is C(O)OH. In another embodiment of Formula (VIIc), $X^1$ is CH; and $X^2$ and $X^3$ are $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

Still another embodiment pertains to compounds having Formula (VIIc), which include tert-butyl 4-{4-[(1,3-dihydro-2H-isoindol-2-ylcarbonyl)amino]phenyl}-3,6-dihydropyridine-1(2H)-carboxylate;

N-[4-(1-butyryl-1,2,3,6-tetrahydropyridin-4-yl)phenyl]-1,3-dihydro-2H-isoindole-2-carboxamide;

N-[4-(1-isobutyryl-1,2,3,6-tetrahydropyridin-4-yl)phenyl]-1,3-dihydro-2H-isoindole-2-carboxamide;

N-[4-(1-benzoyl-1,2,3,6-tetrahydropyridin-4-yl)phenyl]-1,3-dihydro-2H-isoindole-2-carboxamide;

tert-butyl 4-{4-[(1,3-dihydro-2H-isoindol-2-ylcarbonyl)amino]phenyl}piperidine-1-carboxylate;

N-[4-(1-butyrylpiperidin-4-yl)phenyl]-1,3-dihydro-2H-isoindole-2-carboxamide;

N-[4-(1-isobutyrylpiperidin-4-yl)phenyl]-1,3-dihydro-2H-isoindole-2-carboxamide;

N-[4-(1-benzoylpiperidin-4-yl)phenyl]-1,3-dihydro-2H-isoindole-2-carboxamide;

N-{4-[1-(4-methylbenzoyl)-1,2,3,6-tetrahydropyridin-4-yl]phenyl}-1,3-dihydro-2H-isoindole-2-carboxamide;

N-{4-[1-(5-oxo-L-prolyl)-1,2,3,6-tetrahydropyridin-4-yl]phenyl}-1,3-dihydro-2H-isoindole-2-carboxamide;

N-{4-[1-(5-oxo-D-prolyl)-1,2,3,6-tetrahydropyridin-4-yl]phenyl}-1,3-dihydro-2H-isoindole-2-carboxamide;

N-[4-(1-propionyl-1,2,3,6-tetrahydropyridin-4-yl)phenyl]-1,3-dihydro-2H-isoindole-2-carboxamide;

N-{4-[1-(2-methylbutanoyl)-1,2,3,6-tetrahydropyridin-4-yl]phenyl}-1,3-dihydro-2H-isoindole-2-carboxamide;

N-{4-[1-(2-ethylbutanoyl)-1,2,3,6-tetrahydropyridin-4-yl]phenyl}-1,3-dihydro-2H-isoindole-2-carboxamide;

N-{4-[1-(ethoxyacetyl)-1,2,3,6-tetrahydropyridin-4-yl]phenyl}-1,3-dihydro-2H-isoindole-2-carboxamide;

N-(4-{1-[(2-methoxyethoxy)acetyl]-1,2,3,6-tetrahydropyridin-4-yl}phenyl)-1,3-dihydro-2H-isoindole-2-carboxamide;

N-{4-[1-(tetrahydrofuran-2-ylcarbonyl)-1,2,3,6-tetrahydropyridin-4-yl]phenyl}-1,3-dihydro-2H-isoindole-2-carboxamide;

N-{4-[1-(tetrahydrofuran-3-ylcarbonyl)-1,2,3,6-tetrahydropyridin-4-yl]phenyl}-1,3-dihydro-2H-isoindole-2-carboxamide;

N-{4-[1-(cyclopropylacetyl)-1,2,3,6-tetrahydropyridin-4-yl]phenyl}-1,3-dihydro-2H-isoindole-2-carboxamide;

N-{4-[1-(cyclopentylcarbonyl)-1,2,3,6-tetrahydropyridin-4-yl]phenyl}-1,3-dihydro-2H-isoindole-2-carboxamide;

N-{4-[1-(2-methylbenzoyl)-1,2,3,6-tetrahydropyridin-4-yl]phenyl}-1,3-dihydro-2H-isoindole-2-carboxamide;

N-{4-[1-(3-methylbenzoyl)-1,2,3,6-tetrahydropyridin-4-yl]phenyl}-1,3-dihydro-2H-isoindole-2-carboxamide;

N-{4-[1-(2-methoxybenzoyl)-1,2,3,6-tetrahydropyridin-4-yl]phenyl}-1,3-dihydro-2H-isoindole-2-carboxamide;

N-{4-[1-(3-methoxybenzoyl)-1,2,3,6-tetrahydropyridin-4-yl]phenyl}-1,3-dihydro-2H-isoindole-2-carboxamide;

N-{4-[1-(4-methoxybenzoyl)-1,2,3,6-tetrahydropyridin-4-yl]phenyl}-1,3-dihydro-2H-isoindole-2-carboxamide;

N-{4-[1-(2-fluorobenzoyl)-1,2,3,6-tetrahydropyridin-4-yl]phenyl}-1,3-dihydro-2H-isoindole-2-carboxamide;

N-{4-[1-(3-fluorobenzoyl)-1,2,3,6-tetrahydropyridin-4-yl]phenyl}-1,3-dihydro-2H-isoindole-2-carboxamide;

N-{4-[1-(4-fluorobenzoyl)-1,2,3,6-tetrahydropyridin-4-yl]phenyl}-1,3-dihydro-2H-isoindole-2-carboxamide;

N-{4-[1-(4-chlorobenzoyl)-1,2,3,6-tetrahydropyridin-4-yl]phenyl}-1,3-dihydro-2H-isoindole-2-carboxamide;

N-(4-{1-[3-(dimethylamino)benzoyl]-1,2,3,6-tetrahydropyridin-4-yl}phenyl)-1,3-dihydro-2H-isoindole-2-carboxamide;

N-(4-{1-[4-(dimethylamino)benzoyl]-1,2,3,6-tetrahydropyridin-4-yl}phenyl)-1,3-dihydro-2H-isoindole-2-carboxamide;

N-{4-[1-(3-thienylcarbonyl)-1,2,3,6-tetrahydropyridin-4-yl]phenyl}-1,3-dihydro-2H-isoindole-2-carboxamide;

N-{4-[1-(1H-pyrrol-2-ylcarbonyl)-1,2,3,6-tetrahydropyridin-4-yl]phenyl}-1,3-dihydro-2H-isoindole-2-carboxamide;

N-(4-{1-[(2,5-dimethyl-1H-pyrrol-3-yl)carbonyl]-1,2,3,6-tetrahydropyridin-4-yl}phenyl)-1,3-dihydro-2H-isoindole-2-carboxamide;

N-{4-[1-(1,3-thiazol-4-ylcarbonyl)-1,2,3,6-tetrahydropyridin-4-yl]phenyl}-1,3-dihydro-2H-isoindole-2-carboxamide;

N-{4-[1-(1H-pyrazol-4-ylcarbonyl)-1,2,3,6-tetrahydropyridin-4-yl]phenyl}-1,3-dihydro-2H-isoindole-2-carboxamide;

N-(4-{1-[(3,5-dimethyl-1,2-oxazol-4-yl)carbonyl]-1,2,3,6-tetrahydropyridin-4-yl}phenyl)-1,3-dihydro-2H-isoindole-2-carboxamide;
N-{4-[1-(pyridin-2-ylcarbonyl)-1,2,3,6-tetrahydropyridin-4-yl]phenyl}-1,3-dihydro-2H-isoindole-2-carboxamide;
N-{4-[1-(pyridin-3-ylcarbonyl)-1,2,3,6-tetrahydropyridin-4-yl]phenyl}-1,3-dihydro-2H-isoindole-2-carboxamide;
N-[4-(1-isonicotinoyl-1,2,3,6-tetrahydropyridin-4-yl)phenyl]-1,3-dihydro-2H-isoindole-2-carboxamide;
N-{4-[1-(pyridazin-3-ylcarbonyl)-1,2,3,6-tetrahydropyridin-4-yl]phenyl}-1,3-dihydro-2H-isoindole-2-carboxamide;
N-{4-[1-(pyrazin-2-ylcarbonyl)-1,2,3,6-tetrahydropyridin-4-yl]phenyl}-1,3-dihydro-2H-isoindole-2-carboxamide;
N-{4-[1-(pyrimidin-4-ylcarbonyl)-1,2,3,6-tetrahydropyridin-4-yl]phenyl}-1,3-dihydro-2H-isoindole-2-carboxamide;
N-(4-{1-[3-(piperidin-1-yl)propanoyl]-1,2,3,6-tetrahydropyridin-4-yl}phenyl)-1,3-dihydro-2H-isoindole-2-carboxamide;
N-{4-[1-(morpholin-4-ylacetyl)-1,2,3,6-tetrahydropyridin-4-yl]phenyl}-1,3-dihydro-2H-isoindole-2-carboxamide;
N-(4-{1-[(4-methylpiperazin-1-yl)acetyl]-1,2,3,6-tetrahydropyridin-4-yl}phenyl)-1,3-dihydro-2H-isoindole-2-carboxamide;
N-[4-(1-butyryl-1,2,3,6-tetrahydropyridin-4-yl)phenyl]-1,3-dihydro-2H-pyrrolo[3,4-c]pyridine-2-carboxamide;
N-[4-(1-isobutyryl-1,2,3,6-tetrahydropyridin-4-yl)phenyl]-1,3-dihydro-2H-pyrrolo[3,4-c]pyridine-2-carboxamide;
N-[4-(1-benzoyl-1,2,3,6-tetrahydropyridin-4-yl)phenyl]-1,3-dihydro-2H-pyrrolo[3,4-c]pyridine-2-carboxamide;
N-{4-[1-(tetrahydrofuran-3-ylcarbonyl)-1,2,3,6-tetrahydropyridin-4-yl]phenyl}-1,3-dihydro-2H-pyrrolo[3,4-c]pyridine-2-carboxamide;
N-(4-{1-[(2-methoxyethoxy)acetyl]-1,2,3,6-tetrahydropyridin-4-yl}phenyl)-1,3-dihydro-2H-pyrrolo[3,4-c]pyridine-2-carboxamide;
N-[4-(1-isobutyrylpiperidin-4-yl)phenyl]-1,3-dihydro-2H-pyrrolo[3,4-c]pyridine-2-carboxamide;
N-(4-{1-[(2-methoxyethoxy)acetyl]piperidin-4-yl}phenyl)-1,3-dihydro-2H-isoindole-2-carboxamide;
N-{4-[1-(tetrahydrofuran-2-ylcarbonyl)-1,2,3,6-tetrahydropyridin-4-yl]phenyl}-1,3-dihydro-2H-pyrrolo[3,4-c]pyridine-2-carboxamide;
N-{4-[1-(tetrahydro-2H-pyran-4-ylcarbonyl)-1,2,3,6-tetrahydropyridin-4-yl]phenyl}-1,3-dihydro-2H-pyrrolo[3,4-c]pyridine-2-carboxamide;
N-{4-[1-(1,4-dioxan-2-ylcarbonyl)-1,2,3,6-tetrahydropyridin-4-yl]phenyl}-1,3-dihydro-2H-pyrrolo[3,4-c]pyridine-2-carboxamide;
N-(4-{1-[(1-methylpyrrolidin-3-yl)carbonyl]-1,2,3,6-tetrahydropyridin-4-yl}phenyl)-1,3-dihydro-2H-pyrrolo[3,4-c]pyridine-2-carboxamide;
N-(4-{1-[(1,1-dioxidotetrahydrothiophen-3-yl)carbonyl]-1,2,3,6-tetrahydropyridin-4-yl}phenyl)-1,3-dihydro-2H-pyrrolo[3,4-c]pyridine-2-carboxamide;
N-{4-[1-(2-hydroxy-2-methylpropanoyl)-1,2,3,6-tetrahydropyridin-4-yl]phenyl}-1,3-dihydro-2H-pyrrolo[3,4-c]pyridine-2-carboxamide;
N-{4-[1-(tetrahydro-2H-pyran-4-ylcarbonyl)-1,2,3,6-tetrahydropyridin-4-yl]phenyl}-1,3-dihydro-2H-isoindole-2-carboxamide;
N-{4-[1-(1,4-dioxan-2-ylcarbonyl)-1,2,3,6-tetrahydropyridin-4-yl]phenyl}-1,3-dihydro-2H-isoindole-2-carboxamide;
N-(4-{1-[(1-methylpyrrolidin-3-yl)carbonyl]-1,2,3,6-tetrahydropyridin-4-yl}phenyl)-1,3-dihydro-2H-isoindole-2-carboxamide;
N-(4-{1-[(1,1-dioxidotetrahydrothiophen-3-yl)carbonyl]-1,2,3,6-tetrahydropyridin-4-yl}phenyl)-1,3-dihydro-2H-isoindole-2-carboxamide;
N-{4-[1-(2-hydroxy-2-methylpropanoyl)-1,2,3,6-tetrahydropyridin-4-yl]phenyl}-1,3-dihydro-2H-isoindole-2-carboxamide;
N-{4-[1-(morpholin-4-ylacetyl)-1,2,3,6-tetrahydropyridin-4-yl]phenyl}-1,3-dihydro-2H-pyrrolo[3,4-c]pyridine-2-carboxamide;
N-{4-[1-(tetrahydrofuran-3-ylcarbonyl)piperidin-4-yl]phenyl}-1,3-dihydro-2H-pyrrolo[3,4-c]pyridine-2-carboxamide;
N-(4-{1-[(2-methoxyethoxy)acetyl]piperidin-4-yl}phenyl)-1,3-dihydro-2H-pyrrolo[3,4-c]pyridine-2-carboxamide;
N-{4-[1-(tetrahydrofuran-2-ylcarbonyl)piperidin-4-yl]phenyl}-1,3-dihydro-2H-pyrrolo[3,4-c]pyridine-2-carboxamide;
N-{4-[1-(tetrahydro-2H-pyran-4-ylcarbonyl)piperidin-4-yl]phenyl}-1,3-dihydro-2H-pyrrolo[3,4-c]pyridine-2-carboxamide;
N-{4-[1-(1,4-dioxan-2-ylcarbonyl)piperidin-4-yl]phenyl}-1,3-dihydro-2H-pyrrolo[3,4-c]pyridine-2-carboxamide;
N-(4-{1-[(1-methylpyrrolidin-3-yl)carbonyl]piperidin-4-yl}phenyl)-1,3-dihydro-2H-pyrrolo[3,4-c]pyridine-2-carboxamide;
N-(4-{1-[(1,1-dioxidotetrahydrothiophen-3-yl)carbonyl]piperidin-4-yl}phenyl)-1,3-dihydro-2H-pyrrolo[3,4-c]pyridine-2-carboxamide;
N-{4-[1-(2-hydroxy-2-methylpropanoyl)piperidin-4-yl]phenyl}-1,3-dihydro-2H-pyrrolo[3,4-c]pyridine-2-carboxamide;
N-{4-[1-(morpholin-4-ylacetyl)piperidin-4-yl]phenyl}-1,3-dihydro-2H-pyrrolo[3,4-c]pyridine-2-carboxamide;
N-(4-{1-[(2R)-tetrahydrofuran-2-ylcarbonyl]-1,2,3,6-tetrahydropyridin-4-yl}phenyl)-1,3-dihydro-2H-pyrrolo[3,4-c]pyridine-2-carboxamide;
N-(4-{1-[(2S)-tetrahydrofuran-2-ylcarbonyl]-1,2,3,6-tetrahydropyridin-4-yl}phenyl)-1,3-dihydro-2H-pyrrolo[3,4-c]pyridine-2-carboxamide;
N-{4-[1-(tetrahydrofuran-3-ylcarbonyl)piperidin-4-yl]phenyl}-1,3-dihydro-2H-isoindole-2-carboxamide;
N-{4-[1-(tetrahydrofuran-2-ylcarbonyl)piperidin-4-yl]phenyl}-1,3-dihydro-2H-isoindole-2-carboxamide;
N-{4-[1-(tetrahydro-2H-pyran-4-ylcarbonyl)piperidin-4-yl]phenyl}-1,3-dihydro-2H-isoindole-2-carboxamide;
N-{4-[1-(1,4-dioxan-2-ylcarbonyl)piperidin-4-yl]phenyl}-1,3-dihydro-2H-isoindole-2-carboxamide;
N-(4-{1-[(1-methylpyrrolidin-3-yl)carbonyl]piperidin-4-yl}phenyl)-1,3-dihydro-2H-isoindole-2-carboxamide;
N-(4-{1-[(1,1-dioxidotetrahydrothiophen-3-yl)carbonyl]piperidin-4-yl}phenyl)-1,3-dihydro-2H-isoindole-2-carboxamide;
N-{4-[1-(2-hydroxy-2-methylpropanoyl)piperidin-4-yl]phenyl}-1,3-dihydro-2H-isoindole-2-carboxamide;
N-{4-[1-(morpholin-4-ylacetyl)piperidin-4-yl]phenyl}-1,3-dihydro-2H-isoindole-2-carboxamide;
N-(4-{1-[(1-methylpiperidin-4-yl)carbonyl]-1,2,3,6-tetrahydropyridin-4-yl}phenyl)-1,3-dihydro-2H-pyrrolo[3,4-c]pyridine-2-carboxamide;
N-(4-{1-[(1,1-dioxidotetrahydro-2H-thiopyran-4-yl)carbonyl]-1,2,3,6-tetrahydropyridin-4-yl}phenyl)-1,3-dihydro-2H-pyrrolo[3,4-c]pyridine-2-carboxamide;

N-(4-{1-[(3R)-tetrahydrofuran-3-ylcarbonyl]-1,2,3,6-tetrahydropyridin-4-yl}phenyl)-1,3-dihydro-2H-pyrrolo[3,4-c]pyridine-2-carboxamide;
N-(4-{1-[(3S)-tetrahydrofuran-3-ylcarbonyl]-1,2,3,6-tetrahydropyridin-4-yl}phenyl)-1,3-dihydro-2H-pyrrolo[3,4-c]pyridine-2-carboxamide;
5-cyano-N-{4-[1-(2-methylpropanoyl)-1,2,3,6-tetrahydropyridin-4-yl]phenyl}-1,3-dihydro-2H-isoindole-2-carboxamide;
N-{4-[1-(tetrahydro furan-3-ylacetyl)-1,2,3,6-tetrahydropyridin-4-yl]phenyl}-1,3-dihydro-2H-pyrrolo[3,4-c]pyridine-2-carboxamide;
N-{4-[1-(tetrahydro-2H-pyran-4-ylacetyl)-1,2,3,6-tetrahydropyridin-4-yl]phenyl}-1,3-dihydro-2H-pyrrolo[3,4-c]pyridine-2-carboxamide;
N-{4-[1-(N,N-dimethylglycyl)-1,2,3,6-tetrahydropyridin-4-yl]phenyl}-1,3-dihydro-2H-pyrrolo[3,4-c]pyridine-2-carboxamide;
N-(4-{1-[(4-methylpiperazin-1-yl)acetyl]-1,2,3,6-tetrahydropyridin-4-yl}phenyl)-1,3-dihydro-2H-pyrrolo[3,4-c]pyridine-2-carboxamide;
N-{4-[1-(3-methylbutanoyl)-1,2,3,6-tetrahydropyridin-4-yl]phenyl}-1,3-dihydro-2H-pyrrolo[3,4-c]pyridine-2-carboxamide;
N-{4-[1-(cyclopentylacetyl)-1,2,3,6-tetrahydropyridin-4-yl]phenyl}-1,3-dihydro-2H-pyrrolo[3,4-c]pyridine-2-carboxamide;
N-{4-[1-(tetrahydro furan-2-ylacetyl)-1,2,3,6-tetrahydropyridin-4-yl]phenyl}-1,3-dihydro-2H-pyrrolo[3,4-c]pyridine-2-carboxamide;
N-{4-[1-(tetrahydro-2H-pyran-2-ylacetyl)-1,2,3,6-tetrahydropyridin-4-yl]phenyl}-1,3-dihydro-2H-pyrrolo[3,4-c]pyridine-2-carboxamide;
N-{4-[1-(pyrrolidin-1-ylacetyl)-1,2,3,6-tetrahydropyridin-4-yl]phenyl}-1,3-dihydro-2H-pyrrolo[3,4-c]pyridine-2-carboxamide;
N-{4-[1-(pyrazin-2-ylcarbonyl)-1,2,3,6-tetrahydropyridin-4-yl]phenyl}-1,3-dihydro-2H-pyrrolo[3,4-c]pyridine-2-carboxamide;
N-(4-{1-[(2S)-tetrahydrofuran-2-ylcarbonyl]piperidin-4-yl}phenyl)-1,3-dihydro-2H-pyrrolo[3,4-c]pyridine-2-carboxamide;
N-(4-{1-[(3S)-tetrahydrofuran-3-ylcarbonyl]piperidin-4-yl}phenyl)-1,3-dihydro-2H-pyrrolo[3,4-c]pyridine-2-carboxamide;
5-cyano-N-{4-[1-(tetrahydrofuran-3-ylcarbonyl)-1,2,3,6-tetrahydropyridin-4-yl]phenyl}-1,3-dihydro-2H-isoindole-2-carboxamide;
5-cyano-N-{4-[1-(tetrahydro-2H-pyran-4-ylcarbonyl)-1,2,3,6-tetrahydropyridin-4-yl]phenyl}-1,3-dihydro-2H-isoindole-2-carboxamide;
5-cyano-N-{4-[1-(2-hydroxy-2-methylpropanoyl)-1,2,3,6-tetrahydropyridin-4-yl]phenyl}-1,3-dihydro-2H-isoindole-2-carboxamide;
5-cyano-N-{4-[1-(morpholin-4-ylacetyl)-1,2,3,6-tetrahydropyridin-4-yl]phenyl}-1,3-dihydro-2H-isoindole-2-carboxamide;
N-(4-{1-[(2R)-tetrahydrofuran-2-ylcarbonyl]piperidin-4-yl}phenyl)-1,3-dihydro-2H-pyrrolo[3,4-c]pyridine-2-carboxamide;
N-(4-{1-[(3R)-tetrahydrofuran-3-ylcarbonyl]piperidin-4-yl}phenyl)-1,3-dihydro-2H-pyrrolo[3,4-c]pyridine-2-carboxamide;
N-(4-{1-[(3R)-tetrahydrofuran-3-ylcarbonyl]-1,2,3,6-tetrahydropyridin-4-yl}phenyl)-1,3-dihydro-2H-isoindole-2-carboxamide;
N-(4-{1-[(3S)-tetrahydrofuran-3-ylcarbonyl]-1,2,3,6-tetrahydropyridin-4-yl}phenyl)-1,3-dihydro-2H-isoindole-2-carboxamide;
N-(4-{1-[(1,1-dioxidotetrahydro-2H-thiopyran-4-yl)carbonyl]-1,2,3,6-tetrahydropyridin-4-yl}phenyl)-1,3-dihydro-2H-isoindole-2-carboxamide;
N-(4-{1-[(2R)-tetrahydrofuran-2-ylcarbonyl]piperidin-4-yl}phenyl)-1,3-dihydro-2H-isoindole-2-carboxamide;
N-(4-{1-[(2S)-tetrahydrofuran-2-ylcarbonyl]piperidin-4-yl}phenyl)-1,3-dihydro-2H-isoindole-2-carboxamide;
N-(4-{1-[(3R)-tetrahydrofuran-3-ylcarbonyl]piperidin-4-yl}phenyl)-1,3-dihydro-2H-isoindole-2-carboxamide;
N-(4-{1-[(2-methyl-1,3-oxazol-4-yl)carbonyl]-1,2,3,6-tetrahydropyridin-4-yl}phenyl)-1,3-dihydro-2H-pyrrolo[3,4-c]pyridine-2-carboxamide;
N-{4-[1-(furan-3-ylcarbonyl)-1,2,3,6-tetrahydropyridin-4-yl]phenyl}-1,3-dihydro-2H-pyrrolo[3,4-c]pyridine-2-carboxamide;
N-(4-{1-[(2E)-3-(furan-2-yl)prop-2-enoyl]-1,2,3,6-tetrahydropyridin-4-yl}phenyl)-1,3-dihydro-2H-pyrrolo[3,4-c]pyridine-2-carboxamide;
N-{4-[1-(1,3-oxazol-5-ylcarbonyl)-1,2,3,6-tetrahydropyridin-4-yl]phenyl}-1,3-dihydro-2H-pyrrolo[3,4-c]pyridine-2-carboxamide;
N-{4-[1-(3,3,3-trifluoropropanoyl)-1,2,3,6-tetrahydropyridin-4-yl]phenyl}-1,3-dihydro-2H-pyrrolo[3,4-c]pyridine-2-carboxamide;
N-(4-{1-[(1,5-dimethyl-1H-pyrazol-3-yl)carbonyl]-1,2,3,6-tetrahydropyridin-4-yl}phenyl)-1,3-dihydro-2H-pyrrolo[3,4-c]pyridine-2-carboxamide;
N-(4-{1-[(4-methoxycyclohexyl)carbonyl]-1,2,3,6-tetrahydropyridin-4-yl}phenyl)-1,3-dihydro-2H-pyrrolo[3,4-c]pyridine-2-carboxamide;
N-{4-[1-(2,3-dimethylbutanoyl)-1,2,3,6-tetrahydropyridin-4-yl]phenyl}-1,3-dihydro-2H-pyrrolo[3,4-c]pyridine-2-carboxamide;
N-(4-{1-[(2,2-difluorocyclopropyl)carbonyl]-1,2,3,6-tetrahydropyridin-4-yl}phenyl)-1,3-dihydro-2H-pyrrolo[3,4-c]pyridine-2-carboxamide;
N-{4-[1-(1H-pyrazol-5-ylcarbonyl)-1,2,3,6-tetrahydropyridin-4-yl]phenyl}-1,3-dihydro-2H-pyrrolo[3,4-c]pyridine-2-carboxamide;
N-{4-[1-(tert-butoxyacetyl)-1,2,3,6-tetrahydropyridin-4-yl]phenyl}-1,3-dihydro-2H-pyrrolo[3,4-c]pyridine-2-carboxamide;
N-(4-{1-[3-(1H-1,2,4-triazol-1-yl)propanoyl]-1,2,3,6-tetrahydropyridin-4-yl}phenyl)-1,3-dihydro-2H-pyrrolo[3,4-c]pyridine-2-carboxamide;
N-{4-[1-(3-ethoxypropanoyl)-1,2,3,6-tetrahydropyridin-4-yl]phenyl}-1,3-dihydro-2H-pyrrolo[3,4-c]pyridine-2-carboxamide;
N-{4-[1-(3-hydroxy-3-methylbutanoyl)-1,2,3,6-tetrahydropyridin-4-yl]phenyl}-1,3-dihydro-2H-pyrrolo[3,4-c]pyridine-2-carboxamide;
N-{4-[1-[3-(1H-pyrrol-1-yl)propanoyl]-1,2,3,6-tetrahydropyridin-4-yl]phenyl}-1,3-dihydro-2H-pyrrolo[3,4-c]pyridine-2-carboxamide;
N-(4-{1-[(1-methylcyclopropyl)carbonyl]-1,2,3,6-tetrahydropyridin-4-yl}phenyl)-1,3-dihydro-2H-pyrrolo[3,4-c]pyridine-2-carboxamide;
N-(4-{1-[(2-methylpropoxy)acetyl]-1,2,3,6-tetrahydropyridin-4-yl}phenyl)-1,3-dihydro-2H-pyrrolo[3,4-c]pyridine-2-carboxamide;
N-{4-[1-(1-methylprolyl)-1,2,3,6-tetrahydropyridin-4-yl]phenyl}-1,3-dihydro-2H-pyrrolo[3,4-c]pyridine-2-carboxamide;

N-{4-[1-(2-hydroxy-2-methylbutanoyl)-1,2,3,6-tetrahydropyridin-4-yl]phenyl}-1,3-dihydro-2H-pyrrolo[3,4-c]pyridine-2-carboxamide;
N-(4-{1-[(1-hydroxycyclopropyl)carbonyl]-1,2,3,6-tetrahydropyridin-4-yl}phenyl)-1,3-dihydro-2H-pyrrolo[3,4-c]pyridine-2-carboxamide;
N-{4-[1-(cyclopropylacetyl)-1,2,3,6-tetrahydropyridin-4-yl]phenyl}-1,3-dihydro-2H-pyrrolo[3,4-c]pyridine-2-carboxamide;
N-{4-[1-(cyclopentylcarbonyl)-1,2,3,6-tetrahydropyridin-4-yl]phenyl}-1,3-dihydro-2H-pyrrolo[3,4-c]pyridine-2-carboxamide;
N-[4-(1-{[1-(methoxymethyl)cyclopropyl]carbonyl}-1,2,3,6-tetrahydropyridin-4-yl)phenyl]-1,3-dihydro-2H-pyrrolo[3,4-c]pyridine-2-carboxamide;
N-(4-{1-[(methylsulfonyl)acetyl]-1,2,3,6-tetrahydropyridin-4-yl}phenyl)-1,3-dihydro-2H-pyrrolo[3,4-c]pyridine-2-carboxamide;
N-(4-{1-[(1-methyl-1H-pyrazol-4-yl)carbonyl]-1,2,3,6-tetrahydropyridin-4-yl}phenyl)-1,3-dihydro-2H-pyrrolo[3,4-c]pyridine-2-carboxamide;
N-[4-(1-acetyl-1,2,3,6-tetrahydropyridin-4-yl)phenyl]-1,3-dihydro-2H-pyrrolo[3,4-c]pyridine-2-carboxamide;
N-{4-[1-(cyclopropylcarbonyl)-1,2,3,6-tetrahydropyridin-4-yl]phenyl}-1,3-dihydro-2H-pyrrolo[3,4-c]pyridine-2-carboxamide;
N-{4-[1-(2-ethylbutanoyl)-1,2,3,6-tetrahydropyridin-4-yl]phenyl}-1,3-dihydro-2H-pyrrolo[3,4-c]pyridine-2-carboxamide;
N-{4-[1-(5-oxo-L-prolyl)-1,2,3,6-tetrahydropyridin-4-yl]phenyl}-1,3-dihydro-2H-pyrrolo[3,4-c]pyridine-2-carboxamide;
N-(4-{1-[(2E)-4-methylpent-2-enoyl]-1,2,3,6-tetrahydropyridin-4-yl}phenyl)-1,3-dihydro-2H-pyrrolo[3,4-c]pyridine-2-carboxamide;
N-{4-[1-(2-methoxy-2-methylpropanoyl)-1,2,3,6-tetrahydropyridin-4-yl]phenyl}-1,3-dihydro-2H-pyrrolo[3,4-c]pyridine-2-carboxamide;
N-{4-[1-(cyclopent-1-en-1-ylcarbonyl)-1,2,3,6-tetrahydropyridin-4-yl]phenyl}-1,3-dihydro-2H-pyrrolo[3,4-c]pyridine-2-carboxamide;
N-{4-[1-(thiophen-3-ylacetyl)-1,2,3,6-tetrahydropyridin-4-yl]phenyl}-1,3-dihydro-2H-pyrrolo[3,4-c]pyridine-2-carboxamide;
N-{4-[1-(cyclohexylcarbonyl)-1,2,3,6-tetrahydropyridin-4-yl]phenyl}-1,3-dihydro-2H-pyrrolo[3,4-c]pyridine-2-carboxamide;
N-[4-(1-propanoyl-1,2,3,6-tetrahydropyridin-4-yl)phenyl]-1,3-dihydro-2H-pyrrolo[3,4-c]pyridine-2-carboxamide;
N-{4-[1-(2,2-dimethylbutanoyl)-1,2,3,6-tetrahydropyridin-4-yl]phenyl}-1,3-dihydro-2H-pyrrolo[3,4-c]pyridine-2-carboxamide;
N-(4-{1-[(1-methyl-1H-pyrrol-2-yl)carbonyl]-1,2,3,6-tetrahydropyridin-4-yl}phenyl)-1,3-dihydro-2H-pyrrolo[3,4-c]pyridine-2-carboxamide;
N-{4-[1-(methoxyacetyl)-1,2,3,6-tetrahydropyridin-4-yl]phenyl}-1,3-dihydro-2H-pyrrolo[3,4-c]pyridine-2-carboxamide;
N-{4-[1-(2,2-dimethylpropanoyl)-1,2,3,6-tetrahydropyridin-4-yl]phenyl}-1,3-dihydro-2H-pyrrolo[3,4-c]pyridine-2-carboxamide;
N-{4-[1-(4-methylhexanoyl)-1,2,3,6-tetrahydropyridin-4-yl]phenyl}-1,3-dihydro-2H-pyrrolo[3,4-c]pyridine-2-carboxamide;
N-(4-{1-[(2,2-dimethylcyclopropyl)carbonyl]-1,2,3,6-tetrahydropyridin-4-yl}phenyl)-1,3-dihydro-2H-pyrrolo[3,4-c]pyridine-2-carboxamide;
N-(4-{1-[(1,3-dimethyl-1H-pyrazol-5-yl)carbonyl]-1,2,3,6-tetrahydropyridin-4-yl}phenyl)-1,3-dihydro-2H-pyrrolo[3,4-c]pyridine-2-carboxamide;
N-{4-[1-(cyclobutylacetyl)-1,2,3,6-tetrahydropyridin-4-yl]phenyl}-1,3-dihydro-2H-pyrrolo[3,4-c]pyridine-2-carboxamide;
N-{4-[1-(piperidin-1-ylacetyl)-1,2,3,6-tetrahydropyridin-4-yl]phenyl}-1,3-dihydro-2H-pyrrolo[3,4-c]pyridine-2-carboxamide;
N-(4-{1-[2-(pyrrolidin-1-yl)propanoyl]-1,2,3,6-tetrahydropyridin-4-yl}phenyl)-1,3-dihydro-2H-pyrrolo[3,4-c]pyridine-2-carboxamide;
N-(4-{1-[(1,3-dimethyl-1H-pyrazol-4-yl)carbonyl]-1,2,3,6-tetrahydropyridin-4-yl}phenyl)-1,3-dihydro-2H-pyrrolo[3,4-c]pyridine-2-carboxamide; and pharmaceutically acceptable salts thereof.

Embodiments of Formula (VIIIc)

One embodiment of this invention, therefore, pertains to compounds or pharmaceutically acceptable salts thereof, which are useful as inhibitors of NAMPT, the compounds having Formula (VIIIc)

Formula (VIIIc)

wherein
$X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or
$X^1$ is CH; $X^2$ is N; and $X^3$ is $CR^1$; or
$X^1$ is $CR^1$; $X^2$ is N; and $X^3$ is CH; or
$X^1$ is N; $X^2$ is $CR^1$; and $X^3$ is CH; or
$X^1$ is N; $X^2$ is $CR^1$; and $X^3$ is N;
$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, C(O)H, $CF_3$, C(O)OH, or $C(O)NH_2$;
$R^3$, at each occurrence, is independently selected alkyl, alkenyl, alkynyl, aryl, or heterocyclyl; wherein each $R^3$ alkyl, alkenyl, and alkynyl is optionally substituted with one, two, three or four independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, C(O)H, C(O)OH, OH, (O), CN, $N_3$, $NO_2$, $CF_3$, $CF_2CF_3$, $OCF_3$, $OCF_2CF_3$, F, Cl, Br or I;
$R^6$, at each occurrence, is independently selected alkyl, alkenyl, alkynyl, aryl, heterocyclyl, cycloalkyl, or cycloalkenyl; wherein each $R^6$ alkyl, alkenyl, and alkynyl is optionally substituted with one, two, three or four independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, OH, (O), C(O)OH, $N_3$, CN, $NH_2$, $CF_3$, $CF_2CF_3$, F, Cl, Br or I;

$R^8$, at each occurrence, is independently selected alkyl, alkenyl, alkynyl, aryl, heterocyclyl, cycloalkyl, or cycloalkenyl; wherein each $R^8$ alkyl, alkenyl, and alkynyl is optionally substituted with one, two, three or four independently selected $R^{12}$, $OR^{12}$, $SR^{12}$, $S(O)R^{12}$, $SO_2R^{12}$, $NHR^{12}$, $N(R^{12})_2$, $C(O)R^{12}$, $C(O)NH_2$, $C(O)NHR^{12}$, $C(O)N(R^{12})_2$, $NHC(O)R^{12}$, $NR^{12}C(O)R^{12}$, $NHSO_2R^{12}$, $NHC(O)OR^{12}$, $SO_2NH_2$, $SO_2NHR^{12}$, $SO_2N(R^{12})_2$, $NHC(O)NH_2$, $NHC(O)NHR^{12}$, OH, (O), C(O)OH, $N_3$, CN, $NH_2$, $CF_3$, $CF_2CF_3$, F, Cl, Br or I;

$R^{10}$, at each occurrence, is independently selected alkyl, alkenyl, alkynyl, aryl, heterocyclyl, cycloalkyl, or cycloalkenyl;

$R^{12}$, at each occurrence, is independently selected alkyl, alkenyl, alkynyl, aryl, heterocyclyl, cycloalkyl, or cycloalkenyl; wherein each $R^{12}$ alkyl, alkenyl, and alkynyl is optionally substituted with one or more alkoxy;

wherein the cyclic moieties represented by $R^3$, $R^6$, $R^8$, $R^{10}$, and $R^{12}$ are optionally substituted with one, two, three, four, five, or six independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, C(O)H, C(O)OH, OH, CN, $N_3$, $NO_2$, $CF_3$, $CF_2CF_3$, $OCF_3$, $OCF_2CF_3$, $SCF_3$, F, Cl, Br or I;

$R^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, or cycloalkenyl; wherein each $R^{13}$ alkyl, alkenyl, and alkynyl is optionally substituted with one, two, three or four independently selected $R^{14}$, $OR^{14}$, $SR^{14}$, $S(O)R^{14}$, $SO_2R^{14}$, $C(O)R^{14}$, $OC(O)R^{14}$, $OC(O)OR^{14}$, $NH_2$, $NHR^{14}$, $N(R^{14})_2$, $NHC(O)R^{14}$, $NR^{14}C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, C(O)H, C(O)OH, OH, (O), CN, $N_3$, $NO_2$, $CF_3$, $CF_2CF_3$, $OCF_3$, $OCF_2CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, and cycloalkenyl is optionally substituted with one, two, three or four independently selected $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, C(O)H, C(O)OH, OH, CN, $N_3$, $NO_2$, $CF_3$, $CF_2CF_3$, $OCF_3$, $OCF_2CF_3$, F, Cl, Br or I;

$R^{14}$, at each occurrence, is independently selected alkyl, alkenyl, alkynyl, aryl, heterocyclyl, cycloalkyl, or cycloalkenyl; wherein each $R^{14}$ alkyl, alkenyl, and alkynyl is optionally substituted with one, two, three or four independently selected heterocyclyl, alkoxy, $NH_2$, $SO_2NH_2$, C(O)H, C(O)OH, OH, (O), CN, $N_3$, $NO_2$, $CF_3$, $CF_2CF_3$, $OCF_3$, $OCF_2CF_3$, F, Cl, Br or I; wherein each $R^{14}$ aryl, heterocyclyl, cycloalkyl, and cycloalkenyl is optionally substituted with one, two, three or four independently selected $R^{16}$, $OR^{16}$, OH, F, Cl, Br, or I; wherein the $R^{16}$ alkyl is optionally substituted with one, two, three or four alkoxy;

$R^{15}$, at each occurrence, is independently selected alkyl; wherein the $R^{15}$ alkyl is optionally substituted with one, two, three or four alkoxy;

$R^{16}$, at each occurrence, is independently selected alkyl, wherein the $R^{16}$ alkyl is optionally substituted with one, two, three or four alkoxy;

with the proviso that when $R^{13}$ is piperidinyl, it is substituted piperidinyl; and with the proviso that when $R^{13}$ is pyrrolinyl, at least one of $X^1$, $X^2$, and $X^3$ is N.

In one embodiment of Formula (VIIIc), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N; or $X^1$ is CH; $X^2$ is N; and $X^3$ is $CR^1$; or $X^1$ is $CR^1$; $X^2$ is N; and $X^3$ is CH; or $X^1$ is N; $X^2$ is $CR^1$; and $X^3$ is CH; or $X^1$ is N; $X^2$ is $CR^1$; and $X^3$ is N. In another embodiment of Formula (VIIIc), $X^1$, $X^2$, and $X^3$ are CH. In another embodiment of Formula (VIIIc), $X^1$ and $X^3$ are CH; and $X^2$ is N. In another embodiment of Formula (VIIIc), $X^1$ and $X^3$ are CH; and $X^2$ is $CR^1$. In another embodiment of Formula (VIIIc), $X^2$ and $X^3$ are CH; and $X^1$ is $CR^1$. In another embodiment of Formula (VIIIc), $X^1$ is CH; and $X^2$ and $X^3$ are $CR^1$. In another embodiment of Formula (VIIIc), $X^2$ is CH; and $X^1$ and $X^3$ are N. In another embodiment of Formula (VIIIc), $X^2$ and $X^3$ are CH; and $X^1$ is N. In another embodiment of Formula (VIIIc), $X^1$ is CH; $X^2$ is N; and $X^3$ is $CR^1$. In another embodiment of Formula (VIIIc), $X^1$ is $CR^1$; $X^2$ is N; and $X^3$ is CH. In another embodiment of Formula (VIIIc), $X^1$ is N; $X^2$ is $CR^1$; and $X^3$ is CH. In another embodiment of Formula (VIIIc), $X^1$ is N; $X^2$ is $CR^1$; and $X^3$ is N.

In another embodiment of Formula (VIIIc), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (VIIIc), $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (VIIIc), $R^1$ is $R^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (VIIIc), $R^1$ is $OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (VIIIc), $R^1$ is C(O)$OR^3$; wherein $R^3$ is alkyl, alkenyl, or heterocyclyl; wherein each alkyl is optionally substituted with one or more independently selected $R^6$, $OR^6$, $NH_2$, $N(R^6)_2$, $NHC(O)R^6$, or OH; wherein $R^6$ is alkyl or heterocyclyl. In another embodiment of Formula (VIIIc), $R^1$ is C(O)$NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $R^1$ is C(O)$NH_2$. In another embodiment of Formula (VIIIc), $R^1$ is F. In another embodiment of Formula (VIIIc), $R^1$ is Cl. In another embodiment of Formula (VIIIc), $R^1$ is Br. In another embodiment of Formula (VIIIc), $R^1$ is CN. In another embodiment of Formula (VIIIc), $R^1$ is $NH_2$. In another embodiment of Formula (VIIIc), $R^1$ is $NO_2$. In another embodiment of Formula (VIIIc), $R^1$ is $CF_3$. In another embodiment of Formula (VIIIc), $R^1$ is C(O)OH. In another embodiment of Formula (VIIIc), $R^1$ is C(O)$R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl.

In another embodiment of Formula (VIIIc), $X^1$ and $X^3$ are CH; and $X^2$ is $CR^1$; and $R^1$ is $R^3$, $OR^3$, C(O)$OR^3$, C(O)$NH_2$, C(O)$NHR^3$, $NHC(O)R^3$, $NHSO_2R^3$, F, Cl, Br, I, CN, $NH_2$, $NO_2$, $CF_3$, or C(O)OH. In another embodiment of Formula (VIIIc), $X^1$ and $X^3$ are CH; and $X^2$ is $CR^1$; $R^1$ is $R^3$, $OR^3$, C(O)$OR^3$, C(O)$NH_2$, C(O)$NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $X^1$ and $X^3$ are CH; and $X^2$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $X^1$ and $X^3$ are CH; and $X^2$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $X^1$ and $X^3$ are CH; and $X^2$ is $CR^1$; $R^1$ is C(O)$OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $X^1$ and $X^3$ are CH; and $X^2$ is $CR^1$; $R^1$ is C(O)$NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $X^1$ and $X^3$ are CH; and $X^2$ is $CR^1$; $R^1$ is NHC(O)$R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $X^1$ and $X^3$ are CH; and $X^2$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $X^1$ and $X^3$ are CH; and $X^2$ is $CR^1$; and $R^1$ is C(O)$NH_2$. In another embodiment of Formula (VIIIc), $X^1$ and $X^3$ are CH; and $X^2$ is $CR^1$; and $R^1$ is F. In another embodiment of Formula (VIIIc), $X^1$ and $X^3$ are CH; and $X^2$ is $CR^1$; and $R^1$ is Cl. In another embodiment of Formula (VIIIc), $X^1$ and $X^3$ are CH; and $X^2$ is $CR^1$; and $R^1$ is Br. In another embodiment of Formula (VIIIc), $X^1$ and $X^3$ are CH; and $X^2$ is $CR^1$; and $R^1$ is CN. In another embodiment of Formula (VIIIc), $X^1$ and $X^3$ are CH; and $X^2$ is $CR^1$; and $R^1$ is $NH_2$. In another embodiment of Formula (VIIIc), $X^1$ and $X^3$ are CH; and $X^2$ is $CR^1$; and $R^1$ is $NO_2$. In another embodiment of Formula (VIIIc), $X^1$ and $X^3$ are CH; and $X^2$ is $CR^1$; and $R^1$ is $CF_3$. In another embodiment of Formula (VIIIc), $X^1$ and $X^3$ are CH; and $X^2$ is $CR^1$; and $R^1$ is C(O)OH. In another embodiment of Formula (VIIIc), $X^1$ and $X^3$ are CH; and $X^2$ is $CR^1$; $R^1$ is C(O)$R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In another embodiment of Formula (VIIIc), $X^2$ and $X^3$ are CH; and $X^1$ is $CR^1$; and $R^1$ is $R^3$, $OR^3$, C(O)$OR^3$, C(O)$NH_2$, C(O)$NHR^3$, $NHC(O)R^3$, $NHSO_2R^3$, F, Cl, Br, I, CN, $NH_2$, $NO_2$, $CF_3$, or C(O)OH. In another embodiment of Formula (VIIIc), $X^2$ and $X^3$ are CH; and $X^1$ is $CR^1$; and $R^1$ is $R^3$, $OR^3$, C(O)$OR^3$, C(O)$NH_2$, C(O)$NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $X^2$ and $X^3$ are CH; and $X^1$ is $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $X^2$ and $X^3$ are CH; and $X^1$ is $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $X^2$ and $X^3$ are CH; and $X^1$ is $CR^1$; $R^1$ is C(O)$OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $X^2$ and $X^3$ are CH; and $X^1$ is $CR^1$; $R^1$ is C(O)$NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $X^2$ and $X^3$ are CH; and $X^1$ is $CR^1$; $R^1$ is NHC(O)$R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $X^2$ and $X^3$ are CH; and $X^1$ is $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $X^2$ and $X^3$ are CH; and $X^1$ is $CR^1$; and $R^1$ is C(O)$NH_2$. In another embodiment of Formula (VIIIc), $X^2$ and $X^3$ are CH; and $X^1$ is $CR^1$; and $R^1$ is F. In another embodiment of Formula (VIIIc), $X^2$ and $X^3$ are CH; and $X^1$ is $CR^1$; and $R^1$ is Cl. In another embodiment of Formula (VIIIc), $X^2$ and $X^3$ are CH; and $X^1$ is $CR^1$; and $R^1$ is Br. In another embodiment of Formula (VIIIc), $X^2$ and $X^3$ are CH; and $X^1$ is $CR^1$; and $R^1$ is CN. In another embodiment of Formula (VIIIc), $X^2$ and $X^3$ are CH; and $X^1$ is $CR^1$; and $R^1$ is $NH_2$. In another embodiment of Formula (VIIIc), $X^2$ and $X^3$ are CH; and $X^1$ is $CR^1$; and $R^1$ is $NO_2$. In another embodiment of Formula (VIIIc), $X^2$ and $X^3$ are CH; and $X^1$ is $CR^1$; and $R^1$ is $CF_3$. In another embodiment of Formula (VIIIc), $X^2$ and $X^3$ are CH; and $X^1$ is $CR^1$; and $R^1$ is C(O)OH. In another embodiment of Formula (VIIIc), $X^2$ and $X^3$ are CH; and $X^1$ is $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In another embodiment of Formula (VIIIc), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH. In another embodiment of Formula (VIIIc), $X^1$ is CH; and $X^2$ and $X^3$ are $CR^1$; and $R^1$ is $R^3$, $OR^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $X^1$ is CH; and $X^2$ and $X^3$ are $CR^1$; $R^1$ is $R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $X^1$ is CH; and $X^2$ and $X^3$ are $CR^1$; $R^1$ is $OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $X^1$ is CH; and $X^2$ and $X^3$ are $CR^1$; $R^1$ is $C(O)OR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $X^1$ is CH; and $X^2$ and $X^3$ are $CR^1$; $R^1$ is $C(O)NHR^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $X^1$ is CH; and $X^2$ and $X^3$ are $CR^1$; $R^1$ is $NHC(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $X^1$ is CH; and $X^2$ and $X^3$ are $CR^1$; $R^1$ is $NHSO_2R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; wherein $R^6$ is alkyl or heterocyclyl. In another embodiment of Formula (VIIIc), $X^1$ is CH; and $X^2$ and $X^3$ are $CR^1$; and $R^1$ is $C(O)NH_2$. In another embodiment of Formula (VIIIc), $X^1$ is CH; and $X^2$ and $X^3$ are $CR^1$; and $R^1$ is F. In another embodiment of Formula (VIIIc), $X^1$ is CH; and $X^2$ and $X^3$ are $CR^1$; and $R^1$ is Cl. In another embodiment of Formula (VIIIc), $X^1$ is CH; and $X^2$ and $X^3$ are $CR^1$; and $R^1$ is Br. In another embodiment of Formula (VIIIc), $X^1$ is CH; and $X^2$ and $X^3$ are $CR^1$; and $R^1$ is CN. In another embodiment of Formula (VIIIc), $X^1$ is CH; and $X^2$ and $X^3$ are $CR^1$; and $R^1$ is $NH_2$. In another embodiment of Formula (VIIIc), $X^1$ is CH; and $X^2$ and $X^3$ are $CR^1$; and $R^1$ is $NO_2$. In another embodiment of Formula (VIIIc), $X^1$ is CH; and $X^2$ and $X^3$ are $CR^1$; and $R^1$ is $CF_3$. In another embodiment of Formula (VIIIc), $X^1$ is CH; and $X^2$ and $X^3$ are $CR^1$; and $R^1$ is C(O)OH. In another embodiment of Formula (VIIIc), $X^1$ is CH; and $X^2$ and $X^3$ are $CR^1$; and $R^1$ is $C(O)R^3$; wherein $R^3$ is alkyl, alkenyl, or heterocyclyl; wherein each alkyl is optionally substituted with one or more independently selected $R^6$, $OR^6$, $NH_2$, $NHC(O)R^6$, $N(R^6)_2$, or OH; and $R^6$ is alkyl or heterocyclyl.

In one embodiment of Formula (VIIIc), $X^1$, $X^2$, and $X^3$ are CH; or $X^1$ and $X^3$ are CH; and $X^2$ is N; or $X^1$ and $X^3$ are CH; and $X^2$ is $CR^1$; or $X^2$ and $X^3$ are CH; and $X^1$ is $CR^1$; or $X^1$ is CH; and $X^2$ and $X^3$ are $CR^1$; or $X^2$ is CH; and $X^1$ and $X^3$ are N; or $X^2$ and $X^3$ are CH; and $X^1$ is N; or $R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH;

$R^3$, at each occurrence, is independently selected alkyl, alkenyl, or heterocyclyl; wherein each $R^3$ alkyl is optionally substituted with one, two, three or four independently selected $R^6$, $OR^6$, $NH_2$, $N(R^6)_2$, $NHC(O)R^6$, OH, F, Cl, Br or I;

$R^6$, at each occurrence, is independently selected alkyl or heterocyclyl; wherein each $R^6$ alkyl is optionally substituted with one, two, three or four independently selected F, Cl, Br or I;

$R^8$, at each occurrence, is independently selected alkyl, aryl, heterocyclyl, or cycloalkyl; wherein each $R^8$ alkyl is optionally substituted with one, two, three or four independently selected $R^{12}$, $OR^{12}$OH, $CF_3$, F, Cl, Br or I;

$R^{12}$, at each occurrence, is independently selected alkyl, heterocyclyl, or cycloalkyl; wherein each $R^{12}$ alkyl is optionally substituted with one or more alkoxy;

wherein the cyclic moieties represented by $R^3$, $R^6$, $R^8$, and $R^{12}$ are optionally substituted with one, two, three, four, five, or six independently selected $R^{13}$, $OR^{13}$, $SO_2R^{13}$, $C(O)R^{13}$, $CO(O)R^{13}$, $NH_2$, $N(R^{13})_2$, $NHC(O)R^{13}$, $NHC(O)OR^{13}$, $C(O)NH_2$, $C(O)NHR^{13}$, $C(O)N(R^{13})_2$, OH, CN, $CF_3$, $OCF_3$, $SCF_3$, F, Cl, Br or I;

$R^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, or cycloalkenyl; wherein each $R^{13}$ alkyl, alkenyl, and alkynyl is optionally substituted with one, two, three or four independently selected $R^{14}$, $OR^{14}$, $SO_2R^{14}$, $NH_2$, $NHR^{14}$, $N(R^{14})_2$, $NHC(O)R^{14}$, $NHC(O)OR^{14}$, OH, $CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, or cycloalkenyl is optionally substituted with one, two, three or four independently selected $R^{15}$, $OR^{15}$, $SO_2R^{15}$, $C(O)R^{15}$, $N(R^{15})_2$, $NHC(O)R^{15}$, OH, CN, $CF_3$, F, Cl, Br or I;

$R^{14}$, at each occurrence, is independently selected alkyl, aryl, heterocyclyl, or cycloalkyl; wherein each $R^{14}$ alkyl is optionally substituted with one, two, three or four independently selected heterocyclyl, alkoxy, OH, F, Cl, Br or I; wherein each $R^{14}$ aryl, heterocyclyl, and cycloalkyl is optionally substituted with one, two, three or four independently selected $R^{16}$, $OR^{16}$, OH, F, Cl, Br, or I;

$R^{15}$, at each occurrence, is independently selected alkyl; wherein the $R^{15}$ alkyl is optionally substituted with one, two, three or four alkoxy; and $R^{16}$, at each occurrence, is independently selected alkyl, wherein the $R^{16}$ alkyl is optionally substituted with one, two, three or four alkoxy;

with the proviso that when $R^{13}$ is piperidinyl, it is substituted piperidinyl; and with the proviso that when $R^{13}$ is pyrrolinyl, at least one of $X^1$, $X^2$, and $X^3$ is N.

In another embodiment of Formula (VIIIc), $X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$X^2$ is CH; and $X^1$ and $X^3$ are N; or
$X^2$ and $X^3$ are CH; and $X^1$ is N; or
$R^1$ is $R^3$, $OR^3$, $C(O)R^3$, $C(O)OR^3$, $C(O)NH_2$, $C(O)NHR^3$, $NHC(O)R^3$, $NHSO_2R^3$, F, Cl, Br, I, CN, $NH_2$, $NO_2$, $CF_3$, or C(O)OH;

$R^3$, at each occurrence, is independently selected alkyl, alkenyl, or heterocyclyl; wherein each $R^3$ alkyl is optionally substituted with one, two, three or four independently selected $R^6$, $OR^6$, $NH_2$, $N(R^6)_2$, $NHC(O)R^6$, or OH;

$R^6$, at each occurrence, is independently selected alkyl or heterocyclyl;

$R^8$, at each occurrence, is independently selected alkyl, aryl, heterocyclyl, or cycloalkyl; wherein each $R^8$ alkyl is optionally substituted with one, two, three or four independently selected $R^{12}$, $OR^{12}OH$, or $CF_3$;

$R^{12}$, at each occurrence, is independently selected alkyl, heterocyclyl, or cycloalkyl; wherein each $R^{12}$ alkyl is optionally substituted with one or more alkoxy;

wherein the cyclic moieties represented by $R^3$, $R^6$, $R^8$, and $R^{12}$ are optionally substituted with one, two, three, four, five, or six independently selected $R^{13}$, $OR^{13}$, $SO_2R^{13}$, $C(O)R^{13}$, $CO(O)R^{13}$, $NH_2$, $N(R^{13})_2$, $NHC(O)R^{13}$, $NHC(O)OR^{13}$, $C(O)NH_2$, $C(O)NHR^{13}$, $C(O)N(R^{13})_2$, OH, CN, $CF_3$, $OCF_3$, $SCF_3$, F, or Cl;

$R^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, or cycloalkenyl; wherein each $R^{13}$ alkyl and alkynyl is optionally substituted with one, two, three or four independently selected $R^{14}$, $OR^{14}$, $SO_2R^{14}$, $NH_2$, $NHR^{14}$, $N(R^{14})_2$, $NHC(O)R^{14}$, $NHC(O)OR^{14}$, OH, or $CF_3$; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, isooxazolyl, cycloalkyl, and cycloalkenyl is optionally substituted with one, two, three or four independently selected $R^{15}$, $OR^{15}$, $SO_2R^{15}$, $C(O)R^{15}$, $N(R^{15})_2$, $NHC(O)R^{15}$, CN, OH, $CF_3$, F, or Cl;

$R^{14}$, at each occurrence, is independently selected alkyl, aryl, heterocyclyl, or cycloalkyl; wherein each $R^{14}$ alkyl is optionally substituted with one, two, three or four independently selected heterocyclyl, alkoxy, or OH; wherein each $R^{14}$ aryl, heterocyclyl, and cycloalkyl is optionally substituted with one, two, three or four independently selected $R^{16}$, $OR^{16}$, OH, or Cl;

$R^{15}$, at each occurrence, is independently selected alkyl; wherein the $R^{15}$ alkyl is optionally substituted with one, two, three or four alkoxy; and $R^{16}$, at each occurrence, is independently selected alkyl, wherein the $R^{16}$ alkyl is optionally substituted with one, two, three or four independently selected alkoxy;

with the proviso that when $R^{13}$ is piperidinyl, it is substituted piperidinyl; and with the proviso that when $R^{13}$ is pyrrolinyl, at least one of $X^1$, $X^2$, and $X^3$ is N.

Still another embodiment pertains to compounds having Formula (VIIIc), which include N-[4-(1-benzoylpiperidin-4-yl)butyl]-1,3-dihydro-2H-isoindole-2-carboxamide;

N-{4-[1-(pyridin-3-ylcarbonyl)piperidin-4-yl]butyl}-1,3-dihydro-2H-isoindole-2-carboxamide;

N-[4-(1-benzoylpiperidin-4-yl)butyl]-5-cyano-1,3-dihydro-2H-isoindole-2-carboxamide;

N-{4-[1-(pyridin-2-ylcarbonyl)piperidin-4-yl]butyl}-1,3-dihydro-2H-isoindole-2-carboxamide;

N-[4-(1-benzoylpiperidin-4-yl)butyl]-1,3-dihydro-2H-pyrrolo[3,4-c]pyridine-2-carboxamide;

N-{4-[1-(2-chlorobenzoyl)piperidin-4-yl]butyl}-1,3-dihydro-2H-pyrrolo[3,4-c]pyridine-2-carboxamide;

N-{4-[1-(tetrahydrofuran-2-ylacetyl)piperidin-4-yl]butyl}-1,3-dihydro-2H-pyrrolo[3,4-c]pyridine-2-carboxamide;

N-(4-{1-[(1,1-dioxidotetrahydrothiophen-3-yl)carbonyl]piperidin-4-yl}butyl)-1,3-dihydro-2H-pyrrolo[3,4-c]pyridine-2-carboxamide;

N-{4-[1-(tetrahydrofuran-3-ylacetyl)piperidin-4-yl]butyl}-1,3-dihydro-2H-pyrrolo[3,4-c]pyridine-2-carboxamide;

N-{4-[1-(cyclohexylcarbonyl)piperidin-4-yl]butyl}-1,3-dihydro-2H-pyrrolo[3,4-c]pyridine-2-carboxamide;

N-(4-{1-[(4,4-difluorocyclohexyl)carbonyl]piperidin-4-yl}butyl)-1,3-dihydro-2H-pyrrolo[3,4-c]pyridine-2-carboxamide;

N-{4-[1-(2-hydroxy-2-methylpropanoyl)piperidin-4-yl]butyl}-1,3-dihydro-2H-pyrrolo[3,4-c]pyridine-2-carboxamide;

N-(4-{1-[(2R)-tetrahydrofuran-2-ylcarbonyl]piperidin-4-yl}butyl)-1,3-dihydro-2H-pyrrolo[3,4-c]pyridine-2-carboxamide;

N-(4-{1-[(2S)-tetrahydrofuran-2-ylcarbonyl]piperidin-4-yl}butyl)-1,3-dihydro-2H-pyrrolo[3,4-c]pyridine-2-carboxamide;

N-(4-{1-[(2-methoxyethoxy)acetyl]piperidin-4-yl}butyl)-1,3-dihydro-2H-pyrrolo[3,4-c]pyridine-2-carboxamide;

N-{4-[1-(tetrahydrofuran-3-ylcarbonyl)piperidin-4-yl]butyl}-1,3-dihydro-2H-pyrrolo[3,4-c]pyridine-2-carboxamide;

N-(4-{1-[(propan-2-yloxy)acetyl]piperidin-4-yl}butyl)-1,3-dihydro-2H-pyrrolo[3,4-c]pyridine-2-carboxamide;

N-{4-[1-(cyclopropylacetyl)piperidin-4-yl]butyl}-1,3-dihydro-2H-pyrrolo[3,4-c]pyridine-2-carboxamide;

N-{4-[1-(4,4,4-trifluorobutanoyl)piperidin-4-yl]butyl}-1,3-dihydro-2H-pyrrolo[3,4-c]pyridine-2-carboxamide; and pharmaceutically acceptable salts thereof.

Pharmaceutical Compositions, Combination Therapies, Methods of Treatment, and Administration Another embodiment comprises pharmaceutical compositions comprising a compound having Formula (I) and an excipient.

Still another embodiment comprises methods of treating cancer in a mammal comprising administering thereto a therapeutically acceptable amount of a compound having Formula (I).

Still another embodiment pertains to compositions for treating diseases during which NAMPT is expressed, said compositions comprising an excipient and a therapeutically effective amount of the compound having Formula (I).

Still another embodiment pertains to compositions for treating diseases during which ROCK is expressed, said compositions comprising an excipient and a therapeutically effective amount of the compound having Formula (I).

Still another embodiment pertains to methods of treating disease in a patient during which NAMPT is expressed, said methods comprising administering to the patient a therapeutically effective amount of a compound having Formula (I).

Still another embodiment pertains to methods of treating disease in a patient during which ROCK is expressed, said methods comprising administering to the patient a therapeutically effective amount of a compound having Formula (I).

Still another embodiment pertains to compositions for treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia, said compositions comprising an excipient and a therapeutically effective amount of the compound having Formula (I).

Still another embodiment pertains to compositions for treating hypertension, chronic and congestive heart failure, cardiac hypertrophy, restenosis, chronic renal failure, cerebral vasospasm after subarachnoid bleeding, pulmonary hypertension, atherosclerosis, asthma, male erectile dysfunctions, female sexual dysfunction, over-active bladder syndrome, spinal-cord injury, traumatic brain injury, stroke, inflammatory and demyelinating diseases, Alzheimer's disease, pain, multiple sclerosis, amyotrophic lateral sclerosis, Huntington's disease, Parkinson's disease, inflammatory pain, rheumatoid arthritis, osteoarthritis, irritable bowel syndrome, Crohn's disease, psoriasis, ulcerative colitis, lupus, inflammatory bowel disease, cancer, tumor metastasis, viral infections, bacterial infections, insulin resistance, diabetes, ocular hypertension, preterm labor, atherosclerosis, spinal muscular atrophy, encephalomyelitis, osteoporosis, HIV-1, encephalitis, ischemic CNS disorders, vascular or AD type dementia, glaucoma, retinopathy, benign prostatic hypertrophy, psychiatric disorders, in particular depression, schizophrenia, obsessive compulsive disorder and bipolar disorder, epilepsy and seizure disorders, for decreasing ischemia-reperfusion injury, myocardial infarct size and myocardial fibrosis, for the prevention of graft failure, and cystic fibrosis, said compositions comprising an excipient and a therapeutically effective amount of the compound having Formula (I).

Still another embodiment pertains to methods of treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia in a patient, said methods comprising administering to the patient a therapeutically effective amount of a compound having Formula (I).

Still another embodiment pertains to methods of treating hypertension, chronic and congestive heart failure, cardiac hypertrophy, restenosis, chronic renal failure, cerebral vasospasm after subarachnoid bleeding, pulmonary hypertension, atherosclerosis, asthma, male erectile dysfunctions, female sexual dysfunction, over-active bladder syndrome, spinal-cord injury, traumatic brain injury, stroke, inflammatory and demyelinating diseases, Alzheimer's disease, pain, multiple sclerosis, amyotrophic lateral sclerosis, Huntington's disease, Parkinson's disease, inflammatory pain, rheumatoid arthritis, osteoarthritis, irritable bowel syndrome, Crohn's disease, psoriasis, ulcerative colitis, lupus, inflammatory bowel disease, cancer, tumor metastasis, viral infections, bacterial infections, insulin resistance, diabetes, ocular hypertension, preterm labor, atherosclerosis, spinal muscular atrophy, encephalomyelitis, osteoporosis, HIV-1, encephalitis, ischemic CNS disorders, vascular or AD type dementia, glaucoma, retinopathy, benign prostatic hypertrophy, psychiatric disorders, in particular depression, schizophrenia, obsessive compulsive disorder and bipolar disorder, epilepsy and seizure disorders, for decreasing ischemia-reperfusion injury, myocardial infarct size and myocardial fibrosis, for the prevention of graft failure, and cystic fibrosis, said methods comprising administering to the patient a therapeutically effective amount of a compound having Formula (I).

Still another embodiment pertains to compositions for treating diseases during which NAMPT is expressed, said compositions comprising an excipient and a therapeutically effective amount of the compound having Formula (I) and a therapeutically effective amount of one additional therapeutic agent or more than one additional therapeutic agent.

Still another embodiment pertains to compositions for treating diseases during which ROCK is expressed, said compositions comprising an excipient and a therapeutically effective amount of the compound having Formula (I) and a therapeutically effective amount of one additional therapeutic agent or more than one additional therapeutic agent.

Still another embodiment pertains to methods of treating disease in a patient during which NAMPT is expressed, said methods comprising administering to the patient a therapeutically effective amount of a compound having Formula (I) and a therapeutically effective amount of one additional therapeutic agent or more than one additional therapeutic agent.

Still another embodiment pertains to methods of treating disease in a patient during which ROCK is expressed, said methods comprising administering to the patient a therapeutically effective amount of a compound having Formula (I)

and a therapeutically effective amount of one additional therapeutic agent or more than one additional therapeutic agent.

Still another embodiment pertains to compositions for treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia, said compositions comprising an excipient and a therapeutically effective amount of the compound having Formula (I) and a therapeutically effective amount of one additional therapeutic agent or more than one additional therapeutic agent.

Still another embodiment pertains to compositions for treating hypertension, chronic and congestive heart failure, cardiac hypertrophy, restenosis, chronic renal failure, cerebral vasospasm after subarachnoid bleeding, pulmonary hypertension, atherosclerosis, asthma, male erectile dysfunctions, female sexual dysfunction, over-active bladder syndrome, spinal-cord injury, traumatic brain injury, stroke, inflammatory and demyelinating diseases, Alzheimer's disease, pain, multiple sclerosis, amyotrophic lateral sclerosis, Huntington's disease, Parkinson's disease, inflammatory pain, rheumatoid arthritis, osteoarthritis, irritable bowel syndrome, Crohn's disease, psoriasis, ulcerative colitis, lupus, inflammatory bowel disease, cancer, tumor metastasis, viral infections, bacterial infections, insulin resistance, diabetes, ocular hypertension, preterm labor, atherosclerosis, spinal muscular atrophy, encephalomyelitis, osteoporosis, HIV-1, encephalitis, ischemic CNS disorders, vascular or AD type dementia, glaucoma, retinopathy, benign prostatic hypertrophy, psychiatric disorders, in particular depression, schizophrenia, obsessive compulsive disorder and bipolar disorder, epilepsy and seizure disorders, for decreasing ischemia-reperfusion injury, myocardial infarct size and myocardial fibrosis, for the prevention of graft failure, and cystic fibrosis, said compositions comprising an excipient and a therapeutically effective amount of the compound having Formula (I) and a therapeutically effective amount of one additional therapeutic agent or more than one additional therapeutic agent.

Still another embodiment pertains to methods of treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia in a patient, said methods comprising administering to the patient a therapeutically effective amount of the compound having Formula (I) and a therapeutically effective amount of one additional therapeutic agent or more than one additional therapeutic agent.

Still another embodiment pertains to methods of treating hypertension, chronic and congestive heart failure, cardiac hypertrophy, restenosis, chronic renal failure, cerebral vasospasm after subarachnoid bleeding, pulmonary hypertension, atherosclerosis, asthma, male erectile dysfunctions, female sexual dysfunction, over-active bladder syndrome, spinal-cord injury, traumatic brain injury, stroke, inflammatory and demyelinating diseases, Alzheimer's disease, pain, multiple sclerosis, amyotrophic lateral sclerosis, Huntington's disease, Parkinson's disease, inflammatory pain, rheumatoid arthritis, osteoarthritis, irritable bowel syndrome, Crohn's disease, psoriasis, ulcerative colitis, lupus, inflammatory bowel disease, cancer, tumor metastasis, viral infections, bacterial infections, insulin resistance, diabetes, ocular hypertension, preterm labor, atherosclerosis, spinal muscular atrophy, encephalomyelitis, osteoporosis, HIV-1, encephalitis, ischemic CNS disorders, vascular or AD type dementia, glaucoma, retinopathy, benign prostatic hypertrophy, psychiatric disorders, in particular depression, schizophrenia, obsessive compulsive disorder and bipolar disorder, epilepsy and seizure disorders, for decreasing ischemia-reperfusion injury, myocardial infarct size and myocardial fibrosis, for the prevention of graft failure, and cystic fibrosis in a patient, said methods comprising administering to the patient a therapeutically effective amount of the compound having Formula (I) and a therapeutically effective amount of one additional therapeutic agent or more than one additional therapeutic agent.

Metabolites of compounds having Formula (I), produced by in vitro or in vivo metabolic processes, may also have utility for treating diseases associated with NAMPT.

Metabolites of compounds having Formula (I), produced by in vitro or in vivo metabolic processes, may also have utility for treating diseases associated with ROCK.

Certain precursor compounds which may be metabolized in vitro or in vivo to form compounds having Formula (I) may also have utility for treating diseases associated with NAMPT.

Certain precursor compounds which may be metabolized in vitro or in vivo to form compounds having Formula (I) may also have utility for treating diseases associated with ROCK.

Compounds having Formula (I) may exist as acid addition salts, basic addition salts or zwitterions. Salts of the compounds are prepared during isolation or following purification of the compounds. Acid addition salts of the compounds are those derived from the reaction of the compounds with an acid. For example, the acetate, adipate, alginate, bicarbonate, citrate, aspartate, benzoate, benzenesulfonate, bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate, and undecanoate salts of the compounds are contemplated as being embraced by this invention. Basic addition salts of the compounds are those derived from the reaction of the compounds with the hydroxide, carbonate or bicarbonate of cations such as lithium, sodium, potassium, calcium, and magnesium.

The compounds having Formula (I) may be administered, for example, bucally, ophthalmically, orally, osmotically, parenterally (intramuscularly, intraperitoneally intrasternally, intravenously, subcutaneously), rectally, topically, transdermally or vaginally.

Therapeutically effective amounts of compounds having Formula (I) depend on the recipient of the treatment, the disorder being treated and the severity thereof, the composition containing the compound, the time of administration, the route of administration, the duration of treatment, the compound potency, its rate of clearance and whether or not another drug is co-administered. The amount of a compound of this invention having Formula (I) used to make a composition to be administered daily to a patient in a single dose or in divided doses is from about 0.03 to about 200 mg/kg body weight. Single dose compositions contain these amounts or a combination of submultiples thereof.

Compounds having Formula (I) may be administered with or without an excipient. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Excipients for preparation of compositions comprising a compound having Formula (I) to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions comprising a compound of this invention having Formula (I) to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound of this invention having Formula (I) to be administered osmotically include, for example, chlorofluorohydrocarbons, ethanol, water and mixtures thereof. Excipients for preparation of compositions comprising a compound of this invention having Formula (I) to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound of this invention having Formula (I) to be administered rectally or vaginally include, for example, cocoa butter, polyethylene glycol, wax and mixtures thereof.

Compounds having Formula (I) are expected to be useful when used with alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Pik) inhibitors, phosphoinositide-3 kinase (PI3K) inhibitors, proteosome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxy-nucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, trofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERA-MAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145 (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474) and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zoledronic acid), zorubicin and the like.

Data

Determination of the utility of compounds having Formula (I) as binders to and inhibitors of NAMPT was performed using a Time-Resolved Fluorescence Resonance Energy Transfer (TR-FRET) binding assay.

Time-Resolved Fluorescence Resonance Energy Transfer (TR-FRET) Binding Assay of NAMPT The assay was carried out in 18 uL low volume plates (Owens Corning) in reaction buffer (50 mM HEPES (NaOH), pH 7.5, 100 mM NaCl, 10 mM $MgCl_2$, 1 mM DTT, 1% Glycerol) using 6.8 nM recombinant, human, C-terminally-His tagged NAMPT, 1 nM Tb-anti-His antibody (Invitrogen, Cat #PV5895), and 200 nM probe (Oregon Green 488-conjugated APO0866; A-1251667.0 (probe 1) or A-1287128.0 (probe 2)). Plates were covered, and reactions were carried out for 2-3 hours. Plates were read with Envision (Laser Lantha low volume protocol) after 2 to 3 hours. Excitation was carried out at 337 nm, and the ratio of emission of Oregon Green (520 nm) to terbium (492 nm) was determined and used to calculate $IC_{50}$ values of test compounds.

TABLE 1 shows the utility of compounds having Formula I to functionally inhibit NAMPT.

TABLE 1

| Example | TR-FRET Binding IC50 (μM) probe 1, probe 2 |
|---|---|
| 1 | 0.0125, nd |
| 2 | 0.00278, nd |
| 3 | 0.00309, 0.00252 |
| 4 | 0.00371, nd |
| 5 | 0.00692, 0.00832 |
| 6 | 0.00425, nd |
| 7 | 0.0046, nd |
| 8 | 0.00488, nd |
| 9 | 0.00502, nd |
| 10 | 0.00525, nd |
| 11 | 0.00618, nd |
| 12 | 0.00656, nd |
| 13 | 0.00807, nd |
| 14 | 0.00888, nd |
| 15 | 0.00991, nd |
| 16 | 0.0101, nd |
| 17 | 0.0105, nd |
| 18 | 0.011, nd |
| 19 | 0.011, nd |
| 20 | 0.011, nd |
| 21 | 0.0112, nd |
| 22 | 0.0116, nd |
| 23 | 0.0119, nd |
| 24 | 0.0123, nd |
| 25 | 0.008, 0.00299 |
| 26 | 0.0126, nd |
| 27 | 0.0138, nd |
| 28 | 0.0141, nd |
| 29 | 0.0145, nd |
| 30 | 0.0146, nd |
| 31 | 0.0149, nd |
| 32 | 0.015, nd |
| 33 | 0.015, nd |
| 34 | 0.0151, nd |
| 35 | 0.0152, nd |
| 36 | 0.0157, nd |
| 37 | 0.0161, nd |
| 38 | 0.0164, nd |
| 39 | 0.0166, nd |
| 40 | 0.0171, nd |
| 41 | 0.0174, nd |
| 42 | 0.0174, 0.0173 |
| 43 | 0.0178, nd |
| 44 | 0.018, nd |
| 45 | 0.0181, nd |
| 46 | 0.0183, nd |
| 47 | 0.0185, nd |
| 48 | 0.0186, nd |
| 49 | 0.0186, nd |
| 50 | nd, nd |
| 51 | 0.0191, nd |
| 52 | 0.0197, nd |
| 53 | 0.0197, nd |
| 54 | 0.0201, nd |
| 55 | 0.0202, nd |
| 56 | 0.0203, nd |
| 57 | 0.0211, nd |
| 58 | 0.0212, nd |
| 59 | 0.0229, 0.0154 |
| 60 | 0.0224, nd |
| 61 | 0.0225, nd |
| 62 | 0.0231, nd |
| 63 | 0.0236, nd |
| 64 | 0.0237, nd |
| 65 | 0.0238, nd |
| 66 | 0.024, nd |
| 67 | 0.0241, nd |
| 68 | 0.0247, nd |
| 69 | 0.0248, nd |
| 70 | 0.0248, nd |
| 71 | 0.0256, nd |
| 72 | 0.0258, nd |
| 73 | 0.0267, nd |

TABLE 1-continued

| Example | TR-FRET Binding IC50 (μM) probe 1, probe 2 |
|---|---|
| 74 | 0.0273, nd |
| 75 | 0.0274, nd |
| 76 | 0.0278, nd |
| 77 | 0.0284, nd |
| 78 | 0.0293, nd |
| 79 | 0.0295, nd |
| 80 | 0.0299, nd |
| 81 | 0.0301, nd |
| 82 | 0.0301, nd |
| 83 | 0.0306, nd |
| 84 | 0.0308, nd |
| 85 | 0.0313, nd |
| 86 | 0.0319, nd |
| 87 | 0.0326, nd |
| 88 | 0.033, nd |
| 89 | 0.0334, nd |
| 90 | 0.0335, nd |
| 91 | 0.0342, nd |
| 92 | 0.0346, nd |
| 93 | 0.0351, nd |
| 94 | 0.0354, nd |
| 95 | nd, nd |
| 96 | 0.0365, nd |
| 97 | 0.037, nd |
| 98 | 0.0381, nd |
| 99 | 0.0382, nd |
| 100 | nd, nd |
| 101 | 0.0393, nd |
| 102 | 0.0395, nd |
| 103 | 0.0395, nd |
| 104 | 0.0395, nd |
| 105 | 0.0397, nd |
| 106 | 0.0263, nd |
| 107 | 0.0408, nd |
| 108 | 0.0408, nd |
| 109 | 0.0412, nd |
| 110 | 0.0422, nd |
| 111 | 0.044, nd |
| 112 | 0.0445, nd |
| 113 | 0.0445, nd |
| 114 | 0.0461, nd |
| 115 | 0.0465, nd |
| 116 | 0.0465, nd |
| 117 | 0.0481, nd |
| 118 | 0.0481, nd |
| 119 | 0.0484, nd |
| 120 | 0.049, nd |
| 121 | 0.0493, nd |
| 122 | 0.0511, nd |
| 123 | 0.0515, nd |
| 124 | 0.0517, nd |
| 125 | 0.0518, nd |
| 126 | 0.0537, nd |
| 127 | 0.0539, nd |
| 128 | 0.0553, nd |
| 129 | 0.0567, nd |
| 130 | 0.0567, nd |
| 131 | 0.0573, nd |
| 132 | 0.0581, nd |
| 133 | 0.0582, nd |
| 134 | 0.0613, nd |
| 135 | 0.0615, nd |
| 136 | 0.0616, nd |
| 137 | 0.0629, nd |
| 138 | 0.0632, nd |
| 139 | 0.0638, nd |
| 140 | 0.0655, nd |
| 141 | 0.0656, nd |
| 142 | 0.0664, nd |
| 143 | 0.0665, nd |
| 144 | 0.0666, nd |
| 145 | 0.0692, nd |
| 146 | 0.0694, nd |
| 147 | 0.0701, nd |
| 148 | 0.0702, nd |
| 149 | 0.0717, nd |
| 150 | 0.0728, nd |
| 151 | 0.0733, nd |
| 152 | 0.0759, nd |
| 153 | 0.0799, nd |
| 154 | 0.0813, nd |
| 155 | 0.0834, nd |
| 156 | 0.0836, nd |
| 157 | 0.0846, nd |
| 158 | 0.0857, nd |
| 159 | 0.0858, nd |
| 160 | 0.0861, nd |
| 161 | 0.0876, nd |
| 162 | 0.0882, nd |
| 163 | 0.0893, nd |
| 164 | 0.0907, nd |
| 165 | 0.0931, nd |
| 166 | 0.0999, nd |
| 167 | 0.101, nd |
| 168 | 0.105, nd |
| 169 | 0.108, nd |
| 170 | 0.108, nd |
| 171 | 0.11, nd |
| 172 | 0.111, nd |
| 173 | 0.115, nd |
| 174 | 0.12, nd |
| 175 | 0.12, nd |
| 176 | 0.12, nd |
| 177 | 0.123, nd |
| 178 | nd, nd |
| 179 | 0.128, nd |
| 180 | 0.131, nd |
| 181 | 0.133, nd |
| 182 | 0.136, nd |
| 183 | 0.14, nd |
| 184 | 0.141, nd |
| 185 | 0.142, nd |
| 186 | 0.145, nd |
| 187 | 0.146, nd |
| 188 | 0.148, nd |
| 189 | 0.149, nd |
| 190 | 0.15, nd |
| 191 | 0.154, nd |
| 192 | 0.155, nd |
| 193 | 0.164, nd |
| 194 | 0.164, nd |
| 195 | 0.172, nd |
| 196 | 0.176, nd |
| 197 | 0.178, nd |
| 198 | 0.179, nd |
| 199 | 0.179, nd |
| 200 | 0.186, nd |
| 201 | 0.189, nd |
| 202 | 0.192, nd |
| 203 | 0.198, nd |
| 204 | 0.20, nd |
| 205 | 0.203, nd |
| 206 | 0.216, nd |
| 207 | 0.219, nd |
| 208 | 0.223, nd |
| 209 | 0.146, 0.258 |
| 210 | 0.235, Nd |
| 211 | 0.241, nd |
| 212 | 0.252, nd |
| 213 | 0.255, nd |
| 214 | 0.265, nd |
| 215 | 0.267, nd |
| 216 | 0.271, nd |
| 217 | 0.274, nd |
| 218 | 0.279, nd |
| 219 | 0.284, nd |
| 220 | 0.293, nd |
| 221 | 0.295, nd |
| 222 | 0.297, nd |
| 223 | 0.302, nd |
| 224 | 0.317, nd |
| 225 | 0.333, nd |
| 226 | 0.339, nd |
| 227 | 0.359, nd |

TABLE 1-continued

| Example | TR-FRET Binding IC50 (μM) probe 1, probe 2 |
|---|---|
| 228 | 0.359, nd |
| 229 | 0.361, nd |
| 230 | 0.369, nd |
| 231 | 0.414, nd |
| 232 | 0.42, nd |
| 233 | 0.43, nd |
| 234 | 0.43, nd |
| 235 | 0.455, nd |
| 236 | 0.457, nd |
| 237 | 0.46, nd |
| 238 | 0.504, nd |
| 239 | 0.519, nd |
| 240 | 0.52, nd |
| 241 | 0.523, nd |
| 242 | 0.524, nd |
| 243 | 0.543, nd |
| 244 | 0.574, nd |
| 245 | 0.585, nd |
| 246 | 0.618, nd |
| 247 | 0.624, nd |
| 248 | 0.738, nd |
| 249 | 0.778, nd |
| 250 | 0.78, nd |
| 251 | 0.83, nd |
| 252 | 0.837, nd |
| 253 | 0.852, nd |
| 254 | 0.877, nd |
| 255 | 0.969, nd |
| 256 | 1.23, nd |
| 257 | 1.36, nd |
| 258 | 1.52, nd |
| 259 | 1.54, nd |
| 260 | 1.57, 0.152 |
| 261 | 1.63, nd |
| 262 | 1.66, nd |
| 263 | 1.66, nd |
| 264 | 1.92, nd |
| 265 | 2.24, nd |
| 266 | 2.29, nd |
| 267 | 2.75, nd |
| 268 | 2.85, nd |
| 269 | 3.62, nd |
| 270 | 4.7, nd |
| 271 | 11.1, nd |
| 272 | 0.0816, nd |
| 273 | 1.0, nd |
| 274 | 1.03, nd |
| 275 | 0.197, nd |
| 276 | 0.298, nd |
| 277 | 1.02, nd |
| 278 | 0.385, nd |
| 279 | 1.91, nd |
| 280 | 0.04453, 0.0612 |
| 281 | 0.0383, nd |
| 282 | 0.14, nd |
| 283 | 0.387, nd |
| 284 | 0.0333, 0.0344 |
| 285 | 0.00192, 0.00259 |
| 286 | 0.00206, nd |
| 287 | 0.00435, nd |
| 288 | 0.00447, nd |
| 289 | 0.00743, nd |
| 290 | 0.0104, nd |
| 291 | 0.0277, nd |
| 292 | 0.0361, nd |
| 293 | 0.00877, nd |
| 294 | 0.00814, nd |
| 295 | 0.0141, nd |
| 296 | 0.0247, nd |
| 297 | 0.012, nd |
| 298 | 0.097, nd |
| 299 | 0.00673, nd |
| 300 | 0.0103, nd |
| 301 | 0.0546, nd |
| 302 | 0.0157, nd |
| 303 | 0.251, nd |
| 304 | 0.0133, nd |
| 305 | 0.0121, nd |
| 306 | 0.0133, nd |
| 307 | 0.0254, nd |
| 308 | 0.0808, nd |
| 309 | 0.0634, nd |
| 310 | 0.0368, nd |
| 311 | 0.00524, nd |
| 312 | 0.114, nd |
| 313 | 0.00541, 0.00587 |
| 314 | 0.021, nd |
| 315 | 0.00762, nd |
| 316 | 0.287, nd |
| 317 | 0.0421, nd |
| 318 | 0.249, nd |
| 319 | 0.0319, nd |
| 320 | 0.272, nd |
| 321 | 0.203, nd |
| 322 | 0.0255, nd |
| 323 | 0.0988, nd |
| 324 | 0.333, nd |
| 325 | 0.0987, nd |
| 326 | 0.0743, nd |
| 327 | 0.223, nd |
| 328 | 0.331, nd |
| 329 | 2.02, nd |
| 330 | 0.00618, nd |
| 331 | 0.00611, nd |
| 332 | 0.0042, nd |
| 333 | 0.00315, nd |
| 334 | 0.0223, nd |
| 335 | 0.00669, nd |
| 336 | 0.0259, nd |
| 337 | 0.0261, nd |
| 338 | 0.0785, nd |
| 339 | 0.315, nd |
| 340 | 0.783, nd |
| 341 | 0.101, nd |
| 342 | 0.103, nd |
| 343 | 0.0791, nd |
| 344 | 0.216, nd |
| 345 | 0.84, nd |
| 346 | 0.0498, nd |
| 347 | 0.297, nd |
| 348 | 1.56, nd |
| 349 | 0.0022, nd |
| 350 | 0.00825, nd |
| 351 | 0.064, nd |
| 352 | 1.19, nd |
| 353 | 0.00763, nd |
| 354 | 0.0405, nd |
| 355 | 0.124, nd |
| 356 | 0.404, nd |
| 357 | 9.88, nd |
| 358 | 0.0711, nd |
| 359 | 0.0881, nd |
| 360 | 0.239, nd |
| 361 | 0.436, nd |
| 362 | 0.578, nd |
| 363 | 2.04, nd |
| 364 | 6.48, nd |
| 365 | 11.2, nd |
| 366 | 3.34, nd |
| 367 | 4.84, nd |
| 368 | 0.00373, nd |
| 369 | 0.00656, nd |
| 370 | 0.0075, nd |
| 371 | 0.0395, nd |
| 372 | 0.0535, nd |
| 373 | 0.0234, nd |
| 374 | nd, nd |
| 375 | 0.595, nd |
| 376 | nd, nd |
| 377 | 0.105, nd |
| 378 | 0.492, 0.377 |
| 379 | 0.0511, 0.0404 |
| 380 | nd, 0.201 |
| 381 | 0.547, nd |

TABLE 1-continued

| Example | TR-FRET Binding IC50 (μM) probe 1, probe 2 |
|---|---|
| 382 | 0.257, nd |
| 383 | 1.99, 1.34 |
| 384 | 0.00974, 0.00889 |
| 385 | 0.040, 0.0484 |
| 386 | 0.0707, nd |
| 387 | 0.17, nd |
| 388 | 5.7, 4.55 |
| 389 | 0.266, nd |
| 390 | 0.727, 0.616 |
| 391 | 0.0465, 1.41 |
| 392 | 0.282, 0.288 |
| 393 | 0.415, 0.281 |
| 394 | 2.07, 1.45 |
| 395 | 1.84, 1.67 |
| 396 | 0.474, 0.278 |
| 397 | 0.405, 0.353 |
| 398 | 0.346, 0.272 |
| 399 | 0.0903, 0.0736 |
| 400 | 1.89, 2.35 |
| 401 | 0.072, nd |
| 402 | 0.183, nd |
| 403 | 0.606, nd |
| 404 | 0.0277, nd |
| 405 | 0.012, nd |
| 406 | 0.011, nd |
| 407 | 0.00145, nd |
| 408 | 0.372, nd |
| 409 | 1.02, nd |
| 410 | 0.0295, nd |
| 411 | 0.0197, nd |
| 412 | 0.168, 0.109 |
| 413 | 2.01, nd |
| 414 | 0.032, nd |
| 415 | 0.0121, nd |
| 416 | 0.041, nd |
| 417 | 4.91, nd |
| 418 | 0.506, 0.0514 |
| 419 | 0.010, nd |
| 420 | 0.0182, nd |
| 421 | 0.0404, nd |
| 422 | 3.94, nd |
| 423 | 12.5, nd |
| 424 | 0.0826, nd |
| 425 | 0.0814, nd |
| 426 | 0.0104, nd |
| 427 | 0.0154, nd |
| 428 | 0.0327, nd |
| 429 | 0.179, nd |
| 430 | 0.191, nd |
| 431 | 0.0607, nd |
| 432 | 0.00874, nd |
| 433 | 0.00807, nd |
| 434 | 0.0507, nd |
| 435 | 0.00589, nd |
| 436 | 0.00933, nd |
| 437 | 0.0080, nd |
| 438 | 0.60, nd |
| 439 | 1.69, nd |
| 440 | 0.0355, nd |
| 441 | 0.0237, 0.015 |
| 442 | 0.0492, nd |
| 443 | 0.365, nd |
| 444 | 0.281, nd |
| 445 | 0.0141, nd |
| 446 | 0.011, nd |
| 447 | 0.0466, nd |
| 448 | 0.021, nd |
| 449 | 0.0257, nd |
| 450 | 1.03, nd |
| 451 | 0.000946, 0.00124 |
| 452 | 0.0512, nd |
| 453 | 0.0527, nd |
| 454 | 0.0803, nd |
| 455 | 12.2, nd |
| 456 | 0.0598, 0.0475 |
| 457 | 0.0756, nd |
| 458 | nd, nd |
| 459 | 0.00362, nd |
| 460 | 0.0193, nd |
| 461 | nd, 0.00815 |
| 462 | 0.00694, nd |
| 463 | 0.0215, 0.013 |
| 464 | 0.0166, 0.0272 |
| 465 | 0.00823, 0.0238 |
| 466 | nd, nd |
| 467 | 0.0165, 0.047 |
| 468 | 0.00339, 0.00726 |
| 469 | 0.00597, 0.00947 |
| 470 | 0.00445, 0.0080 |
| 471 | 0.00811, 0.019 |
| 472 | 0.0149, 0.0107 |
| 473 | 0.00321, 0.00381 |
| 474 | 0.00389, 0.00775 |
| 475 | 0.0090, 0.0139 |
| 476 | 0.0125, 0.0468 |
| 477 | 0.00996, nd |
| 478 | 0.015, 0.386 |
| 479 | nd, 0.00399 |
| 480 | 0.00571, 0.0676 |
| 481 | nd, nd |
| 482 | 0.00511, nd |
| 483 | 0.00479, 0.00937 |
| 484 | nd, nd |
| 485 | 0.00557, 0.0118 |
| 486 | 0.0047, 0.00497 |
| 487 | 0.00884, 0.0573 |
| 488 | 0.00825, 0.0211 |
| 489 | 0.0123, nd |
| 490 | 0.0212, 0.028 |
| 491 | 0.00455, 0.0113 |
| 492 | 0.0396, 0.0417 |
| 493 | 0.0336, 0.013 |
| 494 | 0.016, 0.021 |
| 495 | 0.0516, 0.0607 |
| 496 | 0.0139, 0.0257 |
| 497 | 0.00331, 0.0048 |
| 498 | 0.307, nd |
| 499 | 0.806, nd |
| 500 | 0.182, nd |
| 501 | 0.0459, 0.018 |
| 502 | 0.157, nd |
| 503 | 0.0786, nd |
| 504 | 0.0766, 0.0563 |
| 505 | 0.0204, 0.0182 |
| 506 | 0.0332, 0.0227 |
| 507 | 0.186, nd |
| 508 | 0.184, nd |
| 509 | 0.211, nd |
| 510 | 0.0337, 0.0221 |
| 511 | 0.0176, 0.0275 |
| 512 | 0.0436, 0.0443 |
| 513 | 0.0539, 0.0681 |
| 514 | 0.0481, 0.0673 |
| 515 | 0.0723, 0.0666 |
| 516 | 0.0106, 0.00847 |
| 517 | 0.0758, nd |
| 518 | 0.266, nd |
| 519 | 0.0968, nd |
| 520 | 0.0488, nd |
| 521 | 0.0601, 0.0631 |
| 522 | 0.0296, 0.0611 |
| 523 | 0.187, nd |
| 524 | 0.115, nd |
| 525 | 0.0375, 0.060 |
| 526 | 0.076, 0.0644 |
| 527 | 0.0168, 0.0243 |
| 528 | 0.0521, 0.0454 |
| 529 | 0.103, nd |
| 530 | 0.124, nd |
| 531 | 0.159, nd |
| 532 | 0.488, nd |
| 533 | 0.294, nd |
| 534 | 0.14, nd |
| 535 | 0.743, nd |

TABLE 1-continued

| Example | TR-FRET Binding IC50 (μM) probe 1, probe 2 |
|---|---|
| 536 | 0.187, nd |
| 537 | 0.0132, 0.0106 |
| 538 | 0.072, 0.0829 |
| 539 | 0.072, 0.0417 |
| 540 | 0.137, nd |
| 541 | 0.225, nd |
| 542 | 0.00277, 0.0026 |
| 543 | 0.00213, 0.00302 |
| 544 | 0.00302, 0.00305 |
| 545 | 0.00278, 0.0020 |
| 546 | 0.00332, 0.00322 |
| 547 | nd, nd |
| 548 | nd, nd |
| 549 | nd, nd |
| 550 | nd, nd |
| 551 | nd, nd |
| 552 | nd, nd |
| 553 | 0.00755, 0.00582 |
| 554 | 0.00401, 0.00519 |
| 555 | 0.0196, 0.0114 |
| 556 | 0.0145, 0.0102 |
| 557 | 0.862, 1.98 |
| 558 | 1.84, 5.63 |
| 559 | 1.98, nd |
| 560 | 5.02, nd |
| 561 | 0.268, nd |
| 562 | 0.0189, 0.0177 |
| 563 | 0.00166, 0.00361 |
| 564 | 0.00196, 0.00159 |
| 565 | 0.0083, 0.00737 |
| 566 | 0.193, nd |
| 567 | 0.00675, 0.00624 |
| 568 | 0.00412, 0.00501 |
| 569 | 0.00808, 0.0085 |
| 570 | 0.00913, 0.00995 |
| 571 | 0.0138, 0.0104 |
| 572 | 0.00845, 0.00972 |
| 573 | 1.26, nd |
| 574 | 0.0794, 0.0621 |
| 575 | 0.0538, 0.0378 |
| 576 | 0.0902, 0.0507 |
| 577 | 0.00439, 0.00297 |
| 578 | 0.060, 0.0707 |
| 579 | 0.00314, 0.00247 |
| 580 | 0.00239, 0.00201 |
| 581 | 0.0040, 0.00338 |
| 582 | 0.00205, 0.00169 |
| 583 | 0.00282, 0.0027 |
| 584 | 0.0147, 0.0117 |
| 585 | nd, 0.0271 |
| 586 | nd, 0.0338 |
| 587 | nd, 0.444 |
| 588 | nd, 0.739 |
| 589 | nd, 0.044 |
| 590 | nd, 0.0428 |
| 591 | nd, 0.661 |
| 592 | nd, 0.0884 |
| 593 | nd, 0.0269 |
| 594 | nd, 0.021 |
| 595 | nd, 0.0651 |
| 596 | nd, 0.00448 |
| 597 | nd, 0.0631 |
| 598 | nd, 0.0322 |
| 599 | nd, 0.0582 |
| 600 | nd, 0.0385 |
| 601 | nd, 0.0326 |
| 602 | nd, 0.0392 |
| 603 | nd, 0.056 |
| 604 | nd, 0.0224 |
| 605 | nd, 0.00759 |
| 606 | nd, 0.0139 |
| 607 | nd, 0.00159 |
| 608 | nd, 0.00985 |
| 609 | nd, 0.196 |
| 610 | nd, 1.3 |
| 611 | nd, 0.328 |
| 612 | nd, 0.365 |

TABLE 1-continued

| Example | TR-FRET Binding IC50 (μM) probe 1, probe 2 |
|---|---|
| 613 | nd, 0.119 |
| 614 | nd, 0.0482 |
| 615 | nd, 0.0842 |
| 616 | nd, 0.097 |
| 617 | nd, 1.13 |
| 618 | nd, 0.00755 |
| 619 | nd, 0.0827 |
| 620 | nd, 0.00755 |
| 621 | nd, 0.0118 |
| 622 | nd, 0.0595 |
| 623 | nd, 1.48 |
| 624 | nd, 0.046 |
| 625 | nd, 0.0107 |
| 626 | nd, 0.00759 |
| 627 | nd, 0.164 |
| 628 | nd, 0.0234 |
| 629 | nd, 0.0335 |
| 630 | nd, 0.0725 |
| 631 | nd, 0.0506 |
| 632 | nd, 0.104 |
| 633 | nd, 0.0873 |
| 634 | nd, 0.0361 |
| 635 | nd, 0.129 |
| 636 | nd, 1.21 |
| 637 | nd, 0.0542 |
| 638 | nd, 0.102 |
| 639 | nd, 0.0882 |
| 640 | nd, 0.135 |
| 641 | nd, 0.163 |
| 642 | nd, 0.507 |
| 643 | nd, 0.0633 |
| 644 | nd, 0.0594 |
| 645 | nd, 0.125 |
| 646 | nd, 0.00568 |
| 647 | nd, 0.0385 |
| 648 | nd, 0.845 |
| 649 | nd, 0.0445 |
| 650 | nd, 0.106 |
| 651 | nd, 0.0207 |
| 652 | nd, 0.00488 |
| 653 | nd, 0.0144 |
| 654 | nd, 0.0256 |
| 655 | nd, 0.0224 |
| 656 | nd, 0.116 |
| 657 | nd, 0.0533 |
| 658 | nd, 0.00549 |
| 659 | nd, 0.00585 |
| 660 | nd, 0.0221 |
| 661 | nd, 0.00253 |
| 662 | nd, 0.00977 |
| 663 | nd, 0.0136 |
| 664 | nd, 0.00412 |
| 665 | nd, 0.00814 |
| 666 | nd, 0.0111 |
| 667 | nd, 0.00905 |
| 668 | nd, 0.00698 |
| 669 | nd, 0.0136 |
| 670 | nd, 0.0183 |
| 671 | nd, 0.0238 |
| 672 | nd, 0.011 |
| 673 | nd, 0.0248 |
| 674 | nd, 0.00839 |
| 675 | nd, 0.0414 |
| 676 | nd, 0.0165 |
| 677 | nd, 0.0126 |
| 678 | nd, 0.00265 |
| 679 | nd, 0.00461 |
| 680 | nd, 0.126 |
| 681 | nd, 0.0603 |
| 682 | nd, 0.019 |
| 683 | nd, 0.0669 |
| 684 | nd, 0.0153 |
| 685 | nd, 0.0205 |
| 686 | nd, 0.653 |
| 687 | nd, 0.0238 |
| 688 | nd, 0.00303 |
| 689 | nd, 0.0123 |

TABLE 1-continued

| Example | TR-FRET Binding IC50 (μM) probe 1, probe 2 |
|---|---|
| 690 | nd, 0.00616 |
| 691 | nd, 0.0392 |
| 692 | nd, 0.0247 |
| 693 | nd, 0.0264 |
| 694 | nd, 0.0359 |
| 695 | nd, 0.027 |
| 696 | nd, 0.00223 |
| 697 | nd, 0.0049 |
| 698 | nd, 0.0327 |
| 699 | nd, 0.00558 |
| 700 | nd, 0.0204 |
| 701 | nd, 0.0227 |
| 702 | nd, 0.0232 |
| 703 | nd, 0.0829 |
| 704 | nd, 0.0126 |
| 705 | nd, 0.00742 |
| 706 | nd, 0.00581 |
| 707 | nd, 0.00573 |
| 708 | nd, 0.00997 |
| 709 | nd, 0.00601 |
| 710 | nd, 0.00336 |
| 711 | nd, 0.0462 |
| 712 | nd, 0.0453 |
| 713 | nd, 0.0529 |
| 714 | nd, 0.121 |
| 715 | nd, 0.136 |
| 716 | nd, 0.102 |
| 717 | nd, 0.0718 |
| 718 | nd, 0.012 |
| 719 | nd, 0.0347 |
| 720 | nd, 0.164 |
| 721 | nd, 0.14 |
| 722 | nd, 0.00157 |
| 723 | nd, 0.0209 |
| 724 | nd, 0.0851 |
| 725 | nd, 0.477 |
| 726 | nd, 0.577 |
| 727 | nd, 1.22 |
| 728 | nd, 0.00752 |
| 729 | nd, 0.0445 |
| 730 | nd, 0.45 |
| 731 | nd, 0.0183 |
| 732 | nd, 0.0241 |
| 733 | nd, 0.0598 |
| 734 | nd, 0.0845 |
| 735 | nd, 0.126 |
| 736 | nd, 0.281 |
| 737 | nd, 0.186 |
| 738 | nd, 0.00417 |
| 739 | nd, 0.0049 |
| 740 | nd, 0.204 |
| 741 | nd, 0.0165 |
| 742 | nd, 0.0331 |
| 743 | nd, 0.00971 |
| 744 | nd, 0.00446 |
| 745 | nd, 0.00868 |
| 746 | nd, 0.0768 |
| 747 | nd, 0.00434 |
| 748 | nd, 0.00455 |
| 749 | nd, 0.0161 |
| 750 | nd, 0.0118 |
| 751 | nd, 0.229 |
| 752 | nd, 0.0108 |
| 753 | nd, 0.0655 |
| 754 | nd, 0.0683 |
| 755 | nd, 0.0407 |
| 756 | nd, 0.0488 |
| 757 | nd, 0.00201 |
| 758 | nd, 0.0293 |
| 759 | nd, 0.00581 |
| 760 | nd, 0.00483 |
| 761 | nd, 0.0131 |
| 762 | nd, 0.0173 |
| 763 | nd, 0.00528 |
| 764 | nd, 0.0581 |
| 765 | nd, 0.0532 |
| 766 | nd, 0.0468 |
| 767 | nd, 0.169 |
| 768 | nd, 0.13 |
| 769 | nd, 0.0695 |
| 770 | nd, 0.135 |
| 771 | nd, 0.0893 |
| 772 | nd, 0.0534 |
| 773 | nd, 0.297 |
| 774 | nd, 0.0826 |
| 775 | nd, 0.0951 |
| 776 | nd, 0.00746 |
| 777 | nd, 0.00625 |
| 778 | nd, 0.0259 |
| 779 | nd, 0.0385 |
| 780 | nd, 0.109 |
| 781 | nd, 0.0158 |
| 782 | nd, 0.0296 |
| 783 | nd, 0.029 |
| 784 | nd, 0.0224 |
| 785 | nd, 0.0262 |
| 786 | nd, 0.0262 |
| 787 | nd, 0.13 |
| 788 | nd, 0.0785 |
| 789 | nd, 0.00318 |
| 790 | nd, 0.159 |
| 791 | nd, 0.00977 |
| 792 | nd, 0.0217 |
| 793 | nd, 0.0118 |
| 794 | nd, 0.017 |
| 795 | nd, 0.991 |
| 796 | nd, 0.00322 |
| 797 | nd, 0.00295 |
| 798 | nd, 0.00221 |
| 799 | nd, 0.00361 |
| 800 | nd, 0.0821 |
| 801 | nd, 0.30 |
| 802 | nd, 0.0258 |
| 803 | nd, 0.0132 |
| 804 | nd, 0.0373 |
| 805 | nd, 0.0287 |
| 806 | nd, 0.286 |
| 807 | nd, 0.0417 |
| 808 | nd, 0.696 |
| 809 | nd, 0.00207 |
| 810 | nd, nd |
| 811 | nd, 0.00359 |
| 812 | nd, 0.00679 |
| 813 | nd, 0.0446 |
| 814 | nd, 0.00713 |
| 815 | nd, 0.00287 |
| 816 | nd, 0.0243 |
| 817 | nd, 0.00251 |
| 818 | nd, 0.0128 |
| 819 | nd, 0.00428 |
| 820 | nd, 0.00631 |
| 821 | nd, 0.012 |
| 822 | nd, 0.00207 |
| 823 | nd, 0.00176 |
| 824 | nd, 0.0066 |
| 825 | nd, 0.0107 |
| 826 | nd, 0.00918 |
| 827 | nd, 0.00311 |
| 828 | nd, 0.00737 |
| 829 | nd, 0.00359 |
| 830 | nd, nd |
| 831 | nd, 0.00918 |
| 832 | nd, 0.00888 |
| 833 | nd, 0.0034 |
| 834 | nd, 0.00358 |
| 835 | nd, 0.00353 |
| 836 | nd, 0.00454 |
| 837 | nd, 0.00367 |
| 838 | nd, 0.00203 |
| 839 | nd, 0.0191 |
| 840 | nd, 0.725 |
| 841 | nd, 1.61 |
| 842 | nd, 0.0746 |
| 843 | nd, 0.704 |

TABLE 1-continued

| Example | TR-FRET Binding IC50 (μM) probe 1, probe 2 |
|---|---|
| 844 | nd, 2.62 |
| 845 | nd, 5.64 |
| 846 | nd, 2.99 |
| 847 | nd, 0.24 |
| 848 | nd, 1.19 |
| 849 | nd, 5.71 |
| 850 | nd, 2.1 |
| 851 | nd, 0.277 |
| 852 | nd, 5.48 |
| 853 | nd, 12.5 |
| 854 | nd, 5.66 |
| 855 | nd, 0.839 |
| 856 | nd, 0.00913 |
| 857 | nd, 0.061 |
| 858 | nd, 0.0082 |
| 859 | nd, 2.14 |
| 860 | nd, 12.5 |
| 861 | nd, 3.15 |
| 862 | nd, 0.599 |
| 863 | nd, 0.143 |
| 864 | nd, 0.122 |
| 865 | nd, 1.56 |
| 866 | nd, 0.14 |
| 867 | nd, 0.0593 |
| 868 | nd, 0.128 |
| 869 | nd, 0.229 |
| 870 | nd, 0.12 |
| 871 | nd, 0.036 |
| 872 | nd, 0.00746 |
| 873 | nd, 0.00465 |
| 874 | nd, 0.00231 |
| 875 | nd, 0.00419 |
| 876 | nd, 0.0022 |
| 877 | nd, 0.00882 |
| 878 | nd, 0.0525 |
| 879 | nd, 0.00298 |
| 880 | nd, 0.0517 |
| 881 | nd, 0.0463 |
| 882 | nd, 0.0377 |
| 883 | nd, 0.0156 |
| 884 | nd, 0.0154 |
| 885 | nd, 0.466 |
| 886 | nd, 0.0246 |
| 887 | nd, 0.826 |
| 888 | nd, 0.0934 |
| 889 | nd, 1.47 |
| 890 | nd, 1.38 |
| 891 | nd, 1.72 |
| 892 | nd, 1.84 |
| 893 | nd, 0.154 |
| 894 | nd, 0.00302 |
| 895 | nd, 0.0261 |
| 896 | nd, 0.444 |
| 897 | nd, 0.969 |
| 898 | nd, 0.288 |
| 899 | nd, 0.19 |
| 900 | nd, 0.0437 |
| 901 | nd, 0.0676 |
| 902 | nd, 0.35 |
| 903 | nd, 0.0491 |
| 904 | nd, 0.0351 |
| 905 | nd, 0.0383 |
| 906 | nd, 0.0569 |
| 907 | nd, 0.0711 |
| 908 | nd, 0.0334 |
| 909 | nd, 0.0019 |
| 910 | nd, 0.00638 |
| 911 | nd, 0.0133 |
| 912 | nd, 0.00832 |
| 913 | nd, 0.0074 |
| 914 | nd, 0.00486 |
| 915 | nd, 0.0188 |
| 916 | nd, 0.0221 |
| 917 | nd, 0.00207 |
| 918 | nd, 0.0128 |
| 919 | nd, 0.00708 |
| 920 | nd, 0.548 |
| 921 | nd, 0.0602 |
| 922 | nd, 0.00567 |
| 923 | nd, 0.00395 |
| 924 | nd, 0.00277 |
| 925 | nd, 0.00683 |
| 926 | nd, 0.0508 |
| 927 | nd, 0.0406 |
| 928 | nd, 0.0725 |
| 929 | nd, 0.21 |
| 930 | nd, 0.146 |
| 931 | nd, 0.0981 |
| 932 | nd, 1.31 |
| 933 | nd, 0.206 |
| 934 | nd, 0.00168 |
| 935 | nd, 0.00584 |
| 936 | nd, 0.121 |
| 937 | nd, 0.0398 |
| 938 | nd, 0.0877 |
| 939 | nd, 0.0105 |
| 940 | nd, 0.0168 |
| 941 | nd, 0.136 |
| 942 | nd, 0.0238 |
| 943 | nd, 0.0090 |
| 944 | nd, 0.0328 |
| 945 | nd, 0.0433 |
| 946 | nd, 0.0172 |
| 947 | nd, 0.0459 |
| 948 | nd, 0.0192 |
| 949 | nd, 0.0309 |
| 950 | nd, 0.0198 |
| 951 | nd, 0.00968 |
| 952 | nd, 0.0128 |
| 953 | nd, 0.426 |
| 954 | nd, 0.341 |
| 955 | nd, 0.222 |
| 956 | nd, 0.346 |
| 957 | nd, 0.374 |
| 958 | nd, 0.148 |
| 959 | nd, 0.307 |
| 960 | nd, 0.22 |
| 961 | nd, 0.161 |
| 962 | nd, 0.201 |
| 963 | nd, 0.198 |
| 964 | nd, 0.128 |
| 965 | nd, 0.17 |
| 966 | nd, 0.223 |
| 967 | nd, 0.0047 |
| 968 | nd, 0.00259 |
| 969 | nd, 0.0234 |
| 970 | nd, 0.0213 |
| 971 | nd, 0.0205 |
| 972 | nd, 0.00919 |
| 973 | nd, 0.0435 |
| 974 | nd, 0.034 |
| 975 | nd, 0.0115 |
| 976 | nd, 0.0225 |
| 977 | nd, 0.0214 |
| 978 | nd, 0.0236 |
| 979 | nd, 0.0365 |
| 980 | nd, 0.0173 |
| 981 | nd, 0.034 |
| 982 | nd, 0.0144 |
| 983 | nd, 0.0296 |
| 984 | nd, 0.0689 |
| 985 | nd, 0.00963 |
| 986 | nd, 0.0407 |
| 987 | nd, 0.111 |
| 988 | nd, nd |
| 989 | nd, 0.0269 |
| 990 | nd, 0.031 |
| 991 | nd, 0.0408 |
| 992 | nd, 0.0168 |
| 993 | nd, 0.00941 |
| 994 | nd, 0.00802 |
| 995 | nd, 0.0285 |
| 996 | nd, 0.101 |
| 997 | nd, 0.175 |

TABLE 1-continued

| Example | TR-FRET Binding IC50 (μM) probe 1, probe 2 |
|---|---|
| 998 | nd, 0.0277 |
| 999 | nd, 0.0166 |
| 1000 | nd, 0.0391 |
| 1001 | nd, 0.00157 |
| 1002 | nd, 0.0426 |
| 1003 | nd, 0.0489 |
| 1004 | nd, 0.0461 |
| 1005 | nd, 0.0385 |
| 1006 | nd, 0.0252 |
| 1007 | nd, 0.0598 |
| 1008 | nd, 0.0349 |
| 1009 | nd, 0.0266 |
| 1010 | nd, 0.114 |
| 1011 | nd, 0.0264 |
| 1012 | nd, 0.0923 |
| 1013 | nd, 0.389 |
| 1014 | nd, 0.00661 |
| 1015 | nd, 0.00631 |
| 1016 | nd, 0.00375 |
| 1017 | nd, 0.00201 |
| 1018 | nd, 0.0244 |
| 1019 | nd, 0.00144 |
| 1020 | nd, 10.0 |
| 1021 | nd, 1.17 |
| 1022 | nd, 0.0135 |
| 1023 | nd, 0.0127 |
| 1024 | nd, 0.0921 |
| 1025 | nd, 0.00795 |
| 1026 | nd, 0.035 |
| 1027 | nd, 0.0842 |
| 1028 | nd, 0.0519 |
| 1029 | nd, 0.035 |
| 1030 | nd, 0.0116 |
| 1031 | nd, 0.0251 |
| 1032 | nd, 0.156 |
| 1033 | nd, 0.113 |
| 1034 | nd, 0.164 |
| 1035 | nd, 0.376 |
| 1036 | nd, 0.20 |
| 1037 | nd, 0.048 |
| 1038 | nd, 0.0248 |
| 1039 | nd, 0.105 |
| 1040 | nd, 0.0163 |
| 1041 | nd, 0.0128 |
| 1042 | nd, 0.00968 |
| 1043 | nd, 0.00489 |
| 1044 | nd, 0.00621 |
| 1045 | nd, 0.00924 |
| 1046 | nd, 0.0469 |
| 1047 | nd, 0.0542 |
| 1048 | nd, 0.0345 |
| 1049 | nd, 0.0398 |
| 1050 | nd, 0.102 |
| 1051 | nd, 0.0626 |
| 1052 | nd, 0.0318 |
| 1053 | nd, 0.0764 |
| 1054 | nd, 0.0563 |
| 1055 | nd, 1.55 |
| 1056 | nd, 0.335 |
| 1057 | nd, 2.32 |
| 1058 | nd, 1.12 |
| 1059 | nd, 0.394 |
| 1060 | nd, 1.57 |
| 1061 | nd, 1.78 |
| 1062 | nd, 0.222 |
| 1063 | nd, 0.00988 |
| 1064 | nd, 0.0621 |
| 1065 | nd, 0.00445 |
| 1066 | nd, 0.318 |
| 1067 | nd, 0.738 |
| 1068 | nd, 0.365 |
| 1069 | nd, 0.122 |
| 1070 | nd, 0.332 |
| 1071 | nd, 0.993 |
| 1072 | nd, 0.117 |
| 1073 | nd, 0.0659 |
| 1074 | nd, 0.0674 |
| 1075 | nd, 0.0931 |
| 1076 | nd, 0.0389 |
| 1077 | nd, 0.0069 |
| 1078 | nd, 0.00347 |
| 1079 | nd, 0.0259 |
| 1080 | nd, 0.00297 |
| 1081 | nd, 0.00682 |
| 1082 | nd, 0.0195 |
| 1083 | nd, 0.0117 |
| 1084 | nd, 0.0296 |
| 1085 | nd, 0.029 |
| 1086 | nd, 0.0152 |
| 1087 | nd, 0.00733 |
| 1088 | nd, 0.0155 |
| 1089 | nd, 0.0771 |
| 1090 | nd, 0.0493 |
| 1091 | nd, 0.0289 |
| 1092 | nd, 0.0192 |
| 1093 | nd, 0.0117 |
| 1094 | nd, 0.044 |
| 1095 | nd, 0.0118 |
| 1096 | nd, 0.028 |
| 1097 | nd, 0.0756 |
| 1098 | nd, 0.0111 |
| 1099 | nd, 0.145 |
| 1100 | nd, 0.0263 |
| 1101 | nd, 0.0448 |
| 1102 | nd, 0.108 |
| 1103 | nd, 0.00784 |
| 1104 | nd, 1.69 |
| 1105 | nd, 0.0619 |
| 1106 | nd, 0.364 |
| 1107 | nd, 0.152 |
| 1108 | nd, 0.0061 |
| 1109 | nd, 0.048 |
| 1110 | nd, 0.0151 |
| 1111 | nd, 0.0139 |
| 1112 | nd, 0.0498 |
| 1113 | nd, 0.00326 |
| 1114 | nd, 0.0281 |
| 1115 | nd, 0.0188 |
| 1116 | nd, 0.0419 |
| 1117 | nd, 0.0332 |
| 1118 | nd, 0.00548 |
| 1119 | nd, 0.0224 |
| 1120 | nd, 0.0227 |
| 1121 | nd, 0.0302 |
| 1122 | nd, 0.162 |
| 1123 | nd, 0.0309 |
| 1124 | nd, 0.0143 |
| 1125 | nd, 0.0764 |
| 1126 | nd, 0.311 |
| 1127 | nd, 0.00569 |
| 1128 | nd, 0.199 |
| 1129 | nd, 0.546 |
| 1130 | nd, 0.0354 |
| 1131 | nd, 0.0414 |
| 1132 | nd, 0.201 |
| 1133 | nd, 0.703 |
| 1134 | nd, 0.175 |
| 1135 | nd, 0.121 |
| 1136 | nd, 0.0498 |
| 1137 | nd, 0.0119 |
| 1138 | nd, 0.0874 |
| 1139 | nd, 0.333 |
| 1140 | nd, 0.138 |
| 1141 | nd, 0.0099 |
| 1142 | nd, 0.136 |
| 1143 | nd, 0.328 |
| 1144 | nd, 0.00515 |
| 1145 | nd, 0.00619 |
| 1146 | nd, 0.0148 |
| 1147 | nd, 0.00824 |
| 1148 | nd, 0.0409 |
| 1149 | nd, 0.0824 |
| 1150 | nd, 0.0132 |
| 1151 | nd, 0.048 |

TABLE 1-continued

| Example | TR-FRET Binding IC50 (μM) probe 1, probe 2 |
|---|---|
| 1152 | nd, 0.233 |
| 1153 | nd, 0.00492 |
| 1154 | nd, 0.00962 |
| 1155 | nd, 0.033 |
| 1156 | nd, 0.216 |
| 1157 | nd, 0.0725 |
| 1158 | nd, 0.0125 |
| 1159 | nd, 0.0179 |
| 1160 | nd, 0.237 |
| 1161 | nd, 0.0044 |
| 1162 | nd, 0.00954 |
| 1163 | nd, 0.0174 |
| 1164 | nd, 0.00544 |
| 1165 | nd, nd |
| 1166 | nd, 0.0562 |
| 1167 | nd, 0.0298 |
| 1168 | nd, nd |
| 1169 | nd, 0.239 |
| 1170 | nd, 0.0214 |
| 1171 | nd, 0.0105 |
| 1172 | nd, 0.00867 |
| 1173 | nd, 0.0437 |
| 1174 | nd, 0.0156 |
| 1175 | nd, 0.00662 |
| 1176 | nd, 0.00915 |
| 1177 | nd, 0.0496 |
| 1178 | nd, 0.112 |
| 1179 | nd, 0.0791 |
| 1180 | nd, 0.0102 |
| 1181 | nd, 0.128 |
| 1182 | nd, nd |
| 1183 | nd, 0.0404 |
| 1184 | nd, 0.109 |
| 1185 | nd, 0.0503 |
| 1186 | nd, 0.0106 |
| 1187 | nd, 0.00878 |
| 1188 | nd, 0.00494 |
| 1189 | nd, 0.0291 |
| 1190 | nd, 0.0843 |
| 1191 | nd, 0.0607 |
| 1192 | nd, 0.17 |
| 1193 | nd, 0.00776 |
| 1194 | nd, 0.171 |
| 1195 | nd, 0.0205 |
| 1196 | nd, 0.0102 |
| 1197 | nd, 0.101 |
| 1198 | nd, nd |
| 1199 | nd, 0.165 |
| 1200 | nd, nd |
| 1201 | nd, 0.0422 |
| 1202 | nd, 0.0227 |
| 1203 | nd, 0.378 |
| 1204 | nd, 0.0772 |
| 1205 | nd, 0.345 |
| 1206 | nd, 0.394 |
| 1207 | nd, 0.283 |
| 1208 | nd, 0.028 |
| 1209 | nd, 0.0387 |
| 1210 | nd, 0.0192 |
| 1211 | nd, 0.879 |
| 1212 | nd, 0.144 |
| 1213 | nd, nd |
| 1214 | nd, 0.035 |
| 1215 | nd, 0.133 |
| 1216 | nd, 0.054 |
| 1217 | nd, 0.0316 |
| 1218 | nd, 0.158 |
| 1219 | nd, 0.0613 |
| 1220 | nd, 0.0181 |
| 1221 | nd, 1.13 |
| 1222 | nd, 0.0513 |
| 1223 | nd, 0.0192 |
| 1224 | nd, 0.497 |
| 1225 | nd, 0.0767 |
| 1226 | nd, 0.0116 |
| 1227 | nd, 0.0534 |
| 1228 | nd, 0.418 |

TABLE 1-continued

| Example | TR-FRET Binding IC50 (μM) probe 1, probe 2 |
|---|---|
| 1229 | nd, 0.393 |
| 1230 | nd, 0.0674 |
| 1231 | nd, 0.576 |
| 1232 | nd, 0.0248 |
| 1233 | nd, 0.351 |
| 1234 | nd, 0.0174 |
| 1235 | nd, 0.0668 |
| 1236 | nd, 0.078 |
| 1237 | nd, 0.561 |
| 1238 | nd, 0.748 |
| 1239 | nd, 0.328 |
| 1240 | nd, 0.592 |
| 1241 | nd, 0.0122 |
| 1242 | nd, 0.0488 |
| 1243 | nd, 0.142 |
| 1244 | nd, 2.23 |
| 1245 | nd, 0.0214 |
| 1246 | nd, 0.803 |
| 1247 | nd, 0.212 |
| 1248 | nd, 0.373 |
| 1249 | nd, 0.17 |
| 1250 | nd, 0.335 |
| 1251 | nd, 0.111 |
| 1252 | nd, 0.125 |
| 1253 | nd, 0.669 |
| 1254 | nd, 0.00222 |
| 1255 | nd, 0.00211 |
| 1256 | nd, 0.00328 |
| 1257 | nd, 0.00482 |
| 1258 | nd, 0.00831 |
| 1259 | nd, 0.00191 |
| 1260 | nd, 0.00491 |
| 1261 | nd, 0.0583 |
| 1262 | nd, 0.109 |
| 1263 | nd, 0.0116 |
| 1264 | nd, 0.309 |
| 1265 | nd, 0.0393 |
| 1266 | nd, 0.113 |
| 1267 | nd, 0.285 |
| 1268 | nd, 0.932 |
| 1269 | nd, 0.216 |
| 1270 | nd, 0.0109 |
| 1271 | nd, 0.0627 |
| 1272 | nd, 0.0224 |
| 1273 | nd, 0.132 |
| 1274 | nd, 0.199 |
| 1275 | nd, 0.097 |
| 1276 | nd, 0.0269 |
| 1277 | nd, 0.0429 |
| 1278 | nd, 0.0136 |
| 1279 | nd, 0.00784 |
| 1280 | nd, 0.00438 |
| 1281 | nd, 0.00122 |
| 1282 | nd, 0.00134 |
| 1283 | nd, 0.00151 |
| 1284 | nd, 0.00172 |
| 1285 | nd, 0.0432 |
| 1286 | nd, 0.00323 |
| 1287 | nd, 0.00325 |
| 1288 | nd, 0.0228 |
| 1289 | nd, 0.0267 |
| 1290 | nd, 0.409 |
| 1291 | nd, 0.00847 |
| 1292 | nd, 0.0252 |
| 1293 | nd, 0.0165 |
| 1294 | nd, 0.0327 |
| 1295 | nd, 0.0607 |
| 1296 | nd, 0.0175 |
| 1297 | nd, 0.0238 |
| 1298 | nd, 0.032 |
| 1299 | nd, 0.0424 |
| 1300 | nd, 0.0111 |
| 1301 | nd, 0.0197 |
| 1302 | nd, 0.0734 |
| 1303 | nd, 0.209 |
| 1304 | nd, 0.204 |
| 1305 | nd, 0.431 |

TABLE 1-continued

| Example | TR-FRET Binding IC50 (μM) probe 1, probe 2 |
|---|---|
| 1306 | nd, 0.224 |
| 1307 | nd, 0.401 |
| 1308 | nd, 0.139 |
| 1309 | nd, 0.0767 |
| 1310 | nd, nd |
| 1311 | nd, 0.0917 |
| 1312 | nd, 0.0265 |
| 1313 | nd, 0.0783 |
| 1314 | nd, 0.0247 |
| 1315 | nd, 0.214 |
| 1316 | nd, 0.379 |
| 1317 | nd, 0.074 |
| 1318 | nd, 0.0456 |
| 1319 | nd, 0.0147 |
| 1320 | nd, 0.0163 |
| 1321 | nd, 0.0148 |
| 1322 | nd, nd |
| 1323 | nd, nd |
| 1324 | nd, 0.0779 |
| 1325 | nd, 0.0903 |
| 1326 | nd, 0.0216 |
| 1327 | nd, 1.46 |
| 1328 | nd, 0.147 |
| 1329 | nd, 0.0143 |
| 1330 | nd, 0.0179 |
| 1331 | nd, 0.206 |
| 1332 | nd, 0.0414 |
| 1333 | nd, 0.0195 |
| 1334 | nd, nd |
| 1335 | nd, 0.0855 |
| 1336 | nd, 0.0746 |
| 1337 | nd, 0.105 |
| 1338 | nd, 0.0244 |
| 1339 | nd, 0.0202 |
| 1340 | nd, 0.257 |
| 1341 | nd, 0.195 |
| 1342 | nd, 0.0269 |
| 1343 | nd, 0.0114 |
| 1344 | nd, 0.0821 |
| 1345 | nd, 0.183 |
| 1346 | nd, 0.275 |
| 1347 | nd, 0.0292 |
| 1348 | nd, 0.0565 |
| 1349 | nd, 0.029 |
| 1350 | nd, 0.0149 |
| 1351 | nd, 0.0184 |
| 1352 | nd, 0.0113 |
| 1353 | nd, 0.00584 |
| 1354 | nd, 0.00438 |
| 1355 | nd, 0.00307 |
| 1356 | nd, 0.00784 |
| 1357 | nd, 0.0082 |
| 1358 | nd, 0.013 |
| 1359 | nd, 0.0129 |
| 1360 | nd, 0.00654 |
| 1361 | nd, 0.00515 |
| 1362 | nd, 0.0055 |
| 1363 | nd, 0.00534 |
| 1364 | nd, 0.0149 |
| 1365 | nd, 0.0119 |
| 1366 | nd, 0.0476 |
| 1367 | nd, 0.0291 |
| 1368 | nd, 0.0151 |
| 1369 | nd, 0.056 |
| 1370 | nd, 0.00237 |
| 1371 | nd, 0.0176 |
| 1372 | nd, 0.0106 |
| 1373 | nd, 0.0937 |
| 1374 | nd, nd |
| 1375 | nd, 0.436 |
| 1376 | nd, 0.381 |
| 1377 | nd, 0.275 |
| 1378 | nd, nd |
| 1379 | nd, 0.0867 |
| 1380 | nd, 0.0936 |
| 1381 | nd, 0.189 |
| 1382 | nd, 0.237 |
| 1383 | nd, 0.225 |
| 1384 | nd, 0.0123 |
| 1385 | nd, 0.00676 |
| 1386 | nd, 0.0815 |
| 1387 | nd, 0.0275 |
| 1388 | nd, 0.00403 |
| 1389 | nd, 0.00592 |
| 1390 | nd, 0.0148 |
| 1391 | nd, 0.00956 |
| 1392 | nd, nd |
| 1393 | nd, 0.0129 |
| 1394 | nd, nd |
| 1395 | nd, 0.0176 |
| 1396 | nd, 0.00585 |
| 1397 | nd, nd |
| 1398 | nd, 0.0559 |
| 1399 | nd, 0.179 |
| 1400 | nd, 0.0241 |
| 1401 | nd, 0.018 |
| 1402 | nd, 0.0412 |
| 1403 | nd, 0.0322 |
| 1404 | nd, 0.0561 |
| 1405 | nd, 0.127 |
| 1406 | nd, 0.194 |
| 1407 | nd, 0.227 |
| 1408 | nd, 0.222 |
| 1409 | nd, 0.0823 |
| 1410 | nd, 0.0722 |
| 1411 | nd, 0.135 |
| 1412 | nd, nd |
| 1413 | nd, 0.364 |
| 1414 | nd, 0.00826 |
| 1415 | nd, 0.0111 |
| 1416 | nd, 0.00622 |
| 1417 | nd, 0.0125 |
| 1418 | nd, 0.0113 |
| 1419 | nd, 0.0116 |
| 1420 | nd, nd |
| 1421 | nd, 0.00753 |
| 1422 | nd, 0.0069 |
| 1423 | nd, 0.00831 |
| 1424 | nd, 0.0135 |
| 1425 | nd, 0.035 |
| 1426 | nd, 0.0267 |
| 1427 | nd, 0.033 |
| 1428 | nd, 0.0184 |
| 1429 | nd, 0.0069 |
| 1430 | nd, 0.266 |
| 1431 | nd, 0.011 |
| 1432 | nd, nd |
| 1433 | nd, 0.0587 |
| 1434 | nd, 0.0574 |
| 1435 | nd, 0.0266 |
| 1436 | nd, 0.0484 |
| 1437 | nd, 0.0738 |
| 1438 | nd, 0.0276 |
| 1439 | nd, nd |
| 1440 | nd, nd |
| 1441 | nd, 0.032 |
| 1442 | nd, 0.0136 |
| 1443 | nd, 0.0148 |
| 1444 | nd, 0.00577 |
| 1445 | nd, 0.0128 |
| 1446 | nd, 0.0113 |
| 1447 | nd, 0.0105 |
| 1448 | nd, 0.0223 |
| 1449 | nd, 0.0186 |
| 1450 | nd, 0.0154 |
| 1451 | nd, 0.0139 |
| 1452 | nd, 0.00765 |
| 1453 | nd, 0.0617 |
| 1454 | nd, 0.0678 |
| 1455 | nd, 0.124 |
| 1456 | nd, 0.0422 |
| 1457 | nd, 0.0715 |
| 1458 | nd, 0.0764 |
| 1459 | nd, 0.0669 |

TABLE 1-continued

| Example | TR-FRET Binding IC50 (μM) probe 1, probe 2 |
|---|---|
| 1460 | nd, 0.126 |
| 1461 | nd, 0.0487 |
| 1462 | nd, 0.0694 |
| 1463 | nd, 0.0779 |
| 1464 | nd, 0.109 |
| 1465 | nd, 0.101 |
| 1466 | nd, 0.0125 |
| 1467 | nd, 0.0164 |
| 1468 | nd, 0.00486 |
| 1469 | nd, 0.0138 |
| 1470 | nd, 0.00221 |
| 1471 | nd, 0.0109 |
| 1472 | nd, 0.0125 |
| 1473 | nd, 0.00872 |
| 1474 | nd, 0.00888 |
| 1475 | nd, 0.00744 |
| 1476 | nd, 0.21 |
| 1477 | nd, 0.0452 |
| 1478 | nd, 0.0682 |
| 1479 | nd, 0.0015 |
| 1480 | nd, 0.00425 |
| 1481 | nd, 0.00416 |
| 1482 | nd, 0.00488 |
| 1483 | nd, nd |
| 1484 | nd, 0.00149 |
| 1485 | nd, 0.00323 |
| 1486 | nd, 0.00137 |
| 1487 | nd, 0.00234 |
| 1488 | nd, 0.00844 |
| 1489 | nd, 0.00656 |
| 1490 | nd, nd |
| 1491 | nd, nd |
| 1492 | nd, 0.00153 |
| 1493 | nd, 0.00295 |
| 1494 | nd, 0.00202 |
| 1495 | nd, 0.00877 |
| 1496 | nd, 0.00844 |
| 1497 | nd, 0.00135 |
| 1498 | nd, 0.00228 |
| 1499 | nd, 0.00152 |
| 1500 | nd, 0.00415 |
| 1501 | nd, 0.00264 |
| 1502 | nd, 0.0101 |
| 1503 | nd, 0.0067 |
| 1504 | nd, 0.0101 |
| 1505 | nd, nd |
| 1506 | nd, 0.00219 |
| 1507 | nd, nd |
| 1508 | nd, 0.00244 |
| 1509 | nd, 0.00397 |
| 1510 | nd, 0.00326 |
| 1511 | nd, 0.00664 |
| 1512 | nd, nd |
| 1513 | nd, 0.0028 |
| 1514 | nd, 0.00183 |
| 1515 | nd, 0.00159 |
| 1516 | nd, 0.00457 |
| 1517 | nd, 0.00103 |
| 1518 | nd, 0.00155 |
| 1519 | nd, 0.00168 |
| 1520 | nd, 0.00203 |
| 1521 | nd, 0.0019 |
| 1522 | nd, 0.0316 |
| 1523 | nd, 0.0134 |
| 1524 | nd, 0.00324 |
| 1525 | nd, 0.0063 |
| 1526 | nd, 0.00714 |
| 1527 | nd, 0.0026 |
| 1528 | nd, 0.00881 |
| 1529 | nd, 0.00174 |
| 1530 | nd, 0.00389 |
| 1531 | nd, 0.124 |
| 1532 | nd, 0.00541 |
| 1533 | nd, 0.0102 |
| 1534 | nd, 0.0213 |
| 1535 | nd, 0.0201 |
| 1536 | nd, 0.0114 |
| 1537 | nd, 0.0118 |
| 1538 | nd, 0.0257 |
| 1539 | nd, 0.0611 |
| 1540 | nd, 0.0644 |
| 1541 | nd, 0.031 |
| 1542 | nd, 0.762 |
| 1543 | nd, 0.20 |
| 1544 | nd, 0.193 |
| 1545 | nd, 0.774 |
| 1546 | nd, 0.0241 |
| 1547 | nd, 0.00501 |
| 1548 | nd, 0.000973 |
| 1549 | nd, 0.00471 |
| 1550 | nd, 0.0112 |
| 1551 | nd, 0.00472 |
| 1552 | nd, 0.00086 |
| 1553 | nd, 0.0216 |
| 1554 | nd, 0.0385 |
| 1555 | nd, 0.0104 |
| 1556 | nd, 0.0488 |
| 1557 | nd, 0.0058 |
| 1558 | nd, 0.0165 |
| 1559 | nd, 0.0447 |
| 1560 | nd, 0.0655 | nd = not determined

ROCK2 Kinase Activity Assays

[$^{33}$P]-ATP assay: ROCK2 activity was initially determined using a radioactive FlashPlate-based assay. In a 96-well format, biotinylated peptide substrates (2 mM final; S6-short for ROCK2), γ-[$^{33}$P]-ATP (5 μM, 2 mCi/mmol), compounds (0.1-10000 nM in 2% DMSO), and ROCK2 (0.2 nM; Upstate) catalytic domains.

HTRF assay: This assay used the CisBio HTRF KinEASE kit (kit 62ST2PEZ) and the kinase reaction containing 0.2 μM biotinylated substrate peptide (S2, CisBio), 5 μM, 100 μM or 1 mM of ATP, inhibitors (0.1-10,000 nM in 2% DMSO) and enzymes as in the $^{33}$P-ATP assay above.

TABLE 2 shows the results of the HTRF assay and the utility of compounds having Formula I to functionally inhibit ROCK2.

TABLE 2

| Example | ROCK2 HTRF Binding Ki (μM) |
|---|---|
| 374 | 0.0036 |
| 375 | 4.06 |
| 376 | 0.00526 |
| 377 | 0.0195 |
| 378 | 0.00237 |
| 379 | 0.0024 |
| 380 | 0.0023 |
| 381 | 0.00412 |
| 382 | 0.00614 |
| 383 | 0.00361 |
| 384 | 0.00424 |
| 385 | 0.00651 |
| 386 | 10 |
| 387 | 0.00139 |
| 388 | 0.0112 |
| 389 | 0.00174 |
| 390 | 0.00245 |
| 391 | 0.00049 |
| 392 | nd |
| 393 | nd |

TABLE 2-continued

| Example | ROCK2 HTRF Binding Ki (µM) |
|---|---|
| 394 | 0.0093 |
| 395 | 0.0321 |
| 396 | 0.182 |
| 397 | 0.138 |
| 398 | 0.0022 |
| 399 | nd |
| 400 | 0.0251 |
| 547 | 0.179 |
| 548 | 0.014 |
| 549 | 0.0031 |
| 550 | 0.0154 |
| 551 | 0.0184 |
| 552 | 3.27 | nd = not determined

Compounds which inhibit NAMPT are useful for treating diseases in which activation of NF-KB is implicated. Such methods are useful in the treatment of a variety of diseases including inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukaemia, lymphoma or Hodgkin's disease, cachexia, inflammation associated with infection and certain viral infections, including Acquired Immune Deficiency Syndrome (AIDS), adult respiratory distress syndrome, and ataxia telengiectasia.

Involvement of NAMPT in the treatment of cancer is described in WO 97/48696. Involvement of NAMPT in immuno-supression is described in WO 97/48397. Involvement of NAMPT for the treatment of diseases involving angiogenesis is described in WO 2003/80054. Involvement of NAMPT for the treatment of rheumatoid arthritis and septic shock is described in WO 2008/025857. Involvement of NAMPT for the prophlaxis and treatment of ischaemia is described in WO 2009/109610.

Cancers include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

Abnormal activation of the Rho/ROCK pathway has been observed in various disorders (Wettschureck, N., Offermanns, S., Rho/Rho-kinase mediated signaling in physiology and pathophysiology. J. Mol. Med. 80, 2002, 629-638; Müller, B. K., Mack, H., Teusch, N., Rho kinase, a promising drug target for neurological discorders. Nat. Drug Discov. Rev. 4, 2005, 387-398; Hu, E, Lee, D., ROCK inhibitors as potential therapeutic agents for cardiovascular diseases. Curr. Opin. Investig. Drugs. 4, 2003, 1065-1075). As already mentioned, ROCKs phosphorylate the myosin binding subunit of myosin light chain (MLC) phosphatase (MLCP), resulting in increased myosin phosphorylation and actin-myosin contraction (Somlyo, A. P., Somlyo, A. V., Ca2+ sensitivity of smooth muscle and nonmuscle myosin II: modulated by G proteins, kinases, and myosin phosphatase. Physiol. Rev. 83, 2003, 1325-1358). Examples of disease states related with abnormal Rho/ROCK activity, in particular with vasospasm activity, include cardiovascular diseases such as hypertension (Satoh S., Kreutz R., Wilm C., Ganten D., Pfitzer G., Augmented agonist-induced $Ca^{2+}$-sensitization of coronary artery contraction in genetically hypertensive rats. Evidence for altered signal transduction in the coronary smooth muscle cells. J. Clin. Invest. 94, 1994, 1397-1403; Mukai, Y., Shimokawa, H., Matoba, T., Kandabashi, T., Satoh, S., Hiroki, J., Kaibuchi, K., Takeshita, A., Involvement of Rho-kinase in hypertensive vascular disease: a novel therapeutic target in hypertension. FASEB J. 15, 2001, 1062-1064; Uehata, M., Ishizaki, T., Satoh, H., Ono, T., Kawahara, T., Morishita, T., Tamakawa, H., Yamagami, K., Inui, J., Maekawa, M., Narumiya, S., Calcium sensitization of smooth muscle mediated by a Rho-associated protein kinase in hypertension. Nature 389, 1997, 990-994; Masumoto, A., Hirooka, Y., Shimokawa, H., Hironaga, K., Setoguchi, S., Takeshita, A., Possible involvement of Rhokinase in the pathogenesis of hypertension in humans. Hypertension 38, 2001, 1307-1310), chronic and congestive heart failure (Fuster, V., Badimon, L., Badimon, J J, Chesebro, J H, The pathogenesis of coronary artery disease and the acute coronary syndromes (2). N Engl J Med 326, 1992, 310-318; Shimokawa, H., Cellular and molecular mechanisms of coronary artery spasm: lessons from animal models. Jpn Circ J 64, 2000, 1-12; Shimokawa, H., Morishige, K., Miyata, K., Kandabashi, T., Eto, Y., Ikegaki, I., Asano, T., Kaibuchi, K., Takeshita, A., Longterm inhibition of Rho-kinase induces a regression of arteriosclerotic coronary lesions in a porcine model in vivo. Cardiovasc Res 51, 2001, 169-177; Utsunomiya, T., Satoh, S., Ikegaki, I., Toshima, Y., Asano, T., Shimokawa, H., Antianginal effects of hydroxyfasudil, a Rho-kinase inhibitor, in a canine model of effort angina. Br J Pharmacol 134, 201, 1724-1730), cardiac hypertrophy (Hoshijima, M., Sah, V. P., Wang, Y., Chien, K. R., Brown, J. H., The low molecular weight GTPase Rho regulates myofibril formation and organization in neonatal rat ventricular myocytes. Involvement of Rho kinase. J Biol Chem 273, 1998, 7725-77230; Sah, V. P., Hoshijima, M., Chien, K. R., Brown, J. H., Rho is required for Galphaq and alpha1-adrenergic receptor signal-637 ing in cardiomyocytes. Dissociation of Ras and Rho pathways. J Biol Chem 271, 1996, 31185-1190; Kuwahara, K., Saito, Y., Nakagawa, O., Kishimoto, I., Harada, M., Ogawa, E., Miyamoto, Y., Hamanaka, I., Kajiyama, N., Takahashi, N., Izumi, T., Kawakami, R., Tamura, N., Ogawa, Y., Nakao, K., The effects of the selective ROCK inhibitor, Y27632, on ET-1-induced hypertrophic response in neonatal rat cardiacmyocytes-possible involvement of Rho/ROCK pathway in cardiac muscle cell hypertrophy. FEBS Lett 452, 1999, 314-318), chronic renal failure (Sharpe, C. C., Hendry, B., M. Signaling: focus on Rho in renal disease. J. Am. Soc. Nephrol. 14, 2003, 261-264), cerebral vasospasm after subarachnoid bleeding (Shibuya, M., Suzuki, Y., Sugita, K., Saito, I., Sasaki, T., Takakura, K., Okamoto, S., Kikuchi, H., Takemae, T., Hidaka, H., Dose escalation trial of a novel calcium antagonist, AT877, in patients 636 with aneurysmal subarachnoid haemorrhage. Acta Neurochir (Wien) 107, 1990, 11-15; Shibuya, M., Suzuki, Y., Sugita, K., Saito, I., Sasaki, T., Takakura, K., Nagata, I., Kikuchi, H., Takemae, T., Hidaka, H., et. al, *Effect of AT877* on cerebral vasospasm after aneurysmal subarachnoid hemorrhage. Results of a prospective placebo-controlled double-blind trial. J Neurosurg 76, 1992, 571-577; Sato, M., Tani, E., Fujikawa, H., Kaibuchi, K., Involvement of Rho-kinase-mediated phosphorylation of myosin light chain in enhancement of cerebral vasospasm. Circ Res 87, 2000, 195-200; Miyagi, Y., Carpenter, R. C., Meguro, T., Parent, A. D., Zhang, J. H., Upregulation of rho A and rho kinase messenger RNAs in the basilar artery of a rat model of subarachnoid hemorrhage. J Neurosurg 93, 2000, 471-476; Tachibana, E., Harada, T., Shibuya, M. Saito, K., Takayasu, M., Suzuki, Y., Yoshida, J., Intra-arterial infusion of fasudil hydrochloride for treating vasospasm following subarachnoid haemorrhage. Acta Neurochir (Wien) 141, 1999, 13-19), pulmonary hypertension (Sylvester, J. T., Am. J. Physiol. Lung Cell. Mol. Physiol. 287, 2004, L624-L630) and ocular hypertension (Honjo, M., Inatani, M., Kido, N., Sawamura, T., Yue, B. Y., Honda, Y., Tanihara, H., Effects of protein kinase inhibitor, HA1077, on intraocular pressure and outflow facility in rabbit eyes. Arch Ophthalmol 119, 2001, 1171-1178; Rao, P. V, Deng, P. F., Kumar, J. Epstein, D. L., Modulation of aqueous humor outflow facility by the Rho kinase-specific inhibitor Y-27632. Invest Ophthalmol V is Sci 42, 2001, 1029-1037). Further diseases related to abnormal Rho/ROCK activity are cancer (Aznar, S., Fernandez-Valeron, P., Espina, C., Lacal, J. C., Rho GTPases: potential candidates for anticancer therapy. Cancer Lett. 206, 2004, 181-191; Yin, L. et al., Fasudil inhibits vascular endothelial growth factor-induced angiogenesis in vitro and in vivo. Mol Cancer Ther 5, 2007, 1517-25; Itoh, K., Yoshioka, K., Akedo, H., Uehata, M., Ishizaki, T., Narumiya, S., An essential part for Rho-associated kinase in the transcellular invasion of tumor cells. Nat Med 5, 1999, 221-225; Genda, T. Sakamoto, M., Ichida, T., Asakura, H., Kojiro, M., Narumiya, S., Hirohashi, S., Cell motility mediated by rho and Rho-associated protein kinase plays a critical role in intrahepatic metastasis of human hepatocellular carcinoma. Hepatology 30, 1999, 1027-1036; Somlyo, A. V., Bradshaw, D., Ramos, S., Murphy, C., Myers, C. E., Somlyo, A. P., Rho-kinase inhibitor retards migration and in vivo dissemination of human prostate cancer cells. Biochem Biophys Res Commun 269, 2000, 652-659), asthma (Roberts, J. A., Raeburn, D., Rodger, I. W., Thomson, N. C., Comparison of in vivo airway responsiveness and in vitro smooth muscle sensitivity to methacholine in man. Thorax 39; 1984, 837-843; Chiba, Y., Misawa, M., Characteristics of muscarinic cholinoceptors in airways of antigen-induced airway hyperresponsive rats. Comp Biochem Physiol C Pharmacol Toxicol Endocrinol 111, 1995, 351-357; Chiba, Y., Takada, Y., Miyamoto, S., MitsuiSaito, M., Karaki, H., Misawa, M., Augmented acetylcholine-induced, Rho mediated $Ca^{2+}$ sensitization of bronchial smooth muscle contraction in antigen-induced airway hyperresponsive rats. Br J Pharmacol 127, 1999, 597-600; Chiba, Y., Sakai, H. Misawa, M., Augmented acetylcholine-induced translocation of RhoA in bronchial smooth muscle from antigen-induced airway hyperresponsive rats. Br J Pharmacol 133, 2001, 886-890; Iizuka, K., Shimizu, Y., Tsukagoshi, H., Yoshii, A., Harada, T. Dobashi, K., Murozono, T., Nakazawa, T., Mori, M., Evaluation of Y-27632, a rho-kinase inhibitor, as a bronchodilator in guinea pigs. Eur J Pharmacol 406, 2000, 273-279), male erectile dysfunctions (Andersson, K. E., Hedlund, P., New directions for erectile dysfunction therapies. Int. J. Impot. Res. 14 (Suppl. 1), 2002, S82-S92; Chitaley, K., Wingard, C. J., Clinton Webb, R., Branam, H., Stopper, V. S., Lewis, R. W., Mills, T. M., Antagonism of Rho-kinase stimulates rat penile erection via a nitric oxideindependent pathway. Nat Med 7, 2001, 119-122; Mills, T. M., Chitaley, K., Wingard, C. J., Lewis, R. W., Webb, R. C., Effect of Rho-kinase inhibition on vasoconstriction in the penile circulation. J Appl Physiol 91, 2001, 1269-1273), female sexual dysfunction, over-active bladder syndrome (Peters, S. L. et al., Rho kinase: a target for treating urinary bladder dysfunction. Trends Pharmacol Sci. 27, 2006, 492-7) and preterm labor (Niiro, N., Nishimura, J., Sakihara, C., Nakano, H., Kanaide, H., Up-regulation of rho A and rho-kinase mRNAs in the rat myometrium during pregnancy. Biochem Biophys Res Commun 230, 1997, 356-359; Tahara, M., Morishige, K., Sawada, K., Ikebuchi, Y., Kawagishi, R., Tasaka, K., Murata, Y., RhoA/Rho-kinase cascade is involved in oxytocin-induced rat uterine contraction. Endocrinology 143, 2002, 920-929; Kupittayanant, S., Burdyga, T., Wray, S., The effects of inhibiting Rho-associated kinase with Y-27632 on force and intracellular calcium in human myometrium. Pflugers Arch. 443, 2001, 112-114).

Inhibitors of ROCKs have been suggested for use in the treatments of a variety of diseases. They include cardiovascular diseases such as hypertension (Satoh S., Kreutz R., Wilm C., Ganten D., Pfitzer G., Augmented agonist-induced $Ca^{2+}$-sensitization of coronary artery contraction in genetically hypertensive rats. Evidence for altered signal transduction in the coronary smooth muscle cells. J. Clin. Invest. 94, 1994, 1397-1403; Mukai, Y., Shimokawa, H., Matoba, T., Kandabashi, T., Satoh, S., Hiroki, J., Kaibuchi, K., Takeshita, A., Involvement of Rho-kinase in hypertensive vascular disease: a novel therapeutic target in hypertension. FASEB J. 15, 2001, 1062-1064; Uehata, M., Ishizaki, T., Satoh, H., Ono, T., Kawahara, T., Morishita, T., Tamakawa, H., Yamagami, K., Inui, J., Maekawa, M., Narumiya, S., Calcium sensitization of smooth muscle mediated by a Rho-associated protein kinase in hypertension. Nature 389, 1997, 990-994; and Masumoto, A., Hirooka, Y., Shimokawa, H., Hironaga, K., Setoguchi, S., Takeshita, A., Possible involvement of Rhokinase in the pathogenesis of hypertension in humans. Hypertension 38, 2001, 1307-1310), chronic and congestive heart failure (Fuster, V., Badimon, L., Badimon, J J, Chesebro, J H, The pathogenesis of coronary artery disease and the acute coronary syndromes (2). N Engl J Med 326, 1992, 310-318; Shimokawa, H., Cellular and molecular mechanisms of coronary artery spasm: lessons from animal models. Jpn Circ J 64, 2000, 1-12; Shimokawa, H., Morishige, K., Miyata, K., Kandabashi, T., Eto, Y., Ikegaki, I., Asano, T., Kaibuchi, K., Takeshita, A., Longterm inhibition of Rho-kinase induces a regression of arteriosclerotic coronary lesions in a porcine model in vivo. Cardiovasc Res 51, 2001, 169-177; Utsunomiya, T., Satoh, S., Ikegaki, I., Toshima, Y., Asano, T., Shimokawa, H., Antianginal effects of hydroxyfasudil, a Rho-kinase inhibitor, in a canine model of effort angina. Br J Pharmacol 134, 201, 1724-1730), cardiac hypertrophy), and cardiac hypertrophy (Hoshijima, M., Sah, V. P., Wang, Y., Chien, K. R., Brown, J. H., The low molecular weight GTPase Rho regulates myofibril formation and organization in neonatal rat ventricular myocytes. Involvement of Rho kinase. J Biol Chem 273, 1998, 7725-77230; Sah, V. P., Hoshijima, M., Chien, K. R., Brown, J. H., Rho is required for Galphaq and alpha1-adrenergic receptor signal-637 ing in cardiomyocytes. Dissociation of Ras and Rho pathways. J Biol Chem 271, 1996, 31185-1190; Kuwahara, K., Saito, Y., Nakagawa, 0., Kishimoto, I., Harada, M., Ogawa, E., Miyamoto, Y., Hamanaka, I., Kajiyama, N., Takahashi, N., Izumi, T., Kawakami, R., Tamura, N., Ogawa, Y., Nakao, K., The effects of the selective ROCK inhibitor, Y27632, on ET-1-induced hypertrophic response in neonatal rat cardiacmyocytes-possible involvement of Rho/ROCK pathway in cardiac muscle cell hypertrophy. FEBS Lett 452, 1999, 314-318), chronic renal failure), chronic renal failure (Sharpe, C. C., Hendry, B., M. Signaling: focus on Rho in renal disease. J. Am. Soc. Nephrol. 14, 2003, 261-264), furthermore cerebral vasospasm after subarachnoid bleeding (Shibuya, M., Suzuki, Y., Sugita, K., Saito, I., Sasaki, T., Takakura, K., Okamoto, S., Kikuchi, H., Takemae, T., Hidaka, H., Dose escalation trial of a novel calcium antagonist, AT877, in patients 636 with aneurysmal subarachnoid haemorrhage. (Acta Neurochir (Wien) 107, 1990, 11-15; Shibuya, M., Suzuki, Y., Sugita, K., Saito, I., Sasaki, T., Takakura, K., Nagata, I., Kikuchi, H., Takemae, T., Hidaka, H., et. al, Effect of AT877 on cerebral vasospasm after aneurysmal subarachnoid hemorrhage. Results of a prospective placebo-controlled double-blind trial. J Neurosurg 76, 1992, 571-577; Sato, M., Tani, E., Fujikawa, H., Kaibuchi, K., Involvement of Rho-kinase-mediated phosphorylation of myosin light chain in enhancement of cerebral vasospasm. Circ Res 87, 2000, 195-200; Miyagi, Y., Carpenter, R. C., Meguro, T., Parent, A. D., Zhang, J. H., Upregulation of rho A and rho kinase messenger RNAs in the basilar artery of a rat model of subarachnoid hemorrhage. J Neurosurg 93, 2000, 471-476; Tachibana, E., Harada, T., Shibuya, M. Saito, K., Takayasu, M., Suzuki, Y., Yoshida, J., Intra-arterial infusion of fasudil hydrochloride for treating vasospasm following subarachnoid haemorrhage. Acta Neurochir (Wien) 141, 1999, 13-19), pulmonary hypertension (Sylvester, J. T., Am. J. Physiol. Lung Cell. Mol. Physiol. 287, 2004, L624-L630) and ocular hypertension (Honjo, M., Inatani, M., Kido, N., Sawamura, T., Yue, B. Y., Honda, Y., Tanihara, H., Effects of protein kinase inhibitor, HA1077, on intraocular pressure and outflow facility in rabbit eyes. Arch Ophthalmol 119, 2001, 1171-1178; Rao, P. V, Deng, P. F., Kumar, J. Epstein, D. L., Modulation of aqueous humor outflow facility by the Rho kinase-specific inhibitor Y-27632. Invest Ophthalmol V is Sci 42, 2001, 1029-1037). In addition, because of their muscle relaxing properties, they are also suitable for asthma (Roberts, J. A., Raeburn, D., Rodger, I. W., Thomson, N. C., Comparison of in vivo airway responsiveness and in vitro smooth muscle sensitivity to methacholine in man. Thorax 39; 1984, 837-843; Chiba, Y., Misawa, M., Characteristics of muscarinic cholinoceptors in airways of antigen-induced airway hyperresponsive rats. Comp Biochem Physiol C Pharmacol Toxicol Endocrinol 111, 1995, 351-357; Chiba, Y., Takada, Y., Miyamoto, S., MitsuiSaito, M., Karaki, H., Misawa, M., Augmented acetylcholine-induced, Rho mediated $Ca^{2+}$ sensitization of bronchial smooth muscle contraction in antigen-induced airway hyperresponsive rats. Br J Pharmacol 127, 1999, 597-600; Chiba, Y., Sakai, H. Misawa, M., Augmented acetylcholine-induced translocation of RhoA in bronchial smooth muscle from antigen-induced airway hyperresponsive rats. BrJ Pharmacol 133, 2001, 886-890; Iizuka, K., Shimizu, Y., Tsukagoshi, H., Yoshii, A., Harada, T. Dobashi, K., Murozono, T., Nakazawa, T., Mori, M., Evaluation of Y-27632, a rho-kinase inhibitor, as a bronchodilator in guinea pigs. Eur J Pharmacol 406, 2000, 273-279), male erectile dysfunctions (Andersson, K. E., Hedlund, P., New directions for erectile dysfunction therapies. Int. J. Impot. Res. 14 (Suppl. 1), 2002, S82-S92; Chitaley, K., Wingard, C. J., Clinton Webb, R., Branam, H., Stopper, V. S., Lewis, R. W., Mills, T. M., Antagonism of Rho-kinase stimulates rat penile erection via a nitric oxideindependent pathway. Nat Med 7, 2001, 119-122; Mills, T. M., Chitaley, K., Wingard, C. J., Lewis, R. W., Webb, R. C., Effect of Rho-kinase inhibition on vasoconstriction in the penile circulation. J Appl Physiol 91, 2001, 1269-1273), female sexual dysfunction and over-active bladder syndrome (Peters, S. L. et al., Rho kinase: a target for treating urinary bladder dysfunction. Trends Pharmacol Sci. 27, 2006, 492-7) and preterm labor (Niiro, N., Nishimura, J., Sakihara, C., Nakano, H., Kanaide, H., Up-regulation of rho A and rho-kinase mRNAs in the rat myometrium during pregnancy. Biochem Biophys Res Commun 230, 1997, 356-359; Tahara, M., Morishige, K., Sawada, K., Ikebuchi, Y., Kawagishi, R., Tasaka, K., Murata, Y., RhoA/Rho-kinase cascade is involved in oxytocin-induced rat uterine contraction. Endocrinology 143, 2002, 920-929; Kupittayanant, S., Burdyga, T., Wray, S., The effects of inhibiting Rho-associated kinase with Y-27632 on force and intracellular calcium in human myometrium. Pflugers Arch. 443, 2001, 112-114). Several recent studies have reported the beneficial effects of ROCK inhibitors in ischemia-reperfusion and myocardial infarction. In these studies, the ROCK inhibitors Y-27632 and fasudil were shown to decrease ischemia-reperfusion injury, myocardial infarct size, and myocardial fibrosis in response to experimental myocardial infarction (MI) and in a rat model of chronic hypertension induced congestive heart failure (see above (Fuster, V., Badimon, L., Badimon, J J, Chesebro, J H, The pathogenesis of coronary artery disease and the acute coronary syndromes (2). N Engl J Med 326, 1992, 310-318; Shimokawa, H., Cellular and molecular mechanisms of coronary artery spasm: lessons from animal models. Jpn Circ J 64, 2000, 1-12; Shimokawa, H., Morishige, K., Miyata, K., Kandabashi, T., Eto, Y., Ikegaki, I., Asano, T., Kaibuchi, K., Takeshita, A., Longterm inhibition of Rho-kinase induces a regression of arteriosclerotic coronary lesions in a porcine model in vivo. Cardiovasc Res 51, 2001, 169-177; Utsunomiya, T., Satoh, S., Ikegaki, I., Toshima, Y., Asano, T., Shimokawa, H., Antianginal effects of hydroxyfasudil, a Rho-kinase inhibitor, in a canine model of effort angina. Br J Pharmacol 134, 201, 1724-1730), cardiac hypertrophy) and Masumoto, A., Mohri, M., Shimokaw, a H., Urakami, L., Usui, M., Takeshita, A., Suppression of coronary artery spasm by the rho-kinase inhibitor fasudil in patients with vasospastic angina. Circulation 105, 2002, 1545-1547; Shimokawa, H., Iinuma, H., Kishida, H., et al., Antianginal effect of fasudil, a Rho-kinase inhibitor, in patients with stable effort angina: a multicenter study (abstract). Circulation 104[Suppl II], 2001, II691; Morishige K, Shimokawa H, Eto Y, Kandabashi T, Miyata K, Matsumoto Y, Hoshijima M, Kaibuchi K, Takeshita A, Adenovirus-mediated transfer of dominant-negative rho-kinase induces a regression of coronary arteriosclerosis in pigs in vivo. Arterioscler Thromb Vasc Biol 21, 2001, 548-554; Kandabashi T, Shimokawa H, Mukai Y, Matoba T, Kunihiro I, Morikawa K, I to M, Takahashi S, Kaibuchi K, Takeshita A, Involvement of rho-kinase in agonists-induced contractions of arteriosclerotic human arteries. Arterioscler Thromb Vasc Biol 22, 2002, 243-248; Liu M W, Roubin G S, King S B 3$^{rd}$, Restenosis after coronary angioplasty. Potential biologic determinants and role of intimal hyperplasia. Circulation 79, 1989, 1374-1387; Shibata R, Kai H, Seki Y, Kato S, Morimatsu M, Kaibuchi K, Imaizumi T, Role of Rho-associated kinase in neointima formation after vascular injury. Circulation 103, 2001, 284-289).

Additionally, ROCKs can interact with other signalling pathways resulting in inhibition of phosphoinositide-3 kinase (PI-3K), endothelial nitric oxide synthase (eNOS) pathways, and activation of plasminogen activator inhibitor-1 (PAI-1) which may contribute to endothelial dysfunction like restenosis and atherosclerosis. Thus ROCK inhibitors have been suggested for the treatment of restenosis and atherosclerosis (see above (Morishige K, Shimokawa H, Eto Y, Kandabashi T, Miyata K, Matsumoto Y, Hoshijima M, Kaibuchi K, Takeshita A, Adenovirus-mediated transfer of dominant-negative rho-kinase induces a regression of coronary arteriosclerosis in pigs in vivo. Arterioscler Thromb Vasc Biol 21, 2001, 548-554; Kandabashi T, Shimokawa H, Mukai Y, Matoba T, Kunihiro I, Morikawa K, Ito M, Takahashi S, Kaibuchi K, Takeshita A, Involvement of rho-kinase in agonists-induced contractions of arteriosclerotic human arteries. Arterioscler Thromb Vasc Biol 22, 2002, 243-248; Liu M W, Roubin G S, King S B 3$^{rd}$, Restenosis after coronary angioplasty. Potential biologic determinants and role of intimal hyperplasia. Circulation 79, 1989, 1374-1387; Shibata R, Kai H, Seki Y, Kato S, Morimatsu M, Kaibuchi K, Imaizumi T, Role of Rho-associated kinase in neointima formation after vascular injury. Circulation 103, 2001, 284-289) and Iwasaki, H. et al., High glucose induces plasminogen activator inhibitor-1 expression through Rho/Rho-kinase-mediated NF-kappaB activation in bovine aortic endothelial cells. Atherosclerosis, 2007, January 31).

Vascular intimal thickening in vein grafts after surgery is the major cause of late graft failure. In a study with the ROCK inhibitor fasudil, the intimal thickening and vascular smooth muscle cell (VSMC) proliferation was significantly suppressed, whereas VSMC apoptosis was enhanced in the weeks following the procedure, suggesting that ROCK inhibitors can be used as a therapeutic agent for the prevention of graft (Morishige K, Shimokawa H, Eto Y, Kandabashi T, Miyata K, Matsumoto Y, Hoshijima M, Kaibuchi K, Takeshita A, Adenovirus-mediated transfer of dominant-negative rho-kinase induces a regression of coronary arteriosclerosis in pigs in vivo. Arterioscler Thromb Vasc Biol 21, 2001, 548-554; Kandabashi T, Shimokawa H, Mukai Y, Matoba T, Kunihiro I, Morikawa K, Ito M, Takahashi S, Kaibuchi K, Takeshita A, Involvement of rho-kinase in agonists-induced contractions of arteriosclerotic human arteries. Arterioscler Thromb Vasc Biol 22, 2002, 243-248; Liu M W, Roubin G S, King S B 3$^{rd}$, Restenosis after coronary angioplasty. Potential biologic determinants and role of intimal hyperplasia. Circulation 79, 1989, 1374-1387; Shibata R, Kai H, Seki Y, Kato S, Morimatsu M, Kaibuchi K, Imaizumi T, Role of Rho-associated kinase in neointima formation after vascular injury. Circulation 103, 2001, 284-289).

Injury to the adult vertebrate brain and spinal cord activates ROCKs, thereby causing neurodegeneration and inhibition of neuroregeneration like neurite growth and sprouting (Bito, H., Furuyashiki, T., Ishihara, H., Shibasaki, Y., Ohashi, K., Mizuno, K., Maekawa, M., Ishizaki, T., Narumiya, S., A critical role for a Rho-associated kinase, p 160ROCK, in determining axon outgrowth in mammalian CNS neurons. Neuron 26, 2000, 431-441). Inhibition of ROCKs results in induction of new axonal growth, axonal rewiring across lesions within the CNS, accelerated regeneration and enhanced functional recovery after acute neuronal injury in mammals (spinal-cord injury, traumatic brain injury) (see above (Peters, S. L. et al., Rho kinase: a target for treating urinary bladder dysfunction. Trends Pharmacol Sci. 27, 2006, 492-7) and Hara, M. et al., Protein kinase inhibition by fasudil hydrochloride promotes neurological recovery after spinal cord injury in rats. J. Neurosurg. Spine 93, 94-101; Fournier, A. E., Takizawa, B. T. & Strittmatter, S. M., ROCK inhibition enhances axonal regeneration in the injured CNS. J. Neurosci. 23, 2003, 1416-1423; Sung, J. K. et al., A possible role of RhoA/Rho-kinase in experimental spinal cord injury in rat. Brain Res. 959, 2003, 29-38; Tanaka, H. et al., Cytoplasmic p21(Cip1/WAF1) enhances axonal regeneration and functional recovery after spinal cord injury in rats. Neuroscience 127, 2004, 155-164). ROCK inhibitors are therefore likely to be useful for regenerative (recovery) treatment of CNS disorders such as spinal cord injury, acute neuronal injury (stroke, traumatic brain injury) (Okamura N et al., Vasodilator effects of fasudil, a Rho-kinase inhibitor, on retinal arterioles in stroke-prone spontaneously hypertensive rats. J Ocul Pharmacol Ther. 23, 2007, 207-12; Yagita Y et al., Rho-kinase activation in endothelial cells contributes to expansion of infarction after focal cerebral ischemia. J Neurosci Res. 85, 2007, 2460-9), Parkinson's disease, Alzheimer disease (Pedrini S et al., Modulation of statin-activated shedding of Alzheimer APP ectodomain by ROCK. PLoS Med. 2, 2005, 18; Burton A., NSAIDS and Alzheimer's disease: it's only Rock and Rho. Lancet Neurol. 3(1), 2004, 6) and other neurodegenerative disorders. Other neurodegenetarive disorders for which ROCK inhibitors are expected to be useful are Huntington's disease (Shao J, Welch W J, Diprospero N A, Diamond M I. Phosphorylation of profilin by ROCK1 regulates polyglutamine aggregation. Mol Cell Biol. 2008 September; 28(17):5196-208; Shao J, Welch W J, Diamond M I. ROCK and PRK-2 mediate the inhibitory effect of Y-27632 on polyglutamine aggregation. FEBS Lett. 2008 May 28; 582(12):1637-42), spinal muscular atrophy (Bowerman M, Shafey D, Kothary R. Smn depletion alters profilin II expression and leads to upregulation of the RhoA/ROCK pathway and defects in neuronal integrity. J Mol. Neurosci. 2007; 32(2):120-31) and amyotrophic lateral sclerosis Inhibition of the Rho/ROCK pathway has also proved to be efficacious in other animal models of neurodegeneration like stroke (Okamura N et al., Vasodilator effects of fasudil, a Rho-kinase inhibitor, on retinal arterioles in stroke-prone spontaneously hypertensive rats. J Ocul Pharmacol Ther. 23, 2007, 207-12; Yagita Y et al., Rho-kinase activation in endothelial cells contributes to expansion of infarction after focal cerebral ischemia. J Neurosci Res. 85, 2007, 2460-9) and in inflammatory and demyelinating diseases like multiple sclerosis (Sun X et al., The selective Rho-kinase inhibitor Fasudil is protective and therapeutic in experimental autoimmune encephalomyelitis. J Neuroimmunol 180, 2006, 126-34), acute and chronic pain (Inoue, M. et al., Initiation of neuropathic pain requires lysophosphatidic acid receptor signaling. Nature Med. 10, 2004, 712-718; Ramer, L. M., Borisoff, J. F. & Ramer, M. S., Rho-kinase inhibition enhances axonal plasticity and attenuates cold hyperalgesia after dorsal rhizotomy. J. Neurosci. 24, 2004, 10796-10805; Tatsumi, S. et al., Involvement of Rho-kinase in inflammatory and neuropathic pain through phosphorylation of myristoylated alanine-rich C-kinase substrate (MARCKS). Neuroscience 131, 2005, 491-498).

ROCK inhibitors have been shown to possess anti-inflammatory properties by decreased cytokine release, e.g. TNFα. Thus they can be used as treatment for neuroinflammatory diseases such as stroke, multiple sclerosis, Alzheimer's disease, Parkinson's disease, amyotrophic lateral sclerosis and inflammatory pain, as well as other inflammatory diseases such as rheumatoid arthritis, osteoarthritis, osteoporosis, asthma, irritable bowel syndrome, or inflammatory bowel disease (Segain J. P., Rho kinase blockade prevents inflammation via nuclear factor kappa B inhibition: evidence in Crohn's disease and experimental colitis. Gastroenterology. 124(5), 2003, 1180-7). In addition, recent reports have demonstrated that inhibition of ROCK results in disruption of inflammatory cell chemotaxis as well as inhibition of smooth muscle contraction in models of pulmonary inflammation associated with asthma. Therefore, the inhibitors of the Rho/ROCK pathway should be useful for the treatment of asthma (see above (Sun X et al., The selective Rho-kinase inhibitor Fasudil is protective and therapeutic in experimental autoimmune encephalomyelitis. J Neuroimmunol 180, 2006, 126-34) and Kawaguchi A, Ohmori M, Harada K, Tsuruoka S, Sugimoto K, Fujimura A., The effect of a Rho kinase inhibitor Y-27632 on superoxide production, aggregation and adhesion inhuman polymorphonuclear leukocytes. Eur J Pharmacol 403, 2000, 203-208; Lou Z, Billadeau D D, Savoy D N, Schoon R A, Leibson P. J., A role for a RhoA/ROCK/LIM-kinase pathway in the regulation of cytotoxic lymphocytes. J Immunol 167, 2001, 5749-5757; Vicente-Manzanares M, Cabrero J R, Rey M, Perez-Martinez M, Ursa A, Itoh K, Sanchez-Madrid F., A role for the Rho-p 160 Rho coiled-coil kinase axis in the chemokine stromal cell-derived factor-1alpha-induced lymphocyte actomyosinand microtubular organization and chemotaxis. J Immunol 168, 2002, 400-410; Thorlacius K et al., Protective effect of fasudil, a Rho-kinase inhibitor, on chemokine expression, leukocyte recruitment, and hepatocellular apoptosis in septic liver injury. J Leukoc Biol. 79, 2006, 923-31).

Since ROCK inhibitors reduce cell proliferation and cell migration, they could be useful in treating cancer and tumor metastasis (Aznar, S., Fernandez-Valeron, P., Espina, C., Lacal, J. C., Rho GTPases: potential candidates for anticancer therapy. Cancer Lett. 206, 2004, 181-191; Yin, L. et al., Fasudil inhibits vascular endothelial growth factor-induced angiogenesis in vitro and in vivo. Mol Cancer Ther 5, 2007, 1517-25. Itoh, K., Yoshioka, K., Akedo, H., Uehata, M., Ishizaki, T., Narumiya, S., An essential part for Rho-associated kinase in the transcellular invasion of tumor cells. Nat Med 5, 1999, 221-225; Genda, T. Sakamoto, M., Ichida, T., Asakura, H., Kojiro, M., Narumiya, S., Hirohashi, S., Cell motility mediated by rho and Rho-associated protein kinase plays a critical role inintrahepatic metastasis of human hepatocellular carcinoma. Hepatology 30, 1999, 1027-1036; Somlyo, A. V., Bradshaw, D., Ramos, S., Murphy, C., Myers, C. E., Somlyo, A. P., Rho-kinase inhibitor retards migration and in vivo dissemination of human prostate cancer cells. Biochem Biophys Res Commun 269, 2000, 652-659). ROCK inhibitors can also be beneficial in diseases with impaired blood brain barrier function, e.g. HIV-1 encephalitis (Persidski Y et al., Rho-mediated regulation of tight junctions during monocyte migration across the blood-brain barrier in HIV-1 encephalitis (HIVE). Blood. 107, 2006, 4770-4780) and Alzheimer's disease (Man S-M et al., Peripheral T cells overexpress MIP-1a to enhance its transendothelial migration in Alzheimer's disease. Neurobiol. Of Aging 28, 2007, 485-496).

Furthermore, there is evidence suggesting that ROCK inhibitors suppress cytoskeletal rearrangement upon virus invasion, thus they also have potential therapeutic value in anti-viral and anti-bacterial applications (Favoreel H W, Cytoskeletal rearrangements and cell extensions induced by the US3 kinase of an alphaherpesvirus are associated with enhanced spread. Proc Natl Acad Sci USA. 102(25), 2006, 8990-5).

ROCKs have been reported to interfere with insulin signalling through serine phosphorylation of insulin receptor substrate-1 (IRS-1), in cultured VSMC. Activation of RhoA/ROCK was observed in skeletal muscles and aortic tissues of Zucker obese rats. Inhibition of ROCK, by fasudil for 4 weeks, reduced blood pressure, corrected glucose and lipid metabolism, improved insulin signalling and endothelial dysfunction. In another experiment administration of high dose fasudil completely suppressed the development of diabetes, obesity, and dyslipidemia and increased serum adiponectin levels in OLETF rats. ROCK inhibitors may therefore be useful for the treatment of insulin resistance and diabetes (Nakamura Y et al., Marked increase of insulin gene transcription by suppression of the Rho/Rho-kinase pathway. Biochem Biophys Res Commun 350(1), 2006, 68-73; Kikuchi Y et al., A Rho-kinase inhibitor, fasudil, prevents development of diabetes and nephropathy in insulin-resistant diabetic rats. J Endocrinol. 192(3), 2007, 595-603; Goyo A et al., The Rho-kinase inhibitor, fasudil, attenuates diabetic nephropathy in streptozotocin-induced diabetic rats. Eur J. Pharmacol. 568(1-3), 2007, 242-7).

The ROCK inhibitor Fasudil increased cerebral blood flow and was neuroprotective under CNS ischemic conditions. ROCK inhibitors are expected to be useful for the treatment of ischemic CNS disorders and may therefore improve functional outcome in patients suffering from stroke, vascular or AD type dementia (Okamura N et al., Vasodilator effects of fasudil, a Rho-kinase inhibitor, on retinal arterioles in stroke-prone spontaneously hypertensive rats. J Ocul Pharmacol Ther. 23, 2007, 207-12; Yagita Y et al., Rho-kinase activation in endothelial cells contributes to expansion of infarction after focal cerebral ischemia. J Neurosci Res. 85, 2007, 2460-9).

Due to the efficacy of Y-27632 and fasudil in animal models of epileptogenesis, ROCK inhibitors have been suggested for the use in the treatments of epilepsy and seizure disorders (Inan S Y, Büyükafsar K. Antiepileptic effects of two Rho-kinase inhibitors, Y-27632 and fasudil, in mice. Br. J. Pharmacol. advance online publication, 9 Jun. 2008; doi:10.1038/bjp.2008.225)

ROCK inhibitors are also expected to be useful for the treatment of glaucoma (Honjo, M., Inatani, M., Kido, N., Sawamura, T., Yue, B. Y., Honda, Y., Tanihara, H., Effects of protein kinase inhibitor, HA1077, on intraocular pressure and outflow facility in rabbit eyes. Arch Ophthalmol 119, 2001, 1171-1178; Rao, P. V, Deng, P. F., Kumar, J. Epstein, D. L., Modulation of aqueous humor outflow facility by the Rho kinase-specific inhibitor Y-27632. Invest Ophthalmol V is Sci 42, 2001, 1029-1037), psoriasis, retinopathy and benign prostatic hypertrophy.

Furthermore, there is evidence suggesting that ROCK inhibitors suppress cytoskeletal rearrangement upon virus invasion, thus they also have potential therapeutic value in anti-viral and anti-bacterial applications.

As ROCKs have been implicated in neuronal morphogenesis, connectivity, and plasticity in general, they are expected to be useful for the treatment of psychiatric disorders, e.g. depression, schizophrenia, obsessive compulsive disorder and bipolar disorders.

ROCK inhibitors have been described in e.g. WO 2007/026920, WO 2005/074643, and WO 2004/016597. However, their affinity and selectivity or their pharmacological profile is not yet satisfactory.

Schemes and Experimentals

The following abbreviations have the meanings indicated. ADDP means 1,1'-(azodicarbonyl)dipiperidine; AD-mix-β means a mixture of $(DHQD)_2PHAL$, $K_3Fe(CN)_6$, $K_2CO_3$, and $K_2SO_4$; 9-BBN means 9-borabicyclo(3.3.1)nonane; Boc means tert-butoxycarbonyl; $(DHQD)_2PHAL$ means hydroquinidine 1,4-phthalazinediyl diethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)-butane; dppe means 1,2-bis(diphenylphosphino)ethane; dppf means 1,1'-bis(diphenylphosphino)ferrocene; dppm means 1,1-bis(diphenylphosphino)methane; EDAC.HCl means 1-(3-dimethylaminopropyl)-3-ethylcarbodiimide hydrochloride; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; $MP-BH_3$ means macroporous triethylammonium methylpolystyrene cyanoborohydride; TEA means triethylamine; TFA means trifluoroacetic acid; tetrahydrofuran means tetrahydrofuran; NCS means N-chlorosuccinimide; NMM means N-methylmorpholine; NMP means N-methylpyrrolidine; $PPh_3$ means triphenylphosphine.

The following schemes are presented to provide what is believed to be the most useful and readily understood description of procedures and conceptual aspects of this invention. Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Schemes

Scheme 1

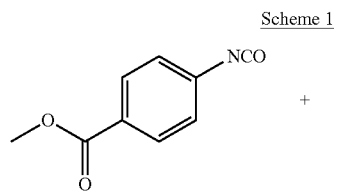

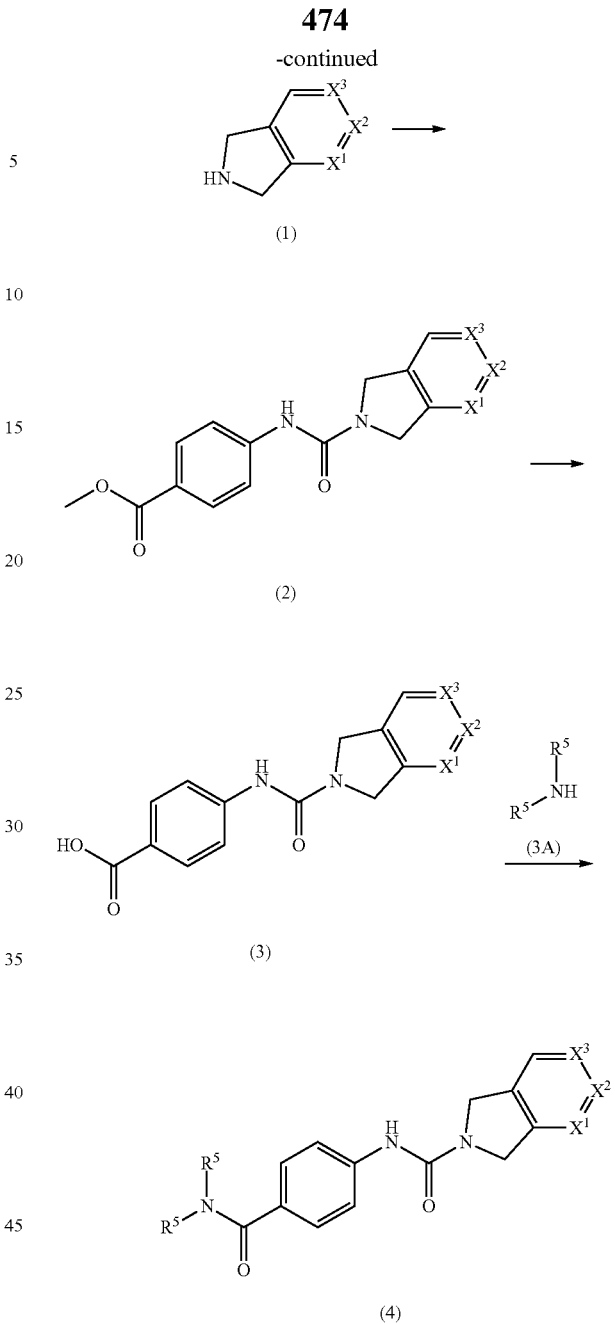

As shown in Scheme 1, compounds of formula (1), wherein $X^1$, $X^2$, and $X^3$ are as described herein, can be reacted with methyl 4-isocyanatobenzoate to provide compounds of formula (2). The reaction is typically performed in a solvent such as but not limited to tetrahydrofuran. The methyl 4-isocyanatobenzoate is typically added at low temperature followed by stirring at room temperature. Compounds of formula (3) can be prepared by reacting compounds of formula (2) with aqueous lithium hydroxide. The reaction is typically performed in a solvent such as but not limited to tetrahydrofuran, methanol, or mixtures thereof. Compounds of formula (3) can be reacted with amine of formula (3A), wherein $R^5$ is hydrogen or is as described herein, using coupling conditions known to those skilled in the art and readily available in the literature to provide compounds of formula (4), which are representative of the compounds of this invention.

Scheme 2

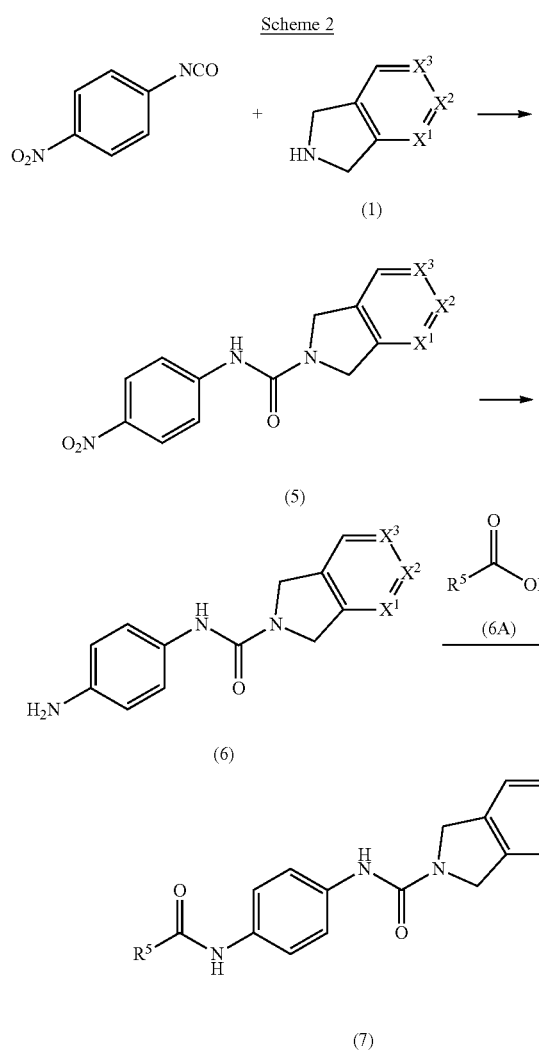

As shown in Scheme 2, compounds of formula (1), wherein $X^1$, $X^2$, and $X^3$ are as described herein, can be reacted with 4-nitrophenylisocyanate to provide compounds of formula (5). The reaction is typically performed in a solvent such as but not limited to tetrahydrofuran. Compounds of formula (5) can be treated with a hydrogen balloon in the presence of 10% Pd on carbon to provide compounds of formula (6). The reaction is typically performed at ambient temperature in a solvent such as but not limited to dimethylformamide. Compounds of formula (6) can be reacted with acid of formula (6A), wherein $R^5$ is as described herein, using coupling conditions known to those skilled in the art and readily available in the literature to provide compounds of formula (7), which are representative of the compounds of this invention.

Scheme 3

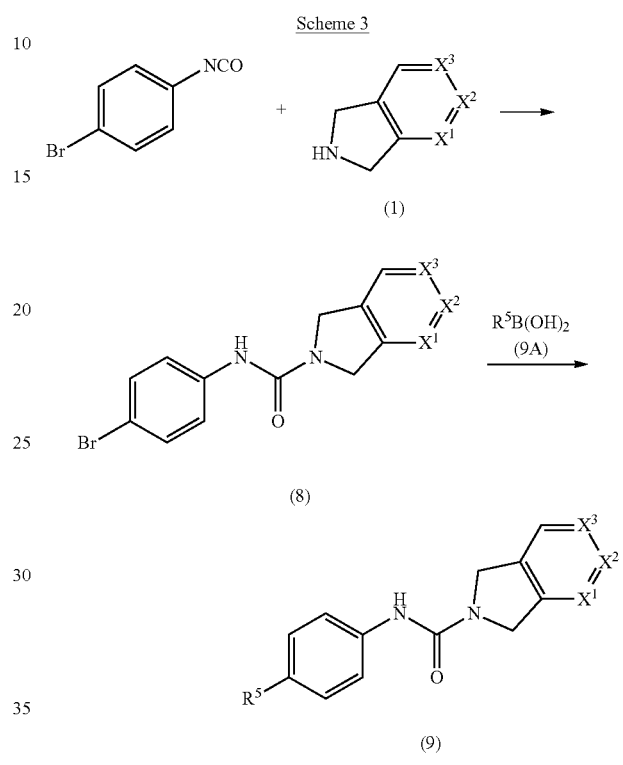

As shown in Scheme 3, compounds of formula (1), wherein $X^1$, $X^2$, and $X^3$ are as described herein, can be reacted with 4-bromophenyl isocyanate to provide compounds of formula (8). The reaction is typically performed in a solvent such as but not limited to tetrahydrofuran. Compounds of formula (8) can be reacted with a boronic acid of formula (9A) (or an appropriate boronate ester), wherein $R^5$ is as described herein, using Suzuki Coupling conditions known to those skilled in the art and readily available in the literature to provide compounds of formula (9), which are representative of the compounds of this invention.

Scheme 4

-continued

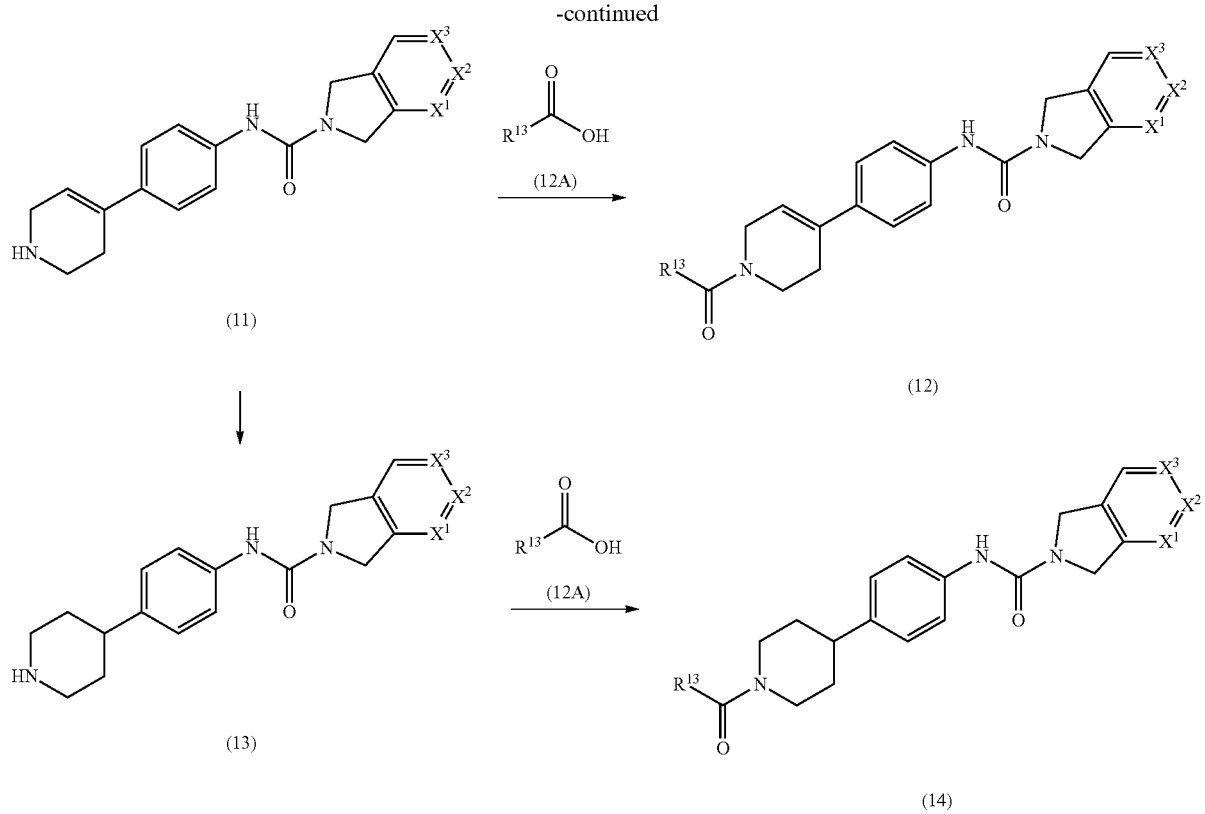

As shown in Scheme 4, compounds of formula (8), wherein $X^1$, $X^2$, and $X^3$ are as described herein, can be reacted with tert-butyl 4-(4,4,5,5-tetramethyl-1,3,2-dioxaborolan-2-yl)-5,6-dihydropyridine-1(2H)-carboxylate under Suzuki coupling conditions known to those skilled in the art and widely available in the literature to provide compounds of formula (10). Compounds of formula (11) can be prepared by treating compounds of formula (10) with an acid such as but not limited to trifluoroacetic acid. The reaction is typically performed at room temperature in a solvent such as but not limited to dichloromethane. Compounds of formula (11) can be reacted with compounds of formula (12A) wherein $R^{13}$ is as described herein, in the presence of a carboxyl activating agent such as but not limited to N-(3-dimethylaminopropyl)-N'-ethylcarbodiimide hydrochloride, and a coupling agent such but not limited to 1-hydroxybenzotriazole hydrate, to provide compounds of formula (12). The reaction is typically performed at room temperature in a solvent such as but not limited to N,N-dimethylformamide.

Alternatively, compounds of formula (12) can be treated with hydrogen in the presence of palladium on carbon to provide compounds of formula (13). The reaction is typically performed under pressure in a solvent such as but not limited to tetrahydrofuran or N,N-dimethylformamide. Compounds of formula (13) can be reacted with compounds of formula (12A) wherein $R^{13}$ is as described herein, in the presence of a carboxyl activating agent such as but not limited to N-(3-dimethylaminopropyl)-N'-ethylcarbodiimide hydrochloride, and a coupling agent such but not limited to 1-hydroxybenzotriazole hydrate, to provide compounds of formula (14). The reaction is typically performed at room temperature in a solvent such as but not limited to N,N-dimethylformamide.

Scheme 5

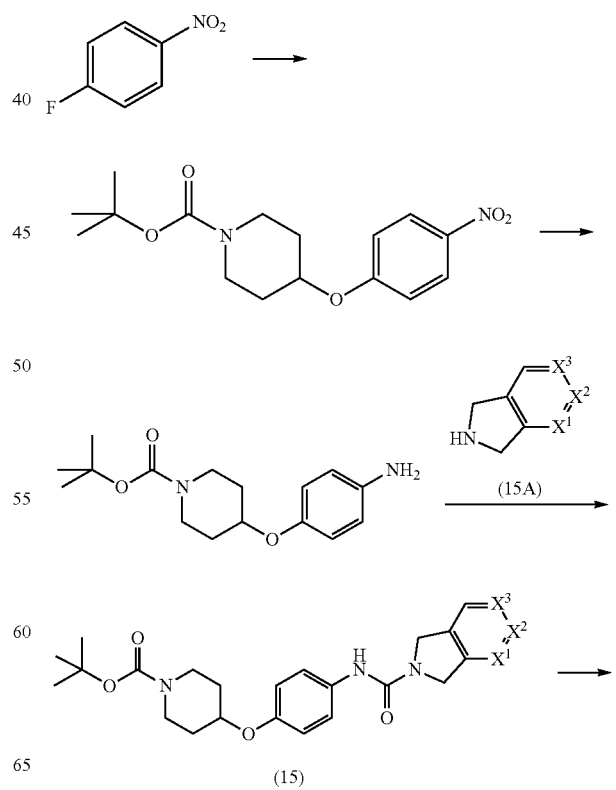

-continued

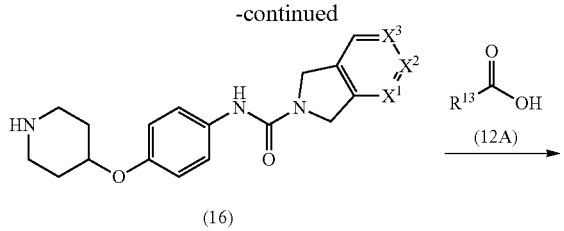

(16)

(17)

Aqueous potassium hydroxide and a phase transfer catalyst such as but not limited to tetrabutylammonium bromide can be added to a mixture of 4-hydroxy-1-piperidine-1-carboxylic acid tert-butyl ester and 1-fluoro-4-nitrobenzene to provide tert-butyl 4-(4-nitrophenoxy)piperidine-1-carboxylate. tert-Butyl 4-(4-aminophenoxy)piperidine-1-carboxylate can be prepared by reacting tert-butyl 4-(4-nitrophenoxy)piperidine-1-carboxylate with hydrogen in the presence of palladium on carbon. The reaction is typically performed under pressure in a solvent such as but not limited to tetrahydrofuran or N,N-dimethylformamide. tert-Butyl 4-(4-aminophenoxy)piperidine-1-carboxylate can be reacted with bis(2,5-dioxopyrrolidin-1-yl) carbonate and pyridine in acetonitrile, followed by the addition of a base such as but not limited to diisopropylethylamine and compounds of formula (15A) to provide compounds of formula (15). The reaction is typically performed at room temperature. Compounds of formula (16) can be prepared by treating compounds of formula (15) with an acid such as but not limited to trifluoroacetic acid. The reaction is typically performed at room temperature in a solvent such as but not limited to dichloromethane. Compounds of formula (16) can be reacted with compounds of formula (12A) wherein $R^{13}$ is as described herein, in the presence of a carboxyl activating agent such as but not limited to N-(3-dimethylaminopropyl)-N'-ethylcarbodiimide hydrochloride, and a coupling agent such but not limited to 1-hydroxybenzotriazole hydrate, to provide compounds of formula (17). The reaction is typically performed at room temperature in a solvent such as but not limited to N,N-dimethylformamide.

The following examples are presented to provide what is believed to be the most useful and readily understood description of procedures and conceptual aspects of this invention. The exemplified compounds were named using ACD/ChemSketch Version 12.01 (13 May 2009), Advanced Chemistry Development Inc., Toronto, Ontario), or ChemDraw® Ver. 9.0.5 (CambridgeSoft, Cambridge, Mass.). Intermediates were named using ChemDraw® Ver. 9.0.5 (CambridgeSoft, Cambridge, Mass.).

EXPERIMENTALS

Example 1

N-{4-[(3-phenylpropyl)carbamoyl]phenyl}-1,3-dihydro-2H-isoindole-2-carboxamide

Example 1A

Methyl 4-(isoindoline-2-carboxamido)benzoate

Isoindoline (1.693 ml, 14.47 mmol) was dissolved in tetrahydrofuran (20 ml) and cooled to 0° C.; and methyl 4-isocyanatobenzoate (2.18 g, 12.06 mmol) was added by syringe and the resulting mixture was warmed to ambient temperature, and then stirred overnight. The solution was concentrated to a slurry, diluted with ether, and filtered to provide the title compound.

Example 1B 4-(isoindoline-2-carboxamido)benzoic acid

Methyl 4-(isoindoline-2-carboxamido)benzoate (1.65 g, 5.57 mmol) was dissolved in tetrahydrofuran (30 ml) and methanol (15.00 ml) followed by the addition of lithium hydroxide (11.14 ml, 22.27 mmol) and the mixture was allowed to stir at ambient temperature over the weekend. The organic solvent was removed under vacuum, the aqueous layer was adjusted to pH ~3 with 2N aqueous HCl, and the resulting solid was filtered with water washes to provide the title compound after drying.

Example 1C

N-{4-[(3-phenylpropyl)carbamoyl]phenyl}-1,3-dihydro-2H-isoindole-2-carboxamide 4-(Isoindoline-2-carboxamido)benzoic acid (150 mg, 0.531 mmol) and 1-hydroxybenzotriazole hydrate (122 mg, 0.797 mmol) were dissolved in dimethylformamide (3 ml) followed by addition of 3-phenylpropan-1-amine (110 mg, 0.797 mmol) and N-(3-dimethylaminopropyl)-N'-ethylcarbodiimide hydrochloride (153 mg, 0.797 mmol). The homogeneous solution was stirred at ambient temperature overnight. The solution was diluted with water to give a precipitate which was filtered, washed with cold ethyl acetate then ether and dried under vacuum to provide the title compound. $^1$H NMR (400 MHz, DMSO-$d_6$, Temp=90° C.) δ ppm 8.27-8.34 (bs, 1H), 7.93-7.98 (m, 1H), 7.73-7.76 (m, 2H), 7.61-7.64 (m, 2H), 7.32-7.36 (m, 2H), 7.27-7.32 (m, 2H), 7.24-7.28 (m, 2H), 7.19-7.24 (m, 2H), 7.13-7.18 (m, 1H), 4.79 (s, 4H), 3.30 (q, J=6.5 Hz, 2H), 2.65 (t, J=7.6 Hz, 2H), 1.86 (p, J=7.3 Hz, 2H); MS (ESI(+)) m/e 400 (M+H)$^+$.

Example 2

N-(4-{[4-(aminomethyl)benzyl]carbamoyl}phenyl)-5-fluoro-1,3-dihydro-2H-isoindole-2-carboxamide Example 2A methyl 4-(5-fluoroisoindoline-2-carboxamido)benzoate The title compound was prepared as described in Example 1A, substituting 5-fluoroisoindoline for isoindoline.

Example 2B

4-(5-fluoroisoindoline-2-carboxamido)benzoic acid

The title compound was prepared as described in Example 1B, substituting methyl 4-(5-fluoroisoindoline-2-carboxamido)benzoate for methyl 4-(isoindoline-2-carboxamido)benzoate.

Example 2C tert-butyl 44(4-(5-fluoroisoindoline-2-carboxamido)benzamido)methyl)benzylcarbamate

The title compound was prepared as described in Example 1C, substituting 4-(5-fluoroisoindoline-2-carboxamido)benzoic acid for 4-(isoindoline-2-carboxamido)benzoic acid and tert-butyl 4-(aminomethyl)benzylcarbamate for 3-phenylpropan-1-amine.

Example 2D

N-(4-{[4-(aminomethyl)benzyl]carbamoyl}phenyl)-5-fluoro-1,3-dihydro-2H-isoindole-2-carboxamide tert-Butyl 4-((4-(5-fluoroisoindoline-2-carboxamido)benzamido)methyl)benzylcarbamate (392 mg, 0.756 mmol) was dissolved in dichloromethane, treated with trifluoroacetic acid (582 µl, 7.56 mmol), stirred for 3 hours at ambient temperature and then concentrated to dryness. The resulting solid was triturated with ether, collected and dried under vacuum to provide the title compound. $^1$H NMR (400 MHz, DMSO-$d_6$) δ ppm 4.01 (q, J=5.6 Hz, 2H), 4.46 (d, J=6.0 Hz, 2H), 4.76 (d, J=7.9 Hz, 4H), 7.08-7.29 (m, 2H), 7.32-7.44 (m, 5H), 7.67 (d, J=8.7 Hz, 2H), 7.76-7.86 (m, 2H), 8.12 (s, 2H), 8.63 (s, 1H), 8.91 (t, J=6.2 Hz, 1H); MS (ESI(+)) m/e 419 (M+H)$^+$.

Table 3.

The following Examples were prepared essentially as described in Example 1, substituting the appropriate substituted isoindoline for isoindoline in Example 1A and the appropriate amine for 3-phenylpropan-1-amine in Example 1C. Some products were purified by flash chromatography while others were purified by reverse-phase HPLC; some compounds also required Boc-deprotection after amide coupling as described in Example 2D. Accordingly, some Examples were isolated as trifluoroacetic acid salts.

| Ex | Name | $^1$H NMR | MS |
|---|---|---|---|
| 3 | 5-cyano-N-{4-[(3-phenylpropyl)carbamoyl]phenyl}-1,3-dihydro-2H-isoindole-2-carboxamide | $^1$H NMR (300 MHz, DMSO-$d_6$) δ ppm 8.65 (s, 1H), 8.29 (t, J = 5.6 Hz, 1H), 7.89 (s, 1H), 7.75-7.81 (m, 3H), 7.63-7.68 (m, 2H), 7.59 (d, J = 8.0 Hz, 1H), 7.15-7.32 (m, 5H), 4.82-4.86 (m, 4H), 3.22-3.30 (m, 2H), 2.63 (t, J = 7.6 Hz, 2H), 1.82 (p, J = 7.4 Hz, 2H) | (ESI (+)) m/e 425 (M + H)$^+$ |
| 4 | N-{4[(cyclopentylmethyl)carbamoyl]phenyl}-5-fluoro-1,3-dihydro-2H-isoindole-2-carboxamide | $^1$H NMR (400 MHz, DMSO-$d_6$) δ 1.16-1.33 (m, 2 H), 1.41-1.75 (m, 6 H), 2.04-2.23 (m, 1 H), 3.11-3.22 (m, 2 H), 4.76 (d, J = 7.9 Hz, 4 H), 7.08-7.19 (m, 1 H), 7.24 (dd, J = 9.12, 2.4 Hz, 1 H), 7.39 (dd, J = 8.3, 5.16 Hz, 1 H), 7.60-7.68 (m, 2 H), 7.72-7.82 (m, 2 H), 8.27 (t, J = 5.8 Hz, 1 H), 8.58 (s, 1 H) | (ESI (+)) m/e 382 (M + H)$^+$ |
| 5 | 5-cyano-N-[4-(propylcarbamoyl)phenyl]-1,3-dihydro-2H-isoindole-2-carboxamide | $^1$H NMR (300 MHz, DMSO-$d_6$) δ ppm 8.65 (s, 1H), 8.26 (t, J = 5.7 Hz, 1H), 7.89 (s, 1H), 7.79 (dd, J = 8.0, 1.7 Hz, 1H), 7.74-7.79 (m, 2H), 7.62-7.67 (m, 2H), 7.59 (d, J = 7.9 Hz, 1H), 4.84 (d, J = 7.5 Hz, 4H), 3.14-3.27 (m, 2H), 1.46-1.59 (m, 2H), 0.89 (t, J = 7.4 Hz, 3H) | (ESI (+)) m/e 349 (M + H)$^+$ |
| 6 | N-(4-{[4-(furo[3,2-c]pyridin-4-yl)piperazin-1-yl]carbonyl}phenyl)-1,3-dihydro-2H-isoindole-2-carboxamide | $^1$H NMR (300 MHz, DMSO-$d_6$) δ ppm 8.65 (s, 1H), 8.26 (t, J = 5.7 Hz, 1H), 7.89 (s, 1H), 7.79 (dd, J = 8.0, 1.7 Hz, 1H), 7.74-7.79 (m, 2H), 7.62-7.67 (m, 2H), 7.59 (d, J = 7.9 Hz, 1H), 4.84 (d, J = 7.5 Hz, 4H), 3.14-3.27 (m, 2H), 1.46-1.59 (m, 2H), 0.89 (t, J = 7.4 Hz, 3H) | (ESI (+)) m/e 468 (M + H)$^+$ |
| 7 | 5-cyano-N-(4-{[4-(pyridin-2-yl)piperazin-1-yl]carbonyl}phenyl)-1,3-dihydro-2H-isoindole-2-carboxamide | $^1$H NMR (300 MHz, DMSO-$d_6$) δ ppm 8.64 (s, 1H), 8.13 (dd, J = 5.0, 1.9 Hz, 1H), 7.89 (s, 1H), 7.79 (d, J = 8.0 Hz, 1H), 7.64-7.68 (m, 2H), 7.51-7.61 (m, 2H), 7.36-7.40 (m, 2H), 6.85 (d, J = 8.6 Hz, 1H), 6.65-6.69 (m, 1H), 4.82-4.85 (bs, 4H), 3.48-3.69 (m, 8H) | (ESI (−)) m/e 451 (M − H)$^-$ |
| 8 | 5-fluoro-N-{4-[(pyridin-2-ylmethyl)carbamoyl]phenyl}-1,3-dihydro-2H-isoindole-2-carboxamide | $^1$H NMR (300 MHz, DMSO-$d_6$) δ ppm 8.93 (t, J = 6.0 Hz, 1H), 8.63 (s, 1H), 8.51 (ddd, J = 4.8, 1.8, 0.9 Hz, 1H), 7.83-7.87 (m, 2H), 7.75 (td, J = 7.7, 1.8 Hz, 1H), 7.66-7.70 (m, 2H), 7.40 (dd, J = 8.4, 5.2 Hz, 1H), 7.22-7.33 (m, 3H), 7.15 (td, J = 8.9, 2.5 Hz, 1H), 4.75-4.80 (m, 4H), 4.55 (d, J = 5.8 Hz, 2H) | (ESI (+)) m/e 391 (M + H)$^+$ |

| Ex | Name | ¹H NMR | MS |
|---|---|---|---|
| 9 | N-[4-(benzylcarbamoyl)phenyl]-5-fluoro-1,3-dihydro-2H-isoindole-2-carboxamide | ¹H NMR (300 MHz, DMSO-$d_6$) δ ppm 8.86 (t, J = 6.0 Hz, 1H), 8.61 (s, 1H), 7.80-7.85 (m, 2H), 7.64-7.70 (m, 2H), 7.39 (dd, J = 8.7, 5.2 Hz, 1H), 7.29-7.35 (m, 4H), 7.20-7.28 (m, 2H), 7.15 (ddd, J = 9.4, 8.5, 2.5 Hz, 1H), 4.74-4.79 (m, 4H), 4.47 (d, J = 5.9 Hz, 2H) | (ESI (+)) m/e 390 (M + H)⁺ |
| 10 | N-{4-[(3,4-dimethoxybenzyl)carbamoyl]phenyl}-1,3-dihydro-2H-isoindole-2-carboxamide | ¹H NMR (500 MHz, DMSO-$d_6$/Deuterium Oxide) δ ppm 7.80-7.82 (m, 2H), 7.64-7.67 (m, 2H), 7.36-7.41 (m, 2H), 7.32-7.35 (m, 2H), 6.96 (d, J = 1.9 Hz, 1H), 6.91 (d, J = 8.2 Hz, 1H), 6.86 (dd, J = 8.2, 2.0 Hz, 1H), 4.79 (s, 4H), 4.39-4.40 (bs, 2H), 3.78 (s, 3H) | (ESI (−)) m/e 430 (M − H)⁻ |
| 11 | 5-methyl-N-(4-{[4-(pyridin-2-yl)piperazin-1-yl]carbonyl}phenyl)-1,3-dihydro-2H-isoindole-2-carboxamide | ¹H NMR (300 MHz, DMSO-$d_6$) δ ppm 8.54 (s, 1H), 8.13 (ddd, J = 4.9, 2.0, 0.8 Hz, 1H), 7.65-7.68 (m, 2H), 7.55 (ddd, J = 8.6, 7.1, 2.0 Hz, 1H), 7.35-7.39 (m, 2H), 7.25 (d, J = 7.7 Hz, 1H), 7.17-7.19 (m, 1H), 7.13 (d, J = 7.8 Hz, 1H), 6.85 (dt, J = 8.6, 0.8 Hz, 1H), 6.67 (ddd, J = 7.1, 4.9, 0.8 Hz, 1H), 4.73-4.75 (bs, 4H), 3.48-3.68 (m, 8H), 2.33 (s, 3H) | (ESI (+)) m/e 442 (M + H)⁺ |
| 12 | N-(4-{[4-(thieno[3,2-c]pyridin-4-yl)piperazin-1-yl]carbonyl}phenyl)-1,3-dihydro-2H-isoindole-2-carboxamide | ¹H NMR (300 MHz, DMSO-$d_6$) δ ppm 8.56 (s, 1H), 8.03 (d, J = 5.6 Hz, 1H), 7.78 (d, J = 5.5 Hz, 1H), 7.64-7.71 (m, 2H), 7.58 (t, J = 5.3 Hz, 2H), 7.30-7.41 (m, 6H), 4.79 (s, 4H), 3.61-3.94 (m, 4H), 3.39-3.63 (m, 4H) | (ESI (+)) m/e 484 (M + H)⁺ |
| 13 | N-{4-[(2,3-dimethoxybenzyl)carbamoyl]phenyl}-1,3-dihydro-2H-isoindole-2-carboxamide | ¹H NMR (400 MHz, Pyridine-$d_5$, Temp = 90° C.) δ ppm 8.30-8.37 (bs, 1H), 8.27-8.31 (m, 1H), 8.13-8.16 (m, 2H), 7.91-7.93 (m, 2H), 7.19-7.24 (m, 2H), 7.16-7.18 (m, 2H), 7.16-7.17 (m, 1H), 6.98 (t, J = 7.8 Hz, 1H), 6.86 (dd, J = 8.1, 1.5 Hz, 1H), 4.91 (d, J = 5.7 Hz, 2H), 4.83-4.85 (m, 4H), 3.85 (s, 3H), 3.71 (s, 3H) | (ESI (+)) m/e 432 (M + H)⁺ |
| 14 | 5-fluoro-N-{4-[(3-phenylpropyl)carbamoyl]phenyl}-1,3-dihydro-2H-isoindole-2-carboxamide | ¹H NMR (300 MHz, DMSO-$d_6$) δ ppm 8.59 (s, 1H), 8.29 (t, J = 5.5 Hz, 1H), 7.75-7.78 (m, 2H), 7.63-7.67 (m, 2H), 7.39 (dd, J = 8.5, 5.1 Hz, 1H), 7.11-7.32 (m, 7H), 4.74-4.78 (m, 4H), 3.22-3.31 (m, 2H), 2.63 (t, J = 7.6 Hz, 2H), 1.82 (p, J = 7.4 Hz, 2H) | (ESI (+)) m/e 418 (M + H)⁺ |
| 15 | 5-fluoro-N-(4-{[4-(pyridazin-3-yl)piperazin-1-yl]carbonyl}phenyl)-1,3-dihydro-2H-isoindole-2-carboxamide | ¹H NMR (300 MHz, DMSO-$d_6$) δ ppm 8.58-8.59 (m, 1H), 8.57-8.60 (m, 1H), 7.65-7.69 (m, 2H), 7.37-7.44 (m, 4H), 7.22-7.29 (m, 2H), 7.15 (td, J = 8.9, 2.5 Hz, 1H), 4.77 (d, J = 8.3 Hz, 4H), 3.49-3.81 (m, 8H) | (ESI (+)) m/e 447 (M + H)⁺ |
| 16 | N-{4-[(2,3-dihydro-1,4-benzodioxin-5-ylmethyl)carbamoyl]phenyl}-1,3-dihydro-2H-isoindole-2-carboxamide | ¹H NMR (400 MHz, Pyridine-$d_5$, Temp = 90° C.) δ ppm 8.33 (d, J = 1.8 Hz, 1H), 8.28-8.29 (bs, 1H), 8.13-8.16 (m, 2H), 7.91-7.93 (m, 2H), 7.19-7.23 (m, 2H), 7.15-7.19 (m, 2H), 7.10-7.13 (m, 1H), 6.86 (dd, J = 8.1, 1.8 Hz, 1H), 6.80 (dd, J = 8.1, 7.4 Hz, 1H), 4.87 (d, J = 5.7 Hz, 2H), 4.84 (s, 4H), 4.03-4.10 (m, 4H) | (ESI (+)) m/e 430 (M + H)⁺ |
| 17 | 5-fluoro-N-(4-{[1-(3-methylbutyl)-1H-pyrazol-4-yl]carbamoyl}phenyl)-1,3-dihydro-2H-isoindole-2-carboxamide | ¹H NMR (300 MHz, DMSO-$d_6$) δ ppm 10.22 (s, 1H), 8.65 (s, 1H), 8.03 (s, 1H), 7.85-7.89 (m, 2H), 7.69-7.73 (m, 2H), 7.56 (d, J = 0.7 Hz, 1H), 7.40 (dd, J = 8.4, 5.2 Hz, 1H), 7.25 (dd, J = 9.1, 2.4 Hz, 1H), 7.15 (td, J = 8.9, 2.5 Hz, 1H), 4.73-4.85 (m, 4H), 4.06-4.14 (m, 2H), 1.65 (q, J = 7.0 Hz, 2H), 1.40-1.54 (m, 1H), 0.90 (d, J = 6.6 Hz, 6H) | (ESI (−)) m/e 434 (M − H)⁻ |
| 18 | N-{4-[(2-fluorobenzyl)carbamoyl]phenyl}-1,3-dihydro-2H-isoindole-2-carboxamide | ¹H NMR (500 MHz, DMSO-$d_6$/Deuterium Oxide) δ ppm 8.92 (t, J = 5.9 Hz, 1H), 8.67 (s, 1H), 7.81-7.84 (m, 2H), 7.66-7.68 (m, 2H), 7.30-7.40 (m, 6H), 7.18 (d, J = 7.2 Hz, 1H), 7.16-7.20 (m, 1H), 4.79-4.80 (bs, 4H), 4.52 (d, J = 5.2 Hz, 2H) | (APCI+) m/e 390 (M + H)⁺ |

| Ex | Name | ¹H NMR | MS |
|---|---|---|---|
| 19 | 5-fluoro-N-(4-{[4-(pyrimidin-2-yl)piperazin-1-yl]carbonyl}phenyl)-1,3-dihydro-2H-isoindole-2-carboxamide | ¹H NMR (300 MHz, DMSO-$d_6$) δ ppm 8.58 (s, 1H), 8.37-8.40 (m, 2H), 7.64-7.68 (m, 2H), 7.36-7.43 (m, 3H), 7.24 (dd, J = 9.1, 2.4 Hz, 1H), 7.15 (td, J = 8.9, 2.5 Hz, 1H), 6.67 (t, J = 4.7 Hz, 1H), 4.75-4.79 (m, 4H), 3.70-3.85 (m, 4H), 3.49-3.69 (m, 4H) | (ESI (+)) m/e 447 (M + H)⁺ |
| 20 | 5-fluoro-N-{4-[(3-methylbutyl)carbamoyl]phenyl}-1,3-dihydro-2H-isoindole-2-carboxamide | ¹H NMR (300 MHz, DMSO-$d_6$) δ ppm 8.58 (s, 1H), 8.22 (t, J = 5.6 Hz, 1H), 7.73-7.77 (m, 2H), 7.62-7.66 (m, 2H), 7.39 (dd, J = 8.4, 5.2 Hz, 1H), 7.24 (dd, J = 9.1, 2.5 Hz, 1H), 7.15 (td, J = 8.9, 2.5 Hz, 1H), 4.74-4.78 (m, 4H), 3.21-3.32 (m, 2H), 1.61 (dp, J = 13.3, 6.6 Hz, 1H), 1.37-1.45 (m, 2H), 0.90 (d, J = 6.6 Hz, 6H) | (ESI (+)) m/e 370 (M + H)⁺ |
| 21 | N-{4-[(2-methoxybenzyl)carbamoyl]phenyl}-1,3-dihydro-2H-isoindole-2-carboxamide | ¹H NMR (400 MHz, Pyridine-$d_5$, Temp = 90° C.) δ ppm 8.27-8.29 (bs, 2H), 8.12-8.14 (m, 2H), 7.90-7.93 (m, 2H), 7.52-7.55 (m, 1H), 7.19-7.24 (m, 2H), 7.14-7.19 (m, 2H), 6.91 (td, J = 7.4, 1.0 Hz, 1H), 6.85 (dd, J = 8.2, 1.1 Hz, 1H), 4.89 (d, J = 5.7 Hz, 2H), 4.83 (s, 4H), 3.65 (s, 3H) | (APCI+) m/e 402 (M + H)⁺ |
| 22 | 5-fluoro-N-(4-{[4-(pyridin-2-yl)piperazin-1-yl]carbonyl}phenyl)-1,3-dihydro-2H-isoindole-2-carboxamide | ¹H NMR (300 MHz, DMSO-$d_6$) δ ppm 8.59 (s, 1H), 8.10 (dd, J = 5.5, 1.8 Hz, 1H), 7.74-7.81 (m, 1H), 7.65-7.69 (m, 2H), 7.37-7.43 (m, 3H), 7.24 (dd, J = 9.1, 2.4 Hz, 1H), 7.07-7.19 (m, 2H), 6.82 (t, J = 6.2 Hz, 1H), 4.77 (d, J = 7.9 Hz, 4H), 3.61-3.69 (bs, 8H) | (ESI (+)) m/e 446 (M + H)⁺ |
| 23 | N-{4-[(3-fluorobenzyl)carbamoyl]phenyl}-1,3-dihydro-2H-isoindole-2-carboxamide | ¹H NMR (500 MHz, DMSO-$d_6$/Deuterium Oxide) δ ppm 8.99 (t, J = 6.0 Hz, 1H), 7.81-7.84 (m, 2H), 7.66-7.69 (m, 2H), 7.36-7.46 (m, 3H), 7.32-7.35 (m, 2H), 7.17 (d, J = 7.7 Hz, 1H), 7.12 (dd, J = 10.3, 2.6 Hz, 1H), 7.07 (td, J = 8.5, 2.8 Hz, 1H), 4.79-4.80 (bs, 4H), 4.48 (d, J = 5.8 Hz, 2H) | (ESI (+)) m/e 390 (M + H)⁺ |
| 24 | 5-fluoro-N-(4-{[3-(2-oxopyrrolidin-1-yl)propyl]carbamoyl}phenyl)-1,3-dihydro-2H-isoindole-2-carboxamide | ¹H NMR (300 MHz, DMSO-$d_6$) δ ppm 8.59 (s, 1H), 8.26 (t, J = 5.6 Hz, 1H), 7.74-7.78 (m, 2H), 7.63-7.67 (m, 2H), 7.39 (dd, J = 8.4, 5.2 Hz, 1H), 7.24 (dd, J = 9.1, 2.8 Hz, 1H), 7.15 (ddd, J = 9.4, 8.5, 2.6 Hz, 1H), 4.74-4.79 (m, 4H), 3.33-3.38 (m, 2H), 3.16-3.27 (m, 4H), 2.22 (t, J = 8.0 Hz, 2H), 1.93 (p, J = 7.5 Hz, 2H), 1.69 (p, J = 7.0 Hz, 2H) | (ESI (+)) m/e 425 (M + H)⁺ |
| 25 | 5-cyano-N-{4-[(3-methylbutyl)carbamoyl]phenyl}-1,3-dihydro-2H-isoindole-2-carboxamide | ¹H NMR (300 MHz, DMSO-$d_6$) δ ppm 8.65 (s, 1H), 8.22 (t, J = 5.6 Hz, 1H), 7.89 (s, 1H), 7.79 (dd, J = 7.9, 1.6 Hz, 1H), 7.73-7.78 (m, 2H), 7.62-7.67 (m, 2H), 7.59 (d, J = 7.9 Hz, 1H), 4.77-4.91 (m, 4H), 3.22-3.32 (m, 2H), 1.53-1.70 (m, 1H), 1.37-1.45 (m, 2H), 0.90 (d, J = 6.6 Hz, 6H) | (ESI (+)) m/e 377 (M + H)⁺ |
| 26 | N-{4-[(cyclopentylmethyl)carbamoyl]phenyl}-5-methyl-1,3-dihydro-2H-isoindole-2-carboxamide | ¹H NMR (300 MHz, DMSO-$d_6$) δ ppm 8.54 (s, 1H), 8.26 (t, J = 5.7 Hz, 1H), 7.73-7.78 (m, 2H), 7.63-7.67 (m, 2H), 7.24 (d, J = 7.7 Hz, 1H), 7.17 (s, 1H), 7.11-7.14 (m, 1H), 4.73-4.74 (bs, 4H), 3.14-3.19 (m, 2H), 2.33 (s, 3H), 2.07-2.21 (m, 1H), 1.42-1.75 (m, 6H), 1.16-1.34 (m, 2H) | (ESI (+)) m/e 378 (M + H)⁺ |
| 27 | N-(4-{[4-(4-cyanophenyl)piperazin-1-yl]carbonyl}phenyl)-1,3-dihydro-2H-isoindole-2-carboxamide | ¹H NMR (400 MHz, Pyridine-$d_5$, Temp = 90° C.) δ ppm 8.34-8.35 (bs, 1H), 7.93-7.96 (m, 2H), 7.56-7.59 (m, 2H), 7.49-7.52 (m, 2H), 7.20-7.24 (m, 2H), 7.16-7.19 (m, 2H), 6.84-6.86 (m, 2H), 4.87 (s, 4H), 3.71-3.74 (m, 4H), 3.24-3.29 (m, 4H) | (ESI (+)) m/e 452 (M + H)⁺ |
| 28 | N-{4-[(4-fluorobenzyl)carbamoyl]phenyl}-1,3-dihydro-2H-isoindole-2-carboxamide | ¹H NMR (500 MHz, DMSO-$d_6$/Deuterium Oxide) δ ppm 8.95 (t, J = 6.0 Hz, 1H), 7.80-7.82 (m, 2H), 7.65-7.68 (m, 2H), 7.32-7.40 (m, 6H), 7.13-7.17 (m, 2H), 4.79-4.80 (bs, 4H), 4.45 (d, J = 5.7 Hz, 2H) | (ESI (+)) m/e 390 (M + H)⁺ |
| 29 | N-{4-[(3,5-dimethoxybenzyl)carbamoyl]phenyl}-1,3-dihydro-2H-isoindole-2-carboxamide | ¹H NMR (500 MHz, DMSO-$d_6$/Deuterium Oxide) δ ppm 7.80-7.83 (m, 2H), 7.66-7.69 (m, 2H), 7.36-7.41 (m, 2H), 7.31-7.36 (m, 2H), 6.49 (d, J = 2.3 Hz, 2H), 6.38 (t, J = 2.3 Hz, 1H), 4.79-4.80 (bs, 4H), 4.40-4.41 (m, 2H), 3.72 (s, 6H) | (ESI (+)) m/e 492 (M + H)⁺ |

| Ex | Name | ¹H NMR | MS |
|---|---|---|---|
| 30 | 5-fluoro-N-{4-[(tetrahydrofuran-3-ylmethyl)carbamoyl]phenyl}-1,3-dihydro-2H-isoindole-2-carboxamide | ¹H NMR (300 MHz, DMSO-$d_6$) δ ppm 8.60 (s, 1H), 8.39 (t, J = 5.7 Hz, 1H), 7.75-7.79 (m, 2H), 7.63-7.68 (m, 2H), 7.40 (dd, J = 8.4, 5.2 Hz, 1H), 7.24 (dd, J = 9.1, 2.5 Hz, 1H), 7.15 (td, J = 8.9, 2.5 Hz, 1H), 4.75-4.79 (m, 4H), 3.57-3.78 (m, 3H), 3.48 (dd, J = 8.5, 5.2 Hz, 1H), 3.16-3.30 (m, 2H), 2.40-2.51 (m, 1H), 1.87-1.99 (m, 1H), 1.54-1.66 (m, 1H) | (ESI (+)) m/e 383 (M + H)⁺ |
| 31 | N-{4-[(2,2-dimethylpropyl)carbamoyl]phenyl}-1,3-dihydro-2H-isoindole-2-carboxamide | ¹H NMR (400 MHz, Pyridine-$d_5$, Temp = 90° C.) δ ppm 8.28-8.30 (bs, 1H), 8.08-8.11 (m, 2H), 7.90-7.93 (m, 2H), 7.66-7.71 (bs, 1H), 7.19-7.23 (m, 2H), 7.15-7.18 (m, 2H), 4.84 (s, 4H), 3.41 (d, J = 6.3 Hz, 2H), 0.98 (s, 9H) | (ESI (+)) m/e 352 (M + H)⁺ |
| 32 | 5-fluoro-N-(4-{[2-(2-oxopyrrolidin-1-yl)ethyl]carbamoyl}phenyl-1,3-dihydro-2H-isoindole-2-carboxamide | ¹H NMR (300 MHz, DMSO-$d_6$) δ ppm 8.59 (s, 1H), 8.31-8.34 (m, 1H), 7.71-7.75 (m, 2H), 7.62-7.66 (m, 2H), 7.39 (dd, J = 8.4, 5.1 Hz, 1H), 7.24 (dd, J = 9.0, 2.4 Hz, 1H), 7.15 (td, J = 8.9, 2.5 Hz, 1H), 4.74-4.79 (m, 4H), 3.34-3.46 (m, 6H), 2.17 (t, J = 8.0 Hz, 2H), 1.91 (p, J = 7.4 Hz, 2H) | (ESI (+)) m/e 411 (M + H)⁺ |
| 33 | N-(4-{[4-(trifluoromethoxy)benzyl]carbamoyl}phenyl)-1,3-dihydro-2H-isoindole-2-carboxamide | ¹H NMR (500 MHz, DMSO-$d_6$/Deuterium Oxide) δ ppm 7.81-7.83 (m, 2H), 7.66-7.68 (m, 2H), 7.43-7.47 (m, 2H), 7.37-7.40 (m, 2H), 7.31-7.35 (m, 4H), 4.79 (s, 4H), 4.49 (s, 2H) | (ESI (+)) m/e 456 (M + H)⁺ |
| 34 | N-(4-{[3-fluoro-5-(trifluoromethyl)benzyl]carbamoyl}phenyl)-1,3-dihydro-2H-isoindole-2-carboxamide | ¹H NMR (500 MHz, DMSO-$d_6$/Deuterium Oxide) δ ppm 9.07 (t, J = 6.0 Hz, 1H), 7.81-7.83 (m, 2H), 7.67-7.70 (m, 2H), 7.53-7.56 (m, 1H), 7.45-7.48 (m, 1H), 7.36-7.41 (m, 2H), 7.31-7.36 (m, 2H), 4.80 (s, 4H), 4.56 (d, J = 5.4 Hz, 2H) | (ESI (+)) m/e 458 (M + H)⁺ |
| 35 | 5-fluoro-N-(4-{[4-(pyrazin-2-yl)piperazin-1-yl]carbonyl}phenyl)-1,3-dihydro-2H-isoindole-2-carboxamide | ¹H NMR (300 MHz, DMSO-$d_6$) δ ppm 8.59 (s, 1H), 8.34 (d, J = 1.5 Hz, 1H), 8.10 (dd, J = 2.6, 1.4 Hz, 1H), 7.87 (d, J = 2.6 Hz, 1H), 7.64-7.68 (m, 2H), 7.36-7.43 (m, 3H), 7.24 (dd, J = 9.1, 2.4 Hz, 1H), 7.11-7.19 (m, 1H), 4.75-4.79 (m, 4H), 3.58-3.69 (bs, 8H) | (ESI (+)) m/e 447 (M + H)⁺ |
| 36 | N-{4-[(3-methylbutyl)carbamoyl]phenyl}-1,3-dihydro-2H-isoindole-2-carboxamide | ¹H NMR (400 MHz, DMSO-$d_6$, Temp = 90° C.) δ ppm 8.31 (s, 1H), 7.86-7.89 (m, 1H), 7.72-7.75 (m, 2H), 7.60-7.64 (m, 2H), 7.28-7.36 (m, 4H), 4.79 (s, 4H), 3.28 (q, J = 6.7 Hz, 2H), 1.58-1.71 (m, 1H), 1.45 (q, J = 7.1 Hz, 2H), 0.92 (d, J = 6.6 Hz, 6H) | (ESI (+)) m/e 352 (M + H)⁺ |
| 37 | 5-methoxy-N-{4-[(3-phenylpropyl)carbamoyl]phenyl}-1,3-dihydro-2H-isoindole-2-carboxamide | ¹H NMR (300 MHz, DMSO-$d_6$) δ ppm 8.55 (s, 1H), 8.29 (t, J = 5.6 Hz, 1H), 7.74-7.79 (m, 2H), 7.63-7.67 (m, 2H), 7.15-7.32 (m, 6H), 6.94 (d, J = 2.3 Hz, 1H), 6.88 (dd, J = 8.3, 2.4 Hz, 1H), 4.65-4.79 (m, 4H), 3.77 (s, 3H), 3.22-3.31 (m, 2H), 2.60-2.68 (m, 2H), 1.77-1.88 (m, 2H) | (ESI (+)) m/e 429 (M + H)⁺ |
| 38 | N-{4-[(4-chlorobenzyl)carbamoyl]phenyl}-1,3-dihydro-2H-isoindole-2-carboxamide | ¹H NMR (500 MHz, DMSO-$d_6$/Deuterium Oxide) δ ppm 8.97 (t, J = 6.0 Hz, 1H), 8.67 (s, 1H), 7.80-7.83 (m, 2H), 7.66-7.68 (m, 2H), 7.32-7.40 (m, 8H), 4.79-4.80 (bs, 4H), 4.45 (d, J = 5.4 Hz, 2H) | (ESI (+)) m/e 406 (M + H)⁺ |
| 39 | N-{4-[(cyclopentylmethyl)carbamoyl]phenyl}-1,3-dihydro-2H-isoindole-2-carboxamide | ¹H NMR (400 MHz, Pyridine-$d_5$, Temp = 90 C.) δ ppm 8.28-8.29 (bs, 1H), 8.09-8.12 (m, 2H), 7.90-7.94 (m, 2H), 7.84-7.91 (m, 1H), 7.19-7.24 (m, 2H), 7.14-7.18 (m, 2H), 4.84 (s, 4H), 3.51 (dd, J = 7.2, 5.8 Hz, 2H), 2.20-2.32 (m, 1H), 1.67-1.76 (m, 2H), 1.51-1.62 (m, 2H), 1.40-1.51 (m, 2H), 1.27-1.38 (m, 2H) | (ESI (+)) m/e 364 (M + H)⁺ |
| 40 | N-{4-[(3,4,5-trimethoxybenzyl)carbamoyl]phenyl}-1,3-dihydro-2H-isoindole-2-carboxamide | ¹H NMR (400 MHz, Pyridine-$d_5$, Temp = 90° C.) δ ppm 8.59-8.64 (m, 1H), 8.29-8.32 (m, 1H), 8.17-8.19 (m, 2H), 7.92-7.94 (m, 2H), 7.19-7.24 (m, 2H), 7.15-7.18 (m, 2H), 6.82 (s, 2H), 4.84 (s, 4H), 4.77 (d, J = 5.8 Hz, 2H), 3.85 (s, 3H), 3.69 (s, 6H) | (ESI (+)) m/e 462 (M + H)⁺ |

| Ex | Name | $^1$H NMR | MS |
|---|---|---|---|
| 41 | N-(4-{[4-(pyrimidin-2-yl)piperazin-1-yl]carbonyl}phenyl)-1,3-dihydro-2H-isoindole-2-carboxamide | $^1$H NMR (300 MHz, DMSO-d$_6$) δ ppm 8.56 (s, 1H), 8.37-8.40 (m, 2H), 7.66-7.69 (m, 2H), 7.30-7.40 (m, 6H), 6.67 (t, J = 4.7 Hz, 1H), 4.79 (s, 4H), 3.77-3.81 (m, 4H), 3.58 (s, 4H) | (ESI (+)) m/e 429 (M + H)$^+$ |
| 42 | 5-nitro-N-[4-(propylcarbamoyl)phenyl]-1,3-dihydro-2H-isoindole-2-carboxamide | $^1$H NMR (300 MHz, DMSO-d$_6$) δ ppm 8.68 (s, 1H), 8.23-8.30 (m, 2H), 8.21 (dd, J = 8.3, 2.4 Hz, 1H), 7.75-7.79 (m, 2H), 7.63-7.67 (m, 3H), 4.88-4.91 (m, 4H), 3.16-3.23 (m, 2H), 1.46-1.59 (m, 2H), 0.89 (t, J = 7.4 Hz, 3H) | (ESI (+)) m/e 369 (M + H)$^+$ |
| 43 | 5-methyl-N-{4-[(3-methylbutyl)carbamoyl]phenyl}-1,3-dihydro-2H-isoindole-2-carboxamide | $^1$H NMR (300 MHz, DMSO-d$_6$) δ ppm 8.54 (s, 1H), 8.21 (t, J = 5.6 Hz, 1H), 7.73-7.77 (m, 2H), 7.63-7.67 (m, 2H), 7.24 (d, J = 7.7 Hz, 1H), 7.17 (s, 1H), 7.11-7.14 (m, 1H), 4.72-4.74 (bs, 4H), 3.22-3.31 (m, 2H), 2.33 (s, 3H), 1.61 (dp, J = 13.3, 6.6 Hz, 1H), 1.37-1.45 (m, 2H), 0.90 (d, J = 6.6 Hz, 6H) | (ESI (+)) m/e 366 (M + H)$^+$ |
| 44 | N-(4-{[4-(4-fluorophenyl)piperazin-1-yl]carbonyl}phenyl)-1,3-dihydro-2H-isoindole-2-carboxamide | $^1$H NMR (300 MHz, DMSO-d$_6$) δ ppm 8.56 (s, 1H), 7.65-7.69 (m, 2H), 7.30-7.39 (m, 6H), 6.96-7.14 (m, 4H), 4.78-4.80 (bs, 4H), 3.52-3.77 (m, 4H), 3.03-3.20 (m, 4H) | (ESI (+)) m/e 445 (M + H)$^+$ |
| 45 | N-{4-[(4-methoxybenzyl)carbamoyl]phenyl}-1,3-dihydro-2H-isoindole-2-carboxamide | $^1$H NMR (400 MHz, Pyridine-d$_5$, Temp = 90° C.) δ ppm 8.46-8.51 (bs, 1H), 8.27-8.29 (bs, 1H), 8.14-8.16 (m, 2H), 7.91-7.93 (m, 2H), 7.36-7.39 (m, 2H), 7.19-7.23 (m, 2H), 7.16-7.18 (m, 2H), 6.88-6.90 (m, 2H), 4.84 (s, 4H), 4.74 (d, J = 5.8 Hz, 2H), 3.65 (s, 3H) | (ESI (+)) m/e 402 (M + H)$^+$ |
| 46 | N-{4-[(2-thienylmethyl)carbamoyl]phenyl}-1,3-dihydro-2H-isoindole-2-carboxamide | $^1$H NMR (400 MHz, Pyridine-d$_5$, Temp = 90° C.) δ ppm 8.73-8.79 (m, 1H), 8.30 (d, J = 2.1 Hz, 1H), 8.11-8.14 (m, 2H), 7.90-7.93 (m, 2H), 7.19-7.24 (m, 2H), 7.20-7.21 (m, 1H), 7.15-7.18 (m, 2H), 7.05-7.07 (m, 1H), 6.90 (dd, J = 5.0, 3.5 Hz, 1H), 4.94 (d, J = 5.8 Hz, 2H), 4.84 (s, 4H) | (ESI (+)) m/e 378 (M + H)$^+$ |
| 47 | N-(4-{[4-(pyrimidin-2-yl)piperazin-1-yl]carbonyl}phenyl)-5-(trifluoromethyl)-1,3-dihydro-2H-isoindole-2-carboxamide | $^1$H NMR (300 MHz, DMSO-d$_6$) δ ppm 8.64 (s, 1H), 8.37-8.40 (m, 2H), 7.77 (s, 1H), 7.66-7.71 (m, 1H), 7.64-7.69 (m, 2H), 7.61 (d, J = 8.1 Hz, 1H), 7.37-7.40 (m, 2H), 6.67 (t, J = 4.7 Hz, 1H), 4.85-4.88 (bs, 4H), 3.73-3.87 (m, 4H), 3.50-3.69 (m, 4H) | (ESI (+)) m/e 497 (M + H)$^+$ |
| 48 | N-{4-[(1-ethyl-1H-pyrazol-4-yl)carbamoyl]phenyl}-5-fluoro-1,3-dihydro-2H-isoindole-2-carboxamide | $^1$H NMR (300 MHz, DMSO-d$_6$) δ ppm 10.22 (s, 1H), 8.65 (s, 1H), 8.03 (s, 1H), 7.85-7.89 (m, 2H), 7.68-7.75 (m, 2H), 7.57 (d, J = 0.7 Hz, 1H), 7.40 (dd, J = 8.4, 5.2 Hz, 1H), 7.25 (dd, J = 9.1, 2.5 Hz, 1H), 7.15 (td, J = 8.9, 2.5 Hz, 1H), 4.71-4.80 (m, 4H), 4.11 (q, J = 7.2 Hz, 2H), 1.36 (t, J = 7.2 Hz, 3H) | (ESI (+)) m/e 394 (M + H)$^+$ |
| 49 | N-{4-[(1-benzyl-1H-pyrazol-4-yl)carbamoyl]phenyl}-5-fluoro-1,3-dihydro-2H-isoindole-2-carboxamide | $^1$H NMR (300 MHz, DMSO-d$_6$) δ ppm 10.26 (s, 1H), 8.65 (s, 1H), 8.11 (d, J = 0.7 Hz, 1H), 7.84-7.88 (m, 2H), 7.68-7.73 (m, 2H), 7.61 (d, J = 0.7 Hz, 1H), 7.38-7.43 (m, 1H), 7.28-7.38 (m, 3H), 7.22-7.27 (m, 3H), 7.11-7.19 (m, 1H), 5.31 (s, 2H), 4.70-4.85 (m, 4H) | (ESI (+)) m/e 456 (M + H)$^+$ |
| 50 | N-(4-{[4-(pyridin-2-yl)piperazin-1-yl]carbonyl}phenyl)-1,3-dihydro-2H-isoindole-2-carboxamide | $^1$H NMR (400 MHz, DMSO-d$_6$/Deuterium Oxide, Temp = 90° C.) δ ppm 8.08 (ddd, J = 5.4, 1.9, 0.8 Hz, 1H), 7.77 (ddd, J = 8.9, 7.0, 1.9 Hz, 1H), 7.65-7.68 (m, 2H), 7.38-7.42 (m, 2H), 7.32-7.39 (m, 4H), 7.03-7.06 (m, 1H), 6.83 (ddd, J = 7.0, 5.4, 0.8 Hz, 1H), 4.82 (s, 4H), 3.64-3.72 (m, 8H) | (ESI (+)) m/e 428 (M + H)$^+$ |
| 51 | N-(4-{[4-(pyrazin-2-yl)piperazin-1-yl]carbonyl}phenyl)-1,3-dihydro-2H-isoindole-2-carboxamide | $^1$H NMR (500 MHz, DMSO-d$_6$/Deuterium Oxide) δ ppm 8.33-8.34 (bs, 1H), 8.13-8.14 (bs, 1H), 7.88-7.89 (bs, 1H), 7.65-7.67 (m, 2H), 7.38-7.42 (m, 2H), 7.37-7.40 (m, 2H), 7.31-7.36 (m, 2H), 4.79-4.80 (bs, 4H), 3.52-3.75 (m, 8H) | (ESI (+)) m/e 429 (M + H)$^+$ |

| Ex | Name | ¹H NMR | MS |
|---|---|---|---|
| 52 | N-(4-{[4-(2-methoxyphenyl)piperazin-1-yl]carbonyl}phenyl)-1,3-dihydro-2H-isoindole-2-carboxamide | ¹H NMR (400 MHz, Pyridine-$d_5$, Temp = 90° C.) δ ppm 8.30-8.32 (bs, 1H), 7.92-7.96 (m, 2H), 7.56-7.59 (m, 2H), 7.20-7.23 (m, 2H), 7.16-7.19 (m, 2H), 6.97-7.03 (m, 1H), 6.90-6.96 (m, 3H), 4.86 (s, 4H), 3.78-3.81 (m, 4H), 3.75 (s, 3H), 3.04-3.07 (m, 4H) | (ESI (+)) m/e 457 (M + H)⁺ |
| 53 | N-{4-[(3,3-dimethylbutyl)carbamoyl]phenyl}-1,3-dihydro-2H-isoindole-2-carboxamide | ¹H NMR (500 MHz, DMSO-$d_6$) δ ppm 8.56 (s, 1H), 8.20 (t, J = 5.7 Hz, 1H), 7.74-7.76 (m, 2H), 7.64-7.66 (m, 2H), 7.34-7.40 (m, 2H), 7.29-7.34 (m, 2H), 4.78-4.79 (bs, 4H), 3.24-3.28 (m, 2H), 1.43-1.46 (m, 2H), 0.93 (s, 9H) | (ESI (+)) m/e 366 (M + H)⁺ |
| 54 | N-(4-{[(2R)-tetrahydrofuran-2-ylmethyl]carbamoyl}phenyl)-1,3-dihydro-2H-isoindole-2-carboxamide | ¹H NMR (400 MHz, Pyridine-$d_5$, Temp = 90° C.) δ ppm 8.33 (d, J = 8.7 Hz, 1H), 8.08-8.10 (m, 2H), 7.90-7.96 (bs, 1H), 7.89-7.93 (m, 2H), 7.19-7.24 (m, 2H), 7.14-7.18 (m, 2H), 4.84 (s, 4H), 4.10-4.19 (m, 1H), 3.74-3.83 (m, 2H), 3.56-3.67 (m, 2H), 1.79-1.91 (m, 1H), 1.56-1.80 (m, 3H) | (ESI (+)) m/e 366 (M + H)⁺ |
| 55 | N-(4-{[4-(3-methoxyphenyl)piperazin-1-yl]carbonyl}phenyl)-1,3-dihydro-2H-isoindole-2-carboxamide | ¹H NMR (400 MHz, Pyridine-$d_5$, Temp = 90° C.) δ ppm 8.32-8.33 (bs, 1H), 7.93-7.96 (m, 2H), 7.55-7.58 (m, 2H), 7.15-7.27 (m, 5H), 6.63 (t, J = 2.3 Hz, 1H), 6.60 (ddd, J = 8.2, 2.4, 0.8 Hz, 1H), 6.54 (ddd, J = 8.1, 2.3, 0.8 Hz, 1H), 4.86 (s, 4H), 3.72-3.76 (m, 4H), 3.71 (s, 3H), 3.14-3.17 (m, 4H) | (ESI (+)) m/e 457 (M + H)⁺ |
| 56 | N-(4-{[4-(4-acetylphenyl)piperazin-1-yl]carbonyl}phenyl)-1,3-dihydro-2H-isoindole-2-carboxamide | ¹H NMR (400 MHz, Pyridine-$d_5$, Temp = 90° C.) δ ppm 8.34 (d, J = 2.2 Hz, 1H), 7.98-8.02 (m, 2H), 7.93-7.96 (m, 2H), 7.56-7.60 (m, 2H), 7.20-7.26 (m, 2H), 7.15-7.20 (m, 2H), 6.89-6.93 (m, 2H), 4.87 (s, 4H), 3.73-3.76 (m, 4H), 3.26-3.32 (m, 4H), 2.47 (s, 3H) | (ESI (+)) m/e 469 (M + H)⁺ |
| 57 | N-(4-{[2-(2,3-dimethoxyphenyl)ethyl]carbamoyl}phenyl)-1,3-dihydro-2H-isoindole-2-carboxamide | ¹H NMR (400 MHz, Pyridine-$d_5$, Temp = 90° C.) δ ppm 8.25-8.26 (bs, 1H), 8.08-8.13 (bs, 1H), 8.07-8.11 (m, 2H), 7.89-7.92 (m, 2H), 7.19-7.23 (m, 2H), 7.17-7.19 (m, 2H), 6.93-6.97 (m, 1H), 6.91 (dd, J = 7.6, 2.0 Hz, 1H), 6.82 (dd, J = 7.7, 1.9 Hz, 1H), 4.84 (s, 4H), 3.85-3.89 (m, 2H), 3.83 (s, 3H), 3.70 (s, 3H), 3.11 (t, J = 7.2 Hz, 2H) | (ESI (+)) m/e 446 (M + H)⁺ |
| 58 | N-{4-[(3-thienylmethyl)carbamoyl]phenyl}-1,3-dihydro-2H-isoindole-2-carboxamide | ¹H NMR (400 MHz, Pyridine-$d_5$, Temp = 90° C.) δ ppm 8.54-8.60 (m, 1H), 8.27-8.31 (bs, 1H), 8.12-8.14 (m, 2H), 7.90-7.93 (m, 2H), 7.26-7.30 (m, 2H), 7.19-7.23 (m, 2H), 7.16-7.19 (m, 3H), 4.84 (s, 4H), 4.77 (d, J = 5.8 Hz, 2H) | (ESI (+)) m/e 378 (M + H)⁺ |
| 59 | 5-methoxy-N-{4-[(3-methylbutyl)carbamoyl]phenyl}-1,3-dihydro-2H-isoindole-2-carboxamide | ¹H NMR (300 MHz, DMSO-$d_6$) δ ppm 8.55 (s, 1H), 8.22 (t, J = 5.6 Hz, 1H), 7.73-7.78 (m, 2H), 7.62-7.67 (m, 2H), 7.26 (d, J = 8.3 Hz, 1H), 6.94 (d, J = 2.0 Hz, 1H), 6.89 (dd, J = 8.3, 2.4 Hz, 1H), 4.70-4.75 (m, 4H), 3.77 (s, 3H), 3.22-3.30 (m, 2H), 1.53-1.69 (m, 1H), 1.37-1.45 (m, 2H), 0.91 (d, J = 6.6 Hz, 6H) | (ESI (+)) m/e 382 (M + H)⁺ |
| 60 | N-{4-[(pyridin-2-ylmethyl)carbamoyl]phenyl}-1,3-dihydro-2H-isoindole-2-carboxamide | ¹H NMR (300 MHz, DMSO-$d_6$) δ ppm 8.93 (t, J = 6.0 Hz, 1H), 8.61 (s, 1H), 8.51 (ddd, J = 4.8, 1.8, 0.9 Hz, 1H), 7.83-7.87 (m, 2H), 7.75 (td, J = 7.7, 1.8 Hz, 1H), 7.67-7.72 (m, 2H), 7.29-7.40 (m, 5H), 7.26 (ddd, J = 7.5, 4.8, 1.1 Hz, 1H), 4.80 (s, 4H), 4.56 (d, J = 5.8 Hz, 2H) | (ESI (+)) m/e 372 (M + H)⁺ |
| 61 | 5-fluoro-N-(4-{[2-(2-thienyl)ethyl]carbamoyl}phenyl)-1,3-dihydro-2H-isoindole-2-carboxamide | ¹H NMR (300 MHz, DMSO-$d_6$) δ ppm 8.60 (s, 1H), 8.45 (t, J = 5.6 Hz, 1H), 7.74-7.78 (m, 2H), 7.63-7.67 (m, 2H), 7.40 (dd, J = 8.4, 5.2 Hz, 1H), 7.33 (dd, J = 5.0, 1.3 Hz, 1H), 7.24 (dd, J = 9.1, 2.3 Hz, 1H), 7.10-7.19 (m, 2H), 6.96 (dd, J = 5.0, 3.4 Hz, 1H), 6.90-6.93 (m, 1H), 4.71-4.84 (m, 4H), 3.44-3.53 (m, 2H), 3.06 (t, J = 7.2 Hz, 2H) | (ESI (+)) m/e 410 (M + H)⁺ |

-continued

| Ex | Name | ¹H NMR | MS |
|---|---|---|---|
| 62 | N-(4-{[(2S)-tetrahydrofuran-2-ylmethyl]carbamoyl}phenyl)-1,3-dihydro-2H-isoindole-2-carboxamide | ¹H NMR (400 MHz, Pyridine-d₅, Temp = 90° C.) δ ppm 8.27-8.31 (bs, 1H), 8.06-8.12 (m, 2H), 7.89-7.93 (m, 2H), 7.89-7.92 (m, 1H), 7.18-7.25 (m, 2H), 7.14-7.19 (m, 2H), 4.84 (s, 4H), 4.14 (qd, J = 6.7, 4.5 Hz, 1H), 3.73-3.83 (m, 2H), 3.55-3.68 (m, 2H), 1.80-1.91 (m, 1H), 1.56-1.79 (m, 3H) | (ESI (+)) m/e 366 (M + H)⁺ |
| 63 | N-(4-{[1-(3-methylbutyl)-1H-pyrazol-4-yl]carbamoyl}phenyl)-1,3-dihydro-2H-isoindole-2-carboxamide | ¹H NMR (300 MHz, DMSO-d₆) δ ppm 10.21 (s, 1H), 8.63 (s, 1H), 8.03 (d, J = 0.7 Hz, 1H), 7.85-7.89 (m, 2H), 7.70-7.74 (m, 2H), 7.56 (d, J = 0.7 Hz, 1H), 7.30-7.40 (m, 4H), 4.80 (s, 4H), 4.10 (t, J = 7.1 Hz, 2H), 1.65 (q, J = 7.0 Hz, 2H), 1.40-1.56 (m, 1H), 0.90 (d, J = 6.6 Hz, 6H) | (ESI (+)) m/e 418 (M + H)⁺ |
| 64 | 4-chloro-N-(4-{[4-(pyridin-2-yl)piperazin-1-yl]carbonyl}phenyl)-1,3-dihydro-2H-isoindole-2-carboxamide | ¹H NMR (300 MHz, DMSO-d₆) δ ppm 8.66 (s, 1H), 8.13 (dd, J = 4.9, 1.9 Hz, 1H), 7.64-7.71 (m, 2H), 7.56 (ddd, J = 8.7, 7.0, 1.9 Hz, 1H), 7.34-7.41 (m, 5H), 6.85 (d, J = 8.6 Hz, 1H), 6.67 (dd, J = 6.9, 4.8 Hz, 1H), 4.76-4.92 (m, 4H), 3.45-3.74 (m, 8H) | (ESI (+)) m/e 462 (M + H)⁺ |
| 65 | N-{4-[(4-phenylpiperazin-1-yl)carbonyl]phenyl}-1,3-dihydro-2H-isoindole-2-carboxamide | ¹H NMR (300 MHz, DMSO-d₆) δ ppm 8.56 (s, 1H), 7.65-7.69 (m, 2H), 7.29-7.41 (m, 6H), 7.18-7.27 (m, 2H), 6.94-6.98 (m, 2H), 6.81 (t, J = 7.3 Hz, 1H), 4.79-4.80 (bs, 4H), 3.58-3.74 (m, 4H), 3.14-3.22 (m, 4H) | (ESI (+)) m/e 427 (M + H)⁺ |
| 66 | N-{4-[(6-aminohexyl)carbamoyl]phenyl}-1,3-dihydro-2H-isoindole-2-carboxamide | ¹H NMR (300 MHz, DMSO-d₆) δ ppm 8.58 (s, 1H), 8.26 (t, J = 5.6 Hz, 1H), 7.73-7.80 (m, 2H), 7.64-7.68 (m, 2H), 7.61-7.69 (m, 2H), 7.30-7.39 (m, 4H), 4.79 (s, 4H), 3.21-3.26 (m, 2H), 2.72-2.84 (m, 2H), 1.48-1.57 (m, 4H), 1.31-1.35 (m, 4H) | (ESI (+)) m/e 381 (M + H)⁺ |
| 67 | 4-chloro-N-{4-[(3-methylbutyl)carbamoyl]phenyl}-1,3-dihydro-2H-isoindole-2-carboxamide | ¹H NMR (300 MHz, DMSO-d₆) δ ppm 8.66 (s, 1H), 8.22 (t, J = 5.6 Hz, 1H), 7.74-7.78 (m, 2H), 7.63-7.68 (m, 2H), 7.35-7.42 (m, 3H), 4.76-4.92 (m, 4H), 3.22-3.30 (m, 2H), 1.54-1.68 (m, 1H), 1.37-1.45 (m, 2H), 0.91 (d, J = 6.6 Hz, 6H) | (ESI (+)) m/e 386 (M + H)⁺ |
| 68 | N-(4-{[2-(2-thienyl)ethyl]carbamoyl}phenyl)-1,3-dihydro-2H-isoindole-2-carboxamide | ¹H NMR (300 MHz, DMSO-d₆) δ ppm 8.58 (s, 1H), 8.45 (t, J = 5.6 Hz, 1H), 7.75-7.78 (m, 2H), 7.65-7.68 (m, 2H), 7.25-7.44 (m, 5H), 6.96 (dd, J = 5.1, 3.4 Hz, 1H), 6.90-6.93 (m, 1H), 4.78-4.79 (bs, 4H), 3.45-3.52 (m, 2H), 3.06 (t, J = 7.2 Hz, 2H) | (ESI (+)) m/e 390 (M + H)⁺ |
| 69 | 5-methoxy-N-(4-{[4-(pyridin-2-yl)piperazin-1-yl]carbonyl}phenyl)-1,3-dihydro-2H-isoindole-2-carboxamide | ¹H NMR (300 MHz, DMSO-d₆) δ ppm 8.56 (s, 1H), 8.10 (dd, J = 5.5, 1.8 Hz, 1H), 7.75-7.82 (m, 1H), 7.65-7.69 (m, 2H), 7.37-7.41 (m, 2H), 7.27 (d, J = 8.3 Hz, 1H), 7.08-7.12 (m, 1H), 6.95 (d, J = 2.3 Hz, 1H), 6.89 (dd, J = 8.3, 2.4 Hz, 1H), 6.82 (t, J = 6.2 Hz, 1H), 4.71-4.75 (m, 4H), 3.95-4.67 (m, 8H), 3.77 (s, 3H) | (ESI (+)) m/e 458 (M + H)⁺ |
| 70 | N-{4-[(1,3-benzodioxol-5-ylmethyl)carbamoyl]phenyl}-1,3-dihydro-2H-isoindole-2-carboxamide | ¹H NMR (500 MHz, DMSO-d₆/Deuterium Oxide) δ ppm 7.79-7.81 (m, 2H), 7.65-7.67 (m, 2H), 7.32-7.39 (m, 4H), 6.89 (d, J = 1.6 Hz, 1H), 6.86 (d, J = 7.9 Hz, 1H), 6.81 (dd, J = 8.0, 1.4 Hz, 1H), 5.97 (s, 2H), 4.79 (s, 4H), 4.37 (d, J = 5.2 Hz, 2H) | (ESI (+)) m/e 416 (M + H)⁺ |
| 71 | N-{4-[(3-methoxybenzyl)carbamoyl]phenyl}-1,3-dihydro-2H-isoindole-2-carboxamide | ¹H NMR (300 MHz, DMSO-d₆) δ ppm 8.83 (t, J = 6.0 Hz, 1 H), 8.59 (s, 1 H), 7.77-7.87 (m, 2 H), 7.68 (d, J = 8.7 Hz, 2 H), 7.28-7.42 (m, 4 H), 7.24 (t, J = 8.1 Hz, 1 H), 6.75-6.94 (m, 3 H), 4.79 (s, 4 H), 4.43 (d, J = 6.0 Hz, 2 H), 3.73 (s, 3 H) | (ESI (+)) m/e 402 (M + H)⁺ |
| 72 | N-(4-{[4-(pyridin-3-yl)piperazin-1-yl]carbonyl}phenyl)-1,3-dihydro-2H-isoindole-2-carboxamide | ¹H NMR (300 MHz, DMSO-d₆) δ ppm 8.56 (s, 1H), 8.33 (d, J = 2.9 Hz, 1H), 8.03 (dd, J = 4.5, 1.3 Hz, 1H), 7.66-7.69 (m, 2H), 7.30-7.41 (m, 7H), 7.24 (dd, J = 8.4, 4.5 Hz, 1H), 4.79 (s, 4H), 3.64-3.67 (m, 4H), 3.21-3.29 (m, 4H) | (ESI (+)) m/e 428 (M + H)⁺ |
| 73 | N-[4-(benzylcarbamoyl)phenyl]-1,3-dihydro-2H-isoindole-2-carboxamide | ¹H NMR (300 MHz, DMSO-d₆) δ ppm 8.86 (t, J = 6.0 Hz, 1H), 8.59 (s, 1H), 7.80-7.84 (m, 2H), 7.66-7.70 (m, 2H), 7.31-7.36 (m, 9H), 4.79 (s, 4H), 4.47 (d, J = 5.9 Hz, 2H) | (ESI (+)) m/e 372 (M + H)⁺ |

| Ex | Name | ¹H NMR | MS |
|---|---|---|---|
| 74 | N-(4-{[4-(pyridazin-3-yl)piperazin-1-yl]carbonyl}phenyl)-1,3-dihydro-2H-isoindole-2-carboxamide | ¹H NMR (300 MHz, DMSO-d$_6$) δ ppm 8.56-8.60 (m, 1H), 8.57-8.58 (m, 1H), 7.64-7.72 (m, 2H), 7.24-7.45 (m, 8H), 4.80 (s, 4H), 3.60-3.70 (m, 8H) | (ESI (−)) m/e 427 (M − H)⁻ |
| 75 | N-{4-[(pyrimidin-4-ylmethyl)carbamoyl]phenyl}-1,3-dihydro-2H-isoindole-2-carboxamide | ¹H NMR (400 MHz, Pyridine-d$_5$, Temp = 90° C.) δ ppm 9.21 (d, J = 1.4 Hz, 1H), 8.86-8.90 (m, 1H), 8.61 (d, J = 5.1 Hz, 1H), 8.34-8.36 (bs, 1H), 8.17-8.20 (m, 2H), 7.95-7.97 (m, 2H), 7.41-7.43 (m, 1H), 7.20-7.23 (m, 2H), 7.15-7.19 (m, 2H), 4.87 (d, J = 5.8 Hz, 2H), 4.85 (s, 4H) | (ESI (−)) m/e 372 (M − H)⁻ |
| 76 | N-(4-{[4-(3-fluorophenyl)piperazin-1-yl]carbonyl}phenyl)-1,3-dihydro-2H-isoindole-2-carboxamide | ¹H NMR (300 MHz, DMSO-d$_6$) δ ppm 8.56 (s, 1H), 7.65-7.69 (m, 2H), 7.15-7.46 (m, 7H), 6.70-6.84 (m, 2H), 6.54-6.61 (m, 1H), 4.79-4.80 (bs, 4H), 3.54-3.75 (m, 4H), 3.12-3.28 (m, 4H) | (ESI (−)) m/e 443 (M − H)⁻ |
| 77 | N-{4-[(2-methylbutyl)carbamoyl]phenyl}-1,3-dihydro-2H-isoindole-2-carboxamide | ¹H NMR (400 MHz, Pyridine-d$_5$, Temp = 90° C.) δ ppm 8.28-8.30 (bs, 1H), 8.09-8.12 (m, 2H), 7.90-7.93 (m, 2H), 7.84 (d, J = 6.2 Hz, 1H), 7.16-7.26 (m, 4H), 4.84 (s, 4H), 3.51 (dt, J = 13.2, 6.1 Hz, 1H), 3.39 (ddd, J = 13.2, 7.1, 6.0 Hz, 1H), 1.71-1.83 (m, 1H), 1.42-1.53 (m, 1H), 1.08-1.24 (m, 1H), 0.93 (d, J = 6.7 Hz, 3H), 0.86 (t, J = 7.4 Hz, 3H) | (ESI (+)) m/e 352 (M + H)⁺ |
| 78 | N-(4-{[4-(pyridin-2-yl)piperazin-1-yl]carbonyl}phenyl)-5-(trifluoromethyl)-1,3-dihydro-2H-isoindole-2-carboxamide | ¹H NMR (300 MHz, DMSO-d$_6$) δ ppm 8.65 (s, 1H), 8.10 (dd, J = 5.5, 1.8 Hz, 1H), 7.46-7.82 (m, 6H), 7.38-7.42 (m, 2H), 7.06-7.10 (m, 1H), 6.81 (t, J = 6.2 Hz, 1H), 4.85-4.88 (bs, 4H), 3.56-3.73 (bs, 8H) | (ESI (+)) m/e 496 (M + H)⁺ |
| 79 | N-{4-[(3-butoxypropyl)carbamoyl]phenyl}-1,3-dihydro-2H-isoindole-2-carboxamide | ¹H NMR (400 MHz, Pyridine-d$_5$, Temp = 90° C.) δ ppm 8.27-8.29 (bs, 1H), 8.07-8.10 (m, 2H), 7.93-7.98 (m, 1H), 7.90-7.94 (m, 2H), 7.19-7.23 (m, 2H), 7.16-7.18 (m, 2H), 4.84 (s, 4H), 3.69 (td, J = 6.7, 5.6 Hz, 2H), 3.51 (t, J = 6.1 Hz, 2H), 3.36 (t, J = 6.5 Hz, 2H), 1.95 (p, J = 6.4 Hz, 2H), 1.44-1.60 (m, 2H), 1.25-1.42 (m, 2H), 0.85 (t, J = 7.3 Hz, 3H) | (ESI (−)) m/e 394 (M − H)⁻ |
| 80 | N-(4-{[(1S)-2-hydroxy-1-phenylethyl]carbamoyl}phenyl)-1,3-dihydro-2H-isoindole-2-carboxamide | ¹H NMR (400 MHz, Pyridine-d$_5$, Temp = 90° C.) δ ppm 8.28-8.30 (bs, 1H), 8.14-8.18 (m, 1H), 8.07-8.11 (m, 2H), 7.87-7.89 (m, 2H), 7.60-7.65 (m, 2H), 7.26-7.32 (m, 2H), 7.20-7.23 (m, 3H), 7.14-7.18 (m, 3H), 5.67-5.73 (m, 1H), 4.83 (s, 4H), 4.21-4.25 (m, 2H) | (ESI (+)) m/e 402 (M + H)⁺ |
| 81 | N-(4-{[2-(3,4-dihydroxyphenyl)ethyl]carbamoyl}phenyl)-1,3-dihydro-2H-isoindole-2-carboxamide | ¹H NMR (500 MHz, DMSO-d$_6$/Deuterium Oxide) δ ppm 7.74-7.76 (m, 2H), 7.64-7.67 (m, 2H), 7.32-7.40 (m, 4H), 6.66 (d, J = 10.7 Hz, 1H), 6.66 (d, J = 2.4 Hz, 1H), 6.51 (dd, J = 8.0, 2.1 Hz, 1H), 4.79-4.80 (bs, 4H), 3.39 (t, J = 7.5 Hz, 2H), 2.66 (t, J = 7.5 Hz, 2H) | (ESI (+)) m/e 418 (M + H)⁺ |
| 82 | N-{4-[(3-propoxypropyl)carbamoyl]phenyl}-1,3-dihydro-2H-isoindole-2-carboxamide | ¹H NMR (400 MHz, Pyridine-d$_5$, Temp = 90° C.) δ ppm 8.28-8.30 (bs, 1H), 8.07-8.10 (m, 2H), 7.93-8.00 (m, 1H), 7.90-7.94 (m, 2H), 7.19-7.24 (m, 2H), 7.15-7.18 (m, 2H), 4.84 (s, 4H), 3.66-3.71 (m, 2H), 3.51 (t, J = 6.1 Hz, 2H), 3.30 (t, J = 6.5 Hz, 2H), 1.94 (p, J = 6.4 Hz, 2H), 1.48-1.57 (m, 2H), 0.85 (t, J = 7.4 Hz, 3H) | (ESI (−)) m/e 380 (M − H)⁻ |
| 83 | N-{4-[(3-furylmethyl)carbamoyl]phenyl}-1,3-dihydro-2H-isoindole-2-carboxamide | ¹H NMR (400 MHz, Pyridine-d$_5$, Temp = 90° C.) δ ppm 8.37-8.53 (m, 1H), 8.28-8.31 (bs, 1H), 8.10-8.13 (m, 2H), 7.90-7.93 (m, 2H), 7.52-7.54 (m, 1H), 7.41 (t, J = 1.7 Hz, 1H), 7.19-7.23 (m, 2H), 7.15-7.18 (m, 2H), 6.51-6.53 (m, 1H), 4.84 (s, 4H), 4.60-4.62 (m, 2H) | (ESI (+)) m/e 362 (M + H)⁺ |

| Ex | Name | ¹H NMR | MS |
|---|---|---|---|
| 84 | N-(4-{[4-(2-cyanophenyl)piperazin-1-yl]carbonyl}phenyl)-1,3-dihydro-2H-isoindole-2-carboxamide | ¹H NMR (400 MHz, Pyridine-d₅, Temp = 90° C.) δ ppm 8.32-8.33 (bs, 1H), 7.92-7.95 (m, 2H), 7.55-7.58 (m, 1H), 7.53-7.59 (m, 2H), 7.39-7.44 (m, 1H), 7.20-7.25 (m, 2H), 7.15-7.20 (m, 2H), 6.93-6.99 (m, 2H), 4.80-4.87 (m, 4H), 3.80-3.83 (m, 4H), 3.15-3.17 (m, 4H) | (ESI (+)) m/e 452 (M + H)⁺ |
| 85 | N-{4-[(3-hydroxy-2-methylphenyl)carbamoyl]phenyl}-1,3-dihydro-2H-isoindole-2-carboxamide | ¹H NMR (500 MHz, DMSO-d₆/Deuterium Oxide) δ ppm 7.89-7.92 (m, 2H), 7.69-7.72 (m, 2H), 7.38-7.41 (m, 2H), 7.33-7.36 (m, 2H), 7.02 (t, J = 7.9 Hz, 1H), 6.79 (d, J = 7.8 Hz, 1H), 6.74 (d, J = 8.0 Hz, 1H), 4.80-4.82 (bs, 4H), 2.02 (s, 3H) | (ESI (−)) m/e 386 (M − H)⁻ |
| 86 | N-{4-[(3-methylbutyl)carbamoyl]phenyl}-5-(trifluoromethyl)-1,3-dihydro-2H-isoindole-2-carboxamide | ¹H NMR (300 MHz, DMSO-d₆) δ ppm 8.64 (s, 1H), 8.21 (t, J = 5.6 Hz, 1H), 7.74-7.78 (m, 3H), 7.56-7.70 (m, 4H), 4.85-4.87 (bs, 4H), 3.22-3.30 (m, 2H), 1.51-1.72 (m, 1H), 1.37-1.45 (m, 2H), 0.91 (d, J = 6.6 Hz, 6H) | (ESI (+)) m/e 420 (M + H)⁺ |
| 87 | N-{4-[(3-methyl-1H-indazol-5-yl)carbamoyl]phenyl}-1,3-dihydro-2H-isoindole-2-carboxamide | ¹H NMR (400 MHz, Pyridine-d₅, Temp = 90° C.) δ ppm 10.02-10.04 (bs, 1H), 8.41-8.42 (m, 1H), 8.33-8.35 (bs, 1H), 8.23-8.26 (m, 2H), 7.95-7.98 (m, 2H), 7.86 (dd, J = 8.8, 1.9 Hz, 1H), 7.48-7.53 (m, 1H), 7.20-7.25 (m, 2H), 7.15-7.19 (m, 2H), 4.86 (s, 4H), 2.58 (s, 3H) | (ESI (+)) m/e 412 (M + H)⁺ |
| 88 | N-{4-[(3-ethoxypropyl)carbamoyl]phenyl}-1,3-dihydro-2H-isoindole-2-carboxamide | ¹H NMR (400 MHz, Pyridine-d₅, Temp = 90° C.) δ ppm 8.27-8.28 (bs, 1H), 8.07-8.10 (m, 2H), 7.94-7.99 (m, 1H), 7.89-7.94 (m, 2H), 7.19-7.23 (m, 2H), 7.15-7.19 (m, 2H), 4.84 (s, 4H), 3.68 (td, J = 6.7, 5.7 Hz, 2H), 3.49 (t, J = 6.1 Hz, 2H), 3.38 (q, J = 6.9 Hz, 2H), 1.93 (p, J = 6.4 Hz, 2H), 1.10 (t, J = 6.9 Hz, 3H) | (ESI (+)) m/e 368 (M + H)⁺ |
| 89 | N-(4-{[4-(pyrazin-2-yl)piperazin-1-yl]carbonyl}phenyl)-5-(trifluoromethyl)-1,3-dihydro-2H-isoindole-2-carboxamide | ¹H NMR (300 MHz, DMSO-d₆) δ ppm 8.65 (s, 1H), 8.34 (s, 1H), 8.09-8.12 (bs, 1H), 7.87 (d, J = 2.6 Hz, 1H), 7.76-7.78 (bs, 1H), 7.64-7.73 (m, 3H), 7.58-7.64 (m, 1H), 7.37-7.41 (m, 2H), 4.85-4.88 (bs, 4H), 3.62-3.65 (m, 8H) | (ESI (−)) m/e 495 (M − H)⁻ |
| 90 | N-(4-{[2-(2,5-dimethoxyphenyl)ethyl]carbamoyl}phenyl)-1,3-dihydro-2H-isoindole-2-carboxamide | ¹H NMR (500 MHz, DMSO-d₆/Deuterium Oxide) δ ppm 7.73-7.75 (m, 2H), 7.62-7.65 (m, 2H), 7.37-7.40 (m, 2H), 7.32-7.35 (m, 2H), 6.90 (d, J = 8.6 Hz, 1H), 6.76-6.78 (m, 2H), 4.78-4.80 (bs, 4H), 3.78 (s, 3H), 3.44 (t, J = 7.3 Hz, 2H), 2.81 (t, J = 7.2 Hz, 2H) | (ESI (−)) m/e 444 (M − H)⁻ |
| 91 | N-{4-[(tetrahydrofuran-3-ylmethyl)carbamoyl]phenyl}-1,3-dihydro-2H-isoindole-2-carboxamide | ¹H NMR (300 MHz, DMSO-d₆) δ ppm 8.58 (s, 1H), 8.39 (t, J = 5.7 Hz, 1H), 7.75-7.79 (m, 2H), 7.65-7.68 (m, 2H), 7.30-7.39 (m, 4H), 4.79 (s, 4H), 3.57-3.78 (m, 3H), 3.48 (dd, J = 8.5, 5.2 Hz, 1H), 3.17-3.28 (m, 2H), 2.41-2.51 (m, 1H), 1.93 (dtd, J = 12.2, 8.0, 5.7 Hz, 1H), 1.54-1.66 (m, 1H) | (ESI (+)) m/e 366 (M + H)⁺ |
| 92 | N-{4-[(1-benzyl-1H-pyrazol-4-yl)carbamoyl]phenyl}-1,3-dihydro-2H-isoindole-2-carboxamide | ¹H NMR (300 MHz, DMSO-d₆) δ ppm 10.25 (s, 1H), 8.63 (s, 1H), 8.11 (s, 1H), 7.84-7.88 (m, 2H), 7.70-7.74 (m, 2H), 7.61 (d, J = 0.7 Hz, 1H), 7.23-7.40 (m, 9H), 5.31 (s, 2H), 4.79-4.80 (bs, 4H) | (ESI (+)) m/e 438 (M + H)⁺ |
| 93 | methyl 5-({4-[(1,3-dihydro-2H-isoindol-2-ylcarbonyl)amino]benzoyl}amino)-1H-indazole-3-carboxylate | ¹H NMR (400 MHz, Pyridine-d₅, Temp = 90° C.) δ ppm 10.25-10.26 (bs, 1H), 8.92 (d, J = 1.9 Hz, 1H), 8.34-8.36 (bs, 1H), 8.23-8.25 (m, 2H), 8.17 (dd, J = 8.9, 2.0 Hz, 1H), 7.95-7.98 (m, 2H), 7.64 (d, J = 8.9 Hz, 1H), 7.20-7.24 (m, 2H), 7.15-7.20 (m, 2H), 4.86 (s, 4H), 3.90 (s, 3H) | (APCI (+)) m/e 456 (M + H)⁺ |
| 94 | N-(4-{[2-(2-oxopyrrolidin-1-yl)ethyl]carbamoyl}phenyl)-1,3-dihydro-2H-isoindole-2-carboxamide | ¹H NMR (400 MHz, DMSO-d₆/Deuterium Oxide, Temp = 90° C.) δ ppm 7.73-7.75 (m, 2H), 7.62-7.65 (m, 2H), 7.32-7.40 (m, 4H), 4.82 (s, 4H), 3.38-3.47 (m, 6H), 2.23 (t, J = 8.0 Hz, 2H), 1.91-1.99 (m, 2H) | (ESI (+)) m/e 393 (M + H)⁺ |

| Ex | Name | ¹H NMR | MS |
|---|---|---|---|
| 95 | N-{4-[(pyridin-4-ylmethyl)carbamoyl]phenyl}-1,3-dihydro-2H-isoindole-2-carboxamide | ¹H NMR (400 MHz, Pyridine-d₅, Temp = 90° C.) δ ppm 8.81-8.88 (m, 1H), 8.57-8.60 (m, 2H), 8.34-8.37 (bs, 1H), 8.16-8.19 (m, 2H), 7.94-7.98 (m, 2H), 7.30-7.32 (m, 2H), 7.19-7.23 (m, 2H), 7.17-7.19 (m, 2H), 4.85 (s, 4H), 4.74 (d, J = 6.0 Hz, 2H) | (ESI (+)) m/e 373 (M + H)⁺ |
| 96 | N-(4-{[4-(5-chloropyridin-2-yl)piperazin-1-yl]carbonyl}phenyl)-1,3-dihydro-2H-isoindole-2-carboxamide | ¹H NMR (300 MHz, DMSO-d₆) δ ppm 8.56 (s, 1H), 8.13 (d, J = 2.7 Hz, 1H), 7.64-7.70 (m, 2H), 7.63 (dd, J = 9.2, 2.7 Hz, 1H), 7.30-7.39 (m, 6H), 6.90 (d, J = 9.1 Hz, 1H), 4.79-4.80 (bs, 4H), 3.47-3.72 (m, 8H) | (ESI (+)) m/e 462 (M + H)⁺ |
| 97 | N-(4-{[2-(1H-indol-3-yl)ethyl]carbamoyl}phenyl)-1,3-dihydro-2H-isoindole-2-carboxamide | ¹H NMR (400 MHz, DMSO-d₆/Deuterium Oxide, Temp = 90° C.) δ ppm 7.75-7.78 (m, 2H), 7.63-7.66 (m, 2H), 7.59-7.63 (m, 1H), 7.32-7.40 (m, 5H), 7.17 (s, 1H), 7.10 (ddd, J = 8.1, 6.9, 1.2 Hz, 1H), 7.01 (ddd, J = 7.9, 6.9, 1.0 Hz, 1H), 4.82 (s, 4H), 3.60 (t, J = 7.4 Hz, 2H), 3.01 (t, J = 7.4 Hz, 2H) | (ESI (+)) m/e 425 (M + H)⁺ |
| 98 | N-(4-{[4-(trifluoromethyl)benzyl]carbamoyl}phenyl)-1,3-dihydro-2H-isoindole-2-carboxamide | ¹H NMR (500 MHz, DMSO-d₆/Deuterium Oxide) δ ppm 9.05 (t, J = 6.0 Hz, 1H), 7.81-7.84 (m, 2H), 7.66-7.71 (m, 4H), 7.53-7.55 (m, 2H), 7.36-7.41 (m, 2H), 7.32-7.36 (m, 2H), 4.79-4.80 (bs, 4H), 4.54-4.56 (m, 2H) | (ESI (+)) m/e 440 (M + H)⁺ |
| 99 | N-{4-[(3,5-dimethoxyphenyl)carbamoyl]phenyl}-1,3-dihydro-2H-isoindole-2-carboxamide | ¹H NMR (500 MHz, DMSO-d₆/Deuterium Oxide) δ ppm 7.88-7.91 (m, 2H), 7.71-7.74 (m, 2H), 7.38-7.41 (m, 2H), 7.33-7.36 (m, 2H), 7.06-7.07 (m, 2H), 6.27 (t, J = 2.2 Hz, 1H), 4.80-4.81 (bs, 4H), 3.78 (s, 6H) | (APCI (+)) m/e 418 (M + H)⁺ |
| 100 | N-{4-[(pyridin-3-ylmethyl)carbamoyl]phenyl}-1,3-dihydro-2H-isoindole-2-carboxamide | ¹H NMR (400 MHz, Pyridine-d₅, Temp = 90° C.) δ ppm 8.81 (d, J = 2.3 Hz, 1H), 8.75-8.80 (m, 1H), 8.53 (dd, J = 4.7, 1.6 Hz, 1H), 8.31-8.33 (bs, 1H), 8.12-8.15 (m, 2H), 7.91-7.94 (m, 2H), 7.71-7.75 (m, 1H), 7.19-7.23 (m, 2H), 7.16-7.18 (m, 2H), 7.10-7.14 (m, 1H), 4.84 (s, 4H), 4.75 (d, J = 5.8 Hz, 2H) | (ESI (+)) m/e 373 (M + H)⁺ |
| 101 | N-[4-(2,3-dihydro-1,4-benzodioxin-6-ylcarbamoyl)phenyl]-1,3-dihydro-2H-isoindole-2-carboxamide | ¹H NMR (400 MHz, Pyridine-d₅, Temp = 90° C.) δ ppm 9.88-9.89 (bs, 1H), 8.30 (d, J = 2.0 Hz, 1H), 8.13-8.16 (m, 2H), 7.89-7.92 (m, 2H), 7.77 (d, J = 2.5 Hz, 1H), 7.41 (dd, J = 8.6, 2.5 Hz, 1H), 7.19-7.23 (m, 2H), 7.17-7.19 (m, 2H), 6.93 (d, J = 8.6 Hz, 1H), 4.84 (s, 4H), 4.07-4.10 (m, 4H) | (ESI (+)) m/e 416 (M + H)⁺ |
| 102 | N-(4-{[4-(2-fluorobenzoyl)piperazin-1-yl]carbonyl}phenyl)-1,3-dihydro-2H-isoindole-2-carboxamide | ¹H NMR (500 MHz, DMSO-d₆/Deuterium Oxide) δ ppm 7.63-7.65 (m, 2H), 7.50-7.57 (m, 1H), 7.42-7.46 (m, 1H), 7.35-7.41 (m, 4H), 7.28-7.35 (m, 4H), 4.78-4.79 (bs, 4H), 3.71-3.76 (m, 2H), 3.51-3.62 (m, 4H), 3.30-3.33 (m, 2H) | (ESI (+)) m/e 473 (M + H)⁺ |
| 103 | N-(4-{[2-(5-methoxy-1H-indol-3-yl)ethyl]carbamoyl}phenyl)-1,3-dihydro-2H-isoindole-2-carboxamide | ¹H NMR (400 MHz, DMSO-d₆/Deuterium Oxide, Temp = 90° C.) δ ppm 7.75-7.78 (m, 2H), 7.62-7.65 (m, 2H), 7.36-7.41 (m, 2H), 7.31-7.36 (m, 2H), 7.27 (dd, J = 8.7, 0.6 Hz, 1H), 7.14 (q, J = 0.7 Hz, 1H), 7.11 (dd, J = 2.4, 0.5 Hz, 1H), 6.76 (dd, J = 8.6, 2.4 Hz, 1H), 4.82 (s, 4H), 3.78 (s, 3H), 3.58 (t, J = 7.3 Hz, 2H), 2.97 (t, J = 7.3 Hz, 2H) | (ESI (+)) m/e 455 (M + H)⁺ |
| 104 | N-{4-[(3-aminobenzyl)carbamoyl]phenyl}-1,3-dihydro-2H-isoindole-2-carboxamide | ¹H NMR (400 MHz, Pyridine-d₅, Temp = 90° C.) δ ppm 8.39-8.43 (m, 1H), 8.30-8.32 (bs, 1H), 8.11-8.14 (m, 2H), 7.90-7.93 (m, 2H), 7.20-7.24 (m, 2H), 7.17-7.19 (m, 2H), 7.09 (t, J = 7.7 Hz, 1H), 6.92 (t, J = 1.9 Hz, 1H), 6.80 (dd, J = 7.5, 1.4 Hz, 1H), 6.67-6.70 (m, 1H), 4.85 (s, 4H), 4.73 (d, J = 5.8 Hz, 2H) | (APCI (+)) m/e 387 (M + H)⁺ |
| 105 | N-(4-{[2-(2-chlorophenyl)ethyl]carbamoyl}phenyl)-1,3-dihydro-2H-isoindole-2-carboxamide | ¹H NMR (500 MHz, DMSO-d₆/Deuterium Oxide) δ ppm 8.49 (t, J = 5.6 Hz, 1H), 7.73-7.75 (m, 2H), 7.63-7.65 (m, 2H), 7.43 (dd, J = 7.4, 1.9 Hz, 1H), 7.36-7.40 (m, 2H), 7.35-7.37 (m, 2H), 7.32-7.36 (m, 2H), 7.24-7.31 (m, 1H), 4.78-4.80 (bs, 4H), 3.49-3.54 (m, 2H), 2.98 (t, J = 7.2 Hz, 2H) | (ESI (+)) m/e 420 (M + H)⁺ |

| Ex | Name | ¹H NMR | MS |
|---|---|---|---|
| 106 | N-(4-{[(2R)-1-hydroxy-4-methylpentan-2-yl]carbamoyl}phenyl)-1,3-dihydro-2H-isoindole-2-carboxamide | ¹H NMR (300 MHz, DMSO-$d_6$) d ppm 8.56 (s, 1 H) 7.71-7.86 (m, 3 H) 7.59-7.71 (m, 2 H) 7.20-7.45 (m, 4 H) 4.79 (s, 4 H) 4.64 (t, J = 5.8 Hz, 1 H) 3.90-4.16 (m, 1 H) 3.21-3.52 (m, 2 H) 1.54-1.72 (m, 1 H) 1.28-1.53 (m, 2 H) 0.88 (t, J = 6.7 Hz, 6 H) | (ESI (+)) m/e 382 (M + H)⁺ |
| 107 | N-{4-[(2-propoxyethyl)carbamoyl]phenyl}-1,3-dihydro-2H-isoindole-2-carboxamide | ¹H NMR (400 MHz, Pyridine-$d_5$, Temp = 90° C.) δ ppm 8.26-8.28 (bs, 1H), 8.08-8.11 (m, 2H), 7.99-8.06 (m, 1H), 7.89-7.92 (m, 2H), 7.19-7.23 (m, 2H), 7.16-7.18 (m, 2H), 4.84 (s, 4H), 3.77 (q, J = 5.7 Hz, 2H), 3.65 (t, J = 5.7 Hz, 2H), 3.35 (t, J = 6.5 Hz, 2H), 1.43-1.59 (m, 2H), 0.84 (t, J = 7.4 Hz, 3H) | (ESI (+)) m/e 368 (M + H)⁺ |
| 108 | N-{4-[(3-isobutoxypropyl)carbamoyl]phenyl}-1,3-dihydro-2H-isoindole-2-carboxamide | ¹H NMR (400 MHz, Pyridine-$d_5$, Temp = 90° C.) δ ppm 8.27-8.29 (bs, 1H), 8.08-8.10 (m, 2H), 7.92-7.98 (m, 1H), 7.90-7.94 (m, 2H), 7.19-7.23 (m, 2H), 7.16-7.19 (m, 2H), 4.84 (s, 4H), 3.66-3.72 (m, 2H), 3.51 (t, J = 6.1 Hz, 2H), 3.13 (d, J = 6.4 Hz, 2H), 1.95 (p, J = 6.4 Hz, 2H), 1.75-1.87 (m, 1H), 0.87 (d, J = 6.7 Hz, 6H) | (ESI (+)) m/e 396 (M + H)⁺ |
| 109 | N-(4-{[4-(pyridin-4-yl)piperazin-1-yl]carbonyl}phenyl)-1,3-dihydro-2H-isoindole-2-carboxamide | ¹H NMR (300 MHz, DMSO-$d_6$) δ ppm 8.57 (s, 1H), 8.16-8.20 (m, 2H), 7.65-7.69 (m, 2H), 7.30-7.40 (m, 6H), 6.81-6.85 (m, 2H), 4.79-4.80 (bs, 4H), 3.60-3.64 (m, 4H) | (ESI (+)) m/e 428 (M + H)⁺ |
| 110 | N-[4-({4-[5-(trifluoromethyl)pyridin-2-yl]piperazin-1-yl}carbonyl)phenyl]-1,3-dihydro-2H-isoindole-2-carboxamide | ¹H NMR (500 MHz, DMSO-$d_6$/Deuterium Oxide) δ ppm 8.42-8.43 (m, 1H), 7.83 (dd, J = 9.1, 2.6 Hz, 1H), 7.65-7.67 (m, 2H), 7.38-7.43 (m, 2H), 7.36-7.41 (m, 2H), 7.32-7.36 (m, 2H), 6.98 (d, J = 9.1 Hz, 1H), 4.79-4.80 (bs, 4H), 3.50-3.74 (m, 8H) | (ESI (−)) m/e 494 (M − H)⁻ |
| 111 | N-{4-[(3,4,5-trimethoxyphenyl)carbamoyl]phenyl}-1,3-dihydro-2H-isoindole-2-carboxamide | ¹H NMR (400 MHz, Pyridine-$d_5$, Temp = 90° C.) δ ppm 9.91-9.93 (bs, 1H), 8.33-8.35 (bs, 1H), 8.17-8.20 (m, 2H), 7.92-7.95 (m, 2H), 7.43 (s, 2H), 7.20-7.25 (m, 2H), 7.15-7.19 (m, 2H), 4.84 (s, 4H), 3.87 (d, J = 0.4 Hz, 3H), 3.74 (s, 6H) | (ESI (−)) m/e 446 (M − H)⁻ |
| 112 | N-{4-[(4-methylpiperidin-1-yl)carbonyl]phenyl}-1,3-dihydro-2H-isoindole-2-carboxamide | ¹H NMR (400 MHz, Pyridine-$d_5$, Temp = 90° C.) δ ppm 8.26-8.28 (bs, 1H), 7.90-7.92 (m, 2H), 7.51-7.54 (m, 2H), 7.19-7.25 (m, 2H), 7.15-7.19 (m, 2H), 4.85 (s, 4H), 4.21-4.27 (m, 2H), 2.82 (ddd, J = 13.2, 12.1, 2.7 Hz, 2H), 1.44-1.50 (m, 3H), 1.01-1.12 (m, 2H), 0.83 (d, J = 6.1 Hz, 3H) | (ESI (+)) m/e 364 (M + H)⁺ |
| 113 | N-[4-({2-[4-(dimethylamino)phenyl]ethyl}carbamoyl)phenyl]-1,3-dihydro-2H-isoindole-2-carboxamide | ¹H NMR (500 MHz, DMSO-$d_6$/Deuterium Oxide) δ ppm 7.73-7.76 (m, 2H), 7.64-7.66 (m, 2H), 7.36-7.41 (m, 2H), 7.30-7.36 (m, 4H), 7.21-7.25 (m, 2H), 4.78-4.80 (bs, 4H), 3.47 (t, J = 7.3 Hz, 2H), 3.05 (s, 6H), 2.83-2.88 (m, 2H) | (APCI (+)) m/e 429 (M + H)⁺ |
| 114 | N-(4-{[3-(trifluoromethoxy)benzyl]carbamoyl}phenyl)-1,3-dihydro-2H-isoindole-2-carboxamide | ¹H NMR (500 MHz, DMSO-$d_6$/Deuterium Oxide) δ ppm 9.03 (t, J = 6.0 Hz, 1H), 8.67-8.69 (bs, 1H), 7.81-7.83 (m, 2H), 7.67-7.69 (m, 2H), 7.48 (t, J = 7.9 Hz, 1H), 7.36-7.41 (m, 2H), 7.34-7.37 (m, 1H), 7.31-7.35 (m, 2H), 7.28-7.29 (bs, 1H), 7.24 (dd, J = 8.2, 2.2 Hz, 1H), 4.79-4.80 (bs, 4H), 4.51 (d, J = 5.6 Hz, 2H) | (ESI (+)) m/e 456 (M + H)⁺ |
| 115 | N-(4-{[(1R)-3-hydroxy-1-phenylpropyl]carbamoyl}phenyl)-1,3-dihydro-2H-isoindole-2-carboxamide | ¹H NMR (400 MHz, Pyridine-$d_5$, Temp = 90° C.) δ ppm 8.45-8.49 (m, 1H), 8.28-8.29 (bs, 1H), 8.08-8.12 (m, 1H), 7.87-7.90 (m, 2H), 7.55-7.59 (m, 2H), 7.26-7.33 (m, 2H), 7.19-7.23 (m, 3H), 7.16-7.18 (m, 2H), 5.79 (td, J = 7.9, 5.4 Hz, 1H), 4.82 (s, 4H), 3.88-3.99 (m, 2H), 2.19-2.43 (m, 2H) | (ESI (−)) m/e 414 (M − H)⁻ |
| 116 | N-{4-[(3-cyanophenyl)carbamoyl]phenyl}-1,3-dihydro-2H-isoindole-2-carboxamide | ¹H NMR (500 MHz, DMSO-$d_6$/Deuterium Oxide) δ ppm 8.23 (t, J = 1.8 Hz, 1H), 8.04 (ddd, J = 8.0, 2.3, 1.5 Hz, 1H), 7.91-7.94 (m, 2H), 7.71-7.78 (m, 2H), 7.59 (t, J = 7.9 Hz, 1H), 7.56 (dt, J = 7.6, 1.5 Hz, 1H), 7.38-7.41 (m, 2H), 7.33-7.36 (m, 2H), 4.75-4.87 (m, 4H) | (ESI (−)) m/e 381 (M − H)⁻ |

| Ex | Name | ¹H NMR | MS |
|---|---|---|---|
| 117 | N-{4-[(3-fluoro-4-methoxyphenyl)carbamoyl]phenyl}-1,3-dihydro-2H-isoindole-2-carboxamide | ¹H NMR (400 MHz, Pyridine-$d_5$, Temp = 90° C.) δ ppm 10.07-10.09 (bs, 1H), 8.33-8.34 (bs, 1H), 8.13-8.16 (m, 2H), 8.01 (dd, J = 13.5, 2.5 Hz, 1H), 7.91-7.93 (m, 2H), 7.57-7.60 (m, 1H), 7.20-7.23 (m, 2H), 7.15-7.19 (m, 2H), 6.98 (t, J = 9.1 Hz, 1H), 4.84 (s, 4H), 3.73 (s, 3H), | (ESI (−)) m/e 404 (M − H)⁻ |
| 118 | N-{4-[(2,3-dimethoxyphenyl)carbamoyl]phenyl}-1,3-dihydro-2H-isoindole-2-carboxamide | ¹H NMR (400 MHz, Pyridine-$d_5$, Temp = 90° C.) δ ppm 9.11-9.13 (bs, 1H), 8.40-8.44 (m, 1H), 8.37 (dd, J = 8.4, 1.3 Hz, 1H), 8.08-8.11 (m, 2H), 7.96-7.99 (m, 2H), 7.21-7.23 (m, 2H), 7.17-7.19 (m, 2H), 7.06 (t, J = 8.3 Hz, 1H), 6.74 (dd, J = 8.3, 1.3 Hz, 1H), 4.85 (s, 4H), 3.88 (s, 3H), 3.74 (s, 3H) | (ESI (+)) m/e 418 (M + H)⁺ |
| 119 | N-(4-{[2-(2-fluorophenyl)ethyl]carbamoyl}phenyl)-1,3-dihydro-2H-isoindole-2-carboxamide | ¹H NMR (500 MHz, DMSO-$d_6$/Deuterium Oxide) δ ppm 8.64-8.65 (bs, 1H), 8.48 (t, J = 5.7 Hz, 1H), 7.72-7.74 (m, 2H), 7.62-7.66 (m, 2H), 7.36-7.42 (m, 2H), 7.31-7.36 (m, 2H), 7.25-7.32 (m, 2H), 7.12-7.17 (m, 2H), 4.79-4.88 (m, 4H), 3.47-3.51 (m, 2H), 2.89 (t, J = 7.2 Hz, 2H) | (ESI (−)) m/e 402 (M − H)⁻ |
| 120 | N-[4-(isobutylcarbamoyl)phenyl]-1,3-dihydro-2H-isoindole-2-carboxamide | ¹H NMR (400 MHz, Pyridine-$d_5$, Temp = 90° C.) δ ppm 8.27-8.29 (bs, 1H), 8.09-8.12 (m, 2H), 7.90-7.93 (m, 2H), 7.84-7.90 (m, 1H), 7.19-7.23 (m, 2H), 7.14-7.19 (m, 2H), 4.84 (s, 4H), 3.39 (dd, J = 6.8, 6.0 Hz, 2H), 1.91-2.03 (m, 1H), 0.93 (d, J = 6.7 Hz, 6H) | (ESI (+)) m/e 338 (M + H)⁺ |
| 121 | N-(4-{[2-(1,3-benzodioxol-5-yl)ethyl]carbamoyl}phenyl)-1,3-dihydro-2H-isoindole-2-carboxamide | ¹H NMR (500 MHz, DMSO-$d_6$/Deuterium Oxide) δ ppm 8.64-8.66 (bs, 1H), 8.42 (t, J = 5.6 Hz, 1H), 7.73-7.75 (m, 2H), 7.63-7.67 (m, 2H), 7.36-7.41 (m, 2H), 7.31-7.36 (m, 2H), 6.81-6.84 (m, 2H), 6.71 (dd, J = 7.8, 1.7 Hz, 1H), 5.95 (s, 2H), 4.78-4.79 (bs, 4H), 3.41-3.46 (m, 2H), 2.73-2.78 (m, 2H) | (ESI (+)) m/e 430 (M + H)⁺ |
| 122 | N-(4-{[2-(2-methoxyphenyl)ethyl]carbamoyl}phenyl)-1,3-dihydro-2H-isoindole-2-carboxamide | ¹H NMR (400 MHz, Pyridine-$d_5$, Temp = 90° C.) δ ppm 8.25-8.27 (bs, 1H), 8.05-8.08 (m, 2H), 7.98-8.02 (bs, 1H), 7.89-7.92 (m, 2H), 7.19-7.25 (m, 3H), 7.14-7.19 (m, 3H), 6.83-6.90 (m, 2H), 4.84 (s, 4H), 3.83-3.88 (m, 2H), 3.66 (s, 3H), 3.09 (t, J = 7.1 Hz, 2H) | (ESI (+)) m/e 416 (M + H)⁺ |
| 123 | N-[4-(butylcarbamoyl)phenyl]-1,3-dihydro-2H-isoindole-2-carboxamide | ¹H NMR (400 MHz, Pyridine-$d_5$, Temp = 90° C.) δ ppm 8.27-8.28 (bs, 1H), 8.09-8.12 (m, 2H), 7.89-7.93 (m, 2H), 7.86-7.92 (m, 1H), 7.19-7.23 (m, 2H), 7.15-7.18 (m, 2H), 4.84 (s, 4H), 3.48-3.61 (m, 2H), 1.62 (p, J = 7.2 Hz, 2H), 1.26-1.44 (m, 2H), 0.85 (t, J = 7.3 Hz, 3H) | (ESI (+)) m/e 338 (M + H)⁺ |
| 124 | N-{4-[(2-isopropoxyethyl)carbamoyl]phenyl}-1,3-dihydro-2H-isoindole-2-carboxamide | ¹H NMR (400 MHz, DMSO-$d_6$/Deuterium Oxide, Temp = 90° C.) δ ppm 7.75-7.78 (m, 2H), 7.63-7.66 (m, 2H), 7.26-7.40 (m, 4H), 4.82 (s, 4H), 3.58-3.68 (m, 1H), 3.52-3.56 (m, 2H), 3.42 (t, J = 6.2 Hz, 2H), 1.12 (d, J = 6.1 Hz, 6H) | (ESI (−)) m/e 366 (M − H)⁻ |
| 125 | N-{4-[(3-isopropoxypropyl)carbamoyl]phenyl}-1,3-dihydro-2H-isoindole-2-carboxamide | ¹H NMR (400 MHz, Pyridine-$d_5$, Temp = 90° C.) δ ppm 8.28-8.30 (bs, 1H), 8.07-8.10 (m, 2H), 7.93-7.97 (m, 1H), 7.90-7.94 (m, 2H), 7.19-7.23 (m, 2H), 7.14-7.19 (m, 2H), 4.85 (s, 4H), 3.62-3.74 (m, 2H), 3.42-3.55 (m, 3H), 1.92 (p, J = 6.4 Hz, 2H), 1.08 (d, J = 6.1 Hz, 6H) | (ESI (+)) m/e 382 (M + H)⁺ |
| 126 | 4-chloro-N-{4-[(3-phenylpropyl)carbamoyl]phenyl}-1,3-dihydro-2H-isoindole-2-carboxamide | ¹H NMR (300 MHz, DMSO-$d_6$) δ ppm 8.66 (s, 1H), 8.29 (t, J = 5.6 Hz, 1H), 7.75-7.79 (m, 2H), 7.64-7.68 (m, 2H), 7.33-7.41 (m, 3H), 7.13-7.32 (m, 5H), 4.77-4.89 (m, 4H), 3.19-3.31 (m, 2H), 2.58-2.68 (m, 2H), 1.76-1.89 (m, 2H) | (ESI (+)) m/e 434 (M + H)⁺ |
| 127 | N-(4-{[2-(4-methoxyphenyl)ethyl]carbamoyl}phenyl)-1,3-dihydro-2H-isoindole-2-carboxamide | ¹H NMR (400 MHz, DMSO-$d_6$/Deuterium Oxide) δ ppm 8.64-8.66 (bs, 1H), 8.43 (t, J = 5.6 Hz, 1H), 7.73-7.76 (m, 2H), 7.63-7.65 (m, 2H), 7.36-7.41 (m, 2H), 7.31-7.35 (m, 2H), 7.16-7.19 (m, 2H), 6.86-6.88 (m, 2H), 4.78-4.80 (bs, 4H), 3.72 (s, 3H), 3.42-3.51 (m, 2H), 2.78 (t, J = 7.4 Hz, 2H) | (ESI (+)) m/e 416 (M + H)⁺ |

| Ex | Name | ¹H NMR | MS |
|---|---|---|---|
| 128 | N-{4-[(3-methoxypropyl)carbamoyl]phenyl}-1,3-dihydro-2H-isoindole-2-carboxamide | ¹H NMR (500 MHz, DMSO-$d_6$/Deuterium Oxide) δ ppm 7.75-7.78 (m, 2H), 7.60-7.69 (m, 2H), 7.37-7.40 (m, 2H), 7.32-7.35 (m, 2H), 4.79-4.80 (bs, 4H), 3.39 (t, J = 6.3 Hz, 2H), 3.30 (t, J = 7.0 Hz, 2H), 3.25 (s, 3H), 1.76 (p, J = 6.7 Hz, 2H) | (ESI (+)) m/e 354 (M + H)⁺ |
| 129 | N-(4-{[2-(4-fluorophenyl)ethyl]carbamoyl}phenyl)-1,3-dihydro-2H-isoindole-2-carboxamide | ¹H NMR (500 MHz, DMSO-$d_6$/Deuterium Oxide) δ ppm 8.64-8.66 (bs, 1H), 8.45 (t, J = 5.6 Hz, 1H), 7.73-7.75 (m, 2H), 7.63-7.66 (m, 2H), 7.36-7.41 (m, 2H), 7.31-7.35 (m, 2H), 7.27-7.31 (m, 2H), 7.09-7.13 (m, 2H), 4.78-4.80 (bs, 4H), 3.47 (t, J = 7.3 Hz, 2H), 2.84 (t, J = 7.3 Hz, 2H) | (ESI (+)) m/e 404 (M + H)⁺ |
| 130 | N-(4-{[3-(2-oxopyrrolidin-1-yl)propyl]carbamoyl}phenyl)-1,3-dihydro-2H-isoindole-2-carboxamide | ¹H NMR (300 MHz, DMSO-$d_6$) δ ppm 8.58 (s, 1H), 8.27 (t, J = 5.7 Hz, 1H), 7.74-7.78 (m, 2H), 7.64-7.69 (m, 2H), 7.30-7.39 (m, 4H), 4.78-4.79 (bs, 4H), 3.32-3.39 (m, 2H), 3.17-3.26 (m, 4H), 2.22 (t, J = 8.0 Hz, 2H), 1.87-1.97 (m, 2H), 1.69 (p, J = 7.0 Hz, 2H) | (ESI (+)) m/e 407 (M + H)⁺ |
| 131 | N-{4-[(2,4-dimethoxyphenyl)carbamoyl]phenyl}-1,3-dihydro-2H-isoindole-2-carboxamide | ¹H NMR (400 MHz, Pyridine-$d_5$, Temp = 90° C.) δ ppm 8.89-8.91 (bs, 1H), 8.53 (d, J = 8.7 Hz, 1H), 8.36-8.37 (bs, 1H), 8.10-8.13 (m, 2H), 7.95-7.98 (m, 2H), 7.19-7.24 (m, 2H), 7.15-7.19 (m, 2H), 6.67 (d, J = 2.6 Hz, 1H), 6.61 (dd, J = 8.7, 2.7 Hz, 1H), 4.85 (s, 4H), 3.72 (s, 3H), 3.69 (s, 3H) | (ESI (+)) m/e 418 (M + H)⁺ |
| 133 | N-{4-[(2-phenoxyethyl)carbamoyl]phenyl}-1,3-dihydro-2H-isoindole-2-carboxamide | ¹H NMR (300 MHz, DMSO-$d_6$) δ ppm 8.59 (s, 1H), 8.52 (t, J = 5.5 Hz, 1H), 7.77-7.81 (m, 2H), 7.65-7.69 (m, 2H), 7.26-7.39 (m, 6H), 6.90-6.99 (m, 3H), 4.79 (s, 4H), 4.10 (t, J = 5.9 Hz, 2H), 3.62 (q, J = 5.7 Hz, 2H) | (ESI (+)) m/e 402 (M + H)⁺ |
| 134 | N-(4-{[2-(4-hydroxyphenyl)ethyl]carbamoyl}phenyl)-1,3-dihydro-2H-isoindole-2-carboxamide | ¹H NMR (500 MHz, DMSO-$d_6$/Deuterium Oxide) δ ppm 7.73-7.76 (m, 2H), 7.63-7.66 (m, 2H), 7.36-7.41 (m, 2H), 7.31-7.36 (m, 2H), 7.04-7.07 (m, 2H), 6.69-6.71 (m, 2H), 4.79-4.80 (bs, 4H), 3.41 (dd, J = 8.5, 6.5 Hz, 2H), 2.73 (t, J = 7.5 Hz, 2H) | (ESI (+)) m/e 402 (M + H)⁺ |
| 135 | N-(4-{[2-(3-fluorophenyl)ethyl]carbamoyl}phenyl)-1,3-dihydro-2H-isoindole-2-carboxamide | ¹H NMR (500 MHz, DMSO-$d_6$/Deuterium Oxide) δ ppm 8.64-8.66 (bs, 1H), 8.46 (t, J = 5.6 Hz, 1H), 7.72-7.75 (m, 2H), 7.63-7.66 (m, 2H), 7.36-7.41 (m, 2H), 7.31-7.35 (m, 3H), 7.08-7.11 (m, 2H), 7.00-7.05 (m, 1H), 4.78-4.79 (bs, 4H), 3.50 (t, J = 6.9 Hz, 2H), 2.88 (t, J = 7.2 Hz, 2H) | (ESI (+)) m/e 404 (M + H)⁺ |
| 136 | N-[4-({1-[(3S)-tetrahydrofuran-3-yl]-1H-pyrazol-4-yl}carbamoyl)phenyl]-1,3-dihydro-2H-isoindole-2-carboxamide | ¹H NMR (300 MHz, DMSO-$d_6$) δ ppm 10.25 (s, 1H), 8.64 (s, 1H), 8.08 (s, 1H), 7.85-7.89 (m, 2H), 7.70-7.75 (m, 2H), 7.61 (s, 1H), 7.29-7.41 (m, 4H), 4.94-5.06 (m, 1H), 4.80-4.81 (bs, 4H), 3.93-4.01 (m, 2H), 3.78-3.89 (m, 2H), 2.30-2.46 (m, 1H), 2.14-2.30 (m, 1H) | (ESI (+)) m/e 418 (M + H)⁺ |
| 137 | 5-methyl-N-{4-[(3-phenylpropyl)carbamoyl]phenyl}-1,3-dihydro-2H-isoindole-2-carboxamide | ¹H NMR (300 MHz, DMSO-$d_6$) δ ppm 8.55 (s, 1H), 8.29 (t, J = 5.6 Hz, 1H), 7.74-7.79 (m, 2H), 7.63-7.68 (m, 2H), 7.11-7.34 (m, 8H), 4.73-4.74 (bs, 4H), 3.20-3.30 (m, 2H), 2.63 (t, J = 7.6 Hz, 2H), 2.33 (s, 3H), 1.82 (p, J = 7.4 Hz, 2H) | (ESI (+)) m/e 414 (M + H)⁺ |
| 138 | N-[4-(1,4-dioxa-8-azaspiro[4.5]dec-8-ylcarbonyl)phenyl]-1,3-dihydro-2H-isoindole-2-carboxamide | ¹H NMR (400 MHz, Pyridine-$d_5$, Temp = 90° C.) δ ppm 8.27-8.28 (bs, 1H), 7.89-7.92 (m, 2H), 7.52-7.55 (m, 2H), 7.19-7.23 (m, 2H), 7.16-7.18 (m, 2H), 4.85 (s, 4H), 3.84 (s, 4H), 3.73-3.76 (m, 4H), 1.71-1.75 (m, 4H) | (ESI (+)) m/e 408 (M + H)⁺ |
| 139 | N-{4-[(2-phenylethyl)carbamoyl]phenyl}-1,3-dihydro-2H-isoindole-2-carboxamide | ¹H NMR (300 MHz, DMSO-$d_6$) δ ppm 8.57 (s, 1H), 8.38 (t, J = 5.6 Hz, 1H), 7.73-7.77 (m, 2H), 7.64-7.67 (m, 2H), 7.20-7.39 (m, 9H), 4.79 (s, 4H), 3.43-3.50 (m, 2H), 2.80-2.88 (m, 2H) | (ESI (+)) m/e 386 (M + H)⁺ |

| Ex | Name | ¹H NMR | MS |
|---|---|---|---|
| 140 | N-(4-{[2-(2,4-dimethoxyphenyl)ethyl]carbamoyl}phenyl)-1,3-dihydro-2H-isoindole-2-carboxamide | ¹H NMR (400 MHz, Pyridine-$d_5$, Temp = 90° C.) δ ppm 8.25-8.26 (bs, 1H), 8.07-8.09 (m, 2H), 7.95-8.02 (m, 1H), 7.88-7.93 (m, 2H), 7.19-7.24 (m, 2H), 7.13-7.19 (m, 2H), 6.57 (d, J = 2.4 Hz, 1H), 6.49 (dd, J = 8.1, 2.4 Hz, 1H), 4.84 (s, 4H), 3.81-3.85 (m, 2H), 3.68 (s, 3H), 3.66 (s, 3H), 3.04 (t, J = 7.0 Hz, 2H) | (ESI (+)) m/e 446 (M + H)⁺ |
| 141 | N-(4-{[3-(methylthio)propyl]carbamoyl}phenyl)-1,3-dihydro-2H-isoindole-2-carboxamide | ¹H NMR (400 MHz, DMSO-$d_6$/Deuterium Oxide, Temp = 90° C.) δ ppm 7.76-7.78 (m, 2H), 7.63-7.65 (m, 2H), 7.32-7.40 (m, 4H), 4.82 (s, 4H), 3.37 (t, J = 6.9 Hz, 2H), 2.53-2.57 (m, 2H), 2.09 (s, 3H), 1.85 (p, J = 7.1 Hz, 2H) | (ESI (+)) m/e 370 (M + H)⁺ |
| 142 | N-{4-[(2-ethoxyethyl)carbamoyl]phenyl}-1,3-dihydro-2H-isoindole-2-carboxamide | ¹H NMR (400 MHz, Pyridine-$d_5$, Temp = 90° C.) δ ppm 8.28-8.34 (m, 1H), 8.07-8.12 (m, 2H), 8.01-8.08 (m, 1H), 7.89-7.92 (m, 2H), 7.19-7.24 (m, 2H), 7.14-7.18 (m, 2H), 4.84 (s, 4H), 3.76 (q, J = 5.7 Hz, 2H), 3.63 (t, J = 5.7 Hz, 2H), 3.43 (q, J = 6.9 Hz, 2H), 1.09 (t, J = 6.9 Hz, 3H) | (ESI (+)) m/e 354 (M + H)⁺ |
| 143 | N-{4-[(2-fluorophenyl)carbamoyl]phenyl}-1,3-dihydro-2H-isoindole-2-carboxamide | ¹H NMR (500 MHz, DMSO-$d_6$/Deuterium Oxide) δ ppm 7.91-7.93 (m, 2H), 7.72-7.75 (m, 2H), 7.56-7.65 (m, 1H), 7.37-7.42 (m, 2H), 7.32-7.37 (m, 2H), 7.26-7.31 (m, 2H), 7.21-7.26 (m, 1H), 4.78-4.82 (m, 4H) | (ESI (−)) m/e 374 (M − H)⁻ |
| 144 | N-(4-{[2-(pyridin-3-yl)ethyl]carbamoyl}phenyl)-1,3-dihydro-2H-isoindole-2-carboxamide | ¹H NMR (300 MHz, DMSO-$d_6$) δ ppm 8.57 (s, 1H), 8.45 (d, J = 2.2 Hz, 1H), 8.41 (dd, J = 4.7, 1.6 Hz, 1H), 8.38 (d, J = 5.5 Hz, 1H), 7.71-7.75 (m, 2H), 7.63-7.68 (m, 3H), 7.29-7.39 (m, 5H), 4.79 (s, 4H), 3.46-3.53 (m, 2H), 2.87 (t, J = 7.1 Hz, 2H) | (ESI (+)) m/e 387 (M + H)⁺ |
| 145 | N-[4-({4-[(trifluoromethyl)thio]benzyl}carbamoyl)phenyl]-1,3-dihydro-2H-isoindole-2-carboxamide | ¹H NMR (500 MHz, DMSO-$d_6$/Deuterium Oxide) δ ppm 9.03 (t, J = 6.0 Hz, 1H), 8.67-8.70 (bs, 1H), 7.82-7.84 (m, 2H), 7.66-7.70 (m, 4H), 7.47-7.49 (m, 2H), 7.36-7.41 (m, 2H), 7.31-7.36 (m, 2H), 4.79-4.80 (bs, 4H), 4.53 (d, J = 5.3 Hz, 2H) | (ESI (+)) m/e 472 (M + H)⁺ |
| 146 | N-{4-[(3,4-dimethoxyphenyl)carbamoyl]phenyl}-1,3-dihydro-2H-isoindole-2-carboxamide | ¹H NMR (400 MHz, Pyridine-$d_5$, Temp = 90° C.) δ ppm 9.90-9.92 (bs, 1H), 8.32-8.33 (bs, 1H), 8.17-8.19 (m, 2H), 7.92-7.94 (m, 2H), 7.77 (d, J = 2.4 Hz, 1H), 7.49-7.53 (m, 1H), 7.20-7.23 (m, 2H), 7.14-7.19 (m, 2H), 6.94 (d, J = 8.6 Hz, 1H), 4.84 (s, 4H), 3.74 (s, 6H) | (ESI (+)) m/e 418 (M + H)⁺ |
| 147 | N-(4-{[3-(2-fluorophenyl)pyrrolidin-1-yl]carbonyl}phenyl)-1,3-dihydro-2H-isoindole-2-carboxamide | ¹H NMR (500 MHz, DMSO-$d_6$/Deuterium Oxide) δ ppm 7.60-7.67 (m, 2H), 7.47-7.55 (m, 2H), 7.26-7.45 (m, 6H), 7.12-7.25 (m, 2H), 4.77-4.82 (m, 4H), 3.83-3.97 (m, 1H), 3.47-3.64 (m, 4H), 2.19-2.36 (m, 1H), 1.98-2.18 (m, 1H) | (ESI (+)) m/e 430 (M + H)⁺ |
| 148 | N-(4-{[3-(1H-imidazol-1-yl)propyl]carbamoyl}phenyl)-1,3-dihydro-2H-isoindole-2-carboxamide | ¹H NMR (400 MHz, Pyridine-$d_5$, Temp = 90° C.) δ ppm 8.36-8.38 (bs, 1H), 8.24-8.31 (m, 1H), 8.08-8.12 (m, 2H), 8.00-8.05 (bs, 1H), 7.91-7.97 (m, 2H), 7.25-7.31 (bs, 1H), 7.19-7.24 (m, 2H), 7.16-7.19 (m, 2H), 4.86 (s, 4H), 4.06 (t, J = 7.0 Hz, 2H), 3.55 (q, J = 6.4 Hz, 2H), 2.11 (p, J = 6.9 Hz, 2H) | (ESI (+)) m/e 390 (M + H)⁺ |
| 149 | N-(4-{[2-(3-chlorophenyl)ethyl]carbamoyl}phenyl)-1,3-dihydro-2H-isoindole-2-carboxamide | ¹H NMR (500 MHz, DMSO-$d_6$/Deuterium Oxide) δ ppm 8.64-8.66 (bs, 1H), 8.45 (t, J = 5.6 Hz, 1H), 7.72-7.75 (m, 2H), 7.63-7.66 (m, 2H), 7.36-7.41 (m, 2H), 7.31-7.36 (m, 4H), 7.25-7.29 (m, 1H), 7.21-7.24 (m, 1H), 4.76-4.81 (bs, 4H), 3.47-3.51 (m, 2H), 2.86 (t, J = 7.2 Hz, 2H) | (APCI (+)) m/e 420 (M + H)⁺ |
| 150 | N-{4-[(4-hydroxybutyl)carbamoyl]phenyl}-1,3-dihydro-2H-isoindole-2-carboxamide | ¹H NMR (400 MHz, DMSO-$d_6$/Deuterium Oxide, Temp = 90° C.) δ ppm 7.75-7.78 (m, 2H), 7.62-7.65 (m, 2H), 7.32-7.40 (m, 4H), 4.81 (s, 4H), 3.48 (t, J = 6.3 Hz, 2H), 3.28-3.32 (m, 2H), 1.49-1.65 (m, 4H) | (ESI (+)) m/e 354 (M + H)⁺ |

| Ex | Name | ¹H NMR | MS |
|---|---|---|---|
| 151 | N-{4-[(3-phenylpropyl)carbamoyl]phenyl}-5-(trifluoromethyl)-1,3-dihydro-2H-isoindole-2-carboxamide | ¹H NMR (300 MHz, DMSO-d₆) δ ppm 8.65 (s, 1H), 8.30 (t, J = 5.6 Hz, 1H), 7.74-7.81 (m, 3H), 7.57-7.73 (m, 4H), 7.15-7.32 (m, 5H), 4.85-4.87 (bs, 4H), 3.27 (q, J = 6.6 Hz, 2H), 2.63 (t, J = 7.6 Hz, 2H), 1.83 (p, J = 7.4 Hz, 2H) | (ESI (+)) m/e 468 (M + H)⁺ |
| 152 | N-(4-{[4-(hydroxymethyl)phenyl]carbamoyl}phenyl)-1,3-dihydro-2H-isoindole-2-carboxamide | ¹H NMR (500 MHz, DMSO-d₆/Deuterium Oxide) δ ppm 7.90-7.92 (m, 2H), 7.68-7.74 (m, 4H), 7.38-7.41 (m, 2H), 7.33-7.36 (m, 2H), 7.29-7.32 (m, 2H), 4.78-4.84 (m, 4H), 4.47 (s, 2H) | (APCI (+)) m/e 388 (M + H)⁺ |
| 153 | N-[4-(1,3-benzodioxol-5-ylcarbamoyl)phenyl]-1,3-dihydro-2H-isoindole-2-carboxamide | ¹H NMR (400 MHz, Pyridine-d₅, Temp = 90° C.) δ ppm 9.95-9.97 (bs, 1H), 8.28-8.36 (m, 1H), 8.13-8.15 (m, 2H), 7.90-7.93 (m, 2H), 7.76 (d, J = 2.1 Hz, 1H), 7.32 (dd, J = 8.3, 2.1 Hz, 1H), 7.19-7.23 (m, 2H), 7.15-7.19 (m, 2H), 6.82 (d, J = 8.3 Hz, 1H), 5.86 (s, 2H), 4.84 (s, 4H) | (APCI (+)) m/e 402 (M + H)⁺ |
| 154 | N-{4-[(1-isopropyl-1H-pyrazol-4-yl)carbamoyl]phenyl}-1,3-dihydro-2H-isoindole-2-carboxamide | ¹H NMR (300 MHz, DMSO-d₆) δ ppm 10.21 (s, 1H), 8.64 (s, 1H), 8.03 (d, J = 0.7 Hz, 1H), 7.85-7.89 (m, 2H), 7.70-7.74 (m, 2H), 7.57 (d, J = 0.7 Hz, 1H), 7.30-7.40 (m, 4H), 4.80-4.81 (bs, 4H), 4.41-4.55 (m, 1H), 1.41 (d, J = 6.7 Hz, 6H) | (ESI (+)) m/e 390 (M + H)⁺ |
| 155 | N-{4-[(4-hydroxyphenyl)carbamoyl]phenyl}-1,3-dihydro-2H-isoindole-2-carboxamide | ¹H NMR (400 MHz, Pyridine-d₅, Temp = 90° C.) δ ppm 9.83-9.85 (bs, 1H), 8.29-8.33 (bs, 1H), 8.16-8.18 (m, 2H), 7.91-7.93 (m, 2H), 7.86-7.89 (m, 2H), 7.19-7.23 (m, 2H), 7.17-7.19 (m, 3H), 7.10-7.12 (m, 2H), 4.84 (s, 4H) | (ESI (+)) m/e 374 (M + H)⁺ |
| 156 | N-{4-[(1-ethyl-1H-pyrazol-4-yl)carbamoyl]phenyl}-1,3-dihydro-2H-isoindole-2-carboxamide | ¹H NMR (300 MHz, DMSO-d₆) δ ppm 10.22 (s, 1H), 8.64 (s, 1H), 8.03 (s, 1H), 7.85-7.90 (m, 2H), 7.70-7.74 (m, 2H), 7.57 (s, 1H), 7.30-7.40 (m, 4H), 4.80-4.81 (bs, 4H), 4.11 (q, J = 7.2 Hz, 2H), 1.36 (t, J = 7.2 Hz, 3H) | (ESI (+)) m/e 376 (M + H)⁺ |
| 157 | N-{4-[(2,5-dimethoxyphenyl)carbamoyl]phenyl}-1,3-dihydro-2H-isoindole-2-carboxamide | ¹H NMR (400 MHz, Pyridine-d₅, Temp = 90° C.) δ ppm 8.97-8.99 (bs, 1H), 8.56 (d, J = 3.0 Hz, 1H), 8.40-8.42 (bs, 1H), 8.07-8.10 (m, 2H), 7.96-7.98 (m, 2H), 7.21-7.24 (m, 2H), 7.16-7.19 (m, 2H), 6.88 (d, J = 8.8 Hz, 1H), 6.69 (dd, J = 8.8, 3.0 Hz, 1H), 4.85 (s, 4H), 3.72 (s, 3H), 3.71 (s, 3H) | (ESI (+)) m/e 418 (M + H)⁺ |
| 158 | N-{4-[methyl(3-phenylpropyl)carbamoyl]phenyl}-1,3-dihydro-2H-isoindole-2-carboxamide | ¹H NMR (300 MHz, DMSO-d₆) δ ppm 8.51 (s, 1H), 7.60-7.64 (m, 2H), 7.11-7.44 (m, 11H), 4.78-4.79 (bs, 4H), 3.26-3.52 (m, 2H), 2.94 (s, 3H), 2.34-2.70 (m, 2H), 1.82-1.91 (m, 2H) | (ESI (+)) m/e 414 (M + H)⁺ |
| 159 | N-{4-[(2-hydroxy-2-methylpropyl)carbamoyl]phenyl}-1,3-dihydro-2H-isoindole-2-carboxamide | ¹H NMR (400 MHz, Pyridine-d₅, Temp = 90° C.) δ ppm 8.30-8.32 (bs, 1H), 8.06-8.09 (m, 2H), 7.89-7.95 (m, 1H), 7.89-7.92 (m, 2H), 7.19-7.23 (m, 2H), 7.15-7.19 (m, 2H), 4.84 (s, 4H), 3.70 (d, J = 5.9 Hz, 2H), 1.38 (s, 6H) | (ESI (−)) m/e 352 (M − H)⁻ |
| 160 | N-(4-{[4-(trifluoromethyl)piperidin-1-yl]carbonyl}phenyl)-1,3-dihydro-2H-isoindole-2-carboxamide | ¹H NMR (400 MHz, Pyridine-d₅, Temp = 90° C.) δ ppm 8.31-8.33 (bs, 1H), 7.91-7.94 (m, 2H), 7.50-7.55 (m, 2H), 7.19-7.24 (m, 2H), 7.15-7.19 (m, 2H), 4.86 (s, 4H), 4.34-4.39 (m, 2H), 2.83 (td, J = 12.9, 2.8 Hz, 2H), 2.24-2.43 (m, 1H), 1.73-1.77 (m, 2H), 1.50 (qd, J = 12.5, 4.4 Hz, 2H) | (ESI (−)) m/e 416 (M − H)⁻ |
| 161 | N-[4-(thiomorpholin-4-ylcarbonyl)phenyl]-1,3-dihydro-2H-isoindole-2-carboxamide | ¹H NMR (400 MHz, Pyridine-d₅, Temp = 90° C.) δ ppm 8.29-8.31 (bs, 1H), 7.90-7.92 (m, 2H), 7.47-7.50 (m, 2H), 7.20-7.23 (m, 2H), 7.15-7.19 (m, 2H), 4.85 (s, 4H), 3.81-3.84 (m, 4H), 2.54-2.58 (m, 4H) | (ESI (+)) m/e 368 (M + H)⁺ |
| 162 | N-[4-(5,6-dihydroimidazo[1,5-a]pyrazin-7(8H)-ylcarbonyl)phenyl]-1,3-dihydro-2H-isoindole-2-carboxamide | ¹H NMR (300 MHz, DMSO-d₆) δ ppm 8.59 (s, 1H), 7.67-7.71 (m, 2H), 7.60-7.62 (bs, 1H), 7.30-7.43 (m, 6H), 6.72-6.77 (bs, 1H), 4.79-4.80 (bs, 4H), 4.73-4.75 (bs, 2H), 4.06-4.18 (m, 2H), 3.81-3.88 (m, 2H) | (ESI (+)) m/e 388 (M + H)⁺ |

| Ex | Name | ¹H NMR | MS |
|---|---|---|---|
| 163 | N-(4-{[4-(2-furoyl)piperazin-1-yl]carbonyl}phenyl)-1,3-dihydro-2H-isoindole-2-carboxamide | ¹H NMR (400 MHz, Pyridine-d₅, Temp = 90° C.) δ ppm 8.31-8.34 (m, 1H), 7.92-7.95 (m, 2H), 7.57-7.59 (m, 1H), 7.53-7.57 (m, 2H), 7.20-7.24 (m, 2H), 7.16-7.19 (m, 2H), 7.08-7.09 (m, 1H), 6.45 (dd, J = 3.4, 1.7 Hz, 1H), 4.86 (s, 4H), 3.75-3.80 (m, 4H), 3.64-3.70 (m, 4H) | (ESI (−)) m/e 443 (M − H)⁻ |
| 164 | N-{4-[(1-benzylpiperidin-4-yl)carbamoyl]phenyl}-1,3-dihydro-2H-isoindole-2-carboxamide | ¹H NMR (400 MHz, DMSO-d₆/Deuterium Oxide, Temp = 90° C.) δ ppm 7.77-7.80 (m, 2H), 7.65-7.67 (m, 2H), 7.49-7.56 (m, 5H), 7.37-7.43 (m, 2H), 7.32-7.36 (m, 2H), 4.82 (s, 4H), 4.31-4.32 (bs, 2H), 4.03-4.10 (m, 1H), 3.39-3.44 (m, 2H), 3.12-3.19 (m, 2H), 2.08-2.14 (m, 2H), 1.88-1.99 (m, 2H) | (ESI (+)) m/e 455 (M + H)⁺ |
| 165 | N-{4-[(4-methoxyphenyl)carbamoyl]phenyl}-1,3-dihydro-2H-isoindole-2-carboxamide | ¹H NMR (400 MHz, Pyridine-d₅, Temp = 90° C.) δ ppm 9.91-9.93 (bs, 1H), 8.33-8.34 (bs, 1H), 8.16-8.18 (m, 2H), 7.86-7.98 (m, 4H), 7.20-7.23 (m, 2H), 7.15-7.19 (m, 2H), 6.95-6.98 (m, 2H), 4.85 (s, 4H), 3.67 (s, 3H) | (ESI (+)) m/e 388 (M + H)⁺ |
| 166 | N-{4-[(3-methoxyphenyl)carbamoyl]phenyl}-1,3-dihydro-2H-isoindole-2-carboxamide | ¹H NMR (400 MHz, Pyridine-d₅, Temp = 90° C.) δ ppm 9.99-10.01 (m, 1H), 8.34-8.35 (bs, 1H), 8.10-8.20 (m, 2H), 7.91-7.94 (m, 2H), 7.82 (t, J = 2.2 Hz, 1H), 7.57-7.60 (m, 1H), 7.21-7.24 (m, 2H), 7.14-7.19 (m, 2H), 6.75 (dd, J = 8.2, 2.5 Hz, 1H), 4.84 (s, 4H), 3.68 (s, 3H) | (ESI (+)) m/e 388 (M + H)⁺ |
| 167 | N-{4-[(5-acetamido-2-methoxyphenyl)carbamoyl]phenyl}-1,3-dihydro-2H-isoindole-2-carboxamide | ¹H NMR (400 MHz, Pyridine-d₅, Temp = 90° C.) δ ppm 9.89-9.92 (bs, 1H), 8.93-8.97 (m, 2H), 8.38-8.39 (bs, 1H), 8.04-8.07 (m, 2H), 7.93-7.96 (m, 2H), 7.87-7.93 (m, 1H), 7.20-7.25 (m, 2H), 7.15-7.19 (m, 2H), 6.91 (d, J = 8.8 Hz, 1H), 4.85 (s, 4H), 3.71 (d, J = 1.1 Hz, 3H), 2.14 (d, J = 0.9 Hz, 3H) | (ESI (+)) m/e 445 (M + H)⁺ |
| 168 | N-(4-{[2-(3,5-dimethoxyphenyl)ethyl]carbamoyl}phenyl)-1,3-dihydro-2H-isoindole-2-carboxamide | ¹H NMR (400 MHz, Pyridine-d₅, Temp = 90° C.) δ ppm 8.25-8.28 (bs, 1H), 8.08-8.13 (m, 1H), 8.07-8.11 (m, 2H), 7.87-7.92 (m, 2H), 7.19-7.24 (m, 2H), 7.14-7.19 (m, 2H), 6.56-6.59 (m, 2H), 6.47-6.50 (m, 1H), 4.84 (s, 4H), 3.82-3.88 (m, 2H), 3.65 (s, 6H), 3.00 (t, J = 7.2 Hz, 2H) | (ESI (−)) m/e 444 (M − H)⁻ |
| 169 | N-[4-({2-[3-(trifluoromethyl)phenyl]ethyl}carbamoyl)phenyl]-1,3-dihydro-2H-isoindole-2-carboxamide | ¹H NMR (500 MHz, DMSO-d₆/Deuterium Oxide) δ ppm 8.63-8.66 (bs, 1H), 8.45 (t, J = 5.6 Hz, 1H), 7.70-7.73 (m, 2H), 7.62-7.65 (m, 2H), 7.53-7.61 (m, 4H), 7.37-7.40 (m, 2H), 7.32-7.35 (m, 2H), 4.78-4.79 (bs, 4H), 3.50-3.56 (m, 2H), 2.96 (t, J = 7.1 Hz, 2H) | (ESI (+)) m/e 454 (M + H)⁺ |
| 170 | N-{4-[(2-methylbutan-2-yl)carbamoyl]phenyl}-1,3-dihydro-2H-isoindole-2-carboxamide | ¹H NMR (400 MHz, Pyridine-d₅, Temp = 90° C.) δ ppm 8.26-8.28 (bs, 1H), 7.96-7.99 (m, 2H), 7.86-7.88 (m, 2H), 7.18-7.24 (m, 2H), 7.14-7.19 (m, 2H), 6.76-6.79 (bs, 1H), 4.83 (s, 4H), 1.94 (q, J = 7.5 Hz, 2H), 1.47 (s, 6H), 0.90 (t, J = 7.4 Hz, 3H) | (ESI (+)) m/e 352 (M + H)⁺ |
| 171 | N-(4-{[2-(1H-imidazol-4-yl)ethyl]carbamoyl}phenyl)-1,3-dihydro-2H-isoindole-2-carboxamide | ¹H NMR (400 MHz, Pyridine-d₅, Temp = 90° C.) δ ppm 8.48-8.52 (bs, 1H), 8.32-8.34 (bs, 1H), 8.27 (s, 1H), 8.09-8.12 (m, 2H), 7.90-7.93 (m, 2H), 7.19-7.23 (m, 2H), 7.16-7.19 (m, 2H), 4.84 (s, 4H), 3.90-3.96 (m, 2H), 3.13 (t, J = 6.7 Hz, 2H) | (ESI (+)) m/e 376 (M + H)⁺ |
| 172 | N-(4-{[(2S)-2-hydroxypropyl]carbamoyl}phenyl)-1,3-dihydro-2H-isoindole-2-carboxamide | ¹H NMR (400 MHz, Pyridine-d₅, Temp = 90° C.) δ ppm 8.28-8.30 (bs, 1H), 8.06-8.10 (m, 2H), 8.03-8.09 (m, 1H), 7.88-7.91 (m, 2H), 7.19-7.23 (m, 2H), 7.15-7.19 (m, 2H), 4.84 (s, 4H), 4.25 (dddd, J = 12.4, 7.0, 6.3, 4.2 Hz, 1H), 3.78 (ddd, J = 13.4, 6.1, 4.3 Hz, 1H), 3.61 (ddd, J = 13.4, 6.9, 5.4 Hz, 1H), 1.31 (d, J = 6.2 Hz, 3H) | (ESI (−)) m/e 338 (M − H)⁻ |
| 173 | N-(4-{[(1R)-1-(3-cyanophenyl)ethyl]carbamoyl}phenyl)-1,3-dihydro-2H-isoindole-2-carboxamide | ¹H NMR (400 MHz, Pyridine-d₅, Temp = 90° C.) δ ppm 8.32-8.37 (m, 1H), 8.28-8.32 (bs, 1H), 8.09-8.12 (m, 2H), 7.88-7.90 (m, 2H), 7.83 (s, 1H), 7.69-7.72 (m, 1H), 7.43-7.47 (m, 1H), 7.30 (t, J = 7.8 Hz, 1H), 7.19-7.24 (m, 2H), 7.14-7.18 (m, 2H), 5.55 (p, J = 7.1 Hz, 1H), 4.83 (s, 4H), 1.56 (d, J = 7.0 Hz, 3H) | (ESI (+)) m/e 411 (M + H)⁺ |

| Ex | Name | ¹H NMR | MS |
|---|---|---|---|
| 174 | N-(4-{[(2S)-1-hydroxy-3-methylbutan-2-yl]carbamoyl}phenyl)-1,3-dihydro-2H-isoindole-2-carboxamide | ¹H NMR (400 MHz, Pyridine-$d_5$, Temp = 90° C.) δ ppm 8.29-8.31 (bs, 1H), 8.05-8.08 (m, 2H), 7.87-7.90 (m, 2H), 7.46-7.53 (bs, 1H), 7.19-7.24 (m, 2H), 7.14-7.18 (m, 2H), 4.84 (s, 4H), 4.29-4.36 (m, 1H), 3.99 (d, J = 4.8 Hz, 2H), 2.17-2.28 (m, 1H), 1.00-1.10 (m, 6H) | (ESI (+)) m/e 366 (M + H)⁺ |
| 175 | N-{4-[benzyl(2-hydroxyethyl)carbamoyl]phenyl}-1,3-dihydro-2H-isoindole-2-carboxamide | ¹H NMR (400 MHz, Pyridine-$d_5$, Temp = 90° C.) δ ppm 8.20-8.21 (bs, 1H), 7.85-7.88 (m, 2H), 7.61-7.64 (m, 2H), 7.37-7.43 (m, 2H), 7.29-7.34 (m, 2H), 7.20-7.27 (m, 3H), 7.14-7.19 (m, 2H), 4.94-4.94 (bs, 2H), 4.84 (s, 4H), 3.94-3.97 (m, 2H), 3.73 (t, J = 6.0 Hz, 2H) | (ESI (−)) m/e 414 (M − H)⁻ |
| 176 | N-{4-[(4-cyanophenyl)carbamoyl]phenyl}-1,3-dihydro-2H-isoindole-2-carboxamide | ¹H NMR (500 MHz, DMSO-$d_6$/Deuterium Oxide) δ ppm 7.97-7.99 (m, 2H), 7.91-7.93 (m, 2H), 7.80-7.83 (m, 2H), 7.72-7.77 (m, 2H), 7.38-7.41 (m, 2H), 7.33-7.36 (m, 2H), 4.81 (s, 4H) | (ESI (−)) m/e 381 (M − H)⁻ |
| 177 | N-(4-{[2-(4-chlorophenyl)ethyl]carbamoyl}phenyl)-1,3-dihydro-2H-isoindole-2-carboxamide | ¹H NMR (500 MHz, DMSO-$d_6$/Deuterium Oxide) δ ppm 8.66 (s, 1H), 8.45 (t, J = 5.6 Hz, 1H), 7.72-7.74 (m, 2H), 7.64 (dd, J = 8.7, 2.3 Hz, 2H), 7.37-7.40 (m, 2H), 7.32-7.36 (m, 4H), 7.27-7.30 (m, 2H), 4.78-4.79 (bs, 4H), 3.45-3.50 (m, 2H), 2.84 (t, J = 7.2 Hz, 2H) | (ESI (+)) m/e 420 (M + H)⁺ |
| 178 | N-(4-{[2-(4-methylpiperazin-1-yl)ethyl]carbamoyl}phenyl)-1,3-dihydro-2H-isoindole-2-carboxamide | ¹H NMR (400 MHz, Pyridine-$d_5$, Temp = 90° C.) δ ppm 8.34-8.35 (bs, 1H), 8.08-8.12 (m, 2H), 8.06-8.10 (m, 1H), 7.92-7.94 (m, 2H), 7.19-7.23 (m, 2H), 7.17-7.19 (m, 2H), 4.85 (s, 4H), 3.71 (q, J = 5.9 Hz, 2H), 2.85-2.90 (m, 4H), 2.81-2.85 (m, 4H), 2.76 (t, J = 6.3 Hz, 2H), 2.48 (s, 3H) | (ESI (+)) m/e 408 (M + H)⁺ |
| 179 | N-(4-{[2-(pyridin-2-yl)ethyl]carbamoyl}phenyl)-1,3-dihydro-2H-isoindole-2-carboxamide | ¹H NMR (500 MHz, DMSO-$d_6$/Deuterium Oxide) δ ppm 8.77 (dd, J = 5.8, 1.6 Hz, 1H), 8.45 (td, J = 7.8, 1.6 Hz, 1H), 7.92 (d, J = 8.0 Hz, 1H), 7.88 (ddd, J = 7.5, 6.0, 1.3 Hz, 1H), 7.66-7.69 (m, 2H), 7.62-7.65 (m, 2H), 7.36-7.39 (m, 2H), 7.32-7.35 (m, 2H), 4.78-4.79 (bs, 4H), 3.68-3.72 (m, 2H), 3.25 (t, J = 6.4 Hz, 2H) | (ESI (+)) m/e 387 (M + H)⁺ |
| 180 | N-{4-[(cyanomethyl)carbamoyl]phenyl}-1,3-dihydro-2H-isoindole-2-carboxamide | ¹H NMR (400 MHz, DMSO-$d_6$/Deuterium Oxide, Temp = 90° C.) δ ppm 7.79-7.81 (m, 2H), 7.68-7.71 (m, 2H), 7.36-7.41 (m, 2H), 7.31-7.36 (m, 2H), 4.82 (s, 4H), 4.28 (s, 2H) | (APCI (+)) m/e 321 (M + H)⁺ |
| 181 | N-[4-(cyclohexylcarbamoyl)phenyl]-1,3-dihydro-2H-isoindole-2-carboxamide | ¹H NMR (400 MHz, Pyridine-$d_5$, Temp = 90° C.) δ ppm 8.26-8.28 (bs, 1H), 8.05-8.08 (m, 2H), 7.88-7.90 (m, 2H), 7.40-7.47 (m, 1H), 7.19-7.24 (m, 2H), 7.14-7.19 (m, 2H), 4.84 (s, 4H), 4.13-4.20 (m, 1H), 2.05-2.08 (m, 2H), 1.63-1.67 (m, 2H), 1.47-1.54 (m, 1H), 1.28-1.41 (m, 4H), 1.04-1.17 (m, 1H) | (ESI (+)) m/e 364 (M + H)⁺ |
| 182 | N-{4-[(3-hydroxyphenyl)carbamoyl]phenyl}-1,3-dihydro-2H-isoindole-2-carboxamide | ¹H NMR (400 MHz, Pyridine-$d_5$, Temp = 90° C.) δ ppm 9.93-9.94 (m, 1H), 8.30-8.32 (m, 1H), 8.10-8.14 (m, 2H), 8.01 (t, J = 2.2 Hz, 1H), 7.87-7.92 (m, 2H), 7.48 (ddd, J = 8.0, 2.0, 0.9 Hz, 1H), 7.25 (t, J = 8.0 Hz, 1H), 7.19-7.25 (m, 2H), 7.13-7.18 (m, 2H), 6.90 (ddd, J = 8.0, 2.4, 1.0 Hz, 1H), 4.83 (s, 4H) | (ESI (+)) m/e 374 (M + H)⁺ |
| 183 | N-{4-[butyl(methyl)carbamoyl]phenyl}-1,3-dihydro-2H-isoindole-2-carboxamide | ¹H NMR (400 MHz, Pyridine-$d_5$, Temp = 90° C.) δ ppm 8.24-8.26 (bs, 1H), 7.89-7.92 (m, 2H), 7.49-7.52 (m, 2H), 7.19-7.24 (m, 2H), 7.15-7.19 (m, 2H), 4.85 (s, 4H), 3.41 (t, J = 7.3 Hz, 2H), 2.95 (s, 3H), 1.52 (p, J = 7.3 Hz, 2H), 1.15-1.33 (m, 2H), 0.82 (t, J = 7.3 Hz, 3H) | (ESI (+)) m/e 350 (M + H)⁺ |
| 184 | N-(4-{[4-(dimethylamino)phenyl]carbamoyl}phenyl)-1,3-dihydro-2H-isoindole-2-carboxamide | ¹H NMR (400 MHz, Pyridine-$d_5$, Temp = 90° C.) δ ppm 9.76-9.77 (bs, 1H), 8.30-8.32 (bs, 1H), 8.16-8.19 (m, 2H), 7.91-7.95 (m, 2H), 7.84-7.86 (m, 2H), 7.20-7.23 (m, 2H), 7.15-7.19 (m, 2H), 6.73-6.81 (m, 2H), 4.85 (s, 4H), 2.77 (s, 6H) | (ESI (−)) m/e 399 (M − H)⁻ |

| Ex | Name | ¹H NMR | MS |
|---|---|---|---|
| 185 | N-[4-(3,4-dihydroisoquinolin-2(1H)-ylcarbonyl)phenyl]-1,3-dihydro-2H-isoindole-2-carboxamide | ¹H NMR (400 MHz, Pyridine-d₅, Temp = 90° C.) δ ppm 8.29-8.30 (bs, 1H), 7.91-7.94 (m, 2H), 7.54-7.60 (m, 2H), 7.19-7.26 (m, 2H), 7.15-7.19 (m, 2H), 7.05-7.11 (m, 1H), 6.98-7.04 (m, 1H), 4.86 (s, 4H), 4.80-4.81 (bs, 2H), 3.75 (t, J = 5.9 Hz, 2H), 2.78 (t, J = 6.0 Hz, 2H) | (ESI (+)) m/e 398 (M + H)⁺ |
| 186 | N-[4-(1,3-dihydro-2H-isoindol-2-ylcarbonyl)phenyl]-1,3-dihydro-2H-isoindole-2-carboxamide | ¹H NMR (400 MHz, Pyridine-d₅, Temp = 90° C.) δ ppm 8.34-8.36 (bs, 1H), 7.96-7.98 (m, 2H), 7.72-7.75 (m, 2H), 7.20-7.24 (m, 4H), 7.16-7.20 (m, 4H), 4.87-4.90 (bs, 4H), 4.88 (s, 4H) | (ESI (+)) m/e 384 (M + H)⁺ |
| 187 | N-[4-(2,3-dihydro-1H-indol-1-ylcarbonyl)phenyl]-1,3-dihydro-2H-isoindole-2-carboxamide | ¹H NMR (400 MHz, Pyridine-d₅, Temp = 90° C.) δ ppm 8.36-8.38 (m, 1H), 7.96-8.00 (m, 1H), 7.93-7.97 (m, 2H), 7.63-7.65 (m, 2H), 7.20-7.24 (m, 2H), 7.15-7.20 (m, 2H), 7.11-7.15 (m, 2H), 6.96-7.00 (m, 1H), 4.87 (s, 4H), 3.94-3.99 (m, 2H), 2.89 (t, J = 8.3 Hz, 2H) | (ESI (+)) m/e 384 (M + H)⁺ |
| 188 | N-[4-(phenylcarbamoyl)phenyl]-1,3-dihydro-2H-isoindole-2-carboxamide | ¹H NMR (500 MHz, DMSO-d₆/Deuterium Oxide) δ ppm 7.90-7.92 (m, 2H), 7.72-7.77 (m, 4H), 7.33-7.40 (m, 6H), 7.12 (t, J = 7.3 Hz, 1H), 4.80-4.82 (bs, 4H) | (ESI (−)) m/e 356 (M − H)⁻ |
| 189 | N-{4-[(4-fluorophenyl)carbamoyl]phenyl}-1,3-dihydro-2H-isoindole-2-carboxamide | ¹H NMR (500 MHz, DMSO-d₆/Deuterium Oxide) δ ppm 10.17-10.19 (bs, 1H), 8.72-8.74 (bs, 1H), 7.89-7.91 (m, 2H), 7.74-7.79 (m, 2H), 7.71-7.75 (m, 2H), 7.37-7.41 (m, 2H), 7.33-7.36 (m, 2H), 7.18-7.22 (m, 2H), 4.80-4.81 (bs, 4H) | (ESI (+)) m/e 376 (M + H)⁺ |
| 190 | N-(4-{[2-(diethylamino)ethyl]carbamoyl}phenyl)-1,3-dihydro-2H-isoindole-2-carboxamide | ¹H NMR (400 MHz, DMSO-d₆/Deuterium Oxide, Temp = 90° C.) δ ppm 7.78-7.81 (m, 2H), 7.67-7.70 (m, 2H), 7.37-7.41 (m, 2H), 7.32-7.36 (m, 2H), 4.82 (s, 4H), 3.66 (t, J = 6.4 Hz, 2H), 3.29-3.33 (m, 2H), 3.24 (q, J = 7.5 Hz, 4H), 1.24-1.33 (m, 6H) | (ESI (+)) m/e 381 (M + H)⁺ |
| 191 | N-{4-[[2-hydroxy-2-phenylethyl](methyl)carbamoyl]phenyl}-1,3-dihydro-2H-isoindole-2-carboxamide | ¹H NMR (400 MHz, Pyridine-d₅, Temp = 90° C.) δ ppm 8.21 (d, J = 1.6 Hz, 1H), 7.85-7.88 (m, 2H), 7.56-7.59 (m, 2H), 7.51-7.54 (m, 2H), 7.29-7.35 (m, 2H), 7.20-7.24 (m, 3H), 7.14-7.19 (m, 2H), 5.29-5.35 (m, 1H), 4.84 (s, 4H), 3.11 (s, 3H) | (ESI (+)) m/e 416 (M + H)⁺ |
| 192 | N-{4-[(2-aminophenyl)carbamoyl]phenyl}-1,3-dihydro-2H-isoindole-2-carboxamide | ¹H NMR (500 MHz, DMSO-d₆/Deuterium Oxide) δ ppm 7.91-7.93 (m, 2H), 7.69-7.72 (m, 2H), 7.38-7.43 (m, 2H), 7.33-7.36 (m, 2H), 7.15-7.18 (m, 1H), 7.01 (ddd, J = 8.0, 7.3, 1.5 Hz, 1H), 6.82 (dd, J = 8.0, 1.4 Hz, 1H), 6.66 (td, J = 7.5, 1.5 Hz, 1H), 4.81 (s, 4H) | (ESI (−)) m/e 371 (M − H)⁻ |
| 193 | N-(4-{[(2R)-2-hydroxypropyl]carbamoyl}phenyl)-1,3-dihydro-2H-isoindole-2-carboxamide | ¹H NMR (400 MHz, Pyridine-d₅, Temp = 90° C.) δ ppm 8.28-8.30 (bs, 1H), 8.05-8.10 (m, 2H), 8.04-8.09 (m, 1H), 7.88-7.91 (m, 2H), 7.19-7.23 (m, 2H), 7.16-7.18 (m, 2H), 4.84 (s, 4H), 4.25 (dqd, J = 6.9, 6.2, 4.2 Hz, 1H), 3.78 (ddd, J = 13.4, 6.1, 4.2 Hz, 1H), 3.61 (ddd, J = 13.4, 6.9, 5.4 Hz, 1H), 1.31 (d, J = 6.2 Hz, 3H) | (ESI (+)) m/e 340 (M + H)⁺ |
| 194 | N-(4-{[(2S)-1-amino-4-methyl-1-oxopentan-2-yl]carbamoyl}phenyl)-1,3-dihydro-2H-isoindole-2-carboxamide | ¹H NMR (400 MHz, DMSO-d₆/Deuterium Oxide, Temp = 90° C.) δ ppm 7.80-7.83 (m, 2H), 7.65-7.68 (m, 2H), 7.36-7.41 (m, 2H), 7.31-7.36 (m, 2H), 4.82 (s, 4H), 4.50 (dd, J = 9.1, 5.0 Hz, 1H), 1.60-1.77 (m, 3H), 0.94 (dd, J = 11.0, 6.1 Hz, 6H) | (ESI (−)) m/e 393 (M − H)⁻ |
| 195 | tert-butyl (1-{4-[(1,3-dihydro-2H-isoindol-2-ylcarbonyl)amino]benzoyl}piperidin-4-yl)carbamate | ¹H NMR (400 MHz, pyridine-d₅) δ ppm 1.49-1.51 (m, 9 H), 1.51-1.61 (m, 1 H), 1.88-2.00 (m, 1 H), 2.98-3.11 (m, 2 H), 3.75-3.90 (m, 1 H), 4.21 (d, J = 13.4 Hz, 1 H), 4.85 (s, 4 H), 6.59 (d, J = 6.1 Hz, 1 H), 7.10-7.25 (m, 5 H), 7.45-7.55 (m, 4 H), 7.89 (d, J = 8.5 Hz, 2 H), 8.26 (s, 1 H) 8.64 (s, 1 H) | (ESI (+)) m/e 465 (M + H)⁺ |

| Ex | Name | ¹H NMR | MS |
|---|---|---|---|
| 196 | N-(4-{[3-(morpholin-4-yl)propyl]carbamoyl}phenyl)-1,3-dihydro-2H-isoindole-2-carboxamide | ¹H NMR (400 MHz, DMSO-d₆/Deuterium Oxide, Temp = 90° C.) δ ppm 7.75-7.78 (m, 2H), 7.63-7.66 (m, 2H), 7.26-7.42 (m, 4H), 4.79 (s, 4H), 3.82-3.86 (m, 4H), 3.37 (t, J = 6.6 Hz, 2H), 3.20-3.26 (m, 4H), 3.12-3.18 (m, 2H), 1.89-2.03 (m, 2H) | (ESI (+)) m/e 409 (M + H)⁺ |
| 197 | N-[4-({4-[3-chloro-5-(trifluoromethyl)pyridin-2-yl]piperazin-1-yl}carbonyl)phenyl]-1,3-dihydro-2H-isoindole-2-carboxamide | ¹H NMR (300 MHz, DMSO-d₆) δ ppm 8.57-8.59 (m, 1H), 8.55-8.57 (bs, 1H), 8.23 (d, J = 2.2 Hz, 1H), 7.65-7.69 (m, 2H), 7.37-7.41 (m, 2H), 7.29-7.38 (m, 4H), 4.79-4.80 (bs, 4H), 3.59-3.84 (m, 4H), 3.45-3.58 (m, 4H) | (ESI (+)) m/e 530 (M + H)⁺ |
| 198 | N-(4-{[4-(cyclohexylmethyl)piperazin-1yl]carbonyl}phenyl)-1,3-dihydro-2H-isoindole-2-carboxamide | ¹H NMR (400 MHz, Pyridine-d₅, Temp = 90° C.) δ ppm 8.31-8.33 (bs, 1H), 7.91-7.95 (m, 2H), 7.50-7.57 (m, 2H), 7.20-7.23 (m, 2H), 7.15-7.19 (m, 2H), 4.86 (s, 4H), 3.63-3.74 (m, 4H), 2.40-2.43 (m, 4H), 2.16 (d, J = 7.0 Hz, 2H), 1.75-1.81 (m, 2H), 1.56-1.70 (m, 3H), 1.43-1.56 (m, 1H), 1.09-1.29 (m, 3H), 0.82-0.97 (m, 2H) | (ESI (−)) m/e 445 (M − H)⁻ |
| 199 | N-(4-{[1-(3-chlorobenzyl)-1H-pyrazol-4-yl]carbamoyl}phenyl)-1,3-dihydro-2H-isoindole-2-carboxamide | ¹H NMR (300 MHz, DMSO-d₆) δ ppm 10.28 (s, 1H), 8.64 (s, 1H), 8.18 (s, 1H), 7.85-7.89 (m, 2H), 7.70-7.74 (m, 2H), 7.63 (s, 1H), 7.28-7.42 (m, 7H), 7.18-7.23 (m, 1H), 5.33-5.34 (bs, 2H), 4.79-4.81 (bs, 4H) | (ESI (−)) m/e 470 (M − H)⁻ |
| 200 | N-(4-{[3-(diethylcarbamoyl)piperidin-1-yl]carbonyl}phenyl)-1,3-dihydro-2H-isoindole-2-carboxamide | ¹H NMR (400 MHz, Pyridine-d₅, Temp = 90° C.) δ ppm 8.27-8.29 (bs, 1H), 7.89-7.92 (m, 2H), 7.52-7.56 (m, 2H), 7.19-7.24 (m, 2H), 7.15-7.19 (m, 2H), 4.85 (s, 4H), 4.17-4.21 (m, 1H), 3.19-3.43 (m, 5H), 2.94 (ddd, J = 13.0, 12.1, 3.3 Hz, 0H), 2.84 (tt, J = 10.6, 4.1 Hz, 1H), 1.89-2.07 (m, 2H), 1.58-1.66 (m, 1H), 1.43-1.58 (m, 1H), 1.04 (t, J = 7.1 Hz, 6H) | (ESI (−)) m/e 447 (M − H)⁻ |
| 201 | N-(4-{[3-(piperidin-1-yl)propyl]carbamoyl}phenyl)-1,3-dihydro-2H-isoindole-2-carboxamide | ¹H NMR (400 MHz, Pyridine-d₅, Temp = 90° C.) δ ppm 8.45-8.51 (m, 1H), 8.32-8.36 (bs, 1H), 8.16-8.18 (m, 2H), 7.93-7.96 (m, 2H), 7.19-7.24 (m, 2H), 7.15-7.19 (m, 2H), 4.85 (s, 4H), 3.61 (q, J = 6.1 Hz, 2H), 3.00-3.05 (m, 2H), 2.88-2.91 (m, 4H), 2.08-2.16 (m, 2H), 1.66-1.76 (m, 4H), 1.32-1.41 (m, 2H) | (ESI (+)) m/e 407 (M + H)⁺ |
| 202 | N-(4-{[4-(2-hydroxyethyl)piperazin-1-yl]carbonyl}phenyl)-1,3-dihydro-2H-isoindole-2-carboxamide | ¹H NMR (300 MHz, DMSO-d₆) δ ppm 8.53 (s, 1H), 7.62-7.66 (m, 2H), 7.24-7.43 (m, 6H), 4.78-4.79 (bs, 4H), 4.39-4.44 (m, 1H), 3.39-3.58 (m, 6H), 2.34-2.45 (m, 6H) | (ESI (+)) m/e 395 (M + H)⁺ |
| 203 | N-{4-[(2-hydroxy-6-methylphenyl)carbamoyl]phenyl}-1,3-dihydro-2H-isoindole-2-carboxamide | ¹H NMR (400 MHz, Pyridine-d₅, Temp = 90° C.) δ ppm 9.59-9.61 (bs, 1H), 8.38-8.40 (bs, 1H), 8.22-8.25 (m, 2H), 7.95-7.98 (m, 2H), 7.20-7.23 (m, 2H), 7.16-7.19 (m, 2H), 7.08 (d, J = 7.1 Hz, 1H), 7.06 (d, J = 2.0 Hz, 1H), 6.82 (dd, J = 7.0, 1.8 Hz, 1H), 4.85 (s, 4H), 2.43 (s, 3H) | (ESI (+)) m/e 388 (M + H)⁺ |
| 204 | N-(4-{[4-(dimethylamino)butyl]carbamoyl}phenyl)-1,3-dihydro-2H-isoindole-2-carboxamide | ¹H NMR (400 MHz, DMSO-d₆/Deuterium Oxide, Temp = 90° C.) δ ppm 7.76-7.79 (m, 2H), 7.64-7.67 (m, 2H), 7.37-7.42 (m, 2H), 7.32-7.36 (m, 2H), 4.82 (s, 4H), 3.32-3.37 (m, 2H), 3.10-3.15 (m, 2H), 2.81 (s, 6H), 1.68-1.79 (m, 2H), 1.59-1.67 (m, 2H) | (ESI (+)) m/e 381 (M + H)⁺ |
| 205 | N-{4-[(3-hydroxypropyl)carbamoyl]phenyl}-1,3-dihydro-2H-isoindole-2-carboxamide | ¹H NMR (400 MHz, DMSO-d₆/Deuterium Oxide, Temp = 90° C.) δ ppm 7.75-7.77 (m, 2H), 7.63-7.65 (m, 2H), 7.36-7.41 (m, 2H), 7.31-7.36 (m, 2H), 4.82 (s, 4H), 3.53 (t, J = 6.3 Hz, 2H), 3.36 (t, J = 6.9 Hz, 2H), 1.74 (p, J = 6.6 Hz, 2H) | (ESI (+)) m/e 340 (M + H)⁺ |

-continued

| Ex | Name | ¹H NMR | MS |
|---|---|---|---|
| 206 | N-{4-[(4-cyclohexylpiperazin-1-yl)carbonyl]phenyl}-1,3-dihydro-2H-isoindole-2-carboxamide | ¹H NMR (400 MHz, Pyridine-d₅, Temp = 90° C.) δ ppm 8.31-8.33 (bs, 1H), 7.91-7.94 (m, 2H), 7.52-7.56 (m, 2H), 7.20-7.25 (m, 2H), 7.15-7.20 (m, 2H), 4.86 (s, 4H), 3.72-3.80 (m, 4H), 2.62-2.65 (m, 4H), 2.36-2.44 (m, 1H), 1.80-1.84 (m, 2H), 1.67-1.72 (m, 2H), 1.48-1.54 (m, 1H), 1.01-1.28 (m, 5H) | (ESI (+)) m/e 433 (M + H)⁺ |
| 207 | N-[4-(5,6-dihydro[1,2,4]triazolo-[4,3-a]pyrazin-7(8H)-ylcarbonyl)phenyl]-1,3-dihydro-2H-isoindole-2-carboxamide | ¹H NMR (300 MHz, DMSO-d₆) δ ppm 8.61 (s, 1H), 8.51 (s, 1H), 7.72 (s, 1H), 7.68-7.70 (m, 1H), 7.41-7.47 (m, 1H), 7.35-7.40 (m, 2H), 7.29-7.35 (m, 2H), 4.86 (s, 2H), 4.79-4.80 (bs, 4H), 4.15 (t, J = 5.3 Hz, 2H), 3.83-3.95 (m, 2H) | (ESI (+)) m/e 389 (M + H)⁺ |
| 208 | N-{4-[methyl(3-methylbutyl)carbamoyl]phenyl}-1,3-dihydro-2H-isoindole-2-carboxamide | ¹H NMR (300 MHz, DMSO-d₆) δ ppm 8.49-8.53 (bs, 1H), 7.60-7.67 (m, 2H), 7.26-7.40 (m, 6H), 4.78 (s, 4H), 3.16-3.49 (m, 2H), 2.92 (s, 3H), 1.13-1.79 (m, 3H), 0.48-1.12 (m, 6H) | (ESI (+)) m/e 366 (M + H)⁺ |
| 209 | N-[4-(propylcarbamoyl)phenyl]-1,3-dihydro-2H-isoindole-2-carboxamide | ¹H NMR (400 MHz, DMSO-d₆/Deuterium Oxide, Temp = 90° C.) δ ppm 7.75-7.78 (m, 2H), 7.62-7.65 (m, 2H), 7.32-7.40 (m, 4H), 4.82 (s, 4H), 3.22-3.30 (m, 2H), 1.53-1.63 (m, 2H), 0.93 (t, J = 7.4 Hz, 3H) | (ESI (+)) m/e 324 (M + H)⁺ |
| 210 | N-(4-{[(2S)-1-hydroxybutan-2-yl]carbamoyl}phenyl)-1,3-dihydro-2H-isoindole-2-carboxamide | ¹H NMR (400 MHz, Pyridine-d₅, Temp = 90° C.) δ ppm 8.28-8.29 (bs, 1H), 8.06-8.08 (m, 2H), 7.87-7.90 (m, 2H), 7.57-7.61 (m, 1H), 7.19-7.23 (m, 2H), 7.15-7.19 (m, 2H), 4.84 (s, 4H), 4.37-4.47 (m, 1H), 3.91-3.99 (m, 2H), 1.84-1.96 (m, 1H), 1.71-1.85 (m, 1H), 1.03 (t, J = 7.5 Hz, 3H) | (ESI (+)) m/e 354 (M + H)⁺ |
| 211 | N-{4-[(5-fluoropyridin-2-yl)carbamoyl]phenyl}-1,3-dihydro-2H-isoindole-2-carboxamide | ¹H NMR (400 MHz, Pyridine-d₅, Temp = 90° C.) δ ppm 10.45-10.47 (bs, 1H), 8.58 (dd, J = 9.1, 4.2 Hz, 1H), 8.42-8.44 (bs, 1H), 8.24 (d, J = 3.0 Hz, 1H), 8.18-8.20 (m, 2H), 7.98-8.00 (m, 2H), 7.45 (ddd, J = 9.0, 8.1, 3.1 Hz, 1H), 7.20-7.24 (m, 2H), 7.15-7.20 (m, 2H), 4.86 (s, 4H) | (ESI (+)) m/e 377 (M + H)⁺ |
| 212 | N-{4-[(cyclopropylmethyl)(propyl)carbamoyl]phenyl}-1,3-dihydro-2H-isoindole-2-carboxamide | ¹H NMR (400 MHz, Pyridine-d₅, Temp = 90° C.) δ ppm 8.23-8.24 (bs, 1H), 7.90-7.92 (m, 2H), 7.48-7.52 (m, 2H), 7.19-7.24 (m, 2H), 7.15-7.19 (m, 2H), 4.85 (s, 4H), 3.49-3.53 (m, 2H), 3.35 (d, J = 6.7 Hz, 2H), 1.58-1.66 (m, 2H), 0.96-1.07 (m, 1H), 0.81 (t, J = 7.4 Hz, 3H), 0.42-0.47 (m, 2H), 0.15-0.19 (m, 2H) | (ESI (+)) m/e 378 (M + H)⁺ |
| 213 | N-(4-{[(2S)-1-methoxypropan-2-yl]carbamoyl}phenyl)-1,3-dihydro-2H-isomdole-2-carboxamide | ¹H NMR (400 MHz, Pyridine-d₅, Temp = 90° C.) δ ppm 8.28-8.34 (m, 1H), 8.05-8.08 (m, 2H), 7.88-7.90 (m, 2H), 7.54-7.63 (m, 1H), 7.18-7.24 (m, 2H), 7.15-7.18 (m, 2H), 4.83 (s, 4H), 4.54-4.64 (m, 1H), 3.53 (dd, J = 9.5, 5.2 Hz, 1H), 3.45 (dd, J = 9.5, 5.5 Hz, 1H), 3.27 (s, 3H), 1.30 (d, J = 6.8 Hz, 3H) | (ESI (+)) m/e 354 (M + H)⁺ |
| 214 | N-[4-(1,3,4,9-tetrahydro-2H-beta-carbolin-2-ylcarbonyl)phenyl]-1,3-dihydro-2H-isoindole-2-carboxamide | ¹H NMR (400 MHz, Pyridine-d₅, Temp = 90° C.) δ ppm 11.10-11.13 (bs, 1H), 8.29-8.30 (bs, 1H), 7.91-7.94 (m, 2H), 7.57-7.61 (m, 2H), 7.57-7.60 (m, 1H), 7.45-7.48 (m, 1H), 7.16-7.25 (m, 6H), 4.96-4.97 (bs, 2H), 4.87 (s, 4H), 3.86-3.92 (m, 2H), 2.85 (t, J = 5.7 Hz, 2H) | (ESI (+)) m/e 437 (M + H)⁺ |
| 215 | N-[4-(tert-butylcarbamoyl)phenyl]-1,3-dihydro-2H-isoindole-2-carboxamide | ¹H NMR (400 MHz, Pyridine-d₅, Temp = 90° C.) δ ppm 8.24-8.26 (bs, 1H), 7.96-7.99 (m, 2H), 7.85-7.88 (m, 2H), 7.19-7.23 (m, 2H), 7.14-7.19 (m, 2H), 6.93-6.96 (bs, 1H), 4.83 (s, 4H), 1.52 (s, 9H) | (ESI (+)) m/e 338 (M + H)⁺ |
| 216 | N-[4-({4-[4-(trifluoromethyl)phenyl]piperazin-1-yl}carbonyl)phenyl]-1,3-dihydro-2H-isoindole-2-carboxamide | ¹H NMR (500 MHz, DMSO-d₆/Deuterium Oxide) δ ppm 7.64-7.67 (m, 2H), 7.53-7.55 (m, 2H), 7.36-7.42 (m, 4H), 7.31-7.36 (m, 2H), 7.09-7.11 (m, 2H), 4.79-4.80 (bs, 4H), 3.55-3.76 (m, 4H), 3.26-3.43 (m, 4H) | (ESI (+)) m/e 495 (M + H)⁺ |

| Ex | Name | ¹H NMR | MS |
|---|---|---|---|
| 217 | N-{4-[(3-methylbutan-2-yl)carbamoyl]phenyl}-1,3-dihydro-2H-isoindole-2-carboxamide | ¹H NMR (400 MHz, Pyridine-$d_5$, Temp = 90° C.) δ ppm 8.28-8.29 (bs, 1H), 8.06-8.09 (m, 2H), 7.88-7.92 (m, 2H), 7.30-7.35 (bs, 1H), 7.19-7.24 (m, 2H), 7.14-7.18 (m, 2H), 4.84 (s, 4H), 4.22-4.32 (m, 1H), 1.82-1.91 (m, 1H), 1.19 (d, J = 6.8 Hz, 3H), 0.97 (d, J = 6.7 Hz, 3H), 0.93 (d, J = 6.7 Hz, 3H) | (ESI (+)) m/e 352 (M + H)⁺ |
| 218 | N-{4-[(3,3-difluoropyrrolidin-1-yl)carbonyl]phenyl}-1,3-dihydro-2H-isoindole-2-carboxamide | ¹H NMR (400 MHz, Pyridine-$d_5$, Temp = 90° C.) δ ppm 8.34-8.36 (bs, 1H), 7.91-7.94 (m, 2H), 7.61-7.65 (m, 2H), 7.20-7.24 (m, 2H), 7.15-7.19 (m, 2H), 4.86 (s, 4H), 3.96-4.04 (m, 2H), 3.76 (t, J = 7.4 Hz, 2H), 2.21-2.35 (m, 2H) | (ESI (−)) m/e 370 (M − H)⁻ |
| 219 | N-{4-[(2-methylpiperidin-1-yl)carbonyl]phenyl}-1,3-dihydro-2H-isoindole-2-carboxamide | ¹H NMR (400 MHz, Pyridine-$d_5$, Temp = 90° C.) δ ppm 8.26-8.28 (bs, 1H), 7.90-7.92 (m, 2H), 7.47-7.51 (m, 2H), 7.19-7.23 (m, 2H), 7.14-7.19 (m, 2H), 4.85 (s, 4H), 4.62-4.67 (m, 1H), 4.02-4.17 (m, 1H), 2.93 (td, J = 12.9, 3.1 Hz, 1H), 1.30-1.65 (m, 6H), 1.14 (d, J = 6.9 Hz, 3H) | (ESI (+)) m/e 364 (M + H)⁺ |
| 220 | N-(4-{[(3S)-1-benzylpyrrolidin-3-yl]carbamoyl}phenyl)-1,3-dihydro-2H-isoindole-2-carboxamide | ¹H NMR (400 MHz, Pyridine-$d_5$, Temp = 90° C.) δ ppm 8.26-8.31 (bs, 1H), 8.20-8.26 (m, 1H), 8.09-8.12 (m, 2H), 7.89-7.92 (m, 2H), 7.41-7.48 (m, 2H), 7.23-7.33 (m, 3H), 7.19-7.24 (m, 2H), 7.14-7.19 (m, 2H), 4.90-5.00 (m, 1H), 4.84 (s, 4H), 3.91 (s, 2H), 3.09-3.17 (m, 3H), 2.68-2.75 (m, 1H), 2.30-2.43 (m, 1H), 2.02 (dtd, J = 13.1, 7.8, 5.2 Hz, 1H) | (ESI (−)) m/e 439 (M − H)⁻ |
| 221 | N-{4-[(4-hydroxypiperidin-1-yl)carbonyl]phenyl}-1,3-dihydro-2H-isoindole-2-carboxamide | ¹H NMR (400 MHz, Pyridine-$d_5$, Temp = 90° C.) δ ppm 8.26-8.28 (bs, 1H), 7.89-7.92 (m, 2H), 7.52-7.56 (m, 2H), 7.19-7.23 (m, 2H), 7.16-7.19 (m, 2H), 4.85 (s, 4H), 3.99-4.12 (m, 3H), 3.35 (ddd, J = 13.2, 9.1, 3.8 Hz, 2H), 1.82-1.98 (m, 2H), 1.59-1.75 (m, 2H) | (ESI (+)) m/e 366 (M + H)⁺ |
| 222 | N-{4-[bis(2-methoxyethyl)carbamoyl]phenyl}-1,3-dihydro-2H-isoindole-2-carboxamide | ¹H NMR (400 MHz, Pyridine-$d_5$, Temp = 90° C.) δ ppm 8.22-8.24 (bs, 1H), 7.88-7.92 (m, 2H), 7.54-7.57 (m, 2H), 7.19-7.23 (m, 2H), 7.16-7.18 (m, 2H), 4.84 (s, 4H), 3.75 (t, J = 5.8 Hz, 4H), 3.57 (t, J = 5.8 Hz, 4H), 3.23 (s, 6H) | (ESI (+)) m/e 398 (M + H)⁺ |
| 223 | N-{4-[(3-fluorophenyl)carbamoyl]phenyl}-1,3-dihydro-2H-isoindole-2-carboxamide | ¹H NMR (400 MHz, Pyridine-$d_5$, Temp = 90° C.) δ ppm 10.17-10.23 (m, 1H), 8.35-8.36 (bs, 1H), 8.12-8.14 (m, 2H), 8.04 (dt, J = 11.5, 2.3 Hz, 1H), 7.90-7.93 (m, 2H), 7.66 (ddd, J = 8.1, 2.0, 1.0 Hz, 1H), 7.20-7.31 (m, 3H), 7.15-7.19 (m, 2H), 6.83 (tdd, J = 8.4, 2.6, 0.9 Hz, 1H), 4.84 (s, 4H) | (ESI (+)) m/e 376 (M + H)⁺ |
| 224 | N-[4-(cyclopentylcarbamoyl)phenyl]-1,3-dihydro-2H-isoindole-2-carboxamide | ¹H NMR (500 MHz, DMSO-$d_6$/Deuterium Oxide) δ ppm 7.76-7.78 (m, 2H), 7.60-7.68 (m, 2H), 7.37-7.42 (m, 2H), 7.32-7.35 (m, 2H), 4.76-4.82 (m, 4H), 4.17-4.25 (m, 1H), 1.86-1.93 (m, 2H), 1.66-1.71 (m, 2H), 1.50-1.59 (m, 4H) | (ESI (+)) m/e 350 (M + H)⁺ |
| 225 | N-{4-[(4-carbamoylpiperidin-1-yl)carbonyl]phenyl}-1,3-dihydro-2H-isoindole-2-carboxamide | ¹H NMR (400 MHz, DMSO-$d_6$/Deuterium Oxide, Temp = 90° C.) δ ppm 7.62-7.64 (m, 2H), 7.30-7.40 (m, 6H), 4.81 (s, 4H), 4.01-4.09 (m, 2H), 2.96-3.04 (m, 2H), 2.42-2.50 (m, 1H), 1.76-1.82 (m, 2H), 1.51-1.62 (m, 2H) | (ESI (−)) m/e 393 (M − H)⁻ |
| 226 | N-[4-(cyclopropylcarbamoyl)phenyl]-1,3-dihydro-2H-isoindole-2-carboxamide | ¹H NMR (500 MHz, DMSO-$d_6$/Deuterium Oxide) δ ppm 7.73-7.76 (m, 2H), 7.60-7.67 (m, 2H), 7.36-7.40 (m, 2H), 7.32-7.36 (m, 2H), 4.78-4.79 (bs, 4H), 2.79-2.84 (m, 1H), 0.67-0.75 (m, 2H), 0.53-0.60 (m, 2H) | (ESI (−)) m/e 320 (M − H)⁻ |
| 227 | N-[4-(methylcarbamoyl)phenyl]-1,3-dihydro-2H-isoindole-2-carboxamide | ¹H NMR (300 MHz, DMSO-$d_6$) δ ppm 8.56 (s, 1H), 8.19-8.26 (m, 1H), 7.73-7.77 (m, 2H), 7.63-7.67 (m, 2H), 7.30-7.39 (m, 4H), 4.79 (s, 4H), 2.76 (d, J = 4.5 Hz, 3H) | (ESI (+)) m/e 296 (M + H)⁺ |

| Ex | Name | ¹H NMR | MS |
|---|---|---|---|
| 228 | N-(4-{[3-(dimethylamino)propyl]carbamoyl}phenyl)-1,3-dihydro-2H-isoindole-2-carboxamide | ¹H NMR (400 MHz, DMSO-d₆/Deuterium Oxide, Temp = 90° C.) δ ppm 7.77-7.80 (m, 2H), 7.65-7.68 (m, 2H), 7.37-7.44 (m, 2H), 7.32-7.36 (m, 2H), 4.82 (s, 4H), 3.39 (t, J = 6.7 Hz, 2H), 3.09-3.19 (m, 2H), 2.83 (s, 6H), 1.89-2.03 (m, 2H) | (ESI (+)) m/e 367 (M + H)⁺ |
| 229 | N-{4-[methyl(tetrahydrofuran-2-ylmethyl)carbamoyl]phenyl}-1,3-dihydro-2H-isoindole-2-carboxamide | ¹H NMR (400 MHz, Pyridine-d₅, Temp = 90° C.) δ ppm 8.24-8.26 (bs, 1H), 7.89-7.91 (m, 2H), 7.52-7.56 (m, 2H), 7.19-7.24 (m, 2H), 7.14-7.19 (m, 2H), 4.85 (s, 4H), 4.09-4.20 (m, 1H), 3.72-3.78 (m, 1H), 3.59-3.71 (m, 2H), 3.46-3.52 (m, 1H), 3.10 (s, 3H), 1.74-1.86 (m, 1H), 1.62-1.72 (m, 2H), 1.39-1.50 (m, 1H) | (ESI (+)) m/e 380 (M + H)⁺ |
| 230 | N-[4-(pentan-2-ylcarbamoyl)phenyl]-1,3-dihydro-2H-isoindole-2-carboxamide | ¹H NMR (400 MHz, Pyridine-d₅, Temp = 90° C.) δ ppm 8.26-8.28 (bs, 1H), 8.07-8.10 (m, 2H), 7.88-7.91 (m, 2H), 7.44 (d, J = 7.0 Hz, 1H), 7.19-7.23 (m, 2H), 7.14-7.18 (m, 2H), 4.84 (s, 4H), 4.35-4.45 (m, 1H), 1.58-1.67 (m, 1H), 1.34-1.56 (m, 3H), 1.24 (d, J = 6.6 Hz, 3H), 0.88 (t, J = 7.2 Hz, 3H) | (ESI (+)) m/e 352 (M + H)⁺ |
| 231 | N-[4-(pentan-3-ylcarbamoyl)phenyl]-1,3-dihydro-2H-isoindole-2-carboxamide | ¹H NMR (400 MHz, Pyridine-d₅, Temp = 90° C.) δ ppm 8.27-8.29 (bs, 1H), 8.08-8.11 (m, 2H), 7.89-7.91 (m, 2H), 7.31-7.37 (m, 1H), 7.19-7.23 (m, 2H), 7.14-7.18 (m, 2H), 4.84 (s, 4H), 4.15-4.24 (m, 1H), 1.42-1.72 (m, 4H), 0.96 (t, J = 7.4 Hz, 6H) | (ESI (+)) m/e 352 (M + H)⁺ |
| 232 | N-[4-(cyclobutylcarbamoyl)phenyl]-1,3-dihydro-2H-isoindole-2-carboxamide | ¹H NMR (400 MHz, Pyridine-d₅, Temp = 90° C.) δ ppm 8.25-8.27 (m, 1H), 8.06-8.10 (m, 1H), 7.92-8.00 (m, 1H), 7.88-7.90 (m, 2H), 7.19-7.23 (m, 2H), 7.14-7.18 (m, 2H), 4.84 (s, 4H), 4.71-4.80 (m, 1H), 2.27-2.46 (m, 2H), 1.99-2.17 (m, 2H), 1.53-1.74 (m, 2H) | (ESI (+)) m/e 336 (M + H)⁺ |
| 233 | N-{4-[(1,3-dioxolan-2-ylmethyl)(methyl)carbamoyl]phenyl}-1,3-dihydro-2H-isoindole-2-carboxamide | ¹H NMR (400 MHz, DMSO-d₆/Deuterium Oxide, Temp = 90° C.) δ ppm 7.61-7.64 (m, 2H), 7.31-7.45 (m, 6H), 5.04 (t, J = 4.3 Hz, 1H), 4.81 (s, 4H), 3.88-3.94 (m, 2H), 3.82-3.86 (m, 2H), 3.54 (d, J = 4.3 Hz, 2H), 3.04 (s, 3H) | (ESI (−)) m/e 280 (M − H)⁻ |
| 234 | N-(4-{[1-(4-fluorophenyl)-1H-pyrazol-4-yl]carbamoyl}phenyl)-1,3-dihydro-2H-isoindole-2-carboxamide | ¹H NMR (300 MHz, DMSO-d₆) δ ppm 10.45 (s, 1H), 8.65-8.68 (m, 2H), 7.82-7.94 (m, 5H), 7.74-7.78 (m, 2H), 7.31-7.40 (m, 6H), 4.80-4.82 (bs, 4H) | (ESI (+)) m/e 442 (M + H)⁺ |
| 235 | N-{4-[(1-hydroxy-2-methylpropan-2-yl)carbamoyl]phenyl}-1,3-dihydro-2H-isoindole-2-carboxamide | ¹H NMR (400 MHz, Pyridine-d₅, Temp = 90° C.) δ ppm 8.23-8.34 (m, 1H), 7.95-7.97 (m, 2H), 7.84-7.88 (m, 2H), 7.19-7.24 (m, 2H), 7.15-7.18 (m, 2H), 4.83 (s, 4H), 3.91 (s, 2H), 1.59 (s, 6H) | (ESI (−)) m/e 352 (M − H)⁻ |
| 236 | N-{4-[(1-phenyl-1H-pyrazol-4-yl)carbamoyl]phenyl}-1,3-dihydro-2H-isoindole-2-carboxamide | ¹H NMR (300 MHz, DMSO-d₆) δ ppm 10.45 (s, 1H), 8.67 (s, 2H), 7.90-7.95 (m, 3H), 7.80-7.84 (m, 2H), 7.74-7.78 (m, 2H), 7.47-7.53 (m, 2H), 7.27-7.40 (m, 5H), 4.80-4.82 (bs, 4H) | (ESI (+)) m/e 424 (M + H)⁺ |
| 237 | N-[4-({2-[4-(trifluoromethyl)phenyl]ethyl}carbamoyl)phenyl]-1,3-dihydro-2H-isoindole-2-carboxamide | ¹H NMR (500 MHz, DMSO-d₆/Deuterium Oxide) δ ppm 7.72-7.74 (m, 2H), 7.63-7.67 (m, 4H), 7.48-7.50 (m, 2H), 7.36-7.41 (m, 2H), 7.31-7.36 (m, 2H), 4.78-4.79 (bs, 4H), 3.52 (t, J = 7.0 Hz, 2H), 2.95 (t, J = 7.2 Hz, 2H) | (ESI (−)) m/e 452 (M − H)⁻ |
| 238 | N-{4-[(2-methoxyethyl)(propyl)carbamoyl]phenyl}-1,3-dihydro-2H-isoindole-2-carboxamide | ¹H NMR (400 MHz, Pyridine-d₅, Temp = 90° C.) δ ppm 8.24-8.26 (bs, 1H), 7.89-7.92 (m, 2H), 7.49-7.53 (m, 2H), 7.19-7.23 (m, 2H), 7.15-7.19 (m, 2H), 4.85 (s, 4H), 3.65 (t, J = 5.7 Hz, 2H), 3.56 (t, J = 5.7 Hz, 2H), 3.46 (t, J = 7.3 Hz, 2H), 3.24 (s, 3H), 1.53-1.67 (m, 2H), 0.78 (t, J = 7.4 Hz, 3H) | (ESI (−)) m/e 380 (M − H)⁻ |

| Ex | Name | ¹H NMR | MS |
|---|---|---|---|
| 239 | N-[4-(sec-butylcarbamoyl)phenyl]-1,3-dihydro-2H-isoindole-2-carboxamide | ¹H NMR (400 MHz, Pyridine-d₅, Temp = 90° C.) δ ppm 8.26-8.28 (bs, 1H), 8.06-8.10 (m, 2H), 7.88-7.91 (m, 2H), 7.42-7.46 (m, 1H), 7.19-7.23 (m, 2H), 7.15-7.18 (m, 2H), 4.84 (s, 4H), 4.21-4.36 (m, 1H), 1.42-1.75 (m, 2H), 1.23 (d, J = 6.6 Hz, 3H), 0.93 (t, J = 7.4 Hz, 3H) | (ESI (+)) m/e 338 (M + H)⁺ |
| 240 | N-(4-{[3-(trifluoromethyl)piperidin-1-yl]carbonyl}phenyl)-1,3-dihydro-2H-isoindole-2-carboxamide | ¹H NMR (500 MHz, DMSO-d₆/Deuterium Oxide) δ ppm 8.61-8.63 (bs, 1H), 7.63-7.65 (m, 2H), 7.36-7.41 (m, 2H), 7.31-7.36 (m, 4H), 4.78-4.79 (bs, 4H), 3.94-4.64 (m, 2H), 2.97-3.12 (m, 2H), 1.97-2.02 (m, 1H), 1.64-1.83 (m, 1H), 1.55-1.66 (m, 1H), 1.42-1.55 (m, 1H) | (ESI (−)) m/e 416 (M − H)⁻ |
| 241 | N-{4-[bis(2-ethoxyethyl)carbamoyl]phenyl}-1,3-dihydro-2H-isoindole-2-carboxamide | ¹H NMR (400 MHz, Pyridine-d₅, Temp = 90° C.) δ ppm 8.20-8.22 (bs, 1H), 7.89-7.92 (m, 2H), 7.57-7.60 (m, 2H), 7.19-7.23 (m, 2H), 7.14-7.19 (m, 2H), 4.84 (s, 4H), 3.77 (t, J = 5.8 Hz, 4H), 3.62-3.65 (m, 4H), 3.42 (q, J = 7.0 Hz, 4H), 1.11 (t, J = 7.0 Hz, 6H) | (ESI (−)) m/e 424 (M − H)⁻ |
| 242 | N-{4-[butyl(ethyl)carbamoyl]phenyl}-1,3-dihydro-2H-isoindole-2-carboxamide | ¹H NMR (400 MHz, Pyridine-d₅, Temp = 90° C.) δ ppm 8.23-8.25 (bs, 1H), 7.89-7.93 (m, 2H), 7.48-7.51 (m, 2H), 7.19-7.23 (m, 2H), 7.15-7.19 (m, 2H), 4.85 (s, 4H), 3.35-3.47 (m, 4H), 1.56 (p, J = 7.3 Hz, 2H), 1.19-1.32 (m, 2H), 1.10 (t, J = 7.1 Hz, 3H), 0.83 (t, J = 7.3 Hz, 3H) | (ESI (+)) m/e 366 (M + H)⁺ |
| 243 | N-{4-[(1-methoxypropan-2-yl)carbamoyl]phenyl}-1,3-dihydro-2H-isoindole-2-carboxamide | ¹H NMR (400 MHz, Pyridine-d₅, Temp = 90° C.) δ ppm 8.28-8.32 (m, 1H), 8.05-8.08 (m, 2H), 7.88-7.90 (m, 2H), 7.56-7.60 (m, 1H), 7.19-7.24 (m, 2H), 7.15-7.19 (m, 2H), 4.84 (s, 4H), 4.54-4.64 (m, 1H), 3.53 (dd, J = 9.6, 5.2 Hz, 1H), 3.45 (dd, J = 9.5, 5.5 Hz, 1H), 3.27 (s, 3H), 1.30 (d, J = 6.7 Hz, 3H) | (ESI (+)) m/e 354 (M + H)⁺ |
| 244 | N-{4-[(2-methoxyethyl)(methyl)carbamoyl]phenyl}-1,3-dihydro-2H-isoindole-2-carboxamide | ¹H NMR (400 MHz, Pyridine-d₅, Temp = 90° C.) δ ppm 8.23-8.28 (bs, 1H), 7.88-7.91 (m, 2H), 7.51-7.56 (m, 2H), 7.19-7.25 (m, 2H), 7.15-7.19 (m, 2H), 4.85 (s, 4H), 3.63 (t, J = 5.6 Hz, 2H), 3.53 (t, J = 5.6 Hz, 2H), 3.23 (s, 3H), 3.04 (s, 3H) | (ESI (+)) m/e 354 (M + H)⁺ |
| 245 | N-{4-[(3R)-tetrahydrofuran-3-ylcarbamoyl]phenyl}-1,3-dihydro-2H-isoindole-2-carboxamide | ¹H NMR (400 MHz, Pyridine-d₅, Temp = 90° C.) δ ppm 8.29-8.31 (bs, 1H), 8.04-8.09 (m, 2H), 7.97-8.04 (m, 1H), 7.88-7.90 (m, 2H), 7.19-7.24 (m, 2H), 7.14-7.19 (m, 2H), 4.80-4.87 (m, 1H), 4.80-4.87 (m, 4H), 4.02 (dd, J = 9.0, 6.1 Hz, 1H), 3.85-3.93 (m, 2H), 3.72 (td, J = 8.2, 6.1 Hz, 1H), 2.21 (tdd, J = 7.9, 12.7, 6.4 Hz, 1H), 1.93-2.02 (m, 1H) | (ESI (−)) m/e 350 (M − H)⁻ |
| 246 | N-[4-(morpholin-4-ylcarbonyl)phenyl]-1,3-dihydro-2H-isoindole-2-carboxamide | ¹H NMR (400 MHz, DMSO-d₆/Deuterium Oxide, Temp = 90° C.) δ ppm 7.62-7.65 (m, 2H), 7.31-7.41 (m, 6H), 4.81 (s, 4H), 3.63-3.65 (m, 4H), 3.50-3.58 (m, 4H) | (ESI (−)) m/e 350 (M − H)⁻ |
| 247 | N-{4-[isobutyl(methyl)carbamoyl]phenyl}-1,3-dihydro-2H-isoindole-2-carboxamide | ¹H NMR (400 MHz, Pyridine-d₅, Temp = 90° C.) δ ppm 8.24-8.26 (bs, 1H), 7.89-7.92 (m, 2H), 7.48-7.52 (m, 2H), 7.19-7.24 (m, 2H), 7.15-7.19 (m, 2H), 4.85 (s, 4H), 3.30 (d, J = 7.3 Hz, 2H), 2.94 (s, 3H), 1.91-2.07 (m, 1H), 0.83 (d, J = 6.6 Hz, 6H) | (ESI (+)) m/e 352 (M + H)⁺ |
| 248 | N-[4-({4-[2-(2-hydroxyethoxy)ethyl]piperazin-1-yl}carbonyl)phenyl]-1,3-dihydro-2H-isoindole-2-carboxamide | ¹H NMR (400 MHz, DMSO-d₆/Deuterium Oxide, Temp = 90° C.) δ ppm 7.66-7.69 (m, 2H), 7.39-7.43 (m, 2H), 7.36-7.40 (m, 2H), 7.32-7.36 (m, 2H), 4.82 (s, 4H), 3.79-3.83 (m, 2H), 3.71-3.90 (m, 4H), 3.58-3.63 (m, 2H), 3.53-3.58 (m, 2H), 3.32-3.35 (m, 2H), 3.22 (s, 4H) | (ESI (+)) m/e 439 (M + H)⁺ |

-continued

| Ex | Name | ¹H NMR | MS |
|---|---|---|---|
| 249 | N-{4-[(3-methylpiperidin-1-yl)carbonyl]phenyl}-1,3-dihydro-2H-isoindole-2-carboxamide | ¹H NMR (400 MHz, Pyridine-$d_5$, Temp = 90° C.) δ ppm 8.25-8.27 (bs, 1H), 7.90-7.92 (m, 2H), 7.51-7.55 (m, 2H), 7.19-7.23 (m, 2H), 7.15-7.19 (m, 2H), 4.85 (s, 4H), 4.09-4.19 (m, 2H), 2.88 (ddd, J = 13.1, 11.1, 3.2 Hz, 1H), 2.57 (dd, J = 12.9, 10.1 Hz, 1H), 1.63-1.69 (m, 1H), 1.47-1.61 (m, 2H), 1.34-1.45 (m, 1H), 1.03 (dddd, J = 13.0, 11.3, 10.6, 4.4 Hz, 1H), 0.75 (d, J = 6.6 Hz, 3H) | (ESI (+)) m/e 364 (M + H)⁺ |
| 250 | N-(4-carbamoylphenyl)-1,3-dihydro-2H-isoindole-2-carboxamide | ¹H NMR (300 MHz, DMSO-$d_6$) δ ppm 8.56 (s, 1H), 7.76-7.83 (m, 2H), 7.73-7.85 (bs, 1H), 7.63-7.67 (m, 2H), 7.30-7.39 (m, 4H), 7.09-7.19 (bs, 1H), 4.79 (s, 4H) | (ESI (+)) m/e 282 (M + H)⁺ |
| 251 | N-(4-{[(2S)-2-(trifluoromethyl)pyrrolidin-1-yl]carbonyl}phenyl)-1,3-dihydro-2H-isoindole-2-carboxamide | ¹H NMR (400 MHz, Pyridine-$d_5$, Temp = 90° C.) δ ppm 8.34-8.36 (bs, 1H), 7.91-7.93 (m, 2H), 7.65-7.68 (m, 2H), 7.20-7.25 (m, 2H), 7.15-7.19 (m, 2H), 5.25-5.34 (m, 1H), 4.85 (s, 4H), 3.50-3.56 (m, 2H), 1.95-2.02 (m, 2H), 1.80-1.89 (m, 1H), 1.58-1.70 (m, 1H) | (ESI (−)) m/e 402 (M − H)⁻ |
| 252 | N-(4-{[(2S)-1-hydroxy-4-methylpentan-2-yl]carbamoyl}phenyl)-1,3-dihydro-2H-isoindole-2-carboxamide | ¹H NMR (400 MHz, Pyridine-$d_5$, Temp = 90° C.) δ ppm 8.29-8.30 (bs, 1H), 8.06-8.11 (m, 2H), 7.88-7.90 (m, 2H), 7.62 (d, J = 8.0 Hz, 1H), 7.19-7.24 (m, 2H), 7.14-7.18 (m, 2H), 4.84 (s, 4H), 4.58-4.67 (m, 1H), 3.95 (d, J = 4.9 Hz, 3H), 1.82-1.93 (m, 1H), 1.73 (ddd, J = 14.0, 8.6, 5.5 Hz, 1H), 1.68 (ddd, J = 13.7, 8.2, 5.5 Hz, 1H), 0.99 (d, J = 6.6 Hz, 3H), 0.93 (d, J = 6.6 Hz, 3H) | (ESI (+)) m/e 382 (M + H)⁺ |
| 253 | N-(4-{[(1R)-2-hydroxy-1-phenylethyl]carbamoyl}phenyl)-1,3-dihydro-2H-isoindole-2-carboxamide | ¹H NMR (400 MHz, Pyridine-$d_5$, Temp = 90° C.) δ ppm 8.29-8.30 (bs, 1H), 8.15-8.18 (m, 1H), 8.08-8.11 (m, 2H), 7.87-7.90 (m, 2H), 7.61-7.64 (m, 2H), 7.27-7.33 (m, 2H), 7.19-7.24 (m, 3H), 7.15-7.19 (m, 2H), 5.68-5.73 (m, 1H), 4.83 (s, 4H), 4.23 (d, J = 5.6 Hz, 2H) | (ESI (+)) m/e 402 (M + H)⁺ |
| 254 | N-{4-[(2-methylpyrrolidin-1-yl)carbonyl]phenyl}-1,3-dihydro-2H-isoindole-2-carboxamide | ¹H NMR (400 MHz, Pyridine-$d_5$, Temp = 90° C.) δ ppm 8.26-8.28 (bs, 1H), 7.89-7.92 (m, 2H), 7.60-7.65 (m, 2H), 7.20-7.24 (m, 2H), 7.15-7.19 (m, 2H), 4.86 (s, 4H), 4.26-4.36 (m, 1H), 3.47 (t, J = 6.8 Hz, 2H), 1.92 (dq, J = 12.2, 7.1 Hz, 1H), 1.67-1.78 (m, 1H), 1.52-1.63 (m, 1H), 1.41 (dtd, J = 12.2, 6.9, 5.2 Hz, 1H), 1.22 (d, J = 6.2 Hz, 3H) | (ESI (+)) m/e 350 (M + H)⁺ |
| 255 | N-{4-[ethyl(2-methoxyethyl)carbamoyl]phenyl}-1,3-dihydro-2H-isoindole-2-carboxamide | ¹H NMR (400 MHz, Pyridine-$d_5$, Temp = 90° C.) δ ppm 8.24-8.26 (bs, 1H), 7.89-7.91 (m, 2H), 7.49-7.53 (m, 2H), 7.19-7.24 (m, 2H), 7.15-7.19 (m, 2H), 4.85 (s, 4H), 3.62-3.66 (m, 2H), 3.53-3.58 (m, 2H), 3.50 (q, J = 7.1 Hz, 2H), 3.24 (s, 3H), 1.11 (t, J = 7.1 Hz, 3H) | (ESI (+)) m/e 368 (M + H)⁺ |
| 256 | N-(4-{[(2R)-1-hydroxy-3-methylbutan-2-yl]carbamoyl}phenyl)-1,3-dihydro-2H-isoindole-2-carboxamide | ¹H NMR (400 MHz, Pyridine-$d_5$, Temp = 90 C.) δ ppm 8.29-8.30 (bs, 1H), 8.05-8.08 (m, 2H), 7.87-7.90 (m, 2H), 7.46-7.53 (m, 1H), 7.19-7.24 (m, 2H), 7.15-7.19 (m, 2H), 4.84 (s, 4H), 4.29-4.36 (m, 1H), 3.99 (d, J = 4.8 Hz, 2H), 2.19-2.28 (m, 1H), 1.08 (d, J = 2.3 Hz, 3H), 1.06 (d, J = 2.4 Hz, 3H) | (ESI (+)) m/e 368 (M + H)⁺ |
| 257 | N-{4-[(2,6-dimethylmorpholin-4-yl)carbonyl]phenyl}-1,3-dihydro-2H-isoindole-2-carboxamide | ¹H NMR (400 MHz, Pyridine-$d_5$, Temp = 90° C.) δ ppm 8.33-8.40 (m, 1H), 7.92-7.96 (m, 2H), 7.54-7.58 (m, 2H), 7.19-7.25 (m, 2H), 7.15-7.19 (m, 2H), 4.86 (s, 4H), 4.14-4.22 (m, 1H), 3.93-4.01 (m, 1H), 3.70 (dd, J = 13.0, 3.4 Hz, 1H), 3.51-3.61 (m, 1H), 3.32 (dd, J = 13.0, 6.3 Hz, 1H), 2.64 (dd, J = 13.1, 10.5 Hz, 1H), 1.02-1.15 (m, 6H) | (ESI (+)) m/e 380 (M + H)⁺ |
| 258 | N-(4-{[(2R)-1-hydroxybutan-2-yl]carbamoyl}phenyl)-1,3-dihydro-2H-isoindole-2-carboxamide | ¹H NMR (400 MHz, Pyridine-$d_5$, Temp = 90° C.) δ ppm 8.25-8.31 (m, 1H), 8.05-8.08 (m, 2H), 7.87-7.90 (m, 2H), 7.58 (d, J = 7.5 Hz, 1H), 7.19-7.24 (m, 2H), 7.14-7.19 (m, 2H), 4.84 (s, 4H), 4.36-4.47 (m, 1H), 3.95 (d, J = 4.9 Hz, 2H), 1.85-1.96 (m, 1H), 1.72-1.84 (m, 1H), 1.02 (t, J = 7.4 Hz, 3H) | (ESI (+)) m/e 354 (M + H)⁺ |

| Ex | Name | ¹H NMR | MS |
|---|---|---|---|
| 259 | N-{4-[(2,5-dimethylpyrrolidin-1-yl)carbonyl]phenyl}-1,3-dihydro-2H-isoindole-2-carboxamide | ¹H NMR (400 MHz, Pyridine-$d_5$, Temp = 90° C.) δ ppm 8.23-8.25 (bs, 1H), 7.90-7.92 (m, 2H), 7.53-7.62 (m, 2H), 7.19-7.23 (m, 2H), 7.15-7.19 (m, 2H), 4.85 (s, 4H), 4.11-4.39 (m, 2H), 1.78-2.11 (m, 2H), 1.35-1.59 (m, 2H), 0.95-1.27 (m, 6H) | (ESI (+)) m/e 364 (M + H)⁺ |
| 260 | N-[4-(prop-2-yn-1-ylcarbamoyl)phenyl]-1,3-dihydro-2H-isoindole-2-carboxamide | ¹H NMR (400 MHz, DMSO-$d_6$, Temp = 90° C.) δ ppm 3.10 (t, J = 2.38 Hz, 1 H), 4.03 (dd, J = 5.55, 2.78 Hz, 2 H), 4.79 (s, 4 H), 7.28-7.42 (m, 4 H), 7.64-7.82 (m, 4 H), 8.60 (s, 1 H), 8.73 (t, J = 5.55 Hz, 1 H) | (ESI (+)) m/e 320 (M + H)⁺ |
| 261 | N-{4-[isopropyl(2-methoxyethyl)carbamoyl]phenyl}-1,3-dihydro-2H-isoindole-2-carboxamide | ¹H NMR (400 MHz, Pyridine-$d_5$, Temp = 90° C.) δ ppm 8.26-8.28 (bs, 1H), 7.90-7.93 (m, 2H), 7.48-7.50 (m, 2H), 7.19-7.23 (m, 2H), 7.15-7.18 (m, 2H), 4.85 (s, 4H), 4.18-4.32 (m, 1H), 3.56-3.68 (m, 4H), 3.26 (s, 3H), 1.13 (d, J = 6.7 Hz, 6H) | (ESI (−)) m/e 380 (M − H)⁻ |
| 262 | N-{4-[isopropyl(propyl)carbamoyl]phenyl}-1,3-dihydro-2H-isoindole-2-carboxamide | ¹H NMR (400 MHz, Pyridine-$d_5$, Temp = 90° C.) δ ppm 8.24-8.26 (bs, 1H), 7.90-7.92 (m, 2H), 7.46-7.48 (m, 2H), 7.19-7.23 (m, 2H), 7.16-7.18 (m, 2H), 4.85 (s, 4H), 4.20-4.32 (m, 1H), 3.25-3.30 (m, 2H), 1.59-1.77 (m, 2H), 1.12-1.17 (m, 6H), 0.82 (t, J = 7.4 Hz, 3H) | (ESI (+)) m/e 366 (M + H)⁺ |
| 263 | N-{4-[(2-cyanoethyl)(cyclopropyl)carbamoyl]phenyl}-1,3-dihydro-2H-isoindole-2-carboxamide | ¹H NMR (400 MHz, Pyridine-$d_5$, Temp = 90° C.) δ ppm 8.27-8.29 (bs, 1H), 7.90-7.93 (m, 2H), 7.65-7.68 (m, 2H), 7.20-7.23 (m, 2H), 7.15-7.19 (m, 2H), 4.85 (s, 4H), 3.81 (t, J = 6.6 Hz, 2H), 2.90-2.96 (m, 1H), 2.83 (t, J = 6.6 Hz, 2H), 0.54-0.61 (m, 2H), 0.45-0.52 (m, 2H) | (ESI (+)) m/e 375 (M + H)⁺ |
| 264 | N-{4-[ethyl(isopropyl)carbamoyl]phenyl}-1,3-dihydro-2H-isoindole-2-carboxamide | ¹H NMR (400 MHz, Pyridine-$d_5$, Temp = 90° C.) δ ppm 8.23-8.25 (bs, 1H), 7.89-7.92 (m, 2H), 7.45-7.48 (m, 2H), 7.19-7.23 (m, 2H), 7.15-7.18 (m, 2H), 4.85 (s, 4H), 4.27 (p, J = 6.7 Hz, 1H), 3.36 (q, J = 7.0 Hz, 2H), 1.18 (t, J = 6.9 Hz, 3H), 1.11 (d, J = 6.7 Hz, 6H) | (ESI (+)) m/e 352 (M + H)⁺ |
| 265 | N-{4-[(3-fluoropyrrolidin-1-yl)carbonyl]phenyl}-1,3-dihydro-2H-isoindole-2-carboxamide | ¹H NMR (500 MHz, DMSO-$d_6$/Deuterium Oxide) δ ppm 7.63-7.66 (m, 2H), 7.36-7.41 (m, 2H), 7.33-7.36 (m, 2H), 7.31-7.35 (m, 2H), 5.21-5.48 (m, 1H), 4.79 (s, 4H), 3.53-3.79 (m, 4H), 1.98-2.25 (m, 2H) | (APCI (+)) m/e 354 (M + H)⁺ |
| 266 | N-{4-[(1,3-dihydro-2H-isoindol-2-ylcarbonyl)amino]benzoyl}-N-isopropyl-beta-alanine | ¹H NMR (500 MHz, DMSO-$d_6$/Deuterium Oxide) δ ppm 7.59-7.62 (m, 2H), 7.37-7.40 (m, 2H), 7.31-7.36 (m, 2H), 7.24-7.27 (m, 2H), 4.78-4.79 (bs, 4H), 1.00-1.27 (m, 6H) | (ESI (+)) m/e 396 (M + H)⁺ |
| 267 | N-{4-[methyl(propyl)carbamoyl]phenyl}-1,3-dihydro-2H-isoindole-2-carboxamide | ¹H NMR (400 MHz, DMSO-$d_6$, Temp = 90° C.) δ ppm 0.82 (t, J = 7.32 Hz, 3 H), 1.49-1.62 (m, 2 H), 2.92 (s, 3 H), 3.27-3.34 (m, 2 H), 4.78 (s, 4 H), 7.23-7.37 (m, 6 H), 7.58-7.63 (m, 2 H), 8.26 (s, 1 H) | (ESI (+)) m/e 338 (M + H)⁺ |
| 268 | 5,6-dimethoxy-N-{4-[(3-phenylpropyl)carbamoyl]phenyl}-1,3-dihydro-2H-isoindole-2-carboxamide | ¹H NMR (300 MHz, DMSO-$d_6$) δ ppm 8.54 (s, 1H), 8.29 (t, J = 5.6 Hz, 1H), 7.75-7.78 (m, 2H), 7.61-7.68 (m, 2H), 7.15-7.32 (m, 5H), 6.95 (s, 2H), 4.69-4.70 (bs, 4H), 3.32 (s, 6H), 3.21-3.30 (m, 2H), 2.59-2.68 (m, 2H), 1.76-1.90 (m, 2H) | (ESI (+)) m/e 460 (M + H)⁺ |
| 269 | N-(4-{[3-(4-chlorophenoxy)propyl]carbamoyl}phenyl)-1,3-dihydro-2H-isoindole-2-carboxamide | ¹H NMR (300 MHz, DMSO-$d_6$) δ ppm 8.57 (s, 1H), 8.36 (t, J = 5.6 Hz, 1H), 7.75-7.79 (m, 2H), 7.64-7.68 (m, 2H), 7.29-7.39 (m, 6H), 6.94-6.98 (m, 2H), 4.79 (s, 4H), 4.03 (t, J = 6.1 Hz, 2H), 3.37-3.44 (m, 2H), 1.97 (p, J = 6.5 Hz, 2H) | (ESI (+)) m/e 450 (M + H)⁺ |
| 270 | N-(4-{[4-(trifluoromethoxy)phenyl]carbamoyl}phenyl)-1,3-dihydro-2H-isoindole-2-carboxamide | ¹H NMR (500 MHz, DMSO-$d_6$/Deuterium Oxide) δ ppm 7.89-7.93 (m, 2H), 7.85-7.89 (m, 2H), 7.72-7.75 (m, 2H), 7.33-7.41 (m, 6H), 4.80-4.82 (bs, 4H) | (ESI (+)) m/e 442 (M + H)⁺ |

| Ex | Name | ¹H NMR | MS |
|---|---|---|---|
| 271 | N-{4-[(4-phenyl-1,3-thiazol-2-yl)carbamoyl]phenyl}-1,3-dihydro-2H-isoindole-2-carboxamide | ¹H NMR (400 MHz, DMSO-d₆/Deuterium Oxide, Temp = 90° C.) δ ppm 8.06-8.09 (m, 2H), 7.94-7.97 (m, 2H), 7.75-7.78 (m, 2H), 7.55 (s, 1H), 7.44-7.49 (m, 2H), 7.37-7.41 (m, 2H), 7.32-7.37 (m, 3H), 4.84 (s, 4H) | (ESI (+)) m/e 441 (M + H)⁺ |
| 284 | 5-bromo-N-[4-(propylcarbamoyl)phenyl]-1,3-dihydro-2H-isoindole-2-carboxamide | ¹H NMR (300 MHz, DMSO-d₆) δ ppm 8.60 (s, 1H), 8.25 (t, J = 5.6 Hz, 1H), 7.74-7.78 (m, 2H), 7.62-7.67 (m, 2H), 7.59-7.62 (m, 1H), 7.50 (dd, J = 8.1, 1.9 Hz, 1H), 7.34 (d, J = 8.1 Hz, 1H), 4.70-4.82 (m, 4H), 3.15-3.26 (m, 2H), 1.45-1.61 (m, 2H), 0.89 (t, J = 7.4 Hz, 3H) | (ESI (+)) m/e 402 (M + H)⁺ |
| 373 | 5-fluoro-N-[4-(propylcarbamoyl)phenyl]-1,3-dihydro-2H-isoindole-2-carboxamide | ¹H NMR (300 MHz, DMSO-d₆) δ ppm 8.58 (s, 1H), 8.25 (t, J = 5.6 Hz, 1H), 7.74-7.78 (m, 2H), 7.62-7.66 (m, 2H), 7.39 (dd, J = 8.4, 5.2 Hz, 1H), 7.24 (dd, J = 9.1, 2.3 Hz, 1H), 7.10-7.19 (m, 1H), 4.74-4.78 (m, 4H), 3.16-3.21 (m, 2H), 1.46-1.59 (m, 2H), 0.89 (t, J = 7.4 Hz, 3H); | (ESI (+)) m/e 342 (M + H)⁺ |
| 412 | N-{4-[(2-methoxyethyl)carbamoyl]phenyl}-1,3-dihydro-2H-isoindole-2-carboxamide | ¹H NMR (400 MHz, DMSO-d₆, Temp = 90° C.) δ ppm 3.27 (s, 3 H), 3.35-3.49 (m, 4 H), 4.79 (s, 4 H), 7.25-7.40 (m, 4 H), 7.62-7.69 (m, 2 H), 7.74-7.81 (m, 2 H), 8.31 (t, J = 5.09 Hz, 1 H), 8.57 (s, 1 H) | (ESI (+)) m/e 340 (M + H)⁺ |
| 413 | N-{4-[(5-chloropyridin-2-yl)carbamoyl]phenyl}-1,3-dihydro-2H-isoindole-2-carboxamide | ¹H NMR (400 MHz, DMSO-d₆/Deuterium Oxide, Temp = 90° C.) δ ppm 8.37 (d, J = 2.7 Hz, 1H), 8.16 (d, J = 8.9 Hz, 1H), 7.94-7.97 (m, 2H), 7.89 (dd, J = 8.8, 2.6 Hz, 1H), 7.69-7.72 (m, 2H), 7.35-7.38 (m, 2H), 7.30-7.33 (m, 2H), 4.81 (s, 4H) | (ESI (+)) m/e 393 (M + H)⁺ |
| 414 | N-{4-[(3-hydroxy-4-methoxyphenyl)carbamoyl]phenyl}-1,3-dihydro-2H-isoindole-2-carboxamide | ¹H NMR (400 MHz, DMSO-d₆/Deuterium Oxide, Temp = 90° C.) δ ppm 7.85-7.88 (m, 2H), 7.66-7.69 (m, 2H), 7.34-7.39 (m, 2H), 7.30-7.34 (m, 1H), 7.28-7.30 (m, 1H), 7.09 (dd, J = 8.6, 2.5 Hz, 1H), 6.88 (d, J = 8.6 Hz, 1H), 4.81 (s, 4H), 3.77 (s, 3H) | (ESI (+)) m/e 404 (M + H)⁺ |
| 415 | N-{4-[(2,4-dimethoxybenzyl)carbamoyl]phenyl}-1,3-dihydro-2H-isoindole-2-carboxamide | ¹H NMR (400 MHz, DMSO-d₆/Deuterium Oxide, Temp = 90° C.) δ ppm 7.77-7.79 (m, 2H), 7.61-7.64 (m, 2H), 7.33-7.38 (m, 2H), 7.28-7.34 (m, 2H), 7.14 (d, J = 8.2 Hz, 1H), 6.55 (d, J = 2.4 Hz, 1H), 6.48 (dd, J = 8.2, 2.4 Hz, 1H), 4.79 (s, 4H), 4.38-4.40 (m, 2H), 3.82 (s, 3H), 3.75 (s, 3H) | (ESI (+)) m/e 432 (M + H)⁺ |
| 416 | N-(4-{[4-(2-oxopyrrolidin-1-yl)benzyl]carbamoyl}phenyl)-1,3-dihydro-2H-isoindole-2-carboxamide | ¹H NMR (400 MHz, DMSO-d₆/Deuterium Oxide, Temp = 90° C.) δ ppm 7.78-7.80 (m, 2H), 7.62-7.68 (m, 2H), 7.54-7.56 (m, 2H), 7.29-7.38 (m, 6H), 4.79 (s, 4H), 4.45-4.47 (m, 2H), 3.82 (t, J = 7.0 Hz, 2H), 2.45-2.50 (m, 2H), 2.04-2.13 (m, 2H) | (ESI (+)) m/e 455 (M + H)⁺ |
| 417 | N-(4-{[(1S,2S)-2-hydroxy-2,3-dihydro-1H-inden-1-yl]carbamoyl}phenyl)-1,3-dihydro-2H-isoindole-2-carboxamide | ¹H NMR (400 MHz, DMSO-d₆, Temp = 90° C.) δ ppm 2.67-2.83 (m, 1 H), 3.18 (dd, J = 15.47, 7.14 Hz, 1 H), 4.34-4.49 (m, 1 H), 4.79 (s, 4 H), 5.25-5.34 (m, 2 H), 7.06-7.24 (m, 4 H), 7.30-7.42 (m, 4 H), 7.69 (d, J = 8.73 Hz, 2 H), 7.87 (d, J = 9.12 Hz, 2 H), 8.50-8.62 (m, 2 H) | (ESI (+)) m/e 414 (M + H)⁺ |
| 418 | N-(4-{[(1-hydroxycyclopropyl)methyl]carbamoyl}phenyl)-1,3-dihydro-2H-isoindole-2-carboxamide | ¹H NMR (400 MHz, DMSO-d₆, Temp = 90° C.) δ ppm 0.55 (s, 4 H), 3.42 (d, J = 5.55 Hz, 2 H), 4.79 (s, 4 H), 5.41 (s, 1 H), 7.28-7.41 (m, 4 H), 7.64-7.70 (m, 2 H), 7.75-7.84 (m, 2 H), 8.20 (t, J = 5.75 Hz, 1 H), 8.58 (s, 1 H) | (ESI (−)) m/e 350 (M + H)⁻ |
| 419 | N-{4-[(tetrahydro-2H-pyran-2-ylmethyl)carbamoyl]phenyl}-1,3-dihydro-2H-isoindole-2-carboxamide | ¹H NMR (300 MHz, DMSO-d₆) δ ppm 8.57 (s, 1H), 8.29 (t, J = 5.8 Hz, 1H), 7.76-7.80 (m, 2H), 7.64-7.68 (m, 2H), 7.30-7.39 (m, 4H), 4.78-4.79 (bs, 4H), 3.84-3.90 (m, 1H), 3.32-3.47 (m, 2H), 3.21-3.30 (m, 2H), 1.75-1.81 (m, 1H), 1.58-1.65 (m, 1H), 1.33-1.54 (m, 3H), 1.06-1.28 (m, 1H) | (ESI (−)) m/e 378 (M + H)⁻ |

| Ex | Name | ¹H NMR | MS |
|---|---|---|---|
| 420 | N-{4-[(tetrahydro-2H-pyran-3-ylmethyl)carbamoyl]phenyl}-1,3-dihydro-2H-isoindole-2-carboxamide | ¹H NMR (300 MHz, DMSO-$d_6$) δ ppm 8.57 (s, 1H), 8.27 (t, J = 5.8 Hz, 1H), 7.74-7.79 (m, 2H), 7.64-7.68 (m, 2H), 7.30-7.39 (m, 4H), 4.78-4.79 (bs, 4H), 3.68-3.80 (m, 2H), 3.26-3.36 (m, 1H), 3.06-3.18 (m, 3H), 1.74-1.82 (m, 2H), 1.38-1.68 (m, 2H), 1.15-1.30 (m, 1H) | (ESI (+)) m/e 380 (M + H)⁺ |
| 421 | N-{4-[(tetrahydro-2H-pyran-4-ylmethyl)carbamoyl]phenyl}-1,3-dihydro-2H-isoindole-2-carboxamide | ¹H NMR (300 MHz, DMSO-$d_6$) δ ppm 8.56 (s, 1H), 8.28 (t, J = 5.8 Hz, 1H), 7.75-7.79 (m, 2H), 7.64-7.68 (m, 2H), 7.25-7.43 (m, 4H), 4.79 (s, 4H), 3.81-3.88 (m, 2H), 3.21-3.31 (m, 2H), 3.14 (t, J = 6.3 Hz, 2H), 1.71-1.86 (m, 1H), 1.56-1.63 (m, 2H), 1.07-1.30 (m, 2H) | (ESI (+)) m/e 380 (M + H)⁺ |
| 425 | N-{4-[(4-benzoylpiperazin-1-yl)carbonyl]phenyl}-1,3-dihydro-2H-isoindole-2-carboxamide | ¹H NMR (300 MHz, DMSO-$d_6$) δ ppm 8.55 (s, 1H), 7.64-7.68 (m, 2H), 7.40-7.50 (m, 5H), 7.29-7.40 (m, 6H), 4.78-4.79 (bs, 4H), 3.33-3.86 (m, 8H) | (ESI (+)) m/e 455 (M + H)⁺ |
| 434 | N-(4-{[4-(tetrahydrofuran-3-ylmethyl)piperazin-1-yl]carbonyl}phenyl)-1,3-dihydro-2H-isoindole-2-carboxamide | ¹H NMR (300 MHz, DMSO-$d_6$) δ ppm 8.54 (s, 1H), 7.62-7.66 (m, 2H), 7.28-7.39 (m, 6H), 4.78-4.79 (bs, 4H), 3.88-3.95 (m, 1H), 3.68-3.77 (m, 1H), 3.55-3.64 (m, 1H), 3.39-3.56 (m, 4H), 2.46-2.56 (m, 2H), 2.35-2.47 (m, 4H), 1.85-1.99 (m, 1H), 1.66-1.86 (m, 2H), 1.39-1.54 (m, 1H) | (ESI (+)) m/e 435 (M + H)⁺ |
| 435 | 5-fluoro-N-[4-({[(2S)-tetrahydrofuran-2-ylmethyl]amino}carbonyl)phenyl]-1,3-dihydro-2H-isoindole-2-carboxamide | ¹H NMR (300 MHz, DMSO-$d_6$) δ ppm 8.60 (s, 1H), 8.33 (t, J = 5.8 Hz, 1H), 7.76-7.80 (m, 2H), 7.63-7.67 (m, 2H), 7.39 (dd, J = 8.4, 5.2 Hz, 1H), 7.24 (dd, J = 9.1, 2.4 Hz, 1H), 7.15 (td, J = 8.9, 2.5 Hz, 1H), 4.74-4.79 (m, 4H), 3.92-4.03 (m, 1H), 3.74-3.82 (m, 1H), 3.58-3.66 (m, 1H), 3.24-3.34 (m, 2H), 1.76-1.96 (m, 3H), 1.52-1.69 (m, 1H) | (ESI (+)) m/e 384 (M + H)⁺ |
| 436 | 5-fluoro-N-[4-({[(2R)-tetrahydrofuran-2-ylmethyl]amino}carbonyl)phenyl]-1,3-dihydro-2H-isoindole-2-carboxamide | ¹H NMR (300 MHz, DMSO-$d_6$) δ ppm 8.60 (s, 1H), 8.33 (t, J = 5.8 Hz, 1H), 7.76-7.80 (m, 2H), 7.63-7.67 (m, 2H), 7.39 (dd, J = 8.4, 5.2 Hz, 1H), 7.24 (dd, J = 9.1, 2.5 Hz, 1H), 7.15 (td, J = 8.9, 2.5 Hz, 1H), 4.74-4.79 (m, 4H), 3.96 (p, J = 6.3 Hz, 1H), 3.74-3.82 (m, 1H), 3.58-3.66 (m, 1H), 3.22-3.34 (m, 2H), 1.74-1.96 (m, 3H), 1.53-1.64 (m, 1H) | (ESI (+)) m/e 384 (M + H)⁺ |
| 438 | N-(4-{[4-(2-methoxyethyl)piperazin-1-yl]carbonyl}phenyl)-1,3-dihydro-2H-isoindole-2-carboxamide | ¹H NMR (300 MHz, DMSO-$d_6$) δ ppm 8.53 (s, 1H), 7.62-7.66 (m, 2H), 7.24-7.43 (m, 6H), 4.78 (s, 4H), 3.44 (t, J = 5.8 Hz, 6H), 3.23 (s, 3H), 2.43 (s, 4H) | (ESI (+)) m/e 409 (M + H)⁺ |
| 439 | N-(4-{[(2S)-2-(2-hydroxyethyl)piperidin-1-yl]carbonyl}phenyl)-1,3-dihydro-2H-isoindole-2-carboxamide | ¹H NMR (300 MHz, DMSO-$d_6$) δ ppm 8.51 (s, 1H), 7.61-7.65 (m, 2H), 7.25-7.39 (m, 6H), 4.78-4.79 (bs, 4H), 4.36 (t, J = 5.1 Hz, 1H), 3.46-4.87 (m, 2H), 3.31-3.43 (m, 2H), 2.78-3.10 (m, 1H), 1.80-1.97 (m, 1H), 1.52-1.76 (m, 6H), 1.26-1.47 (m, 1H) | (ESI (+)) m/e 394 (M + H)⁺ |
| 449 | N-[4-({[(1S)-2-hydroxy-1-pyridin-2-ylethyl]amino}carbonyl)phenyl]-1,3-dihydro-2H-isoindole-2-carboxamide | ¹H NMR (300 MHz, DMSO-$d_6$) δ ppm 8.61 (s, 1H), 8.53 (ddd, J = 4.8, 1.8, 0.9 Hz, 1H), 8.46 (d, J = 7.8 Hz, 1H), 7.84-7.88 (m, 2H), 7.75 (td, J = 7.7, 1.8 Hz, 1H), 7.67-7.73 (m, 2H), 7.29-7.44 (m, 5H), 7.26 (ddd, J = 7.4, 4.9, 1.1 Hz, 1H), 5.10-5.17 (m, 1H), 4.88-4.93 (m, 1H), 4.80 (s, 3H), 3.73-3.88 (m, 2H) | (ESI (−)) m/e 401 (M − H)⁻ |
| 562 | N-[4-(isobutoxycarbamoyl)phenyl]-1,3-dihydro-2H-isoindole-2-carboxamide | ¹H NMR (300 MHz, DMSO-$d_6$) δ ppm 11.42 (s, 1H), 8.60 (s, 1H), 7.67 (s, 4H), 7.41-7.28 (m, 4H), 4.79 (bs, 4H), 3.65 (d, J = 6.7 Hz, 2H), 2.02-1.85 (m, 1H), 0.94 (d, J = 6.7 Hz, 6H) | (ESI (+)) m/e 354 (M + H)⁺ |

-continued

| Ex | Name | ¹H NMR | MS |
|---|---|---|---|
| 567 | 5-fluoro-N-{4-[(tetrahydro-2H-pyran-2-ylmethyl)carbamoyl]phenyl}-1,3-dihydro-2H-isoindole-2-carboxamide | ¹H NMR (300 MHz, DMSO-$d_6$) δ 8.59 (s, 1H), 8.29 (t, J = 5.8 Hz, 1H), 7.81-7.74 (m, 2H), 7.68-7.61 (m, 2H), 7.40 (dd, J = 8.4, 5.2 Hz, 1H), 7.24 (dd, J = 9.1, 2.5 Hz, 1H), 7.15 (td, J = 8.9, 2.5 Hz, 1H), 4.80-4.73 (m, 3H), 4.05-3.99 (m, 1H), 3.87 (dd, J = 11.3, 3.0 Hz, 1H), 3.24 (dd, J = 8.8, 4.0 Hz, 2H), 1.80-1.74 (m, 1H), 1.66-1.56 (m, 1H), 1.57-1.33 (m, 3H), 1.28-1.04 (m, 1H) | (ESI (+)) m/e 398 (M + H)⁺ |
| 568 | 5-fluoro-N-{4-[(tetrahydro-2H-pyran-3-ylmethyl)carbamoyl]phenyl}-1,3-dihydro-2H-isoindole-2-carboxamide | ¹H NMR (300 MHz, DMSO-$d_6$) δ 8.59 (s, 1H), 8.28 (t, J = 5.7 Hz, 1H), 7.76 (d, J = 8.8 Hz, 2H), 7.65 (d, J = 8.8 Hz, 2H), 7.58-7.32 (m, 1H), 7.31-7.06 (m, 2H), 4.76 (d, J = 8.0 Hz, 4H), 3.85-3.62 (m, 2H), 3.23-2.96 (m, 3H), 1.91-1.69 (m, 2H), 1.68-1.35 (m, 2H), 1.35-1.11 (m, 1H) | (ESI (+)) m/e 398 (M + H)⁺ |
| 569 | 5-fluoro-N-{4-[(tetrahydro-2H-pyran-4-ylmethyl)carbamoyl]phenyl}-1,3-dihydro-2H-isoindole-2-carboxamide | ¹H NMR (300 MHz, DMSO-$d_6$) δ 8.58 (s, 1H), 8.28 (t, J = 5.8 Hz, 1H), 7.80-7.73 (m, 2H), 7.68-7.61 (m, 2H), 7.39 (dd, J = 8.4, 5.2 Hz, 1H), 7.24 (dd, J = 9.1, 2.5 Hz, 1H), 7.14 (td, J = 8.9, 2.5 Hz, 1H), 4.80-4.72 (m, 4H), 3.89-3.79 (m, 2H), 3.28-3.20 (m, 1H), 3.14 (t, J = 6.3 Hz, 2H), 1.88-1.69 (m, 1H), 1.64-1.54 (m, 2H), 1.28-1.10 (m, 2H) | (ESI (+)) m/e 398 (M + H)⁺ |
| 570 | 5-fluoro-N-(4-{[(1S)-2-hydroxy-1-phenylethyl]carbamoyl}phenyl)-1,3-dihydro-2H-isoindole-2-carboxamide | ¹H NMR (300 MHz, DMSO-$d_6$) δ 8.61 (s, 1H), 8.49 (d, J = 8.0 Hz, 1H), 7.88-7.80 (m, 2H), 7.71-7.64 (m, 2H), 7.44-7.36 (m, 3H), 7.36-7.27 (m, 2H), 7.28-7.09 (m, 3H), 5.12-5.01 (m, 1H), 4.90 (t, J = 5.8 Hz, 1H), 4.81-4.73 (m, 4H), 3.78-3.59 (m, 2H) | (ESI (+)) m/e 420 (M + H)⁺ |
| 571 | 5-fluoro-N-(4-{[(1S)-2-hydroxy-1-(pyridin-2-yl)ethyl]carbamoyl}phenyl)-1,3-dihydro-2H-isoindole-2-carboxamide | ¹H NMR (300 MHz, DMSO-$d_6$) δ 8.62 (s, 1H), 8.53 (ddd, J = 4.8, 1.8, 0.9 Hz, 1H), 8.46 (d, J = 7.8 Hz, 1H), 7.90-7.82 (m, 2H), 7.78-7.71 (m, 1H), 7.69 (t, J = 5.5 Hz, 2H), 7.44-7.36 (m, 2H), 7.30-7.09 (m, 3H), 5.19-5.08 (m, 1H), 4.90 (t, J = 5.9 Hz, 1H), 4.87-4.72 (m, 4H), 3.89-3.72 (m, 2H);) | (ESI (+)) m/e 421 (M + H)⁺ |
| 572 | 5-fluoro-N-(4-{[(2S)-1-hydroxy-4-methylpentan-2-yl]carbamoyl}phenyl)-1,3-dihydro-2H-isoindole-2-carboxamide | ¹H NMR (300 MHz, DMSO-$d_6$) δ 8.59 (s, 1H), 7.84-7.75 (m, 3H), 7.68-7.61 (m, 2H), 7.40 (dd, J = 8.4, 5.2 Hz, 1H), 7.24 (dd, J = 9.1, 2.5 Hz, 1H), 7.15 (td, J = 8.9, 2.5 Hz, 1H), 4.80-4.73 (m, 4H), 4.65 (t, J = 5.7 Hz, 1H), 4.10-3.97 (m, 1H), 3.49-3.35 (m, 1H), 1.74-1.54 (m, 1H), 1.52-1.31 (m, 2H), 0.88 (t, J = 6.8 Hz, 6H) | (ESI (+)) m/e 400 (M + H)⁺ |
| 585 | N-(4-{[(2S)-1-hydroxy-4-(methylthio)butan-2-yl]carbamoyl}phenyl)-1,3-dihydro-2H-isoindole-2-carboxamide | ¹H NMR (400 MHz, DMSO-$d_6$) δ ppm 8.58 (s, 1H), 7.90 (d, J = 8.3 Hz, 1H), 7.79 (m, 2H), 7.67 (m, 2H), 7.40-7.29 (m, 4H), 4.79 (s, 4H), 4.73 (m, 1H), 4.03 (m, 1H), 3.47 (m, 1H), 3.58 (m, 1H), 2.60-2.40 (m, 2H), 2.04 (s, 3H), 1.90 (m, 1H), 1.74 (m, 1H) | (ESI (+)) m/e 400 (M + H)⁺ |
| 586 | N-(4-{[(2S,3S)-1-hydroxy-3-methylpentan-2-yl]carbamoyl}phenyl)-1,3-dihydro-2H-isoindole-2-carboxamide | ¹H NMR (400 MHz, DMSO-$d_6$) δ ppm 8.57 (s, 1H), 7.80 (m, 3H), 7.66 (m, 2H), 7.34 (m, 4H), 4.79 (bs, 4H), 4.52 (t, J = 5.5 Hz, 1H), 3.84 (m, 1H), 3.53 (m, 2H), 1.69 (m, 1H), 1.49 (m, 1H), 1.10 (m, 1H), 0.91-0.81 (m, 6H) | (ESI (+)) m/e 382 (M + H)⁺ |
| 587 | N-(4-{[(2S)-1-hydroxypropan-2-yl]carbamoyl}phenyl)-1,3-dihydro-2H-isoindole-2-carboxamide | ¹H NMR (400 MHz, DMSO-$d_6$) δ ppm 8.57 (s, 1H), 7.89 (d, J = 8.0 Hz, 1H), 7.78 (m, 2H), 7.66 (m, 2H), 7.40-7.29 (m, 4H), 4.79 (bs, 4H), 4.70 (t, J = 5.7 Hz, 1H), 4.00 (m, 1H), 3.46 (dt, J = 10.8, 3.33 (m, 1H), 5.4 Hz, 1H), 1.13 (d, J = 6.7 Hz, 3H) | (ESI (+)) m/e 340 (M + H)⁺ |
| 588 | N-(4-{[(2S,3R)-1,3-dihydroxybutan-2-yl]carbamoyl}phenyl)-1,3-dihydro-2H-isoindole-2-carboxamide | ¹H NMR (400 MHz, DMSO-$d_6$) δ ppm 8.57 (bs, 1H), 7.78 (m, 3H), 7.67 (m, 2H), 7.40-7.29 (m, 4H), 4.79 (bs, 4H), 4.67 (d, J = 5.2 Hz, 1H), 4.52 (m, 1H), 3.90-3.72 (m, 2H), 3.63 (m, 2H), 1.08 (d, J = 6.12 Hz, 3H) | (ESI (+)) m/e 370 (M + H)⁺ |

| Ex | Name | ¹H NMR | MS |
|---|---|---|---|
| 589 | N-(4-{[(2S)-1-hydroxyhexan-2-yl]carbamoyl}phenyl)-1,3-dihydro-2H-isoindole-2-carboxamide | ¹H NMR (400 MHz, DMSO-d₆) δ ppm 8.57 (s, 1H), 7.80 (m, 3H), 7.66 (m, 2H), 7.40-7.29 (m, 4H), 4.79 (bs, 4H), 4.65 (t, J = 5.7 Hz, 1H), 3.93 (m, 1H), 3.44 (dt, J = 10.8, 5.4 Hz, 1H), 3.32 (m, 1H), 1.63 (m, 1H), 1.44 (m, 1H), 1.28 (m, 4H), 0.86 (t, J = 6.3 Hz, 3H) | (ESI (+)) m/e 382 (M + H)⁺ |
| 590 | N-(4-{[(2S)-1-hydroxypentan-2-yl]carbamoyl}phenyl)-1,3-dihydro-2H-isoindole-2-carboxamide | ¹H NMR (400 MHz, DMSO-d₆) δ ppm 8.57 (s, 1H), 7.80 (m, 3H), 7.66 (m, 2H), 7.40-7.29 (m, 4H), 4.79 (bs, 4H), 4.64 (t, J = 5.7 Hz, 1H), 3.95 (m, 1H), 3.44 (dt, J = 10.8, 5.4 Hz, 1H), 3.32 (m, 1H), 1.58 (m, 1H), 1.50-1.22 (m, 3H), 0.88 (t, J = 7.3 Hz, 3H) | (ESI (+)) m/e 368 (M + H)⁺ |
| 591 | N-(4-{[(1S,2S)-2-hydroxycyclopentyl]carbamoyl}phenyl)-1,3-dihydro-2H-isoindole-2-carboxamide | ¹H NMR (400 MHz, DMSO-d₆) δ ppm 8.57 (s, 1H), 8.03 (m, 1H), 7.78 (m, 2H), 7.66 (m, 2H), 7.40-7.29 (m, 4H), 4.81 (bs, 4H), 4.75 (t, J = 5.7 Hz, 1H), 4.98 (m, 2H), 1.99 (m, 1H), 1.86 (m, 1H), 1.65 (m, 2H), 1.47 (m, 2H) | (ESI (+)) m/e 366 (M + H)⁺ |
| 592 | N-(4-{[(1S,2R)-2-hydroxycyclopentyl]carbamoyl}phenyl)-1,3-dihydro-2H-isoindole-2-carboxamide | ¹H NMR (400 MHz, DMSO-d₆) δ ppm 8.57 (s, 1H), 7.80 (m, 2H), 7.65 (m, 3H), 7.40-7.28 (m, 4H), 4.79 (bs, 4H), 4.71 (d, J = 3.6 Hz, 1H), 4.04 (m, 2H), 1.88-1.44 (m, 6H) | (ESI (+)) m/e 366 (M + H)⁺ |
| 593 | N-(4-{[(2S)-1-cyclohexyl-3-hydroxypropan-2-yl]carbamoyl}phenyl)-1,3-dihydro-2H-isoindole-2-carboxamide | ¹H NMR (400 MHz, DMSO-d₆) δ ppm 8.57 (s, 1H), 7.81 (m, 3H), 7.67 (m, 2H), 7.43-7.26 (m, 4H), 4.79 (s, 4H), 4.64 (t, J = 5.7 Hz, 1H), 4.06 (m, 1H), 3.42 (m, 1H), 3.30 (m, 1H), 1.80 (d, J = 12.6 Hz, 1H), 1.62 (m, 4H), 1.43 (m, 2H), 1.32 (m, 1H), 1.14 (m, 3H), 0.95 (m, 1H), 0.83 (m, 1H) | (ESI (+)) m/e 422 (M + H)⁺ |
| 594 | N-[4-({(2R)-1-hydroxy-3-[(4-methylbenzyl)thio]propan-2-yl}carbamoyl)phenyl]-1,3-dihydro-2H-isoindole-2-carboxamide | ¹H NMR (400 MHz, DMSO-d₆) δ ppm 8.59 (s, 1H), 7.98 (d, J = 8.2 Hz, 1H), 7.79 (m, 2H), 7.68 (m, 2H), 7.40-7.28 (m, 4H), 7.20 (m, 2H), 7.10 (m, 2H), 4.80 (m, 5H), 4.13 (m, 1H), 3.71 (s, 2H), 3.55 (m, 1H), 3.44 (m, 1H), 2.70 (dd, J = 13.3, 5.7 Hz, 1H), 2.55 (m, 1H), 2.27 (s, 3H) | (ESI (+)) m/e 476 (M + H)⁺ |
| 595 | N-(4-{[(1S)-1-(4-tert-butylphenyl)-2-hydroxyethyl]carbamoyl}phenyl)-1,3-dihydro-2H-isoindole-2-carboxamide | ¹H NMR (400 MHz, DMSO-d₆) δ ppm 8.59 (s, 1H), 8.45 (d, J = 8.0 Hz, 1H), 7.83 (m, 2H), 7.68 (m, 2H), 7.40-7.27 (m, 8H), 5.03 (m, 1H), 4.87 (t, J = 5.8 Hz, 1H), 4.79 (bs, 4H), 3.67 (m, 2H), 1.26 (s, 9H) | (ESI (+)) m/e 458 (M + H)⁺ |
| 597 | 5-methoxy-N-[4-(propylcarbamoyl)phenyl]-1,3-dihydro-2H-isoindole-2-carboxamide | ¹H NMR (300 MHz, DMSO-d₆) δ ppm 8.53 (s, 1H), 8.24 (m, 1H), 7.80-7.72 (m, 2H), 7.67-7.61 (m, 2H), 7.26 (d, J = 8.3 Hz, 1H), 6.98-6.91 (m, 1H), 6.88 (dd, J = 8.3, 2.4 Hz, 1H), 4.72 (m, 4H), 3.77 (s, 3H), 3.25-3.14 (m, 2H), 1.60-1.44 (m, 2H), 0.89 (t, J = 7.4 Hz, 3H) | (ESI (+)) m/e 354 (M + H)⁺ |
| 598 | 5-methyl-N-[4-(propylcarbamoyl)phenyl]-1,3-dihydro-2H-isoindole-2-carboxamide | ¹H NMR (300 MHz, DMSO-d₆) δ ppm 8.54 (s, 1H), 8.24 (m, 1H), 7.80-7.72 (m, 2H), 7.69-7.61 (m, 2H), 7.24 (d, J = 7.7 Hz, 1H), 7.17 (bs, 1H), 7.16-7.09 (m, 1H), 4.73 (bs, 4H), 3.23-3.14 (m, 2H), 2.33 (s, 3H), 1.60-1.44 (m, 2H), 0.89 (t, J = 7.4 Hz, 3H) | (ESI (+)) m/e 338 (M + H)⁺ |
| 716 | N-(4-{[(1-methylpyrrolidin-3-yl)methyl]carbamoyl}phenyl)-1,3-dihydro-2H-isoindole-2-carboxamide | ¹H NMR (300 MHz, DMSO-d₆) δ 8.60 (s, 1H), 8.40 (t, J = 5.7 Hz, 1H), 7.81-7.73 (m, 2H), 7.71-7.63 (m, 2H), 7.41-7.28 (m, 6H), 5.83 (dd, J = 19.3, 15.2 Hz, 1H), 4.79 (bs, 4H), 3.30-3.21 (m, 1H), 3.06-2.93 (m, 1H), 2.89-2.69 (m, 1H), 2.60 (dd, J = 17.2, 7.4 Hz, 1H), 2.32 (s, 3H), 2.04-1.85 (m, 1H), 1.58 (tt, J = 13.9, 6.9 Hz, 1H) | (ESI (+)) m/e 379 (M + H)⁺ |
| 719 | N-(4-{[(1-methylpiperidin-4-yl)methyl]carbamoyl}phenyl)-1,3-dihydro-2H-isoindole-2-carboxamide | ¹H NMR (300 MHz, DMSO-d₆) δ 8.57 (s, 1H), 8.27 (t, J = 5.8 Hz, 1H), 7.80-7.73 (m, 2H), 7.69-7.62 (m, 2H), 7.41-7.28 (m, 4H), 3.35-3.27 (m, 2H), 3.13 (t, J = 6.2 Hz, 2H), 3.03-2.93 (m, 1H), 2.86-2.77 (m, 2H), 2.20 (s, 3H), 2.17 (s, 1H), 2.00-1.82 (m, 2H), 1.70-1.45 (m, 3H), 1.28-1.11 (m, 2H) | (ESI (+)) m/e 393 (M + H)⁺ |

-continued

| Ex | Name | ¹H NMR | MS |
|---|---|---|---|
| 781 | N-(4-{[(1,1-dioxidotetrahydrothiophen-3-yl)methyl]carbamoyl}phenyl)-1,3-dihydro-2H-isoindole-2-carboxamide | ¹H NMR (300 MHz, DMSO DMSO-d$_6$) δ 8.58 (s, 1H), 8.44 (t, J = 5.8 Hz, 1H), 7.81-7.74 (m, 2H), 7.71-7.64 (m, 2H), 7.41-7.28 (m, 4H), 4.79 (s, 4H), 3.41-3.31 (m, 2H), 3.30 (s, 2H), 3.11-2.81 (m, 2H), 2.74-2.59 (m, 1H), 2.30-2.15 (m, 1H), 1.94-1.76 (m, 1H) | (ESI (+)) m/e 414 (M + H)⁺ |
| 782 | N-(4-{[(2,2-dimethyl-1,3-dioxolan-4-yl)methyl]carbamoyl}phenyl)-1,3-dihydro-2H-isoindole-2-carboxamide | ¹H NMR (300 MHz, DMSO-d$_6$) δ 8.58 (s, 1H), 8.38 (t, J = 5.8 Hz, 1H), 8.01-7.89 (m, 1H), 7.78 (d, J = 8.9 Hz, 2H), 7.67 (d, J = 8.8 Hz, 2H), 7.44-7.24 (m, 4H), 4.79 (s, 4H), 4.20 (p, J = 5.9 Hz, 1H), 3.98 (dd, J = 8.3, 6.2 Hz, 1H), 3.71 (dd, J = 8.3, 5.8 Hz, 1H), 3.50-3.20 (m, 1H), 1.35 (s, 3H), 1.26 (s, 3H) | (ESI (+)) m/e 396 (M + H)⁺ |
| 783 | N-(4-{[(1S)-2-methoxy-1-phenylethyl]carbamoyl}phenyl)-1,3-dihydro-2H-isoindole-2-carboxamide | ¹H NMR (300 MHz, DMSO-d$_6$) δ 8.61 (d, J = 8.2 Hz, 2H), 7.87-7.79 (m, 2H), 7.70 (s, 1H), 7.67 (s, 1H), 7.46-7.20 (m, 9H), 5.27 (td, J = 8.4, 5.4 Hz, 1H), 4.79 (s, 4H), 3.70 (dd, J = 10.0, 8.6 Hz, 1H), 3.55 (dd, J = 10.0, 5.5 Hz, 1H), 3.30 (d, J = 2.9 Hz, 3H) | (ESI (+)) m/e 416 (M + H)⁺ |
| 784 | N-[4-({[(4S)-2,2-dimethyl-1,3-dioxolan-4-yl]methyl}carbamoyl)phenyl]-1,3-dihydro-2H-isoindole-2-carboxamide | ¹H NMR (300 MHz, DMSO-d$_6$) δ 8.58 (s, 1H), 8.39 (t, J = 5.8 Hz, 1H), 7.81-7.74 (m, 2H), 7.70-7.63 (m, 2H), 7.41-7.28 (m, 4H), 4.79 (s, 4H), 4.20 (p, J = 5.9 Hz, 1H), 3.98 (dd, J = 8.3, 6.2 Hz, 1H), 3.71 (dd, J = 8.3, 5.8 Hz, 1H), 3.30 (s, 1H), 1.35 (s, 3H), 1.26 (s, 3H) | (ESI (+)) m/e 396 (M + H)⁺ |
| 785 | N-[4-({[(4R)-2,2-dimethyl-1,3-dioxolan-4-yl]methyl}carbamoyl)phenyl]-1,3-dihydro-2H-isoindole-2-carboxamide | ¹H NMR (300 MHz, DMSO-d$_6$) δ 8.58 (s, 1H), 8.39 (t, J = 5.8 Hz, 1H), 7.81-7.74 (m, 2H), 7.70-7.63 (m, 2H), 7.43-7.27 (m, 4H), 4.79 (s, 4H), 4.20 (p, J = 5.9 Hz, 1H), 3.98 (dd, J = 8.3, 6.2 Hz, 1H), 3.71 (dd, J = 8.3, 5.8 Hz, 1H), 3.38 (ddd, J = 14.9, 12.8, 5.8 Hz, 1H), 1.35 (s, 3H), 1.26 (s, 3H) | (ESI (+)) m/e 396 (M + H)⁺ |
| 786 | N-[4-({[3-(hydroxymethyl)oxetan-3-yl]methyl}carbamoyl)phenyl]-1,3-dihydro-2H-isoindole-2-carboxamide | ¹H NMR (300 MHz, DMSO-d$_6$) δ 8.60 (s, 1H), 8.43 (t, J = 6.1 Hz, 1H), 7.83-7.76 (m, 2H), 7.72-7.65 (m, 2H), 7.41-7.28 (m, 4H), 4.89 (t, J = 5.6 Hz, 1H), 4.79 (s, 4H), 4.40 (d, J = 5.9 Hz, 2H), 4.29 (d, J = 5.8 Hz, 2H), 3.58 (d, J = 5.6 Hz, 2H), 3.51 (d, J = 6.0 Hz, 2H) | (ESI (+)) m/e 382 (M + H)⁺ |
| 790 | N-{4-[(2R)-butan-2-ylcarbamoyl]phenyl}-1,3-dihydro-2H-isoindole-2-carboxamide | ¹H NMR (400 MHz, DMSO-d$_6$, Temp = 90° C.) δ 7.81-7.71 (m, 2H), 7.71-7.48 (m, 2H), 7.44-7.23 (m, 4H), 4.79 (s, 4H), 3.92 (h, J = 6.7 Hz, 1H), 1.62-1.44 (m, 2H), 1.15 (d, J = 6.6 Hz, 3H), 0.88 (t, J = 7.4 Hz, 3H) | (ESI (+)) m/e 338 (M + H)⁺ |
| 802 | N-(4-{[(3-methyloxetan-3-yl)methyl]carbamoyl}phenyl)-1,3-dihydro-2H-isoindole-2-carboxamide | ¹H NMR (300 MHz, DMSO-d$_6$) δ 8.59 (s, 1H), 8.43 (t, J = 6.1 Hz, 1H), 7.83-7.76 (m, 2H), 7.71-7.65 (m, 2H), 7.41-7.28 (m, 4H), 4.79 (s, 4H), 4.48 (d, J = 5.7 Hz, 2H), 4.20 (d, J = 5.7 Hz, 2H), 3.44 (d, J = 6.0 Hz, 2H), 1.25 (s, 3H) | (ESI (+)) m/e 366 (M + H)⁺ |
| 809 | 5-cyano-N-{4-[(cyclopentylmethyl)carbamoyl]phenyl}-1,3-dihydro-2H-isoindole-2-carboxamide | ¹H NMR (400 MHz, DMSO-D$_2$O, Temp = 90° C.) δ ppm 7.79 (s, 1 H) 7.70-7.77 (m, 3 H) 7.60-7.63 (m, 1 H) 7.58-7.60 (m, 1 H) 7.56 (d, J = 7.93 Hz, 1 H) 4.85 (d, J = 8.24 Hz, 4 H) 3.21 (d, J = 7.02 Hz, 2 H) 2.08-2.25 (m, 1 H) 1.43-1.76 (m, 6 H) 1.19-1.35 (m, 2 H) | (ESI (+)) m/e 389 (M + H)⁺ |
| 810 | 5-cyano-N-{4-[(1,3-thiazol-5-ylmethyl)carbamoyl]phenyl}-1,3-dihydro-2H-isoindole-2-carboxamide | ¹H NMR (400 MHz, DMSO-D$_2$O, Temp = 90° C.) δ ppm 7.74-7.81 (m, 4 H) 7.72 (dd, J = 7.93, 1.53 Hz, 1 H) 7.61-7.65 (m, 2 H) 7.56 (d, J = 7.93 Hz, 2 H) 4.85 (d, J = 9.77 Hz, 4 H) 4.68 (s, 2 H) | (ESI (+)) m/e 404 (M + H)⁺ |

| Ex | Name | ¹H NMR | MS |
|---|---|---|---|
| 811 | 5-cyano-N-(4-{[(1R)-3-hydroxy-1-phenylpropyl]carbamoyl}phenyl)-1,3-dihydro-2H-isoindole-2-carboxamide | ¹H NMR (400 MHz, DMSO-D₂O, Temp = 90° C.) δ ppm 7.75-7.81 (m, 3 H) 7.70-7.73 (m, 1 H) 7.60-7.64 (m, 2 H) 7.56 (d, J = 7.93 Hz, 1 H) 7.37-7.43 (m, 2 H) 7.28-7.35 (m, 2 H) 7.17-7.25 (m, 1 H) 5.11-5.22 (m, 1 H) 4.85 (d, J = 8.24 Hz, 4 H) 3.44-3.52 (m, 2 H) 1.91-2.12 (m, 2 H) | (ESI (+)) m/e 441 (M + H)⁺ |
| 812 | 5-cyano-N-(4-{[2-hydroxy-1-(4-methylphenyl)ethyl]carbamoyl}phenyl)-1,3-dihydro-2H-isoindole-2-carboxamide | ¹H NMR (400 MHz, DMSO-D₂O, Temp = 90° C.) δ ppm 7.77-7.82 (m, 3 H) 7.72 (dd, J = 7.93, 1.53 Hz, 1 H) 7.59-7.65 (m, 2 H) 7.56 (d, J = 7.93 Hz, 1 H) 7.27 (d, J = 8.24 Hz, 2 H) 7.12 (d, J = 7.93 Hz, 2 H) 5.00-5.07 (m, 1 H) 4.85 (d, J = 8.24 Hz, 4 H) 3.67-3.78 (m, 2 H) 2.27 (s, 3 H) | (ESI (+)) m/e 441 (M + H)⁺ |
| 813 | 5-cyano-N-{4-[(1,3-dihydroxypropan-2-yl)carbamoyl]phenyl}-1,3-dihydro-2H-isoindole-2-carboxamide | ¹H NMR (400 MHz, DMSO-D₂O, Temp = 90° C.) δ ppm 7.86-8.00 (m, 1 H) 7.67-7.81 (m, 4 H) 7.53-7.65 (m, 2 H) 4.85 (d, J = 7.02 Hz, 4 H) 4.33-4.52 (m, 1 H) 3.93-4.02 (m, 1 H) 3.59-3.84 (m, 1 H) 3.58 (d, J = 5.80 Hz, 2 H) | (ESI (+)) m/e 381 (M + H)⁺ |
| 814 | 5-cyano-N-(4-{[(2R)-2-hydroxypropyl]carbamoyl}phenyl)-1,3-dihydro-2H-isoindole-2-carboxamide | ¹H NMR (400 MHz, DMSO-D₂O, Temp = 90° C.) δ ppm 7.68-7.84 (m, 4 H) 7.54-7.64 (m, 3 H) 4.85 (d, J = 8.24 Hz, 4 H) 3.77-3.88 (m, 1 H) 3.15-3.26 (m, 2 H) 1.10 (d, J = 6.10 Hz, 3 H) | (ESI (+)) m/e 365 (M + H)⁺ |
| 815 | 5-cyano-N-{4-[(2-hydroxy-2-methylpropyl)carbamoyl]phenyl}-1,3-dihydro-2H-isoindole-2-carboxamide | ¹H NMR (400 MHz, DMSO-D₂O, Temp = 90° C.) δ ppm 7.69-7.81 (m, 4 H) 7.54-7.65 (m, 3 H) 4.85 (d, J = 8.24 Hz, 4 H) 3.28 (s, 2 H) 1.14 (s, 6 H) | (ESI (+)) m/e 379 (M + H)⁺ |
| 816 | 5-cyano-N-(4-{[(2R)-1-hydroxy-3-methylbutan-2-yl]carbamoyl}phenyl)-1,3-dihydro-2H-isoindole-2-carboxamide | ¹H NMR (400 MHz, DMSO-D₂O, Temp = 90° C.) δ ppm 7.69-7.81 (m, 4 H) 7.55-7.64 (m, 3 H) 4.85 (d, J = 8.24 Hz, 4 H) 3.76-3.84 (m, 1 H) 3.56 (d, J = 5.19 Hz, 2 H) 1.87-2.00 (m, 1 H) 0.92 (dd, J = 11.75, 6.87 Hz, 6 H) | (ESI (+)) m/e 393 (M + H)⁺ |
| 817 | 5-cyano-N-(4-{[(2S)-tetrahydrofuran-2-ylmethyl]carbamoyl}phenyl)-1,3-dihydro-2H-isoindole-2-carboxamide | ¹H NMR (400 MHz, DMSO-D₂O, Temp = 90° C.) δ ppm 7.69-7.81 (m, 4 H) 7.54-7.63 (m, 3 H) 4.85 (d, J = 8.24 Hz, 4 H) 3.95-4.05 (m, 1 H) 3.75-3.84 (m, 1 H) 3.60-3.68 (m, 1 H) 3.34 (d, J = 5.80 Hz, 2 H) 1.75-1.98 (m, 3 H) 1.54-1.66 (m, 1 H) | (ESI (+)) m/e 391 (M + H)⁺ |
| 818 | 5-cyano-N-(4-{[2-(4-methylpiperazin-1-yl)ethyl]carbamoyl}phenyl)-1,3-dihydro-2H-isoindole-2-carboxamide | ¹H NMR (400 MHz, DMSO-D₂O, Temp = 90° C.) δ ppm 7.70-7.81 (m, 4 H) 7.60-7.66 (m, 2 H) 7.57 (d, J = 7.93 Hz, 1 H) 4.85 (d, J = 8.85 Hz, 4 H) 3.50 (t, J = 6.41 Hz, 2 H) 3.22-3.26 (m, 4 H) 3.04 (d, J = 4.88 Hz, 4 H) 2.90 (t, J = 6.41 Hz, 2 H) 2.78 (s, 3 H) | (ESI (+)) m/e 433 (M + H)⁺ |
| 819 | 5-cyano-N-(4-{[(1S)-2-hydroxy-1-phenylethyl]carbamoyl}phenyl)-1,3-dihydro-2H-isoindole-2-carboxamide | ¹H NMR (400 MHz, DMSO-D₂O, Temp = 90° C.) δ ppm 7.78-7.85 (m, 3 H) 7.70-7.74 (m, 1 H) 7.60-7.66 (m, 2 H) 7.56 (d, J = 8.24 Hz, 1 H) 7.38-7.43 (m, 2 H) 7.28-7.34 (m, 2 H) 7.19-7.26 (m, 1 H) 5.03-5.13 (m, 1 H) 4.85 (d, J = 8.24 Hz, 4 H) 3.68-3.79 (m, 2 H) | (ESI (+)) m/e 427 (M + H)⁺ |
| 820 | 5-cyano-N-{4-[(4-hydroxybutyl)carbamoyl]phenyl}-1,3-dihydro-2H-isoindole-2-carboxamide | ¹H NMR (400 MHz, DMSO-D₂O, Temp = 90° C.) δ ppm 7.79 (s, 1 H) 7.70-7.76 (m, 3 H) 7.58-7.64 (m, 2 H) 7.56 (d, J = 8.24 Hz, 1 H) 4.85 (d, J = 8.24 Hz, 4 H) 4.44 (t, J = 6.41 Hz, 1 H) 3.45 (t, J = 6.41 Hz, 1 H) 3.27-3.34 (m, 2 H) 1.46-1.81 (m, 4 H) | (ESI (+)) m/e 377 (M + H)⁺ |
| 821 | 5-cyano-N-(4-{[(2S)-2-hydroxypropyl]carbamoyl}phenyl)-1,3-dihydro-2H-isoindole-2-carboxamide | ¹H NMR (400 MHz, DMSO-D₂O, Temp = 90° C.) δ ppm 7.69-7.82 (m, 4 H) 7.53-7.64 (m, 3 H) 4.85 (d, J = 8.24 Hz, 4 H) 3.79-3.87 (m, 1 H) 3.17-3.26 (m, 2 H) 1.10 (d, J = 6.10 Hz, 3 H) | (ESI (+)) m/e 365 (M + H)⁺ |

| Ex | Name | $^1$H NMR | MS |
|---|---|---|---|
| 822 | 5-cyano-N-{4-[(3-furylmethyl)carbamoyl]phenyl}-1,3-dihydro-2H-isoindole-2-carboxamide | $^1$H NMR (400 MHz, DMSO-D$_2$O, Temp = 90° C.) δ ppm 7.79 (s, 1 H) 7.74-7.78 (m, 2 H) 7.72 (d, J = 7.93 Hz, 1 H) 7.59-7.65 (m, 2 H) 7.54-7.58 (m, 1 H) 7.50-7.53 (m, 1 H) 7.25 (d, J = 8.54 Hz, 1 H) 6.46 (s, 1 H) 4.85 (d, J = 8.85 Hz, 4 H) 4.31 (s, 2 H) | (ESI (+)) m/e 387 (M + H)$^+$ |
| 823 | 5-cyano-N-{4-[(tetrahydrofuran-2-ylmethyl)carbamoyl]phenyl}-1,3-dihydro-2H-isoindole-2-carboxamide | $^1$H NMR (400 MHz, DMSO-D$_2$O, Temp = 90° C.) δ ppm 7.70-7.81 (m, 4 H) 7.55-7.64 (m, 3 H) 4.85 (d, J = 8.24 Hz, 4 H) 3.95-4.04 (m, 1 H) 3.75-3.83 (m, 1 H) 3.61-3.68 (m, 1 H) 3.34 (d, J = 5.80 Hz, 2 H) 1.75-1.98 (m, 3 H) 1.54-1.65 (m, 1 H) | (ESI (+)) m/e 391 (M + H)$^+$ |
| 824 | 5-cyano-N-(4-{[4-(2-furoyl)piperazin-1-yl]carbonyl}phenyl)-1,3-dihydro-2H-isoindole-2-carboxamide | $^1$H NMR (400 MHz, DMSO-D$_2$O, Temp = 90° C.) δ ppm 7.79 (s, 1 H) 7.73-7.75 (m, 1 H) 7.71 (d, J = 1.53 Hz, 1 H) 7.60-7.65 (m, 2 H) 7.57 (d, J = 8.54 Hz, 1 H) 7.34-7.40 (m, 2 H) 7.00 (d, J = 2.75 Hz, 1 H) 6.59 (dd, J = 3.51, 1.68 Hz, 1 H) 4.85 (d, J = 8.54 Hz, 4 H) 3.71-3.77 (m, 4 H) 3.54-3.65 (m, 4 H) | (ESI (+)) m/e 470 (M + H)$^+$ |
| 825 | 5-cyano-N-(4-{[4-(tetrahydrofuran-2-ylcarbonyl)piperazin-1-yl]carbonyl}phenyl)-1,3-dihydro-2H-isoindole-2-carboxamide | $^1$H NMR (400 MHz, DMSO-D$_2$O, Temp = 90° C.) δ ppm 7.79 (s, 1 H) 7.72 (dd, J = 7.93, 1.53 Hz, 1 H) 7.59-7.64 (m, 2 H) 7.57 (d, J = 7.93 Hz, 1 H) 7.33-7.37 (m, 2 H) 4.85 (d, J = 8.24 Hz, 4 H) 4.64 (dd, J = 7.48, 5.95 Hz, 1 H) 3.71-3.86 (m, 2 H) 3.48-3.61 (m, 8 H) 1.96-2.14 (m, 2 H) 1.75-1.94 (m, 2 H) | (ESI (+)) m/e 474 (M + H)$^+$ |
| 826 | 5-cyano-N-(4-{[3-(piperidin-1-yl)propyl]carbamoyl}phenyl)-1,3-dihydro-2H-isoindole-2-carboxamide | $^1$H NMR (400 MHz, DMSO-D$_2$O, Temp = 90° C.) δ ppm 7.70-7.81 (m, 4 H) 7.61-7.66 (m, 2 H) 7.57 (d, J = 7.93 Hz, 1 H) 4.85 (d, J = 8.24 Hz, 4 H) 3.36 (t, J = 6.71 Hz, 4 H) 3.02-3.13 (m, 2 H) 2.90 (s, 2 H) 1.90-2.18 (m, 2 H) 1.81 (d, J = 84.53 Hz, 6 H) | (ESI (+)) m/e 432 (M + H)$^+$ |
| 827 | 5-cyano-N-(4-{[(2R)-tetrahydrofuran-2-ylmethyl]carbamoyl}phenyl)-1,3-dihydro-2H-isoindole-2-carboxamide | $^1$H NMR (400 MHz, DMSO-D$_2$O, Temp = 90° C.) δ ppm 7.70-7.81 (m, 4 H) 7.55-7.64 (m, 3 H) 4.85 (d, J = 8.54 Hz, 4 H) 3.96-4.04 (m, 1 H) 3.76-3.85 (m, 1 H) 3.61-3.68 (m, 1 H) 3.34 (d, J = 5.80 Hz, 2 H) 1.75-1.98 (m, 3 H) 1.54-1.67 (m, 1 H) | (ESI (+)) m/e 391 (M + H)$^+$ |
| 828 | 5-cyano-N-(4-{[4-(ethylsulfonyl)piperazin-1-yl]carbonyl}phenyl)-1,3-dihydro-2H-isoindole-2-carboxamide | $^1$H NMR (400 MHz, DMSO-D$_2$O, Temp = 90° C.) δ ppm 7.79 (s, 1 H) 7.72 (dd, J = 7.93, 1.53 Hz, 1 H) 7.59-7.64 (m, 2 H) 7.57 (d, J = 7.63 Hz, 1 H) 7.32-7.37 (m, 2 H) 4.85 (d, J = 8.24 Hz, 4 H) 3.56-3.61 (m, 4 H) 3.27 (s, 4 H) 3.07 (q, J = 7.32 Hz, 2 H) 1.24 (t, J = 7.32 Hz, 3 H) | (ESI (+)) m/e 468 (M + H)$^+$ |
| 829 | 5-cyano-N-{4-[(tetrahydrofuran-3-ylmethyl)carbamoyl]phenyl}-1,3-dihydro-2H-isoindole-2-carboxamide | $^1$H NMR (400 MHz, DMSO-D$_2$O, Temp = 90° C.) δ ppm 7.79 (s, 1 H) 7.72-7.77 (m, 2 H) 7.71 (d, J = 1.22 Hz, 1 H) 7.59-7.64 (m, 2 H) 7.57 (d, J = 7.93 Hz, 1 H) 4.85 (d, J = 8.24 Hz, 4 H) 3.69-3.80 (m, 2 H) 3.60-3.67 (m, 1 H) 3.47 (dd, J = 8.54, 5.49 Hz, 1 H) 3.28-3.30 (m, J = 3.36 Hz, 2 H) 2.45-2.50 (m, 1 H) 1.90-2.01 (m, 1 H) 1.58-1.68 (m, 1 H) | (ESI (+)) m/e 391 (M + H)$^+$ |
| 830 | 5-cyano-N-(4-{[(1R)-2-hydroxy-1-phenylethyl]carbamoyl}phenyl)-1,3-dihydro-2H-isoindole-2-carboxamide | $^1$H NMR (400 MHz, DMSO-D$_2$O, Temp = 90° C.) δ ppm 7.81-7.83 (m, 1 H) 7.78-7.80 (m, 2 H) 7.72 (dd, J = 7.93, 1.53 Hz, 1 H) 7.61-7.64 (m, 2 H) 7.57 (d, J = 8.54 Hz, 1 H) 7.39 (d, J = 7.63 Hz, 2 H) 7.28-7.34 (m, 2 H) 7.20-7.25 (m, 1 H) 5.05-5.11 (m, 1 H) 4.83-4.88 (m, 4 H) 3.69-3.79 (m, 2 H) | (ESI (+)) m/e 427 (M + H)$^+$ |
| 831 | 5-cyano-N-(4-{[(2S)-1-hydroxybutan-2-yl]carbamoyl}phenyl)-1,3-dihydro-2H-isoindole-2-carboxamide | $^1$H NMR (400 MHz, DMSO-D$_2$O, Temp = 90° C.) δ ppm 7.67-7.90 (m, 4 H) 7.52-7.65 (m, 3 H) 4.85 (d, J = 8.24 Hz, 4 H) 3.79-3.93 (m, 1 H) 3.41-3.55 (m, 2 H) 1.41-1.85 (m, 2 H) 0.90 (t, J = 7.48 Hz, 3 H) | (ESI (+)) m/e 379 (M + H)$^+$ |
| 832 | 5-cyano-N-{4-[(2,3-dihydroxypropyl)carbamoyl]phenyl}-1,3-dihydro-2H-isoindole-2-carboxamide | $^1$H NMR (400 MHz, DMSO-D$_2$O, Temp = 90° C.) δ ppm 7.70-7.81 (m, 4 H) 7.54-7.65 (m, 3 H) 4.85 (d, J = 8.24 Hz, 4 H) 3.62-3.73 (m, 1 H) 3.38-3.45 (m, 3 H) 3.29 (d, J = 6.41 Hz, 1 H) | (ESI (+)) m/e 381 (M + H)$^+$ |

| Ex | Name | ¹H NMR | MS |
|---|---|---|---|
| 833 | 5-cyano-N-{4-[(tetrahydro-2H-pyran-4-ylmethyl)carbamoyl]phenyl}-1,3-dihydro-2H-isoindole-2-carboxamide | ¹H NMR (400 MHz, DMSO-D₂O, Temp = 90° C.) δ ppm 7.69-7.84 (m, 4 H) 7.52-7.64 (m, 3 H) 4.85 (d, J = 8.24 Hz, 4 H) 3.80-3.89 (m, 2 H) 3.28-3.35 (m, 2 H) 3.19 (d, J = 7.02 Hz, 2 H) 1.76-1.91 (m, 1 H) 1.61 (dd, J = 12.82, 1.83 Hz, 2 H) 1.17-1.32 (m, 2 H) | (ESI (+)) m/e 405 (M + H)⁺ |
| 834 | 5-cyano-N-(4-{[2-hydroxy-1-(pyridin-2-yl)ethyl]carbamoyl}phenyl)-1,3-dihydro-2H-isoindole-2-carboxamide | ¹H NMR (400 MHz, DMSO-D₂O, Temp = 90° C.) δ ppm 8.60 (d, J = 4.27 Hz, 1 H) 7.96-8.04 (m, 1 H) 7.77-7.86 (m, 3 H) 7.73 (d, J = 7.93 Hz, 1 H) 7.61-7.68 (m, 3 H) 7.57 (d, J = 7.93 Hz, 1 H) 7.45-7.51 (m, 1 H) 5.21 (t, J = 5.95 Hz, 1 H) 4.86 (d, J = 8.24 Hz, 4 H) 3.89 (d, J = 5.80 Hz, 2 H) | (ESI (+)) m/e 428 (M + H)⁺ |
| 835 | 5-cyano-N-{4-[(1-hydroxy-4-methylpentan-2-yl)carbamoyl]phenyl}-1,3-dihydro-2H-isoindole-2-carboxamide | ¹H NMR (400 MHz, DMSO-D₂O, Temp = 90° C.) δ ppm 7.68-7.82 (m, 4 H) 7.52-7.64 (m, 3 H) 4.85 (d, J = 8.24 Hz, 4 H) 4.01-4.09 (m, 1 H) 3.38-3.52 (m, 2 H) 1.59-1.75 (m, 1 H) 1.37-1.55 (m, 2 H) 0.86-0.93 (m, 6 H) | (ESI (+)) m/e 407 (M + H)⁺ |
| 836 | 5-cyano-N-(4-{[(1-methylpyrrolidin-3-yl)methyl]carbamoyl}phenyl)-1,3-dihydro-2H-isoindole-2-carboxamide | ¹H NMR (400 MHz, DMSO-D₂O, Temp = 90° C.) δ ppm 7.70-7.82 (m, 4 H) 7.59-7.67 (m, 2 H) 7.57 (d, J = 7.63 Hz, 1 H) 4.82-4.89 (m, 4 H) 3.41-3.82 (m, 2 H) 3.35-3.41 (m, 2 H) 2.94-3.21 (m, 2 H) 2.85 (s, 3 H) 2.60-2.75 (m, 1 H) 1.61-2.34 (m, 2 H) | (ESI (+)) m/e 404 (M + H)⁺ |
| 837 | 5-cyano-N-(4-{[(1-methylpiperidin-4-yl)methyl]carbamoyl}phenyl)-1,3-dihydro-2H-isoindole-2-carboxamide | ¹H NMR (400 MHz, DMSO-D₂O, Temp = 90° C.) δ ppm 7.67-7.83 (m, 4 H) 7.54-7.65 (m, 3 H) 4.85 (d, J = 8.24 Hz, 4 H) 3.36-3.52 (m, 2 H) 3.18-3.25 (m, 2 H) 2.92 (s, 2 H) 2.76 (s, 3 H) 1.89 (m, 3 H) 1.29-1.54 (m, 2 H) | (ESI (+)) m/e 418 (M + H)⁺ |
| 838 | 5-cyano-N-{4-[(tetrahydro-2H-pyran-3-ylmethyl)carbamoyl]phenyl}-1,3-dihydro-2H-isoindole-2-carboxamide | ¹H NMR (400 MHz, DMSO-D₂O, Temp = 90° C.) δ ppm 7.68-7.82 (m, 4 H) 7.52-7.65 (m, 3 H) 4.85 (d, J = 8.54 Hz, 4 H) 3.65-3.82 (m, 2 H) 3.29-3.40 (m, 1 H) 3.09-3.20 (m, 3 H) 1.73-1.92 (m, 2 H) 1.40-1.69 (m, 2 H) 1.20-1.35 (m, 1 H) | (ESI (+)) m/e 405 (M + H)⁺ |
| 717 | N-{4-[(pyrrolidin-3-ylmethyl)carbamoyl]phenyl}-1,3-dihydro-2H-isoindole-2-carboxamide | 1H NMR (300 MHz, DMSO-d₆) δ 9.07 (bs, 1H), 8.64 (s, 1H), 8.51 (t, J = 5.8 Hz, 1H), 7.83-7.75 (m, 1H), 7.73-7.65 (m, 2H), 7.42-7.28 (m, 3H), 4.86 (bs, 2H), 4.79 (s, 4H), 3.75-3.64 (m, 1H), 3.53-3.43 (m, 1H), 3.40-3.16 (m, 3H), 3.10 (dt, J = 13.6, 7.7 Hz, 1H), 2.98-2.83 (m, 1H), 2.07-1.92 (m, 1H), 1.84-1.46 (m, 1H) | (ESI (+)) m/e 340 (M + H)⁺ |
| 840 | N-[4-(2,6-diazaspiro[3.3]hept-2-ylcarbonyl)phenyl]-1,3-dihydro-2H-isoindole-2-carboxamide | ¹H NMR (400 MHz, DMSO-D₂O) δ 7.67-7.61 (m, 2H), 7.57-7.51 (m, 2H), 7.40-7.26 (m, 4H), 4.79 (s, 4H), 4.36 (bs, 4H), 4.20 (s, 4H) | (ESI (+)) m/e 363 (M + H)⁺ |
| 841 | N-[4-(2,6-diazaspiro[3.4]oct-6-ylcarbonyl)phenyl]-1,3-dihydro-2H-isoindole-2-carboxamide | ¹H NMR (400 MHz, DMSO-D₂O) δ 7.70-7.56 (m, 2H), 7.48-7.42 (m, 2H), 7.38-7.29 (m, 4H), 4.79 (s, 4H), 3.99 (q, J = 10.6 Hz, 4H), 3.74 (s, 2H), 3.52 (t, J = 7.0 Hz, 2H), 2.18 (t, J = 7.1 Hz, 2H) | (ESI (+)) m/e 377 (M + H)⁺ |
| 842 | N-[4-(2,7-diazaspiro[3.5]non-7-ylcarbonyl)phenyl]-1,3-dihydro-2H-isoindole-2-carboxamide | ¹H NMR (400 MHz, DMSO-D₂O) δ 7.73-7.53 (m, 2H), 7.42-7.31 (m, 4H), 7.31-7.25 (m, 2H), 4.79 (s, 4H), 3.81 (d, J = 5.0 Hz, 4H), 3.44 (dd, J = 12.2, 6.6 Hz, 4H), 1.92-1.53 (m, 4H) | (ESI (+)) m/e 391 (M + H)⁺ |
| 843 | N-[4-(2,6-diazaspiro[3.5]non-2-ylcarbonyl)phenyl]-1,3-dihydro-2H-isoindole-2-carboxamide | ¹H NMR (400 MHz, DMSO-D₂O) δ 7.67-7.61 (m, 2H), 7.58-7.54 (m, 2H), 7.39-7.29 (m, 4H), 4.79 (s, 4H), 4.07 (d, J = 7.8 Hz, 2H), 3.95 (d, J = 22.6 Hz, 2H), 2.99 (t, J = 11.8, 6.0 Hz, 2H), 2.55 (s, 2H), 1.97-1.82 (m, 2H), 1.82-1.59 (m, 2H) | (ESI (+)) m/e 391 (M + H)⁺ |

| Ex | Name | ¹H NMR | MS |
|---|---|---|---|
| 844 | N-[4-(1,7-diazaspiro[4.4]non-1-ylcarbonyl)phenyl]-1,3-dihydro-2H-isoindole-2-carboxamide | ¹H NMR (400 MHz, DMSO-D$_2$O) δ 7.72-7.57 (m, 2H), 7.50-7.40 (m, 2H), 7.40-7.22 (m, 4H), 4.79 (s, 4H), 3.83 (d, J = 12.2 Hz, 1H), 3.75-3.63 (m, 1H), 3.57-3.42 (m, 2H), 3.17 (t, J = 13.0 Hz, 1H), 2.61 (m, J = 13.5, 9.0 Hz, 1H), 2.27-1.99 (m, 3H), 1.92-1.61 (m, 2H) | (ESI (+)) m/e 391 (M + H)⁺ |
| 845 | N-[4-(1,7-diazaspiro[4.4]non-7-ylcarbonyl)phenyl]-1,3-dihydro-2H-isoindole-2-carboxamide | ¹H NMR (400 MHz, DMSO-D$_2$O) δ 7.77-7.56 (m, 2H), 7.54-7.42 (m, 2H), 7.41-7.22 (m, 4H), 4.79 (s, 4H), 3.88 (d, J = 12.7 Hz, 1H), 3.75-3.56 (m, 3H), 2.39-2.25 (m, 1H), 2.26-2.11 (m, 1H), 2.10-1.87 (m, 4H) | (ESI (+)) m/e 391 (M + H)⁺ |
| 846 | N-[4-(2,7-diazaspiro[4.4]non-2-ylcarbonyl)phenyl]-1,3-dihydro-2H-isoindole-2-carboxamide | ¹H NMR (400 MHz, DMSO-D$_2$O) δ 7.70-7.54 (m, 2H), 7.50-7.40 (m, 2H), 7.39-7.22 (m, 4H), 4.79 (s, 4H), 3.72-3.42 (m, 4H), 3.17 (t, J = 10.1 Hz, 2H), 2.14-1.81 (m, 4H) | (ESI (+)) m/e 391 (M + H)⁺ |
| 847 | N-[4-(2,8-diazaspiro[4.5]dec-2-ylcarbonyl)phenyl]-1,3-dihydro-2H-isoindole-2-carboxamide | ¹H NMR (400 MHz, DMSO-D$_2$O) δ 7.70-7.55 (m, 2H), 7.52-7.40 (m, 2H), 7.38-7.16 (m, 4H), 4.79 (s, 4H), 3.57 (t, J = 7.2 Hz, 2H), 3.41 (s, 2H), 3.15-2.98 (m, 4H), 2.53-2.50 (m, 2H), 1.82 (t, 2H), 1.76-1.60 (m, 4H) | (ESI (+)) m/e 405 (M + H)⁺ |
| 848 | N-[4-(2,7-diazaspiro[4.5]dec-2-ylcarbonyl)phenyl]-1,3-dihydro-2H-isoindole-2-carboxamide | ¹H NMR (400 MHz, DMSO-D$_2$O) δ 7.71-7.54 (m, 2H), 7.53-7.39 (m, 2H), 7.39-7.20 (m, 4H), 4.79 (s, 4H), 3.63-3.55 (m, 2H), 3.55-3.47 (m, 1H), 3.46-3.39 (m, 1H), 3.07-2.98 (m, 4H), 1.98-1.87 (m, 1H), 1.86-1.77 (m, 1H), 1.77-1.71 (m, 1H), 1.71-1.56 (m, 3H) | (ESI (+)) m/e 405 (M + H)⁺ |
| 849 | N-[4-(2,6-diazaspiro[4.5]dec-2-ylcarbonyl)phenyl]-1,3-dihydro-2H-isoindole-2-carboxamide | ¹H NMR (400 MHz, DMSO-D$_2$O) δ 7.76-7.55 (m, 2H), 7.55-7.41 (m, 2H), 7.41-7.20 (m, 4H), 4.79 (s, 4H), 3.82 (d, J = 12.8 Hz, 1H), 3.77-3.66 (m, 1H), 3.66-3.53 (m, 2H), 3.17-2.98 (m, 2H), 2.36-2.21 (m, 1H), 2.19-2.06 (m, 1H), 1.87-1.77 (m, 2H), 1.76-1.55 (m, 4H) | (ESI (+)) m/e 405 (M + H)⁺ |
| 850 | N-[4-(2,7-diazaspiro[4.5]dec-7-ylcarbonyl)phenyl]-1,3-dihydro-2H-isoindole-2-carboxamide | ¹H NMR (400 MHz, DMSO-D$_2$O) δ 7.76-7.55 (m, 2H), 7.45-7.32 (m, 3H), 7.34-7.19 (m, 4H), 4.79 (s, 4H), 3.66-3.49 (m, 2H), 3.47-3.36 (m, 1H), 3.27-3.12 (m, 1H), 3.10-2.90 (m, 2H), 2.00-1.83 (m, 1H), 1.84-1.62 (m, 3H), 1.62-1.46 (m, 2H) | (ESI (+)) m/e 405 (M + H)⁺ |
| 851 | N-[4-(3,9-diazaspiro[5.5]undec-3-ylcarbonyl)phenyl]-1,3-dihydro-2H-isoindole-2-carboxamide | | (ESI (+)) m/e XXX (M + H)⁺ |
| 852 | N-[4-(2,9-diazaspiro[5.5]undec-2-ylcarbonyl)phenyl]-1,3-dihydro-2H-isoindole-2-carboxamide | ¹H NMR (400 MHz, DMSO-D$_2$O) δ 7.78-7.54 (m, 2H), 7.46-7.21 (m, 6H), 4.79 (s, 4H), 3.66 (d, J = 13.3 Hz, 1H), 3.54 (d, J = 14.2 Hz, 1H), 3.35 (dd, J = 14.9, 8.0 Hz, 2H), 3.09-3.00 (m, 1H), 3.00-2.94 (m, 1H), 2.94-2.85 (m, 2H), 2.54-2.48 (m, 2H), 1.70 (dd, J = 11.6, 5.7 Hz, 2H), 1.63 (dd, J = 16.4, 6.3 Hz, 2H), 1.61-1.50 (m, 4H), 1.50-1.39 (m, 1H) | (ESI (+)) m/e 419 (M + H)⁺ |
| 853 | N-[4-(2,8-diazaspiro[5.5]undec-2-ylcarbonyl)phenyl]-1,3-dihydro-2H-isoindole-2-carboxamide | ¹H NMR (400 MHz, DMSO-D$_2$O) δ 7.79-7.49 (m, 2H), 7.44-7.13 (m, 6H), 4.79 (s, 4H), 3.45 (d, J = 9.0 Hz, 4H), 3.17-2.85 (m, 4H), 1.59 (dd, J = 12.8, 6.9 Hz, 8H) | (ESI (+)) m/e 419 (M + H)⁺ |
| 854 | N-[4-(1,8-diazaspiro[5.5]undec-8-ylcarbonyl)phenyl]-1,3-dihydro-2H-isoindole-2-carboxamide | ¹H NMR (400 MHz, DMSO-D$_2$O) δ 7.74-7.52 (m, 2H), 7.41-7.24 (m, 6H), 4.79 (s, 4H), 3.82 (t, J = 14.5 Hz, 1H), 3.70 (d, J = 13.7 Hz, 1H), 3.55-3.40 (m, 2H), 3.16-2.88 (m, 2H), 2.01-1.81 (m, 2H), 1.75-1.53 (m, 8H) | (ESI (+)) m/e 419 (M + H)⁺ |

| Ex | Name | ¹H NMR | MS |
|---|---|---|---|
| 855 | N-[4-(1,8-diazaspiro[4.6]undec-8-ylcarbonyl)phenyl]-1,3-dihydro-2H-isoindole-2-carboxamide | ¹H NMR (400 MHz, DMSO-D$_2$O) δ 7.73-7.51 (m, 2H), 7.45-7.15 (m, 6H), 4.79 (s, 4H), 3.77-3.59 (m, 1H), 3.62-3.36 (m, 3H), 3.29-3.20 (m, 2H), 2.12-1.95 (m, 4H), 1.91-1.66 (m, 5H) | (ESI (+)) m/e 419 (M + H)$^+$ |
| 856 | N-{4-[(1-oxa-8-azaspiro[4.5]dec-2-ylmethyl)carbamoyl]phenyl}-1,3-dihydro-2H-isoindole-2-carboxamide | ¹H NMR (400 MHz, DMSO-D$_2$O) δ 7.78-7.72 (m, 2H), 7.66-7.61 (m, 2H), 7.39-7.28 (m, 4H), 4.79 (s, 4H), 4.15 (dd, J = 12.2, 6.0 Hz, 1H), 3.38 (qd, J = 13.4, 5.8 Hz, 2H), 3.20-3.00 (m, 4H), 2.53-2.50 (m, 3H), 2.18-1.96 (m, 1H), 1.94-1.56 (m, 8H) | (ESI (+)) m/e 435 (M + H)$^+$ |
| 857 | N-[4-(1-oxa-8-azaspiro[4.5]dec-3-ylcarbamoyl)phenyl]-1,3-dihydro-2H-isoindole-2-carboxamide | ¹H NMR (400 MHz, DMSO-D$_2$O) δ 7.84-7.70 (m, 2H), 7.70-7.54 (m, 2H), 7.46-7.21 (m, 4H), 4.79 (s, 4H), 4.64-4.44 (m, 1H), 4.15-3.95 (m, 1H), 3.73 (dd, J = 9.1, 6.1 Hz, 1H), 3.19-2.97 (m, 4H), 2.21 (dd, J = 13.1, 8.3 Hz, 1H), 1.99-1.84 (m, 3H), 1.84-1.70 (m, 2H) | (ESI (+)) m/e 421 (M + H)$^+$ |
| 858 | N-{4-[(2-oxa-9-azaspiro[5.5]undec-3-ylmethyl)carbamoyl]phenyl}-1,3-dihydro-2H-isoindole-2-carboxamide | ¹H NMR (400 MHz, DMSO-D$_2$O) δ 7.87-7.69 (m, 2H), 7.71-7.53 (m, 2H), 7.45-7.12 (m, 4H), 4.79 (s, 4H), 3.75 (dd, J = 11.5, 2.6 Hz, 1H), 3.55-3.41 (m, 1H), 3.38-3.31 (m, 2H), 3.22-3.12 (m, 1H), 3.11-2.94 (m, 4H), 1.92-1.66 (m, 3H), 1.62-1.49 (m, 1H), 1.49-1.24 (m, 4H) | (ESI (+)) m/e 449 (M + H)$^+$ |
| 859 | N-[4-(1-oxa-4,8-diazaspiro[5.5]undec-4-ylcarbonyl)phenyl]-1,3-dihydro-2H-isoindole-2-carboxamide | ¹H NMR (400 MHz, DMSO-D$_2$O) δ 7.75-7.53 (m, 2H), 7.44-7.15 (m, 6H), 4.79 (s, 4H), 3.82-3.66 (m, 2H), 3.63-3.46 (m, 4H), 3.40-3.32 (m, 1H), 3.25-3.14 (m, 1H), 2.96-2.77 (m, 2H), 2.08-1.92 (m, 1H), 1.92-1.74 (m, 1H), 1.73-1.58 (m, 1H), 1.59-1.38 (m, 1H) | (ESI (+)) m/e 421 (M + H)$^+$ |
| 860 | N-[4-(1,8-diazaspiro[4.5]dec-1-ylcarbonyl)phenyl]-1,3-dihydro-2H-isoindole-2-carboxamide | ¹H NMR (400 MHz, DMSO-D$_2$O) δ 7.71-7.48 (m, 2H), 7.45-7.18 (m, 6H), 4.79 (s, 4H), 3.44 (t, J = 6.7 Hz, 2H), 3.36 (dd, J = 7.3, 5.1 Hz, 1H), 3.24-3.06 (m, 2H), 3.05-2.85 (m, 2H), 2.05 (t, J = 7.0 Hz, 2H), 1.88-1.72 (m, 2H), 1.65 (dd, J = 12.7, 1.4 Hz, 2H) | (ESI (+)) m/e 405 (M + H)$^+$ |
| 861 | N-[4-(1,8-diazaspiro[4.5]dec-8-ylcarbonyl)phenyl]-1,3-dihydro-2H-isoindole-2-carboxamide | ¹H NMR (400 MHz, DMSO-D$_2$O) δ 7.75-7.51 (m, 2H), 7.42-7.10 (m, 6H), 4.79 (s, 4H), 3.92-3.68 (m, 2H), 3.36 (dd, J = 8.1, 5.4 Hz, 1H), 3.31-3.21 (m, 2H), 2.14-1.91 (m, 4H), 1.91-1.68 (m, 4H) | (ESI (+)) m/e 405 (M + H)$^+$ |
| 862 | N-[4-(2,6-diazaspiro[3.4]oct-2-ylcarbonyl)phenyl]-1,3-dihydro-2H-isoindole-2-carboxamide | ¹H NMR (400 MHz, DMSO-D$_2$O) δ 7.72-7.60 (m, 2H), 7.60-7.49 (m, 2H), 7.42-7.21 (m, 4H), 4.79 (s, 4H), 4.20 (dd, J = 29.4, 9.1 Hz, 4H), 3.42 (s, 2H), 3.27 (d, J = 3.7 Hz, 1H), 3.24 (s, 1H), 2.24 (t, J = 7.4 Hz, 2H) | (ESI (+)) m/e 377 (M + H)$^+$ |
| 863 | N-[4-(1,7-diazaspiro[3.5]non-7-ylcarbonyl)phenyl]-1,3-dihydro-2H-isoindole-2-carboxamide | ¹H NMR (400 MHz, DMSO-D$_2$O) δ 7.72-7.52 (m, 2H), 7.43-7.10 (m, 6H), 5.54 (s, 1H), 4.79 (s, 4H), 3.99 (d, J = 11.5 Hz, 2H), 3.68-3.49 (m, 2H), 2.95 (t, J = 7.4 Hz, 2H), 2.53-2.51 (m, 1H), 2.41-2.25 (m, 2H), 2.07 (t, J = 31.9 Hz, 2H) | (ESI (+)) m/e 390 (M + H)$^+$ |
| 864 | N-[4-(1,6-diazaspiro[3.5]non-1-ylcarbonyl)phenyl]-1,3,dihydro-2H-isoindole-2-carboxamide | ¹H NMR (400 MHz, DMSO-D$_2$O) δ 7.75-7.61 (m, 2H), 7.60-7.48 (m, 2H), 7.42-7.12 (m, 4H), 4.79 (s, 4H), 4.54-4.29 (m, 1H), 4.14-3.91 (m, 1H), 3.86-3.55 (m, 1H), 3.26-3.18 (m, 1H), 3.12-2.79 (m, 1H), 2.50 (dd, J = 9.4, 1.3 Hz, 1H), 2.43-2.20 (m, 1H), 2.17-2.01 (m, 1H), 2.01-1.85 (m, 1H), 1.87-1.52 (m, 1H) | (ESI (+)) m/e 391 (M + H)$^+$ |
| 865 | N-[4-(2,5-diazaspiro[3.5]non-2-ylcarbonyl)phenyl]-1,3-dihydro-2H-isoindole-2-carboxamide | ¹H NMR (400 MHz, DMSO-D$_2$O) δ 7.75-7.62 (m, 2H), 7.62-7.52 (m, 2H), 7.44-7.18 (m, 4H), 4.80 (s, 4H), 4.28 (d, J = 10.2 Hz, 2H), 4.19 (s, 2H), 3.10 (t, J = 5.3 Hz, 2H), 2.01 (t, J = 5.4 Hz, 2H), 1.77-1.35 (m, 4H) | (ESI (+)) m/e 391 (M + H)$^+$ |

| Ex | Name | ¹H NMR | MS |
|---|---|---|---|
| 866 | N-[4-(5-oxa-2-azaspiro[3.4]oct-2-ylcarbonyl)phenyl]-1,3-dihydro-2H-isoindole-2-carboxamide | ¹H NMR (400 MHz, DMSO-D$_2$O) δ 7.65-7.60 (m, 2H), 7.57-7.53 (m, 2H), 7.40-6.97 (m, 5H), 4.79 (s, 5H), 4.16 (dd, J = 23.4, 9.6 Hz, 4H), 3.77 (t, J = 6.8 Hz, 2H), 3.35 (q, J = 7.1 Hz, 1H), 2.07 (dd, J = 8.1, 6.6 Hz, 2H), 1.98-1.74 (m, 2H), 1.11 (t, J = 7.1 Hz, 1H) | (ESI (+)) m/e 378 (M + H)⁺ |
| 867 | N-[4-(6-oxa-2-azaspiro[3.5]non-2-ylcarbonyl)phenyl]-1,3-dihydro-2H-isoindole-2-carboxamide | ¹H NMR (400 MHz, DMSO-D$_2$O) δ 7.65-7.60 (m, 2H), 7.58-7.54 (m, 2H), 7.38-7.28 (m, 4H), 4.79 (s, 4H), 3.95-3.67 (m, 4H), 3.59 (s, 2H), 3.55-3.44 (m, 2H), 1.90-1.72 (m, 2H), 1.61-1.39 (m, 2H) | (ESI (+)) m/e 392 (M + H)⁺ |
| 868 | N-[4-(hexahydro-5H-furo[2,3-c]pyrrol-5-ylcarbonyl)phenyl]-1,3-dihydro-2H-isoindole-2-carboxamide | ¹H NMR (400 MHz, DMSO-D$_2$O) δ 7.75-7.52 (m, 2H), 7.46-7.20 (m, 6H), 4.79 (s, 4H), 4.49-4.27 (m, 1H), 3.95-3.78 (m, 1H), 3.77-3.55 (m, 4H), 3.43 (dd, J = 11.8, 5.4 Hz, 1H), 2.98-2.70 (m, 1H), 2.06 (ddd, J = 15.0, 12.5, 7.7 Hz, 1H), 1.82-1.49 (m, 1H) | (ESI (+)) m/e 378 (M + H)⁺ |
| 869 | N-[4-(tetrahydro-1H-furo[3,4-c]pyrrol-5(3H)-ylcarbonyl)phenyl]-1,3-dihydro-2H-isoindole-2-carboxamide | ¹H NMR (400 MHz, DMSO-D$_2$O) δ 7.69-7.61 (m, 1H), 7.60 (d, 1H), 7.47-7.07 (m, 6H), 4.79 (s, 4H), 3.83-3.59 (m, 4H), 3.58-3.33 (m, 4H), 3.05-2.82 (m, 2H) | (ESI (+)) m/e 378 (M + H)⁺ |
| 870 | N-[4-(hexahydrofuro[3,4-c]pyridin-5(3H)-ylcarbonyl)phenyl]-1,3-dihydro-2H-isoindole-2-carboxamide | ¹H NMR (400 MHz, DMSO-D$_2$O) δ 7.71-7.52 (m, 2H), 7.41-7.12 (m, 6H), 4.79 (s, 4H), 3.89-3.65 (m, 2H), 3.67-3.40 (m, 5H), 3.39-3.26 (m, 2H), 2.46-2.25 (m, 2H), 1.88-1.63 (m, 1H), 1.67-1.24 (m, 1H) | (ESI (+)) m/e 392 (M + H)⁺ |
| 885 | N-[4-(2,6-diazaspiro[3.4]oct-6-ylcarbonyl)phenyl]-5-fluoro-1,3-dihydro-2H-isoindole-2-carboxamide | ¹H NMR (400 MHz, DMSO-D$_2$O) δ 7.68-7.51 (m, 2H), 7.51-7.28 (m, 3H), 7.24-7.00 (m, 1H), 4.77 (d, J = 12.1 Hz, 4H), 3.61 (d, J = 17.1 Hz, 2H), 3.54 (d, J = 8.2 Hz, 3H), 3.48 (t, J = 7.0 Hz, 2H), 2.06 (dd, J = 23.6, 16.6 Hz, 2H), 1.89 (s, 1H) | (ESI (+)) m/e 393 (M + H)⁺ |
| 886 | N-[4-(2,7-diazaspiro[3.5]non-7-ylcarbonyl)phenyl]-5-fluoro-1,3-dihydro-2H-isoindole-2-carboxamide | ¹H NMR (400 MHz, DMSO-D$_2$O) δ 7.65-7.53 (m, 2H), 7.37 (dd, J = 8.3, 5.2 Hz, 1H), 7.31-7.22 (m, 2H), 7.17 (d, J = 9.0 Hz, 1H), 7.15-6.92 (m, 1H), 4.77 (d, J = 12.3 Hz, 4H), 3.41 (t, J = 5.5 Hz, 8H), 1.78-1.63 (m, 4H) | (ESI (+)) m/e 407 (M + H)⁺ |
| 887 | N-[4-(1,7-diazaspiro[4.4]non-1-ylcarbonyl)phenyl]-5-fluoro-1,3-dihydro-2H-isoindole-2-carboxamide | ¹H NMR (400 MHz, DMSO-D$_2$O) δ 7.65-7.49 (m, 2H), 7.43-7.32 (m, 3H), 7.22-7.03 (m, 2H), 4.76 (d, J = 12.6 Hz, 4H), 3.54-3.37 (m, 2H), 2.86 (dt, J = 11.3, 7.9 Hz, 1H), 2.70 (d, J = 11.7 Hz, 1H), 2.10-1.96 (m, 1H), 1.90 (d, J = 29.4 Hz, 1H), 1.84-1.67 (m, 2H), 1.25 (s, 1H) | (ESI (+)) m/e 409 (M + H)⁺ |
| 888 | N-[4-(2,8-diazaspiro[4.5]dec-2-ylcarbonyl)phenyl]-5-fluoro-1,3-dihydro-2H-isoindole-2-carboxamide | ¹H NMR (400 MHz, DMSO-D$_2$O) δ 7.70-7.49 (m, 2H), 7.45-7.32 (m, 3H), 7.22-7.03 (m, 2H), 4.77 (d, J = 12.4 Hz, 4H), 3.53 (t, J = 7.2 Hz, 2H), 3.33 (s, 2H), 2.79 (dd, J = 20.6, 14.7 Hz, 3H), 1.88 (s, 1H), 1.78 (t, J = 7.1 Hz, 2H), 1.50 (s, 4H) | (ESI (+)) m/e 423 (M + H)⁺ |
| 889 | N-[4-(2,6-diazaspiro[4.5]dec-2-ylcarbonyl)phenyl]-5-fluoro-1,3-dihydro-2H-isoindole-2-carboxamide | ¹H NMR (400 MHz, DMSO-D$_2$O) δ 7.70-7.54 (m, 2H), 7.50-7.30 (m, 3H), 7.24-7.00 (m, 2H), 4.77 (d, J = 12.5 Hz, 4H), 3.75-3.54 (m, 1H), 3.57-3.47 (m, 2H), 3.40 (d, J = 11.8 Hz, 1H), 3.20 (d, J = 0.5 Hz, 1H), 2.76 (d, J = 21.5 Hz, 2H), 2.07-1.77 (m, 3H), 1.64-1.40 (m, 6H) | (ESI (+)) m/e 423 (M + H)⁺ |
| 890 | N-[4-(2,7-diazaspiro[4.5]dec-7-ylcarbonyl)phenyl]-5-fluoro-1,3-dihydro-2H-isoindole-2-carboxamide | ¹H NMR (400 MHz, DMSO-D$_2$O) δ 7.69-7.54 (m, 2H), 7.37 (dd, J = 8.4, 5.2 Hz, 1H), 7.33-7.22 (m, 2H), 7.23-7.02 (m, 2H), 4.77 (d, J = 12.2 Hz, 4H), 3.53-3.31 (m, 4H), 3.20 (s, 2H), 2.94-2.79 (m, 2H), 2.64 (dd, J = 42.4, 11.2 Hz, 2H), 1.87 (s, 2H), 1.74-1.32 (m, 6H) | (ESI (+)) m/e 423 (M + H)⁺ |

| Ex | Name | ¹H NMR | MS |
|---|---|---|---|
| 891 | N-[4-(2,8-diazaspiro[5.5]undec-2-ylcarbonyl)phenyl]-5-fluoro-1,3-dihydro-2H-isoindole-2-carboxamide | ¹H NMR (400 MHz, DMSO-D$_2$O) δ 7.59 (dd, J = 6.4, 4.5 Hz, 2H), 7.37 (dd, J = 8.4, 5.1 Hz, 1H), 7.33-7.20 (m, 2H), 7.17 (d, J = 9.0 Hz, 1H), 7.13-7.02 (m, 1H), 4.77 (d, J = 12.4 Hz, 4H), 3.51-3.36 (m, 4H), 3.20 (s, 2H), 2.80-2.65 (m, 2H), 2.64 (s, 2H), 1.85 (s, 2H), 1.52 (s, 4H), 1.37 (t, J = 5.7 Hz, 4H) | (ESI (+)) m/e 437 (M + H)⁺ |
| 892 | N-[4-(1,8-diazaspiro[5.5]undec-8-ylcarbonyl)phenyl]-5-fluoro-1,3-dihydro-2H-isoindole-2-carboxamide | ¹H NMR (400 MHz, DMSO-D$_2$O) δ 7.65-7.51 (m, 2H), 7.37 (dd, J = 8.4, 5.1 Hz, 1H), 7.34-7.24 (m, 2H), 7.23-7.05 (m, 2H), 4.77 (d, J = 12.5 Hz, 4H), 3.58-3.36 (m, 4H), 3.20 (s, 2H), 2.72-2.54 (m, 2H), 1.62-1.36 (m, 8H) | (ESI (+)) m/e 437 (M + H)⁺ |
| 893 | N-[4-(1,8-diazaspiro[4.6]undec-8-ylcarbonyl)phenyl]-5-fluoro-1,3-dihydro-2H-isoindole-2-carboxamide | ¹H NMR (400 MHz, DMSO-D$_2$O) δ 7.65-7.51 (m, 2H), 7.37 (dd, J = 8.3, 5.2 Hz, 1H), 7.32-7.23 (m, 2H), 7.19-7.01 (m, 2H), 4.77 (d, J = 12.9 Hz, 4H), 3.49 (d, J = 14.0 Hz, 3H), 3.03-2.76 (m, 2H), 1.84-1.59 (m, 8H), 1.25 (s, 6H) | (ESI (+)) m/e 437 (M + H)⁺ |
| 894 | 5-fluoro-N-{4-[(1-oxa-8-azaspiro[4.5]dec-2-ylmethyl)carbamoyl]phenyl}-1,3-dihydro-2H-isoindole-2-carboxamide | ¹H NMR (400 MHz, DMSO-D$_2$O) δ 7.83-7.68 (m, 2H), 7.68-7.49 (m, 2H), 7.37 (dd, J = 8.4, 5.1 Hz, 1H), 7.21-6.93 (m, 2H), 4.77 (d, J = 12.2 Hz, 4H), 4.10 (t, J = 6.0 Hz, 1H), 3.44-3.31 (m, 2H), 3.06-2.83 (m, 2H), 2.83-2.70 (m, 2H), 2.12-1.92 (m, 1H), 1.81-1.66 (m, 3H), 1.62-1.32 (m, 4H) | (ESI (+)) m/e 453 (M + H)⁺ |
| 895 | 5-fluoro-N-[4-(1-oxa-8-azaspiro[4.5]dec-3-ylcarbamoyl)phenyl]-1,3-dihydro-2H-isoindole-2-carboxamide | ¹H NMR (400 MHz, DMSO-D$_2$O) δ 7.80-7.69 (m, 2H), 7.66-7.50 (m, 2H), 7.37 (dd, J = 8.2, 5.1 Hz, 1H), 7.27-6.90 (m, 2H), 4.77 (d, J = 12.7 Hz, 4H), 4.61-4.39 (m, 1H), 4.02 (dd, J = 8.9, 6.8 Hz, 1H), 3.66 (dd, J = 8.9, 6.3 Hz, 1H), 3.01-2.81 (m, 2H), 2.80-2.61 (m, 2H), 2.15 (dd, J = 12.9, 8.3 Hz, 1H), 1.87-1.73 (m, 1H), 1.70 (t, J = 5.7 Hz, 2H), 1.65-1.49 (m, 2H) | (ESI (+)) m/e 439 (M + H)⁺ |
| 896 | 5-fluoro-N-[4-(1-oxa-4,8-diazaspiro[5.5]undec-4-ylcarbonyl)phenyl]-1,3-dihydro-2H-isoindole-2-carboxamide | ¹H NMR (400 MHz, DMSO-D$_2$O) δ 7.69-7.54 (m, 2H), 7.37 (dd, J = 8.3, 5.1 Hz, 1H), 7.35-7.28 (m, 2H), 7.17 (d, J = 9.0 Hz, 1H), 7.14-6.96 (m, 1H), 4.77 (d, J = 12.4 Hz, 4H), 3.77-3.57 (m, 2H), 3.57-3.36 (m, 4H), 2.71 (dd, J = 25.6, 8.7 Hz, 1H), 2.62 (d, J = 13.1 Hz, 3H), 1.90 (s, 1H), 1.81-1.43 (m, 3H), 1.31 (s, 1H) | (ESI (+)) m/e 439 (M + H)⁺ |
| 897 | N-[4-(1,8-diazaspiro[4.5]dec-1-ylcarbonyl)phenyl]-5-fluoro-1,3-dihydro-2H-isoindole-2-carboxamide | ¹H NMR (400 MHz, DMSO-D$_2$O) δ 7.61-7.51 (m, 2H), 7.37 (dd, J = 8.3, 5.2 Hz, 1H), 7.33-7.25 (m, 2H), 7.16 (d, J = 9.0 Hz, 1H), 7.10 (dd, J = 12.4, 5.4 Hz, 1H), 4.76 (d, J = 13.0 Hz, 4H), 3.39 (t, J = 6.7 Hz, 2H), 3.06 (d, J = 12.4 Hz, 2H), 3.00-2.82 (m, 2H), 2.79-2.61 (m, 2H), 1.99 (t, J = 6.9 Hz, 2H), 1.88 (s, 1H), 1.73 (dd, J = 13.6, 6.9 Hz, 2H), 1.44 (d, J = 13.3 Hz, 2H) | (ESI (+)) m/e 423 (M + H)⁺ |
| 898 | N-[4-(1,8-diazaspiro[4.5]dec-8-ylcarbonyl)phenyl]-5-fluoro-1,3-dihydro-2H-isoindole-2-carboxamide | ¹H NMR (400 MHz, DMSO-D$_2$O) δ 7.71-7.51 (m, 2H), 7.37 (dd, J = 8.4, 5.2 Hz, 1H), 7.33-7.23 (m, 2H), 7.22-7.12 (m, 1H), 7.09 (dd, J = 13.2, 4.7 Hz, 1H), 4.77 (d, J = 12.6 Hz, 4H), 3.62-3.39 (m, 4H), 3.00-2.75 (m, 2H), 1.86-1.67 (m, 2H), 1.67-1.43 (m, 6H) | (ESI (+)) m/e 423 (M + H)⁺ |
| 899 | N-[4-(2,6-diazaspiro[3.4]oct-2-ylcarbonyl)phenyl]-5-fluoro-1,3-dihydro-2H-isoindole-2-carboxamide | ¹H NMR (400 MHz, DMSO-D$_2$O) δ 7.68-7.49 (m, 4H), 7.37 (dd, J = 8.5, 5.2 Hz, 1H), 7.23-7.04 (m, 2H), 4.77 (d, J = 12.3 Hz, 4H), 4.10 (s, 4H), 3.00 (s, 2H), 2.83 (dd, J = 46.1, 39.1 Hz, 2H), 1.98 (t, J = 7.1 Hz, 2H) | (ESI (+)) m/e 395 (M + H)⁺ |
| 900 | N-[4-(1,7-diazaspiro[3.5]non-7-ylcarbonyl)phenyl]-5-fluoro-1,3-dihydro-2H-isoindole-2-carboxamide | ¹H NMR (400 MHz, DMSO-D$_2$O) δ 7.70-7.53 (m, 2H), 7.48-7.23 (m, 3H), 7.23-7.03 (m, 2H), 5.45 (s, 1H), 4.77 (d, J = 12.2 Hz, 4H), 3.98 (s, 2H), 3.56 (t, J = 5.7 Hz, 2H), 2.71 (t, J = 7.1 Hz, 2H), 2.32-2.05 (m, 4H), 1.86 (s, 2H) | (ESI (+)) m/e 409 (M + H)⁺ |

| Ex | Name | ¹H NMR | MS |
|---|---|---|---|
| 901 | N-[4-(1,6-diazaspiro[3.5]non-1-ylcarbonyl)phenyl]-5-fluoro-1,3-dihydro-2H-isoindole-2-carboxamide | ¹H NMR (400 MHz, DMSO-D₂O) δ 7.69-7.52 (m, 2H), 7.47 (d, J = 8.6 Hz, 2H), 7.37 (dd, J = 8.4, 5.1 Hz, 1H), 7.22-7.01 (m, 2H), 4.77 (d, J = 12.9 Hz, 4H), 4.24-3.92 (m, 2H), 3.20 (s, 3H), 2.97 (t, J = 18.2 Hz, 1H), 2.75 (t, J = 21.1 Hz, 1H), 2.29-2.11 (m, 1H), 2.10-1.96 (m, 1H), 1.62 (s, 1H), 1.49 (d, J = 11.0 Hz, 1H) | (ESI (+)) m/e 409 (M + H)⁺ |
| 902 | N-[4-(2,5-diazaspiro[3.5]non-2-ylcarbonyl)phenyl]-5-fluoro-1,3-dihydro-2H-isoindole-2-carboxamide | ¹H NMR (400 MHz, DMSO-D₂O) δ 7.69-7.50 (m, 4H), 7.37 (dd, J = 8.6, 5.2 Hz, 1H), 7.22-7.03 (m, 2H), 4.77 (d, J = 13.2 Hz, 4H), 3.92 (s, 4H), 2.66 (dd, J = 10.8, 5.5 Hz, 2H), 1.70-1.59 (m, 2H), 1.51 (s, 2H), 1.40 (d, J = 4.6 Hz, 2H) | (ESI (+)) m/e 409 (M + H)⁺ |
| 903 | 5-fluoro-N-[4-(5-oxa-2-azaspiro[3.4]oct-2-ylcarbonyl)phenyl]-1,3-dihydro-2H-isoindole-2-carboxamide | ¹H NMR (400 MHz, DMSO-D₂O) δ 7.71-7.47 (m, 4H), 7.37 (dd, J = 8.4, 5.2 Hz, 1H), 7.22-6.96 (m, 2H), 4.77 (d, J = 12.5 Hz, 4H), 4.16 (dd, J = 23.5, 9.7 Hz, 4H), 3.77 (t, J = 6.8 Hz, 2H), 2.07 (t, J = 7.3 Hz, 2H), 1.94-1.70 (m, 2H) | (ESI (+)) m/e 396 (M + H)⁺ |
| 904 | 5-fluoro-N-[4-(6-oxa-2-azaspiro[3.5]non-2-ylcarbonyl)phenyl]-1,3-dihydro-2H-isoindole-2-carboxamide | ¹H NMR (400 MHz, DMSO-D₂O) δ 7.68-7.51 (m, 2H), 7.51-7.33 (m, 1H), 7.36-7.20 (m, 1H), 7.21-6.92 (m, 2H), 4.77 (d, J = 12.5 Hz, 4H), 4.24 (dd, J = 26.5, 6.0 Hz, 4H), 3.48-3.36 (m, 2H), 1.97-1.75 (m, 2H), 1.66-1.25 (m, 4H) | (ESI (+)) m/e 410 (M + H)⁺ |
| 905 | 5-fluoro-N-[4-(2-oxa-7-azaspiro[3.5]non-7-ylcarbonyl)phenyl]-1,3-dihydro-2H-isoindole-2-carboxamide | ¹H NMR (400 MHz, DMSO-D₂O) δ 7.65-7.54 (m, 2H), 7.37 (dd, J = 8.3, 5.2 Hz, 1H), 7.35-7.23 (m, 2H), 7.22-7.03 (m, 2H), 4.77 (d, J = 12.4 Hz, 4H), 4.35 (s, 4H), 3.47-3.36 (m, 4H), 1.87-1.75 (m, 4H) | (ESI (+)) m/e 410 (M + H)⁺ |
| 906 | 5-fluoro-N-[4-(hexahydro-5H-furo[2,3-c]pyrrol-5-ylcarbonyl)phenyl]-1,3-dihydro-2H-isoindole-2-carboxamide | ¹H NMR (400 MHz, DMSO-D₂O) δ 7.67-7.54 (m, 2H), 7.48-7.28 (m, 3H), 7.24-6.92 (m, 2H), 4.77 (d, J = 12.4 Hz, 4H), 4.52-4.31 (m, 1H), 3.86 (dd, J = 15.5, 7.0 Hz, 1H), 3.79-3.53 (m, 4H), 3.43 (dd, J = 11.7, 5.3 Hz, 1H), 2.97-2.81 (m, 1H), 2.17-1.88 (m, 1H), 1.88-1.59 (m, 1H) | (ESI (+)) m/e 396 (M + H)⁺ |
| 907 | 5-fluoro-N-[4-(tetrahydro-1H-furo[3,4-c]pyrrol-5(3H)-ylcarbonyl)phenyl]-1,3-dihydro-2H-isoindole-2-carboxamide | ¹H NMR (400 MHz, DMSO-D₂O) δ 7.65-7.54 (m, 2H), 7.54-7.31 (m, 3H), 7.26-7.03 (m, 2H), 4.77 (d, J = 12.2 Hz, 4H), 3.74 (ddd, J = 19.7, 10.5, 7.2 Hz, 4H), 3.56-3.34 (m, 4H), 3.01-2.84 (m, 2H) | (ESI (+)) m/e 396 (M + H)⁺ |
| 908 | 5-fluoro-N-[4-(hexahydrofuro[3,4-c]pyridin-5(3H)-ylcarbonyl)phenyl]-1,3-dihydro-2H-isoindole-2-carboxamide | ¹H NMR (400 MHz, DMSO-D₂O) δ 7.59 (d, J = 8.7 Hz, 2H), 7.43-7.35 (m, 1H), 7.35-7.24 (m, 1H), 7.22-7.05 (m, 2H), 4.77 (d, J = 12.5 Hz, 4H), 3.81-3.67 (m, 2H), 3.62-3.40 (m, 4H), 1.76 (s, 1H), 1.62-1.36 (m, 1H), 1.28-1.08 (m, 2H) | (ESI (+)) m/e 410 (M + H)⁺ |
| 976 | N-(4-{[(1S)-1-(4-fluorophenyl)-2-hydroxyethyl]carbamoyl}phenyl)-1,3-dihydro-2H-isoindole-2-carboxamide | ¹H NMR (300 MHz, DMSO-d₆) δ 8.59 (s, 1H), 8.49 (d, J = 8.0 Hz, 1H), 7.87-7.79 (m, 2H), 7.72-7.65 (m, 2H), 7.47-7.28 (m, 6H), 7.19-7.09 (m, 2H), 5.06 (d, J = 6.7 Hz, 1H), 4.95-4.87 (m, 1H), 4.79 (s, 4H), 3.77-3.57 (m, 2H) | (ESI (+)) m/e 420 (M + H)⁺ |
| 977 | N-(4-{[(1S)-2-hydroxy-1-(4-methoxyphenyl)ethyl]carbamoyl}phenyl)-1,3-dihydro-2H-isoindole-2-carboxamide | ¹H NMR (300 MHz, DMSO-d₆) δ 8.58 (d, J = 3.8 Hz, 1H), 8.42 (d, J = 8.1 Hz, 1H), 7.86-7.76 (m, 3H), 7.69 (s, 1H), 7.69-7.61 (m, 2H), 7.41-7.27 (m, 6H), 6.91-6.84 (m, 2H), 5.07-4.96 (m, 1H), 3.77-3.59 (m, 4H), 3.31 (s, 4H) | (ESI (+)) m/e 432 (M + H)⁺ |
| 978 | N-(4-{[(1S)-1-(1,3-benzodioxol-5-yl)-2-hydroxyethyl]carbamoyl}phenyl)-1,3-dihydro-2H-isoindole-2-carboxamide | ¹H NMR (300 MHz, DMSO-d₆) δ 8.59 (s, 1H), 8.39 (d, J = 8.1 Hz, 1H), 7.86-7.78 (m, 2H), 7.72-7.64 (m, 2H), 7.41-7.28 (m, 4H), 6.99 (s, 1H), 6.86-6.82 (m, 2H), 5.97 (d, J = 2.3 Hz, 2H), 5.05-4.93 (m, 1H), 4.92-4.82 (m, 1H), 4.81 (d, J = 14.1 Hz, 4H), 3.73-3.53 (m, 2H) | (ESI (+)) m/e 446 (M + H)⁺ |

| Ex | Name | ¹H NMR | MS |
|---|---|---|---|
| 1089 | 5-fluoro-N-(4-{[1-(1,3-thiazol-2-yl)propan-2-yl]carbamoyl}phenyl)-1,3-dihydro-2H-isoindole-2-carboxamide | ¹H NMR (400 MHz, DMSO-d₆, Temp = 90° C.) δ 7.78-7.64 (m, 2H), 7.64-7.53 (m, 2H), 7.52-7.34 (m, 1H), 7.28-7.16 (m, 1H), 7.17-7.03 (m, 1H), 4.77 (d, J = 12.4 Hz, 4H), 4.38 (h, J = 6.6 Hz, 1H), 3.41-3.27 (m, 2H), 3.24-3.15 (m, 1H), 2.51 (dt, J = 3.7, 1.9 Hz, 2H), 1.25 (t, J = 5.6 Hz, 3H), 1.11 (t, J = 7.1 Hz, 1H) | (ESI (+)) m/e 425 (M + H)⁺ |
| 1090 | N-{4-[(4,4-difluorocyclohexyl)carbamoyl]phenyl}-5-fluoro-1,3-dihydro-2H-isoindole-2-carboxamide | ¹H NMR (400 MHz, DMSO-d₆, Temp = 90° C.) δ 7.86-7.70 (m, 2H), 7.67-7.53 (m, 2H), 7.44-7.29 (m, 1H), 7.24-7.03 (m, 2H), 4.76 (t, J = 10.2 Hz, 4H), 4.08-3.87 (m, 1H), 2.16-1.83 (m, 5H), 1.79-1.54 (m, 2H) | (ESI (+)) m/e 418 (M + H)⁺ |
| 1091 | N-(4-{[1-(3,5-dimethyl-1H-pyrazol-1-yl)propan-2-yl]carbamoyl}phenyl)-5-fluoro-1,3-dihydro-2H-isoindole-2-carboxamide | ¹H NMR (400 MHz, DMSO-d₆, Temp = 90° C.) δ 7.81-7.65 (m, 2H), 7.65-7.55 (m, 2H), 7.41-7.31 (m, 1H), 7.23-6.98 (m, 2H), 4.77 (d, J = 12.4 Hz, 4H), 4.35 (h, J = 6.5 Hz, 1H), 4.17-4.06 (m, 1H), 4.06-3.88 (m, 1H), 3.20 (s, 1H), 2.22 (s, 3H), 2.10 (s, 3H), 1.26-1.01 (m, 3H) | (ESI (+)) m/e 436 (M + H)⁺ |
| 1092 | 5-fluoro-N-(4-{[2-methyl-2-(morpholin-4-yl)butyl]carbamoyl}phenyl)-1,3-dihydro-2H-isoindole-2-carboxamide | ¹H NMR (400 MHz, DMSO-d₆, Temp = 90° C.) δ 7.87-7.71 (m, 2H), 7.69-7.58 (m, 2H), 7.46-7.29 (m, 1H), 7.25-7.02 (m, 2H), 4.89-4.69 (m, 4H), 3.90-3.67 (m, 4H), 3.61-3.41 (m, 2H), 3.15-2.96 (m, 2H), 1.84-1.50 (m, 2H), 1.32-1.06 (m, 3H), 1.07-0.72 (m, 3H) | (ESI (+)) m/e 455 (M + H)⁺ |
| 1093 | 5-fluoro-N-(4-{[2-(2-methyl-1,3-thiazol-4-yl)ethyl]carbamoyl}phenyl)-1,3-dihydro-2H-isoindole-2-carboxamide | ¹H NMR (400 MHz, Pyridine-d₅) δ 8.59-8.46 (m, 1H), 7.90 (d, J = 8.6 Hz, 2H), 7.68-7.58 (m, 2H), 7.10 (d, J = 5.0 Hz, 1H), 4.87 (dd, J = 16.8, 9.9 Hz, 4H), 3.86-3.64 (m, 4H), 3.64-3.40 (m, 5H), 2.86-2.58 (m, 2H) | (ESI (+)) m/e 425 (M + H)⁺ |
| 1094 | 5-fluoro-N-(4-{[2-methyl-1-(morpholin-4-yl)propan-2-yl]carbamoyl}phenyl)-1,3-dihydro-2H-isoindole-2-carboxamide | ¹H NMR (400 MHz, DMSO-d₆, Temp = 90° C.) δ 7.70 (d, J = 8.7 Hz, 2H), 7.66-7.54 (m, 2H), 7.37 (dd, J = 8.4, 5.1 Hz, 1H), 7.21-7.05 (m, 2H), 4.77 (d, J = 12.5 Hz, 4H), 3.65 (s, 4H), 2.80 (d, J = 54.6 Hz, 5H), 1.41 (s, 6H) | (ESI (+)) m/e 425 (M + H)⁺ |
| 1095 | 5-fluoro-N-{4-[(4-methoxybenzyl)carbamoyl]phenyl}-1,3-dihydro-2H-isoindole-2-carboxamide | ¹H NMR (400 MHz, DMSO-d₆, Temp = 90° C.) δ 7.89-7.70 (m, 2H), 7.70-7.52 (m, 2H), 7.37 (dd, J = 8.3, 5.2 Hz, 1H), 7.26 (d, J = 8.6 Hz, 2H), 7.20-7.04 (m, 2H), 6.93-6.76 (m, 2H), 4.77 (d, J = 12.5 Hz, 4H), 4.41 (s, 2H), 3.74 (s, 3H) | (ESI (+)) m/e 420 (M + H)⁺ |
| 1096 | 5-fluoro-N-(4-{[3-(morpholin-4-yl)propyl]carbamoyl}phenyl)-1,3-dihydro-2H-isoindole-2-carboxamide | ¹H NMR (400 MHz, DMSO-d₆, Temp = 90° C.) δ 7.83-7.70 (m, 2H), 7.69-7.55 (m, 2H), 7.37 (dd, J = 8.4, 5.1 Hz, 1H), 7.27-7.03 (m, 2H), 4.77 (d, J = 12.4 Hz, 4H), 3.86 (s, 4H), 3.36 (dd, J = 17.9, 11.2 Hz, 3H), 3.22-3.09 (m, 3H), 2.09-1.81 (m, 2H) | (ESI (+)) m/e 427 (M + H)⁺ |
| 1097 | N-alpha-(4-{[(5-fluoro-1,3-dihydro-2H-isoindol-2-yl)carbonyl]amino}benoyl)-D-phenylalaninamide | ¹H NMR (400 MHz, DMSO-d₆, Temp = 90° C.) δ 7.76-7.64 (m, 2H), 7.64-7.52 (m, 2H), 7.44-7.31 (m, 1H), 7.31-7.21 (m, 4H), 7.21-7.04 (m, 3H), 4.82-4.73 (m, 4H), 4.73-4.62 (m, 1H), 3.23-3.12 (m, 2H), 3.07-2.93 (m, 2H) | (ESI (+)) m/e 447 (M + H)⁺ |
| 1098 | N-(4-{[2-(acetylamino)phenyl]carbamoyl}phenyl)-5-fluoro-1,3-dihydro-2H-isoindole-2-carboxamide | ¹H NMR (400 MHz, DMSO-d₆, Temp = 90° C.) δ 7.96-7.78 (m, 2H), 7.77-7.64 (m, 3H), 7.51-7.42 (m, 1H), 7.42-7.31 (m, 1H), 7.28-7.15 (m, 3H), 7.15-7.03 (m, 1H), 4.86-4.70 (m, 4H), 2.09 (s, 3H) | (ESI (+)) m/e 433 (M + H)⁺ |
| 1099 | 5-fluoro-N-[4-({4-[2-(2-hydroxyethoxy)ethyl]piperazin-1-yl}carbonyl)phenyl]-1,3-dihydro-2H-isoindole-2-carboxamide | ¹H NMR (400 MHz, DMSO-d₆, Temp = 90° C.) δ 7.71-7.57 (m, 2H), 7.50-7.33 (m, 3H), 7.25-7.01 (m, 2H), 4.77 (d, J = 12.5 Hz, 4H), 3.65-3.47 (m, 4H), 3.35 (dd, J = 12.2, 7.3 Hz, 6H), 2.52 (dt, J = 3.8, 1.9 Hz, 2H) | (ESI (+)) m/e 457 (M + H)⁺ |

| Ex | Name | ¹H NMR | MS |
|---|---|---|---|
| 1100 | 5-fluoro-N-(4-{[2-(furan-2-yl)-2-(pyrrolidin-1-yl)ethyl]carbamoyl}phenyl)-1,3-dihydro-2H-isoindole-2-carboxamide | ¹H NMR (400 MHz, DMSO-$d_6$, Temp = 90° C.) δ 7.76-7.67 (m, 3H), 7.66-7.53 (m, 2H), 7.37 (dd, J = 8.4, 5.2 Hz, 1H), 7.25-7.02 (m, 2H), 6.78 (d, J = 3.3 Hz, 1H), 6.55 (dd, J = 3.3, 1.9 Hz, 1H), 4.89-4.68 (m, 6H), 4.08-3.94 (m, 1H), 3.87 (dd, J = 14.0, 7.4 Hz, 1H), 3.43 (s, 1H), 2.00-1.78 (m, 4H) | (ESI (+)) m/e 463 (M + H)⁺ |
| 1101 | N-{4-[bis(2-methoxyethyl)carbamoyl]phenyl}-5-fluoro-1,3-dihydro-2H-isoindole-2-carboxamide | ¹H NMR (400 MHz, DMSO-$d_6$, Temp = 90° C.) δ 7.58 (d, J = 8.6 Hz, 2H), 7.37 (dd, J = 8.3, 5.1 Hz, 1H), 7.31-7.22 (m, 2H), 7.17 (d, J = 8.9 Hz, 1H), 7.13-7.03 (m, 1H), 4.76 (d, J = 12.5 Hz, 4H), 3.60-3.41 (m, 8H), 3.24 (s, 6H) | (ESI (+)) m/e 416 (M + H)⁺ |
| 1102 | N-{4-[(1-amino-1-oxohexan-2-yl)carbamoyl]phenyl}-5-fluoro-1,3-dihydro-2H-isoindole-2-carboxamide | ¹H NMR (400 MHz, DMSO-$d_6$, Temp = 90° C.) δ 7.87-7.71 (m, 2H), 7.64 (t, J = 10.2 Hz, 2H), 7.46-7.31 (m, 1H), 7.23-7.03 (m, 2H), 4.78 (d, J = 12.5 Hz, 4H), 4.40 (dd, J = 8.6, 5.6 Hz, 1H), 1.90-1.62 (m, 2H), 1.45-1.18 (m, 4H), 0.87 (t, J = 6.9 Hz, 3H) | (ESI (+)) m/e 413 (M + H)⁺ |
| 1103 | N-(4-{[2-(3,4-dimethoxyphenyl)ethyl]carbamoyl}phenyl)-5-fluoro-1,3-dihydro-2H-isoindole-2-carboxamide | ¹H NMR (400 MHz, DMSO-$d_6$, Temp = 90° C.) δ 7.72 (d, J = 8.7 Hz, 2H), 7.60 (d, J = 8.7 Hz, 2H), 7.43-7.28 (m, 1H), 7.21-7.04 (m, 2H), 6.91-6.81 (m, 2H), 6.81-6.69 (m, 1H), 4.77 (d, J = 12.5 Hz, 4H), 3.73 (d, J = 2.5 Hz, 6H), 3.58-3.39 (m, 2H), 2.93-2.68 (m, 2H) | (ESI (+)) m/e 464 (M + H)⁺ |
| 1104 | N-(4-{[(2S)-3,3-dimethyl-1-(methylamino)-1-oxobutan-2-yl]carbamoyl}phenyl)-5-fluoro-1,3-dihydro-2H-isoindole-2-carboxamide | ¹H NMR (400 MHz, DMSO-$d_6$, Temp = 90° C.) δ 7.88-7.70 (m, 2H), 7.70-7.57 (m, 2H), 7.45-7.30 (m, 1H), 7.26-7.01 (m, 2H), 4.78 (d, J = 12.6 Hz, 4H), 4.41 (d, J = 6.3 Hz, 1H), 2.64 (s, 3H), 1.03 (s, 9H) | (ESI (+)) m/e 427 (M + H)⁺ |
| 1105 | N-alpha-(4-{[(5-fluoro-1,3-dihydro-2H-isoindol-2-yl)carbonyl]amino}benzoyl)-L-phenylalaninamide | ¹H NMR (400 MHz, DMSO-$d_6$, Temp = 90° C.) δ 7.76-7.64 (m, 2H), 7.64-7.54 (m, 2H), 7.44-7.33 (m, 1H), 7.32-7.22 (m, 4H), 7.25-7.13 (m, 3H), 7.12-6.99 (m, 1H), 4.81-4.71 (m, 4H), 4.71-4.61 (m, 1H), 3.20-3.11 (m, 1H), 3.08-2.93 (m, 1H) | (ESI (+)) m/e 447 (M + H)⁺ |
| 1106 | N-(4-{[(2R)-1-amino-4-methyl-1-oxopentan-2-yl]carbamoyl}phenyl)-5-fluoro-1,3-dihydro-2H-isoindole-2-carboxamide | ¹H NMR (400 MHz, DMSO-$d_6$, Temp = 90° C.) δ 7.87-7.72 (m, 2H), 7.70-7.52 (m, 2H), 7.45-7.26 (m, 1H), 7.24-7.03 (m, 2H), 4.78 (d, J = 12.6 Hz, 4H), 4.57-4.38 (m, 1H), 1.90-1.47 (m, 3H), 1.07-0.71 (m, 6H) | (ESI (+)) m/e 413 (M + H)⁺ |
| 1107 | -{4-[(4-cyclohexylpiperazin-1-yl)carbonyl]phenyl}-5-fluoro-1,3-dihydro-2H-isoindole-2-carboxamide | ¹H NMR (400 MHz, DMSO-$d_6$, Temp = 90° C.) δ 7.76-7.57 (m, 2H), 7.51-7.32 (m, 3H), 7.23-7.03 (m, 2H), 4.77 (d, J = 12.4 Hz, 4H), 3.88 (d, J = 76.9 Hz, 4H), 3.22-3.10 (m, 2H), 2.08 (d, J = 11.3 Hz, 2H), 1.86 (d, J = 13.1 Hz, 2H), 1.64 (d, J = 12.9 Hz, 1H), 1.54-1.17 (m, 6H), 1.17-1.04 (m, 1H) | (ESI (+)) m/e 451 (M + H)⁺ |
| 1108 | 5-fluoro-N-(4-{[3-(methylcarbamoyl)phenyl]carbamoyl}phenyl)-1,3-dihydro-2H-isoindole-2-carboxamide | ¹H NMR (400 MHz, DMSO-$d_6$, Temp = 90° C.) δ 8.16 (t, J = 1.8 Hz, 1H), 7.98-7.80 (m, 3H), 7.74-7.59 (m, 2H), 7.59-7.47 (m, 1H), 7.49-7.33 (m, 2H), 7.24-7.05 (m, 2H), 4.79 (d, J = 12.5 Hz, 4H), 2.83 (d, J = 3.6 Hz, 3H) | (ESI (+)) m/e 433 (M + H)⁺ |
| 1109 | N-{4-[(2-amino-2-oxo-1-phenylethyl)carbamoyl]phenyl}-5-fluoro-1,3-dihydro-2H-isoindole-2-carboxamide | ¹H NMR (400 MHz, DMSO-$d_6$, Temp = 90° C.) δ 7.90-7.72 (m, 2H), 7.64 (d, J = 8.7 Hz, 2H), 7.50 (d, J = 7.5 Hz, 2H), 7.43-7.26 (m, 4H), 7.20-7.02 (m, 2H), 5.62 (s, 1H), 4.77 (d, J = 12.5 Hz, 4H) | (ESI (+)) m/e 433 (M + H)⁺ |
| 1110 | N-{4-[(3-tert-butoxypropyl)carbamoyl]phenyl}-5-fluoro-1,3-dihydro-2H-isoindole-2-carboxamide | ¹H NMR (400 MHz, DMSO-$d_6$, Temp = 90° C.) δ 7.79-7.66 (m, 2H), 7.66-7.53 (m, 2H), 7.37 (dd, J = 8.4, 5.1 Hz, 1H), 7.27-7.02 (m, 2H), 4.77 (d, J = 12.4 Hz, 4H), 3.44-3.35 (m, 2H), 3.31 (dd, J = 16.4, 9.5 Hz, 2H), 1.73 (p, J = 6.6 Hz, 2H), 1.15 (s, 9H) | (ESI (+)) m/e 414 (M + H)⁺ |

| Ex | Name | ¹H NMR | MS |
|---|---|---|---|
| 1111 | N-(4-{[2-(2,6-dimethylmorpholin-4-yl)ethyl]carbamoyl}phenyl)-5-fluoro-1,3-dihydro-2H-isoindole-2-carboxamide | ¹H NMR (400 MHz, DMSO-$d_6$, Temp = 90° C.) δ 7.86-7.72 (m, 2H), 7.69-7.55 (m, 2H), 7.47-7.32 (m, 1H), 7.24-6.96 (m, 2H), 4.78 (d, J = 12.5 Hz, 4H), 3.92-3.76 (m, 2H), 3.67 (t, J = 6.2 Hz, 2H), 3.52 (d, J = 12.0 Hz, 2H), 3.31 (dd, J = 13.3, 7.0 Hz, 3H), 2.71 (t, J = 11.7 Hz, 2H), 1.17 (d, J = 6.3 Hz, 6H) | (ESI (+)) m/e 441 (M + H)⁺ |
| 1112 | N-(4-{[(1R)-2-amino-2-oxo-1-phenylethyl]carbamoyl}phenyl)-5-fluoro-1,3-dihydro-2H-isoindole-2-carboxamide | ¹H NMR (400 MHz, DMSO-$d_6$, Temp = 90° C.) δ 7.87-7.70 (m, 2H), 7.70-7.56 (m, 2H), 7.51 (dd, J = 11.1, 9.7 Hz, 2H), 7.44-7.25 (m, 4H), 7.22-7.00 (m, 2H), 5.62 (s, 1H), 4.77 (d, J = 12.5 Hz, 4H) | (ESI (+)) m/e 433 (M + H)⁺ |
| 1113 | -fluoro-N-{4-[(3-methoxybenzyl)carbamoyl]phenyl}-1,3-dihydro-2H-isoindole-2-carboxamide | ¹H NMR (400 MHz, DMSO-$d_6$, Temp = 90° C.) δ 7.89-7.71 (m, 2H), 7.70-7.53 (m, 2H), 7.43-7.30 (m, 1H), 7.27-7.16 (m, 2H), 7.16-6.97 (m, 1H), 6.97-6.85 (m, 2H), 6.86-6.68 (m, 1H), 4.87-4.65 (m, 4H), 4.54-4.25 (m, 2H), 3.75 (s, 3H) | (ESI (+)) m/e 420 (M + H)⁺ |
| 1114 | N-(4-{[2-(3,5-dimethyl-1H-pyrazol-1-yl)ethyl]carbamoyl}phenyl)-5-fluoro-1,3-dihydro-2H-isoindole-2-carboxamide | ¹H NMR (400 MHz, DMSO-$d_6$, Temp = 90° C.) δ 7.78-7.67 (m, 2H), 7.65-7.52 (m, 2H), 7.45-7.29 (m, 1H), 7.25-7.03 (m, 2H), 4.79 (dd, J = 15.9, 8.4 Hz, 4H), 4.16 (t, J = 6.4 Hz, 2H), 3.59 (t, J = 6.4 Hz, 2H), 2.21 (s, 3H), 2.14 (s, 3H) | (ESI (+)) m/e 422 (M + H)⁺ |
| 1115 | 5-fluoro-N-(4-{[2-methyl-2-(morpholin-4-yl)propyl]carbamoyl}phenyl)-1,3-dihydro-2H-isoindole-2-carboxamide | ¹H NMR (400 MHz, DMSO-$d_6$, Temp = 90° C.) δ 7.90-7.74 (m, 2H), 7.74-7.56 (m, 2H), 7.48-7.31 (m, 1H), 7.28-7.03 (m, 2H), 4.78 (d, J = 12.4 Hz, 4H), 4.02-3.80 (m, 4H), 3.63 (s, 2H), 3.46-3.32 (m, 4H), 1.38 (s, 6H) | (ESI (+)) m/e 441 (M + H)⁺ |
| 1116 | 5-fluoro-N-(4-{[(3S)-1-methyl-2-oxoazepan-3-yl]carbamoyl}phenyl)-1,3-dihydro-2H-isoindole-2-carboxamide | ¹H NMR (400 MHz, DMSO-$d_6$, Temp = 90° C.) δ 7.83-7.70 (m, 2H), 7.68-7.58 (m, 2H), 7.37 (dd, J = 8.3, 5.2 Hz, 1H), 7.24-7.03 (m, 2H), 4.82-4.69 (m, 5H), 3.65 (dd, J = 15.6, 11.3 Hz, 1H), 3.03-2.83 (m, 3H), 2.03-1.80 (m, 2H), 1.81-1.66 (m, 2H), 1.62-1.33 (m, 2H) | (ESI (+)) m/e 425 (M + H)⁺ |
| 1117 | 5-fluoro-N-(4-{[2-(4-methylpiperazin-1-yl)ethyl]carbamoyl}phenyl)-1,3-dihydro-2H-isoindole-2-carboxamide | ¹H NMR (400 MHz, DMSO-$d_6$, Temp = 90° C.) δ 7.81-7.69 (m, 2H), 7.69-7.56 (m, 2H), 7.37 (dd, J = 8.3, 5.2 Hz, 1H), 7.21-6.98 (m, 2H), 4.77 (d, J = 12.3 Hz, 4H), 3.50 (t, J = 6.5 Hz, 2H), 3.25-3.16 (m, 4H), 3.08-2.98 (m, 4H), 2.89 (t, J = 6.5 Hz, 2H), 2.58-2.46 (m, 3H) | (ESI (+)) m/e 426 (M + H)⁺ |
| 1118 | 5-fluoro-N-(4-{[4-(morpholin-4-yl)benzyl]carbamoyl}phenyl)-1,3-dihydro-2H-isoindole-2-carboxamide | ¹H NMR (400 MHz, DMSO-$d_6$, Temp = 90° C.) δ 7.87-7.71 (m, 2H), 7.71-7.52 (m, 2H), 7.45-7.29 (m, 1H), 7.19 (dq, J = 9.0, 2.5 Hz, 3H), 7.14-7.02 (m, 1H), 6.92-6.79 (m, 2H), 4.77 (d, J = 12.6 Hz, 4H), 4.38 (s, 2H), 3.83-3.59 (m, 4H), 3.12-2.95 (m, 4H) | (ESI (+)) m/e 474 (M + H)⁺ |
| 1119 | 5-fluoro-N-(4-{[3-(piperidin-1-yl)propyl]carbamoyl}phenyl)-1,3-dihydro-2H-isoindole-2-carboxamide | ¹H NMR (400 MHz, DMSO-$d_6$, Temp = 90° C.) δ 7.84-7.71 (m, 2H), 7.70-7.61 (m, 2H), 7.48-7.32 (m, 1H), 7.27-7.01 (m, 2H), 4.77 (d, J = 12.4 Hz, 4H), 3.37 (dd, J = 12.4, 5.8 Hz, 5H), 3.16-3.01 (m, 3H), 3.01-2.70 (m, 2H), 2.07-1.90 (m, 3H), 1.77 (d, J = 46.1 Hz, 6H), 1.46 (s, 2H) | (ESI (+)) m/e 425 (M + H)⁺ |
| 1144 | 5-fluoro-N-{4-[3-methoxy-2,2-dimethylpropyl)carbamoyl]phenyl}-1,3-dihydro-2H-isoindole-2-carboxamide | ¹H NMR (400 MHz, DMSO-$d_6$, Temp = 90° C.) δ 7.76-7.70 (m, 2H), 7.65-7.59 (m, 2H), 7.37 (dd, J = 8.4, 5.1 Hz, 1H), 7.17 (dd, J = 9.1, 2.5 Hz, 1H), 7.14-7.05 (m, 1H), 4.79 (bs, 2H), 4.76 (bs, 2H), 3.15 (s, 2H), 2.99-2.78 (m, 1H), 0.90 (s, 6H) | (ESI (+)) m/e 400 (M + H)⁺ |

| Ex | Name | ¹H NMR | MS |
|---|---|---|---|
| 1145 | N-{4-[(3,3-dimethylbutyl)carbamoyl]phenyl}-5-fluoro-1,3-dihydro-2H-isoindole-2-carboxamide | ¹H NMR (400 MHz, DMSO-$d_6$, Temp = 90° C.) δ 7.73 (d, J = 8.6 Hz, 2H), 7.68-7.53 (m, 2H), 7.48-7.23 (m, 1H), 7.22-7.05 (m, 2H), 4.77 (d, J = 12.7 Hz, 4H), 3.29 (dd, J = 8.6, 6.6 Hz, 2H), 1.66-1.19 (m, 2H), 0.94 (s, 9H) | (ESI (+)) m/e 384 (M + H)⁺ |
| 1146 | 5-fluoro-N-(4-{[1-(furan-2-yl)propan-2-yl]carbamoyl}phenyl)-1,3-dihydro-2H-isoindole-2-carboxamide | ¹H NMR (400 MHz, DMSO-$d_6$, Temp = 90° C.) δ 7.79-7.66 (m, 2H), 7.62-7.49 (m, 2H), 7.45-7.31 (m, 1H), 7.24-6.96 (m, 2H), 6.51-6.25 (m, 1H), 6.13 (d, J = 3.2 Hz, 1H), 4.77 (d, J = 12.5 Hz, 4H), 4.27 (h, J = 6.7 Hz, 1H), 2.94 (dd, J = 15.0, 6.8 Hz, 2H), 2.87-2.69 (m, 1H), 1.19 (d, J = 6.7 Hz, 3H) | (ESI (+)) m/e 408 (M + H)⁺ |
| 1147 | 5-fluoro-N-(4-{[(3-methyl-1,2-oxazol-5-yl)methyl]carbamoyl}phenyl)-1,3-dihydro-2H-isoindole-2-carboxamide | ¹H NMR (400 MHz, DMSO-$d_6$, Temp = 90° C.) δ 7.86-7.71 (m, 2H), 7.71-7.56 (m, 2H), 7.47-7.24 (m, 1H), 7.22-6.98 (m, 2H), 6.16 (s, 1H), 4.88-4.69 (m, 4H), 4.54 (s, 2H), 2.20 (s, 3H) | (ESI (+)) m/e 395 (M + H)⁺ |
| 1148 | N-(4-{[(2R)-1-cyanobutan-2-yl]carbamoyl}phenyl)-5-fluoro-1,3-dihydro-2H-isoindole-2-carboxamide | ¹H NMR (400 MHz, DMSO-$d_6$, Temp = 90° C.) δ 7.86-7.72 (m, 2H), 7.72-7.54 (m, 2H), 7.37 (dd, J = 8.4, 5.2 Hz, 1H), 7.27-7.02 (m, 2H), 4.78 (d, J = 12.4 Hz, 4H), 4.24-4.01 (m, 1H), 2.90-2.65 (m, 2H), 1.76-1.53 (m, 2H), 0.92 (t, J = 7.4 Hz, 3H) | (ESI (+)) m/e 381 (M + H)⁺ |
| 1149 | N-{4-[(2R)-butan-2-ylcarbamoyl]phenyl}-5-fluoro-1,3-dihydro-2H-isoindole-2-carboxamide | ¹H NMR (400 MHz, DMSO-$d_6$, Temp = 90° C.) δ 7.82-7.68 (m, 2H), 7.68-7.52 (m, 2H), 7.44-7.27 (m, 1H), 7.26-7.04 (m, 2H), 4.77 (d, J = 12.4 Hz, 4H), 4.05-3.76 (m, 1H), 1.82-1.38 (m, 2H), 1.16 (t, J = 5.3 Hz, 3H), 0.88 (t, J = 7.4 Hz, 3H) | (ESI (+)) m/e 356 (M + H)⁺ |
| 1150 | 5-fluoro-N-(4-{[2-(1H-pyrazol-1-yl)ethyl]carbamoyl}phenyl)-1,3-dihydro-2H-isoindole-2-carboxamide | ¹H NMR (400 MHz, DMSO-$d_6$, Temp = 90° C.) δ 7.78-7.66 (m, 2H), 7.66-7.54 (m, 3H), 7.48-7.27 (m, 2H), 7.24-7.02 (m, 2H), 4.77 (d, J = 12.5 Hz, 4H), 4.31 (t, J = 6.4 Hz, 2H), 3.66 (t, J = 6.4 Hz, 2H), 3.04-2.82 (m, 1H) | (ESI (+)) m/e 394 (M + H)⁺ |
| 1151 | 5-fluoro-N-{4-[methyl(3-methylbutyl)carbamoyl]phenyl}-1,3-dihydro-2H-isoindole-2-carboxamide | ¹H NMR (400 MHz, DMSO-$d_6$, Temp = 90° C.) δ 7.65-7.50 (m, 2H), 7.37 (dd, J = 8.4, 5.2 Hz, 1H), 7.32-7.21 (m, 2H), 7.21-7.02 (m, 2H), 4.77 (d, J = 12.6 Hz, 4H), 3.44-3.28 (m, 2H), 2.92 (s, 4H), 1.62-1.19 (m, 3H), 0.84 (d, J = 6.3 Hz, 6H) | (ESI (+)) m/e 384 (M + H)⁺ |
| 1152 | N-(4-{[1-(ethylamino)-1-oxopropan-2-yl]carbamoyl}phenyl)-5-fluoro-1,3-dihydro-2H-isoindole-2-carboxamide | ¹H NMR (400 MHz, DMSO-$d_6$, Temp = 90° C.) δ 7.87-7.71 (m, 2H), 7.71-7.53 (m, 2H), 7.49-7.24 (m, 1H), 7.25-6.98 (m, 2H), 4.77 (d, J = 12.4 Hz, 4H), 4.55-4.28 (m, 1H), 3.19-3.02 (m, 2H), 3.01-2.74 (m, 3H), 1.96 (s, 1H), 1.34 (d, J = 7.1 Hz, 3H), 1.04 (t, J = 7.2 Hz, 2H) | (ESI (+)) m/e 399 (M + H)⁺ |
| 1153 | 5-fluoro-N-(4-{[(1-methyl-1H-pyrazol-3-yl)methyl]carbamoyl}phenyl)-1,3-dihydro-2H-isoindole-2-carboxamide | ¹H NMR (400 MHz, DMSO-$d_6$, Temp = 90° C.) δ 7.89-7.69 (m, 2H), 7.69-7.57 (m, 3H), 7.50 (d, J = 2.1 Hz, 1H), 7.42-7.22 (m, 2H), 7.25-7.00 (m, 2H), 4.77 (d, J = 12.4 Hz, 4H), 4.41 (s, 2H), 3.78 (s, 3H), 2.97 (s, 2H) | (ESI (+)) m/e 394 (M + H)⁺ |
| 1154 | 5-fluoro-N-{4-[(2-methoxybutyl)carbamoyl]phenyl}-1,3-dihydro-2H-isoindole-2-carboxamide | ¹H NMR (400 MHz, DMSO-$d_6$, Temp = 90° C.) δ 7.78-7.72 (m, 2H), 7.64-7.58 (m, 2H), 7.37 (dd, J = 8.4, 5.1 Hz, 1H), 7.17 (dd, J = 9.1, 2.4 Hz, 1H), 7.10 (td, J = 8.9, 2.5 Hz, 1H), 4.79 (bs, 3H), 4.76 (bs, 3H), 3.38-3.32 (m, 5H), 3.32 (s, 4H), 1.61-1.39 (m, 2H), 0.90 (t, J = 7.4 Hz, 3H) | (ESI (+)) m/e 386 (M + H)⁺ |
| 1155 | N-(4-{[4-(dimethylamino)butyl]carbamoyl}phenyl)-5-fluoro-1,3-dihydro-2H-isoindole-2-carboxamide | ¹H NMR (400 MHz, DMSO-$d_6$, Temp = 90° C.) δ 7.86-7.69 (m, 2H), 7.70-7.54 (m, 2H), 7.44-7.27 (m, 1H), 7.23-7.00 (m, 2H), 4.77 (d, J = 12.5 Hz, 4H), 3.31 (dd, J = 13.0, 6.3 Hz, 2H), 3.19-2.99 (m, 3H), 2.79 (s, 7H), 1.71-1.50 (m, 4H) | (ESI (+)) m/e 399 (M + H)⁺ |

| Ex | Name | ¹H NMR | MS |
|---|---|---|---|
| 1156 | 5-fluoro-N-{4-[(3S)-tetrahydrofuran-3-ylcarbamoyl]phenyl}-1,3-dihydro-2H-isoindole-2-carboxamide | ¹H NMR (400 MHz, DMSO-d₆, Temp = 90° C.) δ 7.82-7.70 (m, 2H), 7.70-7.54 (m, 2H), 7.44-7.28 (m, 1H), 7.23-7.03 (m, 2H), 4.77 (d, J = 12.5 Hz, 4H), 4.53-4.35 (m, 1H), 3.98-3.81 (m, 2H), 3.77-3.66 (m, 1H), 3.70-3.53 (m, 1H), 3.01-2.87 (m, 1H), 2.32-2.10 (m, 1H), 2.07-1.81 (m, 1H) | (ESI (+)) m/e 370 (M + H)⁺ |
| 1157 | 5-fluoro-N-{4-[(1-methoxybutan-2-yl)carbamoyl]phenyl}-1,3-dihydro-2H-isoindole-2-carboxamide | ¹H NMR (400 MHz, DMSO-d₆, Temp = 90° C.) δ 7.78-7.72 (m, 2H), 7.63-7.57 (m, 2H), 7.40-7.31 (m, 1H), 7.21-7.04 (m, 2H), 4.77 (d, J = 12.4 Hz, 4H), 4.11-3.94 (m, 1H), 3.55-3.32 (m, 2H), 3.28 (s, 3H), 1.72-1.39 (m, 2H), 0.89 (t, J = 7.4 Hz, 3H) | (ESI (+)) m/e 386 (M + H)⁺ |
| 1158 | N-{4-[(2-ethoxypropyl)carbamoyl]phenyl}-5-fluoro-1,3-dihydro-2H-isoindole-2-carboxamide | ¹H NMR (400 MHz, DMSO-d₆, Temp = 90° C.) δ 7.83-7.70 (m, 2H), 7.69-7.51 (m, 2H), 7.48-7.29 (m, 1H), 7.25-7.00 (m, 2H), 4.77 (d, J = 12.5 Hz, 4H), 3.71-3.55 (m, 1H), 3.58-3.40 (m, 2H), 3.40-3.29 (m, 1H), 1.26-0.98 (m, 6H) | (ESI (+)) m/e 386 (M + H)⁺ |
| 1159 | N-{4-[benzyl(methyl)carbamoyl]phenyl}-5-fluoro-1,3-dihydro-2H-isoindole-2-carboxamide | ¹H NMR (400 MHz, DMSO-d₆, Temp = 90° C.) δ 7.69-7.53 (m, 2H), 7.42-7.29 (m, 6H), 7.28 (dd, J = 13.0, 7.2 Hz, 3H), 7.19-7.01 (m, 2H), 4.76 (d, J = 12.4 Hz, 4H), 4.58 (d, J = 21.5 Hz, 3H), 2.89 (d, J = 3.2 Hz, 3H) | (ESI (+)) m/e 404 (M + H)⁺ |
| 1160 | N-{4-[(2S)-butan-2-ylcarbamoyl]phenyl}-5-fluoro-1,3-dihydro-2H-isoindole-2-carboxamide | ¹H NMR (400 MHz, DMSO_D₂O) δ 7.83-7.68 (m, 2H), 7.66-7.54 (m, 2H), 7.37 (dd, J = 8.4, 5.2 Hz, 1H), 7.20-7.12 (m, 1H), 7.12-7.01 (m, 1H), 4.77 (d, J = 12.5 Hz, 4H), 3.92 (h, J = 6.6 Hz, 1H), 1.70-1.41 (m, 2H), 1.15 (d, J = 6.6 Hz, 3H), 0.88 (t, J = 7.4 Hz, 3H) | (ESI (+)) m/e 356 (M + H)⁺ |
| 1161 | 5-fluoro-N-(4-{[2-(5-methyl-1H-pyrazol-1-yl)ethyl]carbamoyl}phenyl)-1,3-dihydro-2H-isoindole-2-carboxamide | ¹H NMR (400 MHz, DMSO-d₆, Temp = 90° C.) δ 7.83-7.68 (m, 2H), 7.66-7.54 (m, 2H), 7.37 (dd, J = 8.4, 5.2 Hz, 1H), 7.20-7.12 (m, 1H), 7.12-7.01 (m, 1H), 4.77 (d, J = 12.5 Hz, 4H), 3.92 (h, J = 6.6 Hz, 4H), 0.88 (t, J = 7.4 Hz, 3H) | (ESI (+)) m/e 408 (M + H)⁺ |
| 1162 | 5-fluoro-N-(4-{[2-(3-methyl-1H-pyrazol-1-yl)ethyl]carbamoyl}phenyl)-1,3-dihydro-2H-isoindole-2-carboxamide | ¹H NMR (400 MHz, DMSO-d₆, Temp = 90° C.) δ 7.77-7.66 (m, 2H), 7.66-7.56 (m, 2H), 7.50 (d, J = 2.1 Hz, 1H), 7.44-7.29 (m, 1H), 7.17 (dd, J = 9.0, 2.2 Hz, 1H), 7.14-7.00 (m, 1H), 6.00 (d, J = 2.2 Hz, 1H), 4.77 (d, J = 12.5 Hz, 4H), 4.21 (t, J = 6.4 Hz, 2H), 3.63 (t, J = 6.4 Hz, 2H), 2.89 (d, J = 62.0 Hz, 1H), 2.21 (d, J = 32.8 Hz, 3H) | (ESI (+)) m/e 408 (M + H)⁺ |
| 1163 | 5-fluoro-N-{4-[(2-methylpropyl)carbamoyl]phenyl}-1,3-dihydro-2H-isoindole-2-carboxamide | ¹H NMR (400 MHz, DMSO-d₆, Temp = 90° C.) δ 7.82-7.69 (m, 2H), 7.69-7.54 (m, 2H), 7.46-7.26 (m, 1H), 7.29-7.01 (m, 2H), 4.77 (d, J = 12.4 Hz, 4H), 3.15-3.05 (m, 2H), 2.98-2.75 (m, 3H), 2.06-1.89 (m, 2H), 1.92-1.78 (m, 1H), 0.90 (d, J = 6.7 Hz, 7H) | (ESI (+)) m/e 356 (M + H)⁺ |
| 1164 | 5-fluoro-N-{4-[(pyridin-3-ylmethyl)carbamoyl]phenyl}-1,3-dihydro-2H-isoindole-2-carboxamide | ¹H NMR (400 MHz, DMSO-d₆, Temp = 90° C.) δ 8.79-8.58 (m, 2H), 8.19 (t, J = 7.0 Hz, 1H), 7.84-7.73 (m, 2H), 7.73-7.66 (m, 1H), 7.70-7.55 (m, 2H), 7.50-7.27 (m, 1H), 7.27-7.06 (m, 2H), 4.77 (d, J = 12.4 Hz, 4H), 4.59 (s, 2H) | (ESI (+)) m/e 391 (M + H)⁺ |
| 1165 | 5-fluoro-N-{4-[(tetrahydrofuran-2-ylmethyl)carbamoyl]phenyl}-1,3-dihydro-2H-isoindole-2-carboxamide | ¹H NMR (400 MHz, DMSO-d₆, Temp = 90° C.) δ 7.85-7.72 (m, 2H), 7.66-7.53 (m, 2H), 7.46-7.32 (m, 1H), 7.24-7.14 (m, 1H), 7.14-7.04 (m, 1H), 4.93-4.61 (m, 4H), 4.11-3.90 (m, 1H), 3.87-3.72 (m, 1H), 3.72-3.53 (m, 1H), 3.35 (t, J = 7.5 Hz, 2H), 2.06-1.73 (m, 3H), 1.66-1.52 (m, 1H) | (ESI (+)) m/e 384 (M + H)⁺ |
| 1166 | N-(4-{[(1R)-1-cyclopropylethyl]carbamoyl}phenyl)-5-fluoro-1,3-dihydro-2H-isoindole-2-carboxamide | ¹H NMR (400 MHz, DMSO-d₆, Temp = 90° C.) δ 7.83-7.72 (m, 2H), 7.68-7.57 (m, 2H), 7.37 (dd, J = 8.3, 5.1 Hz, 1H), 7.23-7.02 (m, 2H), 4.77 (d, J = 12.5 Hz, 4H), 3.63-3.42 (m, 1H), 1.22 (d, J = 6.7 Hz, 3H), 1.15-0.79 (m, 1H), 0.51-0.24 (m, 3H), 0.24-0.11 (m, 1H) | (ESI (+)) m/e 368 (M + H)⁺ |

| Ex | Name | ¹H NMR | MS |
|---|---|---|---|
| 1167 | 5-fluoro-N-(4-{[1-(1-methylcyclopropyl)ethyl]carbamoyl}phenyl)-1,3-dihydro-2H-isoindole-2-carboxamide | ¹H NMR (400 MHz, DMSO-d$_6$, Temp = 90° C.) δ 7.83-7.68 (m, 2H), 7.68-7.54 (m, 2H), 7.37 (dd, J = 8.4, 5.1 Hz, 1H), 7.24-7.12 (m, 1H), 7.12-7.01 (m, 1H), 4.77 (d, J = 12.5 Hz, 4H), 3.72 (q, J = 6.8 Hz, 1H), 1.17 (d, J = 6.9 Hz, 3H), 1.07 (s, 3H), 0.68-0.51 (m, 1H), 0.49-0.27 (m, 1H), 0.32-0.12 (m, 2H) | (ESI (+)) m/e 382 (M + H)⁺ |
| 1168 | 5-fluoro-N-{4-[(thiophen-2-ylmethyl)carbamoyl]phenyl}-1,3-dihydro-2H-isoindole-2-carboxamide | ¹H NMR (400 MHz, DMSO-d$_6$, Temp = 90° C.) δ 7.89-7.70 (m, 2H), 7.70-7.56 (m, 2H), 7.48-7.26 (m, 2H), 7.24-7.14 (m, 1H), 7.14-7.05 (m, 1H), 7.05-6.95 (m, 1H), 6.98-6.86 (m, 1H), 4.90-4.67 (m, 4H), 4.63 (d, J = 4.2 Hz, 2H) | (ESI (+)) m/e 395 (M + H)⁺ |
| 1169 | -(4-{[(1S)-1-cyclopropylethyl]carbamoyl}phenyl)-5-fluoro-1,3-dihydro-2H-isoindole-2-carboxamide | ¹H NMR (400 MHz, DMSO-d$_6$, Temp = 90° C.) δ 7.85-7.70 (m, 2H), 7.68-7.51 (m, 2H), 7.37 (dd, J = 8.4, 5.2 Hz, 1H), 7.21-7.05 (m, 2H), 4.77 (d, J = 12.4 Hz, 4H), 3.64-3.41 (m, 1H), 1.22 (d, J = 6.7 Hz, 3H), 1.17-0.94 (m, 1H), 0.51-0.41 (m, 1H), 0.41-0.34 (m, 1H), 0.34-0.27 (m, 1H), 0.23-0.11 (m, 1H) | (ESI (+)) m/e 368 (M + H)⁺ |
| 1170 | 5-fluoro-N-{4-[(4-methoxybutyl)carbamoyl]phenyl}-1,3-dihydro-2H-isoindole-2-carboxamide | ¹H NMR (400 MHz, DMSO-d$_6$, Temp = 90° C.) δ 7.81-7.67 (m, 2H), 7.67-7.52 (m, 2H), 7.37 (dd, J = 8.3, 5.2 Hz, 1H), 7.17 (dd, J = 9.1 Hz, 1H), 7.14-7.03 (m, 1H), 4.77 (d, J = 12.5 Hz, 4H), 3.42-3.30 (m, 2H), 3.24 (s, 3H), 1.96 (s, 1H), 1.70-1.29 (m, 4H) | (ESI (+)) m/e 386 (M + H)⁺ |
| 1171 | 5-fluoro-N-(4-{[(5-methyl-1,3-oxazol-2-yl)methyl]carbamoyl}phenyl)-1,3-dihydro-2H-isoindole-2-carboxamide | ¹H NMR (400 MHz, DMSO-d$_6$, Temp = 90° C.) δ 7.93-7.72 (m, 2H), 7.69-7.55 (m, 2H), 7.45-7.29 (m, 1H), 7.17 (dt, J = 5.5, 2.7 Hz, 1H), 7.13-7.04 (m, 1H), 6.72 (dd, J = 6.4, 1.6 Hz, 1H), 4.77 (d, J = 12.6 Hz, 4H), 4.51 (s, 2H), 2.26 (s, 3H) | (ESI (+)) m/e 395 (M + H)⁺ |
| 1172 | 5-fluoro-N-{4-{[2-(tetrahydro-2H-pyran-3-yl)ethyl]carbamoyl}phenyl)-1,3-dihydro-2H-isoindole-2-carboxamide | ¹H NMR (400 MHz, DMSO-d$_6$, Temp = 90° C.) δ 7.74 (dd, J = 9.0, 2.2 Hz, 2H), 7.61 (dd, J = 9.0, 2.1 Hz, 2H), 7.37 (dd, J = 8.3, 5.2 Hz, 1H), 7.17 (dd, J = 9.0, 2.0 Hz, 1H), 7.14-6.99 (m, 1H), 4.77 (d, J = 12.5 Hz, 4H), 3.86-3.57 (m, 2H), 3.38-3.28 (m, 2H), 3.17-2.91 (m, 1H), 1.97-1.73 (m, 1H), 1.74-1.52 (m, 2H), 1.52-1.34 (m, 3H), 1.33-1.06 (m, 1H) | (ESI (+)) m/e 412 (M + H)⁺ |
| 1173 | 5-fluoro-N-(4-{[(2S)-1-methoxypropan-2-yl]carbamoyl}phenyl)-1,3-dihydro-2H-isoindole-2-carboxamide | ¹H NMR (400 MHz, DMSO-d$_6$, Temp = 90° C.) δ 7.81-7.72 (m, 2H), 7.69-7.51 (m, 2H), 7.51-7.28 (m, 1H), 7.23-7.14 (m, 1H), 7.14-6.98 (m, 1H), 4.77 (d, J = 12.5 Hz, 4H), 4.31-4.10 (m, 1H), 3.44 (dd, J = 9.8, 6.2 Hz, 1H), 3.35-3.32 (m, 1H), 3.29 (s, 3H), 1.16 (d, J = 6.8 Hz, 3H) | (ESI (+)) m/e 372 (M + H)⁺ |
| 1174 | N-{4-[(3,3-dimethyl-2-oxobutyl)carbamoyl]phenyl}-5-fluoro-1,3-dihydro-2H-isoindole-2-carboxamide | ¹H NMR (400 MHz, DMSO-d$_6$, Temp = 90° C.) δ 7.89-7.70 (m, 2H), 7.70-7.54 (m, 2H), 7.37 (dd, J = 8.4, 5.1 Hz, 1H), 7.17 (dd, J = 9.1, 2.2 Hz, 1H), 7.14-6.96 (m, 1H), 4.78 (d, J = 12.5 Hz, 4H), 4.30 (d, J = 4.1 Hz, 2H), 1.18 (s, 9H) | (ESI (+)) m/e 398 (M + H)⁺ |
| 1175 | 5-fluoro-N-(4-{[(1-methyl-1H-pyrrol-2-yl)methyl]carbamoyl}phenyl)-1,3-dihydro-2H-isoindole-2-carboxamide | ¹H NMR (400 MHz, DMSO-d$_6$, Temp = 90° C.) δ 7.89-7.70 (m, 2H), 7.70-7.54 (m, 2H), 7.37 (dd, J = 8.4, 5.1 Hz, 2H), 7.17 (dd, J = 9.1, 2.2 Hz, 1H), 7.14-6.96 (m, 1H), 4.78 (d, J = 12.5 Hz, 4H), 4.30 (d, J = 4.1 Hz, 2H), 3.5 (s, 3H) | (ESI (+)) m/e 393 (M + H)⁺ |
| 1176 | 5-fluoro-N-(4-{[2-(propan-2-yloxy)ethyl]carbamoyl}phenyl)-1,3-dihydro-2H-isoindole-2-carboxamide | ¹H NMR (400 MHz, DMSO-d$_6$, Temp = 90° C.) δ 7.87-7.68 (m, 2H), 7.68-7.50 (m, 2H), 7.37 (dd, J = 8.4, 5.2 Hz, 1H), 7.24-7.15 (m, 1H), 7.15-7.05 (m, 1H), 4.77 (d, J = 12.5 Hz, 4H), 3.83 (p, J = 6.7 Hz, 1H), 1.88-1.63 (m, 1H), 1.12 (d, J = 6.8 Hz, 3H), 0.90 (dd, J = 6.8, 1.4 Hz, 6H) | (ESI (+)) m/e 386 (M + H)⁺ |

| Ex | Name | ¹H NMR | MS |
|---|---|---|---|
| 1177 | N-(4-{[3-(dimethylamino)propyl]carbamoyl}phenyl)-5-fluoro-1,3-dihydro-2H-isoindole-2-carboxamide | ¹H NMR (400 MHz, DMSO-d₆, Temp = 90° C.) δ 7.82-7.70 (m, 2H), 7.70-7.55 (m, 2H), 7.37 (dd, J = 8.4, 5.1 Hz, 1H), 7.17 (dd, J = 9.0, 2.2 Hz, 1H), 7.15-7.02 (m, 1H), 4.77 (d, J = 12.4 Hz, 4H), 3.39-3.30 (m, 2H), 3.23-3.02 (m, 2H), 2.81 (d, J = 4.3 Hz, 6H), 2.02-1.84 (m, 2H) | (ESI (+)) m/e 385 (M + H)⁺ |
| 1178 | N-(4-{[(2S)-1-amino-1-oxobutan-2-yl]carbamoyl}phenyl)-5-fluoro-1,3-dihydro-2H-isoindole-2-carboxamide | ¹H NMR (400 MHz, DMSO-d₆, Temp = 90° C.) δ 7.90-7.73 (m, 2H), 7.73-7.50 (m, 2H), 7.50-7.30 (m, 1H), 7.29-7.13 (m, 1H), 7.13-7.02 (m, 1H), 4.78 (d, J = 12.5 Hz, 4H), 4.46-4.31 (m, 1H), 1.96 (s, 1H), 1.91-1.78 (m, 1H), 1.78-1.66 (m, 1H), 1.04-0.82 (m, 3H) | (ESI (+)) m/e 385 (M + H)⁺ |
| 1179 | 5-fluoro-N-[4-(tetrahydro-2H-pyran-3-ylcarbamoyl)phenyl]-1,3-dihydro-2H-isoindole-2-carboxamide | ¹H NMR (400 MHz, DMSO-d₆, Temp = 90° C.) δ 7.83-7.69 (m, 2H), 7.68-7.54 (m, 2H), 7.42-7.28 (m, 1H), 7.22-7.14 (m, 1H), 7.14-7.01 (m, 1H), 4.78 (t, J = 10.5 Hz, 4H), 3.96-3.86 (m, 1H), 3.85-3.70 (m, 2H), 3.41-3.32 (m, 1H), 2.00-1.88 (m, 1H), 1.77-1.65 (m, 1H), 1.65-1.50 (m, 2H) | (ESI (+)) m/e 384 (M + H)⁺ |
| 1180 | 5-fluoro-N-(4-{[2-(1H-pyrrol-1-yl)ethyl]carbamoyl}phenyl)-1,3-dihydro-2H-isoindole-2-carboxamide | ¹H NMR (400 MHz, DMSO-d₆, Temp = 90° C.) δ 7.76-7.66 (m, 2H), 7.66-7.53 (m, 2H), 7.46-7.29 (m, 1H), 7.22-7.13 (m, 1H), 7.13-6.99 (m, 1H), 6.72 (t, J = 1.9 Hz, 1H), 5.99 (t, J = 2.0 Hz, 1H), 4.77 (d, J = 12.5 Hz, 4H), 4.07 (t, J = 6.5 Hz, 2H), 3.57 (t, J = 6.5 Hz, 2H) | (ESI (+)) m/e 393 (M + H)⁺ |
| 1181 | 5-fluoro-N-{4-[(1-methoxypropan-2-yl)carbamoyl]phenyl}-1,3-dihydro-2H-isoindole-2-carboxamide | ¹H NMR (400 MHz, DMSO-d₆, Temp = 90° C.) δ 7.78-7.72 (m, 2H), 7.64-7.58 (m, 2H), 7.37 (dd, J = 8.4, 5.1 Hz, 1H), 7.17 (dd, J = 9.1, 2.4 Hz, 1H), 7.14-7.05 (m, 1H), 4.79 (bs, 2H), 4.76 (bs, 2H), 4.18 (h, J = 6.5 Hz, 1H), 3.44 (dd, J = 9.8, 6.2 Hz, 1H), 2.99-2.78 (m, 1H), 1.16 (d, J = 6.7 Hz, 3H) | (ESI (+)) m/e 372 (M + H)⁺ |
| 1182 | 5-fluoro-N-{4-[(2-methoxyethyl)carbamoyl]phenyl}-1,3-dihydro-2H-isoindole-2-carboxamide | ¹H NMR (400 MHz, DMSO-d₆, Temp = 90° C.) δ 7.78-7.72 (m, 1H), 7.64-7.56 (m, 1H), 7.41-7.28 (m, 1H), 7.20-7.05 (m, 1H), 4.78 (bs, 1H), 4.75 (bs, 1H), 3.49 (d, J = 5.2 Hz, 1H), 3.48-3.39 (m, 1H), 2.97 (s, 2H), 2.88-2.76 (m, 1H), 1.96 (s, 1H) | (ESI (+)) m/e 358 (M + H)⁺ |
| 1183 | N-[4-(cyclopentylcarbamoyl)phenyl]-5-fluoro-1,3-dihydro-2H-isoindole-2-carboxamide | ¹H NMR (400 MHz, DMSO-d₆, Temp = 90° C.) δ 7.83-7.68 (m, 2H), 7.68-7.53 (m, 2H), 7.51-7.28 (m, 1H), 7.20-7.13 (m, 1H), 7.12-7.03 (m, 1H), 4.77 (d, J = 12.4 Hz, 4H), 4.33-4.12 (m, 1H), 2.00-1.84 (m, 2H), 1.82-1.66 (m, 2H), 1.66-1.45 (m, 4H) | (ESI (+)) m/e 368 (M + H)⁺ |
| 1184 | 5-fluoro-N-(4-{[(2S)-3-methylbutan-2-yl]carbamoyl}phenyl)-1,3-dihydro-2H-isoindole-2-carboxamide | ¹H NMR (400 MHz, DMSO-d₆, Temp = 90° C.) δ 7.85-7.69 (m, 2H), 7.66-7.53 (m, 2H), 7.46-7.31 (m, 1H), 7.23-7.16 (m, 1H), 7.16-7.05 (m, 1H), 4.77 (d, J = 12.5 Hz, 4H), 3.85-3.79 (m, 1H), 1.89-1.72 (m, 1H), 1.11 (t, J = 5.6 Hz, 3H), 0.90 (dd, J = 6.8, 1.1 Hz, 6H) | (ESI (+)) m/e 370 (M + H)⁺ |
| 1185 | 5-fluoro-N-(4-{[(2R)-3-methylbutan-2-yl]carbamoyl}phenyl)-1,3-dihydro-2H-isoindole-2-carboxamide | ¹H NMR (400 MHz, DMSO-d₆, Temp = 90° C.) δ 7.87-7.68 (m, 2H), 7.68-7.50 (m, 2H), 7.37 (dd, J = 8.4, 5.2 Hz, 1H), 7.24-7.15 (m, 1H), 7.15-7.05 (m, 1H), 4.77 (d, J = 12.5 Hz, 4H), 3.83 (p, J = 6.7 Hz, 1H), 1.88-1.63 (m, 1H), 1.12 (d, J = 6.8 Hz, 3H), 0.90 (dd, J = 6.8, 1.4 Hz, 6H) | (ESI (+)) m/e 370 (M + H)⁺ |
| 1186 | 5-fluoro-N-(4-{[(2S)-2-methylbutyl]carbamoyl}phenyl)-1,3-dihydro-2H-isoindole-2-carboxamide | ¹H NMR (400 MHz, DMSO-d₆, Temp = 90° C.) δ 7.84-7.70 (m, 2H), 7.70-7.56 (m, 2H), 7.46-7.27 (m, 1H), 7.25-7.03 (m, 2H), 4.77 (d, J = 12.5 Hz, 4H), 3.21 (dd, J = 13.1, 6.4 Hz, 1H), 3.15-2.97 (m, 1H), 1.80-1.61 (m, 1H), 1.53-1.30 (m, 1H), 1.28-1.06 (m, 1H), 0.98-0.79 (m, 6H) | (ESI (+)) m/e 370 (M + H)⁺ |
| 1187 | 5-fluoro-N-{4-[(2-hydroxy-2-methylpropyl)carbamoyl]phenyl}-1,3-dihydro-2H-isoindole-2-carboxamide | ¹H NMR (400 MHz, DMSO-d₆, Temp = 90° C.) δ 7.81-7.71 (m, 2H), 7.67-7.57 (m, 2H), 7.45-7.27 (m, 1H), 7.21-7.13 (m, 1H), 7.13-7.00 (m, 1H), 4.83-4.70 (m, 4H), 1.96 (s, 2H), 1.14 (s, 6H) | (ESI (+)) m/e 372 (M + H)⁺ |

| Ex | Name | ¹H NMR | MS |
|---|---|---|---|
| 1188 | 5-fluoro-N-(4-{[2-(tetrahydro-2H-pyran-4-yl)ethyl]carbamoyl}phenyl)-1,3-dihydro-2H-isoindole-2-carboxamide | ¹H NMR (400 MHz, DMSO-d₆, Temp = 90° C.) δ 7.82-7.67 (m, 2H), 7.69-7.51 (m, 2H), 7.43-7.32 (m, 1H), 7.21-7.01 (m, 2H), 4.78 (t, J = 10.2 Hz, 4H), 3.95-3.70 (m, 2H), 3.38-3.30 (m, 2H), 1.96 (s, 1H), 1.65-1.55 (m, 2H), 1.57-1.43 (m, 2H), 1.29-1.09 (m, 2H) | (ESI (+)) m/e 412 (M + H)⁺ |
| 1189 | N-[4-(butylcarbamoyl)phenyl]-5-fluoro-1,3-dihydro-2H-isoindole-2-carboxamide | ¹H NMR (400 MHz, DMSO-d₆, Temp = 90° C.) δ 7.81-7.69 (m, 2H), 7.68-7.53 (m, 2H), 7.47-7.30 (m, 1H), 7.26-7.13 (m, 1H), 7.13-7.01 (m, 1H), 4.87-4.67 (m, 4H), 3.27 (d, J = 7.1 Hz, 2H), 1.61-1.45 (m, 2H), 1.44-1.26 (m, 2H), 0.91 (t, J = 7.3 Hz, 3H) | (ESI (+)) m/e 356 (M + H)⁺ |
| 1190 | 5-fluoro-N-{4-[methyl(tetrahydrofuran-2-ylmethyl)carbamoyl]phenyl}-1,3-dihydro-2H-isoindole-2-carboxamide | ¹H NMR (400 MHz, DMSO-d₆, Temp = 90° C.) δ 7.69-7.52 (m, 2H), 7.42-7.31 (m, 1H), 7.32-7.24 (m, 2H), 7.20-7.14 (m, 1H), 7.14-7.02 (m, 1H), 4.89-4.63 (m, 4H), 4.12-3.96 (m, 1H), 3.82-3.58 (m, 2H), 3.59-3.34 (m, 2H), 2.00-1.86 (m, 2H), 1.86-1.72 (m, 2H), 1.61-1.33 (m, 1H) | (ESI (+)) m/e 398 (M + H)⁺ |
| 1191 | 5-fluoro-N-{4-[(2-methoxyethyl)(methyl)carbamoyl]phenyl}-1,3-dihydro-2H-isoindole-2-carboxamide | ¹H NMR (400 MHz, DMSO-d₆, Temp = 90° C.) δ 7.69-7.53 (m, 2H), 7.43-7.32 (m, 1H), 7.32-7.24 (m, 2H), 7.19-7.13 (m, 1H), 7.13-7.03 (m, 1H), 4.77 (d, J = 12.4 Hz, 4H), 3.52 (s, 3H), 3.03-2.92 (m, 3H) | (ESI (+)) m/e 372 (M + H)⁺ |
| 1192 | N-{4-[(1-cyanoethyl)carbamoyl]phenyl}-5-fluoro-1,3-dihydro-2H-isoindole-2-carboxamide | ¹H NMR (400 MHz, DMSO-d₆, Temp = 90° C.) δ 7.89-7.74 (m, 2H), 7.74-7.57 (m, 2H), 7.37 (dd, J = 8.4, 5.1 Hz, 1H), 7.17 (dd, J = 9.0, 2.2 Hz, 1H), 7.13-7.04 (m, 1H), 4.93 (q, J = 7.2 Hz, 1H), 4.78 (d, J = 12.4 Hz, 4H), 1.57 (d, J = 7.2 Hz, 3H) | (ESI (+)) m/e 353 (M + H)⁺ |
| 1193 | 5-fluoro-N-(4-{[(5-methyl-1,2-oxazol-3-yl)methyl]carbamoyl}phenyl)-1,3-dihydro-2H-isoindole-2-carboxamide | ¹H NMR (400 MHz, DMSO-d₆, Temp = 90° C.) δ 7.85-7.72 (m, 2H), 7.68-7.56 (m, 2H), 7.42-7.28 (m, 1H), 7.21-7.12 (m, 1H), 7.12-7.01 (m, 1H), 6.24-6.00 (m, 1H), 4.90-4.68 (m, 4H), 4.55-4.37 (m, 2H), 2.42-2.27 (m, 3H) | (ESI (+)) m/e 395 (M + H)⁺ |
| 1194 | 5-fluoro-N-{4-[(3R)-tetrahydrofuran-3-ylcarbamoyl]phenyl}-1,3-dihydro-2H-isoindole-2-carboxamide | ¹H NMR (400 MHz, DMSO-d₆, Temp = 90° C.) δ 7.87-7.72 (m, 2H), 7.66-7.55 (m, 2H), 7.45-7.32 (m, 1H), 7.17 (dd, J = 9.0, 2.1 Hz, 1H), 7.14-7.01 (m, 1H), 4.77 (d, J = 12.4 Hz, 4H), 4.50-4.38 (m, 1H), 3.93-3.80 (m, 2H), 3.80-3.66 (m, 1H), 3.59 (dd, J = 8.9, 4.6 Hz, 1H), 2.27-2.09 (m, 1H), 1.99-1.77 (m, 1H) | (ESI (+)) m/e 370 (M + H)⁺ |
| 1260 | N-{4-[(3-methoxy-2,2-dimethylpropyl)carbamoyl]phenyl}-1,3-dihydro-2H-isoindole-2-carboxamide | ¹H NMR (400 MHz, DMSO-d₆, Temp = 90° C.) δ 7.80-7.70 (m, 2H), 7.68-7.52 (m, 2H), 7.44-7.23 (m, 4H), 4.79 (s, 4H), 3.29 (d, J = 7.7 Hz, 3H), 3.22-3.19 (m, 2H), 3.15 (s, 2H), 0.90 (s, 6H) | (ESI (+)) m/e 382 (M + H)⁺ |
| 1261 | N-{4-[(4,4-difluorocyclohexyl)carbamoyl]phenyl}-1,3-dihydro-2H-isoindole-2-carboxamide | ¹H NMR (400 MHz, DMSO-d₆, Temp = 90° C.) δ 7.86-7.69 (m, 2H), 7.69-7.50 (m, 2H), 7.38-7.22 (m, 4H), 4.99-4.62 (m, 4H), 3.96 (s, 1H), 2.20-1.82 (m, 6H), 1.70 (t, J = 11.7 Hz, 2H) | (ESI (+)) m/e 382 (M + H)⁺ |
| 1262 | N-(4-{[(2R)-1-cyanobutan-2-yl]carbamoyl}phenyl)-1,3-dihydro-2H-isoindole-2-carboxamide | ¹H NMR (400 MHz, DMSO-d₆, Temp = 90° C.) δ 7.87-7.70 (m, 2H), 7.73-7.49 (m, 2H), 7.45-7.17 (m, 4H), 4.80 (s, 4H), 4.23-3.99 (m, 1H), 2.97-2.63 (m, 2H), 1.78-1.56 (m, 2H), 0.91 (q, J = 7.2 Hz, 3H) | (ESI (+)) m/e 362 (M + H)⁺ |
| 1263 | N-{4-[(2-methoxybutyl)carbamoyl]phenyl}-1,3-dihydro-2H-isoindole-2-carboxamide | ¹H NMR (400 MHz, DMSO-d₆, Temp = 90° C.) δ 7.77-7.70 (m, 2H), 7.69-7.52 (m, 2H), 7.42-7.22 (m, 4H), 4.79 (s, 4H), 3.41-3.31 (m, 5H), 1.65-1.30 (m, 2H), 0.90 (t, J = 7.4 Hz, 3H) | (ESI (+)) m/e 368 (M + H)⁺ |

| Ex | Name | ¹H NMR | MS |
|---|---|---|---|
| 1264 | N-(4-{[1-(ethylamino)-1-oxopropan-2-yl]carbamoyl}phenyl)-1,3-dihydro-2H-isoindole-2-carboxamide | ¹H NMR (400 MHz, DMSO-$d_6$, Temp = 90° C.) δ 7.88-7.73 (m, 2H), 7.69-7.55 (m, 2H), 7.48-7.16 (m, 4H), 4.80 (s, 4H), 4.58-4.35 (m, 1H), 3.13 (q, J = 7.2 Hz, 2H), 1.35 (d, J = 7.2 Hz, 3H), 1.05 (t, J = 7.2 Hz, 3H) | (ESI (+)) m/e 381 (M + H)⁺ |
| 1265 | N-(4-{[2-methyl-2-(morpholin-4-yl)butyl]carbamoyl}phenyl)-1,3-dihydro-2H-isoindole-2-carboxamide | ¹H NMR (400 MHz, DMSO-$d_6$, Temp = 90° C.) δ 7.95-7.77 (m, 2H), 7.70 (t, J = 10.6 Hz, 2H), 7.48-7.20 (m, 4H), 4.80 (s, 4H), 3.95 (d, J = 20.8 Hz, 4H), 3.75-3.55 (m, 2H), 3.40 (s, 2H), 1.95-1.63 (m, 2H), 1.34 (s, 3H), 1.02 (t, J = 7.4 Hz, 3H) | (ESI (+)) m/e 437 (M + H)⁺ |
| 1266 | N-(4-{[(1R)-1-cyclopropylethyl]carbamoyl}phenyl)-1,3-dihydro-2H-isoindole-2-carboxamide | ¹H NMR (400 MHz, DMSO-$d_6$, Temp = 90° C.) δ 7.86-7.69 (m, 2H), 7.69-7.53 (m, 2H), 7.49-7.13 (m, 4H), 4.79 (s, 4H), 3.63-3.44 (m, 1H), 1.22 (d, J = 6.7 Hz, 3H), 1.09-0.90 (m, 1H), 0.57-0.12 (m, 4H) | (ESI (+)) m/e 350 (M + H)⁺ |
| 1267 | N-(4-{[(1S)-1-cyclopropylethyl]carbamoyl}phenyl)-1,3-dihydro-2H-isoindole-2-carboxamide | ¹H NMR (400 MHz, DMSO-$d_6$, Temp = 90° C.) δ 7.84-7.71 (m, 2H), 7.66-7.55 (m, 2H), 7.40-7.19 (m, 4H), 4.79 (s, 4H), 3.52 (p, J = 6.9 Hz, 1H), 1.22 (d, J = 6.7 Hz, 3H), 1.13-0.90 (m, 1H), 0.54-0.14 (m, 4H) | (ESI (+)) m/e 350 (M + H)⁺ |
| 1269 | N-{4-[(3S)-tetrahydrofuran-3-ylcarbamoyl]phenyl}-1,3-dihydro-2H-isoindole-2-carboxamide | ¹H NMR (400 MHz, DMSO-$d_6$, Temp = 90° C.) δ 7.84-7.73 (m, 2H), 7.67-7.53 (m, 2H), 7.42-7.19 (m, 4H), 4.80 (d, J = 5.5 Hz, 4H), 4.52-4.35 (m, 1H), 3.93-3.78 (m, 2H), 3.78-3.67 (m, 1H), 3.63-3.52 (m, 1H), 2.29-2.08 (m, 1H), 2.07-1.79 (m, 1H) | (ESI (+)) m/e 351 (M + H)⁺ |
| 1270 | N-(4-{[2-(tetrahydro-2H-pyran-3-yl)ethyl]carbamoyl}phenyl)-1,3-dihydro-2H-isoindole-2-carboxamide | ¹H NMR (400 MHz, DMSO-$d_6$, Temp = 90° C.) δ 7.82-7.69 (m, 2H), 7.65-7.48 (m, 2H), 7.50-7.14 (m, 4H), 4.79 (s, 4H), 3.93-3.60 (m, 2H), 3.41-3.29 (m, 2H), 3.14-2.93 (m, 1H), 2.02-1.79 (m, 2H), 1.69-1.43 (m, 4H), 1.29-1.09 (m, 1H) | (ESI (+)) m/e 394 (M + H)⁺ |
| 1271 | N-(4-{[(5-methyl-1,3-oxazol-2-yl)methyl]carbamoyl}phenyl)-1,3-dihydro-2H-isoindole-2-carboxamide | ¹H NMR (400 MHz, DMSO-$d_6$, Temp = 90° C.) δ 7.92-7.71 (m, 2H), 7.72-7.56 (m, 2H), 7.46-7.24 (m, 4H), 4.80 (d, J = 1.4 Hz, 4H), 4.63-4.41 (m, 2H), 2.26 (t, J = 2.3 Hz, 3H) | (ESI (+)) m/e 377 (M + H)⁺ |
| 1272 | N-[4-({2-[(dimethylamino)methyl]benzyl}carbamoyl)phenyl]-1,3-dihydro-2H-isoindole-2-carboxamide | ¹H NMR (400 MHz, DMSO-$d_6$, Temp = 90° C.) δ 7.85-7.75 (m, 2H), 7.72-7.63 (m, 2H), 7.59-7.50 (m, 1H), 7.50-7.42 (m, 2H), 7.42-7.24 (m, 5H), 4.79 (s, 4H), 4.52 (d, J = 16.7 Hz, 4H), 2.88 (s, 6H) | (ESI (+)) m/e 429 (M + H)⁺ |
| 1273 | N-(4-{[(1R)-2-amino-2-oxo-1-phenylethyl]carbamoyl}phenyl)-1,3-dihydro-2H-isoindole-2-carboxamide | ¹H NMR (400 MHz, DMSO-$d_6$, Temp = 90° C.) δ 7.86-7.76 (m, 2H), 7.70-7.62 (m, 2H), 7.51 (t, J = 6.8 Hz, 2H), 7.40-7.25 (m, 7H), 5.63 (s, 1H), 4.79 (s, 4H) | (ESI (+)) m/e 415 (M + H)⁺ |
| 1274 | N-[4-(1,3-oxazol-2-ylcarbamoyl)phenyl]-1,3-dihydro-2H-isoindole-2-carboxamide | ¹H NMR (400 MHz, DMSO-$d_6$, Temp = 90° C.) δ 8.03-7.85 (m, 2H), 7.85-7.76 (m, 1H), 7.76-7.61 (m, 2H), 7.47-7.25 (m, 4H), 7.18-7.03 (m, 1H), 4.92-4.62 (m, 4H) | (ESI (+)) m/e 329 (M + H)⁺ |
| 1275 | N-[4-(tetrahydro-2H-pyran-3-ylcarbamoyl)phenyl]-1,3-dihydro-2H-isoindole-2-carboxamide | ¹H NMR (400 MHz, DMSO-$d_6$, Temp = 90° C.) δ 7.88-7.65 (m, 2H), 7.69-7.53 (m, 2H), 7.46-7.18 (m, 4H), 4.79 (s, 4H), 3.99-3.66 (m, 3H), 3.44-3.32 (m, 1H), 2.04-1.86 (m, 1H), 1.84-1.50 (m, 3H) | (ESI (+)) m/e 366 (M + H)⁺ |
| 1276 | N-(4-{[2-(2,6-dimethylmorpholin-4-yl)ethyl]carbamoyl}phenyl)-1,3-dihydro-2H-isoindole-2-carboxamide | ¹H NMR (400 MHz, DMSO-$d_6$, Temp = 90° C.) δ 7.85-7.70 (m, 2H), 7.70-7.57 (m, 2H), 7.45-7.22 (m, 4H), 4.80 (s, 4H), 3.94-3.77 (m, 2H), 3.67 (t, J = 6.2 Hz, 2H), 3.53 (d, J = 12.0 Hz, 2H), 3.32 (dd, J = 12.8, 6.6 Hz, 3H), 2.72 (t, J = 11.7 Hz, 2H), 1.18 (d, J = 6.3 Hz, 6H) | (ESI (+)) m/e 423 (M + H)⁺ |

| Ex | Name | ¹H NMR | MS |
|---|---|---|---|
| 1277 | N-(4-{[1-(1-methylcyclopropyl)ethyl]carbamoyl}phenyl)-1,3-dihydro-2H-isoindole-2-carboxamide | ¹H NMR (400 MHz, DMSO-d₆, Temp = 90° C.) δ 7.85-7.69 (m, 2H), 7.69-7.53 (m, 2H), 7.47-6.99 (m, 4H), 4.79 (s, 4H), 3.82-3.62 (m, 1H), 1.17 (d, J = 6.9 Hz, 3H), 1.07 (s, 3H), 0.69-0.53 (m, 1H), 0.47-0.35 (m, 1H), 0.29-0.13 (m, 2H) | (ESI (+)) m/e 364 (M + H)⁺ |
| 1278 | N-(4-{[2-(furan-2-yl)-2-(pyrrolidin-1-yl)ethyl]carbamoyl}phenyl)-1,3-dihydro-2H-isoindole-2-carboxamide | ¹H NMR (400 MHz, DMSO-d₆, Temp = 90° C.) δ 7.79-7.65 (m, 3H), 7.68-7.54 (m, 2H), 7.43-7.17 (m, 4H), 6.78 (d, J = 3.3 Hz, 1H), 6.64-6.46 (m, 1H), 4.91-4.72 (m, 5H), 4.11-3.93 (m, 1H), 3.93-3.77 (m, 1H), 2.01-1.76 (m, 4H) | (ESI (+)) m/e 445 (M + H)⁺ |
| 1310 | N-(4-{[3-(3,5-dimethyl-1H-pyrazol-1-yl)propyl]carbamoyl}phenyl)-1,3-dihydro-2H-isoindole-2-carboxamide | ¹H NMR (400 MHz, DMSO-d₆, Temp = 90° C.) δ 7.80-7.69 (m, 2H), 7.69-7.51 (m, 2H), 7.44-7.25 (m, 4H), 4.79 (s, 4H), 4.03-3.87 (m, 2H), 2.23-2.15 (m, 3H), 2.10 (s, 3H), 2.05-1.88 (m, 2H) | (ESI (+)) m/e 418 (M + H)⁺ |
| 1311 | N-(4-{[(3S)-1-methyl-2-oxoazepan-3-yl]carbamoyl}phenyl)-1,3-dihydro-2H-isoindole-2-carboxamide | ¹H NMR (400 MHz, DMSO-d₆, Temp = 90° C.) δ 7.92-7.83 (m, 1H), 7.79-7.70 (m, 2H), 7.70-7.57 (m, 2H), 7.46-7.13 (m, 5H), 6.63-6.61 (m, 1H), 4.90-4.73 (m, 6H), 3.76-3.57 (m, 1H), 2.95 (s, 3H), 2.02-1.68 (m, 4H), 1.64-1.32 (m, 2H) | (ESI (+)) m/e 407 (M + H)⁺ |
| 1312 | N-(4-{[2-(1H-pyrazol-1-yl)ethyl]carbamoyl}phenyl)-1,3-dihydro-2H-isoindole-2-carboxamide | ¹H NMR (400 MHz, DMSO-d₆, Temp = 90° C.) δ 7.74-7.67 (m, 2H), 7.66-7.59 (m, 3H), 7.39-7.28 (m, 4H), 6.23 (t, J = 2.0 Hz, 1H), 4.79 (s, 4H), 4.31 (t, J = 6.4 Hz, 2H), 3.66 (t, J = 6.4 Hz, 2H) | (ESI (+)) m/e 376 (M + H)⁺ |
| 1313 | N-(4-{[1-(1,3-thiazol-2-yl)ethyl]carbamoyl}phenyl)-1,3-dihydro-2H-isoindole-2-carboxamide | ¹H NMR (400 MHz, DMSO-d₆, Temp = 90° C.) δ 7.91-7.75 (m, 2H), 7.74-7.62 (m, 3H), 7.53 (d, J = 3.3 Hz, 1H), 7.47-7.23 (m, 4H), 5.56-5.34 (m, 1H), 4.80 (s, 4H), 1.65 (d, J = 7.0 Hz, 3H) | (ESI (+)) m/e 393 (M + H)⁺ |
| 1314 | N-(4-{[1-(furan-2-yl)propan-2-yl]carbamoyl}phenyl)-1,3-dihydro-2H-isoindole-2-carboxamide | ¹H NMR (400 MHz, DMSO-d₆, Temp = 90° C.) δ 7.77-7.66 (m, 2H), 7.66-7.55 (m, 2H), 7.50-7.39 (m, 1H), 7.41-7.19 (m, 4H), 6.45-6.23 (m, 1H), 6.13 (d, J = 3.1 Hz, 1H), 4.79 (s, 4H), 4.39-4.14 (m, 1H), 3.03-2.87 (m, 1H), 2.87-2.70 (m, 1H), 1.19 (d, J = 6.7 Hz, 3H) | (ESI (+)) m/e 390 (M + H)⁺ |
| 1315 | N-(4-{[1-(1-methyl-1H-pyrazol-4-yl)ethyl]carbamoyl}phenyl)-1,3-dihydro-2H-isoindole-2-carboxamide | ¹H NMR (400 MHz, DMSO-d₆, Temp = 90° C.) δ 7.81-7.68 (m, 2H), 7.70-7.57 (m, 2H), 7.54 (s, 1H), 7.47-7.20 (m, 4H), 5.14 (q, J = 6.9 Hz, 1H), 4.79 (s, 4H), 3.78 (s, 3H), 1.47 (d, J = 6.9 Hz, 3H) | (ESI (+)) m/e 390 (M + H)⁺ |
| 1316 | N-(4-{[(2R)-1-amino-4-methyl-1-oxopentan-2-yl]carbamoyl}phenyl)-1,3-dihydro-2H-isoindole-2-carboxamide | ¹H NMR (400 MHz, DMSO-d₆, Temp = 90° C.) δ 7.93-7.76 (m, 2H), 7.76-7.52 (m, 2H), 7.46-7.19 (m, 4H), 4.80 (s, 4H), 4.62-4.39 (m, 1H), 1.78-1.50 (m, 3H), 0.92 (dd, J = 11.0, 6.1 Hz, 6H) | (ESI (+)) m/e 395 (M + H)⁺ |
| 1317 | N-(4-{[1-(3,5-dimethyl-1H-pyrazol-1-yl)propan-2-yl]carbamoyl}phenyl)-1,3-dihydro-2H-isoindole-2-carboxamide | ¹H NMR (400 MHz, DMSO-d₆, Temp = 90° C.) δ 7.80-7.67 (m, 2H), 7.66-7.56 (m, 2H), 7.48-7.09 (m, 4H), 4.79 (s, 4H), 4.38 (h, J = 6.6 Hz, 1H), 4.22-4.00 (m, 2H), 2.25 (s, 3H), 2.14 (s, 3H), 1.16 (d, J = 6.8 Hz, 3H) | (ESI (+)) m/e 418 (M + H)⁺ |
| 1318 | N-{4-[(2,2-difluoroethyl)carbamoyl]phenyl}-1,3-dihydro-2H-isoindole-2-carboxamide | ¹H NMR (400 MHz, DMSO-d₆, Temp = 90° C.) δ 7.93-7.72 (m, 2H), 7.73-7.57 (m, 2H), 7.44-7.22 (m, 4H), 6.28-5.80 (m, 1H), 4.79 (s, 4H), 3.78-3.55 (m, 2H) | (ESI (+)) m/e 346 (M + H)⁺ |

| Ex | Name | ¹H NMR | MS |
|---|---|---|---|
| 1319 | N-(4-{[2-(tetrahydro-2H-pyran-4-yl)ethyl]carbamoyl}phenyl)-1,3-dihydro-2H-isoindole-2-carboxamide | ¹H NMR (400 MHz, DMSO-d₆, Temp = 90° C.) δ 7.81-7.68 (m, 2H), 7.68-7.53 (m, 2H), 7.44-7.25 (m, 4H), 4.79 (s, 4H), 3.93-3.74 (m, 2H), 3.34-3.30 (m, 2H), 1.73-1.43 (m, 4H), 1.35-1.06 (m, 2H) | (ESI (+)) m/e 394 (M + H)⁺ |
| 1320 | N-{4-[(tetrahydrofuran-2-ylmethyl)carbamoyl]phenyl}-1,3-dihydro-2H-isoindole-2-carboxamide | ¹H NMR (400 MHz, DMSO-d₆, Temp = 90° C.) δ 7.83-7.72 (m, 2H), 7.67-7.47 (m, 2H), 7.43-7.17 (m, 4H), 4.79 (s, 4H), 4.00 (p, J = 6.2 Hz, 1H), 3.88-3.72 (m, 1H), 3.73-3.55 (m, 1H), 3.34 (d, J = 5.9 Hz, 2H), 2.01-1.76 (m, 3H), 1.71-1.49 (m, 1H) | (ESI (+)) m/e 366 (M + H)⁺ |
| 1321 | N-{4-[(2-methoxy-2-methylpropyl)carbamoyl]phenyl}-1,3-dihydro-2H-isoindole-2-carboxamide | ¹H NMR (400 MHz, DMSO-d₆, Temp = 90° C.) δ 7.86-7.71 (m, 2H), 7.71-7.58 (m, 2H), 7.46-7.22 (m, 4H), 4.79 (s, 4H), 3.35 (s, 2H), 3.18 (s, 3H), 1.14 (s, 6H) | (ESI (+)) m/e 368 (M + H)⁺ |
| 1322 | N-(4-{[(5-methyl-1,2-oxazol-3-yl)methyl]carbamoyl}phenyl)-1,3-dihydro-2H-isoindole-2-carboxamide | ¹H NMR (400 MHz, DMSO-d₆, Temp = 90° C.) δ 7.81-7.75 (m, 2H), 7.67-7.61 (m, 2H), 7.39-7.28 (m, 4H), 4.83-4.76 (m, 5H), 4.46 (s, 2H), 2.36 (d, J = 0.9 Hz, 3H) | (ESI (+)) m/e 377 (M + H)⁺ |
| 1323 | N-(4-{[(1-methyl-1H-pyrazol-4-yl)methyl]carbamoyl}phenyl)-1,3-dihydro-2H-isoindole-2-carboxamide | ¹H NMR (400 MHz, DMSO-d₆, Temp = 90° C.) δ 7.75 (d, J = 8.7 Hz, 2H), 7.62 (d, J = 8.7 Hz, 2H), 7.54 (s, 1H), 7.39-7.20 (m, 4H), 4.79 (s, 4H), 4.30 (s, 2H), 3.78 (s, 3H) | (ESI (+)) m/e 376 (M + H)⁺ |
| 1324 | N-(4-{[2-(3,5-dimethyl-1H-pyrazol-1-yl)ethyl]carbamoyl}phenyl)-1,3-dihydro-2H-isoindole-2-carboxamide | ¹H NMR (400 MHz, DMSO-d₆, Temp = 90° C.) δ 7.83-7.64 (m, 2H), 7.68-7.53 (m, 2H), 7.46-7.13 (m, 4H), 4.79 (s, 4H), 4.13 (t, J = 6.5 Hz, 2H), 3.58 (t, J = 6.5 Hz, 2H), 2.19 (s, 3H), 2.12 (s, 3H) | (ESI (+)) m/e 404 (M + H)⁺ |
| 1325 | N-alpha-{4-[(1,3-dihydro-2H-isoindol-2-ylcarbonyl)amino]benzoyl}-L-phenylalaninamide | ¹H NMR (400 MHz, DMSO-d₆, Temp = 90° C.) δ 7.70-7.66 (m, 2H), 7.66-7.56 (m, 2H), 7.39-7.22 (m, 8H), 7.22-7.12 (m, 1H), 4.79 (s, 4H), 4.72-4.62 (m, 1H), 3.20-3.11 (m, 1H), 3.08-2.91 (m, 1H) | (ESI (+)) m/e 429 (M + H)⁺ |
| 1326 | N-(4-{[2-(2-methyl-1,3-thiazol-4-yl)ethyl]carbamoyl}phenyl)-1,3-dihydro-2H-isoindole-2-carboxamide | ¹H NMR (400 MHz, DMSO-d₆, Temp = 90° C.) δ 7.74 (dd, J = 6.8, 1.8 Hz, 2H), 7.70-7.57 (m, 2H), 7.43-7.23 (m, 4H), 7.19-6.98 (m, 1H), 4.80 (s, 4H), 3.66-3.41 (m, 2H), 3.05-2.85 (m, 2H), 2.65 (d, J = 5.2 Hz, 3H) | (ESI (+)) m/e 477 (M + H)⁺ |
| 1327 | N-(4-{[(2S)-3,3-dimethyl-1-(methylamino)-1-oxobutan-2-yl]carbamoyl}phenyl)-1,3-dihydro-2H-isoindole-2-carboxamide | ¹H NMR (400 MHz, DMSO-d₆, Temp = 90° C.) δ 7.87-7.69 (m, 2H), 7.69-7.49 (m, 2H), 7.49-7.24 (m, 4H), 4.80 (s, 4H), 4.45-4.33 (m, 1H), 2.66 (d, J = 20.0 Hz, 3H), 1.02 (d, J = 18.5 Hz, 9H) | (ESI (+)) m/e 409 (M + H)⁺ |
| 1328 | N-[4-(thiophen-3-ylcarbamoyl)phenyl]-1,3-dihydro-2H-isoindole-2-carboxamide | ¹H NMR (400 MHz, DMSO-d₆, Temp = 90° C.) δ 7.97-7.82 (m, 2H), 7.75-7.61 (m, 3H), 7.46-7.24 (m, 5H), 4.81 (s, 4H) | (ESI (+)) m/e 364 (M + H)⁺ |
| 1329 | N-(4-{[2-(5-methyl-1H-pyrazol-1-yl)ethyl]carbamoyl}phenyl)-1,3-dihydro-2H-isoindole-2-carboxamide | ¹H NMR (400 MHz, DMSO-d₆, Temp = 90° C.) δ 7.80-7.67 (m, 2H), 7.67-7.55 (m, 2H), 7.45-7.20 (m, 5H), 6.00 (dd, J = 5.0, 0.7 Hz, 1H), 4.79 (s, 4H), 4.21 (t, J = 6.6 Hz, 2H), 3.61 (t, J = 6.6 Hz, 2H), 2.25 (s, 3H) | (ESI (+)) m/e 390 (M + H)⁺ |
| 1330 | N-(4-{[2-(3-methyl-1H-pyrazol-1-yl)ethyl]carbamoyl}phenyl)-1,3-dihydro-2H-isoindole-2-carboxamide | ¹H NMR (400 MHz, DMSO-d₆, Temp = 90° C.) δ 7.76-7.68 (m, 2H), 7.68-7.52 (m, 2H), 7.56-7.42 (m, 1H), 7.44-7.24 (m, 4H), 5.99 (d, J = 2.1 Hz, 1H), 4.79 (s, 4H), 4.21 (t, J = 6.4 Hz, 2H), 3.63 (t, J = 6.4 Hz, 2H), 2.21 (d, J = 33.1 Hz, 3H) | (ESI (+)) m/e 390 (M + H)⁺ |

| Ex | Name | ¹H NMR | MS |
|---|---|---|---|
| 1331 | N-{4-[(2S)-butan-2-ylcarbamoyl]phenyl}-1,3-dihydro-2H-isoindole-2-carboxamide | ¹H NMR (400 MHz, DMSO-d₆, Temp = 90° C.) δ 7.88-7.68 (m, 2H), 7.66-7.49 (m, 2H), 7.44-7.19 (m, 4H), 4.79 (s, 4H), 4.01-3.80 (m, 1H), 1.70-1.33 (m, 2H), 1.16 (d, J = 6.6 Hz, 3H), 0.88 (t, J = 7.4 Hz, 3H) | (ESI (+)) m/e 338 (M + H)⁺ |
| 1332 | N-{4-[(3,3-dimethyl-2-oxobutyl)carbamoyl]phenyl}-1,3-dihydro-2H-isoindole-2-carboxamide | ¹H NMR (400 MHz, DMSO-d₆, Temp = 90° C.) δ 7.88-7.69 (m, 2H), 7.72-7.54 (m, 2H), 7.47-7.19 (m, 4H), 4.80 (s, 4H), 4.30 (s, 2H), 1.18 (s, 9H) | (ESI (+)) m/e 380 (M + H)⁺ |
| 1333 | N-(4-{[(1-methyl-1H-pyrazol-3-yl)methyl]carbamoyl}phenyl)-1,3-dihydro-2H-isoindole-2-carboxamide | ¹H NMR (400 MHz, DMSO-d₆, Temp = 90° C.) δ 7.83-7.73 (m, 2H), 7.70-7.59 (m, 2H), 7.55-7.46 (m, 1H), 7.41-7.22 (m, 4H), 6.15 (d, J = 2.2 Hz, 1H), 4.79 (s, 4H), 4.42 (s, 2H) | (ESI (+)) m/e 376 (M + H)⁺ |
| 1334 | N-(4-{[2-(acetylamino)phenyl]carbamoyl}phenyl)-1,3-dihydro-2H-isoindole-2-carboxamide | ¹H NMR (400 MHz, DMSO-d₆, Temp = 90° C.) δ 7.90-7.79 (m, 2H), 7.76-7.66 (m, 3H), 7.51-7.42 (m, 1H), 7.41-7.26 (m, 4H), 7.26-7.13 (m, 2H), 4.85-4.77 (m, 4H), 2.14-2.05 (m, 3H) | (ESI (+)) m/e 415 (M + H)⁺ |
| 1335 | N-{4-[(1-methoxybutan-2-yl)carbamoyl]phenyl}-1,3-dihydro-2H-isoindole-2-carboxamide | ¹H NMR (400 MHz, DMSO-d₆, Temp = 90° C.) δ 7.83-7.70 (m, 2H), 7.70-7.55 (m, 2H), 7.45-7.23 (m, 4H), 4.79 (s, 4H), 4.16-3.89 (m, 1H), 3.52-3.33 (m, 2H), 1.75-1.42 (m, 2H), 0.90 (t, J = 7.4 Hz, 3H) | (ESI (+)) m/e 368 (M + H)⁺ |
| 1336 | N-[4-(tetrahydro-2H-pyran-4-ylcarbamoyl)phenyl]-1,3-dihydro-2H-isoindole-2-carboxamide | ¹H NMR (400 MHz, DMSO-d₆, Temp = 90° C.) δ 7.85-7.71 (m, 2H), 7.66-7.53 (m, 2H), 7.48-7.20 (m, 4H), 4.79 (s, 4H), 4.05-3.82 (m, 3H), 3.48-3.31 (m, 2H), 1.93-1.70 (m, 2H), 1.70-1.48 (m, 2H) | (ESI (+)) m/e 366 (M + H)⁺ |
| 1337 | N-[4-(pyrimidin-4-ylcarbamoyl)phenyl]-1,3-dihydro-2H-isoindole-2-carboxamide | ¹H NMR (400 MHz, DMSO-d₆, Temp = 90° C.) δ 8.93-8.85 (m, 1H), 8.72-8.62 (m, 1H), 8.21-8.11 (m, 1H), 8.03-7.91 (m, 2H), 7.77-7.66 (m, 2H), 7.42-7.26 (m, 4H), 4.81 (d, J = 5.2 Hz, 4H) | (ESI (+)) m/e 359 (M + H)⁺ |
| 1338 | N-(4-{[2-(1H-pyrrol-1-yl)ethyl]carbamoyl}phenyl)-1,3-dihydro-2H-isoindole-2-carboxamide | ¹H NMR (400 MHz, DMSO-d₆, Temp = 90° C.) δ 7.78-7.66 (m, 2H), 7.66-7.57 (m, 2H), 7.37-7.26 (m, 4H), 6.87-6.56 (m, 1H), 6.10-5.80 (m, 1H), 4.79 (s, 4H), 4.08 (t, J = 6.5 Hz, 2H), 3.70-3.48 (m, 2H) | (ESI (+)) m/e 375 (M + H)⁺ |
| 1339 | N-(4-{[(2S)-2-methylbutyl]carbamoyl}phenyl)-1,3-dihydro-2H-isoindole-2-carboxamide | ¹H NMR (400 MHz, DMSO-d₆, Temp = 90° C.) δ 7.83-7.70 (m, 2H), 7.70-7.52 (m, 2H), 7.45-7.17 (m, 4H), 4.79 (s, 4H), 3.24-3.16 (m, 1H), 3.16-2.98 (m, 1H), 1.77-1.55 (m, 1H), 1.51-1.31 (m, 1H), 1.31-1.01 (m, 1H), 0.90 (dd, J = 13.5, 6.4 Hz, 6H) | (ESI (+)) m/e 352 (M + H)⁺ |
| 1340 | N-{4-[(1-amino-1-oxohexan-2-yl)carbamoyl]phenyl}-1,3-dihydro-2H-isoindole-2-carboxamide | ¹H NMR (400 MHz, DMSO-d₆, Temp = 90° C.) δ 7.86-7.70 (m, 3H), 7.68-7.47 (m, 3H), 7.47-6.53 (m, 6H), 4.84-4.32 (m, 7H), 3.27 (s, 73H), 2.61-2.29 (m, 11H), 2.04-1.61 (m, 3H), 1.56-0.69 (m, 10H), 0.18--0.03 (m, 2H) | (ESI (+)) m/e 395 (M + H)⁺ |
| 1341 | N-{4-[(2-amino-2-oxo-1-phenylethyl)carbamoyl]phenyl}-1,3-dihydro-2H-isoindole-2-carboxamide | ¹H NMR (400 MHz, DMSO-d₆, Temp = 90° C.) δ 7.86-7.73 (m, 2H), 7.84-7.78 (m, 2H), 7.70-7.57 (m, 2H), 7.68-7.62 (m, 2H), 7.53-7.49 (m, 1H), 7.51 (dd, J = 6.8, 5.5 Hz, 2H), 7.40-7.26 (m, 7H), 7.36-7.22 (m, 5H), 5.63 (s, 1H), 5.63 (s, 1H), 4.79 (s, 4H), 4.79 (s, 4H) | (ESI (+)) m/e 315 (M + H)⁺ |
| 1342 | N-{4-[(3-tert-butoxypropyl)carbamoyl]phenyl}-1,3-dihydro-2H-isoindole-2-carboxamide | ¹H NMR (400 MHz, DMSO-d₆, Temp = 90° C.) δ 7.80-7.68 (m, 2H), 7.68-7.53 (m, 2H), 7.37-7.18 (m, 4H), 4.79 (s, 4H), 3.44-3.29 (m, 4H), 1.81-1.62 (m, 2H), 1.15 (s, 9H) | (ESI (+)) m/e 396 (M + H)⁺ |
| 1343 | N-(4-{[3-(methylcarbamoyl)phenyl]carbamoyl}phenyl)-1,3-dihydro-2H-isoindole-2-carboxamide | ¹H NMR (400 MHz, DMSO-d₆, Temp = 90° C.) δ 7.97-7.85 (m, 3H), 7.76-7.65 (m, 2H), 7.45-7.26 (m, 6H), 4.85-4.77 (m, 4H), 2.86-2.78 (m, 3H) | (ESI (+)) m/e 415 (M + H)⁺ |

| Ex | Name | ¹H NMR | MS |
|---|---|---|---|
| 1344 | N-(4-{[(2R)-3-methylbutan-2-yl]carbamoyl}phenyl)-1,3-dihydro-2H-isoindole-2-carboxamide | ¹H NMR (400 MHz, DMSO-$d_6$, Temp = 90° C.) δ 7.90-7.68 (m, 2H), 7.66-7.56 (m, 2H), 7.40-7.17 (m, 4H), 4.79 (s, 4H), 4.02-3.72 (m, 1H), 1.94-1.65 (m, 1H), 1.12 (d, J = 6.7 Hz, 3H), 0.90 (d, J = 6.8 Hz, 6H) | (ESI (+)) m/e 352 (M + H)⁺ |
| 1345 | N-(4-{[(2S)-3-methylbutan-2-yl]carbamoyl}phenyl)-1,3-dihydro-2H-isoindole-2-carboxamide | ¹H NMR (400 MHz, DMSO-$d_6$, Temp = 90° C.) δ 7.85-7.68 (m, 2H), 7.67-7.51 (m, 2H), 7.48-7.11 (m, 4H), 4.79 (s, 4H), 3.95-3.74 (m, 1H), 1.92-1.64 (m, 1H), 1.12 (d, J = 6.8 Hz, 3H), 1.00-0.79 (m, 6H) | (ESI (+)) m/e 352 (M + H)⁺ |
| 1346 | N-(4-{[2-methyl-1-(morpholin-4-yl)propan-2-yl]carbamoyl}phenyl)-1,3-dihydro-2H-isoindole-2-carboxamide | ¹H NMR (400 MHz, DMSO-$d_6$, Temp = 90° C.) δ 7.83-7.70 (m, 2H), 7.70-7.52 (m, 2H), 7.45-7.17 (m, 4H), 4.79 (s, 4H), 3.24-3.16 (m, 1H), 3.16-2.98 (m, 1H), 1.77-1.55 (m, 1H), 1.51-1.31 (m, 1H), 1.31-1.01 (m, 1H), 0.90 (dd, J = 13.5, 6.4 Hz, 6H) | (ESI (+)) m/e 423 (M + H)⁺ |
| 1348 | N-(4-{[2-methyl-2-(morpholin-4-yl)propyl]carbamoyl}phenyl)-1,3-dihydro-2H-isoindole-2-carboxamide | ¹H NMR (400 MHz, DMSO-$d_6$, Temp = 90° C.) δ 7.91-7.75 (m, 2H), 7.75-7.60 (m, 2H), 7.44-7.23 (m, 4H), 4.80 (s, 4H), 4.01-3.86 (m, 4H), 3.63 (s, 2H), 3.50-3.35 (m, 4H), 1.38 (s, 6H) | (ESI (+)) m/e 423 (M + H)⁺ |
| 1349 | N-{4-[(2-ethoxypropyl)carbamoyl]phenyl}-1,3-dihydro-2H-isoindole-2-carboxamide | ¹H NMR (400 MHz, DMSO-$d_6$, Temp = 90° C.) δ 7.84-7.70 (m, 2H), 7.70-7.55 (m, 2H), 7.43-7.24 (m, 4H), 4.79 (s, 4H), 3.72-3.55 (m, 1H), 3.58-3.44 (m, 2H), 3.38-3.31 (m, 1H), 1.20-1.01 (m, 6H) | (ESI (+)) m/e 368 (M + H)⁺ |

Example 132

$N^2$-[4-(propylcarbamoyl)phenyl]-1,3-dihydro-2H-isoindole-2,5-dicarboxamide

A solution of 5-cyano-N-(4-(propylcarbamoyl)phenyl)isoindoline-2-carboxamide (30 mg, 0.9 mmol) in sulfuric acid (0.1 mL) and trifluoroacetic acid (0.3 mL) was stirred at room temperature for 16 hours. The reaction was treated with ice and the suspension was stirred for 10 minutes and filtered. The solid collected was washed with water and dried under vacuum; the solid was purified by reverse-phase HPLC to provide the title compound. ¹H NMR (300 MHz, DMSO-$d_6$) δ ppm 8.61 (s, 1H), 8.26 (t, J=5.7 Hz, 1H), 7.97-8.00 (bs, 1H), 7.81-7.86 (m, 2H), 7.75-7.79 (m, 2H), 7.63-7.68 (m, 2H), 7.44 (d, J=7.8 Hz, 1H), 7.34-7.39 (bs, 1H), 4.81-4.82 (bs, 4H), 3.16-3.24 (m, 2H), 1.46-1.59 (m, 2H), 0.89 (t, J=7.4 Hz, 3H); MS (ESI(+)) m/e 367 (M+H)⁺.

Example 272 methyl 2-{[4-(propylcarbamoyl)phenyl]carbamoyl}isoindoline-5-carboxylate

Example 272A 4-amino-N-propylbenzamide 5-amino-N-[4-(propylcarbamoyl)phenyl]-1,3-dihydro-2H-isoindole-2-carboxamide A solution of 4-nitro-N-propylbenzamide (800 mg, 0.1 mmol) in 40 ml tetrahydrofuran in the presence of 160 mg of 20% Pd on carbon was treated in a pressure bottle with 30 psi of hydrogen for 30 minutes at room temperature. The suspension was filtered through a nylon membrane and concentrated to provide the title compound.

Example 272B methyl 2-{[4-(propylcarbamoyl)phenyl]carbamoyl}isoindoline-5-carboxylate A solution of 4-amino-N-propylbenzamide (390 mg, 2.19 mmol), bis(2,5-dioxopyrrolidin-1-yl) carbonate (700 mg, 2.74 mmol), and pyridine (0.18 mL, 2.19 mmol) in acetonitrile (5 mL) was stirred at ambient temperature for 30 minutes. Diisopropylethylamine (0.85 mL, 6.6 mmol)) was added followed by a suspension of methyl isoindoline-5-carboxylate hydrochloride (538 mg, 2.52 mmol) and diisopropylethylamine (0.46 mL, 4.4 mmol) in 1-methyl-2-pyrrolidinone (8 mL) added dropwise via syringe over ~5 minutes. The reaction became a suspension and was stirred 3 hours. The reaction was treated with water (30 mL) and the resulting suspension was stirred 5 minutes and filtered. The solid collected was washed with water and dried under vacuum to provide the title compound. ¹H NMR (300 MHz, DMSO-$d_6$) δ ppm 8.63 (s, 1H), 8.26 (t, J=5.6 Hz, 1H), 7.94-7.97 (m, 1H), 7.90-7.96 (m, 1H), 7.75-7.78 (m, 2H), 7.63-7.67 (m, 2H), 7.52 (d, J=7.9 Hz, 1H), 4.83-4.86 (m, 4H), 3.87 (s, 3H), 3.16-3.22 (m, 2H), 1.46-1.59 (m, 2H), 0.89 (t, J=7.4 Hz, 3H); MS (ESI(+)) m/e 382 (M+H)⁺.

Example 273

2-{[4-(propylcarbamoyl)phenyl]carbamoyl}isoindoline-5-carboxylic acid

The title compound was prepared as described in Example 1B, substituting methyl 2-{[4-(propylcarbamoyl)phenyl]

carbamoyl}isoindoline-5-carboxylate for methyl 4-(isoindoline-2-carboxamido)benzoate. $^1$H NMR (300 MHz, DMSO-d$_6$) δ ppm 12.90-13.07 (bs, 1H), 8.62 (s, 1H), 8.26 (t, J=5.7 Hz, 1H), 7.88-7.93 (m, 2H), 7.75-7.78 (m, 2H), 7.63-7.67 (m, 2H), 7.49 (d, J=7.9 Hz, 1H), 4.83-4.85 (bs, 4H), 3.16-3.24 (m, 2H), 1.46-1.59 (m, 2H), 0.89 (t, J=7.4 Hz, 3H); (ESI(+)) m/e 368 (M+H)$^+$.

Example 274

5-amino-N-[4-(propylcarbamoyl)phenyl]-1,3-dihydro-2H-isoindole-2-carboxamide

A solution of 5-nitro-N-[4-(propylcarbamoyl)phenyl]-1,3-dihydro-2H-isoindole-2-carboxamide (37 mg, 0.1 mmol) in 1 ml dimethylformamide in the presence of 11 mg of 10% Pd on carbon was treated with a hydrogen balloon overnight at room temperature. The suspension was filtered through diatomaceous earth and purified by reverse-phase HPLC to provide the title compound. $^1$H NMR (300 MHz, DMSO-d$_6$) δ ppm 8.51 (s, 1H), 8.24 (t, J=5.6 Hz, 1H), 7.74-7.78 (m, 2H), 7.62-7.66 (m, 2H), 7.19 (d, J=7.9 Hz, 1H), 6.78-6.89 (m, 2H), 4.67-4.71 (m, 4H), 3.15-3.26 (m, 2H), 1.46-1.59 (m, 2H), 0.89 (t, J=7.4 Hz, 3H); MS (ESI(+)) m/e 339 (M+H)$^+$.

Example 275

5-(hydroxymethyl)-N-[4-(propylcarbamoyl)phenyl]-1,3-dihydro-2H-isoindole-2-carboxamide A solution of calcium chloride (0.031 g, 0.277 mmol) in ethanol (0.8 mL) was added to a suspension of methyl 2-(4-(propylcarbamoyl)phenylcarbamoyl)isoindoline-5-carboxylate (0.04 g, 0.105 mmol) in tetrahydrofuran (1 mL). Sodium borohydride (0.02 g, 0.524 mmol) was then added in one portion and the suspension stirred at room temperature. After 18 hours, the mixture was concentrated to remove tetrahydrofuran then saturated aqueous sodium bicarbonate and water was added. The suspension was filtered and the solid was flash chromatographed to provide the title compound. $^1$H NMR (300 MHz, DMSO-d$_6$) δ ppm 8.55 (s, 1H), 8.25 (t, J=5.6 Hz, 1H), 7.74-7.78 (m, 2H), 7.64-7.67 (m, 2H), 7.31 (d, J=4.0 Hz, 1H), 7.30 (d, J=2.3 Hz, 1H), 7.26 (d, J=8.0 Hz, 1H), 5.19 (t, J=5.6 Hz, 1H), 4.71-4.78 (m, 4H), 4.52 (d, J=5.4 Hz, 2H), 3.15-3.25 (m, 2H), 1.46-1.59 (m, 2H), 0.89 (t, J=7.4 Hz, 3H); MS (ESI(+)) m/e 354 (M+H)$^+$.

Example 276

5-(aminomethyl)-N-[4-(propylcarbamoyl)phenyl]-1,3-dihydro-2H-isoindole-2-carboxamide 5-Cyano-N-(4-(propylcarbamoyl)phenyl)isoindoline-2-carboxamide (0.04 g, 0.115 mmol) and 7M ammonia-methanol/tetrahydrofuran/methanol (4 mL) were added to Ra—Ni 2800, water slurry (0.080 g, 1.363 mmol) in a 50 ml pressure bottle and stirred for 16 hours at 30 psi and room temperature. The mixture was filtered through a nylon membrane, concentrated and purified by reverse-phase HPLC to provide the title compound. $^1$H NMR (300 MHz, Methanol-d$_4$) δ ppm 7.76-7.79 (m, 2H), 7.60-7.63 (m, 2H), 7.31-7.35 (m, 3H), 4.82 (s, 4H), 3.86 (s, 2H), 3.30-3.33 (m, 2H), 1.53-1.75 (m, 2H), 0.98 (t, J=7.4 Hz, 3H); MS (ESI(+)) m/e 425 (M+H)$^+$.

Example 277

5-[(2-hydroxy-2-methylpropanoyl)amino]-N-[4-(propylcarbamoyl)phenyl]-1,3-dihydro-2H-isoindole-2-carboxamide The title compound was prepared as described in Example 1C, substituting 5-amino-N-(4-(propylcarbamoyl)phenyl)isoindoline-2-carboxamide for 3-phenylpropan-1-amine and 2-hydroxy-2-methylpropanoic acid for 4-(isoindoline-2-carboxamido)benzoic acid. $^1$H NMR (300 MHz, DMSO-d$_6$) δ ppm 9.59 (s, 1H), 8.55 (s, 1H), 8.25 (t, J=5.7 Hz, 1H), 7.81 (s, 1H), 7.74-7.78 (m, 2H), 7.62-7.68 (m, 2H), 7.59-7.64 (m, 1H), 7.28 (d, J=8.3 Hz, 1H), 5.71-5.75 (m, 1H), 4.72-4.80 (m, 4H), 3.16-3.23 (m, 2H), 1.42-1.59 (m, 2H), 1.36 (s, 6H), 0.89 (t, J=7.4 Hz, 3H); MS (ESI(+)) m/e 425 (M+H)$^+$.

Example 278

5-acetamido-N-[4-(propylcarbamoyl)phenyl]-1,3-dihydro-2H-isoindole-2-carboxamide A solution of 5-amino-N-(4-(propylcarbamoyl)phenyl)isoindoline-2-carboxamide (0.035 g, 0.103 mmol) in dimethylformamide (0.7 mL) was treated with N,N-diisopropylethylamine (0.018 mL, 0.103 mmol) followed by acetyl chloride (0.011 g, 0.134 mmol) and the reaction solution was stirred at room temperature for 16 hours. The reaction was concentrated and purified by reverse-phase HPLC to provide the title compound. $^1$H NMR (300 MHz, DMSO-d$_6$) δ ppm 9.97 (s, 1H), 8.52 (s, 1H), 8.25 (t, J=5.7 Hz, 1H), 7.74-7.78 (m, 2H), 7.65-7.67 (m, 1H), 7.62-7.67 (m, 2H), 7.43 (dd, J=8.2, 1.9 Hz, 1H), 7.27 (d, J=8.2 Hz, 1H), 4.71-4.76 (m, 4H), 3.16-3.21 (m, 2H), 2.04 (s, 3H), 1.46-1.59 (m, 2H), 0.89 (t, J=7.4 Hz, 3H); MS (ESI(+)) m/e 381 (M+H)$^+$.

Example 279

5-[(N,N-dimethylglycyl)amino]-N-[4-(propylcarbamoyl)phenyl]-1,3-dihydro-2H-isoindole-2-carboxamide The title compound was prepared as described in Example 1C, substituting 5-amino-N-(4-(propylcarbamoyl)phenyl)isoindoline-2-carboxamide for 3-phenylpropan-1-amine and 2-(dimethylamino)acetic acid for 4-(isoindoline-2-carboxamido)benzoic acid. $^1$H NMR (300 MHz, DMSO-d$_6$) δ ppm 9.76 (s, 1H), 8.54 (s, 1H), 8.25 (t, J=5.6 Hz, 1H), 7.74-7.78 (m, 2H), 7.73 (d, J=1.8 Hz, 1H), 7.63-7.67 (m, 2H), 7.54 (dd, J=8.2, 1.9 Hz, 1H), 7.28 (d, J=8.2 Hz, 1H), 4.72-4.76 (m, 4H), 3.16-3.24 (m, 2H), 3.07 (s, 2H), 2.28 (s, 6H), 1.46-1.59 (m, 2H), 0.89 (t, J=7.4 Hz, 3H); MS (ESI(−)) m/e 422 (M−H)$^−$.

Example 280

N-[4-(propylcarbamoyl)phenyl]-5-(1H-pyrazol-3-yl)-1,3-dihydro-2H-isoindole-2-carboxamide In a 4 mL vial, a solution of 5-bromo-N-(4-(propylcarbamoyl)phenyl)isoindoline-2-carboxamide (50 mg, 0.12 mmol) and 1H-pyrazol-3-ylboronic acid (17 mg, 0.15 mmol) in dimethylformamide was treated with saturated aqueous sodium bicarbonate followed by bis(triphenylphosphine)palladium (II) chloride (7 mg). The vial was capped under nitrogen and the reaction heated at 85° C. for 6 hours. The reaction was cooled to ambient temperature and water was added. The resulting suspension was stirred for 5 minutes and filtered.

The solid collected was washed with water and dried under vacuum; the solid was purified by reverse-phase HPLC to provide the title compound. $^1$H NMR (300 MHz, DMSO-$d_6$) δ ppm 12.39-13.18 (bs, 1H), 8.59 (s, 1H), 8.24-8.28 (m, 1H), 7.75-7.79 (m, 2H), 7.70-7.80 (m, 3H), 7.62-7.69 (m, 2H), 7.40 (d, J=7.9 Hz, 1H), 6.73 (d, J=2.2 Hz, 1H), 4.79-4.83 (m, 4H), 3.15-3.25 (m, 2H), 1.46-1.57 (m, 2H), 0.89 (t, J=7.4 Hz, 3H); MS (ESI(+)) m/e 390 (M+H)$^+$.

Example 281

N-[4-(propylcarbamoyl)phenyl]-5-(1H-pyrazol-4-yl)-1,3-dihydro-2H-isoindole-2-carboxamide The title compound was prepared as described in Example 280, substituting 4-(4,4,5,5-tetramethyl-1,3,2-dioxaborolan-2-yl)-1H-pyrazole for 1H-pyrazol-3-ylboronic acid. $^1$H NMR (300 MHz, DMSO-$d_6$) δ ppm 10.91-13.69 (bs, 1H), 8.58 (s, 1H), 8.26 (t, J=5.7 Hz, 1H), 8.07-8.08 (bs, 2H), 7.75-7.79 (m, 2H), 7.67 (s, 1H), 7.54-7.65 (m, 2H), 7.57 (d, J=7.8 Hz, 1H), 7.34 (d, J=7.8 Hz, 1H), 4.76-4.79 (m, 4H), 3.15-3.25 (m, 2H), 1.46-1.59 (m, 2H), 0.89 (t, J=7.4 Hz, 3H); MS (ESI(+)) m/e 390 (M+H)$^+$.

Example 282

5-[(methoxyacetyl)amino]-N-[4-(propylcarbamoyl)phenyl]-1,3-dihydro-2H-isoindole-2-carboxamide The title compound was prepared as described in Example 278, substituting 2-methoxyacetyl chloride for acetyl chloride. $^1$H NMR (300 MHz, DMSO-$d_6$) δ ppm 9.80 (s, 1H), 8.54 (s, 1H), 8.25 (t, J=5.7 Hz, 1H), 7.74-7.79 (m, 2H), 7.72-7.74 (m, 1H), 7.63-7.67 (m, 2H), 7.55 (dd, J=8.2, 1.9 Hz, 1H), 7.30 (d, J=8.2 Hz, 1H), 4.72-4.77 (m, 4H), 4.00 (s, 2H), 3.38 (s, 3H), 3.17-3.19 (m, 2H), 1.46-1.59 (m, 2H), 0.89 (t, J=7.4 Hz, 3H); MS (ESI(+)) m/e 411 (M+H)$^+$.

Example 283

5-[(methylsulfonyl)amino]-N-[4-(propylcarbamoyl)phenyl]-1,3-dihydro-2H-isoindole-2-carboxamide A solution of 5-amino-N-(4-(propylcarbamoyl)phenyl)isoindoline-2-carboxamide (0.035 g, 0.103 mmol), pyridine (0.017 mL, 0.207 mmol) and catalytic N,N-dimethylaminopyridine in dimethylformamide (0.7 mL) was cooled to 0° C. Methanesulfonyl chloride (0.014 g, 0.126 mmol) was added and the reaction solution was allowed to stir at room temperature for 2 hours. The reaction mixture was concentrated and purified by reverse-phase HPLC to provide the title compound. $^1$H NMR (300 MHz, DMSO-$d_6$) δ ppm 9.74 (s, 1H), 8.54 (s, 1H), 8.26 (t, J=5.6 Hz, 1H), 7.74-7.78 (m, 2H), 7.63-7.66 (m, 2H), 7.32 (d, J=8.1 Hz, 1H), 7.14-7.20 (m, 2H), 4.73-4.76 (m, 4H), 3.15-3.25 (m, 2H), 2.98 (s, 3H), 1.45-1.62 (m, 2H), 0.89 (t, J=7.4 Hz, 3H); MS (ESI(+)) m/e 417 (M+H)$^+$.

Table 4.

The following Examples were prepared essentially as described in Example 1, substituting 1,3-dihydro-2H-pyrrolo[3,4-c]pyridine, 5,7-dihydro-6H-pyrrolo[3,4-b]pyridine, or 6,7-dihydro-5H-pyrrolo[3,4-d]pyrimidine for isoindoline in Example 1A and using an appropriate amine as described in Example 1C. Some products were purified by flash chromatography while others were purified by reverse-phase HPLC; some compounds also required Boc-deprotection after amide coupling as described in Example 2D. Accordingly, some Examples were isolated as trifluoroacetic acid salts.

| Ex | Name | $^1$H NMR | MS |
|---|---|---|---|
| 285 | N-{4-[(3,5-dimethoxybenzyl)carbamoyl]phenyl}-1,3-dihydro-2H-pyrrolo[3,4-c]pyridine-2-carboxamide | $^1$H NMR (300 MHz, DMSO-$d_6$) δ ppm 8.80 (t, J = 6.0 Hz, 1H), 8.66 (s, 1H), 8.61 (s, 1H), 8.50 (d, J = 5.0 Hz, 1H), 7.80-7.84 (m, 2H), 7.65-7.69 (m, 2H), 7.44 (d, J = 5.1 Hz, 1H), 6.48 (d, J = 2.3 Hz, 2H), 6.37 (t, J = 2.3 Hz, 1H), 4.81-4.85 (m, 4H), 4.39 (d, J = 5.9 Hz, 2H), 3.31 (s, 6H) | (ESI (+)) m/e 433 (M + H)$^+$ |
| 286 | N-{4-[(4-chlorobenzyl)carbamoyl]phenyl}-1,3-dihydro-2H-pyrrolo[3,4-c]pyridine-2-carboxamide | $^1$H NMR (300 MHz, DMSO-$d_6$) δ ppm 8.88 (t, J = 6.0 Hz, 1H), 8.66 (s, 1H), 8.61 (s, 1H), 8.50 (d, J = 5.0 Hz, 1H), 7.80-7.84 (m, 2H), 7.65-7.69 (m, 2H), 7.32-7.45 (m, 5H), 4.78-4.88 (m, 4H), 4.44 (d, J = 5.9 Hz, 2H) | (ESI (+)) m/e 407 (M + H)$^+$ |
| 287 | N-(4-{[4-(pyridin-2-yl)piperazin-1-yl]carbonyl}phenyl)-1,3-dihydro-2H-pyrrolo[3,4-c]pyridine-2-carboxamide | $^1$H NMR (300 MHz, DMSO-$d_6$) δ ppm 8.61-8.64 (m, 2H), 8.51 (d, J = 5.0 Hz, 1H), 8.13 (ddd, J = 4.9, 2.0, 0.8 Hz, 1H), 7.64-7.68 (m, 2H), 7.56 (ddd, J = 8.7, 7.0, 1.9 Hz, 1H), 7.44 (d, J = 5.1 Hz, 1H), 7.36-7.40 (m, 2H), 6.85 (d, J = 8.6 Hz, 1H), 6.65-6.69 (m, 1H), 4.81-4.85 (m, 4H), 3.53-3.63 (m, 8H) | (ESI (+)) m/e 429 (M + H)$^+$ |
| 288 | N-{4-[(3-phenylpropyl)carbamoyl]phenyl}-1,3-dihydro-2H-pyrrolo[3,4-c]pyridine-2-carboxamide | $^1$H NMR (300 MHz, DMSO-$d_6$) δ ppm 8.61-8.64 (m, 2H), 8.50 (d, J = 5.0 Hz, 1H), 8.27-8.31 (m, 1H), 7.75-7.79 (m, 2H), 7.63-7.67 (m, 2H), 7.44 (d, J = 5.1 Hz, 1H), 7.15-7.31 (m, 5H), 4.76-4.89 (m, 4H), 3.20-3.32 (m, 2H), 2.63 (t, J = 7.6 Hz, 2H), 1.77-1.88 (m, 2H) | (ESI (+)) m/e 401 (M + H)$^+$ |
| 289 | N-{4-[(tetrahydrofuran-3-ylmethyl)carbamoyl]phenyl}-1,3-dihydro-2H-pyrrolo[3,4-c]pyridine-2-carboxamide | $^1$H NMR (300 MHz, DMSO-$d_6$) δ ppm 8.65 (s, 1H), 8.61 (s, 1H), 8.50 (d, J = 5.0 Hz, 1H), 8.39 (t, J = 5.7 Hz, 1H), 7.75-7.79 (m, 2H), 7.63-7.68 (m, 2H), 7.44 (d, J = 5.1 Hz, 1H), 4.81-4.84 (m, 4H), 3.57-3.78 (m, 3H), 3.48 (dd, J = 8.5, 5.3 Hz, 1H), 3.14-3.30 (m, 2H), 2.41-2.51 (m, 1H), 1.87-2.12 (m, 1H), 1.54-1.66 (m, 1H) | (ESI (+)) m/e 367 (M + H)$^+$ |

| Ex | Name | $^1$H NMR | MS |
|---|---|---|---|
| 290 | N-{4-[(3-methylbutyl)carbamoyl]phenyl}-1,3-dihydro-2H-pyrrolo[3,4-c]pyridine-2-carboxamide | $^1$H NMR (300 MHz, DMSO-d$_6$) δ ppm 8.61-8.64 (m, 2H), 8.50 (d, J = 5.0 Hz, 1H), 8.21 (t, J = 5.6 Hz, 1H), 7.74-7.78 (m, 2H), 7.62-7.66 (m, 2H), 7.44 (d, J = 5.1 Hz, 1H), 4.81-4.84 (m, 4H), 3.20-3.33 (m, 2H), 1.53-1.69 (m, 1H), 1.37-1.45 (m, 2H), 0.91 (d, J = 6.6 Hz, 6H) | (ESI (+)) m/e 353 (M + H)$^+$ |
| 426 | N-(4-{[(2S)-tetrahydrofuran-2-ylmethyl]carbamoyl}phenyl)-1,3-dihydro-2H-pyrrolo[3,4-c]pyridine-2-carboxamide | $^1$H NMR (300 MHz, DMSO-d$_6$) δ ppm 8.65 (s, 1H), 8.61 (s, 1H), 8.50 (d, J = 5.0 Hz, 1H), 8.33 (t, J = 5.8 Hz, 1H), 7.76-7.81 (m, 2H), 7.63-7.67 (m, 2H), 7.44 (d, J = 5.1 Hz, 1H), 4.76-4.89 (m, 4H), 3.96 (p, J = 6.3 Hz, 1H), 3.73-3.82 (m, 1H), 3.58-3.67 (m, 1H), 3.26-3.35 (m, 2H), 1.73-1.98 (m, 3H), 1.52-1.66 (m, 1H) | (ESI (−)) m/e 367 (M + H)$^-$ |
| 427 | N-(4-{[(2R)-tetrahydrofuran-2-ylmethyl]carbamoyl}phenyl)-1,3-dihydro-2H-pyrrolo[3,4-c]pyridine-2-carboxamide | $^1$H NMR (300 MHz, DMSO-d$_6$) δ ppm 8.63-8.65 (bs, 1H), 8.61-8.62 (bs, 1H), 8.50 (d, J = 5.0 Hz, 1H), 8.32 (t, J = 5.8 Hz, 1H), 7.76-7.81 (m, 2H), 7.63-7.67 (m, 2H), 7.44 (d, J = 5.1 Hz, 1H), 4.81-4.88 (m, 4H), 3.97 (p, J = 6.2 Hz, 1H), 3.74-3.82 (m, 1H), 3.58-3.66 (m, 1H), 3.26-3.32 (m, 2H), 1.74-1.96 (m, 3H), 1.53-1.64 (m, 1H) | (ESI (−)) m/e 411 (M − H)$^+$ |
| 430 | N-(4-{[(3-methylbutyl)amino]carbonyl}phenyl)-5,7-dihydro-6H-pyrrolo[3,4-d]pyrimidine-6-carboxamide | $^1$H NMR (300 MHz, DMSO-d$_6$) δ ppm 9.10-9.12 (bs, 1H), 8.83 (s, 1H), 8.67 (s, 1H), 8.22 (t, J = 5.6 Hz, 1H), 7.75-7.79 (m, 2H), 7.63-7.67 (m, 2H), 4.81-4.84 (m, 4H), 3.20-3.34 (m, 2H), 1.53-1.69 (m, 1H), 1.37-1.45 (m, 2H), 0.91 (d, J = 6.6 Hz, 6H) | (APCI (+)) m/e 354 (M + H)$^+$ |
| 431 | N-(4-{[(3-phenylpropyl)amino]carbonyl}phenyl)-5,7-dihydro-6H-pyrrolo[3,4-d]pyrimidine-6-carboxamide | $^1$H NMR (300 MHz, DMSO-d$_6$) δ ppm 9.11 (s, 1H), 8.83 (s, 1H), 8.68 (s, 1H), 8.30 (t, J = 5.6 Hz, 1H), 7.76-7.80 (m, 2H), 7.64-7.68 (m, 2H), 7.15-7.32 (m, 5H), 4.77-4.89 (m, 4H), 3.21-3.34 (m, 2H), 2.60-2.74 (m, 2H), 2.29-1.90 (m, 2H) | (APCI (+)) m/e 402 (M + H)$^+$ |
| 437 | N-[4-({[(1S)-2-hydroxy-1-phenylethyl]amino}carbonyl)phenyl]-1,3-dihydro-2H-pyrrolo[3,4-c]pyridine-2-carboxamide | $^1$H NMR (300 MHz, DMSO-d$_6$) δ ppm 8.66 (s, 1H), 8.61 (s, 1H), 8.51 (d, J = 2.0 Hz, 1H), 8.49 (d, J = 5.2 Hz, 1H), 7.82-7.87 (m, 2H), 7.66-7.70 (m, 2H), 7.38-7.45 (m, 3H), 7.29-7.34 (m, 2H), 7.19-7.26 (m, 1H), 5.03-5.10 (m, 1H), 4.90 (t, J = 5.8 Hz, 1H), 4.79-4.87 (m, 4H), 3.61-3.76 (m, 2H) | (ESI (+)) m/e 403 (M + H)$^+$ |
| 445 | N-[4-({[(1S)-2-hydroxy-1-pyridin-2-ylethyl]amino}carbonyl)phenyl]-1,3-dihydro-2H-pyrrolo[3,4-c]pyridine-2-carboxamide | $^1$H NMR (300 MHz, DMSO-d$_6$) δ ppm 8.68 (s, 1H), 8.62 (s, 1H), 8.44-8.54 (m, 3H), 7.84-7.89 (m, 2H), 7.75 (td, J = 7.7, 1.8 Hz, 1H), 7.66-7.72 (m, 2H), 7.39-7.45 (m, 2H), 7.26 (ddd, J = 7.5, 4.8, 1.2 Hz, 1H), 5.10-5.17 (m, 1H), 4.90 (t, J = 6.0 Hz, 1H), 4.79-4.87 (m, 4H), 3.73-3.88 (m, 2H) | (ESI (+)) m/e 404 (M + H)$^+$ |
| 446 | N-(4-{[(3-methylbutyl)amino]carbonyl}phenyl)-5,7-dihydro-6H-pyrrolo[3,4-b]pyridine-6-carboxamide | $^1$H NMR (300 MHz, DMSO-d$_6$) δ ppm 8.62 (s, 1H), 8.48 (dd, J = 4.9, 1.5 Hz, 1H), 8.22 (t, J = 5.6 Hz, 1H), 7.81 (dd, J = 7.7, 1.5 Hz, 1H), 7.73-7.79 (m, 2H), 7.64-7.68 (m, 2H), 7.33 (dd, J = 7.7, 4.9 Hz, 1H), 4.78-4.80 (bs, 4H), 3.21-3.33 (m, 2H), 1.61 (dp, J = 13.3, 6.6 Hz, 1H), 1.41 (q, J = 7.1 Hz, 2H), 0.90 (d, J = 6.6 Hz, 6H) | (ESI (+)) m/e 353 (M + H)$^+$ |
| 447 | N-(4-{[(tetrahydrofuran-3-ylmethyl)amino]carbonyl}phenyl)-5,7-dihydro-6H-pyrrolo[3,4-b]pyridine-6-carboxamide | $^1$H NMR (300 MHz, DMSO-d$_6$) δ ppm 8.63 (s, 1H), 8.48 (dd, J = 4.9, 1.5 Hz, 1H), 8.39 (t, J = 5.7 Hz, 1H), 7.76-7.83 (m, 3H), 7.65-7.69 (m, 2H), 7.33 (dd, J = 7.7, 4.9 Hz, 1H), 4.78-4.81 (bs, 4H), 3.57-3.82 (m, 3H), 3.44-3.51 (m, 1H), 3.17-3.28 (m, 2H), 2.42-2.50 (m, 1H), 1.85-2.02 (m, 1H), 1.54-1.68 (m, 1H) | (ESI (+)) m/e 367 (M + H)$^+$ |
| 448 | N-{4-[(4-pyridin-2-ylpiperazin-1-yl)carbonyl]phenyl}-5,7-dihydro-6H-pyrrolo[3,4-b]pyridine-6-carboxamide | $^1$H NMR (300 MHz, DMSO-d$_6$) δ ppm 8.61 (s, 1H), 8.49 (dd, J = 4.9, 1.5 Hz, 1H), 8.13 (dd, J = 5.0, 1.9 Hz, 1H), 7.81 (dd, J = 7.7, 1.5 Hz, 1H), 7.66-7.70 (m, 2H), 7.56 (ddd, J = 8.7, 7.0, 1.8 Hz, 1H), 7.36-7.41 (m, 2H), 7.34 (dd, J = 7.7, 5.0 Hz, 1H), 6.85 (d, J = 8.6 Hz, 1H), 6.67 (dd, J = 6.9, 4.8 Hz, 1H), 4.79-4.81 (bs, 4H), 3.43-3.75 (m, 8H) | (ESI (+)) m/e 429 (M + H)$^+$ |
| 553 | N-{4-[(tetrahydro-2H-pyran-2-ylmethyl)carbamoyl]phenyl}-1,3-dihydro-2H-pyrrolo[3,4-c]pyridine-2-carboxamide | $^1$H NMR (300 MHz, DMSO-d$_6$) δ 8.64 (s, 1H), 8.61 (s, 1H), 8.50 (d, J = 5.0 Hz, 1H), 8.29 (t, J = 5.8 Hz, 1H), 7.82-7.75 (m, 2H), 7.68-7.61 (m, 2H), 7.44 (d, J = 5.1 Hz, 1H), 4.86-4.79 (m, 4H), 3.87 (dd, J = 11.3, 3.0 Hz, 1H), 3.48-3.34 (m, 2H), 3.28-3.17 (m, 2H), 1.82-1.72 (m, 1H), 1.66-1.56 (m, 1H), 1.56-1.33 (m, 3H), 1.28-1.07 (m, 1H) | (ESI (+)) m/e 381 (M + H)$^+$ |

-continued

| Ex | Name | ¹H NMR | MS |
|---|---|---|---|
| 554 | N-{4-[(tetrahydro-2H-pyran-3-ylmethyl)carbamoyl]phenyl}-1,3-dihydro-2H-pyrrolo[3,4-c]pyridine-2-carboxamide | ¹H NMR (300 MHz, DMSO-$d_6$) δ 8.63 (d, J = 8.3 Hz, 2H), 8.50 (d, J = 5.0 Hz, 1H), 8.28 (t, J = 5.7 Hz, 1H), 7.77 (d, J = 8.8 Hz, 2H), 7.65 (d, J = 8.8 Hz, 2H), 7.44 (d, J = 5.0 Hz, 1H), 4.83 (d, J = 4.3 Hz, 4H), 3.82-3.64 (m, 2H), 3.18-3.04 (m, 3H), 1.78 (dd, J = 6.9, 3.6 Hz, 2H), 1.58 (dd, J = 10.2, 6.6 Hz, 1H), 1.53-1.36 (m, 1H), 1.31-1.17 (m, 1H) | (ESI (+)) m/e 381 (M + H)⁺ |
| 555 | N-{4-[(tetrahydro-2H-pyran-4-ylmethyl)carbamoyl]phenyl}-1,3-dihydro-2H-pyrrolo[3,4-c]pyridine-2-carboxamide | ¹H NMR (300 MHz, DMSO-$d_6$) δ 8.66-8.59 (m, 2H), 8.50 (d, J = 5.0 Hz, 1H), 8.33-8.25 (m, 1H), 7.81-7.74 (m, 2H), 7.69-7.61 (m, 2H), 7.44 (d, J = 5.0 Hz, 1H), 4.82 (bs, 4H), 3.89-3.79 (m, 2H), 3.24 (d, J = 11.6 Hz, 1H), 3.14 (t, J = 6.1 Hz, 2H), 1.86-1.69 (m, 1H), 1.64-1.54 (m, 2H), 1.27-1.06 (m, 3H) | (ESI (+)) m/e 381 (M + H)⁺ |
| 556 | N-(4-{[(2S)-1-hydroxy-4-methylpentan-2-yl]carbamoyl}phenyl)-1,3-dihydro-2H-pyrrolo[3,4-c]pyridine-2-carboxamide | ¹H NMR (300 MHz, DMSO-$d_6$) δ 8.66-8.59 (m, 2H), 8.50 (d, J = 5.0 Hz, 1H), 7.83-7.75 (m, 3H), 7.69-7.61 (m, 2H), 7.44 (d, J = 5.1 Hz, 1H), 4.91-4.80 (m, 4H), 4.64 (t, J = 5.7 Hz, 1H), 4.12-3.99 (m, 1H), 3.41 (d, J = 5.3 Hz, 1H), 1.69-1.54 (m, 1H), 1.53-1.31 (m, 2H), 0.88 (t, J = 6.7 Hz, 6H) | (ESI (+)) m/e 383 (M + H)⁺ |
| 599 | N-[4-(propylcarbamoyl)phenyl]-1,3-dihydro-2H-pyrrolo[3,4-c]pyridine-2-carboxamide | ¹H NMR (300 MHz, DMSO-$d_6$) δ ppm 8.62 (d, J = 4.9 Hz, 2H), 8.50 (d, J = 5.0 Hz, 1H), 8.30-8.20 (m, 1H), 7.83-7.72 (m, 2H), 7.68-7.59 (m, 2H), 7.44 (d, J = 5.1 Hz, 1H), 4.87-4.77 (m, 4H), 3.22-3.13 (m, 2H), 1.61-1.45 (m, 2H), 0.89 (t, J = 7.4 Hz, 3H) | (ESI (+)) m/e 325 (M + H)⁺ |
| 600 | N-(4-{[(2S)-tetrahydrofuran-2-ylmethyl]carbamoyl}phenyl)-5,7-dihydro-6H-pyrrolo[3,4-b]pyridine-6-carboxamide | ¹H NMR (300 MHz, DMSO-$d_6$) δ 8.63 (s, 1H), 8.48 (dd, J = 4.9, 1.5 Hz, 1H), 8.34 (t, J = 5.8 Hz, 1H), 7.85-7.75 (m, 3H), 7.70-7.63 (m, 2H), 7.33 (dd, J = 7.7, 4.9 Hz, 1H), 4.80 (bs, 4H), 3.97 (p, J = 6.2 Hz, 1H), 3.83-3.72 (m, 1H), 3.68-3.57 (m, 1H), 3.28 (dd, J = 5.9, 1.7 Hz, 1H), 1.98-1.72 (m, 3H), 1.66-1.51 (m, 1H) | (ESI (+)) m/e 367 (M + H)⁺ |
| 601 | N-(4-{[(2R)-tetrahydrofuran-2-ylmethyl]carbamoyl}phenyl)-5,7-dihydro-6H-pyrrolo[3,4-b]pyridine-6-carboxamide | ¹H NMR (300 MHz, DMSO-$d_6$) δ 8.62 (s, 1H), 8.48 (dd, J = 4.9, 1.5 Hz, 1H), 8.32 (t, J = 5.8 Hz, 1H), 7.85-7.75 (m, 3H), 7.70-7.63 (m, 2H), 7.33 (dd, J = 7.7, 4.9 Hz, 1H), 4.80 (bs, 4H), 3.97 (p, J = 6.2 Hz, 1H), 3.83-3.72 (m, 1H), 3.68-3.57 (m, 1H), 1.98-1.72 (m, 3H), 1.69-1.51 (m, 1H) | (ESI (+)) m/e 367 (M + H)⁺ |
| 602 | N-(4-{[(2S)-1-hydroxy-4-methylpentan-2-yl]carbamoyl}phenyl)-5,7-dihydro-6H-pyrrolo[3,4-b]pyridine-6-carboxamide | ¹H NMR (300 MHz, DMSO-$d_6$) δ 8.61 (s, 1H), 8.48 (dd, J = 4.9, 1.5 Hz, 1H), 7.87-7.71 (m, 4H), 7.70-7.63 (m, 2H), 7.33 (dd, J = 7.7, 4.9 Hz, 1H), 4.79 (bs, 4H), 4.13-3.95 (m, 1H), 3.42 (dd, J = 10.6, 5.4 Hz, 2H), 1.72-1.54 (m, 1H), 1.53-1.31 (m, 2H), 0.88 (t, J = 6.7 Hz, 6H) | (ESI (+)) m/e 383 (M + H)⁺ |
| 603 | N-(4-{[(1S)-2-hydroxy-1-phenylethyl]carbamoyl}phenyl)-5,7-dihydro-6H-pyrrolo[3,4-b]pyridine-6-carboxamide | ¹H NMR (300 MHz, DMSO-$d_6$) δ 8.64 (s, 1H), 8.53-8.45 (m, 2H), 7.88-7.78 (m, 3H), 7.73-7.66 (m, 2H), 7.47-7.27 (m, 5H), 7.27-7.18 (m, 1H), 5.12-5.01 (m, 1H), 4.90 (t, J = 5.8 Hz, 1H), 4.80 (bs, 4H), 3.78-3.59 (m, 2H) | (ESI (+)) m/e 403 (M + H)⁺ |
| 604 | N-{4-[(tetrahydro-2H-pyran-4-ylmethyl)carbamoyl]phenyl}-5,7-dihydro-6H-pyrrolo[3,4-b]pyridine-6-carboxamide | ¹H NMR (300 MHz, DMSO-$d_6$) δ 8.62 (s, 1H), 8.48 (dd, J = 4.9, 1.5 Hz, 1H), 8.30 (t, J = 5.8 Hz, 1H), 7.85-7.74 (m, 3H), 7.70-7.63 (m, 2H), 7.33 (dd, J = 7.7, 4.9 Hz, 1H), 4.79 (bs, 4H), 3.89-3.79 (m, 2H), 3.28-3.19 (m, 2H), 3.14 (t, J = 6.3 Hz, 2H), 1.87-1.70 (m, 1H), 1.64-1.54 (m, 2H), 1.29-1.01 (m, 2H) | (ESI (+)) m/e 381 (M + H)⁺ |
| 613 | N-(4-{[(1S)-2-hydroxy-1-(pyridin-2-yl)ethyl]carbamoyl}phenyl)-5,7-dihydro-6H-pyrrolo[3,4-b]pyridine-6-carboxamide | ¹H NMR (300 MHz, DMSO-$d_6$) δ 8.65 (s, 1H), 8.55-8.51 (m, 1H), 8.47 (d, J = 6.7 Hz, 1H), 7.87 (d, J = 8.8 Hz, 2H), 7.84-7.79 (m, 1H), 7.76 (dd, J = 7.7, 1.8 Hz, 1H), 7.71 (t, J = 5.4 Hz, 2H), 7.41 (d, J = 7.8 Hz, 1H), 7.33 (dd, J = 7.7, 4.9 Hz, 1H), 7.29-7.22 (m, 1H), 5.19-5.09 (m, 1H), 4.90 (t, J = 5.9 Hz, 1H), 4.80 (bs, 4H), 3.90-3.72 (m, 2H) | (ESI (+)) m/e 404 (M + H)⁺ |
| 627 | N-{4-[(4-hydroxypiperidin-1-yl)carbonyl]phenyl}-1,3-dihydro-2H-pyrrolo[3,4-c]pyridine-2-carboxamide | ¹H NMR (300 MHz, DMSO-$d_6$) δ 8.60 (d, J = 5.9 Hz, 2H), 8.50 (d, J = 5.0 Hz, 1H), 7.62 (d, 2H), 7.44 (d, J = 5.1 Hz, 1H), 7.30 (d, 2H), 4.82 (d, J = 4.3 Hz, 4H), 4.76 (d, J = 4.0 Hz, 1H), 3.73 (td, J = 8.3, 4.2 Hz, 2H), 3.22-3.08 (m, 2H), 1.82-1.65 (m, 2H), 1.43-1.26 (m, 2H) | (ESI (+)) m/e 367 (M + H)⁺ |

-continued

| Ex | Name | ¹H NMR | MS |
|---|---|---|---|
| 628 | N-{4-[(2-hydroxy-2-methylpropyl)carbamoyl]phenyl}-1,3-dihydro-2H-pyrrolo[3,4-c]pyridine-2-carboxamide | ¹H NMR (300 MHz, DMSO-d₆) δ 8.64 (d, J = 12.5 Hz, 2H), 8.50 (d, J = 5.0 Hz, 1H), 8.06 (t, J = 6.0 Hz, 1H), 7.80 (d, J = 8.8 Hz, 2H), 7.66 (d, J = 8.8 Hz, 2H), 7.44 (d, J = 5.1 Hz, 1H), 4.83 (d, J = 4.3 Hz, 4H), 4.56 (s, 1H), 3.24 (d, J = 6.0 Hz, 2H), 2.89 (s, 1H), 1.10 (s, 6H) | (ESI (+)) m/e 355 (M + H)⁺ |
| 629 | N-{4-[(4-hydroxybutyl)carbamoyl]phenyl}-1,3-dihydro-2H-pyrrolo[3,4-c]pyridine-2-carboxamide | ¹H NMR (300 MHz, DMSO-d₆) δ 8.62 (d, J = 6.4 Hz, 1H), 8.50 (d, J = 5.0 Hz, 1H), 8.26 (t, J = 5.6 Hz, 1H), 7.76 (d, J = 8.8 Hz, 1H), 7.64 (d, J = 8.8 Hz, 1H), 7.44 (d, J = 5.1 Hz, 1H), 4.82 (d, J = 4.3 Hz, 1H), 4.39 (t, J = 5.1 Hz, 1H), 3.41 (q, J = 6.1 Hz, 2H), 3.25-3.15 (m, 2H), 1.59-1.38 (m, 4H) | (ESI (+)) m/e 355 (M + H)⁺ |
| 630 | N-(4-{[(2S)-1-hydroxy-3-methylbutan-2-yl]carbamoyl}phenyl)-1,3-dihydro-2H-pyrrolo[3,4-c]pyridine-2-carboxamide | ¹H NMR (300 MHz, DMSO-d₆) δ 8.62 (d, J = 6.0 Hz, 2H), 8.50 (d, J = 5.0 Hz, 1H), 7.83-7.77 (m, 2H), 7.74 (d, J = 8.9 Hz, 1H), 7.64 (d, J = 1.8 Hz, 1H), 7.44 (d, J = 5.1 Hz, 1H), 4.83 (d, J = 4.3 Hz, 4H), 4.53 (t, J = 5.6 Hz, 1H), 3.90-3.70 (m, 1H), 3.51 (t, J = 5.8 Hz, 2H), 1.92 (dq, J = 13.6, 6.8 Hz, 1H), 0.89 (dd, J = 7.9, 6.9 Hz, 6H) | (ESI (+)) m/e 369 (M + H)⁺ |
| 631 | N-{4-[(1-hydroxy-2-methylpropan-2-yl)carbamoyl]phenyl}-1,3-dihydro-2H-pyrrolo[3,4-c]pyridine-2-carboxamide | ¹H NMR (300 MHz, DMSO-d₆) δ 8.62 (d, J = 4.0 Hz, 1H), 8.50 (d, J = 5.0 Hz, 1H), 7.73 (d, J = 8.9 Hz, 1H), 7.64 (d, J = 8.9 Hz, 1H), 7.44 (d, J = 5.1 Hz, 1H), 7.35 (s, 1H), 4.94 (t, J = 5.9 Hz, 1H), 4.82 (d, J = 4.3 Hz, 1H), 3.49 (d, J = 6.0 Hz, 2H), 1.31 (s, 6H) | (ESI (+)) m/e 355 (M + H)⁺ |
| 632 | N-(4-{[(2R)-2-hydroxypropyl]carbamoyl}phenyl)-1,3-dihydro-2H-pyrrolo[3,4-c]pyridine-2-carboxamide | ¹H NMR (300 MHz, DMSO-d₆) δ 8.63 (d, J = 9.3 Hz, 2H), 8.50 (d, J = 5.0 Hz, 1H), 8.21 (t, J = 5.7 Hz, 1H), 7.79 (d, J = 8.8 Hz, 2H), 7.65 (d, J = 8.8 Hz, 2H), 7.44 (d, J = 5.0 Hz, 1H), 4.83 (d, J = 4.2 Hz, 4H), 4.72 (d, J = 4.7 Hz, 1H), 3.77 (dt, J = 11.9, 6.1 Hz, 1H), 3.24-3.09 (m, 2H), 3.05 (s, 1H), 1.06 (d, J = 6.2 Hz, 3H) | (ESI (+)) m/e 341 (M + H)⁺ |
| 633 | N-(4-{[(2S)-2-hydroxypropyl]carbamoyl}phenyl)-1,3-dihydro-2H-pyrrolo[3,4-c]pyridine-2-carboxamide | ¹H NMR (300 MHz, DMSO-d₆) δ 8.63 (d, J = 8.5 Hz, 2H), 8.50 (d, J = 5.0 Hz, 1H), 8.20 (t, J = 5.7 Hz, 1H), 7.79 (d, J = 8.8 Hz, 1H), 7.65 (d, J = 8.8 Hz, 1H), 7.44 (d, J = 5.1 Hz, 1H), 4.83 (d, J = 4.3 Hz, 4H), 4.72 (d, J = 4.7 Hz, 1H), 3.87-3.68 (m, 1H), 3.17 (ddd, J = 15.1, 9.4, 3.6 Hz, 2H), 1.06 (d, J = 6.3 Hz, 3H) | (ESI (+)) m/e 341 (M + H)⁺ |
| 634 | N-(4-{[3-(piperidin-1-yl)propyl]carbamoyl}phenyl)-1,3-dihydro-2H-pyrrolo[3,4-c]pyridine-2-carboxamide | ¹H NMR (300 MHz, DMSO-d₆) δ 8.63 (d, J = 11.4 Hz, 2H), 8.50 (d, J = 5.0 Hz, 1H), 8.35 (t, J = 5.4 Hz, 1H), 7.76 (d, J = 8.8 Hz, 2H), 7.65 (d, J = 8.8 Hz, 2H), 7.44 (d, J = 5.0 Hz, 1H), 4.82 (d, J = 4.3 Hz, 4H), 2.37-2.22 (m, 6H), 1.72-1.59 (m, 10H), 1.54-1.43 (m, 20H), 1.38 (d, J = 4.8 Hz, 10H) | (ESI (+)) m/e 408 (M + H)⁺ |
| 635 | N-[4-(5,6-dihydroimidazo[1,5-a]pyrazin-7(8H)-ylcarbonyl)phenyl]-1,3-dihydro-2H-pyrrolo[3,4-c]pyridine-2-carboxamide | ¹H NMR (300 MHz, DMSO-d₆) δ 8.64 (d, J = 11.8 Hz, 2H), 8.51 (d, J = 5.0 Hz, 1H), 7.68 (d, J = 8.6 Hz, 2H), 7.61 (s, 1H), 7.43 (t, J = 6.9 Hz, 3H), 4.83 (d, J = 4.3 Hz, 4H), 4.74 (s, 2H), 4.12 (t, J = 5.4 Hz, 2H), 3.84 (s, 2H) | (ESI (+)) m/e 389 (M + H)⁺ |
| 686 | N-[4-(morpholin-4-ylcarbonyl)phenyl]-1,3-dihydro-2H-pyrrolo[3,4-c]pyridine-2-carboxamide | ¹H NMR (500 MHz, DMSO-d₆, Temp = 90° C.) δ 8.69 (s, 1H), 8.55 (d, J = 3.7, 2H), 7.72 (d, J = 5.6, 1H), 7.48-7.39 (m, 2H), 7.21-7.11 (m, 2H), 4.76 (d, J = 23.4, 4H), 3.40 (s, 8H) | (ESI (+)) m/e 353 (M + H)⁺ |
| 687 | N-(4-{[3-(2-oxopyrrolidin-1-yl)propyl]carbamoyl}phenyl)-1,3-dihydro-2H-pyrrolo[3,4-c]pyridine-2-carboxamide | ¹H NMR (500 MHz, DMSO-d₆, Temp = 90° C.) δ 8.88 (s, 1H), 8.76 (d, J = 5.7, 2H), 8.29 (t, J = 5.7, 1H), 7.91 (d, J = 5.7, 1H), 7.78 (m, 2H), 7.65 (m, 2H), 4.98 (bs, 2H), 4.94 (bs, 2H), 3.35 (t, J = 7.0, 2H), 3.22 (m, 4H), 2.22 (t, J = 8.0, 2H), 1.92 (m, 2H), 1.70 (p, J = 7.0, 2H) | (ESI (+)) m/e 408 (M + H)⁺ |
| 723 | N-{4-[(2-isopropoxyethyl)carbamoyl]phenyl}-1,3-dihydro-2H-pyrrolo[3,4-c]pyridine-2-carboxamide | ¹H NMR (500 MHz, DMSO-D₂O) δ ppm 8.89 (s, 1 H) 8.78 (d, J = 6.10 Hz, 1 H) 8.02 (d, J = 5.80 Hz, 1 H) 7.76-7.81 (m, 2 H) 7.62-7.66 (m, 2 H) 5.01 (d, J = 30.82 Hz, 4 H) 3.54-3.63 (m, 1 H) 3.49 (t, J = 6.10 Hz, 2 H) 3.38 (t, J = 6.10 Hz, 2 H) 1.09 (d, J = 6.10 Hz, 6 H) | (ESI (+)) m/e 369 (M + H)⁺ |
| 724 | N-{4-[methyl(3-methylbutyl)carbamoyl]phenyl}-1,3-dihydro-2H-pyrrolo[3,4-c]pyridine-2-carboxamide | ¹H NMR (500 MHz, DMSO-D₂O) δ ppm 8.89 (s, 1 H) 8.79 (d, J = 6.10 Hz, 1 H) 8.04 (d, J = 5.80 Hz, 1 H) 7.60 (d, J = 8.54 Hz, 2 H) 7.32 (d, J = 7.63 Hz, 2 H) 4.95-5.07 (m, 4 H) 3.44 (s, 2 H) 2.89-2.96 (m, 3 H) 1.44 (s, 3 H) 0.83 (d, J = 107.41 Hz, 6 H) | (ESI (+)) m/e 367 (M + H)⁺ |

| Ex | Name | ¹H NMR | MS |
|---|---|---|---|
| 725 | N-[4-(azetidin-1-ylcarbonyl)phenyl]-1,3-dihydro-2H-pyrrolo[3,4-c]pyridine-2-carboxamide | ¹H NMR (500 MHz, DMSO-D₂O) δ ppm 8.84 (s, 1 H) 8.74 (d, J = 5.80 Hz, 1 H) 7.94 (d, J = 5.80 Hz, 1 H) 7.60-7.64 (m, 2 H) 7.56-7.59 (m, 2 H) 4.98 (d, J = 24.72 Hz, 4 H) 4.34 (s, 2 H) 4.05 (d, J = 6.71 Hz, 2 H) 2.22-2.33 (m, 2 H) | (ESI (+)) m/e 323 (M + H)⁺ |
| 726 | N-[4-(2,6-diazaspiro[3.5]non-2-ylcarbonyl)phenyl]-1,3-dihydro-2H-pyrrolo[3,4-c]pyridine-2-carboxamide | | |
| 727 | N-[4-(1,7-diazaspiro[4.4]non-1-ylcarbonyl)phenyl]-1,3-dihydro-2H-pyrrolo[3,4-c]pyridine-2-carboxamide | | |
| 728 | N-(4-{[4-(morpholin-4-yl)benzyl]carbamoyl}phenyl)-1,3-dihydro-2H-pyrrolo[3,4-c]pyridine-2-carboxamide | ¹H NMR (500 MHz, DMSO-D₂O) δ ppm 8.90 (s, 1 H) 8.80 (d, J = 5.80 Hz, 1 H) 8.05 (d, J = 5.80 Hz, 1 H) 7.80-7.85 (m, 2 H) 7.61-7.68 (m, 2 H) 7.27 (d, J = 8.54 Hz, 2 H) 7.05 (d, J = 8.85 Hz, 2 H) 5.02 (d, J = 33.26 Hz, 4 H) 4.40 (s, 2 H) 3.76-3.81 (m, 4 H) 3.16-3.19 (m, 4 H) | (ESI (+)) m/e 458 (M + H)⁺ |
| 729 | N-{4-[(cyclopropylmethyl)carbamoyl]phenyl}-1,3-dihydro-2H-pyrrolo[3,4-c]pyridine-2-carboxamide | ¹H NMR (500 MHz, DMSO-D₂O) δ ppm 8.90 (s, 1 H) 8.79 (d, J = 5.80 Hz, 1 H) 8.04 (d, J = 6.10 Hz, 1 H) 7.78-7.82 (m, 2 H) 7.62-7.67 (m, 2 H) 5.02 (d, J = 31.73 Hz, 4 H) 3.14 (d, J = 7.02 Hz, 2 H) 0.99-1.08 (m, 1 H) 0.40-0.48 (m, 2 H) 0.21-0.26 (m, 2 H) | (ESI (+)) m/e 337 (M + H)⁺ |
| 730 | N-{4-[methyl(propyl)carbamoyl]phenyl}-1,3-dihydro-2H-pyrrolo[3,4-c]pyridine-2-carboxamide | ¹H NMR (500 MHz, DMSO-D₂O) δ ppm 8.89 (s, 1 H) 8.79 (d, J = 6.10 Hz, 1 H) 8.04 (d, J = 5.80 Hz, 1 H) 7.57-7.64 (m, 2 H) 7.25-7.38 (m, 2 H) 5.01 (d, J = 32.04 Hz, 4 H) 3.17-3.45 (m, 2 H) 2.93 (s, 3 H) 1.53 (d, J = 7.32 Hz, 2 H) 0.64-0.97 (m, 3 H) | (ESI (+)) m/e 339 (M + H)⁺ |
| 731 | N-[4-(isobutylcarbamoyl)phenyl]-1,3-dihydro-2H-pyrrolo[3,4-c]pyridine-2-carboxamide | ¹H NMR (500 MHz, DMSO-D₂O) δ ppm 8.90 (s, 1 H) 8.79 (d, J = 5.80 Hz, 1 H) 8.04 (d, J = 5.80 Hz, 1 H) 7.77-7.81 (m, 2 H) 7.60-7.65 (m, 2 H) 5.02 (d, J = 31.73 Hz, 4 H) 3.08 (d, J = 7.02 Hz, 2 H) 1.79-1.89 (m, 1 H) 0.89 (d, J = 6.71 Hz, 6 H) | (ESI (+)) m/e 339 (M + H)⁺ |
| 732 | N-[4-(butylcarbamoyl)phenyl]-1,3-dihydro-2H-pyrrolo[3,4-c]pyridine-2-carboxamide | ¹H NMR (500 MHz, DMSO-D₂O) δ ppm 8.84 (s, 1 H) 8.74 (d, J = 5.80 Hz, 1 H) 7.94 (d, J = 5.80 Hz, 1 H) 7.76-7.79 (m, 2 H) 7.61-7.65 (m, 2 H) 4.98 (d, J = 24.41 Hz, 4 H) 3.25 (t, J = 7.02 Hz, 2 H) 1.46-1.55 (m, 2 H) 1.28-1.38 (m, 2 H) 0.90 (t, J = 7.32 Hz, 3 H) | (ESI (+)) m/e 339 (M + H)⁺ |
| 733 | N-{4-[(2-methoxyethyl)carbamoyl]phenyl}-1,3-dihydro-2H-pyrrolo[3,4-c]pyridine-2-carboxamide | ¹H NMR (500 MHz, DMSO-D₂O) δ ppm 8.88 (s, 1 H) 8.78 (d, J = 5.80 Hz, 1 H) 8.02 (d, J = 5.80 Hz, 1 H) 7.77-7.81 (m, 2 H) 7.60-7.65 (m, 2 H) 5.01 (d, J = 29.90 Hz, 4 H) 3.40-3.50 (m, 4 H) 3.27 (s, 3 H) | (ESI (+)) m/e 341 (M + H)⁺ |
| 734 | N-[4-(cyclopentylcarbamoyl)phenyl]-1,3-dihydro-2H-pyrrolo[3,4-c]pyridine-2-carboxamide | ¹H NMR (500 MHz, DMSO-D₂O) δ ppm 8.89 (s, 1 H) 8.79 (d, J = 5.80 Hz, 1 H) 8.03 (d, J = 6.10 Hz, 1 H) 7.77-7.81 (m, 2 H) 7.60-7.65 (m, 2 H) 5.01 (d, J = 31.43 Hz, 4 H) 4.14-4.25 (m, 1 H) 1.82-1.99 (m, 2 H) 1.64-1.78 (m, 2 H) 1.47-1.58 (m, 4 H) | (ESI (+)) m/e 351 (M + H)⁺ |
| 735 | N-{4-[(3R)-tetrahydrofuran-3-ylcarbamoyl]phenyl}-1,3-dihydro-2H-pyrrolo[3,4-c]pyridine-2-carboxamide | ¹H NMR (500 MHz, DMSO-D₂O) δ ppm 8.90 (s, 1 H) 8.80 (d, J = 6.10 Hz, 1 H) 8.05 (d, J = 6.10 Hz, 1 H) 7.79-7.83 (m, 2 H) 7.61-7.67 (m, 2 H) 5.02 (d, J = 32.65 Hz, 4 H) 4.39-4.50 (m, 1 H) 3.85-3.90 (m, 2 H) 3.70-3.76 (m, 1 H) 3.58 (dd, J = 8.85, 4.27 Hz, 1 H) 2.11-2.23 (m, 1 H) 1.89-1.97 (m, 1 H) | (ESI (+)) m/e 353 (M + H)⁺ |
| 736 | N-{4-[(2-methoxyethyl)(methyl)carbamoyl]phenyl}-1,3-dihydro-2H-pyrrolo[3,4-c]pyridine-2-carboxamide | ¹H NMR (500 MHz, DMSO-D₂O) δ ppm 8.90 (s, 1 H) 8.79 (d, J = 6.10 Hz, 1 H) 8.04 (d, J = 5.80 Hz, 1 H) 7.60 (d, J = 8.54 Hz, 2 H) 7.34 (d, J = 8.54 Hz, 2 H) 5.01 (d, J = 31.73 Hz, 4 H) 3.51 (d, J = 66.52 Hz, 4 H) 3.15-3.34 (m, 3 H) 2.94-3.02 (m, 3 H) | (ESI (+)) m/e 355 (M + H)⁺ |
| 737 | N-{4-[(1-methoxypropan-2-yl)carbamoyl]phenyl}-1,3-dihydro-2H-pyrrolo[3,4-c]pyridine-2-carboxamide | ¹H NMR (500 MHz, DMSO-D₂O) δ ppm 8.89 (s, 1 H) 8.79 (d, J = 5.49 Hz, 1 H) 8.03 (d, J = 6.10 Hz, 1 H) 7.77-7.81 (m, 2 H) 7.61-7.65 (m, 2 H) 5.02 (d, J = 31.12 Hz, 4 H) 4.15-4.23 (m, 1 H) 3.42 (dd, J = 9.61, 6.56 Hz, 1 H) 3.30 (dd, J = 9.61, 5.95 Hz, 1 H) 3.27 (s, 3 H) 1.14 (d, J = 6.71 Hz, 3 H) | (ESI (+)) m/e 355 (M + H)⁺ |

| Ex | Name | ¹H NMR | MS |
|---|---|---|---|
| 738 | N-{4-[(cyclopentylmethyl)carbamoyl]phenyl}-1,3-dihydro-2H-pyrrolo[3,4-c]pyridine-2-carboxamide | ¹H NMR (500 MHz, DMSO-D$_2$O) δ ppm 8.88 (s, 1 H) 8.78 (d, J = 5.80 Hz, 1 H) 8.01 (d, J = 5.80 Hz, 1 H) 7.74-7.80 (m, 2 H) 7.60-7.66 (m, 2 H) 5.01 (d, J = 29.29 Hz, 4 H) 3.18 (d, J = 7.32 Hz, 2 H) 2.08-2.21 (m, 1 H) 1.45-1.72 (m, 6 H) 1.21-1.29 (m, 2 H) | (ESI (+)) m/e 365 (M + H)$^+$ |
| 739 | N-{4-[(2-thienylmethyl)carbamoyl]phenyl}-1,3-dihydro-2H-pyrrolo[3,4-c]pyridine-2-carboxamide | ¹H NMR (500 MHz, DMSO-D$_2$O) δ ppm 8.86 (s, 1 H) 8.76 (d, J = 5.80 Hz, 1 H) 7.98 (d, J = 5.80 Hz, 1 H) 7.79-7.85 (m, 2 H) 7.63-7.68 (m, 2 H) 7.37 (dd, J = 5.19, 1.22 Hz, 1 H) 7.03 (dd, J = 3.36, 1.22 Hz, 1 H) 6.97 (dd, J = 5.19, 3.36 Hz, 1 H) 5.00 (d, J = 27.16 Hz, 4 H) 4.62 (s, 2 H) | (ESI (+)) m/e 379 (M + H)$^+$ |
| 740 | N-{4-[methyl(tetrahydrofuran-2-ylmethyl)carbamoyl]phenyl}-1,3-dihydro-2H-pyrrolo[3,4-c]pyridine-2-carboxamide | ¹H NMR (500 MHz, DMSO-D$_2$O) δ ppm 8.89 (s, 1 H) 8.78 (d, J = 5.80 Hz, 1 H) 8.02 (d, J = 5.80 Hz, 1 H) 7.60 (d, J = 8.54 Hz, 2 H) 7.34 (d, J = 4.58 Hz, 2 H) 5.01 (d, J = 30.21 Hz, 4 H) 3.93-4.23 (m, 2 H) 3.17-3.72 (m, 3 H) 3.00 (s, 3 H) 1.18-2.07 (m, 4 H) | (ESI (+)) m/e 381 (M + H)$^+$ |
| 741 | N-{4-[(3-isopropoxypropyl)carbamoyl]phenyl}-1,3-dihydro-2H-pyrrolo[3,4-c]pyridine-2-carboxamide | ¹H NMR (500 MHz, DMSO-D$_2$O) δ ppm 8.89 (s, 1 H) 8.79 (d, J = 6.10 Hz, 1 H) 8.03 (d, J = 5.80 Hz, 1 H) 7.75-7.79 (m, 2 H) 7.61-7.67 (m, 2 H) 5.01 (d, J = 31.43 Hz, 4 H) 3.50-3.57 (m, 1 H) 3.42 (t, J = 6.26 Hz, 2 H) 3.31 (t, J = 7.02 Hz, 2 H) 1.69-1.78 (m, 2 H) 1.09 (d, J = 6.10 Hz, 6 H) | (ESI (+)) m/e 383 (M + H)$^+$ |
| 742 | N-{4-[benzyl(methyl)carbamoyl]phenyl}-1,3-dihydro-2H-pyrrolo[3,4-c]pyridine-2-carboxamide | ¹H NMR (500 MHz, DMSO-D$_2$O) δ ppm 8.89 (s, 1 H) 8.78 (d, J = 5.80 Hz, 1 H) 8.03 (d, J = 5.80 Hz, 1 H) 7.61 (s, 2 H) 7.12-7.47 (m, 7 H) 5.00 (d, J = 31.12 Hz, 4 H) 4.49-4.74 (m, 2 H) 2.89 (s, 3 H) | (ESI (+)) m/e 387 (M + H)$^+$ |
| 743 | N-{4-[(3-aminobenzyl)carbamoyl]phenyl}-1,3-dihydro-2H-pyrrolo[3,4-c]pyridine-2-carboxamide | ¹H NMR (500 MHz, DMSO-D$_2$O) δ ppm 8.84 (s, 1 H) 8.73 (d, J = 5.80 Hz, 1 H) 7.92 (d, J = 5.80 Hz, 1 H) 7.83-7.86 (m, 2 H) 7.64-7.68 (m, 2 H) 7.43 (t, J = 7.78 Hz, 1 H) 7.30 (d, J = 7.93 Hz, 1 H) 7.21 (s, 1 H) 7.13-7.16 (m, 1 H) 4.98 (d, J = 23.19 Hz, 4 H) 4.49 (s, 2 H) | (ESI (+)) m/e 386 (M + H)$^+$ |
| 744 | N-{4-[(6-methoxypyridin-3-yl)carbamoyl]phenyl}-1,3-dihydro-2H-pyrrolo[3,4-c]pyridine-2-carboxamide | ¹H NMR (500 MHz, DMSO-D$_2$O) δ ppm 8.88 (s, 1 H) 8.77 (d, J = 5.80 Hz, 1 H) 8.48 (d, J = 2.44 Hz, 1 H) 7.98-8.07 (m, 2 H) 7.89-7.95 (m, 2 H) 7.69-7.74 (m, 2 H) 6.87 (d, J = 8.85 Hz, 1 H) 5.02 (d, J = 29.29 Hz, 4 H) 3.83-3.88 (m, 3 H) | (ESI (+)) m/e 390 (M + H)$^+$ |
| 745 | N-{4-[(3-isobutoxypropyl)carbamoyl]phenyl}-1,3-dihydro-2H-pyrrolo[3,4-c]pyridine-2-carboxamide | ¹H NMR (500 MHz, DMSO-D$_2$O) δ ppm 8.87 (s, 1 H) 8.76 (d, J = 5.80 Hz, 1 H) 7.99 (d, J = 5.80 Hz, 1 H) 7.74-7.80 (m, 2 H) 7.61-7.66 (m, 2 H) 5.00 (d, J = 28.07 Hz, 4 H) 3.43 (t, J = 6.26 Hz, 2 H) 3.31 (t, J = 7.02 Hz, 2 H) 3.15 (d, J = 6.71 Hz, 2 H) 1.71-1.81 (m, 3 H) 0.86 (d, J = 6.71 Hz, 6 H) | (ESI (+)) m/e 397 (M + H)$^+$ |
| 746 | N-{4-[bis(2-methoxyethyl)carbamoyl]phenyl}-1,3-dihydro-2H-pyrrolo[3,4-c]pyridine-2-carboxamide | ¹H NMR (500 MHz, DMSO-D$_2$O) δ ppm 8.88 (s, 1 H) 8.78 (d, J = 5.80 Hz, 1 H) 8.02 (d, J = 6.10 Hz, 1 H) 7.57-7.61 (m, 2 H) 7.29-7.33 (m, 2 H) 5.00 (d, J = 30.82 Hz, 4 H) 3.34-3.58 (m, 8 H) 3.12-3.32 (m, 6 H) | (ESI (+)) m/e 399 (M + H)$^+$ |
| 747 | N-{4-[(4-methoxybenzyl)carbamoyl]phenyl}-1,3-dihydro-2H-pyrrolo[3,4-c]pyridine-2-carboxamide | ¹H NMR (500 MHz, DMSO-D$_2$O) δ ppm 8.84 (s, 1 H) 8.74 (d, J = 5.80 Hz, 1 H) 7.93 (d, J = 5.80 Hz, 1 H) 7.79-7.83 (m, 2 H) 7.62-7.66 (m, 2 H) 7.23-7.30 (m, 2 H) 6.86-6.93 (m, 2 H) 4.98 (d, J = 24.11 Hz, 4 H) 4.40 (s, 2 H) 3.73 (s, 3 H) | (ESI (+)) m/e 403 (M + H)$^+$ |
| 748 | N-{4-[(3-methoxybenzyl)carbamoyl]phenyl}-1,3-dihydro-2H-pyrrolo[3,4-c]pyridine-2-carboxamide | ¹H NMR (500 MHz, DMSO-D$_2$O) δ ppm 8.87 (s, 1 H) 8.77 (d, J = 5.80 Hz, 1 H) 8.00 (d, J = 6.10 Hz, 1 H) 7.81-7.86 (m, 2 H) 7.63-7.68 (m, 2 H) 7.26 (t, J = 7.93 Hz, 1 H) 6.80-6.92 (m, 3 H) 5.01 (d, J = 28.99 Hz, 4 H) 4.44 (s, 2 H) 3.74 (s, 3 H) | (ESI (+)) m/e 403 (M + H)$^+$ |
| 749 | N-(4-{[4-(trifluoromethyl)piperidin-1-yl]carbonyl}phenyl)-1,3-dihydro-2H-pyrrolo[3,4-c]pyridine-2-carboxamide | ¹H NMR (500 MHz, DMSO-D$_2$O) δ ppm 8.88 (s, 1 H) 8.78 (d, J = 6.10 Hz, 1 H) 8.02 (d, J = 6.10 Hz, 1 H) 7.59-7.65 (m, 2 H) 7.32-7.38 (m, 2 H) 5.01 (d, J = 30.51 Hz, 4 H) 4.55 (d, J = 47.91 Hz, 2 H) 2.75-3.24 (m, 2 H) 2.59-2.68 (m, 1 H) 1.87 (s, 2 H) 1.34-1.49 (m, 2 H) | (ESI (+)) m/e 419 (M + H)$^+$ |

| Ex | Name | ¹H NMR | MS |
|---|---|---|---|
| 750 | N-(4-{[4-(pyrazin-2-yl)piperazin-1-yl]carbonyl}phenyl)-1,3-dihydro-2H-pyrrolo[3,4-c]pyridine-2-carboxamide | ¹H NMR (500 MHz, DMSO-D₂O) δ ppm 8.90 (s, 1 H) 8.79 (d, J = 5.80 Hz, 1 H) 8.32 (d, J = 1.22 Hz, 1 H) 8.13 (dd, J = 2.59, 1.37 Hz, 1 H) 8.05 (d, J = 5.80 Hz, 1 H) 7.88 (d, J = 2.75 Hz, 1 H) 7.61-7.68 (m, 2 H) 7.38-7.45 (m, 2 H) 5.02 (d, J = 32.34 Hz, 4 H) 3.44-3.76 (m, 8 H) | (ESI (+)) m/e 430 (M + H)⁺ |
| 751 | N-{4-[(4-cyclohexylpiperazin-1-yl)carbonyl]phenyl}-1,3-dihydro-2H-pyrrolo[3,4-c]pyridine-2-carboxamide | ¹H NMR (500 MHz, DMSO-D₂O) δ ppm 8.88 (s, 1 H) 8.78 (d, J = 6.10 Hz, 1 H) 8.01 (d, J = 6.10 Hz, 1 H) 7.57-7.69 (m, 2 H) 7.36-7.49 (m, 2 H) 5.01 (d, J = 29.29 Hz, 4 H) 3.96 (s, 1 H) 3.23-3.67 (m, 4 H) 2.98-3.27 (m, 4 H) 1.04-2.15 (m, 10 H) | (ESI (+)) m/e 434 (M + H)⁺ |
| 752 | N-(4-{[2-(3,4-dimethoxyphenyl)ethyl]carbamoyl}phenyl)-1,3-dihydro-2H-pyrrolo[3,4-c]pyridine-2-carboxamide | ¹H NMR (500 MHz, DMSO-D₂O) δ ppm 8.88 (s, 1 H) 8.77 (d, J = 5.80 Hz, 1 H) 8.01 (d, J = 6.10 Hz, 1 H) 7.73-7.80 (m, 2 H) 7.58-7.68 (m, 2 H) 6.84-6.89 (m, 2 H) 6.77 (dd, J = 8.09, 1.98 Hz, 1 H) 5.01 (d, J = 29.90 Hz, 4 H) 3.96 (s, 1 H) 3.70-3.73 (m, 6 H) 3.46 (t, J = 7.32 Hz, 2 H) 2.78 (t, J = 7.32 Hz, 2 H) | (ESI (+)) m/e 447 (M + H)⁺ |
| 770 | N-(4-{[3-(dimethylamino)propyl]carbamoyl}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 4.88 Hz, 1 H) 7.70-7.78 (m, 2 H) 7.57-7.65 (m, 2 H) 7.41 (d, J = 4.88 Hz, 1 H) 4.80-4.87 (m, 4 H) 3.30-3.34 (m, 2 H) 2.28-2.40 (m, 2 H) 2.17-2.21 (m, 6 H) 1.61-1.75 (m, 2 H) | (ESI (+)) m/e 368 (M + H)⁺ |
| 771 | N-(4-{[3-(morpholin-4-yl)propyl]carbamoyl}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 5.19 Hz, 1 H) 7.69-7.79 (m, 2 H) 7.57-7.64 (m, 2 H) 7.41 (d, J = 5.19 Hz, 1 H) 4.80-4.87 (m, 4 H) 3.54-3.62 (m, 4 H) 3.31-3.34 (m, 2 H) 2.34-2.42 (m, 6 H) 1.65-1.76 (m, 2 H) | (ESI (+)) m/e 410 (M + H)⁺ |
| 772 | N-(4-{[4-(2-aminoethyl)-1H-imidazol-1-yl]carbonyl}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 4.88 Hz, 1 H) 7.71-7.76 (m, 2 H) 7.57-7.66 (m, 2 H) 7.52 (s, 1 H) 7.41 (d, J = 5.19 Hz, 1 H) 6.82 (s, 1 H) 4.78-4.86 (m, 4 H) 3.51 (t, J = 7.32 Hz, 2 H) 2.80 (t, J = 7.02 Hz, 2 H) | (ESI (+)) m/e 377 (M + H)⁺ |
| 773 | N-[4-({4-[2-(2-hydroxyethoxy)ethyl]piperazin-1-yl}carbonyl)phenyl]-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 5.19 Hz, 1 H) 7.56-7.62 (m, 2 H) 7.41 (d, J = 5.19 Hz, 1 H) 7.27-7.33 (m, 2 H) 4.79-4.87 (m, 4 H) 3.40-3.60 (m, 10 H) 2.53-2.57 (m, 2 H) 2.43-2.50 (m, 4 H) | (ESI (+)) m/e 440 (M + H)⁺ |
| 774 | N-{4-[(3-hydroxypropyl)carbamoyl]phenyl}-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 5.19 Hz, 1 H) 7.71-7.78 (m, 2 H) 7.58-7.63 (m, 2 H) 7.41 (d, J = 5.19 Hz, 1 H) 4.78-4.89 (m, 4 H) 3.51 (t, J = 6.26 Hz, 2 H) 3.34 (t, J = 6.87 Hz, 2 H) 1.65-1.79 (m, 2 H) | (ESI (+)) m/e 341 (M + H)⁺ |
| 775 | N-(4-{[4-(dimethylamino)butyl]carbamoyl}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 4.88 Hz, 1 H) 7.71-7.77 (m, 2 H) 7.58-7.64 (m, 2 H) 7.42 (d, J = 4.88 Hz, 1 H) 4.79-4.88 (m, 4 H) 3.27 (t, J = 6.87 Hz, 2 H) 2.26-2.33 (m, 2 H) 2.16 (s, 6 H) 1.41-1.61 (m, 4 H) | (ESI (+)) m/e 382 (M + H)⁺ |
| 776 | N-{4-[(pyridin-4-ylmethyl)carbamoyl]phenyl}-1,3-dihydro-2H-pyrrolo[3,4-c]pyridine-2-carboxamide | ¹H NMR (400 MHz, DMSO-D₂O, Temp = 90° C.) δ ppm 8.59 (s, 1 H) 8.46-8.50 (m, 3 H) 7.79-7.84 (m, 2 H) 7.62-7.67 (m, 2 H) 7.42 (d, J = 4.88 Hz, 1 H) 7.31 (d, J = 6.10 Hz, 2 H) 4.84 (d, J = 7.02 Hz, 4 H) 4.49 (s, 2 H) | (ESI (+)) m/e 374 (M + H)⁺ |
| 777 | N-{4-[(pyridin-3-ylmethyl)carbamoyl]phenyl}-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.54 (d, J = 1.83 Hz, 1 H) 8.48 (d, J = 5.19 Hz, 1 H) 8.43 (dd, J = 4.88, 1.53 Hz, 1 H) 7.77-7.82 (m, 2 H) 7.71-7.75 (m, 1 H) 7.60-7.66 (m, 2 H) 7.41 (d, J = 5.19 Hz, 1 H) 7.34 (dd, J = 7.93, 5.49 Hz, 1 H) 4.79-4.88 (m, 4 H) 4.44-4.53 (m, 2 H) | (ESI (+)) m/e 374 (M + H)⁺ |
| 778 | N-{4-[(pyrimidin-4-ylmethyl)carbamoyl]phenyl}-1,3-dihydro-2H-pyrrolo[3,4-c]pyridine-2-carboxamide | ¹H NMR (400 MHz, DMSO-D₂O, Temp = 90° C.) δ ppm 9.07 (d, J = 1.22 Hz, 1 H) 8.70 (d, J = 5.19 Hz, 1 H) 8.59 (s, 1 H) 8.49 (d, J = 4.88 Hz, 1 H) 7.79-7.86 (m, 2 H) 7.63-7.68 (m, 2 H) 7.39-7.45 (m, 2 H) 4.81-4.87 (m, 4 H) 4.56 (s, 2 H) | (ESI (+)) m/e 375 (M + H)⁺ |

-continued

| Ex | Name | ¹H NMR | MS |
|---|---|---|---|
| 779 | N-(4-{[2-(pyridin-3-yl)ethyl]carbamoyl}phenyl)-1,3-dihydro-2H-pyrrolo[3,4-c]pyridine-2-carboxamide | ¹H NMR (400 MHz, DMSO-D$_2$O, Temp = 90° C.) δ ppm 8.58 (s, 1 H) 8.48 (d, J = 4.88 Hz, 1 H) 8.45 (d, J = 2.14 Hz, 1 H) 8.39 (dd, J = 4.73, 1.68 Hz, 1 H) 7.69-7.73 (m, 2 H) 7.64-7.68 (m, 1 H) 7.58-7.62 (m, 2 H) 7.42 (d, J = 4.88 Hz, 1 H) 7.30 (dd, J = 7.93, 4.88 Hz, 1 H) 4.81-4.85 (m, 4 H) 3.52-3.57 (m, 2 H) 2.87-2.92 (m, 2 H) | (ESI (+)) m/e 388 (M + H)⁺ |
| 780 | N-(4-{[2-(4-methylpiperazin-1-yl)ethyl]carbamoyl}phenyl)-1,3-dihydro-2H-pyrrolo[3,4-c]pyridine-2-carboxamide | ¹H NMR (400 MHz, DMSO-D$_2$O, Temp = 90° C.) δ ppm 8.58 (s, 1 H) 8.48 (d, J = 5.19 Hz, 1 H) 7.71-7.75 (m, 2 H) 7.58-7.63 (m, 2 H) 7.41 (d, J = 4.88 Hz, 1 H) 4.81-4.86 (m, 4 H) 3.38 (t, J = 6.87 Hz, 2 H) 2.44-2.50 (m, 6 H) 2.33-2.37 (m, 4 H) 2.16 (s, 3 H) | (ESI (+)) m/e 409 (M + H)⁺ |
| 803 | N-(4-{[(3-methyloxetan-3-yl)methyl]carbamoyl}phenyl)-1,3-dihydro-2H-pyrrolo[3,4-c]pyridine-2-carboxamide | ¹H NMR (300 MHz, DMSO-d$_6$) δ 8.66 (s, 1H), 8.61 (s, 1H), 8.51 (d, J = 5.0 Hz, 1H), 8.44 (t, J = 6.1 Hz, 1H), 7.84-7.76 (m, 2H), 7.71-7.63 (m, 2H), 7.44 (d, J = 5.1 Hz, 1H), 4.87-4.80 (m, 4H), 4.48 (d, J = 5.7 Hz, 2H), 4.20 (d, J = 5.7 Hz, 2H), 3.49-3.39 (m, 2H), 1.25 (s, 3H) | (ESI (+)) m/e 367 (M + H)⁺ |
| 875 | N-(4-{[(1,1-dioxidotetrahydrothiophen-3-yl)methyl]carbamoyl}phenyl)-1,3-dihydro-2H-pyrrolo[3,4-c]pyridine-2-carboxamide | ¹H NMR (300 MHz, DMSO-d$_6$) δ 8.72-8.56 (m, 2H), 8.55-8.37 (m, 2H), 7.78 (d, J = 8.8 Hz, 2H), 7.67 (d, J = 8.8 Hz, 2H), 7.43 (t, J = 5.6 Hz, 1H), 4.83 (d, J = 4.3 Hz, 4H), 3.50-3.29 (m, 1H), 3.27-2.99 (m, 3H), 2.88 (dt, J = 13.1, 7.2 Hz, 1H), 2.78-2.58 (m, 1H), 2.33-2.11 (m, 1H), 1.97-1.72 (m, 1H) | (ESI (+)) m/e 415 (M + H)⁺ |
| 880 | N-{4-[(pyrrolidin-3-ylmethyl)carbamoyl]phenyl}-1,3-dihydro-2H-pyrrolo[3,4-c]pyridine-2-carboxamide | ¹H NMR (300 MHz, DMSO-d$_6$) δ 9.08 (s, 2H), 8.93 (d, J = 15.5 Hz, 2H), 8.82 (d, J = 5.8 Hz, 1H), 8.54 (t, J = 5.8 Hz, 1H), 8.02 (d, J = 5.8 Hz, 1H), 7.81 (d, J = 8.6 Hz, 2H), 7.68 (d, J = 8.6 Hz, 2H), 5.06-4.95 (m, 4H), 3.73-3.63 (m, 1H), 3.47-3.05 (m, 4H), 3.02-2.80 (m, 1H), 2.07-1.92 (m, 1H), 1.67 (dq, J = 12.8, 8.1 Hz, 1H) | (ESI (+)) m/e 366 (M + H)⁺ |
| 881 | N-(4-{[(3S)-pyrrolidin-3-ylmethyl]carbamoyl}phenyl)-1,3-dihydro-2H-pyrrolo[3,4-c]pyridine-2-carboxamide | ¹H NMR (300 MHz, DMSO-d$_6$) δ 9.09 (s, 1H), 8.93 (d, J = 15.5 Hz, 1H), 8.82 (d, J = 5.8 Hz, 1H), 8.54 (t, J = 5.8 Hz, 1H), 8.03 (d, J = 5.8 Hz, 1H), 7.81 (d, J = 8.8 Hz, 2H), 7.67 (d, J = 8.9 Hz, 2H), 5.00 (d, J = 19.2 Hz, 4H), 3.69 (dq, J = 5.9, 4.4 Hz, 1H), 3.52-3.44 (m, 1H), 3.35-3.07 (m, 4H), 2.90 (td, J = 13.7, 6.2 Hz, 1H), 2.27 (s, 1H), 2.00 (td, J = 12.8, 7.4 Hz, 1H), 1.66 (dq, J = 16.3, 8.2 Hz, 1H) | (ESI (+)) m/e 366 (M + H)⁺ |
| 882 | N-(4-{[(1-methylpyrrolidin-3-yl)methyl]carbamoyl}phenyl)-1,3-dihydro-2H-pyrrolo[3,4-c]pyridine-2-carboxamide | ¹H NMR (300 MHz, DMSO-d$_6$) δ 9.59 (s, 1H), 8.35 (s, 1H), 7.56-7.49 (m, 2H), 7.41-7.23 (m, 5H), 7.13 (s, 1H), 7.10 (s, 1H), 6.92 (dd, J = 8.3, 2.6 Hz, 1H), 6.89-6.79 (m, 2H), 4.76 (s, 4H), 4.36 (s, 2H), 3.73 (s, 3H) | (ESI (+)) m/e 380 (M + H)⁺ |
| 884 | N-(4-{[(1-methylpiperidin-4-yl)methyl]carbamoyl}phenyl)-1,3-dihydro-2H-pyrrolo[3,4-c]pyridine-2-carboxamide | ¹H NMR (300 MHz, DMSO-d$_6$) δ 8.66-8.59 (m, 2H), 8.50 (d, J = 5.0 Hz, 1H), 8.26 (t, J = 5.8 Hz, 1H), 7.81-7.73 (m, 2H), 7.68-7.61 (m, 2H), 7.44 (d, J = 5.1 Hz, 1H), 4.86-4.75 (m, 4H), 3.12 (t, J = 6.2 Hz, 2H), 2.77-2.69 (m, 2H), 2.12 (s, 3H), 1.78 (td, J = 11.5, 2.4 Hz, 2H), 1.63 (dd, J = 12.5, 2.9 Hz, 2H), 1.54-1.40 (m, 1H), 1.25-1.08 (m, 2H) | (ESI (+)) m/e 394 (M + H)⁺ |
| 922 | N-[4-({[(3R)-1-isobutyrylpyrrolidin-3-yl]methyl}carbamoyl)phenyl]-1,3-dihydro-2H-pyrrolo[3,4-c]pyridine-2-carboxamide | ¹H NMR (300 MHz, DMSO-d$_6$) δ 8.66 (s, 1H), 8.61 (s, 1H), 8.50 (d, J = 5.0 Hz, 1H), 8.41 (t, J = 5.3 Hz, 1H), 7.82-7.74 (m, 2H), 7.70-7.62 (m, 2H), 7.44 (d, J = 5.1 Hz, 1H), 4.84-4.74 (m, 4H), 3.58 (dd, J = 17.0, 9.7 Hz, 1H), 3.44 (dt, J = 22.7, 9.2 Hz, 1H), 3.28-2.93 (m, 2H), 2.64 (pd, J = 6.7, 3.2 Hz, 1H), 2.08-1.83 (m, 1H), 1.78-1.45 (m, 1H), 1.29-1.24 (m, 3H), 1.08-0.91 (m, 6H) | (ESI (+)) m/e 436 (M + H)⁺ |
| 923 | N-[4-({[(3R)-1-benzoylpyrrolidin-3-yl]methyl}carbamoyl)phenyl]-1,3-dihydro-2H-pyrrolo[3,4-c]pyridine-2-carboxamide | ¹H NMR (300 MHz, DMSO-d$_6$) δ 8.68-8.59 (m, 2H), 8.49 (t, J = 5.1 Hz, 1H), 8.47-8.41 (m, 1H), 8.40-8.28 (m, 1H), 7.85-7.76 (m, 1H), 7.76-7.58 (m, 3H), 7.54-7.46 (m, 2H), 7.42 (t, J = 7.6 Hz, 3H), 4.80 (d, J = 15.4 Hz, 4H), 3.68-3.55 (m, 1H), 3.53-3.36 (m, 1H), 3.20 (ddd, J = 9.8, 7.1, 5.7 Hz, 1H), 2.06-1.87 (m, 2H), 1.76-1.58 (m, 2H), 1.31-1.18 (m, 2H) | (ESI (+)) m/e 470 (M + H)⁺ |

-continued

| Ex | Name | $^1$H NMR | MS |
|---|---|---|---|
| 924 | N-[4-({[1-(tetrahydrofuran-3-ylcarbonyl)pyrrolidin-3-yl]methyl}carbamoyl)phenyl]-1,3-dihydro-2H-pyrrolo[3,4-c]pyridine-2-carboxamide | $^1$H NMR (300 MHz, DMSO-d$_6$) δ 8.63 (d, J = 12.1 Hz, 2H), 8.50 (d, J = 5.0 Hz, 1H), 8.41 (s, 1H), 7.78 (d, J = 8.8 Hz, 2H), 7.66 (d, J = 8.1 Hz, 2H), 7.44 (d, J = 5.0 Hz, 1H), 4.83 (d, J = 4.3 Hz, 4H), 3.88 (t, J = 8.1 Hz, 1H), 3.77-3.59 (m, 4H), 3.52-3.40 (m, 1H), 3.27-3.06 (m, 2H), 2.40 (dd, J = 13.9, 6.8 Hz, 1H), 2.07-1.90 (m, 3H), 1.78-1.55 (m, 1H), 1.23 (dd, J = 9.7, 6.6 Hz, 1H) | (ESI (+)) m/e 464 (M + H)$^+$ |
| 925 | N-[4-({[1-(methylsulfonyl)pyrrolidin-3-yl]methyl}carbamoyl)phenyl]-1,3-dihydro-2H-pyrrolo[3,4-c]pyridine-2-carboxamide | $^1$H NMR (300 MHz, DMSO-d$_6$) δ 8.66 (s, 1H), 8.62 (s, 1H), 8.51 (d, J = 5.0 Hz, 1H), 8.42 (t, J = 5.7 Hz, 1H), 7.82-7.74 (m, 2H), 7.70-7.63 (m, 2H), 7.44 (d, J = 5.1 Hz, 1H), 4.86-4.79 (m, 4H), 3.25-3.11 (m, 2H), 3.02 (dd, J = 10.0, 6.7 Hz, 1H), 2.90 (s, 3H), 2.06-1.89 (m, 2H), 1.75-1.59 (m, 2H), 1.28-1.20 (m, 2H) | (ESI (+)) m/e 444 (M + H)$^+$ |
| 939 | N-[4-({[1-(morpholin-4-yl)cyclopentyl]methyl}carbamoyl)phenyl]-1,3-dihydro-2H-pyrrolo[3,4-c]pyridine-2-carboxamide | $^1$H NMR (300 MHz, DMSO-d$_6$) δ 9.35 (s, 1H), 8.77 (s, 1H), 8.72 (s, 1H), 8.60 (d, J = 5.3 Hz, 2H), 7.84 (d, J = 8.8 Hz, 2H), 7.71 (d, J = 8.8 Hz, 2H), 7.61 (d, J = 5.2 Hz, 1H), 4.88 (s, 4H), 4.03 (d, J = 11.7 Hz, 3H), 3.79-3.57 (m, 5H), 3.51 (d, J = 11.5 Hz, 2H), 3.38 (d, J = 9.6 Hz, 2H), 1.95 (d, J = 6.9 Hz, 4H), 1.74 (s, 4H) | (ESI (+)) m/e 451 (M + H)$^+$ |
| 969 | N-(4-{[(1S)-1-(4-fluorophenyl)-2-hydroxyethyl]carbamoyl}phenyl)-1,3-dihydro-2H-pyrrolo[3,4-c]pyridine-2-carboxamide | $^1$H NMR (300 MHz, DMSO-d$_6$) δ 8.66 (s, 1H), 8.62 (s, 1H), 8.50 (d, J = 9.6 Hz, 2H), 7.87-7.80 (m, 2H), 7.71-7.64 (m, 2H), 7.47-7.38 (m, 3H), 7.14 (t, J = 8.7 Hz, 2H), 5.12-5.00 (m, 1H), 4.91 (t, J = 5.8 Hz, 1H), 4.83 (d, J = 4.4 Hz, 4H), 3.76-3.57 (m, 2H) | (ESI (+)) m/e 421 (M + H)$^+$ |
| 970 | N-(4-{[(1S)-2-hydroxy-1-(4-methoxyphenyl)ethyl]carbamoyl}phenyl)-1,3-dihydro-2H-pyrrolo[3,4-c]pyridine-2-carboxamide | $^1$H NMR (300 MHz, DMSO-d$_6$) δ 8.63 (d, J = 10.4 Hz, 2H), 8.49 (t, J = 7.8 Hz, 1H), 8.41 (d, J = 8.2 Hz, 1H), 7.83 (d, J = 8.8 Hz, 2H), 7.67 (d, J = 8.8 Hz, 2H), 7.44 (d, J = 5.1 Hz, 1H), 7.36-7.25 (m, 2H), 6.92-6.82 (m, 2H), 5.01 (dd, J = 13.7, 7.9 Hz, 1H), 4.84 (t, J = 5.7 Hz, 4H), 3.72 (s, 3H), 3.70-3.57 (m, 3H) | (ESI (+)) m/e 433 (M + H)$^+$ |
| 971 | N-[4-({[3-(hydroxymethyl)oxetan-3-yl]methyl}carbamoyl)phenyl]-1,3-dihydro-2H-pyrrolo[3,4-c]pyridine-2-carboxamide | $^1$H NMR (300 MHz, DMSO-d$_6$) δ 8.67 (s, 1H), 8.62 (s, 1H), 8.51 (d, J = 5.1 Hz, 1H), 8.49-8.41 (m, 1H), 7.83-7.76 (m, 2H), 7.71-7.64 (m, 2H), 7.44 (d, J = 5.1 Hz, 1H), 4.93-4.86 (m, 1H), 4.84 (t, J = 7.0 Hz, 2H), 4.40 (d, J = 5.9 Hz, 2H), 4.29 (d, J = 5.8 Hz, 2H), 3.58 (d, J = 5.6 Hz, 2H), 3.51 (d, J = 6.0 Hz, 2H) | (ESI (+)) m/e 383 (M + H)$^+$ |
| 972 | N-(4-{[(1S)-1-(1,3-benzodioxol-5-yl)-2-hydroxyethyl]carbamoyl}phenyl)-1,3-dihydro-2H-pyrrolo[3,4-c]pyridine-2-carboxamide | $^1$H NMR (300 MHz, DMSO-d$_6$) δ 8.70-8.57 (m, 2H), 8.54-8.46 (m, 1H), 8.43-8.27 (m, 1H), 7.87-7.77 (m, 2H), 7.67 (d, J = 8.8 Hz, 2H), 7.49-7.38 (m, 1H), 6.99 (s, 1H), 6.84 (d, J = 0.8 Hz, 2H), 5.96 (dd, J = 2.5, 0.8 Hz, 2H), 5.04-4.94 (m, 1H), 4.89-4.75 (m, 4H), 3.73-3.53 (m, 2H) | (ESI (+)) m/e 447 (M + H)$^+$ |
| 1055 | N-[4-(1,7-diazaspiro[4.4]non-7-ylcarbonyl)phenyl]-1,3-dihydro-2H-pyrrolo[3,4-c]pyridine-2-carboxamide | $^1$H NMR (400 MHz, Pyridine-d$_5$) δ ppm 8.44 (d, J = 20.6 Hz, 1H), 7.88 (t, J = 10.7 Hz, 3H), 7.69-7.57 (m, 3H), 4.22 (d, J = 12.3 Hz, 1H), 3.93 (dt, J = 11.3, 8.0 Hz, 2H), 3.83-3.64 (m, 3H), 3.59-3.46 (m, 3H), 3.45-3.31 (m, 1H), 2.71-2.46 (m, 1H), 2.12-1.80 (m, 8H) | (ESI (+)) m/e 392 (M + H)$^+$ |
| 1056 | N-[4-(2,7-diazaspiro[4.5]dec-2-ylcarbonyl)phenyl]-1,3-dihydro-2H-pyrrolo[3,4-c]pyridine-2-carboxamide | $^1$H NMR (400 MHz, Pyridine-d$_5$) δ ppm 8.55 (dd, J = 10.2, 5.1 Hz, 2H), 7.99-7.83 (m, 2H), 7.70-7.61 (m, 2H), 7.10 (d, J = 4.9 Hz, 1H), 4.99-4.79 (m, 4H), 3.74-3.59 (m, 4H), 3.28-3.10 (m, 4H), 2.13-1.91 (m, 1H), 1.91-1.72 (m, 2H), 1.71-1.60 (m, 1H), 1.64-1.45 (m, 2H) | (ESI (+)) m/e 406 (M + H)$^+$ |
| 1057 | N-[4-(2,6-diazaspiro[4.5]dec-2-ylcarbonyl)phenyl]-1,3-dihydro-2H-pyrrolo[3,4-c]pyridine-2-carboxamide | $^1$H NMR (400 MHz, Pyridine-d$_5$) δ ppm 8.58-8.47 (m, 2H), 7.85 (t, J = 24.8 Hz, 2H), 7.67-7.57 (m, 2H), 7.10 (d, J = 4.9 Hz, 1H), 4.91-4.74 (m, 4H), 4.30 (d, J = 12.6 Hz, 1H), 3.98-3.72 (m, 2H), 3.68-3.58 (m, 1H), 3.27-3.05 (m, 2H), 2.61-2.45 (m, 1H), 2.16-1.92 (m, 1H), 1.92-1.77 (m, 2H), 1.72-1.19 (m, 4H) | (ESI (+)) m/e 406 (M + H)$^+$ |

-continued

| Ex | Name | $^1$H NMR | MS |
|---|---|---|---|
| 1058 | N-[4-(2,7-diazaspiro[4.5]dec-7-ylcarbonyl)phenyl]-1,3-dihydro-2H-pyrrolo[3,4-c]pyridine-2-carboxamide | $^1$H NMR (400 MHz, Pyridine-d$_5$) δ ppm 8.60-8.49 (m, 2H), 8.09-7.83 (m, 2H), 7.53-7.42 (m, 3H), 5.06-4.76 (m, 4H), 3.78-3.57 (m, 3H), 3.48-3.23 (m, 4H), 2.08-1.91 (m, 1H), 1.91-1.76 (m, 1H), 1.76-1.65 (m, 1H), 1.61 (dt, J = 23.9, 13.1 Hz, 1H), 1.56-1.34 (m, 2H) | (ESI (+)) m/e 406 (M + H)$^+$ |
| 1059 | N-[4-(2,9-diazaspiro[5.5]undec-2-ylcarbonyl)phenyl]-1,3-dihydro-2H-pyrrolo[3,4-c]pyridine-2-carboxamide | $^1$H NMR (400 MHz, Pyridine-d$_5$) δ ppm 8.62-8.46 (m, 2H), 7.85 (dd, J = 43.4, 8.8 Hz, 2H), 7.52-7.43 (m, 2H), 7.10 (d, J = 4.9 Hz, 1H), 3.90-3.70 (m, 1H), 3.60-3.43 (m, 3H), 3.41-3.25 (m, 1H), 3.24-3.03 (m, 4H), 1.89-1.56 (m, 4H), 1.54-1.31 (m, 4H) | (ESI (+)) m/e 420 (M + H)$^+$ |
| 1060 | N-[4-(2,8-diazaspiro[5.5]undec-2-ylcarbonyl)phenyl]-1,3-dihydro-2H-pyrrolo[3,4-c]pyridine-2-carboxamide | $^1$H NMR (400 MHz, Pyridine-d$_5$) δ ppm 8.56 (dd, J = 9.9, 4.6 Hz, 2H), 8.12-7.80 (m, 2H), 7.52-7.43 (m, 3H), 4.90-4.83 (m, 6H), 3.67-3.55 (m, 2H), 3.49-3.37 (m, 2H), 3.41-3.23 (m, 4H), 1.99-1.61 (m, 4H), 1.47 (d, J = 10.4 Hz, 4H) | (ESI (+)) m/e 420 (M + H)$^+$ |
| 1061 | N-[4-(1,8-diazaspiro[5.5]undec-8-ylcarbonyl)phenyl]-1,3-dihydro-2H-pyrrolo[3,4-c]pyridine-2-carboxamide | $^1$H NMR (400 MHz, Pyridine-d$_5$) δ ppm 8.60-8.44 (m, 2H), 7.86 (t, J = 25.2 Hz, 2H), 7.54 (t, J = 6.9 Hz, 2H), 7.10 (d, J = 4.9 Hz, 1H), 4.14 (d, J = 13.5 Hz, 1H), 4.02 (d, J = 13.5 Hz, 1H), 3.59 (dd, J = 11.5, 6.5 Hz, 1H), 3.48-3.33 (m, 1H), 3.36-3.13 (m, 2H), 2.23 (ddd, J = 13.3, 8.9, 4.3 Hz, 1H), 1.96-1.82 (m, 2H), 1.83-1.65 (m, 4H), 1.69-1.44 (m, 4H) | (ESI (+)) m/e 420 (M + H)$^+$ |
| 1062 | N-[4-(1,8-diazaspiro[4.6]undec-8-ylcarbonyl)phenyl]-1,3-dihydro-2H-pyrrolo[3,4-c]pyridine-2-carboxamide | $^1$H NMR (400 MHz, Pyridine-d$_5$) δ ppm 8.50 (dd, J = 43.2, 14.6 Hz, 2H), 7.98-7.82 (m, 2H), 7.52-7.41 (m, 2H), 7.10 (d, J = 4.9 Hz, 1H), 3.95-3.75 (m, 1H), 3.67 (d, J = 9.3 Hz, 2H), 3.51-3.37 (m, 6H), 2.52-2.33 (m, 1H), 2.25-2.11 (m, 2H), 2.12-1.99 (m, 1H), 2.03-1.83 (m, 6H), 1.66 (d, J = 41.1 Hz, 1H) | (ESI (+)) m/e 420 (M + H)$^+$ |
| 1063 | N-{4-[(1-oxa-8-azaspiro[4.5]dec-2-ylmethyl)carbamoyl]phenyl}-1,3-dihydro-2H-pyrrolo[3,4-c]pyridine-2-carboxamide | $^1$H NMR (400 MHz, Pyridine-d$_5$) δ ppm 8.61-8.44 (m, 2H), 8.18-8.03 (m, 2H), 7.98-7.81 (m, 2H), 7.10 (d, J = 4.9 Hz, 1H) 4.89-4.79 (m, 6H), 4.28 (dt, J = 12.4, 6.2 Hz, 1H), 3.80-3.64 (m, 2H), 3.51 (s, 1H), 3.45-3.25 (m, 4H), 2.12-1.89 (m, 2H), 1.87-1.48 (m, 4H) | (ESI (+)) m/e 436 (M + H)$^+$ |
| 1064 | N-[4-(1-oxa-8-azaspiro[4.5]dec-3-ylcarbamoyl)phenyl]-1,3-dihydro-2H-pyrrolo[3,4-c]pyridine-2-carboxamide | $^1$H NMR (400 MHz, Pyridine-d$_5$) δ ppm 8.44 (d, J = 20.6 Hz, 1H), 7.88 (t, J = 10.7 Hz, 3H), 7.69-7.57 (m, 3H), 4.22 (d, J = 12.3 Hz, 1H), 3.93 (dt, J = 11.3, 8.0 Hz, 2H), 3.83-3.64 (m, 3H), 3.59-3.46 (m, 3H), 3.45-3.31 (m, 1H), 2.71-2.46 (m, 1H), 2.12-1.80 (m, 8H) | (ESI (+)) m/e 422 (M + H)$^+$ |
| 1065 | N-{4-[(2-oxa-9-azaspiro[5.5]undec-3-ylmethyl)carbamoyl]phenyl}-1,3-dihydro-2H-pyrrolo[3,4-c]pyridine-2-carboxamide | $^1$H NMR (400 MHz, Pyridine-d$_5$) δ ppm 8.56-8.44 (m, 2H), 8.26-8.00 (m, 3H), 7.87 (dd, J = 40.3, 8.7 Hz, 2H), 3.99-3.70 (m, 2H), 3.66-3.56 (m, 2H), 3.51 (s, 1H), 3.35-3.16 (m, 4H), 3.10 (d, J = 11.5 Hz, 1H), 2.09-1.82 (m, 2H), 1.83-1.68 (m, 1H), 1.61-1.36 (m, 4H), 1.33-1.05 (m, 1H) | (ESI (+)) m/e 450 (M + H)$^+$ |
| 1066 | N-[4-(1-oxa-4,8-diazaspiro[5.5]undec-4-ylcarbonyl)phenyl]-1,3-dihydro-2H-pyrrolo[3,4-c]pyridine-2-carboxamide | $^1$H NMR (400 MHz, Pyridine-d$_5$) δ ppm 8.62-8.46 (m, 2H), 7.86 (dd, J = 52.3, 8.6 Hz, 3H), 7.56 (d, J = 15.9 Hz, 2H), 4.94-4.73 (m, 5H), 3.81-3.52 (m, 6H), 3.37 (d, J = 12.4 Hz, 1H), 3.17-2.87 (m, 2H), 2.13-1.83 (m, 2H), 1.63-1.24 (m, 2H) | (ESI (+)) m/e 422 (M + H)$^+$ |
| 1067 | N-[4-(1,8-diazaspiro[4.5]dec-1-ylcarbonyl)phenyl]-1,3-dihydro-2H-pyrrolo[3,4-c]pyridine-2-carboxamide | $^1$H NMR (400 MHz, Pyridine-d$_5$) δ ppm 8.59-8.45 (m, 2H), 7.96-7.80 (m, 2H), 7.59-7.52 (m, 2H), 7.10 (d, J = 4.9 Hz, 1H), 4.87 (d, J = 6.5 Hz, 6H), 3.54 (dt, J = 13.2, 4.8 Hz, 4H), 3.41 (dd, J = 9.0, 4.4 Hz, 2H), 3.28-3.12 (m, 2H), 2.03-1.86 (m, 2H), 1.74-1.46 (m, 4H) | (ESI (+)) m/e 406 (M + H)$^+$ |
| 1068 | N-[4-(1,8-diazaspiro[4.5]dec-8-ylcarbonyl)phenyl]-1,3-dihydro-2H-pyrrolo[3,4-c]pyridine-2-carboxamide | $^1$H NMR (400 MHz, Pyridine-d$_5$) δ ppm 8.50 (dd, J = 44.5, 13.2 Hz, 2H), 7.88 (d, J = 8.5 Hz, 2H), 7.50 (d, J = 8.6 Hz, 2H), 7.10 (d, J = 4.9 Hz, 1H), 4.14-3.91 (m, 2H), 3.66-3.34 (m, 6H), 2.43 (s, 1H), 2.23-2.05 (m, 2H), 2.05-1.66 (m, 8H) | (ESI (+)) m/e 406 (M + H)$^+$ |
| 1069 | N-[4-(1,7-diazaspiro[3.5]non-7-ylcarbonyl)phenyl]-1,3-dihydro-2H-pyrrolo[3,4-c]pyridine-2-carboxamide | $^1$H NMR (400 MHz, Pyridine-d$_5$) δ ppm 8.59-8.43 (m, 2H), 7.90 (d, J = 8.5 Hz, 2H), 7.48 (t, J = 13.3 Hz, 3H), 4.90 (dd, J = 29.4, 12.8 Hz, 4H), 4.01 (d, J = 47.2 Hz, 2H), 3.61 (t, J = 5.7 Hz, 2H), 3.51 (s, 2H), 3.37 (t, J = 7.4 Hz, 2H), 2.61 (t, J = 7.3 Hz, 2H), 2.10 (s, 2H) | (ESI (+)) m/e 392 (M + H)$^+$ |

| Ex | Name | ¹H NMR | MS |
|---|---|---|---|
| 1070 | N-[4-(1,6-diazaspiro[3.5]non-1-ylcarbonyl)phenyl]-1,3-dihydro-2H-pyrrolo[3,4-c]pyridine-2-carboxamide | ¹H NMR (400 MHz, Pyridine-$d_5$) δ ppm 8.56 (d, J = 6.6 Hz, 2H), 8.05-7.86 (m, 2H), 7.82-7.62 (m, 2H), 7.10 (d, J = 4.9 Hz, 1H), 4.98-4.75 (m, 4H), 4.27 (td, J = 8.9, 6.8 Hz, 1H), 3.96 (ddd, J = 25.0, 14.5, 9.4 Hz, 3H), 3.51 (d, J = 6.5 Hz, 1H), 3.44 (t, J = 9.6 Hz, 1H), 3.23 (tdd, J = 12.8, 11.1, 4.3 Hz, 2H), 2.58-2.45 (m, 1H), 2.39-2.19 (m, 1H), 1.97 (ddd, J = 11.3, 9.0, 5.2 Hz, 2H), 1.89-1.63 (m, 2H) | (ESI (+)) m/e 392 (M + H)⁺ |
| 1071 | N-[4-(2,5-diazaspiro[3.5]non-2-ylcarbonyl)phenyl]-1,3-dihydro-2H-pyrrolo[3,4-c]pyridine-2-carboxamide | ¹H NMR (400 MHz, Pyridine-$d_5$) δ ppm 8.59-8.44 (m, 2H), 7.90 (d, J = 8.7 Hz, 2H), 7.84-7.67 (m, 2H), 7.10 (d, J = 4.9 Hz, 1H), 4.89 (dd, J = 31.4, 12.8 Hz, 4H), 4.38 (d, J = 9.7 Hz, 2H), 4.29-4.03 (m, 2H), 3.51 (s, 1H), 3.12-2.82 (m, 2H), 2.01-1.69 (m, 2H), 1.62-1.22 (m, 4H) | (ESI (+)) m/e 392 (M + H)⁺ |
| 1072 | N-[4-(5-oxa-2-azaspiro[3.4]oct-2-ylcarbonyl)phenyl]-1,3-dihydro-2H-pyrrolo[3,4-c]pyridine-2-carboxamide | ¹H NMR (400 MHz, Pyridine-$d_5$) δ ppm 8.60-8.44 (m, 3H), 7.99-7.85 (m, 2H), 7.85-7.74 (m, 2H), 7.10 (d, J = 4.9 Hz, 1H), 4.98-4.74 (m, 4H), 4.41-4.24 (m, 3H), 4.19 (dd, J = 9.6, 1.2 Hz, 2H), 3.85-3.61 (m, 2H), 1.92 (t, J = 7.3 Hz, 2H), 1.80-1.54 (m, 2H) | (ESI (+)) m/e 379 (M + H)⁺ |
| 1073 | N-[4-(6-oxa-2-azaspiro[3.5]non-2-ylcarbonyl)phenyl]-1,3-dihydro-2H-pyrrolo[3,4-c]pyridine-2-carboxamide | ¹H NMR (400 MHz, Pyridine-$d_5$) δ ppm 8.58-8.43 (m, 2H), 7.91 (dd, J = 21.0, 8.7 Hz, 2H), 7.85 (t, J = 7.0 Hz, 2H), 7.11 (d, J = 4.9 Hz, 1H), 4.88 (t, J = 13.2 Hz, 4H), 4.04-3.91 (m, 2H), 3.91-3.76 (m, 2H), 3.62-3.54 (m, 2H), 3.54-3.36 (m, 2H), 1.77-1.52 (m, 2H), 1.52-1.27 (m, 2H) | (ESI (+)) m/e 393 (M + H)⁺ |
| 1074 | N-[4-(hexahydro-5H-furo[2,3-c]pyrrol-5-ylcarbonyl)phenyl]-1,3-dihydro-2H-pyrrolo[3,4-c]pyridine-2-carboxamide | ¹H NMR (400 MHz, Pyridine-$d_5$) δ ppm 8.57-8.46 (m, 2H), 7.98-7.76 (m, 2H), 7.69-7.57 (m, 2H), 7.10 (s, 1H), 4.86 (dd, J = 17.1, 10.2 Hz, 4H), 4.39 (t, J = 5.6 Hz, 1H), 3.98-3.81 (m, 2H), 3.74-3.54 (m, 4H), 3.56-3.41 (m, 1H), 2.78-2.51 (m, 1H), 2.07-1.72 (m, 1H), 1.73-1.36 (m, 1H) | (ESI (+)) m/e 379 (M + H)⁺ |
| 1075 | N-[4-(tetrahydro-1H-furo[3,4-c]pyrrol-5(3H)-ylcarbonyl)phenyl]-1,3-dihydro-2H-pyrrolo[3,4-c]pyridine-2-carboxamide | ¹H NMR (400 MHz, Pyridine-$d_5$) δ ppm 8.59-8.46 (m, 2H), 7.90 (d, J = 8.6 Hz, 2H), 7.68-7.58 (m, 2H), 7.10 (d, J = 5.0 Hz, 1H), 4.87 (dd, J = 16.8, 9.9 Hz, 4H), 3.86-3.64 (m, 4H), 3.64-3.40 (m, 5H), 2.86-2.58 (m, 2H) | (ESI (+)) m/e 379 (M + H)⁺ |
| 1076 | N-[4-(hexahydrofuro[3,4-c]pyridin-5(3H)-ylcarbonyl)phenyl]-1,3-dihydro-2H-pyrrolo[3,4-c]pyridine-2-carboxamide | ¹H NMR (400 MHz, Pyridine-$d_5$) δ ppm 8.62-8.45 (m, 2H), 8.01-7.80 (m, 2H), 7.57-7.52 (m, 2H), 7.10 (d, J = 5.1 Hz, 1H), 4.91-4.78 (m, 4H), 3.83-3.69 (m, 2H), 3.74-3.55 (m, 6H), 3.45-3.26 (m, 1H), 2.37-2.17 (m, 2H), 1.72-1.35 (m, 2H) | (ESI (+)) m/e 393 (M + H)⁺ |
| 1120 | N-(4-{[3-(5-methyl-1H-pyrazol-1-yl)propyl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.47 (d, J = 4.9 Hz, 1H), 7.80 (d, J = 7.7 Hz, 1H), 7.78-7.70 (m, 2H), 7.70-7.54 (m, 2H), 7.42-7.09 (m, 2H), 6.01 (d, J = 0.8 Hz, 1H), 4.81 (d, J = 11.5 Hz, 4H), 4.08 (t, J = 7.0 Hz, 2H), 3.32-3.27 (m, 2H), 2.25 (s, 3H), 2.12-1.94 (m, 2H) | (ESI (+)) m/e 405 (M + H)⁺ |
| 1121 | N-(4-{[2-(4-chloro-1H-pyrazol-1-yl)ethyl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.52-8.38 (m, 1H), 7.87-7.76 (m, 2H), 7.73-7.66 (m, 2H), 7.66-7.55 (m, 2H), 7.54-7.39 (m, 1H), 7.38-7.22 (m, 1H), 4.95-4.64 (m, 4H), 4.28 (dd, J = 8.0, 4.5 Hz, 2H), 3.79-3.50 (m, 2H) | (ESI (+)) m/e 411 (M + H)⁺ |
| 1122 | N-(4-{[1-(3,5-dimethyl-1H-pyrazol-1-yl)propan-2-yl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.47 (t, J = 9.6 Hz, 1H), 7.91-7.78 (m, 1H), 7.79-7.68 (m, 2H), 7.68-7.57 (m, 2H), 7.38-7.31 (m, 1H), 4.82 (d, J = 8.8 Hz, 4H), 4.37 (h, J = 6.7 Hz, 1H), 4.24-3.93 (m, 2H), 2.89-2.68 (m, 1H), 2.63-2.42 (m, 2H), 2.13 (s, 3H), 1.96 (s, 1H), 1.27-1.02 (m, 3H) | (ESI (+)) m/e 419 (M + H)⁺ |
| 1123 | N-(4-{[2-methyl-2-(morpholin-4-yl)butyl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.47 (d, J = 4.8 Hz, 1H), 7.81 (dd, J = 10.0, 8.1 Hz, 3H), 7.75-7.60 (m, 2H), 7.46-7.25 (m, 1H), 4.81 (d, J = 12.8 Hz, 4H), 3.92 (s, 4H), 3.40 (s, 3H), 2.85 (dd, J = 84.9, 29.4 Hz, 2H), 2.57-2.38 (m, 3H), 1.92 (d, J = 35.3 Hz, 1H), 1.87-1.66 (m, 2H), 1.02 (t, J = 7.4 Hz, 3H) | (ESI (+)) m/e 438 (M + H)⁺ |

-continued

| Ex | Name | ¹H NMR | MS |
|---|---|---|---|
| 1124 | N-{4-[(4-methoxybenzyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.55-8.39 (m, 1H), 7.98-7.71 (m, 3H), 7.67-7.52 (m, 2H), 7.36-7.29 (m, 1H), 7.29-7.17 (m, 2H), 6.98-6.73 (m, 2H), 4.90-4.60 (m, 4H), 4.38 (d, J = 17.5 Hz, 2H), 3.74 (d, J = 3.2 Hz, 3H) | (ESI (+)) m/e 403 (M + H)⁺ |
| 1125 | N-(4-{[3-(morpholin-4-yl)propyl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.57-8.35 (m, 1H), 7.89-7.72 (m, 3H), 7.72-7.54 (m, 2H), 7.33 (dd, J = 7.7, 5.0 Hz, 1H), 4.81 (d, J = 11.8 Hz, 4H), 3.86 (s, 4H), 3.47-3.34 (m, 2H), 3.24-3.04 (m, 2H), 2.12-1.78 (m, 2H) | (ESI (+)) m/e 410 (M + H)⁺ |
| 1126 | N-[4-({4-[2-(2-hydroxyethoxy)ethyl]piperazin-1-yl}carbonyl)phenyl]-5,7-dihydro-6H-pyrrolo[3,4-b]pyridine-6-carboxamide | ¹H NMR (400 MHz, DMSO-$d_6$, Temp = 90° C.) δ 8.46 (dd, J = 12.7, 2.9 Hz, 1H), 7.80 (d, J = 7.7 Hz, 1H), 7.73-7.55 (m, 2H), 7.49-7.35 (m, 2H), 7.35-7.25 (m, 1H), 4.81 (d, J = 11.4 Hz, 4H), 3.90-3.71 (m, 6H), 3.66-3.48 (m, 5H), 3.37 (d, J = 5.2 Hz, 5H), 2.88 (d, J = 53.2 Hz, 4H), 1.96 (s, 2H) | (ESI (+)) m/e 440 (M + H)⁺ |
| 1127 | N-{4-[(2-carbamoylbenzyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.46 (d, J = 4.3 Hz, 1H), 7.84-7.73 (m, 3H), 7.73-7.59 (m, 2H), 7.48 (d, J = 7.4 Hz, 1H), 7.44-7.37 (m, 2H), 7.37-7.20 (m, 2H), 4.81 (d, J = 12.6 Hz, 4H), 4.63 (s, 2H) | (ESI (+)) m/e 416 (M + H)⁺ |
| 1128 | N-{4-[bis(2-methoxyethyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.65-8.37 (m, 1H), 7.78 (dd, J = 40.2, 6.3 Hz, 1H), 7.68-7.53 (m, 2H), 7.42-7.31 (m, 1H), 7.32-7.20 (m, 2H), 4.85 (t, J = 26.3 Hz, 4H), 3.67-3.41 (m, 9H), 3.28 (t, J = 8.4 Hz, 6H), 3.06-2.71 (m, 2H), 2.01 (d, J = 38.9 Hz, 1H) | (ESI (+)) m/e 399 (M + H)⁺ |
| 1129 | N-{4-[(1-amino-1-oxohexan-2-yl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.59-8.22 (m, 1H), 7.89-7.75 (m, 3H), 7.70-7.54 (m, 2H), 7.37 (dd, J = 7.7, 5.0 Hz, 1H), 4.83 (d, J = 8.7 Hz, 4H), 4.41 (dd, J = 8.6, 5.5 Hz, 1H), 3.11-2.72 (m, 1H), 2.53-2.31 (m, 1H), 1.90-1.56 (m, 2H), 1.48-1.22 (m, 4H), 1.11-0.77 (m, 3H) | (ESI (+)) m/e 394 (M + H)⁺ |
| 1130 | N-(4-{[2-(3,4-dimethoxyphenyl)ethyl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.55-8.34 (m, 1H), 7.87-7.75 (m, 1H), 7.76-7.67 (m, 2H), 7.67-7.52 (m, 2H), 7.45-7.26 (m, 1H), 6.94-6.79 (m, 2H), 6.77 (dd, J = 8.1, 2.0 Hz, 1H), 4.90-4.61 (m, 4H), 3.73 (d, J = 2.9 Hz, 6H), 3.63-3.35 (m, 2H), 2.87-2.66 (m, 2H) | (ESI (+)) m/e 447 (M + H)⁺ |
| 1131 | N-(4-{[4-(pyrazin-2-yl)piperazin-1-yl]carbonyl}phenyl)-5,7-dihydro-6H-pyrrolo[3,4-b]pyridine-6-carboxamide | ¹H NMR (400 MHz, DMSO-$d_6$, Temp = 90° C.) δ 8.31-8.22 (m, 1H), 8.12-8.04 (m, 1H), 7.90-7.59 (m, 4H), 7.43-7.30 (m, 3H), 4.87-4.75 (m, 4H), 3.69-3.60 (m, 8H) | (ESI (+)) m/e 430 (M + H)⁺ |
| 1132 | Nalpha-{4-[(5,7-dihydro-6H-pyrrolo[3,4-b]pyridin-6-ylcarbonyl)amino]benzoyl}-L-phenylalaninamide | ¹H NMR (400 MHz, DMSO-$d_6$, Temp = 90° C.) δ 8.57-8.27 (m, 1H), 7.83-7.74 (m, 1H), 7.74-7.64 (m, 2H), 7.64-7.54 (m, 2H), 7.39-7.20 (m, 5H), 7.20-7.09 (m, 1H), 4.88-4.73 (m, 4H), 4.73-4.58 (m, 1H), 3.22-3.11 (m, 1H), 3.11-2.92 (m, 1H) | (ESI (+)) m/e 430 (M + H)⁺ |
| 1133 | N-(4-{[(2R)-1-amino-4-methyl-1-oxopentan-2-yl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.61-8.35 (m, 1H), 7.96-7.73 (m, 3H), 7.71-7.53 (m, 2H), 7.47-7.28 (m, 1H), 4.94-4.67 (m, 4H), 4.61-4.34 (m, 1H), 3.08-2.71 (m, 1H), 1.93-1.49 (m, 2H), 1.00-0.70 (m, 6H) | (ESI (+)) m/e 396 (M + H)⁺ |
| 1134 | N-{4-[(4-cyclohexylpiperazin-1-yl)carbonyl]phenyl}-5,7-dihydro-6H-pyrrolo[3,4-b]pyridine-6-carboxamide | ¹H NMR (400 MHz, DMSO-$d_6$, Temp = 90° C.) δ 8.48 (d, J = 4.6 Hz, 1H), 7.91-7.76 (m, 1H), 7.75-7.57 (m, 2H), 7.50-7.27 (m, 3H), 4.86 (t, J = 26.6 Hz, 4H), 3.80 (s, 3H), 3.28-3.13 (m, 2H), 3.05-2.73 (m, 3H), 2.70-2.43 (m, 1H), 2.09 (d, J = 11.0 Hz, 2H), 1.84 (t, J = 13.9 Hz, 2H), 1.64 (d, J = 12.9 Hz, 1H), 1.48-1.22 (m, 4H), 1.22-1.04 (m, 1H) | (ESI (+)) m/e 434 (M + H)⁺ |
| 1135 | N-{4-[(3-tert-butoxypropyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.48 (d, J = 4.4 Hz, 1H), 7.80 (t, J = 17.2 Hz, 1H), 7.76-7.65 (m, 2H), 7.68-7.52 (m, 2H), 7.36 (dd, J = 7.7, 5.0 Hz, 1H), 4.82 (d, J = 9.6 Hz, 4H), 3.48-3.33 (m, 3H), 1.73 (p, J = 6.5 Hz, 2H), 1.15 (s, 9H) | (ESI (+)) m/e 394 (M + H)⁺ |

-continued

| Ex | Name | ¹H NMR | MS |
|---|---|---|---|
| 1136 | N-(4-{[2-(2,6-dimethylmorpholin-4-yl)ethyl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.47 (d, J = 5.0 Hz, 1H), 7.89-7.72 (m, 3H), 7.70-7.53 (m, 2H), 7.48-7.18 (m, 1H), 4.87 (dd, J = 42.6, 12.8 Hz, 4H), 3.97-3.75 (m, 2H), 3.75-3.58 (m, 2H), 3.53 (d, J = 12.0 Hz, 2H), 3.00-2.80 (m, 1H), 2.73 (t, J = 11.7 Hz, 2H), 2.51 (dt, J = 3.7, 1.8 Hz, 2H), 1.18 (d, J = 6.3 Hz, 6H) | (ESI (+)) m/e 424 (M + H)⁺ |
| 1137 | N-{4-[(3-methoxybenzyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.52-8.30 (m, 1H), 7.89-7.70 (m, 3H), 7.70-7.48 (m, 2H), 7.34 (dd, J = 7.7, 5.0 Hz, 1H), 7.23 (t, J = 8.0 Hz, 1H), 6.99-6.84 (m, 2H), 6.86-6.69 (m, 1H), 4.82 (d, J = 10.4 Hz, 4H), 4.45 (s, 2H), 3.75 (s, 3H), 1.96 (s, 1H) | (ESI (+)) m/e 403 (M + H)⁺ |
| 1138 | N-(4-{[2-methyl-2-(morpholin-4-yl)propyl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.45 (t, J = 21.3 Hz, 1H), 7.89-7.74 (m, 3H), 7.80-7.58 (m, 2H), 7.34 (dd, J = 7.7, 5.0 Hz, 1H), 4.82 (d, J = 11.1 Hz, 4H), 3.92 (s, 4H), 3.64 (s, 2H), 3.39 (s, 3H), 1.39 (s, 6H) | (ESI (+)) m/e 424 (M + H)⁺ |
| 1139 | N-(4-{[(3S)-1-methyl-2-oxoazepan-3-yl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.64-8.35 (m, 1H), 7.87-7.78 (m, 1H), 7.78-7.71 (m, 1H), 7.71-7.59 (m, 2H), 7.47-7.28 (m, 1H), 4.99-4.68 (m, 4H), 3.74-3.58 (m, 1H), 3.06-2.86 (m, 3H), 2.90-2.71 (m, 1H), 2.03-1.74 (m, 4H), 1.59-1.28 (m, 2H) | (ESI (+)) m/e 408 (M + H)⁺ |
| 1140 | N-(4-{[2-(4-methylpiperazin-1-yl)ethyl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.48 (d, J = 4.4 Hz, 1H), 7.86-7.72 (m, 3H), 7.72-7.58 (m, 2H), 7.35 (dd, J = 7.7, 5.0 Hz, 1H), 4.82 (d, J = 10.5 Hz, 4H), 3.53 (t, J = 6.4 Hz, 2H), 3.32-3.22 (m, 4H), 3.20-3.02 (m, 4H), 2.97 (t, J = 6.4 Hz, 3H), 2.80 (s, 4H) | (ESI (+)) m/e 409 (M + H)⁺ |
| 1141 | N-(4-{[4-(morpholin-4-yl)benzyl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.60-8.40 (m, 1H), 7.93-7.71 (m, 3H), 7.73-7.49 (m, 2H), 7.42-7.26 (m, 1H), 7.29-7.02 (m, 2H), 6.98-6.81 (m, 2H), 4.81 (d, J = 11.8 Hz, 4H), 4.37 (d, J = 16.6 Hz, 2H), 3.89-3.61 (m, 4H), 3.18-2.93 (m, 4H), 2.98-2.74 (m, 1H) | (ESI (+)) m/e 457 (M + H)⁺ |
| 1142 | N-(4-{[3-(piperidin-1-yl)propyl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.47 (d, J = 4.2 Hz, 1H), 7.89-7.70 (m, 3H), 7.73-7.51 (m, 2H), 7.33 (dd, J = 7.7, 5.0 Hz, 1H), 4.81 (d, J = 11.5 Hz, 4H), 3.38 (dd, J = 18.6, 12.0 Hz, 4H), 3.21-3.00 (m, 2H), 2.92 (d, J = 19.7 Hz, 2H), 1.95 (tt, J = 33.3, 15.0 Hz, 3H), 1.77 (d, J = 48.7 Hz, 6H) | (ESI (+)) m/e 408 (M + H)⁺ |
| 1143 | N-[4-(4,5,6,7-tetrahydro-1H-indazol-5-ylcarbamoyl)phenyl]-5,7-dihydro-6H-pyrrolo[3,4-b]pyridine-6-carboxamide | ¹H NMR (400 MHz, DMSO-$d_6$, Temp = 90° C.) δ 8.45 (d, J = 7.5 Hz, 1H), 7.84-7.74 (m, 2H), 7.65 (dd, J = 18.3, 8.7 Hz, 2H), 7.56 (d, J = 8.7 Hz, 1H), 7.41-7.19 (m, 2H), 4.90 (s, 1H), 4.81 (d, J = 14.4 Hz, 4H), 2.87 (dd, J = 33.4, 22.8 Hz, 6H) | (ESI (+)) m/e 403 (M + H)⁺ |
| 1195 | N-{4-[(3-methoxy-2,2-dimethylpropyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.47 (t, J = 12.9 Hz, 1H), 7.85 (d, J = 7.7 Hz, 1H), 7.79-7.69 (m, 2H), 7.69-7.57 (m, 2H), 7.38 (dd, J = 7.7, 5.0 Hz, 1H), 4.83 (d, J = 8.0 Hz, 4H), 3.30 (s, 3H), 3.21 (s, 2H), 3.15 (s, 2H), 0.90 (s, 6H) | (ESI (+)) m/e 388 (M + H)⁺ |
| 1196 | N-{4-[(3,3-dimethylbutyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.48 (d, J = 4.4 Hz, 1H), 7.82 (d, J = 7.7 Hz, 1H), 7.78-7.69 (m, 2H), 7.69-7.57 (m, 2H), 7.35 (dd, J = 7.7, 5.0 Hz, 1H), 4.82 (d, J = 10.1 Hz, 4H), 3.31 (d, J = 4.0 Hz, 1H), 3.28 (s, 1H), 1.60-1.24 (m, 2H), 0.94 (s, 9H) | (ESI (+)) m/e 367 (M + H)⁺ |
| 1197 | N-(4-{[1-(furan-2-yl)propan-2-yl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.63-8.39 (m, 1H), 7.89-7.79 (m, 1H), 7.79-7.67 (m, 2H), 7.67-7.51 (m, 2H), 7.51-7.27 (m, 1H), 6.32 (dd, J = 3.1, 1.9 Hz, 1H), 6.13 (dd, J = 3.2, 0.7 Hz, 1H), 4.86 (t, J = 25.1 Hz, 4H), 4.28 (h, J = 6.7 Hz, 1H), 3.06-2.73 (m, 4H), 1.96 (s, 1H), 1.19 (t, J = 5.9 Hz, 3H) | (ESI (+)) m/e 391 (M + H)⁺ |

| Ex | Name | ¹H NMR | MS |
|---|---|---|---|
| 1198 | N-(4-{[(3-methyl-1,2-oxazol-5-yl)methyl]carbamoyl}phenyl)-5,7-dihydro-6H-pyrrolo[3,4-b]pyridine-6-carboxamide | ¹H NMR (400 MHz, DMSO-d₆, Temp = 90° C.) δ 8.59-8.37 (m, 1H), 7.87-7.70 (m, 3H), 7.71-7.52 (m, 2H), 7.42-7.20 (m, 1H), 6.24-6.02 (m, 1H), 4.93-4.69 (m, 4H), 4.64-4.44 (m, 2H), 2.20 (s, 3H) | (ESI (+)) m/e 378 (M + H)⁺ |
| 1199 | N-(4-{[(2R)-1-cyanobutan-2-yl]carbamoyl}phenyl)-5,7-dihydro-6H-pyrrolo[3,4-b]pyridine-6-carboxamide | ¹H NMR (400 MHz, DMSO-d₆, Temp = 90° C.) δ 8.49 (t, J = 7.9 Hz, 1H), 7.96-7.83 (m, 2H), 7.71-7.54 (m, 2H), 7.39 (dd, J = 7.7, 5.1 Hz, 1H), 4.83 (d, J = 7.3 Hz, 4H), 4.27-3.97 (m, 1H), 2.89-2.62 (m, 3H), 1.97 (s, 1H), 1.68 (p, J = 7.3 Hz, 2H), 0.93 (t, J = 7.4 Hz, 3H) | (ESI (+)) m/e 364 (M + H)⁺ |
| 1200 | N-{4-[methyl(3-methylbutyl)carbamoyl]phenyl}-5,7-dihydro-6H-pyrrolo[3,4-b]pyridine-6-carboxamide | ¹H NMR (400 MHz, DMSO-d₆, Temp = 90° C.) δ 8.48 (dd, J = 5.4, 4.9 Hz, 1H), 7.84 (d, J = 7.7, 0.7 Hz, 1H), 7.72-7.50 (m, 2H), 7.47-7.32 (m, 1H), 7.34-7.16 (m, 2H), 4.86 (t, J = 25.0 Hz, 4H), 3.37 (dd, J = 14.4, 6.9 Hz, 2H), 2.97-2.84 (m, 4H), 1.97 (s, 2H), 1.66-1.33 (m, 3H), 1.06-0.63 (m, 6H) | (ESI (+)) m/e 367 (M + H)⁺ |
| 1201 | N-(4-{[(1-methyl-1H-pyrazol-3-yl)methyl]carbamoyl}phenyl)-5,7-dihydro-6H-pyrrolo[3,4-b]pyridine-6-carboxamide | ¹H NMR (400 MHz, DMSO-d₆, Temp = 90° C.) δ 8.47 (d, J = 4.9 Hz, 1H), 7.84-7.70 (m, 3H), 7.70-7.55 (m, 2H), 7.51 (t, J = 5.0 Hz, 1H), 7.32 (dd, J = 7.7, 4.9 Hz, 1H), 6.15 (d, J = 2.2 Hz, 1H), 4.85 (t, J = 28.9 Hz, 4H), 4.59-4.31 (m, 2H), 3.78 (d, J = 4.5 Hz, 3H) | (ESI (+)) m/e 377 (M + H)⁺ |
| 1202 | N-{4-[(2-methoxybutyl)carbamoyl]phenyl}-5,7-dihydro-6H-pyrrolo[3,4-b]pyridine-6-carboxamide | ¹H NMR (400 MHz, DMSO-d₆, Temp = 90° C.) δ 8.49 (d, J = 4.9 Hz, 1H), 7.85 (t, J = 10.7 Hz, 1H), 7.78-7.69 (m, 2H), 7.68-7.49 (m, 2H), 7.43-7.30 (m, 1H), 4.86 (t, J = 25.0 Hz, 4H), 3.35 (d, J = 4.6 Hz, 2H), 3.32 (d, J = 2.7 Hz, 3H), 1.71-1.34 (m, 2H), 0.90 (t, J = 7.4 Hz, 3H) | (ESI (+)) m/e 369 (M + H)⁺ |
| 1203 | N-(4-{[4-(dimethylamino)butyl]carbamoyl}phenyl)-5,7-dihydro-6H-pyrrolo[3,4-b]pyridine-6-carboxamide | ¹H NMR (400 MHz, DMSO-d₆, Temp = 90° C.) δ 8.57-8.41 (m, 1H), 7.88-7.73 (m, 3H), 7.68-7.55 (m, 2H), 7.46-7.02 (m, 1H), 4.81 (d, J = 11.6 Hz, 4H), 3.17-3.00 (m, 2H), 2.87-2.67 (m, 8H), 1.96 (s, 1H), 1.78-1.55 (m, 4H) | (ESI (+)) m/e 382 (M + H)⁺ |
| 1204 | N-(4-{[1-(1,3-thiazol-2-yl)ethyl]carbamoyl}phenyl)-5,7-dihydro-6H-pyrrolo[3,4-b]pyridine-6-carboxamide | ¹H NMR (400 MHz, DMSO-d₆, Temp = 90° C.) δ 8.49 (t, J = 5.3 Hz, 1H), 7.83 (d, J = 8.7 Hz, 3H), 7.67 (dt, J = 17.6, 9.5 Hz, 3H), 7.61-7.47 (m, 1H), 7.34 (dt, J = 35.5, 17.8 Hz, 1H), 5.46 (q, J = 7.0 Hz, 1H), 4.83 (d, J = 9.3 Hz, 4H), 1.65 (d, J = 7.0 Hz, 3H) | (ESI (+)) m/e 394 (M + H)⁺ |
| 1205 | N-(4-{[1-(1-methyl-1H-pyrazol-4-yl)ethyl]carbamoyl}phenyl)-5,7-dihydro-6H-pyrrolo[3,4-b]pyridine-6-carboxamide | ¹H NMR (400 MHz, DMSO-d₆, Temp = 90° C.) δ 8.58-8.41 (m, 1H), 7.91-7.81 (m, 1H), 7.79-7.66 (m, 2H), 7.70-7.58 (m, 2H), 7.58-7.51 (m, 1H), 7.37 (dd, J = 7.5, 5.2 Hz, 2H), 5.15 (q, J = 6.9 Hz, 1H), 4.82 (d, J = 8.4 Hz, 4H), 3.78 (s, 3H), 1.47 (t, J = 5.5 Hz, 3H) | (ESI (+)) m/e 391 (M + H)⁺ |
| 1206 | N-{4-[(3S)-tetrahydrofuran-3-ylcarbamoyl]phenyl}-5,7-dihydro-6H-pyrrolo[3,4-b]pyridine-6-carboxamide | ¹H NMR (400 MHz, DMSO-d₆, Temp = 90° C.) δ 8.46 (t, J = 11.6 Hz, 1H), 7.87-7.70 (m, 3H), 7.70-7.52 (m, 2H), 7.35 (dt, J = 14.6, 7.3 Hz, 1H), 4.82 (d, J = 9.9 Hz, 4H), 4.58-4.37 (m, 1H), 3.92-3.81 (m, 2H), 3.81-3.67 (m, 1H), 3.59 (dd, J = 8.9, 4.6 Hz, 1H), 2.31-2.11 (m, 1H), 2.02-1.76 (m, 2H) | (ESI (+)) m/e 353 (M + H)⁺ |
| 1207 | N-{4-[(1-methoxybutan-2-yl)carbamoyl]phenyl}-5,7-dihydro-6H-pyrrolo[3,4-b]pyridine-6-carboxamide | ¹H NMR (400 MHz, DMSO-d₆, Temp = 90° C.) δ 8.47 (dd, J = 15.1, 10.9 Hz, 1H), 7.84 (dd, J = 7.7, 1.0 Hz, 1H), 7.82-7.70 (m, 2H), 7.70-7.56 (m, 2H), 7.36 (dd, J = 7.7, 5.0 Hz, 1H), 4.82 (d, J = 9.1 Hz, 4H), 4.18-3.96 (m, 1H), 3.50-3.36 (m, 2H), 1.75-1.57 (m, 1H), 1.57-1.39 (m, 1H), 0.90 (t, J = 7.4 Hz, 3H) | (ESI (+)) m/e 369 (M + H)⁺ |
| 1208 | N-{4-[(4-aminobenzyl)carbamoyl]phenyl}-5,7-dihydro-6H-pyrrolo[3,4-b]pyridine-6-carboxamide | ¹H NMR (400 MHz, DMSO-d₆, Temp = 90° C.) δ 8.47 (d, J = 4.2 Hz, 1H), 7.87-7.73 (m, 3H), 7.70-7.53 (m, 2H), 7.33 (dd, J = 8.0, 6.1 Hz, 3H), 7.09 (d, J = 8.3 Hz, 2H), 4.81 (d, J = 11.4 Hz, 4H), 4.44 (s, 2H) | (ESI (+)) m/e 388 (M + H)⁺ |
| 1209 | N-{4-[(2-ethoxypropyl)carbamoyl]phenyl}-5,7-dihydro-6H-pyrrolo[3,4-b]pyridine-6-carboxamide | ¹H NMR (400 MHz, DMSO-d₆, Temp = 90° C.) δ 8.47 (t, J = 11.3 Hz, 1H), 7.87-7.81 (m, 1H), 7.80-7.71 (m, 2H), 7.73-7.53 (m, 2H), 7.45-7.08 (m, 1H), 4.82 (d, J = 9.2 Hz, 4H), 3.70-3.56 (m, 1H), 3.56-3.41 (m, 2H), 3.27 (dd, J = 13.4, 5.7 Hz, 1H), 1.18-0.88 (m, 6H) | (ESI (+)) m/e 369 (M + H)⁺ |

| Ex | Name | ¹H NMR | MS |
|---|---|---|---|
| 1210 | N-{4-[(6-methoxypyridin-3-yl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.58-8.32 (m, 2H), 8.10-7.96 (m, 1H), 7.96-7.85 (m, 2H), 7.85-7.74 (m, 1H), 7.74-7.60 (m, 1H), 7.40-7.14 (m, 1H), 6.97-6.64 (m, 1H), 5.01-4.62 (m, 4H), 3.87 (s, 3H) | (ESI (+)) m/e 390 (M + H)⁺ |
| 1211 | N-{4-[(2S)-butan-2-ylcarbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.49 (d, J = 4.9 Hz, 1H), 7.83 (t, J = 12.3 Hz, 1H), 7.84-7.69 (m, 2H), 7.73-7.51 (m, 2H), 7.37 (dd, J = 7.7, 5.0 Hz, 1H), 4.82 (d, J = 8.6 Hz, 4H), 3.92 (h, J = 6.7 Hz, 1H), 1.69-1.44 (m, 2H), 1.16 (d, J = 6.7 Hz, 3H), 0.89 (t, J = 7.4 Hz, 3H) | (ESI (+)) m/e 339 (M + H)⁺ |
| 1212 | N-{4-[(1-cyanocyclopropyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.47 (d, J = 4.7 Hz, 1H), 7.85-7.72 (m, 3H), 7.69-7.52 (m, 2H), 7.43-7.15 (m, 1H), 4.81 (d, J = 11.4 Hz, 4H), 1.61-1.41 (m, 2H), 1.40-1.17 (m, 2H) | (ESI (+)) m/e 348 (M + H)⁺ |
| 1213 | N-(4-{[2-(5-methyl-1H-pyrazol-1-yl)ethyl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.55-8.36 (m, 1H), 7.87-7.75 (m, 2H), 7.75-7.67 (m, 2H), 7.68-7.52 (m, 2H), 7.43-7.22 (m, 2H), 6.09-5.92 (m, 1H), 4.91-4.64 (m, 4H), 4.36-4.10 (m, 2H), 3.74-3.47 (m, 2H), 2.30-2.13 (m, 3H) | (ESI (+)) m/e 391 (M + H)⁺ |
| 1214 | N-(4-{[(4-methyl-1,3-thiazol-2-yl)methyl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.59-8.31 (m, 1H), 7.92-7.72 (m, 3H), 7.71-7.58 (m, 2H), 7.48-7.22 (m, 1H), 7.14-6.93 (m, 1H), 4.82 (d, J = 11.0 Hz, 4H), 4.74-4.63 (m, 2H), 2.35 (d, J = 0.6 Hz, 3H) | (ESI (+)) m/e 394 (M + H)⁺ |
| 1215 | N-{4-[(3-hydroxypropyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.56-8.38 (m, 1H), 7.88-7.79 (m, 1H), 7.79-7.68 (m, 2H), 7.70-7.55 (m, 2H), 7.46-7.23 (m, 1H), 4.82 (d, J = 9.5 Hz, 4H), 3.51 (t, J = 6.3 Hz, 2H), 3.3 (t, J = 6.3 Hz, 2H)1.83-1.60 (m, 2H) | (ESI (+)) m/e 341 (M + H)⁺ |
| 1216 | N-{4-[(2-methylpropyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.62-8.39 (m, 1H), 7.86-7.81 (m, 1H), 7.81-7.70 (m, 2H), 7.70-7.54 (m, 2H), 7.43-7.17 (m, 1H), 4.84 (dd, J = 30.5, 23.8 Hz, 4H), 3.17-3.01 (m, 2H), 2.03-1.72 (m, 2H), 0.89 (t, J = 7.9 Hz, 6H) | (ESI (+)) m/e 339 (M + H)⁺ |
| 1217 | N-{4-[(tetrahydrofuran-2-ylmethyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.57-8.39 (m, 1H), 7.86-7.80 (m, 1H), 7.80-7.69 (m, 2H), 7.69-7.54 (m, 2H), 7.42-7.26 (m, 1H), 4.82 (d, J = 10.1 Hz, 4H), 4.12-3.93 (m, 1H), 3.88-3.75 (m, 1H), 3.74-3.54 (m, 1H), 3.33 (t, J = 5.9 Hz, 2H), 1.98-1.78 (m, 4H), 1.71-1.51 (m, 1H) | (ESI (+)) m/e 367 (M + H)⁺ |
| 1218 | N-(4-{[(1R)-1-cyclopropylethyl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.49 (t, J = 5.8 Hz, 1H), 7.90-7.80 (m, 1H), 7.80-7.69 (m, 2H), 7.68-7.54 (m, 2H), 7.36 (dd, J = 7.7, 5.0 Hz, 1H), 4.82 (d, J = 9.6 Hz, 4H), 3.64-3.41 (m, 1H), 1.23 (d, J = 6.7 Hz, 3H), 1.10-0.86 (m, 1H), 0.53-0.28 (m, 3H), 0.28-0.11 (m, 1H) | (ESI (+)) m/e 351 (M + H)⁺ |
| 1219 | N-(4-{[1-(1-methylcyclopropyl)ethyl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.60-8.35 (m, 1H), 7.93-7.79 (m, 1H), 7.79-7.68 (m, 2H), 7.68-7.53 (m, 2H), 7.49-7.22 (m, 1H), 4.82 (d, J = 9.2 Hz, 4H), 3.72 (q, J = 6.8 Hz, 1H), 1.17 (d, J = 6.8 Hz, 3H), 1.08 (s, 3H), 0.67-0.48 (m, 1H), 0.47-0.34 (m, 1H), 0.32-0.12 (m, 2H) | (ESI (+)) m/e 365 (M + H)⁺ |
| 1220 | N-{4-[(thiophen-2-ylmethyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.45 (t, J = 8.3 Hz, 1H), 7.83-7.71 (m, 3H), 7.68-7.55 (m, 2H), 7.39-7.21 (m, 1H), 7.08-6.98 (m, 1H), 6.99-6.90 (m, 1H), 4.80 (d, J = 12.9 Hz, 4H), 4.63 (s, 2H) | (ESI (+)) m/e 379 (M + H)⁺ |
| 1221 | N-(4-{[(1S)-1-cyclopropylethyl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.49 (d, J = 4.9 Hz, 1H), 7.85 (d, J = 7.7 Hz, 1H), 7.78-7.69 (m, 2H), 7.72-7.54 (m, 2H), 7.37 (dd, J = 7.7, 5.0 Hz, 1H), 4.96-4.68 (m, 4H), 3.70-3.42 (m, 1H), 1.23 (d, J = 6.7 Hz, 3H), 1.15-0.90 (m, 1H), 0.58-0.16 (m, 4H) | (ESI (+)) m/e 350 (M + H)⁺ |

-continued

| Ex | Name | ¹H NMR | MS |
|---|---|---|---|
| 1222 | N-{4-[(4-methoxybutyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.60-8.35 (m, 1H), 7.90-7.79 (m, 1H), 7.79-7.70 (m, 2H), 7.69-7.52 (m, 2H), 7.43-7.29 (m, 1H), 4.86 (t, J = 24.4 Hz, 4H), 3.31-3.25 (m, 2H), 2.68-2.34 (m, 2H), 1.65-1.48 (m, 4H) | (ESI (+)) m/e 369 (M + H)⁺ |
| 1223 | N-(4-{[2-(tetrahydro-2H-pyran-3-yl)ethyl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.55-8.37 (m, 1H), 7.89-7.78 (m, 1H), 7.78-7.68 (m, 2H), 7.68-7.52 (m, 2H), 7.43-7.02 (m, 1H), 4.86 (t, J = 25.4 Hz, 4H), 3.96-3.57 (m, 2H), 3.12-2.98 (m, 1H), 2.95-2.78 (m, 2H), 1.91-1.76 (m, 1H), 1.63-1.40 (m, 4H), 1.28-1.09 (m, 1H) | (ESI (+)) m/e 395 (M + H)⁺ |
| 1224 | N-(4-{[(2S)-1-methoxypropan-2-yl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.58-8.40 (m, 1H), 7.87-7.81 (m, 1H), 7.80-7.72 (m, 2H), 7.69-7.51 (m, 2H), 7.34 (dd, J = 7.7, 5.0 Hz, 1H), 4.81 (d, J = 11.0 Hz, 4H), 4.30-4.08 (m, 1H), 3.49-3.42 (m, 1H), 3.40-3.33 (m, 1H), 3.29 (s, 3H), 1.16 (t, J = 5.4 Hz, 3H) | (ESI (+)) m/e 355 (M + H)⁺ |
| 1225 | N-{4-[(3,3-dimethyl-2-oxobutyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.49 (d, J = 4.3 Hz, 1H), 7.89-7.81 (m, 1H), 7.84-7.73 (m, 2H), 7.74-7.56 (m, 2H), 7.44-7.18 (m, 1H), 4.83 (d, J = 9.2 Hz, 4H), 4.30 (s, 2H), 1.18 (s, 9H) | (ESI (+)) m/e 391 (M + H)⁺ |
| 1226 | N-(4-{[(1-methyl-1H-pyrrol-2-yl)methyl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.58-8.35 (m, 1H), 7.92-7.71 (m, 3H), 7.70-7.49 (m, 2H), 7.44-7.19 (m, 1H), 4.82 (d, J = 9.5 Hz, 4H), 4.44 (s, 2H), 3.59 (s, 3H) | (ESI (+)) m/e 376 (M + H)⁺ |
| 1227 | N-(4-{[2-(propan-2-yloxy)ethyl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.60-8.37 (m, 1H), 7.86-7.72 (m, 3H), 7.71-7.56 (m, 3H), 7.47-7.19 (m, 1H), 4.87-4.66 (m, 4H), 3.67-3.48 (m, 3H), 3.42-3.36 (m, 2H), 1.16-1.02 (m, 6H) | (ESI (+)) m/e 369 (M + H)⁺ |
| 1228 | N-(4-{[3-(dimethylamino)propyl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.59-8.13 (m, 1H), 7.91-7.72 (m, 3H), 7.73-7.58 (m, 2H), 7.43-7.26 (m, 1H), 4.83 (t, J = 9.4 Hz, 4H), 3.37 (d, J = 6.7 Hz, 2H), 3.27-3.07 (m, 2H), 2.81 (d, J = 4.7 Hz, 6H), 1.95 (d, J = 9.3 Hz, 2H) | (ESI (+)) m/e 368 (M + H)⁺ |
| 1229 | N-[4-(tetrahydro-2H-pyran-3-ylcarbamoyl)phenyl]-5,7-dihydro-6H-pyrrolo[3,4-b]pyridine-6-carboxamide | ¹H NMR (400 MHz, DMSO-$d_6$, Temp = 90° C.) δ 8.56-8.35 (m, 1H), 7.90-7.68 (m, 3H), 7.69-7.56 (m, 2H), 7.36 (td, J = 7.9, 4.0 Hz, 1H), 4.82 (d, J = 10.2 Hz, 4H), 3.99-3.86 (m, 1H), 3.86-3.68 (m, 1H), 3.41-3.32 (m, 1H), 3.29-3.17 (m, 1H), 2.07-1.84 (m, 1H), 1.83-1.50 (m, 3H) | (ESI (+)) m/e 367 (M + H)⁺ |
| 1230 | N-(4-{[2-(1H-pyrrol-1-yl)ethyl]carbamoyl}phenyl)-5,7-dihydro-6H-pyrrolo[3,4-b]pyridine-6-carboxamide | ¹H NMR (400 MHz, DMSO-$d_6$, Temp = 90° C.) δ 8.56-8.30 (m, 1H), 7.87-7.76 (m, 1H), 7.76-7.65 (m, 2H), 7.67-7.50 (m, 2H), 7.41-7.20 (m, 1H), 6.73 (t, J = 2.0 Hz, 1H), 6.17-5.79 (m, 1H), 4.86-4.72 (m, 4H), 4.08 (t, J = 6.5 Hz, 2H), 3.57 (t, J = 6.5 Hz, 2H) | (ESI (+)) m/e 376 (M + H)⁺ |
| 1231 | N-{4-[(1-methoxypropan-2-yl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.49 (d, J = 4.8 Hz, 1H), 7.85 (t, J = 8.8 Hz, 1H), 7.81-7.70 (m, 2H), 7.70-7.52 (m, 2H), 7.51-7.22 (m, 1H), 4.82 (d, J = 9.0 Hz, 4H), 4.19 (h, J = 6.6 Hz, 1H), 3.59-3.43 (m, 1H), 3.30 (s, 3H), 2.88 (d, J = 50.6 Hz, 1H), 1.15 (dd, J = 10.7, 6.7 Hz, 3H) | (ESI (+)) m/e 355 (M + H)⁺ |
| 1232 | N-{4-[(3-aminobenzyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.48 (d, J = 4.7 Hz, 1H), 7.92-7.76 (m, 3H), 7.74-7.51 (m, 2H), 7.32 (ddd, J = 15.4, 7.7, 4.6 Hz, 2H), 7.18-7.08 (m, 2H), 7.00 (d, J = 7.9 Hz, 1H), 4.82 (d, J = 11.2 Hz, 4H), 4.47 (s, 2H) | (ESI (+)) m/e 388 (M + H)⁺ |
| 1233 | N-(4-{[(2R)-3-methylbutan-2-yl]carbamoyl}phenyl)-5,7-dihydro-6H-pyrrolo[3,4-b]pyridine-6-carboxamide | ¹H NMR (400 MHz, DMSO_$D_2O$) δ 8.56-8.39 (m, 1H), 7.92-7.80 (m, 1H), 7.80-7.68 (m, 2H), 7.68-7.53 (m, 2H), 7.53-6.97 (m, 1H), 4.83 (d, J = 7.2 Hz, 4H), 3.99-3.74 (m, 1H), 1.91-1.66 (m, 1H), 1.12 (d, J = 6.8 Hz, 3H), 0.99-0.82 (m, 6H) | (ESI (+)) m/e 353 (M + H)⁺ |

-continued

| Ex | Name | ¹H NMR | MS |
|---|---|---|---|
| 1234 | N-{4-[(tetrahydro-2H-pyran-3-ylmethyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.62-8.38 (m, 1H), 7.91-7.80 (m, 1H), 7.80-7.70 (m, 2H), 7.69-7.45 (m, 2H), 7.48-7.24 (m, 1H), 4.83 (d, J = 8.0 Hz, 4H), 3.87-3.61 (m, 2H), 3.19-3.12 (m, 3H), 1.92 (d, J = 34.0 Hz, 1H), 1.87-1.73 (m, 2H), 1.67-1.55 (m, 1H), 1.55-1.37 (m, 1H), 1.39-1.14 (m, 1H) | (ESI (+)) m/e 381 (M + H)⁺ |
| 1235 | N-{4-[(2-hydroxy-2-methylpropyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.61-8.43 (m, 1H), 7.90-7.71 (m, 3H), 7.71-7.50 (m, 2H), 7.42-7.14 (m, 1H), 4.98-4.68 (m, 4H), 3.04-2.66 (m, 2H), 1.29-1.01 (m, 6H) | (ESI (+)) m/e 355 (M + H)⁺ |
| 1236 | N-[4-(butylcarbamoyl)phenyl]-5,7-dihydro-6H-pyrrolo[3,4-b]pyridine-6-carboxamide | ¹H NMR (400 MHz, DMSO-$d_6$, Temp = 90° C.) δ 8.55-8.42 (m, 1H), 7.85-7.77 (m, 1H), 7.79-7.68 (m, 2H), 7.68-7.54 (m, 2H), 7.47-6.86 (m, 1H), 4.80 (t, J = 9.0 Hz, 4H), 3.26-3.17 (m, 2H), 1.63-1.49 (m, 2H), 1.46-1.27 (m, 2H), 0.92 (dd, J = 9.2, 5.5 Hz, 3H) | (ESI (+)) m/e 339 (M + H)⁺ |
| 1237 | N-{4-[methyl(tetrahydrofuran-2-ylmethyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.57-8.37 (m, 1H), 7.90-7.72 (m, 1H), 7.66-7.52 (m, 2H), 7.45-7.34 (m, 1H), 7.33-7.16 (m, 2H), 4.86 (t, J = 24.4 Hz, 4H), 4.21-3.97 (m, 1H), 3.86-3.55 (m, 2H), 3.57-3.39 (m, 2H), 3.08-2.97 (m, 3H), 1.98-1.88 (m, 2H), 1.85-1.68 (m, 2H), 1.60-1.37 (m, 1H) | (ESI (+)) m/e 381 (M + H)⁺ |
| 1238 | N-{4-[(2-methoxyethyl)(methyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.49 (t, J = 5.2 Hz, 1H), 7.95-7.76 (m, 1H), 7.71-7.52 (m, 2H), 7.38-7.33 (m, 1H), 7.33-7.22 (m, 2H), 4.82 (d, J = 9.0 Hz, 4H), 3.61-3.44 (m, 4H), 3.29-3.19 (m, 3H), 2.98 (s, 3H) | (ESI (+)) m/e 355 (M + H)⁺ |
| 1239 | N-{4-[(1-cyanoethyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.59-8.32 (m, 1H), 7.91-7.72 (m, 3H), 7.72-7.59 (m, 2H), 7.40-7.20 (m, 1H), 5.03-4.86 (m, 1H), 4.88-4.68 (m, 4H), 1.72-1.43 (m, 3H) | (ESI (+)) m/e 336 (M + H)⁺ |
| 1240 | N-{4-[(3R)-tetrahydrofuran-3-ylcarbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.48 (d, J = 4.4 Hz, 1H), 7.89-7.74 (m, 3H), 7.68-7.48 (m, 2H), 7.45-7.24 (m, 1H), 4.82 (d, J = 9.2 Hz, 4H), 4.59-4.28 (m, 1H), 3.94-3.83 (m, 2H), 3.80-3.64 (m, 1H), 3.65-3.51 (m, 1H), 2.37-2.00 (m, 1H), 2.05-1.80 (m, 1H) | (ESI (+)) m/e 353 (M + H)⁺ |
| 1241 | N-{4-[(cyclopentylmethyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.49 (d, J = 4.8 Hz, 1H), 7.90-7.80 (m, 1H), 7.80-7.68 (m, 2H), 7.68-7.49 (m, 2H), 7.47-7.11 (m, 1H), 4.82 (d, J = 9.0 Hz, 4H), 3.26-3.10 (m, 2H), 2.36-2.07 (m, 1H), 1.75-1.45 (m, 6H), 1.39-1.18 (m, 2H) | (ESI (+)) m/e 365 (M + H)⁺ |
| 1242 | N-{4-[(2-methoxy-2-methylpropyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.61-8.36 (m, 1H), 7.88-7.71 (m, 3H), 7.71-7.55 (m, 2H), 7.46-7.15 (m, 1H), 4.99-4.66 (m, 4H), 3.35 (d, J = 4.5 Hz, 2H), 3.19-3.16 (m, 3H), 1.46-0.84 (m, 6H) | (ESI (+)) m/e 369 (M + H)⁺ |
| 1243 | N-{4-[(cyclopropylmethyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.60-8.40 (m, 1H), 7.85 (d, J = 7.7 Hz, 1H), 7.82-7.71 (m, 2H), 7.71-7.53 (m, 2H), 7.38 (dd, J = 7.7, 5.0 Hz, 1H), 7.30-7.14 (m, 1H), 5.07-4.65 (m, 4H), 3.16 (t, J = 6.6 Hz, 2H), 1.20-0.87 (m, 1H), 0.52-0.37 (m, 2H), 0.32-0.06 (m, 2H) | (ESI (+)) m/e 337 (M + H)⁺ |
| 1244 | N-{4-[methyl(propyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.61-8.38 (m, 1H), 7.93-7.76 (m, 1H), 7.68-7.54 (m, 2H), 7.46-7.33 (m, 1H), 7.31-7.17 (m, 2H), 4.97-4.59 (m, 4H), 2.92 (d, J = 8.0 Hz, 4H), 1.67-1.47 (m, 2H), 0.96-0.59 (m, 3H) | (ESI (+)) m/e 339 (M + H)⁺ |
| 1245 | N-{4-[(pyridin-4-ylmethyl)carbamoyl]phenyl}-5,7-dihydro-6H-pyrrolo[3,4-b]pyridine-6-carboxamide | ¹H NMR (400 MHz, DMSO-$d_6$, Temp = 90° C.) δ 8.83-8.62 (m, 2H), 8.52-8.39 (m, 1H), 7.96-7.77 (m, 3H), 7.77-7.70 (m, 2H), 7.70-7.59 (m, 2H), 7.43-7.14 (m, 1H), 4.90-4.72 (m, 4H), 4.74-4.48 (m, 2H) | (ESI (+)) m/e 374 (M + H)⁺ |

Example 293

N-{4-[(4-phenylbutanoyl)amino]phenyl}-1,3-dihydro-2H-isoindole-2-carboxamide

Example 293A

N-(4-nitrophenyl)isoindoline-2-carboxamide

A solution of N-(4-aminophenyl)isoindoline-2-carboxamide (100 mg, 0.395 mmol), 4-phenylbutanoic acid (78 mg, 0.474 mmol), 1-hydroxybenzotriazole hydrate (66.5 mg, 0.434 mmol) and N-methylmorpholine (0.109 ml, 0.987 mmol) in N,N-dimethylformamide (1.771 ml) at room temperature was treated with N-(3-dimethylaminopropyl)-N'-ethylcarbodiimide hydrochloride (136 mg, 0.711 mmol). The mixture was stirred overnight and diluted with water (10 ml); the resulting suspension was filtered with water washes to give after drying product with an impurity. This solid was suspended in 2% methanol/dichloromethane and filtered to provide the title compound.

Example 293B

N-(4-aminophenyl)isoindoline-2-carboxamide

The title compound was prepared as described in Example 274, substituting N-(4-nitrophenyl)isoindoline-2-carboxamide for 5-nitro-N-[4-(propylcarbamoyl)phenyl]-1,3-dihydro-2H-isoindole-2-carboxamide.

Example 293C

N-{4-[(4-phenylbutanoyl)amino]phenyl}-1,3-dihydro-2H-isoindole-2-carboxamide

A solution of N-(4-aminophenyl)isoindoline-2-carboxamide (100 mg, 0.395 mmol), 4-phenylbutanoic acid (78 mg, 0.474 mmol), 1-hydroxybenzotriazole hydrate (66.5 mg, 0.434 mmol) and N-methylmorpholine (0.109 ml, 0.987 mmol) in dimethylformamide (1.771 ml) at room temperature was treated with N-(3-dimethylaminopropyl)-N'-ethylcarbodiimide hydrochloride (136 mg, 0.711 mmol). The mixture was stirred overnight and diluted with water (10 ml); the resulting suspension was filtered with water washes to give product with an impurity. This solid was suspended in 2% methanol/methylene chloride and filtered to provide the title compound. $^1$H NMR (300 MHz, DMSO-$d_6$) δ ppm 1.78-2.00 (m, 2H), 2.30 (t, J=7.3 Hz, 2H), 2.62 (t, J=7.5 Hz, 2H), 4.75 (s, 4H), 7.08-7.41 (m, 9H), 7.46 (s, 4H), 8.26 (s, 1H), 9.73 (s, 1H); (ESI(+)) m/e 400 (M+H)$^+$.

Table 5.

The following Examples were prepared essentially as described in Example 293, using an appropriate amine in Example 293A and substituting an appropriate carboxylic acid for 4-phenylbutanoic acid in Example 293C. Some products were purified by flash chromatography while others were purified by reverse-phase HPLC; accordingly, some Examples were isolated as trifluoroacetic acid salts.

| Ex | Name | $^1$H NMR | MS |
|---|---|---|---|
| 291 | N-{4-[(4,4,4-trifluorobutanoyl)amino]phenyl}-1,3-dihydro-2H-isoindole-2-carboxamide | $^1$H NMR (300 MHz, DMSO-$d_6$) δ ppm 2.52-2.69 (m, 4 H), 4.75 (s, 4 H), 7.23-7.40 (m, 4 H), 7.41-7.56 (m, 4 H), 8.28 (s, 1 H), 9.93 (s, 1 H) | (ESI (+)) m/e 378 (M + H)$^+$ |
| 292 | N-{4-[(3-ethoxypropanoyl)amino]phenyl}-1,3-dihydro-2H-isoindole-2-carboxamide | $^1$H NMR (400 MHz, DMSO-$d_6$/Deuterium Oxide, Temp = 90° C.) δ ppm 7.44 (s, 4H), 7.32-7.37 (m, 2H), 7.28-7.32 (m, 2H), 4.76 (s, 4H), 3.68 (t, J = 6.3 Hz, 2H), 3.47 (q, J = 6.9 Hz, 2H), 2.50-2.55 (m, 2H), 1.11 (t, J = 6.9 Hz, 3H) | (ESI (+)) m/e 354 (M + H)$^+$ |
| 294 | N-{4-[(4-methylpentanoyl)amino]phenyl}-1,3-dihydro-2H-isoindole-2-carboxamide | $^1$H NMR (300 MHz, DMSO-$d_6$) δ ppm 0.90 (d, J = 6.4 Hz, 6H), 1.40-1.63 (m, 3 H), 2.18-2.39 (m, 2 H), 4.75 (s, 4 H), 7.20-7.41 (m, 4 H,) 7.45 (s, 4 H), 8.26 (s, 1 H), 9.72 (s, 1 H) | (ESI (+)) m/e 352 (M + H)$^+$ |
| 295 | N-(4-{[(benzyloxy)acetyl]amino}phenyl)-1,3-dihydro-2H-isoindole-2-carboxamide | $^1$H NMR (400 MHz, DMSO-$d_6$/Deuterium Oxide, Temp = 90° C.) δ ppm 7.47 (s, 4H), 7.28-7.43 (m, 9H), 4.76 (s, 4H), 4.64 (s, 2H), 4.07 (s, 2H) | (ESI (+)) m/e 402 (M + H)$^+$ |
| 296 | N-{4-[(3-phenylpropanoyl)amino]phenyl}-1,3-dihydro-2H-isoindole-2-carboxamide | $^1$H NMR (400 MHz, DMSO-$d_6$/Deuterium Oxide, Temp = 90° C.) δ ppm 7.42 (s, 4H), 7.22-7.37 (m, 8H), 7.15-7.20 (m, 1H), 4.76 (s, 4H), 2.93 (t, J = 7.6 Hz, 2H), 2.59-2.63 (m, 2H) | (ESI (−)) m/e 384 (M − H)$^-$ |
| 297 | N-{4-[(3-phenoxypropanoyl)amino]phenyl}-1,3-dihydro-2H-isoindole-2-carboxamide | $^1$H NMR (400 MHz, DMSO-$d_6$/Deuterium Oxide, Temp = 90° C.) δ ppm 7.45 (s, 4H), 7.26-7.36 (m, 6H), 6.92-6.96 (m, 2H), 6.91-6.95 (m, 1H), 4.76 (s, 4H), 4.29 (t, J = 6.2 Hz, 2H), 2.76 (t, J = 6.2 Hz, 2H) | (APCI (+)) m/e 402 (M + H)$^+$ |
| 298 | N-(4-{[N-(2-furoyl)glycyl]amino}phenyl)-1,3-dihydro-2H-isoindole-2-carboxamide | $^1$H NMR (400 MHz, DMSO-$d_6$/Deuterium Oxide, Temp = 90° C.) δ ppm 7.76 (dd, J = 1.8, 0.8 Hz, 1H), 7.42-7.48 (m, 4H), 7.29-7.36 (m, 4H), 7.12 (dd, J = 3.5, 0.9 Hz, 1H), 6.62 (dd, J = 3.4, 1.7 Hz, 1H), 4.76 (s, 4H), 4.04 (s, 2H) | (ESI (+)) m/e 405 (M + H)$^+$ |
| 299 | N-(4-{[4-(2-thienyl)butanoyl]amino}phenyl)-1,3-dihydro-2H-isoindole-2-carboxamide | $^1$H NMR (400 MHz, DMSO-$d_6$/Deuterium Oxide, Temp = 90° C.) δ ppm 7.43 (s, 4H), 7.32-7.38 (m, 2H), 7.28-7.32 (m, 2H), 7.25 (dd, J = 5.2, 1.2 Hz, 1H), 6.94 (dd, J = 5.0, 3.4 Hz, 1H), 6.86 (dq, J = 3.3, 1.1 Hz, 1H), 4.76 (s, 4H), 2.87 (ddd, J = 8.1, 7.1, 1.0 Hz, 2H), 2.37 (t, J = 7.3 Hz, 2H), 1.96 (p, J = 7.4 Hz, 2H) | (APCI (+)) m/e 406 (M + H)$^+$ |

-continued

| Ex | Name | ¹H NMR | MS |
|---|---|---|---|
| 300 | N-{4-[(4-oxo-4-phenylbutanoyl)amino]phenyl}-1,3-dihydro-2H-isoindole-2-carboxamide | ¹H NMR (400 MHz, DMSO-d₆/Deuterium Oxide, Temp = 90° C.) δ ppm 7.96-7.99 (m, 2H), 7.60-7.65 (m, 1H), 7.50-7.56 (m, 2H), 7.43 (s, 4H), 7.32-7.37 (m, 2H), 7.28-7.32 (m, 2H), 4.76 (s, 4H), 3.32 (t, J = 6.6 Hz, 2H), 2.72 (t, J = 6.6 Hz, 2H) | (ESI (−)) m/e 412 (M − H)⁻ |
| 301 | N-{4-[(N-benzoylglycyl)amino]phenyl}-1,3-dihydro-2H-isoindole-2-carboxamide | ¹H NMR (400 MHz, DMSO-d₆/Deuterium Oxide, Temp = 90° C.) δ ppm 7.84-7.94 (m, 2H), 7.52-7.57 (m, 1H), 7.48-7.51 (m, 2H), 7.46 (s, 4H), 7.32-7.37 (m, 2H), 7.28-7.32 (m, 2H), 4.76 (s, 4H), 4.08 (s, 2H) | (ESI (+)) m/e 415 (M + H)⁺ |
| 302 | N-{4-[(4-phenoxybutanoyl)amino]phenyl}-1,3-dihydro-2H-isoindole-2-carboxamide | ¹H NMR (400 MHz, DMSO-d₆/Deuterium Oxide, Temp = 90° C.) δ ppm 7.44 (s, 4H), 7.33-7.37 (m, 2H), 7.29-7.32 (m, 2H), 7.24-7.29 (m, 2H), 6.90-6.94 (m, 3H), 4.76 (s, 4H), 4.04 (t, J = 6.4 Hz, 2H), 2.47 (t, J = 7.3 Hz, 2H), 2.01-2.08 (m, 2H) | (ESI (−)) m/e 414 (M − H)⁻ |
| 303 | N-[4-(propionylamino)phenyl]-1,3-dihydro-2H-isoindole-2-carboxamide | ¹H NMR (400 MHz, DMSO-d₆/Deuterium Oxide, Temp = 90° C.) δ ppm 7.43 (s, 4H), 7.29-7.36 (m, 4H), 4.76 (s, 4H), 2.30 (q, J = 7.6 Hz, 2H), 1.11 (t, J = 7.5 Hz, 3H) | (ESI (+)) m/e 310 (M + H)⁺ |
| 304 | N-[4-(pentanoylamino)phenyl]-1,3-dihydro-2H-isoindole-2-carboxamide | ¹H NMR (400 MHz, DMSO-d₆/Deuterium Oxide, Temp = 90° C.) δ ppm 7.43 (s, 4H), 7.32-7.37 (m, 2H), 7.28-7.32 (m, 2H), 4.76 (s, 4H), 2.28 (t, J = 7.4 Hz, 2H), 1.56-1.64 (m, 2H), 1.30-1.40 (m, 2H), 0.91 (t, J = 7.3 Hz, 3H) | (ESI (+)) m/e 338 (M + H)⁺ |
| 305 | N-[4-(hexanoylamino)phenyl]-1,3-dihydro-2H-isoindole-2-carboxamide | ¹H NMR (400 MHz, DMSO-d₆/Deuterium Oxide, Temp = 90° C.) δ ppm 7.43 (s, 4H), 7.29-7.36 (m, 4H), 4.76 (s, 4H), 2.27 (t, J = 7.4 Hz, 2H), 1.57-1.65 (m, 2H), 1.27-1.37 (m, 4H), 0.86-0.90 (m, 3H) | (ESI (+)) m/e 352 (M + H)⁺ |
| 306 | N-[4-(heptanoylamino)phenyl]-1,3-dihydro-2H-isoindole-2-carboxamide | ¹H NMR (400 MHz, DMSO-d₆/Deuterium Oxide, Temp = 90° C.) δ ppm 7.43 (s, 4H), 7.29-7.36 (m, 4H), 4.76 (s, 4H), 2.28 (t, J = 7.4 Hz, 2H), 1.60 (p, J = 7.1 Hz, 2H), 1.25-1.39 (m, 6H), 0.83-0.91 (m, 3H) | (ESI (+)) m/e 366 (M + H)⁺ |
| 307 | N-[4-(pent-4-enoylamino)phenyl]-1,3-dihydro-2H-isoindole-2-carboxamide | ¹H NMR (300 MHz, DMSO-d₆) δ ppm 2.24-2.44 (m, 4 H), 4.75 (s, 4 H), 4.91-5.14 (m, 2 H), 5.72-5.97 (m, 1 H), 7.25-7.40 (m, 4 H), 7.46 (s, 4 H), 8.26 (s, 1 H), 9.76 (s, 1 H) | (ESI (+)) m/e 336 (M + H)⁺ |
| 308 | N-{4-[(ethoxyacetyl)amino]phenyl}-1,3-dihydro-2H-isoindole-2-carboxamide | ¹H NMR (400 MHz, DMSO-d₆/Deuterium Oxide, Temp = 90° C.) δ ppm 7.47-7.50 (m, 4H), 7.29-7.36 (m, 4H), 4.76 (s, 4H), 3.99 (s, 2H), 3.60 (q, J = 7.0 Hz, 2H), 1.21 (t, J = 6.9 Hz, 3H) | (ESI (+)) m/e 340 (M + H)⁺ |
| 309 | N-(4-{[(2-methoxyethoxy)acetyl]amino}phenyl)-1,3-dihydro-2H-isoindole-2-carboxamide | ¹H NMR (400 MHz, DMSO-d₆/Deuterium Oxide, Temp = 90° C.) δ ppm 7.47 (s, 4H), 7.29-7.36 (m, 4H), 4.76 (s, 4H), 4.04 (s, 2H), 3.68-3.71 (m, 2H), 3.55-3.58 (m, 2H), 3.32 (s, 3H) | (ESI (+)) m/e 370 (M + H)⁺ |
| 310 | N-{4-[(cyclopropylacetyl)amino]phenyl}-1,3-dihydro-2H-isoindole-2-carboxamide | ¹H NMR (400 MHz, DMSO-d₆/Deuterium Oxide, Temp = 90° C.) δ ppm 7.44 (s, 4H), 7.29-7.36 (m, 4H), 4.76 (s, 4H), 2.21 (d, J = 6.9 Hz, 2H), 1.00-1.14 (m, 1H), 0.47-0.52 (m, 2H), 0.18-0.23 (m, 2H) | (ESI (+)) m/e 336 (M + H)⁺ |
| 311 | N-{4-[(cyclopentylacetyl)amino]phenyl}-1,3-dihydro-2H-isoindole-2-carboxamide | ¹H NMR (400 MHz, DMSO-d₆/Deuterium Oxide, Temp = 90° C.) δ ppm 7.43 (s, 4H), 7.29-7.36 (m, 4H), 4.76 (s, 4H), 2.25-2.30 (m, 3H), 1.73-1.81 (m, 2H), 1.49-1.64 (m, 4H), 1.18-1.27 (m, 2H) | (ESI (−)) m/e 362 (M − H)⁻ |
| 312 | N-(4-{[3-(4-methylpiperazin-1-yl)propanoyl]amino}phenyl)-1,3-dihydro-2H-isoindole-2-carboxamide | ¹H NMR (400 MHz, DMSO-d₆/Deuterium Oxide, Temp = 90° C.) δ ppm 7.42-7.48 (m, 4H), 7.29-7.36 (m, 4H), 4.76 (s, 4H), 3.22-3.25 (m, 4H), 3.03 (t, J = 6.9 Hz, 2H), 2.97-3.01 (m, 4H), 2.77 (s, 3H), 2.62 (t, J = 6.9 Hz, 2H) | (ESI (+)) m/e 408 (M + H)⁺ |
| 564 | 5-cyano-N-{4-[(cyclopentylacetyl)amino]phenyl}-1,3-dihydro-2H-isoindole-2-carboxamide | ¹H NMR (300 MHz, DMSO-d₆) δ ppm 9.70 (s, 1H), 8.35 (s, 1H), 7.88 (s, 1H), 7.78 (dd, J = 7.9, 1.5 Hz, 1H), 7.58 (d, J = 7.9 Hz, 1H), 7.51-7.40 (m, 4H), 4.84-4.76 (m, 4H), 2.31-2.15 (m, 3H), 1.81-1.67 (m, 2H), 1.67-1.45 (m, 4H), 1.29-1.11 (m, 2H) | (ESI (+)) m/e 389 (M + H)⁺ |
| 596 | N-{4-[(cyclopentylacetyl)amino]phenyl}-5-methoxy-1,3-dihydro-2H-isoindole-2-carboxamide | ¹H NMR (300 MHz, DMSO-d₆) δ ppm 9.68 (s, 1H), 8.23 (s, 1H), 7.50-7.38 (m, 4H), 7.25 (d, J = 8.4 Hz, 1H), 6.95-6.91 (m, 1H), 6.90-6.83 (m, 1H), 4.68 (m, 4H), 3.76 (s, 3H), 2.31-2.15 (m, 3H), 1.83-1.68 (m, 2H), 1.67-1.40 (m, 4H), 1.29-1.11 (m, 2H) | (ESI (+)) m/e 394 (M + H)⁺ |

| Ex | Name | ¹H NMR | MS |
|---|---|---|---|
| 649 | 5-(hydroxymethyl)-N-{4-[(tetrahydrofuran-3-ylacetyl)amino]phenyl}-1,3-dihydro-2H-isoindole-2-carboxamide | ¹H NMR (300 MHz, DMSO-$d_6$) δ ppm 9.80 (s, 1H), 8.28 (s, 1H), 7.46 (s, 4H), 7.33-7.28 (m, 2H), 7.27-7.21 (m, 1H), 5.21 (t, J = 5.6 Hz, 1H), 4.73 (bs, 4H), 4.51 (d, J = 5.6 Hz, 2H), 3.85-3.70 (m, 2H), 3.64 (q, J = 7.6 Hz, 1H), 2.61-2.52 (m, 2H), 2.42-2.32 (m, 2H), 2.12-1.94 (m, 1H), 1.62-1.47 (m, 1H) | (ESI (+)) m/e 396 (M + H)⁺ |
| 650 | 5-(hydroxymethyl)-N-(4-{[(2-methoxyethoxy)acetyl]amino}phenyl)-1,3-dihydro-2H-isoindole-2-carboxamide | ¹H NMR (300 MHz, DMSO-$d_6$, Temp = 90° C.) δ ppm 9.19 (s, 1H), 8.05 (s, 1H), 7.48 (m, 4H), 7.31-7.19 (m, 3H), 4.86 (bs, 1H), 4.74 (bs, 4H), 4.53 (bs, 2H), 4.04 (s, 2H), 3.74-3.66 (m, 2H), 3.60-3.52 (m, 2H), 3.32 (s, 3H) | (ESI (+)) m/e 400 (M + H)⁺ |
| 682 | 5-(hydroxymethyl)-N-{4-[(tetrahydrofuran-2-ylacetyl)amino]phenyl}-1,3-dihydro-2H-isoindole-2-carboxamide | ¹H NMR (300 MHz, DMSO-$d_6$, Temp = 90° C.) δ ppm 9.41 (bs, 1H), 8.01 (bs, 1H), 7.45-7.41 (m, 4H), 7.30-7.22 (m, 3H), 4.87 (bs, 1H), 4.73 (bs, 4H), 4.52 (bs, 2H), 4.22-4.14 (m, 1H), 3.82-3.75 (m, 1H), 3.66-3.59 (m, 1H), 2.53 (dd, J = 14.1, 7.0 Hz, 1H), 2.40 (dd, J = 14.0, 6.1 Hz, 1H), 2.05-1.94 (m, 1H), 1.92-1.76 (m, 2H), 1.64-1.51 (m, 1H) | (ESI (+)) m/e 396 (M + H)⁺ |
| 683 | N-{4-[(ethoxyacetyl)amino]phenyl}-5-(hydroxymethyl)-1,3-dihydro-2H-isoindole-2-carboxamide | ¹H NMR (300 MHz, DMSO-$d_6$) δ ppm 9.52 (s, 1H), 8.29 (s, 1H), 7.56-7.44 (m, 4H), 7.33-7.20 (m, 3H), 5.20 (t, J = 5.6 Hz, 1H), 4.73 (bs, 4H), 4.51 (d, J = 5.6 Hz, 2H), 4.00 (s, 2H), 3.56 (q, J = 7.0 Hz, 2H), 1.19 (t, J = 7.0 Hz, 3H) | (ESI (+)) m/e 370 (M + H)⁺ |
| 684 | 5-(hydroxymethyl)-N-{4-[(tetrahydro-2H-pyran-4-ylacetyl)amino]phenyl}-1,3-dihydro-2H-isoindole-2-carboxamide | ¹H NMR (300 MHz, DMSO-$d_6$, Temp = 90° C.) δ ppm 9.43 (bs, 1H), 8.00 (bs, 1H), 7.44-7.41 (m, 4H), 7.30-7.20 (m, 3H), 4.89-4.83 (m, 1H), 4.73 (bs, 4H), 4.52 (bs, 2H), 3.86-3.78 (m, 2H), 3.38-3.26 (m, 2H), 2.23 (d, J = 7.0 Hz, 2H), 2.07-1.94 (m, 1H), 1.66-1.58 (m, 2H), 1.35-1.20 (m, 2H) | (ESI (+)) m/e 410 (M + H)⁺ |
| 685 | 5-(hydroxymethyl)-N-{4-[(morpholin-4-ylacetyl)amino]phenyl}-1,3-dihydro-2H-isoindole-2-carboxamide | ¹H NMR (300 MHz, DMSO-$d_6$, Temp = 90° C.) δ ppm 9.32 (bs, 1H), 8.04 (bs, 1H), 7.49-7.45 (m, 4H), 7.32-7.22 (m, 3H), 4.89-4.83 (m, 1H), 4.74 (bs, 4H), 4.53 (bs, 2H), 3.68-3.62 (m, 4H), 3.10 (s, 2H), 2.57-2.51 (m, 4H) | (ESI (+)) m/e 411 (M + H)⁺ |
| 789 | N-{4-[(cyclopentylacetyl)amino]phenyl}-5-fluoro-1,3-dihydro-2H-isoindole-2-carboxamide | ¹H NMR (400 MHz, DMSO-$d_6$/$D_2O$, Temp = 90° C.) δ ppm 7.39 (m, 4H), 7.16 (dd, J = 9.1, 2.6, 1H), 7.09 (m, 1H), 4.75 (bs, 2H), 4.72 (bs, 2H), 2.27 (m, 3H), 1.76 (m, 2H), 1.57 (m, 4H), 1.24 (m, 2H) | (ESI (+)) m/e 382 (M + H)⁺ |
| 791 | N-{4-[(cyclopentylacetyl)amino]phenyl}-5-(trifluoromethyl)-1,3-dihydro-2H-isoindole-2-carboxamide | ¹H NMR (400 MHz, DMSO-$d_6$/$D_2O$, Temp = 90° C.) δ 7.70 (s, 1H), 7.64 (dd, J = 8.0, 1.6, 1H), 7.58 (d, J = 8.0, 1H), 7.48-7.41 (m, 3H), 4.83 (s, 3H), 2.32-2.25 (m, 3H), 1.81-1.71 (m, 2H), 1.66-1.47 (m, 4H), 1.28-1.16 (m, 2H) | (ESI (+)) m/e 432 (M + H)⁺ |
| 792 | 4-cyano-N-{4-[(cyclopentylacetyl)amino]phenyl}-1,3-dihydro-2H-isoindole-2-carboxamide | ¹H NMR (400 MHz, DMSO-$d_6$/$D_2O$, Temp = 90° C.) δ 7.70 (ddd, J = 12.2, 7.7, 0.8, 2H), 7.52 (d, J = 7.7, 1H), 7.45 (m, 5H), 4.93 (d, J = 1.3, 2H), 4.83 (d, J = 0.7, 2H), 2.28 (m, 4H), 1.77 (m, 2H), 1.57 (m, 4H) | (ESI (+)) m/e 389 (M + H)⁺ |
| 793 | N-{4-[(cyclopentylacetyl)amino]phenyl}-5-methyl-1,3-dihydro-2H-isoindole-2-carboxamide | ¹H NMR (400 MHz, DMSO-$d_6$/$D_2O$, Temp = 90° C.) δ 7.42 (s, 4H), 7.22 (d, J = 7.8, 1H), 7.15 (s, 1H), 7.15-7.08 (m, 1H), 4.70 (bs, 4H), 2.35-2.23 (m, 4H), 1.82-1.71 (m, 2H), 1.66-1.47 (m, 4H), 1.30-1.16 (m, 2H) | (ESI (+)) m/e 378 (M + H)⁺ |
| 794 | 4-chloro-N-{4-[(cyclopentylacetyl)amino]phenyl}-1,3-dihydro-2H-isoindole-2-carboxamide | ¹H NMR (400 MHz, DMSO-$d_6$/$D_2O$, Temp = 90° C.) δ 7.43 (m, 4H), 7.33 (m, 3H), 4.83 (m, 2H), 4.78 (m, 2H), 2.28 (m, 3H), 1.77 (m, 2H), 1.57 (m, 4H), 1.22 (m, 2H) | (ESI (+)) m/e 398 (M + H)⁺ |
| 796 | 5-chloro-N-{4-[(cyclopentylacetyl)amino]phenyl}-1,3-dihydro-2H-isoindole-2-carboxamide | ¹H NMR (400 MHz, DMSO-$d_6$/$D_2O$, Temp = 90° C.) δ 7.35 (m, 7H), 4.74 (d, J = 6.7, 4H), 2.27 (m, 3H), 1.78 (m, 2H), 1.57 (m, 4H), 1.21 (m, 2H) | (ESI (+)) m/e 398 (M + H)⁺ |
| 874 | 5-acetyl-N-{4-[(cyclopentylacetyl)amino]phenyl}-1,3-dihydro-2H-isoindole-2-carboxamide | ¹H NMR (300 MHz, DMSO-$d_6$) δ ppm 9.70 (s, 1H), 8.33 (s, 1H), 7.96-7.88 (m, 2H), 7.54-7.40 (m, 5H), 4.81 (bs, 4H), 2.60 (s, 3H), 2.31-2.18 (m, 3H), 1.81-1.68 (m, 2H), 1.68-1.43 (m, 4H), 1.25-1.10 (m, 2H) | (ESI (+)) m/e 406 (M + H)⁺ |
| 878 | N-{4-[(cyclopentylacetyl)amino]phenyl}-5-(1-hydroxyethyl)-1,3-dihydro-2H-isoindole-2-carboxamide | ¹H NMR (300 MHz, DMSO-$d_6$) δ ppm 9.68 (s, 1H), 8.25 (s, 1H), 7.47-7.44 (m, 4H), 7.32 (s, 1H), 7.27 (s, 2H), 5.15 (d, J = 4.0 Hz, 1H), 4.78-4.67 (m, 5H), 2.30-2.15 (m, 3H), 1.82-1.68 (m, 2H), 1.67-1.45 (m, 4H), 1.33 (d, J = 6.4 Hz, 3H), 1.26-1.13 (m, 2H) | (ESI (+)) m/e 408 (M + H)⁺ |

-continued

| Ex | Name | $^1$H NMR | MS |
|---|---|---|---|
| 879 | N-[4-(butyrylamino)phenyl]-5-cyano-1,3-dihydro-2H-isoindole-2-carboxamide | $^1$H NMR (500 MHz, DMSO-$d_6$) δ ppm 9.72 (s, 1H), 8.34 (s, 1H), 7.86 (s, 1H), 7.79-7.73 (m, 1H), 7.59-7.53 (d, J = 7.9 Hz, 1H), 7.48-7.40 (m, 4H), 4.83-4.75 (m, 4H), 2.24 (t, J = 7.3 Hz, 2H), 1.65-1.53 (m, 2H), 0.90 (t, J = 7.4 Hz, 3H) | (ESI (+)) m/e 349 (M + H)$^+$ |
| 919 | 5-(acetamidomethyl)-N-{4-[(cyclopentylacetyl)amino]phenyl}-1,3-dihydro-2H-isoindole-2-carboxamide | $^1$H NMR (400 MHz, DMSO-$d_6$, Temp = 90° C.) δ ppm 9.36 (bs, 1H), 8.04-7.95 (m, 2H), 7.48-7.39 (m, 4H), 7.30-7.17 (m, 3H), 4.73 (bs, 4H), 4.27 (d, J = 5.9 Hz, 2H), 2.33-2.21 (m, 3H), 1.88 (s, 3H), 1.83-1.71 (m, 2H), 1.69-1.47 (m, 4H), 1.29-1.17 (m, 2H) | (ESI (+)) m/e 435 (M + H)$^+$ |
| 932 | N-{4-[(cyclopentylacetyl)amino]phenyl}-5-(2-hydroxypropan-2-yl)-1,3-dihydro-2H-isoindole-2-carboxamide | $^1$H NMR (300 MHz, DMSO-$d_6$) δ ppm 9.70 (s, 1H), 8.25 (s, 1H), 7.50-7.41 (m, 5H), 7.42-7.36 (m, 1H), 7.29-7.23 (m, 1H), 5.03 (s, 1H), 4.72 (bs, 4H), 2.31-2.16 (m, 3H), 1.85-1.68 (m, 2H), 1.68-1.46 (m, 4H), 1.43 (s, 6H), 1.26-1.09 (m, 2H) | (ESI (+)) m/e 422 (M + H)$^+$ |
| 935 | N-{4-[(cyclopentylacetyl)amino]phenyl}-5-(methoxymethyl)-1,3-dihydro-2H-isoindole-2-carboxamide | $^1$H NMR (300 MHz, DMSO-$d_6$) δ ppm 9.69 (s, 1H), 8.27 (s, 1H), 7.51-7.40 (m, 4H), 7.36-7.22 (m, 3H), 4.74 (bs, 4H), 4.42 (s, 2H), 3.29 (s, 3H), 2.35-2.15 (m, 3H), 1.81-1.68 (m, 2H), 1.68-1.43 (m, 4H), 1.26-1.10 (m, 2H) | (ESI (+)) m/e 408 (M + H)$^+$ |

Example 313 methyl 2-({-4-[(cyclopentylacetyl)amino]phenyl}carbamoyl)isoindoline-5-carboxylate

Example 313A methyl 2-(4-nitrophenylcarbamoyl)isoindoline-5-carboxylate

The title compound was prepared as described in Example 1A, substituting 4-nitrophenyl isocyanate for methyl 4-isocyanatobenzoate and methyl isoindoline-5-carboxylate hydrochloride for isoindoline.

Example 313B methyl 2-(4-aminophenylcarbamoyl)isoindoline-5-carboxylate

The title compound was prepared as described in Example 274, substituting methyl 2-(4-nitrophenylcarbamoyl)isoindoline-5-carboxylate for 5-nitro-N-[4-(propylcarbamoyl)phenyl]-1,3-dihydro-2H-isoindole-2-carboxamide.

Example 313C methyl 2-({4-[(cyclopentylacetyl)amino]phenyl}carbamoyl)isoindoline-5-carboxylate The title compound was prepared as described in Example 278, substituting methyl 2-(4-aminophenylcarbamoyl)isoindoline-5-carboxylate for 5-amino-N-(4-(propylcarbamoyl)phenyl)isoindoline-2-carboxamide and 2-cyclopentylacetyl chloride for acetyl chloride. $^1$H NMR (300 MHz, DMSO-$d_6$) δ ppm 9.69 (s, 1H), 8.32 (s, 1H), 7.94-7.94 (m, 1H), 7.89-7.96 (m, 1H), 7.51 (d, J=8.1 Hz, 1H), 7.41-7.49 (m, 4H), 4.75-4.82 (m, 4H), 3.87 (s, 3H), 2.24-2.29 (m, 2H), 2.15-2.28 (m, 1H), 1.68-1.81 (m, 2H), 1.44-1.67 (m, 4H), 1.13-1.24 (m, 2H); MS (ESI(+)) m/e 422 (M+H)$^+$.

Example 314

2-({4-[(cyclopentylacetyl)amino]phenyl}carbamoyl)isoindoline-5-carboxylic acid

The title compound was prepared as described in Example 1B, substituting methyl 2-({4-[(cyclopentylacetyl)amino]phenyl}carbamoyl)isoindoline-5-carboxylate for methyl 4-(isoindoline-2-carboxamido)benzoate. $^1$H NMR (300 MHz, DMSO-$d_6$) δ ppm 12.97 (dd, J=4.1, 2.1 Hz, 1H), 9.70 (s, 1H), 8.32 (s, 1H), 7.88-7.92 (m, 2H), 7.46-7.50 (m, 1H), 7.43-7.48 (m, 4H), 4.79-4.81 (bs, 4H), 2.24-2.30 (m, 2H), 2.16-2.29 (m, 1H), 1.68-1.81 (m, 2H), 1.44-1.67 (m, 4H), 1.10-1.27 (m, 2H); MS (ESI(−)) m/e 406 (M−H)$^−$.

Example 315

N-{4-[(cyclopentylacetyl)amino]phenyl}-5-(hydroxymethyl)-1,3-dihydro-2H-isoindole-2-carboxamide To a stirring suspension of 2-(4-(2-cyclopentylacetamido)phenylcarbamoyl)isoindoline-5-carboxylic acid (18 mg, 0.044 mmol) in tetrahydrofuran was added 1M borane in tetrahydrofuran (0.18 mL, 0.18 mml) dropwise. The mixture was heated at 60° C. for 1 hour. The reaction was cooled to room temperature and treated with several drops of 4M HCl-dioxane and methanol and then the clear solution was stirred at room temperature for 2 hours. The reaction was concentrated and purified by reverse-phase HPLC to provide the title compound. $^1$H NMR (300 MHz, DMSO-$d_6$) δ ppm 9.69 (s, 1H), 8.26 (s, 1H), 7.45 (s, 4H), 7.28-7.32 (m, 2H), 7.22-7.26 (m, 1H), 5.18-5.22 (m, 1H), 4.72-4.73 (bs, 4H), 4.50-4.53 (bs, 2H), 2.17-2.32 (m, 3H), 1.70-1.80 (m, 2H), 1.44-1.67 (m, 4H), 1.13-1.24 (m, 2H); MS (ESI(+)) m/e 394 (M+H)$^+$.

Example 316

N-{4-[(2-cyclopentylethyl)amino]phenyl}-5-(hydroxymethyl)-1,3-dihydro-2H-isoindole-2-carboxamide To a stirring suspension of 2-(4-(2-cyclopentylacetamido)phenylcarbamoyl)isoindoline-5-carboxylic acid (18 mg, 0.044 mmol) in tetrahydrofuran was added 1M borane in tetrahydrofuran (0.18 mL, 0.18 mml) dropwise. The mixture was heated at 60° C. for 1 hour. The reaction was cooled to room temperature and treated with several drops of 4M HCl-dioxane and methanol and then the clear solution was stirred at room temperature for 2 hours. The reaction was concentrated and purified by reverse-phase HPLC to provide the title compound. $^1$H NMR (300 MHz, DMSO-d$_6$) δ ppm 7.92 (s, 1H), 7.27-7.31 (m, 2H), 7.24 (d, J=8.1 Hz, 1H), 7.15-7.20 (m, 2H), 6.45-6.51 (m, 2H), 5.17-5.21 (m, 2H), 4.68-4.69 (bs, 4H), 4.51 (d, J=5.4 Hz, 2H), 2.97 (q, J=6.7 Hz, 2H), 1.70-1.95 (m, 3H), 1.42-1.66 (m, 6H), 1.04-1.20 (m, 2H); MS (ESI(+)) m/e 380 (M+H)$^+$.

Example 317 tert-Butyl 4-{4-[(1,3-dihydro-2H-isoindol-2-ylcarbonyl)amino]phenyl}-3,6-dihydropyridine-1(2H)-carboxylate Example 317A N-(4-bromophenyl)isoindoline-2-carboxamide The title compound was prepared as described in Example 1A, substituting 4-bromophenyl isocyanate for methyl 4-isocyanatobenzoate.

Example 317B tert-butyl 4-{4-[(1,3-dihydro-2H-isoindol-2-ylcarbonyl)amino]phenyl}-3,6-dihydropyridine-1(2H)-carboxylate The title compound was prepared as described in Example 280, substituting tert-butyl 4-(4,4,5,5-tetramethyl-1,3,2-dioxaborolan-2-yl)-5,6-dihydropyridine-1(2H)-carboxylate for 1H-pyrazol-3-ylboronic acid and N-(4-bromophenyl)isoindoline-2-carboxamide for 5-bromo-N-(4-(propylcarbamoyl)phenyl)isoindoline-2-carboxamide. $^1$H NMR (400 MHz, DMSO-d$_6$) δ ppm 8.38 (s, 1H), 7.55-7.57 (m, 2H), 7.26-7.42 (m, 6H), 6.06-6.09 (bs, 1H), 4.76-4.77 (bs, 4H), 3.97-4.00 (m, 2H), 3.51-3.55 (m, 2H), 2.42-2.46 (m, 2H), 1.43 (s, 9H); MS (ESI(−)) m/e 418 (M−H)$^−$.

Example 318

N-[4-(1,2,3,6-tetrahydropyridin-4-yl)phenyl]-1,3-dihydro-2H-isoindole-2-carboxamide The title compound was prepared as described in Example 2D, substituting tert-butyl 4-{4-[(1,3-dihydro-2H-isoindol-2-ylcarbonyl)amino]phenyl}-3,6-dihydropyridine-1(2H)-carboxylate for tert-butyl 4-((4-(5-fluoroisoindoline-2-carboxamido)benzamido)methyl)benzylcarbamate. $^1$H NMR (400 MHz, DMSO-d$_6$) δ ppm 8.44 (s, 1H), 7.58-7.61 (m, 2H), 7.30-7.41 (m, 6H), 6.12-6.14 (bs, 1H), 4.77-4.78 (bs, 4H), 3.70-3.72 (m, 2H), 3.27-3.31 (m, 2H), 2.60-2.64 (m, 2H); MS (ESI(+)) m/e 320 (M+H)$^+$.

Example 319

N-{4-[1-(3-methylbutyl)-1H-pyrazol-4-yl]phenyl}-1,3-dihydro-2H-isoindole-2-carboxamide The title compound was prepared as described in Example 280, substituting 1-isopentyl-4-(4,4,5,5-tetramethyl-1,3,2-dioxaborolan-2-yl)-1H-pyrazole for 1H-pyrazol-3-ylboronic acid and N-(4-bromophenyl)isoindoline-2-carboxamide for 5-bromo-N-(4-(propylcarbamoyl)phenyl)isoindoline-2-carboxamide. $^1$H NMR (300 MHz, DMSO-d$_6$) δ ppm 0.91 (d, J=6.4 Hz, 6H), 1.40-1.60 (m, 1H), 1.70 (q, J=6.8 Hz, 2H), 4.11 (t, J=7.1 Hz, 2H), 4.77 (s, 4H), 7.13-7.40 (m, 4H), 7.42-7.50 (m, 2H), 7.50-7.61 (m, 2H), 7.78 (s, 1H), 8.08 (s, 1H), 8.32 (s, 1H); MS (ESI(+)) m/e 375 (M+H)$^+$.

Example 320

N-[4-(1-methyl-1H-pyrazol-4-yl)phenyl]-1,3-dihydro-2H-isoindole-2-carboxamide

The title compound was prepared as described in Example 280, substituting 1-methyl-4-(4,4,5,5-tetramethyl-1,3,2-dioxaborolan-2-yl)-1H-pyrazole for 1H-pyrazol-3-ylboronic acid and N-(4-bromophenyl)isoindoline-2-carboxamide for 5-bromo-N-(4-(propylcarbamoyl)phenyl)isoindoline-2-carboxamide. $^1$H NMR (300 MHz, DMSO-d$_6$) δ ppm 3.84 (s, 3H), 4.77 (s, 4H), 7.24-7.40 (m, 4H), 7.40-7.49 (m, 2H), 7.50-7.60 (m, 2H), 7.77 (s, 1H), 8.02 (s, 1H), 8.33 (s, 1H); MS (ESI(+)) m/e 319 (M+H)$^+$.

Example 321

N-{4-[(1E)-5-phenylpent-1-en-1-yl]phenyl}-1,3-dihydro-2H-isoindole-2-carboxamide The title compound was prepared as described in Example 280, substituting (E)-4,4,5,5-tetramethyl-2-(5-phenylpent-1-enyl)-1,3,2-dioxaborolane for 1H-pyrazol-3-ylboronic acid and N-(4-bromophenyl)isoindoline-2-carboxamide for 5-bromo-N-(4-(propylcarbamoyl)phenyl)isoindoline-2-carboxamide. $^1$H NMR (300 MHz, DMSO-d$_6$) δ ppm 1.60-1.84 (m, 2H), 2.19 (q, J=7.0 Hz, 2H), 2.55-2.71 (m, 2H), 4.76 (s, 4H), 6.12-6.27 (m, 1H), 6.26-6.43 (m, 1H), 7.09-7.44 (m, 11H), 7.52 (d, J=8.5 Hz, 2H), 8.33 (s, 1H); MS (ESI(+)) m/e 383 (M+H)$^+$.

Example 322

N-[4-(1-propyl-1H-pyrazol-4-yl)phenyl]-1,3-dihydro-2H-isoindole-2-carboxamide

The title compound was prepared as described in Example 280, substituting 1-propyl-4-(4,4,5,5-tetramethyl-1,3,2-dioxaborolan-2-yl)-1H-pyrazole for 1H-pyrazol-3-ylboronic acid and N-(4-bromophenyl)isoindoline-2-carboxamide for 5-bromo-N-(4-(propylcarbamoyl)phenyl)isoindoline-2-carboxamide. $^1$H NMR (300 MHz, DMSO-d$_6$) δ ppm 0.85 (t, J=7.3 Hz, 3H), 1.69-1.93 (m, 2H), 4.05 (t, J=6.9 Hz, 2H), 4.77 (s, 4H), 7.26-7.40 (m, 4H), 7.42-7.49 (m, 2H), 7.52-7.61 (m, 2H), 7.79 (s, 1H), 8.07 (s, 1H), 8.33 (s, 1H); MS (ESI(+)) m/e 347 (M+H)$^+$.

Example 323

N-[4-(1-benzyl-1H-pyrazol-4-yl)phenyl]-1,3-dihydro-2H-isoindole-2-carboxamide

The title compound was prepared as described in Example 280, substituting 1-benzyl-4-(4,4,5,5-tetramethyl-1,3,2-dioxaborolan-2-yl)-1H-pyrazole for 1H-pyrazol-3-ylboronic acid and N-(4-bromophenyl)isoindoline-2-carboxamide for 5-bromo-N-(4-(propylcarbamoyl)phenyl)isoindoline-2-carboxamide. $^1$H NMR (300 MHz, DMSO-d$_6$) δ ppm 4.77 (s, 4H), 5.33 (s, 2H), 7.21-7.42 (m, 9H), 7.41-7.51 (m, 2H), 7.51-7.61 (m, 2H), 7.84 (s, 1H), 8.17 (s, 1H), 8.33 (s, 1H); MS (ESI(+)) m/e 395 (M+H)+.

Example 324

N-{4-[1-(2-hydroxyethyl)-1H-pyrazol-4-yl]phenyl}-1,3-dihydro-2H-isoindole-2-carboxamide The title compound was prepared as described in Example 280, substituting 2-(4-(4,4,5,5-tetramethyl-1,3,2-dioxaborolan-2-yl)-1H-pyrazol-1-yl)ethanol for 1H-pyrazol-3-ylboronic acid and N-(4-bromophenyl)isoindoline-2-carboxamide for 5-bromo-N-(4-(propylcarbamoyl)phenyl)isoindoline-2-carboxamide. $^1$H NMR (300 MHz, DMSO-d$_6$) δ ppm 3.76 (q, J=5.8 Hz, 2H), 4.14 (t, J=5.6 Hz, 2H), 4.77 (s, 4H), 4.90 (t, J=5.4 Hz, 1H), 7.25-7.41 (m, 4H), 7.41-7.51 (m, 2H), 7.51-7.60 (m, 2H), 7.80 (s, 1H), 8.04 (s, 1H), 8.32 (s, 1H); MS (ESI(+)) m/e 349 (M+H)+.

Example 325

N-[6-(1-propyl-1H-pyrazol-4-yl)pyridin-3-yl]-1,3-dihydro-2H-isoindole-2-carboxamide Example 325A N-(6-chloropyridin-3-yl)isoindoline-2-carboxamide The title compound was prepared as described in Example 1A, substituting 2-chloro-5-isocyanatopyridine for methyl 4-isocyanatobenzoate.

Example 325B

N-[6-(1-propyl-1H-pyrazol-4-yl)pyridin-3-yl]-1,3-dihydro-2H-isoindole-2-carboxamide The title compound was prepared as described in Example 280, substituting 1-propyl-4-(4,4,5,5-tetramethyl-1,3,2-dioxaborolan-2-yl)-1H-pyrazole for 1H-pyrazol-3-ylboronic acid and N-(6-chloropyridin-3-yl)isoindoline-2-carboxamide for 5-bromo-N-(4-(propylcarbamoyl)phenyl)isoindoline-2-carboxamide. $^1$H NMR (300 MHz, DMSO-d$_6$) δ ppm 8.90-8.92 (bs, 1H), 8.84 (d, J=2.5 Hz, 1H), 8.39 (s, 1H), 8.25 (dd, J=8.8, 2.5 Hz, 1H), 8.08 (s, 1H), 7.87 (d, J=8.8 Hz, 1H), 7.31-7.41 (m, 4H), 4.79-4.83 (bs, 4H), 4.13 (t, J=6.9 Hz, 2H), 1.77-1.89 (m, 2H), 0.86 (t, J=7.3 Hz, 3H); MS (ESI(+)) m/e 348 (M+H)+.

Example 326

N-{6-[1-(3-methylbutyl)-1H-pyrazol-4-yl]pyridin-3-yl}-1,3-dihydro-2H-isoindole-2-carboxamide The title compound was prepared as described in Example 280, substituting 1-isopentyl-4-(4,4,5,5-tetramethyl-1,3,2-dioxaborolan-2-yl)-1H-pyrazole for 1H-pyrazol-3-ylboronic acid and N-(6-chloropyridin-3-yl)isoindoline-2-carboxamide for 5-bromo-N-(4-(propylcarbamoyl)phenyl)isoindoline-2-carboxamide. $^1$H NMR (300 MHz, DMSO-d$_6$) δ ppm 8.85-8.87 (bs, 1H), 8.81 (d, J=2.5 Hz, 1H), 8.38 (s, 1H), 8.21 (dd, J=8.8, 2.5 Hz, 1H), 8.05 (s, 1H), 7.82 (d, J=8.8 Hz, 1H), 7.31-7.41 (m, 4H), 4.78-4.83 (bs, 4H), 4.19 (t, J=7.1 Hz, 2H), 1.71 (q, J=7.0 Hz, 2H), 1.40-1.59 (m, 1H), 0.92 (d, J=6.6 Hz, 6H); MS (ESI(−)) m/e 374 (M−H)−.

Example 327

N-[4-(5-phenylpentyl)phenyl]-1,3-dihydro-2H-isoindole-2-carboxamide

The title compound was prepared as described in Example 274, substituting N-{4-[(1E)-5-phenylpent-1-en-1-yl]phenyl}-1,3-dihydro-2H-isoindole-2-carboxamide for 5-nitro-N-[4-(propylcarbamoyl)phenyl]-1,3-dihydro-2H-isoindole-2-carboxamide. $^1$H NMR (300 MHz, DMSO-d$_6$) δ ppm 1.21-1.40 (m, 4H), 1.49-1.67 (m, 4H), 2.45-2.62 (m, 2H), 4.75 (s, 4H), 7.05 (d, J=8.7 Hz, 2H), 7.14-7.40 (m, 9H), 7.44 (d, J=8.3 Hz, 2H), 8.23 (s, 1H); MS (ESI(+)) m/e 385 (M+H)+.

Example 328

N-[2-fluoro-4-(1-propyl-1H-pyrazol-4-yl)phenyl]-1,3-dihydro-2H-isoindole-2-carboxamide Example 328A N-(4-bromo-2-fluorophenyl)isoindoline-2-carboxamide The title compound was prepared as described in Example 1A, substituting 4-bromo-2-fluoro-1-isocyanatobenzene for methyl 4-isocyanatobenzoate.

Example 328B

N-[2-fluoro-4-(1-propyl-1H-pyrazol-4-yl)phenyl]-1,3-dihydro-2H-isoindole-2-carboxamide The title compound was prepared as described in Example 280, substituting 1-propyl-4-(4,4,5,5-tetramethyl-1,3,2-dioxaborolan-2-yl)-1H-pyrazole for 1H-pyrazol-3-ylboronic acid and N-(4-bromo-2-fluorophenyl)isoindoline-2-carboxamide for 5-bromo-N-(4-(propylcarbamoyl)phenyl)isoindoline-2-carboxamide. $^1$H NMR (300 MHz, DMSO-d$_6$) δ ppm 8.19 (s, 1H), 8.03 (s, 1H), 7.89 (s, 1H), 7.57 (t, J=8.4 Hz, 1H), 7.46 (dd, J=12.1, 1.9 Hz, 1H), 7.24-7.39 (m, 5H), 4.76-4.78 (bs, 4H), 4.06 (t, J=6.9 Hz, 2H), 1.75-1.88 (m, 2H), 0.86 (t, J=7.3 Hz, 3H); MS (ESI(+)) m/e 365 (M+H)+.

Example 329

N-{2-fluoro-4-[1-(3-methylbutyl)-1H-pyrazol-4-yl]phenyl}-1,3-dihydro-2H-isoindole-2-carboxamide The title compound was prepared as described in Example 280, substituting 1-isopentyl-4-(4,4,5,5-tetramethyl-1,3,2-dioxaborolan-2-yl)-1H-pyrazole for 1H-pyrazol-3-ylboronic acid and N-(4-bromo-2-fluorophenyl)isoindoline-2-carboxamide for 5-bromo-N-(4-(propylcarbamoyl)phenyl)isoindoline-2-carboxamide. $^1$H NMR (300 MHz, DMSO-d$_6$) δ ppm 8.21 (s, 1H), 8.04 (s, 1H), 7.88 (s, 1H), 7.56 (t, J=8.4 Hz, 1H), 7.46 (dd, J=12.1, 1.9 Hz, 1H), 7.25-7.41 (m, 5H), 4.76-4.81 (m, 4H), 4.12 (t, J=7.2 Hz, 2H), 1.70 (q, J=7.1 Hz, 2H), 1.40-1.59 (m, 1H), 0.91 (d, J=6.6 Hz, 6H); MS (ESI(+)) m/e 393 (M+H)+.

Example 330

N-[4-(1-butyryl-1,2,3,6-tetrahydropyridin-4-yl)phenyl]-1,3-dihydro-2H-isoindole-2-carboxamide The title compound was prepared as described in Example 278, substituting butyryl chloride for acetyl chloride and N-[4-(1,2,3,6-tetrahydropyridin-4-yl)phenyl]-1,3-dihydro-2H-isoindole-2-carboxamide for 5-amino-N-(4-(propylcarbamoyl)phenyl)isoindoline-2-carboxamide. $^1$H NMR (400 MHz, DMSO-d$_6$) δ ppm 8.38 (s, 1H), 7.55-7.58 (m, 2H), 7.27-7.38 (m, 6H), 6.09-6.11 (m, 1H), 4.77 (s, 4H), 4.08-4.14 (m, 2H), 3.58-3.68 (m, 2H), 2.39-2.51 (m, 2H), 2.34 (dt, J=19.8, 7.3 Hz, 2H), 1.46-1.62 (m, 2H), 0.88-0.93 (m, 3H); MS (ESI(+)) m/e 390 (M+H)$^+$.

Example 331

N-[4-(1-isobutyryl-1,2,3,6-tetrahydropyridin-4-yl)phenyl]-1,3-dihydro-2H-isoindole-2-carboxamide The title compound was prepared as described in Example 278, substituting isobutyryl chloride for acetyl chloride and N-[4-(1,2,3,6-tetrahydropyridin-4-yl)phenyl]-1,3-dihydro-2H-isoindole-2-carboxamide for 5-amino-N-(4-(propylcarbamoyl)phenyl)isoindoline-2-carboxamide. $^1$H NMR (500 MHz, DMSO-d$_6$) δ ppm 8.40 (s, 1H), 7.55-7.58 (m, 2H), 7.30-7.38 (m, 6H), 6.11-6.13 (bs, 1H), 4.76-4.77 (bs, 4H), 4.19-4.21 (m, 1H), 4.08-4.09 (m, 1H), 3.65-3.72 (m, 2H), 2.85-3.00 (m, 1H), 2.40-2.56 (m, 2H), 1.00-1.07 (m, 6H); MS (ESI(+)) m/e 390 (M+H)$^+$.

Example 332

N-[4-(1-benzoyl-1,2,3,6-tetrahydropyridin-4-yl)phenyl]-1,3-dihydro-2H-isoindole-2-carboxamide The title compound was prepared as described in Example 278, substituting benzoyl chloride for acetyl chloride and N-[4-(1,2,3,6-tetrahydropyridin-4-yl)phenyl]-1,3-dihydro-2H-isoindole-2-carboxamide for 5-amino-N-(4-(propylcarbamoyl)phenyl)isoindoline-2-carboxamide. $^1$H NMR (400 MHz, DMSO-d$_6$) δ ppm 8.39 (s, 1H), 7.56-7.59 (m, 2H), 7.44-7.49 (m, 5H), 7.34-7.40 (m, 4H), 7.29-7.34 (m, 2H), 5.91-6.27 (m, 1H), 4.76-4.77 (bs, 4H), 4.02-4.26 (m, 2H), 3.36-3.59 (m, 2H), 2.51-2.61 (m, 2H); MS (ESI(+)) m/e 424 (M+H)$^+$.

Example 333

N-{4-[1-(isopropylsulfonyl)-1,2,3,6-tetrahydropyridin-4-yl]phenyl}-1,3-dihydro-2H-isoindole-2-carboxamide The title compound was prepared as described in Example 283, substituting propane-2-sulfonyl chloride for methanesulfonyl chloride and N-[4-(1,2,3,6-tetrahydropyridin-4-yl)phenyl]-1,3-dihydro-2H-isoindole-2-carboxamide for 5-amino-N-(4-(propylcarbamoyl)phenyl)isoindoline-2-carboxamide. $^1$H NMR (400 MHz, DMSO-d$_6$) δ ppm 8.38-8.40 (m, 1H), 7.56-7.59 (m, 2H), 7.29-7.38 (m, 6H), 6.11-6.14 (m, 1H), 4.76-4.80 (m, 4H), 3.93-3.96 (m, 2H), 3.49 (t, J=5.5 Hz, 2H), 3.35-3.45 (m, 1H), 2.47-2.51 (m, 2H), 1.24 (d, J=6.9 Hz, 6H); MS (ESI(−)) m/e 424 (M−H)$^−$.

Example 334

N-(1'-isobutyryl-1',2',3',6'-tetrahydro-2,4'-bipyridin-5-yl)-1,3-dihydro-2H-isoindole-2-carboxamide Example 334A tert-butyl 4-(5-(isoindoline-2-carboxamido)pyridin-2-yl)-5,6-dihydropyridine-1(2H)-carboxylate The title compound was prepared as described in Example 280, substituting tert-butyl 4-(4,4,5,5-tetramethyl-1,3,2-dioxaborolan-2-yl)-5,6-dihydropyridine-1(2H)-carboxylate for 1H-pyrazol-3-ylboronic acid and N-(6-chloropyridin-3-yl)isoindoline-2-carboxamide for 5-bromo-N-(4-(propylcarbamoyl)phenyl)isoindoline-2-carboxamide.

Example 334B

N-(6-(1,2,3,6-tetrahydropyridin-4-yl)pyridin-3-yl)isoindoline-2-carboxamide

The title compound was prepared as described in Example 2D, substituting tert-butyl 4-(5-(isoindoline-2-carboxamido)pyridin-2-yl)-5,6-dihydropyridine-1(2H)-carboxylate for tert-butyl 4-((4-(5-fluoroisoindoline-2-carboxamido)benzamido)methyl)benzylcarbamate.

Example 334C tert-butyl 4-(5-(isoindoline-2-carboxamido)pyridin-2-yl)-5,6-dihydropyridine-1(2H)-carboxylate The title compound was prepared as described in Example 278, substituting isobutyryl chloride for acetyl chloride and N-(6-(1,2,3,6-tetrahydropyridin-4-yl)pyridin-3-yl)isoindoline-2-carboxamide for 5-amino-N-(4-(propylcarbamoyl)phenyl)isoindoline-2-carboxamide. $^1$H NMR (400 MHz, DMSO-d$_6$, Temp=90° C.) δ ppm 8.70 (d, J=2.6 Hz, 1H), 8.33-8.37 (m, 1H), 7.95 (dd, J=8.6, 2.6 Hz, 1H), 7.44 (d, J=8.6 Hz, 1H), 7.28-7.36 (m, 4H), 6.54-6.56 (m, 1H), 4.79 (s, 4H), 4.16-4.18 (m, 2H), 3.68 (t, J=5.7 Hz, 2H), 2.86-2.97 (m, 1H), 2.54-2.63 (m, 2H), 1.04 (d, J=6.7 Hz, 6H); MS (ESI(−)) m/e 389 (M−H)$^−$.

Example 335

N-(1'-benzoyl-1',2',3',6'-tetrahydro-2,4'-bipyridin-5-yl)-1,3-dihydro-2H-isoindole-2-carboxamide The title compound was prepared as described in Example 278, substituting benzoyl chloride for acetyl chloride and N-(6-(1,2,3,6-tetrahydropyridin-4-yl)pyridin-3-yl)isoindoline-2-carboxamide for 5-amino-N-(4-(propylcarbamoyl)phenyl)isoindoline-2-carboxamide. $^1$H NMR (400 MHz, DMSO-d$_6$) δ ppm 8.71 (d, J=2.5 Hz, 1H), 8.61 (s, 1H), 8.01 (dd, J=8.6, 2.2 Hz, 1H), 7.42-7.54 (m, 6H), 7.35-7.39 (m, 2H), 7.29-7.35 (m, 2H), 6.46-6.67 (m, 1H), 4.79 (s, 4H), 4.05-4.32 (m, 2H), 3.77-3.94 (m, 1H), 3.47-3.58 (m, 1H), 2.61-2.65 (m, 2H); MS (ESI(+)) m/e 425 (M+H)$^+$.

Example 336

N-[4-(4-benzoylpiperazin-1-yl)phenyl]-1,3-dihydro-2H-isoindole-2-carboxamide

Example 336A

N-(4-(piperazin-1-yl)phenyl)isoindoline-2-carboxamide

The title compound was prepared as described in Example 2D, substituting tert-butyl 4-(4-(isoindoline-2-carboxamido)

Example 336B

N-[4-(4-benzoylpiperazin-1-yl)phenyl]-1,3-dihydro-2H-isoindole-2-carboxamide

The title compound was prepared as described in Example 278, substituting benzoyl chloride for acetyl chloride and N-(4-(piperazin-1-yl)phenyl)isoindoline-2-carboxamide for 5-amino-N-(4-(propylcarbamoyl)phenyl)isoindoline-2-carboxamide. $^1$H NMR (300 MHz, DMSO-$d_6$) δ ppm 8.14 (s, 1H), 7.38-7.50 (m, 7H), 7.28-7.38 (m, 4H), 6.87-6.91 (m, 2H), 4.74 (s, 4H), 3.39-3.90 (m, 4H), 3.01-3.17 (m, 4H); MS (ESI(+)) m/e 427 (M+H)$^+$.

Example 337

N-{4-[4-(isopropylsulfonyl)piperazin-1-yl]phenyl}-1,3-dihydro-2H-isoindole-2-carboxamide The title compound was prepared as described in Example 283, substituting isopropylsulfonyl chloride for methanesulfonyl chloride and N-(4-(piperazin-1-yl)phenyl)isoindoline-2-carboxamide for 5-amino-N-(4-(propylcarbamoyl)phenyl)isoindoline-2-carboxamide. $^1$H NMR (300 MHz, DMSO-$d_6$) δ ppm 8.16 (s, 1H), 7.39-7.45 (m, 2H), 7.27-7.38 (m, 4H), 6.88-6.92 (m, 2H), 4.74 (s, 4H), 3.07-3.12 (m, 4H), 1.25 (d, J=6.8 Hz, 6H); MS (ESI(+)) m/e 429 (M+H)$^+$.

Example 338

N-{4-[4-(phenylsulfonyl)piperazin-1-yl]phenyl}-1,3-dihydro-2H-isoindole-2-carboxamide The title compound was prepared as described in Example 283, substituting benzenesulfonyl chloride for methanesulfonyl chloride and N-(4-(piperazin-1-yl)phenyl)isoindoline-2-carboxamide for 5-amino-N-(4-(propylcarbamoyl)phenyl)isoindoline-2-carboxamide. $^1$H NMR (300 MHz, DMSO-$d_6$) δ ppm 8.14 (s, 1H), 7.65-7.80 (m, 5H), 7.35-7.41 (m, 2H), 7.27-7.37 (m, 4H), 6.81-6.85 (m, 2H), 4.72 (s, 4H), 3.09-3.15 (m, 4H), 2.99-3.04 (m, 4H); MS (ESI(−)) m/e 461 (M−H)$^-$.

Example 339

N-{4-[3-(benzoylamino)pyrrolidin-1-yl]phenyl}-1,3-dihydro-2H-isoindole-2-carboxamide

Example 339A tert-butyl 1-(4-nitrophenyl)pyrrolidin-3-ylcarbamate

A solution of 1-fluoro-4-nitrobenzene (508 mg, 3.6 mmol) and tert-butyl pyrrolidin-3-ylcarbamate (671 mg, 3.6 mmol) in N,N-dimethylformamide (7 mL) was heated at 55° C. for 1.5 hours and then stirred overnight at room temperature. The reaction mixture was poured into water and the suspension was filtered with water washes to provide the title compound after drying.

Example 339B tert-butyl 1-(4-aminophenyl)pyrrolidin-3-ylcarbamate

The title compound was prepared as described in Example 274, substituting (+/−)-tert-butyl 1-(4-nitrophenyl)pyrrolidin-3-ylcarbamate for 5-nitro-N-[4-(propylcarbamoyl)phenyl]-1,3-dihydro-2H-isoindole-2-carboxamide.

Example 339C tert-butyl 1-(4-(isoindoline-2-carboxamido)phenyl)pyrrolidin-3-ylcarbamate The title compound was prepared as described in Example 272, substituting (+/−)-tert-butyl 1-(4-aminophenyl)pyrrolidin-3-ylcarbamate for 4-amino-N-propylbenzamide and isoindoline for methyl isoindoline-5-carboxylate hydrochloride in Example 272B.

Example 339D

N-[4-(3-aminopyrrolidin-1-yl)phenyl]-1,3-dihydro-2H-isoindole-2-carboxamide

The title compound was prepared as described in Example 2, substituting (+/−)-tert-butyl 1-(4-(isoindoline-2-carboxamido)phenyl)pyrrolidin-3-ylcarbamate for tert-butyl 4-((4-(5-fluoroisoindoline-2-carboxamido)benzamido)methyl)benzylcarbamate in Example 2D.

Example 339E

N-{4-[(3R)-3-(benzoylamino)pyrrolidin-1-yl]phenyl}-1,3-dihydro-2H-isoindole-2-carboxamide and
N-{4-[(3S)-3-(benzoylamino)pyrrolidin-1-yl]phenyl}-1,3-dihydro-2H-isoindole-2-carboxamide The title compounds were prepared as described in Example 278, substituting benzoyl chloride for acetyl chloride and (+/−)-N-(4-(3-aminopyrrolidin-1-yl)phenyl)isoindoline-2-carboxamide for 5-amino-N-(4-(propylcarbamoyl)phenyl)isoindoline-2-carboxamide. $^1$H NMR (300 MHz, DMSO-$d_6$) δ ppm 8.61 (d, J=6.8 Hz, 1H), 8.01 (s, 1H), 7.85-7.89 (m, 2H), 7.42-7.56 (m, 3H), 7.28-7.37 (m, 6H), 6.50 (d, J=8.7 Hz, 2H), 4.72 (s, 4H), 4.56-4.67 (m, 1H), 3.53-3.59 (m, 1H), 3.36-3.45 (m, 1H), 3.16-3.24 (m, 1H), 2.22-2.31 (m, 1H), 2.03-2.13 (m, 1H); MS (ESI(+)) m/e 427 (M+H)$^+$.

Example 340

N-{4-[(3R)-3-(butyrylamino)pyrrolidin-1-yl]phenyl}-1,3-dihydro-2H-isoindole-2-carboxamide and
N-{4-[(3S)-3-(butyrylamino)pyrrolidin-1-yl]phenyl}-1,3-dihydro-2H-isoindole-2-carboxamide The title compounds were prepared as described in Example 278, substituting butyryl chloride for acetyl chloride. $^1$H NMR (300 MHz, DMSO-$d_6$) δ ppm 8.06 (d, J=6.9 Hz, 1H), 7.28-7.37 (m, 6H), 6.47 (d, J=8.7 Hz, 2H), 4.72 (s, 4H), 4.36 (h, J=5.7 Hz, 1H), 3.41-3.47 (m, 1H), 3.17-3.23 (m, 1H), 2.89-3.05 (m, 1H), 2.10-2.28 (m, 1H), 2.05 (t, J=7.3 Hz, 2H), 1.81-1.96 (m, 1H), 1.45-1.58 (m, 2H), 0.85 (t, J=7.4 Hz, 3H); MS (ESI(+)) m/e 393 (M+H)$^+$.

Example 341 tert-butyl 4-{4-[(1,3-dihydro-2H-isoindol-2-ylcarbonyl)amino]phenyl}piperazine-1-carboxylate

Example 341A tert-butyl 4-(4-nitrophenyl)piperazine-1-carboxylate

A solution of 1-fluoro-4-nitrobenzene (500 mg, 3.54 mmol) and tert-butyl piperazine-1-carboxylate (726 mg, 3.9 mmol) in dimethylformamide was treated with potassium carbonate (735 mg, 5.32 mmol) and the suspension was heated at 55° C. for 4 hours and then stirred overnight at room temperature. The reaction was poured into water and the suspension was filtered with water washes to provide the title compound after vacuum drying.

Example 341B tert-butyl 4-(4-aminophenyl)piperazine-1-carboxylate

The title compound was prepared as described in Example 274, substituting tert-butyl 4-(4-nitrophenyl)piperazine-1-carboxylate for 5-nitro-N-[4-(propylcarbamoyl)phenyl]-1,3-dihydro-2H-isoindole-2-carboxamide.

Example 341C tert-butyl 4-(4-(isoindoline-2-carboxamido)phenyl)piperazine-1-carboxylate The title compound was prepared as described in Example 272B, substituting tert-butyl 4-(4-aminophenyl)piperazine-1-carboxylate for 4-amino-N-propylbenzamide and isoindoline for methyl isoindoline-5-carboxylate hydrochloride. $^1$H NMR (300 MHz, DMSO-$d_6$) δ ppm 8.14 (s, 1H), 7.38-7.44 (m, 2H), 7.27-7.39 (m, 4H), 6.88-6.90 (m, 1H), 6.86 (s, 1H), 4.73 (s, 4H), 3.40-3.51 (m, 4H), 2.98-3.02 (m, 4H), 1.42 (s, 9H); MS (ESI(−)) m/e 421 (M−H)$^−$.

Example 342

N-[4-(4-propionylpiperazin-1-yl)phenyl]-1,3-dihydro-2H-isoindole-2-carboxamide

The title compound was prepared as described in Example 278, substituting propionyl chloride for acetyl chloride and N-(4-(piperazin-1-yl)phenyl)isoindoline-2-carboxamide for 5-amino-N-(4-(propylcarbamoyl)phenyl)isoindoline-2-carboxamide. $^1$H NMR (300 MHz, DMSO-$d_6$) δ ppm 8.14 (s, 1H), 7.38-7.44 (m, 2H), 7.28-7.39 (m, 4H), 6.87-6.90 (m, 2H), 4.74 (s, 4H), 3.54-3.60 (m, 4H), 2.95-3.10 (m, 4H), 2.36 (q, J=7.4 Hz, 2H), 1.03 (s, 1H), 1.00 (d, J=7.4 Hz, 2H); MS (ESI(+)) m/e 379 (M+H)$^+$.

Example 343

N-{4-[4-(cyclopropylcarbonyl)piperazin-1-yl]phenyl}-1,3-dihydro-2H-isoindole-2-carboxamide The title compound was prepared as described in Example 278, substituting cyclopropanecarbonyl chloride for acetyl chloride and N-(4-(piperazin-1-yl)phenyl)isoindoline-2-carboxamide for 5-amino-N-(4-(propylcarbamoyl)phenyl)isoindoline-2-carboxamide. $^1$H NMR (300 MHz, DMSO-$d_6$) δ ppm 8.15 (s, 1H), 7.38-7.45 (m, 2H), 7.28-7.39 (m, 4H), 6.87-6.93 (m, 2H), 4.74 (s, 4H), 3.73-3.90 (m, 2H), 3.50-3.70 (m, 2H), 3.02-3.18 (m, 4H), 1.98-2.07 (m, 1H), 0.68-0.77 (m, 4H); MS (ESI(−)) m/e 389 (M−H)$^−$.

Example 344

N-(2-butyryl-2,3-dihydro-1H-isoindol-5-yl)-1,3-dihydro-2H-isoindole-2-carboxamide Example 344A tert-butyl 5-(isoindoline-2-carboxamido)isoindoline-2-carboxylate In a 250 mL round bottom flask was mixed at room temperature triphosgene (234 mg, 0.790 mmol) in anhydrous dichloromethane (25 mL). To this solution was added dropwise over 15 minutes, a slurry of tert-butyl 5-aminoisoindoline-2-carboxylate (500 mg, 2.134 mmol) and diisopropylethylamine (0.410 ml, 2.347 mmol) in anhydrous dichloromethane (20 mL). The mixture was stirred overnight at room temperature. A solution of isoindoline (0.242 ml, 2.134 mmol) and diisopropylethylamine (0.410 ml, 2.347 mmol) in anhydrous dichloromethane (20 mL) was added in one portion. The reaction stirred overnight at room temperature. The solvent was removed and the residue was purified by normal phase flash chromatography to provide the title compound.

Example 344B

N-(isoindolin-5-yl)isoindoline-2-carboxamide

The title compound was prepared as described in Example 2D, substituting tert-butyl 5-(isoindoline-2-carboxamido)isoindoline-2-carboxylate for tert-butyl 4-((4-(5-fluoroisoindoline-2-carboxamido)benzamido)methyl)benzylcarbamate.

Example 344C

N-(2-butyryl-2,3-dihydro-1H-isoindol-5-yl)-1,3-dihydro-2H-isoindole-2-carboxamide The title compound was prepared as described in Example 278, substituting butyryl chloride for acetyl chloride and N-(isoindolin-5-yl)isoindoline-2-carboxamide for 5-amino-N-(4-(propylcarbamoyl)phenyl)isoindoline-2-carboxamide. $^1$H NMR (400 MHz, DMSO-$d_6$) δ ppm 8.39 (s, 1H), 7.59-7.61 (bs, 1H), 7.43-7.48 (m, 1H), 7.30-7.41 (m, 4H), 7.22 (t, J=7.7 Hz, 1H), 4.77 (d, J=13.9 Hz, 2H), 4.77 (s, 4H), 4.55-4.60 (m, 2H), 2.33 (td, J=7.3, 3.7 Hz, 2H), 1.54-1.63 (m, 2H), 0.93 (td, J=7.3, 1.4 Hz, 3H); MS (ESI(+)) m/e 350 (M+H)$^+$.

Example 345

N-(2-isobutyryl-2,3-dihydro-1H-isoindol-5-yl)-1,3-dihydro-2H-isoindole-2-carboxamide The title compound was prepared as described in Example 278, substituting isobutyryl chloride for acetyl chloride and N-(isoindolin-5-yl)isoindoline-2-carboxamide for 5-amino-N-(4-(propylcarbamoyl)phenyl)isoindoline-2-carboxamide. $^1$H NMR (400 MHz, DMSO-$d_6$) δ ppm 8.40 (s, 1H), 7.59-7.61 (bs, 1H), 7.46 (ddd, J=10.8, 8.5, 2.1 Hz, 1H), 7.30-7.38 (m, 4H), 7.20-7.24 (m, 1H), 4.82-4.87 (m, 2H), 4.76-4.77 (bs, 4H), 4.55-4.60 (m, 2H), 2.78 (h, J=6.9 Hz, 1H), 1.07 (d, J=6.7 Hz, 6H); MS (ESI(+)) m/e 350 (M+H)$^+$.

Example 346

N-(2-benzoyl-2,3-dihydro-1H-isoindol-5-yl)-1,3-dihydro-2H-isoindole-2-carboxamide The title compound was prepared as described in Example 278, substituting benzoyl chloride for acetyl chloride and N-(isoindolin-5-yl)isoindoline-2-carboxamide for 5-amino-N-(4-(propylcarbamoyl)phenyl)isoindoline-2-carboxamide. $^1$H NMR (400 MHz, DMSO-$d_6$) δ ppm 8.40 (d, J=8.8 Hz, 1H), 7.59-7.67 (m, 3H), 7.11-7.52 (m, 9H), 4.68-4.84 (m, 8H); MS (ESI(+)) m/e 384 (M+H)$^+$.

Example 347

N-[2-(3-methylbutyl)-2,3-dihydro-1H-isoindol-5-yl]-1,3-dihydro-2H-isoindole-2-carboxamide The title compound was prepared as described in Example 429, substituting 3-methylbutanal for isobutyraldehyde and N-(isoindolin-5-yl)isoindoline-2-carboxamide for N-(4-(1,2,3,6-tetrahydropyridin-4-yl)phenyl)isoindoline-2-carboxamide. $^1$H NMR (400 MHz, DMSO-$d_6$) δ ppm 8.28 (s, 1H), 7.47 (s, 1H), 7.29-7.37 (m, 5H), 7.09 (d, J=8.1 Hz, 1H), 4.75 (s, 4H), 3.77-3.79 (m, 2H), 3.74-3.76 (m, 2H), 2.64 (t, J=7.5 Hz, 2H), 1.60-1.71 (m, 1H), 1.37-1.43 (m, 2H), 0.91 (d, J=6.6 Hz, 6H); MS (ESI(+)) m/e 350 (M+H)$^+$.

Example 348

N-[4-(hexyloxy)phenyl]-1,3-dihydro-2H-isoindole-2-carboxamide

The title compound was prepared as described in Example 1A, substituting 1-(hexyloxy)-4-isocyanatobenzene for methyl 4-isocyanatobenzoate. $^1$H NMR (300 MHz, DMSO-$d_6$) δ ppm 8.17 (s, 1H), 7.39-7.45 (m, 2H), 7.27-7.39 (m, 4H), 6.81-6.85 (m, 2H), 4.74 (s, 4H), 3.91 (t, J=6.5 Hz, 2H), 1.64-1.73 (m, 2H), 1.35-1.47 (m, 2H), 1.23-1.38 (m, 4H), 0.85-0.91 (m, 3H); MS (ESI(+)) m/e 339 (M+H)$^+$.

Example 349

N-[4-(1-benzoylpiperidin-4-yl)butyl]-1,3-dihydro-2H-isoindole-2-carboxamide

The title compound was prepared as described in Example 278, substituting benzoyl chloride for acetyl chloride and N-[4-(piperidin-4-yl)butyl]-1,3-dihydro-2H-isoindole-2-carboxamide for 5-amino-N-(4-(propylcarbamoyl)phenyl)isoindoline-2-carboxamide. $^1$H NMR (300 MHz, DMSO-$d_6$) δ ppm 7.39-7.47 (m, 3H) 7.22-7.40 (m, 6H) 6.27 (t, J=5.43 Hz, 1H) 4.56 (s, 4H) 4.36-4.52 (br s, 1H) 3.52 (br s, 1H) 3.00-3.15 (m, 2H) 2.93 (br s, 1H) 0.93-1.86 (series of br m, 12H); MS (ESI(+)) m/e 406 (M+H)$^+$.

Example 350

N-{4-[1-(pyridin-3-ylcarbonyl)piperidin-4-yl]butyl}-1,3-dihydro-2H-isoindole-2-carboxamide The title compound was prepared as described in Example 278, substituting nicotinoyl chloride hydrochloride for acetyl chloride and N-[4-(piperidin-4-yl)butyl]-1,3-dihydro-2H-isoindole-2-carboxamide for 5-amino-N-(4-(propylcarbamoyl)phenyl)isoindoline-2-carboxamide. $^1$H NMR (300 MHz, DMSO-$d_6$) δ ppm 8.58-8.71 (m, 2H) 7.87 (d, J=7.5 Hz, 1H) 7.52 (dd, J=7.5, 4.8 Hz, 1H) 7.22-7.36 (m, 4H) 6.28 (br m, 1H) 4.56 (s, 4H) 4.44 (br m, 1H) 3.38-3.57 (br m, 1H) 2.95-3.15 (br m, 2H) 2.68-2.84 (br m, 1H) 0.95-1.84 (br series of m, 12H); MS (ESI(+)) m/e 407 (M+H)$^+$.

Example 351

N-[6-(4-chlorophenoxy)hexyl]-1,3-dihydro-2H-isoindole-2-carboxamide

The title compound was prepared as described in Example 344A, substituting 6-(4-chlorophenoxy)hexan-1-amine for tert-butyl 5-aminoisoindoline-2-carboxylate. $^1$H NMR (300 MHz, DMSO-$d_6$) δ ppm 1.40 (q, 6H), 1.70 (q, 2H), 3.08 (q, J=6.8 Hz, 2H), 3.95 (t, J=6.4 Hz, 2H), 4.57 (s, 4H), 6.27 (t, J=5.4 Hz, 1H), 6.85-7.01 (m, 2H), 7.21-7.39 (m, 6H); MS (ESI(+)) m/e 373 (M+H)$^+$.

Example 352

N-[4-(piperidin-4-yl)butyl]-1,3-dihydro-2H-isoindole-2-carboxamide

Example 352A tert-butyl 4-(4-(isoindoline-2-carboxamido)butyl)piperidine-1-carboxylate The title compound was prepared as described in Example 344, substituting tert-butyl 4-(4-aminobutyl)piperidine-1-carboxylate for tert-butyl 5-aminoisoindoline-2-carboxylate in Example 344A.

Example 352B

N-[4-(piperidin-4-yl)butyl]-1,3-dihydro-2H-isoindole-2-carboxamide

The title compound was prepared as described in Example 2D, substituting tert-butyl 4-(4-(isoindoline-2-carboxamido)butyl)piperidine-1-carboxylate for tert-butyl 4-((4-(5-fluoroisoindoline-2-carboxamido)benzamido)methyl)benzylcarbamate. $^1$H NMR (300 MHz, DMSO-$d_6$) δ ppm 1.14-1.34 (m, 6H), 1.35-1.57 (m, 3H), 1.76 (d, J=12.30 Hz, 2H), 2.69-2.89 (m, 2H), 3.07 (q, J=6.74 Hz, 2H), 3.21 (d, J=12.70 Hz, 2H), 4.57 (s, 4H), 6.29 (t, J=5.55 Hz, 1H), 7.11-7.41 (m, 4H), 8.31 (s, 1H); MS (ESI(+)) m/e 299 (M+H)$^+$.

Example 353

N,N'-hexane-1,6-diylbis(1,3-dihydro-2H-isoindole-2-carboxamide)

The title compound was prepared as described in Example 1A, substituting 1,6-diisocyanatohexane for methyl 4-isocyanatobenzoate. $^1$H NMR (300 MHz, DMSO-$d_6$) δ ppm 7.19-7.37 (m, 8H) 6.28 (t, J=5.59 Hz, 2H) 4.57 (s, 8H) 3.07 (q, J=6.8 Hz, 4H) 1.37-1.55 (m, 4H) 1.21-1.37 (m, 4H); MS (ESI(+)) m/e 407 (M+H)$^+$.

Example 354

N-(4-phenylbutyl)-1,3-dihydro-2H-isoindole-2-carboxamide

The title compound was prepared as described in Example 1A, substituting (4-isocyanatobutyl)benzene for methyl 4-isocyanatobenzoate. $^1$H NMR (300 MHz, DMSO-$d_6$) δ ppm 7.24-7.33 (m, 6H), 7.13-7.22 (m, 3H), 6.30 (t, J=5.6 Hz, 1H), 4.56 (s, 4H), 3.06-3.13 (m, 2H), 2.59 (t, J=7.4 Hz, 2H), 1.51-1.65 (m, 2H), 1.40-1.53 (m, 2H); MS (ESI(+)) m/e 295 (M+H)$^+$.

Example 355 ethyl 6-[(1,3-dihydro-2H-isoindol-2-ylcarbonyl)amino]hexanoate

The title compound was prepared as described in Example 1A, substituting ethyl 6-isocyanatohexanoate for methyl 4-isocyanatobenzoate. $^1$H NMR (300 MHz, DMSO-$d_6$) δ ppm 7.25-7.33 (m, 4H), 6.29 (t, J=5.6 Hz, 1H), 4.57 (s, 4H), 4.04 (q, J=7.1 Hz, 2H), 3.02-3.09 (m, 2H), 2.28 (t, J=7.3 Hz, 2H), 1.48-1.60 (m, 2H), 1.39-1.50 (m, 2H), 1.23-1.34 (m, 2H), 1.16 (t, J=7.1 Hz, 3H); MS (ESI(+)) m/e 305 (M+H)$^+$.

Example 356

N-hexyl-1,3-dihydro-2H-isoindole-2-carboxamide

The title compound was prepared as described in Example 1A, substituting 1-isocyanatohexane for methyl 4-isocyanatobenzoate. $^1$H NMR (300 MHz, DMSO-d$_6$) δ ppm 7.25-7.33 (m, 4H), 6.27 (t, J=5.6 Hz, 1H), 4.57 (s, 4H), 3.02-3.10 (m, 2H), 1.36-1.51 (m, 2H), 1.25-1.30 (m, 6H), 0.81-0.92 (m, 3H); MS (ESI(−)) m/e 245 (M−H)$^-$.

Example 357

N-(3-phenylpropyl)-1,3-dihydro-2H-isoindole-2-carboxamide

The title compound was prepared as described in Example 1A, substituting (3-isocyanatopropyl)benzene for methyl 4-isocyanatobenzoate. $^1$H NMR (300 MHz, DMSO-d$_6$) δ ppm 7.11-7.37 (m, 9H), 6.31 (t, J=5.5 Hz, 1H), 4.57 (s, 4H), 3.07-3.14 (m, 2H), 2.60 (t, J=7.6 Hz, 2H), 1.71-1.81 (m, 2H); MS (ESI(+)) m/e 281 (M+H)$^+$.

Example 358

N-octyl-1,3-dihydro-2H-isoindole-2-carboxamide

The title compound was prepared as described in Example 1A, substituting 1-isocyanatooctane for methyl 4-isocyanatobenzoate. $^1$H NMR (300 MHz, DMSO-d$_6$) δ ppm 7.24-7.35 (m, 4H), 6.27 (t, J=5.5 Hz, 1H), 4.57 (s, 4H), 3.02-3.09 (m, 2H), 1.40-1.47 (m, 2H), 1.25-1.27 (m, 10H), 0.81-0.89 (m, 3H); MS (ESI(+)) m/e 275 (M+H)$^+$.

Example 359

N-{6-[(1-methyl-1H-pyrazol-4-yl)amino]-6-oxohexyl}-1,3-dihydro-2H-isoindole-2-carboxamide

Example 359A

6-[(1,3-dihydro-2H-isoindol-2-ylcarbonyl)amino]hexanoic acid

The title compound was prepared as described in Example 1B, substituting ethyl 6-[(1,3-dihydro-2H-isoindol-2-ylcarbonyl)amino]hexanoate for methyl 4-(isoindoline-2-carboxamido)benzoate.

Example 359B

N-{6-[(1-methyl-1H-pyrazol-4-yl)amino]-6-oxohexyl}-1,3-dihydro-2H-isoindole-2-carboxamide The title compound was prepared as described in Example 1C, substituting 1-methyl-1H-pyrazol-4-amine for 3-phenylpropan-1-amine and 6-[(1,3-dihydro-2H-isoindol-2-ylcarbonyl)amino]hexanoic acid for 4-(isoindoline-2-carboxamido)benzoic acid. $^1$H NMR (300 MHz, DMSO-d$_6$) δ ppm 9.81 (s, 1H), 7.82 (s, 1H), 7.34-7.36 (m, 1H), 7.24-7.34 (m, 4H), 6.28 (t, J=5.5 Hz, 1H), 4.56 (s, 4H), 3.75 (s, 3H), 3.03-3.10 (m, 2H), 2.22 (t, J=7.3 Hz, 2H), 1.51-1.64 (m, 2H), 1.40-1.52 (m, 2H), 1.23-1.34 (m, 2H); MS (ESI(+)) m/e 356 (M+H)$^+$.

Example 360

N-[6-(methylamino)-6-oxohexyl]-1,3-dihydro-2H-isoindole-2-carboxamide

The title compound was prepared as described in Example 1C, substituting methylamine for 3-phenylpropan-1-amine and 6-[(1,3-dihydro-2H-isoindol-2-ylcarbonyl)amino]hexanoic acid for 4-(isoindoline-2-carboxamido)benzoic acid. $^1$H NMR (300 MHz, DMSO-d$_6$) δ ppm 7.60-7.72 (m, 1H), 7.25-7.33 (m, 4H), 6.24-6.29 (m, 1H), 4.57 (s, 4H), 2.94-3.09 (m, 2H), 2.54 (d, J=4.6 Hz, 3H), 2.30 (t, J=7.3 Hz, 1H), 2.04 (t, J=7.4 Hz, 1H), 1.37-1.58 (m, 4H), 1.18-1.35 (m, 2H); MS (ESI(+)) m/e 290 (M+H)$^+$.

Example 361

N-{6-oxo-6-[(3-phenylpropyl)amino]hexyl}-1,3-dihydro-2H-isoindole-2-carboxamide

The title compound was prepared as described in Example 1C, substituting 6-[(1,3-dihydro-2H-isoindol-2-ylcarbonyl)amino]hexanoic acid for 4-(isoindoline-2-carboxamido)benzoic acid. $^1$H NMR (300 MHz, DMSO-d$_6$) δ ppm 7.75-7.80 (m, 1H), 7.24-7.34 (m, 6H), 7.12-7.22 (m, 3H), 6.27 (t, J=5.5 Hz, 1H), 4.56 (s, 4H), 2.98-3.11 (m, 4H), 2.52-2.58 (m, 2H), 2.06 (t, J=7.3 Hz, 2H), 1.62-1.72 (m, 2H), 1.37-1.58 (m, 4H), 1.12-1.33 (m, 2H); MS (ESI(+)) m/e 394 (M+H)$^+$.

Example 362

N-{6-[(3-methylbutyl)amino]-6-oxohexyl}-1,3-dihydro-2H-isoindole-2-carboxamide

The title compound was prepared as described in Example 1C, substituting 3-methylbutan-1-amine for 3-phenylpropan-1-amine and 6-[(1,3-dihydro-2H-isoindol-2-ylcarbonyl)amino]hexanoic acid for 4-(isoindoline-2-carboxamido)benzoic acid. $^1$H NMR (300 MHz, DMSO-d$_6$) δ ppm 7.64-7.69 (m, 1H), 7.24-7.34 (m, 4H), 6.26 (t, J=5.5 Hz, 1H), 4.57 (s, 4H), 2.99-3.10 (m, 4H), 2.03 (t, J=7.3 Hz, 2H), 1.41-1.59 (m, 5H), 1.21-1.30 (m, 4H), 0.84 (d, J=6.6 Hz, 6H); MS (ESI(+)) m/e 346 (M+H)$^+$.

Example 363

N-{3-oxo-3-[(3-phenylpropyl)amino]propyl}-1,3-dihydro-2H-isoindole-2-carboxamide

Example 363A ethyl 3-(isoindoline-2-carboxamido)propanoate

The title compound was prepared as described in Example 1A, substituting ethyl 3-isocyanatopropanoate for methyl 4-isocyanatobenzoate.

Example 363B 3-(isoindoline-2-carboxamido)propanoic acid

The title compound was prepared as described in Example 1B, substituting ethyl 3-(isoindoline-2-carboxamido)propanoate for methyl 4-(isoindoline-2-carboxamido)benzoate.

Example 363C

N-{3-oxo-3-[(3-phenylpropyl)amino]propyl}-1,3-dihydro-2H-isoindole-2-carboxamide The title compound was prepared as described in Example 1C, substituting 3-(isoindoline-2-carboxamido)propanoic acid for 4-(isoindoline-2-carboxamido)benzoic acid. $^1$H NMR (300 MHz, DMSO-$d_6$) δ ppm 7.87-7.92 (m, 1H), 7.22-7.32 (m, 6H), 7.12-7.19 (m, 3H), 6.36 (t, J=5.5 Hz, 1H), 4.56 (s, 4H), 3.24-3.32 (m, 2H), 3.03-3.10 (m, 2H), 2.52-2.60 (m, 2H), 2.30 (t, J=7.0 Hz, 2H), 1.63-1.74 (m, 2H); MS (ESI(+)) m/e 352 (M+H)$^+$.

Example 364

N-{3-oxo-3-[4-(pyridin-2-yl)piperazin-1-yl]propyl}-1,3-dihydro-2H-isoindole-2-carboxamide The title compound was prepared as described in Example 1C, substituting 1-(pyridin-2-yl)piperazine for 3-phenylpropan-1-amine and 3-(isoindoline-2-carboxamido)propanoic acid for 4-(isoindoline-2-carboxamido)benzoic acid. $^1$H NMR (300 MHz, DMSO-$d_6$) δ ppm 8.11 (ddd, J=4.9, 2.0, 0.8 Hz, 1H), 7.53 (ddd, J=8.7, 7.0, 1.9 Hz, 1H), 7.25-7.34 (m, 4H), 6.83 (d, J=8.6 Hz, 1H), 6.65 (ddd, J=7.1, 4.9, 0.8 Hz, 1H), 6.37 (t, J=5.6 Hz, 1H), 4.57 (s, 4H), 3.44-3.61 (m, 8H), 3.28-3.37 (m, 2H), 2.54-2.61 (m, 2H); MS (ESI(+)) m/e 380 (M+H)$^+$.

Example 365

N-{3-[(3-methylbutyl)amino]-3-oxopropyl}-1,3-dihydro-2H-isoindole-2-carboxamide

The title compound was prepared as described in Example 1C, substituting 1,3-methylbutan-1-amine for 3-phenylpropan-1-amine and 3-(isoindoline-2-carboxamido)propanoic acid for 4-(isoindoline-2-carboxamido)benzoic acid. $^1$H NMR (300 MHz, DMSO-$d_6$) δ ppm 7.76-7.81 (m, 1H), 7.25-7.34 (m, 4H), 6.31-6.36 (m, 1H), 4.56 (s, 4H), 3.23-3.31 (m, 2H), 3.02-3.09 (m, 2H), 2.27 (t, J=7.0 Hz, 2H), 1.46-1.62 (m, 1H), 1.27 (q, J=7.1 Hz, 2H), 0.84 (d, J=6.6 Hz, 6H); MS (ESI(+)) m/e 304 (M+H)$^+$.

Example 366

N-[4-(1-propyl-1H-pyrazol-4-yl)benzyl]-1,3-dihydro-2H-isoindole-2-carboxamide

Example 366A

N-(4-bromobenzyl)isoindoline-2-carboxamide

The title compound was prepared as described in Example 1A, substituting 1-bromo-4-(isocyanatomethyl)benzene for methyl 4-isocyanatobenzoate.

Example 366B

N-[4-(1-propyl-1H-pyrazol-4-yl)benzyl]-1,3-dihydro-2H-isoindole-2-carboxamide

The title compound was prepared as described in Example 280, substituting 1-propyl-4-(4,4,5,5-tetramethyl-1,3,2-dioxaborolan-2-yl)-1H-pyrazole for 1H-pyrazol-3-ylboronic acid and N-(4-bromobenzyl)isoindoline-2-carboxamide for 5-bromo-N-(4-(propylcarbamoyl)phenyl)isoindoline-2-carboxamide. $^1$H NMR (300 MHz, DMSO-$d_6$) δ ppm 0.85 (t, J=7.5 Hz, 3H), 1.70-1.92 (m, 2H), 4.06 (t, J=6.9 Hz, 2H), 4.29 (d, J=6.1 Hz, 2H), 4.63 (s, 4H), 6.91 (t, J=5.9 Hz, 1H), 7.18-7.40 (m, 6H), 7.49 (d, J=8.5 Hz, 2H), 7.82 (s, 1H), 8.12 (s, 1H); MS (ESI(+)) m/e 361 (M+H)$^+$.

Example 367

N-[4-(1-isobutyl-1H-pyrazol-4-yl)benzyl]-1,3-dihydro-2H-isoindole-2-carboxamide

The title compound was prepared as described in Example 280, substituting 1-isobutyl-4-(4,4,5,5-tetramethyl-1,3,2-dioxaborolan-2-yl)-1H-pyrazole for 1H-pyrazol-3-ylboronic acid and N-(4-bromobenzyl)isoindoline-2-carboxamide for 5-bromo-N-(4-(propylcarbamoyl)phenyl)isoindoline-2-carboxamide. $^1$H NMR (300 MHz, DMSO-$d_6$) δ ppm 0.86 (d, J=6.4 Hz, 6H), 2.03-2.21 (m, 1H), 3.91 (d, J=7.1 Hz, 2H), 4.28 (d, J=5.9 Hz, 2H), 4.63 (s, 4H), 6.92 (t, J=5.9 Hz, 1H), 7.25-7.37 (m, 6H), 7.50 (d, J=8.3 Hz, 2H), 7.83 (s, 1H), 8.10 (s, 1H); MS (ESI(+)) m/e 375 (M+H)$^+$.

Example 368

N-(5-{[4-(pyridin-2-yl)piperazin-1-yl]carbonyl}pyridin-2-yl)-1,3-dihydro-2H-isoindole-2-carboxamide The title compound was prepared as described in Example 1C, substituting N-(2-pyridyl)piperazine for 3-phenylpropan-1-amine and 6-(isoindoline-2-carboxamido)nicotinic acid for 4-(isoindoline-2-carboxamido)benzoic acid. $^1$H NMR (400 MHz, DMSO-$d_6$) δ ppm 9.21 (s, 1H), 8.39 (dd, J=2.3, 0.8 Hz, 1H), 8.13 (dd, J=4.9, 1.9 Hz, 1H), 8.00 (dd, J=8.6, 0.8 Hz, 1H), 7.84 (dd, J=8.6, 2.4 Hz, 1H), 7.56 (ddd, J=8.7, 6.9, 1.9 Hz, 1H), 7.34-7.39 (m, 2H), 7.29-7.34 (m, 2H), 6.85 (d, J=8.5 Hz, 1H), 6.67 (dd, J=6.7, 4.9 Hz, 1H), 4.75-4.92 (bs, 4H), 3.47-3.81 (m, 8H); MS (ESI(+)) m/e 429 (M+H)$^+$.

Example 369

N-{5-[(3-phenylpropyl)carbamoyl]pyridin-2-yl}-1,3-dihydro-2H-isoindole-2-carboxamide

Example 369A methyl 6-(isoindoline-2-carboxamido)nicotinate

The title compound was prepared as described in Example 344A, substituting methyl 6-aminonicotinate for tert-butyl 5-aminoisoindoline-2-carboxylate.

Example 369B 6-(isoindoline-2-carboxamido)nicotinic acid

The title compound was prepared as described in Example 1B, substituting methyl 6-(isoindoline-2-carboxamido)nicotinate for methyl 4-(isoindoline-2-carboxamido)benzoate.

Example 369C

N-{5-[(3-phenylpropyl)carbamoyl]pyridin-2-yl}-1,3-dihydro-2H-isoindole-2-carboxamide The title compound was prepared as described in Example 1C, substituting 6-(isoindoline-2-carboxamido)nicotinic acid for 4-(isoindoline-2-carboxamido)benzoic acid. $^1$H NMR (400 MHz, DMSO-$d_6$) δ ppm 9.25 (s, 1H), 8.74 (d, J=2.4 Hz, 1H), 8.47-8.51 (m, 1H), 8.14 (dd, J=8.8, 2.4 Hz, 1H), 8.00 (d, J=8.7 Hz, 1H), 7.33-7.38 (m, 2H), 7.29-7.33 (m, 2H), 7.26-7.30 (m, 2H), 7.21-7.26 (m, 2H), 7.15-7.21 (m, 1H), 4.74-4.92 (bs, 4H), 3.25-3.32 (m, 2H), 2.64 (t, J=7.6 Hz, 2H), 1.84 (p, J=7.4 Hz, 2H); MS (ESI(+)) m/e 401 (M+H)$^+$.

Example 370

N-{5-[(3-methylbutyl)carbamoyl]pyridin-2-yl}-1,3-dihydro-2H-isoindole-2-carboxamide The title compound was prepared as described in Example 1C, substituting 3-methylbutan-1-amine for 3-phenylpropan-1-amine and 6-(isoindoline-2-carboxamido)nicotinic acid for 4-(isoindoline-2-carboxamido)benzoic acid. $^1$H NMR (400 MHz, DMSO-$d_6$) δ ppm 9.24 (s, 1H), 8.73 (d, J=2.4 Hz, 1H), 8.42 (t, J=5.5 Hz, 1H), 8.13 (dd, J=8.8, 2.4 Hz, 1H), 7.99 (d, J=8.7 Hz, 1H), 7.25-7.37 (m, 4H), 4.71-4.95 (bs, 4H), 3.24-3.32 (m, 2H), 1.57-1.68 (m, 1H), 1.43 (q, J=7.1 Hz, 2H), 0.91 (d, J=6.6 Hz, 6H); MS (ESI(+)) m/e 353 (M+H)$^+$.

Example 371

N-{5-[(3-phenylpropyl)carbamoyl]-1,3-thiazol-2-yl}-1,3-dihydro-2H-isoindole-2-carboxamide Example 371A methyl 2-(isoindoline-2-carboxamido)thiazole-5-carboxylate The title compound was prepared as described in Example 272B, substituting methyl 2-aminothiazole-5-carboxylate for 4-amino-N-propylbenzamide and isoindoline for methyl isoindoline-5-carboxylate hydrochloride.

Example 371B 2-(isoindoline-2-carboxamido)thiazole-5-carboxylic acid

The title compound was prepared as described in Example 1B, substituting methyl 2-(isoindoline-2-carboxamido)thiazole-5-carboxylate for methyl 4-(isoindoline-2-carboxamido)benzoate.

Example 371C

N-{5-[(3-phenylpropyl)carbamoyl]-1,3-thiazol-2-yl}-1,3-dihydro-2H-isoindole-2-carboxamide The title compound was prepared as described in Example 1C, substituting 2-(isoindoline-2-carboxamido)thiazole-5-carboxylic acid for 4-(isoindoline-2-carboxamido)benzoic acid. $^1$H NMR (300 MHz, DMSO-$d_6$) δ ppm 11.00-11.19 (bs, 1H), 8.34 (t, J=5.6 Hz, 1H), 7.98 (s, 1H), 7.15-7.37 (m, 9H), 4.70-4.83 (m, 4H), 3.17-3.28 (m, 2H), 2.63 (t, J=7.6 Hz, 2H), 1.81 (p, J=7.4 Hz, 2H); MS (ESI(-)) m/e 405 (M-H)$^-$.

Example 372

N-{5-[(3-methylbutyl)carbamoyl]-1,3-thiazol-2-yl}-1,3-dihydro-2H-isoindole-2-carboxamide The title compound was prepared as described in Example 1C, substituting 3-methylbutan-1-amine for 3-phenylpropan-1-amine and 2-(isoindoline-2-carboxamido)thiazole-5-carboxylic acid for 4-(isoindoline-2-carboxamido)benzoic acid. $^1$H NMR (300 MHz, DMSO-$d_6$) δ ppm 11.01-11.16 (bs, 1H), 8.27 (t, J=5.6 Hz, 1H), 7.96 (s, 1H), 7.29-7.36 (m, 4H), 4.73-4.88 (bs, 4H), 3.18-3.28 (m, 2H), 1.52-1.69 (m, 1H), 1.34-1.44 (m, 2H), 0.90 (d, J=6.6 Hz, 6H); MS (ESI(-)) m/e 357 (M-H)$^-$.

Example 374

N-[4-(4-oxo-3,4-dihydrophthalazin-1-yl)phenyl]-1,3-dihydro-2H-isoindole-2-carboxamide Example 374A N-(4-(4,4,5,5-tetramethyl-1,3,2-dioxaborolan-2-yl)phenyl)isoindoline-2-carboxamide 500 mg (4-Isocyanatophenyl)boronic acid pinacolester (1.979 mmol) and 365 mg isoindoline (2.97 mmol) were dissolved in 10 ml dichloromethane and the resultant mixture was stirred over night at room temperature. After adding water, the mixture was extracted several times with dichloromethane, the combined organic phases were washed with dried over magnesium sulfate and filtered. The solvent was evaporated under reduced pressure. Column chromatography of the residue with dichloromethane resulted in the title compound.

Example 374B

N-[4-(4-oxo-3,4-dihydrophthalazin-1-yl)phenyl]-1,3-dihydro-2H-isoindole-2-carboxamide 105 mg N-(4-(4,4,5,5-tetramethyl-1,3,2-dioxaborolan-2-yl)phenyl)isoindoline-2-carboxamide (0.288 mmol) and 53 mg 4-chloro-1,2-dihydrophthalazin-1-one (0.288 mmol) were dissolved in 2.5 ml dioxane. Cesium carbonate (474 mg, 1.44 mmol) was dissolved in 0.25 ml water and the resulting solution added to the reaction mixture. After the addition of 27.8 mg [1,1'-bis(diphenylphosphino)-ferrocene]dichlorpalladium(II) (0.038 mmol) the reaction mixture was flushed with nitrogen and stirred for 30 minutes in the microwave (Biotage Initiator 2.5) at 110° C. Dioxane was removed under reduced pressure, water and dichloromethane added to the residue and the formed precipitation was filtered. After dissolving the solid matter in a larger amount of dichloromethane/methanol 8:2, silica gel was added and subsequently the solvent was removed under reduced pressure. This residue was was purified by column chromatography using dichloromethane/methanol 95:5. $^1$H NMR (DMSO-$d_6$, 400 MHz): δ ppm 12.73 (s, 1H), 8.55 (s, 1H), 8.33 (dd, 1H), 7.85-7.92 (m, 2H), 7.73-7.78 (m, 3H), 7.48 (d, 2H), 7.35-7.38 (m, 2H), 7.30-7.33 (m, 2H), 4.81 (s, 4H). MS (ESI(-)) m/e 383.2 (M+H)$^+$.

Example 375

N-[4-(isoquinolin-4-yl)phenyl]-1,3-dihydro-2H-isoindole-2-carboxamide

The title compound was prepared as described in Example 374B, substituting 4-chloro-1,2-dihydrophthalazin-1-one with 4-bromoisoquinoline. ESI-MS [M+H+]=366.1.

Example 376

N-[4-(1-oxo-1,2-dihydroisoquinolin-4-yl)phenyl]-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-aminophenyl)isoquinolin-1(2H)-one. ESI-MS [M+H+]=382.1.

Example 377

N-[4-(4-oxo-3,4,5,6,7,8-hexahydrophthalazin-1-yl)phenyl]-1,3-dihydro-2H-isoindole-2-carboxamide

Example 377A 2-(4-Amino-benzoyl)-cyclohex-1-enecarboxylic acid

To a suspension of 2.2 g magnesium turnings (83.5 mmol) in 15 ml tetrahydrofuran were added 0.1 mL 1,2-dibromethane to start the Grignard reaction followed by slow addition of 13.0 g 2-(4-bromphenyl)-1,1,1,3,3,3-hexamethyldisilazane (41 mmol) in 70 mL tetrahydrofuran over a period of 20 minutes at room temperature with subsequent stirring for further 30 minutes. The resulting mixture was added dropwise at −78° C. to a solution of 4,5,6,7-tetrahydro-isobenzofuran-1,3-dione (5.6 g) in 70 mL tetrahydrofuran. The reaction mixture was slowly warmed to room temperature. Sulfuric acid (2 mL, 1 M) was added and the solvent was removed under reduced pressure. The residue was added carefully to 20 mL of 0.5 M sulfuric acid solution and the desired product started to precipitate and was extracted with ethyl acetate. Acidification of the water phase and extraction with ethyl acetate was continued until pH~4-5 (at least three times). The combined organic phases were washed with brine, dried over magnesium sulfate, filtered and the solvent was subsequently evaporated under reduced pressure. Purification of the raw material by column chromatography with ethyl acetate/hexane 1:1 and subsequently 100% ethyl acetate resulted in the desired product.

Example 377B 4-(4-aminophenyl)-5,6,7,8-tetrahydro-2H-phthalazin-1-one 10.3 g of 2-(4-amino-benzoyl)-cyclohex-1-enecarboxylic acid (42 mmol) were dissolved in 45 mL ethanol, 2.7 g (54 mmol) hydrazine hydrate was added and the mixture was heated under reflux for 30 hours. Precipitation of the product already started several hours after heating. After cooling in the refrigerator overnight the precipitated product was filtered and washed with cold ethanol.

Example 377C 1,3-dihydro-isoindole-2-carboxylicacid[4-(4-oxo-3,4,5,6,7,8-hexahydro-phthalazin-1-yl)-phenyl]-amide To a solution of 200 mg 4-(4-aminophenyl)-5,6,7,8-tetrahydro-2H-phthalazin-1-one (0.829 mmol) in 5 ml N,N-dimethylformamide were added 245 mg carbonic acid bis-(2,5-dioxo-pyrrolidin-1-yl) ester (0.912 mmol) and the reaction mixture was stirred overnight. 255 mg of isoindoline were added, the precipitation formed was dissolved by adding 0.8 ml N,N-dimethylformamide, and the reaction mixture was stirred overnight. Water was added, and the formed precipitation was washed with water/methanol and subsequently dried in vacuum to obtain the crude material. The crude material was refluxed in 20 ml ethanol for 2 hours, cooled to room temperature, filtered and dried to obtain the desired product. ESI-MS [M+H+]=387.2.

Example 378

N-[4-(8-fluoro-4-oxo-3,4-dihydrophthalazin-1-yl)phenyl]-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-amino-phenyl)-5-fluoro-2H-phthalazin-1-one. ESI-MS [M+H+]=401.1.

Example 379

5-fluoro-N-[4-(4-oxo-3,4-dihydrophthalazin-1-yl)phenyl]-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-amino-phenyl)-2H-phthalazin-1-one and isoindoline with 5-fluoro-2,3-dihydro-1H-isoindole. ESI-MS [M+H+]=401.1.

Example 380

N-[4-(4-oxo-3,4-dihydrophthalazin-1-yl)phenyl]-5-(pyrrolidin-1-ylmethyl)-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-amino-phenyl)-2H-phthalazin-1-one and isoindoline with 5-pyrrolidin-1-ylmethyl-2,3-dihydro-1H-isoindole. ESI-MS [M+H+]=466.2.

Example 381

5-(morpholin-4-ylmethyl)-N-[4-(1-oxo-1,2-dihydroisoquinolin-4-yl)phenyl]-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-aminophenyl)isoquinolin-1(2H)-one and isoindoline with 5-morpholin-4-ylmethyl-2,3-dihydro-1H-isoindole. ESI-MS [M+H+]=481.3.

Example 382

5-methoxy-N-[4-(1-oxo-1,2-dihydroisoquinolin-4-yl)phenyl]-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-aminophenyl)isoquinolin-1

(2H)-one and isoindoline with 5-methoxy-2,3-dihydro-1H-isoindole. ESI-MS [M+H+]=412.2.

Example 383

5-[(4-methylpiperazin-1-yl)methyl]-N-[4-(4-oxo-3,4-dihydrophthalazin-1-yl)phenyl]-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-amino-phenyl)-2H-phthalazin-1-one and isoindoline with 5-(4-methyl-piperazin-1-ylmethyl)-2,3-dihydro-1H-isoindole. ESI-MS [M+H+]=495.2.

Example 384

5-cyano-N-[4-(1-oxo-1,2-dihydroisoquinolin-4-yl)phenyl]-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-aminophenyl)isoquinolin-1(2H)-one and isoindoline with 2,3-dihydro-1H-isoindole-5-carbonitrile. ESI-MS [M+H+]=407.1.

Example 385

5-chloro-N-[4-(1-oxo-1,2-dihydroisoquinolin-4-yl)phenyl]-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-aminophenyl)isoquinolin-1(2H)-one and isoindoline with 5-chloro-2,3-dihydro-1H-isoindole. ESI-MS [M+H+]=416.1.

Example 386

N-[4-(4-oxo-4,5-dihydro-3H-2,3-benzodiazepin-1-yl)phenyl]-1,3-dihydro-2H-isoindole-2-carboxamide The title compound was prepared as described in Example 377C, substituting 4-(4-aminophenyl)-5,6,7,8-tetrahydro-2H-phthalazin-1-one with 1-(4-amino-phenyl)-3,5-dihydro-benzo[d][1,2]diazepin-4-one. ESI-MS [M+H+]=397.2.

Example 387

N-[4-(1-oxo-1,2-dihydroisoquinolin-4-yl)phenyl]-5-(pyrrolidin-1-ylmethyl)-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-aminophenyl)isoquinolin-1(2H)-one and isoindoline with 5-pyrrolidin-1-ylmethyl-2,3-dihydro-1H-isoindole. ESI-MS [M+H+]=465.2.

Example 388

N-{4-[4-oxo-8-(trifluoromethyl)-3,4-dihydrophthalazin-1-yl]phenyl}-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-amino-phenyl)-5-trifluoromethyl-2H-phthalazin-1-one. ESI-MS [M+H+]=451.1.

Example 389

5-[(dimethylamino)methyl]-N-[4-(1-oxo-1,2-dihydroisoquinolin-4-yl)phenyl]-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-aminophenyl)isoquinolin-1(2H)-one and isoindoline with (2,3-dihydro-1H-isoindol-5-ylmethyl)-dimethyl-amine ESI-MS [M+H+]=439.3.

Example 390

5-[(diethylamino)methyl]-N-[4-(1-oxo-1,2-dihydroisoquinolin-4-yl)phenyl]-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-aminophenyl)isoquinolin-1(2H)-one and isoindoline with (2,3-dihydro-1H-isoindol-5-ylmethyl)-diethyl-amine. ESI-MS [M+H+]=467.3.

Example 391

5-[(4-methylpiperazin-1-yl)methyl]-N-[4-(1-oxo-1,2-dihydroisoquinolin-4-yl)phenyl]-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-aminophenyl)isoquinolin-1(2H)-one and isoindoline with 5-(4-methyl-piperazin-1-ylmethyl)-2,3-dihydro-1H-isoindole. ESI-MS [M+H+]=494.3.

Example 392

5-[(dimethylamino)methyl]-N-[4-(4-oxo-3,4-dihydrophthalazin-1-yl)phenyl]-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-amino-phenyl)-2H-phthalazin-1-one and isoindoline with (2,3-dihydro-1H-isoindol-5-ylmethyl)-dimethyl-amine. ESI-MS [M+H+]=440.2.

Example 393

5-[(diethylamino)methyl]-N-[4-(4-oxo-3,4-dihydrophthalazin-1-yl)phenyl]-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-amino-phenyl)-2H-phthalazin-1-one and isoindoline with (2,3-dihydro-1H-isoindol-5-ylmethyl)-diethyl-amine. ESI-MS [M+H+]=468.2.

Example 394

N-{4-[4-oxo-8-(trifluoromethyl)-3,4-dihydro-phthalazin-1-yl]phenyl}-5-(pyrrolidin-1-ylmethyl)-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-amino-phenyl)-5-trifluoromethyl-2H-phthalazin-1-one and isoindoline with 5-pyrrolidin-1-ylmethyl-2,3-dihydro-1H-isoindole. ESI-MS [M+H+]=534.2.

Example 395

5-[(1-methylpiperidin-4-yl)oxy]-N-[4-(4-oxo-3,4-dihydrophthalazin-1-yl)phenyl]-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-amino-phenyl)-2H-phthalazin-1-one and isoindoline with 5-(1-methyl-piperidin-4-yloxy)-2,3-dihydro-1H-isoindole. ESI-MS [M+H+]=496.2.

Example 396

5-{[(3R)-3-fluoropyrrolidin-1-yl]methyl}-N-[4-(4-oxo-3,4-dihydrophthalazin-1-yl)phenyl]-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-amino-phenyl)-2H-phthalazin-1-one and isoindoline with 5-((R)-3-fluoro-pyrrolidin-1-ylmethyl)-2,3-dihydro-1H-isoindole. ESI-MS [M+H+]=484.2.

Example 397

5-{[(3S)-3-fluoropyrrolidin-1-yl]methyl}-N-[4-(4-oxo-3,4-dihydrophthalazin-1-yl)phenyl]-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-amino-phenyl)-2H-phthalazin-1-one and isoindoline with 54(S)-3-fluoro-pyrrolidin-1-ylmethyl)-2,3-dihydro-1H-isoindole. ESI-MS [M+H+]=484.2.

Example 398

5-(azetidin-1-ylmethyl)-N-[4-(4-oxo-3,4-dihydro-phthalazin-1-yl)phenyl]-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-amino-phenyl)-2H-phthalazin-1-one and isoindoline with 5-azetidin-1-ylmethyl-2,3-dihydro-1H-isoindole. ESI-MS [M+H+]=452.2.

Example 399

N-[4-(1-oxo-1,2-dihydropyrrolo[1,2-d][1,2,4]triazin-4-yl)phenyl]-1,3-dihydro-2H-isoindole-2-carboxamide

Example 399A

N'-(4-bromobenzoyl)-1H-pyrrole-2-carbohydrazide

To 0.750 g of 1H-pyrrole-2-carbohydrazide (5.99 mmol) in 50 ml tetrahydrofuran was added 1.315 g 4-bromobenzoyl chloride (5.99 mmol) and 1 ml pyridine (11.99 mmol) at room temperature under nitrogen. After one hour of stirring at room temperature, the desired product precipitated. The precipitate was filtered, washed with minimum dichloromethane and methanol and dried to afford the title compound. $^1$H NMR (400 MHz, DMSO-$d_6$) δ 11.63 (s, 1H), 10.47 (s, 1H), 10.04 (s, 1H), 7.84-7.88 (m, 2H), 7.75 (d, J=8.8, 1H), 7.75 (q, J=4.2, 1H), 6.91-6.95 (m, 2H), 6.33-6.15 (m, 1H).

Example 399B 2-(4-bromophenyl)-5-(1H-pyrrol-2-yl)-1,3,4-oxadiazole

To 1.2 g of N'-(4-bromobenzoyl)-1H-pyrrole-2-carbohydrazide (3.89 mmol) was added 5 ml phosphoryl trichloride (1.65 mmol). The reaction was stirred for 25 minutes at 120° C. The reaction was cooled to 0° C., and ice was added. The resulting solid was filtered, and washed with water, NH$_4$OH, dichloromethane and ethyl acetate. Purification by silica gel chromatography (dichloromethane:methanol=9:1) resulted in the desired product. $^1$H NMR (400 MHz, DMSO-$d_6$) δ 12.32 (s, 1H), 8.05-8.00 (m, 2H), 7.89-7.83 (m, 2H), 7.18 (td, J=1.5, 2.6, 1H), 6.97 (ddd, J=1.5, 2.4, 3.7, 1H), 6.33 (dt, J=2.4, 3.6, 1H). $^{13}$C NMR (400 MHz, DMSO-$d_6$) δ 110.16, 112.49, 115.12, 122.71, 123.96, 125.23, 128.26, 132.49, 159.37, 161.57.

Example 399C 4-(4-bromophenyl)pyrrolo[1,2-d][1,2,4]triazin-1(2H)-one

To 0.469 g sodium ethanolate (6.89 mmol) dissolved in 20 ml ethanol was added 1.0 g 2-(4-bromophenyl)-5-(1H-pyrrol-2-yl)-1,3,4-oxadiazole (3.45 mmol) at room temperature under nitrogen and the mixture was stirred at room temperature for 5 minutes. The reaction was heated at 160° C. for 2 hours in a microwave (Biotage Initiator 2.5). The reaction was monitored by TLC dichloromethane/methanol=9/1. Additional equivalents of sodium ethanolate were added and additional heating was carried out until completion of the reaction according to TLC. The reaction mixture was concentrated under reduced pressure and adsorbed on silica gel. The product was purified by silica gel chromatography (gradient: cyclohexane/ethylacetate=0-100%) to afford the title compound. $^1$H NMR (400 MHz, DMSO-$d_6$) δ 12.09 (s, 1H), 7.85-7.78 (m, 2H), 7.76-7.69 (m, 2H), 7.39 (dd, J=1.3, 2.9, 1H), 7.16 (dd, J=1.4, 3.8, 1H), 6.77 (dd, J=2.9, 3.8, 1H). $^{13}$C NMR (400 MHz, DMSO-$d_6$) δ 154.22, 136.46, 131.98, 130.90, 129.52, 124.07, 124.00, 118.80, 114.42, 111.01.

Example 399D 4-(4-aminophenyl)pyrrolo[1,2-d][1,2,4]triazin-1 (2H)-one

To 1.181 g 4-(4-bromophenyl)pyrrolo[1,2-d][1,2,4]triazin-1(2H)-one (4.07 mmol) in toluene (10 ml) was added 0.080 g 2-dicyclohexylphosphino-2'-(N,N-dimethylamino) biphenyl (0.2004 mmol), 0.063 g tris(dibenzylideneacetone) dipalladium(O) chloroform adduct (0.061 mmol) and 10.58 ml lithium bis(trimethylsilyl)amide 1M in toluene (10.58 mmol) under nitrogen at room temperature and the reaction was subsequently heated at 150° C. for 5 minutes by microwave (Biotage Initiator 2.5). Thin layer chromatography in cyclohexane/ethyl acetate=1/1 showed no starting material. After cooling the reaction mixture, 7 ml of 2N aqueous HCl was added, the mixture stirred for 30 minutes, and the mixture was basified until pH=10 by addition of aqueous NaOH (2N). A precipitate was formed. The solid was filtered and washed with ether and dried overnight to obtain the title compound. LCMS: m/z 227.0 (M+H). The filtrate was extracted with ethyl acetate. The organic phase was combined with the ether from the washing, dried over $Na_2SO_4$, filtered, and the solvent was evaporated under reduced pressure. The raw material was adsorbed on silica (dissolved in ethyl acetate), then purified by silica gel chromatography (cyclohexane:ethyl acetate gradient, the product was eluted at 80% of ethyl acetate) to afford additional title compound. $^1$H NMR (400 MHz, DMSO-$d_6$) δ 11.85 (br. s., 1H), 7.32-7.44 (m, 3H), 7.09 (dd, J=3.8, 1.3 Hz, 1H), 6.66-6.77 (m, 3H), 5.67 (s, 2H). $^{13}$C NMR (400 MHz, DMSO-$d_6$) δ 154.15, 150.86, 137.98, 129.55, 123.98, 118.70, 116.65, 113.95, 113.32, 110.58.

Example 399E

[4-(1-Oxo-1,2-dihydro-pyrrolo[1,2-d][1,2,4]triazin-4-yl)-phenyl]-carbamic acid phenyl ester To a suspension of 50 mg 4-(4-aminophenyl)pyrrolo[1,2-d][1,2,4]triazin-1(2H)-one (0.22 mmol) in 1 ml tetrahydrofuran at room temperature a solution of 0.03 ml pyridine (0.3 mmol) in 0.5 ml of tetrahydrofuran was added over 5 minutes. Subsequently, 0.03 ml phenylchlorformate (0.23 mmol) dissolved in 3 ml of tetrahydrofuran was added over 30 minutes and the reaction was stirred at room temperature overnight. The solvent was evaporated on vacuo and the mixture was directly incorporated on silica by dichloromethane. The mixture was purified by silica gel chromatography (4 g, cyclohexane:ethylacetate gradient) to afford crude material which was purified by column chromatography (cyclohexane:ethylacetate gradient) to afford the title compound.

Example 399F

N-[4-(1-oxo-1,2-dihydropyrrolo[1,2-d][1,2,4]triazin-4-yl)phenyl]-1,3-dihydro-2H-isoindole-2-carboxamide 40 mg [4-(1-Oxo-1,2-dihydro-pyrrolo[1,2-d][1,2,4]triazin-4-yl)-phenyl]-carbamic acid phenyl ester (0.115 mmol) were dissolved in 0.3 ml DMSO. A mixture of 15 mg isoindoline (0.121 mmol) in 0.2 ml DMSO was added at room temperature and the reaction was stirred at room temperature over night. The reaction mixture was diluted in ethyl acetate and washed with water, aqueous HCl, water, aqueous NaOH, and water. The solvent was evaporated under reduced pressure to afford the title compound.

Example 400

N-[4-(1-oxo-1,2-dihydropyrrolo[1,2-d][1,2,4]triazin-4-yl)phenyl]-5-(pyrrolidin-1-ylmethyl)-1,3-dihydro-2H-isoindole-2-carboxamide

Example 400A 5-pyrrolidin-1-ylmethyl-1,3-dihydro-isoindole-2-carboxylic acid tert-butyl ester To a solution of 1.25 g 5-hydroxymethyl-1,3-dihydro-isoindole-2-carboxylic acid tert-butyl ester (5.01 mmol) in 14 ml dichloromethane was slowly added 0.781 ml methanesulfonyl chloride (10.03 mmol) at room temperature. Subsequently the mixture was heated for 4 hours at reflux. LCMS control indicted a near complete formation of the corresponding mesylate, which was not isolated. After cooling to room temperature, 1.244 ml pyrrolidine (15.04 mmol) were added and the mixture was stirred at room temperature overnight. The reaction was complete according to LCMS. Water was added to the reaction mixture, the acidic aqueous phase was extracted two times with dichloromethane, and the water phase was basified and extracted three times with ethyl acetate. The combined ethyl acetate solutions were extracted with brine, dried over $Na_2SO_4$, filtered, and the organic solvent was removed under reduced pressure to provide the title compound. The dichloromethane phase was extracted two times with diluted NaOH, once with brine and then dried over $Na_2SO_4$. Filtration and removal of the organic solvent under reduced pressure provided additional title compound. Both fractions were combined and used in the next step without further purification. LCMS: m/z 303.2 (M+H).

Example 400B 5-pyrrolidin-1-ylmethyl-2,3-dihydro-1H-isoindole

To a solution of 1.90 g 5-pyrrolidin-1-ylmethyl-1,3-dihydro-isoindole-2-carboxylic acid tert-butyl ester (raw material; 4.96 mmol) in 5 ml dichloromethane was added 3.82 ml trifluoroacetic acid (49.6 mmol) and the reaction mixture was stirred at room temperature overnight. The trifluoroacetic acid and dichloromethane were evaporated under reduced pressure, water was added to the residue, the acidic aqueous phase extracted two times with ethyl acetate, the aqueous phase was basified with diluted NaOH and then subsequently extracted three times with dichloromethane. The dichloromethane phase was washed once with brine, dried over $Na_2SO_4$, filtered, and the solvent was removed under vacuum. The title compound was used without further purification in the next step. LCMS: m/z 203.2 (M+H).

Example 400C 5-pyrrolidin-1-ylmethyl-1,3-dihydro-isoindole-2-carboxylic acid [4-(1-oxo-1,2-dihydro-pyrrolo[1,2-d][1,2,4]triazin-4-yl)-phenyl]-amide The title compound was prepared as described in Example 399E and Example 399F, substituting isoindoline with 5-pyrrolidin-1-ylmethyl-2,3-dihydro-1H-isoindole. LCMS: m/z 455.2 (M+H).

Example 401 tert-butyl 4-{4-[(1,3-dihydro-2H-isoindol-2-ylcarbonyl)amino]phenyl}piperidine-1-carboxylate The title compound was prepared as described in Example 272A, substituting tert-butyl 4-{4-[(1,3-dihydro-2H-isoindol-2-ylcarbonyl)amino]phenyl}-3,6-dihydropyridine-1(2H)-carboxylate for 4-nitro-N-propylbenzamide. $^1$H NMR (400 MHz, DMSO-d$_6$) δ ppm 8.26 (s, 1H), 7.46-7.48 (m, 2H), 7.34-7.39 (m, 2H), 7.28-7.33 (m, 2H), 7.10-7.13 (m, 2H), 4.75 (s, 4H), 4.02-4.08 (m, 2H), 2.71-2.90 (m, 2H), 2.57-2.68 (m, 1H), 1.71-1.76 (m, 2H), 1.40-1.51 (m, 2H), 1.42 (s, 9H); MS (ESI(−)) m/e 420 (M−H)$^-$.

Example 402

N-[4-(5-propyl-1,2,4-oxadiazol-3-yl)phenyl]-1,3-dihydro-2H-isoindole-2-carboxamide

Example 402A

N-(4-cyanophenyl)isoindoline-2-carboxamide

The title compound was prepared as described in Example 1A, substituting 4-isocyanatobenzonitrile for methyl 4-isocyanatobenzoate.

Example 402B (Z)—N-(4-(N'-hydroxycarbamimidoyl)phenyl)isoindoline-2-carboxamide In a 25 mL pressure tube were mixed N-(4-cyanophenyl) isoindoline-2-carboxamide (500 mg, 1.899 mmol), hydroxylamine hydrochloride (264 mg, 3.80 mmol), and triethylamine (1.323 ml, 9.50 mmol) in ethanol (6 ml)/water (0.5 ml). The reaction vessel was sealed and heated at 80° C. for four hours. The reaction mixture was diluted with water and the solid was filtered off with water washes. HPLC purification provided the title compound.

Example 402C

N-[4-(5-propyl-1,2,4-oxadiazol-3-yl)phenyl]-1,3-dihydro-2H-isoindole-2-carboxamide In a 4 mL vial was mixed (Z)—N-(4-(N'-hydroxycarbamimidoyl)phenyl)isoindoline-2-carboxamide (50 mg, 0.169 mmol), butyric acid (0.017 ml, 0.186 mmol), 1-hydroxybenzotriazole hydrate (12.92 mg, 0.084 mmol), and N-methylmorpholine (0.056 ml, 0.506 mmol) in anhydrous dimethylformamide (2 ml). To this solution was added N-(3-dimethylaminopropyl)-N'-ethylcarbodiimide hydrochloride (48.5 mg, 0.253 mmol) and the mixture was stirred overnight at ambient temperature. The solution was diluted with ethyl acetate and washed with water, saturated aqueous sodium bicarbonate, and brine. The organic layer was dried with sodium sulfate, decanted, and concentrated. The residue was taken up in anhydrous toluene (1 ml), and the mixture was heated at 110° C. for 2 days. The reaction was diluted with water; and the solids that formed were filtered and washed with water and ether to provide the title compound. $^1$H NMR (500 MHz, DMSO-d$_6$) δ ppm 8.68 (s, 1H), 7.89-7.91 (m, 2H), 7.78-7.80 (m, 2H), 7.36-7.40 (m, 2H), 7.30-7.34 (m, 2H), 4.76-4.85 (m, 4H), 2.96 (t, J=7.4 Hz, 2H), 1.81 (hex, J=7.4 Hz, 2H), 0.99 (t, J=7.4 Hz, 3H); MS (ESI(−)) m/e 347 (M−H)$^-$.

Example 403

N-[4-(piperidin-4-yl)phenyl]-1,3-dihydro-2H-isoindole-2-carboxamide

The title compound was prepared as described in Example 2D, substituting tert-butyl 4-{4-[(1,3-dihydro-2H-isoindol-2-ylcarbonyl)amino]phenyl}piperidine-1-carboxylate for tert-butyl 4-((4-(5-fluoroisoindoline-2-carboxamido)benzamido)methyl)benzylcarbamate. $^1$H NMR (500 MHz, DMSO-d$_6$) δ ppm 8.28 (s, 1H), 7.46-7.48 (m, 2H), 7.34-7.37 (m, 2H), 7.30-7.33 (m, 2H), 7.09-7.12 (m, 2H), 4.75-4.76 (bs, 4H), 3.09-3.17 (m, 2H), 2.68 (td, J=12.3, 2.6 Hz, 2H), 2.57 (ft, J=12.0, 3.4 Hz, 1H), 1.71-1.75 (m, 2H), 1.56 (qd, J=12.5, 3.9 Hz, 2H); MS (ESI(+)) m/e 322 (M+H)$^+$.

Example 404

N-{5-[((3R)-tetrahydrofuran-3-ylmethyl)carbamoyl]pyridin-2-yl}-1,3-dihydro-2H-isoindole-2-carboxamide and N-{5-[((3S)-tetrahydrofuran-3-ylmethyl)carbamoyl]pyridin-2-yl}-1,3-dihydro-2H-isoindole-2-carboxamide The title compound was prepared as described in Example 1C, substituting (tetrahydrofuran-3-yl)methanamine for 3-phenylpropan-1-amine and 6-(isoindoline-2-carboxamido) nicotinic acid for 4-(isoindoline-2-carboxamido)benzoic acid. $^1$H NMR (400 MHz, DMSO-d$_6$) δ ppm 9.26 (s, 1H), 8.74 (d, J=2.4 Hz, 1H), 8.56-8.60 (m, 1H), 8.14 (dd, J=8.8, 2.5 Hz, 1H), 8.00 (d, J=8.8 Hz, 1H), 7.26-7.40 (m, 4H), 4.59-5.02 (m, 4H), 3.75 (td, J=8.0, 5.7 Hz, 1H), 3.69 (dd, J=8.5, 6.9 Hz, 1H), 3.59-3.66 (m, 1H), 3.48 (dd, J=8.5, 5.2 Hz, 1H), 3.18-3.31 (m, 2H), 2.43-2.51 (m, 1H), 1.90-1.99 (m, 1H), 1.56-1.65 (m, 1H); MS (ESI(−)) m/e 365 (M−H)$^-$.

Example 405

N-[4-(1-butyrylpiperidin-4-yl)phenyl]-1,3-dihydro-2H-isoindole-2-carboxamide

The title compound was prepared as described in Example 278, substituting butyryl chloride for acetyl chloride and N-[4-(piperidin-4-yl)phenyl]-1,3-dihydro-2H-isoindole-2-carboxamide for 5-amino-N-(4-(propylcarbamoyl)phenyl) isoindoline-2-carboxamide. $^1$H NMR (400 MHz, DMSO-d$_6$) δ ppm 8.27 (s, 1H), 7.46-7.49 (m, 2H), 7.34-7.39 (m, 2H), 7.28-7.33 (m, 2H), 7.11-7.14 (m, 2H), 4.75-4.76 (bs, 4H), 4.52-4.57 (m, 1H), 3.94-4.00 (m, 1H), 3.03-3.11 (m, 1H), 2.64-2.75 (m, 1H), 2.51-2.63 (m, 1H), 2.31 (t, J=7.4 Hz, 2H), 1.73-1.81 (m, 2H), 1.47-1.59 (m, 3H), 1.32-1.47 (m, 1H), 0.85-0.95 (m, 3H); MS (ESI(+)) m/e 392 (M+H)$^+$.

Example 406

N-[4-(1-isobutyrylpiperidin-4-yl)phenyl]-1,3-dihydro-2H-isoindole-2-carboxamide

The title compound was prepared as described in Example 278, substituting isobutyryl chloride for acetyl chloride and N-[4-(piperidin-4-yl)phenyl]-1,3-dihydro-2H-isoindole-2-carboxamide for 5-amino-N-(4-(propylcarbamoyl)phenyl) isoindoline-2-carboxamide. $^1$H NMR (500 MHz, DMSO-d$_6$)

δ ppm 8.28 (s, 1H), 7.46-7.48 (m, 2H), 7.34-7.39 (m, 2H), 7.29-7.33 (m, 2H), 7.12-7.14 (m, 2H), 4.75-4.76 (bs, 4H), 4.53-4.58 (m, 1H), 4.03-4.07 (m, 1H), 3.06-3.14 (m, 1H), 2.86-2.93 (m, 1H), 2.67-2.74 (m, 1H), 2.53-2.61 (m, 1H), 1.75-1.84 (m, 2H), 1.45-1.56 (m, 1H), 1.33-1.45 (m, 1H), 1.03 (d, J=6.7 Hz, 3H), 1.00 (d, J=6.6 Hz, 3H); MS (ESI(−)) m/e 390 (M−H)⁻.

Example 407

N-[4-(1-benzoylpiperidin-4-yl)phenyl]-1,3-dihydro-2H-isoindole-2-carboxamide

The title compound was prepared as described in Example 278, substituting benzoyl chloride for acetyl chloride and N-[4-(piperidin-4-yl)phenyl]-1,3-dihydro-2H-isoindole-2-carboxamide for 5-amino-N-(4-(propylcarbamoyl)phenyl)isoindoline-2-carboxamide. $^1$H NMR (500 MHz, DMSO-d$_6$) δ ppm 8.29 (s, 1H), 7.47-7.50 (m, 2H), 7.41-7.47 (m, 5H), 7.34-7.38 (m, 2H), 7.29-7.33 (m, 2H), 7.16-7.18 (m, 2H), 4.75-4.76 (bs, 4H), 4.54-4.64 (m, 1H), 3.57-3.74 (m, 1H), 3.02-3.21 (m, 1H), 2.79-2.93 (m, 1H), 2.75 (tt, J=11.9, 3.4 Hz, 1H), 1.68-1.88 (m, 2H), 1.54-1.63 (m, 2H); MS (ESI(−)) m/e 424 (M−H)⁻.

Example 408

N-{4-[5-(3-methylbutyl)-1,2,4-oxadiazol-3-yl]phenyl}-1,3-dihydro-2H-isoindole-2-carboxamide The title compound was prepared as described in Example 402C, substituting 4-methylpentanoic acid for butyric acid. $^1$H NMR (500 MHz, DMSO-d$_6$) δ ppm 8.69 (s, 1H), 7.89-7.91 (m, 2H), 7.77-7.79 (m, 2H), 7.36-7.39 (m, 2H), 7.31-7.34 (m, 2H), 4.80-4.81 (bs, 4H), 2.96-3.00 (m, 2H), 1.66-1.72 (m, 2H), 1.59-1.67 (m, 1H), 0.93 (d, J=6.4 Hz, 6H); MS (ESI(−)) m/e 375 (M−H)⁻.

Example 409

N-[4-(5-benzyl-1,2,4-oxadiazol-3-yl)phenyl]-1,3-dihydro-2H-isoindole-2-carboxamide The title compound was prepared as described in Example 402C, substituting phenylacetic acid for butyric acid. $^1$H NMR (500 MHz, DMSO-d$_6$) δ ppm 8.69 (s, 1H), 7.87-7.90 (m, 2H), 7.77-7.79 (m, 2H), 7.35-7.42 (m, 6H), 7.29-7.34 (m, 3H), 4.75-4.84 (m, 4H), 4.42 (s, 2H); MS (ESI(+)) m/e 397 (M+H)⁺.

Example 410

N-(4-{[(3R)-tetrahydrofuran-3-ylmethyl]carbamoyl}phenyl)-1,3-dihydro-2H-isoindole-2-carboxamide A racemic mixture of N-(4-{[tetrahydrofuran-3-ylmethyl]carbamoyl}phenyl)-1,3-dihydro-2H-isoindole-2-carboxamide (250 mg) was dissolved in methanol and separated using SCF-LC with a ChiralPak AD-H 21×250 mm column to provide N-(4-{[(3S)-tetrahydrofuran-3-ylmethyl]carbamoyl}phenyl)-1,3-dihydro-2H-isoindole-2-carboxamide. $^1$H NMR (300 MHz, DMSO-d$_6$) δ ppm 8.58 (s, 1H), 8.38 (t, J=5.7 Hz, 1H), 7.75-7.79 (m, 2H), 7.64-7.69 (m, 2H), 7.30-7.41 (m, 4H), 4.78-4.79 (bs, 4H), 3.57-3.78 (m, 3H), 3.48 (dd, J=8.5, 5.2 Hz, 1H), 3.17-3.28 (m, 2H), 2.41-2.50 (m, 1H), 1.87-2.04 (m, 1H), 1.54-1.66 (m, 1H); MS (ESI(+)) m/e 366 (M+H)⁺.

Example 411

N-(4-{[(3S)-tetrahydrofuran-3-ylmethyl]carbamoyl}phenyl)-1,3-dihydro-2H-isoindole-2-carboxamide A racemic mixture of N-(4-{[tetrahydrofuran-3-ylmethyl]carbamoyl}phenyl)-1,3-dihydro-2H-isoindole-2-carboxamide (250 mg) was dissolved in methanol and separated using SCF-LC with a ChiralPak AD-H 21×250 mm column to provide N-(4-{[(3R)-tetrahydrofuran-3-ylmethyl]carbamoyl}phenyl)-1,3-dihydro-2H-isoindole-2-carboxamide. $^1$H NMR (300 MHz, DMSO-d$_6$) δ ppm 8.57 (s, 1H), 8.38 (t, J=5.7 Hz, 1H), 7.75-7.79 (m, 2H), 7.64-7.69 (m, 2H), 7.30-7.39 (m, 4H), 4.78-4.79 (bs, 4H), 3.57-3.78 (m, 3H), 3.48 (dd, J=8.5, 5.3 Hz, 1H), 3.13-3.29 (m, 2H), 2.40-2.50 (m, 1H), 1.87-2.07 (m, 1H), 1.54-1.66 (m, 1H); MS (ESI(+)) m/e 366 (M+H)⁺.

Example 422 tert-butyl 4-{6-[(1,3-dihydro-2H-isoindol-2-ylcarbonyl)amino]-1H-benzimidazol-2-yl}piperazine-1-carboxylate Example 422A tert-butyl 4-(5-nitro-1H-benzo[d]imidazol-2-yl)piperazine-1-carboxylate In a 20 mL sealed tube under nitrogen, a mixture of tert-butyl piperazine-1-carboxylate (0.943 g, 5.06 mmol), 2-chloro-5-nitro-1H-benzo[d]imidazole (0.5 g, 2.53 mmol) and ethanol (9.5 mL) was heated at 135° C. for 2 hours. The reaction was concentrated and the residue was purified by reverse-phase chromatography to provide the title compound.

Example 422B tert-butyl 4-(5-amino-1H-benzo[d]imidazol-2-yl)piperazine-1-carboxylate The title compound was prepared as described in Example 274, substituting tert-butyl 4-(5-nitro-1H-benzo[d]imidazol-2-yl)piperazine-1-carboxylate for 5-nitro-N-[4-(propylcarbamoyl)phenyl]-1,3-dihydro-2H-isoindole-2-carboxamide.

Example 422C tert-butyl 4-{6-[(1,3-dihydro-2H-isoindol-2-ylcarbonyl)amino]-1H-benzimidazol-2-yl}piperazine-1-carboxylate The title compound was prepared as described in Example 272B, substituting tert-butyl 4-(5-amino-1H-benzo[d]imidazol-2-yl)piperazine-1-carboxylate for 4-amino-N-propylbenzamide and isoindoline for methyl isoindoline-5-carboxylate hydrochloride. $^1$H NMR (400 MHz, DMSO-d$_6$, Temp=90° C.) δ ppm 10.90-11.08 (bs, 1H), 7.84-7.85 (m, 1H), 7.46-7.48 (m, 1H), 7.27-7.35 (m, 4H), 7.04-7.06 (m, 2H), 4.76 (s, 4H), 3.46 (s, 8H), 1.44 (s, 9H); MS (ESI(+)) m/e 463 (M+H)⁺.

Example 423

N-[2-(piperazin-1-yl)-1H-benzimidazol-6-yl]-1,3-dihydro-2H-isoindole-2-carboxamide The title compound was prepared as described in Example 2D, substituting tert-butyl 4-{6-[(1,3-dihydro-2H-isoindol-2-ylcarbonyl)amino]-1H-benzimidazol-2-yl}piperazine-1-carboxylate for tert-butyl 44(4-(5-fluoroisoindoline-2-carboxamido)benzamido)methyl)benzylcarbamate. $^1$H NMR (300 MHz, DMSO-$d_6$) δ ppm 11.04-11.29 (m, 1H), 8.08-8.12 (bs, 1H), 7.41-7.58 (m, 1H), 7.24-7.39 (m, 4H), 7.04-7.06 (m, 2H), 4.76 (s, 4H), 3.37-3.44 (m, 4H), 2.85-2.89 (m, 4H); MS (ESI(+)) m/e 363 (M+H)$^+$.

Example 424

N-[4-(propylcarbamoyl)phenyl]-5-vinyl-1,3-dihydro-2H-isoindole-2-carboxamide

In a sealed vial under nitrogen, a mixture of potassium vinyltrifluoroborate (100 mg, 0.75 mmol), 5-bromo-N-(4-(propylcarbamoyl)phenyl)isoindoline-2-carboxamide (150 mg, 0.37 mmol), bis(triphenylphosphine)palladium(II) chloride and saturated aqueous sodium bicarbonate (0.62 ml) in dimethylformamide was heated at 85° C. for 5 hours. The reaction was poured into water, filtered, dried and purified by reverse-phase chromatography to provide the title compound. $^1$H NMR (300 MHz, DMSO-$d_6$) δ ppm 8.57 (s, 1H), 8.25 (t, J=5.7 Hz, 1H), 7.75-7.78 (m, 2H), 7.63-7.67 (m, 2H), 7.47 (s, 1H), 7.42 (dd, J=7.9, 1.5 Hz, 1H), 7.34 (d, J=7.8 Hz, 1H), 6.77 (dd, J=17.6, 10.9 Hz, 1H), 5.85 (dd, J=17.6, 1.0 Hz, 1H), 5.27 (d, J=11.0 Hz, 1H), 4.77-4.78 (bs, 4H), 3.16-3.22 (m, 2H), 1.46-1.59 (m, 2H), 0.89 (t, J=7.4 Hz, 3H); MS (ESI(+)) m/e 350 (M+H)$^+$.

Example 428

N-{4-[5-(tetrahydrofuran-3-yl)-1,2,4-oxadiazol-3-yl]phenyl}-1,3-dihydro-2H-isoindole-2-carboxamide The title compound was prepared as described in Example 402C, substituting tetrahydrofuran-3-carboxylic acid for butyric acid. $^1$H NMR (500 MHz, DMSO-$d_6$) δ ppm 8.69 (s, 1H), 7.89-7.92 (m, 2H), 7.78-7.81 (m, 2H), 7.36-7.40 (m, 2H), 7.30-7.34 (m, 2H), 4.80-4.81 (bs, 4H), 4.08 (dd, J=8.6, 7.6 Hz, 1H), 3.97 (dd, J=8.6, 5.4 Hz, 1H), 3.86-3.95 (m, 2H), 3.79-3.85 (m, 1H), 2.40 (dddd, J=12.5, 9.0, 7.6, 5.9 Hz, 1H), 2.26 (ddt, J=7.7, 12.4, 6.2 Hz, 1H); MS (ESI(−)) m/e 375 (M−H)$^-$.

Example 429

N-[4-(1-isobutyl-1,2,3,6-tetrahydropyridin-4-yl)phenyl]-1,3-dihydro-2H-isoindole-2-carboxamide In a 4 mL were mixed N-(4-(1,2,3,6-tetrahydropyridin-4-yl)phenyl)isoindoline-2-carboxamide (50 mg, 0.157 mmol) and isobutyraldehyde (0.014 ml, 0.157 mmol) in anhydrous dichloroethane (2 ml) at room temperature. Sodium triacetoxyborohydride (46.4 mg, 0.219 mmol) was added, and reaction was stirred overnight. The reaction mixture was diluted with water, ethyl acetate and saturated aqueous sodium bicarbonate. The layers were separated and the organic layer was washed with brine. The organic layer was diluted with methanol, dried with sodium sulfate, filtered and concentrated. The residue was purified by flash chromatography to provide the title compound. $^1$H NMR (400 MHz, DMSO-$d_6$) δ ppm 8.35 (s, 1H), 7.53-7.55 (m, 2H), 7.30-7.38 (m, 6H), 6.06-6.08 (m, 1H), 4.77 (s, 4H), 3.01-3.03 (m, 2H), 2.57 (t, J=5.6 Hz, 2H), 2.41-2.47 (m, 2H), 2.14 (d, J=7.3 Hz, 2H), 1.77-1.88 (m, 1H), 0.88 (d, J=6.5 Hz, 6H); MS (ESI(−)) m/e 374 (M−H)$^-$.

Example 432

N-{4-[1-(4-methylbenzoyl)-1,2,3,6-tetrahydropyridin-4-yl]phenyl}-1,3-dihydro-2H-isoindole-2-carboxamide The title compound was prepared as described in Example 278, substituting 4-methylbenzoyl chloride for acetyl chloride and N-(4-(1,2,3,6-tetrahydropyridin-4-yl)phenyl)isoindoline-2-carboxamide for 5-amino-N-(4-(propylcarbamoyl)phenyl)isoindoline-2-carboxamide. $^1$H NMR (400 MHz, DMSO-$d_6$) δ ppm 8.38 (s, 1H), 7.55-7.58 (m, 2H), 7.20-7.39 (m, 10H), 6.01-6.21 (m, 1H), 4.77 (s, 4H), 3.93-4.36 (m, 2H), 3.43-3.90 (m, 2H), 2.48-2.57 (m, 2H), 2.36 (s, 3H); MS (ESI(+)) m/e 438 (M+H)$^+$.

Example 433

N-[4-(1-benzyl-1,2,3,6-tetrahydropyridin-4-yl)phenyl]-1,3-dihydro-2H-isoindole-2-carboxamide The title compound was prepared as described in Example 429, substituting benzaldehyde for isobutyraldehyde. $^1$H NMR (400 MHz, DMSO-$d_6$) δ ppm 8.36 (s, 1H), 7.52-7.55 (m, 2H), 7.20-7.42 (m, 11H), 6.06-6.08 (m, 1H), 4.76-4.77 (bs, 4H), 3.58 (s, 2H), 3.04-3.06 (m, 2H), 2.63 (t, J=5.6 Hz, 2H), 2.42-2.49 (m, 2H); MS (ESI(+)) m/e 410 (M+H)$^+$.

Example 440

N-{4-[(propylamino)carbonyl]phenyl}-5-pyridin-3-yl-1,3-dihydro-2H-isoindole-2-carboxamide The title compound was prepared as described in Example 280, substituting pyridin-3-ylboronic acid for 1H-pyrazol-3-ylboronic acid and 5-bromo-N-[4-(propylcarbamoyl)phenyl]-1,3-dihydro-2H-isoindole-2-carboxamide for 5-bromo-N-(4-(propylcarbamoyl)phenyl)isoindoline-2-carboxamide. $^1$H NMR (300 MHz, DMSO-$d_6$) δ ppm 8.91 (dd, J=2.4, 0.9 Hz, 1H), 8.63 (s, 1H), 8.58 (dd, J=4.7, 1.6 Hz, 1H), 8.27 (t, J=5.6 Hz, 1H), 8.10 (ddd, J=7.9, 2.4, 1.6 Hz, 1H), 7.73-7.79 (m, 3H), 7.65-7.70 (m, 3H), 7.48-7.53 (m, 2H), 4.79-4.91 (m, 4H), 3.15-3.23 (m, 2H), 1.54 (s, 2H), 0.89 (t, J=7.4 Hz, 3H); MS (ESI(+)) m/e 401 (M+H)$^+$.

Example 441

N-{4-[(propylamino)carbonyl]phenyl}-5-pyridin-4-yl-1,3-dihydro-2H-isoindole-2-carboxamide The title compound was prepared as described in Example 280, substituting pyridin-4-ylboronic acid for 1H-pyrazol-3-ylboronic acid and 5-bromo-N-[4-(propylcarbamoyl)phenyl]-1,3-dihydro-2H-isoindole-2-carboxamide for 5-bromo-N-(4-(propylcarbamoyl)phenyl)isoindoline-2-carboxamide. $^1$H NMR (300 MHz, DMSO-$d_6$) δ ppm 8.62-8.66 (m, 3H), 8.25 (t, J=5.6 Hz, 1H), 7.70-7.81 (m, 6H), 7.64-7.69 (m, 2H), 7.52 (d, J=8.0 Hz, 1H), 4.85-4.92 (m, 4H), 3.16-3.22 (m, 2H), 1.46-1.59 (m, 2H), 0.89 (t, J=7.4 Hz, 3H). MS (ESI(+)) m/e 401 (M+H)$^+$.

Example 442

N$^5$-(2-methoxyethyl)-N$^2$-{4-[(propylamino)carbonyl]phenyl}-1,3-dihydro-2H-isoindole-2,5-dicarboxamide The title compound was prepared as described in Example 1C, substituting 2-methoxyethanamine for 3-phenylpropan-1-amine and 2-{[4-(propylcarbamoyl)phenyl]carbamoyl}isoindoline-5-carboxylic acid for 4-(isoindoline-2-carboxamido)benzoic acid. $^1$H NMR (300 MHz, DMSO-d$_6$) δ ppm 8.61 (s, 1H), 8.54 (d, J=5.3 Hz, 1H), 8.26 (t, J=5.7 Hz, 1H), 7.79-7.85 (m, 2H), 7.73-7.80 (m, 2H), 7.63-7.67 (m, 2H), 7.45 (d, J=7.8 Hz, 1H), 4.81-4.83 (bs, 4H), 3.39-3.51 (m, 4H), 3.27 (s, 3H), 3.03-3.22 (m, 2H), 1.46-1.59 (m, 2H), 0.89 (t, J=7.4 Hz, 3H); MS (ESI(+)) m/e 425 (M+H)$^+$.

Example 443

N-(4-cyanophenyl)-1,3-dihydro-2H-isoindole-2-carboxamide

The title compound was prepared as described in Example 1A, substituting 4-isocyanatobenzonitrile for methyl 4-isocyanatobenzoate. $^1$H NMR (400 MHz, DMSO-d$_6$) δ ppm 8.83 (s, 1H), 7.78-7.82 (m, 2H), 7.69-7.73 (m, 2H), 7.31-7.39 (m, 4H), 4.79-4.81 (bs, 4H); MS (ESI(+)) m/e 264 (M+H)$^+$.

Example 444

N-[4-(trifluoromethyl)phenyl]-1,3-dihydro-2H-isoindole-2-carboxamide

The title compound was prepared as described in Example 1A, substituting 1-isocyanato-4-(trifluoromethyl)benzene for methyl 4-isocyanatobenzoate. $^1$H NMR (400 MHz, DMSO-d$_6$) δ ppm 8.74 (s, 1H), 7.80-7.83 (m, 2H), 7.60-7.63 (m, 2H), 7.30-7.39 (m, 4H), 4.79-4.80 (bs, 4H); MS (ESI(+)) m/e 307 (M+H)$^+$.

Example 450

5-(1,2-dihydroxyethyl)-N-{4-[(propylamino)carbonyl]phenyl}-1,3-dihydro-2H-isoindole-2-carboxamide A suspension of N-[4-(propylcarbamoyl)phenyl]-5-vinyl-1,3-dihydro-2H-isoindole-2-carboxamid (0.03 g, 0.086 mmol) in tetrahydrofuran (1 ml) and 2-propanol (0.3 ml) was treated with osmium tetroxide (2.5% wt. % solution in 2-methyl-2-propanol) (0.108 ml, 8.59 μmol). The reaction mixture was treated with N-methylmorpholine-N-oxide (0.030 g, 0.258 mmol). The reaction mixture was allowed to stir at room temperature overnight, quenched with aqueous sodium sulfite solution and extracted with ethyl acetate. The combined organic layers were washed with brine, dried over anhydrous sodium sulfate, and concentrated under vacuum. Flash chromatography provided the title compound. $^1$H NMR (300 MHz, DMSO-d$_6$) δ ppm 8.55 (s, 1H), 8.25 (t, J=5.7 Hz, 1H), 7.74-7.78 (m, 2H), 7.63-7.68 (m, 2H), 7.27-7.33 (m, 3H), 5.24 (d, J=4.2 Hz, 1H), 4.75-4.77 (bs, 4H), 4.70 (t, J=5.8 Hz, 1H), 4.53-4.59 (m, 1H), 3.43 (t, J=5.8 Hz, 2H), 3.16-3.23 (m, 2H), 1.42-1.63 (m, 2H), 0.89 (t, J=7.4 Hz, 3H); MS (ESI(+)) m/e 384 (M+H)$^+$.

Example 451

N-[4-(1-benzoylpiperidin-4-yl)butyl]-5-cyano-1,3-dihydro-2H-isoindole-2-carboxamide

Example 451A tert-butyl 4-(4-(5-cyanoisoindoline-2-carboxamido)butyl)piperidine-1-carboxylate The title compound was prepared as described in Example 272B, substituting tert-butyl 4-(4-aminobutyl)piperidine-1-carboxylate for 4-amino-N-propylbenzamide and isoindoline-5-carbonitrile for methyl isoindoline-5-carboxylate hydrochloride.

Example 451B 5-cyano-N-(4-(piperidin-4-yl)butyl)isoindoline-2-carboxamide

The title compound was prepared as described in Example 2D, substituting tert-butyl 4-(4-(5-cyanoisoindoline-2-carboxamido)butyl)piperidine-1-carboxylate for tert-butyl 4-((4-(5-fluoroisoindoline-2-carboxamido)benzamido)methyl)benzylcarbamate.

Example 451C

N-[4-(1-benzoylpiperidin-4-yl)butyl]-5-cyano-1,3-dihydro-2H-isoindole-2-carboxamide The title compound was prepared as described in Example 278, substituting benzoyl chloride for acetyl chloride and 5-cyano-N-(4-(piperidin-4-yl)butyl)isoindoline-2-carboxamide for 5-amino-N-(4-(propylcarbamoyl)phenyl)isoindoline-2-carboxamide. $^1$H NMR (300 MHz, DMSO-d$_6$) δ ppm 7.83 (s, 1H), 7.75 (dd, J=7.9, 1.5 Hz, 1H), 7.53 (d, J=7.9 Hz, 1H), 7.41-7.44 (m, 3H), 7.31-7.38 (m, 2H), 6.36 (t, J=5.5 Hz, 1H), 4.60-4.64 (m, 4H), 4.30-4.53 (m, 1H), 3.42-3.71 (m, 1H), 3.02-3.10 (m, 2H), 2.64-3.00 (m, 2H), 1.56-1.84 (m, 2H), 1.37-1.54 (m, 3H), 1.24-1.31 (m, 4H), 0.93-1.16 (m, 2H); MS (ESI(+)) m/e 431 (M+H)$^+$.

Example 452

N-(1'-butyryl-1',2',3',6'-tetrahydro-3,4'-bipyridin-6-yl)-1,3-dihydro-2H-isoindole-2-carboxamide

Example 452A

N-(5-bromopyridin-2-yl)isoindoline-2-carboxamide

The title compound was prepared as described in Example 344A, substituting 5-bromopyridin-2-amine for tert-butyl 5-aminoisoindoline-2-carboxylate.

Example 452B tert-butyl 4-(6-(isoindoline-2-carboxamido)pyridin-3-yl)-5,6-dihydropyridine-1(2H)-carboxylate The title compound was prepared as described in Example 280, substituting tert-butyl 4-(4,4,5,5-tetramethyl-1,3,2-dioxaborolan-2-yl)-5,6-dihydropyridine-1(2H)-carboxylate for 1H-pyrazol-3-ylboronic acid and N-(5-bromopyridin-2-yl)isoindoline-2-carboxamide for 5-bromo-N-(4-(propylcarbamoyl)phenyl)isoindoline-2-carboxamide.

Example 452C

N-(5-(1,2,3,6-tetrahydropyridin-4-yl)pyridin-2-yl)isoindoline-2-carboxamide

The title compound was prepared as described in Example 2D, substituting tert-butyl 4-(6-(isoindoline-2-carboxamido)pyridin-3-yl)-5,6-dihydropyridine-1(2H)-carboxylate for tert-butyl 4-((4-(5-fluoroisoindoline-2-carboxamido)benzamido)methyl)benzylcarbamate.

Example 452D

N-(1'-butyryl-1',2',3',6'-tetrahydro-3,4'-bipyridin-6-yl)-1,3-dihydro-2H-isoindole-2-carboxamide The title compound was prepared as described in Example 278, substituting butyryl chloride for acetyl chloride and N-(5-(1,2,3,6-tetrahydropyridin-4-yl)pyridin-2-yl)isoindoline-2-carboxamide for 5-amino-N-(4-(propylcarbamoyl)phenyl)isoindoline-2-carboxamide. $^1$H NMR (500 MHz, DMSO-$d_6$) δ ppm 8.92-8.95 (bs, 1H), 8.32-8.35 (m, 1H), 7.64-7.97 (m, 2H), 6.94-7.38 (m, 4H), 6.16-6.22 (bs, 1H), 4.45-5.02 (m, 4H), 4.08-4.15 (m, 2H), 3.62-3.68 (m, 2H), 2.23-2.65 (m, 4H), 1.46-1.64 (m, 2H), 0.87-0.93 (m, 3H); MS (ESI(+)) m/e 391 (M+H)$^+$.

Table 6.

The title compound was prepared as described in Example 1C, substituting N-(5-(1,2,3,6-tetrahydropyridin-4-yl)pyridin-2-yl)isoindoline-2-carboxamide for 3-phenylpropan-1-amine and the appropriate carboxylic acid for 4-(isoindoline-2-carboxamido)benzoic acid.

| Ex | Name | $^1$H NMR | MS |
|---|---|---|---|
| 453 | N-(1'-isobutyryl-1',2',3',6'-tetrahydro-3,4'-bipyridin-6-yl)-1,3-dihydro-2H-isoindole-2-carboxamide | $^1$H NMR (500 MHz, DMSO-$d_6$) δ ppm 8.91-8.95 (bs, 1H), 8.33-8.38 (m, 1H), 7.79-7.92 (m, 2H), 7.27-7.36 (m, 3H), 6.17-6.22 (bs, 1H), 4.76-4.83 (bs, 4H), 4.07-4.22 (m, 2H), 3.64-3.73 (m, 2H), 2.84-2.98 (m, 1H), 2.37-2.63 (m, 3H), 0.77-1.20 (m, 6H) | (ESI (+)) m/e 391 (M + H)$^+$ |
| 454 | N-[1'-((3R)-tetrahydrofuran-3-ylcarbonyl)-1',2',3',6'-tetrahydro-3,4'-bipyridin-6-yl]-1,3-dihydro-2H-isoindole-2-carboxamide | $^1$H NMR (500 MHz, DMSO-$d_6$) δ ppm 8.92-8.95 (bs, 1H), 8.32-8.36 (bs, 1H), 7.79-7.92 (m, 2H), 7.11-7.51 (m, 4H), 6.17-6.21 (bs, 1H), 4.59-5.04 (m, 4H), 4.10-4.22 (m, 2H), 3.82-4.01 (m, 1H), 3.59-3.81 (m, 5H), 2.33-2.62 (m, 2H), 1.94-2.15 (m, 2H) | (ESI (+)) m/e 419 (M + H)$^+$ |
| 495 | N-(1'-benzoyl-1',2',3',6'-tetrahydro-3,4'-bipyridin-6-yl)-1,3-dihydro-2H-isoindole-2-carboxamide | $^1$H NMR (400 MHz, DMSO-$d_6$, Temp = 90° C.) δ ppm 8.51 (bs, 1H), 8.32 (d, J = 2.5 Hz, 1H), 7.90 (d, J = 8.7 Hz, 1H), 7.77 (dd, J = 8.7, 2.5 Hz, 1H), 7.48-7.39 (m, 5H), 7.36-7.25 (m, 4H), 6.16 (bs, 1H), 4.81 (s, 4H), 4.18 (m, 2H), 3.68 (m, 2H), 2.55 (m, 2H) | (ESI (+)) m/e 425 (M + H)$^+$ |
| 764 | N-[1'-(tetrahydrofuran-2-ylcarbonyl)-1',2',3',6'-tetrahydro-3,4'-bipyridin-6-yl]-1,3-dihydro-2H-isoindole-2-carboxamide | $^1$H NMR (400 MHz, DMSO-$d_6$, Temp = 90° C.) δ ppm 8.52 (bs, 1H), 8.32 (d, J = 2.5 Hz, 1H), 7.91 (m, 1H), 7.76 (dd, J = 8.7, 2.5 Hz, 1H), 7.37-7.26 (m, 4H), 6.16 (m, 1H), 4.82 (s, 4H), 4.68 (dd, J = 7.6, 5.6 Hz, 1H), 4.17 (m, 2H), 3.86-3.70 (m, 4H), 2.52 (m, 2H), 2.12 (m, 1H), 2.01 (m, 1H), 1.87 (m, 2H) | (ESI (+)) m/e 419 (M + H)$^+$ |
| 765 | N-[1'-(tetrahydro-2H-pyran-4-ylcarbonyl)-1',2',3',6'-tetrahydro-3,4'-bipyridin-6-yl]-1,3-dihydro-2H-isoindole-2-carboxamide | $^1$H NMR (400 MHz, DMSO-$d_6$, Temp = 90° C.) δ ppm 8.52 (s, 1H), 8.32 (d, J = 2.5 Hz, 1H), 7.91 (d, J = 8.7 Hz, 1H), 7.77 (dd, J = 8.7, 2.5 Hz, 1H), 7.37-7.26 (m, 4H), 6.16 (m, 1H), 4.82 (s, 4H), 4.17 (m, 2H), 3.87 (m, 2H), 3.72 (t, J = 5.7 Hz, 2H), 3.43 (td, J = 11.4, 2.6 Hz, 2H), 2.92 (m, 1H), 2.52 (m, 2H), 1.74-1.60 (m, 2H), 1.62-1.53 (m, 2H) | (ESI (+)) m/e 433 (M + H)$^+$ |
| 766 | N-[1'-(1,4-dioxan-2-ylcarbonyl)-1',2',3',6'-tetrahydro-3,4'-bipyridin-6-yl]-1,3-dihydro-2H-isoindole-2-carboxamide | $^1$H NMR (400 MHz, DMSO-$d_6$, Temp = 90° C.) δ ppm 8.52 (s, 1H), 8.32 (d, J = 2.2 Hz, 1H), 7.91 (d, J = 8.8 Hz, 1H), 7.76 (dd, J = 8.8, 2.5 Hz, 1H), 7.40-7.23 (m, 4H), 6.15 (m, 1H), 4.82 (s, 4H), 4.38 (dd, J = 9.2, 2.9 Hz, 1H), 4.16 (m, 2H), 3.83-3.61 (m, 7H), 3.53 (m, 1H), 2.53 (m, 2H) | (ESI (+)) m/e 435 (M + H)$^+$ |
| 767 | N-{1'-[(1-methylpyrrolidin-3-yl)carbonyl]-1',2',3',6'-tetrahydro-3,4'-bipyridin-6-yl}-1,3-dihydro-2H-isoindole-2-carboxamide | $^1$H NMR (400 MHz, DMSO-$d_6$, Temp = 90° C.) δ ppm 8.54 (m, 1H), 8.31 (dd, J = 2.5, 0.8 Hz, 1H), 7.90 (dd, J = 8.7, 0.8 Hz, 1H), 7.75 (dd, J = 8.7, 2.5 Hz, 1H), 7.36-7.25 (m, 4H), 6.15 (m, 1H), 4.81 (s, 4H), 4.13 (m, 2H), 3.69 (t, J = 5.7 Hz, 2H), 3.26 (m, 1H), 2.77 (t, J = 8.6 Hz, 1H), 2.68-2.53 (m, 4H), 2.38 (m, 1H), 2.24 (s, 3H), 2.13-1.92 (m, 2H) | (ESI (+)) m/e 432 (M + H)$^+$ |
| 768 | N-{1'-[(1,1-dioxidotetrahydrothiophen-3-yl)carbonyl]-1',2',3',6'-tetrahydro-3,4'-bipyridin-6-yl}-1,3-dihydro-2H-isoindole-2-carboxamide | $^1$H NMR (400 MHz, DMSO-$d_6$, Temp = 90° C.) δ ppm 8.53 (bs, 1H), 8.33 (d, J = 2.5 Hz, 1H), 7.91 (d, J = 8.7 Hz, 1H), 7.77 (dd, J = 8.7, 2.5 Hz, 1H), 7.37-7.26 (m, 4H), 6.16 (m, 1H), 4.82 (s, 4H), 4.19 (m, 2H), 3.74 (m, 3H), 3.33-3.05 (m, 4H), 2.55 (m, 2H), 2.37 (m, 1H), 2.15 (m, 1H) | (ESI (+)) m/e 467 (M + H)$^+$ |

-continued

| Ex | Name | ¹H NMR | MS |
|---|---|---|---|
| 769 | N-[1'-(2-hydroxy-2-methylpropanoyl)-1',2',3',6'-tetrahydro-3,4'-bipyridin-6-yl]-1,3-dihydro-2H-isoindole-2-carboxamide | ¹H NMR (400 MHz, DMSO-$d_6$, Temp = 90° C.) δ ppm 8.51 (bs, 1H), 8.31 (d, J = 2.5 Hz, 1H), 7.90 (d, J = 8.7 Hz, 1H), 7.76 (dd, J = 8.7, 2.5 Hz, 1H), 7.36-7.25 (m, 4H), 6.17 (m, 1H), 5.11 (bs, 1H), 4.81 (s, 4H), 4.30 (m, 2H), 3.94 (m, 2H), 2.51 (m, 2H), 1.37 (s, 6H) | (ESI (+)) m/e 407 (M + H)⁺ |
| 801 | N-[1'-(morpholin-4-ylacetyl)-1',2',3',6'-tetrahydro-3,4'-bipyridin-6-yl]-1,3-dihydro-2H-isoindole-2-carboxamide | ¹H NMR (400 MHz, DMSO-$d_6$, Temp = 90° C.) δ ppm 8.51 (s, 1H), 8.32 (d, J = 2.5 Hz, 1H), 7.90 (d, J = 8.7 Hz, 1H), 7.76 (dd, J = 8.7, 2.5 Hz, 1H), 7.36-7.26 (m, 4H), 6.15 (m, 1H), 4.81 (s, 4H), 4.13 (m, 2H), 3.73 (m, 2H), 3.58 (m, 4H), 3.21 (s, 2H), 2.48 (m, 2H), 2.45 (m, 4H) | (ESI (+)) m/e 448 (M + H)⁺ |

Example 455

N-[2-(4-acetylpiperazin-1-yl)-1H-benzimidazol-5-yl]-1,3-dihydro-2H-isoindole-2-carboxamide The title compound was prepared as described in Example 278, substituting N-[2-(piperazin-1-yl)-1H-benzimidazol-6-yl]-1,3-dihydro-2H-isoindole-2-carboxamide for 5-amino-N-(4-(propylcarbamoyl)phenyl)isoindoline-2-carboxamide.
¹H NMR (500 MHz, DMSO-$d_6$, Temp=90° C.) δ ppm 11.01-11.10 (bs, 1H), 7.89-7.91 (bs, 1H), 7.44-7.52 (m, 1H), 7.32-7.35 (m, 2H), 7.27-7.31 (m, 2H), 7.03-7.06 (m, 2H), 4.76 (s, 4H), 3.55-3.62 (m, 4H), 3.46-3.51 (m, 4H), 2.04 (s, 3H); MS (ESI(+)) m/e 405 (M+H)⁺.

Table 7.

The following Examples were essentially prepared as described in Example 1C, substituting the appropriate tetrandropyridine for 3-phenylpropan-1-amine and the appropriate carboxylic acid for 4-(isoindoline-2-carboxamido)benzoic acid.

| Ex | Name | ¹H NMR | MS |
|---|---|---|---|
| 456 | N-{4-[1-(5-oxo-L-prolyl)-1,2,3,6-tetrahydropyridin-4-yl]phenyl}-1,3-dihydro-2H-isoindole-2-carboxamide | ¹H NMR (400 MHz, Pyridine-$d_5$, Temp = 90° C.) δ ppm 8.15-8.17 (bs, 1H), 7.85-7.88 (m, 3H), 7.36-7.38 (m, 2H), 7.16-7.25 (m, 4H), 5.97-5.99 (m, 1H), 4.85-4.88 (m, 4H), 4.60-4.64 (m, 1H), 4.09-4.26 (m, 2H), 3.57-3.81 (m, 2H), 2.40-2.50 (m, 3H), 2.25-2.38 (m, 2H), 2.08-2.15 (m, 1H) | (ESI (−)) m/e 429 (M − H)⁻ |
| 457 | N-{4-[1-(5-oxo-D-prolyl)-1,2,3,6-tetrahydropyridin-4-yl]phenyl}-1,3-dihydro-2H-isoindole-2-carboxamide | ¹H NMR (400 MHz, Pyridine-$d_5$, Temp = 90° C.) δ ppm 8.14-8.16 (bs, 1H), 7.85-7.88 (m, 2H), 7.75-7.82 (m, 1H), 7.36-7.38 (m, 2H), 7.20-7.24 (m, 2H), 7.16-7.20 (m, 2H), 5.97-5.99 (m, 1H), 4.83-4.89 (m, 4H), 4.60-4.63 (m, 1H), 3.59-3.79 (m, 2H), 2.40-2.51 (m, 3H), 2.24-2.38 (m, 2H), 2.08-2.15 (m, 1H) | (ESI (−)) m/e 429 (M − H)⁻ |
| 458 | N-[4-(1-propionyl-1,2,3,6-tetrahydropyridin-4-yl)phenyl]-1,3-dihydro-2H-isoindole-2-carboxamide | ¹H NMR (400 MHz, Pyridine-$d_5$, Temp = 90° C.) δ ppm 8.08-8.15 (m, 1H), 7.84-7.87 (m, 2H), 7.37-7.39 (m, 2H), 7.20-7.24 (m, 2H), 7.16-7.19 (m, 2H), 5.99 (t, J = 3.2 Hz, 1H), 4.84-4.87 (m, 4H), 4.08-4.22 (m, 2H), 3.55-3.75 (m, 2H), 2.42-2.49 (m, 2H), 2.31 (q, J = 7.4 Hz, 2H), 1.17 (t, J = 7.5 Hz, 3H) | (ESI (+)) m/e 376 (M + H)⁺ |
| 459 | N-{4-[1-(2-methylbutanoyl)-1,2,3,6-tetrahydropyridin-4-yl]phenyl}-1,3-dihydro-2H-isoindole-2-carboxamide | ¹H NMR (400 MHz, Pyridine-$d_5$, Temp = 90° C.) δ ppm 8.11-8.12 (bs, 1H), 7.84-7.86 (m, 2H), 7.38-7.40 (m, 2H), 7.20-7.24 (m, 2H), 7.18 (d, J = 4.1 Hz, 1H), 7.15-7.18 (m, 1H), 6.00-6.03 (m, 1H), 4.83-4.89 (m, 4H), 4.18-4.27 (m, 2H), 3.67-3.79 (m, 2H), 2.69 (h, J = 6.7 Hz, 1H), 2.48-2.51 (m, 2H), 1.75-1.89 (m, 1H), 1.40-1.53 (m, 1H), 1.15 (d, J = 6.9 Hz, 3H), 0.90 (t, J = 7.4 Hz, 3H) | (ESI (+)) m/e 404 (M + H)⁺ |
| 460 | N-{4-[1-(2-ethylbutanoyl)-1,2,3,6-tetrahydropyridin-4-yl]phenyl}-1,3-dihydro-2H-isoindole-2-carboxamide | ¹H NMR (400 MHz, Pyridine-$d_5$, Temp = 90° C.) δ ppm 8.12 (d, J = −1.9 Hz, 1H), 7.84-7.87 (m, 2H), 7.38-7.41 (m, 2H), 7.21-7.24 (m, 2H), 7.15-7.20 (m, 2H), 6.01-6.04 (m, 1H), 4.86 (s, 4H), 4.21-4.32 (m, 2H), 3.73-3.84 (m, 2H), 2.57-2.67 (m, 1H), 2.48-2.55 (m, 2H), 1.74-1.88 (m, 2H), 1.45-1.57 (m, 2H), 0.90 (t, J = 7.4 Hz, 6H) | (ESI (+)) m/e 418 (M + H)⁺ |
| 461 | N-{4-[1-(methoxyacetyl)-1,2,3,6-tetrahydropyridin-4-yl]phenyl}-1,3-dihydro-2H-isoindole-2-carboxamide | ¹H NMR (400 MHz, DMSO-$d_6$, Temp = 90° C.) δ ppm 2.48-2.54 (m, 2 H), 3.32 (s, 3 H), 3.64 (t, J = 5.80 Hz, 2 H), 4.06-4.13 (m, 4 H), 4.77 (s, 4 H), 6.02-6.09 (m, 1 H), 7.27-7.37 (m, 6 H), 7.51-7.56 (m, 2 H), 8.12 (s, 1 H) | (ESI (+)) m/e 392 (M + H)⁺ |

| Ex | Name | ¹H NMR | MS |
|---|---|---|---|
| 462 | N-{4-[1-(ethoxyacetyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 8.11-8.12 (bs, 1H), 7.84-7.86 (m, 2H), 7.36-7.39 (m, 2H), 7.20-7.25 (m, 2H), 7.13-7.20 (m, 2H), 5.97-6.00 (m, 1H), 4.84-4.88 (m, 4H), 4.24 (s, 2H), 4.18-4.23 (m, 2H), 3.69-3.74 (m, 2H), 3.57 (q, J = 6.9 Hz, 2H), 2.46-2.53 (m, 2H), 1.17 (t, J = 6.9 Hz, 3H) | (ESI (+)) m/e 406 (M + H)⁺ |
| 463 | N-(4-{1-[(2-methoxyethoxy)acetyl]-1,2,3,6-tetrahydropyridin-4-yl}phenyl)-1,3-dihydro-2H-isoindole-2-carboxamide | ¹H NMR (400 MHz, Pyridine-d₅, Temp = 90° C.) δ ppm 8.10-8.13 (bs, 1H), 7.82-7.87 (m, 2H), 7.35-7.40 (m, 2H), 7.19-7.25 (m, 2H), 7.15-7.20 (m, 2H), 5.96-6.00 (m, 1H), 4.84-4.88 (m, 4H), 4.30-4.34 (m, 2H), 4.17-4.25 (m, 2H), 3.73-3.77 (m, 2H), 3.67-3.76 (m, 2H), 3.54-3.58 (m, 2H), 3.28 (s, 3H), 2.46-2.53 (m, 2H) | (ESI (+)) m/e 436 (M + H)⁺ |
| 464 | N-{4-[1-(tetrahydrofuran-2-ylcarbonyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 8.08-8.14 (bs, 1H), 7.82-7.87 (m, 2H), 7.34-7.40 (m, 2H), 7.20-7.25 (m, 2H), 7.15-7.20 (m, 2H), 5.97-6.01 (m, 1H), 4.83-4.89 (m, 4H), 4.69 (dd, J = 7.2, 5.3 Hz, 1H), 4.24-4.31 (m, 2H), 3.87-3.96 (m, 1H), 3.69-3.88 (m, 3H), 2.39-2.60 (m, 3H), 1.84-2.01 (m, 2H), 1.69-1.83 (m, 1H) | (ESI (+)) m/e 418 (M + H)⁺ |
| 465 | N-{4-[1-(tetrahydrofuran-3-ylcarbonyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 8.12-8.14 (bs, 1H), 7.83-7.89 (m, 2H), 7.38-7.40 (m, 2H), 7.20-7.24 (m, 2H), 7.15-7.20 (m, 2H), 5.99-6.02 (m, 1H), 4.83-4.89 (m, 4H), 4.16-4.24 (m, 2H), 4.04-4.13 (m, 2H), 3.91 (td, J = 7.9, 5.9 Hz, 1H), 3.77-3.83 (m, 1H), 3.60-3.79 (m, 2H), 3.23-3.35 (m, 1H), 2.42-2.49 (m, 2H), 2.29 (ddd, J = 7.6, 12.1, 6.1 Hz, 1H), 1.97-2.06 (m, 1H) | (ESI (−)) m/e 416 (M − H)⁻ |
| 466 | N-{4-[1-(cyclopropylacetyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 8.11-8.12 (bs, 1H), 7.84-7.87 (m, 2H), 7.37-7.40 (m, 2H), 7.20-7.23 (m, 2H), 7.15-7.20 (m, 2H), 5.99-6.01 (m, 1H), 4.86 (s, 4H), 4.10-4.28 (m, 2H), 3.55-3.77 (m, 2H), 2.43-2.52 (m, 2H), 2.36 (d, J = 6.5 Hz, 2H), 1.13-1.24 (m, 1H), 0.48-0.54 (m, 2H), 0.19-0.27 (m, 2H) | (ESI (+)) m/e 402 (M + H)⁺ |
| 467 | N-{4-[1-(cyclopentylcarbonyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 8.10-8.13 (bs, 1H), 7.83-7.88 (m, 2H), 7.38-7.41 (m, 2H), 7.21-7.24 (m, 2H), 7.15-7.20 (m, 2H), 6.00-6.03 (m, 1H), 4.83-4.87 (m, 4H), 4.16-4.26 (m, 2H), 3.63-3.83 (m, 2H), 2.96 (s, 1H), 2.44-2.52 (m, 2H), 1.92-2.04 (m, 2H), 1.75-1.87 (m, 2H), 1.65-1.75 (m, 2H), 1.46-1.60 (m, 2H) | (ESI (+)) m/e 416 (M + H)⁺ |
| 468 | N-{4-[1-(2-methylbenzoyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 8.12-8.13 (bs, 1H), 7.84-7.87 (m, 3H), 7.37-7.40 (m, 3H), 7.21-7.30 (m, 5H), 5.94-6.05 (bs, 1H), 4.86 (s, 4H), 4.86 (s, 1H), 4.19-4.48 (m, 2H), 3.35-3.61 (m, 2H), 2.39-2.59 (m, 2H), 2.32 (s, 3H) | (ESI (+)) m/e 438 (M + H)⁺ |
| 469 | N-{4-[1-(3-methylbenzoyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 8.11-8.13 (bs, 1H), 7.84-7.87 (m, 2H), 7.34-7.41 (m, 4H), 7.28 (t, J = 7.5 Hz, 1H), 7.20-7.24 (m, 2H), 7.17-7.19 (m, 3H), 5.98-6.01 (bs, 1H), 4.83-4.90 (m, 4H), 4.26-4.29 (m, 2H), 3.70-3.79 (m, 2H), 2.50-2.54 (m, 2H), 2.26 (s, 3H) | (ESI (+)) m/e 438 (M + H)⁺ |
| 470 | N-{4-[1-(2-methoxybenzoyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 8.11-8.12 (bs, 1H), 7.83-7.86 (m, 2H), 7.37-7.45 (m, 3H), 7.30-7.35 (m, 1H), 7.20-7.23 (m, 2H), 7.15-7.19 (m, 2H), 7.00 (t, J = 7.4 Hz, 1H), 6.96 (d, J = 8.3 Hz, 1H), 5.89-6.08 (m, 1H), 4.85 (s, 4H), 4.31-4.68 (m, 2H), 3.69 (s, 3H), 3.28-3.62 (m, 2H), 2.34-2.68 (m, 2H) | (ESI (+)) m/e 454 (M + H)⁺ |
| 471 | N-{4-[1-(3-methoxybenzoyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 8.11-8.13 (bs, 1H), 7.84-7.87 (m, 2H), 7.37-7.40 (m, 2H), 7.30-7.34 (m, 1H), 7.20-7.24 (m, 3H), 7.16-7.19 (m, 2H), 7.12-7.15 (m, 1H), 7.01 (ddd, J = 8.2, 2.6, 1.0 Hz, 1H), 5.98-6.00 (bs, 1H), 4.84-4.89 (m, 4H), 4.26-4.29 (m, 2H), 3.71-3.78 (m, 2H), 3.69 (s, 3H), 2.49-2.54 (m, 2H) | (ESI (+)) m/e 454 (M + H)⁺ |
| 472 | N-{4-[1-(4-methoxybenzoyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 8.11-8.12 (bs, 1H), 7.84-7.87 (m, 2H), 7.55-7.58 (m, 2H), 7.38-7.41 (m, 2H), 7.20-7.24 (m, 2H), 7.16-7.19 (m, 2H), 6.97-6.99 (m, 2H), 5.99-6.02 (m, 1H), 4.86 (s, 4H), 4.29 (q, J = 2.9 Hz, 2H), 3.77 (t, J = 5.7 Hz, 2H), 3.71 (s, 3H), 2.49-2.59 (m, 2H) | (ESI (+)) m/e 454 (M + H)⁺ |

| Ex | Name | ¹H NMR | MS |
|---|---|---|---|
| 473 | N-{4-[1-(2-fluorobenzoyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 8.11-8.13 (bs, 1H), 7.84-7.87 (m, 2H), 7.48 (td, J = 7.1, 1.8 Hz, 1H), 7.35-7.38 (m, 2H), 7.29-7.34 (m, 1H), 7.20-7.23 (m, 2H), 7.16-7.19 (m, 2H), 7.14-7.17 (m, 1H), 7.10-7.12 (m, 1H), 5.89-6.09 (m, 1H), 4.86 (s, 4H), 4.12-4.67 (m, 2H), 3.28-3.76 (m, 2H), 2.39-2.56 (m, 2H) | (ESI (+)) m/e 442 (M + H)⁺ |
| 474 | N-{4-[1-(3-fluorobenzoyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 8.12-8.14 (bs, 1H), 7.85-7.87 (m, 2H), 7.37-7.40 (m, 2H), 7.29-7.36 (m, 3H), 7.20-7.24 (m, 2H), 7.16-7.19 (m, 2H), 7.09-7.13 (m, 1H), 5.97-6.00 (bs, 1H), 4.86 (s, 4H), 4.22-4.26 (m, 2H), 3.68-3.73 (m, 2H), 2.49-2.53 (m, 2H) | (ESI (+)) m/e 442 (M + H)⁺ |
| 475 | N-{4-[1-(4-fluorobenzoyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 8.12-8.14 (bs, 1H), 7.85-7.87 (m, 2H), 7.53-7.58 (m, 2H), 7.38-7.41 (m, 2H), 7.20-7.25 (m, 2H), 7.16-7.20 (m, 2H), 7.09-7.14 (m, 2H), 5.98-6.01 (m, 1H), 4.86 (s, 4H), 4.24-4.26 (m, 2H), 3.70-3.74 (m, 2H), 2.50-2.55 (m, 2H) | (ESI (+)) m/e 442 (M + H)⁺ |
| 476 | N-{4-[1-(4-chlorobenzoyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 8.12-8.14 (bs, 1H), 7.85-7.87 (m, 2H), 7.46-7.50 (m, 2H), 7.38-7.40 (m, 4H), 7.20-7.25 (m, 2H), 7.15-7.19 (m, 2H), 5.98-6.01 (m, 1H), 4.86 (s, 4H), 4.22-4.25 (m, 2H), 3.68-3.72 (m, 2H), 2.50-2.54 (m, 2H) | (ESI (+)) m/e 458 (M + H)⁺ |
| 477 | N-(4-{1-[3-(dimethylamino)benzoyl]-1,2,3,6-tetrahydropyridin-4-yl}phenyl)-1,3-dihydro-2H-isoindole-2-carboxamide | ¹H NMR (400 MHz, Pyridine-d₅, Temp = 90° C.) δ ppm 8.08-8.15 (m, 1H), 7.84-7.86 (m, 2H), 7.38-7.40 (m, 2H), 7.28 (dd, J = 8.2, 7.5 Hz, 1H), 7.20-7.24 (m, 2H), 7.15-7.20 (m, 2H), 6.98-6.99 (m, 1H), 6.90-6.94 (m, 1H), 6.77-6.80 (m, 1H), 5.99-6.02 (bs, 1H), 4.86 (s, 4H), 4.29-4.34 (m, 2H), 3.71-3.83 (m, 2H), 2.79 (s, 6H), 2.51-2.54 (m, 2H) | (ESI (+)) m/e 467 (M + H)⁺ |
| 478 | N-(4-{1-[4-(dimethylamino)benzoyl]-1,2,3,6-tetrahydropyridin-4-yl}phenyl)-1,3-dihydro-2H-isoindole-2-carboxamide | ¹H NMR (400 MHz, Pyridine-d₅, Temp = 90° C.) δ ppm 8.11 (d, J = 2.1 Hz, 1H), 7.84-7.87 (m, 2H), 7.56-7.59 (m, 2H), 7.39-7.41 (m, 2H), 7.20-7.25 (m, 2H), 7.15-7.18 (m, 2H), 6.70-6.73 (m, 2H), 6.00-6.03 (m, 1H), 4.82-4.91 (m, 4H), 4.34 (q, J = 2.9 Hz, 2H), 3.82 (t, J = 5.7 Hz, 2H), 2.82 (s, 6H), 2.53-2.60 (m, 2H) | (ESI (+)) m/e 467 (M + H)⁺ |
| 479 | N-{4-[1-(3-furoyl)-1,2,3,6-tetrahydropyridin-4-yl]phenyl}-1,3-dihydro-2H-isoindole-2-carboxamide | ¹H NMR (400 MHz, DMSO-d₆, Temp = 90° C.) δ ppm 2.55 (d, J = 1.83 Hz, 2 H), 3.77 (t, J = 5.80 Hz, 2 H) 4.23 (q, J = 2.64 Hz, 2 H), 4.77 (s, 4 H), 6.08 (t, J = 3.51 Hz, 1 H), 6.68 (d, J = 1.22 Hz, 1 H), 7.27-7.37 (m, 6 H), 7.54 (d, J = 8.54 Hz, 2 H), 7.67 (t, J = 1.68 Hz, 1 H), 7.99 (s, 1 H), 8.13 (s, 1 H) | (ESI (+)) m/e 414 (M + H)⁺ |
| 480 | N-{4-[1-(3-thienylcarbonyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 8.11-8.12 (bs, 1H), 7.84-7.87 (m, 2H), 7.72-7.73 (m, 1H), 7.35-7.42 (m, 4H), 7.21-7.24 (m, 2H), 7.17-7.19 (m, 2H), 5.97-5.99 (bs, 1H), 4.82-4.89 (m, 4H), 4.29-4.31 (m, 2H), 3.78 (t, J = 5.6 Hz, 2H), 2.49-2.53 (m, 2H) | (ESI (+)) m/e 430 (M + H)⁺ |
| 481 | N-{4-[1-(1H-pyrrol-2-ylcarbonyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 11.78-11.92 (m, 1H), 8.09-8.11 (m, 1H), 7.83-7.86 (m, 2H), 7.37-7.39 (m, 2H), 7.20-7.23 (m, 2H), 7.16-7.20 (m, 2H), 7.08-7.10 (m, 1H), 6.72-6.74 (m, 1H), 6.35 (dt, J = 3.6, 2.5 Hz, 1H), 5.99-6.02 (m, 1H), 4.86 (s, 4H), 4.46 (q, J = 2.9 Hz, 2H), 3.98 (t, J = 5.7 Hz, 2H), 2.50-2.60 (m, 2H) | (ESI (+)) m/e 413 (M + H)⁺ |
| 482 | N-(4-{1-[(2,5-dimethyl-1H-pyrrol-3-yl)carbonyl]-1,2,3,6-tetrahydropyridin-4-yl}phenyl)-1,3-dihydro-2H-isoindole-2-carboxamide | ¹H NMR (400 MHz, Pyridine-d₅, Temp = 90° C.) δ ppm 10.78-10.83 (m, 1H), 8.06-8.14 (m, 1H), 7.81-7.89 (m, 2H), 7.37-7.44 (m, 2H), 7.20-7.23 (m, 2H), 7.16-7.19 (m, 2H), 6.11 (dd, J = 2.7, 1.2 Hz, 1H), 6.04-6.06 (m, 1H), 4.82-4.91 (m, 4H), 4.41-4.45 (m, 2H), 3.94 (t, J = 5.7 Hz, 2H), 2.54-2.61 (m, 2H), 2.48 (s, 3H), 2.24 (s, 3H) | (ESI (+)) m/e 441 (M + H)⁺ |
| 483 | N-{4-[1-(1,3-thiazol-4-ylcarbonyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 8.97 (d, J = 2.1 Hz, 1H), 8.16 (d, J = 2.1 Hz, 1H), 8.09-8.14 (m, 1H), 7.83-7.86 (m, 2H), 7.37-7.40 (m, 2H), 7.20-7.24 (m, 2H), 7.16-7.19 (m, 2H), 6.01 (t, J = 3.2 Hz, 1H), 4.86 (s, 4H), 4.48-4.51 (m, 2H), 3.98-4.01 (m, 2H), 2.56-2.62 (m, 2H) | (ESI (+)) m/e 431 (M + H)⁺ |
| 484 | N-{4-[1-(1H-pyrazol-4-ylcarbonyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 8.19-8.23 (m, 1H), 8.06-8.15 (m, 1H), 7.82-7.90 (m, 2H), 7.36-7.42 (m, 2H), 7.19-7.24 (m, 2H), 7.16-7.19 (m, 2H), 6.00-6.05 (m, 1H), 4.83-4.89 (m, 4H), 4.40-4.44 (m, 2H), 3.92 (t, J = 5.7 Hz, 2H), 2.52-2.59 (m, 2H) | (ESI (+)) m/e 414 (M + H)⁺ |

| Ex | Name | ¹H NMR | MS |
|---|---|---|---|
| 485 | N-(4-{1-[(3,5-dimethyl-1,2-oxazol-4-yl)carbonyl]-1,2,3,6-tetrahydropyridin-4-yl}phenyl)-1,3-dihydro-2H-isoindole-2-carboxamide | ¹H NMR (400 MHz, Pyridine-d₅, Temp = 90° C.) δ ppm 8.14-8.16 (bs, 1H), 7.85-7.88 (m, 2H), 7.38-7.42 (m, 2H), 7.20-7.24 (m, 2H), 7.16-7.19 (m, 2H), 6.00-6.02 (m, 1H), 4.84-4.88 (m, 4H), 4.19-4.23 (m, 2H), 3.69-3.75 (m, 2H), 2.49-2.58 (m, 2H), 2.32 (s, 3H), 2.29 (s, 3H) | (ESI (−)) m/e 441 (M − H)⁻ |
| 486 | N-{4-[1-(pyridin-2-ylcarbonyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 8.61 (ddd, J = 4.8, 1.7, 0.9 Hz, 1H), 8.10-8.11 (bs, 1H), 7.83-7.86 (m, 2H), 7.76 (dt, J = 7.7, 1.1 Hz, 1H), 7.68 (td, J = 7.6, 1.8 Hz, 1H), 7.36-7.39 (m, 2H), 7.20-7.24 (m, 3H), 7.16-7.19 (m, 2H), 5.89-6.10 (m, 1H), 4.86 (s, 4H), 4.40-4.42 (m, 2H), 3.56-4.22 (m, 2H), 2.52-2.64 (m, 2H) | (ESI (+)) m/e 425 (M + H)⁺ |
| 487 | N-{4-[1-(pyridin-3-ylcarbonyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 8.93 (d, J = 2.2 Hz, 1H), 8.70 (dd, J = 4.8, 1.7 Hz, 1H), 8.13-8.15 (bs, 1H), 7.85-7.88 (m, 2H), 7.80-7.85 (m, 1H), 7.37-7.40 (m, 2H), 7.25-7.29 (m, 1H), 7.20-7.24 (m, 2H), 7.16-7.20 (m, 2H), 5.97-5.99 (bs, 1H), 4.86 (s, 4H), 4.22-4.29 (m, 2H), 3.64-3.78 (m, 2H), 2.47-2.56 (m, 2H) | (ESI (+)) m/e 425 (M + H)⁺ |
| 488 | N-[4-(1-isonicotinoyl-1,2,3,6-tetrahydropyridin-4-yl)phenyl]-1,3-dihydro-2H-isoindole-2-carboxamide | ¹H NMR (400 MHz, Pyridine-d₅, Temp = 90° C.) δ ppm 8.74-8.76 (m, 2H), 8.14-8.15 (bs, 1H), 7.85-7.88 (m, 2H), 7.36-7.42 (m, 2H), 7.20-7.24 (m, 2H), 7.16-7.19 (m, 2H), 5.97-6.00 (bs, 1H), 4.86 (s, 4H), 4.13-4.32 (m, 2H), 3.57-3.79 (m, 2H), 2.46-2.55 (m, 2H) | (ESI (+)) m/e 425 (M + H)⁺ |
| 489 | N-{4-[1-(pyridazin-3-ylcarbonyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 9.22 (dd, J = 5.0, 1.8 Hz, 1H), 8.10-8.12 (bs, 1H), 7.90 (dd, J = 8.3, 1.7 Hz, 1H), 7.83-7.86 (m, 2H), 7.47-7.50 (m, 1H), 7.34-7.38 (m, 2H), 7.20-7.23 (m, 2H), 7.16-7.20 (m, 2H), 5.92-6.05 (m, 1H), 4.86 (s, 4H), 4.36-4.51 (m, 2H), 3.67-3.94 (m, 2H), 2.53-2.64 (m, 2H) | (ESI (+)) m/e 426 (M + H)⁺ |
| 490 | N-{4-[1-(pyrazin-2-ylcarbonyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 9.34 (d, J = 1.2 Hz, 1H), 8.86 (d, J = 4.9 Hz, 1H), 8.12-8.14 (bs, 1H), 7.84-7.87 (m, 2H), 7.69 (dd, J = 5.0, 1.5 Hz, 1H), 7.37-7.39 (m, 2H), 7.20-7.23 (m, 2H), 7.16-7.19 (m, 2H), 5.92-6.05 (m, 1H), 4.86 (s, 4H), 4.29-4.45 (m, 2H), 3.62-4.00 (m, 2H), 2.53-2.61 (m, 2H) | (ESI (+)) m/e 426 (M + H)⁺ |
| 491 | N-{4-[1-(pyrimidin-4-ylcarbonyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 9.13 (d, J = 1.5 Hz, 1H), 8.59 (d, J = 2.5 Hz, 1H), 8.51 (dd, J = 2.5, 1.3 Hz, 1H), 8.11-8.13 (bs, 1H), 7.84-7.87 (m, 2H), 7.37-7.40 (m, 2H), 7.20-7.24 (m, 2H), 7.16-7.19 (m, 2H), 5.95-6.05 (m, 1H), 4.86 (s, 4H), 4.32-4.47 (m, 2H), 3.60-3.91 (m, 2H), 2.55-2.61 (m, 2H) | (ESI (+)) m/e 426 (M + H)⁺ |
| 492 | N-(4-{1-[3-(piperidin-1-yl)propanoyl]-1,2,3,6-tetrahydropyridin-4-yl}phenyl)-1,3-dihydro-2H-isoindole-2-carboxamide | ¹H NMR (400 MHz, Pyridine-d₅, Temp = 90° C.) δ ppm 8.12-8.13 (bs, 1H), 7.84-7.86 (m, 2H), 7.35-7.38 (m, 2H), 7.21-7.25 (m, 2H), 7.16-7.20 (m, 2H), 5.94-5.98 (m, 1H), 4.84-4.89 (m, 4H), 4.06-4.29 (m, 2H), 3.53-3.89 (m, 2H), 3.30 (t, J = 7.2 Hz, 2H), 2.95-3.05 (m, 2H), 2.89-2.92 (m, 4H), 2.42-2.48 (m, 2H), 1.65-1.73 (m, 4H), 1.30-1.40 (m, 2H) | (ESI (+)) m/e 459 (M + H)⁺ |
| 493 | N-{4-[1-(morpholin-4-ylacetyl)-1,2,3,6-tetrahydropyridin-4-yl]phenyl}-1,3-dihydro-2H-isoindole-2-carboxamide | ¹H NMR (400 MHz, Pyridine-d₅, Temp = 90° C.) δ ppm 8.13-8.14 (bs, 1H), 7.85-7.88 (m, 2H), 7.39-7.41 (m, 2H), 7.20-7.24 (m, 2H), 7.16-7.20 (m, 2H), 6.01-6.04 (m, 1H), 4.86-4.87 (m, 4H), 4.27 (q, J = 2.9 Hz, 2H), 3.75-3.80 (m, 2H), 3.64-3.72 (m, 4H), 3.29 (s, 2H), 2.54-2.57 (m, 6H) | (ESI (+)) m/e 447 (M + H)⁺ |
| 494 | N-(4-{1-[(4-methylpiperazin-1-yl)acetyl]-1,2,3,6-tetrahydropyridin-4-yl}phenyl)-1,3-dihydro-2H-isoindole-2-carboxamide | ¹H NMR (400 MHz, Pyridine-d₅, Temp = 90° C.) δ ppm 8.13-8.15 (bs, 1H), 7.85-7.87 (m, 2H), 7.38-7.41 (m, 2H), 7.20-7.25 (m, 2H), 7.19 (d, J = 7.0 Hz, 1H), 7.17-7.19 (m, 1H), 6.00-6.02 (m, 1H), 4.83-4.89 (m, 4H), 4.24-4.26 (m, 2H), 3.74-3.77 (m, 2H), 3.33 (s, 2H), 2.73-2.76 (m, 4H), 2.66-2.69 (m, 4H), 2.49-2.54 (m, 2H), 2.36 (s, 3H) | (ESI (+)) m/e 460 (M + H)⁺ |
| 759 | N-{4-[1-(tetrahydro-2H-pyran-4-ylcarbonyl)-1,2,3,6-tetrahydropyridin-4-yl]phenyl}-1,3-dihydro-2H-isoindole-2-carboxamide | ¹H NMR (400 MHz, DMSO-d₆, Temp = 90° C.) δ ppm 8.13 (s, 1H), 7.54 (m, 2H), 7.38-7.23 (m, 6H), 6.08 (m, 1H), 4.79 (d, J = 13.1 Hz, 4H), 4.15 (m, 2H), 3.86 (m, 2H), 3.70 (t, J = 5.7 Hz, 2H), 3.43 (td, J = 11.4, 2.4 Hz, 2H), 2.90 (m, 1H), 2.50 (m, 2H), 1.76-1.51 (m, 4H) | (ESI (+)) m/e 432 (M + H)⁺ |

-continued

| Ex | Name | ¹H NMR | MS |
|---|---|---|---|
| 760 | N-{4-[1-(1,4-dioxan-2-ylcarbonyl)-1,2,3,6-tetrahydropyridin-4-yl]phenyl}-1,3-dihydro-2H-isoindole-2-carboxamide | ¹H NMR (400 MHz, DMSO-d₆, Temp = 90° C.) δ ppm 8.13 (s, 1H), 7.55 (m, 2H), 7.38-7.26 (m, 6H), 6.07 (m, 1H), 4.79 (m, 4H), 4.37 (dd, J = 9.2, 3.0 Hz, 1H), 4.15 (m, 2H), 3.82-3.62 (m, 7H), 3.53 (m, 1H), 2.50 (m, 2H) | (ESI (+)) m/e 434 (M + H)⁺ |
| 761 | N-(4-{1-[(1-methylpyrrolidin-3-yl)carbonyl]-1,2,3,6-tetrahydropyridin-4-yl}phenyl)-1,3-dihydro-2H-isoindole-2-carboxamide | ¹H NMR (400 MHz, DMSO-d₆, Temp = 90° C.) δ ppm 8.13 (s, 1H), 7.54 (d, J = 8.6 Hz, 2H), 7.40-7.20 (m, 6H), 6.07 (s, 1H), 4.78 (m, 4H), 4.12 (m, 2H), 3.68 (t, J = 5.7 Hz, 2H), 3.27 (m, 1H), 2.77 (m, 1H), 2.63-2.45 (m, 4H), 2.38 (m, 1H), 2.25 (s, 3H), 98 (m, 2H) | (ESI (+)) m/e 431 (M + H)⁺ |
| 762 | N-(4-{1-[(1,1-dioxidotetrahydrothiophen-3-yl)carbonyl]-1,2,3,6-tetrahydropyridin-4-yl}phenyl)-1,3-dihydro-2H-isoindole-2-carboxamide | ¹H NMR (400 MHz, DMSO-d₆, Temp = 90° C.) δ ppm 8.14 (s, 1H), 7.55 (m, 2H), 7.38-7.27 (m, 6H), 6.08 (m, 1H), 4.81 (m, 4H), 4.17 (m, 2H), 3.74 (m, 3H), 3.33-3.10 (m, 3H), 3.07 (m, 1H), 2.53 (m, 2H), 2.37 (m, 1H), 2.14 (m, 1H) | (ESI (+)) m/e 466 (M + H)⁺ |
| 763 | N-{4-[1-(2-hydroxy-2-methylpropanoyl)-1,2,3,6-tetrahydropyridin-4-yl]phenyl}-1,3-dihydro-2H-isoindole-2-carboxamide | ¹H NMR (400 MHz, DMSO-d₆, Temp = 90° C.) δ ppm 8.13 (s, 1H), 7.54 (m, 2H), 7.38-7.27 (m, 6H), 6.09 (m, 1H), 5.10 (s, 1H), 4.78 (s, 4H), 4.28 (m, 2H), 3.94 (m, 2H), 2.50 (m, 2H), 1.37 (s, 6H) | (ESI (+)) m/e 406 (M + H)⁺ |
| 1019 | 5-cyano-N-{4-[1-(2-methylpropanoyl)-1,2,3,6-tetrahydropyridin-4-yl]phenyl}-1,3-dihydro-2H-isoindole-2-carboxamide | -¹H NMR (400 MHz, DMSO-d₆, Temp = 90° C.) δ ppm 8.20 (m, 1H), 7.80 (m, 1H), 7.70 (m, 1H), 7.54 (m, 3H), 7.37 (m, 2H), 6.08 (bs, 1H), 4.90 (m, 4H), 4.13 (m, 2H), 3.69 (m, 2H), 2.90 (m, 1H), 2.50 (m, 2H), 1.02 (m, 6H) | (ESI (+)) m/e 415 (M + H)⁺ |
| 1281 | 5-cyano-N-{4-[1-(tetrahydrofuran-3-ylcarbonyl)-1,2,3,6-tetrahydropyridin-4-yl]phenyl}-1,3-dihydro-2H-isoindole-2-carboxamide | ¹H NMR (400 MHz, DMSO-d₆, Temp = 90° C.) δ ppm 8.21 (s, 1H), 7.80 (s, 1H), 7.71 (d, J = 7.9 Hz, 1H), 7.54 (m, 3H), 7.33 (m, 2H), 6.07 (bs, 1H), 4.83 (m, 4H), 4.14 (m, 2H), 3.91 (t, J = 8.1 Hz, 1H), 3.71 (m, 5H), 3.38 (m, 1H), 2.50 (m, 2H), 2.07 (m, 2H) | (ESI (+)) m/e 443 (M + H)⁺ |
| 1282 | 5-cyano-N-{4-[1-(tetrahydro-2H-pyran-4-ylcarbonyl)-1,2,3,6-tetrahydropyridin-4-yl]phenyl}-1,3-dihydro-2H-isoindole-2-carboxamide | ¹H NMR (400 MHz, DMSO-d₆, Temp = 90° C.) δ ppm 8.22 (bs, 1H), 7.80 (s, 1H), 7.72 (d, J = 7.8 Hz, 1H), 7.54 (m, 3H), 7.33 (m, 2H), 6.08 (bs, 1H), 4.82 (m, 4H), 4.14 (m, 2H), 3.86 (m, 2H), 3.70 (t, J = 5.7 Hz, 2H), 3.42 (td, J = 11.4, 2.5 Hz, 2H), 2.90 (m, 1H), 2.50 (m, 2H), 1.77-1.53 (m, 4H) | (ESI (+)) m/e 457 (M + H)⁺ |
| 1283 | 5-cyano-N-{4-[1-(2-hydroxy-2-methylpropanoyl)-1,2,3,6-tetrahydropyridin-4-yl]phenyl}-1,3-dihydro-2H-isoindole-2-carboxamide | ¹H NMR (400 MHz, DMSO-d₆, Temp = 90° C.) δ ppm 8.21 (s, 1H), 7.80 (s, 1H), 7.71 (d, J = 7.7 Hz, 1H), 7.53 (m, 3H), 7.33 (m, 2H), 6.08 (m, 1H), 5.10 (s, 1H), 4.83 (m, 4H), 4.28 (m, 2H), 3.93 (m, 2H), 2.50 (m, 2H), 1.37 (s, 6H) | (ESI (+)) m/e 431 (M + H)⁺ |
| 1284 | 5-cyano-N-{4-[1-(morpholin-4-ylacetyl)-1,2,3,6-tetrahydropyridin-4-yl]phenyl}-1,3-dihydro-2H-isoindole-2-carboxamide | ¹H NMR (400 MHz, DMSO-d₆, Temp = 90° C.) δ ppm 8.21 (s, 1H), 7.80 (s, 1H), 7.72 (d, J = 7.9 Hz, 1H), 7.51 (m, 3H), 7.33 (m, 2H), 6.07 (m, 1H), 4.83 (m, 4H), 4.15 (m, 2H), 3.71 (m, 2H), 3.58 (m, 4H), 3.21 (s, 2H), 2.50 (m, 2H), 2.45 (m, 4H) | (ESI (+)) m/e 472 (M + H)⁺ |

Example 495

N-(1'-benzoyl-1',2',3',6'-tetrahydro-3,4'-bipyridin-6-yl)-1,3-dihydro-2H-isoindole-2-carboxamide The title compound was prepared as described in Example 1C, substituting N-(5-(1,2,3,6-tetrahydropyridin-4-yl)pyridin-2-yl)isoindoline-2-carboxamide for 3-phenylpropan-1-amine and benzoic acid for 4-(isoindoline-2-carboxamido)benzoic acid. ¹H NMR (400 MHz, DMSO-d₆, Temp=90° C.) δ ppm 8.51 (bs, 1H), 8.32 (d, J=2.5 Hz, 1H), 7.90 (d, J=8.7 Hz, 1H), 7.77 (dd, J=8.7, 2.5 Hz, 1H), 7.48-7.39 (m, 5H), 7.36-7.25 (m, 4H), 6.16 (bs, 1H), 4.81 (s, 4H), 4.18 (m, 2H), 3.68 (m, 2H), 2.55 (m, 2H); MS (ESI(+)) m/e 425 (M+H)⁺.

Example 496

N-(4-{[6-(benzoylamino)hexyl]carbamoyl}phenyl)-1,3-dihydro-2H-isoindole-2-carboxamide The title compound was prepared as described in Example 278, substituting benzoyl chloride for acetyl chloride and N-{4-[(6-aminohexyl)carbamoyl]phenyl}-1,3-dihydro-2H-isoindole-2-carboxamide for 5-amino-N-(4-(propylcarbamoyl)phenyl)isoindoline-2-carboxamide. ¹H NMR (300 MHz, DMSO-d₆) δ ppm 8.57 (s, 1H), 8.43 (t, J=5.6 Hz, 1H), 8.25 (t, J=5.6 Hz, 1H), 7.81-7.86 (m, 2H), 7.74-7.78 (m, 2H), 7.63-7.67 (m, 2H), 7.41-7.54 (m, 3H), 7.29-7.39 (m, 4H), 4.78-4.79 (bs, 4H), 3.15-3.27 (m, 4H), 1.44-1.64 (m, 4H), 1.19-1.39 (m, 4H); MS (ESI(+)) m/e 485 (M+H)+.

Example 497

N-[4-({4-[(benzoylamino)methyl]benzyl}carbamoyl)phenyl]-5-fluoro-1,3-dihydro-2H-isoindole-2-carboxamide The title compound was prepared as described in Example 278, substituting benzoyl chloride for acetyl chloride and N-(4-{[4-(aminomethyl)benzyl]carbamoyl}phenyl)-5-fluoro-1,3-dihydro-2H-isoindole-2-carboxamide for 5-amino-N-(4-(propylcarbamoyl)phenyl)isoindoline-2-carboxamide. $^1$H NMR (300 MHz, DMSO-d$_6$) δ ppm 9.01 (t, J=6.0 Hz, 1H), 8.83 (t, J=5.9 Hz, 1H), 8.60 (s, 1H), 7.85-7.91 (m, 2H), 7.78-7.83 (m, 2H), 7.63-7.68 (m, 2H), 7.36-7.56 (m, 4H), 7.27 (s, 4H), 7.21-7.26 (m, 1H), 7.10-7.19 (m, 1H), 4.72-4.81 (m, 4H), 4.40-4.48 (m, 4H); MS (ESI(+)) m/e 523 (M+H)+.

Table 8.

The following Examples were essentially prepared as described in Example 1C, substituting N-(4-(piperazin-1-yl)phenyl)isoindoline-2-carboxamide for 3-phenylpropan-1-amine and the appropriate carboxylic acid for 4-(isoindoline-2-carboxamido)benzoic acid.

| Ex | Name | $^1$H NMR | MS |
|---|---|---|---|
| 498 | N-{4-[4-(5-oxo-L-prolyl)piperazin-1-yl]phenyl}-1,3-dihydro-2H-isoindole-2-carboxamide | $^1$H NMR (400 MHz, Pyridine-d$_5$, Temp = 90° C.) δ ppm 7.95-7.98 (bs, 1H), 7.81-7.90 (m, 1H), 7.74-7.77 (m, 2H), 7.20-7.23 (m, 2H), 7.16-7.20 (m, 2H), 6.92-6.95 (m, 2H), 4.86 (s, 4H), 4.60-4.64 (m, 1H), 3.55-3.76 (m, 4H), 3.03-3.06 (m, 4H), 2.38-2.47 (m, 1H), 2.25-2.37 (m, 2H), 2.08-2.15 (m, 1H) | (ESI (+)) m/e 434 (M + H)+ |
| 499 | N-{4-[4-(5-oxo-D-prolyl)piperazin-1-yl]phenyl}-1,3-dihydro-2H-isoindole-2-carboxamide | $^1$H NMR (400 MHz, Pyridine-d$_5$, Temp = 90° C.) δ ppm 7.95-7.98 (bs, 1H), 7.80-7.84 (bs, 1H), 7.75-7.77 (m, 2H), 7.20-7.23 (m, 2H), 7.16-7.20 (m, 2H), 6.92-6.95 (m, 2H), 4.86 (s, 4H), 4.60-4.64 (m, 1H), 3.57-3.76 (m, 4H), 3.02-3.08 (m, 4H), 2.38-2.46 (m, 1H), 2.24-2.37 (m, 2H), 2.08-2.15 (m, 1H) | (ESI (+)) m/e 434 (M + H)+ |
| 500 | N-(4-{4-[(1-acetylpiperidin-4-yl)carbonyl]piperazin-1-yl}phenyl)-1,3-dihydro-2H-isoindole-2-carboxamide | $^1$H NMR (400 MHz, Pyridine-d$_5$, Temp = 90° C.) δ ppm 7.93-7.95 (bs, 1H), 7.75-7.77 (m, 2H), 7.20-7.23 (m, 2H), 7.19 (d, J = 4.2 Hz, 1H), 7.16 (d, J = 8.2 Hz, 1H), 6.94-6.97 (m, 2H), 4.86 (s, 4H), 3.66-3.76 (m, 4H), 3.05-3.08 (m, 4H), 2.78-3.03 (m, 3H), 2.01 (s, 3H), 1.81-1.92 (m, 2H), 1.68-1.79 (m, 2H) | (ESI (+)) m/e 476 (M + H)+ |
| 501 | N-{4-[4-(2-acetamidobenzoyl)piperazin-1-yl]phenyl}-1,3-dihydro-2H-isoindole-2-carboxamide | $^1$H NMR (400 MHz, Pyridine-d$_5$, Temp = 90° C.) δ ppm 9.65 (d, J = 5.2 Hz, 1H), 8.26 (d, J = 8.1 Hz, 1H), 7.92-7.93 (bs, 1H), 7.73-7.76 (m, 2H), 7.34-7.39 (m, 2H), 7.20-7.23 (m, 2H), 7.16-7.19 (m, 2H), 7.12 (dd, J = 7.5, 1.2 Hz, 1H), 6.92-6.94 (m, 2H), 4.86 (s, 4H), 3.68-3.83 (m, 4H), 3.07-3.10 (m, 4H), 2.09 (s, 3H) | (ESI (+)) m/e 484 (M + H)+ |
| 502 | N-(4-{4-[4-(methylsulfonyl)benzoyl]piperazin-1-yl}phenyl)-1,3-dihydro-2H-isoindole-2-carboxamide | $^1$H NMR (400 MHz, Pyridine-d$_5$, Temp = 90° C.) δ ppm 8.10-8.13 (m, 2H), 7.94-7.96 (bs, 1H), 7.75-7.78 (m, 2H), 7.68-7.71 (m, 2H), 7.20-7.23 (m, 2H), 7.16-7.20 (m, 2H), 6.94-6.98 (m, 2H), 4.86 (s, 4H), 3.55-3.78 (m, 4H), 3.17 (s, 3H), 3.08-3.11 (m, 4H) | (ESI (+)) m/e 505 (M + H)+ |
| 503 | N-[4-(4-butyrylpiperazin-1-yl)phenyl]-1,3-dihydro-2H-isoindole-2-carboxamide | $^1$H NMR (400 MHz, Pyridine-d$_5$, Temp = 90° C.) δ ppm 7.91-7.93 (m, 1H), 7.73-7.77 (m, 2H), 7.20-7.23 (m, 2H), 7.19 (d, J = 7.3 Hz, 1H), 7.17-7.18 (m, 1H), 6.93-6.96 (m, 2H), 4.86 (s, 4H), 3.48-3.70 (m, 3H), 3.02-3.06 (m, 4H), 2.43 (d, J = 0.6 Hz, 1H), 2.31 (t, J = 7.3 Hz, 2H), 1.65-1.81 (m, 2H), 0.95 (t, J = 7.3 Hz, 3H) | (ESI (+)) m/e 393 (M + H)+ |
| 504 | N-[4-(4-isobutyrylpiperazin-1-yl)phenyl]-1,3-dihydro-2H-isoindole-2-carboxamide | $^1$H NMR (400 MHz, Pyridine-d$_5$, Temp = 90° C.) δ ppm 7.92-7.94 (bs, 1H), 7.74-7.76 (m, 2H), 7.20-7.23 (m, 2H), 7.16-7.20 (m, 2H), 6.93-6.96 (m, 2H), 4.86 (s, 4H), 3.65-3.69 (m, 4H), 3.03-3.06 (m, 4H), 2.76-2.87 (m, 1H), 1.15 (d, J = 6.7 Hz, 6H) | (ESI (+)) m/e 393 (M + H)+ |
| 505 | N-{4-[4-(2-methylbutanoyl)piperazin-1-yl]phenyl}-1,3-dihydro-2H-isoindole-2-carboxamide | $^1$H NMR (400 MHz, Pyridine-d$_5$, Temp = 90° C.) δ ppm 7.92-7.94 (bs, 1H), 7.74-7.77 (m, 2H), 7.20-7.23 (m, 2H), 7.16-7.20 (m, 2H), 6.94-6.97 (m, 2H), 4.86 (s, 4H), 3.68-3.73 (m, 4H), 3.04-3.07 (m, 4H), 2.68 (h, J = 6.7 Hz, 1H), 1.76-1.87 (m, 1H), 1.40-1.51 (m, 1H), 1.15 (d, J = 6.7 Hz, 3H), 0.91 (t, J = 7.4 Hz, 3H) | (ESI (+)) m/e 407 (M + H)+ |
| 506 | N-{4-[4-(3,3,3-trifluoropropanoyl)piperazin-1-yl]phenyl}-1,3-dihydro-2H-isoindole-2-carboxamide | $^1$H NMR (400 MHz, Pyridine-d$_5$, Temp = 90° C.) δ ppm 7.93-7.95 (bs, 1H), 7.74-7.76 (m, 2H), 7.20-7.24 (m, 2H), 7.16-7.19 (m, 2H), 6.92-6.95 (m, 2H), 4.86 (s, 4H), 3.58-3.78 (m, 4H), 3.57 (q, J = 10.5 Hz, 2H), 3.02-3.09 (m, 4H) | (ESI (+)) m/e 433 (M + H)+ |
| 507 | N-{4-[4-(methoxyacetyl)piperazin-1-yl]phenyl}-1,3-dihydro-2H-isoindole-2-carboxamide | $^1$H NMR (400 MHz, Pyridine-d$_5$, Temp = 90° C.) δ ppm 7.92-7.96 (bs, 1H), 7.73-7.76 (m, 2H), 7.16-7.24 (m, 4H), 6.92-6.95 (m, 2H), 4.86 (s, 4H), 4.18 (s, 2H), 3.55-3.78 (m, 4H), 3.39 (s, 3H), 3.03-3.06 (m, 4H) | (ESI (+)) m/e 395 (M + H)+ |

| Ex | Name | ¹H NMR | MS |
|---|---|---|---|
| 508 | N-{4-[4-(tetrahydrofuran-2-ylcarbonyl)piperazin-1-yl]phenyl}-1,3-dihydro-2H-isoindole-2-carboxamide | ¹H NMR (400 MHz, Pyridine-$d_5$, Temp = 90° C.) δ ppm 7.90-7.95 (m, 1H), 7.73-7.75 (m, 2H), 7.19-7.24 (m, 2H), 7.15-7.19 (m, 2H), 6.92-6.95 (m, 2H), 4.86 (s, 4H), 4.66 (dd, J = 7.2, 5.4 Hz, 1H), 3.88-3.94 (m, 1H), 3.67-3.83 (m, 5H), 2.93-3.15 (m, 4H), 2.37-2.48 (m, 1H), 1.84-2.05 (m, 2H), 1.70-1.81 (m, 1H) | (ESI (+)) m/e 421 (M + H)⁺ |
| 509 | N-{4-[4-(tetrahydrofuran-3-ylcarbonyl)piperazin-1-yl]phenyl}-1,3-dihydro-2H-isoindole-2-carboxamide | ¹H NMR (400 MHz, Pyridine-$d_5$, Temp = 90° C.) δ ppm 7.93 (d, J = 2.6 Hz, 1H), 7.74-7.77 (m, 2H), 7.20-7.24 (m, 2H), 7.15-7.20 (m, 2H), 6.94-6.97 (m, 2H), 4.86 (s, 4H), 4.08 (dd, J = 8.3, 6.5 Hz, 1H), 4.04 (t, J = 8.0 Hz, 1H), 3.91 (td, J = 7.9, 5.9 Hz, 1H), 3.74-3.82 (m, 1H), 3.58-3.76 (m, 1H), 3.26-3.34 (m, 1H), 3.00-3.10 (m, 4H), 2.24-2.33 (m, 1H), 1.97-2.07 (m, 1H) | (ESI (+)) m/e 421 (M + H)⁺ |
| 510 | N-{4-[4-(cyclopentylacetyl)piperazin-1-yl]phenyl}-1,3-dihydro-2H-isoindole-2-carboxamide | ¹H NMR (400 MHz, Pyridine-$d_5$, Temp = 90° C.) δ ppm 7.90-7.92 (bs, 1H), 7.73-7.76 (m, 2H), 7.19-7.24 (m, 2H), 7.15-7.19 (m, 2H), 6.94-6.97 (m, 2H), 4.85 (s, 4H), 3.46-3.83 (m, 4H), 3.04-3.07 (m, 4H), 2.28-2.49 (m, 3H), 1.81-1.96 (m, 2H), 1.41-1.67 (m, 4H), 1.17-1.32 (m, 2H) | (ESI (+)) m/e 433 (M + H)⁺ |
| 511 | N-{4-[4-(cyclohexylcarbonyl)piperazin-1-yl]phenyl}-1,3-dihydro-2H-isoindole-2-carboxamide | ¹H NMR (400 MHz, Pyridine-$d_5$, Temp = 90° C.) δ ppm 7.90-7.92 (bs, 1H), 7.73-7.76 (m, 2H), 7.20-7.24 (m, 2H), 7.15-7.20 (m, 2H), 6.94-6.97 (m, 2H), 4.86 (s, 4H), 3.64-3.77 (m, 4H), 3.04-3.07 (m, 4H), 2.60 (tt, J = 11.0, 3.5 Hz, 1H), 1.55-1.85 (m, 7H), 1.14-1.40 (m, 3H) | (ESI (+)) m/e 433 (M + H)⁺ |
| 512 | N-{4-[4-(2-methoxybenzoyl)piperazin-1-yl]phenyl}-1,3-dihydro-2H-isoindole-2-carboxamide | ¹H NMR (400 MHz, Pyridine-$d_5$, Temp = 90° C.) δ ppm 7.90-7.92 (bs, 1H), 7.73-7.76 (m, 2H), 7.41 (dd, J = 7.4, 1.8 Hz, 1H), 7.30-7.35 (m, 1H), 7.19-7.24 (m, 2H), 7.15-7.19 (m, 2H), 7.01 (td, J = 7.4, 1.0 Hz, 1H), 6.92-6.98 (m, 3H), 4.85 (s, 4H), 3.77-4.30 (m, 2H), 3.70 (s, 3H), 3.51 (s, 2H), 2.79-3.24 (m, 4H) | (ESI (+)) m/e 457 (M + H)⁺ |
| 513 | N-{4-[4-(3-methoxybenzoyl)piperazin-1-yl]phenyl}-1,3-dihydro-2H-isoindole-2-carboxamide | ¹H NMR (400 MHz, Pyridine-$d_5$, Temp = 90° C.) δ ppm 7.92 (d, J = 2.1 Hz, 1H), 7.74-7.76 (m, 2H), 7.30-7.34 (m, 1H), 7.19-7.24 (m, 3H), 7.15-7.19 (m, 2H), 7.11-7.14 (m, 1H), 7.01 (ddd, J = 8.2, 2.6, 1.0 Hz, 1H), 6.93-6.96 (m, 2H), 4.86 (s, 4H), 3.67-3.79 (m, 7H), 3.06-3.09 (m, 4H) | (ESI (+)) m/e 457 (M + H)⁺ |
| 514 | N-{4-[4-(4-methoxybenzoyl)piperazin-1-yl]phenyl}-1,3-dihydro-2H-isoindole-2-carboxamide | ¹H NMR (400 MHz, Pyridine-$d_5$, Temp = 90° C.) δ ppm 7.89-7.92 (m, 1H), 7.74-7.76 (m, 2H), 7.53-7.56 (m, 2H), 7.20-7.23 (m, 2H), 7.15-7.20 (m, 2H), 6.90-7.01 (m, 4H), 4.86 (s, 4H), 3.73-3.78 (m, 4H), 3.71 (s, 3H), 3.08-3.11 (m, 4H) | (ESI (+)) m/e 457 (M + H)⁺ |
| 515 | N-{4-[4-(3-fluorobenzoyl)piperazin-1-yl]phenyl}-1,3-dihydro-2H-isoindole-2-carboxamide | ¹H NMR (400 MHz, Pyridine-$d_5$, Temp = 90° C.) δ ppm 7.91-7.93 (bs, 1H), 7.74-7.77 (m, 2H), 7.29-7.41 (m, 3H), 7.20-7.23 (m, 2H), 7.16-7.20 (m, 2H), 7.09-7.14 (m, 1H), 6.94-6.97 (m, 2H), 4.86 (s, 4H), 3.65-3.83 (m, 4H), 3.06-3.09 (m, 4H) | (ESI (+)) m/e 445 (M + H)⁺ |
| 516 | N-{4-[4-(2-chlorobenzoyl)piperazin-1-yl]phenyl}-1,3-dihydro-2H-isoindole-2-carboxamide | ¹H NMR (400 MHz, Pyridine-$d_5$, Temp = 90° C.) δ ppm 7.91-7.94 (bs, 1H), 7.74-7.77 (m, 2H), 7.34-7.45 (m, 2H), 7.25-7.29 (m, 2H), 7.19-7.23 (m, 2H), 7.16-7.19 (m, 2H), 6.94-6.96 (m, 2H), 4.85 (s, 4H), 3.72-4.17 (m, 2H), 3.26-3.50 (m, 2H), 2.84-3.25 (m, 4H) | (ESI (+)) m/e 461 (M + H)⁺ |
| 517 | N-{4-[4-(4-chlorobenzoyl)piperazin-1-yl]phenyl}-1,3-dihydro-2H-isoindole-2-carboxamide | ¹H NMR (400 MHz, Pyridine-$d_5$, Temp = 90° C.) δ ppm 7.91-7.93 (bs, 1H), 7.74-7.77 (m, 2H), 7.47-7.49 (m, 2H), 7.38-7.41 (m, 2H), 7.20-7.23 (m, 2H), 7.16-7.19 (m, 2H), 6.94-6.97 (m, 2H), 4.86 (s, 4H), 3.68-3.71 (m, 4H), 3.07-3.10 (m, 4H) | (ESI (+)) m/e 461 (M + H)⁺ |
| 518 | N-{4-[4-(3-cyanobenzoyl)piperazin-1-yl]phenyl}-1,3-dihydro-2H-isoindole-2-carboxamide | ¹H NMR (400 MHz, Pyridine-$d_5$, Temp = 90° C.) δ ppm 7.92-7.94 (bs, 1H), 7.88-7.89 (m, 1H), 7.75-7.77 (m, 2H), 7.71 (dt, J = 7.7, 1.4 Hz, 1H), 7.65 (dt, J = 7.7, 1.4 Hz, 1H), 7.44 (t, J = 7.7 Hz, 1H), 7.20-7.23 (m, 2H), 7.16-7.20 (m, 2H), 6.94-6.97 (m, 2H), 4.86 (s, 4H), 3.57-3.83 (m, 4H), 3.08-3.11 (m, 4H) | (ESI (−)) m/e 450 (M − H)⁻ |
| 519 | N-{4-[4-(4-cyanobenzoyl)piperazin-1-yl]phenyl}-1,3-dihydro-2H-isoindole-2-carboxamide | ¹H NMR (400 MHz, Pyridine-$d_5$, Temp = 90° C.) δ ppm 7.93-7.94 (bs, 1H), 7.74-7.77 (m, 2H), 7.65-7.71 (m, 2H), 7.56-7.61 (m, 2H), 7.20-7.23 (m, 2H), 7.16-7.19 (m, 2H), 6.94-6.97 (m, 2H), 4.86 (s, 4H), 3.58-3.77 (m, 4H), 3.08-3.11 (m, 4H) | (ESI (+)) m/e 452 (M + H)⁺ |
| 520 | N-(4-{4-[3-(dimethylamino)benzoyl]piperazin-1-yl}phenyl)-1,3-dihydro-2H-isoindole-2-carboxamide | ¹H NMR (400 MHz, Pyridine-$d_5$, Temp = 90° C.) δ ppm 7.91 (d, J = 2.6 Hz, 1H), 7.73-7.76 (m, 2H), 7.26-7.31 (m, 1H), 7.19-7.23 (m, 2H), 7.16-7.19 (m, 2H), 6.96-6.99 (m, 1H), 6.93-6.97 (m, 2H), 6.90 (dt, J = 7.3, 1.1 Hz, 1H), 6.78 (ddd, J = 8.4, 2.7, 0.8 Hz, 1H), 4.85 (s, 4H), 3.71-3.83 (m, 4H), 3.07-3.10 (m, 4H), 2.80 (s, 6H) | (ESI (+)) m/e 470 (M + H)⁺ |

| Ex | Name | ¹H NMR | MS |
|---|---|---|---|
| 521 | N-(4-{4-[4-(dimethylamino)benzoyl]piperazin-1-yl}phenyl)-1,3-dihydro-2H-isoindole-2-carboxamide | ¹H NMR (400 MHz, Pyridine-d₅, Temp = 90° C.) δ ppm 7.89-7.91 (bs, 1H), 7.73-7.76 (m, 2H), 7.55-7.57 (m, 2H), 7.19-7.23 (m, 2H), 7.16-7.19 (m, 2H), 6.94-6.97 (m, 2H), 6.71-6.73 (m, 2H), 4.86 (s, 4H), 3.78-3.81 (m, 4H), 3.09-3.12 (m, 4H), 2.81-2.84 (m, 6H) | (ESI (+)) m/e 470 (M + H)⁺ |
| 522 | N-{4-[4-(3,4-dimethoxybenzoyl)piperazin-1-yl]phenyl}-1,3-dihydro-2H-isoindole-2-carboxamide | ¹H NMR (400 MHz, Pyridine-d₅, Temp = 90° C.) δ ppm 7.91-7.93 (bs, 1H), 7.74-7.77 (m, 2H), 7.26 (d, J = 2.0 Hz, 1H), 7.20-7.24 (m, 2H), 7.16-7.19 (m, 3H), 6.93-7.00 (m, 3H), 4.86 (s, 4H), 3.77-3.80 (m, 4H), 3.77 (s, 3H), 3.77 (s, 3H), 3.07-3.15 (m, 4H) | (ESI (+)) m/e 487 (M + H)⁺ |
| 523 | N-{4-[4-(3,5-dimethoxybenzoyl)piperazin-1-yl]phenyl}-1,3-dihydro-2H-isoindole-2-carboxamide | ¹H NMR (400 MHz, Pyridine-d₅, Temp = 90° C.) δ ppm 7.91-7.93 (bs, 1H), 7.74-7.76 (m, 2H), 7.20-7.24 (m, 2H), 7.16-7.19 (m, 2H), 6.94-6.96 (m, 2H), 6.81-6.82 (m, 2H), 6.67 (t, J = 2.3 Hz, 1H), 4.86 (s, 4H), 3.70-3.77 (m, 4H), 3.71 (s, 6H), 3.07-3.10 (m, 4H) | (ESI (+)) m/e 487 (M + H)⁺ |
| 524 | N-(4-{4-[(3,4-dimethoxyphenyl)acetyl]piperazin-1-yl}phenyl)-1,3-dihydro-2H-isoindole-2-carboxamide | ¹H NMR (400 MHz, Pyridine-d₅, Temp = 90° C.) δ ppm 7.88-7.90 (bs, 1H), 7.71-7.74 (m, 2H), 7.19-7.23 (m, 2H), 7.15-7.19 (m, 2H), 7.09 (d, J = 2.0 Hz, 1H), 6.97 (dd, J = 8.1, 2.0 Hz, 1H), 6.88-6.93 (m, 3H), 4.85 (s, 4H), 3.81 (s, 2H), 3.74 (s, 3H), 3.73 (s, 3H), 3.67-3.78 (m, 4H), 3.00-3.03 (m, 4H) | (ESI (+)) m/e 501 (M + H)⁺ |
| 525 | N-{4-[4-(2-furoyl)piperazin-1-yl]phenyl}-1,3-dihydro-2H-isoindole-2-carboxamide | ¹H NMR (400 MHz, Pyridine-d₅, Temp = 90° C.) δ ppm 7.89-7.91 (bs, 1H), 7.73-7.76 (m, 2H), 7.57 (dd, J = 1.8, 0.9 Hz, 1H), 7.20-7.23 (m, 2H), 7.16-7.19 (m, 2H), 7.08 (dd, J = 3.4, 0.8 Hz, 1H), 6.93-6.96 (m, 2H), 6.45 (dd, J = 3.4, 1.7 Hz, 1H), 4.85 (s, 4H), 3.86-3.89 (m, 4H), 3.09-3.12 (m, 4H) | (ESI (+)) m/e 417 (M + H)⁺ |
| 526 | N-{4-[4-(3-furoyl)piperazin-1-yl]phenyl}-1,3-dihydro-2H-isoindole-2-carboxamide | ¹H NMR (400 MHz, Pyridine-d₅, Temp = 90° C.) δ ppm 7.93 (dd, J = 1.6, 0.8 Hz, 1H), 7.90-7.92 (bs, 1H), 7.73-7.76 (m, 2H), 7.52-7.53 (m, 1H), 7.19-7.23 (m, 2H), 7.16-7.19 (m, 2H), 6.93-6.96 (m, 2H), 6.72 (dd, J = 1.8, 0.9 Hz, 1H), 4.85 (s, 4H), 3.77-3.80 (m, 4H), 3.06-3.10 (m, 4H) | (ESI (+)) m/e 417 (M + H)⁺ |
| 527 | N-{4-[4-(1H-pyrrol-2-ylcarbonyl)piperazin-1-yl]phenyl}-1,3-dihydro-2H-isoindole-2-carboxamide | ¹H NMR (400 MHz, Pyridine-d₅, Temp = 90° C.) δ ppm 11.87-11.96 (bs, 1H), 7.88-7.89 (bs, 1H), 7.72-7.75 (m, 2H), 7.19-7.23 (m, 2H), 7.15-7.19 (m, 2H), 7.10 (td, J = 2.7, 1.3 Hz, 1H), 6.92-6.95 (m, 2H), 6.68-6.70 (m, 1H), 6.33-6.36 (m, 1H), 4.85 (s, 4H), 3.94-3.97 (m, 4H), 3.09-3.12 (m, 4H) | (ESI (−)) m/e 414 (M − H)⁻ |
| 528 | N-{4-[4-(1H-pyrazol-5-ylcarbonyl)piperazin-1-yl]phenyl}-1,3-dihydro-2H-isoindole-2-carboxamide | ¹H NMR (400 MHz, Pyridine-d₅, Temp = 90° C.) δ ppm 7.88 (d, J = 2.5 Hz, 1H), 7.77 (d, J = 2.2 Hz, 1H), 7.71-7.74 (m, 2H), 7.19-7.23 (m, 2H), 7.15-7.19 (m, 2H), 6.91-6.95 (m, 3H), 4.85 (s, 4H), 4.06-4.14 (m, 4H), 3.07-3.18 (m, 4H) | (ESI (+)) m/e 417 (M + H)⁺ |
| 529 | N-{4-[4-(pyridin-2-ylcarbonyl)piperazin-1-yl]phenyl}-1,3-dihydro-2H-isoindole-2-carboxamide | ¹H NMR (400 MHz, Pyridine-d₅, Temp = 90° C.) δ ppm 8.60 (ddd, J = 4.8, 1.8, 0.9 Hz, 1H), 7.84-7.97 (m, 1H), 7.76 (dt, J = 7.7, 1.1 Hz, 1H), 7.72-7.75 (m, 2H), 7.69 (td, J = 7.6, 1.8 Hz, 1H), 7.20-7.24 (m, 2H), 7.17-7.19 (m, 2H), 6.93-6.96 (m, 2H), 4.85 (s, 4H), 3.73-3.99 (m, 4H), 3.08-3.19 (m, 4H) | (ESI (+)) m/e 428 (M + H)⁺ |
| 530 | N-{4-[4-(pyridin-3-ylcarbonyl)piperazin-1-yl]phenyl}-1,3-dihydro-2H-isoindole-2-carboxamide | ¹H NMR (400 MHz, Pyridine-d₅, Temp = 90° C.) δ ppm 8.92 (dd, J = 2.2, 0.9 Hz, 1H), 8.70 (dd, J = 4.8, 1.7 Hz, 1H), 7.90-8.02 (m, 1H), 7.82 (dt, J = 7.8, 2.0 Hz, 1H), 7.74-7.77 (m, 2H), 7.27 (ddd, J = 7.7, 4.8, 0.9 Hz, 1H), 7.20-7.23 (m, 2H), 7.16-7.19 (m, 2H), 6.93-6.96 (m, 2H), 4.86 (s, 4H), 3.68-3.72 (m, 4H), 3.06-3.09 (m, 4H) | (ESI (+)) m/e 428 (M + H)⁺ |
| 531 | N-[4-(4-isonicotinoylpiperazin-1-yl)phenyl]-1,3-dihydro-2H-isoindole-2-carboxamide | ¹H NMR (400 MHz, Pyridine-d₅, Temp = 90° C.) δ ppm 8.74-8.76 (m, 2H), 7.95 (d, J = 2.8 Hz, 1H), 7.75-7.78 (m, 2H), 7.38-7.40 (m, 2H), 7.20-7.23 (m, 2H), 7.16-7.20 (m, 2H), 6.94-6.97 (m, 2H), 4.86 (s, 4H), 3.56-3.76 (m, 4H), 3.06-3.09 (m, 4H) | (ESI (+)) m/e 428 (M + H)⁺ |

| Ex | Name | ¹H NMR | MS |
|---|---|---|---|
| 532 | N-{4-[4-(pyridazin-3-ylcarbonyl)piperazin-1-yl]phenyl}-1,3-dihydro-2H-isoindole-2-carboxamide | ¹H NMR (400 MHz, Pyridine-d₅, Temp = 90° C.) δ ppm 9.22 (dd, J = 5.0, 1.7 Hz, 1H), 7.91 (dd, J = 8.3, 1.8 Hz, 1H), 7.89-7.92 (bs, 1H), 7.72-7.75 (m, 2H), 7.51 (dd, J = 8.5, 5.1 Hz, 1H), 7.19-7.23 (m, 2H), 7.16-7.19 (m, 2H), 6.92-6.95 (m, 2H), 4.85 (s, 4H), 3.60-4.20 (m, 4H), 2.94-3.32 (m, 4H) | (ESI (+)) m/e 429 (M + H)⁺ |
| 533 | N-{4-[4-(pyrazin-2-ylcarbonyl)piperazin-1-yl]phenyl}-1,3-dihydro-2H-isoindole-2-carboxamide | ¹H NMR (400 MHz, Pyridine-d₅, Temp = 90° C.) δ ppm 9.33 (d, J = 1.4 Hz, 1H), 8.87 (d, J = 5.0 Hz, 1H), 7.91-7.93 (bs, 1H), 7.73-7.76 (m, 2H), 7.70 (dd, J = 5.0, 1.4 Hz, 1H), 7.20-7.23 (m, 2H), 7.18 (t, J = 3.4 Hz, 2H), 6.94-6.96 (m, 2H), 4.85 (s, 4H), 3.48-4.06 (m, 4H), 3.12-3.15 (m, 4H) | (ESI (+)) m/e 429 (M + H)⁺ |
| 534 | N-{4-[4-(pyrimidin-4-ylcarbonyl)piperazin-1-yl]phenyl}-1,3-dihydro-2H-isoindole-2-carboxamide | ¹H NMR (400 MHz, Pyridine-d₅, Temp = 90° C.) δ ppm 9.13 (d, J = 1.5 Hz, 1H), 8.59 (d, J = 2.5 Hz, 1H), 8.50 (dd, J = 2.5, 1.5 Hz, 1H), 7.91 (d, J = 0.8 Hz, 1H), 7.73-7.76 (m, 2H), 7.20-7.23 (m, 2H), 7.16-7.18 (m, 2H), 6.94-6.97 (m, 2H), 4.85 (s, 4H), 3.73-3.96 (m, 4H), 3.07-3.22 (m, 4H) | (ESI (+)) m/e 429 (M + H)⁺ |
| 535 | N-{4-[4-(N,N-dimethyl-beta-alanyl)piperazin-1-yl]phenyl}-1,3-dihydro-2H-isoindole-2-carboxamide | ¹H NMR (400 MHz, Pyridine-d₅, Temp = 90° C.) δ ppm 7.90-7.93 (bs, 1H), 7.72-7.75 (m, 2H), 7.20-7.23 (m, 2H), 7.16-7.19 (m, 2H), 6.90-6.93 (m, 2H), 4.85 (s, 4H), 3.55-3.72 (m, 4H), 3.33 (t, J = 7.2 Hz, 2H), 3.00-3.05 (m, 4H), 2.96 (t, J = 7.2 Hz, 2H), 2.64 (s, 6H) | (ESI (+)) m/e 422 (M + H)⁺ |
| 536 | N-[4-(4-acetylpiperazin-1-yl)phenyl]-1,3-dihydro-2H-isoindole-2-carboxamide | ¹H NMR (400 MHz, Pyridine-d₅, Temp = 90° C.) δ ppm 7.89-7.92 (bs, 1H), 7.73-7.75 (m, 2H), 7.20-7.23 (m, 2H), 7.15-7.19 (m, 2H), 6.92-6.95 (m, 2H), 4.85 (s, 4H), 3.48-3.81 (m, 4H), 2.97-3.03 (m, 4H), 2.04 (s, 3H) | (ESI (+)) m/e 365 (M + H)⁺ |
| 537 | N-{4-[4-(2-fluorobenzoyl)piperazin-1-yl]phenyl}-1,3-dihydro-2H-isoindole-2-carboxamide | ¹H NMR (400 MHz, Pyridine-d₅, Temp = 90° C.) δ ppm 7.90-7.92 (bs, 1H), 7.73-7.76 (m, 2H), 7.46-7.51 (m, 1H), 7.29-7.36 (m, 1H), 7.19-7.23 (m, 2H), 7.16-7.18 (m, 3H), 7.09-7.12 (m, 1H), 6.93-6.95 (m, 2H), 4.85 (s, 4H), 3.38-4.02 (m, 4H), 2.90-3.23 (m, 4H) | (ESI (+)) m/e 445 (M + H)⁺ |
| 538 | N-{4-[4-(4-fluorobenzoyl)piperazin-1-yl]phenyl}-1,3-dihydro-2H-isoindole-2-carboxamide | ¹H NMR (400 MHz, Pyridine-d₅, Temp = 90° C.) δ ppm 7.91-7.93 (bs, 1H), 7.74-7.77 (m, 2H), 7.52-7.58 (m, 2H), 7.20-7.25 (m, 2H), 7.16-7.20 (m, 2H), 7.09-7.15 (m, 2H), 6.94-6.97 (m, 2H), 4.86 (s, 4H), 3.69-3.72 (m, 4H), 3.07-3.10 (m, 4H) | (ESI (+)) m/e 445 (M + H)⁺ |
| 539 | N-{4-[4-(phenylacetyl)piperazin-1-yl]phenyl}-1,3-dihydro-2H-isoindole-2-carboxamide | ¹H NMR (400 MHz, Pyridine-d₅-D₂O, Temp = 90° C.) δ ppm 2.95-3.04 (m, 4 H), 3.68 (s, 4 H), 3.83 (s, 2 H), 4.85 (s, 4 H), 6.87-6.93 (m, 2 H), 7.15-7.24 (m, 4 H), 7.27-7.33 (m, 2 H), 7.40 (d, J = 7.02 Hz, 2 H), 7.68-7.75 (m, 2 H), 7.89 (s, 1 H) | (ESI (+)) m/e 441 (M + H)⁺ |
| 540 | N-{4-[4-(1,3-thiazol-4-ylcarbonyl)piperazin-1-yl]phenyl}-1,3-dihydro-2H-isoindole-2-carboxamide | ¹H NMR (400 MHz, Pyridine-d₅, Temp = 90° C.) δ ppm 8.97 (d, J = 2.1 Hz, 1H), 8.17 (d, J = 2.1 Hz, 1H), 7.88-7.89 (bs, 1H), 7.72-7.75 (m, 2H), 7.19-7.23 (m, 2H), 7.16-7.19 (m, 2H), 6.93-6.96 (m, 2H), 4.85 (s, 4H), 3.98-4.01 (m, 4H), 3.13-3.16 (m, 4H) | (ESI (−)) m/e 432 (M − H)⁻ |
| 541 | N-{4-[4-(morpholin-4-ylacetyl)piperazin-1-yl]phenyl}-1,3-dihydro-2H-isoindole-2-carboxamide | ¹H NMR (400 MHz, Pyridine-d₅, Temp = 90° C.) δ ppm 7.85-8.03 (m, 1H), 7.74-7.77 (m, 2H), 7.21-7.23 (m, 2H), 7.16-7.19 (m, 2H), 6.97 (d, J = 7.0 Hz, 1H), 6.95-6.95 (m, 1H), 4.86 (s, 4H), 3.73-3.76 (m, 4H), 3.64-3.71 (m, 4H), 3.29 (s, 2H), 3.07-3.10 (m, 4H), 2.54-2.57 (m, 4H) | (ESI (+)) m/e 450 (M + H)⁺ |

Example 542

5-cyano-N-(4-phenylbutyl)-1,3-dihydro-2H-isoindole-2-carboxamide

The title compound was prepared as described in Example 1A, substituting 4-phenylbutyl isocyanate for methyl 4-isocyanatobenzoate and 5-cyanoisoindoline for isoindoline. $^1$H NMR (300 MHz, DMSO-d$_6$) δ ppm 7.82 (s, 1H), 7.74 (dd, J=7.9, 1.5 Hz, 1H), 7.53 (d, J=7.9 Hz, 1H), 7.24-7.31 (m, 2H), 7.08-7.22 (m, 3H), 6.38 (t, J=5.6 Hz, 1H), 4.59-4.64 (m, 4H), 3.06-3.13 (m, 2H), 2.58 (t, J=7.5 Hz, 2H), 1.53-1.68 (m, 2H), 1.36-1.51 (m, 2H); MS (ESI(+)) m/e 319 (M+H)$^+$.

Example 543

N-[4-(1-butyryl-1,2,3,6-tetrahydropyridin-4-yl)phenyl]-1,3-dihydro-2H-pyrrolo[3,4-c]pyridine-2-carboxamide

Example 543A

N-(4-bromophenyl)-1H-pyrrolo[3,4-c]pyridine-2(3H)-carboxamide

The title compound was prepared as described in Example 1A, substituting 4-bromophenyl isocyanate for methyl 4-isocyanatobenzoate and 2,3-dihydro-1H-pyrrolo[3,4-c]pyridine for isoindoline.

Example 543B tert-butyl 4-(4-(2,3-dihydro-1H-pyrrolo[3,4-c]pyridine-2-carboxamido)phenyl)-5,6-dihydropyridine-1(2H)-carboxylate The title compound was prepared as described in Example 280, substituting tert-butyl 4-(4,4,5,5-tetramethyl-1,3,2-dioxaborolan-2-yl)-5,6-dihydropyridine-1(2H)-carboxylate for 1H-pyrazol-3-ylboronic acid and N-(4-bromophenyl)-1H-pyrrolo[3,4-c]pyridine-2(3H)-carboxamide for 5-bromo-N-(4-(propylcarbamoyl)phenyl)isoindoline-2-carboxamide.

Example 543C

N-(4-(1,2,3,6-tetrahydropyridin-4-yl)phenyl)-1H-pyrrolo[3,4-c]pyridine-2(3H)-carboxamide The title compound was prepared as described in Example 2D, substituting tert-butyl 4-(4-(2,3-dihydro-1H-pyrrolo[3,4-c]pyridine-2-carboxamido)phenyl)-5,6-dihydropyridine-1(2H)-carboxylate for tert-butyl 4-((4-(5-fluoroisoindoline-2-carboxamido)benzamido)methyl)benzylcarbamate.

Example 543D

N-[4-(1-butyryl-1,2,3,6-tetrahydropyridin-4-yl)phenyl]-1,3-dihydro-2H-pyrrolo[3,4-c]pyridine-2-carboxamide The title compound was prepared as described in Example 278, substituting butyryl chloride for acetyl chloride and N-(4-(1,2,3,6-tetrahydropyridin-4-yl)phenyl)-1H-pyrrolo[3,4-c]pyridine-2(3H)-carboxamide for 5-amino-N-(4-(propylcarbamoyl)phenyl)isoindoline-2-carboxamide. $^1$H NMR (400 MHz, DMSO-d$_6$) δ ppm 8.61 (s, 1H), 8.50 (d, J=5.0 Hz, 1H), 8.46 (s, 1H), 7.54-7.57 (m, 2H), 7.43 (d, J=5.0 Hz, 1H), 7.32-7.39 (m, 2H), 6.09-6.11 (m, 1H), 4.79-4.82 (m, 4H), 4.08-4.14 (m, 2H), 3.58-3.68 (m, 2H), 2.39-2.55 (m, 2H), 2.34 (dt, J=19.9, 7.4 Hz, 2H), 1.47-1.62 (m, 2H), 0.88-0.93 (m, 3H); MS (ESI(+)) m/e 391 (M+H)$^+$.

Example 544

N-[4-(1-isobutyryl-1,2,3,6-tetrahydropyridin-4-yl)phenyl]-1,3-dihydro-2H-pyrrolo[3,4-c]pyridine-2-carboxamide The title compound was prepared as described in Example 278, substituting isobutyryl chloride for acetyl chloride and N-(4-(1,2,3,6-tetrahydropyridin-4-yl)phenyl)-1H-pyrrolo[3,4-c]pyridine-2(3H)-carboxamide for 5-amino-N-(4-(propylcarbamoyl)phenyl)isoindoline-2-carboxamide. $^1$H NMR (400 MHz, DMSO-d$_6$) δ ppm 8.61 (s, 1H), 8.50 (d, J=5.0 Hz, 1H), 8.46 (s, 1H), 7.54-7.57 (m, 2H), 7.43 (d, J=5.1 Hz, 1H), 7.34-7.38 (m, 2H), 6.10-6.13 (bs, 1H), 4.79-4.82 (m, 4H), 4.07-4.21 (m, 2H), 3.67-3.70 (m, 2H), 2.85-3.01 (m, 1H), 2.39-2.55 (m, 2H), 0.97-1.08 (m, 6H); MS (ESI(+)) m/e 391 (M+H)$^+$.

Example 545

N-[4-(1-benzoyl-1,2,3,6-tetrahydropyridin-4-yl)phenyl]-1,3-dihydro-2H-pyrrolo[3,4-c]pyridine-2-carboxamide The title compound was prepared as described in Example 278, substituting benzoyl chloride for acetyl chloride and N-(4-(1,2,3,6-tetrahydropyridin-4-yl)phenyl)-1H-pyrrolo[3,4-c]pyridine-2(3H)-carboxamide for 5-amino-N-(4-(propylcarbamoyl)phenyl)isoindoline-2-carboxamide. $^1$H NMR (400 MHz, DMSO-d$_6$) δ ppm 8.61 (s, 1H), 8.50 (d, J=5.0 Hz, 1H), 8.46 (s, 1H), 7.55-7.58 (m, 2H), 7.42-7.49 (m, 6H), 7.35-7.41 (m, 2H), 5.98-6.21 (m, 1H), 4.79-4.82 (m, 4H), 3.95-4.39 (m, 2H), 3.79-3.93 (m, 1H), 3.51-3.61 (m, 1H), 2.46-2.60 (m, 2H); MS (ESI(+)) m/e 425 (M+H)$^+$.

Table 9.

The following Examples were essentially prepared as described in Example 1C, substituting N-(4-(1,2,3,6-tetrahydropyridin-4-yl)phenyl)-1H-pyrrolo[3,4-c]pyridine-2(3H)-carboxamide for 3-phenylpropan-1-amine and the corresponding carboxylic acid for 4-(isoindoline-2-carboxamido)benzoic acid.

| Ex | Name | $^1$H NMR | MS |
|---|---|---|---|
| 546 | N-{4-[1-(tetrahydrofuran-3-ylcarbonyl)-1,2,3,6-tetrahydropyridin-4-yl]phenyl}-1,3-dihydro-2H-pyrrolo[3,4-c]pyridine-2-carboxamide | $^1$H NMR (400 MHz, DMSO-d$_6$) δ ppm 8.61 (s, 1H), 8.50 (d, J = 5.0 Hz, 1H), 8.46 (s, 1H), 7.54-7.57 (m, 2H), 7.43 (d, J = 5.0 Hz, 1H), 7.36 (dd, J = 8.4, 4.2 Hz, 2H), 6.09-6.12 (m, 1H), 4.75-4.87 (m, 4H), 4.10-4.21 (m, 2H), 3.90 (dt, J = 11.3, 8.1 Hz, 1H), 3.66-3.75 (m, 5H), 3.32-3.50 (m, 1H), 2.41-2.57 (m, 2H), 1.95-2.10 (m, 2H) | (ESI (+)) m/e 419 (M + H)$^+$ |

| Ex | Name | ¹H NMR | MS |
|---|---|---|---|
| 620 | N-(4-{1-[(2-methoxyethoxy)acetyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-d₆, Temp = 90° C.) δ ppm 8.58 (s, 1H), 8.48 (d, J = 5.0 Hz, 1H), 8.20 (s, 1H), 7.53 (m, 2H), 7.38 (d, J = 5.5 Hz, 1H), 7.32 (m, 2H), 6.06 (m, 1H), 4.80 (d, J = 8.9 Hz, 4H), 4.18 (s, 2H), 4.10 (m, 2H), 3.65 (t, J = 5.7 Hz, 2H), 3.60 (m, 2H), 3.49 (m, 2H), 3.27 (s, 3H), 2.50 (m, 2H) | (ESI (+)) m/e 437 (M + H)⁺ |
| 705 | N-{4-[1-(tetrahydrofuran-2-ylcarbonyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-d₆, Temp = 90° C.) δ ppm 8.58 (s, 1H), 8.48 (d, J = 5.0 Hz, 1H), 8.20 (s, 1H), 7.53 (m, 2H), 7.38 (d, J = 5.5 Hz, 1H), 7.33 (m, 2H), 6.07 (m, 1H), 4.79 (m, 4H), 4.67 (dd, J = 7.6, 5.6 Hz, 1H), 4.14 (bs, 2H), 3.85-3.64 (m, 4H), 2.50 (m, 2H), 2.11 (m, 1H), 2.00 (m, 1H), 1.85 (m, 2H) | (ESI (+)) m/e 419 (M + H)⁺ |
| 706 | N-{4-[1-(tetrahydro-2H-pyran-4-ylcarbonyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-d₆, Temp = 90° C.) δ ppm 8.58 (s, 1H), 8.48 (d, J = 5.0 Hz, 1H), 8.20 (s, 1H), 7.53 (m, 2H), 7.38 (d, J = 5.2 Hz, 1H), 7.33 (m, 2H), 6.07 (m, 1H), 4.80 (m, 4H), 4.14 (bs, 2H), 3.86 (m, 2H), 3.70 (t, J = 5.8 Hz, 2H), 3.42 (td, J = 11.4, 2.5 Hz, 2H), 2.92 (m, 1H), 2.50 (m, 2H), 1.72-1.52 (m, 4H) | (ESI (+)) m/e 433 (M + H)⁺ |
| 707 | N-{4-[1-(1,4-dioxan-2-ylcarbonyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-d₆, Temp = 90° C.) δ ppm 8.58 (s, 1H), 8.48 (d, J = 5.0 Hz, 1H), 8.20 (s, 1H), 7.53 (m, 2H), 7.38 (d, J = 4.9 Hz, 1H), 7.32 (m, 2H), 6.06 (m, 1H), 4.80 (m, 4H), 4.36 (dd, J = 9.2, 2.9 Hz, 1H), 4.14 (s, 2H), 3.83-3.60 (m, 7H), 3.52 (m, 1H), 2.50 (m, 2H) | (ESI (+)) m/e 435 (M + H)⁺ |
| 708 | N-(4-{1-[(1-methylpyrrolidin-3-yl)carbonyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-d₆, Temp = 90° C.) δ ppm 8.58 (s, 1H), 8.48 (d, J = 5.0 Hz, 1H), 8.20 (s, 1H), 7.53 (m, 2H), 7.38 (dd, J = 5.0, 1.1 Hz, 1H), 7.32 (m, 2H), 6.07 (m, 1H), 4.79 (m, 4H), 4.12 (m, 2H), 3.68 (t, J = 5.7 Hz, 2H), 3.27 (m, 1H), 2.77 (t, J = 8.6 Hz, 1H), 2.62-2.45 (m, 2H), 2.50 (m, 2H), 2.38 (m, 1H), 2.24 (s, 3H), 1.97 (m, 2H) | (ESI (+)) m/e 432 (M + H)⁺ |
| 709 | N-(4-{1-[(1,1-dioxidotetrahydrothiophen-3-yl)carbonyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-d₆, Temp = 90° C.) δ ppm 8.58 (s, 1H), 8.48 (d, J = 5.0 Hz, 1H), 8.21 (s, 1H), 7.53 (m, 2H), 7.38 (d, J = 5.1 Hz, 1H), 7.33 (m, 2H), 6.07 (m, 1H), 4.80 (m, 4H), 4.17 (bs, 2H), 3.72 (m, 3H), 3.31-3.13 (m, 3H), 3.07 (m, 1H), 2.51 (bs, 2H), 2.35 (m, 1H), 2.13 (m, 1H) | (ESI (+)) m/e 467 (M + H)⁺ |
| 710 | N-{4-[1-(2-hydroxy-2-methylpropanoyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-d₆, Temp = 90° C.) δ ppm 8.58 (s, 1H), 8.48 (d, J = 5.0 Hz, 1H), 8.20 (bs, 1H), 7.52 (m, 2H), 7.38 (d, J = 5.0 Hz, 1H), 7.33 (m, 2H), 6.08 (bs, 1H), 5.09 (s, 1H), 4.82 (m, 4H), 4.28 (m, 2H), 3.93 (m, 2H), 2.51 (m, 2H), 1.36 (s, 6H) | (ESI (+)) m/e 407 (M + H)⁺ |
| 799 | N-{4-[1-(morpholin-4-ylacetyl)-1,2,3,6-tetrahydropyridin-4-yl]phenyl}-1,3-dihydro-2H-pyrrolo[3,4-c]pyridine-2-carboxamide | ¹H NMR (501 MHz, DMSO-d₆, Temp = 90° C.) δ ppm 8.59 (s, 1H), 8.49 (d, J = 5.0 Hz, 1H), 8.25 (bs, 1H), 7.54 (m, 2H), 7.39 (d, J = 5.1 Hz, 1H), 7.35 (s, 1H), 7.33 (s, 1H), 6.08 (m, 1H), 4.82 (bs, 2H), 4.80 (bs, 2H), 4.18 (m, 2H), 3.71 (m, 2H), 3.58 (m, 4H), 3.21 (bs, 2H), 2.52 (m, 2H), 2.45 (m, 4H) | (ESI (+)) m/e XXX (M + H)⁺ |
| 967 | N-(4-{1-[(2R)-tetrahydrofuran-2-ylcarbonyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-d₆, Temp = 90° C.) δ ppm 8.58 (s, 1H), 8.48 (d, J = 5.0 Hz, 1H), 8.21 (bs, 1H), 7.53 (m, 2H), 7.38 (d, J = 5.1 Hz, 1H), 7.33 (m, 2H), 6.07 (m, 1H), 4.80 (m, 4H), 4.67 (t, J = 6.5 Hz, 1H), 4.14 (m, 2H), 3.86-3.64 (m, 4H), 2.50 (m, 2H), 2.11 (m, 1H), 2.00 (m, 1H), 1.86 (m, 2H) | (ESI (+)) m/e 419 (M + H)⁺ |
| 968 | N-(4-{1-[(2S)-tetrahydrofuran-2-ylcarbonyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-d₆, Temp = 90° C.) δ ppm 8.58 (s, 1H), 8.48 (d, J = 5.0 Hz, 1H), 8.20 (s, 1H), 7.53 (m, 2H), 7.38 (d, J = 5.1 Hz, 1H), 7.32 (m, 2H), 6.07 (m, 1H), 4.79 (m, 4H), 4.67 (dd, J = 7.5, 5.6 Hz, 1H), 4.14 (m, 2H), 3.85-3.66 (m, 4H), 2.50 (m, 2H), 2.11 (m, 1H), 2.00 (m, 1H), 1.86 (m, 2H) | (ESI (+)) m/e 419 (M + H)⁺ |
| 1014 | N-(4-{1-[(1-methylpiperidin-4-yl)carbonyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-d₆, Temp = 90° C.) δ ppm 8.58 (s, 1H), 8.48 (d, J = 5.0 Hz, 1H), 8.20 (bs, 1H), 7.53 (m, 2H), 7.38 (d, J = 5.0 Hz, 1H), 7.32 (m, 2H), 6.07 (bs, 1H), 4.82 (m, 4H), 4.12 (m, 2H), 3.67 (t, J = 5.7 Hz, 2H), 2.76 (m, 2H), 2.55 (m, 1H), 2.50 (m, 2H), 2.16 (s, 3H), 1.95 (td, J = 11.2, 3.6 Hz, 2H), 1.62 (m, 4H) | (ESI (+)) m/e 446 (M + H)⁺ |

| Ex | Name | ¹H NMR | MS |
|---|---|---|---|
| 1015 | N-(4-{1-[(1,1-dioxidotetrahydro-2H-thiopyran-4-yl)carbonyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-d₆, Temp = 90° C.) δ ppm 8.58 (s, 1H), 8.48 (d, J = 5.0 Hz, 1H), 8.21 (s, 1H), 7.53 (m, 2H), 7.38 (d, J = 5.0 Hz, 1H), 7.33 (m, 2H), 6.08 (m, 1H), 4.82 (m, 4H), 4.15 (m, 2H), 3.71 (t, J = 5.7 Hz, 2H), 3.24-3.04 (m, 5H), 2.50 (m, 2H), 2.06 (m, 4H) | (ESI (+)) m/e 481 (M + H)⁺ |
| 1016 | N-(4-{1-[(3R)-tetrahydrofuran-3-ylcarbonyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-d₆, Temp = 90° C.) δ ppm 8.58 (s, 1H), 8.48 (d, J = 5.0 Hz, 1H), 8.21 (s, 1H), 7.53 (m, 2H), 7.38 (d, J = 5.1 Hz, 1H), 7.33 (m, 2H), 6.07 (m, 1H), 4.79 (m, 4H), 4.14 (m, 2H), 3.91 (t, J = 8.1 Hz, 1H), 3.77-3.67 (m, 5H), 3.38 (m, 1H), 2.50 (m, 2H), 2.05 (m, 2H) | (ESI (+)) m/e 419 (M + H)⁺ |
| 1017 | N-(4-{1-[(3S)-tetrahydrofuran-3-ylcarbonyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-d₆, Temp = 90° C.) δ ppm 8.58 (s, 1H), 8.48 (d, J = 5.0 Hz, 1H), 8.20 (s, 1H), 7.53 (m, 2H), 7.38 (d, J = 5.1 Hz, 1H), 7.33 (m, 2H), 6.07 (m, 1H), 4.79 (m, 4H), 4.14 (m, 2H), 3.91 (t, J = 8.1 Hz, 1H), 3.78-3.64 (m, 5H), 3.38 (m, 1H), 2.50 (m, 2H), 2.05 (m, 2H) | (ESI (+)) m/e 419 (M + H)⁺ |
| 1077 | N-{4-[1-(tetrahydrofuran-3-ylacetyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-d₆, Temp = 90° C.) δ ppm 8.57 (bs, 1H), 8.48 (d, J = 5.0 Hz, 1H), 8.20 (s, 1H), 7.53 (m, 2H), 7.37 (d, J = 5.1 Hz, 1H), 7.32 (m, 2H), 6.06 (m, 1H), 4.81 (m, 4H), 4.11 (d, J = 2.8 Hz, 2H), 3.82 (dd, J = 8.4, 6.8 Hz, 1H), 3.76-3.59 (m, 4H), 3.29 (dd, J = 8.4, 6.1 Hz, 1H), 2.58-2.40 (m, 5H), 2.02 (m, 1H), 1.53 (m, 1H) | (ESI (+)) m/e 433 (M + H)⁺ |
| 1078 | N-{4-[1-(tetrahydro-2H-pyran-4-ylacetyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-d₆, Temp = 90° C.) δ ppm 8.58 (s, 1H), 8.48 (d, J = 5.0 Hz, 1H), 8.20 (s, 1H), 7.52 (m, 2H), 7.38 (d, J = 5.1 Hz, 1H), 7.32 (m, 2H), 6.07 (m, 1H), 4.80 (m, 4H), 4.11 (m, 2H), 3.81 (m, 2H), 3.67 (t, J = 5.7 Hz, 2H), 3.30 (td, J = 11.5, 2.2 Hz, 2H), 2.50 (m, 2H), 2.31 (d, J = 6.8 Hz, 2H), 2.98 (m, 1H), 1.62 (m, 2H), 1.25 (m, 2H) | (ESI (+)) m/e 447 (M + H)⁺ |
| 1079 | N-{4-[1-(N,N-dimethylglycyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-d₆, Temp = 90° C.) δ ppm 8.58 (s, 1H), 8.48 (d, J = 5.0 Hz, 1H), 8.21 (s, 1H), 7.53 (m, 2H), 7.38 (d, J = 5.1 Hz, 1H), 7.33 (m, 2H), 6.07 (m, 1H), 4.80 (m, 4H), 4.15 (m, 2H), 3.70 (t, J = 5.7 Hz, 2H), 3.15 (s, 2H), 2.50 (m, 2H), 2.23 (s, 6H) | (ESI (+)) m/e 406 (M + H)⁺ |
| 1080 | N-(4-{1-[(4-methylpiperazin-1-yl)acetyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-d₆, Temp = 90° C.) δ ppm 8.58 (s, 1H), 8.48 (d, J = 5.0 Hz, 1H), 8.20 (s, 1H), 7.53 (m, 2H), 7.38 (d, J = 5.1 Hz, 1H), 7.32 (m, 2H), 6.06 (m, 1H), 4.80 (m, 4H), 4.15 (m, 2H), 3.71 (m, 2H), 3.19 (m, 4H), 2.44 (m, 4H), 2.33 (m, 4H), 2.15 (s, 3H) | (ESI (+)) m/e 461 (M + H)⁺ |
| 1254 | N-{4-[1-(3-methylbutanoyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-d₆, Temp = 90° C.) δ ppm 8.59 (s, 1H), 8.48 (d, J = 5.0 Hz, 1H), 8.21 (s, 1H), 7.53 (m, 2H), 7.39 (d, J = 5.1 Hz, 1H), 7.33 (m, 2H), 6.07 (m, 1H), 4.81 (m, 4H), 4.12 (m, 2H), 3.67 (t, J = 5.7 Hz, 2H), 2.50 (m, 2H), 2.25 (d, J = 6.9 Hz, 2H), 2.05 (m, 1H), 0.94 (d, J = 6.6 Hz, 6H) | (ESI (+)) m/e 405 (M + H)⁺ |
| 1255 | N-{4-[1-(cyclopentylacetyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-d₆, Temp = 90° C.) δ ppm 8.59 (s, 1H), 8.48 (d, J = 5.0 Hz, 1H), 8.21 (s, 1H), 7.53 (m, 2H), 7.39 (d, J = 5.1 Hz, 1H), 7.33 (m, 2H), 6.07 (m, 1H), 4.82 (m, 4H), 4.11 (m, 2H), 3.67 (t, J = 5.7 Hz, 2H), 2.50 (m, 2H), 2.38 (d, J = 7.1 Hz, 2H), 2.21 (m, 1H), 1.77 (m, 2H), 1.66-1.46 (m, 4H), 1.18 (m, 2H) | (ESI (+)) m/e 431 (M + H)⁺ |
| 1256 | N-{4-[1-(tetrahydrofuran-2-ylacetyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-d₆, Temp = 90° C.) δ ppm 8.59 (s, 1H), 8.48 (d, J = 5.0 Hz, 1H), 8.21 (s, 1H), 7.53 (m, 2H), 7.39 (d, J = 5.0 Hz, 1H), 7.33 (m, 2H), 6.07 (m, 1H), 4.80 (m, 4H), 4.16 (m, 3H), 3.77 (m, 1H), 3.68 (m, 2H), 3.60 (m, 1H), 2.69 (m, 1H), 2.50 (m, 2H), 2.45 (m, 1H), 2.02 (m, 1H), 1.83 (m, 2H), 1.54 (m, 1H) | (ESI (+)) m/e 433 (M + H)⁺ |
| 1257 | N-{4-[1-(tetrahydro-2H-pyran-2-ylacetyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-d₆, Temp = 90° C.) δ ppm 8.59 (s, 1H), 8.48 (d, J = 5.0 Hz, 1H), 8.21 (s, 1H), 7.53 (m, 2H), 7.39 (d, J = 5.0 Hz, 1H), 7.33 (m, 2H), 6.06 (m, 1H), 4.83 (m, 4H), 4.12 (m, 2H), 3.83 (m, 1H), 3.69 (m, 3H), 3.35 (m, 1H), 2.61 (m, 1H), 2.50 (m, 2H), 2.37 (m, 1H), 1.82-1.63 (m, 2H), 1.48 (m, 3H), 1.26 (m, 1H) | (ESI (+)) m/e 447 (M + H)⁺ |

| Ex | Name | ¹H NMR | MS |
|---|---|---|---|
| 1258 | N-{4-[1-(pyrrolidin-1-ylacetyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-d₆, Temp = 90° C.) δ ppm 8.59 (s, 1H), 8.48 (d, J = 5.0 Hz, 1H), 8.21 (bs, 1H), 7.53 (m, 2H), 7.39 (d, J = 5.0 Hz, 1H), 7.33 (m, 2H), 6.07 (bs, 1H), 4.81 (m, 4H), 4.15 (m, 2H), 3.71 (m, 2H), 3.32 (bs, 2H), 2.55 (m, 4H), 2.50 (m, 2H), 1.70 (m, 4H) | (ESI (+)) m/e 432 (M + H)⁺ |
| 1259 | N-{4-[1-(pyrazin-2-ylcarbonyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-d₆, Temp = 90° C.) δ ppm 8.85 (d, J = 1.5 Hz, 1H), 8.72 (d, J = 2.5 Hz, 1H), 8.66 (m, 1H), 8.58 (s, 1H), 8.48 (d, J = 5.0 Hz, 1H), 8.22 (s, 1H), 7.53 (m, 2H), 7.38 (d, J = 5.1 Hz, 1H), 7.34 (m, 2H), 6.09 (m, 1H), 4.82 (m, 4H), 4.22 (m, 2H), 3.69 (m, 2H), 2.57 (m, 2H) | (ESI (+)) m/e 427 (M + H)⁺ |
| 1479 | N-(4-{1-[(2-methyl-1,3-oxazol-4-yl)carbonyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 4.88 Hz, 1 H) 8.25 (s, 1 H) 7.49-7.54 (m, 2 H) 7.41 (d, J = 4.88 Hz, 1 H) 7.33-7.37 (m, 2 H) 6.11 (t, J = 3.51 Hz, 1 H) 4.82 (d, J = 7.93 Hz, 4 H) 4.36 (s, 2 H) 3.95 (s, 2 H) 2.53-2.59 (m, 2 H) 2.45-2.47 (m, 3 H) | (ESI (+)) m/e 430 (M + H)⁺ |
| 1480 | N-{4-[1-(furan-3-ylcarbonyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-D₂O, Temp = 90° C.) δ ppm 8.59 (s, 1 H) 8.49 (d, J = 5.19 Hz, 1 H) 7.98 (s, 1 H) 7.67 (t, J = 1.68 Hz, 1 H) 7.52 (d, J = 8.54 Hz, 2 H) 7.43 (d, J = 4.88 Hz, 1 H) 7.35 (d, J = 8.54 Hz, 2 H) 6.69 (s, 1 H) 6.05-6.13 (m, 1 H) 4.82 (d, 4 H) 4.23-4.28 (m, 2 H) 3.79 (t, J = 5.80 Hz, 2 H) 2.53-2.59 (m, 2 H) | (ESI (+)) m/e 415 (M + H)⁺ |
| 1481 | N-(4-{1-[(2E)-3-(furan-2-yl)prop-2-enoyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 4.88 Hz, 1 H) 7.70 (d, J = 1.53 Hz, 1 H) 7.49-7.55 (m, 2 H) 7.30-7.44 (m, 4 H) 6.91 (d, J = 15.26 Hz, 1 H) 6.81 (d, J = 3.36 Hz, 1 H) 6.57 (dd, J = 3.36, 1.83 Hz, 1 H) 6.12 (t, J = 3.51 Hz, 1 H) 4.81 (d, 4 H) 4.24-4.28 (m, 2 H) 3.81 (t, J = 5.65 Hz, 2 H) 2.55 (s, 2 H) | (ESI (+)) m/e 441 (M + H)⁺ |
| 1482 | N-{4-[1-(1,3-oxazol-5-ylcarbonyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-D₂O, Temp = 90° C.) δ ppm 8.59 (s, 1 H) 8.49 (d, J = 4.88 Hz, 1 H) 8.41 (s, 1 H) 7.67 (s, 1 H) 7.52 (d, J = 8.85 Hz, 2 H) 7.44 (d, J = 5.19 Hz, 1 H) 7.36 (d, J = 8.54 Hz, 2 H) 6.09-6.14 (m, 1 H) 4.83 (d, J = 4.88 Hz, 4 H) 4.32 (d, J = 2.75 Hz, 2 H) 3.87 (t, J = 5.80 Hz, 2 H) 2.60 (m, 2 H) | (ESI (+)) m/e 416 (M + H)⁺ |
| 1483 | N-{4-[1-(3,3,3-trifluoropropanoyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, 1 H) 7.52 (d, J = 8.85 Hz, 2 H) 7.42 (d, 1 H) 7.35 (d, J = 8.85 Hz, 2 H) 6.08 (s, 1 H) 4.81 (d, J = 9.16 Hz, 4 H) 4.12-4.16 (m, 2 H) 3.65-3.73 (m, 2 H) 3.51-3.63 (m, 2 H) 2.52-2.58 (m, 2 H) | (ESI (+)) m/e 431 (M + H)⁺ |
| 1484 | N-(4-{1-[(1,5-dimethyl-1H-pyrazol-3-yl)carbonyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 5.19 Hz, 1 H) 7.51 (d, J = 8.54 Hz, 2 H) 7.41 (d, J = 4.88 Hz, 1 H) 7.35 (d, J = 8.54 Hz, 2 H) 6.33 (s, 1 H) 6.07-6.12 (m, 1 H) 4.81 (d, J = 7.32 Hz, 4 H) 4.36 (s, 2 H) 3.94 (s, 2 H) 3.75-3.78 (m, 3 H) 2.52-2.57 (m, 2 H) 2.26-2.29 (m, 3 H) | (ESI (+)) m/e 443 (M + H)⁺ |
| 1485 | N-(4-{1-[(4-methoxycyclohexyl)carbonyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 4.88 Hz, 1 H) 7.51 (d, J = 8.85 Hz, 2 H) 7.41 (d, J = 5.19 Hz, 1 H) 7.34 (d, J = 8.54 Hz, 2 H) 6.09 (t, J = 3.51 Hz, 1 H) 4.81 (d, J = 7.63 Hz, 4 H) 4.12 (s, 2 H) 3.68 (t, J = 5.80 Hz, 2 H) 3.37-3.43 (m, 1 H) 3.22 (s, 3 H) 2.61-2.74 (m, 1 H) 2.44-2.50 (m, 2 H) 1.82-1.91 (m, J = 12.97, 3.81 Hz, 2 H) 1.62-1.75 (m, 2 H) 1.37-1.55 (m, 4 H) | (ESI (+)) m/e 461 (M + H)⁺ |
| 1486 | N-{4-[1-(2,3-dimethylbutanoyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 4.88 Hz, 1 H) 7.51 (d, J = 8.85 Hz, 2 H) 7.41 (d, J = 5.19 Hz, 1 H) 7.34 (d, J = 8.54 Hz, 2 H) 6.07-6.13 (m, 1 H) 4.81 (d, J = 7.63 Hz, 4 H) 4.15 (s, 2 H) 3.66-3.76 (m, 2 H) 2.56-2.65 (m, 1 H) 2.42-2.50 (m, 2 H) 1.74-1.89 (m, 1 H) 1.00 (d, J = 6.71 Hz, 3 H) 0.87 (dd, J = 13.58, 6.87 Hz, 6 H) | (ESI (+)) m/e 419 (M + H)⁺ |
| 1487 | N-(4-{1-[(2,2-difluorocyclopropyl)carbonyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 4.88 Hz, 1 H) 7.52 (d, J = 8.85 Hz, 2 H) 7.41 (d, J = 5.19 Hz, 1 H) 7.35 (d, J = 8.85 Hz, 2 H) 6.10 (s, 1 H) 4.82 (d, J = 7.32 Hz, 4 H) 4.19 (s, 2 H) 3.65-3.94 (m, 2 H) 2.94-3.16 (m, J = 7.32 Hz, 1 H) 2.52-2.66 (m, 2 H) 1.91-2.00 (m, 1 H) 1.76-1.88 (m, 1 H) | (ESI (+)) m/e 425 (M + H)⁺ |

| Ex | Name | ¹H NMR | MS |
|---|---|---|---|
| 1488 | N-{4-[1-(1H-pyrazol-5-ylcarbonyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 4.88 Hz, 1 H) 7.71 (d, J = 2.14 Hz, 1 H) 7.33-7.55 (m, 5 H) 6.59 (d, J = 2.44 Hz, 1 H) 6.11 (s, 1 H) 4.82 (d, J = 6.41 Hz, 4 H) 4.37 (s, 2 H) 3.95 (s, 2 H) 2.53-2.59 (m, J = 3.05 Hz, 2 H) | (ESI (+)) m/e 415 (M + H)⁺ |
| 1489 | N-{4-[1-(tert-butoxyacetyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 5.19 Hz, 1 H) 7.51 (d, J = 8.54 Hz, 2 H) 7.41 (d, J = 4.88 Hz, 1 H) 7.34 (d, J = 8.54 Hz, 2 H) 6.08 (t, J = 3.36 Hz, 1 H) 4.82 (d, J = 7.93 Hz, 4 H) 4.12 (s, 2 H) 4.05 (s, 2 H) 3.69 (t, J = 5.80 Hz, 2 H) 1.19 (s, 9 H) | (ESI (+)) m/e 435 (M + H)⁺ |
| 1490 | N-(4-{1-[3-(1H-1,2,4-triazol-1-yl)propanoyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 5.19 Hz, 1 H) 8.39 (s, 1 H) 7.88 (s, 1 H) 7.48-7.53 (m, 2 H) 7.42 (d, J = 4.88 Hz, 1 H) 7.33 (d, J = 8.54 Hz, 2 H) 6.05 (s, 1 H) 4.82 (d, J = 6.41 Hz, 4 H) 4.46 (t, J = 6.71 Hz, 2 H) 4.07-4.12 (m, 2 H) 3.60-3.67 (m, 2 H) 2.98 (t, J = 6.26 Hz, 2 H) 2.42-2.49 (m, 2 H) | (ESI (+)) m/e 444 (M + H)⁺ |
| 1491 | N-{4-[1-(3-ethoxypropanoyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 4.88 Hz, 1 H) 7.51 (d, J = 8.54 Hz, 2 H) 7.42 (d, J = 5.19 Hz, 1 H) 7.34 (d, J = 8.54 Hz, 2 H) 6.06-6.10 (m, 1 H) 4.82 (d, J = 7.63 Hz, 4 H) 4.13 (s, 2 H) 3.62-3.72 (m, 4 H) 3.44 (q, J = 7.22 Hz, 2 H) 2.57-2.65 (m, 2 H) 1.09 (t, J = 6.87 Hz, 3 H) | (ESI (+)) m/e 421 (M + H)⁺ |
| 1492 | N-{4-[1-(3-hydroxy-3-methylbutanoyl)-1,2,3,6-tetrahydropyridin-4-yl]phenyl}-1,3-dihydro-2H-pyrrolo[3,4-c]pyridine-2-carboxamide | ¹H NMR (400 MHz, Solvent) δ ppm 8.58 (s, 1 H) 8.48 (d, J = 5.19 Hz, 1 H) 7.49-7.54 (m, 2 H) 7.41 (d, J = 4.88 Hz, 1 H) 7.34 (d, J = 8.54 Hz, 2 H) 6.08 (s, 1 H) 4.81 (d, J = 7.63 Hz, 4 H) 4.16 (s, 2 H) 3.72 (t, J = 5.80 Hz, 2 H) 2.31-2.50 (m, J = 14.04 Hz, 2 H) 1.12-1.33 (m, 8 H) | (ESI (+)) m/e 421 (M + H)⁺ |
| 1493 | N-(4-{1-[3-(1H-pyrrol-1-yl)propanoyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 5.19 Hz, 1 H) 7.51 (d, J = 8.85 Hz, 2 H) 7.41 (d, J = 5.19 Hz, 1 H) 7.32 (d, J = 8.54 Hz, 2 H) 6.72 (t, J = 1.98 Hz, 2 H) 6.04 (t, 1 H) 5.96 (t, J = 2.14 Hz, 2 H) 4.81 (d, J = 7.93 Hz, 4 H) 4.16 (t, J = 6.87 Hz, 2 H) 4.06 (m, 2 H) 3.63 (s, 2 H) 2.82 (s, 2 H) 2.45 (s, 2 H) | (ESI (+)) m/e 442 (M + H)⁺ |
| 1494 | N-(4-{1-[(1-methylcyclopropyl)carbonyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 4.88 Hz, 1 H) 7.48-7.54 (m, 2 H) 7.41 (d, J = 4.88 Hz, 1 H) 7.32-7.37 (m, 2 H) 6.11 (t, J = 3.51 Hz, 1 H) 4.79-4.85 (m, 4 H) 4.12-4.20 (m, 2 H) 3.78 (t, J = 5.65 Hz, 2 H) 2.47-2.51 (m, 2 H) 1.26-1.30 (m, 3 H) 0.81-0.86 (m, 2 H) 0.55-0.62 (m, 2 H) | (ESI (+)) m/e 403 (M + H)⁺ |
| 1495 | N-(4-{1-[(2-methylpropoxy)acetyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 5.19 Hz, 1 H) 7.48-7.53 (m, 2 H) 7.41 (d, J = 4.88 Hz, 1 H) 7.31-7.35 (m, 2 H) 6.05-6.09 (m, 1 H) 4.82 (d, J = 7.93 Hz, 4 H) 4.07-4.20 (m, 4 H) 3.67 (t, J = 5.65 Hz, 2 H) 3.18-3.24 (m, 2 H) 2.47-2.51 (m, 2 H) 1.76-1.89 (m, 1 H) 0.85-0.91 (m, 6 H) | (ESI (+)) m/e 435 (M + H)⁺ |
| 1496 | N-{4-[1-(1-methylprolyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 4.88 Hz, 1 H) 7.49-7.54 (m, 2 H) 7.41 (d, J = 5.19 Hz, 1 H) 7.34 (d, J = 8.85 Hz, 2 H) 6.09 (t, J = 3.36 Hz, 1 H) 4.78-4.84 (m, 4 H) 4.19 (s, 2 H) 3.66-3.89 (m, 2 H) 3.30-3.35 (m, 2 H) 2.98-3.06 (m, 1 H) 2.43-2.50 (m, 2 H) 2.29-2.37 (m, 1 H) 2.27 (s, 3 H) 2.05-2.14 (m, 1 H) 1.71-1.86 (m, 3 H) | (ESI (+)) m/e 432 (M + H)⁺ |
| 1497 | N-{4-[1-(2-hydroxy-2-methylbutanoyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 5.19 Hz, 1 H) 7.49-7.53 (m, 2 H) 7.41 (d, J = 5.19 Hz, 1 H) 7.34 (d, J = 8.85 Hz, 2 H) 6.09 (t, J = 3.66 Hz, 1 H) 4.81 (d, J = 7.02 Hz, 4 H) 4.29 (s, 2 H) 3.85-3.98 (m, 2 H) 2.46-2.51 (m, 2 H) 1.59-1.86 (m, 2 H) 1.32-1.35 (m, 3 H) 0.82 (t, 3 H) | (ESI (+)) m/e 421 (M + H)⁺ |
| 1498 | N-(4-{1-[(1-hydroxycyclopropyl)carbonyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 4.88 Hz, 1 H) 7.51 (d, J = 8.54 Hz, 2 H) 7.42 (d, J = 5.19 Hz, 1 H) 7.33-7.37 (m, 2 H) 6.11 (t, J = 3.36 Hz, 1 H) 4.82 (d, J = 6.41 Hz, 4 H) 4.24 (s, 2 H) 3.87 (t, J = 5.65 Hz, 2 H) 2.52-2.57 (m, 2 H) 0.93-0.99 (m, 2 H) 0.80-0.85 (m, 2 H) | (ESI (+)) m/e 405 (M + H)⁺ |

| Ex | Name | ¹H NMR | MS |
|---|---|---|---|
| 1499 | N-{4-[1-(cyclopropylacetyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-D$_2$O, Temp = 90° C.) δ ppm 8.58 (s, 1 H) 8.48 (d, J = 4.88 Hz, 1 H) 7.51 (d, J = 8.85 Hz, 2 H) 7.42 (d, J = 5.19 Hz, 1 H) 7.31-7.37 (m, 2 H) 6.05-6.11 (m, 1 H) 4.82 (d, J = 6.41 Hz, 4 H) 4.09-4.13 (m, J = 3.05 Hz, 2 H) 3.67 (t, J = 5.80 Hz, 2 H) 2.46-2.50 (m, 2 H) 2.33 (d, J = 6.71 Hz, 2 H) 1.00 (s, 1 H) 0.44-0.51 (m, 2 H) 0.16 (q, J = 4.98 Hz, 2 H) | (ESI (+)) m/e 403 (M + H)$^+$ |
| 1500 | N-{4-[1-(cyclopentylcarbonyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-D$_2$O, Temp = 90° C.) δ ppm 8.58 (s, 1 H) 8.48 (d, J = 4.88 Hz, 1 H) 7.49-7.53 (m, 2 H) 7.41 (d, J = 4.88 Hz, 1 H) 7.31-7.36 (m, 2 H) 6.04-6.12 (m, 1 H) 4.79-4.84 (m, 4 H) 4.14 (s, 2 H) 3.70 (t, J = 5.80 Hz, 2 H) 3.02 (m, J = 7.63 Hz, 1 H) 2.43-2.49 (m, 2 H) 1.48-1.86 (m, 8 H) | (ESI (+)) m/e 417 (M + H)$^+$ |
| 1501 | N-[4-(1-{[1-(methoxymethyl)cyclopropyl]carbonyl}-1,2,3,6-tetrahydroryridin-4-yl)phenyl]-1,3-dihydro-2H-pyrrolo[3,4-c]pyridine-2-carboxamide | ¹H NMR (400 MHz, DMSO-D$_2$O, Temp = 90° C.) δ ppm 8.58 (s, 1 H) 8.48 (d, J = 4.88 Hz, 1 H) 7.48-7.55 (m, 2 H) 7.41 (d, J = 5.19 Hz, 1 H) 7.34 (d, J = 8.85 Hz, 2 H) 6.06-6.12 (m, J = 3.51, 3.51 Hz, 1 H) 4.79-4.85 (m, 4 H) 4.17 (d, J = 3.05 Hz, 2 H) 3.79 (t, J = 5.80 Hz, 2 H) 3.44 (s, 2 H) 3.25 (s, 3 H) 2.46-2.50 (m, 2 H) 0.85-0.90 (m, 2 H) 0.73-0.80 (m, 2 H) | (ESI (+)) m/e 433 (M + H)$^+$ |
| 1502 | N-(4-{1-[(methylsulfonyl)acetyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-D$_2$O, Temp = 90° C.) δ ppm 8.59 (s, 1 H) 8.49 (d, J = 5.19 Hz, 1 H) 7.52 (d, J = 8.85 Hz, 2 H) 7.42 (d, J = 5.49 Hz, 1 H) 7.32-7.38 (m, J = 8.85 Hz, 2 H) 6.08 (s, 1 H) 4.82 (d, J = 6.10 Hz, 4 H) 4.35-4.46 (m, 2 H) 4.11-4.26 (m, 2 H) 3.74 (t, J = 5.80 Hz, 2 H) 3.08-3.12 (m, 3 H) 2.53-2.69 (m, 2 H) | (ESI (+)) m/e 441 (M + H)$^+$ |
| 1503 | N-(4-{1-[(1-methyl-1H-pyrazol-4-yl)carbonyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-D$_2$O, Temp = 90° C.) δ ppm 8.59 (s, 1 H) 8.49 (d, J = 4.88 Hz, 1 H) 8.00 (s, 1 H) 7.69 (s, 1 H) 7.49-7.54 (m, 2 H) 7.42 (d, J = 5.49 Hz, 1 H) 7.33-7.38 (m, 2 H) 6.07-6.12 (m, J = 3.51, 3.51 Hz, 1 H) 4.79-4.85 (m, 4 H) 4.27 (d, J = 3.05 Hz, 2 H) 3.87 (s, 3 H) 3.81 (t, J = 5.65 Hz, 2 H) 2.54-2.61 (m, J = 3.36 Hz, 2 H) | (ESI (+)) m/e 429 (M + H)$^+$ |
| 1504 | N-[4-(1-acetyl-1,2,3,6-tetrahydropyridin-4-yl)phenyl]-1,3-dihydro-2H-pyrrolo[3,4-c]pyridine-2-carboxamide | ¹H NMR (400 MHz, DMSO-D$_2$O, Temp = 90° C.) δ ppm 8.58 (s, 1 H) 8.48 (d, J = 4.88 Hz, 1 H) 7.51 (d, J = 8.85 Hz, 2 H) 7.41 (d, J = 4.88 Hz, 1 H) 7.34 (d, J = 8.54 Hz, 2 H) 6.08 (t, J = 3.51 Hz, 1 H) 4.82 (d, J = 7.32 Hz, 4 H) 4.10 (s, 2 H) 3.65 (t, J = 5.80 Hz, 2 H) 2.41-2.51 (m, 2 H) 2.06 (s, 3 H) | (ESI (+)) m/e 363 (M + H)$^+$ |
| 1505 | N-{4-[1-(cyclopropylcarbonyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-D$_2$O, Temp = 90° C.) δ ppm 8.58 (s, 1 H) 8.48 (d, J = 5.19 Hz, 1 H) 7.52 (d, J = 8.54 Hz, 2 H) 7.41 (d, J = 4.58 Hz, 1 H) 7.35 (d, J = 8.85 Hz, 2 H) 6.10 (s, 1 H) 4.81 (d, J = 8.54 Hz, 4 H) 4.22 (s, 2 H) 3.71-3.84 (m, 2 H) 2.37-2.49 (m, 2 H) 1.90-2.01 (m, J = 13.73 Hz, 1 H) 0.71-0.84 (m, 4 H) | (ESI (+)) m/e 389 (M + H)$^+$ |
| 1506 | N-{4-[1-(2-ethylbutanoyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-D$_2$O, Temp = 90° C.) δ ppm 8.58 (s, 1 H) 8.48 (d, J = 4.88 Hz, 1 H) 7.51 (d, J = 8.85 Hz, 2 H) 7.41 (d, J = 4.88 Hz, 1 H) 7.34 (d, J = 8.85 Hz, 2 H) 6.08-6.12 (m, 1 H) 4.81 (d, J = 7.93 Hz, 4 H) 4.14-4.20 (m, J = 1.83 Hz, 2 H) 3.74 (t, J = 5.80 Hz, 2 H) 2.60-2.71 (m, 1 H) 2.43-2.50 (m, 2 H) 1.37-1.62 (m, 4 H) 0.82 (t, J = 7.32 Hz, 6 H) | (ESI (+)) m/e 419 (M + H)$^+$ |
| 1507 | N-{4-[1-(5-oxo-L-prolyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-D$_2$O, Temp = 90° C.) δ ppm 8.59 (s, 1 H) 8.49 (d, J = 4.88 Hz, 1 H) 7.52 (d, J = 8.85 Hz, 2 H) 7.43 (d, J = 4.88 Hz, 1 H) 7.35 (d, J = 8.85 Hz, 2 H) 6.09 (s, 1 H) 4.82 (d, J = 6.71 Hz, 4 H) 4.58 (s, 1 H) 4.14 (s, 2 H) 3.70 (t, 2 H) 2.55-2.64 (m, 1 H) 2.29-2.46 (m, 2 H) 2.14-2.22 (m, 2 H) 1.92 (s, 1 H) | (ESI (+)) m/e 432 (M + H)$^+$ |

| Ex | Name | ¹H NMR | MS |
|---|---|---|---|
| 1508 | N-(4-{1-[(2E)-4-methylpent-2-enoyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-$D_2$O, Temp = 90° C.) δ ppm 8.58 (s, 1 H) 8.48 (d, J = 5.19 Hz, 1 H) 7.51 (d, J = 8.85 Hz, 2 H) 7.41 (d, J = 5.19 Hz, 1 H) 7.34 (d, J = 8.85 Hz, 2 H) 6.66 (dd, J = 15.26, 6.71 Hz, 1 H) 6.34 (d, J = 15.26 Hz, 1 H) 6.06-6.11 (m, 1 H) 4.81 (d, J = 7.32 Hz, 4 H) 4.18 (d, J = 2.75 Hz, 2 H) 3.74 (t, J = 5.80 Hz, 2 H) 2.38-2.50 (m, 3 H) 1.05 (d, J = 6.71 Hz, 6 H) | (ESI (+)) m/e 417 (M + H)⁺ |
| 1509 | N-{4-[1-(2-methoxy-2-methylpropanoyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-$D_2$O, Temp = 90° C.) δ ppm 8.58 (s, 1 H) 8.48 (d, J = 4.88 Hz, 1 H) 7.51 (d, J = 8.54 Hz, 2 H) 7.41 (d, J = 4.58 Hz, 1 H) 7.35 (d, J = 8.85 Hz, 2 H) 6.07-6.14 (m, 1 H) 4.78-4.84 (m, 4 H) 4.31 (s, 2 H) 3.92 (s, 2 H) 3.16 (s, 3 H) 2.47-2.50 (m, 2 H) 1.35-1.39 (m, 6 H) | (ESI (+)) m/e 421 (M + H)⁺ |
| 1510 | N-{4-[1-(cyclopent-1-en-1-ylcarbonyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-$D_2$O, Temp = 90° C.) δ ppm 8.58 (s, 1 H) 8.48 (d, J = 4.88 Hz, 1 H) 7.51 (d, J = 8.54 Hz, 2 H) 7.41 (d, J = 5.19 Hz, 1 H) 7.32-7.37 (m, 2 H) 6.06-6.11 (m, 1 H) 5.92-5.95 (m, 1 H) 4.81 (d, J = 7.63 Hz, 4 H) 4.15 (q, J = 2.64 Hz, 2 H) 3.71 (t, J = 5.80 Hz, 2 H) 2.53-2.57 (m, 2 H) 2.41-2.50 (m, 4 H) 1.85-1.95 (m, 2 H) | (ESI (+)) m/e 415 (M + H)⁺ |
| 1511 | N-{4-[1-(thiophen-3-ylacetyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-$D_2$O, Temp = 90° C.) δ ppm 8.58 (s, 1 H) 8.48 (d, J = 5.19 Hz, 1 H) 7.50 (d, J = 8.54 Hz, 2 H) 7.39-7.43 (m, J = 4.12, 4.12 Hz, 2 H) 7.31 (d, J = 8.85 Hz, 2 H) 7.23 (s, 1 H) 7.02 (d, J = 5.19 Hz, 1 H) 6.06 (s, 1 H) 4.81 (d, J = 7.32 Hz, 4 H) 4.15 (s, 2 H) 3.77 (s, 2 H) 3.70 (t, J = 5.80 Hz, 2 H) 2.38-2.48 (m, 2 H) | (ESI (+)) m/e 445 (M + H)⁺ |
| 1512 | N-{4-[1-(cyclohexylcarbonyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-$D_2$O, Temp = 90° C.) δ ppm 8.58 (s, 1 H) 8.48 (d, J = 5.19 Hz, 1 H) 7.49-7.53 (m, 2 H) 7.41 (d, J = 5.19 Hz, 1 H) 7.34 (d, J = 8.54 Hz, 2 H) 6.09 (s, 1 H) 4.81 (d, 4 H) 4.12 (s, 2 H) 3.68 (t, J = 5.95 Hz, 2 H) 2.38-2.50 (m, 2 H) 1.61-1.78 (m, 5 H) 1.20-1.45 (m, 6 H) | (ESI (+)) m/e 431 (M + H)⁺ |
| 1513 | N-[4-(1-propanoyl-1,2,3,6-tetrahydropyridin-4-yl)phenyl]-1,3-dihydro-2H-pyrrolo[3,4-c]pyridine-2-carboxamide | ¹H NMR (400 MHz, DMSO-$D_2$O, Temp = 90° C.) δ ppm 8.58 (s, 1 H) 8.48 (d, J = 5.19 Hz, 1 H) 7.51 (d, J = 8.54 Hz, 2 H) 7.41 (d, J = 4.88 Hz, 1 H) 7.32-7.37 (m, 2 H) 6.05-6.11 (m, 1 H) 4.81 (d, J = 7.02 Hz, 4 H) 4.11 (d, J = 3.05 Hz, 2 H) 3.66 (t, J = 5.80 Hz, 2 H) 2.45-2.50 (m, 2 H) 2.33-2.41 (m, 2 H) 1.05 (t, J = 7.32 Hz, 3 H) | (ESI (+)) m/e 377 (M + H)⁺ |
| 1514 | N-{4-[1-(2,2-dimethylbutanoyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-$D_2$O, Temp = 90° C.) δ ppm 8.58 (s, 1 H) 8.48 (d, J = 4.88 Hz, 1 H) 7.48-7.54 (m, 2 H) 7.41 (d, J = 4.88 Hz, 1 H) 7.31-7.37 (m, 2 H) 6.07-6.13 (m, 1 H) 4.81 (d, J = 7.02 Hz, 4 H) 4.14-4.18 (m, 2 H) 3.75 (t, J = 5.65 Hz, 2 H) 2.45-2.50 (m, J = 1.83 Hz, 2 H) 1.64 (q, J = 7.43 Hz, 2 H) 1.18-1.23 (m, 6 H) 0.81 (t, J = 7.48 Hz, 3 H) | (ESI (+)) m/e 419 (M + H)⁺ |
| 1515 | N-(4-{1-[(1-methyl-1H-pyrrol-2-yl)carbonyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-$D_2$O, Temp = 90° C.) δ ppm 8.58 (s, 1 H) 8.48 (d, J = 5.19 Hz, 1 H) 7.52 (d, J = 8.85 Hz, 2 H) 7.41 (d, J = 4.88 Hz, 1 H) 7.36 (d, J = 8.85 Hz, 2 H) 6.83-6.86 (m, 1 H) 6.37 (dd, J = 3.66, 1.53 Hz, 1 H) 6.04-6.12 (m, 2 H) 4.82 (d, J = 7.32 Hz, 4 H) 4.24-4.28 (m, 2 H) 3.82 (t, J = 5.80 Hz, 2 H) 3.67 (s, 3 H) 2.53-2.59 (m, J = 1.83 Hz, 2 H) | (ESI (+)) m/e 428 (M + H)⁺ |
| 1516 | N-{4-[1-(methoxyacetyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-$D_2$O, Temp = 90° C.) δ ppm 8.58 (s, 1 H) 8.48 (d, J = 5.19 Hz, 1 H) 7.51 (d, J = 8.54 Hz, 2 H) 7.41 (d, J = 5.19 Hz, 1 H) 7.30-7.37 (m, 2 H) 6.03-6.12 (m, 1 H) 4.81 (d, J = 7.63 Hz, 4 H) 4.00-4.17 (m, 4 H) 3.57-3.70 (m, J = 5.65, 5.65 Hz, 2 H) 3.31-3.37 (m, 3 H) 2.41-2.50 (m, 2 H) | (ESI (+)) m/e 393 (M + H)⁺ |

-continued

| Ex | Name | ¹H NMR | MS |
|---|---|---|---|
| 1517 | N-{4-[1-(2,2-dimethylpropanoyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 5.19 Hz, 1 H) 7.51 (d, J = 8.85 Hz, 2 H) 7.41 (d, J = 5.19 Hz, 1 H) 7.34 (d, J = 8.85 Hz, 2 H) 6.10 (t, J = 3.51 Hz, 1 H) 4.81 (d, J = 7.32 Hz, 4 H) 4.16 (d, J = 3.05 Hz, 2 H) 3.76 (t, J = 5.80 Hz, 2 H) 2.46-2.50 (m, J = 1.83 Hz, 2 H) 1.25 (s, 9 H) | (ESI (+)) m/e 405 (M + H)⁺ |
| 1518 | N-{4-[1-(4-methylhexanoyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 5.19 Hz, 1 H) 7.51 (d, J = 8.54 Hz, 2 H) 7.41 (d, J = 4.88 Hz, 1 H) 7.34 (d, J = 8.54 Hz, 2 H) 6.05-6.11 (m, 1 H) 4.82 (d, J = 7.93 Hz, 4 H) 4.08-4.16 (m, J = 1.53 Hz, 2 H) 3.67 (t, J = 5.80 Hz, 2 H) 2.43-2.50 (m, 2 H) 2.30-2.40 (m, 2 H) 1.50-1.68 (m, 1 H) 1.27-1.45 (m, 3 H) 1.10-1.22 (m, 1 H) 0.80-0.91 (m, 6 H) | (ESI (+)) m/e 433 (M + H)⁺ |
| 1519 | N-(4-{1-[(2,2-dimethylcyclopropyl)carbonyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 4.88 Hz, 1 H) 7.47-7.53 (m, 2 H) 7.41 (d, J = 4.88 Hz, 1 H) 7.32-7.37 (m, 2 H) 6.08-6.14 (m, 1 H) 4.81 (d, 4 H) 4.18 (s, 2 H) 3.85-3.94 (m, 1 H) 3.60 (s, 1 H) 2.39-2.50 (m, 2 H) 1.73 (t, J = 7.32 Hz, 1 H) 1.18-1.23 (m, 3 H) 0.96-1.01 (m, 1 H) 0.96 (s, 3 H) 0.68 (dd, J = 7.93, 3.97 Hz, 1 H) | (ESI (+)) m/e 417 (M + H)⁺ |
| 1520 | N-(4-{1-[(1,3-dimethyl-1H-pyrazol-5-yl)carbonyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 5.19 Hz, 1 H) 7.49-7.56 (m, 2 H) 7.41 (d, J = 5.19 Hz, 1 H) 7.33-7.38 (m, 2 H) 6.25 (s, 1 H) 6.07-6.12 (m, 1 H) 4.81 (d, J = 7.02 Hz, 4 H) 4.18-4.24 (m, J = 2.75 Hz, 2 H) 3.72-3.79 (m, 5 H) 2.53-2.60 (m, 2 H) 2.18 (s, 3 H) | (ESI (+)) m/e 443 (M + H)⁺ |
| 1521 | N-{4-[1-(cyclobutylacetyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 5.19 Hz, 1 H) 7.51 (d, J = 8.85 Hz, 2 H) 7.41 (d, J = 4.88 Hz, 1 H) 7.34 (d, J = 8.85 Hz, 2 H) 6.08 (t, J = 3.51 Hz, 1 H) 4.81 (d, J = 7.63 Hz, 4 H) 4.10 (s, 2 H) 3.62-3.69 (m, 2 H) 2.55-2.72 (m, 2 H) 2.45-2.50 (m, 2 H) 2.30-2.42 (m, 1 H) 2.01-2.13 (m, 2 H) 1.77-1.88 (m, 2 H) 1.61-1.74 (m, 2 H) | (ESI (+)) m/e 417 (M + H)⁺ |
| 1522 | N-{4-[1-(piperidin-1-ylacetyl)-1,2,3,6-tetrahydropyridin-4-yl]phenyl}-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 4.88 Hz, 1 H) 7.48-7.55 (m, 2 H) 7.41 (d, J = 4.58 Hz, 1 H) 7.31-7.36 (m, 2 H) 6.08 (t, J = 3.36 Hz, 1 H) 4.81 (d, 4 H) 4.14 (s, 2 H) 3.66-3.78 (m, 2 H) 3.16 (s, 2 H) 2.46-2.51 (m, 2 H) 2.36-2.43 (m, 4 H) 1.45-1.59 (m, 4 H) 1.32-1.43 (m, 2 H) | (ESI (+)) m/e 446 (M + H)⁺ |
| 1523 | N-(4-{1-[2-(pyrrolidin-1-yl)propanoyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 4.88 Hz, 1 H) 7.48-7.53 (m, 2 H) 7.41 (d, J = 4.88 Hz, 1 H) 7.31-7.36 (m, 2 H) 6.09 (t, J = 3.51 Hz, 1 H) 4.81 (d, J = 7.02 Hz, 4 H) 4.21 (s, 2 H) 3.69-3.88 (m, 2 H) 3.61-3.70 (m, 1 H) 2.53-2.66 (m, 4 H) 2.43-2.50 (m, 2 H) 1.63-1.73 (m, 4 H) 1.19 (d, J = 6.71 Hz, 3 H) | (ESI (+)) m/e 446 (M + H)⁺ |
| 1524 | N-(4-{1-[(1,3-dimethyl-1H-pyrazol-4-yl)carbonyl]-1,2,3,6-tetrahydropyridin-4-yl}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 4.88 Hz, 1 H) 7.78 (s, 1 H) 7.52 (d, J = 8.54 Hz, 2 H) 7.41 (d, J = 4.88 Hz, 1 H) 7.35 (d, J = 8.85 Hz, 2 H) 6.07-6.11 (m, 1 H) 4.81 (d, J = 7.32 Hz, 4 H) 4.19 (d, J = 3.05 Hz, 2 H) 3.77-3.79 (m, 3 H) 3.72-3.77 (m, 2 H) 2.52-2.57 (m, 2 H) 2.16-2.22 (m, 3 H) | (ESI (+)) m/e 443 (M + H)⁺ |

Example 547

N-[4-(1-oxo-2,3-dihydro-1H-isoindol-4-yl)phenyl]-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-amino-phenyl)-2,3-dihydro-isoindol-1-one. ESI-MS [M+H+]=370.1.

Example 548

N-[4-(4-oxo-3,4-dihydrophthalazin-1-yl)phenyl]-1,3-dihydro-2H-pyrrolo[3,4-c]pyridine-2-carboxamide The title compound was prepared as described in Example 377C, substituting isoindoline with 2,3-dihydro-1H-pyrrolo[3,4-c]pyridine. ESI-MS [M+H+]=384.1.

Example 549

N-[4-(4-oxo-3,4-dihydrophthalazin-1-yl)phenyl]-5,7-dihydro-6H-pyrrolo[3,4-b]pyridine-6-carboxamide The title compound was prepared as described in Example 377C, substituting isoindoline with 6,7-dihydro-5H-pyrrolo[3,4-b]pyridine. ESI-MS [M+H+]=384.1.

Example 550

N-[4-(1-oxo-1,2-dihydroisoquinolin-4-yl)cyclohex-3-en-1-yl]-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-amino-cyclohex-1-enyl)-2H-isoquinolin-1-one. ESI-MS [M+H+]=386.2.

Example 551

N-[4-(4-oxo-3,4-dihydrophthalazin-1-yl)cyclohex-3-en-1-yl]-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-amino-cyclohex-1-enyl)-2H-phthalazin-1-one. ESI-MS [M+H+]=387.2.

Example 552

N-[4-(4-oxo-3,4-dihydrophthalazin-1-yl)cyclohex-3-en-1-yl]-5-(pyrrolidin-1-ylmethyl)-1,3-dihydro-2H-isoindole-2-carboxamide The title compound was prepared as described in Example 377C, substituting 4-(4-aminophenyl)-5,6,7,8-tetrahydro-2H-phthalazin-1-one with 4-(4-amino-cyclohex-1-enyl)-2H-phthalazin-1-one and isoindoline with 5-pyrrolidin-1-ylmethyl-2,3-dihydro-1H-isoindole. ESI-MS [M+H+]=470.2.

Example 557

N-[1-(3-methylbutyl)-1H-pyrazol-4-yl]-1,3-dihydro-2H-isoindole-2-carboxamide

The title compound was prepared as described in Example 272B, substituting 1-isopentyl-1H-pyrazol-4-amine dihydrochloride for 4-amino-N-propylbenzamide and isoindoline for methyl isoindoline-5-carboxylate hydrochloride in Example 272B. $^1$H NMR (300 MHz, DMSO-d$_6$) δ ppm 8.39 (s, 1H), 7.74 (s, 1H), 7.39 (s, 1H), 7.38-7.26 (m, 4H), 4.69 (s, 4H), 4.04 (t, J=7.1 Hz, 2H), 1.81-1.57 (m, 2H), 1.52-1.37 (m, 1H), 0.89 (d, J=6.6 Hz, 6H); MS (ESI(+)) m/e 299 (M+H)$^+$.

Example 558

N-[1-(2-phenylethyl)-1H-pyrazol-4-yl]-1,3-dihydro-2H-isoindole-2-carboxamide

The title compound was prepared as described in Example 272B, substituting 1-phenethyl-1H-pyrazol-4-amine dihydrochloride for 4-amino-N-propylbenzamide and isoindoline for methyl isoindoline-5-carboxylate hydrochloride in Example 272B. $^1$H NMR (300 MHz, DMSO-d$_6$) δ ppm 8.39 (s, 1H), 7.68 (s, 1H), 7.42 (s, 1H), 7.39-7.23 (m, 6H), 7.24-7.15 (m, 3H), 4.68 (bs, 4H), 4.27 (t, J=7.3 Hz, 2H), 3.07 (t, J=7.3 Hz, 2H); MS (ESI(+)) m/e 333 (M+H)$^+$.

Example 559

N$^5$-[2-(dimethylamino)ethyl]-N$^2$-[4-(propylcarbamoyl)phenyl]-1,3-dihydro-2H-isoindole-2,5-dicarboxamide The title compound was prepared as described in Example 1C, substituting N1,N1-dimethylethane-1,2-diamine for 3-phenylpropan-1-amine and 2-{[4-(propylcarbamoyl)phenyl]carbamoyl}isoindoline-5-carboxylic acid for 4-(isoindoline-2-carboxamido)benzoic acid. $^1$H NMR (300 MHz, DMSO-d$_6$) δ ppm 9.28 (s, 1H), 8.70 (t, J=5.6 Hz, 1H), 8.62 (s, 1H), 8.26 (t, J=5.6 Hz, 1H), 7.86-7.74 (m, 4H), 7.68-7.61 (m, 2H), 7.49 (d, J=7.8 Hz, 1H), 4.84 (bs, 4H), 3.66-3.55 (m, 2H), 3.29-3.12 (m, 4H), 2.90-2.80 (m, 6H), 2.28-1.46 (m, 2H), 0.89 (t, J=7.4 Hz, 3H); MS (ESI(+)) m/e 438 (M+H)$^+$.

Example 560

5-(morpholin-4-ylcarbonyl)-N-[4-(propylcarbamoyl)phenyl]-1,3-dihydro-2H-isoindole-2-carboxamide The title compound was prepared as described in Example 1C, substituting morpholine for 3-phenylpropan-1-amine and 2-{[4-(propylcarbamoyl)phenyl]carbamoyl}isoindoline-5-carboxylic acid for 4-(isoindoline-2-carboxamido)benzoic acid. $^1$H NMR (300 MHz, DMSO-d$_6$) δ ppm 8.61 (s, 1H), 8.26 (t, J=5.7 Hz, 1H), 7.80-7.73 (m, 2H), 7.69-7.62 (m, 2H), 7.47-7.41 (m, 2H), 7.35 (dd, J=7.7, 1.6 Hz, 1H), 4.82 (bs, 4H), 3.73-3.43 (m, 6H), 3.28-3.12 (m, 4H), 1.60-1.44 (m, 2H), 0.89 (t, J=7.4 Hz, 3H); MS (ESI(+)) m/e 437 (M+H)$^+$.

Example 561

N-(4-{benzyl[3-(morpholin-4-yl)propyl]carbamoyl}phenyl)-1,3-dihydro-2H-isoindole-2-carboxamide The title compound was prepared as described in Example 1C, substituting N-benzyl-3-morpholinopropan-1-amine for 3-phenylpropan-1-amine $^1$H NMR (400 MHz, DMSO-d$_6$, Temp=90° C.) δ ppm 8.28 (s, 1H), 7.65-7.59 (m, 2H), 7.39-7.25 (m, 11H), 4.79 (bs, 4H), 4.63 (s, 2H), 3.52-3.45 (m, 4H), 3.35-3.27 (m, 2H), 2.27-2.20 (m, 4H), 2.17 (t, 2H), 1.69-1.60 (m, 2H); MS (ESI(+)) m/e 499 (M+H)$^+$.

Example 563

5-bromo-N-{4-[(cyclopentylacetyl)amino]phenyl}-1,3-dihydro-2H-isoindole-2-carboxamide

Example 563A 2-cyclopentyl-N-(4-nitrophenyl)acetamide

The title compound was prepared as described in Example 278, substituting 2-cyclopentylacetyl chloride for acetyl chloride and 4-nitroaniline for 5-amino-N-(4-(propylcarbamoyl)phenyl)isoindoline-2-carboxamide.

Example 563B

N-(4-aminophenyl)-2-cyclopentylacetamide

The title compound was prepared as described in Example 274, substituting 2-cyclopentyl-N-(4-nitrophenyl)acetamide for 5-nitro-N-[4-(propylcarbamoyl)phenyl]-1,3-dihydro-2H-isoindole-2-carboxamide.

Example 563C 5-bromo-N-{4-[(cyclopentylacetyl)amino]phenyl}-1,3-dihydro-2H-isoindole-2-carboxamide The title compound was prepared as described in Example 272B, substituting N-(4-aminophenyl)-2-cyclopentylacetamide for 4-amino-N-propylbenzamide and 5-bromoisoindoline for methyl isoindoline-5-carboxylate hydrochloride. $^1$H NMR (300 MHz, DMSO-d$_6$) δ ppm 9.68 (s, 1H), 8.29 (s, 1H), 7.65-7.55 (m, 1H), 7.53-7.36 (m, 5H), 7.36-7.26 (m, 1H), 4.79-4.65 (m, 4H), 2.33-2.16 (m, 3H), 1.85-1.68 (m, 2H), 1.68-1.41 (m, 4H), 1.29-1.09 (m, 2H); MS (ESI(+)) m/e 442 (M+H)$^+$.

Example 565 methyl 4-{[(5-cyano-1,3-dihydro-2H-isoindol-2-yl)carbonyl]amino}benzoate

The title compound was prepared as described in Example 1A, substituting 5-cyanoisoindoline for isoindoline. $^1$H NMR (300 MHz, DMSO-d$_6$) δ ppm 8.81 (s, 1H), 7.91-7.82 (m, 3H), 7.82-7.77 (m, 1H), 7.76-7.69 (m, 2H), 7.59 (d, J=7.9 Hz, 1H), 4.89-4.81 (m, 4H), 3.81 (s, 3H); MS (ESI(+)) m/e 322 (M+H)$^+$.

Example 566

N-(4-{(E)-[(benzyloxy)imino]methyl}phenyl)-1,3-dihydro-2H-isoindole-2-carboxamide

Example 566A

N-(4-formylphenyl)isoindoline-2-carboxamide

The title compound was prepared as described in Example 272B, substituting 4-aminobenzaldehyde for 4-amino-N-propylbenzamide and isoindoline for methyl isoindoline-5-carboxylate hydrochloride.

Example 566B

N-(4-{(E)-[(benzyloxy)imino]methyl}phenyl)-1,3-dihydro-2H-isoindole-2-carboxamide In a 8 mL sealed vial was mixed N-(4-formylphenyl)isoindoline-2-carboxamide (50 mg, 0.188 mmol) in methanol (1 ml). A solution of O-benzylhydroxylamine hydrochloride (45.0 mg, 0.282 mmol) and sodium acetate (46.0 mg, 0.338 mmol) in water (1.000 ml) was then added and the reaction was stirred overnight at room temperature. The reaction was diluted with water and the product was extracted with dichloromethane. The organic layer was washed with brine, dried with sodium sulfate, decanted, and concentrated. Purification by chromatography provided the title compound. $^1$H NMR (400 MHz, DMSO-d$_6$) δ ppm 8.55 (s, 1H), 8.21 (s, 1H), 7.65 (m, 2H), 7.50 (m, 2H), 7.44-7.28 (m, 9H), 5.14 (s, 2H), 4.78 (bs, 4H); MS (ESI(+)) m/e 372 (M+H)$^+$.

Example 573

N-[4-(3-aminopyrrolidin-1-yl)phenyl]-1,3-dihydro-2H-isoindole-2-carboxamide

The title compound was prepared as described in Example 339D. $^1$H NMR (400 MHz, DMSO-d$_6$, Temp=90° C.) δ ppm 7.76 (bs, 1H), 7.36-7.31 (m, 2H), 7.31-7.25 (m, 4H), 6.46-6.42 (m, 2H), 4.73 (bs, 4H), 3.56 (p, J=5.8 Hz, 1H), 3.41-3.36 (m, 1H), 3.35-3.28 (m, 1H), 3.24-3.15 (m, 3H), 2.85 (dd, J=9.1, 4.9 Hz, 1H), 2.13-2.05 (m, 1H), 1.73-1.64 (m, 1H); MS (ESI(+)) m/e 323 (M+H)$^+$.

Example 574

N-{6-[(3-methylbutyl)carbamoyl]pyridin-3-yl}-1,3-dihydro-2H-isoindole-2-carboxamide

Example 574A methyl 5-(isoindoline-2-carboxamido)picolinate

The title compound was prepared as described in Example 272B, substituting methyl 5-aminopicolinate for 4-amino-N-propylbenzamide and isoindoline for methyl isoindoline-5-carboxylate hydrochloride.

Example 574B 5-(isoindoline-2-carboxamido)picolinic acid

The title compound was prepared as described in Example 1B, substituting methyl 5-(isoindoline-2-carboxamido)picolinate for methyl 4-(isoindoline-2-carboxamido)benzoate.

Example 574C

N-{6-[(3-methylbutyl)carbamoyl]pyridin-3-yl}-1,3-dihydro-2H-isoindole-2-carboxamide The title compound was prepared as described in Example 1C, substituting 3-methylbutan-1-amine for 3-phenylpropan-1-amine and 5-(isoindoline-2-carboxamido)picolinic acid for 4-(isoindoline-2-carboxamido)benzoic acid. $^1$H NMR (400 MHz, DMSO-d$_6$) δ ppm 8.85 (m, 2H), 8.57 (t, J=6.1 Hz, 1H), 8.17 (dd, J=8.5, 2.4 Hz, 1H), 7.94 (d, J=8.5 Hz, 1H), 7.41-7.29

(m, 4H), 4.79 (m, 4H), 3.35 (m, 2H), 1.59 (m, 1H), 1.42 (q, J=7.1 Hz, 2H), 0.90 (d, J=6.6 Hz, 6H); MS (ESI(+)) m/e 353 (M+H)$^+$.

Example 575

N-{6-[(3-phenylpropyl)carbamoyl]pyridin-3-yl}-1,3-dihydro-2H-isoindole-2-carboxamide The title compound was prepared as described in Example 1C, substituting 5-(isoindoline-2-carboxamido)picolinic acid for 4-(isoindoline-2-carboxamido)benzoic acid. $^1$H NMR (400 MHz, DMSO-d$_6$) δ ppm 8.86 (m, 2H), 8.68 (t, J=6.0 Hz, 1H), 8.18 (dd, J=8.6, 2.5 Hz, 1H), 7.95 (d, J=8.5 Hz, 1H), 7.41-7.14 (m, 9H), 4.81 (bs, 4H), 3.35 (m, 2H), 2.61 (t, J=7.6 Hz, 2H), 1.84 (m, 2H); MS (ESI(+)) m/e 401 (M+H)$^+$.

Example 576

N-{6-[(tetrahydrofuran-3-ylmethyl)carbamoyl]pyridin-3-yl}-1,3-dihydro-2H-isoindole-2-carboxamide The title compound was prepared as described in Example 1C, substituting (tetrahydrofuran-3-yl)methanamine for 3-phenylpropan-1-amine and 5-(isoindoline-2-carboxamido) picolinic acid for 4-(isoindoline-2-carboxamido)benzoic acid. $^1$H NMR (400 MHz, DMSO-d$_6$) δ ppm 8.87 (m, 2H), 8.78 (t, J=6.1 Hz, 1H), 8.18 (dd, J=8.5, 2.5 Hz, 1H), 7.95 (d, J=8.5 Hz, 1H), 7.42-7.26 (m, 4H), 4.81 (m, 4H), 3.75 (m, 1H), 3.70-3.56 (m, 2H), 3.47 (dd, J=8.5, 5.3 Hz, 1H), 3.27 (m, 2H), 2.53 (m, 1H), 1.91 (m, 1H), 1.61 (m, 1H); MS (ESI(+)) m/e 368 (M+H)$^+$.

Example 577

N$^2$-{4-[(cyclopentylacetyl)amino]phenyl}-1,3-dihydro-2H-isoindole-2,5-dicarboxamide The title compound was prepared as described in Example 132 substituting 5-cyano-N-{4-[(cyclopentylacetyl)amino]phenyl}-1,3-dihydro-2H-isoindole-2-carboxamide for 5-cyano-N-(4-(propylcarbamoyl)phenyl)isoindoline-2-carboxamide. $^1$H NMR (300 MHz, DMSO-d$_6$) δ ppm 9.69 (s, 1H), 8.31 (s, 1H), 7.98 (s, 1H), 7.87-7.78 (m, 2H), 7.53-7.38 (m, 5H), 7.36 (brs, 1H), 4.78 (bs, 4H), 2.32-2.13 (m, 3H), 1.82-1.67 (m, 2H), 1.67-1.42 (m, 4H), 1.27-1.10 (m, 2H); MS (ESI(+)) m/e 407 (M+H)$^+$.

Example 578

N-[4-({benzyl[3-(morpholin-4-yl)propyl]amino}methyl)phenyl]-1,3-dihydro-2H-isoindole-2-carboxamide To a stirring suspension of N-(4-{benzyl[3-(morpholin-4-yl)propyl]carbamoyl}phenyl)-1,3-dihydro-2H-isoindole-2-carboxamide (0.028 g, 0.056 mmol) in THF (1.1 ml) was added 1M borane tetrahydrofuran complex (0.225 ml, 0.225 mmol) dropwise. The mixture was heated at 60° C. for 5 hours. Additional borane complex (0.084 mL) was added and reaction was heated at 60° C. for 1 hour. The reaction was cooled to ambient temperature and 0.3 mL of 1.25 M HCl in methanol was added. The quenched reaction was stirred 30 min and concentrated. The title compound was isolated after flash chromatography. $^1$H NMR (400 MHz, pyridine-d$_5$, Temp=90° C.) δ ppm 8.05 (s, 1H), 7.88-7.82 (m, 2H), 7.47-7.38 (m, 4H), 7.36-7.29 (m, 2H), 7.26-7.15 (m, 5H), 4.85 (bs, 4H), 3.68-3.59 (m, 8H), 3.48-3.35 (m, 1H), 2.59 (t, J=7.0 Hz, 2H), 2.38-2.29 (m, 6H), 1.79-1.65 (m, 3H); MS (ESI(+)) m/e 485 (M+H)$^+$.

Example 579

N-{4-[(cyclopentylacetyl)amino]phenyl}-5-(1H-pyrazol-3-yl)-1,3-dihydro-2H-isoindole-2-carboxamide The title compound was prepared as described in Example 280, substituting 5-bromo-N-(4-(2-cyclopentylacetamido)phenyl)isoindoline-2-carboxamide for 5-bromo-N-(4-(propylcarbamoyl)phenyl)isoindoline-2-carboxamide. $^1$H NMR (300 MHz, DMSO-d$_6$) δ ppm 13.30 (bs, 0.25H), 12.87 (bs, 0.75H), 9.69 (s, 1H), 8.34-8.23 (m, 1H), 7.83-7.63 (m, 3H), 7.56-7.32 (m, 5H), 6.76-6.68 (m, 1H), 4.81-4.72 (m, 4H), 2.31-2.12 (m, 3H), 1.85-1.67 (m, 2H), 1.67-1.42 (m, 4H), 1.29-1.10 (m, 2H); MS (ESI(+)) m/e 430 (M+H)$^+$.

Example 580

N-{4-[(cyclopentylacetyl)amino]phenyl}-5-(pyridin-3-yl)-1,3-dihydro-2H-isoindole-2-carboxamide The title compound was prepared as described in Example 280, substituting pyridin-3-ylboronic acid for 1H-pyrazol-3-ylboronic acid and 5-bromo-N-(4-(2-cyclopentylacetamido)phenyl)isoindoline-2-carboxamide for 5-bromo-N-(4-(propylcarbamoyl)phenyl)isoindoline-2-carboxamide. $^1$H NMR (300 MHz, DMSO-d$_6$) δ ppm 9.70 (bs, 1H), 8.93-8.89 (m, 1H), 8.58 (dd, J=4.7, 1.6 Hz, 1H), 8.33 (s, 1H), 8.13-8.05 (m, 1H), 7.72 (bs, 1H), 7.71-7.64 (m, 1H), 7.54-7.44 (m, 6H), 4.81 (bs, 4H), 2.31-2.18 (m, 3H), 1.82-1.68 (m, 2H), 1.68-1.43 (m, 4H), 1.26-1.11 (m, 2H); MS (ESI(+)) m/e 441 (M+H)$^+$.

Example 581

N-{4-[(cyclopentylacetyl)amino]phenyl}-5-(1-methyl-1H-pyrazol-4-yl)-1,3-dihydro-2H-isoindole-2-carboxamide The title compound was prepared as described in Example 280, substituting 1-methyl-4-(4,4,5,5-tetramethyl-1,3,2-dioxaborolan-2-yl)-1H-pyrazole for 1H-pyrazol-3-ylboronic acid and 5-bromo-N-(4-(2-cyclopentylacetamido)phenyl)isoindoline-2-carboxamide for 5-bromo-N-(4-(propylcarbamoyl)phenyl)isoindoline-2-carboxamide. $^1$H NMR (300 MHz, DMSO-d$_6$) δ ppm 9.69 (s, 1H), 8.27 (s, 1H), 8.14 (s, 1H), 7.88-7.85 (m, 1H), 7.55-7.40 (m, 6H), 7.36-7.30 (m, 1H), 4.77-4.69 (m, 4H), 3.86 (s, 3H), 2.31-2.16 (m, 3H), 1.81-1.68 (m, 2H), 1.68-1.42 (m, 4H), 1.28-1.12 (m, 2H); MS (ESI(+)) m/e 444 (M+H)$^+$.

Example 582

N$^2$-{4-[(cyclopentylacetyl)amino]phenyl}-N$^5$-(2-methoxyethyl)-1,3-dihydro-2H-isoindole-2,5-dicarboxamide The title compound was prepared as described in Example 1C, substituting 2-methoxyethanamine for 3-phenylpropan-1-amine and 2-({4-[(cyclopentylacetyl)amino]phenyl}carbamoyl)isoindoline-5-carboxylic acid for 4-(isoindoline-2-carboxamido)benzoic acid. $^1$H NMR (300 MHz, DMSO-d$_6$) δ ppm 9.69 (s, 1H), 8.56-8.49 (m, 1H), 8.31

(s, 1H), 7.84-7.77 (m, 2H), 7.50-7.40 (m, 5H), 4.78 (bs, 4H), 3.50-3.39 (m, 4H), 3.27 (s, 3H), 2.31-2.18 (m, 3H), 1.81-1.68 (m, 2H), 1.66-1.43 (m, 4H), 1.26-1.12 (m, 2H); MS (ESI(+)) m/e 465 (M+H)$^+$.

Example 583

N$^2$-{4-[(cyclopentylacetyl)amino]phenyl}-N$^5$-(2-hydroxyethyl)-1,3-dihydro-2H-isoindole-2,5-dicarboxamide The title compound was prepared as described in Example 1C, substituting 2-aminoethanol for 3-phenylpropan-1-amine and 2-({4-[(cyclopentylacetyl)amino]phenyl}carbamoyl)isoindoline-5-carboxylic acid for 4-(isoindoline-2-carboxamido)benzoic acid. $^1$H NMR (300 MHz, DMSO-d$_6$) δ ppm 9.70 (s, 1H), 8.51-8.40 (m, 1H), 8.31 (s, 1H), 7.86-7.75 (m, 2H), 7.51-7.36 (m, 5H), 4.78 (bs, 4H), 4.71 (t, J=5.6 Hz, 1H), 3.58-3.46 (m, 2H), 3.39-3.28 (m, 2H), 2.32-2.13 (m, 3H), 1.82-1.68 (m, 2H), 1.67-1.44 (m, 4H), 1.27-1.10 (m, 2H); MS (ESI(+)) m/e 451 (M+H)$^+$.

Example 584

5-(aminomethyl)-N-{4-[(cyclopentylacetyl)amino]phenyl}-1,3-dihydro-2H-isoindole-2-carboxamide The title compound was prepared as described in Example 276, substituting 5-cyano-N-{4-[(cyclopentylacetyl)amino]phenyl}-1,3-dihydro-2H-isoindole-2-carboxamide for 5-cyano-N-(4-(propylcarbamoyl)phenyl)isoindoline-2-carboxamide. $^1$H NMR (300 MHz, DMSO-d$_6$) δ ppm 9.35 (bs, 1H), 7.99 (bs, 1H), 7.44-7.41 (m, 4H), 7.31-7.20 (m, 3H), 4.72 (bs, 4H), 3.81-3.68 (m, 2H), 2.29-2.25 (m, 3H), 1.80-1.68 (m, 2H), 1.66-1.48 (m, 6H), 1.29-1.14 (m, 2H); MS (ESI(+)) m/e 393 (M+H)$^+$.

Example 605

N-[6-(benzoylamino)hexyl]-1,3-dihydro-2H-isoindole-2-carboxamide

Example 605A tert-butyl 6-(isoindoline-2-carboxamido)hexylcarbamate

The title compound was prepared as described in Example 344A, substituting tert-butyl 6-aminohexylcarbamate for tert-butyl 5-aminoisoindoline-2-carboxylate.

Example 605B

N-(6-aminohexyl)isoindoline-2-carboxamide

The title compound was prepared as described in Example 2D, substituting Boc-tert-butyl 6-(isoindoline-2-carboxamido)hexylcarbamate for tert-butyl 4-((4-(5-fluoroisoindoline-2-carboxamido)benzamido)methyl)benzylcarbamate.

Example 605C

N-[6-(benzoylamino)hexyl]-1,3-dihydro-2H-isoindole-2-carboxamide

The title compound was prepared as described in Example 1C, substituting N-(6-aminohexyl)isoindoline-2-carboxamide for 3-phenylpropan-1-amine and benzoic acid for 4-(isoindoline-2-carboxamido)benzoic acid. $^1$H NMR (300 MHz, DMSO-d$_6$) δ ppm 8.42 (t, J=5.35 Hz, 1H) 7.76-7.90 (m, 2H) 7.36-7.58 (m, 3H) 7.20-7.36 (m, 4H) 6.28 (t, J=5.55 Hz, 1H) 4.57 (s, 4H) 3.21-3.30 (m, 2H) 3.07 (q, J=6.74 Hz, 2H) 1.24-1.66 (m, 8H); (ESI(+)) m/e 366 (M+H)$^+$.
Table 10.

The following Examples were prepared as described in Example 1C, substituting N-(6-aminohexyl)isoindoline-2-carboxamide for 3-phenylpropan-1-amine and the appropriate carboxylic acid for 4-(isoindoline-2-carboxamido)benzoic acid.

| Ex | Name | $^1$H NMR | MS |
|---|---|---|---|
| 606 | N-{6-[(pyridin-3-ylcarbonyl)amino]hexyl}-1,3-dihydro-2H-isoindole-2-carboxamide | $^1$H NMR (300 MHz, DMSO-d$_6$) δ ppm 8.98 (d, J = 1.36 Hz, 1 H) 8.68 (dd, J = 4.75, 1.70 Hz, 1 H) 8.62 (t, J = 5.43 Hz, 1 H) 8.12-8.21 (m, 1 H) 7.48 (dd, J = 8.31, 5.26 Hz, 1 H) 7.20-7.36 (m, 4 H) 6.27 (t, J = 5.43 Hz, 1 H) 4.57 (s, 4 H) 3.23-3.29 (m, 2 H) 2.99-3.13 (m, 2 H) 1.25-1.60 (m, 9 H) | (ESI (+)) m/e 367 (M + H)$^+$ |
| 619 | N-(6-acetamidohexyl)-1,3-dihydro-2H-isoindole-2-carboxamide | $^1$H NMR (300 MHz, DMSO-d$_6$) δ ppm 7.77 (s, 1 H) 7.22-7.38 (m, 4 H) 6.28 (t, J = 5.55 Hz, 1 H) 4.57 (s, 4 H) 2.93-3.14 (m, 4 H) 1.77 (s, 3 H) 1.31-1.61 (m, 4 H) 1.20-1.31 (m, 4 H) | (ESI (+)) m/e 304 (M + H)$^+$ |
| 655 | N-(6-{[4-(methylsulfonyl)benzoyl]amino}hexyl)-1,3-dihydro-2H-isoindole-2-carboxamide | $^1$H NMR (400 MHz, DMSO-d$_6$/Deuterium Oxide, Temp = 90° C.) δ ppm 1.33-1.40 (m, 4 H), 1.45-1.63 (m, 4 H), 3.11 (t, J = 7.02 Hz, 2 H), 3.19 (s, 3 H), 3.30 (t, J = 7.02 Hz, 2 H), 4.59 (s, 4 H), 7.24-7.33 (m, 4 H), 7.95-8.04 (m, 4 H) | (ESI (+)) m/e 444 (M + H)$^+$ |
| 656 | N-{6-[(ethoxyacetyl)amino]hexyl}-1,3-dihydro-2H-isoindole-2-carboxamide | $^1$H NMR (400 MHz, DMSO-d$_6$/Deuterium Oxide, Temp = 90° C.) δ ppm 1.15 (t, J = 7.02 Hz, 3 H), 1.25-1.36 (m, 4 H), 1.42-1.51 (m, 4 H), 3.11 (q, J = 7.43 Hz, 4 H), 3.50 (q, J = 7.02 Hz, 2 H), 3.80 (s, 2 H), 4.59 (s, 4 H), 7.24-7.33 (m, 4 H) | (ESI (+)) m/e 348 (M + H)$^+$ |
| 657 | N-{6-[(cyclopentylcarbonyl)amino]hexyl}-1,3-dihydro-2H-isoindole-2-carboxamide | $^1$H NMR (400 MHz, DMSO-d$_6$/Deuterium Oxide, Temp = 90° C.) δ ppm 1.25-1.35 (m, 5 H), 1.38-1.55 (m, 6 H), 1.56-1.67 (m, 4 H), 1.68-1.81 (m, 2 H), 3.00-3.13 (m, 4 H), 4.59 (s, 4 H), 7.20-7.37 (m, 4 H) | (ESI (+)) m/e 358 (M + H)$^+$ |

-continued

| Ex | Name | $^1$H NMR | MS |
|---|---|---|---|
| 658 | N-{6-[(2-hydroxybenzoyl)amino]hexyl}-1,3-dihydro-2H-isoindole-2-carboxamide | $^1$H NMR (400 MHz, DMSO-d$_6$/Deuterium Oxide, Temp = 90° C.) δ ppm 1.32-1.42 (m, 4 H), 1.45-1.53 (m, 2 H), 1.53-1.63 (m, 2 H), 3.11 (t, 2 H), 3.31 (t, J = 7.02 Hz, 2 H), 4.58 (s, 4 H), 6.83-6.90 (m, 2 H), 7.23-7.32 (m, 4 H), 7.34-7.40 (m, 1 H), 7.78 (dd, J = 7.78, 1.68 Hz, 1 H) | (ESI (+)) m/e 382 (M + H)$^+$ |
| 659 | N-{6-[(3-hydroxybenzoyl)amino]hexyl}-1,3-dihydro-2H-isoindole-2-carboxamide | $^1$H NMR (400 MHz, DMSO-d$_6$/Deuterium Oxide, Temp = 90° C.) δ ppm 1.28-1.41 (m, 4 H), 1.42-1.61 (m, 4 H), 3.08-3.15 (m, 2 H), 3.22-3.25 (m, 2 H), 4.59 (s, 4 H), 6.86-6.93 (m, 1 H), 7.17-7.34 (m, 7 H) | (ESI (+)) m/e 382 (M + H)$^+$ |
| 660 | N-{6-[(4-hydroxybenzoyl)amino]hexyl}-1,3-dihydro-2H-isoindole-2-carboxamide | $^1$H NMR (400 MHz, DMSO-d$_6$/Deuterium Oxide, Temp = 90° C.) δ ppm 1.30-1.38 (m, 4 H), 1.44-1.60 (m, 4 H), 3.09-3.13 (m, 2 H), 3.20-3.25 (m, 2 H), 4.59 (s, 4 H), 6.75-6.83 (m, 2 H), 7.23-7.32 (m, 4 H), 7.65-7.71 (m, 2 H) | (ESI (+)) m/e 382 (M + H)$^+$ |
| 661 | N-{6-[(2-methoxybenzoyl)amino]hexyl}-1,3-dihydro-2H-isoindole-2-carboxamide | $^1$H NMR (400 MHz, DMSO-d$_6$/Deuterium Oxide, Temp = 90° C.) δ ppm 1.29-1.43 (m, 4 H), 1.45-1.61 (m, 4 H), 3.08-3.15 (m, 2 H), 3.30 (t, J = 7.02 Hz, 2 H), 3.89 (s, 3 H), 4.58 (s, 4 H), 6.99-7.04 (m, 1 H), 7.10 (d, J = 8.24 Hz, 1 H), 7.24-7.32 (m, 4 H), 7.41-7.47 (m, 1 H), 7.74 (dd, J = 7.63, 1.83 Hz, 1 H) | (ESI (+)) m/e 396 (M + H)$^+$ |
| 662 | N-{6-[(3-methoxybenzoyl)amino]hexyl}-1,3-dihydro-2H-isoindole-2-carboxamide | $^1$H NMR (400 MHz, DMSO-d$_6$/Deuterium Oxide, Temp = 90° C.) δ ppm 1.30-1.41 (m, 4 H), 1.44-1.62 (m, 4 H), 3.09-3.14 (m, 2 H), 3.26-3.31 (m, 2 H), 3.80 (s, 3 H), 4.58 (s, 4 H), 7.03-7.07 (m, 1 H), 7.24-7.41 (m, 7 H) | (ESI (+)) m/e 396 (M + H)$^+$ |
| 663 | N-{6-[(4-methoxybenzoyl)amino]hexyl}-1,3-dihydro-2H-isoindole-2-carboxamide | $^1$H NMR (400 MHz, DMSO-d$_6$/Deuterium Oxide, Temp = 90° C.) δ ppm 1.31-1.39 (m, 4 H), 1.49 (s, 4 H), 3.11 (t, J = 7.02 Hz, 2 H), 3.26-3.28 (m, 2 H), 3.80 (s, 3 H), 4.58 (s, 4 H), 6.92-6.97 (m, 2 H), 7.24-7.32 (m, 4 H), 7.75-7.80 (m, 2 H) | (ESI (+)) m/e 396 (M + H)$^+$ |
| 664 | N-{6-[(2-fluorobenzoyl)amino]hexyl}-1,3-dihydro-2H-isoindole-2-carboxamide | $^1$H NMR (400 MHz, DMSO-d$_6$/Deuterium Oxide, Temp = 90° C.) δ ppm 1.27-1.42 (m, 4 H), 1.43-1.64 (m, 4 H), 3.11 (t, 2 H), 3.28 (t, J = 7.02 Hz, 2 H), 4.58 (s, 4 H), 7.17-7.33 (m, 6 H), 7.45-7.52 (m, 1 H), 7.57-7.63 (m, 1 H) | (ESI (+)) m/e 384 (M + H)$^+$ |
| 665 | N-{6-[(3-fluorobenzoyl)amino]hexyl}-1,3-dihydro-2H-isoindole-2-carboxamide | $^1$H NMR (400 MHz, DMSO-d$_6$/Deuterium Oxide, Temp = 90° C.) δ ppm 1.32-1.41 (m, 4 H), 1.44-1.61 (m, 4 H), 3.11 (t, 2 H), 3.28 (t, J = 7.02 Hz, 2 H), 4.58 (s, 4 H), 7.24-7.33 (m, 5 H), 7.44-7.51 (m, 1 H), 7.55-7.60 (m, 1 H), 7.65 (d, J = 8.24 Hz, 1 H) | (ESI (+)) m/e 384 (M + H)$^+$ |
| 666 | N-{6-[(4-fluorobenzoyl)amino]hexyl}-1,3-dihydro-2H-isoindole-2-carboxamide | $^1$H NMR (400 MHz, DMSO-d$_6$/Deuterium Oxide, Temp = 90° C.) δ ppm 1.31-1.38 (m, 4 H), 1.44-1.61 (m, 4 H), 3.11 (t, J = 7.02 Hz, 2 H), 3.26 (t, J = 7.02 Hz, 2 H), 4.58 (s, 4 H), 7.16-7.31 (m, 6 H), 7.84-7.89 (m, 2 H) | (ESI (+)) m/e 384 (M + H)$^+$ |
| 667 | N-{6-[(2-chlorobenzoyl)amino]hexyl}-1,3-dihydro-2H-isoindole-2-carboxamide | $^1$H NMR (400 MHz, DMSO-d$_6$/Deuterium Oxide, Temp = 90° C.) δ ppm 1.30-1.42 (m, 4 H), 1.45-1.63 (m, 4 H), 3.12 (t, J = 7.02 Hz, 2 H), 3.26-3.29 (m, 2 H), 4.59 (s, 4 H), 7.24-7.32 (m, 4 H), 7.33-7.45 (m, 4 H) | (ESI (+)) m/e 400 (M + H)$^+$ |
| 668 | N-{6-[(3-chlorobenzoyl)amino]hexyl}-1,3-dihydro-2H-isoindole-2-carboxamide | $^1$H NMR (400 MHz, DMSO-d$_6$/Deuterium Oxide, Temp = 90° C.) δ ppm 1.29-1.40 (m, 4 H), 1.44-1.62 (m, 4 H), 3.11 (t, 2 H), 3.27 (t, 2 H), 4.58 (s, 4 H), 7.24-7.33 (m, 4 H), 7.46 (t, J = 7.78 Hz, 1 H), 7.51-7.55 (m, 1 H), 7.75 (dd, J = 7.63, 1.53 Hz, 1 H), 7.82 (t, J = 1.68 Hz, 1 H) | (ESI (+)) m/e 400 (M + H)$^+$ |
| 669 | N-{6-[(4-chlorobenzoyl)amino]hexyl}-1,3-dihydro-2H-isoindole-2-carboxamide | $^1$H NMR (400 MHz, DMSO-d$_6$/Deuterium Oxide, Temp = 90° C.) δ ppm 1.28-1.40 (m, 4 H), 1.44-1.62 (m, 4 H), 3.11 (t, J = 7.02 Hz, 2 H), 3.27 (t, 2 H), 4.58 (s, 4 H), 7.24-7.32 (m, 4 H), 7.43-7.49 (m, 2 H), 7.78-7.85 (m, 2 H) | (ESI (+)) m/e 400 (M + H)$^+$ |
| 670 | N-{6-[(3-cyanobenzoyl)amino]hexyl}-1,3-dihydro-2H-isoindole-2-carboxamide | $^1$H NMR (400 MHz, DMSO-d$_6$/Deuterium Oxide, Temp = 90° C.) δ ppm 1.28-1.41 (m, 4 H), 1.45-1.63 (m, 4 H), 3.11 (t, 2 H), 3.29 (t, J = 7.02 Hz, 2 H), 4.58 (s, 4 H), 7.24-7.32 (m, 4 H), 7.65 (t, J = 7.78 Hz, 1 H), 7.88-7.92 (m, 1 H), 8.09-8.12 (m, 1 H), 8.18 (t, 1 H) | (ESI (+)) m/e 391 (M + H)$^+$ |
| 671 | N-{6-[(4-cyanobenzoyl)amino]hexyl}-1,3-dihydro-2H-isoindole-2-carboxamide | $^1$H NMR (400 MHz, DMSO-d$_6$/Deuterium Oxide, Temp = 90° C.) δ ppm 1.32-1.39 (m, 4 H), 1.44-1.63 (m, 4 H), 3.11 (t, 2 H), 3.29 (t, J = 7.02 Hz, 2 H), 4.58 (s, 4 H), 7.22-7.33 (m, 4 H), 7.82-7.87 (m, 2 H), 7.92-7.96 (m, 2 H) | (ESI (+)) m/e 391 (M + H)$^+$ |

| Ex | Name | ¹H NMR | MS |
|---|---|---|---|
| 672 | N-(6-{[3-(dimethylamino)benzoyl]amino}hexyl)-1,3-dihydro-2H-isoindole-2-carboxamide | ¹H NMR (400 MHz, DMSO-$d_6$/Deuterium Oxide, Temp = 90° C.) δ ppm 1.30-1.38 (m, 4 H), 1.45-1.60 (m, 4 H), 2.96 (s, 6 H), 3.11 (t, 2 H), 3.27 (t, 2 H), 4.59 (s, 4 H), 6.93-7.00 (m, 1 H), 7.17-7.21 (m, 1 H), 7.24-7.33 (m, 6 H) | (ESI (+)) m/e 409 (M + H)⁺ |
| 673 | N-(6-{[4-(dimethylamino)benzoyl]amino}hexyl)-1,3-dihydro-2H-isoindole-2-carboxamide | ¹H NMR (400 MHz, DMSO-$d_6$/Deuterium Oxide, Temp = 90° C.) δ ppm 1.31-1.37 (m, 4 H), 1.43-1.58 (m, 4 H), 2.95 (s, 6 H), 3.11 (t, 2 H), 3.24 (t, J = 7.02 Hz, 2 H), 4.59 (s, 4 H), 6.68-6.74 (m, 2 H), 7.22-7.33 (m, 4 H), 7.66-7.70 (m, 2 H) | (ESI (+)) m/e 409 (M + H)⁺ |
| 674 | N-(6-{[3-(trifluoromethyl)benzoyl]amino}hexyl)-1,3-dihydro-2H-isoindole-2-carboxamide | ¹H NMR (400 MHz, DMSO-$d_6$/Deuterium Oxide, Temp = 90° C.) δ ppm 1.32-1.41 (m, 4 H), 1.46-1.62 (m, 4 H), 3.09-3.14 (m, 2 H), 3.30 (t, J = 7.02 Hz, 2 H), 4.58 (s, 4 H), 7.24-7.33 (m, 4 H), 7.68 (t, J = 7.78 Hz, 1 H), 7.83 (d, J = 7.63 Hz, 1 H), 8.06-8.14 (m, 2 H) | (ESI (+)) m/e 434 (M + H)⁺ |
| 675 | N-(6-{[4-(trifluoromethyl)benzoyl]amino}hexyl)-1,3-dihydro-2H-isoindole-2-carboxamide | ¹H NMR (400 MHz, DMSO-$d_6$/Deuterium Oxide, Temp = 90° C.) δ ppm 1.32-1.41 (m, 4 H), 1.45-1.62 (m, 4 H), 3.11 (t, 2 H), 3.30 (t, J = 7.17 Hz, 2 H), 4.58 (s, 4 H), 7.24-7.33 (m, 4 H), 7.77 (d, J = 7.93 Hz, 2 H), 7.98 (d, J = 7.93 Hz, 2 H) | (ESI (+)) m/e 434 (M + H)⁺ |
| 676 | N-(6-{[3-(trifluoromethoxy)benzoyl]amino}hexyl)-1,3-dihydro-2H-isoindole-2-carboxamide | ¹H NMR (400 MHz, DMSO-$d_6$/Deuterium Oxide, Temp = 90° C.) δ ppm 1.30-1.41 (m, 4 H), 1.45-1.61 (m, 4 H), 3.12 (t, J = 7.02 Hz, 2 H), 3.29 (t, J = 7.17 Hz, 2 H), 4.59 (s, 4 H), 7.23-7.32 (m, 4 H), 7.41-7.49 (m, 1 H), 7.58 (t, J = 7.93 Hz, 1 H), 7.73 (s, 1 H), 7.84 (d, J = 7.93 Hz, 1 H) | (ESI (+)) m/e 450 (M + H)⁺ |
| 677 | N-{6-[(2,3-dimethoxybenzoyl)amino]hexyl}-1,3-dihydro-2H-isoindole-2-carboxamide | ¹H NMR (400 MHz, DMSO-$d_6$/Deuterium Oxide, Temp = 90° C.) δ ppm 1.33-1.42 (m, 4 H), 1.45-1.61 (m, 4 H), 3.12 (t, J = 7.02 Hz, 2 H), 3.28 (t, J = 7.02 Hz, 2 H), 3.79 (s, 3 H), 3.83 (s, 3 H), 4.58 (s, 4 H), 7.06-7.20 (m, 3 H), 7.24-7.32 (m, 4 H) | (ESI (+)) m/e 426 (M + H)⁺ |
| 678 | N-{6-[(2,4-dimethoxybenzoyl)amino]hexyl}-1,3-dihydro-2H-isoindole-2-carboxamide | ¹H NMR (400 MHz, DMSO-$d_6$/Deuterium Oxide, Temp = 90° C.) δ ppm 1.30-1.41 (m, 4 H), 1.45-1.62 (m, 4 H), 3.11 (t, J = 7.02 Hz, 2 H), 3.29 (t, J = 7.02 Hz, 2 H), 3.81 (s, 3 H), 3.90 (s, 3 H), 4.58 (s, 4 H), 6.56-6.63 (m, 2 H), 7.22-7.33 (m, 4 H), 7.78 (d, J = 8.54 Hz, 1 H) | (ESI (+)) m/e 426 (M + H)⁺ |
| 679 | N-{6-[(2,5-dimethoxybenzoyl)amino]hexyl}-1,3-dihydro-2H-isoindole-2-carboxamide | ¹H NMR (400 MHz, DMSO-$d_6$/Deuterium Oxide, Temp = 90° C.) δ ppm 1.31-1.40 (m, 4 H), 1.44-1.59 (m, 4 H), 3.12 (t, 2 H), 3.30 (t, J = 6.87 Hz, 2 H), 3.73 (s, 3 H), 3.82-3.86 (m, 3 H), 4.58 (s, 4 H), 6.99-7.08 (m, 2 H), 7.23-7.34 (m, 5 H) | (ESI (+)) m/e 426 (M + H)⁺ |
| 680 | N-{6-[(phenylacetyl)amino]hexyl}-1,3-dihydro-2H-isoindole-2-carboxamide | ¹H NMR (500 MHz, DMSO-$d_6$, Temp = 90° C.) δ 8.00 (m, 1H), 7.28 (m, 8H), 7.20 (m, 1H), 6.27 (t, J = 5.5, 1H), 4.57 (s, 4H), 3.04 (m, 4H), 1.40 (m, 4H), 1.27 (m, 4H) | (ESI (+)) m/e 380 (M + H)⁺ |
| 681 | N-(6-{[(3-fluorophenyl)acetyl]amino}hexyl)-1,3-dihydro-2H-isoindole-2-carboxamide | ¹H NMR (400 MHz, DMSO-$d_6$/Deuterium Oxide, Temp = 90° C.) δ ppm 1.22-1.33 (m, 4 H), 1.36-1.53 (m, 4 H), 3.02-3.13 (m, 4 H), 3.43 (s, 2 H), 4.59 (s, 4 H), 6.93-7.12 (m, 3 H), 7.23-7.34 (m, 5 H) | (ESI (+)) m/e 398 (M + H)⁺ |
| 688 | N-[6-(benzoylamino)hexyl]-1,3-dihydro-2H-pyrrolo[3,4-c]pyridine-2-carboxamide | ¹H NMR (300 MHz, DMSO-$d_6$) δ ppm 8.55 (s, 1 H) 8.46 (d, J = 4.75 Hz, 1 H) 8.41 (t, J = 5.43 Hz, 1 H) 7.78-7.86 (m, 2 H) 7.40-7.55 (m, 3 H) 7.38 (d, J = 5.09 Hz, 1 H) 6.36 (t, J = 5.43 Hz, 1 H) 4.60 (d, J = 2.03 Hz, 4 H) 3.21-3.29 (m, 2 H) 3.00-3.13 (m, 2 H) 1.25-1.60 (m, 8 H) | (ESI (+)) m/e 367 (M + H)⁺ |
| 689 | 4-fluoro-N-{6-[(pyridin-3-ylcarbonyl)amino]hexyl}-1,3-dihydro-2H-isoindole-2-carboxamide | ¹H NMR (500 MHz, DMSO-$d_6$, Temp = 90° C.) δ 9.02 (d, J = 2.2, 1H), 8.71 (m, 2H), 8.26 (dt, J = 7.9, 1.9, 1H), 7.58 (ddd, J = 7.9, 4.8, 0.8, 1H), 7.34 (td, J = 7.8, 5.1, 1H), 7.16 (d, J = 7.5, 1H), 7.10 (t, J = 8.8, 1H), 6.39 (bs, 1H), 4.62 (s, 4H), 3.28 (m, 2H), 3.07 (m, 2H), 1.54 (m, 2H), 1.46 (m, 2H), 1.34 (m, 4H) | (ESI (+)) m/e 385 (M + H)⁺ |
| 690 | 5-fluoro-N-{6-[(pyridin-3-ylcarbonyl)amino]hexyl}-1,3-dihydro-2H-isoindole-2-carboxamide | ¹H NMR (400 MHz, DMSO-$d_6$_D₂O, Temp = 90° C.) δ 8.99 (dd, J = 2.2, 0.9, 1H), 8.71 (m, 1H), 8.26 (m, 1H), 7.58 (m, 1H), 7.32 (m, 1H), 7.08 (m, 2H), 4.58 (d, J = 2.5, 2H), 4.55 (m, 2H), 3.11 (t, J = 7.0, 2H), 1.47 (m, 11H) | (ESI (+)) m/e 385 (M + H)⁺ |

-continued

| Ex | Name | ¹H NMR | MS |
|---|---|---|---|
| 691 | 5-methoxy-N-{6-[(pyridin-3-ylcarbonyl)amino]hexyl}-1,3-dihydro-2H-isoindole-2-carboxamide | ¹H NMR (400 MHz, DMSO-$d_6$_$D_2O$, Temp = 90° C.) δ 9.01 (dd, J = 2.2, 0.9, 1H), 8.73 (dd, J = 5.0, 1.6, 1H), 8.33 (ddd, J = 7.9, 2.2, 1.6, 1H), 7.63 (ddd, J = 7.9, 5.0, 0.9, 1H), 7.20 (m, 1H), 6.85 (m, 2H), 4.55 (m, 2H), 4.50 (d, J = 2.4, 2H), 3.76 (s, 3H), 3.11 (t, J = 7.0, 2H), 1.58 (t, J = 7.0, 3H), 1.50 (t, J = 6.8, 2H), 1.36 (m, 5H) | (ESI (+)) m/e 397 (M + H)⁺ |
| 692 | N-{6-[(pyridin-3-ylcarbonyl)amino]hexyl}-5-(trifluoromethyl)-1,3-dihydro-2H-isoindole-2-carboxamide | ¹H NMR (400 MHz, DMSO-$d_6$_$D_2O$, Temp = 90° C.) δ 8.99 (dd, J = 2.2, 0.9, 1H), 8.71 (dd, J = 4.9, 1.6, 1H), 8.27 (m, 1H), 7.58 (m, 4H), 4.66 (s, 4H), 3.12 (t, J = 7.0, 2H), 1.54 (m, 5H), 1.37 (m, 5H) | (ESI (+)) m/e 435 (M + H)⁺ |
| 693 | 4-cyano-N-{6-[(pyridin-3-ylcarbonyl)amino]hexyl}-1,3-dihydro-2H-isoindole-2-carboxamide | ¹H NMR (400 MHz, DMSO-$d_6$_$D_2O$, Temp = 90° C.) δ 8.99 (m, 1H), 8.71 (dd, J = 5.0, 1.6, 1H), 8.28 (ddd, J = 8.0, 2.3, 1.6, 1H), 7.67 (m, 2H), 7.59 (ddd, J = 7.9, 5.0, 0.9, 1H), 7.48 (t, J = 7.7, 1H), 4.75 (d, J = 2.2, 2H), 4.67 (m, 2H), 3.12 (t, J = 7.0, 2H), 1.56 (m, 5H), 1.37 (m, 5H) | (ESI (+)) m/e 392 (M + H)⁺ |
| 694 | 5-methyl-N-{6-[(pyridin-3-ylcarbonyl)amino]hexyl}-1,3-dihydro-2H-isoindole-2-carboxamide | ¹H NMR (400 MHz, DMSO-$d_6$_$D_2O$, Temp = 90° C.) δ 9.01 (m, 1H), 8.73 (dd, J = 5.0, 1.6, 1H), 8.32 (ddd, J = 7.9, 2.2, 1.6, 1H), 7.62 (ddd, J = 8.0, 5.0, 0.9, 1H), 7.17 (d, J = 7.7, 1H), 7.08 (d, J = 7.8, 2H), 4.54 (bs, 4H), 3.11 (t, J = 7.0, 2H), 2.31 (s, 3H), 1.56 (m, 5H), 1.37 (m, 5H) | (ESI (+)) m/e 381 (M + H)⁺ |
| 695 | 4-chloro-N-{6-[(pyridin-3-ylcarbonyl)amino]hexyl}-1,3-dihydro-2H-isoindole-2-carboxamide | ¹H NMR (400 MHz, DMSO-$d_6$_$D_2O$, Temp = 90° C.) δ 9.00 (dd, J = 2.2, 0.8, 1H), 8.71 (dd, J = 5.0, 1.6, 1H), 8.29 (ddd, J = 8.0, 2.2, 1.7, 1H), 7.60 (m, 1H), 7.30 (m, 3H), 4.63 (m, 4H), 3.32 (m, 2H), 3.12 (m, 2H), 1.54 (m, 5H), 1.36 (m, 5H) | (ESI (+)) m/e 401 (M + H)⁺ |
| 696 | 5-cyano-N-{6-[(pyridin-3-ylcarbonyl)amino]hexyl}-1,3-dihydro-2H-isoindole-2-carboxamide | ¹H NMR (400 MHz, DMSO-$d_6$_$D_2O$, Temp = 90° C.) δ 8.98 (d, J = 1.7, 1H), 8.70 (dd, J = 4.9, 1.6, 1H), 8.24 (m, 1H), 7.68 (m, 2H), 7.54 (m, 2H), 4.65 (m, 4H), 3.11 (m, 2H), 1.54 (m, 5H), 1.36 (m, 5H) | (ESI (+)) m/e 392 (M + H)⁺ |
| 697 | 5-chloro-N-{6-[(pyridin-3-ylcarbonyl)amino]hexyl}-1,3-dihydro-2H-isoindole-2-carboxamide | ¹H NMR (400 MHz, DMSO-$d_6$_$D_2O$, Temp = 90° C.) δ 8.99 (dd, J = 2.2, 0.7, 1H), 8.71 (dd, J = 5.0, 1.6, 1H), 8.27 (ddd, J = 8.0, 2.2, 1.7, 1H), 7.58 (m, 1H), 7.32 (m, 3H), 4.57 (dd, J = 8.2, 1.9, 4H), 3.11 (m, 2H), 1.54 (m, 5H), 1.37 (m, 5H) | (ESI (+)) m/e 401 (M + H)⁺ |
| 698 | N-{6-[(pyridin-2-ylcarbonyl)amino]hexyl}-1,3-dihydro-2H-isoindole-2-carboxamide | ¹H NMR (300 MHz, DMSO-$d_6$) δ ppm 8.74 (t, J = 5.76 Hz, 1 H) 8.63 (d, J = 4.75 Hz, 1 H) 7.89-8.12 (m, 2 H) 7.50-7.65 (m, 1 H) 7.19-7.39 (m, 4 H) 6.26 (t, J = 5.43 Hz, 1 H) 4.57 (s, 4 H) 3.23-3.35 (m, 2 H) 3.06 (q, J = 6.67 Hz, 2 H) 1.22-1.61 (m, 8 H) | (ESI (+)) m/e 367 (M + H)⁺ |

Example 607

N-{4-[(cyclopentylacetyl)amino]phenyl}-5-(pyridin-4-yl)-1,3-dihydro-2H-isoindole-2-carboxamide The title compound was prepared as described in Example 280, substituting pyridin-4-ylboronic acid for 1H-pyrazol-3-ylboronic acid and 5-bromo-N-(4-(2-cyclopentylacetamido)phenyl)isoindoline-2-carboxamide for 5-bromo-N-(4-(propylcarbamoyl)phenyl)isoindoline-2-carboxamide. ¹H NMR (300 MHz, DMSO-$d_6$) δ ppm 9.70 (s, 1H), 8.69-8.61 (m, 2H), 8.33 (s, 1H), 7.82-7.69 (m, 4H), 7.54-7.41 (m, 5H), 4.81 (bs, 4H), 2.31-2.15 (m, 3H), 1.82-1.68 (m, 2H), 1.68-1.43 (m, 4H), 1.26-1.11 (m, 2H); MS (ESI(+)) m/e 441 (M+H)⁺.

Example 608

5-(hydroxymethyl)-N-{4-[(3-methylbutyl)carbamoyl]phenyl}-1,3-dihydro-2H-isoindole-2-carboxamide The title compound was prepared as described in Example 272B, substituting 4-amino-N-isopentylbenzamide for 4-amino-N-propylbenzamide and isoindolin-5-ylmethanol hydrochloride for methyl isoindoline-5-carboxylate hydrochloride. ¹H NMR (300 MHz, DMSO-$d_6$) δ ppm 8.55 (s, 1H), 8.24-8.17 (m, 1H), 7.79-7.72 (m, 2H), 7.68-7.61 (m, 2H), 7.37-7.21 (m, 3H), 5.19 (t, J=5.7 Hz, 1H), 4.76 (bs, 4H), 4.52 (d, J=5.7 Hz, 2H), 3.30-3.21 (m, 2H), 1.70-1.54 (m, 1H), 1.47-1.36 (m, 2H), 0.90 (d, J=6.6 Hz, 6H); MS (ESI(+)) m/e 382 (M+H)⁺.

Example 609

N-{3-[(1-benzoylpiperidin-4-yl)oxy]propyl}-1,3-dihydro-2H-isoindole-2-carboxamide

Example 609A tert-butyl 4-(3-(isoindoline-2-carboxamido)propoxy)piperidine-1-carboxylate The title compound was prepared as described in Example 344A, substituting tert-butyl 4-(3-aminopropoxy)piperidine-1-carboxylate for tert-butyl 5-aminoisoindoline-2-carboxylate.

Example 609B

N-(3-(piperidin-4-yloxy)propyl)isoindoline-2-carboxamide

The title compound was prepared as described in Example 2D, substituting tert-butyl 4-(3-(isoindoline-2-carboxamido)propoxy)piperidine-1-carboxylate for tert-butyl 4-((4-(5-fluoroisoindoline-2-carboxamido)benzamido)methyl)benzylcarbamate.

Example 609C

N-{3-[(1-benzoylpiperidin-4-yl)oxy]propyl}-1,3-dihydro-2H-isoindole-2-carboxamide The title compound was prepared as described in Example 278, substituting benzoyl chloride for acetyl chloride and N-(3-(piperidin-4-yloxy)propyl)isoindoline-2-carboxamide for 5-amino-N-(4-(propylcarbamoyl)phenyl)isoindoline-2-carboxamide. $^1$H NMR (300 MHz, DMSO-$d_6$) δ ppm 7.21-7.50 (m, 9H) 6.27 (t, J=5.43 Hz, 1H) 4.57 (s, 4H) 3.40-3.58 (m, 6H) 3.07-3.21 (m, 2H) 1.74-1.93 (br m, 2H) 1.62-1.75 (m, 2H) 1.44 (br m, 2H); MS (ESI(+)) m/e 408 (M+H)$^+$.

Example 610

N-(3-{[1-(pyridin-3-ylcarbonyl)piperidin-4-yl]oxy}propyl)-1,3-dihydro-2H-isoindole-2-carboxamide The title compound was prepared as described in Example 278, substituting nicotinoyl chloride for acetyl chloride and N-(3-(piperidin-4-yloxy)propyl)isoindoline-2-carboxamide for 5-amino-N-(4-(propylcarbamoyl)phenyl)isoindoline-2-carboxamide. $^1$H NMR (300 MHz, DMSO-$d_6$) δ ppm 8.51-8.70 (m, 2H) 7.75-7.88 (m, 1H) 7.46 (dd, J=7.73, 4.96 Hz, 1H) 7.20-7.38 (m, 3H) 6.28 (t, J=5.35 Hz, 1H) 4.57 (s, 4H) 3.83-4.01 (m, 1H) 3.40-3.63 (m, 6H) 3.16 (q, J=6.35 Hz, 2H) 1.35-1.95 (m, 7H); MS (ESI(+)) m/e 409 (M+H)$^+$.

Table 11.

The following Examples were essentially prepared as described in Example 1C, substituting N-(6-(1,2,3,6-tetrahydropyridin-4-yl)pyridin-3-yl)isoindoline-2-carboxamide for 3-phenylpropan-1-amine and the corresponding carboxylic acid for 4-(isoindoline-2-carboxamido)benzoic acid.

| Ex | Name | $^1$H NMR | MS |
|---|---|---|---|
| 614 | N-[1'-(tetrahydrofuran-3-ylcarbonyl)-1',2',3',6'-tetrahydro-2,4'-bipyridin-5-yl]-1,3-dihydro-2H-isoindole-2-carboxamide | $^1$H NMR (400 MHz, DMSO-$d_6$, Temp = 90° C.) δ ppm 8.70 (d, J = 2.6 Hz, 1H), 8.35 (s, 1H), 7.95 (dd, J = 8.7, 2.6 Hz, 1H), 7.44 (d, J = 8.7 Hz, 1H), 7.40-7.24 (m, 4H), 6.54 (m, 1H), 4.79 (s, 4H), 4.19 (s, 2H), 3.91 (t, J = 8.1 Hz, 1H), 3.72 (m, 5H), 3.40 (m, 1H), 2.60 (s, 2H), 2.05 (m, 2H) | (ESI (+)) m/e 419 (M + H)$^+$ |
| 615 | N-{1'-[(2-methoxyethoxy)acetyl]-1',2',3',6'-tetrahydro-2,4'-bipyridin-5-yl}-1,3-dihydro-2H-isoindole-2-carboxamide | $^1$H NMR (400 MHz, DMSO-$d_6$, Temp = 90° C.) δ ppm 8.69 (d, J = 2.6 Hz, 1H), 8.35 (s, 1H), 7.95 (dd, J = 8.6, 2.6 Hz, 1H), 7.44 (d, J = 8.6 Hz, 1H), 7.38-7.27 (m, 4H), 6.54 (m, 1H), 4.79 (s, 4H), 4.19 (s, 2H), 4.15 (m, 2H), 3.65 (t, J = 5.7 Hz, 2H), 3.60 (m, 2H), 3.48 (m, 2H), 3.27 (s, 3H), 2.61 (m, 2H) | (ESI (+)) m/e 437 (M + H)$^+$ |
| 711 | N-[1'-(tetrahydrofuran-2-ylcarbonyl)-1',2',3',6'-tetrahydro-2,4'-bipyridin-5-yl]-1,3-dihydro-2H-isoindole-2-carboxamide | $^1$H NMR (400 MHz, DMSO-$d_6$, Temp = 90° C.) δ ppm 8.69 (d, J = 2.6 Hz, 1H), 8.34 (s, 1H), 7.95 (dd, J = 8.7, 2.6 Hz, 1H), 7.43 (d, J = 8.9 Hz, 1H), 7.39-7.23 (m, 4H), 6.54 (m, 1H), 4.79 (bs, 4H), 4.68 (dd, J = 7.4, 5.8 Hz, 1H), 4.19 (bs, 2H), 3.88-3.62 (m, 4H), 2.63 (m, 2H), 2.11 (m, 1H), 2.01 (m, 1H), 1.86 (m, 2H) | (ESI (+)) m/e 419 (M + H)$^+$ |
| 712 | N-[1'-(tetrahydro-2H-pyran-4-ylcarbonyl)-1',2',3',6'-tetrahydro-2,4'-bipyridin-5-yl]-1,3-dihydro-2H-isoindole-2-carboxamide | $^1$H NMR (400 MHz, DMSO-$d_6$, Temp = 90° C.) δ ppm 8.69 (dd, J = 2.6, 0.7 Hz, 1H), 8.34 (s, 1H), 7.95 (dd, J = 8.6, 2.6 Hz, 1H), 7.43 (d, J = 8.9 Hz, 1H), 7.38-7.26 (m, 4H), 6.55 (m, 1H), 4.79 (s, 4H), 4.19 (m, 2H), 3.86 (m, 2H), 3.70 (t, J = 5.7 Hz, 2H), 3.42 (td, J = 11.4, 2.5 Hz, 2H), 2.92 (m, 1H), 2.60 (m, 2H), 1.73-1.60 (m, 2H), 1.56 (m, 2H) | (ESI (+)) m/e 433 (M + H)$^+$ |
| 713 | N-[1'-(1,4-dioxan-2-ylcarbonyl)-1',2',3',6'-tetrahydro-2,4'-bipyridin-5-yl]-1,3-dihydro-2H-isoindole-2-carboxamide | $^1$H NMR (400 MHz, DMSO-$d_6$, Temp = 90° C.) δ ppm 8.70 (d, J = 2.6 Hz, 1H), 8.35 (s, 1H), 7.96 (dd, J = 8.6, 2.6 Hz, 1H), 7.43 (d, J = 8.6 Hz, 1H), 7.38-7.26 (m, 4H), 6.54 (m, 1H), 4.79 (s, 4H), 4.37 (dd, J = 9.1, 3.0 Hz, 1H), 4.20 (m, 2H), 3.83-3.61 (m, 7H), 3.52 (m, 1H), 2.61 (m, 2H) | (ESI (+)) m/e 435 (M + H)$^+$ |
| 714 | N-{1'-[(1-methylpyrrolidin-3-yl)carbonyl]-1',2',3',6'-tetrahydro-2,4'-bipyridin-5-yl}-1,3-dihydro-2H-isoindole-2-carboxamide | $^1$H NMR (400 MHz, DMSO-$d_6$, Temp = 90° C.) δ ppm 8.69 (dd, J = 2.6, 0.7 Hz, 1H), 8.34 (s, 1H), 7.95 (dd, J = 8.6, 2.6 Hz, 1H), 7.43 (d, J = 8.6 Hz, 1H), 7.38-7.26 (m, 4H), 6.54 (m, 1H), 4.79 (s, 4H), 4.16 (m, 2H), 3.68 (t, J = 5.7 Hz, 2H), 3.28 (m, 1H), 2.78 (t, J = 8.6 Hz, 1H), 2.58 (m, 2H), 2.52 (m, 2H), 2.38 (q, J = 7.7 Hz, 1H), 2.24 (s, 3H), 2.98 (m, 2H) | (ESI (+)) m/e 432 (M + H)$^+$ |
| 715 | N-{1'-[(1,1-dioxidotetrahydrothiophen-3-yl)carbonyl]-1',2',3',6'-tetrahydro-2,4'-bipyridin-5-yl}-1,3-dihydro-2H-isoindole-2-carboxamide | $^1$H NMR (400 MHz, DMSO-$d_6$, Temp = 90° C.) δ ppm 8.70 (d, J = 2.6 Hz, 1H), 8.35 (s, 1H), 7.96 (dd, J = 8.6, 2.6 Hz, 1H), 7.45 (d, J = 8.6 Hz, 1H), 7.38-7.27 (m, 4H), 6.55 (m, 1H), 4.79 (s, 4H), 4.21 (m, 2H), 3.79-3.65 (m, 3H), 3.36-3.13 (m, 3H), 3.08 (m, 1H), 2.63 (m, 2H), 2.37 (m, 1H), 2.14 (m, 1H) | (ESI (+)) m/e 467 (M + H)$^+$ |

| Ex | Name | ¹H NMR | MS |
|---|---|---|---|
| 758 | N-[1'-(2-hydroxy-2-methylpropanoyl)-1',2',3',6'-tetrahydro-2,4'-bipyridin-5-yl]-1,3-dihydro-2H-isoindole-2-carboxamide | ¹H NMR (400 MHz, DMSO-$d_6$, Temp = 90° C.) δ ppm 8.69 (d, J = 2.6 Hz, 1H), 8.34 (bs, 1H), 7.95 (dd, J = 8.6, 2.6 Hz, 1H), 7.43 (d, J = 8.6 Hz, 1H), 7.38-7.26 (m, 4H), 6.55 (m, 1H), 5.09 (s, 1H), 4.79 (s, 4H), 4.32 (m, 2H), 3.93 (t, J = 5.7 Hz, 2H), 2.60 (m, 2H), 1.37 (s, 6H) | (ESI (+)) m/e 407 (M + H)⁺ |
| 800 | N-[1'-(morpholin-4-ylacetyl)-1',2',3',6'-tetrahydro-2,4'-bipyridin-5-yl]-1,3-dihydro-2H-isoindole-2-carboxamide | ¹H NMR (400 MHz, DMSO-$d_6$, Temp = 90° C.) δ ppm 8.70 (d, J = 2.6 Hz, 1H), 8.34 (s, 1H), 7.95 (dd, J = 8.6, 2.6 Hz, 1H), 7.44 (d, J = 8.6 Hz, 1H), 7.38-7.27 (m, 4H), 6.54 (m, 1H), 4.79 (s, 4H), 4.20 (m, 2H), 3.71 (t, J = 5.2 Hz, 2H), 3.58 (m, 4H), 3.21 (s, 2H), 2.48 (m, 2H), 2.45 (m, 4H) | (ESI (+)) m/e 448 (M + H)⁺ |
| 1466 | N-(4-{1-[(3R)-tetrahydrofuran-3-ylcarbonyl]-1,2,3,6-tetrahydropyridin-4-yl}phenyl)-1,3-dihydro-2H-isoindole-2-carboxamide | -¹H NMR (400 MHz, DMSO-$d_6$, Temp = 90° C.) δ ppm 8.13 (s, 1H), 7.54 (m, 2H), 7.31 (m, 6H), 6.07 (m, 1H), 4.77 (s, 4H), 4.14 (m, 2H), 3.91 (t, J = 8.1 Hz, 1H), 3.77-3.67 (m, 5H), 3.38 (m, 1H), 2.50 (m, 2H), 2.02 (m, 2H) | (ESI (+)) m/e 418 (M + H)⁺ |
| 1467 | N-(4-{1-[(3S)-tetrahydrofuran-3-ylcarbonyl]-1,2,3,6-tetrahydropyridin-4-yl}phenyl)-1,3-dihydro-2H-isoindole-2-carboxamide | ¹H NMR (400 MHz, DMSO-$d_6$, Temp = 90° C.) δ ppm 8.12 (s, 1H), 7.54 (m, 2H), 7.31 (m, 6H), 6.07 (m, 1H), 4.77 (s, 4H), 4.14 (m, 2H), 3.91 (t, J = 8.1 Hz, 1H), 3.77-3.67 (m, 5H), 3.38 (m, 1H), 2.50 (m, 2H), 2.05 (m, 2H) | (ESI (+)) m/e 418 (M + H)⁺ |
| 1468 | N-(4-{1-[(1,1-dioxidotetrahydro-2H-thiopyran-4-yl)carbonyl]-1,2,3,6-tetrahydropyridin-4-yl}phenyl)-1,3-dihydro-2H-isoindole-2-carboxamide | ¹H NMR (400 MHz, DMSO-$d_6$, Temp = 90° C.) δ ppm 8.13 (s, 1H), 7.54 (m, 2H), 7.31 (m, 6H), 6.07 (m, 1H), 4.77 (s, 4H), 4.15 (m, 2H), 3.71 (t, J = 5.7 Hz, 2H), 3.25-3.02 (m, 5H), 2.50 (m, 2H), 2.07 (m, 4H) | (ESI (+)) m/e 480 (M + H)⁺ |

Example 611

N-(6-{[(3S)-tetrahydrofuran-3-ylmethyl]carbamoyl}pyridazin-3-yl)-1,3-dihydro-2H-isoindole-2-carboxamide

Example 611A methyl 6-aminopyridazine-3-carboxylate

To a solution of 6-chloropyridazin-3-amine (32 g, 248 mmol), Et₃N (75 mL, 744 mmol) in MeOH (500 mL), Pd(dppf)Cl₂ (12 g, 16.4 mmol) was added and the mixture was heated at 60° C. overnight under CO atmosphere at 50 psi. After cooling to room temperature, the reaction mixture was filtered and the filtrate was concentrated under reduced pressure. The residue was washed with MeOH and the precipitate was dried by high vacuum to give the title compound as a solid.

Example 611B methyl 6-isocyanatopyridazine-3-carboxylate

To the solution of methyl 6-aminopyridazine-3-carboxylate (14 g, 91.5 mmol) in anhydrous toluene (700 mL) was added Et₃N (11.1, 109.8 mmol). A solution of triphosgene (27.2 g, 91.5 mmol) in anhydrous toluene was added slowly at 0° C. The reaction mixture was stirred for 2 hrs at room temperature and then heated at 90° C. for 5 hrs. After cooling to room temperature, toluene and water were added to the mixture, the mixture was separated and the organic layer was dried over anhydrous Na₂SO₄, concentrated under reduced pressure to give the title compound as a solid.

Example 611C methyl 6-(isoindoline-2-carboxamido)pyridazine-3-carboxylate

To a solution of methyl 6-isocyanatopyridazine-3-carboxylate (5.26 g, 29.4 mmol) in THF (100 mL), a solution of isoindoline (5.24 g, 4.41 mmol) in THF (50 mL) was added at 0° C. The reaction mixture was stirred overnight at room temperature. The reaction mixture was filtered and the precipitate was washed with cold EtOAc and dried in high vacuum to give the title compound as a solid.

Example 611D 6-(isoindoline-2-carboxamido)pyridazine-3-carboxylic acid

To a solution of methyl 6-(isoindoline-2-carboxamido)pyridazine-3-carboxylate (3.7 g, 12.4 mmol) in MeOH (40 mL) and THF (40 mL), a solution of LiOH (0.7 g, 29.2 mmol) in water (10 mL) was added at room temperature. The reaction mixture was stirred overnight at room temperature. The reaction mixture was poured into water (100 mL), extracted with EtOAc (2×50 mL) and the aqueous layer was acidified by addition of 2 NHCl to pH 3 to give a precipitate. The precipitate was washed with water and dried in high vacuum to give the title compound.

Example 611E

N-(6-{[(3S)-tetrahydrofuran-3-ylmethyl]carbamoyl}pyridazin-3-yl)-1,3-dihydro-2H-isoindole-2-carboxamide The title compound was prepared as described in Example 1C, substituting (S)-(tetrahydrofuran-3-yl)methamine for 3-phenylpropan-1-amine and 6-(isoindoline-2-carboxamido)pyridazine-3-carboxylic acid for 4-(isoindoline-2-carboxamido)benzoic acid. $^1$H NMR (300 MHz, DMSO-$d_6$) δ 9.94 (s, 1H), 9.12 (t, J=6.1 Hz, 1H), 8.31 (d, J=9.3 Hz, 1H), 8.11 (d, J=9.3 Hz, 1H), 7.41-7.28 (m, 4H), 4.89 (s, 4H), 3.80-3.55 (m, 3H), 3.50 (dd, J=8.5, 5.2 Hz, 1H), 3.37-3.31 (m, 2H), 2.63-2.51 (m, 1H), 2.01-1.85 (m, 1H), 1.71-1.55 (m, 1H); MS (ESI(+)) m/e 368 (M+H)$^+$.

Example 612

N-{6-[(cyclopentylmethyl)carbamoyl]pyridazin-3-yl}-1,3-dihydro-2H-isoindole-2-carboxamide The title compound was prepared as described in Example 1C, substituting cyclopentylmethamine for 3-phenylpropan-1-amine and 6-(isoindoline-2-carboxamido)pyridazine-3-carboxylic acid for 4-(isoindoline-2-carboxamido)benzoic acid. $^1$H NMR (300 MHz, DMSO-$d_6$) δ 9.97 (s, 1H), 9.00 (t, J=6.1 Hz, 1H), 8.31 (d, J=9.3 Hz, 1H), 8.11 (d, J=9.3 Hz, 1H), 7.41-7.28 (m, 4H), 5.13-4.72 (m, 4H), 3.31-3.16 (m, 2H), 2.22 (p, J=7.3 Hz, 1H), 1.70-1.45 (m, 6H), 1.38-1.20 (m, 2H); MS (ESI(+)) m/e 366 (M+H)$^+$.

Example 616

5-(hydroxymethyl)-N-(4-phenylbutyl)-1,3-dihydro-2H-isoindole-2-carboxamide

The title compound was prepared as described in Example 1A, substituting (4-isocyanatobutyl)benzene for methyl 4-isocyanatobenzoate and isoindolin-5-ylmethanol hydrochloride for isoindoline. $^1$H NMR (300 MHz, DMSO-$d_6$) δ ppm 7.32-7.12 (m, 8H), 6.32-6.24 (m, 1H), 5.16 (t, J=5.6 Hz, 1H), 4.54 (bs, 4H), 4.49 (d, J=5.7 Hz, 2H), 3.14-3.05 (m, 2H), 2.64-2.54 (m, 2H), 1.63-1.39 (m, 4H); MS (ESI(+)) m/e 325 (M+H)$^+$.

Example 617

5-(hydroxymethyl)-N-[1-(3-methylbutyl)-1H-pyrazol-4-yl]-1,3-dihydro-2H-isoindole-2-carboxamide The title compound was prepared as described in Example 272B, substituting 1-isopentyl-1H-pyrazol-4-amine dihydrochloride for 4-amino-N-propylbenzamide and isoindolin-5-ylmethanol hydrochloride for methyl isoindoline-5-carboxylate hydrochloride. $^1$H NMR (300 MHz, DMSO-$d_6$) δ ppm 8.39 (s, 1H), 7.73 (s, 1H), 7.39 (s, 1H), 7.34-7.18 (m, 3H), 5.19 (t, J=5.6 Hz, 1H), 4.67 (bs, 4H), 4.51 (d, J=5.5 Hz, 2H), 4.04 (t, J=7.1 Hz, 2H), 1.71-1.55 (m, 2H), 1.55-1.33 (m, 1H), 0.89 (d, J=6.5 Hz, 6H); MS (ESI(+)) m/e 329 (M+H)$^+$.

Example 618

N-{5-[(3-methylbutyl)carbamoyl]pyrazin-2-yl}-1,3-dihydro-2H-isoindole-2-carboxamide

Example 618A ethyl 5-(isoindoline-2-carboxamido)pyrazine-2-carboxylate

The title compound was prepared as described in Example 344A, substituting ethyl 5-aminopyrazine-2-carboxylate for tert-butyl 5-aminoisoindoline-2-carboxylate.

Example 618B 5-(isoindoline-2-carboxamido)pyrazine-2-carboxylic acid

The title compound was prepared as described in Example 1B, substituting ethyl 5-(isoindoline-2-carboxamido)pyrazine-2-carboxylate for methyl 4-(isoindoline-2-carboxamido)benzoate.

Example 618C

N-{5-[(3-methylbutyl)carbamoyl]pyrazin-2-yl}-1,3-dihydro-2H-isoindole-2-carboxamide The title compound was prepared as described in Example 1C, substituting 3-methylbutan-1-amine for 3-phenylpropan-1-amine and 5-(isoindoline-2-carboxamido)pyrazine-2-carboxylic acid for 4-(isoindoline-2-carboxamido)benzoic acid. $^1$H NMR (300 MHz, DMSO-$d_6$, Temp=90° C.) δ ppm 9.34 (bs, 1H), 9.17 (d, J=1.4 Hz, 1H), 8.82 (d, J=1.4 Hz, 1H), 8.30-8.23 (m, 1H), 7.36-7.26 (m, 4H), 4.86 (bs, 4H), 3.37-3.30 (m, 2H), 1.69-1.58 (m, 1H), 1.50-1.44 (m, 2H), 0.92 (d, J=6.5 Hz, 6H); MS (ESI(+)) m/e 354 (M+H)$^+$.

Example 621

N-(4-{(1E)-3-[benzyl(methyl)amino]prop-1-en-1-yl}phenyl)-1,3-dihydro-2H-isoindole-2-carboxamide

Example 621A (E)-N-benzyl-N-methyl-3-(4,4,5,5-tetramethyl-1,3,2-dioxaborolan-2-yl)prop-2-en-1-amine In a 4 mL vial were mixed (E)-2-(3-chloroprop-1-enyl)-4,4,5,5-tetramethyl-1,3,2-dioxaborolane (0.195 ml, 0.988 mmol) and potassium carbonate (273 mg, 1.975 mmol) in anhydrous acetonitrile (2 ml). Benzylmethylamine (0.166 ml, 1.284 mmol) was added to this mixture, and the reaction was stirred vigorously overnight at room temperature. The reaction was diluted with ethyl acetate and washed with water and brine. The organic layer was dried with sodium sulfate, decanted, and concentrated to provide the title compound.

Example 621B

N-(4-{(1E)-3-[benzyl(methyl)amino]prop-1-en-1-yl}-phenyl)-1,3-dihydro-2H-isoindole-2-carboxamide The title compound was prepared as described in Example 280, substituting (E)-N-benzyl-N-methyl-3-(4,4,5,5-tetramethyl-1,3,2-dioxaborolan-2-yl)prop-2-en-1-amine for 1H-pyrazol-3-ylboronic acid and N-(4-bromophenyl)isoindoline-2-carboxamide for 5-bromo-N-(4-(propylcarbamoyl)phenyl)isoindoline-2-carboxamide. $^1$H NMR (400 MHz, DMSO-d$_6$, Temp=90° C.) δ ppm 8.12 (s, 1H), 7.52 (m, 2H), 7.37-7.18 (m, 11H), 6.48 (d, J=15.8 Hz, 1H), 6.18 (dt, J=15.8, 6.5 Hz, 1H), 4.77 (s, 4H), 3.53 (s, 2H), 3.15 (dd, J=6.5, 1.4 Hz, 2H), 2.18 (s, 3H); MS (ESI(+)) m/e 398 (M+H)$^+$.

Example 622

N-[4-(4-phenoxypiperidin-1-yl)phenyl]-1,3-dihydro-2H-isoindole-2-carboxamide

Example 622A 1-(4-nitrophenyl)-4-phenoxypiperidine

A solution of 1-fluoro-4-nitrobenzene (0.15 g, 1.063 mmol) and 4-phenoxypiperidine hydrochloride (0.250 g, 1.169 mmol) in dimethylformamide (2.126 ml) was treated with potassium carbonate (0.367 g, 2.66 mmol). The suspension was stirred at ambient temperature 2 hours, at 55° C. for 4 hours and at ambient temperature for 16 hours. The reaction was poured into water and the suspension was filtered and vacuum dried to provide the title compound.

Example 622B 4-(4-phenoxypiperidin-1-yl)aniline

The title compound was prepared as described in Example 272A, substituting 1-(4-nitrophenyl)-4-phenoxypiperidine for 4-nitro-N-propylbenzamide.

Example 622C

N-[4-(4-phenoxypiperidin-1-yl)phenyl]-1,3-dihydro-2H-isoindole-2-carboxamide

The title compound was prepared as described in Example 272B, substituting 4-(4-phenoxypiperidin-1-yl)aniline for 4-amino-N-propylbenzamide and isoindoline for methyl isoindoline-5-carboxylate hydrochloride. $^1$H NMR (300 MHz, DMSO-d$_6$) δ ppm 8.11 (s, 1H), 7.42-7.24 (m, 8H), 7.02-6.86 (m, 5H), 4.74 (bs, 4H), 4.59-4.47 (m, 1H), 3.49-3.39 (m, 2H), 3.03-2.91 (m, 2H), 2.11-1.98 (m, 2H), 1.81-1.66 (m, 2H); MS (ESI(+)) m/e 414 (M+H)$^+$.

Example 623

N-[4-(3-phenoxyazetidin-1-yl)phenyl]-1,3-dihydro-2H-isoindole-2-carboxamide

The title compound was prepared as described in Example 622, substituting 3-phenoxyazetidine for 4-phenoxypiperidine hydrochloride in Example 622A. $^1$H NMR (300 MHz, DMSO-d$_6$) δ ppm 8.06 (s, 1H), 7.44-7.25 (m, 8H), 7.03-6.93 (m, 1H), 6.92-6.85 (m, 2H), 6.47-6.40 (m, 2H), 5.19-5.08 (m, 1H), 4.73 (bs, 4H), 4.32-4.23 (m, 2H), 3.69 (dd, J=8.2, 4.2 Hz, 2H); MS (ESI(+)) m/e 386 (M+H)$^+$.

Example 624

N-(4-{[benzyl(methyl)amino]methyl}phenyl)-1,3-dihydro-2H-isoindole-2-carboxamide A suspension of isoindoline (0.1 g, 0.839 mmol) and N-ethyl-N-isopropylpropan-2-amine (0.219 ml, 1.259 mmol) in acetonitrile (2.80 ml) was treated with N-methylpyrrolidine (2.80 ml). The solution was cooled to 0° C. and 1-(chloromethyl)-4-isocyanatobenzene (0.155 g, 0.923 mmol) was added. After stirring for 2 hours at 0° C., the reaction was treated with a solution of N-methyl-1-phenylmethanamine (0.102 g, 0.839 mmol) in 0.5 mL acetonitrile. The reaction was stirred at 0° C. for 5 minutes and at ambient temperature for 30 minutes. The reaction was treated with water and the mixture was stirred for 4 hours. The suspension was filtered and the solid collected was washed with water and dried under vacuum to provide the title compound. $^1$H NMR (300 MHz, DMSO-d$_6$) δ ppm 8.31 (s, 1H), 7.56-7.49 (m, 2H), 7.40-7.28 (m, 8H), 7.27-7.19 (m, 3H), 4.76 (bs, 4H), 3.47 (s, 2H), 3.43 (s, 2H), 2.06 (s, 3H); MS (ESI(+)) m/e 372 (M+H)$^+$.

Example 625

5-fluoro-N-(4-{[(3R)-tetrahydrofuran-3-ylmethyl]carbamoyl}phenyl)-1,3-dihydro-2H-isoindole-2-carboxamide The title compound was prepared as described in Example 410, substituting 5-fluoro-N-(4-{[tetrahydrofuran-3-ylmethyl]carbamoyl}phenyl)-1,3-dihydro-2H-isoindole-2-carboxamide for N-(4-{[tetrahydrofuran-3-ylmethyl]carbamoyl}phenyl)-1,3-dihydro-2H-isoindole-2-carboxamide. $^1$H NMR (300 MHz, DMSO-d$_6$) δ 8.60 (s, 1H), 8.39 (t, J=5.7 Hz, 1H), 7.81-7.73 (m, 2H), 7.69-7.62 (m, 2H), 7.40 (dd, J=8.4, 5.2 Hz, 1H), 7.24 (dd, J=9.1, 2.5 Hz, 1H), 7.15 (td, J=8.9, 2.5 Hz, 1H), 4.80-4.72 (m, 4H), 3.80-3.68 (m, 1H), 3.68-3.56 (m, 2H), 3.47 (dd, J=8.5, 5.2 Hz, 2H), 3.21 (dt, J=13.3, 5.9 Hz, 2H), 2.01-1.86 (m, 1H), 1.67-1.53 (m, 1H); MS (ESI(+)) m/e 384 (M+H)$^+$.

Example 626

5-fluoro-N-(4-{[(3S)-tetrahydrofuran-3-ylmethyl]carbamoyl}phenyl)-1,3-dihydro-2H-isoindole-2-carboxamide The title compound was prepared as described in Example 411, substituting 5-fluoro-N-(4-{[tetrahydrofuran-3-ylmethyl]carbamoyl}phenyl)-1,3-dihydro-2H-isoindole-2-carboxamide for N-(4-{[tetrahydrofuran-3-ylmethyl]carbamoyl}phenyl)-1,3-dihydro-2H-isoindole-2-carboxamide. $^1$H NMR (300 MHz, DMSO-d$_6$) δ 8.60 (s, 1H), 8.39 (t, J=5.7 Hz, 1H), 7.80-7.73 (m, 2H), 7.69-7.62 (m, 2H), 7.40 (dd, J=8.4, 5.2 Hz, 1H), 7.24 (dd, J=9.1, 2.5 Hz, 1H), 7.15 (td, J=8.9, 2.5 Hz, 1H), 4.80-4.73 (m, 4H), 3.80-3.56 (m, 3H), 3.47 (dd, J=8.5, 5.2 Hz, 1H), 3.24-3.13 (m, 2H), 2.01-1.86 (m, 1H), 1.67-1.53 (m, 1H); MS (ESI(+)) m/e 384 (M+H)$^+$.

Example 636

N-[4-(1-benzyl-1H-1,2,3-triazol-4-yl)phenyl]-1,3-dihydro-2H-isoindole-2-carboxamide Example 636A N-(4-ethynylphenyl)isoindoline-2-carboxamide The title compound was prepared as described in Example 1A, substituting 1-ethynyl-4-isocyanatobenzene for methyl 4-isocyanatobenzoate.

Example 636B

N-[4-(1-benzyl-1H-1,2,3-triazol-4-yl)phenyl]-1,3-dihydro-2H-isoindole-2-carboxamide A mixture of N-(4-ethynylphenyl)isoindoline-2-carboxamide (100 mg, 0.381 mmol), benzylamine (33.2 mg, 0.381 mmol), and sodium ascorbate (15 mg, 0.076 mmol) in methanol (1.9 ml) was treated with 1H-imidazole-1-sulfonyl azide hydrochloride (66.0 mg, 0.381 mmol), copper(II) sulfate pentahydrate (9.52 mg, 0.038 mmol) and triethylamine (63.8 μl, 0.457 mmol). Additional methanol (2 mL) was added and the vial was flushed with nitrogen and stirred for 2 days. The mixture was diluted with water and the resulting suspension was filtered with water washes to provide the title compound as a white solid. $^1$H NMR (300 MHz, DMSO-d$_6$) δ 8.51 (s, 1H), 8.45 (s, 1H), 7.73 (d, J=8.7 Hz, 2H), 7.65 (d, J=8.9 Hz, 2H), 7.49-7.24 (m, 9H), 5.63 (s, 2H), 4.78 (s, 4H), 1.11-1.00 (m, 1H); MS (ESI(+)) m/e 396 (M+H)$^+$.

Table 12.

The following Examples were essentially prepared as described in Example 636B, substituting the appropriate amine for benzylamine

| Ex | Name | $^1$H NMR | MS |
|---|---|---|---|
| 637 | N-{4-[1-(3-methylbutyl)-1H-1,2,3-triazol-4-yl]phenyl}-1,3-dihydro-2H-isoindole-2-carboxamide | $^1$H NMR (300 MHz, DMSO-d$_6$) δ 8.47 (s, 1H), 8.44 (s, 1H), 7.73 (d, J = 8.8 Hz, 2H), 7.65 (d, J = 8.8 Hz, 2H), 7.41-7.27 (m, 6H), 4.79 (s, 5H), 4.40 (t, J = 7.3 Hz, 2H), 1.77 (dd, J = 14.5, 7.0 Hz, 2H), 1.52 (dt, J = 13.4, 6.7 Hz, 1H), 0.93 (d, J = 6.6 Hz, 7H) | (ESI (+)) m/e 376 (M + H)$^+$ |
| 638 | N-{4-[1-(tetrahydrofuran-3-ylmethyl)-1H-1,2,3-triazol-4-yl]phenyl}-1,3-dihydro-2H-isoindole-2-carboxamide | $^1$H NMR (300 MHz, DMSO-d$_6$) δ 8.50 (s, 1H), 8.45 (s, 1H), 7.73 (d, J = 8.9 Hz, 2H), 7.66 (d, J = 8.8 Hz, 2H), 7.34 (ddd, J = 8.9, 4.2, 2.5 Hz, 4H), 4.79 (s, 4H), 4.39 (d, J = 7.5 Hz, 2H), 3.84-3.59 (m, 3H), 3.51 (dd, J = 8.8, 5.4 Hz, 1H), 2.88-2.69 (m, 1H), 2.04-1.86 (m, 1H), 1.73-1.55 (m, 1H) | (ESI (+)) m/e 390 (M + H)$^+$ |
| 639 | N-(4-{1-[2-(2-oxopyrrolidin-1-yl)ethyl]-1H-1,2,3-triazol-4-yl}phenyl)-1,3-dihydro-2H-isoindole-2-carboxamide | $^1$H NMR (400 MHz, DMSO-d$_6$) δ 8.46 (s, 2H), 7.72 (d, J = 8.8 Hz, 2H), 7.66 (d, J = 8.9 Hz, 2H), 7.37 (d, J = 5.5 Hz, 2H), 7.32 (dd, J = 5.6, 3.1 Hz, 2H), 4.79 (s, 4H), 4.53 (t, J = 5.9 Hz, 2H), 3.66 (t, J = 5.9 Hz, 2H), 3.23 (t, J = 7.0 Hz, 2H), 2.15 (t, J = 8.0 Hz, 2H), 1.94-1.76 (m, 2H) | (ESI (+)) m/e 417 (M + H)$^+$ |
| 640 | N-{4-[1-(1-benzylpiperidin-4-yl)-1H-1,2,3-triazol-4-yl]phenyl}-1,3-dihydro-2H-isoindole-2-carboxamide | $^1$H NMR (300 MHz, DMSO-d$_6$) δ 8.57 (s, 1H), 8.43 (s, 1H), 7.73 (d, J = 8.7 Hz, 1H), 7.65 (d, J = 8.8 Hz, 1H), 7.41-7.24 (m, 9H), 4.79 (s, 3H), 4.53 (td, J = 10.6, 5.1 Hz, 1H), 3.54 (s, 2H), 2.98-2.88 (m, 2H), 2.33-1.93 (m, 6H) | (ESI (+)) m/e 479 (M + H)$^+$ |
| 641 | N-{4-[1-(3-phenylpropyl)-1H-1,2,3-triazol-4-yl]phenyl}-1,3-dihydro-2H-isoindole-2-carboxamide | $^1$H NMR (300 MHz, DMSO-d$_6$) δ 8.50 (s, 1H), 8.45 (s, 1H), 7.74 (d, J = 8.7 Hz, 1H), 7.66 (d, J = 8.8 Hz, 1H), 7.50-7.26 (m, 6H), 7.27-7.16 (m, 3H), 4.79 (s, 2H), 4.40 (t, J = 7.0 Hz, 2H), 2.62 (t, J = 7.7 Hz, 2H), 2.29-2.07 (m, 1H) | (ESI (+)) m/e 424 (M + H)$^+$ |
| 642 | N-(4-{1-[4-(morpholin-4-yl)benzyl]-1H-1,2,3-triazol-4-yl}phenyl)-1,3-dihydro-2H-isoindole-2-carboxamide | $^1$H NMR (300 MHz, DMSO-d$_6$) δ 8.44 (s, 2H), 7.72 (d, J = 8.7 Hz, 2H), 7.64 (d, J = 8.8 Hz, 2H), 7.42-7.19 (m, 6H), 6.94 (d, J = 8.7 Hz, 2H), 5.49 (s, 2H), 4.78 (s, 4H), 3.79-3.65 (m, 4H), 3.23-2.97 (m, 4H) | (ESI (+)) m/e 481 (M + H)$^+$ |
| 643 | N-[4-(1-isobutyl-1H-1,2,3-triazol-4-yl)phenyl]-1,3-dihydro-2H-isoindole-2-carboxamide | $^1$H NMR (300 MHz, DMSO-d$_6$) δ 8.44 (s, 2H), 7.74 (d, J = 8.7 Hz, 2H), 7.66 (d, J = 8.8 Hz, 2H), 7.41-7.27 (m, 5H), 4.79 (s, 4H), 4.21 (d, J = 7.2 Hz, 2H), 2.29-2.06 (m, 1H), 0.90 (d, J = 6.7 Hz, 3H) | (ESI (+)) m/e 362 (M + H)$^+$ |
| 644 | N-{4-[1-(cyclopentylmethyl)-1H-1,2,3-triazol-4-yl]phenyl}-1,3-dihydro-2H-isoindole-2-carboxamide | $^1$H NMR (300 MHz, DMSO-d$_6$) δ 8.46 (s, 1H), 8.44 (s, 1H), 7.73 (d, J = 8.7 Hz, 1H), 7.66 (d, J = 8.8 Hz, 1H), 7.41-7.28 (m, 4H), 4.79 (s, 2H), 4.31 (d, J = 7.5 Hz, 1H), 3.31 (s, 2H), 2.40 (dt, J = 15.1, 7.4 Hz, 1H), 1.73-1.47 (m, 6H), 1.36-1.21 (m, 2H) | (ESI (+)) m/e 388 (M + H)$^+$ |
| 645 | N-{4-[1-(3-methoxypropyl)-1H-1,2,3-triazol-4-yl]phenyl}-1,3-dihydro-2H-isoindole-2-carboxamide | $^1$H NMR (300 MHz, DMSO-d$_6$) δ 8.46 (s, 1H), 8.45 (s, 1H), 7.73 (d, J = 8.8 Hz, 2H), 7.66 (d, J = 8.8 Hz, 2H), 7.42-7.26 (m, 4H), 4.79 (s, 4H), 4.43 (t, J = 7.1 Hz, 2H), 3.38-3.32 (m, 1H), 3.25 (s, 3H), 2.10 (p, J = 6.4 Hz, 2H) | (ESI (+)) m/e 378 (M + H)$^+$ |

Example 646

N-[4-(1-isobutyrylpiperidin-4-yl)phenyl]-1,3-dihydro-2H-pyrrolo[3,4-c]pyridine-2-carboxamide N-[4-(1-isobutyryl-1,2,3,6-tetrahydropyridin-4-yl)phenyl]-1,3-dihydro-2H-pyrrolo[3,4-c]pyridine-2-carboxamide (50 mg, 0.128 mmol) and methanol (10 ml) were added to 5% Pd—C, wet (10.00 mg, 0.094 mmol) in a 50 ml pressure bottle and stirred for 16 hours at 30 psi and room temperature. The mixture was filtered through a nylon membrane and concentrated. Chromatography provided the title compound. $^1$H NMR (500 MHz, DMSO-$d_6$) δ ppm 8.60 (s, 1H), 8.50 (d, J=5.0 Hz, 1H), 8.35 (s, 1H), 7.49-7.40 (m, 3H), 7.13 (m, 2H), 4.79 (m, 4H), 4.56 (m, 1H), 4.05 (m, 1H), 3.12 (m, 1H), 2.90 (m, 1H), 2.71 (m, 1H), 2.57 (m, 1H), 1.79 (m, 2H), 1.55-1.30 (m, 2H), 1.02 (m, 6H); MS (ESI(+)) m/e 393 (M+H)$^+$.

Example 647

N-(4-{1-[(2-methoxyethoxy)acetyl]piperidin-4-yl}phenyl)-1,3-dihydro-2H-isoindole-2-carboxamide The title compound was prepared as described in Example 646, substituting N-(4-{1-[(2-methoxyethoxy)acetyl]-1,2,3,6-tetrahydropyridin-4-yl}phenyl)-1,3-dihydro-2H-isoindole-2-carboxamide for N-[4-(1-isobutyryl-1,2,3,6-tetrahydropyridin-4-yl)phenyl]-1,3-dihydro-2H-pyrrolo[3,4-c]pyridine-2-carboxamide. $^1$H NMR (500 MHz, DMSO-$d_6$) δ ppm 8.27 (s, 1H), 7.47 (m, 2H), 7.39-7.28 (m, 4H), 7.12 (m, 2H), 4.75 (bs, 4H), 4.47 (m, 1H), 4.24-4.09 (m, 2H), 3.90 (m, 1H), 3.57 (m, 2H), 3.47 (t, J=4.7 Hz, 2H), 3.26 (s, 3H), 3.06 (m, 1H), 2.70 (m, 1H), 2.62 (m, 1H), 1.77 (m, 2H), 1.57 (m, 1H), 1.42 (m, 1H); MS (ESI(+)) m/e 438 (M+H)$^+$.

Example 648

N-{5-[1-(tetrahydrofuran-3-ylcarbonyl)piperidin-4-yl]pyridin-2-yl}-1,3-dihydro-2H-isoindole-2-carboxamide The title compound was prepared as described in Example 646, substituting N-[1'-(tetrahydrofuran-3-ylcarbonyl)-1',2',3',6'-tetrahydro-3,4'-bipyridin-6-yl]-1,3-dihydro-2H-isoindole-2-carboxamide for N-[4-(1-isobutyryl-1,2,3,6-tetrahydropyridin-4-yl)phenyl]-1,3-dihydro-2H-pyrrolo[3,4-c]pyridine-2-carboxamide. $^1$H NMR (500 MHz, DMSO-$d_6$) δ ppm 8.81 (s, 1H), 8.16 (d, J=2.4 Hz, 1H), 7.85 (d, J=8.6 Hz, 1H), 7.63 (dd, J=8.7, 2.4 Hz, 1H), 7.39-7.25 (m, 4H), 4.80 (s, 4H), 4.56 (d, J=13.1 Hz, 1H), 4.08 (d, J=12.3 Hz, 1H), 3.88 (m, 1H), 3.72 (m, 3H), 3.38 (m, 1H), 3.11 (m, 1H), 2.78 (dd, J=11.9, 9.2 Hz, 1H), 2.63 (m, 1H), 2.03 (m, 2H), 1.80 (t, J=15.4 Hz, 2H), 1.51 (m, 2H); MS (ESI(+)) m/e 421 (M+H)$^+$.

Example 651

N-(1'-isobutyryl-1',2',3',6'-tetrahydro-2,4'-bipyridin-5-yl)-1,3-dihydro-2H-pyrrolo[3,4-c]pyridine-2-carboxamide

Example 651A

N-(6-chloropyridin-3-yl)-1H-pyrrolo[3,4-c]pyridine-2(3H)-carboxamide

The title compound was prepared as described in Example 1A, substituting 2-chloro-5-isocyanatopyridine for methyl 4-isocyanatobenzoate and 2,3-dihydro-1H-pyrrolo[3,4-c]pyridine for isoindoline.

Example 651B tert-butyl 4-(5-(2,3-dihydro-1H-pyrrolo[3,4-c]pyridine-2-carboxamido)pyridin-2-yl)-5,6-dihydropyridine-1(2H)-carboxylate The title compound was prepared as described in Example 280, substituting tert-butyl 4-(4,4,5,5-tetramethyl-1,3,2-dioxaborolan-2-yl)-5,6-dihydropyridine-1(2H)-carboxylate for 1H-pyrazol-3-ylboronic acid and N-(6-chloropyridin-3-yl)-1H-pyrrolo[3,4-c]pyridine-2(3H)-carboxamide for 5-bromo-N-(4-(propylcarbamoyl)phenyl)isoindoline-2-carboxamide.

Example 651C

N-(6-(1,2,3,6-tetrahydropyridin-4-yl)pyridin-3-yl)-1H-pyrrolo[3,4-c]pyridine-2(3H)-carboxamide The title compound was prepared as described in Example 2D, substituting tert-butyl 4-(5-(2,3-dihydro-1H-pyrrolo[3,4-c]pyridine-2-carboxamido)pyridin-2-yl)-5,6-dihydropyridine-1(2H)-carboxylate for tert-butyl 4-((4-(5-fluoroisoindoline-2-carboxamido)benzamido)methyl)benzylcarbamate.

Example 651D

N-(1'-isobutyryl-1',2',3',6'-tetrahydro-2,4'-bipyridin-5-yl)-1,3-dihydro-2H-pyrrolo[3,4-c]pyridine-2-carboxamide The title compound was prepared as described in Example 1C, substituting N-(6-(1,2,3,6-tetrahydropyridin-4-yl)pyridin-3-yl)isoindoline-2-carboxamide for 3-phenylpropan-1-amine and isobutanoic acid for 4-(isoindoline-2-carboxamido)benzoic acid. $^1$H NMR (501 MHz, DMSO-$d_6$, Temp=90° C.) δ ppm 8.73 (d, J=2.6 Hz, 1H), 8.64 (s, 1H), 8.52 (m, 2H), 7.99 (dd, J=8.6, 2.6 Hz, 1H), 7.49 (d, J=8.7 Hz, 1H), 7.44 (d, J=5.0 Hz, 1H), 6.60 (m, 1H), 4.88 (bs, 2H), 4.85 (d, J=2.3 Hz, 2H), 4.22 (m, 2H), 3.73 (t, J=5.7 Hz, 2H), 2.96 (m, 1H), 2.63 (m, 2H), 1.08 (d, J=6.7 Hz, 6H); MS (ESI(+)) m/e 392 (M+H)$^+$.

Table 13.

The following Examples were essentially prepared as described in Example 1C, substituting N-(6-(1,2,3,6-tetrahydropyridin-4-yl)pyridin-3-yl)-1H-pyrrolo[3,4-c]pyridine-2(3H)-carboxamide for 3-phenylpropan-1-amine and the corresponding carboxylic acid for 4-(isoindoline-2-carboxamido)benzoic acid.

| Ex | Name | $^1$H NMR | MS |
| --- | --- | --- | --- |
| 652 | N-(1'-benzoyl-1',2',3',6'-tetrahydro-2,4'-bipyridin-5-yl)-1,3-dihydro-2H-pyrrolo[3,4-c]pyridine-2-carboxamide | $^1$H NMR (400 MHz, DMSO-$d_6$, Temp = 90° C.) δ ppm 8.70 (d, J = 2.6 Hz, 1H), 8.60 (s, 1H), 8.49 (d, J = 5.0 Hz, 1H), 8.44 (s, 1H), 7.96 (dd, J = 8.6, 2.6 Hz, 1H), 7.49-7.37 (m, 7H), 6.56 (bs, 1H), 4.83 (m, 4H), 4.22 (m, 2H), 3.64 (m, 2H), 2.64 (m, 2H) | (ESI (+)) m/e 426 (M + H)$^+$ |

-continued

| Ex | Name | ¹H NMR | MS |
|----|------|--------|-----|
| 653 | N-[1'-(tetrahydrofuran-3-ylcarbonyl)-1',2',3',6'-tetrahydro-2,4'-bipyridin-5-yl]-1,3-dihydro-2H-pyrrolo[3,4-c]pyridine-2-carboxamide | ¹H NMR (400 MHz, DMSO-$d_6$, Temp = 90° C.) δ ppm 8.70 (s, 1H), 8.60 (bs, 1H), 8.49 (dd, J = 8.6, 2.7 Hz, 1H), 8.43 (s, 1H), 7.95 (d, J = 2.7 Hz, 1H), 7.45 (d, J = 8.6, 1H), 7.40 (d, J = 2.7 Hz, 1H) 6.56 (bs, 1H), 4.78 (m, 4H), 4.20 (m, 2H), 3.92 (m, 1H), 3.72 (m, 4H), 3.40 (m, 1H), 2.60 (m, 2H), 2.05 (m, 3H) | (ESI (+)) m/e 420 (M + H)⁺ |
| 654 | N-{1'-[(2-methoxyethoxy)acetyl]-1',2',3',6'-tetrahydro-2,4'-bipyridin-5-yl}-1,3-dihydro-2H-pyrrolo[3,4-c]pyridine-2-carboxamide | ¹H NMR (501 MHz, DMSO-$d_6$, Temp = 90° C.) δ ppm 8.69 (d, J = 2.6 Hz, 1H), 8.59 (s, 1H), 8.49 (d, J = 5.0 Hz, 1H), 8.47 (m, 1H), 7.95 (dd, J = 8.6, 2.6 Hz, 1H), 7.45 (d, J = 8.7 Hz, 1H), 7.40 (d, J = 5.1 Hz, 1H), 6.55 (bs, 1H), 4.84 (bs, 2H), 4.81 (bs, 2H), 4.19 (s, 2H), 4.14 (m, 2H), 3.65 (m, 2H), 3.60 (m, 2H), 3.48 (m, 2H), 3.26 (s, 3H), 2.60 (m, 2H) | (ESI (+)) m/e 438 (M + H)⁺ |
| 700 | N-[1'-(tetrahydrofuran-2-ylcarbonyl)-1',2',3',6'-tetrahydro-2,4'-bipyridin-5-yl]-1,3-dihydro-2H-pyrrolo[3,4-c]pyridine-2-carboxamide | ¹H NMR (400 MHz, DMSO-$d_6$, Temp = 90° C.) δ ppm 8.69 (dd, J = 8.7, 2.6 Hz, 1H), 8.59 (s, 1H), 8.48 (d, J = 8.7, 1H), 8.42 (bs, 1H), 7.94 (dd, J = 8.7, 2.6 Hz, 1H), 7.44 (m, 1H), 7.39 (d, J = 5.1, 1H) 6.55 (m, 1H), 4.82 (m, 4H), 4.68 (dd, J = 7.5, 5.8 Hz, 1H), 4.19 (bs, 2H), 3.88-3.62 (m, 4H), 2.60 (m, 2H), 2.10 (m, 1H), 2.01 (m, 1H), 1.87 (m, 2H) | (ESI (+)) m/e 420 (M + H)⁺ |
| 701 | N-[1'-(tetrahydro-2H-pyran-4-ylcarbonyl)-1',2',3',6'-tetrahydro-2,4'-bipyridin-5-yl]-1,3-dihydro-2H-pyrrolo[3,4-c]pyridine-2-carboxamide | ¹H NMR (400 MHz, DMSO-$d_6$, Temp = 90° C.) δ ppm 8.69 (d, J = 2.5 Hz, 1H), 8.59 (s, 1H), 8.48 (d, J = 5.0 Hz, 1H), 8.42 (s, 1H), 7.94 (dd, J = 8.7, 2.6 Hz, 1H), 7.44 (d, J = 8.6 Hz, 1H), 7.39 (d, J = 4.9 Hz, 1H), 6.55 (m, 1H), 4.82 (m, 4H), 4.18 (bs, 2H), 3.85 (m, 2H), 3.70 (t, J = 5.8 Hz, 2H), 3.42 (td, J = 11.4, 2.5 Hz, 2H), 2.92 (m, 1H), 2.60 (bs, 2H), 1.66 (m, 2H), 1.57 (m, 2H) | (ESI (+)) m/e 434 (M + H)⁺ |
| 702 | N-[1'-(1,4-dioxan-2-ylcarbonyl)-1',2',3',6'-tetrahydro-2,4'-bipyridin-5-yl]-1,3-dihydro-2H-pyrrolo[3,4-c]pyridine-2-carboxamide | ¹H NMR (400 MHz, DMSO-$d_6$, Temp = 90° C.) δ ppm 8.69 (dd, J = 2.7, 0.5 Hz, 1H), 8.59 (s, 1H), 8.48 (d, J = 5.0 Hz, 1H), 8.43 (bs, 1H), 7.94 (dd, J = 8.7, 2.6 Hz, 1H), 7.43 (m, 1H), 7.39 (m, 1H), 6.54 (m, 1H), 4.82 (m, 4H), 4.37 (dd, J = 9.2, 2.9 Hz, 1H), 4.18 (bs, 2H), 3.82-3.61 (m, 7H), 3.52 (m, 1H), 2.61 (s, 2H) | (ESI (+)) m/e 436 (M + H)⁺ |
| 703 | N-{1'-[(1,1-dioxidotetrahydrothiophen-3-yl)carbonyl]-1',2',3',6'-tetrahydro-2,4'-bipyridin-5-yl}-1,3-dihydro-2H-pyrrolo[3,4-c]pyridine-2-carboxamide | ¹H NMR (400 MHz, DMSO-$d_6$, Temp = 90° C.) δ ppm 8.69 (d, J = 2.4 Hz, 1H), 8.59 (s, 1H), 8.48 (d, J = 5.0 Hz, 1H), 8.43 (s, 1H), 7.95 (dd, J = 8.7, 2.6 Hz, 1H), 7.45 (d, J = 8.7 Hz, 1H), 7.39 (d, J = 4.9 Hz, 1H), 6.55 (m, 1H), 4.82 (m, 4H), 4.21 (s, 2H), 3.85-3.65 (m, 3H), 3.35-3.13 (m, 3H), 3.06 (m, 1H), 2.63 (bs, 2H), 2.37 (m, 1H), 2.13 (m, 1H) | (ESI (+)) m/e 468 (M + H)⁺ |
| 704 | N-[1'-(2-hydroxy-2-methylpropanoyl)-1',2',3',6'-tetrahydro-2,4'-bipyridin-5-yl]-1,3-dihydro-2H-pyrrolo[3,4-c]pyridine-2-carboxamide | ¹H NMR (400 MHz, DMSO-$d_6$, Temp = 90° C.) δ ppm 8.68 (s, 1H), 8.59 (s, 1H), 8.48 (d, J = 4.8 Hz, 1H), 8.41 (s, 1H), 7.94 (m, 1H), 7.43 (m, 8.6 Hz, 1H), 7.39 (d, J = 4.7 Hz, 1H), 6.55 (m, 1H), 5.09 (s, 1H), 4.82 (m, 4H), 4.32 (bs, 2H), 3.92 (bs, 2H), 2.59 (bs, 2H), 1.37 (s, 6H) | (ESI (+)) m/e 408 (M + H)⁺ |

Example 699

N-{4-[1-(pyridin-2-ylcarbonyl)piperidin-4-yl]butyl}-1,3-dihydro-2H-isoindole-2-carboxamide The title compound was prepared as described in Example 278, substituting picolinoyl chloride for acetyl chloride and N-[4-(piperidin-4-yl)butyl]-1,3-dihydro-2H-isoindole-2-carboxamide for 5-amino-N-(4-(propylcarbamoyl)phenyl)isoindoline-2-carboxamide. ¹H NMR (300 MHz, DMSO-$d_6$) δ ppm 8.56 (d, J=4.76 Hz, 1H) 7.83-7.97 (m, 1H) 7.38-7.57 (m, 2H) 7.18-7.40 (m, 4H) 6.27 (t, J=5.55 Hz, 1H) 4.56 (s, 4H) 4.47 (d, J=13.09 Hz, 1H) 3.59 (d, J=13.88 Hz, 1H) 3.00-3.16 (m, 3H) 2.92-3.01 (m, 1H) 2.68-2.81 (m, 1H) 1.77 (d, J=12.69 Hz, 1H) 0.97-1.64 (m, 11H); MS (ESI(+)) m/e 407 (M+H)⁺.

Example 718

N-(4-{[(3S)-tetrahydrofuran-3-ylmethyl]carbamoyl}phenyl)-1,3-dihydro-2H-pyrrolo[3,4-c]pyridine-2-carboxamide

Example 718A benzyl (tetrahydrofuran-3-yl)methylcarbamate

Racemic (tetrahydrofuran-3-yl)methanamine (3.84 g, 38.0 mmol) and diisopropylethylamine (13.26 ml, 76 mmol), were dissolved in dichloromethane (100 ml) and cooled to 0° C. The mixture was treated dropwise via an addition funnel with benzyl carbonochloridate (6.19 ml, 41.8 mmol) dissolved in 30 ml dichlormethane. After the addition the cooling bath was removed and the homogeneous solution was stirred at ambient temperature overnight. The reaction mixture was parti-

Example 718B (S)-benzyl (tetrahydrofuran-3-yl)methylcarbamate

A racemic mixture of benzyl (tetrahydrofuran-3-yl)methylcarbamate was dissolved in tetrahydrofuran and separated by liquid chromatography with a Chiralpak IC 2.5 cm ID×25 cm, 20 micron column, eluting with hexane/tetrahydrofuran/isopropanol (85/10/5), to provide (R)-benzyl (tetrahydrofuran-3-yl)methylcarbamate and (S)-benzyl (tetrahydrofuran-3-yl)methylcarbamate.

Example 718C (S)-(tetrahydrofuran-3-yl)methanamine (R)-Benzyl (tetrahydrofuran-3-yl)methylcarbamate (8.9 g, 37.8 mmol) and ethanol (160 ml) were added to 20% wet palladium (II) hydroxide (0.890 g, 6.34 mmol) in a 250 mL stainless steel pressure bottle and stirred for 40 minutes at 30 psi and room temperature. The mixture was filtered through a nylon filter and acidified with 4N HCl in dioxane (5 eq). Concentration and drying provided the title compound.

Example 718D

N-(4-{[(3S)-tetrahydrofuran-3-ylmethyl]carbamoyl}phenyl)-1,3-dihydro-2H-pyrrolo[3,4-c]pyridine-2-carboxamide The title compound was prepared as described in Example 1C, substituting (S)-(tetrahydrofuran-3-yl)methanamine for 3-phenylpropan-1-amine and 4-(2,3-dihydro-1H-pyrrolo[3,4-c]pyridine-2-carboxamido)benzoic acid for 4-(isoindoline-2-carboxamido)benzoic acid. $^1$H NMR (300 MHz, DMSO-$d_6$) δ 8.64 (s, 2H), 8.61 (s, 1H), 8.50 (d, J=5.0 Hz, 1H), 8.38 (t, J=5.7 Hz, 1H), 7.81-7.74 (m, 2H), 7.69-7.62 (m, 2H), 7.44 (d, J=5.1 Hz, 1H), 4.86-4.79 (m, 4H), 3.80-3.66 (m, 2H), 3.67-3.56 (m, 1H), 3.47 (dd, J=8.5, 5.3 Hz, 1H), 3.21 (dt, J=13.2, 5.8 Hz, 1H), 2.01-1.86 (m, 1H), 1.67-1.53 (m, 1H); MS (ESI(+)) m/e 367 (M+H)$^+$.

Example 720

N-(7-oxo-7-{[(3R)-tetrahydrofuran-3-ylmethyl]amino}heptyl)-1,3-dihydro-2H-isoindole-2-carboxamide

Example 720A methyl 7-(isoindoline-2-carboxamido)heptanoate

The title compound was prepared as described in Example 344A, substituting methyl 7-aminoheptanoate for tert-butyl 5-aminoisoindoline-2-carboxylate.

Example 720B 7-(isoindoline-2-carboxamido)heptanoic acid

The title compound was prepared as described in Example 1B, substituting methyl 7-(isoindoline-2-carboxamido)heptanoate for methyl 4-(isoindoline-2-carboxamido)benzoate.

Example 720C

N-(7-oxo-7-{[(3R)-tetrahydrofuran-3-ylmethyl]amino}heptyl)-1,3-dihydro-2H-isoindole-2-carboxamide The title compound was prepared as described in Example 1C, substituting (R)-(tetrahydrofuran-3-yl)methanamine for 3-phenylpropan-1-amine and 7-(isoindoline-2-carboxamido)heptanoic acid for 4-(isoindoline-2-carboxamido)benzoic acid. $^1$H NMR (300 MHz, DMSO-$d_6$) δ ppm 7.85 (t, J=5.76 Hz, 1H) 7.20-7.37 (m, 4H) 6.26 (t, J=5.59 Hz, 1H) 4.57 (s, 4H) 3.49-3.79 (m, 3H) 3.35 (dd, J=8.48, 5.43 Hz, 1H) 2.94-3.15 (m, 4H) 2.18-2.38 (m, 1H) 2.05 (t, J=7.29 Hz, 2H) 1.79-1.98 (m, 1H) 1.35-1.60 (m, 7H) 1.17-1.35 (m, 2H); MS (ESI(+)) m/e 374 (M+H)$^+$.

Example 721

N-{7-oxo-7-[(tetrahydro-2H-pyran-4-ylmethyl)amino]heptyl}-1,3-dihydro-2H-isoindole-2-carboxamide The title compound was prepared as described in Example 1C, substituting (tetrahydro-2H-pyran-4-yl)methanamine for 3-phenylpropan-1-amine and 7-(isoindoline-2-carboxamido)heptanoic acid for 4-(isoindoline-2-carboxamido)benzoic acid. $^1$H NMR (300 MHz, DMSO-$d_6$) δ ppm 7.76 (t, J=5.75 Hz, 1H) 7.20-7.40 (m, 4H) 6.26 (t, J=5.55 Hz, 1H) 4.57 (s, 4H) 3.82 (dd, J=11.10, 2.78 Hz, 2H) 3.14-3.29 (m, 2H) 3.05 (q, J=6.74 Hz, 2H) 2.92 (t, J=6.15 Hz, 2H) 2.06 (t, J=7.54 Hz, 2H) 1.33-1.65 (m, 9H) 1.19-1.34 (m, 2H) 0.98-1.22 (m, 2H); MS (ESI(+)) m/e 388 (M+H)$^+$.

Example 722

N-[4-(1-benzoylpiperidin-4-yl)butyl]-1,3-dihydro-2H-pyrrolo[3,4-c]pyridine-2-carboxamide

Example 722A tert-butyl 4-(4-(2,3-dihydro-1H-pyrrolo[3,4-c]pyridine-2-carboxamido)butyl)piperidine-1-carboxylate The title compound was prepared as described in Example 344, substituting tert-butyl 4-(4-aminobutyl)piperidine-1-carboxylate for tert-butyl 5-aminoisoindoline-2-carboxylate and substituting 1,3-dihydro-2H-pyrrolo[3,4-c]pyridine for isoindoline in Example 344A.

Example 722B

N-(4-(piperidin-4-yl)butyl)-1H-pyrrolo[3,4-c]pyridine-2(3H)-carboxamide

The title compound was prepared as described in Example 2D, substituting tert-butyl 4-(4-(2,3-dihydro-1H-pyrrolo[3,4-c]pyridine-2-carboxamido)butyl)piperidine-1-carboxylate The title compound was prepared as described, mentioned between water and ethyl acetate and the separated aqueous layer was extracted with ethyl acetate. The combined organic layers were washed with brine, dried over magnesium sulfate, filtered and concentrated. Chromatography provided the title compound.

for tert-butyl 4-((4-(5-fluoroisoindoline-2-carboxamido)benzamido)methyl)benzylcarbamate.

Example 722C

N-[4-(1-benzoylpiperidin-4-yl)butyl]-1,3-dihydro-2H-pyrrolo[3,4-c]pyridine-2-carboxamide The title compound was prepared as described in Example 1C, substituting N-(4-(piperidin-4-yl)butyl)-1H-pyrrolo[3,4-c]pyridine-2(3H)-carboxamide for 3-phenylpropan-1-amine and benzoic acid for 4-(isoindoline-2-carboxamido)benzoic acid. $^1$H NMR (500 MHz, DMSO-$d_6$, Temp=90° C.) δ ppm 8.54 (s, 1H) 8.45 (d, J=5.04 Hz, 1H) 7.38-7.46 (m, 3H) 7.28-7.37 (m, 3H) 6.09 (s, 1H) 4.62 (dd, J=9.08, 1.60 Hz, 4H) 3.07-3.15 (m, 2H) 2.79-2.94 (m, 2H) 1.61-1.75 (m, 2H) 1.41-1.58 (m, 3H) 1.20-1.40 (m, 4H) 0.99-1.17 (m, 2H); MS (ESI (+)) m/e 407 (M+H)$^+$.

Table 14.

The following Examples were essentially prepared as described in Example 722C, substituting an appropriate carboxylic acid for benzoic acid.

| Ex | Name | $^1$H NMR | MS |
|---|---|---|---|
| 757 | N-{4-[1-(2-chlorobenzoyl)piperidin-4-yl]butyl}-1,3-dihydro-2H-pyrrolo[3,4-c]pyridine-2-carboxamide | $^1$H NMR (300 MHz, DMSO-$d_6$) δ 8.55 (s, 1 H) 8.46 (d, J = 5.16 Hz, 1 H) 7.25-7.57 (m, 5 H) 6.36 (t, J = 5.55 Hz, 1 H) 4.60 (s, 2 H) 4.60 (s, 2 H) 4.43-4.54 (m, 1 H) 3.13-3.28 (m, 3 H) 2.85-3.12 (m, 3 H) 2.74 (t, J = 12.10 Hz, 1 H) 1.76 (d, J = 13.09 Hz, 1 H) 0.86-1.67 (m, 10 H) | (ESI (+)) m/e 441 (M + H)$^+$ |
| 1350 | N-{4-[1-(tetrahydrofuran-2-ylacetyl)piperidin-4-yl]butyl}-1,3-dihydro-2H-pyrrolo[3,4-c]pyridine-2-carboxamide | $^1$H NMR (400 MHz, DMSO, Temp = 90° C.) δ 8.63 (s, 1H), 8.53 (d, J = 5.3 Hz, 1H), 7.52 (d, J = 5.3 Hz, 1H), 6.13-5.96 (m, 1H), 4.67 (s, 1H), 4.09 (p, J = 6.6 Hz, 2H), 3.73 (q, J = 7.2 Hz, 5H), 3.10 (t, J = 7.0 Hz, 2H), 2.82-2.55 (m, 3H), 2.35 (dd, J = 14.8, 6.5 Hz, 2H), 2.04-1.92 (m, 2H), 1.79 (tt, J = 12.8, 6.3 Hz, 2H), 1.66 (d, J = 12.9 Hz, 2H), 1.54-1.42 (m, 3H), 1.39-1.29 (m, 2H), 1.24 (dd, J = 14.3, 5.9 Hz, 2H), 1.06-0.90 (m, 2H) | (ESI (+)) m/e 415 (M + H)$^+$ |
| 1351 | N-(4-{1-[(1,1-dioxidotetrahydrothiophen-3-yl)carbonyl]piperidin-4-yl}butyl)-1,3-dihydro-2H-pyrrolo[3,4-c]pyridine-2-carboxamide | 1H NMR (400 MHz, DMSO, Temp = 90° C.) δ 8.64 (s, 1H), 8.55 (d, J = 5.2 Hz, 1H), 7.55 (d, J = 5.3 Hz, 1H), 6.08 (s, 1H), 4.68 (s, 5H), 3.70-3.58 (m, 2H), 3.22-3.15 (m, 3H), 3.15-3.00 (m, 3H), 2.29 (td, J = 12.8, 7.0 Hz, 2H), 2.08 (ddd, J = 17.0, 13.4, 8.8 Hz, 2H), 1.69 (d, J = 12.9 Hz, 2H), 1.50 (ddt, J = 21.4, 14.3, 7.3 Hz, 3H), 1.40-1.21 (m, 4H), 1.03 (d, J = 11.6 Hz, 2H) | (ESI (+)) m/e 449 (M + H)$^+$ |
| 1352 | N-{4-[1-(tetrahydrofuran-3-ylacetyl)piperidin-4-yl]butyl}-1,3-dihydro-2H-pyrrolo[3,4-c]pyridine-2-carboxamide | $^1$H NMR (400 MHz, DMSO, Temp = 90° C.) δ 8.62 (s, 1H), 8.52 (d, J = 5.3 Hz, 1H), 7.51 (d, J = 5.1 Hz, 1H), 6.13-5.95 (m, 1H), 4.65 (d, J = 7.1 Hz, 4H), 3.83-3.75 (m, 1H), 3.70 (td, J = 8.0, 5.3 Hz, 1H), 3.57 (dd, J = 24.8, 17.4 Hz, 2H), 3.28-3.14 (m, 3H), 3.10 (t, J = 7.0 Hz, 2H), 2.40-2.26 (m, 3H), 1.99 (dt, J = 12.8, 7.6 Hz, 2H), 1.66 (d, J = 10.4 Hz, 3H), 1.55-1.40 (m, 3H), 1.36-1.16 (m, 3H), 0.99 (d, J = 9.4 Hz, 3H) | (ESI (+)) m/e 415 (M + H)$^+$ |
| 1353 | N-{4-[1-(cyclohexylcarbonyl)piperidin-4-yl]butyl}-1,3-dihydro-2H-pyrrolo[3,4-c]pyridine-2-carboxamide | $^1$H NMR (400 MHz, DMSO, Temp = 90° C.) δ 8.64 (s, 1H), 8.54 (d, J = 5.2 Hz, 1H), 7.54 (d, J = 5.3 Hz, 1H), 6.08 (s, 1H), 4.68 (s, 4H), 4.17-3.95 (m, 4H), 3.10 (t, J = 7.0 Hz, 2H), 2.78-2.53 (m, 3H), 1.72-1.62 (m, 5H), 1.57 (d, J = 14.8 Hz, 3H), 1.46 (dd, J = 14.3, 7.3 Hz, 3H), 1.39-1.13 (m, 6H), 1.03-0.91 (m, 2H) | (ESI (+)) m/e 413 (M + H)$^+$ |
| 1354 | N-(4-{1-[(4,4-difluorocyclohexyl)carbonyl]piperidin-4-yl}butyl)-1,3-dihydro-2H-pyrrolo[3,4-c]pyridine-2-carboxamide | $^1$H NMR (400 MHz, DMSO, Temp = 90° C.) δ 8.61 (s, 1H), 8.52 (d, J = 5.2 Hz, 1H), 7.49 (d, J = 5.2 Hz, 1H), 6.17-5.91 (m, 1H), 4.66 (s, 4H), 4.17-3.95 (m, 3H), 3.10 (t, J = 7.0 Hz, 2H), 2.84-2.68 (m, 3H), 2.09-1.96 (m, 2H), 1.93-1.77 (m, 2H), 1.65 (dd, J = 27.2, 12.8 Hz, 6H), 1.56-1.40 (m, 2H), 1.41-1.20 (m, 4H), 1.06-0.92 (m, 2H) | (ESI (+)) m/e 449 (M + H)$^+$ |
| 1355 | N-{4-[1-(2-hydroxy-2-methylpropanoyl)piperidin-4-yl]butyl}-1,3-dihydro-2H-pyrrolo[3,4-c]pyridine-2-carboxamide | $^1$H NMR (400 MHz, DMSO, Temp = 90° C.) δ 8.62 (s, 1H), 8.53 (d, J = 5.2 Hz, 1H), 7.51 (d, J = 5.2 Hz, 1H), 6.18-5.92 (m, 1H), 4.67 (s, 4H), 4.52-4.43 (m, 2H), 3.10 (t, J = 7.0 Hz, 2H), 2.82-2.70 (m, 2H), 1.70-1.62 (m, 2H), 1.56-1.42 (m, 4H), 1.32 (s, 8H), 1.28 (d, J = 13.3 Hz, 2H), 1.08-1.02 (m, 2H) | (ESI (+)) m/e 389 (M + H)$^+$ |
| 1356 | N-(4-{1-[(2R)-tetrahydrofuran-2-ylcarbonyl]piperidin-4-yl}butyl)-1,3-dihydro-2H-pyrrolo[3,4-c]pyridine-2-carboxamide | $^1$H NMR (400 MHz, DMSO, Temp = 90° C.) δ 8.63 (s, 1H), 8.53 (d, J = 5.2 Hz, 1H), 7.53 (d, J = 5.2 Hz, 1H), 6.08 (s, 1H), 4.67 (s, 4H), 4.58 (dd, J = 7.5, 5.6 Hz, 2H), 4.20-4.05 (m, 3H), 3.83-3.62 (m, 3H), 3.10 (t, J = 7.0 Hz, 2H), 2.76 (bs, 2H), 2.11-1.99 (m, 1H), 2.00-1.75 (m, 3H), 1.71-1.63 (m, 2H), 1.46 (dd, J = 14.2, 7.2 Hz, 2H), 1.37-1.19 (m, 2H), 1.10-0.92 (m, 2H) | (ESI (+)) m/e 401 (M + H)$^+$ |

| Ex | Name | ¹H NMR | MS |
|---|---|---|---|
| 1357 | N-(4-{1-[(2S)-tetrahydrofuran-2-ylcarbonyl]piperidin-4-yl}butyl)-1,3-dihydro-2H-pyrrolo[3,4-c]pyridine-2-carboxamide | ¹H NMR (400 MHz, DMSO, Temp = 90° C.) δ 8.62 (s, 1H), 8.53 (d, J = 5.2 Hz, 1H), 7.51 (d, J = 5.2 Hz, 1H), 6.07 (s, 1H), 4.67 (s, 4H), 4.58 (dd, J = 7.5, 5.6 Hz, 1H), 3.77 (q, J = 7.2 Hz, 2H), 3.82-3.67 (m, 3H), 3.10 (t, J = 7.0 Hz, 2H), 2.75 (bs, 1H), 2.11-1.99 (m, 1H), 2.00-1.75 (m, 3H), 1.71-1.62 (m, 2H), 1.53-1.21 (m, 7H), 1.08-0.92 (m, 2H) | (ESI (+)) m/e 401 (M + H)⁺ |
| 1358 | N-{4-{1-[(2-methoxyethoxy)acetyl]piperidin-4-yl}butyl)-1,3-dihydro-2H-pyrrolo[3,4-c]pyridine-2-carboxamide | ¹H NMR (400 MHz, DMSO, Temp = 90° C.) δ 8.62 (s, 1H), 8.53 (d, J = 5.2 Hz, 1H), 7.51 (d, J = 5.2 Hz, 1H), 6.15-5.99 (m, 1H), 4.67 (s, 4H), 4.58 (dd, J = 7.5, 5.6 Hz, 2H), 3.77 (q, J = 7.2 Hz, 2H), 3.82-3.67 (m, 3H), 3.10 (t, J = 7.0 Hz, 2H), 2.75 (bs, 1H), 2.11-1.99 (m, 1H), 1.95 (ddd, J = 17.4, 9.9, 6.6 Hz, 1H), 1.88-1.77 (m, 1H), 1.71-1.62 (m, 2H), 1.46 (dd, J = 14.4, 7.4 Hz, 3H), 1.37-1.19 (m, 4H), 1.08-0.92 (m, 2H) | (ESI (+)) m/e 419 (M + H)⁺ |
| 1359 | N-{4-[1-(tetrahydrofuran-3-ylcarbonyl)piperidin-4-yl]butyl}-1,3-dihydro-2H-pyrrolo[3,4-c]pyridine-2-carboxamide | ¹H NMR (400 MHz, DMSO, Temp = 90° C.) δ 8.64 (s, 4H), 8.54 (d, J = 5.3 Hz, 1H), 7.55 (d, J = 5.3 Hz, 1H), 6.08 (s, 1H), 4.68 (s, 4H), 3.85 (t, J = 8.1 Hz, 1H), 3.73-3.58 (m, 2H), 3.33-3.22 (m, 2H), 3.10 (t, J = 7.0 Hz, 2H), 1.99 (dd, J = 14.3, 7.1 Hz, 3H), 1.68 (d, J = 12.7 Hz, 2H), 1.55-1.41 (m, 3H), 1.33 (dt, J = 13.8, 6.4 Hz, 2H), 1.24 (dd, J = 13.4, 6.3 Hz, 2H), 0.99 (dd, J = 24.0, 12.4 Hz, 2H) | (ESI (+)) m/e 401 (M + H)⁺ |
| 1360 | N-(4-{1-[(propan-2-yloxy)acetyl]piperidin-4-yl}butyl)-1,3-dihydro-2H-pyrrolo[3,4-c]pyridine-2-carboxamide | ¹H NMR (400 MHz, DMSO; Temp = 90° C.) δ 8.63 (s, 4H), 8.53 (d, J = 5.3 Hz, 1H), 7.53 (d, J = 5.2 Hz, 1H), 6.09 (s, 1H), 4.66 (d, J = 7.5 Hz, 5H), 3.60 (dt, J = 12.2, 6.1 Hz, 2H), 3.10 (t, J = 7.0 Hz, 2H), 1.67 (d, J = 13.1 Hz, 2H), 1.54-1.41 (m, 3H), 1.33 (dd, J = 15.9, 7.1 Hz, 2H), 1.24 (dd, J = 14.3, 5.7 Hz, 3H), 1.10 (d, J = 6.1 Hz, 6H), 1.02 (d, J = 11.2 Hz, 2H) | (ESI (+)) m/e 403 (M + H)⁺ |
| 1361 | N-{4-[1-(cyclopropylacetyl)piperidin-4-yl]butyl}-1,3-dihydro-2H-pyrrolo[3,4-c]pyridine-2-carboxamide | ¹H NMR (400 MHz, DMSO, Temp = 90°) δ 8.63 (s, 4H), 8.54 (d, J = 5.3 Hz, 1H), 7.54 (d, J = 5.3 Hz, 1H), 6.13-6.00 (m, 1H), 4.67 (s, 4H), 3.10 (t, J = 7.0 Hz, 2H), 2.22 (d, J = 6.6 Hz, 2H), 1.63 (t, J = 21.9 Hz, 2H), 1.47 (dt, J = 14.1, 7.0 Hz, 3H), 1.38-1.28 (m, 2H), 1.24 (dd, J = 14.3, 5.8 Hz, 2H), 1.07-0.85 (m, 4H), 0.47-0.39 (m, 2H), 0.15-0.05 (m, 2H) | (ESI (+)) m/e 385 (M + H)⁺ |
| 1362 | N-{4-[1-(4,4,4-trifluorobutanoyl)piperidin-4-yl]butyl}-1,3-dihydro-2H-pyrrolo[3,4-c]pyridine-2-carboxamide | ¹H NMR (400 MHz, DMSO Temp = 90°) δ 8.63 (s, 4H), 8.53 (d, J = 5.3 Hz, 1H), 7.52 (d, J = 5.3 Hz, 1H), 6.07 (s, 1H), 4.67 (s, 4H), 3.10 (t, J = 7.0 Hz, 2H), 1.67 (d, J = 13.3 Hz, 2H), 1.47 (dt, J = 14.3, 7.1 Hz, 3H), 1.38-1.29 (m, 4H), 1.25 (dt, J = 13.6, 6.8 Hz, 3H), 1.03 (s, 3H) | (ESI (+)) m/e 427 (M + H)⁺ |

Example 753

N-{4-[5-(morpholin-4-ylmethyl)-1,2,4-oxadiazol-3-yl]phenyl}-1,3-dihydro-2H-isoindole-2-carboxamide

Example 753A

N-(4-(5-(chloromethyl)-1,2,4-oxadiazol-3-yl)phenyl)isoindoline-2-carboxamide

To a 25 mL round-bottomed flask containing (Z)—N-(4-(N'-hydroxycarbamimidoyl)phenyl)isoindoline-2-carboxamide (1.5 g, 5.06 mmol) in acetone (5 ml) was added potassium carbonate (7.00 g, 50.6 mmol) in a single portion. The reaction mixture was cooled to 0° C. and 2-chloroacetyl chloride (3.22 ml, 40.5 mmol) was added slowly. The resulting mixture was warmed to room temperature and stirred for two hours. The solvent was removed and the solid was triturated with water and then filtered with water washes. The dried solid was dissolved in DMF, heated to 100° C. and stirred for two hours. Work-up with water and dichlormethane followed by chromatography provided the title compound.

Example 753B

N-{4-[5-(morpholin-4-ylmethyl)-1,2,4-oxadiazol-3-yl]phenyl}-1,3-dihydro-2H-isoindole-2-carboxamide To a 20 mL vial was added N-(4-(5-(chloromethyl)-1,2,4-oxadiazol-3-yl)phenyl)isoindoline-2-carboxamide (50 mg, 0.141 mmol) and morpholine (36.8 mg, 0.423 mmol) in DMF (470 µl). The mixture was heated to 50° C. for 30 minutes, cooled, and diluted with 2 mL methanol. Chromatography provided the title compound. ¹H NMR (300 MHz, DMSO-d₆) δ 8.69 (s, 1H), 7.92 (d, J=8.8 Hz, 2H), 7.80 (d, J=8.9 Hz, 2H), 7.35 (ddd, J=8.8, 3.9, 2.4 Hz, 4H), 4.80 (s, 4H), 3.95 (s, 2H), 3.68-3.48 (m, 4H), 2.62-2.51 (m, 5H); MS (ESI(+)) m/e 406 (M+H)⁺.

Example 754

N-(4-{5-[(4-methylpiperazin-1-yl)methyl]-1,2,4-oxadiazol-3-yl}phenyl)-1,3-dihydro-2H-isoindole-2-carboxamide The title compound was prepared as described in Example 753B, substituting 1-methylpiperazine for morpholine. ¹H NMR (300 MHz, DMSO-d₆) δ 8.69 (s, 1H), 7.91 (d, J=8.8 Hz, 3H), 7.80 (d, J=8.8 Hz, 3H), 7.45-7.23 (m, 5H), 4.80 (s, 5H), 3.93 (s, 2H), 2.65-2.51 (m, 75H), 2.34 (s, 5H), 2.15 (s, 4H); MS (ESI(+)) m/e 419 (M+H)+.

Example 755

N-[4-(5-{[(3-methylbutyl)amino]methyl}-1,2,4-oxadiazol-3-yl)phenyl]-1,3-dihydro-2H-isoindole-2-carboxamide The title compound was prepared as described in Example 753B, substituting 3-methylbutan-1-amine for morpholine. $^1$H NMR (300 MHz, DMSO-$d_6$) δ ppm 8.68 (s, 1H), 7.91 (d, J=8.8 Hz, 2H), 7.79 (d, J=8.8 Hz, 2H), 7.35 (tdd, J=8.9, 5.4, 3.4 Hz, 4H), 4.80 (s, 4H), 4.02 (s, 2H), 2.66-2.53 (m, 1H), 2.43-2.30 (m, 1H), 1.63 (dt, J=13.4, 6.7 Hz, 1H), 1.32 (dd, J=14.4, 7.0 Hz, 2H), 0.86 (d, J=6.5 Hz, 6H); MS (ESI(+)) m/e 406 (M+H)+.

Example 756

N-(4-{5-[(4-hydroxypiperidin-1-yl)methyl]-1,2,4-oxadiazol-3-yl}phenyl)-1,3-dihydro-2H-isoindole-2-carboxamide The title compound was prepared as described in Example 753B, substituting piperidin-4-ol for morpholine. $^1$H NMR (300 MHz, DMSO-$d_6$) δ ppm 8.68 (s, 1H), 7.91 (d, J=8.8 Hz, 2H), 7.79 (d, J=8.8 Hz, 2H), 7.45-7.25 (m, 4H), 4.80 (s, 4H), 4.56 (d, J=4.2 Hz, 1H), 3.91 (s, 2H), 3.45 (dd, J=8.7, 4.3 Hz, 1H), 3.17 (d, J=5.2 Hz, 1H), 2.76 (dd, J=10.6, 5.0 Hz, 2H), 2.42-2.18 (m, 3H), 1.72 (d, J=8.9 Hz, 2H), 1.43 (dt, J=18.5, 6.4 Hz, 2H); MS (ESI(+)) m/e 420 (M+H)+.

Example 787

N-[4-(2-{benzyl[3-(morpholin-4-yl)propyl]amino}-2-oxoethyl)phenyl]-1,3-dihydro-2H-isoindole-2-carboxamide Example 787A N-benzyl-N-(3-morpholinopropyl)-2-(4-nitrophenyl)acetamide The title compound was prepared as described in Example 1C, substituting N-benzyl-3-morpholinopropan-1-amine for 3-phenylpropan-1-amine and 2-(4-nitrophenyl)acetic acid for 4-(isoindoline-2-carboxamido)benzoic acid.

Example 787B 2-(4-aminophenyl)-N-benzyl-N-(3-morpholinopropyl)acetamide

The title compound was prepared as described in Example 272A, substituting N-benzyl-N-(3-morpholinopropyl)-2-(4-nitrophenyl)acetamide for 4-nitro-N-propylbenzamide.

Example 787C

N-[4-(2-{benzyl[3-(morpholin-4-yl)propyl]amino}-2-oxoethyl)phenyl]-1,3-dihydro-2H-isoindole-2-carboxamide The title compound was prepared as described in Example 272B, substituting 2-(4-aminophenyl)-N-benzyl-N-(3-morpholinopropyl)acetamide for 4-amino-N-propylbenzamide and isoindoline for methyl isoindoline-5-carboxylate hydrochloride. $^1$H NMR (400 MHz, DMSO-$d_6$, Temp=90° C.) δ ppm 8.05 (bs, 1H), 7.47 (d, J=8.5 Hz, 2H), 7.37-7.17 (m, 9H), 7.15-7.08 (m, 2H), 4.76 (s, 4H), 4.56 (bs, 2H), 3.77-3.55 (m, 2H), 3.56-3.50 (m, 4H), 3.30 (t, J=7.3 Hz, 2H), 2.33-2.24 (m, 4H), 2.21 (t, J=6.8 Hz, 2H), 1.60 (p, J=7.1 Hz, 2H); MS (ESI(+)) m/e 513 (M+H)+.

Example 788

N-[4-(3-{benzyl[3-(morpholin-4-yl)propyl]amino}-3-oxopropyl)phenyl]-1,3-dihydro-2H-isoindole-2-carboxamide The title compound was prepared as described in Example 787, substituting 3-(4-nitrophenyl)propanoic acid for 2-(4-nitrophenyl)acetic acid in Example 787A. $^1$H NMR (400 MHz, DMSO-$d_6$, Temp=90° C.) δ ppm 7.99 (bs, 1H), 7.48-7.39 (m, 2H), 7.37-7.19 (m, 7H), 7.19-7.13 (m, 2H), 7.13-7.00 (m, 2H), 4.76 (s, 4H), 4.53 (s, 2H), 3.56-3.45 (m, 4H), 3.31-3.23 (m, 2H), 2.87-2.78 (m, 2H), 2.72-2.57 (m, 2H), 2.29-2.22 (m, 4H), 2.20 (t, J=6.8 Hz, 2H), 1.63-1.54 (m, 2H); MS (ESI(+)) m/e 527 (M+H)+.

Example 795

N-{6-[(tetrahydro-2H-pyran-4-ylmethyl)carbamoyl]pyridazin-3-yl}-1,3-dihydro-2H-isoindole-2-carboxamide The title compound was prepared as described in Example 1C, substituting tetrahydro-2H-pyran-4-ylmethamine for 3-phenylpropan-1-amine and 6-(isoindoline-2-carboxamido)pyridazine-3-carboxylic acid for 4-(isoindoline-2-carboxamido)benzoic acid. $^1$H NMR (300 MHz, DMSO-$d_6$) δ 9.98 (s, 1H), 9.03 (t, J=6.2 Hz, 1H), 8.31 (d, J=9.3 Hz, 1H), 8.10 (d, J=9.3 Hz, 1H), 7.41-7.28 (m, 4H), 5.03-4.67 (m, 4H), 3.89-3.79 (m, 2H), 3.29-3.11 (m, 4H), 2.01-1.78 (m, 1H), 1.63-1.53 (m, 2H), 1.30-1.12 (m, 2H); MS (ESI(+)) m/e 382 (M+H)+.

Example 797

N-[4-(6-bromo-2-oxoquinolin-1(2H)-yl)butyl]-1,3-dihydro-2H-isoindole-2-carboxamide Example 797A tert-butyl 4-(6-bromo-2-oxoquinolin-1(2H)-yl)butylcarbamate To a solution of 6-bromoquinolin-2(1H)-one (430 mg, 1.91 mmol) in tetrahydrofuran (8 ml) was added sodium bis(trimethylsilyl)amide (2.1 ml, 2.08 mmol). After 15 minutes, 4-(boc-amino)butyl bromide (403 mg, 1.6 mmol) was added. The solution was stirred for 15 hours, concentrated and purified by flash chromatography to provide the title compound.

Example 797B 1-(4-aminobutyl)-6-bromoquinolin-2(1H)-one

The title compound was prepared as described in Example 2D, substituting tert-butyl 4-(6-bromo-2-oxoquinolin-1(2H)- yl)butylcarbamate for tert-butyl 4-((4-(5-fluoroisoindoline-2-carboxamido)benzamido)methyl)benzylcarbamate.

Example 797C

N-[4-(6-bromo-2-oxoquinolin-1(2H)-yl)butyl]-1,3-dihydro-2H-isoindole-2-carboxamide The title compound was prepared as described in Example 272B, substituting 1-(4-aminobutyl)-6-bromoquinolin-2(1H)-one for 4-amino-N-propylbenzamide and isoindoline for methyl isoindoline-5-carboxylate hydrochloride. $^1$H NMR (400 MHz, CDCl$_3$) δ ppm 7.67 (d, J=2.2 Hz, 2H), 7.61 (d, J=2.3 Hz, 1H), 7.60 (d, J=2.3 Hz, 1H), 7.57 (d, J=9.6 Hz, 2H), 7.28 (s, 1H), 7.24 (s, 1H), 6.70 (d, J=9.5 Hz, 2H), 4.76 (t, J=5.7 Hz, 2H), 4.70 (s, 4H), 4.29 (m, 2H), 3.42 (m, 2H), 1.79 (m, 2H), 1.69 (m, 2H); MS (ESI(+)) m/e 440.1 (M+H).

Example 798

N-{4-[6-(3-acetylphenyl)-2-oxoquinolin-1(2H)-yl]butyl}-1,3-dihydro-2H-isoindole-2-carboxamide The title compound was prepared as described in Example 280, substituting 3-acetylphenyl boronic acid for 1H-pyrazol-3-ylboronic acid and N-[4-(6-bromo-2-oxoquinolin-1(2H)-yl)butyl]-1,3-dihydro-2H-isoindole-2-carboxamide for 5-bromo-N-(4-(propylcarbamoyl)phenyl)isoindoline-2-carboxamide. $^1$H NMR (400 MHz, CDCl$_3$) δ ppm 8.20 (t, J=1.5 Hz, 1H), 7.94 (d, J=7.7 Hz, 1H), 7.80 (m, 3H), 7.75 (d, J=9.5 Hz, 2H), 7.56 (t, J=7.7 Hz, 1H), 7.49 (d, J=9.4 Hz, 2H), 7.24 (s, 1H), 6.75 (t, J=9.4 Hz, 2H), 4.82 (t, J=5.4 Hz, 1H), 4.72 (s, 4H), 4.37 (m, 2H), 3.45 (m, 2H), 2.66 (s, 3H), 1.88 (m, 2H), 1.74 (m, 2H); MS (ESI(+)) m/e 480.3 (M+H).

Example 804

5-(hydroxymethyl)-N-(3-phenylpropyl)-1,3-dihydro-2H-isoindole-2-carboxamide

The title compound was prepared as described in Example 272B, substituting 3-phenylpropan-1-amine for 4-amino-N-propylbenzamide and isoindol-5-ylmethanol hydrochloride for methyl isoindoline-5-carboxylate hydrochloride. $^1$H NMR (300 MHz, DMSO-d$_6$) δ ppm 7.30-7.14 (m, 8H), 6.30 (t, J=5.5 Hz, 1H), 5.16 (t, J=5.5 Hz, 1H), 4.55 (bs, 4H), 4.49 (d, J=4.9 Hz, 2H), 3.16-3.05 (m, 2H), 2.64-2.56 (m, 2H), 1.76 (p, J=7.4 Hz, 2H); MS (ESI(+)) m/e 311 (M+H)$^+$.

Example 805

N-(2-{(4-fluorobenzyl)[4-(pyridin-3-yl)benzyl]amino}-1,3-thiazol-5-yl)-1,3-dihydro-2H-pyrrolo[3,4-c]pyridine-2-carboxamide

Example 805A methyl 2-(4-(pyridin-3-yl)benzylamino)thiazole-5-carboxylate

In a 250 mL round-bottomed flask was added 4-(pyridin-3-yl)benzaldehyde (4 g, 21.83 mmol), methyl 2-aminothiazole-5-carboxylate (3.45 g, 21.83 mmol), and acetic acid (0.375 ml, 6.55 mmol) in toluene (109 ml). The mixture was heated at reflux under Dean-Stark conditions for 3 hours, cooled, concentrated and redissolved in methanol. The mixture was cooled to 0° C. and sodium borohydride (1.322 g, 34.9 mmol) was carefully added. The mixture was warmed to room temperature and the resulting suspension was filtered with water washes to provide the title compound after drying.

Example 805B 2-((4-fluorobenzyl)(4-(pyridin-3-yl)benzyl)amino)thiazole-5-carboxylic acid In a 250 mL round-bottomed flask was added methyl 2-(4-(pyridin-3-yl)benzylamino)thiazole-5-carboxylate (3 g, 9.22 mmol) and 1-(bromomethyl)-4-fluorobenzene (1.264 ml, 10.14 mmol) in dimethylformamide (46.1 ml). The mixture was cooled to 0° C., sodium hydride (0.738 g, 18.44 mmol) was added carefully; and the mixture was warmed to room temperature. After the mixture was stirred for about 30 minutes, it was found to be predominantely carboxylic acid. 1 N NaOH was added to complete the conversion; and a water work up followed by chromatography provided the title compound.

Example 805C

N-(4-fluorobenzyl)-5-isocyanato-N-(4-(pyridin-3-yl)benzyl)thiazol-2-amine

To a 50 mL round-bottomed flask was added 2-((4-fluorobenzyl)(4-(pyridin-3-yl)benzyl)amino)thiazole-5-carboxylic acid (850 mg, 2.026 mmol) in dichloromethane (10.100 ml) and the solution was cooled to 0° C. Oxalyl chloride (0.266 ml, 3.04 mmol) and dimethylformamide (0.016 ml, 0.203 mmol) were added and some bubbling occurred. The solution was warmed to room temperature and stirred for 1 hour. The mixture was cooled to 0° C., and trimethylsilyl azide (0.538 ml, 4.05 mmol) was added. The mixture was warmed to room temperature, stirred for 30 minutes and concentrated under vacuum. Toluene (5 ml) was added and the mixture was heated to 95° C. for 2.5 hours. The toluene was removed and the resulting solid was triturated/sonicated with ether and filtered with ether washes to provide the title compound.

Example 805D

N-(2-{(4-fluorobenzyl)[4-(pyridin-3-yl)benzyl]amino}-1,3-thiazol-5-yl)-1,3-dihydro-2H-pyrrolo[3,4-c]pyridine-2-carboxamide The title compound was prepared as described in Example 1A, substituting N-(4-fluorobenzyl)-5-isocyanato-N-(4-(pyridin-3-yl)benzyl)thiazol-2-amine for methyl 4-isocyanatobenzoate and 1,3-dihydro-2H-pyrrolo[3,4-c]pyridine for isoindoline. $^1$H NMR (300 MHz, DMSO-d$_6$) δ ppm 9.27 (s, 1H), 8.99 (d, J=2.1 Hz, 1H), 8.76 (s, 1H), 8.71-8.56 (m, 2H), 8.29 (d, J=7.8 Hz, 1H), 7.81-7.56 (m, 5H), 7.51-7.27 (m, 5H), 7.27-7.06 (m, 2H), 6.86 (s, 1H), 4.80 (d, J=3.6 Hz, 4H), 4.72 (d, J=7.7 Hz, 4H); MS (ESI(+)) m/e 537 (M+H)$^+$.

Example 806

N-[4-(2-benzyl-1,3-thiazol-4-yl)phenyl]-1,3-dihydro-2H-isoindole-2-carboxamide

Example 806A 4-(2-benzylthiazol-4-yl)aniline

2-Bromo-1-(4-nitrophenyl)ethanone (0.5 g, 2.049 mmol) and 2-phenylethanethioamide (0.310 g, 2.049 mmol) were combined in ethanol (10 ml) in a 20 mL microwave reaction vessel and heated at 140° C. for 15 minutes. The solution was transferred to a 250 mL round bottom flask where it immediately solidified. The material was diluted with an additional ethanol (10 ml) and was heated at reflux with stirring until the solids were dissolved. Water (5.0 ml, 278 mmol), and hydrochloric acid (1 ml, 12.00 mmol) were added. Iron (0.625 g, 11.19 mmol) was added and the mixture was heated at reflux for 2 hours. The mixture was allowed to cool and 5 mL NH$_4$OH was added. The material was filtered through a pad of diatomaceous earth and the pad was washed with 50 mL of ethyl acetate. The filtrate was washed with 100 mL of water and the aqueous phase was extracted with an additional 50 mL of ethyl acetate. The combined organic fractions were dried over sodium sulfate, filtered, and the solvent was removed under reduced pressure. The material was re-dissolved in 50 mL of ethyl acetate and filtered through a ¼-inch pad of silica gel. The pad was washed with an additional 50 mL of ethyl acetate and the combined filtrate was concentrated to provide the title compound.

Example 806B

N-[4-(2-benzyl-1,3-thiazol-4-yl)phenyl]-1,3-dihydro-2H-isoindole-2-carboxamide

The title compound was prepared as described in Example 272B, substituting 4-(2-benzylthiazol-4-yl)aniline for 4-amino-N-propylbenzamide and isoindoline for methyl isoindoline-5-carboxylate hydrochloride. $^1$H NMR (400 MHz, CDCl$_3$) δ ppm 7.79 (d, J=8.7 Hz, 2H), 7.48 (d, J=8.7 Hz, 2H), 7.30 (s, 1H), 7.29 (d, J=3.8 Hz, 2H), 7.26 (m, 5H), 7.20 (d, J=3.7 Hz, 2H), 6.29 (s, 1H), 4.80 (s, 4H), 4.32 (s, 2H); MS (ESI(+)) m/e 412 (M+H).

Example 807

N-(7-{benzyl[3-(morpholin-4-yl)propyl]amino}-7-oxoheptyl)-1,3-dihydro-2H-isoindole-2-carboxamide The title compound was prepared as described in Example 1C, substituting N-benzyl-3-morpholinopropan-1-amine for 3-phenylpropan-1-amine and 7-(isoindoline-2-carboxamido)heptanoic acid for 4-(isoindoline-2-carboxamido)benzoic acid. $^1$H NMR (300 MHz, DMSO-d$_6$) δ ppm 7.41-7.13 (m, 9H), 6.32-6.22 (m, 1H), 4.59-4.48 (m, 6H), 3.58-3.47 (m, 4H), 3.27-3.20 (m, 2H), 3.11-2.98 (m, 2H), 2.44-2.36 (m, 1H), 2.31-2.23 (m, 5H), 2.23-2.12 (m, 2H), 1.70-1.17 (m, 10H); MS (ESI(+)) m/e 507 (M+H)$^+$.

Example 808

N-{4-[(3-methylbutyl)sulfamoyl]phenyl}-1,3-dihydro-2H-isoindole-2-carboxamide

Example 808A

N-isopentyl-4-nitrobenzenesulfonamide

4-Nitrobenzene-1-sulfonyl chloride (1.5 g, 6.57 mmol) was dissolved in dichloromethane (30 ml) and cooled to 0° C. followed by addition of diisopropylethylamine (2.293 ml, 13.13 mmol). 3-Methylbutan-1-amine (0.926 ml, 7.88 mmol) was dissolved in 5 ml dichloromethane and added via syringe. After the addition, the mixture was allowed to warm to room temperature for 3 hours. The solution was diluted with aqueous sodium bicarbonate and extracted twice with dichloromethane. The organics were combined, dried over magnesium sulfate, filtered and concentrated. Chromatography provided the title compound.

Example 808B 4-amino-N-isopentylbenzenesulfonamide

The title compound was prepared as described in Example 272A, substituting N-isopentyl-4-nitrobenzenesulfonamide for 4-nitro-N-propylbenzamide.

Example 808C

N-{4-[(3-methylbutyl)sulfamoyl]phenyl}-1,3-dihydro-2H-isoindole-2-carboxamide

The title compound was prepared as described in Example 272B, substituting 4-amino-N-isopentylbenzenesulfonamide for 4-amino-N-propylbenzamide and isoindoline for methyl isoindoline-5-carboxylate hydrochloride. $^1$H NMR (300 MHz, DMSO-d$_6$) δ ppm 8.75 (s, 1H), 7.82-7.74 (m, 2H), 7.70-7.64 (m, 2H), 7.41-7.27 (m, 5H), 4.80 (s, 4H), 2.77-2.67 (m, 2H), 1.64-1.47 (m, 1H), 1.30-1.19 (m, 2H), 0.79 (d, J=6.6 Hz, 6H); MS (ESI(+)) m/e 388 (M+H)$^+$.

Example 839

N-(5-{[(3S)-tetrahydrofuran-3-ylmethyl]carbamoyl}pyridin-2-yl)-1,3-dihydro-2H-isoindole-2-carboxamide The title compound was prepared as described in Example 1C, substituting (S)-benzyl (tetrahydrofuran-3-yl)methylcarbamate for 3-phenylpropan-1-amine and 6-(isoindoline-2-carboxamido)nicotinic acid for 4-(isoindoline-2-carboxamido)benzoic acid. $^1$H NMR (500 MHz, DMSO-d$_6$) δ ppm 9.27 (s, 1H), 8.74 (d, J=2.1 Hz, 1H), 8.60 (t, J=5.7 Hz, 1H), 8.14 (dd, J=8.8, 2.4 Hz, 1H), 8.00 (d, J=8.7 Hz, 1H), 7.41-7.27 (m, 4H), 4.89 (m, 4H), 3.75 (m, 1H), 3.69 (m, 1H), 3.62 (m, 1H), 3.48 (dd, J=8.5, 5.3 Hz, 1H), 3.25 (m, 2H), 2.48 (m, 1H), 1.95 (m, 1H), 1.61 (m, 1H); MS (ESI(+)) m/e 367 (M+H).

Example 871

N-[4-(4-{benzyl[3-(morpholin-4-yl)propyl]amino}-4-oxobutyl)phenyl]-1,3-dihydro-2H-isoindole-2-carboxamide The title compound was prepared as described in Example 787, substituting 3-(4-nitrophenyl)butanoic acid for 2-(4-nitrophenyl)acetic acid in Example 787A. $^1$H NMR (300 MHz, DMSO-d$_6$) δ ppm 8.29-8.21 (m, 1H), 7.51-7.41 (m, 2H), 7.40-7.13 (m, 9H), 7.11-6.98 (m, 2H), 4.75 (s, 4H), 4.57-4.47 (m, 2H), 3.60-3.44 (m, 4H), 3.27-3.13 (m, 2H), 2.60-2.53 (m, 1H), 2.48-2.34 (m, 2H), 2.33-2.11 (m, 7H), 1.90-1.71 (m, 2H), 1.66-1.51 (m, 2H); MS (ESI(+)) m/e 541 (M+H)$^+$.

Example 872

N-(4-phenylbutyl)-1,3-dihydro-2H-pyrrolo[3,4-c]pyridine-2-carboxamide

The title compound was prepared as described in Example 1A, substituting (4-isocyanatobutyl)benzene for methyl 4-isocyanatobenzoate and 1,3-dihydro-2H-pyrrolo[3,4-c]pyridine for isoindoline. $^1$H NMR (300 MHz, DMSO-d$_6$) δ ppm 8.55 (s, 1H), 8.46 (d, J=5.0 Hz, 1H), 7.38 (d, J=5.1 Hz, 1H), 7.32-7.22 (m, 2H), 7.23-7.11 (m, 3H), 6.38 (t, J=5.6 Hz, 1H), 4.63-4.57 (m, 4H), 3.10-3.07 (m, 2H), 2.59 (t, J=7.5 Hz, 2H), 1.66-1.39 (m, 4H); MS (ESI(+)) m/e 296 (M+H)$^+$.

Example 873

N-[4-(2-{benzyl[3-(morpholin-4-yl)propyl] amino}ethyl)phenyl]-1,3-dihydro-2H-isoindole-2-carboxamide Example 873A N-benzyl-3-morpholino-N-(4-nitrophenethyl)propan-1-amine A suspension of 1-(2-bromoethyl)-4-nitrobenzene (0.314 g, 1.366 mmol), N-benzyl-3-morpholinopropan-1-amine (0.128 g, 0.546 mmol), and potassium carbonate (0.189 g, 1.366 mmol) in dimethylformamide (1.821 ml) was heated at 65° C. for 20 hours. The reaction was partitioned in ethyl acetate and water. The organic layer was washed with brine, dried over anhydrous sodium sulfate, filtered, and concentrated. The concentrate was purified by flash chromatography to provide the title compound.

Example 873B 4-(2-(benzyl(3-morpholinopropyl)amino)ethyl) aniline

The title compound was prepared as described in Example 272A, substituting N-benzyl-3-morpholino-N-(4-nitrophenethyl)propan-1-amine for 4-nitro-N-propylbenzamide.

Example 873C

N-[4-(2-{benzyl[3-(morpholin-4-yl)propyl] amino}ethyl)phenyl]-1,3-dihydro-2H-isoindole-2-carboxamide The title compound was prepared as described in Example 272B, substituting 4-(2-(benzyl(3-morpholinopropyl)amino) ethyl)aniline for 4-amino-N-propylbenzamide and isoindoline for methyl isoindoline-5-carboxylate hydrochloride. $^1$H NMR (300 MHz, DMSO-d$_6$) δ ppm 8.24 (s, 1H), 7.43 (d, J=8.5 Hz, 2H), 7.38-7.18 (m, 9H), 7.04 (d, J=8.5 Hz, 2H), 4.75 (s, 4H), 3.60 (s, 2H), 3.54-3.47 (m, 4H), 2.70-2.54 (m, 4H), 2.48-2.41 (m, 2H), 2.29-2.16 (m, 6H), 1.62-1.46 (m, 2H); MS (ESI(+)) m/e 499 (M+H)$^+$.

Example 876

5-cyano-N-{4-[(3-methylbutyl)sulfamoyl]phenyl}-1,3-dihydro-2H-isoindole-2-carboxamide The title compound was prepared as described in Example 272B, substituting 4-amino-N-isopentylbenzenesulfonamide for 4-amino-N-propylbenzamide and isoindoline-5-carbonitrile for methyl isoindoline-5-carboxylate hydrochloride. $^1$H NMR (300 MHz, DMSO-d$_6$) δ ppm 8.82 (s, 1H), 7.89 (s, 1H), 7.83-7.74 (m, 3H), 7.71-7.64 (m, 2H), 7.59 (d, J=7.9 Hz, 1H), 7.31 (t, J=5.8 Hz, 1H), 4.89-4.81 (m, 4H), 2.78-2.67 (m, 2H), 1.56 (dp, J=13.3, 6.7 Hz, 1H), 1.30-1.19 (m, 2H), 0.78 (d, J=6.6 Hz, 6H); MS (ESI(+)) m/e 413 (M+H)$^+$.

Example 877

N-{4-[(3-methylbutyl)sulfamoyl]phenyl}-1,3-dihydro-2H-pyrrolo[3,4-c]pyridine-2-carboxamide The title compound was prepared as described in Example 272B, substituting 4-amino-N-isopentylbenzenesulfonamide for 4-amino-N-propylbenzamide and 1,3-dihydro-2H-pyrrolo[3,4-c]pyridine for methyl isoindoline-5-carboxylate hydrochloride. $^1$H NMR (300 MHz, DMSO-d$_6$) δ ppm 8.82 (s, 1H), 8.62 (s, 1H), 8.51 (d, J=5.0 Hz, 1H), 7.81-7.74 (m, 2H), 7.71-7.64 (m, 2H), 7.44 (d, J=5.1 Hz, 1H), 7.32 (t, J=5.8 Hz, 1H), 4.87-4.80 (m, 4H), 2.78-2.67 (m, 2H), 1.56 (dp, J=13.3, 6.7 Hz, 1H), 1.30-1.13 (m, 2H), 0.78 (d, J=6.6 Hz, 6H); MS (ESI(+)) m/e 389 (M+H)$^+$.

Example 883

N-(4-{[(3-methoxybenzyl)sulfonyl]amino}phenyl)-1,3-dihydro-2H-isoindole-2-carboxamide N-(4-aminophenyl)isoindoline-2-carboxamide (0.0585 g, 0.231 mmol) was suspended in dichloromethane (2 ml) followed by addition of triisopropylethylamine (0.081 ml, 0.462 mmol). (3-Methoxyphenyl)methanesulfonyl chloride (0.061 g, 0.277 mmol) was dissolved in 1 ml dichloromethane and added to the mixture via syringe slowly. The mixture was quenched with water and the separated aqueous layer was extracted with dichloromethane. The combined organic layers were dried over magnesium sulfate, filtered and concentrated. Reverse-phase HPLC provided the title compound. $^1$H NMR (300 MHz, DMSO-d$_6$) δ ppm 8.65 (s, 1H), 8.61 (s, 1H), 8.50 (d, J=5.0 Hz, 1H), 8.34 (t, J=5.6 Hz, 1H), 7.80-7.73 (m, 2H), 7.69-7.61 (m, 2H), 7.44 (d, J=5.0 Hz, 1H), 4.86-4.79 (m, 4H), 3.20 (t, J=6.2 Hz, 2H), 2.46-2.25 (m, 3H), 2.20 (d, J=7.9 Hz, 3H), 2.06-1.78 (m, 1H), 1.52-1.37 (m, 1H); MS (ESI(+)) m/e 438 (M+H)$^+$.

Example 909

N-{4-[6-(3-acetylphenyl)-4-(3-hydroxypropyl)-2-oxoquinolin-1(2H)-yl]butyl}-1,3-dihydro-2H-isoindole-2-carboxamide Example 909A 6-bromo-4-(3-(tert-butyldiphenylsilyloxy)propyl) quinolin-2(1H)-one 6-Bromo-4-(3-hydroxypropyl)quinolin-2(1H)-one (4.7 g, 16.67 mmoles), imidazole (2.84 g, 41.7 mmoles) and tert-butyldiphenylsilyl chloride (5.14 mL, 20 mmoles) were stirred in dimethylformamide (60 mL) overnight at room temperature. The reaction mixture was poured into water and extracted with ethyl acetate twice. The organic layers were combined, dried over magnesium sulfate, filtered and concentrated. The crude product was purified by normal phase chromatography to provide the title compound.

Example 909B tert-butyl 4-(6-bromo-4-(3-(tert-butyldiphenylsilyloxy)propyl)-2-oxoquinolin-1(2H)-yl)butylcarbamate The title compound was prepared as described in Example 797A, substituting 6-bromo-4-(3-(tert-butyldiphenylsilyloxy)propyl)quinolin-2(1H)-one for 6-bromoquinolin-2(1H)-one.

Example 909C 1-(4-aminobutyl)-6-bromo-4-(3-(tert-butyldiphenylsilyloxy)propyl)quinolin-2(1H)-one The title compound was prepared as described in Example 2D, substituting tert-butyl 4-(6-bromo-4-(3-(tert-butyldiphenylsilyloxy)propyl)-2-oxoquinolin-1(2H)-yl)butylcarbamate for tert-butyl 4-((4-(5-fluoroisoindoline-2-carboxamido)benzamido)methyl)benzylcarbamate.

Example 909D

N-(4-(6-bromo-4-(3-hydroxypropyl)-2-oxoquinolin-1(2H)-yl)butyl)isoindoline-2-carboxamide The title compound was prepared as described in Example 272B, substituting 1-(4-aminobutyl)-6-bromo-4-(3-(tert-butyldiphenylsilyloxy)propyl)quinolin-2(1H)-one for 4-amino-N-propylbenzamide and isoindoline for methyl isoindoline-5-carboxylate hydrochloride followed by TBAF deprotection and work up.

Example 909E

N-{4-[6-(3-acetylphenyl)-4-(3-hydroxypropyl)-2-oxoquinolin-1(2H)-yl]butyl}-1,3-dihydro-2H-isoindole-2-carboxamide The title compound was prepared as described in Example 280, substituting 3-acetylphenylboronic acid for 1H-pyrazol-3-ylboronic acid and N-(4-(6-bromo-4-(3-hydroxypropyl)-2-oxoquinolin-1(2H)-yl)butyl)isoindoline-2-carboxamide for 5-bromo-N-(4-(propylcarbamoyl)phenyl)isoindoline-2-carboxamide. $^1$H NMR (400 MHz, CDCl$_3$) δ ppm 8.24 (s, 1H), 8.08 (d, J=2.0 Hz, 1H), 7.96 (d, J=7.9 Hz, 1H), 7.87-7.79 (m, 2H), 7.58 (t, J=7.7 Hz, 1H), 7.54 (d, J=8.8 Hz, 1H), 7.28 (s, 4H), 6.71 (s, 1H), 4.74 (s, 4H), 4.41 (t, J=7.4 Hz, 2H), 3.82 (t, J=6.0 Hz, 2H), 3.46 (t, J=6.7 Hz, 2H), 3.12-2.99 (m, 2H), 2.68 (s, 3H), 2.10-1.96 (m, 2H), 1.96-1.83 (m, 2H), 1.79-1.72 (m, 2H); MS (APCI(+)) m/e 538 (M+H).

Example 910

N-{4-[1-(tetrahydrofuran-3-ylcarbonyl)piperidin-4-yl]phenyl}-1,3-dihydro-2H-pyrrolo[3,4-c]pyridine-2-carboxamide

Example 910A

N-(4-(piperidin-4-yl)phenyl)-1H-pyrrolo[3,4-c]pyridine-2(3H)-carboxamide

N-(4-(1,2,3,6-tetrahydropyridin-4-yl)phenyl)-1H-pyrrolo[3,4-c]pyridine-2(3H)-carboxamide (2.0 g, 6.24 mmol) in 80 mL of 1:1 THF:methanol was added to 5% Pd on carbon (wet) (0.500 g) in a 250 mL SS pressure bottle and the mixture was stirred for 38 hours at 30 atm and 25° C. The mixture was filtered through a nylon membrane, concentrated and suspended in ether. Filtration with ether washes provided the title compound.

Example 910B

N-{4-[1-(tetrahydrofuran-3-ylcarbonyl)piperidin-4-yl]phenyl}-1,3-dihydro-2H-pyrrolo[3,4-c]pyridine-2-carboxamide The title compound was prepared as described in Example 1C, substituting N-(4-(piperidin-4-yl)phenyl)-1H-pyrrolo[3,4-c]pyridine-2(3H)-carboxamide for 3-phenylpropan-1-amine and tetrahydrofuran-3-carboxylic acid for 4-(isoindoline-2-carboxamido)benzoic acid. $^1$H NMR (400 MHz, DMSO-d$_6$) δ ppm 8.60 (s, 1H), 8.50 (d, J=5.0 Hz, 1H), 8.35 (s, 1H), 7.46 (m, 2H), 7.43 (d, J=5.0 Hz, 1H), 7.14 (m, 2H), 4.79 (m, 4H), 4.54 (m, 1H), 4.07 (m, 1H), 3.88 (dt, J=10.4, 8.1 Hz, 1H), 3.71 (m, 3H), 3.37 (m, 1H), 3.13 (m, 1H), 2.64-2.59 (m, 2H), 2.01 (m, 2H), 1.79 (m, 2H), 1.46 (m, 2H); MS (ESI(+)) m/e 421 (M+H).

Table 15.

The following Examples were essentially prepared as described in Example 1C, substituting N-(4-(piperidin-4-yl)phenyl)-1H-pyrrolo[3,4-c]pyridine-2(3H)-carboxamide for 3-phenylpropan-1-amine and the appropriate carboxylic acid for 4-(isoindoline-2-carboxamido)benzoic acid.

| Ex | Name | $^1$H NMR | MS |
| --- | --- | --- | --- |
| 911 | N-(4-{1-[(2-methoxyethoxy)acetyl]piperidin-4-yl}phenyl)-1,3-dihydro-2H-pyrrolo[3,4-c]pyridine-2-carboxamide | $^1$H NMR (400 MHz, DMSO-d$_6$) δ ppm 8.62 (m, 1H), 8.51 (d, J = 7.4 Hz, 1H), 8.37 (s, 1H), 7.45 (m, 3H), 7.13 (d, J = 8.6 Hz, 2H), 4.83 (m, 4H), 4.48 (m, 1H), 4.17 (m, 2H), 3.89 (m, 1H), 3.60 (m, 2H), 3.46 (m, 2H), 3.26 (s, 3H), 3.07 (m, 1H), 2.78-2.56 (m, 2H), 1.74 (m, 2H), 1.57 (m, 1H), 1.42 (m, 1H) | (ESI (+)) m/e 439 (M + H)$^+$ |
| 912 | N-{4-[1-(tetrahydrofuran-2-ylcarbonyl)piperidin-4-yl]phenyl}-1,3-dihydro-2H-pyrrolo[3,4-c]pyridine-2-carboxamide | $^1$H NMR (400 MHz, DMSO-d$_6$) δ ppm 8.60 (s, 1H), 8.50 (d, J = 5.0 Hz, 1H), 8.35 (s, 1H), 7.48 (s, 2H), 7.43 (d, J = 5.0 Hz, 1H), 7.13 (m, 2H), 4.79 (m, 4H), 4.68 (dd, J = 7.6, 5.7 Hz, 1H), 4.49 (m, 1H), 4.11 (m, 1H), 3.78 (m, 2H), 3.10 (m, 1H), 2.79-2.57 (m, 2H), 2.03 (m, 2H), 1.84 (m, 4H), 1.61-1.36 (m, 2H) | (ESI (+)) m/e 421 (M + H)$^+$ |

| Ex | Name | ¹H NMR | MS |
|---|---|---|---|
| 913 | N-{4-[1-(tetrahydro-2H-pyran-4-ylcarbonyl)piperidin-4-yl]phenyl}-1,3-dihydro-2H-pyrrolo[3,4-c]pyridine-2-carboxamide | ¹H NMR (500 MHz, DMSO-d₆) δ ppm 8.60 (s, 1H), 8.50 (d, J = 5.0 Hz, 1H), 8.35 (s, 1H), 7.46 (m, 2H), 7.43 (d, J = 5.0 Hz, 1H), 7.13 (m, 2H), 4.79 (m, 4H), 4.55 (m, 1H), 4.09 (m, 1H), 3.85 (m, 2H), 3.41 (m, 2H), 3.10 (m, 1H), 2.91 (m, 1H), 2.71 (m, 1H), 2.58 (m, 1H), 1.79 (m, 2H), 1.68-1.33 (m, 6H) | (ESI (+)) m/e 435 (M + H)⁺ |
| 914 | N-{4-[1-(1,4-dioxan-2-ylcarbonyl)piperidin-4-yl]phenyl}-1,3-dihydro-2H-pyrrolo[3,4-c]pyridine-2-carboxamide | ¹H NMR (400 MHz, DMSO-d₆) δ ppm 8.60 (s, 1H), 8.50 (d, J = 4.9 Hz, 1H), 8.35 (s, 1H), 7.45 (m, 3H), 7.13 (s, 2H), 4.79 (d, J = 7.1 Hz, 4H), 4.45 (m, 1H), 4.34 (m, 1H), 4.07 (m, 1H), 3.80-3.55 (m, 5H), 3.50 (m, 1H), 3.09 (m, 1H), 2.65 (m, 2H), 1.79 (m, 2H), 1.67-1.29 (m, 2H) | (ESI (+)) m/e 437 (M + H)⁺ |
| 915 | N-(4-{1-[(1-methylpyrrolidin-3-yl)carbonyl]piperidin-4-yl}phenyl)-1,3-dihydro-2H-pyrrolo[3,4-c]pyridine-2-carboxamide | ¹H NMR (500 MHz, DMSO-d₆) δ ppm 8.60 (s, 1H), 8.50 (d, J = 5.0 Hz, 1H), 8.35 (s, 1H), 7.47 (m, 2H), 7.43 (d, J = 5.0 Hz, 1H), 7.12 (m, 2H), 4.79 (m, 4H), 4.49 (m, 1H), 4.16 (m, 1H), 3.58 (m, 4H), 3.26 (m, 1H), 3.06 (m, 2H), 2.71 (m, 1H), 2.61 (m, 1H), 2.39 (m, 4H), 1.78 (m, 2H), 1.57 (m, 1H), 1.40 (m, 1H) | (ESI (+)) m/e 434 (M + H)⁺ |
| 916 | N-(4-{1-[(1,1-dioxidotetrahydrothiophen-3-yl)carbonyl]piperidin-4-yl}phenyl)-1,3-dihydro-2H-pyrrolo[3,4-c]pyridine-2-carboxamide | ¹H NMR (400 MHz, DMSO-d₆) δ ppm 8.61 (s, 1H), 8.50 (d, J = 5.0 Hz, 1H), 8.35 (s, 1H), 7.47 (m, 2H), 7.43 (d, J = 5.0 Hz, 1H), 7.14 (m, 2H), 4.79 (m, 4H), 4.53 (m, 1H), 4.08 (m, 1H), 3.73 (m, 1H), 3.26-3.04 (m, 5H), 2.69 (m, 2H), 2.35 (m, 1H), 2.07 (m, 1H), 1.81 (m, 2H), 1.51 (m, 2H) | (ESI (+)) m/e 469 (M + H)⁺ |
| 917 | N-{4-[1-(2-hydroxy-2-methylpropanoyl)piperidin-4-yl]phenyl}-1,3-dihydro-2H-pyrrolo[3,4-c]pyridine-2-carboxamide | ¹H NMR (400 MHz, DMSO-d₆) δ ppm 8.60 (s, 1H), 8.50 (d, J = 5.0 Hz, 1H), 8.35 (s, 1H), 7.45 (m, 3H), 7.13 (m, 2H), 5.38 (s, 1H), 4.75 (m, 4H), 4.60 (m, 2H), 2.95 (m, 1H), 2.80 (m, 2H), 1.77 (m, 2H), 1.48 (m, 2H), 1.34 (s, 6H) | (ESI (+)) m/e 409 (M + H)⁺ |
| 918 | N-{4-[1-(morpholin-4-ylacetyl)piperidin-4-yl]phenyl}-1,3-dihydro-2H-pyrrolo[3,4-c]pyridine-2-carboxamide | ¹H NMR (500 MHz, DMSO-d₆) δ ppm 8.60 (s, 1H), 8.50 (d, J = 5.0 Hz, 1H), 8.35 (s, 1H), 7.47 (m, 2H), 7.43 (d, J = 5.0 Hz, 1H), 7.12 (m, 2H), 4.79 (m, 4H), 4.49 (m, 1H), 4.16 (m, 1H), 3.58 (m, 4H), 3.26 (m, 1H), 3.06 (m, 2H), 2.71 (m, 1H), 2.61 (m, 1H), 2.39 (m, 4H), 1.78 (m, 2H), 1.57 (m, 1H), 1.40 (m, 1H) | (ESI (+)) m/e 450 (M + H)⁺ |
| 1279 | N-(4-{1-[(2S)-tetrahydrofuran-2-ylcarbonyl]piperidin-4-yl}phenyl)-1,3-dihydro-2H-pyrrolo[3,4-c]pyridine-2-carboxamide | ¹H NMR (400 MHz, DMSO-d₆) δ ppm 8.60 (s, 1H), 8.50 (d, J = 5.0 Hz, 1H), 8.35 (s, 1H), 7.46 (m, 2H), 7.43 (d, J = 5.1 Hz, 1H), 7.13 (m, 2H), 4.79 (m, 4H), 4.68 (dd, J = 7.4, 5.8 Hz, 1H), 4.49 (d, J = 12.8 Hz, 1H), 4.10 (m, 1H), 3.78 (m, 2H), 3.08 (m, 1H), 2.78-2.57 (m, 2H), 2.04 (m, 2H), 1.90-1.71 (m, 4H), 1.61-1.32 (m, 2H) | (ESI (+)) m/e 421 (M + H)⁺ |
| 1280 | N-(4-{1-[(3S)-tetrahydrofuran-3-ylcarbonyl]piperidin-4-yl}phenyl)-1,3-dihydro-2H-pyrrolo[3,4-c]pyridine-2-carboxamide | ¹H NMR (400 MHz, DMSO-d₆) δ ppm 8.60 (s, 1H), 8.50 (d, J = 5.0 Hz, 1H), 8.35 (s, 1H), 7.49-7.40 (m, 3H), 7.14 (m, 2H), 4.79 (m, 4H), 4.54 (m, 1H), 4.06 (m, 1H), 3.88 (dt, J = 10.4, 8.1 Hz, 1H), 3.78-3.54 (m, 3H), 3.38 (m, 1H), 3.15 (m, 1H), 2.77-2.56 (m, 2H), 2.04 (m, 2H), 1.79 (m, 2H), 1.59-1.29 (m, 2H) | (ESI (+)) m/e 421 (M + H)⁺ |
| 1384 | N-(4-{1-[(2R)-tetrahydrofuran-2-ylcarbonyl]piperidin-4-yl}phenyl)-1,3-dihydro-2H-pyrrolo[3,4-c]pyridine-2-carboxamide | ¹H NMR (400 MHz, DMSO-d₆) δ ppm 8.60 (s, 1H), 8.50 (d, J = 5.0 Hz, 1H), 8.35 (s, 1H), 7.45 (m, 3H), 7.13 (m, 2H), 4.79 (m, 4H), 4.68 (dd, J = 7.4, 5.8 Hz, 1H), 4.48 (d, J = 12.7 Hz, 1H), 4.10 (d, J = 12.8 Hz, 1H), 3.78 (m, 2H), 3.08 (dd, J = 26.0, 12.3 Hz, 1H), 2.77-2.55 (m, 2H), 2.04 (m, 2H), 1.83 (m, 4H), 1.62-1.32 (m, 2H) | (ESI (+)) m/e 421 (M + H)⁺ |
| 1385 | N-(4-{1-[(3R)-tetrahydrofuran-3-ylcarbonyl]piperidin-4-yl}phenyl)-1,3-dihydro-2H-pyrrolo[3,4-c]pyridine-2-carboxamide | ¹H NMR (400 MHz, DMSO-d₆) δ ppm 8.60 (s, 1H), 8.50 (d, J = 5.0 Hz, 1H), 8.35 (s, 1H), 7.45 (m, 3H), 7.14 (m, 2H), 4.79 (m, 4H), 4.54 (m, 1H), 4.07 (m, 1H), 3.88 (dt, J = 10.4, 8.1 Hz, 1H), 3.71 (m, 3H), 3.37 (m, 1H), 3.10 (m, 1H), 2.80-2.55 (m, 2H), 2.00 (m, 2H), 1.79 (m, 2H), 1.59-1.33 (m, 2H) | (ESI (+)) m/e 421 (M + H)⁺ |

Example 920

N-{5-[2-(2-chlorobenzyl)-1,3-thiazol-4-yl]-2-thienyl}-1,3-dihydro-2H-isoindole-2-carboxamide

Example 920A 5-(2-(2-chlorobenzyl)thiazol-4-yl)thiophen-2-amine

The title compound was prepared as described in Example 806A, substituting 2-bromo-1-(5-nitrothiophen-2-yl)ethanone for 2-bromo-1-(4-nitrophenyl)ethanone and 2-(2-chlorophenyl)ethanethioamide for 2-phenylethanethioamide.

Example 920B

N-{5-[2-(2-chlorobenzyl)-1,3-thiazol-4-yl]-2-thienyl}-1,3-dihydro-2H-isoindole-2-carboxamide The title compound was prepared as described in Example 272B, substituting 5-(2-(2-chlorobenzyl)thiazol-4-yl)thiophen-2-amine for 4-amino-N-propylbenzamide and isoindoline for methyl isoindoline-5-carboxylate hydrochloride. $^1$H NMR (400 MHz, DMSO-d$_6$) δ ppm 9.73 (s, 1H), 7.46-7.55 (m, 3H), 7.34-7.40 (m, 4H), 7.28-7.34 (m, 2H), 7.20 (d, J=3.9 Hz, 1H), 6.62 (d, J=3.9 Hz, 1H), 4.76 (s, 4H), 4.45 (s, 2H); MS (ESI(+)) m/e 452.0 (M+H).

Example 921

N-[4-(4-fluorophenyl)butyl]-5-(hydroxymethyl)-1,3-dihydro-2H-isoindole-2-carboxamide The title compound was prepared as described in Example 272B, substituting 4-(4-fluorophenyl)butylamine for 4-amino-N-propylbenzamide and isoindolin-5-ylmethanol hydrochloride for methyl isoindoline-5-carboxylate hydrochloride. $^1$H NMR (300 MHz, DMSO-d$_6$) δ ppm 7.28-7.17 (m, 5H), 7.13-7.03 (m, 2H), 6.29 (t, J=5.6 Hz, 1H), 5.16 (t, J=5.6 Hz, 1H), 4.54 (bs, 4H), 4.49 (d, J=5.5 Hz, 2H), 3.15-3.04 (m, 2H), 2.58 (t, J=7.4 Hz, 2H), 1.63-1.37 (m, 4H); MS (ESI(+)) m/e 343 (M+H)$^+$.

Example 926

N-[4-(1-isobutyl-1,2,3,6-tetrahydropyridin-4-yl)phenyl]-1,3-dihydro-2H-pyrrolo[3,4-c]pyridine-2-carboxamide In a 20 mL scintillation vial were mixed N-(4-(1,2,3,6-tetrahydropyridin-4-yl)phenyl)-1H-pyrrolo[3,4-c]pyridine-2(3H)-carboxamide (100 mg, 0.312 mmol), isobutyraldehyde (0.343 mmol), and sodium triacetoxyborohydride (0.43 mmol) in anhydrous dichloroethane (4 ml). The reaction mixture was stirred overnight at room temperature. This mixture was diluted with water and the resulting suspension was stirred again overnight at room temperature. The solid was filtered through a 30 mL plastic disposable Buchner funnel, and the collected solid was washed with water, dried for 2 hours, washed with ether, and dried again to provide the title compound. $^1$H NMR (400 MHz, DMSO-d$_6$, Temp=90° C.) δ ppm 8.58 (s, 1H), 8.47 (d, J=5.0 Hz, 1H), 8.18 (m, 1H), 7.50 (m, 2H), 7.38 (d, J=5.1 Hz, 1H), 7.30 (m, 2H), 6.03 (m, 1H), 4.80 (m, 4H), 3.06 (m, 2H), 2.61 (t, J=5.6 Hz, 2H), 2.44 (m, 2H), 2.17 (d, J=7.2 Hz, 2H), 1.82 (m, 1H), 0.89 (d, J=6.6 Hz, 6H); MS (ESI(+)) m/e 377 (M+H).

Example 927

N-{4-[1-(tetrahydrofuran-3-ylmethyl)-1,2,3,6-tetrahydropyridin-4-yl]phenyl}-1,3-dihydro-2H-pyrrolo[3,4-c]pyridine-2-carboxamide The title compound was prepared as described in Example 926, substituting tetrahydrofuran-3-carbaldehyde for isobutraldehyde. $^1$H NMR (400 MHz, DMSO-d$_6$, Temp=90° C.) δ ppm 8.58 (s, 1H), 8.48 (d, J=5.0 Hz, 1H), 8.17 (bs, 1H), 7.60 (m, 2H), 7.38 (d, J=5.0 Hz, 1H), 7.30 (m, 2H), 6.05 (m, 1H), 4.83 (m, 4H), 3.77 (m, 2H), 3.62 (q, J=7.6 Hz, 1H), 3.39 (m, 1H), 3.10 (t, J=3.1 Hz, 2H), 2.95 (m, 1H), 2.65 (m, 2H), 2.43 (m, 2H), 2.38 (m, 2H), 1.95 (m, 1H), 1.54 (m, 1H); MS (ESI(+)) m/e 405 (M+H).

Example 928

N-{4-[1-(tetrahydro-2H-pyran-4-ylmethyl)-1,2,3,6-tetrahydropyridin-4-yl]phenyl}-1,3-dihydro-2H-pyrrolo[3,4-c]pyridine-2-carboxamide The title compound was prepared as described in Example 926, substituting tetrahydro-2H-pyran-4-carbaldehyde for isobutraldehyde. $^1$H NMR (400 MHz, DMSO-d$_6$, Temp=90° C.) δ ppm 8.58 (s, 1H), 8.48 (d, J=5.0 Hz, 1H), 8.17 (bs, 1H), 7.50 (m, 2H), 7.38 (d, J=5.1 Hz, 1H), 7.30 (m, 2H), 6.03 (m, 1H), 4.79 (m, 4H), 3.83 (m, 2H), 3.31 (td, J=11.5, 2.2 Hz, 2H), 3.07 (m, 2H), 2.63 (t, J=5.6 Hz, 2H), 2.43 (m, 2H), 2.27 (d, J=7.1 Hz, 2H), 1.80 (m, 1H), 1.64 (m, 2H), 1.17 (m, 2H); MS (ESI(+)) m/e 419 (M+H).

Example 929

N-[4-(1-isobutylpiperidin-4-yl)phenyl]-1,3-dihydro-2H-pyrrolo[3,4-c]pyridine-2-carboxamide The title compound was prepared as described in Example 926, substituting N-(4-(piperidin-4-yl)phenyl)-1H-pyrrolo[3,4-c]pyridine-2(3H)-carboxamide for N-(4-(1,2,3,6-tetrahydropyridin-4-yl)phenyl)-1H-pyrrolo[3,4-c]pyridine-2(3H)-carboxamide. $^1$H NMR (400 MHz, DMSO-d$_6$) δ ppm 8.60 (s, 1H), 8.50 (d, J=5.0 Hz, 1H), 8.33 (s, 1H), 7.43 (m, 3H), 7.13 (m, 2H), 4.79 (m, 4H), 2.41 (m, 1H), 2.92 (m, 2H), 2.15-1.85 (m, 4H), 1.85-1.50 (m, 5H), 0.87 (d, J=6.5 Hz, 6H); MS (ESI(+)) m/e 379 (M+H).

Example 930

N-{4-[1-(tetrahydrofuran-3-ylmethyl)piperidin-4-yl]phenyl}-1,3-dihydro-2H-pyrrolo[3,4-c]pyridine-2-carboxamide The title compound was prepared as described in Example 926, substituting N-(4-(piperidin-4-yl)phenyl)-1H-pyrrolo[3,4-c]pyridine-2(3H)-carboxamide for N-(4-(1,2,3,6-tetrahydropyridin-4-yl)phenyl)-1H-pyrrolo[3,4-c]pyridine-2(3H)-carboxamide and tetrahydrofuran-3-carbaldehyde for isobutraldehyde. $^1$H NMR (400 MHz, DMSO-d$_6$) δ ppm 8.60 (s, 1H), 8.50 (d, J=5.0 Hz, 1H), 8.33 (s, 1H), 7.44 (m, 3H), 7.13 (m, 2H), 4.78 (m, 4H), 3.71 (m, 2H), 3.61 (q, J=7.6 Hz, 1H), 3.36 (m, 2H), 2.96 (m, 2H), 2.40 (m, 1H), 2.27 (m, 2H), 96 (m, 3H), 1.72 (m, 2H), 1.66-1.46 (m, 3H); MS (ESI(+)) m/e 407 (M+H).

Example 931

N-{4-[1-(tetrahydro-2H-pyran-4-ylmethyl)piperidin-4-yl]phenyl}-1,3-dihydro-2H-pyrrolo[3,4-c]pyridine-2-carboxamide The title compound was prepared as described in Example 926, substituting N-(4-(piperidin-4-yl)phenyl)-1H-pyrrolo[3,4-c]pyridine-2(3H)-carboxamide for N-(4-(1,2,3,6-tetrahydropyridin-4-yl)phenyl)-1H-pyrrolo[3,4-c]pyridine-2(3H)-carboxamide and tetrahydro-2H-pyran-4-carbaldehyde for isobutraldehyde. $^1$H NMR (400 MHz, DMSO-d$_6$) δ ppm 8.60 (s, 1H), 8.49 (d, J=5.0 Hz, 1H), 8.33 (s, 1H), 7.44 (m, 3H), 7.12 (m, 2H), 4.79 (m, 4H), 3.83 (m, 2H), 3.27 (m, 2H), 2.92 (m, 2H), 2.40 (m, 1H), 2.14 (d, J=7.2 Hz, 2H), 1.95 (m, 2H), 1.74 (m, 3H), 1.61 (m, 4H), 1.12 (m, 2H); MS (ESI(+)) m/e 421 (M+H).

Example 933 tert-butyl {4-[(1,3-dihydro-2H-isoindol-2-ylcarbonyl)amino]benzyl}carbamate

The title compound was prepared as described in Example 272B, substituting tert-butyl 4-aminobenzylcarbamate for 4-amino-N-propylbenzamide and isoindoline for methyl isoindoline-5-carboxylate hydrochloride. $^1$H NMR (300 MHz, DMSO-d$_6$) δ ppm 8.29 (s, 1H), 7.52-7.45 (m, 2H), 7.40-7.24 (m, 5H), 7.15-7.08 (m, 2H), 4.76 (bs, 4H), 4.09-3.99 (m, 2H), 1.39 (s, 9H); MS (ESI(+)) m/e 368 (M+H)$^+$.

Example 934

N-{4-[(cyclopentylacetyl)amino]phenyl}-1,3-dihydro-2H-pyrrolo[3,4-c]pyridine-2-carboxamide

Example 934A

N-(4-nitrophenyl)-1H-pyrrolo[3,4-c]pyridine-2(3H)-carboxamide

The title compound was prepared as described in Example 1A, substituting 1-isocyanato-4-nitrobenzene for methyl 4-isocyanatobenzoate and 1,3-dihydro-2H-pyrrolo[3,4-c]pyridine for isoindoline.

Example 934B

N-(4-aminophenyl)-1H-pyrrolo[3,4-c]pyridine-2(3H)-carboxamide

The title compound was prepared as described in Example 272A, substituting N-(4-nitrophenyl)-1H-pyrrolo[3,4-c]pyridine-2(3H)-carboxamide for 4-nitro-N-propylbenzamide.

Example 934C

N-{4-[(cyclopentylacetyl)amino]phenyl}-1,3-dihydro-2H-pyrrolo[3,4-c]pyridine-2-carboxamide The title compound was prepared as described in Example 1C, substituting N-(4-aminophenyl)-1H-pyrrolo[3,4-c]pyridine-2(3H)-carboxamide for 3-phenylpropan-1-amine and cyclopentylacetic acid for 4-(isoindoline-2-carboxamido)benzoic acid. $^1$H NMR (300 MHz, DMSO-d$_6$) δ ppm 9.70 (s, 1H), 8.60 (s, 1H), 8.50 (d, J=5.0 Hz, 1H), 8.34 (s, 1H), 7.51-7.40 (m, 5H), 4.82-4.75 (m, 4H), 2.33-2.17 (m, 3H), 1.81-1.68 (m, 2H), 1.68-1.43 (m, 4H), 1.27-1.13 (m, 2H); (ESI(+)) m/e 365 (M+H)$^+$.

Example 936

N-[4-(5-{[(tetrahydrofuran-2-ylmethyl)amino]methyl}-1,2,4-oxadiazol-3-yl)phenyl]-1,3-dihydro-2H-isoindole-2-carboxamide The title compound was prepared as described in Example 753B, substituting (tetrahydrofuran-2-yl)methanamine for morpholine. $^1$H NMR (300 MHz, DMSO-d$_6$) δ ppm 8.68 (s, 1H), 7.91 (d, J=8.7 Hz, 2H), 7.79 (d, J=8.8 Hz, 2H), 7.45-7.20 (m, 4H), 4.80 (s, 4H), 4.08 (s, 2H), 3.95-3.78 (m, 1H), 3.79-3.66 (m, 1H), 3.66-3.49 (m, 1H), 2.66 (d, J=5.6 Hz, 2H), 2.00-1.67 (m, 4H), 1.67-1.41 (m, 2H), 1.40-1.16 (m, 2H), 0.87 (dd, J=9.3, 5.4 Hz, 1H); MS (ESI(+)) m/e 420 (M+H)$^+$.

Example 937

N-(4-{5-[(4-methoxypiperidin-1-yl)methyl]-1,2,4-oxadiazol-3-yl}phenyl)-1,3-dihydro-2H-isoindole-2-carboxamide The title compound was prepared as described in Example 753B, substituting 4-methoxypiperidine for morpholine. $^1$H NMR (300 MHz, DMSO-d$_6$) δ ppm 8.69 (s, 1H), 7.92 (d, J=8.8 Hz, 2H), 7.80 (d, J=8.8 Hz, 2H), 7.45-7.20 (m, 4H), 4.80 (s, 4H), 3.93 (s, 2H), 3.21 (s, 3H), 3.20-3.10 (m, 1H), 2.82-2.68 (m, 2H), 2.50 (dt, J=3.6, 1.8 Hz, 2H), 2.41-2.24 (m, 2H), 1.92-1.75 (m, 2H), 1.56-1.37 (m, 2H); MS (ESI(+)) m/e 434 (M+H)$^+$.

Example 938

N-[4-(5-{[4-(2-methoxyethyl)piperazin-1-yl]methyl}-1,2,4-oxadiazol-3-yl)phenyl]-1,3-dihydro-2H-isoindole-2-carboxamide The title compound was prepared as described in Example 753B, substituting N-(2-methoxyethyl)piperazine for morpholine. $^1$H NMR (300 MHz, DMSO-d$_6$) δ ppm 8.69 (s, 1H), 7.92 (d, J=8.8 Hz, 2H), 7.86-7.70 (m, 2H), 7.46-7.23 (m, 4H), 4.80 (s, 4H), 3.93 (s, 2H), 3.40 (t, J=5.8 Hz, 3H), 3.21 (s, 3H), 2.55 (s, 4H), 2.45 (t, J=5.8 Hz, 6H); MS (ESI(+)) m/e 463 (M+H)$^+$.

Example 940

N-{4-[(1-pentanoylpiperidin-4-yl)oxy]phenyl}-1,3-dihydro-2H-pyrrolo[3,4-c]pyridine-2-carboxamide

Example 940A tert-butyl 4-(4-nitrophenoxy)piperidine-1-carboxylate

4-Hydroxy-1-piperidine-1-carboxylic acid tert-butyl ester (6.04 g, 30 mmol) was dissolved in 1-fluoro-4-nitrobenzene (7.83 g, 55.5 mmol). Aqueous potassium hydroxide solution (25 percent wt, 44 mL) was added, followed by addition of tetrabutylammonium bromide (1.26 g). The reaction mixture was stirred at 35° C. for 17 hours. The solid was collected by filtration and washed with water (4×50 mL) to provide the title compound after vacuum drying.

Example 940B tert-butyl 4-(4-aminophenoxy)piperidine-1-carboxylate

The title compound was prepared as described in Example 274, substituting tert-butyl 4-(4-nitrophenoxy)piperidine-1-carboxylate for 5-nitro-N-[4-(propylcarbamoyl)phenyl]-1,3-dihydro-2H-isoindole-2-carboxamide.

Example 940C tert-butyl 4-(4-(2,3-dihydro-1H-pyrrolo[3,4-c]pyridine-2-carboxamido)phenoxy)piperidine-1-carboxylate The title compound was prepared as described in Example 272B, substituting tert-butyl 4-(4-aminophenoxy)piperidine-1-carboxylate for 4-amino-N-propylbenzamide and 1,3-dihydro-2H-pyrrolo[3,4-c]pyridine for methyl isoindoline-5-carboxylate hydrochloride.

Example 940D

N-(4-(piperidin-4-yloxy)phenyl)-1H-pyrrolo[3,4-c]pyridine-2(3H)-carboxamide

The title compound was prepared as described in Example 2D, substituting tert-butyl 4-(4-(2,3-dihydro-1H-pyrrolo[3,4-c]pyridine-2-carboxamido)phenoxy)piperidine-1-carboxylate for tert-butyl 44(4-(5-fluoroisoindoline-2-carboxamido)benzamido)methyl)benzylcarbamate.

Example 940E

N-{4-[(1-pentanoylpiperidin-4-yl)oxy]phenyl}-1,3-dihydro-2H-pyrrolo[3,4-c]pyridine-2-carboxamide The title compound was prepared as described in Example 1C, substituting N-(4-(piperidin-4-yloxy)phenyl)-1H-pyrrolo[3,4-c]pyridine-2(3H)-carboxamide for 3-phenylpropan-1-amine and pentanoic acid for 4-(isoindoline-2-carboxamido)benzoic acid. $^1$H NMR (300 MHz, DMSO-$d_6$) δ ppm 8.80 (s, 1H), 8.68 (d, J=5.5 Hz, 1H), 8.36 (s, 1H), 7.77 (d, J=5.5 Hz, 1H), 7.42 (d, J=9.0 Hz, 1H), 6.95-6.87 (m, 2H), 4.87 (d, J=6.4 Hz, 4H), 4.64-4.45 (m, 1H), 3.92-3.79 (m, 1H), 3.76-3.63 (m, 1H), 3.38-3.15 (m, 2H), 2.31 (t, J=7.4 Hz, 2H), 1.96-1.81 (m, 2H), 1.61-1.41 (m, 4H), 1.38-1.22 (m, 2H), 0.88 (t, J=7.2 Hz, 3H); MS (ESI(+)) m/e 423 (M+H)$^+$.

Table 16.

The following Examples were essentially prepared as described in Example 940, substituting the appropriate alcohol, in place of 4-hydroxy-1-piperidine-1-carboxylic acid tert-butyl ester in Example 940A, and the appropriate carboxylic acid in Example 940E.

| Ex | Name | $^1$H NMR | MS |
|---|---|---|---|
| 941 | N-{4-[(1-acetylpiperidin-4-yl)oxy]phenyl}-1,3-dihydro-2H-pyrrolo[3,4-c]pyridine-2-carboxamide | 1H NMR (300 MHz, DMSO-$d_6$) δ 8.83 (s, 1H), 8.71 (d, J = 5.6 Hz, 1H), 8.38 (s, 1H), 7.83 (d, J = 5.6 Hz, 1H), 7.42 (d, J = 8.9 Hz, 2H), 6.91 (d, J = 9.0 Hz, 2H), 4.89 (d, J = 9.8 Hz, 4H), 4.57-4.44 (m, 1H), 3.91-3.76 (m, 1H), 3.76-3.57 (m, 1H), 3.43-3.12 (m, 2H), 2.02 (s, 3H), 1.97-1.77 (m, 2H), 1.68-1.33 (m, 2H) | (ESI (+)) m/e 381 (M + H)$^+$ |
| 942 | N-{4-[(1-butyrylpiperidin-4-yl)oxy]phenyl}-1,3-dihydro-2H-pyrrolo[3,4-c]pyridine-2-carboxamide | $^1$H NMR (300 MHz, DMSO-$d_6$) δ 8.60 (s, 1H), 8.50 (d, J = 5.0 Hz, 1H), 8.28 (s, 1H), 7.43 (dd, J = 7.0, 1.8 Hz, 3H), 6.90 (d, J = 9.0 Hz, 2H), 4.78 (d, J = 4.0 Hz, 4H), 4.57-4.39 (m, 1H), 3.95-3.76 (m, 1H), 3.70 (d, J = 14.0 Hz, 1H), 3.23 (dd, J = 15.9, 6.4 Hz, 1H), 2.30 (t, J = 7.4 Hz, 2H), 1.90 (s, 2H), 1.51 (dq, J = 14.6, 7.3 Hz, 4H), 0.89 (t, J = 7.4 Hz, 3H) | (ESI (+)) m/e 409 (M + H)$^+$ |
| 943 | N-(4-{[1-(2-methylbutanoyl)piperidin-4-yl]oxy}phenyl)-1,3-dihydro-2H-pyrrolo[3,4-c]pyridine-2-carboxamide | $^1$H NMR (300 MHz, DMSO-$d_6$) δ 8.79 (s, 1H), 8.67 (d, J = 5.5 Hz, 1H), 8.36 (s, 1H), 7.76 (d, J = 5.5 Hz, 1H), 7.42 (d, J = 9.0 Hz, 1H), 6.91 (d, J = 9.0 Hz, 1H), 4.87 (d, J = 5.8 Hz, 2H), 4.66-4.47 (m, 1H), 3.98-3.74 (m, 2H), 3.43-3.14 (m, 2H), 2.81-2.63 (m, 1H), 1.99-1.82 (m, 2H), 1.55 (dt, J = 20.8, 7.2 Hz, 1H), 1.31 (td, J = 13.9, 7.1 Hz, 1H), 0.98 (d, J = 6.7 Hz, 3H), 0.81 (t, J = 7.4 Hz, 1H) | (ESI (+)) m/e 423 (M + H)$^+$ |
| 944 | N-(4-{[1-(3,3,3-trifluoropropanoyl)piperidin-4-yl]oxy}phenyl)-1,3-dihydro-2H-pyrrolo[3,4-c]pyridine-2-carboxamide | $^1$H NMR (300 MHz, DMSO-$d_6$) δ 8.80 (s, 1H), 8.68 (d, J = 5.5 Hz, 1H), 8.37 (s, 1H), 7.78 (d, J = 5.5 Hz, 1H), 7.42 (d, J = 8.9 Hz, 2H), 6.91 (d, J = 8.9 Hz, 2H), 4.88 (d, J = 7.3 Hz, 5H), 4.60-4.44 (m, 1H), 3.85 (dd, J = 14.1, 5.4 Hz, 1H), 3.67 (q, J = 11.0 Hz, 3H), 3.41-3.21 (m, 2H), 1.92 (dd, J = 16.5, 13.5 Hz, 2H), 1.73-1.35 (m, 2H) | (ESI (+)) m/e 449 (M + H)$^+$ |
| 945 | N-(4-{[1-(methoxyacetyl)piperidin-4-yl]oxy}phenyl)-1,3-dihydro-2H-pyrrolo[3,4-c]pyridine-2-carboxamide | $^1$H NMR (300 MHz, DMSO-$d_6$) δ 8.60 (s, 1H), 8.50 (d, J = 5.0 Hz, 1H), 8.28 (s, 1H), 7.43 (dd, J = 6.9, 1.9 Hz, 3H), 6.90 (d, J = 9.0 Hz, 2H), 4.78 (d, J = 3.9 Hz, 5H), 4.51 (dd, J = 7.8, 3.9 Hz, 1H), 4.09 (s, 2H), 3.89-3.74 (m, 1H), 3.62 (ddd, J = 8.2, 4.1, 1.1 Hz, 1H), 3.29 (s, 3H), 1.91 (d, J = 1.3 Hz, 2H), 1.69-1.39 (m, 2H) | (ESI (+)) m/e 411 (M + H)$^+$ |

| Ex | Name | ¹H NMR | MS |
|---|---|---|---|
| 946 | N-(4-{[1-(tetrahydrofuran-2-ylcarbonyl)piperidin-4-yl]oxy}phenyl)-1,3-dihydro-2H-pyrrolo[3,4-c]pyridine-2-carboxamide | ¹H NMR (300 MHz, DMSO-d₆) δ 8.80 (s, 1H), 8.69 (d, J = 5.5 Hz, 1H), 8.36 (s, 1H), 7.78 (d, J = 5.5 Hz, 1H), 7.42 (d, J = 9.0 Hz, 2H), 6.91 (d, J = 9.0 Hz, 2H), 4.88 (d, J = 8.2 Hz, 4H), 4.76-4.62 (m, 1H), 4.52 (s, 1H), 3.75 (dd, J = 12.0, 6.6 Hz, 5H), 3.48-3.14 (m, 2H), 1.91 (dddd, J = 19.4, 15.1, 7.6, 5.2 Hz, 6H), 1.51 (dd, J = 20.6, 12.0 Hz, 2H) | (ESI (+)) m/e 437 (M + H)⁺ |
| 947 | N-(4-{[1-(cyclopropylcarbonyl)piperidin-4-yl]oxy}phenyl)-1,3-dihydro-2H-pyrrolo[3,4-c]pyridine-2-carboxamide | ¹H NMR (300 MHz, DMSO-d₆) δ 8.60 (s, 1H), 8.50 (d, J = 5.0 Hz, 1H), 8.27 (s, 1H), 7.43 (d, J = 8.9 Hz, 3H), 6.91 (d, J = 9.0 Hz, 2H), 4.78 (d, J = 4.0 Hz, 4H), 4.53 (dt, J = 7.9, 4.0 Hz, 1H), 4.06-3.66 (m, 2H), 3.64-3.39 (m, 1H), 2.08-1.73 (m, 3H), 1.73-1.37 (m, 2H), 0.84-0.52 (m, 4H) | (ESI (+)) m/e 407 (M + H)⁺ |
| 948 | N-(4-{[1-(cyclopropylacetyl)piperidin-4-yl]oxy}phenyl)-1,3-dihydro-2H-pyrrolo[3,4-c]pyridine-2-carboxamide | ¹H NMR (300 MHz, DMSO-d₆) δ 8.60 (s, 1H), 8.50 (d, J = 5.0 Hz, 1H), 8.27 (s, 1H), 7.42 (dd, J = 7.0, 1.8 Hz, 2H), 6.90 (d, J = 9.0 Hz, 1H), 4.81-4.74 (m, 4H), 4.57-4.45 (m, 1H), 3.93-3.81 (m, 1H), 3.73-3.62 (m, 1H), 2.27 (d, J = 6.7 Hz, 2H), 1.99-1.82 (m, 2H), 1.68-1.35 (m, 2H), 1.04-0.87 (m, 1H), 0.50-0.40 (m, 2H), 0.16-0.07 (m, 2H) | (ESI (+)) m/e 421 (M + H)⁺ |
| 949 | N-(4-{[1-(cyclobutylcarbonyl)piperidin-4-yl]oxy}phenyl)-1,3-dihydro-2H-pyrrolo[3,4-c]pyridine-2-carboxamide | ¹H NMR (300 MHz, DMSO-d₆) δ 8.83 (s, 1H), 8.71 (d, J = 5.6 Hz, 1H), 8.37 (s, 1H), 7.82 (d, J = 5.6 Hz, 1H), 7.41 (d, J = 9.0 Hz, 2H), 6.90 (d, J = 9.0 Hz, 2H), 4.89 (d, J = 9.7 Hz, 4H), 4.61-4.38 (m, 1H), 3.90-3.75 (m, 1H), 3.64-3.46 (m, 1H), 3.27-3.06 (m, 2H), 2.12 (ddd, J = 13.8, 12.3, 7.5 Hz, 4H), 2.00-1.77 (m, 3H), 1.74 (dd, J = 9.1, 4.8 Hz, 1H), 1.59-1.28 (m, 2H) | (ESI (+)) m/e 421 (M + H)⁺ |
| 950 | N-(4-{[1-(cyclopentylcarbonyl)piperidin-4-yl]oxy}phenyl)-1,3-dihydro-2H-pyrrolo[3,4-c]pyridine-2-carboxamide | ¹H NMR (300 MHz, DMSO-d₆) δ 8.78 (s, 1H), 8.66 (d, J = 5.5 Hz, 1H), 8.35 (s, 1H), 7.74 (d, J = 5.4 Hz, 1H), 7.42 (d, J = 9.0 Hz, 2H), 6.91 (d, J = 9.0 Hz, 2H), 4.87 (d, J = 4.5 Hz, 4H), 4.51 (dd, J = 7.7, 3.9 Hz, 1H), 3.92-3.70 (m, 2H), 3.45-3.30 (m, 1H), 3.21 (dd, J = 18.3, 8.9 Hz, 1H), 2.98 (dd, J = 15.4, 7.5 Hz, 1H), 2.01-1.38 (m, 12H) | (ESI (+)) m/e 435 (M + H)⁺ |
| 951 | N-(4-{[1-(cyclopentylacetyl)piperidin-4-yl]oxy}phenyl)-1,3-dihydro-2H-pyrrolo[3,4-c]pyridine-2-carboxamide | ¹H NMR (300 MHz, DMSO-d₆) δ 8.78 (s, 1H), 8.67 (d, J = 5.4 Hz, 1H), 8.35 (s, 1H), 7.75 (d, J = 5.5 Hz, 1H), 7.42 (d, J = 9.0 Hz, 2H), 6.91 (d, J = 9.0 Hz, 2H), 4.87 (d, J = 5.1 Hz, 5H), 4.55-4.45 (m, 1H), 3.86 (d, J = 12.3 Hz, 1H), 3.71 (d, J = 14.1 Hz, 1H), 3.39-3.08 (m, 2H), 2.34 (d, J = 7.1 Hz, 2H), 2.13 (dt, J = 15.3, 7.6 Hz, 1H), 1.90 (s, 2H), 1.74 (dt, J = 11.2, 6.5 Hz, 2H), 1.65-1.36 (m, 6H), 1.23-1.02 (m, 2H) | (ESI (+)) m/e 449 (M + H)⁺ |
| 952 | N-(4-{[1-(cyclohexylcarbonyl)piperidin-4-yl]oxy}phenyl)-1,3-dihydro-2H-pyrrolo[3,4-c]pyridine-2-carboxamide | ¹H NMR (300 MHz, DMSO-d₆) δ 8.78 (s, 1H), 8.66 (d, J = 5.4 Hz, 1H), 8.35 (s, 1H), 7.74 (d, J = 5.3 Hz, 1H), 7.42 (d, J = 9.0 Hz, 2H), 6.91 (d, J = 9.0 Hz, 2H), 4.87 (d, J = 4.5 Hz, 4H), 4.54-4.44 (m, 1H), 3.83 (s, 2H), 3.17 (d, J = 0.9 Hz, 2H), 2.63-2.52 (m, 1H), 1.91 (s, 3H), 1.61 (dd, J = 38.7, 30.1 Hz, 7H), 1.43-1.02 (m, 7H) | (ESI (+)) m/e 449 (M + H)⁺ |
| 987 | N-(4-{[1-(3,3,3-trifluoropropanoyl)azetidin-3-yl]oxy}phenyl)-1,3-dihydro-2H-pyrrolo[3,4-c]pyridine-2-carboxamide | ¹H NMR (300 MHz, DMSO-d₆) δ 8.77 (s, 1H), 8.65 (d, J = 5.4 Hz, 1H), 8.38 (s, 1H), 7.72 (d, J = 5.5 Hz, 2H), 7.45 (d, J = 9.1 Hz, 2H), 6.78 (d, J = 9.1 Hz, 2H), 5.06-4.93 (m, 1H), 4.87 (d, J = 3.6 Hz, 4H), 4.60 (dd, J = 8.6, 6.5 Hz, 1H), 4.34 (dd, J = 11.0, 6.1 Hz, 1H), 4.15 (dd, J = 9.6, 2.9 Hz, 1H), 3.81 (dd, J = 10.7, 3.8 Hz, 1H), 3.40 (q, J = 11.2 Hz, 2H) | (ESI (+)) m/e 421 (M + H)⁺ |
| 988 | N-(4-{[1-(4,4,4-trifluorobutanoyl)azetidin-3-yl]oxy}phenyl)-1,3-dihydro-2H-pyrrolo[3,4-c]pyridine-2-carboxamide | ¹H NMR (300 MHz, DMSO-d₆) δ 8.69 (s, 1H), 8.58 (d, J = 5.3 Hz, 1H), 8.34 (s, 1H), 7.58 (d, J = 5.2 Hz, 1H), 7.45 (d, J = 9.1 Hz, 2H), 6.78 (d, J = 9.0 Hz, 2H), 4.98 (dd, J = 8.4, 4.4 Hz, 1H), 4.82 (s, 4H), 4.66-4.49 (m, 1H), 4.31 (dd, J = 10.6, 6.5 Hz, 1H), 4.13 (dd, J = 9.4, 3.5 Hz, 1H), 3.78 (dd, J = 10.5, 3.7 Hz, 2H), 2.40-2.29 (m, 4H) | (ESI (+)) m/e 435 (M + H)⁺ |

| Ex | Name | ¹H NMR | MS |
|---|---|---|---|
| 989 | N-(4-{[1-(tetrahydrofuran-2-ylcarbonyl)azetidin-3-yl]oxy}phenyl)-1,3-dihydro-2H-pyrrolo[3,4-c]pyridine-2-carboxamide | ¹H NMR (400 MHz, DMSO, Temp = 90° C.) δ 8.57 (s, 1H), 8.47 (d, J = 5.0 Hz, 1H), 8.06 (s, 1H), 7.50-7.39 (m, 2H), 7.37 (d, J = 4.9 Hz, 1H), 6.82-6.70 (m, 2H), 4.98 (tt, J = 6.5, 4.1 Hz, 1H), 4.83-4.73 (m, 5H), 4.34 (dd, J = 7.6, 6.2 Hz, 1H), 3.85-3.61 (m, 4H), 2.10-1.90 (m, 2H), 1.90-1.70 (m, 2H) | (ESI (+)) m/e 409 (M + H)⁺ |
| 990 | N-(4-{[1-(tetrahydrofuran-3-ylacetyl)azetidin-3-yl]oxy}phenyl)-1,3-dihydro-2H-pyrrolo[3,4-c]pyridine-2-carboxamide | ¹H NMR (400 MHz, DMSO, Temp = 90° C.) δ 8.57 (s, 1H), 8.47 (d, J = 5.0 Hz, 1H), 8.06 (s, 1H), 7.50-7.41 (m, 2H), 7.37 (d, J = 5.0 Hz, 1H), 6.92-6.66 (m, 2H), 5.03-4.91 (m, 1H), 4.83-4.73 (m, 5H), 3.78 (dd, J = 8.3, 7.1 Hz, 1H), 3.71 (td, J = 8.1, 5.4 Hz, 1H), 3.62 (dd, J = 15.4, 7.4 Hz, 1H), 3.27 (dd, J = 8.4, 6.5 Hz, 1H), 2.24-2.09 (m, 3H), 2.05-1.89 (m, 1H), 1.50 (dt, J = 14.7, 7.0 Hz, 1H) | (ESI (+)) m/e 423 (M + H)⁺ |
| 991 | N-(4-{[1-(cyclobutylcarbonyl)azetidin-3-yl]oxy}phenyl)-1,3-dihydro-2H-pyrrolo[3,4-c]pyridine-2-carboxamide | ¹H NMR (300 MHz, DMSO-d₆) δ 8.76 (s, 1H), 8.64 (d, J = 5.4 Hz, 1H), 8.38 (s, 1H), 7.70 (d, J = 5.4 Hz, 1H), 7.44 (d, J = 9.0 Hz, 2H), 6.77 (d, J = 9.0 Hz, 2H), 5.05-4.90 (m, 1H), 4.86 (s, 4H), 4.52-4.40 (m, 1H), 4.30-4.20 (m, 1H), 3.97 (dd, J = 9.5, 3.8 Hz, 1H), 3.74 (dd, J = 10.4, 3.8 Hz, 1H), 3.12 (p, J = 8.4 Hz, 1H), 2.19-1.96 (m, 4H), 1.96-1.79 (m, 1H), 1.79-1.62 (m, 1H) | (ESI (+)) m/e 393 (M + H)⁺ |
| 992 | N-(4-{[1-(cyclopentylcarbonyl)azetidin-3-yl]oxy}phenyl)-1,3-dihydro-2H-pyrrolo[3,4-c]pyridine-2-carboxamide | ¹H NMR (300 MHz, DMSO-d₆) δ 8.77 (s, 1H), 8.66 (d, J = 5.4 Hz, 1H), 8.38 (s, 1H), 7.73 (d, J = 5.3 Hz, 1H), 7.45 (d, J = 9.0 Hz, 2H), 6.78 (d, J = 9.0 Hz, 2H), 4.97 (t, J = 5.1 Hz, 1H), 4.87 (d, J = 3.9 Hz, 4H), 4.64-4.47 (m, 1H), 4.27 (dd, J = 10.3, 6.6 Hz, 1H), 4.14-4.02 (m, 1H), 3.82-3.65 (m, 1H), 2.76-2.55 (m, 1H), 1.89-1.39 (m, 8H) | (ESI (+)) m/e 407 (M + H)⁺ |
| 993 | N-(4-{[1-(3-phenylpropanoyl)pyrrolidin-3-yl]oxy}phenyl)-1,3-dihydro-2H-pyrrolo[3,4-c]pyridine-2-carboxamide | ¹H NMR (300 MHz, DMSO-d₆) δ 8.80 (s, 1H), 8.68 (d, J = 5.4 Hz, 1H), 8.37 (s, 1H), 7.77 (d, J = 5.3 Hz, 1H), 7.49-7.37 (m, 2H), 7.33-7.11 (m, 5H), 6.87 (dd, J = 9.1, 2.3 Hz, 2H), 4.91 (dd, J = 22.6, 11.0 Hz, 5H), 3.51 (d, J = 9.0 Hz, 4H), 2.81 (dd, J = 13.6, 7.3 Hz, 2H), 2.63-2.51 (m, 2H), 2.07 (dd, J = 17.7, 8.2 Hz, 2H) | (ESI (+)) m/e 457 (M + H)⁺ |
| 994 | N-(4-{[1-(phenylacetyl)pyrrolidin-3-yl]oxy}phenyl)-1,3-dihydro-2H-pyrrolo[3,4-c]pyridine-2-carboxamide | ¹H NMR (300 MHz, DMSO-d₆) δ 8.60 (s, 1H), 8.49 (d, J = 5.0 Hz, 1H), 8.29 (s, 1H), 7.43 (dd, J = 6.8, 4.6 Hz, 3H), 7.38-7.10 (m, 5H), 6.86 (dd, J = 8.9, 1.9 Hz, 2H), 4.98 (d, J = 21.6 Hz, 1H), 4.78 (d, J = 4.4 Hz, 4H), 3.59 (dd, J = 29.8, 8.4 Hz, 6H), 2.24-1.94 (m, 2H) | (ESI (+)) m/e 443 (M + H)⁺ |
| 995 | N-[4-({1-[(4-methoxyphenyl)acetyl]pyrrolidin-3-yl}oxy)phenyl]-1,3-dihydro-2H-pyrrolo[3,4-c]pyridine-2-carboxamide | ¹H NMR (300 MHz, DMSO-d₆) δ 8.60 (s, 1H), 8.49 (d, J = 5.0 Hz, 1H), 8.29 (s, 1H), 7.52-7.34 (m, 3H), 7.14 (t, J = 8.1 Hz, 2H), 6.95-6.73 (m, 4H), 4.97 (d, J = 21.7 Hz, 1H), 4.78 (d, J = 4.4 Hz, 4H), 3.70 (t, J = 10.2 Hz, 5H), 3.63-3.47 (m, 4H), 2.31-1.91 (m, 2H) | (ESI (+)) m/e 473 (M + H)⁺ |
| 996 | N-(4-{[1-(methoxyacetyl)pyrrolidin-3-yl]oxy}phenyl)-1,3-dihydro-2H-pyrrolo[3,4-c]pyridine-2-carboxamide | ¹H NMR (300 MHz, DMSO-d₆) δ 8.82 (s, 1H), 8.70 (d, J = 5.5 Hz, 1H), 8.39 (s, 1H), 7.81 (d, J = 5.3 Hz, 1H), 7.44 (d, J = 9.0 Hz, 2H), 6.96-6.81 (m, 2H), 4.91 (t, J = 9.8 Hz, 5H), 4.05 (s, 1H), 3.99 (s, 1H), 3.76-3.32 (m, 4H), 3.30 (s, 1.5H), 3.28 (s, 1.5H), 2.13 (dd, J = 7.4, 3.7 Hz, 1H), 2.07-1.96 (m, 1H) | (ESI (+)) m/e 397 (M + H)⁺ |
| 997 | N-(4-{[1-(cyclopropylcarbonyl)pyrrolidin-3-yl]oxy}phenyl)-1,3-dihydro-2H-pyrrolo[3,4-c]pyridine-2-carboxamide | ¹H NMR (300 MHz, DMSO-d₆) δ 8.60 (s, 1H), 8.50 (d, J = 5.0 Hz, 1H), 8.29 (s, 1H), 7.53-7.32 (m, 3H), 6.89 (dd, J = 9.0, 7.4 Hz, 2H), 5.03 (dd, J = 18.0, 16.5 Hz, 1H), 4.78 (d, J = 3.8 Hz, 4H), 3.98-3.61 (m, 2H), 3.51 (m, 2H), 2.31-1.91 (m, 2H), 1.76 (d, J = 20.7 Hz, 1H), 0.83-0.59 (m, 4H) | (ESI (+)) m/e 393 (M + H)⁺ |

-continued

| Ex | Name | ¹H NMR | MS |
|---|---|---|---|
| 998 | N-(4-{[1-(cyclohexylcarbonyl)pyrrolidin-3-yl]oxy}phenyl)-1,3-dihydro-2H-pyrrolo[3,4-c]pyridine-2-carboxamide | ¹H NMR (300 MHz, DMSO-$d_6$) δ 8.80 (s, 1H), 8.68 (d, J = 5.5 Hz, 1H), 8.37 (s, 1H), 7.77 (d, J = 5.0 Hz, 1H), 7.43 (dd, J = 9.0, 1.8 Hz, 2H), 6.88 (dd, J = 9.0, 7.5 Hz, 2H), 5.01 (s, 1H), 4.89 (t, J = 8.6 Hz, 4H), 3.82-3.25 (m, 4H), 2.43-1.93 (m, 3H), 1.67 (d, J = 10.0 Hz, 5H), 1.47-1.03 (m, 5H) | (ESI (+)) m/e 435 (M + H)⁺ |
| 999 | N-(4-{[1-(cyclopentylacetyl)pyrrolidin-3-yl]oxy}phenyl)-1,3-dihydro-2H-pyrrolo[3,4-c]pyridine-2-carboxamide | ¹H NMR (300 MHz, DMSO-$d_6$) δ 8.76 (s, 1H), 8.65 (d, J = 5.4 Hz, 1H), 8.35 (s, 1H), 7.71 (d, J = 5.2 Hz, 1H), 7.44 (d, J = 8.6 Hz, 2H), 7.02-6.78 (m, 2H), 4.96 (d, J = 21.3 Hz, 1H), 4.86 (d, J = 2.2 Hz, 4H), 3.67-3.44 (m, 4H), 2.31-2.01 (m, 5H), 1.75 (s, 2H), 1.62-1.38 (m, 4H), 1.10 (dd, J = 13.0, 5.9 Hz, 2H) | (ESI (+)) m/e 435 (M + H)⁺ |
| 1000 | N-(4-{[1-(cyclopentylcarbonyl)pyrrolidin-3-yl]oxy}phenyl)-1,3-dihydro-2H-pyrrolo[3,4-c]pyridine-2-carboxamide | ¹H NMR (300 MHz, DMSO-$d_6$) δ 8.76 (s, 1H), 8.64 (d, J = 5.4 Hz, 1H), 8.35 (s, 1H), 7.70 (d, J = 5.0 Hz, 1H), 7.54-7.34 (m, 2H), 6.97-6.77 (m, 2H), 4.97 (m, 1H), 4.86 (s, 4H), 3.69-3.36 (m, 4H), 2.95-2.68 (m, 1H), 2.11 (ddd, J = 17.8, 8.5, 4.2 Hz, 2H), 1.86-1.41 (m, 8H) | (ESI (+)) m/e 421 (M + H)⁺ |
| 1001 | N-{4-[(1-benzoylpyrrolidin-3-yl)oxy]phenyl}-1,3-dihydro-2H-pyrrolo[3,4-c]pyridine-2-carboxamide | ¹H NMR (300 MHz, DMSO-$d_6$) δ 8.78 (d, J = 2.9 Hz, 1H), 8.67 (d, J = 4.0 Hz, 1H), 8.36 (d, J = 14.5 Hz, 1H), 7.75 (d, J = 4.4 Hz, 1H), 7.61-7.33 (m, 7H), 6.88 (dd, J = 27.8, 8.9 Hz, 2H), 4.98 (m, 1H), 4.87 (m, 4H), 3.90-3.75 (m, 1H), 3.71-3.57 (m, 2H), 3.46 (d, J = 24.5 Hz, 1H), 2.11 (d, J = 13.7 Hz, 2H) | (ESI (+)) m/e 429 (M + H)⁺ |
| 1002 | N-(4-{[1-(3-ethoxypropanoyl)pyrrolidin-3-yl]oxy}phenyl)-1,3-dihydro-2H-pyrrolo[3,4-c]pyridine-2-carboxamide | ¹H NMR (300 MHz, DMSO-$d_6$) δ 8.73 (s, 1H), 8.61 (d, J = 5.3 Hz, 1H), 8.34 (s, 1H), 7.65 (d, J = 5.1 Hz, 1H), 7.44 (dd, J = 9.0, 1.1 Hz, 2H), 6.88 (dd, J = 9.0, 5.3 Hz, 2H), 4.97 (d, J = 19.1 Hz, 1H), 4.84 (s, 4H), 3.62-3.47 (m, 6H), 3.47-3.32 (m, 4H), 2.19-2.09 (m, 1H), 2.09-2.00 (m, 1H), 1.07 (dt, J = 9.8, 7.0 Hz, 3H) | (ESI (+)) m/e 425 (M + H)⁺ |
| 1003 | N-[4-({1-[(2-methylcyclopropyl)carbonyl]pyrrolidin-3-yl}oxy)phenyl]-1,3-dihydro-2H-pyrrolo[3,4-c]pyridine-2-carboxamide | ¹H NMR (300 MHz, DMSO-$d_6$) δ 8.78 (s, 1H), 8.66 (d, J = 5.4 Hz, 1H), 8.36 (s, 1H), 7.74 (d, J = 5.3 Hz, 1H), 7.54-7.35 (m, 2H), 6.88 (td, J = 9.9, 5.3 Hz, 2H), 4.99 (d, J = 30.6 Hz, 1H), 4.87 (d, J = 4.1 Hz, 4H), 3.94-3.58 (m, 2H), 3.52 (t, J = 5.2 Hz, 2H), 2.29-2.01 (m, 2H), 1.57-1.42 (m, 1H), 1.12-1.01 (m, 4H), 0.94 (ddd, J = 9.5, 7.6, 4.7 Hz, 1H), 0.62-0.50 (m, 1H) | (ESI (+)) m/e 407 (M + H)⁺ |
| 1004 | N-[4-({1-[(1-methylcyclopropyl)carbonyl]pyrrolidin-3-yl}oxy)phenyl]-1,3-dihydro-2H-pyrrolo[3,4-c]pyridine-2-carboxamide | ¹H NMR (300 MHz, DMSO-$d_6$) δ 8.77 (s, 1H), 8.65 (d, J = 5.4 Hz, 1H), 8.36 (s, 1H), 7.72 (d, J = 5.4 Hz, 1H), 7.57-7.37 (m, 2H), 6.88 (d, J = 9.0 Hz, 2H), 4.97 (s, 1H), 4.87 (d, J = 3.5 Hz, 4H), 4.26 (s, 2H), 3.77 (s, 2H), 2.10 (s, 2H), 1.26-1.17 (m, 3H), 0.92-0.80 (m, 1H), 0.66 (s, 1H), 0.48 (s, 2H) | (ESI (+)) m/e 407 (M + H)⁺ |
| 1005 | N-(4-{[1-(cyclobutylcarbonyl)pyrrolidin-3-yl]oxy}phenyl)-1,3-dihydro-2H-pyrrolo[3,4-c]pyridine-2-carboxamide | ¹H NMR (300 MHz, DMSO-$d_6$) δ 8.75 (s, 1H), 8.63 (d, J = 5.3 Hz, 1H), 8.34 (s, 1H), 7.68 (d, J = 5.1 Hz, 1H), 7.49-7.34 (m, 2H), 6.94-6.76 (m, 2H), 4.95 (d, J = 17.9 Hz, 1H), 4.85 (s, 4H), 3.67-3.10 (m, 5H), 2.10 (dtd, J = 19.7, 15.3, 8.2 Hz, 6H), 1.96-1.64 (m, 2H) | (ESI (+)) m/e 407 (M + H)⁺ |
| 1006 | N-(4-{[1-(3-methylbutanoyl)pyrrolidin-3-yl]oxy}phenyl)-1,3-dihydro-2H-pyrrolo[3,4-c]pyridine-2-carboxamide | ¹H NMR (300 MHz, DMSO-$d_6$) δ 8.79 (s, 1H), 8.67 (d, J = 5.4 Hz, 1H), 8.37 (s, 1H), 7.75 (d, J = 5.4 Hz, 1H), 7.44 (d, J = 9.0 Hz, 2H), 6.96-6.76 (m, 2H), 4.97 (d, J = 21.3 Hz, 1H), 4.87 (d, J = 5.4 Hz, 4H), 3.83-3.24 (m, 4H), 2.25-1.98 (m, 5H), 0.98-0.81 (m, 6H) | (ESI (+)) m/e 409 (M + H)⁺ |

| Ex | Name | ¹H NMR | MS |
|---|---|---|---|
| 1007 | N-(4-{[1-(2-methylpropanoyl)pyrrolidin-3-yl]oxy}phenyl)-1,3-dihydro-2H-pyrrolo[3,4-c]pyridine-2-carboxamide | ¹H NMR (300 MHz, DMSO-$d_6$) δ 8.76 (s, 1H), 8.65 (d, J = 5.4 Hz, 1H), 8.36 (s, 1H), 7.71 (d, J = 5.0 Hz, 1H), 7.44 (d, J = 8.8 Hz, 2H), 6.88 (dd, J = 9.0, 6.9 Hz, 2H), 4.97 (d, J = 25.9 Hz, 1H), 4.86 (d, J = 2.6 Hz, 4H), 3.80-3.26 (m, 4H), 2.64 (ddt, J = 27.4, 13.9, 7.1 Hz, 1H), 2.31-2.00 (m, 2H), 0.99 (ddd, J = 16.0, 9.0, 4.2 Hz, 6H) | (ESI (+)) m/e 395 (M + H)⁺ |
| 1008 | N-{4-[(1-acetylpyrrolidin-3-yl)oxy]phenyl}-1,3-dihydro-2H-pyrrolo[3,4-c]pyridine-2-carboxamide | ¹H NMR (300 MHz, DMSO-$d_6$) δ 8.79 (s, 1H), 8.67 (d, J = 5.5 Hz, 1H), 8.37 (s, 1H), 7.75 (d, J = 5.4 Hz, 1H), 7.44 (d, J = 8.9 Hz, 2H), 6.95-6.79 (m, 2H), 5.07-4.90 (m, 1H), 4.87 (d, J = 5.3 Hz, 4H), 3.83-3.22 (m, 4H), 2.26-2.00 (m, 2H), 1.97 (s, 1.5H), 1.93 (s, 1.5H) | (ESI (+)) m/e 367 (M + H)⁺ |
| 1009 | N-(4-{[1-(4,4,4-trifluorobutanoyl)pyrrolidin-3-yl]oxy}phenyl)-1,3-dihydro-2H-pyrrolo[3,4-c]pyridine-2-carboxamide | ¹H NMR (300 MHz, DMSO-$d_6$) δ 8.76 (s, 1H), 8.64 (d, J = 5.4 Hz, 1H), 8.36 (s, 1H), 7.71 (d, J = 5.4 Hz, 1H), 7.44 (dd, J = 9.0, 1.7 Hz, 2H), 6.88 (dd, J = 8.9, 6.4 Hz, 2H), 4.99 (d, J = 21.2 Hz, 1H), 4.86 (d, J = 2.1 Hz, 4H), 3.85-3.29 (m, 4H), 2.56 (d, J = 5.1 Hz, 4H), 2.11 (dd, J = 24.1, 8.1 Hz, 2H) | (ESI (+)) m/e 449 (M + H)⁺ |
| 1010 | N-(4-{[1-(tetrahydrofuran-3-ylcarbonyl)pyrrolidin-3-yl]oxy}phenyl)-1,3-dihydro-2H-pyrrolo[3,4-c]pyridine-2-carboxamide | ¹H NMR (300 MHz, DMSO-$d_6$) δ 8.77 (s, 1H), 8.66 (d, J = 5.4 Hz, 1H), 8.37 (s, 1H), 7.73 (d, J = 5.1 Hz, 1H), 7.44 (dd, J = 8.9, 1.6 Hz, 2H), 6.89 (dd, J = 8.8, 6.9 Hz, 2H), 4.98 (d, J = 21.7 Hz, 1H), 4.86 (d, J = 3.8 Hz, 4H), 3.95-3.46 (m, 8H), 3.20 (dd, J = 14.8, 7.8 Hz, 1H), 1.97 (d, J = 7.5 Hz, 4H) | (ESI (+)) m/e 423 (M + H)⁺ |
| 1011 | N-(4-{[1-(tetrahydrofuran-2-ylcarbonyl)pyrrolidin-3-yl]oxy}phenyl)-1,3-dihydro-2H-pyrrolo[3,4-c]pyridine-2-carboxamide | ¹H NMR (300 MHz, DMSO-$d_6$) δ 8.80 (s, 1H), 8.68 (d, J = 5.5 Hz, 1H), 8.38 (s, 1H), 7.78 (d, J = 5.4 Hz, 1H), 7.44 (d, J = 9.0 Hz, 2H), 6.88 (dd, J = 8.2, 4.6 Hz, 2H), 4.98 (d, J = 23.0 Hz, 1H), 4.88 (d, J = 7.4 Hz, 4H), 4.51 (dt, J = 13.2, 6.2 Hz, 2H), 3.89-3.46 (m, 5H), 2.33-1.67 (m, 6H) | (ESI (+)) m/e 423 (M + H)⁺ |
| 1012 | N-(4-{[1-(ethoxyacetyl)pyrrolidin-3-yl]oxy}phenyl)-1,3-dihydro-2H-pyrrolo[3,4-c]pyridine-2-carboxamide | ¹H NMR (300 MHz, DMSO-$d_6$) δ 8.79 (s, 1H), 8.67 (d, J = 5.5 Hz, 1H), 8.38 (s, 1H), 7.76 (d, J = 5.1 Hz, 1H), 7.44 (d, J = 9.0 Hz, 2H), 6.94-6.76 (m, 2H), 4.98 (d, J = 22.7 Hz, 2H), 4.87 (d, J = 5.8 Hz, 5H), 4.07 (s, 1H), 4.01 (s, 1H), 3.75-3.27 (m, 7H), 2.24-1.98 (m, 2H), 1.11 (dt, J = 10.8, 6.9 Hz, 3H) | (ESI (+)) m/e 411 (M + H)⁺ |
| 1026 | N-(4-{[1-(cyclohexylacetyl)piperidin-4-yl]oxy}phenyl)-1,3-dihydro-2H-pyrrolo[3,4-c]pyridine-2-carboxamide | ¹H NMR (300 MHz, DMSO-$d_6$) δ 8.77 (s, 1H), 8.65 (d, J = 5.4 Hz, 1H), 8.34 (s, 1H), 7.72 (d, J = 5.4 Hz, 1H), 7.50-7.34 (m, 2H), 6.99-6.82 (m, 2H), 4.86 (d, J = 3.5 Hz, 4H), 4.56-4.45 (m, 1H), 3.60-3.89 (m, 2H), 3.39-3.14 (m, 2H), 2.20 (d, J = 6.7 Hz, 2H), 1.90 (s, 2H), 1.72-1.39 (m, 8H), 1.29-1.06 (m, 3H), 0.94 (t, J = 11.6 Hz, 2H) | (ESI (+)) m/e 463 (M + H)⁺ |
| 1027 | N-(4-{[1-(tetrahydro-2H-pyran-4-ylacetyl)piperidin-4-yl]oxy}phenyl)-1,3-dihydro-2H-pyrrolo[3,4-c]pyridine-2-carboxamide | ¹H NMR (300 MHz, DMSO-$d_6$) δ 8.79 (s, 1H), 8.67 (d, J = 5.5 Hz, 1H), 8.36 (s, 1H), 7.76 (d, J = 5.5 Hz, 1H), 7.42 (d, J = 9.0 Hz, 2H), 6.91 (d, J = 9.0 Hz, 2H), 4.87 (d, J = 6.1 Hz, 5H), 4.50 (dd, J = 7.7, 3.9 Hz, 2H), 3.81 (ddd, J = 27.5, 21.4, 10.7 Hz, 4H), 3.39-3.14 (m, 4H), 2.27 (d, J = 6.5 Hz, 2H), 2.01-1.77 (m, 3H), 1.65-1.35 (m, 4H), 1.19 (tdd, J = 13.5, 9.2, 4.4 Hz, 2H) | (ESI (+)) m/e 465 (M + H)⁺ |
| 1037 | N-(4-{[1-(tetrahydrofuran-2-ylacetyl)azetidin-3-yl]oxy}phenyl)-1,3-dihydro-2H-pyrrolo[3,4-c]pyridine-2-carboxamide | ¹H NMR (300 MHz, DMSO-$d_6$) δ 8.75 (s, 1H), 8.63 (d, J = 5.4 Hz, 1H), 8.37 (s, 1H), 7.68 (d, J = 5.2 Hz, 1H), 7.45 (d, J = 9.0 Hz, 2H), 6.78 (d, J = 9.0 Hz, 2H), 4.97 (dd, J = 10.3, 6.6 Hz, 1H), 4.85 (s, 4H), 4.63-4.48 (m, 1H), 4.27 (s, 2H), 4.05 (dd, J = 13.5, 6.8 Hz, 2H), 3.62-3.45 (m, 2H), 2.28 (dddd, J = 20.3, 14.5, 10.4, 7.5 Hz, 3H), 2.06-1.90 (m, 1H), 1.81 (dd, J = 13.8, 6.4 Hz, 2H), 1.47 (ddd, J = 15.7, 11.8, 7.2 Hz, 1H) | (ESI (+)) m/e 423 (M + H)⁺ |

| Ex | Name | ¹H NMR | MS |
|---|---|---|---|
| 1038 | N-(4-{[1-(tetrahydro-2H-pyran-4-ylacetyl)azetidin-3-yl]oxy}phenyl)-1,3-dihydro-2H-pyrrolo[3,4-c]pyridine-2-carboxamide | ¹H NMR (300 MHz, DMSO-$d_6$) δ 8.77 (s, 1H), 8.65 (d, J = 5.4 Hz, 1H), 8.38 (s, 1H), 7.71 (d, J = 5.5 Hz, 1H), 7.45 (d, J = 9.1 Hz, 2H), 6.78 (d, J = 9.0 Hz, 2H), 4.96 (s, 1H), 4.86 (d, J = 3.0 Hz, 4H), 4.62-4.47 (m, 1H), 4.27 (dd, J = 10.7, 6.3 Hz, 1H), 4.03 (dd, J = 14.3, 7.2 Hz, 1H), 3.76 (dd, J = 18.7, 8.0 Hz, 3H), 3.25 (dd, J = 27.4, 15.8 Hz, 2H), 2.01 (t, J = 7.5 Hz, 2H), 1.89 (s, 1H), 1.56 (d, J = 11.3 Hz, 2H), 1.34-1.03 (m, 2H) | (ESI (+)) m/e 437 (M + H)⁺ |
| 1039 | N-(4-{[1-(morpholin-4-ylacetyl)azetidin-3-yl]oxy}phenyl)-1,3-dihydro-2H-pyrrolo[3,4-c]pyridine-2-carboxamide | ¹H NMR (300 MHz, DMSO-$d_6$) δ 8.70 (s, 1H), 8.59 (d, J = 5.3 Hz, 1H), 8.37 (s, 1H), 7.59 (d, J = 5.1 Hz, 1H), 7.47 (d, J = 9.0 Hz, 2H), 6.80 (d, J = 9.0 Hz, 2H), 5.06 (s, 1H), 4.83 (s, 4H), 4.65-4.53 (m, 1H), 4.44 (dd, J = 10.8, 6.2 Hz, 1H), 4.21-4.12 (m, 2H), 4.07 (s, 5H), 3.23 (s, 4H) | (ESI (+)) m/e 438 (M + H)⁺ |
| 1040 | N-(4-{[1-(cyclohexylacetyl)azetidin-3-yl]oxy}phenyl)-1,3-dihydro-2H-pyrrolo[3,4-c]pyridine-2-carboxamide | ¹H NMR (300 MHz, DMSO-$d_6$) δ 8.77 (s, 1H), 8.66 (d, J = 5.4 Hz, 1H), 8.38 (s, 1H), 7.73 (d, J = 5.4 Hz, 1H), 7.45 (d, J = 9.0 Hz, 2H), 6.78 (d, J = 9.0 Hz, 2H), 5.05-4.91 (m, 1H), 4.87 (d, J = 3.9 Hz, 4H), 4.62-4.45 (m, 1H), 4.27 (dd, J = 10.4, 6.5 Hz, 1H), 4.04 (dd, J = 9.1, 3.5 Hz, 1H), 3.74 (dd, J = 10.6, 3.7 Hz, 1H), 2.05-1.88 (m, 2H), 1.64 (d, J = 12.0 Hz, 6H), 1.16 (m, 3H), 0.94 (t, J = 11.8 Hz, 2H) | (ESI (+)) m/e 435 (M + H)⁺ |
| 1041 | N-(4-{[1-(2-methylbutanoyl)azetidin-3-yl]oxy}phenyl)-1,3-dihydro-2H-pyrrolo[3,4-c]pyridine-2-carboxamide | ¹H NMR (300 MHz, DMSO-$d_6$) δ 8.76 (s, 1H), 8.65 (d, J = 5.4 Hz, 1H), 8.38 (s, 1H), 7.71 (d, J = 5.4 Hz, 1H), 7.51-7.37 (m, 2H), 6.79 (d, J = 9.0 Hz, 2H), 4.98 (d, J = 2.5 Hz, 1H), 4.86 (d, J = 2.9 Hz, 4H), 4.64-4.48 (m, 1H), 4.33-4.21 (m, 1H), 4.12-4.02 (m, 1H), 3.76 (dd, J = 10.5, 3.8 Hz, 1H), 2.29 (dd, J = 13.8, 6.9 Hz, 1H), 1.58-1.39 (m, 1H), 1.39-1.20 (m, 1H), 0.97 (dd, J = 6.8, 4.1 Hz, 3H), 0.82 (q, J = 7.3 Hz, 3H) | (ESI (+)) m/e 395 (M + H)⁺ |
| 1042 | N-(4-{[1-(2,2-dimethylpropanoyl)azetidin-3-yl]oxy}phenyl)-1,3-dihydro-2H-pyrrolo[3,4-c]pyridine-2-carboxamide | ¹H NMR (300 MHz, DMSO-$d_6$) δ 8.78 (s, 1H), 8.67 (d, J = 5.5 Hz, 1H), 8.39 (s, 1H), 7.74 (d, J = 5.4 Hz, 1H), 7.54-7.33 (m, 2H), 6.82-6.64 (m, 2H), 4.94 (td, J = 6.3, 3.2 Hz, 1H), 4.87 (d, J = 4.8 Hz, 4H), 4.55-4.12 (m, 4H), 1.12 (s, 9H) | (ESI (+)) m/e 395 (M + H)⁺ |
| 1043 | N-(4-{[1-(3,3-dimethylbutanoyl)azetidin-3-yl]oxy}phenyl)-1,3-dihydro-2H-pyrrolo[3,4-c]pyridine-2-carboxamide | ¹H NMR (300 MHz, DMSO-$d_6$) δ 8.80 (s, 1H), 8.68 (d, J = 5.5 Hz, 1H), 8.39 (s, 1H), 7.77 (d, J = 5.5 Hz, 1H), 7.44 (d, J = 9.0 Hz, 2H), 6.78 (d, J = 9.0 Hz, 2H), 5.01-4.90 (m, 1H), 4.88 (d, J = 6.5 Hz, 4H), 4.60-4.45 (m, 1H), 4.27 (dd, J = 10.4, 6.5 Hz, 1H), 4.04 (dd, J = 8.9, 5.2 Hz, 1H), 3.74 (dd, J = 10.6, 3.8 Hz, 1H), 1.96 (s, 2H), 0.98 (s, 9H) | (ESI (+)) m/e 409 (M + H)⁺ |
| 1044 | N-(4-{[1-(tricyclo[3.3.1.1~3,7~]dec-1-ylacetyl)azetidin-3-yl]oxy}phenyl)-1,3-dihydro-2H-pyrrolo[3,4-c]pyridine-2-carboxamide | ¹H NMR (300 MHz, DMSO-$d_6$) δ 8.76 (s, 1H), 8.64 (d, J = 5.4 Hz, 1H), 8.38 (s, 1H), 7.70 (d, J = 5.4 Hz, 1H), 7.52-7.36 (m, 2H), 6.82-6.69 (m, 2H), 4.97-4.90 (m, 1H), 4.86 (s, 4H), 4.61-4.47 (m, 1H), 4.26 (dd, J = 10.3, 6.4 Hz, 1H), 4.08-3.99 (m, 1H), 3.74 (dd, J = 10.6, 3.9 Hz, 1H), 1.92 (s, 2H), 1.83 (s, 2H), 1.70-1.52 (m, 13H) | (ESI (+)) m/e 487 (M + H)⁺ |
| 1045 | N-[4-({1-[(4-methoxycyclohexyl)carbonyl]azetidin-3-yl}oxy)phenyl]-1,3-dihydro-2H-pyrrolo[3,4-c]pyridine-2-carboxamide | ¹H NMR (300 MHz, DMSO-$d_6$) δ 8.76 (s, 1H), 8.65 (d, J = 5.4 Hz, 1H), 8.38 (s, 1H), 7.71 (d, J = 5.4 Hz, 1H), 7.45 (d, J = 9.0 Hz, 2H), 6.78 (d, J = 9.0 Hz, 2H), 4.96 (s, 1H), 4.86 (d, J = 2.7 Hz, 4H), 4.58 (s, 1H), 4.31-4.19 (m, 1H), 4.05 (dd, J = 14.5, 7.4 Hz, 1H), 3.74 (d, J = 10.3 Hz, 1H), 3.36 (s, 3H), 3.19 (s, 3H), 2.27 (s, 1H), 1.81 (s, 2H), 1.57 (t, J = 12.2 Hz, 2H), 1.38 (s, 4H) | (ESI (+)) m/e 451 (M + H)⁺ |
| 1288 | N-(4-{[1-(tetrahydro-2H-pyran-2-ylcarbonyl)azetidin-3-yl]oxy}phenyl)-1,3-dihydro-2H-pyrrolo[3,4-c]pyridine-2-carboxamide | ¹H NMR (400 MHz, DMSO, Temp = 90° C.) δ 8.57 (s, 1H), 8.47 (d, J = 5.0 Hz, 1H), 8.06 (s, 1H), 7.50-7.40 (m, 2H), 7.37 (d, J = 5.0 Hz, 1H), 6.82-6.70 (m, 2H), 4.97 (tt, J = 6.4, 4.0 Hz, 1H), 4.83-4.73 (m, 4H), 4.69-4.44 (m, 1H), 4.44-4.19 (m, 1H), 4.21-3.98 (m, 1H), 3.89 (ddd, J = 14.6, 10.3, 2.3 Hz, 3H), 3.48-3.33 (m, 1H), 1.79 (dt, J = 6.0, 4.3 Hz, 1H), 1.70 (dt, J = 6.7, 2.5 Hz, 1H), 1.61-1.39 (m, 4H) | (ESI (+)) m/e 423 (M + H)⁺ |

| Ex | Name | ¹H NMR | MS |
|---|---|---|---|
| 1289 | N-(4-{[1-(tetrahydro-2H-pyran-2-ylcarbonyl)pyrrolidin-3-yl]oxy}phenyl)-1,3-dihydro-2H-pyrrolo[3,4-c]pyridine-2-carboxamide | ¹H NMR (400 MHz, DMSO, Temp = 90° C.) δ 8.57 (s, 1H), 8.47 (d, J = 5.0 Hz, 1H), 8.08-7.96 (m, 1H), 7.46-7.39 (m, 2H), 7.37 (d, J = 5.2 Hz, 1H), 6.84 (t, J = 5.9 Hz, 2H), 5.00-4.86 (m, 4H), 4.86-4.72 (m, 4H), 4.08-3.92 (m, 1H), 3.92-3.36 (m, 6H), 2.21-1.95 (m, 2H), 1.69-1.40 (m, 6H) | (ESI (+)) m/e 437 (M + H)⁺ |
| 1292 | N-{4-[(1-acetylpiperidin-3-yl)oxy]phenyl}-1,3-dihydro-2H-pyrrolo[3,4-c]pyridine-2-carboxamide | ¹H NMR (300 MHz, DMSO-d₆) δ 8.83 (s, 1H), 8.71 (d, J = 5.4 Hz, 1H), 8.38 (s, 1H), 7.83 (dd, J = 5.2, 3.0 Hz, 1H), 7.42 (dd, J = 8.9, 6.6 Hz, 2H), 6.89 (t, J = 8.5 Hz, 2H), 4.89 (d, J = 9.6 Hz, 4H), 4.43 (s, 1H), 4.22-3.94 (m, 1H), 3.67-3.47 (m, 2H), 3.36-3.02 (m, 1H), 2.02 (s, 1.5H), 1.87 (s, 1.5H), 1.83-1.32 (m, 3H) | (ESI (+)) m/e 381 (M + H)⁺ |
| 1293 | N-{4-[(1-butanoylpiperidin-3-yl)oxy]phenyl}-1,3-dihydro-2H-pyrrolo[3,4-c]pyridine-2-carboxamide | ¹H NMR (400 MHz, DMSO, Temp = 90° C.) δ 8.66 (s, 1H), 8.55 (d, J = 5.3 Hz, 1H), 8.07 (s, 1H), 7.54 (d, J = 5.1 Hz, 1H), 7.41 (d, J = 8.9 Hz, 2H), 6.95-6.70 (m, 2H), 4.83 (s, 4H), 4.23 (bs, 2H), 3.45 (bs, 2H), 2.24 (bs, 2H), 1.96 (bs, 1H), 1.73 (bs, 2H), 1.51 (dt, J = 14.8, 7.4 Hz, 3H), 0.87 (t, J = 7.4 Hz, 3H) | (ESI (+)) m/e 409 (M + H)⁺ |
| 1294 | N-(4-{[1-(3-methylbutanoyl)piperidin-3-yl]oxy}phenyl)-1,3-dihydro-2H-pyrrolo[3,4-c]pyridine-2-carboxamide | ¹H NMR (400 MHz, DMSO, Temp = 90° C.) δ 8.65 (s, 1H), 8.54 (d, J = 5.2 Hz, 1H), 8.07 (s, 1H), 7.52 (d, J = 5.2 Hz, 1H), 7.41 (d, J = 8.9 Hz, 2H), 6.92-6.79 (m, 2H), 4.82 (s, 4H), 4.25 (bs, 2H), 3.46 (bs, 2H), 2.14 (s, 2H), 2.05-1.90 (m, 2H), 1.73 (bs, 2H), 1.45 (bs, 1H), 0.90 (dd, J = 9.3, 6.5 Hz, 6H) | (ESI (+)) m/e 423 (M + H)⁺ |
| 1295 | N-(4-{[1-(methoxyacetyl)piperidin-3-yl]oxy}phenyl)-1,3-dihydro-2H-pyrrolo[3,4-c]pyridine-2-carboxamide | ¹H NMR (400 MHz, DMSO, Temp = 90° C.) δ 8.64 (s, 1H), 8.54 (d, J = 5.2 Hz, 1H), 8.07 (s, 1H), 7.51 (d, J = 5.1 Hz, 1H), 7.42 (d, J = 9.0 Hz, 2H), 6.86 (d, J = 9.0 Hz, 2H), 4.82 (s, 4H), 4.26 (bs, 1H), 4.05 (d, J = 13.6 Hz, 1H), 3.96 (m, 1H), 3.42 (m, 4H), 3.27 (bs, 3H), 1.93 (d, J = 28.0 Hz, 1H), 1.74 (bs, 2H), 1.49 (bs, 1H) | (ESI (+)) m/e 411 (M + H)⁺ |
| 1296 | N-(4-{[1-(2-methylbutanoyl)piperidin-3-yl]oxy}phenyl)-1,3-dihydro-2H-pyrrolo[3,4-c]pyridine-2-carboxamide | ¹H NMR (400 MHz, DMSO, Temp = 90° C.) δ 8.64 (s, 1H), 8.53 (d, J = 5.1 Hz, 1H), 8.06 (d, J = 2.1 Hz, 1H), 7.51 (d, J = 5.2 Hz, 1H), 7.44-7.38 (m, 2H), 6.85 (dd, J = 8.7, 1.2 Hz, 2H), 4.82 (s, 4H), 4.28-4.17 (m, 1H), 3.67 (s, 2H), 3.51-3.37 (m, 2H), 2.65 (s, 1H), 2.02-1.88 (m, 1H), 1.79-1.65 (m, 2H), 1.63-1.39 (m, 2H), 1.38-1.22 (m, 1H), 0.98 (dd, J = 6.7, 4.4 Hz, 3H), 0.90-0.76 (m, 3H) | (ESI (+)) m/e 423 (M + H)⁺ |
| 1297 | N-(4-{[1-(3,3,3-trifluoropropanoyl)piperidin-3-yl]oxy}phenyl)-1,3-dihydro-2H-pyrrolo[3,4-c]pyridine-2-carboxamide | ¹H NMR (400 MHz, DMSO, Temp = 90° C.) δ 8.64 (s, 1H), 8.54 (d, J = 5.2 Hz, 1H), 8.08 (m, 1H), 7.52 (d, J = 5.1 Hz, 1H), 7.42 (d, J = 8.9 Hz, 2H), 6.86 (d, J = 9.0 Hz, 2H), 4.82 (s, 4H), 4.26 (s, 1H), 3.63-3.41 (m, 6H), 1.93 (d, J = 26.2 Hz, 1H), 1.75 (m, 2H), 1.49 (m, 1H) | (ESI (+)) m/e 449 (M + H)⁺ |
| 1298 | N-(4-{[1-(cyclopropylacetyl)piperidin-3-yl]oxy}phenyl)-1,3-dihydro-2H-pyrrolo[3,4-c]pyridine-2-carboxamide | ¹H NMR (400 MHz, DMSO, Temp = 90° C.) δ 8.64 (s, 1H), 8.53 (d, J = 5.2 Hz, 1H), 8.06 (s, 1H), 7.51 (d, J = 5.3 Hz, 1H), 7.48-7.35 (m, 2H), 6.92-6.79 (m, 2H), 4.82 (s, 4H), 4.23 (m, 1H), 3.42-3.13 (m, 4H), 2.27 (d, J = 33.4 Hz, 3H), 1.93 (d, J = 26.2 Hz, 1H), 1.72 (m, 2H), 1.46 (m, 1H), 0.95 (m, 1H), 0.43 (d, J = 8.0 Hz, 2H), 0.09 (m, 2H) | (ESI (+)) m/e 421 (M + H)⁺ |
| 1299 | N-(4-{[1-(cyclobutylcarbonyl)piperidin-3-yl]oxy}phenyl)-1,3-dihydro-2H-pyrrolo[3,4-c]pyridine-2-carboxamide | ¹H NMR (400 MHz, DMSO, Temp = 90° C.) δ 8.64 (s, 1H), 8.53 (d, J = 5.1 Hz, 1H), 8.07 (bs, 1H), 7.50 (d, J = 5.2 Hz, 1H), 7.45-7.39 (m, 2H), 6.88-6.82 (m, 2H), 4.82 (s, 4H), 4.27-4.15 (m, 1H), 3.48-3.38 (m, 2H), 2.24-1.65 (m, 9H), 1.50-1.38 (m, 1H) | (ESI (+)) m/e 421 (M + H)⁺ |

| Ex | Name | ¹H NMR | MS |
|---|---|---|---|
| 1300 | N-(4-{[1-(cyclobutylacetyl)piperidin-3-yl]oxy}phenyl)-1,3-dihydro-2H-pyrrolo[3,4-c]pyridine-2-carboxamide | ¹H NMR (400 MHz, DMSO, Temp = 90° C.) δ 8.64 (s, 1H), 8.53 (d, J = 5.1 Hz, 1H), 8.10-8.05 (m, 1H), 7.51 (d, J = 5.2 Hz, 1H), 7.42 (d, J = 7.7 Hz, 1H), 6.89-6.82 (m, 2H), 4.82 (s, 4H), 4.51-3.84 (m, 1H), 2.67-2.53 (m, 1H), 2.30 (d, J = 7.4 Hz, 1H), 2.11-1.91 (m, 3H), 1.88-1.58 (m, 7H) | (ESI (+)) m/e 435 (M + H)⁺ |
| 1301 | N-(4-{[1-(cyclopentylcarbonyl)piperidin-3-yl]oxy}phenyl)-1,3-dihydro-2H-pyrrolo[3,4-c]pyridine-2-carboxamide | ¹H NMR (400 MHz, DMSO, Temp = 90° C.) δ 8.64 (s, 1H), 8.53 (d, J = 5.1 Hz, 1H), 8.07 (s, 1H), 7.51 (d, J = 5.2 Hz, 1H), 7.42 (dd, J = 9.0, 3.7 Hz, 2H), 6.86 (d, J = 9.0 Hz, 2H), 4.82 (s, 4H), 4.45-3.57 (m, 5H), 2.92 (s, 2H), 1.97 (s, 1H), 1.67 (m, 12H) | (ESI (+)) m/e 435 (M + H)⁺ |
| 1302 | N-(4-{[1-(cyclopentylacetyl)piperidin-3-yl]oxy}phenyl)-1,3-dihydro-2H-pyrrolo[3,4-c]pyridine-2-carboxamide | ¹H NMR (400 MHz, DMSO, Temp = 90° C.) δ 8.65 (s, 1H), 8.54 (d, J = 5.2 Hz, 1H), 8.07 (s, 1H), 7.52 (d, J = 5.2 Hz, 1H), 7.49-7.35 (m, 2H), 6.92-6.79 (m, 2H), 4.82 (s, 4H), 4.24 (s, 1H), 3.46 (s, 4H), 2.36-2.07 (m, 3H), 1.93 (m, 1H), 1.73 (m, 4H), 1.51 (dd, J = 22.2, 13.1 Hz, 5H), 1.13 (m, 2H) | (ESI (+)) m/e 449 (M + H)⁺ |
| 1303 | N-[4-({1-[(2S)-tetrahydrofuran-2-ylcarbonyl]piperidin-3-yl}oxy)phenyl]-1,3-dihydro-2H-pyrrolo[3,4-c]pyridine-2-carboxamide | ¹H NMR (400 MHz, DMSO, Temp = 90° C.) δ 8.64 (bs, 1H), 8.53 (m, 1H), 8.07 (bs, 1H), 7.51 (d, J = 5.2 Hz, 1H), 7.44-7.38 (m, 3H), 6.87 (dd, J = 9.0, 3.3 Hz, 3H), 4.82 (s, 4H), 4.64-4.50 (m, 1H), 4.30-4.17 (m, 1H), 3.99-3.87 (m, 1H), 3.83-3.55 (m, 4H), 2.03-1.68 (m, 7H), 1.48 (m, 1H) | (ESI (+)) m/e 437 (M + H)⁺ |
| 1304 | N-[4-({1-[(2R)-tetrahydrofuran-2-ylcarbonyl]piperidin-3-yl}oxy)phenyl]-1,3-dihydro-2H-pyrrolo[3,4-c]pyridine-2-carboxamide | ¹H NMR (400 MHz, DMSO, Temp = 90° C.) δ 8.64 (bs, 1H), 8.54 (m, 1H), 8.07 (bs, 1H), 7.52 (d, J = 4.8 Hz, 1H), 7.44-7.38 (m, 3H), 6.91-6.83 (m, 3H), 4.82 (bs, 4H), 4.64-4.49 (m, 1H), 4.30-4.16 (m, 1H), 3.93 (s, 1H), 3.43-3.20 (m, 3H), 2.05-1.75 (m, 7H), 1.48 (s, 1H) | (ESI (+)) m/e 437 (M + H)⁺ |
| 1305 | N-(4-{[1-(tetrahydro-2H-pyran-4-ylcarbonyl)piperidin-3-yl]oxy}phenyl)-1,3-dihydro-2H-pyrrolo[3,4-c]pyridine-2-carboxamide | ¹H NMR (400 MHz, DMSO, Temp = 90° C.) δ 8.62 (s, 1H), 8.52 (d, J = 5.1 Hz, 1H), 8.06 (s, 1H), 7.53-7.42 (m, 2H), 7.41 (s, 1H), 6.91-6.79 (m, 2H), 4.81 (s, 4H), 4.26 (s, 1H), 3.81 (m, 3H), 3.45 (s, 2H), 2.76 (s, 2H), 2.14 (m, 2H), 1.88-1.42 (m, 7H) | (ESI (+)) m/e 451 (M + H)⁺ |
| 1306 | N-(4-{[1-(tetrahydro-2H-pyran-2-ylcarbonyl)piperidin-3-yl]oxy}phenyl)-1,3-dihydro-2H-pyrrolo[3,4-c]pyridine-2-carboxamide | ¹H NMR (400 MHz, DMSO, Temp = 90° C.) δ 8.62 (s, 1H), 8.52 (d, J = 5.1 Hz, 1H), 8.06 (s, 1H), 7.47 (d, J = 5.2 Hz, 1H), 7.42 (dd, J = 9.1, 2.6 Hz, 2H), 6.86 (dd, J = 9.0, 2.1 Hz, 2H), 4.81 (s, 4H), 4.08 (m, 3H), 3.93-3.54 (m, 3H), 3.28-3.13 (m, 2H), 2.00 (s, 1H), 1.85-1.36 (m, 9H) | (ESI (+)) m/e 451 (M + H)⁺ |
| 1307 | N-(4-{[1-(tetrahydro-2H-pyran-4-ylacetyl)piperidin-3-yl]oxy}phenyl)-1,3-dihydro-2H-pyrrolo[3,4-c]pyridine-2-carboxamide | ¹H NMR (400 MHz, DMSO, Temp = 90° C.) δ 8.64 (s, 1H), 8.54 (d, J = 5.2 Hz, 1H), 8.07 (s, 1H), 7.51 (d, J = 5.1 Hz, 1H), 7.42 (d, J = 8.9 Hz, 2H), 6.85 (d, J = 9.0 Hz, 2H), 4.24 (s, 2H), 3.32 (dd, J = 50.2, 38.3 Hz, 6H), 2.20 (m, 2H), 1.92 (m, 2H), 1.73 (m, 2H), 1.56 (m, 2H), 1.46 (m, 1H), 1.20 (m, 2H) | (ESI (+)) m/e 465 (M + H)⁺ |
| 1308 | N-(4-{[1-(tetrahydrofuran-2-ylacetyl)piperidin-3-yl]oxy}phenyl)-1,3-dihydro-2H-pyrrolo[3,4-c]pyridine-2-carboxamide | ¹H NMR (400 MHz, DMSO, Temp = 90° C.) δ 8.63 (s, 1H), 8.52 (d, J = 5.2 Hz, 1H), 8.06 (s, 1H), 7.49 (d, J = 5.2 Hz, 1H), 7.42 (d, J = 8.8 Hz, 2H), 6.86 (d, J = 9.0 Hz, 2H), 4.81 (s, 5H), 4.37-4.03 (m, 2H), 3.71 (s, 2H), 3.63-3.50 (m, 3H), 2.61 (m, 2H), 2.44-2.25 (m, 1H), 1.96 (m, 2H), 1.87-1.63 (m, 4H), 1.47 (m, 2H) | (ESI (+)) m/e 451 (M + H)⁺ |

-continued

| Ex | Name | ¹H NMR | MS |
|---|---|---|---|
| 1309 | N-(4-{[1-(tetrahydrofuran-3-ylacetyl)piperidin-3-yl]oxy}phenyl)-1,3-dihydro-2H-pyrrolo[3,4-c]pyridine-2-carboxamide | ¹H NMR (400 MHz, DMSO, Temp = 90° C.) δ 8.64 (s, 1H), 8.54 (d, J = 5.2 Hz, 1H), 8.07 (s, 1H), 7.51 (d, J = 5.2 Hz, 1H), 7.42 (d, J = 8.9 Hz, 2H), 6.89-6.76 (m, 2H), 4.82 (s, 5H), 4.27 (s, 1H), 3.67-3.17 (m, 11H), 2.34 (d, J = 26.3 Hz, 5H), 1.93 (d, J = 29.4 Hz, 3H), 1.73 (s, 3H), 1.47 (s, 1H) | (ESI (+)) m/e 451 (M + H)⁺ |
| 1347 | N-(4-{[1-(5-oxo-L-prolyl)piperidin-4-yl]oxy}phenyl)-1,3-dihydro-2H-pyrrolo[3,4-c]pyridine-2-carboxamide | ¹H NMR (400 MHz, DMSO-D₂O, Temp = 90° C.) δ ppm 8.57 (s, 1 H) 8.48 (d, J = 4.88 Hz, 1 H) 7.40 (d, J = 8.54 Hz, 3 H) 6.90 (d, J = 8.85 Hz, 2 H) 4.79 (d, J = 7.63 Hz, 4 H) 4.45-4.58 (m, 2 H) 3.75 (s, 2 H) 3.34-3.42 (m, 4 H) 2.30-2.43 (m, 1 H) 2.10-2.21 (m, 2 H) 1.94 (d, J = 5.80 Hz, 1 H) 1.54-1.69 (m, 2 H) | (APCI (+)) m/e 450 (M + H)⁺ |
| 1386 | N-(4-{[1-(5-oxo-L-prolyl)azetidin-3-yl]oxy}phenyl)-1,3-dihydro-2H-pyrrolo[3,4-c]pyridine-2-carboxamide | ¹H NMR (400 MHz, DMSO-D₂O, Temp = 90° C.) δ ppm 8.57 (s, 1 H) 8.48 (d, J = 4.88 Hz, 1 H) 7.38-7.48 (m, 3 H) 6.75-6.83 (m, 2 H) 4.98-5.06 (m, 1 H) 4.79 (d, J = 7.93 Hz, 4 H) 4.29-4.72 (m, 2 H) 4.18 (dd, J = 8.39, 4.73 Hz, 1 H) 3.64-4.12 (m, 2 H) 2.06-2.41 (m, 3 H) 1.90-2.06 (m, 1 H) | (APCI (+)) m/e 421 (M + H)⁺ |
| 1387 | N-{4-[(1-propanoylazetidin-3-yl)oxy]phenyl}-1,3-dihydro-2H-pyrrolo[3,4-c]pyridine-2-carboxamide | ¹H NMR (400 MHz, DMSO-D₂O, Temp = 90° C.) δ ppm 8.57 (s, 1 H) 8.48 (d, J = 5.19 Hz, 1 H) 7.38-7.46 (m, 3 H) 6.74-6.82 (m, 2 H) 4.94-5.03 (m, 1 H) 4.79 (d, J = 7.02 Hz, 4 H) 4.35 (s, 2 H) 3.90 (s, 2 H) 2.10 (q, J = 7.43 Hz, 2 H) 1.00 (t, J = 7.48 Hz, 3 H) | (APCI (+)) m/e 367 (M + H)⁺ |
| 1388 | N-(4-{[1-(2,2-dimethylbutanoyl)azetidin-3-yl]oxy}phenyl)-1,3-dihydro-2H-pyrrolo[3,4-c]pyridine-2-carboxamide | ¹H NMR (400 MHz, DMSO-D₂O, Temp = 90° C.) δ ppm 8.57 (s, 1 H) 8.48 (d, J = 5.19 Hz, 1 H) 7.39-7.46 (m, 3 H) 6.78 (d, J = 8.85 Hz, 2 H) 4.90-5.02 (m, 1 H) 4.79 (d, J = 7.93 Hz, 4 H) 4.51 (s, 2 H) 4.01 (d, J = 8.54 Hz, 2 H) 1.49 (q, J = 7.32 Hz, 2 H) 1.09 (s, 6 H) 0.81 (t, J = 7.48 Hz, 3 H) | (APCI (+)) m/e 409 (M + H)⁺ |
| 1389 | N-(4-{[1-(2-ethylbutanoyl)azetidin-3-yl]oxy}phenyl)-1,3-dihydro-2H-pyrrolo[3,4-c]pyridine-2-carboxamide | ¹H NMR (400 MHz, DMSO-D₂O, Temp = 90° C.) δ ppm 8.57 (s, 1 H) 8.48 (d, J = 5.19 Hz, 1 H) 7.37-7.47 (m, 3 H) 6.79 (d, J = 8.85 Hz, 2 H) 4.95-5.03 (m, 1 H) 4.79 (d, J = 7.93 Hz, 4 H) 4.44 (s, 2 H) 3.95 (s, 2 H) 2.08-2.22 (m, 1 H) 1.32-1.55 (m, 4 H) 0.83 (t, J = 7.32 Hz, 6 H) | (APCI (+)) m/e 409 (M + H)⁺ |
| 1390 | N-(4-{[1-(pent-4-ynoyl)azetidin-3-yl]oxy}phenyl)-1,3-dihydro-2H-pyrrolo[3,4-c]pyridine-2-carboxamide | ¹H NMR (400 MHz, DMSO-D₂O, Temp = 90° C.) δ ppm 8.57 (s, 1 H) 8.48 (d, J = 4.88 Hz, 1 H) 7.34-7.49 (m, 3 H) 6.78 (d, J = 8.85 Hz, 2 H) 4.92-5.06 (m, 1 H) 4.79 (d, J = 7.93 Hz, 4 H) 4.42 (d, J = 78.13 Hz, 2 H) 3.66-4.19 (m, 2 H) 2.54 (t, J = 2.44 Hz, 1 H) 2.27-2.43 (m, 4 H) | (APCI (+)) m/e 391 (M + H)⁺ |
| 1391 | N-(4-{[1-(furan-2-ylcarbonyl)azetidin-3-yl]oxy}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 5.19 Hz, 1 H) 7.77 (s, 1 H) 7.37-7.48 (m, 3 H) 7.04 (d, J = 3.66 Hz, 1 H) 6.81 (d, J = 8.85 Hz, 2 H) 6.57-6.63 (m, 1 H) 5.01-5.14 (m, 1 H) 4.79 (d, J = 8.24 Hz, 4 H) 4.67 (s, 2 H) 4.17 (s, 2 H) | (APCI (+)) m/e 405 (M + H)⁺ |
| 1392 | N-(4-{[1-(furan-3-ylcarbonyl)azetidin-3-yl]oxy}phenyl)-1,3-dihydro-2H-pyrrolo[3,4-c]pyridine-2-carboxamide | ¹H NMR (400 MHz, DMSO-D₂O, Temp = 90° C.) δ ppm 8.57 (s, 1 H) 8.48 (d, J = 5.19 Hz, 1 H) 8.07 (s, 1 H) 7.67 (s, 1 H) 7.38-7.47 (m, 3 H) 6.80 (d, J = 8.85 Hz, 2 H) 6.72 (s, 1 H) 5.03-5.11 (m, 1 H) 4.79 (d, J = 7.63 Hz, 4 H) 4.60 (s, 2 H) 4.12 (s, 2 H) | (APCI (+)) m/e 405 (M + H)⁺ |
| 1393 | N-(4-{[1-(thiophen-3-ylcarbonyl)azetidin-3-yl]oxy}phenyl)-1,3-dihydro-2H-pyrrolo[3,4-c]pyridine-2-carboxamide | ¹H NMR (400 MHz, DMSO-D₂O, Temp = 90° C.) δ ppm 8.57 (s, 1 H) 8.48 (d, J = 4.88 Hz, 1 H) 7.97 (d, J = 1.83 Hz, 1 H) 7.55 (dd, J = 5.04, 2.90 Hz, 1 H) 7.35-7.46 (m, 4 H) 6.80 (d, J = 8.85 Hz, 2 H) 5.01-5.11 (m, 1 H) 4.79 (d, J = 7.93 Hz, 4 H) 4.62 (s, 2 H) 4.16 (s, 2 H) | (APCI (+)) m/e 421 (M + H)⁺ |

| Ex | Name | ¹H NMR | MS |
|---|---|---|---|
| 1394 | N-(4-{[1-(1H-pyrrol-2-ylcarbonyl)azetidin-3-yl]oxy}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 5.19 Hz, 1 H) 7.37-7.48 (m, 3 H) 6.93 (s, 1 H) 6.81 (d, J = 8.85 Hz, 2 H) 6.51 (d, J = 3.36 Hz, 1 H) 6.14-6.18 (m, 1 H) 5.02-5.14 (m, 1 H) 4.79 (d, J = 7.93 Hz, 4 H) 4.57-4.66 (m, 2 H) 4.13 (d, J = 7.93 Hz, 2 H) | (APCI (+)) m/e 404 (M + H)⁺ |
| 1395 | N-(4-{[1-(pyrimidin-4-ylcarbonyl)azetidin-3-yl]oxy}phenyl)-1,3-dihydro-2H-pyrrolo[3,4-c]pyridine-2-carboxamide | ¹H NMR (400 MHz, DMSO-D₂O, Temp = 90° C.) δ ppm 9.09 (s, 1 H) 8.75 (d, J = 2.14 Hz, 1 H) 8.66 (s, 1 H) 8.58 (s, 1 H) 8.48 (d, J = 4.88 Hz, 1 H) 7.37-7.47 (m, 3 H) 6.81 (d, J = 8.85 Hz, 2 H) 5.06-5.13 (m, 1 H) 4.92-5.04 (m, 1 H) 4.79 (d, J = 7.63 Hz, 4 H) 4.50 (s, 2 H) 4.09 (s, 1 H) | (APCI (+)) m/e 417 (M + H)⁺ |
| 1396 | N-[4-({1-[(5-methylpyrazin-2-yl)carbonyl]azetidin-3-yl}oxy)phenyl]-1,3-dihydro-2H-pyrrolo[3,4-c]pyridine-2-carboxamide | ¹H NMR (400 MHz, DMSO-D₂O, Temp = 90° C.) δ ppm 8.96 (s, 1 H) 8.58 (s, 1 H) 8.54 (s, 1 H) 8.48 (d, J = 4.88 Hz, 1 H) 7.38-7.47 (m, 3 H) 6.80 (d, J = 8.85 Hz, 2 H) 5.04-5.13 (m, 1 H) 4.89-5.02 (m, 1 H) 4.79 (d, J = 7.63 Hz, 4 H) 4.48 (s, 2 H) 4.06 (s, 1 H) 2.57 (s, 3 H) | (APCI (+)) m/e 431 (M + H)⁺ |
| 1397 | N-(4-{[1-(N,N-dimethylglycyl)azetidin-3-yl]oxy}phenyl)-1,3-dihydro-2H-pyrrolo[3,4-c]pyridine-2-carboxamide | ¹H NMR (400 MHz, DMSO-d₆/Deuterium Oxide, Temp = 90° C.) δ ppm 8.57-8.59 (bs, 1H), 8.48 (dd, J = 4.9, 1.8 Hz, 1H), 7.43-7.47 (m, 2H), 7.41 (d, J = 6.7 Hz, 1H), 6.80-6.83 (m, 2H), 5.08-5.16 (m, 1H), 4.82 (s, 2H), 4.79 (s, 2H), 4.67-4.74 (m, 2H), 4.30 (dd, J = 10.1, 4.1 Hz, 2H), 2.91 (s, 8H) | (APCI (+)) m/e 396 (M + H)⁺ |
| 1398 | N-(4-{[1-(N,N-dimethyl-beta-alanyl)azetidin-3-yl]oxy}phenyl)-1,3-dihydro-2H-pyrrolo[3,4-c]pyridine-2-carboxamide | ¹H NMR (400 MHz, DMSO-d₆/Deuterium Oxide, Temp = 90° C.) δ ppm 8.57 (s, 1H), 8.48 (d, J = 5.2 Hz, 1H), 7.44-7.48 (m, 2H), 7.40 (d, J = 4.6 Hz, 1H), 6.80-6.84 (m, 2H), 5.09-5.16 (m, 1H), 4.83 (s, 2H), 4.79 (s, 2H), 4.70 (ddd, J = 10.4, 6.6, 1.2 Hz, 2H), 4.30 (ddd, J = 10.4, 4.1, 1.2 Hz, 2H), 2.91 (s, 6H), 2.50 (t, J = 7.3 Hz, 2H), 2.23 (t, J = 7.2 Hz, 2H) | (APCI (+)) m/e 410 (M + H)⁺ |
| 1399 | N-(4-{[1-(pyrrolidin-1-ylacetyl)azetidin-3-yl]oxy}phenyl)-1,3-dihydro-2H-pyrrolo[3,4-c]pyridine-2-carboxamide | ¹H NMR (400 MHz, DMSO-d₆/Deuterium Oxide, Temp = 90° C.) δ ppm 8.58 (s, 1H), 8.48 (dd, J = 5.2, 1.8 Hz, 1H), 7.43-7.47 (m, 2H), 7.40 (d, J = 5.2 Hz, 1H), 6.80-6.84 (m, 2H), 5.09-5.16 (m, 1H), 4.82 (s, 2H), 4.79 (s, 2H), 4.70 (ddd, J = 10.2, 6.4, 1.1 Hz, 2H), 4.30 (ddd, J = 10.3, 4.2, 1.1 Hz, 2H), 3.18 (s, 2H), 2.55-2.62 (m, 4H), 1.68-1.75 (m, 4H) | (APCI (+)) m/e 422 (M + H)⁺ |
| 1400 | N-[4-({1-[3-(pyrrolidin-1-yl)propanoyl]azetidin-3-yl}oxy)phenyl]-1,3-dihydro-2H-pyrrolo[3,4-c]pyridine-2-carboxamide | ¹H NMR (400 MHz, DMSO-d₆/Deuterium Oxide, Temp = 90° C.) δ ppm 8.57-8.58 (bs, 1H), 8.48 (dd, J = 5.0, 2.0 Hz, 1H), 7.41-7.45 (m, 2H), 7.40 (d, J = 4.9 Hz, 1H), 6.76-6.80 (m, 2H), 4.94-5.01 (m, 1H), 4.82 (s, 2H), 4.79 (s, 2H), 4.19-4.64 (m, 2H), 3.70-4.17 (m, 2H), 2.66 (t, J = 7.3 Hz, 2H), 2.44-2.50 (m, 4H), 2.27 (t, J = 7.3 Hz, 2H), 1.65-1.71 (m, 4H) | (APCI (+)) m/e 436 (M + H)⁺ |
| 1401 | N-[4-({1-[3-(piperidin-1-yl)propanoyl]azetidin-3-yl}oxy)phenyl]-1,3-dihydro-2H-pyrrolo[3,4-c]pyridine-2-carboxamide | ¹H NMR (400 MHz, DMSO-D₂O, Temp = 90° C.) δ ppm 8.57 (s, 1 H) 8.48 (d, J = 4.88 Hz, 1 H) 7.35-7.48 (m, 3 H) 6.74-6.83 (m, 2 H) 4.92-5.02 (m, 1 H) 4.79 (d, J = 7.93 Hz, 4 H) 4.18-4.71 (m, 2 H) 3.94 (d, J = 92.77 Hz, 2 H) 2.53-2.58 (m, 2 H) 2.32-2.40 (m, 4 H) 2.24 (t, J = 7.17 Hz, 2 H) 1.44-1.54 (m, 4 H) 1.33-1.41 (m, 2 H) | (APCI (+)) m/e 450 (M + H)⁺ |
| 1402 | N-[4-({1-[(4-methylpiperazin-1-yl)acetyl]azetidin-3-yl}oxy)phenyl]-1,3-dihydro-2H-pyrrolo[3,4-c]pyridine-2-carboxamide | ¹H NMR (400 MHz, DMSO-d₆/Deuterium Oxide, Temp = 90° C.) δ ppm 8.58 (s, 1H), 8.48 (dd, J = 5.0, 2.0 Hz, 1H), 7.41-7.45 (m, 2H), 7.40 (d, J = 5.2 Hz, 1H), 6.75-6.80 (m, 2H), 5.08-5.17 (m, 1H), 4.82 (s, 2H), 4.79 (s, 2H), 4.70 (ddd, J = 10.0, 6.3, 1.3 Hz, 2H), 4.30 (ddd, J = 10.0, 4.0, 1.0 Hz, 2H), 3.00 (s, 2H), 2.41-2.48 (m, 4H), 2.30-2.37 (m, 4H), 2.15 (s, 3H) | (APCI (+)) m/e 451 (M + H)⁺ |

| Ex | Name | ¹H NMR | MS |
|---|---|---|---|
| 1403 | N-[4-({1-[3-(4-methylpiperazin-1-yl)propanoyl]azetidin-3-yl}oxy)phenyl]-1,3-dihydro-2H-pyrrolo[3,4-c]pyridine-2-carboxamide | ¹H NMR (400 MHz, DMSO-D₂O, Temp = 90° C.) δ ppm 8.57 (s, 1 H) 8.48 (d, J = 4.88 Hz, 1 H) 7.38-7.48 (m, 3 H) 6.78 (d, J = 9.16 Hz, 2 H) 4.93-5.01 (m, 1 H) 4.79 (d, J = 7.93 Hz, 4 H) 4.19-4.64 (m, 2 H) 3.94 (d, J = 87.28 Hz, 2 H) 2.53-2.58 (m, 2 H) 2.36-2.43 (m, 4 H) 2.29-2.35 (m, 4 H) 2.24 (t, J = 7.17 Hz, 2 H) 2.15 (s, 3 H) | (APCI (+)) m/e 456 (M + H)⁺ |
| 1423 | N-[4-({1-[(2S)-2-methylbutanoyl]piperidin-4-yl}oxy)phenyl]-1,3-dihydro-2H-pyrrolo[3,4-c]pyridine-2-carboxamide | ¹H NMR (300 MHz, DMSO-d₆) δ 8.60 (s, 1H), 8.50 (d, J = 5.0 Hz, 1H), 8.27 (s, 1H), 7.51-7.34 (m, 3H), 6.90 (d, J = 9.0 Hz, 2H), 4.78 (d, J = 4.0 Hz, 4H), 4.60-4.44 (m, 1H), 3.84 (d, J = 39.0 Hz, 2H), 3.46-3.12 (m, 2H), 2.73 (dd, J = 13.4, 6.8 Hz, 1H), 1.99 (s, 2H), 1.55 (dt, J = 21.7, 7.3 Hz, 3H), 1.42-1.21 (m, 1H), 0.97 (t, J = 5.7 Hz, 3H), 0.81 (t, J = 7.4 Hz, 3H) | (ESI (+)) m/e 423 (M + H)⁺ |
| 1424 | N-[4-({1-[(2S)-tetrahydrofuran-2-ylcarbonyl]piperidin-4-yl}oxy)phenyl]-1,3-dihydro-2H-pyrrolo[3,4-c]pyridine-2-carboxamide | ¹H NMR (300 MHz, DMSO-d₆) δ 8.60 (s, 1H), 8.50 (d, J = 5.0 Hz, 1H), 8.28 (s, 1H), 7.46-7.39 (m, 3H), 6.94-6.87 (m, 2H), 4.86-4.74 (m, 4H), 4.67 (t, J = 6.6 Hz, 1H), 4.57-4.46 (m, 1H), 3.93-3.67 (m, 4H), 3.31 (s, 2H), 2.12-1.77 (m, 6H), 1.65-1.39 (m, 2H) | (ESI (+)) m/e 437 (M + H)⁺ |
| 1425 | N-[4-({1-[(2R)-tetrahydrofuran-2-ylcarbonyl]piperidin-4-yl}oxy)phenyl]-1,3-dihydro-2H-pyrrolo[3,4-c]pyridine-2-carboxamide | ¹H NMR (300 MHz, DMSO-d₆) δ 8.60 (s, 1H), 8.50 (d, J = 5.0 Hz, 1H), 8.27 (s, 1H), 7.53-7.33 (m, 3H), 6.90 (d, J = 9.0 Hz, 2H), 4.78 (d, J = 4.0 Hz, 4H), 4.73-4.60 (m, 1H), 4.52 (s, 1H), 3.93-3.63 (m, 4H), 3.49-3.07 (m, 2H), 2.11-1.72 (m, 6H), 1.66-1.40 (m, 2H) | (ESI (+)) m/e 437 (M + H)⁺ |
| 1426 | N-[4-({1-[(4,4-difluorocyclohexyl)carbonyl]azetidin-3-yl}oxy)phenyl]-1,3-dihydro-2H-pyrrolo[3,4-c]pyridine-2-carboxamide | ¹H NMR (400 MHz, DMSO, Temp = 90° C.) δ 8.57 (s, 1H), 8.47 (d, J = 5.0 Hz, 1H), 8.05 (d, J = 8.0 Hz, 1H), 7.48-7.39 (m, 2H), 7.37 (d, J = 4.8 Hz, 1H), 6.86-6.60 (m, 2H), 4.96 (m, 1H), 4.78 (d, J = 8.8 Hz, 5H), 4.19 (m, 2H), 3.74 (m, 2H), 3.22 (d, J = 6.2 Hz, 1H), 2.42 (t, J = 10.6 Hz, 1H), 2.26 (t, J = 6.9 Hz, 1H), 2.04 (d, J = 10.0 Hz, 2H), 1.81 (ddd, J = 26.3, 15.5, 8.4 Hz, 3H), 1.68-1.49 (m, 2H) | (ESI (+)) m/e 457 (M + H)⁺ |
| 1427 | N-(4-{[1-(5-oxo-D-prolyl)piperidin-4-yl]oxy}phenyl)-1,3-dihydro-2H-pyrrolo[3,4-c]pyridine-2-carboxamide | ¹H NMR (400 MHz, DMSO-D₂O, Temp = 90° C.) δ ppm 8.57 (s, 1 H) 8.48 (d, J = 4.88 Hz, 1 H) 7.40 (d, J = 8.54 Hz, 3 H) 6.90 (d, J = 8.85 Hz, 2 H) 4.79 (d, J = 7.63 Hz, 4 H) 4.46-4.60 (m, 2 H) 3.75 (s, 2 H) 3.34-3.41 (m, 2 H) 2.30-2.41 (m, 1 H) 2.10-2.23 (m, 2 H) 1.92-2.05 (m, 3 H) 1.56-1.74 (m, 2 H) | (APCI (+)) m/e 450 (M + H)⁺ |
| 1428 | N-(4-{[1-(2,2-dimethylpropanoyl)piperidin-4-yl]oxy}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 4.88 Hz, 1 H) 7.36-7.44 (m, 3 H) 6.89 (d, J = 8.85 Hz, 2 H) 4.79 (d, J = 7.32 Hz, 4 H) 4.43-4.53 (m, 1 H) 3.80-3.93 (m, 2 H) 3.34-3.42 (m, 2 H) 1.94-1.99 (m, J = 3.36 Hz, 2 H) 1.50-1.68 (m, 2 H) 1.22 (s, 9 H) | (APCI (+)) m/e 423 (M + H)⁺ |
| 1429 | N-(4-{[1-(2-methylpentanoyl)piperidin-4-yl]oxy}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 5.19 Hz, 1 H) 7.40 (d, J = 8.85 Hz, 3 H) 6.89 (d, J = 8.85 Hz, 2 H) 4.79 (d, J = 7.32 Hz, 4 H) 4.45-4.54 (m, 1 H) 3.81 (dd, J = 11.14, 5.34 Hz, 2 H) 3.35 (s, 2 H) 2.75-2.84 (m, 1 H) 1.93-1.98 (m, 2 H) 1.49-1.64 (m, 3 H) 1.19-1.35 (m, 3 H) 1.01 (d, J = 6.71 Hz, 3 H) 0.86 (t, J = 7.02 Hz, 3 H) | (APCI (+)) m/e 437 (M + H)⁺ |
| 1430 | N-(4-{[1-(2-ethylbutanoyl)piperidin-4-yl]oxy}phenyl)-1,3-dihydro-2H-pyrrolo[3,4-c]pyridine-2-carboxamide | ¹H NMR (400 MHz, DMSO-D₂O, Temp = 90° C.) δ ppm 8.58 (s, 1 H) 8.48 (d, J = 5.19 Hz, 1 H) 7.40 (d, J = 9.16 Hz, 3 H) 6.90 (d, J = 8.85 Hz, 2 H) 4.79 (d, J = 7.63 Hz, 4 H) 4.46-4.56 (m, J = 11.22, 7.40, 3.66 Hz, 1 H) 3.80-3.92 (m, 2 H) 3.35-3.43 (m, 2 H) 2.58-2.68 (m, 1 H) 1.87-1.95 (m, 2 H) 1.47-1.64 (m, 4 H) 1.34-1.46 (m, 2 H) 0.82 (t, J = 7.48 Hz, 6 H) | (APCI (+)) m/e 437 (M + H)⁺ |

-continued

| Ex | Name | ¹H NMR | MS |
|---|---|---|---|
| 1431 | N-(4-{[1-(1H-pyrrol-2-ylcarbonyl)piperidin-4-yl]oxy}phenyl)-1,3-dihydro-2H-pyrrolo[3,4-c]pyridine-2-carboxamide | ¹H NMR (400 MHz, DMSO-D₂O, Temp = 90° C.) δ ppm 8.57 (s, 1 H) 8.48 (d, J = 5.19 Hz, 1 H) 7.37-7.46 (m, 3 H) 6.85-6.95 (m, 3 H) 6.49 (d, J = 3.05 Hz, 1 H) 6.13 (t, J = 2.90 Hz, 1 H) 4.79 (d, J = 7.93 Hz, 4 H) 4.47-4.60 (m, 1 H) 3.93-4.09 (m, 2 H) 3.49-3.59 (m, 2 H) 1.95-2.03 (m, 2 H) 1.56-1.74 (m, 2 H) | (APCI (+)) m/e 432 (M + H)⁺ |
| 1432 | N-(4-{[1-(1,2-oxazol-5-ylcarbonyl)piperidin-4-yl]oxy}phenyl)-1,3-dihydro-2H-pyrrolo[3,4-c]pyridine-2-carboxamide | ¹H NMR (400 MHz, Solvent) δ ppm 8.57 (s, 1 H) 8.47 (d, J = 4.88 Hz, 1 H) 7.36-7.44 (m, 3 H) 6.89 (d, J = 8.54 Hz, 2 H) 4.79 (d, J = 7.93 Hz, 4 H) 3.44-4.62 (m, 4 H) 1.79-1.89 (m, 2 H) 1.40-1.80 (m, 3 H) | (APCI (+)) m/e 434 (M + H)⁺ |
| 1433 | N-(4-{[1-(pyridin-3-ylcarbonyl)piperidin-4-yl]oxy}phenyl)-1,3-dihydro-2H-pyrrolo[3,4-c]pyridine-2-carboxamide | ¹H NMR (400 MHz, DMSO-D₂O, Temp = 90° C.) δ ppm 8.62 (d, J = 4.58 Hz, 1 H) 8.58 (d, J = 7.32 Hz, 2 H) 8.47 (d, J = 5.19 Hz, 1 H) 7.82 (d, J = 7.93 Hz, 1 H) 7.47 (dd, J = 7.63, 4.88 Hz, 1 H) 7.40 (d, J = 8.54 Hz, 3 H) 6.91 (d, J = 8.85 Hz, 2 H) 4.79 (d, J = 7.63 Hz, 4 H) 4.50-4.58 (m, 1 H) 3.75 (s, 2 H) 3.38-3.50 (m, J = 8.85 Hz, 2 H) 1.93-2.05 (m, 2 H) 1.62-1.76 (m, 2 H) | (APCI (+)) m/e 444 (M + H)⁺ |
| 1434 | N-(4-{[1-(pyridazin-3-ylcarbonyl)piperidin-4-yl]oxy}phenyl)-1,3-dihydro-2H-pyrrolo[3,4-c]pyridine-2-carboxamide | ¹H NMR (400 MHz, DMSO-D₂O, Temp = 90° C.) δ ppm 9.26 (dd, J = 4.58, 2.14 Hz, 1 H) 8.58 (s, 1 H) 8.49 (d, J = 4.88 Hz, 1 H) 7.76-7.85 (m, 2 H) 7.37-7.45 (m, 3 H) 6.91 (t, J = 9.16 Hz, 2 H) 4.80 (d, J = 6.10 Hz, 4 H) 4.48-4.63 (m, 1 H) 3.99 (s, 2 H) 3.60 (s, 2 H) 1.95-2.14 (m, 2 H) 1.72 (s, 2 H) | (APCI (+)) m/e 445 (M + H)⁺ |
| 1435 | N-(4-{[1-(pyrazin-2-ylcarbonyl)piperidin-4-yl]oxy}phenyl)-1,3-dihydro-2H-pyrrolo[3,4-c]pyridine-2-carboxamide | ¹H NMR (400 MHz, DMSO-D₂O, Temp = 90° C.) δ ppm 9.20 (s, 1 H) 8.93 (d, J = 5.19 Hz, 1 H) 8.57 (s, 1 H) 8.47 (d, J = 4.88 Hz, 1 H) 7.60-7.65 (m, 1 H) 7.36-7.44 (m, 3 H) 6.87-6.94 (m, 2 H) 4.79 (d, J = 7.63 Hz, 4 H) 4.47-4.62 (m, 1 H) 3.94 (s, 2 H) 3.55 (s, 2 H) 1.93-2.11 (m, 2 H) 1.61-1.78 (m, J = 15.87 Hz, 2 H) | (APCI (+)) m/e 445 (M + H)⁺ |
| 1436 | N-(4-{[1-(pyrimidin-4-ylcarbonyl)piperidin-4-yl]oxy}phenyl)-1,3-dihydro-2H-pyrrolo[3,4-c]pyridine-2-carboxamide | ¹H NMR (400 MHz, DMSO-D₂O, Temp = 90° C.) δ ppm 8.40-8.87 (m, 5 H) 7.33-7.47 (m, 3 H) 6.91 (d, J = 8.85 Hz, 2 H) 4.79 (d, J = 7.93 Hz, 4 H) 4.48-4.63 (m, 1 H) 3.45-4.22 (m, 4 H) 1.94-2.12 (m, 2 H) 1.56-1.79 (m, 2 H) | (APCI (+)) m/e 445 (M + H)⁺ |
| 1437 | N-[4-({1-[(5-methylpyrazin-2-yl)carbonyl]piperidin-4-yl}oxy)phenyl]-1,3-dihydro-2H-pyrrolo[3,4-c]pyridine-2-carboxamide | ¹H NMR (400 MHz, DMSO-D₂O, Temp = 90° C.) δ ppm 8.66 (s, 1 H) 8.57 (s, 1 H) 8.52 (s, 1 H) 8.48 (d, J = 4.88 Hz, 1 H) 7.40 (d, J = 8.54 Hz, 3 H) 6.91 (d, J = 9.16 Hz, 2 H) 4.79 (d, J = 7.63 Hz, 4 H) 4.51-4.60 (m, 1 H) 3.63-4.07 (m, 2 H) 3.39-3.62 (m, 2 H) 2.55 (s, 3 H) 1.93-2.06 (m, 2 H) 1.62-1.78 (m, J = 10.38 Hz, 2 H) | (APCI (+)) m/e 459 (M + H)⁺ |
| 1438 | N-[4-({1-[3-(piperidin-1-yl)propanoyl]piperidin-4-yl}oxy)phenyl]-1,3-dihydro-2H-pyrrolo[3,4-c]pyridine-2-carboxamide | ¹H NMR (400 MHz, DMSO-D₂O, Temp = 90° C.) δ ppm 8.57 (s, 1 H) 8.48 (d, J = 4.88 Hz, 1 H) 7.33-7.45 (m, 3 H) 6.89 (d, J = 8.85 Hz, 2 H) 4.79 (d, J = 7.93 Hz, 4 H) 4.43-4.52 (m, 1 H) 3.66-3.92 (m, 2 H) 3.34-3.40 (m, 2 H) 2.55-2.62 (m, J = 7.02, 7.02 Hz, 2 H) 2.46-2.50 (m, 2 H) 2.37-2.43 (m, 4 H) 1.91-2.00 (m, 2 H) 1.55-1.68 (m, 2 H) 1.45-1.55 (m, 4 H) 1.33-1.42 (m, 2 H) | (APCI (+)) m/e 478 (M + H)⁺ |
| 1439 | N-(4-{[1-(morpholin-4-ylacetyl)piperidin-4-yl]oxy}phenyl)-1,3-dihydro-2H-pyrrolo[3,4-c]pyridine-2-carboxamide | ¹H NMR (400 MHz, DMSO-D₂O, Temp = 90° C.) δ ppm 8.57 (s, 1 H) 8.48 (d, J = 5.19 Hz, 1 H) 7.34-7.48 (m, 3 H) 6.90 (d, J = 8.85 Hz, 2 H) 4.79 (d, J = 7.63 Hz, 4 H) 4.40-4.59 (m, 1 H) 3.72-3.91 (m, 2 H) 3.53-3.64 (m, 4 H) 3.35-3.45 (m, 2 H) 3.16 (s, 2 H) 2.39-2.47 (m, 4 H) 1.90-2.01 (m, 2 H) 1.50-1.68 (m, 2 H) | (APCI (+)) m/e 466 (M + H)⁺ |

-continued

| Ex | Name | ¹H NMR | MS |
|---|---|---|---|
| 1440 | N-[4-({1-[3-(4-methylpiperazin-1-yl)propanoyl]piperidin-4-yl}oxy)phenyl]-1,3-dihydro-2H-pyrrolo[3,4-c]pyridine-2-carboxamide | ¹H NMR (400 MHz, DMSO-D$_2$O, Temp = 90° C.) δ ppm 8.57 (s, 1 H) 8.48 (d, J = 4.88 Hz, 1 H) 7.36-7.44 (m, 3 H) 6.89 (d, J = 8.85 Hz, 2 H) 4.79 (d, J = 7.93 Hz, 4 H) 4.40-4.60 (m, 1 H) 3.69-3.85 (m, 2 H) 3.36-3.50 (m, 2 H) 2.55-2.63 (m, 2 H) 2.46-2.50 (m, 2 H) 2.40-2.45 (m, 4 H) 2.30-2.36 (m, 4 H) 2.16 (s, 3 H) 1.91-2.00 (m, 2 H) 1.52-1.67 (m, 2 H) | (APCI (+)) m/e 493 (M + H)⁺ |
| 1532 | N-(4-{[(3R)-1-(3-methylbutanoyl)pyrrolidin-3-yl]oxy}phenyl)-1,3-dihydro-2H-pyrrolo[3,4-c]pyridine-2-carboxamide | ¹H NMR (300 MHz, DMSO-d$_6$) δ 8.60 (s, 1H), 8.49 (d, J = 5.0 Hz, 1H), 8.28 (s, 1H), 7.49-7.36 (m, 3H), 6.95-6.79 (m, 2H), 4.96 (d, J = 21.2 Hz, 1H), 4.78 (d, J = 4.0 Hz, 5H), 3.81-3.44 (m, 4H), 2.21-1.84 (m, 6H), 0.99-0.79 (m, 6H) | (ESI (+)) m/e 409 (M + H)⁺ |
| 1533 | N-(4-{[(3R)-1-(cyclobutylcarbonyl)pyrrolidin-3-yl]oxy}phenyl)-1,3-dihydro-2H-pyrrolo[3,4-c]pyridine-2-carboxamide | ¹H NMR (300 MHz, DMSO-d$_6$) δ 8.60 (s, 1H), 8.49 (d, J = 5.0 Hz, 1H), 8.28 (s, 1H), 7.53-7.38 (m, 3H), 6.96-6.81 (m, 2H), 5.04-4.85 (m, 1H), 4.78 (d, J = 3.9 Hz, 4H), 3.72-3.07 (m, 5H), 2.24-1.56 (m, 8H) | (ESI (+)) m/e 407 (M + H)⁺ |
| 1534 | N-[4-({(3R)-1-[(2R)-tetrahydrofuran-2-ylcarbonyl]pyrrolidin-3-yl}oxy)phenyl]-1,3-dihydro-2H-pyrrolo[3,4-c]pyridine-2-carboxamide | ¹H NMR (300 MHz, DMSO-d$_6$) δ 8.60 (s, 1H), 8.50 (d, J = 5.0 Hz, 1H), 8.29 (s, 1H), 7.48-7.43 (m, 2H), 7.45-7.39 (m, 2H), 6.92-6.83 (m, 2H), 5.05-4.90 (m, 1H), 4.82-4.75 (m, 4H), 4.59-4.42 (m, 1H), 3.89-3.42 (m, 5H), 2.25-1.68 (m, 6H) | (ESI (+)) m/e 423 (M + H)⁺ |
| 1535 | N-[4-({(3R)-1-[(2S)-tetrahydrofuran-2-ylcarbonyl]pyrrolidin-3-yl}oxy)phenyl]-1,3-dihydro-2H-pyrrolo[3,4-c]pyridine-2-carboxamide | ¹H NMR (300 MHz, DMSO-d$_6$) δ 8.60 (s, 1H), 8.50 (d, J = 5.0 Hz, 1H), 8.29 (s, 1H), 7.45-7.39 (m, 2H), 6.93-6.83 (m, 2H), 5.06-4.90 (m, 1H), 4.82-4.75 (m, 4H), 4.60-4.42 (m, 1H), 3.85-3.63 (m, 3H), 3.63-3.41 (m, 2H), 2.30-1.71 (m, 6H) | (ESI (+)) m/e 423 (M + H)⁺ |
| 1536 | N-(4-{[(3R)-1-(cyclopropylacetyl)pyrrolidin-3-yl]oxy}phenyl)-1,3-dihydro-2H-pyrrolo[3,4-c]pyridine-2-carboxamide | ¹H NMR (300 MHz, DMSO-d$_6$) δ 8.60 (s, 1H), 8.50 (d, J = 5.0 Hz, 1H), 8.29 (s, 1H), 7.48-7.40 (m, 3H), 6.92-6.82 (m, 2H), 5.03-4.90 (m, 1H), 4.81-4.75 (m, 4H), 3.79-3.43 (m, 2H), 2.32-1.95 (m, 5H), 1.05-0.88 (m, 1H), 0.49-0.36 (m, 2H), 0.20-0.07 (m, 2H) | (ESI (+)) m/e 407 (M + H)⁺ |
| 1537 | N-(4-{[(3S)-1-(3-methylbutanoyl)pyrrolidin-3-yl]oxy}phenyl)-1,3-dihydro-2H-pyrrolo[3,4-c]pyridine-2-carboxamide | ¹H NMR (300 MHz, DMSO-d$_6$) δ 8.60 (s, 1H), 8.50 (d, J = 5.0 Hz, 1H), 8.29 (s, 1H), 7.49-7.39 (m, 3H), 6.92-6.81 (m, 2H), 5.04-4.89 (m, 1H), 4.81-4.75 (m, 4H), 3.66-3.42 (m, 4H), 2.25-1.90 (m, 5H), 0.96-0.82 (m, 6H) | (ESI (+)) m/e 409 (M + H)⁺ |
| 1538 | N-(4-{[(3S)-1-(cyclobutylcarbonyl)pyrrolidin-3-yl]oxy}phenyl)-1,3-dihydro-2H-pyrrolo[3,4-c]pyridine-2-carboxamide | ¹H NMR (300 MHz, DMSO-d$_6$) δ 8.60 (s, 1H), 8.50 (d, J = 5.0 Hz, 1H), 8.29 (s, 1H), 7.48-7.40 (m, 3H), 6.91-6.81 (m, 2H), 5.02-4.89 (m, 1H), 4.81-4.75 (m, 4H), 3.32 (s, 5H), 2.27-1.65 (m, 8H) | (ESI (+)) m/e 407 (M + H)⁺ |
| 1539 | N-[4-({(3S)-1-[(2R)-tetrahydrofuran-2-ylcarbonyl]pyrrolidin-3-yl}oxy)phenyl]-1,3-dihydro-2H-pyrrolo[3,4-c]pyridine-2-carboxamide | ¹H NMR (300 MHz, DMSO-d$_6$) δ 8.60 (s, 1H), 8.50 (d, J = 5.0 Hz, 1H), 8.29 (s, 1H), 7.48-7.41 (m, 3H), 7.43 (d, J = 5.4 Hz, 2H), 6.93-6.82 (m, 2H), 5.05-4.91 (m, 1H), 4.81-4.75 (m, 4H), 4.60-4.42 (m, 1H), 3.89-3.64 (m, 4H), 3.65-3.43 (m, 2H), 2.26-1.73 (m, 6H) | (ESI (+)) m/e 423 (M + H)⁺ |

-continued

| Ex | Name | ¹H NMR | MS |
|---|---|---|---|
| 1540 | N-[4-({(3S)-1-[(2S)-tetrahydrofuran-2-ylcarbonyl]pyrrolidin-3-yl}oxy)phenyl]-1,3-dihydro-2H-pyrrolo[3,4-c]pyridine-2-carboxamide | ¹H NMR (300 MHz, DMSO-$d_6$) δ 8.60 (s, 1H), 8.50 (d, J = 5.0 Hz, 1H), 8.29 (s, 1H), 7.48-7.40 (m, 3H), 6.93-6.83 (m, 2H), 5.05-4.91 (m, 1H), 4.81-4.75 (m, 3H), 4.59-4.42 (m, 1H), 3.89-3.42 (m, 6H), 2.25-1.70 (m, 6H) | (ESI (+)) m/e 423 (M + H)⁺ |
| 1541 | N-(4-{[(3S)-1-(cyclopropylacetyl)pyrrolidin-3-yl]oxy}phenyl)-1,3-dihydro-2H-pyrrolo[3,4-c]pyridine-2-carboxamide | ¹H NMR (300 MHz, DMSO-$d_6$) δ 8.60 (s, 1H), 8.50 (d, J = 5.0 Hz, 1H), 8.29 (s, 1H), 7.48-7.40 (m, 3H), 6.93-6.82 (m, 2H), 5.03-4.90 (m, 1H), 4.81-4.75 (m, 4H), 3.80-3.33 (m, 2H), 2.30-1.95 (m, 5H), 1.07-0.88 (m, 1H), 0.49-0.35 (m, 2H), 0.19-0.07 (m, 2H) | (ESI (+)) m/e 407 (M + H)⁺ |

Example 953

N-{6-[(1-acetylpiperidin-4-yl)oxy]pyridin-3-yl}-1,3-dihydro-2H-isoindole-2-carboxamide Example 953A tert-butyl 4-(5-nitropyridin-2-yloxy)piperidine-1-carboxylate A suspension of pre-washed NaH (0.1 g, 2.48 mmol, 60% percent dispersion in mineral oil) in THF (2 mL) was added to an ice cold solution of 4-hydroxy-piperidine-1-carboxylic acid tert-butyl ester (0.5 g, 2.48 mmol) in dry THF (3 mL). The mixture was stirred for 20 minutes, and added to 2-chloro-5-nitro-pyridine (0.36 g, 2.26 mmol) in portions. After the addition was completed, the cooling bath was removed and the reaction mixture was stirred at 22° C. overnight. The reaction mixture was cooled in an ice bath and treated with a saturated aqueous sodium bicarbonate solution (5 mL). The reaction mixture was diluted with ethyl acetate (25 mL) and distilled water (25 mL). The separated aqueous phase was extracted with ethyl acetate (3×35 mL), and the combined organic phases were dried over sodium sulfate, filtered and concentrated under reduced pressure. Chromatography provided the title compound.

Example 953B tert-butyl 4-(5-aminopyridin-2-yloxy)piperidine-1-carboxylate

The title compound was prepared as described in Example 274, substituting tert-butyl 4-(5-nitropyridin-2-yloxy)piperidine-1-carboxylate for 5-nitro-N-[4-(propylcarbamoyl)phenyl]-1,3-dihydro-2H-isoindole-2-carboxamide.

Example 953C tert-butyl 4-(5-(isoindoline-2-carboxamido)pyridin-2-yloxy)piperidine-1-carboxylate The title compound was prepared as described in Example 272B, substituting tert-butyl 4-(5-aminopyridin-2-yloxy)piperidine-1-carboxylate for 4-amino-N-propylbenzamide and isoindoline for methyl isoindoline-5-carboxylate hydrochloride.

Example 953D

N-(6-(piperidin-4-yloxy)pyridin-3-yl)isoindoline-2-carboxamide

The title compound was prepared as described in Example 2D, substituting tert-butyl 4-(5-(isoindoline-2-carboxamido)pyridin-2-yloxy)piperidine-1-carboxylate for tert-butyl 4-((4-(5-fluoroisoindoline-2-carboxamido)benzamido)methyl)benzylcarbamate.

Example 953E

N-{6-[(1-acetylpiperidin-4-yl)oxy]pyridin-3-yl}-1,3-dihydro-2H-isoindole-2-carboxamide The title compound was prepared as described in Example 1C, substituting N-(6-(piperidin-4-yloxy)pyridin-3-yl)isoindoline-2-carboxamide for 3-phenylpropan-1-amine and acetic acid for 4-(isoindoline-2-carboxamido)benzoic acid. ¹H NMR (300 MHz, DMSO-$d_6$) δ ppm 8.37 (s, 1H), 8.26 (d, J=2.7 Hz, 1H), 7.86 (dd, J=8.9, 2.7 Hz, 1H), 7.44-7.24 (m, 4H), 6.75 (d, J=8.8 Hz, 1H), 5.21-5.07 (m, 1H), 4.75 (s, 4H), 3.72-3.63 (m, 1H), 3.40-3.11 (m, 2H), 1.97-1.85 (m, 1H), 1.73-1.38 (m, 2H); MS (ESI(+)) m/e 495 (M+H)⁺.
Table 17.

The following Examples were essentially prepared as described in Example 1C, substituting N-(6-(piperidin-4-yloxy)pyridin-3-yl)isoindoline-2-carboxamide for 3-phenylpropan-1-amine and the appropriate carboxylic acid for 4-(isoindoline-2-carboxamido)benzoic acid.

| Ex | Name | ¹H NMR | MS |
|---|---|---|---|
| 954 | N-{6-[(1-isobutyrylpiperidin-4-yl)oxy]pyridin-3-yl}-1,3-dihydro-2H-isoindole-2-carboxamide | 1H NMR (300 MHz, DMSO-$d_6$) δ 8.37 (s, 1H), 8.26 (dd, J = 2.7, 0.7 Hz, 1H), 7.86 (dd, J = 8.8, 2.7 Hz, 1H), 7.41-7.26 (m, 4H), 6.74 (d, J = 8.5 Hz, 1H), 5.21-5.09 (m, 1H), 4.75 (s, 4H), 3.99-3.72 (m, 2H), 3.44-3.14 (m, 2H), 2.98-2.80 (m, 1H), 2.07-1.87 (m, 2H), 1.67-1.42 (m, 2H), 1.00 (d, J = 6.7 Hz, 6H) | (ESI (+)) m/e 409 (M + H)⁺ |

-continued

| Ex | Name | ¹H NMR | MS |
|---|---|---|---|
| 955 | N-(6-{[1-(3-methylbutanoyl)piperidin-4-yl]oxy}pyridin-3-yl)-1,3-dihydro-2H-isoindole-2-carboxamide | ¹H NMR (300 MHz, DMSO-d₆) δ 8.37 (s, 1H), 8.26 (d, J = 2.9 Hz, 1H), 7.85 (dd, J = 8.8, 2.7 Hz, 1H), 7.41-7.26 (m, 4H), 6.74 (d, J = 8.8 Hz, 1H), 5.21-5.09 (m, 1H), 4.75 (s, 4H), 3.99-3.88 (m, 1H), 3.80-3.67 (m, 1H), 3.45-3.13 (m, 3H), 2.22 (d, J = 1.4 Hz, 1H), 2.05-1.87 (m, 3H), 1.65-1.41 (m, 2H), 0.91 (d, J = 6.6 Hz, 6H) | (ESI (+)) m/e 423 (M + H)⁺ |
| 956 | N-(6-{[1-(4,4,4-trifluorobutanoyl)piperidin-4-yl]oxy}pyridin-3-yl)-1,3-dihydro-2H-isoindole-2-carboxamide | ¹H NMR (300 MHz, DMSO-d₆) δ 8.37 (s, 1H), 8.26 (d, J = 2.7 Hz, 1H), 7.86 (dd, J = 8.8, 2.7 Hz, 1H), 7.42-7.26 (m, 4H), 6.75 (d, J = 8.8 Hz, 1H), 5.21-5.09 (m, 1H), 4.75 (s, 4H), 3.98-3.85 (m, 1H), 3.77-3.66 (m, 1H), 3.42-3.15 (m, 2H), 2.68-2.56 (m, 2H), 2.03-1.88 (m, 2H), 1.71-1.41 (m, 2H) | (ESI (+)) m/e 463 (M + H)⁺ |
| 957 | N-(6-{[1-(methoxyacetyl)piperidin-4-yl]oxy}pyridin-3-yl)-1,3-dihydro-2H-isoindole-2-carboxamide | ¹H NMR (300 MHz, DMSO-d₆) δ 8.37 (s, 1H), 8.26 (d, J = 2.6 Hz, 1H), 7.86 (dd, J = 8.9, 2.7 Hz, 1H), 7.34 (tdd, J = 9.0, 5.6, 3.5 Hz, 4H), 6.75 (d, J = 8.8 Hz, 1H), 5.25-5.06 (m, 1H), 4.75 (s, 4H), 4.08 (t, J = 6.0 Hz, 3H), 3.63 (s, 1H), 3.42-3.11 (m, 5H), 1.96 (s, 2H), 1.59 (d, J = 25.8 Hz, 2H) | (ESI (+)) m/e 411 (M + H)⁺ |
| 958 | N-(6-{[1-(tetrahydrofuran-2-ylcarbonyl)piperidin-4-yl]oxy}pyridin-3-yl)-1,3-dihydro-2H-isoindole-2-carboxamide | ¹H NMR (300 MHz, DMSO-d₆) δ 8.38 (s, 1H), 8.26 (d, J = 2.7 Hz, 1H), 7.86 (dd, J = 8.8, 2.7 Hz, 1H), 7.40-7.28 (m, 4H), 6.75 (d, J = 8.8 Hz, 1H), 5.15 (d, J = 4.1 Hz, 1H), 4.75 (s, 3H), 4.73-4.63 (m, 1H), 3.92-3.63 (m, 5H), 3.62-3.12 (m, 2H), 2.09-1.89 (m, 2H), 1.89-1.69 (m, 1H), 1.70-1.32 (m, 1H) | (ESI (+)) m/e 437 (M + H)⁺ |
| 959 | N-(6-{[1-(tetrahydrofuran-3-ylcarbonyl)piperidin-4-yl]oxy}pyridin-3-yl)-1,3-dihydro-2H-isoindole-2-carboxamide | ¹H NMR (300 MHz, DMSO-d₆) δ 8.38 (s, 1H), 8.26 (d, J = 2.7 Hz, 1H), 7.86 (dd, J = 8.8, 2.8 Hz, 1H), 7.40-7.22 (m, 4H), 6.75 (d, J = 8.8 Hz, 1H), 5.16 (dq, J = 8.2, 4.1 Hz, 1H), 4.75 (bs, 4H), 3.98-3.70 (m, 4H), 3.74-3.63 (m, 2H), 3.45-3.14 (m, 3H), 2.08-1.88 (m, 4H), 1.68-1.43 (m, 2H) | (ESI (+)) m/e 437 (M + H)⁺ |
| 960 | N-(6-{[1-(cyclopropylcarbonyl)-piperidin-4-yl]oxy}pyridin-3-yl)-1,3-dihydro-2H-isoindole-2-carboxamide | ¹H NMR (300 MHz, DMSO-d₆) δ 8.39 (d, J = 8.2 Hz, 1H), 8.31-8.20 (m, 1H), 7.91-7.78 (m, 1H), 7.44-7.24 (m, 4H), 6.82-6.68 (m, 1H), 5.27-5.07 (m, 1H), 4.75 (s, 4H), 4.07-3.86 (m, 2H), 3.61-3.46 (m, 1H), 3.26-3.13 (m, 1H), 2.10-1.86 (m, 3H), 1.70-1.42 (m, 2H), 0.79-0.62 (m, 4H) | (ESI (+)) m/e 407 (M + H)⁺ |
| 961 | N-(6-{[1-(cyclopropylacetyl)piperidin-4-yl]oxy}pyridin-3-yl)-1,3-dihydro-2H-isoindole-2-carboxamide | ¹H NMR (300 MHz, DMSO-d₆) δ 8.38 (s, 1H), 8.26 (d, J = 3.1 Hz, 1H), 7.86 (dd, J = 8.9, 2.9 Hz, 1H), 7.43-7.22 (m, 4H), 6.74 (d, J = 8.4 Hz, 1H), 5.21-5.09 (m, 1H), 4.75 (bs, 4H), 3.98-3.87 (m, 1H), 3.76-3.64 (m, 1H), 3.38-3.14 (m, 2H), 2.28 (d, J = 6.7 Hz, 2H), 2.21-1.89 (m, 2H), 1.67-1.43 (m, 2H), 1.05-0.87 (m, 1H), 0.51-0.35 (m, 2H), 0.22-0.08 (m, 2H) | (ESI (+)) m/e 421 (M + H)⁺ |
| 962 | N-(6-{[1-(cyclobutylcarbonyl)-piperidin-4-yl]oxy}pyridin-3-yl)-1,3-dihydro-2H-isoindole-2-carboxamide | ¹H NMR (300 MHz, DMSO-d₆) δ 8.37 (s, 1H), 8.24 (t, J = 4.4 Hz, 1H), 7.93-7.77 (m, 1H), 7.44-7.24 (m, 4H), 6.74 (t, J = 6.5 Hz, 1H), 5.23-5.03 (m, 1H), 4.75 (s, 4H), 3.98-3.81 (m, 1H), 3.66-3.50 (m, 1H), 3.27-3.10 (m, 2H), 2.26-1.99 (m, 4H), 1.99-1.80 (m, 3H), 1.80-1.42 (m, 3H) | (ESI (+)) m/e 421 (M + H)⁺ |
| 963 | N-(6-{[1-(cyclopentylcarbonyl)-piperidin-4-yl]oxy}pyridin-3-yl)-1,3-dihydro-2H-isoindole-2-carboxamide | ¹H NMR (300 MHz, DMSO-d₆) δ 8.38 (s, 1H), 8.26 (d, J = 2.7 Hz, 1H), 7.85 (dd, J = 8.8, 2.7 Hz, 1H), 7.40-7.28 (m, 4H), 6.74 (d, J = 8.8 Hz, 1H), 5.21-5.09 (m, 1H), 4.75 (s, 4H), 3.98-3.75 (m, 3H), 3.45-3.31 (m, 1H), 3.26-3.14 (m, 1H), 3.00 (p, J = 7.6 Hz, 1H), 2.03-1.87 (m, 2H), 1.81-1.44 (m, 10H) | (ESI (+)) m/e 435 (M + H)⁺ |
| 964 | N-(6-{[1-(cyclopentylacetyl)piperidin-4-yl]oxy}pyridin-3-yl)-1,3-dihydro-2H-isoindole-2-carboxamide | ¹H NMR (300 MHz, DMSO-d₆) δ 8.37 (s, 1H), 8.26 (dd, J = 2.7, 0.7 Hz, 1H), 7.85 (dd, J = 8.8, 2.7 Hz, 1H), 7.41-7.26 (m, 4H), 6.74 (d, J = 8.5 Hz, 1H), 5.20-5.08 (m, 1H), 4.75 (s, 3H), 3.99-3.86 (m, 1H), 3.79-3.68 (m, 1H), 3.25-3.05 (m, 1H), 2.36 (d, J = 0.8 Hz, 1H), 2.35-2.06 (m, 3H), 2.04-1.85 (m, 2H), 1.82-1.68 (m, 2H), 1.65-1.40 (m, 6H), 1.23-0.99 (m, 2H) | (ESI (+)) m/e 449 (M + H)⁺ |
| 965 | N-(6-{[1-(cyclohexylcarbonyl)-piperidin-4-yl]oxy}pyridin-3-yl)-1,3-dihydro-2H-isoindole-2-carboxamide | ¹H NMR (300 MHz, DMSO-d₆) δ 8.37 (s, 1H), 8.26 (d, J = 2.3 Hz, 1H), 7.85 (dd, J = 8.8, 2.7 Hz, 1H), 7.33 (s, 2H), 6.74 (d, J = 8.8 Hz, 1H), 5.21-5.09 (m, 1H), 4.75 (s, 4H), 3.99-3.72 (m, 2H), 3.25-3.11 (m, 1H), 2.56 (d, J = 19.6 Hz, 1H), 2.06-1.85 (m, 2H), 1.74-1.08 (m, 13H) | (ESI (+)) m/e 449 (M + H)⁺ |

Example 966 tert-butyl (2-{4-[(1,3-dihydro-2H-isoindol-2-ylcarbonyl)amino]phenyl}ethyl)carbamate The title compound was prepared as described in Example 272B, substituting tert-butyl 4-aminophenethylcarbamate for 4-amino-N-propylbenzamide and isoindoline for methyl isoindoline-5-carboxylate hydrochloride. $^1$H NMR (300 MHz, DMSO-d$_6$) δ ppm 8.26 (s, 1H), 7.50-7.43 (m, 2H), 7.40-7.26 (m, 4H), 7.11-7.03 (m, 2H), 6.87-6.79 (m, 1H), 4.75 (s, 4H), 3.18-3.02 (m, 2H), 2.66-2.58 (m, 2H), 1.37 (s, 9H); MS (ESI(+)) m/e 382 (M+H)$^+$.

Example 973

N-{4-[(tetrahydrofuran-3-ylmethyl)sulfamoyl]phenyl}-1,3-dihydro-2H-isoindole-2-carboxamide The title compound was prepared as described in Example 808, substituting (tetrahydrofuran-3-yl)methanamine for 3-methylbutan-1-amine in Example 808A. $^1$H NMR (300 MHz, DMSO-d$_6$) δ ppm 8.76 (s, 1H), 7.82-7.75 (m, 2H), 7.71-7.64 (m, 2H), 7.54 (t, J=6.1 Hz, 1H), 7.41-7.25 (m, 4H), 4.80 (bs, 4H), 3.70-3.49 (m, 3H), 2.69 (t, J=6.7 Hz, 2H), 2.34-2.16 (m, 1H), 1.94-1.79 (m, 1H), 1.54-1.39 (m, 1H); MS (ESI(+)) m/e 402 (M+H)$^+$.

Example 974

N-{4-[(tetrahydrofuran-3-ylmethyl)sulfamoyl]phenyl}-1,3-dihydro-2H-pyrrolo[3,4-c]pyridine-2-carboxamide The title compound was prepared as described in Example 272B, substituting 4-amino-N-((tetrahydrofuran-3-yl)methyl)benzenesulfonamide for 4-amino-N-propylbenzamide and 1,3-dihydro-2H-pyrrolo[3,4-c]pyridine for methyl isoindoline-5-carboxylate hydrochloride. $^1$H NMR (300 MHz, DMSO-d$_6$) δ ppm 8.83 (s, 1H), 8.62 (s, 1H), 8.51 (d, J=5.0 Hz, 1H), 7.82-7.75 (m, 2H), 7.72-7.65 (m, 2H), 7.55 (t, J=6.0 Hz, 1H), 7.44 (d, J=5.1 Hz, 1H), 4.87-4.75 (m, 4H), 3.76-3.49 (m, 3H), 2.69 (t, J=6.7 Hz, 2H), 2.34-2.16 (m, 1H), 1.94-1.79 (m, 1H), 1.54-1.39 (m, 1H); MS (ESI(+)) m/e 403 (M+H)$^+$.

Example 975

5-cyano-N-{4-[(tetrahydrofuran-3-ylmethyl)sulfamoyl]phenyl}-1,3-dihydro-2H-isoindole-2-carboxamide The title compound was prepared as described in Example 272B, substituting 4-amino-N-((tetrahydrofuran-3-yl)methyl)benzenesulfonamide for 4-amino-N-propylbenzamide and isoindoline-5-carbonitrile for methyl isoindoline-5-carboxylate hydrochloride. $^1$H NMR (300 MHz, DMSO-d$_6$) δ ppm 8.83 (s, 1H), 7.89 (s, 1H), 7.83-7.74 (m, 3H), 7.72-7.64 (m, 2H), 7.59 (d, J=7.9 Hz, 1H), 7.54 (t, J=6.1 Hz, 1H), 4.93-4.76 (m, 4H), 3.70-3.49 (m, 3H), 2.69 (t, J=6.7 Hz, 2H), 2.31-2.05 (m, 1H), 1.94-1.78 (m, 1H), 1.54-1.39 (m, 1H); MS (ESI(+)) m/e 427 (M+H)$^+$.

Example 979

N-{4-[1-(tetrahydrofuran-3-ylcarbonyl)piperidin-4-yl]phenyl}-1,3-dihydro-2H-isoindole-2-carboxamide

Example 979A

N-(4-(piperidin-4-yl)phenyl)isoindoline-2-carboxamide tert-Butyl 4-(4-(isoindoline-2-carboxamido)phenyl)-5,6-dihydropyridine-1(2H)-carboxylate (1.00 g, 2.38 mmol) in 20 ml of 1:1 methanol/tetrahydrofuran was added to 5% Pd on carbon (wet) (0.200 g) in a 50 ml pressure bottle and stirred for 16 hours at 30 atm and room temperature. The mixture was filtered through a nylon membrane and concentrated. The residue was suspended in dichloromethane, stirred 1 hour and filtered with dichloromethane washes to provide the title compound.

Example 979B

N-{4-[1-(tetrahydrofuran-3-ylcarbonyl)piperidin-4-yl]phenyl}-1,3-dihydro-2H-isoindole-2-carboxamide The title compound was prepared as described in Example 1C, substituting N-(4-(piperidin-4-yl)phenyl)isoindoline-2-carboxamide for 3-phenylpropan-1-amine and tetrahydrofuran-3-carboxylic acid for 4-(isoindoline-2-carboxamido)benzoic acid. $^1$H NMR (400 MHz, DMSO-d$_6$) δ ppm 8.26 (s, 1H), 7.46 (m, 2H), 7.31 (m, 4H), 7.12 (m, 2H), 4.74 (bs, 4H), 4.53 (m, 1H), 4.05 (m, 1H), 3.87 (m, 1H), 3.70 (m, 3H), 3.36 (m, 2H), 3.12 (m, 1H), 2.75-2.58 (m, 1H), 2.01 (m, 2H), 1.76 (m, 2H), 1.45 (m, 2H); MS (ESI(+)) m/e 420 (M+H).

Table 18.

The following Examples were essentially prepared as described in Example 1C, substituting the appropriate amine for 3-phenylpropan-1-amine and the appropriate carboxylic acid for 4-(isoindoline-2-carboxamido)benzoic acid.

| Ex | Name | $^1$H NMR | MS |
|---|---|---|---|
| 980 | N-{4-[1-(tetrahydrofuran-2-ylcarbonyl)piperidin-4-yl]phenyl}-1,3-dihydro-2H-isoindole-2-carboxamide | $^1$H NMR (400 MHz, DMSO-d$_6$) δ ppm 8.26 (d, J = 8.7 Hz, 1H), 7.47 (m, 2H), 7.33 (m, 4H), 7.14 (m, 2H), 4.75 (s, 4H), 4.68 (m, 1H), 4.45 (m, 1H), 4.09 (m, 1H), 3.75 (m, 2H), 3.10 (m, 1H), 2.76-2.56 (m, 2H), 2.04 (m, 2H), 1.80 (m, 4H), 1.61-1.33 (m, 2H) | (ESI (+)) m/e 420 (M + H)$^+$ |
| 981 | N-{4-[1-(tetrahydro-2H-pyran-4-ylcarbonyl)piperidin-4-yl]phenyl}-1,3-dihydro-2H-isoindole-2-carboxamide | $^1$H NMR (400 MHz, DMSO-d$_6$) δ ppm 8.26 (s, 1H), 7.47 (m, 2H), 7.33 (m, 4H), 7.12 (m, 2H), 4.75 (bs, 4H), 4.55 (m, 1H), 4.09 (m, 1H), 3.85 (m, 2H), 3.40 (m, 2H), 3.09 (m, 1H), 2.91 (m, 1H), 2.70 (m, 1H), 2.56 (m, 1H), 1.79 (m, 2H), 1.68-1.35 (m, 6H) | (ESI (+)) m/e 434 (M + H)$^+$ |

-continued

| Ex | Name | ¹H NMR | MS |
|----|------|--------|-----|
| 982 | N-{4-[1-(1,4-dioxan-2-ylcarbonyl)piperidin-4-yl]phenyl}-1,3-dihydro-2H-isoindole-2-carboxamide | ¹H NMR (400 MHz, DMSO-$d_6$) δ ppm 8.26 (s, 1H), 7.48 (t, J = 10.0 Hz, 2H), 7.32 (m, 4H), 7.10 (d, J = 7.5 Hz, 2H), 4.74 (s, 4H), 4.44 (d, J = 12.2 Hz, 1H), 4.34 (t, J = 9.2 Hz, 1H), 4.07 (d, J = 11.4 Hz, 1H), 3.83-3.56 (m, 4H), 3.50 (m, 2H), 3.08 (m, 1H), 2.66 (m, 2H), 1.78 (m, 2H), 1.67-1.30 (m, 2H) | (ESI (+)) m/e 436 (M + H)⁺ |
| 983 | N-(4-{1-[(1-methylpyrrolidin-3-yl)carbonyl]piperidin-4-yl}phenyl)-1,3-dihydro-2H-isoindole-2-carboxamide | ¹H NMR (400 MHz, DMSO-$d_6$) δ ppm 8.26 (s, 1H), 7.46 (d, J = 8.3 Hz, 2H), 7.31 (m, 4H), 7.11 (d, J = 8.3 Hz, 2H), 4.74 (s, 4H), 4.52 (d, J = 12.0 Hz, 1H), 4.01 (d, J = 13.0 Hz, 1H), 3.25 (m, 1H), 3.06 (m, 1H), 2.71 (m, 2H), 2.63-2.43 (m, 3H), 2.32 (m, 1H), 2.21 (s, 3H), 1.94 (m, 2H), 1.75 (m, 2H), 1.59-1.30 (m, 2H) | (ESI (+)) m/e 433 (M + H)⁺ |
| 984 | N-(4-{1-[(1,1-dioxidotetrahydrothiophen-3-yl)carbonyl]piperidin-4-yl}phenyl)-1,3-dihydro-2H-isoindole-2-carboxamide | ¹H NMR (400 MHz, DMSO-$d_6$) δ ppm 8.27 (s, 1H), 7.48 (m, 2H), 7.31 (m, 4H), 7.14 (m, 2H), 4.75 (s, 4H), 4.53 (m, 1H), 4.08 (m, 1H), 3.75 (m, 1H), 3.30-3.04 (m, 5H), 2.71 (m, 2H), 2.33 (m, 1H), 2.08 (m, 1H), 1.79 (m, 2H), 1.66-1.36 (m, 2H) | (ESI (+)) m/e 468 (M + H)⁺ |
| 985 | N-{4-[1-(2-hydroxy-2-methylpropanoyl)piperidin-4-yl]phenyl}-1,3-dihydro-2H-isoindole-2-carboxamide | ¹H NMR (400 MHz, DMSO-$d_6$) δ ppm 8.26 (s, 1H), 7.48 (m, 2H), 7.31 (m, 4H), 7.11 (d, J = 8.5 Hz, 2H), 5.37 (s, 1H), 4.74 (s, 4H), 4.53 (m, 2H), 3.30 (m, 1H), 2.71 (m, 2H), 1.76 (d, J = 11.8 Hz, 2H), 1.50 (m, 2H), 1.32 (s, 6H) | (ESI (+)) m/e 408 (M + H)⁺ |
| 986 | N-{4-[1-(morpholin-4-ylacetyl)piperidin-4-yl]phenyl}-1,3-dihydro-2H-isoindole-2-carboxamide | ¹H NMR (400 MHz, DMSO-$d_6$) δ ppm 8.26 (s, 1H), 7.46 (m, 2H), 7.33 (m, 4H), 7.10 (m, 2H), 4.74 (bs, 4H), 4.46 (m, 1H), 4.13 (m, 1H), 3.57 (m, 3H), 3.06 (m, 3H), 2.71-2.50 (m, 2H), 2.40 (m, 4H), 1.77 (m, 2H), 1.56 (m, 1H), 1.40 (m, 1H) | (ESI (+)) m/e 449 (M + H)⁺ |
| 1469 | N-(4-{1-[(2R)-tetrahydrofuran-2-ylcarbonyl]piperidin-4-yl}phenyl)-1,3-dihydro-2H-isoindole-2-carboxamide | ¹H NMR (400 MHz, DMSO-$d_6$) δ ppm 8.28 (s, 1H), 7.47 (m, 2H), 7.32 (m, 4H), 7.13 (m, 2H), 4.75 (s, 4H), 4.70 (m, 1H), 4.48 (m, 1H), 4.10 (m, 1H), 3.76 (m, 2H), 3.08 (m, 1H), 2.69 (m, 2H), 2.03 (m, 2H), 1.81 (m, 4H), 1.54 (m, 1H), 1.42 (m, 1H) | (ESI (+)) m/e 420 (M + H)⁺ |
| 1470 | N-(4-{1-[(2S)-tetrahydrofuran-2-ylcarbonyl]piperidin-4-yl}phenyl)-1,3-dihydro-2H-isoindole-2-carboxamide | ¹H NMR (400 MHz, DMSO-$d_6$) δ ppm 8.28 (s, 1H), 7.47 (m, 2H), 7.33 (m, 4H), 7.12 (dd, J = 8.3, 2.5 Hz, 2H), 4.75 (s, 4H), 4.68 (dd, J = 7.5, 5.7 Hz, 1H), 4.49 (m, 1H), 4.10 (m, 1H), 3.76 (m, 2H), 3.13 (m, 1H), 268 (m, 2H), 2.01 (m, 2H), 1.80 (m, 4H), 1.50 (m, 2H) | (ESI (+)) m/e 420 (M + H)⁺ |
| 1471 | N-(4-{1-[(3R)-tetrahydrofuran-3-ylcarbonyl]piperidin-4-yl}phenyl)-1,3-dihydro-2H-isoindole-2-carboxamide | A-1361467.0 - ¹H NMR (400 MHz, DMSO-$d_6$) δ 8.28 (s, 1H), 7.47 (m, 2H), 7.34 (m, 4H), 7.13 (m, 2H), 4.75 (s, 4H), 4.54 (m, 1H), 4.08 (m, 1H), 3.88 (m, 1H), 3.71 (m, 3H), 3.39 (m, 1H), 3.14 (m, 1H), 2.66 (m, 2H), 2.01 (m, 2H), 1.79 (m, 2H), 1.46 (m, 2H) | (ESI (+)) m/e 420 (M + H)⁺ |

Example 1013

N-(4-{[1-(tetrahydro furan-3-ylcarbonyl)piperidin-4-yl]oxy}phenyl)-1,3-dihydro-2H-isoindole-2-carboxamide

Example 1013A tert-butyl 4-(4-(isoindoline-2-carboxamido)phenoxy)piperidine-1-carboxylate The title compound was prepared as described in Example 272B, substituting tert-butyl 4-(4-aminophenoxy)piperidine-1-carboxylate for 4-amino-N-propylbenzamide and isoindoline for methyl isoindoline-5-carboxylate hydrochloride.

Example 1013B

N-(4-(piperidin-4-yloxy)phenyl)isoindoline-2-carboxamide

The title compound was prepared as described in Example 2D, substituting tert-butyl 4-(4-(isoindoline-2-carboxamido)phenoxy)piperidine-1-carboxylate for tert-butyl 4-((4-(5-fluoroisoindoline-2-carboxamido)benzamido)methyl)benzylcarbamate.

Example 1013C

N-(4-{[1-(tetrahydro furan-3-ylcarbonyl)piperidin-4-yl]oxy}phenyl)-1,3-dihydro-2H-isoindole-2-carboxamide The title compound was prepared as described in Example 1C, substituting N-(4-(piperidin-4-yloxy)phenyl)isoindoline-2-carboxamide for 3-phenylpropan-1-amine and tetrahydrofuran-3-carboxylic acid for 4-(isoindoline-2-carboxamido)benzoic acid. ¹H NMR (300 MHz, DMSO-$d_6$) δ ppm 8.20 (s, 1H), 7.47-7.27 (m, 6H), 6.93-6.86 (m, 2H), 4.74 (s, 4H), 4.58-4.47 (m, 1H), 3.93-3.56 (m, 6H), 3.44-3.32 (m, 3H), 2.06-1.83 (m, 4H), 1.69-1.40 (m, 2H); MS (ESI(+)) m/e 436 (M+H)⁺.

Table 19.

The following Examples were essentially prepared as described in Example 1C, substituting an appropriate amine for 3-phenylpropan-1-amine and appropriate acid for 4-(isoindoline-2-carboxamido)benzoic acid.

| Ex | Name | ¹H NMR | MS |
|---|---|---|---|
| 1028 | N-(4-{[1-(2-methylbutanoyl)piperidin-4-yl]oxy}phenyl)-1,3-dihydro-2H-isoindole-2-carboxamide | ¹H NMR (300 MHz, DMSO-$d_6$) δ 8.20 (s, 1H), 7.42 (dd, J = 12.5, 10.6 Hz, 2H), 7.37-7.23 (m, 4H), 6.90 (d, J = 9.0 Hz, 2H), 4.74 (s, 4H), 4.66-4.42 (m, 1H), 3.90 (s, 2H), 3.45-3.11 (m, 2H), 2.73 (dd, J = 13.4, 6.8 Hz, 1H), 1.92 (s, 2H), 1.68-1.12 (m, 4H), 0.98 (d, J = 6.7 Hz, 3H), 0.81 (t, J = 7.4 Hz, 3H) | (ESI (+)) m/e 422 (M + H)⁺ |
| 1029 | N-(4-{[1-(3-methylbutanoyl)piperidin-4-yl]oxy}phenyl)-1,3-dihydro-2H-isoindole-2-carboxamide | ¹H NMR (300 MHz, DMSO-$d_6$) δ 8.20 (s, 1H), 7.48-7.38 (m, 2H), 7.33 (tdd, J = 8.9, 5.6, 3.5 Hz, 4H), 6.98-6.81 (m, 2H), 4.74 (s, 4H), 4.50 (dt, J = 8.0, 4.1 Hz, 1H), 3.85 (s, 1H), 3.69 (s, 1H), 3.21 (d, J = 9.3 Hz, 1H), 2.34-2.14 (m, 2H), 2.13-1.80 (m, 3H), 1.53 (d, J = 21.1 Hz, 2H), 0.90 (d, J = 6.6 Hz, 6H) | (ESI (+)) m/e 422 (M + H)⁺ |
| 1030 | N-(4-{[1-(2,3-dimethylbutanoyl)piperidin-4-yl]oxy}phenyl)-1,3-dihydro-2H-isoindole-2-carboxamide | ¹H NMR (300 MHz, DMSO-$d_6$) δ 8.20 (s, 1H), 7.47-7.27 (m, 6H), 6.94-6.86 (m, 2H), 4.74 (s, 4H), 4.72-4.47 (m, 1H), 4.02-3.76 (m, 2H), 3.50-3.12 (m, 2H), 2.00-1.63 (m, 3H), 1.63-1.39 (m, 2H), 0.95 (d, J = 6.7 Hz, 3H), 0.85 (t, J = 6.6 Hz, 6H) | (ESI (+)) m/e 436 (M + H)⁺ |
| 1031 | N-(4-{[1-(tetrahydrofuran-2-ylcarbonyl)piperidin-4-yl]oxy}phenyl)-1,3-dihydro-2H-isoindole-2-carboxamide | ¹H NMR (300 MHz, DMSO-$d_6$) δ 8.20 (s, 1H), 7.44 (d, J = 9.0 Hz, 2H), 7.34 (tdd, J = 8.9, 5.5, 3.5 Hz, 4H), 6.90 (d, J = 9.0 Hz, 2H), 4.74 (s, 4H), 4.70-4.63 (m, 1H), 4.51 (s, 1H), 3.80-3.68 (m, 4H), 3.47-3.08 (m, 2H), 2.13-1.68 (m, 6H), 1.66-1.33 (m, 2H) | (ESI (+)) m/e 436 (M + H)⁺ |
| 1032 | N-(4-{[1-(cyclohexylcarbonyl)-piperidin-4-yl]oxy}phenyl)-1,3-dihydro-2H-isoindole-2-carboxamide | ¹H NMR (300 MHz, DMSO-$d_6$) δ 8.18 (d, J = 6.7 Hz, 1H), 7.48-7.39 (m, 2H), 7.39-7.22 (m, 4H), 6.96-6.81 (m, 2H), 4.74 (s, 4H), 4.56-4.41 (m, 1H), 3.97-3.64 (m, 2H), 3.28-3.10 (m, 2H), 2.67-2.54 (m, 1H), 2.02-1.78 (m, 2H), 1.74-1.39 (m, 7H), 1.39-1.04 (m, 5H) | (ESI (+)) m/e 448 (M + H)⁺ |
| 1033 | N-(4-{[1-(cyclohexylacetyl)piperidin-4-yl]oxy}phenyl)-1,3-dihydro-2H-isoindole-2-carboxamide | ¹H NMR (300 MHz, DMSO-$d_6$) δ 8.20 (s, 1H), 7.41 (t, J = 11.1 Hz, 2H), 7.37-7.20 (m, 4H), 6.89 (d, J = 9.0 Hz, 2H), 4.74 (s, 4H), 4.57-4.38 (m, 1H), 3.77 (d, J = 47.0 Hz, 2H), 3.21 (t, J = 9.7 Hz, 2H), 2.20 (d, J = 6.6 Hz, 2H), 1.89 (s, 2H), 1.60 (t, J = 30.4 Hz, 8H), 1.17 (dd, J = 28.3, 16.2 Hz, 3H), 0.94 (t, J = 11.4 Hz, 2H) | (ESI (+)) m/e 462 (M + H)⁺ |
| 1034 | N-(4-{[1-(tetrahydro-2H-pyran-4-ylacetyl)piperidin-4-yl]oxy}phenyl)-1,3-dihydro-2H-isoindole-2-carboxamide | ¹H NMR (300 MHz, DMSO-$d_6$) δ 8.20 (s, 1H), 7.40 (dd, J = 19.8, 6.3 Hz, 3H), 7.36-7.23 (m, 3H), 6.89 (d, J = 9.0 Hz, 2H), 4.74 (s, 4H), 4.50 (s, 1H), 3.95-3.64 (m, 4H), 3.28 - 3.14 (m, 2H), 2.27 (d, J=6.4 Hz, 2H), 1.91 (d, J = 3.7 Hz, 3H), 1.55 (t, J = 18.1 Hz, 4H), 1.32-1.07 (m, 2H) | (ESI (+)) m/e 464 (M + H)⁺ |
| 1035 | N-(4-{[1-(morpholin-4-ylacetyl)piperidin-4-yl]oxy}phenyl)-1,3-dihydro-2H-isoindole-2-carboxamide | ¹H NMR (300 MHz, DMSO-$d_6$) δ 10.01 (s, 1H), 8.21 (s, 1H), 7.43 (t, J = 13.2 Hz, 2H), 7.37-7.24 (m, 3H), 6.91 (d, J = 9.1 Hz, 2H), 4.74 (s, 4H), 4.71-4.45 (m, 1H), 4.37 (s, 2H), 4.04-3.71 (m, 6H), 3.56 (d, J = 15.9 Hz, 2H), 3.47-3.20 (m, 4H), 3.13 (s, 2H), 1.97 (s, 2H), 1.62 (dd, J = 33.2, 8.7 Hz, 2H) | (ESI (+)) m/e 465 (M + H)⁺ |
| 1036 | N-(4-{[1-(tetrahydrofuran-3-ylacetyl)piperidin-4-yl]oxy}phenyl)-1,3-dihydro-2H-isoindole-2-carboxamide | ¹H NMR (300 MHz, DMSO-$d_6$) δ 8.20 (s, 1H), 7.51-7.35 (m, 3H), 7.35-7.23 (m, 3H), 6.89 (d, J = 9.0 Hz, 2H), 4.74 (s, 4H), 4.50 (dd, J = 7.7, 3.9 Hz, 1H), 3.92-3.71 (m, 3H), 3.71-3.52 (m, 2H), 3.22 (dd, J = 9.8, 4.3 Hz, 3H), 2.45 (s, 3H), 2.13-1.80 (m, 3H), 1.67-1.37 (m, 3H) | (ESI (+)) m/e 450 (M + H)⁺ |

Example 1018

N-(4-{4-[(2-methylpropanoyl)amino]cyclohex-1-en-1-yl}phenyl)-1,3-dihydro-2H-pyrrolo[3,4-c]pyridine-2-carboxamide

Example 1018A

N-(4-(4,4,5,5-tetramethyl-1,3,2-dioxaborolan-2-yl)phenyl)-1H-pyrrolo[3,4-c]pyridine-2(3H)-carboxamide 2,3-Dihydro-1H-pyrrolo[3,4-c]pyridine 2.HCl (1.55 g, 8.03 mmol) was suspended in dimethylformamide (30 ml) and treated with triisopropylethylamine (4.21 ml, 24.08 mmol). After stirring for 20 minutes, the mixture was cooled to −15° C. 2-(4-Isocyanatophenyl)-4,4,5,5-tetramethyl-1,3,2-dioxaborolane (2.028 g, 8.03 mmol) was dissolved in 10 ml tetrahydrofuran and added via syringe over 10 minutes. The mixture was allowed to warm to room temperature, and it was stirred for 3 hours and concentrated under a stream of nitrogen to minimal volume. The residue was diluted with cold water to give a turbid mixture which was filtered with water washes to provide the title compound after drying.

Example 1018B tert-butyl 4-(4-(2,3-dihydro-1H-pyrrolo[3,4-c]pyridine-2-carboxamido)phenyl)cyclohex-3-enylcarbamate N-(4-(4,4,5,5-Tetramethyl-1,3,2-dioxaborolan-2-yl)phenyl)-1H-pyrrolo[3,4-c]pyridine-2(3H)-carboxamide (1.692 g, 4.63 mmol), 4-(tert-butoxycarbonylamino)cyclohex-1-enyl trifluoromethanesulfonate (1.6 g, 4.63 mmol) and cesium carbonate (3.77 g, 11.58 mmol) were suspended in

Example 1018C

N-(4-(4-aminocyclohex-1-enyl)phenyl)-1H-pyrrolo[3,4-c]pyridine-2(3H)-carboxamide The title compound was prepared as described in Example 2D, substituting tert-butyl 4-(4-(2,3-dihydro-1H-pyrrolo[3,4-c]pyridine-2-carboxamido)phenyl)cyclohex-3-enylcarbamate for tert-butyl 4-((4-(5-fluoroisoindoline-2-carboxamido)benzamido)methyl)benzylcarbamate.

Example 1018D

N-(4-{4-[(2-methylpropanoyl)amino]cyclohex-1-en-1-yl}phenyl)-1,3-dihydro-2H-pyrrolo[3,4-c]pyridine-2-carboxamide The title compound was prepared as described in Example 1C, substituting N-(4-(4-aminocyclohex-1-enyl)phenyl)-1H-pyrrolo[3,4-c]pyridine-2(3H)-carboxamide for 3-phenylpropan-1-amine and isobutyric acid for 4-(isoindoline-2-carboxamido)benzoic acid. $^1$H NMR (300 MHz, DMSO-d$_6$) δ ppm 8.61 (s, 1H), 8.50 (d, J=5.0 Hz, 1H), 8.41 (s, 1H), 7.66 (d, J=7.6 Hz, 1H), 7.56-7.48 (m, 2H), 7.43 (d, J=5.1 Hz, 1H), 7.37-7.29 (m, 2H), 6.06-5.99 (m, 1H), 4.83-4.77 (m, 4H), 3.87-3.73 (m, 1H), 2.37 (t, J=6.7 Hz, 2H), 2.11-1.97 (m, 1H), 1.95-1.82 (m, 1H), 1.80-1.50 (m, 1H), 1.38-1.20 (m, 2H), 1.00 (dd, J=6.8, 2.5 Hz, 6H); MS (ESI(+)) m/e 405 (M+H)$^+$. Table 20.

The title compound was prepared as described in Example 1C, substituting N-(4-(4-aminocyclohex-1-enyl)phenyl)-1H-pyrrolo[3,4-c]pyridine-2(3H)-carboxamide for 3-phenylpropan-1-amine and the appropriate carboxylic acid for 4-(isoindoline-2-carboxamido)benzoic acid.

| Ex | Name | $^1$H NMR | MS |
|---|---|---|---|
| 1022 | N-(4-{4-[(tetrahydrofuran-3-ylcarbonyl)amino]cyclohex-1-en-1-yl}phenyl)-1,3-dihydro-2H-pyrrolo[3,4-c]pyridine-2-carboxamide | $^1$H NMR (300 MHz, DMSO-d$_6$) δ 8.61 (s, 1H), 8.50 (d, J = 5.0 Hz, 1H), 8.42 (s, 1H), 7.91 (d, J = 7.5 Hz, 1H), 7.52 (d, J = 8.6 Hz, 2H), 7.43 (d, J = 5.0 Hz, 1H), 7.33 (d, J = 8.6 Hz, 2H), 6.02 (s, 1H), 4.80 (d, J = 4.1 Hz, 4H), 3.84 (td, J = 8.1, 3.7 Hz, 2H), 3.76-3.52 (m, 3H), 2.93 (p, J = 7.7 Hz, 1H), 2.11-1.79 (m, 5H), 1.60 (s, 1H) | (ESI (+)) m/e 433 (M + H)$^+$ |
| 1023 | N-(4-{4-[(tetrahydro-2H-pyran-4-ylcarbonyl)amino]cyclohex-1-en-1-yl}phenyl)-1,3-dihydro-2H-pyrrolo[3,4-c]pyridine-2-carboxamide | $^1$H NMR (300 MHz, DMSO-d$_6$) δ 8.61 (s, 1H), 8.50 (d, J = 5.0 Hz, 1H), 8.42 (s, 1H), 7.77-7.69 (m, 1H), 7.56-7.48 (m, 2H), 7.43 (d, J = 5.1 Hz, 1H), 7.37-7.29 (m, 2H), 6.02 (bs, 1H), 4.84-4.72 (m, 4H), 3.90-3.78 (m, 4H), 2.48-2.41 (m, 2H), 2.36 (s, 2H), 2.11-1.98 (m, 1H), 1.93-1.81 (m, 1H), 1.69-1.52 (m, 6H) | (ESI (+)) m/e 447 (M + H)$^+$ |
| 1024 | N-(4-{4-[(morpholin-4-ylacetyl)amino]cyclohex-1-en-1-yl}phenyl)-1,3-dihydro-2H-pyrrolo[3,4-c]pyridine-2-carboxamide | $^1$H NMR (300 MHz, DMSO-d$_6$) δ 8.61 (s, 1H), 8.50 (d, J = 4.9 Hz, 1H), 8.42 (s, 1H), 7.62 (d, J = 8.1 Hz, 1H), 7.53 (d, J = 8.7 Hz, 2H), 7.43 (d, J = 5.0 Hz, 1H), 7.33 (d, J = 8.7 Hz, 2H), 6.02 (s, 1H), 4.80 (d, J = 4.2 Hz, 4H), 3.91 (s, 1H), 3.64-3.49 (m, 5H), 2.92 (s, 2H), 2.41 (dd, J = 12.8, 8.2 Hz, 5H), 2.18 (s, 1H), 1.86 (s, 1H), 1.77-1.59 (m, 1H) | (ESI (+)) m/e 462 (M + H)$^+$ |
| 1025 | N-[4-(4-{[(2-methoxyethoxy)acetyl]amino}cyclohex-1-en-1-yl)phenyl]-1,3-dihydro-2H-pyrrolo[3,4-c]pyridine-2-carboxamide | $^1$H NMR (300 MHz, DMSO-d$_6$) δ 8.61 (s, 1H), 8.50 (d, J = 4.9 Hz, 1H), 8.42 (s, 1H), 7.59-7.49 (m, 3H), 7.43 (d, J = 5.1 Hz, 1H), 7.37-7.30 (m, 2H), 6.03 (bs, 1H), 4.83-4.77 (m, 4H), 3.88 (s, 4H), 3.60 (d, J = 3.8 Hz, 2H), 3.48 (d, J = 2.8 Hz, 2H), 3.25 (s, 3H), 2.36-1.97 (m, 3H), 1.93-1.82 (m, 1H), 1.77-1.57 (m, 1H) | (ESI (+)) m/e 451 (M + H)$^+$ |
| 1081 | N-(4-{4-[(tetrahydrofuran-2-ylacetyl)amino]cyclohex-1-en-1-yl}phenyl)-1,3-dihydro-2H-pyrrolo[3,4-c]pyridine-2-carboxamide | $^1$H NMR (300 MHz, DMSO-d$_6$) δ 8.61 (s, 1H), 8.50 (d, J = 5.0 Hz, 1H), 8.42 (s, 1H), 7.79 (d, J = 7.4 Hz, 1H), 7.52 (d, J = 8.7 Hz, 2H), 7.43 (d, J = 5.1 Hz, 1H), 7.33 (d, J = 8.7 Hz, 2H), 6.02 (s, 1H), 4.80 (d, J = 4.0 Hz, 4H), 4.07 (p, J = 6.7 Hz, 1H), 3.83 (s, 1H), 3.73 (dd, J = 14.2, 7.3 Hz, 1H), 3.58 (dd, J = 14.5, 7.6 Hz, 1H), 2.45 (s, 2H), 2.34 (dd, J = 13.8, 6.9 Hz, 2H), 2.28-2.16 (m, 1H), 2.11-1.96 (m, 1H), 1.96-1.71 (m, 4H), 1.68-1.39 (m, 2H) | (ESI (+)) m/e 447 (M + H)$^+$ |
| 1082 | N-(4-{4-[(tetrahydrofuran-3-ylacetyl)amino]cyclohex-1-en-1-yl}phenyl)-1,3-dihydro-2H-pyrrolo[3,4-c]pyridine-2-carboxamide | $^1$H NMR (300 MHz, DMSO-d$_6$) δ 8.61 (s, 1H), 8.50 (d, J = 5.0 Hz, 1H), 8.42 (s, 1H), 7.84 (d, J = 7.6 Hz, 1H), 7.52 (d, J = 8.8 Hz, 2H), 7.43 (d, J = 5.1 Hz, 1H), 7.36-7.29 (m, 2H), 6.02 (bs, 1H), 4.83-4.77 (m, 4H), 3.91-3.79 (m, 1H), 3.78-3.67 (m, 1H), 3.66-3.55 (m, 1H), 3.26 (q, J = 3.7 Hz, 1H), 2.44 (dd, J = 10.1, 4.1 Hz, 2H), 2.41-2.33 (m, 1H), 2.21-2.12 (m, 1H), 2.11-1.82 (m, 4H), 1.67-1.41 (m, 3H) | (ESI (+)) m/e 447 (M + H)$^+$ |

-continued

| Ex | Name | ¹H NMR | MS |
|---|---|---|---|
| 1083 | N-(4-{4-[(cyclohexylcarbonyl)amino]cyclohex-1-en-1-yl}phenyl)-1,3-dihydro-2H-pyrrolo[3,4-c]pyridine-2-carboxamide | ¹H NMR (300 MHz, DMSO-d₆) δ 8.61 (s, 1H), 8.50 (d, J = 5.0 Hz, 1H), 8.42 (s, 1H), 7.62 (d, J = 7.6 Hz, 1H), 7.56-7.48 (m, 2H), 7.43 (d, = 5.1 Hz, 1H), 7.36-7.29 (m, 2H), 6.01 (bs, 1H), 4.83-4.77 (m, 4H), 3.84-3.74 (m, 1H), 2.43-2.29 (m, 2H), 2.29-1.97 (m, 2H), 1.91-1.80 (m, 1H), 1.74-1.48 (m, 6H), 1.43-1.03 (m, 5H) | (ESI (+)) m/e 445 (M + H)⁺ |
| 1084 | N-[4-(4-{[(1,1-dioxidotetrahydrothiophen-3-yl)carbonyl]amino}cyclohex-1-en-1-yl)phenyl]-1,3-dihydro-2H-pyrrolo[3,4-c]pyridine-2-carboxamide | ¹H NMR (300 MHz, DMSO-d₆) δ 8.61 (s, 1H), 8.50 (d, J = 5.0 Hz, 1H), 8.42 (s, 1H), 8.12 (d, J = 7.4 Hz, 1H), 8.10-8.05 (m, 1H), 7.53 (d, J = 8.8 Hz, 2H), 7.43 (d, J = 5.1 Hz, 1H), 7.34 (d, J = 8.7 Hz, 2H), 6.02 (s, 1H), 4.80 (d, J = 4.1 Hz, 4H), 3.85 (s, 1H), 3.21 (ddd, J = 16.3, 11.0, 6.6 Hz, 3H), 3.14-2.96 (m, 2H), 2.31 (dd, J = 12.3, 6.1 Hz, 2H), 2.19-1.97 (m, 2H), 1.88 (s, 1H), 1.62 (s, 1H) | (ESI (+)) m/e 481 (M + H)⁺ |
| 1085 | N-[4-(4-{[(4,4-difluorocyclohexyl)carbonyl]amino}cyclohex-1-en-1-yl)phenyl]-1,3-dihydro-2H-pyrrolo[3,4-c]pyridine-2-carboxamide | ¹H NMR (300 MHz, DMSO-d₆) δ 8.61 (s, 1H), 8.50 (d, J = 5.0 Hz, 1H), 8.42 (s, 1H), 7.80 (d, J = 7.5 Hz, 1H), 7.56-7.48 (m, 2H), 7.43 (d, J = 5.1 Hz, 1H), 7.37-7.29 (m, 2H), 6.02 (bs, 1H), 4.83-4.77 (m, 4H), 3.89-3.77 (m, 1H), 2.41 (d, J = 23.9 Hz, 1H), 2.24-2.14 (m, 1H), 2.12-1.96 (m, 4H), 1.80 (d, J = 22.0 Hz, 4H), 1.70-1.50 (m, 4H) | (ESI (+)) m/e 481 (M + H)⁺ |
| 1086 | N-(4-{4-[(2-hydroxy-2-methylpropanoyl)amino]cyclohex-1-en-1-yl}phenyl)-1,3-dihydro-2H-pyrrolo[3,4-c]pyridine-2-carboxamide | ¹H NMR (300 MHz, DMSO-d₆) δ 8.61 (s, 1H), 8.50 (d, J = 5.0 Hz, 1H), 8.42 (s, 1H), 7.56-7.49 (m, 2H), 7.42 (d, J = 3.1 Hz, 2H), 7.37-7.30 (m, 2H), 6.03 (bs, 1H), 5.38 (s, 1H), 4.84-4.72 (m, 4H), 3.89-3.79 (m, 1H), 2.35 (s, 1H), 2.39-2.05 (m, 2H), 1.80 (d, J = 19.6 Hz, 1H), 1.77-1.61 (m, 1H), 1.25 (s, 6H) | (ESI (+)) m/e 421 (M + H)⁺ |
| 1087 | N-(4-{4-[(tetrahydrofuran-2-ylcarbonyl)amino]cyclohex-1-en-1-yl}phenyl)-1,3-dihydro-2H-pyrrolo[3,4-c]pyridine-2-carboxamide | ¹H NMR (300 MHz, DMSO-d₆) δ 8.61 (s, 1H), 8.50 (d, J = 5.0 Hz, 1H), 8.42 (s, 1H), 7.65-7.54 (m, 1H), 7.52 (d, J = 8.7 Hz, 2H), 7.43 (d, J = 5.0 Hz, 1H), 7.33 (d, J = 8.7 Hz, 2H), 6.02 (s, 1H), 4.80 (d, J = 4.0 Hz, 4H), 4.20 (dd, J = 8.1, 5.1 Hz, 1H), 3.89 (dd, J = 13.8, 7.1 Hz, 2H), 3.76 (dd, J = 14.4, 6.7 Hz, 1H), 2.30 (dd, J = 28.6, 11.2 Hz, 1H), 2.26-2.01 (m, 3H), 1.93-1.60 (m, 6H) | (ESI (+)) m/e 433 (M + H)⁺ |
| 1291 | N-(4-{4-[(cyclopropylacetyl)amino]cyclohex-1-en-1-yl}phenyl)-1,3-dihydro-2H-pyrrolo[3,4-c]pyridine-2-carboxamide | ¹H NMR (300 MHz, DMSO-d₆) δ 8.61 (s, 1H), 8.50 (d, J = 5.0 Hz, 1H), 8.42 (s, 1H), 7.67 (d, J = 7.6 Hz, 1H), 7.56-7.49 (m, 2H), 7.43 (d, J = 5.1 Hz, 1H), 7.37-7.29 (m, 2H), 6.02 (bs, 1H), 4.84-4.77 (m, 4H), 3.92-3.75 (m, 1H), 2.42 (d, J = 23.1 Hz, 2H), 2.10-2.03 (m, 1H), 1.99 (d, J = 7.0 Hz, 2H), 1.94-1.84 (m, 1H), 1.83-1.51 (m, 1H), 1.05-0.88 (m, 1H), 0.43 (dd, J = 9.8, 4.2 Hz, 2H), 0.21-0.07 (m, 2H) | (ESI (+)) m/e 417 (M + H)⁺ |
| 1442 | N-[4-(4-{[(4-methylpiperazin-1-yl)acetyl]amino}cyclohex-1-en-1-yl)phenyl]-1,3-dihydro-2H-pyrrolo[3,4-c]pyridine-2-carboxamide | ¹H NMR (300 MHz, DMSO-d₆) δ 8.61 (s, 1H), 8.50 (d, J = 5.0 Hz, 1H), 8.42 (s, 1H), 7.59-7.49 (m, 3H), 7.43 (d, J = 4.6 Hz, 1H), 7.37-7.30 (m, 2H), 6.06-5.98 (m, 1H), 5.75 (s, 1H), 4.84-4.77 (m, 4H), 4.00-3.85 (m, 1H), 3.05-2.90 (m, 2H), 2.90 (s, 3H), 2.32-2.13 (m, 5H), 2.12 (s, 3H), 2.12 (s, 3H), 1.91-1.80 (m, 1H), 1.75-1.61 (m, 1H) | (ESI (+)) m/e 475 (M + H)⁺ |
| 1443 | N-(4-{4-[(tetrahydro-2H-pyran-4-ylacetyl)amino]cyclohex-1-en-1-yl}phenyl)-1,3-dihydro-2H-pyrrolo[3,4-c]pyridine-2-carboxamide | ¹H NMR (300 MHz, DMSO-d₆) δ 8.65-8.57 (m, 1H), 8.55-8.45 (m, 1H), 8.44-8.36 (m, 2H), 7.88-7.75 (m, 1H), 7.60-7.47 (m, 2H), 7.47-7.37 (m, 1H), 7.36-7.24 (m, 2H), 6.07-5.86 (m, 1H), 4.87-4.62 (m, 4H), 3.90-3.68 (m, 2H), 3.29-3.17 (m, 2H), 2.45-2.28 (m, 2H), 2.09-1.91 (m, 4H), 1.93-1.79 (m, 2H), 1.64-1.42 (m, 3H), 1.28-1.07 (m, 2H) | (ESI (+)) m/e 461 (M + H)⁺ |
| 1444 | N-{4-[4-(benzoylamino)cyclohex-1-en-1-yl]phenyl}-1,3-dihydro-2H-pyrrolo[3,4-c]pyridine-2-carboxamide | ¹H NMR (300 MHz, DMSO-d₆) δ 8.61 (s, 1H), 8.49 (t, J = 4.7 Hz, 1H), 8.43 (s, 1H), 8.32 (d, J = 7.7 Hz, 1H), 7.91-7.83 (m, 2H), 7.57-7.41 (m, 6H), 7.38-7.28 (m, 2H), 6.07 (d, J = 1.8 Hz, 1H), 4.87-4.71 (m, 4H), 4.16-3.95 (m, 1H), 2.35-2.19 (m, 2H), 2.08-1.93 (m, 2H), 1.81-1.65 (m, 2H) | (ESI (+)) m/e 439 (M + H)⁺ |
| 1445 | N-[4-(4-{[(2S)-tetrahydrofuran-2-ylcarbonyl]amino}cyclohex-1-en-1-yl)phenyl]-1,3-dihydro-2H-pyrrolo[3,4-c]pyridine-2-carboxamide | ¹H NMR (300 MHz, DMSO-d₆) δ 8.62 (d, J = 5.8 Hz, 1H), 8.54-8.45 (m, 1H), 8.44-8.35 (m, 1H), 7.63-7.54 (m, 1H), 7.56-7.46 (m, 2H), 7.46-7.38 (m, 1H), 7.33 (d, J = 8.7 Hz, 2H), 6.06-5.90 (m, 1H), 4.86-4.65 (m, 4H), 4.26-4.11 (m, 1H), 3.94-3.80 (m, 2H), 3.80-3.62 (m, 1H), 2.40-2.25 (m, 2H), 2.27-2.02 (m, 2H), 1.92-1.77 (m, 4H), 1.75-1.60 (m, 1H) | (ESI (+)) m/e 433 (M + H)⁺ |

| Ex | Name | ¹H NMR | MS |
|---|---|---|---|
| 1446 | N-[4-(4-{[(2R)-tetrahydrofuran-2-ylcarbonyl]amino}cyclohex-1-en-1-yl)phenyl]-1,3-dihydro-2H-pyrrolo[3,4-c]pyridine-2-carboxamide | ¹H NMR (300 MHz, DMSO-d₆) δ 8.60 (s, 1H), 8.53-8.44 (m, 1H), 8.41 (d, J = 6.7 Hz, 1H), 7.65-7.56 (m, 1H), 7.56-7.47 (m, 2H), 7.46-7.39 (m, 1H), 7.33 (d, J = 8.7 Hz, 2H), 6.01 (t, J = 4.3 Hz, 1H), 4.80 (d, J = 4.0 Hz, 4H), 4.24-4.16 (m, 1H), 3.93-3.82 (m, 3H), 3.80-3.70 (m, 1H), 2.33 (dd, J = 5.3, 3.1 Hz, 1H), 2.24-2.01 (m, 3H), 2.01-1.63 (m, 5H) | (ESI (+)) m/e 433 (M + H)⁺ |
| 1447 | N-[4-(4-{[(1-methylpiperidin-4-yl)carbonyl]amino}cyclohex-1-en-1-yl)phenyl]-1,3-dihydro-2H-pyrrolo[3,4-c]pyridine-2-carboxamide | ¹H NMR (300 MHz, DMSO-d₆) δ 8.68-8.56 (m, 1H), 8.50 (d, J = 5.0 Hz, 1H), 8.42 (s, 1H), 7.70 (d, J = 7.6 Hz, 1H), 7.56-7.48 (m, 2H), 7.43 (d, J = 5.2 Hz, 1H), 7.37-7.29 (m, 2H), 6.02 (bs, 1H), 4.83-4.77 (m, 4H), 3.86-3.76 (m, 1H), 2.81-2.70 (m, 3H), 2.38-2.25 (m, 1H), 2.13 (s, 3H), 2.10-1.97 (m, 2H), 1.90-1.74 (m, 3H), 1.68-1.49 (m, 5H) | (ESI (+)) m/e 460 (M + H)⁺ |
| 1448 | N-[4-(4-{[(1,1-dioxidotetrahydro-2H-thiopyran-4-yl)carbonyl]amino}cyclohex-1-en-1-yl)phenyl]-1,3-dihydro-2H-pyrrolo[3,4-c]pyridine-2-carboxamide | ¹H NMR (300 MHz, DMSO-d₆) δ 8.61 (s, 1H), 8.50 (d, J = 5.0 Hz, 1H), 8.42 (s, 1H), 7.92 (d, J = 7.5 Hz, 1H), 7.56-7.49 (m, 2H), 7.43 (d, J = 5.1 Hz, 1H), 7.37-7.29 (m, 2H), 6.02 (bs, 1H), 4.87-4.77 (m, 4H), 3.83 (d, J = 3.0 Hz, 1H), 3.16-3.01 (m, 4H), 2.42 (d, J = 24.4 Hz, 4H), 2.11-1.91 (m, 5H), 1.93-1.78 (m, 1H), 1.72-1.52 (m, 1H) | (ESI (+)) m/e 495 (M + H)⁺ |
| 1449 | N-[4-(4-{[(3R)-tetrahydrofuran-3-ylcarbonyl]amino}cyclohex-1-en-1-yl)phenyl]-1,3-dihydro-2H-pyrrolo[3,4-c]pyridine-2-carboxamide | ¹H NMR (300 MHz, DMSO-d₆) δ 8.61 (s, 1H), 8.50 (d, J = 5.0 Hz, 1H), 8.42 (s, 1H), 7.92 (d, J = 7.5 Hz, 1H), 7.56-7.49 (m, 2H), 7.43 (d, J = 5.1 Hz, 1H), 7.37-7.29 (m, 2H), 6.02 (bs, 1H), 4.88-4.72 (m, 4H), 3.84 (td, J = 8.1, 3.8 Hz, 2H), 3.76-3.55 (m, 3H), 2.93 (p, J = 7.6 Hz, 1H), 2.42 (d, J = 19.4 Hz, 3H), 2.12-1.84 (m, 4H), 1.69-1.51 (m, 1H) | (ESI (+)) m/e 433 (M + H)⁺ |
| 1450 | N-[4-(4-{[(3S)-tetrahydrofuran-3-ylcarbonyl]amino}cyclohex-1-en-1-yl)phenyl]-1,3-dihydro-2H-pyrrolo[3,4-c]pyridine-2-carboxamide | ¹H NMR (300 MHz, DMSO-d₆) δ 8.61 (s, 1H), 8.50 (d, J = 5.0 Hz, 1H), 8.41 (s, 1H), 7.91 (d, J = 7.6 Hz, 1H), 7.54 (s, 2H), 7.43 (d, J = 5.1 Hz, 1H), 7.37-7.29 (m, 2H), 6.02 (bs, 1H), 4.85-4.72 (m, 4H), 3.84 (td, J = 8.1, 3.8 Hz, 2H), 3.78-3.55 (m, 3H), 2.93 (p, J = 7.7 Hz, 1H), 2.43 (d, J = 18.2 Hz, 2H), 2.11-1.79 (m, 4H), 1.60 (s, 1H) | (ESI (+)) m/e 433 (M + H)⁺ |
| 1451 | N-[4-(4-{[(2S)-2-methylbutanoyl]amino}cyclohex-1-en-1-yl)phenyl]-1,3-dihydro-2H-pyrrolo[3,4-c]pyridine-2-carboxamide | ¹H NMR (300 MHz, DMSO-d₆) δ 8.61 (s, 1H), 8.53-8.43 (m, 1H), 8.42 (d, J = 6.6 Hz, 1H), 7.76-7.62 (m, 1H), 7.56-7.46 (m, 2H), 7.49-7.36 (m, 1H), 7.35-7.28 (m, 2H), 6.05-5.94 (m, 1H), 4.91-4.65 (m, 4H), 4.06-3.70 (m, 1H), 2.48-2.31 (m, 2H), 2.24-1.98 (m, 2H), 1.94-1.77 (m, 1H), 1.70-1.40 (m, 2H), 1.39-1.14 (m, 2H), 1.04-0.86 (m, 3H), 0.82 (td, J = 7.4, 3.3 Hz, 3H) | (ESI (+)) m/e 419 (M + H)⁺ |

Example 1020 tert-butyl 3-{[(1,3-dihydro-2H-isoindol-2-ylcarbonyl)amino]methyl}azetidine-1-carboxylate The title compound was prepared as described in Example 272B, substituting tert-butyl 3-(aminomethyl)azetidine-1-carboxylate for 4-amino-N-propylbenzamide and isoindoline for methyl isoindoline-5-carboxylate hydrochloride. ¹H NMR (300 MHz, DMSO-d₆) δ ppm 7.37-7.23 (m, 4H), 6.58-6.48 (m, 1H), 4.58 (s, 4H), 3.91-3.75 (m, 2H), 3.65-3.51 (m, 2H), 3.30-3.20 (m, 2H), 2.68-2.55 (m, 1H), 1.35 (s, 9H); MS (ESI(+)) m/e 332 (M+H)⁺.

Example 1021 tert-butyl [(1-{4-[(1,3-dihydro-2H-isoindol-2-ylcarbonyl)amino]phenyl}azetidin-3-yl)methyl]carbamate

Example 1021A tert-butyl (1-(4-nitrophenyl)azetidin-3-yl)methylcarbamate

A solution of 1-fluoro-4-nitrobenzene (0.61 g, 4.32 mmol) and tert-butyl azetidin-3-ylmethylcarbamate (0.886 g, 4.76 mmol) in dimethylformamide (8.65 ml) was treated with potassium carbonate (0.896 g, 6.48 mmol) and the suspension was heated at 55° C. (12 pm) for 3 hours and at ambient temperature for 16 hours. The reaction was poured into water and the suspension was filtered. The solid was washed with water and dried to provide the title compound.

Example 1021B tert-butyl (1-(4-aminophenyl)azetidin-3-yl)methylcarbamate

The title compound was prepared as described in Example 272A, substituting tert-butyl (1-(4-nitrophenyl)azetidin-3-yl) methylcarbamate for 4-nitro-N-propylbenzamide.

Example 1021C tert-butyl [(1-{4-[(1,3-dihydro-2H-isoindol-2-ylcarbonyl)amino]phenyl}azetidin-3-yl)methyl]carbamate The title compound was prepared as described in Example 272B, substituting tert-butyl (1-(4-aminophenyl)azetidin-3-yl)methylcarbamate for 4-amino-N-propylbenzamide and isoindoline for methyl isoindoline-5-carboxylate hydrochloride. $^1$H NMR (300 MHz, DMSO-d$_6$) δ ppm 8.03 (s, 1H), 7.39-7.25 (m, 6H), 7.07-6.94 (m, 1H), 6.33 (d, J=8.8 Hz, 2H), 4.72 (s, 4H), 3.75 (t, J=7.4 Hz, 2H), 3.48-3.40 (m, 2H), 3.22-3.14 (m, 2H), 2.76-2.65 (m, 1H), 1.38 (s, 9H); MS (ESI(+)) m/e 423 (M+H)$^+$.

Example 1046

N-[4-({[4-(acetylamino)phenyl]sulfonyl}amino)phenyl]-1,3-dihydro-2H-pyrrolo[3,4-c]pyridine-2-carboxamide The title compound was prepared as described in Example 883, substituting N-(4-aminophenyl)-1H-pyrrolo[3,4-c]pyridine-2(3H)-carboxamide for N-(4-aminophenyl)isoindoline-2-carboxamide and 4-(acetylamino)phenylsulfonyl chloride for (3-methoxyphenyl)methanesulfonyl chloride. $^1$H NMR (400 MHz, DMSO-D$_2$O, Temp=90° C.) δ ppm 8.72 (s, 1H) 8.62 (d, J=4.88 Hz, 1H) 7.73 (d, J=5.49 Hz, 1H) 7.61-7.69 (m, 4H) 7.36 (d, J=8.54 Hz, 2H) 6.98 (d, J=8.85 Hz, 2H) 4.88 (d, J=7.02 Hz, 4H) 2.00-2.10 (m, 3H); MS (APCI(+)) m/e 452 (M+H)$^+$.

Example 1047

N-{4-[(propylsulfonyl)amino]phenyl}-1,3-dihydro-2H-pyrrolo[3,4-c]pyridine-2-carboxamide The title compound was prepared as described in Example 883, substituting N-(4-aminophenyl)-1H-pyrrolo[3,4-c]pyridine-2(3H)-carboxamide for N-(4-aminophenyl)isoindoline-2-carboxamide and propylsulfonyl chloride for (3-methoxyphenyl)methanesulfonyl chloride. $^1$H NMR (400 MHz, DMSO-D$_2$O, Temp=90° C.) δ ppm 8.72 (s, 1H) 8.62 (d, J=5.49 Hz, 1H) 7.73 (d, J=5.49 Hz, 1H) 7.46 (d, J=8.54 Hz, 2H) 7.14 (d, J=8.85 Hz, 2H) 4.91 (d, J=6.10 Hz, 4H) 2.98-3.06 (m, 2H) 1.66-1.78 (m, 2H) 0.96 (t, J=7.48 Hz, 3H); MS (APCI(+)) m/e 361 (M+H)$^+$.

Example 1048

N-(4-{[(4-propylphenyl)sulfonyl]amino}phenyl)-1,3-dihydro-2H-pyrrolo[3,4-c]pyridine-2-carboxamide The title compound was prepared as described in Example 883, substituting N-(4-aminophenyl)-1H-pyrrolo[3,4-c]pyridine-2(3H)-carboxamide for N-(4-aminophenyl)isoindoline-2-carboxamide and (4-propylphenyl)sulfonyl chloride for (3-methoxyphenyl)methanesulfonyl chloride. $^1$H NMR (300 MHz, DMSO-d$_6$) δ 9.90 (s, 1H), 8.59 (s, 1H), 8.49 (d, J=5.0 Hz, 1H), 8.33 (s, 1H), 7.64-7.58 (m, 2H), 7.45-7.33 (m, 4H), 7.33 (s, 1H), 6.99-6.92 (m, 2H), 4.79-4.72 (m, 4H), 2.57 (dd, J=17.1, 9.3 Hz, 1H), 1.65-1.49 (m, 2H), 0.86 (t, J=7.3 Hz, 3H); MS (ESI(+)) m/e 437 (M+H)$^+$.

Example 1049

N-{4-[(butylsulfonyl)amino]phenyl}-1,3-dihydro-2H-pyrrolo[3,4-c]pyridine-2-carboxamide The title compound was prepared as described in Example 883, substituting N-(4-aminophenyl)-1H-pyrrolo[3,4-c]pyridine-2(3H)-carboxamide for N-(4-aminophenyl)isoindoline-2-carboxamide and butylsulfonyl chloride for (3-methoxyphenyl)methanesulfonyl chloride. $^1$H NMR (400 MHz, DMSO-D$_2$O, Temp=90° C.) δ ppm 8.71 (s, 1H) 8.61 (d, J=5.19 Hz, 1H) 7.70 (d, J=5.49 Hz, 1H) 7.47 (d, J=8.85 Hz, 2H) 7.14 (d, J=8.85 Hz, 2H) 4.90 (d, J=3.66 Hz, 4H) 2.97-3.08 (m, 2H) 1.61-1.72 (m, 2H) 1.30-1.44 (m, 2H) 0.85 (t, J=7.32 Hz, 3H); MS (APCI(+)) m/e 375 (M+H)$^+$.

Example 1050

N-{4-[({[(1S,4R)-7,7-dimethyl-2-oxobicyclo[2.2.1]hept-1-yl]methyl}sulfonyl)amino]phenyl}-1,3-dihydro-2H-pyrrolo[3,4-c]pyridine-2-carboxamide The title compound was prepared as described in Example 883, substituting N-(4-aminophenyl)-1H-pyrrolo[3,4-c]pyridine-2(3H)-carboxamide for N-(4-aminophenyl)isoindoline-2-carboxamide and (1S,4R)-7,7-dimethyl-2-oxobicyclo[2.2.1]hept-1-yl]methyl}sulfonyl chloride for (3-methoxyphenyl)methanesulfonyl chloride. $^1$H NMR (400 MHz, DMSO-D$_2$O, Temp=90° C.) δ ppm 8.72 (s, 1H) 8.61 (d, J=5.19 Hz, 1H) 7.71 (d, J=5.49 Hz, 1H) 7.49 (d, J=8.85 Hz, 2H) 7.18 (d, J=8.85 Hz, 2H) 4.90 (d, J=3.97 Hz, 4H) 2.81 (s, 2H) 2.27-2.41 (m, 2H) 2.07 (t, J=4.43 Hz, 1H) 1.94-2.03 (m, 2H) 1.34-1.66 (m, 2H) 1.02 (s, 3H) 0.79 (s, 3H); MS (APCI(+)) m/e 469 (M+H)$^+$.

Example 1051

N-{4-[(ethylsulfonyl)amino]phenyl}-1,3-dihydro-2H-pyrrolo[3,4-c]pyridine-2-carboxamide The title compound was prepared as described in Example 883, substituting N-(4-aminophenyl)-1H-pyrrolo[3,4-c]pyridine-2(3H)-carboxamide for N-(4-aminophenyl)isoindoline-2-carboxamide and ethylsulfonyl chloride for (3-methoxyphenyl)methanesulfonyl chloride. $^1$H NMR (400 MHz, DMSO-D$_2$O, Temp=90° C.) δ ppm 8.70-8.75 (m, 1H) 8.60-8.64 (m, J=5.65, 5.65 Hz, 1H) 7.74 (d, J=5.19 Hz, 1H) 7.46 (d, J=8.85 Hz, 2H) 7.15 (d, J=8.54 Hz, 2H) 4.91 (d, J=7.02 Hz, 4H) 3.04 (q, J=7.32 Hz, 2H) 1.23 (t, J=7.32 Hz, 3H); MS (APCI(+)) m/e 347 (M+H)$^+$.

Example 1052

N-{4-[(benzylsulfonyl)amino]phenyl}-1,3-dihydro-2H-pyrrolo[3,4-c]pyridine-2-carboxamide The title compound was prepared as described in Example 883, substituting N-(4-aminophenyl)-1H-pyrrolo[3,4-c]pyridine-2(3H)-carboxamide for N-(4-aminophenyl)isoindoline-2-carboxamide and benzylsulfonyl chloride for (3-methoxyphenyl)methanesulfonyl chloride. $^1$H NMR (400 MHz, DMSO-D$_2$O, Temp=90° C.) δ ppm 8.72 (s, 1H) 8.61 (d, J=4.88 Hz, 1H) 7.70 (d, J=5.19 Hz, 1H) 7.46 (d, J=8.85 Hz, 2H) 7.28-7.37 (m, 5H) 7.11 (d, J=8.85 Hz, 2H) 4.90 (d, J=3.05 Hz, 4H) 4.37 (s, 2H); MS (APCI(+)) m/e 409 (M+H)$^+$.

Example 1053

N-(4-{[(4-fluorophenyl)sulfonyl]amino}phenyl)-1,3-dihydro-2H-pyrrolo[3,4-c]pyridine-2-carboxamide The title compound was prepared as described in Example 883, substituting N-(4-aminophenyl)-1H-pyrrolo[3,4-c]pyridine-2(3H)-carboxamide for N-(4-aminophenyl)isoindoline-2-carboxamide and (4-fluorophenyl)sulfonyl chloride for (3-methoxyphenyl)methanesulfonyl chloride. $^1$H NMR (400 MHz, DMSO-D$_2$O, Temp=90° C.) δ ppm 8.71 (s, 1H) 8.61 (d, J=5.19 Hz, 1H) 7.78 (dd, J=8.85, 5.19 Hz, 2H) 7.67-7.73 (m, 1H) 7.28-7.43 (m, 4H) 6.98 (d, J=8.85 Hz, 2H) 4.87 (d, J=4.27 Hz, 4H); MS (APCI(+)) m/e 412 (M+H)$^+$.

Example 1054

N-{4-[(thiophen-2-ylsulfonyl)amino]phenyl}-1,3-dihydro-2H-pyrrolo[3,4-c]pyridine-2-carboxamide The title compound was prepared as described in Example 883, substituting N-(4-aminophenyl)-1H-pyrrolo[3,4-c]pyridine-2(3H)-carboxamide for N-(4-aminophenyl)isoindoline-2-carboxamide and thiophen-2-ylsulfonyl chloride for (3-methoxyphenyl)methanesulfonyl chloride. $^1$H NMR (400 MHz, DMSO-D$_2$O, Temp=90° C.) δ ppm 8.70 (s, 1H) 8.61 (d, J=4.88 Hz, 1H) 7.81 (d, J=4.88 Hz, 1H) 7.69 (d, J=5.19 Hz, 1H) 7.49 (d, J=2.75 Hz, 1H) 7.42 (d, J=8.85 Hz, 2H) 7.09-7.13 (m, 1H) 7.04 (d, J=8.85 Hz, 2H) 4.88 (d, J=3.36 Hz, 4H); MS (APCI(+)) m/e 401 (M+H)$^+$.

Example 1088

N-[4-(piperidin-1-ylsulfonyl)phenyl]-1,3-dihydro-2H-pyrrolo[3,4-c]pyridine-2-carboxamide The title compound was prepared as described in Example 272B, substituting 4-(piperidin-1-ylsulfonyl)aniline for 4-amino-N-propylbenzamide and 1,3-dihydro-2H-pyrrolo[3,4-c]pyridine for methyl isoindoline-5-carboxylate hydrochloride. $^1$H NMR (300 MHz, DMSO-d$_6$) δ ppm 8.89 (s, 1H), 8.62 (s, 1H), 8.51 (d, J=5.0 Hz, 1H), 7.86-7.79 (m, 2H), 7.66-7.59 (m, 2H), 7.44 (d, J=5.0 Hz, 1H), 4.89-4.76 (m, 4H), 3.25-3.00 (m, 1H), 2.95-2.82 (m, 4H), 1.57-1.44 (m, 4H), 1.41-1.31 (m, 1H); MS (ESI(+)) m/e 387 (M+H)$^+$.

Example 1246 methyl 1-{4-[(1,3-dihydro-2H-pyrrolo[3,4-c]pyridin-2-ylcarbonyl)amino]phenyl}azetidine-3-carboxylate Example 1246A methyl 1-(4-nitrophenyl)azetidine-3-carboxylate A solution of methyl azetidine-3-carboxylate hydrochloride (1.236 g, 8.15 mmol) and N-methylmorpholine (2.338 ml, 21.26 mmol) in dimethylformamide (10 mL) was treated with a solution of 1-fluoro-4-nitrobenzene (1 g, 7.09 mmol) in dimethylformamide (7 mL) and the reaction was allowed to stir at room temperature for 60 hours. Water (50 mL) was added and the resulting suspension was stirred 10 minutes and filtered. The collected solid was washed with water and dried under vacuum. Flash chromatography of the collected solid provided the title compound.

Example 1246B methyl 1-(4-aminophenyl)azetidine-3-carboxylate

The title compound was prepared as described in Example 272A, substituting methyl 1-(4-nitrophenyl)azetidine-3-carboxylate for 4-nitro-N-propylbenzamide.

Example 1246C methyl 1-{4-[(1,3-dihydro-2H-pyrrolo[3,4-c]pyridin-2-ylcarbonyl)amino]phenyl}azetidine-3-carboxylate The title compound was prepared as described in Example 272B, substituting methyl 1-(4-aminophenyl)azetidine-3-carboxylate for 4-amino-N-propylbenzamide and 1,3-dihydro-2H-pyrrolo[3,4-c]pyridine for methyl isoindoline-5-carboxylate hydrochloride. $^1$H NMR (300 MHz, DMSO-d$_6$) δ ppm 8.60 (s, 1H), 8.49 (d, J=5.0 Hz, 1H), 8.15 (s, 1H), 7.42 (d, J=5.1 Hz, 1H), 7.36-7.29 (m, 2H), 6.44-6.37 (m, 2H), 4.80-4.72 (m, 4H), 4.02-3.93 (m, 2H), 3.86-3.77 (m, 2H), 3.68 (s, 3H), 3.66-3.56 (m, 1H); MS (ESI(+)) m/e 353 (M+H)$^+$.

Example 1247

N-(4-{3-[(3-methylbutyl)carbamoyl]azetidin-1-yl}phenyl)-1,3-dihydro-2H-pyrrolo[3,4-c]pyridine-2-carboxamide Example 1247A 1-(4-(2,3-dihydro-1H-pyrrolo[3,4-c]pyridine-2-carboxamido)phenyl)azetidine-3-carboxylic acid The title compound was prepared as described in Example 1B, substituting methyl 1-{4-[(1,3-dihydro-2H-pyrrolo[3,4-c]pyridin-2-ylcarbonyl)amino]phenyl}azetidine-3-carboxylate for methyl 4-(isoindoline-2-carboxamido)benzoate.

Example 1247B

N-(4-{3-[(3-methylbutyl)carbamoyl]azetidin-1-yl}phenyl)-1,3-dihydro-2H-pyrrolo[3,4-c]pyridine-2-carboxamide The title compound was prepared as described in Example 1C, substituting 3-methylbutan-1-amine for 3-phenylpropan-1-amine and 1-(4-(2,3-dihydro-1H-pyrrolo[3,4-c]pyridine-2-carboxamido)phenyl)azetidine-3-carboxylic acid for 4-(isoindoline-2-carboxamido)benzoic acid. $^1$H NMR (300 MHz, DMSO-d$_6$) δ ppm 8.59 (s, 1H), 8.49 (d, J=5.0 Hz, 1H), 8.13 (s, 1H), 7.90 (t, J=5.5 Hz, 1H), 7.42 (d, J=4.8 Hz, 1H), 7.34-7.27 (m, 2H), 6.41-6.34 (m, 2H), 4.79-4.73 (m, 4H), 3.94-3.85 (m, 2H), 3.76-3.69 (m, 2H), 3.47-3.36 (m, 1H), 3.13-3.04 (m, 2H), 1.65-1.48 (m, 1H), 1.35-1.24 (m, 2H), 0.87 (d, J=6.6 Hz, 6H); MS (ESI(+)) m/e 408 (M+H)+.

Example 1248

N-(4-{3-[(tetrahydrofuran-2-ylmethyl)carbamoyl] azetidin-1-yl}phenyl)-1,3-dihydro-2H-pyrrolo[3,4-c] pyridine-2-carboxamide The title compound was prepared as described in Example 1C, substituting (tetrahydrofuran-2-yl)methanamine for 3-phenylpropan-1-amine and 1-(4-(2,3-dihydro-1H-pyrrolo[3,4-c]pyridine-2-carboxamido)phenyl)azetidine-3-carboxylic acid for 4-(isoindoline-2-carboxamido)benzoic acid. $^1$H NMR (300 MHz, DMSO-d$_6$) δ ppm 8.59 (s, 1H), 8.49 (d, J=5.0 Hz, 1H), 8.13 (s, 1H), 8.05 (t, J=5.8 Hz, 1H), 7.42 (d, J=5.1 Hz, 1H), 7.35-7.27 (m, 2H), 6.41-6.34 (m, 2H), 4.79-4.73 (m, 4H), 3.94-3.68 (m, 6H), 3.68-3.55 (m, 1H), 3.54-3.39 (m, 1H), 3.20-3.07 (m, 2H), 1.93-1.71 (m, 3H), 1.55-1.41 (m, 1H); MS (ESI(+)) m/e 422 (M+H)+.

Example 1249

N-(4-{3-[(tetrahydro-2H-pyran-4-ylmethyl)carbamoyl]azetidin-1-yl}phenyl)-1,3-dihydro-2H-pyrrolo[3,4-c]pyridine-2-carboxamide The title compound was prepared as described in Example 1C, substituting (tetrahydro-2H-pyran-4-yl)methanamine for 3-phenylpropan-1-amine and 1-(4-(2,3-dihydro-1H-pyrrolo[3,4-c]pyridine-2-carboxamido)phenyl)azetidine-3-carboxylic acid for 4-(isoindoline-2-carboxamido)benzoic acid. $^1$H NMR (300 MHz, DMSO-d$_6$) δ ppm 8.59 (s, 1H), 8.49 (d, J=5.0 Hz, 1H), 8.13 (s, 1H), 7.97 (t, J=5.8 Hz, 1H), 7.42 (d, J=5.1 Hz, 1H), 7.34-7.27 (m, 2H), 6.41-6.34 (m, 2H), 4.79-4.73 (m, 4H), 3.95-3.86 (m, 2H), 3.86-3.78 (m, 2H), 3.77-3.69 (m, 2H), 3.51-3.40 (m, 1H), 3.31-3.19 (m, 2H), 3.02-2.94 (m, 2H), 1.69-1.48 (m, 3H), 1.22-1.04 (m, 2H); MS (ESI(+)) m/e 436 (M+H)+.

Example 1250

N-{4-[3-(benzylcarbamoyl)azetidin-1-yl]phenyl}-1,3-dihydro-2H-pyrrolo[3,4-c]pyridine-2-carboxamide The title compound was prepared as described in Example 1C, substituting benzylamine for 3-phenylpropan-1-amine and 1-(4-(2,3-dihydro-1H-pyrrolo[3,4-c]pyridine-2-carboxamido)phenyl)azetidine-3-carboxylic acid for 4-(isoindoline-2-carboxamido)benzoic acid. $^1$H NMR (300 MHz, DMSO-d$_6$) δ ppm 8.59 (s, 1H), 8.53-8.45 (m, 2H), 8.13 (s, 1H), 7.42 (d, J=5.0 Hz, 1H), 7.37-7.22 (m, 7H), 6.43-6.35 (m, 2H), 4.76 (m, 4H), 4.30 (d, J=5.9 Hz, 2H), 3.99-3.88 (m, 2H), 3.83-3.72 (m, 2H), 3.57-3.46 (m, 1H); MS (ESI(+)) m/e 428 (M+H)+.

Example 1251

N-{4-[3-(cyclopentylcarbamoyl)azetidin-1-yl]phenyl}-1,3-dihydro-2H-pyrrolo[3,4-c]pyridine-2-carboxamide The title compound was prepared as described in Example 1C, substituting cyclopentylamine for 3-phenylpropan-1-amine and 1-(4-(2,3-dihydro-1H-pyrrolo[3,4-c]pyridine-2-carboxamido)phenyl)azetidine-3-carboxylic acid for 4-(isoindoline-2-carboxamido)benzoic acid. $^1$H NMR (300 MHz, DMSO-d$_6$) δ ppm 8.59 (s, 1H), 8.49 (d, J=5.0 Hz, 1H), 8.13 (s, 1H), 7.91 (d, J=7.2 Hz, 1H), 7.42 (d, J=5.1 Hz, 1H), 7.34-7.27 (m, 2H), 6.41-6.33 (m, 2H), 4.79-4.73 (m, 4H), 4.06-3.94 (m, 1H), 3.92-3.84 (m, 2H), 3.76-3.66 (m, 2H), 3.46-3.33 (m, 1H), 1.86-1.72 (m, 2H), 1.67-1.30 (m, 6H); MS (ESI(+)) m/e 406 (M+H)+.

Example 1252

N-(4-{3-[(cyclopentylmethyl)carbamoyl]azetidin-1-yl}phenyl)-1,3-dihydro-2H-pyrrolo[3,4-c]pyridine-2-carboxamide The title compound was prepared as described in Example 1C, substituting cyclopentylmethamine for 3-phenylpropan-1-amine and 1-(4-(2,3-dihydro-1H-pyrrolo[3,4-c]pyridine-2-carboxamido)phenyl)azetidine-3-carboxylic acid for 4-(isoindoline-2-carboxamido)benzoic acid. $^1$H NMR (300 MHz, DMSO-d$_6$) δ ppm 8.59 (s, 1H), 8.49 (d, J=5.0 Hz, 1H), 8.13 (s, 1H), 7.96 (t, J=5.7 Hz, 1H), 7.42 (d, J=4.7 Hz, 1H), 7.34-7.27 (m, 2H), 6.41-6.33 (m, 2H), 4.81-4.72 (m, 4H), 3.94-3.85 (m, 2H), 3.77-3.68 (m, 2H), 3.50-3.37 (m, 1H), 3.04-2.97 (m, 2H), 2.04-1.89 (m, 1H), 1.71-1.39 (m, 6H), 1.25-1.08 (m, 2H); MS (ESI(+)) m/e 420 (M+H)+.

Example 1253

N-(4-{3-[(2-methoxyethyl)carbamoyl]azetidin-1-yl}phenyl)-1,3-dihydro-2H-pyrrolo[3,4-c]pyridine-2-carboxamide The title compound was prepared as described in Example 1C, substituting 2-methoxyeth-1-ylamine for 3-phenylpropan-1-amine and 1-(4-(2,3-dihydro-1H-pyrrolo[3,4-c]pyridine-2-carboxamido)phenyl)azetidine-3-carboxylic acid for 4-(isoindoline-2-carboxamido)benzoic acid. $^1$H NMR (300 MHz, DMSO-d$_6$) δ ppm 8.59 (s, 1H), 8.49 (d, J=5.0 Hz, 1H), 8.13 (s, 1H), 8.05 (t, J=5.5 Hz, 1H), 7.42 (d, J=5.1 Hz, 1H), 7.35-7.27 (m, 2H), 6.42-6.34 (m, 2H), 4.79-4.73 (m, 4H), 3.93-3.86 (m, 2H), 3.73 (t, J=6.6 Hz, 2H), 3.52-3.41 (m, 1H), 3.38-3.30 (m, 2H), 3.27-3.21 (m, 5H); MS (ESI(+)) m/e 396 (M+H)+.

Example 1268

N-(6-{[(2S)-tetrahydrofuran-2-ylmethyl] carbamoyl}pyridazin-3-yl)-1,3-dihydro-2H-isoindole-2-carboxamide The title compound was prepared as described in Example 1C, substituting (S)-(tetrahydrofuran-2-yl)methamine for 3-phenylpropan-1-amine and 6-(isoindoline-2-carboxamido)pyridazine-3-carboxylic acid for 4-(isoindoline-2-carboxamido)benzoic acid. $^1$H NMR (300 MHz, DMSO-d$_6$) δ 10.03 (s, 1H), 8.85 (t, J=6.1 Hz, 1H), 8.32 (d, J=9.3 Hz, 1H), 8.12 (d, J=9.3 Hz, 1H), 7.41-7.28 (m, 4H), 5.04-4.72 (m, 4H), 4.04 (p, J=6.2 Hz, 1H), 3.85-3.74 (m, 1H), 3.69-3.58 (m, 1H), 3.38 (dd, J=11.2, 5.0 Hz, 2H), 2.01-1.74 (m, 3H), 1.71-1.54 (m, 1H); MS (ESI(+)) m/e 368 (M+H)+.

Example 1285

N-{4-[(4-fluorobenzyl)(3-methylbutanoyl)amino] butyl}-1,3-dihydro-2H-isoindole-2-carboxamide Example 1285A tert-butyl 4-(4-fluorobenzylamino)butylcarbamate Tert-butyl 4-bromobutylcarbamate (0.735 g, 2.91 mmoles), (4-fluorophenyl)methanamine (0.333 g, 2.91 mmoles) and potassium carbonate (0.806 g, 5.83 mmoles) were stirred in acetonitrile (15 mL) at 100° C. for 1 hour. The reaction mixture was cooled, the solvent waqs concentrated and the residue was taken into dichloromethane and washed with water twice. The organic layers were combined, dried over magnesium sulfate, filtered and concentrated to provide the title compound which was used without further purification in the next step.

Example 1285B tert-butyl 4-(N-(4-fluorobenzyl)-3-methylbutanamido)butylcarbamate The title compound was prepared as described in Example 278, substituting 3-methylbutanoyl chloride for acetyl chloride and tert-butyl 4-(4-fluorobenzylamino)butylcarbamate for 5-amino-N-(4-(propylcarbamoyl)phenyl)isoindoline-2-carboxamide.

Example 1285C

N-(4-aminobutyl)-N-(4-fluorobenzyl)-3-methylbutanamide

The title compound was prepared as described in Example 2D, substituting tert-butyl 4-(N-(4-fluorobenzyl)-3-methylbutanamido)butylcarbamate for tert-butyl 4-((4-(5-fluoroisoindoline-2-carboxamido)benzamido)methyl)benzylcarbamate.

Example 1285D

N-{4-[(4-fluorobenzyl)(3-methylbutanoyl)amino]butyl}-1,3-dihydro-2H-isoindole-2-carboxamide The title compound was prepared as described in Example 272B, substituting N-(4-aminobutyl)-N-(4-fluorobenzyl)-3-methylbutanamide for 4-amino-N-propylbenzamide and isoindoline for methyl isoindoline-5-carboxylate hydrochloride. $^1$H NMR (400 MHz, CDCl$_3$) δ ppm 7.34-7.27 (m, 4H), 7.23 (dd, J=8.5, 5.5 Hz, 1H), 7.13 (dd, J=8.5, 5.5 Hz, 1H), 7.06 (t, J=8.6 Hz, 1H), 6.99 (t, J=8.6 Hz, 1H), 5.49-5.17 (m, 1H), 4.72 (m, 4H), 4.56 (d, J=17.7 Hz, 2H), 3.34 (m, 4H), 2.29 (m, 2H), 2.23-2.12 (m, 1H), 1.68-1.50 (m, 4H), 1.01-0.93 (d, J=6.9 Hz, 6H); MS (APCI(+)) m/e 426 (M+H)$^+$.

Example 1286

N-[4-(9-chloro-5-oxo-2,3,3a,4,4a,5-hexahydro-6H-furo[2',3':2,3]cyclobuta[1,2-c]quinolin-6-yl)butyl]-1,3-dihydro-2H-pyrrolo[3,4-c]pyridine-2-carboxamide

Example 1286A 4-(but-3-enyloxy)-6-chloroquinolin-2(1H)-one

To a solution of 6-chloro-4-hydroxyquinolin-2(1H)-one (800 mg, 4.09 mmol) and N,N-diisopropylethylamine (1415 μl, 8.18 mmol) in dimethylformamide (13.6 ml) was added 4-bromo-1-butene (415 μl, 4.09 mmol). The solution was heated to 60° C. and stirred for 18 hours. The reaction mixture was purified by column chromatography to provide the title compound.

Example 1286B 9-chloro-3,3a,4,4a-tetrahydro-2H-furo[2',3':2,3]cyclobuta[1,2-c]quinolin-5(6H)-one A solution of 4-(but-3-enyloxy)-6-chloroquinolin-2(1H)-one (600 mg, 2.403 mmol) in benzene (240 mL) was placed under a 450 W Hg UV lamp (fitted with a condenser for cooling) and stirred for 4 days (96 hours). The mixture was then cooled, concentrated in vacuo, and taken up in ~75 mL of methylene chloride (with mild heating to dissolve as much as possible). The sample, which was a mixture of regioisomers, was purified by column chromatography. Concentration of the compound that eleuted second provided the title compound.

Example 1286C tert-butyl [4-(9-chloro-5-oxo-2,3,3a,4,4a,5-hexahydro-6H-furo[2',3':2,3]cyclobuta[1,2-c]quinolin-6-yl)butyl]carbamate To a solution of 9-chloro-3,3a,4,4a-tetrahydro-2H-furo[2',3':2,3]cyclobuta[1,2-c]quinolin-5(6H)-one (200 mg, 0.801 mmol) in dimethylformamide (4 ml) at 0° C. was slowly added sodium hydride (19 mg, 0.801 mmol) over 15 minutes. The suspension was allowed to warm to room temperature. The mixture stirred for 45 minutes and 4-(Boc-amino)butyl bromide (202 mg, 0.801 mmol) was added. The solution was stirred for 15 hours, followed by addition of 0.25 mL methanol. Column chromatography provided the title compound.

Example 1286D 6-(4-aminobutyl)-9-chloro-3,3a,4,4a-tetrahydro-2H-furo[2',3':2,3]cyclobuta[1,2-c]quinolin-5(6H)-one The title compound was prepared as described in Example 2D, substituting tert-butyl [4-(9-chloro-5-oxo-2,3,3a,4,4a,5-hexahydro-6H-furo[2',3':2,3]cyclobuta[1,2-c]quinolin-6-yl)butyl]carbamate for tert-butyl 44(4-(5-fluoroisoindoline-2-carboxamido)benzamido)methyl)benzylcarbamate.

Example 1286E

N-[4-(9-chloro-5-oxo-2,3,3a,4,4a,5-hexahydro-6H-furo[2',3':2,3]cyclobuta[1,2-c]quinolin-6-yl)butyl]-1,3-dihydro-2H-pyrrolo[3,4-c]pyridine-2-carboxamide The title compound was prepared as described in Example 272B, substituting 6-(4-aminobutyl)-9-chloro-3,3a,4,4a-tetrahydro-2H-furo[2',3':2,3]cyclobuta[1,2-c]quinolin-5(6H)-one for 4-amino-N-propylbenzamide and 1,3-dihydro-2H-pyrrolo[3,4-c]pyridine for methyl isoindoline-5-carboxylate hydrochloride. $^1$H NMR (400 MHz, CDCl$_3$) δ ppm 8.58 (s, 1H), 8.54 (d, J=4.9 Hz, 1H), 7.29 (d, J=4.9 Hz, 1H), 7.25 (m, 1H), 7.23 (d, J=2.6 Hz, 1H), 6.92 (d, J=8.9 Hz, 1H), 4.84 (t, J=5.6 Hz, 1H), 4.74 (bs, 4H), 4.46 (t, J=8.1 Hz, 1H), 4.22 (m, 1H), 4.05 (m, 1H), 3.91 (m, 1H), 3.39 (m, 3H), 2.93 (m, 1H), 2.31 (m, 1H), 2.22 (m, 1H), 1.84 (m, 1H), 1.69 (m, 5H); MS (ESI(+)) m/e 467 (M+H)$^+$.

Example 1287

N-{4-[7-chloro-1-(2-hydroxyethyl)-3-oxo-1,3-dihydrocyclobuta[c]quinolin-4(2H)-yl]butyl}-1,3-dihydro-2H-pyrrolo[3,4-c]pyridine-2-carboxamide To a solution of N-[4-(9-chloro-5-oxo-2,3,3a,4,4a,5-hexahydro-6H-furo[2',3':2,3]cyclobuta[1,2-c]quinolin-6-yl)butyl]-1,3-dihydro-2H-pyrrolo[3,4-c]pyridine-2-carboxamide (30 mg, 0.064 mmol) in dimethylformamide (292 uL) and water (292 uL) was added sodium hydroxide (1.679 μl, 0.064 mmol). The solution was stirred for 18 hours and then brought to pH ~7 by dropwise addition of 1M HCl. Column chromatography of the wet, crude mixture provided the title compound. $^1$H NMR (400 MHz, CDCl$_3$) δ ppm 8.58 (s, 1H), 8.54 (d, J=5.1 Hz, 1H), 7.54 (d, J=2.4 Hz, 1H), 7.46 (dd, J=9.1, 2.4 Hz, 1H), 7.37 (d, J=9.1 Hz, 1H), 7.25 (m, 1H), 5.06 (t, J=5.7 Hz, 1H) 4.77 (bs, 2H), 4.75 (bs, 2H), 4.33 (t, J=7.4 Hz, 2H), 3.87 (m, 2H), 3.74 (m, 2H), 3.46 (m, 2H), 3.37 (dd, J=14.0, 4.5 Hz, 1H), 2.86 (dd, J=14.0, 1.3 Hz, 1H), 2.27 (m, 1H), 1.97 (m, 1H), 1.82 (m, 2H), 1.71 (m, 2H); MS (ESI(+)) m/e 467 (M+H)$^+$.

Example 1290

N-(6-{[(2R)-tetrahydrofuran-2-ylmethyl]carbamoyl}pyridazin-3-yl)-1,3-dihydro-2H-isoindole-2-carboxamide The title compound was prepared as described in Example 1C, substituting (R)-(tetrahydrofuran-2-yl)methamine for 3-phenylpropan-1-amine and 6-(isoindoline-2-carboxamido)pyridazine-3-carboxylic acid for 4-(isoindoline-2-carboxamido)benzoic acid. $^1$H NMR (300 MHz, DMSO-d$_6$) δ 10.02 (s, 1H), 8.85 (t, J=6.1 Hz, 1H), 8.32 (d, J=9.3 Hz, 1H), 8.12 (d, J=9.3 Hz, 1H), 7.41-7.28 (m, 4H), 5.00-4.71 (m, 4H), 4.04 (p, J=6.2 Hz, 1H), 3.85-3.74 (m, 1H), 3.70-3.58 (m, 1H), 3.44-3.33 (m, 3H), 1.99-1.71 (m, 2H), 1.69-1.54 (m, 1H); MS (ESI(+)) m/e 368 (M+H)$^+$.

Table 21.

The following Examples were essentially prepared as described in Example 1C, substituting N-(4-aminophenyl)-1H-pyrrolo[3,4-c]pyridine-2(3H)-carboxamide for 3-phenylpropan-1-amine and the appropriate carboxylic acid for 4-(isoindoline-2-carboxamido)benzoic acid.

| Ex | Name | $^1$H NMR | MS |
|---|---|---|---|
| 1363 | N-{4-[(3-ethoxypropanoyl)amino]phenyl}-1,3-dihydro-2H-pyrrolo[3,4-c]pyridine-2-carboxamide | $^1$H NMR (400 MHz, DMSO/D$_2$O, 90° C.) δ 8.71 (s, 1H), 8.61 (d, J = 5.4 Hz, 1H), 7.70 (d, J = 5.5 Hz, 1H), 7.44 (m, 4H), 4.89 (m, 4H), 3.68 (t, J = 4.7 Hz, 2H), 3.47 (q, J = 7.0 Hz, 2H), 2.52 (m, 2H), 1.11 (t, J = 7.0 Hz, 3H) | (APCI (+)) m/e 355 (M + H)$^+$ |
| 1364 | N-(4-{[(1-acetylpiperidin-4-yl)carbonyl]amino}phenyl)-1,3-dihydro-2H-pyrrolo[3,4-c]pyridine-2-carboxamide | $^1$H NMR (400 MHz, DMSO/D$_2$O, 90° C.) δ 8.73 (s, 1H), 8.62 (d, J = 5.46 Hz, 1H), 7.75 (m, 1H), 7.41 (m, 4H), 4.91 (m, 4H), 4.13 (m, 2H), 2.95 (m, 2H), 2.60 (m, 1H), 1.99 (m, 3H), 1.84 (m, 2H), 1.52 (m, 2H) | (APCI (+)) m/e 408 (M + H)$^+$ |
| 1365 | N-{4-[(ethoxyacetyl)amino]phenyl}-1,3-dihydro-2H-pyrrolo[3,4-c]pyridine-2-carboxamide | $^1$H NMR (400 MHz, DMSO/D$_2$O, 90° C.) δ 8.69 (s, 1H), 8.59 (d, J = 5.4 Hz, 1H), 7.66 (d, J = 5.5 Hz, 1H), 7.48 (m, 4H), 4.89 (bs, 4H), 4.00 (s, 2H), 3.60 (q, J = 7.0 Hz, 2H), 1.21 (t, J = 6.9 Hz, 3H) | (APCI (+)) m/e 341 (M + H)$^+$ |
| 1366 | N-{4-[(tetrahydrofuran-2-ylcarbonyl)amino]phenyl}-1,3-dihydro-2H-pyrrolo[3,4-c]pyridine-2-carboxamide | $^1$H NMR (400 MHz, DMSO/D$_2$O, 90° C.) δ 8.70 (s, 1H), 8.60 (d, J = 5.4 Hz, 1H), 7.69 (d, J = 5.5 Hz, 1H), 7.48 (m, 4H), 4.89 (m, 4H), 4.35 (dd, J = 8.1, 5.6 Hz, 1H), 4.00 (m, 1H), 3.83 (dt, J = 8.1, 6.7 Hz, 1H), 2.92 (m, 1H), 2.71 (s, 1H), 2.23 (m, 1H), 2.00 (m, 1H), 1.92 (m, 2H) | (APCI (+)) m/e 353 (M + H)$^+$ |
| 1367 | N-{4-[(tetrahydrofuran-3-ylcarbonyl)amino]phenyl}-1,3-dihydro-2H-pyrrolo[3,4-c]pyridine-2-carboxamide | $^1$H NMR (400 MHz, DMSO/D$_2$O, 90° C.) δ 8.73 (m, 1H), 8.61 (m, 1H), 7.70 (m, 1H), 7.43 (m, 4H), 4.90 (d, J = 8.2 Hz, 4H), 3.93 (m, 1H), 3.76 (m, 3H), 3.13 (m, 1H), 2.10 (q, J = 7.2 Hz, 2H) | (APCI (+)) m/e 353 (M + H)$^+$ |
| 1368 | N-{4-[(cyclopentylcarbonyl)amino]phenyl}-1,3-dihydro-2H-pyrrolo[3,4-c]pyridine-2-carboxamide | $^1$H NMR (400 MHz, DMSO/D$_2$O, 90° C.) δ 8.67 (s, 1H), 8.57 (d, J = 5.3 Hz, 1H), 7.62 (d, J = 5.4 Hz, 1H), 7.44 (m, 4H), 4.87 (s, 4H), 2.77 (m, 1H), 1.70 (m, 8H) | (APCI (+)) m/e 351 (M + H)$^+$ |
| 1370 | N-{4-[(bicyclo[2.2.1]hept-2-ylacetyl)amino]phenyl}-1,3-dihydro-2H-pyrrolo[3,4-c]pyridine-2-carboxamide | $^1$H NMR (400 MHz, DMSO/D$_2$O, 90° C.) δ 8.66 (s, 1H), 8.56 (d, J = 5.3 Hz, 1H), 7.60 (d, J = 5.2 Hz, 1H), 7.43 (m, 4H), 4.86 (s, 4H), 2.25 (dd, J = 14.1, 7.8 Hz, 1H), 2.20 (s, 1H), 2.12 (dd, J = 14.0, 7.6 Hz, 1H), 1.98 (d, J = 17.2 Hz, 1H), 1.90 (s, 1H), 1.41 (m, 4H), 1.14 (m, 4H) | (APCI (+)) m/e 391 (M + H)$^+$ |
| 1371 | N-{4-[(1,3-thiazol-5-ylcarbonyl)amino]phenyl}-1,3-dihydro-2H-pyrrolo[3,4-c]pyridine-2-carboxamide | $^1$H NMR (400 MHz, DMSO/D$_2$O, 90° C.) δ 9.20 (s, 1H), 8.67 (s, 1H), 8.60 (d, J = 5.3 Hz, 1H), 7.61 (d, J = 5.3 Hz, 4H), 7.55 (m, 4H) | (APCI (+)) m/e 366 (M + H)$^+$ |
| 1372 | N-(4-{[(4-oxo-4,5,6,7-tetrahydro-1-benzofuran-3-yl)carbonyl]amino}phenyl)-1,3-dihydro-2H-pyrrolo[3,4-c]pyridine-2-carboxamide | $^1$H NMR (400 MHz, DMSO/D$_2$O, 90° C.) δ 8.65 (s, 1H), 8.55 (d, J = 5.2 Hz, 1H), 8.26 (d, J = 14.4 Hz, 1H), 7.55 (m, 5H), 4.86 (s, 4H), 2.96 (m, 2H), 2.64 (m, 2H), 2.18 (m, 2H) | (APCI (+)) m/e 417 (M + H)$^+$ |

Example 1369

N-{7-oxo-7-[(3-phenylpropyl)amino]heptyl}-1,3-dihydro-2H-isoindole-2-carboxamide The title compound was prepared as described in Example 1C, substituting 7-(isoindoline-2-carboxamido)heptanoic acid for 4-(isoindoline-2-carboxamido)benzoic acid.

Example 1373

N-(4-{2-[(3-methylbutanoyl)amino]ethyl}phenyl)-1,3-dihydro-2H-isoindole-2-carboxamide

Example 1373A

N-(4-(2-aminoethyl)phenyl)isoindoline-2-carboxamide

The title compound was prepared as described in Example 2D, substituting tert-butyl (2-{4-[(1,3-dihydro-2H-isoindol-2-ylcarbonyl)amino]phenyl}ethyl)carbamate for tert-butyl 4-((4-(5-fluoroisoindoline-2-carboxamido)benzamido)methyl)benzylcarbamate.

Example 1373B

N-(4-{2-[(3-methylbutanoyl)amino]ethyl}phenyl)-1,3-dihydro-2H-isoindole-2-carboxamide The title compound was prepared as described in Example 1C, substituting N-(4-(2-aminoethyl)phenyl)isoindoline-2-carboxamide for 3-phenylpropan-1-amine and 3-methylbutanoic acid for 4-(isoindoline-2-carboxamido)benzoic acid. $^1$H NMR (400 MHz, DMSO-$d_6$, Temp=90° C.) δ 7.50-7.40 (m, 2H), 7.40-7.24 (m, 4H), 7.13-7.02 (m, 2H), 4.76 (s, 4H), 2.68 (t, J=7.3 Hz, 2H), 2.07-1.84 (m, 3H), 0.95-0.76 (m, 6H). MS (ESI (+)) m/e 366 (M+H)$^+$.

Table 22.

The following Examples were essentially prepared as described in Example 1C, substituting N-(4-(2-aminoethyl)phenyl)isoindoline-2-carboxamide for 3-phenylpropan-1-amine and the appropriate carboxylic acid for 4-(isoindoline-2-carboxamido)benzoic acid.

| Ex | Name | $^1$H NMR | MS |
|---|---|---|---|
| 1374 | N-(4-{2-[(4-methylpentanoyl)amino]ethyl}phenyl)-1,3-dihydro-2H-isoindole-2-carboxamide | $^1$H NMR (400 MHz, DMSO-$d_6$, Temp = 90° C.) δ 7.44 (t, J = 8.2 Hz, 2H), 7.38-7.18 (m, 4H), 7.18-6.99 (m, 2H), 4.76 (s, 4H), 2.78-2.60 (m, 2H), 2.13-1.99 (m, 2H), 1.58-1.33 (m, 3H), 0.90-0.79 (m, 6H) | (ESI (+)) m/e 380 (M + H)$^+$ |
| 1375 | N-(4-{2-[(ethoxyacetyl)amino]ethyl}phenyl)-1,3-dihydro-2H-isoindole-2-carboxamide | $^1$H NMR (400 MHz, DMSO-$d_6$, Temp = 90° C.) δ 8.07-7.98 (m, 1H), 7.50-7.25 (m, 7H), 7.11 (t, J = 6.6 Hz, 2H), 4.76 (s, 4H), 3.80 (s, 2H), 3.55-3.41 (m, 2H), 3.41-3.33 (m, 2H), 2.78-2.64 (m, 2H), 1.19-1.07 (m, 3H) | (ESI (+)) m/e 368 (M + H)$^+$ |
| 1376 | N-[4-(2-{[(2-methoxyethoxy)acetyl]amino}ethyl)phenyl]-1,3-dihydro-2H-isoindole-2-carboxamide | $^1$H NMR (400 MHz, DMSO-$d_6$, Temp = 90° C.) δ 7.45 (d, J = 8.4 Hz, 2H), 7.40-7.25 (m, 4H), 7.20-6.98 (m, 2H), 4.76 (s, 4H), 3.85 (s, 2H), 3.67-3.51 (m, 2H), 3.51-3.42 (m, 2H), 3.41-3.33 (m, 2H), 3.28 (s, 5H), 2.76-2.64 (m, 2H) | (ESI (+)) m/e 398 (M + H)$^+$ |
| 1377 | N-(4-{2-[(tetrahydrofuran-2-ylcarbonyl)amino]ethyl}phenyl)-1,3-dihydro-2H-isoindole-2-carboxamide | $^1$H NMR (400 MHz, DMSO-$d_6$, Temp = 90° C.) δ 7.52-7.37 (m, 2H), 7.37-7.21 (m, 4H), 7.10 (t, J = 7.3 Hz, 2H), 4.76 (s, 4H), 4.28-4.03 (m, 1H), 3.89-3.78 (m, 1H), 3.80-3.65 (m, 1H), 3.53-3.31 (m, 2H), 2.75-2.60 (m, 2H), 2.20-2.02 (m, 1H), 1.94-1.64 (m, 3H) | (ESI (+)) m/e 380 (M + H)$^+$ |
| 1378 | N-(4-{2-[(cyclopentylcarbonyl)amino]ethyl}phenyl)-1,3-dihydro-2H-isoindole-2-carboxamide | $^1$H NMR (400 MHz, DMSO-$d_6$, Temp = 90° C.) δ 7.43 (d, J = 8.5 Hz, 2H), 7.37-7.21 (m, 4H), 7.09 (d, J = 8.4 Hz, 2H), 4.76 (s, 4H), 2.68 (t, J = 7.3 Hz, 2H), 1.61 (t, J = 44.5 Hz, 8H) | (ESI (+)) m/e 378 (M + H)$^+$ |
| 1379 | N-(4-{2-[(cyclopentylacetyl)amino]ethyl}phenyl)-1,3-dihydro-2H-isoindole-2-carboxamide | $^1$H NMR (400 MHz, DMSO-$d_6$, Temp = 90° C.) δ 7.43 (dd, J = 6.3, 4.5 Hz, 2H), 7.37-7.24 (m, 4H), 7.09 (d, J = 8.4 Hz, 2H), 4.76 (s, 4H), 2.67 (dd, J = 9.4, 5.3 Hz, 2H), 2.23-1.94 (m, 4H), 1.76-1.42 (m, 6H), 1.22-1.05 (m, 2H) | (ESI (+)) m/e 392 (M + H)$^+$ |
| 1380 | N-{4-[2-(benzoylamino)ethyl]phenyl}-1,3-dihydro-2H-isoindole-2-carboxamide | $^1$H NMR (400 MHz, DMSO-$d_6$, Temp = 90° C.) δ 7.82-7.73 (m, 2H), 7.56-7.40 (m, 5H), 7.37-7.25 (m, 4H), 7.20-7.07 (m, 2H), 4.76 (s, 4H), 3.51 (t, J = 7.4 Hz, 2H), 2.93-2.67 (m, 2H) | (ESI (+)) m/e 386 (M + H)$^+$ |
| 1381 | N-(4-{2-[(tetrahydro-2H-pyran-4-ylcarbonyl)amino]ethyl}phenyl)-1,3-dihydro-2H-isoindole-2-carboxamide | $^1$H NMR (400 MHz, DMSO-$d_6$, Temp = 90° C.) δ 7.49-7.38 (m, 2H), 7.37-7.24 (m, 4H), 7.09 (d, J = 8.4 Hz, 2H), 4.76 (s, 4H), 3.90-3.74 (m, 2H), 3.37-3.30 (m, 2H), 2.68 (t, J = 7.3 Hz, 2H), 2.39-2.23 (m, 1H), 1.66-1.48 (m, 4H) | (ESI (+)) m/e 394 (M + H)$^+$ |
| 1382 | N-(4-{2-[(tetrahydro-2H-pyran-4-ylacetyl)amino]ethyl}phenyl)-1,3-dihydro-2H-isoindole-2-carboxamide | $^1$H NMR (400 MHz, DMSO-$d_6$, Temp = 90° C.) δ 7.43 (t, J = 5.4 Hz, 2H), 7.40-7.24 (m, 4H), 7.09 (d, J = 8.4 Hz, 2H), 4.76 (s, 4H), 3.85-3.68 (m, 2H), 3.28-3.24 (m, 4H), 2.68 (t, J = 7.3 Hz, 2H), 2.01 (d, J = 7.1 Hz, 2H), 1.94-1.76 (m, 1H), 1.59-1.42 (m, 2H), 1.29-1.03 (m, 2H) | (ESI (+)) m/e 408 (M + H)$^+$ |

-continued

| Ex | Name | ¹H NMR | MS |
|---|---|---|---|
| 1383 | N-(4-{2-[(tetrahydrofuran-3-ylacetyl)amino]ethyl}-phenyl)-1,3-dihydro-2H-isoindole-2-carboxamide | ¹H NMR (400 MHz, DMSO-d₆, Temp = 90° C.) δ 7.53-7.35 (m, 3H), 7.42-7.22 (m, 4H), 7.09 (d, J = 8.4 Hz, 2H), 4.76 (s, 4H), 3.82-3.55 (m, 3H), 3.35-3.30 (m, 1H), 3.26 (dd, J = 7.1, 5.3 Hz, 2H), 2.68 (t, J = 7.3 Hz, 2H), 2.48-2.36 (m, 1H), 2.22-2.07 (m, 2H), 2.04-1.81 (m, 1H), 1.62-1.29 (m, 1H) | (ESI (+)) m/e 394 (M + H)⁺ |

Example 1404

N-(4-{[1-(2-cyclopropylethyl)piperidin-4-yl]oxy}phenyl)-1,3-dihydro-2H-pyrrolo[3,4-c]pyridine-2-carboxamide The title compound was prepared as described in Example 429, substituting 2-cyclopropylacetaldehyde for isobutyraldehyde and N-(4-(piperidin-4-yloxy)phenyl)-1H-pyrrolo[3,4-c]pyridine-2(3H)-carboxamide for N-(4-(1,2,3,6-tetrahydropyridin-4-yl)phenyl)isoindoline-2-carboxamide. ¹H NMR (400 MHz, Pyridine-d₅. Temp=90° C.) δ ppm 8.54-8.58 (m, 2H) 8.08 (s, 1H) 7.72-7.77 (m, 2H) 7.10 (d, J=4.88 Hz, 1H) 7.01 (d, J=9.16 Hz, 2H) 4.82-4.88 (m, 4H) 3.71 (s, 1H) 2.74-2.82 (m, 2H) 2.43-2.50 (m, 2H) 2.22-2.31 (m, 2H) 1.97 (s, 2H) 1.79-1.90 (m, 2H) 1.35-1.47 (m, 2H) 0.70 (s, 1H) 0.36-0.45 (m, 2H) 0.05 (q, J=4.78 Hz, 2H); MS (APCI(+)) m/e 407 (M+H)⁺.

Example 1405

N-(4-{[1-(2-cyclopentylethyl)piperidin-4-yl]oxy}phenyl)-1,3-dihydro-2H-pyrrolo[3,4-c]pyridine-2-carboxamide The title compound was prepared as described in Example 429, substituting 2-cyclopentylacetaldehyde for isobutyraldehyde and N-(4-(piperidin-4-yloxy)phenyl)-1H-pyrrolo[3,4-c]pyridine-2(3H)-carboxamide for N-(4-(1,2,3,6-tetrahydropyridin-4-yl)phenyl)isoindoline-2-carboxamide. ¹H NMR (400 MHz, Pyridine-d₅. Temp=90° C.) δ ppm 8.54-8.58 (m, 2H) 8.08 (s, 1H) 7.72-7.78 (m, 2H) 7.10 (d, J=4.88 Hz, 1H) 7.00-7.04 (m, 2H) 4.82-4.90 (m, 4H) 4.21-4.31 (m, 1H) 2.73-2.83 (m, 2H) 2.34-2.40 (m, 2H) 2.20-2.29 (m, 2H) 1.96-2.03 (m, 2H) 1.67-1.93 (m, 5H) 1.40-1.62 (m, 6H) 1.04-1.17 (m, 2H); MS (APCI(+)) m/e 435 (M+H)⁺.

Example 1406

N-(4-{[1-(2-methylbutyl)piperidin-4-yl]oxy}phenyl)-1,3-dihydro-2H-pyrrolo[3,4-c]pyridine-2-carboxamide The title compound was prepared as described in Example 429, substituting 2-methylbutanal for isobutyraldehyde and N-(4-(piperidin-4-yloxy)phenyl)-1H-pyrrolo[3,4-c]pyridine-2(3H)-carboxamide for N-(4-(1,2,3,6-tetrahydropyridin-4-yl)phenyl)isoindoline-2-carboxamide. ¹H NMR (400 MHz, Pyridine-d₅. Temp=90° C.) δ ppm 8.52-8.58 (m, 2H) 8.08 (s, 1H) 7.74 (d, J=8.85 Hz, 2H) 7.10 (d, J=4.58 Hz, 1H) 6.97-7.05 (m, 2H) 4.84 (d, J=6.71 Hz, 4H) 2.72 (d, J=10.68 Hz, 2H) 2.13-2.26 (m, 3H) 2.01-2.07 (m, 2H) 1.91-2.00 (m, 2H) 1.83 (s, 2H) 1.54 (s, 2H) 1.14 (s, 1H) 0.81-0.95 (m, 6H); MS (APCI(+)) m/e 409 (M+H)⁺.

Example 1407

N-(4-{[1-(tetrahydrofuran-3-ylmethyl)piperidin-4-yl]oxy}phenyl)-1,3-dihydro-2H-pyrrolo[3,4-c]pyridine-2-carboxamide The title compound was prepared as described in Example 429, substituting tetrahydrofuran-3-carbaldehyde for isobutyraldehyde and N-(4-(piperidin-4-yloxy)phenyl)-1H-pyrrolo[3,4-c]pyridine-2(3H)-carboxamide for N-(4-(1,2,3,6-tetrahydropyridin-4-yl)phenyl)isoindoline-2-carboxamide. ¹H NMR (400 MHz, Pyridine-d₅. Temp=90° C.) δ ppm 8.53-8.58 (m, 1H) 8.08 (s, 1H) 7.70-7.77 (m, 2H) 7.10 (d, J=5.19 Hz, 1H) 7.01 (d, J=8.85 Hz, 2H) 4.84 (d, J=7.63 Hz, 4H) 4.19-4.27 (m, 1H) 3.75-3.90 (m, 2H) 3.67-3.72 (m, 1H) 3.56 (dd, J=8.55, 5.80 Hz, 1H) 2.65-2.82 (m, 2H) 2.31-2.45 (m, 1H) 2.15-2.31 (m, 4H) 1.71-2.00 (m, 5H) 1.48-1.59 (m, 1H); MS (APCI(+)) m/e 423 (M+H)⁺.

Example 1408

N-(4-{[1-(3,3-dimethylbutyl)piperidin-4-yl]oxy}phenyl)-1,3-dihydro-2H-pyrrolo[3,4-c]pyridine-2-carboxamide The title compound was prepared as described in Example 429, substituting 3,3-dimethylbutanal for isobutyraldehyde and N-(4-(piperidin-4-yloxy)phenyl)-1H-pyrrolo[3,4-c]pyridine-2(3H)-carboxamide for N-(4-(1,2,3,6-tetrahydropyridin-4-yl)phenyl)isoindoline-2-carboxamide. ¹H NMR (400 MHz, Pyridine-d₅. Temp=90° C.) δ ppm 8.52-8.58 (m, 2H) 8.09 (s, 1H) 7.71-7.78 (m, 2H) 7.10 (d, J=4.88 Hz, 1H) 6.99-7.04 (m, 2H) 4.84 (dd, J=8.39, 1.68 Hz, 4H) 3.85 (d, J=13.43 Hz, 1H) 2.75-2.85 (m, 2H) 2.38-2.47 (m, 2H) 2.21-2.34 (m, 2H) 1.98 (d, J=2.14 Hz, 2H) 1.78-1.91 (m, 2H) 1.39-1.49 (m, 2H) 0.84-0.92 (m, 9H); MS (APCI(+)) m/e 423 (M+H)⁺.

Example 1409

N-(4-{[1-(cyclohexylmethyl)piperidin-4-yl]oxy}phenyl)-1,3-dihydro-2H-pyrrolo[3,4-c]pyridine-2-carboxamide The title compound was prepared as described in Example 429, substituting cyclohexanecarbaldehyde for isobutyraldehyde and N-(4-(piperidin-4-yloxy)phenyl)-1H-pyrrolo[3,4-c]pyridine-2(3H)-carboxamide for N-(4-(1,2,3,6-tetrahydropyridin-4-yl)phenyl)isoindoline-2-carboxamide. ¹H NMR (400 MHz, Pyridine-d₅. Temp=90° C.) δ ppm 8.53-8.57 (m, 2H) 8.08 (s, 1H) 7.69-7.77 (m, 2H) 7.10 (s, 1H) 6.97-7.04 (m, 2H) 4.82-4.87 (m, 4H) 4.20-4.27 (m, 1H) 2.73 (t, J=10.68 Hz, 2H) 2.17-2.26 (m, 2H) 2.13 (d, J=7.02 Hz, 2H) 1.93-2.01 (m,

Example 1410

N-(4-{[1-(3-methylbutyl)piperidin-4-yl]oxy}phenyl)-1,3-dihydro-2H-pyrrolo[3,4-c]pyridine-2-carboxamide The title compound was prepared as described in Example 429, substituting 3-methylbutanal for isobutyraldehyde and N-(4-(piperidin-4-yloxy)phenyl)-1H-pyrrolo[3,4-c]pyridine-2(3H)-carboxamide for N-(4-(1,2,3,6-tetrahydropyridin-4-yl)phenyl)isoindoline-2-carboxamide. $^1$H NMR (400 MHz, Pyridine-$d_5$. Temp=90° C.) δ ppm 8.53-8.57 (m, 2H) 8.09 (s, 1H) 7.70-7.78 (m, 2H) 7.10 (d, J=5.19 Hz, 1H) 6.98-7.04 (m, 2H) 4.79-4.89 (m, 4H) 4.26 (d, J=3.66 Hz, 1H) 2.72-2.83 (m, 2H) 2.34-2.41 (m, 2H) 2.21-2.30 (m, 2H) 1.96-2.03 (m, 2H) 1.79-1.91 (m, 2H) 1.54-1.68 (m, 1H) 1.35-1.44 (m, 2H) 0.86-0.90 (m, 6H); MS (APCI(+)) m/e 408 (M+H)$^+$.

Example 1411

N-(4-{[1-(cyclopentylmethyl)piperidin-4-yl]oxy}phenyl)-1,3-dihydro-2H-pyrrolo[3,4-c]pyridine-2-carboxamide The title compound was prepared as described in Example 429, substituting cyclopentanecarbaldehyde for isobutyraldehyde and N-(4-(piperidin-4-yloxy)phenyl)-1H-pyrrolo[3,4-c]pyridine-2(3H)-carboxamide for N-(4-(1,2,3,6-tetrahydropyridin-4-yl)phenyl)isoindoline-2-carboxamide. $^1$H NMR (400 MHz, Pyridine-$d_5$. Temp=90° C.) δ ppm 8.53-8.57 (m, 2H) 8.08 (s, 1H) 7.70-7.77 (m, 2H) 7.10 (d, J=4.88 Hz, 1H) 6.97-7.05 (m, 2H) 4.84 (dd, J=8.54, 1.53 Hz, 4H) 4.23-4.27 (m, 1H) 2.75 (d, J=10.99 Hz, 2H) 2.18-2.29 (m, 4H) 2.04 (s, 1H) 1.94-2.02 (m, 2H) 1.77-1.90 (m, 2H) 1.65-1.76 (m, 2H) 1.42-1.59 (m, 4H) 1.17-1.32 (m, 2H); MS (APCI(+)) m/e 420 (M+H)$^+$.

Example 1412

N-(4-{[1-(tetrahydrofuran-2-ylmethyl)piperidin-4-yl]oxy}phenyl)-1,3-dihydro-2H-pyrrolo[3,4-c]pyridine-2-carboxamide The title compound was prepared as described in Example 429, substituting tetrahydrofuran-2-carbaldehyde for isobutyraldehyde and N-(4-(piperidin-4-yloxy)phenyl)-1H-pyrrolo[3,4-c]pyridine-2(3H)-carboxamide for N-(4-(1,2,3,6-tetrahydropyridin-4-yl)phenyl)isoindoline-2-carboxamide. $^1$H NMR (400 MHz, Pyridine-$d_5$. Temp=90° C.) δ ppm 8.53-8.59 (m, 2H) 8.07 (s, 1H) 7.73 (d, J=9.16 Hz, 2H) 7.10 (d, J=5.49 Hz, 1H) 6.97-7.02 (m, 2H) 4.80-4.87 (m, 4H) 4.03 (d, J=11.60 Hz, 1H) 3.77-3.84 (m, 1H) 3.61-3.69 (m, 1H) 2.88 (d, J=41.81 Hz, 2H) 2.25-2.63 (m, 4H) 1.97 (s, 2H) 1.77-1.91 (m, 4H) 1.64-1.76 (m, 2H) 1.44-1.58 (m, 1H); MS (APCI(+)) m/e 423 (M+H)$^+$.

Example 1413

N-(4-{[1-(2-methylpropyl)piperidin-4-yl]oxy}phenyl)-1,3-dihydro-2H-pyrrolo[3,4-c]pyridine-2-carboxamide The title compound was prepared as described in Example 429, substituting isobutyraldehyde for isobutyraldehyde and N-(4-(piperidin-4-yloxy)phenyl)-1H-pyrrolo[3,4-c]pyridine-2(3H)-carboxamide for N-(4-(1,2,3,6-tetrahydropyridin-4-yl)phenyl)isoindoline-2-carboxamide. $^1$H NMR (400 MHz, Pyridine-$d_5$. Temp=90° C.) δ ppm 8.49-8.60 (m, 2H) 8.09 (s, 1H) 7.68-7.80 (m, 2H) 7.10 (d, J=5.19 Hz, 1H) 6.96-7.04 (m, 2H) 4.85 (s, 4H) 4.21-4.28 (m, 1H) 2.65-2.79 (m, 2H) 2.13-2.24 (m, 2H) 2.06 (m, 2H) 1.98 (s, 2H) 1.77-1.88 (m, 2H) 1.67-1.77 (m, 1H) 0.89 (d, J=6.71 Hz, 6H); MS (APCI(+)) m/e 395 (M+H)$^+$.

Example 1414

N-(4-{[1-(butylsulfonyl)piperidin-4-yl]oxy}phenyl)-1,3-dihydro-2H-pyrrolo[3,4-c]pyridine-2-carboxamide The title compound was prepared as described in Example 883, substituting N-(4-(piperidin-4-yloxy)phenyl)-1H-pyrrolo[3,4-c]pyridine-2(3H)-carboxamide for N-(4-aminophenyl)isoindoline-2-carboxamide and 1-butylsulfonyl chloride for (3-methoxyphenyl)methanesulfonyl chloride. $^1$H NMR (400 MHz, DMSO-$D_2$O, Temp=90° C.) δ ppm 8.59 (s, 1H) 8.49 (d, J=4.88 Hz, 1H) 7.36-7.48 (m, 3H) 6.90 (d, J=8.85 Hz, 2H) 4.80 (d, J=6.10 Hz, 4H) 4.39-4.50 (m, 1H) 3.41-3.49 (m, 2H) 3.13-3.20 (m, 2H) 2.99-3.06 (m, 2H) 1.94-2.01 (m, 2H) 1.63-1.76 (m, 4H) 1.37-1.49 (m, 2H) 0.91 (t, J=7.48 Hz, 3H); MS (APCI(+)) m/e 459 (M+H)$^+$.

Example 1415

N-(4-{[1-(cyclopropylsulfonyl)piperidin-4-yl]oxy}phenyl)-1,3-dihydro-2H-pyrrolo[3,4-c]pyridine-2-carboxamide The title compound was prepared as described in Example 883, substituting N-(4-(piperidin-4-yloxy)phenyl)-1H-pyrrolo[3,4-c]pyridine-2(3H)-carboxamide for N-(4-aminophenyl)isoindoline-2-carboxamide and cyclopropylsulfonyl chloride for (3-methoxyphenyl)methanesulfonyl chloride. $^1$H NMR (400 MHz, DMSO-$D_2$O, Temp=90° C.) δ ppm 8.57 (s, 1H) 8.48 (d, J=4.88 Hz, 1H) 7.40 (d, J=8.54 Hz, 3H) 6.90 (d, J=8.85 Hz, 2H) 4.79 (d, J=8.24 Hz, 4H) 4.39-4.49 (m, 1H) 3.44-3.51 (m, 2H) 3.17-3.23 (m, 2H) 2.54-2.58 (m, 1H) 1.95-2.03 (m, 2H) 1.68-1.78 (m, 2H) 0.91-1.07 (m, 4H); MS (APCI(+)) m/e 442 (M+H)$^+$.

Example 1416

N-(4-{[1-(phenylsulfonyl)piperidin-4-yl]oxy}phenyl)-1,3-dihydro-2H-pyrrolo[3,4-c]pyridine-2-carboxamide The title compound was prepared as described in Example 883, substituting N-(4-(piperidin-4-yloxy)phenyl)-1H-pyrrolo[3,4-c]pyridine-2(3H)-carboxamide for N-(4-aminophenyl)isoindoline-2-carboxamide and phenylsulfonyl chloride for (3-methoxyphenyl)methanesulfonyl chloride. $^1$H NMR (400 MHz, DMSO-$D_2$O, Temp=90° C.) δ ppm 8.59 (s, 1H) 8.49 (d, J=4.88 Hz, 1H) 7.77 (d, J=7.32 Hz, 2H) 7.71 (t, J=7.32 Hz, 1H) 7.65 (t, J=7.32 Hz, 2H) 7.44 (d, J=4.88 Hz, 1H) 7.35 (d, J=8.85 Hz, 2H) 6.79 (d, J=9.16 Hz, 2H) 4.79 (d, J=4.27 Hz, 4H) 4.29-4.37 (m, 1H) 3.22-3.25 (m, 2H) 2.92-3.06 (m, 2H) 1.87-2.04 (m, 2H) 1.61-1.79 (m, 2H); MS (APCI(+)) m/e 479 (M+H)$^+$.

Example 1417

N-[4-({1-[(4-fluorophenyl)sulfonyl]piperidin-4-yl}oxy)phenyl]-1,3-dihydro-2H-pyrrolo[3,4-c]pyridine-2-carboxamide The title compound was prepared as described in Example 883, substituting N-(4-(piperidin-4-yloxy)phenyl)-1H-pyrrolo[3,4-c]pyridine-2(3H)-carboxamide for N-(4-aminophenyl)isoindoline-2-carboxamide and (4-fluorophenyl)sulfonyl chloride for (3-methoxyphenyl)methanesulfonyl chloride. $^1$H NMR (400 MHz, DMSO-D$_2$O, Temp=90° C.) δ ppm 8.58 (s, 1H) 8.49 (d, J=4.88 Hz, 1H) 7.84 (dd, J=8.85, 5.19 Hz, 2H) 7.40-7.49 (m, 3H) 7.36 (d, J=8.85 Hz, 2H) 6.80 (d, J=8.85 Hz, 2H) 4.79 (d, J=4.88 Hz, 4H) 4.28-4.41 (m, 1H) 3.21-3.26 (m, 2H) 2.94-3.05 (m, 2H) 1.89-2.02 (m, 2H) 1.62-1.76 (m, 2H); MS (APCI(+)) m/e 497 (M+H)$^+$.

Example 1418

N-(4-{[1-(ethylsulfonyl)piperidin-4-yl]oxy}phenyl)-1,3-dihydro-2H-pyrrolo[3,4-c]pyridine-2-carboxamide The title compound was prepared as described in Example 883, substituting N-(4-(piperidin-4-yloxy)phenyl)-1H-pyrrolo[3,4-c]pyridine-2(3H)-carboxamide for N-(4-aminophenyl)isoindoline-2-carboxamide and ethylsulfonyl chloride for (3-methoxyphenyl)methanesulfonyl chloride. $^1$H NMR (400 MHz, DMSO-D$_2$O, Temp=90° C.) δ ppm 8.58 (s, 1H) 8.48 (d, J=5.19 Hz, 1H) 7.40 (d, J=8.85 Hz, 3H) 6.90 (d, J=8.85 Hz, 2H) 4.79 (d, J=7.32 Hz, 4H) 4.39-4.48 (m, 1H) 3.41-3.49 (m, 2H) 3.14-3.22 (m, 2H) 3.05 (q, J=7.43 Hz, 2H) 1.94-2.03 (m, 2H) 1.64-1.78 (m, 2H) 1.24 (t, J=7.32 Hz, 3H); MS (APCI(+)) m/e 431 (M+H)$^+$.

Example 1419

N-(4-{[1-(propan-2-ylsulfonyl)piperidin-4-yl]oxy}phenyl)-1,3-dihydro-2H-pyrrolo[3,4-c]pyridine-2-carboxamide The title compound was prepared as described in Example 883, substituting N-(4-(piperidin-4-yloxy)phenyl)-1H-pyrrolo[3,4-c]pyridine-2(3H)-carboxamide for N-(4-aminophenyl)isoindoline-2-carboxamide and isopropylsulfonyl chloride for (3-methoxyphenyl)methanesulfonyl chloride. $^1$H NMR (400 MHz, DMSO-D$_2$O, Temp=90° C.) δ ppm 8.59 (s, 1H) 8.49 (d, J=5.19 Hz, 1H) 7.36-7.47 (m, 3H) 6.89 (d, J=8.85 Hz, 2H) 4.80 (d, J=5.49 Hz, 4H) 4.40-4.49 (m, 1H) 3.46-3.55 (m, 2H) 3.33-3.36 (m, 1H) 3.15-3.24 (m, 2H) 1.93-2.01 (m, 2H) 1.62-1.74 (m, 2H) 1.25 (d, J=6.71 Hz, 6H); MS (APCI(+)) m/e 445 (M+H)$^+$.

Example 1420

N-(4-{[1-(benzylsulfonyl)piperidin-4-yl]oxy}phenyl)-1,3-dihydro-2H-pyrrolo[3,4-c]pyridine-2-carboxamide The title compound was prepared as described in Example 883, substituting N-(4-(piperidin-4-yloxy)phenyl)-1H-pyrrolo[3,4-c]pyridine-2(3H)-carboxamide for N-(4-aminophenyl)isoindoline-2-carboxamide and benzylsulfonyl chloride for (3-methoxyphenyl)methanesulfonyl chloride. $^1$H NMR (400 MHz, DMSO-D$_2$O, Temp=90° C.) δ ppm 8.58 (s, 1H) 8.48 (d, J=4.88 Hz, 1H) 7.31-7.46 (m, 8H) 6.87 (d, J=9.16 Hz, 2H) 4.79 (d, J=7.02 Hz, 4H) 4.38-4.44 (m, 1H) 4.36 (s, 2H) 3.34-3.38 (m, 2H) 3.07-3.16 (m, 2H) 1.82-1.90 (m, 2H) 1.57-1.71 (m, 2H); MS (APCI(+)) m/e 493 (M+H)$^+$.

Example 1421

N-(4-{[1-(propylsulfonyl)piperidin-4-yl]oxy}phenyl)-1,3-dihydro-2H-pyrrolo[3,4-c]pyridine-2-carboxamide The title compound was prepared as described in Example 883, substituting N-(4-(piperidin-4-yloxy)phenyl)-1H-pyrrolo[3,4-c]pyridine-2(3H)-carboxamide for N-(4-aminophenyl)isoindoline-2-carboxamide and 1-propylsulfonyl chloride for (3-methoxyphenyl)methanesulfonyl chloride. $^1$H NMR (400 MHz, DMSO-D$_2$O, Temp=90° C.) δ ppm 8.59 (s, 1H) 8.49 (d, J=4.88 Hz, 1H) 7.35-7.46 (m, 3H) 6.90 (d, J=8.85 Hz, 2H) 4.80 (d, J=5.80 Hz, 4H) 4.39-4.48 (m, 1H) 3.39-3.49 (m, 2H) 3.12-3.22 (m, 2H) 2.96-3.06 (m, 2H) 1.93-2.03 (m, 2H) 1.62-1.79 (m, 4H) 1.01 (t, J=7.48 Hz, 3H); MS (APCI(+)) m/e 445 (M+H)$^+$.

Example 1422

N-(4-{[1-(thiophen-2-ylsulfonyl)piperidin-4-yl]oxy}phenyl)-1,3-dihydro-2H-pyrrolo[3,4-c]pyridine-2-carboxamide The title compound was prepared as described in Example 883, substituting N-(4-(piperidin-4-yloxy)phenyl)-1H-pyrrolo[3,4-c]pyridine-2(3H)-carboxamide for N-(4-aminophenyl)isoindoline-2-carboxamide and thiophene-2-sulfonyl chloride for (3-methoxyphenyl)methanesulfonyl chloride. $^1$H NMR (400 MHz, DMSO-D$_2$O, Temp=90° C.) δ ppm 8.58 (s, 1H) 8.49 (d, J=5.19 Hz, 1H) 7.96 (d, J=4.27 Hz, 1H) 7.63 (d, J=3.05 Hz, 1H) 7.44 (d, J=4.88 Hz, 1H) 7.37 (d, J=8.85 Hz, 2H) 7.23-7.30 (m, 1H) 6.81 (d, J=8.85 Hz, 2H) 4.79 (d, J=4.88 Hz, 4H) 4.29-4.43 (m, 1H) 3.31-3.38 (m, 2H) 2.97-3.09 (m, 2H) 1.93-2.06 (m, 2H) 1.65-1.81 (m, 2H); MS (APCI(+)) m/e 485 (M+H)$^+$.

Example 1441 benzyl trans-3-[(1,3-dihydro-2H-pyrrolo[3,4-c]pyridin-2-ylcarbonyl)amino]cyclobutanecarboxylate

Example 1441A benzyl trans-3-(tert-butoxycarbonylamino)cyclobutanecarboxylate A suspension of trans-3-(tert-butoxycarbonylamino)cyclobutanecarboxylic acid (0.5 g, 2.323 mmol) and potassium carbonate (0.321 g, 2.323 mmol) in dimethylformamide (2.323 ml) was treated with (bromomethyl)benzene (0.401 g, 2.346 mmol) added from a syringe over 3 minutes. The reaction mixture was stirred at room temperature for 17 hours and water was added. The suspension was filtered and the solid collected was washed with water and dried under vacuum to give the title compound.

Example 1441B trans-benzyl 3-aminocyclobutanecarboxylate

The title compound was prepared as described in Example 2D, substituting benzyl trans-3-(tert-butoxycarbonylamino)

cyclobutanecarboxylate for tert-butyl 4-((4-(5-fluoroisoindoline-2 carboxamido)benzamido)methyl)benzylcarbamate.

Example 1441C benzyl trans-3-[(1,3-dihydro-2H-pyrrolo[3,4-c]pyridin-2-ylcarbonyl)amino]cyclobutanecarboxylate The title compound was prepared as described in Example 272B, substituting trans-benzyl 3-aminocyclobutanecarboxylate for 4-amino-N-propylbenzamide and 1,3-dihydro-2H-pyrrolo[3,4-c]pyridine for methyl isoindoline-5-carboxylate hydrochloride. $^1$H NMR (300 MHz, DMSO-d$_6$) δ ppm 8.56 (s, 1H), 8.47 (d, J=5.0 Hz, 1H), 7.43-7.31 (m, 6H), 6.68 (d, J=7.6 Hz, 1H), 5.14 (s, 2H), 4.65-4.58 (m, 4H), 4.41-4.29 (m, 1H), 3.11-2.99 (m, 1H), 2.46-2.25 (m, 4H); MS (ESI(+)) m/e 352 (M+H)$^+$.

Example 1452

N-(4-{3-[(3-methylbutanoyl)amino]oxetan-3-yl}phenyl)-1,3-dihydro-2H-pyrrolo[3,4-c]pyridine-2-carboxamide

Example 1452A 2-methyl-N-(oxetan-3-ylidene)propane-2-sulfinamide

To a 250 mL round-bottomed flask was added 2-methylpropane-2-sulfinamide (3.36 g, 27.8 mmol) followed by tetraethoxytitanium (11.64 ml, 55.5 mmol) to a tetrahydrofuran (69.4 ml) solution of oxetan-3-one (2 g, 27.8 mmol) at room temperature. The mixture was stirred at 50° C. for 5 hours, cooled and poured into brine. The suspension was filtered through a pad of diatomaceous earth eluting with ethyl acetate. The organics were combined, dried with sodium sulfate, filtered and concentrated under vacuum. The residue was purified by regular phase flash column chromatography to give the title compound.

Example 1452B

N-(3-(4-bromophenyl)oxetan-3-yl)-2-methylpropane-2-sulfinamide

To a 50 mL round-bottomed flask was added 1,4-dibromobenzene (2.85 g, 12.07 mmol) in tetrahydrofuran (40.2 ml). The solution was cooled to −78° C. and n-butyl lithium (4.51 ml, 11.26 mmol) was added dropwise. The mixture was stirred for 1 hour at −78° C. 2-methyl-N-(oxetan-3-ylidene) propane-2-sulfinamide (1.41 g, 8.05 mmol) was added as a tetrahydrofuran solution (ca 1 ml) and the reaction was stirred for 10 minutes and warmed to room temperature. Saturated ammonium chloride was added followed by water and dichloromethane. The aqueous layer was extracted twice with dichloromethane and the combined organics were dried with magnesium sulfate, filtered and concentrated under vacuum. The residue was purified by regular phase, flash column chromatography to give the title compound.

Example 1452C

N-(4-(3-(1,1-dimethylethylsulfinamido)oxetan-3-yl)phenyl)acetamide

To a 5 mL microwave tube was added N-(3-(4-bromophenyl)oxetan-3-yl)-2-methylpropane-2-sulfinamide (436 mg, 1.312 mmol), cesium carbonate (1283 mg, 3.94 mmol), and acetamide (116 mg, 1.968 mmol) in dioxane (6.5 ml). Xantphos (76 mg, 0.131 mmol) and tris(dibenzylideneacetone) dipalladium(O) (60.1 mg, 0.066 mmol) were added; the tube was flushed with nitrogen and capped. The mixture was heated at 100° C. for 45 minutes. Aqueous work up with dichloromethane extraction gave an organic layer that was dried with sodium sulfate, filtered and concentrated under vacuum. Regular phase chromatography provided the title compound.

Example 1452D

N-(3-(4-aminophenyl)oxetan-3-yl)-2-methylpropane-2-sulfinamide

Claisen's alkali (potassium hydroxide, 12.7 g in 9 ml water and 33 ml methanol) was added to N-(4-(3-(1,1-dimethylethylsulfinamido)oxetan-3-yl)phenyl)acetamide (300 mg, 0.966 mmol) and the reaction was stirred at 90° C. for 2 hours. The mixture was cooled to room temperature when water and ethyl acetate were added. The aqueous layer was extracted twice with ethyl acetate and the combined organics were dried with magnesium sulfate, filtered and concentrated under vacuum. The residue was purified by regular phase flash column chromatography to give the title compound.

Example 1452E

N-(4-(3-(1,1-dimethylethylsulfinamido)oxetan-3-yl)phenyl)-1H-pyrrolo[3,4-c]pyridine-2(3H)-carboxamide The title compound was prepared as described in Example 272B, substituting N-(3-(4-aminophenyl)oxetan-3-yl)-2-methylpropane-2-sulfinamide for 4-amino-N-propylbenzamide and 1,3-dihydro-2H-pyrrolo[3,4-c]pyridine for methyl isoindoline-5-carboxylate hydrochloride.

Example 1452F

N-(4-(3-amino oxetan-3-yl)phenyl)-1H-pyrrolo[3,4-c]pyridine-2(3H)-carboxamide

In a 20 mL vial was added N-(4-(3-(1,1-dimethylethylsulfinamido)oxetan-3-yl)phenyl)-1H-pyrrolo[3,4-c]pyridine-2 (3H)-carboxamide (253 mg, 0.610 mmol) and methanol (6.1 ml). 4N HCl in dioxane (229 µl, 0.916 mmol) was added and the reaction was stirred for 2 hours. The mixture was concentrated under vacuum to give the title compound which was used without further purification.

Example 1452G

N-(4-{3-[(3-methylbutanoyl)amino]oxetan-3-yl}phenyl)-1,3-dihydro-2H-pyrrolo[3,4-c]pyridine-2-carboxamide The title compound was prepared as described in Example 1C, substituting N-(4-(3-aminooxetan-3-yl)phenyl)-1H-pyrrolo[3,4-c]pyridine-2(3H)-carboxamide for 3-phenylpropan-1-amine and 3-methylbutanoic acid for 4-(isoindoline-2-carboxamido)benzoic acid. $^1$H NMR (300 MHz, DMSO-d$_6$) δ 8.84 (s, 1H), 8.61 (s, 1H), 8.50 (d, J=5.0 Hz, 1H), 8.44 (s, 1H), 7.54 (d, J=8.7 Hz, 2H), 7.43 (d, J=4.8 Hz, 1H), 7.36 (d, J=8.8

Hz, 2H), 4.81 (d, J=6.5 Hz, 6H), 4.69 (d, J=6.5 Hz, 2H), 2.10-1.87 (m, 3H), 0.90 (d, J=6.4 Hz, 6H); MS (ESI(+)) m/e 395 (M+H)+.

Example 1453 tert-butyl 4-({4-[(1,3-dihydro-2H-pyrrolo[3,4-c]pyridin-2-ylcarbonyl)amino]phenyl}sulfonyl)piperidine-1-carboxylate

Example 1453A tert-butyl 4-(4-aminophenylthio)piperidine-1-carboxylate

To a 100 mL round-bottomed flask was added 4-aminobenzenethiol (4.9 g, 39.1 mmol) and potassium carbonate (9.72 g, 70.3 mmol) in dimethylformamide (20 ml). tert-Butyl 4-(tosyloxy)piperidine-1-carboxylate (5 g, 14.07 mmol) was added and the reaction was stirred in a sealed flask at 70° C. for 20 hours. The mixture was cooled and filtered through a plug of silica gel with dichloromethane. The filtrate was concentrated under vacuum and chromatographed to give the title compound.

Example 1453B tert-butyl 4-(4-acetamidophenylthio)piperidine-1-carboxylate

To a 10 mL round-bottomed flask was added tert-butyl 4-(4-aminophenylthio)piperidine-1-carboxylate (100 mg, 0.324 mmol) and triethylamine (249 µl, 1.783 mmol) in dichloromethane (3242 µl). The mixture was cooled to −78° C. and acetyl chloride (115 µl, 1.621 mmol) was added. The solution was warmed to room temperature, stirred for 1 h and then diluted with water and additional dichloromethane. The aqueous phase was extracted twice with dichloromethane and the combined organics were dried with sodium sulfate, filtered and concentrated to give the title compound.

Example 1453C tert-butyl 4-(4-acetamidophenylsulfonyl)piperidine-1-carboxylate In a 10 mL round-bottomed flask was added tert-butyl 4-(4-acetamidophenylthio)piperidine-1-carboxylate (100 mg, 0.285 mmol) in dichloromethane (2.9 ml). The solution was cooled to −20° C. and mCPBA (192 mg, 0.856 mmol) was added. The reaction mixture was allowed to warm to room temperature and treated with 1N aqueous NaOH. The aqueous layer was extracted with dichloromethane and the combined organics were dried with sodium sulfate, filtered and concentrated to give the title compound.

Example 1453D tert-butyl 4-(4-aminophenylsulfonyl)piperidine-1-carboxylate

The title compound was prepared as described in Example 1452D, substituting tert-butyl 4-(4-acetamidophenylsulfonyl)piperidine-1-carboxylate for N-(4-(3-(1,1-dimethylethylsulfinamido)oxetan-3-yl)phenyl)acetamide.

Example 1453E tert-butyl 4-({4-[(1,3-dihydro-2H-pyrrolo[3,4-c]pyridin-2-ylcarbonyl)amino]phenyl}sulfonyl)piperidine-1-carboxylate The title compound was prepared as described in Example 272B, substituting tert-butyl 4-(4-aminophenylsulfonyl)piperidine-1-carboxylate for 4-amino-N-propylbenzamide and 1,3-dihydro-2H-pyrrolo[3,4-c]pyridine for methyl isoindoline-5-carboxylate. $^1$H NMR (300 MHz, DMSO-$d_6$) δ 8.95 (s, 1H), 8.62 (s, 1H), 8.51 (d, J=5.0 Hz, 1H), 7.90-7.83 (m, 2H), 7.76-7.69 (m, 2H), 7.44 (d, J=5.1 Hz, 1H), 4.93-4.76 (m, 4H), 4.09-3.93 (m, 2H), 2.84-2.56 (m, 1H), 1.83 (d, J=10.8 Hz, 1H), 1.48-1.16 (m, 6H); MS (ESI(+)) m/e 431 (M+H)+.

Example 1454

N-{4-[4-(propylcarbamoyl)piperidin-1-yl]phenyl}-1,3-dihydro-2H-pyrrolo[3,4-c]pyridine-2-carboxamide

Example 1454A 1-(4-(2,3-dihydro-1H-pyrrolo[3,4-c]pyridine-2-carboxamido)phenyl)piperidine-4-carboxylic acid The title compound was prepared as described in Example 1246, substituting methyl piperidine-4-carboxylate for methyl azetidine-3-carboxylate hydrochloride in Example 1246A.

Example 1454B

N-{4-[4-(propylcarbamoyl)piperidin-1-yl]phenyl}-1,3-dihydro-2H-pyrrolo[3,4-c]pyridine-2-carboxamide The title compound was prepared as described in Example 1C, substituting propan-1-amine for 3-phenylpropan-1-amine and 1-(4-(2,3-dihydro-1H-pyrrolo[3,4-c]pyridine-2-carboxamido)phenyl)piperidine-4-carboxylic acid for 4-(isoindoline-2-carboxamido)benzoic acid. $^1$H NMR (300 MHz, DMSO-$d_6$) δ ppm 8.60 (s, 1H), 8.49 (d, J=5.0 Hz, 1H), 8.19 (s, 1H), 7.77 (t, J=5.6 Hz, 1H), 7.42 (d, J=5.1 Hz, 1H), 7.39-7.33 (m, 2H), 6.89-6.83 (m, 2H), 4.77 (d, J=6.2 Hz, 4H), 3.64-3.56 (m, 2H), 3.05-2.94 (m, 2H), 2.63-2.52 (m, 2H), 2.28-2.14 (m, 1H), 1.79-1.59 (m, 4H), 1.47-1.33 (m, 2H), 0.84 (t, J=7.4 Hz, 3H); MS (ESI(+)) m/e 408 (M+H)+.

Table 23.

The following examples were essentially prepared as described in Example 1C, substituting the appropriate amine for 3-phenylpropan-1-amine and 1-(4-(2,3-dihydro-1H-pyrrolo[3,4-c]pyridine-2-carboxamido)phenyl)piperidine-4-carboxylic acid for 4-(isoindoline-2-carboxamido)benzoic acid.

| Ex | Name | ¹H NMR | MS |
|---|---|---|---|
| 1455 | N-(4-{4-[(2-methoxyethyl)carbamoyl]-piperidin-1-yl}phenyl)-1,3-dihydro-2H-pyrrolo[3,4-c]pyridine-2-carboxamide | ¹H NMR (400 MHz, DMSO-d₆, Temp = 90° C.) δ ppm 8.57 (s, 1H), 8.47 (d, J = 5.0 Hz, 1H), 7.91 (s, 1H), 7.47-7.41 (m, 1H), 7.40-7.30 (m, 3H), 6.86-6.80 (m, 2H), 4.80-4.74 (m, 4H), 3.61-3.52 (m, 2H), 3.36 (t, J = 5.9 Hz, 2H), 3.28-3.17 (m, 5H), 2.64 (td, J = 11.7, 3.2 Hz, 2H), 2.32-2.20 (m, 1H), 1.82-1.63 (m, 4H) | (ESI (+)) m/e 424 (M + H)⁺ |
| 1456 | N-(4-{4-[(cyclopentylmethyl)-carbamoyl]piperidin-1-yl}phenyl)-1,3-dihydro-2H-pyrrolo[3,4-c]pyridine-2-carboxamide | ¹H NMR (400 MHz, DMSO-d₆) δ ppm 8.60 (s, 1H), 8.49 (d, J = 5.0 Hz, 1H), 8.19 (s, 1H), 7.79 (t, J = 5.7 Hz, 1H), 7.42 (d, J = 5.0 Hz, 1H), 7.39-7.33 (m, 2H), 6.89-6.83 (m, 2H), 4.80-4.74 (m, 4H), 3.64-3.56 (m, 2H), 3.01-2.94 (m, 2H), 2.64-2.53 (m, 2H), 2.30-2.16 (m, 1H), 2.04-1.91 (m, 1H), 1.74-1.43 (m, 10H), 1.29-1.06 (m, 2H) | (ESI (+)) m/e 448 (M + H)⁺ |
| 1457 | N-(4-{4-[(1,4-dioxan-2-ylmethyl)carbamoyl]-piperidin-1-yl}phenyl)-1,3-dihydro-2H-pyrrolo[3,4-c]pyridine-2-carboxamide | ¹H NMR (400 MHz, DMSO-d₆) δ ppm 8.60 (s, 1H), 8.49 (d, J = 5.0 Hz, 1H), 8.19 (s, 1H), 7.90 (t, J = 5.8 Hz, 1H), 7.42 (d, J = 5.1 Hz, 1H), 7.39-7.33 (m, 2H), 6.89-6.83 (m, 2H), 4.78-4.74 (m, 4H), 3.75-3.41 (m, 8H), 3.21-3.13 (m, 1H), 3.13-3.02 (m, 2H), 2.63-2.53 (m, 2H), 2.30-2.20 (m, 1H), 1.77-1.59 (m, 4H) | (ESI (+)) m/e 466 (M + H)⁺ |
| 1458 | N-{4-[4-(cyclopentylcarbamoyl)-piperidin-1-yl]phenyl}-1,3-dihydro-2H-pyrrolo[3,4-c]pyridine-2-carboxamide | ¹H NMR (400 MHz, DMSO-d₆) δ ppm 8.60 (s, 1H), 8.49 (d, J = 5.0 Hz, 1H), 8.19 (s, 1H), 7.73 (d, J = 7.2 Hz, 1H), 7.42 (d, J = 5.1 Hz, 1H), 7.39-7.33 (m, 2H), 6.89-6.83 (m, 2H), 4.82-4.71 (m, 4H), 4.04-3.92 (m, 1H), 3.64-3.56 (m, 2H), 2.61-2.51 (m, 2H), 2.24-2.13 (m, 1H), 1.84-1.56 (m, 8H), 1.55-1.42 (m, 2H), 1.40-1.29 (m, 2H) | (ESI (+)) m/e 434 (M + H)⁺ |
| 1459 | N-{4-[4-(tetrahydro-2H-pyran-4-ylcarbamoyl)piperidin-1-yl]phenyl}-1,3-dihydro-2H-pyrrolo[3,4-c]pyridine-2-carboxamide | ¹H NMR (400 MHz, DMSO-d₆, Temp = 90° C.) δ ppm 8.57 (s, 1H), 8.47 (d, J = 5.0 Hz, 1H), 7.91 (s, 1H), 7.41-7.31 (m, 4H), 6.86-6.80 (m, 2H), 4.80-4.74 (m, 4H), 3.85-3.71 (m, 3H), 3.62-3.53 (m, 2H), 3.41-3.29 (m, 2H), 2.70-2.58 (m, 2H), 2.28-2.18 (m, 1H), 1.81-1.64 (m, 6H), 1.49-1.36 (m, 2H) | (ESI (+)) m/e 450 (M + H)⁺ |
| 1460 | N-{4-[4-(morpholin-4-ylcarbonyl)piperidin-1-yl]phenyl}-1,3-dihydro-2H-pyrrolo[3,4-c]pyridine-2-carboxamide | ¹H NMR (400 MHz, DMSO-d₆) δ ppm 8.60 (s, 1H), 8.49 (d, J = 5.0 Hz, 1H), 8.19 (s, 1H), 7.42 (d, J = 5.1 Hz, 1H), 7.39-7.33 (m, 2H), 6.89-6.83 (m, 2H), 4.81-4.72 (m, 4H), 3.65-3.42 (m, 10H), 2.79-2.59 (m, 3H), 1.73-1.64 (m, 4H) | (ESI (+)) m/e 436 (M + H)⁺ |
| 1461 | N-(4-{4-[(tetrahydro-2H-pyran-4-ylmethyl)carbamoyl]-piperidin-1-yl}phenyl)-1,3-dihydro-2H-pyrrolo[3,4-c]pyridine-2-carboxamide | ¹H NMR (400 MHz, DMSO-d₆) δ ppm 8.60 (s, 1H), 8.49 (d, J = 5.0 Hz, 1H), 8.19 (s, 1H), 7.81 (t, J = 5.8 Hz, 1H), 7.42 (d, J = 5.1 Hz, 1H), 7.39-7.33 (m, 2H), 6.89-6.83 (m, 2H), 4.80-4.74 (m, 4H), 3.87-3.79 (m, 2H), 3.64-3.56 (m, 2H), 3.28-3.18 (m, 2H), 2.95 (t, J = 6.2 Hz, 2H), 2.64-2.52 (m, 2H), 2.29-2.18 (m, 1H), 1.78-1.56 (m, 5H), 1.57-1.47 (m, 2H), 1.20-1.06 (m, 2H) | (ESI (+)) m/e 464 (M + H)⁺ |
| 1462 | N-{4-[4-(cyclopropylcarbamoyl)-piperidin-1-yl]phenyl}-1,3-dihydro-2H-pyrrolo[3,4-c]pyridine-2-carboxamide | ¹H NMR (400 MHz, DMSO-d₆) δ ppm 8.60 (s, 1H), 8.49 (d, J = 5.0 Hz, 1H), 8.19 (s, 1H), 7.84 (d, J = 4.3 Hz, 1H), 7.42 (d, J = 5.1 Hz, 1H), 7.39-7.33 (m, 2H), 6.89-6.83 (m, 2H), 4.80-4.74 (m, 4H), 3.63-3.55 (m, 2H), 2.66-2.48 (m, 3H), 2.20-2.08 (m, 1H), 1.76-1.58 (m, 4H), 0.63-0.55 (m, 2H), 0.41-0.33 (m, 2H) | (ESI (+)) m/e 406 (M + H)⁺ |
| 1463 | N-(4-{4-[(tetrahydrofuran-3-ylmethyl)carbamoyl]-piperidin-1-yl}phenyl)-1,3-dihydro-2H-pyrrolo-[3,4-c]pyridine-2-carboxamide | ¹H NMR (400 MHz, DMSO-d₆) δ ppm 8.59 (s, 1H), 8.49 (d, J = 5.0 Hz, 1H), 8.19 (s, 1H), 7.91 (t, J = 5.7 Hz, 1H), 7.42 (d, J = 4.5 Hz, 1H), 7.39-7.33 (m, 2H), 6.89-6.83 (m, 2H), 4.80-4.74 (m, 4H), 3.73-3.54 (m, 5H), 3.40-3.34 (m, 1H), 3.09-2.98 (m, 2H), 2.64-2.53 (m, 2H), 2.37-2.27 (m, 1H), 2.27-2.17 (m, 1H), 1.94-1.83 (m, 1H), 1.79-1.61 (m, 4H), 1.57-1.46 (m, 1H) | (ESI (+)) m/e 450 (M + H)⁺ |
| 1464 | N-(4-{4-[(2-hydroxy-2-methylpropyl)carbamoyl]-piperidin-1-yl}phenyl)-1,3-dihydro-2H-pyrrolo[3,4-c]pyridine-2-carboxamide | ¹H NMR (400 MHz, DMSO-d₆) δ ppm 8.60 (s, 1H), 8.49 (d, J = 5.0 Hz, 1H), 8.19 (s, 1H), 7.66 (t, J = 6.0 Hz, 1H), 7.42 (d, J = 4.6 Hz, 1H), 7.39-7.33 (m, 2H), 6.90-6.83 (m, 2H), 4.83-4.71 (m, 4H), 4.44 (s, 1H), 3.65-3.57 (m, 2H), 3.03 (d, J = 6.0 Hz, 2H), 2.64-2.53 (m, 2H), 2.39-2.27 (m, 1H), 1.79-1.61 (m, 4H), 1.04 (s, 6H) | (ESI (+)) m/e 438 (M + H)⁺ |
| 1465 | N-{4-[4-(butan-2-ylcarbamoyl)piperidin-1-yl]phenyl}-1,3-dihydro-2H-pyrrolo[3,4-c]pyridine-2-carboxamide | ¹H NMR (400 MHz, DMSO-d₆) δ ppm 8.60 (s, 1H), 8.49 (d, J = 5.0 Hz, 1H), 8.19 (s, 1H), 7.56 (d, J = 8.2 Hz, 1H), 7.42 (d, J = 4.5 Hz, 1H), 7.39-7.33 (m, 2H), 6.89-6.83 (m, 2H), 4.81-4.70 (m, 4H), 3.72-3.54 (m, 3H), 2.62-2.50 (m, 2H), 2.27-2.14 (m, 1H), 1.78-1.58 (m, 4H), 1.44-1.28 (m, 2H), 1.01 (d, J = 6.6 Hz, 3H), 0.81 (t, J = 7.4 Hz, 3H) | (ESI (+)) m/e 422 (M + H)⁺ |

Example 1472

N-(4-{(4R)-4-[(2-methylpropanoyl)amino]cyclohex-1-en-1-yl}phenyl)-1,3-dihydro-2H-pyrrolo[3,4-c]pyridine-2-carboxamide A racemic mixture of N-(4-{4-[(2-methylpropanoyl)amino]cyclohex-1-en-1-yl}phenyl)-1,3-dihydro-2H-pyrrolo[3,4-c]pyridine-2-carboxamide (250 mg) was dissolved in methanol and separated using SCF-LC with a ChiralPak AD-H 21×250 mm column to provide N-(4-{(4R)-4-[(2-methylpropanoyl)amino]cyclohex-1-en-1-yl}phenyl)-1,3-dihydro-2H-pyrrolo[3,4-c]pyridine-2-carboxamide. $^1$H NMR (300 MHz, DMSO-$d_6$) δ 8.61 (s, 1H), 8.50 (d, J=5.0 Hz, 1H), 8.41 (s, 1H), 7.66 (d, J=7.6 Hz, 1H), 7.56-7.48 (m, 2H), 7.43 (d, J=5.1 Hz, 1H), 7.37-7.29 (m, 2H), 6.02 (bs, 1H), 4.84-4.77 (m, 4H), 3.89-3.73 (m, 1H), 2.44 (ddd, J=12.7, 8.7, 4.6 Hz, 2H), 2.41-2.26 (m, 2H), 2.14-1.97 (m, 1H), 1.93-1.81 (m, 1H), 1.67-1.49 (m, 1H), 1.00 (dd, J=6.8, 2.4 Hz, 6H); MS (ESI(+)) m/e 405 (M+H)$^+$.

Example 1473

N-(4-{(4S)-4-[(2-methylpropanoyl)amino]cyclohex-1-en-1-yl}phenyl)-1,3-dihydro-2H-pyrrolo[3,4-c]pyridine-2-carboxamide A racemic mixture of N-(4-{4-[(2-methylpropanoyl)amino]cyclohex-1-en-1-yl}phenyl)-1,3-dihydro-2H-pyrrolo[3,4-c]pyridine-2-carboxamide (250 mg) was dissolved in methanol and separated using SCF-LC with a ChiralPak AD-H 21×250 mm column to provide N-(4-{(4S)-4-[(2-methylpropanoyl)amino]cyclohex-1-en-1-yl}phenyl)-1,3-dihydro-2H-pyrrolo[3,4-c]pyridine-2-carboxamide. $^1$H NMR (300 MHz, DMSO-$d_6$) δ 8.61 (s, 1H), 8.50 (d, J=5.0 Hz, 1H), 8.41 (s, 1H), 7.66 (d, J=7.6 Hz, 1H), 7.56-7.49 (m, 2H), 7.43 (d, J=5.1 Hz, 1H), 7.37-7.29 (m, 2H), 6.05-5.99 (m, 1H), 4.84-4.77 (m, 4H), 3.89-3.73 (m, 1H), 2.47-2.39 (m, 1H), 2.41-2.30 (m, 2H), 2.11-1.97 (m, 1H), 1.93-1.82 (m, 1H), 1.67-1.50 (m, 1H), 1.00 (dd, J=6.8, 2.4 Hz, 6H); MS (ESI(+)) m/e 405 (M+H)$^+$.

Example 1474

N-[4-(1-benzoylazetidin-3-yl)butyl]-1,3-dihydro-2H-isoindole-2-carboxamide

Example 1474A tert-butyl 3-(2-hydroxyethyl)azetidine-1-carboxylate

A solution of 2-(1-(tert-butoxycarbonyl)azetidin-3-yl)acetic acid (1 g, 4.65 mmol) in tetrahydrofuran (5 ml) was cooled to 0° C. and treated with borane tetrahydrofuran complex (7.00 ml, 7 mmol) dropwise by syringe. After 1 hour at 0° C. the solution was allowed to warm to room temperature and stirred overnight and then it was quenched with 20 ml of 1M aqueous NaOH. The separated aqueous layer was extracted with ether (2×15 ml), dried with magnesium sulfate, filtered and concentrated to give the title compound which was used without purification.

Example 1474B tert-butyl 3-(2-oxoethyl)azetidine-1-carboxylate

To a solution of oxalyl chloride (488 μl, 5.58 mmol) in 40 ml dichloromethane at −78° C. was added dimethyl sulfoxide (792 μl, 11.16 mmol) dropwise by syringe. The mixture was stirred for 15 minutes at −78° C. when a solution of tert-butyl 3-(2-hydroxyethyl)azetidine-1-carboxylate (936 mg, 4.65 mmol) in 10 ml dichloromethane was added dropwise by syringe. After 1 hour at −78° C., triethylamine (3241 μl, 23.25 mmol) was added and the suspension was warmed to room temperature and stirred for an additional hour. The mixture was quenched with water (25 ml) and saturated aqueous potassium carbonate (10 ml), stirred vigorously and separated. The aqueous layer was extracted with dichloromethane (2×20 ml) and the combined organic layers were dried with magnesium sulfate, filtered and concentrated. The crude material was flash chromatographed to give the title compound.

Example 1474C tert-butyl 3-(3-cyanoallyl)azetidine-1-carboxylate

To a solution of potassium tert-butoxide, 1M in tetrahydrofuran (3694 μl, 3.69 mmol) at 0° C. was added dropwise by syringe a solution of diethyl cyanomethylphosphonate (570 μl, 3.52 mmol) in 5 ml tetrahydrofuran. The reaction mixture was warmed to room temperature and then cooled to 0° C. again. This solution was treated with tert-butyl 3-(2-oxoethyl)azetidine-1-carboxylate (701 mg, 3.52 mmol) in 2 ml tetrahydrofuran dropwise by syringe and then allowed to warm to room temperature. After stirring overnight the gelatinous mixture was quenched with water (20 ml) and extracted with ethyl acetate (2×20 ml); the organic layers were washed with brine (20 ml), dried with magnesium sulfate, filtered and concentrated. The liquid residue was flash chromatographed to give the title compound as a 1:1 mixture of E/Z isomers.

Example 1474D tert-butyl 3-(4-aminobutyl) azetidine-1-carboxylate

7M $NH_3$—$CH_3OH$ (10 mL) was added to tert-butyl 3-(3-cyanoallyl)azetidine-1-carboxylate (640 mg, 2.88 mmol) and Ra—Ni 2800, water slurry (881 mg, 6.75 mmol) in a 20 mL pressure bottle. The mixture was stirred under 30 psi of hydrogen at room temperature for 16 hours. The mixture was filtered through a polypropylene membrane, concentrated by rotovap and dried under vacuum to provide the title compound which was used without purification.

Example 1474E tert-butyl 3-(4-(isoindoline-2-carboxamido)butyl) azetidine-1-carboxylate The title compound was prepared as described in Example 344A, substituting tert-butyl 3-(4-aminobutyl)azetidine-1-carboxylate for tert-butyl 5-aminoisoindoline-2-carboxylate.

Example 1474F

N-(4-(azetidin-3-yl)butyl)isoindoline-2-carboxamide

The title compound was prepared as described in Example 2D, substituting tert-butyl 3-(4-(isoindoline-2-carboxamido)butyl)azetidine-1-carboxylate for tert-butyl 4-((4-(5-fluoroisoindoline-2-carboxamido)benzamido)methyl)benzylcarbamate.

Example 1474G

N-[4-(1-benzoylazetidin-3-yl)butyl]-1,3-dihydro-2H-isoindole-2-carboxamide

The title compound was prepared as described in Example 278, substituting benzoyl chloride for acetyl chloride and N-(4-(azetidin-3-yl)butyl)isoindoline-2-carboxamide for 5-amino-N-(4-(propylcarbamoyl)phenyl)isoindoline-2-carboxamide. $^1$H NMR (300 MHz, DMSO-$d_6$) δ 7.67-7.57 (m, 2H), 7.57-7.39 (m, 3H), 7.39-7.23 (m, 4H), 6.28 (s, 1H), 4.56 (s, 4H), 4.34 (t, J=8.3 Hz, 1H), 4.11 (t, J=9.0 Hz, 1H), 4.01-3.82 (m, 1H), 3.65 (dd, J=9.8, 5.8 Hz, 1H), 3.07 (dd, J=12.7, 6.8 Hz, 2H), 2.66-2.53 (m, 1H), 1.59 (dd, J=15.3, 7.7 Hz, 2H), 1.51-1.36 (m, 2H), 1.25 (dd, J=13.5, 6.4 Hz, 2H); MS (ESI (+)) m/e 378 (M+H)$^+$.

Example 1475

N-[4-(1-benzoylazetidin-3-yl)butyl]-1,3-dihydro-2H-pyrrolo[3,4-c]pyridine-2-carboxamide

Example 1475A tert-butyl 3-(4-(2,3-dihydro-1H-pyrrolo[3,4-c]pyridine-2-carboxamido)butyl)azetidine-1-carboxylate The title compound was prepared as described in Example 344A, substituting tert-butyl 3-(4-aminobutyl)azetidine-1-carboxylate for tert-butyl 5-aminoisoindoline-2-carboxylate and 1,3-dihydro-2H-pyrrolo[3,4-c]pyridine for isoindoline.

Example 1475B

N-(4-(azetidin-3-yl)butyl)-1H-pyrrolo[3,4-c]pyridine-2(3H)-carboxamide

The title compound was prepared as described in Example 2D, substituting tert-butyl 3-(4-(2,3-dihydro-1H-pyrrolo[3,4-c]pyridine-2-carboxamido)butyl)azetidine-1-carboxylate for tert-butyl 4-((4-(5-fluoroisoindoline-2-carboxamido)benzamido)methyl)benzylcarbamate.

Example 1475C

N-[4-(1-benzoylazetidin-3-yl)butyl]-1,3-dihydro-2H-pyrrolo[3,4-c]pyridine-2-carboxamide The title compound was prepared as described in Example 278, substituting benzoyl chloride for acetyl chloride and N-(4-(azetidin-3-yl)butyl)-1H-pyrrolo[3,4-c]pyridine-2(3H)-carboxamide for 5-amino-N-(4-(propylcarbamoyl)phenyl)isoindoline-2-carboxamide. $^1$H NMR (300 MHz, DMSO-$d_6$) δ 8.55 (s, 1H), 8.46 (d, J=5.0 Hz, 1H), 7.67-7.55 (m, 2H), 7.55-7.34 (m, 4H), 6.37 (t, J=5.5 Hz, 1H), 4.60 (d, J=2.3 Hz, 4H), 4.35 (t, J=8.3 Hz, 1H), 4.11 (t, J=9.1 Hz, 1H), 3.96-3.83 (m, 1H), 3.65 (dd, J=9.7, 5.7 Hz, 1H), 3.07 (dd, J=12.8, 6.7 Hz, 2H), 2.65-2.53 (m, 1H), 1.59 (dd, J=15.2, 7.6 Hz, 2H), 1.43 (dd, J=14.4, 7.2 Hz, 2H), 1.34-1.09 (m, 2H); MS (ESI(+)) m/e 379 (M+H)$^+$.

Example 1476

N-[trans-3-(benzylcarbamoyl)cyclobutyl]-1,3-dihydro-2H-pyrrolo[3,4-c]pyridine-2-carboxamide

Example 1476A trans-3-(2,3-dihydro-1H-pyrrolo[3,4-c]pyridine-2-carboxamido)cyclobutanecarboxylic acid The title compound was prepared as described in Example 272A, substituting benzyl trans-3-[(1,3-dihydro-2H-pyrrolo[3,4-c]pyridin-2-ylcarbonyl)amino]cyclobutanecarboxylate for 4-nitro-N-propylbenzamide.

Example 1476B

N-[trans-3-(benzylcarbamoyl)cyclobutyl]-1,3-dihydro-2H-pyrrolo[3,4-c]pyridine-2-carboxamide The title compound was prepared as described in Example 1C, substituting benzylamine for 3-phenylpropan-1-amine and trans-3-(2,3-dihydro-1H-pyrrolo[3,4-c]pyridine-2-carboxamido)cyclobutanecarboxylic acid for 4-(isoindoline-2-carboxamido)benzoic acid. $^1$H NMR (400 MHz, DMSO-$d_6$) δ ppm 8.56 (s, 1H), 8.47 (d, J=5.0 Hz, 1H), 8.26 (t, J=5.9 Hz, 1H), 7.39 (d, J=5.1 Hz, 1H), 7.36-7.28 (m, 2H), 7.27-7.20 (m, 3H), 6.60 (d, J=7.6 Hz, 1H), 4.65-4.59 (m, 4H), 4.45-4.29 (m, 1H), 4.28 (d, J=5.9 Hz, 2H), 2.96-2.84 (m, 1H), 2.41-2.29 (m, 2H), 2.30-2.15 (m, 2H); MS (ESI(+)) m/e 351 (M+H)$^+$.

Example 1477

N-{trans-3-[(2-phenylethyl)carbamoyl]cyclobutyl}-1,3-dihydro-2H-pyrrolo[3,4-c]pyridine-2-carboxamide The title compound was prepared as described in Example 1C, substituting 2-phenylethylamine for 3-phenylpropan-1-amine and trans-3-(2,3-dihydro-1H-pyrrolo[3,4-c]pyridine-2-carboxamido)cyclobutanecarboxylic acid for 4-(isoindoline-2-carboxamido)benzoic acid. $^1$H NMR (400 MHz, DMSO-$d_6$) δ ppm 8.56 (s, 1H), 8.47 (d, J=5.0 Hz, 1H), 7.80 (t, J=5.6 Hz, 1H), 7.39 (d, J=5.1 Hz, 1H), 7.33-7.24 (m, 2H), 7.23-7.16 (m, 3H), 6.57 (d, J=7.6 Hz, 1H), 4.65-4.58 (m, 4H), 4.38-4.24 (m, 1H), 3.33-3.23 (m, 2H), 2.84-2.74 (m, 1H), 2.72 (t, J=7.3 Hz, 2H), 2.32-2.22 (m, 2H), 2.24-2.09 (m, 2H); MS (ESI(+)) m/e 365 (M+H)$^+$.

Example 1478

N-{trans-3-[(3-phenylpropyl)carbamoyl]cyclobutyl}-1,3-dihydro-2H-pyrrolo[3,4-c]pyridine-2-carboxamide The title compound was prepared as described in Example 1C, substituting 3-phenylpropylamine for 3-phenylpropan-1-amine and trans-3-(2,3-dihydro-1H-pyrrolo[3,4-c]pyridine-2-carboxamido)cyclobutanecarboxylic acid for 4-(isoindoline-2-carboxamido)benzoic acid. $^1$H NMR (400 MHz, DMSO-$d_6$) δ ppm 8.56 (s, 1H), 8.47 (d, J=5.0 Hz, 1H), 7.75 (t, J=5.5 Hz, 1H), 7.38 (d, J=5.1 Hz, 1H), 7.32-7.24 (m, 2H), 7.24-7.13 (m, 3H), 6.58 (d, J=7.6 Hz, 1H), 4.66-4.55 (m, 4H), 4.41-4.27 (m, 1H), 3.11-3.03 (m, 2H), 2.89-2.75 (m, 1H), 2.62-2.52 (m, 2H), 2.39-2.25 (m, 2H), 2.26-2.11 (m, 2H), 1.76-1.63 (m, 2H); MS (ESI(+)) m/e 379 (M+H)$^+$.

Example 1525

N-[4-(cis-4-{[(2-methoxyethoxy)acetyl]amino}cyclohexyl)phenyl]-1,3-dihydro-2H-pyrrolo[3,4-c]pyridine-2-carboxamide Example 1525A tert-butyl 4-(4-(2,3-dihydro-1H-pyrrolo[3,4-c]pyridine-2-carboxamido)phenyl)cyclohexylcarbamate The title compound was prepared as described in Example 979A, substituting tert-butyl 4-(4-(2,3-dihydro-1H-pyrrolo[3,4-c]pyridine-2-carboxamido)phenyl)cyclohex-3-enylcarbamate for tert-Butyl 4-(4-(isoindoline-2-carboxamido)phenyl)-5,6-dihydropyridine-1(2H)-carboxylate.

Example 1525B

N-(4-(4-aminocyclohexyl)phenyl)-1H-pyrrolo[3,4-c]pyridine-2(3H)-carboxamide

The title compound was prepared as described in Example 2D, substituting tert-butyl 4-(4-(2,3-dihydro-1H-pyrrolo[3,4-c]pyridine-2-carboxamido)phenyl)cyclohexylcarbamate for tert-butyl 4-((4-(5-fluoroisoindoline-2-carboxamido)benzamido)methyl)benzylcarbamate.

Example 1525C

N-[4-(cis-4-{[(2-methoxyethoxy)acetyl]amino}cyclohexyl)phenyl]-1,3-dihydro-2H-pyrrolo[3,4-c]pyridine-2-carboxamide The title compound was prepared as described in Example 1C as a 1:1 cis/trans mixture, substituting N-(4-(4-aminocyclohexyl)phenyl)-1H-pyrrolo[3,4-c]pyridine-2(3H)-carboxamide for 3-phenylpropan-1-amine and 2-(2-methoxyethoxy)acetic acid for 4-(isoindoline-2-carboxamido)benzoic acid. HPLC separation of the cis/trans isomers provided N-[4-(cis-4-{[(2-methoxyethoxy)acetyl]amino}cyclohexyl)phenyl]-1,3-dihydro-2H-pyrrolo[3,4-c]pyridine-2-carboxamide. $^1$H NMR (501 MHz, DMSO-d$_6$) δ 8.59 (bs, 1H), 8.51-8.45 (m, 1H), 8.32 (bs, 1H), 7.44 (dd, J=11.5, 5.2 Hz, 3H), 7.40 (t, J=7.6 Hz, 1H), 7.17-7.11 (m, 2H), 4.81-4.74 (m, 4H), 4.03-3.96 (m, 1H), 3.90 (d, J=2.2 Hz, 2H), 3.63-3.58 (m, 2H), 3.52-3.46 (m, 2H), 3.27-3.23 (m, 3H), 1.80-1.30 (m, 8H); MS (ESI(+)) m/e 453 (M+H)$^+$.

Example 1526

N-[4-(trans-4-{[(2-methoxyethoxy)acetyl]amino}cyclohexyl)phenyl]-1,3-dihydro-2H-pyrrolo[3,4-c]pyridine-2-carboxamide The title compound was prepared as described in Example 1C as a 1:1 cis/trans mixture, substituting N-(4-(4-aminocyclohexyl)phenyl)-1H-pyrrolo[3,4-c]pyridine-2(3H)-carboxamide for 3-phenylpropan-1-amine and 2-(2-methoxyethoxy)acetic acid for 4-(isoindoline-2-carboxamido)benzoic acid. HPLC separation of the cis/trans isomers provided N-[4-(trans-4-{[(2-methoxyethoxy)acetyl]amino}cyclohexyl)phenyl]-1,3-dihydro-2H-pyrrolo[3,4-c]pyridine-2-carboxamide. $^1$H NMR (501 MHz, DMSO-d$_6$) δ 8.58 (s, 1H), 8.48 (d, J=5.0 Hz, 1H), 8.31 (s, 1H), 7.50-7.39 (m, 4H), 7.15-7.09 (m, 2H), 4.81-4.74 (m, 4H), 3.85 (s, 2H), 3.74-3.58 (m, 1H), 3.58-3.55 (m, 2H), 3.49-3.46 (m, 2H), 3.28 (s, 3H), 2.45-2.37 (m, 1H), 1.89-1.82 (m, 2H), 1.83-1.75 (m, 2H), 1.58-1.42 (m, 2H), 1.44-1.29 (m, 2H); MS (ESI(+)) m/e 453 (M+H)$^+$.

Example 1527

N-[4-(cis-4-{[(2S)-tetrahydrofuran-2-ylcarbonyl]amino}cyclohexyl)phenyl]-1,3-dihydro-2H-pyrrolo[3,4-c]pyridine-2-carboxamide The title compound was prepared as described in Example 1C as a 1:1 cis/trans mixture, substituting N-(4-(4-aminocyclohexyl)phenyl)-1H-pyrrolo[3,4-c]pyridine-2(3H)-carboxamide for 3-phenylpropan-1-amine and (S)-tetrahydrofuran-2-carboxylic acid for 4-(isoindoline-2-carboxamido)benzoic acid. HPLC separation of the cis/trans isomers provided N-[4-(cis-4-{[(2S)-tetrahydrofuran-2-ylcarbonyl]amino}cyclohexyl)phenyl]-1,3-dihydro-2H-pyrrolo[3,4-c]pyridine-2-carboxamide. $^1$H NMR (501 MHz, DMSO-d$_6$) δ 8.59 (s, 1H), 8.48 (d, J=5.0 Hz, 1H), 8.32 (s, 1H), 7.47-7.38 (m, 4H), 7.17-7.12 (m, 2H), 4.81-4.75 (m, 4H), 4.29-4.22 (m, 1H), 3.94-3.86 (m, 2H), 3.77 (t, J=7.1 Hz, 1H), 2.14-2.02 (m, 1H), 1.88-1.78 (m, 3H), 1.70 (dd, J=22.1, 8.6 Hz, 3H), 1.63 (t, J=17.3 Hz, 6H); MS (ESI(+)) m/e 435 (M+H)$^+$.

Example 1528

N-[4-(trans-4-{[(2S)-tetrahydrofuran-2-ylcarbonyl]amino}cyclohexyl)phenyl]-1,3-dihydro-2H-pyrrolo[3,4-c]pyridine-2-carboxamide The title compound was prepared as described in Example 1C as a 1:1 cis/trans mixture, substituting N-(4-(4-aminocyclohexyl)phenyl)-1H-pyrrolo[3,4-c]pyridine-2(3H)-carboxamide for 3-phenylpropan-1-amine and (S)-tetrahydrofuran-2-carboxylic acid for 4-(isoindoline-2-carboxamido)benzoic acid. HPLC separation of the cis/trans isomers provided N-[4-(trans-4-{[(2S)-tetrahydrofuran-2-ylcarbonyl]amino}cyclohexyl)phenyl]-1,3-dihydro-2H-pyrrolo[3,4-c]pyridine-2-carboxamide. $^1$H NMR (501 MHz, DMSO-d$_6$) δ 8.58 (bs, 1H), 8.51-8.45 (m, 1H), 8.30 (bs, 1H), 7.53-7.45 (m, 1H), 7.42 (d, J=8.3 Hz, 2H), 7.14-7.08 (m, 2H), 4.81-4.74 (m, 4H), 4.20-4.13 (m, 1H), 3.92-3.85 (m, 1H), 3.78-3.71 (m, 1H), 3.66-3.58 (m, 1H), 2.39 (s, 1H), 2.09 (dd, J=10.8, 6.4 Hz, 1H), 1.79 (s, 7H), 1.62 (s, 1H), 1.45 (dd, J=26.5, 15.7 Hz, 4H); MS (ESI(+)) m/e 435 (M+H)$^+$.

Example 1529

N-[4-(cis-4-{[(2R)-tetrahydrofuran-2-ylcarbonyl]amino}cyclohexyl)phenyl]-1,3-dihydro-2H-pyrrolo[3,4-c]pyridine-2-carboxamide The title compound was prepared as described in Example 1C as a 1:1 cis/trans mixture, substituting N-(4-(4-aminocyclohexyl)phenyl)-1H-pyrrolo[3,4-c]pyridine-2(3H)-carboxamide for 3-phenylpropan-1-amine and (R)-tetrahydrofuran-2-carboxylic acid for 4-(isoindoline-2-carboxamido)benzoic acid. HPLC separation of the cis/trans isomers provided N-[4-(cis-4-{[(2R)-tetrahydrofuran-2-ylcarbonyl]amino}cyclohexyl)phenyl]-1,3-dihydro-2H-pyrrolo[3,4-c]pyridine-2-carboxamide. $^1$H NMR (501 MHz, DMSO-d$_6$) δ 8.55 (t, J=21.5 Hz, 1H), 8.46 (s, 1H), 8.32 (d, J=9.4 Hz, 1H), 7.47-7.37 (m, 4H), 7.14 (bs, 2H), 4.77 (bs, 4H), 4.29-4.20 (m, 1H), 3.96-3.84 (m, 2H), 3.80-3.71 (m, 1H), 2.12-2.01 (m, 1H), 1.76 (d, J=48.5 Hz, 4H), 1.60 (s, 7H); MS (ESI(+)) m/e 435 (M+H)$^+$.

Example 1530

N-[4-(trans-4-{[(2R)-tetrahydrofuran-2-ylcarbonyl]amino}cyclohexyl)phenyl]-1,3-dihydro-2H-pyrrolo[3,4-c]pyridine-2-carboxamide The title compound was prepared as described in Example 1C as a 1:1 cis/trans mixture, substituting N-(4-(4-aminocyclohexyl)phenyl)-1H-pyrrolo[3,4-c]pyridine-2(3H)-carboxamide for 3-phenylpropan-1-amine and (R)-tetrahydrofuran-2-carboxylic acid for 4-(isoindoline-2-carboxamido)benzoic acid. HPLC separation of the cis/trans isomers provided N-[4-(trans-4-{[(2R)-tetrahydrofuran-2-ylcarbonyl]amino}cyclohexyl)phenyl]-1,3-dihydro-2H-pyrrolo[3,4-c]pyridine-2-carboxamide. $^1$H NMR (501 MHz, DMSO-d$_6$) δ 8.58 (bs, 1H), 8.50-8.45 (m, 1H), 8.31 (bs, 1H), 7.52-7.46 (m, 1H), 7.45-7.39 (m, 3H), 7.14-7.08 (m, 2H), 4.81-4.74 (m, 4H), 4.20-4.13 (m, 1H), 3.92-3.84 (m, 1H), 3.78-3.70 (m, 1H), 3.66-3.57 (m, 1H), 2.43-2.34 (m, 1H), 2.14-2.02 (m, 1H), 2.04-1.52 (m, 7H), 1.54-1.24 (m, 4H); MS (ESI(+)) m/e 435 (M+H)$^+$.

Example 1531

N-(6-{[(2S)-tetrahydrofuran-2-ylmethyl]carbamoyl}pyridazin-3-yl)-1,3-dihydro-2H-pyrrolo[3,4-c]pyridine-2-carboxamide

Example 1531A methyl 6-(2,3-dihydro-1H-pyrrolo[3,4-c]pyridine-2-carboxamido)pyridazine-3-carboxylate Methyl 6-aminopyridazine-3-carboxylate (2 g, 13.06 mmol) was suspended in dichloromethane (50 ml) followed by addition of dry pyridine (1.265 ml, 15.67 mmol) under nitrogen. To this suspension was added a dichloromethane solution of 4-nitrophenyl carbonochloridate (2.99 g, 14.37 mmol) via syringe at ambient temperature. The mixture was stirred overnight to give a suspension that was concentrated to half volume under a stream of nitrogen. 2,3-Dihydro-1H-pyrrolo[3,4-c]pyridine, dihydrochloride (2.52 g, 13.06 mmol) was dissolved in 30 ml dimethylformamide with tri-isopropylethylamine (6.84 ml, 39.2 mmol) and added to the carbamate mixture via syringe. After stirring the mixture overnight and removing most of the solvent under vacuum, water was added; and the resulting suspension was stirred for 30 minutes and filtered to give a solid which was washed with water. Flash chromatography of the dried solid gave the title compound.

Example 1531B 6-(2,3-dihydro-1H-pyrrolo[3,4-c]pyridine-2-carboxamido)pyridazine-3-carboxylic acid The title compound was prepared as described in Example 1B, substituting methyl 6-(2,3-dihydro-1H-pyrrolo[3,4-c]pyridine-2-carboxamido)pyridazine-3-carboxylate for methyl 4-(isoindoline-2-carboxamido)benzoate.

Example 1531C

N-(6-{[(2S)-tetrahydrofuran-2-ylmethyl]carbamoyl}pyridazin-3-yl)-1,3-dihydro-2H-pyrrolo[3,4-c]pyridine-2-carboxamide The title compound was prepared as described in Example 1C, substituting (2S)-tetrahydrofuran-2-ylmethamine for 3-phenylpropan-1-amine and 6-(2,3-dihydro-1H-pyrrolo[3,4-c]pyridine-2-carboxamido)pyridazine-3-carboxylic acid for 4-(isoindoline-2-carboxamido)benzoic acid. $^1$H NMR (300 MHz, DMSO-d$_6$) δ 10.09 (s, 1H), 8.81 (t, J=6.1 Hz, 1H), 8.62 (s, 1H), 8.51 (d, J=5.0 Hz, 1H), 8.31 (d, J=9.3 Hz, 1H), 8.12 (d, J=9.3 Hz, 1H), 7.44 (d, J=5.1 Hz, 1H), 5.05-4.76 (m, 4H), 4.04 (p, J=6.2 Hz, 1H), 3.85-3.74 (m, 1H), 3.70-3.59 (m, 1H), 3.45-3.31 (m, 2H), 1.99-1.72 (m, 3H), 1.69-1.54 (m, 1H); MS (ESI(+)) m/e 369 (M+H)$^+$.

Example 1542

N-(6-{[(2R)-tetrahydrofuran-2-ylmethyl]carbamoyl}pyridazin-3-yl)-1,3-dihydro-2H-pyrrolo[3,4-c]pyridine-2-carboxamide The title compound was prepared as described in Example 1C, substituting (2R)-tetrahydrofuran-2-ylmethamine for 3-phenylpropan-1-amine and 6-(2,3-dihydro-1H-pyrrolo[3,4-c]pyridine-2-carboxamido)pyridazine-3-carboxylic acid for 4-(isoindoline-2-carboxamido)benzoic acid. $^1$H NMR (300 MHz, DMSO-d$_6$) δ 10.09 (bs, 1H), 8.81 (t, J=6.1 Hz, 1H), 8.61 (s, 1H), 8.51 (d, J=5.0 Hz, 1H), 8.31 (d, J=9.3 Hz, 1H), 8.12 (d, J=9.3 Hz, 1H), 7.44 (d, J=5.1 Hz, 1H), 5.05-4.76 (m, 4H), 4.04 (p, J=6.2 Hz, 1H), 3.85-3.74 (m, 1H), 3.70-3.59 (m, 1H), 3.35 (d, J=25.7 Hz, 2H), 1.99-1.72 (m, 3H), 1.69-1.54 (m, 1H); MS (ESI(+)) m/e 369 (M+H)$^+$.

Example 1543

N-{6-[(tetrahydro-2H-pyran-4-ylmethyl)carbamoyl]pyridazin-3-yl}-1,3-dihydro-2H-pyrrolo[3,4-c]pyridine-2-carboxamide The title compound was prepared as described in Example 1C, substituting tetrahydro-2H-pyran-4-ylmethamine for 3-phenylpropan-1-amine and 6-(2,3-dihydro-1H-pyrrolo[3,4-c]pyridine-2-carboxamido)pyridazine-3-carboxylic acid for 4-(isoindoline-2-carboxamido)benzoic acid. $^1$H NMR (300 MHz, DMSO-d$_6$) δ 10.06 (s, 1H), 9.00 (t, J=6.2 Hz, 1H), 8.62 (s, 1H), 8.51 (d, J=5.0 Hz, 1H), 8.29 (d, J=9.3 Hz, 1H), 8.11 (d, J=9.3 Hz, 1H), 7.44 (d, J=5.1 Hz, 1H), 4.96-4.89 (m, 4H), 3.89-3.79 (m, 2H), 3.22 (d, J=2.6 Hz, 3H), 1.96-1.75 (m, 1H), 1.64-1.53 (m, 2H), 1.31-1.10 (m, 2H); MS (ESI(+)) m/e 383 (M+H)$^+$.

Example 1544

N-{6-[(cyclopentylmethyl)carbamoyl]pyridazin-3-yl}-1,3-dihydro-2H-pyrrolo[3,4-c]pyridine-2-carboxamide The title compound was prepared as described in Example 1C, substituting cyclopentylmethamine for 3-phenylpropan-1-amine and 6-(2,3-dihydro-1H-pyrrolo[3,4-c]pyridine-2-carboxamido)pyridazine-3-carboxylic acid for 4-(isoindoline-2-carboxamido)benzoic acid. ¹H NMR (300 MHz, DMSO-d₆) δ 10.03 (bs, 1H), 8.95 (t, J=6.1 Hz, 1H), 8.62 (s, 1H), 8.51 (d, J=5.0 Hz, 1H), 8.29 (d, J=9.3 Hz, 1H), 8.11 (d, J=9.3 Hz, 1H), 7.44 (d, J=5.1 Hz, 1H), 4.99-4.75 (m, 4H), 3.28-3.20 (m, 2H), 2.31-2.13 (m, 1H), 1.75-1.38 (m, 6H), 1.39-1.18 (m, 2H); MS (ESI(+)) m/e 367 (M+H)⁺.

Example 1545

N-{6-[(tetrahydrofuran-3-ylmethyl)carbamoyl]pyridazin-3-yl}-1,3-dihydro-2H-pyrrolo[3,4-c]pyridine-2-carboxamide The title compound was prepared as described in Example 1C, substituting tetrahydrofuran-3-ylmethamine for 3-phenylpropan-1-amine and 6-(2,3-dihydro-1H-pyrrolo[3,4-c]pyridine-2-carboxamido)pyridazine-3-carboxylic acid for 4-(isoindoline-2-carboxamido)benzoic acid. ¹H NMR (300 MHz, DMSO-d₆) δ 10.05 (s, 1H), 9.13 (t, J=6.1 Hz, 1H), 8.62 (s, 1H), 8.51 (d, J=5.0 Hz, 1H), 8.30 (d, J=9.3 Hz, 1H), 8.12 (d, J=9.3 Hz, 1H), 7.44 (d, J=5.1 Hz, 1H), 5.05-4.76 (m, 4H), 3.80-3.57 (m, 4H), 3.48 (dd, J=12.1, 6.8 Hz, 1H), 3.37-3.31 (m, 1H), 2.62-2.52 (m, 1H), 2.01-1.80 (m, 1H), 1.71-1.56 (m, 1H); MS (ESI(+)) m/e 369 (M+H)⁺.

Example 1546

N-{6-[(bicyclo[2.2.1]hept-2-ylmethyl)carbamoyl]pyridazin-3-yl}-1,3-dihydro-2H-pyrrolo[3,4-c]pyridine-2-carboxamide The title compound was prepared as described in Example 1C, substituting bicyclo[2.2.1]hept-2-ylmethamine for 3-phenylpropan-1-amine and 6-(2,3-dihydro-1H-pyrrolo[3,4-c]pyridine-2-carboxamido)pyridazine-3-carboxylic acid for 4-(isoindoline-2-carboxamido)benzoic acid. ¹H NMR (300 MHz, DMSO-d₆) δ 10.05 (bs, 1H), 8.92 (d, J=42.7 Hz, 1H), 8.61 (s, 1H), 8.51 (d, J=5.0 Hz, 1H), 8.29 (d, J=9.3 Hz, 1H), 8.10 (d, J=9.3 Hz, 1H), 7.47-7.41 (m, 1H), 5.07-4.74 (m, 4H), 3.23-2.84 (m, 2H), 2.30-2.02 (m, 3H), 1.86-1.57 (m, 2H), 1.58-0.99 (m, 6H); MS (ESI(+)) m/e 393 (M+H)⁺.

Example 1547

N-(4-{trans-4-[(2-methylpropanoyl)amino]cyclohexyl}phenyl)-1,3-dihydro-2H-pyrrolo[3,4-c]pyridine-2-carboxamide The title compound was prepared as described in Example 1C as a 1:1 cis/trans mixture, substituting N-(4-(4-aminocyclohexyl)phenyl)-1H-pyrrolo[3,4-c]pyridine-2(3H)-carboxamide for 3-phenylpropan-1-amine and isobutyric acid for 4-(isoindoline-2-carboxamido)benzoic acid. HPLC separation of the cis/trans isomers provided N-(4-{trans-4-[(2-methylpropanoyl)amino]cyclohexyl}phenyl)-1,3-dihydro-2H-pyrrolo[3,4-c]pyridine-2-carboxamide. ¹H NMR (300 MHz, DMSO-d₆) δ 8.60 (s, 1H), 8.50 (d, J=5.0 Hz, 1H), 8.32 (s, 1H), 7.58 (d, J=7.8 Hz, 1H), 7.48-7.40 (m, 3H), 7.17-7.09 (m, 2H), 4.82-4.76 (m, 4H), 3.65-3.47 (m, 1H), 2.41-2.23 (m, 2H), 1.93-1.69 (m, 4H), 1.62-1.38 (m, 2H), 1.39-1.12 (m, 2H), 0.99 (d, J=6.8 Hz, 6H); MS (ESI(+)) m/e 407 (M+H)⁺.

Example 1548

N-(4-{cis-4-[(2-methylpropanoyl)amino]cyclohexyl}phenyl)-1,3-dihydro-2H-pyrrolo[3,4-c]pyridine-2-carboxamide The title compound was prepared as described in Example 1C as a 1:1 cis/trans mixture, substituting N-(4-(4-aminocyclohexyl)phenyl)-1H-pyrrolo[3,4-c]pyridine-2(3H)-carboxamide for 3-phenylpropan-1-amine and isobutyric acid for 4-(isoindoline-2-carboxamido)benzoic acid. HPLC separation of the cis/trans isomers provided N-(4-{cis-4-[(2-methylpropanoyl)amino]cyclohexyl}phenyl)-1,3-dihydro-2H-pyrrolo[3,4-c]pyridine-2-carboxamide. ¹H NMR (300 MHz, DMSO-d₆) δ 8.60 (s, 1H), 8.50 (d, J=5.0 Hz, 1H), 8.33 (s, 1H), 7.68-7.61 (m, 1H), 7.49-7.40 (m, 3H), 7.21-7.14 (m, 2H), 4.83-4.76 (m, 4H), 3.98-3.90 (m, 1H), 1.97-1.49 (m, 9H), 1.04-0.97 (m, 6H); MS (ESI(+)) m/e 407 (M+H)⁺.

Example 1549

N-(4-{cis-4-[(cyclohexylcarbonyl)amino]cyclohexyl}phenyl)-1,3-dihydro-2H-pyrrolo[3,4-c]pyridine-2-carboxamide The title compound was prepared as described in Example 1C as a 1:1 cis/trans mixture, substituting N-(4-(4-aminocyclohexyl)phenyl)-1H-pyrrolo[3,4-c]pyridine-2(3H)-carboxamide for 3-phenylpropan-1-amine and cyclohexanecarboxylic acid for 4-(isoindoline-2-carboxamido)benzoic acid. HPLC separation of the cis/trans isomers provided N-(4-{cis-4-[(cyclohexylcarbonyl)amino]cyclohexyl}phenyl)-1,3-dihydro-2H-pyrrolo[3,4-c]pyridine-2-carboxamide. ¹H NMR (300 MHz, DMSO-d₆) δ 8.61 (s, 1H), 8.50 (d, J=5.0 Hz, 1H), 8.33 (s, 1H), 7.66-7.59 (m, 1H), 7.47 (s, 1H), 7.47-7.40 (m, 2H), 7.21-7.14 (m, 2H), 4.83-4.76 (m, 4H), 3.98-3.90 (m, 1H), 2.45 (s, 1H), 2.31-2.19 (m, 1H), 1.89-1.46 (m, 12H), 1.46-1.05 (m, 6H); MS (ESI(+)) m/e 447 (M+H)⁺.

Example 1550

N-(4-{trans-4-[(cyclohexylcarbonyl)amino]cyclohexyl}phenyl)-1,3-dihydro-2H-pyrrolo[3,4-c]pyridine-2-carboxamide The title compound was prepared as described in Example 1C as a 1:1 cis/trans mixture, substituting N-(4-(4-aminocyclohexyl)phenyl)-1H-pyrrolo[3,4-c]pyridine-2(3H)-carboxamide for 3-phenylpropan-1-amine and cyclohexanecarboxylic acid for 4-(isoindoline-2-carboxamido)benzoic acid. HPLC separation of the cis/trans isomers provided N-(4-{trans-4-[(cyclohexylcarbonyl)amino]cyclohexyl}phenyl)-1,3-dihydro-2H-pyrrolo[3,4-c]pyridine-2-carboxamide. ¹H NMR (300 MHz, DMSO-d₆) δ 8.60 (s, 1H), 8.49 (d, J=5.0 Hz, 1H), 8.32 (s, 1H), 7.54 (d, J=7.9 Hz, 1H), 7.47-7.40 (m, 3H), 7.16-7.09 (m, 2H), 4.82-4.75 (m, 4H), 3.62-3.42 (m, 1H), 2.42-2.33 (m, 1H), 2.12-1.99 (m, 1H), 1.87-1.61 (m, 8H), 1.55-1.37 (m, 3H), 1.38-1.08 (m, 7H); MS (ESI(+)) m/e 447 (M+H)⁺.

Example 1551

N-(4-{trans-4-[(cyclopropylacetyl)amino]cyclohexyl}phenyl)-1,3-dihydro-2H-pyrrolo[3,4-c]pyridine-2-carboxamide The title compound was prepared as described in Example 1C as a 1:1 cis/trans mixture, substituting N-(4-(4-aminocyclohexyl)phenyl)-1H-pyrrolo[3,4-c]pyridine-2(3H)-carboxamide for 3-phenylpropan-1-amine and 2-cyclopropylacetic acid for 4-(isoindoline-2-carboxamido)benzoic acid. HPLC separation of the cis/trans isomers provided N-(4-{trans-4-[(cyclopropylacetyl)amino]cyclohexyl}phenyl)-1,3-dihydro-2H-pyrrolo[3,4-c]pyridine-2-carboxamide. ¹H NMR (300 MHz, DMSO-d₆) δ 8.60 (s, 1H), 8.50 (d, J=5.0 Hz, 1H), 8.32 (s, 1H), 7.59 (d, J=7.8 Hz, 1H), 7.48-7.40 (m, 3H), 7.11 (s, 2H), 4.82-4.76 (m, 4H), 3.66-3.50 (m, 1H), 2.40 (t, J=10.1 Hz, 1H), 1.94 (t, J=11.8 Hz, 1H), 1.83 (dd, J=23.4, 12.2 Hz, 4H), 1.61-1.39 (m, 2H), 1.40-1.18 (m, 3H), 1.04-0.83 (m, 1H), 0.46-0.33 (m, 2H), 0.18-0.07 (m, 2H); MS (ESI(+)) m/e 419 (M+H)$^+$.

Example 1552

N-(4-{cis-4-[(cyclopropylacetyl)amino]cyclohexyl}phenyl)-1,3-dihydro-2H-pyrrolo[3,4-c]pyridine-2-carboxamide The title compound was prepared as described in Example 1C as a 1:1 cis/trans mixture, substituting N-(4-(4-aminocyclohexyl)phenyl)-1H-pyrrolo[3,4-c]pyridine-2(3H)-carboxamide for 3-phenylpropan-1-amine and 2-cyclopropylacetic acid for 4-(isoindoline-2-carboxamido)benzoic acid. HPLC separation of the cis/trans isomers provided N-(4-{cis-4-[(cyclopropylacetyl)amino]cyclohexyl}phenyl)-1,3-dihydro-2H-pyrrolo[3,4-c]pyridine-2-carboxamide. $^1$H NMR (300 MHz, DMSO-d$_6$) δ 8.61 (s, 1H), 8.50 (d, J=5.0 Hz, 1H), 8.33 (s, 1H), 7.67-7.60 (m, 1H), 7.49-7.40 (m, 3H), 7.21-7.13 (m, 2H), 4.83-4.76 (m, 4H), 4.02-3.92 (m, 1H), 2.06 (d, J=7.0 Hz, 2H), 1.84-1.65 (m, 4H), 1.65-1.47 (m, 4H), 1.25-0.90 (m, 1H), 0.47-0.34 (m, 2H), 0.23-0.11 (m, 2H); MS (ESI(+)) m/e 419 (M+H)$^+$.

Example 1553

N-(4-{4-[(2-methylpropanoyl)amino]cyclohex-1-en-1-yl}phenyl)-1,3-dihydro-2H-isoindole-2-carboxamide Example 1553A tert-butyl 4-(4-nitrophenyl)cyclohex-3-enylcarbamate The title was prepared as in Example 1018B, substituting 4,4,5,5-tetramethyl-2-(4-nitrophenyl)-1,3,2-dioxaborolane for N-(4-(4,4,5,5-Tetramethyl-1,3,2-dioxaborolan-2-yl)phenyl)-1H-pyrrolo[3,4-c]pyridine-2(3H)-carboxamide.

Example 1553B tert-butyl 4-(4-aminophenyl)cyclohex-3-enylcarbamate tert-Butyl 4-(4-nitrophenyl)cyclohex-3-enylcarbamate (2.55 g, 8.01 mmol) was suspended in ethanol (30 ml) followed by addition of sodium sulfide, nonahydrate (10.37 ml, 80 mmol) dissolved in water (30 ml). The mixture was heated to 80° C. for 1.5 h and extracted with dichloromethane; the organic layers were combined, dried over magnesium sulfate, filtered and concentrated to give the title compound.

Example 1553C tert-butyl 4-(4-(isoindoline-2-carboxamido)phenyl)cyclohex-3-enylcarbamate The title compound was prepared as described in Example 272B, substituting tert-butyl 4-(4-aminophenyl)cyclohex-3-enylcarbamate for 4-amino-N-propylbenzamide and isoindoline for methyl isoindoline-5-carboxylate hydrochloride.

Example 1553D

N-(4-(4-aminocyclohex-1-enyl)phenyl)isoindoline-2-carboxamide

The title compound was prepared as described in Example 2D, substituting tert-butyl 4-(4-(isoindoline-2-carboxamido)phenyl)cyclohex-3-enylcarbamate for tert-butyl 4-((4-(5-fluoroisoindoline-2-carboxamido)benzamido)methyl)benzylcarbamate.

Example 1553E

N-(4-{4-[(2-methylpropanoyl)amino]cyclohex-1-en-1-yl}phenyl)-1,3-dihydro-2H-isoindole-2-carboxamide The title compound was prepared as described in Example 1C, substituting N-(4-(4-aminocyclohex-1-enyl)phenyl)isoindoline-2-carboxamide for 3-phenylpropan-1-amine and isobutyric acid for 4-(isoindoline-2-carboxamido)benzoic acid. $^1$H NMR (300 MHz, DMSO-d$_6$) δ 8.36 (s, 1H), 7.70 (d, J=7.6 Hz, 1H), 7.54 (d, J=2.1 Hz, 2H), 7.46-7.23 (m, 6H), 6.06-5.96 (m, 1H), 4.76 (s, 4H), 3.85-3.75 (m, 1H), 2.43-2.26 (m, 3H), 2.11-1.96 (m, 1H), 1.95-1.75 (m, 1H), 1.69-1.48 (m, 1H), 1.10-0.82 (m, 6H); MS (ESI(+)) m/e 404 (M+H)$^+$.

Example 1554

N-[4-(4-{[(2R)-tetrahydrofuran-2-ylcarbonyl]amino}cyclohex-1-en-1-yl)phenyl]-1,3-dihydro-2H-isoindole-2-carboxamide The title compound was prepared as described in Example 1C, substituting N-(4-(4-aminocyclohex-1-enyl)phenyl)isoindoline-2-carboxamide for 3-phenylpropan-1-amine and -(2R)-tetrahydrofuran-2-carboxylic acid for 4-(isoindoline-2-carboxamido)benzoic acid. $^1$H NMR (300 MHz, DMSO-d$_6$) δ 8.36 (s, 1H), 7.61 (dt, J=9.2, 4.6 Hz, 1H), 7.58-7.45 (m, 2H), 7.49-7.23 (m, 6H), 6.02 (bs, 1H), 4.77 (s, 4H), 4.25-4.16 (m, 1H), 3.97-3.66 (m, 3H), 2.42-2.24 (m, 1H), 2.26-1.98 (m, 3H), 1.98-1.53 (m, 6H); MS (ESI(+)) m/e 432 (M+H)$^+$.

Example 1555

N-[4-(4-{[(2S)-tetrahydrofuran-2-ylcarbonyl]amino}cyclohex-1-en-1-yl)phenyl]-1,3-dihydro-2H-isoindole-2-carboxamide The title compound was prepared as described in Example 1C, substituting N-(4-(4-aminocyclohex-1-enyl)phenyl)isoindoline-2-carboxamide for 3-phenylpropan-1-amine and -(2S)-tetrahydrofuran-2-carboxylic acid for 4-(isoindoline-2-carboxamido)benzoic acid. $^1$H NMR (300 MHz, DMSO-d$_6$) δ 8.37 (s, 1H), 7.63 (dd, J=8.2, 3.5 Hz, 1H), 7.57-7.50 (m, 2H), 7.49-7.23 (m, 6H), 6.04-5.96 (m, 1H), 4.76 (s, 4H), 4.25-4.16 (m, 1H), 3.96-3.67 (m, 4H), 2.38-2.29 (m, 1H), 2.27-1.99 (m, 3H), 1.97-1.56 (m, 5H); MS (ESI(+)) m/e 432 (M+H)$^+$.

Example 1556

N-(4-{4-[(cyclopentylacetyl)amino]cyclohex-1-en-1-yl}phenyl)-1,3-dihydro-2H-isoindole-2-carboxamide The title compound was prepared as described in Example 1C, substituting N-(4-(4-aminocyclohex-1-enyl)phenyl)

isoindoline-2-carboxamide for 3-phenylpropan-1-amine and cyclopentylacetic acid for 4-(isoindoline-2-carboxamido)benzoic acid. $^1$H NMR (300 MHz, DMSO-d$_6$) δ 8.34 (s, 1H), 7.72 (d, J=7.6 Hz, 1H), 7.57-7.49 (m, 2H), 7.49-7.23 (m, 6H), 6.01 (bs, 1H), 4.76 (s, 4H), 3.90-3.74 (m, 1H), 2.49-2.25 (m, 2H), 2.20-1.99 (m, 3H), 1.94-1.82 (m, 1H), 1.68 (tdd, J=9.4, 8.9, 4.4 Hz, 2H), 1.64-1.42 (m, 7H), 1.31-1.01 (m, 2H); MS (ESI(+)) m/e 444 (M+H)$^+$.

Example 1557

N-(4-{4-[(cyclopropylacetyl)amino]cyclohex-1-en-1-yl}phenyl)-1,3-dihydro-2H-isoindole-2-carboxamide The title compound was prepared as described in Example 1C, substituting N-(4-(4-aminocyclohex-1-enyl)phenyl)isoindoline-2-carboxamide for 3-phenylpropan-1-amine and cyclopropylacetic acid for 4-(isoindoline-2-carboxamido)benzoic acid. $^1$H NMR (300 MHz, DMSO-d$_6$) δ 8.36 (s, 1H), 7.70 (d, J=7.6 Hz, 1H), 7.66-7.47 (m, 2H), 7.47-7.24 (m, 6H), 6.02 (bs, 1H), 4.76 (s, 4H), 3.88-3.78 (m, 1H), 2.49-2.26 (m, 3H), 2.12-1.82 (m, 4H), 1.72-1.50 (m, 1H), 1.13-0.88 (m, 1H), 0.52-0.33 (m, 2H), 0.18-0.01 (m, 2H); MS (ESI(+)) m/e 416 (M+H)$^+$.

Example 1558

N-(4-{4-[(2-hydroxy-2-methylpropanoyl)amino]cyclohex-1-en-1-yl}phenyl)-1,3-dihydro-2H-isoindole-2-carboxamide The title compound was prepared as described in Example 1C, substituting N-(4-(4-aminocyclohex-1-enyl)phenyl)isoindoline-2-carboxamide for 3-phenylpropan-1-amine and 2-hydroxy-2-methylpropanoic acid for 4-(isoindoline-2-carboxamido)benzoic acid. $^1$H NMR (300 MHz, DMSO-d$_6$) δ 8.36 (s, 1H), 7.52 (t, J=8.6 Hz, 2H), 7.46-7.39 (m, 1H), 7.35 (tdd, J=8.8, 7.1, 3.7 Hz, 6H), 6.07-5.96 (m, 1H), 5.40 (s, 1H), 4.77 (s, 4H), 3.92-3.76 (m, 1H), 2.46 (s, 1H), 2.39-2.25 (m, 1H), 2.24-2.09 (m, 2H), 1.93-1.78 (m, 1H), 1.70 (dt, J=12.4, 7.7 Hz, 1H), 1.25 (s, 6H); MS (ESI(+)) m/e 420 (M+H)$^+$.

Example 1559

N-(4-{4-[(tetrahydro-2H-pyran-4-ylcarbonyl)amino]cyclohex-1-en-1-yl}phenyl)-1,3-dihydro-2H-isoindole-2-carboxamide The title compound was prepared as described in Example 1C, substituting N-(4-(4-aminocyclohex-1-enyl)phenyl)isoindoline-2-carboxamide for 3-phenylpropan-1-amine and tetrahydro-2H-pyran-4-carboxylic acid for 4-(isoindoline-2-carboxamido)benzoic acid. $^1$H NMR (300 MHz, DMSO-d$_6$) δ 8.36 (s, 1H), 7.76 (d, J=7.6 Hz, 1H), 7.57-7.49 (m, 2H), 7.46-7.23 (m, 6H), 6.02 (bs, 1H), 4.76 (s, 4H), 3.91-3.75 (m, 4H), 3.31-3.17 (m, 2H), 2.43-2.26 (m, 2H), 2.12-1.97 (m, 1H), 1.93-1.81 (m, 1H), 1.71-1.48 (m, 6H); MS (ESI(+)) m/e 446 (M+H)$^+$.

Example 1560

N-(4-{4-[(cyclohexylcarbonyl)amino]cyclohex-1-en-1-yl}phenyl)-1,3-dihydro-2H-isoindole-2-carboxamide The title compound was prepared as described in Example 1C, substituting N-(4-(4-aminocyclohex-1-enyl)phenyl)isoindoline-2-carboxamide for 3-phenylpropan-1-amine and cyclohexanecarboxylic acid for 4-(isoindoline-2-carboxamido)benzoic acid. $^1$H NMR (300 MHz, DMSO-d$_6$) δ 8.35 (s, 1H), 7.64 (d, J=7.6 Hz, 1H), 7.57-7.49 (m, 2H), 7.47-7.23 (m, 6H), 6.01 (bs, 1H), 4.76 (s, 4H), 3.84-3.54 (m, 1H), 2.49-2.24 (m, 2H), 2.20-1.93 (m, 2H), 1.91-1.77 (m, 1H), 1.78-1.48 (m, 6H), 1.47-1.06 (m, 6H); MS (ESI(+)) m/e 444 (M+H)$^+$.

What is claimed is:

1. A compound of Formula (Ic), or a pharmaceutically acceptable salt thereof

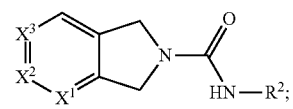

Formula (Ic)

wherein
$X^1$, $X^2$, and $X^3$ are CH; or
$X^1$ and $X^3$ are CH; and $X^2$ is N; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$; or
$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NO_2$, $N_3$, OH, C(O)H, $CF_3$, C(O)OH, or $C(O)NH_2$;
$R^2$ is alkyl, alkenyl, alkynyl, phenyl, thiophenyl, pyrazolyl, thiazolyl, pyridinyl, pyridazinyl, pyrazinyl, benzo[d]imidazolyl, isoindolinyl, cycloalkyl, or cycloalkenyl; wherein each $R^2$ alkyl, alkenyl, and alkynyl is substituted with one, two, three or four independently selected $R^4$, $OR^4$, $SR^4$, $S(O)R^4$, $SO_2R^4$, $C(O)R^4$, $CO(O)R^4$, $OC(O)R^4$, $OC(O)OR^4$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, C(O)H, (O), CN, $N_3$, $NO_2$, $CF_3$, $CF_2CF_3$, $OCF_3$, $OCF_2CF_3$, F, Cl, Br or I; wherein each $R^2$ phenyl is substituted at the para position with one independently selected $R^5$, $OR^5$, $SR^5$, $S(O)R^5$, $SO_2R^5$, $C(O)R^5$, CO(O)$R^5$, $OC(O)R^5$, $OC(O)OR^5$, $NH_2$, $NHR^5$, $N(NHC(O)R^5$, $NR^5C(O)R$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $CHNOR^5$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, C(O)H, C(O)OH, OH, CN, $N_3$, $CF_3$, $CF_2CF_3$, $OCF_3$, $OCF_2CF_3$, Br or I; wherein each $R^2$ phenyl is optionally additionally substituted with one F; wherein each $R^2$ heterocyclyl and cycloalkenyl is optionally substituted with one, two, three or four independently selected $R^5$, $OR^5$, $SR^5$, $S(O)R^5$, $SO_2R^5$, $C(O)R^5$, CO(O)$R^5$, OC(O)$R^5$, OC(O)O$R^5$, $NH_2$, $NHR^5$, $N(R^5)_2$, $NHC(O)R^5$, $NR^5C(O)R^5$, $NHS(O)_2R^5$, $NR^5(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, C(O)H, C(O)OH, OH, CN, N$_3$, CF$_3$, CF$_2$CF$_3$, OCF$_3$, OCF$_2$CF$_3$, F, Cl, Br or I; wherein each R$^2$ cycloalkyl is substituted with one, two, three or four independently selected R$^5$, OR$^5$, SR$^5$, S(O)R$^5$, SO$_2$R$^5$, C(O)R$^5$, CO(O)R$^5$, OC(O) R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O) N(R$^5$)$_2$, NR$^5$C(O)NHR$^2$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, OH, CN, N$_3$, CF$_3$, CF$_2$CF$_3$, OCF$_3$, OCF$_2$CF$_3$, F, Cl, Br or I;

R$^3$, at each occurrence, is independently selected alkyl, alkenyl, alkynyl, aryl, or heterocyclyl; wherein each R$^3$ alkyl, alkenyl, and alkynyl is optionally substituted with one, two, three or four independently selected R$^6$, OR$^6$, SR$^6$, S(O)R$^6$, SO$_2$R$^°$, C(O)R$^6$, CO(O)R$^6$, OC(O)R$^6$, OC(O)OR$^6$, NH$_2$, NHR$^6$, N(R$^6$)$_2$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)NHR$^6$, NR$^6$C(O)N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, SO$_2$NH$_2$, SO$_2$NHR$^6$, SO$_2$N(R$^6$)$_2$, C(O)H, C(O)OH, OH, (O), CN, N$_3$, NO$_2$, CF$_3$, CF$_2$CF$_3$, OCF$_3$, OCF$_2$CF$_3$, F, Cl, Br or I;

R$^4$, at each occurrence, is independently selected alkyl, alkenyl, alkynyl, aryl, cycloalkyl, or heterocyclyl; wherein each R$^4$ alkyl, alkenyl, and alkynyl is optionally substituted with one, two, three or four independently selected R$^7$, OR$^7$, SR$^7$, S(O)R$^7$, SO$_2$R$^7$, C(O)R$^7$, OC(O) R$^7$, OC(O)OR$^7$, NH$_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, C(O)H, OH, (O), CN, N$_3$, NO$_2$, CF$_3$, CF$_2$CF$_3$, OCF$_3$, OCF$_2$CF$_3$, F, Cl, Br or I; wherein each R$^4$ aryl and heterocycyl is optionally substituted with one, two, three or four independently selected R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, NHC(O)R$^8$, NR$^8$C(O)R$^8$, NHS(O)$_2$R$^8$, NR$^8$S(O)$_2$R$^8$, NHC(O)OR$^8$, NR$^8$C(O) OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O) NHR$^8$, C(O)N(R$^8$)$_2$, C(O)NHOH, C(O)NHOR$^8$, C(O) NHSO$_2$R$^8$, C(O)NR$^8$SO$_2$R$^8$, SO$_2$NH$_2$, SO$_2$NHR$^8$, SO$_2$N(R$^8$)$_2$, C(O)H, C(O)OH, OH, CN, N$_3$, NO$_2$, CF$_3$, CF$_2$CF$_3$, OCF$_3$, OCF$_2$CF$_3$, F, Cl, Br or I;

R$^5$, at each occurrence, is independently selected alkyl, alkenyl, alkynyl, aryl, heterocyclyl, cycloalkyl, or cycloalkenyl; wherein each R$^5$ alkyl, alkenyl, and alkynyl is optionally substituted with one, two, three or four independently selected R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N(R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O)NHSO$_2$R$^9$, C(O) NR$^9$SO$_2$R$^9$, SO$_2$NH$_2$, SO$_2$NHR$^9$, SO$_2$N(R$^9$)$_2$, C(O)H, C(O)OH, OH, (O), CN, N$_3$, NO$_2$, CF$_3$, CF$_2$CF$_3$, OCF$_1$, OCF$_2$CF$_3$, F, Cl, Br or I;

R$^6$, at each occurrence, is independently selected alkyl, alkenyl, alkynyl, aryl, heterocyclyl, cycloalkyl, or cycloalkenyl; wherein each R$^6$ alkyl, alkenyl, and alkynyl is optionally substituted with one, two, three or four independently selected R$^{10}$, OR$^{10}$, SR$^{10}$, S(O)R$^{10}$, SO$_2$R$^{10}$, NHR$^{10}$, N(R$^{10}$)$_2$, C(O)R$^{10}$, C(O)NH$_2$, C(O) NHR$^{10}$, C(O)N(R$^{10}$)$_2$, NHC(O)R$^{10}$, NR$^{10}$C(O)R$^{10}$, NHSO$_2$R$^{10}$, NHC(O)OR$^{10}$, SO$_2$NH$_2$, SO$_2$NHR$^{10}$, SO$_2$N(R$^{10}$)$_2$, NHC(O)NH$_2$, NHC(O)NHR$^{10}$, OH, (O), C(O)OH, N$_3$, CN, NH$_2$, CF$_3$, CF$_2$CF$_3$, F, Cl, Br or I;

R$^7$, at each occurrence, is independently selected alkyl, alkenyl, alkynyl, aryl, heterocyclyl, cycloalkyl, or cycloalkenyl; wherein each R$^7$ alkyl, alkenyl, and alkynyl is optionally substituted with one, two, three or four independently selected R$^{11}$, OR$^{11}$, SR$^{11}$, S(O)R$^{11}$, SO$_2$R$^{11}$, NHR$^{11}$, N(R$^{11}$)$_2$, C(O)R$^{11}$, C(O)NH$_2$, C(O) NHR$^{11}$, C(O)N(R$^{11}$)$_2$, NHC(O)R$^{11}$, NR$^{11}$C(O)R$^{11}$, NHSO$_2$R$^{11}$, NHC(O)OR$^{11}$, SO$_2$NH$_2$, SO$_2$NHR$^{11}$, SO$_2$N(R$^{11}$)$_2$, NHC(O)NH$_2$, NHC(O)NHR$^{11}$, OH, (O), C(O)OH, N$_3$, CN, NH$_2$, CF$_3$, CF$_2$CF$_3$, F Cl, Br or I;

R$^8$, at each occurrence, is independently selected alkyl, alkenyl, alkynyl, aryl, heterocyclyl, cycloalkyl, or cycloalkenyl; wherein each R$^8$ alkyl, alkenyl, and alkynyl is optionally substituted with one, two, three or four independently selected R$^{12}$, OR$^{12}$, SR$^{12}$, S(O)R$^{12}$, SO$_2$R$^{12}$, NHR$^{12}$, N(R$^{12}$)$_2$, C(O)R$^{12}$, C(O)NH$_2$, C(O) NHR$^{12}$, C(O)N(R$^{12}$)$_2$, NHC(O)R$^{12}$, NR$^{12}$C(O)R$^{12}$, NHSO$_2$R$^{12}$, NHC(O)OR$^{12}$, SO$_2$NH$_2$, SO$_2$NHR$^{12}$, SO$_2$N(R$^{12}$)$_2$, NHC(O)NH$_2$, NHC(O)NHR$^{12}$, OH, (O), C(O)OH, N$_3$, CN, NH$_2$, CF$_3$, CF$_2$CF$_3$, F, Cl, Br or I;

R$^9$, at each occurrence, is independently selected alkyl, alkenyl, alkynyl, aryl, heterocyclyl, cycloalkyl, or cycloalkenyl; wherein each R$^9$ alkyl, alkenyl, and alkynyl is optionally substituted with one, two, three or four independently selected alkoxy, OH, cycloalkyl, aryl, or heterocyclyl;

R$^{10}$, at each occurrence, is independently selected alkyl, alkenyl, alkynyl, aryl, heterocyclyl, cycloalkyl, or cycloalkenyl;

R$^{11}$, at each occurrence, is independently selected alkyl, alkenyl, alkynyl, aryl, heterocyclyl, cycloalkyl, or cycloalkenyl;

R$^{12}$, at each occurrence, is independently selected alkyl, alkenyl, alkynyl, aryl, heterocyclyl, cycloalkyl, or cycloalkenyl; wherein each R$^{12}$ alkyl, alkenyl, and alkynyl is optionally substituted with one or more alkoxy;

wherein the cyclic moieties represented by R$^3$, R$^5$, R$^6$, R$^7$, R$^8$, R$^9$, R$^{10}$, R$^{11}$, and R$^{12}$ are optionally substituted with one, two, three, four, five, or six independently selected R$^{13}$, OR$^{13}$, SR$^{13}$, S(O)R$^{13}$, SO$_2$R$^{13}$, C(O)R$^{13}$, CO(O) R$^{13}$, OC(O)R$^{13}$, OC(O)OR$^{13}$, NH$_2$, NHR$^{13}$, N(R$^{13}$)$_2$, NHC(O)R$^{13}$, NR$^{13}$C(O)R$^{13}$, NHS(O)$_2$R$^{13}$, NR$^{13}$S(O)$_2$R$^{13}$, NHC(O)OR$^{13}$, NR$^{13}$C(O)OR$^{13}$, NHC(O)NH$_2$, NHC(O)NHR$^{13}$, NHC(O)N(R$^{13}$)$_2$, NR$^{13}$C(O) NHR$^{13}$, NR$^{13}$C(O)N(R$^{13}$)$_2$, C(O)NH$_2$, C(O)NHR$^{13}$, C(O)N(R$^{13}$)$_2$, C(O)NHOH, C(O)NHOR$^{13}$, C(O) NHSO$_2$R$^{13}$, C(O)NR$^{13}$SO$_2$R$^{13}$, SO$_2$NH$_2$, SO$_2$NHR$^{13}$, SO$_2$N(R$^{13}$)$_2$, C(O)H, C(O)OH, OH, CN, N$_3$, NO$_2$, CF$_3$, CF$_2$CF$_3$, OCF$_3$, OCF$_2$CF$_3$, SCF$_3$, F, Cl, Br or I;

R$^{13}$, at each occurrence, is independently selected alkyl, alkenyl, alkynyl, aryl, tetrahydrofuranyl, pyridazinyl, pyrazinyl, primidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolyl, thienyl, furanyl, morpholinyl, isooxazolyl, cycloalkyl, or cycloalkenyl; wherein each R$^{13}$ alkyl, alkenyl, and alkynyl is optionally substituted with one, two, three or four independently selected R$^{14}$, OR$^{14}$, SR$^{14}$, S(O)R$^{14}$, SO$_2$R$^{14}$, C(O)R$^{14}$, OC(O)R$^{14}$, OC(O)OR$^{14}$, NH$_2$, NHR¹⁴, N(R¹⁴)₂, NHC(O)R¹⁴, NR¹⁴C(O)R¹⁴, NHS(O)₂R¹⁴, NR¹⁴S(O)₂R¹⁴, NHC(O)OR¹⁴, NR¹⁴C(O)OR¹⁴, NHC(O)NH₂, NHC(O)NHR¹⁴, NHC(O)N(R¹⁴)₂, NR¹⁴C(O)NHR¹⁴, NR¹⁴C(O)N(R¹⁴)₂, C(O)NH₂, C(O)NHR¹⁴, C(O)N(R¹⁴)₂, C(O)NHOH, C(O)NHOR¹⁴, C(O)NHSO₂R¹⁴, C(O)NR¹⁴SO₂R¹⁴, SO₂NH₂, SO₂NHR¹⁴, SO₂N(R¹⁴)₂, C(O)H, C(O)OH, OH, (O), CN, N₃, NO₂, CF₃, CF₂CF₃, OCF₃, OCF₂CF₃, F, Cl, Br or I; wherein each R¹³ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolyl, thienyl, furanyl, morpholinyl, isooxazolyl, cycloalkyl, and cycloalkenyl is optionally substituted with one, two, three or four independently selected R¹⁵, OR¹⁵, SR¹⁵, S(O)R¹⁵, SO₂R¹⁵, C(O)R¹⁵, CO(O)R¹⁵, OC(O)R¹⁵, OC(O)OR¹⁵, NH₂, NHR¹⁵, N(R¹⁵)₂, NHC(O)R¹⁵, NR¹⁵C(O)R¹⁵, NHS(O)₂R¹⁵, NR¹⁵S(O)₂R¹⁵, NHC(O)OR¹⁵, NR¹⁵C(O)OR¹⁵, NHC(O)NH₂, NHC(O)NHR¹⁵, NHC(O)N(R¹⁵)₂, NR¹⁵C(O)NHR¹⁵, NR¹⁵C(O)N(R¹⁵)₂, C(O)NH₂, C(O)NHR¹⁵, C(O)N(R¹⁵)₂, C(O)NHOH, C(O)NHOR¹⁵, C(O)NHSO₂R¹⁵, C(O)NR¹⁵SO₂R¹⁵, SO₂NH₂, SO₂NHR¹⁵, SO₂N(R¹⁵)₂, C(O)H, C(O)OH, OH, CN, N₃, NO₂, CF₃, CF₂CF₃, OCF₃, OCF₂CF₃, F, Cl, Br or I;

R¹⁴, at each occurrence, is independently selected alkyl, alkenyl, alkynyl, aryl, heterocyclyl, cycloalkyl, or cycloalkenyl; wherein each R¹⁴ alkyl, alkenyl, and alkynyl is optionally substituted with one, two, three or four independently selected heterocyclyl, alkoxy, NH₂, SO₂NH₂, C(O)H, C(O)OH, OH, (O), CN, N₃, NO₂, CF₃, CF₂CF₃, OCF₃, OCF₂CF₃, F, Cl, Br or I; wherein each R¹⁴ aryl, heterocyclyl, cycloalkyl, and cycloalkenyl is optionally substituted with one, two, three or four independently selected R¹⁶, OR¹⁶, OH, F, Cl, Br, or I; wherein the R¹⁶ alkyl is optionally substituted with one, two, three or four alkoxy;

R¹⁵, at each occurrence, is independently selected alkyl; wherein the R¹⁵ alkyl is optionally substituted with one, two, three or four alkoxy;

R¹⁶, at each occurrence, is independently selected alkyl, wherein the R¹⁶ alkyl is optionally substituted with one, two, three or four alkoxy;

with the proviso that when X¹, X², and X³ are CH and R² is phenyl; R⁵ is not methyl;

with the proviso that when X¹, X², and X³ are CH, and R² is phenyl substituted with OR⁵; R⁵ is not methyl;

with the proviso that when R² is alkyl; R² is C₄-C₆-alkyl; and with the proviso that when R¹³ is piperidinyl, it is substituted piperidinyl.

2. A compound having Formula (Vc), or a pharmaceutically acceptable salt thereof

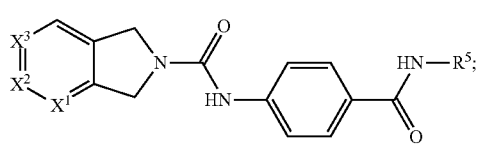

(Vc)

wherein
X¹, X², and X³ are CH; or
X¹ and X³ are CH; and X² is CR¹; or
X² and X³ are CH; and X¹ is CR¹; or
X¹ is CH; and X² and X³ are CR¹;
R¹ is R³, OR³, SR³, S(O)R³, SO₂R³, C(O)R³, C(O)OR³, OC(O)R³, NHR³, N(R³)₂, C(O)NH₂, C(O)NHR³, C(O)N(R³)₂, NHC(O)R³, NR³C(O)R³, NHC(O)OR³, NR³C(O)OR³, SO₂NH₂, SO₂NHR³, SO₂N(R³)₂, NHSO₂R³, NR³SO₂R³, NHSO₂NHR³, NHSO₂N(R³)₂, NR³SO₂NHR³, NR³SO₂N(R³)₂, C(O)NHSO₂R³, NHSO₂NHR³ , F, Cl, Br, I, CN, NH₂, NO₂, N₃, OH, C(O)H, CF₃, C(O)OH, or C(O)NH₂;

R³, at each occurrence, is independently selected alkyl, alkenyl, alkynyl, aryl, or heterocyclyl; wherein each R³ alkyl, alkenyl, and alkynyl is optionally substituted with one, two, three or four independently selected R⁶, OR⁶, SR⁶, S(O)R⁶, SO₂R⁶, C(O)R⁶, CO(O)R⁶ OC(O)R⁶, OC(O)OR⁶, NH₂, NHR⁶, N(R⁶)₂, NHC(O)R⁶, NR⁶C(O)R⁶, NHS(O)₂R⁶, NR⁶S(O)₂R⁶, NHC(O)OR⁶, NR⁶C(O)OR⁶, NHC(O)NH₂, NHC(O)NHR⁶, NHC(O)N(R⁶)₂, NR⁶C(O)NHR⁶, NR⁶C(O)N(R⁶)₂, C(O)NH₂, C(O)NHR⁶, C(O)N(R⁶)₂, C(O)NHOH, C(O)NHOR⁶, C(O)NHSO₂R⁶, C(O)NR⁶SO₂R⁶, SO₂NH₂, SO₂NHR⁶, SO₂N(R⁶)₂, C(O)H, C(O)OH, (O), CN, N₃, NO₂, CF₃, CF₂CF₃, OCF₃, OCF₂CF₃, F, Cl, Br or I;

R⁵, at each occurrence, is independently selected alkyl, alkenyl, alkynyl, aryl, heterocyclyl, cycloalkyl, or cycloalkenyl; wherein each R⁵ alkyl, alkenyl, and alkynyl is optionally substituted with one, two, three or four independently selected R⁹, OR⁹, SR⁹, S(O)R⁹, SO₂R⁹, C(O)R⁹, CO(O)R⁹, OC(O)R⁹, OC(O)OR⁹, NH₂, NHR⁹, N(R⁹)₂, NHC(O)R, NR⁹C(O)R⁹, NHS(O)₂R⁹, NR⁹S(O)₂R⁹, NHC(O)OR⁹, NR⁹C(O)OR⁹, NHC(O)NH₂, NHC(O)NHR⁹, NHC(O)N(R⁹)₂, NR⁹C(O)NHR⁹, NR⁹C(O)N(R⁹)₂, C(O)NH₂, C(O)NHR⁹, C(O)N(R⁹)₂, C(O)NHOH, C(O)NHOR⁹, C(O)NHSO₂R⁹, C(O)NR⁹SO₂R⁹, SO₂NH₂, SO₇NHR⁹, SO₂N(R⁹)₂, C(O)H, C(O)OH, OH, (O), CN, N₃, NO₂, CF₃, CF₂CF₃, OCF₃, OCF₂CF₃, F, Cl, Br or I;

R⁶, at each occurrence, is independently selected alkyl, alkenyl, alkynyl, aryl, heterocyclyl, cycloalkyl, or cycloalkenyl; wherein each R⁶ alkyl, alkenyl, and alkynyl is optionally substituted with one, two, three or four independently selected R¹⁰, OR¹⁰, SR¹⁰, S(O)R¹⁰, SO₂R¹⁰, NHR¹⁰, N(R¹⁰)₂, C(O)R¹⁰, C(O)NH₂, C(O)NHR¹⁰, C(O)N(R¹⁰)₂, NHC(O)R¹⁰, NR¹⁰C(O)R¹⁰, NHSO₂R¹⁰, NHC(O)OR¹⁰, SO₂NH₂, SO₂NHR¹⁰, SO₂N(R¹⁰)₂, NHC(O)NH₂, NHC(O)NHR¹⁰, OH, (O), C(O)OH, N₃, CN, NH₂, CF₃, CF₂CF₃, F, Cl, Br or I;

R⁹, at each occurrence, is independently selected alkyl, alkenyl, alkynyl, aryl, heterocyclyl, cycloalkyl, or cycloalkenyl; wherein each R⁹ alkyl, alkenyl, and alkynyl is optionally substituted with one, two, three or four independently selected alkoxy, OH, cycloalkyl, aryl, or heterocyclyl;

R¹⁰, at each occurrence, is independently selected alkyl, alkenyl, alkynyl, aryl, heterocyclyl, cycloalkyl, or cycloalkenyl;

wherein the cyclic moieties represented by R³, R⁵, R⁶, R⁹, and R¹⁰ are optionally substituted with one, two, three, four, five, or six independently selected R¹³, OR¹³, SR¹³, S(O)R¹³, SO₂R¹³, C(O)R¹³, CO(O)R¹³, OC(O)R¹³, OC(O)OR¹³, NH₂, NHR¹³, N(R¹³)₂, NHC(O)R¹³, NR³C(O)R¹³, NHS(O)₂R¹³, NR¹³S(O)₂R¹³, NHC(O)OR¹³, NR¹³C(O)OR NHC(O)NH₂, NHC(O)NHR¹³, NHC(O)N(R¹³)₂, NR¹³C(O)NHR¹³, NR¹³C(O)N(R¹³)₃, C(O)NH₂, C(O)NHR¹³, C(O)N(R¹³)₂, C(O)NHOH, C(O)NHOR¹³, C(O)NHSO₂R¹³, C(O)

NR$^{13}$SO$_2$R$^{13}$, SO$_2$NH$_2$, SO$_2$NHR$^{13}$, SO$_2$N(R$^{13}$)$_2$, C(O)H, C(O)OH, OH, CN, N$_3$, NO$_2$, CF$_3$, CF$_2$CF$_3$, OCF$_3$, OCF$_2$CF$_3$, SCF$_3$, F, Cl, Br or I;

R$^{13}$, at each occurrence, is independently selected alkyl, alkenyl, alkynyl, aryl, tetrahydrofuranyl, pyridazinyl, pyrazinyl, primidinyl; pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolyl, thienyl, furanyl, morpholinyl, isooxazolyl, cycloalkyl, or cycloalkenyl; wherein each R$^{13}$ alkyl, alkenyl, and alkynyl is optionally substituted with one, two, three or four independently selected R$^{14}$, OR$^{14}$, SR$^{14}$, S(O)R$^{14}$, SO$_2$R$^{14}$, C(O)R$^{14}$, OC(O)R$^{14}$, OC(O)OR$^{14}$, NH$_2$, NHR$^{14}$, N(R$^{14}$)$_2$, NHC(O)R$^{14}$, NR$^{14}$C(O)R$^{14}$, NHS(O)$_2$R$^{14}$, NR$^{14}$S(O)$_2$R$^{14}$, NHC(O)OR$^{14}$, NR$^{14}$C(O)OR$^{14}$, NHC(O)NH$_2$, NHC(O)NHR$^{14}$, NHC(O)N(R$^{14}$)$_2$, NR$^{14}$C(O)NHR$^{14}$, NR$^{14}$C(O)N(R$^{14}$)$_2$, C(O)NH$_2$, C(O)NHR$^{14}$, C(O)N(R$^{14}$)$_2$, C(O)NHOH, C(O)NHOR$^{14}$, C(O)NHSO$_2$R$^{14}$, C(O)NR$^{14}$SO$_2$R$^{14}$, SO$_2$NH$_2$, SO$_2$NHR$^{14}$, SO$_2$N(R$^{14}$)$_2$, C(O)H, C(O)OH, OH, (O), CN, N$_3$, NO$_2$, CF$_3$, CF$_2$CF$_3$, OCF$_3$, OCF$_2$CF$_3$, F, Cl, Br or I; wherein each R$^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolyl, thienyl, furanyl, morpholinyl, isooxazolyl, cycloalkyl, and cycloalkenyl is optionally substituted with one, two, three or four independently selected R$^{15}$, OR$^{15}$, SR$^{15}$, S(O)R$^{15}$, SO$_2$R$^{15}$, C(O)R$^{15}$, CO(O)R$^{15}$, OC(O)R$^{15}$, OC(O)OR$^{15}$, NH$_2$, NHR$^{15}$, N(R$^{15}$)$_2$, NHC(O)R$^{15}$, NR$^{15}$C(O)R$^{15}$, NHS(O)$_2$R$^{15}$, NR$^{15}$S(O)$_2$R$^{15}$, NHC(O)OR$^{15}$, NR$^{15}$C(O)OR$^{15}$, NHC(O)NH$_2$, NHC(O)NHR$^{15}$, NHC(O)N(R$^{15}$)$_2$, NR$^{15}$C(O)NHR$^{15}$, NR$^{15}$C(O)N(R$^{15}$)$_2$, C(O)NH$_2$, C(O)NHR$^{15}$, C(O)N(R$^{15}$)$_2$, C(O)NHOH, C(O)NHOR$^{15}$, C(O)NHSO$_2$R$^{15}$, C(O)NR$^{15}$SO$_2$R$^{15}$, SO$_2$NH$_2$, SO$_2$NHR$^{15}$, SO$_2$N(R$^{15}$)$_2$, C(O)H, C(O)OH, OH, CN, N$_3$, NO$_2$, CF$_3$, CF$_2$CF$_3$, OCF$_3$, OCF$_2$CF$_3$, F, Cl, Br or I;

R$^{14}$, at each occurrence, is independently selected alkyl, alkenyl, alkynyl, aryl, heterocyclyl, cycloalkyl, or cycloalkenyl; wherein each R$^{14}$ alkyl, alkenyl, and alkynyl is optionally substituted with one, two, three or four independently selected heterocyclyl, alkoxy, NH$_2$, SO$_2$NH$_2$, C(O)H, C(O)OH, OH, (O), CN, N$_3$, NO$_2$, CF$_3$, CF$_2$CF$_3$, OCF$_3$, OCF$_2$CF$_3$, F, Br or I; wherein each R$^{14}$ aryl, heterocyclyl, cycloalkyl, and cycloalkenyl is optionally substituted with one, two, three or four independently selected R$^{16}$, OR$^{16}$, OH, F, Cl, Br, or I;

R$^{15}$, at each occurrence, is independently selected alkyl, wherein the R$^{15}$ alkyl is optionally substituted with one, two, three or four alkoxy; and R$^{16}$, at each occurrence, is independently selected alkyl, wherein the R$^{16}$ alkyl is optionally substituted with one, two, three or four alkoxy;

with the proviso that when R$^{13}$ is piperidinyl, it is substituted piperidinyl.

3. A compound having Formula (VIIc), or a pharmaceutically acceptable salt thereof

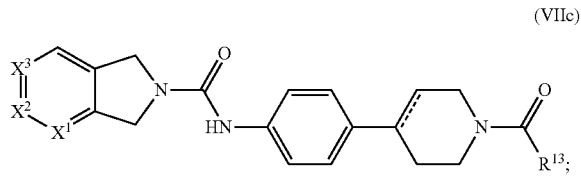

(VIIc)

wherein

X$^1$, X$^2$, and X$^3$ are CH; or
X$^1$ and X$^3$ are CH; and X$^2$ is CR$^1$; or
X$^2$ and X$^3$ are CH; and X$^1$ is CR$^1$; or
X$^1$ is CH; and X$^2$ and X$^3$ are CR$^1$;

⁓ indicates a single or double bond;

R$^3$ is R$^3$, OR$^3$, SR$^3$, S(O)R$^3$, SO$_2$R$^3$, C(O)R$^3$, C(O)OR$^3$, OC(O)R$^3$, N(R$^3$)$_2$, C(O)NH$_2$, C(O)NHR$^3$, C(O)N(R$^3$)$_2$, NHC(O)R$^3$, NR$^3$C(O)R$^3$, NHC(O)OR$^3$, NR$^3$C(O)OR$^3$, SO$_2$NH$_2$, SO$_2$NHR$^3$, SO$_2$N(R$^3$)$_2$, NHSO$_2$R$^3$, NR$^3$SO$_2$R$^3$, NHSO$_2$NHR$^3$, NHSO$_2$N(R)$_2$, NR$^3$SO$_2$NHR$^3$, NR$^3$SO$_2$N(R$^3$)$_2$, C(O)NHSO$_2$R$^3$, NHSO$_2$NHR$^3$, F, Cl, Br, I, CN, NH$_2$, NO$_2$, N$_3$, OH, C(O)H, CF$_3$, C(O)OH, or C(O)NH$_2$;

R$^3$, at each occurrence, is independently selected alkyl, alkenyl, alkynyl, aryl, or heterocyclyl wherein each R$^3$ alkyl, alkenyl, and alkynyl is optionally substituted with one, two, three or four independently selected R$^6$, OR$^6$, SR$^6$, S(O)R$^6$, SO$_2$R$^6$, C(O)R$^6$, CO(O)R$^6$, OC(O)R$^6$, OC(O)OR$^6$, N(R$^6$)$_2$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)NHR$^6$, NR$^6$C(O)N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, SO$_2$NH$_2$, SO$_2$NHR$^6$, SO$_2$N(R$^6$)$_2$, C(O)H, C(O)OH, OH, (O), CN, N$_3$, —NO$_2$, CF$_3$, CF$_2$CF$_3$, OCF$_2$CF$_3$, F, Cl, Br or I;

R$^6$, at each occurrence, is independently selected alkyl, alkenyl, alkynyl, aryl, heterocyclyl, cycloalkyl, or cycloalkenyl; wherein each R$^6$ alkyl, alkenyl, and alkynyl is optionally substituted with one, two, three or four independently selected R$^{10}$, OR$^{10}$, SR$^{10}$, S(O)R$^{10}$, SO$_2$R$^{10}$, NHR$^{10}$, N(R$^{10}$)$_2$, C(O)R$^{10}$, C(O)NH$_2$, C(O)NHR$^{10}$, C(O)N(R$^{10}$)$_2$, NHC(O)R$^{10}$, NR$^{10}$C(O)R$^{10}$, NHSO$_2$R$^{10}$, —NHC(O)OR$^{10}$, SO$_2$NH$_2$, SO$_2$NHR$^{10}$, SO$_2$N(R$^{10}$)$_2$, NHC(O)NH$_2$, NHC(O)NHR$^{10}$, OH, (O), C(O)OH, N$_3$, CN, NH$_2$, CF$_3$, CF$_2$CF$_3$, Cl, Br or I;

R$^{10}$, at each occurrence, is independently selected alkyl, alkenyl, alkynyl, aryl, heterocyclyl, cycloalkyl, or cycloalkenyl;

wherein the cyclic moieties represented by R$^3$, R$^6$, and R$^{10}$ are optionally substituted with one, two, three, four, five, or six independently selected R$^{13}$, OR$^{13}$, SR$^{13}$, S(O)R$^{13}$, SO$_2$R$^{13}$, C(O)R$^{13}$, CO(O)R$^{13}$, OC(O)R$^{13}$, OC(O)OR$^{13}$, NH, NHR$^{13}$, N(R$^{13}$)$_2$, NHC(O)R$^{13}$, NR$^{13}$C(O)R$^{13}$, NHS(O)$_2$R$^{13}$, NR$^{13}$S(O)$_2$R$^{13}$, NHC(O)OR$^{13}$, NR$^{13}$C(O)OR$^{13}$, NHC(O)NH$_2$, NHC(O)NHR$^{13}$, NHC(O)N(R$^{13}$)$_2$, NR$^{13}$C(O)NHR$^{13}$, NR$^{13}$C(O)N(R$^{13}$)$_2$, C(O)NH$_2$, C(O)NHR$^{13}$, C(O)N(R$^{13}$)$_2$, C(O)NHOH, C(O)NHOR$^{13}$, C(O)NHSO$_2$R$^{13}$, C(O)NR$^{13}$SO$_2$R$^{13}$, SO$_2$NH$_2$, SO$_2$NHR$^{13}$, SO$_2$N(R$^{13}$)$_2$, C(O)H, C(O)OH, OH, CN, N$_3$, NO, CF$_3$, CF$_2$CF$_3$, OCF$_3$, OCF$_2$CF$_3$, SCF$_3$, F, Br or I, R$^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]-pyridinyl, furo[3,2-c]pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolyl, thienyl, furanyl, morpholinyl, isooxazolyl, cycloalkyl, or cycloalkenyl; wherein each $R^{13}$ alkyl, alkenyl, and alkynyl is optionally substituted with one, two, three or four independently selected $R^{14}$, $OR^{14}$, $S(O)R^{14}$, $SO_2R^{14}$, $C(O)R^{14}$, $OC(O)R^{14}$, $OC(O)OR^{14}$, $NH_2$, $NHR^{14}$, $N(R^{14})_2$, $NHC(O)R^{14}$, $NR^{14}C(O)R^{14}$, $NH S(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $S(O)_2N(R^{14})_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolyl, thienyl, furanyl, morpholinyl, isooxazolyl, cycloalkyl, and cycloalkenyl is optionally substituted with one, two, three or four independently selected $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $C(O)H$, $C(O)OH$, $OH$, $CN$, $N_3$, $NO_2$, $CF_3$, $CF_2CF_3$, $OCF_3$, $OCF_2CF_3$, F, Cl, Br or I;

$R^{14}$, at each occurrence, is independently selected alkyl, alkenyl, alkynyl, aryl, heterocyclyl, cycloalkyl, or cycloalkenyl; wherein each $R^{14}$ alkyl, alkenyl, and alkynyl is optionally substituted with one, two, three or four independently selected heterocyclyl, alkoxy, $NH_2$, $SO_2NH_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{14}$ aryl, heterocyclyl, cycloalkyl, and cycloalkenyl is optionally substituted with one, two, three or four independently selected $R^{16}$, $R^{16}$, OH, F, Cl, Br, or I;

$R^{15}$, at each occurrence, is independently selected alkyl, wherein the $R^{15}$ alkyl is optionally substituted with one, two, three or four alkoxy; and $R^{16}$, at each occurrence, is independently selected alkyl, wherein the $R^{10}$ alkyl is optionally substituted with one, two, three or four alkoxy;

with the proviso that when $R^{13}$ is piperidinyl, it is substituted piperidinyl.

4. A compound having Formula (VIIc), or a pharmaceutically acceptable salt thereof

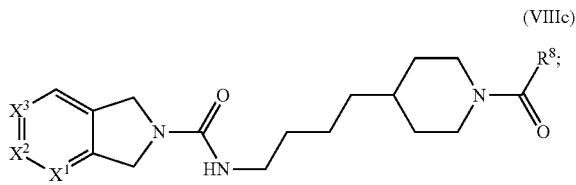

(VIIIc)

wherein
$X^1$, $X^2$, and $X^3$ are CH; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$;

$R^1$ is $R^3$, $OR^3$, $SR^3$, $S(O)R^3$, $SO_2R^3$, $C(O)R^3$, $C(O)OR^3$, $OC(O)R^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, $C(O)H$, $CF_3$, $C(O)OH$, or $C(O)NH_2$;

$R^3$, at each occurrence, is independently selected alkyl, alkenyl, alkynyl, aryl, or heterocyclyl wherein each $R^3$ alkyl, alkenyl, and alkynyl is optionally substituted with one, two, three or four independently selected $R^6$, $OR^6$, $SR^6$, $S(O)R^6$, $SO_2R^6$, $C(O)R^6$, $CO(O)R^6$, $OC(O)R^6$, $OC(O)OR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $OH$, $(O)$, $CN$, $N_3$, $—NO_2$, $CF_3$, $CF_2CF_3$, $OCF_2CF_3$, F, Cl, Br or I;

$R^6$, at each occurrence, is independently selected alkyl, alkenyl, alkynyl, aryl, heterocyclyl, cycloalkyl, or cycloalkenyl; wherein each $R^6$ alkyl, alkenyl, and alkynyl is optionally substituted with one, two, three or four independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $—NHC(O)OR^{10}$, $SO_2NH_2$, $SO_2NHR^{10}$, $SO_2N(R^{10})_2$, $NHC(O)NH_2$, $NHC(O)NHR^{10}$, OH, $(O)$, $C(O)OH$, $N_3$, $CN$, $NH_2$, $CF_3$, $CF_2CF_3$, Cl, Br or I;

$R^8$, at each occurrence, is independently selected alkyl, alkenyl, alkynyl, aryl, heterocyclyl, cycloalkyl, or cycloalkenyl; wherein each $R^8$ alkyl, alkenyl, and alkynyl is optionally substituted with one, two, three or four independently selected $R^{12}$, $OR^{12}$, $SR^{12}$, $S(O)R^{12}$, $SO_2R^{12}$, $NHR^{12}$, $N(R^{12})_2$, $C(O)R^{12}$, $C(O)NH_2$, $C(O)NHR^{12}$, $C(O)N(R^{12})_2$, $NHC(O)R^{12}$, $NR^{12}C(O)R^{12}$, $NHSO_2R^{12}$, $NHC(O)OR^{12}$, $SO_2NH_2$, $SO_2NHR^{12}$, $SO_2N(R^{12})_2$, $NHC(O)NH_2$, $NHC(O)NHR^{12}$, OH, $(O)$, $C(O)OH$, $N_3$, $CN$, $NH_2$, $CF_3$, $CF_2CF_3$, F, Cl, Br or I;

$R^{10}$, at each occurrence, is independently selected alkyl, alkenyl, alkynyl, aryl, heterocyclyl, cycloalkyl, or cycloalkenyl;

$R^{12}$, at each occurrence, is independently selected alkyl, alkenyl, alkynyl, aryl, heterocyclyl, cycloalkyl, or cycloalkenyl; wherein each $R^{12}$ alkyl, alkenyl, and alkynyl is optionally substituted with one or more alkoxy;

wherein the cyclic moieties represented by $R^3$, $R^6$, $R^8$, $R^{10}$, and $R^{12}$ are optionally substituted with one, two, three, four, five, or six independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, $C(O)H$, $C(O)OH$, $OH$, $CN$, $N_3$, $NO$, $CF_3$, $CF_2CF_3$, $OCF_3$, $OCF_2CF_3$, $SCF_3$, F, Br or I, $R^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]-pyridinyl, furo[3,2-c]pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolyl, thienyl, furanyl, morpholinyl, isooxazolyl, cycloalkyl, or cycloalkenyl; wherein each $R^{13}$ alkyl, alkenyl, and alkynyl is optionally substituted with one, two, three or four independently selected $R^{14}$, $OR^{14}$, $S(O)R^{14}$, $SO_2R^{14}$, $C(O)R^{14}$, $OC(O)R^{14}$, $OC(O)OR^{14}$, $NH_2$, $NHR^{14}$, $N(R^{14})_2$, $NHC(O)R^{14}$, $NR^{14}C(O)R^{14}$, $NH\,S(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $S(O)_2N(R^{14})_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolyl, thienyl, furanyl, morpholinyl, isooxazolyl, cycloalkyl, and cycloalkenyl is optionally substituted with one, two, three or four independently selected $R^{15}$, $OR^{15}$, $SR^{15}$, $S(O)R^{15}$, $SO_2R^{15}$, $C(O)R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $C(O)H$, $C(O)OH$, $OH$, $CN$, $N_3$, $NO_2$, $CF_3$, $CF_2CF_3$, $OCF_3$, $OCF_2CF_3$, F, Cl, Br or I;

$R^{14}$, at each occurrence, is independently selected alkyl, alkenyl, alkynyl, aryl, heterocyclyl, cycloalkyl, or cycloalkenyl; wherein each $R^{14}$ alkyl, alkenyl, and alkynyl is optionally substituted with one, two, three or four independently selected heterocyclyl, alkoxy, $NH_2$, $SO_2NH_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I; wherein each $R^{14}$ aryl, heterocyclyl, cycloalkyl, and cycloalkenyl is optionally substituted with one, two, three or four independently selected $R^{16}$, $R^{16}$, OH, F, Cl, Br, or I; wherein the $R^{16}$ alkyl is optionally substituted with one, two, three or four alkoxy;

$R^{15}$, at each occurrence, is independently selected alkyl, wherein the $R^{15}$ alkyl is optionally substituted with one, two, three or four alkoxy; and $R^{16}$, at each occurrence, is independently selected alkyl, wherein the $R^{10}$ alkyl is optionally substituted with one, two, three or four alkoxy;

with the proviso that when $R^{13}$ is piperidinyl, it is substituted piperidinyl.

5. The compound of claim 1, or a pharmaceutically acceptable salt thereof; wherein $R^2$ is phenyl which is substituted at the para position with $R^5$; and $R^5$ is phthalazin-1(2H)-onyl, isoquinolinyl, isoquinolin-1(2H)-onyl, 5,6,7,8-tetrahydrophthalazin-1(2H)-onyl, 5-fluorophthalazin-1 (2H)-onyl, (Z)-3H-benzo[d][1,2]diazepin-4(5H)-onyl, 5-(trifluoromethyl)phthalazin-1(2H)-onyl, pyrrolo[1,2-d][1,2,4]triazin-1(2H)-one, or isoindolin-1-onyl.

6. The compound of claim 1, selected from the group consisting of:

N-(4-{[(3S)-tetrahydrofuran-3-ylmethyl]carbamoyl}phenyl)-1,3-dihydro-2H-isoindole-2-carboxamide;

5-fluoro-N-(4-{[(3S)-tetrahydrofuran-3-ylmethyl]carbamoyl}phenyl)-1,3-dihydro-2H-isoindole-2-carboxamide;

or a pharmaceutically acceptable salt thereof.

7. The compound of claim 1, selected from the group consisting of

N-(4-{[(3S)-tetrahydrofuran-3-ylmethyl]carbamoyl}phenyl)-1,3-dihydro-2H-isoindole-2-carboxamide;

or a pharmaceutically acceptable salt thereof.

8. The compound of claim 4, selected from the group consisting of:

N-[4-(1-benzoylpiperidin-4-yl)butyl]-1,3-dihydro-2H-isoindole-2-carboxamide;

N-{4-[1-(pyridin-3-ylcarbonyl)piperidin-4-yl]butyl}-1,3-dihydro-2H-isoindole-2-carboxamide;

N-[4-(1-benzoylpiperidin-4-yl)butyl]-5-cyano-1,3-dihydro-2H-isoindole-2-carboxamide;

N-{4-[1-(pyridin-2-ylcarbonyl)piperidin-4-yl]butyl}-1,3-dihydro-2H-isoindole-2-carboxamide;

or a pharmaceutically acceptable salt thereof.

9. A composition comprising an excipient and a therapeutically effective amount of a compound of claim 1, or a pharmaceutically acceptable salt thereof.

10. A compound having Formula (IIc), or a pharmaceutically acceptable salt thereof

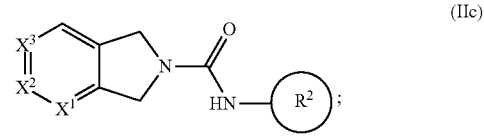

(IIc)

wherein $X^1$, $X^2$, and $X^3$ are CH; or $X^1$ and $X^3$ are CH; and $X^2$ is $CR^1$; or $X^2$ and $X^3$ are CH; and $X^1$ is $CR^1$; or X is CH; and $X^2$ and $X^3$ are $CR^1$;

$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NO_2$, $N_3$, $C(O)H$, CF, $C(O)OH$, or $C(O)NH_2$;

$R^2$ is phenyl, thiophenyl, pyrazolyl, thiazolyl, pyridinyl, pyridazinyl, pyrazinyl, cycloalkyl, or cycloalkenyl; wherein each $R^2$ phenyl is substituted at the para position with one independently selected $R^5$, $OR^5$, $SR^5$, $S(O)R^5$, $SO_2R^5$, $C(O)R^5$, $CO(O)R$, $OC(O)R^5$, $OC(O)OR^5$, $NH_2$, $NHR^5$, $N(R^5)_2$, $NHC(O)R^5$, $NHC(O)R^5$, $NHS(O)_2R^5$, $NR^5S(O)_2R^5$, $NHC(O)OR^5$, $NR^5C(O)OR$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $CHNOR^5$, $C(O)NHOH$, $C(O)NHOR^5$, $C(O)NHSO_2R^5$, $C(O)NR^5SO_2R^2$, $SO_2NH_2$, $SO_2NHR^5$, $SO_2N(R^5)_2$, $C(O)H$, $C(O)OH$, $OH$, $CN$, $N_3$, $CF_3$, $CF_2CF_3$, $OCF_3$, $OCF_2CF_3$, Br or I; wherein each $R^2$ phenyl is optionally additionally substituted with one F;

wherein each $R^2$ heterocyclyl and cycloalkenyl is optionally substituted with one, two, three or four independently selected $R^5$, $OR^5$, $SR$, $S(O)R^5$, $SO_2R^5$, $C(O)R^5$, $CO(O)R^5$, $OC(O)R^5$, $OC(O)OR^5$, $NH_2$, $NHR^3$, $N(R^3)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^3$, $SO_2N(R^3)_2$, $C(O)H$, $C(O)OH$, $OH$, $CN$, $N_3$, $CF_3$, $CF_2CF_3$, $OCF_2$, $OCF_2CF_3$, F, Cl, Br or I; wherein each $R^2$ cycloalkyl is substituted with one, two, three or four independently selected $R^5$, $OR^5$, $SR$, $S(O)R^5$, $SO_2R^5$, $C(O)R^3$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^3S(O)_2R^5$, $NHC(O)OR^3$, $NR^3C(O)OR^5$, $NHC(O)NH_2$, $NHC(O)NHR^5$, $NHC(O)N(R^5)_2$, $NR^5C(O)NHR^3$, $NR^5C(O)N(R^5)_2$, $C(O)NH_2$, $C(O)NHR^3$, $C(O)N(R^5)_2$, $C(O)NHOH$, $C(O)NHOR^5$, $C(O)NHSO_2R^3$, $C(O)NR^5SO_2R^5$, $SO_2NH_2$, $SO_2NHR^5$, $SO_2N(R^5)_2$; $C(O)H$, $C(O)OH$, $OH$, $CN$, N, $CF_3$, $CF_2CF_3$, $OCF_3$, $OCF_2CF_3$, F, Cl, Br or I;

$R^3$, at each occurrence, is independently selected alkyl, alkenyl, alkynyl, aryl, or heterocyclyl; wherein each $R^3$ alkyl, alkenyl, and alkynyl is optionally substituted with one, two, three or four independently selected $R^6$, $OR^6$, $SR^6$, $S(O)R^6$, $SO_2R^6$, $C(O)R^6$, $CO(O)R^o$, $OC(O)R^6$, $OC(O)OR^6$, $NH_2$, $NHR^6$, $N(R^6)_2$, $NHC(O)R^6$, $NR^6C(O)R^6$, $NHS(O)_2$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I;

$R^5$, at each occurrence, is independently selected alkyl, alkenyl, alkynyl, aryl, heterocyclyl, cycloalkyl, or cycloalkenyl; wherein each $R^5$ alkyl, alkenyl, and alkynyl is optionally substituted with one, two, three or four independently selected $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $OH$, $(O)$, $CN$, $N_3$, $NO_2$, $CF_3$, $CF_2CF_3$, $OCF_3$, $OCF_2CF_3$, F, Cl, Br or I;

$R^6$, at each occurrence, is independently selected alkyl, alkenyl, alkynyl, aryl, heterocyclyl, cycloalkyl, or cycloalkenyl; wherein each $R^6$ alkyl, alkenyl, and alkynyl is optionally substituted with one, two, three or four independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, Oil, $(O)$, $C(O)OH$, N, CN, $NH_2$, $CF_3$, $CF_2CF_3$, F, Cl, Br or I;

$R^9$, at each occurrence, is independently selected alkyl, alkenyl, alkynyl, aryl, heterocyclyl, cycloalkyl, or cycloalkenyl; wherein each $R^9$ alkyl, alkenyl, and alkynyl is optionally substituted with one, two, three or four independently selected alkoxy, OH, cycloalkyl, aryl, or heterocyclyl;

$R^{10}$, at each occurrence, is independently selected alkyl, alkenyl, alkynyl, aryl, heterocyclyl, cycloalkyl, or cycloalkenyl;

wherein the cyclic moieties represented by $R^3$, $R^5$, $R^6$, $R^9$, and $R^{10}$ are optionally substituted with one, two, three, four, five, or ix independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^3$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R,^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, $C(O)H$, $C(O)OH$, $OH$, $CN$, $N_3$, $NO_2$, $CF$, $CF_2CF_3$, $OCF_3$, $OCF_2CF_3$, $SCF_3$, F, Cl, Br or I;

$R^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolyl, thienyl, furanyl, morpholinyl, isooxazolyl, cycloalkyl, or cycloalkenyl; wherein each $R^{13}$ alkyl, alkenyl, and alkynyl is optionally substituted with one, two, three or four independently selected $R^{14}$, $OR^{14}$, $SR^{14}$, $S(O)R^{14}$, $SO_2R^{14}$, $C(O)R^{14}$, $OC(O)R^4$, $OC(O)OR^{14}$, $NH_2$, $NHR^{14}$, $N(R^{14})_2$, $NHC(O)R^{14}$, $NR^{14}C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, $C(O)H$, $C(O)OH$, $OH$, $(O)$, $CN$, $NO_2$, $CF_3$, $CF_2CF_3$, $OCF_3$, $OCF_2CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, thiazolyl, pyrrolyl, thienyl, furanyl, morpholinyl, isooxazolyl, cycloalkyl, and cycloalkenyl is optionally substituted with one, two, three or four independently selected $R^{15}$; $OR^{15}$, $SR^{15}$, $S(O)R^{15}$, $SO_2R^{15}$, $C(O)R^{15}$, $COOR^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, $C(O)H$, $C(O)OH$, $OH$, $CN$, $N_3$, $NO_2$, $CF_3$, $CF_2CF_3$, $OCF_2CF_3$, F, Cl, Br or I;

$R^{14}$, at each occurrence, is independently selected alkyl, alkenyl, alkynyl, aryl, heterocyclyl, cycloalkyl, or cycloalkenyl; wherein each $R^{14}$ alkyl; alkenyl, and alkynyl is optionally substituted with one, two, three or four independently selected heterocyclyl, alkoxy, $NH_2$, $SO_2NH_2$, $C(O)H$, $C(O)OH$, OH, $(O)$, CN, $N_3$, $NO_2$, $CF_3$, $CF_2CF_3$, OCT, $OCF_2CF_3$, F, Br or I; wherein each $R^{14}$ aryl, heterocyclyl, cycloalkyl, and cycloalkenyl is optionally substituted with one, two, three or four independently selected $R^{16}$, $OR^{16}$, OH, F, Cl, Br, or I;

$R^{15}$, at each occurrence, is independently selected alkyl; wherein the $R^{15}$ alkyl is optionally substituted with one, two, three or four alkoxy; and $R^{16}$, at each occurrence, is independently selected alkyl, wherein the $R^{16}$ alkyl is optionally substituted with one, two, three or four alkoxy;

with the proviso that when $X^1$, $X^2$, and $X^3$ are CH and $R^2$ is phenyl; $R^5$ is not methyl;

with the proviso that when $X^1$, $X^2$, and $X^3$ are CH, and $R^2$ is phenyl substituted with $OR^5$; $R^5$ is not methyl; and with the proviso that when $R^{13}$ is piperidinyl, it is substituted piperidinyl.

11. A compound having Formula (IIIc), or a pharmaceutically acceptable salt thereof

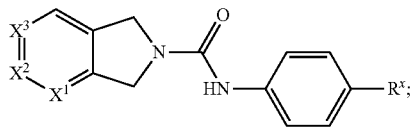

(IIIc)

wherein $X^1$, $X^2$, and $X^3$ are CH; or
$X^1$ and $X^3$ are CH; and $X^2$ is $CR^1$; or
$X^2$ and $X^3$ are CH; and $X^1$ is $CR^1$; or
$X^1$ is CH; and $X^2$ and $X^3$ are $CR^1$;

$R^1$ is $R^3$, $OR^3$, $SR^3$, $S(O)R^3$, $SO_2R^3$, $C(O)R^3$, $C(O)OR^3$, $OC(O)R^3$, $NHR^3$, $N(R^3)_2$, $C(O)NH_2$, $C(O)NHR^3$, $C(O)N(R^3)_2$, $NHC(O)R^3$, $NR^3C(O)R^3$, $NHC(O)OR^3$, $NR^3C(O)OR^3$, $SO_2NH_2$, $SO_2NHR^3$, $SO_2N(R^3)_2$, $NHSO_2R^3$, $NR^3SO_2R^3$, $NHSO_2NHR^3$, $NHSO_2N(R^3)_2$, $NR^3SO_2NHR^3$, $NR^3SO_2N(R^3)_2$, $C(O)NHSO_2R^3$, $NHSO_2NHR^3$, F, Cl, Br, I, CN, $NH_2$, $NO_2$, $N_3$, OH, $C(O)H$, $CF_3$, $C(O)OH$, or $C(O)NH_2$;

$R^x$ is $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $CHNOR^5$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, OH, CN, $N_3$, $NO_2$, $CF_3$, $CF_2CF_3$, $OCF_3$, $OCF_2CF_3$, Br or I;

$R^3$, at each occurrence, is independently selected alkyl, alkenyl, alkynyl, aryl, or heterocyclyl; wherein each $R^3$ alkyl, alkenyl, and alkynyl is optionally substituted with one, two, three or four independently selected $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I;

$R^5$, at each occurrence, is independently selected alkyl, alkenyl, alkynyl, aryl, heterocyclyl, cycloalkyl, or cycloalkenyl; wherein each $R^5$ alkyl, alkenyl, and alkynyl is optionally substituted with one, two, three or four independently selected $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I;

$R^6$, at each occurrence, is independently selected alkyl, alkenyl, alkynyl, aryl, heterocyclyl, cycloalkyl, or cycloalkenyl; wherein each $R^6$ alkyl, alkenyl, and alkynyl is optionally substituted with one, two, three or four independently selected $R^{10}$, $OR^{10}$, $SR^{10}$, $S(O)R^{10}$, $SO_2R^{10}$, $NHR^{10}$, $N(R^{10})_2$, $C(O)R^{10}$, $C(O)NH_2$, $C(O)NHR^{10}$, $C(O)N(R^{10})_2$, $NHC(O)R^{10}$, $NR^{10}C(O)R^{10}$, $NHSO_2R^{10}$, $NHC(O)OR^{10}$, $SO_2NH_2$, $SO_2NHR^{10}$, $SO_2N(R^{10})_2$, $NHC(O)NH_2$, $NHC(O)NHR^{10}$, OH, (O), $C(O)OH$, $N_3$, CN, $NH_2$, $CF_3$, $CF_2CF_3$, F, Cl, Br or I;

$R^9$, at each occurrence, is independently selected alkyl, alkenyl, alkynyl, aryl, heterocyclyl, cycloalkyl, or cycloalkenyl; wherein each $R^9$ alkyl, alkenyl, and alkynyl is optionally substituted with one, two, three or four independently selected alkoxy, OH, cycloalkyl, aryl, or heterocyclyl;

$R^{10}$, at each occurrence, is independently selected alkyl, alkenyl, alkynyl, aryl, heterocyclyl, cycloalkyl, or cycloalkenyl;

wherein the cyclic moieties represented by $R^3$, $R^5$, $R^6$, $R^9$, and $R^{10}$ are optionally substituted with one, two, three, four, five, or six independently selected $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, $C(O)H$, $C(O)OH$, OH, CN, $N_3$, $NO_2$, $CF_3$, $CF_2CF_3$, $OCF_3$, $OCF_2CF_3$, $SCF_3$, F, Cl, Br or I;

$R^{13}$, at each occurrence, is independently selected alkyl, alkenyl, alkynyl, aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolidinyl, pyrrolyl, thienyl, furanyl, morpholinyl, cycloalkyl, or cycloalkenyl; wherein each $R^{13}$ alkyl, alkenyl, and alkynyl is optionally substituted with one, two, three or four independently selected $R^{14}$, $OR^{14}$, $SR^{14}$, $S(O)R^{14}$, $SO_2R^{14}$, $C(O)R^{14}$, $OC(O)R^{14}$, $OC(O)OR^{14}$, $NH_2$, $NHR^{14}$, $N(R^{14})_2$, $NHC(O)R^{14}$, $NR^{14}$, $C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, $C(O)H$, $C(O)OH$, OH, (O), CN, $N_3$, $NO_2$, $CF_3$, $CF_2CF_3$, $OCF_3$, $OCF_2CF_3$, F, Cl, Br or I; wherein each $R^{13}$ aryl, tetrahydrofuranyl, pyridazinyl, pyrazinyl, pyrimidinyl, pyridinyl, thieno[3,2-c]pyridinyl, furo[3,2-c]pyridinyl, pyrrolidin-2-onyl, 1,1-dioxidotetrahydrothien-3-yl, 1,1-dioxidotetrahydro-2H-thiopyran-3-yl, dioxanyl, tetrahydropyranyl, piperidinyl, pyrimidinyl, oxazolyl, pyrazolyl, thiazolyl, pyrrolyl, thienyl, furanyl, morpholinyl, cycloalkyl, and cycloalkenyl is optionally substituted with one, two, three or four independently selected $R^{15}$, $OR^{15}$, $SR^{15}$, S(O)R$^{15}$, SO$_2$R$^{15}$, C(O)R$^{15}$, CO(O)R$^{15}$, OC(O)R$^{15}$, OC(O)OR$^{15}$, NH$_2$, NHR$^{15}$, N(R$^{15}$)$_2$, NHC(O)R$^{15}$, NR$^{15}$C(O)R$^{15}$, NHS(O)$_2$R$^{15}$, NR$^{15}$S(O)$_2$R$^{15}$, NHC(O)OR$^{15}$, NR$^{15}$C(O)OR$^{15}$, NHC(O)NH$_2$, NHC(O)NHR$^{15}$, NHC(O)N(R$^{15}$)$_2$, NR$^{15}$C(O)NHR$^{15}$, NR$^{15}$C(O)N(R$^{15}$)$_2$, C(O)NH$_2$, C(O)NHR$^{15}$, C(O)N(R$^{15}$)$_2$, C(O)NHOH, C(O)NHOR$^{15}$, C(O)NHSO$_2$R$^{15}$, C(O)NR$^{15}$SO$_2$R$^{15}$, SO$_2$NH$_2$, SO$_2$NHR$^{15}$, SO$_2$N(R$^{15}$)$_2$, C(O)H, C(O)OH, OH, CN, N$_3$, NO$_2$, CF$_3$, CF$_2$CF$_3$, OCF$_3$, OCF$_2$CF$_3$, F, Cl, Br or I;

R$^{14}$, at each occurrence, is independently selected alkyl, alkenyl, alkynyl, aryl, heterocyclyl, cycloalkyl, or cycloalkenyl; wherein each R$^{14}$ alkyl, alkenyl, and alkynyl is optionally substituted with one, two, three or four independently selected heterocyclyl, alkoxy, NH$_2$, SO$_2$NH$_2$, C(O)H, C(O)OH, OH, (O), CN, N$_3$, NO$_2$, CF$_3$, CF$_2$CF$_3$, OCF$_3$, OCF$_2$CF$_3$, F, Cl, Br or I; wherein each R$^{14}$ aryl, heterocyclyl, cycloalkyl, and cycloalkenyl is optionally substituted with one, two, three or four independently selected R$^{16}$, OR$^{16}$, OH, F, Cl, Br, or I;

R$^{15}$, at each occurrence, is independently selected alkyl, wherein the R$^{15}$ alkyl is optionally substituted with one, two, three or four alkoxy; and R$^{16}$, at each occurrence, is independently selected alkyl, wherein the R$^{16}$ alkyl is optionally substituted with one, two, three or four alkoxy;

with the proviso that when X$^1$, X$^2$, and X$^3$ are CH; R$^x$ is not methyl;

with the proviso that when X$^1$, X$^2$, and X$^3$ are CH; R$^x$ is not methoxy;

with the proviso that when R$^{13}$ is piperidinyl, it is substituted piperidinyl.

12. The compound of claim 11, wherein

R$^x$ is R$^5$; and

R$^5$ is heterocyclyl optionally substituted with one, two, three, four, five, or six independently selected R$^{13}$, OR$^{13}$, SR$^{13}$, S(O)R$^{13}$, SO$_2$R$^{13}$, C(O)R$^{13}$, CO(O)R$^{13}$, OC(O)R$^{13}$, OC(O)OR$^{13}$, NH$_2$, NHR$^{13}$, N(R$^{13}$)$_2$, NHC(O)R$^{13}$, NR$^{13}$C(O)R$^{13}$, NHS(O)R$^{13}$, NR$^{13}$S(O)$_2$R$^{13}$, NHC(O)OR$^{13}$, NR$^{13}$C(O)OR$^{13}$, NHC(O)NH$_2$, NHC(O)NHR$^{13}$, NHC(O)N(R$^{13}$)$_2$, NR$^{13}$C(O)NHR$^{13}$, NR$^{13}$C(O)N(R$^{13}$)$_2$, C(O)NH$_2$, C(O)NHR$^{13}$, C(O)N(R$^{13}$)$_2$, C(O)NHOH, C(O)NHOR$^{13}$, C(O)NHSO$_2$R$^{13}$, C(O)NR$^{13}$SO$_2$R$^{13}$, SO$_2$NH$_2$, SO$_2$NHR$^{13}$, SO$_2$N(R$^{13}$)$_2$, C(O)H, C(O)OH, OH, CN, N$_3$, NO$_2$, CF$_3$, CF$_2$CF$_3$, OCF$_3$, OCF$_2$CF$_3$, SCF$_3$, F, Cl, Br or I.

13. The compound of claim 12, wherein R is piperidinyl optionally substituted with one, two, three, four, five, or six independently selected R$^{13}$, OR$^{13}$, SR$^{13}$, S(O)R$^{13}$, SO$_2$R$^{13}$, C(O)R$^{13}$, CO(O)R$^{13}$, OC(O)R$^{13}$, OC(O)OR$^{13}$, NH$_2$, NHR$^{13}$, N(R$^{13}$)$_2$, NHC(O)R$^{13}$, NR$^{13}$C(O)R$^{13}$, NHS(O)$_2$R$^{13}$, NR$^{13}$S(O)$_2$R$^{13}$, NHC(O)OR$^{13}$, NR$^{13}$C(O)OR$^{13}$, NHC(O)NH$_2$, NHC(O)NHR$^{13}$, NHC(O)N(R$^{13}$)$_2$, NR$^{13}$C(O)NHR$^{13}$, NR$^{13}$C(O)N(R$^{13}$)$_2$, C(O)NH$_2$, C(O)NHR$^{13}$, C(O)N(R$^{13}$)$_2$, C(O)NHOH, C(O)NHOR$^{13}$, C(O)NHSO$_2$R$^{13}$, CONR$^{13}$SO$_2$R$^{13}$, SO$_2$NH$_2$, SO$_2$NHR$^{13}$, SO$_2$N(R$^{13}$)$_2$, C(O)H, C(O)OH, OH, CN, N$_3$, NO$_2$, CF$_3$, CF$_2$CF$_3$, OCF$_3$, OCF$_2$CF$_3$, SCF$_3$, F, Cl, Br or I.

14. The compound of claim 13, wherein

R$^5$ piperidinyl is substituted with one R$^{13}$; and

R$^{13}$ is alkyl optionally substituted with one, two, three or four independently selected R$^{14}$, OR$^{14}$, SR$^{14}$, S(O)R$^{14}$, SO$_2$R$^{14}$, C(O)R$^{14}$, OC(O)R$^{14}$, OC(O)OR$^{14}$, NHR$^{14}$, N(R$^{14}$)$_2$, NHC(O)R$^{14}$, NR$^{14}$C(O)R$^{14}$, NHS(O)$_2$R$^{14}$, NR$^{14}$S(O)$_2$R$^{14}$, NHC(O)OR$^{14}$, NR$^{14}$C(O)OR$^{14}$, NHC(O)NH$_2$, NHC(O)NHR$^{14}$, NHC(O)N(R$^{14}$)$_2$, NR$^{14}$C(O)NHR$^{14}$, $^4$C(O)N(R$^{14}$)$_2$, C(O)NH$_2$, C(O)NHR$^{14}$, C(O)N(R$^{14}$)$_2$, C(O)NHOH, C(O)NHOR$^{14}$, C(O)NHSO$_2$R$^{14}$, C(O)NR$^{14}$SO$_2$R$^{14}$, SO$_2$NH$_2$, SO$_2$NHR$^{14}$, SO$_2$N(R$^{14}$)$_2$, C(O)H, C(O)OH, OH, (O), CN, N$_3$, NO$_2$, CF$_3$, CF$_2$CF$_3$, OCF$_3$, OCF$_2$CF$_1$, F, Cl, Br or I.

15. The compound of claim 14, wherein

R$^{13}$ alkyl is substituted with one R$^{14}$ and (O); and

R$^{14}$ is heterocyclyl optionally substituted with one, two, three or four independently selected R$^{16}$, OR, OH, F, Cl, Br, or I.

16. The compound of claim 14, wherein R$^{14}$ heterocyclyl is oxetanyl optionally substituted with one, two, three or four independently selected R$^{16}$, OR$^{16}$, OH, F, Cl, Br, or I.

17. The compound of claim 3, wherein

R$^{13}$ is alkyl optionally substituted with one, two, three or four independently selected R$^{14}$, OR$^{14}$, SR$^{14}$, S(O)R$^{14}$, SO$_2$R$^{14}$, C(O)R$^{14}$, OC(O)R$^{14}$, OC(O)OR$^{14}$, NH$_2$, NHR$^{14}$, N(R$^{14}$)$_2$, NHC(O)R$^{14}$, NR$^{14}$C(O)R$^{14}$, NHS(O)$_2$R$^{14}$, NR$^{14}$S(O)$_2$R$^{14}$, NHC(O)OR$^{14}$, NR$^{14}$C(O)OR$^{14}$, NHC(O)NH$_2$, NHC(O)NHR$^{14}$, NHC(O)N(R$^{14}$)$_2$, NR$^{14}$C(O)NHR$^{14}$, NR$^{14}$C(O)N(R$^{14}$)$_2$, C(O)NH$_2$, C(O)NHR$^{14}$, C(O)N(R$^{14}$)$_2$, C(O)NHOH, C(O)NHOR$^{14}$, C(O)NHSO$_2$R$^{14}$, C(O)NR$^{14}$SO$_2$R$^{14}$, SO$_2$NH$_2$, SO$_2$NHR$^{14}$, SO$_2$N(R$^{14}$)$_2$, C(O)H, C(O)OH, OH, (O), CN, N$_3$, NO$_2$, CF, CF$_2$CF$_3$, OCF$_2$CF$_3$, F, Cl, Br or I.

18. The compound of claim 1, selected from the group consisting of:

N-{4-[(3-phenylpropyl)carbamoyl]phenyl}-1,3-dihydro-2H-isoindole-2-carboxamide;

N-(4-{[4-(aminomethyl)benzyl]carbamoyl}phenyl)-5-fluoro-1,3-dihydro-2H-isoindole-2-carboxamide;

5-cyano-N-{4-[(3-phenylpropyl)carbamoyl]phenyl}-1,3-dihydro-2H-isoindole-2-carboxamide;

N-{4-[(cyclopentylmethyl)carbamoyl]phenyl}-5-fluoro-1,3-dihydro-2H-isoindole-2-carboxamide;

5-cyano-N-[4-(propylcarbamoyl)phenyl]-1,3-dihydro-2H-isoindole-2-carboxamide;

N-(4-{[4-(furo[3,2-c]pyridin-4-yl)piperazin-1-yl]carbonyl}phenyl)-1,3-dihydro-2H-isoindole-2-carboxamide;

5-cyano-N-(4-[4-(pyridin-2-yl)piperazin-1-yl]carbonyl}phenyl)-1,3-dihydro-2H-isoindole-2-carboxamide;

5-fluoro-N-{4-[(pyridin-2-ylmethyl)carbamoyl]phenyl}-1,3-dihydro-2H-isoindole-2-carboxamide;

N-[4-(benzylcarbamoyl)phenyl]-5-fluoro-1,3-dihydro-2H-isoindole-2-carboxamide;

N-{4-[(3,4-dimethoxybenzyl)carbamoyl]phenyl}-1,3-dihydro-2H-isoindole-2-carboxamide;

5-methyl-N-(4-{[4-(pyridin-2-yl)piperazin-1-yl]carbonyl}phenyl)-1,3-dihydro-2H-isoindole-2-carboxamide;

N-(4-{[4-(thieno[3,2-c]pyridin-4-yl)piperazin-1-yl]carbonyl}phenyl)-1,3-dihydro-2H-isoindole-2-carboxamide;

N-{4-[(2,3-dimethoxybenzyl)carbamoyl]phenyl}-1,3-dihydro-2H-isoindole-2-carboxamide;

5-fluoro-N-{4-[(3-phenylpropyl)carbamoyl]phenyl}-1,3-dihydro-2H-isoindole-2-carboxamide;

5-fluoro-N-(4-{[4-(pyridazin-3-yl)piperazin-1-yl]carbonyl})phenyl)-1,3-dihydro-2H-isoindole-2-carboxamide;

N-{4-[(2,3-dihydro-1,4-benzodioxin-5-ylmethyl)carbamoyl]phenyl}-1,3-dihydro-2-isoindole-2-carboxamide;

5-fluoro-N-(4-{[1-(3-methylbutyl)-1H-pyrazol-4-yl]carbamoyl}phenyl)-1,3-dihydro-2H-isoindole-2-carboxamide;

N-{4-[(2-fluorobenzyl)carbamoyl]phenyl}-1,3-dihydro-2H-isoindole-2-carboxamide;
5-fluoro-N-(4-{[4-(pyrimidin-2-yl)piperazin-1-yl]carbonyl}phenyl)-1,3-dihydro-2H-isoindole-2-carboxamide;
5-fluoro-N-{4-[(3-methylbutyl)carbamoyl]phenyl)-1,3-dihydro-2H-isoindole-2-carboxamide;
N-{4-[(2-methoxybenzyl)carbamoyl]phenyl}-1,3-dihydro-2H-isoindole-2-carboxamide;
5-fluoro-N-(4-([4-(pyridin-2-yl)piperazin-1-yl]carbonyl}phenyl)-1,3-dihydro-2H-isoindole-2-carboxamide;
N-{4-[(3-fluorobenzyl)carbamoyl]phenyl}-1,3-dihydro-2H-isoindole-2-carboxamide;
5-fluoro-N-(4-{[3-(2-oxopyrrolidin-1-yl)propyl]carbamoyl}phenyl)-1,3-dihydro-2H-isoindole-2-carboxamide;
5-cyano-N-{4-[(3-methylbutyl)carbamoyl]phenyl}-1,3-dihydro-2H-isoindole-2-carboxamide;
N-{4-[(cyclopentylmethyl)carbamoyl]phenyl}-5-methyl-1,3-dihydro-2H-isoindole-2-carboxamide;
N-(4-{[4-(4-cyanophenyl)piperazin-1-yl]carbonyl}phenyl)-1,3-dihydro-2H-isoindole-2-carboxamide;
N-{4-[(4-fluorobenzyl)carbamoyl]phenyl}-1,3-dihydro-2H-isoindole-2-carboxamide;
N-{4-[(3,5-dimethoxybenzyl)carbamoyl]phenyl}-1,3-dihydro-2H-isoindole-2-carboxamide;
5-fluoro-N-{4-[(tetrahydrofuran-3-ylmethyl)carbamoyl]phenyl}-1,3-dihydro-2H-isoindole-2-carboxamide;
N-{4-[(2,2-dimethyl propyl)carbamoyl]phenyl)}-1,3-dihydro-2H-isoindole-2-carboxamide;
5-fluoro-N-(4-{[2-(2-oxopyrrolidin-1-yl)ethyl]carbamoyl}phenyl)-1,3-dihydro-2H-isoindole-2-carboxamide;
N-(4-{[4-(trifluoromethoxy)benzyl]carbamoyl}phenyl)-1,3-dihydro-2H-isoindole-2-carboxamide;
N-(4-{[3-fluoro-5-(trifluoromethyl)benzyl]carbamoyl)phenyl}-1,3-dihydro-2H-isoindole-2-carboxamide;
5-fluoro-N-(4-{[4-(pyrazin-2-yl)piperazin-1-yl]carbonyl}phenyl)-1,3-dihydro-2H-isoindole-2-carboxamide;
N-{4-[(3-methylbutyl)carbamoyl]phenyl}-1,3-dihydro-2H-isoindole-2-carboxamide;
5-methoxy-N-{4-[(3-phenylpropyl)carbamoyl]phenyl}-1,3-dihydro-2H-isoindole-2-carboxamide;
N-{4-[(4-chlorobenzyl)carbamoyl]phenyl}-1,3-dihydro-2H-isoindole-2-carboxamide;
N-{4-[(cyclopentylmethyl)carbamoyl]phenyl}-1,3-dihydro-2H-isoindole-2-carboxamide;
N-{4-[(3,4,5-trimethoxybenzyl)carbamoyl]phenyl}-1,3-dihydro-2H-isoindole-2-carboxamide;
N-(4-{[4-(pyrimidin-2-yl)piperazin-1-yl]carbonyl}phenyl)-1,3-dihydro-2H-isoindole-2-carboxamide;
5-nitro-N-[4-(propylcarbamoyl)phenyl]-1,3-dihydro-2H-isoindole-2-carboxamide;
5-methyl-N-{4-[(3-methylbutyl)carbamoyl]phenyl}-1,3-dihydro-2H-isoindole-2-carboxamide;
N-(4-{[4-(4-fluorophenyl)piperazin-1-yl]carbonyl}phenyl)-1,3-dihydro-2H-isoindole-2-carboxamide;
N-{4-[(4-methoxybenzyl)carbamoyl]phenyl}-1,3-dihydro-2H-isoindole-2-carboxamide;
N-{4-[(2-thienylmethyl)carbamoyl]phenyl}-1,3-dihydro-2H-isoindole-2-carboxamide;
N-(4-{[4-(pyrimidin-2-yl)piperazin-1-yl]carbonyl}phenyl)-5-(trifluoromethyl)-1,3-dihydro-2H-isoindole-2-carboxamide;
N-{4-[(1-ethyl-1H-pyrazol-4-yl)carbamoyl]phenyl)}-5-fluoro-1,3-dihydro-2H-isoindole-2-carboxamide;
N-{4-[(1-benzyl-1H-pyrazol-4-yl)carbamoyl]phenyl)}-5-fluoro-1,3-dihydro-2H-isoindole-2-carboxamide;
N-(4-{[4-(pyridin-2-yl)piperazin-1-yl]carbonyl}phenyl)-1,3-dihydro-2H-isoindole-2-carboxamide;
N-(4-{[4-(pyrazin-2-yl)piperazin-1-yl]carbonyl}phenyl)-1,3-dihydro-2H-isoindole-2-carboxamide;
N-(4-([4-(2-methoxyphenyl)piperazin-1-yl]carbonyl phenyl)-1,3-dihydro-2H-isoindole-2-carboxamide;
N-{4-[(3,3-dimethylbutyl)carbamoyl]phenyl}-1,3-dihydro-2H-isoindole-2-carboxamide;
N-(4-{[(2R)-tetrahydrofuran-2-ylmethyl]carbamoyl}phenyl)-1,3-dihydro-2H-isoindole-2-carboxamide;
N-(4-{[4-(3-methoxyphenyl)piperazin-1-yl]carbonyl}phenyl)-1,3-dihydro-2H-isoindole-2-carboxamide;
N-(4-{[4-(4-acetylphenyl)piperazin-1-yl]carbonyl}phenyl)-1,3-dihydro-2H-isoindole-2-carboxamide;
N-(4-{[2-(2,3-dimethoxyphenyl)ethyl]carbamoyl}phenyl)-1,3-dihydro-2H-isoindole-2-carboxamide;
N-{4-[(3-thienylmethyl)carbamoyl]phenyl}-1,3-dihydro-2H-isoindole-2-carboxamide;
5-methoxy-N-{4-[(3-methylbutyl)carbamoyl]phenyl}-1,3-dihydro-2H-isoindole-2-carboxamide;
N-{4-[(pyridin-2-ylmethyl)carbamoyl]phenyl}-1,3-dihydro-2H-isoindole-2-carboxamide;
5-fluoro-N-(4-{[2-(2-thienyl)ethyl]carbamoyl}phenyl)-1,3-dihydro-2H-isoindole-2-carboxamide;
N-(4-{[(2S)-tetrahydrofuran-2-ylmethyl]carbamoyl}phenyl)-1,3-dihydro-2H-isoindole-2-carboxamide;
N-(4-{[1-(3-methylbutyl)-1H-pyrazol-4-yl]carbamoyl}phenyl)-1,3-dihydro-2H-isoindole-2-carboxamide;
4-chloro-N-(4-4 [4-(pyridin-2-yl)piperazin-1-yl]carbonyl}phenyl)-1,3-dihydro-2H-isoindole-2-carboxamide;
N-{4-[(4-phenylpiperazin-1-yl)carbonyl]phenyl}-1,3-dihydro-2H-isoindole-2-carboxamide;
N-{4-[(6-aminohexyl)carbamoyl]phenyl}-1,3-dihydro-2H-isoindole-2-carboxamide;
4-chloro-N-{4-[(3-methylbutyl)carbamoyl]phenyl}-1,3-dihydro-2H-isoindole-2-carboxamide;
N-(4-{[2-(2-thienyl)ethyl]carbamoyl}phenyl)-1,3-dihydro-2H-isoindole-2-carboxamide;
5-methoxy-N-(4-{[4-(pyridin-2-yl)piperazin-1-yl]carbonyl}phenyl)-1,3-dihydro-2H-isoindole-2-carboxamide;
N-{4-[(1,3-benzodioxol-5-ylmethyl)carbamoyl]phenyl}-1,3-dihydro-2H-isoindole-2-carboxamide;
N-{4-[(3-methoxybenzyl)carbamoyl]phenyl}-1,3-dihydro-2H-isoindole-2-carboxamide;
N-(4-{[4-(pyridin-3-yl)piperazin-1-yl]carbonyl}phenyl)-1,3-dihydro-2H-isoindole-2-carboxamide;
N-[4-(benzylcarbamoyl)phenyl]-1,3-dihydro-2H-isoindole-2-carboxamide;
N-(4-{[4-(pyridazin-3-yl)piperazin-1-yl]carbonyl}phenyl)-1,3-dihydro-2H-isoindole-2-carboxamide;

N-{4-[(pyrimidin-4-ylmethyl)carbamoyl]phenyl}-1,3-dihydro-2H-isoindole-2-carboxamide;
N-(4-{[4-(3-fluorophenyl)piperazin-1-yl]carbonyl}phenyl)-1,3-dihydro-2H-isoindole-2-carboxamide;
N-{4-[(2-methylbutyl)carbamoyl]phenyl}-1,3-dihydro-2H-isoindole-2-carboxamide;
N-(4-{[4-(pyridin-2-yl)piperazin-1-yl]carbonyl}phenyl)-5-(trifluoromethyl)-1,3-dihydro-2H-isoindole-2-carboxamide;
N-{4-[(3-butoxypropyl)carbamoyl]phenyl}-1,3-dihydro-2H-isoindole-2-carboxamide;
N-(4-{[(1S)-2-hydroxy-1-phenylethyl]carbamoyl}phenyl)-1,3-dihydro-2H-isoindole-2-carboxamide;
N-(4-{[2-(3,4-dihydroxyphenyl)ethyl]carbamoyl}phenyl)-1,3-dihydro-2H-isoindole-2-carboxamide;
N-{4-[(3-propoxypropyl)carbamoyl]phenyl}-1,3-dihydro-2H-isoindole-2-carboxamide;
N-{4-[(3-furylmethyl)carbamoyl]phenyl}-1,3-dihydro-2H-isoindole-2-carboxamide;
N-(4-{[4-(2-cyanophenyl)piperazin-1-yl]carbonyl}phenyl)-1,3-dihydro-2H-isoindole-2-carboxamide;
N-{4-[(3-hydroxy-2-methylphenyl)carbamoyl]phenyl}-1,3-dihydro-2H-isoindole-2-carboxamide;
N-{4-[(3-methylbutyl)carbamoyl]phenyl}-5-(trifluoromethyl)-1,3-dihydro-2H-isoindole-2-carboxamide;
N-{4-[(3-methyl-1H-indazol-5-yl)carbamoyl]phenyl}-1,3-dihydro-2H-isoindole-2-carboxamide;
N-{4-[(3-ethoxypropyl)carbamoyl]phenyl}-1,3-dihydro-2H-isoindole-2-carboxamide;
N-(4-{[4-(pyrazin-2-yl)piperazin-1-yl]carbonyl}phenyl)-5-(trifluoromethyl)-1,3-dihydro-2H-isoindole-2-carboxamide;
N-(4-{[2-(2,5-dimethoxyphenyl)ethyl]carbamoyl}phenyl)-1,3-dihydro-2H-isoindole-2-carboxamide;
N-{4-[(tetrahydrofuran-3-ylmethyl)carbamoyl]phenyl}-1,3-dihydro-2H-isoindole-2-carboxamide;
N-{4-[(1-benzyl-1H-pyrazol-4-yl)carbamoyl]phenyl}-1,3-dihydro-2H-isoindole-2-carboxamide;
methyl 5-({4-[(1,3-dihydro-2H-isoindol-2-ylcarbonyl)amino]benzoyl}amino)-1H-indazole-3-carboxylate;
N-(4-{[2-(2-oxopyrrolidin-1-yl)ethyl]carbamoyl}phenyl)-1,3-dihydro-2H-isoindole-2-carboxamide;
N-{4-[(pyridin-4-ylmethyl)carbamoyl]phenyl}-1,3-dihydro-2H-isoindole-2-carboxamide;
N-(4-{[4-(5-chloropyridin-2-yl)piperazin-1-yl]carbonyl}phenyl)-1,3-dihydro-2H-isoindole-2-carboxamide;
N-(4-{[2-(1H-indol-3-yl)ethyl]carbamoyl}phenyl)-1,3-dihydro-2H-isoindole-2-carboxamide;
N-(4-{[4-(trifluoromethyl)benzyl]carbamoyl}phenyl)-1,3-dihydro-2H-isoindole-2-carboxamide;
N-{4-[(3,5-dimethoxyphenyl)carbamoyl]phenyl}-1,3-dihydro-2H-isoindole-2-carboxamide;
N-{4-[(pyridin-3-ylmethyl)carbamoyl]phenyl}-1,3-dihydro-2H-isoindole-2-carboxamide;
N-[4-(2,3-dihydro-1,4-benzodioxin-6-ylcarbamoyl)phenyl]-1,3-dihydro-2H-isoindole-2-carboxamide;
N-(4-{[4-(2-fluorobenzoyl)piperazin-1-yl]carbonyl}phenyl)-1,3-dihydro-2H-isoindole-2-carboxamide;
N-(4-{[2-(5-methoxy-1H-indol-3-yl)ethyl]carbamoyl}phenyl)-1,3-dihydro-2H-isoindole-2-carboxamide;
N-{4-[(3-aminobenzyl)carbamoyl]phenyl}-1,3-dihydro-2H-isoindole-2-carboxamide;
N-(4-{[2-(2-chlorophenyl)ethyl]carbamoyl)}phenyl)-1,3-dihydro-2H-isoindole-2-carboxamide;
N-(4-{[(2R)-1-hydroxy-4-methylpentan-2-yl]carbamoyl}phenyl)-1,3-dihydro-2H-isoindole-2-carboxamide;
N-{4-[(2-propoxyethyl)carbamoyl]phenyl}-1,3-dihydro-2H-isoindole-2-carboxamide;
N-{4-[(3-isobutoxypropyl)carbamoyl]phenyl)-1,3-dihydro-2H-isoindole-2-carboxamide;
N-(4-{[4-(pyridin-4-yl)piperazin-1-yl]carbonyl}phenyl)-1,3-dihydro-2H-isoindole-2-carboxamide;
N-[4-((4-[5-(trifluoromethyl)pyridin-2-yl]piperazin-1-yl}carbonyl)phenyl]-1,3-dihydro-2H-isoindole-2-carboxamide;
N-{4-[(3,4,5-trimethoxyphenyl)carbamoyl]phenyl)}-1,3-dihydro-2H-isoindole-2-carboxamide;
N-{4-[(4-methylpiperidin-1-yl)carbonyl]phenyl}-1,3-dihydro-2H-isoindole-2-carboxamide;
N-[4-({2-[4-(dimethylamino)phenyl]ethyl}carbamoyl)phenyl]-1,3-dihydro-2H-isoindole-2-carboxamide;
N-(4-{[3-(trifluoromethoxy)benzyl]carbamoyl}phenyl)-1,3-dihydro-2H-isoindole-2-carboxamide;
N-(4-{[(1R)-3-hydroxy-1-phenylpropyl]carbamoyl}phenyl)-1,3-dihydro-2H-isoindole-2-carboxamide;
N-{4-[(3-cyanophenyl)carbamoyl]phenyl}-1,3-dihydro-2H-isoindole-2-carboxamide;
N-{4-[(3-fluoro-4-methoxyphenyl)carbamoyl]phenyl}-1,3-dihydro-2H-isoindole-2-carboxamide;
N-{4-[(2,3-dimethoxyphenyl)carbamoyl]phenyl}-1,3-dihydro-2H-isoindole-2-carboxamide;
N-(4-{[2-(2-fluorophenyl)ethyl]carbamoyl}phenyl}-1,3-dihydro-2H-isoindole-2-carboxamide;
N-[4-(isobutylcarbamoyl)phenyl]-1,3-dihydro-2H-isoindole-2-carboxamide;
N-(4-{[2-(1,3-benzodioxol-5-yl)ethyl]carbamoyl}phenyl)-1,3-dihydro-2H-isoindole-2-carboxamide;
N-(4-{[2-(2-methoxyphenyl)ethyl]carbamoyl}phenyl)-1,3-dihydro-2H-isoindole-2-carboxamide;
N-[4-(butylcarbamoyl)phenyl]-1,3-dihydro-2H-isoindole-2-carboxamide;
N-{4-[(2-isopropoxyethyl)carbamoyl]phenyl)}-1,3-dihydro-2H-isoindole-2-carboxamide;
N-{4-[(3-isopropoxypropyl)carbamoyl]phenyl}-1,3-dihydro-2H-isoindole-2-carboxamide;
4-chloro-N-{4-[(3-phenylpropyl)carbamoyl]phenyl}-1,3-dihydro-2H-isoindole-2-carboxamide;
N-(4-{[2-(4-methoxyphenyl)ethyl]carbamoyl}phenyl)-1,3-dihydro-2H-isoindole-2-carboxamide;
N-{4-[(3-methoxypropyl)carbamoyl]phenyl}-1,3-dihydro-2H-isoindole-2-carboxamide;
N-(4-{[2-(4-fluorophenyl)ethyl]carbamoyl}phenyl)-1,3-dihydro-2H-isoindole-2-carboxamide;
N-(4-{[3-(2-oxopyrrolidin-1-yl)propyl]carbamoyl}phenyl)-1,3-dihydro-2H-isoindole-2-carboxamide;
N-{4-[(2,4-dimethoxyphenyl)carbamoyl]phenyl}-1,3-dihydro-2H-isoindole-2-carboxamide;
$N^2$-[4-(propylcarbamoyl)phenyl]-1,3-dihydro-2H-isoindole-2,5-dicarboxamide;

N-{4-[(2-phenoxyethyl)carbamoyl]phenyl}-1,3-dihydro-2H-isoindole-2-carboxamide;
N-(4-{[2-(4-hydroxyphenyl)ethyl]carbamoyl}phenyl)-1,3-dihydro-2H-isoindole-2-carboxamide;
N-(4-{[2-(3-fluorophenyl)ethyl]carbamoyl}phenyl)-1,3-dihydro-2H-isoindole-2-carboxamide;
N-[4-({1-[(3S)-tetrahydrofuran-3-yl]-1H-pyrazol-4-yl}carbamoyl)phenyl]-1,3-dihydro-2H-isoindole-2-carboxamide;
5-methyl-N-{4-[(3-phenylpropyl)carbamoyl]phenyl}-1,3-dihydro-2H-isoindole-2-carboxamide;
N-[4-(1,4-dioxa-8-azaspiro[4.5]dec-8-ylcarbonyl)phenyl]-1,3-dihydro-2H-isoindole-2-carboxamide;
N-{4-[(2-phenylethyl)carbamoyl]phenyl}-1,3-dihydro-2H-isoindole-2-carboxamide;
N-(4-([2-(2,4-dimethoxyphenyl)ethyl]carbamoyl)phenyl)-1,3-dihydro-2H-isoindole-2-carboxamide;
N-{4-{[3-(methylthio)propyl]carbamoyl]phenyl}-1,3-dihydro-2H-isoindole-2-carboxamide;
N-{4-[(2-ethoxyethyl)carbamoyl]phenyl}-1,3-dihydro-2H-isoindole-2-carboxamide;
N-{4-[(2-fluoro phenyl)carbamoyl]phenyl}-1,3-dihydro-2H-isoindole-2-carboxamide;
N-(4-{[2-(pyridin-3-yl)ethyl]carbamoyl}phenyl)-1,3-dihydro-2H-isoindole-2-carboxamide;
N-[4-({4-[(trifluoromethyl)thio]benzyl}carbamoyl)phenyl]-1,3-dihydro-2H-isoindole-2-carboxamide;
N-{4-[(3,4-dimethoxyphenyl)carbamoyl]phenyl}-1,3-dihydro-2H-isoindole-2-carboxamide;
N-(4-{[3-(2-fluorophenyl)pyrrolidin-1-yl]carbonyl}phenyl)-1,3-dihydro-2H-isoindole-2-carboxamide;
N-(4-{[3-(1H-imidazol-1-yl)propyl]carbamoyl}phenyl)-1,3-dihydro-2H-isoindole-2-carboxamide;
N-(4-([2-(3-chlorophenyl)ethyl]carbamoyl)phenyl)-1,3-dihydro-2H-isoindole-2-carboxamide;
N-{4-[(4-hydroxybutyl)carbamoyl]phenyl}-1,3-dihydro-2H-isoindole-2-carboxamide;
N-{4-[(3-phenylpropyl)carbamoyl]phenyl}-5-(trifluoromethyl)-1,3-dihydro-2H-isoindole-2-carboxamide;
N-(4-{[4-(hydroxymethyl)phenyl]carbamoyl}phenyl)-1,3-dihydro-2H-isoindole-2-carboxamide;
N-[4-(1,3-benzodioxol-5-ylcarbamoyl)phenyl]-1,3-dihydro-2H-isoindole-2-carboxamide;
N-{4-[(1-isopropyl-1H-pyrazol-4-yl)carbamoyl]phenyl}-1,3-dihydro-2H-isoindole-2-carboxamide;
N-{4-[(4-hydroxyphenyl)carbamoyl]phenyl}-1,3-dihydro-2H-isoindole-2-carboxamide;
N-{4-[(1-ethyl-1H-pyrazol-4-yl)carbamoyl]phenyl}-1,3-dihydro-2H-isoindole-2-carboxamide;
N-{4-[(2,5-dimethoxyphenyl)carbamoyl]phenyl}-1,3-dihydro-2H-isoindole-2-carboxamide;
N-{4-[methyl(3-phenylpropyl)carbamoyl]phenyl}-1,3-dihydro-2H-isoindole-2-carboxamide;
N-{4-[(2-hydroxy-2-methylpropyl)carbamoyl]phenyl}-1,3-dihydro-2H-isoindole-2-carboxamide;
N-(4-{[4-(trifluoromethyl)piperidin-1-yl]carbonyl}phenyl)-1,3-dihydro-2H-isoindole-2-carboxamide;
N-[4-(thiomorpholin-4-ylcarbonyl)phenyl]-1,3-dihydro-2H-isoindole-2-carboxamide;
N-[4-(5,6-dihydroimidazo[1,5-a]pyrazin-7(8H)-ylcarbonyl)phenyl]-1,3-dihydro-2H-isoindole-2-carboxamide;
N-(4-{[4-(2-furoyl)piperazin-1-yl]carbonyl}phenyl)-1,3-dihydro-2H-isoindole-2-carboxamide;
N-{4-[(1-benzylpiperidin-4-yl)carbamoyl]phenyl}-1,3-dihydro-2H-isoindole-2-carboxamide;
N-{4-[(4-methoxyphenyl)carbamoyl]phenyl}-1,3-dihydro-2H-isoindole-2-carboxamide;
N-{4-[(3-methoxyphenyl)carbamoyl]phenyl}-1,3-dihydro-2H-isoindole-2-carboxamide;
N-{4-[(5-acetamido-2-methoxyphenyl)carbamoyl]phenyl}-1,3-dihydro-2H-isoindole-2-carboxamide;
N-(4-{[2-(3,5-dimethoxyphenyl)ethyl]carbamoyl}phenyl)-1,3-dihydro-2H-isoindole-2-carboxamide;
N-[4-({2-[3-(trifluoromethyl)phenyl]ethyl}carbamoyl)phenyl]-1,3-dihydro-2H-isoindole-2-carboxamide;
N-{4-[(2-methylbutan-2-yl)carbamoyl]phenyl}-1,3-dihydro-2H-isoindole-2-carboxamide;
N-(4-{[2-(1H-imidazol-4-yl)ethyl]carbamoyl}phenyl)-1,3-dihydro-2H-isoindole-2-carboxamide;
N-(4-{[(2S)-2-hydroxypropyl]carbamoyl}phenyl)-1,3-dihydro-2H-isoindole-2-carboxamide;
N-(4-{[(1R)-1-(3-cyanophenyl)ethyl]carbamoyl}phenyl)-1,3-dihydro-2H-isoindole-2-carboxamide;
N-(4-{[(2S)-1-hydroxy-3-methylbutan-2-yl]carbamoyl}phenyl)-1,3-dihydro-2H-isoindole-2-carboxamide;
N-{4-[benzyl(2-hydroxyethyl)carbamoyl]phenyl}-1,3-dihydro-2H-isoindole-2-carboxamide;
N-{4-[(4-cyanophenyl)carbamoyl]phenyl}-1,3-dihydro-2H-isoindole-2-carboxamide;
N-(4-([2-(4-chlorophenyl)ethyl]carbamoyl)phenyl)-1,3-dihydro-2H-isoindole-2-carboxamide;
N-(4-{[2-(4-methylpiperazin-1-yl)ethyl]carbamoyl}phenyl)-1,3-dihydro-2H-isoindole-2-carboxamide;
N-(4-{[2-(pyridin-2-yl)ethyl]carbamoyl})phenyl)-1,3-dihydro-2H-isoindole-2-carboxamide;
N-{4-[(cyanomethyl)carbamoyl]phenyl}-1,3-dihydro-2H-isoindole-2-carboxamide;
N-[4-(cyclohexylcarbamoyl)phenyl]-1,3-dihydro-2H-isoindole-2-carboxamide;
N-{4-[(3-hydroxyphenyl)carbamoyl]phenyl}-1,3-dihydro-2H-isoindole-2-carboxamide;
N-{4-[butyl(methyl)carbamoyl]phenyl}-1,3-dihydro-2H-isoindole-2-carboxamide;
N-(4-{[4-(dimethylamino)phenyl]carbamoyl}phenyl)-1,3-dihydro-2H-isoindole-2-carboxamide;
N-[4-(3,4-dihydroisoquinolin-2(1H)-ylcarbonyl)phenyl]-1,3-dihydro-2H-isoindole-2-carboxamide;
N-[4-(1,3-dihydro-2H-isoindol-2-ylcarbonyl)phenyl]-1,3-dihydro-2H-isoindole-2-carboxamide;
N-[4-(2,3-dihydro-1H-indol-1-ylcarbonyl)phenyl]-1,3-dihydro-2H-isoindole-2-carboxamide;
N-[4-(phenylcarbamoyl)phenyl]-1,3-dihydro-2H-isoindole-2-carboxamide;
N-{4-[(4-fluorophenyl)carbamoyl]phenyl}-1,3-dihydro-2H-isoindole-2-carboxamide;
N-(4-{[2-(diethylamino)ethyl]carbamoyl}phenyl)-1,3-dihydro-2H-isoindole-2-carboxamide;
N-{4-[(2-hydroxy-2-phenylethyl)(methyl)carbamoyl]phenyl}-1,3-dihydro-2H-isoindole-2-carboxamide;
N-{4-[(2-aminophenyl)carbamoyl]phenyl}-1,3-dihydro-2H-isoindole-2-carboxamide;
N-(4-{[(2R)-2-hydroxypropyl]carbamoyl}phenyl)-1,3-dihydro-2H-isoindole-2-carboxamide;
N-(4-{[(2S)-1-amino-4-methyl-1-oxopentan-2-yl]carbamoyl}phenyl)-1,3-dihydro-2H-isoindole-2-carboxamide;
tert-butyl (1-{4-[(1,3-dihydro-2H-isoindol-2-ylcarbonyl)amino]benzoyl}piperidin-4-yl)carbamate;

N-(4-{[3-(morpholin-4-yl)propyl]carbamoyl})phenyl)-1,3-dihydro-2H-isoindole-2-carboxamide;
N-[4-((4-[3-chloro-5-(trifluoromethyl)pyridin-2-yl]piperazin-1-yl) carbonyl)phenyl]-1,3-dihydro-2H-isoindole-2-carboxamide;
N-(4-{[4-(cyclohexylmethyl)piperazin-1-yl]carbonyl}phenyl)-1,3-dihydro-2H-isoindole-2-carboxamide;
N-(4-{[1-(3-chlorobenzyl)-1H-pyrazol-4-yl]carbamoyl}phenyl)-1,3-dihydro-2H-isoindole-2-carboxamide;
N-(4-{[3-(diethylcarbamoyl)piperidin-1-yl]carbonyl}phenyl)-1,3-dihydro-2H-isoindole-2-carboxamide;
N-(4-{[3-(piperidin-1-yl)propyl]carbamoyl}phenyl)-1,3-dihydro-2H-isoindole-2-carboxamide;
N-(4-([4-(2-hydroxyethyl)piperazin-1-yl]carbonyl)phenyl)-1,3-dihydro-2H-isoindole-2-carboxamide;
N-{4-[(2-hydroxy-6-methylphenyl)carbamoyl]phenyl}-1,3-dihydro-2H-isoindole-2-carboxamide;
N-(4-{[4-(dimethylamino)butyl]carbamoyl}phenyl)-1,3-dihydro-2H-isoindole-2-carboxamide;
N-{4-[(3-hydroxypropyl)carbamoyl]phenyl}-1,3-dihydro-2H-isoindole-2-carboxamide;
N-{4-[(4-cyclohexylpiperazin-1-yl)carbonyl]phenyl}-1,3-dihydro-2H-isoindole-2-carboxamide;
N-[4-(5,6-dihydro[1,2,4]triazolo[4,3-a]pyrazin-7(8H)-ylcarbonyl)phenyl]-1,3-dihydro-2H-isoindole-2-carboxamide;
N-{4-[methyl(3-methylbutyl)carbamoyl]phenyl}-1,3-dihydro-2H-isoindole-2-carboxamide;
N-[4-(propylcarbamoyl)phenyl]-1,3-dihydro-2H-isoindole-2-carboxamide;
N-(4-{[(2S)-1-hydroxybutan-2-yl]carbamoyl}phenyl)-1,3-dihydro-2H-isoindole-2-carboxamide;
N-{4-[(5-fluoropyridin-2-yl)carbamoyl]phenyl}-1,3-dihydro-2H-isoindole-2-carboxamide;
N-{4-[(cyclopropylmethyl)(propyl)carbamoyl]phenyl}-1,3-dihydro-2H-isoindole-2-carboxamide;
N-(4-{[(2S)-1-methoxypropan-2-yl]carbamoyl}phenyl)-1,3-dihydro-2H-isoindole-2-carboxamide;
N-[4-(1,3,4,9-tetrahydro-2H-beta-carbolin-2-ylcarbonyl)phenyl]-1,3-dihydro-2H-isoindole-2-carboxamide;
N-[4-(tert-butylcarbamoyl)phenyl]-1,3-dihydro-2H-isoindole-2-carboxamide;
N-[4-({4-[4-(trifluoromethyl)phenyl]piperazin-1-yl}carbonyl)phenyl]-1,3-dihydro-2H-isoindole-2-carboxamide;
N-{4-[(3-methylbutan-2-yl)carbamoyl]phenyl}-1,3-dihydro-2H-isoindole-2-carboxamide;
N-{4-[(3,3-difluoropyrrolidin-1-yl)carbonyl]phenyl}-1,3-dihydro-2H-isoindole-2-carboxamide;
N-{4-[(2-methylpiperidin-1-yl)carbonyl]phenyl}-1,3-dihydro-2H-isoindole-2-carboxamide;
N-(4-1{[(3S)-1-benzylpyrrolidin-3-yl]carbamoyl}phenyl)-1,3-dihydro-2H-isoindole-2-carboxamide;
N-{4-[(4-hydroxypiperidin-1-yl)carbonyl]phenyl}-1,3-dihydro-2H-isoindole-2-carboxamide;
N-{4-[bis(2-methoxyethyl)carbamoyl]phenyl)}-1,3-dihydro-2H-isoindole-2-carboxamide;
N-{4-[(3-fluorophenyl)carbamoyl]phenyl}-1,3-dihydro-2H-isoindole-2-carboxamide;
N-[4-(cyclopentylcarbamoyl)phenyl]-1,3-dihydro-2H-isoindole-2-carboxamide;
N-{4-[(4-carbamoylpiperidn-1-yl)carbonyl]phenyl}-1,3-dihydro-2H-isoindole-2-carboxamide;
N-[4-(cyclopropylcarbamoyl)phenyl]-1,3-dihydro-2H-isoindole-2-carboxamide;
N-[4-(methylcarbamoyl)phenyl]-1,3-dihydro-2H-isoindole-2-carboxamide;
N-(4-{[3-(dimethylamino)propyl]carbamoyl}phenyl)-1,3-dihydro-2H-isoindole-2-carboxamide;
N-{4-[methyl(tetrahydrofuran-2-ylmethyl)carbamoyl]phenyl}-1,3-dihydro-2H-isoindole-2-carboxamide;
N-[4-(pentan-2-ylcarbamoyl)phenyl]-1,3-dihydro-2H-isoindole-2-carboxamide;
N-[4-(pentan-3-ylcarbamoyl)phenyl]-1,3-dihydro-2H-isoindole-2-carboxamide;
N-[4-(cyclobutylcarbamoyl)phenyl]-1,3-dihydro-2H-isoindole-2-carboxamide;
N-{4-[(1,3-dioxolan-2-ylmethyl methyl)carbamoyl]phenyl}-1,3-dihydro-2H-isoindole-2-carboxamide;
N-(4-{[1-(4-fluorophenyl)-1H-pyrazol-4-yl]carbamoyl}phenyl)-1,3-dihydro-2H-isoindole-2-carboxamide;
N-{4-[(1-hydroxy-2-methylpropan-2-yl)carbamoyl]phenyl}-1,3-dihydro-2H-isoindole-2-carboxamide;
N-{4-[(1-phenyl-1H-pyrazol-4-yl)carbamoyl]phenyl}-1,3-dihydro-2H-isoindole-2-carboxamide;
N-[4-({2-[4-(trifluoromethyl)phenyl]ethyl}carbamoyl)phenyl]-1,3-dihydro-2H-isoindole-2-carboxamide;
N-{4-[(2-methoxyethyl)(propyl)carbamoyl]phenyl}-1,3-dihydro-2H-isoindole-2-carboxamide;
N-[4-(sec-butylcarbamoyl)phenyl]-1,3-dihydro-2H-isoindole-2-carboxamide;
N-(4-{[3-(trifluoromethyl)piperidin-1-yl]carbonyl}phenyl)-1,3-dihydro-2H-isoindole-2-carboxamide;
N-{4-[bis(2-ethoxyethyl)carbamoyl]phenyl}-1,3-dihydro-2H-isoindole-2-carboxamide;
N-{4-[butyl(ethyl)carbamoyl]phenyl}-1,3-dihydro-2H-isoindole-2-carboxamide;
N-{4-[(1-methoxypropan-2-yl)carbamoyl]phenyl}-1,3-dihydro-2H-isoindole-2-carboxamide;
N-{4-[(2-methoxyethyl)(methyl)carbamoyl]phenyl}-1,3-dihydro-2H-isoindole-2-carboxamide;
N-{4-[(3R)-tetrahydrofuran-3-ylcarbamoyl]phenyl}-1,3-dihydro-2H-isoindole-2-carboxamide;
N-[4-(morpholin-4-ylcarbonyl)phenyl]-1,3-dihydro-2H-isoindole-2-carboxamide;
N-{4-[isobutyl(methyl)carbamoyl]phenyl}-1,3-dihydro-2H-isoindole-2-carboxamide;
N-[4-({4-[2-(2-hydroxyethoxy)ethyl]piperazin-1-yl}carbonyl)phenyl]-1,3-dihydro-2H-isoindole-2-carboxamide;
N-{4-[(3-methylpiperidin-1-yl)carbonyl]phenyl}-1,3-dihydro-2H-isoindole-2-carboxamide;
N-(4-carbamoylphenyl)-1,3-dihydro-2H-isoindole-2-carboxamide;
N-(4-{[(2S)-2-(trifluoromethyl)pyrrolidin-1-yl]carbonyl}phenyl)-1,3-dihydro-2H-isoindole-2-carboxamide;
N-(4-{[(2S)-1-hydroxy-4-methylpentan-2-yl]carbamoyl}phenyl)-1,3-dihydro-2H-isoindole-2-carboxamide;
N-(4-{[(1R)-2-hydroxy-1-phenylethyl]carbamoyl})phenyl)-1,3-dihydro-2H-isoindole-2-carboxamide;
N-{4-[(2-methylpyrrolidin-1-yl)carbonyl]phenyl}-1,3-dihydro-2H-isoindole-2-carboxamide;
N-{4-[ethyl(2-methoxyethyl)carbamoyl]phenyl}-1,3-dihydro-2H-isoindole-2-carboxamide;

N-(4-{[(2R)-1-hydroxy-3-methylbutan-2-yl]carbamoyl}phenyl)-1,3-dihydro-2H-isoindole-2-carboxamide;
N-{4-[(2,6-dimethylmorpholin-4-yl)carbonyl]phenyl}-1,3-dihydro-2H-isoindole-2-carboxamide;
N-(4-{[(2R)-1-hydroxybutan-2-yl]carbamoyl}phenyl)-1,3-dihydro-2H-isoindole-2-carboxamide;
N-{4-[(2,5-dimethylpyrrolidin-1-yl)carbonyl]phenyl}-1,3-dihydro-2H-isoindole-2-carboxamide;
N-[4-(prop-2-yn-1-ylcarbamoyl)phenyl]-1,3-dihydro-2H-isoindole-2-carboxamide;
N-{4-[isopropyl(2-methoxyethyl)carbamoyl]phenyl}-1,3-dihydro-2H-isoindole-2-carboxamide;
N-{4-[isopropyl(propyl)carbamoyl]phenyl}-1,3-dihydro-2H-isoindole-2-carboxamide;
N-{4-[(2-cyanoethyl)(cyclopropyl)carbamoyl]phenyl}-1,3-dihydro-2H-isoindole-2-carboxamide;
N-{4-[ethyl(isopropyl)carbamoyl]phenyl}-1,3-dihydro-2H-isoindole-2-carboxamide;
N-{4-[(3-fluoropyrrolidin-1-yl)carbonyl]phenyl}-1,3-dihydro-2H-isoindole-2-carboxamide;
N-{4-[(1,3-dihydro-2H-isoindol-2-ylcarbonyl)amino]benzoyl}-N-isopropyl-beta-alanine;
N-{4-[methyl(propyl)carbamoyl]phenyl}-1,3-dihydro-2H-isoindole-2-carboxamide;
5,6-dimethoxy-N-{4-[(3-phenylpropyl)carbamoyl]phenyl}-1,3-dihydro-2H-isoindole-2-carboxamide;
N-(4-{[3-(4-chlorophenoxyl)propyl]carbamoyl}phenyl)-1,3-dihydro-2H-isoindole-2-carboxamide;
N-(4-{[4-(trifluoromethoxy)phenyl]carbamoyl}phenyl)-1,3-dihydro-2H-isoindole-2-carboxamide;
N-{4-[(4-phenyl-1,3-thiazol-2-yl)carbamoyl]phenyl}-1,3-dihydro-2H-isoindole-2-carboxamide;
methyl 2-{[4-(propylcarbamoyl)phenyl]carbamoyl}isoindoline-5-carboxylate;
2-{[4-(propylcarbamoyl)phenyl]carbamoyl}isoindoline-5-carboxylic acid;
5-amino-N-[4-(propylcarbamoyl)phenyl]-1,3-dihydro-2H-isoindole-2-carboxamide;
5-(hydroxymethyl)-N-[4-(propylcarbamoyl)phenyl]-1,3-dihydro-2H-isoindole-2-carboxamide;
5-(aminomethyl)-N-[4-(propylcarbamoyl)phenyl]-1,3-dihydro-2H-isoindole-2-carboxamide;
5-[(2-hydroxy-2-methylpropanoyl)amino]-N-[4-(propylcarbamoyl)phenyl]-1,3-dihydro-2H-isoindole-2-carboxamide;
5-acetamido-N-[4-(propylcarbamoyl)phenyl]-1,3-dihydro-2H-isoindole-2-carboxamide;
5-[(N,N-dimethylglycyl)amino]-N-[4-(propylcarbamoyl)phenyl]-1,3-dihydro-2H-isoindole-2-carboxamide;
N-[4-(propylcarbamoyl)phenyl]-5-(1H-pyrazol-3-yl)-1,3-dihydro-2H-isoindole-2-carboxamide;
N-[4-(propylcarbamoyl)phenyl]-5-(1H-pyrazol-4-yl)-1,3-dihydro-2H-isoindole-2-carboxamide;
5-[(methoxyacetyl)amino]-N-[4-(propylcarbamoyl)phenyl]-1,3-dihydro-2H-isoindole-2-carboxamide;
5-[(methylsulfonyl)amino]-N-[4-(propylcarbamoyl)phenyl]-1,3-dihydro-2H-isoindole-2-carboxamide;
5-bromo-N-[4-(propylcarbamoyl)phenyl]-1,3-dihydro-2H-isoindole-2-carboxamide;
N-{4-[(4,4,4-trifluorobutanoyl)amino]phenyl}-1,3-dihydro-2H-isoindole-2-carboxamide;
N-{4-[(3-ethoxypropanoyl)amino]phenyl}-1,3-dihydro-2H-isoindole-2-carboxamide;
N-{4-[(4-phenylbutanoyl)amino]phenyl}-1,3-dihydro-2H-isoindole-2-carboxamide;
N-{4-[(4-methylpentanoyl)amino]phenyl}-1,3-dihydro-2H-isoindole-2-carboxamide;
N-(4-{[(benzyloxy)acetyl]amino}phenyl)-1,3-dihydro-2H-isoindole-2-carboxamide;
N-{4-[(3-phenylpropanoyl)amino]phenyl}-1,3-dihydro-2H-isoindole-2-carboxamide;
N-{4-[(3-phenoxypropanoyl)amino]phenyl}-1,3-dihydro-2H-isoindole-2-carboxamide;
N-(4-{[N-(2-furoyl)glycyl]amino}phenyl)-1,3-dihydro-2H-isoindole-2-carboxamide;
N-(4-{[4-(2-thienyl)butanoyl]amino}phenyl)-1,3-dihydro-2H-isoindole-2-carboxamide;
N-{4-[(4-oxo-4-phenylbutanoyl)amino]phenyl}-1,3-dihydro-2H-isoindole-2-carboxamide;
N-{4-[(N-benzoylglycyl)amino]phenyl}-1,3-dihydro-2H-isoindole-2-carboxamide;
N-{4-[(4-phenoxybutanoyl)amino]phenyl}-1,3-dihydro-2H-isoindole-2-carboxamide;
N-[4-(propionylamino)phenyl]-1,3-dihydro-2H-isoindole-2-carboxamide;
N-[4-(pentanoylamino)phenyl]-1,3-dihydro-2H-isoindole-2-carboxamide;
N-[4-(hexanoylamino)phenyl]-1,3-dihydro-2H-isoindole-2-carboxamide;
N-[4-(heptanoylamino)phenyl]-1,3-dihydro-2H-isoindole-2-carboxamide;
N-[4-(pent-4-enoylamino)phenyl]-1,3-dihydro-2H-isoindole-2-carboxamide;
N-{4-[(ethoxyacetyl)amino]phenyl}-1,3-dihydro-2H-isoindole-2-carboxamide;
N-(4-{[(2-methoxyethoxy)acetyl]amino}phenyl)-1,3-dihydro-2H-isoindole-2-carboxamide;
N-{4-[(cyclopropylacetyl)amino]phenyl}-1,3-dihydro-2H-isoindole-2-carboxamide;
N-{4-[(cyclopentylacetyl)amino]phenyl}-1,3-dihydro-2H-isoindole-2-carboxamide;
N-(4-{[3-(4-methylpiperazin-1-yl)propanoyl]amino}phenyl)-1,3-dihydro-2H-isoindole-2-carboxamide;
methyl 2-({4-[(cyclopentylacetyl)amino]phenyl}carbamoyl)isoindoline-5-carboxylate;
2-({4-[(cyclopentylacetyl)amino]phenyl}carbamoyl)isoindoline-5-carboxylic acid;
N-{4-[(cyclopentylacetyl)amino]phenyl}-5-(hydroxymethyl)-1,3-dihydro-2H-isoindole-2-carboxamide;
N-{4-[(2-cyclopentylethyl)amino]phenyl}-5-(hydroxymethyl)-1,3-dihydro-2H-isoindole-2-carboxamide;
tert-butyl 4-{4-[(1,3-dihydro-2H-isoindol-2-ylcarbonyl)amino]phenyl}-3,6-dihydropyridine-1(2H)-carboxylate;
N-[4-(1,2,3,6-tetrahydropyridin-4-yl)phenyl]-1,3-dihydro-2H-isoindole-2-carboxamide;
N-{4-[1-(3-methylbutyl)-1H-pyrazol-4-yl]phenyl}-1,3-dihydro-2H-isoindole-2-carboxamide;
N-[4-(1-methyl-1H-pyrazol-4-yl)phenyl]-1,3-dihydro-2H-isoindole-2-carboxamide;
N-{4-[(1E)-5-phenylpent-1-en-1-yl]phenyl}-1,3-dihydro-2H-isoindole-2-carboxamide;
N-[4-(1-propyl-1H-pyrazol-4-yl)phenyl]-1,3-dihydro-2H-isoindole-2-carboxamide;
N-[4-(1-benzyl-1H-pyrazol-4-yl)phenyl]-1,3-dihydro-2H-isoindole-2-carboxamide;
N-{4-[1-(2-hydroxyethyl)-1H-pyrazol-4-yl]phenyl}-1,3-dihydro-2H-isoindole-2-carboxamide;
N-[6-(1-propyl-1H-pyrazol-4-yl)pyridin-3-yl]-1,3-dihydro-2H-isoindole-2-carboxamide;

N-{6-[1-(3-methylbutyl)-1H-pyrazol-4-yl]pyridin-3-yl}-1,3-dihydro-2H-isoindole-2-carboxamide;
N-[4-(5-phenylpentyl)phenyl]-1,3-dihydro-2H-isoindole-2-carboxamide;
N-[2-fluoro-4-(1-propyl-1H-pyrazol-4-yl)phenyl]-1,3-dihydro-2H-isoindole-2-carboxamide;
N-{2-fluoro-4-[1-(3-methylbutyl)-1H-pyrazol-4-yl]phenyl}-1,3-dihydro-2H-isoindole-2-carboxamide;
N-[4-(1-butyryl-1,2,3,6-tetrahydropyridin-4-yl)phenyl]-1,3-dihydro-2H-isoindole-2-carboxamide;
N-[4-(1-isobutyryl-1,2,3,6-tetrahydropyridin-4-yl)phenyl]-1,3-dihydro-2H-isoindole-2-carboxamide;
N-[4-(1-benzoyl-1,2,3,6-tetrahydropyridin-4-yl)phenyl]-1,3-dihiydro-2H-isoindole-2-carboxamide;
N-{4-[1-(isopropylsulfonyl)-1,2,3,6-tetrahydropyridin-4-yl]phenyl}-1,3-dihydro-2H-isoindole-2-carboxamide;
N-(1'-isobutyryl-1',2',3',6'-tetrahydro-2,4'-bipyridin-5-yl)-1,3-dihydro-2H-isoindole-2-carboxamide;
N-(1'-benzoyl-1',2',3',6'-tetrahydro-2,4'-bipyridin-5-yl)-1,3-dihydro-2H-isoindole-2-carboxamide;
N-[4-(4-benzoylpiperazin-1-yl)phenyl]-1,3-dihydro-2H-isoindole-2-carboxamide;
N-{4-[4-(isopropylsulfonyl)piperazin-1-yl]phenyl}-1,3-dihydro-2H-isoindole-2-carboxamide;
N-{4-[4-(phenylsulfonyl)piperazin-1-yl]phenyl}-1,3-dihydro-2H-isoindole-2-carboxamide;
N-{4-[3-(benzoylamino)pyrrolidin-1-yl]phenyl}-1,3-dihydro-2H-isoindole-2-carboxamide;
N-{4-[3-(butyrylamino)pyrrolidin-1-yl]phenyl}-1,3-dihydro-2H-isoindole-2-carboxamide;
tert-butyl 4-{4-[(1,3-dihydro-2H-isoindol-2-ylcarbonyl)amino]phenyl}piperazine-1-carboxylate;
N-[4-(4-propionylpiperazin-1-yl)phenyl]-1,3-dihydro-2H-isoindole-2-carboxamide;
N-{4-[4-(cyclopropylcarbonyl)piperazin-1-yl]phenyl}-1,3-dihydro-2H-isoindole-2-carboxamide;
N-(2-butyryl-2,3-dihydro-1H-isoindol-5-yl)-1,3-dihydro-2H-isoindole-2-carboxamide;
N-(2-isobutyryl-2,3-dihydro-1H-isoindol-5-yl)-1,3-dihydro-2H-isoindole-2-carboxamide;
N-(2-benzoyl-2,3-dihydro-11H-isoindol-5-yl)-1,3-dihydro-2H-isoindole-2-carboxamide;
N-[2-(3-methylbutyl)-2,3-dihydro-1H-isoindol-5-yl]-1,3-dihydro-2H-isoindole-2-carboxamide;
N-[4-(hexyloxy)phenyl]-1,3-dihydro-2H-isoindole-2-carboxamide;
N-[4-(1-benzoylpiperidin-4-yl)butyl]-1,3-dihydro-2H-isoindole-2-carboxamide;
N-{4-[1-(pyridin-3-ylcarbonyl)piperidin-4-yl]butyl}-1,3-dihydro-2H-isoindole-2-carboxamide;
N-[6-(4-chlorophenoxy)hexyl]-1,3-dihydro-2H-isoindole-2-carboxamide;
N-[4-(piperidin-4-yl)butyl]-1,3-dihydro-2H-isoindole-2-carboxamide;
N,N'-hexane-1,6-diylbis(1,3-dihydro-2H-isoindole-2-carboxamide);
N-(4-phenylbutyl)-1,3-dihydro-2H-isoindole-2-carboxamide;
ethyl 6-[(1,3-dihydro-2H-isoindol-2-ylcarbonyl)amino]hexanoate;
N-hexyl-1,3-dihydro-2H-isoindole-2-carboxamide;
N-octyl-1,3-dihydro-2H-isoindole-2-carboxamide;
N-{6-[(1-methyl-1H-pyrazol-4-yl)amino]-6-oxohexyl}-1,3-dihydro-2H-isoindole-2-carboxamide;
N-[6-(methylamino)-6-oxohexyl]-1,3-dihydro-2H-isoindole-2-carboxamide;
N-{6-oxo-6-[(3-phenylpropyl)amino]hexyl}-1,3-dihydro-2H-isoindole-2-carboxamide;
N-{6-[(3-methylbutyl)amino]-6-oxohexyl}-1,3-dihydro-2H-isoindole-2-carboxamide;
N-(5-{[4-(pyridin-2-yl)piperazin-1-yl]carbonyl}pyridin-2-yl)-1,3-dihydro-2H-isoindole-2-carboxamide;
N-{5-[(3-phenylpropyl)carbamoyl]pyridin-2-yl}-1,3-dihydro-2H-isoindole-2-carboxamide;
N-{5-[(3-methylbutyl)carbamoyl]pyridin-2-yl}-1,3-dihydro-2H-isoindole-2-carboxamide;
N-{5-[(3-phenylpropyl)carbamoyl]-1,3-thiazol-2-yl}-1,3-dihydro-2H-isoindole-2-carboxamide;
N-{5-[(3-methylbutyl)carbamoyl]-1,3-thiazol-2-yl}-1,3-dihydro-2H-isoindole-2-carboxamide;
5-fluoro-N-[4-(propylcarbamoyl)phenyl]-1,3-dihydro-2H-isoindole-2-carboxamide;
N-[4-(4-oxo-3,4-dihydrophthalazin-1-yl)phenyl]-1,3-dihydro-2H-isoindole-2-carboxamide;
N-[4-(isoquinolin-4-yl)phenyl]-1,3-dihydro-2H-isoindole-2-carboxamide;
N-[4-(1-oxo-1,2-dihydroisoquinolin-4-yl)phenyl]-1,3-dihydro-2H-isoindole-2-carboxamide;
N-[4-(4-oxo-3,4,5,6,7,8-hexahydrophthalazin-1-yl)phenyl]-1,3-dihydro-2H-isoindole-2-carboxamide;
N-[4-(8-fluoro-4-oxo-3,4-dihydrophthalazin-1-yl)phenyl]-1,3-dihydro-2H-isoindole-2-carboxamide;
5-fluoro-N-[4-(4-oxo-3,4-dihydrophthalazin-1-yl)phenyl]-1,3-dihydro-2H-isoindole-2-carboxamide;
N-[4-(4-oxo-3,4-dihydrophthalazin-1-yl)phenyl]-5-(pyrrolidin-1-ylmethyl)-1,3-dihydro-2H-isoindole-2-carboxamide;
5-(morpholin-4-ylmethyl)-N-[4-(1-oxo-1,2-dihydroisoquinolin-4-yl)phenyl]-1,3-dihydro-2H-isoindole-2-carboxamide;
5-methoxy-N-[4-(1-oxo-1,2-dihydroisoquinolin-4-yl)phenyl]-1,3-dihydro-2H-isoindole-2-carboxamide;
5-[(4-methylpiperazin-1-yl)methyl]-N-[4-(4-oxo-3,4-dihydrophthalazin-1-yl)phenyl]-1,3-dihydro-2H-isoindole-2-carboxamide;
5-cyano-N-[4-(1-oxo-1,2-dihydroisoquinolin-4-yl)phenyl]-1,3-dihydro-2H-isoindole-2-carboxamide;
5-chloro-N-[4-(1-oxo-1,2-dihydroisoquinolin-4-yl)phenyl]-1,3-dihydro-2H-isoindole-2-carboxamide;
N-[4-(4-oxo-4,5-dihydro-3H-2,3-benzodiazepin-1-yl)phenyl]-1,3-dihydro-2H-isoindole-2-carboxamide;
N-[4-(1-oxo-1,2-dihydroisoquinolin-4-yl)phenyl]-5-(pyrrolidin-1-yl methyl)-1,3-dihydro-2H-isoindole-2-carboxamide;
N-{4-[4-oxo-8-(trifluoromethyl)-3,4-dihydrophthalazin-1-yl]phenyl}-1,3-dihydro-2H-isoindole-2-carboxamide;
5-[(dimethylamino)methyl]-N-[4-(1-oxo-1,2-dihydroisoquinolin-4-yl)phenyl]-1,3-dihydro-2H-isoindole-2-carboxamide;
5-[(diethylamino)methyl]-N-[4-(1-oxo-1,2-dihydroisoquinolin-4-yl)phenyl]-1,3-dihydro-2H-isoindole-2-carboxamide;
5-[(4-methylpiperazin-1-yl)methyl]-N-[4-(1-oxo-1,2-dihydroisoquinolin-4-yl)phenyl]-1,3-dihydro-2H-isoindole-2-carboxamide;
5-[(dimethylamino)methyl]-N-[4-(4-oxo-3,4-dihydrophthalazin-1-yl)phenyl]-1,3-dihydro-2H-isoindole-2-carboxamide;
5-[(diethylamino)methyl]-N-[4-(4-oxo-3,4-dihydrophthalazin-1-yl)phenyl]-1,3-dihydro-2H-isoindole-2-carboxamide;

N-{4-[4-oxo-8-(trifluoromethyl)-3,4-dihydrophthalazin-1-yl]phenyl}-5-(pyrrolidin-1-ylmethyl)-1,3-dihydro-2H-isoindole-2-carboxamide;

5-[(1-methylpiperidin-4-yl)oxy]-N-[4-(4-oxo-3,4-dihydrophthalazin-1-yl)phenyl]-1,3-dihydro-2H-isoindole-2-carboxamide;

5-{[(3R)-3-fluoropyrrolidin-1-yl]methyl}-N-[4-(4-oxo-3,4-dihydrophthalazin-1-yl)phenyl]-1,3-dihydro-2H-isoindole-2-carboxamide;

5-{[(3S)-3-fluoropyrrolidin-1-yl]methyl}-N-[4-(4-oxo-3,4-dihydrophthalazin-1-yl)phenyl]-1,3-dihydro-2H-isoindole-2-carboxamide;

5-(azetidin-1-ylmethyl)-N-[4-(4-oxo-3,4-dihydrophthalazin-1-yl)phenyl]-1,3-dihydro-2H-isoindole-2-carboxamide;

N-[4-(1-oxo-1,2-dihydropyrrolo[1,2-d][1,2,4]triazin-4-yl)phenyl]-1,3-dihydro-2H-isoindole-2-carboxamide;

N-[4-(1-oxo-1,2-dihydropyrrolo[1,2-d][1,2,4]triazin-4-yl)phenyl]-5-(pyrrolidin-1-ylmethyl)-1,3-dihydro-2H-isoindole-2-carboxamide;

tert-butyl 4-{4-[(1,3-dihydro-2H-isoindol-2-ylcarbonyl)amino]phenyl}piperidine-1-carboxylate;

N-[4-(5-propyl-1,2,4-oxadiazol-3-yl)phenyl]-1,3-dihydro-2H-isoindole-2-carboxamide;

N-[4-(piperidin-4-yl)phenyl]-1,3-dihydro-2H-isoindole-2-carboxamide;

N-{5-[(tetrahydrofuran-3-ylmethyl)carbamoyl]pyridin-2-yl)}-1,3-dihydro-2H-isoindole-2-carboxamide;

N-[4-(1-butyrylpiperidin-4-yl)phenyl]-1,3-dihydro-2H-isoindole-2-carboxamide;

N-[4-(1-isobutyrylpiperidin-4-yl)phenyl]-1,3-dihydro-2H-isoindole-2-carboxamide;

N-[4-(1-benzoylpiperidin-4-yl)phenyl]-1,3-dihydro-2H-isoindole-2-carboxamide;

N-{4-[5-(3-methylbutyl)-1,2,4-oxadiazol-3-yl]phenyl}-1,3-dihydro-2H-isoindole-2-carboxamide;

N-[4-(5-benzyl-1,2,4-oxadiazol-3-yl)phenyl]-1,3-dihydro-2H-isoindole-2-carboxamide;

N-(4-{[(3R)-tetrahydrofuran-3-ylmethyl]carbamoyl}phenyl)-1,3-dihydro-2H-isoindole-2-carboxamide;

N-(4-{[(3S)-tetrahydrofuran-3-ylmethyl]carbamoyl}phenyl)-1,3-dihydro-2H-isoindole-2-carboxamide;

N-{4-[(2-methoxyethyl)carbamoyl]phenyl}-1,3-dihydro-2H-isoindole-2-carboxamide;

N-{4-[(5-chloropyridin-2-yl)carbamoyl]phenyl}-1,3-dihydro-2H-isoindole-2-carboxamide;

N-{4-[(3-hydroxy-4-methoxyphenyl)carbamoyl]phenyl}-1,3-dihydro-2H-isoindole-2-carboxamide;

N-{4-[(2,4-dimethoxybenzyl)carbamoyl]phenyl}-1,3-dihydro-2H-isoindole-2-carboxamide;

N-(4-{[4-(2-oxopyrrolidin-1-yl)benzyl]carbamoyl}phenyl)-1,3-dihydro-2H-isoindole-2-carboxamide;

N-(4-{[(1S,2S)-2-hydroxy-2,3-dihydro-1H-inden-1-yl]carbamoyl}phenyl)-1,3-dihydro-2H-isoindole-2-carboxamide;

N-(4-{[(1-hydroxycyclopropyl)methyl]carbamoyl}phenyl)-1,3-dihydro-2H-isoindole-2-carboxamide;

N-{4-[(tetrahydro-2H-pyran-2-ylmethyl)carbamoyl]phenyl}-1,3-dihydro-2H-isoindole-2-carboxamide;

N-{4-[(tetrahydro-2H-pyran-3-ylmethyl)carbamoyl]phenyl}-1,3-dihydro-2H-isoindole-2-carboxamide;

N-{4-[(tetrahydro-2H-pyran-4-ylmethyl)carbamoyl]phenyl}-1,3-dihydro-2H-isoindole-2-carboxamide;

tert-butyl 4-{6-[(1,3-dihydro-2H-isoindol-2-ylcarbonyl)amino]-1H-benzimidazol-2-yl}piperazine-1-carboxylate;

N-[2-(piperazin-1-yl)-1H-benzimidazol-6-yl]-1,3-dihydro-2H-isoindole-2-carboxamide;

N-[4-(propylcarbamoyl)phenyl]-5-vinyl-1,3-dihydro-2H-isoindole-2-carboxamide;

N-{4-[(4-benzoylpiperazin-1-yl)carbonyl]phenyl}-1,3-dihydro-2H-isoindole-2-carboxamide;

N-{4-[5-(tetrahydrofuran-3-yl)-1,2,4-oxadiazol-3-yl]phenyl}-1,3-dihydro-2H-isoindole-2-carboxamide;

N-[4-(1-isobutyl-1,2,3,6-tetrahydropyridin-4-yl)phenyl]-1,3-dihydro-2H-isoindole-2-carboxamide;

N-{4-[1-(4-methylbenzoyl)-1,2,3,6-tetrahydropyridin-4-yl]phenyl)}-1,3-dihydro-2H-isoindole-2-carboxamide;

N-[4-(1-benzyl-1,2,3,6-tetrahydropyridin-4-yl)phenyl]-1,3-dihydro-2H-isoindole-2-carboxamide;

N-(4-{[4-(tetrahydrofuran-3-ylmethyl)piperazin-1-yl]carbonyl}phenyl)-1,3-dihydro-2H-isoindole-2-carboxamide;

5-fluoro-N-[4-({[(2S)-tetrahydropyridin-2-ylmethyl]amino}carbonyl)phenyl]-1,3-dihydro-2H-isoindole-2-carboxamide;

5-fluoro-N-[4-(4-{[(2R)-tetrahydrofuran-2-ylmethyl]amino}carbonyl)phenyl]-1,3-dihydro-2H-isoindole-2-carboxamide;

N-(4-4 [4-(2-methoxyethyl)piperazin-1-yl]carbonyl)phenyl)-1,3-dihydro-2H-isoindole-2-carboxamide;

N-(4-{[(2S)-2-(2-hydroxyethyl)piperidin-1-yl]carbonyl}phenyl)-1,3-dihydro-2H-isoindole-2-carboxamide;

N-{4-[(propylamino)carbonyl]phenyl}-5-pyridin-3-yl-1,3-dihydro-2H-isoindole-2-carboxamide;

N-{4-[(propylamino)carbonyl]phenyl}-5-pyridin-4-yl-1,3-dihydro-2H-isoindole-2-carboxamide;

$N^5$-(2-methoxyethyl)-$N^2$-{4-[(propylamino)carbonyl]phenyl}-1,3-dihydro-2H-isoindole-2,5-dicarboxamide;

N-(4-cyanophenyl)-1,3-dihydro-2H-isoindole-2-carboxamide;

N-[4-(trifluoromethyl)phenyl]-1,3-dihydro-2H-isoindole-2-carboxamide;

N-[4-({[(1S)-2-hydroxy-1-pyridin-2-ylethyl]amino}carbonyl)phenyl]-1,3-dihydro-2H-isoindole-2-carboxamide;

5-(1,2-dihydroxyethyl)-N-{4-[(propylamino)carbonyl]phenyl}-1,3-dihydro-2H-isoindole-2-carboxamide;

N-[4-(1-benzoylpiperidin-4-yl)butyl]-5-cyano-1,3-dihydro-2H-isoindole-2-carboxamide;

N-(1'-butyryl-1',2',3',6'-tetrahydro-3,4'-bipyridin-6-yl)-1,3-dihydro-2H-isoindole-2-carboxamide;

N-(1'-isobutyryl-1',2',3',6'-tetrahydro-3,4'-bipyridin-6-yl)-1,3-dihydro-2H-isoindole-2-carboxamide;

N-[1'-(tetrahydrofuran-3-ylcarbonyl)-1' 2',3',6'-tetrahydro-3,4'-bipyridin-6-yl]-1,3-dihydro-2H-isoindole-2-carboxamide; and N-[2-(4-acetylpiperazin-1-yl)-1H-benzimidazol-5-yl]-1,3-dihydro-2H-isoindole-2-carboxamide;

N-{4-[1-(5-oxo-L-prolyl)-1,2,3,6-tetrahydropyridin-4-yl]phenyl}-1,3-dihydro-2H-isoindole-2-carboxamide;

N-{4-[1-(5-oxo-D-prolyl)-1,2,3,6-tetrahydropyridin-4-yl]phenyl}-1,3-dihydro-2H-isoindole-2-carboxamide;

N-[4-(1-propionyl-1,2,3,6-tetrahydropyridin-4-yl)phenyl]-1,3-dihydro-2H-isoindole-2-carboxamide;

N-{4-[1-(2-methylbutanoyl)-1,2,3,6-tetrahydropyridin-4-yl]phenyl)}-1,3-dihydro-2H-isoindole-2-carboxamide;

N-{4-[1-(2-ethylbutanoyl)-1,2,3,6-tetrahydropyridin-4-yl]phenyl}-1,3-dihydro-2H-isoindole-2-carboxamide;

N-{4-[1-(methoxyacetyl)-1,2,3,6-tetrahydropyridin-4-yl]
phenyl}-1,3-dihydro-2H-isoindole-2-carboxamide;
N-{4-[1-(ethoxyacetyl)-1,2,3,6-tetrahydropyridin-4-yl]
phenyl}-1,3-dihydro-2H-isoindole-2-carboxamide;
N-(4-{1-[(2-methoxyethoxy)acetyl]-1 2,3,6-tetrahydro-
pyridin-4-yl}phenyl)-1,3-dihydro-2H-isoindole-2-car-
boxamide;
N-{4-[1-(tetrahydrofuran-2-ylcarbonyl)-1,2,3,6-tetrahy-
dropyridin-4-yl]phenyl}-1,3-dihydro-2H-isoindole-2-
carboxamide;
N-{4-[1-(tetrahydrofuran-3-ylcarbonyl)-1,2,3,6-tetrahy-
dropyridin-4-yl]phenyl}-1,3-dihydro-2H-isoindole-2-
carboxamide;
N-{4-[1-(cyclopropylacetyl)-1,2,3,6-tetrahydropyridin-4-
yl]phenyl}-1,3-dihydro-2-isoindole-2-carboxamide;
N-{4-[1-(cyclopentylcarbonyl)-1,2,3,6-tetrahydropyri-
din-4-yl]phenyl}-1,3-dihydro-2H-isoindole-2-carboxa-
mide;
N-{4-[1-(2-methylbenzoyl)-1,2,3,6-tetrahydropyridin-4-
yl]phenyl}-1,3-dihydro-2H-isoindole-2-carboxamide;
N-{4-[1-(3-methylbenzoyl)-1,2,3,6-tetrahydropyridin-4-
yl]phenyl}-1,3-dihydro-2H-isoindole-2-carboxamide;
N-{4-[1-(2-methoxybenzoyl)-1,2,3,6-tetrahydropyridin-
4-yl]phenyl}-1,3-dihydro-2H-isoindole-2-carboxam-
ide;
N-{4-[1-(3-methoxybenzoyl)-1,2,3,6-tetrahydropyridin-
4-yl]phenyl}-1,3-dihydro-2H-isoindole-2-carboxam-
ide;
N-{4-[1-(4-methoxybenzoyl)-1,2,3,6-tetrahydropyridin-
4-yl]phenyl}-1,3-dihydro-2H-isoindole-2-carboxam-
ide;
N-{4-[1-(2-fluorobenzoyl)-1,2,3,6-tetrahydropyridin-4-
yl]phenyl}-1,3-dihydro-2H-isoindole-2-carboxamide;
N-{4-[1-(3-fluorobenzoyl)-1,2,3,6-tetrahydropyridin-4-
yl]phenyl}-1,3-dihydro-2H-isoindole-2-carboxamide;
N-{4-[1-(4-fluorobenzoyl)-1,2,3,6-tetrahydropyridin-4-
yl]phenyl}-1,3-dihydro-2H-isoindole-2-carboxamide;
N-{4-[1-(4-chlorobenzoyl)-1,2,3,6-tetrahydropyridin-4-
yl]phenyl}-1,3-dihydro-2H-isoindole-2-carboxamide;
N-(4-{1-[3-(dimethylamino)benzoyl]-1,2,3,6-tetrahydro-
pyridin-4-yl)phenyl}-1,3-dihydro-2H-isoindole-2-car-
boxamide;
N-(4-{1-[4-(dimethylamino)benzoyl]-1,2,3,6-tetrahydro-
pyridin-4-yl}phenyl)-1,3-dihydro-2H-isoindole-2-car-
boxamide;
N-{4-[1-(3-furoyl)-1,2,3,6-tetrahydropyridin-4-yl]phe-
nyl}-1,3-dihydro-2H-isoindole-2-carboxamide;
N-{4-[1-(3-thienylcarbonyl)-1,2,3,6-tetrahydropyridin-4-
yl]phenyl}-1,3-dihydro-2H-isoindole-2-carboxamide;
N-{4-[1-(1H-pyrrol-2-ylcarbonyl)-1,2,3,6-tetrahydropy-
ridin-4-yl]phenyl}-1,3-dihydro-2H-isoindole-2-car-
boxamide;
N-(4-{1-[(2,5-dimethyl-1H-pyrrol-3-yl)carbonyl]-1,2,3,
6-tetrahydropyridin-4-yl}phenyl)-1,3-dihydro-2H-
isoindole-2-carboxamide;
N-{4-[1-(1,3-thiazol-4-ylcarbonyl)-1,2,3,6-tetrahydropy-
ridin-4-yl]phenyl}-1,3-dihydro-2H-isoindole-2-car-
boxamide;
N-{4-[1-(1H-pyrazol-4-ylcarbonyl)-1,2,3,6-tetrahydro-
pyridin-4-yl]phenyl}-1,3-dihydro-2H-isoindole-2-car-
boxamide;
N-(4-{1-[(3,5-dimethyl-1,2-oxazol-4-yl)carbonyl]-1,2,3,
6-tetrahydropyridin-4-yl}phenyl)-1,3-dihydro-2H-
isoindole-2-carboxamide;
N-{4-[1-(pyridin-2-ylcarbonyl)-1,2,3,6-tetrahydropyri-
din-4-yl]phenyl}-1,3-dihydro-2H-isoindole-2-carboxa-
mide;
N-{4-[1-(pyridin-3-ylcarbonyl)-1,2,3,6-tetrahydropyri-
din-4-yl]phenyl}-1,3-dihydro-2H-isoindole-2-carboxa-
mide;
N-[4-(1-isonicotinoyl-1,2,3,6-tetrahydropyridin-4-yl)
phenyl]-1,3-dihydro-2H-isoindole-2-carboxamide;
N-{4-[1-(pyridazin-3-ylcarbonyl)-1,2,3,6-tetrahydropyri-
din-4-yl]phenyl}-1,3-dihydro-2H-isoindole-2-carboxa-
mide;
N-{4-[1-(pyrazin-2-ylcarbonyl)-1,2,3,6-tetrahydropyri-
din-4-yl]phenyl}-1,3-dihydro-2H-isoindole-2-carboxa-
mide;
N-{4-[1-(pyrimidin-4-ylcarbonyl)-1,2,3,6-tetrahydropy-
ridin-4-yl]phenyl}-1,3-dihydro-2H-isoindole-2-car-
boxamide;
N-(4-{1-[3-(piperidin-1-yl)propanoyl]-1,2,3,6-tetrahy-
dropyridin-4-yl}phenyl)-1,3-dihydro-2H-isoindole-2-
carboxamide;
N-{4-[1-(morpholin-4-ylacetyl)-1,2,3,6-tetrahydropyri-
din-4-yl]phenyl}-1,3-dihydro-2H-isoindole-2-carboxa-
mide;
N-(4-{1-[(4-methylpiperazin-1-yl)acetyl]-1,2,3,6-tet-
rahydropyridin-4-yl}phenyl)-1,3-dihydro-2H-isoin-
dole-2-carboxamide;
N-(1'-benzoyl-1',2',3',6-tetrahydro-3,4'-bipyridin-6-yl)-1,
3-dihydro-2H-isoindole-2-carboxamide;
N-(4-{[6-(benzoylamino)hexyl]carbamoyl}phenyl)-1,3-
dihydro-2H-isoindole-2-carboxamide;
N-[4-({4-[(benzoylamino)methyl]benzyl}carbamoyl)
phenyl]-5-fluoro-1,3-dihydro-2H-isoindole-2-carboxa-
mide;
N-{4-[4-(5-oxo-L-prolyl)piperazin-1-yl]phenyl}-1,3-di-
hydro-2H-isoindole-2-carboxamide;
N-{4-[4-(5-oxo-D-prolyl)piperazin-1-yl]phenyl}-1,3-di-
hydro-2H-isoindole-2-carboxamide;
N-(4-{4-[(1-acetylpiperidin-4-yl)carbonyl]piperazin-1-
yl}phenyl)-1,3-dihydro-2H-isoindole-2-carboxamide;
N-{4-[4-(2-acetamidobenzoyl)piperazin-1-yl]phenyl}-1,
3-dihydro-2H-isoindole-2-carboxamide;
N-(4-{4-[4-(methylsulfonyl)benzoyl]piperazin-1-
yl}phenyl)-1,3-dihydro-2H-isoindole-2-carboxamide;
N-[4-(4-butyrylpiperazine-1-yl)phenyl]-1,3-dihydro-2H-
isoindole-2-carboxamide;
N-[4-(4-isobutyrylpiperazin-1-yl)phenyl]-1,3-dihydro-
2H-isoindole-2-carboxamide;
N-{4-[4-(2-methylbutanoyl)piperazin-1-yl]phenyl}-1,3-
dihydro-2H-isoindole-2-carboxamide;
N-{4-[4-(3,3,3-trifluoropropanoyl)piperazin-1-yl]phe-
nyl}-1,3-dihydro-2H-isoindole-2-carboxamide;
N-{4-[4-(methoxyacetyl)piperazin-1-yl]phenyl}-1,3-di-
hydro-2H-isoindole-2-carboxamide;
N-{4-[4-(tetrahydrofuran-2-ylcarbonyl)piperazin-1-yl]
phenyl}-1,3-dihydro-2H-isoindole-2-carboxamide;
N-{4-[4-(tetrahydrofuran-3-ylcarbonyl)piperazin-1-yl]
phenyl}-1,3-dihydro-2H-isoindole-2-carboxamide;
N-{4-[4-(cyclopentylacetyl)piperazin-1-yl]phenyl}-1,3-
dihydro-2H-isoindole-2-carboxamide;
N-{4-[4-(cyclohexylcarbonyl)piperazin-1-yl]phenyl}-1,
3-dihydro-2H-isoindole-2-carboxamide;
N-{4-[4-(2-methoxybenzoyl)piperazin-1-yl]phenyl}-1,3-
dihydro-2H-isoindole-2-carboxamide;
N-{4-[4-(3-methoxybenzoyl)piperazin-1-yl]phenyl}-1,3-
dihydro-2H-isoindole-2-carboxamide;
N-{4-[4-(4-methoxybenzoyl)piperazin-1-yl]phenyl}-1,3-
dihydro-2H-isoindole-2-carboxamide;
N-{4-[4-(3-fluorobenzoyl)piperazin-1-yl]phenyl}-1,3-di-
hydro-2H-isoindole-2-carboxamide;

N-{4-[4-(2-chlorobenzoyl)piperazin-1-yl]phenyl}-1,3-dihydro-2H-isoindole-2-carboxamide;
N-{4-[4-(4-chlorobenzoyl)piperazin-1-yl]phenyl}-1,3-dihydro-2H-isoindole-2-carboxamide;
N-{4-[4-(3-cyanobenzoyl)piperazin-1-yl]phenyl}-1,3-dihydro-2H-isoindole-2-carboxamide;
N-{4-[4-(4-cyanobenzoyl)piperazin-1-yl]phenyl}-1,3-dihydro-2H-isoindole-2-carboxamide;
N-(4-{4-[3-(dimethylamino)benzoyl]piperazin-1-yl}phenyl)-1,3-dihydro-2H-isoindole-2-carboxamide;
N-(4-(4-[(dimethylamino)benzoyl]piperazin-1-yl)phenyl)-1,3-dihydro-2H-isoindole-2-carboxamide;
N-{4-[4-(3,4-dimethoxybenzoyl)piperazin-1-yl]phenyl}-1,3-dihydro-2H-isoindole-2-carboxamide;
N-{4-[4-(3,5-dimethoxybenzoyl)piperazin-1-yl]phenyl}-1,3-dihydro-2H-isoindole-2-carboxamide;
N-(4-{4-[(3,4-dimethoxyphenyl)acetyl]piperazin-1-yl}phenyl)-1,3-dihydro-2H-isoindole-2-carboxamide;
N-{4-[4-(2-furoyl)piperazin-1-yl]phenyl}-1,3-dihydro-2H-isoindole-2-carboxamide;
N-{4-[4-(3-furoyl)piperazin-1-yl]phenyl}-1,3-dihydro-2H-isoindole-2-carboxamide;
N-{4-[4-(1H-pyrrol-2-ylcarbonyl)piperazin-1-yl]phenyl}-1,3-dihydro-2H-isoindole-2-carboxamide;
N-{4-[4-(1H-pyrazol-5-ylcarbonyl)piperazin-1-yl]phenyl)}-1,3-dihydro-2H-isoindole-2-carboxamide;
N-{4-[4-(pyridin-2-ylcarbonyl)piperazin-1-yl]phenyl}-1,3-dihydro-2H-isoindole-2-carboxamide;
N-{4-[4-(pyridin-3-ylcarbonyl)piperazin-1-yl]phenyl}-1,3-dihydro-2H-isoindole-2-carboxamide;
N-[4-(4-isonicotinoylpiperazine-1-yl)phenyl]-1,3-dihydro-2H-isoindole-2-carboxamide;
N-{4-[4-(pyridazin-3-ylcarbonyl)piperazin-1-yl]phenyl}-1,3-dihydro-2H-isoindole-2-carboxamide;
N-{4-[4-(pyrazin-2-ylcarbonyl)piperazin-1-yl]phenyl}-1,3-dihydro-2H-isoindole-2-carboxamide;
N-{4-[4-(pyrimidin-4-ylcarbonyl)piperazin-1-yl]phenyl}-1,3-dihydro-2H-isoindole-2-carboxamide;
N-{4-[4-(N,N-dimethyl-beta-alanyl)piperazin-1-yl]phenyl}-1,3-dihydro-2H-isoindole-2-carboxamide;
N-[4-(4-acetylpiperazin-1-yl)phenyl]-1,3-dihydro-2H-isoindole-2-carboxamide;
N-{4-[4-(2-fluorobenzoyl)piperazin-1-yl]phenyl}-1,3-dihydro-2H-isoindole-2-carboxamide;
N-{4-[4-(4-fluorobenzoyl)piperazin-1-yl]phenyl}-1,3-dihydro-2H-isoindole-2-carboxamide;
N-{4-[4-(phenylacetyl)piperazin-1-yl]phenyl}-1,3-dihydro-2H-isoindole-2-carboxamide;
N-{4-[4-(1,3-thiazol-4-ylcarbonyl)piperazin-1-yl]phenyl}-1,3-dihydro-2H-isoindole-2-carboxamide;
N-{4-[4-(morpholin-4-ylacetyl)piperazin-1-yl]phenyl}-1,3-dihydro-2H-isoindole-2-carboxamide;
5-cyano-N-(4-phenylbutyl)-1,3-dihydro-2H-isoindole-2-carboxamide;
N-[4-(1-oxo-2,3-dihydro-1H-isoindol-4-yl)phenyl]-1,3-dihydro-2H-isoindole-2-carboxamide;
N-[4-(1-oxo-1,2-dihydroisoquinolin-4-yl)cyclohex-3-en-1-yl]-1,3-dihydro-2H-isoindole-2-carboxamide;
N-[4-(4-oxo-3,4-dihydrophthalazin-1-yl)cyclohex-3-en-1-yl]-1,3-dihydro-2H-isoindole-2-carboxamide;
N-[4-(4-oxo-3,4-dihydrophthalazin-1-yl)cyclohex-3-en-1-yl]-5-(pyrrolidin-1-ylmethyl)-1,3-dihydro-2H-isoindole-2-carboxamide;
N-[1-(3-methylbutyl)-1H-pyrazol-4-yl]-1,3-dihydro-2H-isoindole-2-carboxamide;
N-[1-(2-phenylethyl)-1H-pyrazol-4-yl]-1,3-dihydro-2H-isoindole-2-carboxamide;
$N^5$-[2-(dimethylamino)ethyl]-$N^2$-[4-(propylcarbamoyl)phenyl]-1,3-dihydro-2H-isoindole-2,5-dicarboxamide;
5-(morpholin-4-ylcarbonyl)-N-[4-(propylcarbamoyl)phenyl]-1,3-dihydro-2H-isoindole-2-carboxamide;
N-(4-(benzyl[3-(morpholin-4-yl)propyl]carbamoyl)phenyl)-1,3-dihydro-2H-isoindole-2-carboxamide;
N-[4-(isobutoxycarbamoyl)phenyl]-1,3-dihydro-2H-isoindole-2-carboxamide;
5-bromo-N-{4-[(cyclopentylacetyl)amino]phenyl}-1,3-dihydro-2H-isoindole-2-carboxamide;
5-cyano-N-{4-[(cyclopentylacetyl)amino]phenyl}-1,3-dihydro-2H-isoindole-2-carboxamide;
methyl 4-{[(5-cyano-1,3-dihydro-2H-isoindol-2-yl)carbonyl]amino)benzoate;
N-(4-{(E)-[(benzyloxy)imino]methyl}Jphenyl)-1,3-dihydro-2H-isoindole-2-carboxamide;
5-fluoro-N-{4-[(tetrahydro-2H-pyran-2-ylmethyl)carbamoyl]phenyl}-1,3-dihydro-2H-isoindole-2-carboxamide;
5-fluoro-N-{4-[(tetrahydro-2H-pyran-3-ylmethyl)carbamoyl]phenyl}-1,3-dihydro-2H-isoindole-2-carboxamide;
5-fluoro-N-{4-[(tetrahydro-2H-pyran-4-yl methyl)carbamoyl]phenyl}-1,3-dihydro-2H-isoindole-2-carboxamide;
5-fluoro-N-(4-{[(1S)-2-hydroxy-1-phenylethyl]carbamoyl}phenyl)-1,3-dihydro-2H-isoindole-2-carboxamide;
5-fluoro-N-(4-([(1S)-2-hydroxy-1-(pyridin-2-yl)ethyl]carbamoyl}phenyl)-1,3-dihydro-2H-isoindole-2-carboxamide;
5-fluoro-N-(4-{[(2S)-1-hydroxy-4-methylpentan-2-yl]carbamoyl}phenyl)-1,3-dihydro-2H-isoindole-2-carboxamide;
N-[4-(3-aminopyrrolidin-1-yl)phenyl]-1,3-dihydro-2H-isoindole-2-carboxamide;
N-{6-[(3-methylbutyl)carbamoyl]pyridin-3-yl}-1,3-dihydro-2H-isoindole-2-carboxamide;
N-{6-[(3-phenylpropyl)carbamoyl]pyridin-3-yl}-1,3-dihydro-2H-isoindole-2-carboxamide;
N-{6-[(tetrahydrofuran-3-ylmethyl)carbamoyl]pyridin-3-yl}-1,3-dihydro-2H-isoindole-2-carboxamide;
$N^2$-{4-[(cyclopentylacetyl)amino]phenyl}-1,3-dihydro-2H-isoindole-2,5-dicarboxamide;
N-[4-({benzyl[3-(morpholin-4-yl)propyl]amino})methyl)phenyl]-1,3-dihydro-2H-isoindole-2-carboxamide;
N-{4-[(cyclopentylacetyl)amino]phenyl}-5-(1H-pyrazol-3-yl)-1,3-dihydro-2H-isoindole-2-carboxamide;
N-{4-[(cyclopentylacetyl)amino]phenyl}-5-(pyridin-3-yl)-1,3-dihydro-2H-isoindole-2-carboxamide;
N-{4-[(cyclopentylacetyl)amino]phenyl}-5-(1-methyl-1H-pyrazol-4-yl)-1,3-dihydro-2H-isoindole-2-carboxamide;
$N^2$-{4-[(cyclopentylacetyl)amino]phenyl}-$N^5$-(2-methoxyethyl)-1,3-dihydro-2H-isoindole-2,5-dicarboxamide;
$N^2$-{4-[(cyclopentylacetyl)amino]phenyl}-$N^5$-(2-hydroxyethyl)-1,3-dihydro-2H-isoindole-2,5-dicarboxamide;
5-(aminomethyl)-N-{4-[(cyclopentylacetyl)amino]phenyl}-1,3-dihydro-2H-isoindole-2-carboxamide;
N-(4-{[(2S)-1-hydroxy-4-(methylthio)butan-2-yl]carbamoyl}phenyl)-1,3-dihydro-2H-isoindole-2-carboxamide;
N-(4-{[(2S,3S)-1-hydroxy-3-methylpentan-2-yl]carbamoyl}phenyl)-1,3-dihydro-2H-isoindole-2-carboxamide;

N-(4-{[(2S)-1-hydroxypropan-2-yl]carbamoyl}phenyl)-1,3-dihydro-2H-isoindole-2-carboxamide;
N-(4-{[(2S,3R)-1,3-dihydroxybutan-2-yl]carbamoyl}phenyl)-1,3-dihydro-2H-isoindole-2-carboxamide;
N-(4-{[(2S)-1-hydroxyhexan-2-yl]carbamoyl)phenyl)-1,3-dihydro-2H-isoindole-2-carboxamide;
N-(4-([(2S)-1-hydroxypentan-2-yl]carbamoyl)phenyl)-1,3-dihydro-2H-isoindole-2-carboxamide;
N-(4-{[(1S,2S)-2-hydroxycyclopentyl]carbamoyl}phenyl)-1,3-dihydro-2H-isoindole-2-carboxamide;
N-(4-{[(1S,2R)-2-hydroxycyclopentyl]carbamoyl}phenyl)-1,3-dihydro-2H-isoindole-2-carboxamide;
N-(4-{[(2S)-1-cyclohexyl-3-hydroxypropan-2-yl]carbamoyl}phenyl)-1,3-dihydro-2H-isoindole-2-carboxamide;
N-[4-(((2R)-1-hydroxy-3-[(4-methylbenzyl)thio]propan-2-yl}carbamoyl)phenyl]-1,3-dihydro-2H-isoindole-2-carboxamide;
N-(4-{[(1S)-1-(4-tert-butylphenyl)-2-hydroxyethyl]carbamoyl}phenyl)-1,3-dihydro-2H-isoindole-2-carboxamide;
N-{4-[(cyclopentylacetyl)amino]phenyl}-5-methoxy-1,3-dihydro-2H-isoindole-2-carboxamide;
5-methoxy-N-[4-(propyl carbamoyl)phenyl]-1,3-dihydro-2H-isoindole-2-carboxamide;
5-methyl-N-[4-(propylcarbamoyl)phenyl]-1,3-dihydro-2H-isoindole-2-carboxamide;
N-[6-(benzoylamino)hexyl]-1,3-dihydro-2H-isoindole-2-carboxamide;
N-{6-[(pyridin-3-ylcarbonyl)amino]hexyl}-1,3-dihydro-2H-isoindole-2-carboxamide;
N-{4-[(cyclopentylacetyl)amino]phenyl}-5-(pyridin-4-yl)-1,3-dihydro-2H-isoindole-2-carboxamide;
5-(hydroxymethyl)-N-{4-[(3-methylbutyl)carbamoyl]phenyl}-1,3-dihydro-2H-isoindole-2-carboxamide;
N-(6-{[(3S)-tetrahydrofuran-3-ylmethyl]carbamoyl}pyridazin-3-yl)-1,3-dihydro-2H-isoindole-2-carboxamide;
N-{6-[(cyclopentylmethyl)carbamoyl]pyridazin-3-yl}-1,3-dihydro-2H-isoindole-2-carboxamide;
N-[1'-(tetrahydrofuran-3-ylcarbonyl)-1',2',3',6'-tetrahydro-2,4'-bipyridin-5-yl]-1,3-dihydro-2H-isoindole-2-carboxamide;
N-{1'-[(2-methoxyethoxy)acetyl]-1',2',3',6'-tetrahydro-2,4'-bipyridin-5-yl}-1,3-dihydro-2H-isoindole-2-carboxamide;
5-(hydroxymethyl)-N-(4-phenylbutyl)-1,3-dihydro-2H-isoindole-2-carboxamide;
5-(hydroxymethyl)-N-[1-(3-methylbutyl)-1H-pyrazol-4-yl]-1,3-dihydro-2H-isoindole-2-carboxamide;
N-{5-[(3-methylbutyl)carbamoyl]pyrazin-2-yl}-1,3-dihydro-2H-isoindole-2-carboxamide;
N-(6-acetamidohexyl)-1,3-dihydro-2H-isoindole-2-carboxamide;
N-(4-{(1E)-3-[benzyl(methyl)amino]prop-1-en-1-yl}phenyl)-1,3-dihydro-2H-isoindole-2-carboxamide;
N-[4-(4-phenoxypiperidin-1-yl)phenyl]-1,3-dihydro-2H-isoindole-2-carboxamide;
N-[4-(3-phenoxyazetidin-1-yl)phenyl]-1,3-dihydro-2H-isoindole-2-carboxamide;
N-(4-{[benzyl(methyl)amino]methyl}phenyl)-1,3-dihydro-2H-isoindole-2-carboxamide;
5-fluoro-N-(4-{[(3R)-tetrahydrofuran-3-ylmethyl]carbamoyl}phenyl)-1,3-dihydro-2H-isoindole-2-carboxamide;
5-fluoro-N-(4-{[(3S)-tetrahydrofuran-3-ylmethyl]carbamoyl}phenyl)-1,3-dihydro-2H-isoindole-2-carboxamide;
N-[4-(1-benzyl-1H-1,2,3-triazol-4-yl)phenyl]-1,3-dihydro-2H-isoindole-2-carboxamide;
N-{4-[1-(3-methylbutyl)-1H-1,2,3-triazol-4-yl]phenyl}-1,3-dihydro-2H-isoindole-2-carboxamide;
N-{4-[1-(tetrahydrofuran-3-ylmethyl)-1H-1,2,3-triazol-4-yl]phenyl}-1,3-dihydro-2H-isoindole-2-carboxamide;
N-(4-{1-[2-(2-oxopyrrolidin-1-yl)ethyl]-1H-1,2,3-triazol-4-yl}phenyl)-1,3-dihydro-2H-isoindole-2-carboxamide;
N-{4-[1-(1-benzylpiperidin-4-yl)-1H-1,2,3-triazol-4-yl]phenyl}-1,3-dihydro-2H-isoindole-2-carboxamide;
N-{4-[1-(3-phenylpropyl)-1H-1,2,3-triazol-4-yl]phenyl}-1,3-dihydro-2H-isoindole-2-carboxamide;
N-(4-{1-[4-(morpholin-4-yl)benzyl]-1H-1,2,3-triazol-4-yl}phenyl)-1,3-dihydro-2H-isoindole-2-carboxamide;
N-[4-(1-isobutyl-1H-1,2,3-triazol-4-yl)phenyl]-1,3-dihydro-2H-isoindole-2-carboxamide;
N-{4-[1-(cyclopentylmethyl)-1H-1,2,3-triazol-4-yl]phenyl}-1,3-dihydro-2H-isoindole-2-carboxamide;
N-{4-[1-(3-methoxypropyl)-1H-1,2,3-triazol-4-yl]phenyl}-1,3-dihydro-2H-isoindole-2-carboxamide;
N-(4-{1-[(2-methoxyethoxy)acetyl]piperidin-4-yl}phenyl)-1,3-dihydro-2H-isoindole-2-carboxamide;
N-{5-[1-(tetrahydrofuran-3-ylcarbonyl)piperidin-4-yl]pyridin-2-yl}-1,3-dihydro-2H-isoindole-2-carboxamide;
5-(hydroxymethyl)-N-{4-[(tetrahydrofuran-3-ylacetyl)amino]phenyl}-1,3-dihydro-2H-isoindole-2-carboxamide;
5-(hydroxymethyl)-N-(4-{[(2-methoxyethoxy)acetyl]amino}phenyl)-1,3-dihydro-2H-isoindole-2-carboxamide;
N-(6-{[4-(methylsulfonyl)benzoyl]amino}hexyl)-1,3-dihydro-2H-isoindole-2-carboxamide;
N-{6-[(ethoxyacetyl)amino]hexyl}-1,3-dihydro-2H-isoindole-2-carboxamide;
N-{6-[(cyclopentylcarbonyl)amino]hexyl}-1,3-dihydro-2H-isoindole-2-carboxamide;
N-{6-[(2-hydroxybenzoyl)amino]hexyl}-1,3-dihydro-2H-isoindole-2-carboxamide;
N-{6-[(3-hydroxybenzoyl)amino]hexyl}-1,3-dihydro-2H-isoindole-2-carboxamide;
N-{6-[(4-hydroxybenzoyl)amino]hexyl}-1,3-dihydro-2H-isoindole-2-carboxamide;
N-{6-[(2-methoxybenzoyl)amino]hexyl}-1,3-dihydro-2H-isoindole-2-carboxamide;
N-{6-[(3-methoxybenzoyl)amino]hexyl}-1,3-dihydro-2H-isoindole-2-carboxamide;
N-{6-[(4-methoxybenzoyl)amino]hexyl}-1,3-dihydro-2H-isoindole-2-carboxamide;
N-{6-[(2-fluorobenzoyl)amino]hexyl}-1,3-dihydro-2H-isoindole-2-carboxamide;
N-{6-[(3-fluorobenzoyl)amino]hexyl})-1,3-dihydro-2H-isoindole-2-carboxamide;
N-{6-[(4-fluorobenzoyl)amino]hexyl}-1,3-dihydro-2H-isoindole-2-carboxamide;
N-{6-[(2-chlorobenzoyl)amino]hexyl}-1,3-dihydro-2H-isoindole-2-carboxamide;
N-{6-[(3-chlorobenzoyl)amino]hexyl}-1,3-dihydro-2H-isoindole-2-carboxamide;

N-{6-[(4-chlorobenzoyl)amino]hexyl}-1,3-dihydro-2H-isoindole-2-carboxamide;
N-{6-[(3-cyanobenzoyl)amino]hexyl}-1,3-dihydro-2H-isoindole-2-carboxamide;
N-{6-[(4-cyanobenzoyl)amino]hexyl}-1,3-dihydro-2H-isoindole-2-carboxamide;
N-(6-{[3-(dimethylamino)benzoyl]amino}hexyl)-1,3-dihydro-2H-isoindole-2-carboxamide;
N-(6-{[4-(dimethylamino)benzoyl]amino}J hexyl)-1,3-dihydro-2H-isoindole-2-carboxamide;
N-(6-{[3-(trifluoromethyl)benzoyl]amino}hexyl)-1,3-dihydro-2H-isoindole-2-carboxamide;
N-(6-[4-(trifluoromethyl)benzoyl]amino}hexyl)-1,3-dihydro-2H-isoindole-2-carboxamide;
N-(6-{[3-(trifluoromethoxy)benzoyl]amino}hexyl)-1,3-dihydro-2H-isoindole-2-carboxamide;
N-{6-[(2,3-dimethoxybenzoyl)amino]hexyl)}-1,3-dihydro-2H-isoindole-2-carboxamide;
N-{6-[(2,4-dimethoxybenzoyl)amino]hexyl}-1,3-dihydro-2H-isoindole-2-carboxamide;
N-{6-[(2,5-dimethoxybenzoyl)amino]hexyl}-1,3-dihydro-2H-isoindole-2-carboxamide;
N-{6-[(phenylacetyl)amino]hexyl}-1,3-dihydro-2H-isoindole-2-carboxamide;
N-(6-{[(3-fluorophenyl)acetyl]amino)}hexyl)-1,3-dihydro-2H-isoindole-2-carboxamide;
5-(hydroxymethyl)-N-{4-[(tetrahydrofuran-2-ylacetyl)amino]phenyl}-1,3-dihydro-2H-isoindole-2-carboxamide;
N-{4-[(ethoxyacetyl)amino]phenyl}-5-(hydroxymethyl)-1,3-dihydro-2H-isoindole-2-carboxamide;
5-(hydroxymethyl)-N-{4-[(tetrahydro-2H-pyran-4-ylacetyl)amino]phenyl}-1,3-dihydro-2H-isoindole-2-carboxamide;
5-(hydroxymethyl)-N-{4-[(morpholin-4-ylacetyl)amino]phenyl}-1,3-dihydro-2H-isoindole-2-carboxamide;
4-fluoro-N-{6-[(pyridin-3-ylcarbonyl)amino]hexyl}-1,3-dihydro-2H-isoindole-2-carboxamide;
5-fluoro-N-(6-[(pyridin-3-ylcarbonyl)amino]hexyl-1,3-dihydro-2H-isoindole-2-carboxamide;
5-methoxy-N-{6-[(pyridin-3-ylcarbonyl)amino]hexyl}-1,3-dihydro-2H-isoindole-2-carboxamide;
N-{6-[(pyridin-3-ylcarbonyl)amino]hexyl}-5-(trifluoromethyl)-1,3-dihydro-2H-isoindole-2-carboxamide;
4-cyano-N-{6-[(pyridin-3-ylcarbonyl)amino]hexyl}-1,3-dihydro-2H-isoindole-2-carboxamide;
5-methyl-N-{6-[(pyridin-3-ylcarbonyl)amino]hexyl}-1,3-dihydro-2H-isoindole-2-carboxamide;
4-chloro-N-{6-[(pyridin-3-ylcarbonyl)amino]hexyl}-1,3-dihydro-2H-isoindole-2-carboxamide;
5-cyano-N-{6-[(pyridin-3-ylcarbonyl)amino]hexyl}-1,3-dihydro-2H-isoindole-2-carboxamide;
5-chloro-N-{6-[(pyridin-3-ylcarbonyl)amino]hexyl}-1,3-dihydro-2H-isoindole-2-carboxamide;
N-{6-[(pyridin-2-ylcarbonyl)amino]hexyl}-1,3-dihydro-2H-isoindole-2-carboxamide;
N-{4-[1-(pyridin-2-ylcarbonyl)piperidin-4-yl]butyl}-1,3-dihydro-2H-isoindole-2-carboxamide;
N-[1'-(tetrahydrofuran-2-ylcarbonyl)-1',2',3',6'-tetrahydro-2,4'-bipyridin-5-yl]-1,3-dihydro-2H-isoindole-2-carboxamide;
N-[1'-(tetrahydro-2H-pyran-4-ylcarbonyl)-1',2',3',6'-tetrahydro-2,4'-bipyridin-5-yl]-1,3-dihydro-2H-isoindole-2-carboxamide;
N-[1'-(1,4-dioxan-2-ylcarbonyl)-1',2',3',6'-tetrahydro-2,4'-bipyridin-5-yl]-1,3-dihydro-2H-isoindole-2-carboxamide;
N-{1'-[(1-methylpyrrolidin-3-yl)carbonyl]-1',2',3',6'-tetrahydro-2,4'-bipyridin-5-yl}-1,3-dihydro-2H-isoindole-2-carboxamide;
N-{1'-[(1,1-dioxidotetrahydrothiophen-3-yl)carbonyl]-1',2',3',6'-tetrahydro-2,4'-bipyridin-5-yl}-1,3-dihydro-2H-isoindole-2-carboxamide;
N-(4-{[(1-methylpyrrolidin-3-yl)methyl]carbamoyl}phenyl)-1,3-dihydro-2H-isoindole-2-carboxamide;
N-{4-[(pyrrolidin-3-ylmethyl)carbamoyl]phenyl}-1,3-dihydro-2H-isoindole-2-carboxamide;
N-(4-{[(1-methylpiperidin-4-yl)methyl]carbamoyl}phenyl)-1,3-dihydro-2H-isoindole-2-carboxamide;
N-(7-oxo-7-{[(3R)-tetrahydrofuran-3-ylmethyl]amino}heptyl)-1,3-dihydro-2H-isoindole-2-carboxamide;
N-{7-oxo-7-[(tetrahydro-2H-pyran-4-ylmethyl)amino]heptyl}-1,3-dihydro-2H-isoindole-2-carboxamide;
N-{4-[5-(morpholin-4-ylmethyl)-1,2,4-oxadiazol-3-yl]phenyl}-1,3-dihydro-2H-isoindole-2-carboxamide;
N-(4-{5-[(4-methylpiperazin-1-yl)methyl]-1,2,4-oxadiazol-3-yl}phenyl)-1,3-dihydro-2H-isoindole-2-carboxamide;
N-[4(5 [(3-methylbutyl)amino]methyl)}-1,2,4-oxadiazol-3-yl)phenyl]-1,3-dihydro-2H-isoindole-2-carboxamide;
N-(4-{5-[(4-hydroxypiperidin-1-yl)methyl]-1,2,4-oxadiazol-3-yl}phenyl)-1,3-dihydro-2H-isoindole-2-carboxamide;
N-[1'-(2-hydroxy-2-methylpropanoyl)-1',2',3',6'-tetrahydro-2,4'-bipyridin-5-yl]-1,3-dihydro-2H-isoindole-2-carboxamide;
N-{4-[1-(tetrahydro-2H-pyran-4-ylcarbonyl)-1 2,3,6-tetrahydropyridin-4-yl]phenyl}-1,3-dihydro-2H-isoindole-2-carboxamide;
N-{4-[1-(1,4-dioxan-2-ylcarbonyl)-1,2,3,6-tetrahydropyridin-4-yl]phenyl}-1,3-dihydro-2H-isoindole-2-carboxamide;
N-(4-{1-[(1-methylpyrrolidin-3-yl)carbonyl]-1,2,3,6-tetrahydropyridin-4-yl)}phenyl)-1,3-dihydro-2H-isoindole-2-carboxamide;
N-(4-{1-[(1,1-dioxidotetrahydrothiophen-3-yl)carbonyl]-1,2,3,6-tetrahydropyridin-4-yl}phenyl)-1,3-dihydro-2H-isoindole-2-carboxamide;
N-{4-[1-(2-hydroxy-2-methylpropanoyl)-1,2,3,6-tetrahydropyridin-4-yl]phenyl}-1,3-dihydro-2H-isoindole-2-carboxamide;
N-[1'-(tetrahydrofuran-2-ylcarbonyl)-1',2',3',6'-tetrahydro-3,4'-bipyridin-6-yl]-1,3-dihydro-2H-isoindole-2-carboxamide;
N-[1'-(tetrahydro-2H-pyran-4-ylcarbonyl)-1',2',3',6'-tetrahydro-3,4'-bipyridin-6-yl]-1,3-dihydro-2H-isoindole-2-carboxamide;
N-[1'-(1,4-dioxan-2-ylcarbonyl)-1',2',3',6'-tetrahydro-3,4'-bipyridin-6-yl]-1,3-dihydro-2H-isoindole-2-carboxamide;
N-{1'-[(1-methylpyrrolidin-3-yl)carbonyl]-1',2',3',6'-tetrahydro-3,4'-bipyridin-6-yl}-1,3-dihydro-2H-isoindole-2-carboxamide;
N-{1-[(1,1-dioxidotetrahydrothiophen-3-yl)carbonyl]-1',2',3',6'-tetrahydro-3,4'-bipyridin-6-yl}-1,3-dihydro-2H-isoindole-2-carboxamide;
N-[1'-(2-hydroxy-2-methylpropanoyl)-1',2',3,6'-tetrahydro-3,4'-bipyridin-6-yl]-1,3-dihydro-2H-isoindole-2-carboxamide;

N-(4-([(1,1-dioxidotetrahydrothiophen-3-yl)methyl] carbamoyl}phenyl)-1,3-dihydro-2H-isoindole-2-carboxamide;
N-(4-{[(2,2-dimethyl-1,3-dioxolan-4-yl)methyl] carbamoyl}phenyl)-1,3-dihydro-2H-isoindole-2-carboxamide;
N-(4-{[(1S)-2-methoxy-1-phenylethyl] carbamoyl}phenyl)-1,3-dihydro-2H-isoindole-2-carboxamide;
N-[4-({[(4S)-2,2-dimethyl-1,3-dioxolan-4-yl] methyl}carbamoyl)phenyl]-1,3-dihydro-2H-isoindole-2-carboxamide;
N-[4-({[(4R)-2,2-dimethyl-1,3-dioxolan-4-yl] methyl}carbamoyl)phenyl]-1,3-dihydro-2H-isoindole-2-carboxamide;
N-[4-(4-({[3-(hydroxymethyl)oxetan-3-yl] methyl}carbamoyl)phenyl]-1,3-dihydro-2H-isoindole-2-carboxamide;
N-[4-(2-{benzyl[3-(morpholin-4-yl)propyl]amino}-2-oxoethyl)phenyl]-1,3-dihydro-2H-isoindole-2-carboxamide;
N-[4-(3-{benzyl[3-(morpholin-4-yl)propyl]amino}-3-oxopropyl)phenyl]-1,3-dihydro-2H-isoindole-2-carboxamide;
N-{4-[(cyclopentylacetyl)amino]phenyl}-5-fluoro-1,3-dihydro-2H-isoindole-2-carboxamide;
N-{4-[(2R)-butan-2-ylcarbamoyl]phenyl}-1,3-dihydro-2H-isoindole-2-carboxamide;
N-{4-[(cyclopentylacetyl)amino]phenyl}-5-(trifluoromethyl)-1,3-dihydro-2H-isoindole-2-carboxamide;
4-cyano-N-{4-[(cyclopentylacetyl)amino]phenyl}-1,3-dihydro-2H-isoindole-2-carboxamide;
N-{4-[(cyclopentylacetyl)amino]phenyl}-5-methyl-1,3-dihydro-2H-isoindole-2-carboxamide;
4-chloro-N-{4-[(cyclopentylacetyl)amino]phenyl}-1,3-dihydro-2H-isoindole-2-carboxamide;
N-{6-[(tetrahydro-2H-pyran-4-ylmethyl)carbamoyl]pyridazin-3-yl}-1,3-dihydro-2H-isoindole-2-carboxamide;
5-chloro-N-{4-[(cyclopentylacetyl)amino]phenyl}-1,3-dihydro-2H-isoindole-2-carboxamide;
N-[4-(6-bromo-2-oxoquinolin-1(2H)-yl)butyl]-1,3-dihydro-2H-isoindole-2-carboxamide;
N-{4-[6-(3-acetylphenyl)-2-oxoquinolin-1(2H)-yl]butyl}-1,3-dihydro-2H-isoindole-2-carboxamide;
N-[1'-(morpholin-4-ylacetyl)-1',2',3,6'-tetrahydro-2,4'-bipyridin-5-yl]-1,3-dihydro-2H-isoindole-2-carboxamide;
N-[1'-(morpholin-4-ylacetyl)-1',2',3',6'-tetrahydro-3,4'-bipyridin-6-yl]-1,3-dihydro-2H-isoindole-2-carboxamide;
N-(4-{[(3-methyloxetan-3-yl)methyl] carbamoyl}phenyl)-1,3-dihydro-2H-isoindole-2-carboxamide;
N-[4-(2-benzyl-1,3-thiazol-4-yl)phenyl]-1,3-dihydro-2H-isoindole-2-carboxamide;
N-(7-{benzyl[3-(morpholin-4-yl)propyl]amino}-7-oxoheptyl)-1,3-dihydro-2H-isoindole-2-carboxamide;
N-{4-[(3-methylbutyl)sulfamoyl]phenyl}-1,3-dihydro-2H-isoindole-2-carboxamide;
5-cyano-N-{4-[(cyclopentylmethyl)carbamoyl]phenyl}-1,3-dihydro-2H-isoindole-2-carboxamide;
5-cyano-N-{4-[(1,3-thiazol-5-ylmethyl)carbamoyl]phenyl}-1,3-dihydro-2H-isoindole-2-carboxamide;
5-cyano-N-{4-{[(1R)-3-hydroxy-1-phenylpropyl] carbamoyl}phenyl)-1,3-dihydro-2H-isoindole-2-carboxamide;
5-cyano-N4(4-{[2-hydroxy-1-(4-methylphenyl)ethyl] carbamoyl}phenyl)-1,3-dihydro-2H-isoindole-2-carboxamide;
5-cyano-N-{4-[(1,3-dihydroxypropan-2-yl)carbamoyl] phenyl}-1,3-dihydro-2H-isoindole-2-carboxamide;
5-cyano-N-(4-{[(2R)-2-hydroxypropyl] carbamoyl}phenyl)-1,3-dihydro-2H-isoindole-2-carboxamide;
5-cyano-N-{4-[(2-hydroxy-2-methylpropyl)carbamoyl] phenyl)-1,3-dihydro-2H-isoindole-2-carboxamide;
5-cyano-N-(4-1 [(2R)-1-hydroxy-3-methylbutan-2-yl] carbamoyl}phenyl)-1,3-dihydro-2H-isoindole-2-carboxamide;
5-cyano-N-(4-{[(2S)-tetrahydrofuran-2-ylmethyl] carbamoyl}phenyl)-1,3-dihydro-2H-isoindole-2-carboxamide;
5-cyano-N-(4-1 [1-(4-methylpiperazin-1-yl)ethyl]carbamoyl}phenyl)-1,3-dihydro-2H-isoindole-2-carboxamide;
5-cyano-N-(4-{[(1S)-2-hydroxy-1-phenylethyl] carbamoyl}phenyl)-1,3-dihydro-2H-isoindole-2-carboxamide;
5-cyano-N-{4-[(4-hydroxybutyl)carbamoyl]phenyl}-1,3-dihydro-2H-isoindole-2-carboxamide;
5-cyano-N-{4-([(2S)-2-hydroxypropyl] carbamoyl}phenyl)-1,3-dihydro-2H-isoindole-2-carboxamide;
5-cyano-N-{4-[(3-furylmethyl)carbamoyl]phenyl}-1,3-dihydro-2H-isoindole-2-carboxamide;
5-cyano-N-{4-[(tetrahydrofuran-2-ylmethyl)carbamoyl] phenyl}-1,3-dihydro-2H-isoindole-2-carboxamide;
5-cyano-N-(4-{[4-(2-furoyl)piperazin-1-yl] carbonyl}phenyl)-1,3-dihydro-2H-isoindole-2-carboxamide;
5-cyano-N-(4-{[4-(tetrahydrofuran-2-ylcarbonyl)piperazin-1-yl]carbonyl}phenyl)-1,3-dihydro-2H-isoindole-2-carboxamide;
5-cyano-N-(4-{[3-(piperidin-1-yl)propyl]carbamoyl}phenyl)-1,3-dihydro-2H-isoindole-2-carboxamide;
5-cyano-N-(4-{[(1R)-tetrahydrofuran-2-ylmethyl] carbamoyl}phenyl)-1,3-dihydro-2H-isoindole-2-carboxamide;
5-cyano-N-(4-{[4-(ethylsulfonyl)piperazin-1-yl] carbonyl}phenyl)-1,3-dihydro-2H-isoindole-2-carboxamide;
5-cyano-N-{4-[(tetrahydrofuran-3-ylmethyl)carbamoyl] phenyl}-1,3-dihydro-2-isoindole-2-carboxamide;
5-cyano-N4(4-{[(1R)-2-hydroxy-1-phenylethyl]carbamoyl)}phenyl)-1,3-dihydro-2H-isoindole-2-carboxamide;
5-cyano-N-(4-{[(2S)-1-hydroxybutan-2-yl] carbamoyl}phenyl)-1,3-dihydro-2H-isoindole-2-carboxamide;
5-cyano-N-{4-[(2,3-dihydroxypropyl)carbamoyl]phenyl}-1,3-dihydro-2H-isoindole-2-carboxamide;
5-cyano-N-{4-[(tetrahydro-2H-pyran-4-ylmethyl)carbamoyl]phenyl}-1,3-dihydro-2H-isoindole-2-carboxamide;
5-cyano-N-(4-{[2-hydroxy-1-(pyridin-2-yl)ethyl] carbamoyl}phenyl)-1,3-dihydro-2H-isoindole-2-carboxamide;
5-cyano-N-{4-[(1-hydroxy-4-methylpentan-2-yl)carbamoyl]phenyl}-1,3-dihydro-2H-isoindole-2-carboxamide;
5-cyano-N-{4-([(1-methylpyrrolidin-3-yl)methyl] carbamoyl}phenyl)-1,3-dihydro-2H-isoindole-2-carboxamide;

5-cyano-N4(4-{[(1-methylpiperidin-4-yl)methyl] carbamoyl}phenyl)-1,3-dihydro-2H-isoindole-2-carboxamide;
5-cyano-N-{4-[(tetrahydro-2H-pyran-3-ylmethyl)carbamoyl]phenyl}-1,3-dihydro-2H-isoindole-2-carboxamide;
N-(5-{[(3S)-tetrahydrofuran-3-ylmethyl] carbamoyl}pyridin-2-yl)-1,3-dihydro-2H-isoindole-2-carboxamide;
N-[4-(2,6-diazaspiro[3.3]hept-2-ylcarbonyl)phenyl]-1,3-dihydro-2H-isoindole-2-carboxamide;
N-[4-(2,6-diazaspiro[3.4]oct-6-ylcarbonyl)phenyl]-1,3-dihydro-2H-isoindole-2-carboxamide;
N-[4-(2,7-diazaspiro[3.5]non-7-ylcarbonyl)phenyl]-1,3-dihydro-2H-isoindole-2-carboxamide;
N-[4-(2,6-diazaspiro[3.5]non-2-ylcarbonyl)phenyl]-1,3-dihydro-2H-isoindole-2-carboxamide;
N-[4-(1 7-diazaspiro[4.4]non-1-ylcarbonyl)phenyl]-1,3-dihydro-2H-isoindole-2-carboxamide;
N-[4-(1,7-diazaspiro[4.4]non-7-ylcarbonyl)phenyl]-1,3-dihydro-2H-isoindole-2-carboxamide;
N-[4-(2,7-diazaspiro[4.4]non-2-ylcarbonyl)phenyl]-1,3-dihydro-2H-isoindole-2-carboxamide;
N-[4-(2,8-diazaspiro[4.5]dec-2-ylcarbonyl)phenyl]-1,3-dihydro-2H-isoindole-2-carboxamide;
N-[4-(2,7-diazaspiro[4.5]dec-2-ylcarbonyl)phenyl]-1,3-dihydro-2H-isoindole-2-carboxamide;
N-[4-(2,6-diazaspiro[4.5]dec-2-ylcarbonyl)phenyl]-1,3-dihydro-2H-isoindole-2-carboxamide;
N-[4-(1,7-diazaspiro[4.5]dec-7-ylcarbonyl)phenyl]-1,3-dihydro-2H-isoindole-2-carboxamide;
N-[4-(3,9-diazaspiro[5.5]undec-3-ylcarbonyl)phenyl]-1,3-dihydro-2H-isoindole-2-carboxamide;
N-[4-(2,9-diazaspiro[5.5]undec-2-ylcarbonyl)phenyl]-1,3-dihydro-2H-isoindole-2-carboxamide;
N-[4-(2,8-diazaspiro[5.5]undec-2-ylcarbonyl)phenyl]-1,3-dihydro-2H-isoindole-2-carboxamide;
N-[4-(1,8-diazaspiro[5.5]undec-8-ylcarbonyl)phenyl]-1,3-dihydro-2H-isoindole-2-carboxamide;
N-[4-(1,8-diazaspiro[4.6]undec-8-ylcarbonyl)phenyl]-1,3-dihydro-2H-isoindole-2-carboxamide;
N-[4-(1-oxa-8-azaspiro[4.5]dec-2-ylmethyl)carbamoyl] phenyl)-1,3-dihydro-2H-isoindole-2-carboxamide;
N-[4-(1-oxa-8-azaspiro[4.5]dec-3-ylcarbamoyl)phenyl]-1,3-dihydro-2H-isoindole-2-carboxamide;
N-{4-[(2-oxa-9-azaspiro[5.5]undec-3-ylmethyl)carbamoyl]phenyl}-1,3-dihydro-2-isoindole-2-carboxamide;
N-[4-(1-oxa-4,8-diazaspiro[5.5]undec-4-ylcarbonyl)phenyl]-1,3-dihydro-2H-isoindole-2-carboxamide;
N-[4-(1,8-diazaspiro[4.5]dec-1-ylcarbonyl)phenyl]-1,3-dihydro-2H-isoindole-2-carboxamide;
N-[4-(1 8-diazaspiro[4.5]dec-8-ylcarbonyl)phenyl]-1,3-dihydro-2H-isoindole-2-carboxamide;
N-[4-(2,6-diazaspiro[3.4]oct-2-ylcarbonyl)phenyl]-1,3-dihydro-2H-isoindole-2-carboxamide;
N-[4-(1,7-diazaspiro[3.5]non-7-ylcarbonyl)phenyl]-1,3-dihydro-2H-isoindole-2-carboxamide;
N-[4-(1,6-diazaspiro[3.5]non-1-ylcarbonyl)phenyl]-1,3-dihydro-2H-isoindole-2-carboxamide;
N-[4-(2,5-diazaspiro[3.5]non-2-ylcarbonyl)phenyl]-1,3-dihydro-2H-isoindole-2-carboxamide;
N-[4-(5-oxa-2-azaspiro[3.4]oct-2-ylcarbonyl)phenyl]-1,3-dihydro-2H-isoindole-2-carboxamide;
N-[4-(6-oxa-2-azaspiro[3.5]non-2-ylcarbonyl)phenyl]-1,3-dihydro-2H-isoindole-2-carboxamide;
N-[4-(hexahydro-5H-furo[2,3-c]pyrrol-5-ylcarbonyl)phenyl]-1,3-dihydro-2H-isoindole-2-carboxamide;
N-[4-(tetrahydro-11H-furo[3,4-c]pyrrol-5(3H)-ylcarbonyl)phenyl]-1,3-dihydro-2H-isoindole-2-carboxamide;
N-[4-(hexahydrofuro[3,4-c]pyridin-5(3H)-ylcarbonyl) phenyl]-1,3-dihydro-2H-isoindole-2-carboxamide;
N-[44(4-{benzyl[3-(morpholin-4-yl)propyl]amino}-4-oxobutyl)phenyl]-1,3-dihydro-2H-isoindole-2-carboxamide;
N-[4-(2-{benzyl[3-(morpholin-4-yl)propyl]amino}ethyl) phenyl]-1,3-dihydro-2H-isoindole-2-carboxamide;
5-acetyl-N-{4-[(cyclopentylacetyl)amino]phenyl}-1,3-dihydro-2H-isoindole-2-carboxamide;
5-cyano-N-{4-[(3-methylbutyl)sulfamoyl]phenyl}-1,3-dihydro-2H-isoindole-2-carboxamide;
N-{4-[(cyclopentylacetyl)amino]phenyl}-5-(1-hydroxyethyl)-1,3-dihydro-2H-isoindole-2-carboxamide;
N-[4-(butyrylamino)phenyl]-5-cyano-1,3-dihydro-2H-isoindole-2-carboxamide;
N-(4-{[(3-methoxybenzyl)sulfonyl]amino}phenyl)-1,3-dihydro-2H-isoindole-2-carboxamide;
N-[4-(2,6-diazaspiro[3.4]oct-6-ylcarbonyl)phenyl]-5-fluoro-1,3-dihydro-2H-isoindole-2-carboxamide;
N-[4-(2,7-diazaspiro[3.5]non-7-ylcarbonyl)phenyl]-5-fluoro-1,3-dihydro-2H-isoindole-2-carboxamide;
N-[4-(1,7-diazaspiro[4.4]non-1-ylcarbonyl)phenyl]-5-fluoro-1,3-dihydro-2H-isoindole-2-carboxamide;
N-[4-(1,8-diazaspiro[4.5]dec-2-ylcarbonyl)phenyl]-5-fluoro-1,3-dihydro-2H-isoindole-2-carboxamide;
N-[4-(2,6-diazaspiro[4.5]dec-2-yl carbonyl)phenyl]-5-fluoro-1,3-dihydro-2H-isoindole-2-carboxamide;
N-[4-(2,7-diazaspiro[4.5]dec-7-ylcarbonyl)phenyl]-5-fluoro-1,3-dihydro-2H-isoindole-2-carboxamide;
N-[4-(2,8-diazaspiro[5.5]undec-2-ylcarbonyl)phenyl]-5-fluoro-1,3-dihydro-2H-isoindole-2-carboxamide;
N-[4-(1,8-diazaspiro[5.5]undec-8-ylcarbonyl)phenyl]-5-fluoro-1,3-dihydro-2H-isoindole-2-carboxamide;
N-[4-(1,8-diazaspiro[4.6]undec-8-ylcarbonyl)phenyl]-5-fluoro-1,3-dihydro-2H-isoindole-2-carboxamide;
5-fluoro-N-{4-[(1-oxa-8-azaspiro[4.5]dec-2-ylmethyl)carbamoyl]phenyl}-1,3-dihydro-2H-isoindole-2-carboxamide;
5-fluoro-N-[4-(1-oxa-8-azaspiro[4.5]dec-3-ylcarbamoyl)phenyl]-1,3-dihydro-2H-isoindole-2-carboxamide;
5-fluoro-N-[4-(1-oxa-4,8-diazaspiro[5.5]undec-4-ylcarbonyl)phenyl]-1,3-dihydro-2H-isoindole-2-carboxamide;
N-[4-(1 8-diazaspiro[4.5]dec-1-ylcarbonyl)phenyl]-5-fluoro-1,3-dihydro-2H-isoindole-2-carboxamide;
N-[4-(1,8-diazaspiro[4.5]dec-8-ylcarbonyl)phenyl]-5-fluoro-1,3-dihydro-2H-isoindole-2-carboxamide;
N-[4-(2,6-diazaspiro[3.4]oct-2-ylcarbonyl)phenyl]-5-fluoro-1,3-dihydro-2H-isoindole-2-carboxamide;
N-[4-(1,7-diazaspiro[3.5]non-7-ylcarbonyl)phenyl]-5-fluoro-1,3-dihydro-2H-isoindole-2-carboxamide;
N-[4-(1,6-diazaspiro[3.5]non-1-ylcarbonyl)phenyl]-5-fluoro-1,3-dihydro-2H-isoindole-2-carboxamide;
N-[4-(2,5-diazaspiro[3.5]non-2-ylcarbonyl)phenyl]-5-fluoro-1,3-dihydro-2H-isoindole-2-carboxamide;
5-fluoro-N-[4-(5-oxa-2-azaspiro[3.4]oct-2-ylcarbonyl) phenyl]-1,3-dihydro-2H-isoindole-2-carboxamide;
5-fluoro-N-[4-(6-oxa-2-azaspiro[3.5]non-2-ylcarbonyl) phenyl]-1,3-dihydro-2H-isoindole-2-carboxamide;
5-fluoro-N-[44(2-oxa-7-azaspiro[3.5]non-7-ylcarbonyl) phenyl]-1,3-dihydro-2H-isoindole-2-carboxamide;
5-fluoro-N-[4-(hexahydro-5H-furo[2,3-c]pyrrol-5-ylcarbonyl)phenyl]-1,3-dihydro-2H-isoindole-2-carboxamide;

5-fluoro-N-[4-(tetrahydro-1H-furo[3,4-c]pyrrol-5(3H)-ylcarbonyl)phenyl]-1,3-dihydro-2H-isoindole-2-carboxamide;
5-fluoro-N-[4-(hexahydrofuro[3,4-c]pyridin-5(3H)-ylcarbonyl)phenyl]-1,3-dihydro-2H-isoindole-2-carboxamide;
N-{4-[6-(3-acetylphenyl)-4-(3-hydroxypropyl)-2-oxoquinolin-1(2H)-yl]butyl}-1,3-dihydro-2H-isoindole-2-carboxamide;
5-(acetamidomethyl)-N-{4-[(cyclopentylacetyl)amino]phenyl}-1,3-dihydro-2H-isoindole-2-carboxamide;
N-{5-[2-(2-chlorobenzyl)-1,3-thiazol-4-yl]-2-thienyl}-1,3-dihydro-2H-isoindole-2-carboxamide;
N-[4-(4-fluorophenyl)butyl]-5-(hydroxymethyl)-1,3-dihydro-2H-isoindole-2-carboxamide;
N-{4-[(cyclopentylacetyl)amino]phenyl}-5-(2-hydroxypropan-2-yl)-1,3-dihydro-2H-isoindole-2-carboxamide;
tert-butyl {4-[(1,3-dihydro-2H-isoindol-2-ylcarbonyl)amino]benzyl}carbamate;
N-{4-[(cyclopentylacetyl)amino]phenyl}-5-(methoxymethyl)-1,3-dihydro-2H-isoindole-2-carboxamide;
N-[4-(5-{[(tetrahydrofuran-2-ylmethyl)amino]methyl}-1,2,4-oxadiazol-3-yl)phenyl]-1,3-dihydro-2H-isoindole-2-carboxamide;
N-(4-{5-[(4-methoxypiperidin-1-yl)methyl]-1,2,4-oxadiazol-3-yl}phenyl)-1,3-dihydro-2H-isoindole-2-carboxamide;
N-[4-(5-{[4-(2-methoxyethyl)piperazin-1-yl]methyl}-1,2,4-oxadiazol-3-yl)phenyl]-1,3-dihydro-2H-isoindole-2-carboxamide;
N-{6-[(1-acetylpiperidin-4-yl)oxy]pyridin-3-yl}-1,3-dihydro-2H-isoindole-2-carboxamide;
N-{6-[(1-isobutyrylpiperidin-4-yl)oxy]pyridin-3-yl}-1,3-dihydro-2H-isoindole-2-carboxamide;
N-(6-{[1-(3-methylbutanoyl)piperidin-4-yl]oxy}pyridin-3-yl)-1,3-dihydro-2H-isoindole-2-carboxamide;
N-(6-{[1-(4,4,4-trifluorobutanoyl)piperidin-4-yl]oxy}pyridin-3-yl)-1,3-dihydro-2H-isoindole-2-carboxamide;
N-(6-([1-(methoxyacetyl)piperidin-4-yl]oxy}pyridin-3-yl)-1,3-dihydro-2H-isoindole-2-carboxamide;
N-(6-{[1-(tetrahydrofuran-2-ylcarbonyl)piperidin-4-yl]oxy}pyridin-3-yl)-1,3-dihydro-2H-isoindole-2-carboxamide;
N-(6-([1-(tetrahydrofuran-3-ylcarbonyl)piperidin-4-yl]oxy) pyridin-3-yl)-1,3-dihydro-2H-isoindole-2-carboxamide;
N-(6-{[1-(cyclopropylcarbonyl)piperidin-4-yl]oxy}pyridin-3-yl)-1,3-dihydro-2H-isoindole-2-carboxamide;
N-(6-{[1-(cyclopropylacetyl)piperidin-4-yl]oxy}pyridin-3-yl)-1,3-dihydro-2H-isoindole-2-carboxamide;
N-(6-{[1-(cyclobutylcarbonyl)piperidin-4-yl]oxy}pyridin-3-yl)-1,3-dihydro-2H-isoindole-2-carboxamide;
N-(6-{[1-(cyclopentylcarbonyl)piperidin-4-yl]oxy}pyridin-3-yl)-1,3-dihydro-2H-isoindole-2-carboxamide;
N-(6-{[1-(cyclopentylacetyl)piperidin-4-yl]oxy}pyridin-3-yl)-1,3-dihydro-2H-isoindole-2-carboxamide;
N-(6-{[1-(cyclohexylcarbonyl)piperidin-4-yl]oxy}pyridin-3-yl)-1,3-dihydro-2H-isoindole-2-carboxamide;
tert-butyl (2-{4-[(1,3-dihydro-2H-isoindol-2-ylcarbonyl)amino]phenyl}ethyl)carbamate;
N-{4-[(tetrahydrofuran-3-ylmethyl)sulfamoyl]phenyl}-1,3-dihydro-2H-isoindole-2-carboxamide;
5-cyano-N-{4-[(tetrahydrofuran-3-ylmethyl)sulfamoyl]phenyl}-1,3-dihydro-2H-isoindole-2-carboxamide;
N-(4-{[[(1S)-1-(4-fluorophenyl)-2-hydroxyethyl]carbamoyl)]}phenyl)-1,3-dihydro-2H-isoindole-2-carboxamide;
N-(4-([(1S)-2-hydroxy-1-(4-methoxyphenyl)ethyl]carbamoyl}phenyl)-1,3-dihydro-2H-isoindole-2-carboxamide;
N-(4-{[(1S)-1-(1,3-benzodioxol-5-yl)-2-hydroxyethyl]carbamoyl}phenyl)-1,3-dihydro-2H-isoindole-2-carboxamide;
N-{4-[1-(tetrahydrofuran-3-ylcarbonyl)piperidin-4-yl]phenyl}-1,3-dihydro-2H-isoindole-2-carboxamide;
N-{4-[1-(tetrahydrofuran-2-ylcarbonyl)piperidin-4-yl]phenyl}-1,3-dihydro-2H-isoindole-2-carboxamide;
N-{4-[1-(tetrahydro-2H-pyran-4-ylcarbonyl)piperidin-4-yl]phenyl}-1,3-dihydro-2H-isoindole-2-carboxamide;
N-{4-[1-(1,4-dioxan-2-ylcarbonyl)piperidin-4-yl]phenyl}-1,3-dihydro-2H-isoindole-2-carboxamide;
N-(4-1 {1-[(1-methylpyrrolidin-3-yl)carbonyl]piperidin-4-yl}phenyl)-1,3-dihydro-2H-isoindole-2-carboxamide;
N-(4-{1-[(1,1-dioxidotetrahydrothiophen-3-yl)carbonyl]piperidin-4-yl}phenyl)-1,3-dihydro-2H-isoindole-2-carboxamide;
N-{4-[1-(2-hydroxy-2-methylpropanoyl)piperidin-4-yl]phenyl}-1,3-dihydro-2H-isoindole-2-carboxamide;
N-{4-[1-(morpholin-4-ylacetyl)piperidin-4-yl]phenyl}-1,3-dihydro-2H-isoindole-2-carboxamide;
N-(4-{[1-(tetrahydrofuran-3-ylcarbonyl)piperidin-4-yl]oxy}phenyl)-1,3-dihydro-2H-isoindole-2-carboxamide;
5-cyano-N-{4-[1-(2-methylpropanoyl)-1,2,3,6-tetrahydropyridin-4-yl]phenyl)}-1,3-dihydro-2H-isoindole-2-carboxamide;
tert-butyl [(1-{4-[(1,3-dihydro-2H-isoindol-2-ylcarbonyl)amino]phenyl}azetidin-3-yl)methyl]carbamate;
N-(4-{[1-(2-methylbutanoyl)piperidin-4-yl]oxy}phenyl)-1,3-dihydro-2H-isoindole-2-carboxamide;
N-(4-{[1-(3-methylbutanoyl)piperidin-4-yl]oxy}phenyl)-1,3-dihydro-2H-isoindole-2-carboxamide;
N-(4-{[1-(2,3-dimethylbutanoyl)piperidin-4-yl]oxy}phenyl)-1,3-dihydro-2H-isoindole-2-carboxamide;
N-(4-{[1-(tetrahydrofuran-2-ylcarbonyl)piperidin-4-yl]oxy)phenyl)-1,3-dihydro-2H-isoindole-2-carboxamide;
N-(4-{[1-(cyclohexylcarbonyl)piperidin-4-yl]oxy}phenyl)-1,3-dihydro-2H-isoindole-2-carboxamide;
N-(4-[1-(cyclohexylacetyl)piperidin-4-yl]oxy}phenyl)-1,3-dihydro-2H-isoindole-2-carboxamide;
N-(4-{[1-(tetrahydro-2H-pyran-4-ylacetyl)piperidin-4-yl]oxy}phenyl)-1,3-dihydro-2H-isoindole-2-carboxamide;
N-(4-([1-(morpholin-4-ylacetyl)piperidin-4-yl]oxy)phenyl)-1,3-dihydro-2H-isoindole-2-carboxamide;
N-(4-{[1-(tetrahydrofuran-3-ylacetyl)piperidin-4-yl]oxy}phenyl)-1,3-dihydro-2H-isoindole-2-carboxamide;
5-fluoro-N-(4-{[1-(1,3-thiazol-2-yl)propan-2-yl]carbamoyl}phenyl)-1,3-dihydro-2H-isoindole-2-carboxamide;
N-{4-[(4,4-di fluorocyclohexyl)carbamoyl]phenyl}-5-fluoro-1,3-dihydro-2H-isoindole-2-carboxamide;

N-(4-{[1-(3,5-dimethyl-1H-pyrazol-1-yl)propan-2-yl]carbamoyl}phenyl)-5-fluoro-1,3-dihydro-2H-isoindole-2-carboxamide;

5-fluoro-N-(4-{[2-methyl-1-(morpholin-4-yl)butyl]carbamoyl}phenyl)-1,3-dihydro-2H-isoindole-2-carboxamide;

5-fluoro-N-(4-{[2-(2-methyl-1,3-thiazol-4-yl)ethyl]carbamoyl}phenyl)-1,3-dihydro-2H-isoindole-2-carboxamide;

5-fluoro-N-{4-([2-methyl-1-(morpholin-4-yl)propan-2-yl]carbamoyl}phenyl)-1,3-dihydro-2H-isoindole-2-carboxamide;

5-fluoro-N-{4-[(4-methoxybenzyl)carbamoyl]phenyl}-1,3-dihydro-2H-isoindole-2-carboxamide;

5-fluoro-N-(4-{[3-(morpholin-4-yl)propyl]carbamoyl}phenyl)-1,3-dihydro-2H-isoindole-2-carboxamide;

Nalpha-(4-{[(5-fluoro-1,3-dihydro-2H-isoindol-2-yl)carbonyl]amino}benzoyl)-D-phenylalaninamide;

N-(4-{[2-(acetylamino)phenyl]carbamoyl)}phenyl)-5-fluoro-1,3-dihydro-2H-isoindole-2-carboxamide;

5-fluoro-N-[4-({4-[2-(2-hydroxyethoxy)ethyl]piperazin-1-yl}carbonyl)phenyl]-1,3-dihydro-2H-isoindole-2-carboxamide;

5-fluoro-N-(4-{[2-(furan-2-yl)-2-(pyrrolidin-1-yl)ethyl]carbamoyl}phenyl)-1,3-dihydro-2H-isoindole-2-carboxamide;

N-{4-[bis(2-methoxyethyl)carbamoyl]phenyl}-5-fluoro-1,3-dihydro-2H-isoindole-2-carboxamide;

N-{4-[(1-amino- 1-xohexan-2-yl)carbamoyl]phenyl}-5-fluoro-1,3-dihydro-2H-isoindole-2-carboxamide;

N-(4-{[2-(3,4-dimethoxyphenyl)ethyl]carbamoyl}phenyl)-5-fluoro-1,3-dihydro-2H-isoindole-2-carboxamide;

N-(4-{[(2S)-3,3-dimethyl-1-(methylamino)-1-oxobutan-2-yl]carbamoyl)}phenyl)-5-fluoro-1,3-dihydro-2H-isoindole-2-carboxamide;

Nalpha-{4-{[(5-fluoro-1,3-dihydro-2H-isoindol-2-yl)carbonyl]amino}benzoyl)-L-phenylalaninamide;

N-(4-{[(2R)-1-amino-4-methyl-1-oxopentan-1-yl]carbamoyl}phenyl)-5-fluoro-1,3-dihydro-2H-isoindole-2-carboxamide;

N-{4-[(4-cyclohexylpiperazin-1-yl)carbonyl]phenyl}-5-fluoro-1,3-dihydro-2H-isoindole-2-carboxamide;

5-fluoro-N-(4-{[3-(methylcarbamoyl)phenyl]carbamoyl)}phenyl)-1,3-dihydro-2H-isoindole-2-carboxamide;

N-{4-[(2-amino-2-oxo-1-phenylethyl)carbamoyl]phenyl}-5-fluoro-1,3-dihydro-2H-isoindole-2-carboxamide;

N-{4-[(3-tert-butoxypropyl)carbamoyl]phenyl}-5-fluoro-1,3-dihydro-2H-isoindole-2-carboxamide;

N-(4-{[2-(2,6-dimethylmorpholin-4-yl)ethyl]carbamoyl}phenyl)-5-fluoro-1,3-dihydro-2H-isoindole-2-carboxamide;

N-(4-{[(1R)-2-amino-2-oxo-1-phenylethyl]carbamoyl}phenyl)-5-fluoro-1,3-dihydro-2H-isoindole-2-carboxamide;

5-fluoro-N-{4-[(3-methoxybenzyl)carbamoyl]phenyl}-1,3-dihydro-2H-isoindole-2-carboxamide;

N-(4-{[2-(3,5-dimethyl-1H-pyrazol-1-yl)ethyl]carbamoyl}phenyl)-5-fluoro-1,3-dihydro-2H-isoindole-2-carboxamide;

5-fluoro-N-(4-{[2-methyl-2-(morpholin-4-yl)propyl]carbamoyl}phenyl)-1,3-dihydro-2H-isoindole-2-carboxamide;

5-fluoro-N-(4-{[(3S)-1-methyl-2-oxoazepan-3-yl]carbamoyl}phenyl)-1,3-dihydro-2H-isoindole-2-carboxamide;

5-fluoro-N-(4-{[2-(4-methylpiperazin-1-yl)ethyl]carbamoyl}phenyl)-1,3-dihydro-2H-isoindole-2-carboxamide;

5-fluoro-N-(4-{[4-(morpholin-4-yl)benzyl]carbamoyl}phenyl)-1,3-dihydro-2H-isoindole-2-carboxamide;

5-fluoro-N-(4-{[3-(piperidin-1-yl)propyl]carbamoyl}phenyl)-1,3-dihydro-2H-isoindole-2-carboxamide;

5-fluoro-N-{4-[(3-methoxy-2,2-dimethylpropyl)carbamoyl]phenyl}-1,3-dihydro-2H-isoindole-2-carboxamide;

N-{4-[(3,3-dimethylbutyl)carbamoyl]phenyl}-5-fluoro-1,3-dihydro-2H-isoindole-2-carboxamide;

5-fluoro-N-(4-{[1-(furan-2-yl)propan-2-yl]carbamoyl}phenyl)-1,3-dihydro-2H-isoindole-2-carboxamide;

5-fluoro-N-(4-{[(3-methyl-1,2-oxazol-5-yl)methyl]carbamoyl}phenyl)-1,3-dihydro-2H-isoindole-2-carboxamide;

N-(4-{[(2R)-1-cyanobutan-2-yl]carbamoyl}phenyl)-5-fluoro-1,3-dihydro-2H-isoindole-2-carboxamide;

N-{4-[(2R)-butan-2-ylcarbamoyl]phenyl}-5-fluoro-1,3-dihydro-2H-isoindole-2-carboxamide;

5-fluoro-N-(4-{[2-(1H-pyrazol-1-yl)ethyl]carbamoyl}phenyl)-1,3-dihydro-2H-isoindole-2-carboxamide;

5-fluoro-N-{4-[methyl(3-methylbutyl)carbamoyl]phenyl}-1,3-dihydro-2H-isoindole-2-carboxamide;

N-(4-{[1-(ethylamino)-1-oxopropan-2-yl]carbamoyl}phenyl)-5-fluoro-1,3-dihydro-2H-isoindole-2-carboxamide;

5-fluoro-N-(4-{[(1-methyl-1H-pyrazol-3-yl)methyl]carbamoyl}phenyl)-1,3-dihydro-2H-isoindole-2-carboxamide;

5-fluoro-N-{4-[(2-methoxybutyl)carbamoyl]phenyl}-1,3-dihydro-2H-isoindole-2-carboxamide;

N-(4-{[4-(dimethylamino)butyl]carbamoyl}phenyl)-5-fluoro-1,3-dihydro-2H-isoindole-2-carboxamide;

5-fluoro-N-{4-[(3S)-tetrahydrofuran-3-ylcarbamoyl]phenyl}-1,3-dihydro-2H-isoindole-2-carboxamide;

5-fluoro-N-{4-[(1-methoxybutan-2-yl)carbamoyl]phenyl}-1,3-dihydro-2H-isoindole-2-carboxamide;

N-{4-[(2-ethoxypropyl)carbamoyl]phenyl}-5-fluoro-1,3-dihydro-2H-isoindole-2-carboxamide;

N-{4-[benzyl(methyl)carbamoyl]phenyl}-5-fluoro-1,3-dihydro-2H-isoindole-2-carboxamide;

N-{4-[(2S)-butan-2-ylcarbamoyl]phenyl}-5-fluoro-1,3-dihydro-2H-isoindole-2-carboxamide;

5-fluoro-N-(4-{[2-(5-methyl-1H-pyrazol-1-yl)ethyl]carbamoyl}phenyl)-1,3-dihydro-2H-isoindole-2-carboxamide;

5-fluoro-N-(4-{[2-(3-methyl-1H-pyrazol-1-yl)ethyl]carbamoyl}phenyl)-1,3-dihydro-2H-isoindole-2-carboxamide;

5-fluoro-N-{4-[(2-methylpropyl)carbamoyl]phenyl}-1,3-dihydro-2H-isoindole-2-carboxamide;

5-fluoro-N-{4-[(pyridin-3-ylmethyl)carbamoyl]phenyl}-1,3-dihydro-2H-isoindole-2-carboxamide;

5-fluoro-N-{4-[(tetrahydrofuran-2-ylmethyl)carbamoyl]phenyl}-1,3-dihydro-2H-isoindole-2-carboxamide;

N-(4-{[(1R)-1-cyclopropylethyl]carbamoyl}phenyl)-5-fluoro-1,3-dihydro-2H-isoindole-2-carboxamide;

5-fluoro-N-(4-[1-(1-methylcyclopropyl)ethyl]carbamoyl)phenyl)-1,3-dihydro-2H-isoindole-2-carboxamide;

5-fluoro-N-{4-[(thiophen-2-ylmethyl)carbamoyl]phenyl}-1,3-dihydro-2H-isoindole-2-carboxamide;
N-(4-{[(1S)-1-cyclopropylethyl]carbamoyl}phenyl)-5-fluoro-1,3-dihydro-2H-isoindole-2-carboxamide;
5-fluoro-N-{4-[(4-methoxybutyl)carbamoyl]phenyl}-1,3-dihydro-2H-isoindole-2-carboxamide;
5-fluoro-N-(4-{[(5-methyl-1,3-oxazol-2-yl)methyl]carbamoyl}phenyl)-1,3-dihydro-2H-isoindole-2-carboxamide;
5-fluoro-N-(4-{[2-(tetrahydro-2H-pyran-3-yl)ethyl]carbamoyl}phenyl)-1,3-dihydro-2H-isoindole-2-carboxamide;
5-fluoro-N-(4-{[(2S)-1-methoxypropan-2-yl]carbamoyl}phenyl)-1,3-dihydro-2H-isoindole-2-carboxamide;
N-{4-[(3,3-dimethyl-2-oxobutyl)carbamoyl]phenyl}-5-fluoro-1,3-dihydro-2H-isoindole-2-carboxamide;
5-fluoro-N-(4-{[(1-methyl-1H-pyrrol-2-yl)methyl]carbamoyl}phenyl)-1,3-dihydro-2H-isoindole-2-carboxamide;
5-fluoro-N-(4-{[2-(propan-2-yloxy)ethyl]carbamoyl}phenyl)-1,3-dihydro-2H-isoindole-2-carboxamide;
N-(4-{[3-(dimethylamino)propyl]carbamoyl}phenyl)-5-fluoro-1,3-dihydro-2H-isoindole-2-carboxamide;
N-(4-{[(2S)-1-amino-1-oxobutan-2-yl]carbamoyl}phenyl)-5-fluoro-1,3-dihydro-2H-isoindole-2-carboxamide;
5-fluoro-N-[4-(tetrahydro-2H-pyran-3-ylcarbamoyl)phenyl]-1,3-dihydro-2H-isoindole-2-carboxamide;
5-fluoro-N-(4-{[2-(1H-pyrrol-1-yl)ethyl]carbamoyl}phenyl)-1,3-dihydro-2H-isoindole-2-carboxamide;
5-fluoro-N-(4-[(1-methoxypropan-2-yl)carbamoyl]phenyl)-1,3-dihydro-2H-isoindole-2-carboxamide;
5-fluoro-N-{4-[(2-methoxyethyl)carbamoyl]phenyl}-1,3-dihydro-2H-isoindole-2-carboxamide;
N-[4-(cyclopentylcarbamoyl)phenyl]-5-fluoro-1,3-dihydro-2H-isoindole-2-carboxamide;
5-fluoro-N-(4-{[(2S)-3-methylbutan-2-yl]carbamoyl}phenyl)-1,3-dihydro-2H-isoindole-2-carboxamide;
5-fluoro-N-(4-{[(2R)-3-methylbutan-2-yl]carbamoyl}phenyl)-1,3-dihydro-2H-isoindole-2-carboxamide;
5-fluoro-N-(4-{[(2S)-2-methylbutyl]carbamoyl}phenyl)-1,3-dihydro-2H-isoindole-2-carboxamide;
5-fluoro-N-{4-[(2-hydroxy-2-methylpropyl)carbamoyl]phenyl}-1,3-dihydro-2H-isoindole-2-carboxamide;
5-fluoro-N-(4-{[2-(tetrahydro-2H-pyran-4-yl)ethyl]carbamoyl}phenyl)-1,3-dihydro-2H-isoindole-2-carboxamide;
N-[4-(butylcarbamoyl)phenyl]-5-fluoro-1,3-dihydro-2H-isoindole-2-carboxamide;
5-fluoro-N-{4-[methyl(tetrahydrofuran-2-yl methyl)carbamoyl]phenyl}-1,3-dihydro-2H-isoindole-2-carboxamide;
5-fluoro-N-{4-[(2-methoxyethyl)(methyl)carbamoyl]phenyl}-1,3-dihydro-2H-isoindole-2-carboxamide;
N-{4-[(1-cyanoethyl)carbamoyl]phenyl}-5-fluoro-1,3-dihydro-2H-isoindole-2-carboxamide;
5-fluoro-N-{4-1 [(5-methyl-1,2-oxazol-3-yl)methyl]carbamoyl}phenyl)-1,3-dihydro-2H-isoindole-2-carboxamide;
5-fluoro-N-{4-[(3R)-tetrahydrofuran-3-ylcarbamoyl]phenyl}-1,3-dihydro-2H-isoindole-2-carboxamide;
N-{4-[(3-methoxy-2,2-dimethylpropyl)carbamoyl]phenyl}-1,3-dihydro-2H-isoindole-2-carboxamide;
N-{4-[(4,4-difluorocyclohexyl)carbamoyl]phenyl}-1,3-dihydro-2H-isoindole-2-carboxamide;
N-(4-{[(2R)-1-cyanobutan-2-yl]carbamoyl}phenyl)-1,3-dihydro-2H-isoindole-2-carboxamide;
N-{4-[(2-methoxybutyl)carbamoyl]phenyl}-1,3-dihydro-2H-isoindole-2-carboxamide;
N-(4-{[1-(ethylamino)-1-oxopropan-2-yl]carbamoyl}phenyl)-1,3-dihydro-2H-isoindole-2-carboxamide;
N-(4-{[2-methyl-2-(morpholin-4-yl)butyl]carbamoyl}phenyl)-1,3-dihydro-2H-isoindole-2-carboxamide;
N-(4-{[(1R)-1-cyclopropylethyl]carbamoyl}phenyl)-1,3-dihydro-2H-isoindole-2-carboxamide;
N-(4-{[(1S)-1-cyclopropylethyl]carbamoyl}phenyl)-1,3-dihydro-2H-isoindole-2-carboxamide;
N-(6-{[(2S)-tetrahydrofuran-2-ylmethyl]carbamoyl}pyridazin-3-yl)-1,3-dihydro-2H-isoindole-2-carboxamide;
N-{4-[(3S)-tetrahydrofuran-3-ylcarbamoyl]phenyl}-1,3-dihydro-2H-isoindole-2-carboxamide;
N-(4-{[2-(tetrahydro-2H-pyran-3-yl)ethyl]carbamoyl}phenyl)-1,3-dihydro-2H-isoindole-2-carboxamide;
N-(4-{[(5-methyl-1,3-oxazol-2-yl)methyl]carbamoyl}phenyl)-1,3-dihydro-2H-isoindole-2-carboxamide;
N-[4-({2-[(dimethylamino)methyl]benzyl}carbamoyl)phenyl]-1,3-dihydro-2H-isoindole-2-carboxamide;
N-(4-{[(1R)-2-amino-2-oxo-1-phenylethyl]carbamoyl}phenyl)-1,3-dihydro-2H-isoindole-2-carboxamide;
N-[4-(1,3-oxazol-2-ylcarbamoyl)phenyl]-1,3-dihydro-2H-isoindole-2-carboxamide;
N-[4-(tetrahydro-2H-pyran-3-ylcarbamoyl)phenyl]-1,3-dihydro-2H-isoindole-2-carboxamide;
N-(4-{[2-(2,6-dimethylmorpholin-4-yl)ethyl]carbamoyl}phenyl)-1,3-dihydro-2H-isoindole-2-carboxamide;
N-(4-{[1-(1-methylcyclopropyl)ethyl]carbamoyl)}phenyl)-1,3-dihydro-2H-isoindole-2-carboxamide;
N-(4-{[2-(furan-2-yl)-2-(pyrrolidin-1-yl)ethyl]carbamoyl}phenyl)-1,3-dihydro-2H-isoindole-2-carboxamide;
5-cyano-N-(4-[1-(tetrahydrofuran-3-ylcarbonyl)-1,2,3,6-tetrahydropyridin-4-yl]phenyl)}-1,3-dihydro-2H-isoindole-2-carboxamide;
5-cyano-N-{4-[1-(tetrahydro-2H-pyran-4-ylcarbonyl)-1 2,3,6-tetrahydropyridin-4-yl]phenyl}-1,3-dihydro-2H-isoindole-2-carboxamide;
5-cyano-N-{4-[1-(2-hydroxy-2-methylpropanoyl)-1,2,3,6-tetrahydropyridin-4-yl]phenyl}-1,3-dihydro-2H-isoindole-2-carboxamide;
5-cyano-N-{4-[1-(morpholin-4-ylacetyl)-1,2,3,6-tetrahydropyridin-4-yl]phenyl}-1,3-dihydro-2H-isoindole-2-carboxamide;
N-{4-[(4-fluorobenzyl)(3-methylbutanoyl)amino]butyl}-1,3-dihydro-2H-isoindole-2-carboxamide;
N-(6-{[(2R)-tetrahydrofuran-2-ylmethyl]carbamoyl)}pyridazin-3-yl)-1,3-dihydro-2H-isoindole-2-carboxamide;
N-(4-{[3-(3,5-dimethyl-1H-pyrazol-1-yl)propyl]carbamoyl}phenyl)-1,3-dihydro-2H-isoindole-2-carboxamide;
N-(4-{[(3S)-1-methyl-2-oxoazepan-3-yl]carbamoyl}phenyl)-1,3-dihydro-2H-isoindole-2-carboxamide;

N-(4-{[2-(1H-pyrazol-1-yl)ethyl]carbamoyl}phenyl)-1,3-dihydro-2H-isoindole-2-carboxamide;
N-(4-{[1-(1,3-thiazol-2-yl)ethyl]carbamoyl}phenyl)-1,3-dihydro-2H-isoindole-2-carboxamide;
N-(4-{[1-(furan-2-yl)propan-2-yl]carbamoyl}phenyl)-1,3-dihydro-2H-isoindole-2-carboxamide;
N-(4-{[1-(1-methyl-1H-pyrazol-4-yl)ethyl]carbamoyl}phenyl)-1,3-dihydro-2H-isoindole-2-carboxamide;
N-(4-{[(2R)-1-amino-4-methyl-1-oxopentan-2-yl]carbamoyl}phenyl)-1,3-dihydro-2H-isoindole-2-carboxamide;
N-(4-{[1-(3,5-dimethyl-1H-pyrazol-1-yl)propan-2-yl]carbamoyl}phenyl)-1,3-dihydro-2H-isoindole-2-carboxamide;
N-{4-[(2,2-difluoroethyl)carbamoyl]phenyl}-1,3-dihydro-2H-isoindole-2-carboxamide;
N-(4-{[2-(tetrahydro-2H-pyran-4-yl)ethyl]carbamoyl}phenyl)-1,3-dihydro-2H-isoindole-2-carboxamide;
N-{4-[(tetrahydrofuran-2-ylmethyl)carbamoyl]phenyl}-1,3-dihydro-2H-isoindole-2-carboxamide;
N-{4-[(2-methoxy-2-methylpropyl)carbamoyl]phenyl}-1,3-dihydro-2H-isoindole-2-carboxamide;
N-(4-{[(5-methyl-1,2-oxazol-3-yl)methyl]carbamoyl}phenyl)-1,3-dihydro-2H-isoindole-2-carboxamide;
N-(4-{[(1-methyl-1H-pyrazol-4-yl)methyl]carbamoyl}phenyl)-1,3-dihydro-2H-isoindole-2-carboxamide;
N-(4-{[2-(3,5-dimethyl-1H-pyrazol-1-yl)ethyl]carbamoyl}phenyl)-1,3-dihydro-2H-isoindole-2-carboxamide;
Nalpha-{4-[(1,3-dihydro-2H-isoindol-2-ylcarbonyl)amino]benzoyl}-L-phenylalaninamide;
N-(4-{[2-(2-methyl-1,3-thiazol-4-yl)ethyl]carbamoyl}phenyl)-1,3-dihydro-2H-isoindole-2-carboxamide;
N-(4-{[(2S)-3,3-dimethyl-1-(methylamino)-1-oxobutan-2-yl]carbamoyl}phenyl)-1,3-dihydro-2H-isoindole-2-carboxamide;
N-[4-(thiophen-3-ylcarbamoyl)phenyl]-1,3-dihydro-2H-isoindole-2-carboxamide;
N-(4-{[2-(5-methyl-1H-pyrazol-1-yl)ethyl]carbamoyl}phenyl)-1,3-dihydro-2H-isoindole-2-carboxamide;
N-(4-{[2-(3-methyl-1H-pyrazol-1-yl)ethyl]carbamoyl}phenyl)-1,3-dihydro-2H-isoindole-2-carboxamide;
N-{4-[(2S)-butan-2-ylcarbamoyl]phenyl}-1,3-dihydro-2H-isoindole-2-carboxamide;
N-{4-[(3,3-dimethyl-2-oxobutyl)carbamoyl]phenyl}-1,3-dihydro-2H-isoindole-2-carboxamide;
N-(4-{[(1-methyl-1H-pyrazol-3-yl)methyl]carbamoyl}phenyl)-1,3-dihydro-2H-isoindole-2-carboxamide;
N-(4-{[2-(acetylamino)phenyl]carbamoyl}phenyl)-1,3-dihydro-2H-isoindole-2-carboxamide;
N-{4-[(1-methoxybutan-2-yl)carbamoyl]phenyl}-1,3-dihydro-2H-isoindole-2-carboxamide;
N-[4-(tetrahydro-2H-pyran-4-ylcarbamoyl)phenyl]-1,3-dihydro-2H-isoindole-2-carboxamide;
N-[4-(pyrimidin-4-ylcarbamoyl)phenyl]-1,3-dihydro-2H-isoindole-2-carboxamide;
N-(4-{[2-(1H-pyrrol-1-yl)ethyl]carbamoyl}phenyl)-1,3-dihydro-2H-isoindole-2-carboxamide;
N-(4-{[(2S)-2-methylbutyl]carbamoyl}phenyl)-1,3-dihydro-2H-isoindole-2-carboxamide;
N-{4-[(1-amino-1-oxohexan-2-yl)carbamoyl]phenyl}-1,3-dihydro-2H-isoindole-2-carboxamide;
N-{4-[(2-amino-2-oxo-1-phenylethyl)carbamoyl]phenyl}-1,3-dihydro-2H-isoindole-2-carboxamide;
N-{4-[(3-tert-butoxypropyl)carbamoyl]phenyl}-1,3-dihydro-2H-isoindole-2-carboxamide;
N-(4-{[3-(methylcarbamoyl)phenyl]carbamoyl}phenyl)-1,3-dihydro-2H-isoindole-2-carboxamide;
N-(4-{[(2R)-3-methylbutan-2-yl]carbamoyl}phenyl)-1,3-dihydro-2H-isoindole-2-carboxamide;
N-(4-{[(2S)-3-methylbutan-2-yl]carbamoyl}phenyl)-1,3-dihydro-2H-isoindole-2-carboxamide;
N-(4-{[2-methyl-1-(morpholin-4-yl)propan-2-yl]carbamoyl}phenyl)-1,3-dihydro-2H-isoindole-2-carboxamide;
N-(4-{[2-methyl-2-(morpholin-4-yl)propyl]carbamoyl}phenyl)-1,3-dihydro-2H-isoindole-2-carboxamide;
N-{4-[(2-ethoxypropyl)carbamoyl]phenyl}-1,3-dihydro-2H-isoindole-2-carboxamide;
N-{7-oxo-7-[(3-phenylpropyl)amino]heptyl}-1,3-dihydro-2H-isoindole-2-carboxamide;
N-(4-{2-[(3-methylbutanoyl)amino]ethyl}phenyl)-1,3-dihydro-2H-isoindole-2-carboxamide;
N-(4-{2-[(4-methylpentanoyl)amino]ethyl}phenyl)-1,3-dihydro-2H-isoindole-2-carboxamide;
N-(4-{2-[(ethoxyacetyl)amino]ethyl}phenyl)-1,3-dihydro-2H-isoindole-2-carboxamide;
N-[4-({[(2-methoxyethoxy)acetyl]amino}ethyl)phenyl]-1,3-dihydro-2H-isoindole-2-carboxamide;
N-(4-{2-[(tetrahydrofuran-2-ylcarbonyl)amino]ethyl}phenyl)-1,3-dihydro-2H-isoindole-2-carboxamide;
N-(4-{2-[(cyclopentylcarbonyl)amino]ethyl}phenyl)-1,3-dihydro-2H-isoindole-2-carboxamide;
N-(4-(2-{[(cyclopentylacetyl)amino]ethyl}phenyl)-1,3-dihydro-2H-isoindole-2-carboxamide;
N-{4-[2-(benzoylamino)ethyl]phenyl}-1,3-dihydro-2H-isoindole-2-carboxamide;
N-(4-{2-[(tetrahydro-2H-pyran-4-ylcarbonyl)amino]ethyl}phenyl)-1,3-dihydro-2H-isoindole-2-carboxamide;
N-(4-{2-[(tetrahydro-2H-pyran-4-ylacetyl)amino]ethyl}phenyl)-1,3-dihydro-2H-isoindole-2-carboxamide;
N-(4-{2-[(tetrahydrofuran-3-ylacetyl)amino]ethyl}phenyl)-1,3-dihydro-2H-isoindole-2-carboxamide;
N-(4-{1-[(3R)-tetrahydrofuran-3-ylcarbonyl]-1,2,3,6-tetrahydropyridin-4-yl}phenyl)-1,3-dihydro-2H-isoindole-2-carboxamide;
N-(4-{1-[(3S)-tetrahydrofuran-3-ylcarbonyl]-1,2,3,6-tetrahydropyridin-4-yl}phenyl)-1,3-dihydro-2H-isoindole-2-carboxamide;
N-(4-11-[(1,1-dioxidotetrahydro-2H-thiopyran-4-yl)carbonyl]-1,2,3,6-tetrahydropyridin-4-yl}phenyl)-1,3-dihydro-2H-isoindole-2-carboxamide;
N-(4-{(1-[(2R)-tetrahydrofuran-2-ylcarbonyl]piperidin-4-yl}phenyl)-1,3-dihydro-2H-isoindole-2-carboxamide;
N-(4-{1-[(2S)-tetrahydrofuran-2-ylcarbonyl]piperidin-4-yl}phenyl)-1,3-dihydro-2H-isoindole-2-carboxamide;
N-(4-{1-[(3R)-tetrahydrofuran-3-ylcarbonyl]piperidin-4-yl}phenyl)-1,3-dihydro-2H-isoindole-2-carboxamide;
N-[4-(1-benzoylazetidin-3-yl)butyl]-1,3-dihydro-2H-isoindole-2-carboxamide;

N-(4-{4-[(2-methylpropanoyl)amino]cyclohex-1-en-1-yl}phenyl)-1,3-dihydro-2H-isoindole-2-carboxamide;
N-[4-(4-{[(2R)-tetrahydrofuran-2-ylcarbonyl]amino}cyclohex-1-en-1-yl)phenyl]-1,3-dihydro-2H-isoindole-2-carboxamide;
N-[4-(4-{[(2S)-tetrahydrofuran-2-ylcarbonyl]amino}cyclohex-1-en-1-yl)phenyl]-1,3-dihydro-2H-isoindole-2-carboxamide;
N-(4-{4-[(cyclopentylacetyl)amino]cyclohex-1-en-1-yl}phenyl)-1,3-dihydro-2H-isoindole-2-carboxamide;
N-(4-(4-[(cyclopropylacetyl)amino]cyclohex-1-en-1-yl}phenyl)-1,3-dihydro-2H-isoindole-2-carboxamide;
N-(4-{4-[(2-hydroxy-2-methylpropanoyl)amino]cyclohex-1-en-1-yl}phenyl)-1,3-dihydro-2H-isoindole-2-carboxamide;
N-(4-{4-[(tetrahydro-2H-pyran-4-ylcarbonyl)amino]cyclohex-1-en-1-yl}phenyl)-1,3-dihydro-2H-isoindole-2-carboxamide;
N-(4-{4-[(cyclohexylcarbonyl)amino]cyclohex-1-en-1-yl}phenyl)-1,3-dihydro-2H-isoindole-2-carboxamide;
or a pharmaceutically acceptable salt thereof.

19. The compound of claim 2, selected from the group consisting of:
N-{4-[(3-phenylpropyl)carbamoyl]phenyl}-1,3-dihydro-2H-isoindole-2-carboxamide;
N-(4-{[4-(aminomethyl)benzyl]carbamoyl}phenyl)-5-fluoro-1,3-dihydro-2H-isoindole-2-carboxamide;
5-cyano-N-{4-[(3-phenylpropyl)carbamoyl]phenyl}-1,3-dihydro-2H-isoindole-2-carboxamide;
N-{4-[(cyclopentylmethyl)carbamoyl]phenyl}-5-fluoro-1,3-dihydro-2H-isoindole-2-carboxamide;
5-cyano-N-[4-(propylcarbamoyl)phenyl]-1,3-dihydro-2H-isoindole-2-carboxamide;
5-fluoro-N-{4-[(pyridin-2-ylmethyl)carbamoyl]phenyl}-1,3-dihydro-2H-isoindole-2-carboxamide;
N-[4-(benzylcarbamoyl)phenyl]-5-fluoro-1,3-dihydro-2H-isoindole-2-carboxamide;
N-{4-[(3,4-dimethoxybenzyl)carbamoyl]phenyl}-1,3-dihydro-2H-isoindole-2-carboxamide;
N-{4-[(2,3-dimethoxybenzyl)carbamoyl]phenyl}-1,3-dihydro-2H-isoindole-2-carboxamide;
5-fluoro-N-{4-[(3-phenylpropyl)carbamoyl]phenyl}-1,3-dihydro-2H-isoindole-2-carboxamide;
N-{4-[(2,3-dihydro-1,4-benzodioxin-5-ylmethyl)carbamoyl]phenyl}-1,3-dihydro-2H-isoindole-2-carboxamide;
5-fluoro-N-(4-{[1-(3-methylbutyl)-1H-pyrazol-4-yl]carbamoyl}phenyl)-1,3-dihydro-2H-isoindole-2-carboxamide;
N-{4-[(2-fluorobenzyl)carbamoyl]phenyl}-1,3-dihydro-2H-isoindole-2-carboxamide;
5-fluoro-N-{4-[(3-methylbutyl)carbamoyl]phenyl}-1,3-dihydro-2H-isoindole-2-carboxamide;
N-{4-[(2-methoxybenzyl)carbamoyl]phenyl}-1,3-dihydro-2H-isoindole-2-carboxamide;
N-{4-[(3-fluorobenzyl)carbamoyl]phenyl}-1,3-dihydro-2H-isoindole-2-carboxamide;
5-fluoro-N-(4-{[3-(2-oxopyrrolidin-1-yl)propyl]carbamoyl}phenyl)-1,3-dihydro-2H-isoindole-2-carboxamide;
5-cyano-N-{4-[(3-methylbutyl)carbamoyl]phenyl}-1,3-dihydro-2H-isoindole-2-carboxamide;
N-{4-[(cyclopentylmethyl)carbamoyl]phenyl}-5-methyl-1,3-dihydro-2H-isoindole-2-carboxamide;
N-{4-[(4-fluorobenzyl)carbamoyl]phenyl}-1,3-dihydro-2H-isoindole-2-carboxamide;
N-{4-[(3,5-dimethoxybenzyl)carbamoyl]phenyl}-1,3-dihydro-2H-isoindole-2-carboxamide;
5-fluoro-N-{4-[(tetrahydrofuran-3-ylmethyl)carbamoyl]phenyl}-1,3-dihydro-2H-isoindole-2-carboxamide;
N-{4-[(2,2-dimethylpropyl)carbamoyl]phenyl}-1,3-dihydro-2H-isoindole-2-carboxamide;
5-fluoro-N-(4-{[2-(2-oxopyrrolidin-1-yl)ethyl]carbamoyl}phenyl)-1,3-dihydro-2H-isoindole-2-carboxamide;
N-(4-{[4-(trifluoromethoxy)benzyl]carbamoyl}phenyl)-1,3-dihydro-2H-isoindole-2-carboxamide;
N-(4-{[3-fluoro-5-(trifluoromethyl)benzyl]carbamoyl}phenyl)-1,3-dihydro-2H-isoindole-2-carboxamide;
N-{4-[(3-methylbutyl)carbamoyl]phenyl}-1,3-dihydro-2H-isoindole-2-carboxamide;
5-methoxy-N-{4-[(3-phenylpropyl)carbamoyl]phenyl}-1,3-dihydro-2H-isoindole-2-carboxamide;
N-{4-[(4-chlorobenzyl)carbamoyl]phenyl)}-1,3-dihydro-2H-isoindole-2-carboxamide;
N-{4-[(cyclopentylmethyl)carbamoyl]phenyl}-1,3-dihydro-2H-isoindole-2-carboxamide;
N-{4-[(3,4,5-trimethoxybenzyl)carbamoyl]phenyl}-1,3-dihydro-2H-isoindole-2-carboxamide;
5-nitro-N-[4-(propylcarbamoyl)phenyl]-1,3-dihydro-2H-isoindole-2-carboxamide; 5-methyl-N-{4-[(3-methylbutyl)carbamoyl]phenyl}-1,3-dihydro-2H-isoindole-2-carboxamide;
N-{4-[(4-methoxybenzyl)carbamoyl]phenyl}-1,3-dihydro-2H-isoindole-2-carboxamide;
N-{4-[(2-thienylmethyl)carbamoyl]phenyl}-1,3-dihydro-2H-isoindole-2-carboxamide;
N-{4-[(1-ethyl-1H-pyrazol-4-yl)carbamoyl]phenyl}-5-fluoro-1,3-dihydro-2H-isoindole-2-carboxamide;
N-{4-[(1-benzyl-1H-pyrazol-4-yl)carbamoyl]phenyl}-5-fluoro-1,3-dihydro-2H-isoindole-2-carboxamide;
N-{4-[(3,3-dimethylbutyl)carbamoyl]phenyl}-1,3-dihydro-2H-isoindole-2-carboxamide;
N-(4-{[(2R)-tetrahydrofuran-2-ylmethyl]carbamoyl}phenyl}-1,3-dihydro-2H-isoindole-2-carboxamide;
N-(4-{[2-(2,3-dimethoxyphenyl)ethyl]carbamoyl}phenyl)-1,3-dihydro-2H-isoindole-2-carboxamide;
N-{4-[(3-thienylmethyl)carbamoyl]phenyl}-1,3-dihydro-2H-isoindole-2-carboxamide;
5-methoxy-N-{4-[(3-methylbutyl)carbamoyl]phenyl}-1,3-dihydro-2H-isoindole-2-carboxamide;
N-{4-[(pyridin-2-ylmethyl)carbamoyl]phenyl)-1,3-dihydro-2H-isoindole-2-carboxamide;
5-fluoro-N-(4-1 [2-(2-thienyl)ethyl]carbamoyl}phenyl)-1,3-dihydro-2H-isoindole-2-carboxamide;
N-(4-{[(2S)-tetrahydrofuran-2-ylmethyl]carbamoyl}phenyl)-1,3-dihydro-2H-isoindole-2-carboxamide;
N-(4-{[1-(3-methylbutyl)-11H-pyrazol-4-yl]carbamoyl}phenyl)-1,3-dihydro-2H-isoindole-2-carboxamide;
N-{4-[(6-aminohexyl)carbamoyl]phenyl}-1,3-dihydro-2H-isoindole-2-carboxamide;
4-chloro-N-{4-[(3-methylbutyl)carbamoyl]phenyl}-1,3-dihydro-2H-isoindole-2-carboxamide;
N-(4-{[2-(2-thienyl)ethyl]carbamoyl}phenyl)-1,3-dihydro-2H-isoindole-2-carboxamide;
N-{4-[(1,3-benzodioxol-5-ylmethyl)carbamoyl]phenyl}-1,3-dihydro-2H-isoindole-2-carboxamide;
N-{4-[(3-methoxybenzyl)carbamoyl]phenyl}-1,3-dihydro-2H-isoindole-2-carboxamide;
N-[4-(benzylcarbamoyl)phenyl]-1,3-dihydro-2H-isoindole-2-carboxamide;

N-{4-[(pyrimidin-4-ylmethyl)carbamoyl]phenyl}-1,3-dihydro-2H-isoindole-2-carboxamide;
N-{4-[(2-methylbutyl)carbamoyl]phenyl}-1,3-dihydro-2H-isoindole-2-carboxamide;
N-{4-[(3-butoxypropyl)carbamoyl]phenyl}-1,3-dihydro-2H-isoindole-2-carboxamide;
N-(4-{[(1S)-2-hydroxy-1-phenylethyl]carbamoyl}phenyl)-1,3-dihydro-2H-isoindole-2-carboxamide;
N-(4-{[2-(3,4-dihydroxyphenyl)ethyl]carbamoyl}phenyl)-1,3-dihydro-2H-isoindole-2-carboxamide;
N-{4-[(3-propoxypropyl)carbamoyl]phenyl}-1,3-dihydro-2H-isoindole-2-carboxamide;
N-{4-[(3-furylmethyl)carbamoyl]phenyl}-1,3-dihydro-2H-isoindole-2-carboxamide;
N-{4-[(3-hydroxy-2-methylphenyl)carbamoyl]phenyl}-1,3-dihydro-2H-isoindole-2-carboxamide;
N-{4-[(3-methylbutyl)carbamoyl]phenyl)}-5-(trifluoromethyl)-1,3-dihydro-2H-isoindole-2-carboxamide;
N-{4-[(3-methyl-1H-indazol-5-yl)carbamoyl]phenyl}-1,3-dihydro-2H-isoindole-2-carboxamide;
N-{4-[(3-ethoxypropyl)carbamoyl]phenyl}-1,3-dihydro-2H-isoindole-2-carboxamide;
N-(4-{[2-(2,5-dimethoxyphenyl)ethyl]carbamoyl}phenyl)-1,3-dihydro-2H-isoindole-2-carboxamide;
N-{4-[(tetrahydrofuran-3-ylmethyl)carbamoyl]phenyl}-1,3-dihydro-2H-isoindole-2-carboxamide;
N-{4-[(1-benzyl-1H-pyrazol-4-yl)carbamoyl]phenyl}-1,3-dihydro-2H-isoindole-2-carboxamide;
methyl 5-({4-[(1,3-dihydro-2H-isoindol-2-ylcarbonyl)amino]benzoyl}amino)-1H-indazole-3-carboxylate;
N-(4-{[2-(2-oxopyrrolidin-1-yl)ethyl]carbamoyl}phenyl)-1,3-dihydro-2H-isoindole-2-carboxamide;
N-{4-[(pyridin-4-ylmethyl)carbamoyl]phenyl}-1,3-dihydro-2H-isoindole-2-carboxamide;
N-(4-{[2-(1H-indol-3-yl)ethyl]carbamoyl}phenyl)-1,3-dihydro-2H-isoindole-2-carboxamide;
N-(4-{[4-(trifluoromethyl)benzyl]carbamoyl}phenyl)-1,3-dihydro-2H-isoindole-2-carboxamide;
N-{4-[(3,5-dimethoxyphenyl)carbamoyl]phenyl}-1,3-dihydro-2H-isoindole-2-carboxamide;
N-{4-[(pyridin-3-ylmethyl)carbamoyl]phenyl}-1,3-dihydro-2H-isoindole-2-carboxamide;
N-[4-(2,3-dihydro-1,4-benzodioxin-6-ylcarbamoyl)phenyl]-1,3-dihydro-2H-isoindole-2-carboxamide;
N-(4-{[2-(5-methoxy-1H-indol-3-yl)ethyl]carbamoyl}phenyl)-1,3-dihydro-2H-isoindole-2-carboxamide;
N-{4-[(3-aminobenzyl)carbamoyl]phenyl}-1,3-dihydro-2H-isoindole-2-carboxamide;
N-(4-{[2-(2-chlorophenyl)ethyl]carbamoyl}phenyl)-1,3-dihydro-2H-isoindole-2-carboxamide;
N-(4-{[(2R)-1-hydroxy-4-methylpentan-2-yl]carbamoyl}phenyl)-1,3-dihydro-2H-isoindole-2-carboxamide;
N-{4-[(2-propoxyethyl)carbamoyl]phenyl}-1,3-dihydro-2H-isoindole-2-carboxamide;
N-{4-[(3-isobutoxypropyl)carbamoyl]phenyl}-1,3-dihydro-2H-isoindole-2-carboxamide;
N-{4-[(3,4,5-trimethoxyphenyl)carbamoyl]phenyl}-1,3-dihydro-2H-isoindole-2-carboxamide;
N-{4-[(4-methylpiperidin-1-yl)carbonyl]phenyl}-1,3-dihydro-2H-isoindole-2-carboxamide;
N-[4-({42-[4-(dimethylamino)phenyl]ethyl}carbamoyl)phenyl]-1,3-dihydro-2H-isoindole-2-carboxamide;
N-(4-{[3-(trifluoromethoxy)benzyl]carbamoyl}phenyl)-1,3-dihydro-2H-isoindole-2-carboxamide;
N-(4-{[(1R)-3-hydroxy-1-phenylpropyl]carbamoyl}phenyl)-1,3-dihydro-2H-isoindole-2-carboxamide;
N-{4-[(3-cyanophenyl)carbamoyl]phenyl)-1,3-dihydro-2H-isoindole-2-carboxamide;
N-{4-[(3-fluoro-4-methoxyphenyl)carbamoyl]phenyl}-1,3-dihydro-2H-isoindole-2-carboxamide;
N-{4-[(2,3-dimethoxyphenyl)carbamoyl]phenyl}-1,3-dihydro-2H-isoindole-2-carboxamide;
N-(4-{[2-(2-fluorophenyl)ethyl]carbamoyl}phenyl)-1,3-dihydro-2H-isoindole-2-carboxamide;
N-[4-(isobutylcarbamoyl)phenyl]-1,3-dihydro-2H-isoindole-2-carboxamide;
N-(4-4 [2-(1,3-benzodioxol-5-yl)ethyl]carbamoyl}phenyl)-1,3-dihydro-2H-isoindole-2-carboxamide;
N-(4-{[2-(2-methoxyphenyl)ethyl]carbamoyl)}phenyl)-1,3-dihydro-2H-isoindole-2-carboxamide;
N-[4-(butylcarbamoyl)phenyl]-1,3-dihydro-2H-isoindole-2-carboxamide;
N-{4-[(2-isopropoxyethyl)carbamoyl]phenyl}-1,3-dihydro-2H-isoindole-2-carboxamide;
N-{4-[(3-isopropoxypropyl)carbamoyl]phenyl}-1,3-dihydro-2H-isoindole-2-carboxamide;
4-chloro-N-{4-[(3-phenylpropyl)carbamoyl]phenyl}-1,3-dihydro-2H-isoindole-2-carboxamide;
N-(4-{[2-(4-methoxyphenyl)ethyl]carbamoyl}phenyl)-1,3-dihydro-2H-isoindole-2-carboxamide;
N-{4-[(3-methoxypropyl)carbamoyl]phenyl}-1,3-dihydro-2H-isoindole-2-carboxamide;
N-(4-{[2-(4-fluorophenyl)ethyl]carbamoyl}phenyl)-1,3-dihydro-2H-isoindole-2-carboxamide;
N-(4-{[3-(2-oxopyrrolidin-1-yl)propyl]carbamoyl}phenyl)-1,3-dihydro-2H-isoindole-2-carboxamide;
N-{4-[(2,4-dimethoxyphenyl)carbamoyl]phenyl}-1,3-dihydro-2H-isoindole-2-carboxamide;
$N^2$-[4-(propylcarbamoyl)phenyl]-1,3-dihydro-2H-isoindole-2,5-dicarboxamide;
N-{4-[(2-phenoxyethyl)carbamoyl]phenyl}-1,3-dihydro-2H-isoindole-2-carboxamide;
N-(4-{[2-(4-hydroxyphenyl)ethyl]carbamoyl}phenyl)-1,3-dihydro-2H-isoindole-2-carboxamide;
N-(4-{[2-(3-fluorophenyl)ethyl]carbamoyl}phenyl)-1,3-dihydro-2H-isoindole-2-carboxamide;
N-[4-(({1-[(3S)-tetrahydrofuran-3-yl]-1H-pyrazol-4-yl}carbamoyl)phenyl]-1,3-dihydro-2H-isoindole-2-carboxamide;
5-methyl-N-{4-[(3-phenylpropyl)carbamoyl]phenyl}-1,3-dihydro-2H-isoindole-2-carboxamide;
N-{4-[(2-phenylethyl)carbamoyl]phenyl}-1,3-dihydro-2H-isoindole-2-carboxamide;
N-(4-{[2-(2,4-dimethoxyphenyl)ethyl]carbamoyl}phenyl)-1,3-dihydro-2H-isoindole-2-carboxamide;
N-(4-{[3-(methylthio)propyl]carbamoyl}phenyl)-1,3-dihydro-2H-isoindole-2-carboxamide;
N-{4-[(2-ethoxyethyl)carbamoyl]phenyl}-1,3-dihydro-2H-isoindole-2-carboxamide;
N-{4-[(2-fluorophenyl)carbamoyl]phenyl}-1,3-dihydro-2H-isoindole-2-carboxamide;
N-(4-{[2-(pyridin-3-yl)ethyl]carbamoyl}phenyl)-1,3-dihydro-2H-isoindole-2-carboxamide;

N-[4-({4-[(trifluoromethyl)thio]benzyl}carbamoyl)phenyl]-1,3-dihydro-2H-isoindole-2-carboxamide;
N-{4-[(3,4-dimethoxyphenyl)carbamoyl]phenyl)-1,3-dihydro-2H-isoindole-2-carboxamide;
N-(4-{[3-(1H-imidazol-1-yl)propyl]carbamoyl}phenyl)-1,3-dihydro-2H-isoindole-2-carboxamide;
N-(4-{[2-(3-chlorophenyl)ethyl]carbamoyl}phenyl)-1,3-dihydro-2H-isoindole-2-carboxamide;
N-{4-[(4-hydroxybutyl)carbamoyl]phenyl}-1,3-dihydro-2H-isoindole-2-carboxamide;
N-{4-[(3-phenylpropyl)carbamoyl]phenyl}-5-(trifluoromethyl)-1,3-dihydro-2H-isoindole-2-carboxamide;
N-(4-{[4-(hydroxymethyl)phenyl]carbamoyl}phenyl)-1,3-dihydro-2H-isoindole-2-carboxamide;
N-[4-(1,3-benzodioxol-5-ylcarbamoyl)phenyl]-1,3-dihydro-2H-isoindole-2-carboxamide;
N-{4-[(1-isopropyl-1H-pyrazol-4-yl)carbamoyl]phenyl}-1,3-dihydro-2H-isoindole-2-carboxamide;
N-{4-[(4-hydroxyphenyl)carbamoyl]phenyl}-1,3-dihydro-2H-isoindole-2-carboxamide;
N-{4-[(1-ethyl- H-pyrazol-4-yl)carbamoyl]phenyl}-1,3-dihydro-2H-isoindole-2-carboxamide;
N-{4-[(2,5-dimethoxyphenyl)carbamoyl]phenyl}-1,3-dihydro-2H-isoindole-2-carboxamide;
N-{4-[(2-hydroxy-2-methylpropyl)carbamoyl]phenyl}-1,3-dihydro-2H-isoindole-2-carboxamide;
N-{4-[(1-benzylpiperidin-4-yl)carbamoyl]phenyl}-1,3-dihydro-2H-isoindole-2-carboxamide;
N-{4-[(4-methoxyphenyl)carbamoyl]phenyl}-1,3-dihydro-2H-isoindole-2-carboxamide;
N-{4-[(3-methoxyphenyl)carbamoyl]phenyl}-1,3-dihydro-2H-isoindole-2-carboxamide;
N-{4-[(5-acetamido-2-methoxyphenyl)carbamoyl]phenyl}-1,3-dihydro-2H-isoindole-2-carboxamide;
N-(4-{[2-(3,5-dimethoxyphenyl)ethyl]carbamoyl}phenyl)-1,3-dihydro-2H-isoindole-2-carboxamide;
N-[4-({2-[3-(trifluoromethyl)phenyl]ethyl}carbamoyl)phenyl]-1,3-dihydro-2H-isoindole-2-carboxamide;
N-{4-[(2-methylbutan-2-yl)carbamoyl]phenyl}-1,3-dihydro-2H-isoindole-2-carboxamide;
N-(4-{[2-(1H-imidazol-4-yl)ethyl]carbamoyl}phenyl)-1,3-dihydro-2H-isoindole-2-carboxamide;
N-(4-{[(2S)-2-hydroxypropyl]carbamoyl}phenyl)-1,3-dihydro-2H-isoindole-2-carboxamide;
N-(4-{[(1R)-1-(3-cyanophenyl)ethyl]carbamoyl}phenyl)-1,3-dihydro-2H-isoindole-2-carboxamide;
N-(4-{[(2S)-1-hydroxy-3-methylbutan-2-yl]carbamoyl}phenyl)-1,3-dihydro-2H-isoindole-2-carboxamide;
N-{4-[(4-cyanophenyl)carbamoyl]phenyl}-1,3-dihydro-2H-isoindole-2-carboxamide;
N-(4-{[2-(4-chlorophenyl)ethyl]carbamoyl}phenyl)-1,3-dihydro-2H-isoindole-2-carboxamide;
N-(4-{[2-(4-methylpiperazin-1-yl)ethyl]carbamoyl}phenyl)-1,3-dihydro-2H-isoindole-2-carboxamide;
N-(4-{[2-(pyridin-2-yl)ethyl]carbamoyl}phenyl)-1,3-dihydro-2H-isoindole-2-carboxamide;
N-[4-(cyanomethyl)carbamoyl]phenyl-1,3-dihydro-2H-isoindole-2-carboxamide;
N-[4-(cyclohexylcarbamoyl)phenyl]-1,3-dihydro-2H-isoindole-2-carboxamide;
N-{4-[(3-hydroxyphenyl)carbamoyl]phenyl}-1,3-dihydro-2H-isoindole-2-carboxamide;
N-(4-([4-(dimethylamino)phenyl]carbamoyl}phenyl)-1,3-dihydro-2H-isoindole-2-carboxamide;
N-[4-(phenylcarbamoyl)phenyl]-1,3-dihydro-2H-isoindole-2-carboxamide;
N-{4-[(4-fluorophenyl)carbamoyl]phenyl}-1,3-dihydro-2H-isoindole-2-carboxamide;
N-(4-{[2-(diethylamino)ethyl]carbamoyl}phenyl)-1,3-dihydro-2H-isoindole-2-carboxamide;
N-{4-[(2-aminophenyl)carbamoyl]phenyl}-1,3-dihydro-2H-isoindole-2-carboxamide;
N-(4-{[(2R)-2-hydroxypropyl]carbamoyl}phenyl)-1,3-dihydro-2H-isoindole-2-carboxamide;
N-(4-{[(2S)-1-amino-4-methyl-1-oxopentan-2-yl]carbamoyl}phenyl)-1,3-dihydro-2H-isoindole-2-carboxamide;
N-(4-{[3-(morpholin-4-yl)propyl]carbamoyl}phenyl)-1,3-dihydro-2H-isoindole-2-carboxamide;
N-(4-{[1-(3-chlorobenzyl)-1H-pyrazol-4-yl]carbamoyl}phenyl)-1,3-dihydro-2H-isoindole-2-carboxamide;
N-(4-{[3-(piperidin-1-yl)propyl]carbamoyl}phenyl)-1,3-dihydro-2H-isoindole-2-carboxamide;
N-{4-[(2-hydroxy-6-methylphenyl)carbamoyl]phenyl}-1,3-dihydro-2H-isoindole-2-carboxamide;
N-(4-{[4-(dimethylamino)butyl]carbamoyl}phenyl)-1,3-dihydro-2H-isoindole-2-carboxamide;
N-{4-[(3-hydroxypropyl)carbamoyl]phenyl}-1,3-dihydro-2H-isoindole-2-carboxamide;
N-[4-(propylcarbamoyl)phenyl]-1,3-dihydro-2H-isoindole-2-carboxamide;
N-(4-{[(2S)-1-hydroxybutan-2-yl]carbamoyl}phenyl)-1,3-dihydro-2H-isoindole-2-carboxamide;
N-{4-[(5-fluoropyridin-2-yl)carbamoyl]phenyl}-1,3-dihydro-2H-isoindole-2-carboxamide;
N-(4-{[(2S)-1-methoxypropan-2-yl]carbamoyl)}phenyl)-1,3-dihydro-2H-isoindole-2-carboxamide;
N-[4-(tert-butylcarbamoyl)phenyl]-1,3-dihydro-2H-isoindole-2-carboxamide;
N-{4-[(3-methylbutan-2-yl)carbamoyl]phenyl}-1,3-dihydro-2H-isoindole-2-carboxamide;
N-(4-([(3S)-1-benzylpyrrolidin-3-yl]carbamoyl J phenyl)-1,3-dihydro-2H-isoindole-2-carboxamide;
N-{4-[(3-fluorophenyl)carbamoyl]phenyl}-1,3-dihydro-2H-isoindole-2-carboxamide;
N-[4-(cyclopentylcarbamoyl)phenyl]-1,3-dihydro-2H-isoindole-2-carboxamide;
N-[4-(cyclopropylcarbamoyl)phenyl]-1,3-dihydro-2H-isoindole-2-carboxamide;
N-[4-(methylcarbamoyl)phenyl]-1,3-dihydro-2H-isoindole-2-carboxamide;
N-(4-{[34(dimethylamino)propyl]carbamoyl}phenyl)-1,3-dihydro-2H-isoindole-2-carboxamide;
N-[4-(pentan-2-ylcarbamoyl)phenyl]-1,3-dihydro-2H-isoindole-2-carboxamide;
N-[4-(pentan-3-ylcarbamoyl)phenyl]-1,3-dihydro-2H-isoindole-2-carboxamide;
N-[4-(cyclobutylcarbamoyl)phenyl]-1,3-dihydro-2H-isoindole-2-carboxamide;
N-(4-{[1-(4-fluorophenyl)-1H-pyrazol-4-yl]carbamoyl}phenyl)-1,3-dihydro-2H-isoindole-2-carboxamide;
N-{4-[(1-hydroxy-2-methylpropan-2-yl)carbamoyl]phenyl}-1,3-dihydro-2H-isoindole-2-carboxamide;
N-{4-[(1-phenyl-1H-pyrazol-4-yl)carbamoyl]phenyl}-1,3-dihydro-2H-isoindole-2-carboxamide;
N-[4-{2-[4-(trifluoromethyl)phenyl]ethyl}carbamoyl)phenyl]-1,3-dihydro-2H-isoindole-2-carboxamide;
N-[4-(sec-butylcarbamoyl)phenyl]-1,3-dihydro-2H-isoindole-2-carboxamide;

N-{4-[(1-methoxypropan-2-yl)carbamoyl]phenyl}-1,3-dihydro-2H-isoindole-2-carboxamide;
N-{4-[(3R)-tetrahydrofuran-3-ylcarbamoyl]phenyl)-1,3-dihydro-2H-isoindole-2-carboxamide;
N-(4-{[(2S)-1-hydroxy-4-methyl pentan-2-yl] carbamoyl}phenyl)-1,3-dihydro-2H-isoindole-2-carboxamide;
N-(4-{[(1R)-2-hydroxy-1-phenylethyl]carbamoyl)}phenyl)-1,3-dihydro-2H-isoindole-2-carboxamide;
N-(4-{[(2R)-1-hydroxy-3-methylbutan-2-yl]carbamoyl}phenyl)-1,3-dihydro-2H-isoindole-2-carboxamide;
N-(4-{[(2R)-1-hydroxybutan-2-yl]carbamoyl)}phenyl)-1,3-dihydro-2H-isoindole-2-carboxamide;
N-[4-(prop-2-yn-1-ylcarbamoyl)phenyl]-1,3-dihydro-2H-isoindole-2-carboxamide;
5,6-dimethoxy-N-{4-[(3-phenylpropyl)carbamoyl]phenyl}-1,3-dihydro-2H-isoindole-2-carboxamide;
N-(4-{[3-(4-chlorophenoxy)propyl]carbamoyl}phenyl)-1,3-dihydro-2H-isoindole-2-carboxamide;
N-(4-{[4-(trifluoromethoxy)phenyl]carbamoyl}phenyl)-1,3-dihydro-2H-isoindole-2-carboxamide;
N-{4-[(4-phenyl-1,3-thiazol-2-yl)carbamoyl]phenyl}-1,3-dihydro-2H-isoindole-2-carboxamide;
methyl 2-{[4-(propylcarbamoyl)phenyl]carbamoyl)}isoindoline-5-carboxylate;
2-{[4-(propylcarbamoyl)phenyl]carbamoyl}isoindoline-5-carboxylic acid;
5-amino-N-[4-(propylcarbamoyl)phenyl]-1,3-dihydro-2H-isoindole-2-carboxamide;
5-(hydroxymethyl)-N-[4-(propylcarbamoyl)phenyl]-1,3-dihydro-2H-isoindole-2-carboxamide;
5-(aminomethyl)-N-[4-(propylcarbamoyl)phenyl]-1,3-dihydro-2H-isoindole-2-carboxamide;
5-[(2-hydroxy-2-methylpropanoyl)amino]-N-[4-(propylcarbamoyl)phenyl]-1,3-dihydro-2H-isoindole-2-carboxamide;
5-acetamido-N-[4-(propylcarbamoyl)phenyl]-1,3-dihydro-2H-isoindole-2-carboxamide;
5-[(N,N-dimethylglycyl)amino]-N-[4-(propylcarbamoyl)phenyl]-1,3-dihydro-2H-isoindole-2-carboxamide;
N-[4-(propylcarbamoyl)phenyl]-5-(1H-pyrazol-3-yl)-1,3-dihydro-2H-isoindole-2-carboxamide;
N-[4-(propylcarbamoyl)phenyl]-5-(11H-pyrazol-4-yl)-1,3-dihydro-2H-isoindole-2-carboxamide;
5-[(methoxyacetyl)amino]-N-[4-(propylcarbamoyl)phenyl]-1,3-dihydro-2H-isoindole-2-carboxamide;
5-[(methylsulfonyl)amino]-N-[4-(propylcarbamoyl)phenyl]-1,3-dihydro-2H-isoindole-2-carboxamide;
5-bromo-N-[4-(propylcarbamoyl)phenyl]-1,3-dihydro-2H-isoindole-2-carboxamide;
5-fluoro-N-[4-(propylcarbamoyl)phenyl]-1,3-dihydro-2H-isoindole-2-carboxamide;
N-(4-{[(3R)-tetrahydrofuran-3-ylmethyl]carbamoyl}phenyl)-1,3-dihydro-2H-isoindole-2-carboxamide;
N-(4-{[(3S)-tetrahydrofuran-3-ylmethyl]carbamoyl}phenyl)-1,3-dihydro-2H-isoindole-2-carboxamide;
N-{4-[(2-methoxyethyl)carbamoyl]phenyl}-1,3-dihydro-2H-isoindole-2-carboxamide;
N-{4-[(5-chloropyridin-2-yl)carbamoyl]phenyl}-1,3-dihydro-2H-isoindole-2-carboxamide;
N-{4-[(3-hydroxy-4-methoxyphenyl)carbamoyl]phenyl}-1,3-dihydro-2H-isoindole-2-carboxamide;
N-{4-[(2,4-dimethoxybenzyl)carbamoyl]phenyl}-1,3-dihydro-2H-isoindole-2-carboxamide;
N-(4-{[4-(2-oxopyrrolidin-1-yl)benzyl]carbamoyl}phenyl)-1,3-dihydro-2H-isoindole-2-carboxamide;
N-(4-{[(1S,2S)-2-hydroxy-2,3-dihydro-11H-inden-1-yl]carbamoyl}phenyl)-1,3-dihydro-2H-isoindole-2-carboxamide;
N-(4-{[(1-hydroxycyclopropyl)methyl]carbamoyl}phenyl)-1,3-dihydro-2H-isoindole-2-carboxamide;
N-{4-[(tetrahydro-2H-pyran-2-ylmethyl)carbamoyl]phenyl}-1,3-dihydro-2H-isoindole-2-carboxamide;
N-{4-[(tetrahydro-2H-pyran-3-ylmethyl)carbamoyl]phenyl}-1,3-dihydro-2H-isoindole-2-carboxamide;
N-{4-[(tetrahydro-2H-pyran-4-ylmethyl)carbamoyl]phenyl}-1,3-dihydro-2H-isoindole-2-carboxamide;
N-[4-(propylcarbamoyl)phenyl]-5-vinyl-1,3-dihydro-2H-isoindole-2-carboxamide;
5-fluoro-N-[4-({[(2S)-tetrahydrofuran-2-ylmethyl]amino}carbonyl)phenyl]-1,3-dihydro-2H-isoindole-2-carboxamide;
5-fluoro-N-[4-({[(2R)-tetrahydrofuran-2-ylmethyl]amino}carbonyl)phenyl]-1,3-dihydro-2H-isoindole-2-carboxamide;
N-{4-[(propylamino)carbonyl]phenyl}-5-pyridin-3-yl-1,3-dihydro-2H-isoindole-2-carboxamide;
N-{4-[(propylamino)carbonyl]phenyl}-5-pyridin-4-yl-1,3-dihydro-2H-isoindole-2-carboxamide;
$N^5$-(2-methoxyethyl)-$N^2$-{4-[(propylamino)carbonyl]phenyl}-1,3-dihydro-2H-isoindole-2,5-dicarboxamide;
N-[4-({[(1S)-2-hydroxy-1-pyridin-2-ylethyl]amino}carbonyl)phenyl]-1,3-dihydro-2H-isoindole-2-carboxamide;
5-(1,2-dihydroxyethyl)-N-{4-[(propylamino)carbonyl]phenyl}-1,3-dihydro-2H-isoindole-2-carboxamide;
N-(4-{[6-(benzoylamino)hexyl]carbamoyl}phenyl)-1,3-dihydro-2H-isoindole-2-carboxamide;
N-[4-({4-[(benzoylamino)methyl]benzyl}carbamoyl)phenyl]-5-fluoro-1,3-dihydro-2H-isoindole-2-carboxamide;
$N^5$-[2-(dimethylamino)ethyl]-$N^2$-[4-(propylcarbamoyl)phenyl]-1,3-dihydro-2H-isoindole-2,5-dicarboxamide;
5-(morpholin-4-ylcarbonyl)-N-[4-(propylcarbamoyl)phenyl]-1,3-dihydro-2H-isoindole-2-carboxamide;
N-[4-(isobutoxycarbamoyl)phenyl]-1,3-dihydro-2H-isoindole-2-carboxamide;
5-fluoro-N-{4-[(tetrahydro-2H-pyran-2-ylmethyl)carbamoyl]phenyl}-1,3-dihydro-2H-isoindole-2-carboxamide;
5-fluoro-N-{4-[(tetrahydro-2H-pyran-3-ylmethyl)carbamoyl]phenyl}-1,3-dihydro-2H-isoindole-2-carboxamide;
5-fluoro-N-{4-[(tetrahydro-2H-pyran-4-ylmethyl)carbamoyl]phenyl}-1,3-dihydro-2H-isoindole-2-carboxamide;
5-fluoro-N-(4-{[(1S)-2-hydroxy-1-phenylethyl]carbamoyl}phenyl)-1,3-dihydro-2H-isoindole-2-carboxamide;
5-fluoro-N-(4-{[(1S)-2-hydroxy-1-(pyridin-2-yl)ethyl]carbamoyl}phenyl)-1,3-dihydro-2H-isoindole-2-carboxamide;
5-fluoro-N-(4-{[(2S)-1-hydroxy-4-methylpentan-2-yl]carbamoyl}phenyl)-1,3-dihydro-2H-isoindole-2-carboxamide;
N-(4-{[(2S)-1-hydroxy-4-(methylthio)butan-2-yl]carbamoyl}phenyl)-1,3-dihydro-2H-isoindole-2-carboxamide;

N-(4-{[(2S,3S)-1-hydroxy-3-methylpentan-2-yl] carbamoyl}phenyl)-1,3-dihydro-2H-isoindole-2-carboxamide;
N-(4-{[(2S)-1-hydroxypropan-2-yl]carbamoyl)phenyl)-1, 3-dihydro-2H-isoindole-2-carboxamide;
N-(4-{[(2S,3R)-1,3-dihydroxybutan-2-yl] carbamoyl}phenyl)-1,3-dihydro-2H-isoindole-2-carboxamide;
N-(4-{[(2S)-1-hydroxyhexan-2-yl]carbamoyl}phenyl)-1, 3-dihydro-2H-isoindole-2-carboxamide;
N-(4-{[(2S)-1-hydroxypentan-2-yl]carbamoyl}phenyl)-1,3-dihydro-2H-isoindole-2-carboxamide;
N-(4-{[(1S,2S)-2-hydroxycyclopentyl] carbamoyl}phenyl)-1,3-dihydro-2H-isoindole-2-carboxamide;
N-(4-([(1S,2R)-2-hydroxycyclopentyl] carbamoyl}phenyl)-1,3-dihydro-2H-isoindole-2-carboxamide;
N-(4-{[(2S)-1-cyclohexyl-3-hydroxypropan-2-yl] carbamoyl}phenyl)-1,3-dihydro-2H-isoindole-2-carboxamide;
N-[4-({(2R)-1-hydroxy-3-[(4-methylbenzyl)thio]propan-2-yl}carbamoyl)phenyl]-1,3-dihydro-2H-isoindole-2-carboxamide;
N-(4-{[(1S)-1-(4-tert-butylphenyl)-2-hydroxyethyl] carbamoyl}phenyl)-1,3-dihydro-2H-isoindole-2-carboxamide;
5-methoxy-N-[4-(propylcarbamoyl)phenyl]-1,3-dihydro-2H-isoindole-2-carboxamide;
5-methyl-N-[4-(propylcarbamoyl)phenyl]-1,3-dihydro-2H-isoindole-2-carboxamide;
5-(hydroxymethyl)-N-{4-[(3-methylbutyl)carbamoyl] phenyl}-1,3-dihydro-2H-isoindole-2-carboxamide;
5-fluoro-N-(4-{[(3R)-tetrahydrofuran-3-ylmethyl] carbamoyl}phenyl)-1,3-dihydro-2H-isoindole-2-carboxamide;
5-fluoro-N-(4-{[(3S)-tetrahydrofuran-3-ylmethyl] carbamoyl}phenyl)-1,3-dihydro-2H-isoindole-2-carboxamide;
N-(4-{[(1-methylpyrrolidin-3-yl)methyl] carbamoyl}phenyl)-1,3-dihydro-2H-isoindole-2-carboxamide;
N-{4-[(pyrrolidin-3-ylmethyl)carbamoyl]phenyl}-1,3-dihydro-2H-isoindole-2-carboxamide;
N-(4-{[(1-methylpiperidin-4-yl)methyl] carbamoyl}phenyl)-1,3-dihydro-2H-isoindole-2-carboxamide;
N-(4-{[(1,1-dioxidotetrahydrothiophen-3-yl)methyl] carbamoyl}phenyl)-1,3-dihydro-2H-isoindole-2-carboxamide;
N-(4-{[(2,2-dimethyl-1,3-dioxolan-4-yl)methyl] carbamoyl}phenyl)-1,3-dihydro-2H-isoindole-2-carboxamide;
N-(4-{[(1S)-2-methoxy-1-phenylethyl] carbamoyl}phenyl)-1,3-dihydro-2H-isoindole-2-carboxamide;
N-[4-({[(4S)-2,2-dimethyl-1,3-dioxolan-4-yl] methyl}carbamoyl)phenyl]-1,3-dihydro-2H-isoindole-2-carboxamide;
N-[4-({[(4R)-2,2-dimethyl-1,3-dioxolan-4-yl] methyl}carbamoyl)phenyl]-1,3-dihydro-2H-isoindole-2-carboxamide;
N-[4-({[3-(hydroxymethyl)oxetan-3-yl] methyl}carbamoyl)phenyl]-1,3-dihydro-2H-isoindole-2-carboxamide;
N-{4-[(2R)-butan-2-ylcarbamoyl]phenyl}-1,3-dihydro-2H-isoindole-2-carboxamide;
N-(4-{[(3-methyloxetan-3-yl)methyl] carbamoyl}phenyl)-1,3-dihydro-2H-isoindole-2-carboxamide;
5-cyano-N-{4-[(cyclopentylmethyl)carbamoyl]phenyl}-1,3-dihydro-2H-isoindole-2-carboxamide;
5-cyano-N-{4-[(1,3-thiazol-5-ylmethyl)carbamoyl]phenyl}-1,3-dihydro-2H-isoindole-2-carboxamide;
5-cyano-N-(4-{[(1R)-3-hydroxy-1-phenylpropyl] carbamoyl}phenyl)-1,3-dihydro-2H-isoindole-2-carboxamide;
5-cyano-N-(4-{[2-hydroxy-1-(4-methylphenyl)ethyl] carbamoyl}phenyl)-1,3-dihydro-2H-isoindole-2-carboxamide;
5-cyano-N-{4-[(1,3-dihydroxypropan-2-yl)carbamoyl] phenyl}-1,3-dihydro-2H-isoindole-2-carboxamide;
5-cyano-N-(4-{[(2R)-2-hydroxypropyl] carbamoyl}phenyl)-1,3-dihydro-2H-isoindole-2-carboxamide;
5-cyano-N-{4-[(2-hydroxy-2-methylpropyl)carbamoyl] phenyl}-1,3-dihydro-2H-isoindole-2-carboxamide;
5-cyano-N4-{[(2R)-1-hydroxy-3-methylbutan-2-yl] carbamoyl}phenyl)-1,3-dihydro-2H-isoindole-2-carboxamide;
5-cyano-N-(4-{[(2S)-tetrahydrofuran-2-ylmethyl]carbamoyl)}phenyl)-1,3-dihydro-2H-isoindole-2-carboxamide;
5-cyano-N-(4-{[2-(4-methylpiperazin-1-yl)ethyl] carbamoyl}phenyl)-1,3-dihydro-2H-isoindole-2-carboxamide;
5-cyano-N4-{[(1S)-2-hydroxy-1-phenylethyl] carbamoyl}phenyl)-1,3-dihydro-2H-isoindole-2-carboxamide;
5-cyano-N-{4-[(4-hydroxybutyl)carbamoyl]phenyl}-1,3-dihydro-2H-isoindole-2-carboxamide;
5-cyano-N-(4-{[(2S)-2-hydroxypropyl] carbamoyl}phenyl)-1,3-dihydro-2H-isoindole-2-carboxamide;
5-cyano-N-{4-[(3-furylmethyl)carbamoyl]phenyl}-1,3-dihydro-2H-isoindole-2-carboxamide;
5-cyano-N-{4-[(tetrahydrofuran-2-ylmethyl)carbamoyl] phenyl}-1,3-dihydro-2H-isoindole-2-carboxamide;
5-cyano-N-(4-{[3-(piperidin-1-yl)propyl] carbamoyl}phenyl)-1,3-dihydro-2H-isoindole-2-carboxamide;
5-cyano-N-(4-{[(2R)-tetrahydrofuran-2-ylmethyl] carbamoyl}phenyl)-1,3-dihydro-2H-isoindole-2-carboxamide;
5-cyano-N-{4-[(tetrahydrofuran-3-ylmethyl)carbamoyl] phenyl}-1,3-dihydro-2H-isoindole-2-carboxamide;
5-cyano-N-(4-{[(1R)-2-hydroxy-1-phenylethyl] carbamoyl}phenyl)-1,3-dihydro-2H-isoindole-2-carboxamide;
5-cyano-N-(4-{[(2S)-1-hydroxybutan-2-yl] carbamoyl}phenyl)-1,3-dihydro-2H-isoindole-2-carboxamide;
5-cyano-N-{4-[(2,3-di hydroxypropyl)carbamoyl]phenyl)-1,3-dihydro-2H-isoindole-2-carboxamide;
5-cyano-N-{4-[(tetrahydro-2H-pyran-4-ylmethyl)carbamoyl]phenyl}-1,3-dihydro-2H-isoindole-2-carboxamide;
5-cyano-N4-{[2-hydroxy-1-(pyridin-2-yl)ethyl] carbamoyl}phenyl)-1,3-dihydro-2H-isoindole-2-carboxamide;
5-cyano-N-{4-[(1-hydroxy-4-methylpentan-2-yl)carbamoyl]phenyl}-1,3-dihydro-2H-isoindole-2-carboxamide;

5-cyano-N-(4-([(1-methylpyrrolidin-3-yl)methyl]carbamoyl}phenyl)-1,3-dihydro-2H-isoindole-2-carboxamide;
5-cyano-N4(4-{[(1-methylpiperidin-4-yl)methyl]carbamoyl}phenyl)-1,3-dihydro-2H-isoindole-2-carboxamide;
5-cyano-N-{4-[(tetrahydro-2H-pyran-3-ylmethyl)carbamoyl]phenyl}-1,3-dihydro-2H-isoindole-2-carboxamide;
N-{4-[(1-oxa-8-azaspiro[4.5]dec-2-ylmethyl)carbamoyl]phenyl}-1,3-dihydro-2H-isoindole-2-carboxamide;
N-[4-(1-oxa-8-azaspiro[4.5]dec-3-ylcarbamoyl)phenyl]-1,3-dihydro-2H-isoindole-2-carboxamide;
N-{4-[(2-oxa-9-azaspiro[5.5]undec-3-ylmethyl)carbamoyl]phenyl}-1,3-dihydro-2H-isoindole-2-carboxamide;
5-fluoro-N-{4-[(1-oxa-8-azaspiro[4.5]dec-2-ylmethyl)carbamoyl]phenyl}-1,3-dihydro-2H-isoindole-2-carboxamide;
5-fluoro-N-[4-(1-oxa-8-azaspiro[4.5]dec-3-ylcarbamoyl)phenyl]-1,3-dihydro-2H-isoindole-2-carboxamide;
N-(4-{[(1S)-1-(4-fluorophenyl)-2-hydroxyethyl]carbamoyl}phenyl)-1,3-dihydro-2H-isoindole-2-carboxamide;
N-(4-{[(1S)-2-hydroxy-1-(4-methoxyphenyl)ethyl]carbamoyl}phenyl)-1,3-dihydro-2H-isoindole-2-carboxamide;
N-(4-([(1S)-1-(1,3-benzodioxol-5-yl)-2-hydroxyethyl]carbamoyl}phenyl)-1,3-dihydro-2H-isoindole-2-carboxamide;
5-fluoro-N-(4-{[1-(1,3-thiazol-2-yl)propan-2-yl]carbamoyl}phenyl)-1,3-dihydro-2H-isoindole-2-carboxamide;
N-{4-[(4,4-difluorocyclohexyl)carbamoyl]phenyl)-5-fluoro-1,3-dihydro-2H-isoindole-2-carboxamide;
N-(4-{[1-(3,5-dimethyl-1H-pyrazol-1-yl)propan-2-yl]carbamoyl}phenyl)-5-fluoro-1,3-dihydro-2H-isoindole-2-carboxamide;
5-fluoro-N-(4-{[2-methyl-2-(morpholin-4-yl)butyl]carbamoyl}phenyl)-1,3-dihydro-2H-isoindole-2-carboxamide;
5-fluoro-N-(4-{[2-(2-methyl-1,3-thiazol-4-yl)ethyl]carbamoyl}phenyl)-1,3-dihydro-2H-isoindole-2-carboxamide;
5-fluoro-N-(4-([2-methyl-1-(morpholin-4-yl)propan-2-yl]carbamoyl}phenyl)-1,3-dihydro-2H-isoindole-2-carboxamide;
5-fluoro-N-{4-[(4-methoxybenzyl)carbamoyl]phenyl}-1,3-dihydro-2H-isoindole-2-carboxamide;
5-fluoro-N-(4-{[3-(morpholin-4-yl)propyl]carbamoyl}phenyl)-1,3-dihydro-2H-isoindole-2-carboxamide;
Nalpha-(4-{[(5-fluoro-1,3-dihydro-2H-isoindol-2-yl)carbonyl]amino}benzoyl)-D-phenylalaninamide;
N-(4-{[2-(acetylamino)phenyl]carbamoyl}phenyl)-5-fluoro-1,3-dihydro-2H-isoindole-2-carboxamide;
5-fluoro-N-(4-{[2-(furan-2-yl)-2-(pyrrolidin-1-yl)ethyl]carbamoyl}phenyl)-1,3-dihydro-2H-isoindole-2-carboxamide;
N-{4-[(1-amino-1-oxohexan-2-yl)carbamoyl]phenyl}-5-fluoro-1,3-dihydro-2H-isoindole-2-carboxamide;
N-(4-{[2-(3,4-dimethoxyphenyl)ethyl]carbamoyl}phenyl)-5-fluoro-1,3-dihydro-2H-isoindole-2-carboxamide;
N-(4-{[(2S)-3,3-dimethyl-1-(methylamino)-1-oxobutan-2-yl]carbamoyl}phenyl)-5-fluoro-1,3-dihydro-2H-isoindole-2-carboxamide;
Nalpha-(4-{[(5-fluoro-1,3-dihydro-2H-isoindol-2-yl)carbonyl]amino}benzoyl)-L-phenylalaninamide;
N-(4-{[(2R)-1-amino-4-methyl-1-oxopentan-2-yl]carbamoyl}phenyl)-5-fluoro-1,3-dihydro-2H-isoindole-2-carboxamide;
5-fluoro-N-(4-{[3-(methylcarbamoyl)phenyl]carbamoyl}phenyl)-1,3-dihydro-2H-isoindole-2-carboxamide;
N-{4-[(2-amino-2-oxo-1-phenylethyl)carbamoyl]phenyl}-5-fluoro-1,3-dihydro-2H-isoindole-2-carboxamide;
N-{4-[(3-tert-butoxypropyl)carbamoyl]phenyl}-5-fluoro-1,3-dihydro-2H-isoindole-2-carboxamide;
N-(4-{[2-(2,6-dimethylmorpholin-4-yl)ethyl]carbamoyl}phenyl)-5-fluoro-1,3-dihydro-2H-isoindole-2-carboxamide;
N-(4-{[(1R)-2-amino-2-oxo-1-phenylethyl]carbamoyl}phenyl)-5-fluoro-1,3-dihydro-2H-isoindole-2-carboxamide;
5-fluoro-N-{4-[(3-methoxybenzyl)carbamoyl]phenyl}-1,3-dihydro-2H-isoindole-2-carboxamide;
N-(4-{[2-(3,5-dimethyl-1H-pyrazol-1-yl)ethyl]carbamoyl}phenyl)-5-fluoro-1,3-dihydro-2H-isoindole-2-carboxamide;
5-fluoro-N-(4-{[2-methyl-2-(morpholin-4-yl)propyl]carbamoyl}phenyl)-1,3-dihydro-2H-isoindole-2-carboxamide;
5-fluoro-N-(4-{[(3S)-1-methyl-2-oxoazepan-3-yl]carbamoyl}phenyl)-1,3-dihydro-2H-isoindole-2-carboxamide;
5-fluoro-N-(4-{[2-(4-methylpiperazin-1-yl)ethyl]carbamoyl}phenyl)-1,3-dihydro-2H-isoindole-2-carboxamide;
5-fluoro-N-(4-{[4-(morpholin-4-yl)benzyl]carbamoyl}phenyl)-1,3-dihydro-2H-isoindole-2-carboxamide;
5-fluoro-N-(4-[3-(piperidin-1-yl)propyl]carbamoyl}phenyl)-1,3-dihydro-2H-isoindole-2-carboxamide;
5-fluoro-N-{4-[(3-methoxy-2,2-dimethylpropyl)carbamoyl]phenyl}-1,3-dihydro-2H-isoindole-2-carboxamide;
N-{4-[(3,3-dimethylbutyl)carbamoyl]phenyl}-5-fluoro-1,3-dihydro-2H-isoindole-2-carboxamide;
5-fluoro-N-(4-{[1-(furan-2-yl)propan-2-yl]carbamoyl}phenyl)-1,3-dihydro-2H-isoindole-2-carboxamide;
5-fluoro-N-(4-{[(3-methyl-1,2-oxazol-5-yl)methyl]carbamoyl}phenyl)-1,3-dihydro-2H-isoindole-2-carboxamide;
N-(4-{[(2R)-1-cyanobutan-2-yl]carbamoyl}phenyl)-5-fluoro-1,3-dihydro-2H-isoindole-2-carboxamide;
N-{4-[(2R)-butan-2-ylcarbamoyl]phenyl}-5-fluoro-1,3-dihydro-2H-isoindole-2-carboxamide;
5-fluoro-N-(4-{[2-(1H-pyrazol-1-yl)ethyl]carbamoyl}phenyl)-1,3-dihydro-2H-isoindole-2-carboxamide;
N-(4-{[1-(ethylamino)-1-oxopropan-2-yl]carbamoyl}phenyl)-5-fluoro-1,3-dihydro-2H-isoindole-2-carboxamide;
5-fluoro-N-(4-{[(1-methyl-1H-pyrazol-3-yl)methyl]carbamoyl}phenyl)-1,3-dihydro-2H-isoindole-2-carboxamide;
5-fluoro-N-{4-[(2-methoxybutyl)carbamoyl]phenyl}-1,3-dihydro-2H-isoindole-2-carboxamide;
N-(4-{[4-(dimethylamino)butyl]carbamoyl}phenyl)-5-fluoro-1,3-dihydro-2H-isoindole-2-carboxamide;
5-fluoro-N-{4-[(3S)-tetrahydrofuran-3-ylcarbamoyl]phenyl}-1,3-dihydro-2H-isoindole-2-carboxamide;
5-fluoro-N-{4-[(1-methoxybutan-2-yl)carbamoyl]phenyl}-1,3-dihydro-2H-isoindole-2-carboxamide;

N-{4-[(2-ethoxypropyl)carbamoyl]phenyl)}-5-fluoro-1,3-dihydro-2H-isoindole-2-carboxamide;
N-{4-[(2S)-butan-2-ylcarbamoyl]phenyl}-5-fluoro-1,3-dihydro-2H-isoindole-2-carboxamide;
5-fluoro-N-(4-{[2-(5-methyl-1H-pyrazol-1-yl)ethyl]carbamoyl}phenyl)-1,3-dihydro-2H-isoindole-2-carboxamide;
5-fluoro-N-(4-{[2-(3-methyl-1H-pyrazol-1-yl)ethyl]carbamoyl}phenyl)-1,3-dihydro-2H-isoindole-2-carboxamide;
5-fluoro-N-{4-[(2-methylpropyl)carbamoyl]phenyl}-1,3-dihydro-2H-isoindole-2-carboxamide;
5-fluoro-N-{4-[(pyridin-3-ylmethyl)carbamoyl]phenyl}-1,3-dihydro-2H-isoindole-2-carboxamide;
5-fluoro-N-{4-[(tetrahydrofuran-2-ylmethyl)carbamoyl]phenyl}-1,3-dihydro-2H-isoindole-2-carboxamide;
N-(4-{[(1R)-1-cyclopropylethyl]carbamoyl)}phenyl)-5-fluoro-1,3-dihydro-2H-isoindole-2-carboxamide;
5-fluoro-N-(4-([1-(1-methylcyclopropyl)ethyl]carbamoyl)phenyl)-1,3-dihydro-2H-isoindole-2-carboxamide;
5-fluoro-N-{4-[(thiophen-2-ylmethyl)carbamoyl]phenyl}-1,3-dihydro-2H-isoindole-2-carboxamide;
N-(4-{[(1S)-1-cyclopropylethyl]carbamoyl}phenyl)-5-fluoro-1,3-dihydro-2H-isoindole-2-carboxamide;
5-fluoro-N-{4-[(4-methoxybutyl)carbamoyl]phenyl}-1,3-dihydro-2H-isoindole-2-carboxamide;
5-fluoro-N-(4-([(5-methyl-1,3-oxazol-2-yl)methyl]carbamoyl}phenyl)-1,3-dihydro-2H-isoindole-2-carboxamide;
5-fluoro-N-(4-{[2-(tetrahydro-2H-pyran-3-yl)ethyl]carbamoyl}phenyl)-1,3-dihydro-2H-isoindole-2-carboxamide;
5-fluoro-N-(4-{[(2S)-1-methoxypropan-2-yl]carbamoyl}phenyl)-1,3-dihydro-2H-isoindole-2-carboxamide;
N-{4-[(3,3-dimethyl-2-oxobutyl)carbamoyl]phenyl}-5-fluoro-1,3-dihydro-2H-isoindole-2-carboxamide;
5-fluoro-N-(4-{[(1-methyl-1H-pyrrol-2-yl)methyl]carbamoyl}phenyl)-1,3-dihydro-2H-isoindole-2-carboxamide;
5-fluoro-N-(4-{[2-(propan-2-yloxy)ethyl]carbamoyl}phenyl)-1,3-dihydro-2H-isoindole-2-carboxamide;
N-(4-{[3-(di methylamino)propyl]carbamoyl}phenyl)-5-fluoro-1,3-dihydro-2H-isoindole-2-carboxamide;
N-(4-{[(2S)-1-amino-1-oxobutan-2-yl]carbamoyl}phenyl)-5-fluoro-1,3-dihydro-2H-isoindole-2-carboxamide;
5-fluoro-N-[4-(tetrahydro-2H-pyran-3-ylcarbamoyl)phenyl]-1,3-dihydro-2H-isoindole-2-carboxamide;
5-fluoro-N-(4-{[2-(11H-pyrrol-1-yl)ethyl]carbamoyl}phenyl)-1,3-dihydro-2H-isoindole-2-carboxamide;
5-fluoro-N-{4-[(1-methoxypropan-2-yl)carbamoyl]phenyl}-1,3-dihydro2H-isoindole-2-carboxamide;
5-fluoro-N-{4-[(2-methoxyethyl)carbamoyl]phenyl}-1,3-dihydro-2H-isoindole-2-carboxamide;
N-[4-(cyclopentylcarbamoyl)phenyl]-5-fluoro-1,3-dihydro-2H-isoindole-2-carboxamide;
5-fluoro-N-(4-{[(2S)-3-methylbutan-2-yl]carbamoyl}phenyl)-1,3-dihydro-2H-isoindole-2-carboxamide;
5-fluoro-N-(4-{[(2R)-3-methylbutan-2-yl]carbamoyl}phenyl)-1,3-dihydro-2H-isoindole-2-carboxamide;
5-fluoro-N-(4-{[(2S)-2-methylbutyl]carbamoyl}phenyl)-1,3-dihydro-2H-isoindole-2-carboxamide;
5-fluoro-N-{4-[(2-hydroxy-2-methylpropyl)carbamoyl]phenyl}-1,3-dihydro-2H-isoindole-2-carboxamide;
5-fluoro-N-(4-{[2-(tetrahydro-2H-pyran-4-yl)ethyl]carbamoyl}phenyl)-1,3-dihydro-2H-isoindole-2-carboxamide;
N-[4-(butylcarbamoyl)phenyl]-5-fluoro-1,3-dihydro-2H-isoindole-2-carboxamide;
N-{4-[(1-cyanoethyl)carbamoyl]phenyl}-5-fluoro-1,3-dihydro-2H-isoindole-2-carboxamide;
5-fluoro-N-(4-{[(5-methyl-1,2-oxazol-3-yl)methyl]carbamoyl}phenyl)-1,3-dihydro-2H-isoindole-2-carboxamide;
5-fluoro-N-{4-[(3R)-tetrahydrofuran-3-ylcarbamoyl]phenyl}-1,3-dihydro-2H-isoindole-2-carboxamide;
N-{4-[(3-methoxy-2,2-dimethylpropyl)carbamoyl]phenyl}-1,3-dihydro-2H-isoindole-2-carboxamide;
N-{4-[(4,4-difluorocyclohexyl)carbamoyl]phenyl}-1,3-dihydro-2H-isoindole-2-carboxamide;
N-(4-{[(2R)-1-cyanobutan-2-yl]carbamoyl}phenyl)-1,3-dihydro-2H-isoindole-2-carboxamide;
N-{4-[(2-methoxybutyl)carbamoyl]phenyl}-1,3-dihydro-2H-isoindole-2-carboxamide;
N-(4-{[1-(ethylamino)-1-oxopropan-2-yl]carbamoyl}phenyl)-1,3-dihydro-2H-isoindole-2-carboxamide;
N-(4-{[(1R)-1-cyclopropylethyl]carbamoyl}phenyl)-1,3-dihydro-2H-isoindole-2-carboxamide;
N-(4-{[(1S)-1-cyclopropylethyl]carbamoyl}phenyl)-1,3-dihydro-2H-isoindole-2-carboxamide;
N-{4-[(3S)-tetrahydrofuran-3-ylcarbamoyl]phenyl}-1,3-dihydro-2H-isoindole-2-carboxamide;
N-(4-{[2-(tetrahydro-2H-pyran-3-yl)ethyl]carbamoyl}phenyl)-1,3-dihydro-2H-isoindole-2-carboxamide;
N-(4-{[(5-methyl-1,3-oxazol-2-yl)methyl]carbamoyl}phenyl)-1,3-dihydro-2H-isoindole-2-carboxamide;
N-[4-({2-[(dimethylamino)methyl]benzyl}carbamoyl)phenyl]-1,3-dihydro-2H-isoindole-2-carboxamide;
N-(4-{[(1R)-2-amino-2-oxo-1-phenylethyl]carbamoyl}phenyl)-1,3-dihydro-2H-isoindole-2-carboxamide;
N-[4-(1,3-oxazol-2-ylcarbamoyl)phenyl]-1,3-dihydro-2H-isoindole-2-carboxamide;
N-[4-(tetrahydro-2H-pyran-3-ylcarbamoyl)phenyl]-1,3-dihydro-2H-isoindole-2-carboxamide;
N-(4-{[2-(2,6-dimethylmorpholin-4-yl)ethyl]carbamoyl}phenyl)-1,3-dihydro-2H-isoindole-2-carboxamide;
N-(4-{[1-(1-methylcyclopropyl)ethyl]carbamoyl}phenyl)-1,3-dihydro-2H-isoindole-2-carboxamide;
N-(4-{[2-(furan-2-yl)-2-(pyrrolidin-1-yl)ethyl]carbamoyl}phenyl)-1,3-dihydro-2H-isoindole-2-carboxamide;
N-(4-([3-(3,5-dimethyl-1H-pyrazol-1-yl)propyl]carbamoyl)phenyl)-1,3-dihydro-2H-isoindole-2-carboxamide;
N-(4-1{[(3S)-1-methyl-2-oxoazepan-3-yl]carbamoyl}phenyl)-1,3-dihydro-2H-isoindole-2-carboxamide;
N-(4-{[2-(1H-pyrazol-1-yl)ethyl]carbamoyl}phenyl)-1,3-dihydro-2H-isoindole-2-carboxamide;
N-(4-{[1-(1,3-thiazol-2-yl)ethyl]carbamoyl}phenyl)-1,3-dihydro-2H-isoindole-2-carboxamide;
N-(4-{[1-(furan-2-yl)propan-2-yl]carbamoyl}phenyl)-1,3-dihydro-2H-isoindole-2-carboxamide;

N-(4-{[1-(1-methyl-1H-pyrazol-4-yl)ethyl]
carbamoyl}phenyl)-1,3-dihydro-2H-isoindole-2-carboxamide;
N-(4-{[(2R)-1-amino-4-methyl-1-oxopentan-2-yl]
carbamoyl}phenyl)-1,3-dihydro-2H-isoindole-2-carboxamide;
N-(4-{[1-(3,5-dimethyl-1H-pyrazol-1-yl)propan-2-yl]
carbamoyl}phenyl)-1,3-dihydro-2H-isoindole-2-carboxamide;
N-{4-[(2,2-difluoroethyl)carbamoyl]phenyl}-1,3-dihydro-2H-isoindole-2-carboxamide;
N-(4-{[2-(tetrahydro-2H-pyran-4-yl)ethyl]
carbamoyl}phenyl)-1,3-dihydro-2H-isoindole-2-carboxamide;
N-{4-[(tetrahydrofuran-2-ylmethyl)carbamoyl]phenyl}-1,3-dihydro-2H-isoindole-2-carboxamide;
N-{4-[(2-methoxy-2-methylpropyl)carbamoyl]phenyl}-1,3-dihydro-2H-isoindole-2-carboxamide;
N-(4-{[(5-methyl-1,2-oxazol-3-yl)methyl]
carbamoyl}phenyl)-1,3-dihydro-2H-isoindole-2-carboxamide;
N-(4-({[(1-methyl-1H-pyrazol-4-yl)methyl]
carbamoyl}phenyl)-1,3-dihydro-2H-isoindole-2-carboxamide;
N-(4-{[2-(3,5-dimethyl-1H-pyrazol-1-yl)ethyl]
carbamoyl}phenyl)-1,3-dihydro-2H-isoindole-2-carboxamide;
Nalpha-{4-[(1,3-dihydro-2H-isoindol-2-ylcarbonyl)
amino]benzoyl}-L-phenylalaninamide;
N-(4-{[2-(2-methyl-1,3-thiazol-4-yl)ethyl]
carbamoyl}phenyl)-1,3-dihydro-2H-isoindole-2-carboxamide;
N-(4-{[(2S)-3,3-dimethyl-1-(methylamino)-1-oxobutan-2-yl]carbamoyl)phenyl}-1,3-dihydro-2H-isoindole-2-carboxamide;
N-[4-(thiophen-3-ylcarbamoyl)phenyl]-1,3-dihydro-2H-isoindole-2-carboxamide;
N-(4-{[2-(5-methyl-1H-pyrazol-1-yl)ethyl]
carbamoyl}phenyl)-1,3-dihydro-2H-isoindole-2-carboxamide;
N-(4-{[2-(3-methyl-1H-pyrazol-1-yl)ethyl]
carbamoyl}phenyl)-1,3-dihydro-2H-isoindole-2-carboxamide;
N-{4-[(2S)-butan-2-ylcarbamoyl]phenyl}-1,3-dihydro-2H-isoindole-2-carboxamide;
N-{4-[(3,3-dimethyl-2-oxobutyl)carbamoyl]phenyl}-1,3-dihydro-2H-isoindole-2-carboxamide;
N-(4-{[(1-methyl-1H-pyrazol-3-yl)methyl]
carbamoyl}phenyl)-1,3-dihydro-2H-isoindole-2-carboxamide;
N-(4-{[2-(acetylamino)phenyl]carbamoyl}phenyl)-1,3-dihydro-2H-isoindole-2-carboxamide;
N-{4-[(1-methoxybutan-2-yl)carbamoyl]phenyl}-1,3-dihydro-2H-isoindole-2-carboxamide;
N-[4-(tetrahydro-2H-pyran-4-ylcarbamoyl)phenyl]-1,3-dihydro-2H-isoindole-2-carboxamide;
N-[4-(pyrimidin-4-ylcarbamoyl)phenyl]-1,3-dihydro-2H-isoindole-2-carboxamide;
N-(4-{[2-(1H-pyrrol-1-yl)ethyl]carbamoyl}phenyl)-1,3-dihydro-2H-isoindole-2-carboxamide;
N-(4-{[(2S)-2-methylbutyl]carbamoyl phenyl}-1,3-dihydro-2H-isoindole-2-carboxamide;
N-{4-[(1-amino-1-oxohexan-2-yl)carbamoyl]phenyl}-1,3-dihydro-2H-isoindole-2-carboxamide;
N-{4-[(2-amino-2-oxo-1-phenylethyl)carbamoyl]phenyl}-1,3-dihydro-2H-isoindole-2-carboxamide;
N-{4-[(3-tert-butoxypropyl)carbamoyl]phenyl}-1,3-dihydro-2H-isoindole-2-carboxamide;
N-(4-{[3-(methylcarbamoyl)phenyl]carbamoyl}phenyl)-1,3-dihydro-2H-isoindole-2-carboxamide;
N-(4-{[(2R)-3-methylbutan-2-yl]carbamoyl}phenyl)-1,3-dihydro-2H-isoindole-2-carboxamide;
N-(4-{[(2S)-3-methylbutan-2-yl]carbamoyl}phenyl)-1,3-dihydro-2H-isoindole-2-carboxamide;
N-(4-{[2-methyl-1-(morpholin-4-yl)propan-2-yl]
carbamoyl}phenyl)-1,3-dihydro-2H-isoindole-2-carboxamide;
N-(4-{[2-methyl-2-(morpholin-4-yl)propyl]
carbamoyl}phenyl)-1,3-dihydro-2H-isoindole-2-carboxamide;
N-{4-[(2-ethoxypropyl)carbamoyl]phenyl}-1,3-dihydro-2H-isoindole-2-carboxamide;
or a pharmaceutically acceptable salt thereof.

20. The compound of claim 3, selected from the group consisting of:
tert-butyl 4-{4-[(1,3-dihydro-2H-isoindol-2-ylcarbonyl)amino]phenyl}-3,6-dihydropyridine-1(2H)-carboxylate;
N-[4-(1-butyryl-1,2,3,6-tetrahydropyridin-4-yl)phenyl]-1,3-dihydro-2H-isoindole-2-carboxamide;
N-[4-(1-isobutyryl-1,2,3,6-tetrahydropyridin-4-yl)phenyl]-1,3-dihydro-2H-isoindole-2-carboxamide;
N-[4-(1-benzoyl-1,2,3,6-tetrahydropyridin-4-yl)phenyl]-1,3-dihydro-2H-isoindole-2-carboxamide;
tert-butyl 4-{4-[(1,3-dihydro-2H-isoindol-2-ylcarbonyl)amino]phenyl}piperidine-1-carboxylate;
N-[4-(1-butyrylpiperidin-4-yl)phenyl]-1,3-dihydro-2H-isoindole-2-carboxamide;
N-[4-(1-isobutyrylpiperidin-4-yl)phenyl]-1,3-dihydro-2H-isoindole-2-carboxamide;
N-[4-(1-benzoylpiperidin-4-yl)phenyl]-1,3-dihydro-2H-isoindole-2-carboxamide;
N-{4-[1-(4-methylbenzoyl)-1,2,3,6-tetrahiydropyridin-4-yl]phenyl}-1,3-dihydro-2H-isoindole-2-carboxamide;
N-{4-[1-(5-oxo-L-prolyl)-1,2,3,6-tetrahydropyridin-4-yl]phenyl}-1,3-dihydro-2H-isoindole-2-carboxamide;
N-{4-[1-(5-oxo-D-prolyl)-1,2,3,6-tetrahydropyridin-4-yl]phenyl}-1,3-dihydro-2H-isoindole-2-carboxamide;
N-[4-(1-propionyl-1,2,3,6-tetrahydropyridin-4-yl)phenyl]-1,3-dihydro-2H-isoindole-2-carboxamide;
N-{4-[1-(2-methylbutanoyl)-1,2,3,6-tetrahydropyridin-4-yl]phenyl}-1,3-dihydro-2H-isoindole-2-carboxamide;
N-{4-[1-(2-ethylbutanoyl)-1,2,3,6-tetrahydropyridin-4-yl]phenyl}-1,3-dihydro-2H-isoindole-2-carboxamide;
N-{4-[1-(ethoxyacetyl)-1,2,3,6-tetrahydropyridin-4-yl]phenyl}-1,3-dihydro-2H-isoindole-2-carboxamide;
N-(4-{1-[(2-methoxyethoxy)acetyl]-1,2,3,6-tetrahydropyridin-4-yl}phenyl)-1,3-dihydro-2H-isoindole-2-carboxamide;
N-{4-[1-(tetrahydrofuran-2-ylcarbonyl)-1,2,3,6-tetrahydropyridin-4-yl]phenyl}1,3 -dihydro-2H-isoindole-2-carboxamide;
N-{4-[1-(tetrahydrofuran-3-ylcarbonyl)-1,2,3,6-tetrahydropyridin-4-yl]phenyl}-1,3-dihydro-2H-isoindole-2-carboxamide;
N-{4-[1-(cyclopropylacetyl)-1,2,3,6-tetrahydropyridin-4-yl]phenyl}-1,3-dihydro-2H-isoindole-2-carboxamide;
N-{4-[1-(cyclopentylcarbonyl)-1,2,3,6-tetrahydropyridin-4-yl]phenyl}-1,3-dihydro-2H-isoindole-2-carboxamide;
N-{4-[1-(2-methylbenzoyl)-1,2,3,6-tetrahydropyridin-4-yl]phenyl)}-1,3-dihydro-2H-isoindole-2-carboxamide;

N-{4-[1-(3-methylbenzoyl)-1,2,3,6-tetrahydropyridin-4-yl]phenyl}-1,3-dihydro-2-isoindole-2-carboxamide;
N-{4-[1-(2-methoxybenzoyl)-1,2,3,6-tetrahydropyridin-4-yl]phenyl}-1,3-dihydro-2H-isoindole-2-carboxamide;
N-{4-[1-(3-methoxybenzoyl)-1,2,3,6-tetrahydropyridin-4-yl]phenyl}-1,3-dihydro-2H-isoindole-2-carboxamide;
N-{4-[1-(4-methoxybenzoyl)-1,2,3,6-tetrahydropyridin-4-yl]phenyl}-1,3-dihydro-2H-isoindole-2-carboxamide;
N-{4-[1-(2-fluorobenzoyl)-1,2,3,6-tetrahydropyridin-4-yl]phenyl)}-1,3-dihydro-2H-isoindole-2-carboxamide;
N-{4-[1-(3-fluorobenzoyl)-1,2,3,6-tetrahydropyridin-4-yl]phenyl}-1,3-dihydro-2H-isoindole-2-carboxamide;
N-{4-[1-(4-fluorobenzoyl)-1,2,3,6-tetrahydropyridin-4-yl]phenyl}-1,3-dihydro-2H-isoindole-2-carboxamide;
N-{4-[1-(4-chlorobenzoyl)-1,2,3,6-tetrahydropyridin-4-yl]phenyl}-1,3-dihydro-2H-isoindole-2-carboxamide;
N-(4-{1-[3-(dimethylamino)benzoyl]-1,2,3,6-tetrahydropyridin-4-yl}phenyl)-1,3-dihydro-2H-isoindole-2-carboxamide;
N-(4-{1-[4-(dimethylamino)benzoyl]-1,2,3,6-tetrahydropyridin-4-yl}phenyl)-1,3-dihydro-2H-isoindole-2-carboxamide;
N-{4-[1-(3-thienylcarbonyl)-1,2,3,6-tetrahydropyridin-4-yl]phenyl}-1,3-dihydro-2H-isoindole-2-carboxamide;
N-{4-[1-(1H-pyrrol-2-ylcarbonyl)-1,2,3,6-tetrahydropyridin-4-yl]phenyl}-1,3-dihydro-2H-isoindole-2-carboxamide;
N-(4-{1-[(2,5-dimethyl-1H-pyrrol-3-yl)carbonyl]-1,2,3,6-tetrahydropyridin-4-yl}phenyl)-1,3-dihydro-2H-isoindole-2-carboxamide;
N-{4-[1-(1,3-thiazol-4-ylcarbonyl)-1,2,3,6-tetrahydropyridin-4-yl]phenyl}-1,3-dihydro-2H-isoindole-2-carboxamide;
N-{4-[1-(1H-pyrazol-4-ylcarbonyl)-1,2,3,6-tetrahydropyridin-4-yl]phenyl}-1,3-dihydro-2H-isoindole-2-carboxamide;
N-(4-{1-[(3,5-dimethyl-1,2-oxazol-4-yl)carbonyl]-1,2,3,6-tetrahydropyridin-4-yl}phenyl)-1,3-dihydro-2H-isoindole-2-carboxamide;
N-{4-[1-(pyridin-2-ylcarbonyl)-1,2,3,6-tetrahydropyridin-4-yl]phenyl}-1,3-dihydro-2H-isoindole-2-carboxamide;
N-{4-[1-(pyridin-3-ylcarbonyl)-1,2,3,6-tetrahydropyridin-4-yl]phenyl}-1,3-dihydro-2H-isoindole-2-carboxamide;
N-[4-(1-isonicotinoyl-1,2,3,6-tetrahydropyridin-4-yl)phenyl]-1,3-dihydro-2H-isoindole-2-carboxamide;
N-{4-[1-(pyridazin-3-ylcarbonyl)-1,2,3,6-tetrahydropyridin-4-yl]phenyl}-1,3-dihydro-2H-isoindole-2-carboxamide;
N-{4-[1-(pyrazin-2-ylcarbonyl)-1,2,3,6-tetrahydropyridin-4-yl]phenyl}-1,3-dihydro-2H-isoindole-2-carboxamide;
N-{4-[1-(pyrimidin-4-ylcarbonyl)-1,2,3,6-tetrahydropyridin-4-yl]phenyl}-1,3-dihydro-2H-isoindole-2-carboxamide;
N-(4-{1-[3-(piperidin-1-yl)propanoyl]-1,2,3,6-tetrahydropyridin-4-yl}phenyl)-1,3-dihydro-2H-isoindole-2-carboxamide;
N-{4-[1-(morpholin-4-ylacetyl)-1,2,3,6-tetrahydropyridin-4-yl]phenyl}-1,3-dihydro-2H-isoindole-2-carboxamide;
N-(4-{1-[(4-methylpiperazin-1-yl)acetyl]-1,2,3,6-tetrahydropyridin-4-yl}phenyl)-1,3-dihydro-2H-isoindole-2-carboxamide;
N-(4-{1-[(2-methoxyethoxy)acetyl]piperidin-4-yl}phenyl)-1,3-dihydro-2H-isoindole-2-carboxamide;
N-{4-[1-(tetrahydro-2H-pyran-4-ylcarbonyl)-1,2,3,6-tetrahydropyridin-4-yl]phenyl}-1,3-dihydro-2H-isoindole-2-carboxamide;
N-{4-[1-(1,4-dioxan-2-ylcarbonyl)-1,2,3,6-tetrahydropyridin-4-yl]phenyl}-1,3-dihydro-2H-isoindole-2-carboxamide;
N-(4-{1-[(1-methylpyrrolidin-3-yl)carbonyl]-1,2,3,6-tetrahydropyridin-4-yl}phenyl)-1,3-dihydro-2H-isoindole-2-carboxamide;
N-(4-{1-[(1,1-dioxidotetrahydrothiophen-3-yl)carbonyl]-1,2,3,6-tetrahydropyridin-4-yl}phenyl)-1,3-dihydro-2H-isoindole-2-carboxamide;
N-{4-[1-(2-hydroxy-2-methylpropanoyl)-1,2,3,6-tetrahydropyridin-4-yl]phenyl}-1,3-dihydro-2H-isoindole-2-carboxamide;
N-{4-[1-(tetrahydrofuran-3-ylcarbonyl)piperidin-4-yl]phenyl)}-1,3-dihydro-2H-isoindole-2-carboxamide;
N-{4-[1-(tetrahydrofuran-2-ylcarbonyl)piperidin-4-yl]phenyl)-1,3-dihydro-2H-isoindole-2-carboxamide;
N-{4-[1-(tetrahydro-2H-pyran-4-ylcarbonyl)piperidin-4-yl]phenyl}-1,3-dihydro-2H-isoindole-2-carboxamide;
N-{4-[1-(1,4-dioxan-2-ylcarbonyl)piperidin-4-yl]phenyl}-1,3-dihydro-2H-isoindole-2-carboxamide;
N-(4-{1-[(1-methylpyrrolidin-3-yl)carbonyl]piperidin-4-yl}phenyl)-1,3-dihydro-2H-isoindole-2-carboxamide;
N-(4-{1-[(1,1-dioxidotetrahydrothiophen-3-yl)carbonyl]piperidin-4-yl}phenyl)-1,3-dihydro-2H-isoindole-2-carboxamide;
N-{4-[1-(2-hydroxy-2-methylpropanoyl)piperidin-4-yl]phenyl}-1,3-dihydro-2H-isoindole-2-carboxamide;
N-{4-[1-(morpholin-4-ylacetyl)piperidin-4-yl]phenyl}-1,3-dihydro-2H-isoindole-2-carboxamide;
5-cyano-N-{4-[1-(2-methylpropanoyl)-1,2,3,6-tetrahydropyridin-4-yl]phenyl}-1,3-dihydro-2H-isoindole-2-carboxamide;
5-cyano-N-{4-[1-(tetrahydrofuran-3-ylcarbonyl)-1,2,3,6-tetrahydropyridin-4-yl]phenyl}-1,3-dihydro-2H-isoindole-2-carboxamide;
5-cyano-N-{4-[1-(tetrahydro-2H-pyran-4-ylcarbonyl)-1,2,3,6-tetrahydropyridin-4-yl]phenyl}-1,3-dihydro-2H-isoindole-2-carboxamide;
5-cyano-N-(4-[1-(2-hydroxy-2-methylpropanoyl)-1 2,3,6-tetrahydropyridin-4-yl]phenyl}-1,3-dihydro-2H-isoindole-2-carboxamide;
5-cyano-N-{4-[1-(morpholin-4-ylacetyl)-1,2,3,6-tetrahydropyridin-4-yl]phenyl}-1,3-dihydro-2H-isoindole-2-carboxamide;
N-(4-{1-[(3R)-tetrahydrofuran-3-ylcarbonyl]-1,2,3,6-tetrahydropyridin-4-yl}phenyl)-1,3-dihydro-2H-isoindole-2-carboxamide;
N-(4-{1-[(3S)-tetrahydrofuran-3-ylcarbonyl]-1,2,3,6-tetrahydropyridin-4-yl}phenyl)-1,3-dihydro-2H-isoindole-2-carboxamide;
N-(4-{1-[(1,1-dioxidotetrahydro-2H-thiopyran-4-yl)carbonyl]-1,2,3,6-tetrahydropyridin-4-yl}phenyl)-1,3-dihydro-2H-isoindole-2-carboxamide;
N-(4-{1-[(2R)-tetrahydrofuran-2-ylcarbonyl]piperidin-4-yl}phenyl)-1,3-dihydro-2H-isoindole-2-carboxamide;
N-(4-{1-[(2S)-tetrahydrofuran-2-ylcarbonyl]piperidin-4-yl}phenyl)-1,3-dihydro-2H-isoindole-2-carboxamide;
N-(4-{1-[(3R)-tetrahydrofuran-3-ylcarbonyl]piperidin-4-yl}phenyl)-1,3-dihydro-2H-isoindole-2-carboxamide;
or a pharmaceutically acceptable salt thereof.

* * * * *